US011976083B2

(12) United States Patent
Canales et al.

(10) Patent No.: US 11,976,083 B2
(45) Date of Patent: May 7, 2024

(54) INHIBITORS OF PEPTIDYLARGININE DEIMINASES

(71) Applicant: Gilead Sciences, Inc., Foster City, CA (US)

(72) Inventors: Eda Y. Canales, San Mateo, CA (US); Weng K. Chang, San Lorenzo, CA (US); Laurent P. Debien, San Francisco, CA (US); Petr Jansa, Foster City, CA (US); Jennifer A. Loyer-Drew, Seattle, WA (US); Luisruben P. Martinez, San Mateo, CA (US); Stephane Perreault, Brier, WA (US); Gary B Phillips, Issaquah, WA (US); Hyung-Jung Pyun, Fremont, CA (US); Roland D. Saito, San Mateo, CA (US); Michael S. Sangi, San Mateo, CA (US); Adam J. Schrier, Redwood City, CA (US); Marina E. Shatskikh, San Francisco, CA (US); James G. Taylor, Burlingame, CA (US); Jennifer A. Treiberg, Redmond, WA (US); Joshua J. Van Veldhuizen, Seattle, WA (US)

(73) Assignee: Gilead Sciences, Inc., Foster City, CA (US)

( * ) Notice: Subject to any disclaimer, the term of this patent is extended or adjusted under 35 U.S.C. 154(b) by 100 days.

(21) Appl. No.: 17/242,617

(22) Filed: Apr. 28, 2021

(65) Prior Publication Data

US 2023/0002412 A1    Jan. 5, 2023

Related U.S. Application Data

(60) Provisional application No. 63/129,430, filed on Dec. 22, 2020, provisional application No. 63/018,411, filed on Apr. 30, 2020.

(51) Int. Cl.

| C07D 471/18 | (2006.01) |
| A61K 31/4184 | (2006.01) |
| A61K 31/4188 | (2006.01) |
| A61K 31/437 | (2006.01) |
| A61K 45/06 | (2006.01) |
| A61P 3/10 | (2006.01) |
| A61P 7/02 | (2006.01) |
| A61P 19/02 | (2006.01) |
| A61P 35/00 | (2006.01) |
| C07D 471/12 | (2006.01) |
| C07D 471/14 | (2006.01) |
| C07D 487/08 | (2006.01) |
| C07D 491/22 | (2006.01) |
| C07D 498/18 | (2006.01) |
| C07D 498/22 | (2006.01) |
| C07D 513/18 | (2006.01) |
| C07D 519/00 | (2006.01) |

(52) U.S. Cl.
CPC ............ C07D 519/00 (2013.01); A61K 45/06 (2013.01); C07D 471/14 (2013.01)

(58) Field of Classification Search
CPC .. C07D 471/18; C07D 471/12; C07D 471/14; C07D 487/08; C07D 491/22; C07D 498/18; C07D 498/22; C07D 513/18; A61K 31/4184; A61K 31/4188; A61K 31/437; A61K 45/06; A61P 3/10; A61P 7/02; A61P 19/02; A61P 35/00
See application file for complete search history.

(56) References Cited

U.S. PATENT DOCUMENTS

2018/0297983 A1* 10/2018 Amans .................... A61P 37/02

FOREIGN PATENT DOCUMENTS

| WO | WO-2014015905 A1 | 1/2014 |
| WO | WO-2016185279 A1 | 11/2016 |
| WO | WO-2017100594 A1 | 6/2017 |
| WO | WO-2017100601 A1 | 6/2017 |
| WO | WO-2017147102 A1 | 8/2017 |
| WO | WO-2018022897 A1 | 2/2018 |
| WO | WO-2018049296 A1 | 3/2018 |
| WO | WO-2019057910 A1 | 3/2019 |
| WO | WO-2019058393 A1 | 3/2019 |
| WO | WO-2019077631 A1 | 4/2019 |
| WO | WO-2019152883 A1 | 8/2019 |
| WO | WO-2019161803 A1 | 8/2019 |
| WO | WO-2020033488 A1 | 2/2020 |
| WO | WO-2020033490 A1 | 2/2020 |
| WO | WO-2020033514 A1 | 2/2020 |
| WO | WO-2020033520 A1 | 2/2020 |
| WO | WO-2021057910 A1 | 4/2021 |
| WO | WO-2021061803 A1 | 4/2021 |

(Continued)

OTHER PUBLICATIONS

International Search Report and Written Opinion received for PCT Application No. PCT/US2021/029557, dated Jul. 20, 2021, 12 pages.

(Continued)

*Primary Examiner* — Bruck Kifle

(57) ABSTRACT

The present disclosure relates to novel compounds for use in therapeutic treatment of a disease associated with peptidylarginine deiminases (PADs), such as peptidylarginine deiminase type 4 (PAD4). The present disclosure also relates to processes and intermediates for the preparation of such compounds, methods of using such compounds and pharmaceutical compositions comprising the compounds described herein.

15 Claims, No Drawings

Specification includes a Sequence Listing.

(56) References Cited

FOREIGN PATENT DOCUMENTS

| WO | WO-2021158840 A1 | 8/2021 |
|----|------------------|--------|
| WO | WO-2021163254 A1 | 8/2021 |

OTHER PUBLICATIONS

Wermuth, C. G. (1998) "The Practice of Medicinal Chemistry" First Volume Technomics, Inc., p. 273-296, Chapter 14, conversion of ring structure.

* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcccagggga cattgatccg t                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcagggcacc atgttccacc a                                            21

INHIBITORS OF PEPTIDYLARGININE DEIMINASES

CROSS REFERENCE TO RELATED APPLICATIONS

This application claims priority to U.S. Provisional Application No. 63/018,411, filed Apr. 30, 2020, and U.S. Provisional Application No. 63/129,430, filed Dec. 22, 2020, both of which are incorporated herein in their entireties for all purposes.

SEQUENCE LISTING

The instant application contains a Sequence Listing which has been submitted electronically in ASCII format and is hereby incorporated by reference in its entirety. Said ASCII copy, created on Apr. 8, 2021, is named 1304-US-NP_SL.txt and is 740 bytes in size.

FIELD

The present disclosure relates to novel compounds for use in therapeutic treatment of a disease associated with peptidylarginine deiminases (PADs). The present disclosure also relates to processes and intermediates for the preparation of such compounds, methods of using such compounds and pharmaceutical compositions comprising the compounds described herein.

BACKGROUND

Peptidylarginine deiminases catalyze the posttranslational modification of peptidyl arginine to peptidyl citrulline. There are five known PAD isozymes with 45% to 58% amino acid sequence identity between human isozymes and at least 70% identity across each vertebrate orthologue. PADs have diverse tissue distribution, different putative physiological functions, and reported associations with various disease states. PAD6 is thought to be the only catalytically inactive PAD and is expressed mainly in oocyte, ovary and early embryo; it is proposed to be involved in oocyte cytoskeletal sheet formation and female fertility. PAD1 and PAD3 are expressed in epidermis and hair follicles and are proposed to be involved in cornification of epidermal tissues, hair growth and maintenance of the stratum corneum. PAD2 is expressed more broadly and can be found in multiple tissues and cell types including brain, spinal cord, skeletal muscles, pituitary glands, spleen, neutrophils and macrophages. It is proposed to be involved in plasticity of CNS, transcription regulation, chemokine signaling, and female reproduction. Expression of PAD4 is restricted to cells of the myeloid lineage, in particular: neutrophils, eosinophils and monocyte/macrophages. PAD4 is hypothesized to be involved in an array of functions, including regulation of transcription, cell cycle, apoptosis, formation of neutrophil extracellular traps (NETs), and tumorgenesis. Accordingly, there is a need for inhibitors of PADs that have therapeutic potential in treatment of disease linked to pathological consequences of citrullination and NETosis including, for example, rheumatoid arthritis, systemic lupus erythematous, antiphospholipid antibody syndrome, small vessels vasculitis, colitis, thrombosis, atherosclerosis, sepsis, diabetes and certain types of cancer.

SUMMARY

Provided herein are macrocyclic compounds for inhibiting peptidylarginine deiminase type 4 (PAD4). The present disclosure provides a compound of Formula (I):

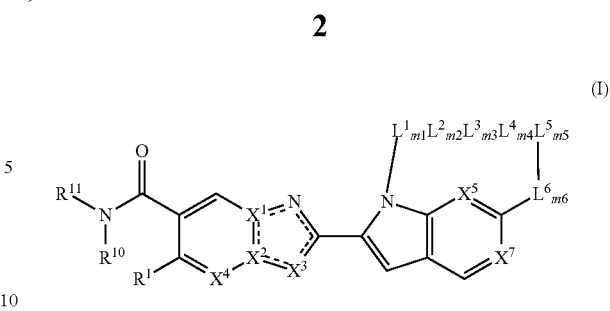

(I)

or a pharmaceutically acceptable salt, stereoisomer, mixture of stereoisomers, or tautomer thereof, wherein:

$X^1$ and $X^2$ are C or N;

$X^3$ is $N-R^3$ or $C-R^3$; provided that two of $X^1$, $X^2$, and $X^3$ are C; where each dashed line represents an optional bond to complete valency requirements of each $X^1$, $X^2$ and $X^3$;

$X^4$ is N or $C-R^2$;

$X^5$ is N or $CR^6$;

$X^7$ is N or $CR^7$;

$R^1$ is hydrogen, halo, $-CN$, $-OR^{12}$, $-N(R^{12})_2$, $-SR^{12}$, $-C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^2$ is hydrogen, halo, $-CN$, $-OR^{12}$, $-N(R^{12})_2$, $-SR^{12}$, $-C_{1-8}$ alkyl optionally substituted with 1 to 3 $Z^2$, $C_{3-6}$ cycloalkyl optionally substituted with 1 to 3 $Z^2$, or 4-6 membered heterocyclyl optionally substituted with 1 to 3 $Z^2$;

when $X^3$ is $N-R^3$, $R^3$ is hydrogen, $C_{1-8}$ alkyl optionally substituted with 1 to 3 $Z^3$, $C_{3-10}$ alkenyl optionally substituted with 1 to 3 $Z^3$, $C_{3-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; and when $X^3$ is $C-R^3$; $R^3$ is hydrogen, halo, $-CN$, $-OR^{12}$, $-N(R^{12})_2$, $-SR^{12}$, $C_{1-8}$ alkyl optionally substituted with 1 to 3 $Z^3$, $C_{2-10}$ alkenyl optionally substituted with 1 to 3 $Z^3$, $C_{2-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; or when $R^2$ is $-C_{1-8}$ alkyl, $-OR^{12}$, or $-N(R^{12})_2$, and $R^3$ is $C_{1-8}$ alkyl, then $R^2$ and $R^3$ may be taken together with the atoms to which they are attached to form an optionally substituted 6 to 8 membered ring;

$R^6$ is hydrogen, halo, $-CN$, $-OR^{12}$, $-C_{1-8}$ alkyl optionally substituted with 1 to 3 $Z^6$, $C_{3-6}$ cycloalkyl optionally substituted with 1 to 3 $Z^6$, or 4-6 membered heterocyclyl optionally substituted with 1 to 3 $Z^6$;

$R^7$ is hydrogen, halo, $-CN$, $-OR^{12}$, $-C_{1-8}$ alkyl optionally substituted with 1 to 3 $Z^7$, $C_{3-6}$ cycloalkyl optionally substituted with 1 to 3 $Z^7$, or 4-6 membered heterocyclyl optionally substituted with 1 to 3 $Z^7$;

$L^1$, $L^2$, $L^3$, $L^4$, $L^5$, and $L^6$ are each independently:

$C_{1-10}$ alkylene, optionally substituted with 1 to 3 $Z^8$;

$C_{2-10}$ alkenylene, optionally substituted with 1 to 3 $Z^8$;

$C_{2-10}$ alkynylene, optionally substituted with 1 to 3 $Z^8$;

2-6 membered heteroalkylene, optionally substituted with 1 to 3 $Z^8$;

$C_3$-$C_{10}$ cycloalkylene, optionally substituted with 1 to 3 $Z^8$;

4-10 membered heterocyclene, optionally substituted with 1 to 3 $Z^8$;

$C_{6-10}$ arylene, optionally substituted with 1 to 3 $Z^8$;

5-10 membered heteroarylene, optionally substituted with 1 to 3 $Z^8$; or
—O—, —N($R^8$)—, —S—, —C(O)—, —C(O)O—, —C(O)N($R^8$)—, —SO—, —SO$_2$—, —SO$_2$N($R^8$)—, —N($R^8$)C(O)O—, —OC(O)O—, —N($R^8$)C(O)N($R^8$)—, —N($R^8$)S(O)$_2$N($R^8$)—, —N($R^8$)C(N—CN)—S(O)(N$R^8$)—, or —S(O)(N$R^8$)N($R^8$)—; and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring;

each $R^8$ and $R^9$ are each independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{10}$ is hydrogen, —$C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, —$C_{1-8}$ alkyl optionally substituted with 1 to 4 $Z^{11}$, —$C_{3-8}$ cycloalkyl optionally substituted with 1 to 4 $Z^{11}$, or 4-12-membered heterocyclyl optionally substituted with 1 to 4 $Z^{11}$; or $R^{10}$ and $R^{11}$ are taken together to form a 4-12-membered heterocyclyl optionally substituted with 1 to 4 $Z^{11}$;

each $R^{12}$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^1$, $Z^2$, $Z^3$, $Z^6$, $Z^7$, and $Z^8$ is independently oxo, halo, —NO$_2$, —N$_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —OR$^9$, —C(O)R$^9$, —C(O)OR$^9$, —C(O)N(R$^9$)$_2$, —N(R$^9$)$_2$, —N(R$^9$)$_3^+$, —N(R$^9$)C(O)R$^9$, —N(R$^9$)C(O)OR$^9$, —N(R$^9$)C(O)N(R$^9$)$_2$, —N(R$^9$)S(O)$_2$(R$^9$), —NR$^9$S(O)$_2$N(R$^9$)$_2$, —NR$^9$S(O)$_2$O(R$^9$), —NS(O)(R$^9$)$_2$, —OC(O)R$^9$, —OC(O)OR$^9$, —OC(O)N(R$^9$)$_2$, —Si(R$^9$)$_3$, —SR$^9$, —S(O)R$^9$, —SF$_5$, —S(O)(NR$^9$)R$^9$, —S(NR$^9$)(NR$^9$)R$^9$, —S(O)(NR$^9$)N(R$^9$)$_2$, —S(O)(NCN)R$^9$, —S(O)$_2$R$^9$, —S(O)$_2$N(R$^9$)$_2$, —C(O)N(R$^9$)S(O)$_2$R$^9$, or —S(O)$_2$N(R$^9$)C(O)R$^9$, wherein each $Z^2$, $Z^3$, $Z^6$, $Z^7$, and $Z^8$ is independently optionally substituted with 1 to 3 $Z^{1a}$;

each $Z^{1a}$ is independently oxo, halo, —NO$_2$, —N$_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —OR$^{13}$, —C(O)R$^{13}$, —C(O)OR$^{13}$, —C(O)N(R$^{13}$)$_2$, —N(R$^{13}$)$_2$, —N(R$^{13}$)$_3^+$, —N(R$^{13}$)C(O)R$^{13}$, —N(R$^{13}$)C(O)OR$^{13}$, —N(R$^{13}$)C(O)N(R$^{13}$)$_2$, —N(R$^{13}$)S(O)$_2$(R$^{13}$), —NR$^{13}$S(O)$_2$N(R$^{13}$)$_2$, —NR$^{13}$S(O)$_2$O(R$^{13}$), —NS(O)(R$^{13}$)$_2$, —OC(O)R$^{13}$, —OC(O)OR$^{13}$, —OC(O)N(R$^{13}$)$_2$, —Si(R$^{13}$)$_3$, —SR$^{13}$, —S(O)R$^{13}$, —SF$_5$, —S(O)(NR$^{13}$)R$^{13}$, —S(NR$^{13}$)(NR$^{13}$)R$^{13}$, —S(O)(NR$^{13}$)N(R$^{13}$)$_2$, —S(O)(NCN)R$^{13}$, —S(O)$_2$R$^{13}$, —S(O)$_2$N(R$^{13}$)$_2$, —C(O)N(R$^{13}$)S(O)$_2$R$^{13}$, or —S(O)$_2$N(R$^{13}$)C(O)R$^{13}$;

each $Z^{10}$ and $Z^{11}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —OR$^{13}$, —C(O)R$^{13}$, —C(O)OR$^{13}$, —C(O)N(R$^{13}$)$_2$, —N(R$^{13}$)$_2$, —N(R$^{13}$)$_3^+$, —N(R$^{13}$)C(O)R$^{13}$, —N(R$^{13}$)C(O)OR$^{13}$, —N(R$^{13}$)C(O)N(R$^{13}$)$_2$, —OC(O)R$^{13}$, —OC(O)OR$^{13}$, —OC(O)—N(R$^{13}$)$_2$, and —S—R$^{13}$; and each $Z^{1b}$ is independently oxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)(aryl), —OC(O)(heteroaryl), —OC(O)(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC (O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl of $Z^{1b}$ is optionally substituted with one or more halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), —S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl).

Also provided herein are compounds of Tables 1 and 1A or a pharmaceutically acceptable salt, stereoisomer, mixture of stereoisomers, or tautomer thereof.

The present disclosure provides a method of inhibiting peptidylarginine deiminase type 4 (PAD4) comprising contacting an effective amount of a compound of Formula (I), or any formula described herein, or a pharmaceutically acceptable salt, stereoisomer, mixture of stereoisomers, or tautomer thereof, with a cell.

The present disclosure provides a method of inhibiting peptidylarginine deiminase type 4 (PAD4) comprising administering an effective amount of a compound of Formula (I), or any formula described herein, or a pharmaceutically acceptable salt, stereoisomer, mixture of stereoisomers, or tautomer thereof, to a patient in need thereof.

The present disclosure provides a method for treating a disease or disorder mediated by peptidylarginine deiminase type 4 (PAD4), comprising administering an effective amount of a compound of Formula (I), or any formula described herein, or a pharmaceutically acceptable salt, stereoisomer, mixture of stereoisomers, or tautomer thereof, to a patient in need thereof.

The present disclosure provides a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula (I), or any formula described herein, or a pharmaceutically acceptable salt, stereoisomer, mixture of stereoisomers, or tautomer thereof, to a patient in need thereof.

In one embodiment, the present disclosure provides a pharmaceutical composition comprising a compound of Formula (I), or any formula described herein, or a pharmaceutically acceptable salt, stereoisomer, mixture of stereoisomers, or tautomer thereof, and a pharmaceutically acceptable carrier or excipient.

In one embodiment, the present disclosure provides a pharmaceutical composition comprising a compound of Formula (I), or any formula described herein, or a pharmaceutically acceptable salt, stereoisomer, mixture of stereoisomers, or tautomer thereof, and at least one additional therapeutic agent and at least one pharmaceutically acceptable carrier or excipient.

In one embodiment, the present disclosure provides a pharmaceutical composition comprising a compound of Formula (I), or any formula described herein, or a pharmaceutically acceptable salt, stereoisomer, mixture of stereoisomers, or tautomer thereof, at least one additional therapeutic agent suitable for treating rheumatoid arthritis, and at least one pharmaceutically acceptable carrier or excipient.

In one embodiment, the present disclosure provides a kit that includes a compound of Formula (I), or any formula described herein, or a pharmaceutically acceptable salt, stereoisomer, mixture of stereoisomers, or tautomer thereof, a label and/or instructions for use of the compound in the treatment of rheumatoid arthritis or a disease or condition mediated by peptidylarginine deiminase type 4 (PAD4).

In one embodiment, the present disclosure provides a compound of Formula (I), or any formula described herein, or a pharmaceutically acceptable salt, stereoisomer, mixture of stereoisomers, or tautomer thereof, for use in therapy.

In another embodiment, the present disclosure provides a compound of Formula (I), or any formula described herein, or a pharmaceutically acceptable salt, stereoisomer, mixture of stereoisomers, or tautomer thereof, for use in the manufacture of a medicament for treating rheumatoid arthritis or a disease or condition mediated by peptidylarginine deiminase type 4 (PAD4).

DETAILED DESCRIPTION

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A wavy line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the "include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 10 carbon atoms (i.e., $C_{1-10}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to any group derived from a straight or branched hydrocarbon with at least one carbon-carbon double bond. Unless otherwise specified, alkenyl groups have from 2 to 20 carbon atoms (i.e., $C_{2-20}$ alkenyl), 2 to 12 carbon atoms (i.e., $C_{2-12}$ alkenyl), 2 to 10 carbon atoms (i.e., $C_{2-10}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl, and 1,3-butadienyl).

"Alkynyl" refers to any group derived from a straight or branched hydrocarbon with at least one carbon-carbon triple bond. Unless otherwise specified, alkynyl groups have from 2 to 20 carbon atoms (i.e., $C_{2-20}$ alkynyl), 2 to 12 carbon atoms (i.e., $C_{2-12}$ alkynyl), 2 to 10 carbon atoms (i.e., $C_{2-10}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond. Examples of alkynyl groups include, but are not limited to, ethynyl (—C≡C—), propargyl (—CH$_2$C≡C—), (E)-pent-3-en-1-ynyl, and the like.

The term "aryl" as used herein refers to a single all carbon aromatic ring or a multiple condensed all carbon ring system wherein at least one of the rings is aromatic. For example, in certain embodiments, an aryl group 6 to 20 ring carbon atoms (i.e., $C_{6-20}$ aryl), 6 to 14 carbon ring atoms (i.e., $C_{6-14}$ aryl), 6 to 12 carbon ring atoms (i.e., $C_{6-12}$ aryl), or 6 to 10 carbon ring atoms (i.e., $C_{6-10}$ aryl). Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. Aryl, however, does not encompass or overlap in any way with heteroaryl defined below. If one or more aryl groups are fused with a heteroaryl ring, the resulting ring system is heteroaryl. It is also to be understood that when reference is made to a certain atom-range membered aryl (e.g., $C_{6-10}$ aryl), the atom range is for the total ring atoms of the aryl. For example, a 6-membered aryl would include phenyl and a 10-membered aryl would include naphthyl and 1,2,3,4-tetrahydronaphthyl. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene, and the like. Non-limiting examples of aryl groups include, but are not limited to, phenyl, indenyl, naphthyl, 1,2,3,4-tetrahydronaphthyl, anthracenyl, and the like.

The term "cycloalkyl" refers to a single saturated or partially unsaturated all carbon ring having 3 to 20 annular carbon atoms (i.e., $C_{3-20}$ cycloalkyl), 3 to 14 ring carbon atoms (i.e., $C_{3-14}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). As used herein the term "cycloalkenyl" refers to the non-aromatic carbocyclic (partially saturated cyclic alkyl) group having at least one double bond. Accordingly, cycloalkyl includes multicyclic carbocycles such as a bicyclic carbocycles (e.g., bicyclic carbocycles having about 6 to 12 annular carbon atoms such as bicyclo[3.1.0]hexane, bicyclo[2.1.1]hexane), bicyclo[1.1.1]pentane, and polycyclic carbocycles (e.g., tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, spiro[3.3]heptane, and 1-cyclohex-3-enyl.

"Halo" and "halogen" refer to fluoro, chloro, bromo and iodo.

"Haloalkyl" refers to an alkyl group as defined herein, wherein one or more hydrogen atoms (e.g., 1-5, or 1-3) are replaced by a halogen. Examples include, but are not limited to, —CH$_2$Cl, —CH$_2$F, —CH$_2$Br, —CFClBr, —CH$_2$CH$_2$Cl, —CH$_2$CH$_2$F, —CF$_3$, —CH$_2$CF$_3$, —CH$_2$CCl$_3$, and the like, as well as alkyl groups such as perfluoroalkyl in which all hydrogen atoms are replaced by fluorine atoms.

"Heteroalkyl" refers to an alkyl in which one or more of the carbon atoms (and any associated hydrogen atoms) are each independently replaced with the same or different heteroatom or heteroatomic group. Heteroatoms include, but are not limited to, N, P, O, S, etc. Heteroatomic groups include, but are not limited to, —NR—, —O—, —S—, —PH—, —P(O)$_2$—, —S(O)—, —S(O)$_2$—, and the like, where R is H, alkyl, aryl, cycloalkyl, heteroalkyl, heteroaryl or cycloheteroalkyl. Heteroalkyl groups include, but are not limited to, —OCH$_3$, —CH$_2$OCH$_3$, —SCH$_3$, —CH$_2$SCH$_3$, —NRCH$_3$, —CH$_2$NRCH$_3$, —CH$_2$OH and the like, where R is hydrogen, alkyl, aryl, arylalkyl, heteroalkyl, or heteroaryl. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include, but are not limited to, groups derived from acridine, benzimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms, 2 to 12 ring carbon atoms, 2 to 10 ring carbon atoms, 2 to 8 ring carbon atoms, 3 to 12 ring carbon atoms, 3 to 8 ring carbon atoms, or 3 to 6 ring carbon atoms; and having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Non-limiting examples of bridged-heterocyclyl include 8-azabicyclo[3.2.1]octan-8-yl, 2-azabicyclo[3.2.1]octan-2-yl, 2-azabicyclo[2.2.1]heptan-2-yl, and 7-azabicyclo[2.2.1]heptan-7-yl. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, 5-azaspiro[2.4]heptanyl, and 6-oxa-1-azaspiro[3.3]heptanyl. Examples of the fused-heterocyclyl rings include, but are not limited to, 3-azabicyclo[3.1.0]hexanyl, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. Additional examples include dihydroquinolines, e.g., 3,4-dihydroquinoline, dihydroisoquinolines, e.g., 1,2-dihydroisoquinoline, dihydroimidazole, tetrahydroimidazole, etc., indoline, isoindoline, isoindolones (e.g., isoindolin-1-one), isatin, dihydrophthalazine, quinolinone, spiro[cyclopropane-1,1'-isoindolin]-3'-one, and the like. Additional examples of heterocycles include 2-azabicyclo[2.2.1]heptane, 8-azabicyclo[3.2.1]octane, 3-azabicyclo[4.1.0]heptane, octahydro-2H-pyrido[4,3-b][1,4]oxazine, hexahydropyridazine, 3,8-diazabicyclo[3.2.1]octanyl, 2,5-diazabicyclo[2.2.1]heptanyl, 3,6-diazabicyclo[3.1.1]heptanyl, 3-oxa-7,9-diazabicyclo[3.3.1]nonanyl, 7-azabicyclo[2.2.1]heptane, 2-azabicyclo[2.2.2]octane, 6-oxa-2-azabicyclo[3.2.1]octane, and hexahydropyrazino[2,1-c][1,4]oxazinyl, for example, where the heterocyclyl can be bound via either ring of the fused system.

The term "macrocyclic ring" as used herein refers to a ring having at least 11 annular atoms within a single mono-cyclic ring. The macrocyclic ring may be monocyclic or polycyclic, including but not limited to bridged, fused and spiro rings, provided that the ring system comprises at least one mono-cyclic ring having at least 11 annular atoms. The number of members or atoms in a macrocyclic ring is determined by counting total ring members in the shortest path around the macrocycle. In certain embodiments, the macrocyclic ring is a 12 to 20 membered ring, a 12 to 19 membered ring, a 13 to 19 membered ring, a 12 to 18 membered ring, a 12 to 16 membered ring, a 14 to 20 membered ring, a 14 to 19 membered ring, a 14 to 18 membered ring, a 14 to 16 membered ring, a 20 membered ring, a 19 membered ring, a 18 membered ring, a 17 membered ring, a 16 membered ring, a 15 membered ring, a 14 membered ring, a 13 membered ring, or a 12 membered ring. Examples of a 14-membered macrocyclic ring include, e.g.:

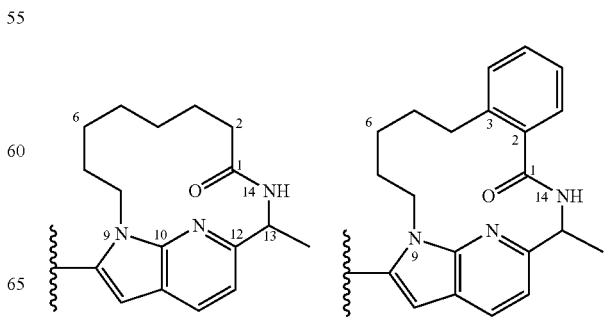

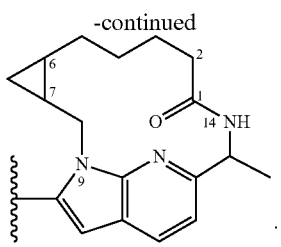

Examples of a 12-membered macrocyclic ring include, e.g.:

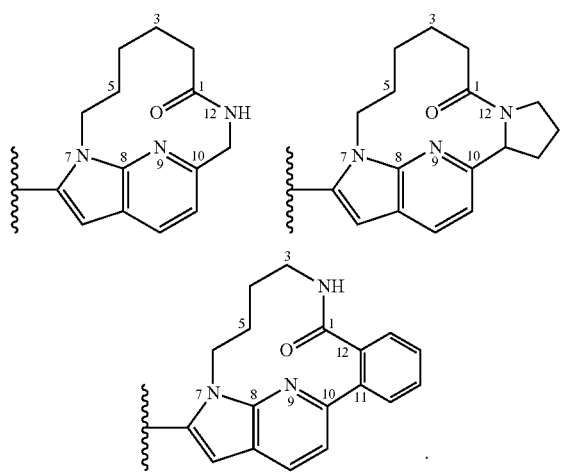

"Bridged" refers to a ring fusion wherein non-adjacent atoms on a ring are joined by a divalent substituent, such as an alkylene or heteroalkylene group or a single heteroatom. Quinuclidinyl and adamantyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents bound to the same atom join together (e.g., two $Z^8$ groups join together) they may be taken from the same point of attachment to form a spiro ring.

The term "fused" refers to a ring which is bound to an adjacent ring.

"Oxo" refers to =O or —O−. "Hydroxyl" and "hydroxy" are used interchangeably and refer to —OH. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g., $CH_3CH_2NHC(O)$—), $C_{1-6}$ alkoxycarbonyl (e.g., $CH_3O$—C(O)—), 5-7 membered heterocyclyl-$C_{1-6}$ alkyl (e.g., piperazinyl-$CH_2$—), $C_{1-6}$ alkylsulfonyl-5-7 membered heterocyclyl (e.g., $CH_3S(O)_2$-morpholinyl-), 5-7 membered heterocyclyl $C_{1-6}$ alkoxy, 5-7 membered heterocyclyloxy, (4-7 membered heterocyclyl)-4-7 membered heterocyclyl (e.g., oxetanyl-pyrrolidinyl-), $C_{3-6}$ cycloalkylaminocarbonyl (e.g., cyclopropyl-NH—C(O)—), 5-7 membered heterocyclyl-$C_{2-6}$ alkynyl (e.g., N-piperazinyl-$CH_2C\equiv CCH_2$—), and $C_{6-10}$ arylaminocarbonyl (e.g., phenyl-NH—C(O)—).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. The suffix "ene" is often used to refer to a group that has two single bond points of attachments to other groups. For example, methylene refers to —$CH_2$—. Similarly, alkylene, alkenylene, alkynylene, cycloalkylene, heterocyclene, arylene, and heteroarylene refer to respective alkyl, alkenyl, alkynyl, cycloalkyl, heterocyclyl, aryl, and heteroaryl groups as defined herein having two single bond points of attachments to other groups. Also, unless indicated explicitly otherwise, where combinations of groups are referred to herein as one moiety, e.g., arylalkyl, the last-mentioned group contains the atom by which the moiety is attached to the rest of the molecule.

The compounds described herein include isomers, stereoisomers and the like. As used herein, the term "isomers" refers to different compounds that have the same molecular formula but differ in arrangement and configuration of the atoms. Also as used herein, the term "a stereoisomer" refers to any of the various stereo isomeric configurations which may exist for a given compound disclosed herein and includes geometric isomers. It is understood that a substituent may be attached at a chiral center of a carbon atom. Therefore, the compound disclosed herein includes enantiomers, diastereomers or racemates of the compound.

"Enantiomers" are a pair of stereoisomers that are non-superimposable mirror images of each other. A 1:1 mixture of a pair of enantiomers is a "racemic" mixture.

The term is used to designate a racemic mixture where appropriate. "Diastereoisomers" are stereoisomers that have at least two stereocenters, but which are not mirror-images of each other.

The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. To the extent that compounds depicted herein are represented as having a particular stereochemistry, it is understood by one of skill in the art that such compounds may contain some detectable or undetectable levels of compounds sharing the same structure, but having different stereochemistry.

"IC$_{95}$" or "EC$_{95}$" refers to the inhibitory concentration required to achieve 95% of the maximum desired effect, which in many cases herein is the inhibition of the PAD4 enzyme.

"IC$_{50}$" or "EC$_{50}$" refers to the inhibitory concentration required to achieve 50% of the maximum desired effect, which in many cases herein is the inhibition of the PAD4 enzyme.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, PA, (2005), at p. 732, Table 38-5, both of which are hereby incorporated by reference herein.

Compounds disclosed herein include isotopically labeled, solvates, hydrates, tautomers, stereoisomers and salt forms thereof.

Provided are also compounds in which from 1 to n hydrogen atoms attached to a carbon atom may be replaced by deuterium atom or D, in which n is the number of hydrogen atoms in the molecule. As known in the art, the deuterium atom is a non-radioactive isotope of the hydrogen atom. Such compounds exhibit may increase resistance to metabolism, and thus may be useful for increasing the half-life of the compounds when administered to a mammal. See, e.g., Foster, "Deuterium Isotope Effects in Studies of Drug Metabolism," Trends Pharmacol. Sci., 5(12):524-527 (1984). Such compounds are synthesized by means well known in the art, for example by employing starting materials in which one or more hydrogen atoms have been replaced by deuterium.

Any formula or structure given herein, including Formula (I), or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The present disclosure also provides for prodrugs of the compounds disclosed herein. A "prodrug" is defined in the pharmaceutical field as a biologically inactive derivative of a drug that upon administration to the human body is converted to the biologically active parent drug according to some chemical or enzymatic pathway.

Compounds

Provided herein are compounds that function as inhibitors of peptidylarginine deiminase type 4 (PAD4), methods of using such compounds and compositions comprising such compounds optionally in combination with one or more additional agents or therapies. In all embodiments discussed herein where there is more than one occurrence of a group or variable, it is intended that the group or variable is independently selected the list that follows. All embodiments directed to compounds also include any salt, stereoisomer, mixture of stereoisomers, prodrug, isotopically labeled, solvate, hydrate, or tautomer thereof. It is further contemplated that the macrocycle moiety of the compounds disclosed herein confers enhanced potency as inhibitors of peptidylarginine deiminase type 4 (PAD4).

Provided is a compound of Formula (I):

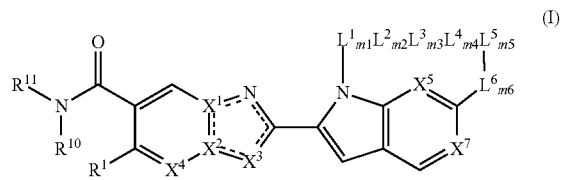

or a pharmaceutically acceptable salt, stereoisomer, mixture of stereoisomers, or tautomer thereof, wherein:

$X^1$ and $X^2$ are C or N;

$X^3$ is N—$R^3$ or C—$R^3$; provided that two of $X^1$, $X^2$, and $X^3$ are C; where each dashed line represents an optional bond to complete valency requirements of each $X^1$, $X^2$ and $X^3$;

$X^4$ is N or C—$R^2$;

$X^5$ is N or $CR^6$;

$X^7$ is N or $CR^7$;

$R^1$ is hydrogen, halo, —CN, —$OR^{12}$, —$N(R^{12})_2$, —$SR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^2$ is hydrogen, halo, —CN, —$OR^{12}$, —$N(R^{12})_2$, —$SR^{12}$, —$C_{1-8}$ alkyl optionally substituted with 1 to 3 $Z^2$, $C_{3-6}$ cycloalkyl optionally substituted with 1 to 3 $Z^2$, or 4-6 membered heterocyclyl optionally substituted with 1 to 3 $Z^2$;

when $X^3$ is N—$R^3$, $R^3$ is hydrogen, $C_{1-8}$ alkyl optionally substituted with 1 to 3 $Z^3$, $C_{3-10}$ alkenyl optionally substituted with 1 to 3 $Z^3$, $C_{3-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; and when $X^3$ is C—$R^3$; $R^3$ is hydrogen, halo, —CN, —$OR^{12}$, —$N(R^{12})_2$, —$SR^{12}$, $C_{1-8}$ alkyl optionally substituted with 1 to 3 $Z^3$, $C_{2-10}$ alkenyl optionally substituted with 1 to 3 $Z^3$, $C_{2-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; or when $R^2$ is —$C_{1-8}$ alkyl, —$OR^{12}$, or —$N(R^{12})_2$, and $R^3$ is $C_{1-8}$ alkyl, then $R^2$ and $R^3$ may be taken together with the atoms to which they are attached to form an optionally substituted 6 to 8 membered ring;

$R^6$ is hydrogen, halo, —CN, —$OR^{12}$, —$C_{1-8}$ alkyl optionally substituted with 1 to 3 $Z^6$, $C_{3-6}$ cycloalkyl optionally substituted with 1 to 3 $Z^6$, or 4-6 membered heterocyclyl optionally substituted with 1 to 3 $Z^6$;

$R^7$ is hydrogen, halo, —CN, —$OR^{12}$, —$C_{1-8}$ alkyl optionally substituted with 1 to 3 $Z^7$, $C_{3-6}$ cycloalkyl optionally substituted with 1 to 3 $Z^7$, or 4-6 membered heterocyclyl optionally substituted with 1 to 3 $Z^7$;

$L^1$, $L^2$, $L^3$, $L^4$, $L^5$, and $L^6$ are each independently:

$C_{1-10}$ alkylene, optionally substituted with 1 to 3 $Z^8$;

$C_{2-10}$ alkenylene, optionally substituted with 1 to 3 $Z^8$;

$C_{2-10}$ alkynylene, optionally substituted with 1 to 3 $Z^8$;

2-6 membered heteroalkylene, optionally substituted with 1 to 3 $Z^8$;

$C_3$-$C_{10}$ cycloalkylene, optionally substituted with 1 to 3 $Z^8$;

4-10 membered heterocyclene, optionally substituted with 1 to 3 $Z^8$;

$C_{6-10}$ arylene, optionally substituted with 1 to 3 $Z^8$;

5-10 membered heteroarylene, optionally substituted with 1 to 3 $Z^8$; or

—O—, —$N(R^8)$—, —S—, —C(O)—, —C(O)O—, —C(O)$N(R^8)$—, —SO—, —$SO_2$—, —$SO_2N(R^8)$—, —$N(R^8)$C(O)O—, —OC(O)O—, —$N(R^8)$C(O)N($R^8$)—, —$N(R^8)S(O)_2N(R^8)$—, —$N(R^8)$C(N—CN)—, —S(O)($NR^8$)—, or —S(O)($NR^8$)$N(R^8)$—; each of $L^1$, $L^2$, $L^3$, $L^4$, $L^5$, and $L^6$ may be the same or different; and m1, m2, m3, m4, m5, and m6 are each independently 0 or 1; each of m1, m2, m3, m4, m5, and m6 may be the same or different;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring;

each $R^8$ and $R^9$ are each independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$; each $R^8$ and $R^9$ may be the same or different;

$R^{10}$ is hydrogen, —$C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, —$C_{1-8}$ alkyl optionally substituted with 1 to 4 $Z^{11}$, —$C_{3-8}$ cycloalkyl optionally substituted with 1 to 4 $Z^{11}$, or 4-12-membered heterocyclyl optionally substituted with 1 to 4 $Z^{11}$; or $R^{10}$ and $R^{11}$ are taken together to form a 4-12-membered heterocyclyl optionally substituted with 1 to 4 $Z^{11}$;

each $R^{12}$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$; each $R^{12}$ and $R^{13}$ may be the same or different;

each $Z^1$, $Z^2$, $Z^3$, $Z^6$, $Z^7$, and $Z^8$ is independently oxo, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^9$, —C(O)$R^9$, —C(O)$OR^9$, —C(O)$N(R^9)_2$, —$N(R^9)_2$, —$N(R^9)_3^+$, —$N(R^9)$C(O)$R^9$, —$N(R^9)$C(O)$OR^9$, —$N(R^9)$C(O)$N(R^9)_2$, —$N(R^9)S(O)_2(R^9)$, —$NR^9S(O)_2N(R^9)_2$, —$NR^9S(O)_2O(R^9)$, —NS(O)$(R^9)_2$, —OC(O)$R^9$, —OC(O)$OR^9$, —OC(O)$N(R^9)_2$, —Si$(R^9)_3$, —$SR^9$, —S(O)$R^9$, —$SF_5$, —S(O)($NR^9$)$R^9$, —S($NR^9$)($NR^9$)$R^9$, —S(O)($NR^9$)$N(R^9)_2$, —S(O)(NCN)$R^9$, —S(O)$_2R^9$, —S(O)$_2N(R^9)_2$, —C(O)$N(R^9)S(O)_2R^9$, or —S(O)$_2N(R^9)C(O)R^9$, wherein each $Z^1$, $Z^2$, $Z^3$, $Z^6$, $Z^7$, and $Z^8$ is independently optionally substituted with 1 to 3 $Z^{1a}$; each $Z^1$, $Z^2$, $Z^3$, $Z^6$, $Z^7$, and $Z^8$ may be the same or different;

each $Z^{1a}$ is independently oxo, halo, —$NO_2$, —$N_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{13}$, —C(O)$R^{13}$, —C(O)$OR^{13}$, —C(O)$N(R^{13})_2$, —$N(R^{13})_2$, —$N(R^{13})_3^+$, —$N(R^{13})$C(O)$R^{13}$, —$N(R^{13})$C(O)$OR^{13}$, —$N(R^{13})$C(O)$N(R^{13})_2$, —$N(R^{13})S(O)_2(R^{13})$, —$NR^{13}S(O)_2N(R^{13})_2$, —$NR^{13}S(O)_2O(R^{13})$, —NS(O)$(R^{13})_2$, —OC(O)$R^{13}$, —OC(O)$OR^{13}$, —OC(O)$N(R^{13})_2$, —Si$(R^{13})_3$, —$SR^{13}$, —S(O)$R^{13}$, —$SF_5$, —S(O)($NR^{13}$)$R^{13}$, —S($NR^{13}$)($NR^{13}$)$R^{13}$, —S(O)($NR^{13}$)$N(R^{13})_2$, —S(O)

(NCN)R$^{13}$, —S(O)$_2$R$^{13}$, —S(O)$_2$N(R$^{13}$)$_2$, —C(O)N(R$^{13}$)S(O)$_2$R$^{13}$, or —S(O)$_2$N(R$^{13}$)C(O)R$^{13}$;

each Z$^{10}$ and Z$^{11}$ is independently selected from oxo, halo, —CN, C$_{1-8}$ alkyl optionally substituted by 1 to 3 Z$^{1b}$, C$_{3-8}$ cycloalkyl optionally substituted by 1 to 3 Z$^{1b}$, aryl optionally substituted by 1 to 3 Z$^{1b}$, 4-10 membered heterocyclyl optionally substituted by 1 to 3 Z$^{1b}$, 5-10 membered heteroaryl optionally substituted with 1 to 3 Z$^{1b}$, —OR$^{13}$, —C(O)R$^{13}$, —C(O)OR$^{13}$, —C(O)N(R$^{13}$)$_2$, —N(R$^{13}$)$_2$, —N(R$^{13}$)$_3^+$, —N(R$^{13}$)C(O)R$^{13}$, —N(R$^{13}$)C(O)OR$^{13}$, —N(R$^{13}$)C(O)N(R$^{13}$)$_2$, —OC(O)R$^{13}$, —OC(O)OR$^{13}$, —OC(O)—N(R$^{13}$)$_2$, and —S—R$^{13}$; each Z$^{10}$ and Z$^{11}$ may be the same or different; and each Z$^{1b}$ is independently oxo, hydroxy, halo, —NO$_2$, —N$_3$, —CN, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —OC(O) (C$_{1-9}$ alkyl), —OC(O)(C$_{2-6}$ alkenyl), —OC(O)(C$_{2-6}$ alkenyl), —OC(O)(C$_{2-6}$ alkynyl), —OC(O)(C$_{3-15}$ cycloalkyl), —OC(O)(C$_{1-8}$ haloalkyl), —OC(O)(aryl), —OC(O)(heteroaryl), —OC(O)(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl of Z$^{1b}$ is optionally substituted with one or more halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), —S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl).

Also provided is a compound of Formula (I):

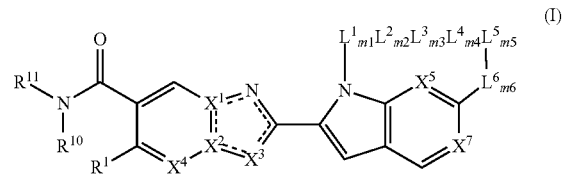

or a pharmaceutically acceptable salt, stereoisomer, mixture of stereoisomers, or tautomer thereof, wherein:

X$^1$ and X$^2$ are C or N;

X$^3$ is N—R$^3$ or C—R$^3$; provided that two of X$^1$, X$^2$, and X$^3$ are C; where each dashed line represents an optional bond to complete valency requirements of each X$^1$, X$^2$ and X$^3$;

X$^4$ is N or C—R$^2$;

X$^5$ is N or CR$^6$;

X$^7$ is N or CR$^7$;

R$^1$ is hydrogen, halo, —CN, —OR$^{12}$, —N(R$^{12}$)$_2$, —SR$^{12}$, —C$_{1-8}$ alkyl optionally substituted with 1 to 3 Z$^1$, C$_{3-6}$ cycloalkyl optionally substituted with 1 to 3 Z$^1$, or 4-6 membered heterocyclyl optionally substituted with 1 to 3 Z$^1$;

R$^2$ is hydrogen, halo, —CN, —OR$^{12}$, —N(R$^{12}$)$_2$, —SR$^{12}$, —C$_{1-8}$ alkyl optionally substituted with 1 to 3 Z$^1$, C$_{3-6}$ cycloalkyl optionally substituted with 1 to 3 Z$^2$, or 4-6 membered heterocyclyl optionally substituted with 1 to 3 Z$^2$;

when X$^3$ is N—R$^3$, R$^3$ is hydrogen, C$_{1-8}$ alkyl optionally substituted with 1 to 3 Z$^3$, C$_{3-10}$ alkenyl optionally substituted with 1 to 3 Z$^3$, C$_{3-10}$ alkynyl optionally substituted with 1 to 3 Z$^3$, C$_{3-10}$ cycloalkyl optionally substituted with 1 to 3 Z$^3$, or 4-10 membered heterocyclyl optionally substituted with 1 to 3 Z$^3$; and when $X^3$ is C—$R^3$; $R^3$ is hydrogen, halo, —CN, —$OR^{12}$, —$N(R^{12})_2$, —$SR^{12}$, $C_{1-8}$ alkyl optionally substituted with 1 to 3 $Z^3$, $C_{2-10}$ alkenyl optionally substituted with 1 to 3 $Z^3$, $C_{2-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; or when $R^2$ is —$C_{1-8}$ alkyl, —$OR^{12}$, or —$N(R^{12})_2$, and $R^3$ is $C_{1-8}$ alkyl, then $R^2$ and $R^3$ may be taken together with the atoms to which they are attached to form an optionally substituted 6 to 8 membered ring;

$R^6$ is hydrogen, halo, —CN, —$OR^{12}$, —$C_{1-8}$ alkyl optionally substituted with 1 to 3 $Z^6$, $C_{3-6}$ cycloalkyl optionally substituted with 1 to 3 $Z^6$, or 4-6 membered heterocyclyl optionally substituted with 1 to 3 $Z^6$;

$R^7$ is hydrogen, halo, —CN, —$OR^{12}$, —$C_{1-8}$ alkyl optionally substituted with 1 to 3 $Z^7$, $C_{3-6}$ cycloalkyl optionally substituted with 1 to 3 $Z^7$, or 4-6 membered heterocyclyl optionally substituted with 1 to 3 $Z^7$;

$L^1$, $L^2$, $L^3$, $L^4$, $L^5$, and $L^6$ are each independently:
$C_{1-10}$ alkylene, optionally substituted with 1 to 3 $Z^8$;
$C_{2-10}$ alkenylene, optionally substituted with 1 to 3 $Z^8$;
$C_{2-10}$ alkynylene, optionally substituted with 1 to 3 $Z^8$;
2-6 membered heteroalkylene, optionally substituted with 1 to 3 $Z^8$;
$C_3$-$C_{10}$ cycloalkylene, optionally substituted with 1 to 3 $Z^8$;
4-10 membered heterocyclene, optionally substituted with 1 to 3 $Z^8$;
$C_{6-10}$ arylene, optionally substituted with 1 to 3 $Z^8$;
5-10 membered heteroarylene, optionally substituted with 1 to 3 $Z^8$; or
—O—, —$N(R^8)$—, —S—, —C(O)—, —C(O)O—, —C(O)N($R^8$)—, —SO—, —$SO_2$—, —$SO_2N(R^8)$—, —N($R^8$)C(O)O—, —OC(O)O—, —N($R^8$)C(O)N($R^8$)—, —N($R^8$)$S(O)_2N(R^8)$—, —N($R^8$)C(N—CN)—S(O)N($R^8$)—, or —S(O)N($R^8$)N($R^8$)—; and m1, m2, m3, m4, m5, and m6 are each independently 0 or 1;
provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring;

each $R^8$ and $R^9$ are each independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{10}$ is hydrogen, —$C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, —$C_{1-8}$ alkyl optionally substituted with 1 to 4 $Z^{11}$, —$C_{3-8}$ cycloalkyl optionally substituted with 1 to 4 $Z^{11}$, or 4-12-membered heterocyclyl optionally substituted with 1 to 4 $Z^{11}$; or $R^{10}$ and $R^{11}$ are taken together to form a 4-12-membered heterocyclyl optionally substituted with 1 to 4 $Z^{11}$;

each $R^{12}$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^1$, $Z^2$, $Z^3$, $Z^6$, $Z^7$, and $Z^8$ is independently oxo, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^9$, —$C(O)R^9$, —$C(O)OR^9$, —$C(O)N(R^9)_2$, —$N(R^9)_2$, —$N(R^9)_3^+$, —$N(R^9)C(O)R^9$, —$N(R^9)C(O)OR^9$, —$N(R^9)C(O)N(R^9)_2$, —$N(R^9)S(O)_2(R^9)$, —$NR^9S(O)_2N(R^9)_2$, —$NR^9S(O)_2O(R^9)$, —$NS(O)(R^9)_2$, —$OC(O)R^9$, —$OC(O)OR^9$, —$OC(O)N(R^9)_2$, —$Si(R^9)_3$, —$SR^9$, —$S(O)R^9$, —$SF_5$, —$S(O)(NR^9)R^9$, —$S(NR^9)(NR^9)R^9$, —$S(O)(NR^9)N(R^9)_2$, —$S(O)(NCN)R^9$, —$S(O)_2R^9$, —$S(O)_2N(R^9)_2$, —$C(O)N(R^9)S(O)_2R^9$, or —$S(O)_2N(R^9)C(O)R^9$, wherein each $Z^2$, $Z^3$, $Z^6$, $Z^7$, and $Z^8$ is independently optionally substituted with 1 to 3 $Z^{1a}$;

each $Z^{1a}$ is independently oxo, halo, —$NO_2$, —$N_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{13}$, —$C(O)R^{13}$, —$C(O)OR^{13}$, —$C(O)N(R^{13})_2$, —$N(R^{13})_2$, —$N(R^{13})_3^+$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$NR^{13}S(O)_2N(R^{13})_2$, —$NR^{13}S(O)_2O(R^{13})$, —$NS(O)(R^{13})_2$, —$OC(O)R^{13}$, —$OC(O)OR^{13}$, —$OC(O)N(R^{13})_2$, —$Si(R^{13})_3$, —$SR^{13}$, —$S(O)R^{13}$, —$SF_5$, —$S(O)(NR^{13})R^{13}$, —$S(NR^{13})(NR^{13})R^{13}$, —$S(O)(NR^{13})N(R^{13})_2$, —$S(O)(NCN)R^{13}$, —$S(O)_2R^{13}$, —$S(O)_2N(R^{13})_2$, —$C(O)N(R^{13})S(O)_2R^{13}$, or —$S(O)_2N(R^{13})C(O)R^{13}$;

each $Z^{10}$ and $Z^{11}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{13}$, —$C(O)R^{13}$, —$C(O)OR^{13}$, —$C(O)N(R^{13})_2$, —$N(R^{13})_2$, —$N(R^{13})_3^+$, —$N(R^{13})C(O)R^{13}$, —$N(R^{13})C(O)OR^{13}$, —$N(R^{13})C(O)N(R^{13})_2$, —$OC(O)R^{13}$, —$OC(O)OR^{13}$, —$OC(O)$—$N(R^{13})_2$, and —$S$—$R^{13}$; and each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)(aryl), —OC(O)(heteroaryl), —OC(O)(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)₂, —N(heteroaryl)₂, —N(heterocyclyl)₂, —N(C₁₋₉ alkyl)(C₃₋₁₅ cycloalkyl), —N(C₁₋₉ alkyl)(C₂₋₆ alkenyl), —N(C₁₋₉ alkyl)(C₂₋₆ alkynyl), —N(C₁₋₉ alkyl)(C₃₋₁₅ cycloalkyl), —N(C₁₋₉ alkyl)(C₁₋₈ haloalkyl), —N(C₁₋₉ alkyl)(aryl), —N(C₁₋₉ alkyl)(heteroaryl), —N(C₁₋₉ alkyl)(heterocyclyl), —C(O)(C₁₋₉ alkyl), —C(O)(C₂₋₆ alkenyl), —C(O)(C₂₋₆ alkynyl), —C(O)(C₃₋₁₅ cycloalkyl), —C(O)(C₁₋₈ haloalkyl), —C(O)(aryl), —C(O)(heteroaryl), —C(O)(heterocyclyl), —C(O)O(C₁₋₉ alkyl), —C(O)O(C₂₋₆ alkenyl), —C(O)O(C₂₋₆ alkynyl), —C(O)O(C₃₋₁₅ cycloalkyl), —C(O)O(C₁₋₈ haloalkyl), —C(O)O(aryl), —C(O)O(heteroaryl), —C(O)O(heterocyclyl), —C(O)NH₂, —C(O)NH(C₁₋₉ alkyl), —C(O)NH(C₂₋₆ alkenyl), —C(O)NH(C₂₋₆ alkynyl), —C(O)NH(C₃₋₁₅ cycloalkyl), —C(O)NH(C₁₋₈ haloalkyl), —C(O)NH(aryl), —C(O)NH(heteroaryl), —C(O)NH(heterocyclyl), —C(O)N(C₁₋₉ alkyl)₂, —C(O)N(C₃₋₁₅ cycloalkyl)₂, —C(O)N(C₂₋₆ alkenyl)₂, —C(O)N(C₂₋₆ alkynyl)₂, —C(O)N(C₁₋₈ haloalkyl)₂, —C(O)N(aryl)₂, —C(O)N(heteroaryl)₂, —C(O)N(heterocyclyl)₂, —NHC(O)(C₁₋₉ alkyl), —NHC(O)(C₂₋₆ alkenyl), —NHC(O)(C₂₋₆ alkynyl), —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkenyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —NHC(O)NH(C₂₋₆ alkenyl), —NHC(O)NH(C₂₋₆ alkynyl), —NHC(O)NH(C₃₋₁₅ cycloalkyl), —NHC(O)NH(C₁₋₈ haloalkyl), —NHC(O)NH(aryl), —NHC(O)NH(heteroaryl), —NHC(O)NH(heterocyclyl), —SH, —S(C₁₋₉ alkyl), —S(C₂₋₆ alkenyl), —S(C₂₋₆ alkynyl), —S(C₃₋₁₅ cycloalkyl), —S(C₁₋₈ haloalkyl), —S(aryl), —S(heteroaryl), —S(heterocyclyl), —NHS(O)(C₁₋₉ alkyl), —N(C₁₋₉ alkyl)(S(O)(C₁₋₉ alkyl), —S(O)N(C₁₋₉ alkyl)₂, —S(O)(C₁₋₉ alkyl), —S(O)(NH)(C₁₋₉ alkyl), —S(O)(C₂₋₆ alkenyl), —S(O)(C₂₋₆ alkynyl), —S(O)(C₃₋₁₅ cycloalkyl), —S(O)(C₁₋₈ haloalkyl), —S(O)(aryl), —S(O)(heteroaryl), —S(O)(heterocyclyl), —S(O)₂(C₁₋₉ alkyl), —S(O)₂(C₂₋₆ alkenyl), —S(O)₂(C₂₋₆ alkynyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), or —S(O)₂N(C₁₋₉ alkyl)₂;

wherein any alkyl, cycloalkyl, aryl, heteroaryl, or heterocyclyl of $Z^{1b}$ is optionally substituted with one or more halo, C₁₋₉ alkyl, C₁₋₈ haloalkyl, —OH, —NH₂, —NH(C₁₋₉ alkyl), —NH(C₃₋₁₅ cycloalkyl), —NH(C₁₋₈ haloalkyl), —NH(aryl), —NH(heteroaryl), —NH(heterocyclyl), —N(C₁₋₉ alkyl)₂, —N(C₃₋₁₅ cycloalkyl)₂, —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —S(O)(NH)(C₁₋₉ alkyl), —S(O)₂(C₁₋₉ alkyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), —S(O)₂N(C₁₋₉ alkyl)₂, —O(C₃₋₁₅ cycloalkyl), —O(C₁₋₈ haloalkyl), —O(aryl), —O(heteroaryl), —O(heterocyclyl), or —O(C₁₋₉ alkyl).

Provided is a compound of Formula (I):

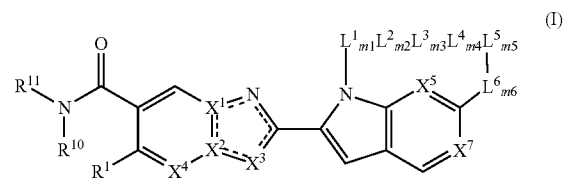

or a pharmaceutically acceptable salt, stereoisomer, mixture of stereoisomers, or tautomer thereof, wherein:

$X^1$ and $X^2$ are C or N;

$X^3$ is N—$R^3$ or C—$R^3$; provided that two of $X^1$, $X^2$, and $X^3$ are C; where each dashed line represents an optional bond to complete valency requirements of each $X^1$, $X^2$ and $X^3$;

$X^4$ is N or C—$R^2$;

$X^5$ is N or $CR^6$;

$X^7$ is N or $CR^7$;

$R^1$ is hydrogen, halo, —CN, —$OR^{12}$, —$N(R^{12})_2$, —$SR^{12}$, —C₁₋₈ alkyl optionally substituted with 1 to 3 $Z^1$, C₃₋₆ cycloalkyl optionally substituted with 1 to 3 $Z^1$, or 4-6 membered heterocyclyl optionally substituted with 1 to 3 $Z^1$;

$R^2$ is hydrogen, halo, —CN, —$OR^{12}$, —$N(R^{12})_2$, —$SR^{12}$, —C₁₋₈ alkyl optionally substituted with 1 to 3 $Z^2$, C₃₋₆ cycloalkyl optionally substituted with 1 to 3 $Z^2$, or 4-6 membered heterocyclyl optionally substituted with 1 to 3 $Z^2$;

when $X^3$ is N—$R^3$, $R^3$ is hydrogen, C₁₋₈ alkyl optionally substituted with 1 to 3 $Z^3$, C₃₋₁₀ alkenyl optionally substituted with 1 to 3 $Z^3$, C₃₋₁₀ alkynyl optionally substituted with 1 to 3 $Z^3$, C₃₋₁₀ cycloalkyl optionally substituted with 1 to 3 $Z^3$, or 4-10 membered heterocyclyl optionally substituted with 1 to 3 $Z^3$; and when $X^3$ is C—$R^3$; $R^3$ is hydrogen, halo, —CN, —$OR^{12}$, —$N(R^{12})_2$, —$SR^{12}$, C₁₋₈ alkyl optionally substituted with 1 to 3 $Z^3$, C₂₋₁₀ alkenyl optionally substituted with 1 to 3 $Z^3$, C₂₋₁₀ alkynyl optionally substituted with 1 to 3 $Z^3$, C₃₋₁₀ cycloalkyl optionally substituted with 1 to 3 $Z^3$, or 4-10 membered heterocyclyl optionally substituted with 1 to 3 $Z^3$; or when $R^2$ is —C₁₋₈ alkyl, —$OR^{12}$, or —$N(R^{12})_2$, and $R^3$ is C₁₋₈ alkyl, then $R^2$ and $R^3$ may be taken together with the atoms to which they are attached to form an optionally substituted 6 to 8 membered ring;

$R^6$ is hydrogen, halo, —CN, —$OR^{12}$, —C₁₋₈ alkyl optionally substituted with 1 to 3 $Z^6$, C₃₋₆ cycloalkyl optionally substituted with 1 to 3 $Z^6$, or 4-6 membered heterocyclyl optionally substituted with 1 to 3 $Z^6$;

$R^7$ is hydrogen, halo, —CN, —$OR^{12}$, —C₁₋₈ alkyl optionally substituted with 1 to 3 $Z^7$, C₃₋₆ cycloalkyl optionally substituted with 1 to 3 $Z^7$, or 4-6 membered heterocyclyl optionally substituted with 1 to 3 $Z^7$;

$L^1$, $L^2$, $L^3$, $L^4$, $L^5$, and $L^6$ are each independently:

C₁₋₁₀ alkylene, optionally substituted with 1 to 3 $Z^8$;
C₂₋₁₀ alkenylene, optionally substituted with 1 to 3 $Z^8$;
C₂₋₁₀ alkynylene, optionally substituted with 1 to 3 $Z^8$;
2-6 membered heteroalkylene, optionally substituted with 1 to 3 $Z^8$;
$C_3$-$C_{10}$cycloalkylene, optionally substituted with 1 to 3 $Z^8$;
4-10 membered heterocyclene, optionally substituted with 1 to 3 $Z^8$;
C₆₋₁₀ arylene, optionally substituted with 1 to 3 $Z^8$;

5-10 membered heteroarylene, optionally substituted with 1 to 3 $Z^8$; or
—O—, —N($R^8$)—, —S—, —C(O)—, —C(O)O—, —C(O)N($R^8$)—, —SO—, —SO$_2$—, —SO$_2$N($R^8$)—, —N($R^8$)C(O)O—, —OC(O)O—, —N($R^8$)C(O)N($R^8$)—, —N($R^8$)S(O)$_2$N($R^8$)—, —N($R^8$)C(N—CN)—S(O)(N$R^8$)—, or —S(O)(N$R^8$)N($R^8$)—; and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring;

each $R^8$ and $R^9$ are each independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{10}$ is hydrogen, —$C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, —$C_{1-8}$ alkyl optionally substituted with 1 to 4 $Z^{11}$, —$C_{3-8}$ cycloalkyl optionally substituted with 1 to 4 $Z^{11}$, or 4-12-membered heterocyclyl optionally substituted with 1 to 4 $Z^{11}$; or $R^{10}$ and $R^{11}$ are taken together to form a 4-12-membered heterocyclyl optionally substituted with 1 to 4 $Z^{11}$;

each $R^{12}$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^1$, $Z^2$, $Z^3$, $Z^6$, $Z^7$, and $Z^8$ is independently oxo, halo, —NO$_2$, —N$_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1a}$, —O$R^9$, —C(O)$R^9$, —C(O)O$R^9$, —C(O)N($R^9$)$_2$, —N($R^9$)$_2$, —N($R^9$)$_3^+$, —N($R^9$)C(O)$R^9$, —N($R^9$)C(O)O$R^9$, —N($R^9$)C(O)N($R^9$)$_2$, —N($R^9$)S(O)$_2$($R^9$), —N$R^9$S(O)$_2$N($R^9$)$_2$, —N$R^9$S(O)$_2$O($R^9$), —NS(O)($R^9$)$_2$, —OC(O)$R^9$, —OC(O)O$R^9$, —OC(O)N($R^9$)$_2$, —Si($R^9$)$_3$, —S$R^9$, —S(O)$R^9$, —SF$_5$, —S(O)(N$R^9$)$R^9$, —S(N$R^9$)(N$R^9$)$R^9$, —S(O)(N$R^9$)N($R^9$)$_2$, —S(O)(NCN)$R^9$, —S(O)$_2$$R^9$, —S(O)$_2$N($R^9$)$_2$, —C(O)N($R^9$)S(O)$_2$$R^9$, or —S(O)$_2$N($R^9$)C(O)$R^9$, each $Z^{10}$ and $Z^{11}$ is independently selected from oxo, halo, —CN, $C_{1-8}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —O$R^{13}$, —C(O)$R^{13}$, —C(O)O$R^{13}$, —C(O)N($R^{13}$)$_2$, —N($R^{13}$)$_2$, —N($R^{13}$)$_3^+$, —N($R^{13}$)C(O)$R^{13}$, —N($R^{13}$)C(O)O$R^{13}$, —N($R^{13}$)C(O)N($R^{13}$)$_2$, —OC(O)$R^{13}$, —OC(O)O$R^{13}$, —OC(O)—N($R^{13}$)$_2$, and —S—$R^{13}$;

each $Z^{1b}$ is independently oxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)(aryl), —OC(O)(heteroaryl), —OC(O)(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl).

In certain embodiments, each $Z^1$, $Z^2$, $Z^3$, $Z^6$, $Z^7$, and $Z^8$, $Z^{10}$, and $Z^{11}$ are independently oxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —OC(O) ($C_{1-9}$ alkyl), —OC(O)($C_{2-6}$ alkenyl), —OC(O)($C_{2-6}$ alkenyl), —OC(O)($C_{2-6}$ alkynyl), —OC(O)($C_{3-15}$ cycloalkyl), —OC(O)($C_{1-8}$ haloalkyl), —OC(O)(aryl), —OC(O)(heteroaryl), —OC(O)(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl) ($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O) (heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O ($C_{3-15}$ cycloalkyl), —C(O)O($C_{1-8}$ haloalkyl), —C(O)O (aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O) (heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl) (S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —NH$_2$, —NH ($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O) O(aryl), —NHC(O)O(heteroaryl), —NHC(O)O(heterocyclyl), —NHC(O)NH($C_{1-9}$ alkyl), —S(O)(NH) ($C_{1-9}$ alkyl), —S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl).

In certain embodiments, $R^1$ is hydrogen, fluoro, chloro, —CN, —OR$^{12}$, $C_{1-6}$ alkyl optionally substituted with 1 to 3 $Z^1$, or $C_{3-5}$ cycloalkyl optionally substituted with 1 to 3 $Z^1$. In certain embodiments, $R^1$ is hydrogen, fluoro, chloro, —CN, —OR$^{12}$, —$C_{1-6}$ alkyl, or $C_{3-5}$ cycloalkyl. In certain embodiments, $R^1$ is hydrogen, fluoro, chloro, —CH$_3$, or —OCH$_3$. In certain embodiments, $R^1$ is hydrogen. In certain embodiments, $R^1$ is fluoro.

In certain embodiments, $R^2$ is hydrogen, fluoro, chloro, —OR$^{12}$, —N(R$^{12}$)$_2$, $C_{1-5}$ alkyl optionally substituted with 1 to 3 $Z^2$, or $C_{3-5}$ cycloalkyl optionally substituted with 1 to 3 $Z^2$. In certain embodiments, $R^2$ is hydrogen, fluoro, chloro, —OR$^{12}$, —N(R$^{12}$)$_2$, $C_{1-5}$ alkyl optionally substituted with 1 to 3 halo, or $C_{3-5}$ cycloalkyl optionally substituted with 1 to 3 halo.

In certain embodiments, $R^2$ is hydrogen, —F, —Cl—CH$_3$, —CF$_3$, —CHF$_2$, cyclopropyl, —OCH$_3$, —O-ethyl, —O-propyl, —O-isopropyl, —O-cyclopropyl, —OCF$_3$, or —OCHF$_2$. In certain embodiments, $R^2$ is fluoro. In certain embodiments, $R^2$ is —OCH$_3$.

In certain embodiments, $R^3$ is hydrogen, $C_{1-6}$ alkyl optionally substituted with 1 to 3 $Z^3$, $C_{2-6}$ alkenyl optionally substituted with 1 to 3 $Z^3$, $C_{2-6}$ alkynyl optionally substituted with 1 to 3 $Z^3$, or $C_{3-6}$ cycloalkyl optionally substituted with 1 to 3 $Z^3$.

In certain embodiments, $X^3$ is C—$R^3$ and $R^3$ is hydrogen, fluoro, chloro, —CN, —OR$^{12}$, —N(R$^{12}$)$_2$, $C_{1-6}$ alkyl optionally substituted with 1 to 3 $Z^3$, $C_{2-6}$ alkenyl optionally substituted with 1 to 3 $Z^3$, $C_{2-6}$ alkynyl optionally substituted with 1 to 3 $Z^3$, or $C_{3-6}$ cycloalkyl optionally substituted with 1 to 3 $Z^3$.

In certain embodiments, $X^3$ is N—$R^3$ and $R^3$ is hydrogen, $C_{1-6}$ alkyl optionally substituted with 1 to 3 $Z^3$, $C_{3-6}$ alkenyl optionally substituted with 1 to 3 $Z^3$, $C_{3-6}$ alkynyl optionally substituted with 1 to 3 $Z^3$, $C_{3-6}$ cycloalkyl optionally substituted with 1 to 3 $Z^3$, or 4-6 membered heterocyclyl optionally substituted with 1 to 3 $Z^3$.

In certain embodiments, $X^3$ is N—$R^3$ and $R^3$ is —CH$_3$, —C$_2$H$_5$, —CH$_2$CHF$_2$, —CH$_2$CF$_3$, —CH$_2$CH$_2$OCH$_3$, —CH$_2$CH(CH$_3$)OCH$_3$, —CH$_2$CH$_2$OCH(CH$_3$)$_2$, —CH$_2$C —C(CH$_3$)$_3$, —CH$_2$CH$_2$OCH$_2$CH$_3$, —CH$_2$CH$_2$CN, —CH$_2$CH$_2$CONH$_2$, —CH$_2$CH(CH$_3$)OCH$_3$, cyclopropyl, cyclobutyl,

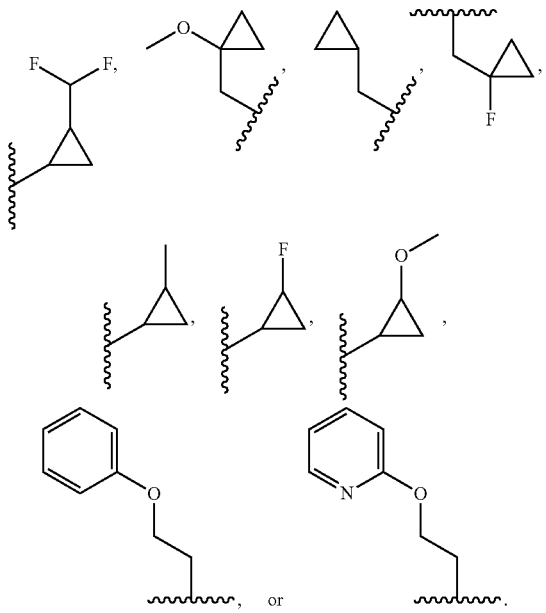

In certain embodiments, X is N—R and R is C$_{1-6}$ alkyl optionally substituted with 1 to 3 Z$^3$ or C$_{3-6}$ cycloalkyl optionally substituted with 1 to 3 Z$^3$. In certain embodiments, X$^3$ is N and N—R$^3$ is methyl, (1-fluorocyclopropyl)methyl, (1-cyanocyclopropyl)methyl, 2-(difluoromethyl)cyclopropyl, 2-methylcyclopropyl, (1-methoxycyclopropyl)methyl. 2-methoxyethyl, 2,2-difluoroethyl, 2,2,2-trifluoroethyl, cyclobutyl, isopropyl, ethyl, 2-isopropoxyethyl, 2-ethoxyethyl, 2-cyanoethyl, 2-(2-methoxyethoxy)ethyl, 3-amino-3-oxopropyl, 2-phenoxyethyl, 2-methoxypropyl, 2-(pyridin-2-yloxy)ethyl, 2-fluorocyclopropyl, or 2-methoxy cyclopropyl.

In certain embodiments, X$^3$ is N—R$^3$. In certain embodiments, X$^3$ is N—R$^3$ and R$^3$ is alkyl or cycloalkyl. In certain embodiments, X$^3$ is N—R$^3$ and R$^3$ is methyl or cyclopropyl. In certain embodiments, X$^3$ is N—R$^3$ and R$^3$ is alkyl. In certain embodiments, X$^3$ is N—R$^3$ and R$^3$ is methyl. In certain embodiments, X$^3$ is N—R$^3$ and R$^3$ is cycloalkyl. In certain embodiments, X$^3$ is N—R$^3$ and R$^3$ is cyclopropyl.

In certain embodiments, X$^3$ is C—R$^3$. In certain embodiments, X$^3$ is C—R$^3$ and R$^3$ is alkyl or cycloalkyl. In certain embodiments, X$^3$ is C—R$^3$ and R$^3$ is methyl or cyclopropyl. In certain embodiments, X$^3$ is C—R$^3$ and R$^3$ is alkyl. In certain embodiments, X$^3$ is C—R$^3$ and R$^3$ is methyl. In certain embodiments, X$^3$ is C—R$^3$ and R$^3$ is cycloalkyl. In certain embodiments, X$^3$ is C—R$^3$ and R$^3$ is cyclopropyl.

In certain embodiments, X$^4$ is N. In certain embodiments, X$^4$ is C—R$^2$. In certain embodiments, X$^4$ is C—R$^2$ and R$^2$ is hydrogen, halo, or —OR$^{12}$. In certain embodiments, X$^4$ is C—R$^2$ and R$^2$ is hydrogen, fluoro, or —O—CH$_3$. In certain embodiments, X$^4$ is C—R$^2$ and R$^2$ is hydrogen, fluoro, chloro, or —O—CH$_3$. In certain embodiments, X$^4$ is C—H. In certain embodiments, X$^4$ is C—F. In certain embodiments, X$^4$ is C—Cl. In certain embodiments, X$^4$ is C—CH$_3$.

In certain embodiments, X$^5$ is N. In certain embodiments, X$^5$ is C—R$^6$. In certain embodiments, R$^6$ is hydrogen, fluoro, chloro, —CN, —CF$_3$, —CHF$_2$, —OR$^{12}$, —C$_{1-5}$ alkyl, or C$_{3-5}$ cycloalkyl. In certain embodiments, R$^6$ is hydrogen, fluoro, chloro, —CH$_3$, —OCH$_3$, or cyclopropyl. In certain embodiments, R$^6$ is hydrogen, fluoro, or chloro. In certain embodiments, R$^6$ is hydrogen or fluoro. In certain embodiments, R$^6$ is hydrogen. In certain embodiments, R$^6$ is fluoro.

In certain embodiments, X$^7$ is N. In certain embodiments, X$^7$ is C—R$^7$. In certain embodiments, R$^7$ is hydrogen, fluoro, chloro, —CN, —CF$_3$, —CHF$_2$, —OR$^{12}$, —C$_{1-3}$ alkyl, or C$_{3-5}$ cycloalkyl. In certain embodiments, R$^7$ is hydrogen, fluoro, chloro, —CH$_3$, —OCH$_3$, or cyclopropyl. In certain embodiments, X$^7$ is C—H. In certain embodiments, R$^7$ is hydrogen, fluoro, or chloro. In certain embodiments, R$^7$ is hydrogen or fluoro. In certain embodiments, R$^7$ is hydrogen. In certain embodiments, R$^7$ is fluoro.

In certain embodiments, X$^5$ is N and X$^7$ is C—R$^7$. In certain embodiments, X$^5$ is N and X$^7$ is C—H.

In certain embodiments, R$^{10}$ is hydrogen or —CH$_3$, and R$^{11}$ is hydrogen, C$_{1-6}$ alkyl optionally substituted with 1 to 3 Z$^{11}$, C$_{3-6}$ cycloalkyl optionally substituted with 1 to 3 Z$^{11}$, or 4-12-membered heterocyclyl optionally substituted with 1 to 3 Z$^{11}$; or R$^{10}$ and R$^{11}$ taken together form a 4-10-membered heterocyclyl optionally substituted with 1 to 3 Z$^{11}$.

In certain embodiments, R$^{10}$ is hydrogen or —CH$_3$, and R$^{11}$ is hydrogen, C$_{1-6}$ alkyl, C$_{3-6}$ cycloalkyl, or 4-12-membered heterocyclyl optionally substituted with 1 to 3 Z$^{11}$; or R$^{10}$ and R$^{11}$ taken together with the nitrogen to which they are attached to form a 4-10-membered heterocyclyl optionally substituted with 1 to 3 Z$^{11}$.

In certain embodiments, R$^{10}$ is hydrogen or —CH$_3$, and R$^{11}$ is 4-12 membered heterocyclyl optionally substituted with 1 to 3 Z$^{11}$.

In certain embodiments, R$^{10}$ is hydrogen, and R$^{11}$ is 5-10 membered heterocyclyl optionally substituted with 1 to 3 substituents selected from the group consisting of —CH$_3$, —CF$_3$, fluoro, —OH, —NH$_2$, —COOH, and —OCH$_3$. In certain embodiments, R$^{10}$ is hydrogen, and R$^{11}$ is pyrrolidinyl or piperidinyl, wherein pyrrolidinyl or piperidinyl may be monocyclic or part of a bicyclic system, and may be optionally substituted with 1 to 3 substituents selected from the group consisting of —CH$_3$, —CF$_3$, fluoro, —OH, —COOH, and —OCH$_3$.

In certain embodiments, R$^{10}$ and R$^{11}$ taken together with the nitrogen to which they are attached to form a 4-10 membered heterocyclyl optionally substituted with 1 to 3 Z$^{11}$.

In certain embodiments of Formula (I), the moiety

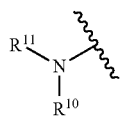

is:

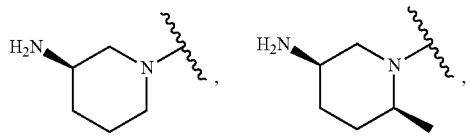

-continued
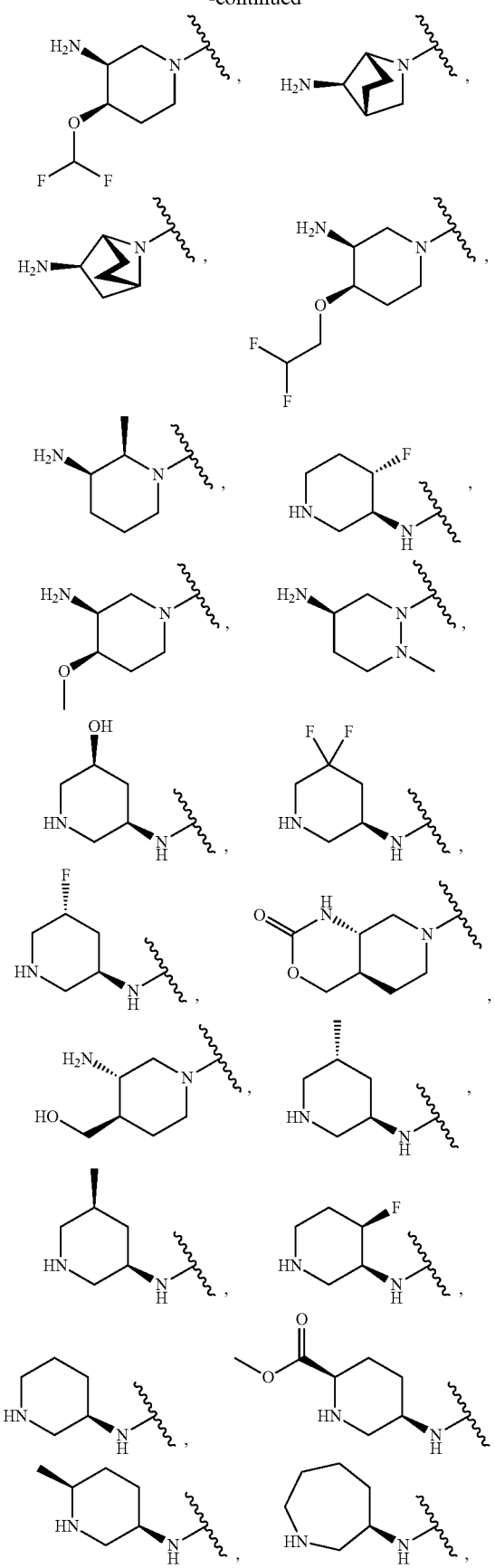
-continued
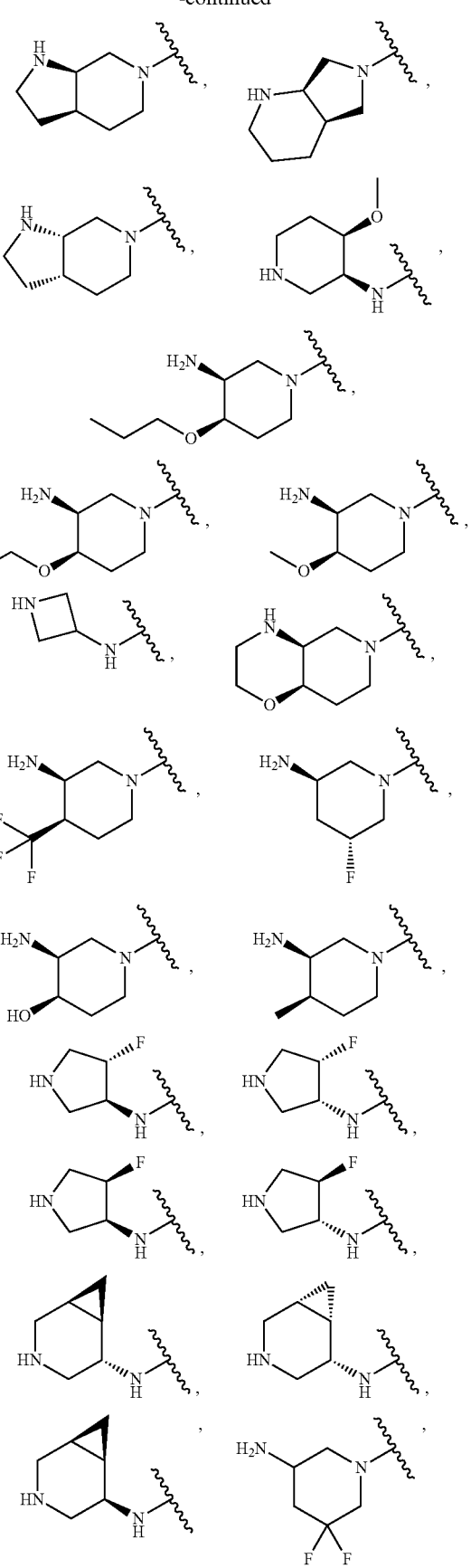

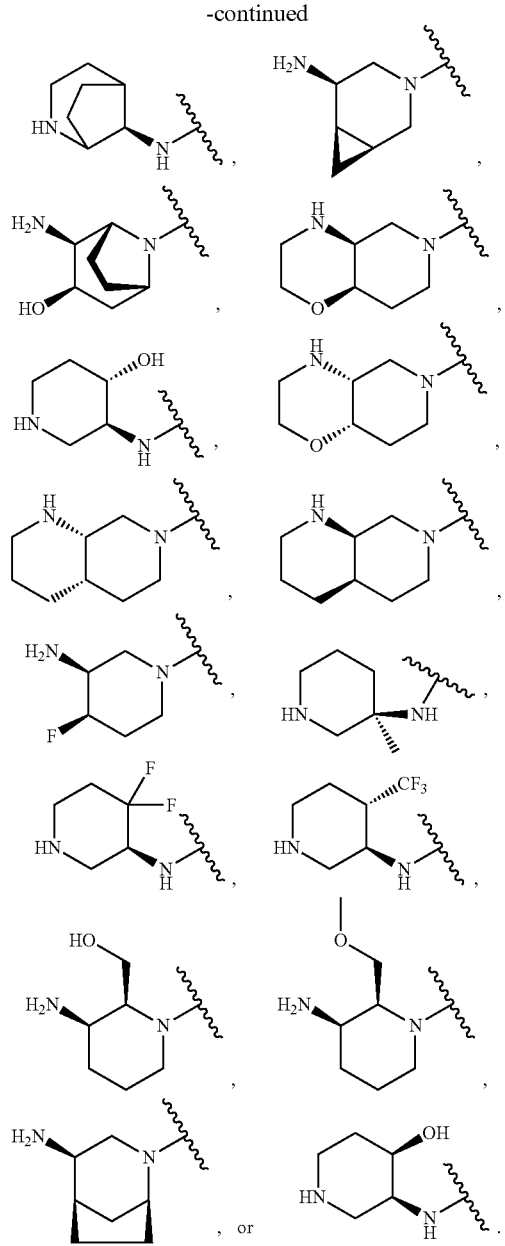
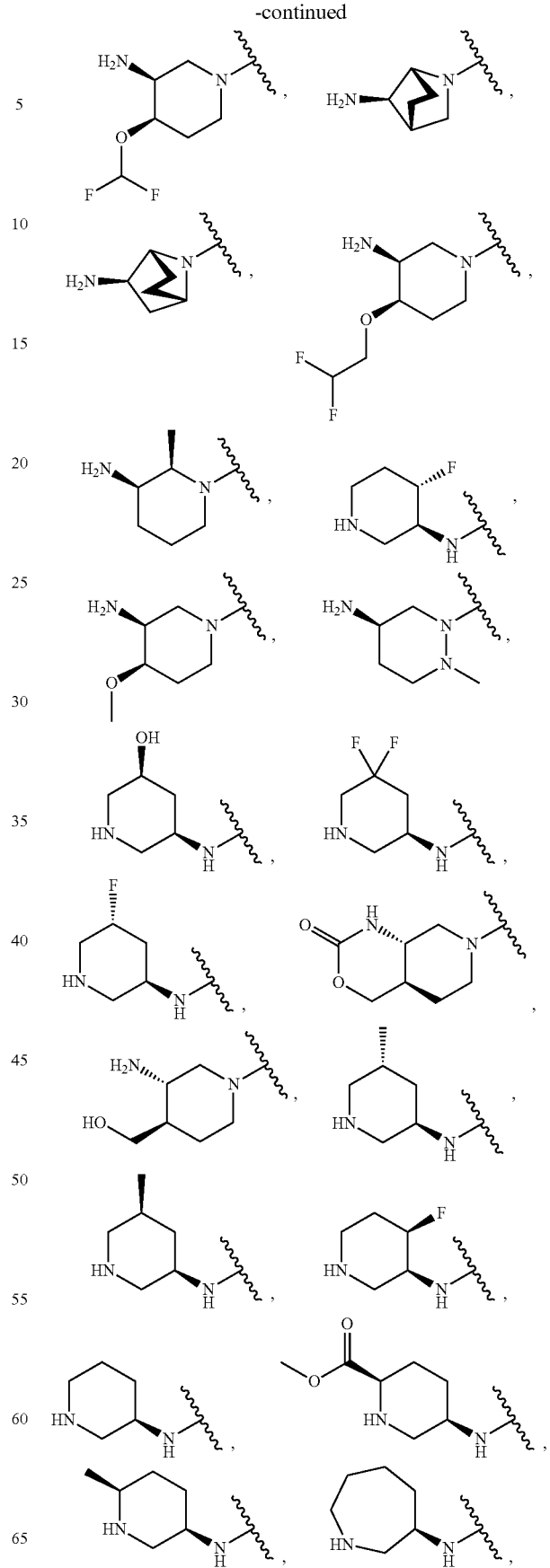
In certain embodiments of Formula (I), the moiety
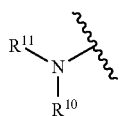
is:
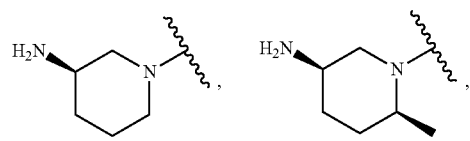

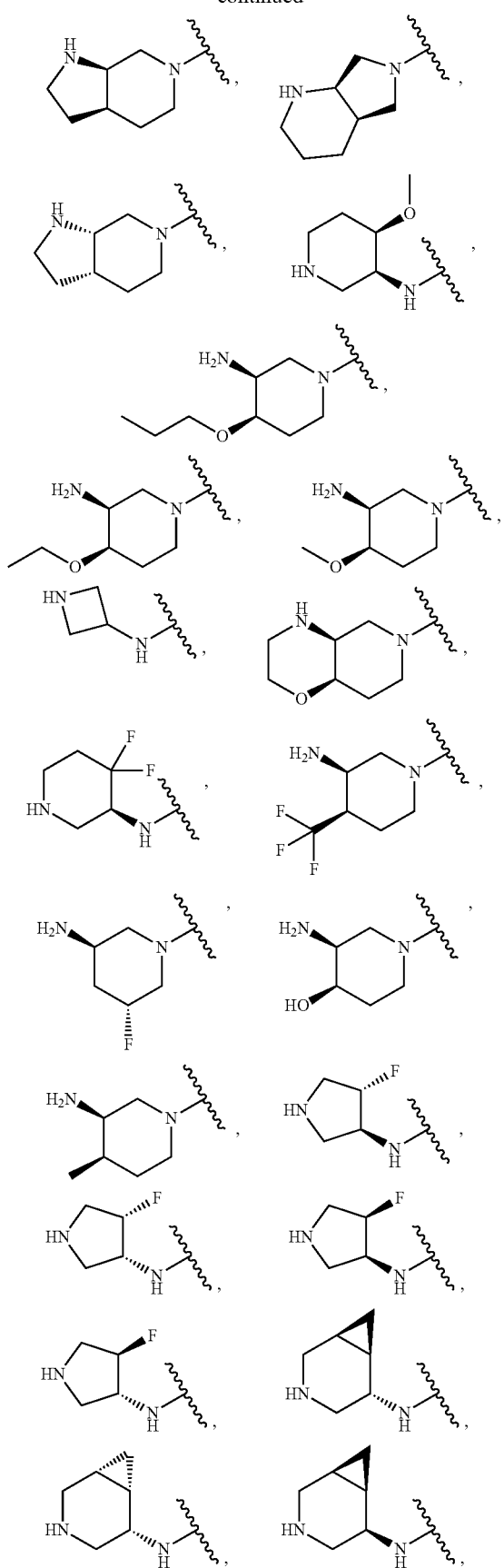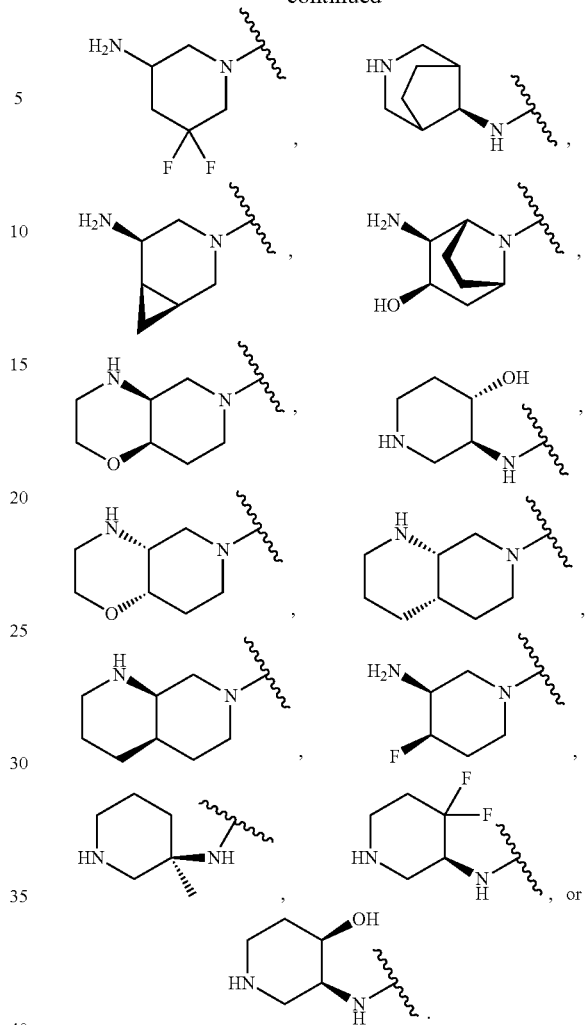
In certain embodiments of Formula (I), the moiety
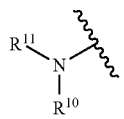
is:
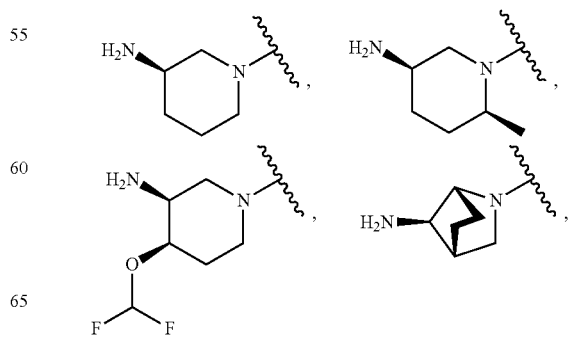

-continued
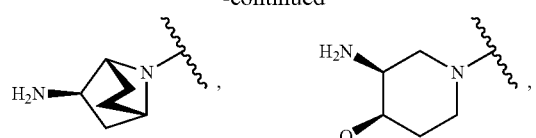
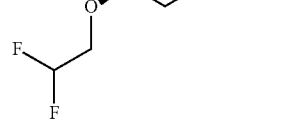
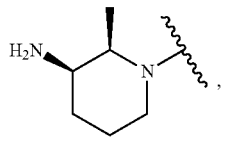, 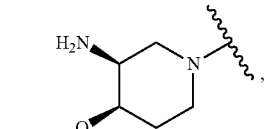
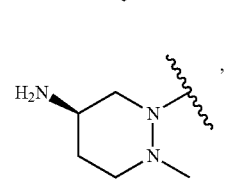, 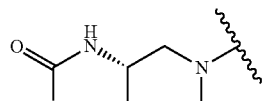
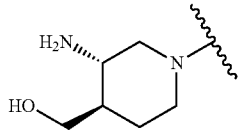, 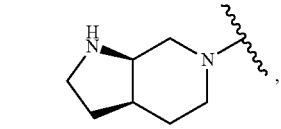
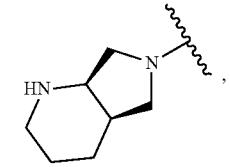, 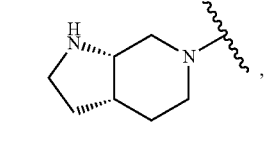
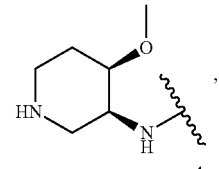, 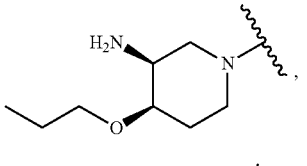
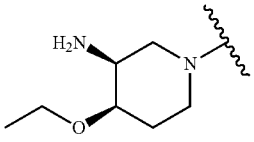, 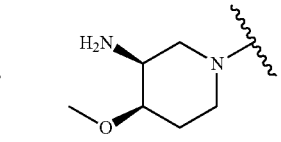
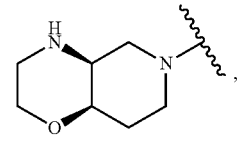, 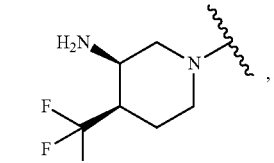
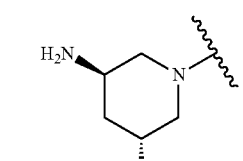, 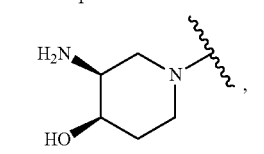
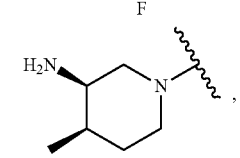, 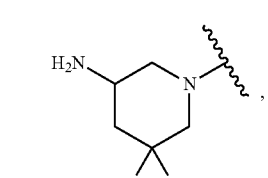
-continued
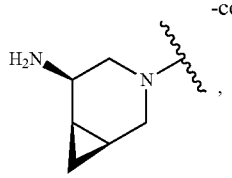, 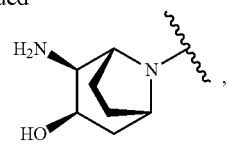
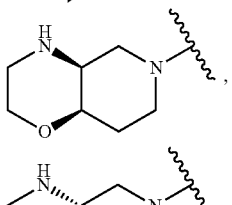, 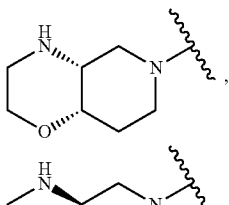
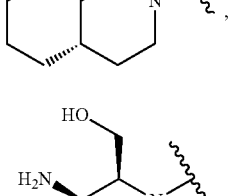, 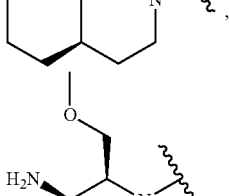
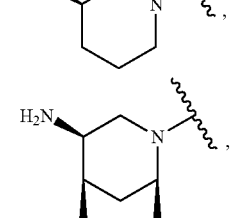, 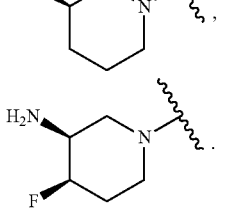
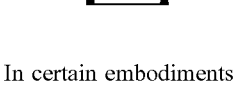, or 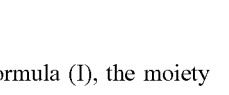.
In certain embodiments of Formula (I), the moiety
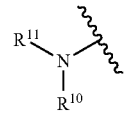
is:
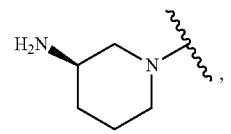, 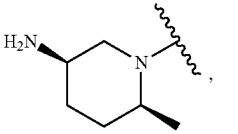
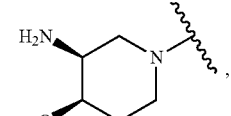, 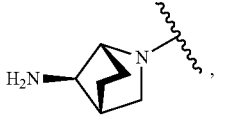
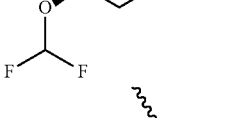, 
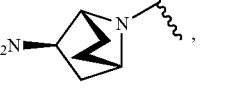, 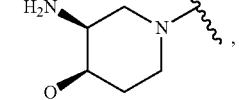
, 
, 

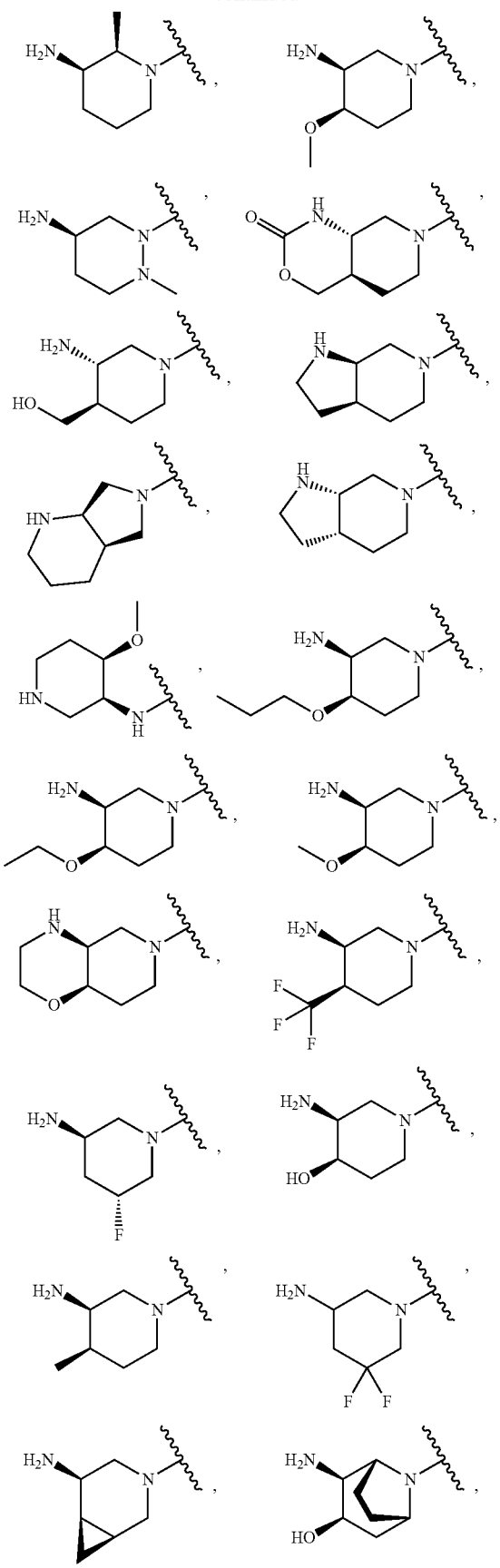
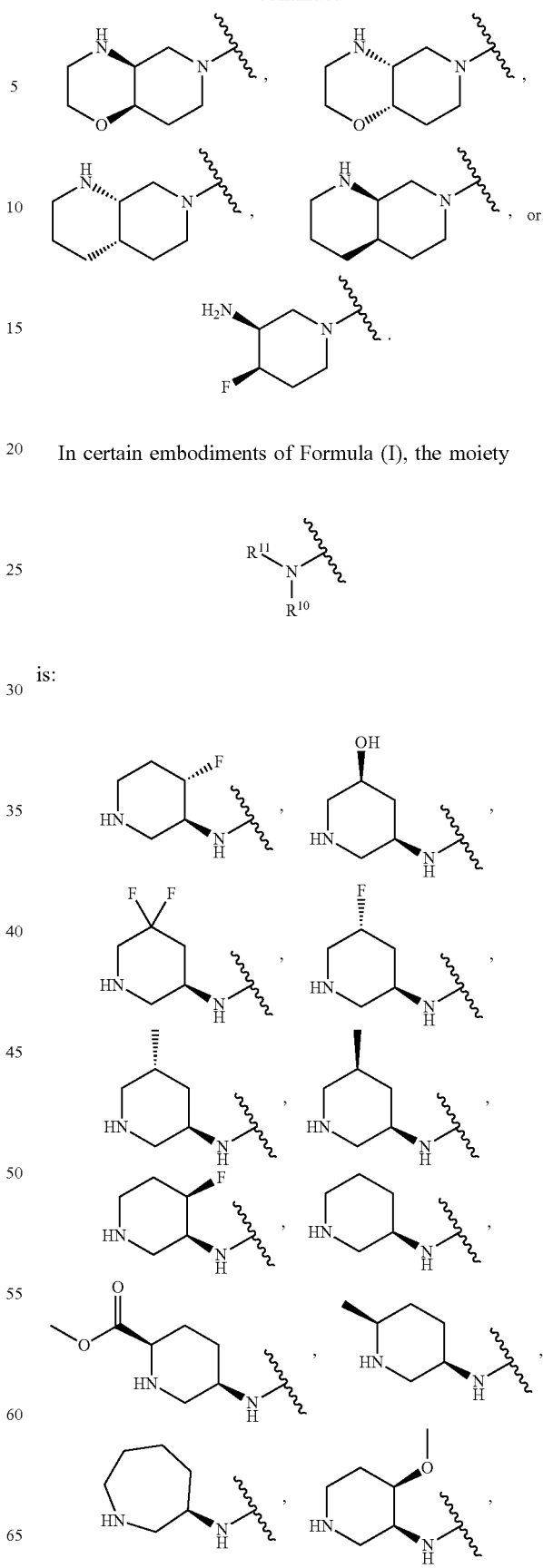
In certain embodiments of Formula (I), the moiety
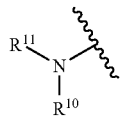
is:
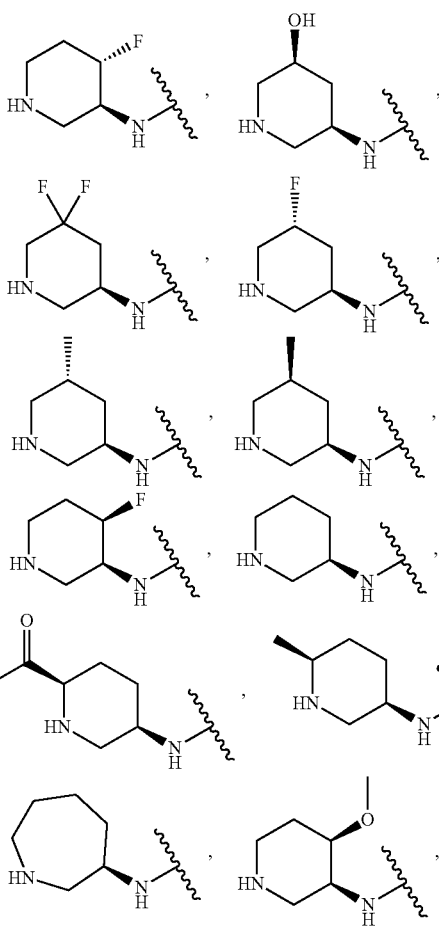

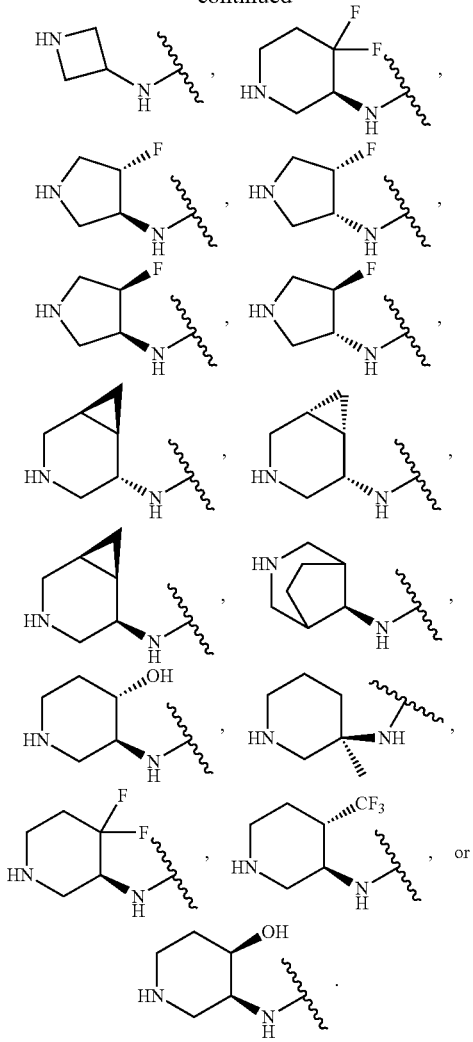

In certain embodiments of Formula (I), the moiety

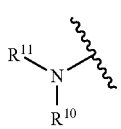

is:

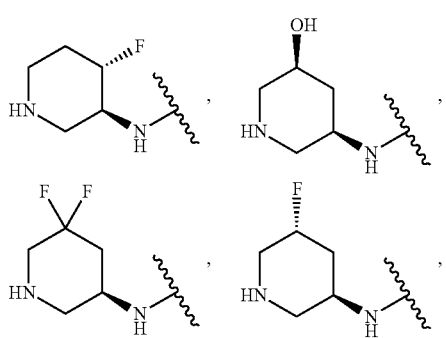

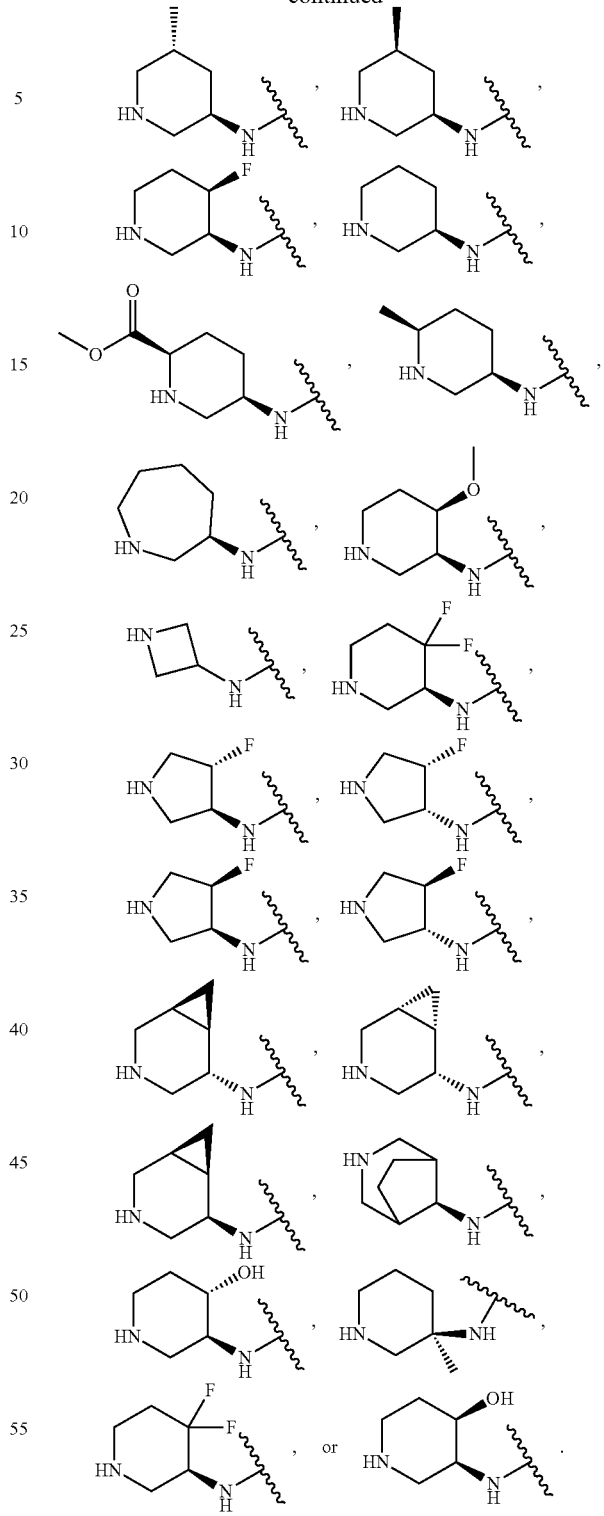

In certain embodiments, $L^1$, $L^2$, $L^3$, $L^4$, $L^5$, and $L^6$ are each independently:

$C_{1-10}$ alkylene optionally substituted with 1 to 2 $Z^8$;
$C_{2-10}$ alkenylene optionally substituted with 1 to 2 $Z^8$;
$C_{2-10}$ alkynylene optionally substituted with 1 to 2 $Z^8$;
2 to 6 membered heteroalkylene having 1 to 2 heteroatoms selected from O and N and optionally substituted with 1 to 2 $Z^8$;

$C_3$-$C_{10}$ cycloalkylene optionally substituted with 1 to 2 $Z^8$;

4-8 membered heterocyclene having 1 to 2 heteroatoms selected from O and N and optionally substituted with 1 to 2 $Z^8$;

$C_{6-10}$ arylene optionally substituted with 1 to 3 $Z^8$;

5-10 membered heteroarylene having 1 to 3 heteroatoms selected from O, N, and S and optionally substituted with 1 to 3 $Z^8$; or —O—, —N($R^8$)—, —C(O)—, —C(O)O—, —C(O)N($R^8$)—, —SO$_2$N($R^8$)—, —SO$_2$—, —N($R^8$)C(O)O—, —OC(O)O—, or —N($R^8$)C(O)N($R^8$); and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring.

It is to be understood that the directionality of the $L^1_{m1}$, $L^2_{m2}$, $L^3_{m3}$, $L^4_{m4}$, $L^5_{m5}$, and $L^6_{m6}$ moieties recited above is not intended to be limiting. For example, —C(O)O— also encompasses —OC(O)—, —C(O)N($R^8$)— also encompasses —N($R^8$)C(O)—, —SO$_2$N($R^8$)— also encompasses —N($R^8$)SO$_2$—, and —N($R^8$)C(O)O— also encompasses —OC(O)N($R^8$)—.

In certain embodiments, $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 12 to 18 membered macrocyclic ring. In certain embodiments, $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 12 to 16 membered macrocyclic ring. In certain embodiments, $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 12 to 14 membered macrocyclic ring. In certain embodiments, $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 14 to 16 membered macrocyclic ring. In certain embodiments, $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 14 membered macrocyclic ring.

In certain embodiments, $L^1$, $L^2$, $L^3$, $L^4$, $L^5$, and $L^6$ are each independently:

$C_{1-10}$ alkylene optionally substituted with 1 to 2 $Z^8$;

$C_{2-10}$ alkenylene optionally substituted with 1 to 2 $Z^8$;

2 to 6 membered heteroalkylene having 1 to 2 heteroatoms selected from O and N and optionally substituted with 1 to 2 $Z^8$;

$C_3$-$C_{10}$ cycloalkylene optionally substituted with 1 to 2 $Z^8$;

4-8 membered heterocyclene having 1 to 2 heteroatoms selected from O and N and optionally substituted with 1 to 2 $Z^8$;

$C_{6-10}$ arylene optionally substituted with 1 to 3 $Z^8$;

5-10 membered heteroarylene having 1 to 3 heteroatoms selected from O, N, and S and optionally substituted with 1 to 3 $Z^8$; or —O—, —N($R^8$)—, —C(O)—, —C(O)N($R^8$)—, —SO$_2$N($R^8$)—, or —N($R^8$)C(O)N($R^8$); and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring, or an optionally substituted 12 to 18 membered macrocyclic ring, or an optionally substituted 12 to 16 membered macrocyclic ring, or an optionally substituted 14 membered macrocyclic ring.

In certain embodiments, $L^1$, $L^2$, $L^3$, $L^4$, $L^5$, and $L^6$ are each independently:

$C_{1-3}$ alkylene optionally substituted with 1 to 2 $Z^8$;

$C_{2-3}$ alkenylene optionally substituted with 1 to 2 $Z^8$;

2 to 5 membered heteroalkylene having 1 to 2 heteroatoms selected from O and N and optionally substituted with 1 to 2 $Z^8$;

$C_3$-$C_{10}$ cycloalkylene optionally substituted with 1 to 2 $Z^8$;

4-8 membered heterocyclene having 1 to 2 heteroatoms selected from O and N and optionally substituted with 1 to 2 $Z^8$;

$C_6$ arylene optionally substituted with 1 to 3 $Z^8$;

5-10 membered heteroarylene having 1 to 3 heteroatoms selected from O, N, and S and optionally substituted with 1 to 3 $Z^8$; or —O—, —N($R^8$)—, —C(O)—, —C(O)N($R^8$)—, —SO$_2$N($R^8$)—, or —N($R^8$)C(O)N($R^8$); and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring, or an optionally substituted 12 to 18 membered macrocyclic ring, or an optionally substituted 12 to 16 membered macrocyclic ring, or an optionally substituted 14 membered macrocyclic ring.

In certain embodiments, the macrocyclic ring moiety

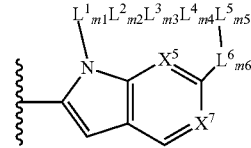

is an optionally substituted 12 to 18 membered macrocyclic ring, or an optionally substituted 12 to 16 membered macrocyclic ring, or an optionally substituted 14 membered macrocyclic ring.

In certain embodiments, at least one of $L^1$, $L^2$, $L^3$, $L^4$, $L^5$, and $L^6$ is $C_{1-3}$ alkylene optionally substituted with 1 to 2 $Z^8$.

In certain embodiments, at least one of $L^1$, $L^2$, $L^3$, $L^4$, $L^5$, and $L^6$ is $C_3$-$C_{10}$ cycloalkylene optionally substituted with 1 to 2 $Z^8$.

In certain embodiments, at least one of $L^1$, $L^2$, $L^3$, $L^4$, $L^5$, and $L^6$ is —O—, —N($R^8$)—, —C(O)—, —C(O)N($R^8$)—, —SO$_2$N($R^8$)—, or —N($R^8$)C(O)N($R^8$). In certain embodiments, at least one of $L^1$, $L^2$, $L^3$, $L^4$, $L^5$, and $L^6$ is —O—. In certain embodiments, at least one of $L^1$, $L^2$, $L^3$, $L^4$, $L^5$, and $L^6$ is —N($R^8$)—. In certain embodiments, at least one of $L^1$, $L^2$, $L^3$, $L^4$, $L^5$, and $L^6$ is —C(O)—. In certain embodiments, at least one of $L^1$, $L^2$, $L^3$, $L^4$, $L^5$, and $L^6$ is —C(O)N($R^8$)—. In certain embodiments, at least one of $L^1$, $L^2$, $L^3$, $L^4$, $L^5$, and $L^6$ is —SO$_2$N($R^8$)—. In certain embodiments, at least one of $L^1$, $L^2$, $L^3$, $L^4$, $L^5$, and $L^6$ is —N($R^8$)C(O)N($R^{12}$). In certain embodiments, at least one of $L^1$, $L^2$, $L^3$, $L^4$, $L^5$, and $L^6$ is —CONH—.

In certain embodiments, at least one of m1, m2, m3, m4, m5, and m6 is 0. In certain embodiments, one of m1, m2, m3, m4, m5, and m6 is 0. In certain embodiments, two of m1, m2, m3, m4, m5, and m6 are 0. In certain embodiments, three of m1, m2, m3, m4, m5, and m6 are 0. In certain embodiments, four of m1, m2, m3, m4, m5, and m6 are 0. In certain embodiments, each of m1, m2, m3, m4, m5, and m6 are 1. In certain embodiments, m1 is 0. In certain embodiments, m1 is 1. In certain embodiments, m2 is 0. In certain embodiments, m2 is 1. In certain embodiments, m3 is 0. In certain embodiments, m3 is 1. In certain embodiments, m4 is 0. In certain embodiments, m4 is 1. In certain embodiments, m5 is 0. In certain embodiments, m5 is 1. In certain embodiments, m6 is 0. In certain embodiments, m6 is 1. In certain embodiments, m1 is 0, and each of m2, m3, m4, m5, and m6 are 1.

In certain embodiments, $L^1$, $L^2$, and $L^3$ are each independently:

- $C_{1-10}$ alkylene optionally substituted with 1 to 2 $Z^8$;
- $C_{2-10}$ alkenylene optionally substituted with 1 to 2 $Z^8$;
- 2 to 6 membered heteroalkylene having 1 to 2 heteroatoms selected from O and N and optionally substituted with 1 to 2 $Z^8$;
- $C_3$-$C_{10}$ cycloalkylene optionally substituted with 1 to 2 $Z^8$;

and $L^4$, $L^5$, and $L^6$ are each independently:

- $C_{1-10}$ alkylene optionally substituted with 1 to 2 $Z^8$;
- 4-8 membered heterocyclene having 1 to 2 heteroatoms selected from O and N and optionally substituted with 1 to 2 $Z^8$;
- $C_{6-10}$ arylene optionally substituted with 1 to 3 $Z^8$;
- 5-10 membered heteroarylene having 1 to 3 heteroatoms selected from O, N, and S and optionally substituted with 1 to 3 $Z^8$; or
- —O—, —N($R^8$)—, —C(O)—, —C(O)N($R^8$)—, —SO$_2$N($R^8$)—, or —N($R^8$)C(O)N($R^8$); and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring, or an optionally substituted 12 to 18 membered macrocyclic ring, or an optionally substituted 12 to 16 membered macrocyclic ring, or an optionally substituted 14 membered macrocyclic ring.

In certain embodiments, $L^1$, $L^2$, and $L^3$ are each independently:

- $C_{1-10}$ alkylene optionally substituted with 1 to 2 $Z^8$;
- $C_{2-10}$ alkenylene optionally substituted with 1 to 2 $Z^8$;
- 2 to 6 membered heteroalkylene having 1 to 2 heteroatoms selected from O and N and optionally substituted with 1 to 2 $Z^8$;
- $C_3$-$C_{10}$ cycloalkylene optionally substituted with 1 to 2 $Z^8$;

and $L^4$ and $L^5$ are each independently:

- 4-8 membered heterocyclene having 1 to 2 heteroatoms selected from O and N and optionally substituted with 1 to 2 $Z^8$;
- $C_{6-10}$ arylene optionally substituted with 1 to 3 $Z^8$;
- 5-10 membered heteroarylene having 1 to 3 heteroatoms selected from O, N, and S and optionally substituted with 1 to 3 $Z^8$; or
- —O—, —N($R^8$)—, —C(O)—, —C(O)N($R^8$)—, —SO$_2$N($R^8$)—, or —N($R^8$)C(O)N($R^8$);

$L^6$ is:

- $C_{1-10}$ alkylene optionally substituted with 1 to 2 $Z^8$; and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring, or an optionally substituted 12 to 18 membered macrocyclic ring, or an optionally substituted 12 to 16 membered macrocyclic ring, or an optionally substituted 14 membered macrocyclic ring.

In certain embodiments, $L^1$ is $C_{1-10}$ alkylene, optionally substituted with 1 to 3 substituents selected from the group consisting of halo, —OCH$_3$, and 5-6 membered heteroaryl optionally substituted with halo; $L^2$ is $C_3$-$C_{10}$cycloalkylene or $C_{2-10}$ alkenylene, wherein $C_3$-$C_{10}$ cycloalkylene or $C_{2-10}$ alkenylene is optionally substituted with 1 to 3 substituents selected from the group consisting of halo, and $C_{1-5}$ alkyl optionally substituted with halo; $L^3$ is —O— or —O—$C_{1-6}$ alkylene; $L^4$ is $C_{1-10}$ alkylene optionally substituted with 1 to 3 $Z^8$, 4-10 membered heterocyclene optionally substituted with 1 to 3 $Z^8$, $C_3$-$C_{10}$ cycloalkylene optionally substituted with 1 to 3 $Z^8$, 5-10 membered heteroarylene optionally substituted with 1 to 3 $Z^8$, or $C_{6-10}$ arylene optionally substituted with 1 to 3 $Z^8$; and m1 is 1.

In certain embodiments, $X^5$ is N and $X^7$ is C—H. In certain embodiments, $X^5$ and $X^7$ are C—H.

In certain embodiments, the macrocyclic ring moiety

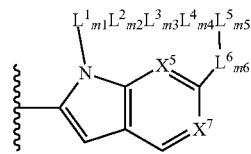

is:

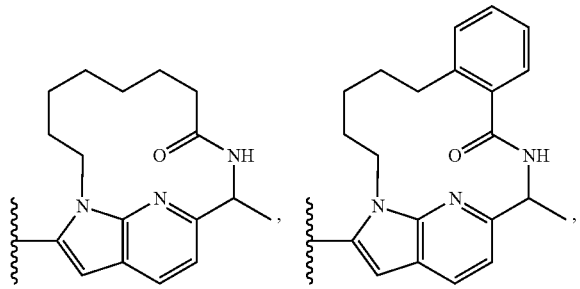

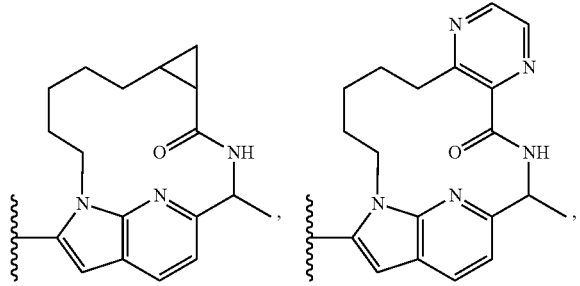

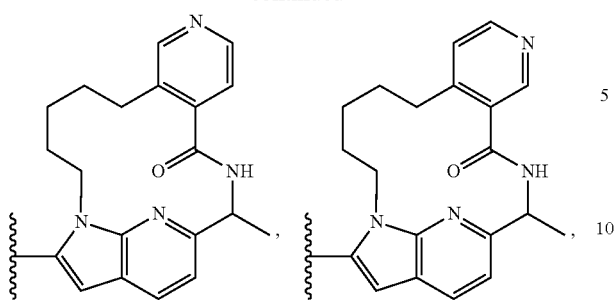
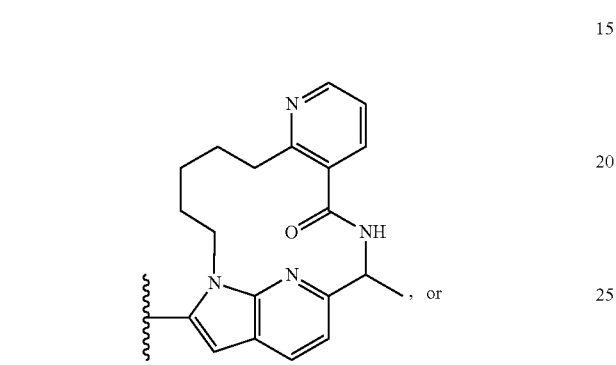
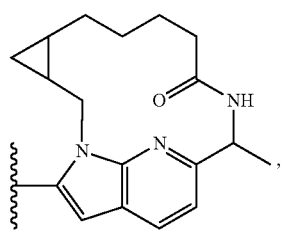
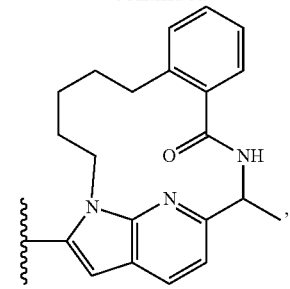
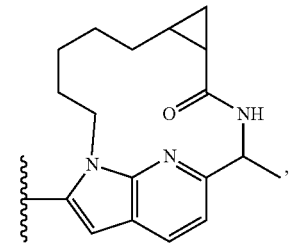
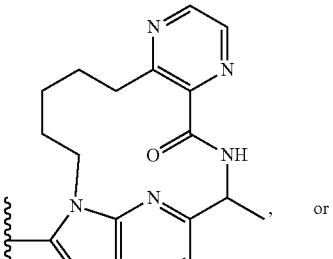, or
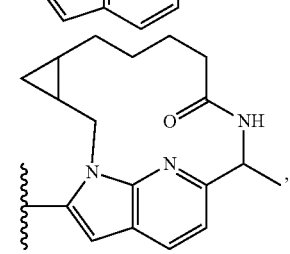
wherein each macrocyclic ring is further optionally substituted with 1-8 $Z^8$.
In certain embodiments, the macrocyclic ring moiety
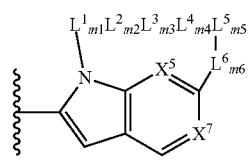
is:
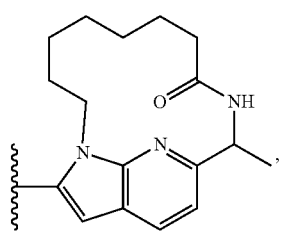
wherein each macrocyclic ring is further optionally substituted with 1-8 $Z^8$.
In certain embodiments, the macrocyclic ring moiety
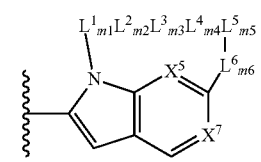
is:
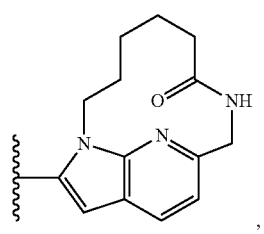

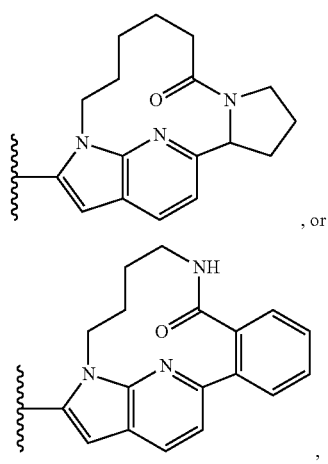

, or

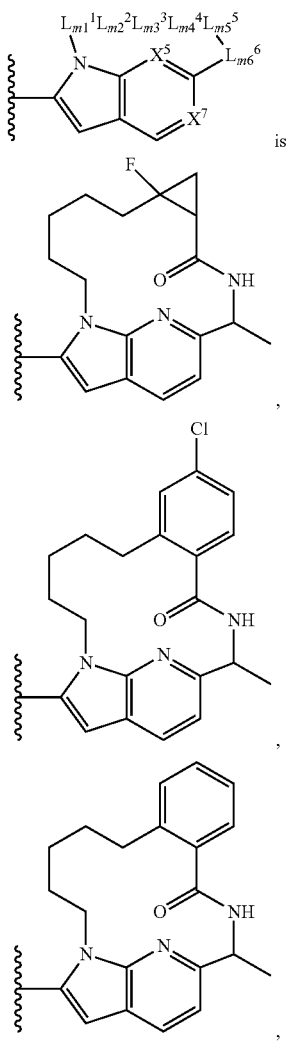

wherein each macrocyclic ring is further optionally substituted with 1-8 $Z^8$.

In certain embodiments of any one of Formulas (I), (Ia)-(Id), and (Ip)-(It), the macrocyclic ring moiety

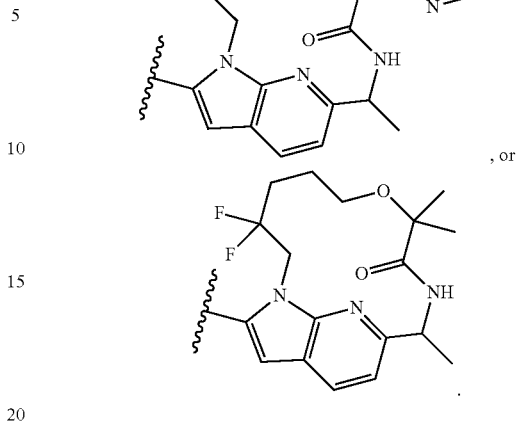

, or

In certain embodiments, each $R^8$ is hydrogen. In certain embodiments, each $R^8$ is $C_{1-6}$ alkyl optionally substituted with 1 to 3 $Z^{1b}$. In certain embodiments, each $R^8$ is hydrogen or $C_{1-6}$ alkyl optionally substituted with 1 to 3 $Z^{1b}$. In certain embodiments, each $R^8$ is $C_{1-6}$ alkyl.

In certain embodiments, each $R^8$ is $C_{3-6}$ cycloalkyl optionally substituted with 1 to 3 $Z^{1b}$. In certain embodiments, each $R^8$ is hydrogen, $C_{3-6}$ cycloalkyl optionally substituted with 1 to 3 $Z^{1b}$, or $C_{1-6}$ alkyl optionally substituted with 1 to 3 $Z^{1b}$. In certain embodiments, each $R^8$ is hydrogen, $C_{3-6}$ cycloalkyl optionally substituted with 1 to 3 halo, or $C_{1-6}$ alkyl optionally substituted with 1 to 3 halo.

In certain embodiments, each $R^8$ is a 4-6 membered heterocyclyl having 1 to 2 heteroatoms selected from O and N optionally substituted with 1 to 3 $Z^{1b}$, $C_{6-10}$ aryl optionally substituted with 1 to 3 $Z^{1b}$, or 5-6 membered heteroaryl optionally substituted with 1 to 3 $Z^{1b}$. In certain embodiments, each $R^8$ is independently hydrogen, $C_{1-6}$ alkyl optionally substituted with 1 to 3 $Z^{1b}$, $C_{3-6}$ cycloalkyl optionally substituted with 1 to 3 $Z^{1b}$, 4-6 membered heterocyclyl having 1 to 2 heteroatoms selected from O and N optionally substituted with 1 to 3 $Z^{1b}$, $C_{6-10}$ aryl optionally substituted with 1 to 3 $Z^{1b}$, or 5-6 membered heteroaryl optionally substituted with 1 to 3 $Z^{1b}$.

In certain embodiments, each $R^8$ is independently hydrogen, —$CH_3$, ethyl, isopropyl, cyclopropyl, cyclobutyl, tert-butyl, $CH_2$-cyclopropyl, fluorocyclopropyl, —$CHF_2$, —$CF_3$, —$CH_2CF_3$, or —$CH_2CHF_2$.

In certain embodiments, each $R^{12}$ and $R^{13}$ is independently hydrogen, $C_{1-6}$ alkyl optionally substituted with $Z^{1b}$, $C_{3-6}$ cycloalkyl optionally substituted with $Z^{1b}$, 4-6 membered heterocyclyl having 1 to 2 heteroatoms selected from O and N optionally substituted with 1 to 3 $Z^{1b}$, $C_{6-10}$ aryl optionally substituted with 1 to 3 $Z^{1b}$, or 5-6 membered heteroaryl optionally substituted with 1 to 3 $Z^{1b}$.

In certain embodiments, each $R^{12}$ and $R^{13}$ is independently hydrogen, —$CH_3$, ethyl, isopropyl, cyclopropyl, cyclobutyl, tert-butyl, $CH_2$-cyclopropyl, fluorocyclopropyl, —$CHF_2$, —$CF_3$, —$CH_2CF_3$, or —$CH_2CHF_2$.

In certain embodiments, each $R^{12}$ is independently hydrogen, $C_{1-6}$ alkyl optionally substituted with 1 to 3 $Z^{1b}$, $C_{3-6}$ cycloalkyl optionally substituted with 1 to 3 $Z^{1b}$, 4-6 membered heterocyclyl having 1 to 2 heteroatoms selected from O and N optionally substituted with 1 to 3 $Z^{1b}$, $C_{6-10}$ aryl optionally substituted with 1 to 3 $Z^{1b}$, or 5-6 membered heteroaryl optionally substituted with 1 to 3 $Z^{1b}$.

In certain embodiments, each $R^{12}$ is independently hydrogen, —$CH_3$, ethyl, isopropyl, cyclopropyl, cyclobutyl, tert-butyl, $CH_2$-cyclopropyl, fluorocyclopropyl, —$CHF_2$, —$CF_3$, —$CH_2CF_3$, or —$CH_2CHF_2$.

In certain embodiments, each $Z^1$, $Z^2$, $Z^3$, $Z^6$, $Z^7$, and $Z^8$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^1$, $Z^2$, $Z^3$, $Z^6$, $Z^7$, and $Z^8$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O-isopropyl, —O-cyclopropyl, —$OCF_3$, —$OCF_2H$, —C(O)-alkyl, —C(O)-cycloalkyl, —C(O)-aryl, —C(O)-heteroaryl, or —$NH_2$.

In certain embodiments, each $Z^1$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^1$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^2$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^2$ is independently fluoro, chloro, —CN, $C_{1-6}$ alkyl optionally substituted with 1 to 3 $Z^{1b}$, $C_{3-6}$ cycloalkyl optionally substituted by 1 to 3 $Z^{1b}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^2$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^2$ is independently fluoro, chloro, —CN, —OH, —$OCH_3$, —$OCHF_2$, —$OCF_3$, —$CH_3$, —$CHF_2$, —$CF_3$, —$CH_2OH$, —$CH_2OCH_3$, or —$NH_2$.

In certain embodiments, each $Z^3$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^3$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^6$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^6$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^7$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^7$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^8$ is independently halo, oxo, —CN, $C_{1-6}$ alkyl optionally substituted by 1 to 3 $Z^{1a}$, $C_{3-6}$ cycloalkyl optionally substituted with 1 to 3 $Z^{1b}$, 4-6 membered heterocyclyl having 1 to 2 heteroatoms selected from O and N that is optionally substituted by 1 to 3 $Z^{1a}$, 5-6 membered heteroaryl having 1 to 4 heteroatoms selected from O and N and optionally substituted with 1 to 3 $Z^{1a}$, —$OR^{12}$, —$N(R^{12})_2$, —$C(O)R^{12}$, $N(R^{12})C(O)R^{12}$, —$N(R^{12})$ $C(O)OR^{12}$, —$N(R^{12})S(O)_2R^{12}$, —$OC(O)R^{12}$, —$OC(O)$ $OR^{12}$, —$OC(O)N(R^{12})_2$, or —$S(O)_2R^{12}$.

In certain embodiments, each $Z^8$ is independently oxo, hydroxy, fluoro, chloro, —CN, —$CH_3$, ethyl, isopropyl, tert-butyl, —$CF_3$, —$CHF_2$, cyclopropyl, cyclobutyl, —$OCH_3$, —O-ethyl, —O— isopropyl, —O-cyclopropyl, —$OCF_3$, —$OCF_2H$, —C(O)-alkyl, —C(O)-cycloalkyl, —C(O)-aryl, —C(O)— heteroaryl, or —$NH_2$.

In certain embodiments, each $Z^8$ is independently halo, $C_{1-8}$ alkyl optionally substituted by 1 to 3 $Z^{1a}$, or —$OR^9$. In certain embodiments, each $Z^8$ is independently halo, $C_{1-8}$ alkyl, $C_{1-8}$ haloalkyl, or —O—$C_{1-8}$ alkyl. In certain embodiments, each $Z^8$ is independently fluoro, methyl, —$CF_3$, or —O—$CH_3$.

In certain embodiments of any one of Formulas (I), (Ia)-(It), (Iv), and (Iv-1), each $Z^8$ is independently halo, $C_{1-5}$ alkyl, —O($C_{1-5}$ alkyl), $C_{3-6}$ cycloalkyl, 6-10 membered aryl, or 5-10 membered heteroaryl, wherein $C_{1-5}$ alkyl, —O($C_{1-5}$ alkyl), $C_{3-6}$ cycloalkyl, 6-10 membered aryl, or 5-10 membered heteroaryl, is optionally substituted with 1 to 2 halo or —O($C_{1-5}$ alkyl).

In certain embodiments, each $Z_8$ is independently —$CF_3$, —$CHF_2$, —$OCH_3$, —$OCHF_2$, —$OCF_3$, fluoro, chloro, cyclopropyl, or —$CH_3$ optionally substituted with —$OCH_3$.

In certain embodiments, each $Z^8$ is independently fluoro, chloro, cyclopropyl, or —$CH_3$. In certain embodiments, $Z^8$ is fluoro. In certain embodiments, $Z^8$ is absent.

In certain embodiments, each $Z^{1a}$ is independently halo, —CN, $C_{1-6}$ alkyl optionally substituted by 1 to 3 $Z^{1b}$, $C_{3-6}$ cycloalkyl optionally substituted by 1 to 3 $Z^{1b}$, 6 membered aryl optionally substituted by 1 to 3 $Z^{1b}$, 4-6 membered heterocyclyl having 1 to 2 heteroatoms selected from O or N that is optionally substituted by 1 to 3 $Z^{1b}$, 5-6 membered heteroaryl having 1 to 2 heteroatoms selected from O and N and optionally substituted with 1 to 3 $Z^{1b}$, —$OR^{12}$, —$N(R^{12})_2$, —$C(O)R^{12}$, $N(R^{12})C(O)R^{12}$, —$N(R^{12})C(O)OR^{12}$, —$N(R^{12})S(O)_2R^{12}$, —$OC(O)R^{12}$, —$OC(O)OR^{12}$, —$OC(O)N(R^{12})_2$, or —$S(O)_2R^{12}$.

In certain embodiments, each $Z^{1a}$ is independently halo, —$CH_3$, cyclopropyl, or —$OCH_3$.

In certain embodiments, each $Z^{1b}$ is independently hydroxy, halo, —CN, $C_{1-6}$ alkyl, $C_{2-6}$ alkenyl, $C_{2-6}$ alkynyl, $C_{3-6}$ cycloalkyl, $C_{1-6}$ haloalkyl, aryl, heteroaryl, heterocyclyl, or —O($C_{1-6}$ alkyl).

In certain embodiments, each $Z^{10}$ and $Z^{11}$ is independently fluoro, chloro, —CN, $C_{1-6}$ alkyl optionally substituted with 1 to 3 $Z^{1b}$, $C_{3-6}$ cycloalkyl optionally substituted with 1 to 3 $Z^{1b}$, —$OR^{13}$, —$C(O)R^{13}$, —$OC(O)R^{13}$, —$OC(O)OR^{13}$, —$OC(O)N(R^{13})_2$, —$N(R^{13})C(O)R^{13}$, —$N(R^{13})C(O)OR^{13}$, or —$N(R^{13})_2$.

In certain embodiments, each $Z^{10}$ and $Z^{11}$ is independently fluoro, chloro, —CN, —OH, —$OCH_3$, —$OCHF_2$, —$OCF_3$, —$CH_3$, —$CHF_2$, —$CF_3$, —$CH_2OH$, —$CH_2OCH_3$, or —$NH_2$.

In certain embodiments, each $Z^{10}$ is independently fluoro, chloro, —CN, $C_{1-6}$ alkyl optionally substituted with 1 to 3 $Z^{1b}$, $C_{3-6}$ cycloalkyl optionally substituted with 1 to 3 $Z^{1b}$, —$OR^{13}$, —$C(O)R^{13}$, —$OC(O)R^{13}$, —$OC(O)OR^{13}$, —$OC(O)N(R^{13})_2$, —$N(R^{13})C(O)R^{13}$, —$N(R^{13})C(O)OR^{13}$, or —$N(R^{13})_2$.

In certain embodiments, each $Z^{10}$ is independently fluoro, chloro, —CN, —OH, —$OCH_3$, —$OCHF_2$, —$OCF_3$, —$CH_3$, —$CHF_2$, —$CF_3$, —$CH_2OH$, —$CH_2OCH_3$, or —$NH_2$.

In certain embodiments, each $Z^{11}$ is independently fluoro, chloro, —CN, $C_{1-6}$ alkyl optionally substituted with 1 to 3 $Z^{1b}$, $C_{3-6}$ cycloalkyl optionally substituted with 1 to 3 $Z^{1b}$, —$OR^{13}$, —$C(O)R^{13}$, —$OC(O)R^{13}$, —$OC(O)OR^{13}$, —$OC(O)N(R^{13})_2$, —$N(R^{13})C(O)R^{13}$, —$N(R^{13})C(O)OR^{13}$, or —$N(R^{13})_2$.

In certain embodiments, each $Z^{11}$ is independently fluoro, chloro, —CN, —OH, —$OCH_3$, —$OCHF_2$, —$OCF_3$, —$CH_3$, —$CHF_2$, —$CF_3$, —$CH_2OH$, —$CH_2OCH_3$, or —$NH_2$.

In certain embodiments, provided is a compound of Formula (Ia):

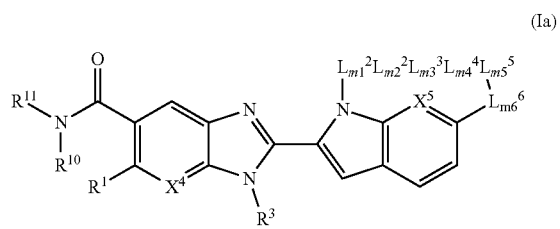

(Ia)

or a pharmaceutically acceptable salt, stereoisomer, mixture of stereoisomers, or tautomer thereof, wherein:

$R^1$, $R^3$, $R^{10}$, $R^{11}$, $L^1$, $L^2$, $L^3$, $L^4$, $L^5$, $L^6$, $X^4$, $X^5$, m1, m2, m3, m4, m5, and m6 are as disclosed herein.

In certain embodiments of Formula (I) or (Ia), the moiety

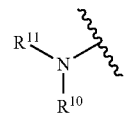

is:

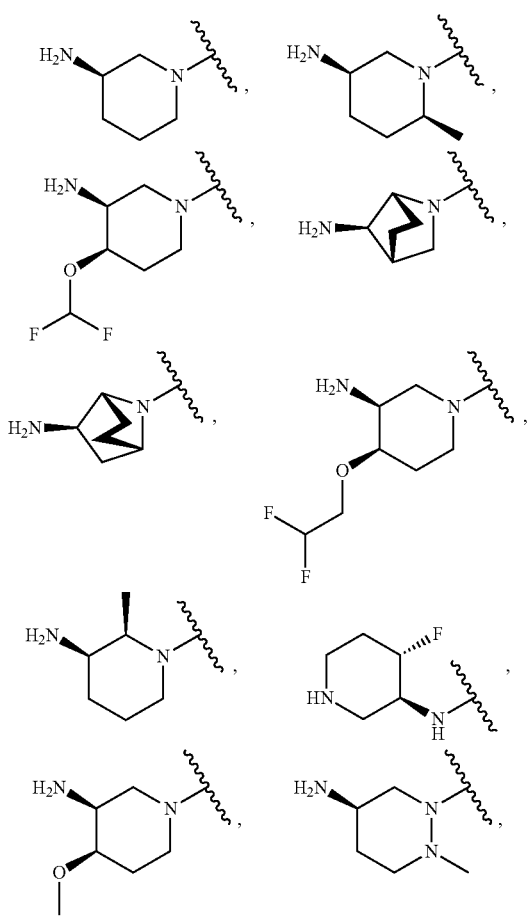

53
-continued
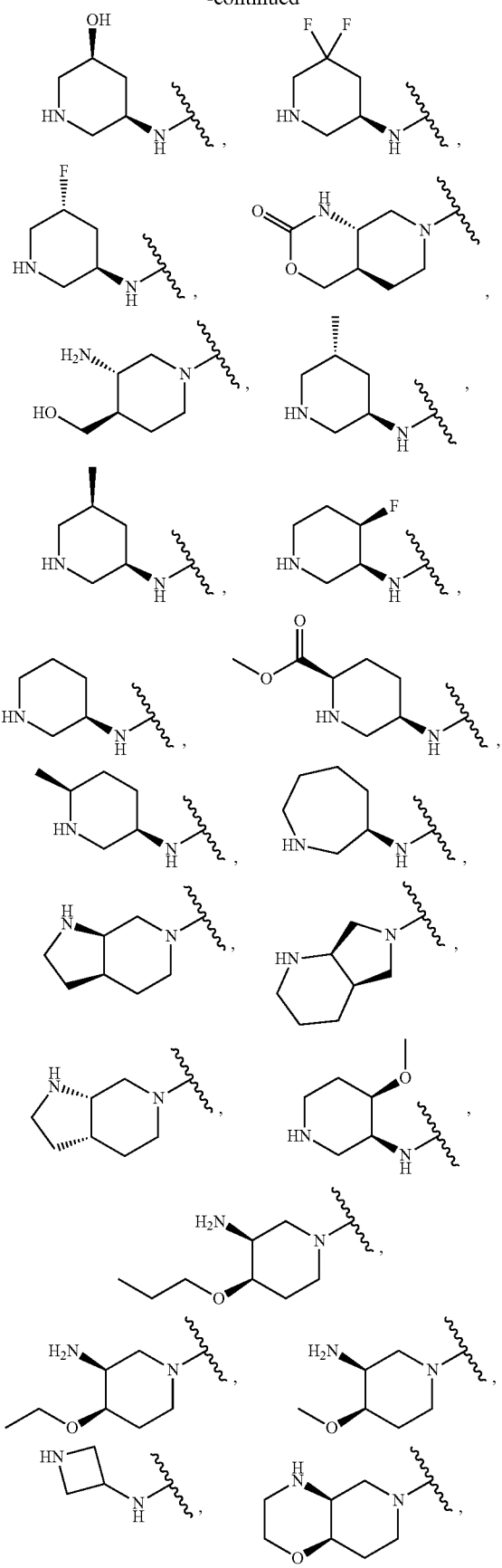
54
-continued
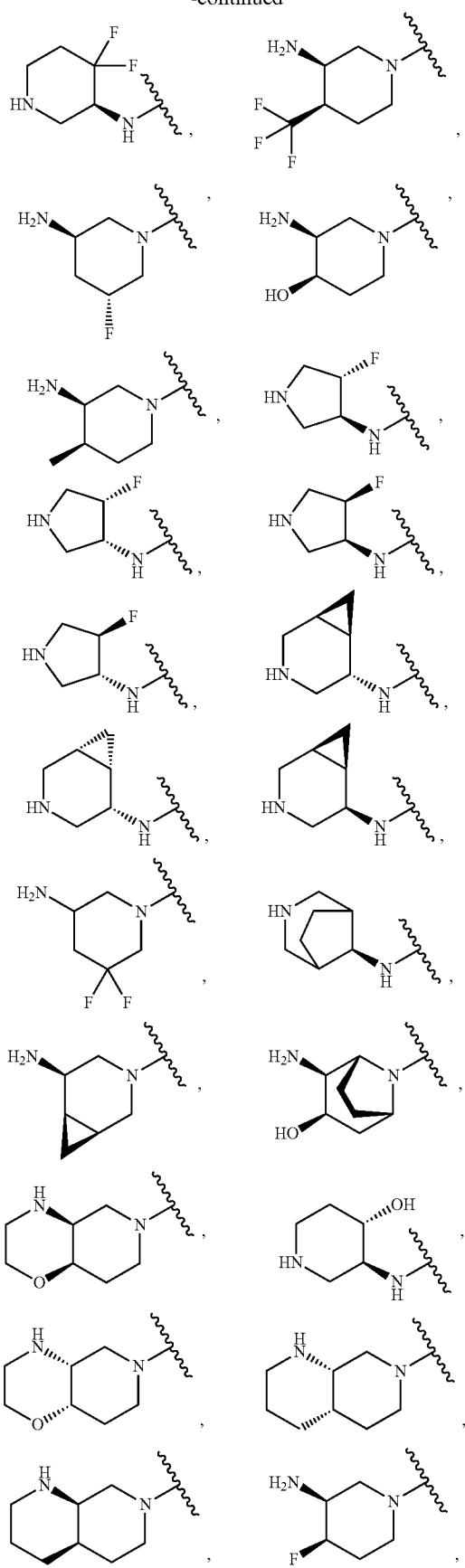

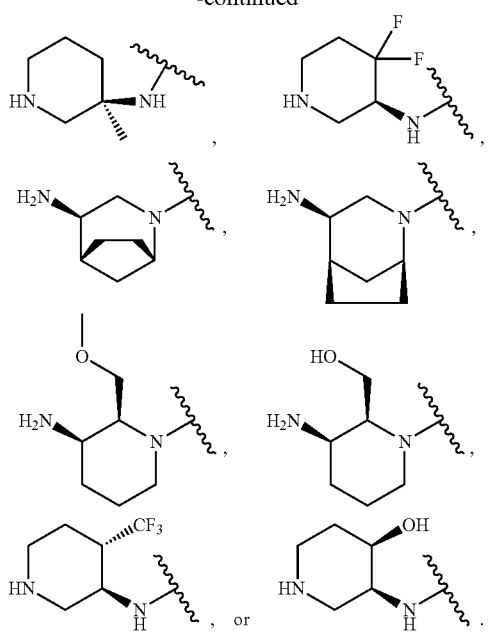
In certain embodiments of Formula (I) or (Ia), the moiety
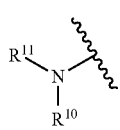
is:
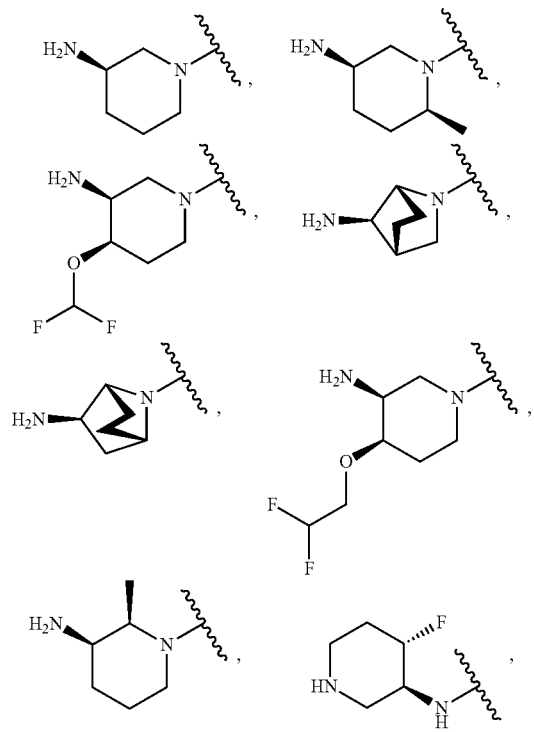
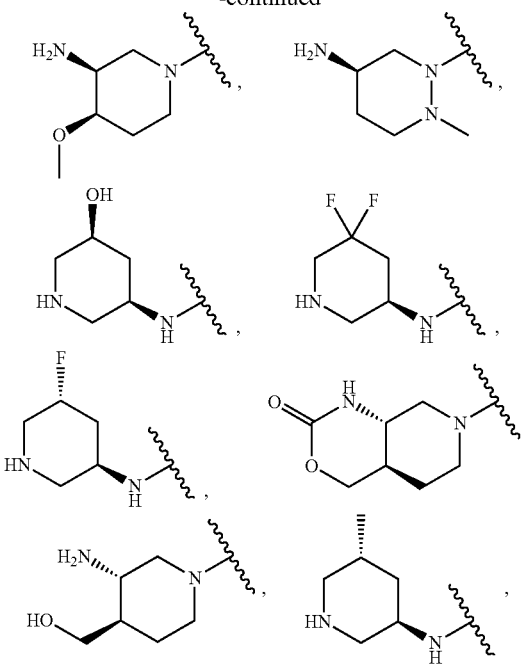

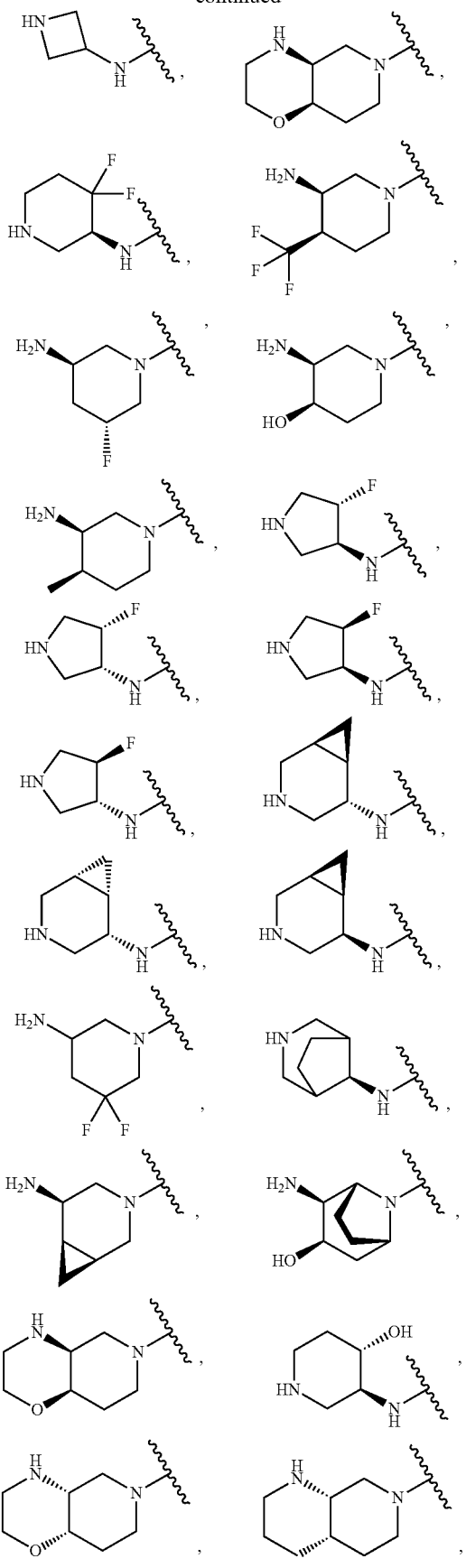
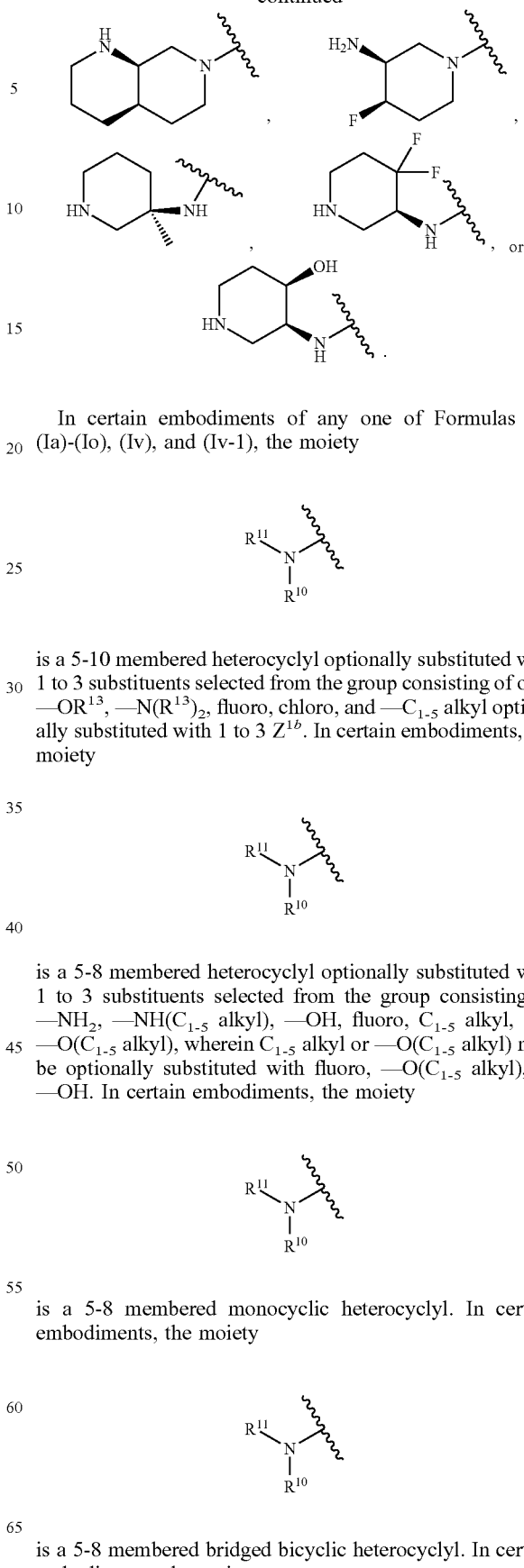

In certain embodiments of any one of Formulas (I), (Ia)-(Io), (Iv), and (Iv-1), the moiety $$\underset{R^{10}}{\overset{R^{11}}{N}}\wr$$

is a 5-10 membered heterocyclyl optionally substituted with 1 to 3 substituents selected from the group consisting of oxo, —OR$^{13}$, —N(R$^{13}$)$_2$, fluoro, chloro, and —C$_{1-5}$ alkyl optionally substituted with 1 to 3 Z$^{1b}$. In certain embodiments, the moiety $$\underset{R^{10}}{\overset{R^{11}}{N}}\wr$$

is a 5-8 membered heterocyclyl optionally substituted with 1 to 3 substituents selected from the group consisting of —NH$_2$, —NH(C$_{1-5}$ alkyl), —OH, fluoro, C$_{1-5}$ alkyl, and —O(C$_{1-5}$ alkyl), wherein C$_{1-5}$ alkyl or —O(C$_{1-5}$ alkyl) may be optionally substituted with fluoro, —O(C$_{1-5}$ alkyl), or —OH. In certain embodiments, the moiety $$\underset{R^{10}}{\overset{R^{11}}{N}}\wr$$

is a 5-8 membered monocyclic heterocyclyl. In certain embodiments, the moiety $$\underset{R^{10}}{\overset{R^{11}}{N}}\wr$$

is a 5-8 membered bridged bicyclic heterocyclyl. In certain embodiments, the moiety

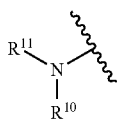

is a 5-8 membered fused bicyclic heterocyclyl. In certain embodiments, the moiety

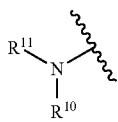

is a 5-8 membered spiro bicyclic heterocyclyl. In certain embodiments, the moiety

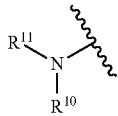

is a bridged bicyclic piperidyl or pyrrolidinyl, wherein piperidyl or pyrrolidinyl is optionally substituted with one to three substituents selected from the group consisting of —$NH_2$, —$NH(C_{1-5}$ alkyl), —OH, fluoro, and $C_{1-5}$ alkyl or —$O(C_{1-5}$ alkyl) optionally substituted with fluoro, —$O(C_{1-5}$ alkyl), or —OH.

In certain embodiments, the moiety

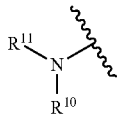

is

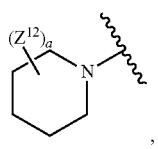

wherein each $Z^{12}$ is independently —$NH_2$, fluoro, —OH, $C_{1-6}$ alkyl, or —$OCH_3$ optionally substituted with F; a is 1, 2, or 3. In certain embodiments, the moiety

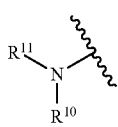

is

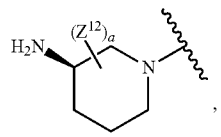

wherein each $Z^{12}$ is independently —F, —OH, $C_{1-6}$ alkyl, or —$OCH_3$ optionally substituted with F; a is 0, 1, or 2. In certain embodiments, the moiety

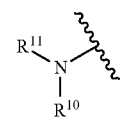

is

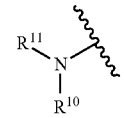

In certain embodiments, the moiety

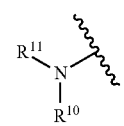

is

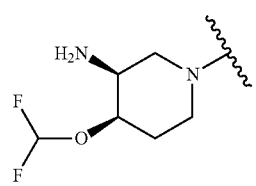

In certain embodiments, the moiety is

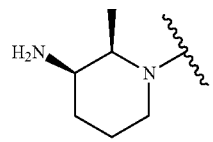

In certain embodiments, the moiety

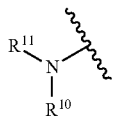

is

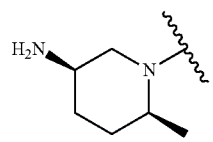

In certain embodiments, the moiety

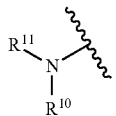

is

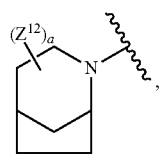, wherein each $Z^{12}$ is independently —NH$_2$, F, or —OCH$_3$ optionally substituted with F; a is 1, 2, or 3. In certain embodiments, at least one $Z^{12}$ is —NH$_2$. In certain embodiments, the moiety

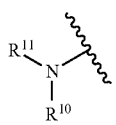

is

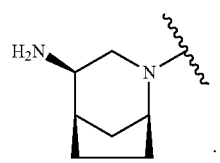.

In certain embodiments, the moiety

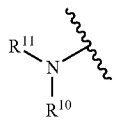

is

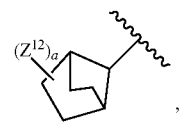, wherein each $Z^{12}$ is independently —NH$_2$, fluoro, —OH, or —OCH$_3$ optionally substituted with F; and a is 1, 2, or 3. In certain embodiments, the moiety

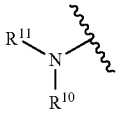

is

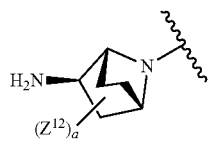, wherein each $Z^{12}$ is independently fluoro, —OH, or —OCH$_3$ optionally substituted with F; and a is 0, 1, or 2. In certain embodiments, the moiety

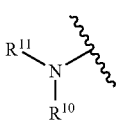

is

.

In certain embodiments, the moiety

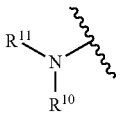

is

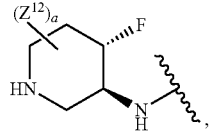

wherein each $Z^{12}$ is independently fluoro, —CH$_3$, —CF$_3$, —CHF$_2$, or —OCH$_3$ optionally substituted with fluoro; and a is 0, 1, or 2.

In certain embodiments of any one of Formulas (I), (Id), (Ie), (If), (Ig), (Ih), (Ii), (Ij), (Ik), (Iv), (Ip), (Iq), (Ir), (Is), and (It), the moiety

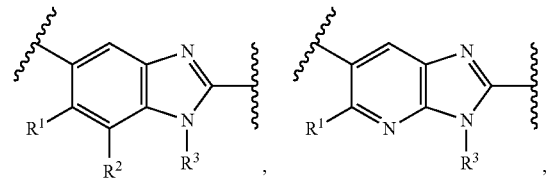

is

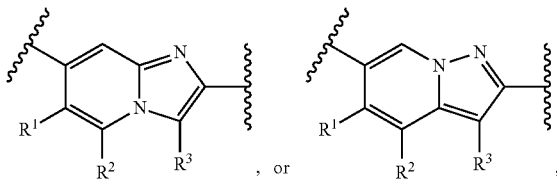

wherein $R^1$, $R^2$, and $R^3$ are as disclosed herein. In certain embodiments, the moiety

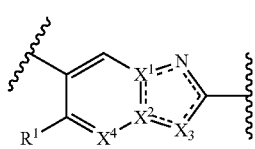

is

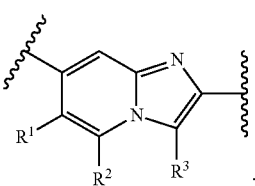

In certain embodiments, the moiety

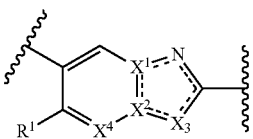

is

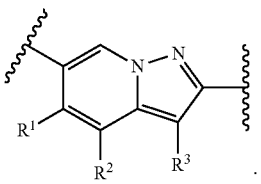

In certain embodiments, the moiety

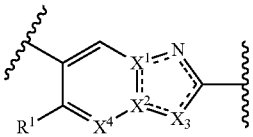

is

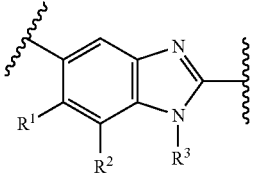

In certain embodiments, $R^1$ is hydrogen or fluoro; $R^2$ is hydrogen, fluoro, or —OCH$_3$; and $R^3$ is methyl or cyclopropyl.

In certain embodiments of Formula (Ia), $R^1$ is hydrogen or halo. In certain embodiments of Formula (Ia), $R^1$ is hydrogen or fluoro. In certain embodiments of Formula (Ia), $R^1$ is hydrogen. In certain embodiments of Formula (Ia), $R^1$ is halo. In certain embodiments of Formula (Ia), $R^1$ is fluoro.

In certain embodiments of Formula (Ia), $X^3$ is N—$R^3$ and $R^3$ is $C_{1-6}$ alkyl optionally substituted with 1 to 3 $Z^3$ or $C_{3-6}$ cycloalkyl optionally substituted with 1 to 3 $Z^3$. In certain embodiments of Formula (Ia), $X^3$ is N and N—$R^3$ is methyl, (1-fluorocyclopropyl)methyl, (1-cyanocyclopropyl)methyl, 2-(difluoromethyl)cyclopropyl, 2-methylcyclopropyl, (1-methoxycyclopropyl)methyl. 2-methoxyethyl, 2,2-difluoroethyl, 2,2,2-trifluoroethyl, cyclobutyl, isopropyl, ethyl, 2-isopropoxyethyl, 2-ethoxyethyl, 2-cyanoethyl, 2-(2-methoxyethoxy)ethyl, 3-amino-3-oxopropyl, 2-phenoxyethyl, 2-methoxypropyl, 2-(pyridin-2-yloxy)ethyl, 2-fluorocyclopropyl, or 2-methoxycyclopropyl.

In certain embodiments of Formula (Ia), $R^3$ is alkyl or cycloalkyl. In certain embodiments of Formula (Ia), $R^3$ is methyl or cyclopropyl. In certain embodiments of Formula (Ia), $R^3$ is alkyl. In certain embodiments of Formula (Ia), $R^3$ is methyl. In certain embodiments of Formula (Ia), $R^3$ is cycloalkyl. In certain embodiments of Formula (Ia), $R^3$ is cyclopropyl.

In certain embodiments of Formula (Ia), $X^4$ is N. In certain embodiments of Formula (Ia), $X^4$ is C—$R^2$. In certain embodiments of Formula (Ia), $X^4$ is C—$R^2$ and $R^2$ is hydrogen, halo, or —O-alkyl. In certain embodiments of Formula (Ia), $X^4$ is C—$R^2$ and $R^2$ is hydrogen, fluoro, or methoxy. In certain embodiments of Formula (Ia), $X^4$ is C—$R^2$ and $R^2$ is hydrogen, fluoro, chloro, or —O—$CH_3$. In certain embodiments of Formula (Ia), $X^4$ is C—$R^2$ and $R^2$ is hydrogen. In certain embodiments of Formula (Ia), $X^4$ is C—$R^2$ and $R^2$ is halo. In certain embodiments of Formula (Ia), $X^4$ is C—$R^2$ and $R^2$ is fluoro. In certain embodiments of Formula (Ia), $X^4$ is C—$R^2$ and $R^2$ is —O-alkyl. In certain embodiments of Formula (Ia), $X^4$ is C—$R^2$ and $R^2$ is methoxy.

In certain embodiments, provided is a compound of Formula (Ib):

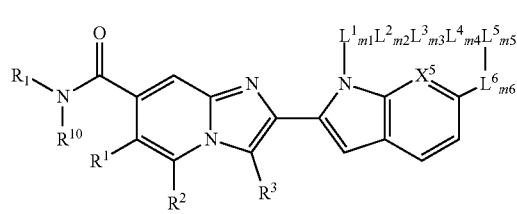

(Ib)

or a pharmaceutically acceptable salt, stereoisomer, mixture of stereoisomers, or tautomer thereof, wherein:
$R^1$, $R^2$, $R^3$, $R^{10}$, $R^{11}$, $L^1$, $L^2$, $L^3$, $L^4$, $L^5$, $L^6$, $X^5$, m1, m2, m3, m4, m5, and m6 are as disclosed herein.

In certain embodiments of Formula (Ib), the moiety

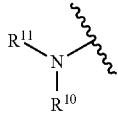

is

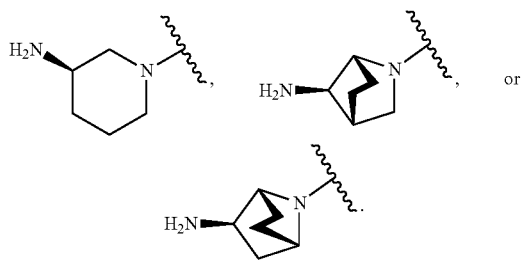

In certain embodiments of Formula (Ib), $R^1$ is hydrogen.
In certain embodiments of Formula (Ib), $R^2$ is hydrogen or —O-alkyl. In certain embodiments of Formula (Ib), $R^2$ is hydrogen or methoxy. In certain embodiments of Formula (Ib), $R^2$ is hydrogen. In certain embodiments of Formula (Ib), $R^2$ is —O-alkyl. In certain embodiments of Formula (Ib), $R^2$ is methoxy.

In certain embodiments of Formula (Ib), $R^3$ is alkyl or cycloalkyl. In certain embodiments of Formula (Ib), $R^3$ is methyl or cyclopropyl. In certain embodiments of Formula (Ib), $R^3$ is alkyl. In certain embodiments of Formula (Ib), $R^3$ is methyl. In certain embodiments of Formula (Ib), $R^3$ is cycloalkyl. In certain embodiments of Formula (Ib), $R^3$ is cyclopropyl.

In certain embodiments, provided is a compound of Formula (Ic):

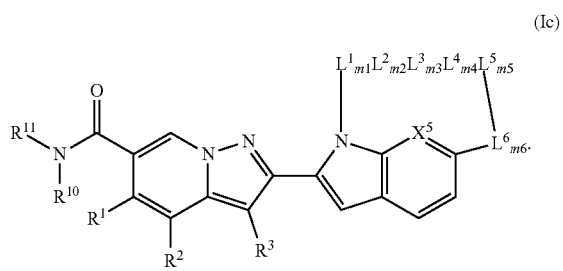

(Ic)

or a pharmaceutically acceptable salt, stereoisomer, mixture of stereoisomers, or tautomer thereof, wherein:
$R^1$, $R^2$, $R^3$, $R^{10}$, $R^{11}$, $L^1$, $L^2$, $L^3$, $L^4$, $L^5$, $L^6$, $X^5$, m1, m2, m3, m4, m5, and m6 are as disclosed herein.

In certain embodiments of Formula (Ic), the moiety

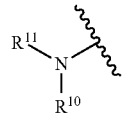

is

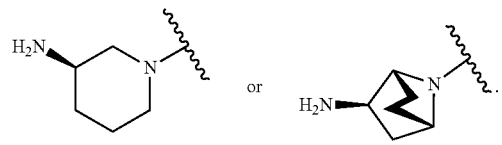

In certain embodiments of Formula (Ic), $R^1$ is hydrogen.
In certain embodiments of Formula (Ic), $R^2$ is hydrogen or —O-alkyl. In certain embodiments of Formula (Ic), $R^2$ is hydrogen or methoxy. In certain embodiments of Formula (Ic), $R^2$ is hydrogen. In certain embodiments of Formula (Ic), $R^2$ is —O-alkyl. In certain embodiments of Formula (Ic), $R^2$ is methoxy.

In certain embodiments of Formula (Ic), $R^3$ is alkyl. In certain embodiments of Formula (Ic), $R^3$ is methyl or ethyl. In certain embodiments of Formula (Ic), $R^3$ is methyl. In certain embodiments of Formula (Ic), $R^3$ is ethyl.

In certain embodiments, provided is a compound of Formula (Id):

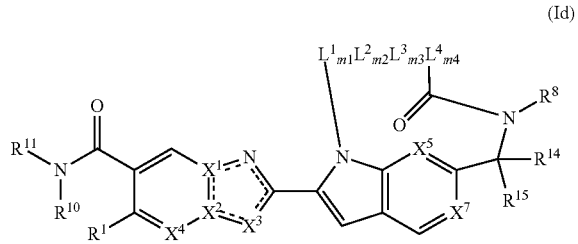

(Id)

or a pharmaceutically acceptable salt, stereoisomer, mixture of stereoisomers, or tautomer thereof, wherein:

$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;

$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; or $R^{14}$ and $R^{15}$ can be taken together to form a 3-6-membered cycloalkyl that is optionally substituted with 1 to 3 $Z^{1a}$ or 4-6-membered heterocyclyl containing 1-2 heteroatoms independently selected from O, N, and S that is optionally substituted with 1-3 $Z^{1a}$; and $X^1$, $X^2$, $X^3$, $X^4$, $X^5$, $X^7$, $R^1$, $R^8$, $R^{10}$, $R^{11}$, $L^1$, $L^2$, $L^3$, $L^4$, m1, m2, m3, and m4 are as disclosed herein.

In certain embodiments, provided is a compound of Formula (Ie):

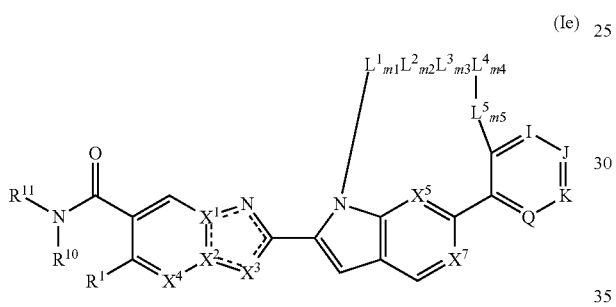

(Ie)

or a pharmaceutically acceptable salt, stereoisomer, mixture of stereoisomers, or tautomer thereof, wherein:

$X^1$, $X^2$, $X^3$, $X^4$, $X^5$, $X^7$, $R^1$, $R^{10}$, $R^{11}$, $L^1$, $L^2$, $L^3$, $L^4$, $L^5$, m1, m2, m3, m4, and m5 are as disclosed herein; and I, J, K, Q are each independently N, CH or C—$Z^8$ provided that at least two of I, J, K, Q are CH or C—$Z^8$.

In certain embodiments, provided is a compound of Formula (If):

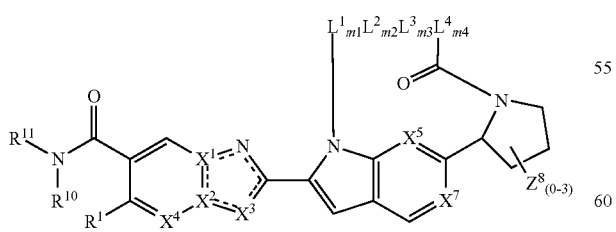

(If)

or a pharmaceutically acceptable salt, stereoisomer, mixture of stereoisomers, or tautomer thereof, wherein:

$X^1$, $X^2$, $X^3$, $X^4$, $X^5$, $X^7$, $R^1$, $R^{10}$, $R^{11}$, $L^1$, $L^2$, $L^3$, $L^4$, $Z^8$, m1, m2, m3, and m4 are as disclosed herein.

In certain embodiments, provided is a compound of Formula (Ig):

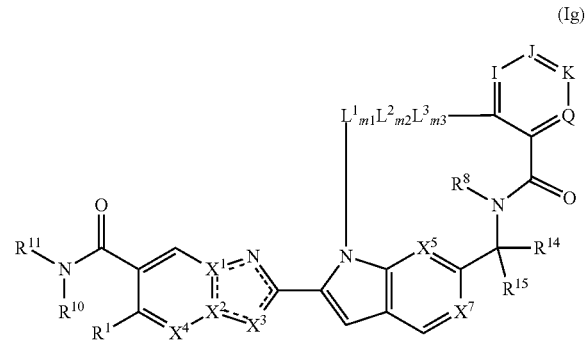

(Ig)

or a pharmaceutically acceptable salt, stereoisomer, mixture of stereoisomers, or tautomer thereof, wherein:

$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;

$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; or $R^{14}$ and $R^{15}$ can be taken together to form a 3-6-membered cycloalkyl that is optionally substituted with 1 to 3 $Z^{1a}$ or 4-6-membered heterocyclyl containing 1-2 heteroatoms independently selected from O, N, and S that is optionally substituted with 1-3 $Z^{1a}$;

I, J, K, Q are each independently N, CH or C—$Z^8$ provided that at least two of I, J, K, Q are CH or C—$Z^8$; and $X^1$, $X^2$, $X^3$, $X^4$, $X^5$, $X^7$, $R^1$, $R^8$, $R^{10}$, $R^{11}$, $L^1$, $L^2$, $L^3$, $Z^8$, m1, m2, m3, and m4 are as disclosed herein.

In certain embodiments, provided is a compound of Formula (Ih):

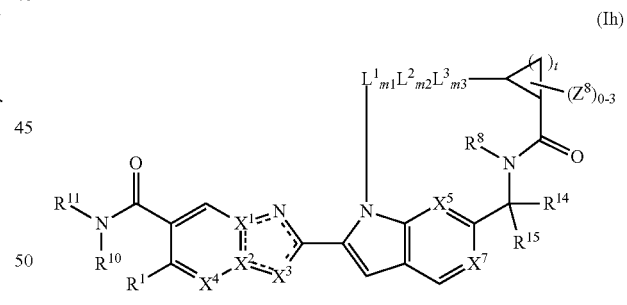

(Ih)

or a pharmaceutically acceptable salt, stereoisomer, mixture of stereoisomers, or tautomer thereof, wherein:

$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, or S, optionally substituted with 1-3 $Z^{1a}$;

$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, or S, optionally substituted with 1-3 $Z^{1a}$; or $R^{14}$ and $R^{15}$ can be taken together to form a 3-6-membered cycloalkyl that is optionally substituted with 1 to 3 $Z^{1a}$ or 4-6-membered heterocyclyl containing 1-2 heteroatoms independently selected from O, N, or S that is optionally substituted with 1-3 $Z^{1a}$;

t is 1, 2, 3, or 4; and $X^1, X^2, X^3, X^4, X^5, X^7, R^1, R^8, R^{10}, R^{11}, L^1, L^2, L^3, L^4, Z^8$, m1, m2, m3, and m4 are as disclosed herein.

In certain embodiments, provided is a compound of Formula (Ii):

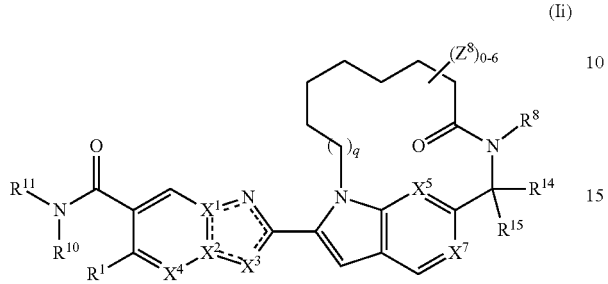

(Ii)

or a pharmaceutically acceptable salt, stereoisomer, mixture of stereoisomers, or tautomer thereof, wherein:
$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;
$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; or
$R^{14}$ and $R^{15}$ can be taken together to form a 3-6-membered cycloalkyl that is optionally substituted with 1 to 3 $Z^{1a}$ or 4-6-membered heterocyclyl containing 1-2 heteroatoms independently selected from O, N, or S that is optionally substituted with 1-3 $Z^{1a}$;
q is 0, 1 or 2; and
$X^1, X^2, X^3, X^4, X^5, X^7, R^1, R^8, R^{10}, R^{11}$, and $Z^8$ are as disclosed herein.

In certain embodiments, provided is a compound of Formula (Ij):

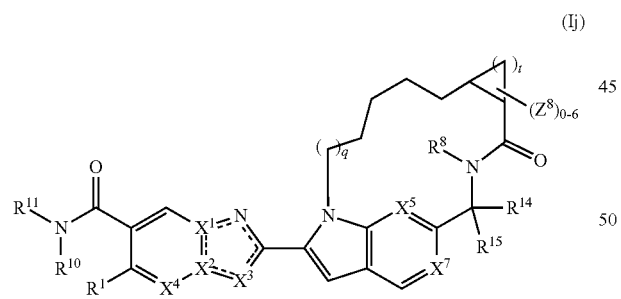

(Ij)

or a pharmaceutically acceptable salt, stereoisomer, mixture of stereoisomers, or tautomer thereof, wherein:
$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;
$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; or
$R^{14}$ and $R^{15}$ can be taken together to form a 3-6-membered cycloalkyl that is optionally substituted with 1 to 3 $Z^{1a}$ or 4-6-membered heterocyclyl containing 1-2 heteroatoms independently selected from O, N, and S that is optionally substituted with 1-3 $Z^{1a}$;
t is 1, 2, 3, or 4;
q is 0, 1 or 2; and
$X^1, X^2, X^3, X^4, X^5, X^7, R^1, R^8, R^{10}, R^{11}$, and $Z^8$ are as disclosed herein.

In certain embodiments, provided is a compound of Formula (Ij-1):

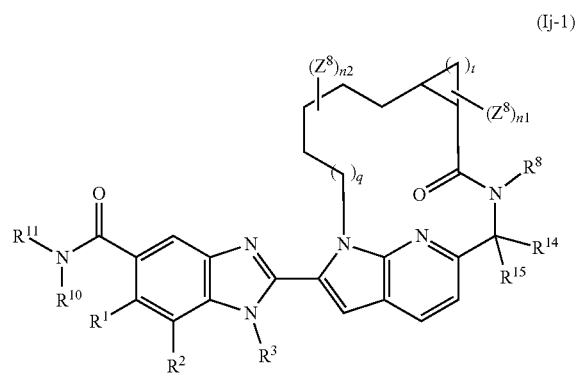

(Ij-1)

or a pharmaceutically acceptable salt, stereoisomer, mixture of stereoisomers, or tautomer thereof, wherein:
$R^{14}$ and $R^{15}$ are each independently hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;
t is 1, 2, 3, or 4;
q is 0, 1 or 2;
n1 is 0, 1, 2, or 3;
n2 is 0, 1, 2, or 3; and
$R^1, R^2, R^3, R^8, R^{10}, R^{11}$, and $Z^8$ are as described herein.

In certain embodiments, provided is a compound of Formula (Ik):

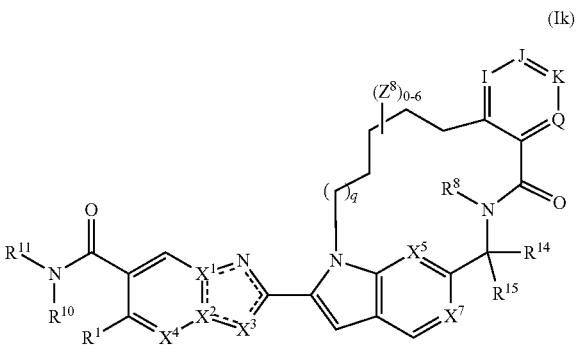

(Ik)

or a pharmaceutically acceptable salt, stereoisomer, mixture of stereoisomers, or tautomer thereof, wherein:
$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;
$R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; or R[14] and R[15] can be taken together to form a 3-6-membered cycloalkyl that is optionally substituted with 1 to 3 $Z^{1a}$ or 4-6-membered heterocyclyl containing 1-2 heteroatoms independently selected from O, N, and S that is optionally substituted with 1-3 $Z^{1a}$;

I, J, K, Q are each independently N, CH or C—$Z^8$ provided that at least two of I, J, K, Q are CH or C—$Z^8$;

q is 0, 1 or 2; and $X^1$, $X^2$, $X^3$, $X^4$, $X^5$, $X^7$, $R^1$, $R^8$, $R^{10}$, $R^{11}$, and $Z^8$ are as disclosed herein.

In certain embodiments, provided is a compound of Formula (Iv):

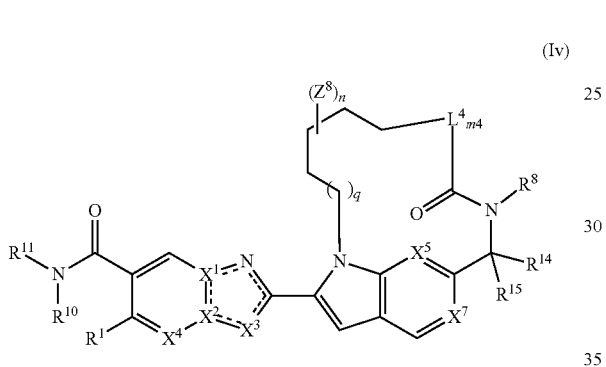

(Iv)

or a pharmaceutically acceptable salt, stereoisomer, mixture of stereoisomers, or tautomer thereof, wherein:

$L^4$ is methylene optionally substituted with 1 to 2 $Z^{13}$, $C_{3-6}$ cycloalkylene optionally substituted with 1 to 2 $Z^8$, 4-10 membered heterocyclene optionally substituted with 1 to 2 $Z^8$, 6-10 membered arylene optionally substituted with 1 to 2 $Z^8$, or heteroarylene optionally substituted with 1 to 2 $Z^8$;

each $Z^{13}$ is independently selected from the group consisting of fluoro, —$C_{1-6}$ alkyl, —$CF_3$, —O—$C_{1-5}$ alkyl, —$OCF_3$, —O—$C_{3-6}$ cycloalkyl, $C_{3-6}$ cycloalkyl, 4-10 membered heterocyclyl, 6-10 membered aryl, or 5-10 membered heteroaryl, wherein each of —$C_{1-6}$ alkyl, —O—$C_{1-5}$ alkyl, $C_{3-6}$ cycloalkyl, 4-10 membered heterocyclyl, 6-10 membered aryl, and 5-10 membered heteroaryl is optionally substituted with 1 to 2 $Z^8$;

m4 is 1;

q is 0, 1 or 2;

n is 0, 1, 2, 3, or 4;

$R^{14}$ and $R^{15}$ are each independently hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; and $X^1$, $X^2$, $X^3$, $X^4$, $X^5$, $X^7$, $R^1$, $R^8$, $R^{10}$, $R^{11}$, and $Z^8$ are as described herein.

In certain embodiments, Formula (Iv) is represented by Formula (Iv-1):

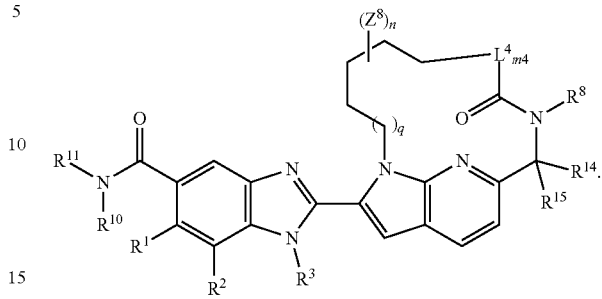

(Iv-1)

In certain embodiments, $L^4$ is selected from the group consisting of:

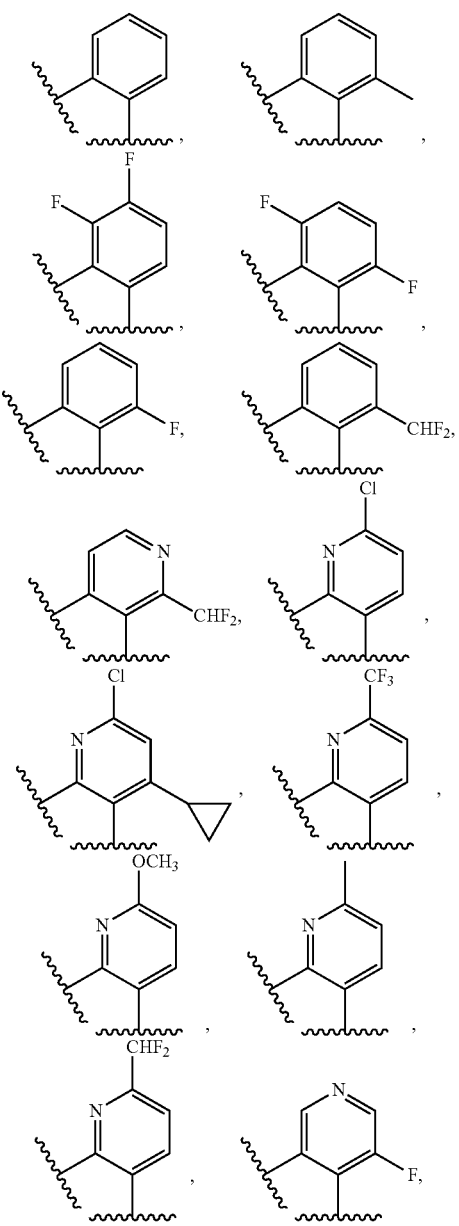

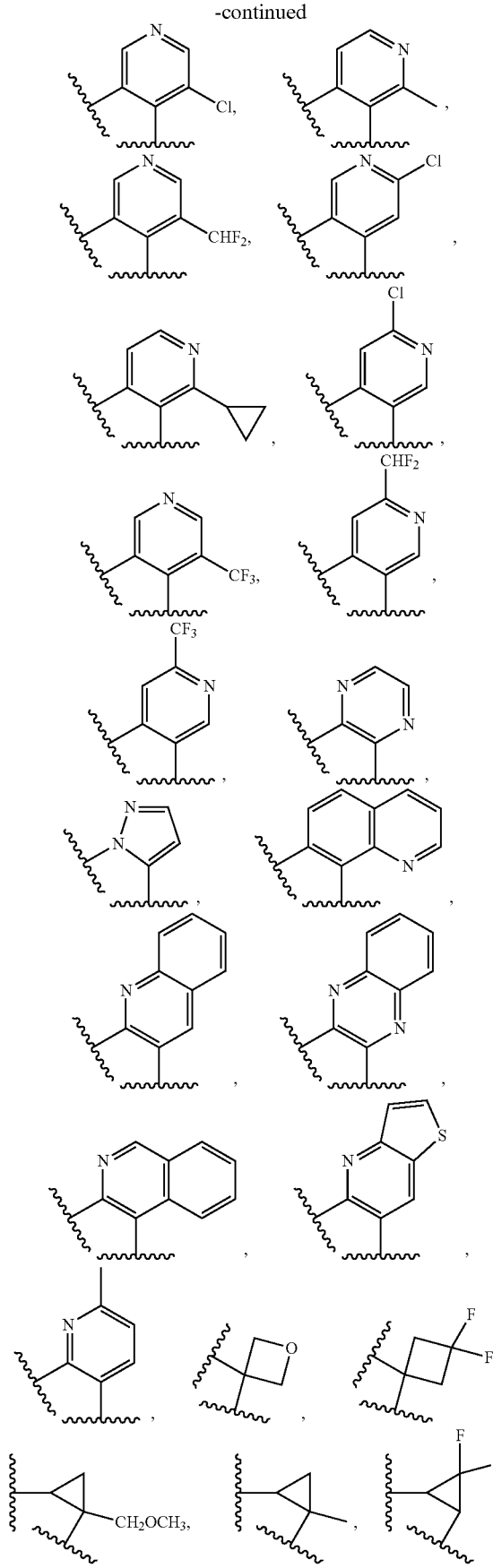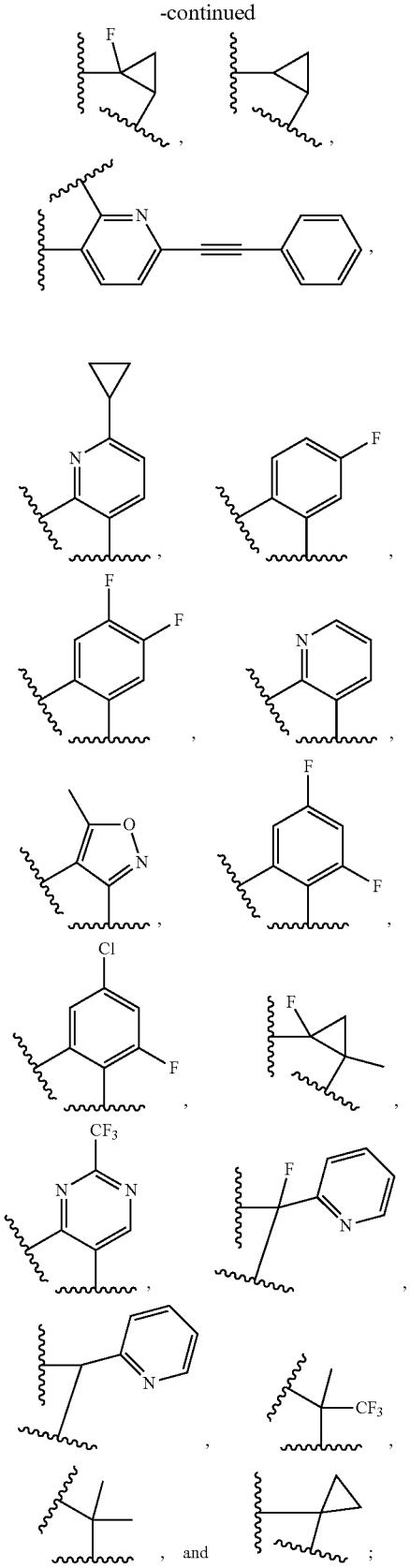
wherein either of the two broken bonds may be attached to —CO— in —CO—NR$^8$.

In certain embodiments, L⁴ is

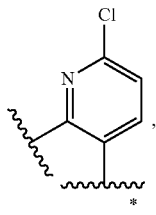

wherein the broken bond with * is attached to —CO— of —NR⁸—CO—. In certain embodiments, L⁴ is

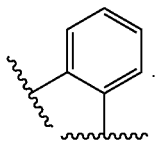

In certain embodiments, L⁴ is

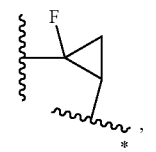

wherein the broken bond with * is attached to —CO— of —NR⁸—CO—. In certain embodiments, L⁴ is

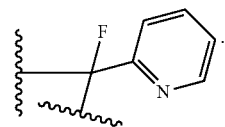 [SMILES: *C(*)(F)c1ccccn1]

In certain embodiments of Formula (Ig), or (Ik), at least two of I, J, K, and Q are C—H, C—Cl, C—F, C—OCH₃, C—CH₃, C-cyclopropyl, C—CH₂F, or C—CF₃.

In certain embodiments, provided is a compound of Formula (Il):

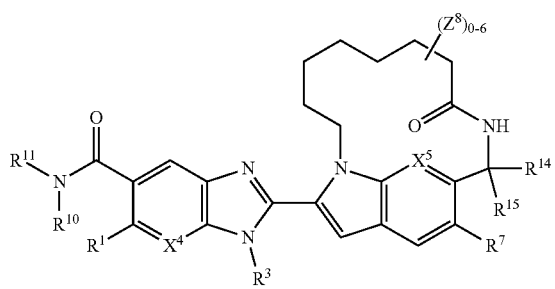

(Il)

or a pharmaceutically acceptable salt, stereoisomer, mixture of stereoisomers, or tautomer thereof, wherein:

R¹⁴ is hydrogen, C₁₋₈ alkyl optionally substituted with 1-3 Z¹ᵃ, C₃₋₈ cycloalkyl optionally substituted with 1-3 Z¹ᵃ, C₄₋₆ heterocyclyl having 1-3 heteroatoms selected from O, N, and S, optionally substituted with 1-3 Z¹ᵃ;

R¹⁵ is hydrogen, C₁₋₈ alkyl optionally substituted with 1-3 Z¹ᵃ, C₃₋₈ cycloalkyl optionally substituted with 1-3 Z¹ᵃ, C₄₋₆ heterocyclyl having 1-3 heteroatoms selected from O, N, and S, optionally substituted with 1-3 Z¹ᵃ; or R¹⁴ and R¹⁵ can be taken together to form a 3-6-membered cycloalkyl that is optionally substituted with 1 to 3 Z¹ᵃ or 4-6-membered heterocyclyl containing 1-2 heteroatoms independently selected from O, N, and S that is optionally substituted with 1-3 Z¹ᵃ; and X⁴, X⁵, R¹, R³, R⁷, R⁸, R¹⁰, R¹¹, and Z⁸ are as disclosed herein.

In certain embodiments, provided is a compound of Formula (Im):

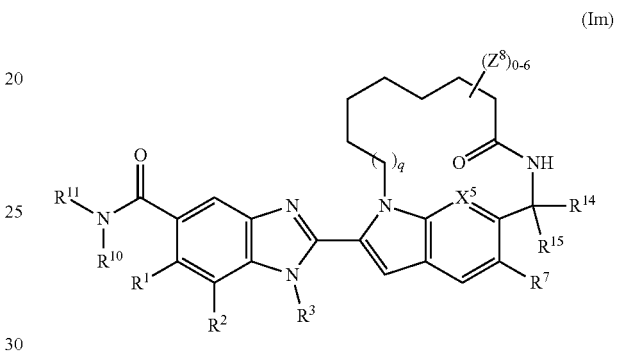

(Im)

or a pharmaceutically acceptable salt, stereoisomer, mixture of stereoisomers, or tautomer thereof, wherein:

R¹⁴ is hydrogen, C₁₋₈ alkyl optionally substituted with 1-3 Z¹ᵃ, C₃₋₈ cycloalkyl optionally substituted with 1-3 Z¹ᵃ, C₄₋₆ heterocyclyl having 1-3 heteroatoms selected from O, N, and S, optionally substituted with 1-3 Z¹ᵃ;

R¹⁵ is hydrogen, C₁₋₈ alkyl optionally substituted with 1-3 Z¹ᵃ, C₃₋₈ cycloalkyl optionally substituted with 1-3 Z¹ᵃ, C₄₋₆ heterocyclyl having 1-3 heteroatoms selected from O, N, and S, optionally substituted with 1-3 Z¹ᵃ; or R¹⁴ and R¹⁵ can be taken together to form a 3-6-membered cycloalkyl that is optionally substituted with 1 to 3 Z¹ᵃ or 4-6-membered heterocyclyl containing 1-2 heteroatoms independently selected from O, N, and S that is optionally substituted with 1-3 Z¹ᵃ;

q is 0, 1 or 2; and

X⁵, R¹, R², R³, R⁷, R¹⁰, R¹¹, and Z⁸ are as disclosed herein.

In certain embodiments, provided is a compound of Formula (In):

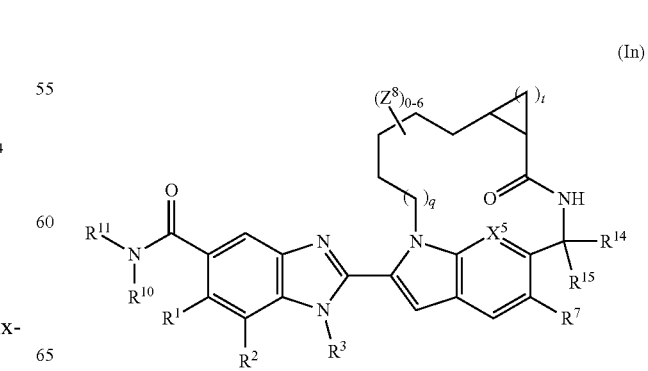

(In)

or a pharmaceutically acceptable salt, stereoisomer, mixture of stereoisomers, or tautomer thereof, wherein:

R$^{14}$ is hydrogen, C$_{1-8}$ alkyl optionally substituted with 1-3 Z$^{1a}$, C$_{3-8}$ cycloalkyl optionally substituted with 1-3 Z$^{1a}$, C$_{4-6}$ heterocyclyl having 1-3 heteroatoms selected from O, N, and S, optionally substituted with 1-3 Z$^{1a}$;

R$^{15}$ is hydrogen, C$_{1-8}$ alkyl optionally substituted with 1-3 Z$^{1a}$, C$_{3-8}$ cycloalkyl optionally substituted with 1-3 Z$^{1a}$, C$_{4-6}$ heterocyclyl having 1-3 heteroatoms selected from O, N, and S, optionally substituted with 1-3 Z$^{1a}$; or R$^{14}$ and R$^{15}$ can be taken together to form a 3-6-membered cycloalkyl that is optionally substituted with 1 to 3 Z$^{1a}$ or 4-6-membered heterocyclyl containing 1-2 heteroatoms independently selected from O, N, and S that is optionally substituted with 1-3 Z$^{1a}$;

t is 1, 2, 3, or 4;
q is 0, 1 or 2; and
X$^5$, R$^1$, R$^2$, R$^3$, R$^7$, R$^{10}$, R$^{11}$, and Z$^8$ are as disclosed herein.

In certain embodiments, provided is a compound of Formula (Io):

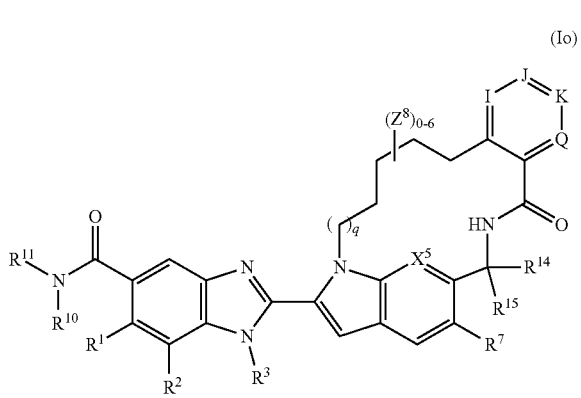

(Io)

or a pharmaceutically acceptable salt, stereoisomer, mixture of stereoisomers, or tautomer thereof, wherein:

R$^{14}$ is hydrogen, C$_{1-8}$ alkyl optionally substituted with 1-3 Z$^{1a}$, C$_{3-8}$ cycloalkyl optionally substituted with 1-3 Z$^{1a}$, C$_{4-6}$ heterocyclyl having 1-3 heteroatoms selected from O, N, and S, optionally substituted with 1-3 Z$^{1a}$;

R$^{15}$ is hydrogen, C$_{1-8}$ alkyl optionally substituted with 1-3 Z$^{1a}$, C$_{3-8}$ cycloalkyl optionally substituted with 1-3 Z$^{1a}$, C$_{4-6}$ heterocyclyl having 1-3 heteroatoms selected from O, N, and S, optionally substituted with 1-3 Z$^{1a}$; or R$^{14}$ and R$^{15}$ can be taken together to form a 3-6-membered cycloalkyl that is optionally substituted with 1 to 3 Z$^{1a}$ or 4-6-membered heterocyclyl containing 1-2 heteroatoms independently selected from O, N, and S that is optionally substituted with 1-3 Z$^{1a}$;

I, J, K, Q are each independently N, CH, or C—Z$^8$ provided that at least two of I, J, K, Q are CH, or C—Z$^8$;

q is 0, 1 or 2; and
X$^5$, R$^1$, R$^2$, R$^3$, R$^{10}$, R$^{11}$, and Z$^8$ are as disclosed herein.

In certain embodiments of any one of the Formulas disclosed herein (e.g., Formula (Id), (Ig), (Ih), (Ii), (Ij), (Ik), (Il), (Im), (In), or (Io)), R$^{14}$ is hydrogen, C$_{1-8}$ alkyl optionally substituted with 1-3 Z$^{1a}$, or C$_{3-8}$ cycloalkyl optionally substituted with 1-3 Z$^{1a}$; and R$^{15}$ is hydrogen, C$_{1-8}$ alkyl optionally substituted with 1-3 Z$^{1a}$, or C$_{3-8}$ cycloalkyl optionally substituted with 1-3 Z$^{1a}$.

In certain embodiments of any one of the Formulas disclosed herein (e.g., Formula (Id), (Ig), (Ih), (Ii), (Ij), (Ik), (Il), (Im), (In), or (Io)), R$^{14}$ is hydrogen, C$_{1-8}$ alkyl, or C$_{3-8}$ cycloalkyl; and R$^{15}$ is hydrogen, C$_{1-8}$ alkyl, or C$_{3-8}$ cycloalkyl.

In certain embodiments of any one of the Formulas disclosed herein (e.g., Formula (Id), (Ig), (Ih), (Ii), (Ij), (Ik), (Il), (Im), (In), or (Io)), R$^{14}$ is hydrogen, —C$_{1-8}$ alkyl optionally substituted with 1-3 Z$^{1a}$, or C$_{3-8}$ cycloalkyl optionally substituted with 1-3 Z$^{1a}$;

R$^{15}$ is hydrogen, —C$_{1-8}$ alkyl optionally substituted with 1-3 Z$^{1a}$, or C$_{3-8}$ cycloalkyl optionally substituted with 1-3 Z$^{1a}$;

X$^5$ is N, C—H, or C—F; and
R$^7$ is hydrogen or fluoro.

In certain embodiments, provided is a compound of Formula (Ip):

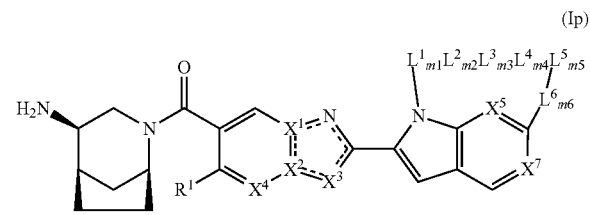

(Ip)

or a pharmaceutically acceptable salt, stereoisomer, mixture of stereoisomers, or tautomer thereof, wherein X$^1$, X$^2$, X$^3$, X$^4$, X$^5$, X$^7$, L$^1$-L$^6$, m1-m6, and R$^1$ are as disclosed herein.

In certain embodiments, provided is a compound of Formula (Iq):

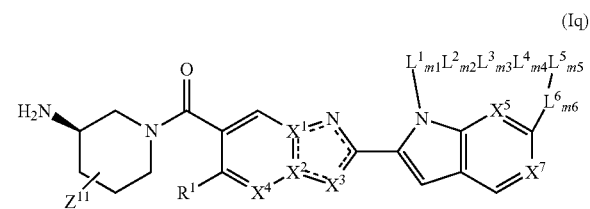

(Iq)

or a pharmaceutically acceptable salt, stereoisomer, mixture of stereoisomers, or tautomer thereof, wherein Z$^{11}$, X$^1$, X$^2$, X$^3$, X$^4$, X$^5$, X$^7$, L$^1$-L$^6$, m1-m6, and R$^1$ are as disclosed herein.

In certain embodiments, provided is a compound of Formula (Ir):

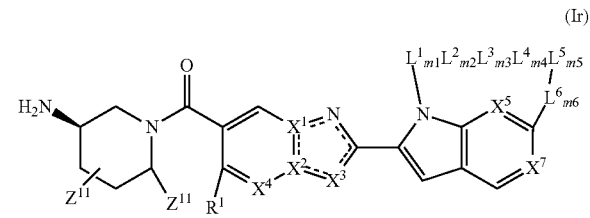

(Ir)

or a pharmaceutically acceptable salt, stereoisomer, mixture of stereoisomers, or tautomer thereof, wherein Z$^{11}$, X$^1$, X$^2$, X$^3$, X$^4$, X$^5$, X$^7$, L$^1$-L$^6$, m1-m6, and R$^1$ are as disclosed herein.

In certain embodiments, provided is a compound of Formula (Is):

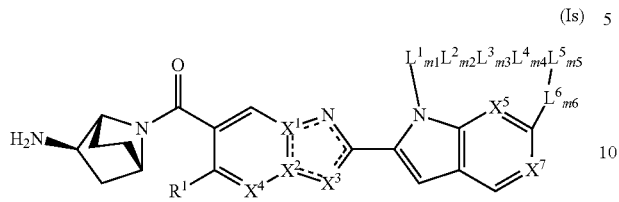

(Is)

or a pharmaceutically acceptable salt, stereoisomer, mixture of stereoisomers, or tautomer thereof, wherein $X^1$, $X^2$, $X^3$, $X^4$, $X^5$, $X^7$, $L^1$-$L^6$, m1-m6, and $R^1$ are as disclosed herein.

In certain embodiments, provided is a compound of Formula (It):

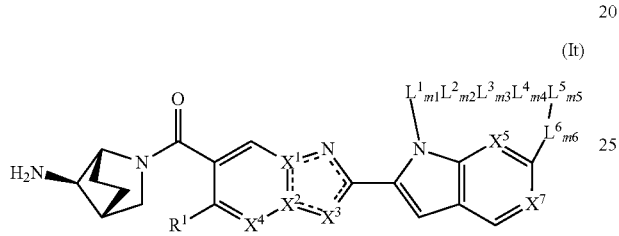

(It)

or a pharmaceutically acceptable salt, stereoisomer, mixture of stereoisomers, or tautomer thereof, wherein $X^1$, $X^2$, $X^3$, $X^4$, $X^5$, $X^7$, $L^1$-$L^6$, m1-m6, and $R^1$ are as disclosed herein.

In certain embodiments, provided is a compound of Formula (Iu):

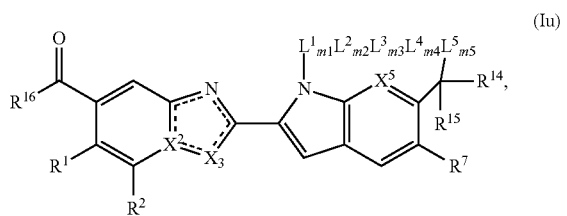

(Iu)

or a pharmaceutically acceptable salt, stereoisomer, mixture of stereoisomers, or tautomer thereof, wherein the moiety

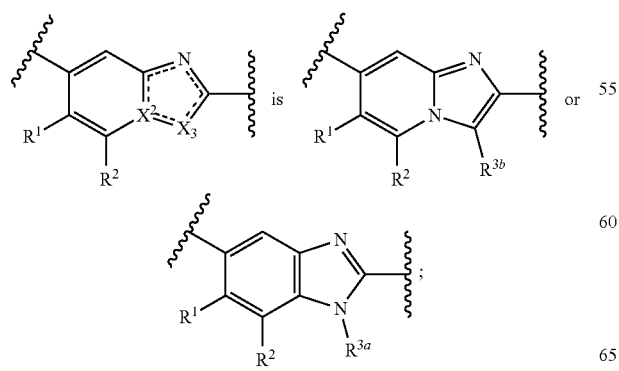

$R^1$ is hydrogen or fluoro;
$R^2$ is hydrogen, —$OCH_3$, —$CH_3$, fluoro, chloro, —$OCHF_2$, or —$OCF_3$;
$R^{3a}$ is —$CH_3$, —$CH_2CH_3$, —$CH_2$-cyclopropyl, —$CH_2CHF_2$, —$CH_2CH_2OCH_3$, or cyclopropyl optionally substituted with 1 to 3 fluoro or —$CHF_2$;
$R^{3b}$ is —$CH_3$ or cyclopropyl;
$X^5$ is CH, N, or CF;
$R^7$ is hydrogen or fluoro;
$R^{14}$ and $R^{15}$ are each independently hydrogen, $C_{1-6}$ alkyl, cyclopropyl, or —$CF_3$; or $R^{14}$ and $R^{15}$ taken together with the carbon to which they are attached form a 3-6 membered cycloalkyl;
$R^{16}$ is

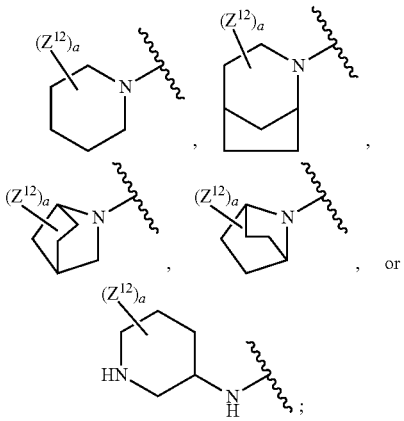

each $Z^{12}$ is independently —$NH_2$, fluoro, —OH, $C_{1-6}$ alkyl optionally substituted with 1 to 3 fluoro, or —$OCH_3$ optionally substituted with 1 to 3 fluoro; a is 1, 2, or 3;
$L^1$ is $C_{1-10}$ alkylene optionally substituted with 1 to 3 $Z^8$;
$L^2$ is $C_3$-$C_6$ cycloalkylene optionally substituted with 1 to 3 $Z^8$ or $C_{2-6}$ alkenylene optionally substituted with 1 to 3 $Z^8$;
$L^3$ is —O—, —O—$C_{1-8}$ alkylene optionally substituted with 1 to 3 $Z^8$, or $C_{1-8}$ alkylene optionally substituted with 1 to 3 $Z^8$;
$L^4$ is $C_{1-10}$ alkylene optionally substituted with 1 to 3 $Z^8$, 4-10 membered heterocyclene optionally substituted with 1 to 3 $Z^{8b}$, $C_3$-$C_{10}$ cycloalkylene optionally substituted with 1 to 3 $Z^8$, 5-10 membered heteroarylene optionally substituted with 1 to 3 $Z^8$, or $C_{6-10}$ arylene optionally substituted with 1 to 3 $Z^8$;
each $Z^8$ is independently halo, —CN, $C_{1-8}$ alkyl optionally substituted with 1 to 3 $Z^{1a}$, $C_{2-8}$ alkenyl optionally substituted with 1 to 3 $Z^{1a}$, $C_{2-8}$ alkynyl optionally substituted with 1 to 3 $Z^{1a}$, $C_{3-8}$ cycloalkyl optionally substituted with 1 to 3 $Z^{1a}$, 6-10 membered aryl optionally substituted with 1 to 3 $Z^{1a}$, 4-10 membered heterocyclyl optionally substituted with 1 to 3 $Z^{1a}$, 5-10 membered heteroaryl optionally substituted with 1 to 3 $Z^{1a}$, —$OR^9$, —$C(O)R^9$, or —$C(O)OR^9$;
each $Z^{1a}$ is independently halo, —CN, $C_{1-8}$ alkyl optionally substituted with 1 to 3 $Z^{1b}$, $C_{2-8}$ alkenyl optionally substituted by 1 to 3 $Z^{1b}$, or $C_{2-8}$ alkynyl optionally substituted with 1 to 3 $Z^{1b}$; $C_{3-8}$ cycloalkyl optionally substituted with 1 to 3 $Z^{1b}$, 6-10 membered aryl optionally substituted with 1 to 3 $Z^{1b}$, 4-10 membered heterocyclyl optionally substituted with 1 to 3 $Z^{1b}$, 5-10 membered heteroaryl optionally substituted with 1 to 3 $Z^{1b}$, —$OR^{13}$, —$C(O)R^{13}$, or —$C(O)OR^{13}$;

each $Z^{1b}$ is independently hydroxy, halo, —CN, $C_{1-9}$ alkyl, $C_{2-6}$ alkenyl, $C_{2-6}$ alkynyl, $C_{3-15}$ cycloalkyl, $C_{1-8}$ haloalkyl, 6-10 membered aryl, 5-10 membered heteroaryl, 4-10 membered heterocyclyl, —O($C_{1-9}$ alkyl), —O($C_{3-15}$ cycloalkyl), —O($C_{1-8}$ haloalkyl), —C(O)O ($C_{1-9}$ alkyl), —C(O)O($C_{3-15}$ cycloalkyl), or —C(O)O ($C_{1-8}$ haloalkyl);

each $R^9$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$L^5$ is —NHCO—, —N($CH_3$)CO—, or —N(COCH_3)—;

m1 is 1;

m2 is 0 or 1;

m3 is 0 or 1;

m4 is 0 or 1; and m5 is 1.

In certain embodiments, the compound of formula (Iu) is represented by Formula (Iu-1):

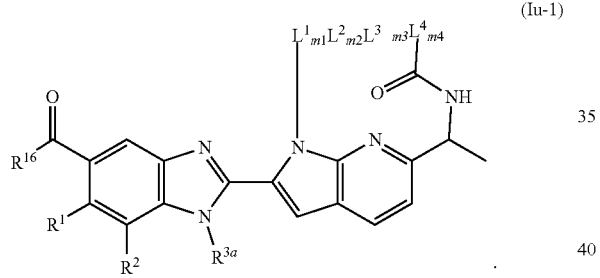

(Iu-1)

In certain embodiments, the compound of Formula (Iu), or (Iu-1), or a pharmaceutically acceptable salt, stereoisomer, mixture of stereoisomers, or tautomer thereof, is a compound wherein $L^1$ is $C_{1-10}$ alkylene optionally substituted with 1 to 3 halo;

$L^2$ is $C_3$-$C_6$ cycloalkylene optionally substituted with 1 to 3 halo or $C_{2-6}$ alkenylene optionally substituted with 1 to 3 halo;

$L^3$ is —O—, —O—$C_{1-8}$ alkylene optionally substituted with 1 to 3 halo, or $C_{1-8}$ alkylene optionally substituted with 1 to 3 halo;

$L^4$ is $C_{1-6}$ alkylene optionally substituted with 1 to 3 $Z^{8a}$, 5-10 membered nitrogen-containing heteroarylene optionally substituted with 1 to 3 $Z^{8b}$, $C_{6-10}$ arylene optionally substituted with 1 to 3 $Z^{8b}$, or $C_3$-$C_6$ cycloalkylene optionally substituted with 1 to 3 $Z^{8b}$;

each $Z^{8a}$ is independently halo, or 5-10 membered heteroaryl optionally substituted with 1-2 halo; and each $Z^{8b}$ is independently halo, $C_{1-6}$ alkyl, $C_{1-6}$ haloalkyl, —O($C_{1-6}$ alkyl), —O($C_{1-6}$ haloalkyl), —O($C_{3-6}$ cycloalkyl), cyclopropyl, or phenylethynyl.

In certain embodiments, the compound of Formula (Iu), or (Iu-1), is represented by Formula (Iu-2):

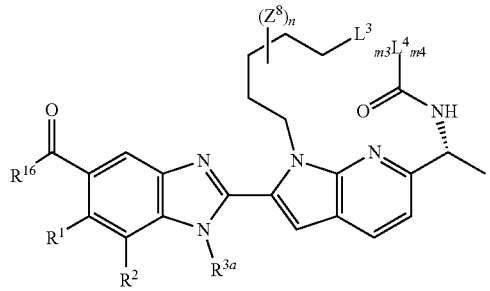

(Iu-2)

wherein $L^3$ is —O—;

m3 is 0 or 1;

m4 is 1;

$Z^8$ is fluoro;

n is 0, 1, 2, or 3; and q is 0, 1, or 2.

In certain embodiments, the compound of Formula (Iu), (Iu-1), or (Iu-2), or a pharmaceutically acceptable salt, stereoisomer, mixture of stereoisomers, or tautomer thereof, is a compound wherein $L^4$ is selected from the group consisting of

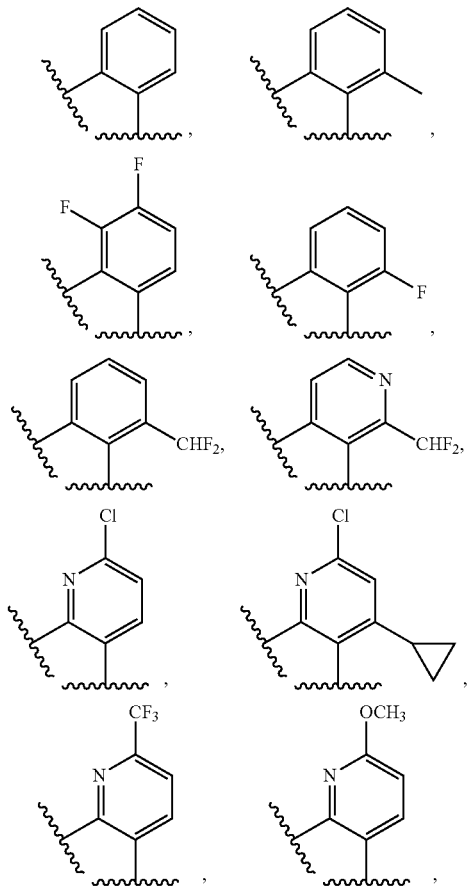

-continued
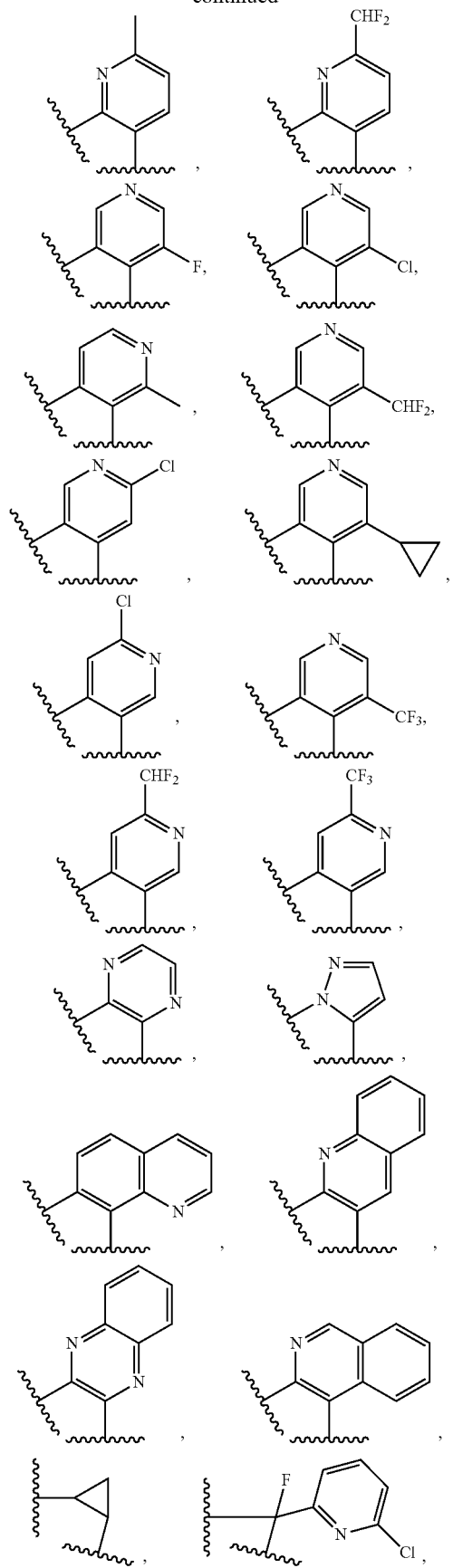
-continued
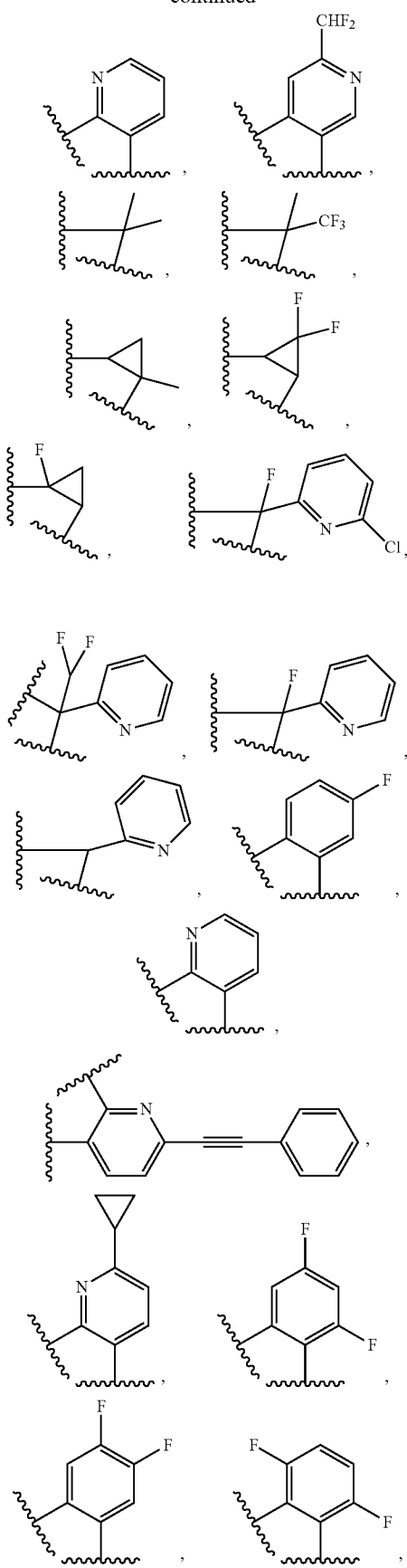

-continued

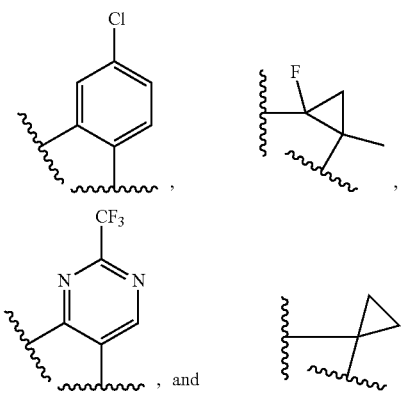

either of the two broken bonds may be attached to $L^5$ or —CO— in —CO—NH—.

In certain embodiments of Formula (Iu-2), m3 is 0; q is 1 or 2; and $L^4$ is selected from the group consisting of

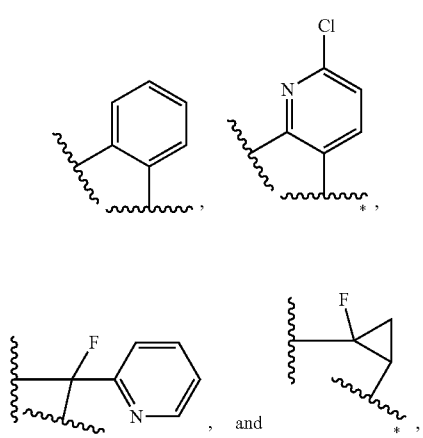

and when $L^4$ is

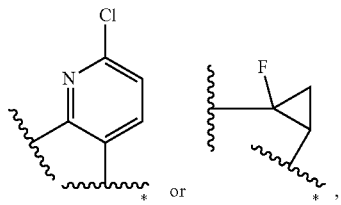 [SMILES: *c1ccc(Cl)nc1* ; *C1CC1(*)F]

the broken bond with * is attached to —CO— of —NR$^8$—CO—. In certain embodiments, $L^4$ is

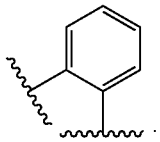

In certain embodiments, $L^4$ is

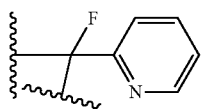

In certain embodiments, $L^4$ is

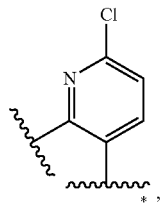 [SMILES: *c1ccc(Cl)nc1*]

wherein the broken bond with * is attached to —CO— of —NH—CO—. In certain embodiments, $L^4$ is

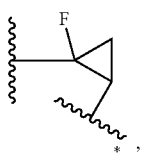

wherein the broken bond with * is attached to —CO— of —NH—CO—.

In certain embodiments of Formula (Iu-2), m3 is 1; n is 0 or 2; q is 1 or 2; and $L^4$ is

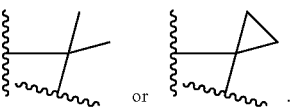

In certain embodiments, $L^4$ is

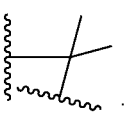

In certain embodiments, $L^4$ is

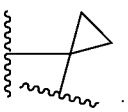

In certain embodiments of any one of Formulas (Iu), (Iu-1), or (Iu-2), at least one Z is —NH$_2$.

In certain embodiments of any one of Formulas (Iu), (Iu-1), or (Iu-2), $R^1$ is hydrogen.

In certain embodiments of any one of Formulas (Iu), (Iu-1), or (Iu-2), $R^2$ is hydrogen. In certain embodiments of any one of Formulas (Iu), (Iu-1), or (Iu-2), $R^2$ is fluoro. In certain embodiments of any one of Formulas (Iu), (Iu-1), or (Iu-2), $R^2$ is —OCH$_3$.

In certain embodiments of any one of Formulas (Iu), (Iu-1), or (Iu-2), $R^{3a}$ is —CH$_3$. In certain embodiments of any one of Formulas (Iu), (Iu-1), or (Iu-2), wherein $R^{3a}$ is cyclopropyl.

In certain embodiments of any one of Formulas (Iu), (Iu-1), or (Iu-2), $L^4$ is $C_{1-6}$ alkylene, optionally substituted with 1 to 3 substituents selected from the group consisting of halo, and pyridyl optionally substituted with 1-2 halo.

In certain embodiments, $R^{16}$ is

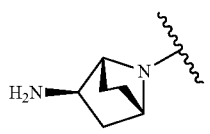

In certain embodiments, $R^{16}$ is

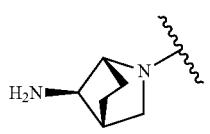

In certain embodiments, $R^{16}$ is

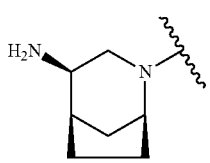

In certain embodiments, provided is a compound as shown in Table 1, or a pharmaceutically acceptable salt, stereoisomer, mixture of stereoisomers, or tautomer thereof. In certain embodiments, provided is a compound as shown in Table 1, or a pharmaceutically acceptable salt. In certain embodiments, provided is a compound as shown in Table 1.

In certain embodiments, provided is a compound as shown in Table 1A, or a pharmaceutically acceptable salt, stereoisomer, mixture of stereoisomers, or tautomer thereof. In certain embodiments, provided is a compound as shown in Table 1A, or a pharmaceutically acceptable salt. In certain embodiments, provided is a compound as shown in Table 1A.

One of skill in the art is aware that each and every embodiment of a group (e.g., $R^1$) disclosed herein may be combined with any other embodiment of each of the remaining groups (e.g., $R^{10}$, $R^{11}$, $Z^1$, $Z^8$, etc.) to generate a complete compound of Formula (I), or any Formula described herein or a pharmaceutically acceptable salt, stereoisomer, mixture of stereoisomers, or tautomer thereof, each of which is deemed within the ambit of the present disclosure.

Methods and Compositions

Peptidylarginine deiminase type 4 (PAD4) is hypothesized to be involved in an array of functions, including regulation of transcription, cell cycle, apoptosis, formation of neutrophil extracellular traps (NETs), and tumorgenesis. Expression of PAD4 is restricted to cells of the myeloid lineage, in particular: neutrophils, eosinophils and monocyte/macrophages.

The present disclosure provides compounds and compositions capable of inhibiting peptidylarginine deiminase type 4 (PAD4), and thus, the present disclosure provides a method for treating a disease or disorder mediated by peptidylarginine deiminase type 4 (PAD4), comprising administering an effective amount of a compound of Formula (I), or any formula described herein, or a pharmaceutically acceptable salt, stereoisomer, mixture of stereoisomers, or tautomer thereof, to a patient in need thereof.

As used herein, "treatment" or "treating" is an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and/or c) relieving the disease or condition, e.g., causing the regression of clinical symptoms, ameliorating the disease state, delaying the progression of the disease, increasing the quality of life, and/or prolonging survival.

As used herein, "delaying" development of a disease or condition means to defer, hinder, slow, retard, stabilize and/or postpone development of the disease or condition. This delay can be of varying lengths of time, depending on the history of the disease and/or subject being treated.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of disease are detectable in the subject.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease or to an amount that is effective to protect against the contracting or onset of a disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment outcome. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Patient" and "subject" refer to humans, domestic animals (e.g., dogs and cats), farm animals (e.g., cattle, horses, sheep, goats and pigs), laboratory animals (e.g., mice, rats, hamsters, guinea pigs, pigs, pocket pets, rabbits, dogs, and monkeys), and the like. In certain embodiments, the patient is a human.

Protein arginine deiminases (PADs) have been contemplated to display some level of substrate specificity possibly related to their tissue specific expression pattern. For example, keratins are physiological substrates of PAD1 and PAD3, myelin basic protein, enolase are citrullinated by PAD2, whereas histones and transcription factors are citrullinated by PAD4. In vitro, PADs are capable of citrullinating various substrates including intracellular and extracellular arginine containing proteins, peptides and peptide mimetics such as benzoyl arginine ethyl ester, used frequently in biochemical assays. Hydrolysis of peptidyl arginine to citrulline removes positive charge, and therefore may affect protein folding, stability, activity, and ability to form hydrogen bonds. Moreover, citrullinated proteins in susceptible individuals such as rheumatoid arthritis (RA) patients become neo-antigens and elicit an autoimmune response leading to the production of anti-citrullinated protein antibodies known as ACPA. The immunogenic property of citrullinated epitopes appears to be specific to RA, with ACPA detectable in 75% of RA patients and displaying 98% specificity for the disease. RA is a disabling autoimmune disease characterized by chronic inflammation of the joints and synovial tissues, pain and progressive bone destruction. ACPA may appear years prior to the onset of clinical RA and their presence correlates with disease prognosis. ACPA are regarded not only as a useful biomarker for RA diagnosis and for predicting a severe disease course, but they have also been postulated to contribute to a disease pathogenesis. Although the antigens recognized by ACPA are diverse and differ between RA patients, a number of common autoantigens have been reported: citrullinated forms of vimentin, enolase, fibrinogen, collagen II, and histones. PAD4 and also PAD2 are contemplated to be responsible for the generation of citrullinated neo-epitopes in RA as their expression is elevated in the inflamed synovium. Neutrophils and macrophages are the main source of these enzymes. Neutrophils are the most abundant white blood cells in circulation. As critical players in the early innate immune response, they hone quickly to sites of inflammation, are abundant in RA synovial fluid and have been shown to be involved in disease pathology. Neutrophils are also short-lived and may undergo inflammatory forms of cell death, including NETosis and necroptosis, which have been implicated in driving inflammation in the RA synovium. Several lines of evidence point to a putative role for citrullination and ACPAs in driving RA. Genetic (HLA-DR-SE risk allele) and environmental (smoking, periodontitis) factors linked to RA are intimately associated with citrullination and ACPAs. Multiple intracellular and extracellular citrullinated proteins (for example enolase, vimentin, fibrinogen, histones, actin, and collagen) are present in RA synovial tissues but absent in healthy or non-RA synovial tissue. Moreover, PADI4 polymorphisms are linked to RA susceptibility and have been identified in large GWAS studies. PAD4 itself is a target of an autoimmune response and 13-18% of RA patients develop anti-PAD4 antibodies; these auto-antibodies have been shown to activate PAD4 by modulating the enzyme's requirement for calcium and are associated with increased risk of progressive joint damage, interstitial lung disease, and poorer response to SOC.

Currently, it is not fully understood what drives excessive citrullination in RA, or even RA "at risk" individuals. It is contemplated that stimulation of synovial protein citrullination might be linked to the neutrophil cell death/lysis that can occur via one of several proinflammatory mechanisms. Moreover, it is hypothesized that citrullinated proteins are not only acting as neo-epitopes, but are involved directly in disease pathology. PAD4 is postulated to contribute to inflammatory processes in RA via the generation of ACPA neo-epitopes and formation of ACPA-immune complexes which could promote further citrullination, inflammation and pathology through engagement of Fc receptors. Aberrant protein citrullination might also modify the function of critical processes in the RA synovium, either independently or upon association of with cognate ACPAs. For example, it was demonstrated that osteoclast differentiation is linked to the citrullination of proteins and that some ACPAs were able to bind to osteoclast precursor cells promoting differentiation and activation in vitro and stimulation of IL-8 production. Moreover, infusion of some ACPAs into mice causes IL-8 dependent bone loss and IL-8 mediated pain behavior and exaggerate bone erosion in a methylate bovine serum albumin induced arthritis.

Therefore, PAD4 inhibitors should be explored as novel therapeutics for treatment of ACPA positive RA (over 75% of all RA patients) where disease could be exaggerated by citrullination and ACPA immune complexes and other types of RA. Animal studies with the use of knockout (KO) animals or PAD inhibitors provided additional rationale for the use of PAD4 inhibitors in treatment of RA. For example, in a chronic joint inflammation models such as collagen induced arthritis (CIA) or glucose-6 phosphate isomerase induced arthritis, PAD4 KO (DBA/1J) mice display improved clinical (around 60% reduction), histological scores, reduced antibody titer, and reduction of some pro inflammatory cytokines. Similarly, prophylactic treatment with pan-PAD covalent inhibitors such as chloroamidine and BB-chloroamidine or reversible PAD4-specific inhibitor GSK199 in a murine CIA model led to improvement of clinical and histological scores, reduction of antibodies titer and epitope spreading, reduction of citrullinated proteins in joints and shift from pro-inflammatory to pro-resolution immunological responses.

Beyond RA, activated PAD4 was also shown to be necessary and sufficient for citrullination of a histone H3 on neutrophil extracellular traps (NETs). Therefore, it is thought that PAD4 might be involved in a formation of NETs and citrullination of additional proteins associated with these structures. NETs are composed of chromatin and nuclear, cytoplasmic and granules proteins extruded from neutrophils during programmed cell death known as NETosis. NETosis is often regarded as a doubled-edged sword, because although it is a part of a normal antimicrobial defense, excessive NETs formation and/or defective NETs clearance induce inflammatory responses. NETosis results in a release of citrullinated proteins, granules' enzymes, antimicrobial proteins and DNA-protein complexes that can become neo-antigens and fuel autoimmunity in susceptible individuals. Moreover, active PADs are released during NETosis and can citrullinate cellular proteins associated with NETs and extracellular proteins in synovium or vasculature. NETs were also contemplated to serve as scaffolds for thrombosis. For that reason, NETosis has been postulated to exacerbate autoimmune and other inflammatory diseases with neutrophil infiltration. Thus, it was contemplated that targeting PAD4 may have therapeutic potential in diseases associated with sterile inflammation. PAD4 KO mice show improved outcome, protection from tissue and organs injury, deceased disease parameters and attenuation of NETosis markers in several murine models of acute or chronic injury such as stenosis model of deep vein thrombosis, myocardial ischemia/reperfusion, LPS endotoxemic shock and cecal ligation puncture (CLP) sepsis. Moreover, pan-PAD covalent inhibitors such as BB-chloroamidine, chloroamidine, or YW3-56 resulted in reduction of clinical, inflammatory, histopathological and mechanical end points, attenuation of NETosis and improved outcome in various models of chronic and acute inflammatory diseases including MRL/lpr mouse model of lupus, hemorrhagic shock in rats, mouse CLP sepsis model, mouse DSS-colitis, mouse ApoE$^{-/-}$ and high fat diet arteriosclerosis model, mouse streptozotocin induced diabetic wound healing model. Therefore, PAD4 inhibitors may have therapeutic potential in treatment of disease linked to pathological consequences of NETosis beyond RA, such as systemic lupus erythematous, antiphospholipid antibody syndrome, small vessels vasculitis, colitis, thrombosis, atherosclerosis, sepsis, diabetes, among others.

In certain embodiments, the disease or disorder mediated by peptidylarginine deiminase type 4 (PAD4) is acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis. Accordingly, provided is a method for treating acute lymphocytic leukemia, ankylosing spondylitis, cancer, chronic lymphocytic leukemia, colitis, lupus, systemic lupus erythematosus, cutaneous lupus erythematosus, rheumatoid arthritis, multiple sclerosis, or ulcerative colitis, comprising administering an effective amount of a compound of Formula (I), or any formula described herein, or a pharmaceutically acceptable salt, stereoisomer, mixture of stereoisomers, or tautomer thereof, to a patient in need thereof.

As PAD4 may contribute to the initiation and propagation of RA, PAD4 inhibitors can be envisioned as a prophylactic treatment for individuals that are at risk of developing clinical RA, as identified by ACPA positivity, family history of RA, exposure to environmental factors, genetic predisposition and presence of arthralgia.

In certain embodiments, the disease or disorder is inflammatory arthritis. In certain embodiments, the disease or disorder is rheumatoid arthritis. In certain embodiments, the disease or disorder is systemic lupus. In certain embodiments, the disease or disorder is vasculitis. In certain embodiments, the disease or disorder is cutaneous lupus erythematosus. In certain embodiments, the disease or disorder is psoriasis. In certain embodiments, the disease or disorder is a fibrotic lung disease, such as idiopathic pulmonary fibrosis (IPF). In certain embodiments, the disease or disorder is fibroproliferative lung disease. In certain embodiments, the disease or disorder is rheumatoid arthritis with joint and/or lung disease. In certain embodiments, the disease or disorder is inflammatory bowel disease.

In certain embodiments, the disease or disorder is acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotrophic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Behcet's disease, Behcet's syndrome, Bells Palsy, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, Crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, fibrotic lung disease, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis *nodosa*, polychondritis, polycystic kidney disease, polymyositis, psoriasis, psoriasis, psoriasis, psoriasis, psychosocial stress diseases, pulmonary disease, pulmonary hypertension, pulmonary fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid haemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjögren's syndrome, antineutrophil cytoplasmic antibody (ANCA)-associated Alzheimer's, scleroderma or CREST syndrome.

In certain embodiments, the disease or disorder is one or more of anti-neutrophil cytoplasm antibodies (ANCA) vasculitis, antiphospholipid syndrome, psoriasis, lung inflammatory diseases, interstitial lung disease (ILD), idiopathic pulmonary fibrosis (IPF), acute lung injury (ALI), acute respiratory distress syndrome (ARDS), chronic obstructive pulmonary disease (COPD), cystic fibrosis (CF), and COVID 19 ARDS.

In certain embodiments, the disease or disorder is one or more of rheumatoid arthritis, systemic lupus erythematosus, multiple sclerosis, or cancer.

Also provided is a pharmaceutical composition comprising a compound of Formula (I)-(Iv) or shown in Tables 1 and 1A, or any formula described herein, or a pharmaceutically acceptable salt, stereoisomer, mixture of stereoisomers, or tautomer thereof, and a pharmaceutically acceptable carrier or excipient.

The pharmaceutical compositions of compounds of Formula (I)-(Iv) may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

In some embodiments, the compounds or pharmaceutical compositions disclosed herein exhibit high inhibitory potency for PAD4 in a whole blood assay.

In one aspect, the compounds described herein may be administered orally. Oral administration may be via, for example, capsule or enteric coated tablets. In making the pharmaceutical compositions that include at least one compound of Formula (I)-(Iv) or shown in Tables 1 and 1A, or a pharmaceutically acceptable salt, is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions may, in some embodiments, be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, for oral administration, each dosage unit contains from about 10 mg to about 1000 mg of a compound described herein, for example from about 50 mg to about 500 mg, for example about 50 mg, about 75 mg, about 100 mg, about 150 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg. In other embodiments, for parenteral administration, each dosage unit contains from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual subject, and the severity of the subject's symptoms.

In certain embodiments, dosage levels of the compound of Formula (I)-(Iv) or shown in Tables 1 and 1A may be from 0.1 mg to 100 mg per kilogram of body weight per day, for example from about 1 mg to about 50 mg per kilogram, for example from about 5 mg to about 30 mg per kilogram. Such dosage levels may, in certain instances, be useful in the treatment of the above-indicated conditions. In other embodiments, dosage levels may be from about 10 mg to about 2000 mg per subject per day. The amount of active ingredient that may be combined with the vehicle to produce a single dosage form will vary depending upon the host treated and the particular mode of administration. Dosage unit forms may contain from 1 mg to 1000 mg of an active ingredient.

The compounds disclosed herein, or a pharmaceutically acceptable salt thereof, may be administered to a subject in accordance with an effective dosing regimen for a desired period of time or duration, such as at least about one day, at least about one week, at least about one month, at least about 2 months, at least about 3 months, at least about 4 months, at least about 6 months, or at least about 12 months or longer. In one variation, the compound is administered on a daily or intermittent schedule. In one variation, the compound is administered on a monthly schedule. In one variation, the compound is administered every two months. In one variation, the compound is administered every three months. In one variation, the compound is administered every four months. In one variation, the compound is administered every five months. In one variation, the compound is administered every 6 months.

The dosage or dosing frequency of a compound disclosed herein, or a pharmaceutically acceptable salt thereof, may be adjusted over the course of the treatment, based on the judgment of the administering physician. The compound may be administered to a subject (e.g., a human) in an effective amount. In certain embodiments, the compound is administered once daily.

For preparing solid compositions such as tablets, the principal active ingredient may be mixed with a pharmaceutical excipient to form a solid preformulation composition containing a homogeneous mixture of a compound of Formula (I), or a pharmaceutically acceptable salt, thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

In certain embodiments, a method of treating or preventing rheumatoid arthritis (RA) comprising administering a therapeutically effective amount of a compound disclosed herein, or a pharmaceutically acceptable salt thereof, to a subject in need thereof, is provided. In certain embodiments, a method of treating RA comprising administering a therapeutically effective amount of a compound disclosed herein, or a pharmaceutically acceptable salt thereof, to a subject in need thereof, is provided. In certain embodiments, the method comprises administering a compound disclosed herein, or a pharmaceutically acceptable salt thereof, in combination with one, two, three, or four additional therapeutic agents. In certain embodiments, the subject may have not previously received prior treatment (treatment naïve) for RA. In certain embodiments, the subject may have previously received treatment (treatment experienced) for RA.

In certain embodiments, a compound disclosed herein, or a pharmaceutically acceptable salt thereof for use in the manufacture of a medicament for treating RA in a subject (e.g., a human) is disclosed.

Also disclosed herein is a compound disclosed herein, or a pharmaceutically acceptable salt thereof, for use in the therapeutic treatment or delaying the onset of RA.

Also disclosed herein is a compound disclosed herein, or a pharmaceutically acceptable salt thereof, for use in the therapeutic treatment of RA.

In certain embodiments, a compound disclosed herein, or a pharmaceutically acceptable salt thereof can be used as a research tool (e.g., to study the inhibition of PAD4 in a subject or in vitro).

Kits that include a compound of Formula (I)-(Iv) or shown in Tables 1 and 1A, or a pharmaceutically acceptable salt, thereof, and suitable packaging are provided. In one embodiment, a kit further includes instructions for use. In one aspect, a kit includes a compound of Formula (I)-(Iv) or shown in Tables 1 and 1A, or a pharmaceutically acceptable salt thereof, and instructions for use of the compounds in the treatment of the diseases or conditions described herein.

Articles of manufacture that include a compound of Formula (I)-(Iv), or a pharmaceutically acceptable salt thereof, in a suitable container are provided. The container may be a vial, jar, ampoule, preloaded syringe, and intravenous bag.

Combination Therapy

In certain embodiments, a compound disclosed herein is administered with one or more additional therapeutic agents. In one embodiment, the present disclosure provides a pharmaceutical composition comprising a compound of Formula (I), or any formula described herein, or a pharmaceutically acceptable salt, stereoisomer, mixture of stereoisomers, or tautomer thereof, and at least one additional therapeutic agent and at least one pharmaceutically acceptable carrier or excipient.

In one embodiment, the present disclosure provides a pharmaceutical composition comprising a compound of Formula (I), or any formula described herein, or a pharmaceutically acceptable salt, stereoisomer, mixture of stereoisomers, or tautomer thereof, at least one additional therapeutic agent suitable for treating rheumatoid arthritis, and at least one pharmaceutically acceptable carrier or excipient.

Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the patient. When administered sequentially, the combination may be administered in two or more administrations.

Co-administration includes administration of unit dosages of the compounds disclosed herein before or after administration of unit dosages of one or more additional therapeutic agents. For example, the compound disclosed herein may be administered within seconds, minutes, or hours of the administration of the one or more additional therapeutic agents. In some embodiments, a unit dose of a compound disclosed herein is administered first, followed within seconds or minutes by administration of a unit dose of one or more additional therapeutic agents. Alternatively, a unit dose of one or more additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one or more additional therapeutic agents. In yet other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments, a compound of Formula (I)-(Iv) or shown in Tables 1 and 1A is formulated as a tablet, which may optionally contain one or more other compounds useful for treating the target indication. In certain embodiments, such tablets are suitable for once daily dosing. In other embodiments, the tablets are suitable for twice a day dosing.

Combination Drugs

In one embodiment, a compound as disclosed herein, such as a compound of Formula (I)-(Iv) or shown in Tables 1 and 1A, may be combined with one or more other active agents.

For example, in certain embodiments, a compound as disclosed herein, such as a compound of Formula (I)-(Iv) or shown in Tables 1 and 1A, may be used in combination with conventional synthetic and targeted synthetic disease-modifying antirheumatic drugs (DMARDs) or biological DMARDs due to orthogonal or complementary mechanisms of action.

The one or more active agents may be chosen from 14-3-3 protein eta inhibitors, 5-Lipoxygenase inhibitors, Abl tyrosine kinase inhibitors, ACTH receptor agonists, Adenosine A3 receptor agonists, adenosine deaminase inhibitors, ADP ribosyl cyclase-1 inhibitors, ADP ribosyl cyclase-1 modulators, ADP ribosylation factor 6 inhibitors, Adrenocorticotrophic hormone ligands, Aggrecanase-2 inhibitors, Albumin modulators, API transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, branched amino acid aminotransferase 1 inhibitors, Bromodomain containing protein inhibitors, BTK tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD 126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement C5 factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABA A receptor modulators, glucocorticoid agonists, Glucocorticoid antagonists, Glucocorticoid induced leucine zipper stimulators, GM-CSF ligand inhibitors, GM-CSF receptor antagonists, GM-CSF receptor modulators, growth regulated protein alpha ligand inhibitors, H+ K+ ATPase inhibitors, histamine H4 receptor antagonists, histone deacetylase inhibitors, histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-8 ligand inhibitors, IL-2 agonists, IL-2 antagonists, IL-21 antagonists, IL-23 antagonists, IL-3 antagonists, IL-4 agonists, IL-6 antagonists, IL-6 receptor modulators, IL-6 neutralizing human antibodies, anti-IL6 antibody, immunoglobulin antagonists, immunoglobulin G1 agonists, immunoglobulin G1 antagonists, Immunoglobulin G1 modulators, Immunoglobulin G2 antagonists, immunoglobulin G2 modulators, immunoglobulin gamma Fc receptor II modulators, immunoglobulin gamma Fc receptor IIB antagonists, immunoglobulin kappa modulators, immunoglobulin M antagonists, inducible nitric oxide synthase inhibitors, Inosine monophosphate dehydrogenase inhibitors, insulin sensitizers, integrin alpha-1/beta-1 antagonists, integrin alpha-4/beta-1 antagonists, integrin alpha-9 antagonist, integrin antagonists, interferon beta ligands, interferon gamma ligands, interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, Kelch like ECH associated protein 1 modulators, Kit tyrosine kinase inhibitors, LanC like protein 2 modulators, Leukotriene BLT receptor antagonist, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, methylprednisolone, Midkine ligand inhibitors, Mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, peptidylarginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type IIL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, or Zap70 tyrosine kinase inhibitors.

Examples of active agents that may be combined with the compounds described herein include 99mTc labelled annexin V-128, abatacept, abatacept biosimilar, ABBV-257, ABT-122, ABT-494, acalabrutinib, aceclofenac, actarit, AdMSCs, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, CR-6086, CreaVax-RA, CWG-92, CWG-940, Cx-611, DE-098, DEN-181, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), IB-RA (oral, rheumatoid arthritis), ICP-022, iguratimod, IMD-2560, imidazole salicylate, infliximab, infliximab biobetter, infliximab biosimilar, CT-P13, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen+omeprazole, leflunomide, lenzilumab, LLDT-8, LNP-1955, lumiracoxib, LY-3090106, masitinib, mavrilimumab, MBS-2320, MEDI-5117, meloxicam, methotrexate, MGD-010, misoprostol+diclofenac, MM-A01-01, monalizumab, MORAb-022, MPC-300-IV, MRC-375, nabumetone, namilumab, naproxen+esomeprazole, naproxen+esomeprazole strontium, ocaratuzumab, ofatumumab, OHR-118, olokizumab, OM-89, once-daily naproxen (oral controlled release, pain), ONO-4059, Oralgam, ozoralizumab, peficitinib, pelubiprofen, PF-06687234, piperidone hydrochloridum, piroxicam, prednisolone, prednisone, Procell, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), RA-Curcusome, recombinant human interleukin-1 receptor antagonist (rheumatoid arthritis), recombinant human interleukin-2 recombinant TNF receptor 2-Fc fusion protein mutant, RG-6125, RhuDex, rifabutin+clarithromycin+clofazimine, rituximab, rituximab biosimilar, Toritz, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), technetium Tc 99m tilmanocept, technetium[99Tc] methylenediphosphonate, tenoxicam, Debio-0512, tocilizumab, tofacitinib, tofacitinib citrate, *Trichuris suis* ova, umbilical cord-derived mesenchymal stem cells (iv, RA/liver disease), ustekinumab, VAY-736, VB-201, WF-10, XmAb-5871, YHB-1411-2, or YRA-1909.

In certain embodiments, a compound described herein may be combined with a 14-3-3 protein eta inhibitor, such as anti-AGX-020 mAbs (rheumatoid arthritis) or Augurex; a 5-Lipoxygenase inhibitor, such as darbufelone, tebufelone, ZD-2138, etalocib, PGV-20229, L-708780, T-0757, T-0799, ZM-216800, L-699333, BU-4601A, or SKF-104351; a 5-Lipoxygenase/Cyclooxygenase inhibitor, such as tenoxicam, licofelone, tenidap, tepoxalin, flobufen, SKF-86002, WY-28342, or CI-986; or a 5-Lipoxygenase/PPAR gamma agonist, such as etalocib; a Abl tyrosine kinase inhibitor/Bcr protein inhibitor/Kit tyrosine kinase inhibitor/PDGF receptor antagonist/or Signal transduction inhibitors, such as imatinib; a ACTH receptor agonist/Adrenocorticotrophic hormone ligand/Opioid growth factor receptor agonist, such as FAR-404, or metenkefalin acetate+tridecactide acetate; an adenosine A3 receptor agonist, such as CF-101 (piclidenoson); an adenosine deaminase inhibitor, such as cladribine, pentostatin, or FR-221647; a ADP ribosyl cyclase-1 inhibitor, such as daratumumab; a ADP ribosyl cyclase-1 modulator/Syndecan-1 inhibitor, such as indatuximab ravtansine; a ADP ribosylation factor 6 inhibitor, such as NAV-2729; a adrenocorticotrophic hormone ligand, such as corticotropin or Mallinckrodt; aggrecanase-2/TNF gene inhibitors, such as GIBH-R-001-2; albumin modulators, such as ONS-1210; albumin modulators/IL-6 antagonists, such as ALX-0061 (vobarilizumab); albumin modulators/TNF alpha ligand inhibitors, such as HOT-3010; a API transcription factor/Nuclear factor kappa B inhibitor, such astarenflurbil or SP-100030; anti-TNF steroid antibody-drug conjugates (anti-TNF-GRM), such as ABBV-3373; Basigin inhibitors/Branched amino acid aminotransferase l/Metalloprotease-9 inhibitors/Metalloprotease-2 inhibitors, such as ERG-240; BET inhibitors such as GSK-3358699; Bispecic anti-CD86/IL-10, such as APVO-210; bispecific humanized monoclonal antibody targeted against BAFF and IL-17A, such as tibulizumab; bispecific antibody-peptide conjugate (BAFF/ICOSL), such as AMG-570; B-lymphocyte antigen CD19 inhibitors, such as MDX-1342; B-lymphocyte antigen CD19 inhibitors/Immunoglobulin gamma Fc receptor IIB antagonists, such as XmAb-5871; B-lymphocyte antigen CD20 inhibitors, such as ocrelizumab, ofatumumab, rituximab, ABP-798, Maball, Mabtas, Reditux, Zytux, veltuzumab, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101, or JHL-1101; B-lymphocyte antigen CD20 modulators, such as SBI-087, TRU-015, DXL-625, or MabionCD20; B-lymphocyte stimulator ligand inhibitors, such as belimumab, RCT-18, blisibimod, tabalumab, or briobacept; B-lymphocyte stimulator ligand/Tumor necrosis factor ligand 13 inhibitors, such as atacicept; bradykinin receptor modulators/Histone deacetylase inhibitors/P2X7 purinoceptor agonists, such asgivinostat; BRAF gene/MEK protein kinase/PERK gene inhibitors, such as binimetinib; Bromodomain containing protein inhibitors, such as RVX-297 or ZEN-003694; Btk tyrosine kinase inhibitors, such as AC-0058, acalabrutinib, HM-71224, spebrutinib, BMS-986142, TAK-020, tirabrutinib (ONO-4059), TAS-5315, ABBV-105, GDC-0834, EBI-1459, BMS-986195, evobrutinib, or fenebrutinib; Btk tyrosine kinase inhibitors/Syk tyrosine kinase inhibitors/VEGF-2 receptor antagonists, such as CG-026806; Btk tyrosine kinase inhibitors/IL-6 antagonists, such as RN-486; Btk tyrosine kinase/Jak1 tyrosine kinase inhibitors, such as upadacitinib+ABBV-105; Btk tyrosine kinase/Jak3 tyrosine kinase inhibitors, such as AC-0025; cadherin-11 antagonists, such as RG-6125; calcineurin inhibitors, such as ciclosporin; calcineurin inhibitors/opioid receptor delta antagonists, such as HS-378; calcium channel inhibitors, such as RP-3128; carbonic anhydrase/Cyclooxygenase 2 inhibitors, such as polmacoxib; cathepsin K inhibitors, such as CRA-013783 or VEL-0230; cathepsin K/cathepsin S inhibitors, such as AM-3876 or NPI-2019; cathepsin S inhibitors, such as MIV-247 or RWJ-445380; CCR1 chemokine antagonists, such as BX-471, BMS-817399, BI-638683, CCX-354, MLN-3701, MLN-3897, CP-481715 or PS-375179; CCR2 chemokine antagonists, such as MK-0812 or AZD-6942; CCR3 gene modulators/Eotaxin 2 ligand inhibitors, such as CM-102; CCR5 chemokine antagonists, such as OHR-118, NIBR-6465, AZD-5672, or AZD-8566; CD29 modulators/Interleukin-10 ligands, such as PF-06687234; CD3 modulators, such as otelixizumab; CD39/CD73 agonists, such as AAV5-CD39/CD73 (rheumatoid arthritis), or Arthrogen; CCR5 chemokine antagonists/CD4 agonists/HIV-1 gp120 protein inhibitors, such as maraviroc; CD4 antagonists, such as zanolimumab, MTRX-1011A, BW-4162W94, EP-1645, or clenoliximab; CD40 ligand inhibitors, such as dapirolizumab pegol; CD40 ligand receptor antagonists, such as BI-655064, anti-CD40-XTEN, teneliximab, VIB-4920, or iscalimab; CD40 ligand receptor modulators/Immunoglobulin G1 modulators, such as CFZ-533; CD52 antagonists/Clusterin stimulators, such as alemtuzumab; bispecific CD32B/CD79B antibody, such as PRV-3279 (MGD-010); CD80 antagonists, such as abatacept biobetter; CD80 antagonists/T cell surface glycoprotein CD28 inhibitors, such as RhuDex; CD80 antagonists/CD86 antagonists, such as XENP-9523 or ASP-2408; CD86 antagonists, such as abatacept or biosuperior; CD86 antagonists/Cytotoxic T-lymphocyte protein-4 modulators, such as ES-210; CD95 antagonists, such as DE-098 or CS-9507; cell adhesion molecule inhibitors, such as alicaforsen, NPC-17923, TK-280 and PD-144795; chemokine receptor antagonists, such as PF-06835375; complement C5 factor inhibitors, such as eculizumab; complement C5 factor inhibitors/IL-1 antagonists, such as antisense oligonucleotides (rheumatoid arthritis); Leiden University Medical CenterComplement Factor stimulators, such as CM-101; C-reactive protein inhibitors, such as ISIS-353512; C-reactive protein inhibitors/Cyclooxygenase 2 inhibitors/Nuclear factor kappa B inhibitors/Immunoglobulin M antagonists/IL-2 receptor antagonists/PGE2 antagonists, such as IB-RACSF-1 antagonists: masitinib, FPA-008, JNJ-27301937, JNJ-40346527, PLX-5622, CT-1578, PD-360324, or JNJ-28312141; CSF-1 antagonists/Fyn tyrosine kinase inhibitors/Kit tyrosine kinase inhibitors/Lyn tyrosine kinase inhibitors/NK cell receptor modulators/PDGF receptor antagonists, such as masitinib; CXC10 chemokine ligand inhibitors, such as 946414-98-8 or BMS-936557; CXCR4 chemokine antagonists, such as plerixafor; CDK-2/7/9 inhibitors/MCL1 gene inhibitors, such as seliciclib; CDK-1/2/5/7/9 inhibitors, such as BP-14; cyclooxygenase 2 inhibitors, such as celecoxib, etoricoxib, meloxicam, or lumiracoxib; cyclooxygenase 2/Oxidoreductase inhibitors, such as etodolac; cyclooxygenase 2 modulators, such as DRGT-46; cyclooxygenase inhibitors, such as aceclofenac, diclofenac, naproxcinod, naproxen etemesil, nabumetone, Aleve, pelubiprofen, LY-210073, NS-398, bromfenac, L-746483, LY-255283, ibuprofen, flurbiprofen, SC-57666, or bermoprofen; cyclooxygenase inhibitors/H+ K+ ATPase inhibitors, such as naproxen+esomeprazole strontium; cyclooxygenase inhibitors/PGE1 agonists, such as misoprostol+diclofenac; cyclooxygenase inhibitors/Oxidoreductase inhibitors, such as imidazole salicylate; cytosolic phospholipase A2 inhibitors/Phospholipase A2 inhibitors, such as AVX-002; cytotoxic T-lymphocyte protein-4 stimulators/T cell surface glycoprotein CD28 inhibitors, such as abatacept, (BMS-188667) or belatacept; DHFR inhibitors, such as MPI-2505, Jylamvo, or ZeNEO-Methotrexate; DHFR inhibitors/Folate antagonists/Transferrin modulators, such as methotrexate; Diamine acetyltransferase inhibitors, such as diminazene aceturate; dihydroorotate dehydrogenase inhibitors, such as ASLAN-003, HWA-486, or ABR-224050; dihydroorotate dehydrogenase/Protein tyrosine kinase inhibitors, such as leflunomide; elongation factor 2 inhibitors/interleukin-2 ligands/NAD ADP ribosyltransferase stimulators, such as denileukin diftitox; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators/mTOR inhibitors, such as temsirolimus; folate antagonists/Transferrin modulators/DHFR inhibitors, such as MBP-Y003; folate receptor modulators, such as technetium (99mTc) etarfolatide; fractalkine ligand inhibitors, such as E-6011; Fyn tyrosine kinase inhibitors/GABA A receptor modulators/Cyclooxygenase 2 inhibitors/Dihydroorotate dehydrogenase inhibitors, such as laflunimus; Glucocorticoid agonists, such as prednisone, prednisolone, or fosdagrocorat; Glucocorticoid antagonists, such as REC-200; Glucocorticoid induced leucine zipper stimulators, such as ART-G01; GM-CSF ligand inhibitors, such as namilumab, gimsilumab (MORAb-022), or TJM-2; GM-CSF receptor antagonists, such as mavrilimumab; GM-CSF receptor modulators, such as GSK-3196165 or otilimab; growth regulated protein alpha ligand inhibitors/AP1 transcription factor; inhibitors/IF-6 antagonists/Interleukin-1 beta ligand inhibitors/Cathepsin K inhibitors/NFAT gene inhibitors, such as T-5224; H+K+ATPase inhibitors, such as naproxen+esomeprazole, ketoprofen+omeprazole, KEO-25001, HC-1004, or PN-40020; histamine H4 receptor antagonists, such as toreforant or GD-48; histone deacetylase inhibitors, such as CHR-5154 (GSK-3117391); histone deacetylase-6 inhibitors, such as CKD-506; HFA class II antigen DQ-2 alpha modulators, such as NexVax2; HFA class II antigen inhibitors, such as HFA-DR1/DR4 inhibitors (rheumatoid arthritis) or Provid; HFA class II antigen modulators, such as recombinant T-cell receptor ligand (rheumatoid arthritis) or Artielle; Hsp 70 family inhibitors, such as gusperimus trihydrochloride; hypoxia inducible factor-1 inhibitors/VEGF receptor antagonists, such as 2-methoxyestradiol; IFNB gene stimulators, such as ART-102; I-kappa B kinase beta inhibitors, such as IMD-2560; I-kappa B kinase beta inhibitors/Nuclear factor kappa B inhibitors, such as IMD-0560; I-kappa B kinase inhibitors/NFE2F2 gene stimulators/Nuclear factor kappa B inhibitors/STAT3 gene inhibitors, such as bardoxolone methyl; IF-1 antagonists, such as recombinant human interleukin-1 receptor antagonist (rheumatoid arthritis), Shanghai Fudan-Zhangjiang Bio-Pharmaceutical; IF-1 antagonists/Interleukin-1 beta ligand inhibitors, such as rilonacept; IF-10 agonists, such as pegilodecakin; IF-11 agonists/PDGF receptor agonists, such as oprelvekin; IF-12 antagonists/IF-23 antagonists, such as ustekinumab or briakinumab; IF-15 antagonists, such as AMG-714; IF-17 antagonists, such as ixekizumab or secukinumab; IF-17 receptor modulators, such as CNTO-6785; IF-2 receptor agonists, such as interleukin-2 follow-on biologic (IF-2), Anteluke or Interking; IF-2/IF-21/IF-15 antagonists, such as BNZ-132-2; IL-21 antagonists, such as NN-8828; IL-4 agonists, such as SER-130-AMI; IL-6 antagonists, such as BCD-089, olokizumab, clazakizumab, sirukumab, SA-237,FB-704A, OP-R003, peptide IL-6 antagonist, MEDI-5117, AMG-220, FM-101, BLX-1025, esonarimod, TA-383, or sarilumab; IL-6 antagonists/Interleukin-1 beta ligand inhibitors/TNF alpha ligand inhibitors, such as K-832; IL-6 antagonists/Insulin sensitizers/Interleukin-1 beta ligand inhibitors, such as BLX-1002; IL-6 receptor antagonists/modulators, such as tocilizumab, HS-628, or LusiNEX; IL-6 receptor modulators, such as BAT-1806 or RO-4877533; immunoglobulin antagonists, such as iguratimod; immunoglobulin G1 agonists, such as BX-2922 and HF-1020; immunoglobulin G1 agonists/Interleukin-1 beta ligand inhibitors, such as canakinumab; immunoglobulin G1 agonists/TNF alpha ligand inhibitors, such as STI-002; immunoglobulin G1 antagonists/TNF alpha ligand inhibitors, such as YHB-1411-2; immunoglobulin G1 modulators/GM-CSF ligand inhibitors/immunoglobulin kappa modulators, such as lenzilumab; immunoglobulin G2 antagonists/NF kappa B inhibitor stimulators/Osteoclast differentiation factor antagonists/Osteoclast differentiation factor ligand inhibitors/TNFSF11 gene inhibitors, such as denosumab; immunoglobulin gamma Fc receptor II modulators, such as MGD-010; inducible nitric oxide synthase inhibitors/Cyclooxygenase 2 inhibitors/MAP kinase modulators/Nuclear factor kappa B inhibitors, such as SKLB-023; inosine monophosphate dehydrogenase inhibitors, such as mizoribine; insulin sensitizers/Nuclear factor kappa B inhibitors/interleukin ligand inhibitors, such as HE-3286; integrin alpha-1/beta-1 antagonists, such as SAN-300; integrin alpha-4/beta-1 antagonists/cell adhesion molecule inhibitors, such as natalizumab; integrin alpha-9 antagonist, such as ASP-5094; integrin antagonists, such as PEG-HM-3 or CY-9652; interferon beta ligands, such as recombinant interferon beta-la; interferon beta ligands/IL-6 antagonists, such as TA-383; interferon gamma ligands, such as Li Zhu Yin De Fu or Clongamma; interleukin 17A ligand inhibitors/Tumor necrosis factor ligand inhibitors, such as ABT-122 or ABBV-257; interleukin 17F ligand inhibitors, such as bimekizumab; interleukin 18 ligand inhibitors, such as tadekinig alfa; interleukin 23A inhibitors, such as guselkumab; interleukin ligands/IL-1 antagonists, such as IBPB-007-IL; interleukin receptor 17A antagonists, such as brodalumab; interleukin-1 beta ligand inhibitors, such as gevokizumab, LY-2189102 or CDP-484; interleukin-1 beta ligand inhibitors/TNF alpha ligand inhibitors, such as PMI-001; interleukin-1 beta ligands/TNF alpha ligand modulators, such as PUR-0110; interleukin-2 ligands, such as recombinant interleukin-2; IL-2 modulators, such as AMG-592; interleukin-4 ligands/Tenascin modulators, such as Tetravil; interleukin-6 ligand inhibitors, such as gerilimzumab or PF-4236921; IRAK-4 protein kinase inhibitor, such as BAY-1830839, BAY-1834845, or PF-06650833; Itk tyrosine kinase inhibitors, such as JTE-051; Itk tyrosine kinase inhibitors/Jak3 tyrosine kinase inhibitors, such as ARN-4079; JAK tyrosine kinase inhibitors, such as deuterated tofacitinib analog or SD-900; JAK tyrosine kinase inhibitors/Syk tyrosine kinase inhibitors, such as cerdulatinib or CVXL-0074; Jak1 tyrosine kinase inhibitors, such as ABT-494 (upadacitinib), ruxolitinib, filgotinib, itacitinib, NIP-585, YJC-50018, GLPG-0555, MRK-12, or SHR-0302; Jak1/3 tyrosine kinase inhibitors, such as tofacitinib, tofacitinib citrate, peficitinib, CKD-374, or CS-944X; Jak1/2 tyrosine kinase inhibitors, such as baricitinib or ruxolitinib; Jak2 tyrosine kinase inhibitors/CSF-1 antagonists, such as CT-1578; JAK3 gene inhibitors, such as PF-06651600; Jak3 tyrosine kinase inhibitors, such as decemotinib, DNX-04042, MTF-003, or PS-020613; Jun N terminal kinase inhibitors, such as IQ-1S; KCNA voltage-gated potassium channel-3 modulators, such as MRAD-P1; Kelch like ECH associated protein 1 modulators/Nuclear erythroid 2-related factor 2 stimulators, such as dimethyl fumarate; FanC like protein 2 modulators, such as BT-11; FDF receptor related protein-1 stimulator, such as SP-16; Feukotriene BET receptor antagonists/complement C5 factor inhibitors, such as nomacopan; FITAF gene inhibitors/JAK3 gene inhibitors/MAP3K2 gene inhibitors/TNF antagonists, such as GBF-5b; Fymphocyte function antigen-3 receptor antagonists, such as alefacept; Macrophage mannose receptor 1 modulators, such as technetium Tc 99m tilmanocept; MAdCAM inhibitors/Immunoglobulin G2 modulators, such as PF-547659; MAPKAPK5 inhibitors/matrix metalloprotease inhibitors, such as GFPG-0259; MEK protein kinase inhibitors, such as AD-GF0001; Membrane copper amine oxidase inhibitors, such as BTT-1023, PRX-167700, or vepalimomab; Metalloprotease-9 inhibitors, such as GS-5745; Microbiome modulator, such as EDP-1815; Midkine ligand inhibitors, such as CAB-102; Mitochondrial 10 kDa heat shock protein stimulators, such as INV-103; mTOR inhibitors, such as everolimus; NAMPT gene inhibitors, such as ART-D01; Nicotinic acetylcholine receptor antagonists, such as RPI-78 or RPI-MN; NKG2 A B activating NK receptor antagonists, such as monalizumab; NKG2 D activating NK receptor antagonists, such as NNC-0142-002; Nuclear factor kappa B inhibitors, such as dehydroxymethylepoxyquinomicin, MP-42, VGX-1027,SP-650003, MG-132, SIM-916, VGX-350, VGX-300, GIT-027, MLN-1145, or NVP-IKK-005; Nuclear factor kappa B modulators/Nuclear factor kappa B p105 inhibitors/Transcription factor RelB inhibitors/Transcription factor p65 inhibitors, such as REM-1086; Osteoclast differentiation factor antagonists, such as cyclic peptidomimetics (rheumatoid arthritis/osteoporosis), University of Michigan; p38 MAP kinase alpha inhibitors, such as VX-745, BMS-582949, or BMS-751324; p38 MAP kinase inhibitors, such as BCT-197, losmapimod, or ARRY-797; PDE 4 inhibitors, such as apremilast; PDE 5 inhibitors, such as PDE5 inhibitors (rheumatoid arthritis), University of Rochester; PDGF-B ligand inhibitors/VEGF receptor antagonists, such as SL-1026; Phosphoinositide-3 kinase delta inhibitors, such as CT-732, INK-007 or GNE-293; Phosphoinositide-3 kinase delta/gamma inhibitors, such as duvelisib or RP-6503; Phospholipase A2 inhibitors, such as AK-106, varespladib methyl, Ro-31-4493, BM-162353, Ro-23-9358, or YM-26734; Platelet activating factor receptor antagonists, such as piperidone hydrochloridum; PPAR gamma agonists, such as rosiglitazone XR; PPAR gamma agonists/Insulin sensitizers, such as rosiglitazone; Programmed cell death protein 1 modulators, such as INSIX RA; Prostaglandin D synthase stimulators, such as HF-0220; Protein tyrosine kinase inhibitors, such as tairuimide; PurH purine biosynthesis protein inhibitors/Inosine monophosphate dehydrogenase inhibitors, such as mycophenolate mofetil; Rev protein modulators, such as ABX-464; RIP-1 kinase inhibitors, such as GSK-2982772; IL-17 antagonist/Rho associated protein kinase 2 inhibitor, such as KD-025; Signal transducer CD24 modulators, such as CD24-IgFc; Sodium glucose transporter-2 inhibitors/PPAR gamma agonists/Insulin sensitizers, such as THR-0921; STAT3 gene inhibitors, such as vidofludimus; STAT-3 inhibitors, such as HL-237; Superoxide dismutase stimulators, such as imisopasem manganese; SYK family tyrosine kinase inhibitors/Zap70 tyrosine kinase inhibitors, such as MK-8457; Syk tyrosine kinase inhibitors, such as fostamatinib, entospletinib, KDDF-201110-06, HMPL-523,AB-8779, GS-9876, PRT-2607, CG-103065, or SKI-O-703; T cell receptor antagonists, such as TCR inhibiting SCHOOL peptides (systemic/topical, rheumatoid arthritis/dermatitis/scleroderma), SignaBlok, CII modified peptide (rheumatoid arthritis), or Peking University; T cell receptor modulators/HLA class II antigen modulators, such as ARG-301; T cell surface glycoprotein CD28 stimulators, such as TAB-08 or theralizumab; TAK1 binding protein modulators, such as epigallocatechin 3-gallate; Talin modulators, such as short-form talin regulators (rheumatoid arthritis) or KayteeBio; T-cell differentiation antigen CD6 inhibitors, such as itolizumab; T-cell surface glycoprotein CD8 inhibitors/TGF beta agonists/CD4 antagonists, such as tregalizumab; Thymulin agonists, such as Syn-1002; TLR-2/TLR-4 antagonists, such as VB-201; TLR-4 antagonists, such as NI-0101; TLR-2/4/9 antagonists, such as P-13; TNF agonists/TNF antagonists/Type II TNF receptor modulators, such as Lifmior; TNF alpha ligand inhibitors, such as Adfrar, FKB-327, Exemptia, Cinnora, Mabura, adalimumab, infliximab, Flixabi, PF-06438179, hadlima, recombinant humanized anti-TNF-alpha monoclonal antibody, CMAB-008, CT-P13, GB-242, golimumab (CNTO-148), ozoralizumab, AT-132, ISIS-104838, ISU-202, CT-P17, MB-612, Debio-0512, anti-TNF alpha human monoclonal antibody, UB-721, KN-002, DA-3113, BX-2922, R-TPR-015, BOW-050, PF-06410293, CKD-760, CHS-1420, GS-071, ABP-710, BOW-015, HLX-03, BI-695501, MYL-1401A, ABP-501, BAX-2923, SCH-215596, ABT-D2E7, BAT-1406, XPro-1595, Atsttrin, SSS-07, golimumab biosimilar, TA-101, BLX-1002, ABX-0401, TAQ-588, TeHL-1, placulumab, CYT-007-TNFQb, SSR-150106, PassTNF, Verigen, DOM-0200, DOM-0215, AME-527, anti-TNF-alpha mAb, GENZ-38167, BEX-1028, CYT-020-TNFQb, CC-1080, CC-1069, LBAL, GP-2017, Idacio, IBI-303, or HS-016; TNF alpha ligand inhibitors/TNF antagonists/Type II TNF receptor modulators, such as BAX-2200; TNF alpha ligand inhibitors/Type II TNF receptor modulators, such as Eucept, TNF alpha ligand modulators, such as MM-A01-01, CDP-571, camobucol, or JNJ-63823539; TNF antagonists, such as DNX-114, TNF antagonist+IF-12 antagonist (rheumatoid arthritis), University of Oxford, BN-006, pegsunercept, ACE-772, onercept, DE-096, PN-0615, lenercept, ITF-1779, MDF-201112,HD-203, Qiangke, or TNF a Fc; TNF antagonists/Type II TNF receptor modulators, such as Altebrel, Intacept, QF-0902, etanercept, Erelzi, opinercept, YISAIPU, Anbainuo, Benepali, YFB-113, SCB-808, DA-3853, or SCB-131; TNF antagonists/TNF alpha ligand inhibitors, such as certolizumab pegol; TNF receptor modulators, such as recombinant TNF receptor 2-Fc fusion protein mutant or T-0001; TNF receptor modulators/TNF alpha ligand inhibitors, such as tgAAV-TNFR:Fc; tumor necrosis factor 13C receptor antagonists, such as VAY-736; tumor necrosis factor 15 ligand inhibitors, such as anti-TF1A antibodies (rheumatoid arthritis/inflammatory bowel disease), or NIAMS; Tumor necrosis factor ligand inhibitors, such as etanercept biosimilar; Type IIF-1 receptor antagonists, such as anakinra, IF-1 Ra, anakinra follow-on biologic or AXXO; Type I TNF receptor antagonists, such as NM-9405; Type II TNF receptor modulators, such as FBEC-0101, DMB-3853, DWP-422, or BT-D001; Unspecified GPCR agonists, such as NCP-70X; VEGF receptor antagonists, such as NSC-650853; VEGF-2 receptor modulators, such as VEGFR2 neutralizing antibody (rheumatoid arthritis), University of Rochester; VEGF-B ligand inhibitors, such as CSF-346; X-linked inhibitor of apoptosis protein inhibitors, such as IAP inhibitors (oral) or Pharmascience; or Zap70 tyrosine kinase inhibitors, such as CT-5332.

In one embodiment, the compound of Formula (I), or any formula described herein, or a pharmaceutically acceptable salt, stereoisomer, mixture of stereoisomers, or tautomer thereof, is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GFPG0634), gandotinib (FY2784544), INCB039110 (itacitinib), lestaurtinib, momelotinib (CYT0387), NS-018, pacritinib (SB 1518), peficitinib (ASP015K), ruxolitinib, tofacitinib (formerly tasocitinib), INCB052793, and XF019. In one embodiment, a compound as disclosed herein, such as a compound of Formula (I) or any formula described herein, or a pharmaceutically acceptable salt, stereoisomer, mixture of stereoisomers, or tautomer thereof, may be combined with filgotinib (GLPG0634).

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, or tautomer thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (e.g., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein. Protective groups can be added or removed at any appropriate stage in order to enable the syntheses described herein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The following is a list of abbreviations and acronyms used throughout the application:

| Abbreviation | Meaning |
|---|---|
| ° C. | Degree Celsius |
| ATP | Adenosine-5'-triphosphate |
| AcOH | Acetic acid |
| Boc | Tert-butyloxycarbonyl |
| Bn | Benzyl |
| Bs | Benzenesulfonyl |
| CDI | 1,1'-Carbonyldiimidazole |
| d | Doublet |
| Dba | Dibenzylideneacetone |
| DBU | 1,8-Diazabicyclo[5.4.0]undec-7-ene |
| dd | Doublet of doublets |
| DCE | 1,2-dichloroethane |
| DCM | Dichloromethane |
| DEAD | Diethyl azodicarboxylate |
| Dess-Martin periodinane | 1,1,1-Tris(acetyloxy)-1,1-dihydro-1,2-benziodoxol-3-(1H)-one |
| DIAD | Diisopropyl azodicarboxylate |
| DIPEA, DIEA | N,N-diisopropylethylamine |
| DMAP | 4-Dimethylaminopyridine |
| DME | 1,2-dimethoxyethane |
| DMF | Dimethylformamide |
| DMSO | Dimethylsulfoxide |
| DMPU | 1,3-dimethyl-3,4,5,6-tetrahydro-2(1H)-pyrimidinone |
| Dppf | 1,1'-Bis(diphenylphosphino)ferrocene |
| DPPA | Diphenylphosphoryl azide |
| EDC | 1-Ethyl-3-(3-dimethylaminopropyl)carbodiimide |
| EDTA | Ethylenediaminetetraacetic acid |
| EGTA | Ethylene glycol tetraacetic acid |
| EtOAc | Ethyl acetate |
| equiv/eq | Equivalents |
| ESI | Electrospray ionization |
| Ac | Acetate |
| Et | Ethyl |
| g | Grams |
| HATU | 2-(7-Aza-1H-Benzotriazole-1-yl)-1,1,3,3-tetramethyluronium hexafluorophosphate |
| HCl | Hydrochloric acid |
| hERG | human Ether-à-go-go Related Gene |
| HPLC | High-performance liquid chromatography |
| h/hr | Hours |
| Hunig's Base | N,N-diisopropylethylamine |
| Hz | Hertz |
| IC$_{50}$ | The half maximal inhibitory concentration |
| IPTG | Isopropyl β-d-1-thiogalactopyranoside |
| Ir[dF(CF$_3$)ppy]$_2$(dtbbpy)PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| J | Coupling constant |
| Jackiephos | 2-{Bis[3,5-bis(trifluoromethyl)phenyl]phosphino}-3,6-dimethoxy-2',4',6'-triisopropyl-1,1'-biphenyl |
| Jackiephos Pd G3 | [(2-{Bis[3,5-bis(trifluoromethyl)phenyl]phosphine}-3,6-dimethoxy-2',4',6'-triisopropyl-1,1'-biphenyl)-2-(2'-amino-1,1'-biphenyl)]palladium(II) methanesulfonate |
| kg | Kilogram |
| LC/MS, LCMS | Liquid chromatography mass spectrometry |
| LDA | Lithium diisopropylamide |
| LiHMDS | Lithium bis(trimethylsilyl)amide |

| Abbreviation | Meaning |
|---|---|
| L-selectride | Lithium tri-sec-butylborohydride solution |
| M | Molar |
| m | Multiplet |
| m/z | mass-to-charge ratio |
| M+ | Mass peak |
| M + H | Mass peak plus hydrogen |
| Me | Methyl |
| MeOH | Methyl alcohol/methanol |
| Mg | Milligram |
| MHz | Megahertz |
| min/m | Minute |
| ml/mL | Milliliter |
| mM | Millimolar |
| mmol | Millimole |
| MS | Mass spectroscopy |
| MTBE | Methyl tert-butyl ether |
| Mw | Microwave |
| N | Normal |
| Mol | Mole |
| NaHMDS | Sodium bis(trimethylsilyl)amide |
| NCS | N-chlorosuccinimide |
| NIS | N-iodosuccinimide |
| NMP | N-methylpyrrolidinone |
| NMR | Nuclear magnetic resonance |
| p | Pentuplet |
| PCR | Polymerase chain reaction |
| Ph | Phenyl |
| ppm | Parts per million |
| PPTS | Pyridinium para-toluenesulfonate |
| Prep | Preparative |
| Rf | Retention factor |
| RP | Reverse phase |
| RT/rt | Room temperature |
| s | Second |
| s | Singlet |
| SEM | Trimethylsilylethoxymethyl |
| SPhos | 2-Dicyclohexylphosphino-2',6'-dimethoxybiphenyl |
| SUMO | Small ubiquitin-like modifier |
| t | Triplet |
| TBAF | Tetrabutylammonium fluoride |
| TBAI | Tetrabutylammonium iodide |
| TBS | Tert-butyldimethylsilyl |
| TBDPS | Tert-butyldiphenylsilyl |
| TCEP | Tris(2-carboxyethyl)phosphine |
| TEA | Triethylamine |
| Tf | Trifluoromethylsulfonyl |
| TFA | Trifluoroacetic acid |
| THP | Tetrahydropyranyl |
| TLC | Thin layer chromatography |
| Trt/Trityl | Triphenylmethyl |
| TMS | Trimethylsilyl |
| Ts | Toluenesulfonyl |
| WT | Wild type |
| Xantphos | 4,5-Bis(diphenylphosphino)-9,9-dimethylxanthene |
| XPhos | 2-Dicyclohexylphosphino-2',4',6'-triisopropylbiphenyl |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |
| Zhan 1b | 1,3-Bis(2,4,6-trimethylphenyl)-4,5-dihydroimidazol-2-ylidene[2-(i-propoxy)-5-(N,N-dimethylaminosulfonyl)phenyl]methyleneruthenium (II) dichloride |
| δ | Chemical shift |
| µg | Microgram |
| µL/µl | Microliter |
| µM | Micromolar |
| µm | Micrometer |
| µmol | Micromole |

Compounds as provided herein may be synthesized according to the general schemes provided below. In the Schemes below, it should be appreciated that each of the compounds shown therein may have protecting groups as required present at any step. Standard protecting groups are well within the purview of one skilled in the art. Further, unless otherwise defined, the various substituents depicted in the following Schemes (e.g., $X^1$, $X^2$, $X^3$, $X^4$, $X^5$, $X^7$, $L^1_{m1}$, $L^2_{m2}$, $L^3_{m3}$, $L^4_{m4}$, $L^5_{m5}$, $L^6_{m6}$, $R^1$, $R^2$, $R^3$, $R^{10}$, $R^{11}$, etc.) are as defined in the embodiments and compounds disclosed herein. In certain Schemes, $L^1_{m1}$, $L^2_{m2}$, $L^3_{m3}$, $L^4_{m4}$, $L^5_{m5}$, and $L^6_{m6}$ are generalized using $L^n$ and $L^m$. It is to be understood that either of $L^n$ and $L^m$ can include any combination of $L^1_{m1}$, $L^2_{m2}$, $L^3_{m3}$, $L^4_{m4}$, $L^5_{m5}$, and $L^6_{m6}$, provided that upon closure of the macrocycle ring, the resulting compound can be defined by the $L^1_{m1}$, $L^2_{m2}$, $L^3_{m3}$, $L^4_{m4}$, $L^5_{m5}$, and $L^6_{m6}$ provided herein.

Scheme A shows an exemplary synthetic route for the synthesis of compounds provided herein (e.g., compounds of Formula (I)). In Scheme A, $X^1$, $X^2$, $X^3$, $X^4$, $X^5$, $X^7$, $L^1_{m1}$, $L^2_{m2}$, $L^3_{m3}$, $L^4_{m4}$, $L^5_{m5}$, $L^6_{m6}$, $R^1$, $R^{10}$, and $R^{11}$, are as defined herein, Pi is hydrogen or a suitable protecting group, Z is the moiety —$NR^{10}R^{11}$, or a suitable precurser thereto (e.g., —OH or —O-alkyl, and the like), and $R^{100}$ and $R^{101}$, X and Y are each, respectively, suitable complimentary functional groups capable of forming a covalent bond therebetween.

formation of compound A-102 as desired. Cyclization of compound A-102 provides compound A-103. Exemplary functional groups and methods for achieving cyclization, and well as other functional group modifications, are detailed in the Schemes and Procedures below.

In Scheme A, compound A-103, shown both generalized using $L^n$ and $L^m$, and specifically using $L^1_{m1}$, $L^2_{m2}$, $L^3_{m3}$, $L^4_{m4}$, $L^5_{m5}$, and $L^6_{m6}$, can be further modified to install the —$NR^{10}R^{11}$ moiety and thus provide compounds of Formula (I). In certain embodiments of compound A-100, A-102 or A-103, Z is —$NR^{10}R^{11}$. Thus, it can be understood that at any point in the synthesis prior to the formation of the macrocyclic ring, an intermediate can be modified to convert Scheme A

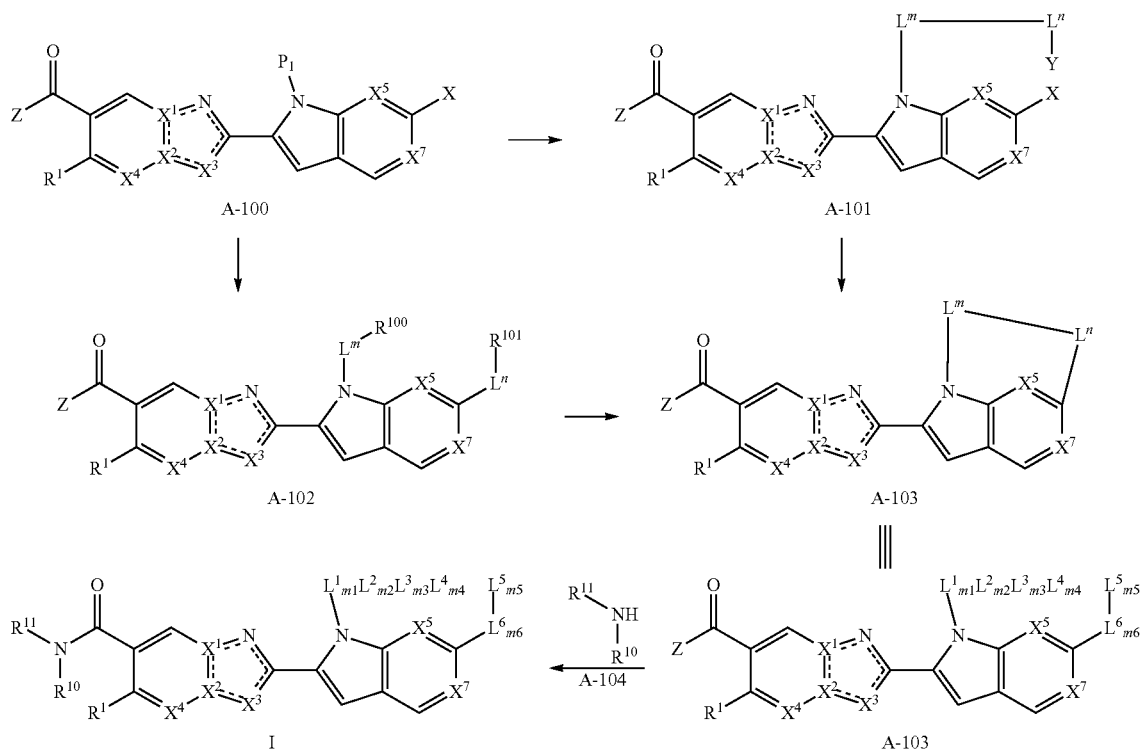

In Scheme A, a compound A-100 can first be deprotected as needed and then reacted with a compound of formula Y-$L^n$-$L^m$-LG, where LG is a leaving group (e.g., halo), under suitable conditions to provide compound A-101. Compound A-101 can then be converted to compound A-103 under suitable cyclization conditions. Alternatively, compound A-100 can be deprotected as needed and reacted with a compound of formula $R^{100}$-$L^m$-LG, where LG is a leaving group (e.g., halo), and then, when X comprises a nucleophilic functional group, a compound of formula $R^{101}$-$L^n$-LG, where LG is a leaving group (e.g., halo), or alternatively, when X is a leaving group (e.g., halo), a compound of formula $R^{101}$-$L^n$-M, to provide compound A-102, where M is a suitable cross coupling functional group, such as a boronic ester, acid, or trifluoroborate group, a zinc or magnesium halide species, or a trialkylstannane in the presence of a palladium catalyst. It should also be understood that the order in which the installation of the respective macrocyclic precursers (i.e., $R^{100}$-$L^m$- and $R^{101}$-$L^n$-) can be reversed, and/or the various groups can be further modified after the a Z group, where Z is suitable precurser (e.g., —OH or —O-alkyl, and the like), to Z is —$NR^{10}R^{11}$.

In certain embodiments, $R^{10}$ or $R^{11}$ may contain a protected amine substituent (e.g., —$NHP^1$, —$NP^1P^2$, or —$NR^{12}P^1$, where examples of $P^1$ and $P^2$ include -Boc, -Cbz, -trityl, or any other group known to be useful as an amine protective group). Additionally, $R^{11}$ may be a nitrogen-containing heterocycle wherein the ring nitrogen is protected with $P^1$, as defined above. In these cases, removal of $P^1$ and $P^2$ can be carried out using standard conditions, including TFA or HCl for -Boc or -trityl, and hydrogenolysis over a suitable catalyst (e.g., Pd/C) for -Cbz to afford amine products.

Where the individual steps do not provide a desired isomer (e.g., stereoisomer), resolution of the isomers of Formula (I), or any intermediate used in the preparation thereof, can be performed as needed using standard chiral separation/resolution conditions (e.g., chromatography, crystallization, etc.).

Suitably substituted compounds A-100, A-101, A-102, and A-103 for use in the methods provided herein can be purchased from commercial sources or synthesized by known methods, or according to methods described in the Schemes and Procedures detailed herein.

For example, Scheme B shows exemplary methods for the synthesis of compound of formula A-100 for use in Scheme A. In Scheme B, compound B-102 (i.e., compound A-100 where $X^1$ and $X^2$ are C and $X^3$ is N—$R^3$) can be prepared by contacting compound B-100 with compound B-101 under conditions sufficient to provide compound B-102. Further, compound B-105 (i.e., compound A-100 where $X^3$ is C—$R^3$) can be prepared by contacting compound B-103 with compound B-104 under conditions sufficient to provide compound B-105.

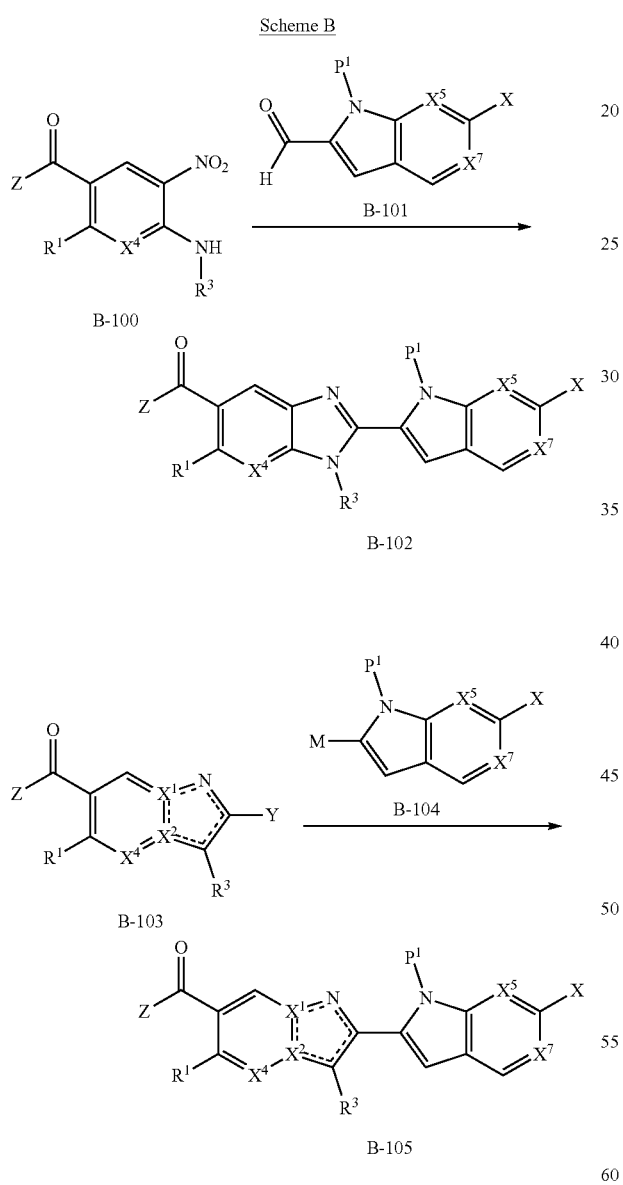

Suitably substituted compounds for use in Scheme B (i.e., compounds B-100, B-101, B-103, and B-104) can be purchased from commercial sources, synthesized by known methods, or synthesized according to the general Schemes detailed below, and/or the specific Procedures disclosed herein.

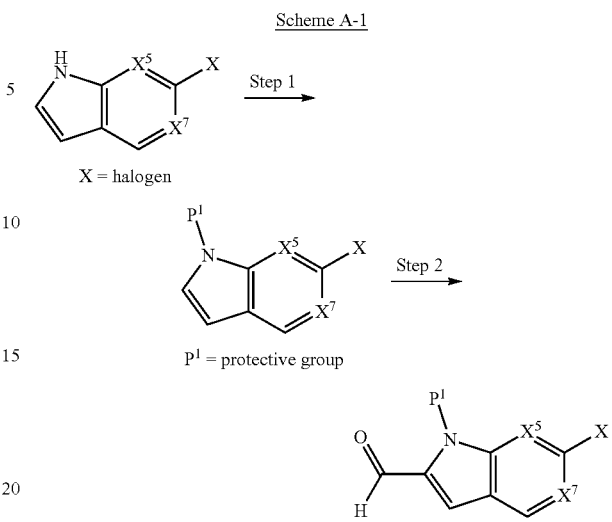

Scheme A-1 depicts the preparation of an indole or azaindole aldehyde intermediate that contains a halogen functional handle.

Step 1 describes the protection of a halogenated indole or aza-indole with $P^1$. Such protective groups can be installed using standard procedures, including treatment with SEM-Cl, $BOC_2O$, or benzenesulfonyl chloride in the presence of a suitable base (e.g., Hunig's base, $Et_3N$, NaH, NaHMDS, etc.) to provide $P^1$=SEM, $P^1$=Boc, and $P^1$=benzenesulfonyl, respectively.

Step 2 describes installation of a carbaldehyde moiety by deprotonation of the protected indole or azaindole derivative with a suitable base (e.g., BuLi, LDA) followed by treatment with a suitable formyl transfer reagent (e.g., N,N-dimethylformamide, N-formylpiperidine, N-formylmorpholine, ethyl formate, etc.). Additives such as TMEDA or HMPA facilitate the deprotonation in certain cases. An example intermediate prepared by this approach was described in the synthesis of I-8a.

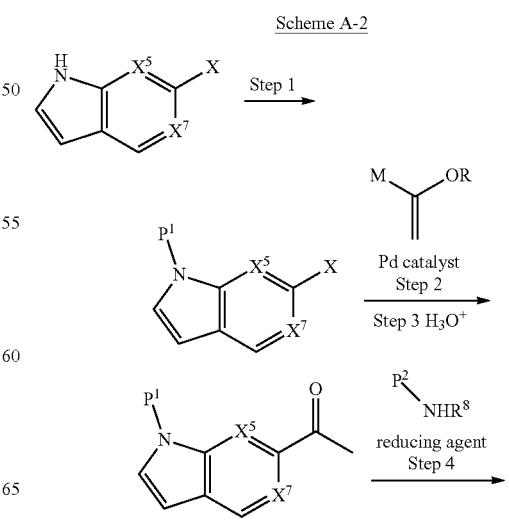

-continued

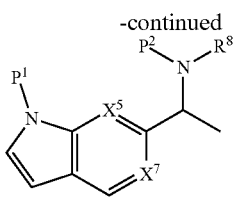

Step 5

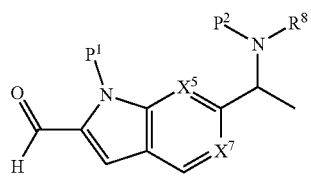

Scheme A-2 depicts the synthesis of an aminoethyl-containing indole or azaindole aldehyde intermediate, where X, M, $P^1$ and $P^2$ are as defined herein.

Step 1 is as described in Scheme A-1.

Steps 2 and 3 describes installation of an acetyl moiety by cross coupling of a vinyl ether nucleophile mediated by a suitable palladium catalyst followed by acidic hydrolysis. In this sequence, M is often trialkylstannane, but can also be boronic ester, acid, or trifluoroborate salt, or magnesium or zinc halide. Alternatively, a Heck coupling can be employed where M=H.

Step 4 describes the installation of a amino moiety —N($R^8$)($P^2$) by initial condensation with a suitable amine derivative followed by reduction of the formed imine intermediate. It is understood that this transformation can be accomplished in several ways, including but not limited to: a) in situ reductive amination, where the acetyl intermediate is treated with an amine derivative and a suitable reducing agent (e.g., NaBH(OAc)$_3$, NaBH$_3$CN) concurrently, and b) stepwise amine installation, where a suitable amine derivative (especially tert-butyl sulfinamide) is condensed in the presence of a Lewis acid dehydrating reagent (e.g., Ti(OiPr)$_4$, Ti(OEt)$_4$) to provide a imine (or sulfinimine) that is then reduced in a second step with a suitable reducing agent (e.g., NaBH$_4$, L-selectride). The stepwise method using a sulfinamide is particularly useful to afford control over the resulting stereoconfiguration. It is understood that protective group/auxiliary manipulation can take place following this sequence (e.g., $P^3$=S(O)tBu can be removed and/or converted to Boc) using standard conditions.

Step 5 describes a lithiation/formylation sequence as described in Scheme A-1. An example intermediate prepared by this approach is I-139.

Scheme A-3

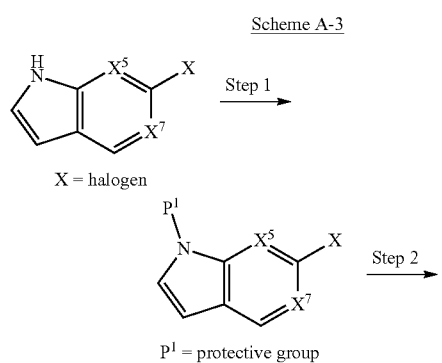

$P^1$ = protective group

-continued

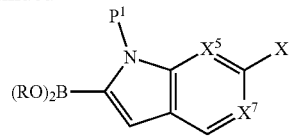

Scheme A-3 depicts the preparation of an indole or azaindole boronic acid or ester intermediate that contains a halogen functional handle.

Step 1 is as described in Scheme A-1.

Step 2 describes installation of a boronic acid or ester group by deprotonation of the protected indole or azaindole derivative with a suitable base (e.g., BuLi, LDA) followed by treatment with a suitable borate ester, including 2-isopropoxy-4,4,5,5-tetramethyl-1,3,2-dioxaborolane where B(OR)$_2$=pinacolboronate or tri-isopropylborate where B(OR)$_2$=B(OH)$_2$ following appropriate workup. An example intermediate prepared by this sequence is I-2.

Scheme A-4

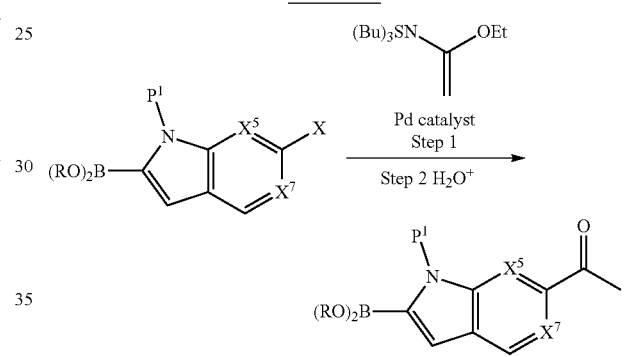

Scheme A-4 describes the synthesis of an acetyl containing indole or azaindole boronic ester. This is accomplished by a Stille cross coupling using tributyl(1-ethoxyvinyl)stannane along with a suitable palladium catalyst (e.g., PdCl$_2$(dppf), bis(tri-tert-butylphosphine)palladium(O), etc.) followed by acidic hydrolysis. A preferred boronic ester moiety is the cyclic methyimino-diacetic acid (MIDA) derivative. An example intermediate prepared using this sequence is I-4.

Scheme A-5

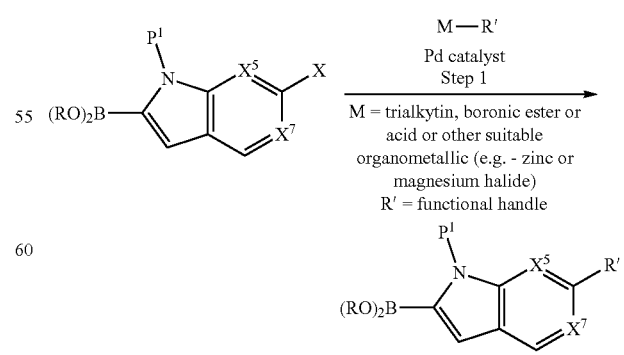

M = trialkytin, boronic ester or acid or other suitable organometallic (e.g. - zinc or magnesium halide)
R' = functional handle Scheme A-5 presents a more generalized synthesis of a functionalized indole or azaindole intermediate according to the same approach described in Scheme A-4. In a general sense, a functional handle R' can be incorporated by cross coupling with M-R', where M=trialkyltin, boronic acid or ester, or other metal species. A preferred substrate B(OR)₂ group is the cyclic methyiminodiacetic acid (MIDA) derivative. An example of M-R' is tributyl(vinyl)tin.

Scheme A-6

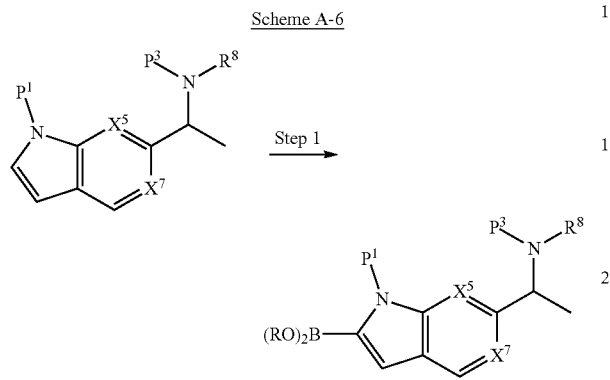

Scheme A-6 depicts the synthesis of an aminoethyl-containing indole or azaindole boronic acid or ester intermediate. This is accomplished as described in Step 2 of Scheme A-3 starting with an aminoethyl-containing indole or azaindole as described in Scheme A-2. An example intermediate prepared by this approach is I-16.

Scheme B-1

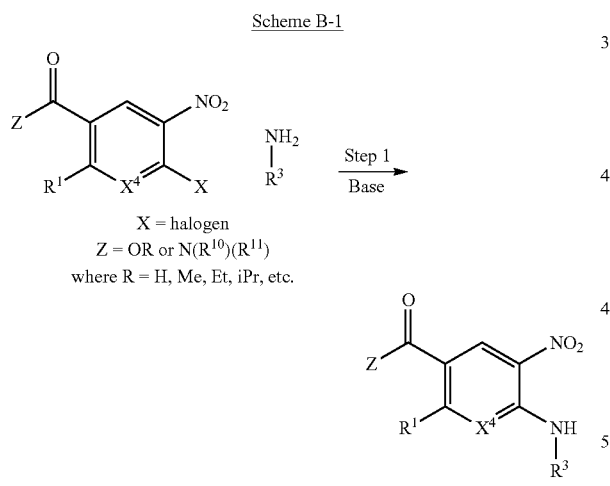

Scheme B-1 describes the synthesis of amino nitroarenes or heteroarenes useful for construction of benzimidazole or azabenzimidazole intermediates.

Step 1 describes the synthesis of 2-amino nitroarene or heteroarenes by treatment of a suitable halo nitroarene or halo nitroheteroarene (especially when X=F, Cl) with a functionalized amine along with base (e.g., triethylamine, Hunig's base). Alternatively, NH—R³ can be installed by palladium-mediated cross coupling (especially when X=Cl, Br, I). In certain cases, similar amino nitroarenes or nitroheteroarenes may also be prepared by direct nitration of the corresponding aryl or heteroaryl amine. Examples of intermediates prepared by this approach include I-7a-f.

Scheme B-2

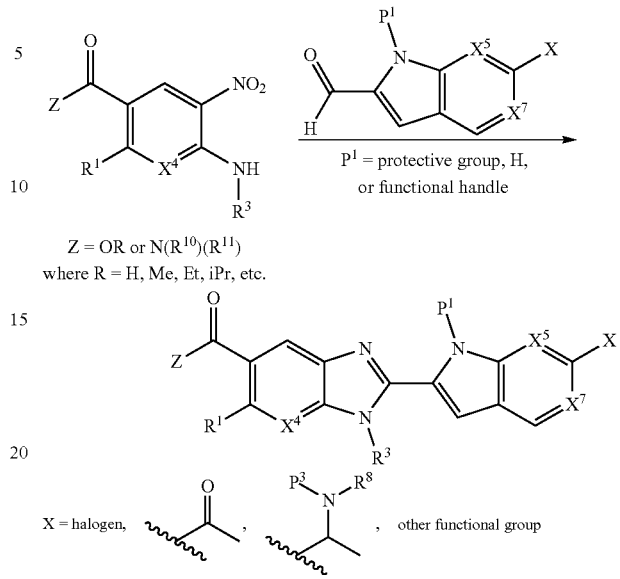

Scheme B-2 describes benzimidazole synthesis can be accomplished by treating 2-amino nitroarene or heteroarenes described in Scheme B-1 with a suitably protected and/or functionalized heteroaryl aldehyde described in Scheme A-1 in the presence of sodium dithionite, generally in aqueous alcohol solvent and at elevated temperature (e.g., 50-100° C.). P¹ is a protective group (e.g., -SEM), H, or functional precursor to intermediates described in subsequent sections (for example, P¹ may be 4-pentenyl). Example intermediates prepared by this approach include I-8a-c and I-13a Scheme B-3

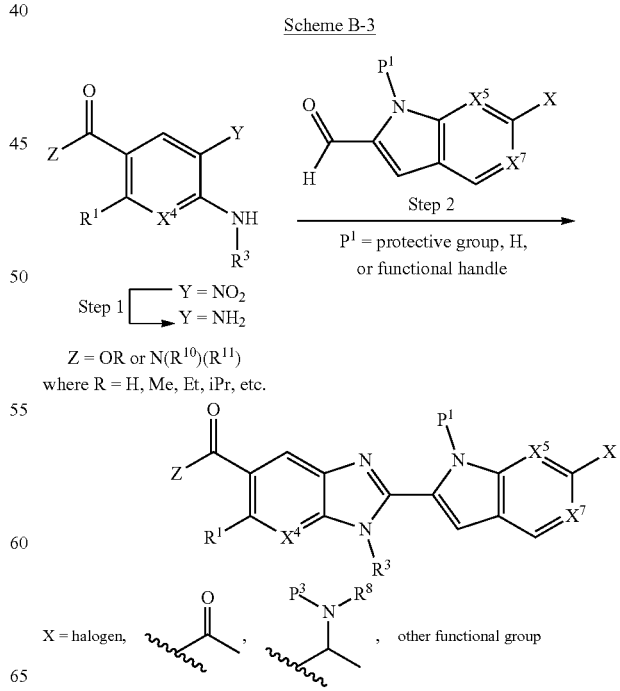

Scheme B-3 describes an alternate approach for benzimidazole synthesis.

Step 1 describes the reduction of 2-amino nitroarene or heteroarenes to the corresponding arylenediamine or heteroarylenediamine. This can be accomplished using standard methods, including hydrogenation over a suitable catalyst (e.g., Pd/C). In certain cases (especially when $R^3$=cyclopropyl), this can be accomplished by hydrogenation over a 1% Pt, 2% V catalyst. Other methods known to reduce aryl nitro groups (e.g., $Na_2S_2O_4$, Fe/HOAc, Zn/HOAc, etc.) may also be used to effect this transformation.

Step 2 describes benzimidazole synthesis from arylenediamines or heteroarylenediamines by treatment with a functionalized heteroaryl aldehyde along with a suitable oxidant (e.g., Oxone, oxygen). A preferred reaction condition consists of combining the diamine and aldehyde in acetic acid under air at elevated temperature (e.g., 50-100° C.). Example intermediates prepared by this sequence include I-9a-d and I-141a.

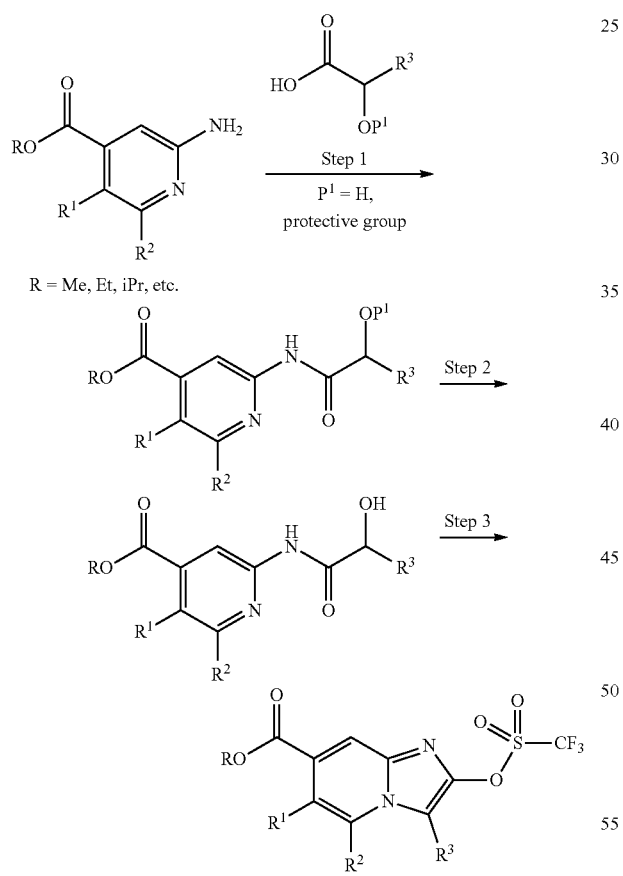

Scheme B-4

Scheme B-4 describes the synthesis of imidazopyridine triflate derivatives that can be used as coupling partners in subsequent transformations.

Step 1 describes the acylation of an aminopyridine with either a free ($P^1$=H) or protected ($P^1$=Bn, $SiMe_3$, $SiMe_2tBu$, $SiPh_2tBu$, etc.) hydroxyacid. Free ($P^1$=H) hydroxyacids can be protected in situ and converted to corresponding acid chlorides by initial treatment with TMS-Cl and pyridine followed by oxalyl chloride, and exposure to the aminopyridine in the presence of a suitable base (e.g., $Et_3N$, pyridine, Hunig's base) provides the amide product. Alternatively, protected hydroxyacids ($P^1$=Bn, $SiMe_3$, $SiMe_2tBu$, $SiPh_2tBu$, etc.) can be directly coupled with using standard peptide coupling reagents (e.g., HATU, EDC, etc.) in the presence of a suitable base or can also be converted to their corresponding acid chlorides and coupled as described above.

Step 2 describes the removal of the $P^1$ protective group, which can be accomplished in situ in step 1 with a mild acidic (citric acid, MeOH) workup when $P^1$=TMS. Alternatively, standard deprotection conditions can be used according protective group $P^1$; for instance, removal of the $P^1$=benzyl can be accomplished with $H_2$ over Pd/C in a suitable solvent.

Step 3 describes the direct cyclization of hydroxyamides to imidazopyridine triflate derivatives, which is accomplished by treatment with $Tf_2O$ in the presence of a suitable base (especially 2-methoxypyridine). This method is particularly useful when $R^2$ is other than H. An example intermediate prepared by this sequence is I-1.

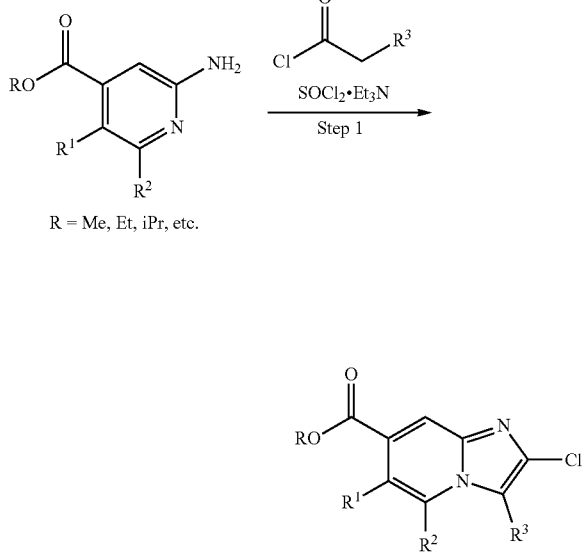

Scheme B-5

Scheme B5 describes the synthesis of chloroimidazopyridine intermediates by treatment of an aminopyridine intermediate with a suitable acid chloride (which can be prepared from the corresponding acid using standard procedures, e.g., oxalyl chloride) and base (e.g., triethylamine) in a suitable solvent (chloroform preferred) followed by thionyl chloride, generally at elevated temperature (e.g., −50° C.-100° C.). This method is particularly useful when $R^2 \neq H$, for example when $R^2$=OMe. This transformation may be accomplished in stepwise fashion, where the intermediate amide formed can be isolated using standard approaches and subsequently treated with thionyl chloride and triethylamine to effect cyclization. An example intermediate prepared by this approach is I-5b.

Scheme B-6

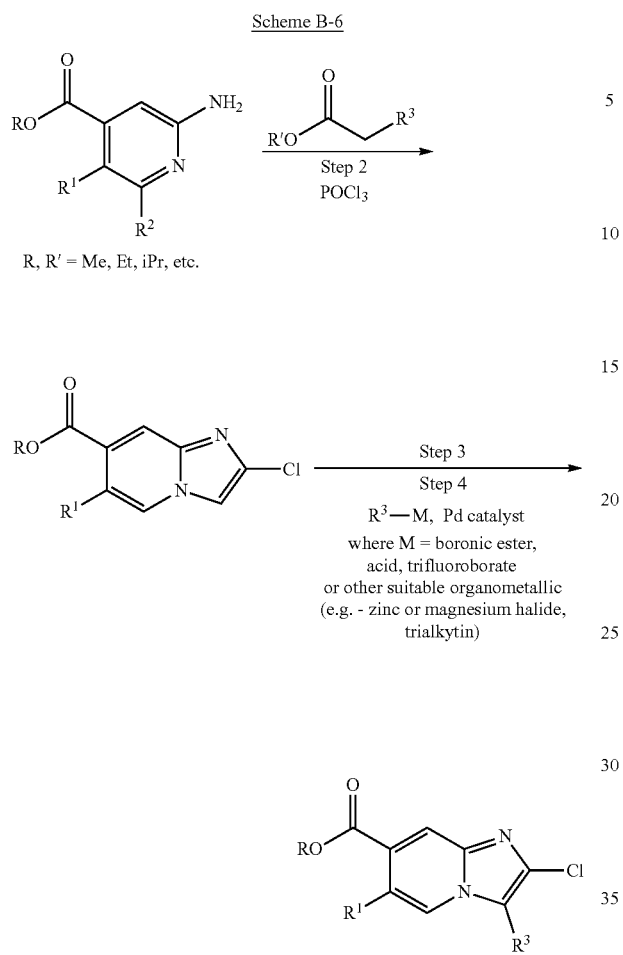

Scheme B-6 describes an alternate preparation of chloroimidazopyridine intermediates.

Step 1 describes the initial alkylation of 2-aminopyridines on the ring nitrogen with a suitable bromoacetate derivative (e.g., ethyl bromoacetate) to provide a pyridinium bromide salt.

Step 2 describes the conversion of the pyridinium bromide salt from Step 1 to the corresponding 2-chloroimidazopyridine using phosphorous oxychloride.

Step 3 describes halogenation of the 2-chloroimidazopyridine heterocycle with an electrophilic halogenation reagent (e.g., N-iodosuccinimide) to provide the corresponding 3-halo 2-chloroimidazopyridine intermediate.

Step 4 describes the selective functionalization of the 3-position of prepared 3-halo 2-chloroimidazopyridine intermediates (especially when 3-iodo or 3-bromo intermediates are used). This can be accomplished using a variety of conditions known to those verse in the art, and include palladium-mediated cross coupling reactions (e.g., by treatment with $R^3$-M, where M is a boronic ester, acid, or trifluoroborate group, or when M is a zinc or magnesium halide species, or when M is a trialkylstannane in the presence of a palladium catalyst). An example intermediate prepared by this approach is I-5a.

Scheme B-7

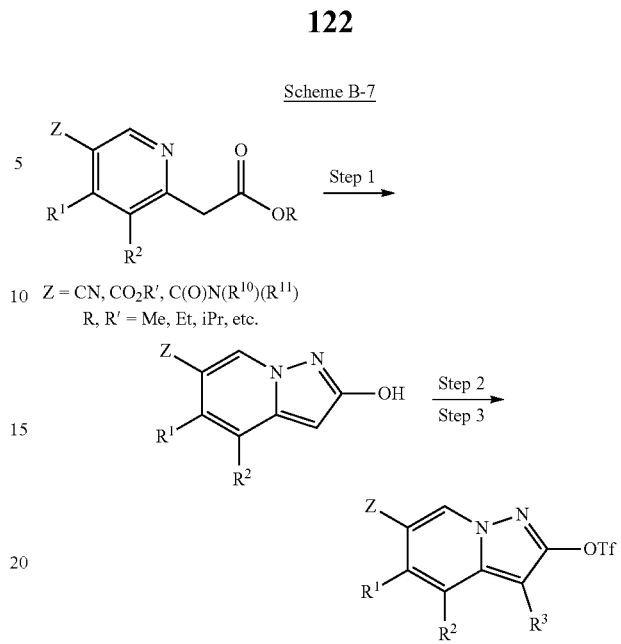

Scheme B-7 describes the synthesis of substituted pyrazolopyridine triflate intermediates.

Step 1 describes the cyclization of a carboalkoxymethyl pyridine derivative, which is accomplished by treatment with a suitable electrophilic amination reagent (e.g., —O-(mesitylsulfonyl)hydroxylamine). This aminates the ring nitrogen, the product of which then cyclizes spontaneously to the depicted hydroxy pyrazolopyridine.

Step 2 describes the installation of $R^3$ groups, which can be accomplished in several ways. One method utilizes a reductive Friedel-Crafts type reaction wherein the heterocycle is treated with a suitable aldehyde in the presence of TFA and triethylsilane (for an example see I-14, where acetaldehyde is used for $R^3$=Et). Alternatively, $R^3$ may be installed in stepwise fashion by electrophilic halogenation (e.g., using NIS) followed by cross-coupling with M-$R^3$ in the presence of a suitable palladium catalyst, where M=M is boronic ester, acid, trifluoroborate salt, trialkylstannane or organozinc or organomagnesium halide. In cases where $R^3$=H, this step is omitted.

Step 3 describes the conversion of the resulting hydroxypyrazolopyridine heterocycle to the corresponding triflate, which may be accomplished using a suitable base (e.g., NaH, $Et_3N$, pyridine) in the presence of a triflate transfer reagent (e.g., $Tf_2O$, $PhN(Tf)_2$, N-(5-chloropyridin-2-yl)-1,1,1-trifluoro-N-((trifluoromethyl)sulfonyl)methanesulfonamide). An example intermediate prepared using this sequence is I-14.

Scheme B-8

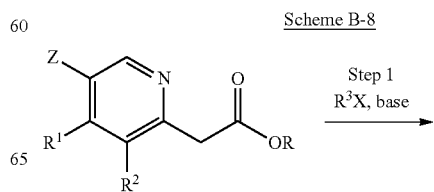

123

-continued

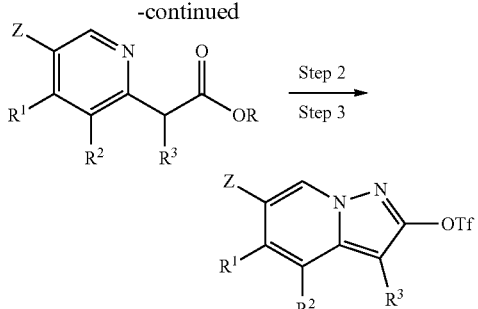

Z = CN, CO₂R', C(O)N(R¹⁰)(R¹¹) R, R' = Me, Et, iPr, etc.

Scheme B-8 described an alternate synthesis of substituted pyrazolopyridine heterocycles with suitable functionality to access described compounds.

Step 1 describes the alkylation of a carboalkoxymethyl pyridine derivative with $R^3$—X, where X=halogen or pseudohalide, in the presence of a suitable base (e.g., LDA, LiHMDS, etc.).

Step 2 and 3 describe the same cyclization and triflation steps described in steps 1 and 3 in Scheme B-7, respectively. An example intermediate prepared using this sequence is I-15.

Scheme B-9

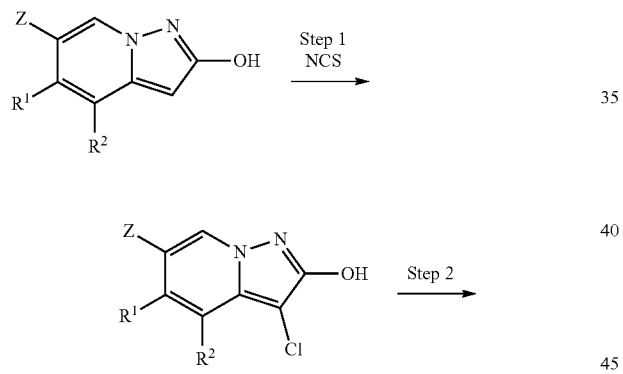

Z = CN, CO₂R', C(O)N(R¹⁰)(R¹¹) R = Me, Et, iPr, etc.

Scheme B-9 describes the synthesis of a pyrazolopyridine triflate containing a chloro group that can be used for subsequent $R^3$ installation following derivatization as described in Scheme B-10 below.

Step 1 describes the treatment of a depicted hydroxypyrazolopyridine with an electrophilic chlorination reagent (e.g., NCS) to provide the depicted chlorinated intermediate.

Step 2 describes the same triflation method described in Step 3 of Scheme B-7.

124

Scheme B-10

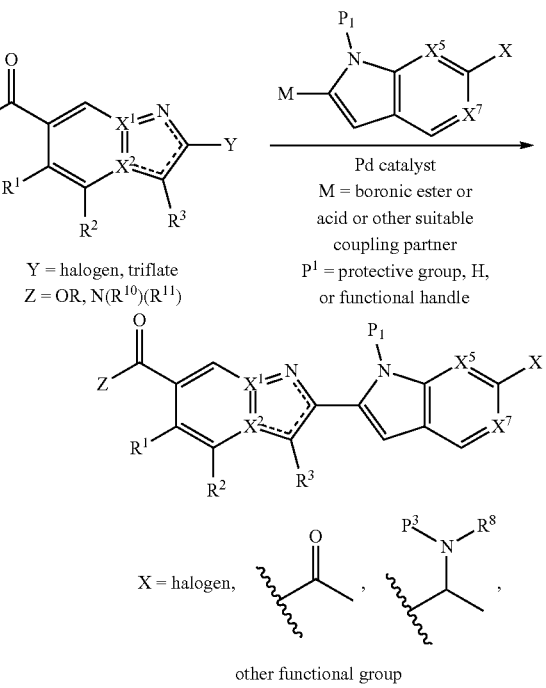

Y = halogen, triflate
Z = OR, N(R¹⁰)(R¹¹)

P¹ = protective group, H, or functional handle

X = halogen, other functional group

Scheme B-10 describes the cross coupling of a suitably substituted imidazopyridine (described in Schemes B-4, B-5, B-6) or pyrazolopyridine (described in Scheme B-7, B-8, B-9) halogen or pseudohalide (e.g., triflate) intermediate with a functionalized indole or azaindole partner (described in Schemes A-3, A-4, A-5, A-6), where M=boronic acid or ester, in the presence of a suitable palladium catalyst. It is understood that M=magnesium halide or zinc halide could be accessed by transmetalation from M=Li (prepared according to Step 2 in Scheme A-1). Example intermediates prepared using this sequence are I-3 and I-136a.

Scheme C-1

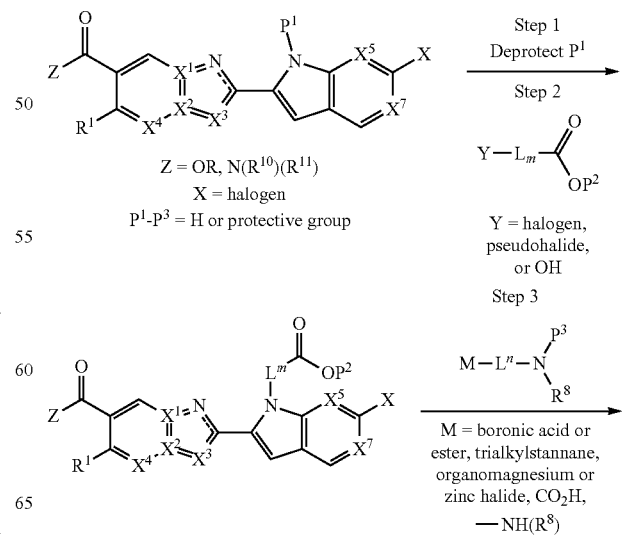

Z = OR, N(R¹⁰)(R¹¹)
X = halogen
P¹-P³ = H or protective group

Step 1 Deprotect P¹
Step 2
Y = halogen, pseudohalide, or OH
Step 3
M = boronic acid or ester, trialkylstannane, organomagnesium or zinc halide, CO₂H, —NH(R⁸)

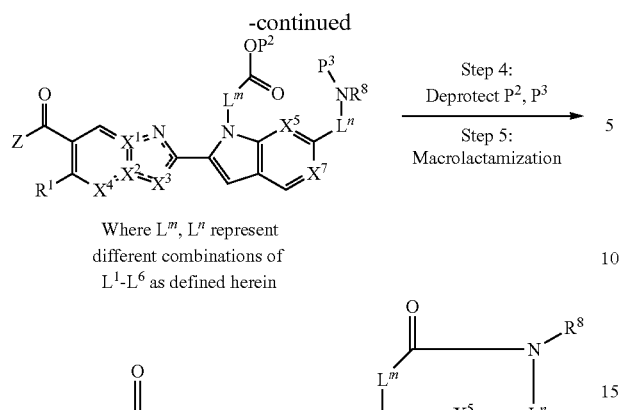

Where $L^m$, $L^n$ represent different combinations of $L^1$-$L^6$ as defined herein Scheme C-1 depicts synthesis of a macrocyclic lactam by incorporation of acid- and amine-containing fragments followed by amide bond formation.

Steps 1 and 2 describe the installation of a protected carboxylic acid macrocycle fragment by deprotection of $P^1$ (for example, using TFA/DCM when $P^1$=Boc or SEM; or using TBAF when $P^1$=benzenesulfonyl) followed by alkylation with Y-$L^m$-$CO_2P^2$ where Y=halogen (preferably Br or I) or pseudohalide (e.g., tosylate, triflate, mesylate, etc.) in the presence of a suitable base (e.g., $Cs_2CO_3$, NaH, NaHMDS). In certain cases, $P^1$=H, wherein the deprotection step is omitted. In certain cases, Y=OH, wherein the alkylation described in Step 2 is accomplished using a Mitsunobu protocol (for example, treatment with DIAD and $PPh_3$). One example of Y-$L^m$-$CO_2P^2$ is tert-butyl 8-bromooctanoate L1a.

Step 3 describes the installation of an amine-containing macrocycle precursor fragment. This can be accomplished by direct cross-coupling of M-$L^n$-N($P^3$)($R^8$) in the presence of a suitable palladium catalyst when M is a boronic ester, acid, trifluoroborate salt, trialkylstannane or organozinc or organomagnesium halide, or —NH($R^8$). One specific example of M-$L^n$-N($P^3$)($R^8$) is I-108. When M=—NH($R^8$), this group becomes part of $L^n$ as depicted following the coupling step. When M=$CO_2H$, the coupling may be carried out in the presence of a suitable photocatalyst (e.g., Ir[dF($CF_3$)ppy]$_2$(dtbbpy)$PF_6$), nickel precatalyst (e.g., $NiCl_2$) and light of an appropriate wavelength. An example of an intermediate prepared by this protocol is described in the synthesis of Example 134.

Step 4 describes the deprotection of $P^2$ and $P^3$ protective groups to reveal acid and amine coupling partners, respectively. In certain cases (e.g., $P^2$=tert-butyl and $P^3$=Boc), this may be accomplished in a single step using suitable conditions (e.g., TFA or HCl). In other cases deprotection is accomplished stepwise using suitable conditions. $P^2$ and $P^3$ may optionally and independently be hydrogen, in which case an associated protecting group removal step is omitted.

Step 5 describes an intramolecular amide bond formation to provide a macrocyclic lactam. This can be accomplished using standard amide bond forming reagents (e.g., HATU, EDC, etc.) along with a suitable base (e.g., $Et_3N$, Hunig's base, etc.). An example prepared according to this sequence is Example 316.

It is understood that the order of events depicted in Scheme C-1 could be rearranged; for example, step 3 could precede steps 1 and 2.

It is understood that fragments containing functional precursors to —$CO_2P^2$ (for example —$CH_2OP^4$, where $P^4$=H or suitable protective group) may also be used in Step 2, where —$CO_2P^2$ may be subsequently accessed by functional group transformation (for example by deprotection/oxidation of —$CH_2OP^4$).

It is also understood that that fragments containing functional precursors to —N($R^8$)$P^3$ may also be used in step 3, where —N($R^8$)$P^3$ may be subsequently accessed by functional group transformation, for example by Curtius rearrangement of a carboxylic acid, or by reductive amination upon a ketone or aldehyde. Several specific cases are outlined in Scheme C-2, C-3, and C-4.

Scheme C-2

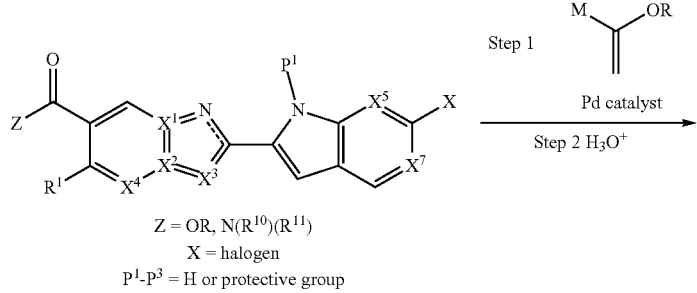

Z = OR, N($R^{10}$)($R^{11}$)
X = halogen
$P^1$-$P^3$ = H or protective group

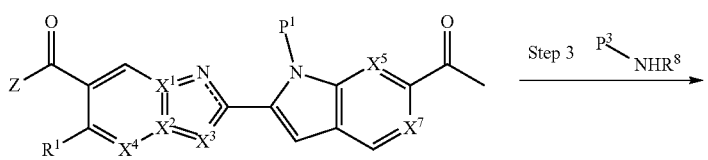

-continued

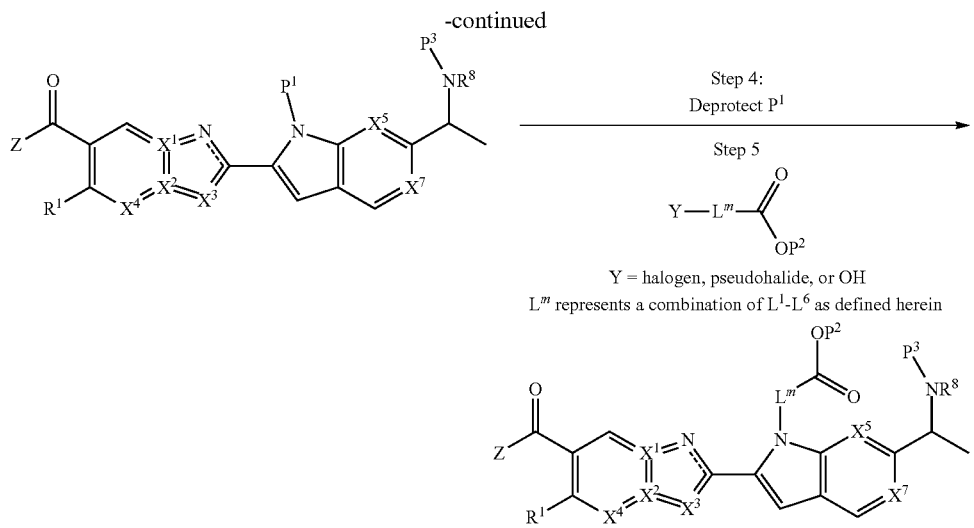

Scheme C-2 depicts a synthesis of a macrocyclic lactam precursor wherein the amine-containing macrocycle fragment is accessed from an acetyl precursor.

Step 1 and 2 describe installation of an acetyl moiety by cross coupling of a vinyl ether nucleophile mediated by a suitable palladium catalyst followed by acidic hydrolysis. In this sequence, M is often trialkylstannane (for example, as in 1-ethoxyvinyltributylstannane), but other suitable organometallic species for cross-coupling may also be used. Alternatively, a Heck coupling mediated by a suitable palladium catalyst may be used where M=H.

Step 3 describes the installation of a protected or unprotected amino moiety condensation of a suitable amine derivative followed by reduction of the formed imine intermediate. This transformation may be accomplished in several ways, including in situ reductive amination, where the acetyl intermediate is treated with amine and a suitable reducing agent (e.g., NaBH(OAc)$_3$, NaBH$_3$CN) concurrently. Alternatively, this can be accomplished stepwise, where a suitable amine derivative is condensed in the presence of a Lewis acid dehydrating reagent (e.g., Ti(OiPr)$_4$, Ti(OEt)$_4$, CuSO$_4$) to provide an imine followed by reduction in a second step with a suitable reducing agent (e.g., NaBH$_4$, L-selectride). tert-butyl sulfinamide is an especially useful amine derivative, due to the availability of enantiomeric forms and the known ability of these to exert control over stereoconfiguration in the reduction step. It is understood that protective group/auxiliary manipulation can take after amine installation (e.g., P$^3$=S(O)tBu can be removed and/or converted to Boc), or that the amine can be deprotected (to provide P$^3$=H) using known conditions.

Steps 4 and 5 are analogous to Steps 1 and 2 in Scheme C-1.

This product can be treated as described in Steps 4 and 5 of Scheme C-1 to deliver macrolactam products. The product of Step 3 can also be derivatized and treated as described in Scheme C-7 to deliver macrolactam products via ring closing metathesis.

It is understood that the order of events depicted in Scheme C-2 could be rearranged; for example, steps 4 and 5 could precede steps 1-3.

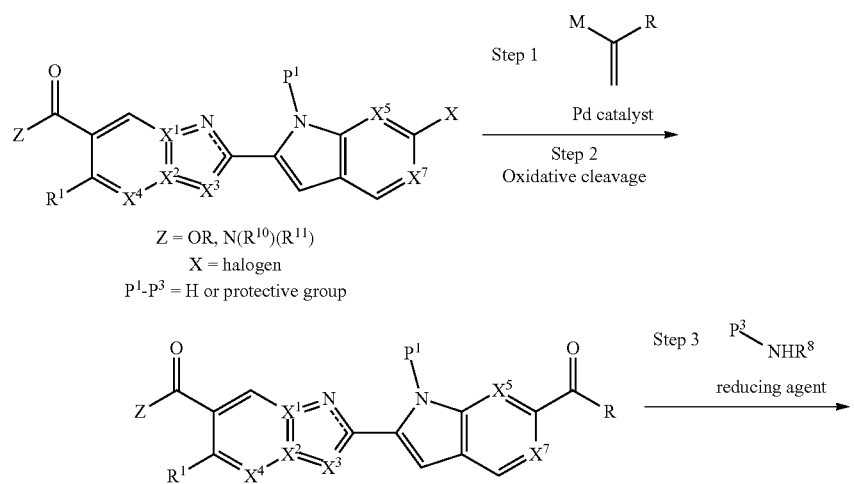

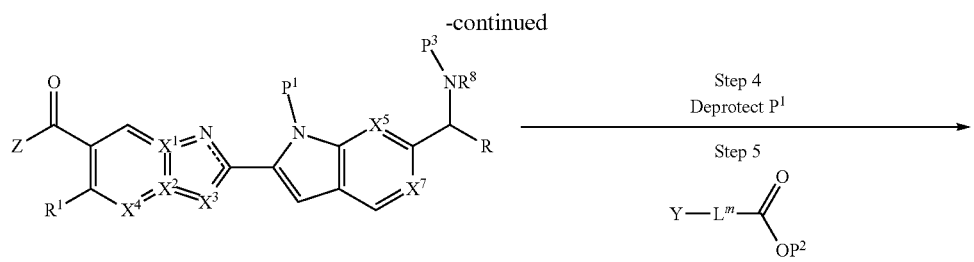

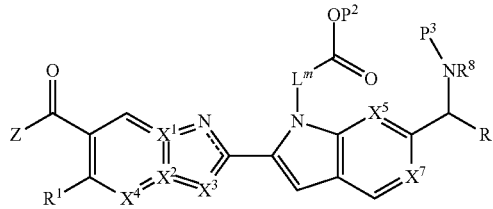

Y = halogen, pseudohalide, or OH
L$^m$ represents a combination of L$^1$-L$^1$ as defined herein Scheme C-3 depicts a synthesis of a macrocyclic lactam precursor similar to that described in Scheme C-2 but with a modified method for carbonyl group installation. Step 1 and 2 describe the preparation of a ketone (R=Me, alkyl, or other groups) or aldehyde (R=H) intermediate by cross coupling with an olefin-containing partner mediated by a suitable palladium catalyst, where M=boronic ester, acid, trifluoroborate salt, trialkylstannane or organozinc or organomagnesium halide, followed by oxidative cleavage using standard methods (e.g., OsO$_4$/NaIO$_4$, O$_3$/PPh$_3$, etc.).

Steps 3 through 5 are analogous to Steps 3 through 5 in Scheme C-2 above.

The product of this sequence can be used as described in Steps 4 and 5 of Scheme C-1. The product of Step 3 can also be derivatized and treated as described in Scheme C-7 to deliver macrolactam products via ring closing metathesis.

It is understood that the order of events depicted in Scheme C-3 could be rearranged; for example, steps 4 and 5 could precede steps 1-3.

Scheme C-4

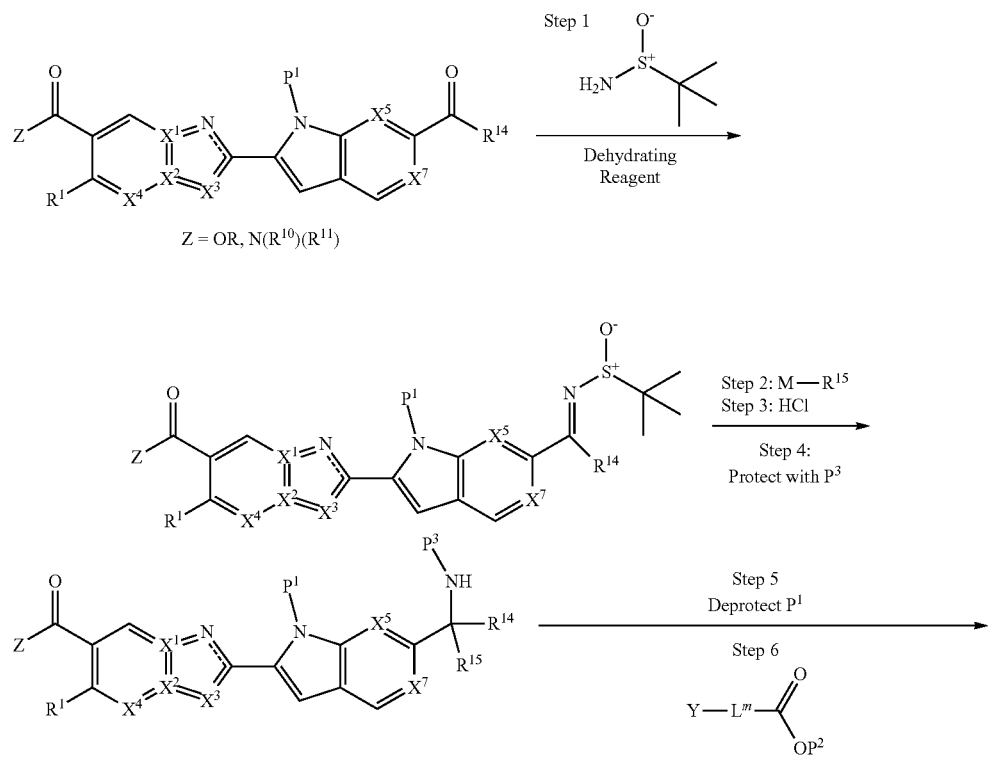

Y = halogen, pseudohalide, or OH
L$^m$ represents a combination of L$^1$-L$^6$ as defined herein

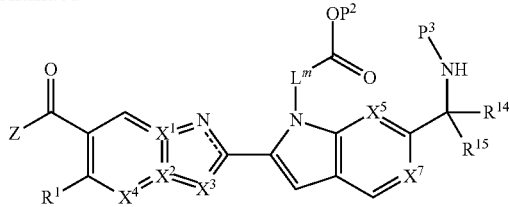

Scheme C-4 depicts a synthesis of a macrocyclic lactam precursor that allows for variable substitution (e.g., $R^{15}$) on the amine-containing fragment.

Step 1 describes the initial condensation of a tert-butyl sulfinamide with an aldehyde (R=H) or ketone (R=Me, alkyl, or other group) in the presence of a Lewis acid dehydrating reagent (e.g., $Ti(OiPr)_4$, $Ti(OEt)_4$, $CuSO_4$) to provide a sulfinimine product.

Step 2 describes the reaction of the sulfinimine above with a suitable nucleophile (e.g., M=Li, magnesium halide or zinc halide, R=alkyl, aryl, alkenyl, etc.). This reaction can be facilitated by Lewis acid promoters (e.g., $BF_3 \cdot OEt_2$, $AlMe_3$, etc.). In certain cases, M-R' refers to a fluoroalkylsilane, where M=trialkylsilane (e.g., TMS-$CF_3$, TMS-$CHF_2$), and in these cases a suitable promoter is used to facilitate the reaction (e.g., tetrabutylammonium difluorotriphenylsilicate, tetraalkylammonium fluoride, etc.)

Steps 3 and 4 describe the optional removal of the tert-butanesulfinyl group and protection of the resulting amine with a suitable $P^3$ group (e.g., Boc).

Steps 5 and 6 are analogous to Steps 1 and 2 in Scheme C-1.

It is understood that the sulfinamide described in Step 1 could be racemic or enriched to good enantiomeric excess as a either enantiomer, and that enantioenriched forms may allow for control over the stereocenter formed on addition of $R^{15}$.

The product of this sequence can be used as described in Steps 4 and 5 of Scheme C-1. The product of Step 4 can also be derivatized and treated as described in Scheme C-7 to deliver macrolactam products via ring closing metathesis.

It is understood that the order of events depicted in Scheme C-4 could be rearranged; for example, steps 5 and 6 could precede steps 1-4. An example intermediate prepared by this sequence is described in the synthesis of Example 259.

Scheme C-5

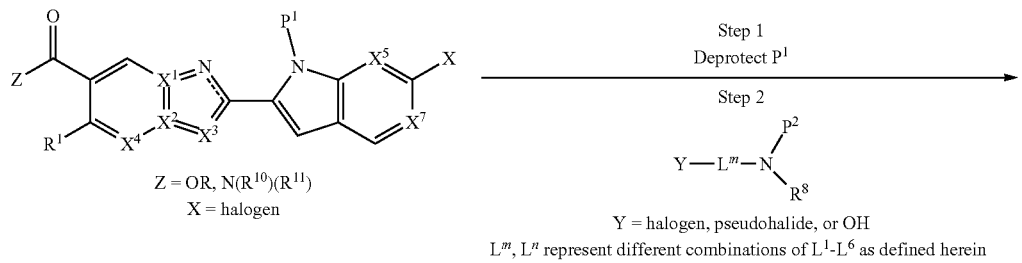

$Z = OR, N(R^{10})(R^{11})$
$X$ = halogen

Step 1
Deprotect $P^1$

Step 2

$Y—L^m—N{\overset{P^2}{\underset{R^8}{}}}$

Y = halogen, pseudohalide, or OH
$L^m$, $L^n$ represent different combinations of $L^1$-$L^6$ as defined herein

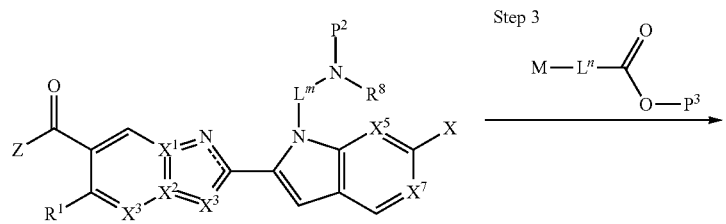

Step 3

$M—L^n{\overset{O}{\underset{O—P^3}{\diagdown}}}$

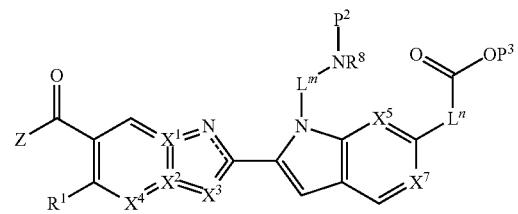

Scheme C-5 depicts the synthesis of an alternate macrocyclic lactam precursor by installation of an amine-containing and carboxylic acid containing fragments.

Steps 1 and 2 describe the installation of a protected amine-containing macrocycle precursor fragment by deprotection of $P^1$ (for example, using TFA/DCM when $P^1$=Boc or SEM; or using TBAF when $P^1$=benzenesulfonyl) followed by alkylation with Y-$L^m$-N($R^8$)($P^2$), where Y=halogen (preferably Br or I) in the presence of a suitable base (e.g., $Cs_2CO_3$, NaH, NaHMDS). When Y=OH, the alkylation described in Step 2 is accomplished using a Mitsunobu protocol (for example, using DIAD and $PPh_3$). In certain cases, $P^1$=H, wherein the deprotection step is omitted.

Step 3 describes the installation of a carboxylic acid-containing macrocycle precursor fragment by coupling M-$L^n$-$CO_2P^3$, where M=boronic ester, acid, or trifluoroborate salt, trialkylstannane, or magnesium or zinc halide, in the presence of a suitable palladium catalyst. One specific example of M-$L^n$-$CO_2P^3$ is (2-(tert-butoxycarbonyl)phenyl)boronic acid, where M=B(OH)$_2$, $L^n$=Ph, and $P^3$=tert-butyl. Another example of M-$L^n$-$CO_2P^3$ is the lithium enolate of tert-butyl isobutyrate.

The product of this sequence can be used as described in Steps 4 and 5 of Scheme C-1 to deliver macrocyclic lactam products. An example prepared by this protocol is Example 227.

It is understood that the order of events depicted in Scheme C-5 could be reversed or modified; for example, step 3 could precede steps 1 and 2.

It is understood that fragments containing functional precursors to —$CO_2P^3$ (for example —$CH_2OP^4$, where $P^4$=H or suitable protective group) may also be used in Step 2, where —$CO_2P^3$ may be subsequently accessed by functional group transformation (for example by deprotection/oxidation of —$CH_2OP^4$).

It is also understood that that fragments containing functional precursors to —N($R^8$)$P^2$ may also be used in step 3, where —N($R^8$)$P^2$ may be subsequently accessed by functional group transformation, for example by Curtius rearrangement of a carboxylic acid, or by reductive amination upon a ketone or aldehyde.

Scheme C-6

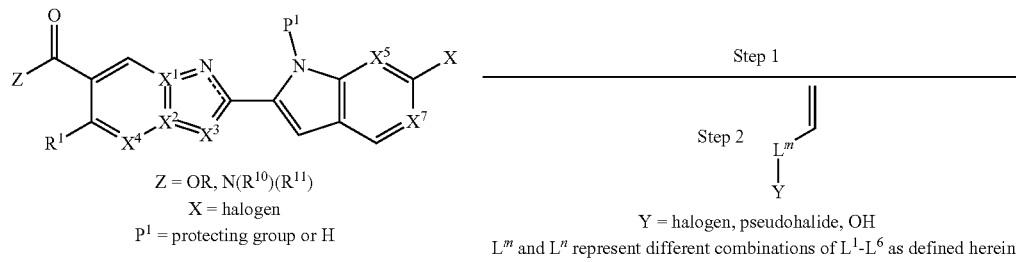

Z = OR, N($R^{10}$)($R^{11}$)
X = halogen
$P^1$ = protecting group or H

Y = halogen, pseudohalide, OH
$L^m$ and $L^n$ represent different combinations of $L^1$-$L^6$ as defined herein

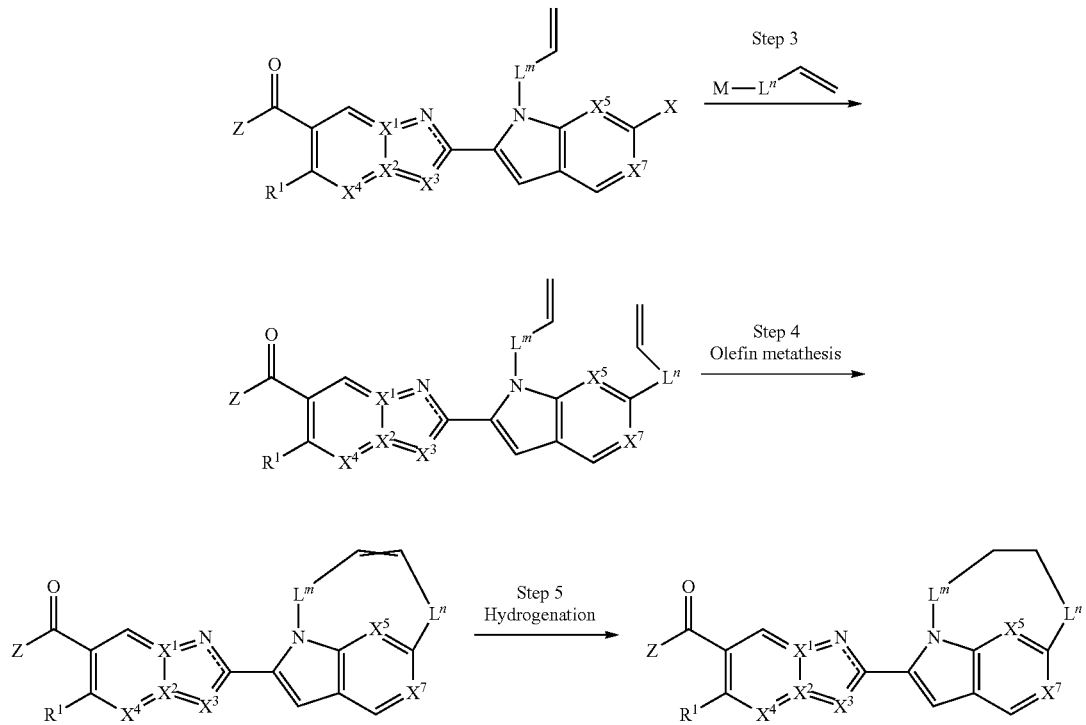

Scheme C-6 describes the synthesis of a macrocycle using a ring closing olefin metathesis approach.

Step 1 is carried out as described in Step 1 of Scheme C-1 or is omitted when $P^1$=H.

Step 2 describes incorporation of one olefin-containing fragment by alkylation with Y-L'''-CHCH$_2$ where Y=halogen or pseudohalide (e.g., triflate, tosylate, mesylate) in the presence of a suitable base (e.g., Cs$_2$CO$_3$, NaH, NaHMDS, etc.). This transformation can be accomplished when Y=OH using a Mitsunobu-type protocol (e.g., by treatment with DIAD and PPh$_3$). One example of Y-L'''-CHCH$_2$ is 5-bromopent-1-ene.

Step 3 describes the installation of a second olefin-containing fragment by cross-coupling with M-L''-CHCH$_2$, where M=boronic ester, acid, or trifluoroborate salt, trialkylstannane, or magnesium or zinc halide, in the presence of a suitable palladium catalyst. One example of M-L''-CHCH$_2$ is (2-vinylphenyl)boronic acid.

Step 4 describes ring closing macrocyclization of the bis-olefin intermediate by treatment with a suitable metathesis catalyst, including (1,3-bis-(2,4,6-trimethylphenyl)-2-imidazolidinylidene)dichloro(o-isopropoxyphenylmethylene)mthenium (Grubbs-Hoveyda II), (1,3-bis(2,4,6-trimethylphenyl)-2-imidazolidinylidene)dichloro(phenylmethylene)(tricyclohexylphosphine)ruthenium (Grubbs II), dichloro[1,3-bis(2,4,6-trimethylphenyl)-2-imidazolidinylidene][[5-[(dimethylamino)sulfonyl]-2-(1-methylethoxy-0)phenyl]methylene-C]ruthenium(II) (Zhan-1b), and other suitable metal-carbene complexes, under appropriate conditions. The olefin product may be formed as a single geometric isomer or mixtures of isomers.

Step 5 describes the optional reduction of the macrocyclic olefin. This can be accomplished by hydrogenation over a suitable metal catalyst (e.g., Pd/C). Alternatively, this may be accomplished using diimide, which can be generated in situ under a variety of conditions, one preferred method being use of p-toluenesulfonhydrazide and sodium acetate in aqueous/organic solvent mixtures (e.g., water/THF) at elevated temperature (e.g., 90° C.). The latter method is useful to avoid undesired hydrogenation/hydrogenolysis, for example hydrogenolytic ring opening of a vinylcyclopropane motif.

It is understood that the order of events depicted in Scheme C-6 can be modified, e.g., Step 3 may precede steps 1 and 2.

It is also understood that —CHCH$_2$ fragments are depicted in this sequence for convenience, but that substituted olefins may also be used that productively engage in metathesis chemistry.

It is also understood that the olefin moieties depicted in Scheme C-6 may be accessed from a suitable functional precursor after installation of said precursor-containing fragment according to the sequence depicted. For example, an olefin could be accessed from an alcohol moiety by oxidation to the corresponding aldehyde followed by Wittig-type olefination, among other possibilities. Additionally, olefin moieties could also be incorporated by coupling of an olefin-containing fragment with a suitable partner in L'' or L'''. For instance, an olefin moiety could be accessed from a corresponding aryl halide (e.g., where L''=phenyl) by cross-coupling of M-CHCH$_2$, where M=boronic ester, acid, trifluoroborate salt, trialkylstannane, or magnesium or zinc halide, in the presence of a suitable palladium catalyst. Alternatively, an olefin-containing carboxylic acid fragment could be coupled with an amine moiety in L''' or L'' to form an amide-containing ring-closing metathesis precursor; a more specific version of this general approach is outlined in Scheme C-7 below.

Scheme C-7

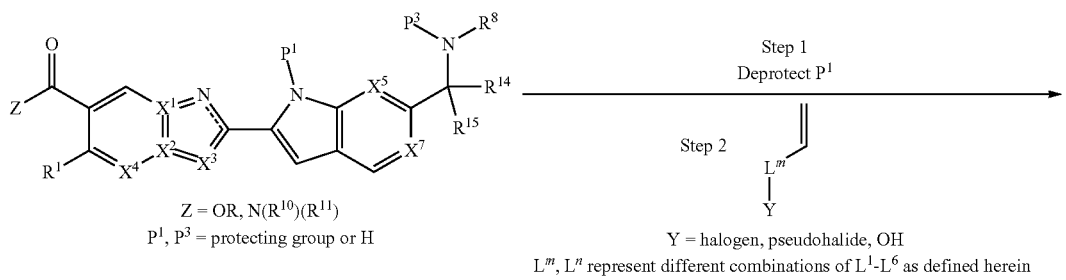

Z = OR, N(R$^{10}$)(R$^{11}$)
P$^1$, P$^3$ = protecting group or H

Y = halogen, pseudohalide, OH
L''', L'' represent different combinations of L$^1$-L$^6$ as defined herein

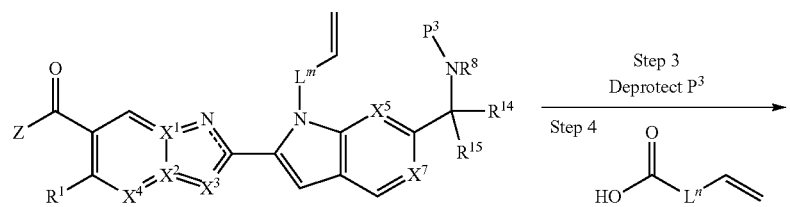

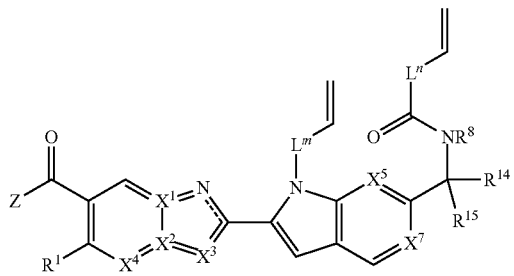

Scheme C-7 described the synthesis of an amide-containing ring closing metathesis macrocyclization precursor.

Step 1 is as described in Step 1 of Scheme C-1 or is omitted when $P^1$=H.

Step 2 describes alkylation with Y-$L^m$-CHCH$_2$ (where Y=halogen) in the presence of a suitable base (e.g., Cs$_2$CO$_3$, NaH, NaHMDS). When Y=OH, the alkylation described in this step is accomplished using a Mitsunobu protocol (for example, using DIAD and PPh$_3$).

Steps 3 and 4 describe the installation of a second olefin-containing fragment by removal of the $P^3$ protective group (for example, using TFA/DCM when $P^3$=Boc) followed by amide bond formation with CH$_2$CH-$L^n$-CO$_2$H. The amide bond forming step is mediated by standard peptide coupling reagents (e.g., DIC, EDC, HATU, etc.) in the presence of a suitable base (e.g., Et$_3$N, Hunig's base), or the acid can first be converted to its corresponding acid chloride with oxalyl chloride.

The product of this sequence can be used as described as in Steps 5 and/or 6 in Scheme C-6 to afford macrocyclic products. Examples of compounds prepared by this approach are Examples 1-3 and Example 273.

It is understood that the order of events depicted in Scheme C-7 can be changed; for example, where Steps 3 and 4 precede Steps 1 and 2.

It is also understood that —CHCH$_2$ fragments are depicted in this sequence for convenience, but that substituted olefins may also be used that productively engage in metathesis chemistry.

It is also understood that functional precursors to the olefins depicted in Scheme C-7 could be installed using the same fragment coupling approaches, and that the depicted olefins could be subsequently installed using transformations known to those versed in the art to the olefins as depicted. For example, an olefin moiety could be accessed from a corresponding aryl halide (e.g., where $L^n$=phenyl) by cross-coupling of M-CHCH$_2$, where M=boronic ester, acid, trifluoroborate salt, trialkylstannane, or magnesium or zinc halide, in the presence of a suitable palladium catalyst.

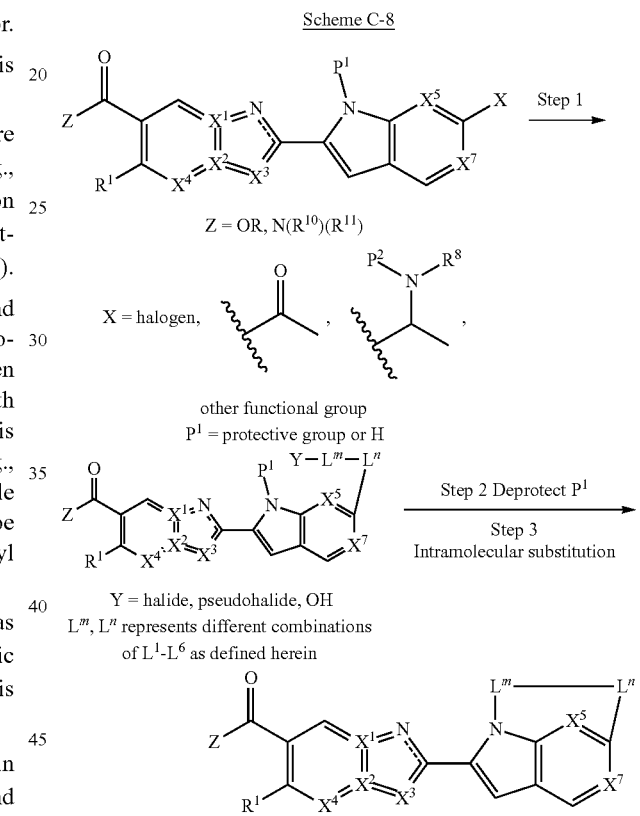

Scheme C-8

Scheme C-8 describes the preparation of an intramolecular substitution macrocyclization precursor.

Step 1 describes the generalized installation of a fragment -$L^n$-$L^m$-Y, where $L^m$ and $L^n$ comprise desired combinations of L groups described herein or precursors thereof, and where Y=OH, halogen, or pseudohalide (e.g., triflate, mesylate, etc.). This is accomplished using methods described herein or other methods known to those versed in the art, starting from group X, which may be halogen, acetyl, aminoalkyl fragment, or other functional precursor to any L group described herein.

Step 2 describes the deprotection of a protective group $P^1$ to reveal a nucleophilic indole or azaindole. Selected examples are described in Step 1 of Scheme C-1. When $P^1$=H, this step is omitted. Protecting group $P^1$ may also be removed before, after, or at any appropriate stage during the sequence used to install $L^n$-$L^m$-Y.

Step 3 describes intramolecular displacement to form a macrocycle, which can be accomplished in cases where Y=halogen or pseudohalide (e.g., tosylate, triflate, mesylate, etc.) by treatment with a suitable base (e.g., —Cs₂CO₃, K₂CO₃, NaHMDS). When Y=OH, this displacement may be accomplished using a Mitsunobu protocol, for example by treatment with DIAD and PPh₃. Examples prepared using this sequence are Example 127, Example 291 and Example 25.

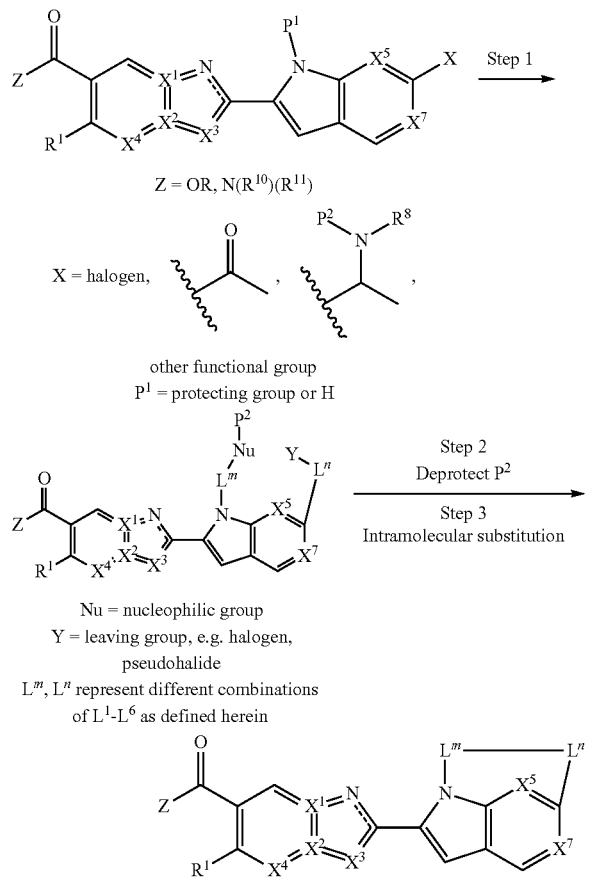

Scheme C-9 describes an alternative synthesis of a macrocycle using an intramolecular substitution strategy.

Step 1 describes a general approach to a macrocycle precursor that contains fragments Nu-P² where Nu=nucleophilic group (e.g., oxygen, nitrogen, or sulfur) and leaving group Y (e.g., halogen, triflate, mesylate, etc.). In some cases, Y=OH. These fragments may be elaborated in any suitable order using approaches similar to those described herein or by transformations known to those versed in the art.

Step 2 describes the deprotection of Nu-P², which can be accomplished using standard conditions. When P²=H, this step is omitted. In the case where Nu-P² represents a protected nitrogen nucleophile with suitable nucleophilicity (e.g., NH-nosyl, NHBoc), this deprotection step can be omitted or carried out following the macrocyclization described in Step 3.

Step 3 describes macrocycle synthesis by intramolecular, which can be accomplished in cases where Y=halogen or pseudohalide (e.g., tosylate, triflate, mesylate, etc.) by treatment with a suitable base (e.g., Cs₂CO₃, K₂CO₃, NaHMDS). When X=OH, this displacement may be accomplished using a Mitsunobu protocol, for example by treatment with DIAD and PPh₃.

It is understood that the connectivity of the macrocycle precursor may be reversed (e.g., where Y is bonded to $L^m$ and Nu-P² is bonded to $L^n$ as depicted) but that the same sequence can be employed to effect macrocyclization.

An example of a compound prepared by this approach is Example 96.

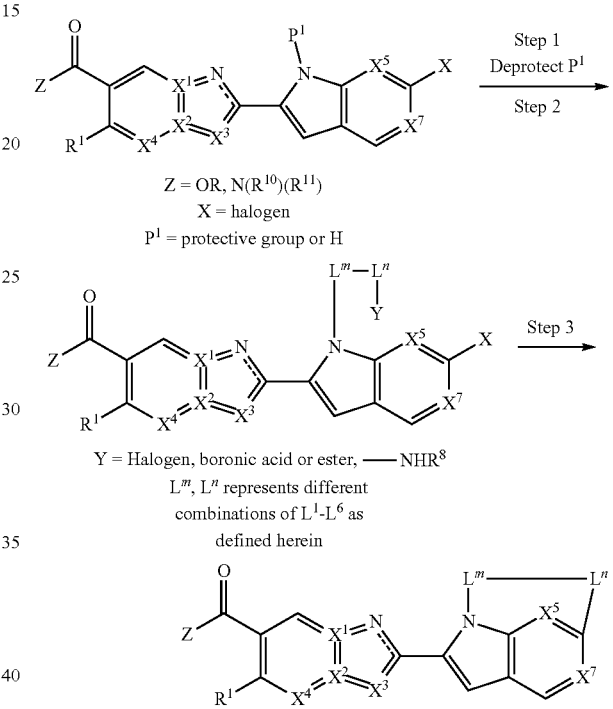

Scheme C-10 describes synthesis of a macrocycle by intramolecular cross-coupling.

Step 1 is as described in Scheme C-1.

Step 2 describes the generalized installation of a fragment -$L^n$-$L^m$-Y, where $L^m$ and $L^n$ comprise desired combinations of L groups described herein or precursors thereof, and where Y=halogen, boronic acid, ester, other suitable organometallic derivative, or —NH(R⁸). This is accomplished using protocols similar to those described herein or by transformations known to those versed in the art. In the case where Y=boronic acid, ester, other suitable organometallic derivative, or —NH (R⁸), the macrocyclization may be accomplished by treatment with a suitable palladium catalyst under appropriate conditions. In the case where Y=halogen, the intermediate may be treated with 4,4,5,5-tetramethyl-2-(4,4,5,5-tetramethyl-1,3,2-dioxaborolan-2-yl)-1,3,2-dioxaborolane and a suitable palladium catalyst under appropriate conditions to provide the macrocycle product by intermediacy of a pinacolboronic ester. An example prepared by this strategy is Example 85.

Scheme D-1

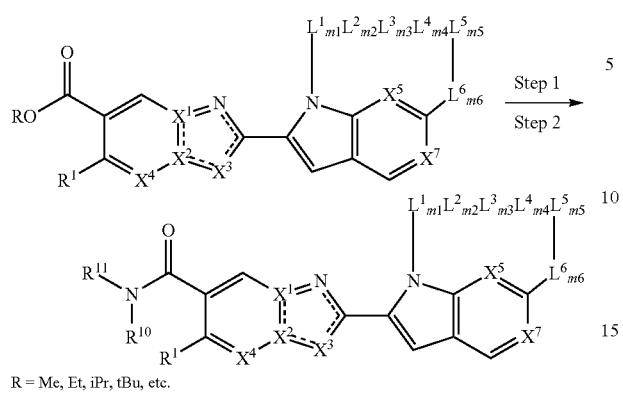

R = Me, Et, iPr, tBu, etc.

Scheme D-1 describes the installation of —N(R¹⁰)(R″) groups via amide bond formation.

Step 1 describes the hydrolysis of an ester motif to afford the corresponding carboxylic acid. This can be accomplished using a variety of conditions well known to those versed in the art, including treatment with hydroxide (e.g., LiOH, NaOH, KOH, etc.) in a suitable solvent mixture and temperature. This can also be accomplished under acidic conditions (e.g., TFA, HCl), especially when R=tert-butyl. Other known R groups that are compatible with the chemistry outlined herein can also be used, and these can be removed using standard conditions known to those versed in the art.

Step 2 shows the preparation of compounds of Formula (I) via amide bond forming chemistry. Suitable coupling conditions, reagents and/or catalysts are well known in the art.

It is understood that the sequence described above can be carried out at any appropriate stage prior to elaboration of the macrocyclic intermediate depicted in Scheme D-1.

PREPARATION EXAMPLES

Methods for preparing the novel compounds described herein will be apparent to those of skill in the art with suitable procedures being described, for example, in the reaction schemes and examples below.

The chemical names of the Examples in Tables 1 and 1A were generated using OpenEye, implemented in Dassault Systemes' Biovia Pipeline Pilot (version 19.1.0.1963). ChemBioDraw Ultra 14.0 or the naming function residing within Biovia Notebook 2019 (version 19.1.0.23) was used to generate names for intermediates reported herein. It should be understood that other names may be used to identify Examples or intermediates of the same structure. Other compounds, such as reactants, reagents and solvents, may be named with common names, or systematic or non-systematic names. The compounds may also be named using other nomenclature systems and symbols that are commonly recognized in the art of chemistry including, for example, Chemical Abstract Service (CAS) and International Union of Pure and Applied Chemistry (IUPAC). The naming and numbering of the compounds of the present disclosure is illustrated with representative compounds of formula (I), or (Ia)-(Iv) shown in Tables 1 and 1A below. The compounds provided in Tables 1 and 1A may be a single enantiomer (e.g., (S)-enantiomer, (R)-enantiomer), or the compounds may be present in a racemic or scalemic composition having one or more diastereomers or enantiomers as mixture.

1. Synthesis of Intermediates I-1 to I-25

Preparation of methyl 5-methoxy-3-methyl-2-(((trifluoromethyl)sulfonyl)oxy)imidazo[1,2-a]pyridine-7-carboxylate (I-1)

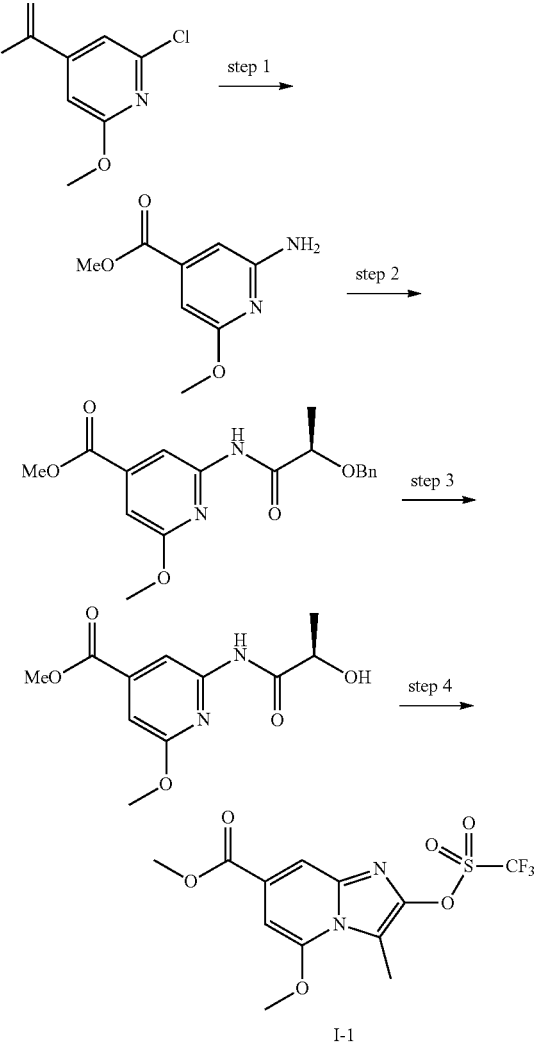

Step 1

Methyl 2-chloro-6-methoxyisonicotinate (10 g, 50 mmol), $Pd_2(dba)_3$ (900 mg, 1.0 mmol), Xantphos (1150 mg, 1.99 mmol), and cesium carbonate (33 g, 100 mmol) were taken up in 1,4-dioxane (300 mL) under $N_2$. Benzophenone imine (9.6 mL, 57 mmol) was added, and the resulting mixture was stirred at 90° C. for 16 h. The mixture was then cooled and partitioned between EtOAc and water. The phases were separated, and the organic phase was washed with brine, dried over $Na_2SO_4$, filtered, and concentrated. The crude residue was dissolved in THF (300 mL) and water (150 mL). Hydrochloric acid (12 M, 21 mL, 250 mmol) was added, and the resulting mixture was stirred until LC/MS indicated completion (~1 h). Solid NaHCO₃ (25 g, 300 mmol) was added, and the resulting mixture was diluted with EtOAc and water. The phases were separated, and the aqueous phase was extracted with EtOAc. The combined organic phase was dried over Na₂SO₄, filtered, and concentrated. The resulting residue was purified by silica gel chromatography (0-60% EtOAc in hexanes) to afford methyl 2-amino-6-methoxyisonicotinate. ES/MS: m/z 183.1 [M+H]⁺.

Step 2

(R)-2-(benzyloxy)propanoic acid (3.84 g, 21.3 mmol) was dissolved in DCM (64 mL) under N₂. DMF (100 uL) was added followed by dropwise addition of oxalyl chloride (1.80 mL, 21.3 mmol). The resulting mixture was stirred for 2 h at rt and was then added to a solution of methyl 2-amino-6-methoxyisonicotinate (3 g, 16.5 mmol) and trimethylamine (6.9 mL, 50 mmol) in DCM (40 mL) cooled in an ice water bath. The stirred mixture was let warm to rt. After 90 min, the mixture was diluted with DCM and water. The phases were separated, and the aqueous phase was extracted with DCM. The combined organic phase was dried over Na₂SO₄, filtered, and concentrated. The crude residue was purified by silica gel chromatography (10-50% EtOAc in hexanes) to afford methyl (R)-2-(2-(benzyloxy)propanamido)-6-methoxyisonicotinate. ES/MS: m/z 345.1 [M+H]⁺.

Step 3

Methyl (R)-2-(2-(benzyloxy)propanamido)-6-methoxyisonicotinate (5.19 g, 15 mmol) was dissolved in THF (100 mL) and EtOH (50 mL). Palladium on carbon (Degussa, 10% dry wt., 50% overall water wt.) (2 g, 0.94 mmol) was added and the reaction vessel was purged with H₂. The resulting mixture was stirred under 1 atm H₂ for 90 min and was then filtered through a pad of celite with THF. The filtrate was concentrated to afford methyl (R)-2-(2-hydroxypropanamido)-6-methoxyisonicotinate which was used without further purification. ES/MS: m/z 255.1 [M+H]⁺.

Step 4

Methyl (R)-2-(2-hydroxypropanamido)-6-methoxyisonicotinate (3.78 g, 14.9 mmol) was dissolved in DCM (150 mL) under N₂ and was cooled in a CO₂/acetone bath. 2-Methoxypyridine (4.7 mL, 44.7 mmol) was added followed by dropwise trifluoromethanesulfonic anhydride (7.53 mL, 44.6 mmol). The resulting mixture was stirred for 5 min and was then allowed to warm to rt. After 5 h, the reaction mixture was partitioned between DCM and water, and the aqueous phase was acidified with HCl. The phases were separated, and the aqueous phase was extracted with DCM. The combined organic phase was dried over Na₂SO₄, filtered, and concentrated to afford a crude residue. Purification by silica gel chromatography (20-100% EtOAc in hexanes) provided methyl 5-methoxy-3-methyl-2-(((trifluoromethyl)sulfonyl)oxy)imidazo[1,2-a]pyridine-7-carboxylate. ES/MS: m/z 368.9 [M+H]⁺. ¹H NMR (400 MHz, Chloroform-d) δ 7.89 (d, J=1.4 Hz, 1H), 6.64 (d, J=1.4 Hz, 1H), 4.07 (s, 3H), 3.94 (s, 3H), 2.71 (s, 3H).

Preparation of 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine (I-2)

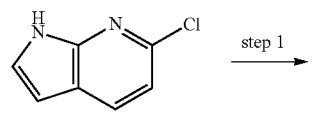

step 1

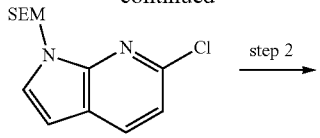

step 2

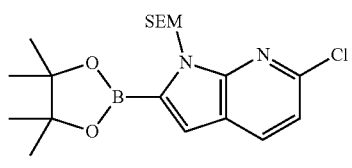

I-2

Step 1

Under an argon atmosphere, 6-chloro-1H-pyrrolo[2,3-b]pyridine (37.9 g, 248.1 mmol) and dry DMF (800 mL) were added to a 3 L oven-dried round bottom flask containing a magnetic stirring bar. The mixture was cooled to 0° C. and sodium hydride (60% dispersion in mineral oil, 10.9 g, 273 mmol, 1.1 equiv) was added in portion over 10 minutes. The resulting mixture was vigorously stirred for 1 hour and 2-(trimethylsilyl)ethoxymethyl chloride (45.5 g, 273 mmol, 1.1 equiv) was added. The resulting mixture was warmed to rt and stirred overnight, diluted with dichloromethane (1.5 L), and then quenched with water (100 mL). Additional water (500 mL) was added. The organic layer was washed with water, and brine, and dried over magnesium sulfate, filtered and evaporated to dryness. The residue was purified by chromatography over silica gel (EtOAc in Hexane, 0 to 5%) to afford 6-chloro-1-((2-(trimethylsilyl)ethoxy)methyl)-1H-pyrrolo[2,3-b]pyridine. ES/MS: m/z 283.2 [M+H]⁺. ¹H NMR (300 MHz, Chloroform-d) δ 7.84 (d, J=8.1 Hz, 1H), 7.32 (d, J=3.6 Hz, 1H), 7.10 (d, J=8.1 Hz, 1H), 6.52 (d, J=3.6 Hz, 1H), 5.64 (s, 2H), 3.53 (t, J=7.2 Hz, 1H), 2H), 0.91 (t, J=7.2 Hz, 2H), −0.06 (s, 9H).

Step 2

A solution of 6-chloro-1-((2-(trimethylsilyl)ethoxy)methyl)-1H-pyrrolo[2,3-b]pyridine (8.8 g, 31.1 mmol) in THF (100 mL) was cooled to −78° C. and n-BuLi (2.5 M in hexanes, 37.3 mmol, 1.2 equiv.) was added dropwise over 10 minutes. The resulting solution was stirred for an additional 2 h at this temperature. 2-Isopropoxy-4,4,5,5-tetramethyl-1,3,2-dioxaborolane (6.94 g, 37.3 mmol, 1.2 equiv.) was then added and the mixture was warmed to −20° C. over one hour. Then mixture was then stirred for 5 additional minutes at −20° C. before being quenched with HCl (1 M, 60 mL). The mixture was diluted with EtOAc and water. The organic phase was dired and concentrated, and the residual orange oil was purified by chromatography over silica gel (Hexanes:EtOAc 0 to 10%). 6-Chloro-2-(4,4,5,5-tetramethyl-1,3,2-dioxaborolan-2-yl)-1-((2-(trimethylsilyl)ethoxy)methyl)-1H-pyrrolo[2,3-b]pyridine was obtained. ES/MS: m/z 409.3 [M+H]⁺. ¹H NMR (400 MHz, CDCl₃) δ 7.87 (d, J=8.2 Hz, 1H), 7.13-7.06 (m, 2H), 5.91 (s, 2H), 3.59-3.50 (m, 2H), 1.39 (s, 12H), 0.96-0.85 (m, 2H), −0.07 (s, 9H).

145

Preparation of methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate (I-3)

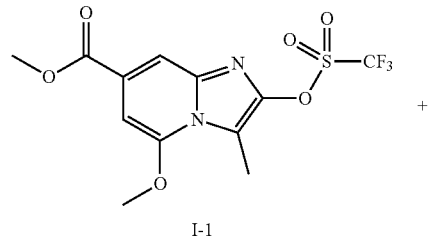

I-1

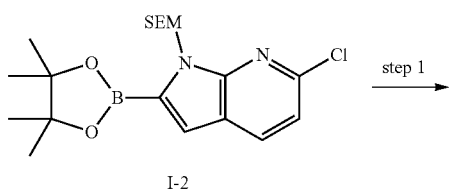

I-2

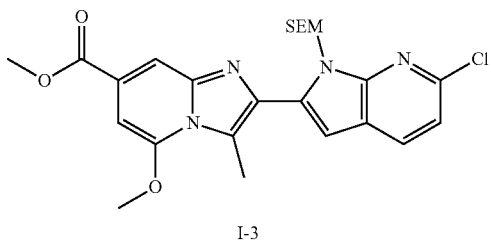

I-3

Step 1.

A round bottom flask was loaded with 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine (I-2, 11.5 g, 1.1 equiv.), methyl 5-methoxy-3-methyl-2-(((trifluoromethyl)sulfonyl)oxy)imidazo[1,2-a]pyridine-7-carboxylate (I-1, 9.4 g, 1 equiv.) and potassium phosphate tribasic (16.2 g, 3 equiv.). Dioxane (120 mL) and water (14 mL) were added, and the mixture was degassed with argon for 15 minutes. PdCl$_2$(dppf) (1.56 g, 7.5 mol %) was added in one portion and the mixture was heated to 45° C. for 6 hours. The reaction was worked up using EtOAc and water, and the combined organics were dried over sodium sulfate then evaporated to dryness. Purification via silica gel column chromatography using a solid loading over silica (0-45% ether/(hexanes:DCM 1:1)) delivered methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate. ES/MS: m/z 501.2 [M+H]$^+$. $^1$H NMR (400 MHz, CDCl$_3$) δ 8.08 (brs, 1H), 7.88 (d, J=8.1 Hz, 1H), 7.16 (d, J=8.1 Hz, 1H), 6.68 (brs, 1H), 6.66 (brs, 1H), 6.08 (s, 2H), 4.13 (s, 3H), 3.99 (s, 3H), 3.48-3.37 (m, 2H), 2.89 (s, 3H), 0.82-0.71 (m, 2H), −0.18 (s, 9H).

146

Preparation of 2-(6-acetyl-1-((2-(trimethylsilyl)ethoxy)methyl)-1H-pyrrolo[2,3-b]pyridin-2-yl)-6-methyl-1,3,6,2-dioxazaborocane-4,8-dione (I-4)

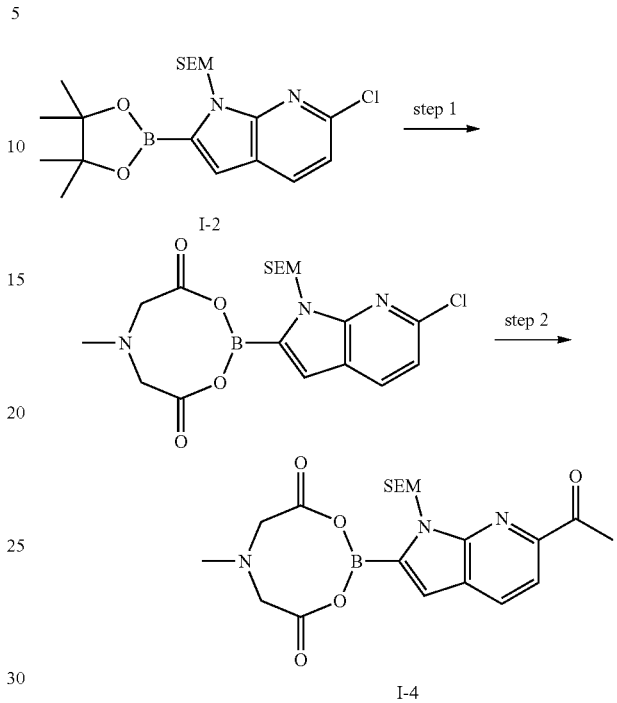

Step 1.

To a solution of 6-chloro-2-(4,4,5,5-tetramethyl-1,3,2-dioxaborolan-2-yl)-1-((2-(trimethylsilyl)ethoxy)methyl)-1H-pyrrolo[2,3-b]pyridine (I-2, 9.6 g, 23.5 mmol) in THF (120 mL) and water (30 mL) was added sodium periodate (14 g, 70.5 mmol). After stirring 20 min at rt, hydrochloric acid (1 M, 18 mL) was added. After an additional 2.5 h, the reaction mixture was partitioned between EtOAc and water. The organic phase was washed with brine, dried over Na$_2$SO$_4$, filtered, and concentrated under reduced pressure. The resulting residue along with methyliminodiacetic acid (10.4 g, 70 mmol), and 4 A MS (15 g) were taken up in DMF (52 mL), and that mixture was heated to 120° C. under N$_2$ for 2 h. The mixture was cooled and filtered to remove sieves, washing with DMF. The filtrate was concentrated in vacuo and the resulting residue was partitioned between EtOAc and water (~100 mL each). The phases were separated, and the organic phase was washed with water and brine, dried over Na$_2$SO$_4$, filtered and concentrated under reduced pressure. The resulting crude residue was purified on silica gel (5-25% acetone in hexanes) to yield 2-(6-chloro-1-((2-(trimethylsilyl)ethoxy)methyl)-1H-pyrrolo[2,3-b]pyridin-2-yl)-6-methyl-1,3,6,2-dioxazaborocane-4,8-dione. $^1$H NMR (400 MHz, Chloroform-d) δ 7.82 (d, J=8.1 Hz, 1H), 7.09 (d, J=8.1 Hz, 1H), 6.84 (s, 1H), 5.76 (s, 2H), 4.09 (d, J=16.5 Hz, 2H), 3.94 (d, J=16.5 Hz, 2H), 3.68-3.59 (m, 2H), 2.75 (s, 3H), 1.00-0.81 (m, 2H), 0.00 (s, 9H).

Step 2

2-(6-chloro-1-((2-(trimethylsilyl)ethoxy)methyl)-1H-pyrrolo[2,3-b]pyridin-2-yl)-6-methyl-1,3,6,2-dioxazaborocane-4,8-dione (4.51 g, 10.3 mmol) was taken up in dioxane (100 mL) under N$_2$. The reaction mixture was degassed by Ar bubbling for 10 min. 1-ethoxyvinyltributylstannane (7.4 mL, 20.6 mmol) and PdCl$_2$(dppf) (750 mg, 1.23 mmol) were added and the resulting mixture was heated to 100° C. After 20 h, LCMS showed complete conversion, and the reaction was cooled to room temperature, filtered over a plug of celite and the plug was rinsed with EtOAc three times. The resulting solution was evaporated to dryness. The resulting residue was dissolved in THF (100 mL) and aqueous 1 M HCl (50 mL, 50 mmol) was added. The resulting mixture was stirred vigorously for 45 minutes and was then diluted with DCM (200 mL) and water (150 mL). The phases were separated, the aqueous layer was extracted with DCM (150 mL) and the organic phase was dried over $Na_2SO_4$, filtered, and concentrated. Purification by silica gel chromatography (5-70% acetone in hexanes) afforded 2-(6-acetyl-1-((2-(trimethylsilyl)ethoxy)methyl)-1H-pyrrolo[2,3-b]pyridin-2-yl)-6-methyl-1,3,6,2-dioxazaborocane-4,8-dione. $^1$H NMR (400 MHz, DMSO-d6) δ 8.15 (d, J=8.1 Hz, 1H), 7.80 (d, J=8.1 Hz, 1H), 6.85 (s, 1H), 5.82 (s, 2H), 4.46 (d, J=17.3 Hz, 2H), 4.17 (d, J=17.2 Hz, 2H), 3.59-3.50 (m, 2H), 3.32 (s, 3H), 2.72 (s, 2H), 2.64 (s, 3H), 1.01-0.92 (m, 2H), −0.03--0.11 (m, 1H), −0.08 (s, 9H).

Preparation of methyl 2-chloro-3-cyclopropylimidazo[1,2-a]pyridine-7-carboxylate (I-5a)

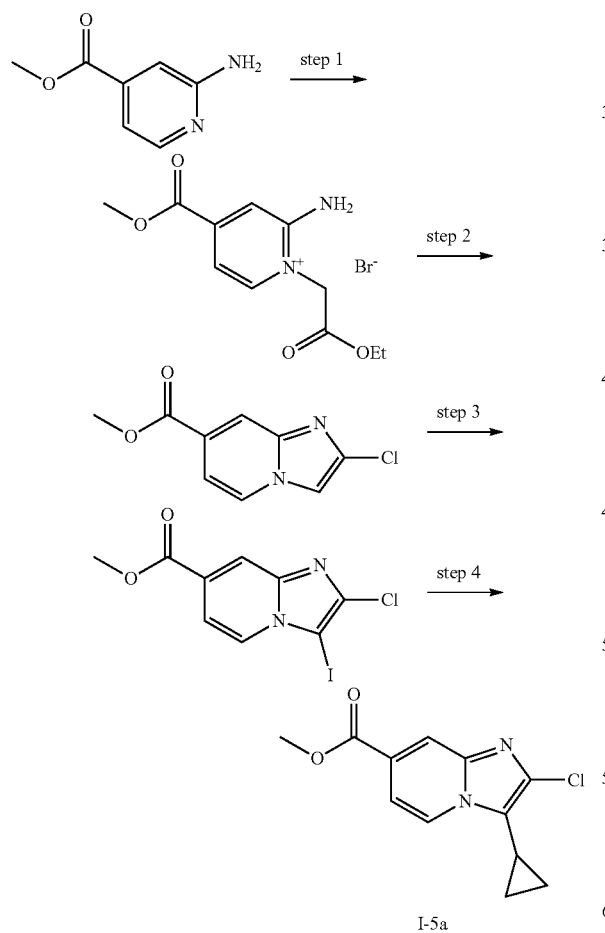

I-5a

Step 1

Methyl 2-aminoisonicotinate (7 g, 46 mmol) was suspended in ethyl bromoacetate (22 mL) and the reaction mixture was stirred at rt for 96 h. The reaction mixture was diluted with ether, stirred for 1 h, and filtered. The solids were washed with diethyl ether, and then dried in vacuo to provide 2-amino-1-(2-ethoxy-2-oxoethyl)-4-(methoxycarbonyl)pyridin-1-ium bromide. $^1$H NMR (400 MHz, DMSO-d6) δ 9.02 (s, 2H), 8.15 (d, J=7.0 Hz, 1H), 7.62 (d, J=1.8 Hz, 1H), 7.25 (dd, J=7.0, 1.8 Hz, 1H), 5.21 (s, 2H), 4.21 (q, J=7.1 Hz, 2H), 3.92 (s, 3H), 1.25 (t, J=7.1 Hz, 3H).

Step 2

A mixture of 2-amino-1-(2-ethoxy-2-oxoethyl)-4-(methoxycarbonyl)pyridin-1-ium bromide (580 mg, 1.82 mmol) and phosphorus oxychloride (3.4 mL, 36.6 mmol) was heated at 110° C. for 2 h. The reaction mixture was cooled to rt and quenched in portions into room temperature water. The mixture was then diluted with EtOAc and quenched with saturated $NaHCO_3$ (aq). The layers were separated and the aqueous phase was extracted with EtOAc. The combined organics were dried ($MgSO_4$), filtered, and concentrated under reduced pressure. The resulting residue was purified via silica gel column chromatography (0-50% acetone in hexanes) to yield methyl 2-chloroimidazo[1,2-a]pyridine-7-carboxylate. ES/MS: m/z 211.1 [M+H]$^+$.

Step 3

To a solution of methyl 2-chloroimidazo[1,2-a]pyridine-7-carboxylate (1.04 g, 4.94 mmol) in acetonitrile (50 mL) was added N-iodosuccinimide (1.35 g, 6 mmol). After 90 min, the reaction mixture was quenched with 10% aqueous sodium thiosulfate and diluted with water. The heterogeneous mixture was filtered, and the solids were washed with water and dried in vacuo to yield methyl 2-chloro-3-iodoimidazo[1,2-a]pyridine-7-carboxylate. ES/MS: m/z 337.2 [M+H]$^+$.

Step 4

A mixture of methyl 2-chloro-3-iodoimidazo[1,2-a]pyridine-7-carboxylate (2.09 g, 6.21 mmol), potassium cyclopropyltrifluoroborate (2315 mg, 15.64 mmol), palladium(II) acetate (167 mg, 0.74 mmol), butyldi-1-adamantylphosphine (539 mg, 1.5 mmol) and cesium carbonate (8150 mg, 25.01 mmol) in dioxane (15 mL) and water (1.5 mL) was heated at reflux for 15 h. After cooling to rt, the mixture was partioned between ethyl acetate and water. The layers were separated and the aqueous was extracted with ethyl acetate. The combined organics were washed with brine, dried ($MgSO_4$), filtered, and concentrated under reduced pressure. The resulting residue was purified via silica gel column chromatography (0-40% ethyl acetate in hexanes) to yield methyl 2-chloro-3-cyclopropylimidazo[1,2-a]pyridine-7-carboxylate. ES/MS: m/z 251.1 [M+H]$^+$.

Preparation of methyl 2-chloro-3-cyclopropyl-5-methoxyimidazo[1,2-a]pyridine-7-carboxylate (I-5b)

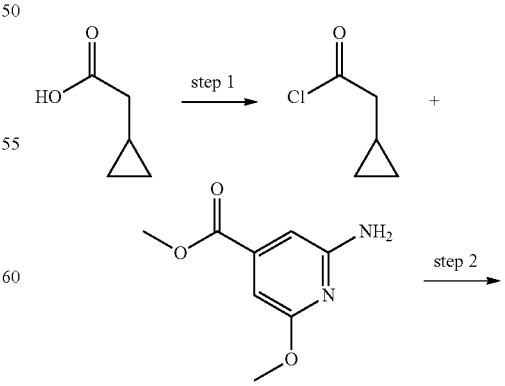

intermediate described in the synthesis of I-1

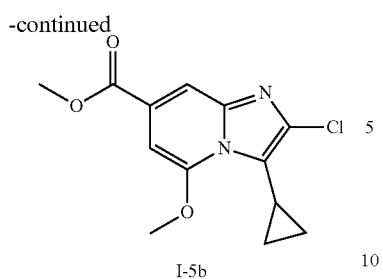

I-5b

Step 1

A solution of oxalyl chloride (2 M, 10.3 mL, 20.6 mmol) in dichloromethane was added to a solution of 2-cyclopropylacetic acid (1.0 mL, 10.3 mmol) in dichloromethane (17 mL) at room temperature. DMF (4 drops) was added and the reaction mixture was stirred at room temperature. After 4 h, the reaction mixture was concentrated under reduced pressure to yield 2-cyclopropylacetyl chloride, which was used directly in the next step without purification.

Step 2

To a mixture of 2-cyclopropylacetyl chloride (1.22 g, 10.3 mmol, above) and methyl 2-amino-6-methoxyisonicotinate (intermediate described in the syntheise of I-1, 1.50 g, 8.23 mmol) in chloroform (50 mL) was added triethylamine (2.3 mL, 16.5 mmol) at room temperature. After stirring overnight, the reaction mixture was transferred into 5×10 mL sealed reaction vessels. Triethylamine (0.24 mL, 1.72 mmol) and thionyl chloride (0.26 mL, 3.6 mmol) was added to each vessel. Each vessel was sealed and the reaction mixtures were heated at 70° C. for 90 minutes. After cooling to room temperature, the reaction mixtures were combined, diluted with dichloromethane, and quenched with sat. NaHCO$_3$(aq). The organic and aqueous layers were separated and the aqueous layer was extracted with dichloromethane. The combined organic layers were dried (MgSO$_4$), filtered, and concentrated under reduced pressure. The resulting residue was purified via silica gel column chromatography (0-40% ethyl acetate/hexanes) to yield methyl 2-chloro-3-cyclopropyl-5-methoxyimidazo[1,2-a]pyridine-7-carboxylate. ES/MS: m/z 281.0 [M+H]$^+$.

methyl 2-chloro-3-cyclopropyl-6-fluoroimidazo[1,2-a]pyridine-7-carboxylate (I-5c)

Prepared following a similar procedure to I-5a using methyl 2-amino-5-fluoroisonicotinate. ES/MS: m/z 269.2 [M+H]$^+$.

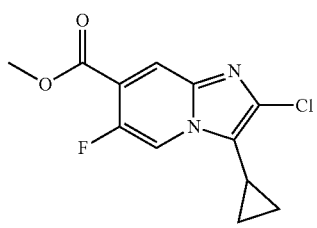

I-5c

Preparation of methyl 2-(6-acetyl-1-((2-(trimethylsilyl)ethoxy)methyl)-1H-pyrrolo[2,3-b]pyridin-2-yl)-3-cyclopropylimidazo[1,2-a]pyridine-7-carboxylate (I-6a)

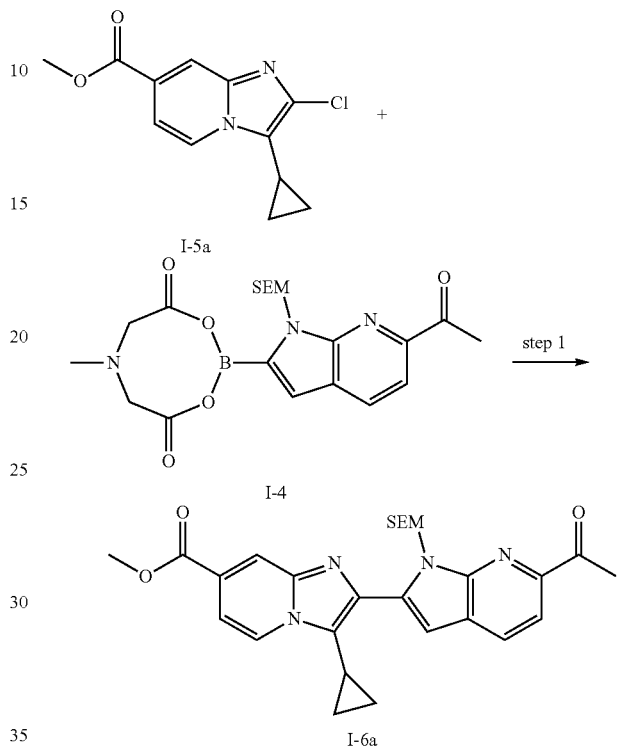

Step 1

A mixture of methyl 2-chloro-3-cyclopropylimidazo[1,2-a]pyridine-7-carboxylate (I-5a, 800 mg, 3.19 mmol), K$_3$PO$_4$ (5.08 g, 23.9 mmol), 2-(6-acetyl-1-((2-(trimethylsilyl)ethoxy)methyl)-1H-pyrrolo[2,3-b]pyridin-2-yl)-6-methyl-1,3,6,2-dioxazaborocane-4,8-dione (I-4, 1.84 g, 4.13 mmol), and XPhos Pd G3 (271 mg, 0.32 mmol) in dioxane (25 mL) and water (5 mL) was heated at 100° C. After 3 h, additional I-4 (923 mg, 2.07 mmol), and XPhos Pd G3 (270 mg, 0.32 mmol) were added and the reaction mixture was heated at 100° C. After 1 h, the reaction mixture was cooled to rt and partitioned between ethyl acetate and water. The layers were separated and the aqueous was extracted with ethyl acetate. The combined organics were washed with brine, dried (MgSO$_4$), filtered, and concentrated under reduced pressure. The resulting residue was purified via silica gel column chromatography (0-50% ethyl acetate in hexanes) to yield methyl 2-(6-acetyl-1-((2-(trimethylsilyl)ethoxy)methyl)-1H-pyrrolo[2,3-b]pyridin-2-yl)-3-cyclopropylimidazo[1,2-a]pyridine-7-carboxylate. ES/MS: m/z 505.0 [M+H]$^+$.

methyl 2-(6-acetyl-1-((2-(trimethylsilyl)ethoxy)methyl)-1H-pyrrolo[2,3-b]pyridin-2-yl)-3-cyclopropyl-5-methoxyimidazo[1,2-a]pyridine-7-carboxylate (I-6b)

Prepared following a similar procedure to I-6a starting with I-5b. ES/MS: m/z 535.0 [M+H]$^+$.

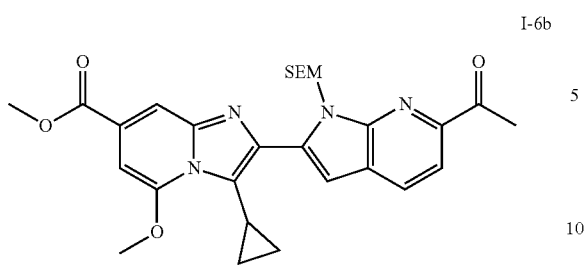

I-6b

Preparation of methyl 2-(6-bromo-1H-indol-2-yl)-7-methoxy-1-methyl-1H-benzo[d]imidazole-5-carboxylate (I-7a)

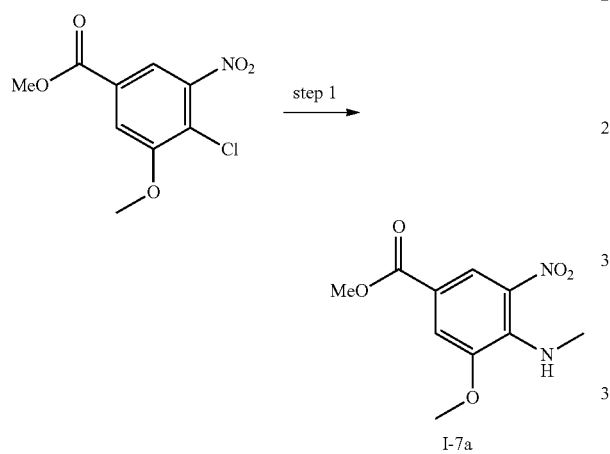

I-7a

Step 1

A 250 mL round bottom flask was charged with methyl 4-chloro-3-methoxy-5-nitrobenzoate (14.0 g, 57 mmol) and methylamine hydrochloride salt (4.65 g, 69 mmol). The solids were taken in DMF (100 mL) and triethylamine (14.1 g, 143 mmol) was added. The flask was sealed and the reaction mixture was stirred at 75° C. for 16 h. The reaction was partitioned between water and DCM. The aqueous layer was extracted with DCM and the combined organics were washed with water then brine. The combined organic layer was dried over sodium sulfate, filtered, and evaporated to dryness. The crude product was dissolved in hot EtOAc (80 mL) and hexanes (220 mL) were added. The mixture was allowed to cool to room temperature and the crystallization was aged overnight before collecting solids by filtration to afford methyl 2-(6-bromo-1H-indol-2-yl)-7-methoxy-1-methyl-1H-benzo[d]imidazole-5-carboxylate. ES/MS: m/z 241.0 [M+H]$^+$.

methyl 4-(cyclopropylamino)-3-methoxy-5-nitrobenzoate (I-7b)

Prepared following a similar procedure to I-7a using cyclopropylamine instead of methylamine. ES/MS: m/z 267.0 [M+H]$^+$.

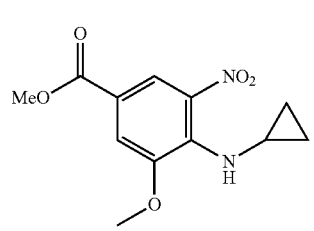

I-7b methyl 2-fluoro-4-(methylamino)-5-nitrobenzoate (I-7c)

Prepared following a similar procedure to I-7a using methyl 2,4-difluoro-5-nitrobenzoate. ES/MS: 227.1 [M−H]$^+$.

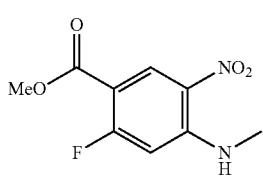

I-7c methyl 4-(cyclopropylamino)-2-fluoro-5-nitrobenzoate (I-7d)

Prepared following a similar procedure to I-7a using methyl 2,4-difluoro-5-nitrobenzoate and cyclopropylamine instead of methylamine. $^1$H NMR (400 MHz, DMSO-d6) δ 8.64 (d, J=7.8 Hz, 1H), 8.45 (s, 1H), 7.16 (d, J=14.0 Hz, 1H), 3.84 (s, 3H), 2.76-2.64 (m, 1H), 0.98-0.87 (m, 2H), 0.76-0.64 (m, 2H).

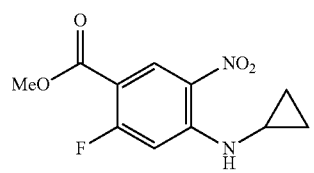

I-7d methyl 4-(cyclopropylamino)-3-nitrobenzoate (I-7e)

Prepared following a similar procedure to I-7a using methyl 4-fluoro-3-nitrobenzoate and cyclopropylamine instead of methylamine. ES/MS: m/z 237.8 [M+H]$^+$.

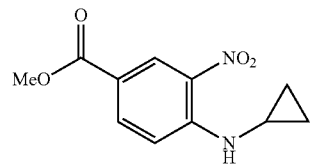

I-7e methyl 6-(methylamino)-5-nitronicotinate (I-7f)

Prepared following a similar procedure to I-7a using methyl 6-fluoro-5-nitronicotinate. $^1$H NMR (400 MHz, DMSO-d$_6$) δ 8.97 (q, J=4.8 Hz, 1H), 8.92 (d, J=2.1 Hz, 1H), 8.72 (d, J=2.1 Hz, 1H), 3.86 (s, 3H), 3.10 (d, J=4.8 Hz, 3H).

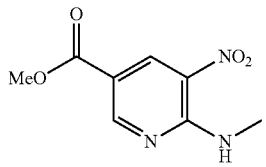

methyl 2-fluoro-4-[(1-methoxycyclopropyl)methyl-amino]-5-nitro-benzoate (I-7g)

Prepared following a similar procedure to I-7a using methyl 2,4-difluoro-5-nitrobenzoate and (1-methoxycyclopropyl)methanamine instead of methylamine. $^1$H NMR (400 MHz, Chloroform-d) δ 8.95 (d, J=7.7 Hz, 1H), 8.63 (s, 1H), 6.50 (d, J=13.2 Hz, 1H), 3.93 (s, 3H), 3.42 (d, J=4.5 Hz, 2H), 3.35 (d, J=1.0 Hz, 3H), 1.06-1.01 (m, 2H), 0.71-0.65 (m, 2H). $^{19}$F NMR (376 MHz, Chloroform-d) δ −98.29 (d, J=13.5 Hz).

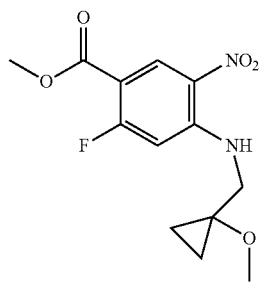

methyl 2-fluoro-4-((2-methoxyethyl)amino)-5-nitrobenzoate (I-7h)

Prepared following a similar procedure to I-7a using methyl 2,4-difluoro-5-nitrobenzoate and 2-methoxyethanamine. ES/MS: m/z 273.0 [M−H]$^+$.

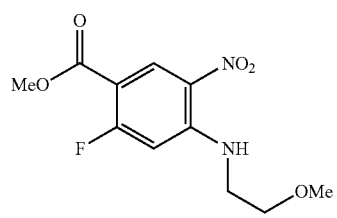

methyl 4-((2,2-difluoroethyl)amino)-2-fluoro-5-nitrobenzoate (I-7i)

Prepared following a similar procedure to I-7a using methyl 2,4-difluoro-5-nitrobenzoate and 2,2-difluoroethane-1-amine. ES/MS: Does not ionize.

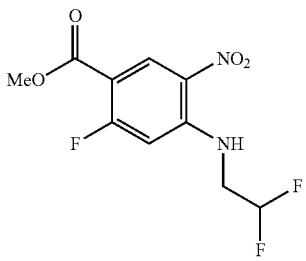

methyl 2-fluoro-5-nitro-4-((2,2,2-trifluoroethyl)amino)benzoate (I-7j)

Prepared following a similar procedure to I-7a using methyl 2,4-difluoro-5-nitrobenzoate and 2,2,2-trifluoroethan-1-amine. ES/MS: m/z 297.1 [M−H]$^+$.

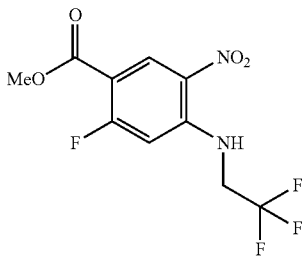

methyl 3-methoxy-4-((2-methoxyethyl)amino)-5-nitrobenzoate (I-7k)

Prepared following a similar procedure to I-7a using methyl 3-methoxy-4-((2-methoxyethyl)amino)-5-nitrobenzoate. ES/MS: m/z 285.1 [M−H]$^+$.

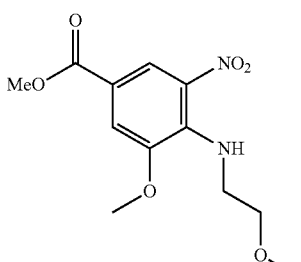

methyl 2-fluoro-4-[(1-methoxycyclopropyl)methyl-amino]-5-nitro-benzoate (I-7l)

Prepared following a similar procedure to I-7a using methyl 2,4-difluoro-5-nitrobenzoate and (1-methoxycyclopropyl)methanamine instead of methylamine. $^1$H NMR (400 MHz, Chloroform-d) δ 8.95 (d, J=7.7 Hz, 1H), 8.63 (s, 1H), 6.50 (d, J=13.2 Hz, 1H), 3.93 (s, 3H), 3.42 (d, J=4.5 Hz, 2H), 3.35 (d, J=1.0 Hz, 3H), 1.06-1.01 (m, 2H), 0.71-0.65 (m, 2H). $^{19}$F NMR (376 MHz, Chloroform-d) δ −98.29 (d, J=13.5 Hz).

I-7l

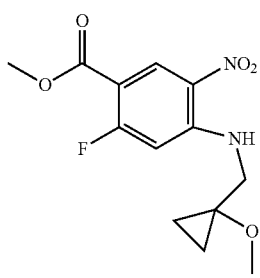

methyl 2-methoxy-4-(methylamino)-5-nitrobenzoate (I-7m)

Prepared following a similar procedure to I-7a using methyl 4-fluoro-2-methoxy-5-nitro-benzoate. ES/MS: m/z 241.0 [M–H]+.

I-7m

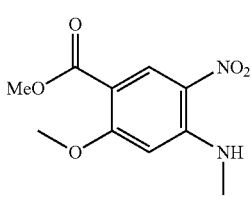

methyl 2-methyl-4-(methylamino)-5-nitrobenzoate (I-7n)

Prepared following a similar procedure to I-7a using methyl 4-fluoro-2-methyl-5-nitrobenzoate. ES/MS: m/z 225.2 [M–H]+.

I-7n

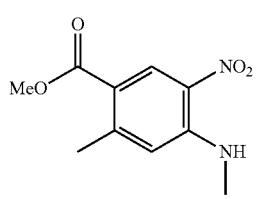

methyl 2,3-difluoro-4-(methylamino)-5-nitrobenzoate (I-7o)

Prepared following a similar procedure to I-7a using methyl 2,3,4-trifluoro-5-nitrobenzoate. ES/MS: m/z does not ionize.

I-7o

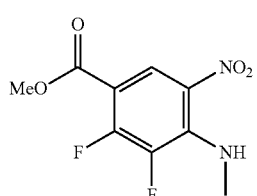

methyl 2,3-difluoro-4-((2-methoxyethyl)amino)-5-nitrobenzoate (I-7p)

Prepared following a similar procedure to I-7a using methyl 2,3,4-trifluoro-5-nitrobenzoate and 2-methoxyethan-1-amine. ES/MS: m/z does not ionize.

I-7p

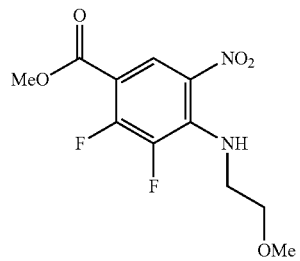

methyl 6-(cyclopropylamino)-5-nitronicotinate (I-7q)

Prepared following a similar procedure to I-7a using methyl 6-fluoro-5-nitronicotinate and cyclopropylamine. ES/MS: m/z 238.0 [M–H]+.

I-7q

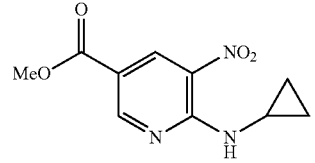

methyl 3-chloro-4-(methylamino)-5-nitrobenzoate (I-7r)

Prepared following a similar procedure to I-7a using methyl 3,4-dichloro-5-nitrobenzoate. ES/MS: m/z 246.0 [M+H]+.

I-7r

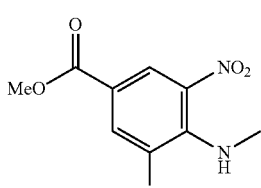

methyl 3-fluoro-4-(methylamino)-5-nitrobenzoate (I-7s)

Prepared following a similar procedure to I-7a using methyl 3,4-difluoro-5-nitrobenzoate. ES/MS: m/z 229.2 [M+H]+.

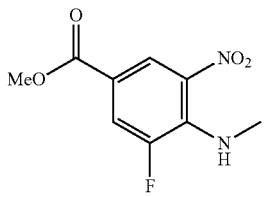

methyl 3-fluoro-4-(isopropylamino)-5-nitrobenzoate
(I-107t)

Prepared following a similar procedure to I-140c using isopropylamine. ES/MS: m/z 256.9 [M+H]⁺.

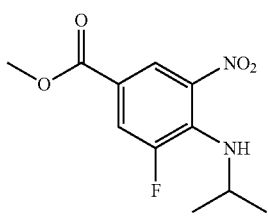

methyl 4-(2,2-dimethylpropylamino)-3-fluoro-5-nitro-benzoate (I-107u)

Prepared following a similar procedure to I-140c using 2,2-dimethylpropan-1-amine. ES/MS: m/z 285.0 [M+H]⁺.

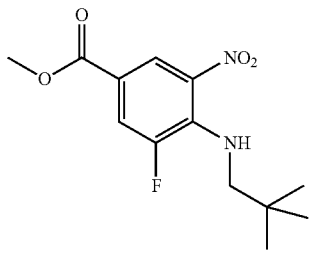

Preparation of methyl 2-(6-bromo-1H-pyrrolo[2,3-b]pyridin-2-yl)-7-methoxy-1-methyl-1H-benzo[d]imidazole-5-carboxylate (I-8a)

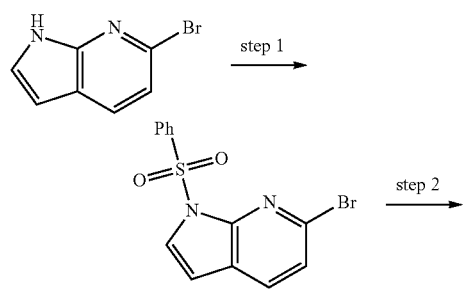

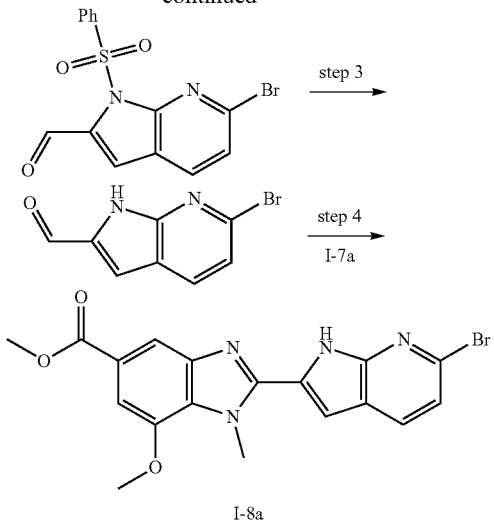

Step 1
To a stirred solution of 6-bromo-1H-pyrrolo[2,3-b]pyridine (10.0 g, 50.8 mmol) in DMF (100 mL) was added NaH (2.43 g, 101.3 mmol) at 0° C. After stirring for 10 minutes, benzenesulfonyl chloride (7.1 mL, 55.9 mmol) was added and the reaction mixture was held for 2 h at 0° C. The reaction mixture was quenched with ice-water, filtered, washed with cold water and the solid was dried under vacuum to afford 6-bromo-1-(phenylsulfonyl)-1H-pyrrolo[2,3-b]pyridine, which was used directly without any further purification. ¹H NMR (400 MHz, Chloroform-d) δ 8.27-8.20 (m, 2H), 7.72-7.65 (m, 2H), 7.65-7.57 (m, 1H), 7.56-7.48 (m, 2H), 7.32 (dd, J=8.1, 0.6 Hz, 1H), 6.56 (d, J=4.0 Hz, 1H).

Step 2
To a stirred solution of 6-bromo-1-(phenylsulfonyl)-1H-pyrrolo[2,3-b]pyridine (5 g, 14.8 mmol) in THF (50 mL) was added 2 M LDA solution in THF (11.5 mL, 16.3 mmol) under argon at −78° C. The reaction mixture was stirred for 30 min at −78° C., then quenched with DMF (1.62 g) and stirred for 1 h at −78° C. The reaction mixture was quenched with sat. aq. NH₄Cl solution and extracted with ethyl acetate. The organic layer was washed with brine, dried over anhydrous sodium sulfate, and concentrated under reduced pressure. The crude mixture was purified by silica gel column chromatography, eluting with 30% ethyl acetate in petroleum ether to afford 6-bromo-1-(phenylsulfonyl)-1H-pyrrolo[2,3-b]pyridine-2-carbaldehyde. ES/MS: m/z 364.9, 366.9 [M+H]⁺.

Step 3
To a stirred solution of 6-bromo-1-(phenylsulfonyl)-1H-pyrrolo[2,3-b]pyridine-2-carbaldehyde (13.5 g, 37.1 mmol) in methanol (130 mL) under argon was added 1 M NaOH aqueous solution (270 mL) at 0° C., and the reaction was stirred for 6 h at 0° C. The reaction mixture was filtered through a plug of Celite, washed with methanol and the filtrate was evaporated under reduced pressure. The crude mixture was purified by silica gel column chromatography, eluting with 30% ethyl acetate in petroleum ether to obtain 6-bromo-1H-pyrrolo[2,3-b]pyridine-2-carbaldehyde. ES/MS: m/z 225.1, 227.1 [M+H]⁺.

Step 4
Methyl 3-methoxy-4-(methylamino)-5-nitrobenzoate (I-7a, 4 g, 16.65 mmol) and 6-bromo-1H-pyrrolo[2,3-b]

pyridine-2-carbaldehyde (3.75 g, 16.65 mmol) were charged in a sealable 500 mL round bottom flask. The mixture was dissolved in 300 mL of EtOH/H₂O (2:1) and sodium dithionite (8.70 g, 50 mmol) was added in one portion. The flask was immediately sealed and heated to 90° C. A white precipitate quickly forms and the reaction was stirred ~ 2 h. Water (300 mL) was added to the reaction mixture and it was allowed to cool to room temperature. The white solid was then filtered and washed with water (2×100 mL) followed by diethyl ether (2×75 mL). The solid was dried to afford methyl 2-(6-bromo-1H-pyrrolo[2,3-b]pyridin-2-yl)-7-methoxy-1-methyl-1H-benzo[d]imidazole-5-carboxylate. ES/MS: m/z 415.1, 417.1 [M+H]⁺.

methyl 2-(6-bromo-1H-indol-2-yl)-7-methoxy-1-methyl-1H-benzo[d]imidazole-5-carboxylate (I-8b)

Prepared following a similar procedure to I-8a using commercially available 6-bromo-1H-indole-2-carbaldehyde instead of 6-bromo-1H-pyrrolo[2,3-b]pyridine-2-carbaldehyde. ES/MS: m/z 414.2, 416.2 [M+H]⁺.

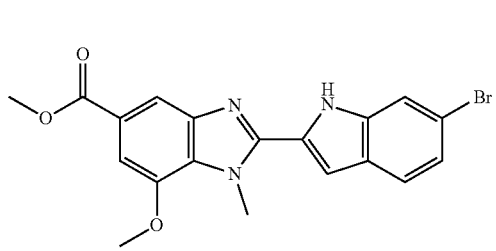

I-8b methyl 2-(6-bromo-1H-pyrrolo[2,3-b]pyridin-2-yl)-6-fluoro-1-methyl-1H-benzo[d]imidazole-5-carboxylate (I-8c)

Prepared following a similar procedure to I-8a using I-7c. ES/MS: m/z 403.2, 405.2 [M+H]⁺.

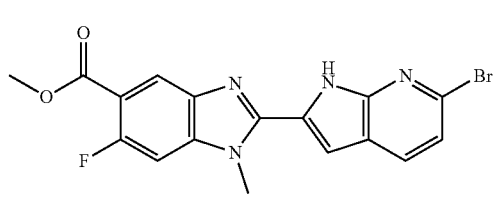

I-8c

Preparation of methyl 2-(6-acetyl-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate (I-9a)

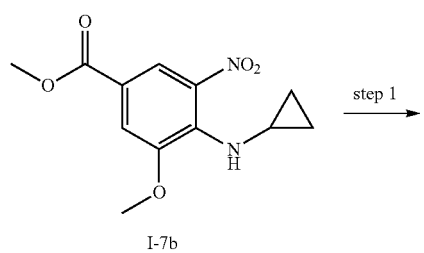

I-7b

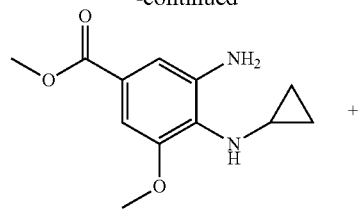

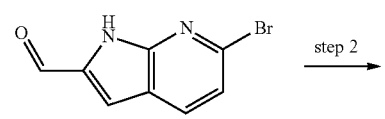

intermediate described in the synthesis of I-8a

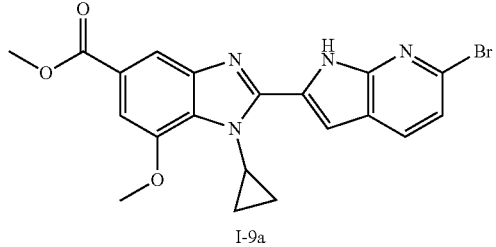

I-9a

Step 1

10% Pd/C (631 mg, 0.59 mmol) was added to a mixture of methyl 4-(cyclopropylamino)-3-methoxy-5-nitrobenzoate (1580 mg, 5.93 mmol) in ethanol (30 mL) and ethyl acetate (15 mL). The reaction mixture was placed under 1 atm of hydrogen. After 4 h, the reaction mixture was filtered through celite and the filtrate was concentrated under reduced pressure. The resulting residue was purified via silica gel column chromatography (10-40% ethyl acetate in hexanes) to yield methyl 3-amino-4-(cyclopropylamino)-5-methoxybenzoate. ES/MS: m/z 237.1 [M+H]⁺.

Step 2

OXONE®, monopersulfate compound (711 mg, 2.31 mmol) was added to a mixture of methyl 3-amino-4-(cyclopropylamino)-5-methoxybenzoate (455 mg, 1.93 mmol) and 6-bromo-1H-pyrrolo[2,3-b]pyridine-2-carbaldehyde (intermediate described in the synthesis of I-8a, 477 mg, 2.12 mmol) in DMF (6 mL) and water (2.5 mL). After 2 h, water was added to precipitate solids. The solid was filtered, washed with water, and dried in vacuo to yield methyl methyl 2-(6-bromo-1H-pyrrolo[2,3-b]pyridin-2-yl)-1-cyclopropyl-7-methoxy-1H-benzo[d]imidazole-5-carboxylate. ES/MS: m/z 441.1, 443.1 [M+H]⁺.

methyl 2-(6-bromo-1H-indol-2-yl)-1-cyclopropyl-7-methoxy-1H-benzo[d]imidazole-5-carboxylate (I-9b)

Prepared following a similar procedure to I-9a using 6-bromo-1H-indole-2-carbaldehyde (cas 105191-12-6) instead of 6-bromo-1H-pyrrolo[2,3-b]pyridine-2-carbaldehyde. ES/MS: m/z 440.1, 442.1 [M+H]⁺.

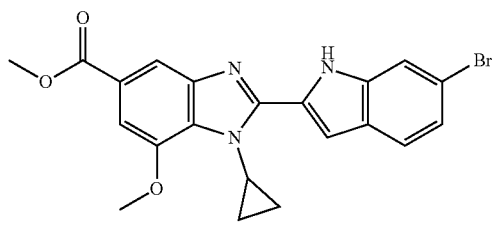

methyl 2-(6-bromo-1H-pyrrolo[2,3-b]pyridin-2-yl)-1-cyclopropyl-6-fluoro-1H-benzo[d]imidazole-5-carboxylate (I-9c)

Prepared following a similar procedure to I-9a using I-7d. ES/MS: m/z 429.2, 431.2 [M+H]+.

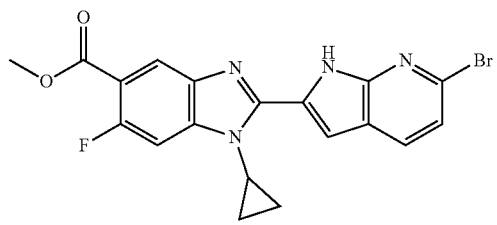

methyl 2-(6-bromo-1H-pyrrolo[2,3-b]pyridin-2-yl)-1-cyclopropyl-1H-benzo[d]imidazole-5-carboxylate (I-9d)

Prepared following a similar procedure to I-9a using I-7e. ES/MS: m/z 411.2, 413.1 [M+H]+.

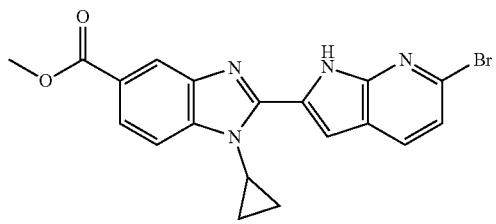

methyl 2-(6-bromo-1H-pyrrolo[2,3-b]pyridin-2-yl)-1-methyl-1H-benzo[d]imidazole-5-carboxylate (I-9e)

Prepared following a similar procedure to I-9a using methyl 4-(methylamino)-3-nitrobenzoate. ES/MS: m/z 385.1, 387.1 [M+H]+.

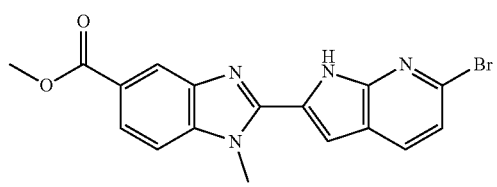

methyl 2-(6-bromo-1H-indol-2-yl)-6-fluoro-1-methyl-1H-benzo[d]imidazole-5-carboxylate (I-9f)

Prepared following a similar procedure to I-9a using 6-bromo-1H-indole-2-carbaldehyde (cas 105191-12-6) instead of 6-bromo-1H-pyrrolo[2,3-b]pyridine-2-carbaldehyde and methyl 2-fluoro-4-(methylamino)-5-nitrobenzoate (I-7c). ES/MS: m/z 403.4 [M+H]+.

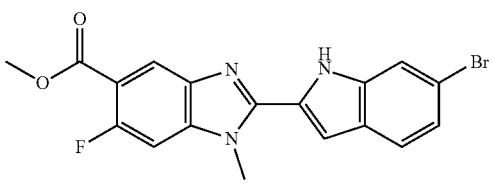

Preparation of methyl 2-(6-bromo-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-10a)

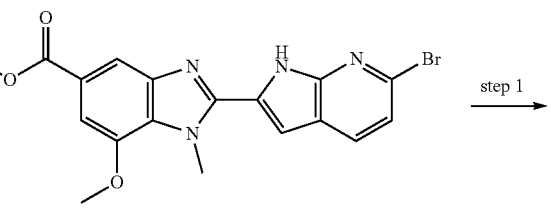

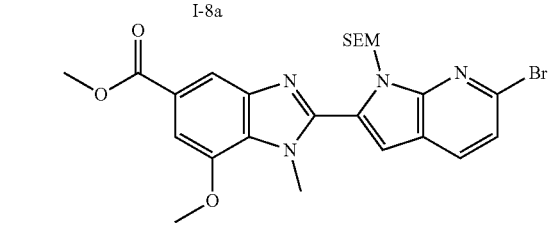

Step 1

A suspension of methyl 2-(6-bromo-1H-pyrrolo[2,3-b]pyridin-2-yl)-7-methoxy-1-methyl-1H-benzo[d]imidazole-5-carboxylate (I-8a, 10.68 g, 25.7 mmol) in DMF 260 mL was cooled to −15° C. (sodium chloride ice bath) and a solution of NaHMDS (2M in THF, 14.1 mL, 28.3 mmol) was added dropwise over 10 minutes. The resulting mixture was stirred 1 hour at −15° C. and then 4 hours at 0° C. before 2-(chloromethoxy) ethyl-trimethyl-silane (5.14 g, 30.8 mmol) was added. The resulting mixture was stirred at 0° C. until full conversion (about one hour). The mixture was then carefully quenched with saturated aqueous ammonium chloride and after usual work up (EtOAc/water) the residual oil was purified by silica gel column chromatography (0-40% EtOAc in hexanes) to afford methyl 2-(6-bromo-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 544.8, 546.8 [M+H]+.

methyl 2-(6-bromo-1-((2-(trimethylsilyl)ethoxy) methyl)-1H-pyrrolo[2,3-b]pyridin-2-yl)-1-cyclopropyl-7-methoxy-1H-benzo[d]imidazole-5-carboxylate (I-10b)

Prepared following a similar procedure to I-10a starting with I-9a. ES/MS: m/z 571.2, 573.2 [M+H]⁺.

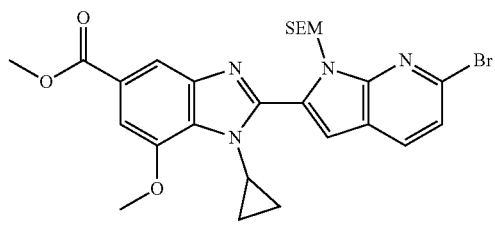

methyl 2-(6-bromo-1-((2-(trimethylsilyl)ethoxy) methyl)-1H-pyrrolo[2,3-b]pyridin-2-yl)-6-fluoro-1-methyl-1H-benzo[d]imidazole-5-carboxylate (I-10c)

Prepared following a similar procedure to I-10a starting with I-8c. ES/MS: m/z 533.2, 535.2 [M+H]⁺.

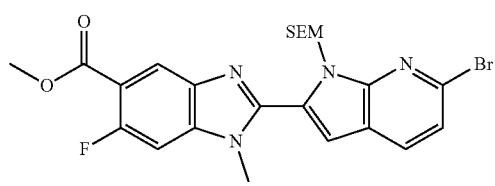

methyl 2-(6-bromo-1-((2-(trimethylsilyl)ethoxy) methyl)-1H-pyrrolo[2,3-b]pyridin-2-yl)-1-cyclopropyl-6-fluoro-1H-benzo[d]imidazole-5-carboxylate (I-10d)

Prepared following a similar procedure to I-10a starting with I-9c. ES/MS: m/z 558.8, 560.8 [M+H]⁺.

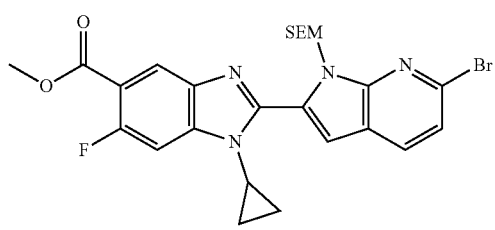

methyl 2-(6-bromo-1-((2-(trimethylsilyl)ethoxy) methyl)-1H-pyrrolo[2,3-b]pyridin-2-yl)-1-cyclopropyl-1H-benzo[d]imidazole-5-carboxylate (I-10e)

Prepared following a similar procedure to I-10a starting with I-9d. ES/MS: m/z 541.2, 543.2 [M+H]⁺.

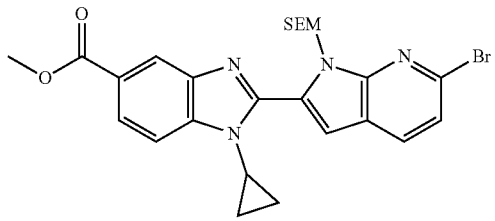

methyl 2-(6-bromo-1-((2-(trimethylsilyl)ethoxy) methyl)-1H-pyrrolo[2,3-b]pyridin-2-yl)-1-methyl-1H-benzo[d]imidazole-5-carboxylate (I-10f)

Prepared following a similar procedure to I-10a starting with I-9e. ES/MS: m/z 515.2, 517.2 [M+H]⁺.

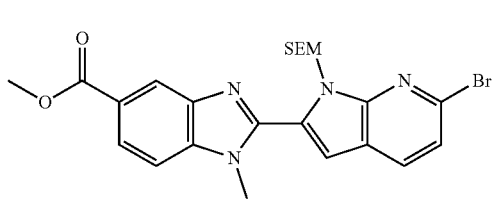

Preparation of methyl 2-(6-bromo-1-(tert-butoxycarbonyl)-1H-indol-2-yl)-7-methoxy-1-methyl-1H-benzo[d]imidazole-5-carboxylate (I-11a)

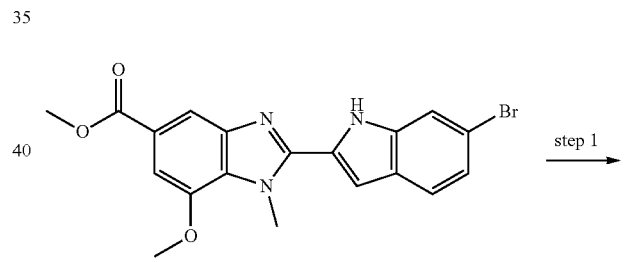

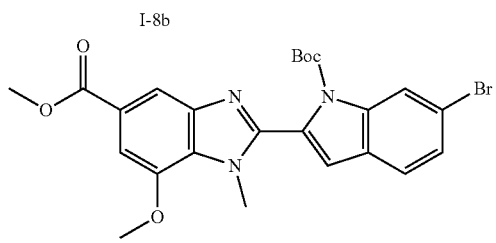

Step 1

Methyl 2-(6-bromo-1H-indol-2-yl)-7-methoxy-1-methyl-1H-benzo[d]imidazole-5-carboxylate (19.9 g, 48 mmol) was suspended in DCM (150 mL). Triethylamine (7 mL, 50 mmol) was added followed by Boc₂O (11.5 g, 52.8 mmol) and DMAP (4.18 g, 24 mmol). The mixture was stirred until full conversion as judged by LCMS analysis. Silica was added to the reaction mixture and the crude was evaporated to dryness. The residue was then purified by column chromatography (0-35% EtOAc in Heptane) to afford methyl 2-(6-bromo-1-(tert-butoxycarbonyl)-1H-indol-2-yl)-7- methoxy-1-methyl-H-benzo[d]imidazole-5-carboxylate. ES/MS: does not ionize, see I-13b for next intermediate.

methyl 2-(6-bromo-1-(tert-butoxycarbonyl)-1H-indol-2-yl)-1-cyclopropyl-7-methoxy-1H-benzo[d]imidazole-5-carboxylate (I-11b)

Prepared following a similar procedure to I-11a starting with I-9b. ES/MS: does not ionize, see I-13c for next intermediate.

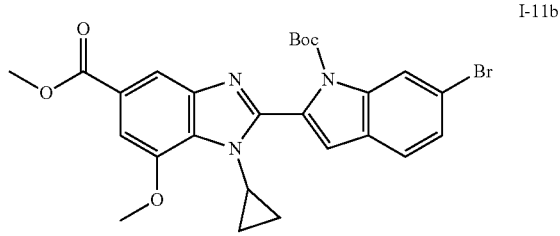 [SMILES: COC(=O)c1cc(OC)c2c(c1)nc(-c1cc3ccc(Br)cc3n1C(=O)OC(C)(C)C)n2C1CC1]

methyl 2-(6-bromo-1-(tert-butoxycarbonyl)-1H-indol-2-yl)-6-fluoro-1-methyl-1H-benzo[d]imidazole-5-carboxylate (I-11c)

Prepared following a similar procedure to I-11a starting with I-9f. ES/MS: does not ionize, see I-13j for next intermediate.

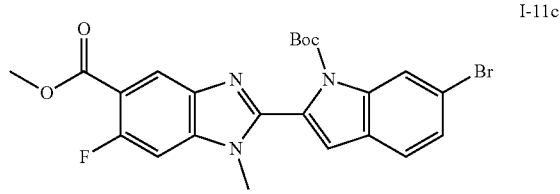 [SMILES: COC(=O)c1cc2nc(-c3cc4ccc(Br)cc4n3C(=O)OC(C)(C)C)n(C)c2cc1F]

Preparation of methyl 2-(6-acetyl-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate (I-12)

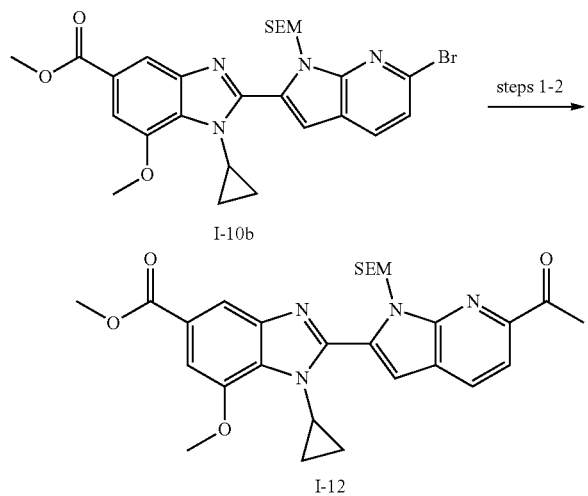

Step 1

Methyl 2-(6-bromo-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate (I-10b, ca. 2.95 mmol) was dissolved in ethanol (30 mL) and potassium trifluoro(isopropenyl)boronate (1.33 g, 9 mmol), dichloro 1,1'-bis(diphenylphosphino)ferrocene palladium (II) dichloromethane (0.24 g, 0.3 mmol) and triethylamine (2.1 mL, 15.1 mmol) were added. The system was evacuated, placed under argon, and the reaction mixture was heated at reflux. After 3 h, the reaction mixture was cooled to rt and filtered through celite. The filtrate was concentrated to yield methyl 1-cyclopropyl-7-methoxy-2-(6-(prop-1-en-2-yl)-1-((2-(trimethylsilyl)ethoxy)methyl)-1H-pyrrolo[2,3-b]pyridin-2-yl)-1H-benzo[d]imidazole-5-carboxylate, which was used below without further purification. ES/MS: m/z 533.0 [M+H]$^+$.

Step 2

Potassium osmate(VI) dihydrate (54 mg, 0.15 mmol) and sodium periodate (2270 mg, 10.61 mmol) were added to a mixture of methyl 1-cyclopropyl-7-methoxy-2-(6-(prop-1-en-2-yl)-1-((2-(trimethylsilyl)ethoxy)methyl)-1H-pyrrolo[2,3-b]pyridin-2-yl)-1H-benzo[d]imidazole-5-carboxylate (1.57 g, 2.98 mmol) in THF (60 mL) and water (50 mL) at rt. After stirring overnight, the reaction mixture was diluted with water and ethyl acetate. The layers were separated and the aqueous was extracted with ethyl acetate. The combined organics were washed with water, brine, dried (MgSO$_4$), filtered, and concentrated under reduced pressure. The resulting residue was purified via silica gel column chromatography (5-45% ethyl acetate in hexanes) to yield methyl 2-(6-acetyl-1-((2-(trimethylsilyl)ethoxy)methyl)-1H-pyrrolo[2,3-b]pyridin-2-yl)-1-cyclopropyl-7-methoxy-1H-benzo[d]imidazole-5-carboxylate. ES/MS: m/z 534.9 [M+H]$^+$.

Preparation of methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-13a)

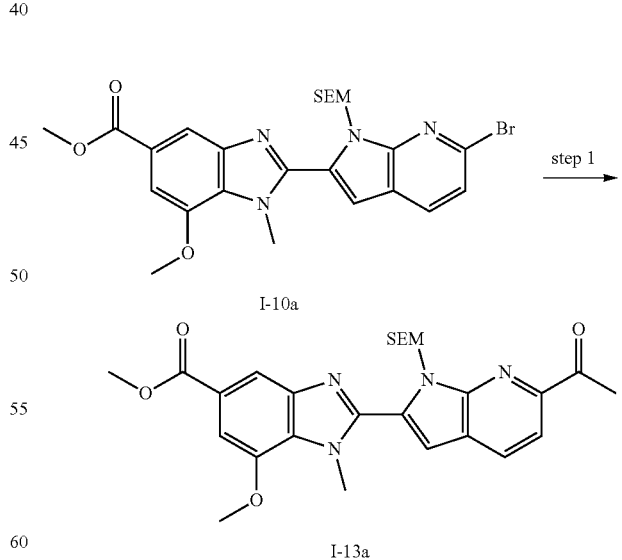

Step 1

Methyl 2-(6-bromo-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-10a, 6.92 g, 12.7 mmol) and PdCl$_2$(dppf).CH$_2$Cl$_2$ (600 mg, 0.735 mmol, 6 mol %)

were taken up in dioxane (150 mL), and the headspace was flushed with N₂. 1-Ethoxyvinyltributyltin (7.5 mL, 22.2 mmol, 1.75 equiv.) was added, and the resulting mixture was stirred at 100° C. for 6 h. Upon cooling, the mixture was filtered with EtOAc through Celite and the filtrate was concentrated. The resulting residue was dissolved in DCM and was filtered through a plug of silica gel with 1:1 DCM to remove most of the dark coloration. The filtrate was concentrated and was dissolved in THF (200 mL) and water (50 mL). Hydrochloric acid (3 M, 4.2 mL, 12.6 mmol) was added, and the resulting solution was stirred 20 min. Solid NaHCO₃ (2.5 g, 30 mmol) was added, and the mixture was diluted further with brine and DCM (50 mL). The organic phase was washed with brine, dried over Na₂SO₄, filtered, and concentrated. The resulting crude solid was slurried in 10 mL EtOAc and 100 mL hexanes. The product was collected via filtration, and the filter cake was washed with additional 15% EtOAc in hexanes (30 mL) and 100% hexanes to afford methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 509.3 [M+H]⁺.

methyl 2-(6-acetyl-1-(tert-butoxycarbonyl)-1H-indol-2-yl)-7-methoxy-1-methyl-1H-benzo[d]imidazole-5-carboxylate (I-13b)

Prepared following a similar procedure to I-13a using I-11a. ES/MS: m/z 478.0 [M+H]⁺.

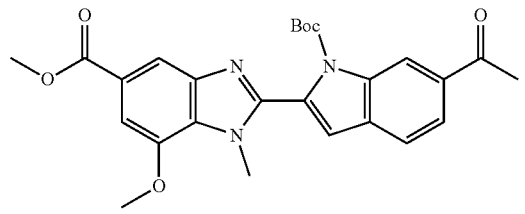

methyl 2-(6-acetyl-1-(tert-butoxycarbonyl)-1H-indol-2-yl)-1-cyclopropyl-7-methoxy-1H-benzo[d]imidazole-5-carboxylate (I-13c)

Prepared following a similar procedure to I-13a using I-11b. ES/MS: m/z 504.0 [M+H]⁺.

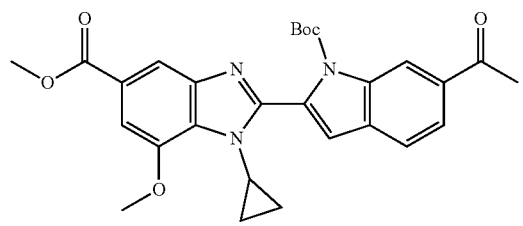

methyl 2-(6-acetyl-1-((2-(trimethylsilyl)ethoxy)methyl)-1H-pyrrolo[2,3-b]pyridin-2-yl)-6-fluoro-1-methyl-1H-benzo[d]imidazole-5-carboxylate (I-13d)

Prepared following a similar procedure to I-13a using I-10c. ES/MS: m/z 497.0 [M+H]⁺.

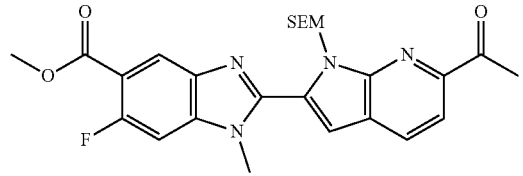

methyl 2-(6-acetyl-1-((2-(trimethylsilyl)ethoxy)methyl)-1H-pyrrolo[2,3-b]pyridin-2-yl)-1-cyclopropyl-6-fluoro-1H-benzo[d]imidazole-5-carboxylate (I-13e)

Prepared following a similar procedure to I-13a using I-10d. ES/MS: m/z 550.9 [M+H]⁺.

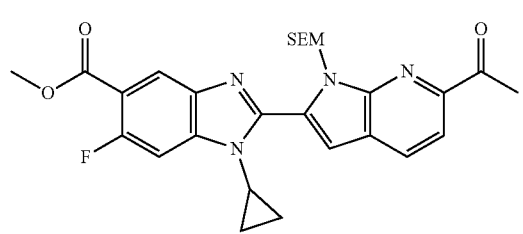

methyl 2-(6-acetyl-1-((2-(trimethylsilyl)ethoxy)methyl)-1H-pyrrolo[2,3-b]pyridin-2-yl)-1-cyclopropyl-1H-benzo[d]imidazole-5-carboxylate (I-13f)

Prepared following a similar procedure to I-13a using I-10e. ES/MS: m/z 505.0 [M+H]⁺.

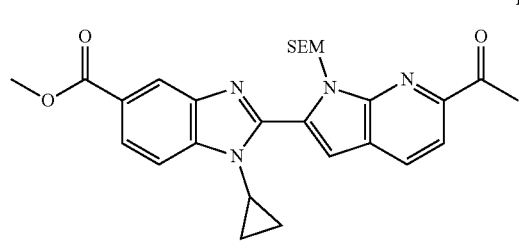

1-(5-fluoro-1-(phenylsulfonyl)-1H-indol-6-yl)ethan-1-one (I-13g)

Prepared following a similar procedure to I-13a using 6-bromo-5-fluoro-1-(phenylsulfonyl)-1H-indole (which was obtained from 6-bromo-5-fluoro-1H-indole following step 1 of I-8a). ES/MS: m/z 318.0 [M+H]⁺. ¹HNMR (400 MHz, DMSO-d6): δ 8.37 (d, J=6.0 Hz, 1H), 8.11 (d, J=3.6 Hz, 1H), 7.96 (dd, J=7.2, 1.2 Hz, 2H), 7.74-7.70 (m, 1H), 7.64-7.56 (m, 3H), 6.92 (d, J=3.6 Hz, 1H), 2.62 (d, J=5.2 Hz, 3H).

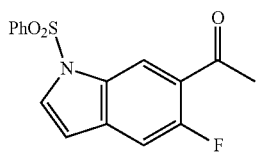

1-(1-(phenylsulfonyl)-1H-indol-6-yl)ethan-1-one (I-13h)

Prepared following a similar procedure to I-13a using 6-bromo-1-(phenylsulfonyl)-1H-indole (which was obtained from 6-bromo-1H-indole following step 1 of I-8a). ES/MS: m/z 300.1 [M+H]⁺. ¹H NMR (400 MHz, CDCl3): δ 8.60 (s, 1H), 7.91 (d, J=5.2 Hz, 2H), 7.88 (dd, J=11.2, 1.2 Hz, 1H), 7.73 (d, J=4.0 Hz, 1H), 7.59-7.54 (m, 2H), 7.48-7.44 (m, 2H), 6.71 (dd, J=3.6, 0.4 Hz, 1H), 2.68 (s, 3H).

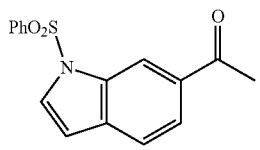

methyl 2-(6-acetyl-1-((2-(trimethylsilyl)ethoxy)methyl)-1H-pyrrolo[2,3-b]pyridin-2-yl)-1-methyl-1H-benzo[d]imidazole-5-carboxylate (I-13i)

Prepared following a similar procedure to I-13a using I-10f. ES/MS: m/z 479.2 [M+H]⁺.

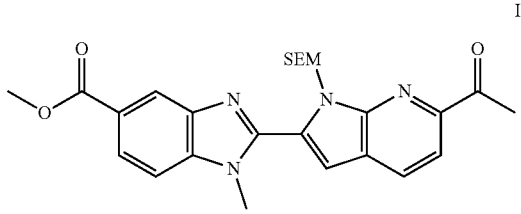

methyl 2-(6-acetyl-1-(tert-butoxycarbonyl)-1H-indol-2-yl)-6-fluoro-1-methyl-1H-benzo[d]imidazole-5-carboxylate (I-13g)

Prepared following a similar procedure to I-13a using I-11c. ES/MS: m/z 466.7 [M+H]⁺.

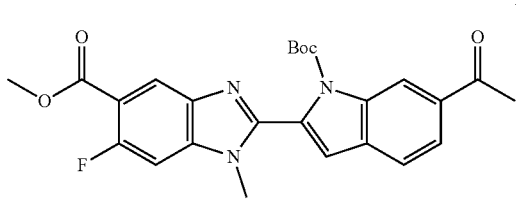

Preparation of 6-cyano-3-ethylpyrazolo[1,5-a]pyridin-2-yl trifluoromethanesulfonate (I-14)

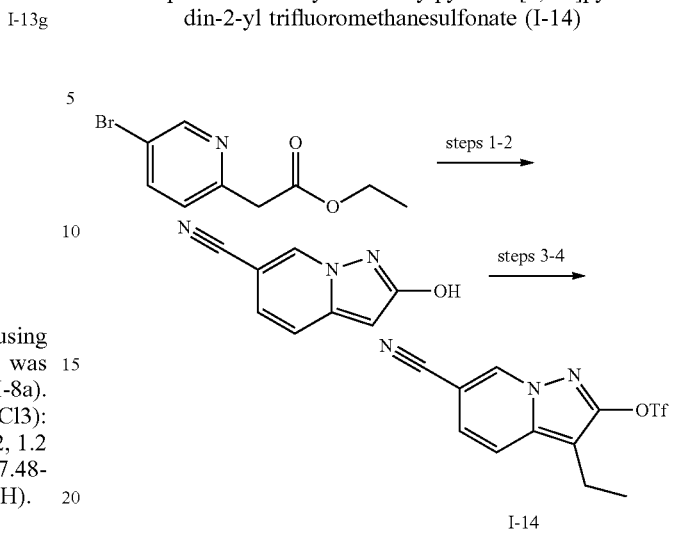

Step 1

A mixture of ethyl 2-(5-bromopyridin-2-yl)acetate (454 mg, 1.86 mmol), zinc cyanide (616 mg, 5.24 mmol), and tetrakis(triphenylphosphine)palladium(0) (322 mg, 0.28 mmol) was taken up in DMF (8 mL) and the resulting reaction mixture was heated at 100° C. under argon for 17 h. After cooling to rt, the reaction mixture was poured into water and extracted with ethyl acetate. The combined organics were washed with water, dried (MgSO₄), filtered, and concentrated under reduced pressure. The resulting residue was purified via silica gel column chromatography (0-35% ethyl acetate/hexanes) to yield ethyl 2-(5-cyanopyridin-2-yl)acetate. ES/MS: m/z 191.0 [M+H]⁺.

Step 2

To a cooled solution of ethyl 2-(5-cyanopyridin-2-yl)acetate (118 mg, 0.62 mmol) in dichloromethane (4 mL) at 0° C. was added portionwise freshly prepared (according to Organic Process Research & Development 2009, 13, 263-267)O-(mesitylsulfonyl)hydroxylamine (~50% purity with remaining mass H₂O, 335 mg, 0.78 mmol). The reaction mixture was warmed to rt and stirred for 18 h. The reaction mixture was concentrated under reduced pressure and the resulting solid residue was suspended in water (8 mL) and filtered. The filtered solid was washed with water (3×8 mL) and dried in vacuo to yield 2-hydroxypyrazolo[1,5-a]pyridine-6-carbonitrile. ES/MS: m/z 160.0 [M+H]⁺.

Step 3

To a mixture of 2-hydroxypyrazolo[1,5-a]pyridine-6-carbonitrile (1200 mg, 7.54 mmol) in DCM (40 mL) was added a solution of acetaldehyde (0.7 mL, 13 mmol) in 3 mL of DCM. Trifluoroacetic acid (1.4 mL, 18 mmol) was added followed by dropwise addition of triethylsilane (2 mL, 13 mmol). After 72 hours, the reaction mixture was concentrated under reduced pressure and dried in vacuo to afford 3-ethyl-2-hydroxypyrazolo[1,5-a]pyridine-6-carbonitrile.

Step 4

A mixture of 3-ethyl-2-hydroxypyrazolo[1,5-a]pyridine-6-carbonitrile in 12 mL of THF and 18 mL of DMF was cooled to 0° C. Sodium hydride (60% dispersion, 670 mg, 17 mmol) was added, followed by N-phenyl-bis(trifluoromethanesulfonimide) (3232 mg, 9.05 mmol). After 2 h at 0° C., the reaction mixture was quenched with cold water and extracted with ethyl acetate. The organic phase was washed with water, dried (MgSO₄), filtered, and concentrated under reduced pressure. The resulting residue was purified via silica gel column chromatography (0-35% ethyl acetate/hexanes) to yield 6-cyano-3-ethylpyrazolo[1,5-a]pyridin-2-yl trifluoromethanesulfonate. ¹H NMR (400 MHz, DMSO-d6) δ 9.58 (s, 1H), 7.98 (dd, J=9.3, 1.0 Hz, 1H), 7.60 (dd, J=9.3, 1.5 Hz, 1H), 2.73 (q, J=7.6 Hz, 2H), 1.19 (t, J=7.6 Hz, 3H).

Preparation of 6-cyano-3-methylpyrazolo[1,5-a]pyridin-2-yl trifluoromethanesulfonate (I-15)

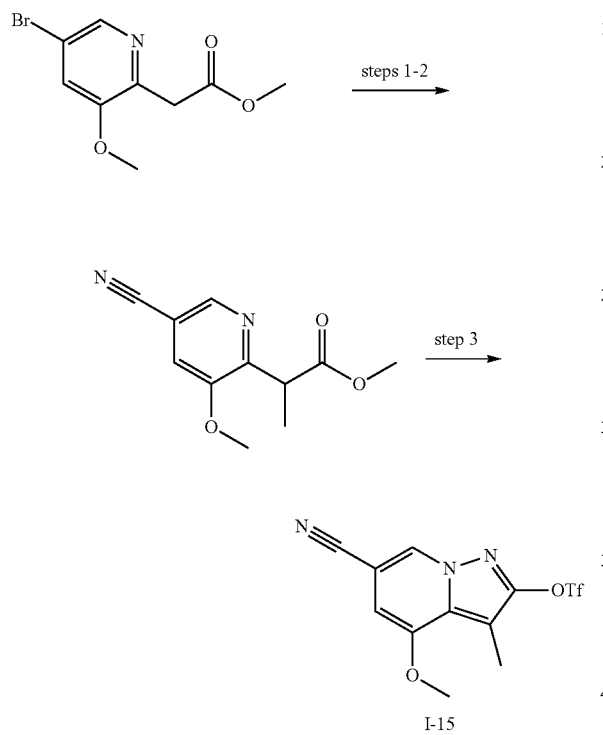

I-15

Step 1

Step 1 of I-14 was followed to produce methyl 2-(5-cyano-3-methoxypyridin-2-yl)acetate from methyl 2-(5-bromo-3-methoxypyridin-2-yl)acetate. ES/MS: m/z 207.0 [M+H]⁺.

Step 2

To a solution of methyl 2-(5-cyano-3-methoxypyridin-2-yl)acetate (0.261 g, 1.27 mmol) in THF (6 mL) at 0° C. was added LiHMDS (1.35 mL of 1 M solution in THF, 1.35 mmol). The reaction mixture was stirred at 0° C. for 30 min. Iodomethane (0.14 mL, 2.26 mmol) was added and the reaction mixture was stirred at rt for 16 h. The reaction mixture was diluted with EtOAc/water. The aqueous layer was extracted with EtOAc. The organic layer was washed with water, dried (MgSO₄), filtered, and concentrated. The residue was purified via column chromatography on silica gel to afford methyl 2-(5-cyano-3-methoxypyridin-2-yl)propanoate. ES/MS: m/z 221.0 [M+H]⁺.

Step 3

Steps 3 and 4 of I-14 were followed to afford 6-cyano-4-methoxy-3-methylpyrazolo[1,5-a]pyridin-2-yl trifluoromethanesulfonate. ES/MS: m/z 336.0 [M+H]⁺.

Preparation of tert-butyl (R)-(1-(2-(6-methyl-4,8-dioxo-1,3,6,2-dioxazaborocane-2-yl)-1H-pyrrolo[2,3-b]pyridin-6-yl)ethyl)carbamate (I-16)

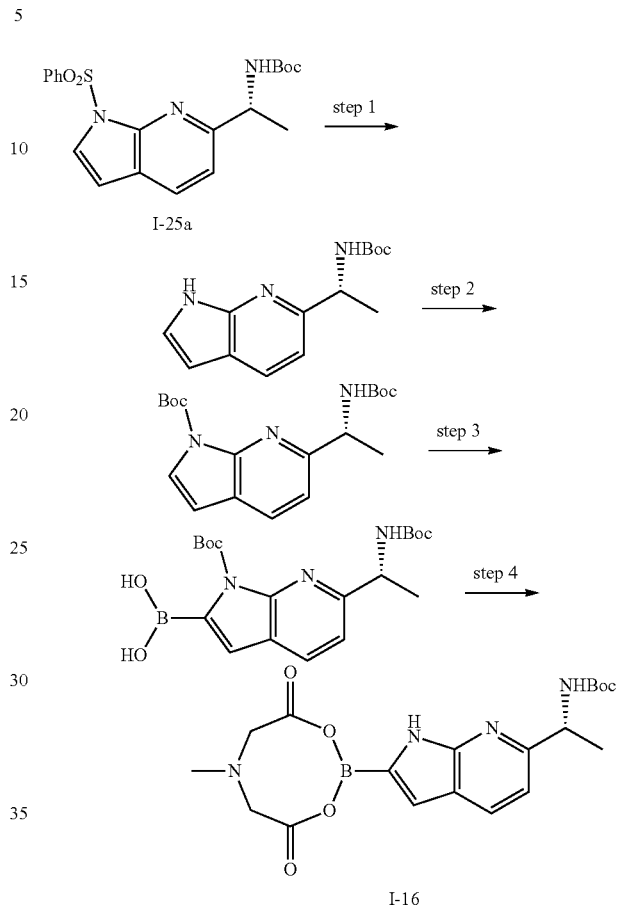

I-16

Step 1

A mixture tert-butyl (R)-(1-(1-(phenylsulfonyl)-1H-pyrrolo[2,3-b]pyridin-6-yl)ethyl)carbamate (2.5 g, 6.23 mmol), 10M NaOH (3 mL), and MeOH (10 mL) was heated in a microwave reactor at 100° C. for 20 min. The methanol was removed and the product was extracted with MeTHF and water. The organic layer was dried with Na₂SO₄, filtered, and concentrated. The crude product was taken to next step without further purification. ES/MS: m/z 262.1 [M+H]⁺.

Step 2

Step 1 of I-11a was followed to produce tert-butyl (R)-6-(1-((tert-butoxycarbonyl)amino)ethyl)-1H-pyrrolo[2,3-b]pyridine-1-carboxylate from tert-butyl (R)-(1-(1H-pyrrolo[2,3-b]pyridin-6-yl)ethyl)carbamate. ES/MS: m/z 362.2 [M+H]⁺.

Step 3

To a solution of tert-butyl 6-[(1R)-1-(tert-butoxycarbonylamino)ethyl]pyrrolo[2,3-b]pyridine-1-carboxylate (1 g, 2.77 mmol) in THF (20 mL) was added triisopropyl borate (1.28 mL, 5.53 mmol). The mixture was cooled to −40° C. and a solution of 0.5 M LDA in THF (16.6 mL, 8.4 mmol) was added dropwise maintaining an internal temperature below −10° C. The mixture was stirred for 5 mins after addition of LDA and the mixture was warmed to 0° C. and quenched with NH₄Cl (aq). The mixture was diluted with ethyl acetate and the layers were separated. The organic layer was dried with Na₂SO₄, filtered, and concentrated. The resulting residue was purified by silica chromatography (0-5% MeOH in DCM) to yield (R)-(1-(tert-butoxycarbonyl)-6-(1-((tert-butoxycarbonyl)amino)ethyl)-1H-pyrrolo[2,3-b]pyridin-2-yl)boronic acid. ES/MS: m/z 406.2 [M+H]+.

Step 4

A mixture of (R)-(1-(tert-butoxycarbonyl)-6-(1-((tert-butoxycarbonyl)amino)ethyl)-1H-pyrrolo[2,3-b]pyridin-2-yl)boronic acid (490 mg, 1.21 mmol) and 2-[carboxymethyl(methyl)amino]acetic acid (0.178 g, 1.21 mmol) in acetonitrile (2 mL) was heated at 130° C. in a microwave reactor. After 6 minutes, the reaction mixture was concentrated under reduced pressure and the resulting residue was purified by silica chromatography (50-100% ethyl acetate in hexanes) to yield tert-butyl (R)-(1-(2-(6-methyl-4,8-dioxo-1,3,6,2-dioxazaborocane-2-yl)-1H-pyrrolo[2,3-b]pyridin-6-yl)ethyl)carbamate (I-16). ES/MS: m/z 417.1 [M+H]+.

(R)-(6-(1-((tert-butoxycarbonyl)amino)ethyl)-1-(phenylsulfonyl)-1H-pyrrolo[2,3-b]pyridin-2-yl)boronic Acid (I-16b)

Prepared following steps 2 and 3 of I-16 using I-25a. ES/MS: m/z 445.9 [M+H]+.

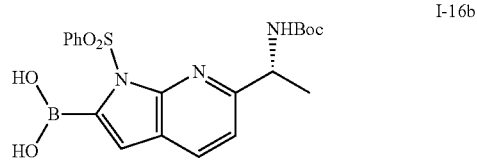

I-16b

Preparation of rac-((1R,3R)-2,2-difluoro-3-vinylcyclopropyl)methanol (I-17)

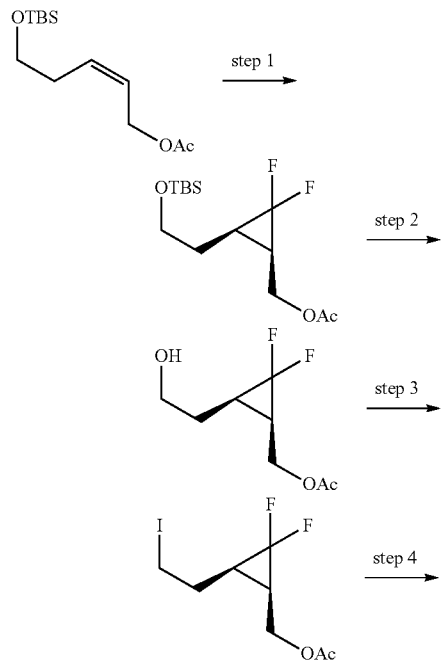

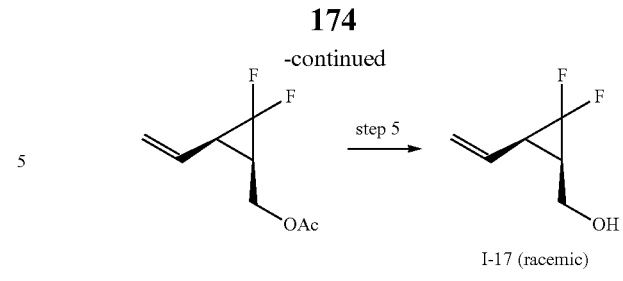

I-17 (racemic)

(Z)-5-((tert-butyldimethylsilyl)oxy)pent-2-en-1-yl acetate is prepared as described in Z. Al-Shuhaib, H. Böckemeier, L. Coghlan, E. Dörksen, I. V. Jones, P. J. Murphy, R. Nash, J. M. Page, *Tetrahedron Letters*, 54, 2013, 6716-6718.

Step 1

To a solution of (Z)-5-((tert-butyldimethylsilyl)oxy)pent-2-en-1-yl acetate (1.5 g, 5.8 mmol) in diglyme (5.8 mL) at 180° C. was added a solution of sodium chlorodifluoroacetate (8.8 g, 58 mmol) in diglyme (12 mL) dropwise over 1 hr. The solution stirred for another 15 min at 180° C. and then, was allowed to cool to room temperature. The mixture was poured onto ice and the aqueous layer was washed with 1:1 EtOAc:hexanes twice. The combined organic layers were washed with water, dried over Na$_2$SO$_4$, filtered and concentrated. The residue was purified by silica gel chromatography (0-25% EtOAc in hex) to give rac-((1R,3R)-3-(2-((tert-butyldimethylsilyl)oxy)ethyl)-2,2-difluorocyclopropyl)methyl acetate. $^1$H NMR (400 MHz, Chloroform-d) δ 4.25-4.09 (m, 2H), 3.68 (t, J=6.1 Hz, 2H), 2.08 (s, 3H), 2.00-1.87 (m, 1H), 1.87-1.75 (m, 1H), 1.74-1.65 (m, 2H), 0.90 (s, 9H), 0.07 (s, 6H).

Step 2

To a solution of rac-((1R,3R)-3-(2-((tert-butyldimethylsilyl)oxy)ethyl)-2,2-difluorocyclopropyl)methyl acetate (1.5 g, 5.0 mmol) in THF (20 mL) was added a 1M solution of tetrabutylammonium fluoride in THF (7.5 mL, 7.5 mmol). The solution stirred for 2 hr. Saturated sodium bicarbonate was added and the aqueous layer was washed twice with diethylether. The combined organic layers were dried over MgSO$_4$, filtered and concentrated. The residue was purified by silica gel chromatography (0-100% diethyl ether in hex) to afford rac-((1R,3R)-2,2-difluoro-3-(2-hydroxyethyl)cyclopropyl)methyl acetate. $^1$H NMR (400 MHz, Chloroform-d) δ 4.28-4.11 (m, 2H), 3.74 (t, J=5.9 Hz, 2H), 2.08 (s, 3H), 2.04-1.88 (m, 1H), 1.87-1.72 (m, 3H).

Step 3

To a solution rac-((1R,3R)-2,2-difluoro-3-(2-hydroxyethyl)cyclopropyl)methyl acetate (480 mg, 2.4 mmol), triethylamine (0.55 mL, 3.9 mmol), imidazole (180 mg, 2.7 mmol), and triphenylphosphine (710 mg, 2.7 mmol) in dichloromethane (4 mL) in an ice bath was added iodine (620 mg, 2.5 mmol). The reaction stirred for 20 min in an ice bath. The ice bath was removed, and the reaction was allowed to warm to room temperature. The reaction stirred for 2 hr. The reaction mixture was diluted with EtOAc and washed with water and diluted NaHSO$_3$, dried over Na$_2$SO$_4$, filtered and concentrated. The residue was purified by silica gel chromatography (0-50% EtOAc in hex) to afford rac-((1R,3R)-2,2-difluoro-3-(2-iodoethyl)cyclopropyl)methyl acetate. $^1$H NMR (400 MHz, Chloroform-d) δ 4.30-4.07 (m, 2H), 3.22 (t, J=7.0 Hz, 2H), 2.09 (s, 3H), 2.08-1.68 (m, 3H).

Step 4

A solution of rac-((1R,3R)-2,2-difluoro-3-(2-iodoethyl)cyclopropyl)methyl acetate (510 mg, 1.7 mmol) and 1,8-diazabicyclo[5.4.0]undec-7-ene (0.99 mL, 6.6 mmol) in THF (10 mL) was stirred at room temperature for 2 days.

The solution was diluted with diethyl ether and washed with 1 N HCl and saturated sodium bicarbonate, dried over MgSO₄, filtered and concentrated to afford rac-((1R,3R)-2,2-difluoro-3-vinylcyclopropyl)methyl acetate. ¹H NMR (400 MHz, Chloroform-d) δ 5.66-5.51 (m, 1H), 5.36 (d, J=17.2 Hz, 1H), 5.27 (d, J=10.4 Hz, 1H), 4.25-4.13 (m, 2H), 2.47-2.36 (m, 1H), 2.20-2.04 (m, 4H).

Step 5

To a solution rac-((1R,3R)-2,2-difluoro-3-vinylcyclopropyl)methyl acetate (190 mg, 1.1 mmol) in 1:1 THF/MeOH (4 mL) was added a 1N solution of lithium hydroxide (2.1 mL, 2.1 mmol). The resulting solution stirred for 2 hr. Saturated sodium bicarbonate was added and the aqueous layer was washed three times with diethyl ether. The combined organic layers were dried over MgSO₄, filtered and concentrated. The residue was purified by silica gel chromatography (0-100% Et₂O in hex) to afford rac-((1R,3R)-2,2-difluoro-3-vinylcyclopropyl)methanol. ¹H NMR (400 MHz, Chloroform-d) δ 5.65 (dddt, J=17.2, 10.4, 8.9, 1.5 Hz, 1H), 5.38 (d, J=17.3 Hz, 1H), 5.28 (d, J=10.5 Hz, 1H), 3.92-3.68 (m, 3H), 2.46-2.34 (m, 1H), 2.09 (ddtd, J=13.4, 11.6, 7.8, 1.8 Hz, 1H).

Preparation of ((1S,2S)-2-vinylcyclopropyl)methanol (I-18)

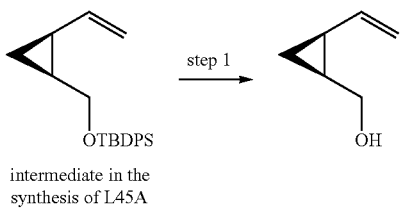

intermediate in the synthesis of L45A

Step 1.

((1S,2S)-2-vinylcyclopropyl)methanol was prepared using a similar procedure to step 9 of L45a with tert-butyldiphenyl(((1S,2S)-2-vinylcyclopropyl)methoxy)silane.

Preparation of rac-((1R,3S)-2,2-difluoro-3-vinylcyclopropyl)methanol (I-19)

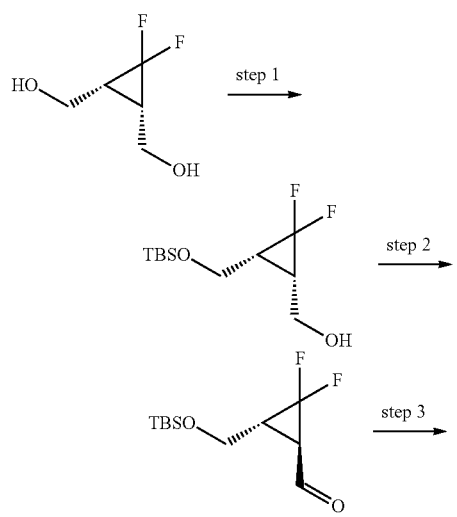

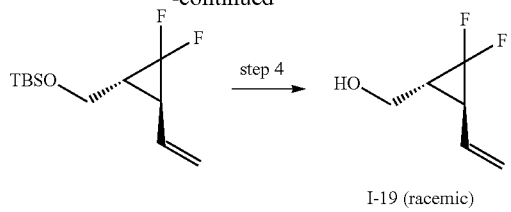

I-19 (racemic)

Cis-(3,3-difluorocyclopropane-1,2-diyl)dimethanol was prepared as described in T. Itoh, N. Ishida, K. Mitsukura, S. Hayase, K. Ohashi, *Journal of Fluorine Chemistry* 125 (2004) 775-783.

Step 1

To a mixture of 60% sodium hydride (810 mg, 21 mmol) in THF (100 mL) in an ice bath was added a solution of (3,3-difluorocyclopropane-1,2-diyl)dimethanol (2.9 g, 21 mmol) in THF (50 mL). The mixture stirred for 5 min, and then, tert-butyldimethylsilyl chloride (3.2 g, 21 mmol) was added. The mixture stirred for 30 min. Water was added to the reaction mixture and the aqueous layer was washed three times with EtOAc. The combined organic layers were dried over Na₂SO₄, filtered and concentrated. The residue was purified by silica gel chromatography (0-50% EtOAc in hex) to give rac-((1S,3R)-3-(((tert-butyldimethylsilyl)oxy)methyl)-2,2-difluorocyclopropyl)methanol. ¹H NMR (400 MHz, Chloroform-d) δ 4.06 (ddd, J=12.0, 6.3, 3.0 Hz, 1H), 3.96-3.84 (m, 1H), 3.77-3.63 (m, 2H), 3.05 (dd, J=11.1, 2.2 Hz, 1H), 2.18-1.93 (m, 2H), 0.91 (s, 9H), 0.13 (s, 3H), 0.12 (s, 3H).

Step 2.

rac-(1R,3R)-3-(((tert-butyldimethylsilyl)oxy)methyl)-2,2-difluorocyclopropane-1-carbaldehyde was prepared using a similar procedure to step 1 of L30a with rac-((1S,3R)-3-(((tert-butyldimethylsilyl)oxy)methyl)-2,2-difluorocyclopropyl)methanol Step 3.

To a mixture of methyl(triphenyl)phosphonium bromide (8.1 g, 23 mmol) in THF (30 mL) cooled in an ice bath was added a 1 M solution of sodium bis(trimethylsilyl)amide in THF (23 mL, 23 mmol). The reaction mixture stirred at room temperature for 30 min and was placed back in the ice bath. To the cooled mixture was added a solution of rac-(1R,3R)-3-(((tert-butyldimethylsilyl)oxy)methyl)-2,2-difluorocyclopropane-1-carbaldehyde (3.5 g, 14 mmol) in THF (20 mL) over 10 min. The reaction stirred in the ice bath for 2 hr. To the mixture was added saturated ammonium chloride and the aqueous layer was washed with EtOAc three times. The combined organic layers were dried over Na₂SO₄, filtered and concentrated. The residue was purified by silica gel chromatography (0-30% EtOAc in hex) to give rac-tert-butyl(((1R,3S)-2,2-difluoro-3-vinylcyclopropyl)methoxy)dimethylsilane. ¹H NMR (400 MHz, Chloroform-d) δ 5.55 (dddd, J=17.1, 10.1, 8.5, 1.7 Hz, 1H), 5.32-5.06 (m, 2H), 3.83-3.66 (m, 2H), 2.38-1.71 (m, 2H), 0.89 (s, 9H), 0.16 (s, 3H), 0.07 (s, 5H).

Step 4

To a solution of rac-tert-butyl(((1R,3S)-2,2-difluoro-3-vinylcyclopropyl)methoxy)dimethylsilane (3.5 g, 14 mmol) in THF (20 mL) was added a 1M solution of tetrabutylammonium fluoride in THF (21 mL, 21 mmol). The solution stirred for 2 hr. Saturated sodium bicarbonate was added and the aqueous layer was washed twice with diethylether. The combined organic layers were dried over MgSO₄, filtered and concentrated. The residue was purified by silica gel chromatography (0-100% diethyl ether in hex) to afford rac-((1R,3S)-2,2-difluoro-3-vinylcyclopropyl)methanol. $^1$H NMR (400 MHz, Chloroform-d) δ 5.63-5.48 (m, 0H), 5.26 (d, J=17.3 Hz, 0H), 5.18 (d, J=10.5 Hz, 0H), 3.89-3.68 (m, 2H), 2.17-2.05 (m, 1H), 1.87 (dq, J=14.3, 7.1 Hz, 1H).

Preparation of ((1S,2S)-2-(((tert-butyldiphenylsilyl)oxy)methyl)-1-fluorocyclopropyl)methanol (I-20a) and ((1R,2R)-2-(((tert-butyldiphenylsilyl)oxy)methyl)-1-fluorocyclopropyl)methanol (I-20b)

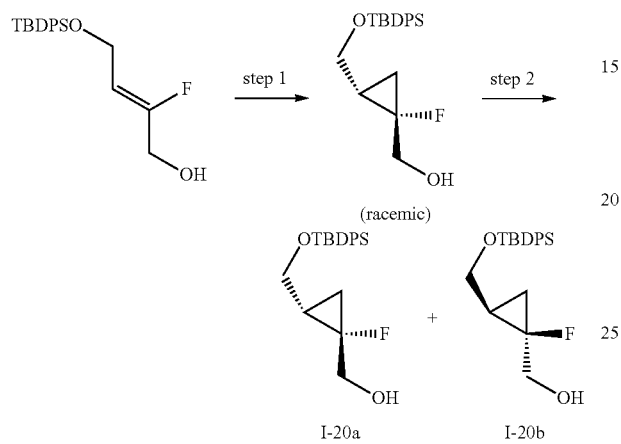

(Z)-4-((tert-butyldiphenylsilyl)oxy)-2-fluorobut-2-en-1-ol was prepared as described in Nucleosides, *Nucleotides & Nucleic Acids*, 22 (5-8), 659-661; 2003.

Step 1

Diiodomethane (3.42 g, 1.02 mL, 12.8 mmol) was added to a solution of Et$_2$Zn (1.0 M in hexane, 6.96 mmol, 6.96 mL) in CH$_2$Cl$_2$ (20 mL) at 0° C. and stirred for 15 min. The resulting white slurry was cooled to −78° C. and a solution of (Z)-4-((tert-butyldiphenylsilyl)oxy)-2-fluorobut-2-en-1-ol (2.0 g, 5.8 mmol) in CH$_2$Cl$_2$ (10 mL) was added. The reaction was allowed to warm to room temperature by removal of the cooling bath and stirring continued for 17 h. The reaction was cooled to 0° C., saturated aqueous NH$_4$Cl was added and the layers were separated. The aqueous phase was extracted with CH$_2$Cl$_2$ (3×6 mL) and the combined organic fractions dried (MgSO$_4$) and concentrated under reduced pressure. The crude residue was purified by flash chromatography eluting with EtOAc/hexane (5-100%) to give rac-((1S,2S)-2-(((tert-butyldiphenylsilyl)oxy)methyl)-1-fluorocyclopropyl)methanol. $^1$H NMR: (CDCl$_3$ 400 MHz): δ 7.70-7.68 (m, 4H), 7.43-7.39 (m, 6H), 3.90-3.72 (m, 4H), 1.29-1.27 (m, 1H), 1.06 (s, 9H), 0.89-0.81 (m, 2H).

Step 2

((1S,2S)-2-(((tert-butyldiphenylsilyl)oxy)methyl)-1-fluorocyclopropyl)methanol (I-20a) and ((1R,2R)-2-(((tert-butyldiphenylsilyl)oxy)methyl)-1-fluorocyclopropyl)methanol (I-20b) were obtained from SFC (column: DAICEL CHIRALCEL OJ (250 mm*50 mm, 10 um); mobile phase: [0.1% NH$_3$H$_2$O IPA]; B %: 11%-11%, 2.6 min).

((1S,2R)-2-(((tert-butyldiphenylsilyl)oxy)methyl)-1-fluorocyclopropyl)methanol (I-20c) and ((1R,2S)-2-(((tert-butyldiphenylsilyl)oxy)methyl)-1-fluorocyclopropyl)methanol (I-20d)

Prepared following a similar procedure to I-20a/I-20b using (E)-4-((tert-butyldiphenylsilyl)oxy)-2-fluorobut-2-en-1-ol ((E)-4-((tert-butyldimethylsilyl)oxy)-2-fluorobut-2-en-1-ol is reported in Tetrahedron 2004, 60, 10907-10914). $^1$H NMR: (CDCl3 400 MHz): δ7.70-7.66 (m, 4H), 7.52-7.35 (m, 6H), 4.49-4.19 (m, 1H), 4.01-4.10 (m, 1H), 3.78-3.57 (m, 1H), 3.28-3.25 (m, 1H), 3.19-3.14 (m, 1H), 1.75-1.62 (m, 1H), 1.20-1.18 (m, 1H), 1.07 (s, 9H), 0.59-0.56 (m, 1H).

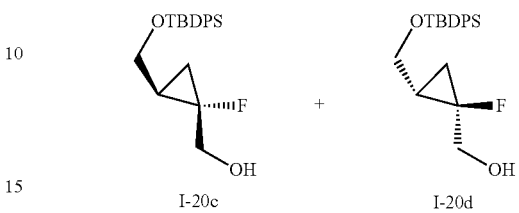

Preparation of methyl 4-(methylamino)-5-nitro-2-(trifluoromethyl)benzoate (I-21)

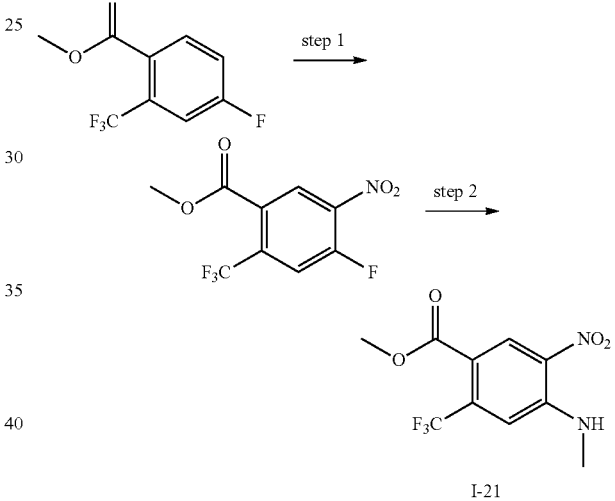

Step 1

Methyl 4-fluoro-2-(trifluoromethyl)benzoate (1.4 mL, 6.3 mmol) was dissolved in concentrated sulfuric acid (1.4 mL, 26.3 mmol) and the resulting reaction mixture was cooled to 0° C. Fuming nitric acid (99%) (2.63 mL, 41.1 mmol) was added dropwise and the reaction mixture was stirred at room temperature for 30 min. Then, the mixture was warmed to 45° C. and stirred for 16 h. The reaction mixture was added dropwise into ice-water (9 mL), diluted with ethyl acetate (9 mL) and left to stir for 30 min. The mixture was extracted with ethyl acetate and the organic layer was washed with water and saturated sodium bicarbonate solution. The organics were collected, dried over anhydrous magnesium sulfate, filtered and concentrated to produce the crude product, which was purified via silica gel column chromatography (0-30% ethyl acetate in hexanes) to yield methyl 4-fluoro-5-nitro-2-(trifluoromethyl)benzoate. $^1$H NMR (400 MHz, Chloroform-d) δ 7.92-7.82 (m, 1H), 7.59 (t, J=8.4 Hz, 1H), 3.99 (s, 3H). $^{19}$F NMR (376 MHz, Chloroform-d) δ−56.16, −117.55 (dd, J=8.1, 5.0 Hz).

Step 2

Triethylamine (0.26 mL, 1.88 mmol) was added to a solution of methyl 4-fluoro-5-nitro-2-(trifluoromethyl)benzoate (167 mg, 0.63 mmol) in tetrahydrofuran (2 mL) at 0° C., followed by 2 M methylamine in tetrahydrofuran (0.7 mL, 1.37 mmol). The resulting reaction mixture was stirred at room temperature for 16 h. The reaction mixture was diluted with water to crash out the product, filtering and washing the cake with water, repeating twice. The resulting cake was dissolved in dichloromethane, dried over anhydrous magnesium sulfate and concentrated to yield methyl 4-(methylamino)-5-nitro-2-(trifluoromethyl)benzoate, which was carried forward without further purification. $^1$H NMR (400 MHz, Chloroform-d) δ 7.73 (d, J=8.9 Hz, 1H), 6.99 (d, J=8.9 Hz, 1H), 3.93 (s, 3H), 2.99 (d, J=4.9 Hz, 3H). $^{19}$F NMR (376 MHz, Chloroform-d) δ −56.16.

Preparation of tert-butyl (3S,4S)-3-(4-(cyclobutylamino)-2-fluoro-5-nitrobenzamido)-4-fluoropiperidine-1-carboxylate (I-22a)

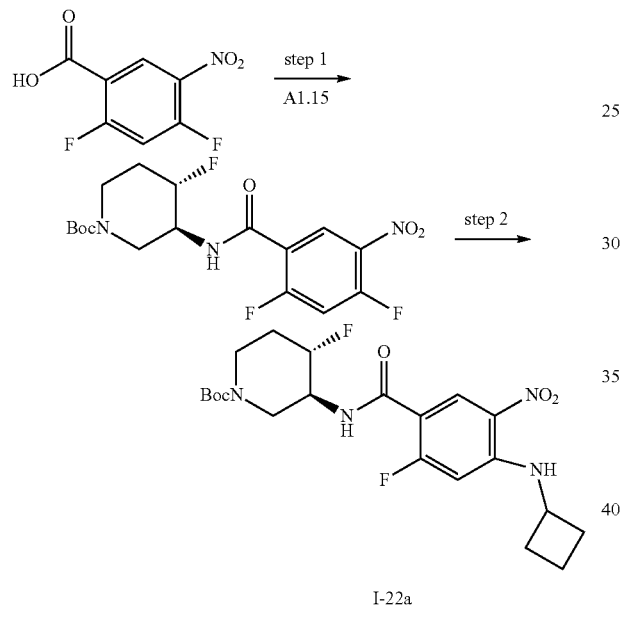

I-22a

Step 1.

A mixture of 2,4-difluoro-5-nitro-benzoic acid (512 mg, 2.52 mmol), (1-chloro-2-methyl-propenyl)-dimethylamine (0.371 mL, 2.80 mmol) and DCM (37 mL) is stirred for 30 min, then A1.15 (500 mg, 2.29 mmol) and N,N-diisopropylethylamine (0.650 mL, 3.80 mmol) are added and it is stirred for 2 h. The mixture is concentrated and purified by silica gel chromatography (5-50% EtOAc in hexanes) provided tert-butyl (3S,4S)-3-[(2,4-difluoro-5-nitro-benzoyl)amino]-4-fluoro-piperidine-1-carboxylate. ES/MS: m/z 402.1 [M+H]$^+$.

Step 2

A 50 mL round bottom flask was charged with tert-butyl (3S,4S)-3-[(2,4-difluoro-5-nitro-benzoyl)amino]-4-fluoro-piperidine-1-carboxylate (100 mg, 0.248 mmol) a stir bar and THF (5 mL). The solution was cooled to 0° C. and Hunig's base (42.4 μL, 0.248 mmol) was added followed by dropwise addition of cyclopropylamine (25.4 μL, 0.298 mmol). The remaining mixture was stirred at 0° C. for 2 hr. The mixture is concentrated and purified by silica gel chromatography (5-80% EtOAc in hexanes) provided tert-butyl (3S,4S)-3-[[4-(cyclobutylamino)-2-fluoro-5-nitrobenzoyl]amino]-4-fluoro-piperidine-1-carboxylate. ES/MS: m/z 455.3 [M+H]$^+$.

tert-butyl (3S,4S)-4-fluoro-3-(2-fluoro-4-(isopropylamino)-5-nitrobenzamido)piperidine-1-carboxylate (I-22b)

Prepared following a similar procedure to I-22a using isopropylamine. ES/MS: m/z 443.3 [M+H]$^+$.

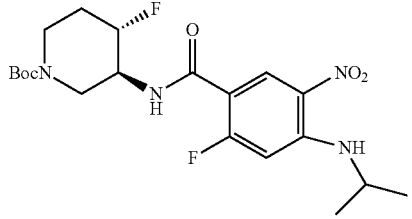

I-22b tert-butyl (3S,4S)-3-(4-(ethylamino)-2-fluoro-5-nitrobenzamido)-4-fluoropiperidine-1-carboxylate (I-22c)

Prepared following a similar procedure to I-22a using ethylylamine. ES/MS: m/z 429.3 [M+H]$^+$.

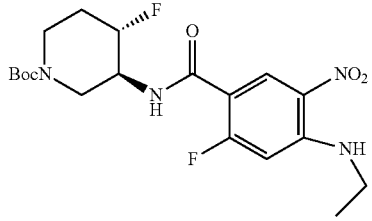

I-22c tert-butyl (3S,4S)-3-(4-((2-ethoxyethyl)amino)-2-fluoro-5-nitrobenzamido)-4-fluoropiperidine-1-carboxylate (I-22d)

Prepared following a similar procedure to I-22a using 2-ethoxyethane-1-amine. ES/MS: m/z 473.3 [M+H]$^+$.

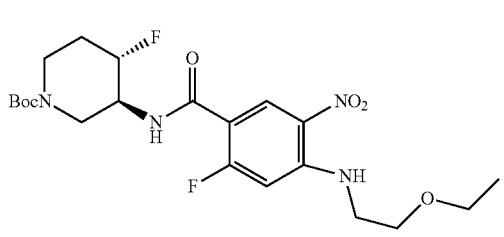

I-22d tert-butyl (3S,4S)-3-(4-((2-cyanoethyl)amino)-2-fluoro-5-nitrobenzamido)-4-fluoropiperidine-1-carboxylate (I-22e)

Prepared following a similar procedure to I-22a using 2-aminoacetonitrile. ES/MS: m/z Does not ionize.

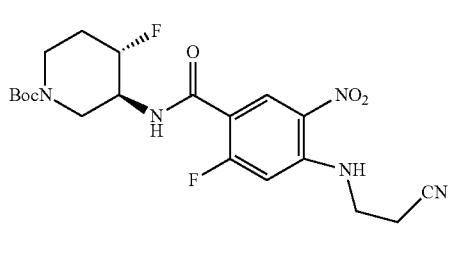

I-22e tert-butyl (3S,4S)-4-fluoro-3-(2-fluoro-4-((2-(2-methoxyethoxy)ethyl)amino)-5-nitrobenzamido)piperidine-1-carboxylate (I-22f)

Prepared following a similar procedure to I-22a using 2-(2-methoxyethoxy)ethan-1-amine. ES/MS: m/z 503.3 [M+H]+.

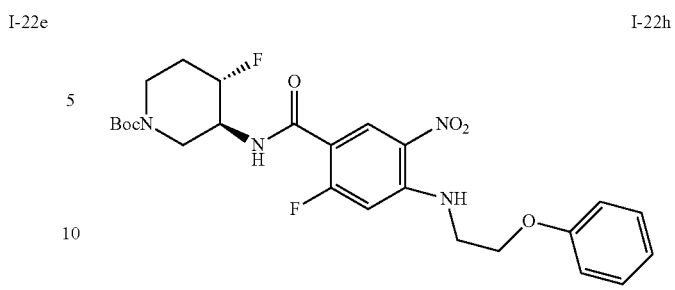

I-22h tert-butyl (3S,4S)-4-fluoro-3-(2-fluoro-4-((2-methoxypropyl)amino)-5-nitrobenzamido)piperidine-1-carboxylate (I-22i)

Prepared following a similar procedure to I-22a using 2-methoxypropan-1-amine. ES/MS: m/z Does not ionize.

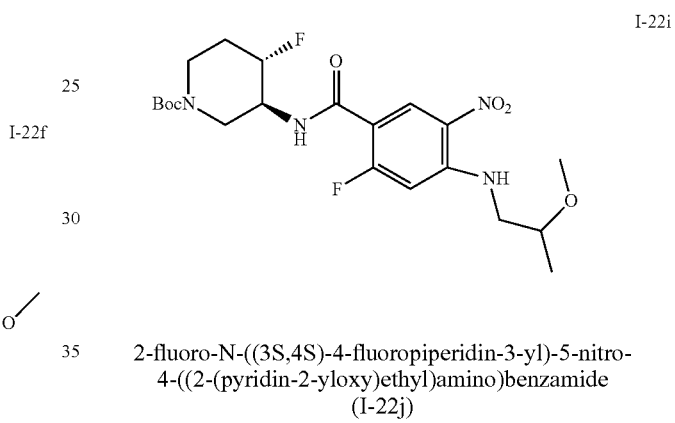

I-22f

I-22i 2-fluoro-N-((3S,4S)-4-fluoropiperidin-3-yl)-5-nitro-4-((2-(pyridin-2-yloxy)ethyl)amino)benzamide (I-22j)

Prepared following a similar procedure to I-22a using 2-(pyridin-2-yloxy)ethan-1-amine. ES/MS: m/z 422.0 [M+H]+.

tert-butyl (3S,4S)-3-(4-((3-amino-3-oxopropyl)amino)-2-fluoro-5-nitrobenzamido)-4-fluoropiperidine-1-carboxylate (I-22g)

Prepared following a similar procedure to I-22a using 3-aminopropanamide. ES/MS: m/z 471.7 [M+H]+.

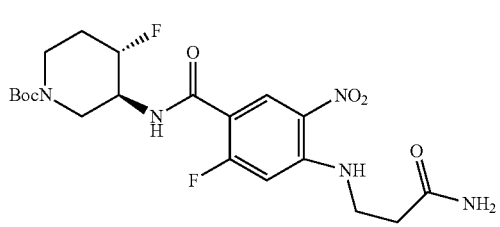

I-22g

I-22j tert-butyl (3S,4S)-4-fluoro-3-(2-fluoro-5-nitro-4-((2-phenoxyethyl)amino)benzamido)piperidine-1-carboxylate (I-22h)

Prepared following a similar procedure to I-22a using 2-phenoxyethan-1-amine. ES/MS: m/z 520.2 [M+H]+.

tert-butyl ((3S,4R)-1-(3-fluoro-4-((2-methoxyethyl)amino)-5-nitrobenzoyl)-4-methoxypiperidin-3-yl)carbamate (I-22k)

Prepared following a similar procedure to I-22a using 3,4-difluoro-5-nitrobenzoic acid, A1.03 and 2-methoxyethan-1-amine. ES/MS: m/z 470.8 [M+H]+.

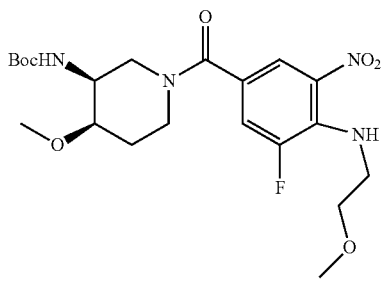

tert-butyl (3S,4S)-4-fluoro-3-(2-fluoro-4-((2-isopropoxyethyl)amino)-5-nitrobenzamido)piperidine-1-carboxylate (I-22l)

Prepared following a similar procedure to I-22a using 2-isopropoxyethan-1-amine. ES/MS: m/z 486.6 [M+H]⁺.

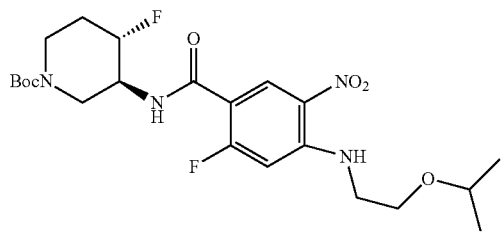

tert-butyl (3S,4S)-4-fluoro-3-(2-fluoro-4-(((1-fluorocyclopropyl)methyl)amino)-5-nitrobenzamido)piperidine-1-carboxylate (I-22m)

Prepared following a similar procedure to I-22a using (1-fluorocyclopropyl)methanamine. ES/MS: m/z 473.73 [M+H]⁺.

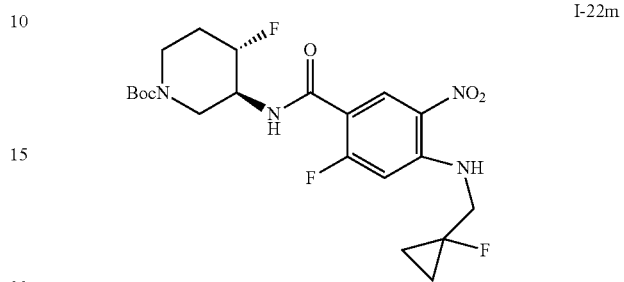

tert-butyl (3S,4S)-3-(4-(((1-cyanocyclopropyl)methyl)amino)-2-fluoro-5-nitrobenzamido)-4-fluoropiperidine-1-carboxylate (I-22n)

Prepared following a similar procedure to I-22a using 1-(aminomethyl)cyclopropanecarbonitrile. ES/MS: m/z 479.94 [M+H]⁺.

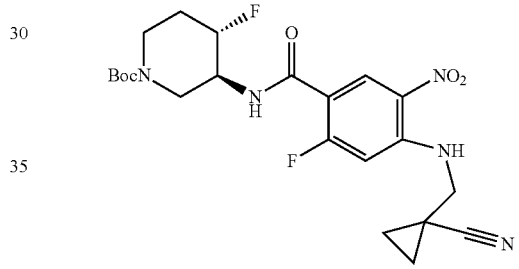

tert-butyl (3S,4S)-3-(4-(((1R,2S)-2-(difluoromethyl)cyclopropyl)amino)-2-fluoro-5-nitrobenzamido)-4-fluoropiperidine-1-carboxylate and tert-butyl (3S,4S)-3-(4-(((1S,2R)-2-(difluoromethyl)cyclopropyl)amino)-2-fluoro-5-nitrobenzamido)-4-fluoropiperidine-1-carboxylate (I-22p)

Prepared following a similar procedure to I-22a using rac-(1R,2S)-2-(difluoromethyl)cyclopropanamine. ES/MS: m/z 490.8 [M+H]⁺.

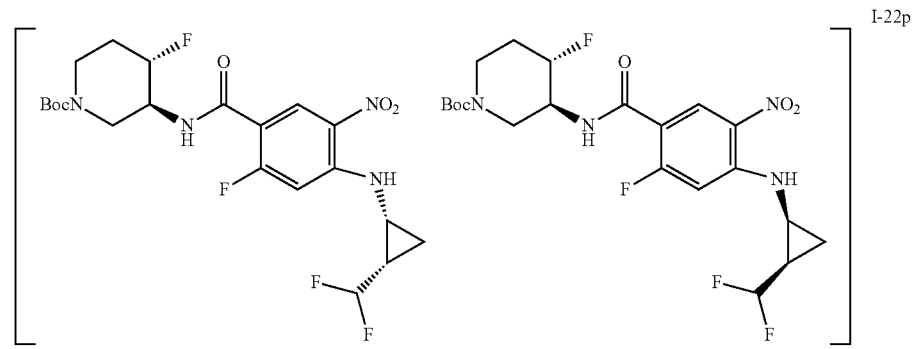

tert-butyl (3S,4S)-4-fluoro-3-(2-fluoro-4-(((1S,2S)-2-methylcyclopropyl)amino)-5-nitrobenzamido)piperidine-1-carboxylate (I-22q)

Prepared following a similar procedure to I-22a using (1S,2S)-2-methylcyclopropanamine. ES/MS: m/z 454.3 [M+H]$^+$.

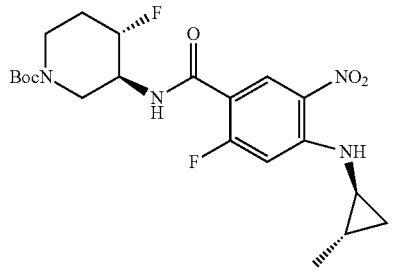

I-22q tert-butyl (3S,4S)-4-fluoro-3-(2-fluoro-4-(((1R,2R)-2-methylcyclopropyl)amino)-5-nitrobenzamido)piperidine-1-carboxylate (I-22r)

Prepared following a similar procedure to I-22a using (1R,2R)-2-methylcyclopropanamine. ES/MS: m/z 455.6 [M+H]$^+$.

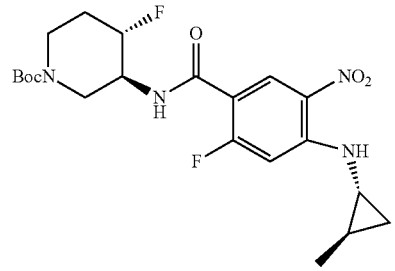

I-22r tert-butyl (3S,4S)-3-(4-(((1R,2R)-2-(difluoromethyl)cyclopropyl)amino)-2-fluoro-5-nitrobenzamido)-4-fluoropiperidine-1-carboxylate and tert-butyl (3S,4S)-3-(4-(((1S,2S)-2-(difluoromethyl)cyclopropyl)amino)-2-fluoro-5-nitrobenzamido)-4-fluoropiperidine-1-carboxylate (I-22s)

Prepared following a similar procedure to I-22a using rac-(1R,2R)-2-(difluoromethyl)cyclopropanamine. ES/MS: m/z 490.6 [M+H]$^+$.

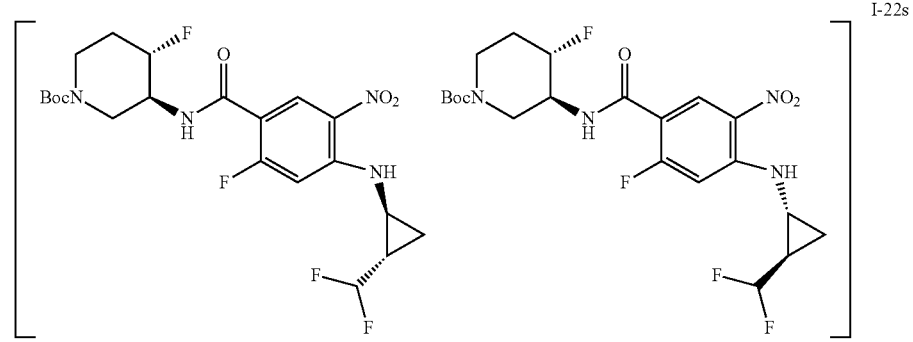

I-22s tert-butyl (3S,4S)-4-fluoro-3-(2-fluoro-5-nitro-4-((2-(trifluoromethoxy)ethyl)amino)benzamido)piperidine-1-carboxylate (I-22t)

Prepared following a similar procedure to I-22a using 2-(trifluoromethoxy)ethanamine hydrochloride. ES/MS: m/z 512.6 [M+H]⁺.

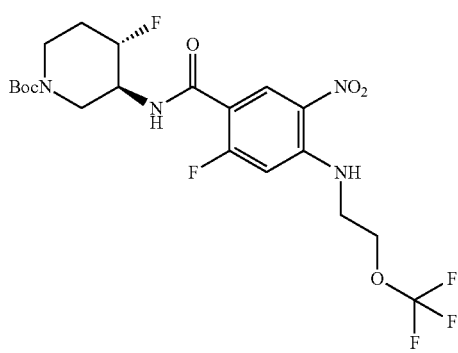

tert-butyl (3S,4S)-3-(4-((2-cyclopropoxyethyl)amino)-2-fluoro-5-nitrobenzamido)-4-fluoropiperidine-1-carboxylate (I-22u)

Prepared following a similar procedure to I-22a using 2-(cyclopropoxy)ethanamine hydrochloride. ES/MS: m/z 484.6 [M+H]⁺.

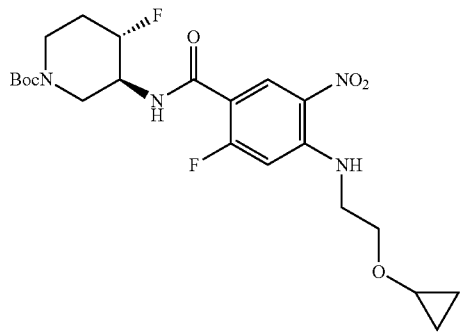

tert-butyl (3S,4S)-3-(4-((2-(difluoromethoxy)ethyl)amino)-2-fluoro-5-nitrobenzamido)-4-fluoropiperidine-1-carboxylate (I-22v)

Prepared following a similar procedure to I-22a using 2-(difluoromethoxy)ethanamine hydrochloride. ES/MS: m/z 495.2 [M+H]⁺.

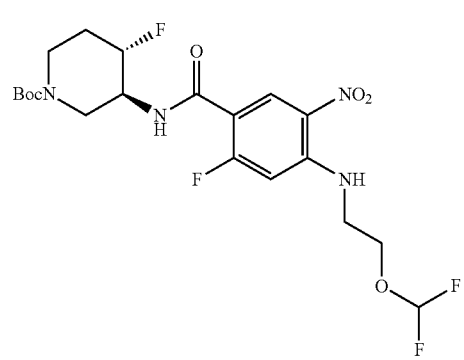

tert-butyl (3S,4S)-4-fluoro-3-(4-(methylamino)-3-nitro-5-(trifluoromethyl)benzamido)piperidine-1-carboxylate (I-22w)

Prepared following a similar procedure to I-22a using 4-fluoro-3-nitro-5-(trifluoromethyl)benzoic acid. ES/MS: m/z 465.6 [M+H]⁺.

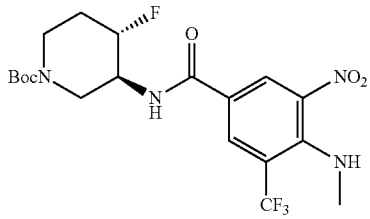

tert-butyl (3S,4S)-4-fluoro-3-(2-fluoro-5-nitro-4-(spiro[2.2]pentan-1-ylamino)benzamido)piperidine-1-carboxylate (I-22x)

Prepared following a similar procedure to I-22a. ES/MS: m/z 466.4 [M+H]⁺.

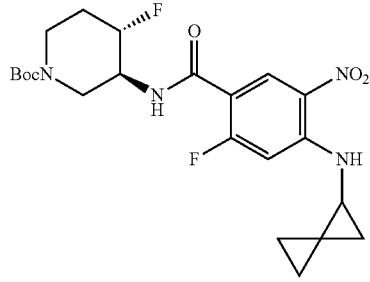

189 tert-butyl ((3S,4R)-1-(4-(cyclopropylamino)-3-fluoro-5-nitrobenzoyl)-4-methoxypiperidin-3-yl)carbamate (I-22y)

Prepared following a similar procedure to I-22a using 3,4-difluoro-5-nitrobenzoic acid, A1.03 and cyclopropylamine.

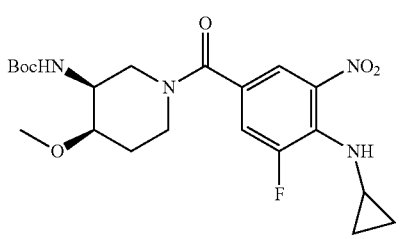

I-22y

Preparation of tert-butyl (3S,4S)-3-(5-amino-2-fluoro-4-((2-methoxypropyl)amino)benzamido)-4-fluoropiperidine-1-carboxylate (I-23a)

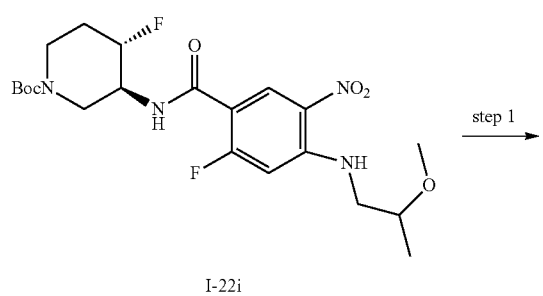

Step 1 tert-butyl (3S,4S)-3-(5-amino-2-fluoro-4-((2-methoxypropyl)amino)benzamido)-4-fluoropiperidine-1-carboxylate was prepared following a similar procedure to step 2 of I-140a. ES/MS: m/z 442.8 [M+H]+.

190

5-amino-2-fluoro-N-((3S,4S)-4-fluoropiperidin-3-yl)-4-((2-(pyridin-2-yloxy)ethyl)amino)benzamide (I-23c)

Prepared following a similar procedure to I-23a using I-22j. ES/MS: m/z 491.9 [M+H]+.

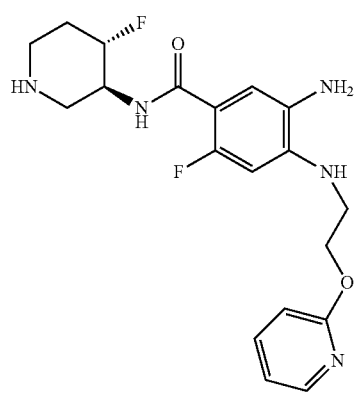

tert-butyl ((3S,4R)-1-(3-amino-5-fluoro-4-((2-methoxyethyl)amino)benzoyl)-4-methoxypiperidin-3-yl)carbamate (I-23d)

Prepared following a similar procedure to I-23a using I-22k. ES/MS: m/z 440.9 [M+H]+.

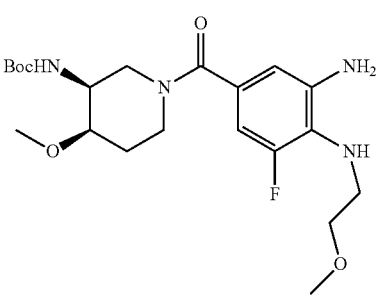

tert-butyl (3S,4S)-3-(5-amino-4-(((1R,2S)-2-(difluoromethyl)cyclopropyl)amino)-2-fluorobenzamido)-4-fluoropiperidine-1-carboxylate and tert-butyl (3S,4S)-3-(5-amino-4-(((1S,2R)-2-(difluoromethyl)cyclopropyl)amino)-2-fluorobenzamido)-4-fluoropiperidine-1-carboxylate (I-23f)

Prepared following a similar procedure to I-23a using I-22p. ES/MS: m/z 460.79 [M+H]+. Note: Dianiline doesn't ionize well.

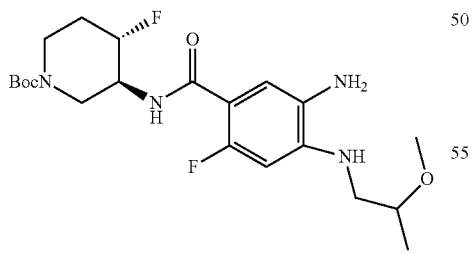

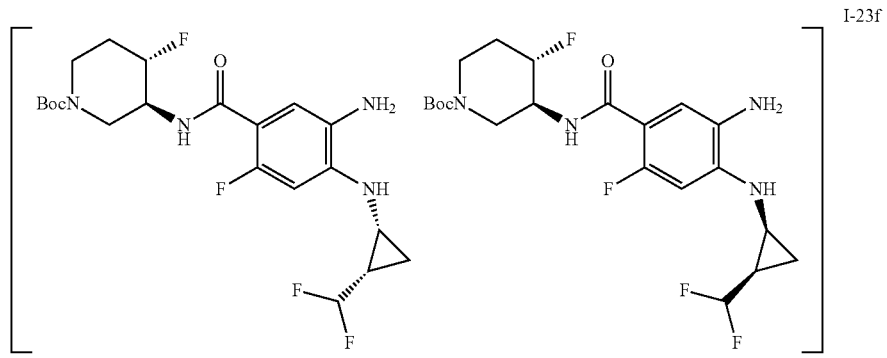

tert-butyl (3S,4S)-3-(5-amino-2-fluoro-4-(((1S,2S)-2-methylcyclopropyl)amino)benzamido)-4-fluoropiperidine-1-carboxylate (I-23g)

Prepared following a similar procedure to I-23a using I-22q. ES/MS: Dianiline does not ionize well; retention time: 1.65 min.

tert-butyl (3S,4S)-3-(5-amino-2-fluoro-4-(((1R,2R)-2-methylcyclopropyl)amino)benzamido)-4-fluoropiperidine-1-carboxylate (I-23h)

Prepared following a similar procedure to I-23a using I-22r. ES/MS: m/z 424.93 [M+H]$^+$. Note: Dianiline does not ionize well.

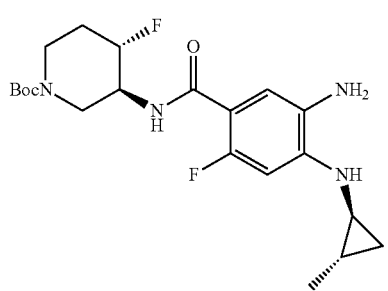

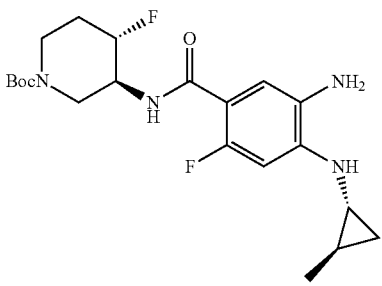

tert-butyl (3S,4S)-3-(5-amino-4-(((1R,2R)-2-(difluoromethyl)cyclopropyl)amino)-2-fluorobenzamido)-4-fluoropiperidine-1-carboxylate and tert-butyl (3S,4S)-3-(5-amino-4-(((1S,2S)-2-(difluoromethyl)cyclopropyl)amino)-2-fluorobenzamido)-4-fluoropiperidine-1-carboxylate (I-23i)

Prepared following a similar procedure to I-23a using I-22s. ES/MS: m/z 460.29 [M+H]$^+$.

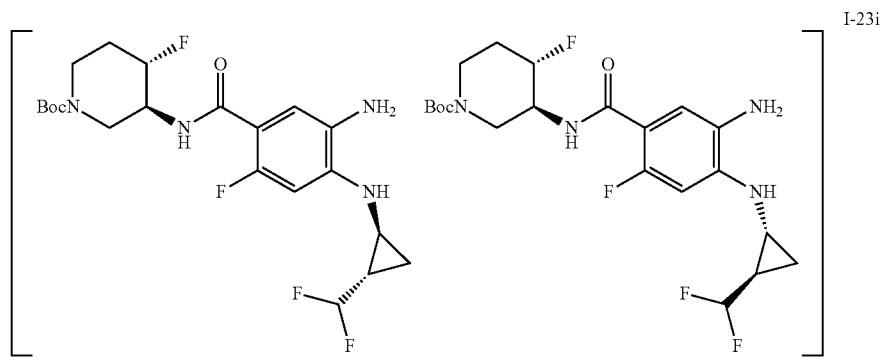

tert-butyl (3S,4S)-3-(5-amino-2-fluoro-4-(spiro[2.2]pentan-1-ylamino)benzamido)-4-fluoropiperidine-1-carboxylate (I-23k)

Prepared following a similar procedure to I-23a using I-22x. ES/MS: m/z 436.8 [M+H]$^+$.

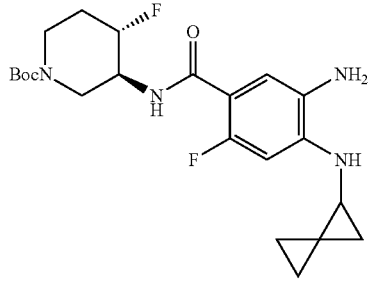

I-23k tert-butyl ((3S,4R)-1-(3-amino-4-(cyclopropylamino)-5-fluorobenzoyl)-4-methoxypiperidin-3-yl)carbamate (I-23m)

Prepared following a similar procedure to I-23a using I-22y.

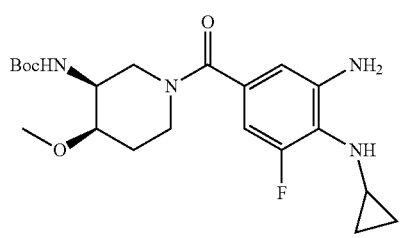

I-23m

Preparation of 6-bromo-7-fluoro-1-(phenylsulfonyl)-1H-indole-2-carbaldehyde (I-24a)

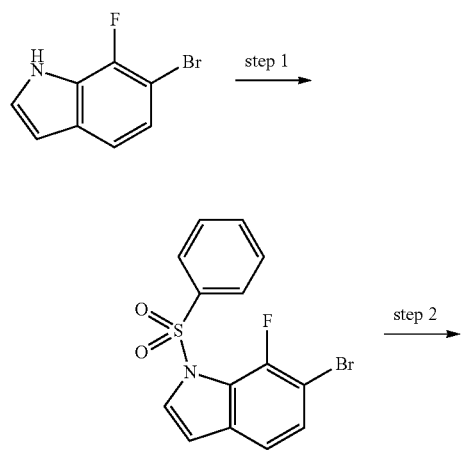

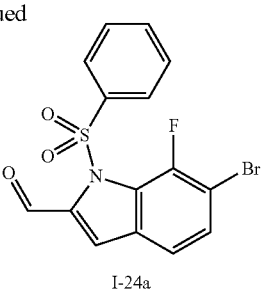

I-24a

Step 1

6-bromo-7-fluoro-1H-indole (14 g, 65 mmol) was dissolved in THF (140 mL) and cooled to 0° C. NaH (60% dispersion, 3.92 g, 98.1 mmol) was added, and the mixture was allowed to warm to r.t. and stirred for 1 h. The mixture was cooled to 0° C., and benzenesulfonyl chloride (13.9 g, 78.5 mmol) was then added, and the mixture was allowed to warm to r.t. and was stirred for 1 h. The mixture was then poured into saturated aqueous NH$_4$Cl below 5° C., and the aqueous phase was extracted with EtOAc. The combined organic phase was dried over Na$_2$SO$_4$, filtered, and concentrated. The obtained residue was triturated with 2/1 EtOAc/hexanes (90 mL), and the mixture was filtered to collect 6-bromo-7-fluoro-1-(phenylsulfonyl)-1H-indole. $^1$H NMR: (CDCl$_3$ 400 MHz): δ 7.96-7.98 (m, 2H), 7.79 (d, J=3.67 Hz, 1H), 7.60-7.64 (m, 1H), 7.51-7.55 (m, 2H), 7.34 (dd, J=8.38, 5.69 Hz, 1H), 7.21 (d, J=8.44 Hz, 1H), 6.67 (dd, J=3.67, 2.20 Hz, 1H).

Step 2

6-bromo-7-fluoro-1-(phenylsulfonyl)-1H-indole (22.7 g, 63.2 mmol) was dissolved in THF (220 mL) under N$_2$ and cooled to −65° C. A solution of LDA (2 M, 47.4 mL, 94.8 mmol) was added followed by the dropwise addition of TMEDA (16.7 mL, 111 mmol). The mixture was stirred for 1 h at −65° C. and DMF (24.3 mL, 316 mmol) was added. After an additional 3 h, the mixture was poured into saturated aqueous NH$_4$Cl (300 mL) and was extracted with DCM. The combined organic phase was washed with brine, dried over Na$_2$SO$_4$, filtered, and concentrated. The obtained residue was triturated with EtOAc (60 mL), and solids were collected by filtration. The trituration was repeated to afford 6-bromo-7-fluoro-1-(phenylsulfonyl)-1H-indole-2-carbaldehyde. $^1$H NMR: (CDCl3 400 MHz): δ 10.4 (s, 1H), 8.10-8.13 (m, 2H), 7.65-7.70 (m, 1H), 7.56-7.60 (m, 2H), 7.42-7.47 (m, 2H), 7.32 (d, J=8.44 Hz, 1H).

6-bromo-5-fluoro-1-(phenylsulfonyl)-1H-indole-2-carbaldehyde (I-24b)

Prepared following a similar procedure to I-24a from 6-bromo-5-fluoro-1H-indole. $^1$H NMR (CDCl$_3$ 400 MHz): δ 10.5 (s, 1H), 8.51 (d, J=5.75 Hz, 1H), 7.78-7.81 (m, 2H), 7.59-7.63 (m, 1H), 7.47-7.50 (m, 2H), 7.39 (d, J=0.490 Hz, 1H), 7.35 (d, J=7.82 Hz, 1H).

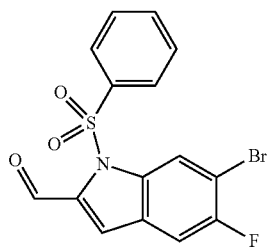

I-24b

Preparation of tert-butyl (R)-(1-(1-(phenylsulfonyl)-1H-pyrrolo[2,3-b]pyridin-6-yl)ethyl)carbamate (I-25a)

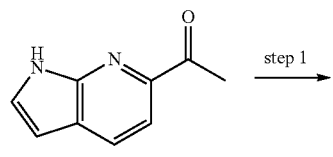

step 1

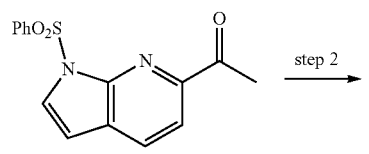

step 2

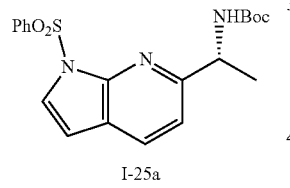

I-25a

Step 1

Step 1 of I-8a was followed to produce 1-(1-(phenylsulfonyl)-1H-pyrrolo[2,3-b]pyridin-6-yl)ethan-1-one from 1-(1H-pyrrolo[2,3-b]pyridin-6-yl)ethan-1-one. ES/MS: m/z 301.0 [M+H]⁺.

Step 2

Steps 1-4 of I-102 were followed to produce tert-butyl (R)-(1-(1-(phenylsulfonyl)-1H-pyrrolo[2,3-b]pyridin-6-yl)ethyl)carbamate from 1-(1-(phenylsulfonyl)-1H-pyrrolo[2,3-b]pyridin-6-yl)ethan-1-one. ES/MS: m/z 401.8 [M+H]⁺.

tert-butyl (R)-(1-(5-fluoro-1-(phenylsulfonyl)-1H-indol-6-yl)ethyl)carbamate (I-25b)

Prepared following a similar procedure to I-25a starting with I-13g. ES/MS: m/z 441.1 [M+Na]⁺. ¹H NMR (400 MHz, DMSO-d6) δ 8.02-7.97 (m, 3H), 7.81-7.77 (m, 2H), 7.70-7.67 (m, 1H), 7.57-7.53 (m, 2H), 7.35 (d, J=10.4 Hz, 1H), 6.78 (d, J=3.6 Hz, 1H), 4.94-4.91 (m, 1H), 1.40 (s, 9H), 1.31 (d, J=6.8 Hz, 3H).

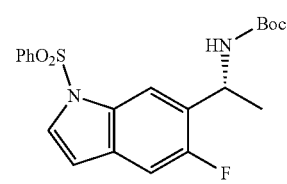

I-25b tert-butyl (R)-(1-(1-(phenylsulfonyl)-1H-indol-6-yl)ethyl)carbamate (I-25c)

Prepared following a similar procedure to I-25a starting with I-13h. ES/MS: m/z 423.0 [M+Na]⁺. ¹H NMR (400 MHz, CDCl3): δ 7.95 (s, 1H), 7.86 (dd, J=7.2, 1.6 Hz, 2H), 7.54-7.50 (m, 2H), 7.48-7.40 (m, 3H), 7.18 (dd, J=8.4, 1.2 Hz, 1H), 6.62 (d, J=3.6 Hz, 1H), 4.89-4.87 (m, 2H), 1.49-1.45 (m, 3H), 1.44 (s, 9H).

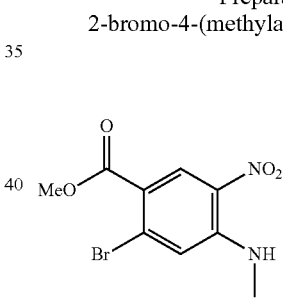

I-25c

Preparation of methyl 2-bromo-4-(methylamino)-5-nitrobenzoate (I-26)

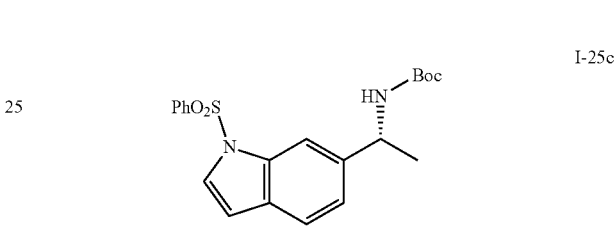

step 1

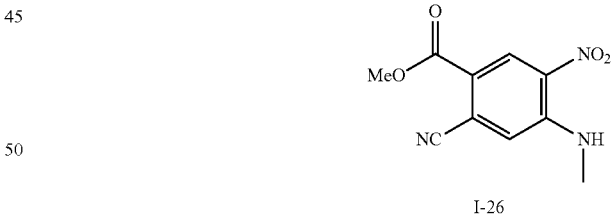

I-26

Step 1

A mixture of methyl 2-bromo-4-(methylamino)-5-nitrobenzoate (0.167 g, 0.578 mmol), zinc cyanide (0.271 g, 2.31 mmol), and tetrakis(triphenylphosphine)-palladium(0) (0.0668 g, 0.058 mmol) in DMF (2 mL) was heated at 90° C. After stirring overnight, the reaction mixture was cooled to rt and poured into water. The resulting solid was filtered, washed with water, and dried in vacuo. Purification via silica gel column chromatography (10-100% ethyl acetate/hexanes) yields methyl 2-cyano-4-(methylamino)-5-nitrobenzoate. 1H NMR (400 MHz, DMSO-d6) δ 8.77 (d, J=5.4 Hz, 1H), 8.69 (s, 1H), 7.63 (s, 1H), 3.88 (s, 3H), 3.06 (d, J=5.0 Hz, 3H).

197
Preparation of methyl 3-(difluoromethoxy)-4-(methylamino)-5-nitrobenzoate (I-27a)

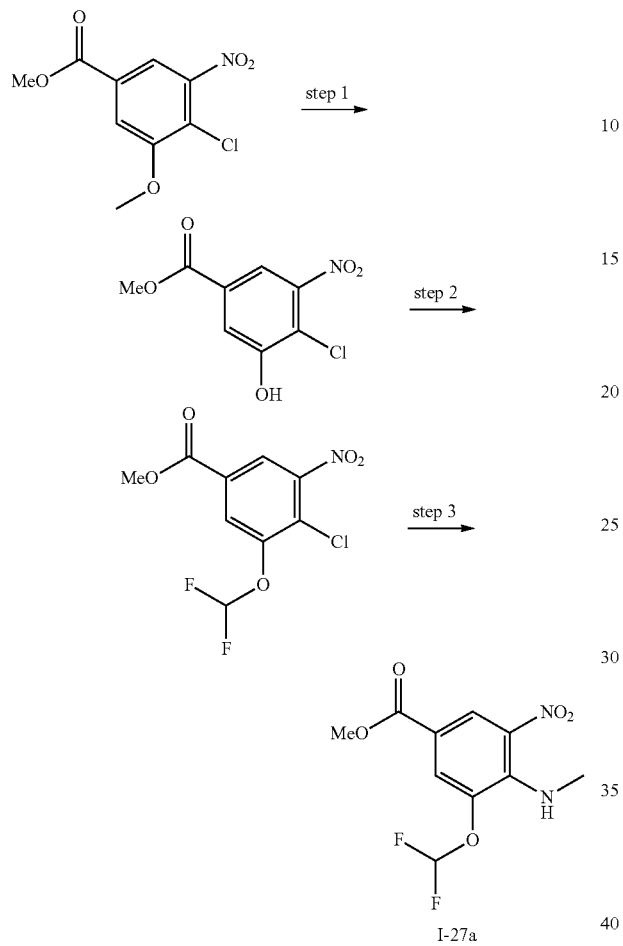

I-27a

198
methyl 4-(cyclopropylamino)-3-(difluoromethoxy)-5-nitrobenzoate (I-27b)

Prepared following a similar procedure to I-27a using cyclopropylamine. ES/MS: m/z 302.1 [M+H]$^+$.

Preparation of 6-chloro-2-vinyl-pyridine-3-carboxylic Acid (I-29)

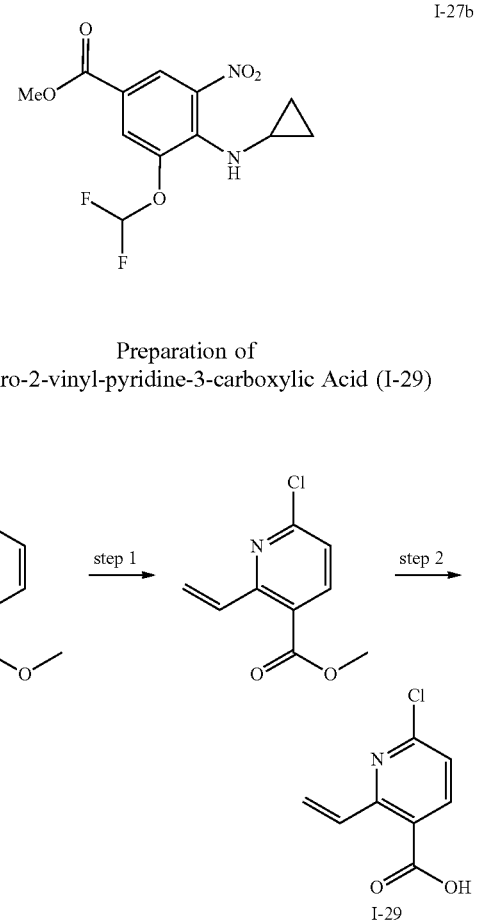

Step 1

To a solution of methyl 4-chloro-3-methoxy-5-nitrobenzoate (1.0 g, 4.07 mmol) in DCM (10 mL) at −78° C. was added BBr$_3$ (3.1 g, 12.2 mmol). The reaction was warm to rt and attired o/n. The reaction was cooled to 0° C., MeOH was added and the reaction mixture was stirred at rt for o/n. Concentration and purification via silica gel column chromatography (0-100% ethyl acetate/hexanes) affords methyl 4-chloro-3-hydroxy-5-nitrobenzoate.

Step 2

To a solution of methyl 4-chloro-3-hydroxy-5-nitrobenzoate (350 mg, 1.51 mmol) was added K$_2$CO$_3$ (3.1 g, 22.7 mmol) and the mixture was heated you 90° C. Chlorodifluoromethane was bubbled for 15 minutes. Upon cooling, the reaction was portioned between water and EtOAc. The organic phase was washed with brine and dried with MgSO$_4$. The crude mixture was used as is in the next step.

Step 3 methyl 3-(difluoromethoxy)-4-(methylamino)-5-nitrobenzoate was prepared following a similar procedure to I-7a from methyl 4-chloro-3-(difluoromethoxy)-5-nitrobenzoate. ES/MS: m/z 277.0 [M+H]$^+$.

Step 1.

A mixture of methyl 2-bromo-6-chloro-pyridine-3-carboxylate (211 mg, 0.842 mmol), Vinylboronic Acid Pinacol Ester (0.163 mL, 0.842 mmol), Bis(triphenylphosphine) palladium Chloride (59.1 mg, 0.0842 mmol), and cesium fluoride (384 mg, 2.53 mmol) in dioxane (1.5 mL) and water (0.75 mL) was heated at 80 degrees under argon overnight. After cooling to rt, the reaction mixture was diluted with ethyl acetate and water. The layers were separated and the aqueous was extracted with ethyl acetate. The combined organics were dried, filtered, and concentrated under reduced pressure. The resulting residue was purified via silica gel column chromatography (0-8% ethyl acetate/hexanes) to yield methyl 6-chloro-2-vinyl-pyridine-3-carboxylate. ES/MS: m/z 198.0 [M+H]$^+$.

Step 2

Lithium hydroxide, monohydrate (40.8 mg, 0.972 mmol) was added to a solution of methyl 6-chloro-2-vinyl-pyridine-3-carboxylate (48.0 mg, 0.243 mmol) in THF (1 mL), MeOH (0.5 mL), and water (0.5 mL) at rt. After 2 hours, an aqueous solution of hydrochloric acid (6N, 0.243 mL, 1.46 mmol) was added and the reaction mixture was diluted with ethyl acetate and water. The layers were separated and the aqueous was extracted with ethyl acetate. The combined organics were dried, filtered, and concentrated under reduced pressure to yield 6-chloro-2-vinyl-pyridine-3-carboxylic acid. ES/MS: m/z 183.9 [M+H]+.

Preparation of ethyl rac-(1S,2R)-2-((benzyloxy)methyl)-1-(trifluoromethyl)cyclopropane-1-carboxylate (I-30a) and ethyl rac-(1S,2S)-2-((benzyloxy)methyl)-1-(trifluoromethyl)cyclopropane-1-carboxylate (I-30b)

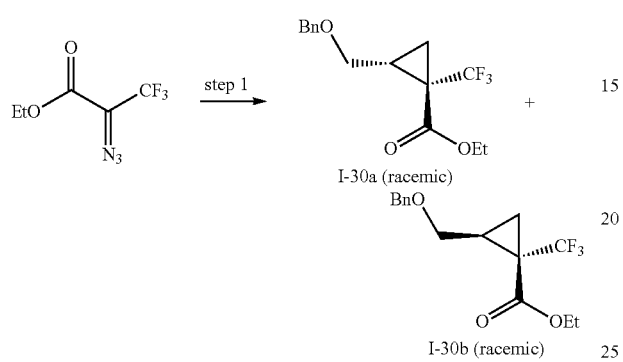

I-30a (racemic)

I-30b (racemic)

Step 1

A solution of allyl benzyl ether (48.8 g, 329 mmol) in DCM (300 mL) was degassed and purged with $N_2 \cdot Rh_2(OAc)_4$ (1.82 g, 8.24 mmol) was added followed by a solution of ethyl 2-diazo-3,3,3-trifluoropropanoate (30 g, 164 mmol) (prepared according to Shi, G. et. al. *J. Org. Chem.* 1990, 55, 3383-3386) in DCM (300 mL). The reaction mixture was stirred for 8 h at r.t. and was filtered. The filtrate was concentrated in vacuo, and the crude residue was purified by silica gel chromatography (1-5% EtOAc in hexanes) to provide ethyl rac-(1S,2R)-2-((benzyloxy)methyl)-1-(trifluoromethyl)cyclopropane-1-carboxylate and ethyl rac-(1S,2S)-2-((benzyloxy)methyl)-1-(trifluoromethyl)cyclopropane-1-carboxylate. Relative stereochemistry was assigned on the basis of NOEs observed in the hydroxymethyl products following ester reduction using $LiAlH_4$.

HNMR data for ethyl rac-(1S,2R)-2-((benzyloxy)methyl)-1-(trifluoromethyl)cyclopropane-1-carboxylate $^1H$ NMR: ($CDCl_3$ 400 MHz): δ 7.37-7.30 (m, 5H), 4.55 (s, 2H), 4.24-4.20 (m, 2H), 3.71-3.65 (m, 2H), 2.10-2.09 (m, 1H), 1.76-1.75 (m, 1H), 1.38-1.35 (m, 1H), 1.31-1.28 (m, 3H).

HNMR data for ethyl rac-(1S,2S)-2-((benzyloxy)methyl)-1-(trifluoromethyl)cyclopropane-1-carboxylate: $^1H$ NMR: ($CDCl_3$ 400 MHz): δ 7.36-7.29 (m, 5H), 4.52-4.23 (m, 2H), 4.23-4.18 (m, 2H), 3.77-3.76 (m, 1H), 3.53-3.48 (m, 1H), 2.04-2.02 (m, 1H), 1.59-1.52 (m, 2H), 1.29-1.25 (m, 3H).

Preparation of methyl 4-(methylamino)-3-nitro-5-(trifluoromethoxy)benzoate (I-31)

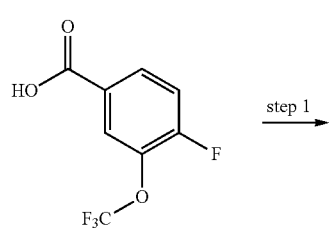

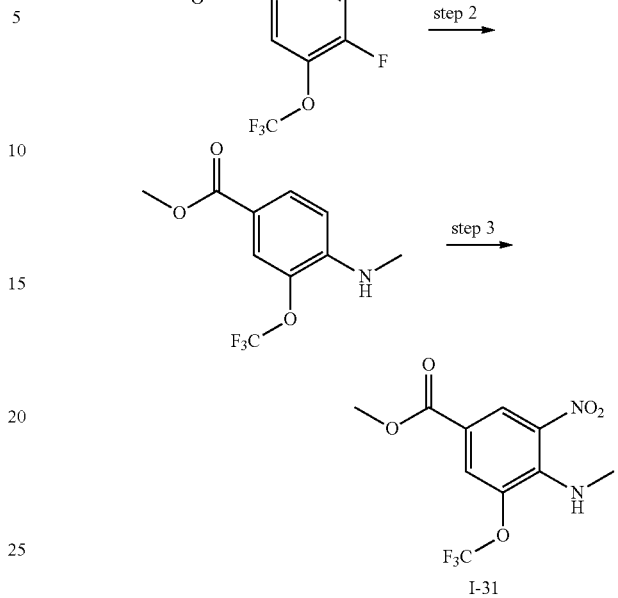

I-31

Step 1

To a stirring solution of 4-fluoro-3-(trifluoromethoxy)benzoic acid (2.0 g, 8.9 mmol) in MeOH (160 mL) at 0° C. was added acetyl chloride (2.5 mL, 36 mmol) dropwise. The reaction mixture was stirred overnight, and concentrated. The residue was diluted with dichloromethane and a saturated sodium bicarbonate solution. The aqueous layer was washed twice with dichloromethane. The combined organic layers were dried over $Na_2SO_4$, filtered and concentrated. The crude residue was purified by flash chromatography eluting with hexanes/EtOAc to give a colorless oil (1.5 g, 72%). 1H NMR (400 MHz, Chloroform-d) δ 8.05-7.97 (m, 2H), 7.33-7.22 (m, 1H), 3.94 (s, 3H).

Step 2

A mixture of methyl 4-fluoro-3-(trifluoromethoxy)benzoate (1.5 g, 6.4 mmol), methylamine hydrochloride (520 mg, 7.7 mmol), and potassium carbonate (1.8 g, 13 mmol) in DMF (12 mL) was stirred at 80° C. for 18 hr. The reaction was allowed to cool and water was added. The aqueous layer was washed three time with diethyl ether. The combined organic layers were washed twice with brine, dried over $MgSO_4$, filtered and concentrated. The crude residue was purified by flash chromatography eluting with hexanes/EtOAc to give a colorless oil (930 mg, 58%). ES/MS: m/z 250.00 [M+H]+.

Step 3

To a solution of methyl 4-(methylamino)-3-(trifluoromethoxy)benzoate (808 mg, 3.24 mmol) in sulfuric acid (5 mL) at 0° C. was added nitric acid (0.180 mL, 3.9 mmol). The reaction stirred at 0° C. for 30 min. Ice was added and saturated sodium bicarbonate until basic. The aqueous layer was washed three times with diethyl ether. The combined organic layers were dried over $MgSO_4$, filtered and concentrated. The crude residue was purified by flash chromatography eluting with hexanes/EtOAc to give a colorless oil (282 mg, 30%). ES/MS: m/z 294.99 [M+H]+.

Preparation of methyl 5-nitro-3,4-dihydro-2H-benzo[b][1,4]oxazine-7-carboxylate (I-32)

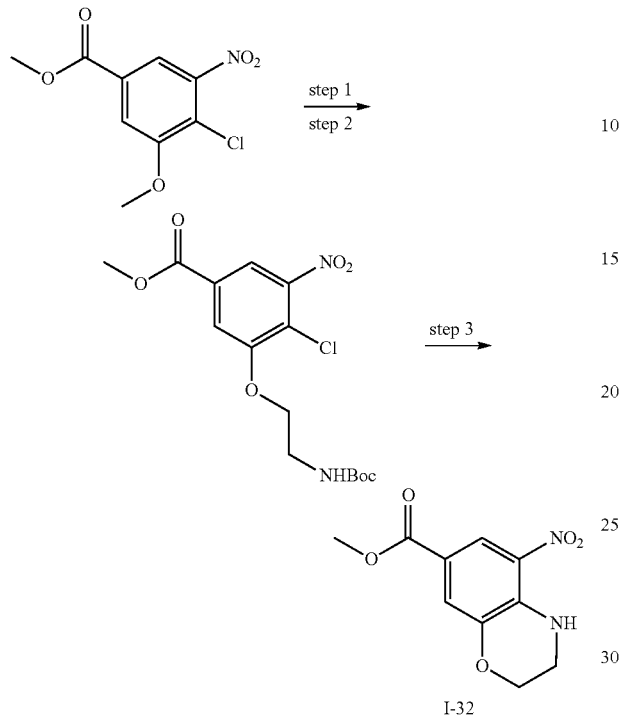

Step 1

To a solution of methyl 4-chloro-3-methoxy-5-nitrobenzoate (39.0 g, 0.16 mol) in DCM (500 mL) was added BBr$_3$ (1M in DCM, 78.6 g, 0.32 mol) at 0° C. dropwise over 30 minutes. The reaction mixture was stirred at room temperature for 5 h. After completion, the mixture was cooled to 0° C., quenched carefully with methanol, combined and concentrated in vacuo to give methyl 4-chloro-3-hydroxy-5-nitrobenzoate as a red solid. $^1$H NMR (400 MHz, CDCl$_3$): δ ppm 8.09 (s, 1H), 8.08 (s, 1H), 6.16 (s, 1H), 3.90 (s, 3H).

Step 2

To a solution of methyl 4-chloro-3-hydroxy-5-nitrobenzoate (43.0 g, 0.19 mmol, 1.0 eq) and tert-butyl (2-bromoethyl)carbamate (104.0 g, 0.46 mol, 2.5 eq) in DMF was added cesium carbonate (60.6 g, 0.19 mol, 1.0 eq) and the reaction mixture was stirred at room temperature for 8 h. After HPLC showed completion, the mixture was poured into ice-water and extracted with EtOAc (200 ml×3). The organic layer was separated, dried over MgSO$_4$ and solvent removed by evaporation. Purification by silica gel chromatography (EtOAc:petroleum ether=1:10) to give methyl 3-(2-((tert-butoxycarbonyl)amino)ethoxy)-4-chloro-5-nitrobenzoate as a yellow solid. $^1$H NMR (400 MHz, CDCl$_3$): δ ppm 7.98 (d, J=1.2 Hz, 1H), 7.68 (d, J=1.6 Hz, 2H), 4.14 (t, J=4.8 Hz, 2H), 3.83 (s, 3H), 3.57 (d, J=5.2 Hz, 2H), 1.38 (s, 9H).

Step 3

To a solution of methyl 3-(2-((tert-butoxycarbonyl)amino)ethoxy)-4-chloro-5-nitrobenzoate (41.6 g, 0.11 mmol, 1.0 eq) in DCM (400 mL) was added TFA (60 mL) in room temperature. After stirring at room temperature until starting material was consumed, the solution was concentrated in vacuo and use directly without purification for the next step. DMSO (400 mL) and trimethylamine (56.1 g, 0.55 mol, 5.0 eq) was added. The reaction stirred for 14 h before partitioning between water (500.0 mL) and EtOAc (400.0 mL). The organic layer was separated, dried with MgSO$_4$ and the solvent removed by evaporation. Purification by recrystallization from EtOAc (50 mL) to give methyl 5-nitro-3,4-dihydro-2H-benzo[b][1,4]oxazine-7-carboxylate as yellow solid. $^1$H NMR (400 MHz, CDCl$_3$): δ ppm 8.53 (d, J=2.0 Hz, 1H), 8.27 (s, 1H), 7.62 (dd, J1=0.8 Hz, J1=2.0 Hz, 1H), 4.29 (t, J=4.4 Hz, 2H), 3.91 (s, 3H), 3.74-3.71 (m, 2H).

Preparation of tert-butyl (R)-(1-(5-fluoro-2-formyl-1-((2-(trimethylsilyl)ethoxy)methyl)-1H-pyrrolo[2,3-b]pyridin-6-yl)ethyl)carbamate (I-33)

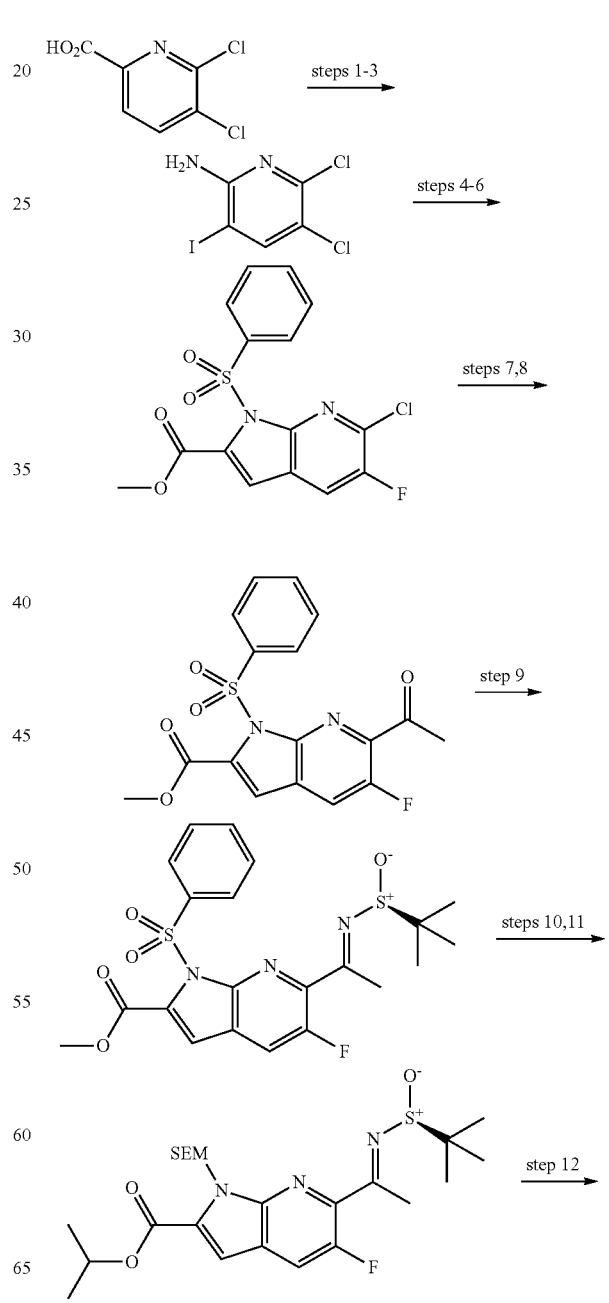

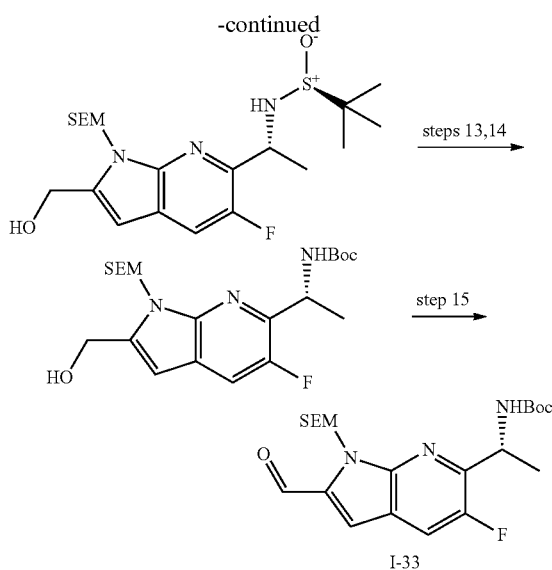

Step 1

6-chloro-5-fluoro-pyridine-2-carboxylic acid (7.5 g, 43 mmol) was taken up in t-BuOH (120 mL), and triethylamine (4.8 mL, 34 mmol) was added followed by diphenylphosphoryl azide (7.2 mL, 33 mmol). The mixture was allowed to stir at r.t. overnight and was then heated to 50° C. for 2 h. The reaction mixture was then heated to 85° C. for an additional 6 h and was then partitioned between EtOAc and water, dried over $Na_2SO_4$, filtered, and concentrated. Purification by silica gel chromatography (0-15% EtOAc in hexanes) provided tert-butyl N-(6-chloro-5-fluoro-2-pyridyl)carbamate. $^1$H NMR (400 MHz, DMSO-d6) δ 10.20 (s, 1H), 7.88 (dd, J=9.0, 8.0 Hz, 1H), 7.80 (dd, J=8.9, 3.2 Hz, 1H), 3.33 (s, 1H), 1.47 (s, 9H).

Step 2 tert-butyl N-(6-chloro-5-fluoro-2-pyridyl)carbamate (6.78 g, 27.5 mmol) was dissolved in DCM (50 mL), and TFA (25 mL) was added. The mixture was allowed to stir for 1 h and was then concentrated. The mixture was partitioned between EtOAc and sat. $NaHCO_3$. The organic phase was cried over $Na_2SO_4$, filtered, and concentrated to afford crude 6-chloro-5-fluoro-pyridin-2-amine which was carried on without further purification. ES/MS: m/z 146.93 [M+H]$^+$.

Step 3

6-chloro-5-fluoro-pyridin-2-amine (27 mmol) was dissolved in DMF. TFA (2.38 mL, 31 mmol) was added followed by N-iodosuccinimide (6.7 g, 30 mmol). After stirring for 2 h, additional N-iodosuccinimide (0.45 g, 2 mmol) was added. After an additional 30 min, the mixture was diluted with EtOAc, saturated aqueous $NaHCO_3$, and saturated aqueous sodium thiosulfate. The mixture was stirred for 5 min and the phases were separated. The organic phase was washed twice with 5% aqueous LiCl, dried over $Na_2SO_4$, filtered, and concentrated. Purification by silica gel chromatography (0-20% EtOAc in hexanes) provided 6-chloro-5-fluoro-3-iodo-pyridin-2-amine. ES/MS: m/z 146.93 [M+H]$^+$. $^1$H NMR (400 MHz, DMSO-d6) δ 8.09 (d, J=7.6 Hz, 1H), 6.43 (s, 2H).

Step 4

6-chloro-5-fluoro-3-iodo-pyridin-2-amine (5.6 g, 21 mmol) and $Pd_2(dba)_3$ (565 mg, 0.62 mmol) were taken up in DMA (55 mL) under $N_2$. N,N-dicyclohexylmethylamine (15.3 mL, 72 mmol) was added followed by pyruvic acid (4.3 mL, 62 mmol). The reaction was heated to 60° C. for 3 h, at which time it was cooled and diluted with EtOAc and water. 6 M Hydrochloric acid (17 mL, 100 mmol) was added and the phases were separated. The organic phase was washed with 5% aqueous LiCl, dried over $Na_2SO_4$, filtered, and concentrated. The crude product was slurried in 1:1 EtOAc:hexanes and filtered to afford 6-chloro-5-fluoro-1H-pyrrolo[2,3-b]pyridine-2-carboxylic acid. ES/MS: m/z 214.92 [M+H]$^+$. $^1$H NMR (400 MHz, DMSO-d6) δ 13.41 (s, 1H), 12.82-12.62 (m, 1H), 8.21 (d, J=9.1 Hz, 1H), 7.13 (d, J=2.1 Hz, 1H).

Step 5

6-chloro-5-fluoro-1H-pyrrolo[2,3-b]pyridine-2-carboxylic acid (2.3 g, 10.7 mmol) was suspended in MeOH (20 mL) under $N_2$ and concentrated sulfuric acid (1.73 mL, 32 mmol) was added. The mixture was heated to reflux for 18 h. The mixture was then cooled, diluted with DCM, and washed with saturated aqueous $NaHCO_3$ and water. The organic phase was dried over $Na_2SO_4$, filtered, and concentrated to afford methyl 6-chloro-5-fluoro-1H-pyrrolo[2,3-b]pyridine-2-carboxylate which was used without further purification. $^1$H NMR (400 MHz, DMSO-d6) δ 12.91 (s, 1H), 8.23 (d, J=9.1 Hz, 1H), 7.20 (d, J=1.9 Hz, 1H), 3.90 (s, 3H).

Step 6 methyl 6-chloro-5-fluoro-1H-pyrrolo[2,3-b]pyridine-2-carboxylate (2.29 g, 10 mmol) was dissolved in DMF (45 mL) under $N_2$ and the solution was cooled in an ice water bath. NaH (60% dispersion) (520 mg, 13.6 mmol) wad added in portions over 1 min. The mixture was stirred for 5 min, and was then removed from the cold bath and allowed to stir an additional 10 min. Benzenesulfonyl chloride (1.6 mL, 12.5 mmol) was then added. The reaction mixture was stirred for 1 h and was then diluted with saturated aqueous $NH_4Cl$, EtOAc, and water. The phases were separated, and the organic phase was washed with 10% aqueous LiCl, dried over $Na_2SO_4$, filtered, and concentrated. Purification by silica gel chromatography provided methyl 1-(benzenesulfonyl)-6-chloro-5-fluoro-pyrrolo[2,3-b]pyridine-2-carboxylate. $^1$H NMR (400 MHz, DMSO-d6) δ 8.31 (d, J=8.4 Hz, 1H), 8.24-8.17 (m, 2H), 7.86-7.80 (m, 1H), 7.78-7.71 (m, 2H), 7.38 (s, 1H), 3.95 (s, 3H).

Step 7 methyl 1-(benzenesulfonyl)-6-chloro-5-fluoro-pyrrolo[2,3-b]pyridine-2-carboxylate (3.1 g, 8.4 mmol) and potassium isopropyltrifluoroborate (2.49 g, 16.8 mmol) and $PdCl_2$(dppf).$CH_2Cl_2$ were taken up in EtOH (90 mL) under $N_2$. Triethylamine (5.9 mL, 42 mmol) was added and the mixture was heated to 80° C. After 3 h, the mixture was concentrated by half in vacuo, and cooled in an ice water bath. The resulting solids were collected by filtration and washed with additional EtOH (15 mL) to provide methyl 1-(benzenesulfonyl)-5-fluoro-6-isopropenyl-pyrrolo[2,3-b]pyridine-2-carboxylate. ES/MS: m/z 374.96 [M+H]$^+$.

Step 8 methyl 1-(benzenesulfonyl)-5-fluoro-6-isopropenyl-pyrrolo[2,3-b]pyridine-2-carboxylate (2.54 g, 6.78 mmol) was dissolved in THF (70 mL) and water (50 mL). Potassium osmate (VI) dihydrate (75 mg, 0.2 mmol) was added followed by sodium periodate (4.35 g, 20.4 mmol). The mixture was stirred for 18 h and was then partitioned between EtOAc and water. The organic phase was washed with water and brine, dried over $Na_2SO_4$, filtered, and concentrated to afford crude methyl 6-acetyl-1-(benzenesulfonyl)-5-fluoro-pyrrolo[2,3-b]pyridine-2-carboxylate that was used without further purification. ES/MS: m/z 376.99 [M+H]$^+$. $^1$H NMR (400 MHz, DMSO-d6) δ 8.30-8.25 (m, 2H), 8.22 (d, J=10.9 Hz, 1H), 7.87-7.79 (m, 1H), 7.79-7.71 (m, 2H), 7.39 (s, 1H), 3.99 (s, 3H), 2.72 (s, 3H).

Step 9 methyl 6-acetyl-1-(benzenesulfonyl)-5-fluoro-pyrrolo[2,3-b]pyridine-2-carboxylate (1.2 g, 3.2 mmol) and (S)-2-methylpropane-2-sulfinamide were dissolved in THF (30 mL) under $N_2$. Titanium (IV) isopropoxide (7.5 mL, 25 mmol) was added, and the resulting mixture was heated to 80° C. After stirring for 20 h, the mixture was diluted with EtOAc, and brine (2.5 mL) was slowly added, resulting in precipitation of solids. Additional water (2.5 mL) was added, and the mixture was filtered through Celite. Purification by silica gel chromatography provided [(E)-1-[1-(benzenesulfonyl)-5-fluoro-2-isopropoxycarbonyl-pyrrolo[2,3-b]pyridin-6-yl]ethylideneamino]-tert-butyl-oxido-sulfonium. ES/MS: m/z 507.78 $[M+H]^+$.

Step 10

[(E)-1-[1-(benzenesulfonyl)-5-fluoro-2-isopropoxycarbonyl-pyrrolo[2,3-b]pyridin-6-yl]ethylideneamino]-tert-butyl-oxido-sulfonium (1.14 g, 2.25 mmol) was dissolved in THF (25 mL) and a 1 M solution of TBAF in THF (2.7 mL, 2.7 mmol) was added. The reaction was stirred for 3 h, and was then partitioned between EtOAc and water. The organic phase was washed with brine, dried over $Na_2SO_4$, filtered, and concentrated to afford crude tert-butyl-[(E)-1-(5-fluoro-2-isopropoxycarbonyl-1H-pyrrolo[2,3-b]pyridin-6-yl]ethylideneamino]-oxido-sulfonium that was used without further purification. ES/MS: m/z 367.89 $[M+H]^+$.

Step 11 tert-butyl-[(E)-1-(5-fluoro-2-isopropoxycarbonyl-1H-pyrrolo[2,3-b]pyridin-6-yl)ethylideneamino]-oxido-sulfonium (2.25 mmol) was dissolved in DMF. Hunig's base (2 mL, 12 mmol) was added, followed by 2-(Trimethylsilyl)ethoxymethyl chloride (0.48 mL, 2.7 mmol). The reaction was stirred until complete by LCMS and was then partitioned between EtOAc and water. The organic phase was washed with 10% aq. LiCl, dried over $Na_2SO_4$, filtered and concentrated. Purification by silica gel chromatography provided tert-butyl-[(E)-1-[5-fluoro-2-isopropoxycarbonyl-1-(2-trimethylsilylethoxymethyl)pyrrolo[2,3-b]pyridin-6-yl]ethylideneamino]-oxido-sulfonium. (1.08 g, 96%) ES/MS: m/z 497.86 $[M+H]^+$.

Step 12 tert-butyl-[(E)-1-[5-fluoro-2-isopropoxycarbonyl-1-(2-trimethylsilylethoxymethyl)pyrrolo[2,3-b]pyridin-6-yl]ethylideneamino]-oxido-sulfonium (0.95 g, 1.9 mmol) was dissolved in THF (20 mL) under $N_2$. The solution was cooled to −78° C. and a 1 M solution of L-selectride in THF (2.3 mL, 2.3 mmoL) was added. The reaction mixture was allowed to stir 1 h and was removed from the cold bath. Once the temperature approached 0° C., the reaction mixture was placed in an ice water bath and stirred an additional 30 min. The mixture was recooled to −78° C., and additional L-selectride (0.35 mL, 0.35 mmol) was added.

The reaction mixture was stirred 5 min, and was then placed in an ice water bath. After an additional 15 min, the mixture was quenched with saturated aqueous $NH_4Cl$ and diluted with EtOAc. The phases were separated, and the organic phase was dried over $Na_2SO_4$, filtered, and concentrated. Purification by silica gel chromatography provided tert-butyl-[[(1R)-1-[5-fluoro-2-isopropoxycarbonyl-1-(2-trimethylsilylethoxymethyl)pyrrolo[2,3-b]pyridin-6-yl]ethyl]amino]-oxido-sulfonium. ES/MS: m/z 499.78 $[M+H]^+$.

Step 13 and 14.

tert-butyl-[[(1R)-1-[5-fluoro-2-(hydroxymethyl)-1-(2-trimethylsilylethoxymethyl)pyrrolo[2,3-b]pyridin-6-yl]ethyl]amino]-oxido-sulfonium (450 mg, 1.0 mmol) was dissolved in $Et_2O$ (15 mL). A solution of hydrochloric acid in dioxane (4 M, 0.51 mL) was added dropwise, and the resulting mixture was stirred 30 min and concentrated. The crude residue was triturated twice with hexanes and was dissolved in DCM (15 mL). Triethylamine (0.62 mL, 4.4 mmol) was added followed by di-tert-butyl dicarbonate (205 mg, 0.94 mmol). The mixture was stirred overnight, concentrated directly onto silica gel, and purified by silica gel chromatography (0-60% EtOAc in hexanes) to afford tert-butyl N-[(1R)-1-[5-fluoro-2-(hydroxymethyl)-1-(2-trimethylsilylethoxymethyl)pyrrolo[2,3-b]pyridin-6-yl]ethyl]carbamate. ES/MS: m/z 439.86 $[M+H]^+$.

Step 15.

tert-butyl N-[(1R)-1-[5-fluoro-2-(hydroxymethyl)-1-(2-trimethylsilylethoxymethyl)pyrrolo[2,3-b]pyridin-6-yl]ethyl]carbamate (300 mg, 0.68 mmol) was dissolved in DCM (6 mL). $MnO_2$ (330 mg, 3.8 mmol) was added and the reaction mixture was stirred at r.t. for 3 h, at which time additional $MnO_2$ (150 mg, 1.7 mmol) was added. The mixture was stirred an additional 18 h and was then filtered through a short pad of silica gel with 1:1 EtOAc:DCM. The filtrate was concentrated to provide tert-butyl (R)-(1-(5-fluoro-2-formyl-1-((2-(trimethylsilyl)ethoxy)methyl)-1H-pyrrolo[2,3-b]pyridin-6-yl)ethyl)carbamate. ES/MS: m/z 437.71 $[M+H]^+$.

Preparation of tert-butyl (2-(2-formyl-1H-pyrrolo[2,3-b]pyridin-6-yl)propan-2-y)carbamate (I-34)

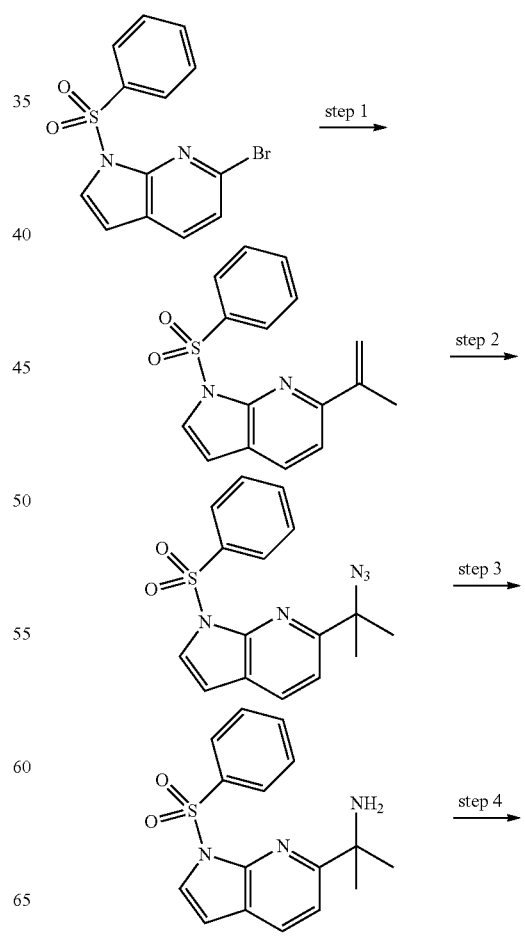

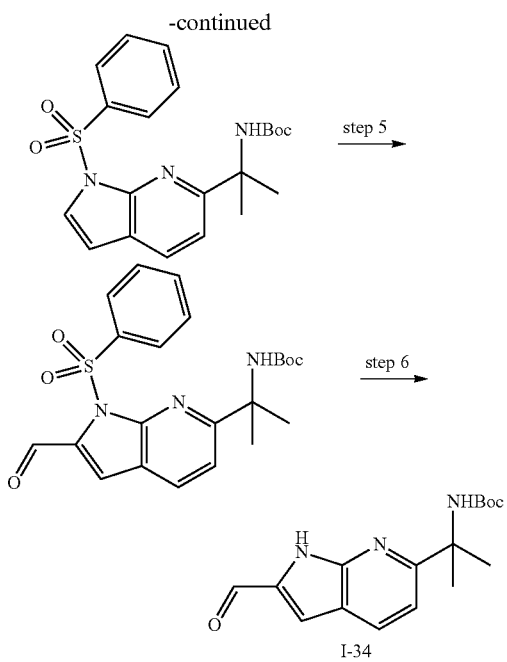

Step 1

A mixture of 1-(benzenesulfonyl)-6-bromo-pyrrolo[2,3-b]pyridine (1.31 g, 3.88 mmol), potassium vinyltrifluoroborate (1.15 g, 7.78 mmol), Dichloro 1,1'-bis(diphenylphosphino)ferrocene palladium (II) dichloromethane (0.222 g, 0.271 mmol) and triethylamine (2.7 mL, 19.4 mmol) in ethanol (60 mL) was heated at 75 degrees under argon overnight. After cooling to rt, the reaction mixture was diluted with ethyl acetate and filtered over celite. The filtrate was concentrated under reduced pressure and the resulting residue was purified via silica gel column chromatography (0-35% ethyl acetate/hexanes) to yield 1-(phenylsulfonyl)-6-(prop-1-en-2-yl)-1H-pyrrolo[2,3-b]pyridine. ES/MS: m/z 300.0 [M+H]⁺.

Step 2

Iron(III) oxalate hexahydrate (1.86 g, 0.00385 mol) was stirred in water (30 mL) until completely dissolved (~3 hours). After cooling to zero degrees, sodium azide (401 mg, 6.17 mmol) and THF (15 mL) was added. To the cooled mixture was added a solution of 1-(benzenesulfonyl)-6-isopropenyl-pyrrolo[2,3-b]pyridine (230 mg, 0.771 mmol) in THF (20 mL) followed by slow addition of sodium borohydride (0.0933 g, 0.00247 mol). After 5 minutes, a second batch of sodium borohydride (0.0933 g, 0.00247 mol) was slowly added. After 30 minutes, the reaction mixture was quenched with 28% aq NH₄OH (12 mL) and diluted with ethyl acetate and brine. The layers were separated and the aqueous extracted with ethyl acetate. The combined organics were dried, filtered, and concentrated under reduced pressure to yield 6-(2-azidopropan-2-yl)-1-(phenylsulfonyl)-1H-pyrrolo[2,3-b]pyridine, which was used without purification. ES/MS: m/z 341.8 [M+H]⁺.

Step 3

A mixture of 6-(1-azido-1-methyl-ethyl)-1-(benzenesulfonyl)pyrrolo[2,3-b]pyridine (263 mg, 0.770 mmol) and palladium on carbon (10%, 82 mg, 0.077 mmol) in ethanol (6 mL) was hydrogenated under an atmosphere of hydrogen. After 2 hours, the reaction mixture was diluted with ethyl acetate and filtered over celite. The filtrate was concentrated to yield 2-(1-(phenylsulfonyl)-1H-pyrrolo[2,3-b]pyridin-6-yl)propan-2-amine. ES/MS: m/z 315.9 [M+H]⁺.

Step 4

Di-tert-butyl dicarbonate (0.202 g, 0.000925 mol) was added to a mixture of 2-(1-(phenylsulfonyl)-1H-pyrrolo[2,3-b]pyridin-6-yl)propan-2-amine (243 mg, 0.770 mmol) and triethylamine (0.23 mL, 0.925 mmol) in DCM (4 mL) at rt. After 4 hours, the reaction mixture was concentrated and the resulting residue purified via silica gel column chromatography (0-35% ethyl acetate in hexanes) to yield tert-butyl (2-(1-(phenylsulfonyl)-1H-pyrrolo[2,3-b]pyridin-6-yl)propan-2-yl)carbamate. ES/MS: m/z 415.9 [M+H]⁺.

Step 5

To a cooled solution of tert-butyl (2-(1-(phenylsulfonyl)-1H-pyrrolo[2,3-b]pyridin-6-yl)propan-2-yl)carbamate (196 mg, 0.472 mmol) in THF (4 mL) at −78 degrees was slowly added a solution of BuLi in hexanes (2.5M, 0.57 mL, 1.4 mmoL) dropwise). After 30 min, DMF (0.18 mL, 2.36 mmol) was added dropwise. After 30 min, the reaction mixture was quenched with sat. NH₄Cl (aq) and diluted with ethyl acetate. The layers were separated and the aqueous extracted with ethyl acetate. The combined organics were dried, filtered, and concentrated under reduced pressure to yield tert-butyl (2-(2-formyl-1-(phenylsulfonyl)-1H-pyrrolo[2,3-b]pyridin-6-yl)propan-2-yl)carbamate. ES/MS: m/z 443.9 [M+H]⁺.

Step 6

A solution of TBAF in THF (1M, 0.87 mL, 0.87 mmol) was added to solution of crude tert-butyl (2-(2-formyl-1-(phenylsulfonyl)-1H-pyrrolo[2,3-b]pyridin-6-yl)propan-2-yl)carbamate (258 mg, 0.582 mmol) in THF (5 mL) at rt. After one hour, the reaction mixture was concentrated and the resulting residue purified via silica gel column chromatography (0-50% ethyl acetate in hexanes) to yield tert-butyl (2-(2-formyl-1H-pyrrolo[2,3-b]pyridin-6-yl)propan-2-yl)carbamate. ES/MS: m/z 303.8 [M+H]⁺.

2. Synthesis of Intermediates I-100 to I-157

Preparation of ethyl (R)-2-(6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (I-100)

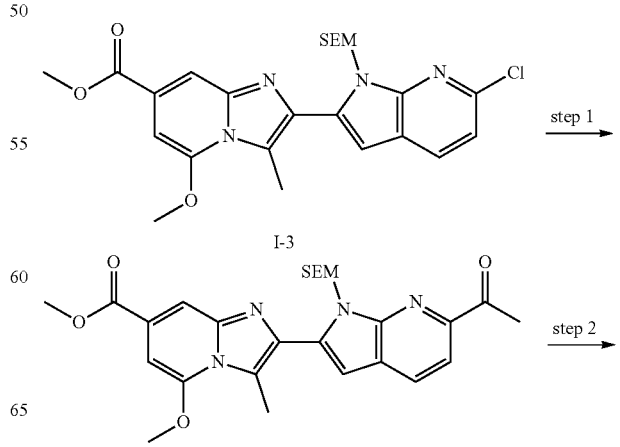

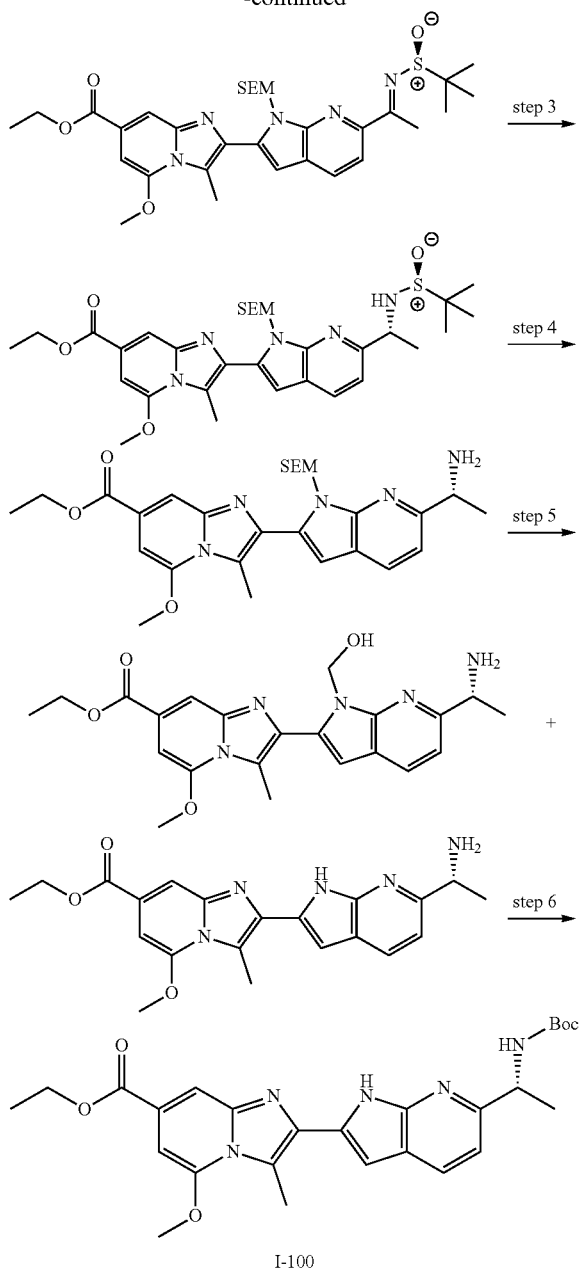

I-100

Step 1

Methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate (I-3, 2.1 g, 4.17 mmol) and PdCl$_2$(dppf).CH$_2$Cl$_2$ (341 mg, 0.42 mmol, 10 mol %) were taken up in dioxane (20 mL) in a pressure flask. The mixture was stirred and degassed with nitrogen for 10 minutes. 1-Ethoxyvinyltributyltin (2.8 ml, 8.34 mmol, 2 equiv.) was added and the resulting mixture was stirred at 100° C. for 3 hours. Upon cooling, the mixture was filtered with EtOAc through Celite and the filtrate was concentrated. The resulting residue was dissolved in THF (30 mL), and 1N HCl (4.0 mL, 4.0 mmol, 0.95 equiv.) was added. The mixture was stirred 30 min, at which time it was diluted with EtOAc and water. Phases were separated, and the aqueous phase was extracted with EtOAc. The organic phase was dried over MgSO$_4$, filtered, and concentrated to crude solid. The solid was slurried in 30 mL hexanes for 30 min, and the mixture was filtered to collect solids. The filter cake was slurried in ~30 mL hexanes for 30 minutes and the mixture was filtered to collect methyl 2-(6-acetyl-1-((2-(trimethylsilyl)ethoxy)methyl)-1H-pyrrolo[2,3-b]pyridin-2-yl)-5-methoxy-3-methylimidazo[1,2-a]pyridine-7-carboxylate which was used without further purification for the next step. ES/MS: m/z 509.3 [M+H]$^+$.

Step 2

Methyl 2-(6-acetyl-1-((2-(trimethylsilyl)ethoxy)methyl)-1H-pyrrolo[2,3-b]pyridin-2-yl)-5-methoxy-3-methylimidazo[1,2-a]pyridine-7-carboxylate (4.17 mmol) and (S)-2-methylpropane-2-sulfinamide (2.02 g, 16.7 mmol. 4 equiv.) were suspended in THF (30 mL) under nitrogen. Titanium (IV) ethoxide* (5.2 mL, 25 mmol, 6 equiv.) was added, and the resulting stirred mixture was heated at 60° C. After 18 h, the reaction mixture was poured into a vigorously stirred mixture of brine (150 mL) and EtOAc (100 mL). The heterogeneous mixture was diluted further with EtOAc and the phases were separated. The aqueous phase was diluted with EtOAc, Celite (~50 g) was added and stirred with the resulting emulsion. The mixture was filtered through a pad of Celite with EtOAc, and the resulting clear biphasic mixture was separated. The combined organic phase was dried over Na$_2$SO$_4$, filtered and concentrated. Purification by silica gel (10-60% EtOAc in hexanes) provided ethyl (S)-2-(6-(1-(((tert-butylsulfinyl)imino)ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate. ES/MS: m/z 626.4 [M+H]$^+$.

*Titanium (IV) isopropoxide can also be used; in that case, the resulting product of this step would be an isopropyl ester.

Step 3

Ethyl (S)-2-(6-(1-(((tert-butylsulfinyl)imino)ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (2.6 g, 4.2 mmol) was dissolved in THF (40 mL) under nitrogen. The resulting mixture was cooled in a CO$_2$/acetone bath to approximately −78° C. L-Selectride (1 M in THF, 4.6 mL, 4.6 mmol, 1.1 equiv.) was then added dropwise over 30 min, and the resulting mixture was stirred for 20 min at −78° C. The reaction was quenched with sat. aq. NH$_4$Cl and diluted with EtOAc and water. The phases were separated, and the organic phase was dried over MgSO$_4$, filtered, and concentrated. The obtained residue was purified by silica gel chromatography (5-100% 3:1 EA/EtOH in hexane) to afford ethyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate. ES/MS: m/z 628.4 [M+H]$^+$.

Step 4

Ethyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (675 mg, 1.08 mmol) was dissolved in dioxane (10 mL) at 0° C. 4M HCl in dioxane (1.34 mL, 5.4 mmol, 5 equiv.) was added, resulting in the immediate precipitation of solids. After stirring 15 min, the reaction mixture was concentrated in vacuo to provide crude ethyl (R)-2-(6-(1-aminoethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (putative bis-HCl salt) which was used without further purification. ES/MS: m/z 524.3 [M+H]$^+$.

Step 5

Ethyl (R)-2-(6-(1-aminoethyl)-1-((2-(trimethylsilyl)ethoxy)methyl)-1H-pyrrolo[2,3-b]pyridin-2-yl)-5-methoxy-3-methylimidazo[1,2-a]pyridine-7-carboxylate (1.08 mmol, putative bis-HCl salt) was dissolved in DCM (10 mL) at room temperature. TFA (1.6 mL, 20 equiv.) was added. After stirring 60 min, the reaction mixture was concentrated in vacuo and dried under vacuum to provide crude mixture of ethyl (R)-2-(6-(1-aminoethyl)-1-(hydroxymethyl)-1H-pyrrolo[2,3-b]pyridin-2-yl)-5-methoxy-3-methylimidazo[1,2-a]pyridine-7-carboxylate and ethyl (R)-2-(6-(1-aminoethyl)-1H-pyrrolo[2,3-b]pyridin-2-yl)-5-methoxy-3-methylimidazo[1,2-a]pyridine-7-carboxylate which was used without further purification. ES/MS: m/z 424.2 [M+H]$^+$, 394.2 [M+H]$^+$.

Step 6. Part A:

The above crude mixture (ca. 1.08 mmol) was dissolved in DCM (5 mL). Di-tert-butyl dicarbonate (235 mg, 1.08 mmol, 1.0 equiv) and diisopropylethylamine (0.94 mL, 5.4 mmol, 5.0 equiv.) were added. The mixture was stirred at room temperature for 2 h. Water and EtOAc were added, phases were separated, and the aqueous phase was extracted with EtOAc. The organic phase was dried over MgSO$_4$, filtered, and concentrated. Part B: The resulting residue was dissolved in methanol (5 mL) and ethylenediamine (0.72 mL, 10.8 mmol, 10 equiv.) was added. The mixture was stirred at room temperature for 3.5 h. The mixture was concentrated and purified by silica gel chromatography (5-80% 3:1 EA/EtOH in hexane) to afford ethyl (R)-2-(6-(1-((tert-butoxycarbonyl)amino)ethyl)-1H-pyrrolo[2,3-b]pyridin-2-yl)-5-methoxy-3-methylimidazo[1,2-a]pyridine-7-carboxylate. ES/MS: m/z 494.3 [M+H]$^+$.

Preparation of isopropyl (R)-2-(6-(1-(((benzyloxy)carbonyl)amino)ethyl)-1H-pyrrolo[2,3-b]pyridin-2-yl)-3-cyclopropylimidazo[1,2-a]pyridine-7-carboxylate (I-101a)

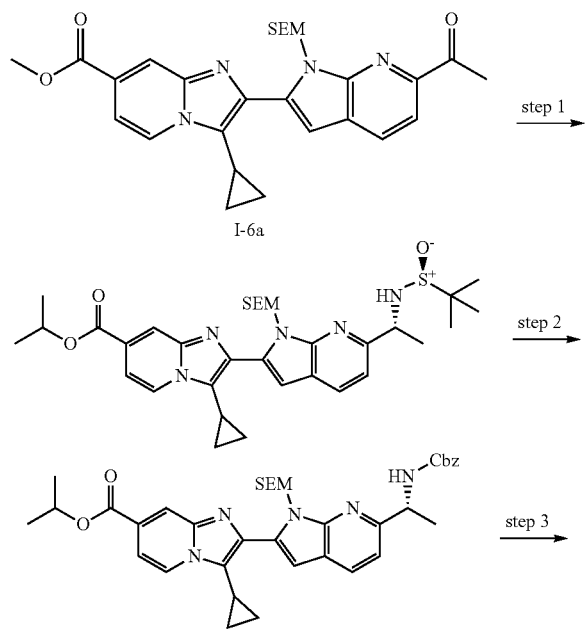

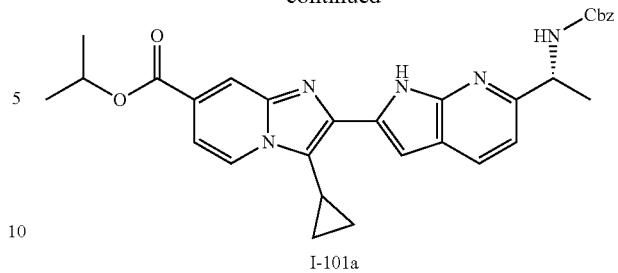

I-101a

Step 1

Isopropyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-3-cyclopropylimidazo[1,2-a]pyridine-7-carboxylate was prepared following steps 2 and 3 of I-100 using I-6a. ES/MS: m/z 637.9 [M+H]$^+$.

Step 2

A solution of 4M HCl in Dioxane, (1.1 mL, 4.4 mmol) was added to a solution of isopropyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-3-cyclopropylimidazo[1,2-a]pyridine-7-carboxylate (562 mg, 0.881 mmol) in dioxane (12 mL). After 4 hours, the reaction mixture was concentrated under reduced pressure. To the resulting residue in DCM (12 mL) was added triethylamine (0.7 mL, 5.0 mmol) and N-carbobenzoxyoxysuccinimide (0.26 g, 1.06 mmol). After stirring 3 days, sat. NaHCO$_3$ (aq) was added and the reaction mixture was diluted with DCM. The layers were separated and the aqueous was extracted with DCM. The combined organics were washed with brine, dried (MgSO$_4$), filtered, and concentrated under reduced pressure. The resulting residue was purified via silica gel column chromatography (0-85% ethyl acetate in hexanes) to yield isopropyl (R)-2-(6-(1-(((benzyloxy)carbonyl)amino)ethyl)-1-((2-(trimethylsilyl)ethoxy)methyl)-1H-pyrrolo[2,3-b]pyridin-2-yl)-3-cyclopropylimidazo[1,2-a]pyridine-7-carboxylate. ES/MS: m/z 666.9 [M+H]$^+$.

Step 3

Isopropyl (R)-2-(6-(1-(((benzyloxy)carbonyl)amino)ethyl)-1H-pyrrolo[2,3-b]pyridin-2-yl)-3-cyclopropylimidazo[1,2-a]pyridine-7-carboxylate was prepared following step 5 and Part B of step 6 of I-100. ES/MS: m/z 537.9 [M+H]$^+$.

isopropyl (R)-2-(6-(1-((tert-butoxycarbonyl)amino)ethyl)-1H-pyrrolo[2,3-b]pyridin-2-yl)-3-cyclopropyl-5-methoxyimidazo[1,2-a]pyridine-7-carboxylate (I-101b)

Prepared following a similar procedure to I-101a using I-6b. $^1$H NMR (400 MHz, Chloroform-d) δ 11.99 (brs, 1H), 8.11 (d, J=8.0 Hz, 1H), 7.99 (s, 1H), 7.46-7.31 (m, 4H), 7.20 (d, J=8.0 Hz, 1H), 7.04 (s, 1H), 6.67 (s, 1H), 6.40 (d, J=7.8 Hz, 1H), 5.36-5.24 (m, 1H), 5.16 (d, J=12.4 Hz, 1H), 5.12 (d, J=7.6 Hs, 1H), 5.08 (d, J=12.3 Hz, 1H), 4.15 (s, 3H), 2.51-2.41 (m, 1H), 1.64 (d, J=7.0 Hz, 3H), 1.62-1.50 (m, 1H), 1.43 (d, J=6.2 Hz, 6H), 1.25-1.19 (m, 2H), 0.76-0.66 (m, 2H).

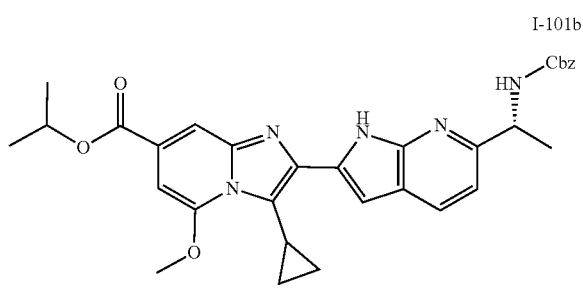 [SMILES: COc1cc(C(=O)OC(C)C)cc2nc(-c3cc4ccc([C@@H](C)NC(=O)OCc5ccccc5)nc4[nH]3)c(C3CC3)n12]

Preparation of isopropyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate (I-102)

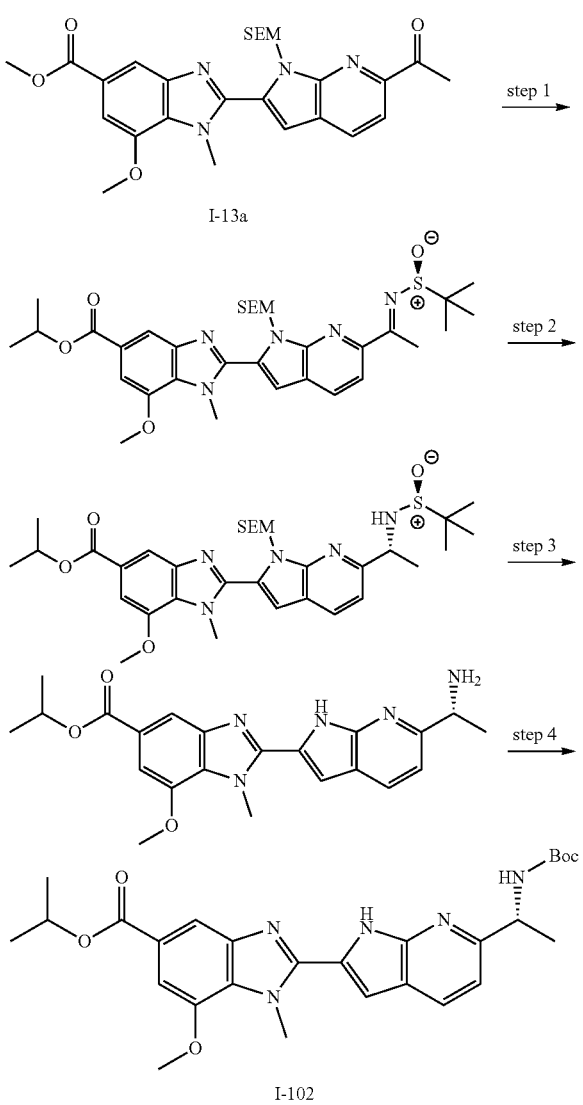

Step 1.

Methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-13a, 5.58 g, 11.0 mmol) and (S)-2-methylpropane-2-sulfinamide (5.3 g, 44 mmol. 4 equiv.) were taken up in THF (100 mL) under nitrogen. Titanium(IV) isopropoxide (26 mL, 88 mmol, 8 equiv.) was added, and the resulting stirred mixture was heated at 60° C. After 16 h, brine (7 mL) and EtOAc (200 mL) were added and the reaction mixture was stirred vigorously. The organic phase was decanted off, and EtOAc (150 mL) was added with stirring followed by some DCM to cut the emulsion. The organic layer was decanted, and this process was repeated once more. The aqueous phase was diluted with EtOAc (150 mL), and Celite (40 g) was added. The mixture was filtered through Celite. The combined organic phase was dried over $Na_2SO_4$, filtered, and concentrated. Purification by silica gel (15-80% EtOAc in hexanes) provided isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate. ES/MS: m/z 640.3 $[M+H]^+$.

Step 2

Isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate (5.7 g, 4.2 mmol) was dissolved in THF (120 mL) under nitrogen. The resulting mixture was cooled to −78° C. 1 M L-Selectride in THF (5.1 mL, 5.1 mmol, 1.2 equiv.) was then added dropwise over 5 min, and the resulting mixture was stirred for 6 h at −78° C. The reaction was removed from the cold bath and placed in an ice bath once the internal temperature was −5° C. The reaction was stirred an additional 20 min, whereupon LCMS indicated complete conversion. The reaction was quenched with sat. aq. $NH_4Cl$ and diluted with EtOAc and water. The phases were separated, and the organic phase was dried over $MgSO_4$, filtered, and concentrated. The obtained residue was purified by silica gel chromatography (10-60% acetone in hexanes) to afford product isopropyl 2-(6-((R)-1-(((S)-tert-butylsulfinyl)amino)ethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 642.4 $[M+H]^+$.

Step 3

Isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1 methyl-1H-benzo[d]imidazole-5-carboxylate (3.48 g, 3.86 mmol) was dissolved in MeCN (50 mL). 4M HCl in dioxane (24 mL, 97 mmol) was added, resulting in an immediate precipitation of solids that redissolved on further addition of HCl. The resulting solution was heated to 45° C. and stirred for 6 h, over which time solids precipitated out. The reaction mixture was then concentrated in vacuo, suspended in DCM (20 mL), and diluted with diethyl ether (60 mL). Filtration followed by washing with diethyl ether provided isopropyl (R)-2-(6-(1-aminoethyl)-1H-pyrrolo[2,3-b]pyridin-2-yl)-7-methoxy-1-methyl-1H-benzo[d]imidazole-5-carboxylate (putative bis-HCl salt) that was used without further purification. ES/MS: m/z 408.3 $[M+H]^+$. *This procedure was also followed in the case where Boc was used instead of SEM as protecting group (see I-13b and I-13c, used for the synthesis of I-104a and I-104b, respectively).

*Alternatively, a Mitsunobu reaction can be performed using the corresponding primary alcohol as electrophile (see step 1 of Procedure 27).

Step 4

Isopropyl (R)-2-(6-(1-aminoethyl)-1H-pyrrolo[2,3-b]pyridin-2-yl)-7-methoxy-1-methyl-1H-benzo[d]imidazole-5-carboxylate (HCl salt) from above was taken up in DCM (50 mL, suspension), and trimethylamine (5.4 mL, 38 mmol, 10 equiv.) was added. The resulting mixture was cooled in an ice water bath, and Boc₂O (842 mg, 3.85 mmol) was added as a solution in DCM (5 mL). The resulting mixture was removed from the cold bath and stirred an additional 10 min. The mixture was diluted with DCM and washed with a mixture of 5% aq. Na₂CO₃ and water. DCM was used to extract, and the combined organic phase was dried (Na₂SO₄), filtered, and concentrated. The resulting residue was slurried in 20 mL EtOAc, and 60 mL hexane was added in portions. After stirring an additional 30 min, the mixture was filtered to collect solids. The solids were washed with additional 20% EtOAC in hexanes (20 mL) followed by hexanes. Drying afforded isopropyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate. ES/MS: m/z 508.3 [M+H]⁺. ¹H NMR (400 MHz, DMSO-d6) δ 12.33 (d, J=2.1 Hz, 1H), 8.06 (d, J=8.2 Hz, 1H), 7.93 (d, J=1.3 Hz, 1H), 7.38 (d, J=8.1 Hz, 1H), 7.36 (d, J=1.3 Hz, 1H), 7.19 (d, J=8.2 Hz, 1H), 7.13 (d, J=2.0 Hz, 1H), 5.16 (hept, J=6.3 Hz, 1H), 4.77 (p, J=7.2 Hz, 1H), 4.29 (s, 3H), 4.03 (s, 3H), 1.43-1.34 (m, 18H).

isopropyl (R)-2-(6-(1-((tert-butoxycarbonyl)amino)ethyl)-1H-pyrrolo[2,3-b]pyridin-2-yl)-1-cyclopropyl-7-methoxy-1H-benzo[d]imidazole-5-carboxylate (I-103a)

Prepared following a similar procedure to I-102 starting with I-12. ES/MS: m/z 534.1 [M+H]⁺.

I-103a

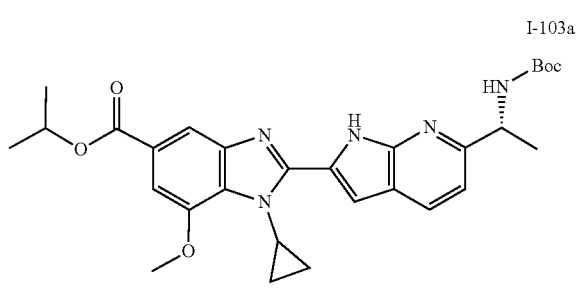 [SMILES: COc1cc(C(=O)OC(C)C)cc2nc(-c3cc4ccc([C@@H](C)NC(=O)OC(C)(C)C)nc4[nH]3)n(C3CC3)c12]

isopropyl (R)-2-(6-(1-((tert-butoxycarbonyl)amino)ethyl)-1H-indol-2-yl)-7-methoxy-1-methyl-1H-benzo[d]imidazole-5-carboxylate (I-104a)

Prepared following a similar procedure to I-102 starting with I-13b. ES/MS: m/z 507.3 [M+H]⁺. ¹H NMR (400 MHz, DMSO-d6) δ 11.92 (d, J=2.2 Hz, 1H), 7.91 (d, J=1.3 Hz, 1H), 7.59 (d, J=8.3 Hz, 1H), 7.46 (d, J=8.3 Hz, 1H), 7.42 (s, 1H), 7.34 (d, J=1.3 Hz, 1H), 7.15 (d, J=2.1 Hz, 1H), 7.06 (d, J=8.3, 1H), 5.22-5.16 (m, 1H), 4.77-4.64 (m, 1H), 4.32 (s, 3H), 4.02 (s, 3H), 1.38 (brs, 9H), 1.37 (s, 6H), 1.36 (s, 3H).

I-104a

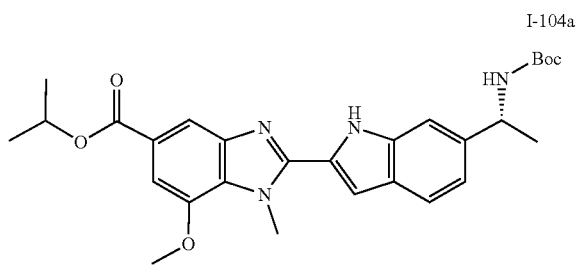 [SMILES: COc1cc(C(=O)OC(C)C)cc2nc(-c3cc4ccc([C@@H](C)NC(=O)OC(C)(C)C)cc4[nH]3)n(C)c12]

isopropyl (R)-2-(6-(1-((tert-butoxycarbonyl)amino)ethyl)-1H-indol-2-yl)-1-cyclopropyl-7-methoxy-1H-benzo[d]imidazole-5-carboxylate (I-104b)

Prepared following a similar procedure to I-102 starting with I-13c. ES/MS: m/z 533.3 [M+H]⁺. ¹H NMR (400 MHz, DMSO-d6) δ 11.86 (brs, 1H), 7.86 (d, J=1.3 Hz, 1H), 7.59 (d, J=8.2 Hz, 1H), 7.46 (d, J=8.2 Hz, 1H), 7.41 (s, 1H), 7.37 (d, J=1.4 Hz, 1H), 7.31-7.28 (m, 1H), 7.05 (dd, J=8.3, 1.5 Hz, 1H), 5.20-5.12 (m, 1H), 4.76-4.63 (m, 1H), 4.02 (s, 3H), 3.95-3.84 (m, 1H), 1.39 (s, 9H), 1.37 (d, J=6.3 Hz, 6H), 1.32-1.23 (m, 2H), 1.25 (brs, 3H), 0.91-0.85 (m, 2H).

I-104b

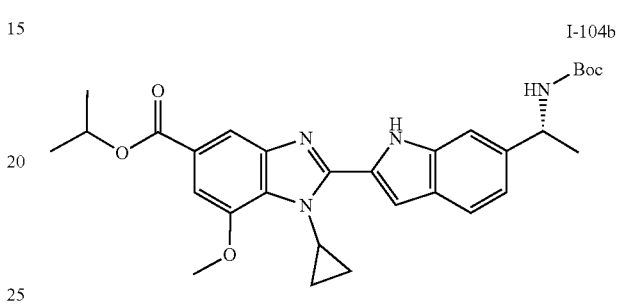

isopropyl (R)-2-(6-(1-((tert-butoxycarbonyl)amino)ethyl)-1H-pyrrolo[2,3-b]pyridin-2-yl)-1-cyclopropyl-1H-benzo[d]imidazole-5-carboxylate (I-104c)

Prepared following a similar procedure to I-102 starting with I-13f. ES/MS: m/z 504.1 [M+H]⁺.

I-104c

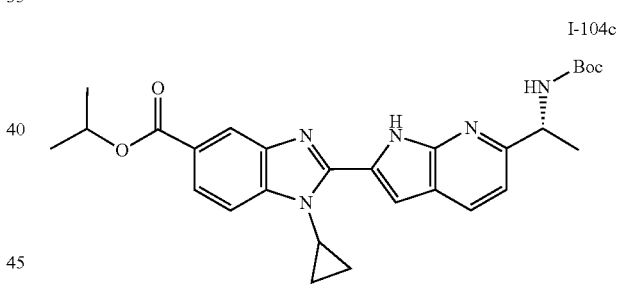

isopropyl (R)-2-(6-(1-((tert-butoxycarbonyl)amino)ethyl)-1H-pyrrolo[2,3-b]pyridin-2-yl)-1-methyl-1H-benzo[d]imidazole-5-carboxylate (I-104d)

Prepared following a similar procedure to I-102 starting with I-13i. ES/MS: m/z 478.2 [M+H]⁺.

I-104d

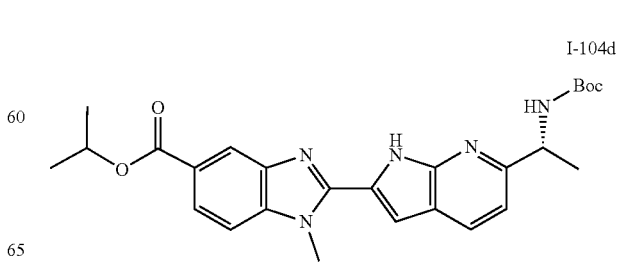

isopropyl (R)-2-(6-(1-((tert-butoxycarbonyl)amino)ethyl)-1H-pyrrolo[2,3-b]pyridin-2-yl)-6-fluoro-1-methyl-1H-benzo[d]imidazole-5-carboxylate (I-105a)

Prepared following a similar procedure to I-102 starting with I-13d. ES/MS: m/z 496.0 [M+H]⁺.

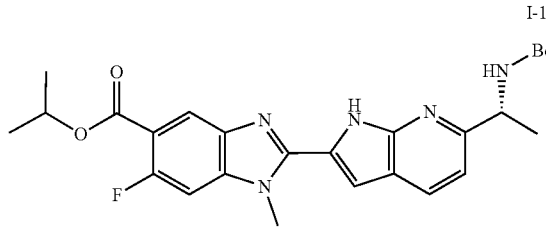

I-105a isopropyl (R)-2-(6-(1-((tert-butoxycarbonyl)amino)ethyl)-1H-pyrrolo[2,3-b]pyridin-2-yl)-1-cyclopropyl-6-fluoro-1H-benzo[d]imidazole-5-carboxylate (I-105b)

Prepared following a similar procedure to I-102 starting with I-13e. ES/MS: m/z 522.1 [M+H]⁺.

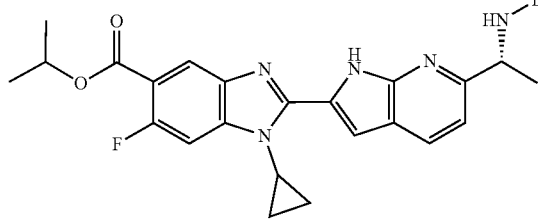

I-105b isopropyl (R)-2-(6-(1-((tert-butoxycarbonyl)amino)ethyl)-1H-indol-2-yl)-6-fluoro-1-methyl-1H-benzo[d]imidazole-5-carboxylate (I-105c)

Prepared following a similar procedure to I-102 starting with I-13j. ES/MS: m/z 522.1 [M+H]⁺.

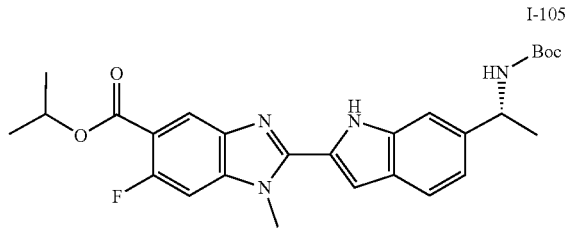

I-105c

Preparation of isopropyl 2-(6-(2-((tert-butoxycarbonyl)amino)propan-2-yl)-1H-pyrrolo[2,3-b]pyridin-2-yl)-7-methoxy-1-methyl-1H-benzo[d]imidazole-5-carboxylate (I-106)

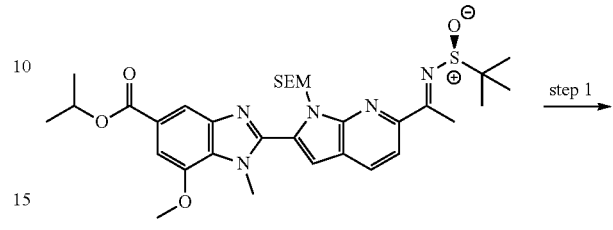

intermediate described in the synthesis of I-102

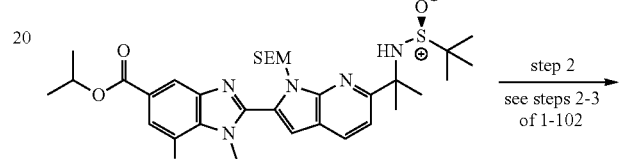

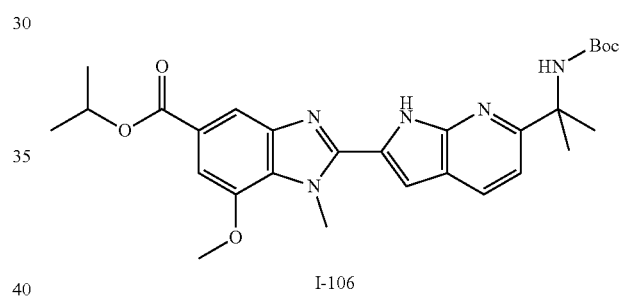

I-106

Step 1.

To a cooled solution of isopropyl (S,E)-2-(6-(1-((tert-butylsulfinyl)imino)ethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate (54 mg, 0.0844 mmol) in toluene (0.4 mL) at −78° C. was added dropwise a solution of AlMe₃ in toluene (2 M, 0.046 mL, 0.092 mmol). After 5 minutes, a solution of methylmagnesium bromide in ether (3 M, 0.062 mL, 0.186 mmol). After 2 hours, the reaction mixture was warmed to 0° C. and then gradually warmed to room temperature overnight. The reaction mixture was quenched with NH₄Cl (aq) and extracted with ethyl acetate. The combined organics were dried (MgSO₄), filtered, and concentrated under reduced pressure to give isopropyl (S)-2-(6-(2-((tert-butylsulfinyl)amino)propan-2-yl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 655.9 [M+H]⁺.

Step 2

Isopropyl 2-(6-(2-((tert-butoxycarbonyl)amino)propan-2-yl)-1H-pyrrolo[2,3-b]pyridin-2-yl)-7-methoxy-1-methyl-1H-benzo[d]imidazole-5-carboxylate was made following steps 3-4 for the preparation of I-102. ES/MS: m/z 522.0 [M+H]⁺.

Preparation of isopropyl (R)-2-(6-(1-aminoethyl)-1-(pent-4-en-1-yl)-1H-pyrrolo[2,3-b]pyridin-2-yl)-7-methoxy-1-methyl-1H-benzo[d]imidazole-5-carboxylate (I-107a)

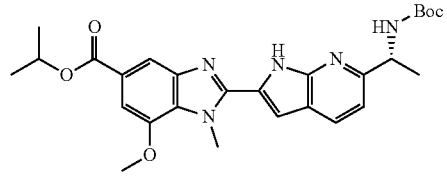

I-102 steps 1,2

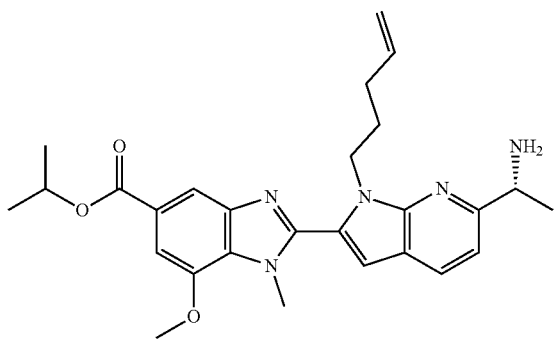

I-107a

Note:
Methyl ester analogs of all intermediates I-107 can also be made from any methyl ester intermediates I-141 or I-143.

Step 1
Isopropyl 2-[6-[(1R)-1-(tert-butoxycarbonylamino) ethyl]-1H-pyrrolo[2,3-b]pyridin-2-yl]-7-methoxy-1-methyl-benzimidazole-5-carboxylate (500 mg, 0.985 mmol) was dissolved in DMF (8 mL). 5-bromopent-1-ene (0.17 mL, 1.6 mmol) was added followed by $Cs_2CO_3$. The reaction mixture was heated to 60° C. After 1 h, the reaction mixture was filtered to remove solids and partitioned between EtOAc and water. The phases were separated, and the organic phase was washed with water and brine, dried over $Na_2SO_4$, filtered, and concentrated to afford isopropyl 2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carboxylate. ES/MS: m/z 576.3 [M+H]$^+$.

*Alternatively, a Mitsunobu reaction can be performed using the corresponding primary alcohol as electrophile (see step 1 of Procedure 27).

Step 2
Isopropyl 2-[6-[(1R)-1-(tert-butoxycarbonylamino) ethyl]-1-pent-4-enyl-pyrrolo[2,3-b]pyridin-2-yl]-7-methoxy-1-methyl-benzimidazole-5-carboxylate (509 mg, 0.884 mmol) was dissolved in DCM (15 mL). TFA (7.5 mL) was added and the reaction mixture was stirred for 30 min and then concentrated in vacuo to provide isopropyl (R)-2-(6-(1-aminoethyl)-1-(pent-4-en-1-yl)-1H-pyrrolo[2,3-b] pyridin-2-yl)-7-methoxy-1-methyl-1H-benzo[d]imidazole-5-carboxylate as its TFA salt. ES/MS: m/z 475.9 [M+H]$^+$.

isopropyl (R)-2-(1-(2-allylbenzyl)-6-(1-aminoethyl)-1H-pyrrolo[2,3-b]pyridin-2-yl)-7-methoxy-1-methyl-1H-benzo[d]imidazole-5-carboxylate (I-107b)

Prepared following a similar procedure to I-107a using 1-allyl-2-(bromomethyl)benzene instead of 5-bromopent-1-ene. ES/MS: m/z 538.1 [M+H]$^+$.

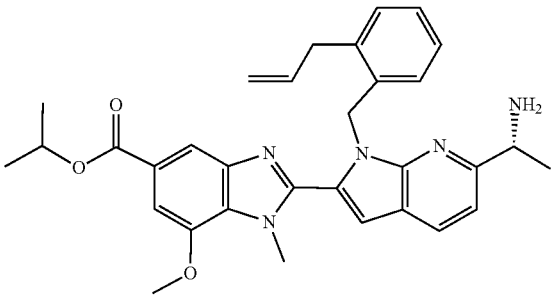

I-107b isopropyl (R)-2-(6-(1-aminoethyl)-1-(pent-4-en-1-yl)-1H-indol-2-yl)-7-methoxy-1-methyl-1H-benzo[d]imidazole-5-carboxylate (I-107c)

Prepared following a similar procedure to I-107a using I-104a instead of I-102. ES/MS: m/z 475.2 [M+H]$^+$.

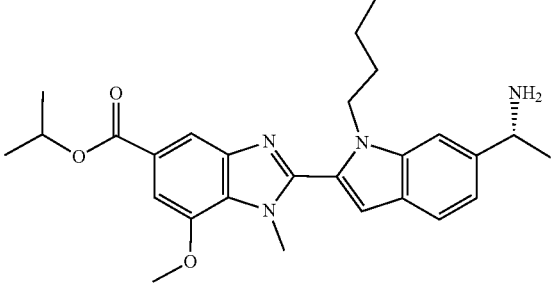

I-107c isopropyl (R)-2-(6-(1-aminoethyl)-1-(but-3-en-1-yl)-1H-pyrrolo[2,3-b]pyridin-2-yl)-7-methoxy-1-methyl-1H-benzo[d]imidazole-5-carboxylate (I-107d)

Prepared following a similar procedure to I-107a using 4-bromobut-1-ene instead of 5-bromopent-1-ene. ES/MS: m/z 461.9 [M+H]$^+$.

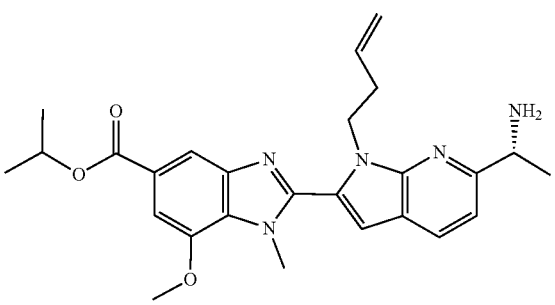

I-107d isopropyl (R)-2-(6-(1-aminoethyl)-1-(but-3-en-1-yl)-1H-pyrrolo[2,3-b]pyridin-2-yl)-1-cyclopropyl-6-fluoro-1H-benzo[d]imidazole-5-carboxylate (I-107e)

Prepared using a similar procedure to I-107d using I-141b instead of I-102. ES/MS: m/z 448.6 [M+H]⁺.

ethyl (R)-2-(1-allyl-6-(1-aminoethyl)-1H-pyrrolo[2,3-b]pyridin-2-yl)-5-methoxy-3-methylimidazo[1,2-a]pyridine-7-carboxylate (I-107g)

Prepared following a similar procedure to I-107a using I-100 and allyl bromide instead of 5-bromopent-1-ene. ES/MS: m/z 433.8 [M+H]⁺.

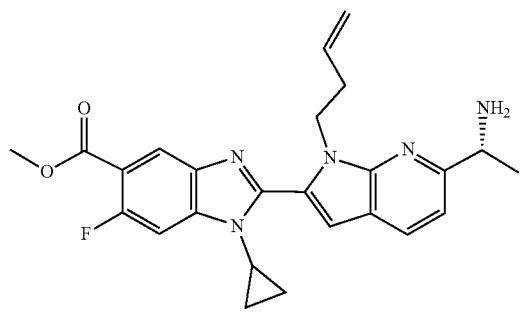
I-107e

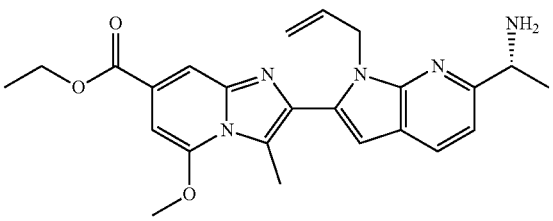
I-107g isopropyl (R)-2-(1-allyl-6-(1-aminoethyl)-1H-pyrrolo[2,3-b]pyridin-2-yl)-7-methoxy-1-methyl-1H-benzo[d]imidazole-5-carboxylate (I-107f)

Prepared following a similar procedure to I-107a using allyl bromide instead of 5-bromopent-1-ene. ES/MS: m/z 447.9 [M+H]⁺.

isopropyl 2-(6-((R)-1-((tert-butoxycarbonyl)amino)ethyl)-1-(((1S,2S)-2-vinylcyclopropyl)methyl)-1H-pyrrolo[2,3-b]pyridin-2-yl)-7-methoxy-1-methyl-1H-benzo[d]imidazole-5-carboxylate (I-107h)

Prepared following a similar procedure to I-107a using I-18 (Mitsunobu reaction, see step 1 of Procedure 27). ES/MS: m/z 488.3 [M+H]⁺.

I-107f

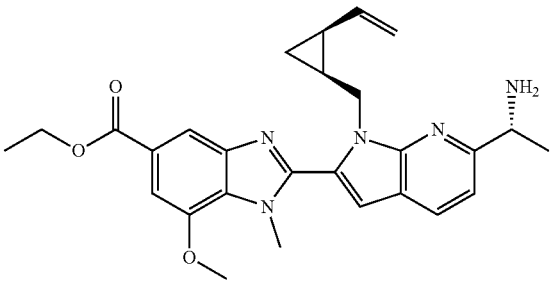
I-107h isopropyl 2-(6-((R)-1-aminoethyl)-1-(((trans)-2,2-difluoro-3-vinylcyclopropyl)methyl)-1H-pyrrolo[2,3-b]pyridin-2-yl)-7-methoxy-1-methyl-1H-benzo[d]imidazole-5-carboxylate (I-107i)

Prepared following a similar procedure to I-107a using I-19 (Mitsunobu reaction, see step 1 of Procedure 27). ES/MS: m/z 524.3 [M+H]+.

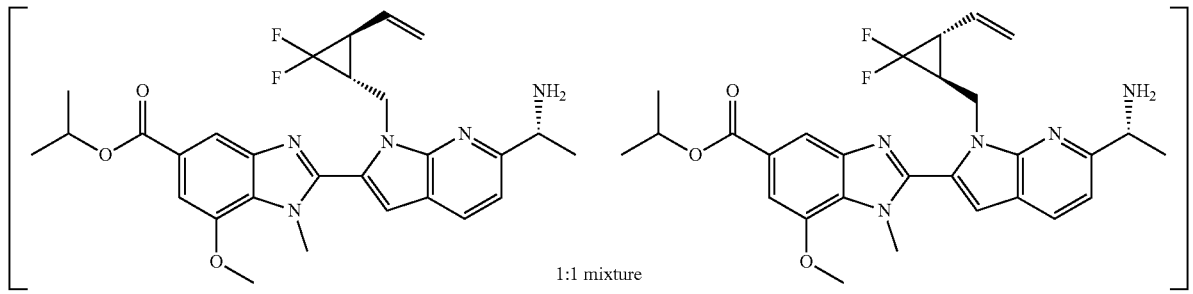

I-107i

1:1 mixture methyl 2-(6-((R)-1-aminoethyl)-1-(((1S,2S)-2-vinylcyclopropyl)methyl)-1H-pyrrolo[2,3-b]pyridin-2-yl)-6-fluoro-1-methyl-1H-benzo[d]imidazole-5-carboxylate (I-107j)

Prepared following a similar procedure to I-107a using I-143b and I-18 (Mitsunobu reaction, see step 1 of Procedure 27). ES/MS: m/z 447.9 [M+H]+.

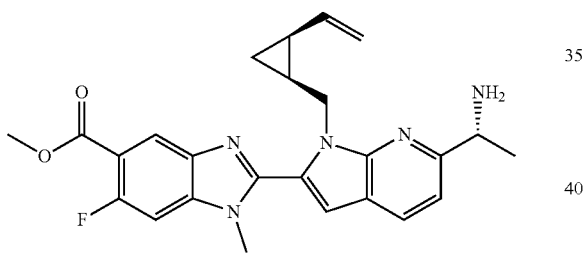

I-107j methyl 2-(6-((R)-1-aminoethyl)-1-(((cis)-2,2-difluoro-3-vinylcyclopropyl)methyl)-1H-pyrrolo[2,3-b]pyridin-2-yl)-6-fluoro-1-methyl-1H-benzo[d]imidazole-5-carboxylate (I-107k)

Prepared following a similar procedure to I-107a using I-143b and I-17 (Mitsunobu reaction, see step 1 of Procedure 27). ES/MS: m/z 584.2 [M+H]+.

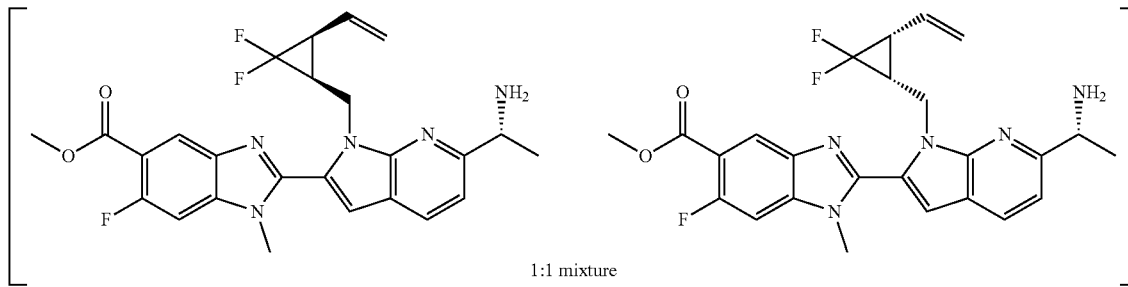

I-107k

1:1 mixture methyl (R)-2-(6-(1-aminoethyl)-1-(pent-4-en-1-yl)-1H-pyrrolo[2,3-b]pyridin-2-yl)-6-fluoro-1-methyl-1H-benzo[d]imidazole-5-carboxylate (I-107l)

Prepared following a similar procedure to I-107a using I-143b. ES/MS: m/z 436.3 [M+H]+.

methyl (R)-2-(6-(1-aminoethyl)-1-(but-3-en-1-yl)-1H-pyrrolo[2,3-b]pyridin-2-yl)-6-fluoro-1-(2-methoxyethyl)-1H-benzo[d]imidazole-5-carboxylate (I-107n)

Prepared following a similar procedure to I-107a using I-143e. ES/MS: m/z 466.3 [M+H]+.

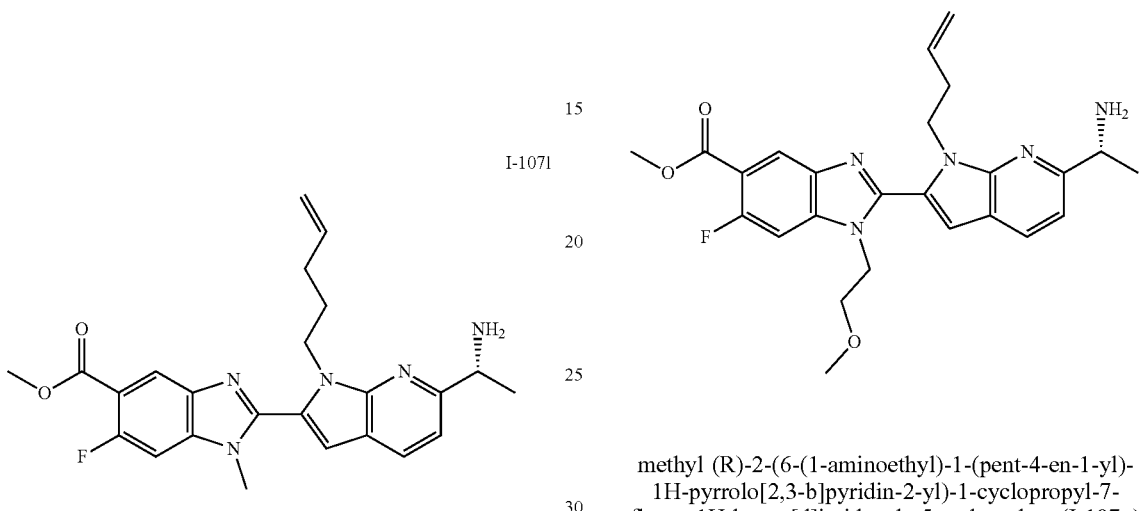

methyl (R)-2-(6-(1-aminoethyl)-1-(pent-4-en-1-yl)-1H-pyrrolo[2,3-b]pyridin-2-yl)-1-cyclopropyl-7-fluoro-1H-benzo[d]imidazole-5-carboxylate (I-107o)

Prepared following a similar procedure to I-107a using I-141c. ES/MS: m/z 462.0 [M+H]+.

methyl (R)-2-(6-(1-aminoethyl)-1-(pent-4-en-1-yl)-1H-pyrrolo[2,3-b]pyridin-2-yl)-1-cyclopropyl-6-fluoro-1H-benzo[d]imidazole-5-carboxylate (I-107m)

Prepared following a similar procedure to I-107a using I-141b. ES/MS: m/z 462.3 [M+H]+.

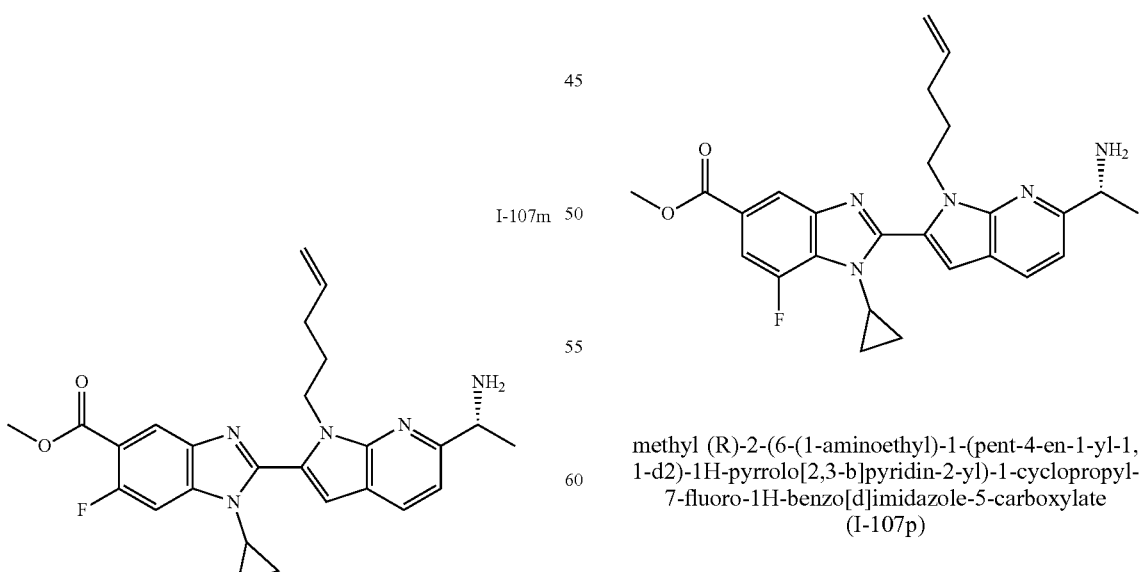

methyl (R)-2-(6-(1-aminoethyl)-1-(pent-4-en-1-yl-1,1-d2)-1H-pyrrolo[2,3-b]pyridin-2-yl)-1-cyclopropyl-7-fluoro-1H-benzo[d]imidazole-5-carboxylate (I-107p)

Prepared following a similar procedure to I-107a using I-141c and 1,1-dideuteriopent-4-en-1-ol (Mitsunobu reaction, see step 1 of Procedure 27). ES/MS: m/z 464.3 [M+H]+.

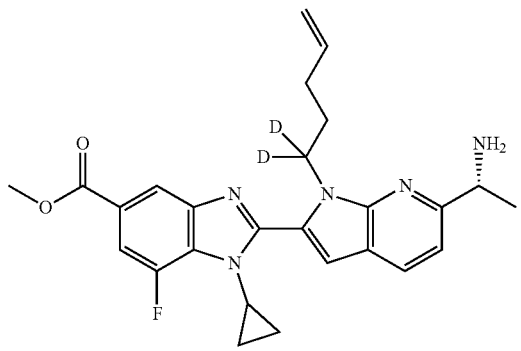

methyl (R)-2-(1-allyl-6-(1-aminoethyl)-1H-pyrrolo[2,3-b]pyridin-2-yl)-6-fluoro-1-methyl-1H-benzo[d]imidazole-5-carboxylate (I-107q)

Prepared following a similar procedure to I-107l using allyl bromide. ES/MS: m/z 408.2 [M+H]⁺.

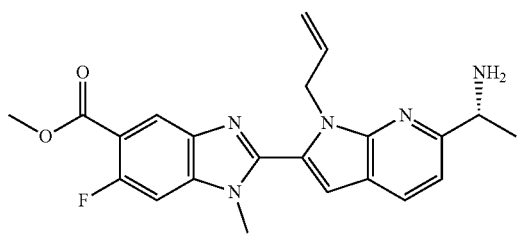

methyl (R)-2-(6-(1-aminoethyl)-1-(but-3-en-1-yl)-1H-pyrrolo[2,3-b]pyridin-2-yl)-6-fluoro-1-methyl-1H-benzo[d]imidazole-5-carboxylate (I-107r)

Prepared following a similar procedure to I-107l using 4-bromobut-1-ene. ES/MS: m/z 422.2 [M+H]⁺.

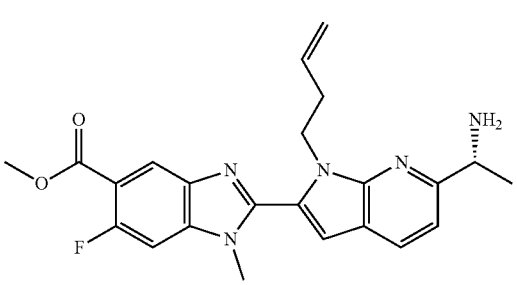

methyl (R)-2-(6-(1-aminoethyl)-1-(but-3-en-1-yl)-1H-pyrrolo[2,3-b]pyridin-2-yl)-3-cyclopropyl-6-fluoroimidazo[1,2-a]pyridine-7-carboxylate (I-107s)

Prepared following a similar procedure to I-107a using I-136c. ES/MS: m/z 448.3 [M+H]⁺.

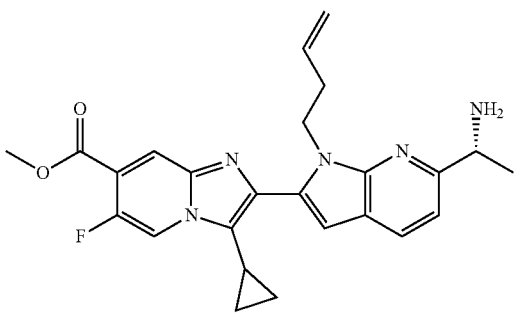

isopropyl (R)-2-(6-(1-aminoethyl)-1-(pent-4-en-1-yl)-1H-pyrrolo[2,3-b]pyridin-2-yl)-5-methoxy-3-methylimidazo[1,2-a]pyridine-7-carboxylate (I-107t)

Prepared following a similar procedure to I-107a using I-100. ES/MS: m/z 476.3 [M+H]⁺.

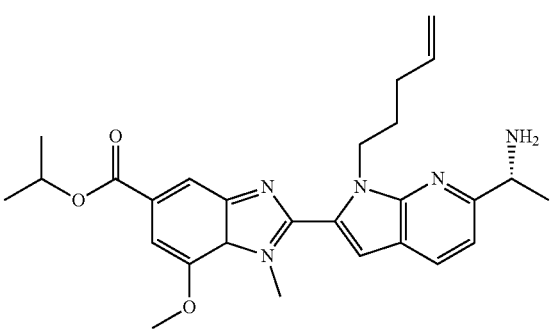

methyl (R)-2-(6-(1-aminoethyl)-1-(pent-4-en-1-yl)-1H-pyrrolo[2,3-b]pyridin-2-yl)-1-cyclopropyl-7-methoxy-1H-benzo[d]imidazole-5-carboxylate (I-107u)

Prepared following a similar procedure to I-107a using I-101b. ES/MS: m/z 474.3 [M+H]⁺.

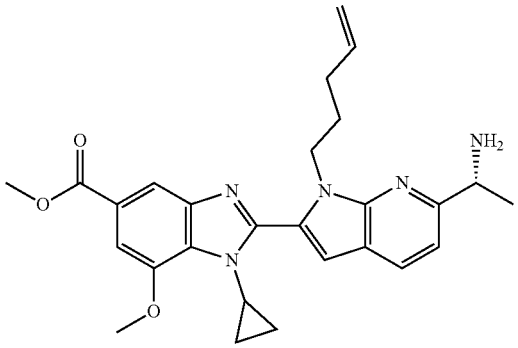

isopropyl (R)-2-(6-(1-aminoethyl)-1-(but-3-en-1-yl)-
1H-pyrrolo[2,3-b]pyridin-2-yl)-1-cyclopropyl-1H-
benzo[d]imidazole-5-carboxylate (I-107v)

Prepared following a similar procedure to I-107d using
I-104c. ES/MS: m/z 458.3 [M+H]$^+$.

methyl (R)-2-(6-(1-aminoethyl)-1-(but-3-en-1-yl)-
1H-pyrrolo[2,3-b]pyridin-2-yl)-1-cyclopropyl-7-
methoxy-1H-benzo[d]imidazole-5-carboxylate
(I-107x)

Prepared following a similar procedure to I-107a using
I-141i. ES/MS: m/z 460.3 [M+H]$^+$.

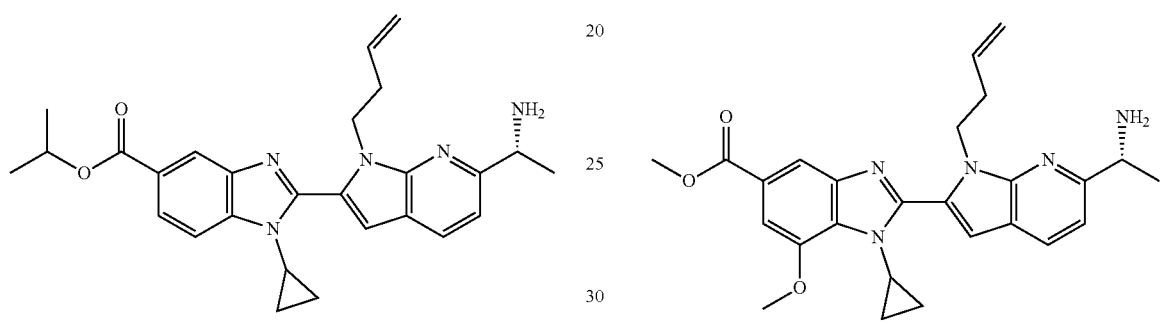

methyl (R)-2-(6-(1-aminoethyl)-1-(pent-4-en-1-yl)-
1H-pyrrolo[2,3-b]pyridin-2-yl)-7-fluoro-1-methyl-
1H-benzo[d]imidazole-5-carboxylate (I-107w)

Prepared following a similar procedure to I-107a using
I-143j. ES/MS: m/z 436.3 [M+H]$^+$.

methyl 2-(6-((R)-1-aminoethyl)-1-(((1S,2S)-2-vinyl-
cyclopropyl)methyl)-1H-pyrrolo[2,3-b]pyridin-2-yl)-
1-cyclopropyl-7-methoxy-1H-benzo[d]imidazole-5-
carboxylate (I-107y)

Prepared following a similar procedure to I-107a using
I-143i and I-18 (Mitsunobu reaction, see step 1 of Procedure
27). ES/MS: m/z 486.3 [M+H]$^+$.

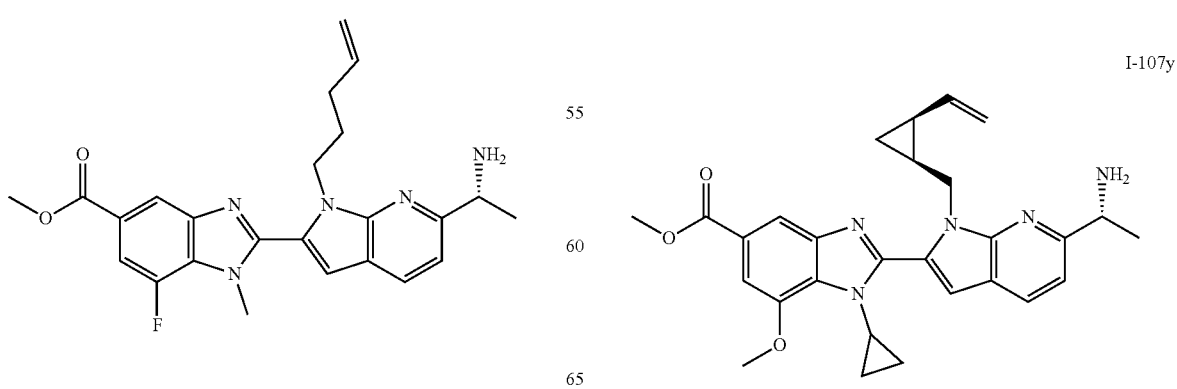

methyl (R)-2-(1-allyl-6-(1-aminoethyl)-1H-pyrrolo[2,3-b]pyridin-2-yl)-6-fluoro-1-methyl-1H-benzo[d]imidazole-5-carboxylate (I-107z)

Prepared following a similar procedure to I-107l using allyl bromide. ES/MS: m/z 408.2 [M+H]⁺.

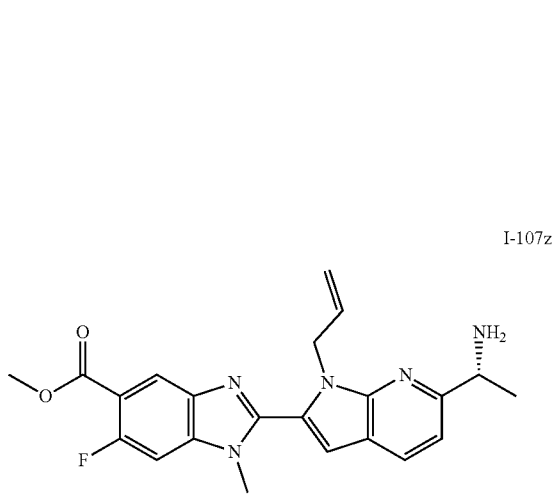 [SMILES: C=CCn1c(-c2nc3cc(C(=O)OC)c(F)cc3n2C)cc2ccc([C@@H](C)N)nc21]

methyl (R)-2-(6-(1-aminoethyl)-1-(pent-4-en-1-yl)-1H-pyrrolo[2,3-b]pyridin-2-yl)-3-cyclopropyl-5-methoxyimidazo[1,2-a]pyridine-7-carboxylate (I-107aa)

Prepared following a similar procedure to I-107a using I-141i. ES/MS: m/z 474.3 [M+H]⁺.

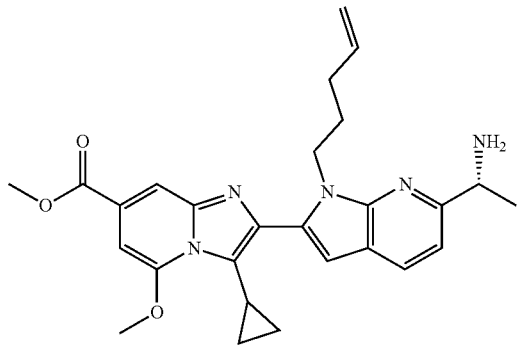

methyl 2-(6-(2-aminopropan-2-yl)-1-(pent-4-en-1-yl)-1H-pyrrolo[2,3-b]pyridin-2-yl)-7-methoxy-1-methyl-1H-benzo[d]imidazole-5-carboxylate (I-107bb)

Prepared following a similar procedure to I-107a using I-141k. ES/MS: m/z 461.9 [M+H]⁺.

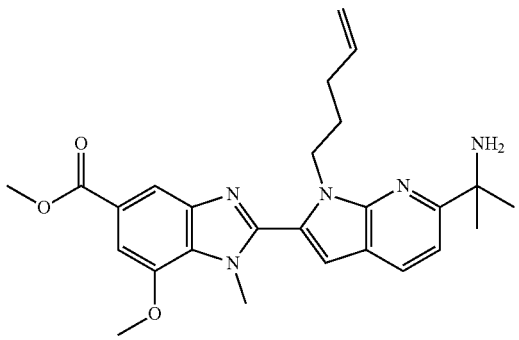

methyl 2-(6-((R)-1-aminoethyl)-1-(((1S,2S)-2-vinylcyclopropyl)methyl)-1H-pyrrolo[2,3-b]pyridin-2-yl)-1-cyclopropyl-7-fluoro-1H-benzo[d]imidazole-5-carboxylate (I-107cc)

Prepared following a similar procedure to I-107a using I-141c and I-18 (Mitsunobu reaction, see step 1 of Procedure 27). ES/MS: m/z 474.3 [M+H]⁺.

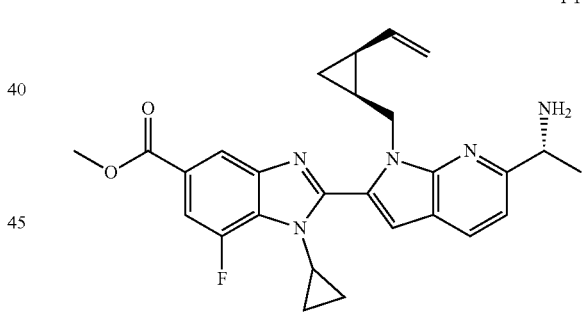

Preparation of methyl 2-(1-(6-(((tert-butoxycarbonyl)amino)hexyl)-6-(2-(tert-butoxycarbonyl)pyridin-3-yl)-1H-pyrrolo[2,3-b]pyridin-2-yl)-7-methoxy-1-methyl-1H-benzo[d]imidazole-5-carboxylate (I-108)

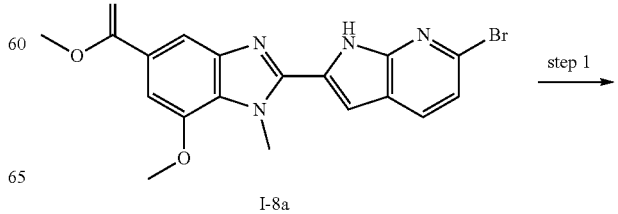

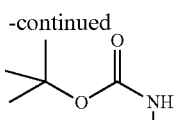

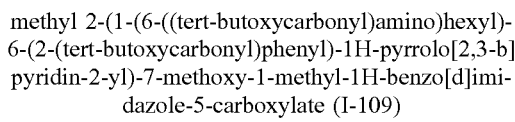

methyl 2-(1-(6-((tert-butoxycarbonyl)amino)hexyl)-6-(2-(tert-butoxycarbonyl)phenyl)-1H-pyrrolo[2,3-b]pyridin-2-yl)-7-methoxy-1-methyl-1H-benzo[d]imidazole-5-carboxylate (I-109)

Prepared following a similar procedure to I-108 using tert-butyl 2-(4,4,5,5-tetramethyl-1,3,2-dioxaborolan-2-yl)benzoate instead of tert-butyl 3-(4,4,5,5-tetramethyl-1,3,2-dioxaborolan-2-yl)pyridine-2-carboxylate. ES/MS: m/z 712.4 [M+H]⁺.

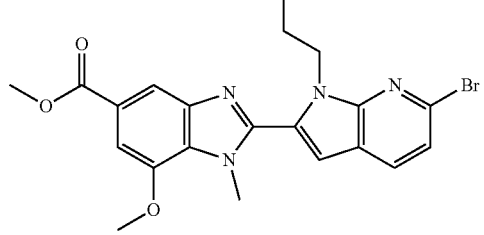

I-108

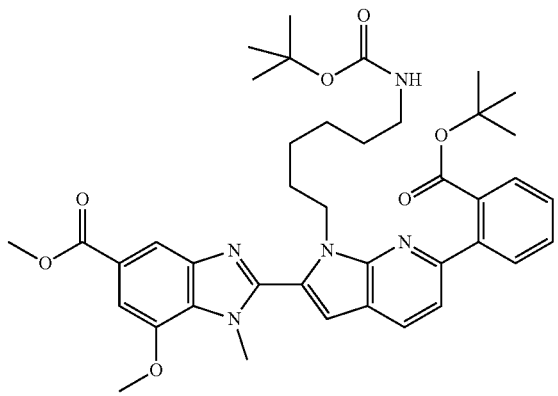

I-109

Step 1

To a mixture of methyl 2-(6-bromo-1H-pyrrolo[2,3-b]pyridin-2-yl)-7-methoxy-1-methyl-1H-benzo[d]imidazole-5-carboxylate (I-8a, 250 mg, 0.60 mmol), tert-butyl N-(6-bromohexyl)carbamate (202 mg, 0.72 mmol), and cesium carbonate (588 mg, 1.8 mmol) was added 2.5 mL of DMF. The reaction mixture was stirred at ambient temperature overnight, then heated to 60° C. for 1 h. After cooling to ambient temperature, the mixture was poured into EtOAc and washed with water, then brine. The organic phase was concentrated, adsorbed to isolute, and purified by silica gel chromatography (eluent: EtOAc/hexane) to provide methyl 2-(6-bromo-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate. ES/MS: m/z 614.2 [M+H]⁺.

Step 2

To a solution of methyl 2-(6-bromo-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate (174 mg, 0.28 mmol) in dioxane (2 mL) was added tert-butyl 3-(4,4,5,5-tetramethyl-1,3,2-dioxaborolan-2-yl)pyridine-2-carboxylate (173 mg, 0.57 mmol), dichloro 1,1'-bis(diphenylphosphino)ferrocene palladium (II) dichloromethane (23 mg, 0.03 mmol), and aqueous sodium carbonate (0.28 mL of 2 M solution, 0.57 mmol). N₂ was bubbled through the mixture, and the reaction heated to 100° C. for 2 h. After removing from heat, the reaction was filtered through a celite pad and adsorbed to isolute. Purification by silica gel chromatography (eluent: 3:1 EtOAc/EtOH with 0.25% triethylamine in heptane) provided methyl 2-(1-(6-((tert-butoxycarbonyl)amino)hexyl)-6-(2-(tert-butoxycarbonyl)pyridin-3-yl)-1H-pyrrolo[2,3-b]pyridin-2-yl)-7-methoxy-1-methyl-H-benzo[d]imidazole-5-carboxylate. ES/MS: m/z 713.4 [M+H]⁺.

methyl 2-(1-(6-((tert-butoxycarbonyl)amino)hexyl)-6-(2-(tert-butoxycarbonyl)phenyl)-1H-indol-2-yl)-7-methoxy-1-methyl-1H-benzo[d]imidazole-5-carboxylate (I-110a)

Prepared following a similar procedure to I-108 using I-8b instead of I-8a, and tert-butyl 2-(4,4,5,5-tetramethyl-1,3,2-dioxaborolan-2-yl)benzoate instead of tert-butyl 3-(4,4,5,5-tetramethyl-1,3,2-dioxaborolan-2-yl)pyridine-2-carboxylate. ES/MS: m/z 711.4 [M+H]⁺.

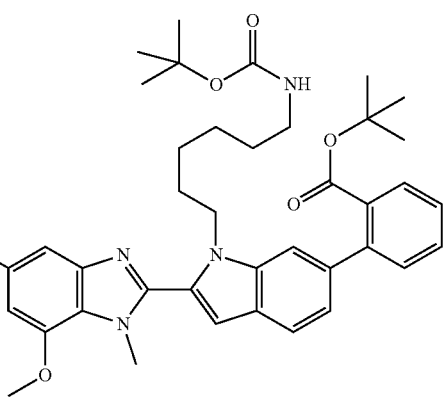

I-110a methyl 2-(6-(2-(tert-butoxycarbonyl)phenyl)-1-(3-(1-(tert-butoxycarbonyl)piperidin-4-yl)propyl)-1H-indol-2-yl)-7-methoxy-1-methyl-1H-benzo[d]imidazole-5-carboxylate (I-110b)

Prepared following a similar procedure to I-110a using tert-butyl 4-(3-bromopropyl)piperidine-1-carboxylate instead of tert-butyl N-(6-bromohexyl)carbamate. ES/MS: m/z 737.4 [M+H]⁺.

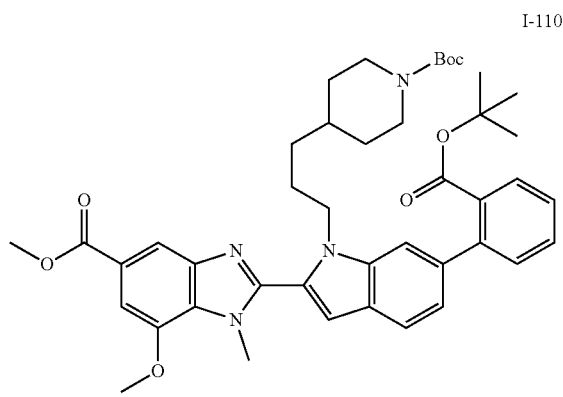

I-110b methyl 2-(1-(6-((tert-butoxycarbonyl)amino)hexyl)-6-(2-(tert-butoxycarbonyl)pyridin-3-yl)-1H-indol-2-yl)-7-methoxy-1-methyl-1H-benzo[d]imidazole-5-carboxylate (I-111)

Prepared following a similar procedure to I-108 using I-8b instead of I-8a. ES/MS: m/z 712.4 [M+H]⁺.

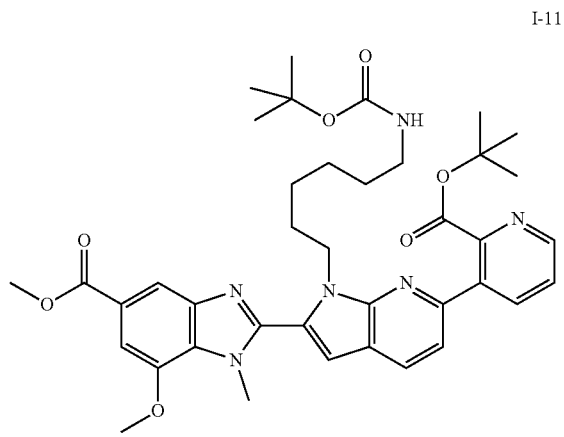

I-111 methyl 2-(6-(2-(tert-butoxycarbonyl)-6-methylphenyl)-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate (I-112)

Prepared following a similar procedure to I-108 using tert-butyl 3-methyl-2-(4,4,5,5-tetramethyl-1,3,2-dioxaborolan-2-yl)benzoate (synthesized in one chemical step starting from tert-butyl 2-iodo-3-methylbenzoate) instead of tert-butyl 3-(4,4,5,5-tetramethyl-1,3,2-dioxaborolan-2-yl)pyridine-2-carboxylate. ES/MS: m/z 726.4 [M+H]⁺.

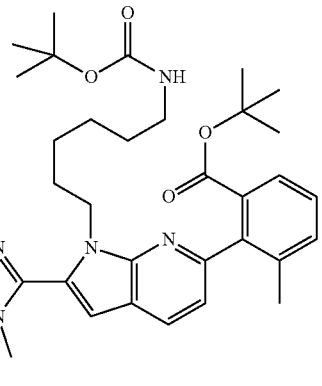

I-112 methyl 2-(6-(3-(tert-butoxycarbonyl)-2-fluoropyridin-4-yl)-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate (I-113)

Prepared following a similar procedure to I-108 using tert-butyl 2-fluoro-4-(4,4,5,5-tetramethyl-1,3,2-dioxaborolan-2-yl)nicotinate (synthesized in two chemical steps starting from 2-fluoro-4-iodonicotinic acid) instead of tert-butyl 3-(4,4,5,5-tetramethyl-1,3,2-dioxaborolan-2-yl)pyridine-2-carboxylate. ES/MS: m/z 731.3 [M+H]⁺.

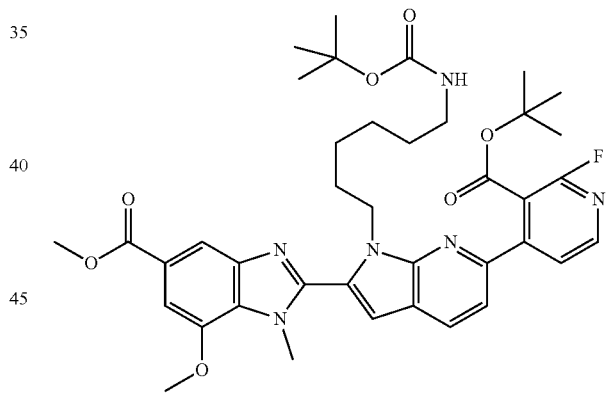

I-113

Preparation of methyl 2-(1-(7-(tert-butoxy)-7-oxoheptyl)-6-(2-((tert-butoxycarbonyl)amino)pyridin-3-yl)-1H-indol-2-yl)-7-methoxy-1-methyl-1H-benzo[d]imidazole-5-carboxylate (I-114)

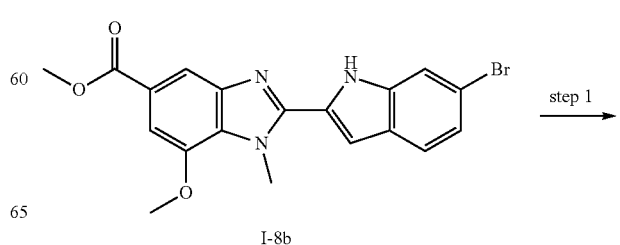

I-8b    step 1

237
-continued

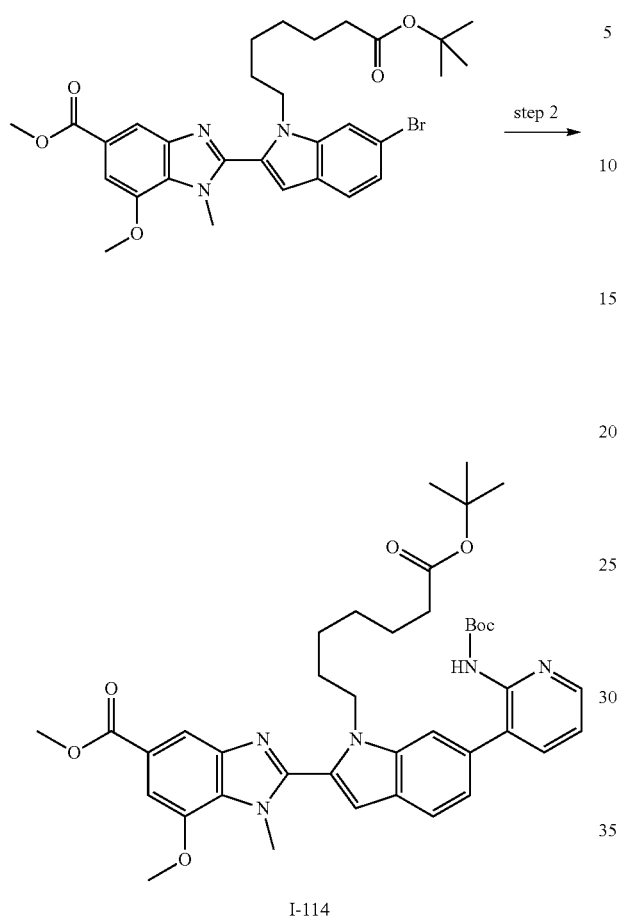

I-114

Step 1

Followed step 1 of I-108 using I-8b (500 mg, 1.2 mmol) and tert-butyl 7-bromoheptanoate (384 mg, 1.45 mmol) and heating to 60° C. for 2 hours. Purification by silica gel column chromatography provided methyl 2-(6-bromo-1-(7-(tert-butoxy)-7-oxoheptyl)-1H-indol-2-yl)-7-methoxy-1-methyl-1H-benzo[d]imidazole-5-carboxylate. ES/MS: m/z 598.2 [M+H]⁺.

Step 2

Followed step 2 of I-108 using methyl 2-(6-bromo-1-(7-(tert-butoxy)-7-oxoheptyl)-1H-indol-2-yl)-7-methoxy-1-methyl-1H-benzo[d]imidazole-5-carboxylate (120 mg, 0.20 mmol) and tert-butyl N-[3-(4,4,5,5-tetramethyl-1,3,2-dioxaborolan-2-yl)-2-pyridyl]carbamate (84 mg, 0.26 mmol) and stirring at 100° C. for 1.5 hours. The reaction was poured into EtOAc and washed with water, aq. NaHCO₃, then brine. The organic phase was dried over MgSO₄, filtered, and concentrated, which was used in the next step (Procedure 15) without purification. ES/MS: m/z 712.3 [M+H]⁺. Note: Methyl 2-(6-(2-aminopyridin-3-yl)-1-(7-(tert-butoxy)-7-oxoheptyl)-1H-indol-2-yl)-7-methoxy-1-methyl-1H-benzo[d]imidazole-5-carboxylate (ES/MS: m/z 612.3 [M+H]⁺) was also observed in the crude mixture.

238 methyl 2-(1-(7-(tert-butoxy)-7-oxoheptyl)-6-(2-((tert-butoxycarbonyl)amino)pyridin-3-yl)-1H-pyrrolo[2,3-b]pyridin-2-yl)-7-methoxy-1-methyl-1H-benzo[d]imidazole-5-carboxylate (I-115)

Prepared following a similar procedure to I-114 using I-8a instead of I-8b. ES/MS: m/z 613.1 [(M-Boc)+H]⁺.

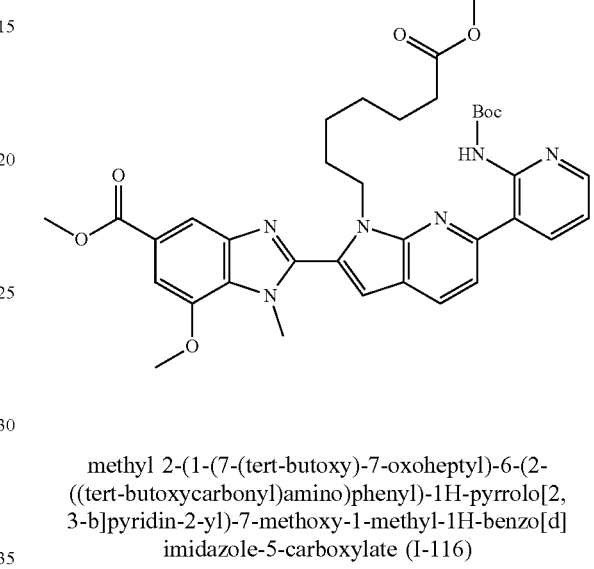

I-115 methyl 2-(1-(7-(tert-butoxy)-7-oxoheptyl)-6-(2-((tert-butoxycarbonyl)amino)phenyl)-1H-pyrrolo[2,3-b]pyridin-2-yl)-7-methoxy-1-methyl-1H-benzo[d]imidazole-5-carboxylate (I-116)

Prepared following a similar procedure to I-115 using tert-butyl (2-(4,4,5,5-tetramethyl-1,3,2-dioxaborolan-2-yl)phenyl)carbamate instead of tert-butyl N-[3-(4,4,5,5-tetramethyl-1,3,2-dioxaborolan-2-yl)-2-pyridyl]carbamate. ES/MS: m/z 712.4 [M+H]⁺.

I-116

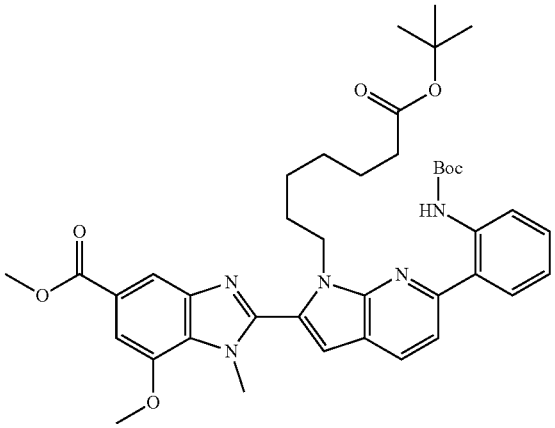

239 methyl 2-(1-(8-(tert-butoxy)-8-oxooctyl)-6-(2-((tert-butoxycarbonyl)amino)pyridin-3-yl)-1H-pyrrolo[2,3-b]pyridin-2-yl)-7-methoxy-1-methyl-1H-benzo[d]imidazole-5-carboxylate (I-117)

Prepared following a similar procedure to I-115 using tert-butyl 8-bromooctanoate instead of tert-butyl 7-bromoheptanoate. ES/MS: m/z 627.3 [(M-Boc)+H]+.

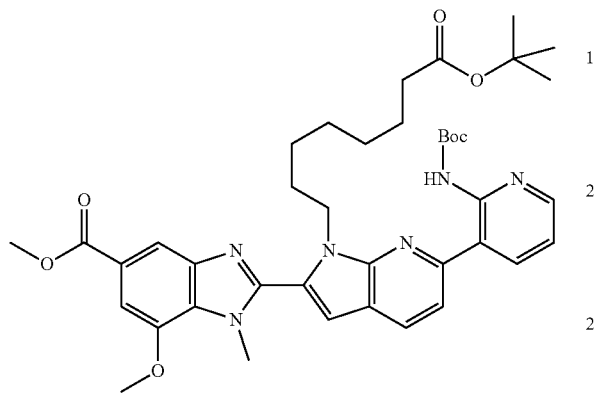

I-117 methyl 2-(1-(7-(tert-butoxy)-7-oxoheptyl)-6-(4-((tert-butoxycarbonyl)amino)pyridin-3-yl)-1H-pyrrolo[2,3-b]pyridin-2-yl)-7-methoxy-1-methyl-1H-benzo[d]imidazole-5-carboxylate (I-118)

Prepared following a similar procedure to I-115 using tert-butyl (3-(4,4,5,5-tetramethyl-1,3,2-dioxaborolan-2-yl)pyridin-4-yl)carbamate instead of tert-butyl N-[3-(4,4,5,5-tetramethyl-1,3,2-dioxaborolan-2-yl)-2-pyridyl]carbamate. ES/MS: m/z 713.4 [M+H]+.

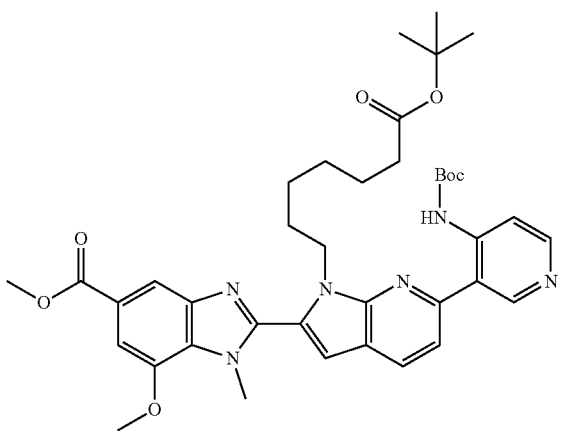

I-118

240 methyl 2-(1-(8-(tert-butoxy)-8-oxooctyl)-6-(2-((tert-butoxycarbonyl)amino)phenyl)-1H-pyrrolo[2,3-b]pyridin-2-yl)-7-methoxy-1-methyl-1H-benzo[d]imidazole-5-carboxylate (I-119)

Prepared following a similar procedure to I-116 using tert-butyl 8-bromooctanoate instead of tert-butyl 7-bromoheptanoate. ES/MS: m/z 726.4 [M+H]+.

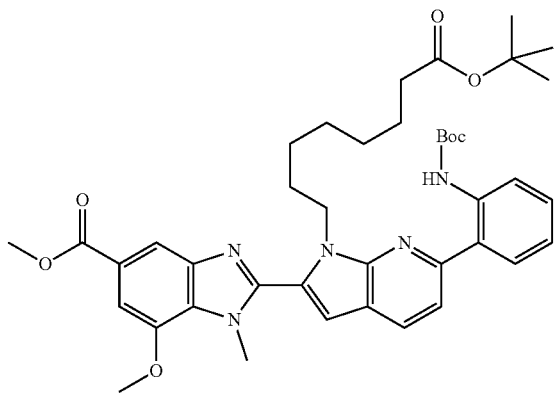

I-119 methyl 2-(1-(7-(tert-butoxy)-7-oxoheptyl)-6-(2-((tert-butoxycarbonyl)amino)phenyl)-1H-indol-2-yl)-7-methoxy-1-methyl-1H-benzo[d]imidazole-5-carboxylate (I-120)

Prepared following a similar procedure to I-114 using tert-butyl (2-(4,4,5,5-tetramethyl-1,3,2-dioxaborolan-2-yl)phenyl)carbamate instead of tert-butyl N-[3-(4,4,5,5-tetramethyl-1,3,2-dioxaborolan-2-yl)-2-pyridyl]carbamate. ES/MS: m/z 711.4 [M+H]+.

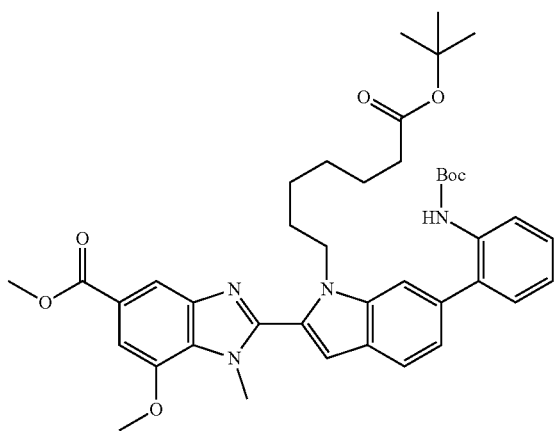

I-120 methyl 2-(1-(7-(tert-butoxy)-7-oxoheptyl)-6-(3-((tert-butoxycarbonyl)amino)pyridin-4-yl)-1H-pyrrolo[2,3-b]pyridin-2-yl)-7-methoxy-1-methyl-1H-benzo[d]imidazole-5-carboxylate (I-121)

Prepared following a similar procedure to I-115 using tert-butyl (2-(4,4,5,5-tetramethyl-1,3,2-dioxaborolan-2-yl)phenyl)carbamate instead of tert-butyl N-[3-(4,4,5,5-tetramethyl-1,3,2-dioxaborolan-2-yl)-2-pyridyl]carbamate. ES/MS: m/z 713.4 [M+H]⁺.

methyl 2-(1-(8-(tert-butoxy)-7,7-dimethyl-8-oxooctyl)-6-(2-((tert-butoxycarbonyl)amino)phenyl)-1H-indol-2-yl)-7-methoxy-1-methyl-1H-benzo[d]imidazole-5-carboxylate (I-123)

Prepared following a similar procedure to I-120 using tert-butyl 8-bromo-2,2-dimethyloctanoate (L4a) instead of tert-butyl 7-bromoheptanoate. ES/MS: m/z 753.4 [M+H]⁺.

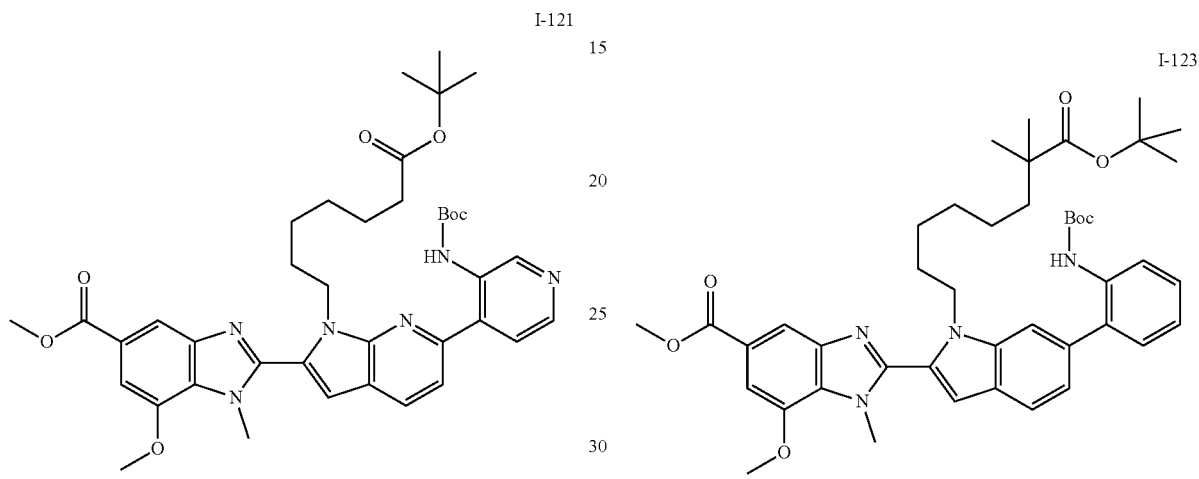

methyl 2-(1-(8-(tert-butoxy)-7,7-dimethyl-8-oxooctyl)-6-(2-((tert-butoxycarbonyl)amino)pyridin-3-yl)-1H-indol-2-yl)-7-methoxy-1-methyl-1H-benzo[d]imidazole-5-carboxylate (I-122)

Prepared following a similar procedure to I-114 using tert-butyl 8-bromo-2,2-dimethyloctanoate (L4a) instead of tert-butyl 7-bromoheptanoate. ES/MS: m/z 654.1 [(M-Boc)+H]⁺.

methyl 2-(1-(6-(tert-butoxy)-6-oxohexyl)-6-(2-((tert-butoxycarbonyl)amino)pyridin-3-yl)-1H-pyrrolo[2,3-b]pyridin-2-yl)-7-methoxy-1-methyl-1H-benzo[d]imidazole-5-carboxylate (I-124)

Prepared following a similar procedure to I-115 using tert-butyl 6-bromohexanoate instead of tert-butyl 7-bromoheptanoate. ES/MS: m/z 599.3 [(M-Boc)+H]⁺.

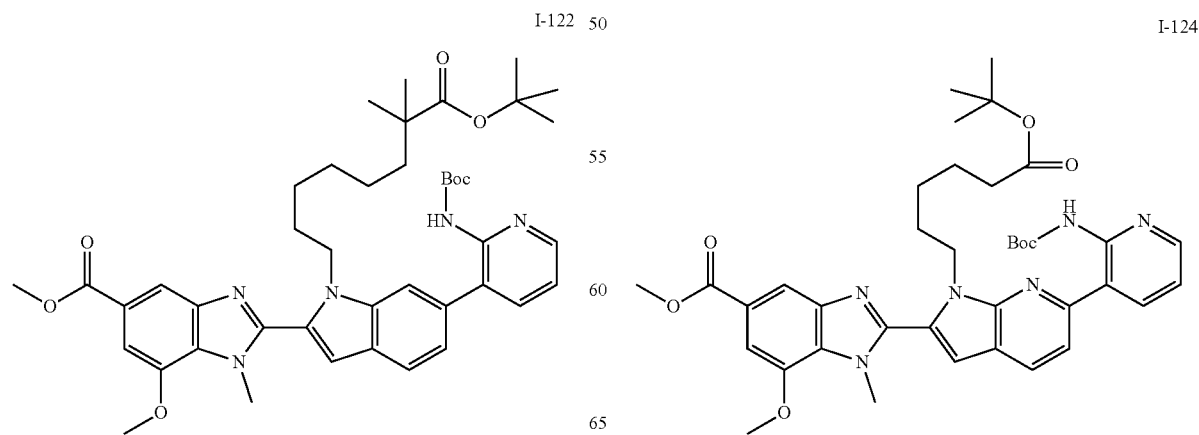

Preparation of methyl 2-(6-bromo-1-(7-((3-bromopyridin-2-yl)oxy)heptyl)-1H-pyrrolo[2,3-b]pyridin-2-yl)-7-methoxy-1-methyl-1H-benzo[d]imidazole-5-carboxylate (I-125)

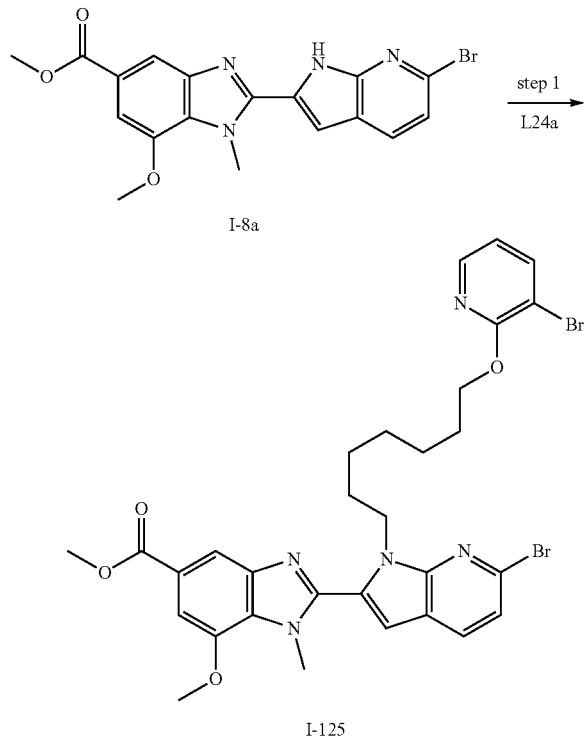

Step 1

Followed step 1 of I-108 using 3-bromo-2-(7-bromoheptoxy)pyridine (L24a, 122 mg, 0.35 mmol). Purification by silica gel column chromatography provided methyl 2-(6-bromo-1-(7-(tert-butoxy)-7-oxoheptyl)-1H-indol-2-yl)-7-methoxy-1-methyl-1H-benzo[d]imidazole-5-carboxylat. ES/MS: m/z 686.1[M+H]$^+$.

methyl 2-(6-bromo-1-(6-((3-bromopyridin-2-yl)oxy)hexyl)-1H-pyrrolo[2,3-b]pyridin-2-yl)-7-methoxy-1-methyl-1H-benzo[d]imidazole-5-carboxylate (I-126)

Prepared following a similar procedure to I-125 using L24b instead of L24a. ES/MS: m/z 672.1 [M+H]$^+$.

methyl 2-(6-bromo-1-(8-((3-bromopyridin-2-yl)oxy)octyl)-1H-pyrrolo[2,3-b]pyridin-2-yl)-7-methoxy-1-methyl-1H-benzo[d]imidazole-5-carboxylate (I-127)

Prepared following a similar procedure to I-125 using L24c instead of L24a. ES/MS: m/z 700.1 [M+H]$^+$.

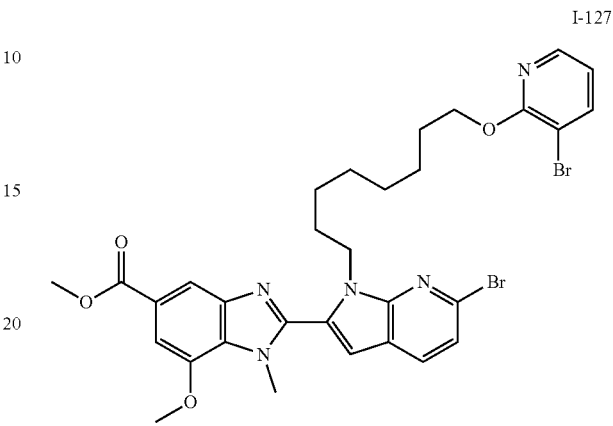

Preparation of methyl 2-[1-[6-[bis(tert-butoxycarbonyl)amino]hexyl]-6-bromo-pyrrolo[2,3-b]pyridin-2-yl]-7-methoxy-1-methyl-benzimidazole-5-carboxylate (I-128)

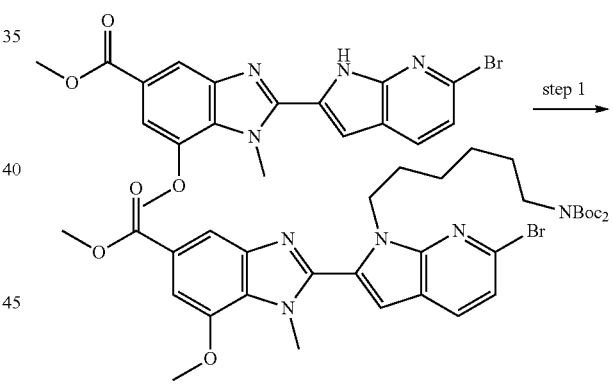

Step 1

Methyl 2-(6-bromo-1H-pyrrolo[2,3-b]pyridin-2-yl)-7-methoxy-1-methyl-1H-benzo[d]imidazole-5-carboxylate (102 mg, 0.247 mmol) and di(tert-butyl) 6-bromohexylcarbonate (140 mg, 0.37 mmol) were charged in a vial and dissolved in DMF (1 mL) and Cs$_2$CO$_3$ (241 mg, 0.74 mmol) was added. The vial was sealed and the mixture was heated to 60° C. overnight. The mixture was cooled down to room temperature and was worked up with EtOAc and water. The organic layer was dried over sodium sulfate, filtered and evaporated to dryness. The residue was purified by column chromatography over silica gel (Hexanes/EtOAc 0-15%) to afford methyl 2-[1-[6-[bis(tert-butoxycarbonyl)amino]hexyl]-6-bromo-pyrrolo[2,3-b]pyridin-2-yl]-7-methoxy-1-methyl-benzimidazole-5-carboxylate.

245

Preparation of methyl 7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carboxylate (I-129)

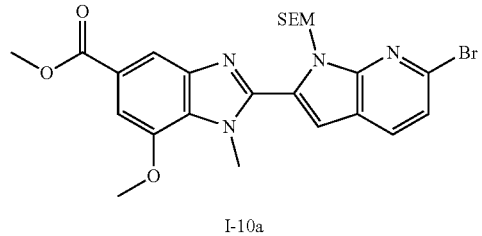

I-10a

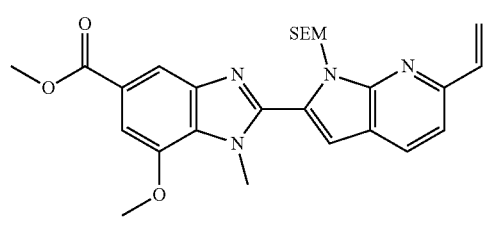

I-129

Step 1

A mixture of methyl 2-[6-bromo-1-(2-trimethylsilylethoxymethyl)pyrrolo[2,3-b]pyridin-2-yl]-7-methoxy-1-methyl-benzimidazole-5-carboxylate (1000 mg, 1.83 mmol), potassium vinyltrifluoroborate (614 mg, 4.58 mmol), and dichloro 1,1'-bis(diphenylphosphino)ferrocene palladium (II) dichloromethane (75 mg, 0.0917 mmol) in isopropanol (40 mL) was heated at reflux overnight. After cooling to rt, the reaction mixture was filtered and the filtrate was concentrated under reduced pressure. The resulting residue was purified via silica gel column chromatography (0-35% ethyl acetate in hexanes) to yield methyl 7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carboxylate. ES/MS: m/z 492.9 [M+H]$^+$.

Preparation of methyl (E)-2-(1-(8-(tert-butoxy)-8-oxooctyl)-6-(((tert-butylsulfinyl)imino)methyl)-1H-pyrrolo[2,3-b]pyridin-2-yl)-7-methoxy-1-methyl-1H-benzo[d]imidazole-5-carboxylate (I-130)

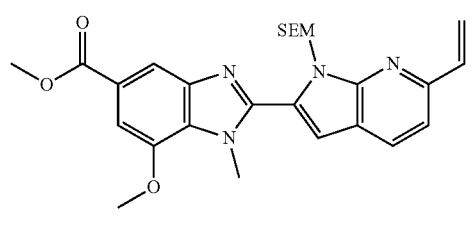

I-129

246

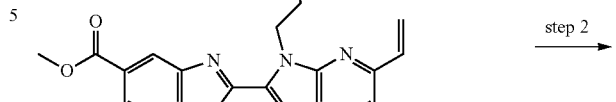

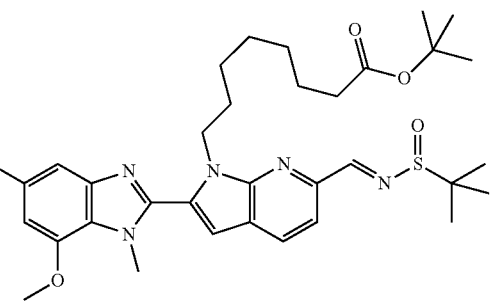

I-130

Step 1

Methyl 2-(1-(8-(tert-butoxy)-8-oxooctyl)-6-vinyl-1H-pyrrolo[2,3-b]pyridin-2-yl)-7-methoxy-1-methyl-1H-benzo[d]imidazole-5-carboxylate was made following step 3 of Procedure 20. ES/MS: m/z 561.1 [M+H]$^+$.

Step 2

Methyl (E)-2-(1-(8-(tert-butoxy)-8-oxooctyl)-6-(((tert-butylsulfinyl)imino)methyl)-1H-pyrrolo[2,3-b]pyridin-2-yl)-7-methoxy-1-methyl-1H-benzo[d]imidazole-5-carboxylate was made following step 4 of Procedure 20. ES/MS: m/z 666.0 [M+H]$^+$.

Preparation of methyl (E)-2-(1-(8-(tert-butoxy)-7,7-dimethyl-8-oxooctyl)-6-(((tert-butylsulfinyl)imino)methyl)-1H-pyrrolo[2,3-b]pyridin-2-yl)-7-methoxy-1-methyl-1H-benzo[d]imidazole-5-carboxylate (I-130b)

Prepared following a similar procedure to I-130 using L4a instead of L1a. ES/MS: m/z 694.2 [M+H]$^+$.

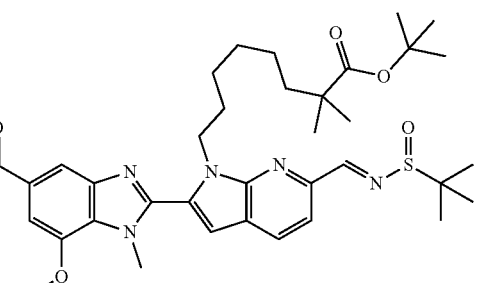

I-130b

Preparation of methyl 2-(1-(8-(tert-butoxy)-8-oxooctyl)-6-(((tert-butylsulfinyl)amino)methyl)-1H-pyrrolo[2,3-b]pyridin-2-yl)-7-methoxy-1-methyl-1H-benzo[d]imidazole-5-carboxylate (I-131)

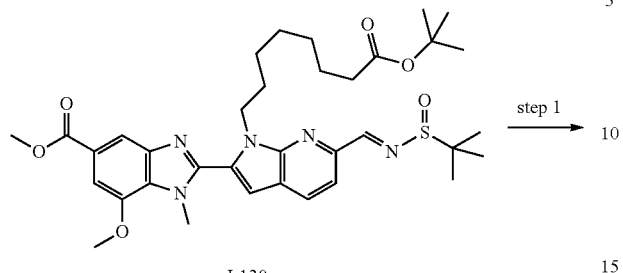

I-130 step 1

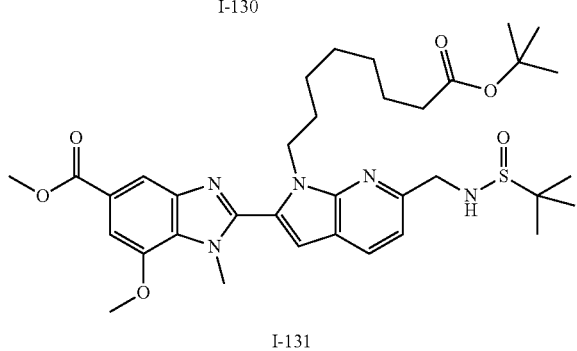

I-131

Step 1

To a cooled solution of methyl (E)-2-(1-(8-(tert-butoxy)-8-oxooctyl)-6-((((tert-butylsulfinyl)imino)methyl)-1H-pyrrolo[2,3-b]pyridin-2-yl)-7-methoxy-1-methyl-1H-benzo[d]imidazole-5-carboxylate (60 mg, 0.090 mmol) in methanol (1 mL) at −40° C. was added sodium borohyride (4 mg, 0.106 mmol). After 90 minutes, additional sodium borohyride (4 mg, 0.106 mmol) was added. After warming to rt and stirring overnight, sodium borohyride (4 mg, 0.106 mmol) was added. After one hour, the reaction mixture was diluted with ethyl acetate and water. The layers were separated and the aqueous was extracted with ethyl acetate. The combined organics were washed with water, brine, dried (MgSO₄), filtered, and concentrated under reduced pressure to yield methyl 2-(1-(8-(tert-butoxy)-8-oxooctyl)-6-(((tert-butylsulfinyl)amino)methyl)-1H-pyrrolo[2,3-b]pyridin-2-yl)-7-methoxy-1-methyl-1H-benzo[d]imidazole-5-carboxylate, which was used without purification. ES/MS: m/z 668.0 [M+H]⁺.

Preparation of methyl 2-(1-(8-(tert-butoxy)-8-oxooctyl)-6-(1-((tert-butylsulfinyl)amino)-2,2,2-trifluoroethyl)-1H-pyrrolo[2,3-b]pyridin-2-yl)-7-methoxy-1-methyl-1H-benzo[d]imidazole-5-carboxylate (I-132)

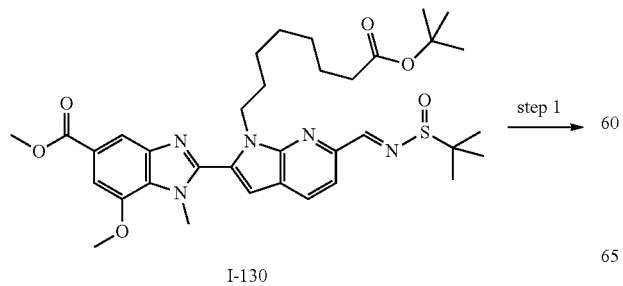

I-130 step 1

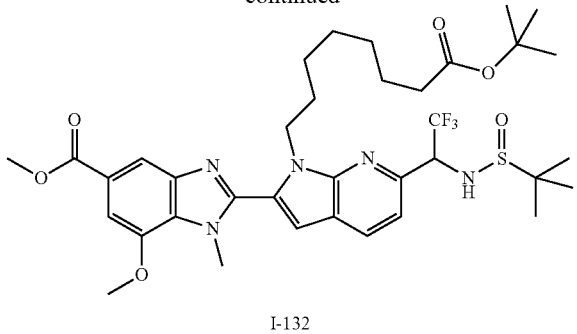

I-132

Step 1.

Trimethyl(trifluoromethyl)silane (0.18 mL, 1.22 mmol) was added to a mixture of methyl 2-[1-(8-tert-butoxy-8-oxo-octyl)-6-[(E)-tert-butylsulfinyliminomethyl]pyrrolo[2,3-b]pyridin-2-yl]-7-methoxy-1-methyl-benzimidazole-5-carboxylate (450 mg, 0.68 mmol) and tetrabutylammonium difluorotriphenylsilicate (640 mg, 1.19 mmol) in THF (15 mL) at −45° C. After four hours, additional tetrabutylammonium difluorotriphenylsilicate (1277 mg, 2.37 mmol) and trimethyl(trifluoromethyl)silane (0.35 ml, 2.37 mmol) were added at −45° C. After 2 hours, the reaction mixture was quenched with sat. NH₄Cl(aq), warmed to rt, and diluted with ethyl acetate and water. The layers were separated and the aqueous was extracted with ethyl acetate. The combined organics washed with water, brine, dried (MgSO₄), filtered, and concentrated under reduced pressure. The resulting residue was purified via silica gel column chromatography (5-100% ethyl acetate in hexanes) to yield methyl 2-(1-(8-(tert-butoxy)-8-oxooctyl)-6-(1-((tert-butylsulfinyl)amino)-2,2,2-trifluoroethyl)-1H-pyrrolo[2,3-b]pyridin-2-yl)-7-methoxy-1-methyl-1H-benzo[d]imidazole-5-carboxylate. ES/MS: m/z 736.0 [M+H]⁺.

methyl 2-(1-(8-(tert-butoxy)-7,7-dimethyl-8-oxooctyl)-6-(1-((tert-butylsulfinyl)amino)-2,2,2-trifluoroethyl)-1H-pyrrolo[2,3-b]pyridin-2-yl)-7-methoxy-1-methyl-1H-benzo[d]imidazole-5-carboxylate (I-132b)

Prepared following a similar procedure to I-132 using I-130b instead of I-130. ES/MS: m/z 764.0 [M+H]⁺.

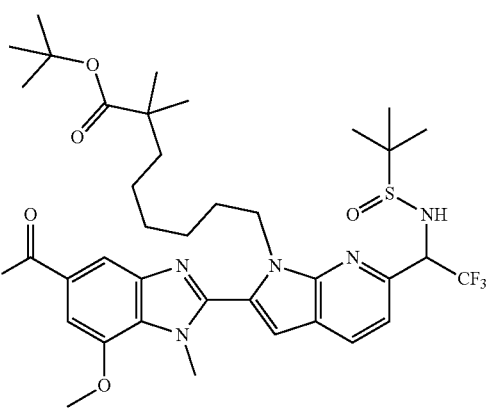

I-132b

Preparation of methyl 2-(1-(8-(tert-butoxy)-8-oxooctyl)-6-(1-((tert-butylsulfinyl)amino)-2,2-difluoroethyl)-1H-pyrrolo[2,3-b]pyridin-2-yl)-7-methoxy-1-methyl-1H-benzo[d]imidazole-5-carboxylate (I-133)

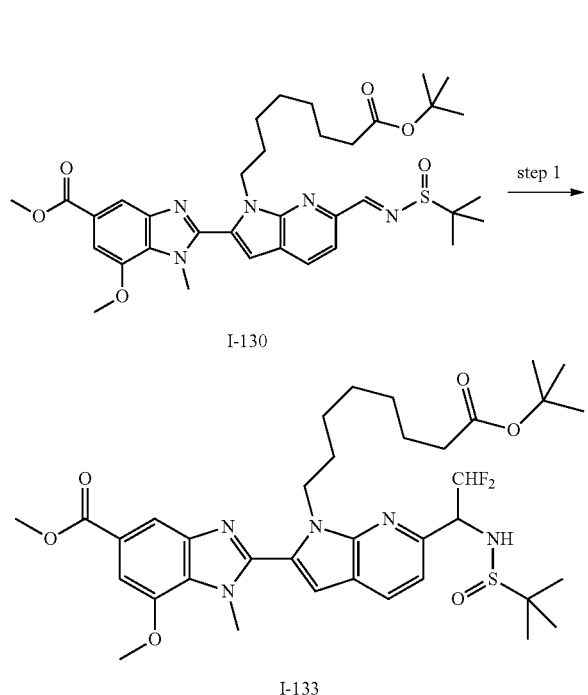

Step 1

Difluoromethyltrimethylsilane (0.697 mL, 5.11 mmol) was added to a solution of methyl 2-[1-(8-tert-butoxy-8-oxo-octyl)-6-[(E)-tert-butylsulfinyliminomethyl]pyrrolo[2,3-b]pyridin-2-yl]-7-methoxy-1-methyl-benzimidazole-5-carboxylate (425 mg, 0.638 mmol) in THF (12 mL). After 72 hours, the reaction mixture was diluted with water and ethyl acetate. The layers were separated and the aqueous extracted with ethyl acetate. The combined organics were dried (MgSO$_4$), filtered, and concentrated under reduced pressure. The resulting residue was purified via silica gel column chromatography (0-100% ethyl acetate/hexanes) to yield methyl 2-(1-(8-(tert-butoxy)-8-oxooctyl)-6-(1-((tert-butylsulfinyl)amino)-2,2-difluoroethyl)-1H-pyrrolo[2,3-b]pyridin-2-yl)-7-methoxy-1-methyl-H-benzo[d]imidazole-5-carboxylate. ES/MS: m/z 718.0 [M+H]$^+$.

Preparation of isopropyl (R)-2-(6-(1-aminoethyl)-1-(2,2-difluoropent-4-en-1-yl)-1H-pyrrolo[2,3-b]pyridin-2-yl)-7-methoxy-1-methyl-1H-benzo[d]imidazole-5-carboxylate (I-135a)

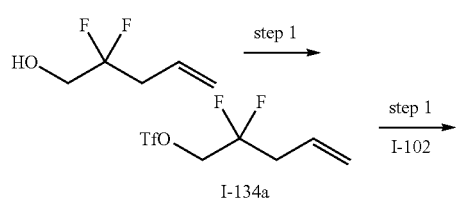

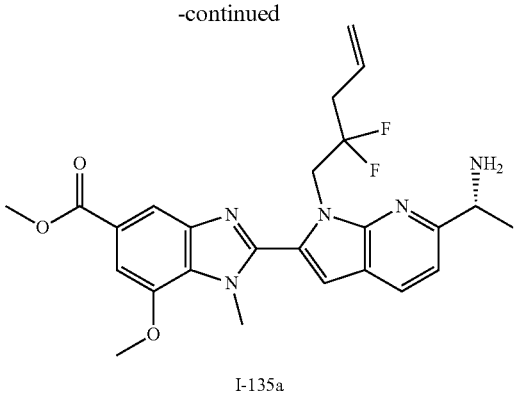

Step 1

A solution of 2,2-difluoropent-4-en-1-ol (1.0 g, 8.2 mmol) in DCM (16 mL) was cooled to 0° C. and 2,6-lutidine (1.92 mL, 16.4 mmol) was added followed by trifluoromethanesulfonic anhydride (1.51 mL, 9 mmol). The resulting mixture was stirred for 30 minutes at 0° C. then 30 minutes at room temperature. It was cooled back to 0° C. and quenched with a saturated solution of ammonium chloride. After work up, the organics were carefully evaporated and the residue was purified by column chromatography over silica gel (Pentane/diethyl ether 0-5%) to afford 2,2-difluoropent-4-en-1-yl trifluoromethanesulfonate. Analytical data matches the literature: Kendrick, D. A.; Danzin, C.; Kolb, M. *J. Med. Chem.* 1989, 32, 170-173.

Step 2

Isopropyl (R)-2-(6-(1-aminoethyl)-1-(2,2-difluoropent-4-en-1-yl)-1H-pyrrolo[2,3-b]pyridin-2-yl)-7-methoxy-1-methyl-1H-benzo[d]imidazole-5-carboxylate was prepared following a similar procedure to steps 1-2 of I-107a using 2,2-difluoropent-4-en-1-yl trifluoromethanesulfonate (I-134a) instead of 5-bromopent-1-ene. ES/MS: m/z 511.9 [M+H]$^+$.

methyl (R)-2-(6-(1-aminoethyl)-1-(2,2-difluorobut-3-en-1-yl)-1H-pyrrolo[2,3-b]pyridin-2-yl)-1-cyclopropyl-6,7-difluoro-1H-benzo[d]imidazole-5-carboxylate (I-135b)

Prepared following a similar procedure to I-135a using I-141a instead of I-102 and using 2,2-difluorobut-3-en-1-ol instead of 2,2-difluoropent-4-en-1-ol. ES/MS: m/z 502.1 [M+H]$^+$.

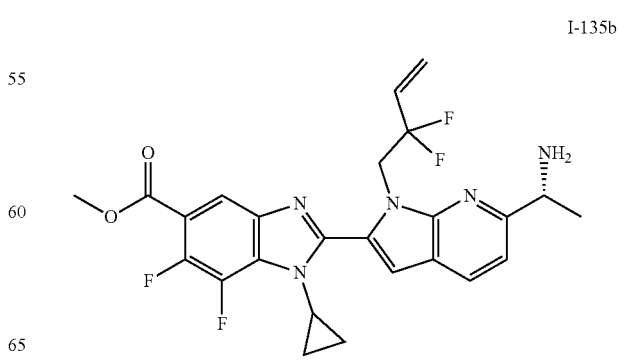

251 methyl (R)-2-(6-(1-aminoethyl)-1-(2,2-difluoropent-4-en-1-yl)-1H-pyrrolo[2,3-b]pyridin-2-yl)-1-cyclopropyl-6-fluoro-1H-benzo[d]imidazole-5-carboxylate (I-135c)

Prepared following a similar procedure to I-135a using I-141b instead of I-102. ES/MS: m/z 497.3 [M+H]⁺.

252 methyl (R)-2-(6-(1-aminoethyl)-1-(2,2-difluoropent-4-en-1-yl)-1H-pyrrolo[2,3-b]pyridin-2-yl)-1-cyclopropyl-7-fluoro-1H-benzo[d]imidazole-5-carboxylate (I-135e)

Prepared following a similar procedure to I-135a using I-141c instead of I-102. ES/MS: m/z 498.0 [M+H]⁺.

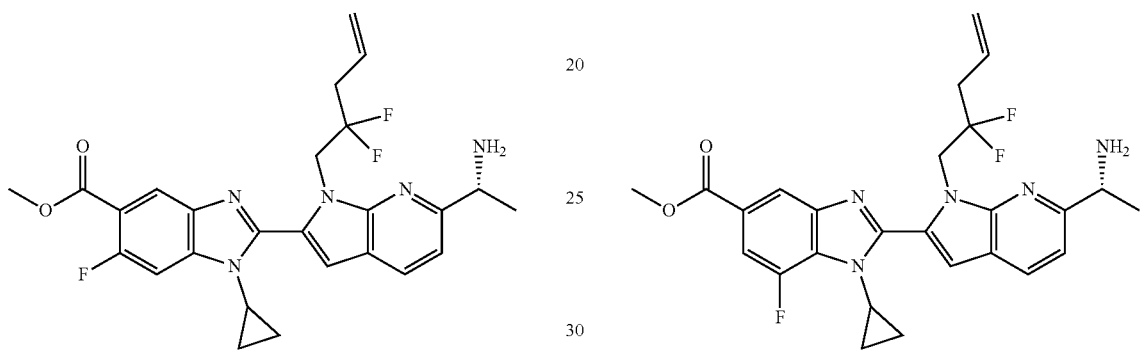

methyl (R)-2-(6-(1-aminoethyl)-1-(2,2-difluoropent-4-en-1-yl)-1H-pyrrolo[2,3-b]pyridin-2-yl)-6-fluoro-1-methyl-1H-benzo[d]imidazole-5-carboxylate (I-135d)

Prepared following a similar procedure to I-135a using I-143b instead of I-102. ES/MS: m/z 472.3 [M+H]⁺.

isopropyl (R)-2-(6-(1-aminoethyl)-1-(2,2-difluorobut-3-en-1-yl)-7-fluoro-1H-indol-2-yl)-7-methoxy-1-methyl-1H-benzo[d]imidazole-5-carboxylate (I-135f)

Prepared following a similar procedure to I-135a using I-146a instead of I-102 and using 2,2-difluorobut-3-en-1-ol instead of 2,2-difluoropent-4-en-1-ol. ES/MS: m/z 516.15 [M+H]⁺.

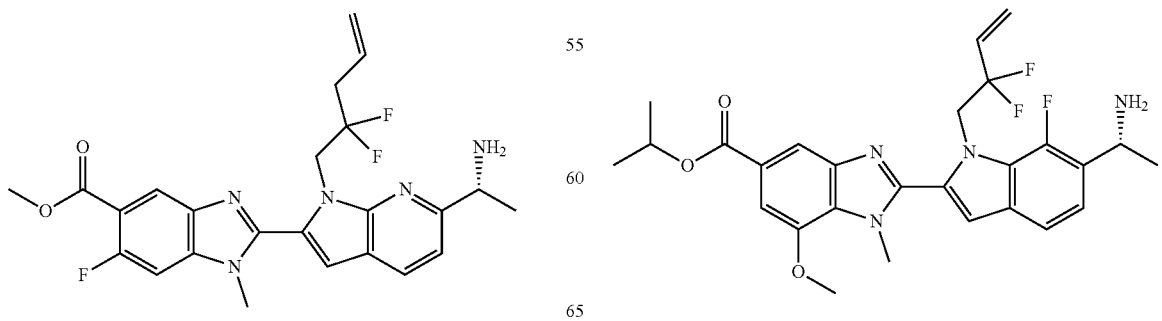

isopropyl (R)-2-(6-(1-aminoethyl)-1-(2,2-difluorobut-3-en-1-yl)-1H-pyrrolo[2,3-b]pyridin-2-yl)-7-methoxy-1-methyl-1H-benzo[d]imidazole-5-carboxylate (I-135g)

Prepared following a similar procedure to I-135a using 2,2-difluorobut-3-en-1-ol instead of 2,2-difluoropent-4-en-1-ol. ES/MS: m/z 498.43 [M+H]⁺.

methyl (R)-2-(6-(1-((tert-butoxycarbonyl)amino)ethyl)-1-(2,2-difluorobut-3-en-1-yl)-5-fluoro-1H-indol-2-yl)-1-cyclopropyl-7-fluoro-1H-benzo[d]imidazole-5-carboxylate (I-135i)

Prepared following a similar procedure to I-135a using 1-149b and 2,2-difluorobut-3-en-1-ol instead of 2,2-difluoropent-4-en-1-ol. ES/MS: m/z 501.03 [M+H]⁺.

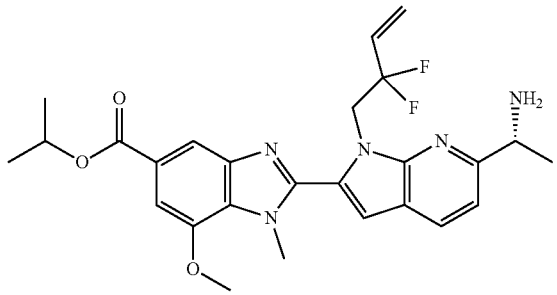

I-135g

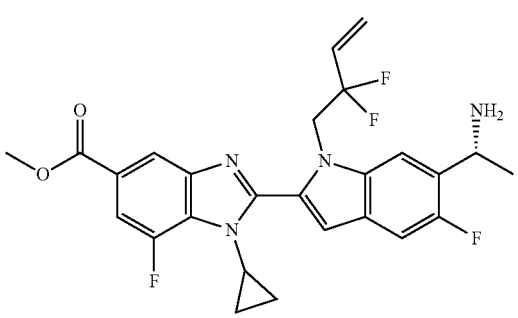

I-135i methyl (R)-2-(6-(1-aminoethyl)-1-(2,2-difluorobut-3-en-1-yl)-1H-pyrrolo[2,3-b]pyridin-2-yl)-1-cyclopropyl-6-fluoro-1H-benzo[d]imidazole-5-carboxylate (I-135h)

Prepared following a similar procedure to I-135a using 1-141b and 2,2-difluorobut-3-en-1-ol instead of 2,2-difluoropent-4-en-1-ol. ES/MS: m/z 483.90 [M+H]⁺.

methyl (R)-2-(6-(1-((tert-butoxycarbonyl)amino)ethyl)-1-(2,2-difluorobut-3-en-1-yl)-5-fluoro-1H-indol-2-yl)-7-methoxy-1-methyl-1H-benzo[d]imidazole-5-carboxylate (I-135j)

Prepared following a similar procedure to I-135a using 1-149a and 2,2-difluorobut-3-en-1-ol instead of 2,2-difluoropent-4-en-1-ol. ES/MS: m/z 487.03 [M+H]⁺.

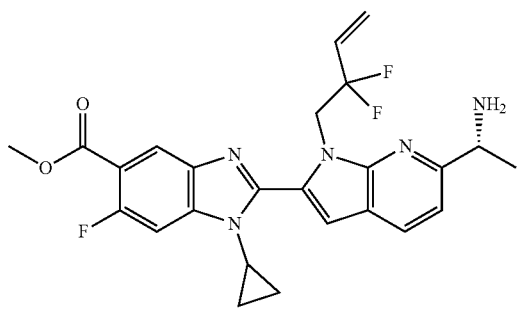

I-135h

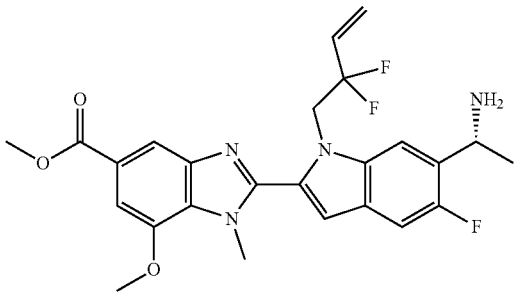

I-135j isopropyl (R)-2-(6-(1-aminoethyl)-1-(2,2-difluoro-hept-6-en-1-yl)-1H-pyrrolo[2,3-b]pyridin-2-yl)-7-methoxy-1-methyl-1H-benzo[d]imidazole-5-carboxylate (I-135k)

Prepared following a similar procedure to I-135a using 2,2-difluorooct-7-en-1-yl trifluoromethanesulfonate. ES/MS: m/z 540.4 [M+H]⁺.

methyl (R)-2-(6-(1-aminoethyl)-1-(2,2-difluorobut-3-en-1-yl)-1H-pyrrolo[2,3-b]pyridin-2-yl)-6-fluoro-1-methyl-1H-benzo[d]imidazole-5-carboxylate (I-135m)

Prepared following a similar procedure to I-135a using I-143b instead of I-102 and using 2,2-difluorobut-3-en-1-ol instead of 2,2-difluoropent-4-en-1-ol. ES/MS: m/z 458.3 [M+H]⁺.

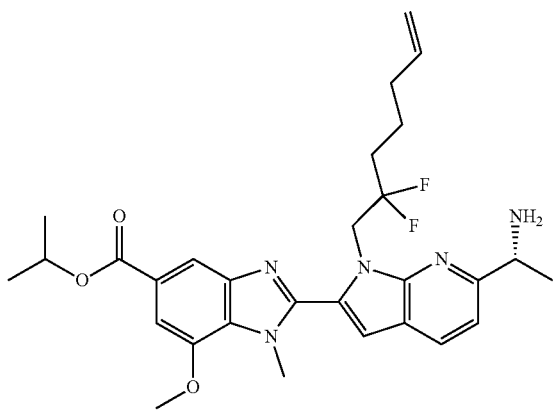

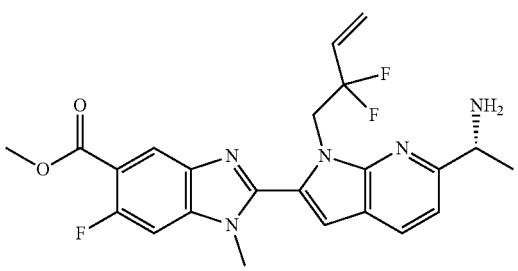

methyl (R)-2-(6-(1-aminoethyl)-1-(2,2-difluorobut-3-en-1-yl)-1H-pyrrolo[2,3-b]pyridin-2-yl)-6,7-difluoro-1-methyl-1H-benzo[d]imidazole-5-carboxylate (I-135l)

Prepared following a similar procedure to I-135a using I-143i instead of I-102 and using 2,2-difluorobut-3-en-1-ol instead of 2,2-difluoropent-4-en-1-ol. ES/MS: m/z 476.2 [M+H]⁺.

methyl (R)-2-(6-(1-aminoethyl)-1-(2,2-difluorobut-3-en-1-yl)-1H-pyrrolo[2,3-b]pyridin-2-yl)-1,6-dimethyl-1H-benzo[d]imidazole-5-carboxylate (I-135n)

Prepared following a similar procedure to I-135a using I-143h instead of I-102 and using 2,2-difluorobut-3-en-1-ol instead of 2,2-difluoropent-4-en-1-ol. ES/MS: m/z 454.3 [M+H]⁺.

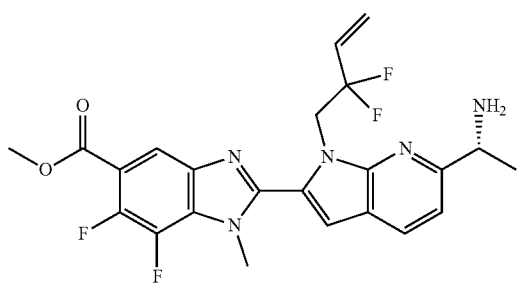

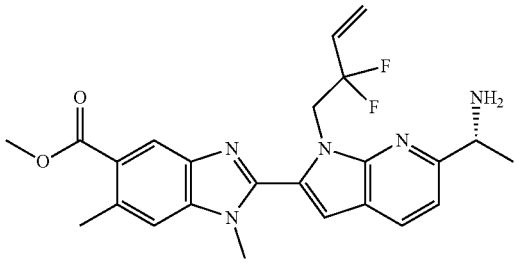

methyl (R)-2-(6-(1-aminoethyl)-1-(2,2-difluorobut-3-en-1-yl)-1H-pyrrolo[2,3-b]pyridin-2-yl)-1-cyclopropyl-7-fluoro-1H-benzo[d]imidazole-5-carboxylate (I-135o)

Prepared following a similar procedure to I-135a using 2,2-difluorobut-3-en-1-ol instead of 2,2-difluoropent-4-en-1-ol and I-141c. ES/MS: m/z 484.2 [M+H]+.

methyl (R)-2-(6-(1-aminoethyl)-1-(2,2-difluorobut-3-en-1-yl)-1H-pyrrolo[2,3-b]pyridin-2-yl)-7-fluoro-1-methyl-1H-benzo[d]imidazole-5-carboxylate (I-135q)

Prepared following a similar procedure to I-135a using 2,2-difluorobut-3-en-1-ol instead of 2,2-difluoropent-4-en-1-ol and I-141j. ES/MS: m/z 458.2 [M+H]+.

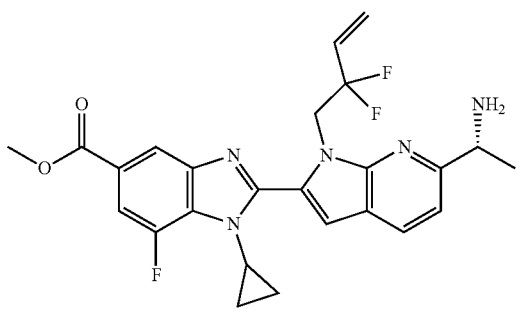

I-135o

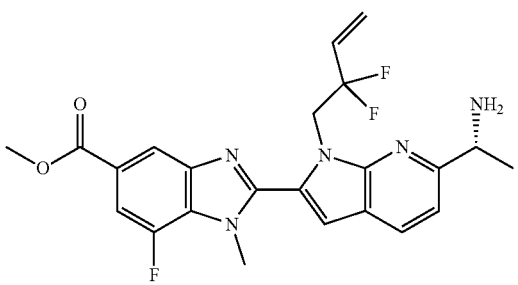

I-135q isopropyl (R)-2-(6-(1-aminoethyl)-1-(2,2-difluorobut-3-en-1-yl)-1H-pyrrolo[2,3-b]pyridin-2-yl)-1-cyclopropyl-1H-benzo[d]imidazole-5-carboxylate (I-135p)

Prepared following a similar procedure to I-135b starting with I-104c. ES/MS: m/z 494.3 [M+H]+.

methyl (R)-2-(6-(1-aminoethyl)-1-(2,2-difluorobut-3-en-1-yl)-1H-pyrrolo[2,3-b]pyridin-2-yl)-1-cyclopropyl-7-methoxy-1H-benzo[d]imidazole-5-carboxylate (I-135r)

Prepared following a similar procedure to I-141a using I-141i. ES/MS: m/z 496.3 [M+H]+.

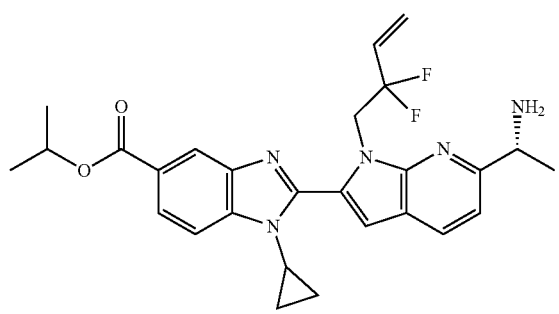

I-135p

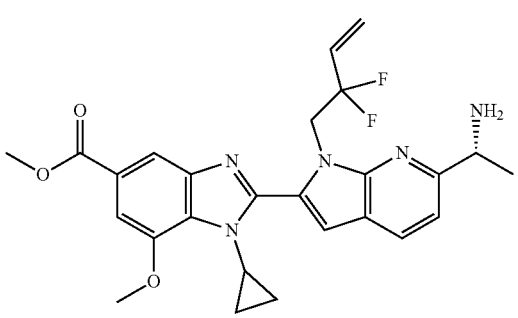

I-135r methyl (R)-2-(6-(1-aminoethyl)-1-(2,2-difluoropent-4-en-1-yl)-1H-pyrrolo[2,3-b]pyridin-2-yl)-1-cyclopropyl-7-methoxy-1H-benzo[d]imidazole-5-carboxylate (I-135s)

Prepared following a similar procedure to I-141a using I-141i. ES/MS: m/z 510.3 [M+H]$^+$.

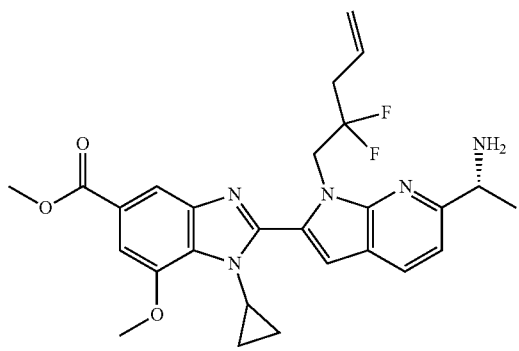

Preparation of tert-butyl (R)-(1-(2-(6-cyano-3-ethylpyrazolo[1,5-a]pyridin-2-yl)-1H-pyrrolo[2,3-b]pyridin-6-yl)ethyl)carbamate (I-136a)

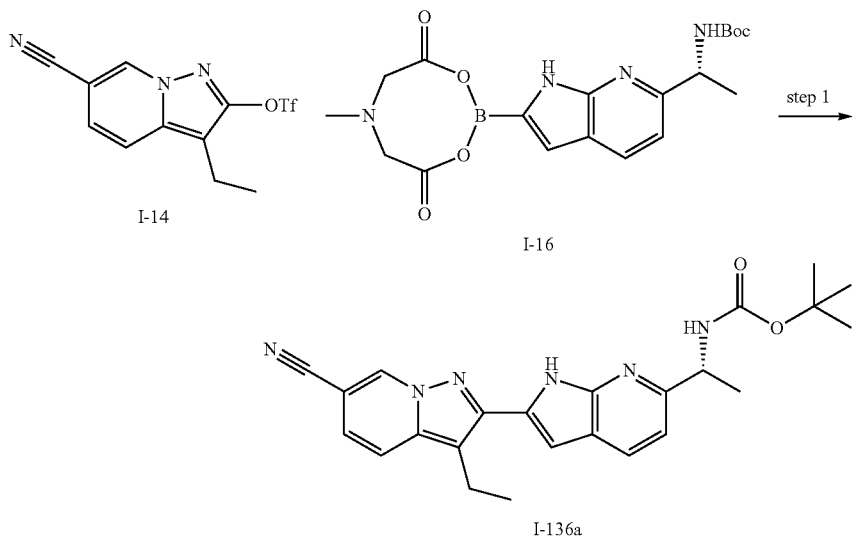

Step 1

A mixture of 6-cyano-3-ethylpyrazolo[1,5-a]pyridin-2-yl trifluoromethanesulfonate (I-14, 85 mg, 0.266 mmol), tert-butyl (R)-(1-(2-(6-methyl-4,8-dioxo-1,3,6,2-dioxazaborocane-2-yl)-1H-pyrrolo[2,3-b]pyridin-6-yl)ethyl)carbamate (I-16, 221 mg, 0.532 mmol), bis(triphenylphosphine) palladium (II) dichloride 23.1 mg, 0.032 mmol), and sodium carbonate (227 mg, 2.16 mmol) in dioxane (3.9 mL) and water (0.75 mL) was heated at 100° C. under argon. After 2.5 h, the reaction mixture was cooled to rt and diluted with ethyl acetate and water. The layers were separated and the aqueous was extracted with ethyl acetate. The combined organics washed with water, dried (MgSO$_4$), filtered, and concentrated under reduced pressure. The resulting residue was purified via silica gel column chromatography (0-55% ethyl acetate/hexanes) to yield tert-butyl (R)-(1-(2-(6-cyano-3-ethylpyrazolo[1,5-a]pyridin-2-yl)-1H-pyrrolo[2,3-b]pyridin-6-yl)ethyl)carbamate. ES/MS: m/z 431.4 [M+H]$^+$.

tert-butyl (R)-(1-(2-(6-cyano-4-methoxy-3-methylpyrazolo[1,5-a]pyridin-2-yl)-1H-pyrrolo[2,3-b]pyridin-6-yl)ethyl)carbamate (I-136b)

Prepared following a similar procedure to I-136a using I-15 instead of I-14. ES/MS: m/z 447.2 [M+H]$^+$.

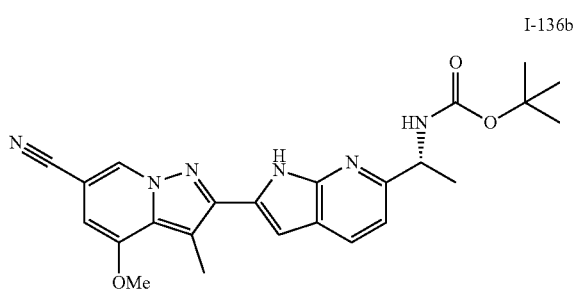 [SMILES: COc1cc(C#N)cn2nc(-c3cc4ccc([C@@H](C)NC(=O)OC(C)(C)C)nc4[nH]3)c(C)c12]

methyl (R)-2-(6-(1-((tert-butoxycarbonyl)amino)ethyl)-1H-pyrrolo[2,3-b]pyridin-2-yl)-3-cyclopropyl-6-fluoroimidazo[1,2-a]pyridine-7-carboxylate (I-136c)

Prepared following a similar procedure to I-136a using I-5c instead of I-14. ES/MS: m/z 494.3 [M+H]$^+$.

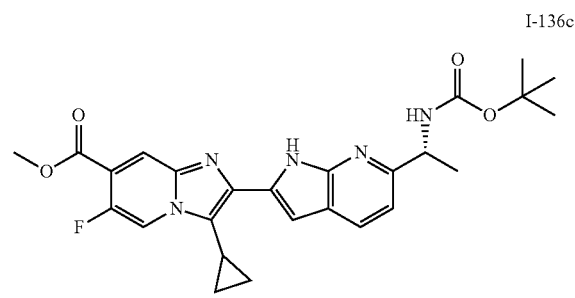 [SMILES: COC(=O)c1cc2nc(-c3cc4ccc([C@@H](C)NC(=O)OC(C)(C)C)nc4[nH]3)c(C3CC3)n2cc1F]

Preparation of (6-(benzyloxy)-1-(tert-butoxycarbonyl)-1H-pyrrolo[2,3-b]pyridin-2-yl)boronic Acid (I-137)

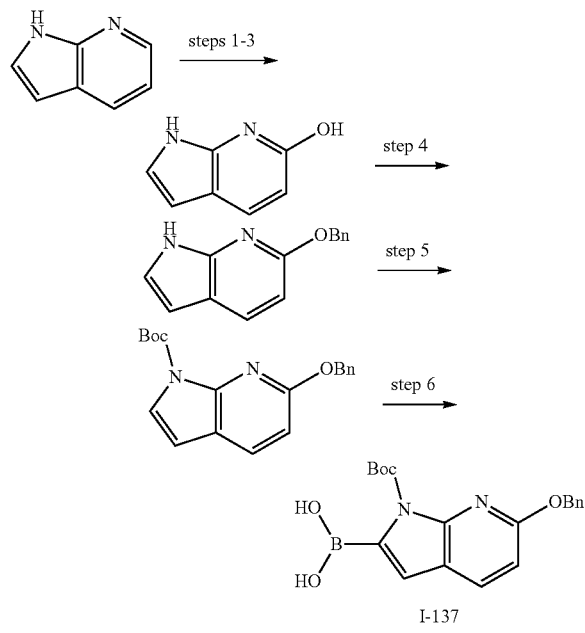

Step 1

To a solution of 1H-pyrrolo[2,3-b]pyridine (150 g, 1.27 mol) in ethyl acetate (1500 mL) at 0° C. was added a solution of 85% m-CPBA (335 g, 1.65 mol) in ethyl acetate (1500 mL) over 1.5 h. The resulting solution was stirred at room temperature for 4 h. After cooling to 0° C. the resulting slurry was filtered and the solid was washed with ethyl acetate (3×50 mL). The solid was added to 30% potassium carbonate solution (200 mL) and this mixture was stirred for 2 h at 0° C. The solid was collected by filtration, washed with water (2×30 mL) and dried in vacuo to give crude 1H-pyrrolo[2,3-b]pyridine 7-oxide.

Step 2

Crude 1H-pyrrolo[2,3-b]pyridine 7-oxide (150 g, 670.9 mmol, ca. 60% purity) in acetic anhydride (450 mL) was heated to reflux for 12 h. The mixture was cooled, concentrated to half of its volume, diluted with DCM (500 mL), washed with water (2×100 mL), dried over anhydrous sodium sulfate and concentrated to give crude 1-acetyl-1H-pyrrolo[2,3-b]pyridin-6-yl acetate.

Step 3

A mixture of crude 1-acetyl-1H-pyrrolo[2,3-b]pyridin-6-yl acetate (150 g, 412 mmol, 60% purity) and potassium carbonate (250 g, 1810 mmol) in methanol/water (1:1, 2600 mL) was stirred at room temperature for 12 h. The reaction mixture was concentrated to half its volume and extracted with chloroform (6×300 mL). The organic layer was dried over anhydrous sodium sulfate and concentrated in vacuo. The crude product was purified by column chromatography on silica gel (MeOH/DCM=1:10) to give 1H-pyrrolo[2,3-b]pyridin-6-ol. $^1$H NMR (400 MHz, DMSO) δ 11.09 (s, 1H), 10.37 (s, 1H), 7.73 (d, J=8.4 Hz, 1H), 7.18-6.89 (m, 1H), 6.41-6.18 (m, 2H).

Step 4

A mixture of 1H-pyrrolo[2,3-b]pyridin-6-ol (60 g, 447 mmol), potassium carbonate (250 g, 1809 mmol) and benzyl bromide (76 g, 447 mmol) in acetone (1500 mL) was stirred at 50° C. for 16 h. The reaction mixture was cooled and filtered through Celite. The filtrate was concentrated and the crude product was purified by column chromatography on silica gel (3:1 petroleum ether:ethyl acetate) to give 6-(benzyloxy)-1H-pyrrolo[2,3-b]pyridine. $^1$H NMR: (400 MHz, DMSO) δ 11.43 (s, 1H), 7.85 (d, J=8.2 Hz, 0H), 7.45 (d, J=7.3 Hz, 1H), 7.39-7.26 (m, 1H), 7.17 (s, 1H), 6.56 (d, J=8.4 Hz, 1H), 6.33 (s, 1H), 5.34 (s, 2H).

Step 5

A mixture of 6-(benzyloxy)-1H-pyrrolo[2,3-b]pyridine (70 g, 310 mmol), triethylamine (34.7 g, 343 mmol), DMAP (2.29 g, 18.7 mmol), and di-tert-butyl dicarbonate (74.85 g, 343 mmol) in DCM (1000 mL) was stirred at rt for 2h. The reaction mixture was concentrated and the crude product was purified by column chromatography on silica gel (3:1 petroleum ether:ethyl acetate) to give tert-butyl 6-(benzyloxy)-1H-pyrrolo[2,3-b]pyridine-1-carboxylate. $^1$H NMR: $^1$H NMR (400 MHz, DMSO) δ 7.90 (t, J=22.5 Hz, 1H), 7.61-7.44 (m, 3H), 7.42-7.20 (m, 3H), 6.75 (d, J=8.4 Hz, 1H), 6.57 (dd, J=21.0, 19.9 Hz, 1H), 5.38 (d, J=37.9 Hz, 2H), 1.60 (s, 9H).

Step 6

To a solution of tert-butyl 6-(benzyloxy)-1H-pyrrolo[2,3-b]pyridine-1-carboxylate (60 g, 185 mmol) and triisopropyl borate (76.5 g, 407 mmol) in THF (600 mL) under N$_2$ at −78° C. was added LDA (2 M in THF, 123 mL) dropwise. The reaction was stirred at this temperature for 5 h. The reaction mixture was quenched with 600 mL of 1 M pH ~7 phosphate buffer. The mixture was diluted with EtOAc, and the phases were separated. The organic phase was washed with water and brine, dried over Na₂SO₄, filtered and concentrated. The crude product was purified by column chromatography on silica gel (1:1 petroleum ether:ethyl acetate) to give tert-butyl 6-(benzyloxy)-1H-pyrrolo[2,3-b]pyridine-1-carboxylate. ES/MS: m/z 368.9 [M+H]⁺. ¹H NMR: (400 MHz, DMSO) δ 8.13 (s, 1H), 7.88 (d, J=8.4 Hz, 0H), 7.50 (d, J=7.2 Hz, 1H), 7.34 (d, J=7.4 Hz, 2H), 6.71 (d, J=8.4 Hz, 1H), 6.57 (s, 1H), 5.43 (s, 2H), 1.58 (s, 5H).

Preparation of methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate (I-138)

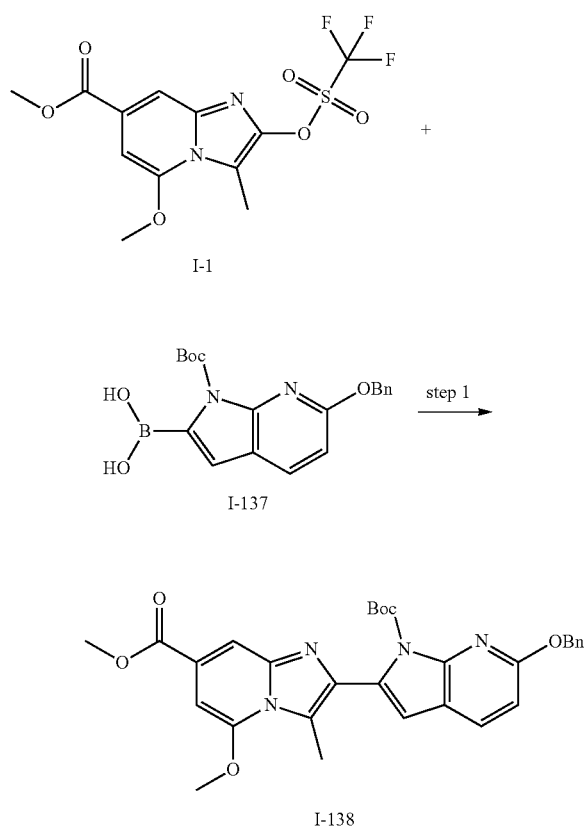 [SMILES: COC(=O)c1cc(OC)n2c(C)c(OS(=O)(=O)C(F)(F)F)nc2c1 ; [I-] ; CC(C)(C)OC(=O)n1c(B(O)O)cc2ccc(OCc3ccccc3)nc21 ; COC(=O)c1cc(OC)n2c(C)c(-c3cc4ccc(OCc5ccccc5)nc4n3C(=O)OC(C)(C)C)nc2c1]

Step 1

A solution of methyl 5-methoxy-3-methyl-2-(trifluoromethylsulfonyloxy)imidazo[1,2-a]pyridine-7-carboxylate (I-1, 0.5 g, 1.36 mmol) and (6-benzyloxy-1-tert-butoxycarbonyl-pyrrolo[2,3-b]pyridin-2-yl)boronic acid (I-137, 0.65 g, 1.76 mmol), cesium carbonate (1.11 g, 3.39 mmol), and Jackiephos (0.05 g, 0.04 mmol) in MeTHF (5 mL) and water (0.5 mL) was purged with argon. The mixture was stirred at ambient temperature for 18 h. The aqueous layer was removed and the organic layer washed with water, dried with Na₂SO₄, filtered, and concentrated. The product was purified by silica chromatography using EtOAc in hexanes to afford methyl 2-(6-(benzyloxy)-1-(tert-butoxycarbonyl)-1H-pyrrolo[2,3-b]pyridin-2-yl)-5-methoxy-3-methylimidazo[1,2-a]pyridine-7-carboxylate. ES/MS: m/z 543.2 [M+H]⁺.

Preparation of tert-butyl (R)-(1-(2-formyl-1H-pyrrolo[2,3-b]pyridin-6-yl)ethyl)carbamate (I-139)

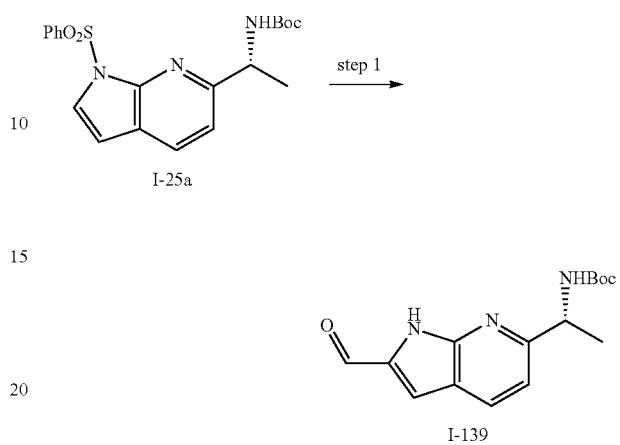

Step 1

A solution of s-BuLi in cyclohexane (1.4 M, 24.9 mL, 34.9 mmol) was added dropwise to cooled solution of tert-butyl N-[(1R)-1-[1-(benzenesulfonyl)pyrrolo[2,3-b]pyridin-6-yl]ethyl]carbamate (intermediate described in the synthesis of I-16) (4.0 g, 10.0 mmol) in THF (100 mL) at −78° C. After 2 h, N,N-dimethylformamide (5.3 mL, 7.1 mmol) was added dropwise. The reaction mixture was stirred at −78° C. After two hours, the reaction mixture was quenched with aqueous ammonium chloride and extracted with ethyl acetate. The combined organics were washed with water, brine, dried (MgSO₄), filtered, and concentrated under reduced pressure. The resulting residue was purified via silica gel column chromatography (0-35% ethyl acetate/hexanes) to yield tert-butyl (R)-(1-(2-formyl-1H-pyrrolo[2,3-b]pyridin-6-yl)ethyl)carbamate. ¹H NMR (400 MHz, DMSO-d6) δ 12.45 (s, 1H), 9.85 (s, 1H), 8.17 (d, J=8.3 Hz, 1H), 7.40 (d, J=8.3 Hz, 1H), 7.37 (s, 1H), 7.21 (d, J=8.3 Hz, 1H), 4.83-4.61 (m, 1H), 1.38 (d, J=4.8 Hz, 3H), 1.37 (s, 9H).

Preparation of methyl 5-amino-4-(cyclopropylamino)-2,3-difluorobenzoate (I-140a)

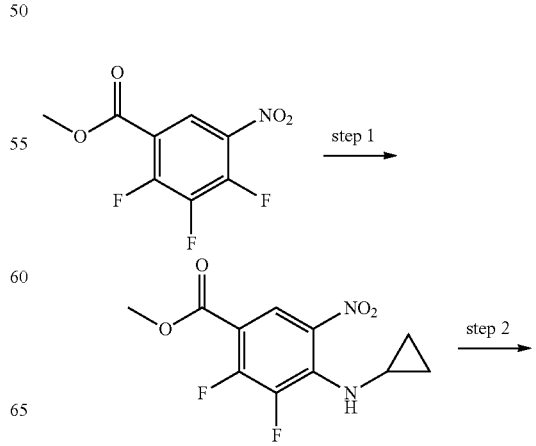

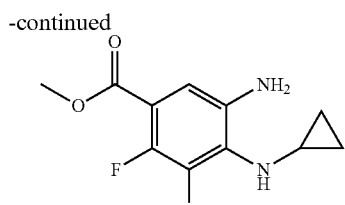

I-140a

Step 1
A 100 mL round bottom flask was charged with methyl 2,3,4-trifluoro-5-nitrobenzoate (1.18 g, 5 mmol) a stir bar and THF (20 mL). The solution was cooled to −78° C. and Hunig's base (1.3 mL, 7.5 mmol) was added followed by dropwise addition of cyclopropylamine (346 μL, 5 mmol). The remaining mixture was stirred at −78° C. (acetone dry ice bath) for 30 minutes then at −46° C. (acetonitrile dry ice bath) for 1 h. It was then slowly warmed up to 0° C. over 1 h and quenched with water. After usual work up (EtOAc, water) the residue was purified by flash chromatography over silica gel (Hexanes/EtOAc 0-10%) to afford methyl 4-(cyclopropylamino)-2,3-difluoro-5-nitrobenzoate. ES/MS: m/z 270.8 [M+H]$^+$.

Step 2
Methyl 4-(cyclopropylamino)-2,3-difluoro-5-nitrobenzoate (272 mg, 1 mmol) was charged in a vial and (1% Pt)/(2% V) on carbon (Strem Chemical 78-1536) (55 mg) was added followed by ethyl acetate (3 mL). The mixture was degassed with nitrogen for 5 minutes and then placed under an atmosphere of hydrogen for 12 hours at which point the LCMS analysis showed full conversion of the starting material. Filtration and evaporation yielded the crude methyl 5-amino-4-(cyclopropylamino)-2,3-difluorobenzoate which was used in the next step without further purification. ES/MS: m/z 243.1 [M+H]$^+$.

methyl 5-amino-4-(cyclopropylamino)-2-fluorobenzoate (I-140b)

Prepared following a similar procedure to I-140a using methyl 2,4-difluoro-5-nitrobenzoate. ES/MS: m/z 225.1 [M+H]$^+$.

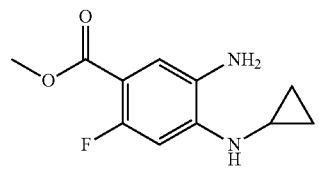

I-140b methyl 3-amino-4-(cyclopropylamino)-5-fluorobenzoate (I-140c)

Intermediate I-140c (ES/MS: m/z 225.05 [M+H]$^+$) prepared following a similar procedure to I-140a starting with methyl 3,4-difluoro-5-nitrobenzoate prepared as described here: 3,4-difluoro-5-nitro-benzoic acid (8.26 g, 40.7 mmol) was dissolved in DCM under N$_2$. Oxalyl chloride (3.7 mL, 43.1 mmol) was added over 2 min. After 3 h, the mixture was cooled to −20° C., and methanol (2.1 mL) was added slowly followed by Et$_3$N (11.3 mL, 81.3 mmol). The mixture was stirred 15 min and was then allowed to warm to r.t. After an additional 90 min, the mixture was partitioned between DCM and water. Phases were separated, and the organic phase was dried over Na$_2$SO$_4$, filtered, and concentrated. Purification by silica gel (5-15% EtOAc in hexanes) provided methyl 3,4-difluoro-5-nitro-benzoate.

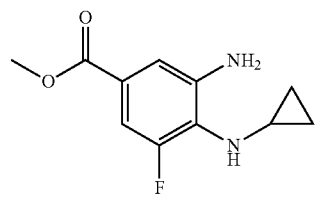

I-140c methyl 3-amino-5-fluoro-4-(((1R,2R)-2-fluorocyclopropyl)amino)benzoate (I-140d)

Prepared following a similar procedure to I-140c using (1R,2R)-2-fluorocyclopropane-1-amine. ES/MS: m/z 242.96 [M+H]$^+$.

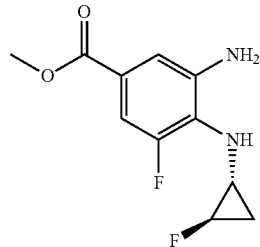

I-140d methyl 3-amino-5-fluoro-4-(((1S,2S)-2-fluorocyclopropyl)amino)benzoate (I-140e)

Prepared following a similar procedure to I-140c using (1S,2S)-2-fluorocyclopropane-1-amine. ES/MS: m/z 242.96 [M+H]$^+$.

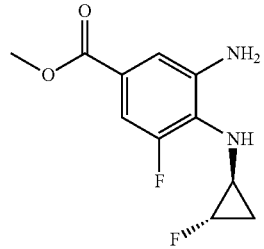

I-140e methyl 3-amino-5-fluoro-4-(((1R,2S)-2-fluorocyclo-
propyl)amino)benzoate (I-140f)

Prepared following a similar procedure to I-140c using (1R,2S)-2-fluorocyclopropane-1-amine. ES/MS: m/z 242.96 [M+H]⁺.

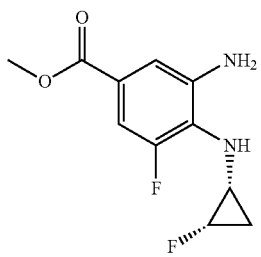

I-140f methyl (rac)-3-amino-4-(((1S,2S)-2-(difluorom-
ethyl)cyclopropyl)amino)-5-fluorobenzoate (I-140g)

Prepared following a similar procedure to I-140c using trans-2-(difluoromethyl)cyclopropane-1-amine. ES/MS: m/z 274.98 [M+H]⁺.

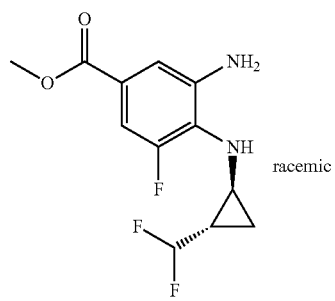

I-140g methyl 5-amino-6-(cyclopropylamino)nicotinate
(I-140h)

Prepared following a similar procedure to I-140a using methyl 6-fluoro-5-nitro-pyridine-3-carboxylate. ES/MS: m/z 208.05 [M+H]⁺.

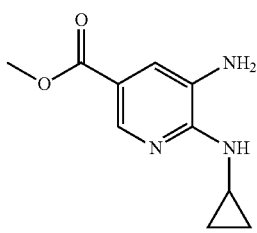

I-140h methyl 3-amino-5-fluoro-4-(((1S,2R)-2-fluorocyclo-
propyl)amino)benzoate (I-140i)

Prepared following a similar procedure to I-140c using (1S,2R)-2-fluorocyclopropane-1-amine. ES/MS: m/z 242.96 [M+H]⁺.

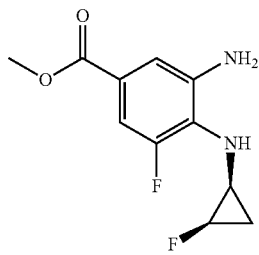

I-140i methyl 3-amino-5-fluoro-4-(methylamino)benzoate
(I-140j)

Prepared following a similar procedure to I-140c using methylamine instead of cyclopropylamine. ES/MS: m/z 199.0 [M+H]⁺.

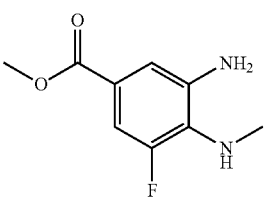

I-140j methyl
3-amino-5-chloro-4-(cyclopropylamino)benzoate
(I-140k)

Prepared following a similar procedure to I-140a using methyl 3-chloro-4-fluoro-5-nitrobenzoate. ES/MS: m/z 241.1 [M+H]⁺.

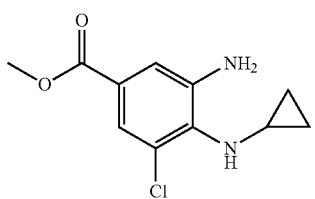

I-140k methyl 3-amino-5-fluoro-4-(((1S,2S)-2-methoxycy-
clopropyl)amino)benzoate (I-140l)

Prepared following a similar procedure to I-140c using (1S,2S)-2-methoxycyclopropane-1-amine instead of cyclopropylamine. ES/MS: m/z 254.7 [M+H]⁺.

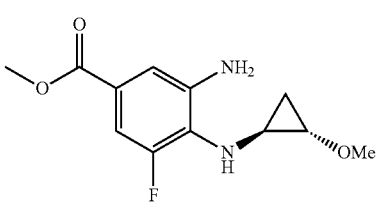

I-140l methyl 5-amino-2-fluoro-4-(((1R,2S)-2-fluorocyclopropyl)amino)benzoate (I-140m)

Prepared following a similar procedure to I-140f using methyl 2,4-difluoro-5-nitrobenzoate and (1R,2S)-2-fluorocyclopropane-1-amine. ES/MS: m/z 243.1 [M+H]⁺.


methyl 5-amino-2-fluoro-4-(((1R,2S)-2-fluorocyclopropyl)amino)benzoate (I-140n)

Prepared following a similar procedure to I-140f using methyl 2,4-difluoro-5-nitrobenzoate and 2-methoxycyclopropanamine hydrochloride. ES/MS: m/z 254.8 [M+H]⁺.

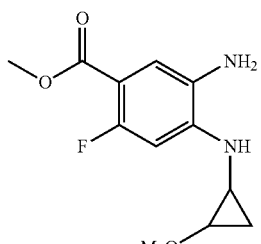

methyl 5-amino-2-chloro-4-(methylamino)benzoate (I-140o)

Prepared following a similar procedure to I-140j using methyl 2-chloro-4-fluoro-5-nitrobenzoate. ES/MS: m/z 215.0 [M+H]⁺.

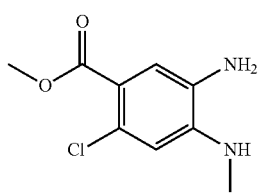

methyl 3-amino-5-methoxy-4-((2-methoxyethyl)amino)benzoate (I-140p)

Prepared following a similar procedure to I-140a using I-7k. ES/MS: m/z 255.0 [M+H]⁺.

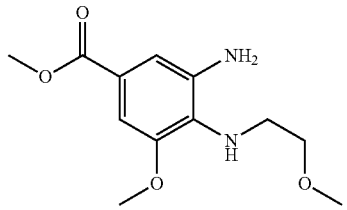

methyl 3-amino-5-methoxy-4-(methylamino)benzoate (I-140q)

Prepared following a similar procedure to I-140a using I-7a. ES/MS: m/z 211.04 [M+H]⁺.

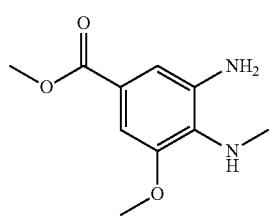

methyl 3-amino-4-(cyclopropylamino)-5-methoxybenzoate (I-140r)

Prepared following a similar procedure to I-140a using I-7b. ES/MS: m/z 237.2 [M+H]⁺.

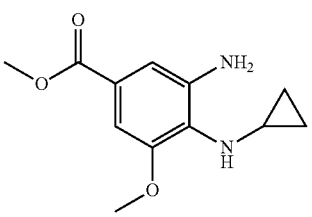

methyl 5-amino-2-fluoro-4-(((1S,2R)-2-fluorocyclopropyl)amino)benzoate (I-140s)

Prepared following a similar procedure to I-140a using methyl 2,4-difluoro-5-nitrobenzoate and (1S,2R)-2-fluorocyclopropanamine. ES/MS: m/z 243.1 [M+H]⁺.

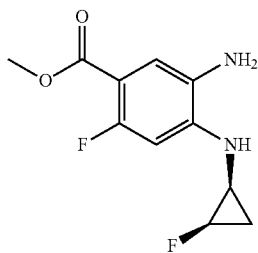

methyl 3-amino-5-fluoro-4-[[(1S,2S)-2-fluorocyclopropyl]amino]benzoate (I-140t)

Prepared following a similar procedure to I-140a using methyl 3,4-difluoro-5-nitro-benzoate and (1S,2S)-2-fluorocyclopropanamine. ES/MS: m/z 243.0 [M+H]$^+$.

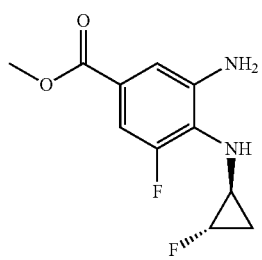

methyl 3-amino-5-fluoro-4-[[(1R,2R)-2-fluorocyclopropyl]amino]benzoate (I-140u)

Prepared following a similar procedure to I-140a using methyl 3,4-difluoro-5-nitro-benzoate and (1R,2R)-2-fluorocyclopropanamine. ES/MS: m/z 243.0 [M+H]$^+$.

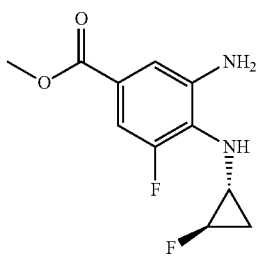

methyl 3-amino-5-fluoro-4-(((1S,2R)-2-fluorocyclopropyl)amino)benzoate (I-140v)

Prepared following a similar procedure to I-140a using methyl 3,4-difluoro-5-nitro-benzoate and (1S,2R)-2-fluorocyclopropanamine. ES/MS: m/z 243.0 [M+H]$^+$.

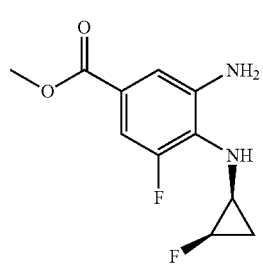

methyl 3-amino-4-(cyclopropylamino)-2-fluorobenzoate (I-140w)

Prepared following a similar procedure to I-140a using methyl 2,4-difluoro-3-nitrobenzoate. ES/MS: m/z 225.0 [M+H]$^+$.

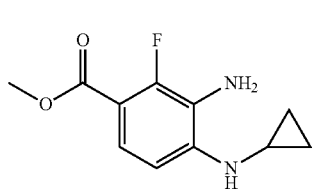

methyl 3-amino-4-(((1S,2R)-2-(difluoromethyl)cyclopropyl)amino)-5-fluorobenzoate (I-140x)

Prepared following a similar procedure to I-140c using cis-2-(difluoromethyl)cyclopropane-1-amine. ES/MS: m/z 274.98 [M+H]$^+$.

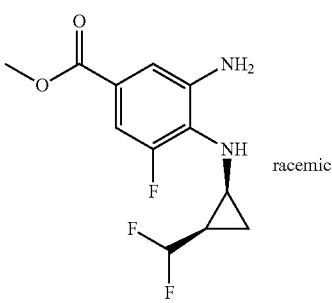

methyl 3-amino-4-(cyclopropylamino)-5-(difluoromethoxy)benzoate (I-140y)

Prepared following a similar procedure to I-140a using I-27b. ES/MS: m/z 273.9 [M+H]$^+$.

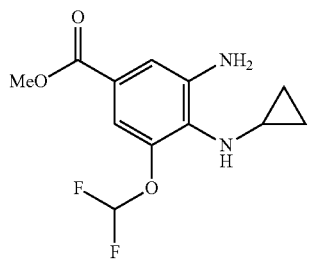

I-140y methyl 3-amino-5-(difluoromethoxy)-4-(methyl-amino)benzoate (I-140z)

Prepared following a similar procedure to I-140a using I-27a. ES/MS: m/z 246.9 [M+H]$^+$.

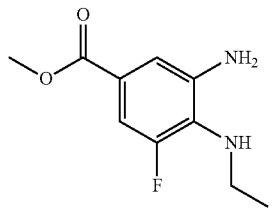

I-140dd methyl 3-amino-4-((2,2-difluoroethyl)amino)-5-fluorobenzoate (I-140ee)

Prepared following a similar procedure to I-140a using methyl 2,4-difluoro-5-nitrobenzoate and 2,2-difluoroethane-1-amine. ES/MS: m/z 250.0 [M+H]$^+$.

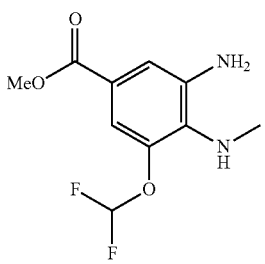

I-140z methyl 5-amino-3,4-dihydro-2H-benzo[b][1,4]oxazine-7-carboxylate (I-140aa)

Prepared following a similar procedure to I-140a using I-32. ES/MS: m/z 209.1 [M+H]$^+$.

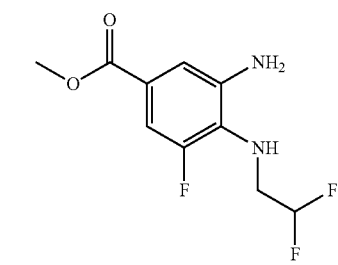

I-140ee methyl 3-amino-4-((cyclopropylmethyl)amino)-5-fluorobenzoate (I-140ff)

Prepared following a similar procedure to I-140a using methyl 2,4-difluoro-5-nitrobenzoate and cyclopropylmethanamine. ES/MS: m/z 239.9 [M+H]$^+$.

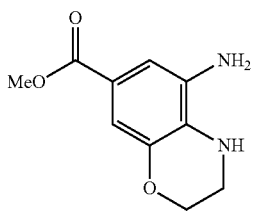

I-140aa methyl 3-amino-4-(ethylamino)-5-fluorobenzoate (I-140dd)

Prepared following a similar procedure to I-140a using methyl 3,4-difluoro-5-nitro-benzoate and ethylamine. ES/MS: m/z 213.98 [M+H]$^+$.

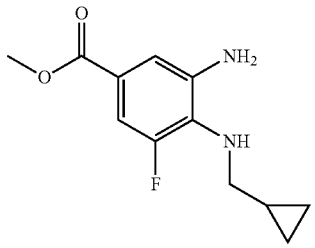

I-140ff methyl 3-amino-4-(cyclopropylamino)benzoate (I-140gg)

Prepared following a similar procedure to I-140a using methyl 4-fluoro-3-nitrobenzoate and cyclopropylamine. ES/MS: m/z 208.0 [M+H]$^+$.

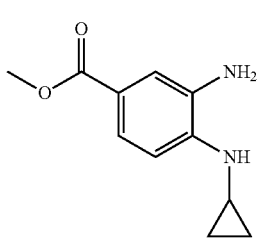

I-140gg

Preparation of methyl (R)-2-(6-(1-((tert-butoxycarbonyl)amino)ethyl)-1H-pyrrolo[2,3-b]pyridin-2-yl)-1-cyclopropyl-6,7-difluoro-1H-benzo[d]imidazole-5-carboxylate (I-141a)

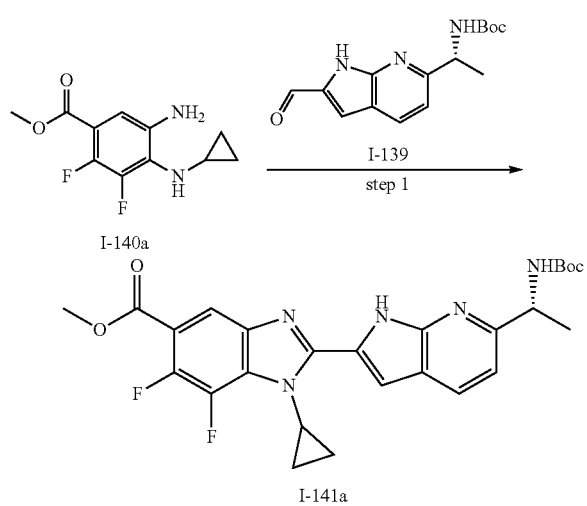

Step 1

Methyl 5-amino-4-(cyclopropylamino)-2,3-difluorobenzoate (190 mg, 0.78 mmol) and tert-butyl (R)-(1-(2-formyl-1H-pyrrolo[2,3-b]pyridin-6-yl)ethyl)carbamate (227 mg, 0.78 mmol) were charged in a vial equipped with a stir bar and acetic acid was added (5 mL). The resulting mixture was stirred at 50° C. for 12 h. The acetic acid was removed under vacuo and the residue was purified by flash chromatography over silica gel (10-100% EtOAc in DCM) to afford methyl (R)-2-(6-(1-((tert-butoxycarbonyl)amino)ethyl)-1H-pyrrolo[2,3-b]pyridin-2-yl)-1-cyclopropyl-6,7-difluoro-1H-benzo[d]imidazole-5-carboxylate. ES/MS: 511.9 (M+H)+. $^1$H NMR (400 MHz, DMSO-d6) δ 12.41 (brs, 1H), 8.08 (d, J=8.2 Hz, 1H), 7.98-7.95 (m, 1H), 7.38 (d, J=7.9 Hz, 1H), 7.34 (d, J=2.1 Hz, 1H), 7.19 (d, J=8.2 Hz, 1H), 4.85-4.66 (m, 1H), 4.06-4.00 (m, 1H), 3.91 (s, 3H), 1.42 (s, 3H), 1.40 (s, 9H), 1.31-1.25 (m, 2H), 1.04-0.96 (m, 2H).

methyl (R)-2-(6-(1-((tert-butoxycarbonyl)amino)ethyl)-1H-pyrrolo[2,3-b]pyridin-2-yl)-1-cyclopropyl-6-fluoro-1H-benzo[d]imidazole-5-carboxylate (I-141b)

Prepared following a similar procedure to I-141a using I-140b instead of I-140a. ES/MS: m/z 461.9 [M+H]+.

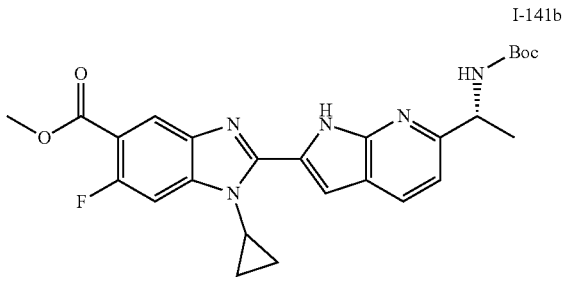 [SMILES: COC(=O)c1cc2nc(-c3cc4ccc([C@@H](C)NC(=O)OC(C)(C)C)nc4[nH]3)n(C3CC3)c2cc1F]

methyl (R)-2-(6-(1-((tert-butoxycarbonyl)amino)ethyl)-1H-pyrrolo[2,3-b]pyridin-2-yl)-1-cyclopropyl-7-fluoro-1H-benzo[d]imidazole-5-carboxylate (I-141c)

Prepared following a similar procedure to I-141a using methyl 3-amino-4-(cyclopropylamino)-5-fluorobenzoate (I-140c) and I-139. ES/MS: m/z 493.94 [M+H]+.

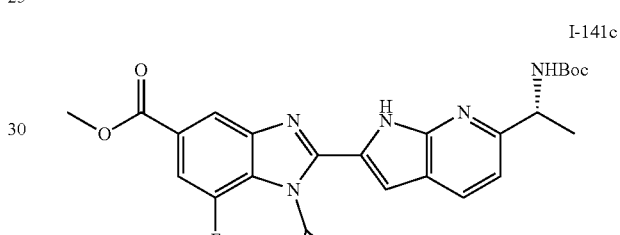

methyl (R)-2-(6-(1-((tert-butoxycarbonyl)amino)ethyl)-1H-pyrrolo[2,3-b]pyridin-2-yl)-7-fluoro-1-methyl-1H-benzo[d]imidazole-5-carboxylate (I-141d)

Prepared following a similar procedure to I-141a using I-140j and I-139. ES/MS: m/z 467.96 [M+H]+.

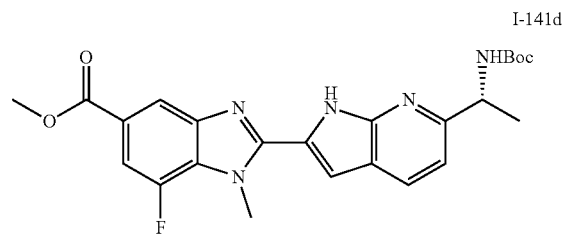

methyl (R)-2-(6-(1-((tert-butoxycarbonyl)amino)ethyl)-1H-pyrrolo[2,3-b]pyridin-2-yl)-7-chloro-1-cyclopropyl-1H-benzo[d]imidazole-5-carboxylate (I-141e)

Prepared following a similar procedure to I-141a using I-140k and I-139. ES/MS: m/z 509.84 [M+H]+.

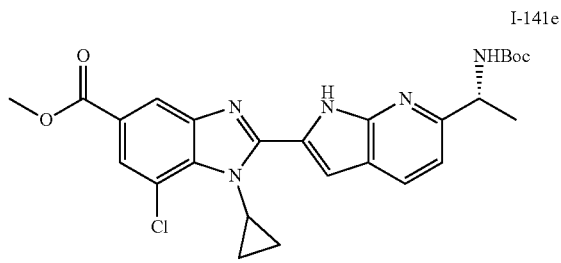 [SMILES: COC(=O)c1cc(F)c2c(c1)nc(-c1cc3ccc([C@@H](C)NC(=O)OC(C)(C)C)nc3[nH]1)n2C1CC1]

I-141e methyl (R)-2-(6-(1-((tert-butoxycarbonyl)amino)
ethyl)-1H-indol-2-yl)-1-cyclopropyl-7-fluoro-1H-
benzo[d]imidazole-5-carboxylate (I-141f)

Prepared following a similar procedure to I-141a using methyl 3-amino-4-(cyclopropylamino)-5-fluorobenzoate (I-140c) and I-148a. ES/MS: m/z 493.03 [M+H]⁺. ¹H NMR (400 MHz, DMSO-d6) δ 11.98 (s, 1H), 8.07 (d, J=2.8 Hz, 1H), 7.66-7.60 (m, 2H), 7.50-7.35 (m, 3H), 7.07 (d, J=8.6 Hz, 1H), 4.83-4.66 (m, 1H), 3.33 (s, 3H), 3.07-2.95 (m, 1H), 1.43-1.34 (m, 12H), 1.29-0.99 (in, 4H).

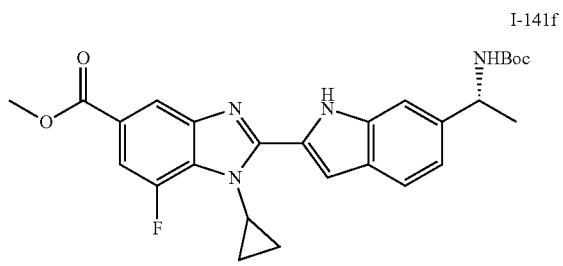

I-141f methyl (R)-2-(6-(1-((tert-butoxycarbonyl)amino)
ethyl)-1H-indol-2-yl)-cyclopropyl-7-methoxy-1-
methyl-1H-benzo[d]imidazole-5-carboxylate
(I-141f)

Prepared following a similar procedure to I-141a using I-23i and I-148a. ES/MS: m/z 479.0 [M+H]⁺.

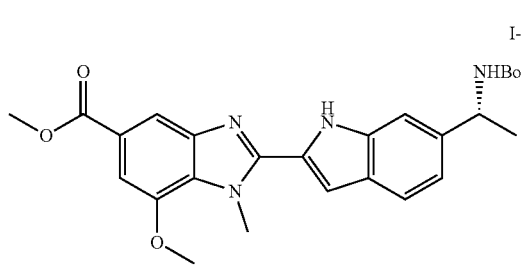

I-141g methyl (R)-2-(6-(1-((tert-butoxycarbonyl)amino)
ethyl)-1H-pyrrolo[2,3-b]pyridin-2-yl)-6-chloro-1-
methyl-1H-benzo[d]imidazole-5-carboxylate
(I-141h)

Prepared following a similar procedure to I-141a using I-140o. ES/MS: m/z 484.3 [M+H]⁺.

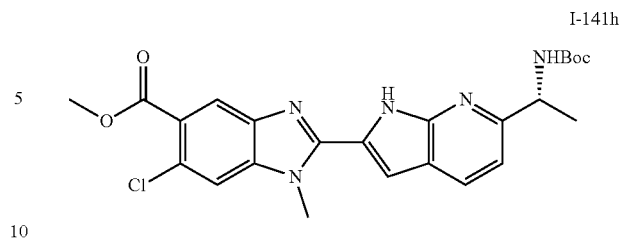

I-141h methyl (R)-2-(6-(1-((tert-butoxycarbonyl)amino)
ethyl)-1H-pyrrolo[2,3-b]pyridin-2-yl)-1-cyclopro-
pyl-7-methoxy-1H-benzo[d]imidazole-5-carboxylate
(I-141i)

Prepared following a similar procedure to I-141a using I-140r. ES/MS: m/z 506.3 [M+H]⁺.

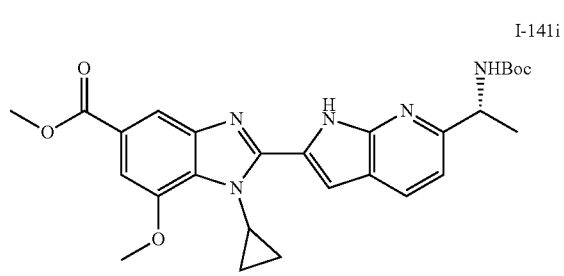 [SMILES: COC(=O)c1cc(Cl)c2c(c1)nc(-c1cc3ccc([C@@H](C)NC(=O)OC(C)(C)C)nc3[nH]1)n2C1CC1]

I-141i methyl 2-(6-((R)-1-((tert-butoxycarbonyl)amino)
ethyl)-1H-pyrrolo[2,3-b]pyridin-2-yl)-7-fluoro-1-
((1R,2R)-2-fluorocyclopropyl)-1H-benzo[d]imida-
zole-5-carboxylate (I-141j)

Prepared following a similar procedure to I-141a using I-140u. ES/MS: m/z 512.77 [M+H]⁺. ¹H NMR (400 MHz, DMSO-d6) δ 12.45 (s, 1H), 8.16-8.08 (m, 3H), 7.69 (d, J=11.9 Hz, 1H), 7.39 (d, J=7.9 Hz, 1H), 7.34 (d, J=2.0 Hz, 1H), 7.20 (d, J=8.2 Hz, 1H), 5.28-4.98 (m, 1H), 4.87 (t, J=7.4 Hz, 1H), 4.63-4.54 (m, 1H), 3.91 (s, 3H), 2.06-1.91 (m, 1H), 1.42 (brs, 3H), 1.39 (s, 9H).

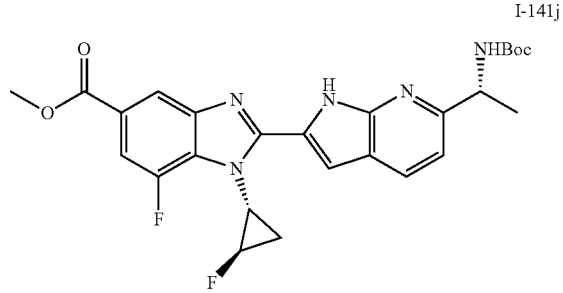 [SMILES: COC(=O)c1cc(F)c2c(c1)nc(-c1cc3ccc([C@@H](C)NC(=O)OC(C)(C)C)nc3[nH]1)n2[C@@H]1C[C@H]1F]

I-141j methyl 2-(6-(2-((tert-butoxycarbonyl)amino)propan-
2-yl)-1H-pyrrolo[2,3-b]pyridin-2-yl)-7-methoxy-1-
methyl-1H-benzo[d]imidazole-5-carboxylate
(I-141k)

Prepared following a similar procedure to I-141a using tert-butyl (2-(2-formyl-1H-pyrrolo[2,3-b]pyridin-6-yl)pro-pan-2-yl)carbamate (I-34) and I-140q. ES/MS: m/z 494.3 [M+H]⁺.

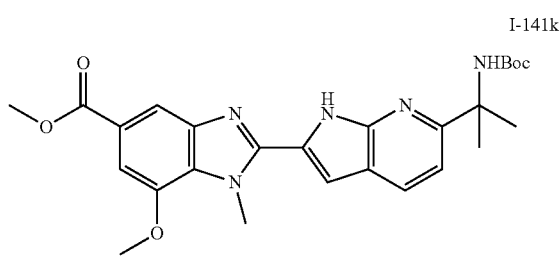 [SMILES: COC(=O)c1cc(OC)c2c(c1)nc(-c1cc3ccc(C(C)(C)NC(=O)OC(C)(C)C)nc3[nH]1)n2C]

I-141k

Preparation of (2R,5R,7R,9E)-2-methyl-4-oxo-3,13, 19-triazatetracyclo[11.5.2.0⁵,⁷.0¹⁶,²⁰]icosa-1(19),9, 14,16(20),17-pentaene-14-carbaldehyde (I-142a)

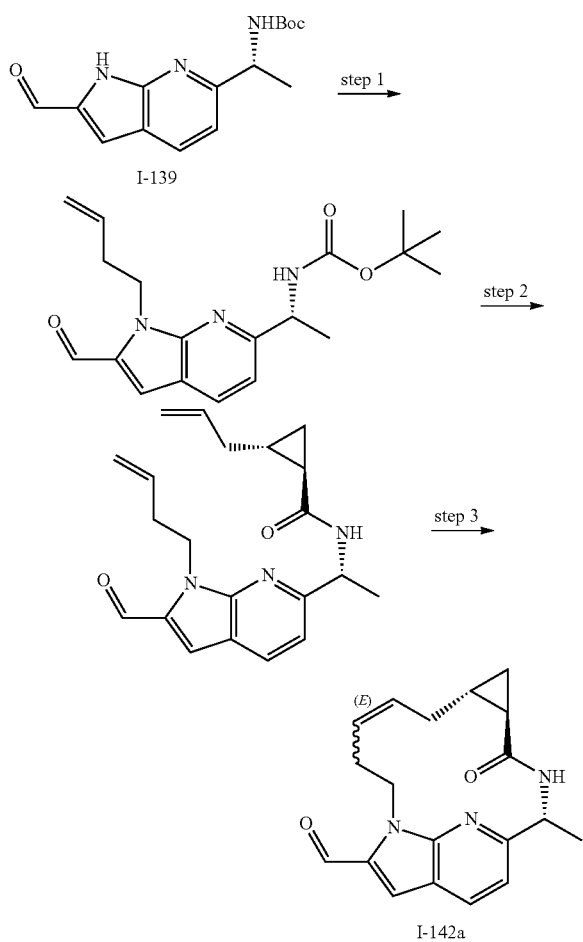

I-142a

Step 1

A mixture of tert-butyl N-[(1R)-1-(2-formyl-1H-pyrrolo[2,3-b]pyridin-6-yl)ethyl]carbamate (3 g, 10.4 mmol), 4-bromobut-1-ene (1.5 mL, 14.5 mmol), and cesium carbonate (10.1 g, 31.1 mmol) in N,N-dimethylformamide (55.0 mL) was heated at 60° C. for 45 minutes. The reaction was cooled to room temperature. The mixture was quenched with saturated ammonium chloride solution and diluted with brine and 5% lithium chloride solution. The aqueous layer was extracted with EtOAc and the combined organic layers were dried over magnesium sulfate. Filtration and evaporation of solvents yielded the crude product, which was purified by silica gel chromatography (0 to 20% EtOAc/hexanes) to afford tert-butyl (R)-(1-(1-(but-3-en-1-yl)-2-formyl-1H-pyrrolo[2,3-b]pyridin-6-yl)ethyl)carbamate. ES/MS: m/z 343.8 [M+H]⁺.

Step 2

A mixture of tert-butyl N-[(1R)-1-(1-but-3-enyl-2-formyl-pyrrolo[2,3-b]pyridin-6-yl)ethyl]carbamate (3.3 g, 9.6 mmol), and trifluoroacetic acid (4.0 mL, 331 mmol) in dichloromethane (50 mL) was stirred at room temperature for 4 h. The solvents were evaporated and the crude intermediate was dissolved in N,N-dimethylformamide (50 mL). N,N-Diisopropylethylamine (8.4 mL, 48.1 mmol) and (1R, 2R)-2-allylcyclopropanecarboxylic acid (L48) (1.3 g, 10.6 mmol) pre-mixed with HATU (4.0 g 10.6 mmol) were added. The reaction mixture was stirred at room temperature for 1 h. Saturated ammonium chloride and dichloromethane were added. The aqueous layer was extracted with dichloromethane and the combined organic layers were dried over magnesium sulfate. Filtration and evaporation of solvents yielded the crude product, which was purified by silica gel chromatography (eluent: 0 to 50% EtOAc/hexanes) to afford (1R,2R)-2-allyl-N—((R)-1-(1-(but-3-en-1-yl)-2-formyl-1H-pyrrolo[2,3-b]pyridin-6-yl)ethyl)cyclopropane-1-carboxamide. ES/MS: m/z 352.1 [M+H]⁺.

Step 3

(1R,2R)-2-allyl-N-[(1R)-1-(1-but-3-enyl-2-formyl-pyrrolo[2,3-b]pyridin-6-yl)ethyl]cyclopropanecarboxamide (2.4 g, 6.8 mmol) was dissolved in 1,2-Dichloroethane (327 mL). To the mixture, added Zhan 1b catalyst (512 mg, 0.7 mmol) and purged vessel with Argon. The resulting mixture was heated at 80° C. for 3 hours. The solvents were evaporated to yield the crude material, which was purified by silica gel chromatography (eluent: 0 to 50% EtOAc/dichloromethane) to afford (2R,5R,7R,9E)-2-methyl-4-oxo-3,13,19-triazatetracyclo[11.5.2.0⁵,⁷.0¹⁶,²⁰]icosa-1(19),9, 14,16(20),17-pentaene-14-carbaldehyde. ES/MS: 324.2 (M+H)+. ¹H NMR (400 MHz, DMSO-d6) δ 9.92 (s, 1H), 8.55 (d, J=8.0 Hz, 1H), 8.13 (d, J=8.1 Hz, 1H), 7.49 (s, 1H), 7.21 (d, J=8.2 Hz, 1H), 5.69-5.50 (m, 2H), 4.97 (p, J=7.2 Hz, 1H), 4.71-4.60 (m, 2H), 2.71-2.57 (m, 1H), 2.44 (d, J=18.9 Hz, 2H), 1.47 (m, J=7.9, 4.5 Hz, 1H), 1.40 (d, J=7.1 Hz, 3H), 1.37-1.27 (m, 1H), 0.91-0.76 (m, 2H), 0.58 (m, J=8.2, 5.6, 3.2 Hz, 1H).

(5E,11R)-8,8,11-trimethyl-9-oxo-1,10,19-triazatricyclo[10.5.2.0¹⁵,¹⁸]nonadeca-5,12(19),13,15(18),16-pentaene-17-carbaldehyde (I-142b)

Prepared following a similar procedure to I-142a using 5-bromopent-1-ene and 2,2-dimethyl-4-pentenoic acid. ES/MS: m/z 340.3 [M+H]⁺.

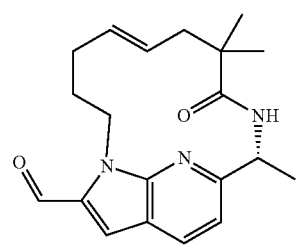

I-142b

281

(2R,5R,7R,9Z)-11,11-difluoro-2-methyl-4-oxo-3,13,19-triazatetracyclo[11.5.2.0⁵,⁷.0¹⁶,²⁰]icosa-1(19),9,14,16(20),17-pentaene-14-carbaldehyde (I-142c)

Prepared following a similar procedure to I-142a using 2,2-difluorobut-3-en-1-yl trifluoromethanesulfonate and (1R,2R)-2-allylcyclopropane-1-carboxylic acid. ES/MS: m/z 359.96 [M+H]⁺.

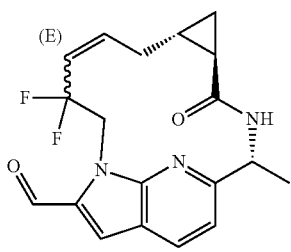

I-142c (2R,5S,7R,8E)-7-fluoro-2-methyl-4-oxo-3,13,19-triazatetracyclo[11.5.2.0⁵,⁷.0¹⁶,²⁰]icosa-1(19),8,14,16(20),17-pentaene-14-carbaldehyde (I-142d)

Prepared following a similar procedure to I-142a using 5-bromopent-1-ene and L55a. ES/MS: m/z 342.3 [M+H]⁺.

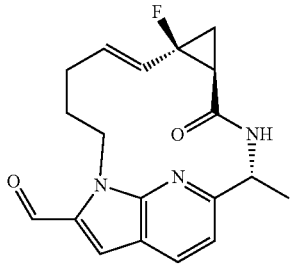

I-142d

Preparation of methyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate (I-143a)

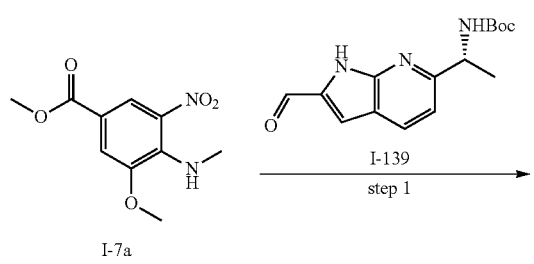

282

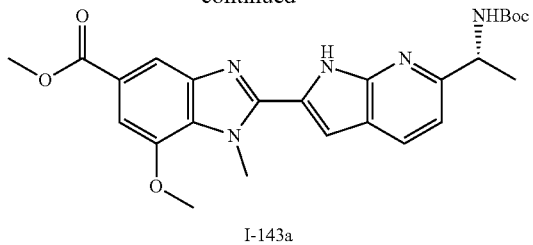

I-143a

Step 1

Methyl 3-methoxy-4-(methylamino)-5-nitrobenzoate (I-7a, 10 g, 41.6 mmol) and tert-butyl (R)-(1-(2-formyl-1H-pyrrolo[2,3-b]pyridin-6-yl)ethyl)carbamate (I-139, 12.2 g, 42.0 mmol) were charged in a flask equipped with a stir bar. The mixture was suspended in EtOH/water (2:1, 300 mL) and sodium dithionite (25.6 g, 125 mmol) was added. The vial was sealed, and the reaction was heated to 80° C. for 3 h. Upon cooling, the precipitate was filtered off, washed with water and dried under vacuum to afford methyl (R)-2-(6-(1-((tert-butoxycarbonyl)amino)ethyl)-1H-pyrrolo[2,3-b]pyridin-2-yl)-7-methoxy-1-methyl-1H-benzo[d]imidazole-5-carboxylate. ES/MS: m/z 480.2 [M+H]⁺.

methyl (R)-2-(6-(1-((tert-butoxycarbonyl)amino)ethyl)-1H-pyrrolo[2,3-b]pyridin-2-yl)-6-fluoro-1-methyl-1H-benzo[d]imidazole-5-carboxylate (I-143b)

Prepared following a similar procedure to I-143a using I-7c instead of I-7a. ES/MS: m/z 468.3 [M+H]⁺.

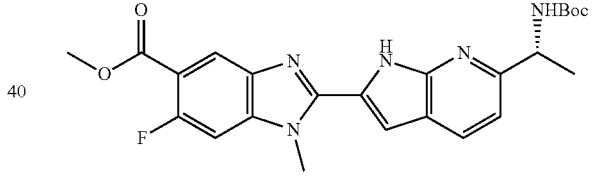

I-143b methyl (R)-2-(6-(1-((tert-butoxycarbonyl)amino)ethyl)-1H-pyrrolo[2,3-b]pyridin-2-yl)-1-(2,2-difluoroethyl)-6-fluoro-1H-benzo[d]imidazole-5-carboxylate (I-143c)

Prepared following a similar procedure to I-143a using I-7i instead of I-7a. ES/MS: m/z 517.9 [M+H]⁺.

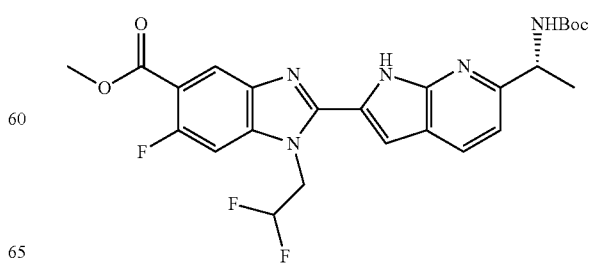

I-143c methyl (R)-2-(6-(1-((tert-butoxycarbonyl)amino)ethyl)-1H-pyrrolo[2,3-b]pyridin-2-yl)-6-fluoro-1-(2,2,2-trifluoroethyl)-1H-benzo[d]imidazole-5-carboxylate (I-143d)

Prepared following a similar procedure to I-143a using I-7j instead of I-7a. ES/MS: m/z 536.3 [M+H]⁺.

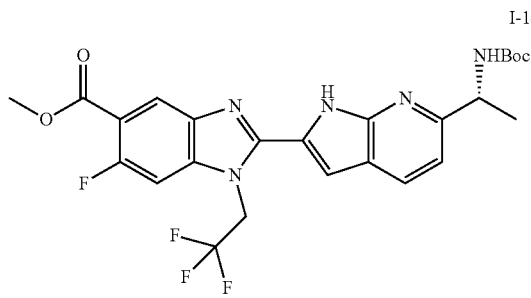

methyl (R)-2-(6-(1-((tert-butoxycarbonyl)amino)ethyl)-1H-pyrrolo[2,3-b]pyridin-2-yl)-6-fluoro-1-(2-methoxyethyl)-1H-benzo[d]imidazole-5-carboxylate (I-143e)

Prepared following a similar procedure to I-143a using I-7h instead of I-7a. ES/MS: m/z 512.3 [M+H]⁺.

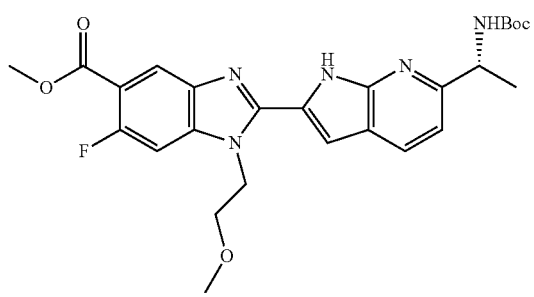

methyl (R)-2-(6-(1-((tert-butoxycarbonyl)amino)ethyl)-1H-pyrrolo[2,3-b]pyridin-2-yl)-6-methoxy-1-methyl-1H-benzo[d]imidazole-5-carboxylate (I-143f)

Prepared following a similar procedure to I-143a using I-7m. ES/MS: m/z 480.0 [M–H]⁺.

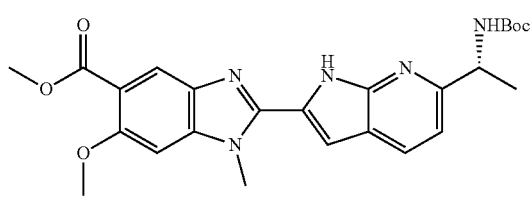

methyl (R)-2-(6-(1-((tert-butoxycarbonyl)amino)ethyl)-1H-pyrrolo[2,3-b]pyridin-2-yl)-6-methoxy-1-methyl-1H-benzo[d]imidazole-5-carboxylate (I-143g)

Prepared following a similar procedure to I-143a using I-26. ES/MS: m/z 480.0 [M–H]⁺.

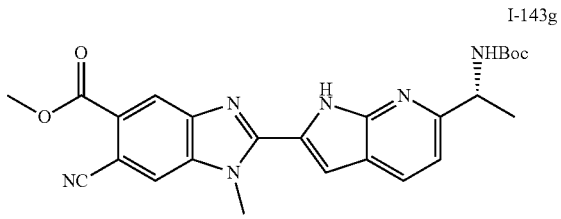 [SMILES: COC(=O)c1cc2nc(-c3cc4ccc([C@@H](C)NC(=O)OC(C)(C)C)nc4[nH]3)n(C)c2cc1C#N]

methyl (R)-2-(6-(1-((tert-butoxycarbonyl)amino)ethyl)-1H-pyrrolo[2,3-b]pyridin-2-yl)-1,6-dimethyl-1H-benzo[d]imidazole-5-carboxylate (I-143h)

Prepared following a similar procedure to I-143a using I-7n. ES/MS: m/z 464.3 [M–H]⁺.

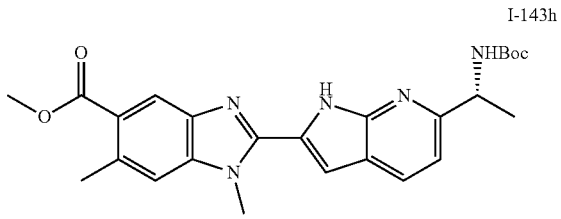 [SMILES: COC(=O)c1cc2nc(-c3cc4ccc([C@@H](C)NC(=O)OC(C)(C)C)nc4[nH]3)n(C)c2cc1C]

methyl (R)-2-(6-(1-((tert-butoxycarbonyl)amino)ethyl)-1H-pyrrolo[2,3-b]pyridin-2-yl)-6,7-difluoro-1-methyl-1H-benzo[d]imidazole-5-carboxylate (I-143i)

Prepared following a similar procedure to I-143a using I-7o. ES/MS: m/z 484.9 [M–H]⁺.

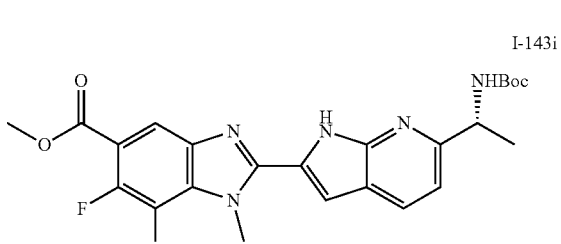

methyl (R)-2-(6-(1-((tert-butoxycarbonyl)amino)ethyl)-1H-pyrrolo[2,3-b]pyridin-2-yl)-7-fluoro-1-methyl-1H-benzo[d]imidazole-5-carboxylate (I-143j)

Prepared following a similar procedure to I-143a using I-7s. ES/MS: m/z 468.3 [M–H]⁺.

I-143j

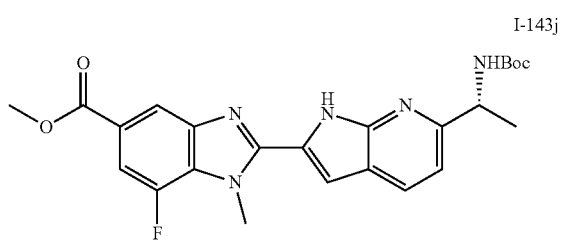 [SMILES: COC(=O)c1cc(F)c2c(c1)nc(-c1cc3ccc([C@@H](C)NC(=O)OC(C)(C)C)nc3[nH]1)n2C]

Preparation of benzyl (3S,4S)-3-[[2-[6-[(1R)-1-aminoethyl]-1-pent-4-enyl-pyrrolo[2,3-b]pyridin-2-yl]-7-methoxy-1-methyl-benzimidazole-5-carbonyl]amino]-4-fluoro-piperidine-1-carboxylate (I-144a)

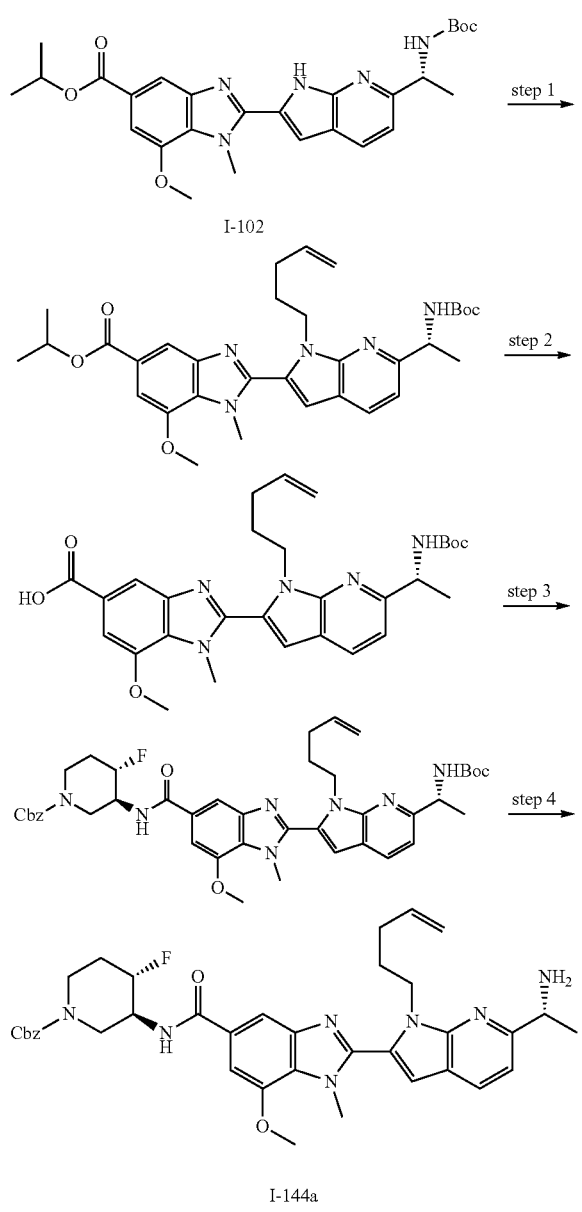

Step 1

Isopropyl 2-[6-[(1R)-1-(tert-butoxycarbonylamino)ethyl]-1H-pyrrolo[2,3-b]pyridin-2-yl]-7-methoxy-1-methyl-benzimidazole-5-carboxylate (I-102) (500 mg, 0.99 mmol), 5-bromopent-1-ene (0.24 mL, 1.97 mmol) and cesium carbonate (965 mg, 2.96 mmol) were dissolved in N,N-dimethylformamide (8 mL) and the resulting reaction mixture was stirred at 60° C. for 90 min. The cooled reaction mixture was quenched with saturated ammonium chloride solution, diluted with copious amounts of water, and extracted with dichloromethane three times. The collected organics were dried over magnesium sulfate and concentrated to produce the crude product, which was purified via silica gel column chromatography (0-65% ethyl acetate in hexanes) to yield isopropyl 2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carboxylate. ES/MS: m/z 576.25 [M+H]$^+$.

Step 2

2 N lithium hydroxide solution (0.4 mL, 0.80 mmol) was added to a solution of isopropyl 2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carboxylate (110 mg, 0.19 mmol) in methanol (1 mL) and tetrahydrofuran (1 mL). The resulting reaction mixture was heated at 60° C. for 6 h. The reaction mixture was concentrated and re-dissolved in dichloromethane, diluted with water and quenched with 1 N hydrochloride solution (0.8 mL), extracting with dichloromethane (3×). The organics were collected, dried over magnesium sulfate and concentrated to yield 2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carboxylic acid, which was carried over to the consequent step without further purification assuming quantitative yield. ES/MS: m/z 534.13 [M+H]$^+$.

Step 3

N,N-diisopropylethylamine (0.12 mL, 0.71 mmol) was added to a solution of 2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carboxylic acid (102 mg, 0.18 mmol) dissolved in dichloromethane (2 mL), followed by addition of [dimethylamino(triazolo[4,5-b]pyridin-3yloxy)methylene]-dimethyl-ammonium (101 mg, 0.27 mmol) and benzyl (3S,4S)-3-amino-4-fluoro-piperidine-1-carboxylate (A1.39) (49 mg, 0.20 mmol). The resulting reaction mixture was stirred at room temperature for 16 h. The reaction mixture was quenched with saturated ammonium chloride solution and extracted with dichloromethane twice. The collected organics were dried over magnesium sulfate and concentrated to produce the crude product, which was purified via silica gel column chromatography to yield benzyl (3S,4S)-3-[[2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carbonyl]amino]-4-fluoro-piperidine-1-carboxylate. ES/MS: m/z 768.22 [M+H]$^+$.

Step 4

Trifluoroacetic acid (0.3 mL, 3.92 mmol) was added to a solution of benzyl (3S,4S)-3-[[2-[6-[(1R)-1-(tert-butoxycarbonylamino)ethyl]-1-pent-4-enyl-pyrrolo[2,3-b]pyridin-2-yl]-7-methoxy-1-methyl-benzimidazole-5-carbonyl]amino]-4-fluoro-piperidine-1-carboxylate (121 mg, 0.16 mmol) dissolved in dichloromethane (2 mL). The resulting reaction mixture was stirred at room temperature for 1 h. The reaction mixture was concentrated to yield benzyl (3S,4S)-3-[[2-[6-[(1R)-1-aminoethyl]-1-pent-4-enyl-pyrrolo[2,3-b]pyridin-2-yl]-7-methoxy-1-methyl-benzimidazole-5-carbonyl]amino]-4-fluoro-piperidine-1-carboxylate, which was carried over to the consequent step without further purification assuming quantitative yield. ES/MS: m/z 668.50 [M+H]+.

benzyl (3S,4S)-3-[[2-[6-[(1R)-1-aminoethyl]-1-pent-4-enyl-pyrrolo[2,3-b]pyridin-2-yl]-6-fluoro-1-methyl-benzimidazole-5-carbonyl]amino]-4-fluoro-piperidine-1-carboxylate (I-144b)

Prepared using a similar procedure to I-144a using I-143b as starting material. ES/MS: m/z 656.28 [M+H]+.

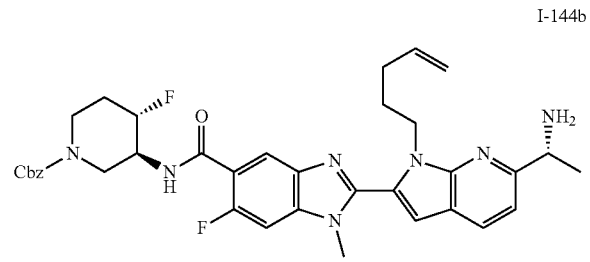 [SMILES: C=CCCCn1c(-c2nc3cc(C(=O)N[C@H]4CN(C(=O)OCc5ccccc5)CC[C@@H]4F)c(F)cc3n2C)cc2ccc([C@@H](C)N)nc21]

I-144b

Preparation of (11R)-8,8,11-trimethyl-9-oxo-1,10,19-triazatricyclo[10.5.2.015,18]nonadeca-12(19),13,15(18),16-tetraene-17-carbaldehyde (I-145a)

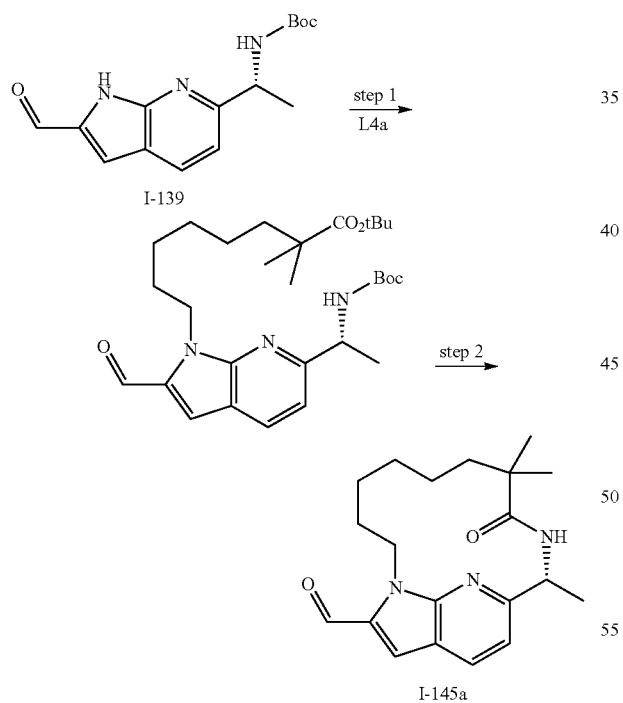

I-145a

Step 1
tert-butyl N-[(1R)-1-(2-formyl-1H-pyrrolo[2,3-b]pyridin-6-yl)ethyl]carbamate (I-139, 900 mg, 3.11 mmol) and tert-butyl 8-bromo-2,2-dimethyloctanoate (L4a, 1.22g, 4.04 mmol) were dissolved in DMF (50.0 mL). Cesium carbonate (3.07g, 9.42 mmol) was added and the resulting mixture was allowed to stir 1 h at 60° C. The reaction mixture was partitioned between EtOAc and water, and the organic phase was washed with brine, dried with MgSO4, filtered, and concentrated. Purification by silica gel chromatography (5-20% EtOAc in hexanes) provided tert-butyl 8-[6-[(1R)-1-(tert-butoxycarbonylamino)ethyl]-2-formyl-pyrrolo[2,3-b]pyridin-1-yl]-2,2-dimethyl-octanoate. ES/MS: m/z 516.3 [M+H]+.

Step 2
The product from above was dissolved in DCM (2 mL) and TFA (0.5 mL) was added. The reaction mixture was stirred 3 h at room temperature and was concentrated in vacuo to afford crude 8-[6-[(1R)-1-aminoethyl]-2-formyl-pyrrolo[2,3-b]pyridin-1-yl]-2,2-dimethyl-octanoic acid which was used below without further purification. The crude product (1.11 mmol) from above was dissolved in DCM (2.5 mL). N,N-diisopropylethylamine (0.97 mL, 5.56 mmol) was added followed by HATU (208 mg, 1.34 mmol). After 1 h, the reaction mixture was partitioned between EtOAc and water, and the organic phase was washed with brine, dried with MgSO4, filtered, and concentrated. Purification by silica gel chromatography (5-50% EtOAc in hexanes) provided (11R)-8,8,11-trimethyl-9-oxo-1,10,19-triazatricyclo[10.5.2.015,18]nonadeca-12(19),13,15(18),16-tetraene-17-carbaldehyde. ES/MS: m/z 342.1 [M+H]+.

(2R)-2-methyl-4-oxo-3,6,9,16,22-pentazatetracyclo[14.5.2.05,10.019,23]tricosa-1(22),5(10),6,8,17,19(23),20-heptaene-17-carbaldehyde (I-145b)

Prepared using a similar procedure to I-145a using L49. ES/MS: m/z 364.2 [M+H]+.

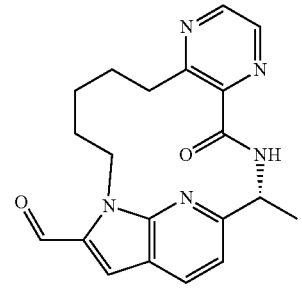

I-145b (2R)-8-chloro-2-methyl-4-oxo-3,9,16,22-tetrazatetracyclo[14.5.2.05,10.019,23]tricosa-1(22),5(10),6,8,17,19(23),20-heptaene-17-carbaldehyde (I-145c)

Prepared using a similar procedure to I-145a using L60a. ES/MS: m/z 397.16 [M+H]+.

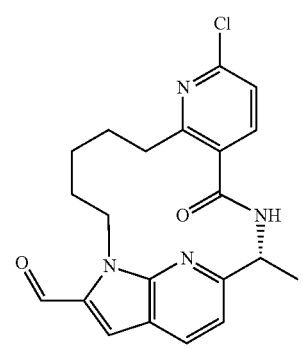

I-145c

289

Preparation of isopropyl (R)-2-(6-(1-((tert-butoxy-carbonyl)amino)ethyl)-7-fluoro-1H-indol-2-yl)-7-methoxy-1-methyl-1H-benzo[d]imidazole-5-carboxylate (I-146a)

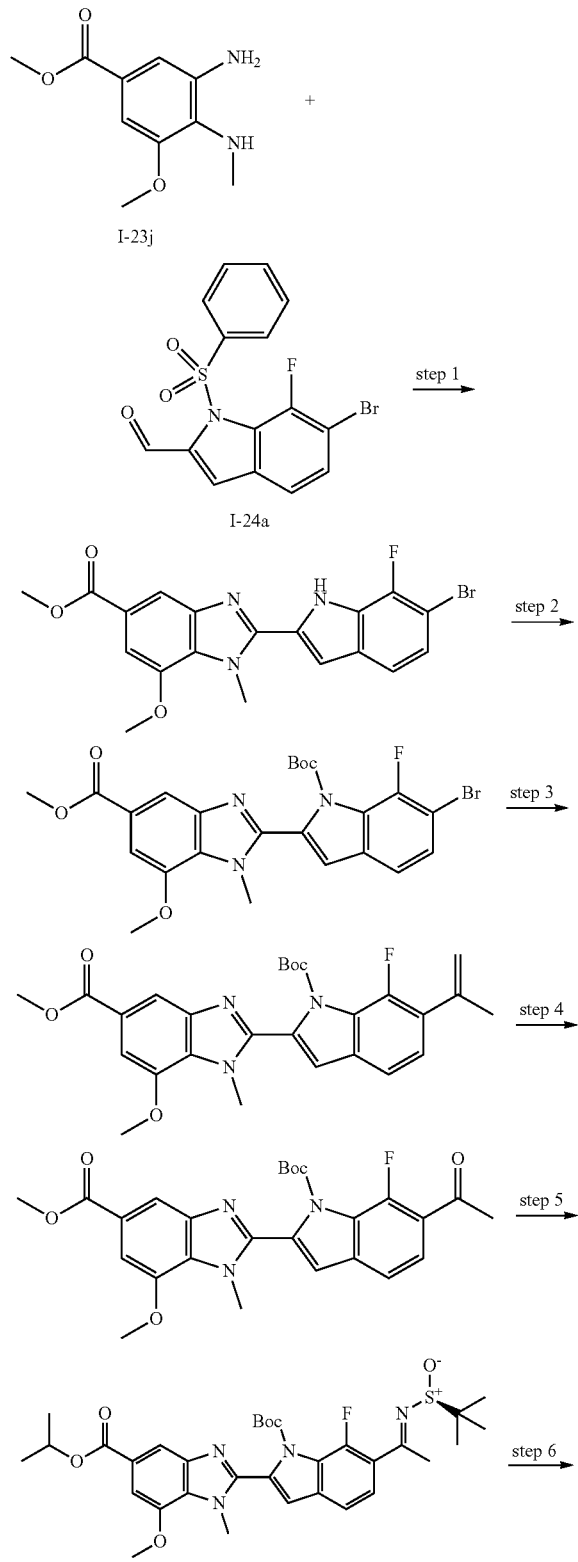

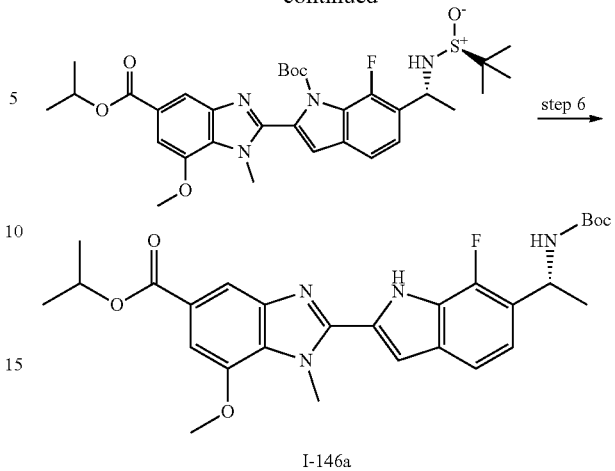

Step 1 methyl 3-amino-5-methoxy-4-(methylamino)benzoate (1.59 g, 7.56 mmol) and 1-(benzenesulfonyl)-6-bromo-7-fluoro-indole-2-carbaldehyde (2.5 g, 6.54 mmol) were taken up in HOAc (30 mL). The solution was heated to 70° C. and stirred for 18 h. The temperature was then increased to 90° C. and stirred for an additional 2 h. The mixture was concentrated, leading to precipitation of solids. Solids were collected by filtration, and the filtrate was concentrated and purified by silica gel chromatography. The solids were combined with the product purified by chromatography to afford methyl 2-(6-bromo-7-fluoro-1H-indol-2-yl)-7-methoxy-1-methyl-benzimidazole-5-carboxylate. ES/MS: m/z 432.0 [M+H]$^+$.

Step 2 methyl 2-(6-bromo-7-fluoro-1H-indol-2-yl)-7-methoxy-1-methyl-benzimidazole-5-carboxylate (2.15 g, 4.97 mmol) was dissolved in DCM (25 mL) and triethylamine (2.1 mL, 15 mmol) was added, followed by DMAP (122 mg, 1 mmol) and di-tert-butyl decarbonate (1.19 g, 5.47 mmol). The reaction mixture was stirred at r.t., and additional portions of triethylamine and di-tert-butyl decarbonate were added to effect full conversion. The mixture was then partitioned between DCM and water, and the organic phase was washed with water, dried over Na$_2$SO$_4$, filtered, and concentrated. Purification by silica gel provided methyl 2-(6-bromo-1-(tert-butoxycarbonyl)-7-fluoro-1H-indol-2-yl)-7-methoxy-1-methyl-1H-benzo[d]imidazole-5-carboxylate. ES/MS: m/z 531.9 [M+H]$^+$.

Step 3 methyl 2-(6-bromo-1-(tert-butoxycarbonyl)-7-fluoro-1H-indol-2-yl)-7-methoxy-1-methyl-1H-benzo[d]imidazole-5-carboxylate (1.65 g, 3.1 mmol) was taken up in EtOH (40 mL). Potassium isopropenyltrifluoroborate (690 mg, 4.7 mmol) was added, followed by Dichloro 1,1'-bis(diphenylphosphino)ferrocene palladium (II) dichloromethane (177 mg, 0.22 mmol) and triethylamine (2.16 mL, 0.016 mmol). The reaction vessel was flushed with N$_2$, and the mixture was heated to 80° C. Once complete, the reaction mixture was partitioned between EtOAc and water. The phases were separated, and the organic phase was dried over Na$_2$SO$_4$, filtered, and concentrated. The obtained residue was purified by silica gel chromatography to afford methyl 2-(1-tert-butoxycarbonyl-7-fluoro-6-isopropenyl-indol-2-yl)-7-methoxy-1-methyl-benzimidazole-5-carboxylate. ES/MS: m/z 493.82 [M+H]$^+$.

Step 4 methyl 2-(1-tert-butoxycarbonyl-7-fluoro-6-isopropenyl-indol-2-yl)-7-methoxy-1-methyl-benzimidazole-5-carboxylate (1.0 g, 2.0 mmol) was dissolved in THF (30 mL) and water (15 mL). Potassium osmate(VI) dihydrate (22 mg, 0.07 mmol) was added followed by sodium periodate (1.3 g, 6.1 mmol). The reaction mixture was stirred overnight, and was then partitioned between EtOAc and water. The phases were separated, and the organic phase was washed with brine, dried over Na$_2$SO$_4$, filtered and concentrated. Purification by silica gel provided methyl 2-(6-acetyl-1-tert-butoxycarbonyl-7-fluoro-indol-2-yl)-7-methoxy-1-methyl-benzimidazole-5-carboxylate. ES/MS: m/z 495.78 [M+H]$^+$.

Step 5 methyl 2-(6-acetyl-1-tert-butoxycarbonyl-7-fluoro-indol-2-yl)-7-methoxy-1-methyl-benzimidazole-5-carboxylate (740 mg, 1.5 mmol) and (S)-2-methylpropane-2-sulfinamide (740 mg, 6.1 mmol) were dissolved in THF (30 mL) under N$_2$. Ti(OiPr)$_4$ (3.54 mL, 12 mmol) was added, and the mixture was stirred at 60° C. for 22 h. The temperature was then increased to 75° C. and the reaction mixture was stirred an additional 24 h. The mixture was then poured into a vigorously stirred mixture of EtOAc and brine. The organic layer was decanted, and the aqueous mixture was extracted with EtOAc several times. Celite was added to the combined organic phase, which was then filtered and concentrated to provide a crude residue that was purified by silica gel chromatography (10-40% acetone in hexanes) to provide [(E)-1-[1-tert-butoxycarbonyl-7-fluoro-2-(5-isopropoxycarbonyl-7-methoxy-1-methyl-benzimidazol-2-yl)indol-6-yl]ethylideneamino]-tert-butyl-oxido-sulfonium. ES/MS: m/z 627.81 [M+H]$^+$.

Step 6

[(E)-1-[1-tert-butoxycarbonyl-7-fluoro-2-(5-isopropoxycarbonyl-7-methoxy-1-methyl-benzimidazol-2-yl)indol-6-yl]ethylideneamino]-tert-butyl-oxido-sulfonium (712 mg, 1.1 mmol) was dissolved in THF (15 mL) and the mixture was cooled in a dry ice/acetone bath to −78° C. A solution of L-selectride (1 M, 1.19 mL, 1.19 mmol) was added dropwise, and the mixture was stirred for 2 h. The mixture was removed from the cold bath, allowed to slowly warm to ca. 0° C., and was then placed in an ice water bath. After an additional 30 min, the reaction was quenched by addition of saturated aqueous NH$_4$Cl and diluted with EtOAc. The phases were separated, and the organic phase was dried over Na$_2$SO$_4$, filtered, and concentrated. Purification by silica gel provided [[(1R)-1-[1-tert-butoxycarbonyl-7-fluoro-2-(5-isopropoxycarbonyl-7-methoxy-1-methyl-benzimidazol-2-yl)indol-6-yl]ethyl]amino]-tert-butyl-oxido-sulfonium. ES/MS: m/z 628.80 [M+H]$^+$.

Step 7

[[(1R)-1-[1-tert-butoxycarbonyl-7-fluoro-2-(5-isopropoxycarbonyl-7-methoxy-1-methyl-benzimidazol-2-yl)indol-6-yl]ethyl]amino]-tert-butyl-oxido-sulfonium (600 mg, 0.95 mmol) was dissolved in 1,4-dioxane (10 mL). A solution of HCl in dioxane (4 M, 2.4 mL, 9.5 mmol) was added. DCM (10 mL) was added, followed by additional HCl in dioxane (4 M, 2.4 mL, 9.5 mmol) and the reaction mixture was heated to 40° C. After stirring 2 days, the mixture was cooled and diluted with Et$_2$O. Solids were collected by filtration and were then dissolved in DCM (20 mL). Triethylamine (1.2 mL, 0.89 mmol) was added followed by di-tert-butyl decarbonate (192 mg, 0.88 mmol). The mixture was stirred 30 min and was partitioned between DCM and water. The phases were separated, and the organic phase was concentrated to afford a residue that was purified by silica gel chromatography (20-70% EtOAc in hexanes) to afford isopropyl 2-[6-[(1R)-1-(tert-butoxycarbonylamino)ethyl]-7-fluoro-1H-indol-2-yl]-7-methoxy-1-methyl-benzimidazole-5-carboxylate. ES/MS: m/z 525.08 [M+H]$^+$.

Preparation of tert-butyl (R)-(1-(2-formyl-1-(phenylsulfonyl)-1H-indol-6-yl)ethyl)carbamate (I-147a)

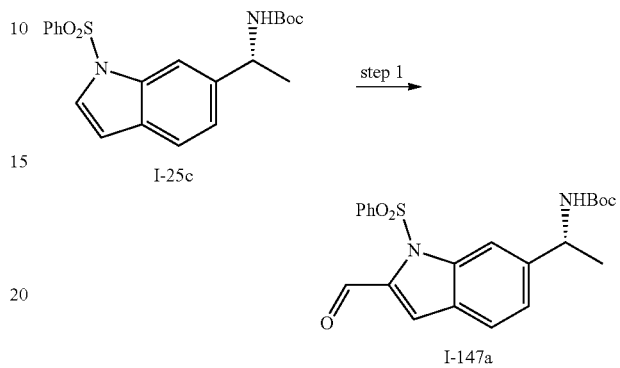

Step 1

A dry reaction vial equipped with stir bar was charged with tert-butyl (R)-(1-(1-(phenylsulfonyl)-1H-indol-6-yl)ethyl)carbamate (I-25c) (51.0 g, 127.0 mmol, 1.0 eq). The vial was evacuated and backfilled with argon (three times). Anhydrous THF (510 mL) was added and the mixture was cooled to −78° C. A commercial solution of LDA (2 M, 255 mL, 509 mmol, 4.0 eq) was added dropwise to the mixture at −78° C. followed by dropwise addition of dry TMEDA (74.0 g, 636.0 mmol, 5.0 eq). The mixture was allowed to stir at −78° C. for 15 minutes. Anhydrous DMF (55.9 g, 764 mmol, 6.0 eq) was then added dropwise to the mixture. The mixture was stirred for 1 hour at −78° C. The reaction mixture was quenched with sat. NH$_4$Cl aq. (500 mL) at −78° C. Then the mixture was allowed to warm to room temperature. The mixture was further diluted with water (1 L) and the aqueous phase was extracted with EtOAc (1 L×2). The combined organic extracts were washed with brine (500 mL), dried over Na$_2$SO$_4$ and concentrated under vacuum. The crude residue was purified by silica gel column chromatography (eluted with petroleum ether/EtOAc=2:1) to afford tert-butyl (R)-(1-(2-formyl-1-(phenylsulfonyl)-1H-indol-6-yl)ethyl)carbamate. ES/MS: m/z 429.1 [M+H]$^+$. $^1$H NMR (400 MHz, CDCl3): δ 10.47 (s, 1H), 8.18 (s, 1H), 7.74 (d, J=7.2 Hz, 2H), 7.56-7.49 (m, 2H), 7.42-7.36 (m, 3H), 7.25 (d, J=3.6 Hz, 1H), 4.89-4.92 (m, 2H), 1.48 (d, J=6.4 Hz, 3H), 1.43 (s, 9H).

tert-butyl (R)-(1-(5-fluoro-2-formyl-1-(phenylsulfonyl)-1H-indol-6-yl)ethyl)carbamate (I-147b)

Prepared using a similar procedure to I-147a using I-25b. ES/MS: m/z 364.2 [M+H]$^+$.

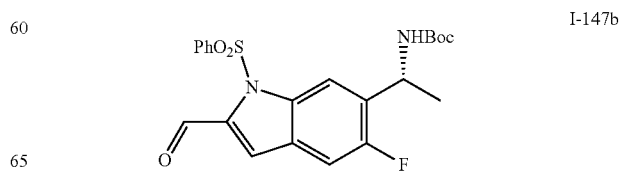

Preparation of tert-butyl (R)-(1-(2-formyl-1H-indol-6-yl)ethyl)carbamate (I-148a)

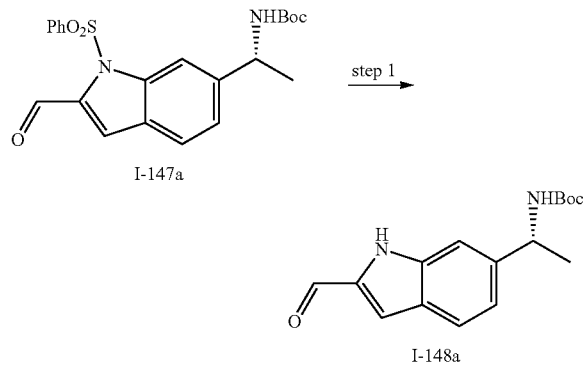

Step 1

To the stirred solution of tert-butyl (R)-(1-(2-formyl-1-(phenylsulfonyl)-1H-indol-6-yl)ethyl)carbamate (37.5 g, 87.7 mmol, 1.0 eq) in THF (450 mL), was added solution of tetrabutyl ammonium fluoride in THF (1 M, 175 mL, 175.4 mmol, 2.0 eq) and stirred at 40° C. for 1 h. Reaction mixture was cooled to room temperature, added water (500 mL) and extracted with EtOAc (2 L). Organic layer was dried over anhydrous $Na_2SO_4$ and evaporated under vacuum. The crude product was triturated with EtOAc/hexanes (2:1, 500 mL) and filtered to afford tert-butyl (R)-(1-(2-formyl-1H-indol-6-yl)ethyl)carbamate. ES/MS: m/z 599.2 $[2M+Na]^+$. $^1H$ NMR (400 MHz, CDCl3): δ 9.81 (s, 1H), 9.17 (brs, 1H), 7.69 (d, J=8.4 Hz, 1H), 7.37 (s, 1H), 7.23 (s, 1H), 7.13 (d, J=8.4 Hz, 1H), 4.90 (brs, 2H), 1.49 (d, J=6.4 Hz, 3H), 1.42 (s, 9H).

Preparation of methyl (R)-2-(6-(1-((tert-butoxycarbonyl)amino)ethyl)-5-fluoro-1H-indol-2-yl)-7-methoxy-1-methyl-1H-benzo[d]imidazole-5-carboxylate (I-149a)

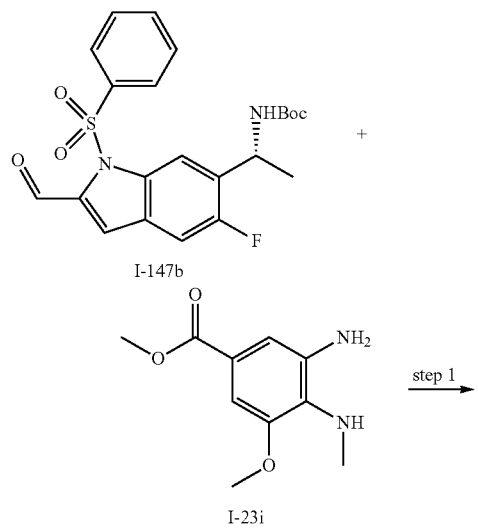

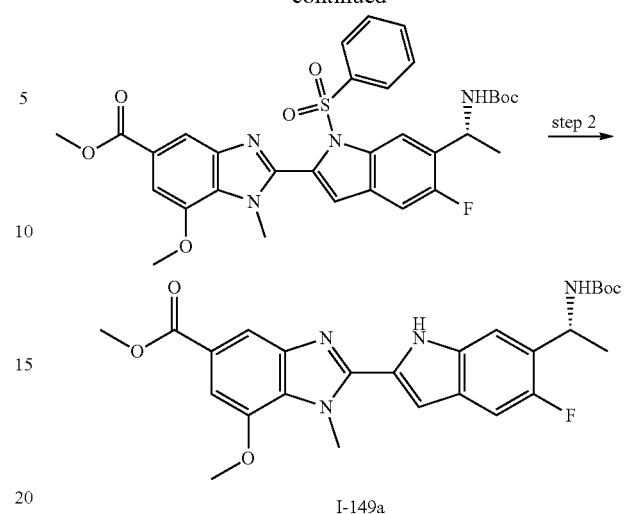

Step 1

Methyl (R)-2-(6-(1-((tert-butoxycarbonyl)amino)ethyl)-5-fluoro-1-(phenylsulfonyl)-1H-indol-2-yl)-7-methoxy-1-methyl-1H-benzo[d]imidazole-5-carboxylate was prepared following a similar procedure to step 1 of I-141a using I-147b and I-23i. ES/MS: m/z 497.02 $[M-SO_2Ph+2H]^+$.

Step 1

Methyl (R)-2-(6-(1-((tert-butoxycarbonyl)amino)ethyl)-5-fluoro-1H-indol-2-yl)-7-methoxy-1-methyl-1H-benzo[d]imidazole-5-carboxylate was prepared following a similar procedure to step 1 of I-148a. ES/MS: m/z 497.02 $[M-H]^+$. $^1H$ NMR (400 MHz, DMSO-d6) δ 12.09 (d, J=2.2 Hz, 1H), 7.93 (d, J=1.2 Hz, 1H), 7.58 (d, J=7.9 Hz, 1H), 7.48 (d, J=6.5 Hz, 1H), 7.41-7.34 (m, 2H), 7.18-7.12 (m, 1H), 4.98-4.83 (m, 1H), 4.33 (s, 3H), 4.03 (s, 3H), 3.90 (s, 3H), 1.40 (s, 9H), 1.36 (d, J=7.0 Hz, 3H).

methyl (R)-2-(6-(1-((tert-butoxycarbonyl)amino)ethyl)-5-fluoro-1H-indol-2-yl)-1-cyclopropyl-7-fluoro-1H-benzo[d]imidazole-5-carboxylate (I-149b)

Prepared using a similar procedure to I-149a using I-140c. ES/MS: m/z 511.01 $[M+H]^+$. $^1H$ NMR (400 MHz, DMSO-d6) δ 12.05 (s, 1H), 9.83 (s, 1H), 7.62 (d, J=7.9 Hz, 1H), 7.48 (d, J=11.1 Hz, 1H), 7.44 (d, J=6.4 Hz, 1H), 7.35 (s, 1H), 5.02-4.79 (m, 1H), 3.42-3.27 (m, 1H) 3.33 (s, 3H), 1.44-1.29 (m, 2H), 1.38 (s, 9H), 1.34 (d, J=7.0 Hz, 3H), 1.28-1.10 (m, 1H).

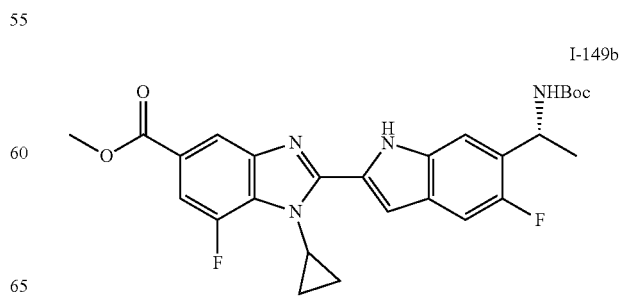

Preparation of methyl 2-(1-(8-(tert-butoxy)-7,7-dimethyl-8-oxooctyl)-6-((((tert-butylsulfinyl)amino)(cyclopropyl)methyl)-1H-pyrrolo[2,3-b]pyridin-2-yl)-7-methoxy-1-methyl-1H-benzo[d]imidazole-5-carboxylate (I-150a)

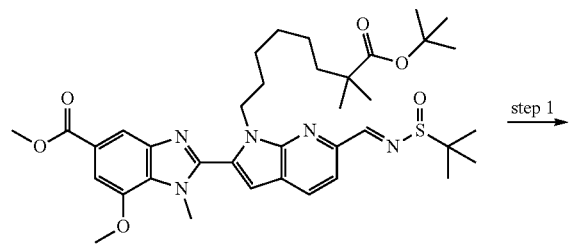

I-130b

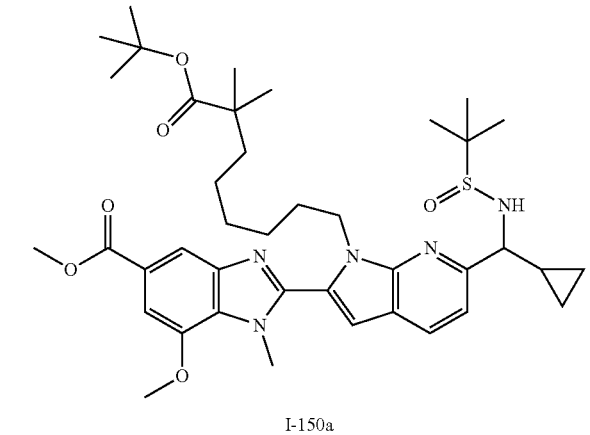

I-150a

Step 1

To a cooled solution of methyl 2-[1-(8-tert-butoxy-7,7-dimethyl-8-oxo-octyl)-6-[(E)-tert-butylsulfinyliminomethyl]pyrrolo[2,3-b]pyridin-2-yl]-7-methoxy-1-methyl-benzimidazole-5-carboxylate (200 mg, 0.288 mmol) in dry THF (4 mL) at 0° C. was added dropwise a solution of 1 M cyclopropylmagnesium bromide in 2-MeTHF (0.72 mL, 0.72 mmol). After 4 hours, an additional of 1 M cyclopropylmagnesium bromide in 2-MeTHF (1.4 mL, 1.4 mmol). After 5 minutes, warmed to rt and stirred for 3 hours. The reaction mixture was diluted with a saturated aqueous solution of ammonium chloride and ethyl acetate. The layers were separated and the aqueous was extracted with ethyl acetate. The combined organics were dried, filtered, and concentrated under reduced pressure to yield methyl 2-(1-(8-(tert-butoxy)-7,7-dimethyl-8-oxooctyl)-6-((((tert-butylsulfinyl)amino)(cyclopropyl)methyl)-1H-pyrrolo[2,3-b]pyridin-2-yl)-7-methoxy-1-methyl-1H-benzo[d]imidazole-5-carboxylate. ES/MS: m/z 736.0 [M+H]$^+$.

methyl 2-(1-(8-(tert-butoxy)-7,7-dimethyl-8-oxooctyl)-6-(1-(((tert-butylsulfinyl)amino)propyl)-1H-pyrrolo[2,3-b]pyridin-2-yl)-7-methoxy-1-methyl-1H-benzo[d]imidazole-5-carboxylate (I-150b)

Prepared following a similar procedure to I-150a using ethylmagnesium bromide instead of cyclopropyl magnesium bromide. ES/MS: m/z 724.2 [M+H]$^+$.

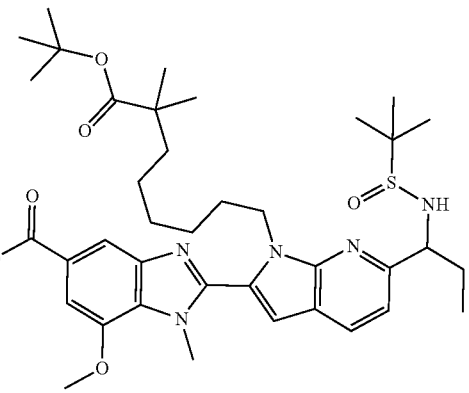

I-150b

Preparation of methyl 2-(6-(1-aminocylopropyl)-1-(pent-4-en-1-yl)-1H-pyrrolo[2,3-b]pyridin-2-yl)-7-methoxy-1-methyl-1H-benzo[d]imidazole-5-carboxylate (I-151a)

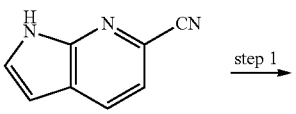

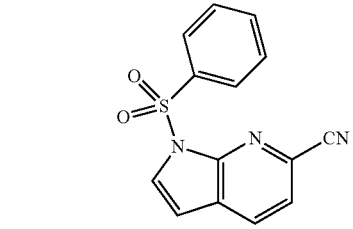

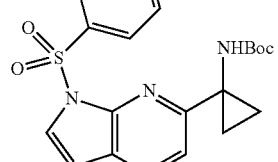

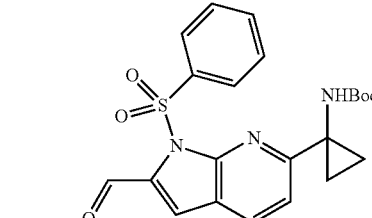

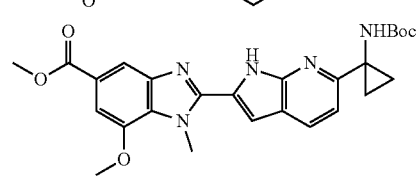

step 5
see synthesis of I-107a

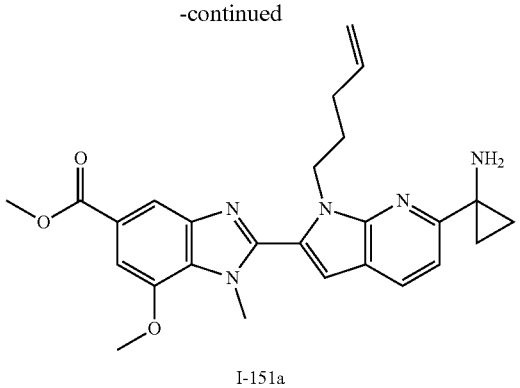

I-151a

Step 1.

To a solution of 1H-pyrrolo[2,3-b]pyridine-6-carbonitrile (3.40 g, 23.8 mmol) in MeTHF (45 mL) was added 1M NaHMDS in THF (26 mL) at 0 degrees. After stirring for 15 mins, benzenesulfonyl chloride (3.33 mL, 26.1 mmol) was added dropwise maintaining an internal temperature below 5 degrees. After stirring warming slowly to rt overnight, the reaction mixture was quenched with sat. NH₄Cl (aq). After stirring 15 minutes, the precipitated solid was filtered, washed with water, and dried in vacuo to yield 1-(benzenesulfonyl)pyrrolo[2,3-b]pyridine-6-carbonitrile. ES/MS: m/z 284.0 [M+H]⁺.

Step 2

To a solution of 1-(benzenesulfonyl)pyrrolo[2,3-b]pyridine-6-carbonitrile (1.00 g, 3.53 mmol) and Titanium isopropoxide (1.2 mL, 3.88 mmol) in THF (80 mL) at −78 degrees was added dropwise a solution of EtMgBr in THF (3.4 mL, 10.6 mmol). After 10 minutes, the reaction mixture was warmed to rt. BF3-Et2O (0.70 mL, 7.06 mmol) was added. After stirring overnight, the reaction mixture was cooled to −78 degrees and the above process was repeated. After warming to rt, the reaction mixture was stirred for 90 minutes and diluted with ethyl acetate and brine. The resulting solids were filtered, washing with ethyl acetate. The filtrate was separated and the aqueous extracted with ethyl acetate. The combined organics were dried, filtered, and concentrated under reduced pressure. The resulting residue was dissolved in DCM (16 mL) and Di-tert-butyl dicarbonate (0.651 g, 2.98 mmol) and triethylamine (1.32 mL, 9.50 mmol) were added. After 24 hours, the reaction mixture was concentrated under reduced pressure and the resulting residue was purified via silica gel column chromatography (0-70% ethyl acetate in hexanes) to yield tert-butyl (1-(1-(phenylsulfonyl)-1H-pyrrolo[2,3-b]pyridin-6-yl)cyclopropyl)carbamate. ES/MS: m/z 413.9 [M+H]⁺.

Step 3 tert-butyl N-[1-[1-(benzenesulfonyl)-2-formyl-pyrrolo[2,3-b]pyridin-6-yl]cyclopropyl]carbamate was synthesized following the preparation of I-139 using tert-butyl (1-(1-(phenylsulfonyl)-1H-pyrrolo[2,3-b]pyridin-6-yl)cyclopropyl)carbamate instead of I-25a. ES/MS: m/z 441.8 [M+H]⁺.

Step 4

A mixture of tert-butyl N-[1-[1-(benzenesulfonyl)-2-formyl-pyrrolo[2,3-b]pyridin-6-yl]cyclopropyl]carbamate (139 mg, 0.315 mmol) and I-23j in acetic acid (1.7 mL) was heated at 80 degrees for 2 hours. The reaction mixture was concentrated under reduced pressure and dissolved in THF (5 mL). A solution of TBAF in THF (1N, 0.315 mL, 0.315 mmol) was added and the reaction mixture was stirred overnight. An additional quantity of solution of TBAF in THF (1N, 0.315 mL, 0.315 mmol) was added and the reaction mixture was heated at 70 degrees. After 30 minutes, the reaction mixture was diluted with ethyl acetate and water. The layers were separated and the aqueous extracted with ethyl acetate. The combined organics were washed with a saturated solution of NH₄Cl (aq), dried, filtered, and concentrated under reduced pressure to yield methyl 2-(6-(1-((tert-butoxycarbonyl)amino)cyclopropyl)-1H-pyrrolo[2,3-b]pyridin-2-yl)-7-methoxy-1-methyl-1H-benzo[d]imidazole-5-carboxylate. ES/MS: m/z 492.1 [M+H]⁺.

Step 5 methyl 2-(6-(1-aminocyclopropyl)-1-(pent-4-en-1-yl)-1H-pyrrolo[2,3-b]pyridin-2-yl)-7-methoxy-1-methyl-1H-benzo[d]imidazole-5-carboxylate was synthesized following the preparation of I-107a using methyl 2-(6-(1-((tert-butoxycarbonyl)amino)cyclopropyl)-1H-pyrrolo[2,3-b]pyridin-2-yl)-7-methoxy-1-methyl-1H-benzo[d]imidazole-5-carboxylate instead of I-102. ES/MS: m/z 560.1 [M+H]⁺.

Preparation of isopropyl 7-methoxy-1-methyl-2-(1-(pent-4-en-1-yl)-6-(((1R)-1-((1,1,1-trifluorohex-5-en-2-yl)amino)ethyl)-1H-pyrrolo[2,3-b]pyridin-2-yl)-1H-benzo[d]imidazole-5-carboxylate (I-152)

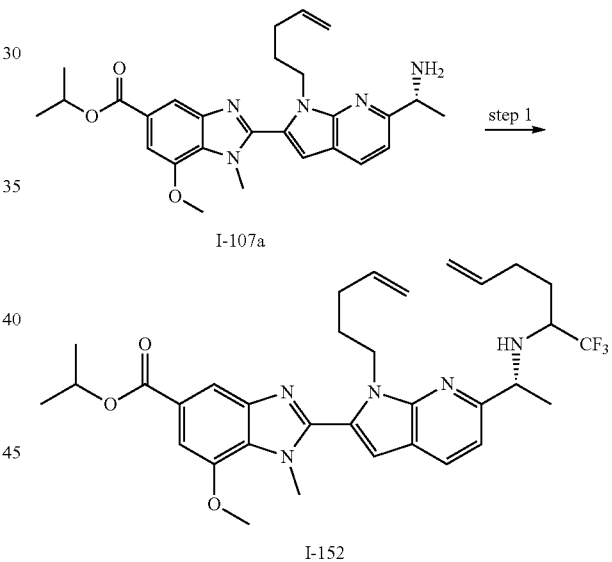

Step 1

A solution of isopropyl (R)-2-(6-(1-aminoethyl)-1-(pent-4-en-1-yl)-1H-pyrrolo[2,3-b]pyridin-2-yl)-7-methoxy-1-methyl-1H-benzo[d]imidazole-5-carboxylate (I-107a) (150 mg, 0.49 mmol) and acetic acid (30 mg, 0.49 mmol) in dichloromethane (3 mL) was stirred at room temperature for 5 min, after which a solution of 1,1,1-trifluorohex-5-en-2-one (50 mmol) in dichloromethane (1 mL) was added. After stirring for 5 h under reflux, the solvent was evaporated under reduced pressure. The residue was brought up in methanol (2.5 mL) and to this solution was added sodium cyanoborohydride (32 mg, 0.50 mmol). The reaction was stirred for 30 min and concentrated. Saturated sodium bicarbonate was added and the aqueous layer was washed with dichloromethane 3 times. The combined organic layers were dried over Na₂SO₄, filtered and concentrated. The crude residue was purified by flash chromatography eluting with hexanes/EtOAc to give a colorless oil. ES/MS: m/z 612.20 [M+H]+.

Preparation of methyl (R)-7-methoxy-1-methyl-2-(1-(pent-4-en-1-yl)-6-(1-(N-(pent-4-en-1-yl)acetamido)ethyl)-1H-pyrrolo[2,3-b]pyridin-2-yl)-1H-benzo[d]imidazole-5-carboxylate (I-153a)

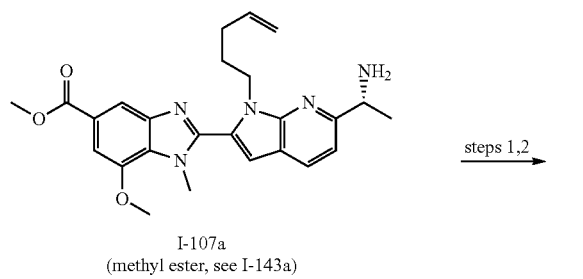

I-107a
(methyl ester, see I-143a)

steps 1,2

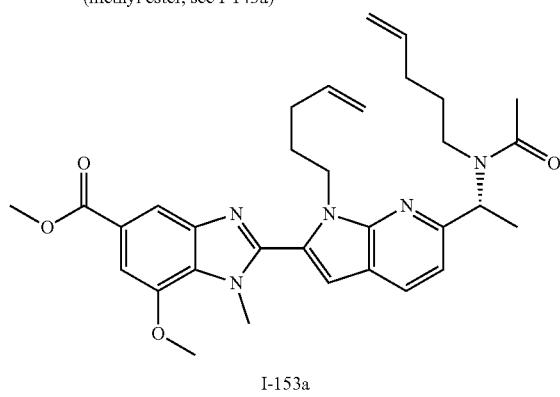

I-153a

Step 1

The HCl salt of methyl 2-[6-[(1R)-1-aminoethyl]-1-pent-4-enyl-pyrrolo[2,3-b]pyridin-2-yl]-7-methoxy-1-methyl-benzimidazole-5-carboxylate (180 mg, 0.37 mmol) and cesium carbonate (364 mg, 1.1 mmol) were combined in DMF (6 mL) and stirred at ambient temperature. After 5 minutes, 5-bromopent-1-ene (0.04 mL, 0.37 mmol) was added and the resulting mixture stirred at 60° C. After 4 days, the reaction was allowed to cool and was poured into water. The mixture was extracted 3× with EtOAc, and the combined extracts were washed once with brine, concentrated, and purified by silica chromatography using 1:3 EtOH/EtOAc with 0.25% TEA in heptane to afford methyl 7-methoxy-1-methyl-2-[1-pent-4-enyl-6-[(1R)-1-(pent-4-enylamino)ethyl]pyrrolo[2,3-b]pyridin-2-yl]benzimidazole-5-carboxylate. ES/MS: m/z 516.0 [M+H]$^+$.

Step 2

To a solution of methyl 7-methoxy-1-methyl-2-[1-pent-4-enyl-6-[(1R)-1-(pent-4-enylamino)ethyl]pyrrolo[2,3-b]pyridin-2-yl]benzimidazole-5-carboxylate (76 mg, 0.15 mmol), DIEA (0.05 mL, 0.30 mmol), and DMAP (2 mg, 0.02 mmol) in DCM (3 mL) was added acetyl chloride (0.014 mL, 0.19 mmol). The reaction was allowed to stir at ambient temperature for 4 days, then was poured into aq. NaHCO$_3$. The mixture was extracted 3× into DCM, and the combined extracts were concentrated and purified by silica chromatography using EtOAc in hexane to afford methyl 2-[6-[(1R)-1-[acetyl(pent-4-enyl)amino]ethyl]-1-pent-4-enyl-pyrrolo[2,3-b]pyridin-2-yl]-7-methoxy-1-methyl-benzimidazole-5-carboxylate. ES/MS: m/z 558.4 [M+H]$^+$.

Preparation of tert-butyl N-[(1R)-1-[2-[5-[(3S,4R)-3-(benzyloxycarbonylamino)-4-methoxy-piperidine-1-carbonyl]-7-methoxy-1-methyl-benzimidazol-2-yl]-1H-pyrrolo[2,3-b]pyridin-6-yl]ethyl]carbamate (I-153)

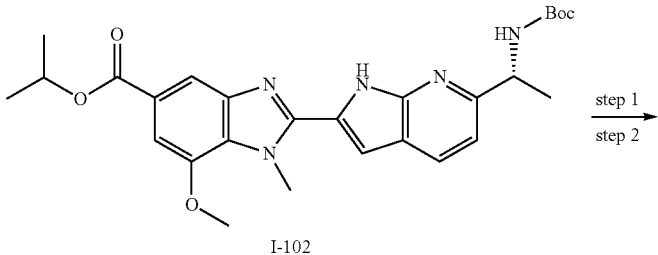

I-102 step 1
step 2

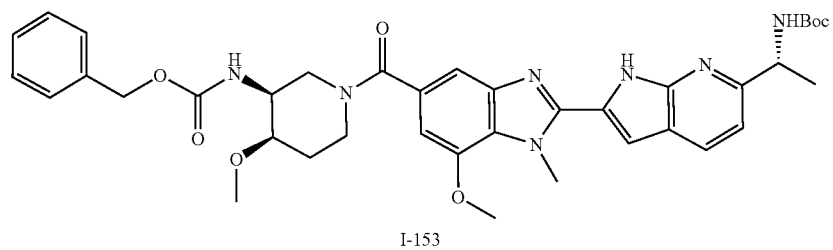

I-153

Step 1.
2 N lithium hydroxide solution (0.39 mL, 0.79 mmol) was added to a solution of isopropyl 2-[6-[(1R)-1-(tert-butoxycarbonylamino)ethyl]-1H-pyrrolo[2,3-b]pyridin-2-yl]-7-methoxy-1-methyl-benzimidazole-5-carboxylate (200 mg, 0.39 mmol) in methanol (1 mL) and tetrahydrofuran (1 mL). The resulting reaction mixture was heated at 60° C. for 90 min. The reaction mixture was concentrated and re-dissolved in dichloromethane, diluted with water and quenched with 4 N hydrochloride solution in dioxane (0.2 mL), extracting with dichloromethane (3×). The resulting mixture was concentrated to yield 2-[6-[(1R)-1-(tert-butoxycarbonylamino)ethyl]-1H-pyrrolo[2,3-b]pyridin-2-yl]-7-methoxy-1-methyl-benzimidazole-5-carboxylic acid, which was carried over to the consequent step without further purification assuming quantitative yield. ES/MS: m/z 466.02 [M+H]$^+$.

Step 2
N,N-diisopropylethylamine (0.27 mL, 1.57 mmol) was added to a solution of 2-[6-[(1R)-1-(tert-butoxycarbonylamino)ethyl]-1H-pyrrolo[2,3-b]pyridin-2-yl]-7-methoxy-1-methyl-benzimidazole-5-carboxylic acid (183 mg, 0.39 mmol) dissolved in dichloromethane (2 mL), followed by addition of [dimethylamino(triazolo[4,5-b]pyridin-3yloxy)methylene]-dimethyl-ammonium (224 mg, 0.59 mmol) and benzyl N-[(3S,4R)-4-methoxy-3-piperidyl]carbamate (57.2 mg, 0.22 mmol). The resulting reaction mixture was stirred at room temperature for 16 h. The reaction mixture was quenched with saturated ammonium chloride solution and extracted with dichloromethane twice. The collected organics were dried over magnesium sulfate, filtrated and concentrated, to produce the crude product, which was purified via silica gel column chromatography (0-15% methanol in dichloromethane) to yield tert-butyl N-[(1R)-1-[2-[5-[(3S,4R)-3-(benzyloxycarbonylamino)-4-methoxy-piperidine-1-carbonyl]-7-methoxy-1-methyl-benzimidazol-2-yl]-1H-pyrrolo[2,3-b]pyridin-6-yl]ethyl]carbamate. ES/MS: m/z 712.25 [M+H]$^+$.

Preparation of isopropyl (R)-2-(6-(1-((2,2-difluoroethyl)amino)ethyl)-1-(2,2-difluoropent-4-en-1-yl)-1H-pyrrolo[2,3-b]pyridin-2-yl)-7-methoxy-1-methyl-1H-benzo[d]imidazole-5-carboxylate
(I-154a)

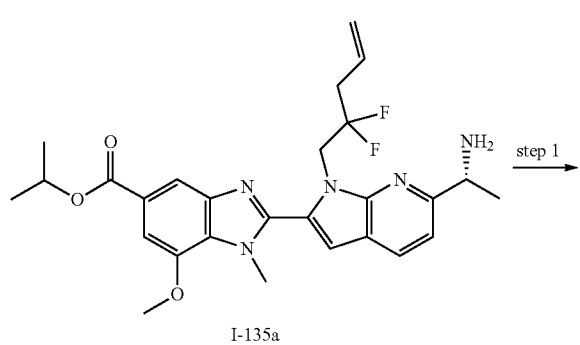

I-135a

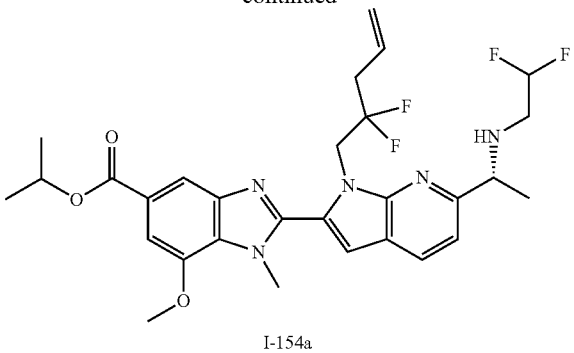

I-154a

Step 1
To a solution of isopropyl (R)-2-(6-(1-aminoethyl)-1-(2,2-difluoropent-4-en-1-yl)-1H-pyrrolo[2,3-b]pyridin-2-yl)-7-methoxy-1-methyl-1H-benzo[d]imidazole-5-carboxylate (150 mg, 0.293) in DMF (2 mL) were added DIEA (0.102 mL, 0.586 mmol) and 2,2-difluoroethyl trifluoromethanesulfonate (94 mg, 0.586 mmol). After 1 h, the reaction mixture was quenched with water and extracted with EtOAc twice. The collected organics were dried over magnesium sulfate, filtrated and concentrated. The crude produce was used directly is the next step. ES/MS: m/z 576.3 [M+H]$^+$.

Preparation of isopropyl (R)-2-(6-(1-((cyclopropylmethyl)amino)ethyl)-1-(2,2-difluoropent-4-en-1-yl)-1H-pyrrolo[2,3-b]pyridin-2-yl)-7-methoxy-1-methyl-1H-benzo[d]imidazole-5-carboxylate
(I-155a)

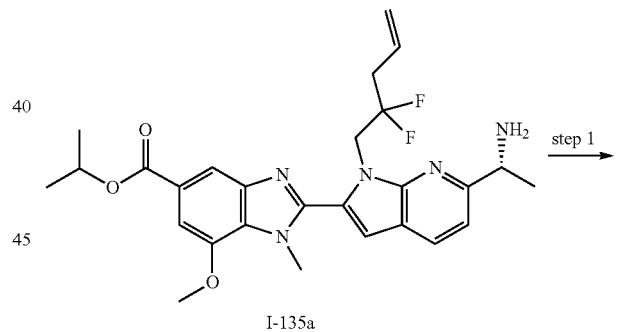

I-135a

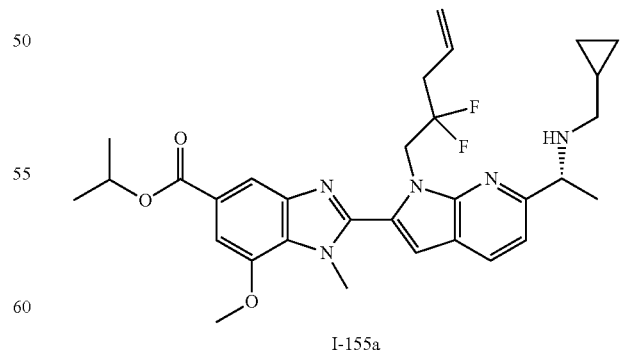

I-155a

Step 1
To a solution of isopropyl (R)-2-(6-(1-aminoethyl)-1-(2,2-difluoropent-4-en-1-yl)-1H-pyrrolo[2,3-b]pyridin-2-yl)-7-methoxy-1-methyl-1H-benzo[d]imidazole-5-carboxylate (150 mg, 0.293) in DCE (3 mL) were added NaBH(AcO)₃ (87 mg, 0.411 mmol), AcOH (0.017 mL, 0.293 mmol) and cyclopropanecarboxaldehyde (0.023 mL, 0.308 mmol). The reaction mixture was allowed to stir at rt for 2 h and quenched with 1 N NaOH. The mixture was extracted twice with DCM. The collected organics were dried over magnesium sulfate, filtrated and concentrated. The crude produce was used directly is the next step. ES/MS: m/z 566.3 [M+H]⁺.

Preparation of methyl (R)-2-(6-(1-((tert-butoxycarbonyl)amino)ethyl)-5-fluoro-1H-pyrrolo[2,3-b]pyridin-2-yl)-1-cyclopropyl-7-fluoro-1H-benzo[d]imidazole-5-carboxylate (I-156)

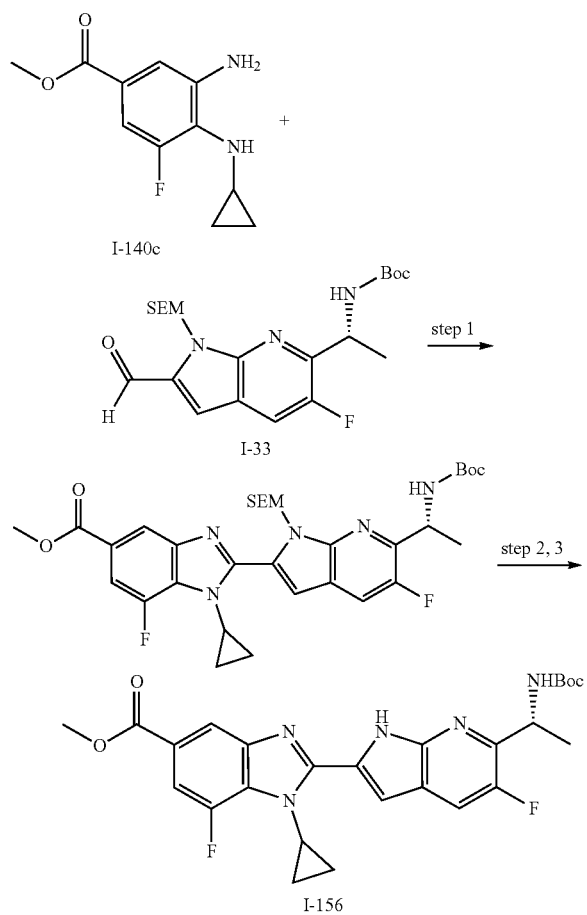

Step 1.
methyl (R)-2-(6-(1-((tert-butoxycarbonyl)amino)ethyl)-5-fluoro-1-((2-(trimethylsilyl)ethoxy)methyl)-1H-pyrrolo[2,3-b]pyridin-2-yl)-1-cyclopropyl-7-fluoro-1H-benzo[d]imidazole-5-carboxylate was prepared using a similar procedure to that described for I-141a, but starting with I-140c and tert-butyl (R)-(1-(5-fluoro-2-formyl-1-((2-(trimethylsilyl)ethoxy)methyl)-1H-pyrrolo[2,3-b]pyridin-6-yl)ethyl)carbamate (I-33). ES/MS: m/z 641.87 [M+H]⁺.
Steps 2 and 3.
methyl (R)-2-(6-(1-((tert-butoxycarbonyl)amino)ethyl)-5-fluoro-1-((2-(trimethylsilyl)ethoxy)methyl)-1H-pyrrolo[2,3-b]pyridin-2-yl)-1-cyclopropyl-7-fluoro-1H-benzo[d]imidazole-5-carboxylate (179 mg, 0.28 mmol) was dissolved in MeCN (4 mL). A solution of hydrochloric acid in dioxane (4 M, 2 mL, 8 mmol) was added, and the mixture was heated to 45° C. for 18 h. The mixture was concentrated, and the obtained residue was dissolved in DCM (4 mL). Hunig's base (0.24 mL, 1.4 mmol) was added followed by di-tert-butyl dicarbonate (61 mg, 0.28 mmol). The mixture was stirred until LCMS indicated complete conversion and was then concentrated directly onto silica gel and purified by silica gel chromatography (EA/hexanes gradient) to afford methyl (R)-2-(6-(1-((tert-butoxycarbonyl)amino)ethyl)-5-fluoro-1H-pyrrolo[2,3-b]pyridin-2-yl)-1-cyclopropyl-7-fluoro-1H-benzo[d]imidazole-5-carboxylate. ES/MS: m/z 511.99 [M+H]⁺.

Preparation of methyl (R,Z)-7-methoxy-1-methyl-2-(1-(pent-3-en-1-yl)-6-(pyrrolidin-2-yl)-1H-pyrrolo[2,3-b]pyridin-2-yl)-1H-benzo[d]imidazole-5-carboxylate (I-157)

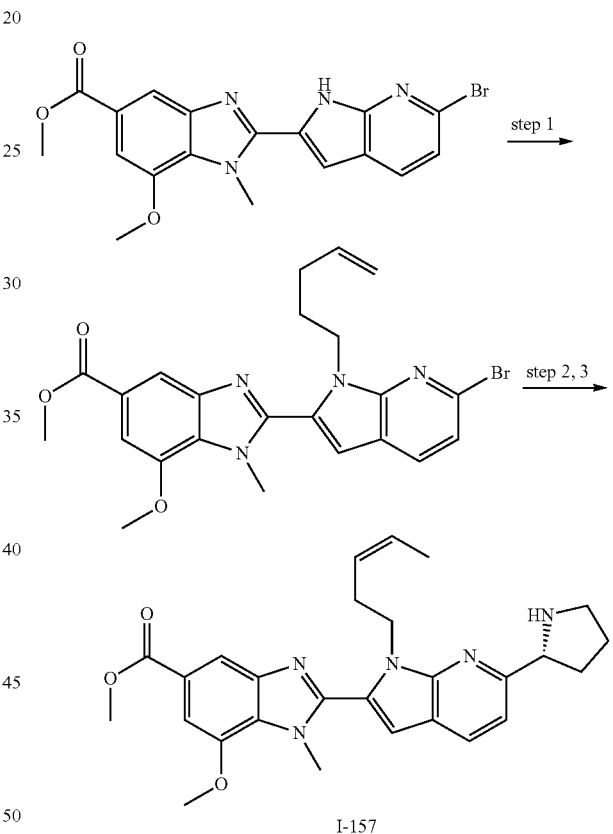

Step 1
methyl 2-(6-bromo-1-(pent-4-en-1-yl)-1H-pyrrolo[2,3-b]pyridin-2-yl)-7-methoxy-1-methyl-1H-benzo[d]imidazole-5-carboxylate was made according to Procedure 8, step 1, using methyl 2-(6-bromo-1H-pyrrolo[2,3-b]pyridin-2-yl)-7-methoxy-1-methyl-1H-benzo[d]imidazole-5-carboxylate, and 5-bromo-1-pentene. ES/MS: m/z 483.4 [M+H]+.
Step 2
methyl (R,Z)-2-(6-(1-(tert-butoxycarbonyl)pyrrolidin-2-yl)-1-(pent-3-en-1-yl)-1H-pyrrolo[2,3-b]pyridin-2-yl)-7-methoxy-1-methyl-1H-benzo[d]imidazole-5-carboxylate was made following step 2 of Procedure 12 using methyl 2-(6-bromo-1-(pent-4-en-1-yl)-1H-pyrrolo[2,3-b]pyridin-2-yl)-7-methoxy-1-methyl-1H-benzo[d]imidazole-5-. ES/MS: m/z 574.3 [M+H]+.

Step 3 methyl (R,Z)-7-methoxy-1-methyl-2-(1-(pent-3-en-1-yl)-6-(pyrrolidin-2-yl)-1H-pyrrolo[2,3-b]pyridin-2-yl)-1H-benzo[d]imidazole-5-carboxylate was prepared following a similar procedure to step 2 of I-107a using methyl (R,Z)-2-(6-(1-(tert-butoxycarbonyl)pyrrolidin-2-yl)-1-(pent-3-en-1-yl)-1H-pyrrolo[2,3-b]pyridin-2-yl)-7-methoxy-1-methyl-1H-benzo[d]imidazole-5-carboxylate. ES/MS: m/z 474.3 [M+H]+.

3. Synthesis of Intermediates L1 to L83

Preparation of tert-butyl 8-bromooctanoate (L1a)

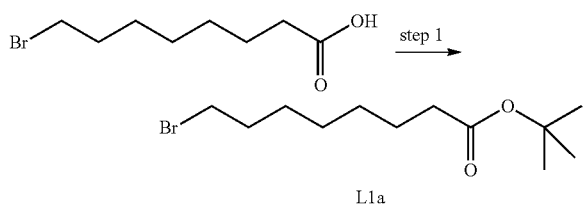

L1a

Step 1.

To a solution of 8-bromooctanoic acid (2.0 g, 9.96 mmol) in dichloromethane (25 mL) and tert-butanol (25 mL) were added di-tert-butyl dicarbonate (3.91 g, 17.9 mmol) and DMAP (329 mg, 2.69 mmol). The reaction mixture was stirred at room temperature for 16 h. After concentration in vacuo, ethyl acetate was added and the solution was washed with saturated aqueous $NaHCO_3$, followed by saturated aqueous $NH_4Cl$ and brine. The organic phase was dried with $MgSO_4$, filtered, and concentrated. Purification by silica gel chromatography (0-20% EtOAc in hexanes) provided tert-butyl 8-bromooctanoate. $^1$H NMR (400 MHz, DMSO-d6) δ 3.40 (td, J=6.8, 1.6 Hz, 2H), 2.20 (td, J=7.4, 1.5 Hz, 2H), 1.90-1.78 (m, 2H), 1.64-1.53 (m, 2H), 1.53-1.25 (m, 8H), 1.44 (s, 9H). Commercially available (cas 77383-17-6).

tert-butyl 7-bromoheptanoate (L1b)

Commercially available (cas 51100-47-1) or prepared following a similar procedure to L1a starting with 7-bromoheptanoic acid.

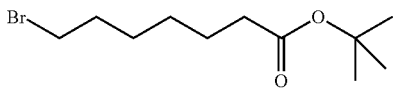

L1b tert-butyl 9-bromononanoate (L1c)

Commercially available (cas 77383-17-6) or prepared following a similar procedure to L1a starting with 9-bromononanoic.

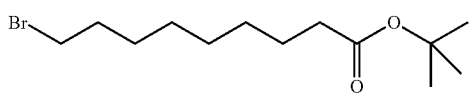

L1c tert-butyl 6-bromohexanoate (L1d)

Commercially available (cas 65868-63-5) or prepared following a similar procedure to L1a starting with 6-bromohexanoic acid.

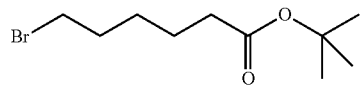

L1d tert-butyl 10-bromodecanoate (L1e)

Commercially available (cas 1644575-06-3) or prepared following a similar procedure to L1a starting with 10-bromodecanoic acid.

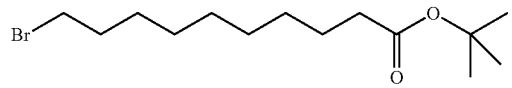

L1e

Preparation of tert-butyl 3-(4-(tosyloxy)butoxy)propanoate (L2a)

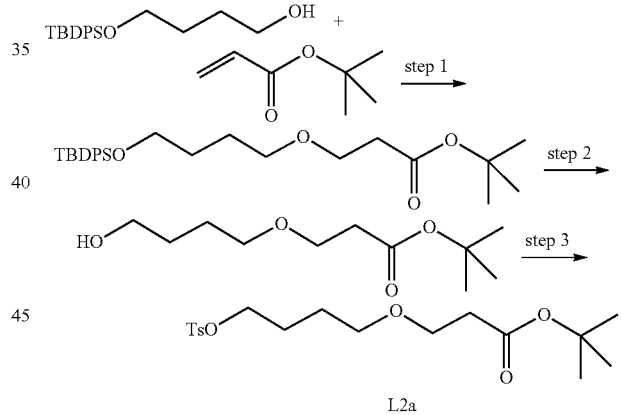

L2a

Step 1

To a solution of 4-((tert-butyldiphenylsilyl)oxy)butan-1-ol (1.0 g, 3.04 mmol, Synlett 2014, 25(12), 1764-1768) in tert-butanol (15 mL) were added tert-butyl acrylate (6.7 mL, 45.7 mmol) and $Cs_2CO_3$ (992 mg, 3.04 mmol). The reaction mixture was stirred at room temperature for 16 h. The reaction mixture was diluted with ethyl acetate and washed brine. The organic phase was dried with $MgSO_4$, filtered, and concentrated. Purification by silica gel chromatography (0-20% EtOAc in hexanes) provided tert-butyl 3-(4-((tert-butyldiphenylsilyl)oxy)butoxy)propanoate. $^1$H NMR (400 MHz, Chloroform-d) δ 7.71-7.62 (m, 4H), 7.52-7.30 (m, 6H), 3.72-3.58 (m, 4H), 3.42 (t, J=6.1 Hz, 2H), 2.52-2.36 (m, 2H), 1.69-1.55 (m, 6H), 1.44 (s, 9H), 1.04 (s, 9H).

Step 2

To a solution of tert-butyl 3-(4-((tert-butyldiphenylsilyl)oxy)butoxy)propanoate (1.1 g, 2.41 mmol) in THF (10 mL)

was added 1.0 M TBAF in THF (3.61 mL). The reaction mixture was stirred at room temperature for 1 h. Ethyl acetate was added and the solution was washed with saturated aqueous NaHCO$_3$ followed by brine. The organic phase was dried with MgSO$_4$, filtered, and concentrated. Purification by silica gel chromatography (0-80% EtOAc in hexanes) provided tert-butyl 3-(4-hydroxybutoxy)propanoate. $^1$H NMR (400 MHz, Chloroform-d) δ 3.72-3.61 (m, 4H), 3.49 (t, J=5.5 Hz, 2H), 2.49 (td, J=6.4, 0.8 Hz, 2H), 2.12 (t, J=5.6 Hz, 1H), 1.73-1.59 (m, 4H), 1.45 (s, 9H).

Step 3

To a solution of tert-butyl 3-(4-hydroxybutoxy)propanoate (452 mg, 2.07 mmol) in dichloromethane (10 mL) at 0° C. was added TsCl (671 mg, 3.52 mmol), triethylamine (0.87 mL, 6.21 mmol) and DMAP (25 mg, 0.21 mmol). The reaction mixture was stirred at room temperature for 4 h. The reaction mixture was diluted with DCM then washed with water and brine. The organic phase was dried with MgSO$_4$, filtered, and concentrated. Purification by silica gel chromatography (0-80% EtOAc in hexanes) provided tert-butyl 3-(4-(tosyloxy)butoxy)propanoate. $^1$H NMR (400 MHz, Chloroform-d) δ 7.79 (d, J=8.1 Hz, 2H), 7.34 (d, J=8.0 Hz, 2H), 4.04 (t, J=6.3 Hz, 2H), 3.60 (t, J=6.4 Hz, 2H), 3.38 (t, J=6.1 Hz, 2H), 2.49-2.39 (m, 5H), 1.72 (dq, J=8.2, 6.4 Hz, 2H), 1.62-1.52 (m, 2H), 1.44 (s, 9H).

Preparation of tert-butyl 2-(4-(tosyloxy)butoxy)acetate (L3a)

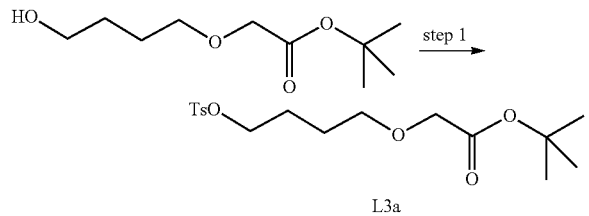

Step 1

To a solution of tert-butyl 2-(4-hydroxybutoxy)acetate (329 mg, 1.61 mmol, PCT Int. Appl., 2012143703) in dichloromethane (10 mL) at 0° C. were added TsCl (461 mg, 2.42 mmol), triethylamine (0.67 mL, 4.83 mmol) and DMAP (20 mg, 0.16 mmol). The reaction mixture was stirred at room temperature for 4 h. The reaction mixture was diluted with DCM then washed with water and brine. The organic phase was dried with MgSO$_4$, filtered, and concentrated. Purification by silica gel chromatography (0-80% EtOAc in hexanes) provided tert-butyl 2-(4-(tosyloxy)butoxy)acetate. $^1$H NMR (400 MHz, Chloroform-d) δ 7.82-7.75 (m, 2H), 7.34 (d, J=7.9 Hz, 2H), 4.07 (t, J=6.2, 2H), 3.89 (s, 2H), 3.47 (t, J=6.6, 6.1, 2H), 2.45 (s, 3H), 1.83-1.73 (m, 2H), 1.70-1.59 (m, 2H), 1.47 (s, 9H).

Preparation of tert-butyl 8-bromo-2,2-dimethyloctanoate (L4a)

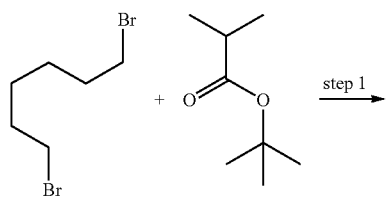

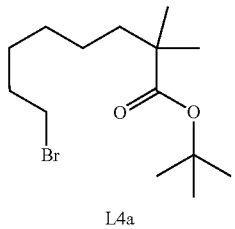

Step 1

To a solution of tert-butyl isobutyrate (0.50 g, 3.5 mmol) in anhydrous THF (10 mL) under nitrogen, at −40° C., was added a solution of lithium diisopropylamide (1.0 M solution in THF, 3.5 mL, 3.5 mmol) dropwise over 10 min. After 1 h, 1,6-dibromohexane (1.6 g, 6.5 mmol) was added. The mixture was stirred for 30 min at −40° C. and then allowed to warm to room temperature and stirred overnight. Ice water was added and the THF was removed under reduced pressure. The residue was brought up in ethyl acetate and washed with brine. The organic layer was dried over Na$_2$SO$_4$ and concentrated to afford a crude yellow oil. The residue was purified by silica gel column chromatography (0-30% EtOAc in hexanes) to provide tert-butyl 8-bromo-2,2-dimethyloctanoate. $^1$H NMR (400 MHz, Chloroform-d) δ 3.40 (t, J=6.9 Hz, 1H), 1.85 (p, J=6.9 Hz, 2H), 1.50-1.37 (m, 11H), 1.36-1.18 (m, 6H), 1.11 (s, 6H).

tert-butyl 7-bromo-2,2-dimethylheptanoate (L4b)

Prepared following a similar procedure to L4a using 1,5-dibromopentane instead of 1,6-dibromohexane. $^1$H NMR (400 MHz, CDCl3): δ 3.38 (m, 2H), 1.85-1.81 (m, 2H), 1.45 (m, 3H), 1.40 (m, 9H), 1.23 (m, 3H), 1.08 (m, 6H).

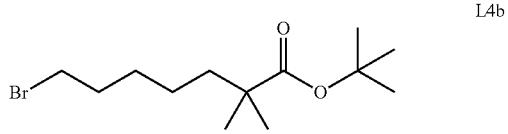 [SMILES: CC(C)(C)OC(=O)C(C)(C)CCCCCBr]

tert-butyl 1-(6-bromohexyl)cyclobutane-1-carboxylate (L4c)

Prepared following a similar procedure to L4a using tert-butyl cyclobutanecarboxylate instead of tert-butyl isobutyrate. $^1$H NMR (400 MHz, Chloroform-d) δ 3.42 (t, J=6.8 Hz, 2H), 2.42-2.32 (m, 2H), 1.92-1.79 (m, 6H), 1.75-1.70 (m, 2H), 1.47 (s, 9H), 1.45 (s, 2H), 1.38-1.27 (m, 2H), 1.27-1.16 (m, 2H).

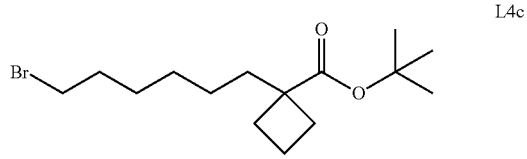 [SMILES: CC(C)(C)OC(=O)C1(CCCCCCBr)CCC1]

tert-butyl 1-(6-bromohexyl)cyclopropane-1-carboxylate (L4d)

Prepared following a similar procedure to L4a using tert-butyl cyclopropanecarboxylate instead of tert-butyl isobutyrate. $^1$H NMR (400 MHz, Chloroform-d) δ 3.42 (t, J=6.8 Hz, 2H), 1.87 (dt, J=14.7, 6.9 Hz, 2H), 1.56-1.49 (m, 1H), 1.44 (s, 9H), 1.32 (m, J=16.5, 9.3, 4.2, 1.6 Hz, 3H), 1.12 (q, J=3.8 Hz, 2H), 0.95-0.89 (m, 2H), 0.82-0.75 (m, 2H), 0.63-0.59 (m, 2H).

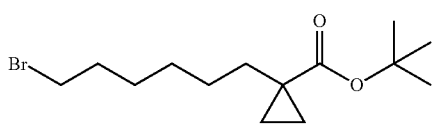

L4d tert-butyl 1-(7-bromoheptyl)cyclobutane-1-carboxylate (L4e)

Prepared following a similar procedure to L4a using 1,7-dibromoheptane instead of 1,6-dibromohexane and tert-butyl cyclobutanecarboxylate instead of tert-butyl isobutyrate. $^1$H NMR (400 MHz, Chloroform-d) δ 3.43 (t, J=6.8 Hz, 2H), 2.42-2.31 (m, 2H), 1.93-1.78 (m, 6H), 1.74-1.67 (m, 2H), 1.47 (s, 9H), 1.44 (s, 2H), 1.38-1.26 (m, 4H), 1.25-1.14 (m, 2H).

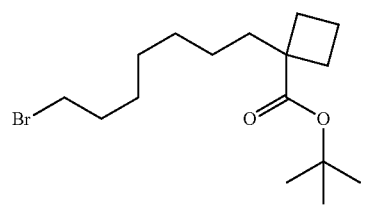

L4e tert-butyl 1-(7-bromoheptyl)cyclopropane-1-carboxylate (L4f)

Prepared following a similar procedure to L4a using 1,7-dibromoheptane instead of 1,6-dibromohexane and tert-butyl cyclopropanecarboxylate instead of tert-butyl isobutyrate. $^1$H NMR (400 MHz, Chloroform-d) δ 3.43 (t, J=6.9 Hz, 2H), 1.92-1.82 (m, 2H), 1.49-1.45 (m, 4H), 1.44 (s, 9H), 1.43 (s, 2H), 1.37-1.27 (m, 4H), 1.12 (q, J=3.8 Hz, 2H), 0.61 (q, J=3.9 Hz, 2H).

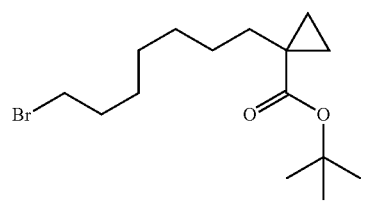

L4f

Preparation of tert-butyl (R)-8-bromo-2-methyloctanoate (L5a)

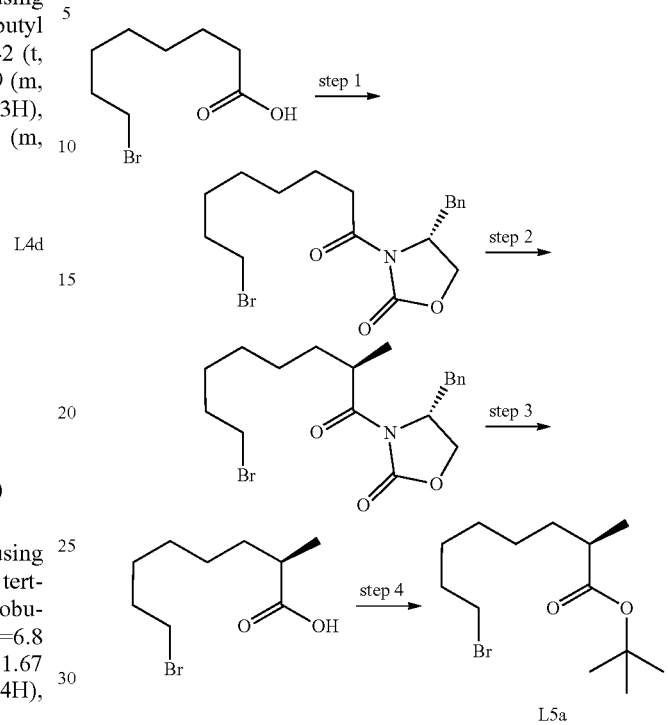

Step 1

To a solution of 8-bromooctanoic acid (630 mg, 2.8 mmol) in dry THF (14 mL) at 0° C. was added with triethylamine (0.98 mL, 7.1 mmol) and pivaloyl chloride (0.37 mL, 3.0 mmol). The suspension was stirred for 20 min. Then, lithium chloride (120 mg, 2.8 mmol) and (R)-4-benzyl-2-oxazolidinone (620 mg, 2.8 mmol) were added. The suspension was warmed to room temperature and stirred for another 30 min. Then, water (5 mL) was added and the solution was concentrated under reduced pressure. The aqueous phase was extracted with EtOAc. The combined organic phases were dried over MgSO$_4$, filtered and concentrated. The residue was purified by silica gel column chromatography (0-100% EtOAc in hexanes) to provide (R)-4-benzyl-3-(8-bromooctanoyl)oxazolidin-2-one. $^1$H NMR (400 MHz, Chloroform-d) δ 7.34 (t, J=7.1 Hz, 2H), 7.30-7.25 (m, 1H), 7.24-7.17 (m, 2H), 4.67 (ddt, J=10.3, 6.9, 3.3 Hz, 1H), 4.24-4.14 (m, 2H), 3.41 (t, J=6.8 Hz, 2H), 3.30 (dd, J=13.4, 3.4 Hz, 1H), 3.04-2.83 (m, 2H), 2.77 (dd, J=13.3, 9.6 Hz, 1H), 1.87 (p, J=6.9 Hz, 2H), 1.70 (p, J=7.6, 6.8 Hz, 2H), 1.51-1.31 (m, 6H).

Step 2

To a solution of (R)-4-benzyl-3-(8-bromooctanoyl)oxazolidin-2-one (620 mg, 1.6 mmol) in dry THF (5 mL) at −78° C. was added a solution of sodium bis(trimethylsilyl)amide (1 M in THF, 1.9 mL, 1.9 mmol). The solution was stirred for 20 min and then, methyl iodide (0.60 mL, 9.7 mmol) was added. The solution was allowed to warm to room temperature for 30 min. Then, water (1 mL) was added and the solution was concentrated under reduced pressure. The aqueous phase was extracted with EtOAc. The combined organic phases were dried over Na$_2$SO$_4$, filtered and concentrated. The residue was purified by silica gel column chromatography (0-100% EtOAc in hexanes) to provide (R)-4-benzyl-3-((R)-8-bromo-2-methyloctanoyl)oxazolidin-2-one. $^1$H NMR (400 MHz, Chloroform-d) δ 7.36-7.25 (m, 3H), 7.21 (d, J=7.3 Hz, 2H), 4.68 (ddt, J=10.3, 6.8, 3.2 Hz, 1H), 4.24-4.15 (m, 2H), 3.71 (h, J=6.7 Hz, 1H), 3.40 (t, J=6.8 Hz, 2H), 3.27 (dd, J=13.4, 3.4 Hz, 1H), 2.77 (dd, J=13.3, 9.6 Hz, 1H), 1.85 (p, J=6.9 Hz, 2H), 1.47-1.19 (m, 11H).

Step 3

To a solution of (R)-4-benzyl-3-((R)-8-bromo-2-methyloctanoyl)oxazolidin-2-one (490 mg, 1.2 mmol) in THF (5 mL) and water (1 mL) at 0° C. was added an solution of 30% hydrogen peroxide in water (0.44 mL, 4.3 mmol) followed lithium hydroxide (100 mg, 2.5 mmol). The solution was allowed to warm to room temperature and stirred for 3 h. Then, a solution of sodium sulfite (880 mg, 6.2 mmol in 5 mL water) and saturated sodium bicarbonate (15 mL) were added. The THF was removed in vacuo and the remaining aqueous solution was washed with dichloromethane three times and these organic layers were discarded. The aqueous layer was acidified to pH 2 with 25% HCl and extracted three times with EtOAc. The EtOAc fractions were combined and concentrated in vacuo to give (R)-8-bromo-2-methyloctanoic acid. $^1$H NMR (400 MHz, Chloroform-d) δ 3.40 (t, J=6.8 Hz, 2H), 2.47 (h, J=7.0 Hz, 1H), 1.85 (p, J=6.9 Hz, 2H), 1.50-1.30 (m, 8H), 1.19 (d, J=7.2 Hz, 3H).

Step 4

A solution of (R)-8-bromo-2-methyloctanoic acid (223 mg, 0.96 mmol), 4-(dimethylamino)pyridine (12 mg, 0.096 mmol), and di-tert-butyl dicarbonate (420 mg, 1.9 mmol) in dichloromethane (1.2 mL) and tert-butanol (1.2 mL) was allowed to stir at room temperature overnight. The reaction was concentrated and brought up in EtOAc and washed with saturated sodium bicarbonate, saturated ammonium chloride, brine, and dried over MgSO$_4$, filtered and concentrated. The residue was purified by silica gel column chromatography (0-40% EtOAc in hexanes) to provide tert-butyl (R)-8-bromo-2-methyloctanoate. $^1$H NMR (400 MHz, Chloroform-d) δ 3.40 (td, J=6.9, 0.9 Hz, 2H), 2.30 (h, J=6.9 Hz, 1H), 1.85 (p, J=6.9 Hz, 2H), 1.50-1.20 (m, 17H), 1.09 (dd, J=7.0, 1.0 Hz, 3H).

tert-butyl (S)-8-bromo-2-methyloctanoate (L5b)

Prepared following a similar procedure to L5a using (S)-4-benzyl-2-oxazolidinone instead of (R)-4-benzyl-2-oxazolidinone. $^1$H NMR (400 MHz, Chloroform-d) δ 3.40 (td, J=6.9, 0.9 Hz, 2H), 2.30 (h, J=6.9 Hz, 1H), 1.85 (p, J=6.9 Hz, 2H), 1.50-1.20 (m, 17H), 1.09 (dd, J=7.0, 1.0 Hz, 3H).

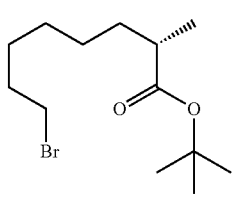

L5b tert-butyl (R)-2-allyl-8-bromooctanoate (L5c)

Prepared using a similar procedure to L5a using (S)-4-benzyl-2-oxazolidinone instead of (R)-4-benzyl-2-oxazolidinone and allyl bromide instead of methyl iodide. $^1$H NMR (400 MHz, Chloroform-d) δ 5.76 (ddt, J=16.9, 10.2, 6.9 Hz, 1H), 5.15-5.04 (m, 2H), 3.40 (t, J=6.9 Hz, 2H), 2.55-2.37 (m, 2H), 2.32-2.23 (m, 1H), 1.85 (p, J=6.9 Hz, 2H), 1.73-1.19 (m, 17H).

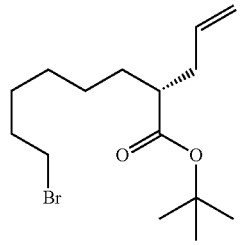

L5c

Preparation of tert-butyl 2-methyl-2-((5-(tosyloxy)pentyl)oxy)propanoate (L6a)

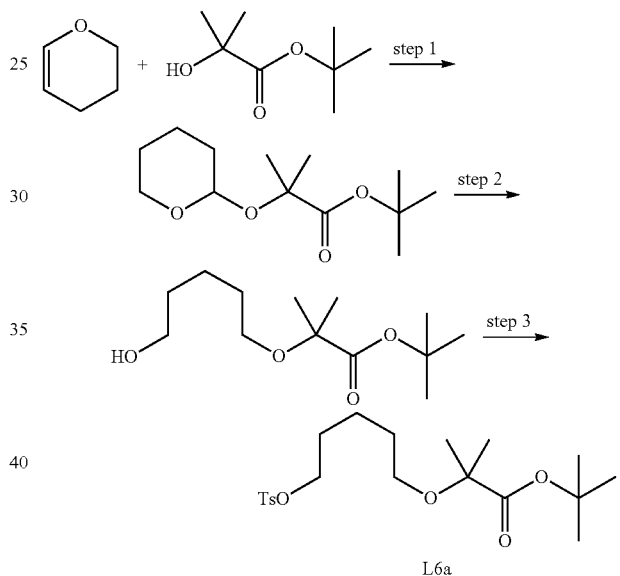

L6a

Step 1

A mixture of tert-butyl 2-hydroxy-2-methyl-propanoate (0.5 g, 3.1 mmol), 3,4-dihydropyran (0.78 g, 9 mmol) in DCM (5 mL) and pyridinium p-toluenesulfonic acid (78 mg, 0.3 mmol) was stirred at rt for 16 h. Water and EtOAc were added. The aqueous layer was extracted with EtOAc and the combined organic layers were dried over sodium sulfate. Filtration and evaporation of solvents yielded the crude tert-butyl 2-methyl-2-((tetrahydro-2H-pyran-2-yl)oxy)propanoate which was used in the subsequent step with no further purification. ES/MS: m/z 267.0 [M+Na]$^+$.

Step 2

The crude material from the previous reaction (ca. 2 mmol) was cooled to 0° C. and treated neat with borane-THF (1M, 5 mmol, 4.6 mL). The reaction was allowed to slowly reach rt, and was stirred for 16 h followed by an additional 24 h at 40° C. The reaction was quenched with methanol followed by the addition of water and EtOAc. The aqueous layer was extracted with EtOAc and the combined organic layers were dried over sodium sulfate and concentrated to a light yellow oil. Purification by silica gel (0-100%

EtOAc in hexanes) provided tert-butyl 2-((5-hydroxypentyl)oxy)-2-methylpropanoate. ¹H NMR (400 MHz, Chloroform-d) δ 3.71-3.62 (m, 2H), 3.39 (t, J=6.6 Hz, 2H), 1.66-1.55 (m, 7H), 1.48 (s, 9H), 1.38 (s, 6H). ES/MS: m/z 269.0 [M+Na]⁺.

Step 3 tert-Butyl 2-methyl-2-((5-(tosyloxy)pentyl)oxy)propanoate (L6a) was then prepared following a similar procedure to L3a.

tert-butyl 3-((5-hydroxypentyl)oxy)-2,2-dimethylpropanoate (L6b)

Prepared following a similar procedure to L6a using tert-butyl 3-hydroxy-2,2-dimethylpropanoate instead of tert-butyl 2-hydroxy-2-methyl-propanoate. ES/MS: m/z 437.2 [M+Na]⁺.

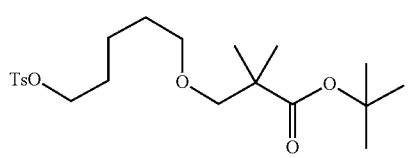

L6b

Preparation of tert-butyl 1-(5-bromopentyl)-1H-pyrazole-5-carboxylate (L7a) and tert-butyl 1-(5-bromopentyl)-1H-pyrazole-3-carboxylate (L7b)

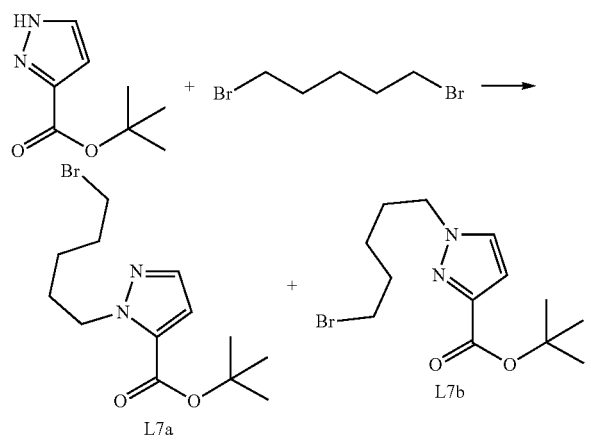

Step 1

To a mixture of tert-butyl 1H-pyrazole-3-carboxylate (0.25 g, 1.49 mmol) and cesium carbonate (0.53 g, 1.64 mmol) in MeCN (15 mL) was added 1,5-dibromopentane (0.4 mL, 3.0 mmol). The reaction mixture was stirred overnight at rt. The reaction mixture was filtered through a pad of Celite and the filter pad was rinsed with EtOAc. The filtrate was concentrated onto silica gel and purified via flash chromatography on a silica gel column (0-40% EtOAc in hexanes) to isolate regioisomeric products tert-butyl 1-(5-bromopentyl)-1H-pyrazole-5-carboxylate (L7a) and tert-butyl 1-(5-bromopentyl)-1H-pyrazole-3-carboxylate (L7b). Regiochemistry was determined by HMBC. L7a: 1H NMR (400 MHz, CDCl3) δ 7.44 (s, 1H), 6.75 (s, 1H), 4.55 (t, J=7.0 Hz, 2H), 3.39 (t, J=6.2 Hz, 2H), 1.95-1.77 (m, 4H), 1.58 (s, 9H), 1.53-1.37 (m, 2H); ES/MS: m/z 317.1, 319.1 [M+H]⁺. L7b: ¹H NMR (400 MHz, CDCl3) δ 7.36 (s, 1H), 6.70 (s, 1H), 4.18 (t, J=7.0 Hz, 2H), 3.39 (t, J=6.8 Hz, 2H), 1.99-1.81 (m, 4H), 1.60 (s, 9H), 1.53-1.36 (m, 2H); ES/MS: m/z 339.1, 341.1 [M+Na]⁺.

tert-butyl 1-(4-bromobutyl)-1H-pyrazole-5-carboxylate (L7c)

Prepared following a similar procedure to L7a using 1,4-dibromobutane instead of 1,5-dibromopentane. ES/MS: m/z 303.1, 305.1 [M+H]⁺.

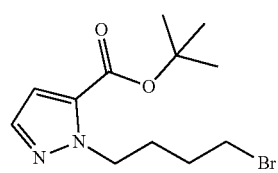

tert-butyl 1-(6-bromohexyl)-1H-pyrazole-5-carboxylate (L7d)

Prepared following a similar procedure to L7a using 1,6-dibromohexane instead of 1,5-dibromopentane. ES/MS: m/z 331.1, 333.1 [M+H]⁺.

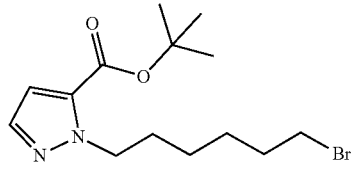

tert-butyl 1-(6-bromohexyl)-1H-pyrazole-3-carboxylate (L7e)

Prepared following a similar procedure to L7b using 1,6-dibromohexane instead of 1,5-dibromopentane. ES/MS: m/z 353.1, 355.1 [M+Na]⁺.

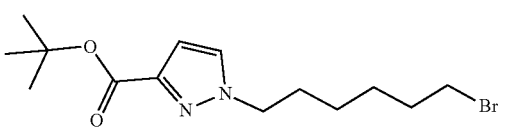

Preparation of tert-butyl 2-fluoro-3-(4-(tosyloxy)butyl)benzoate (L8a)

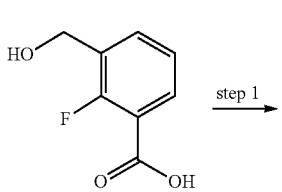

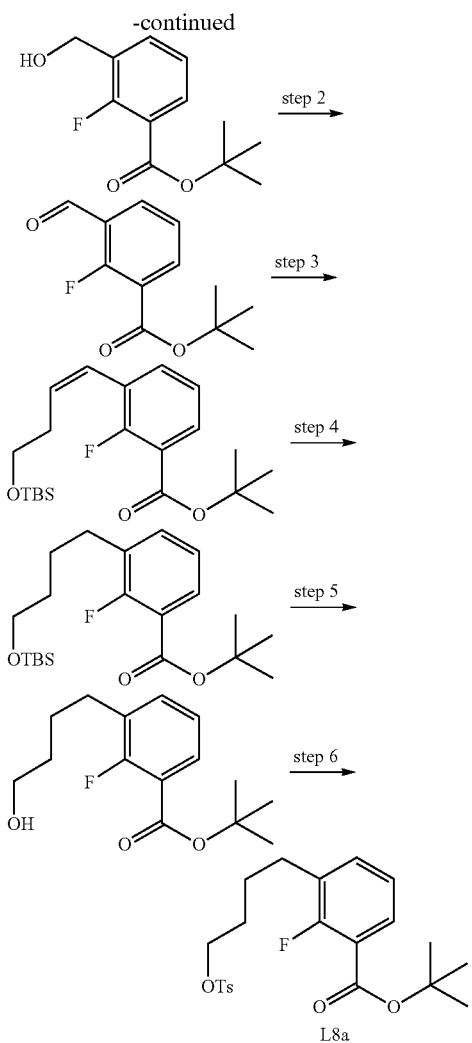

Step 1

To a solution of 2-tert-butyl-1,3-diisopropylisourea (0.59 g, 2.94 mmol) in DCM (12 mL) at 0° C. was added 2-fluoro-3-(hydroxymethyl)benzoic acid (0.50 g, 2.94 mmol). The reaction mixture was allowed to warm to rt and was stirred overnight. The reaction mixture was cooled to 0° C. and another portion of 2-tert-butyl-1,3-diisopropylisourea (0.59 g, 2.94 mmol) was added. The mixture was allowed to warm to rt and was stirred overnight. The reaction mixture was cooled to 0° C. and another portion of 2-tert-butyl-1,3-diisopropylisourea (0.59 g, 2.94 mmol) was added. After 1 h, the reaction mixture was filtered. The filtrate was washed successively with 10% citric acid soln, sat bicarb soln and brine. The organic layer was dried ($Na_2SO_4$), filtered and concentrated. The residue was purified via flash chromatography on a silica gel column (0-100% EtOAc in hexanes) to afford tert-butyl 2-fluoro-3-(hydroxymethyl)benzoate. ES/MS: m/z 249.1 $[M+Na]^+$.

Step 2

To a solution of oxalyl chloride (0.14 mL, 1.60 mmol) in DCM (10 mL) at −78° C. was added a solution of DMSO (0.24 mL, 3.33 mmol) in DCM (1 mL), dropwise. The reaction mixture was stirred for 10 min before a solution of tert-butyl 2-fluoro-3-(hydroxymethyl)benzoate (0.30 g, 1.33 mmol) in DCM (2 mL) was added, dropwise. The reaction mixture was stirred at −78° C. for 40 min. TEA (0.93 mL, 6.65 mmol) was added. The reaction mixture was stirred for 10 min at −78° C. and was then allowed to warm to rt over 30 min. The reaction mixture was diluted with water and DCM. The aqueous layer was extracted twice with DCM. The combined organic layers were washed sequentially with sat aq. $NaHCO_3$ and brine, dried ($Na_2SO_4$), filtered and concentrated to afford tert-butyl 2-fluoro-3-formylbenzoate. ES/MS: m/z 265.1 $[M+H_2O+Na]^+$.

Step 3

To a slurry of (3-((tert-butyldimethylsilyl)oxy)propyl)triphenylphosphonium bromide (0.75 g, 1.46 mmol) in THF (22 mL) at −78° C. was added LiHMDS solution (1.7 mL, 1 M in THF, 1.7 mmol), dropwise. The mixture was stirred at −78° C. for 1 h. A solution of tert-butyl 2-fluoro-3-formylbenzoate (0.30 g, 1.33 mmol) in THF (4 mL) was added. The reaction mixture was stirred at −78° C. for 1 h and was then allowed to warm to rt overnight. The reaction mixture was diluted with water and EtOAc. The aqueous layer was extracted twice with EtOAc. The combined organic layers were washed with water, dried ($Na_2SO_4$), filtered and concentrated. The residue was purified via flash chromatography on a silica gel column (0-40% EtOAc in hexanes) to afford tert-butyl 3-(4-((tert-butyldimethylsilyl)oxy)but-1-en-1-yl)-2-fluorobenzoate. ES/MS: m/z 403.2 $[M+Na]^+$.

Step 4

A mixture of tert-butyl 3-(4-((tert-butyldimethylsilyl)oxy)but-1-en-1-yl)-2-fluorobenzoate (0.35 g, 0.93 mmol) and Pd/C (0.05 g of 10% Pd/C, wet) in EtOAc and MeOH (9 mL and 1 mL, respectively) was shaken on a Parr shaker at 20 psi $H_2$ for 3 h. The mixture was filtered through Celite and the filter pad was rinsed with EtOAc/MeOH. The filtrate was concentrated to afford tert-butyl 3-(4-((tert-butyldimethylsilyl)oxy)butyl)-2-fluorobenzoate. ES/MS: m/z 405.3 $[M+Na]^+$.

Step 5

To a solution of tert-butyl 3-(4-((tert-butyldimethylsilyl)oxy)butyl)-2-fluorobenzoate (0.30 g, 0.77 mmol) in THF (7.5 mL) was added TBAF (1.5 mL of a 1 M soln in THF, 1.5 mmol). The reaction mixture was stirred at rt overnight. The reaction mixture was diluted with water and EtOAc. The aqueous layer was extracted twice with EtOAc. The combined organic layers were washed with brine, dried ($Na_2SO_4$), filtered, and concentrated. The residue was purified via flash chromatography on a silica gel column (0-50% EtOAc in hexanes) to afford tert-butyl 2-fluoro-3-(4-hydroxybutyl)benzoate. ES/MS: m/z 291.1 $[M+Na]^+$.

Step 6

To a solution of tert-butyl 2-fluoro-3-(4-hydroxybutyl)benzoate (0.21 g, 0.77 mmol), TEA (0.32 mL, 2.33 mmol) and DMAP (0.009 g, 0.078 mmol) in DCM (8 mL) at 0° C. was added p-toluenesulfonyl chloride (0.22 g, 1.16 mmol). The reaction mixture was allowed to warm to rt and was stirred overnight. The reaction mixture was diluted with water and DCM. The aqueous layer was extracted twice with DCM. The combined organic layers were washed with brine, dried ($Na_2SO_4$), filtered, and concentrated. The residue was purified via flash chromatography on a silica gel column (0-50% EtOAc in hexanes) to afford tert-butyl 2-fluoro-3-(4-(tosyloxy)butyl)benzoate. ES/MS: m/z 445.2 $[M+Na]^+$.

Preparation of tert-butyl
6-(4-(tosyloxy)butyl)picolinate (L9a)

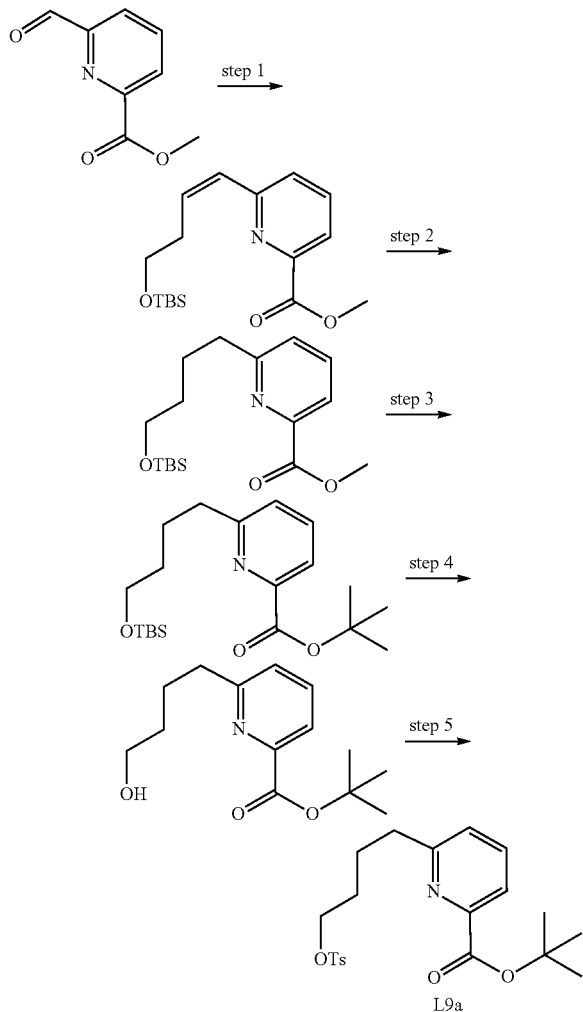

Step 1

To a slurry of (3-((tert-butyldimethylsilyl)oxy)propyl)triphenylphosphonium bromide (1.05 g, 2.03 mmol) in THF (20 mL) at −78° C. was added LiHMDS (2.2 mL of a 1 M soln in THF, 2.2 mmol), dropwise. The mixture was stirred at −78° C. for 1 h. Methyl 6-formylpicolinate (0.34 g, 2.03 mmol) was added. The reaction mixture was stirred at −78° C. for 1 h and was then allowed to warm to rt overnight. The reaction mixture was diluted with water and EtOAc. The aqueous layer was extracted twice with EtOAc. The combined organic layers were washed with water, dried (Na$_2$SO$_4$), filtered and concentrated. The residue was purified via flash chromatography on a silica gel column (0-50% EtOAc in hexanes) to afford methyl 6-(4-((tert-butyldimethylsilyl)oxy)but-1-en-1-yl)picolinate. ES/MS: m/z 322.3 [M+H]$^+$.

Step 2

A mixture of methyl 6-(4-((tert-butyldimethylsilyl)oxy)but-1-en-1-yl)picolinate (0.30 g, 0.93 mmol) and Pd/C (0.05 g of 10% Pd/C, wet) in EtOAc and MeOH (18 mL and 3 mL, respectively) was shaken on a Parr shaker at 20 psi H$_2$ for 3 h. The mixture was filtered through Celite and the filter pad was rinsed with EtOAc/MeOH. The filtrate was concentrated to afford methyl 6-(4-((tert-butyldimethylsilyl)oxy)butyl)picolinate. ES/MS: m/z 324.2 [M+H]$^+$.

Step 3

To a solution of t-BuOH (0.07 mL, 0.75 mmol) in THF (1 mL) at 0° C. was added n-BuLi (0.30 mL of a 2.5 M soln in hexanes, 0.75 mmol), followed by a solution of methyl 6-(4-((tert-butyldimethylsilyl)oxy)butyl)picolinate (0.24 g, 0.75 mmol) in THF (1.25 mL). The reaction mixture was stirred at 0° C. for 1 h. The reaction was quenched by addition of water, and the mixture was diluted with EtOAc. The aqueous layer was extracted twice with EtOAc. The combined organic layers were washed with brine, dried (Na$_2$SO$_4$), filtered, and concentrated. The residue was purified via flash chromatography on a silica gel column (0-50% EtOAc in hexanes) to afford tert-butyl 6-(4-((tert-butyldimethylsilyl)oxy)butyl)picolinate. ES/MS: m/z 366.3 [M+H]$^+$.

Step 4

To a solution of tert-butyl 6-(4-((tert-butyldimethylsilyl)oxy)butyl)picolinate (0.18 g, 0.50 mmol) in THF (5.0 mL) was added TBAF (1.0 mL of a 1 M soln in THF, 1.0 mmol). The reaction mixture was stirred at rt overnight. The reaction mixture was diluted with water and EtOAc. The aqueous layer was extracted twice with EtOAc. The combined organic layers were washed with brine, dried (Na$_2$SO$_4$), filtered, and concentrated. The residue was purified via flash chromatography on a silica gel column (0-100% EtOAc in hexanes) to afford tert-butyl 6-(4-hydroxybutyl)picolinate. ES/MS: m/z 252.2 [M+H]$^+$.

Step 5

To a solution of tert-butyl 6-(4-hydroxybutyl)picolinate (0.11 g, 0.42 mmol), TEA (0.18 mL, 1.27 mmol) and DMAP (0.005 g, 0.042 mmol) in DCM (4.2 mL) at 0° C. was added p-toluenesulfonyl chloride (0.12 g, 0.63 mmol). The reaction mixture was allowed to warm to rt and was stirred overnight. The reaction mixture was diluted with water and DCM. The aqueous layer was extracted twice with DCM. The combined organic layers were washed with brine, dried (Na$_2$SO$_4$), filtered, and concentrated. The residue was purified via flash chromatography on a silica gel column (0-100% EtOAc in hexanes) to afford tert-butyl 6-(4-(tosyloxy)butyl)picolinate. ES/MS: m/z 406.2 [M+H]$^+$.

Preparation of tert-butyl rac-3-(((1S,3R)-3-(hydroxymethyl)-2,2-dimethylcyclopropyl)methoxy)propanoate (L10)

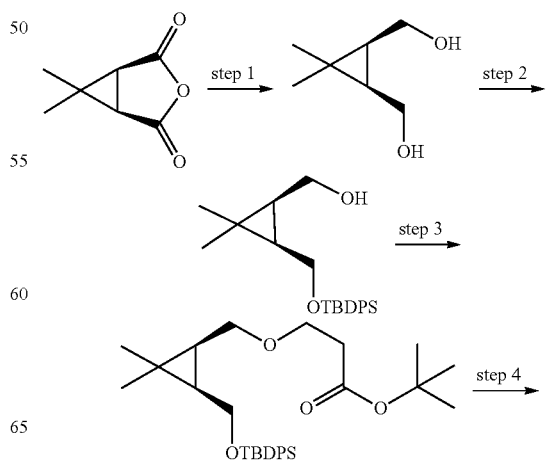

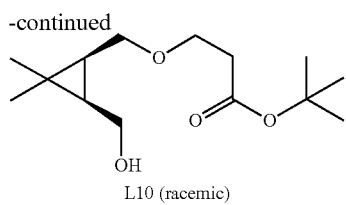

L10 (racemic)

Step 1

A solution of lithium aluminum hydride (2.0 M in THF, 28.0 mL, 56.0 mmol) was cooled under N₂ atmosphere in an ice water bath. 6,6-dimethyl-3-oxabicyclo[3.1.0]hexane-2,4-dione (2500 mg, 17.8 mmol) was then added dropwise as a solution in THF (20 mL) over ca. 20 min to maintain internal temperature below 6° C. Additional THF (2×5 mL) was used to wash.

The mixture was allowed to stir for 5 h, during which time the ice bath expired. The reaction mixture was cooled in an ice bath, and water (2.1 mL) was slowly added, maintaining internal temperature below 10° C. Then, 15% aqueous NaOH (2.1 mL) was slowly added, maintaining internal temperature below 10° C. Then, water (6.6. mL) was slowly added. Reaction mixture was removed from cold bath and allowed to stir 10 min. MgSO₄ was added, and the mixture was filtered through Celite and concentrated to afford rac-((1R,3S)-3-(((tert-butyldiphenylsilyl)oxy)methyl)-2,2-dimethylcyclopropyl)methanol that was used without further purification. ¹H NMR (400 MHz, DMSO-d6) δ 4.28 (t, J=5.2 Hz, 2H), 3.52-3.38 (m, 4H), 1.03 (s, 3H), 1.00 (s, 3H), 0.78 (ddd, J=7.5, 5.2, 2.4 Hz, 2H).

Step 2 rac-((1R,3S)-3-(((tert-Butyldiphenylsilyl)oxy)methyl)-2,2-dimethylcyclopropyl)methanol (2.08 g, 16 mmol) was dissolved in THF (100 mL) under N₂ and the resulting solution was cooled in an ice water bath. NaH as a 60% dispersion in mineral oil (0.735 g, 18.4 mmol) was added portionwise. After 2 h, tert-butylchlorodiphenylsilane (4.15 mL, 0.0160 mol) was added. The reaction mixture was stirred for 10 min and allowed to warm to r.t. After 1 h, the reaction was quenched with sat. aq. NH₄Cl and diluted with Et₂O. The organic phase was washed with brine, dried over MgSO₄, filtered, and concentrated. Purification by silica gel (0-40% EtOAc in hexanes) provided rac-((1R,3S)-3-(((tert-butyldiphenylsilyl)oxy)methyl)-2,2-dimethylcyclopropyl)methanol. ¹H NMR (400 MHz, DMSO-d6) δ 7.68-7.60 (m, 4H), 7.52-7.39 (m, 6H), 4.21 (t, J=5.1 Hz, 1H), 3.79 (dd, J=11.2, 6.2 Hz, 1H), 3.64 (dd, J=11.3, 8.3 Hz, 1H), 3.46-3.35 (m, 2H), 1.05 (s, 3H), 0.99 (s, 9H), 0.99 (s, 3H), 0.91-0.78 (m, 2H).

Step 3 rac-((1R,3S)-3-(((tert-Butyldiphenylsilyl)oxy)methyl)-2,2-dimethylcyclopropyl)methanol (2.05 g, 5.56 mmol) was dissolved in tBuOH (25 mL) and tert-butyl prop-2-enoate (16.3 mL, 111 mmol) and cesium carbonate (1.81 g, 5.56 mmol) were added. The resulting mixture was stirred at r.t. for 5 h and at 60° C. for 19 h. Reaction mixture was diluted with Et₂O and water. Organic phase was washed brine, dried over MgSO₄, filtered, and concentrated. Purification by silica gel (0-30% EtOAc in hexanes) provided tert-butyl rac-3-(((1R,3S)-3-(((tert-butyldiphenylsilyl)oxy)methyl)-2,2-dimethylcyclopropyl)methoxy)propanoate.

Step 4 tert-Butyl rac-3-[[(1S,3R)-3-[[tert-butyl(diphenyl)silyl]oxymethyl]-2,2-dimethylcyclopropyl]methoxy]propanoate (2.78 g, 5.6 mmol) was dissolved in THF (25 mL). TBAF (1.0 M in THF, 8.40 mL, 8.4 mmol) was added and the resulting mixture was stirred 5 h at r.t. Reaction mixture was partitioned between Et₂O and water. Organic phase was washed brine, dried over MgSO₄, filtered, and concentrated. Purification by silica gel (20-60% EtOAc in hexanes) provided tert-butyl rac-3-[[(1S,3R)-3-(hydroxymethyl)-2,2-dimethylcyclopropyl]methoxy]propanoate. ¹H NMR (400 MHz, DMSO-d6) δ 3.54 (t, J=6.2 Hz, 2H), 3.50-3.31 (m, 4H), 2.40 (t, J=6.1 Hz, 2H), 1.40 (s, 9H), 1.04 (s, 3H), 1.00 (s, 3H), 0.87-0.73 (m, 2H).

Preparation of tert-butyl rac-3-(((1R,2S)-2-((tosyloxy)methyl)cyclobutyl)methoxy)propanoate (L11)

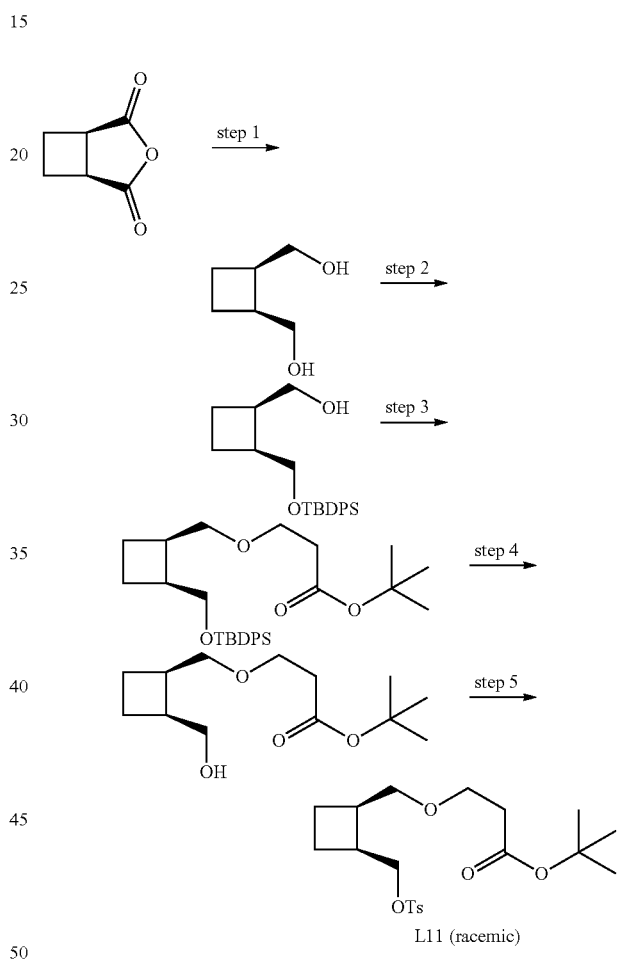

L11 (racemic)

Step 1 rac-((1R,2S)-cyclobutane-1,2-diyl)dimethanol was prepared analogously to rac-((1R,3S)-3-(((tert-butyldiphenylsilyl)oxy)methyl)-2,2-dimethylcyclopropyl)methanol (step 1 of L10), but starting with rac-(1R,5S)-3-oxabicyclo[3.2.0]heptane-2,4-dione. ¹H NMR (400 MHz, DMSO-d6) δ 4.48 (dd, J=5.7, 4.7 Hz, 2H), 3.64-3.51 (m, 2H), 3.46-3.36 (m, 2H), 2.52-2.39 (m, 2H), 1.97-1.81 (m, 2H), 1.63-1.51 (m, 2H).

Step 2 rac-((1R,2S)-2-(((tert-butyldiphenylsilyl)oxy)methyl)cyclobutyl)methanol was prepared analogously to rac-((1R,3S)-3-(((tert-butyldiphenylsilyl)oxy)methyl)-2,2-dimethylcyclopropyl)methanol (step 2 of L10), but starting with rac-((1R,2S)-cyclobutane-1,2-diyl)dimethanol. ¹H NMR (400 MHz, DMSO-d6) δ 7.66-7.57 (m, 4H), 7.51-7.39 (m, 6H), 4.27 (t, J=5.1 Hz, 1H), 3.82 (dd, J=10.4, 7.0 Hz, 1H), 3.69 (dd, J=10.4, 7.0 Hz, 1H), 3.60 (ddd, J=10.6, 6.9, 4.9 Hz, 1H), 3.46 (ddd, J=10.6, 7.6, 5.2 Hz, 1H), 2.63-2.53 (m, 1H), 2.50-2.43 (m, 1H), 1.99-1.85 (m, 2H), 1.73-1.59 (m, 2H), 0.99 (s, 9H).

Step 3 tert-butyl rac-3-(((1R,2S)-2-(((tert-butyldiphenylsilyl)oxy)methyl)cyclobutyl)methoxy)propanoate was prepared analogously to tert-butyl rac-3-(((1R,3S)-3-(((tert-butyldiphenylsilyl)oxy)methyl)-2,2-dimethylcyclopropyl)methoxy)propanoate (step 3 of L10), but starting with rac-((1R,2S)-2-(((tert-butyldiphenylsilyl)oxy)methyl)cyclobutyl)methanol. $^1$H NMR (400 MHz, DMSO-d6) δ 7.64-7.59 (m, 4H), 7.50-7.40 (m, 6H), 3.82-3.73 (m, 1H), 3.72-3.62 (m, 1H), 3.58-3.51 (m, 1H), 3.48 (t, J=6.2 Hz, 2H), 3.46-3.40 (m, 1H), 2.62-2.52 (m, 2H), 2.34 (t, J=6.2 Hz, 2H), 1.97-1.87 (m, 2H), 1.76-1.60 (m, 2H), 1.36 (s, 9H), 1.00 (s, 9H).

Step 4 tert-butyl rac-3-(((1R,2S)-2-(hydroxymethyl)cyclobutyl)methoxy)propanoate was prepared analogously to tert-butyl rac-3-[[(1S,3R)-3-(hydroxymethyl)-2,2-dimethylcyclopropyl]methoxy]propanoate (step 4 of L10), but starting with tert-butyl rac-3-(((1R,2S)-2-(((tert-butyldiphenylsilyl)oxy)methyl)cyclobutyl)methoxy)propanoate. $^1$H NMR (400 MHz, DMSO-d6) δ 4.18 (dd, J=5.6, 5.0 Hz, 1H), 3.58-3.48 (m, 4H), 3.44-3.35 (m, 2H), 2.58-2.47 (m, 1H), 2.47-2.36 (m, 3H), 1.97-1.83 (m, 2H), 1.71-1.56 (m, 2H), 1.40 (s, 9H).

Step 5 tert-butyl rac-3-(((1R,2S)-2-(hydroxymethyl)cyclobutyl)methoxy)propanoate (122 mg, 0.499 mmol) was dissolved in DCM (1.5 mL), and trimethylamine (0.21 mL, 1.5 mmol) and 4-dimethylaminopyridine (15 mg, 0.12 mmol) were added. Solution was cooled in an ice water bath and p-toluenesulfonyl chloride (0.14 g, 0.75 mmol) was added. The mixture was stirred 80 min, and then let warm to r.t. Once complete, the mixture was purified directly by silica gel chromatography to afford tert-butyl rac-3-(((1R,2S)-2-((tosyloxy)methyl)cyclobutyl)methoxy)propanoate. ES/MS: 420.93 m/z [M+Na]$^+$.

Preparation of tert-butyl 2-((6-bromohexyl)oxy)benzoate (L12)

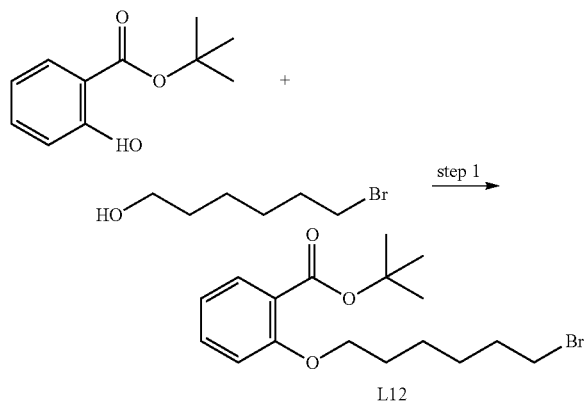

L12

Step 1

PPh$_3$ (393 mg, 1.5 mmol) was dissolved in THF (3 mL) and the solution was cooled to 0° C. DIAD (303 mg, 1.5 mmol) was added and the resulting solution was warmed to room temperature and stirred for 30 minutes. The yellow suspension was cooled back to 0° C. and a solution tert-butyl 2-hydroxybenzoate (130 mg, 1 mmol) and 6-bromohexan-1-ol (217 mg, 1.2 mmol) in THF (1 mL) was added dropwise. The reaction was warmed to room temperature and stirred overnight. Purification (Hexanes/Diethyl ether 0-10%) afforded tert-butyl 2-((6-bromohexyl)oxy)benzoate. $^1$H NMR (400 MHz, Chloroform-d) δ 7.69 (dd, J=7.6, 1.8 Hz, 1H), 7.44-7.37 (m, 1H), 7.01-6.88 (m, 2H), 4.03 (t, J=6.4 Hz, 2H), 3.45 (t, J=6.8 Hz, 2H), 2.05-1.75 (m, 4H), 1.61 (s, 9H), 1.60-1.50 (m, 4H).

Preparation of tert-butyl rac-3-(((1R,2S)-2-((tosyloxy)methyl)cyclopropyl)methoxy)propanoate (L13a)

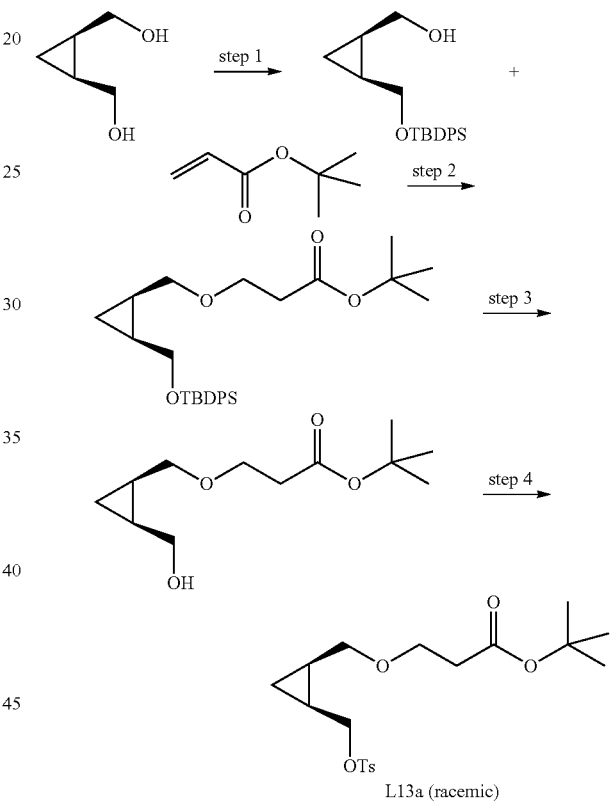

L13a (racemic)

Step 1

To a solution of cis-(cyclopropane-1,2-diyl)dimethanol (3.0 g, 29.4 mmol) in THF (50 mL) at 0° C. was added NaH (60%, 1.41 g, 35.2 mmol) and the mixture was stirred for 15 min. TBDPSCl (7.6 mL, 29.4 mmol) was then added and the reaction mixture was warmed to rt and stirred for 2 h. Saturated aqueous NH$_4$Cl was added slowly and the mixture was extracted twice with Et$_2$O. The combined organic layers were washed with brine, dried with MgSO$_4$, filtered and concentrated to provide crude rac-((1R,2S)-2-(((tert-butyldiphenylsilyl)oxy)methyl)cyclopropyl)methanol which was used below without further purification. ES/MS: m/z 363.0 [M+Na]$^+$.

Step 2

To a solution of rac-((1R,2S)-2-(((tert-butyldiphenylsilyl)oxy)methyl)cyclopropyl)methanol (ca. 7.34 mmol) in tert-BuOH (35 mL) was added tert-butyl acrylate (16.1 mL, 110 mmol) and Cs₂CO₃ (2.39 mg, 7.34 mmol). The reaction mixture was stirred at rt overnight, diluted with EtOAc, washed with brine, dried with MgSO₄, filtered and concentrated. Purification by silica gel chromatography (0-20% EtOAc in hexanes) provided tert-butyl rac-3-(((1R,2S)-2-(((tert-butyldiphenylsilyl)oxy)methyl)cyclopropyl)methoxy)propanoate. ES/MS: m/z 491.3 [M+Na]⁺.

Step 3

To a solution of tert-butyl rac-3-(((1R,2S)-2-(((tert-butyldiphenylsilyl)oxy)methyl)cyclopropyl)methoxy)propanoate (1.4 g, 2.99 mmol) in THF (15 mL) was added 1.0M TBAF in THF (4.5 mL, 4.48 mmol). The reaction mixture was stirred at room temperature for 1 h. Ethyl acetate was added and the solution was washed with saturated aqueous NaHCO₃ followed by brine. The organic phase was dried with MgSO₄, filtered, and concentrated. Purification by silica gel chromatography (0-60% EtOAc in hexanes) provided tert-butyl rac-3-(((1R,2S)-2-(hydroxymethyl)cyclopropyl)methoxy)propanoate. ¹H NMR (400 MHz, Chloroform-d) δ 4.01-3.83 (m, 2H), 3.82-3.61 (m, 2H), 3.28-3.11 (m, 2H), 3.01-2.95 (m, 1H), 2.54-2.48 (m, 2H), 1.46 (s, 9H), 1.41-1.22 (m, 2H), 0.84-0.75 (m, 1H), 0.23-0.17 (m, 1H).

Step 4

To a solution of tert-butyl rac-3-(((1R,2S)-2-(hydroxymethyl)cyclopropyl)methoxy)propanoate (260 mg, 1.13 mmol) in dichloromethane (5 mL) at 0° C. were added TsCl (323 mg, 1.69 mmol), triethylamine (0.47 mL, 3.39 mmol) and DMAP (14 mg, 0.11 mmol). The reaction mixture was stirred at room temperature overnight. The reaction mixture was diluted with DCM then washed with water and brine. The organic phase was dried with MgSO₄, filtered, and concentrated. Purification by silica gel chromatography (0-80% EtOAc in hexanes) provided tert-butyl rac-3-(((1R,2S)-2-((tosyloxy)methyl)cyclopropyl)methoxy)propanoate. ES/MS: m/z 407.2 [M+Na]⁺. 1H NMR (400 MHz, Chloroform-d) δ 7.86-7.72 (m, 2H), 7.34 (d, J=7.8 Hz, 2H), 4.17-4.03 (m, 2H), 3.66-3.54 (m, 2H), 3.43 (dd, J=10.7, 5.9 Hz, 1H), 3.32 (dd, J=10.6, 6.7 Hz, 1H), 2.50-2.40 (m, 5H), 1.44 (s, 9H), 1.32-1.20 (m, 2H), 0.91-0.81 (m, 1H), 0.32 (q, J=5.7 Hz, 1H).

tert-butyl rac-3-(((1S,2S)-2-((tosyloxy)methyl)cyclopropyl)methoxy)propanoate (L13b)

Prepared following a similar procedure to L13a from rac-((1S,2S)-2-(((tert-butyldimethylsilyl)oxy)methyl)cyclopropyl)methanol (WO 2008115381 A1). ¹H NMR (400 MHz, Chloroform-d) δ 7.78 (d, J=7.9 Hz, 2H), 7.34 (d, J=8.1 Hz, 2H), 3.96 (dd, J=10.6, 7.1 Hz, 1H), 3.92-3.84 (m, 1H), 3.63 (tt, J=6.4, 1.3 Hz, 2H), 3.32 (dd, J=10.4, 6.3 Hz, 1H), 3.26-3.19 (m, 1H), 2.50-2.42 (m, 5H), 1.44 (s, 9H), 1.09-0.92 (m, 2H), 0.60-0.45 (m, 2H).

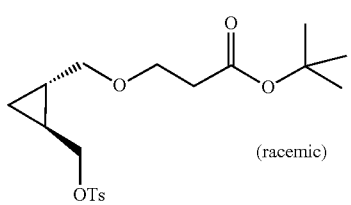

(racemic)

L13b tert-butyl 3-((1-((tosyloxy)methyl)cyclopropyl)methoxy)propanoate (L13c)

Prepared following a similar procedure to L13a from cyclopropane-1,1-diyldimethanol. ES/MS: m/z 407.2 [M+Na]⁺.

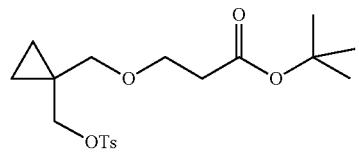

L13c tert-butyl 3-(((1R,2S)-2-((tosyloxy)methyl)cyclopropyl)methoxy)propanoate (L13d)

Prepared following a similar procedure to L13a from ((1R,2S)-2-(((tert-butyldiphenylsilyl)oxy)methyl)cyclopropyl)methanol (J. Am. Chem. Soc. 2008, 16424). ES/MS: m/z 407.2 [M+Na]⁺.

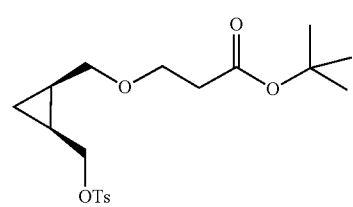

L13d tert-butyl 3-(((1S,2R)-2-((tosyloxy)methyl)cyclopropyl)methoxy)propanoate (L13e)

Prepared following a similar procedure to L13a from ((1S,2R)-2-(((tert-butyldiphenylsilyl)oxy)methyl)cyclopropyl)methanol (J. Am. Chem. Soc. 2008, 16424). ES/MS: m/z 407.2 [M+Na]⁺.

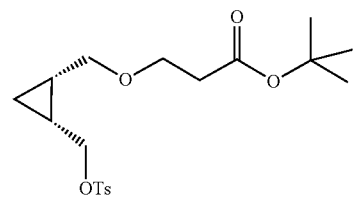

L13e tert-butyl 3-(((1R,2S)-2-(hydroxymethyl)cyclopropyl)methoxy)propanoate (L3f)

Prepared following a similar procedure to L13d stopping the sequence after step 3. ES/MS: m/z 253.2 [M+Na]⁺.

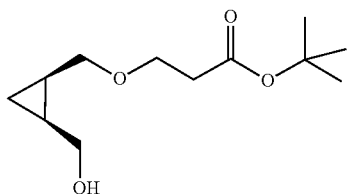

tert-butyl 3-(((1R,2S)-2-(hydroxymethyl)cyclopropyl)methoxy)-2-methylpropanoate (L13g)

Prepared following a similar procedure to L13a using tert-butyl methacrylate instead of tert-butyl acrylate and stopping the sequence after step 3. ES/MS: m/z 267.2 [M+Na]⁺.

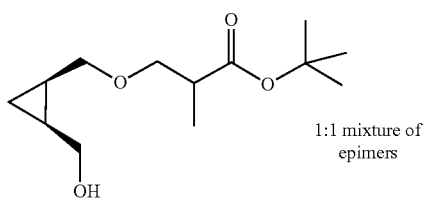

1:1 mixture of epimers

Preparation of tert-butyl rac-3-(((1R,2S)-2-((tosyloxy)methyl)cyclopropyl)methoxy)propanoate (L14a)

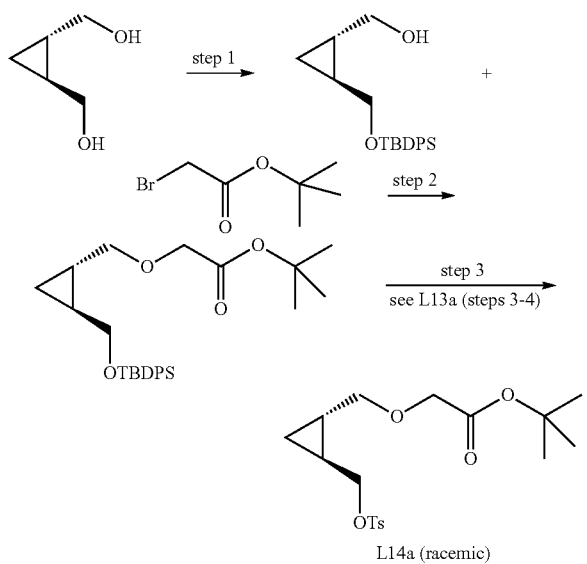

L14a (racemic)

Step 1

To a solution of trans-(cyclopropane-1,2-diyl)dimethanol (3.0 g, 29.4 mmol) in THF (50 mL) at 0° C. was added NaH (60% dispersion, 1.41 g, 35.2 mmol) and the mixture was stirred for 15 min. TBDPSCl (7.6 mL, 29.4 mmol) was then added and the reaction mixture was warmed to rt and stirred for 2 h. Saturated aqueous NH₄Cl was added slowly and the mixture was extracted twice with Et₂O. The combined organic layers were washed with brine, dried with MgSO₄, filtered and concentrated to provide crude rac-((1S,2S)-2-(((tert-butyldiphenylsilyl)oxy)methyl)cyclopropyl)methanol which was used below without further purification. ES/MS: m/z 363.0 [M+Na]⁺.

Step 2

To a solution of rac-((1S,2S)-2-(((tert-butyldiphenylsilyl)oxy)methyl)cyclopropyl)methanol (375 mg, 1.10 mmol) and Bu₄NCl (101 mg, 0.33 mmol) in toluene (6 mL) at 0° C. was added 35% aqueous NaOH (6 mL). Tert-butylbromoacetate (0.244 mL, 1.65 mmol) was then added dropwise at 0° C. The reaction mixture was stirred at rt overnight, diluted with EtOAc, washed with water and brine, dried with MgSO₄, filtered and concentrated. Purification by silica gel chromatography (0-30% EtOAc in hexanes) provided tert-butyl 2-(((1S,2S)-2-(((tert-butyldiphenylsilyl)oxy)methyl)cyclopropyl)methoxy)acetate. ES/MS: m/z 477.3 [M+Na]⁺.

Step 3 tert-butyl 2-(((1S,2S)-2-((tosyloxy)methyl)cyclopropyl)methoxy)acetate was made following steps 3-4 of intermediate L13a using tert-butyl 2-(((1S,2S)-2-(((tert-butyldiphenylsilyl)oxy)methyl)cyclopropyl)methoxy)acetate. ES/MS: m/z 393.2 [M+Na]⁺.

tert-butyl 2-(2-(1-(2-(tosyloxy)ethyl)cyclopropyl)ethoxy)acetate (L14b)

Prepared following a similar procedure to L14a from 2,2'-(cyclopropane-1,1-diyl)bis(ethan-1-ol). ES/MS: m/z 421.2 [M+Na]⁺.

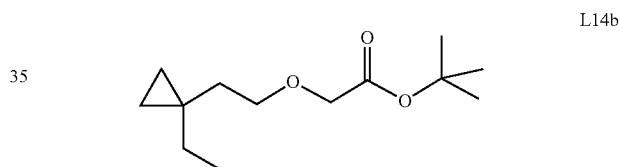

Preparation of tert-butyl 3-((1-(2-(tosyloxy)ethyl)cyclopropyl)methoxy)propanoate (L15a)

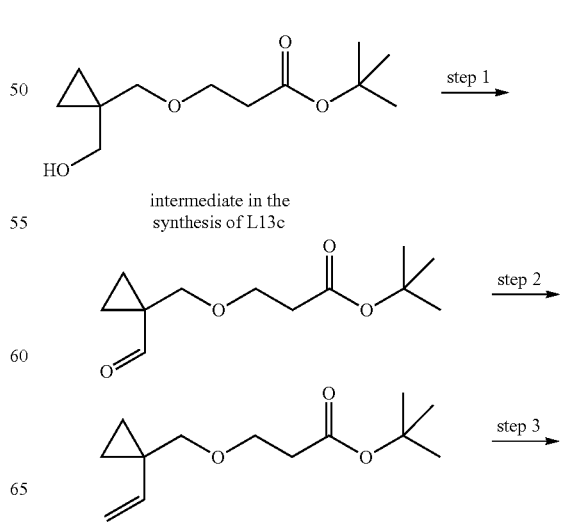

intermediate in the synthesis of L13c

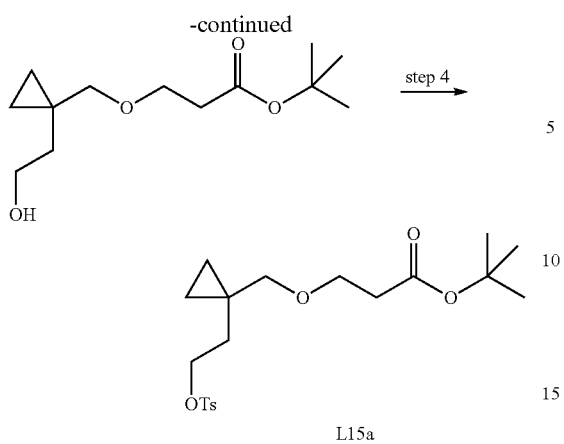

L15a

Step 1

To a solution of DMSO (0.57 mL, 8.1 mmol) in DCM (40 mL) at −78° C. was added oxalyl chloride (0.56 mL, 6.6 mmol). The solution was stirred at −78° C. for 30 minutes before the addition of a solution of tert-butyl 3-((1-(hydroxymethyl)cyclopropyl)methoxy)propanoate (intermediate in the synthesis of L13c, 1.16 g, 5.04 mmol) in DCM (10 mL). The mixture was stirred at −78° C. for 30 minutes before the addition of Et$_3$N (3.5 mL, 25.2 mmol). The reaction mixture was warmed to room temperature and stirred for 15 minutes. 1N HCl was added slowly and the mixture was extracted twice with DCM. The combined organic layers were washed with brine, dried with MgSO$_4$, filtered and concentrated to provide crude tert-butyl 3-((1-formylcyclopropyl)methoxy)propanoate which was used below without further purification. $^1$H NMR (400 MHz, Chloroform-d) δ 9.03 (s, 1H), 3.76-3.60 (m, 4H), 2.48 (t, J=6.3 Hz, 2H), 1.45 (s, 9H), 1.25-1.06 (m, 4H).

Step 2

To a suspension of methyltriphenylphosphonium bromide (1.36 g, 3.8 mmol) in THF (35 mL) at 0° C. was added n-BuLi (1.7 M in hexane, 2.24 mL, 3.8 mmol). The resulting solution was stirred for 10 minutes. A solution of tert-butyl 3-((1-formylcyclopropyl)methoxy)propanoate (580 mg, 2.54 mmol) in THF (15 mL) was added dropwise at 0° C. and the resulting solution was stirred at 0° C. for 1 h. Water was then added and the mixture was extracted with diethyl ether. The combined organic layers were washed with brine, dried over MgSO$_4$ and concentrated under reduced pressure. Purification by silica gel chromatography (0-30% EtOAc in hexanes) provided tert-butyl 3-((1-vinylcyclopropyl)methoxy)propanoate. $^1$H NMR (400 MHz, Chloroform-d) δ 5.63 (dd, J=17.4, 10.7 Hz, 1H), 5.02 (d, J=10.8 Hz, 1H), 4.94 (d, J=10.8 Hz, 1H), 3.68 (t, J=6.5 Hz, 2H), 3.44 (s, 2H), 2.49 (t, J=6.5 Hz, 2H), 1.45 (s, 9H), 0.83-0.52 (m, 4H).

Step 3

A solution of tert-butyl 3-((1-vinylcyclopropyl)methoxy)propanoate in THF was added to a solution of 1 M borane in THF at 0° C. The solution was stirred at 0° C. for 2 h. The mixture was subsequently treated with water, 15% aqueous NaOH and 30% aqueous H$_2$O$_2$. The mixture was then stirred 2 h at rt. Water was added slowly and the mixture was extracted twice with EtOAc. The combined organic layers were washed with brine, dried with MgSO$_4$, filtered and concentrated to provide crude tert-butyl 3-((1-(2-hydroxyethyl)cyclopropyl)methoxy)propanoate which was used below without further purification. ES/MS: m/z 266.9 [M+Na]$^+$.

Step 4 tert-butyl 3-((1-(2-(tosyloxy)ethyl)cyclopropyl)methoxy)propanoate was made following step 4 of intermediate L13a using tert-butyl 3-((1-(2-hydroxyethyl)cyclopropyl)methoxy)propanoate. ES/MS: m/z 421.2 [M+Na]$^+$.

tert-butyl 3-(((1R,2R)-2-(2-(tosyloxy)ethyl)cyclopropyl)methoxy)propanoate (L15b)

Prepared using a similar procedure to L15a from tert-butyl 3-(((1R,2S)-2-(hydroxymethyl)cyclopropyl)methoxy)propanoate (intermediate in the synthesis of L13d). ES/MS: m/z 421.2 [M+Na]$^+$.

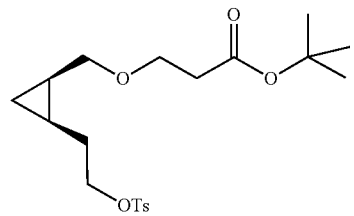

L15b

Preparation of tert-butyl (R)-3-methoxy-8-(tosyloxy)octanoate (L16a)

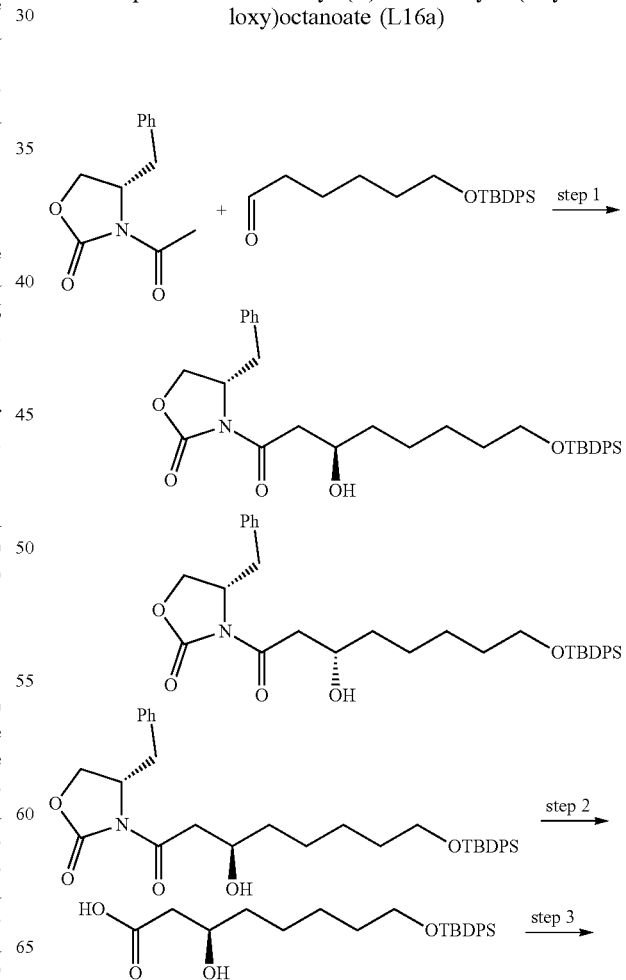

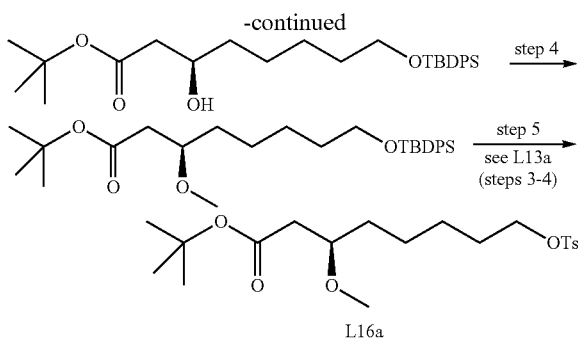

Step 1

A solution of (S)-3-acetyl-4-benzyloxazolidin-2-one (2.8 g, 13 mmol) in DCM (35 mL) was cooled to −78° C. before adding TiCl$_4$ (1.43 mL, 13 mmol). DIEA (2.26 mL, 13 mmol) was then added and the mixture was stirred at −78° C. for 1 h. A solution of 6-((tert-butyldiphenylsilyl)oxy) hexanal (4.6 g, 13 mmol, J. Am. Chem. Soc. 2013, 9358) in DCM (5 mL) was then added. The mixture was stirred at −78° C. for 1 h and quenched with 40 mL of 1N HCl. After stirring for 15 min at rt, saturated aqueous NH$_4$Cl was added and the mixture was extracted twice with DCM. The combined organics were washed with water, brine, dried (MgSO$_4$), filtered, and concentrated under reduced pressure. The resulting residue (3:1 mixture of diastereoisomers) was purified via silica gel column chromatography (0-40% ethyl acetate in hexanes) to yield (S)-4-benzyl-3-((R)-8-((tert-butyldiphenylsilyl)oxy)-3-hydroxyoctanoyl)oxazolidin-2-one (major) and (S)-4-benzyl-3-((S)-8-((tert-butyldiphenylsilyl)oxy)-3-hydroxyoctanoyl)oxazolidin-2-one (minor). $^1$H NMR of major product (400 MHz, Chloroform-d) δ 7.67 (d, J=7.6 Hz, 4H), 7.48-7.13 (m, 11H), 4.74-4.65 (m, 1H), 4.28-4.00 (m, 4H), 3.66 (t, J=6.4 Hz, 2H), 3.29 (dd, J=13.5, 3.5 Hz, 1H), 3.17-2.98 (m, 2H), 2.93 (d, J=4.3 Hz, 1H), 2.81 (dd, J=13.4, 9.4 Hz, 1H), 1.63-1.32 (m, 6H), 1.05 (s, 9H). $^1$H NMR of minor product (400 MHz, Chloroform-d) δ 7.74-7.58 (m, 4H), 7.48-7.13 (m, 11H), 4.69 (ddt, J=10.5, 7.0, 3.3 Hz, 1H), 4.32-4.02 (m, 4H), 3.67 (t, J=6.4 Hz, 2H), 3.31 (dd, J=13.4, 3.4 Hz, 1H), 3.17 (dd, J=17.7, 2.5 Hz, 1H), 2.97 (dd, J=17.5, 9.4 Hz, 1H), 2.87-2.68 (m, 2H), 1.69-1.32 (m, 6H), 1.05 (s, 9H).

Step 2

30% aqueous H$_2$O$_2$ (3.6 mL, 31.8 mmol) was added to a solution of LiOH·H$_2$O (444 mg, 10.6 mmol) in THF (25 mL) and water (10 mL) at 0° C. The mixture was stirred for 15 min at 0° C. followed by the addition of (S)-4-benzyl-3-((R)-8-((tert-butyldiphenylsilyl)oxy)-3-hydroxyoctanoyl) oxazolidin-2-one (2.43 g, 4.23 mmol) in THF (10 mL). The reaction mixture was stirred at rt overnight and quenched with 1N HCl. The reaction mixture was partitioned between DCM and water, and the organic phase was washed with brine, dried with MgSO$_4$, filtered, and concentrated to provide crude (R)-8-((tert-butyldiphenylsilyl)oxy)-3-hydroxyoctanoic acid which was used below without further purification. ES/MS: m/z 437.3 [M+Na]$^+$.

Step 3

A solution of (R)-8-((tert-butyldiphenylsilyl)oxy)-3-hydroxyoctanoic acid (800 mg, 1.93 mmol) and tert-butyl 2,2,2-trichloroethanimidate (1.73 mL, 9.65 mmol) in DCM (20 mL) was stirred at rt for 4 days. Concentration and purification by silica gel chromatography (0-50% EtOAc in hexanes) provided tert-butyl (R)-8-((tert-butyldiphenylsilyl)oxy)-3-hydroxyoctanoate. ES/MS: m/z 493.3 [M+Na]$^+$.

Step 4

To a stirred solution of tert-butyl (R)-8-((tert-butyldiphenylsilyl)oxy)-3-hydroxyoctanoate (309 mg, 0.66 mmol) in DMF (3 mL) at 0° C. were added MeI (0.2 mL, 3.3 mmol) and NaH (60% oil suspension, 66 mg, 1.6 mmol). The mixture was stirred at rt for 30 min, diluted with water and EtOAc, then extracted with EtOAc. The combined extracts were washed with brine, dried with MgSO$_4$, and concentrated. Purification by silica gel chromatography (0-20% EtOAc in hexanes) provided tert-butyl (R)-8-((tert-butyldiphenylsilyl)oxy)-3-hydroxyoctanoate. ES/MS: m/z 507.3 [M+Na]$^+$.

Step 5 tert-Butyl (R)-3-methoxy-8-(tosyloxy)octanoate (L16a) was made following steps 3-4 of intermediate L13a using tert-butyl (R)-8-((tert-butyldiphenylsilyl)oxy)-3-hydroxyoctanoate. ES/MS: m/z 423.2 [M+Na]$^+$.

tert-Butyl (S)-3-methoxy-8-(tosyloxy)octanoate (L16b)

Prepared following a similar procedure to L16a from (S)-4-benzyl-3-((S)-8-((tert-butyldiphenylsilyl)oxy)-3-hydroxyoctanoyl)oxazolidin-2-one. ES/MS: m/z 423.2 [M+Na]$^+$.

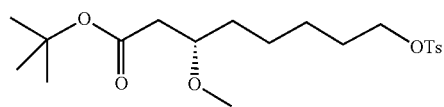

Preparation of tert-butyl 2-methoxy-2-methyl-8-(tosyloxy)octanoate (L17, Approximatively a 2:1 Mixture of Unspecified Enantiomers)

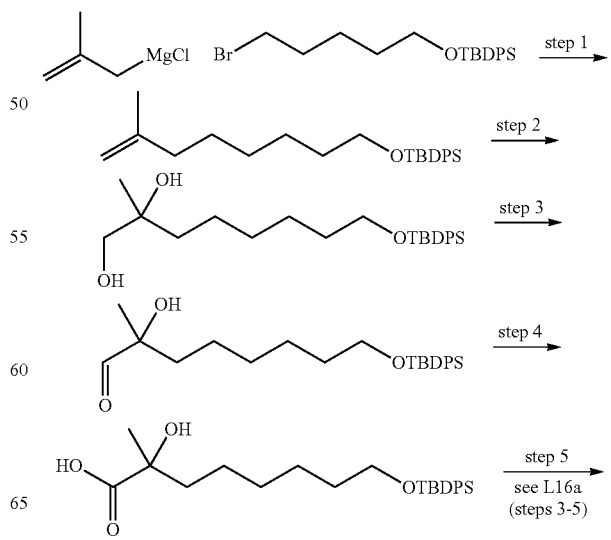

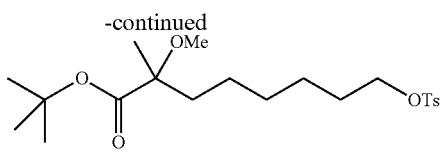

L17
(2:1 mixture of enantiomers based on the macocyclized intermediate after step 3 of Procedure 8/9)

Step 1

To a solution of ((5-bromopentyl)oxy)(tert-butyl)diphenylsilane (2.0 g, 4.93 mmol) in THF (3.0 mL) at −78° C. was added $Li_2CuCl_4$ (19 mg, 0.1 mmol). A solution of chloro(2-methylallyl)magnesium (0.5 M in THF, 19.7 mL, 9.9 mmol) was the added dropwise over 20 min. The reaction mixture was stirred at −78° C. for 1 h followed by 4 h at 0° C. to rt. The reaction mixture was partitioned between EtOAc and brine, and the organic phase was dried with $MgSO_4$, filtered, and concentrated. Purification by silica gel chromatography (100% hexanes) provided tert-butyl((7-methyloct-7-en-1-yl)oxy)diphenylsilane. $^1$H NMR (400 MHz, Chloroform-d) δ 7.72-7.59 (m, 4H), 7.46-7.31 (m, 6H), 4.67 (d, J=12.1 Hz, 2H), 3.65 (td, J=6.7, 2.2 Hz, 2H), 1.98 (t, J=7.5 Hz, 2H), 1.70 (d, J=2.3 Hz, 3H), 1.61-1.49 (m, 2H), 1.47-1.20 (m, 6H), 1.04 (d, J=2.4 Hz, 9H).

Step 2

AD-mix-β (1.4 g per mmol of alkene) was dissolved in tBuOH (25 mL) and $H_2O$ (25 mL) at rt. The clear orange solution was cooled to 0° C. and tert-butyl((7-methyloct-7-en-1-yl)oxy)diphenylsilane (1.88 g, 4.94 mmol) was added dropwise. The mixture was stirred for overnight at 0° C. to rt, quenched with saturated $Na_2SO_3$, stirred for 1 h at rt, diluted with $H_2O$ and extracted with EtOAc. The organic layers were combined, dried with $MgSO_4$ and concentrated. Purification by silica gel chromatography (0-100% EtOAc in hexanes) provided 8-((tert-butyldiphenylsilyl)oxy)-2-methyloctane-1,2-diol. ES/MS: m/z 437.2 $[M+Na]^+$.

Step 3

To a solution of 8-((tert-butyldiphenylsilyl)oxy)-2-methyloctane-1,2-diol (1.45 g, 3.0 mmol), DMSO (0.87 mL, 12.2 mmol), and $Et_3N$ (1.7 mL, 12.2 mmol) in DCM (17 mL) was added sulfur pyridine trioxide complex (1.39 g, 8.74 mmol) at 0° C. The reaction mixture was stirred at 0° C. to rt for 5 h. The reaction mixture was quenched with saturated aqueous $NH_4Cl$. The mixture was extracted twice with DCM. The organic layers were combined, dried with $MgSO_4$ and concentrated. Purification by silica gel chromatography (0-100% EtOAc in hexanes) provided 8-((tert-butyldiphenylsilyl)oxy)-2-hydroxy-2-methyloctanal. ES/MS: m/z 435.3 $[M+Na]^+$.

Step 4

To a solution of 8-((tert-butyldiphenylsilyl)oxy)-2-hydroxy-2-methyloctanal (934 mg, 2.26 mmol) in tBuOH (10 mL), THF (5 mL) and water (5 mL) was added $KH_2PO_4$ (1.97 g, 11.3 mmol) followed by 2-methyl-2-butene (1.2 mL, 11.3 mmol). Sodium chlorite (512 mg, 5.66 mmol) in water (1 mL) was the added dropwise. The reaction mixture was stirred at rt for 1 h. The reaction mixture was then partitioned between 1 N HCl and EtOAc, and the organic phase was washed with brine, dried with $MgSO_4$, filtered, and concentrated to provide crude 8-((tert-butyldiphenylsilyl)oxy)-2-hydroxy-2-methyloctanoic acid which was used below without further purification. ES/MS: m/z 451.3 $[M+Na]^+$.

Step 5 tert-Butyl 2-methoxy-2-methyl-8-(tosyloxy)octanoate (approximatively a 2:1 mixture of unspecified enantiomers) was made following steps 3-5 of intermediate L16a using 8-((tert-butyldiphenylsilyl)oxy)-2-hydroxy-2-methyloctanoic acid. ES/MS: m/z 437.2 $[M+Na]^+$.

Preparation of tert-butyl rac-2-methoxy-8-(tosyloxy)octanoate (L18)

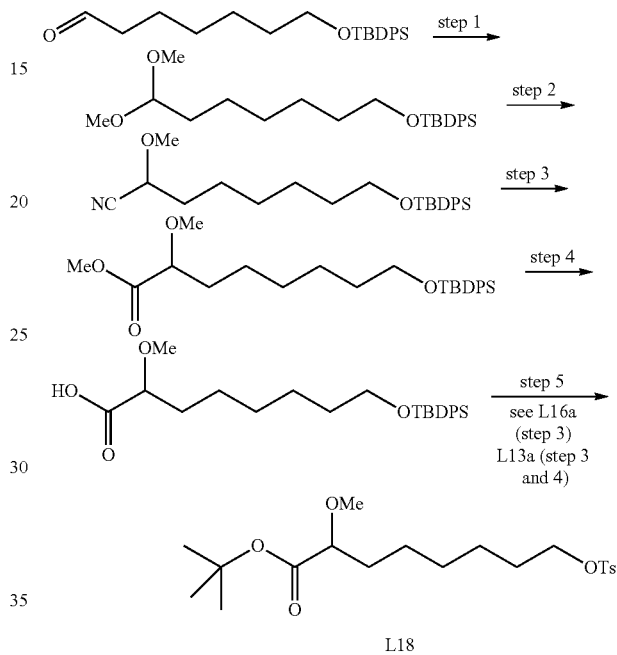

Step 1.

A solution of 7-((tert-butyldiphenylsilyl)oxy)heptanal (3.64 g, 9.88 mmol), 10-camphorsulfonic acid (344 mg, 1.48 mmol) and methanol (40 mL) in dry DCM (100 mL) was stirred at room temperature for 4h (disappearance of SM by TLC). Saturated $NaHCO_3$ aq. was added to the reaction mixture and the solution was extracted with DCM. The organic layer was washed with brine, dried with $MgSO_4$, filtered, and evaporated under vacuum. Purification by silica gel chromatography (0-15% EtOAc in hexanes) provided tert-butyl((7,7-dimethoxyheptyl)oxy)diphenylsilane. $^1$H NMR (400 MHz, Chloroform-d) δ 7.66 (d, J=7.8 Hz, 4H), 7.52-7.31 (m, 6H), 4.37-4.33 (m, 1H), 3.3.67-3.58 (m, 2H), 3.31 (d, J=1.1 Hz, 6H), 1.66-1.49 (m, 4H), 1.45-1.23 (m, 6H), 1.04 (s, 9H).

Step 2

A solution of tert-butyl((7,7-dimethoxyheptyl)oxy)diphenylsilane (1.5 g, 3.62 mmol) and 2,2'-bipyridyl (1.69 g, 10.9 mmol) in DCM (20 mL) was added TESOTf (1.64 mL, 7.23 mmol) at 0° C. After disappearance of SM by TLC, TMSCN (1.79 g, 18.1 mmol) was added and the solution was warmed to rt and stirred for 4 h. Saturated $NaHCO_3$ aq. was added to the reaction mixture and the solution was extracted with DCM. The organic layer was washed with brine, dried with $MgSO_4$, filtered, and evaporated under vacuum. Purification by silica gel chromatography (0-100% EtOAc in hexanes) provided 8-((tert-butyldiphenylsilyl)oxy)-2-methoxyoctanenitrile. ES/MS: m/z 432.3 $[M+Na]^+$.

Step 3

A solution of 8-((tert-butyldiphenylsilyl)oxy)-2-methoxyoctanenitrile (1.4 g, 3.42 mmol) and MeONa (25% in MeOH, 2.34 mL, 10.3 mmol) in MeOH (17 mL) was stirred at rt overnight. 10% aqueous citric acid was added and the solution was extracted with EtOAc. The organic layer was washed with brine, dried with MgSO$_4$, filtered, and evaporated under vacuum. Purification by silica gel chromatography (0-80% EtOAc in hexanes) provided methyl 8-((tert-butyldiphenylsilyl)oxy)-2-methoxyoctanoate. ES/MS: m/z 465.3 [M+Na]$^+$.

Step 4

To a solution of methyl 8-((tert-butyldiphenylsilyl)oxy)-2-methoxyoctanoate (331 mg, 0.748 mmol) in THF (4 mL), MeOH (4 mL) and 1 M LiOH (1.5 mL) was stirred at rt for 2 h.

The reaction mixture was then partitioned between 1N HCl and EtOAc, and the organic phase was washed with brine, dried with MgSO$_4$, filtered, and concentrated to provide crude 8-((tert-butyldiphenylsilyl)oxy)-2-methoxyoctanoic acid which was used below without further purification. ES/MS: m/z 451.1 [M+Na]$^+$.

Step 5 tert-butyl rac-2-methoxy-8-(tosyloxy)octanoate was made following step 3 of intermediate L16a and steps 3-4 of L13a using 8-((tert-butyldiphenylsilyl)oxy)-2-methoxyoctanoic acid. ES/MS: m/z 423.2 [M+Na]$^+$.

Preparation of tert-butyl 3-(((1R,2R)-2-((tosyloxy)methyl)cyclopropyl)methoxy)propanoate (L19a)

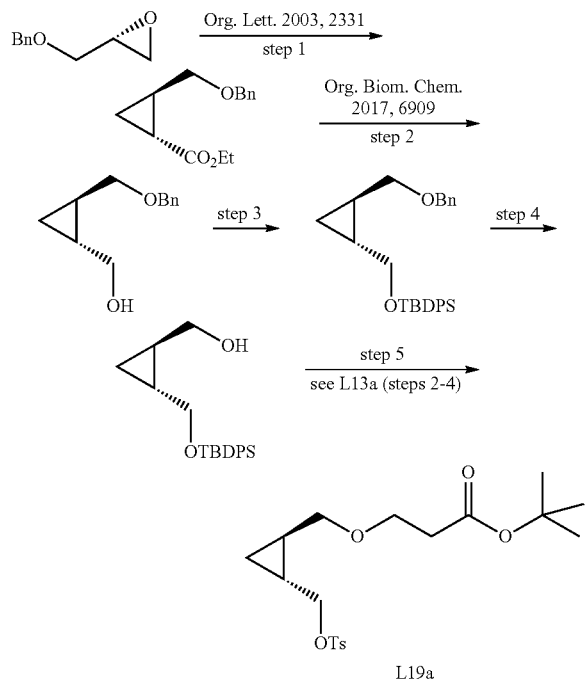

L19a

Step 1 and 2.

See Org. Lett. 2003, 2331 and Org. Biomol. Chem. 2017, 6909.

Step 3.

To a solution of ((1R,2R)-2-((benzyloxy)methyl)cyclopropyl)methanol (60 g, 312 mmol) in THF (420 mL) were added imidazole (21.2 g, 312 mmol) and TBDPSCl (102 g, 374 mmol) at 0° C. The mixture was stirred at rt for overnight. Water was added to the reaction mixture and the solution was extracted with EtOAc. The organic layer was washed with brine, dried with MgSO$_4$, filtered, and evaporated under vacuum. Purification by silica gel chromatography (10% EtOAC in petroleum ether) provided (((1R,2R)-2-((benzyloxy)methyl)cyclopropyl)methoxy)(tert-butyl)diphenylsilane.

Step 4

To a solution of (((1R,2R)-2-((benzyloxy)methyl)cyclopropyl)methoxy)(tert-butyl)diphenylsilane (65 g, 150 mmol) in EtOH (455 mL) was added wet Pd/C (6.5 g, 10%). The flask was degassed twice, purged with H$_2$ (50 psi) and stirred at 45° C. for overnight. The reaction mixture was filtered and evaporated under vacuum. Purification by silica gel chromatography (10% EtOAC in petroleum ether) provided ((1R,2R)-2-(((tert-butyldiphenylsilyl)oxy)methyl)cyclopropyl)methanol. $^1$H NMR (CDCl$_3$ 400 MHz): δ 7.70-7.67 (m, 4H), 7.44-7.38 (m, 6H), 3.72-3.68 (m, 1H), 3.49-3.44 (m, 3H), 1.35 (s, 1H), 1.06 (s, 9H), 1.00-0.96 (m, 2H), 0.47-0.40 (m, 2H).

Step 5 tert-butyl 3-(((1R,2R)-2-((tosyloxy)methyl)cyclopropyl)methoxy)propanoate was made following steps 2-4 of L13a using ((1R,2R)-2-(((tert-butyldiphenylsilyl)oxy)methyl)cyclopropyl)methanol. ES/MS: m/z 407.2 [M+Na]$^+$.

tert-Butyl 3-(((1S,2S)-2-((tosyloxy)methyl)cyclopropyl)methoxy)propanoate (L19b)

Prepared following a similar procedure to L19a from (S)-2-((benzyloxy)methyl)oxirane. ES/MS: m/z 407.2 [M+Na]$^+$.

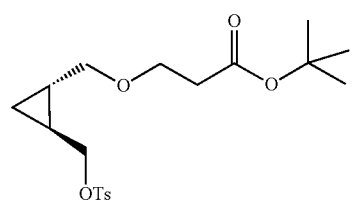

L19b tert-butyl 3-(((1R,2R)-2-(hydroxymethyl)cyclopropyl)methoxy)-2-methylpropanoate (L19c)

Prepared following a similar procedure to L19a using tert-butyl methacrylate instead of tert-butyl acrylate in step 5. ES/MS: m/z 277.2 [M+Na]$^+$.

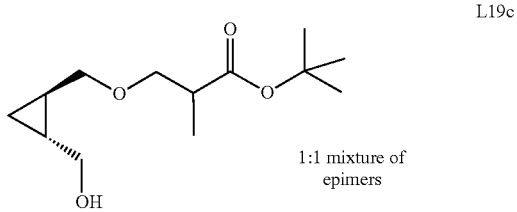 [SMILES: CC(COC[C@@H]1C[C@H]1CO)C(=O)OC(C)(C)C]

L19c

1:1 mixture of epimers tert-butyl 3-(((1R,2R)-2-(hydroxymethyl)cyclopropyl)methoxy)butanoate (L19d)

Prepared following a similar procedure to L19a using tert-butyl (E)-but-2-enoate instead of tert-butyl acrylate in step 5. ES/MS: m/z 277.2 [M+Na]$^+$.

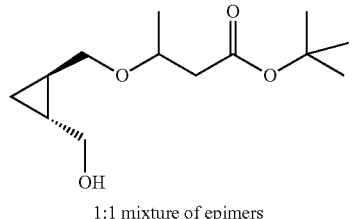

L19d

1:1 mixture of epimers tert-butyl 3-(((1S,2S)-2-(hydroxymethyl)cyclopropyl)methoxy)butanoate (L19e)

Prepared following a similar procedure to L19b using tert-butyl (E)-but-2-enoate instead of tert-butyl acrylate. ES/MS: m/z 277.2 [M+Na]$^+$.

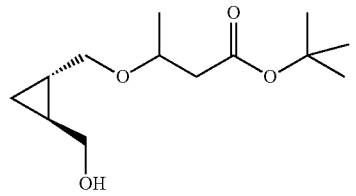

L19e

1:1 mixture of epimers

Preparation of tert-butyl rac-(1R,2R)-2-(4-(tosyloxy)butyl)cyclopropane-1-carboxylate (L20a)

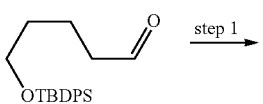

step 1

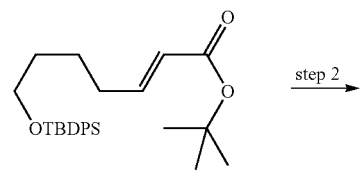

step 2

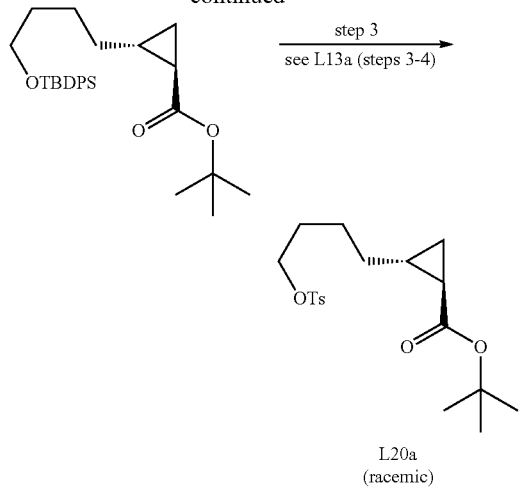

L20a (racemic)

Step 1 tert-Butyl 2-(triphenyl-λ5-phosphanylidene)acetate (1.85 g, 4.9 mmol) was added to a solution of 5-[tert-butyl(diphenyl)silyl]oxypentanal (1.67 g, 4.9 mmol) in THF (15 mL). The resulting mixture was stirred overnight. It was evaporated to dryness, redissolved in DCM (8 mL) and purified by column chromatography over silica gel (Hexanes/EtOAc 0-15%) to afford tert-butyl (E)-7-[tert-butyl(diphenyl)silyl]oxyhept-2-enoate. $^1$H NMR (400 MHz, Chloroform-d) δ, 7.72-7.65 (m, 4H), 7.48-7.37 (m, 6H), 6.87 (dt, J=15.6, 6.9 Hz, 1H), 5.74 (d, J=15.6 Hz, 1H), 3.68 (t, J=5.8 Hz, 2H), 2.22-2.14 (m, 2H), 1.64-1.55 (m, 2H), 1.51 (s, 9H), 1.39-1.18 (m, 2H), 1.07 (s, 9H).

Step 2

Trimethylsulfoxonium iodide (610 mg, 2.77 mmol) was suspended in DMSO (10 mL) and NaH (60% in mineral oil, 67 mg, 2.77 mmol) was added. The resulting mixture was stirred for 1 hour before a solution of tert-butyl (E)-7-[tert-butyl(diphenyl)silyl]oxyhept-2-enoate (760 mg, 1.73 mmol) in DMSO (2 mL) was added. The reaction mixture was stirred vigorously for 2 hours and then work up was carried out using water/ethyl acetate. The residue was purified by column chromatography over silica gel (Hexanes/EtOAc 0-10%) to afford tert-butyl rac-(trans)-2-[4-[tert-butyl(diphenyl)silyl]oxybutyl]cyclopropanecarboxylate. $^1$H NMR (400 MHz, Chloroform-d) δ 7.68 (dd, J=7.9, 1.7 Hz, 4H), 7.49-7.35 (m, 6H), 3.68 (td, J=6.2, 2.0 Hz, 2H), 2.94-2.75 (m, 2H), 2.50-2.32 (m, 4H), 1.58 (dd, J=8.4, 5.0 Hz, 2H), 1.54-1.36 (m, 2H), 1.46 (s, 9H), 1.07 (s, 9H).

Step 3 tert-Butyl rac-(1R,2R)-2-(4-(tosyloxy)butyl)cyclopropane-1-carboxylate was made following steps 3-4 of L13a using tert-butyl rac-(trans)-2-[4-[tert-butyl(diphenyl)silyl]oxybutyl]cyclopropanecarboxylate. $^1$H NMR (400 MHz, Chloroform-d) δ 7.81 (d, J=8.3 Hz, 2H), 7.37 (d, J=8.3 Hz, 2H), 4.04 (t, J=6.5 Hz, 2H), 2.48 (s, 3H), 1.74-1.63 (m, 1H), 1.63-1.55 (m, 1H), 1.51-1.40 (m, 2H), 1.45 (s, 9H), 1.36-1.15 (m, 4H), 1.08-1.02 (m, 1H), 0.61-0.55 (m, 1H).

tert-butyl rac-(1R,2R)-2-(5-(tosyloxy)pentyl)cyclopropane-1-carboxylate (L20b)

Prepared following a similar procedure to L20a from 6-((tert-butyldiphenylsilyl)oxy)hexanal.

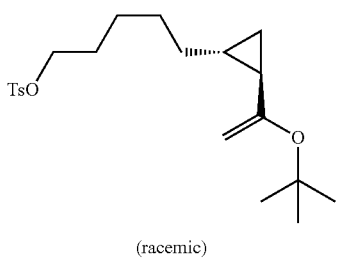

(racemic)

Preparation of tert-butyl rac-3-methoxy-2,2-dimethyl-8-(tosyloxy)octanoate (L21)

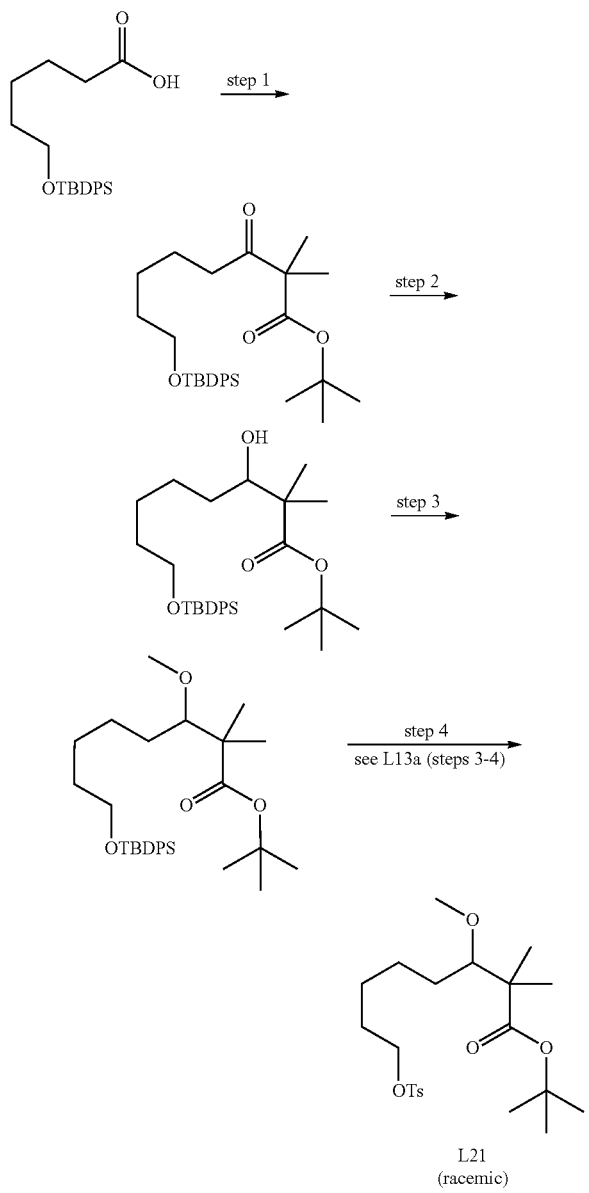

L21
(racemic)

Step 1

Oxalyl chloride (226 mg, 1.78 mmol) and DMF (2 drops) were added to a solution of 6-[tert-butyl(diphenyl)silyl]oxyhexanoic acid (600 mg, 1.62 mmol, Synlett 2006, 2670) in DCM (10 mL) at 0° C. and the solution was stirred for 1 h. The reaction was warmed up to room temperature and evaporated to dryness. The crude acid chloride was dissolved in THF (5 mL). In a separate flask, a solution of tert-butyl 2-methylpropanoate (304 mg, 2.1 mmol) in THF (4 mL) was cooled to −78° C. and a solution of LDA in THF (1 M, 2.1 mL) was added dropwise. The resulting solution was stirred at −78° C. for 1 hour. The solution of acid chloride prepared above was added and the reaction medium was slowly warmed up to 0° C. before it was quenched with aqueous $NH_4Cl$(sat.). After work up the residue was purified by flash chromatography over silica gel (Hexanes/EtOAc 0-15%) to afford tert-butyl 8-((tert-butyldiphenylsilyl)oxy)-2,2-dimethyl-3-oxooctanoate.

Step 2

$NaBH_4$ (27 mg, 0.72 mmol) was added to a 0° C. solution of tert-butyl 8-((tert-butyldiphenylsilyl)oxy)-2,2-dimethyl-3-oxooctanoate (325 mg, 0.65 mmol) in THF/MeOH (2:1, 2 mL). The resulting solution was stirred until full conversion of the starting material. Work up ($NH_4Cl$ (aq)/EtOAc) followed by chromatography over silica gel (Hexanes/EtOAc 5-25%) afforded tert-butyl 8-((tert-butyldiphenylsilyl)oxy)-3-hydroxy-2,2-dimethyloctanoate. $^1H$ NMR (400 MHz, Chloroform-d) δ 7.75-7.67 (m, 4H), 7.48-7.37 (m, 6H), 3.68 (t, J=6.5 Hz, 2H), 3.54 (d, J=9.7 Hz, 1H), 2.49 (brs, 1H), 1.68-1.55 (m, 2H), 1.48 (s, 9H), 1.45-1.23 (m, 6H), 1.17 (s, 3H), 1.14 (s, 3H), 1.07 (s, 9H).

Step 3

A solution of tert-butyl 8-((tert-butyldiphenylsilyl)oxy)-3-hydroxy-2,2-dimethyloctanoate (240 mg, 0.48 mmol) in THF (1 mL) was cooled to 0° C. LiHMDS (1 M in THF, 0.58 mL) was added dropwise and the resulting solution was stirred for 30 minutes before MeI (150 mg, 0.11 mmol) was added. The reaction mixture was warmed up to room temperature and stirred for an additional hour. Work up ($NH_4Cl$ (aq)/EtOAc) followed by chromatography over silica gel (Hexanes/EtOAc 0-10%) afforded tert-butyl 8-((tert-butyldiphenylsilyl)oxy)-3-methoxy-2,2-dimethyloctanoate. $^1H$ NMR (400 MHz, Chloroform-d) δ 7.78-7.65 (m, 4H), 7.47-7.36 (m, 6H), 3.68 (t, J=6.4 Hz, 2H), 3.46 (s, 3H), 3.36-3.33 (m, 1H), 1.59 (q, J=7.6 Hz, 4H), 1.47 (s, 9H), 1.46-1.27 (m, 4H), 1.17 (s, 3H), 1.07 (s, 9H), 1.05 (s, 3H).

Step 4 tert-butyl rac-3-methoxy-2,2-dimethyl-8-(tosyloxy)octanoate was made following steps 3-4 of L13a using tert-butyl 8-((tert-butyldiphenylsilyl)oxy)-3-methoxy-2,2-dimethyloctanoate. $^1H$ NMR (400 MHz, Chloroform-d) δ 7.81 (d, J=8.3 Hz, 2H), 7.37 (d, J=8.3 Hz, 2H), 4.05 (td, J=6.4 Hz, 2H), 3.44 (s, 3H), 3.31 (dd, J=9.0, 2.2 Hz, 1H), 2.47 (s, 3H), 1.71-1.52 (m, 3H), 1.46 (s, 9H), 1.45-1.25 (m, 5H), 1.15 (s, 3H), 1.03 (s, 3H).

Preparation of ethyl 2-(45-iodopentyl)oxy)acetate (L22)

L22 was prepared as described in Tetrahedron 2003, 53, 149.

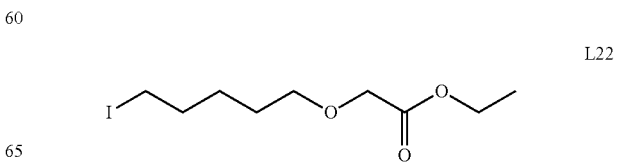

L22

Preparation of ethyl 2-((6-bromohexyl)oxy)acetate (L23)

L23 was prepared as described in U.S. Pat. No. 4,981,873 (example 12a).

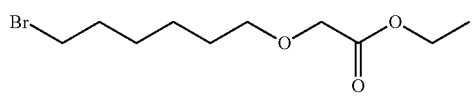

L23

Preparation of 3-bromo-2-((7-bromoheptyl)oxy)pyridine (L24a)

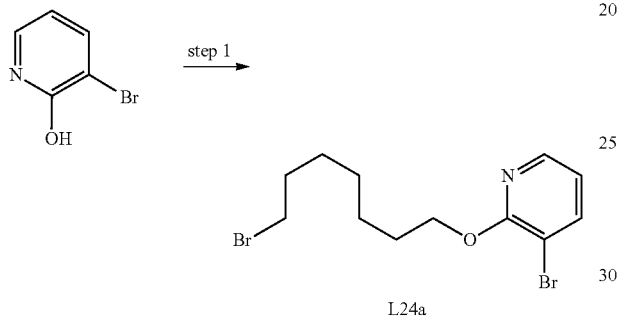

L24a

Step 1

3-Bromopyridin-2-ol (200 mg, 1.15 mmol), 7-bromoheptane-1-ol (0.19 mL, 1.38 mmol), and triphenylphosphine (392 mg, 1.49 mmol) were combined in THF (5 mL) under $N_2$. Diisopropyl azodicarboxylate (0.29 mL, 1.5 mmol) was added dropwise and the resulting mixture allowed to stir at ambient temperature overnight. The reaction was adsorbed directly to isolate and purified by silica gel chromatography (eluent: EtOAc in hexane) to give 3-bromo-2-((7-bromoheptyl)oxy)pyridine. ES/MS: m/z 351.9 [M+H]$^+$. $^1$H NMR (400 MHz, DMSO-d$_6$) δ 8.14 (d, J=4.7 Hz, 1H), 8.02 (d, J=7.6 Hz, 1H), 6.93 (dd, J=7.5, 5.2 Hz, 1H), 5.19 (hept, J=6.1 Hz, 2H), 4.31 (t, J=6.6 Hz, 2H), 1.91-1.67 (m, 4H), 1.50-1.22 (m, 6H).

3-bromo-2-((6-bromohexyl)oxy)pyridine (L24b)

Prepared following a similar procedure to L24a from 6-bromohexan-1-ol. ES/MS: m/z 337.8 [M+H]$^+$.

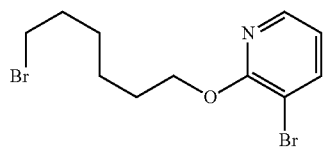

L24b

3-bromo-2-((8-bromooctyl)oxy)pyridine (L24c)

Prepared following a similar procedure to L24a from 8-bromooctan-1-ol. ES/MS: m/z 365.9 [M+H]$^+$.

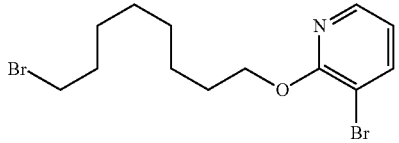

L24c

Preparation of 9-((tert-butyldimethylsilyl)oxy)-N-methylnonanamide (L25)

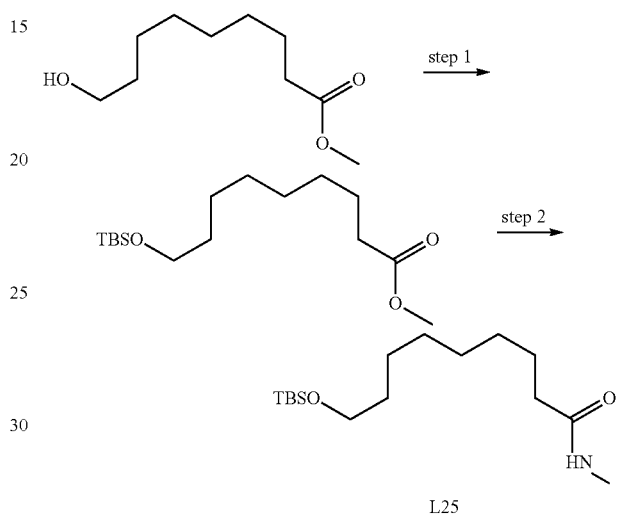

L25

Step 1.

A solution of methyl 9-hydroxynonanoate (300 mg, 1.6 mmol), tert-butyldimethylchlorosilane (480 mg, 3.2 mmol), and imidazole (240 mg, 3.5 mmol) in DCM (5 mL) was allowed to stir overnight. Brine was added and the mixture was washed with DCM three times. The combined organic layers were dried over MgSO$_4$, filtered and concentrated. Purification by silica gel column chromatography (0-50% EtOAc in hexanes) provided methyl 9-[tert-butyl(dimethyl)silyl]oxynonanoate. $^1$H NMR (400 MHz, Chloroform-d) δ 3.62 (s, 3H), 3.55 (t, J=6.6 Hz, 2H), 2.26 (t, J=7.5 Hz, 2H), 1.61-1.53 (m, 2H), 1.49-1.39 (m, 2H), 1.34-1.18 (m, 8H), 0.85 (s, 9H), −0.00 (s, 6H).

Step 2

A solution of methyl 9-[tert-butyl(dimethyl)silyl]oxynonanoate (470 mg, 1.6 mmol) and methylamine (33% in ethanol, 5.8 mL) was allowed to stir for 6 h. The reaction was concentrated and purified by silica gel column chromatography (0-100% EtOAc in hexanes) to provide 9-[tert-butyl(dimethyl)silyl]oxy-N-methyl-nonanamide. $^1$H NMR (400 MHz, Chloroform-d) δ 5.35 (s, 1H), 3.55 (t, J=6.8 Hz, 2H), 2.76 (d, J=2.9 Hz, 2H), 2.11 (t, J=6.9 Hz, 2H), 1.62-1.55 (m, 2H), 1.51-1.41 (m, 2H), 0.85 (s, 9H), 0.00 (s, 6H).

Preparation of tert-butyl (5-bromopentyl)(methyl)carbamate (L26a)

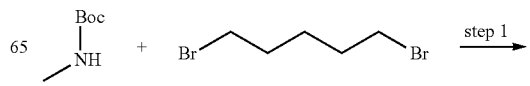

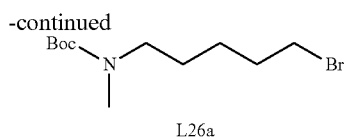

L26a

Step 1

Tert-butyl methylcarbamate (656 mg, 5 mmol) was taken in DMF/THF (2:1, 20 mL) and cooled to 0° C. under an argon atmosphere. NaH (60% dispersion, 240 mg, 6 mmol) was added and the remaining suspension was stirred for 1 hour at 0° C. before 1,5-dibromopentane (12.8 g, 20 mmol) was added at once. The resulting solution was stirred at 0° C. for 1 h then warmed to room temperature and stirred for an additional hour. A saturated solution of ammonium chloride was added and after work up the residue was purified by column chromatography (Hexane:diethyl ether, 0-10%) to afford tert-butyl (5-bromopentyl)(methyl)carbamate. $^1$H NMR (400 MHz, Chloroform-d) δ 3.43 (t, J=6.8 Hz, 2H), 3.23 (t, J=6.8 Hz, 2H), 2.85 (s, 3H), 1.98-1.82 (m, 2H), 1.61-1.50 (m, 2H), 1.48 (s, 9H), 1.49-1.39 (m, 2H).

tert-butyl (7-bromoheptyl)(methyl)carbamate (L26b)

Prepared following a similar procedure to L26a from 1,7-dibromoheptane. $^1$H NMR (400 MHz, Chloroform-d) δ 3.43 (t, J=6.8 Hz, 2H), 3.19 (t, J=6.8 Hz, 2H), 2.85 (s, 3H), 1.97-1.81 (m, 2H), 1.60-1.49 (m, 2H), 1.48 (s, 9H), 1.44-1.27 (m, 6H).

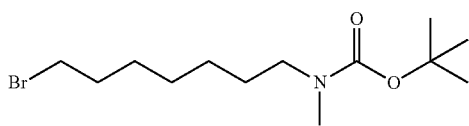

L26b tert-butyl (4-bromobutyl)(methyl)carbamate (L26c)

Prepared following a similar procedure to L26a from 1,4-dibromobutane. Also reported in J. Med. Chem. 2013, 56, 5115.

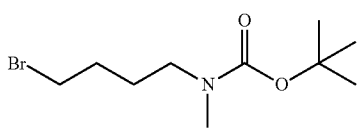

L26c tert-butyl (6-bromohexyl)(methyl)carbamate (L26d)

Prepared following a similar procedure to L26a from 1,6-dibromohexane. Also reported in J. Chem. Soc., Perk. Trans. 1: Org. Bio-Org. Chem. 1995, 20, 2581.

L26d

Preparation of 2-methyl-2-(trifluoromethyl)pent-4-enoic Acid (L27)

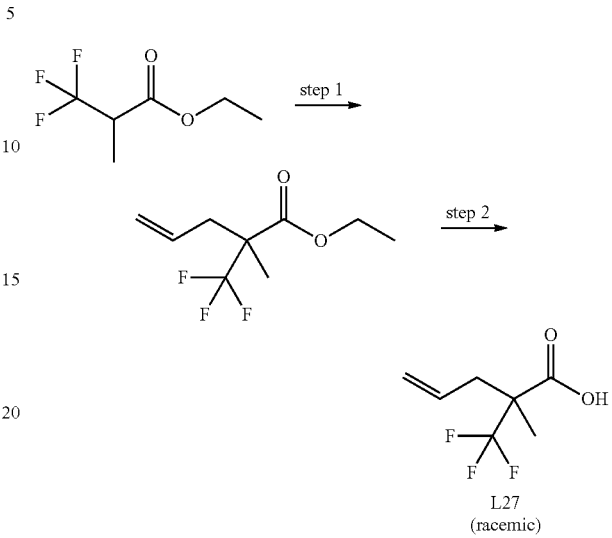

L27
(racemic)

Step 1

Tris(dibenzylideneacetone)dipalladium (135 mg, 0.15 mmol), 2,2'-bis(diphenylphosphino)-1,1'-binaphthyl (366 mg, 0.59 mmol) and 5A molecular sieves (dried at 100° C. under high vacuum prior to use) were taken up in THF under $N_2$. Ethyl 3,3,3-trifluoro-2-methylpropanoate (1.0 g, 5.9 mmol) and allyl ethyl carbonate (0.97 mL, 7.4 mmol) were added, and the reaction mixture was stirred at 50° C. overnight. The reaction mixture was cooled, filtered through celite, and concentrated. Purification by silica gel (0-10% EtOAc in hexanes) provided ethyl 2-methyl-2-(trifluoromethyl)pent-4-enoate. $^1$H NMR (400 MHz, DMSO-d$_6$) δ 5.68 (ddt, J=17.2, 10.1, 7.3 Hz, 1H), 5.29-5.11 (m, 2H), 4.19 (q, J=7.1 Hz, 2H), 2.67 (dd, J=13.8, 7.1 Hz, 1H), 2.44 (dd, J=13.8, 7.6 Hz, 1H), 1.33 (s, 3H), 1.21 (t, J=7.1 Hz, 3H).

Step 2

2-methyl-2-(trifluoromethyl)pent-4-enoate (520 mg, 2.47 mmol) was dissolved in THF (10 mL), MeOH (5 mL), and water (5 mL). Lithium hydroxide monohydrate (560 mg, 13.3 mmol) was added and the reaction mixture was stirred at r.t. After 38 h, 3 M aqueous hydrochloric acid (6.2 mL, 19 mmol) was added and the reaction mixture was partitioned between DCM and water. The organic phase was dried over $Na_2SO_4$, filtered, and concentrated to afford 2-methyl-2-(trifluoromethyl)pent-4-enoic acid that was used without further purification. 1H NMR (400 MHz, DMSO-d6) δ 13.50 (s, 1H), 5.70 (ddt, J=17.2, 10.0, 7.4 Hz, 1H), 5.27-5.11 (m, 2H), 2.63 (dd, J=13.8, 7.0 Hz, 1H), 2.41 (dd, J=13.8, 7.6 Hz, 1H), 1.29 (s, 3H).

Preparation of tert-butyl 2-(5-(tosyloxy)pentyl)benzoate (L28a)

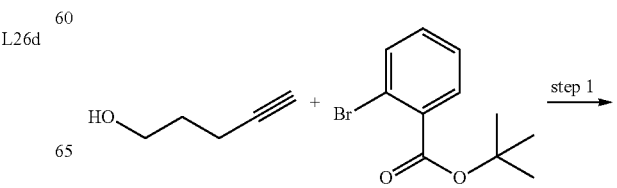

-continued

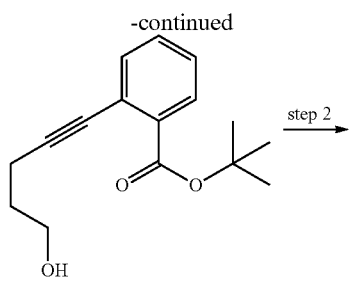

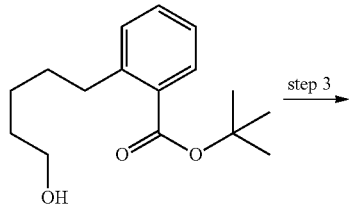

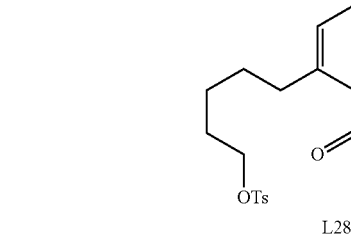

L28a

Step 1

A mixture of tert-butyl 2-bromobenzoate (1.00 g, 3.89 mmol), pent-4-yn-1-ol (0.491 g, 5.83 mmol), and tricyclohexylphosphine (0.044 g, 0.156 mmol) in triethylamine (8 mL) was sparged with $N_2$ for 3 min. Copper(I) iodide (0.030 g, 0.156 mmol) and dichlorobis(triphenylphosphine)palladium(II) (0.055 g, 0.078 mmol) were added. The reaction mixture was stirred at 80° C. for 16 h. The reaction mixture was cooled to rt and diluted with water/EtOAc. The aqueous layer was extracted twice with EtOAc. The combined organic layers were washed with brine, dried ($Na_2SO_4$), filtered, and concentrated. The residue was purified via flash column chromatography on silica gel to afford tert-butyl 2-(5-hydroxypent-1-yn-1-yl)benzoate. ES/MS: m/z 283.2 $[M+Na]^+$.

Step 2

A solution of tert-butyl 2-(5-hydroxypent-1-yn-1-yl)benzoate (1.01 g, 3.89 mmol) in EtOH (20 mL) was sparged with $N_2$ for 3 min. Palladium hydroxide on carbon (0.273 g of 20% Pd(OH)$_2$/C) was added. The mixture was shaken on a Parr shaker under 40 psi $H_2$ for 72 h. The reaction mixture was filtered through a pad of Celite. The filter pad was rinsed with EtOAc/MeOH. The filtrate was concentrated to afford tert-butyl 2-(5-hydroxypentyl)benzoate. ES/MS: m/z 287.2 $[M+Na]^+$.

Step 3

To a solution of tert-butyl 2-(5-hydroxypentyl)benzoate (0.947 g, 3.58 mmol), TEA (1.50 mL, 10.7 mmol), and DMAP (0.044 g, 0.358 mmol) in DCM (18 mL) at 0° C. was added para-toluenesulfonyl chloride (1.02 g, 5.37 mmol). The reaction mixture was allowed to warm to rt and was stirred for 16 h. The reaction mixture was diluted with DCM/water. The aqueous layer was extracted twice with DCM. The combined organic layers were washed with brine, dried ($Na_2SO_4$), filtered, and concentrated. The residue was purified via flash column chromatography on silica gel to afford tert-butyl 2-(5-(tosyloxy)pentyl)benzoate. ES/MS: m/z 441.2 $[M+Na]^+$.

tert-butyl 2-(6-(tosyloxy)hexyl)benzoate (L28b)

Prepared following a similar procedure to L28a using hex-5-yn-1-ol instead of pent-4-yn-1-ol. ES/MS: m/z 455.2 $[M+Na]^+$.

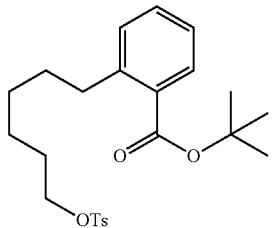

tert-butyl 2-(4-bromobutoxy)benzoate (L29)

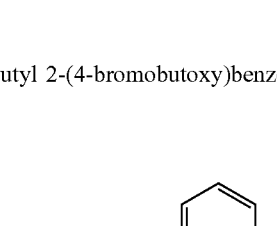

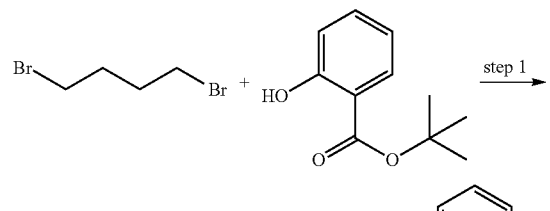

Step 1

To a mixture of tert-butyl 2-hydroxybenzoate (0.500 g, 2.57 mmol) and potassium carbonate (0.717 g, 5.15 mmol) in MeCN (25 mL) was added 1,4-dibromobutane (0.46 mL, 3.9 mmol). The reaction mixture was stirred at 80° C. for 16 h. The reaction mixture was diluted with EtOAc/water. The aqueous layer was extracted twice with EtOAc. The combined organic layers were washed with brine, dried ($Na_2SO_4$), filtered, and concentrated. The residue was purified via flash column chromatography on silica gel to afford tert-butyl 2-(4-bromobutoxy)benzoate. ES/MS: m/z 351.1, 353.1 $[M+Na]^+$.

Preparation of tert-butyl (R)-5-methoxy-5-((1R,2R)-2-((tosyloxy)methyl)cyclopropyl)pentanoate (L30a)

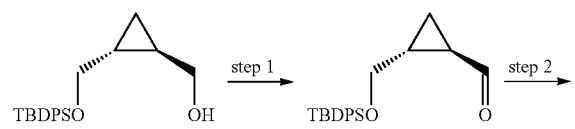

-continued

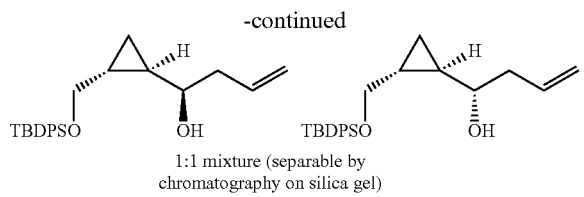

1:1 mixture (separable by
chromatography on silica gel)

Each isomer was then separately submitted to this sequence:

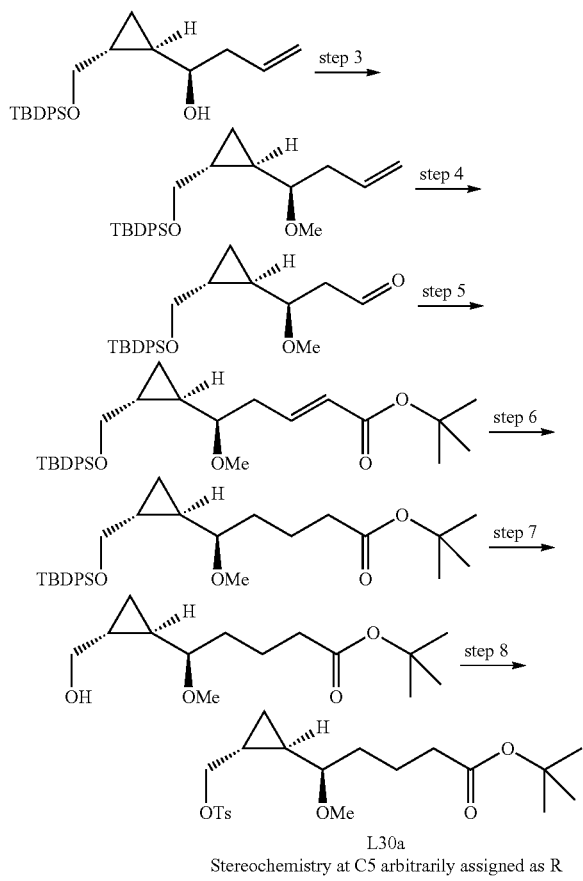

L30a
Stereochemistry at C5 arbitrarily assigned as R

Step 1

A solution of oxalyl chloride (9.35 mL, 18.7 mmol) in dichloromethane (175 mL) was cooled to −78° C. Dimethylsulfoxide (2.56 mL, 36 mmol) was added dropwise and the mixture was stirred for 30 minutes at −78° C. ((1R,2R)-2-(((tert-butyldiphenylsilyl)oxy)methyl)cyclopropyl)methanol (intermediate in the synthesis of L19a, 4.90 g, 14.4 mmol) in dichloromethane was added and the mixture was stirred for 30 minutes at −78° C. Triethylamine (10 mL, 71.9 mmol) was added and the vessel was warmed to room temperature and left to stir for 90 minutes. The reaction was quenched with saturated ammonium chloride solution and the aqueous layer was extracted with dichloromethane. The organic layers were dried over magnesium sulfate, filtered and concentrated to yield crude product, which was purified by silica gel chromatography (eluent: EtOAc/hexanes) to afford (1R,2R)-2-(((tert-butyldiphenylsilyl)oxy)methyl)cyclopropane-1-carbaldehyde. $^1$H NMR (400 MHz, Chloroform-d) δ 9.09 (d, J=5.3 Hz, 1H), 7.71-7.64 (m, 4H), 7.50-7.37 (m, 6H), 3.79 (dd, J=10.9, 4.7 Hz, 1H), 3.66 (dd, J=10.9, 5.4 Hz, 1H), 1.91-1.70 (m, 2H), 1.32-1.20 (m, 1H), 1.15-1.10 (m, 1H), 1.07 (s, 9H).

Step 2

A solution of (1R,2R)-2-(((tert-butyldiphenylsilyl)oxy)methyl)cyclopropane-1-carbaldehyde (677 mg, 2 mmol) dissolved in diethyl ether (40 mL) was cooled to −78° C. A 1 M solution of allylmagnesium chloride in methyl tetrahydrofuran (4 mL, 4 mmol) was added. The mixture was warmed to room temperature and left to stir for 4 h. The mixture was diluted with water and the aqueous layer extracted with ethyl acetate. The organic layers were dried over magnesium sulfate, filtered and concentrated to yield crude product, which was purified by silica gel chromatography (eluent: EtOAc/hexanes) with diastereomers eluting separately in about a 1:1 mixture. First eluting was arbitrarily assigned as R.

Step 3

A solution of (R)-1-((1R,2R)-2-(((tert-butyldiphenylsilyl)oxy)methyl)cyclopropyl)but-3-en-1-ol (694 mg, 1.82 mmol) in tetrahydrofuran (6 mL) was cooled to 0° C. under an atmosphere of Argon. Sodium bis(trimethylsilyl) amide (2.19 mL, 2.19 mmol) was added dropwise, followed by addition of iodomethane (0.25 mL, 4.01 mmol). The mixture was allowed to warm to room temperature and left to stir for 1 hour. The reaction was quenched with saturated ammonium chloride solution and the aqueous layer was extracted with ethyl acetate. The organic layers were dried over magnesium sulfate, filtered and concentrated to yield the crude product, which was purified by silica gel chromatography (eluent: EtOAc/hexanes). $^1$H NMR (400 MHz, Chloroform-d) δ 7.70 (m, J=6.3, 1.8 Hz, 4H), 7.48-7.35 (m, 6H), 5.92 (m, J=17.2, 10.2, 7.0 Hz, 1H), 5.15-4.99 (m, 2H), 3.68 (dd, J=10.7, 5.7 Hz, 1H), 3.52 (dd, J=10.7, 6.6 Hz, 1H), 3.45 (s, 3H), 2.65 (m, J=8.6, 6.5, 5.3 Hz, 1H), 2.36 (m, J=7.4, 1.3 Hz, 2H), 1.20-1.11 (m, 1H), 1.07 (s, 9H), 0.77-0.70 (m, 1H), 0.37 (m, J=8.9, 5.0 Hz, 1H), 0.28 (m, J=8.5, 5.1 Hz, 1H).

Step 4

To a solution of tert-butyl(((1R,2R)-2-((R)-1-methoxybut-3-en-1-yl)cyclopropyl)methoxy)diphenylsilane (281 mg, 0.712 mmol) in 6 mL 2:1 tetrahydrofuran/water was added potassium osmate(VI) (7.87 mg, 0.021 mmol) and sodium periodate (457 mg, 2.14 mmol). The mixture was left to stir for 1 h until full conversion. The reaction mixture was diluted with ethyl acetate and quenched with sodium thiosulfate and left to stir overnight. The aqueous layer was extracted with ethyl acetate. The organic layers were dried over magnesium sulfate, filtered and concentrated to yield the crude product, which was used in the next step with no further purification. $^1$H NMR (400 MHz, Chloroform-d) δ 9.80 (dd, J=2.7, 2.0 Hz, 1H), 7.73-7.62 (m, 4H), 7.42 (m, J=13.2, 7.5, 6.6, 0.9 Hz, 6H), 3.80-3.69 (m, 1H), 3.49-3.42 (m, 4H), 3.12 (m, J=8.4, 4.2 Hz, 1H), 2.71 (m, J=15.9, 8.1, 2.7 Hz, 1H), 2.59 (m, J=15.9, 4.2, 2.0 Hz, 1H), 1.23-1.18 (m, 1H), 1.06 (d, J=1.7 Hz, 9H), 0.84-0.73 (m, 1H), 0.40 (m, J=8.8, 5.1 Hz, 1H), 0.27 (m, J=8.7, 5.2 Hz, 1H).

Step 5

To a solution of (R)-3-((1R,2R)-2-(((tert-butyldiphenylsilyl)oxy)methyl)cyclopropyl)-3-methoxypropanal (308 mg, 0.777 mmol) in THF (6 mL) was added tert-butoxycarbonylmethylene)triphenylphosphorane (439 mg, 1.17 mmol) and stirred at room temperature overnight. The reaction mixture was concentrated and purified by silica gel chromatography (eluent: EtOAc/hexanes). $^1$H NMR (400 MHz, Chloroform-d) δ 7.69 (m, J=6.3, 1.8 Hz, 4H), 7.46-7.37 (m, 6H), 6.92 (m, J=15.6, 7.2 Hz, 1H), 5.81 (m, J=15.6, 1.5 Hz, 1H), 3.69 (dd, J=10.8, 5.6 Hz, 1H), 3.50 (dd, J=10.7, 6.6 Hz, 1H), 3.44 (s, 3H), 2.68 (m, J=8.6, 5.8 Hz, 1H), 2.45 (m, J=6.7, 6.1, 1.7 Hz, 2H), 1.50 (s, 9H), 1.20-1.11 (m, 1H), 1.06 (s, 9H), 0.74 (t, J=4.9 Hz, 1H), 0.39 (m, J=8.9, 5.1 Hz, 1H), 0.25 (m, J=8.6, 5.1 Hz, 1H).

Step 6

To a solution of tert-butyl (R,E)-5-((1R,2R)-2-(((tert-butyldiphenylsilyl)oxy)methyl)cyclopropyl)-5-methoxypent-2-enoate (199 mg, 0.777 mmol) in ethyl acetate (2 mL) was added 5% palladium on carbon (100 mg, 0.094 mmol) and the mixture was hydrogenated under an atmosphere of hydrogen for 2 hours at room temperature. The mixture was filtered over celite, washing with ethyl acetate. The organics were concentrated to yield the crude product, which was used in the next step with no further purification. $^1$H NMR (400 MHz, Chloroform-d) δ 7.69 (m, J=8.0, 1.7 Hz, 4H), 7.47-7.33 (m, 6H), 3.67 (dd, J=10.7, 5.8 Hz, 1H), 3.50 (dd, J=10.7, 6.7 Hz, 1H), 3.43 (s, 3H), 2.55 (m, J=8.6, 5.8 Hz, 1H), 2.23 (t, J=7.3 Hz, 2H), 1.76 (dd, J=13.2, 7.5 Hz, 1H), 1.69-1.62 (m, 1H), 1.46 (s, 9H), 1.18-1.10 (m, 1H), 1.06 (s, 9H), 1.00-0.92 (d, 2H), 0.69 (m, J=8.9, 4.8 Hz, 1H), 0.35 (m, J=9.3, 5.0 Hz, 1H), 0.24 (m, J=8.5, 5.1 Hz, 1H).

Step 7

To a solution of tert-butyl (R)-5-((1R,2R)-2-(((tert-butyldiphenylsilyl)oxy)methyl)cyclopropyl)-5-methoxypentanoate (146 mg, 0.295 mmol) in tetrahydrofuran (3 mL) was added TBAF (1 M in THF, 0.442 mL, 0.442 mmol) and left to stir for 3 hours at room temperature. The mixture was quenched with saturated sodium bicarbonate solution. The aqueous layer was extracted with diethyl ether and the combined organics were dried over magnesium sulfate. Filtration and evaporation of solvents yielded the crude product, which was purified by silica gel chromatography (eluent: EtOAc/hexanes). $^1$H NMR (400 MHz, Chloroform-d) δ 3.57-3.49 (m, 2H), 3.41 (s, 3H), 2.60 (m, J=8.4, 5.7 Hz, 1H), 2.25 (t, J=7.3 Hz, 2H), 1.71-1.56 (m, 4H), 1.46 (s, 9H), 1.20 (m, J=8.5, 6.7, 4.8 Hz, 1H), 0.80-0.66 (m, 1H), 0.42 (m, J=27.9, 8.4, 5.0 Hz, 2H).

Step 8

A solution of tert-butyl (R)-5-((1R,2R)-2-(hydroxymethyl)cyclopropyl)-5-methoxypentanoate (52 mg, 0.201 mmol) in dichloromethane (2 mL) was cooled to 0° C. for 10 minutes. 4-(Dimethylamino)-pyridine (35.7 mg, 0.302 mmol) and p-Toluenesulfonyl chloride (42.2 mg, 0.221 mmol) were added. The solution was warmed to room temperature and stirred overnight. The mixture was quenched with saturated ammonium chloride solution. The aqueous layer was extracted with dichloromethane and the combined organics were dried over magnesium sulfate. Filtration and evaporation of solvents yielded the crude product, which was purified by silica gel chromatography (eluent: EtOAc/hexanes) to afford tert-butyl (R)-5-methoxy-5-((1R,2R)-2-((tosyloxy)methyl)cyclopropyl)pentanoate. $^1$H NMR (400 MHz, Chloroform-d) δ 7.84-7.77 (m, 2H), 7.40-7.33 (m, 2H), 4.01-3.86 (m, 2H), 3.36 (s, 3H), 2.59 (m, J=8.0, 5.7 Hz, 1H), 2.47 (s, 3H), 2.22 (t, J=7.3 Hz, 2H), 1.75-1.50 (m, 4H), 1.46 (s, 9H), 1.21 (m, J=7.6, 4.8 Hz, 1H), 0.75 (m, J=8.4, 5.8, 4.3 Hz, 1H), 0.49-0.38 (m, 2H).

tert-butyl (S)-5-methoxy-5-((1R,2R)-2-((tosyloxy)methyl)cyclopropyl)pentanoate (L30b)

Prepared following a similar procedure to L30a. $^1$H NMR (400 MHz, Chloroform-d) δ 7.85-7.76 (m, 2H), 7.40-7.33 (m, 2H), 4.01-3.85 (m, 2H), 3.36 (s, 3H), 2.59 (dt, J=8.0, 5.7 Hz, 1H), 2.47 (s, 3H), 2.22 (t, J=7.3 Hz, 2H), 1.74-1.50 (m, 4H), 1.24-1.16 (m, 1H), 0.75 (tdd, J=8.4, 5.8, 4.3 Hz, 1H), 0.45 (ddt, J=12.6, 8.2, 5.4 Hz, 2H).

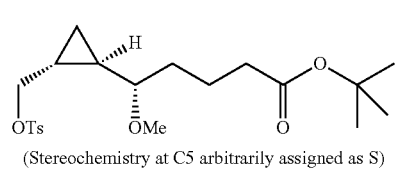

(Stereochemistry at C5 arbitrarily assigned as S)

Preparation of tert-butyl 5-((1R,2R)-2-(hydroxymethyl)cyclopropyl)pentanoate (L31)

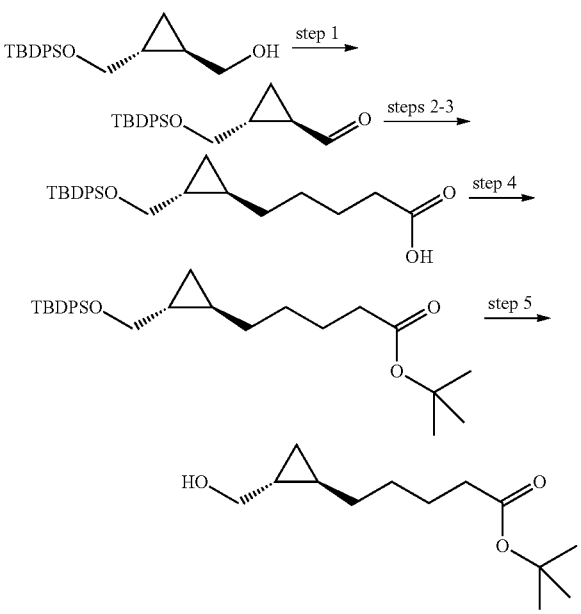

Step 1

A solution of oxalyl chloride (9.35 mL, 18.7 mmol) in dichloromethane (175 mL) was cooled to −78° C. Dimethylsulfoxide (2.56 mL, 36 mmol) was added dropwise and the mixture was stirred for 30 minutes at −78° C. ((1R,2R)-2-(((tert-butyldiphenylsilyl)oxy)methyl)cyclopropyl)methanol (4.90 g, 14.4 mmol) in dichloromethane was added and the mixture was stirred for 30 minutes at −78° C. Triethylamine (10 mL, 71.9 mmol) was added and the vessel was warmed to room temperature and left to stir for 90 minutes. The reaction was quenched with saturated ammonium chloride solution and the aqueous layer was extracted with dichloromethane. The organic layers were dried over magnesium sulfate, filtered and concentrated to yield crude product, which was purified by silica gel chromatography (eluent: EtOAc/Hexanes) to provide (1R,2R)-2-(((tert-butyldiphenylsilyl)oxy)methyl)cyclopropane-1-carbaldehyde. $^1$H NMR (400 MHz, Chloroform-d) δ 9.09 (d, J=5.3 Hz, 1H), 7.71-7.64 (m, 4H), 7.50-7.37 (m, 6H), 3.79 (m, J=10.9, 4.7 Hz, 1H), 3.66 (m, J=10.9, 5.4 Hz, 1H), 1.91-1.70 (m, 2H), 1.32-1.20 (m, 1H), 1.15-1.10 (m, 1H), 1.07 (s, 9H).

Step 2

A solution of (3-carboxypropyl)triphenylphosphonium bromide (5.09 g, 11.8 mmol) in 4:1 tetrahydrofuran:dimethylsulfoxide (50 mL) was cooled to 0° C. 1.0 M potassium tert-butoxide solution in tetrahydrofuran was added (23.7 mL, 23.7 mmol) and the mixture let stir for 16 h. Added (1R,2R)-2-(((tert-butyldiphenylsilyl)oxy)methyl)cyclopropane-1-carbaldehyde (2.51 g, 7.41 mmol) at 0° C. and left to warm to room temperature for 5 h. The reaction mixture was quenched with saturated ammonium chloride solution and extracted with ethyl acetate. The organics were collected, dried over magnesium sulfate and concentrated to yield the crude product, which was purified by silica gel chromatography (eluent: EtOAc/Hexanes) to yield 5-((1S,2R)-2-(((tert-butyldiphenylsilyl)oxy)methyl)cyclopropyl)pent-4-enoic acid with Z:E ratio of 8:2. ES/MS: m/z 409.5 [M+H]$^+$.

Step 3

To a solution of 5-((1S,2R)-2-(((tert-butyldiphenylsilyl)oxy)methyl)cyclopropyl)pent-4-enoic acid (1.60 g, 3.90 mmol) in isopropyl acetate (36 mL) was added platinum, 5 wt. % on activated carbon (305 mg, 1.56 mmol), and submitted to an atmosphere of H$_2$ at 20 psi, and stirred for 16 h. The reaction mixture was filtered and rinsed with ethyl acetate. The organics were concentrated to yield the crude product which was purified by HPLC (eluent: MeCN/H$_2$O) to provide 5-((1R,2R)-2-(((tert-butyldiphenylsilyl)oxy)methyl)cyclopropyl)pentanoic acid. ES/MS: m/z 411.1 [M+H]$^+$.

Step 4

To a solution of 5-((1R,2R)-2-(((tert-butyldiphenylsilyl)oxy)methyl)cyclopropyl)pentanoic acid (1000 mg, 2.44 mmol) in tetrahydrofuran (28 mL) was added 2-tert-butyl-1,3-diisopropylisourea (3.26 mL, 14.6 mmol) and stirred at room temperature for 3 h. The reaction mixture was filtered to remove formed solids, washing with ethyl acetate. The organics were concentrated to yield the crude product which was purified by silica gel chromatography (eluent: EtAOc/Hexanes) to provide tert-butyl 5-((1R,2R)-2-(((tert-butyldiphenylsilyl)oxy)methyl)cyclopropyl)pentanoate. ES/MS: m/z 467.2 [M+H]$^+$. $^1$H NMR (400 MHz, Chloroform-d) δ 7.69 (m, J=7.9, 1.5 Hz, 4H), 7.48-7.35 (m, 6H), 3.63 (m, J=10.7, 5.9 Hz, 1H), 3.44 (m, J=10.7, 6.8 Hz, 1H), 2.22 (t, J=7.5 Hz, 2H), 1.61 (m, J=17.7, 10.0, 4.9 Hz, 3H), 1.46 (s, 9H), 1.43-1.35 (m, 2H), 1.23-1.13 (m, 1H), 1.07 (s, 9H), 0.79 (m, J=8.6, 6.2, 4.7 Hz, 1H), 0.57-0.48 (m, 1H), 0.25 (m, J=32.5, 8.3, 4.8 Hz, 2H).

Step 5 tert-butyl 5-((1R,2R)-2-(hydroxymethyl)cyclopropyl)pentanoate was made following step 2 of L33 using tert-butyl 5-((1R,2R)-2-(((tert-butyldiphenylsilyl)oxy)methyl)cyclopropyl)pentanoate.

Preparation of tert-butyl 5-((1R,2R)-2-(hydroxymethyl)cyclopropyl)-2-methylpentanoate (L32)

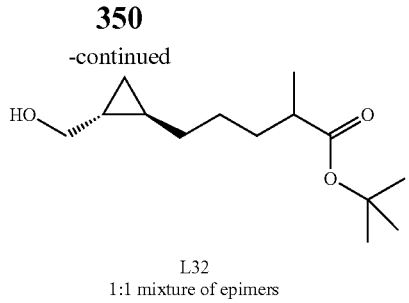

L32
1:1 mixture of epimers

Step 1

To a dry flask charged with tetrahydrofuran (5 mL) under argon, cooled to −78° C., was added 1M lithium diisopropylamide in THF/Hexanes (1.84 mL, 1.84 mmol), followed by dropwise addition of DMPU (0.09 mL, 0.74 mmol) and tert-butyl 5-((1R,2R)-2-(((tert-butyldiphenylsilyl)oxy)methyl)cyclopropyl)pentanoate (intermediate described in the synthesis of L31, 0.343 g, 0.74 mmol) in tetrahydrofuran (1 mL). The reaction was stirred at −78° C. for 1 hour. Methyl iodide (0.14 mL, 2.21 mmol) was added dropwise and the reaction was stirred for an additional 30 minutes at −78° C. and then warmed to room temperature over 2 hours. The reaction was quenched with saturated sodium bicarbonate and extracted with ethyl acetate. The organic layer was dried over sodium sulfate, filtered, and concentrated to yield the crude product which was purified by silica gel chromatography (eluent: EtOAc/Hexanes) to afford tert-butyl 5-((1R,2R)-2-(((tert-butyldiphenylsilyl)oxy)methyl)cyclopropyl)-2-methylpentanoate. $^1$H NMR (400 MHz, Chloroform-d) δ 7.77-7.61 (m, 4H), 7.50-7.32 (m, 6H), 3.61 (m, J=10.7, 6.0 Hz, 1H), 3.47 (m, J=10.7, 6.7 Hz, 1H), 2.31 (m, J=7.2, 5.6 Hz, 1H), 1.63 (m, J=12.1, 7.4, 2.4 Hz, 1H), 1.46 (s, 9H), 1.43-1.35 (m, 3H), 1.27-1.18 (m, 2H), 1.11 (d, J=7.0 Hz, 3H), 1.07 (s, 9H), 0.79 (m, J=11.0, 5.3, 4.8 Hz, 1H), 0.53 (m, J=7.3, 3.8 Hz, 1H), 0.30 (m, J=8.7, 4.7 Hz, 1H), 0.21 (m, J=9.2, 4.8 Hz, 1H).

Step 2 tert-butyl 5-((1R,2R)-2-(hydroxymethyl)cyclopropyl)-2-methylpentanoate was made following step 2 of L33 using tert-butyl 5-((1R,2R)-2-(((tert-butyldiphenylsilyl)oxy)methyl)cyclopropyl)-2-methylpentanoate. $^1$H NMR (400 MHz, Chloroform-d) δ 3.54-3.38 (m, 3H), 2.37-2.27 (m, 1H), 1.47 (s, 9H), 1.40 (m, J=7.3, 5.7, 4.1, 2.0 Hz, 1H), 1.22 (q, J=6.9 Hz, 2H), 1.12 (m, J=7.0, 1.1 Hz, 3H), 0.94-0.80 (m, 3H), 0.69-0.57 (m, 1H), 0.42-0.35 (m, 1H), 0.35-0.29 (m, 1H).

Preparation of tert-butyl 5-((1R,2R)-2-(hydroxymethyl)cyclopropyl)-2,2-dimethylpentanoate (L33)

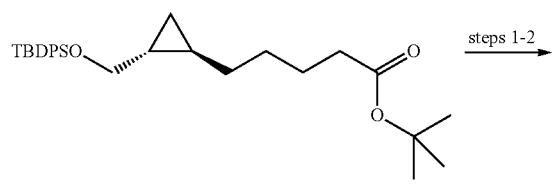

intermediate described
in the synthesis of L31 steps 1-2 →

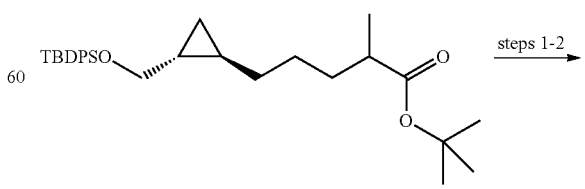

intermediate described
in the synthesis of L32 steps 1-2 →

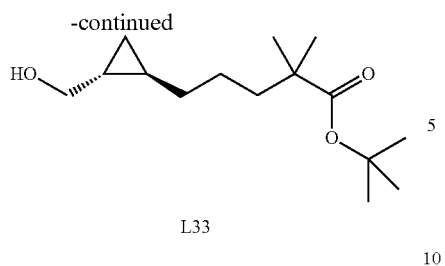

L33

Step 1

To a dry flask charged with tetrahydrofuran (5 mL) under argon, cooled to −78° C., was added 1M Lithium diisopropylamide in THF/Hexanes (1.84 mL, 1.84 mmol), followed by dropwise addition of DMPU (0.09 mL, 0.74 mmol) and tert-butyl 5-((1R,2R)-2-(((tert-butyldiphenylsilyl)oxy)methyl)cyclopropyl)-2-methylpentanoate (intermediate of in the synthesis of L32, 0.354 g, 0.74 mmol) in tetrahydrofuran (1 mL). The reaction was stirred at −78° C. for 1 hour. Methyl iodide (0.14 mL, 2.21 mmol) was added dropwise, and the reaction was stirred 30 minutes at −78° C. and then warmed to room temperature for 3 hours. The reaction was quenched with saturated sodium bicarbonate and extracted with ethyl acetate. The organic layer was dried over sodium sulfate, filtered, and concentrated to yield the crude product which was purified by silica gel chromatography (eluent: EtOAc/Hexanes) to afford tert-butyl 5-((1R,2R)-2-(((tert-butyldiphenylsilyl)oxy)methyl)cyclopropyl)-2,2-dimethylpentanoate. $^1$H NMR (400 MHz, Chloroform-d) δ 7.69 (m, J=7.8, 1.7, 0.9 Hz, 4H), 7.46-7.37 (m, 6H), 3.60 (m, J=10.7, 6.2 Hz, 1H), 3.49 (m, J=10.7, 6.6 Hz, 1H), 1.52-1.48 (m, 1H), 1.44 (s, 9H), 1.38-1.25 (m, 3H), 1.24-1.16 (m, 2H), 1.12 (s, 6H), 1.07 (s, 9H), 0.84-0.75 (m, 1H), 0.58-0.49 (m, 1H), 0.30 (m, J=8.8, 4.7 Hz, 1H), 0.21 (m, J=8.2, 4.8 Hz, 1H).

Step 2

To a solution of tert-butyl 5-((1R,2R)-2-(((tert-butyldiphenylsilyl)oxy)methyl)cyclopropyl)-2,2-dimethylpentanoate (224 mg, 0.45 mmol) dissolved in tetrahydrofuran (6 mL) was added 1 M TBAF solution in tetrahydrofuran (1.13 mL, 1.13 mmol) and stirred for 90 minutes. Partitioned reaction mixture between diethyl ether and saturated sodium bicarbonate, and extracted with ethyl acetate. The collected organics were dried over magnesium sulfate, filtered and concentrated to yield the crude product, which was purified by silica gel chromatography (eluent: EtOAc/Hexanes) to afford tert-butyl 5-((1R,2R)-2-(hydroxymethyl)cyclopropyl)-2,2-dimethylpentanoate. $^1$H NMR (400 MHz, Chloroform-d) δ 3.53-3.39 (m, 2H), 1.56-1.50 (m, 3H), 1.46 (s, 9H), 1.41-1.25 (m, 2H), 1.20 (p, J=6.4 Hz, 1H), 1.14 (s, 6H), 0.85 (m, J=11.8, 7.3, 3.6 Hz, 1H), 0.69-0.58 (m, 1H), 0.39 (m, J=8.7, 4.7 Hz, 1H), 0.32 (m, J=8.2, 4.9 Hz, 1H).

Preparation of tert-butyl 2-(methoxymethyl)-2-methyl-8-(tosyloxy)octanoate (L34)

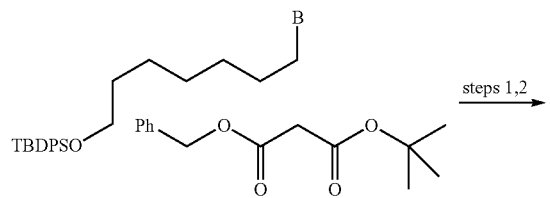

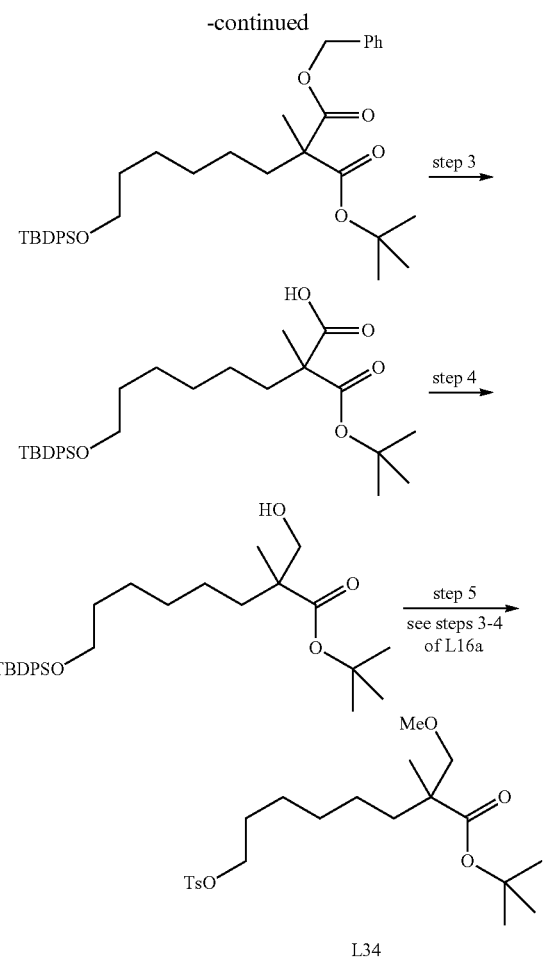

L34

Step 1

To a solution of benzyl tert-butyl malonate (2.98 g, 11.9 mmol) in DMF (60 mL) at 0° C. was added NaH (60%, 457 mg, 11.9 mmol). After stirring for 1 hour at 0° C., ((7-bromoheptyl)oxy)(tert-butyl)diphenylsilane was added and the mixture was stirred at rt overnight. The reaction was quenched with water and extracted with ethyl acetate. The organic layer was washed with brine, dried with MgSO$_4$, filtered, and concentrated. Purification by silica gel chromatography (0-20% EtOAC in hexane) provided 1-benzyl 3-(tert-butyl) 2-(6-((tert-butyldiphenylsilyl)oxy)hexyl)malonate. ES/MS: m/z 611.4 [M+Na]$^+$.

Step 2

1-benzyl 3-(tert-butyl) 2-(6-((tert-butyldiphenylsilyl)oxy)hexyl)-2-methylmalonate was made following the same previous step starting with 1-benzyl 3-(tert-butyl) 2-(6-((tert-butyldiphenylsilyl)oxy)hexyl)malonate and using methyl iodide instead of ((7-bromoheptyl)oxy)(tert-butyl)diphenylsilane. ES/MS: m/z 625.4 [M+Na]$^+$. $^1$H NMR (400 MHz, Chloroform-d) δ 7.70-7.63 (m, 4H), 7.45-7.28 (m, 11H), 5.21-5.07 (ABq, 2H), 3.63 (t, J=6.5 Hz, 2H), 1.85-1.77 (m, 2H), 1.58-1.46 (m, 2H), 1.33 (s, 3H), 1.37-1.14 (m, 6H), 1.04 (s, 9H).

Step 3

2-(tert-butoxycarbonyl)-8-((tert-butyldiphenylsilyl)oxy)-2-methyloctanoic acid was made following step 4 of A5a using 1-benzyl 3-(tert-butyl) 2-(6-((tert-butyldiphenylsilyl)oxy)hexyl)-2-methylmalonate instead of benzyl (3S,4R)-4-

(2,2-difluoroethoxy)-3-(tritylamino)piperidine-1-carboxylate. ES/MS: m/z 535.3 [M+Na]$^+$.

Step 4

To a solution of 2-(tert-butoxycarbonyl)-8-((tert-butyldiphenylsilyl)oxy)-2-methyloctanoic acid (3.91 g, 7.6 mmol) in THF (25 mL) at 0° C. were added 4-methylmorpholine (1.26 mL, 11.4 mmol) and ethyl chloroformate (1.09 mL, 11.4 mmol). The mixture was stirred at 0° C. for 20 minutes followed by filtration. The filtrate was cooled to 5° C. then water (7 mL) and NaBH$_4$ (1.10 g, 26.7 mmol) were added. The mixture was stirred at rt for 2 h. The reaction was quenched with saturated aqueous NH$_4$Cl and extracted with ethyl acetate. The organic layer was washed with brine, dried with MgSO$_4$, filtered, and concentrated. Purification by silica gel chromatography (0-70% EtOAC in hexane) provided tert-butyl 8-((tert-butyldiphenylsilyl)oxy)-2-(hydroxymethyl)-2-methyloctanoate. ES/MS: m/z 521.4 [M+Na]$^+$.

Step 5 tert-butyl 2-(methoxymethyl)-2-methyl-8-(tosyloxy)octanoate was made following step 3-4 of L16a using tert-butyl 8-((tert-butyldiphenylsilyl)oxy)-2-(hydroxymethyl)-2-methyloctanoate. ES/MS: m/z 451.3 [M+Na]$^+$.

Preparation of tert-butyl (1S,2S)-2-((3-hydroxypropoxy)methyl)cyclopropane-1-carboxylate (L35a)

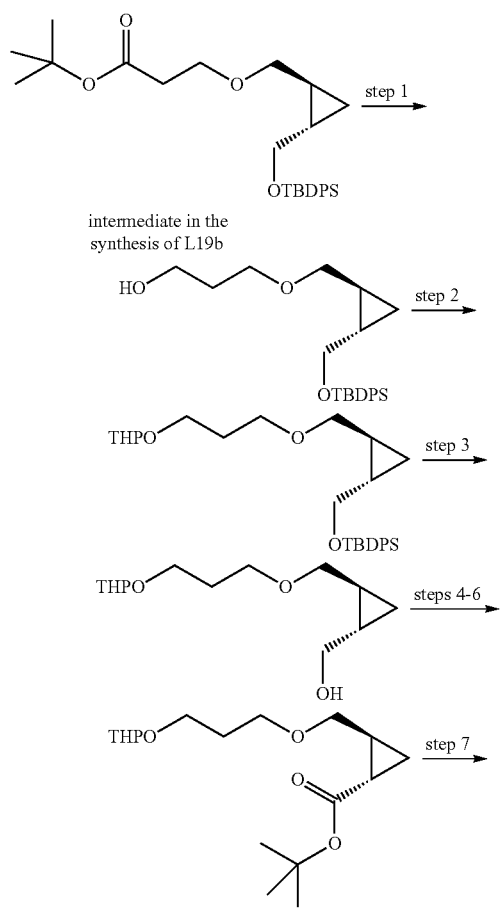

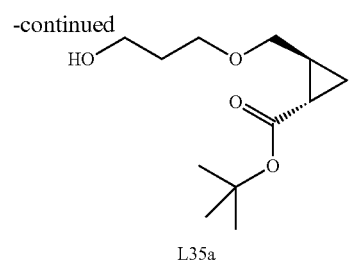

Step 1

To a solution of tert-butyl 3-(((1S,2S)-2-(((tert-butyldiphenylsilyl)oxy)methyl)cyclopropyl)methoxy)propanoate (3.7 g, 7.9 mmol, intermediate in the synthesis of L19b) in THF (40 mL) at 0° C. was added LiAlH$_4$ (2.0 M in THF, 4.34 mL, 8.7 mmol). The reaction mixture was stirred at 0° C. for 2 h. The reaction was quenched using the Fieser work-up according to X g of LiAlH$_4$: 1. Dilute with ether and cool to 0° C.; 2. Slowly add X mL of water (0.330 mL); 3. Add X mL of 15% aqueous NaOH (0.330 mL); 4. Add 3X mL of water (0.990 mL); 4. Warm to rt and stir for 15 min; 6. Add MgSO$_4$, stir for 10 minutes, filtration and concentration. Crude 3-(((1S,2S)-2-(((tert-butyldiphenylsilyl)oxy)methyl)cyclopropyl)methoxy)propan-1-ol was used in the next step. ES/MS: m/z 421.2 [M+Na]$^+$.

Step 2

A solution of 3-(((1S,2S)-2-(((tert-butyldiphenylsilyl)oxy)methyl)cyclopropyl)methoxy)propan-1-ol (1.45 g, 3.6 mmol), 3,4-dihydro-2H-pyran (0.5 mL, 5.5 mmol) and PPTS (45 mg, 018 mmol) in DCM (20 mL) was stirred at rt overnight. The reaction was quenched with saturated aqueous NaHCO$_3$ and extracted with ethyl acetate. The organic layer was washed with brine, dried with MgSO$_4$, filtered, and concentrated. Purification by silica gel chromatography (0-50% EtOAC in hexane) provided tert-butyldiphenyl(((1S,2S)-2-((3-((tetrahydro-2H-pyran-2-yl)oxy)propoxy)methyl)cyclopropyl)methoxy)silane. ES/MS: m/z 505.3 [M+Na]$^+$.

Step 3

To a solution of tert-butyldiphenyl(((1S,2S)-2-((3-((tetrahydro-2H-pyran-2-yl)oxy)propoxy)methyl)cyclopropyl)methoxy)silane (1.29 g, 2.67 mmol) in THF (15 mL) was added 1M tetra-n-butyl ammonium fluoride solution in tetrahydrofuran (4.0 mL) and stirred for 90 minutes. The reaction was quenched with saturated aqueous NaHCO$_3$ and extracted with ethyl acetate. The organic layer was washed with brine, dried with MgSO$_4$, filtered, and concentrated. Purification by silica gel chromatography (0-100% EtOAC in hexane) provided ((1S,2S)-2-((3-((tetrahydro-2H-pyran-2-yl)oxy)propoxy)methyl)cyclopropyl)methanol. ES/MS: m/z 267.2 [M+Na]$^+$.

Step 4

To a solution of ((1S,2S)-2-((3-((tetrahydro-2H-pyran-2-yl)oxy)propoxy)methyl)cyclopropyl)methanol (420 mg, 1.72 mmol) in DCM (8 mL) at 0° C. were added DMSO (0.43 mL, 6.02 mmol), Et$_3$N (0.84 mL, 6.02 mmol) and sulfur trioxide pyridine complex (684 mg, 4.30 mmol). The reaction was stirred at rt overnight. The reaction was quenched with saturated aqueous NH$_4$Cl and extracted with DCM. The organic layer was washed with brine, dried with MgSO$_4$, filtered, and concentrated. Crude (1S,2S)-2-((3-((tetrahydro-2H-pyran-2-yl)oxy)propoxy)methyl)cyclopropane-1-carbaldehyde was used in the next step. ES/MS: m/z 265.2 [M+Na]$^+$.

Step 5

To a solution of (1S,2S)-2-((3-((tetrahydro-2H-pyran-2-yl)oxy)propoxy)methyl)cyclopropane-1-carbaldehyde (1.15 mmol) in t-BuOH (4 mL), THF (2 mL) and water (2 mL) was added $KH_2PO_4$ (1.0 g, 5.74 mmol) and 2-methyl-2-butene followed by a dropwise addition of $NaClO_2$ (259 mg, 2.9 mmol) in 1 mL of water. The reaction was stirred at rt for 1 h. The reaction was quenched with 1 N HCl and extracted with ethyl acetate. The organic layer was washed with brine, dried with $MgSO_4$, filtered, and concentrated. Crude ((1S,2S)-2-((3-((tetrahydro-2H-pyran-2-yl)oxy)propoxy)methyl)cyclopropane-1-carboxylic acid was used in the next step. ES/MS: m/z 281.2 [M+Na]+.

Step 6

A solution of ((1S,2S)-2-((3-((tetrahydro-2H-pyran-2-yl)oxy)propoxy)methyl)cyclopropane-1-carboxylic acid (1.15 mmol) and 2-tert-butyl-1,3-diisopropyl-isourea (1.2 mL, approximately 5 equiv.) in THF was stirred at reflux for 24 h. The solids were filtered off and the filtrate was concentrated. Purification by silica gel chromatography (0-100% EtOAC in hexane) provided tert-butyl (1S,2S)-2-((3-((tetrahydro-2H-pyran-2-yl)oxy)propoxy)methyl)cyclopropane-1-carboxylate. ES/MS: m/z 337.2 [M+Na]+.

Step 7

A solution of tert-butyl (1S,2S)-2-((3-((tetrahydro-2H-pyran-2-yl)oxy)propoxy)methyl)cyclopropane-1-carboxylate (175 mg, 0.57 mmol) and PPTS (142 mg, 0.57 mmol) in MeOH (5 mL) was stirred at rt for 24 h. Concentration and purification by silica gel chromatography (0-100% EtOAC in hexane) provided tert-butyl tert-butyl (1S,2S)-2-((3-hydroxypropoxy)methyl)cyclopropane-1-carboxylate. ES/MS: m/z 253.2 [M+Na]+.

tert-butyl (1R,2R)-2-((3-hydroxypropoxy)methyl)cyclopropane-1-carboxylate (L35b)

Prepared following a similar procedure to L35a starting with tert-butyl 3-(((1R,2R)-2-(((tert-butyldiphenylsilyl)oxy)methyl)cyclopropyl)methoxy)propanoate (intermediate in the synthesis of L19a). ES/MS: m/z 253.2 [M+Na]+.

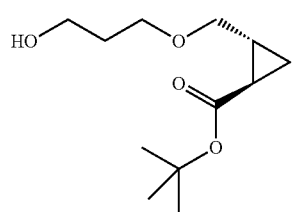

L35b tert-butyl (1S,2R)-2-((3-hydroxypropoxy)methyl)cyclopropane-1-carboxylate (L35c)

Prepared following a similar procedure to L35a starting with tert-butyl 3-(((1R,2S)-2-(((tert-butyldiphenylsilyl)oxy)methyl)cyclopropyl)methoxy)propanoate (intermediate in the synthesis of L13d). ES/MS: m/z 253.2 [M+Na]+.

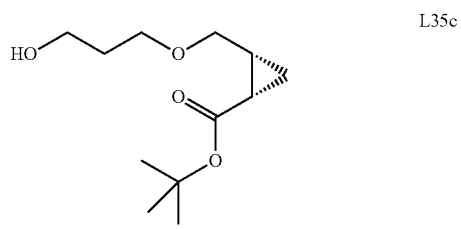 [SMILES: CC(C)(C)OC(=O)[C@H]1C[C@H]1COCCCO]

L35c tert-butyl (1R,2S)-2-((3-hydroxypropoxy)methyl)cyclopropane-1-carboxylate (L35d)

Prepared following a similar procedure to L35a starting with tert-butyl 3-(((1S,2R)-2-(((tert-butyldiphenylsilyl)oxy)methyl)cyclopropyl)methoxy)propanoate (intermediate in the synthesis of L13e). ES/MS: m/z 253.2 [M+Na]+.

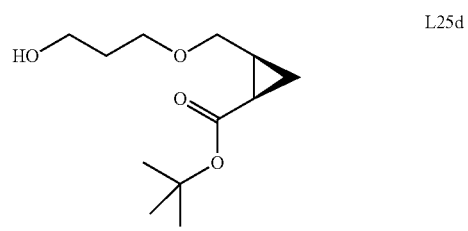 [SMILES: CC(C)(C)OC(=O)[C@@H]1C[C@@H]1COCCCO]

L25d

Preparation of tert-butyl 3-(((1R,2S)-2-(hydroxymethyl)cyclopropyl)methoxy)-2,2-dimethylpropanoate (L36a)

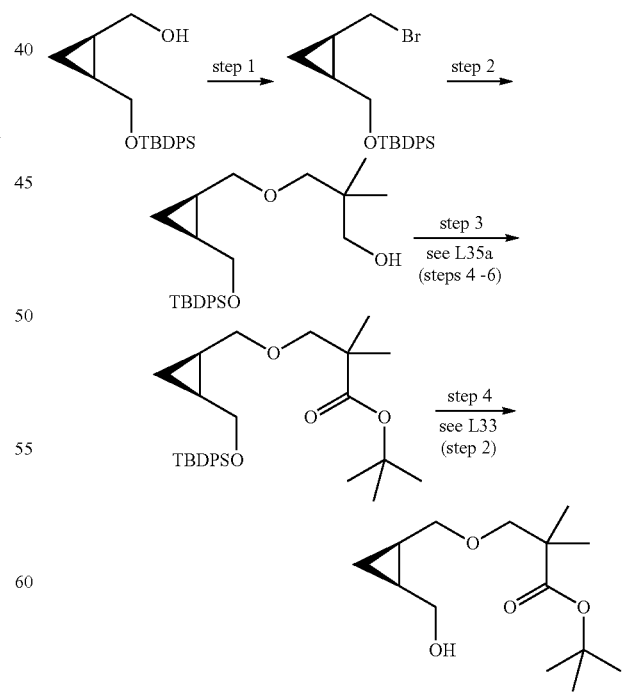

L36a

Step 1

To a DCM (15 mL) solution of (((1R,2S)-2-(((tert-butyl-diphenylsilyl)oxy)methyl)cyclopropyl)methanol (1.0 g, 2.94 mmol, J. Am. Chem. Soc. 2008, 16424), PPh₃ (924 mg, 3.52 mmol) and CBr₄ (1.46 g, 4.40 mmol) were added at 0° C. The mixture was stirred at rt for 2 h. The reaction was quenched with water and extracted with ethyl acetate. The organic layer was washed with brine, dried with MgSO₄, filtered, and concentrated. Purification by silica gel chromatography (0-50% EtOAC in hexane) provided ((((1S,2R)-2-(bromomethyl)cyclopropyl)methoxy)(tert-butyl)diphenylsilane. ¹H NMR (400 MHz, Chloroform-d) δ 7.72-7.65 (tt, J=6.2, 1.6 Hz, 4H), 7.48-7.34 (m, 6H), 3.86 (dd, J=11.3, 5.6 Hz, 1H), 3.68-3.56 (m, 2H), 3.42 (dd, J=10.3, 8.5 Hz, 1H), 1.49-1.32 (m, 2H), 1.05 (s, 9H), 0.92-0.85 (m, 1H), 0.32 (q, J=5.6 Hz, 1H).

Step 2

A solution of ((((1S,2R)-2-(bromomethyl)cyclopropyl)methoxy)(tert-butyl)diphenylsilane (1.3 g, 3.2 mmol), 2,2-dimethylpropane-1,3-diol (3.75 g, 36.1 mmol), TBAI (238 mg, 0.64 mmol) and sodium tert-butoxide (310 mg, 3.2 mmol) in THF was stirred at reflux for 24 h. The reaction was quenched with water and extracted with ethyl acetate. The organic layer was washed with brine, dried with MgSO₄, filtered, and concentrated. Purification by silica gel chromatography (0-100% EtOAC in hexane) provided 3-(((1R,2S)-2-(((tert-butyldiphenylsilyl)oxy)methyl)cyclopropyl)methoxy)-2,2-dimethylpropan-1-ol. ES/MS: m/z 449.3 [M+Na]⁺.

Step 3 tert-butyl 3-(((1R,2S)-2-(((tert-butyldiphenylsilyl)oxy)methyl)cyclopropyl)methoxy)-2,2-dimethylpropanoate was made following steps 4-6 of L35a using 3-(((1R,2S)-2-(((tert-butyldiphenylsilyl)oxy)methyl)cyclopropyl)methoxy)-2,2-dimethylpropan-1-ol. ES/MS: m/z 519.3 [M+Na]⁺.

Step 4 tert-butyl 3-(((1R,2S)-2-(hydroxymethyl)cyclopropyl)methoxy)-2,2-dimethylpropanoate was made following step 2 of L33 using tert-butyl 3-(((1R,2S)-2-(((tert-butyldiphenylsilyl)oxy)methyl)cyclopropyl)methoxy)-2,2-dimethylpropanoate. ES/MS: m/z 281.2 [M+Na]⁺.

tert-butyl 1-((((1R,2S)-2-(hydroxymethyl)cyclopropyl)methoxy)methyl)cyclopropane-1-carboxylate (L36b)

Prepared using a similar procedure to L36a using cyclopropane-1,1-diyldimethanol instead of 2,2-dimethylpropane-1,3-diol in step 2. ES/MS: m/z 279.2 [M+Na]⁺.

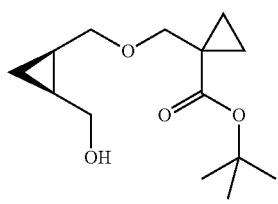

L36b

Preparation of tert-butyl (1S,2S)-2-((3-hydroxypropoxy)methyl)cyclopropane-1-carboxylate (L37)

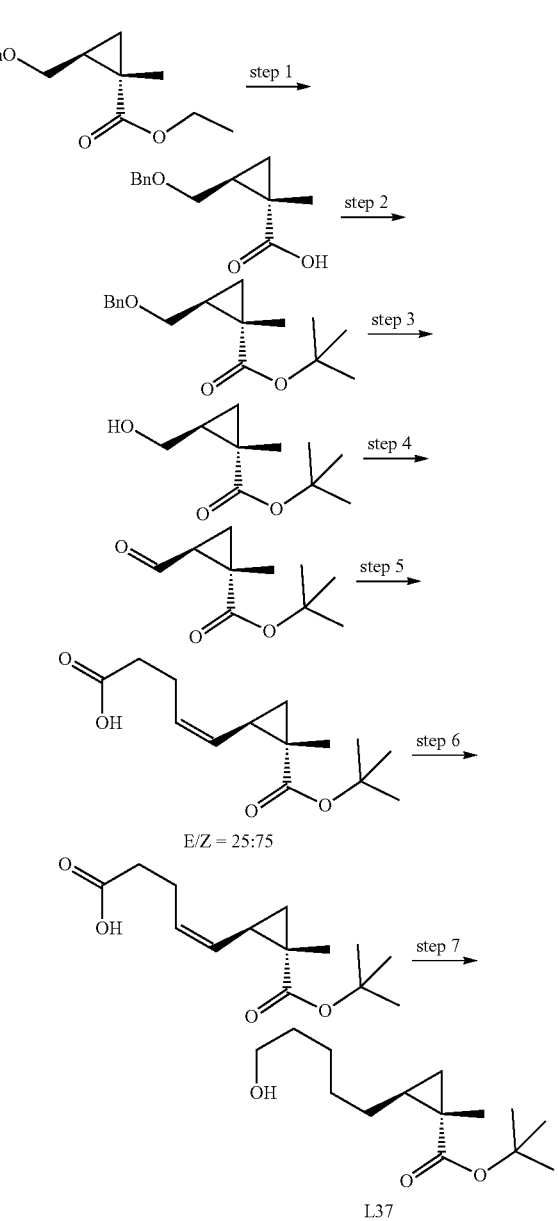

Step 1

Ethyl (1S,2S)-2-((benzyloxy)methyl)-1-methylcyclopropane-1-carboxylate (3 mmol, intermediate from Chem. Comm. 2010, 46, 5867-5869) was dissolved in THF/MeOH/H₂O (3:2:1, 15 mL) and LiOH(s) (6 mmol) was added. The resulting mixture was stirred overnight at 75° C. The solvents were evaporated and after usual work up (DCM/HCl 1N), the combined organics were dried over anhydrous Na₂S₂O₄ and evaporated to dryness to afford (1S,2S)-2-((benzyloxy)methyl)-1-methylcyclopropane-1-carboxylic acid.

Step 2

(1S,2S)-2-((benzyloxy)methyl)-1-methylcyclopropane-1-carboxylic acid (3 mmol) was dissolved in THF (9 mL) and 2-tert-butyl-1,3-diisopropylisourea (9 mmol) was added.

The resulting mixture was stirred at 65° C. overnight. The resulting mixture was cooled down to room temperature and silica (6 g) was added. After evaporation to dryness the residue was purified base column chromatography over silica gel (Hexane/EtOAc 0-5%) to afford tert-butyl (1S,2S)-2-((benzyloxy)methyl)-1-methylcyclopropane-1-carboxylate.
Step 3
tert-butyl (1S,2S)-2-((benzyloxy)methyl)-1-methylcyclopropane-1-carboxylate (2.5 mmol) was dissolved in EtOH (10 mL) and wet Pd/C (10% w/w, 10% mol) was added the resulting mixture was degassed with nitrogen and was then purged with H$_2$. The suspension was stirred at room temperature for 12 h at which point LCMS analysis showed full conversion. After filtration the organics were evaporated and the residue was purified by column chromatography over silica gel (Hexane/EtOAc 5-35%) to afford tert-butyl (1S,2S)-2-(hydroxymethyl)-1-methylcyclopropane-1-carboxylate.
Step 4
A solution of oxalyl chloride (3 mmol) in DCM (8 mL) was cooled down to −78° C. and DMSO (7 mmol) was added dropwise. The resulting mixture was stirred at −78° C. for 30 minutes before a solution of (1S,2S)-2-(hydroxymethyl)-1-methylcyclopropane-1-carboxylate (2 mmol) in DCM (n mL) was added dropwise. The mixture was stirred for an additional 30 minutes before triethylamine (10 mmol) was added. The reaction mixture was stirred at −78° C. and then slowly warmed up to 0° C. before being quenched with a saturated solution of ammonium chloride. After work up (DCM/NH$_4$Cl$_{(sat.)}$) the combined organics were filtered through a pad of silica (Pentane/Et$_2$O 95:5). The solvents were then carefully evaporated and tert-butyl (1S,2S)-2-formyl-1-methylcyclopropane-1-carboxylate was used without further purification.
Step 5
5-((1R,2S)-2-(tert-butoxycarbonyl)-2-methylcyclopropyl)pent-4-enoic acid was prepared as a E/Z mixture (E/Z=25:75) following the procedure reported for L31 (step 2) starting with (1S,2S)-2-formyl-1-methylcyclopropane-1-carboxylate.
Step 6.
5-((1R,2S)-2-(tert-butoxycarbonyl)-2-methylcyclopropyl)pent-4-enoic acid (E/Z=25:75) (2 mmol), sodium acetate (14 mmol) and tosylhydrazide (10 mmol) were charged into a sealed tube. THF (12 mL) and water (6 mL) were added and the tube was sealed. The reaction was heated to 80° C. for 12 hours. It was then cooled to room temperature and the pressure was carefully released. After usual work up (EtOAc/H$_2$O) the combined organics were dried over sodium sulfate and evaporated to dryness. The residue was purified by column chromatography (Hexane/EtOAc 5-50%) to afford 5-((1S,2S)-2-(tert-butoxycarbonyl)-2-methylcyclopropyl)pentanoic acid.
Step 7.
5-((1S,2S)-2-(tert-butoxycarbonyl)-2-methylcyclopropyl)pentanoic acid (1.5 mmol) was dissolved in THF (6 mL) and the reaction was cooled to 0° C. A solution of BH$_3$ in THF (1 N, 3.8 mL) was added dropwise and the reaction media was slowly warmed to room temperature. After full conversion of the starting acid as judged by TLC analysis the reaction was quenched with water at 0° C. After usual work up (EtOAc/H$_2$O) the combined organics were dried over sodium sulfate and evaporated to dryness. The residue was purified by column chromatography over silica gel (Hexane/EtOAc 5-30%) to afford tert-butyl (1S,2S)-2-(5-hydroxypentyl)-1-methylcyclopropane-1-carboxylate. $^1$H NMR (400 MHz, Chloroform-d) δ 3.67 (t, J=6.6 Hz, 2H), 1.38-1.25 (m, 2H), 1.53-1.37 (m, 5H), 1.44 (s, 9H), 1.38-1.25 (m, 3H), 1.23 (s, 3H), 0.30 (dd, J=5.7, 3.2 Hz, 1H).

Preparation of tert-butyl 5-(5-hydroxypentyl)-1-methyl-1H-pyrazole-4-carboxylate (L38a)

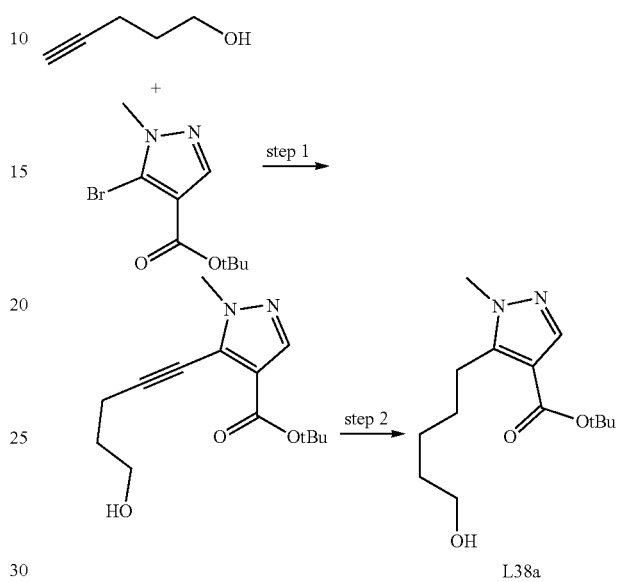

Step 1
tert-Butyl 5-bromo-1-methyl-1H-pyrazole-4-carboxylate (550 mg, 2.1 mmol) and pent-4-yne-1-ol (1.64 g, 6.3 mmol) were charged in a vial and dissolved in THF (2 mL) and triethylamine (2 mL). The resulting solution was degassed with Ar for 10 minutes. CuI (40 mg, 0.21 mmol) and PdCl$_2$(PPh$_3$)$_2$(74 mg, 0.10 mmol) were then added and the vial was sealed. The mixture was then heated at 90° C. overnight. The reaction was cooled to room temperature and silica was added. After evaporation to dryness, the residue was purified by column chromatography over silica gel (Hexanes/ethyl acetate 10% to 100%) to afford tert-butyl 5-(5-hydroxypent-1-yn-1-yl)-1-methyl-1H-pyrazole-4-carboxylate.
Step 2
tert-Butyl 5-(5-hydroxypent-1-yn-1-yl)-1-methyl-1H-pyrazole-4-carboxylate (320 mg, 1.2 mmol) was dissolved in EtOAc (4 mL). Pd/C (10% w/w, 200 mg) was added and the reaction vessel was placed under an H$_2$(g) atmosphere. It was then heated at 40° C. until LCMS analysis showed full conversion to the desired product. The reaction mixture was cooled to room temperature, filtered and evaporated to dryness. The resulting oil was purified by column chromatography over silica gel (Hexanes/ethyl acetate 10% to 100%) to afford tert-butyl 5-(5-hydroxypentyl)-1-methyl-1H-pyrazole-4-carboxylate. $^1$H NMR (400 MHz, Chloroform-d) δ 7.79 (s, 1H), 3.81 (s, 3H), 3.65 (t, J=6.4 Hz, 2H), 2.97-2.91 (m, 2H), 1.68-1.57 (m, 5H), 1.55 (s, 9H), 1.51-1.43 (m, 2H).

tert-butyl 4-(5-hydroxypent-1-yn-1-yl)-1-methyl-1H-pyrazole-5-carboxylate (L38b)

Prepared following a similar procedure to L38a (step 1 only) starting with tert-butyl 4-bromo-1-methyl-1H-pyrazole-5-carboxylate. ES/MS: m/z 265.5 [M+H]$^+$.

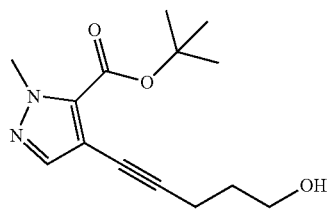

tert-butyl 4-(5-hydroxypentyl)-1-methyl-1H-pyrazole-5-carboxylate (L38c)

Prepared following a similar procedure to L38a starting with tert-butyl 4-bromo-1-methyl-1H-pyrazole-5-carboxylate. ES/MS: m/z 270.0 [M+H]$^+$.

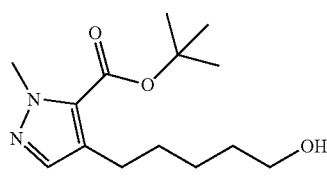

tert-butyl 5-(5-hydroxypentyl)-2-methyl-2H-1,2,3-triazole-4-carboxylate (L38d)

Prepared following a similar procedure to L38a starting with tert-butyl 5-bromo-2-methyl-2H-1,2,3-triazole-4-carboxylate ES/MS: m/z 270.9 [M+H]$^+$.

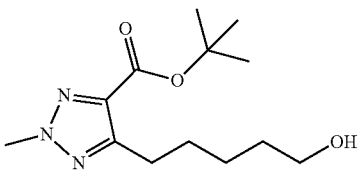

tert-butyl 4-(5-hydroxypentyl)-1-methyl-1H-1,2,3-triazole-5-carboxylate (L38e)

Prepared following a similar procedure to L38a starting with tert-butyl 4-bromo-1-methyl-1H-1,2,3-triazole-5-carboxylate. ES/MS: m/z 270.7 [M+H]$^+$.

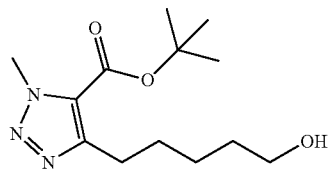

Preparation of tert-butyl 3-(5-hydroxypentyl)pyrazine-2-carboxylate (L39a)

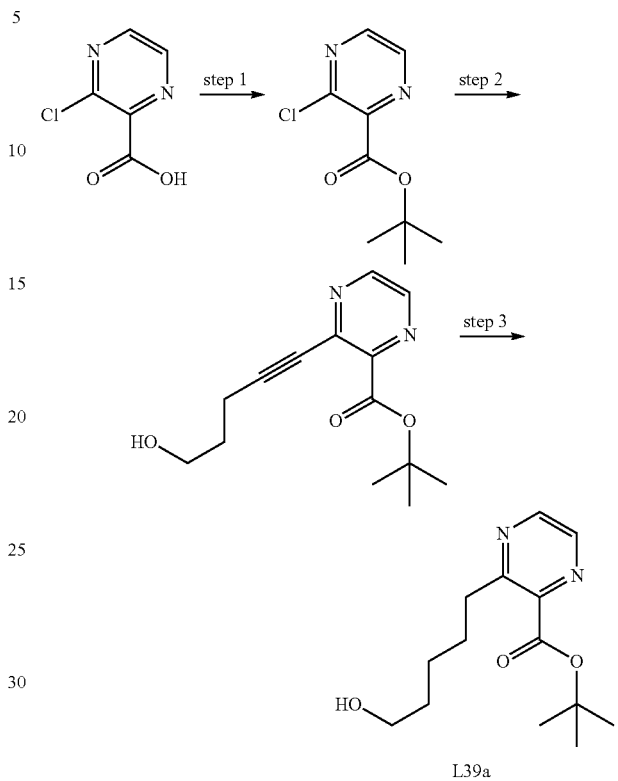

Step 1

2-tert-Butyl-1,3-diisopropylisourea (5 mL, 22.3 mmol) was added to a solution of 3-chloropyrazine-2-carboxylic acid (1.18 g, 7.44 mmol) in THF (34 mL) at rt. The reaction mixture was heated at 60° C. overnight. After cooling to rt, the reaction mixture was concentrated under reduced pressure and the resulting residue was purified via silica gel column chromatography (0-35% ethyl acetate in hexanes) to yield tert-butyl 3-chloropyrazine-2-carboxylate. ES/MS: m/z 214.6 [M+H]$^+$.

Step 2

A mixture of tert-butyl 3-chloropyrazine-2-carboxylate (600 mg, 2.8 mmol), tricyclohexylphosphine (31 mg, 0.112 mmol), and pent-4-yn-1-ol (0.39 mL, 4.2 mmol) in triethylamine (5.8 mL) was degassed with argon for 5 minutes. PdCl$_2$(PPh$_3$)$_2$ (39 mg, 0.056 mmol) and CuI (21 mg, 0.112 mmol) were then added and the reaction mixture was heated at 80° C. under argon for 24 h. After cooling to rt, the reaction mixture was concentrated under reduced pressure and the resulting residue was purified via silica gel column chromatography (25-100% ethyl acetate in hexanes) to yield tert-butyl 3-(5-hydroxypent-1-yn-1-yl)pyrazine-2-carboxylate. ES/MS: m/z 262.8 [M+H]$^+$.

Step 3

A mixture of tert-butyl 3-(5-hydroxypent-1-yn-1-yl)pyrazine-2-carboxylate (267 mg, 1.02 mmol) and palladium on carbon (10%, 28 mg, 0.0264 mmol) in ethanol (6 mL) was hydrogenated under an atmosphere of hydrogen. After 3 hours, the reaction mixture was filtered over celite and the filtrate was concentrated under reduced pressure to yield tert-butyl 3-(5-hydroxypentyl)pyrazine-2-carboxylate, which was used without further purification. ES/MS: m/z 266.9 [M+H]$^+$.

tert-butyl 3-(6-hydroxyhexyl)pyrazine-2-carboxylate
(L39b)

Prepared following a similar procedure to L39a using hex-5-yn-1-ol in place of pent-4-yn-1-ol during Step 2. ES/MS: m/z 276.9 [M+H]+.

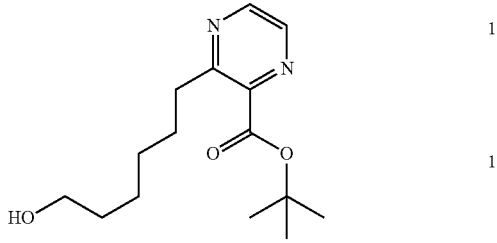

Preparation of tert-butyl 5-((1S,2S)-2-(hydroxymethyl)cyclopropyl)pentanoate (L40)

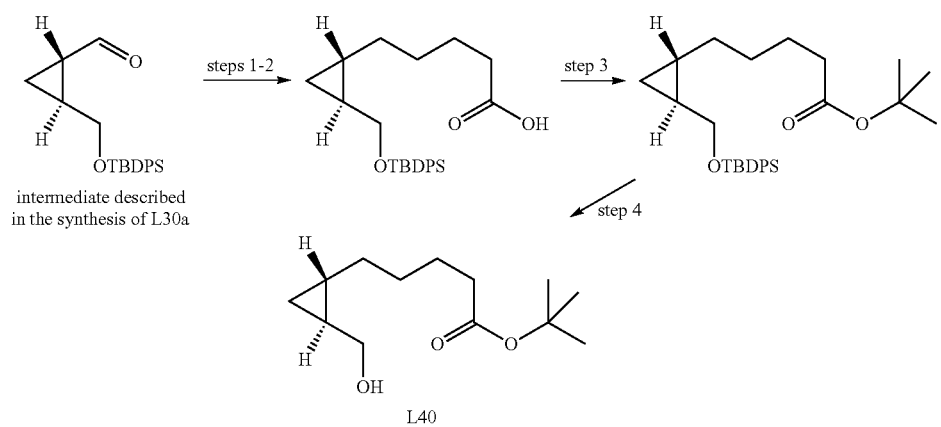

Step 1

4-(triphenyl-λ5-phosphanyl)butanoic acid hydrobromide (3.04 g, 7.1 mmol) was suspended in a mixture of anhydrous DMSO (30 mL) and THF (10 mL) and the mixture was placed in an ice bath. Shortly after a solution of tBuOK (1 M in THF, 14 mL) was added dropwise. The deep orange solution was then stirred at room temperature for one hour before a solution of (1S,2S)-2-(((tert-butyldiphenylsilyl)oxy)methyl)cyclopropane-1-carbaldehyde (intermediate described in the synthesis of L30a, 1.5 g, 4.43 mmol) in THF (5 mL) was added. The resulting mixture was stirred at room temperature until full conversion of the starting aldehyde (2 h). It was then quenched with NH4Cl(sat.) and extracted with EtOAc (2×50 mL). After evaporation to dryness the residue was purified by column chromatography (Hexane/EtOAc 10-40%) to afford 5-((1R,2S)-2-(((tert-butyldiphenylsilyl)oxy)methyl) cyclopropyl)pent-4-enoic acid as a Z/E mixture (Z/E=80:20). ES/MS: m/z 407.2 [M+H]+.

Step 2

5-((1R,2S)-2-(((tert-butyidiphenylsilyl)oxy)methyl) cyclopropyl)pent-4-enoic acid (1.3 g, 3.18 mmol) was dissolved in iPrOAc (30 mL) in a Parr shaker jar and Pt/C (2 mol %) was added. The resulting suspension was shaken under an atmosphere of H2(g) (20 psi) for 12 hours at which point LCMS analysis showed full conversion of the starting material. The suspension was filtered, evaporated to dryness and purified by reverse phase preparative HPLC to deliver 5-((1S,2S)-2-(((tert-butyldiphenylsilyl)oxy)methyl))cyclopropyl)pentanoic acid. ES/MS: m/z 409.3 [M+H]+.

Step 3

5-((1S,2S)-2-(((tert-butyldiphenylsilyl)oxy)methyl)cyclopropyl)pentanoic acid (910 mg, 2.21 mmol) was dissolved in THF (4 mL) and 2-tert-butyl-1,3-diisopropylisourea (2.11 mL, 8.84 mmol) was added. The resulting mixture was stirred at 65° C. for 12 hours; it was then cooled to room temperature and silica (3 g) was added. After evaporation of the volatiles under vacuum, the residue was purified by column chromatography over silica gel (Hexane/EtOAc 0-10%) to afford tert-butyl 5-((1S,2S)-2-(((tert-butyidiphenylsilyl)oxy)methy)cyclopropyl)pentanoate.

Step 4.

tert-Butyl 5-((1S,2S)-2-(((tert-butyldiphenylsilyl)oxy) methyl)cyclopropyl)pentanoate (550 mg, 1.18 mmol) was dissolved in THF (1 mL) and a solution of TBAF (1 M in THF, 1.77 mL) was added. The resulting solution was stirred for 2 h and then quenched with NaHCO3(sat.). After usual work up the organics were evaporated and the residue was purified by column chromatography over silica gel (Hexane/EtOAc 5-30%) to afford tert-butyl 5-((1S,2S)-2-(hydroxymethyl)cyclopropyl)pentanoate. $^1$H NMR (400 MHz, Chloroform-d) δ 3.63 (dd, J=10.7, 5.9 Hz, 1H), 3.45 (dd, J=10.7, 6.8 Hz, 1H), 2.22 (t. J=7.5 Hz, 2H), 1.68-1.57 (m, 2H), 1.46-1.37 (m, 2H), 1.37-1.12 (m, 2H), 1.07 (s, 9H), 0.98-0.76 (m, 1H), 0.59-0.49 (m, 1H), 0.33-0.25 (m, 1H), 0.24-0.19 (m, 1H).

Preparation of tert-butyl 5-((1S,2S)-2-(hydroxymethyl)cyclopropyl)-2-methylpentanoate (L41)

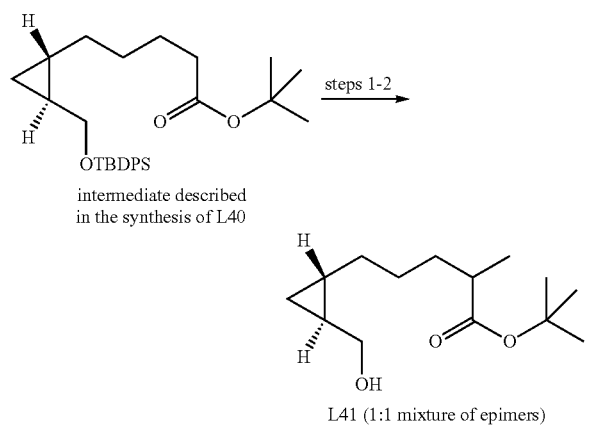

Step 1

A solution of tert-butyl 5-((1S,2S)-2-(((tert-butyldiphenylsilyl)oxy)methyl)cyclopropyl) pentanoate (120 mg, 0.26 mmol) (intermediate described in the synthesis of L40) in THF (1 mL) was cooled to −78° C. and LDA (1 1 in THF, 0.39 mL) was added dropwise. The solution was stirred at this temperature for 1 h before iodomethane (109 mg, 0.77 mmol) was added. The mixture was slowly warmed up to room temperature and stirred for an additional hour at room temperature. After aqueous work up, the residue was purified by column chromatography over silica gel (Hexane/EtOAc 0-5% c) to afford tert-butyl 5-((1S,2S)-2-(((tert-butyldiphenylsilyl)oxy)methyl)cyclopropyl)-2-methylpentanoate.

Step 2 tert-Butyl 5-((1S,2S)-2-(((tert-butyldiphenylsilyl)oxy)methyl)cyclopropyl)-2-methylpentanoate (110 mg, 0.23 mmol) was dissolved in THF (0.5 mL) and a solution of TBAF (1 N in THF, 0.35 mL) was added. The resulting solution was stirred for 2 hours and then quenched with NaHCO$_3$(sat.). After aqueous work up the organics were evaporated and the residue was purified by column chromatography over silica gel (Hexane/EtOAc 5-30%) to afford tert-butyl 5-((1S,2S)-2-(hydroxymethyl)cyclopropyl)-2-methylpentanoate. $^1$H NMR (400 MHz, Chloroform-d) δ 3.61 (dd, J=10.7, 6.0 Hz, 1H), 3.47 (dd, J=10.7, 6.7 Hz, 1H), 2.37-2.24 (m, 1H), 1.69-1.59 (m, 1H), 1.46 (s, 9H), 1.44-1.19 (m, 5H), 1.11 (d, J=7.0 Hz, 3H), 0.84-0.75 (m, 1H), 0.61-0.49 (m, 1H), 0.33-0.25 (m, 1H), 0.25-0.18 (m, 1H).

Preparation of tert-butyl 3-((R)-1-((1S,2S)-2-(hydroxymethyl)cyclopropyl)ethoxy)propanoate (L42a) and tert-butyl 3-((S)-1-((1S,2S)-2-(hydroxymethyl)cyclopropyl)ethoxy)propanoate (L42b)

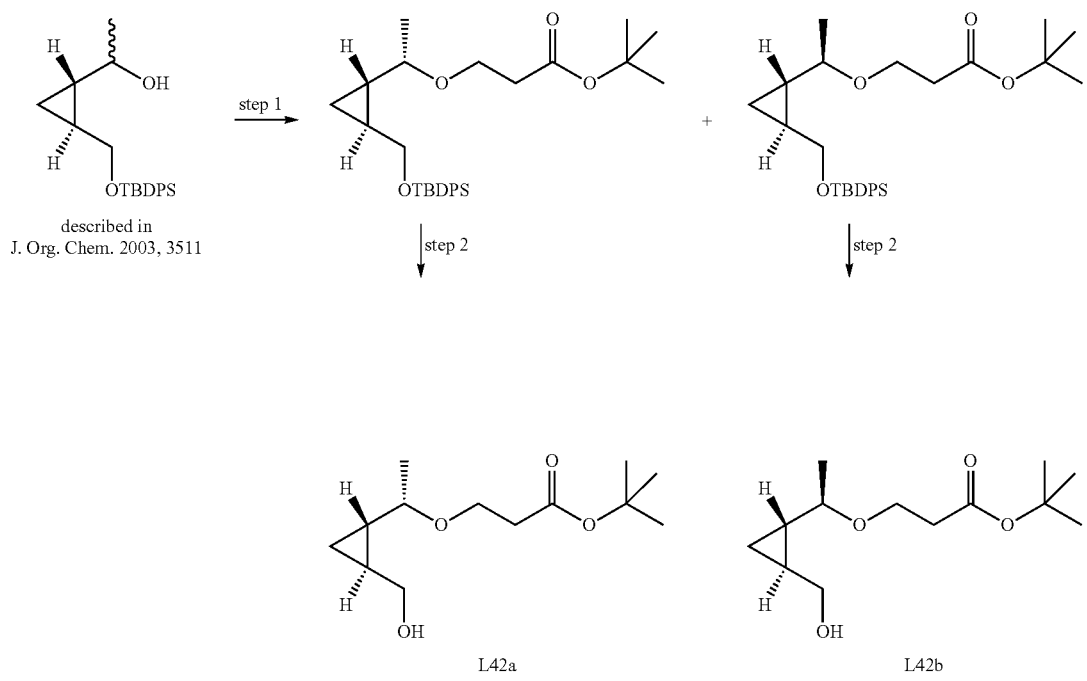

Step 1 and 2.

Prepared using a similar procedure to L13a steps 2-3 using 1-((1S,2S)-2-(((tert-butyldiphenylsilyl)oxy)methyl)cyclopropyl)ethan-1-ol (J. Org. Chem. 2003, 3511). The epimers were separated by purification on silica gel after step 1 and were separately submitted to step 2. L42a (derived from first eluting product of step 1): $^1$H NMR (400 MHz, Chloroform-d) δ 4.07-3.93 (m, 1H), 3.71 (dd, J=11.4, 5.7 Hz, 1H), 3.63 (ddd, J=9.2, 5.8, 5.1 Hz, 1H), 3.27 (dd, J=11.4, 8.3 Hz, 1H), 2.89-2.79 (m, 1H), 2.59-2.42 (m, 2H), 2.20 (d, J=10.3 Hz, 1H), 1.48 (s, 9H), 1.23 (d, J=6.3 Hz, 3H), 1.24-1.16 (m, 1H), 0.81-0.65 (m, 1H), 0.43-0.30 (m, 2H). L42b (derived from second eluting product of step 1): $^1$H NMR (400 MHz, Chloroform-d) δ 3.80 (dt, J=9.3, 6.4 Hz, 1H), 3.67 (dt, J=9.3, 6.4 Hz, 1H), 3.52 (dd, J=11.2, 6.9 Hz, 1H), 3.45 (dd, J=11.2, 7.1 Hz, 1H), 3.00 (dq, J=7.7, 6.2 Hz, 1H), 2.49 (t, J=6.4 Hz, 2H), 1.47 (s, 9H), 1.22 (d, J=6.2 Hz, 3H), 1.04-0.88 (m, 2H), 0.85-0.77 (m, 1H), 0.69-0.62 (m, 1H), 0.59-0.52 (m, 1H).

Preparation of tert-butyl 5-((1R,2S)-2-(hydroxymethyl)cyclopropyl)pentanoate (L43) and tert-butyl 5-((1R,2S)-2-(hydroxymethyl)cyclopropyl)-2,2-dimethylpentanoate (L44a)

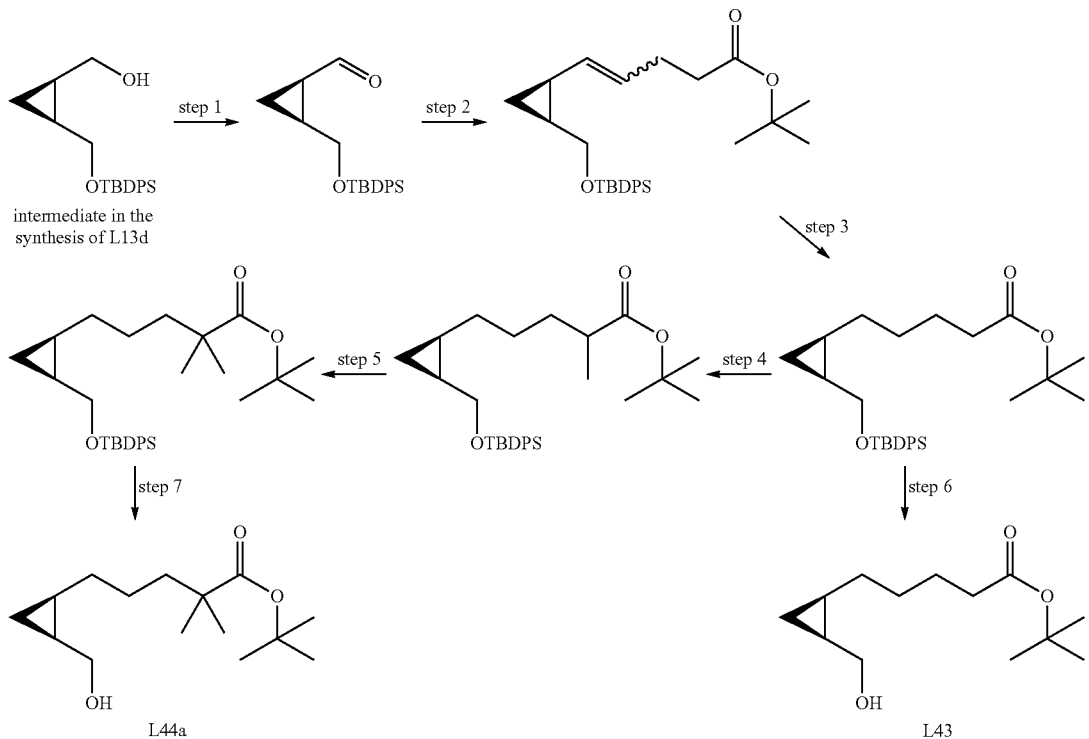

Step 1.

(1R,2S)-2-(((tert-butyldiphenylsilyl)oxy)methyl)cyclopropane-1-carbaldehyde was prepared using a similar procedure to using step 1 of L30a with ((1R,2S)-2-(((tert-butyldiphenylsilyl)oxy)methyl)cyclopropyl)methanol (intermediate in the synthesis of L13d). $^1$H NMR (400 MHz, Chloroform-d) δ 9.36 (d, J=5.4 Hz, 1H), 7.68-7.61 (m, 4H), 7.48-7.34 (m, 6H), 4.00 (dd, J=11.4, 5.6 Hz, 1H), 3.66 (dd, J=11.4, 8.1 Hz, 1H), 2.01-1.91 (m, 1H), 1.77 (qdd, J=8.3, 6.8, 5.6 Hz, 1H), 1.27 (dt, J=6.9, 5.2 Hz, 1H), 1.19 (td, J=8.0, 5.0 Hz, 1H), 1.03 (s, 9H).

Step 2 tert-butyl 5-((1S,2S)-2-(((tert-butyldiphenylsilyl)oxy)methyl)cyclopropyl)pent-4-enoate was prepared using a similar procedure to step 2 of L15a with (1R,2S)-2-(((tert-butyldiphenylsilyl)oxy)methyl)cyclopropane-1-carbaldehyde and (4-tert-butoxy-4-oxobutyl) triphenylphosphonium bromide. ES/MS: m/z 487.3 [M+Na]$^+$.

Step 3

To a solution of tert-butyl-5-((1S,2S)-2-(((tert-butyldiphenylsilyl)oxy)methyl)cyclopropyl)pent-4-enoate (1.35 g, 2.90 mmol) and N,N-diisopropylethylamine (8.7 mmol, 1.5 mL) in diethylether (20 mL) was added 2,4,6-triisopropylbenzenesulfonyl hydrazide (1.7 g, 5.8 mmol). The reaction stirred overnight. N,N-diisopropylethylamine (4.3 mmol, 0.76 mL) 2,4,6-triisopropylbenzenesulfonyl hydrazide (0.86 g, 2.9 mmol) were added twice a day until the reaction was complete. Saturated ammonium chloride was added and the aqueous layer was washed twice with diethyl ether. The combined organic layers were washed with saturated sodium bicarbonate and dried over magnesium sulfate, filtered and concentrated. Purification by silica gel chromatography (0 to 50% EtOAc in hexanes) gave tert-butyl 5-(((1R,2S)-2-(((tert-butyldiphenylsilyl)oxy)methyl)cyclopropyl)pentanoate (1.25g, 92%). ES/MS: m/z 489.3 [M+H]+.

Step 4

A flame dried flask under nitrogen was charged with THF (10 mL) and cooled to −78° C. To this cooled flask was added 1 M lithium diisopropylamide (2.78 mL, 2.78 mmol) and 1,3-dimethyl-3,4,5,6-tetrahydro-2(1H)-pyrimidinone (0.134 mL, 1.11 mmol). To this solution was added a solution of tert-butyl 5-((1R,2S)-2-(((tert-butyldiphenylsilyl)oxy)methyl)cyclopropyl)pentanoate (519 mg, 1.11 mmol) in THF (10 mL). The reaction stirred at −78° C. for 1 hr. Methyl iodide (0.210 mL, 3.34 mmol) was added dropwise, and the reaction stirred 30 min at −78° C., and then, warmed to room temperature for 1 h. To the reaction mixture was added water and the aqueous layer was washed with EtOAc. The organic layer was washed with 1 N HCl, saturated sodium bicarbonate, and brine, dried over sodium sulfate, filtered and concentrated. Purification by silica gel chromatography (0 to 60% EtOAc in hexanes) gave tert-butyl 5-((1R,2S)-2-(((tert-butyldiphenylsilyl)oxy)methyl)cyclopropyl)-2-methylpentanoate. $^1$H NMR (400 MHz, Chloroform-d) δ 7.72-7.65 (m, 4H), 7.44-7.34 (m, 6H), 3.75 (ddd, J=11.0, 6.2, 1.5 Hz, 1H), 3.55 (ddd, J=11.1, 8.3, 2.9 Hz, 1H), 1.66-1.57 (m, 1H), 1.48-1.02 (m, 28H), 0.85-0.74 (m, 1H), 0.59 (tdd, J=8.4, 4.6, 2.2 Hz, 1H), −0.17 (p, J=5.1 Hz, 1H).

Step 5 tert-butyl 5-((1R,2S)-2-(((tert-butyldiphenylsilyl)oxy)methyl)cyclopropyl)-2,2-dimethylpentanoate was prepared using a similar procedure to step 4 just above using tert-butyl 5-((1R,2S)-2-(((tert-butyldiphenylsilyl)oxy)methyl)cyclopropyl)-2-methylpentanoate. $^1$H NMR (400 MHz, Chloroform-d) δ 7.72-7.65 (m, 4H), 7.45-7.33 (m, 6H), 3.73 (dd, J=11.0, 6.4 Hz, 1H), 3.57 (dd, J=11.1, 8.1 Hz, 1H), 1.53-0.99 (m, 31H), 0.85-0.74 (m, 1H), 0.60 (td, J=8.3, 4.6 Hz, 1H), −0.17 (q, J=5.2 Hz, 1H).

Step 6 tert-butyl 5-((1R,2S)-2-(hydroxymethyl)cyclopropyl)pentanoate (L43) was prepared using a similar procedure to step 2 of L41 with tert-butyl 5-((1R,2S)-2-(((tert-butyldiphenylsilyl)oxy)methyl)cyclopropyl)pentanoate. $^1$H NMR (400 MHz, Chloroform-d) δ 3.67 (dt, J=11.8, 6.0 Hz, 1H), 3.56 (ddd, J=11.5, 8.1, 4.8 Hz, 1H), 2.22 (t, J=7.4 Hz, 2H), 1.68-1.58 (m, 1H), 1.50-1.36 (m, 11H), 1.34-1.21 (m, 2H), 1.15-1.08 (m, 2H), 0.93-0.81 (m, 1H), 0.71 (td, J=8.3, 4.6 Hz, 1H), −0.03 (q, J=5.3 Hz, 1H).

Step 7 tert-butyl 5-((1R,2S)-2-(hydroxymethyl)cyclopropyl)-2,2-dimethylpentanoate was prepared using a similar procedure to step 2 of L41 with tert-butyl 5-((1R,2S)-2-(((tert-butyldiphenylsilyl)oxy)methyl)cyclopropyl)-2,2-dimethylpentanoate. $^1$H NMR (400 MHz, Chloroform-d) δ 3.70-3.60 (m, 1H), 3.57 (ddd, J=11.6, 7.9, 4.7 Hz, 1H), 1.54-1.03 (m, 21H), 0.92-0.81 (m, 1H), 0.71 (td, J=8.3, 4.6 Hz, 1H), −0.03 (q, J=5.2 Hz, 1H).

tert-butyl 5-((1S,2S)-2-(hydroxymethyl)cyclopropyl)-2,2-dimethylpentanoate (L44b)

Prepared following a similar procedure to L44a starting with (1S,2S)-2-(((tert-butyldiphenylsilyl)oxy)methyl)cyclopropane-1-carbaldehyde (intermediate described in the synthesis of L30a). $^1$H NMR (400 MHz, Chloroform-d) δ 3.50 (dd, J=11.2, 6.9 Hz, 1H), 3.42 (dd, J=11.2, 7.3 Hz, 1H), 1.61-1.49 (m, 3H), 1.46 (s, 9H), 1.40-1.16 (m, 3H), 1.14 (s, 6H), 0.91-0.80 (m, 1H), 0.69-0.58 (m, 1H), 0.42-0.35 (m, 1H), 0.35-0.28 (m, 1H).

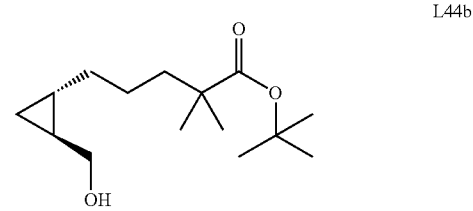 [SMILES: CC(C)(C)OC(=O)C(C)(C)CCC[C@H]1C[C@@H]1CO]

L44b

Preparation of tert-butyl 2-(2-((1R,2S)-2-(hydroxymethyl)cyclopropyl)ethyl)cyclopropane-1-carboxylate (L45a)

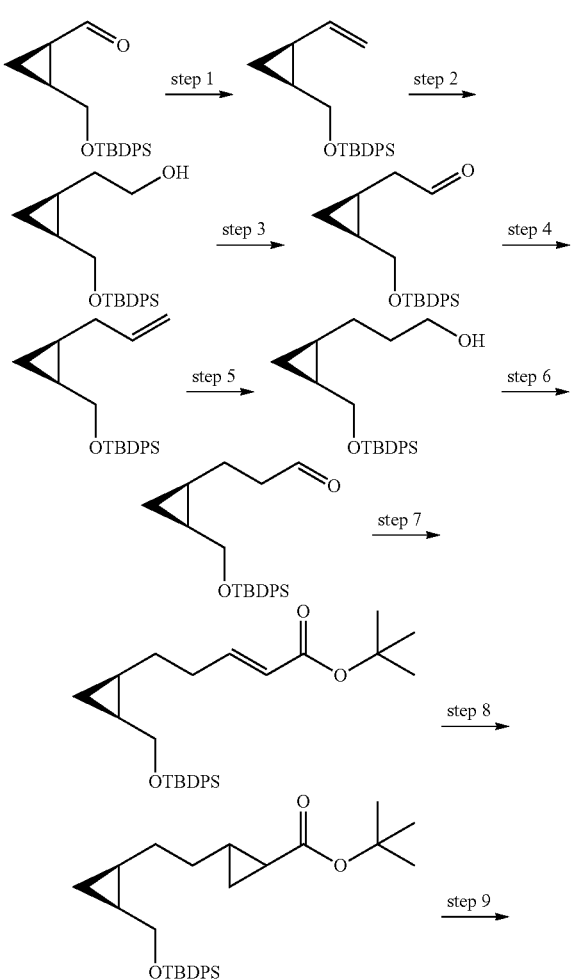

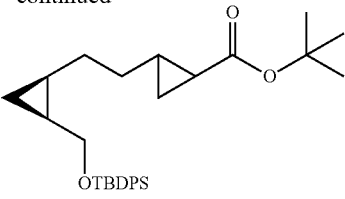

L45a

1:1 mixture of trans-cyclopropyl diastereoisomers

Step 1 tert-butyldiphenyl(((1S,2S)-2-vinylcyclopropyl)methoxy)silane was prepared using a similar procedure to step 2 of L15a with (1R,2S)-2-(((tert-butyldiphenylsilyl)oxy)methyl)cyclopropane-1-carbaldehyde (intermediate described in the synthesis of L43). $^1$H NMR (400 MHz, Chloroform-d) δ 7.71-7.65 (m, 4H), 7.45-7.31 (m, 6H), 5.55 (ddd, J=17.0, 10.2, 8.4 Hz, 1H), 5.07 (ddd, J=17.0, 1.9, 0.8 Hz, 1H), 4.93 (ddd, J=10.3, 2.0, 0.7 Hz, 1H), 3.72 (dd, J=11.0, 6.4 Hz, 1H), 3.61 (dd, J=11.0, 7.6 Hz, 1H), 1.64-1.53 (m, 1H), 1.36-1.23 (m, 1H), 1.04 (s, 9H), 0.85 (td, J=8.2, 4.9 Hz, 1H), 0.35 (q, J=5.5 Hz, 1H).

Step 2

2-((1S,2S)-2-(((tert-butyldiphenylsilyl)oxy)methyl)cyclopropyl)ethan-1-ol was prepared using a similar procedure to step 3 of L15a with tert-butyldiphenyl(((1S,2S)-2-vinylcyclopropyl)methoxy)silane. ES/MS: m/z 354.7 [M+H]$^+$.

Step 3

2-((1S,2S)-2-(((tert-butyldiphenylsilyl)oxy)methyl)cyclopropyl)acetaldehyde was prepared using a similar procedure to using step 1 of L30a with 2-((1S,2S)-2-(((tert-butyldiphenylsilyl)oxy)methyl)cyclopropyl)ethan-1-ol. $^1$H NMR (400 MHz, Chloroform-d) δ 9.85 (t, J=2.0 Hz, 1H), 7.73-7.62 (m, 4H), 7.46-7.35 (m, 6H), 3.89 (dd, J=11.4, 5.3 Hz, 1H), 3.43 (dd, J=11.4, 8.6 Hz, 1H), 2.52 (ddd, J=17.4, 7.0, 1.9 Hz, 1H), 2.33 (ddd, J=17.4, 7.4, 2.1 Hz, 1H), 1.29-1.12 (m, 2H), 1.04 (s, 9H), 0.78 (td, J=8.5, 5.0 Hz, 1H), 0.06 (q, J=5.4 Hz, 1H).

Step 4

(((1S,2R)-2-allylcyclopropyl)methoxy)(tert-butyl)diphenylsilane was prepared using a similar procedure to step 2 of L15a with 2-((1S,2S)-2-(((tert-butyldiphenylsilyl)oxy)methyl)cyclopropyl)acetaldehyde. $^1$H NMR (400 MHz, Chloroform-d) δ 7.72-7.65 (m, 4H), 7.45-7.32 (m, 6H), 5.94 (ddt, J=16.7, 10.2, 6.3 Hz, 1H), 5.06 (dd, J=17.2, 1.9 Hz, 1H), 4.95 (dd, J=10.2, 1.8 Hz, 1H), 3.77 (dd, J=11.1, 6.2 Hz, 1H), 3.58 (dd, J=11.1, 8.2 Hz, 1H), 2.15 (dt, J=15.1, 6.4 Hz, 1H), 1.99-1.90 (m, 1H), 1.18-1.09 (m, 1H), 0.93-0.82 (m, 1H), 0.65 (td, J=8.4, 4.7 Hz, 1H), −0.08 (q, J=5.3 Hz, 1H).

Step 5

3-((1R,2S)-2-(((tert-butyldiphenylsilyl)oxy)methyl)cyclopropyl)propan-1-ol was prepared using a similar procedure to step 3 of L15a with (((1S,2R)-2-allylcyclopropyl)methoxy)(tert-butyl)diphenylsilane. ES/MS: m/z 368.7 [M+H]$^+$.

Step 6.

3-((1R,2S)-2-(((tert-butyldiphenylsilyl)oxy)methyl)cyclopropyl)propanal was prepared using a similar procedure to using step 1 of L30a with 3-((1R,2S)-2-(((tert-butyldiphenylsilyl)oxy)methyl)cyclopropyl)propan-1-ol. $^1$H NMR (400 MHz, Chloroform-d) δ 9.78 (t, J=1.7 Hz, 1H), 7.71-7.63 (m, 4H), 7.45-7.33 (m, 6H), 3.85 (dd, J=11.2, 5.6 Hz, 1H), 3.46 (dd, J=11.3, 8.9 Hz, 1H), 2.73-2.53 (m, 2H), 1.71-1.59 (m, 2H), 1.19-1.08 (m, 1H), 1.05 (s, 9H), 0.86 (pd, J=7.8, 5.7 Hz, 1H), 0.63 (td, J=8.4, 4.8 Hz, 1H), −0.12 (q, J=5.4 Hz, 1H).

Step 7 tert-butyl (E)-5-((1R,2S)-2-(((tert-butyldiphenylsilyl)oxy)methyl)cyclopropyl)pent-2-enoate was prepared using a similar procedure to step 1 of L20a with using 3-((1R,2S)-2-(((tert-butyldiphenylsilyl)oxy)methyl)cyclopropyl)propanal. $^1$H NMR (400 MHz, Chloroform-d) δ 7.71-7.64 (m, 4H), 7.45-7.34 (m, 6H), 6.88 (dt, J=15.6, 6.9 Hz, 1H), 5.74 (dd, J=15.6, 1.7 Hz, 1H), 3.81 (dd, J=11.1, 5.7 Hz, 1H), 3.48 (dd, J=11.1, 8.7 Hz, 1H), 2.42-2.23 (m, 2H), 1.49 (s, 9H), 1.41-1.28 (m, 2H), 1.15-1.06 (m, 1H), 1.05 (s, 9H), 0.91-0.78 (m, 1H), 0.61 (td, J=8.4, 4.7 Hz, 1H), −0.15 (q, J=5.3 Hz, 1H).

Step 8 tert-butyl 2-(2-((1R,2S)-2-(((tert-butyldiphenylsilyl)oxy)methyl)cyclopropyl)ethyl)cyclopropane-1-carboxylate was prepared using a similar procedure to using step 2 of L20a with 3-((1R,2S)-2-(((tert-butyldiphenylsilyl)oxy)methyl)cyclopropyl)propanal. ES/MS: m/z 501.3 [M+Na]$^+$.

Step 9 tert-butyl 2-(2-((1R,2S)-2-(hydroxymethyl)cyclopropyl)ethyl)cyclopropane-1-carboxylate (1:1 mixture of trans-cyclopropyl diastereoisomers) was prepared using a similar procedure to step 2 of L41 with tert-butyl 2-(2-((1R,2S)-2-(((tert-butyldiphenylsilyl)oxy)methyl)cyclopropyl)ethyl)cyclopropane-1-carboxylate. $^1$H NMR (400 MHz, Chloroform-d) δ 3.73-3.64 (m, 1H), 3.61-3.52 (m, 1H), 1.64-1.57 (m, 1H), 1.49-1.20 (m, 13H), 1.18-1.03 (m, 2H), 0.97-0.82 (m, 2H), 0.77-0.69 (m, 1H), 0.66-0.59 (m, 1H), 0.01-−0.05 (m, 1H).

tert-butyl 2-(2-((1R,2R)-2-(hydroxymethyl)cyclopropyl)ethyl)cyclopropane-1-carboxylate (L45b)

Prepared following a similar procedure to L45a starting with (1R,2R)-2-(((tert-butyldiphenylsilyl)oxy)methyl)cyclopropane-1-carbaldehyde (intermediate in the synthesis of L31).

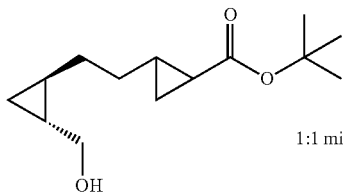

L45b

1:1 mixture of trans-cyclopropyl diastereoisomers

Preparation of tert-butyl 8-bromo-7,7-dimethyloctanoate (L46)

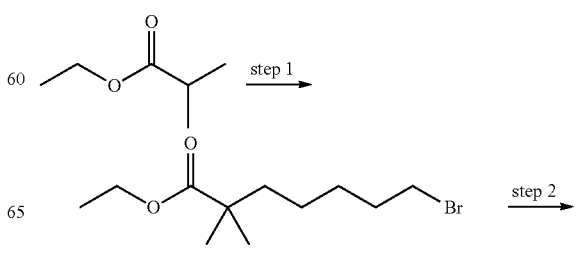

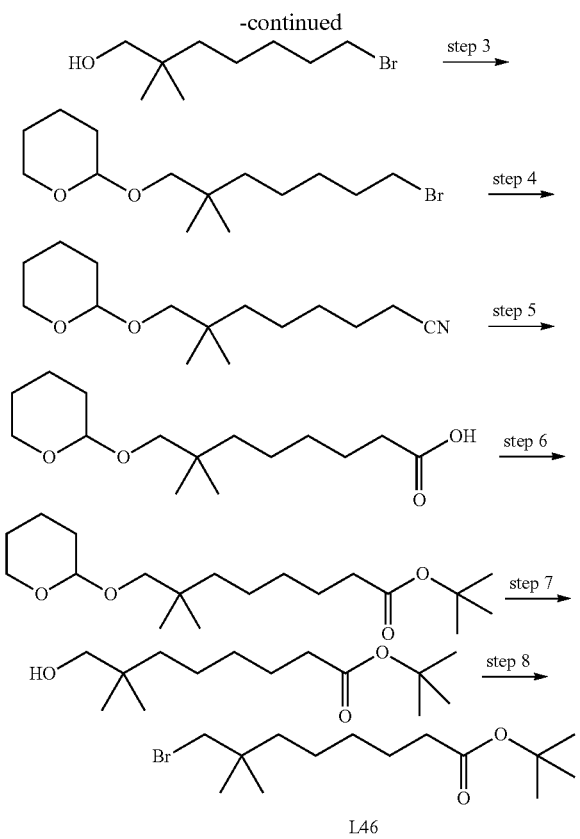

L46

Step 1

To a stirred solution of ethyl isobutyrate (5.00 g, 43.04 mmol) in anhydrous THF (50 mL) under argon, at −40° C., was added dropwise a solution of lithium diisopropylamide (2.0 M solution in THF, 26.9 mL, 53.80 mmol). After 1 h, dibromopentane (14.9 g, 64.56 mmol) was added at −40° C. The mixture was stirred for 30 min at −40° C. and then allowed to warm to room temperature and stirred overnight. The reaction was quenched with ice cold water (50 mL). The THF was removed under reduced pressure. The residue was extracted with DCM (3×30 mL) The combined organic layers were washed with brine (50 mL), dried over anhydrous $Na_2SO_4$, filtered and concentrated. The residue was purified by silica gel column chromatography (100% of PE) to afford ethyl 7-bromo-2,2-dimethylheptanoate. $^1$H NMR (400 MHz, $CDCl_3$): δ (ppm) 4.12 (q, J=7.2 Hz, 2H), 3.39 (t, J=6.8 Hz, 2H), 1.87-1.84 (m, 2H), 1.54-1.50 (m, 2H), 1.43-1.40 (m, 2H), 1.26-1.23 (m, 5H), 1.16 (s, 6H).

Step 2

To a stirred solution of ethyl 7-bromo-2,2-dimethylheptanoate (3.20 g, 12.06 mmol) in anhydrous THF (20 mL) was added dropwise $BH_3$/THF (21.7 mL, 1.0 M, 21.7 mmol) under Ar atmosphere at 0° C. The mixture was stirred at 75° C. for 6 h and then cooled to room temperature. The reaction was quenched with $NH_4Cl$ (sat., 30 mL) extracted with DCM (30 mL×3). The combined organic layers were washed with brine (30 mL), dried over anhydrous $Na_2SO_4$, filtered and concentrated. The residue is purified by silica gel column chromatography using a gradient from petroleum ether to petroleum ether/EtOAc=10/1(V/V) to afford 7-bromo-2,2-dimethylheptan-1-ol. $^1$H NMR (400 MHz, DMSO-d6): δ (ppm) 4.39-4.41 (m, 1H), 3.52 (t, J=6.8 Hz, 2H), 3.07 (d, J=4.4 Hz, 2H), 1.82-1.78 (m, 2H), 1.36-1.32 (m, 2H), 1.24-1.13 (m, 4H), 0.77 (s, 6H).

Step 3

To a solution of 7-bromo-2,2-dimethylheptan-1-ol (1.84 g, 8.25 mmol) in DCM (20 mL) was added p-TsOH (8 mg, 0.04 mmol) and 3,4-dihydro-2H-pyran (1.11g, 13.2 mmol) under Ar atmosphere at 0° C. The mixture was stirred at room temperature for 16 h. The reaction is quenched with $NH_4Cl$ (sat., 30 mL) and extracted with DCM (20 mL×3). The combined organic layers was washed with brine (30 mL), dried over anhydrous $Na_2SO_4$ and concentrated. The residue is purified by silica gel column chromatography using a gradient from petroleum ether to petroleum ether/EtOAc=30/1(V/V) to afford 2-((7-bromo-2,2-dimethylheptyl)oxy)tetrahydro-2H-pyran. $^1$H NMR (400 MHz, $CDCl_3$): δ (ppm) 4.55-4.54 (m, 1H), 3.87-3.81 (m, 1H), 3.53-3.39 (m, 4H), 3.99-3.97 (m, 1H), 1.91-1.82 (m, 3H), 1.73-1.62 (m, 5H), 1.52-1.38 (m, 2H), 1.37-1.27 (m, 4H), 0.87 (s, 6H).

Step 4

To a solution of NaCN (718 mg, 14.64 mmol) in DMSO (10 mL) was added 2-((7-bromo-2,2-dimethylheptyl)oxy) tetrahydro-2H-pyran (1.50 g, 4.88 mmol) and 18-Crown-6 (259 mg, 0.98 mmol) under $N_2$ atmosphere at rt. The mixture was stirred at 115° C. for 24 h. The mixture was cooled to rt and poured into water (30 mL), extracted with DCM (20 mL×3). The combined organic layers were washed with brine (30 mL) and dried over $Na_2SO_4$, filtered and concentrated. The residue was purified by silica gel column chromatography using a gradient from petroleum ether to petroleum ether/EtOAc=10/1 (V/V) to afford 7,7-dimethyl-8-((tetrahydro 2H-pyran-2-yl)oxy)octanenitrile. $^1$H NMR (400 MHz, $CDCl_3$): δ (ppm) 4.55-4.53 (m, 1H), 3.87-3.81 (m, 1H), 3.53-3.45 (m, 2H), 2.99-2.97 (m, 1H), 2.36-2.32 (m, 2H), 1.84-1.80 (m, 1H), 1.73-1.60 (m, 7H), 1.54-1.41 (m, 2H), 1.40-1.24 (m, 4H), 0.87 (s, 6H).

Step 5

To a solution of 7,7-dimethyl-8((tetrahydro-2H-pyran-2-yl)oxy)octanenitrile (1.50 g, 5.92 mmol) in EtOH (15 mL) was added NaOH (1.18 g, 29.6 mmol) and $H_2O$ (5 mL) at r.t. The mixture was heated to 75° C. for 24 h. The mixture was cooled to rt and poured into water (30 mL), extracted with DCM (20 mL×3). The aqueous phase was acidified by HCl (1 N) to pH=5 and extracted with EtOAc (30 mL×3). The combined organic layers was with brine brine (30 mL), dried over $Na_2SO_4$, filtered and concentrated afford 7,7-dimethyl-8-((tetrahydro-2H-pyran-2-yl)oxy)octanoic acid.

Step 6

To a solution of 7,7-dimethyl-8-((tetrahydro-2H-pyran-2-yl)oxy)octanoic acid (1.05 g, 3.85 mmol) in DCM/t-BuOH (v/v=1/1) (11 mL) was added triethylamine (778 mg, 7.70 mmol), DMAP (95 mg, 0.77 mmol) and di-tert-butyl dicarbonate (1.26 g, 5.78 mmol) at rt. The mixture was stirred at room temperature for 3 hours. The reaction is quenched with $NaHCO_3$ (sat. 30 mL) and extracted with DCM (20 mL×3). The combined organic layers were washed with brine (30 mL), dried over anhydrous $Na_2SO_4$, filtered and concentrated. The residue is purified by silica gel column chromatography using a gradient from petroleum ether to petroleum ether/EtOAc=50/1(V/V) to afford tert-butyl 7,7-dimethyl-8-((tetrahydro-2H-pyran-2-yl)oxy)octanoate. $^1$H NMR (400 MHz, $CDCl_3$): δ (ppm) 4.55-4.54 (m, 1H), 3.86-3.81 (m, 1H), 3.51-3.44 (m, 2H), 2.99-2.96 (m, 1H), 2.22-2.18 (m, 2H), 1.84-1.82 (m, 1H), 1.69-1.68 (m, 1H), 1.60-1.49 (m, 7H), 1.44 (s, 9H), 1.26-1.22 (m, 6H), 0.87 (s, 6H).

Step 7

To a solution of tert-butyl 7,7-dimethyl-8-((tetrahydro-2H-pyran-2-yl)oxy)octanoate (760 mg, 2.31 mmol) in MeOH (8 mL) was added p-TsOH (527 mg, 2.77 mmol) at 0° C. The mixture was stirred at room temperature for 1 hour. The reaction was quenched with NaHCO₃ (sat. 10 mL) and extracted with DCM (20 mL×3). The combined organic layers were washed with brine (20 mL), dried over anhydrous Na₂SO₄, filtered and concentrated. The residue was purified by silica gel column chromatography using a gradient from petroleum ether to petroleum ether/EtOAc=15/1 (v/v) to afford tert-butyl 8-hydroxy-7,7-dimethyloctanoate, ¹H NMR (400 MHz, CDCl₃): δ (ppm) 3.39 (s, 2H), 2.22-2.19 (m, 2H), 1.59-1.55 (m, 3H), 1.44 (s, 9H), 1.30-1.23 (m, 6H), 0.87 (s, 6H).

Step 8

To a solution of tert-butyl 8-hydroxy-7,7-dimethyloctanoate (6.6 g, 40.9 mmol) in THF (66 mL) was added PPh₃ (16.10 g, 61.4 mmol) and CBr₄ (20.4 g, 61.4 mmol) at rt. The mixture was stirred at room temperature for 16 h. The reaction was filtered and the filtrate was concentrated. The residue is purified by silica gel column chromatography using a gradient from petroleum ether to petroleum ether/EtOAc-=50/1(V/V) to afford title compound tert-butyl 8-bromo-7,7-dimethyloctanoate. ¹H NMR (400 MHz, CDCl₃): δ (ppm) 3.28 (s, 2H), 2.23-2.19 (m, 2H), 1.61-1.59 (m, 3H), 1.44 (s, 9H), 1.32-1.26 (m, 6H), 0.99 (s, 6H).

Preparation of tert-butyl 6-(1-(bromomethyl)cyclopropyl)hexanoate (L47)

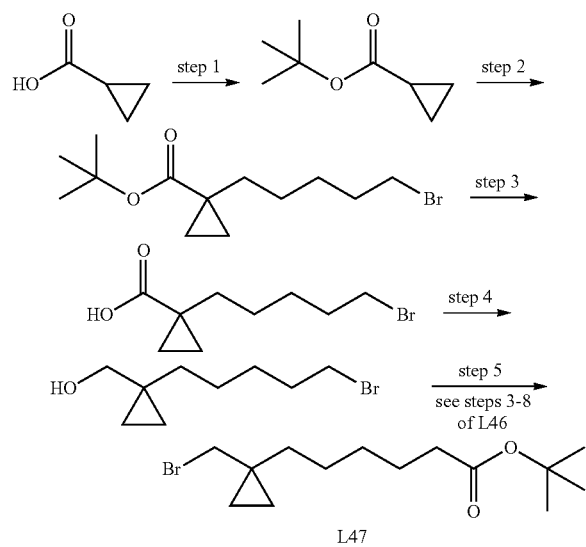

Step 1

Concentrated sulfuric acid (32 mL, 581 mmol) was added to a vigorously stirred suspension of anhydrous magnesium sulfate (278 g, 2.33 mmol) in dichloromethane (250 mL). The mixture was stirred for 15 minutes at rt, after which cyclopropanecarboxylic acid (50.0 g, 581.3 mmol) and 2-methyl-propan-2-ol (278 mL, 2.91 mol) were added sequentially. The mixture was stoppered tightly and stirred at ambient temperature for 16 h. The reaction mixture was then quenched with saturated aqueous sodium bicarbonate (4.2 L) and stirred until all the magnesium sulfate had dissolved. The phases were separated and the organic phase washed with water (500 mL), saturated aqueous sodium chloride (500 mL), dried over anhydrous magnesium sulfate, filtered and concentrated in vacuo to afford tert-butyl cyclopropanecarboxylate. ¹H NMR (400 MHz, CDCl₃): δ 1.45 (s, 9H), 0.93-0.88 (m, 2H), 0.79-0.73 (m, 2H).

Step 2

To a stirred solution of lithium diisopropylamide (2.0 M solution in THF, 169 mL, 338 mmol) was added dropwise a solution of tert-butyl cyclopropanecarboxylate (32 g, 225 mmol) in anhydrous THF (300 mL) under Ar atmosphere at −70° C., After the addition was complete, the mixture was allowed to stir at −30° C. for 0.5 h. The mixture was cooled to −70° C., 1,5-dibromopentane (61.6 g, 270.4 mmol) was added dropwise. The mixture was stirred for another 30 min at −70° C. and then allowed to warm to room temperature and stirred overnight. The mixture was quenched by ice water (300 mL) and extracted with EtOAc (200 mL×3). The combined organic layers was washed with brine, dried over Na₂SO₄, filtered and concentrated under reduce pressure. The residue was purified by chromatography on silica gel (petroleum ether:EtOAc 50:1) to afford tert-butyl 1-(5-bromopentyl)cyclopropane-1-carboxylate. ¹H NMR (400 MHz, CDCl₃): δ 3.36-3.32 (m, 2H), 1.81-1.78 (m, 2H), 1.42-1.41 (m, 2H), 1.40-1.38 (m, 4H), 1.37 (s, 9H), 1.05-1.03 (m, 2H), 0.54-0.51 (m, 2H).

Step 3

A solution of tert-butyl 1-(5-bromopentyl)cyclopropane-1-carboxylate (73.0 g, crude) and HCl (350) mL, 4 N in dioxane) was stirred at room temperature overnight. The mixture was concentrated under reduced pressure and the residue was purified by column chromatography on silica gel (petroleum ether:EtOAc=1:1, v/v) to afford 1-(5-bromopentyl)cyclopropane-1-carboxylic acid. ¹H NMR (400 MHz, DMSO-d6): δ 12.01 (br s, 1H), 3.56-3.50 (m, 2H), 1.86-1.77 (m, 2H), 1.53-1.38 (m, 6H), 1.03-1.00 (m, 2H), 0.67-0.66 (m, 2H).

Step 4

To a stirred solution of 1-(5-bromopentyl)cyclopropane-1-carboxylic acid (65.0 g, crude) in THF (300 mL), a solution of BH₃ (1 M solution in THF, 361 mL, 361 mmol) was added dropwise under Ar atmosphere at 0° C. The reaction mixture was stirred at 75° C. for 16 h. The solution was quenched by saturated aqueous NH₄Cl (500 mL) and extracted with DCM (500 mL×3). The organic layers were concentrated under reduced pressure and purified by chromatograph on silica gel (petroleum ether:EtOAc=3:1) to afford (1-(5-bromopentyl)cyclopropyl)methanol. ¹H NMR (400 MHz, DMSO-d6): δ 4.33 (br s, 1H), 3.52 (t, J=6.8 Hz, 2H), 3.20 (s, 2H), 1.81-1.77 (m, 2H), 1.36-1.31 (m, 6H), 0.31-0.28 (m, 2H), 0.20-0.19 (m, 2H).

Step 5

3-((1R,2S)-2-(((tert-butyldiphenylsilyl)oxy)methyl)cyclopropyl)propan-1-ol was prepared using a similar procedure to steps 3-8 of L46 with (1-(5-bromopentyl)cyclopropyl)methanol. ¹H NMR (400 MHz, CDCl3): δ 3.36 (s, 2H), 2.23-2.19 (m, 2H), 1.63-1.57 (m, 3H), 1.45 (s, 9H), 1.35-1.33 (m, 5H), 0.60-0.53 (m, 4H).

Preparation of (1R,2R)-2-allylcyclopropane-1-carboxylic Acid (L48)

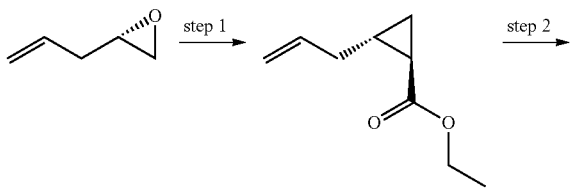

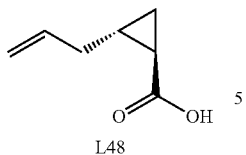

L48

Step 1

To a stirred solution of NaH (2.85 g) in toluene (35 mL) at 0° C. under argon was added ethyl 2-(diethoxyphosphoryl)acetate (15.3 mL) dropwise. After 10 min the (S)-2-allyloxirane (5 g, (S)-2-allyloxirane was synthesized from (S)-2-(chloromethyl)oxirane following a procedure reported in *Org. Lett.* 2012, 2462) was added dropwise at 0° C. Then the reaction mixture was stirred at 120° C. for 16 h. The progress of the reaction was monitored by TLC. The reaction mixture was poured into cold sat aq NH₄Cl solution. The resulting mixture was extracted with ethyl acetate (2×100 mL), organic layer was washed with brine solution (1×100 mL). Resulting organic layer was dried over Na₂SO₄ filtered and evaporated. The resulting crude was purified by silica gel (100-200 mesh) column chromatography and eluted with 0-20% ethyl acetate in petroleum ether to afford ethyl (1R,2R)-2-allylcyclopropane-1-carboxylate.

Step 2

Ethyl ((1R,2R)-2-allylcyclopropane-1-carboxylate (1.54 g) was dissolved in THF/MeOH/H₂O (2:2:1, 15 mL) and LiOH·H₂O (630 mg) was added and the mixture was stirred at 75° C. for 5 h. The solvents were evaporated to dryness and a work up was carried out using DCM and HCl (1M). The organic were dried over sodium sulfate, filtered and evaporated to dryness to afford (1R,2R)-2-allylcyclopropane-1-carboxylic acid. $^1$H NMR (400 MHz, DMSO-d6) δ 12.02 (brs, 1H), 5.90-5.77 (m, 1H), 5.13-4.97 (m, 2H), 2.17-1.95 (m, 2H), 1.39-1.20 (m, 2H), 0.98 (dt, J=8.7, 4.3 Hz, 1H), 0.74 (ddd, J=8.1, 6.2, 3.8 Hz, 1H).

(1S,2S)-2-allylcyclopropane-1-carboxylic Acid (L48b)

Prepared following a similar procedure to L48 starting (R)-2-allyloxirane. $^1$H NMR (400 MHz, DMSO-d6) δ 12.02 (brs, 1H), 5.90-5.77 (m, 1H), 5.13-4.97 (m, 2H), 2.17-1.95 (m, 2H), 1.39-1.20 (m, 2H), 0.98 (dt, J=8.7, 4.3 Hz, 1H), 0.74 (ddd, J=8.1, 6.2, 3.8 Hz, 1H).

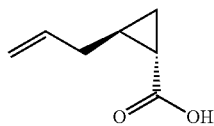

L48b

(1R,2R)-2-allyl-1-methylcyclopropane-1-carboxylic Acid (L48c)

Prepared following a similar procedure to L48 using ethyl 2-(diethoxyphosphoryl)propanoate instead of ethyl 2-(diethoxyphosphoryl)acetate.

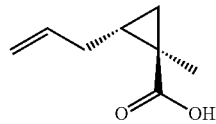

L48c

(1S,2S)-2-allyl-1-methylcyclopropane-1-carboxylic Acid (L48d)

Prepared following a similar procedure to L48 starting with (R)-2-allyloxirane and using ethyl 2-(diethoxyphosphoryl)propanoate instead of ethyl 2-(diethoxyphosphoryl)acetate.

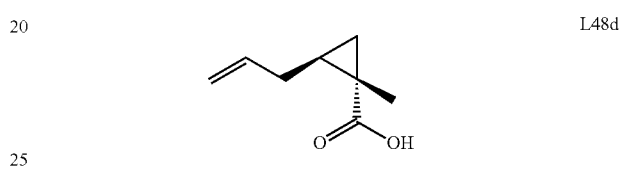

L48d

Preparation of tert-butyl 3-(5-(tosyloxy)pentyl)pyrazine-2-carboxylate (L49)

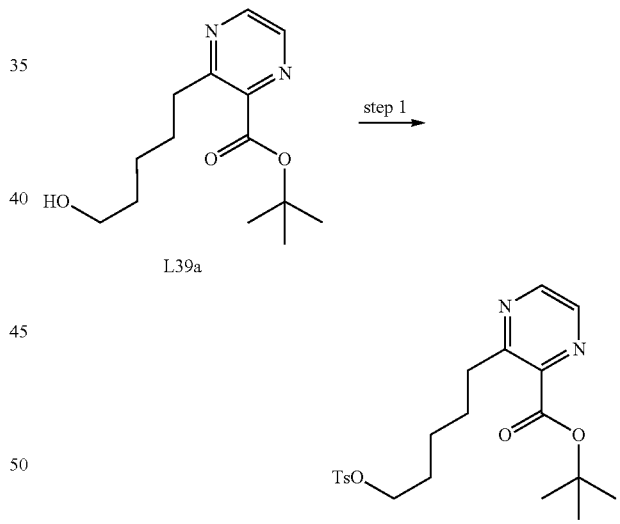

Step 1

To a solution of tert-butyl 3-(5-hydroxypentyl)pyrazine-2-carboxylate (100 mg, 0.375 mmol) and triethylamine (0.16 mL, 1.13 mmoL) in DCM (3.3 mL) at 0° C. was added 4-methylbenzenesulfonyl chloride (107 mg, 0.563 mmol) and DMAP (4.6 mg, 0.0375 mmol). The reaction mixture was warmed to rt and stirred overnight. The reaction mixture was concentrated under reduced pressure and the resulting residue was purified via silica gel column chromatography (0-40% ethyl acetate in hexanes) to yield tert-butyl 3-(5-(tosyloxy)pentyl)pyrazine-2-carboxylate. MS: m/z 420.9 [M+H]⁺.

Preparation of tert-butyl 3-(5-hydroxypentyl)isonicotinate (L50a)

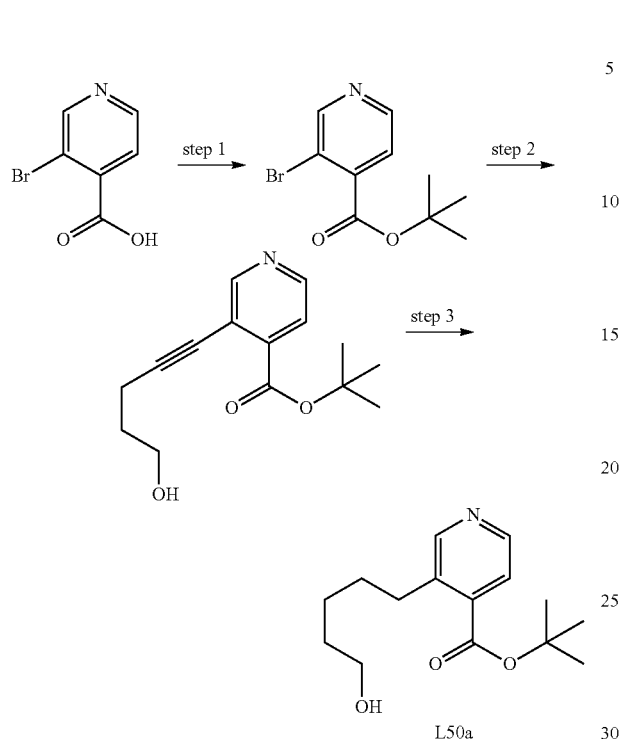

L50a

Step 1

2-tert-butyl-1,3-diisopropylisourea (2.91 g, 14.5 mmol) was added to a solution of 3-bromopyridine-4-carboxylic acid (0.979 g, 4.84 mmol) in DCM (20 mL) at 0° C. The mixture was allowed to warm to rt and was stirred 72 h. The reaction mixture was filtered and the filter pad was rinsed with DCM. The filtrate was washed successively with 10% citric acid soln and sat bicarb soln, dried (Na$_2$SO$_4$), filtered, and concentrated. The residue was purified via flash column chromatography on silica gel (0-100% EtOAc/hexanes) to yield tert-butyl 3-bromopyridine-4-carboxylate. ES/MS: m/z 258.1, 260.1 [M+H]$^+$.

Step 2 tert-butyl 3-(5-hydroxypent-1-yn-1-yl)isonicotinate was prepared according to the procedure described in Step 2 for L39, using tert-butyl 3-bromopyridine-4-carboxylate in place of tert-butyl 3-chloropyrazine-2-carboxylate. ES/MS: m/z 262.2 [M+H]$^+$.

Step 3 tert-butyl 3-(5-hydroxypentyl)isonicotinate was prepared according to the procedure described in Step 4 for L8a, using tert-butyl 3-(5-hydroxypent-1-yn-1-yl)isonicotinate in place of tert-butyl 3-(4-(((tert-butyldimethylsilyl)oxy)but-1-en-1-yl)-2-fluorobenzoate. ES/MS: m/z 266.2 [M+H]$^+$. For more sensitive substrate (e.g., alkene substrate with halogenated pyridine), Pt/C (0.042 g of 10% Pt on C, wet) can be used.

tert-butyl 2-fluoro-6-(5-hydroxypentyl)benzoate (L50b)

Prepared in a manner similar to L50a, using 2-bromo-5-fluorobenzoic acid in place of 3-bromopyridine-4-carboxylic acid. ES/MS: m/z 305.2 [M+Na]$^+$.

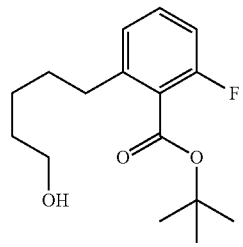

L50b tert-butyl 4-(5-hydroxypentyl)nicotinate (L50c)

Prepared in a manner similar to L50a, using 4-bromonicotinic acid in place of 3-bromopyridine-4-carboxylic acid. ES/MS: m/z 266.2 [M+H]$^+$.

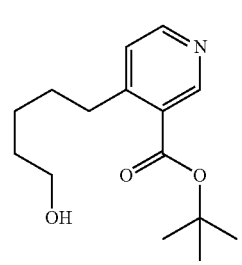

L50c tert-butyl 3-fluoro-2-(5-hydroxypentyl)benzoate (L50d)

Prepared in a manner similar to L50a, using 2-bromo-3-fluorobenzoic acid in place of 3-bromopyridine-4-carboxylic acid. ES/MS: m/z 305.2 [M+Na]$^+$.

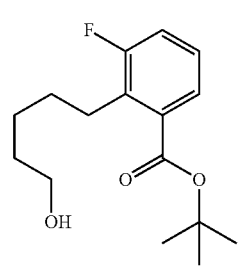

L50d tert-butyl 3-fluoro-5-(5-hydroxypentyl)isonicotinate (L50e)

Prepared in a manner similar to L50a, using 3-bromo-5-fluoroisonicotinic acid in place of 3-bromopyridine-4-carboxylic acid. ES/MS: m/z 284.2 [M+H]$^+$.

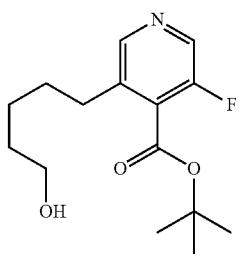

tert-butyl 3-chloro-5-(5-hydroxypentyl)isonicotinate (L50f)

Prepared in a manner similar to L50a, using 3-bromo-5-chloroisonicotinic acid in place of 3-bromopyridine-4-carboxylic acid. ES/MS: m/z 300.2 [M+H]$^+$.

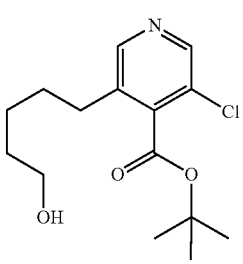

tert-butyl 2-(5-hydroxypentyl)-6-methylbenzoate (L50g)

Prepared following a similar procedure to L50a using 2-bromo-6-methylbenzoic acid. ES/MS: m/z 278.6 [M+H]$^+$.

tert-butyl 2-(difluoromethyl)-6-(5-hydroxypentyl)benzoate (L50h)

Prepared following a similar procedure to L50a using 2-bromo-6-difluoromethylbenzoic acid. $^1$H NMR (400 MHz, Chloroform-d) δ 7.47 (d, J=7.3 Hz, 1H), 7.40 (t, J=7.7 Hz, 1H), 7.32 (d, J=6.4 Hz, 1H), 6.87 (t, J=56.1 Hz, 1H), 3.65 (t, J=6.5 Hz, 2H), 2.75-2.66 (m, 2H), 1.71-1.54 (m, 13H), 1.49-1.38 (m, 2H).

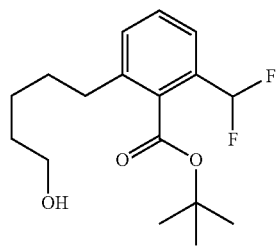

tert-butyl 4-(5-hydroxypentyl)-2-methylnicotinate (L50i)

Prepared following a similar procedure to L50a using 4-bromo-2-methylnicotinic acid. ES/MS: m/z 280.1 [M+H]$^+$.

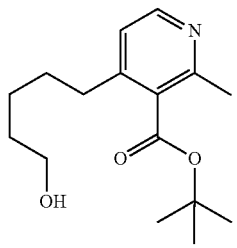

tert-butyl 3-(5-hydroxypentyl)-5-methylisonicotinate (L50j)

Prepared following a similar procedure to L50a using 3-bromo-5-methylisonicotinic acid. ES/MS: m/z 279.9 [M+H]$^+$.

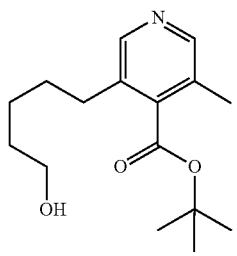

tert-butyl 2-(5-hydroxypentyl)benzoate (L50k)

Prepared following a similar procedure to L50a using 2-bromobenzoic acid. ES/MS: m/z 287.2 [M+Na]$^+$.

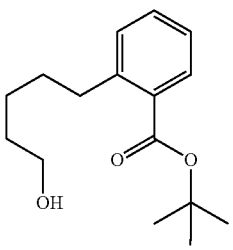

tert-butyl 3-(5-hydroxypentyl)pyrazine-2-carboxylate (L50l)

Prepared following a similar procedure to L50a using 3-chloropyrazine-2-carboxylic acid. ES/MS: m/z 267.2 [M+H]⁺.

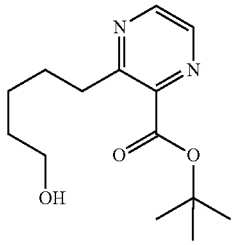

tert-butyl 3-(5-hydroxypentyl)picolinate (L50m)

Prepared in a manner similar to L50a, using 3-bromopicolinic acid in place of 3-bromopyridine-4-carboxylic acid. ES/MS: m/z 266.2 [M+H]⁺.

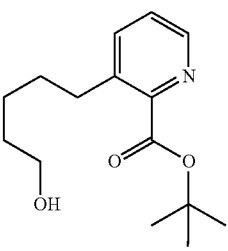

tert-butyl 2-(5-hydroxypentyl)benzoate (L50n)

Prepared in a manner similar to L50a, using 2-bromobenzoic acid in place of 3-bromopyridine-4-carboxylic acid. ES/MS: m/z 265.2 [M+H]⁺.

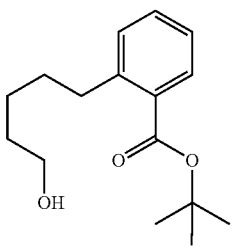

tert-butyl 5-(5-hydroxypentyl)-2-methylpyrimidine-4-carboxylate (L50o)

Prepared following a similar procedure to L50a using 5-bromo-2-methyl-pyrimidine-4-carboxylic acid in place of 3-bromopyridine-4-carboxylic acid. ES/MS: m/z 280.9 [M+H]⁺.

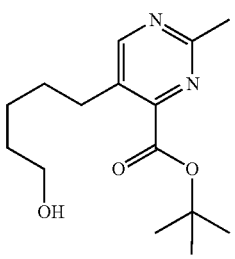

tert-butyl 5-(5-hydroxypentyl)thieno[3,2-b]pyridine-6-carboxylate (L50a)

Prepared following a similar procedure to L50a using 5-chlorothieno[3,2-b]pyridine-6-carboxylic acid in place of 3-bromopyridine-4-carboxylic acid. ES/MS: m/z 322 [M+H]⁺.

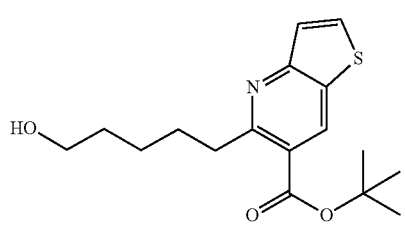

tert-butyl 4-fluoro-2-(5-hydroxypentyl)nicotinate (L50r)

Prepared in a manner similar to L50a, using 2-bromo-4-fluoronicotinic acid in place of 3-bromopyridine-4-carboxylic acid. ES/MS: m/z 284.2 [M+H]⁺.

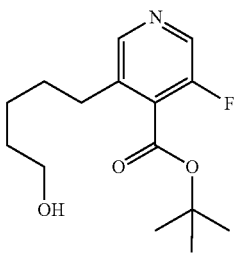

L50r tert-butyl 2-chloro-4-(5-hydroxypentyl)nicotinate
(L50s)

Prepared in a manner similar to L50a using 3 4-bromo-2-chloronicotinic acid. ES/MS: m/z 300.2 [M+H]$^+$.

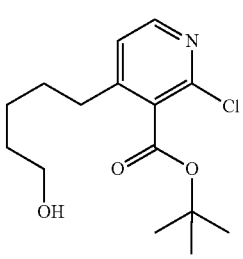

L50s tert-butyl 4-fluoro-2-(5-hydroxypentyl)nicotinate
(L50t)

Prepared in a manner similar to L50a, using 2-bromo-4-fluoronicotinic acid in place of 3-bromopyridine-4-carboxylic acid. ES/MS: m/z 284.2 [M+H]$^+$.

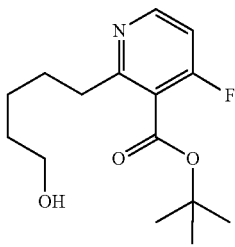

L50t tert-butyl 6-chloro-2-(5-hydroxypentyl)nicotinate
(L50u)

Prepared in a manner similar to L50a, using 2-bromo-6-chloronicotinic acid. ES/MS: m/z 300.2 [M+H]$^+$.

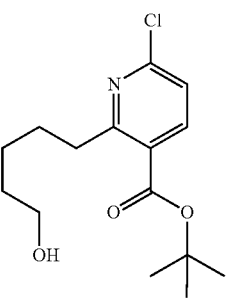

L50u tert-butyl 2-chloro-5-(5-hydroxypentyl)isonicotinate
(L50v)

Prepared in a manner similar to L50a, using 5-bromo-2-chloroisonicotinic acid. ES/MS: m/z 300.2 [M+H]$^+$.

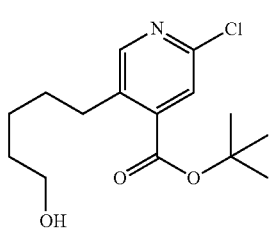

L50v tert-butyl 6-chloro-4-(5-hydroxypentyl)nicotinate
(L50w)

Prepared in a manner similar to L50a, using 4-bromo-6-chloronicotinic acid in place of 5-bromo-2-chloroisonicotinic acid. ES/MS: m/z 300.2 [M+H]$^+$.

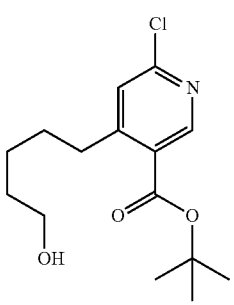

L50w tert-butyl 2-(5-hydroxypentyl)-6-methylnicotinate
(L50x)

Prepared in a manner similar to L50a, using 2-bromo-6-methylnicotinic acid. ES/MS: m/z 280.2 [M+H]$^+$.

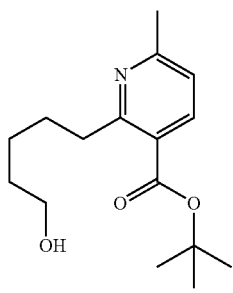

tert-butyl 6-(difluoromethyl)-2-(5-hydroxypentyl)nicotinate (L50y)

Prepared in a manner similar to L50a, using 4-chloro-6-(difluoromethyl)nicotinic acid. ES/MS: m/z 316.2 [M+H]$^+$.

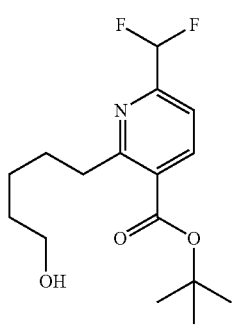

tert-butyl 2-fluoro-4-(5-hydroxypentyl)nicotinate (L50z)

Prepared in a manner similar to L50a, using tert-butyl 5-bromo-2-fluoroisonicotinate. ES/MS: m/z 284.2 [M+H]$^+$.

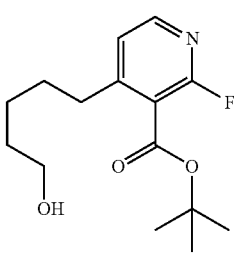

tert-butyl 2-(5-hydroxypentyl)-6-methoxybenzoate (L50aa)

Prepared in a manner similar to L50a, using 2-bromo-6-methoxybenzoic acid. ES/MS: m/z 317.2 [M+Na]$^+$.

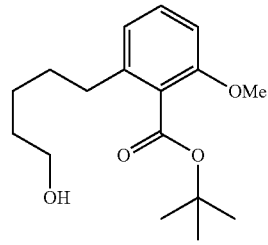

Preparation of (1S,3R)-3-allyl-2,2-difluoro-1-methylcyclopropane-1-carboxylic Acid (L51a)

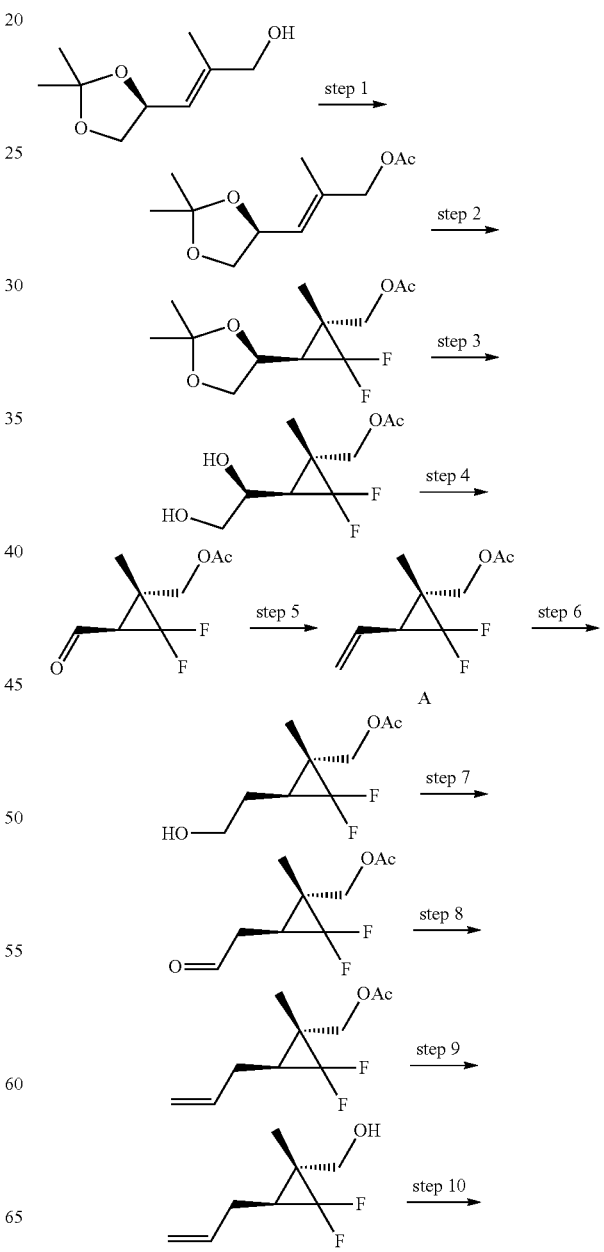

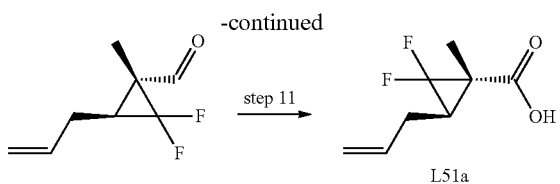

(S,E)-3-(2,2-dimethyl-1,3-dioxolan-4-yl)-2-methylprop-2-en-1-ol is prepared as described in *Angew. Chem. Int. Ed.,* 2014, 53, 12205.

Step 1.
(S,E)-3-(2,2-dimethyl-1,3-dioxolan-4-yl)-2-methylallyl acetate was prepared using standard conditions with (S,E)-3-(2,2-dimethyl-1,3-dioxolan-4-yl)-2-methylprop-2-en-1-ol, acetyl anhydride and triethylamine in THF.

Step 2
((1R,3R)-3-((S)-2,2-dimethyl-1,3-dioxolan-4-yl)-2,2-difluoro-1-methylcyclopropyl)methyl acetate was prepared using a similar procedure to step 1 of I-17 with (S,E)-3-(2,2-dimethyl-1,3-dioxolan-4-yl)-2-methylallyl acetate.

Step 3
((1R,3R)-3-((S)-1,2-dihydroxyethyl)-2,2-difluoro-1-methylcyclopropyl)methyl acetate was prepared using standard conditions with ((1R,3R)-3-((S)-2,2-dimethyl-1,3-dioxolan-4-yl)-2,2-difluoro-1-methylcyclopropyl)methyl acetate in acetic acid.

Step 4
((1R,3R)-2,2-difluoro-3-formyl-1-methylcyclopropyl)methyl acetate was prepared using standard conditions with ((1R,3R)-3-((S)-1,2-dihydroxyethyl)-2,2-difluoro-1-methylcyclopropyl)methyl acetate and sodium periodate in THF and water.

Step 5
((1R,3S)-2,2-difluoro-1-methyl-3-vinylcyclopropyl)methyl acetate was prepared using a similar procedure to step 2 of L15a with ((1R,3R)-2,2-difluoro-3-formyl-1-methylcyclopropyl)methyl acetate.

Step 6
((1R,3S)-2,2-difluoro-3-(2-hydroxyethyl)-1-methylcyclopropyl)methyl acetate was prepared using a similar procedure to step 3 of L15a with ((1R,3S)-2,2-difluoro-1-methyl-3-vinylcyclopropyl)methyl acetate.

Step 7
((1R,3S)-2,2-difluoro-1-methyl-3-(2-oxoethyl)cyclopropyl)methyl acetate was prepared using a similar procedure to step 1 of L30a with ((1R,3S)-2,2-difluoro-3-(2-hydroxyethyl)-1-methylcyclopropyl)methyl acetate. ES/MS: m/z 207.24 [M+H]+.

Step 8
((1R,3S)-3-allyl-2,2-difluoro-1-methylcyclopropyl)methyl acetate was prepared using a similar procedure to step 2 of L15a with ((1R,3S)-2,2-difluoro-1-methyl-3-(2-oxoethyl)cyclopropyl)methyl acetate.

Step 9
((1R,3S)-3-allyl-2,2-difluoro-1-methylcyclopropyl)methanol was prepared using a similar procedure to step 2 of L27 with ((1R,3S)-3-allyl-2,2-difluoro-1-methylcyclopropyl)methyl acetate.

Step 10
(1R,3S)-3-allyl-2,2-difluoro-1-methylcyclopropane-1-carbaldehyde was prepared using a similar procedure to step 1 of L30a with ((1R,3S)-3-allyl-2,2-difluoro-1-methylcyclopropyl)methanol.

Step 11
(1S,3R)-3-allyl-2,2-difluoro-1-methylcyclopropane-1-carboxylic acid was prepared using a similar procedure to step 4 of L17 with (1R,3S)-3-allyl-2,2-difluoro-1-methylcyclopropane-1-carbaldehyde.

Preparation of tert-butyl 2-(2-((1R,2R)-2-(hydroxymethyl)cyclopropyl)ethyl)benzoate (L52a)

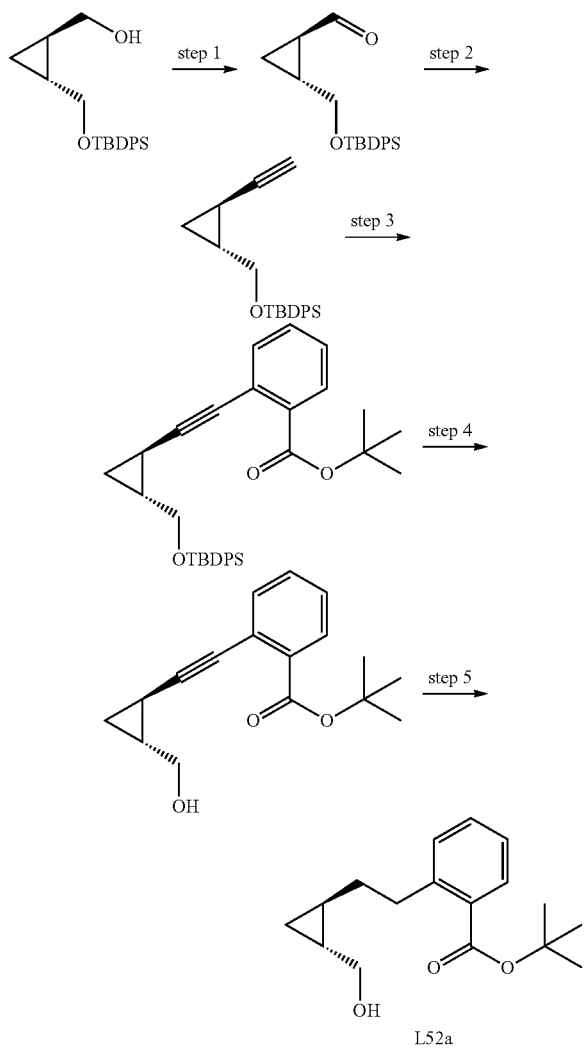

Step 1
DMSO (1.0 mL, 14.7 mmol) was added, dropwise, to a solution of oxalyl chloride (0.6 mL, 7.05 mmol) in DCM (50 mL) at −78° C. The mixture was stirred at −78° C. for 10 min before ((1R,2R)-2-(((tert-butyldiphenylsilyl)oxy)methyl)cyclopropyl)methanol (2.00 g, 5.87 mmol) in DCM (10 mL) was added. The reaction mixture was stirred at −78° C. for 30 min. TEA (4.1 mL, 29.4 mmol) was added and the reaction mixture was allowed to warm to rt over 30 min. The mixture was diluted with DCM and water. The aqueous layer was extracted twice with DCM. The combined organic layers were washed sequentially with sat bicarb soln and brine, dried (Na$_2$SO$_4$), filtered, and concentrated. The residue was purified via flash column chromatography on silica gel (0-20% EtOAc/hexanes) to afford (1R,2R)-2-(((tert-butyldiphenylsilyl)oxy)methyl)cyclopropane-1-carbaldehyde. ES/MS: m/z 361.2 [M+Na]$^+$.

Step 2

Dimethyl (1-diazo-2-oxopropyl)phosphonate (1.69 g, 8.82 mmol) was added, dropwise, to a mixture of (1R,2R)-2-(((tert-butyldiphenylsilyl)oxy)methyl)cyclopropane-1-carbaldehyde (1.99 g, 5.88 mmol) and potassium carbonate (1.62 g, 11.7 mmol) in MeOH (60 mL). The mixture was stirred at rt for 16 h. The reaction mixture was diluted with hexanes and water. The aqueous layer was extracted with hexanes. The combined organic layers were washed with brine, dried (Na$_2$SO$_4$), filtered, and concentrated. The residue was purified via flash column chromatography on silica gel to afford tert-butyl(((1R,2R)-2-ethynylcyclopropyl)methoxy)diphenylsilane. ES/MS: m/z 334.9 [M+H]$^+$.

Step 3 tert-butyl 2-(((1R,2R)-2-(((tert-butyldiphenylsilyl)oxy)methyl)cyclopropyl)ethynyl)benzoate was prepared according to the procedure described in Step 2 for L39, using tert-butyl(((1R,2R)-2-ethynylcyclopropyl)methoxy)diphenylsilane in place of 4-pentyn-1-ol. ES/MS: m/z 533.3 [M+Na]$^+$.

Step 4

TBAF (0.82 mL of a 1 M soln in THF, 0.82 mmol) was added to a solution of tert-butyl 2-(((1R,2R)-2-(((tert-butyldiphenylsilyl)oxy)methyl)cyclopropyl)ethynyl)benzoate (0.209 g, 0.409 mmol) in THF (4 mL). The reaction mixture was stirred at rt for 1 h. The mixture was diluted with EtOAc and water, and the aqueous layer was extracted with EtOAc. The combined organic layers were washed with brine, dried (Na$_2$SO$_4$), filtered, and concentrated. The residue was purified via flash column chromatography on silica gel (0-100% EtOAc/hexanes) to afford tert-butyl 2-(((1R,2R)-2-(hydroxymethyl)cyclopropyl)ethynyl)benzoate. ES/MS: m/z 295.2 [M+Na]$^+$.

Step 5

Pd/C (0.003 g, 5% Pd on C, wet) was added to a solution of tert-butyl 2-(((1R,2R)-2-(hydroxymethyl)cyclopropyl)ethynyl)benzoate (0.056 g, 0.206 mmol) in EtOH (10 mL). The mixture was shaken on a Parr shaker under 20 psi H$_2$ for 1 h. The reaction mixture was filtered. The filtrate was concentrated to afford tert-butyl 2-(2-((1R,2R)-2-(hydroxymethyl)cyclopropyl)ethyl)benzoate. ES/MS: m/z 299.2 [M+Na]$^+$.

tert-butyl 2-(2-((1S,2S)-2-(hydroxymethyl)cyclopropyl)ethyl)benzoate (L52b)

Prepared in a manner similar to L52a, using ((1S,2S)-2-(((tert-butyldiphenylsilyl)oxy)methyl)cyclopropyl)methanol in place of ((1R,2R)-2-(((tert-butyldiphenylsilyl)oxy)methyl)cyclopropyl)methanol. ES/MS: m/z 299.2 [M+Na]$^+$.

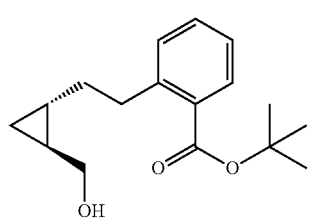

L52b

Preparation of rac-(1R,3S)-2,2-difluoro-3-vinylcyclopropane-1-carboxylic Acid (L53)

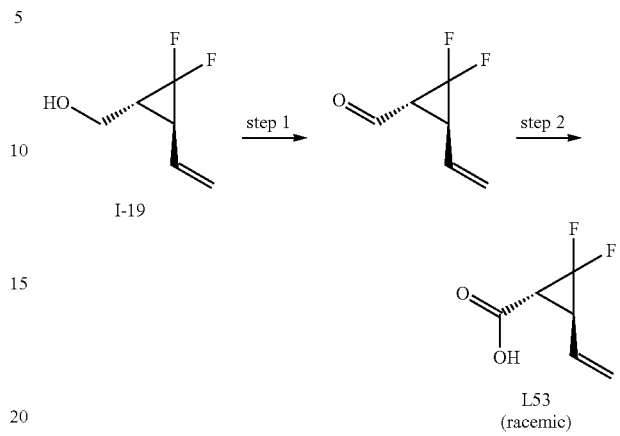

Step 1 rac-(1R,3S)-2,2-difluoro-3-vinylcyclopropane-1-carbaldehyde was prepared using a similar procedure to step 1 of L30a with rac-((1R,3S)-2,2-difluoro-3-vinylcyclopropyl)methanol

Step 2.

A solution of rac-(1R,3S)-2,2-difluoro-3-vinylcyclopropane-1-carbaldehyde (1.2 g, 9.1 mmol) and 2-methyl-2-butene (4.8 mL, 45 mmol) in THF (20 mL), tBuOH (40 mL), and water (20 mL) was allowed to stir for 5 min. To this solution was added a solution of sodium chlorite (2.1 g, 23 mmol) in water (5 mL) dropwise over 5 min. The mixture was allowed to stir vigorously for 1 hr. 1 N HCl was added and the organic layer was separated. The aqueous layer was washed twice with Et$_2$O. The combined organic layers were dried over MgSO$_4$, filtered, and concentrated to give rac-(1R,3S)-2,2-difluoro-3-vinylcyclopropane-1-carboxylic acid (L53) (1.3 g, 8.7 mmol, 96%). $^1$H NMR (400 MHz, Chloroform-d) δ 5.62-5.51 (m, 1H), 5.40 (d, J=16.7 Hz, 1H), 5.32 (d, J=10.4 Hz, 1H), 3.04-2.92 (m, 1H), 2.41 (dd, J=13.6, 7.2 Hz, 1H).

Preparation of (1S,2S)-1-fluoro-2-vinylcyclopropane-1-carboxylic Acid (L54a)

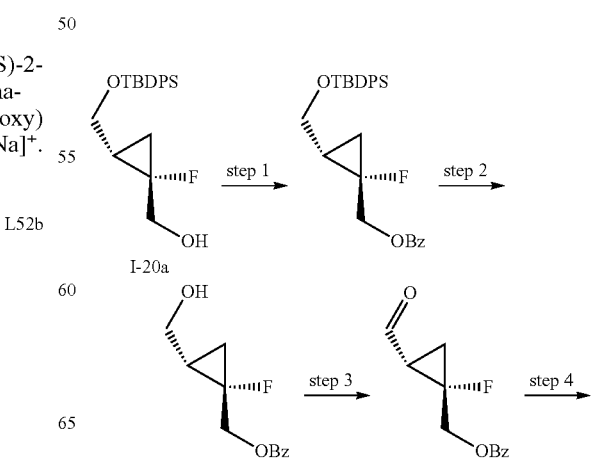

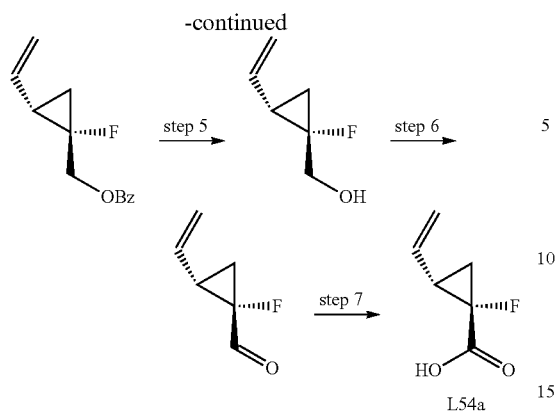

Step 1.

To a solution of ((1S,2S)-2-(((tert-butyldiphenylsilyl)oxy)methyl)-1-fluorocyclopropyl)methanol (I-20a) (1.0 g, 2.8 mmol) and triethylamine (0.59 mL, 4.2 mmol) in dichloromethane (12 mL) was added benzoyl chloride (0.36 mL, 3.1 mmol) dropwise over 5 min. The reaction stirred for 1 hr. Saturated sodium bicarbonate was added to the reaction mixture and the aqueous layer was washed three times with dichloromethane. The combined organic layers were dried over $Na_2SO_4$, filtered and concentrated to give ((1S,2S)-2-(((tert-butyldiphenylsilyl)oxy)methyl)-1-fluorocyclopropyl)methyl benzoate which was used below without further purification. $^1$H NMR (400 MHz, Chloroform-d) δ 8.19-8.08 (m, 3H), 7.73-7.64 (m, 4H), 7.59-7.50 (m, 2H), 7.45-7.33 (m, 6H), 4.62 (dd, J=21.6, 13.0 Hz, 1H), 4.51 (ddd, J=23.6, 12.9, 1.2 Hz, 1H), 3.94 (ddd, J=11.0, 5.6, 1.6 Hz, 1H), 3.70 (ddd, J=11.0, 8.4, 1.3 Hz, 1H), 1.51-1.40 (m, 1H), 1.02 (s, 9H), 1.00-0.78 (m, 2H).

Step 2

((1S,2S)-1-fluoro-2-(hydroxymethyl)cyclopropyl)methyl benzoate was prepared using a similar procedure to step 2 of L2a with ((1S,2S)-2-(((tert-butyldiphenylsilyl)oxy)methyl)-1-fluorocyclopropyl)methyl benzoate. $^1$H NMR (400 MHz, Chloroform-d) δ 8.11-8.05 (m, 2H), 7.62-7.56 (m, 1H), 7.50-7.42 (m, 2H), 4.65 (dd, J=22.5, 13.0 Hz, 1H), 4.60-4.50 (m, 1H), 3.97 (dt, J=12.3, 6.2 Hz, 1H), 3.72-3.63 (m, 1H), 1.55-1.46 (m, 1H), 1.14-1.02 (m, 2H).

Step 3.

((1S,2S)-1-fluoro-2-formylcyclopropyl)methyl benzoate was prepared using a similar procedure to step 1 of L30a with ((1S,2S)-1-fluoro-2-(hydroxymethyl)cyclopropyl)methyl benzoate.

Step 4

((1S,2S)-1-fluoro-2-vinylcyclopropyl)methyl benzoate was prepared using a similar procedure to step 2 of L15a with ((1S,2S)-1-fluoro-2-formylcyclopropyl)methyl benzoate. $^1$H NMR (400 MHz, Chloroform-d) δ 8.12-8.07 (m, 2H), 7.61-7.55 (m, 1H), 7.50-7.42 (m, 2H), 5.64 (dddd, J=17.1, 10.3, 8.7, 1.5 Hz, 1H), 5.26 (dd, J=17.2, 1.6 Hz, 1H), 5.13 (dd, J=10.4, 1.6 Hz, 1H), 4.65-4.51 (m, 2H), 1.90-1.79 (m, 1H), 1.30-1.14 (m, 2H).

Step 5

((1S,2S)-1-fluoro-2-vinylcyclopropyl)methanol was prepared using a similar procedure to step 5 of I-17 with ((1S,2S)-1-fluoro-2-vinylcyclopropyl)methyl benzoate. $^1$H NMR (400 MHz, Chloroform-d) δ 5.62 (dddd, J=17.2, 10.3, 8.8, 1.5 Hz, 1H), 5.24 (dd, J=17.2, 1.6 Hz, 1H), 5.10 (dd, J=10.4, 1.7 Hz, 1H), 3.83 (d, J=21.9 Hz, 2H), 1.71 (qd, J=9.0, 3.2 Hz, 1H), 1.19-1.05 (m, 2H).

Step 6

(1S,2S)-1-fluoro-2-vinylcyclopropane-1-carbaldehyde was prepared using a similar procedure to step 1 of L30a with ((1S,2S)-1-fluoro-2-vinylcyclopropyl)methanol.

Step 7

(1S,2S)-1-fluoro-2-vinylcyclopropane-1-carboxylic acid was prepared using a similar procedure to step 4 of L17 with (1S,2S)-1-fluoro-2-vinylcyclopropane-1-carbaldehyde. $^1$H NMR (400 MHz, Chloroform-d) δ 5.59 (dddd, J=17.2, 10.3, 8.6, 1.5 Hz, 1H), 5.33 (dd, J=17.5, 1.2 Hz, 1H), 5.22 (dd, J=10.3, 1.4 Hz, 1H), 1.76 (td, J=10.0, 6.5 Hz, 1H), 1.28-1.13 (m, 2H).

(1R,2R)-1-fluoro-2-vinylcyclopropane-1-carboxylic Acid (L54b)

Prepared in a manner similar to L54a, using I-20b. $^1$H NMR (400 MHz, Chloroform-d) δ 5.59 (dddd, J=17.2, 10.3, 8.6, 1.5 Hz, 1H), 5.33 (dd, J=17.5, 1.2 Hz, 1H), 5.22 (dd, J=10.3, 1.4 Hz, 1H), 1.76 (td, J=10.0, 6.5 Hz, 1H), 1.28-1.13 (m, 2H).

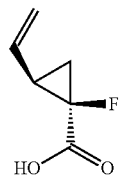

Preparation of (1S,2R)-2-fluoro-2-vinylcyclopropane-1-carboxylic Acid (L55a)

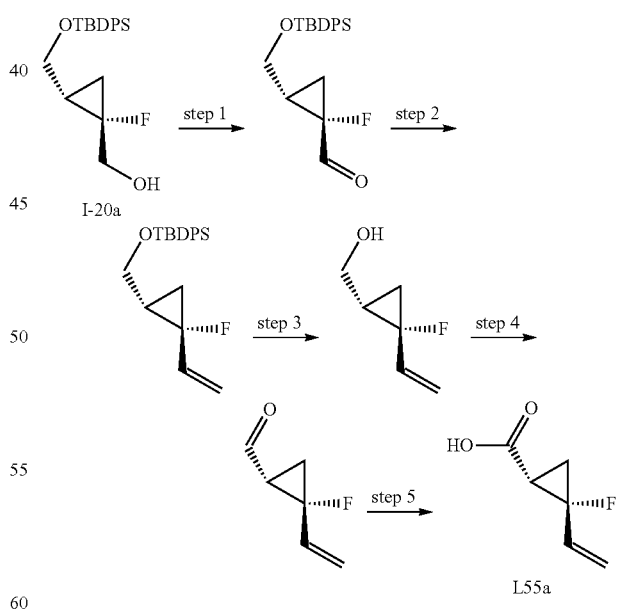

Step 1

(1S,2S)-2-(((tert-butyldiphenylsilyl)oxy)methyl)-1-fluorocyclopropane-1-carbaldehyde was prepared using a similar procedure to step 1 of L30a with ((1S,2S)-2-(((tert-butyldiphenylsilyl)oxy)methyl)-1-fluorocyclopropyl)methanol.

Step 2 tert-butyl(((1S,2R)-2-fluoro-2-vinylcyclopropyl)methoxy)diphenylsilane was prepared using a similar procedure to step 2 of L15a with (1S,2S)-2-(((tert-butyldiphenylsilyl)oxy)methyl)-1-fluorocyclopropane-1-carbaldehyde. ¹H NMR (400 MHz, Chloroform-d) δ 7.71-7.65 (m, 4H), 7.45-7.32 (m, 6H), 5.68 (ddd, J=21.1, 17.2, 11.0 Hz, 1H), 5.28 (dt, J=17.2, 1.0 Hz, 1H), 5.11 (dt, J=10.9, 1.2 Hz, 1H), 3.88 (ddd, J=11.1, 6.2, 1.7 Hz, 1H), 3.80 (ddd, J=11.1, 7.7, 1.3 Hz, 1H), 1.40-1.29 (m, 1H), 1.04-0.89 (m, 2H).

Step 3

((1S,2R)-2-fluoro-2-vinylcyclopropyl)methanol was prepared using a similar procedure to step 2 of L2a with tert-butyl(((1S,2R)-2-fluoro-2-vinylcyclopropyl)methoxy)diphenylsilane. ¹H NMR (400 MHz, Chloroform-d) δ 5.71 (ddd, J=21.4, 17.2, 11.0 Hz, 1H), 5.32 (d, J=17.2 Hz, 1H), 5.15 (dt, J=11.0, 1.2 Hz, 1H), 3.95 (dddd, J=11.8, 7.5, 5.8, 1.5 Hz, 1H), 3.70 (dddd, J=11.8, 8.6, 4.8, 1.4 Hz, 1H), 1.52-1.36 (m, 2H), 1.24-0.98 (m, 2H).

Step 4

(1S,2R)-2-fluoro-2-vinylcyclopropane-1-carbaldehyde was prepared using a similar procedure to step 1 of L30a with ((1S,2R)-2-fluoro-2-vinylcyclopropyl)methanol.

Step 5

(1S,2R)-2-fluoro-2-vinylcyclopropane-1-carboxylic acid was prepared using a similar procedure to step 4 of L17 with (1S,2R)-2-fluoro-2-vinylcyclopropane-1-carbaldehyde. ¹H NMR (400 MHz, Chloroform-d) δ 5.67 (ddd, J=19.7, 17.2, 10.9 Hz, 1H), 5.45 (d, J=17.1 Hz, 1H), 5.28 (d, J=10.7 Hz, 1H), 1.98 (ddd, J=9.8, 7.6, 2.4 Hz, 1H), 1.45-1.33 (m, 2H).

(1S,2S)-2-fluoro-2-vinylcyclopropane-1-carboxylic Acid (L55b)

Prepared in a manner similar to L55a, using I-20d. 1H NMR (400 MHz, Chloroform-d) δ 5.96 (ddd, J=23.6, 17.3, 11.2 Hz, 1H), 5.55 (dd, J=17.3, 1.2 Hz, 1H), 5.34 (dd, J=11.2, 1.6 Hz, 1H), 2.40 (ddd, J=17.9, 10.1, 7.9 Hz, 1H), 1.80 (ddd, J=18.7, 10.2, 6.9 Hz, 1H), 1.60 (dt, J=12.6, 7.5 Hz, 1H).

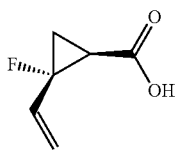

L55b

Preparation of tert-butyl 4-(5-hydroxypentyl)-5-methyl-isoxazole-3-carboxylate (L56a)

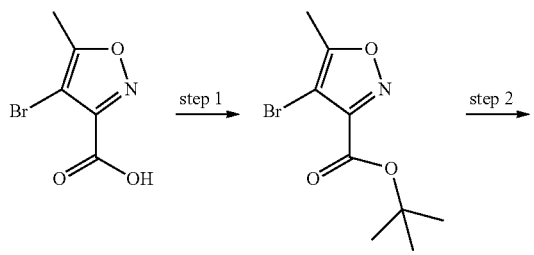

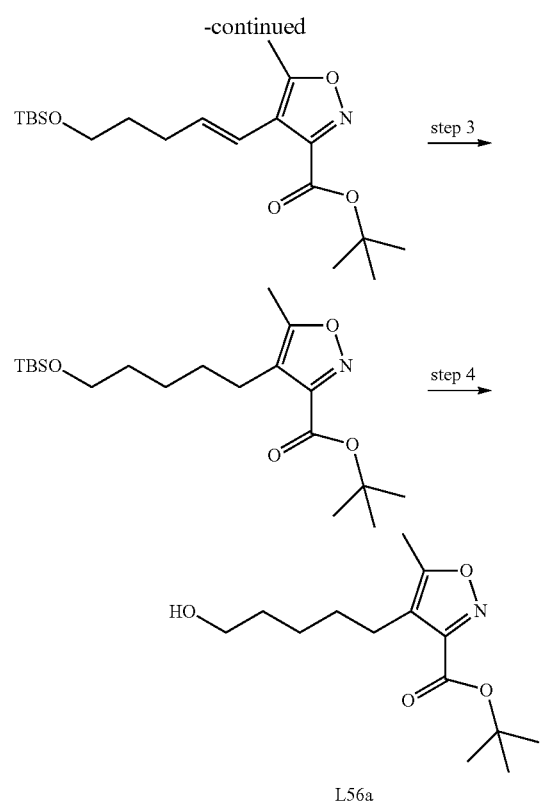

L56a

Step 1

2-tert-Butyl-1,3-diisopropylisourea (4.05 mL, 18.2 mmol) was added to a solution of 4-bromo-5-methyl-isoxazole-3-carboxylic acid (1.25 g, 6.07 mmol) in tetrahydrofuran (15 mL), and the resultant mixture was heated at 65° C. overnight. The formed solid was filtered and washed with ethyl acetate to yield the crude product, which was purified by silica gel column chromatography (0-20% ethyl acetate in hexanes) to yield tert-butyl 4-bromo-5-methyl-isoxazole-3-carboxylate. ES/MS: m/z 263.56 [M+H]⁺.

Step 2

Cesium carbonate (404 mg, 1.24 mmol) was added to a solution of tert-butyl 4-bromo-5-methyl-isoxazole-3-carboxylate (250 mg, 0.95 mmol) and tert-butyl-dimethyl-[(E)-5-(4,4,5,5-tetramethyl-1,3,2-dioxaborolan-2-yl)pent-4-enoxy]silane (prepared according to *J. Am. Chem. Soc.* 2014, 16140) (342 mg, 1.05 mmol) in 1,4-dioxane (1.25 mL) and water (0.25 mL) at room temperature. This reaction mixture was degassed with argon gas for 10 minutes. Then, [1,1'-Bis(diphenylphosphino)ferrocene]palladium(II) dichloride (78 mg, 0.01 mmol) was added and the mixture was heated at 110° C. for 16 h. The reaction mixture was concentrated and purified by silica gel column chromatography (0-20% ethyl acetate in hexanes) to yield tert-butyl 4-[(E)-5-[tert-butyl(dimethyl)silyl]oxypent-1-enyl]-5-methyl-isoxazole-3-carboxylate. ¹H NMR (400 MHz, Chloroform-d) δ 6.42 (d, J=16.2 Hz, 1H), 5.89 (m, J=16.2, 6.9 Hz, 1H), 3.66 (t, J=6.4 Hz, 2H), 2.47 (s, 3H), 2.31-2.23 (m, 2H), 1.73-1.64 (m, 2H), 1.60 (s, 9H), 0.89 (s, 9H), 0.05 (s, 6H).

Step 3

10% Palladium on carbon (66.9 mg, 0.063 mmol) was added to a solution of tert-butyl 4-[(E)-5-[tert-butyl(dimethyl)silyl]oxypent-1-enyl]-5-methyl-isoxazole-3-carboxylate (120 mg, 0.31 mmol) in ethyl acetate (2 mL). The reaction vessel was purged with argon and subjected to an atmosphere of hydrogen, stirring for 16 h. The reaction mixture was filtered to remove the palladium and washed with ethyl acetate. The organics were concentrated to yield tert-butyl 4-[5-[tert-butyl(dimethyl)silyl]oxypentyl]-5-methyl-isoxazole-3-carboxylate, which was used crude in the next step with no further purification. $^1$H NMR (400 MHz, Chloroform-d) δ 3.62 (t, J=6.4 Hz, 2H), 2.58-2.52 (m, 2H), 2.20 (s, 3H), 1.63 (s, 9H), 1.58-1.48 (m, 3H), 1.42-1.33 (m, 3H), 0.91 (s, 9H), 0.06 (s, 6H).

Step 4

Tetrabutylammonium fluoride (0.32 mL, 0.32 mmol) was added to a solution of tert-butyl 4-[5-[tert-butyl(dimethyl)silyl]oxypentyl]-5-methyl-isoxazole-3-carboxylate (101.2 mg, 0.26 mmol) in tetrahydrofuran (2 mL) and the resulting reaction mixture was left to stir at room temperature for 2 h. The organics were concentrated in vacuo to yield the crude product, which was purified by silica gel column chromatography (10-65% ethyl acetate in hexanes) to yield tert-butyl 4-(5-hydroxypentyl)-5-methyl-isoxazole-3-carboxylate. ES/MS: m/z 269.72 [M+H]$^+$.

tert-butyl 4-(5-hydroxypentyl)-2-(trifluoromethyl)pyrimidine-5-carboxylate (L58b)

Prepared following a similar procedure to L58a using 4-chloro-2-(trifluoromethyl)pyrimidine-5-carboxylic acid in place of 3-chloroquinoxaline-2-carboxylic acid. ES/MS: m/z 334.9 [M+H]$^+$.

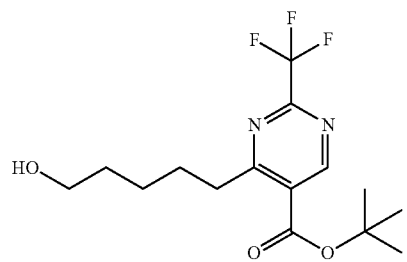

L58b

Preparation of tert-butyl 4-[(E)-5-hydroxypent-1-enyl]-5-methyl-isoxazole-3-carboxylate (L57a)

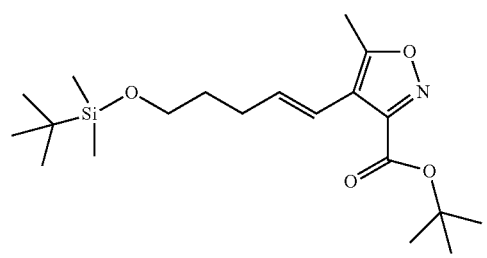

intermediate in
the synthesis of L56a

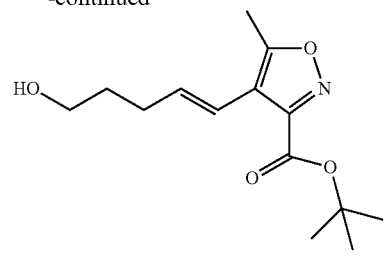

L57a

Step 1

1 M solution of tetrabutylammonium fluoride in tetrahydrofuran (0.25 mL, 0.25 mmol) was added to tert-butyl 4-[(E)-5-[tert-butyl(dimethyl)silyl]oxypent-1-enyl]-5-methyl-isoxazole-3-carboxylate (80 mg, 0.21 mmol) in tetrahydrofuran (2 mL) and the resulting solution was left to stir at room temperature for 3 h. The reaction mixture was concentrated in vacuo to yield the crude product, which was purified by silica gel column chromatography (0-55% ethyl acetate in hexanes) to yield tert-butyl 4-[(E)-5-hydroxypent-1-enyl]-5-methyl-isoxazole-3-carboxylate. ES/MS: m/z 267.70 [M+H]$^+$.

Preparation of tert-butyl 3-[5-(p-tolylsulfonyloxy)pentyl]qiuinoxaline-2-carboxylate (L58a)

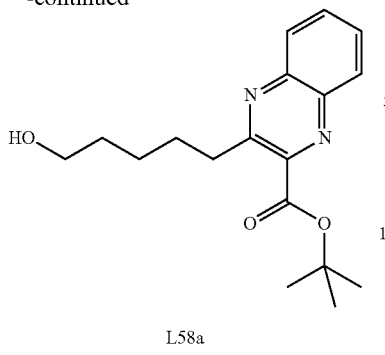

L58a

Step 1

2-tert-Butyl-1,3-diisopropylisourea (1.87 mL, 8.4 mmol) was added to a solution of 3-chloroquinoxaline-2-carboxylic acid (500 mg, 2.4 mmol) dissolved in tetrahydrofuran (6 mL) in a sealed flask and the resulting reaction mixture was heated at 65° C. for 90 min. The resulting solid was filtered and washed with ethyl acetate. The organics were collected and concentrated in vacuo to produce the crude product, which was purified via silica gel column chromatography (0-30% ethyl acetate in hexanes) to yield tert-butyl 3-chloroquinoxaline-2-carboxylate. $^1$H NMR (400 MHz, Chloroform-d) δ 8.22-8.17 (m, 1H), 8.10-8.02 (m, 1H), 7.91-7.80 (m, 2H), 1.72 (s, 9H).

Step 2

Cesium carbonate (480 mg, 1.47 mmol) was added to a solution of tert-butyl 3-chloroquinoxaline-2-carboxylate (300 mg, 1.13 mmol) and tert-butyl-diphenyl-[(E)-5-(4,4,5,5-tetramethyl-1,3,2-dioxaborolan-2-yl)pent-4-enoxy]silane silane (prepared according to *J. Am. Chem. Soc.* 2020, 11506) (562 mg, 1.25 mmol) in 1,4-dioxane (2 mL) and water (0.5 mL) at room temperature. This reaction mixture was degassed with argon gas for 10 minutes. Then, [1,1'-Bis(diphenylphosphino)ferrocene]palladium(II) dichloride (93 mg, 0.11 mmol) was added and the mixture was heated at 110° C. for 16 h. The reaction mixture was concentrated to produce the crude product, which was purified via silica gel column chromatography (0-15% ethyl acetate in hexanes) to yield tert-butyl 3-[(E)-5-[tert-butyl(diphenyl)silyl]oxypent-1-enyl]quinoxaline-2-carboxylate as an orange gel. ES/MS: m/z 552.97 [M+H]$^+$.

Step 3 p-Toluenesulfonhydrazide (1.4 g, 7.54 mmol) and sodium acetate (743 mg, 9.05 mmol) were added to a solution of tert-butyl 3-[(E)-5-[tert-butyl(diphenyl)silyl]oxypent-1-enyl]quinoxaline-2-carboxylate (417 mg, 0.75 mmol) in tetrahydrofuran (14 mL) and water (7 mL), and the resulting reaction mixture was stirred at 80° C. for 16 h. The reaction mixture was quenched with saturated sodium bicarbonate and extracted with ethyl acetate twice. The organics were collected, dried over magnesium sulfate and concentrated to yield tert-butyl 3-[5-[tert-butyl(diphenyl)silyl]oxypentyl]quinoxaline-2-carboxylate, which was carried over to the next step without further purification. ES/MS: m/z 554.59 [M+H]$^+$.

Step 4

1 M tetrabutylammonium fluoride solution in tetrahydrofuran (2.58 mL, 2.58 mmol) was added to a solution of tert-butyl 3-[5-[tert-butyl(diphenyl)silyl]oxypentyl]quinoxaline-2-carboxylate (477 mg, 0.86 mmol) in tetrahydrofuran (2 mL) and stirred at room temperature for 30 minutes. The reaction mixture was concentrated to produce the crude product, which was purified via silica gel column chromatography (0-60% ethyl acetate in hexanes) to yield tert-butyl 3-(5-hydroxypentyl)quinoxaline-2-carboxylate as a yellow oil. ES/MS: m/z 316.94 [M+H]$^+$.

Preparation of tert-butyl 3-[5-(p-tolylsulfonyloxy)pentyl]quinoxaline-2-carboxylate (L59a)

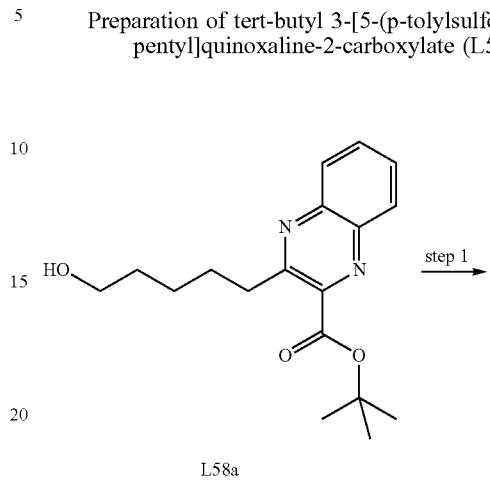

Step 1 p-Toluenesulfonyl chloride (171 mg, 0.90 mmol) was added to a solution of tert-butyl 3-(5-hydroxypentyl)quinoxaline-2-carboxylate (236 mg, 0.75 mmol) in dichloromethane (1 mL) and pyridine (0.2 mL) as co-solvent, and the resulting reaction mixture was stirred for 16 h. The reaction mixture was diluted in excess water and extracted with dichloromethane twice. The resulting organics were collected, dried over magnesium sulfate and concentrated to produce the crude product, which was purified via silica gel column chromatography (0-40% ethyl acetate in hexanes) to yield tert-butyl 3-[5-(p-tolylsulfonyloxy)pentyl]quinoxaline-2-carboxylate. ES/MS: m/z 470.89 [M+H]$^+$.

tert-butyl 2-(5-(tosyloxy)pentyl)nicotinate (L59b)

Prepared in a manner similar to L58a/L59a using tert-butyl 2-bromopyridine-3-carboxylate as starting material. ES/MS: m/z 420.9 [M+H]$^+$.

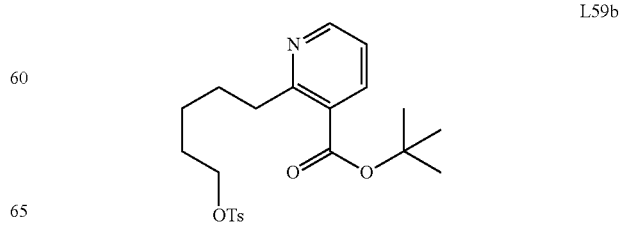

L59b tert-butyl 2-(5-(tosyloxy)pentyl)quinoline-3-carboxylate (L59c)

Prepared in a manner similar to L50a/L59a using tert-butyl 2-chloroquinoline-3-carboxylate. ES/MS: m/z 470.62 [M+H]$^+$.

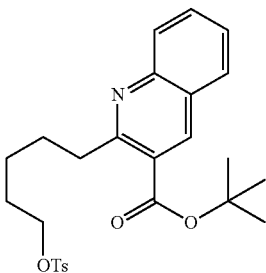

L59c tert-butyl 2-(5-(tosyloxy)pentyl)-6-(trifluoromethyl)nicotinate (L59d)

Prepared in a manner similar to L50a/L59a using tert-butyl 2-chloro-6-(trifluoromethyl)pyridine-2-carboxylate. ES/MS: m/z 487.86 [M+H]$^+$.

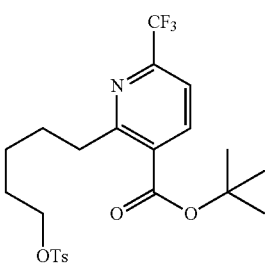

L59d tert-butyl 4-(5-(tosyloxy)pentyl)-2-(trifluoromethyl)nicotinate (L59e)

Prepared in a manner similar to L50a/L59a using tert-butyl 4-chloro-2-(trifluoromethyl)pyridine-3-carboxylate. ES/MS: m/z 487.90 [M+H]$^+$.

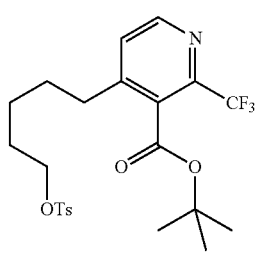

L59e tert-butyl 3-(5-(tosyloxy)pentyl)isoquinoline-4-carboxylate (L59f)

Prepared in a manner similar to L50a/L59a using 3-chloroisoquinoline-4-carboxylic acid. ES/MS: m/z 469.97 [M+H]$^+$.

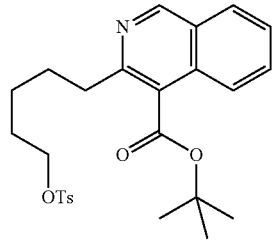

L59f tert-butyl 3-(5-(tosyloxy)pentyl)quinoline-2-carboxylate (L59g)

Prepared in a manner similar to L50a/L59a using tert-butyl 3-bromoquinoline-2-carboxylate. ES/MS: m/z 469.79 [M+H]$^+$.

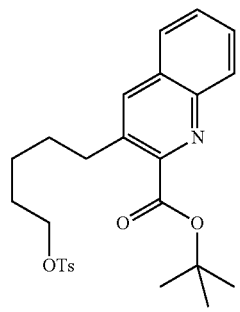

L59g tert-butyl (E)-5-chloro-3-(5-(tosyloxy)pent-1-en-1-yl)picolinate (L59h)

Prepared following a similar procedure to steps 1, 2 and 4 in the synthesis of L58a and step 1 of L59a, using 3-bromo-5-chloropicolinic acid in place of 3-chloroquinoxaline-2-carboxylic acid. ES/MS: m/z 451.7 [M+H]$^+$.

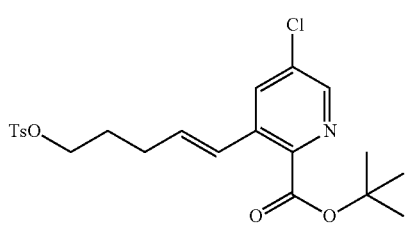

L59h tert-butyl (E)-6-chloro-3-(5-(tosyloxy)pent-1-en-1-yl)picolinate (L59i)

Prepared following a similar procedure to steps 1, 2 and 4 in the synthesis of L58a and step 1 to L59a, using 3-bromo-6-chloropicolinic acid in place of 3-chloroquinoxaline-2-carboxylic acid. ES/MS: m/z 451.6 [M+H]$^+$.

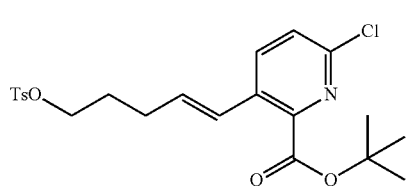

tert-butyl 5-(5-(tosyloxy)pentyl)thieno[3,2-b]pyridine-6-carboxylate (L59j)

Prepared following a similar procedure to L59a using L50q. ES/MS: m/z 475.9 [M+H]⁺.

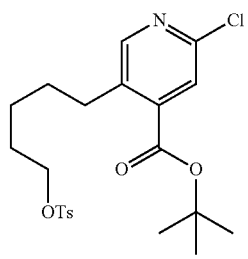

tert-butyl 2-cyclopropyl-4-(5-(tosyloxy)pentyl)nicotinate (L59m)

Prepared in a manner similar to L59a, using L60a. ES/MS: ES/MS: m/z 460.3 [M+H]⁺.

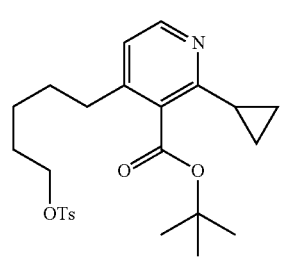

tert-butyl 6-chloro-4-(5-(tosyloxy)pentyl)nicotinate (L59k)

Prepared in a manner similar to L59a using L50w. ES/MS: m/z 454.2 [M+H]⁺.

tert-butyl 6-chloro-2-(5-(tosyloxy)pentyl)nicotinate (L59n)

Prepared in a manner similar to L59a, using L50u. ES/MS: m/z 454.2 [M+H]⁺.

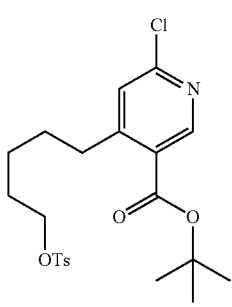

tert-butyl 2-chloro-5-(5-(tosyloxy)pentyl)isonicotinate (L59l)

Prepared in a manner similar to L59a, using tert-butyl 2-chloro-5-(5-hydroxypentyl)isonicotinate (L50v). ES/MS: m/z 454.2 [M+H]⁺.

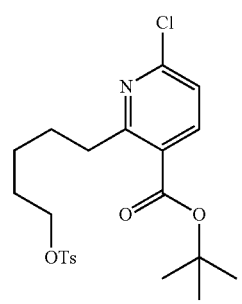

tert-butyl 6-methyl-2-(5-(tosyloxy)pentyl)nicotinate (L59o)

Prepared in a manner similar to L59a, using L50x. ES/MS: m/z 434.2 [M+H]⁺.

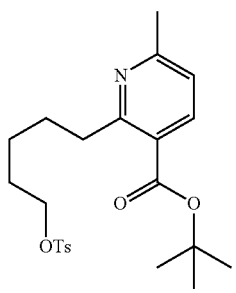

tert-butyl 6-(difluoromethyl)-2-(5-(tosyloxy)pentyl) nicotinate (L59p)

Prepared in a manner similar to L59a, using L50y. ES/MS: m/z 470.2 [M+H]$^+$.

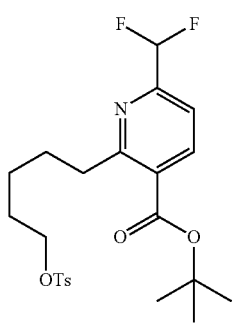

tert-butyl 2-fluoro-4-(5-(tosyloxy)pentyl)nicotinate (L59q)

Prepared in a manner similar to L59a, using L50z. ES/MS: m/z 438.9 [M+H]$^+$.

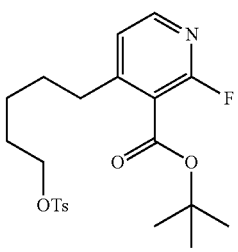

tert-butyl 4-chloro-2-[5-(p-tolylsulfonyloxy)pentyl] pyridine-3-carboxylate (L59r)

Prepared in a manner similar to L50a/L59a using tert-butyl 2-bromo-4-chloro-pyridine-3-carboxylate. ES/MS: m/z 455.0 [M+H]$^+$.

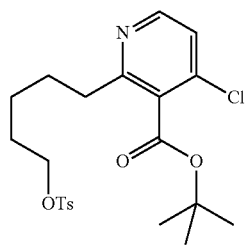

tert-butyl 4-(5-(tosyloxy)pentyl)-2-(trifluoromethyl) nicotinate (L59s)

Prepared in a manner similar to L50a/L59a using tert-butyl 4-chloro-2-(trifluoromethyl)pyridine-3-carboxylate. ES/MS: m/z 487.9 [M+H]$^+$.

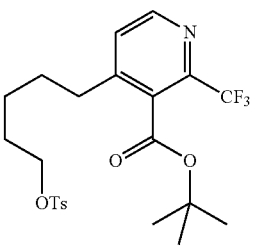

tert-butyl 2-[5-(p-tolylsulfonyloxy)pentyl]-6-(trifluoromethyl)pyridine-3-carboxylate (L59t)

Prepared in a manner similar to L50a/L59a using tert-butyl 2-chloro-6-(trifluoromethyl)pyridine-3-carboxylate. ES/MS: m/z 487.9 [M+H]$^+$.

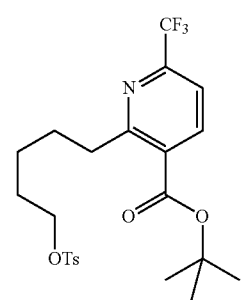

tert-butyl 7-(5-(tosyloxy)pentyl)quinoline-8-carboxylate (L59u)

Prepared in a manner similar to L50a/L59a using tert-butyl 7-chloroquinoline-8-carboxylate. ES/MS: m/z 470.7 [M+H]$^+$.

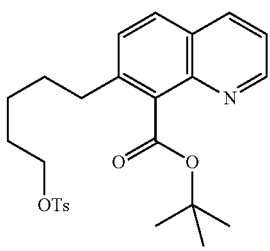

tert-butyl 6-(difluoromethyl)-2-(5-(tosyloxy)pentyl)nicotinate (L59v)

Prepared in a manner similar to L50a/L59a using tert-butyl 2-chloro-6-(difluoromethyl)pyridine-3-carboxylate. ES/MS: m/z 469.9 [M+H]$^+$.

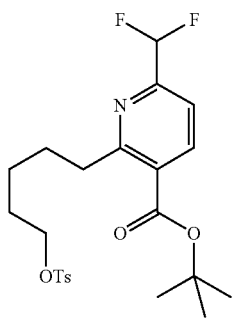

tert-butyl 4-[5-(p-tolylsulfonyloxy)pentyl]-6-(trifluoromethyl)pyridine-3-carboxylate (L59w)

Prepared in a manner similar to L50a/L59a using tert-butyl 4-chloro-6-(trifluoromethyl)pyridine-3-carboxylate. ES/MS: m/z 487.9 [M+H]$^+$.

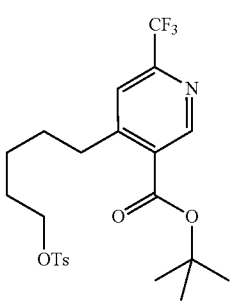

tert-butyl 2-(5-(tosyloxy)pentyl)benzoate (L59x)

Prepared following a similar procedure to L59a using tert-butyl 2-(5-hydroxypentyl)benzoate (L50n) in place of L58a. ES/MS: m/z 441.2 [M+Na]$^+$.

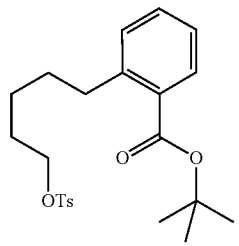

tert-butyl 3,6-difluoro-2-[5-(p-tolylsulfonyloxy)pentyl]benzoate (L59y)

Prepared following a similar procedure to L50a/L59a using 2-bromo-3,6-difluoro-benzoic acid. ES/MS: m/z 477.2 [M+Na]$^+$.

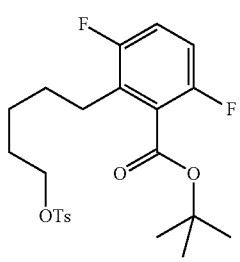

tert-butyl 3,4-difluoro-2-[5-(p-tolylsulfonyloxy)pentyl]benzoate (L59z)

Prepared following a similar procedure to L50a/L59a using 2-bromo-3,4-difluoro-benzoic acid. ES/MS: m/z 477.2 [M+Na]$^+$.

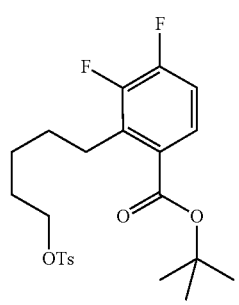

tert-butyl 4-(difluoromethyl)-2-(5-(tosyloxy)pentyl)benzoate (L59aa)

Prepared in a manner similar to L50a/L59a, using 2-bromo-4-(difluoromethyl)benzoic acid. ES/MS: m/z 491.2 [M+Na]$^+$.

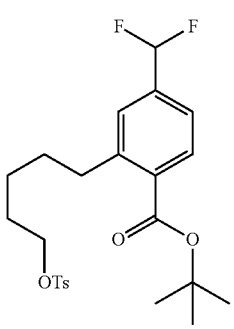

tert-butyl 2,3-difluoro-6-(5-(tosyloxy)pentyl)benzoate (L59bb)

Prepared in a manner similar to L50a/L59a, using 6-bromo-2,3-difluorobenzoic acid. ES/MS: m/z 477.2 [M+Na]$^+$.

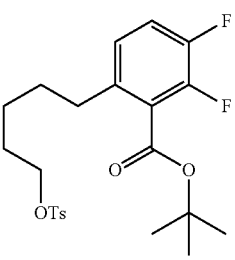

tert-butyl 4-chloro-3-fluoro-2-(5-(tosyloxy)pentyl)benzoate (L59cc)

Prepared in a manner similar to L50a/L59a, using 2-bromo-4-chloro-3-fluorobenzoic acid. ES/MS: m/z 493.2 [M+Na]$^+$.

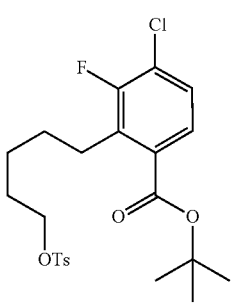

tert-butyl 5-fluoro-2-(5-(tosyloxy)pentyl)benzoate (L59dd)

Prepared in a manner similar to L50a/L59a, using 2-bromo-5-fluorobenzoic acid. ES/MS: m/z 459.2 [M+Na]$^+$.

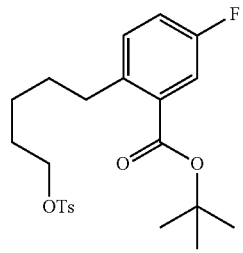

tert-butyl 4-fluoro-2-(5-(tosyloxy)pentyl)benzoate (L59ee)

Prepared in a manner similar to L50a/L59a, using 2-bromo-4-fluorobenzoic acid. ES/MS: m/z 459.2 [M+Na]$^+$.

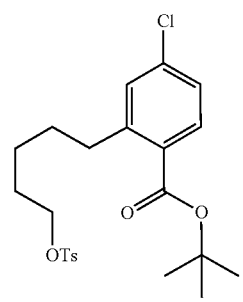

tert-butyl 4-chloro-2-(5-(tosyloxy)pentyl)benzoate (L59ff)

Prepared in a manner similar to L50a/L59a, using 2-bromo-4-chlorobenzoic acid. ES/MS: m/z 475.2 [M+Na]$^+$.

tert-butyl 2-fluoro-6-(5-(tosyloxy)pentyl)benzoate (L59gg)

Prepared in a manner similar to L59a, using L50b. ES/MS: m/z 459.2 [M+Na]$^+$.

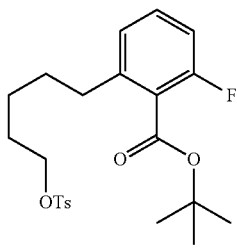

tert-butyl 2-fluoro-6-(5-(tosyloxy)pentyl)benzoate (L59gg)

Prepared in a manner similar to L50a/L59a, using 2-bromo-3-fluorobenzoic acid. ES/MS: m/z 458.88 [M+H]⁺ *(not shown on image, value as printed)*

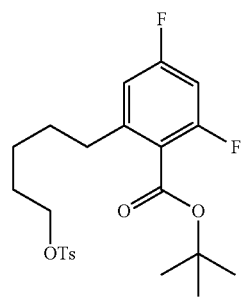

tert-butyl 2,4-difluoro-6-(5-(tosyloxy)pentyl)benzoate (L59ii)

Prepared in a manner similar to L50a/L59a, using 2-bromo-4,6-difluorobenzoic acid. ES/MS: m/z 476.8 [M+Na]⁺.

tert-butyl 4,5-difluoro-2-(5-(tosyloxy)pentyl)benzoate (L59jj)

Prepared in a manner similar to L50a/L59a, using 2-bromo-4,6-difluorobenzoic acid. $^1$H NMR (400 MHz, Chloroform-d) δ 7.81 (d, J=8.4 Hz, 2H), 7.64 (dd, J=11.2, 8.3 Hz, 1H), 7.40-7.34 (m, 2H), 6.96 (dd, J=11.2, 7.7 Hz, 1H), 4.05 (t, J=6.5 Hz, 2H), 2.92-2.82 (m, 2H), 1.78-1.66 (m, 2H), 1.59 (s, 9H), 1.58-1.48 (m, 4H), 1.46-1.27 (m, 3H).

tert-butyl 6-chloro-2-(5-(tosyloxy)pentyl-1,1,2,2-d4)nicotinate (L59hh)

Prepared in a manner similar to L50a/L59a, starting with 2-bromo-6-chloronicotinic acid and using deuterium gas (5% Pt/C, 50° C. in ethyl acetate, 16 h) in step 3 instead of hydrogen gas. ES/MS: m/z 458.88 [M+H]⁺.

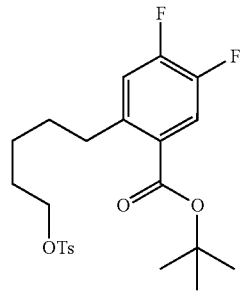

tert-butyl 2-fluoro-2-(pyridin-2-yl)-8-(tosyloxy)octanoate (L59kk)

Prepared in a manner similar to L58a using L65b. ES/MS: m/z 466.3 [M+H]⁺.

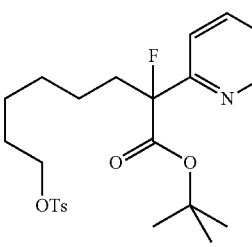

tert-butyl 2-(difluoromethyl)-2-(pyridin-2-yl)-8-(tosyloxy)octanoate (L59ll)

Prepared in a manner similar to L58a using L65d. ES/MS: m/z 498.3 [M+H]⁺.

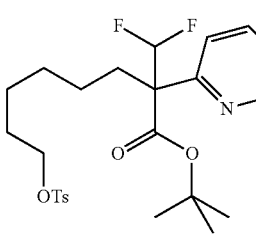

tert-butyl 7-(3-(tosyloxy)propyl)-1-naphthoate (L59 mm)

Prepared in a manner similar to L50a/L59a, using 7-bromo-1-naphthoic acid and propargyl alcohol. $^1$H NMR (400 MHz, Chloroform-d) δ 8.67 (s, 1H), 8.13-8.08 (m, 1H), 7.95 (d, J=8.1 Hz, 1H), 7.81 (d, J=8.3 Hz, 2H), 7.78 (d, J=8.5 Hz, 1H), 7.45 (dd, J=8.1, 7.3 Hz, 1H), 7.36-7.30 (m, 3H), 4.10 (t, J=6.3 Hz, 2H), 2.92-2.44 (m, 2H), 2.45 (s, 3H), 2.22-2.08 (m, 2H), 1.70 (s, 9H).

L59mm

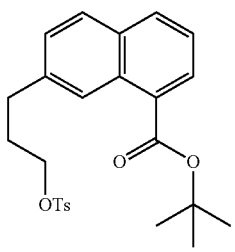

Preparation of tert-butyl 2-cyclopropyl-4-(5-hydroxypentyl)nicotinate (L60a)

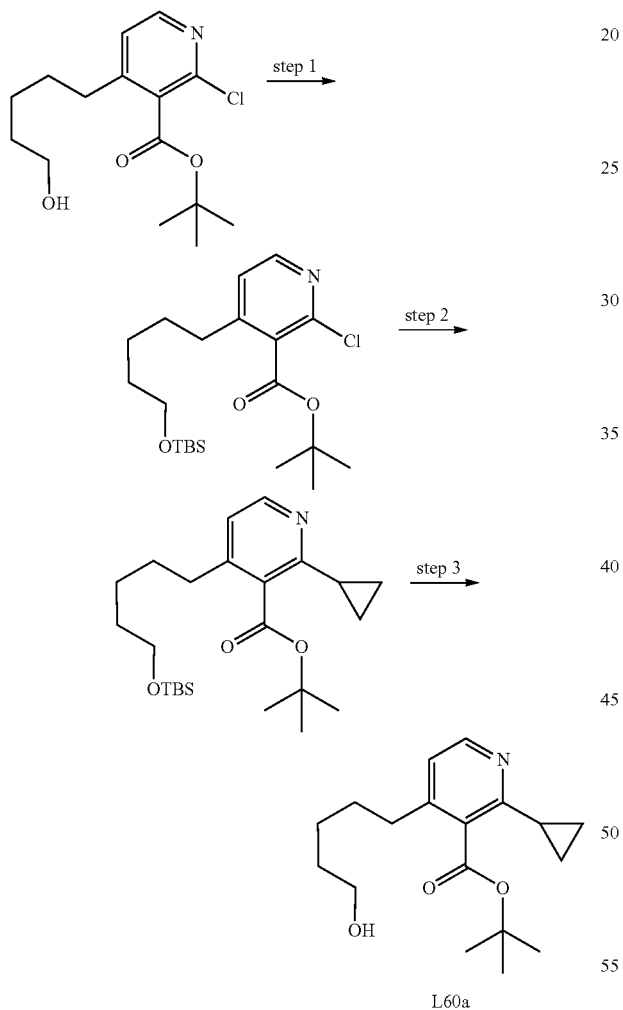

L60a

Step 1.

tert-butyl 4-(5-((tert-butyldimethylsilyl)oxy)pentyl)-2-chloronicotinate was prepared according to the procedure described in Step 1 for L25, using tert-butyl 2-chloro-4-(5-hydroxypentyl)nicotinate (L50s) in place of methyl 9-hydroxynonanoate. ES/MS: m/z 414.3 [M+H]$^+$.

Step 2

A mixture of tert-butyl 4-(5-((tert-butyldimethylsilyl)oxy)pentyl)-2-chloronicotinate (0.222 g, 0.537 mmol), cyclopropylboronic acid (0.138 g, 1.61 mmol), tricyclohexylphosphine (0.015 g, 0.054 mmol) and potassium phosphate tribasic (0.399 g, 1.88 mmol) in toluene (3.0 mL) and water (0.15 mL) was sparged with N$_2$ for approximately 3 min. Palladium(II) acetate (0.012 g, 0.054 mmol) was added and the mixture was stirred at 110° C. for 16 h. The mixture was cooled to rt and filtered through Celite to remove solids. The filtrate was concentrated onto silica gel and purified via flash column chromatography on silica gel to afford tert-butyl 4-(5-((tert-butyldimethylsilyl)oxy)pentyl)-2-cyclopropylnicotinate. ES/MS: m/z 420.3 [M+H]$^+$.

Step 3 tert-butyl 2-cyclopropyl-4-(5-hydroxypentyl)nicotinate was prepared according to the procedure describe in Step 4 for L52a, using tert-butyl 4-(5-((tert-butyldimethylsilyl)oxy)pentyl)-2-cyclopropylnicotinate in place of tert-butyl 2-(((1R,2R)-2-(((tert-butyldiphenylsilyl)oxy)methyl)cyclopropyl)ethynyl)benzoate. ES/MS: m/z 306.3 [M+H]$^+$.

Preparation of 1-allyl-3,3-difluoro-cyclobutanecarboxylic Acid (L61a)

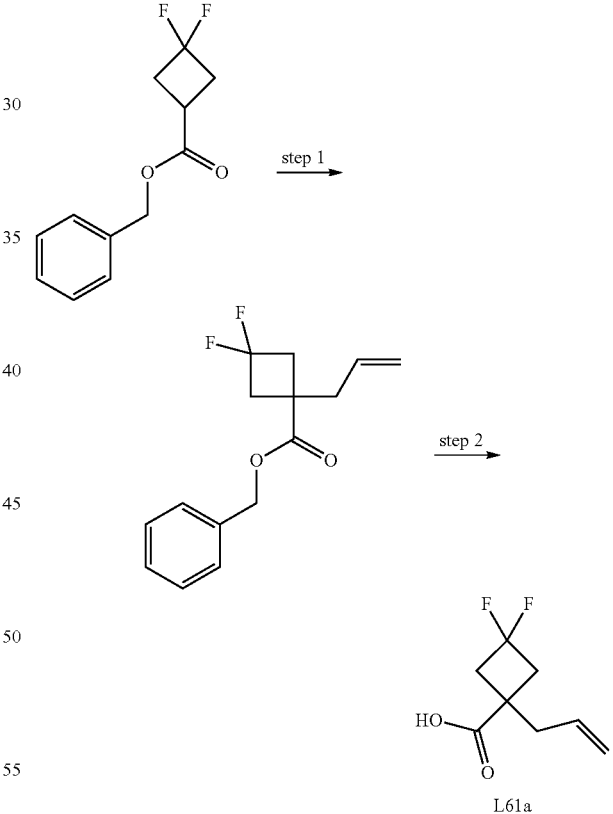

L61a

Step 1

Benzyl 3,3-difluorocyclobutanecarboxylate (500 mg, 2.21 mmol) was dissolved in anhydrous tetrahydrofuran (10 mL), subjected to an atmosphere of argon and cooled to −78° C. 1M Lithium bis(trimethylsilyl)amide solution in tetrahydrofuran (2.43 mL, 2.43 mmol) was added and the reaction mixture was stirred for 1 h at −78° C. Allyl iodide (0.26 mL, 2.87 mmol) was added dropwise and the reaction mixture was warmed to room temperature over 2 h. The reaction mixture was quenched with saturated ammonium chloride solution and extracted with ethyl acetate. The combined organics were collected, dried over magnesium sulfate and concentrated. The resulting residue was purified via silica gel column chromatography (0-20% ethyl acetate in hexanes) to yield benzyl 1-allyl-3,3-difluoro-cyclobutanecarboxylate. $^1$H NMR (400 MHz, Chloroform-d) δ 7.44-7.33 (m, 5H), 5.65 (m, J=17.3, 10.4, 7.0 Hz, 1H), 5.19 (s, 2H), 5.14-5.04 (m, 2H), 3.11-2.96 (m, 2H), 2.66-2.47 (m, 4H). $^{19}$F NMR (376 MHz, Chloroform-d) δ −87.58 (m, J=196.7, 13.3, 8.7 Hz), −88.54-−91.38 (m).

Step 2

Benzyl 1-allyl-3,3-difluoro-cyclobutanecarboxylate (150 mg, 0.56 mmol) was dissolved anhydrous dichloromethane (3 mL), subjected to an atmosphere of argon and cooled to −78° C. 1M boron tribromide solution in dichloromethane (1.13 mL, 1.13 mmol) was added dropwise and the reaction mixture was left to stir at −78° C. for 2 h. The reaction mixture was quenched with methanol (1.3 mL) and concentrated. The resulting residue was purified via silica gel column chromatography (20-70% ethyl acetate in hexanes) to yield 1-allyl-3,3-difluoro-cyclobutanecarboxylic acid. $^1$H NMR (400 MHz, Chloroform-d) δ 5.81-5.68 (m, 1H), 5.22-5.14 (m, 2H), 3.14-2.99 (m, 2H), 2.66-2.52 (m, 4H). $^{19}$F NMR (376 MHz, Chloroform-d) δ −87.53 (m, J=197.4, 13.2, 8.7 Hz), −90.30 (m, J=197.1, 13.4 Hz).

Preparation of (1R,2S)-2-vinylcyclopropane-1-carboxylic Acid (L62a)

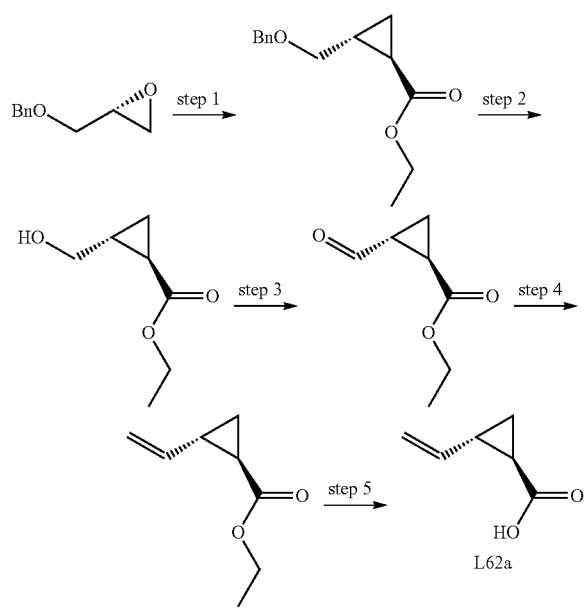

Step 1

Sodium hydride (60%, 40.9 g, 1.02 mol) was added to toluene (1.05 L). Triethyl phosphonoacetate (248 g, 1.11 mol) was added dropwise, and the mixture was allowed to stir an additional 30 min. (R)-2-((benzyloxy)methyl)oxirane was then added dropwise to the mixture. The reaction mixture was then heated to 130° C. and stirred 12 h. The mixture was cooled and was poured into saturated aqueous NH$_4$Cl cooled in an ice water bath. The phases were separated, and the aqueous phase was extracted with EtOAc twice. The combine organic layer was washed with brine, dried over Na$_2$SO$_4$, filtered, and concentrated to afford a crude product that was purified by silica gel chromatography (2%-100% EtOAc in petroleum ether) to afford ethyl (1R,2R)-2-((benzyloxy)methyl)cyclopropane-1-carboxylate. $^1$H NMR: (CDCl$_3$, 400 MHz): δ7.32-7.24 (m, 5H), 4.50 (s, 2H), 4.12-4.07 (m, 2H), 3.43-3.41 (m, 1H), 3.36-3.33 (m, 1H), 1.72-1.71 (m, 1H), 1.55-1.54 (m, 1H), 1.25-1.18 (m, 4H), 0.84-0.84 (m, 1H).

Step 2

Palladium on carbon (16.5 g) was taken up in EtOH (700 mL) in a hydrogenation bottle. Ethyl (1R,2R)-2-((benzyloxy)methyl)cyclopropane-1-carboxylate (70 g, 298 mmol) was added in one portion. The mixture was purged with hydrogen and was stirred under 30 psi hydrogen for 24 h. The mixture was filtered and the filtrate was concentrated to obtain a crude residue that was purified by silica gel chromatography (10:1 petroleum ether/EtOAc) to afford ethyl (1R,2R)-2-(hydroxymethyl)cyclopropane-1-carboxylate. $^1$H NMR: (CDCl$_3$, 400 MHz): δ 1.03 (d, J=2.5 Hz, 1H), 4.11-4.06 (m, 2H), 3.58-3.55 (m, 1H), 3.44-3.40 (m, 1H), 2.00 (m, 1H), 1.24-1.20 (m, 3H), 1.17-1.14 (m, 1H).

Step 3 ethyl (1R,2R)-2-(hydroxymethyl)cyclopropane-1-carboxylate (74 g, 513 mmol) was dissolved in DCM (1.1 L). PCC (221 g, 1.03 mol) was added, and the mixture was stirred at r.t. for 12 h. The mixture was filtered and concentrated to afford a crude residue that was purified by silica gel chromatography (10:1 petroleum ether/EtOAc) to afford ethyl (1R,2R)-2-formylcyclopropane-1-carboxylate. $^1$H NMR (CDCl$_3$, 400 MHz): δ 9.32 (d, J=4.8 Hz, 1H), 4.14-4.09 (m, 2H), 2.38-2.37 (m, 1H), 2.22-2.20 (m, 1H), 1.56-1.54 (m, 1H), 1.48-1.46 (m, 1H), 1.24-1.21 (m, 1H).

Step 4

Methyl triphenylphosphonium bromide (50.2 g, 140 mmol) was dissolved in THF. Potassium tert-butoxide (15 g, 133 mmol) was added, and the mixture was stirred for 20 min. Ethyl (1R,2R)-2-formylcyclopropane-1-carboxylate (20 g, 140 mmol) was added dropwise as a solution in THF (760 mL). The mixture was stirred 20 min, and was concentrated in vacuo. The crude product was purified by silica gel (Pentane/DCM 10/1 to 3/1) to provide ethyl (1R,2S)-2-vinylcyclopropane-1-carboxylate. $^1$H NMR (CDCl$_3$, 400 MHz): δ 5.39-5.37 (m, 1H), 5.18-5.14 (d, J=16.4 Hz, 1H), 4.99-4.97 (d, J=10.0 Hz, 1H), 4.15-4.10 (m, 2H), 2.02-2.00 (m, 1H), 1.63-162 (m, 1H), 1.37-1.35 (m, 1H), 1.27-1.24 (t, J=7.2 Hz, 3H), 0.97-0.97 (m, 1H).

Step 5

(1R,2S)-2-vinylcyclopropane-1-carboxylic acid was prepared using a similar procedure to steps 2 of L48 and used without further purification.

(1S,2R)-2-vinylcyclopropane-1-carboxylic Acid (L62b)

Prepared following a similar procedure to L62a from (S)-2-((benzyloxy)methyl)oxirane and used without further purification.

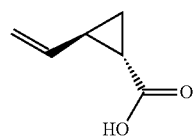

Preparation of 3-fluoro-5-vinylisonicotinic Acid (L63)

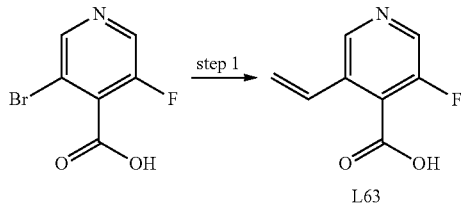

Step 1

3-bromo-5-fluoropyridine-4-carboxylic acid (200 mg, 0.91 mmol) was combined with 1,1'-bis(diphenylphosphino)ferrocene dichloropalladium (II) (33 mg, 0.05 mmol) in dioxane (3 mL) and degassed with $N_2$. Tributyl(vinyl)tin (0.32 mL, 1.1 mmol) was added, and the mixture heated to 100° C. for 24 hours. The resulting mixture was concentrated to give crude 3-fluoro-5-vinylpyridine-4-carboxylic acid, which was used without further purification. ES/MS: m/z 167.94 $[M+H]^+$.

Preparation of tert-butyl 8-hydroxy-2-(pyridin-2-yl)octanoate (L64a)

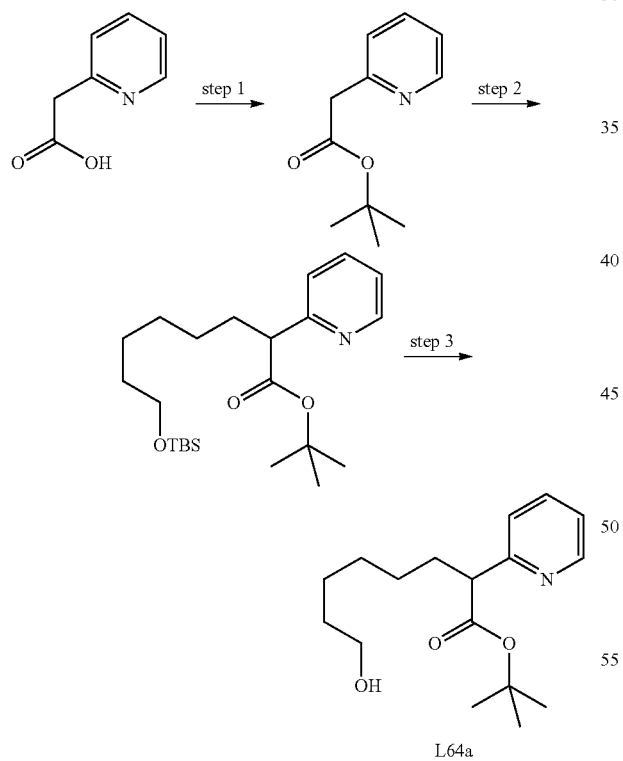

Step 1 tert-butyl 2-(pyridin-2-yl)acetate was prepared following a similar procedure to step 1 of L50a starting with 2-(pyridin-2-yl)acetic acid. ES/MS: m/z 194.1 $[M+H]^+$.

Step 2.

tert-butyl 2-(pyridin-2-yl)acetate (12.0 g, 62.1 mmol) was dissolved in THF (60 mL) and the solution was cooled to −70° C. 1 M LiHMDS (93.2 mL, 1.5 equiv) was then added over 30 minutes. The mixture was stirred at −70° C. for 1 h and 6-((tert-butyldimethylsilyl)oxy)hexyl trifluoromethanesulfonate (from J. Am. Chem. Soc. 2015, 137, 1424-1427) (27.2 g, 74.5 mmol) was added. The mixture was stirred at −70° C. for 4 h and quenched with sat. $NH_4Cl$. The phases were separated, and the aqueous phase was extracted with EtOAc twice. The combine organic layer was washed with brine, dried over $MgSO_4$, filtered, and concentrated to afford a crude product that was purified by silica gel chromatography (2%-100% EtOAc in petroleum ether) to afford tert-butyl 8-((tert-butyldimethylsilyl)oxy)-2-(pyridin-2-yl)octanoate. ES/MS: m/z 408.3 $[M+H]^+$.

Step 3

A solution of tert-butyl 8-((tert-butyldimethylsilyl)oxy)-2-(pyridin-2-yl)octanoate (4.0 g, 9.81 mmol) in DCM (40 mL) was treated with 4 M HCl in dioxane (4.0 mL, 1.6 equiv). The mixture was stirred at room temperature for 2 h and quenched with sat. $NaHCO_3$. The phases were separated, and the aqueous phase was extracted with DCM twice. The combine organic layer was washed with brine, dried over $MgSO_4$, filtered, and concentrated to afford a crude product that was purified by silica gel chromatography (2%-100% EtOAc in petroleum ether) to afford tert-butyl 8-hydroxy-2-(pyridin-2-yl)octanoate. ES/MS: m/z 294.1 $[M+H]^+$. $^1H$ NMR: (DMSO-d6 400 MHz): δ 8.48-8.43 (m, 1H), 7.72 (dt, J=1.9, 7.7 Hz, 1H), 7.28 (d, J=7.9 Hz, 1H), 7.25-7.19 (m, 1H), 4.28 (t, J=5.2 Hz, 1H), 3.62 (t, J=7.6 Hz, 1H), 3.35-3.30 (m, 2H), 1.96-1.82 (m, 1H), 1.79-1.64 (m, 1H), 1.37-1.32 (m, 2H), 1.30 (s, 9H), 1.24-1.05 (m, 6H).

tert-butyl 2-(6-chloropyridin-2-yl)-8-hydroxyoctanoate (L64b)

Prepared in a manner similar to L64a using 2-(6-chloropyridin-2-yl)acetic acid. ES/MS: m/z 328.2 $[M+H]^+$.

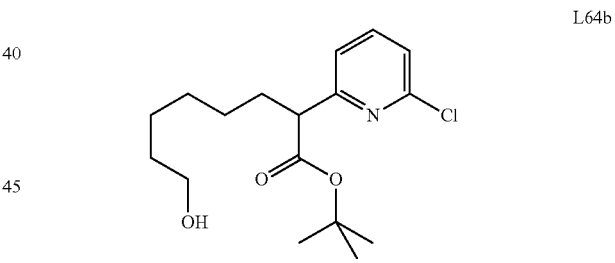

Preparation of tert-butyl 8-hydroxy-2-methyl-2-(pyridin-2-yl)octanoate (L65a)

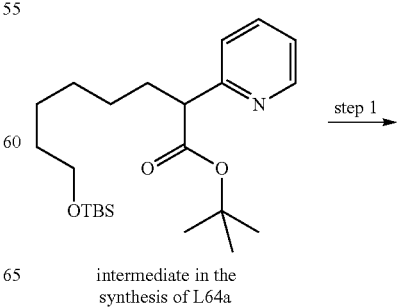

intermediate in the synthesis of L64a

-continued

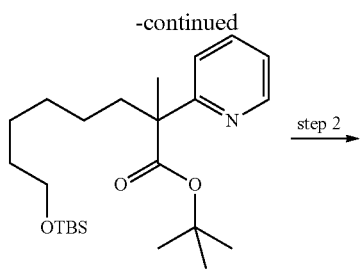

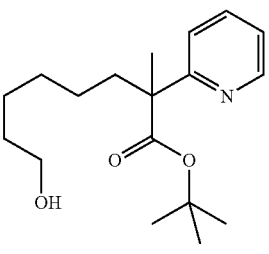

L65a

Step 1 tert-butyl 8-((tert-butyldimethylsilyl)oxy)-2-(pyridin-2-yl)octanoate (9.0 g, 22.1 mmol) was dissolved in THF (45 mL) and the solution was cooled to −70° C. 1 M LiHMDS (33.1 mL, 1.5 equiv) was then added over a periode of 30 minutes. The mixture was stirred at −70° C. for 1 h and MeI (2.06 mL, 33.1 mmol) was added. The mixture was stirred at −70° C. for 4 h and quenched with sat. NH$_4$Cl. The phases were separated, and the aqueous phase was extracted with EtOAc twice. The combine organic layer was washed with brine, dried over MgSO$_4$, filtered, and concentrated to afford a crude product that was purified by silica gel chromatography (2%-100% EtOAc in petroleum ether) to afford tert-butyl 8-((tert-butyldimethylsilyl)oxy)-2-methyl-2-(pyridin-2-yl)octanoate. ES/MS: m/z 422.2 [M+H]$^+$.

Step 3 tert-butyl 8-hydroxy-2-methyl-2-(pyridin-2-yl)octanoate was prepared following a similar procedure to step 3 of L64a. ES/MS: m/z 308.1 [M+H]$^+$. $^1$H NMR: (DMSO-d6 400 MHz): δ 8.51-8.46 (m, 1H), 7.74 (dt, J=1.9, 7.7 Hz, 1H), 7.29 (d, J=8.1 Hz, 1H), 7.22 (ddd, J=0.9, 4.9, 7.4 Hz, 1H), 4.30 (t, J=5.1 Hz, 1H), 3.38-3.33 (m, 2H), 1.96-1.87 (m, 2H), 1.41-1.39 (m, 3H), 1.36 (br d, J=6.5 Hz, 1H), 1.32 (s, 9H), 1.28-1.22 (m, 4H), 1.18-1.09 (m, 2H).

tert-butyl 2-fluoro-8-hydroxy-2-(pyridin-2-yl)octanoate (L65b)

Prepared in a manner similar to L65a using NFSI instead of MeI in step 1 of L65a. ES/MS: m/z 312.2 [M+H]$^+$.

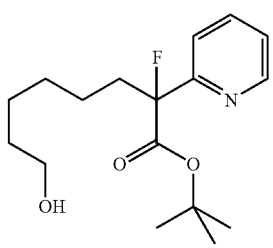

L65b tert-butyl 2-(6-chloropyridin-2-yl)-2-fluoro-8-hydroxyoctanoate (L65c)

Prepared in a manner similar to L64a/L65a using 2-(6-chloropyridin-2-yl)acetic acid and NFSI instead of MeI in step 1 of L65a. ES/MS: m/z 368.2 [M+Na]$^+$.

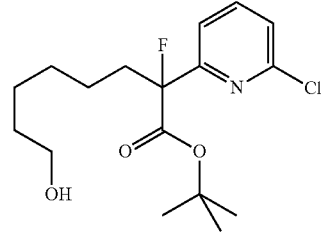

L65c tert-butyl 2-(difluoromethyl)-8-hydroxy-2-(pyridin-2-yl)octanoate (L65d)

Prepared in a manner similar to L64a/L65a using CF$_2$BrTMS/KHMDS/tBuOK instead of MeI/LiHMDS in step 1. ES/MS: m/z 344.2 [M+H]$^+$.

L65d

Preparation 2-(allyloxy)-2-methylpropanoic Acid (L66a)

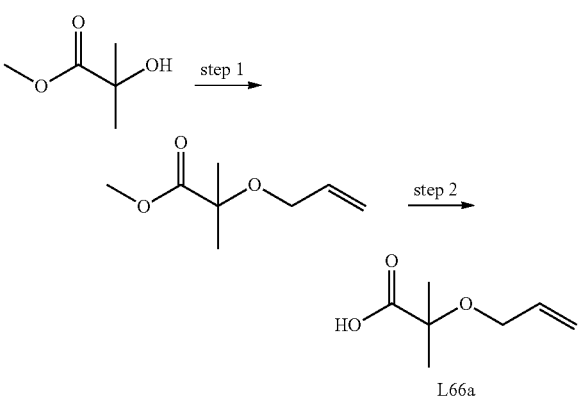

L66a

Step 1

NaH in mineral oil 60% (217 mg, 9.45 mmol) was added to a solution of methyl 2-hydroxy-2-methylpropanoate (1.015 g, 8.6 mmol) in DMF 16 mL under an atmosphere of argon. The resulting mixture was stirred at room temperature for 1 hour before allylbromide (1.04 g, 8.6 mmol) was added. The reaction mixture was stirred overnight at room temperature then quenched with NH4Cl sat., extracted with DCM (3 times). The combined organic layers were dried over sodium sulfate, filtered, evaporated carefully in the rotavapor and purified by column chromatography over silica gel (pentane/diethyl ether 0-10%) to afford methyl 2-(allyloxy)-2-methylpropanoate (897 mg, 66%).

Step 2

Methyl 2-(allyloxy)-2-methylpropanoate (850 mg, 5.37 mmol) was dissolved in THF/MeOH/H2O (1:1:1, 4 mL) and LiOH monohydrate (360 mg, 8.6 mmol) was added. The mixture was stirred overnight at 60° C. at which point TLC analysis showed no remaining ester. The solvents were removed under reduced pressure and after usual work up (HCl 0.5N, DCM), the desired 2-allyloxy-2-methyl-propanoic acid was obtained (750 mg, 97%). ¹H NMR (400 MHz, Chloroform-d) δ 6.20 (brs, 1H), 5.96 (ddt, J=17.2, 10.4, 5.5 Hz, 1H), 5.36-5.30 (m, 1H), 5.22 (dd, J=10.4, 1.4 Hz, 1H), 4.04 (d, J=5.5 Hz, 2H), 1.52 (s, 6H).

1-(allyloxy)cyclopropane-1-carboxylic Acid (L66b)

Prepared following a similar procedure to L66a methyl 1-hydroxycyclopropane-1-carboxylate. ¹H NMR of ethyl ester of L62b (intermediate after step 4): (CDCl₃, 400 MHz): δ 6 8.25 (brs, 1H), 5.95 (ddt, J=17.2, 10.4, 5.6 Hz, 1H), 5.36-5.28 (m, 1H), 5.20 (dq, J=10.4, 1.4 Hz, 1H), 4.17 (dt, J=5.6, 1.5 Hz, 2H), 1.47-1.38 (m, 2H), 1.35-1.27 (m, 2H).

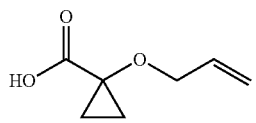

L66b 2-allyltetrahydrofuran-2-carboxylic Acid (L66c)

From WO2001012183.

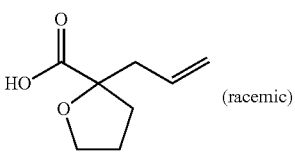

L66c (racemic)

Preparation of 3-vinylpyrazine-2-carboxylic Acid (L67a)

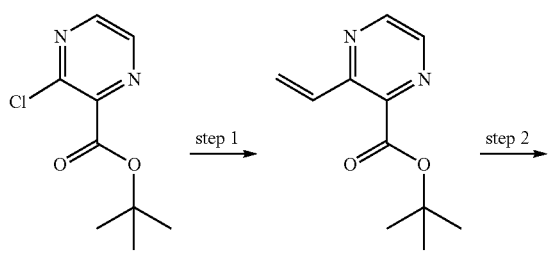

intermediate in the synthesis of L39a

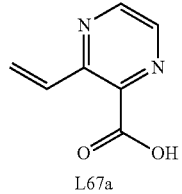

L67a

Step 1

A mixture of tert-butyl 3-chloropyrazine-2-carboxylate (400 mg, 1.86 mmol), 4,4,5,5-tetramethyl-2-vinyl-1,3,2-dioxaborolane (373 mg, 2.42 mmol), Pd(dtbpf)Cl₂ (121 mg, 0.19 mmol) and 1 M K₃PO₄ (3.7 mL) in THF (8 mL) was stirred at 100° C. in a sealed tube for 6 h. Upon cooling, the mixture was diluted with ethyl acetate, washed with brine, dried over MgSO₄, filtered, and concentrated to afford a crude product that was purified by silica gel chromatography (5%-50% EtOAc in hexane) to afford tert-butyl 3-vinylpyrazine-2-carboxylate. ES/MS: m/z 207.2 [M+H]⁺.

Step 2

To a solution of tert-butyl 3-vinylpyrazine-2-carboxylate (175 mg, 0.849 mmol) in 1:1 THF/MeOH (3 mL) was added 1 M NaOH (2.55 mL). The mixture was stirred at 50° C. for 1 h and concentrated under reduced pressure. The lithium salt of 3-vinylpyrazine-2-carboxylic acid was used without further manipulation for the synthesis of Example 484 following the general Procedure 25. ES/MS: m/z 151.1 [M+H]⁺.

Preparation of
rac-(1S,2R)-2-vinylcyclobutane-1-carboxylic Acid (L68)

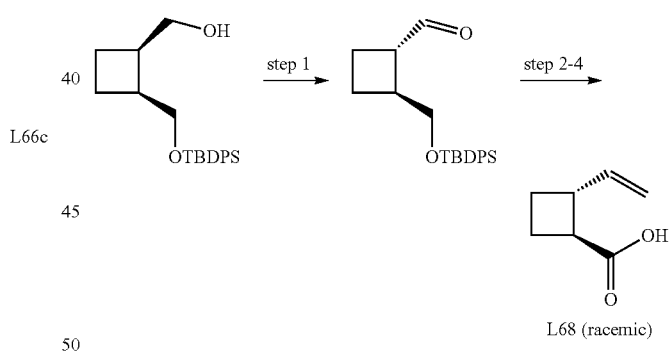

L68 (racemic)

Step 1.

A solution of DMSO (2.85 mL, 40 mmol) in DCM (100 mL) was cooled under N₂ in a CO₂/acetone bath. Oxalyl chloride (2M in DCM, 9.9 mL, 20 mmol) was added over 3 min, and the resulting mixture was allowed to stir 40 min. rac-((1R,2S)-2-(((tert-butyldiphenylsilyl)oxy)methyl)cyclobutyl)methanol (prepared analogously to rac-((1R,3S)-3-(((tert-butyldiphenylsilyl)oxy)methyl)-2,2-dimethylcyclopropyl)methanol as described in the synthesis of L10 but starting from 3-oxabicyclo[3.2.0]heptane-2,4-dione) (4.66 g, 13.1 mmol) was added as a solution in DCM (25 mL) over 5 min, washing with 2×12.5 mL DCM. The resulting mixture was stirred for 45 min, at which time Et₃N (9.3 mL, 66 mmol) was added over 3 min. The reaction was stirred 5 min and removed from the cold bath and allowed to warm to r.t. After stirring for 90 min, the mixture was partitioned between DCM and water, and the aqueous phase was extracted with DCM, dried over Na$_2$SO$_4$, filtered, and concentrated. The crude material was allowed to stand for several days and was then purified by silica gel chromatography (0-30% EtOAc in hexanes) to provide rac-(1S,2S)-2-(((tert-butyldiphenylsilyl)oxy)methyl)cyclobutane-1-carbaldehyde as a ~16.5:1 ratio of isomers. $^1$H NMR (400 MHz, DMSO-d6) δ 9.92 (d, J=1.8 Hz, 1H), 9.65 (d, J=2.0 Hz, 0H), 7.59 (dt, J=7.6, 1.6 Hz, 4H), 7.51-7.40 (m, 6H), 3.72-3.63 (m, 2H), 3.40-3.30 (m, 1H), 3.04-2.92 (m, 1H), 2.41-2.30 (m, 1H), 2.06-1.85 (m, 2H), 1.73-1.62 (m, 1H), 0.98 (s, 9H).

Step 2

A suspension of methyl triphenylphosphonium bromide (3.4 g, 9.5 mmol) in THF (34 mL) was cooled in an ice bath under N$_2$. KOtBu (1 M in THF, 8.7 mL, 8.7 mmol) was added over 2 min, and the resulting mixture was allowed to warm to r.t. for 30 min. The mixture was cooled in an ice bath, and rac-(1S,2S)-2-(((tert-butyldiphenylsilyl)oxy)methyl)cyclobutane-1-carbaldehyde (2.2 g, 6.2 mmol) was added as a solution in THF (30 mL). The reaction mixture was stirred overnight, at which time additional methylenetriphenyl-λ$^5$-phosphane (ca. 8.7 mmol, prepared analogously as described above) was added via canula. The resulting mixture was stirred overnight and was partitioned between Et$_2$O, sat. NH$_4$Cl, and water. The organic layer was dried over MgSO$_4$, filtered, and concentrated. Purification by silica gel provided rac-tert-butyldiphenyl(((1S,2R)-2-vinylcyclobutyl)methoxy)silane.

Step 3 rac-tert-butyldiphenyl(((1S,2R)-2-vinylcyclobutyl)methoxy)silane (1.96 g, 5.6 mmol) was dissolved in THF, and TBAF (1 M in THF, 7.3 mL, 7.3 mmol) was added. The resulting mixture was stirred until TLC indicated completion, at which time the mixture was concentrated directly onto silica gel and purified by silica gel chromatography to provide rac-((1S,2R)-2-vinylcyclobutyl)methanol.

Step 4

Periodic acid dihydrate (2.33 g, 8.8 mmol) was stirred in MeCN (40 mL) for 30 min. rac-((1S,2R)-2-vinylcyclobutyl)methanol (450 mg, 4.0 mmol) was added and the mixture was cooled in an ice water bath. Pyridinium chlorochromate (30 mg, 0.14 mmol) was added in one portion, and the mixture was stirred for 30 min and partitioned between EtOAc and water/brine. The aqueous phase was extracted with EtOAc and the combined organic phase was washed with saturated sodium bisulfite followed by brine. The organic phase was concentrated to afford rac-(1R,2S)-2-vinylcyclobutanecarboxylic acid that was used without further purification. 1H NMR (400 MHz, DMSO-d6) δ 12.00 (s, 1H), 6.07-5.81 (m, 1H), 5.07-4.98 (m, 2H), 3.31-3.18 (m, 2H), 2.22-2.03 (m, 2H), 2.03-1.85 (m, 2H).

Preparation of tert-butyl (1R,2S)-2-((Z)-5-hydroxypent-2-en-1-yl)cyclopropane-1-carboxylate (L69a)

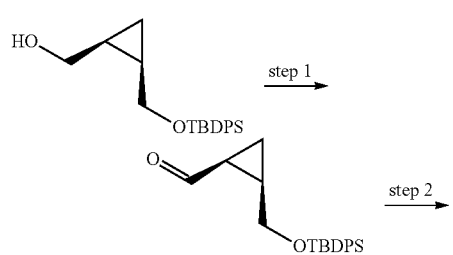

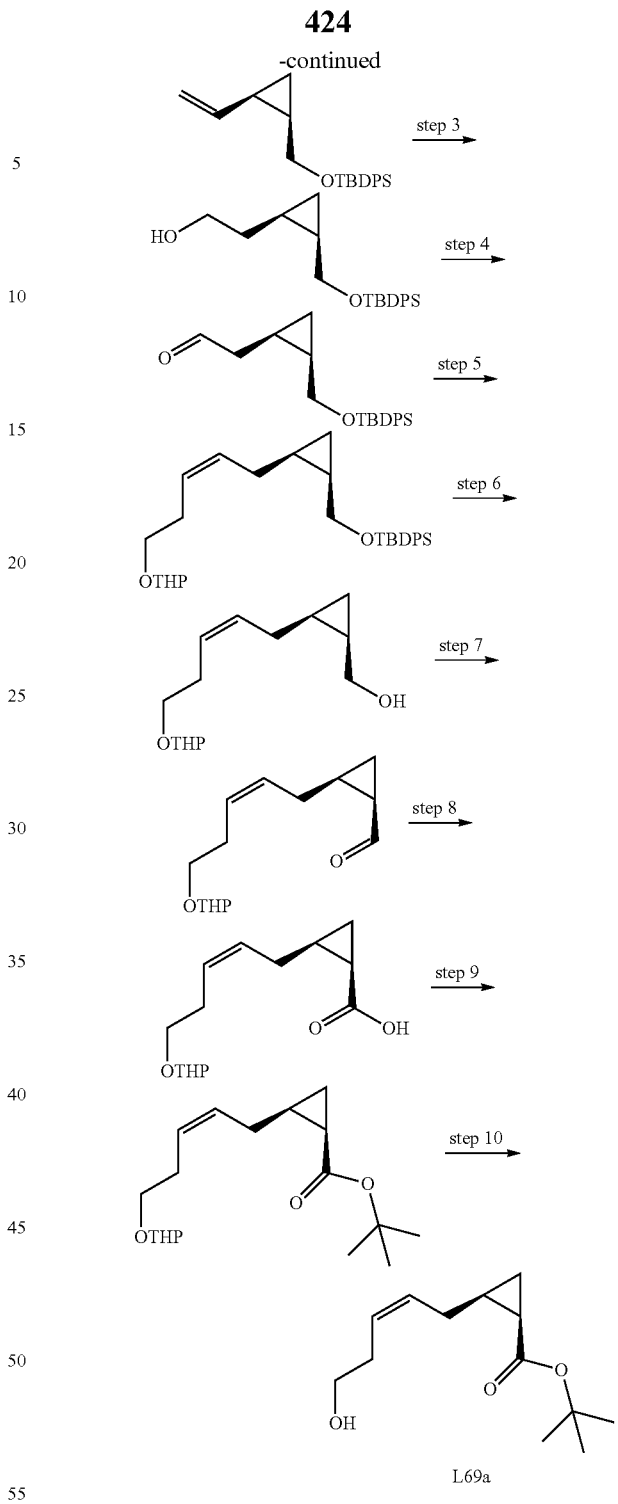

Step 1

(1S,2R)-2-[[tert-butyl(diphenyl)silyl]oxymethyl]cyclopropanecarbaldehyde was prepared as for L35a, step 4 using [(1S,2R)-2-[[tert-butyl(diphenyl)silyl]oxymethyl]-cyclopropyl]methanol. ES/MS: m/z 360.9 [M+Na]$^+$.

Step 2 tert-Butyl-diphenyl-[[(1R,2R)-2-vinylcyclopropyl]methoxy]silane was prepared as for L15a, step 2 using (1S,2R)-2-[[tert-butyl(diphenyl)silyl]oxymethyl]-cyclopropanecarbaldehyde.

ES/MS: m/z 337.2 [M+H]$^+$.

Step 3

2-[(1R,2R)-2-[[tert-butyl(diphenyl)silyl]oxymethyl]cyclopropyl]ethanol was prepared in a similar manner as for L15a, step 3 using tert-butyl-diphenyl-[[(1R,2R)-2-vinylcyclopropyl]methoxy]silane. ES/MS: m/z 354.7 [M+H]⁺.

Step 4

2-[(1R,2R)-2-[[tert-butyl(diphenyl)silyl]oxymethyl]cyclopropyl]acetaldehyde was prepared in a similar manner as for L37, step 4 using 2-[(1R,2R)-2-[[tert-butyl(diphenyl)silyl]oxymethyl]cyclopropyl]ethanol. ES/MS: m/z 375.3 [M+Na]⁺.

Step 5 triphenyl(3-tetrahydropyran-2-yloxypropyl)phosphonium bromide (2.79 g, 5.7 mmol) was suspended in THF (25 mL) and cooled to 0° C. under N₂. NaHMDS (1.0 M THF; 6.2 mL, 6.2 mmol) was added slowly to give an orange suspension. The reaction was removed from cooling bath, allowed to stir at ambient temperature for 45 minutes, and cooled to 0° C. A solution of 2-[(1R,2R)-2-[[tert-butyl(diphenyl)silyl]oxymethyl]cyclopropyl]acetaldehyde (1.45 g, 4.1 mmol) in THF (5 mL) was added dropwise. The mixture was allowed to attain ambient temperature and stir overnight. Aq. NH4Cl and EtOAc were added, and the phases separated. The organic phase was washed once with brine, then adsorbed onto isolute and purified by silica gel chromatography (0-60% EtOAc in hexanes) with ELS detection to afford tert-butyl-diphenyl-[[(1R,2S)-2-(5-tetrahydropyran-2-yloxypent-2-enyl)cyclopropyl]methoxy]silane as a yellow oil. ES/MS: m/z 501.3 [M+Na]⁺.

Step 6

[(1R,2S)-2-[(Z)-5-tetrahydropyran-2-yloxypent-2-enyl]cyclopropyl]methanol was prepared in a similar manner to step 3 for L35a using tert-butyl-diphenyl-[[(1R,2S)-2-(5-tetrahydropyran-2-yloxypent-2-enyl)cyclopropyl]methoxy]silane. ES/MS: m/z 263.1 [M+Na]⁺. 1H NMR (400 MHz, DMSO-d6) δ 5.54 (dtt, J=10.4, 7.1, 1.6 Hz, 1H), 5.36 (dtt, J=10.9, 7.3, 1.5 Hz, 1H), 4.55 (dd, J=4.3, 2.8 Hz, 1H), 4.36 (t, J=5.2 Hz, 1H), 3.73 (ddd, J=11.3, 8.1, 3.2 Hz, 1H), 3.59 (dtd, J=9.6, 7.0, 1.6 Hz, 1H), 3.48 (ddd, J=11.4, 6.4, 5.0 Hz, 1H), 3.45-3.32 (m, 3H), 2.26 (q, J=6.8 Hz, 2H), 2.11 (dt, J=14.2, 6.9 Hz, 1H), 1.99 (dt, J=15.1, 7.7 Hz, 1H), 1.77-1.53 (m, 2H), 1.53-1.37 (m, 4H), 1.03-0.88 (m, 1H), 0.76 (qdd, J=8.2, 6.8, 5.5 Hz, 1H), 0.58 (td, J=8.3, 4.4 Hz, 1H), −0.06 (dd, J=5.5, 4.4 Hz, 1H).

Step 7

(1R,2S)-2-[(Z)-5-tetrahydropyran-2-yloxypent-2-enyl]cyclopropanecarbaldehyde was prepared in a similar manner as for L37, step 4 using [(1R,2S)-2-[(Z)-5-tetrahydropyran-2-yloxypent-2-enyl]cyclopropyl]methanol. ES/MS: m/z 261.2 [M+Na]⁺.

Step 8

(1R,2S)-2-[(Z)-5-tetrahydropyran-2-yloxypent-2-enyl]cyclopropanecarboxylic acid was prepared in a similar manner as for L35a, step 5 using (1R,2S)-2-[(Z)-5-tetrahydropyran-2-yloxypent-2-enyl]cyclopropanecarbaldehyde. ES/MS: m/z 277.1 [M+Na]⁺.

Step 9

Prepared in a similar manner to step 6 for L35a using (1R,2S)-2-[(Z)-5-tetrahydropyran-2-yloxypent-2-enyl]cyclopropanecarboxylic acid. Purification by silica gel chromatography (0-100% EtOAc in hexanes) with ELS detection provided tert-butyl (1R,2S)-2-[(Z)-5-tetrahydropyran-2-yloxypent-2-enyl]cyclopropanecarboxylate. ES/MS: m/z 333.2 [M+Na]⁺.

Step 10

Prepared in a similar manner to step 7 for L35a using tert-butyl (1R,2S)-2-[(Z)-5-tetrahydropyran-2-yloxypent-2-enyl]cyclopropanecarboxylate. Purification by silica gel chromatography (0-100% EtOAc in hexanes) with ELS detection provided tert-butyl (1R,2S)-2-[(Z)-5-hydroxypent-2-enyl]cyclopropanecarboxylate. ES/MS: m/z 249.1 [M+Na]⁺. 1H NMR (400 MHz, DMSO-d6) δ 5.45-5.31 (m, 2H), 4.48 (t, J=5.3 Hz, 1H), 3.37 (td, J=6.9, 5.3 Hz, 2H), 2.39-2.01 (m, 4H), 1.65-1.54 (m, 1H), 1.40 (s, 9H), 1.30-1.15 (m, 1H), 0.95 (td, J=8.1, 4.2 Hz, 1H), 0.72 (ddd, J=7.1, 5.4, 4.2 Hz, 1H).

1-(allyloxy)cyclopropane-1-carboxylic Acid (L66b)

Prepared following a similar procedure to L69a starting with [(1R,2S)-2-[[tert-butyl(diphenyl)silyl]oxymethyl]-cyclopropyl]methanol.

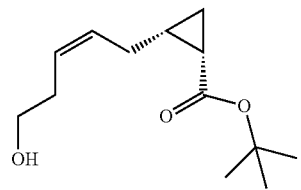

L69b

Preparation of tert-butyl (E)-3-((2-fluoro-4-hydroxybut-2-en-1-yl)oxy)propanoate (L70)

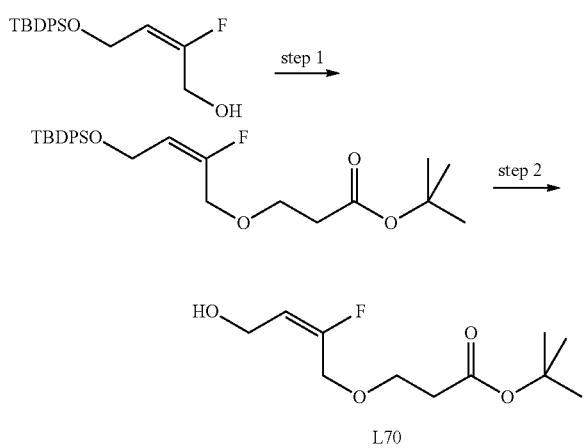

L70

(E)-4-((tert-butyldiphenylsilyl)oxy)-2-fluorobut-2-en-1-ol was prepared as described in Nucleosides, *Nucleotides* & *Nucleic Acids*, 22 (5-8), 659-661; 2003.

Step 1 tert-butyl (E)-3-((4-((tert-butyldiphenylsilyl)oxy)-2-fluorobut-2-en-1-yl)oxy)propanoate was prepared following a similar procedure to step 4 of L10. ES/MS: m/z 495.3 [M+Na]⁺.

Step 2 tert-butyl (E)-3-((2-fluoro-4-hydroxybut-2-en-1-yl)oxy)propanoate was prepared following a similar procedure to step 2 of L2a. ES/MS: m/z 257.2 [M+Na]⁺.

Preparation of 4-methoxy-2-vinylnicotinic acidate (L71a)

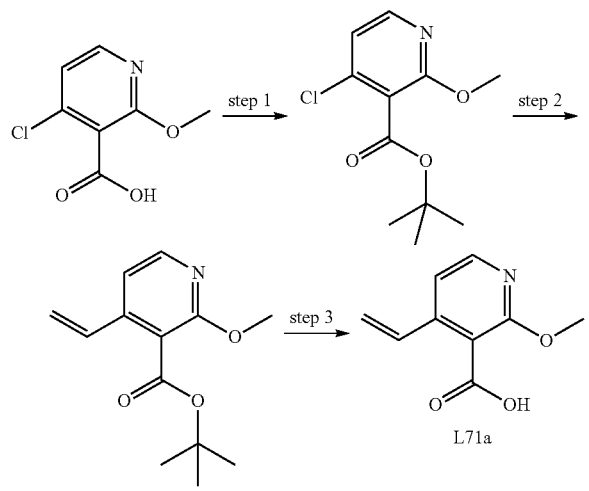

Step 1
tert-butyl 4-chloro-2-methoxynicotinate was prepared following a similar procedure to step 1 of L50a starting with 4-chloro-2-methoxynicotinic acid. ES/MS: m/z 244.1 [M+H]$^+$.

Step 2
tert-butyl 2-methoxy-4-vinylnicotinate was prepared following a similar procedure to step 1 of L67a starting with tert-butyl 4-chloro-2-methoxynicotinate. ES/MS: m/z 236.2 [M+H]$^+$.

Step 3
A solution of tert-butyl 2-methoxy-4-vinylnicotinate (98 mg, 0.417 mmol) in DCM (1.0 mL) and TFA (1.0 mL) was stirred at rt for o/n. Upon concentration under reduce pressure, the resulting intermediate L71a was used without further purification. ES/MS: m/z 180.1 [M+H]$^+$.

Preparation of tert-butyl rac-(1S,2S)-2-(5-hydroxypentyl)-2-methylcyclopropane-1-carboxylate (L72)

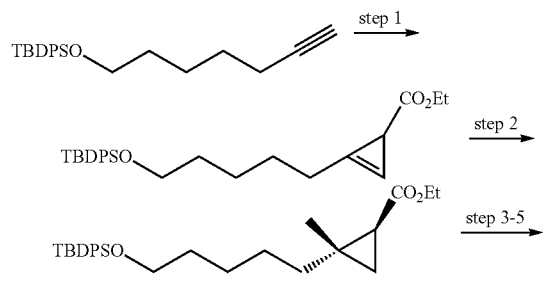

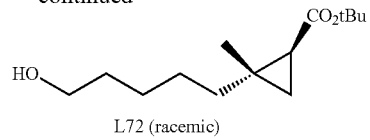

L72 (racemic)

Step 1
ethyl 2-(5-((tert-butyldiphenylsilyl)oxy)pentyl)cycloprop-2-ene-1-carboxylate was prepared following a similar procedure for compound 2 in Org. Lett. 2010, 248-251 using tert-butyl(hept-6-yn-1-yloxy)diphenylsilane. $^1$H NMR (400 MHz, Chloroform-d) δ 7.68-7.64 (m, 4H), 7.44-7.35 (m, 6H), 6.31 (q, J=1.5 Hz, 1H), 4.17-4.07 (m, 3H), 3.66 (t, J=6.4 Hz, 2H), 2.50-2.44 (m, 2H), 2.12 (d, J=1.5 Hz, 1H), 1.62-1.52 (m, 4H), 1.48-1.38 (m, 2H), 1.27-1.21 (m, 3H), 1.04 (s, 9H).

Step 2
ethyl rac-(1S,2S)-2-(5-((tert-butyldiphenylsilyl)oxy)pentyl)-2-methylcyclopropane-1-carboxylate was prepared following a similar procedure for compound 6a in J. Am. Chem. Soc. 2009, 5382-5382 using ethyl 2-(5-((tert-butyldiphenylsilyl)oxy)pentyl)-cycloprop-2-ene-1-carboxylate. $^1$H NMR (400 MHz, Chloroform-d) δ 7.71-7.63 (m, 4H), 7.46-7.33 (m, 6H), 4.19-4.04 (m, 2H), 3.65 (t, J=6.5 Hz, 2H), 1.60-1.52 (m, 1H), 1.44 (dd, J=8.1, 5.5 Hz, 1H), 1.41-1.22 (m, 11H), 1.15 (s, 3H), 1.04 (s, 9H), 0.81 (dd, J=8.1, 4.3 Hz, 1H).

Step 3
rac-(1S,2S)-2-(5-((tert-butyldiphenylsilyl)oxy)pentyl)-2-methylcyclopropane-1-carboxylic acid was prepared following step 2 of L66a using ethyl rac-(1S,2S)-2-(5-((tert-butyldiphenylsilyl)oxy)pentyl)-2-methylcyclopropane-1-carboxylate. ES/MS: m/z 447.3 [M+Na]$^+$.

Step 4
tert-butyl rac-(1S,2S)-2-(5-((tert-butyldiphenylsilyl)oxy)pentyl)-2-methylcyclopropane-1-carboxylate was prepared following step 1 of L50a using rac-(1S,2S)-2-(5-((tert-butyldiphenylsilyl)oxy)pentyl)-2-methylcyclopropane-1-carboxylic acid. ES/MS: m/z 503.3 [M+Na]$^+$.

Step 5
tert-butyl rac-(1S,2S)-2-(5-hydroxypentyl)-2-methylcyclopropane-1-carboxylate was prepared following step 3 of L35a using tert-butyl rac-(1S,2S)-2-(5-((tert-butyldiphenylsilyl)oxy)pentyl)-2-methylcyclopropane-1-carboxylate. ES/MS: m/z 265.2 [M+Na]$^+$.

Preparation of tert-butyl rac-(1R,2R)-2-(2,2-difluoro-5-hydroxypentyl)cyclopropane-1-carboxylate (L73a) and tert-butyl rac-(1R,2S)-2-(2,2-difluoro-5-hydroxypentyl)cyclopropane-1-carboxylate (L73b)

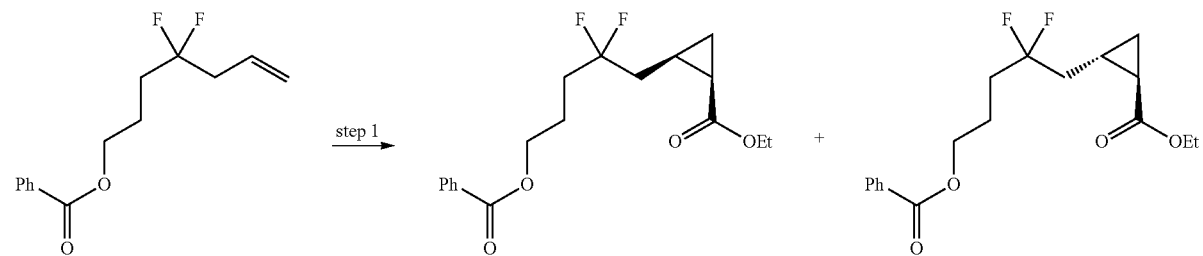

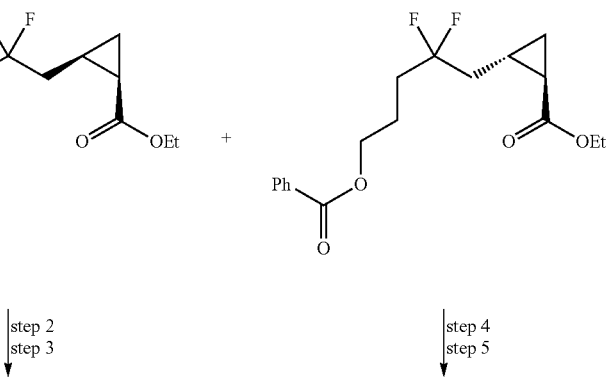

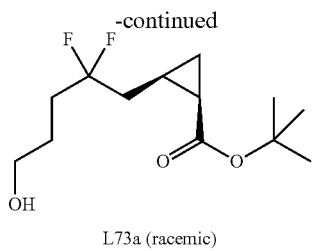

L73a (racemic)

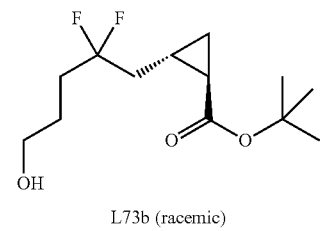

L73b (racemic)

Step 1

To solution of 4,4-difluorohept-6-en-1-yl benzoate (J. Org. Chem. 2014, 818-822; 2.0 g, 7.87 mmol) and Rh$_2$(OAc)$_4$ in DCM (70 mL) at rt was added a solution of ethyl diazoacetate in DCM (10 mL) over 5 h and the mixture was stirred o/n. Upon concentration, the crude product (1:1 mixture of cis/trans isomers) was purify by silica gel chromatography (0-30% EtOAc in hexanes) to afford rac-5-((1R,2R)-2-(ethoxycarbonyl)cyclopropyl)-4,4-difluoropentyl benzoate (first eluting peak) and rac-5-((1S,2R)-2-(ethoxycarbonyl)cyclopropyl)-4,4-difluoropentyl benzoate (last eluting peak).

rac-5-((1R,2R)-2-(ethoxycarbonyl)cyclopropyl)-4,4-difluoropentyl benzoate (cis): $^1$H NMR (400 MHz, Chloroform-d) δ 8.06-8.01 (m, 2H), 7.60-7.54 (m, 1H), 7.48-7.42 (m, 2H), 4.36 (t, J=5.9 Hz, 2H), 4.13 (q, J=7.1 Hz, 2H), 2.25-2.12 (m, 2H), 2.10-1.92 (m, 4H), 1.78 (td, J=8.3, 5.5 Hz, 1H), 1.44 (ddt, J=15.8, 8.7, 7.1 Hz, 1H), 1.25 (t, J=7.1 Hz, 3H), 1.11 (td, J=8.3, 4.6 Hz, 1H), 0.98 (dt, J=7.1, 5.1 Hz, 1H). Relative stereochemistry confirmed by ROESY.

rac-5-((1S,2R)-2-(ethoxycarbonyl)cyclopropyl)-4,4-difluoropentyl benzoate (trans): $^1$H NMR (400 MHz, Chloroform-d) δ 8.07-8.01 (m, 2H), 7.60-7.54 (m, 1H), 7.48-7.42 (m, 2H), 4.37 (t, J=6.1 Hz, 2H), 4.12 (q, J=7.1 Hz, 2H), 2.13-1.90 (m, 5H), 1.80 (qd, J=15.1, 7.1 Hz, 1H), 1.57-1.46 (m, 2H), 1.31-1.20 (m, 4H), 0.83-0.77 (m, 1H). Relative stereochemistry confirmed by ROESY.

Step 2 and 3.

tert-butyl rac-(1R,2R)-2-(2,2-difluoro-5-hydroxypentyl)cyclopropane-1-carboxylate was prepared following step 2 of L66a and step 1 of L50a using rac-5-((1R,2R)-2-(ethoxycarbonyl)cyclopropyl)-4,4-difluoropentyl benzoate (L73a). $^1$H NMR (400 MHz, Chloroform-d) δ 3.69 (t, J=6.3 Hz, 2H), 2.15 (ddd, J=17.7, 15.5, 7.0 Hz, 2H), 2.03-1.89 (m, 2H), 1.81-1.65 (m, 3H), 1.45 (s, 8H), 1.36 (td, J=8.7, 7.0 Hz, 1H), 1.07-0.96 (m, 1H), 0.89 (dt, J=7.0, 5.1 Hz, 1H).

Step 4 and 5.

tert-butyl rac-(1R,2S)-2-(2,2-difluoro-5-hydroxypentyl)cyclopropane-1-carboxylate was prepared following step 2 of L66a and step 1 of L50a using rac-5-((1S,2R)-2-(ethoxycarbonyl)cyclopropyl)-4,4-difluoropentyl benzoate (L73b). $^1$H NMR (400 MHz, Chloroform-d) δ 3.71 (t, J=6.3 Hz, 2H), 2.08-1.91 (m, 3H), 1.82-1.71 (m, 3H), 1.44 (s, 9H), 1.46-1.36 (m, 1H), 1.22-1.14 (m, 1H), 0.73 (ddd, J=8.3, 6.3, 4.4 Hz, 1H).

Preparation of rac-(1S,2S)-1-(trifluoromethyl)-2-vinylcyclopropane-1-carboxylic Acid (L74)

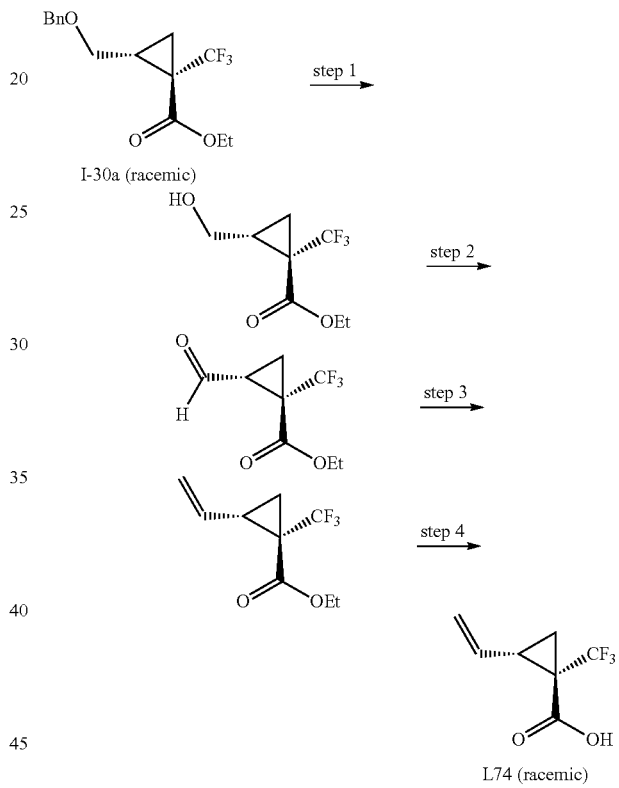

Step 1

To a solution of ethyl rac-(1S,2R)-2-((benzyloxy)methyl)-1-(trifluoromethyl)cyclopropane-1-carboxylate (I-30a) (2.0 g, 6.6 mmol) in EtOAc (5 mL) and EtOH (5 mL) was added Pd/C (10% dry basis, 50% water weight) (500 mg, 0.23 mmol). The vessel was purged twice with H$_2$ and the mixture was stirred under 1 atm. H$_2$ for 90 min. The mixture was filtered and concentrated to provide ethyl rac-(1S,2R)-2-(hydroxymethyl)-1-(trifluoromethyl)cyclopropane-1-carboxylate.

Step 2

Oxalyl chloride (1.1 mL, 13 mmol) was added to DCM (15 mL) under N$_2$. The solution was cooled in a CO$_2$/acetone bath to −78° C., and DMSO (1.9 mL, 27 mmol) was added dropwise via syringe. After stirring 20 min, a solution of ethyl rac-(1S,2R)-2-(hydroxymethyl)-1-(trifluoromethyl)cyclopropane-1-carboxylate (1.4 g, 6.6 mmol) in DCM (5 mL) was added slowly via syringe. Additional portions of DCM (2×2.5 mL) were used to wash. After stirring 45 min, triethylamine (7.4 mL, 53 mmol) was added slowly via syringe. The mixture was removed from the cold bath and allowed to reach r.t., at which time TLC showed complete consumption of SM. The mixture was partitioned between DCM and water, and the organic phase was dried over Na$_2$SO$_4$, filtered, and concentrated directly onto silica gel. Purification by silica gel chromatography (EA:hexanes gradient) provided ethyl rac-(1S,2R)-2-formyl-1-(trifluoromethyl)cyclopropane-1-carboxylate.

Step 3

Methyltriphenylphosphonium bromide (5.3 g, 15 mmol) was taken up in THF (60 mL) under N$_2$. A solution of potassium tert-butoxide in THF (1 M, 13.4 mL, 13.4 mmol) was added over 5 min via syringe. After stirring 30 min, as solution of ethyl rac-(1S,2R)-2-formyl-1-(trifluoromethyl)cyclopropane-1-carboxylate (1.4 g, 6.6 mmol) was added as a solution in THF (5 mL). The reaction mixture was stirred until TLC showed complete consumption of starting material, and was then partitioned between Et$_2$O and water. The organic phase was dried over MgSO$_4$, filtered, and carefully concentrated (product is volatile) to afford a residue that was purified by silica gel chromatography (Et$_2$O in hexanes gradient) to afford ethyl rac-(1S,2S)-1-(trifluoromethyl)-2-vinylcyclopropane-1-carboxylate.

Step 4 ethyl rac-(1S,2S)-1-(trifluoromethyl)-2-vinylcyclopropane-1-carboxylate (780 mg) was dissolved in THF (5 mL), MeOH (2.5 mL) and water (2.5 mL). The mixture was stirred until TLC indicated complete consumption of starting material, and was then partitioned between DCM and aq. HCl. The aqueous phase was extracted with DCM, and the combined organic phase was dried over Na$_2$SO$_4$, filtered, and concentrated to afford rac-(1S,2S)-1-(trifluoromethyl)-2-vinylcyclopropane-1-carboxylic acid. 1H NMR (400 MHz, DMSO-d6) δ 13.50 (s, 1H), 5.70-5.55 (m, 1H), 5.49 (dd, J=17.0, 1.9 Hz, 1H), 5.26 (dd, J=10.1, 1.9 Hz, 1H), 2.49-2.38 (m, 1H), 1.79-1.71 (m, 1H), 1.60 (dd, J=7.8, 5.3 Hz, 1H).

Preparation of tert-butyl 6-chloro-2-(2-((1R,2S)-2-(hydroxymethyl)cyclopropyl)ethyl)nicotinate (L75a)

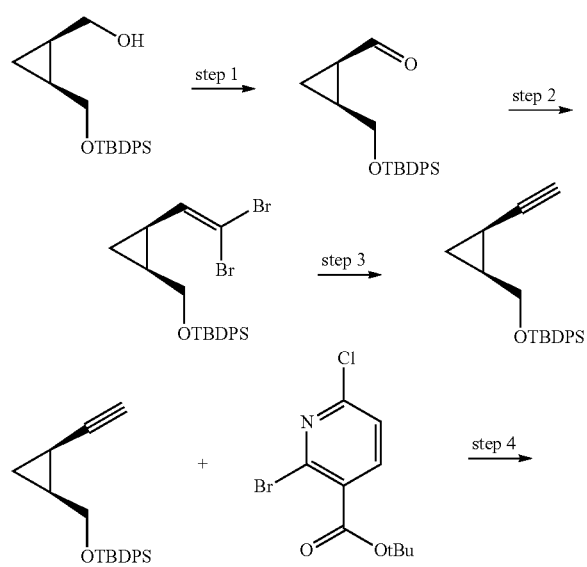

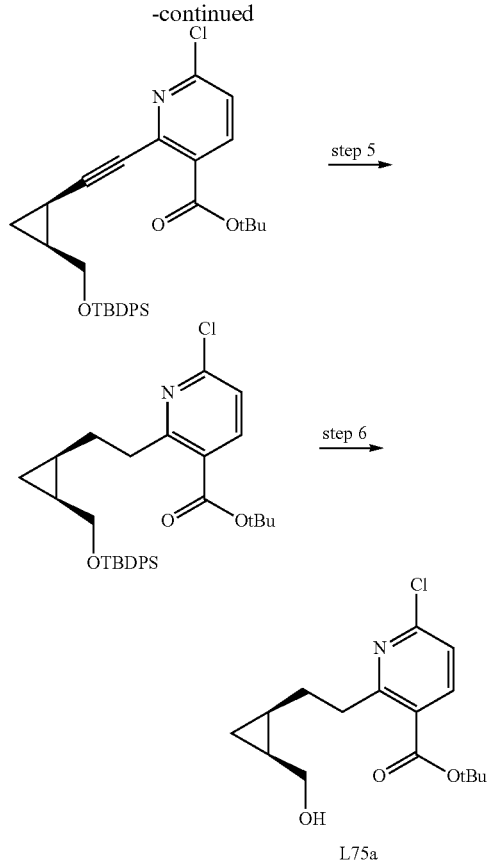

Step 1

(1R,2S)-2-(((tert-butyldiphenylsilyl)oxy)methyl)cyclopropane-1-carbaldehyde was prepared using a similar procedure to step 1 of L31 with ((1R,2S)-2-(((tert-butyldiphenylsilyl)oxy)methyl)cyclopropyl)methanol. 1H NMR (400 MHz, Chloroform-d) δ 9.76 (d, J=7.6 Hz, 1H), 7.68-7.59 (m, 4H), 7.47-7.35 (m, 6H), 3.92 (ddd, J=11.6, 5.6, 2.5 Hz, 1H), 3.55 (ddd, J=11.6, 8.4, 1.0 Hz, 1H), 2.21-2.04 (m, 1H), 1.61 (ddd, J=17.2, 10.7, 6.7 Hz, 1H), 1.44 (td, J=8.8, 6.7 Hz, 1H), 1.06-1.00 (m, 10H).

Step 2

To a solution of triphenylphosphine (5.9 g, 23 mmol) and carbon tetrabromide (3.8 g, 11 mmol) in DCM (12 mL) at 0° C. was added a solution of (1R,2S)-2-(((tert-butyldiphenylsilyl)oxy)methyl)cyclopropane-1-carbaldehyde (1.9 g, 5.6 mmol) in DCM (12 mL). The reaction was allowed to warm to room temperature and stirred for 4 hr. Water was added and the aqueous layer was washed 3 times with DCM. The combined organic layers were dried over Na$_2$SO$_4$, filtered and concentrated. The crude residue was purified by flash chromatography eluting with hexanes/EtOAc to give a colorless oil (1.8 g, 63%). 1H NMR (400 MHz, Chloroform-d) δ 7.71-7.62 (m, 4H), 7.47-7.35 (m, 6H), 6.18 (d, J=9.1 Hz, 1H), 3.86 (dd, J=11.2, 5.1 Hz, 1H), 3.53 (dd, J=11.2, 7.6 Hz, 1H), 1.74 (qd, J=8.6, 5.4 Hz, 1H), 1.45 (dtd, J=13.7, 8.2, 5.9 Hz, 1H), 1.06 (s, 10H), 0.57 (q, J=5.5 Hz, 1H).

Step 3

To a solution of tert-butyl(((1S,2R)-2-(2,2-dibromovinyl)cyclopropyl)methoxy)diphenylsilane (530 mg, 1.1 mmol) in THF (7.2 mL) at −78° C. was slowly added a 2.5 M solution of nBuLi (1.7 mL, 4.3 mmol). The reaction was stirred for 20 min. Saturated sodium bicarbonate was added and the aqueous layer was washed 2 times with EtOAc. The combined organic layers were dried over Na₂SO₄, then filtered through a small plug of silica gel and concentrated to afford an oil (270 mg, 0.80 mmol). 1H NMR (400 MHz, Chloroform-d) δ 7.75-7.63 (m, 4H), 7.45-7.32 (m, 6H), 3.83 (dd, J=11.1, 7.2 Hz, 1H), 3.76 (dd, J=11.0, 6.4 Hz, 1H), 1.74 (d, J=2.2 Hz, 1H), 1.44 (tdd, J=8.0, 5.4, 2.2 Hz, 1H), 1.36-1.23 (m, 2H), 1.07 (s, 9H), 0.47 (q, J=5.5 Hz, 1H).
Step 4
tert-butyl 2-(((1R,2S)-2-(((tert-butyldiphenylsilyl)oxy) methyl)cyclopropyl)ethynyl)-6-chloronicotinate was prepared using a similar procedure to step 1 of L28a with tert-butyl 2-bromo-6-chloronicotinate and tert-butyl(((1S,2R)-2-ethynylcyclopropyl)methoxy)diphenylsilane. ES/MS: m/z 546.03 [M+H]⁺.
Step 5
tert-butyl 2-(2-((1R,2S)-2-(((tert-butyldiphenylsilyl)oxy) methyl)cyclopropyl)ethyl)-6-chloronicotinate was prepared using a similar procedure to step 3 of L58a with tert-butyl 2-(((1R,2S)-2-(((tert-butyldiphenylsilyl)oxy)methyl)cyclopropyl)ethynyl)-6-chloronicotinate. ES/MS: m/z 550.20 [M+H]⁺.
Step 6
tert-butyl 6-chloro-2-(2-((1R,2S)-2-(hydroxymethyl)cyclopropyl)ethyl)nicotinate was prepared using a similar procedure to step 2 of L2a with tert-butyl 2-(2-((1R,2S)-2-(((tert-butyldiphenylsilyl)oxy)methyl)cyclopropyl)ethyl)-6-chloronicotinate. ES/MS: m/z 312.10 [M+H]+.

tert-butyl 6-chloro-2-(2-((1S,2R)-2-(hydroxymethyl) cyclopropyl)ethyl)nicotinate (L75b)

Prepared following a similar procedure to L69a starting with [(1R,2S)-2-[[tert-butyl(diphenyl)silyl]oxymethyl]-cyclopropyl]methanol. ES/MS: m/z 312.10 [M+H]+.

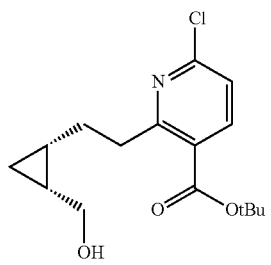

L75b tert-butyl 6-chloro-2-(2-((1S,2S)-2-(hydroxymethyl) cyclopropyl)ethyl)nicotinate (L75c)

Prepared following a similar procedure to L69a starting with ((1S,2S)-2-(((tert-butyldiphenylsilyl)oxy)methyl)cyclopropyl)methanol. ES/MS: m/z 312.10 [M+H]+.

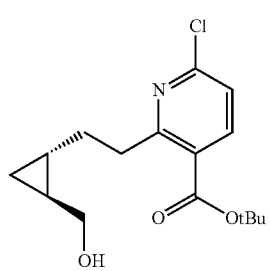

L75c tert-butyl 6-chloro-2-(2-((1R,2R)-2-(hydroxymethyl) cyclopropyl)ethyl)nicotinate (L75d)

Prepared following a similar procedure to L69a starting with ((1R,2R)-2-(((tert-butyldiphenylsilyl)oxy)methyl)cyclopropyl)methanol. ES/MS: m/z 312.10 [M+H]+.

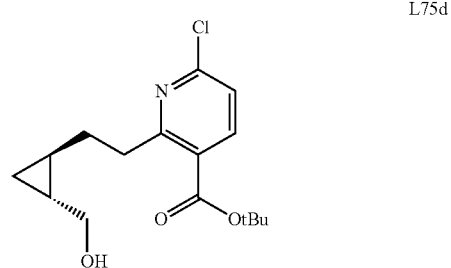 [SMILES: CC(C)(C)OC(=O)c1ccc(Cl)nc1CC[C@@H]1C[C@H]1CO]

L75d

Preparation of tert-butyl 2-(difluoromethyl)-4-(5-hydroxypentyl)nicotinate (L76a)

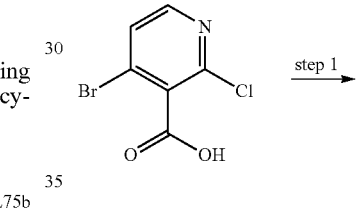

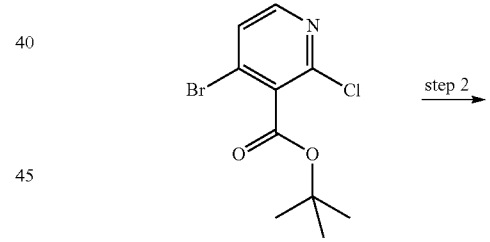

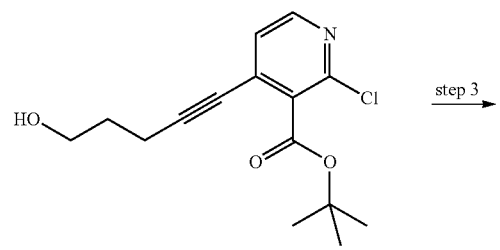

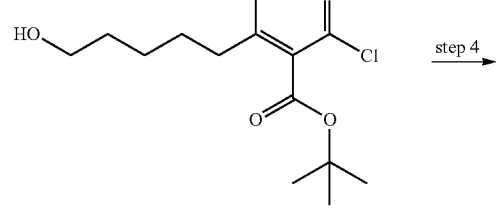

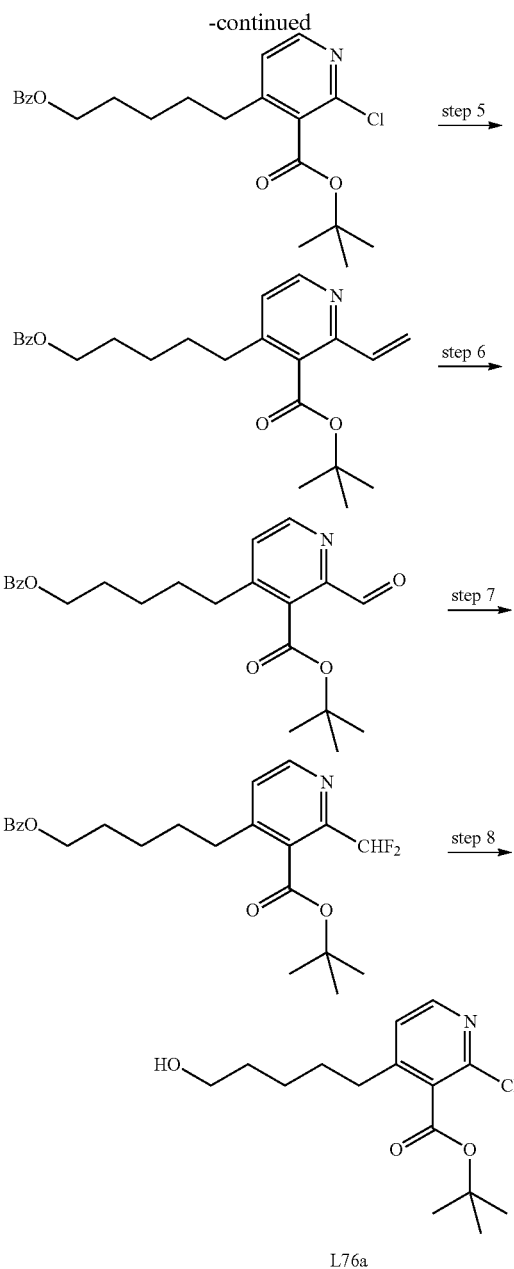

L76a

Step 1
tert-butyl 4-bromo-2-chloronicotinate was made following step 1 of L56a using 4-bromo-2-chloronicotinic acid. ES/MS: m/z 291.87 [M+H]+.

Step 2
tert-butyl 2-chloro-4-(5-hydroxypent-1-yn-1-yl)nicotinate was made following step 1 of L38a using tert-butyl 4-bromo-2-chloronicotinate. ES/MS: m/z 295.76 [M+H]+.

Step 3
tert-butyl 2-chloro-4-(5-hydroxypentyl)nicotinate was made following step 2 of L38a using tert-butyl 2-chloro-4-(5-hydroxypent-1-yn-1-yl)nicotinate. ES/MS: m/z 299.87 [M+H]+.

Step 4
tert-butyl 4-(5-(benzoyloxy)pentyl)-2-chloronicotinate was made following step 1 of L54a using tert-butyl 2-chloro-4-(5-hydroxypentyl)nicotinate. ES/MS: m/z 403.88 [M+H]+.

Step 5
tert-butyl 4-(5-(benzoyloxy)pentyl)-2-vinylnicotinate was made following step 1 of I-129 using tert-butyl 4-(5-(benzoyloxy)pentyl)-2-chloronicotinate. ES/MS: m/z 396.00 [M+H]+.

Step 6
tert-butyl 4-(5-(benzoyloxy)pentyl)-2-formylnicotinate was made following step 4 of I-146a using tert-butyl 4-(5-(benzoyloxy)pentyl)-2-vinylnicotinate. ES/MS: m/z 397.86 [M+H]+.

Step 7
To a solution of tert-butyl 4-(5-(benzoyloxy)pentyl)-2-formylnicotinate (378 mg, 0.951 mmol) in dichloromethane (25 mL) in an ice bath was added diethylaminosulfur trifluoride (230 mg, 1.43 mmol). The ice bath was removed and the reaction stirred for 2 hr. Saturated sodium bicarbonate solution was carefully added and the aqueous layer was washed three times with dichloromethane. The combined organic layers were dried over $Na_2SO_4$, filtered and concentrated. The crude residue was purified by flash chromatography eluting with hexanes/EtOAc to give a colorless oil (200 mg, 50%). ES/MS: m/z 419.92 [M+H]+.

Step 8.
tert-butyl 2-(difluoromethyl)-4-(5-hydroxypentyl)nicotinate was made following step 4 of L18 using tert-Butyl 4-(5-(benzoyloxy)pentyl)-2-(difluoromethyl)nicotinate. ES/MS: m/z 315.86 [M+H]+.

Preparation of rac-(1S,2S)-1-(methoxymethyl)-2-vinylcyclopropane-1-carboxylic acid (L77)

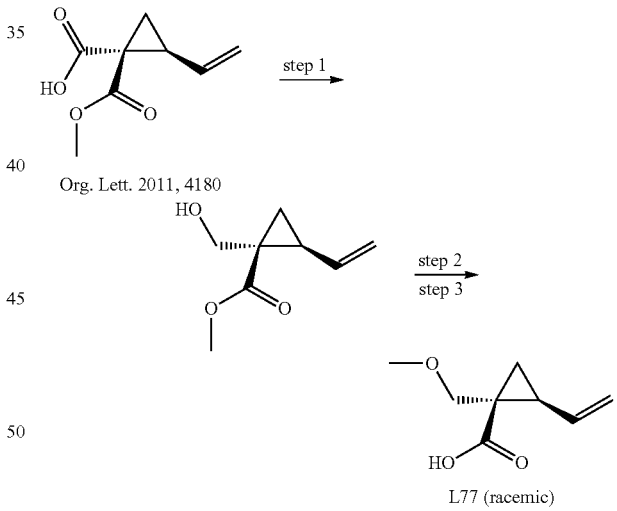

L77 (racemic)

Step 1
To a solution of rac-(1S,2S)-1-(methoxycarbonyl)-2-vinylcyclopropane-1-carboxylic acid (39.7 g, 233 mmol) in THF (400 mL) was added CDI (41.6 g, 256 mmol). The reaction mixture was stirred at rt for 2 h. $NaBH_4$ (8.8 g, 233 mmol) was then added portionwise. The reaction mixture was stirred at rt for 16 h. The reaction was quenched with water and extracted with EtOAc. The combined organic phase was dried over anhydrous $Na_2SO_4$, filtrated and evaporated to give oil. The crude product was purified by column chromatography ($SiO_2$, Petroleum ether/Ethyl acetate=I/O to 2/1) and evaporated to give methyl rac-(1S,2S)-1-(methoxymethyl)-2-vinylcyclopropane-1-carboxylate. ¹H NMR: (DMSO-d6 400 MHz): δ 5.52 (td, J=9.7, 17.2 Hz, 1H), 5.23-5.12 (m, 1H), 4.98 (dd, J=1.8, 10.4 Hz, 1H), 4.75 (t, J=5.8 Hz, 1H), 3.92 (dd, J=6.3, 11.4 Hz, 1H), 3.63-3.54 (m, 4H), 3.20 (dd, J=5.4, 11.4 Hz, 1H), 1.95-1.85 (m, 1H), 1.33-1.26 (m, 1H), 1.25-1.16 (m, 1H)

Step 2.

methyl rac-(1S,2S)-1-(methoxymethyl)-2-vinylcyclopropane-1-carboxylate was made following step 4 of L16a using methyl rac-(1S,2S)-1-(hydroxymethyl)-2-vinylcyclopropane-1-carboxylate.

Step 3 rac-(1S,2S)-1-(methoxymethyl)-2-vinylcyclopropane-1-carboxylic acid was made following step 4 of L66a using methyl rac-(1S,2S)-1-(methoxymethyl)-2-vinylcyclopropane-1-carboxylate. ¹H NMR: (DMSO-d6 400 MHz): δ 12.38 (s, 1H), 5.72-5.47 (m, 1H), 5.20 (dd, J=1.5, 17.2 Hz, 1H), 4.99 (dd, J=1.7, 10.3 Hz, 1H), 3.85 (d, J=10.1 Hz, 1H), 3.20 (s, 3H), 3.05 (d, J=10.1 Hz, 1H), 1.94-1.79 (m, 1H), 1.38-1.28 (m, 1H), 1.17 (dd, J=4.4, 8.8 Hz, 1H).

Preparation of 6-methoxy-2-vinylnicotinic Acid (L78)

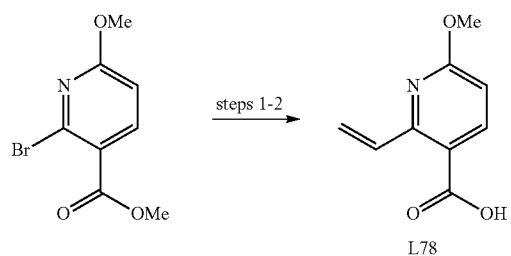

Step 1

Methyl 2-bromo-6-methoxy-pyridine-3-carboxylate (100 mg, 0.406 mmol) was combined with Potassium vinyltrifluoroborate (75 mg, 0.560 mmol), Dichloro 1,1'-bis(diphenylphosphino)ferrocene palladium (II) dichloromethane (26 mg, 0.032 mmol), sodium carbonate (2M aqueous solution, 0.41 mL, 0.813 mmol), and dioxane (2 mL). The mixture was degassed with N₂, then heated to 90 C and stirred o/n. The reaction was adsorbed to isolute and purified by silica gel chromatography (0-50% 3:1 EtOAc/EtOH in heptane) to afford methyl 6-methoxy-2-vinyl-pyridine-3-carboxylate. ES/MS: m/z 194.0 [M+H]⁺.

Step 2

Methyl 6-methoxy-2-vinyl-pyridine-3-carboxylate (92 mg, 143 mmol) was dissolved in a mixture of THF (1 mL), MeOH (0.2 mL), and H2O (0.6 mL), then treated with lithium hydroxide (0.43 mL of a 1M aqueous solution, 0.43 mmol). After stirring o/n, the reaction was concentrated and dried to afford 6-methoxy-2-vinyl-pyridine-3-carboxylic acid, which was used without purification in the next step. ES/MS: m/z 180.0 [M+H]⁺.

Preparation of methyl (1R,2R)-2-vinylcyclopropane-1-carboxylate (L79)

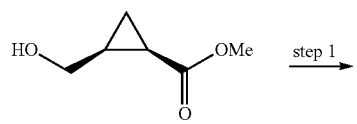

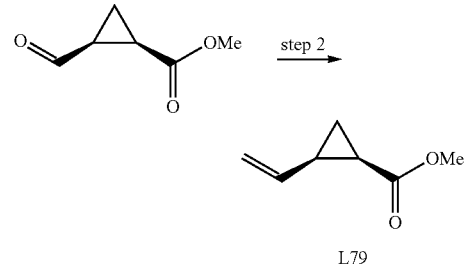

Synlett, (10), 1641-1644; 2002

Step 1.

PCC (67.9 g, 315 mmol) was added to a solution of methyl (1R,2S)-2-(hydroxymethyl)cyclopropane-1-carboxylate (20.5 g, 157 mmol) in DCM (140 mL). The mixture was stirred at 15° C. for 12 hours, then was diluted with DCM and purified directly by silica gel chromatography (2-100% EtOAc in pet. ether) to afford methyl (1R,2S)-2-formylcyclopropane-1-carboxylate. ¹H NMR: (CDCl₃ 400 MHz): δ 9.33 (d, J=6.8 Hz, 1H), 3.72 (s, 3H), 2.27-2.21 (m, 1H), 2.07-2.03 (m, 1H), 1.94-1.90 (m, 1H), 1.57-1.51 (m, 1H).

Step 2

KOt-Bu (3.0 g, 27 mmol) was added to Ph₃P⁺Br⁻Me (13.0 g, 36.5 mmol) in Et₂O (54 mL) and was stirred at 20° C. for 30 minutes. A solution of methyl (1R,2S)-2-formyl-cyclopropane-1-carboxylate (3.6 g, 28.1 mmol) in Et₂O (54 mL) was added dropwise and the reaction allowed to stir at 20° C. for 2 hours. The mixture was cooled to 10° C. and filtered to removed solids. The resulting filtrate was purified by silica gel chromatography (0-100% DCM in pentane), then partially to afford methyl (1R,2R)-2-vinylcyclopropane-1-carboxylate as a solution containing approx. 30% pentane. GC/MS: m/z 126 [M]⁺. ¹H NMR: (CDCl₃ 400 MHz): δ 5.82-5.73 (m, 1H), 5.26-5.21 (m, 1H), 5.06-5.03 (m, 1H), 3.68 (s, 3H), 1.97-1.91 (m, 2H), 1.33-1.21 (m, 2H).

Preparation of trans-tert-butyl 2-(2-(3-(tosyloxy)propyl)cyclopropyl)benzoate (L80)

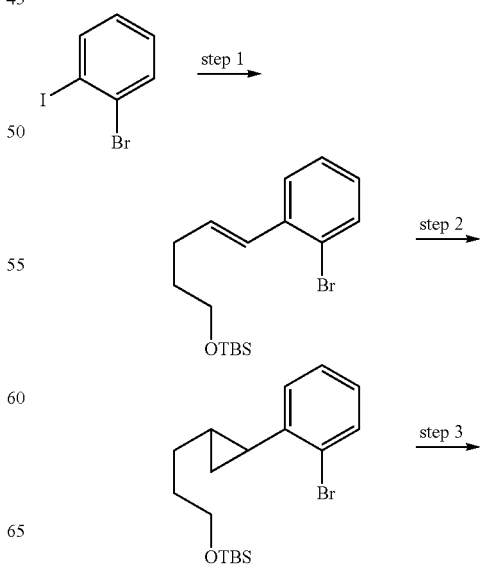

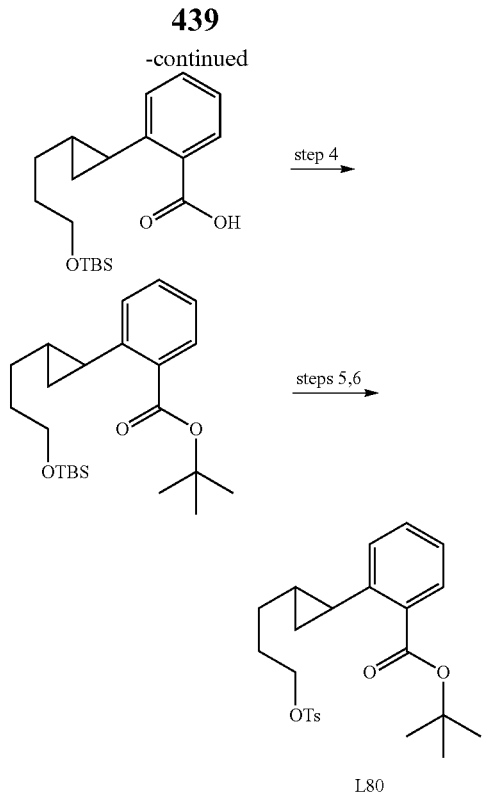

L80

Step 1

(E)-((5-(2-bromophenyl)pent-4-en-1-yl)oxy)(tert-butyl)dimethylsilane was prepared according to Step 2 in the synthesis of L56a using 1-bromo-2-iodobenzene in place of tert-butyl 4-bromo-5-methyl-isoxazole-3-carboxylate. 1H NMR (400 MHz, DMSO-d6) δ 7.65-7.56 (m, 2H), 7.38-7.31 (m, 1H), 7.20-7.13 (m, 1H), 6.67-6.60 (m, 1H), 6.32 (dt, J=15.7, 6.9 Hz, 1H), 3.64 (t, J=6.2 Hz, 2H), 2.28 (qd, J=7.1, 1.5 Hz, 2H), 1.70-1.56 (m, 2H), 0.88 (s, 9H), 0.04 (s, 6H).

Step 2

Under $N_2$ and in an ice bath, a solution of diethylzinc in THF (1 M, 14.8 mL, 14.8 mmol) was added to dichloromethane (20 mL). TFA (1.15 mL, 15 mmol) was added dropwise in over 10 min. After stirring an additional 30 min, diiodomethane (1.2 mL, 15 mmol) was added dropwise over 2 min. The mixture was stirred an additional 75 min, and (E)-((5-(2-bromophenyl)pent-4-en-1-yl)oxy)(tert-butyl)dimethylsilane (1.35 g, 3.8 mmol) was added as a solution in DCM (5 mL) over 3 min, washing with 2×1.5 mL DCM. The mixture was removed from the ice bath and stirred 16 h, at which time it was diluted with EtOAc and sat. $NH_4Cl$. The organic phase was dried over $Na_2SO_4$, filtered, and concentrated, and the obtained residue was purified by silica gel to afford trans-(3-(2-(2-bromophenyl)cyclopropyl)propoxy)(tert-butyl)dimethylsilane (1.04 g, 74%). $^1$H NMR (400 MHz, DMSO-d6) δ 7.60-7.54 (m, 1H), 7.30-7.24 (m, 1H), 7.12-7.06 (m, 1H), 7.00-6.95 (m, 1H), 3.62 (t, J=6.4 Hz, 2H), 1.86 (dt, J=8.6, 5.0 Hz, 1H), 1.68-1.57 (m, 2H), 1.50-1.42 (m, 2H), 1.03-0.91 (m, 2H), 0.86 (s, 9H), 0.84-0.80 (m, 1H), 0.02 (s, 6H).

Step 3 trans-(3-(2-(2-bromophenyl)cyclopropyl)propoxy)(tert-butyl)dimethylsilane (1.03 g, 2.9 mmol) was dissolved in THF (20 mL) under $N_2$ and the solution was cooled to −78° C. A solution of n-BuLi in hexanes (2.5 M, 1.5 mL, 3.8 mmol) was added dropwise over 1 min, and the resulting solution was stirred for 25 min. Solid $CO_2$ (excess) was added, and the reaction was removed from the cold bath and allowed to warm to r.t. with a vent. The mixture was then partitioned between DCM and water, and the aqueous phase was acidified with HCl. The aqueous phase was extracted with DCM, and the combined organics were dried over $Na_2SO_4$, filtered, and concentrated to afford crude trans-2-(2-(3-((tert-butyldimethylsilyl)oxy)propyl)cyclopropyl)benzoic acid. ES/MS: m/z 334.84 $[M+H]^+$.

Step 4

Crude trans-2-(2-(3-((tert-butyldimethylsilyl)oxy)propyl)cyclopropyl)benzoic acid (0.54 mmol) was dissolved in THF (4 mL), and 2-tert-Butyl-1,3-diisopropylisourea (0.4 mL, 1.8 mmol) was added. The mixture was heated to 70° C. overnight. After 18 h, the mixture was filtered to remove solids, and the filtrate was concentrated. The crude residue was purified by silica gel chromatography (0-10% EtOAc in hexanes) to provide trans-tert-butyl 2-(2-(3-((tert-butyldimethylsilyl)oxy)propyl)cyclopropyl)benzoate. $^1$H NMR (400 MHz, DMSO-d6) δ 7.57-7.53 (m, 1H), 7.41-7.35 (m, 1H), 7.22-7.17 (m, 1H), 6.97-6.92 (m, 1H), 3.60 (t, J=6.4 Hz, 2H), 2.24 (dt, J=8.5, 5.0 Hz, 1H), 1.63-1.56 (m, 2H), 1.55 (s, 9H), 1.46-1.37 (m, 2H), 1.06-0.95 (m, 1H), 0.95-0.89 (m, 1H), 0.85 (s, 9H), 0.80-0.73 (m, 1H), 0.01 (s, 6H).

Step 5 and 6.

trans-tert-butyl 2-(2-(3-(tosyloxy)propyl)cyclopropyl)benzoate was prepared following a procedure similar to that described in Steps 2 and 3 in the synthesis of L2a, but starting with trans-tert-butyl 2-(2-(3-((tert-butyldimethylsilyl)oxy)propyl)cyclopropyl)benzoate. $^1$H NMR (400 MHz, DMSO-d6) δ 7.79-7.74 (m, 2H), 7.59-7.54 (m, 1H), 7.48-7.42 (m, 2H), 7.41-7.35 (m, 1H), 7.24-7.17 (m, 1H), 6.94-6.88 (m, 1H), 4.06 (t, J=6.4 Hz, 2H), 2.40 (s, 3H), 2.19 (dt, J=9.4, 5.0 Hz, 1H), 1.75-1.65 (m, 2H), 1.54 (s, 9H), 1.47-1.36 (m, 1H), 1.36-1.27 (m, 1H), 0.95-0.88 (m, 1H), 0.87-0.80 (m, 1H), 0.75-0.67 (m, 1H).

Preparation of 2-fluoro-2-methylpent-4-enoic Acid (L81)

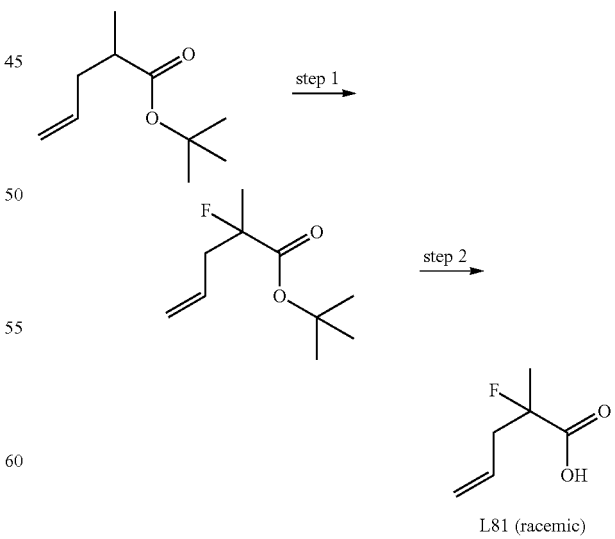

L81 (racemic)

Step 1 tert-butyl 2-fluoro-2-methylpent-4-enoate. Prepared in a manner similar to step 1 of L65a using tert-butyl 2-methylpent-4-enoate and NFSI instead of MeI in step 1 of L65c. 1H NMR (400 MHz, Chloroform-d) δ 5.87-5.73 (m, 1H), 5.19-5.10 (m, 2H), 2.68-2.43 (m, 2H), 1.52 (d, J=21.3 Hz, 3H), 1.48 (s, 9H).

Step 2

2-fluoro-2-methylpent-4-enoic acid. Prepared in a manner similar to step 3 of L71a using tert-butyl 2-fluoro-2-methylpent-4-enoate. 1H NMR (400 MHz, Chloroform-d) δ 7.97 (br s, 1H), 5.82 (ddt, J=16.1, 11.3, 7.2 Hz, 1H), 5.26-5.06 (m, 2H), 2.80-2.51 (m, 2H), 1.62 (d, J=21.3 Hz, 3H).

Preparation of tert-butyl 6-chloro-4-cyclopropyl-2-(5-hydroxypentyl)nicotinate (L82)

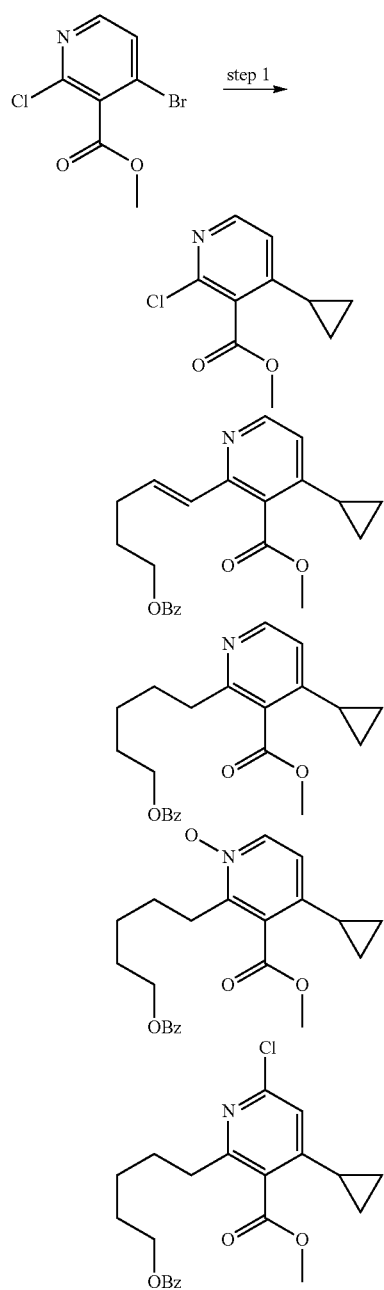

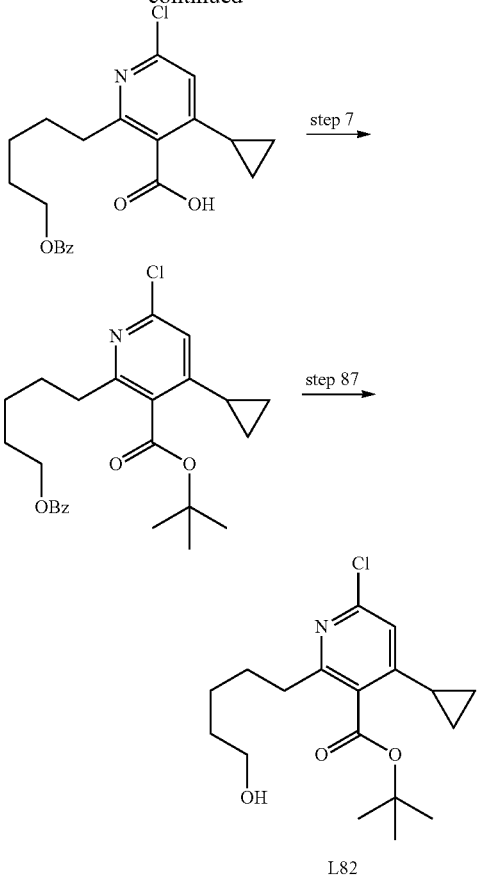

L82

Step 1

Methyl 2-chloro-4-cyclopropylnicotinate was made following the General Procedure of Pd-Catalyzed Cross-Coupling from J. Org. Chem. 2010, 75, 19, 6677-6680. ES/MS: m/z 212.0 [M+H]+.

Step 2

Methyl (E)-2-(5-(benzoyloxy)pent-1-en-1-yl)-4-cyclopropylnicotinate was made following step 1 of L78 using methyl 2-chloro-4-cyclopropylnicotinate, (E)-5-(4,4,5,5-tetramethyl-1,3,2-dioxaborolan-2-yl)pent-4-en-1-yl benzoate (prepared according to Organic Letters (2006), 8(7), 1399-1401), and Cesium carbonate. ES/MS: m/z 366.2 [M+H]+.

Step 3

Methyl 2-(5-(benzoyloxy)pentyl)-4-cyclopropylnicotinate was made following step 5 of L52a using methyl (E)-2-(5-(benzoyloxy)pent-1-en-1-yl)-4-cyclopropylnicotinate and Pt/C.

ES/MS: m/z 368.2 [M+H]+.

Step 4

Methyl 2-(5-(benzoyloxy)pentyl)-4-cyclopropyl-1-(11-oxidanyl)-1λ4-pyridine-3-carboxylate. To a solution of methyl 2-(5-(benzoyloxy)pentyl)-4-cyclopropylnicotinate (460 mg, 1.2 mmol) in dichloromethane (5.5 mL) was added 3-chloroperbenzoic acid (830 mg, 3.7 mmol). The mixture was allowed to stir for 2 hr. Saturated bicarbonate was added and the aqueous layer was washed 3× with dichloromethane. The combined organic layers were dried over sodium sulfate, filtered and concentrated. The crude residue was purified by flash chromatography eluting with EtOAc/MeOH. ES/MS: m/z 384.1 [M+H]+.

Step 5

Methyl 2-(5-(benzoyloxy)pentyl)-6-chloro-4-cyclopropylnicotinate. A mixture of methyl 2-(5-(benzoyloxy)pentyl)-4-cyclopropyl-1-(1λ-oxidanyl)-1λ4-pyridine-3-carboxylate (740 mg, 1.9 mmol) and phosphorus(V) oxychloride (3.6 mL, 38 mmol)) was stirred at 105° C. for 3 days and then concentrated. The residue was brought up in dichloromethane and saturated bicarbonate. The aqueous layer was washed 2 time with dichloromethane. The organic layers were combined, dried over sodium sulfate, filtered and concentrated. The crude residue was purified by flash chromatography eluting with hexanes/EtOAc to give an oil (310 mg, 40%). ES/MS: m/z 402.1 [M+H]+.

Step 6.

2-(5-(benzoyloxy)pentyl)-6-chloro-4-cyclopropylnicotinic acid. A mixture of methyl 2-(5-(benzoyloxy)pentyl)-6-chloro-4-cyclopropylnicotinate (300 mg, 0.75 mmol) and lithium chloride (320 mg, 7.5 mmol) in dimethylformamide (3.5 mL) was stirred in a microwave at 150° C. for 6 hr and concentrated. Added 1N hydrogen chloride and washed with ethyl acetate 3X. The combined organic layers were dried over sodium sulfate, filtered and concentrated to give an oil that was carried on without further purification. ES/MS: m/z 388.1 [M+H]+.

Step 7 tert-butyl 2-(5-(benzoyloxy)pentyl)-6-chloro-4-cyclopropylnicotinate was made following step 1 of L56a using 2-(5-(benzoyloxy)pentyl)-6-chloro-4-cyclopropylnicotinic acid. ES/MS: m/z 444.1 [M+H]+.

Step 8 tert-butyl 6-chloro-4-cyclopropyl-2-(5-hydroxypentyl)nicotinate was made following step 4 of L18 using tert-butyl 2-(5-(benzoyloxy)pentyl)-6-chloro-4-cyclopropylnicotinate. ES/MS: m/z 340.0 [M+H]+.

Preparation of Rac-(1S,2R)-2-Fluoro-1-Methyl-2-Vinylcyclopropane-1-Carboxylic Acid (L83)

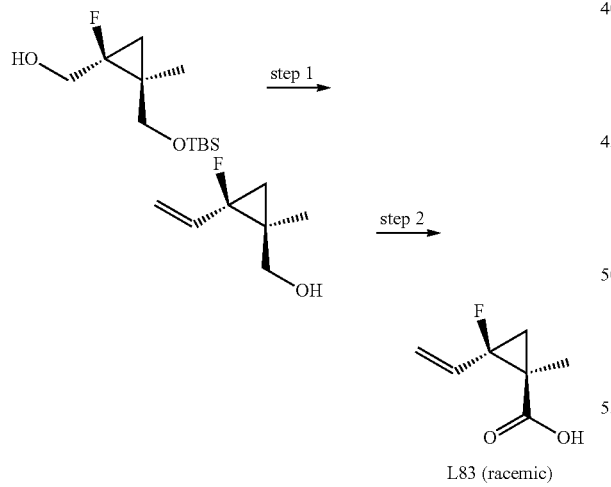

L83 (racemic)

Step 1

Rac-((1S,2R)-2-fluoro-1-methyl-2-vinylcyclopropyl)methanol was prepared following a similar procedure as step 1-3 of L55a using rac-((1S,2S)-2-(((tert-butyldimethylsilyl)oxy)methyl)-1-fluoro-2-methylcyclopropyl)methanol, which was prepared as described in European Journal of Medicinal Chemistry, 42, 2007, 487-493. $^1$H NMR (400 MHz, Chloroform-d) δ 5.84 (ddd, J=21.1, 17.2, 11.0 Hz, 1H), 5.39 (dt, J=17.2, 1.2 Hz, 1H), 5.27 (dt, J=11.1, 1.2 Hz, 1H), 3.87-3.78 (m, 1H), 3.74-3.65 (m, 1H), 1.28-1.22 (m, 1H), 1.18 (d, J=2.4 Hz, 3H), 0.82 (dd, J=9.7, 6.9 Hz, 1H).

Step 2

To a mixture of rac-[(1S,2R)-2-fluoro-1-methyl-2-vinylcyclopropyl]methanol (610 mg, 4.7 mmol) and 4-methylmorpholine N-oxide (6.4 g, 47 mmol) in acetonitrile (22 mL) was added Tetra-n-propylammonium perruthenate(VII) (170 mg, 0.47 mmol). The mixture stirred for 2 hr. To the mixture was added 2-propanol (3.6 mL, 47 mmol) and the mixture was allowed to stir for 30 min and then concentrated. The residue was brought up in 1 N hydrogen chloride and washed three times with ethyl ether. The combined organic layers were combined and washed with brine, dried over magnesium sulfate, filtered and concentrated to give a solid. $^1$H NMR (400 MHz, Chloroform-d) δ 5.83 (dddd, J=18.5, 17.2, 10.9, 0.5 Hz, 1H), 5.50 (dt, J=17.1, 1.2 Hz, 1H), 5.42 (dt, J=10.9, 1.0 Hz, 1H), 2.26 (dd, J=20.8, 7.2 Hz, 1H), 1.31 (d, J=2.3 Hz, 3H), 1.11 (dd, J=11.0, 7.2 Hz, 1H).

4. Synthesis of Intermediates A1 to A38

The following intermediates were purchased from various vendors:

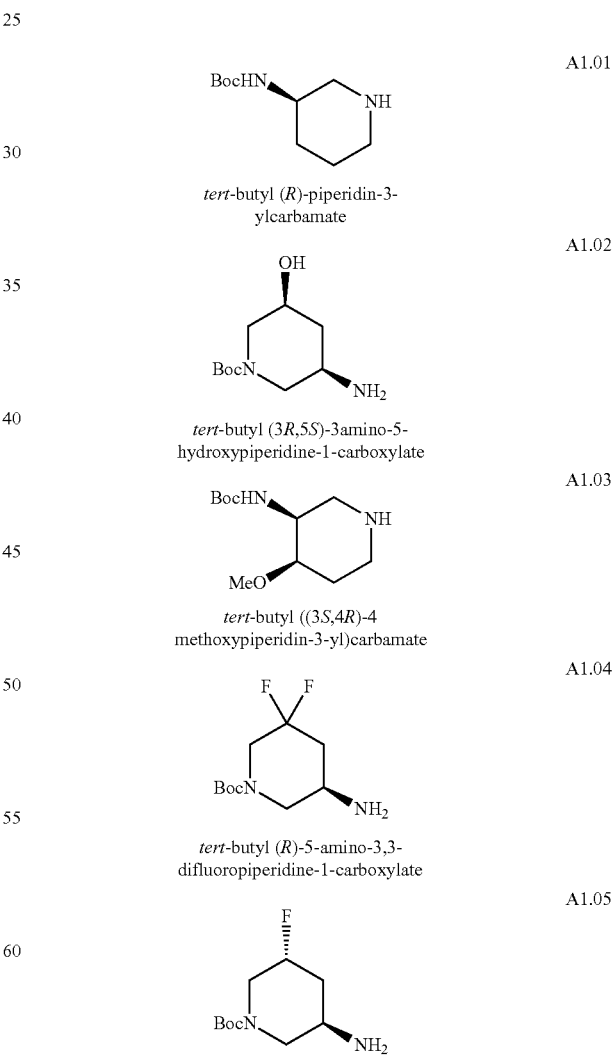

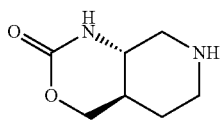

rac-(4aR,8aS)-octahydro-2-H-
pyrido[3,4-d][1,3]oxazin-2-one

A1.06

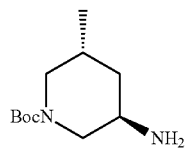

tert-butyl (3R,5R)-3-amino-5-
methylpiperidine-1-carboxylate

A1.07

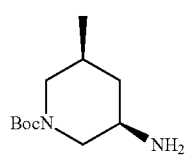

tert-butyl (3R,5S)-3-amino-5-
methylpiperidine-1-carboxylate

A1.08

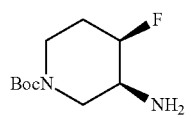

tert-butyl (3S,4R)-3-amino-4-
fluoropiperidine-1-carboxylate

A1.09

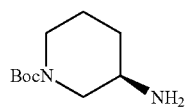

tert-butyl (R)-3-aminopiperidine-
1-carboxylate

A1.10

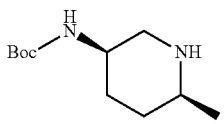

tert-butyl ((3R,6S)-6-
methylpiperidin-3-yl)carbamate

A1.11

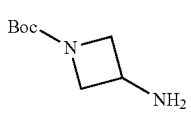

tert-butyl 3-aminoazetidine-
1-carboxylate

A1.12

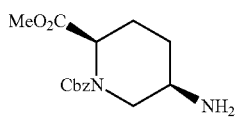

1-benzyl 2-methyl (+/-)-(2R,5R)-5-
aminopiperidine-1,2-dicarboxylate

A1.13

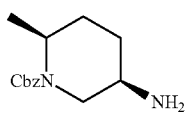

benzyl (2S,5R)-5-amino-2-
methylpiperidine-1-carboxylate

A1.14

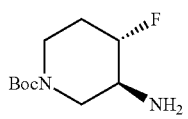

tert-butyl (3S,4S)-3-amino-4-
fluorpiperidine-1-carboxylate

A1.15

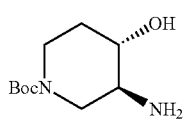

tert-butyl (3S,4S)-3-amino-4-
hydroxypiperidine-1-carboxylate

A1.16

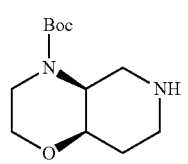

tert-butyl (+/-)-(4aS,8aR)-octahydro-4H-
pyrido[4,3-b][1,4]oxazine-4-carboxylate

A1.17

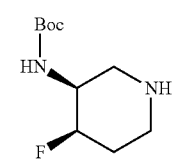

tert-butyl ((3S,4R)-4-
fluoropiperidin-3-yl)carbamate

A1.18

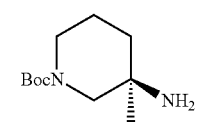

tert-butyl (R)-3-amino-3-
methylpiperidine-1-carboxylate

A1.19

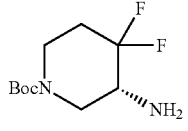

tert-butyl (S)-3-amino-4,4-
difluoropiperidine-1-carboxylate

A1.20

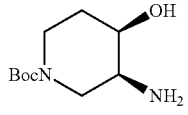

tert-butyl (3S,4R)-3-amino-4-
hydroxypiperidine-1-carboxylate

A1.21

-continued

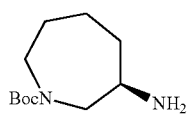

tert-butyl (R)-3-aminoazepane-1-carboxylate

A1.22

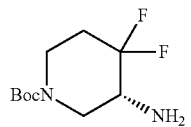

tert-butyl (R)-3-amino-4,4-difluoropiperdine-1-carboxylate

A1.23

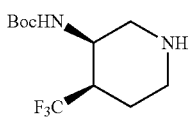

tert-butyl (+/-)-((3R,4R)-4-(trifluoromethyl)piperidin-3-yl)carbamate

A1.24

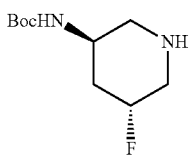

tert-butyl ((3R,5R)-5-fluoropiperidin-3-yl)carbamate

A1.25

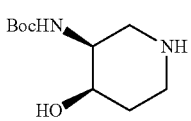

tert-butyl ((3S,4R)-4-hydroxypiperidin-3-yl)carbamate

A1.26

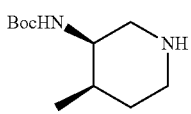

tert-butyl ((3R,4R)-4-methylpiperidin-3-yl)carbamate

A1.27

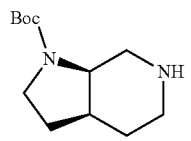

tert-butyl (+/-)-(3aS,7aR)-octahydro-1H-pyrrolo[2,3-c]pyridine-1-carboxylate

A1.28

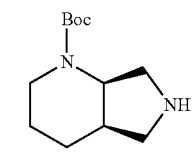

tert-butyl (4aR,7aR)-octahydro-1H-pyrrolo[3,4-b]pyridine-1-carboxylate

A1.29

-continued

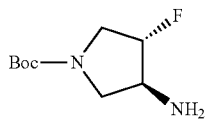

tert-butyl (3S,4S)-3-amino-4-fluoropyrrolidine-1-carboxylate

A1.30

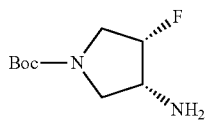

tert-butyl (3R,4S)-3-amino-4-fluoropyrrolidine-1-carboxylate

A1.31

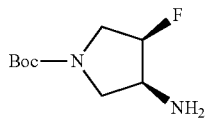

tert-butyl (3S,4R)-3-amino-4-fluoropyrrolidine-1-carboxylate

A1.32

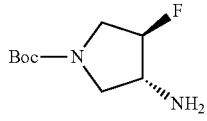

tert-butyl (3R,4R)-3-amino-4-fluoropyrrolidine-1-carboxylate

A1.33

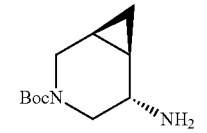

tert-butyl (+/-)-(1S,5S,6R)-5-amino-3-azabicyclo[4.1.0]heptane-3-carboxylate

A1.34

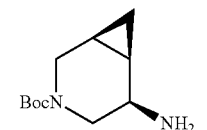

tert-butyl (+/-)-(1S,5R,6R)-5-amino-3-azabicyclo[4.1.0]heptane-3-carboxylate

A1.35

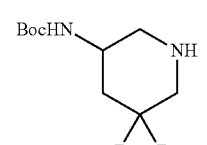

tert-butyl (5,5-difluoropiperidie-3-yl)carbamate

A1.36

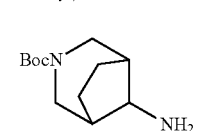

tert-butyl 8-amino-3-azabicyclo[3.2.1]octane-3-carboxylate (mixture of exo/endo)

A1.37

449
-continued

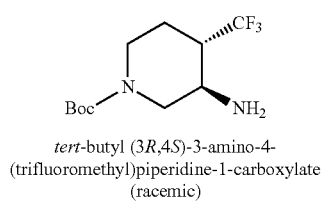
A1.38
tert-butyl (3R,4S)-3-amino-4-
(trifluoromethyl)piperidine-1-carboxylate
(racemic)

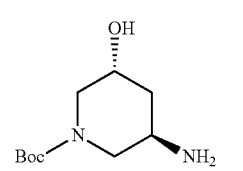
A1.39
tert-butyl (3R,5R)-3-amino-5-
hydroxypiperidine-1-carboxylate

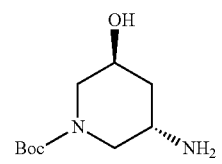
A1.40
tert-butyl (3S,5S)-3-amino-5-
hydroxypiperidine-1-carboxylate
(racemic)

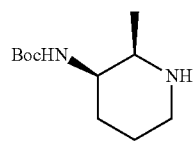
A1.41
tert-butyl ((2R,3R)-2-
methylpiperidin-3-yl)carbamate

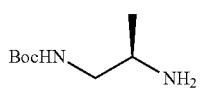
A1.42
tert-butyl (R)-(2-aminopropyl)carbamate

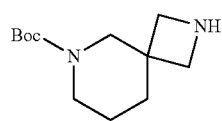
A1.43
tert-butyl 2,6-diazaspiro[3.5]nonane-
6-carboxylate

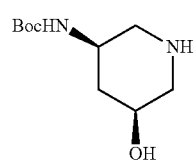
A1.44
tert-butyl ((3R,5S)-5-
hydroxypiperidin-3-yl)carbamate

450
-continued

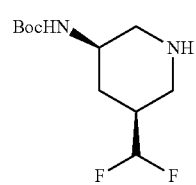
A1-45
tert-butyl ((3R,5S)-5-
(difluoromethyl)piperidin-3-yl)carbamate

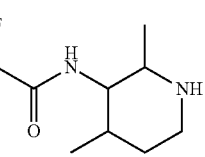
A1.46
tert-butyl ((3R,5R)-5-
fluoropiperidin-3-yl)carbamate

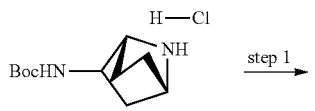
A1.47
EN300-1697642

Preparation of tert-butyl ((1R,2R,4S)-7-azabicyclo
[2.2.1]heptan-2-yl)carbamate (A2)

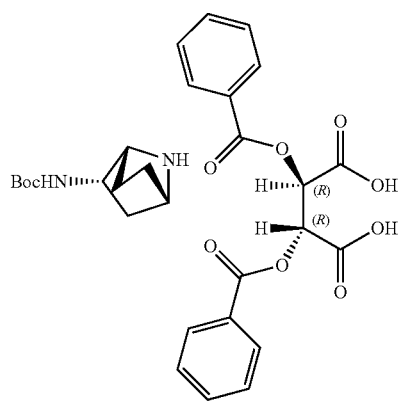

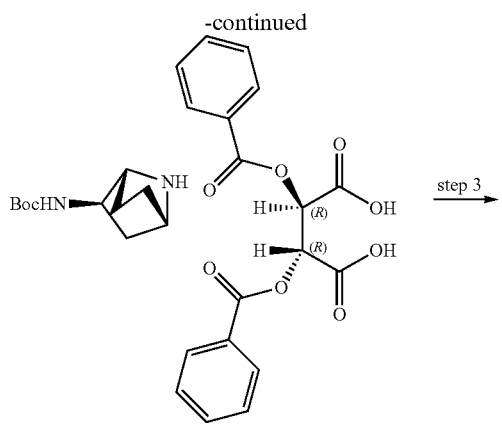

The combined extracts were dried over Na$_2$SO$_4$, filtered, and concentrated to provide the product as a white foam, 21.72 g (91%). $^1$H NMR (400 MHz, DMSO-d6) δ 6.93 (d, J=6.8 Hz, 1H), 3.65-3.54 (m, 1H), 3.39 (t, J=4.6 Hz, 1H), 3.33 (t, J=4.7 Hz, 1H), 2.18 (s, 1H), 1.74 (tdd, J=11.8, 5.2, 2.6 Hz, 1H), 1.69-1.58 (m, 1H), 1.38 (s, 9H), 1.44-1.26 (m, 2H), 1.28-1.16 (m, 1H), 0.95 (dd, J=12.0, 4.7 Hz, 1H). Chiral purity 94.5-95.5% ee (see procedure below for determination). Note—chiral purity can be improved to >99% ee by repeating steps 2 (single treatment with MeCN rather than 5 treatments) and 3.

Determination of Chiral Purity of A2:

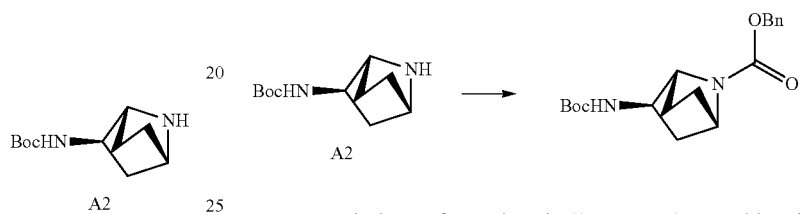

To a solution of tert-butyl ((1R,2R,4S)-7-azabicyclo[2.2.1]heptan-2-yl)carbamate (100 mg, 0.175 mmol) in dioxane and water (1 mL each) was added sodium carbonate (0.84 mL of a 2 M aqueous solution, 1.7 mmol) and carbobenzoxysuccinimide (82 mg, 0.33 mmol). The mixture was allowed to stir at ambient temperature for 5 hours, at which point the thick suspension was diluted further with water. The mixture was extracted into EtOAc, then concentrated and adsorbed to isolute. Purification by silica gel chromatography (eluent: EtOAc in hexane) provided the benzyl (1R,2R,4S)-2-((tert-butoxycarbonyl)amino)-7-azabicyclo[2.2.1]heptane-7-carboxylate. ES/MS: m/z 369.1 [M+Na]$^+$. $^1$H NMR (400 MHz, DMSO-d6) δ 7.42-7.27 (m, 5H), 7.22 (d, J=6.4 Hz, 1H), 5.09-5.00 (m, 2H), 4.17 (t, J=4.4 Hz, 1H), 4.09 (t, J=4.9 Hz, 1H), 3.81-3.70 (m, 1H), 2.08-1.95 (m, 1H), 1.83-1.72 (m, 1H), 1.66-1.54 (m, 1H), 1.53-1.42 (m, 2H), 1.39 (s, 9H), 1.18 (dd, J=12.4, 4.8 Hz, 1H). Chiral purity determined by SFC using AZ-H column (5 mic, 4.6×100 mm) with 10% EtOH as cosolvent, or with IF column (5mic, 4.6×100 mm) using 10% EtOH-TFA as cosolvent.

Step 1.

The HCl salt of tert-butyl ((1R,4S)-7-azabicyclo[2.2.1]heptan-2-yl)carbamate (60.2 g, 242 mmol, commercially available as [2098589-07-0]) was dissolved in 100 mL water. To this was added a solution of sodium carbonate (38.5 g, 363 mmol) in 200 mL water, producing a volumnous white precipitate. The reaction was extracted into EtOAc (4×200 mL), dried over Na$_2$SO$_4$, filtered, and concentrated to give the free base. This material is commercially available as [2098589-06-9].

Step 2 tert-Butyl ((1R,4S)-7-azabicyclo[2.2.1]heptan-2-yl)carbamate (49.7 g, 234 mmol) was added to 900 mL MeCN in a 2-L erlenmeyer flask to give a cloudy solution. (−)-Dibenzoyl-L-tartaric acid [2743-38-6] (83.9 g, 234 mmol) was added as a solid to give a white suspension, which was stirred at ambient temperature. The solids were collected by filtration and washed with cold MeCN, then were re-suspended in MeCN and allowed to stir at ambient temperature. The solids were collected and treated 4 additional times with MeCN to provide. $^1$H NMR (400 MHz, DMSO-d6) δ 9.28 (br. s, 2H), 7.97-7.90 (m, 4H), 7.68-7.58 (m, 2H), 7.50 (t, J=7.8 Hz, 4H), 7.35 (d, J=5.9 Hz, 1H), 5.64 (s, 2H), 4.04-3.92 (m, 3H), 2.14-2.02 (m, 1H), 1.89-1.68 (m, 2H), 1.67-1.49 (m, 2H), 1.38 (s, 9H), 1.28 (dd, J=13.2, 4.1 Hz, 1H).

Step 3 tert-Butyl ((1R,2R,4S)-7-azabicyclo[2.2.1]heptan-2-yl)carbamate (2R,3R)-2,3-bis(benzoyloxy)succinate (64.3 g, 113 mmol) was added to a solution of sodium carbonate (17.9 g, 169 mmol) in water (500 mL). EtOAc (1000 mL) was added and the mixture stirred until all solids had dissolved. The phases were separated and the aqueous phase was extracted repeatedly with EtOAc, followed by DCM.

Preparation of tert-butyl ((1R,4R,7R)-2-azabicyclo[2.2.1]heptan-7-yl)carbamate (A3)

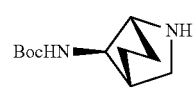

tert-Butyl ((1R,4R,7R)-2-azabicyclo[2.2.1]heptan-7-yl)carbamate was prepared according to a literature procedure (Advanced Synthesis and Catalysis, 2005, vol. 347, #9, p. 1242-1246).

Preparation of benzyl ((1R,2R,4S)-7-azabicyclo[2.2.1]heptan-2-yl)carbamate (A4)

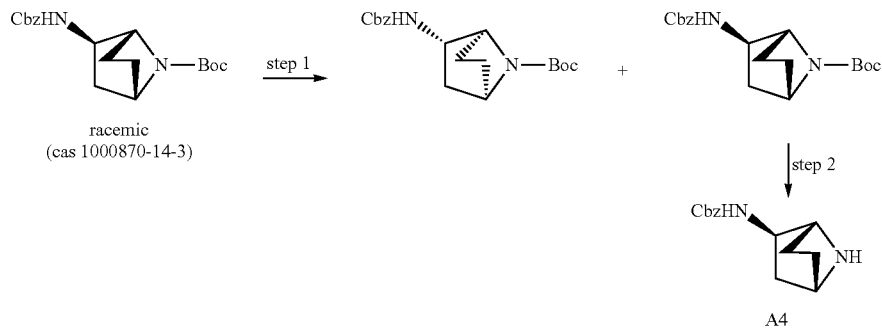

Step 1

A racemic mixture (cas 1000870-14-3) of tert-butyl (1S,2S,4R)-2-(((benzyloxy)carbonyl)amino)-7-azabicyclo[2.2.1]heptane-7-carboxylate and tert-butyl (1R,2R,4S)-2-(((benzyloxy)carbonyl)amino)-7-azabicyclo[2.2.1]heptane-7-carboxylate was separated by chiral SFC.

Step 2 tert-butyl (1R,2R,4S)-2-(((benzyloxy)carbonyl)amino)-7-azabicyclo[2.2.1]heptane-7-carboxylate (46 mg, 0.13 mmol) was dissolved in dioxane. 4 M hydrochloric acid in dioxane (2 mL) was added, and the resulting mixture was stirred at ambient temperature for 1 h. The reaction mixture was concentrated to provide benzyl ((1R,2R,4S)-7-azabicyclo[2.2.1]heptan-2-yl)carbamate as the HCl salt. ES/MS: m/z 247.0 [M+H]$^+$.

Preparation of (3S,4R)-4-(2,2-difluoroethoxy)-N-tritylpiperidin-3-amine (A5a)

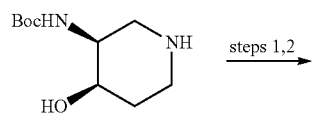

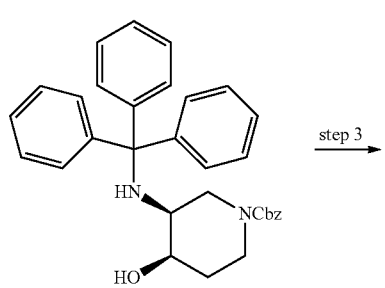

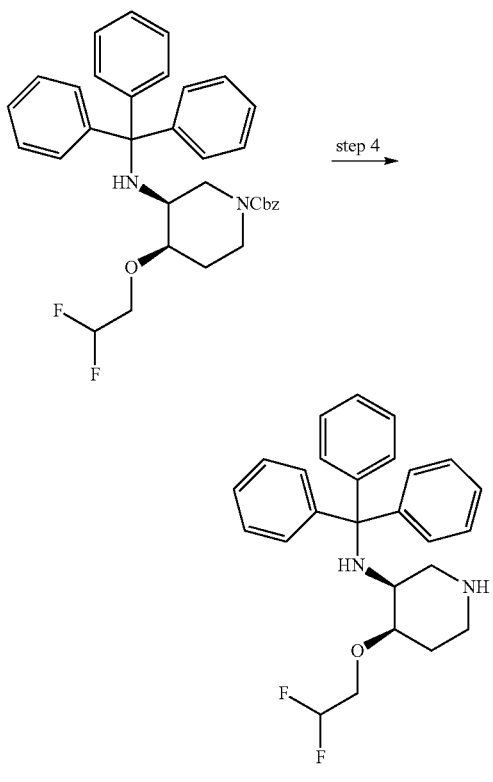

Step 1 tert-Butyl ((3S,4R)-4-hydroxypiperidin-3-yl)carbamate (Pharmablock) (4.98 g, 23 mmol) was dissolved in DCM (100 mL). Triethylamine (10 mL, 71 mmol) and benzyl (2,5-dioxopyrrolidin-1-yl) carbonate (6.05 g, 24.3 mmol) were added. After stirring 24 h, the reaction mixture was diluted with water and the aqueous phase was acidified with hydrochloric acid. The phases were separated, and the aqueous phase was extracted with DCM. The organic phase was concentrated directly onto silica gel. Purification by silica gel chromatography (0-60% acetone in hexanes) provided benzyl (3S,4R)-3-(tert-butoxycarbonylamino)-4-hydroxy-piperidine-1-carboxylate. ES/MS: m/z 350.7 [M+H]$^+$.

Step 2

(3S,4R)-3-(tert-butoxycarbonylamino)-4-hydroxy-piperidine-1-carboxylate (7.86 g, 22.4 mmol) was dissolved in dioxane. 4 M hydrochloric acid in dioxane (56 mL, 224 mmol) was added, and the resulting mixture was stirred at ambient temperature for 48 h. The reaction mixture was concentrated, and the crude product was dissolved in DCM (150 mL). N,N-diisopropylethylamine (19.5 mL, 112 mmol) was added followed by [chloro(diphenyl)methyl]benzene (7.19 g, 25.8 mmol). The reaction mixture was stirred until LCMS indicated complete conversion and was then diluted with EtOAc and water. The phases were separated, and the organic phase was dried over Na$_2$SO$_4$, filtered, and concentrated. Purification by silica gel (20-70% EtOAc in hexanes) provided benzyl (3S,4R)-4-hydroxy-3-(tritylamino)piperidine-1-carboxylate. ES/MS: m/z 515.3 [M+Na]$^+$.

Step 3

Benzyl (3S,4R)-4-hydroxy-3-(tritylamino)piperidine-1-carboxylate (200 mg, 0.41 mmol) was dissolved in DMF (2 mL) under N$_2$. 60% NaH dispersion in mineral oil (19.5 mg, 0.487 mmol) was added and the mixture was stirred several minutes. 2,2-difluoroethyl trifluoromethanesulfonate (0.11 mL, 0.832 mmol) was added. After 3.5 h, an additional portion of 60% NaH dispersion in mineral oil (11 mg, 0.28 mmol) and 2,2-difluoroethyl trifluoromethanesulfonate (0.05 mL, 0.4 mmol) were added. After stirring an additional 1 h, the mixture was partitioned between EtOAc and sat. aq. NH$_4$Cl. The organic phase was washed with water, dried over Na$_2$SO$_4$, filtered and concentrated to afford a crude residue that was purified by silica gel chromatography (0-50% EtOAc in hexanes) to afford benzyl (3S,4R)-4-(2,2-difluoroethoxy)-3-(tritylamino)piperidine-1-carboxylate. $^1$H NMR (400 MHz, DMSO-d$_6$) δ 7.60-7.10 (m, 21H), 6.07 (tt, J=55.0, 3.7 Hz, 1H), 5.00 (s, 2H), 4.14-3.86 (m, 1H), 3.67-3.56 (m, 1H), 3.58-3.40 (m, 1H), 3.20-2.97 (m, 1H), 2.97-2.64 (m, 2H), 2.48-2.43 (m, 1H), 1.95-1.71 (m, 1H), 1.69-1.53 (m, 1H), 1.08-0.91 (m, 1H).

Step 4

Benzyl (3S,4R)-4-(2,2-difluoroethoxy)-3-(tritylamino)piperidine-1-carboxylate (130 mg, 0.234 mmol) was dissolved in EtOAc. Pd/C (10%) (50 mg, 0.047 mmol) was added and the vessel was purged with H$_2$. The reaction mixture was stirred under 1 atm H$_2$ until full consumption of starting material was observed, at which time the reaction mixture was filtered. Filtrate was concentrated to afford (3S,4R)-4-(2,2-difluoroethoxy)-N-tritylpiperidin-3-amine. ES/MS: m/z 422.7 [M+H]$^+$.

(3S,4R)-4-propoxy-N-tritylpiperidin-3-amine (A5b)

Prepared following a similar procedure to A5a using propyl iodide instead of 2,2-difluoroethyl trifluoromethanesulfonate. ES/MS: m/z 401.2 [M+H]$^+$.

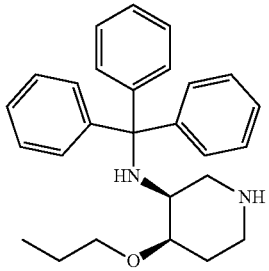

A5b (3S,4R)-4-ethoxy-N-tritylpiperidin-3-amine (A5c)

Prepared following a similar procedure to A5a using ethyl iodide instead of 2,2-difluoroethyl trifluoromethanesulfonate. ES/MS: m/z 387.2 [M+H]$^+$.

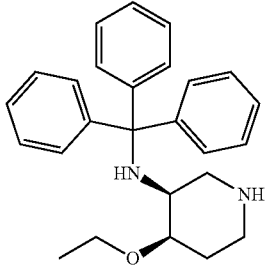

A5c (3S,4R)-4-(cyclopropylmethoxy)-N-tritylpiperidin-3-amine (A5d)

Prepared following a similar procedure to A5a using (bromomethyl)cyclopropane instead of 2,2-difluoroethyl trifluoromethanesulfonate. ES/MS: m/z 412.65 [M+H]$^+$.

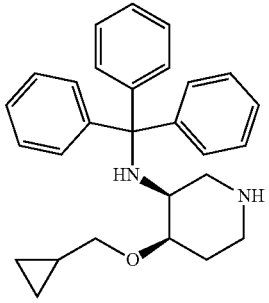

A5d (3S,4R)-4-((3-fluorobicyclo[1.1.1]pentan-1-yl)methoxy)-N-tritylpiperidin-3-amine (A5e)

Prepared following a similar procedure to A5a using 1-(bromomethyl)-3-fluorobicyclo[1.1.1]pentane instead of 2,2-difluoroethyl trifluoromethanesulfonate. ES/MS: m/z 457.56 [M+H]$^+$.

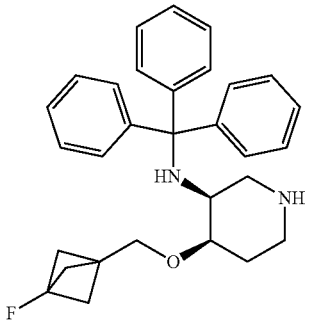

A5e

(3S,4R)-4-(2-methoxyethoxy)-N-tritylpiperidin-3-amine (A5f)

Prepared following a similar procedure to A5a using 1-iodo-2-methoxyethane instead of 2,2-difluoroethyl trifluoromethanesulfonate. ES/MS: m/z 417.81 [M+H]$^+$.

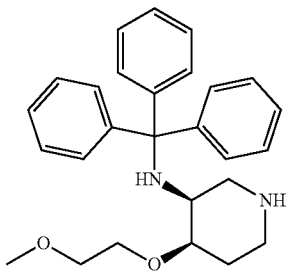

A5f

(3S,4R)-4-(methoxy-d$_3$)-N-tritylpiperidin-3-amine (A5g)

Prepared following a similar procedure to A5a using iodomethane-d$_3$ instead of 2,2-difluoroethyl trifluoromethanesulfonate. ES/MS: m/z 375.70 [M+H]$^+$.

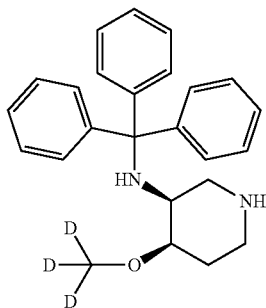

A5g

Preparation of tert-butyl ((2R,3R)-2-methylpiperidin-3-yl)carbamate (A6)

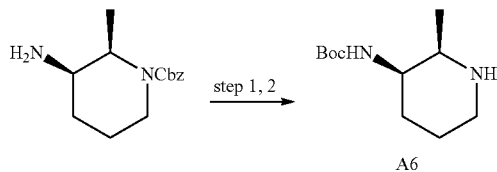

A6

Step 1

Benzyl (2R,3R)-3-amino-2-methyl-piperidine-1-carboxylate (from Synthonix) (7.4 g, 21 mmol) was dissolved in DCM (100 mL). Hunig's base (6.5 mL, 42 mmol) was added followed by tert-butoxycarbonyl tert-butyl carbonate (4.5 g, 21 mmol). The reaction mixture was stirred 24 h and was then partitioned between DCM and aq. HCl. The phases were separated, and the aqueous phase was extracted with DCM. The combined organic phase was dried over Na$_2$SO$_4$, filtered, and concentrated to afford crude benzyl (2R,3R)-3-((tert-butoxycarbonyl)amino)-2-methylpiperidine-1-carboxylate material that was used directly in step 2.

Step 2

Benzyl (2R,3R)-3-((tert-butoxycarbonyl)amino)-2-methylpiperidine-1-carboxylate (ca. 21 mmol) was dissolved in THF (200 mL). Palladium on carbon (10% dry basis, 50% total water content) (7.4 g, 3.5 mmol) was added and the vessel was purged with 1 atm H$_2$. After stirring 18 h, the reaction mixture was filtered through a pad of Celite, and the filtrate was concentrated to afford tert-butyl N-[(2R,3R)-2-methyl-3-piperidyl]carbamate. $^1$H NMR (400 MHz, DMSO-d$_6$) δ 6.30 (d, J=9.1 Hz, 1H), 3.49-3.39 (m, 1H), 2.87-2.77 (m, 1H), 2.76-2.65 (m, 1H), 2.49-2.42 (m, 1H), 1.73-1.58 (m, 1H), 1.56-1.43 (m, 2H), 1.39 (s, 9H), 1.33-1.20 (m, 1H), 0.87 (d, J=6.5 Hz, 3H).

Preparation of tert-butyl rac-(4aR,8aR)-octahydro-1,7-naphthyridine-1(2H)-carboxylate (A7)

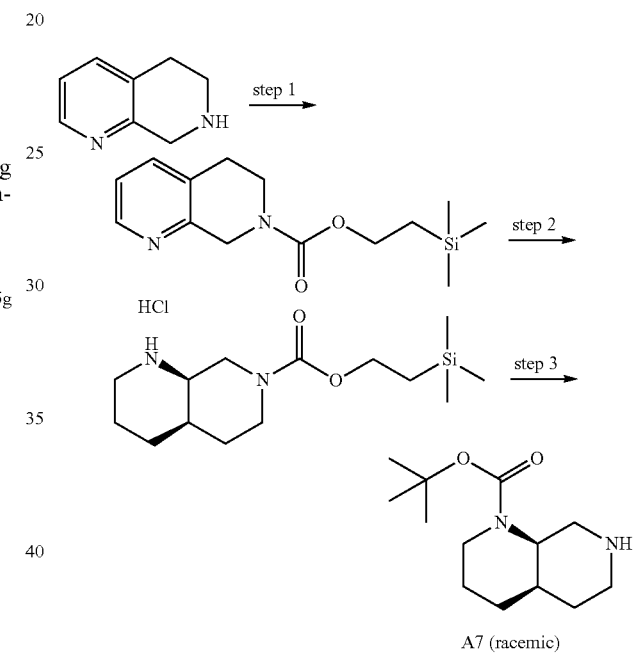

A7 (racemic)

Step 1

To a mixture of 5,6,7,8-tetrahydro-1,7-naphthyridine dihydrochloride (500 mg, 2.41 mmol) and 1-[2-(Trimethylsilyl)ethoxycarbonyloxy]pyrrolidin-2,5-dione (1.22 g, 4.70 mmol) in DCM (20 mL) was added DIPEA (1.26 mL, 7.23 mmol) at rt. After stirring overnight, the reaction mixture was concentrated under reduced pressure and the residue purified via silica gel column chromatography (15-60% ethyl acetate/hexanes) to yield 2-(trimethylsilyl)ethyl 5,8-dihydro-1,7-naphthyridine-7(6H)-carboxylate. ES/MS: m/z 278.8 [M+H]$^+$.

Step 2

PtO$_2$ (236 mg, 1.04 mmol) was added to a mixture of 2-(trimethylsilyl)ethyl 5,8-dihydro-1,7-naphthyridine-7(6H)-carboxylate (672 mg, 2.41 mmol) in ethanol (25 mL) and aqueous HCl solution (6 N, 0.5 mL, 3 mmol) and the reaction mixture was hydrogenated under an atmosphere of hydrogen for 15 h. The reaction mixture was filtered over celite and the filtrate was concentrated and dried in vacuo to yield rac-2-(trimethylsilyl)ethyl (4aR,8aR)-octahydro-1,7-naphthyridine-7(1H)-carboxylate hydrochloride. ES/MS: m/z 285.0 [M+H]$^+$.

Step 3

To a solution of rac-2-(trimethylsilyl)ethyl (4aR,8aR)-octahydro-1,7-naphthyridine-7(1H)-carboxylate hydrochloride (350 mg, 1.09 mmol) and triethylamine (0.38 mL, 2.73 mmol) in DCM (8 mL) was added di-tert-butyl dicarbonate (358 mg, 1.64 mmol) and DMAP (21 mg, 0.174 mmol). After 5 h, the reaction mixture was diluted with water and the layers were separated. The aqueous was extracted with DCM and the combined organics washed with 1 N HCl, dried (MgSO$_4$), filtered and concentrated. The resulting residue was dissolved in THF (6 mL) and a solution of TBAF in THF (1M, 1.95 mL, 1.95 mmol) was added. After 10 minutes, the reaction mixture was heated at 55° C. overnight. After cooling to rt, the reaction mixture was diluted with DCM, ethyl acetate, and water. The layers were separated and the organics were dried (MgSO$_4$), filtered, and concentrated under reduced pressure to yield tert-butyl rac-(4aR,8aR)-octahydro-1,7-naphthyridine-1(2H)-carboxylate. ES/MS: m/z 240.9 [M+H]$^+$.

Preparation of tert-butyl (R)-(1-methylhexahydropyridazin-4-yl)carbamate (A8)

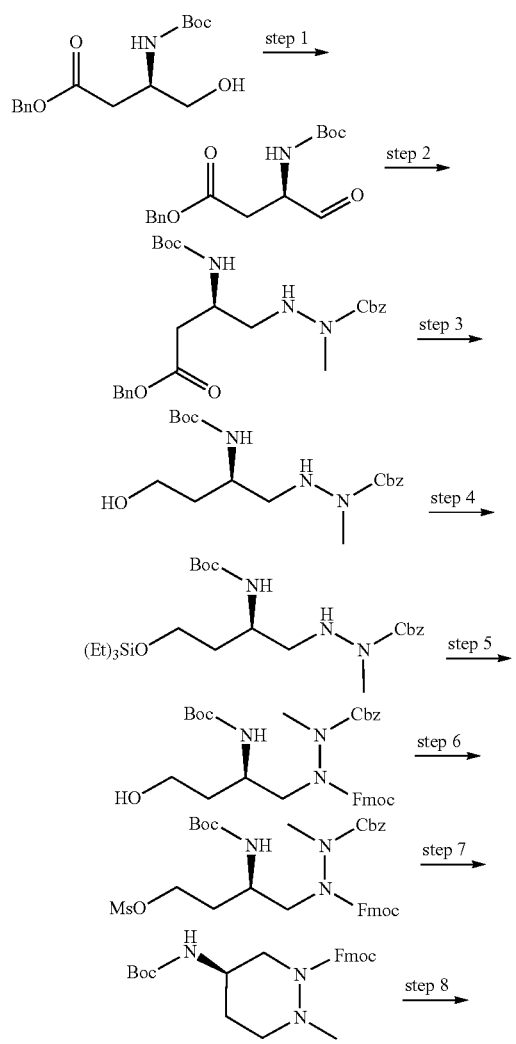

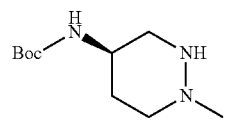

A8

Step 1

To a solution of benzyl (3R)-3-(tert-butoxycarbonylamino)-4-hydroxy-butanoate (3.4 g, 10.99 mmol) in dichloromethane (34 mL) was added Dess-Martin periodinane (5.13 g, 12.09 mmol) in several portions over 15 minutes. After stirring for 4 h, the mixture was concentrated, diluted with ethyl acetate (50 mL), and washed with 1 M aqueous NaS$_2$O$_3$ (50 mL), followed by 1 M NaHCO$_3$(aq, 50 mL). The organic layer was dried with Na$_2$SO$_4$, filtered, and concentrated under vacuum. The crude product was purified by silica chromatography using ethyl acetate in hexanes to afford benzyl (R)-3-((tert-butoxycarbonyl)amino)-4-hydroxybutanoate. $^1$H NMR (400 MHz, Methanol-d4) δ 9.55 (s, 1H), 7.37 (td, J=4.7, 1.7 Hz, 5H), 5.16 (d, J=1.0 Hz, 2H), 4.30 (ddd, J=7.8, 5.2, 2.4 Hz, 1H), 2.95 (dd, J=16.5, 5.4 Hz, 1H), 2.76 (dd, J=16.4, 7.2 Hz, 1H), 1.46 (s, 9H).

Step 2

A solution of benzyl (R)-3-((tert-butoxycarbonyl)amino)-4-hydroxybutanoate (3.4 g, 11.06 mmol), benzyl 1-methylhydrazine-1-carboxylate (1.99 g, 11.06 mmol), and acetic acid (1.99 g, 33.19 mmol) was stirred at ambient temperature for 30 minutes. To the mixture was added sodium cyanoborohydride (2.78 g, 44.25 mmol) over 5 minutes and the mixture was stirred at ambient temperature for 1 hour followed by heating at 40° C. for 30 minutes. The mixture was concentrated, diluted with EtOAc (50 ml), and washed with 1 M aqueous K$_2$HPO$_4$ (50 ml). The organic layer was dried with Na$_2$SO$_4$, filtered, and concentrated. Crude benzyl (R)-3-((tert-butoxycarbonyl)amino)-4-oxobutanoate was taken to next step without further purification. $^1$H NMR (400 MHz, Methanol-d4) δ 7.44-7.27 (m, 10H), 5.18-5.03 (m, 4H), 4.05-3.92 (m, 1H), 3.06 (s, 3H), 3.00-2.92 (m, 1H), 2.92-2.81 (m, 1H), 2.79-2.66 (m, 1H), 2.61-2.43 (m, 1H), 1.43 (s, 9H). ES/MS: m/z 472.2 [M+H]$^+$.

Step 3

To a solution of benzyl (R)-3-((tert-butoxycarbonyl)amino)-4-oxobutanoate (5.2 g, 11.03 mmol) in MeTHF (11 mL) was added 2 M LiBH$_4$ in THF (11 mL). After stirring for 1 h, the mixture was carefully quenched with 4N NH$_4$Cl (aq, 20 ml) and stirred for 1 h. The organic layer was dried with Na$_2$SO$_4$, filtered, and concentrated under vacuum. The crude product was purified by silica chromatography using EtOAc in hexane to afford benzyl (R)-2-(2-((tert-butoxycarbonyl)amino)-4-hydroxybutyl)-1-methylhydrazine-1-carboxylate. ES/MS: m/z 368.2 [M+H]$^+$.

Step 4

To a solution of benzyl (R)-2-(2-((tert-butoxycarbonyl)amino)-4-hydroxybutyl)-1-methylhydrazine-1-carboxylate (2.5 g, 6.8 mmol) and EtN(i-Pr)$_2$ (1.77 ml, 10.21 mmol) in dichloromethane (30 mL) was added triethylsilyl trifluoromethanesulfonate (2.15 ml, 9.53 mmol) at −78° C. The mixture was warmed to ambient over 1 h. The mixture was washed with water (30 mL) and the organic layer was dried with Na$_2$SO$_4$, filtered, and concentrated under vacuum. The product was purified by silica chromatography using ethyl acetate in hexane. The partially purified product was refluxed in methanol for 1 h. The mixture was concentrated under vacuum and repurified by silica chromatography using ethyl acetate in hexane to afford benzyl (R)-2-(2-((tert-butoxycarbonyl)amino)-4-((triethylsilyl)oxy)butyl)-1-methylhydrazine-1-carboxylate. $^1$H NMR (400 MHz, Chloroform-d) δ 7.43-7.28 (m, 6H), 5.23-5.05 (m, 3H), 4.70 (s, 1H), 3.79-3.53 (m, 2H), 3.09 (s, 3H), 3.02-2.84 (m, 2H), 1.86-1.52 (m, 2H), 1.43 (s, 9H), 0.95 (t, J=7.9 Hz, 9H), 0.59 (q, J=8.0 Hz, 6H). ES/MS: m/z 482.3 [M+H]$^+$.

Step 5

To a solution of benzyl (R)-2-(2-((tert-butoxycarbonyl)amino)-4-((triethylsilyl)oxy)butyl)-1-methylhydrazine-1-carboxylate (2.7 g, 5.61 mmol) and EtN(i-Pr)$_2$ (1.46 ml, 8.41 mmol) in dichloromethane (10 mL) was added FmocCl (1.89 g, 7.29 mmol) at 0° C. The mixture was warmed to ambient temperature and stirred for 2 h. To the reaction was added triethylamine trihydrofluoride (1.8 g, 11.21 mmol). After the stirring for 1 h, the crude product was purified by silica chromatography using EtOAc in hexane to afford 1-((9H-fluoren-9-yl)methyl) 2-benzyl (R)-1-(2-((tert-butoxycarbonyl)amino)-4-hydroxybutyl)-2-methylhydrazine-1,2-dicarboxylate. ES/MS: m/z 590.0 [M+H]$^+$.

Step 6

To a solution of 1-((9H-fluoren-9-yl)methyl) 2-benzyl (R)-1-(2-((tert-butoxycarbonyl)amino)-4-hydroxybutyl)-2-methylhydrazine-1,2-dicarboxylate (2.4 g, 4.07 mmol) and EtN(i-Pr)$_2$ (0.85 ml, 4.88 mmol) in dichloromethane (10 ml) was added methanesulfonyl chloride (0.35 ml, 4.48 mmol) at 0° C. After stirring for 30 minutes, the product was purified by silica chromatography using ethyl acetate in hexane to afford 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate. ES/MS: m/z 568.2 [M+H]$^+$.

Step 7.

A mixture of 1-((9H-fluoren-9-yl)methyl) 2-benzyl (R)-1-(2-((tert-butoxycarbonyl)amino)-4-((methylsulfonyl)oxy)butyl)-2-methylhydrazine-1,2-dicarboxylate (2.3 g, 3.44 mmol) and 10% palladium on carbon (0.18 g, 0.17 mmol) in methanol (20 mL) was stirred for 2 h under 1 atm hydrogen. The mixture was filtered through celite and washed with methanol (10 ml). The filtrate was treated with pyridine (0.28 mL, 3.44 mmol) and stirred for 18 h. The mixture was concentrated under vacuum. The crude product was taken to next step without further purification. ES/MS: m/z 438.0 [M+H]$^+$.

Step 8

Crude (9H-fluoren-9-yl)methyl (R)-5-(((tert-butoxycarbonyl)amino)-2-methyltetrahydropyridazine-1(2H)-carboxylate (0.91 g, 2.1 mmol) in 1:1 dichloromethane:diethylamine (5 mL) was stirred at ambient temperature for 2 h. The mixture was concentrated under vacuum and purified by silica chromatography using methanol in dichloromethane to afford tert-butyl (R)-(1-methylhexahydropyridazin-4-yl)carbamate. $^1$H NMR (400 MHz, Methanol-d4) δ 3.48-3.34 (m, 1H), 3.16-3.08 (m, 1H), 3.03-2.89 (m, 1H), 2.79-2.68 (m, 1H), 2.49 (s, 3H), 2.48-2.41 (m, 1H), 2.01-1.90 (m, 1H), 1.75-1.64 (m, 1H), 1.46 (s, 9H). ES/MS: m/z 216.2 [M+H]$^+$.

Preparation of tert-butyl ((3S,4R)-4-methoxypiperidin-3-yl)(methyl)carbamate (A9)

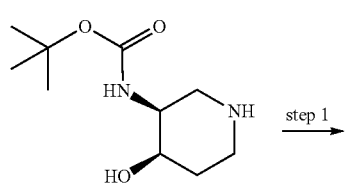

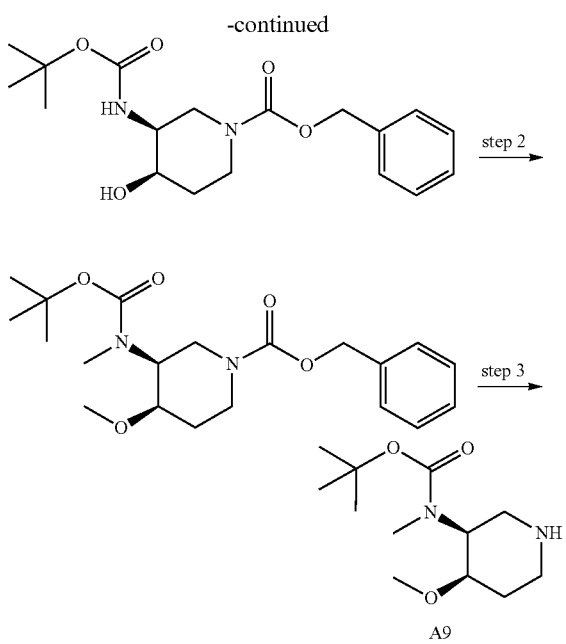

Step 1

To a solution of tert-butyl N-[(3S,4R)-4-hydroxy-3-piperidyl]carbamate (5.0 g, 23 mmol) in DCM (100 mL) was added triethylamine (10 mL, 71 mmol) and benzyl (2,5-dioxopyrrolidin-1-yl) carbonate (6.1 g, 24 mmol). The mixture was allowed to stir at ambient temperature for 24 h. Water and HCl (3 M, 15 mL, 45 mmol) were added, and the product was extracted into DCM, concentrated, and purified by silica chromatography (eluent: 0-60% acetone in hexanes) to give benzyl (3S,4R)-3-(tert-butoxycarbonylamino)-4-hydroxy-piperidine-1-carboxylate as a white foam. ES/MS: m/z 350.7 [M+H]$^+$.

Step 2

To a solution of benzyl (3S,4R)-3-(tert-butoxycarbonylamino)-4-hydroxy-piperidine-1-carboxylate (500 mg, 1.4 mmol) in DMF (4 mL) at 0° C. under N$_2$ was added sodium hydride (60% dispersion in mineral oil, 69 mg, 1.7 mmol). The reaction was removed from ice bath and allowed to stir for 5 minutes, then returned to ice bath. Methyl iodide (0.14 mL, 2.3 mmol) was added. The reaction was allowed to stir for 1 h, then was quenched with water. The mixture was poured into EtOAc and washed with water, then brine. The organic phase was adsorbed to isolute and purified by silica gel chromatography (0-100% EA in hexane) to afford benzyl (3S,4R)-3-(tert-butoxycarbonylamino)-4-methoxy-piperidine-1-carboxylate (also commercially available, see A1.03), and benzyl (3S,4R)-3-[tert-butoxycarbonyl(methyl)amino]-4-methoxy-piperidine-1-carboxylate (used in the next steps). ES/MS: m/z 401.2 [M+Na]$^+$.

Step 3

Benzyl (3S,4R)-3-[tert-butoxycarbonyl(methyl)amino]-4-methoxy-piperidine-1-carboxylate (105 mg, 0.28 mmol) was combined with 10% Pd/C in a mixture of EtOH (2 mL) and EtOAc (2 mL) and treated with H$_2$ gas. After 18 h, the reaction was filtered through celite and the filtrate concentrated to give tert-butyl N-[(3S,4R)-4-methoxy-3-piperidyl]-N-methylcarbamate, which was used directly in subsequent steps.

Preparation of benzyl (3S,4R)-3-amino-4-methoxypiperidine-1-carboxylate (A10)

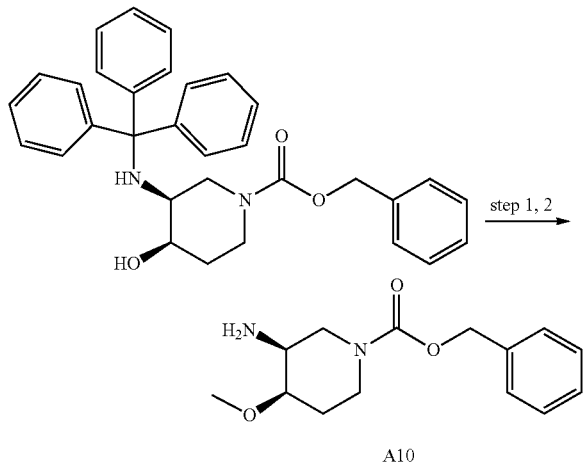

A10

Step 1
To a solution of benzyl (3S,4R)-4-hydroxy-3-(tritylamino)piperidine-1-carboxylate (150 mg, 0.31 mmol, intermediate described in the synthesis of A5a) in DMF (1 mL) was added sodium hydride (60% dispersion in mineral oil, 23 mg, 0.61 mmol). After stirring for 35 minutes, methyl iodide (28 uL, 0.46 mmol) was added. The reaction was allowed to stir for 2 h, then was quenched with water. The mixture was poured into EtOAc and washed with aq. NaHCO$_3$, then brine. The organic phase was adsorbed to isolute and purified by silica gel chromatography (0-100% EA in hexane) to afford benzyl (3S,4R)-4-methoxy-3-(tritylamino)piperidine-1-carboxylate. ES/MS: m/z 529.2 [M+Na]$^+$.

Step 2
Benzyl (3S,4R)-4-methoxy-3-(tritylamino)piperidine-1-carboxylate (26 mg, 0.052 mmol) was dissolved in DCM and treated with TFA at ambient temperature. The resulting mixture was concentrated to give benzyl (3S,4R)-3-amino-4-methoxypiperidine-1-carboxylate, which was used directly in subsequent steps.

Preparation of benzyl rac-((1S,5R,6R)-3-azabicyclo[4.1.0]heptan-5-yl)carbamate (A11a)

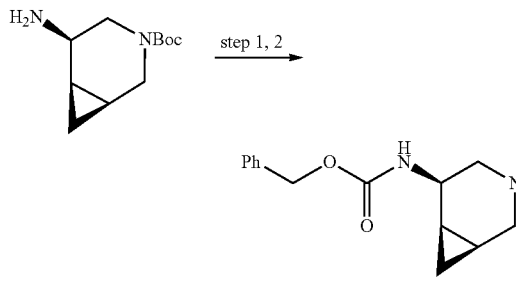

A11a

Step 1
Triethylamine (430 mg, 4.2 mmol) was added to a solution of tert-butyl rac-(1S,5R,6R)-5-amino-3-azabicyclo[4.1.0]heptane-3-carboxylate (300 mg, 1.41 mmol) and N-(Benzyloxycarbonyloxy)succinimide (481 mg, 1.70 mmol). The mixture was stirred overnight then evaporated to dryness and purified by column chromatography (Hexane, EtOAc 0-15%) to afford tert-butyl rac-(1S,5R,6R)-5-(((benzyloxy)carbonyl)amino)-3-azabicyclo[4.1.0]heptane-3-carboxylate.

Step 2
tert-butyl rac-(1S,5R,6R)-5-(((benzyloxy)carbonyl)amino)-3-azabicyclo[4.1.0]heptane-3-carboxylate was dissolved in DCM (4 mL) and HCl in dioxane (4 N, 1 mL) was added. The resulting mixture was stirred at 35° C. until full conversion of the starting material. The solvents were then evaporated to afford benzyl rac-((1S,5R,6R)-3-azabicyclo[4.1.0]heptan-5-yl)carbamate hydrochloride. $^1$H NMR (400 MHz, DMSO-d6) δ 8.96 (brs, 2H), 7.49 (d, J=8.2 Hz, 1H), 7.42-7.35 (m, 4H), 7.35-7.31 (m, 1H), 5.05 (s, 2H), 4.40-4.29 (m, 1H), 3.52-3.42 (m, 1H), 3.07 (dd, J=12.6, 6.1 Hz, 1H), 2.88-2.79 (m, 1H), 2.27 (t, J=11.9 Hz, 1H), 1.43-1.22 (m, 2H), 0.77-0.72 (m, 1H), 0.67-0.58 (m, 1H).

benzyl rac-((1R,5R,6S)-3-azabicyclo[4.1.0]heptan-5-yl)carbamate (A11b)

Prepared following a similar procedure to A11a starting with tert-butyl rac-(1R,5R,6S)-5-amino-3-azabicyclo[4.1.0]heptane-3-carboxylate. $^1$H NMR (400 MHz, DMSO-d6) δ 8.89 (brs, 2H), 7.80 (d, J=7.8 Hz, 1H), 7.44-7.21 (m, 5H), 5.14-4.98 (m, 2H), 4.00-3.91 (m, 1H), 3.41 (dd, J=13.0, 7.1 Hz, 1H), 3.12-2.87 (m, 2H), 2.78 (dd, J=13.0, 5.7 Hz, 1H), 1.28-1.03 (m, 2H), 0.80 (dt, J=9.0, 4.5 Hz, 1H), 0.62-0.56 (m, 1H).

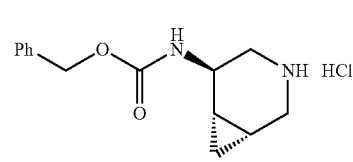

A11b

Preparation of benzyl ((1R,2S,3R,5S)-3-hydroxy-8-azabicyclo[3.2.1]octan-2-yl)carbamate (A12)

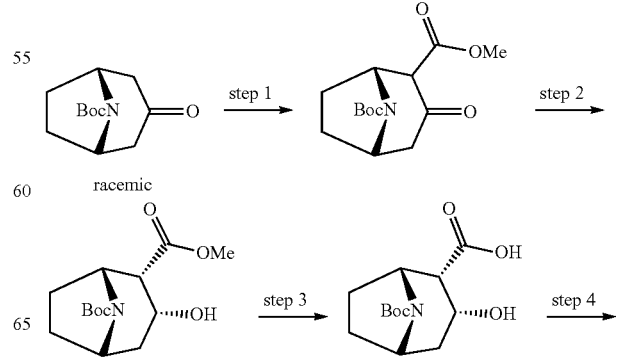

-continued

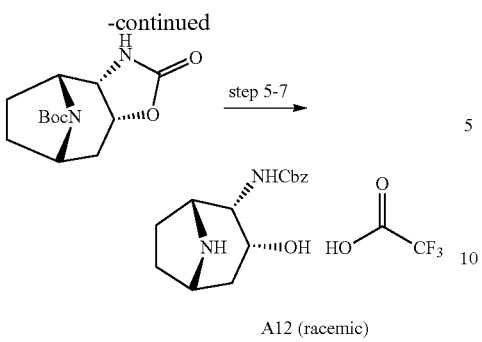

A12 (racemic)

Step 1

A solution of dimethyl carbonate (4.0 g, 44 mmol) in toluene (20 mL) was added dropwise (using an addition funnel) to a suspension of NaH (60% in mineral oil, 1.06 g, 44 mmol) in toluene (60 mL) at room temperature under argon. The mixture was heated to 80° C. upon completion of the addition and MeOH (0.5 mL) followed by a solution of Boc-tropinone (5 g, 22 mmol) in toluene (20 mL) were added dropwise via the addition funnel. The resulting mixture was stirred at 80° C. overnight. Water (4 mL) was added and the mixture was evaporated to dryness. The thick mixture was suspended in DCM and silica was added. After evaporation to dryness the solid was purified by column over silica gel (hexanes/EtOAc, 20% to 40%) to afford 8-(tert-butyl) rac-2-methyl (1R,5R)-3-oxo-8-azabicyclo[3.2.1]octane-2,8-dicarboxylate. $^1$H NMR (400 MHz, Chloroform-d) δ 11.81 (s, 0.78H enol), 4.85 (brs, 1H), 4.56 (brs, 1H), 4.38 (brs, 1H), 3.80 (s, 2.34H enol), 3.73 (s, 0.66H ketone), 3.27 (s, 0.22H ketone), 3.10-3.03 (m, 0.22H ketone), 2.94 (brs, 1H), 2.41 (dd, J=15.1, 1.9 Hz, 0.44H, ketone), 2.36-1.96 (m, 2.66H), 1.92-1.82 (m, 0.78H, enol), 1.50 (s, 2H ketone), 1.46 (s, 7H enol).

Step 2

A solution of 8-(tert-butyl) rac-2-methyl (1R,5R)-3-oxo-8-azabicyclo[3.2.1]octane-2,8-dicarboxylate (2.5 g, 9 mmol) in methanol (27 mmol) was cooled to −20° C. and sodium borohydride (367 mg, 10 mmol) was added in small portions over 15 minutes. The mixture was warmed up to 0° C. over 2 h. LC/MS analysis showed full conversion and a solution of saturated ammonium chloride (30 mL) was added followed by DCM (60 mL). After usual work-up the organic layer was evaporated to dryness and the residue was purified by column chromatography over silica gel (Hexanes/EtOAc 5 to 70%). The top spot was found to be 8-(tert-butyl) 2-methyl rac-(1R,2S,3R,5R)-3-hydroxy-8-azabicyclo[3.2.1]octane-2,8-dicarboxylate. $^1$H NMR (400 MHz, Chloroform-d) δ 4.51 (brs, 1H), 4.40 (t, J=4.4 Hz, 1H), 4.20 (brs, 1H), 3.78 (s, 3H), 3.32 (s, 1H), 2.92 (brs, 1H), 2.24-2.12 (m, 2H), 2.09-1.82 (m, 3H), 1.48 (s, 9H).

Step 3

A solution of lithium hydroxide (2N in water, 5 mL) was added to a solution of 8-(tert-butyl) 2-methyl rac-(1R,2S,3R,5R)-3-hydroxy-8-azabicyclo[3.2.1]octane-2,8-dicarboxylate (1.43 g, 5 mmol) in THF (40 mL). The resulting biphasic mixture was stirred vigorously at room temperature until the starting ester was fully consumed as judged by TLC analysis. The reaction was then quenched with HCl (2 N, 5.5 mL) and DCM was added (100 mL) followed by distilled water (30 mL). After work-up, the organic layer was dried over anhydrous sodium sulfate and evaporated to dryness to afford rac-(1R,2S,3R,5R)-8-(tert-butoxycarbonyl)-3-hydroxy-8-azabicyclo[3.2.1]octane-2-carboxylic acid which was used without further purification.

Step 4

Crude rac-(1R,2S,3R,5R)-8-(tert-butoxycarbonyl)-3-hydroxy-8-azabicyclo[3.2.1]octane-2-carboxylic acid from above (ca. 1 mmol) was suspended in toluene (4 mL) and DPPA (1 mmol) was added. Triethylamine (1 mmol) was added and the mixture was stirred 80° C. overnight. LCMS shows the desired product mass and TLC analysis (Hex: EtOAc 1:1) using ninhydrin stain reveals the desired product. The crude was directly purified by silica gel (Hex: EtOAc 5% to 60%) to provide tert-butyl rac-(3aS,4R,7R,8aR)-2-oxooctahydro-2H-4,7-epiminocyclohepta[d] oxazole-9-carboxylate. $^1$H NMR (400 MHz, Chloroform-d) δ 6.00 (brs, 1H), 4.69 (t, J=6.2 Hz, 1H), 4.29 (brs, 1H), 4.21 (brs, 1H), 3.93 (brs, 1H), 2.21 (brs, 1H), 2.16-1.95 (m, 2H), 1.98-1.95 (m, 3H), 1.47 (s, 9H).

Step 5

LiOH (840 mg, 20 mmol) was added to a solution of (tert-butyl rac-(3aS,4R,7R,8aR)-2-oxooctahydro-2H-4,7-epiminocyclohepta[d]oxazole-9-carboxylate (1.07 g, 4 mmol) in THF/MeOH (1:2, 20 mL) and the reaction vessel was capped. The reaction was then heated at 90° C. for 48 h. After cooling the reaction to room temperature, excess acetic acid was added and the mixture was stirred for 15 minutes before silica (8 g) was added. After evaporation to dryness the residue was purified by column chromatography over silica gel (DCM/MeOH 0-10%) to afford tert-butyl rac-(1R,2S,3R,5S)-2-amino-3-hydroxy-8-azabicyclo[3.2.1]octane-8-carboxylate.

Step 6

Triethylamine (1.11 g, 10.8 mmol) was added to a solution of tert-butyl rac-(1R,2S,3R,5S)-2-amino-3-hydroxy-8-azabicyclo[3.2.1]octane-8-carboxylate (872 mg, 3.6 mmol) and N-(Benzyloxycarbonyloxy)succinimide (1.22 g, 4.3 mmol). The mixture was stirred overnight then evaporated to dryness and purified by column chromatography (Hexane, EtOAc 0-30%) to afford tert-butyl rac-(1R,2S,3R,5S)-2-(((benzyloxy)carbonyl)amino)-3-hydroxy-8-azabicyclo[3.2.1]octane-8-carboxylate.

Step 7 tert-Butyl rac-(1R,2S,3R,5S)-2-(((benzyloxy)carbonyl)amino)-3-hydroxy-8-azabicyclo[3.2.1]octane-8-carboxylate (1.19 g, 3.17 mmol) was dissolved in DCM (12 mL) and TFA (1 mL) was added. The mixture was stirred until full conversion of the starting material and then evaporated to dryness to afford benzyl ((1R,2S,3R,5S)-3-hydroxy-8-azabicyclo[3.2.1]octan-2-yl)carbamate. $^1$H NMR (400 MHz, DMSO-d6) δ 8.87 (s, 1H), 8.81 (s, 1H), 7.44-7.36 (m, 4H), 7.37-7.32 (m, 1H), 7.18 (d, J=8.3 Hz, 1H), 5.40 (brs, 1H), 5.07 (s, 2H), 4.02-3.86 (m, 3H), 3.80-3.75 (m, 1H), 2.48-2.41 (m, 1H), 2.24-2.16 (m, 1H), 2.12-1.98 (m, 1H), 1.94-1.80 (m, 2H), 1.77-1.62 (m, 1H).

Preparation of (3S,4R)-4-(difluoromethoxy)-N-trityl-piperidin-3-amine (A13)

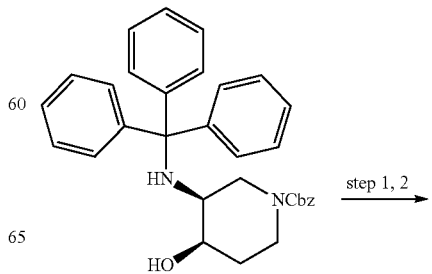

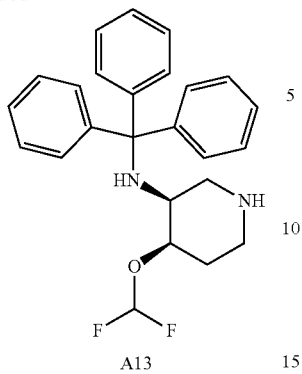

A13

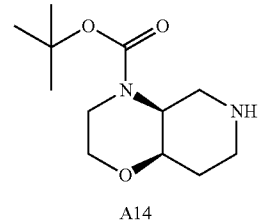

A14

Step 1:

benzyl (3S,4R)-4-hydroxy-3-(tritylamino)piperidine-1-carboxylate (500 mg, 1.0 mmol, intermediate described in the synthesis of A5a) was dissolved in DCM (0.8 mL) and water (0.8 mL). [bromo(difluoro)methyl]-trimethyl-silane (0.48 mL, 3.1 mmol) was added followed by potassium acetate (600 mg, 6 mmol). The reaction mixture was stirred overnight and was then partitioned between DCM and water. Phases were separated, and the organic phase was dried over $Na_2SO_4$, filtered, and concentrated. Purification by silica gel provided benzyl (3S,4R)-4-(difluoromethoxy)-3-(tritylamino)piperidine-1-carboxylate. ES/MS: m/z 546.6 $[M+H]^+$.

Step 2:

Benzyl (3S,4R)-4-(difluoromethoxy)-3-(tritylamino)piperidine-1-carboxylate (89 mg, 0.16 mmol) was dissolved in EtOAc (2 mL) and Pd/C (10% Pd loading) (60 mg, 0.056 mmol) was added. The reaction was stirred for 2 h, and was then filtered and concentrated to afford (3S,4R)-4-(difluoromethoxy)-N-trityl-piperidin-3-amine. ES/MS: m/z 408.5 $[M+H]^+$.

Preparation of tert-butyl (4aS,8aR)-octahydro-4H-pyrido[4,3-b][1,4]oxazine-4-carboxylate (A14)

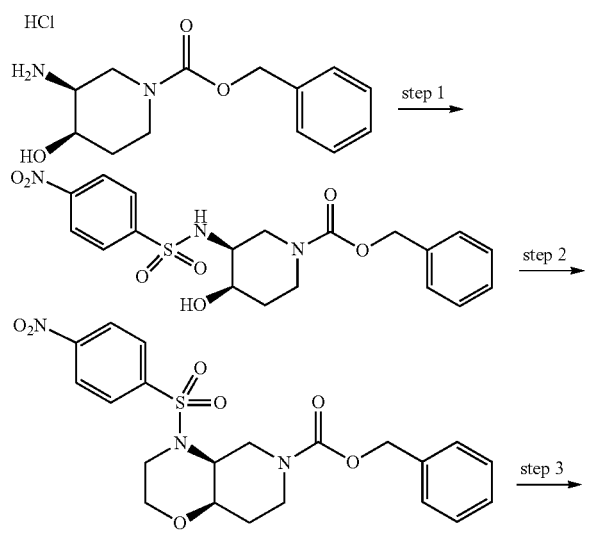

Step 1

To a cooled solution of benzyl (3S,4R)-3-amino-4-hydroxypiperidine-1-carboxylate hydrochloride (350 mg, 1.22 mmol) and triethylamine (0.46 mL, 3.30 mmol) in DCM (7 mL) at 0° C. was added 4-nitrobenzenesulfonyl chloride (300 mg, 1.35 mmol). After 5 minutes, the reaction mixture was warmed to rt. After 30 minutes, the reaction mixture was diluted with DCM and water, and layers separated. The aqueous layer was extracted with DCM. The combined organic layers were dried ($MgSO_4$), filtered, and concentrated under reduced pressure to yield benzyl (3S,4R)-4-hydroxy-3-((4-nitrophenyl)sulfonamido)piperidine-1-carboxylate, that was used in the next step without purification. ES/MS: m/z 240.9 $[M+H]^+$.

Step 2

To a cooled solution of benzyl (3S,4R)-4-hydroxy-3-((4-nitrophenyl)sulfonamido)piperidine-1-carboxylate (345 mg, 0.742 mmol) in DCM (40 mL) at 0° C., was added sodium hydride (60.0% dispersion, 160 mg, 4.00 mmol). After 5 minutes, (2-bromoethyl)diphenylsulfonium trifluoromethanesulfonate (880 mg, 1.99 mmol) was added. The reaction mixture was stirred at 0° C., slowly warming as ice melts. After stirring overnight, triethylamine (0.270 mL, 1.94 mmol) was added. After 8 h, the reaction mixture was diluted with DCM and quenched with sat $NH_4Cl$. The layers were separated and the aqueous layer was extracted with DCM. The combined organic layers were dried ($MgSO_4$), filtered, and concentrated under reduced pressure. The resulting residue was purified via silica gel column chromatography (0-65% ethyl acetate/hexanes) to yield the desired benzyl (4aS,8aR)-4-((4-nitrophenyl)sulfonyl)hexahydro-2H-pyrido[4,3-b][1,4]oxazine-6(5H)-carboxylate. ES/MS: m/z 461.7 $[M+H]^+$.

Step 3

To a solution of benzyl (4aS,8aR)-4-((4-nitrophenyl)sulfonyl)hexahydro-2H-pyrido[4,3-b][1,4]oxazine-6(5H)-carboxylate (166 mg, 0.360 mmol) in DMF (3 mL) at rt was added thioglycolic acid (0.060 mL, 0.864 mmol) followed by lithium hydroxide, monohydrate (84.5 mg, 2.01 mmol). After stirring overnight, the reaction mixture was diluted with ethyl acetate and water. The layers were separated and aqueous extracted with ethyl acetate. The combined organics were dried ($MgSO_4$), filtered, and concentrated under reduced pressure. The resulting residue was dissolved in DCM (4 mL) and triethylamine (0.0800 mL, 0.574 mmol), di-tert-butyl dicarbonate (118 mg, 0.541 mmol), and 4-(dimethylamino)pyridine (7.00 mg, 0.0573 mmol) were added. After 2 h, the aqueous workup above was repeated, extracting with DCM. The combined organics washed with 1 N HCl, dried ($MgSO_4$), filtered, and concentrated under reduced pressure. The resulting residue was dissolved in EtOAc. Pd/C, (10.0%, 77.0 mg, 0.0724 mmol) was added and the mixture hydrogenated under atmosphere of hydrogen. After 1 h, the reaction mixture was diluted with ethyl acetate and filtered over celite. The filtrate was concentrated under reduced pressure to yield tert-butyl (4aS,8aR)-octahydro-4H-pyrido[4,3-b][1,4]oxazine-4-carboxylate. ES/MS: m/z 242.9 [M+H]+.

Preparation of benzyl (3S,4S)-3-amino-4-fluoropiperidine-1-carboxylate (A15)

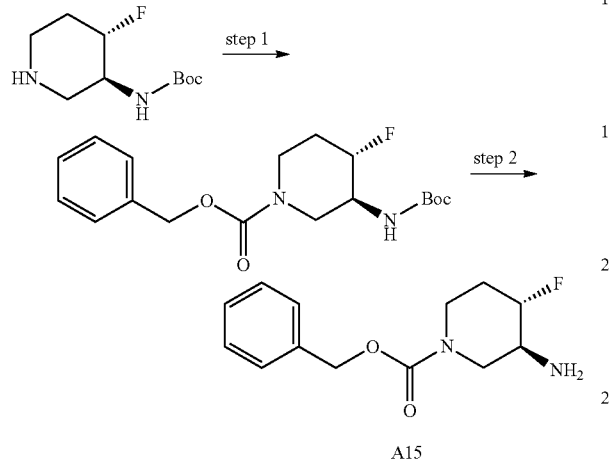

Step 1

Triethylamine (0.19 mL, 1.37 mmol) was added to a solution of tert-butyl N-[(3S,4S)-4-fluoro-3-piperidyl]carbamate (250 mg, 1.15 mmol) in tetrahydrofuran (3 mL), followed by addition of N-(Benzyloxycabronyloxy) succinimide (430 mg, 1.73 mmol). The resulting reaction mixture was stirred at room temperature for 24 h. The reaction mixture was diluted with ethyl acetate and quenched with saturated ammonium chloride solution, extracting with ethyl acetate twice. The combined organics were dried over magnesium sulfate and concentrated to produce the crude product, which was purified via silica gel column chromatography (0-40% ethyl acetate in hexanes) to yield benzyl (3S,4S)-3-(tert-butoxycarbonylamino)-4-fluoro-piperidine-1-carboxylate. ES/MS: m/z 353.74 [M+H]+.

Step 2

Trifluoroacetic acid (1 mL, 13.07 mmol) was added to a solution of benzyl (3S,4S)-3-(tert-butoxycarbonylamino)-4-fluoro-piperidine-1-carboxylate (200 mg, 0.57 mmol) dissolved in dichloromethane (2 mL), and the resulting reaction mixture was stirred at room temperature for 1 h. The reaction mixture was concentrated to yield benzyl (3S,4S)-3-amino-4-fluoro-piperidine-1-carboxylate, which was carried over to the consequent step without further purification assuming quantitative yield. 1H NMR (400 MHz, Chloroform-d) δ 7.42-7.30 (m, 5H), 5.32 (s, 1H), 5.12 (q, J=12.1 Hz, 2H), 4.85 (d, J=48.4 Hz, 1H), 3.90 (s, 1H), 3.39 (d, J=45.7 Hz, 3H), 2.29-2.14 (m, 1H), 1.91-1.75 (m, 1H).

benzyl 2,6-diazaspiro[3.6]decane-6-carboxylate (A15b)

Prepared following a similar procedure to A15 starting with tert-butyl 2,9-diazaspiro[3.6]decane-2-carboxylate. ES/MS: m/z 275.07 [M+H]+.

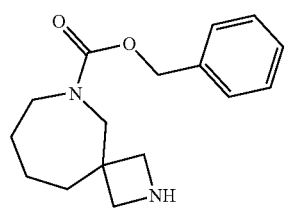

benzyl (3R,5S)-3-amino-5-(difluoromethyl)piperidine-1-carboxylate (A15c)

Prepared following a similar procedure to A15 starting with A1.45.

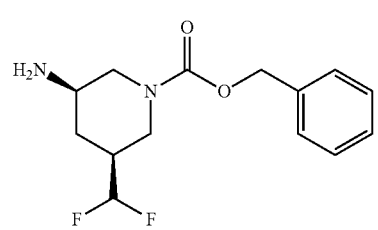

Preparation of tert-butyl ((2S,3R)-2-(hydroxymethyl)piperidin-3-yl)carbamate (A16) and tert-butyl ((2S,3R)-2-(methoxymethyl)piperidin-3-yl)carbamate (A17)

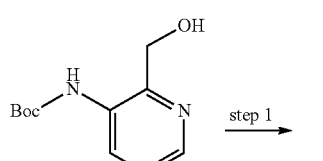

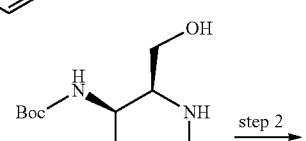

A16 (racemic)

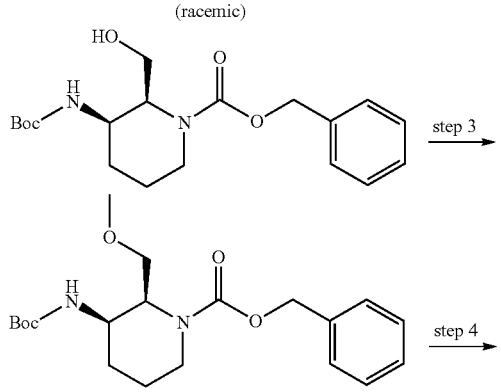

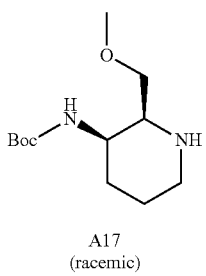

A17
(racemic)

Step 1

Platinum (IV) oxide (46.2 mg, 0.20 mmol) was added to a solution of tert-butyl [2-(hydroxymethyl)pyridin-3-yl]carbamate (135 mg, 0.60 mmol) dissolved in AcOH (2 mL) under nitrogen in a high pressure vessel. The high pressure vessel was evacuated under reduced pressure and placed on a Parr hydrogenation apparatus at 50 psi for 16 h. The reaction mixture was then evacuated under nitrogen, filtered over a bed of silica, and rinsed with copious amounts of methanol. The collected filtrate was flushed through a basic column and concentrated in vacuo to yield tert-butyl N-[2-(hydroxymethyl)-3-piperidyl]carbamate (A16) as acetic acid salt. ES/MS: m/z 231.92 [M+H]$^+$.

Step 2

Triethylamine (0.1 mL, 0.71 mmol) was added to a solution of tert-butyl N-[2-(hydroxymethyl)-3-piperidyl]carbamate (135.5 mg, 0.59 mmol) in tetrahydrofuran (1.5 mL), followed by addition of N-(Benzyloxycabronyloxy)succinimide (220 mg, 0.89 mmol). The resulting reaction mixture was stirred at room temperature for 16 h. The reaction mixture was diluted with ethyl acetate and quenched with saturated ammonium chloride solution, extracting with ethyl acetate twice. The combined organics were dried over magnesium sulfate and concentrated to produce the crude product, which was purified via silica gel column chromatography (0-80% ethyl acetate in hexanes) to yield benzyl 3-(tert-butoxycarbonylamino)-2-(hydroxymethyl)piperidine-1-carboxylate. ES/MS: m/z 365.81 [M+H]$^+$.

Step 3

Potassium hydroxide (9.2 mg, 0.17 mmol) was added to a solution of benzyl 3-(tert-butoxycarbonylamino)-2-(hydroxymethyl)piperidine-1-carboxylate (20 mg, 0.05 mmol) dissolved in dichloromethane (0.5 mL) stirring under an argon stream (9.2 mg) at 0° C. The resulting reaction mixture was stirred at 0° C. for 15 minutes. Next, dimethyl sulfate (10.4 μL, 0.11 mmol) was added dropwise at 0° C., and the mixture was stirred at room temperature over 3 days. The reaction mixture was quenched with ammonium hydroxide and extracted with dichloromethane twice. The collected organics were dried over magnesium sulfate, filtered and concentrated to produce the crude product, which was purified using silica gel column chromatography (0-60% ethyl acetate in hexanes) to yield benzyl 3-(tert-butoxycarbonylamino)-2-(methoxymethyl)piperidine-1-carboxylate. ES/MS: m/z 378.69 [M+H]$^+$.

Step 4

Palladium on carbon (18.9 mg, 0.02 mmol) was added to a solution of benzyl 3-(tert-butoxycarbonylamino)-2-(methoxymethyl)piperidine-1-carboxylate (33.6 mg, 0.09 mmol) dissolved in ethyl acetate (2 mL), and the resulting reaction mixture was subjected to an atmosphere of hydrogen for 16 h. The reaction mixture was filtered to remove the catalyst, washing the filter cake with ethyl acetate. The collected organics were concentrated to yield tert-butyl N-[2-(methoxymethyl)-3-piperidyl]carbamate (19.4 mg, 89% yield) as a 3:1 mixture of cis/trans enantiomers. ES/MS: m/z 245.93 [M+H]$^+$.

Preparation of tert-butyl ((1S,4R,5R)-2-azabicyclo[3.2.1]octan-4-yl)carbamate (A18)

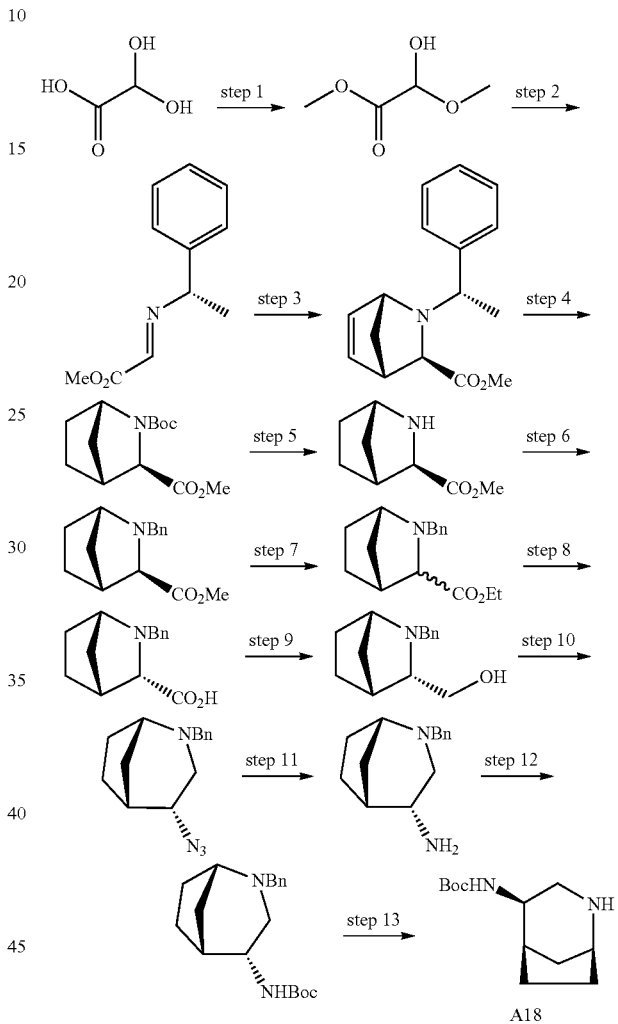

A18

Step 1

A mixture of 2,2-dihydroxyacetic acid (320 g, 3.48 mol) and MeOH (2.24 L) was refluxed for 20 h. The mixture was cooled to rt, concentrated to 1.4 L, and diluted with toluene (1.4 L). The mixture was concentrated to 500 mL, diluted with toluene (1.4 L), and concentrated to 800 mL. The mixture was diluted with toluene to 1.2 L total volume to produce methyl 2-hydroxy-2-methoxyacetate as a 2.3 M solution in toluene (concentration determined by $^1$H NMR). $^1$H NMR (400 MHz, CDCl$_3$) δ 4.79 (s, 1H), 3.74 (s, 3H), 3.41 (s, 3H).

Step 2

The solution of methyl 2-hydroxy-2-methoxyacetate (2.40 L of a 2.3 M soln in toluene, 5.54 mol) was sparged with N$_2$ and then cooled to −10° C. (S)-1-phenylethan-1-amine (714 mL, 5.54 mol) was added while maintaining reaction temperature below 5° C. The mixture was then allowed to warm to rt and was stirred for 2 h. The reaction mixture was diluted with toluene (150 mL) and water (750 mL) and stirred vigorously for 10 min. The mixture was extracted with toluene. The organic layer was washed with brine, dried ($Na_2SO_4$), filtered, and concentrated to yield methyl (S,E)-2-((1-phenylethyl)imino)acetate.
Step 3
A mixture of methyl (S,E)-2-((1-phenylethyl)imino)acetate (1.04 kg, 5.46 mol) in DMA (728 mL) was sparged with $N_2$ and cooled to −10° C. TFA (403 mL, 5.46 mol) was added, maintaining reaction temperature below −5° C. Cyclopentadiene (360 g, 5.46 mol) was added, maintaining reaction temperature below −5° C. Water (10 mL) was added, dropwise. The reaction mixture was stirred at −10° C. for 2 h. The mixture was diluted with heptane (400 mL), quenched with $K_2CO_3$ (360 g in 2 L water), and stirred vigorously for 20 min. The mixture was extracted with heptane. The organic layer was washed with brine, dried ($Na_2SO_4$), filtered, and concentrated. The resulting residue was purified via flash column chromatography on silica gel to afford methyl (1R,3R,4S)-2-((S)-1-phenylethyl)-2-azabicyclo[2.2.1]hept-5-ene-3-carboxylate. $^1$H NMR (400 MHz, $CDCl_3$): δ 7.29-7.21 (m, 5H), 6.43-6.42 (m, 1H), 6.29-6.27 (m, 1H), 4.31 (s, 1H), 3.36 (s, 3H), 3.04 (q, J=6.8 Hz, 1H), 2.92-2.91 (m, 1H), 2.22 (s, 1H), 2.11 (d, J=8.4 Hz, 1H), 1.44-1.41 (m, 4H).
Step 4
To a mixture of Pd(OH)$_2$ (12.0 g, 85.4 mol) in MeOH (1.1 L) was added methyl (1R,3R,4S)-2-((S)-1-phenylethyl)-2-azabicyclo[2.2.1]hept-5-ene-3-carboxylate (110 g, 427 mol) and DIEA (111 mL, 641 mol). The mixture was stirred under 50 psi $H_2$ at 50° C. for 16 h. The mixture was cooled to rt and $Boc_2O$ (139 g, 641 mol) was added. The mixture was stirred under 15 psi $H_2$ at rt for 16 h. The mixture was filtered to remove Pd(OH)$_2$. The filtrate was concentrated and the resulting residue was purified via flash column chromatography on silica gel. The crude product was slurried with EtOAc at 0° C. The resulting solid was collected via filtration to yield 2-(tert-butyl) 3-methyl (1S,3R,4R)-2-azabicyclo[2.2.1]heptane-2,3-dicarboxylate. $^1$H NMR (400 MHz, $CDCl_3$): δ 4.34-4.21 (m, 1H), 3.83-3.71 (m, 1H), 3.70 (s, 3H), 2.65 (s, 1H), 1.92-1.85 (m, 1H), 1.81-1.59 (m, 3H), 1.55-1.31 (m, 10H), 1.24-1.15 (m, 1H).
Step 5
A mixture of 2-(tert-butyl) 3-methyl (1S,3R,4R)-2-azabicyclo[2.2.1]heptane-2,3-dicarboxylate (150 g, 0.58 mol) in HCl solution (734 mL of a 4 M soln in MeOH) was stirred at rt for 3 h. The mixture was concentrated to afford methyl (1S,3R,4R)-2-azabicyclo[2.2.1]heptane-3-carboxylate.
Step 6
To a mixture of $K_2CO_3$ (240 g, 1.74 mol) in MeCN (1.4 L) was added methyl (1S,3R,4R)-2-azabicyclo[2.2.1]heptane-3-carboxylate (90 g, 0.58 mol). The mixture was sparged with $N_2$ and cooled to 0° C. (Bromomethyl)benzene (69 mL, 0.58 mol) was added, dropwise. The reaction mixture was allowed to warm to rt and was stirred for 16 h. The mixture was filtered to remove solids, and the filtrate was concentrated. The residue was purified via flash column chromatography on silica gel to yield methyl (1S,3R,4R)-2-benzyl-2-azabicyclo[2.2.1]heptane-3-carboxylate.
Step 7
To a solution of diisopropylamine (19 mL, 0.13 mol) in THF (1.38 L) at −78° C. was added n-BuLi (56.2 mL of a 2.5 M soln, 0.14 mol). The reaction mixture was stirred at −78° C. for 30 min and was then warmed to −20° C. A solution of methyl (1S,3R,4R)-2-benzyl-2-azabicyclo[2.2.1]heptane-3-carboxylate (30 g, 0.12 mol) in THF (300 mL) was added and the resulting mixture was stirred at −20° C.
for 40 min. The mixture was warmed to −5° C. and sat $NH_4Cl$ soln (1.5 mL) was added. The mixture was stirred at −5° C. for 15 min before it was allowed to warm to rt and stirred for 16 h. Brine was added, and the mixture was extracted with MTBE. The organic layer was concentrated and the resulting residue was purified via flash column chromatography on silica gel to give a mixture of ethyl (1S,3R,4R)-2-benzyl-2-azabicyclo[2.2.1]heptane-3-carboxylate and ethyl (1S,3S,4R)-2-benzyl-2-azabicyclo[2.2.1] heptane-3-carboxylate.
Step 8
The epimeric mixture of ethyl (1S,3R,4R)-2-benzyl-2-azabicyclo[2.2.1]heptane-3-carboxylate and ethyl (1S,3S, 4R)-2-benzyl-2-azabicyclo[2.2.1]heptane-3-carboxylate (20 g, 0.81 mol) in HCl (204 mL of a 4 M aq soln) was refluxed for 16 h. The mixture was cooled to rt and concentrated. The resulting residue was purified via preparative reverse phase HPLC to isolate (1S,3S,4R)-2-benzyl-2-azabicyclo[2.2.1] heptane-3-carboxylic acid. $^1$H NMR (400 MHz, Methanol-$d_4$) δ 7.58-7.55 (m, 2H), 7.44-7.43 (m, 3H), 4.56 (d, J=12.8 Hz, 1H), 4.10-3.97 (m, 2H), 3.96 (t, J=2.0 Hz, 1H), 2.95 (s, 1H), 2.39-2.36 (m, 1H), 1.97-1.87 (m, 3H), 1.73 (m, 1H), 1.51 (m, 1H).
Step 9
To a slurry of (1S,3S,4R)-2-benzyl-2-azabicyclo[2.2.1] heptane-3-carboxylic acid hydrochloride (7.00 g, 26.1 mmol) in THF (130 mL) at 0° C. was added $BH_3$-DMS (12.4 mL, 131 mmol). The mixture was allowed to warm to rt over 16 h. Reaction progress was monitored by LC-MS. The mixture was cooled to 0° C. and $BH_3$-DMS (3.1 mL, 33 mmol) was added. The mixture was allowed to warm to rt overnight and was then cooled to 0° C. and quenched via slow addition of MeOH. The mixture was partially concentrated and then diluted with EtOAc and washed successively with sat $NaHCO_3$ soln and brine. The organic layer was dried ($Na_2SO_4$), filtered, and concentrated. The residue was purified via flash column chromatography to afford ((1S,3S, 4R)-2-benzyl-2-azabicyclo[2.2.1]heptan-3-yl)methanol. $^1$H NMR (400 MHz, $CDCl_3$) δ 7.37-7.28 (m, 4H), 7.25-7.21 (m, 1H), 3.68 (d, J=13.4 Hz, 1H), 3.58 (d, J=13.4 Hz, 1H), 3.48 (dd, J=10.6, 3.9 Hz, 1H), 3.40 (dd, J=10.6, 6.3 Hz, 1H), 3.16-3.08 (m, 1H), 2.84-2.74 (m, 1H), 2.45-2.35 (m, 1H), 1.84-1.69 (m, 2H), 1.60-1.40 (m, 2H), 1.40-1.25 (m, 2H).
Step 10
To a solution of ((1S,3S,4R)-2-benzyl-2-azabicyclo [2.2.1]heptan-3-yl)methanol (0.496 g, 2.28 mmol) and TEA (0.56 mL, 3.99 mmol) in DMF (11 mL) at −40° C. was added $Ms_2O$ (0.497 g, 2.85 mmol). The reaction mixture was stirred at −40° C. and reaction progress was monitored via LC-MS. After 30 min, $Ms_2O$ (0.099 g, 0.568 mmol) was added. The mixture was stirred at −40° C. for 25 min. $NaN_3$ (0.163 g, 2.51 mmol) was added and the mixture was allowed to warm to rt overnight. The mixture was diluted with EtOAc and water. The aq layer was extracted with EtOAc and the combined organic layers were washed successively with water and brine, dried ($Na_2SO_4$), filtered, and concentrated. The residue was purified via flash column chromatography to afford (1S,4R,5R)-4-azido-2-benzyl-2-azabicyclo[3.2.1]octane. $^1$H NMR (400 MHz, $CDCl_3$) δ 7.32-7.21 (m, 5H), 3.67 (ddd, J=10.7, 5.8, 2.9 Hz, 1H), 3.50 (d, J=13.3 Hz, 1H), 3.43 (d, J=13.3 Hz, 1H), 3.14-3.07 (m, 1H), 2.82 (dd, J=11.2, 5.8 Hz, 1H), 2.42-2.35 (m, 1H), 2.00 (t, J=10.9 Hz, 1H), 1.79-1.32 (m, 6H).
Step 11
To LAH (16.8 mL of a 2 M soln in THF, 33.5 mmol) in THF (100 mL) at 0° C. was added a soln of (1S,4R,5R)-4-azido-2-benzyl-2-azabicyclo[3.2.1]octane (4.64 g, 19.1 mmol) in THF (25 mL), slowly. The ice bath was removed and the mixture was stirred at rt for 2 h. The mixture was cooled to 0° C. and quenched via slow addition of water (1.3 mL) followed by NaOH (1.3 mL of a 15 w/v % aq soln) and another portion of water (3.8 mL). The mixture was warmed to rt and was stirred for 15 min before it was dried (Mg$_2$SO$_4$), filtered, and concentrated to afford (1S,4R,5R)-2-benzyl-2-azabicyclo[3.2.1]octan-4-amine. ES/MS: m/z 217.2 [M+H]$^+$.

Step 12

To a solution of (1S,4R,5R)-2-benzyl-2-azabicyclo[3.2.1]octan-4-amine (3.75 g, 17.3 mmol) in DCM (115 mL) was added TEA (3.0 mL, 22 mmol), followed by Boc$_2$O (4.16 g, 19.1 mmol). The mixture was stirred at rt for 16 h. The mixture was diluted with DCM and water. The aq layer was extracted with DCM and the combined organic layers were washed with brine, dried (Na$_2$SO$_4$), filtered, and concentrated. The resulting residue was purified via flash column chromatography to afford tert-butyl ((1S,4R,5R)-2-benzyl-2-azabicyclo[3.2.1]octan-4-yl)carbamate. ES/MS: m/z 317.2 [M+H]$^+$.

Step 13.

A solution of tert-butyl ((1S,4R,5R)-2-benzyl-2-azabicyclo[3.2.1]octan-4-yl)carbamate (0.578 g, 1.83 mmol) in MeOH (12 mL) was sparged with N$_2$. Pd/C (0.116 g of 10% Pd/C) was added and the mixture was stirred under H$_2$ (1 atm) overnight. The mixture was filtered to remove Pd/C and the filtrate was concentrated to afford tert-butyl ((1S,4R,5R)-2-azabicyclo[3.2.1]octan-4-yl)carbamate. $^1$H NMR (400 MHz, CDCl$_3$) δ 4.46-4.33 (m, 1H), 3.66-3.52 (m, 1H), 3.43-3.35 (m, 1H), 3.06 (dd, J=12.8, 5.7 Hz, 1H), 2.44 (dd, J=12.8, 11.0 Hz, 1H), 2.39-2.31 (m, 1H), 1.85-1.70 (m, 1H), 1.67-1.51 (m, 5H), 1.44 (s, 9H).

Preparation of benzyl (3S,4S)-3-amino-4-fluoro-piperidine-1-carboxylate (A19)

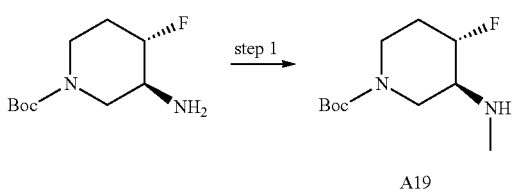 [SMILES: CC(C)(C)OC(=O)N1CC[C@H](F)[C@@H](N)C1 ; CN[C@H]1CN(C(=O)OC(C)(C)C)CC[C@@H]1F ; "A19"]

Step 1 tert-butyl (3S,4S)-3-amino-4-fluoro-piperidine-1-carboxylate (100 mg, 0.46 mmol) was dissolved in MeOH (1 mL). Aqueous formaldehyde (34 uL, 0.46 mmol) was added, followed by 4A molecular sieves (325 mesh, 50 mg). The mixture was stirred for two days, then treated with sodium borohydride (35 mg, 0.92 mmol) and stirred overnight. The reaction was filtered to remove solids and the filtrate concentrated. The resulting residue was dissolved in water and extracted 3× into EtOAc. The combined extracts were washed with brine, dried over Na$_2$SO$_4$, filtered, and concentrated to give tert-butyl (3S,4S)-4-fluoro-3-(methylamino)piperidine-1-carboxylate as a colorless oil. ES/MS: m/z 233.1 [M+H]$^+$.

Preparation of ((3R,4R)-3-(((S)-1-phenylethyl)amino)piperidin-4-yl)methanol (A20)


The synthesis of tert-butyl (3R,4R)-4-(hydroxymethyl)-3-(((S)-1-phenylethyl)amino)piperidine-1-carboxylate is described in J. Med. Chem. 2006, 49, 7843-7853.

Step 1 tert-butyl (3R,4R)-4-(hydroxymethyl)-3-(((S)-1-phenylethyl)amino)piperidine-1-carboxylate was dissolved in DCM and treated with TFA (25 equiv) at ambient temperature. After consumption of starting material, the reaction was concentrated and used in the following step without purification. ES/MS: m/z 235.2 [M+H]$^+$.

benzyl rac-((1R,2S,3R,5S)-3-(difluoromethoxy)-8-azabicyclo[3.2.1]octan-2-yl)carbamate (A21)

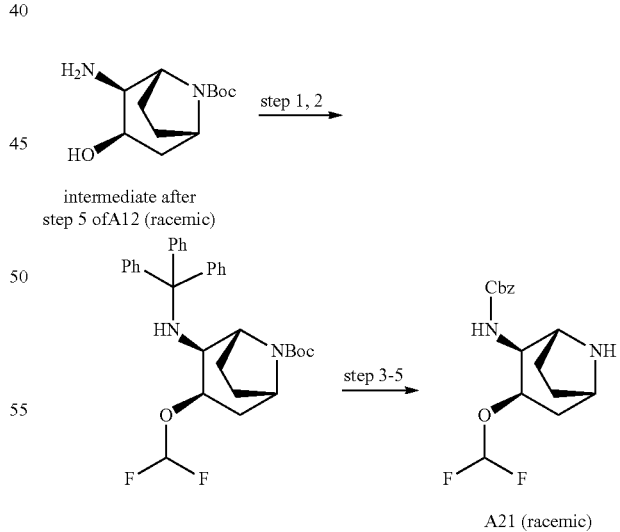

Step 1 tert-butyl rac-(1R,2S,3R,5S)-3-hydroxy-2-(tritylamino)-8-azabicyclo[3.2.1]octane-8-carboxylate was prepared following a similar procedure to the second part of step 2 for A5a. $^1$H NMR (400 MHz, DMSO-d$_6$) δ 7.53 (d, J=7.8 Hz, 6H), 7.33-7.26 (m, 6H), 7.25-7.16 (m, 3H), 4.73 (brs, 1H), 4.11 (brs, 1H), 3.79 (brs, 1H), 3.27 (d, J=7.8 Hz, 1H), 2.58 (brs, 1H), 2.48-2.33 (m, 1H), 2.01 (brs, 1H), 1.98-1.66 (m, 2H), 1.64-1.23 (m, 3H), 1.12 (s, 9H).

Step 2

Bromo(difluoro)methyl]-trimethyl-silane (1.26 g, 62 mmol) was added to a well stirred mixture of tert-butyl rac-(1R,2S,3R,5S)-3-hydroxy-2-(tritylamino)-8-azabicyclo[3.2.1]octane-8-carboxylate (1.0 g, 2.06 mmol) and potassium acetate (1.22g, 12.4 mmol) in DCM/water (1:1, mL) in a microwave vial. The resulting mixture was vigorously stirred for 12 hours before being worked up (DCM/NaHCO$_3$). The combined organic layers were dried over sodium sulfate evaporated to dryness and the crude material was re-subjected to the reaction conditions then purified by column chromatography over silica gel (Hexanes/EtOAc 0-15%) to afford rac-tert-butyl (1R,2S,3R,5S)-3-(difluoromethoxy)-2-(tritylamino)-8-azabicyclo[3.2.1]octane-8-carboxylate.

Step 3 tert-butyl rac-(1R,2S,3R,5S)-3-(difluoromethoxy)-2-(tritylamino)-8-azabicyclo[3.2.1]octane-8-carboxylate (390 mg, 0.73 mmol) was dissolved in diethyl ether (3 mL) and HCl in dioxane (4N, 1.2 mL) was added. The reaction was monitored by LCMS and upon completion excess HCl was removed with a flow of nitrogen. Silica was added to the mixture and after evaporation to dryness the residue was purified by flash chromatography over silica gel (DCM/EtOAc 1% of TEA, 0-75%) to afford rac-tert-butyl (1R,2S,3R,5S)-2-amino-3-(difluoromethoxy)-8-azabicyclo[3.2.1]octane-8-carboxylate. $^1$H NMR (400 MHz, DMSO-d$_6$) δ 6.72 (t, J=78.2 Hz, 0.5H), 6.72 (t, J=73.3 Hz, 0.5H), 4.48 (brs, 1H), 4.09 (brs, 3H), 2.23-2.09 (m, 2H), 2.07-1.95 (m, 1H), 1.94-1.68 (m, 6H), 1.42 (s, 9H).

Step 4

CBz-ONSU (485 mg, 1.95 mmol) was added to a solution of rac-tert-butyl (1R,2S,3R,5S)-2-amino-3-(difluoromethoxy)-8-azabicyclo[3.2.1]octane-8-carboxylate (190 mg, 0.65 mmol) and triethylamine (363 μL, 2.6 mmol) in DCM (3 mL). The resulting solution was stirred for 5 days at room temperature then evaporated to dryness and purified by column chromatography over silica gel to afford rac-tert-butyl (1R,2S,3R,5S)-2-(((benzyloxy)carbonyl)amino)-3-(difluoromethoxy)-8-azabicyclo[3.2.1]octane-8-carboxylate.

Step 5

HCl in dioxane (4N, 0.5 mL) was added to a solution of rac-tert-butyl (1R,2S,3R,5S)-2-(((benzyloxy)carbonyl)amino)-3-(difluoromethoxy)-8-azabicyclo[3.2.1]octane-8-carboxylate (111 mg, 0.26 mmol) in DCM (2 mL) and the resulting mixture was stirred overnight at which point LCMS analysis showed all the starting material was consumed. Evaporation to dryness deliver the hydrochloric salt of rac-benzyl ((1R,2S,3R,5S)-3-(difluoromethoxy)-8-azabicyclo[3.2.1]octan-2-yl)carbamate. $^1$H NMR (400 MHz, Chloroform-d) δ 7.48-7.32 (m, 4H), 6.20 (t, J=74.3 Hz, 1H), 5.14 (brs, 1H), 4.55-4.48 (m, 1H), 4.24 (brs, 1H), 4.14 (q, J=7.1 Hz, 2H), 4.08 (brs, 1H), 3.12-3.01 (m, 1H), 2.03-1.57 (m, 8H).

benzyl rac-((1R,2S,3R,5S)-3-methoxy-8-azabicyclo[3.2.1]octan-2-yl)carbamate (A22)


Step 1.

tert-butyl rac-(1R,2S,3R,5S)-3-hydroxy-2-(tritylamino)-8-azabicyclo[3.2.1]octane-8-carboxylate was prepared following a similar procedure to the second part of step 2 for A5a. $^1$H NMR (400 MHz, DMSO-d$_6$) δ 7.53 (d, J=7.8 Hz, 6H), 7.33-7.26 (m, 6H), 7.25-7.16 (m, 3H), 4.73 (brs, 1H), 4.11 (brs, 1H), 3.79 (brs, 1H), 3.27 (d, J=7.8 Hz, 1H), 2.58 (brs, 1H), 2.48-2.33 (m, 1H), 2.01 (brs, 1H), 1.98-1.66 (m, 2H), 1.64-1.23 (m, 3H), 1.12 (s, 9H).

Step 2 tert-butyl rac-(1R,2S,3R,5S)-3-methoxy-2-(tritylamino)-8-azabicyclo[3.2.1]octane-8-carboxylate was prepared following a similar procedure to the second part of step 2 for A5a. $^1$H NMR (400 MHz, DMSO-d$_6$) δ 7.53 (d, J=7.8 Hz, 6H), 7.36-7.27 (m, 6H), 7.23-7.17 (m, 3H), 4.17 (brs, 1H), 3.82 (s, 1H), 3.05 (d, J=7.9 Hz, 1H), 2.84 (s, 3H), 2.71 (s, 1H), 2.21 (brs, 1H), 1.95-1.58 (m, 4H), 1.33 (brs, 2H), 1.15 (s, 9H).

Step 3 benzyl rac-((1R,2S,3R,5S)-3-methoxy-8-azabicyclo[3.2.1]octan-2-yl)carbamate was prepared following a similar procedure to the second part of steps 3-5 for A21. $^1$H NMR (400 MHz, Chloroform-d) δ 7.48-7.33 (m, 5H), 5.68 (brs, 1H), 5.27-5.04 (m, 2H), 4.16 (brs, 2H), 3.94 (brs, 1H), 3.50 (brs, 1H), 3.30 (s, 3H), 2.11-1.69 (m, 6H), 1.36 (brs, 2H). ES/MS: m/z 291.12 [M+H]$^+$.

rac-2-((3S,4R)-4-cyclopropoxypiperidin-3-yl)isoindoline-1,3-dione (A23)

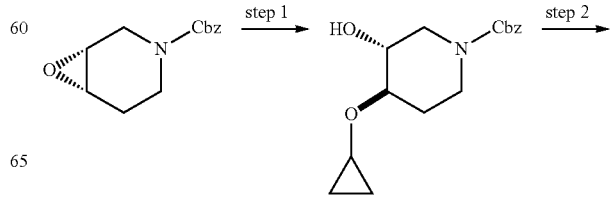

479

-continued

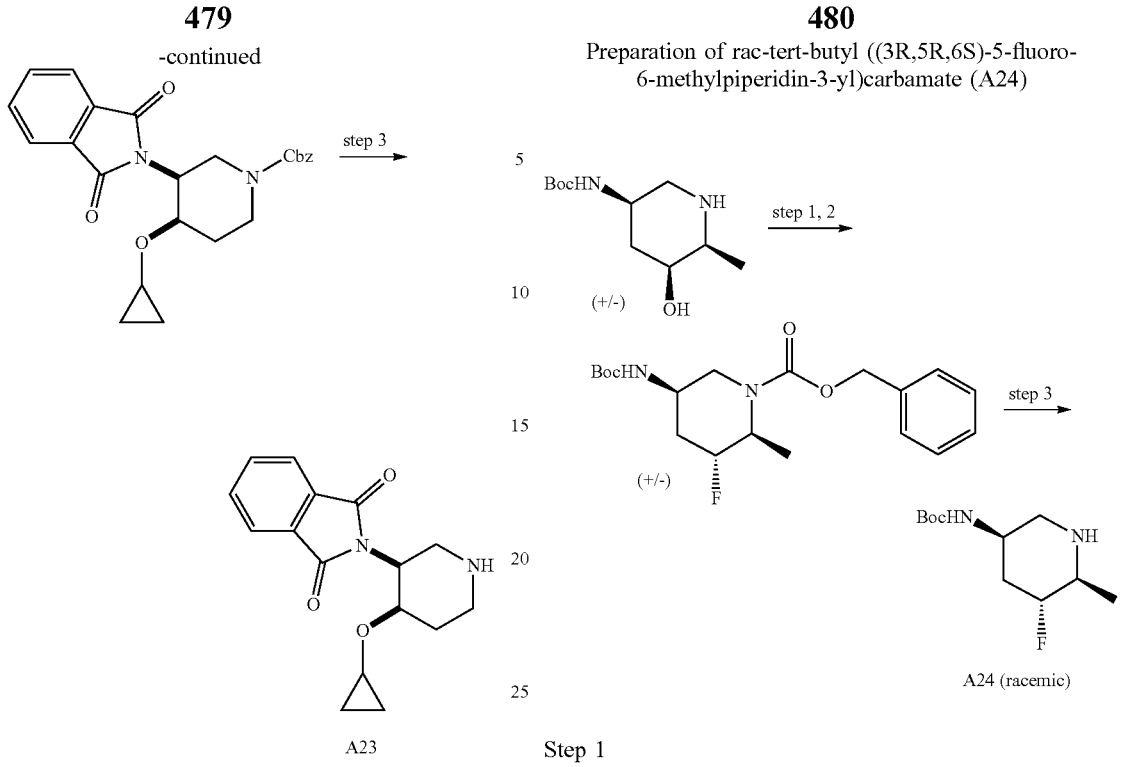

A23

Step 1.

Erbium(III) triflate (130 mg, 0.21 mmol) was added to a mixture of benzyl 7-oxa-3-azabicyclo[4.1.0]heptane-3-carboxylate (1.0 g, 4.3 mmol) and cyclopropanol (2.0 g, 34 mmol). After 5 hours, the reaction was poured into water and extracted 3× into EtOAc. The combined extracts were washed with brine, dried over MgSO$_4$, filtered, and adsorbed to isolate. Purification on silica gel chromatography (0-100% EtOAc in hexanes) with ELS detection provided two regioisomers. The first-eluting predominant isomer was determined by NMR to be benzyl rac-(3R,4R)-4-(cyclopropoxy)-3-hydroxy-piperidine-1-carboxylate, ES/MS: m/z 292.2 [M+H]$^+$. $^1$H NMR (400 MHz, Chloroform-d) δ 7.41-7.26 (m, 5H), 5.12 (s, 2H), 4.15 (ddd, J=11.8, 4.8, 2.5 Hz, 1H), 4.09-3.86 (m, 1H), 3.61-3.44 (m, 1H), 3.44-3.33 (m, 2H), 3.10-2.83 (m, 2H), 2.37 (d, J=2.6 Hz, 1H), 2.18-2.06 (m, 1H), 1.54-1.40 (m, 1H), 0.68-0.41 (m, 4H).

Step 2

A suspension of benzyl rac-(3R,4R)-4-(cyclopropoxy)-3-hydroxy-piperidine-1-carboxylate, phthalimide (121 mg, 0.82 mmol), and triphenylphosphine (216 mg, 0.82 mmol) in THF (3 mL) was cooled to 0° C. under N$_2$. Di-tert-butyl azodicarboxylate (190 mg, 0.82 mmol) was added dropwise, and the reaction allowed to attain ambient temperature and stir overnight. The mixture was adsorbed to isolute and purified twice by silica gel chromatography (0-100% EtOAc in hexanes) with ELS detection to afford benzyl rac-(3S,4R)-4-(cyclopropoxy)-3-(1,3-dioxoisoindolin-2-yl)piperidine-1-carboxylate as a white solid. ES/MS: m/z 421.2 [M+H]$^+$.

Step 3

Benzyl rac-(3S,4R)-4-(cyclopropoxy)-3-(1,3-dioxoisoindolin-2-yl)piperidine-1-carboxylate was subjected to conditions similar to step 4 of A17 to afford rac-2-((3S,4R)-4-cyclopropoxypiperidin-3-yl)isoindoline-1,3-dione. ES/MS: m/z 287.2 [M+H]$^+$.

480

Preparation of rac-tert-butyl ((3R,5R,6S)-5-fluoro-6-methylpiperidin-3-yl)carbamate (A24)

Step 1

The acetic acid salt of tert-butyl rac-((3R,5S,6S)-5-hydroxy-6-methylpiperidin-3-yl)carbamate (289 mg, 0.825 mmol) was dissolved in THF (2.3 mL) and the reaction mixture cooled to zero degrees. Triethylamine (0.920 mL, 6.60 mmol) and N-(Benzyloxycarbonyloxy) succinimide (0.247 g, 0.990 mmol) were added and the reaction mixture was warmed to rt. After stirring overnight, the reaction mixture was concentrated under reduced pressure. The resulting residue was diluted with water and DCM. The layers were separated and aqueous extracted with DCM. The combined organics were washed with sat. NaHCO$_3$ (aq), brine, dried, filtered, and concentrated under reduced pressure to yield benzyl rac-(2S,3S,5R)-5-((tert-butoxycarbonyl)amino)-3-hydroxy-2-methylpiperidine-1-carboxylate. ES/MS: m/z 364.8 [M+H]$^+$.

Step 2

To a cooled solution of benzyl rac-(2S,3S,5R)-5-((tert-butoxycarbonyl)amino)-3-hydroxy-2-methylpiperidine-1-carboxylate (150 mg, 0.412 mmol) in DCM (7.5 mL) at −78 degrees was added dropwise DAST (0.14 mL, 1.03 mmol). The mixture was slowly warmed to rt overnight, diluted with DCM, and transferred slowly via plastic pipet to a cooled solution of sat. NaHCO$_3$ (aq). The layers were separated and the aqueous extracted with DCM. The combined organics were dried, filtered, and concentrated under reduced pressure to yield benzyl rac-(2S,3R,5R)-5-((tert-butoxycarbonyl)amino)-3-fluoro-2-methylpiperidine-1-carboxylate. ES/MS: m/z 366.7 [M+H]$^+$.

Step 3

A mixture of benzyl rac-(2S,3R,5R)-5-((tert-butoxycarbonyl)amino)-3-fluoro-2-methylpiperidine-1-carboxylate (168 mg, 0.458 mmol) and palladium on carbon (10%, 168 mg, 0.158 mmol) in ethyl acetate (5.6 mL) was hydrogenated under an atmosphere of hydrogen. After 45 minutes, the reaction mixture was diluted with ethyl acetate and filtered over celite. The filtrate was concentrate under reduced pressure to yield tert-butyl rac-((3R,5R,6S)-5-fluoro-6-methylpiperidin-3-yl)carbamate. ES/MS: m/z 232.9 [M+H]$^+$.

Preparation of tert-butyl rac-((3R,5S,6S)-5-hydroxy-6-methylpiperidin-3-yl)carbamate (A25a)

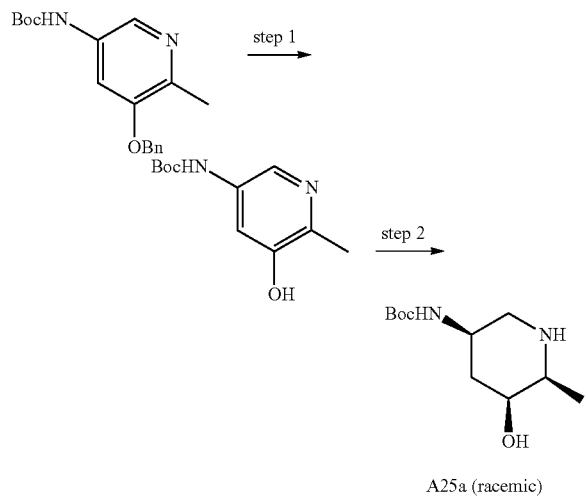

A25a (racemic)

Step 1

A mixture of tert-butyl N-(5-benzyloxy-6-methyl-3-pyridyl)carbamate (262 mg, 0.833 mmol) and palladium on carbon (10%, 222 mg, 0.208 mmol) in EtOH (5 mL) was hydrogenated under an atmosphere of hydrogen. After 17 hours, the reaction mixture was diluted with ethyl acetate and filtered over celite. The filtrate was concentrate under reduced pressure to yield tert-butyl (5-hydroxy-6-methylpyridin-3-yl)carbamate. ES/MS: m/z 224.8 [M+H]+.

Step 2

A mixture of tert-butyl N-(5-benzyloxy-6-methyl-3-pyridyl)carbamate (185 mg, 0.825 mmol) and Rh on Alumina (5%, 124 mg, 0.0602 mmol) was hydrogenated in a Parr apparatus at 50 PSI for 6 hours. The reaction mixture was diluted with ethyl acetate and filtered over celite. The filtrate was concentrate under reduced pressure to yield rac-tert-butyl ((3R,5S,6S)-5-hydroxy-6-methylpiperidin-3-yl)carbamate. ES/MS: m/z 230.9 [M+H]+.

tert-butyl rac-((2R,3R,5S)-5-hydroxy-2-methylpiperidin-3-yl)carbamate

Prepared as shown for rac-tert-butyl ((3R,5S,6S)-5-hydroxy-6-methylpiperidin-3-yl)carbamate using tert-butyl (5-(benzyloxy)-2-methylpyridin-3-yl)carbamate in step 1 instead of tert-butyl N-(5-benzyloxy-6-methyl-3-pyridyl)carbamate

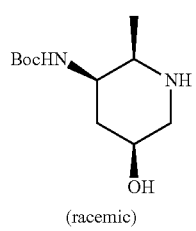

A25b (racemic)

Preparation of rac-tert-butyl (4aS,7S,8aR)-7-methyl-octahydro-4H-pyrido[4,3-b][1,4]oxazine-4-carboxylate (A26)

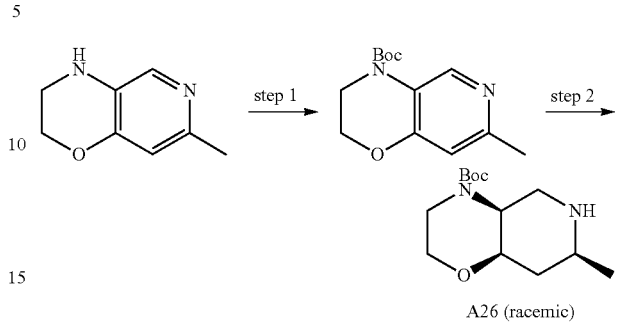

A26 (racemic)

Step 1.

7-methyl-3,4-dihydro-2H-pyrido[4,3-b][1,4]oxazine (190 mg, 1.27 mmol) was dissolved in DCM (4.3 mL) and DMAP (170 mg, 1.39 mmol), di-tert-butyl dicarbonate (552 mg, 2.53 mmol) and triethylamine (0.35 mL, 2.53 mmol) were added. After 24 hours, the reaction mixture was concentrated under reduced pressure and the resulting residue was purified via silica gel column chromatography (45-100% ethyl acetate in hexanes) to yield tert-butyl 7-methyl-2,3-dihydro-4H-pyrido[4,3-b][1,4]oxazine-4-carboxylate. ES/MS: m/z 250.9 [M+H]+.

Step 2

A mixture of tert-butyl 7-methyl-2,3-dihydro-4H-pyrido[4,3-b][1,4]oxazine-4-carboxylate (190 mg, 0.76 mmol) and Rh on Alumina (5%, 114 mg, 0.056 mmol) was hydrogenated in a Parr apparatus at 50 PSI for 16 hours. Additional Rh on Alumina (5%, 114 mg, 0.056 mmol) was added and the reaction mixture was hydrogenated in a Parr apparatus at 50 PSI for 26 hours. The reaction mixture was diluted with ethyl acetate and filtered over celite. The filtrate was concentrate under reduced pressure to yield rac-tert-butyl (4aS,7S,8aR)-7-methyloctahydro-4H-pyrido[4,3-b][1,4]oxazine-4-carboxylate. ES/MS: m/z 250.9 [M+H]+.

Preparation of tert-butyl rac-((2S,3R)-2-(difluoromethyl)piperidin-3-yl)carbamate (A27)

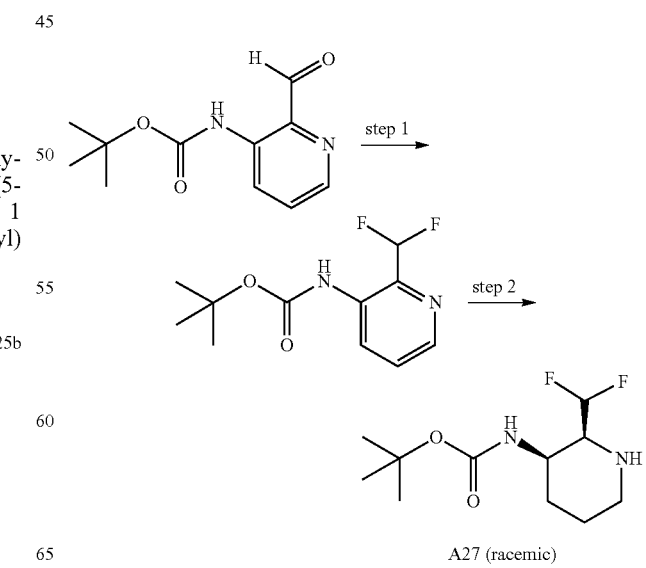

A27 (racemic)

Step 1 tert-butyl N-(2-formyl-3-pyridyl)carbamate (500 mg, 2.25 mmol) was dissolved in DCM (3 mL) in a polypropylene vial and the solution was cooled in an ice water bath. Diethylaminosulfur trifluoride (1.05 mL, 7.95 mmol) was added, and the resulting mixture was allowed to warm to r.t. After 5.5 h, the reaction mixture was quenched by addition to stirred saturated aqueous NaHCO$_3$. The mixture was diluted with DCM and the phases were separated. Purification by silica gel provided tert-butyl N-[2-(difluoromethyl)-3-pyridyl]carbamate. $^1$H NMR (400 MHz, DMSO-d6) δ 9.17 (s, 1H), 8.47 (dd, J=4.5, 1.5 Hz, 1H), 7.93 (dd, J=8.3, 1.3 Hz, 1H), 7.59-7.51 (m, 1H), 7.10 (t, J=53.7 Hz, 1H), 1.47 (s, 9H).

Step 2 tert-butyl N-[2-(difluoromethyl)-3-pyridyl]carbamate (291 mg, 1.2 mmol) was dissolved in acetic acid (1.5 mL), and 5% Rh on alumina (125 mg, 0.061 mmol) was added). The reaction vessel was shaken under H$_2$ (55 psi) for 15 h and was filtered. The filtrate was concentrated, and the resulting residue was partitioned between EtOAc and 5% aqueous Na$_2$CO$_3$. The organic layer was dried over Na$_2$SO$_4$, filtered, and concentrated to afford a residue that was purified by silica gel chromatography (EA/hexanes gradient) to provide tert-butyl rac-((2S,3R)-2-(difluoromethyl)piperidin-3-yl)carbamate. ES/MS: m/z 250.86 [M+H]$^+$. $^1$H NMR (400 MHz, DMSO-d$_6$) δ 6.67 (d, J=9.1 Hz, 1H), 5.73 (td, J=56.0, 5.5 Hz, 1H), 3.77-3.70 (m, 1H), 2.94-2.84 (m, 2H), 2.48-2.40 (m, 1H), 2.27 (s, 1H), 1.72-1.63 (m, 1H), 1.58-1.48 (m, 2H), 1.39 (s, 9H), 1.34-1.26 (m, 1H).

Preparation of tert-butyl rac-((1R,4R,5R)-2-azabicyclo[2.1.1]hexan-5-yl)carbamate (A28)

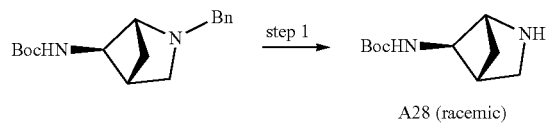

Step 1

To a solution of N-benzyl-rac-5-(tert-butoxycarbonylamino)-2-azabicyclo[2.1.1]hexane (synthesized according to J. Org. Chem. 2009, 74, 8232; 0.050 g, 0.173 mmol) in EtOH (3.4 mL) was added Pd/C (0.010 g of 10% Pd on C, wet). The mixture was stirred at rt under 1 atm H$_2$ (balloon) for 16 h. The mixture was filtered and the filtrate was concentrated to yield crude tert-butyl rac-((1R,4R,5R)-2-azabicyclo[2.1.1]hexan-5-yl)carbamate. ES/MS: m/z 199.1 [M+H]$^+$.

Preparation of tert-butyl ((1S,4R,5S,8S)-8-fluoro-2-azabicyclo[3.2.1]octan-4-yl)carbamate (A29)

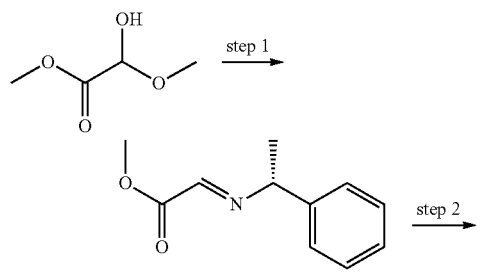

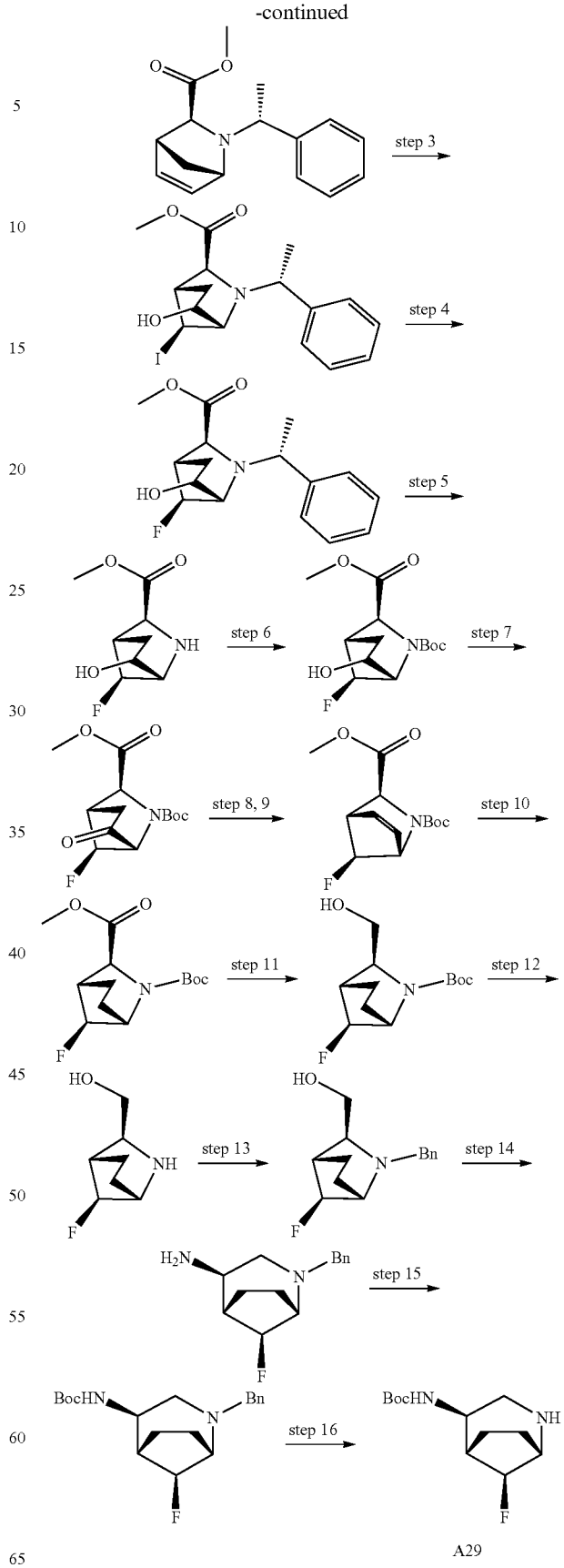

Step 1
To (1R)-1-phenylethan-1-amine (2 kg, 16.5 mol) in DCM (25 L) was added methyl 2-hydroxy-2-methoxyacetate (1.98 kg, 16.5 mol). The reaction mixture was stirred at rt for 3 h before it was concentrated en vacuo, giving crude methyl (R,E)-2-((1-phenylethyl)imino)acetate. $^1$H NMR (400 MHz, Chloroform-d) δ 7.74 (s, 1H), 7.35-7.26 (m, 5H), 4.61 (q, J=8.8 Hz, 1H), 3.87 (s, 3H), 1.62 (d, J=9.2 Hz, 3H).

Step 2
To methyl (R,E)-2-((1-phenylethyl)imino)acetate (2.7 kg, 14.1 mol) in DCM (27 L) at −78° C. was added TFA (1.08 L, 14.1 mol), dropwise. BF$_3$—OEt$_2$ (1.84 L, 14.9 mol) was subsequently added, dropwise, followed by cyclopenta-1,3-diene (1.1 kg, 16.8 mol). The reaction mixture was stirred at −78° C. for 3 h. The mixture was allowed to warm to rt before it was quenched by the addition of Na$_2$CO$_3$ soln (aq). The aqueous layer was extracted with DCM. The combined organic layers were washed with brine, dried (Na$_2$SO$_4$), and concentrated to give crude methyl (1S,3S,4R)-2-((R)-1-phenylethyl)-2-azabicyclo[2.2.1]hept-5-ene-3-carboxylate.

Step 3
To a solution of methyl 2-[(1R)-1-phenylethyl]-2-azabicyclo[2.2.1]hept-5-ene-3-carboxylate (60 g, 230 mmol) in DMSO (300 mL) and water (50 mL) at rt was added NIS (55.1 g, 245 mmol) in portions over 30 min. The mixture was stirred at rt for 1 h at room temperature. The mixture was diluted with EtOAc and quenched by addition of aqueous sodium bicarbonate solution. The organic layer was washed sequentially with 10% Na$_2$S$_2$O$_3$ solution and brine, dried (Na$_2$SO$_4$), filtered and concentrated. The residue was purified via flash column chromatography on silica gel to give methyl (1S,3S,4S,6R,7S)-6-hydroxy-7-iodo-2-((R)-1-phenylethyl)-2-azabicyclo[2.2.1]heptane-3-carboxylate. ES/MS: m/z 402.1 [M+H]$^+$. $^1$H NMR (400 MHz, Chloroform-d) δ 7.26 (m, 5H), 4.21 (s, 1H), 3.81-3.71 (m, 2H), 3.50 (m, 4H), 3.33 (s, 1H), 2.73 (s, 1H), 2.14 (dd, J=14.2, 7.7 Hz, 1H), 2.05 (m, 2H), 1.92 (d, J=14.2 Hz, 1H), 1.43 (d, J=6.5 Hz, 3H).

Step 4
To a solution of methyl (1S,3S,4S,6R,7S)-6-hydroxy-7-iodo-2-((R)-1-phenylethyl)-2-azabicyclo[2.2.1]heptane-3-carboxylate (150 g, 374 mmol) in MeCN (1.5 L) was added TBAF (147 g, 561 mmol). The mixture was stirred at 90° C. for 16 h. The mixture was cooled to rt and concentrated. The resulting residue was diluted with EtOAc and solids were removed via filtration. The filtrate was diluted with water and the aqueous layer was extracted with EtOAc. The combined organic layers were washed with brine, dried (Na$_2$SO$_4$), filtered, and concentrated. The residue was purified via flash column chromatography on silica gel to afford methyl (1S,3S,4S,6R,7S)-7-fluoro-6-hydroxy-2-((R)-1-phenylethyl)-2-azabicyclo[2.2.1]heptane-3-carboxylate. ES/MS: m/z 294.2 [M+H]$^+$.

Step 5
To a solution of methyl (1S,3S,4S,6R,7S)-7-fluoro-6-hydroxy-2-((R)-1-phenylethyl)-2-azabicyclo[2.2.1]heptane-3-carboxylate (50 g, 170 mmol) in EtOH (300 mL) was added HCl (60 mL of a 4 M soln in dioxane). The mixture was stirred at rt for 5 min before it was concentrated. The residue was taken up in EtOH (350 mL) and Pd/C (50 g of 10% Pd/C) was added. The mixture was stirred under H$_2$ at rt for 2 h. The solids were removed via filtration. The filtrate was concentrated to yield methyl (1S,3S,4S,6R,7S)-7-fluoro-6-hydroxy-2-azabicyclo[2.2.1]heptane-3-carboxylate as the hydrochloride salt. ES/MS: m/z 190.2 [M+H]$^+$. $^1$H NMR (400 MHz, Chloroform-d) δ 5.46 (d, J=52.5 Hz, 1H), 4.53 (m, 1H), 4.46 (m, 1H), 4.30 (s, 1H), 3.89 (s, 3H), 3.05 (s, 1H), 2.05 (d, J=10.5 Hz, 2H).

Step 6
To a solution of methyl (1S,3S,4S,6R,7S)-7-fluoro-6-hydroxy-2-azabicyclo[2.2.1]heptane-3-carboxylate hydrochloride (43 g, 190 mmol) in THF (500 mL) was added DIEA (146 mL, 843 mmol) followed by di-tert-butyl decarbonate (73.6 g, 341 mmol). The mixture was stirred at rt for 16 h. The mixture was concentrated under vacuum and the residue was purified via flash column chromatography on silica gel to afford 2-(tert-butyl) 3-methyl (1S,3S,4S,6R,7S)-7-fluoro-6-hydroxy-2-azabicyclo[2.2.1]heptane-2,3-dicarboxylate. ES/MS: m/z 233.9 [M+H-tBu]$^+$.

Step 7
To a solution of 2-(tert-butyl) 3-methyl (1S,3S,4S,6R,7S)-7-fluoro-6-hydroxy-2-azabicyclo[2.2.1]heptane-2,3-dicarboxylate (50 g, 173 mmol) in DCM (500 mL) at 0° C. was added DMP (88 g, 208 mmol) in portions over 30 min. The mixture was stirred at rt for 1 h before it was quenched by the addition of sat Na$_2$S$_2$O$_3$ soln (aq) and sat NaHCO$_3$ soln (aq). The aqueous layer was extracted with DCM. The combined organic layers were washed with brine, dried (Na$_2$SO$_4$), filtered, and concentrated. The residue was purified via flash column chromatography on silica gel to give 2-(tert-butyl) 3-methyl (1S,3S,4S,7S)-7-fluoro-6-oxo-2-azabicyclo[2.2.1]heptane-2,3-dicarboxylate. ES/MS: m/z 231.8 [M+H-tBu]$^+$.

Step 8
To a solution of 2-(tert-butyl) 3-methyl (1S,3S,4S,7S)-7-fluoro-6-oxo-2-azabicyclo[2.2.1]heptane-2,3-dicarboxylate (40 g, 139 mmol) in THF (400 mL) at −78° C. was added KHMDS (209 mL of a 1 M soln in THF, 209 mmol), dropwise. The mixture was stirred at −78° C. for 1 h. A solution of N-(5-chloro-2-pyridyl)bis(trifluoromethanesulfonimide) (82 g, 209 mmol) in THF (200 mL) was then added, dropwise, over 30 min. The mixture was stirred at −78° C. for 30 min and then at rt for 40 min. The mixture was diluted with EtOAc and quenched by the addition of sat NH$_4$Cl solution (aq). The aqueous layer was extracted with EtOAc. The combined organic layers were washed with brine, dried (Na$_2$SO$_4$), filtered, and concentrated.

The residue was purified via flash column chromatography on silica gel to afford 2-(tert-butyl) 3-methyl (1S,3S,4S,7S)-7-fluoro-6-(((trifluoromethyl)sulfonyl)oxy)-2-azabicyclo[2.2.1]hept-5-ene-2,3-dicarboxylate. ES/MS: m/z 363.8 [M+H-tBu]$^+$.

Step 9
To a solution of 2-(tert-butyl) 3-methyl (1S,3S,4S,7S)-7-fluoro-6-(((trifluoromethyl)sulfonyl)oxy)-2-azabicyclo[2.2.1]hept-5-ene-2,3-dicarboxylate (35 g, 83 mmol) in DMF (150 mL) were added TEA (38 mL, 275 mmol), Pd(PPh$_3$)$_2$Cl$_2$ (2.45 g, 3.3 mmol), and formic acid (6.6 mL, 176 mmol). The mixture was stirred at 60° C. for 1 h. The mixture was cooled to rt and the solids were removed via filtration. The filtrate was diluted with water and the aqueous layer was extracted with EtOAc. The organic layers were washed with brine, dried (Na$_2$SO$_4$), filtered, and concentrated. The residue was purified via flash column chromatography on silica gel to yield 2-(tert-butyl) 3-methyl (1S,3S,4S,7S)-7-fluoro-2-azabicyclo[2.2.1]hept-5-ene-2,3-dicarboxylate. $^1$H-NMR (300 MHz, CDCl$_3$): δ 6.54 (s, 1H), 6.12 (s, 1H), 4.65-4.95 (m, 2H), 4.31 (d, J=10.5 Hz, 1H), 3.68 (s, 3H), 3.46 (d, J=2.3 Hz, 1H), 1.26 (d, J=16.7 Hz, 9H).

Step 10
To a mixture of 2-(tert-butyl) 3-methyl (1S,3S,4S,7S)-7-fluoro-2-azabicyclo[2.2.1]hept-5-ene-2,3-dicarboxylate (8.41 g, 31.0 mmol) in EtOH (100 mL) was added Pd(OH)$_2$/C (1.09 g of 20% Pd(OH)$_2$/C). The mixture was stirred under H$_2$ for 1 h before it was diluted with DCM and filtered through Celite. The filtrate was concentrated to yield crude 2-(tert-butyl) 3-methyl (1S,3S,4S,7S)-7-fluoro-2-azabicyclo[2.2.1]heptane-2,3-dicarboxylate. ES/MS: m/z 218.1 [M+H-tBu]$^+$.

Step 11

To 2-(tert-butyl) 3-methyl (1S,3S,4S,7S)-7-fluoro-2-azabicyclo[2.2.1]heptane-2,3-dicarboxylate (6.47 g, 23.7 mmol) in MeTHF (25 mL) at 0° C. was added LAH (35.5 mL of a 1 M soln in THF, 35.5 mmol). The mixture was stirred for 5 min and was then quenched carefully by the addition of water (1.4 mL) followed by NaOH (1.4 mL of 15% NaOH) and an additional portion of water (4.5 mL). The mixture was diluted with ether, warmed to rt, dried (Na$_2$SO$_4$), filtered, and concentrated to yield crude tert-butyl (1S,3S,4S,7S)-7-fluoro-3-(hydroxymethyl)-2-azabicyclo[2.2.1]heptane-2-carboxylate. ES/MS: m/z 190.1 [M+H-tBu]$^+$.

Step 12

To a solution of tert-butyl (1S,3S,4S,7S)-7-fluoro-3-(hydroxymethyl)-2-azabicyclo[2.2.1]heptane-2-carboxylate (0.510 g, 2.08 mmol) in DCM (15 mL) was added HCl soln (10.4 mL of 4 M HCl in dioxane, 41.6 mmol). The mixture sat at rt for 48 h and was then concentrated to give crude ((1S,3S,4S,7S)-7-fluoro-2-azabicyclo[2.2.1]heptan-3-yl)methanol, which was used directly. ES/MS: m/z 146.1 [M+H]$^+$.

Step 13.

To crude ((1S,3S,4S,7S)-7-fluoro-2-azabicyclo[2.2.1]heptan-3-yl)methanol (ca. 2.08 mmol) in MeCN (20 mL) at 0° C. was added K$_2$CO$_3$ (0.863 g, 6.24 mmol) followed by BnBr (0.27 mL, 2.3 mmol). The mixture was allowed to warm to rt and was stirred for 72 h. The mixture was filtered. The filtrate was concentrated and the residue was purified via flash column chromatography on silica gel to afford ((1S,3S,4S,7S)-2-benzyl-7-fluoro-2-azabicyclo[2.2.1]heptan-3-yl)methanol. $^1$H NMR (400 MHz, Chloroform-d) δ 7.35-7.22 (m, 5H), 5.03 (dt, J=57.4, 2.1 Hz, 1H), 3.76 (d, J=13.4 Hz, 1H), 3.67 (d, J=13.4 Hz, 1H), 3.46 (ddd, J=10.8, 4.3, 1.3 Hz, 1H), 3.40 (ddd, J=10.8, 6.4, 1.2 Hz, 1H), 3.10-3.02 (m, 1H), 3.02-2.94 (m, 1H), 2.52-2.45 (m, 1H), 1.92-1.78 (m, 2H), 1.78-1.65 (m, 1H), 1.60-1.48 (m, 1H). ES/MS: m/z 236.1 [M+H]$^+$.

Step 14.

To a mixture of ((1S,3S,4S,7S)-2-benzyl-7-fluoro-2-azabicyclo[2.2.1]heptan-3-yl)methanol (0.113 g, 0.480 mmol) and TEA (0.13 mL, 0.96 mmol) in MeCN (2.4 mL) at 0° C. was added Ms$_2$O (0.134 g, 0.786 mmol) portionwise over 10 min. The mixture was stirred at 0° C. for 10 min before ammonia soln (3.4 mL of 7 M NH$_3$ in MeOH, 24 mmol) was added. The mixture was stirred at 75° C. for 20 min. The mixture was cooled to rt and concentrated to give crude (1S,4R,5S,8S)-2-benzyl-8-fluoro-2-azabicyclo[3.2.1]octan-4-amine, which was used directly. ES/MS: m/z 235.1 [M+H]$^+$.

Step 15.

To a solution of (1S,4R,5S,8S)-2-benzyl-8-fluoro-2-azabicyclo[3.2.1]octan-4-amine (ca. 0.480 mmol) and TEA (0.08 mL, 0.60 mmol) in DCM (1.6 mL) was added Boc$_2$O (0.116 g, 0.530 mmol). The mixture was stirred at rt for 16 h before it was diluted with DCM and washed successively with water and brine, dried (Na$_2$SO$_4$), filtered, and concentrated. The residue was purified via flash column chromatography on silica gel to afford tert-butyl ((1S,4R,5S,8S)-2-benzyl-8-fluoro-2-azabicyclo[3.2.1]octan-4-yl)carbamate.

$^1$H NMR (400 MHz, Chloroform-d) δ 7.36-7.19 (m, 5H), 4.66 (d, J=53.3 Hz, 1H), 4.49-4.33 (m, 1H), 3.90-3.73 (m, 1H), 3.50 (s, 2H), 3.30-3.20 (m, 1H), 2.76 (ddd, J=11.2, 5.7, 3.4 Hz, 1H), 2.57 (dd, J=11.6, 6.0 Hz, 1H), 1.84-1.58 (m, 4H), 1.48-1.34 (m, 10H). ES/MS: m/z 335.2 [M+H]$^+$.

Step 16.

To a solution of tert-butyl ((1S,4R,5S,8S)-2-benzyl-8-fluoro-2-azabicyclo[3.2.1]octan-4-yl)carbamate (0.099 g, 0.287 mmol) in EtOH (3.0 mL) was added Pd/C (0.020 g of 10% Pd on C, wet). The mixture was stirred under 1 atm H$_2$ (balloon) for 72 h before it was filtered. The filtrate was concentrated to yield crude tert-butyl ((1S,4R,5S,8S)-8-fluoro-2-azabicyclo[3.2.1]octan-4-yl)carbamate. ES/MS: m/z 245.1 [M+H]$^+$.

Preparation of tert-butyl ((1R,4S,7S)-2-oxa-5-azabicyclo[2.2.1]heptan-7-yl)carbamate (A30)

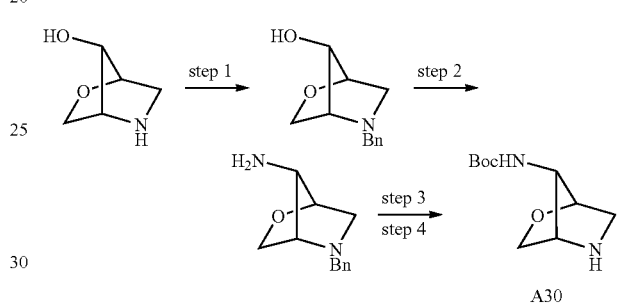

Step 1

(1R,4R,7S)-5-benzyl-2-oxa-5-azabicyclo[2.2.1]heptan-7-ol (1R,4R,7S)-5-benzyl-2-oxa-5-azabicyclo[2.2.1]heptan-7-ol. A solution of A solution of (1R,4R,7S)-5-benzyl-2-oxa-5-azabicyclo[2.2.1]heptan-7-ol HCl (380 mg, 2.5 mmol), benzaldehyde (0.35 mL, 3.5 mmol), acetic acid (1.4 mL, 25 mmol) in 1,2-dichloroethane (22 mL) was stirred for 5 min. Then, sodium triacetoxyborohydride (1.1 g, 5 mmol) was added and the reaction mixture stirred for 24 hr. Added saturated sodium bicarbonate and washed three times with DCM. The combined organic layers were dried over Na$_2$SO$_4$, filtered and concentrated. The crude residue was purified by flash chromatography eluting with hexanes/EtOAc to give a colorless oil (350 mg, 68%). ES/MS: m/z 206.10 [M+H]+.

Step 2

(1R,4S,7S)-5-benzyl-2-oxa-5-azabicyclo[2.2.1]heptan-7-amine. To a solution of (1R,4R,7S)-5-benzyl-2-oxa-5-azabicyclo[2.2.1]heptan-7-ol (55 mg, 0.27 mmol) and triethylamine (75 µL, 0.54 mmol) in DCM (2.7 mL) at 0° C. was added methanesulfonic anhydride (58 mg, 0.34 mmol). The solution stirred at 0° C. for 30 min. To this solution was added 7 N ammonia in MeOH (0.77 mL, 5.4 mmol). The solution stirred in a sealed vessel at 60° C. for 18 hr and then concentrated. ES/MS: m/z 204.99 [M+H]+.

Step 3 tert-butyl ((1R,4S,7S)-5-benzyl-2-oxa-5-azabicyclo[2.2.1]heptan-7-yl)carbamate was prepared using a similar procedure to step 3 of A7 with (1R,4S,7S)-5-benzyl-2-oxa-5-azabicyclo[2.2.1]heptan-7-amine. ES/MS: m/z 305.06 [M+H]+.

Step 4 tert-butyl ((1R,4S,7S)-2-oxa-5-azabicyclo[2.2.1]heptan-7-yl)carbamate (A30) was prepared using a similar procedure to step 7 of A8 with tert-butyl ((1R,4S,7S)-5-benzyl-2-oxa-5-azabicyclo[2.2.1]heptan-7-yl)carbamate. ES/MS: m/z 215.10 [M+H]+.

Preparation of tert-butyl ((3S,4R)-4-(trifluoromethoxy)piperidin-3-yl)carbamate (A31)

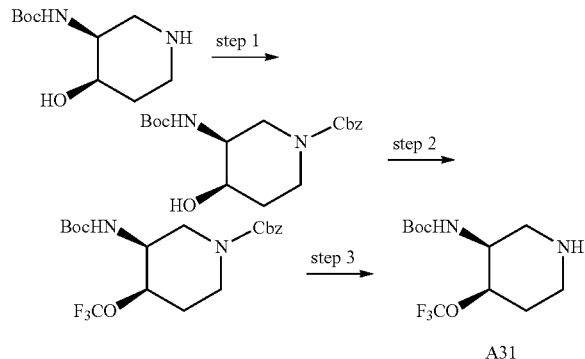

Step 1
benzyl (3S,4R)-3-((tert-butoxycarbonyl)amino)-4-hydroxypiperidine-1-carboxylate was prepared using a similar procedure to step 1 of A24 using A1.26. ES/MS: m/z 250.9 [M+H]+.

Step 2
To a reaction tube equipped with a stirring bar, AgOTf (385.4 mg, 1.5 mmol, 3.0 equiv), Selectfluor (265.7 mg, 0.75 mmol, 1.5 equiv), KF (116.2 mg, 2.0 mmol, 4.0 equiv), benzyl (3S,4R)-3-((tert-butoxycarbonyl)amino)-4-hydroxypiperidine-1-carboxylate (0.5 mmol, 1.0 equiv) were added successively under argon. Then ethyl acetate (2.5 mL), 2-fluoropyridine (145.5 mg, 1.5 mmol, 3.0 equiv) and CF$_3$TMS (213.3 mg, 1.5 mmol, 3.0 equiv) were added successively under Ar atmosphere. The reaction mixture was stirred at room temperature for 12 h. The reaction mixture was filtered through a plug of silica (eluted with ethyl acetate). The filtrate was concentrated, and the product was purified by column chromatography on silica gel to give the desired product. ES/MS: m/z 419.65 [M+H]+.

Step 3
tert-butyl ((3S,4R)-4-(trifluoromethoxy)piperidin-3-yl)carbamate was prepared using a similar procedure to step 3 of A24 using A1.26. ES/MS: m/z 285.8 [M+H]+.

Preparation of tert-butyl (4-(methoxymethyl)piperidin-3-yl)carbamate (A32)

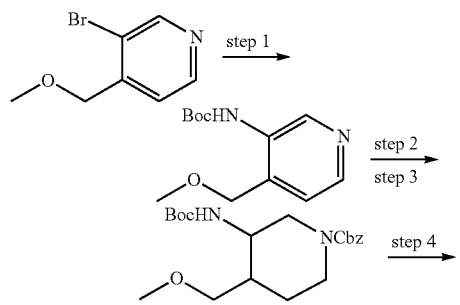

-continued

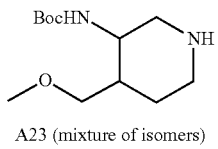

A23 (mixture of isomers)

Step 1
3-bromo-4-(methoxymethyl)pyridine (200 mg, 0.99 mmol) was combined with tert-Butyl carbamate (139 mg, 1.2 mmol), XantPhos Pd G3 (94 mg, 0.10 mmol), and cesium carbonate (484 mg, 1.5 mmol) in dioxane (5 mL). The mixture was degassed under N$_2$, capped, and heated to 100° C. overnight. The reaction was filtered through celite and the filtrate was concentrated, adsorbed to isolute, and purified by silica gel chromatography (0-100% 3:1 EtOAc/EtOH in heptane) to afford tert-butyl N-[4-(methoxymethyl)-3-pyridyl]carbamate as an amber oil. ES/MS: m/z 238.9 [M+H]$^+$.

Steps 2-3.
Benzyl 3-(tert-butoxycarbonylamino)-4-(methoxymethyl)piperidine-1-carboxylate was prepared following steps 1-2 of A16 using tert-butyl N-[4-(methoxymethyl)-3-pyridyl]carbamate. ES/MS: m/z 378.7 [M+H]$^+$.

Step 4
tert-butyl N-[4-(methoxymethyl)-3-piperidyl]carbamate was prepared following step 4 of A16 using benzyl 3-(tert-butoxycarbonylamino)-4-(methoxymethyl)piperidine-1-carboxylate and adding HOAc to reaction mixture. ES/MS: m/z 244.9 [M+H]$^+$.

Preparation of tert-butyl rac-(3S,4S,5S)-3-(((benzyloxy)carbonyl)amino)-5-fluoro-4-hydroxypiperidine-1-carboxylate and tert-butyl rac-(3S,4R,5R)-3-(((benzyloxy)carbonyl)amino)-4-fluoro-5-hydroxypiperidine-1-carboxylate (A33)

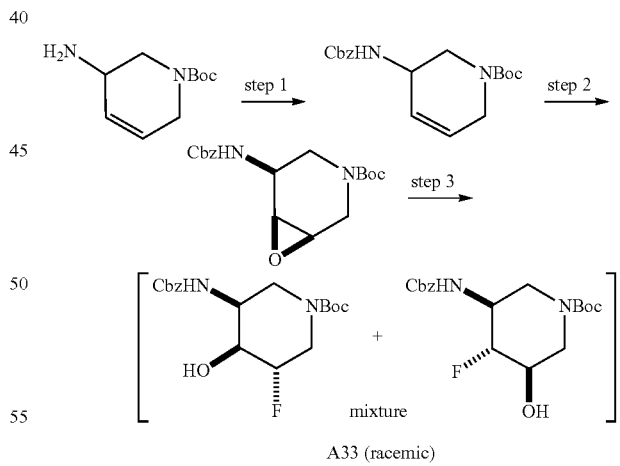

A33 (racemic)

Step 1
tert-Butyl 3-amino-3,6-dihydro-2H-pyridine-1-carboxylate (5.0 g, 25 mmol) was dissolved in DCM (100 mL) and treated with triethylamine (10.6 mL, 76 mmol), then CbzOSu (6.6 g, 27 mmol). The mixture was stirred at ambient temperature for 24 hours, then was diluted with water and HCl (1M aqueous, 50 mL, 50 mmol). The mixture was extracted into DCM, then purified by silica gel chromatography (0-50% EtOAc in hexane) to afford tert-butyl 3-(benzyloxycarbonylamino)-3,6-dihydro-2H-pyridine-1-carboxylate. ES/MS: m/z 355.2 [M+Na]+.

Step 2 mCPBA (7.1 g, 29 mmol) was added to a suspension of tert-butyl 3-(benzyloxycarbonylamino)-3,6-dihydro-2H-pyridine-1-carboxylate (4.8 g, 14 mmol) and NaHCO$_3$ (2.4 g, 29 mmol) in DCM (120 mL) and the resulting mixture stirred at ambient temperature. The reaction was quenched with aq. Na$_2$SO$_3$ and NaHCO$_3$ and extracted into DCM. The combined extracts were concentrated and purified by silica gel chromatography (0-50% EtOAc in hexane) to afford tert-butyl rac-(1R,5S,6S)-5-(benzyloxycarbonylamino)-7-oxa-3-azabicyclo[4.1.0]heptane-3-carboxylate, ES/MS: m/z 371.1 [M+Na]+.

Step 3 tert-Butyl rac-(1R,5S,6S)-5-(benzyloxycarbonylamino)-7-oxa-3-azabicyclo[4.1.0]heptane-3-carboxylate (800 mg, 2.3 mmol) and Et$_3$N-3HF (3.0 mL, 18 mmol) were combined in THF (2 mL) in a pressure flask, which was sealed and heated at 130° C. for 16 hours. The cooled reaction was quenched with aq. NaHCO$_3$ and extracted 2× into DCM. The combined extracts were adsorbed to isolute and purified by silica gel chromatography (0-100% EtOAc in hexane) using ELS detection. The product was isolated as a mixture of isomers: tert-butyl rel-(3S,4S,5S)-3-(benzyloxycarbonylamino)-5-fluoro-4-hydroxy-piperidine-1-carboxylate and tert-butyl rel-(3S,4R,5R)-3-(benzyloxycarbonylamino)-4-fluoro-5-hydroxy-piperidine-1-carboxylate. ES/MS: m/z 391.1 [M+Na]+.

Preparation of tert-butyl (3S,4S,5S)-3-(((benzyloxy)carbonyl)amino)-5-fluoro-4-methoxypiperidine-1-carboxylate (A34b)

Step 1

The above isomer mixture was dissolved in acetone (3 mL) and treated with dimethyl sulfate (0.42 mL, 4.4 mmol). The resulting solution was cooled to 0° C., then NaOH (0.86 mL of a 15% aqueous solution, 3.8 mmol) was added dropwise. The reaction was stored at 2° C. o/n, then diluted with EtOAc and washed with brine. The organic phase was adsorbed to isolute and purified by silica gel chromatography (0-70% EtOAc in hexane) using ELS detection. A34a: tert-butyl rel-(3S,4R,5R)-3-(benzyloxycarbonylamino)-4-fluoro-5-methoxy-piperidine-1-carboxylate, ES/MS: m/z 405.1 [M+Na]+. A34b: tert-butyl rel-(3S,4S,5S)-3-(benzyloxycarbonylamino)-5-fluoro-4-methoxy-piperidine-1-carboxylate, ES/MS: m/z 405.1 [M+Na]+.

tert-butyl ((1S,4R,5R)-2-azabicyclo[3.2.1]octan-4-yl-3,3-d2)carbamate (A35)

tert-butyl ((1S,4R,5R)-2-azabicyclo[3.2.1]octan-4-yl-3,3-d2)carbamate was prepared using a similar procedure to A18 using LiALD$_4$ instead of BH$_3$-DMS in step 9. ES/MS: m/z 229.97 (M+H+). $^1$H NMR (400 MHz, DMSO-d6) δ 8.41 (brs, 2H), 7.08 (d, J=8.0 Hz, 1H), 3.77 (t, J=4.4 Hz, 1H), 3.73-3.61 (m, 1H), 2.25 (brs, 1H), 1.95-1.54 (m, 5H), 1.39 (s, 9H).

Preparation of tert-butyl ((1R,5R,8R)-2-azabicyclo[3.2.1]octan-8-yl)carbamate (A36)

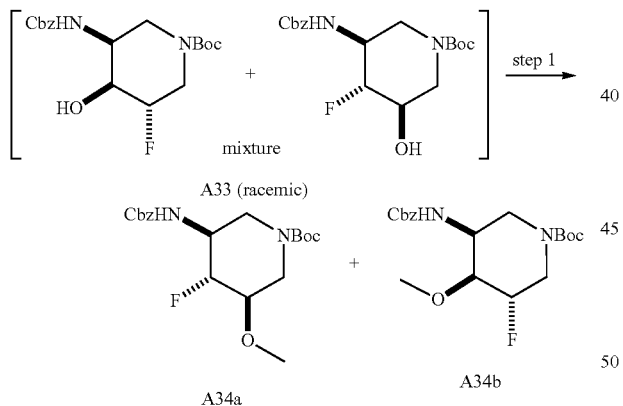

Step 1

Methyl (1R,3R,4S)-2-((S)-1-phenylethyl)-2-azabicyclo[2.2.1]hept-5-ene-3-carboxylate (1.40 g, 5.44 mmol) was dissolved in THF (6 mL) and cooled to −78° C. and LiAlH$_4$ (1M in THF, 8.2 mL) was added dropwise. The reaction was monitored by LCMS and upon completion was worked up using Fieser work up. The residue was then purified by column chromatography to afford ((1R,3R,4S)-2-((S)-1-phenylethyl)-2-azabicyclo[2.2.1]hept-5-en-3-yl)methanol. ES/MS: m/z 230.78 [M+H]+.

Step 2

((1R,3R,4S)-2-((S)-1-phenylethyl)-2-azabicyclo[2.2.1]hept-5-en-3-yl)methanol (1.24 g, 5.4 mmol) was dissolved in DCM (10 mL), cooled to 0° C. and triethylamine (552 mg, 5.4 mmol) was added followed by acetyl chloride (428 mg, 5.4 mmol). The mixture was stirred for 1 hour then evaporated to dryness and purified by column chromatography over silica gel to afford ((1R,3R,4S)-2-((S)-1-phenylethyl)-2-azabicyclo[2.2.1]hept-5-en-3-yl)methyl acetate.

Step 3

((1R,3R,4S)-2-((S)-1-phenylethyl)-2-azabicyclo[2.2.1]hept-5-en-3-yl)methyl acetate (350 mg, 1.29 mmol) was dissolved in DCM (6 mL) and cooled to 0° C. Bromine (227 mg, 1.42 mmol) was added dropwise and the mixture was stirred from 0° C. to room temperature over 2 hours. The mixture was then evaporated to dryness and used as is. [(2S,3R,4R,6R,7R)-3-bromo-1-[(1S)-1-phenylethyl]-1-azoniatricyclo[2.2.1.02,6]heptan-7-yl]methyl acetate. ES/MS: m/z 548.05 [M+H]$^+$.

Step 4

Bromo-1-[(1S)-1-phenylethyl]-1-azoniatricyclo[2.2.1.02,6]heptan-7-yl]methyl acetate; bromide (556 mg, 1.29 mmol) was dissolved in 2-MeTHF (3 mL) and the solution was cooled to 0° C. LiAlH$_4$ (1M in THF, 3.23 mL) was then added dropwise and the reaction was monitored by LCMS. Upon completion the reaction mixture was worked up using Fieser work up. The residue was then purified by column chromatography to afford [(1R,3R,4R,7R)-7-bromo-2-[(1S)-1-phenylethyl]-2-azabicyclo[2.2.1]heptan-3-yl]methanol. ES/MS: m/z 311.97 [M+H]$^+$.

Step 5

[(1R,3R,4R,7R)-7-bromo-2-[(1S)-1-phenylethyl]-2-azabicyclo[2.2.1]heptan-3-yl]methanol (300 mg, 0.96 mmol) was dissolved in ammonia in methanol (7N, 5 mL) in a microwave vial. The vial was then sealed, and the mixture was heated to 65° C. for 3 hours. The volatiles were evaporated, and the residue was then taken in DCM. Di-tert-butyl decarbonate (422 mg, 1.5 mmol) was then added followed by triethylamine (1 mL). Upon completion the mixture was evaporated to dryness and purified by column chromatography over silica gel to afford tert-butyl ((1R,3R,4S,7R)-3-(hydroxymethyl)-2-((S)-1-phenylethyl)-2-azabicyclo[2.2.1]heptan-7-yl)carbamate. ES/MS: m/z 347.06 [M+H]$^+$.

Step 6

((1R,3R,4S,7R)-3-(hydroxymethyl)-2-((S)-1-phenylethyl)-2-azabicyclo[2.2.1]heptan-7-yl)carbamate (110 mg, 0.32 mmol) was dissolved in EtOH (10 mL) and Pd(OH)$_2$ (15 mg) was added. The mixture was then agitated in a Parr Shaker at 30 PSI for 2 hours. LCMS indicated full conversion. After filtration and evaporation to dryness the residue was used without further purification. It was dissolved in MeCN (3 mL); K$_2$CO$_3$ (48 mg, 0.35 mmol) was added followed by benzyl bromide (59 mg, 0.35 mmol). The mixture was then stirred at room temperature overnight. After filtration the volatiles were evaporated and the residue was purified by chromatography over silica gel to afford tert-butyl ((1R,3R,4S,7R)-2-benzyl-3-(hydroxymethyl)-2-azabicyclo[2.2.1]heptan-7-yl)carbamate. ES/MS: m/z 333.02 [M+H]$^+$.

Step 7

Tert-butyl ((1R,3R,4S,7R)-2-benzyl-3-(hydroxymethyl)-2-azabicyclo[2.2.1]heptan-7-yl)carbamate (56 mg, 0.17 mmol) was dissolved in DMF (1 mL) and cooled to −40° C. Triethylamine (51 mg, 0.50 mmol) followed by methanesulfonic anhydride (65 mg, 0.37 mmol) and the reaction mixture was stirred from −40° C. to room temperature overnight. After work up the residue was purified by column chromatography over silica gel to afford (1R,4S,5S,8R)-2-benzyl-8-((tert-butoxycarbonyl)amino)-2-azabicyclo[3.2.1]octan-4-yl methanesulfonate. ES/MS: m/z 411.87 [M+H]$^+$.

Step 8

(1R,4S,5S,8R)-2-benzyl-8-((tert-butoxycarbonyl)amino)-2-azabicyclo[3.2.1]octan-4-yl methanesulfonate (29 mg, 0.07 mmol) was dissolved in diethyl ether (1 mL) and LiAlH$_4$ (1 M in Et$_2$O, 0.15 mL) was added dropwise. The reaction progressed was monitored by LCMS and upon completion the reaction was worked up using Fieser protocol. The residue was then purified by chromatography over silica gel to afford tert-butyl ((1R,5R,8R)-2-benzyl-2-azabicyclo[3.2.1]octan-8-yl)carbamate.

Step 9

(1R,5R,8R)-2-benzyl-2-azabicyclo[3.2.1]octan-8-yl)carbamate (10 mg, 0.03 mmol) was dissolved in EtOAc/MeOH (3:1, 5 mL) and one drop of TFA was added followed by Pd/C (10% w/w, 2 mg). The system was agitated in a Parr Shaker under an atmosphere of hydrogen (30 PSI) for 2 hours. Upon completion the residue was filtered and evaporated to dryness to afford tert-butyl ((1R,5R,8R)-2-azabicyclo[3.2.1]octan-8-yl)carbamate. ES/MS: 226.94 (M+H+). $^1$H NMR (400 MHz, Chloroform-d) δ 3.97-3.52 (m, 4H), 3.37-3.18 (m, 2H), 3.19-2.57 (m, 2H), 2.41-1.49 (m, 3H), 1.38 (s, 9H), 1.35-1.13 (m, 1H), 0.88-0.73 (m, 1H).

benzyl rac-((1R,4S,6R)-2-azabicyclo[2.2.2]octan-6-yl)carbamate (A37)

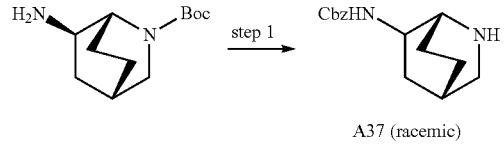 [SMILES: CC(C)(C)OC(=O)N1C[C@H]2CC[C@@H]1[C@H](N)C2 ; O=C(NC1C[C@@H]2CC[C@H]1NC2)OCc1ccccc1]

A37 (racemic)

Step 1 benzyl ((1R,4S,6R)-2-azabicyclo[2.2.2]octan-6-yl)carbamate was prepared using a similar procedure to A15 using tert-butyl rac-(1R,4S,6R)-6-amino-2-azabicyclo[2.2.2]octane-2-carboxylate. ES/MS: m/z 261.29 [M+H]$^+$. $^1$H NMR (400 MHz, DMSO-d6) δ 7.48-7.28 (m, 6H), 5.08-4.97 (m, 2H), 3.83 (brs, 1H), 3.68 (brs, 1H), 3.21-3.09 (m, 2H), 1.92-1.73 (m, 2H), 1.64-1.48 (m, 2H), 1.45-1.23 (m, 4H).

benzyl ((1R,2R,5S)-8-azabicyclo[3.2.1]octan-2-yl)carbamate (A38)

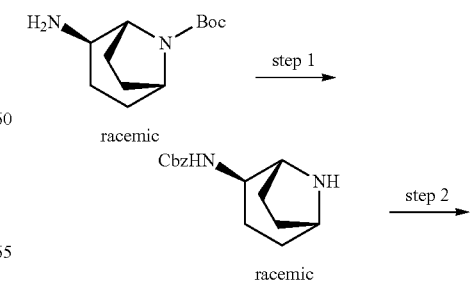

-continued

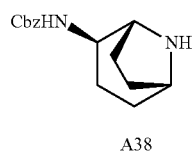

A38

Step 1 benzyl rac-((1R,2R,5S)-8-azabicyclo[3.2.1]octan-2-yl)carbamate was prepared using a similar procedure to A15 using tert-butyl rac-(1R,2R,5R)-2-amino-8-azabicyclo[3.2.1]octane-8-carboxylate.

Step 2

The racemic mixture of benzyl rac-((1R,2R,5S)-8-azabicyclo[3.2.1]octan-2-yl)carbamate was separated via chiral SFC (column IC-25, 30% MeOH). The second eluting peak was assigned as benzyl ((1R,2R,5S)-8-azabicyclo[3.2.1]octan-2-yl)carbamate. ES/MS: m/z 261.08 [M+H]+. 1H NMR (400 MHz, DMSO-d6) δ 9.13 (brs, 2H), 7.60 (d, J=7.7 Hz, 1H), 7.49-7.30 (m, 5H), 5.12-4.95 (m, 2H), 3.97-3.81 (m, 2H), 3.75 (dd, J=6.9, 2.9 Hz, 1H), 2.15-1.40 (m, 8H).

5. Example Procedures

Procedure 1 (Example 316)

(11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-1,10,19-triazatricyclo[10.5.2.0^{15,18}]nonadeca-12(19),13,15(18),16-tetraen-9-one

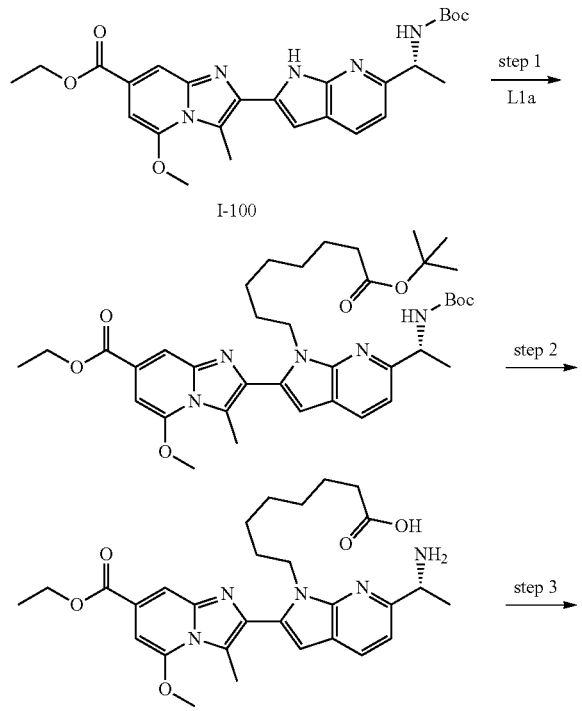

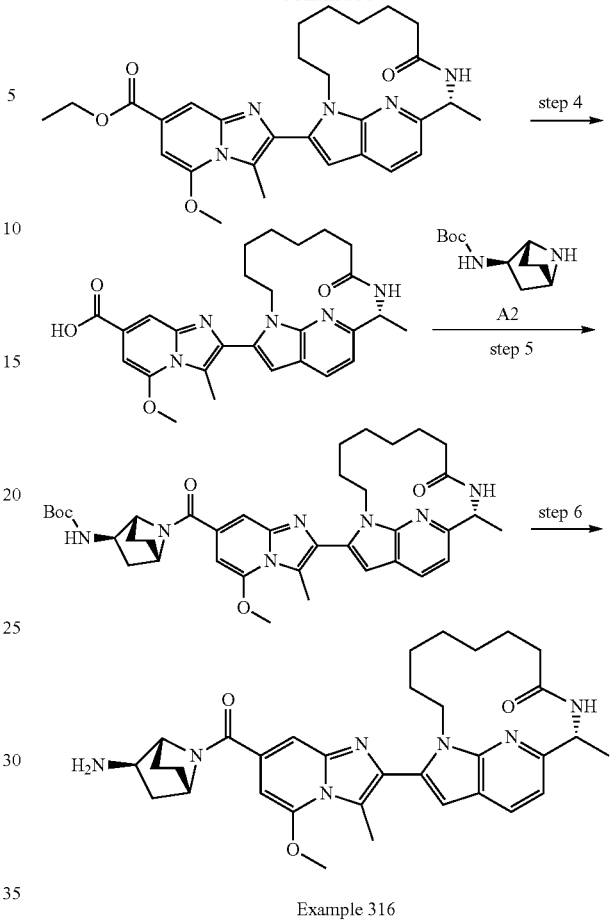

Example 316

Step 1

Ethyl (R)-2-(6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (I-100, 145 mg, 0.294 mmol) and tert-butyl 8-bromooctanoate (L1a, 98 mg, 0.353 mmol) were dissolved in DMF (1.5 mL). Cesium carbonate (287 mg, 0.881 mmol) was added and the resulting mixture was allowed to stir 1 h at 60° C. The reaction mixture was partitioned between EtOAc and water, and the organic phase was washed with brine, dried with MgSO4, filtered, and concentrated to provide crude ethyl (R)-2-(1-(8-(tert-butoxy)-8-oxooctyl)-6-(1-((tert-butoxycarbonyl)amino)ethyl)-1H-pyrrolo[2,3-b]pyridin-2-yl)-5-methoxy-3-methylimidazo[1,2-a]pyridine-7-carboxylate which was used below without further purification. ES/MS: m/z 692.5 [M+H]+.

Step 2

Crude ethyl (R)-2-(1-(8-(tert-butoxy)-8-oxooctyl)-6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (ca. 0.294 mml) was dissolved in DCM (2 mL) and TFA (0.5 mL) was added (4N HCl in dioxane can also be used). The reaction mixture was stirred 3 h at room temperature and was concentrated in vacuo to afford crude (R)-8-(6-(1-aminoethyl)-2-(7-(ethoxycarbonyl)-5-methoxy-3-methylimidazo[1,2-a]pyridin-2-yl)-1H-pyrrolo[2,3-b]pyridin-1-yl)octanoic acid which was used below without further purification. ES/MS: m/z 536.4 [M+H]+.

*If a Cbz was used instead of a Boc as protecting group, a standard hydrogenolysis (as per step 4 of A5a) was performed prior to step 2.

Step 3

Crude (R)-8-(6-(1-aminoethyl)-2-(7-(ethoxycarbonyl)-5-methoxy-3-methylimidazo[1,2-a]pyridin-2-yl)-1H-pyrrolo[2,3-b]pyridin-1-yl)octanoic acid (ca. 0.294 mmol) was dissolved in DCM (14 mL). N,N-diisopropylethylamine (396 uL, 2.27 mmol) was added followed by HATU (216 mg, 0.568 mmol). After 1 h, the reaction mixture was partitioned between EtOAc and water, and the organic phase was washed with brine, dried with MgSO₄, filtered, and concentrated. Purification by silica gel chromatography (5-80% (3:1 EtOAc/EtOH) in hexanes) provided ethyl 5-methoxy-3-methyl-2-[(11R)-11-methyl-9-oxo-1,10,19-triazatricyclo[10.5.2.0¹⁵,¹⁸]nonadeca-12(19),13,15(18),16-tetraen-17-yl]imidazo[1,2-a]pyridine-7-carboxylate. ES/MS: m/z 518.3 [M+H]⁺.

Step 4

Ethyl 5-methoxy-3-methyl-2-[(11R)-11-methyl-9-oxo-1,10,19-triazatricyclo[10.5.2.0¹⁵,¹⁸]nonadeca-12(19),13,15(18),16-tetraen-17-yl]imidazo[1,2-a]pyridine-7-carboxylate (85 mg, 0.164 mmol) was dissolved in THF (1 mL) and MeOH (1 mL). 1 M lithium hydroxide (0.5 mL) was added and the resulting mixture was stirred at rt for 30 min.

The resulting mixture can be concentrated to afford a crude solid that can be used directly below. Alternatively, the crude solid can be suspended in THF (1.5 mL) and before adding 4N HCl in dioxane (6 equiv.). The resulting solution is then evaporated to dryness and used directly below. ES/MS: m/z 490.3 [M+H]⁺.

Step 5

Crude product from above (ca. 0.135 mmol) was dissolved in DMF (1 mL), and tert-butyl ((1R,2R,4S)-7-azabicyclo[2.2.1]heptan-2-yl)carbamate (37 mg, 0.176 mmol) was added followed by N,N-diisopropylethylamine (106 µL, 0.607 mmol) and HATU (77 mg, 0.202 mmol). After 30 min, the reaction mixture was partitioned between EtOAc and water, and the organic phase was washed with brine, dried with MgSO₄, filtered, and concentrated to afford crude tert-butyl N-[(1R,2R,4S)-7-[5-methoxy-3-methyl-2-[(11R)-11-methyl-9-oxo-1,10,19-triazatricyclo[10.5.2.0¹⁵,¹⁸]nonadeca-12(19),13,15(18),16-tetraen-17-yl]imidazo[1,2-a]pyridine-7-carbonyl]-7-azabicyclo[2.2.1]heptan-2-yl]carbamate which was used below without further purification. ES/MS: m/z 684.3 [M+H]⁺.

Step 6

Crude tert-butyl N-[(1R,2R,4S)-7-[5-methoxy-3-methyl-2-[(11R)-11-methyl-9-oxo-1,10,19-triazatricyclo[10.5.2.0¹⁵,¹⁸]nonadeca-12(19),13,15(18),16-tetraen-17-yl]imidazo[1,2-a]pyridine-7-carbonyl]-7-azabicyclo[2.2.1]heptan-2-yl]carbamate (ca. 0.135 mmol) was dissolved in DCM (2 mL) and TFA (1 mL). After stirring 20 min, the reaction mixture was concentrated and purified directly by preparative HPLC (5-100% MeCN in water, 0.1% TFA) to afford Example 316.

Alternative Step 6 when Cbz was Used as Protecting Group for Intermediate A.

The Cbz-protected intermediate was combined with 10% Pd/C (0.2 equiv.) in a 1:1 mixture of EtOH/EtOAc (0.2M) and treated with H₂ gas. After stirring 3 hours, the reaction mixture was filtered through celite, concentrated and purified directly by preparative HPLC.

Note:

For compounds made by this sequence, alternative reagents, solvent, temperature, or isolation methods may have been used.

Procedure 2 (Examples 327 and 328)

(3~{S},5~{R},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one (Example 327)

(3~{R},5~{S},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one Example 328

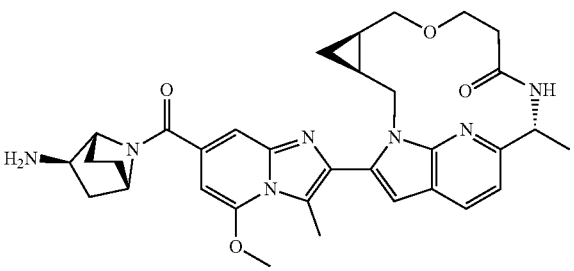

Example 327

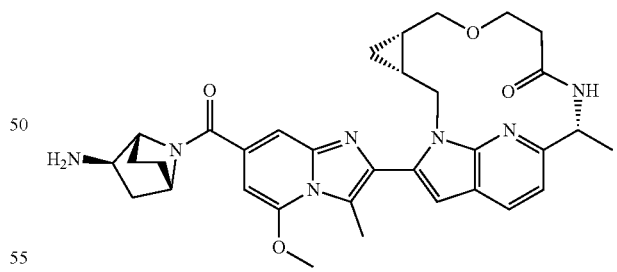

Example 328

The 1:1 diastereoisomeric mixture of Examples 327 and 328 was prepared following Procedure 1 using L13a instead of L1a. Examples 327 and 328 were separated via chiral SFC. The first eluting peak was arbitrarily assigned as the (3S,5R)-configuration (Example 327), and the second eluting peak was assigned as the (3R,5S)-configuration (Example 328).

*In other instances, diastereoisomeric mixtures of Examples can be separated via preparative HPLC or preparative chiral HPLC.

499

Procedure 3 (Examples 334 and 335)

(8~{R},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8-methoxy-11-methyl-1,10,19-triazatricyclo[10.5.2^{15,18}]nonadeca-12(19),13,15(18),16-tetraen-9-one (Example 334)

(8~{S},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8-methoxy-11-methyl-1,10,19-triazatricyclo[10.5.2.0^{15,18}]nonadeca-12(19),13,15(18),16-tetraen-9-one (Example 335)

Example 334

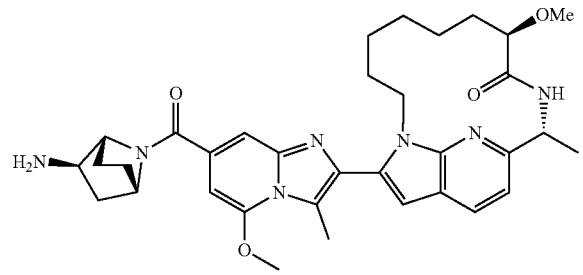

Example 335

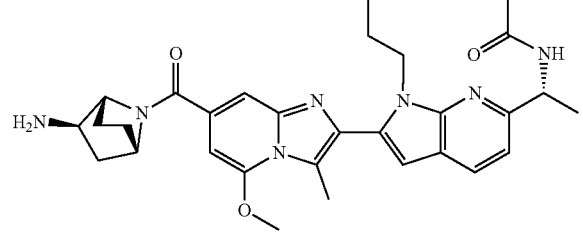

Examples 334 and 335 were prepared following Procedure 1 using L18 instead of L1a. After purification by silica gel chromatography at the macrocyclization step (step 3 of Procedure 1), the first eluting peak was arbitrarily assigned as the 8R-configuration, and the second eluting peak was assigned as the 8S-configuration. Both diastereoisomers were separately submitted to steps 4-6 of Procedure 1 to provide Examples 334 and 335.

500

Procedure 4 (Example 120)

(12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-1,11,20-triazatricyclo[11.5.2.0^{16,19}]icosa-3,13(20),14,16(19),17-pentaen-10-one

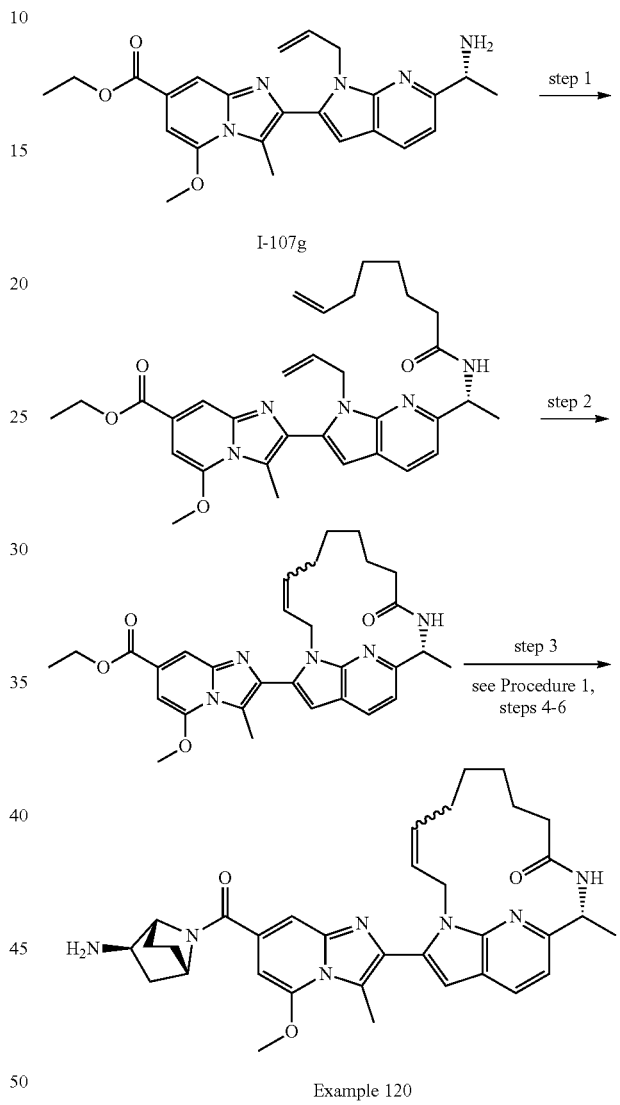

Step 1

To a solution of ethyl (R)-2-(1-allyl-6-(1-aminoethyl)-1H-pyrrolo[2,3-b]pyridin-2-yl)-5-methoxy-3-methylimidazo[1,2-a]pyridine-7-carboxylate (20 mg, 0.46 mmol), oct-7-enoic acid (0.014 mL, 0.92 mmol), and N,N-diisopropylethylamine (0.08 ml, 0.46 mmol) in DMF (0.5 mL) was added HATU (35 mg, 0.092 mmol). The mixture was allowed to stir for 1 h. Sat. aq. NaHCO$_3$ was added and the mixture was extracted twice with dichloromethane. The combined organic phases were dried over Na$_2$SO$_4$, filtered, and adsorbed onto silica. Purification by silica gel chromatography (50-100% EtOAc in hexanes) provided ethyl (R)-2-(1-allyl-6-(1-(oct-7-enamido)ethyl)-1H-pyrrolo[2,3-b]pyridin-2-yl)-5-methoxy-3-methylimidazo[1,2-a]pyridine-7-carboxylate. ES/MS: m/z 558.4 [M+H]$^+$.

Step 2

A solution of ethyl (R)-2-(1-allyl-6-(1-(oct-7-enamido)ethyl)-1H-pyrrolo[2,3-b]pyridin-2-yl)-5-methoxy-3-methylimidazo[1,2-a]pyridine-7-carboxylate (20 mg, 0.036 mmol) and (1,3-dimesitylimidazolidin-2-ylidene)dichloro(2-isopropoxy-5-nitrobenzylidene)ruthenium(II) (5 mg, 0.007 mmol) in 1,2-dichloroethane (5 mL) under $N_2$ atmosphere was allowed to stir at 60° C. for 18 h. To this solution was added more (1,3-dimesitylimidazolidin-2-ylidene)dichloro(2-isopropoxy-5-nitrobenzylidene)ruthenium(II) (5 mg, 0.007 mmol.) The solution was allowed to stir at 60° C. for 4 h and then the reaction mixture was adsorbed onto silica gel. Purification by silica gel chromatography (0-100% EtOAc in hexanes, then 0-40% methanol in EtOAc) provided ethyl 5-methoxy-3-methyl-2-[(3Z,12R)-12-methyl-10-oxo-1,11,20-triazatricyclo[11.5.2.016,19]icosa-3,13(20),14,16(19),17-pentaen-18-yl]imidazo[1,2-a]pyridine-7-carboxylate. ES/MS: m/z 530.3 [M+H]$^+$.

Step 3

Example 120 was made following steps 4-6 of Procedure 1 using ethyl 5-methoxy-3-methyl-2-[(3Z,12R)-12-methyl-10-oxo-1,11,20-triazatricyclo[11.5.2.016,19]icosa-3,13(20),14,16(19),17-pentaen-18-yl]imidazo[1,2-a]pyridine-7-carboxylate.

Procedure 5 (Example 127)

17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-1,11,19-triazatricyclo[10.5.2.0^{15,18}]nonadeca-12(19),13,15(18),16-tetraen-10-one

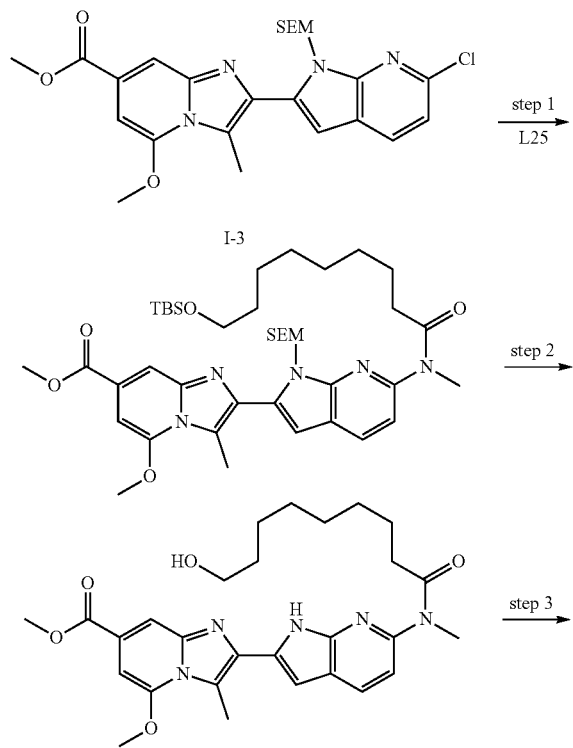

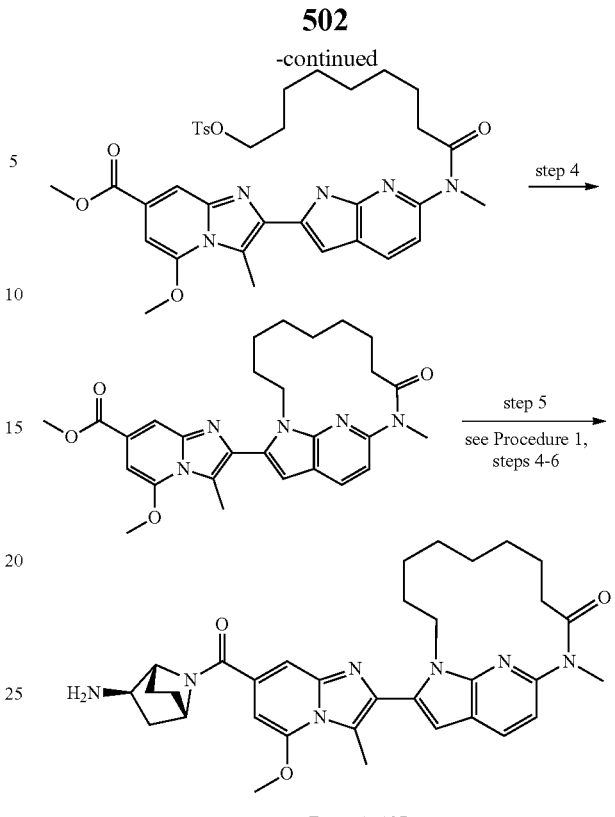

Example 127

Step 1.

A solution of methyl 2-(6-chloro-1-((2-(trimethylsilyl)ethoxy)methyl)-1H-pyrrolo[2,3-b]pyridin-2-yl)-5-methoxy-3-methylimidazo[1,2-a]pyridine-7-carboxylate (160 mg, 0.32 mmol), 9-[tert-butyl(dimethyl)silyl]oxy-N-methylnonanamide (L25) (190 mg, 0.64), JackiPhos Pd G3 (37 mg, 0.032 mmol), and cesium carbonate (310 mg, 0.96 mmol) in toluene (1 mL) was degassed by bubbling nitrogen for 5 min and then, stirred in a microwave at 130° C. for 1 h. The reaction mixture filtered through Celite, washing with DCM, and the supernatant was adsorbed onto silica gel and purified by silica gel chromatography (50-100% EtOAc in hexanes, then 0-40% MeOH in EtOAc) to provide methyl 2-[6-[9-[tert-butyl(dimethyl)silyl]oxynonanoyl-methyl-amino]-1-(2-trimethylsilylethoxymethyl)pyrrolo[2,3-b]pyridin-2-yl]-5-methoxy-3-methyl-imidazo[1,2-a]pyridine-7-carboxylate. ES/MS: m/z 766.0 [M+H]$^+$.

Step 2

A solution of methyl 2-[6-[9-[tert-butyl(dimethyl)silyl]oxynonanoyl-methyl-amino]-1-(2-trimethylsilylethoxymethyl)pyrrolo[2,3-b]pyridin-2-yl]-5-methoxy-3-methyl-imidazo[1,2-a]pyridine-7-carboxylate (212 mg, 0.28 mmol) and conc. HCl (0.046 mL) in MeOH (2.5 mL) was allowed to stir at room temperature for 1 h. The reaction was concentrated and brought up in DCM (1 mL). TFA (1 mL) was added and the mixture was allowed to stir overnight. Saturated sodium bicarbonate was added and the aqueous layer was washed three times with DCM. The combined organic layers were dried over $Na_2SO_4$, filtered and concentrated. The residue was brought up in MeOH (2.5 mL) and to this solution was added ethylenediamine (0.056 mL, 0.83 mmol). The reaction was allowed to stir for 3 h. Solution was adsorbed onto silica and purified by silica gel chromatography (0-60% MeOH in EtOAc w/20% DCM additive) to provide methyl 2-(6-(9-hydroxy-N-methylnonanamido)-1H-pyrrolo[2,3-b]

pyridin-2-yl)-5-methoxy-3-methylimidazo[1,2-a]pyridine-7-carboxylate. ES/MS: m/z 522.2 [M+H]+.

Step 3

To a solution of methyl 2-(6-(9-hydroxy-N-methyl-nonanamido)-1H-pyrrolo[2,3-b]pyridin-2-yl)-5-methoxy-3-methylimidazo[1,2-a]pyridine-7-carboxylate (60 mg, 0.12 mmol), triethylamine (0.048 mL, 0.35 mmol), and 4-dimethylaminopyridine (2 mg, 0.01 mmol) in DCM (1 mL) was added 4-toluenesulfonyl chloride (27 mg, 0.11 mmol). The solution was stirred for 1 h. More 4-toluenesulfonyl chloride (5 mg, 0.002 mmol) was added every hour until the reaction was complete. After 5 h, the reaction was concentrated and purified by silica gel chromatography (0-60% MeOH in EtOAc) to provide methyl 5-methoxy-3-methyl-2-(6-(N-methyl-9-(tosyloxy)nonanamido)-1H-pyrrolo[2,3-b]pyridin-2-yl)imidazo[1,2-a]pyridine-7-carboxylate. ES/MS: m/z 676.2 [M+H]+.

Step 4

A mixture of methyl 5-methoxy-3-methyl-2-(6-(N-methyl-9-(tosyloxy)nonanamido)-1H-pyrrolo[2,3-b]pyridin-2-yl)imidazo[1,2-a]pyridine-7-carboxylate (60 mg, 0.089 mmol) and cesium carbonate (145 mg, 0.44 mmol) in THF (6 mL) was allowed to stir at 60° C. overnight. Brine was added to the solution and the mixture was extracted twice with EtOAc. The combined organic layers were dried over Na2SO4, filtered and concentrated. The residue was purified by silica gel chromatography (0-50% MeOH in EtOAc) to provide methyl 5-methoxy-3-methyl-2-(11-methyl-10-oxo-1,11,19-triazatricyclo[10.5.2.015,18]nonadeca-12(19),13,15(18),16-tetraen-17-yl)imidazo[1,2-a]pyridine-7-carboxylate. ES/MS: m/z 504.3 [M+H]+.

Step 5

Example 127 was made following steps 4-6 of Procedure 1 using methyl 5-methoxy-3-methyl-2-(11-methyl-10-oxo-1,11,19-triazatricyclo[10.5.2.015,18]nonadeca-12(19),13,15(18),16-tetraen-17-yl)imidazo[1,2-a]pyridine-7-carboxylate.

Procedure 6 (Example 209)

(9~{R})-15-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-6,9-dimethyl-1,6,8,17-tetrazatricyclo[8.5.2.0^{13,16}]heptadeca-10(17),11,13(16),14-tetraen-7-one

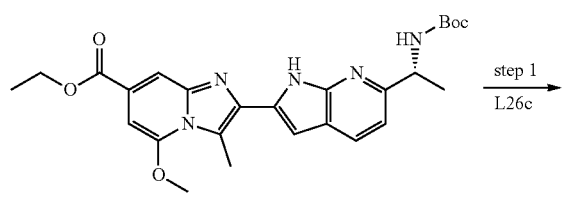

I-100

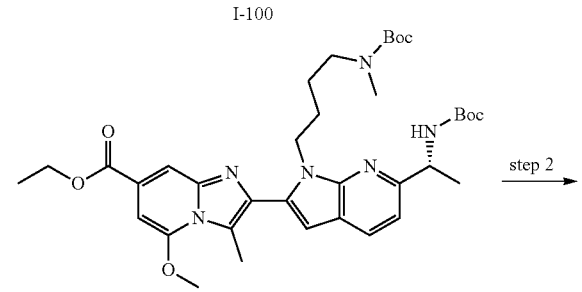

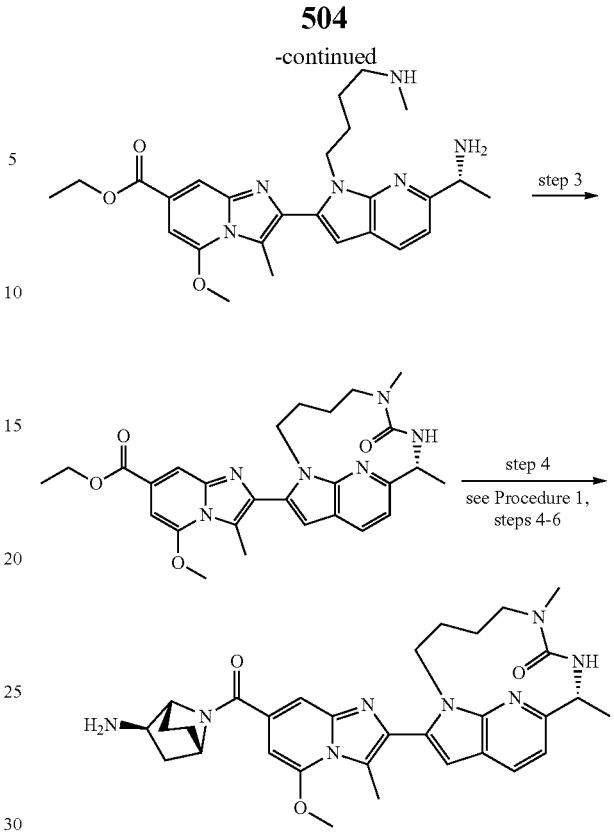

Example 209

Step 1

A vial was charged with the ethyl (R)-2-(6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (I-100, 32.4 mg, 0.122 mmol), L26c (47 mg, 0.171 mmol, 1.2 equiv.) and cesium carbonate (99 mg, 0.304 mmol, 3 equiv.). DMF (0.4 mL) was added and the mixture was heated at 70° C. for 5 h. Upon cooling to room temperature, ethyl acetate (5 mL) and water (10 mL) were added. The layers were separated and the aqueous layer was extracted with ethyl acetate (5 mL). The combined organic layers were dried over sodium sulfate, filtered and evaporated to dryness. Purification by silica gel chromatography (Heptane/Ethyl acetate 0% to 50%) afforded ethyl (R)-2-(1-(4-((tert-butoxycarbonyl)(methyl)amino)butyl)-6-(1-((tert-butoxycarbonyl)amino)ethyl)-1H-pyrrolo[2,3-b]pyridin-2-yl)-5-methoxy-3-methylimidazo[1,2-a]pyridine-7-carboxylate. ES/MS: m/z 679.5 [M+H]+.

Step 2

Ethyl (R)-2-(1-(4-((tert-butoxycarbonyl)(methyl)amino)butyl)-6-(1-((tert-butoxycarbonyl)amino)ethyl)-1H-pyrrolo[2,3-b]pyridin-2-yl)-5-methoxy-3-methylimidazo[1,2-a]pyridine-7-carboxylate (62 mg, 0.091 mmol) was dissolved in DCM (1 mL) and TFA (1 mL). The mixture was stirred at room temperature until LCMS analysis showed full conversion to the desired diamine (1 h). The mixture was evaporated to dryness, dried under vacuum for 1 h and the crude ethyl (R)-2-(6-(1-aminoethyl)-1-(4-(methylamino)butyl)-1H-pyrrolo[2,3-b]pyridin-2-yl)-5-methoxy-3-methylimidazo[1,2-a]pyridine-7-carboxylate was used without further purification in the next step.

Step 3

To crude ethyl (R)-2-(6-(1-aminoethyl)-1-(4-(methylamino)butyl)-1H-pyrrolo[2,3-b]pyridin-2-yl)-5-methoxy-3-methylimidazo[1,2-a]pyridine-7-carboxylate (ca. 0.091 mmol) in DCM (5 mL) was added Hunigs base (95 µL, 0.548 mmol) followed by CDI (14.8 mg, 0.091 mmol). The mixture was stirred at 45° C. for 2 h. Another portion of CDI (3 mg, 0.018 mmol) was added and the reaction was stirred for an additional 4 h at 45° C. The mixture was then evaporated to dryness and purified by column chromatography over silica gel (DCM/EtOAc 30-100%) to afford ethyl 2-[(9R)-6,9-dimethyl-7-oxo-1,6,8,17-tetrazatricyclo[8.5.2.013,16]heptadeca-10(17),11,13(16),14-tetraen-15-yl]-5-methoxy-3-methyl-imidazo[1,2-a]pyridine-7-carboxylate. ES/MS: m/z 519.1 [M+H]+.

Step 4

Example 209 was made following steps 4-6 of Procedure 1 using ethyl 2-[(9R)-6,9-dimethyl-7-oxo-1,6,8,17-tetrazatricyclo[8.5.2.013,16]heptadeca-10(17),11,13(16),14-tetraen-15-yl]-5-methoxy-3-methyl-imidazo[1,2-a]pyridine-7-carboxylate.

Procedure 7 (Example 293)

17-[7-[(3~{R})-3-aminopiperidine-1-carbonyl]-5-methoxy-3-methyl-imidazo[1,2-a]pyridin-2-yl]-11l-oxa-1,8,19-triazatricyclo[10.5.2.0^{15,18}]nonadeca-12(19),13,15(18),16-tetraen-9-one

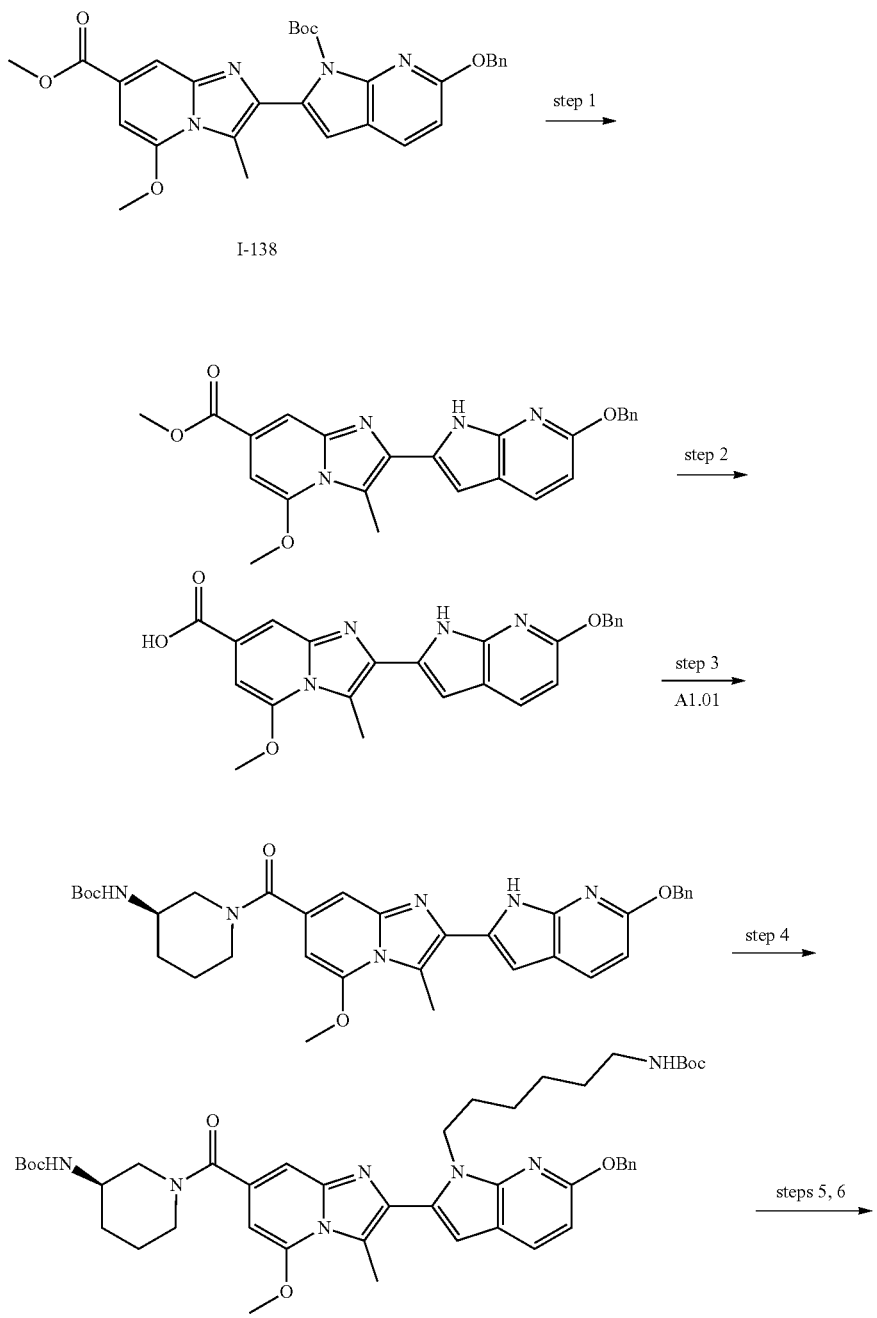

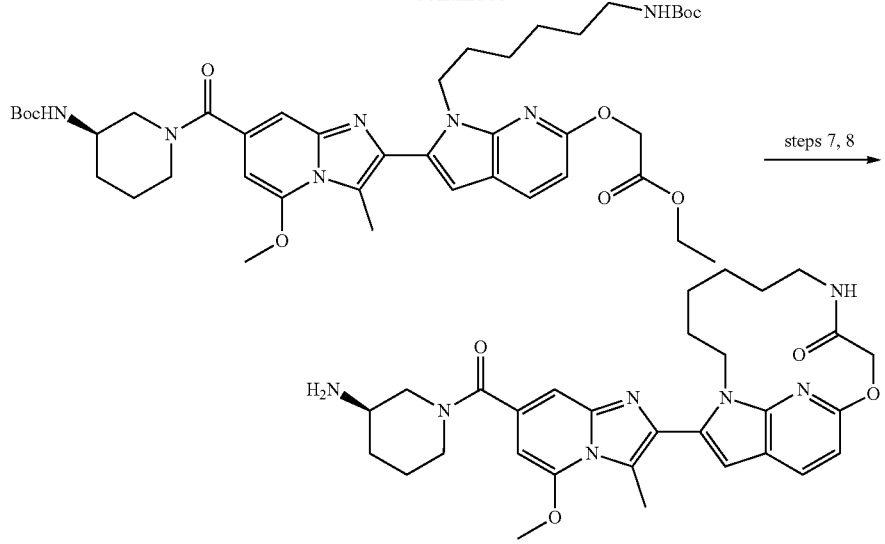

Example 293

Step 1

A solution of methyl 2-(6-benzyloxy-1-tert-butoxycarbonyl-pyrrolo[2,3-b]pyridin-2-yl)-5-methoxy-3-methyl-imidazo[1,2-a]pyridine-7-carboxylate (0.36 g, 0.66 mmol) in dichloromethane (2 mL) and trifluoroacetic acid (2 mL) was stirred for 1 h. The mixture was concentrated, diluted with EtOAc (10 ml) and washed with 1 M $Na_2HPO_4$ (aq, 10 mL), followed by water (2×10 mL). The organic layer was dried with $Na_2SO_4$, filtered, and concentrated. The crude methyl 2-(6-(benzyloxy)-1H-pyrrolo[2,3-b]pyridin-2-yl)-5-methoxy-3-methylimidazo[1,2-a]pyridine-7-carboxylate was taken to next step without further purification. ES/MS: m/z 443.1 $[M+H]^+$.

Step 2

A solution of methyl 2-(6-benzyloxy-1-tert-butoxycarbonyl-pyrrolo[2,3-b]pyridin-2-yl)-5-methoxy-3-methyl-imidazo[1,2-a]pyridine-7-carboxylate (0.7 g, 1.29 mmol) in methanol (10 mL) and 10 M NaOH (0.5 mL) was heated in a microwave reactor at 80° C. for 20 minutes. The mixture was concentrated, diluted with water (5 mL), and acidified to pH 3 with 2 M HCl. The solids were filtered and the filtrate was extracted with MeTHF (2×10 mL). The organic layer was dried with $Na_2SO_4$, filtered, and concentrated. The solids were combined and the crude 2-(6-(benzyloxy)-1H-pyrrolo[2,3-b]pyridin-2-yl)-5-methoxy-3-methylimidazo[1,2-a]pyridine-7-carboxylic acid was taken to next step without further purification. ES/MS: m/z 429.1 $[M+H]^+$.

Step 3

To a solution of 2-(6-benzyloxy-1H-pyrrolo[2,3-b]pyridin-2-yl)-5-methoxy-3-methyl-imidazo[1,2-a]pyridine-7-carboxylic acid (400 mg, 0.93 mmol), tert-butyl (R)-piperidin-3-ylcarbamate (A1.01, 223 mg, 1.12 mmol), and EtN(i-Pr)$_2$ (0.24 ml, 1.4 mmol) in DMF (2 mL) was added HATU (390 mg, 1.03 mmol). After stirring for 15 minutes, the mixture was diluted with EtOAc (10 mL) and washed with 5% LiCl (aq, 10 mL). The organic layer was dried with $Na_2SO_4$, filtered, and concentrated. The crude tert-butyl (R)-(1-(2-(6-(benzyloxy)-1H-pyrrolo[2,3-b]pyridin-2-yl)-5-methoxy-3-methylimidazo[1,2-a]pyridine-7-carbonyl)piperidin-3-yl)carbamate was taken to next step without further purification. ES/MS: m/z 611.3 $[M+H]^+$.

Step 4

A mixture of tert-butyl (R)-(1-(2-(6-(benzyloxy)-1H-pyrrolo[2,3-b]pyridin-2-yl)-5-methoxy-3-methylimidazo[1,2-a]pyridine-7-carbonyl)piperidin-3-yl)carbamate (75 mg, 122 µmol), tert-butyl N-(6-iodohexyl)carbamate (48 mg, 147 µmol), and $Cs_2CO_3$ (120 mg, 36 µmol) in DMF (0.4 mL) was stirred at 50° C. for 18 h. The mixture was diluted with EtOAc (3 mL) and washed with water (3 mL). The organic layer was dried with $Na_2SO_4$, filtered, and concentrated. The crude tert-butyl (R)-(1-(2-(6-(benzyloxy)-1-(6-((tert-butoxycarbonyl)amino)hexyl)-1H-pyrrolo[2,3-b]pyridin-2-yl)-5-methoxy-3-methylimidazo[1,2-a]pyridine-7-carbonyl)piperidin-3-yl)carbamate was taken to next step without further purification. ES/MS: m/z 810.3 $[M+H]^+$.

Step 5

A mixture of tert-butyl (R)-(1-(2-(6-(benzyloxy)-1-(6-((tert-butoxycarbonyl)amino)hexyl)-1H-pyrrolo[2,3-b]pyridin-2-yl)-5-methoxy-3-methylimidazo[1,2-a]pyridine-7-carbonyl)piperidin-3-yl)carbamate (100 mg, 123 µmol) and 10% palladium on carbon (13 mg) in methanol (2 ml) was stirred under an atmosphere of hydrogen for 2 h. The catalyst was filtered through a 0.45 M filter and the filtrate was concentrated. The crude product was taken to next step without further purification. ES/MS: m/z 720.3 $[M+H]^+$.

Step 6

A mixture of tert-butyl (R)-(1-(2-(1-(6-((tert-butoxycarbonyl)amino)hexyl)-6-hydroxy-1H-pyrrolo[2,3-b]pyridin-2-yl)-5-methoxy-3-methylimidazo[1,2-a]pyridine-7-carbonyl)piperidin-3-yl)carbamate (30 mg, 41.7 µmol), ethyl 2-iodoacetate (4.9 µl, 41.7 µmol), and $Cs_2CO_3$ (20.4 mg, 62.5 µmol) in DMF (0.2 ml) was stirred at ambient temperature for 30 minutes. The mixture was diluted with EtOAc (2 ml) and washed with 5% LiCl (aq, 3×2 ml). The organic layer was dried with $Na_2SO_4$, filtered, and concentrated. The crude ethyl (R)-2-((1-(6-((tert-butoxycarbonyl)amino)hexyl)-2-(7-(3-((tert-butoxycarbonyl)amino)piperidine-1-carbonyl)-5-methoxy-3-methylimidazo[1,2-a]pyridin-2-yl)-1H-pyrrolo[2,3-b]pyridin-6-yl)oxy)acetate was taken to next step without further purification. ES/MS: m/z 806.3 $[M+H]^+$.

Step 7.

A mixture of ethyl (R)-2-((1-(6-((tert-butoxycarbonyl)amino)hexyl)-2-(7-(3-((tert-butoxycarbonyl)amino)piperidine-1-carbonyl)-5-methoxy-3-methylimidazo[1,2-a]pyridin-2-yl)-1H-pyrrolo[2,3-b]pyridin-6-yl)oxy)acetate (34 mg, 42.2 μmol) in methanol (500 μl) and 10 M aqueous NaOH (4.5 μl) was stirred overnight at ambient temperature. The mixture was concentrated and dried under vacuum. The mixture was suspended in EtOAc (0.5 ml) and treated with 3 M HCl in CPME. The suspension was stirred at ambient temperature for 2 h. The solids were allowed to settle and solution was decanted from the settled solids, washed with EtOAc, and dried under vacuum. The crude product was taken to next step without further purification. ES/MS: m/z 578.3 [M+H]$^+$.

Step 8

To a suspension of (R)-2-((1-(6-aminohexyl)-2-(7-(3-aminopiperidine-1-carbonyl)-5-methoxy-3-methylimidazo[1,2-a]pyridin-2-yl)-1H-pyrrolo[2,3-b]pyridin-6-yl)oxy)acetic acid trihydrochloride (29 mg, 42 μmol) and DIPEA (44 μl, 252 μmol) in DMA (0.8 ml) was added HATU (16 mg, 42 μmol) in 4 mg portions. After stirring for 15 mins, the mixture was diluted with water (2 ml) followed by trifluoroacetic acid (40 μl). The crude material was purified HPLC (eluent: water/MeCN*0.1% TFA) to afford 17-[7-[(3~{R})-3-aminopiperidine-1-carbonyl]-5-methoxy-3-methyl-imidazo[1,2-a]pyridin-2-yl]-11-oxa-1,8,19-triazatricyclo [10.5.2.0^{15,18}]nonadeca-12(19),13,15(18),16-tetraen-9-one Example 293.

Procedure 8 (Example 215)

(11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-1,10-diazatricyclo[10.5.2.0^{15,18}]nonadeca-12(19),13,15(18),16-tetraen-9-one

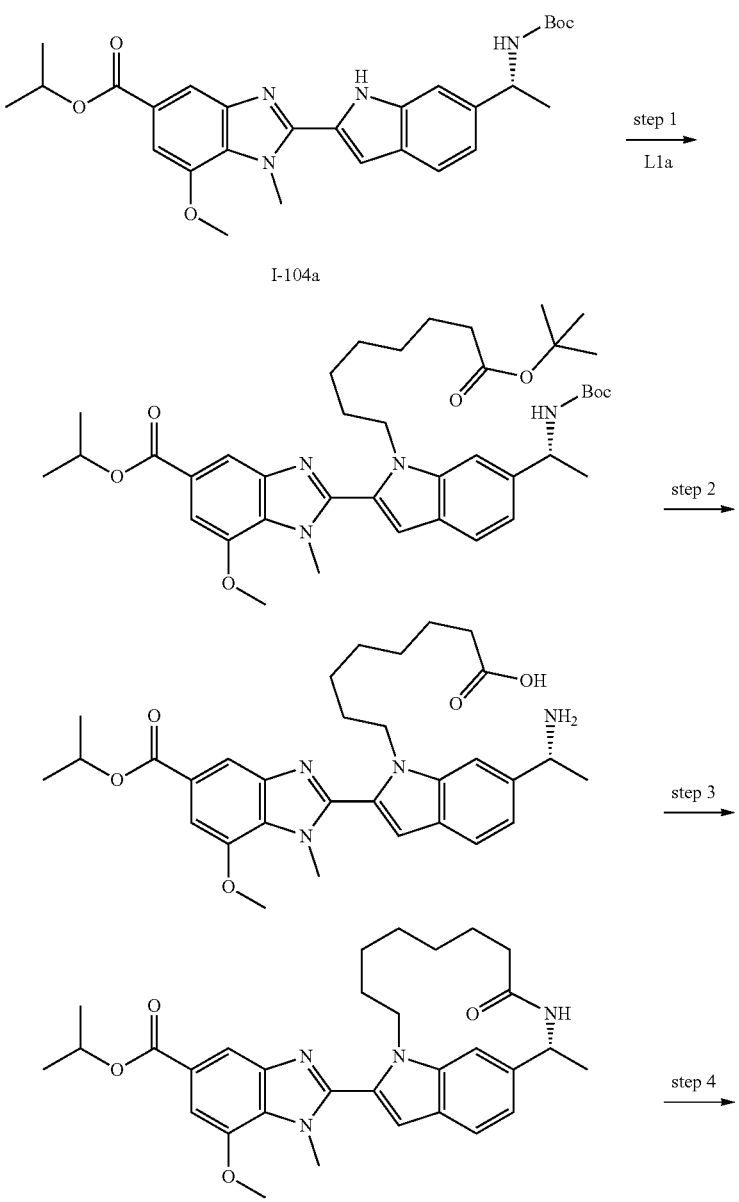

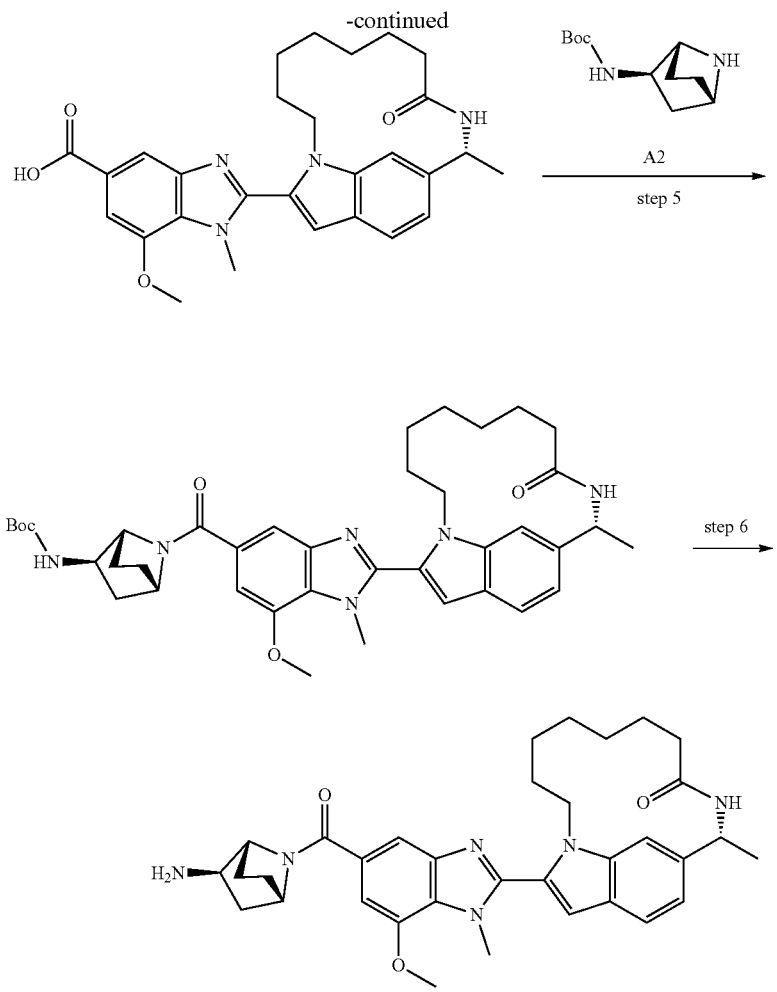

Example 215

Step 1

A vial was charged with isopropyl (R)-2-(6-(1-((tert-butoxycarbonyl)amino)ethyl)-1H-indol-2-yl)-7-methoxy-1-methyl-1H-benzo[d]imidazole-5-carboxylate (I-104a, 58 mg, 0.114 mmol), tert-butyl 8-bromooctanoate (L1a, 47 mg, 0.171 mmol, 1.5 equiv.) and cesium carbonate (186 mg, 0.57 mmol, 5 equiv.). NMP (1.1 mL, 0.1 M) was added and the mixture was heated at 95° C. for 3 hours.

Notes:

For the alkylation of azaindole intermediates such as I-102, DMF at 65° C. was used instead of NMP at 95° C. Additional L1a may be required to reach full conversion.

The crude mixture was cooled to room temperature and ethyl acetate (5 mL) and water (10 mL) were added. The layers were separated and the aqueous layer was extracted with ethyl acetate. The combined organic layers were dried over sodium sulfate, filtered and evaporated to dryness. Purification by silica gel chromatography (Heptane/Ethyl acetate 0% to 40%) to afford isopropyl (R)-2-(1-(8-(tert-butoxy)-8-oxooctyl)-6-(1-((tert-butoxycarbonyl)amino)ethyl)-1H-indol-2-yl)-7-methoxy-1-methyl-1H-benzo[d]imidazole-5-carboxylate. ES/MS: m/z 705.4 [M+H]$^+$.

Step 2

Isopropyl (R)-2-(1-(8-(tert-butoxy)-8-oxooctyl)-6-(1-((tert-butoxycarbonyl)amino)ethyl)-1H-indol-2-yl)-7-methoxy-1-methyl-1H-benzo[d]imidazole-5-carboxylate (72 mg, 0.101 mmol) was dissolved in DCM and HCl in dioxane (4 N, 0.38 mL, 15 equiv.) was added. The mixture was stirred at room temperature until full conversion of the starting material as judged by LCMS analysis. The reaction mixture was then evaporated to dryness and crude (R)-8-(6-(1-aminoethyl)-2-(5-(isopropoxycarbonyl)-7-methoxy-1-methyl-1H-benzo[d]imidazol-2-yl)-1H-indol-1-yl)octanoic acid was used directly in the next step without further purification. ES/MS: m/z 549.2 [M+H]$^+$.

Step 3

Crude (R)-8-(6-(1-aminoethyl)-2-(5-(isopropoxycarbonyl)-7-methoxy-1-methyl-1H-benzo[d]imidazol-2-yl)-1H-indol-1-yl)octanoic was dissolved in DCM (5 mL, 0.02 M) and Hunig's base (70 µL, 0.404 mmol, 4 equiv.) was added. The mixture was stirred for 1 minute before HATU was added in one portion. The resulting solution was stirred at room temperature for 1 h. Ethyl acetate (10 mL) and water (30 mL) were added. After regular work-up the residue was purified by column chromatography over silica gel (Heptane/Ethyl acetate 5% to 70%) to afford isopropyl 7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carboxylate. ES/MS: m/z 531.2 [M+H]$^+$.

Step 4

Isopropyl 7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carboxylate (37 mg, 0.070 mmol) was dissolved in a 1:1 mixture of THF/MeOH (1 mL) and a solution of LiOH (2 M in water, 70 µL, 0.140 mmol) was added. The resulting mixture was stirred vigorously at 50° C. until full conversion of the starting ester to the corresponding acid. The solution was then cooled to room temperature and evaporated to dryness. The crude solid was suspended in THF (1.5 mL) and HCl in dioxane (4 N, 105 µL, 6 equiv.) was added. A solution was obtained and evaporated to dryness after 5 minutes. Crude 7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carboxylic acid was used without further purification. ES/MS: m/z 488.3 [M+H]⁺.

Step 5

Crude 7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carboxylic acid (36 mg, 0.07 mmol) and A2 (18 mg, 0.084 mmol, 1.2 equiv.) were charged in a vial. DMF (0.7 mL, 0.1 M), Hunig's base (37 µL, 0.21 mmol, 3 equiv.) and HATU (40 mg, 0.105 mmol, 1.5 equiv.) were then added. The resulting mixture was stirred at room temperature. After 30 min, the reaction mixture was partitioned between EtOAc and water, and the organic phase was washed with brine, dried with MgSO₄, filtered, and concentrated to afford crude tert-butyl N-[(1R,2R,4S)-7-[7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carbonyl]-7-azabicyclo[2.2.1]heptan-2-yl]carbamate which was used below without further purification. ES/MS: m/z 683.4 [M+H]⁺.

Step 6 (Deprotection of Boc- and Trityl-Protected Amines).

Crude product from above (ca. 0.07 mmol) was dissolved in DCM (1 mL) and TFA (1 mL). After stirring 20 min, the reaction mixture was concentrated and purified directly by preparative HPLC (5-100% MeCN in water, 0.1% TFA) to afford Example 215.

Alternative Step 6 when Cbz was Used as Protecting Group for Intermediate A.

The Cbz-protected intermediate was combined with 10% Pd/C (0.2 equiv.) in a 1:1 mixture of EtOH/EtOAc (0.2M) and treated with H₂ gas. After stirring 3 hours, the reaction mixture was filtered through celite, concentrated and purified directly by preparative HPLC.

Alternative Step 6 when a Phthalimide was Used as Protecting Group for Intermediate A.

Hydrazine hydrate (4 drops) was added to a solution of the penultimate intermediate above (0.05 mmol) in EtOH (1 mL) and the resulting mixture allowed to stir at ambient temperature overnight. The reaction was heated to 60° C. for one hour to ensure completion, then was concentrated and purified directly by preparative HPLC.

Note:

For compounds made by this sequence, alternative reagents, solvent, temperature, or isolation methods may have been used. Additional examples of this procedure are described below.

Procedure 8—Additional Example (Example 472)

(2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one

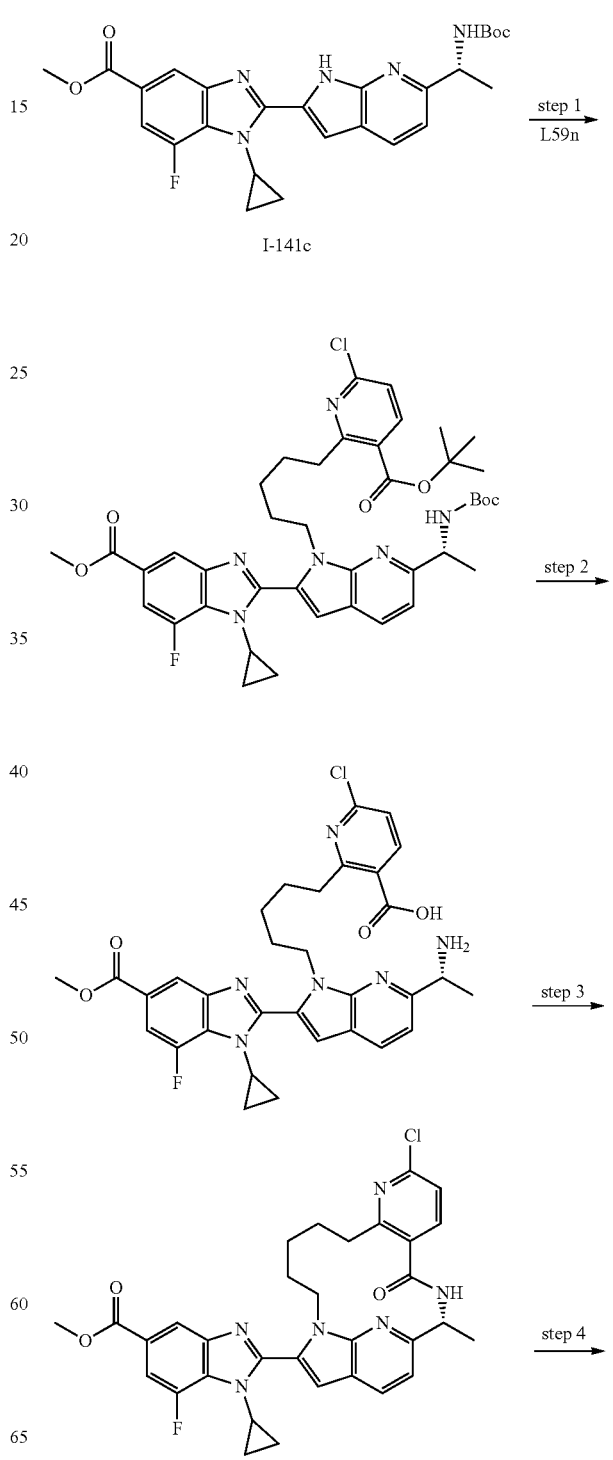

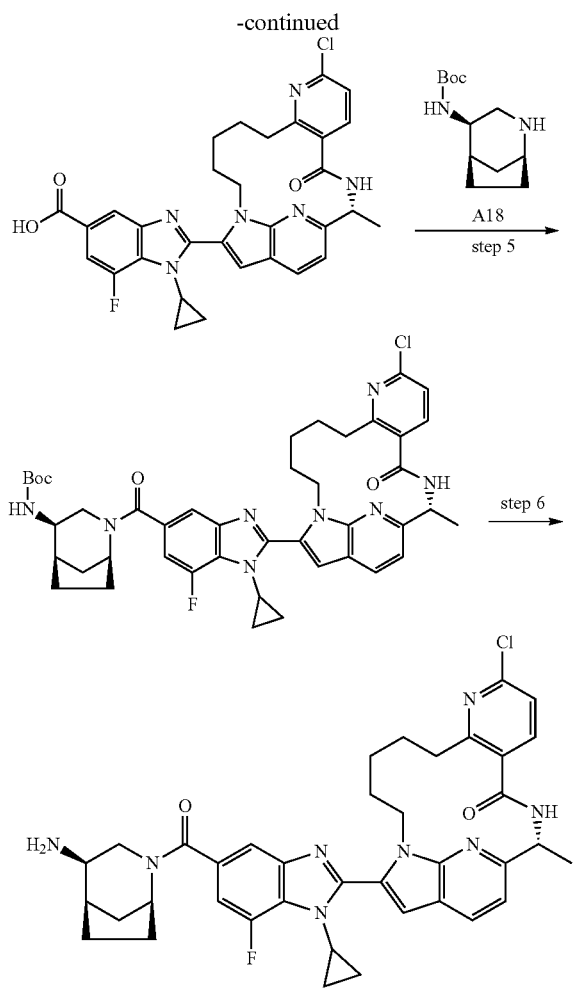

Example 472

Step 1 methyl (R)-2-(6-(1-((tert-butoxycarbonyl)amino)ethyl)-1H-pyrrolo[2,3-b]pyridin-2-yl)-1-cyclopropyl-7-fluoro-1H-benzo[d]imidazole-5-carboxylate (I-141c, 3.5 g, 7.1 mmol) was dissolved in DMF (15 mL) and tert-butyl 6-chloro-2-[5-(p-tolylsulfonyloxy)pentyl]pyridine-3-carboxylate (L59n, 3.4 g, 7.5 mmol) was added) followed by cesium carbonate (6.9 g, 21 mmol). The mixture was heated to 60° C. and stirred until judged complete by LCMS. The mixture was partitioned between EtOAc and water. The organic phase was washed with 10% aqueous LiCl, dried over Na$_2$SO$_4$, filtered and concentrated. Purification silica gel (10-100% EtOAc in hexanes) provided methyl 2-[6-[(1R)-1-(tert-butoxycarbonylamino)ethyl]-1-[5-(3-tert-butoxycarbonyl-6-chloro-2-pyridyl)pentyl]pyrrolo[2,3-b]pyridin-2-yl]-1-cyclopropyl-7-fluoro-benzimidazole-5-carboxylate. ES/MS: m/z 775.2 [M+H]$^+$.

Step 2 methyl 2-[6-[(1R)-1-(tert-butoxycarbonylamino)ethyl]-1-[5-(3-tert-butoxycarbonyl-6-chloro-2-pyridyl)pentyl]pyrrolo[2,3-b]pyridin-2-yl]-1-cyclopropyl-7-fluoro-benzimidazole-5-carboxylate (5.3 g, 6.8 mmol) was dissolved in DCM (100 mL). A solution of hydrochloric acid in 1,4-dioxane (4 M, 51 mL, 204 mmol) was added and the mixture was heated to 40° C. and for 18 h. The mixture was concentrated in vacuo, and the resulting crude residue was dissolved in MeCN and concentrated twice in vacuo to afford a crude 2-[5-[6-[(1R)-1-aminoethyl]-2-(1-cyclopropyl-7-fluoro-5-methoxycarbonyl-benzimidazol-2-yl)pyrrolo[2,3-b]pyridin-1-yl]pentyl]-6-chloro-pyridine-3-carboxylic acid that was used without further purification. ES/MS: m/z 619.36 [M+H]$^+$.

Step 3

2-[5-[6-[(1R)-1-aminoethyl]-2-(1-cyclopropyl-7-fluoro-5-methoxycarbonyl-benzimidazol-2-yl)pyrrolo[2,3-b]pyridin-1-yl]pentyl]-6-chloro-pyridine-3-carboxylic acid (6.8 mmol) was dissolved in DMF (450 mL) and Hunig's base (6 mL, 34 mmol) was added followed by HATU (3.12 g, 8.2 mmol). The mixture was stirred at r.t. for 1 h and was then concentrated to half volume and partitioned between EtOAc and water. The organic phase was washed with 10% aqueous LiCl, dried over Na$_2$SO$_4$, filtered, and concentrated. The crude product was purified by silica gel chromatography to provide methyl 2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carboxylate. ES/MS: m/z 601.12 [M+H]$^+$.

Step 4 methyl 2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carboxylate was dissolved in THF (20 mL), MeOH (10 mL), and water (10 mL). Lithium hydroxide monohydrate (1.5 g, 36 mmol) was added and the resulting mixture was heated to 45° C. for 1 h. The mixture was cooled and hydrochloric acid (6 M, 6.7 mL, 40 mmol) was added. The mixture was partially concentrated in vacuo and MeOH and water were added in quantities needed to effect precipitation of solids. The mixture was further diluted with water, and the solids were collected by filtration, washing with additional water, to afford 2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carboxylic acid. ES/MS: m/z 587.31 [M+H]$^+$.

Step 5

2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carboxylic acid (2.72 g, 4.63 mmol) was dissolved in DMF (20 mL). tert-butyl N-[(1S,4R,5R)-2-azabicyclo[3.2.1]octan-4-yl]carbamate (A18, 1.12 g, 5.0 mmol) was added, followed by Hunig's base (4 mL, 23 mmol) and HATU (2.2 g, 5.8 mmol). The mixture was for 1 h and saturated NaHCO$_3$ was added to effect precipitation of solids. The mixture was further diluted with water and the solids were collected by filtration. The product was further purified by silica gel chromatography to afford tert-butyl N-[(1S,4R,5R)-2-[2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carbonyl]-2-azabicyclo[3.2.1]octan-4-yl]carbamate. ES/MS: m/z 795.10 [M+H]$^+$.

Step 6 tert-butyl N-[(1S,4R,5R)-2-[2-[(2R)-8-chloro-2-methyl-4-oxo-3,9,16,22-tetrazatetracyclo[14.5.2.0$^{5,10}$.0$^{19,23}$]tricosa-1(22),5(10),6,8,17,19(23),20-heptaen-17-yl]-1-cyclopropyl-7-fluoro-benzimidazole-5-carbonyl]-2-azabicyclo[3.2.1]octan-4-yl]carbamate (3.3 g, 4.2 mmol) was dissolved in DCM (30 mL) and TFA (15 mL) was added. The mixture was stirred for 1 h and was concentrated to afford a crude residue that was purified by preparative C18 HPLC (5-100% MeCN in water, 0.1% TFA) to provide Example 472.

517

Procedure 8—Additional Example (Example 809)

(2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one

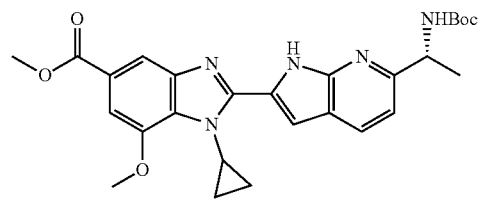

I-141i step 1
L59n

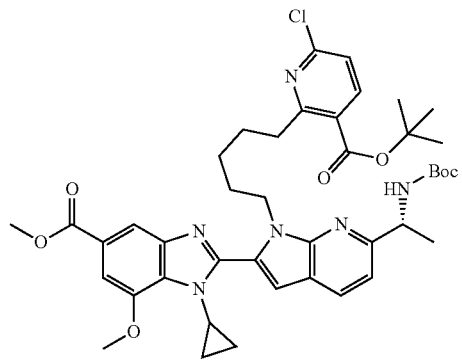

step 2

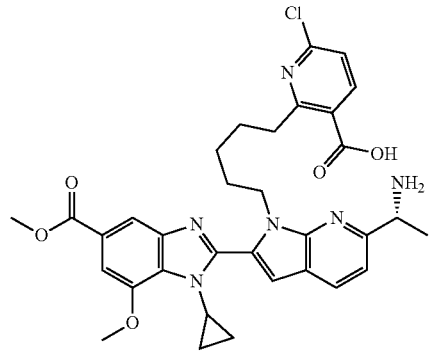

step 3

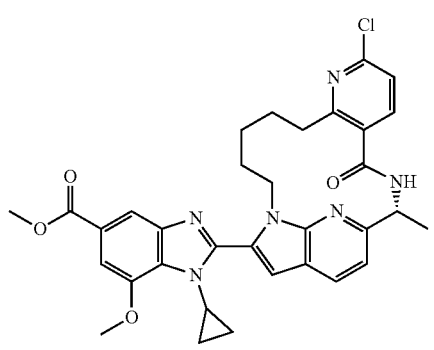

step 4

518

-continued

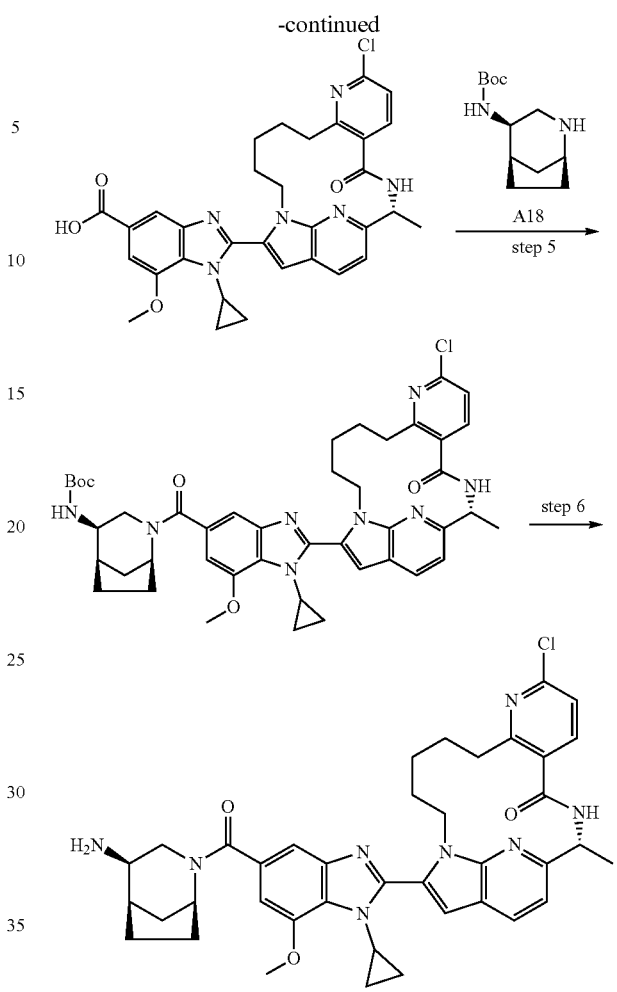

Example 809

Step 1

A mixture of methyl 2-[6-[(1R)-1-(tert-butoxycarbonylamino)ethyl]-1H-pyrrolo[2,3-b]pyridin-2-yl]-1-cyclopropyl-7-methoxy-benzimidazole-5-carboxylate (I-141i, 120 mg, 0.237 mmol), tert-butyl 6-chloro-2-[5-(p-tolylsulfonyloxy)pentyl]pyridine-3-carboxylate (L59n, 124 mg, 0.273 mmol), and cesium carbonate (232 mg, 0.712 mmol) in DMF (2.7 mL) was heated at 70° C. for four hours. After cooling to rt, the reaction mixture was diluted with 50% brine and ethyl acetate. The layers were separated and the aqueous extracted with ethyl acetate. The combined organics were washed with water, dried, filtered, and concentrated under reduced pressure. The resulting residue was purified via silica gel column chromatography (10-60% ethyl acetate in hexanes) to yield methyl 2-[6-[(1R)-1-(tert-butoxycarbonylamino)ethyl]-1-[5-(3-tert-butoxycarbonyl-6-chloro-2-pyridyl)pentyl]pyrrolo[2,3-b]pyridin-2-yl]-1-cyclopropyl-7-methoxy-benzimidazole-5-carboxylate. ES/MS: m/z 786.8 [M+H]$^+$.

Step 2

To a solution of methyl 2-[6-[(1R)-1-(tert-butoxycarbonylamino)ethyl]-1-[5-(3-tert-butoxycarbonyl-6-chloro-2-pyridyl)pentyl]pyrrolo[2,3-b]pyridin-2-yl]-1-cyclopropyl-7-methoxy-benzimidazole-5-carboxylate (167 mg, 0.212 mmol) in DCM (4 mL) was added a solution of hydrochloric acid in 1,4-dioxane (4 M, 2.7 mL, 10.8 mmol). After stirring overnight, the reaction mixture was concentrated under reduced pressure to yield crude 2-[5-[6-[(1R)-1-aminoethyl]-2-(1-cyclopropyl-7-methoxy-5-methoxycarbonyl-benzimidazol-2-yl)pyrrolo[2,3-b]pyridin-1-yl]pentyl]-6-chloro-pyridine-3-carboxylic acid, which was used without purification. ES/MS: m/z 631.0 [M+H]$^+$.

Step 3

To a solution of 2-[5-[6-[(1R)-1-aminoethyl]-2-(1-cyclopropyl-7-methoxy-5-methoxycarbonyl-benzimidazol-2-yl)pyrrolo[2,3-b]pyridin-1-yl]pentyl]-6-chloro-pyridine-3-carboxylic acid (0.255 mmol) in DMF (4.5 mL) was added DIPEA (0.36 mL, 2.04 mmol) and HATU (116 mg, 0.306 mmol). After 30 minutes, the reaction mixture was diluted with 50% brine and ethyl acetate. The layers were separated and the aqueous extracted with ethyl acetate. The combined organics were washed with water, dried, filtered, and concentrated under reduced pressure. The resulting residue was purified via silica gel column chromatography (5-60% acetone in hexanes) to yield methyl 2-[(2R)-8-chloro-2-methyl-4-oxo-3,9,16,22-tetrazatetracyclo[14.5.2.0⁵,10.0¹⁹,²³]tricosa-1(22),5(10),6,8,17,19(23),20-heptaen-17-yl]-1-cyclopropyl-7-methoxy-benzimidazole-5-carboxylate. ES/MS: m/z 613.2 [M+H]$^+$.

Step 4

Lithium hydroxide, monohydrate (103 mg, 2.45 mmol) was added to a solution of methyl 2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-methoxy-benzimidazole-5-carboxylate (250 mg, 0.408 mmol) in THF (7 mL), MeOH (3.5 mL) and water (3.5 mL). The reaction mixture was heated at 50° C. for four hours and cooled to rt. A solution of hydrochloric acid in water (6M, 0.54 mL, 3.26 mmol) was added and the reaction mixture was diluted with 50% brine and DCM. The layers were separated and the aqueous extracted with DCM. The combined organics were dried, filtered, and concentrated under reduced pressure to yield 2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-methoxy-benzimidazole-5-carboxylic acid, which was used without purification. ES/MS: m/z 599.3 [M+H]$^+$.

Step 5

To a mixture of 2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-methoxy-benzimidazole-5-carboxylic acid (244 mg, 0.407 mmol) and tert-butyl N-[(1S,4R,5R)-2-azabicyclo[3.2.1]octan-4-yl]carbamate (A18, 100 mg, 0.442 mmol) in DMF (5 mL) was added DIPEA (0.28 mL, 1.63 mmol) and HATU (0.232 g, 0.611 mmol). After 30 minutes, water was added and the precipitated solid was filtered, washed with water, and dried in vacuo to yield tert-butyl N-[(1S,4R,5R)-2-[2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-methoxy-benzimidazole-5-carbonyl]-2-azabicyclo[3.2.1]octan-4-yl]carbamate, which was used without purification. ES/MS: m/z 807.3 [M+H]$^+$.

Step 6

To a solution of tert-butyl N-[(1S,4R,5R)-2-[2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-methoxy-benzimidazole-5-carbonyl]-2-azabicyclo[3.2.1]octan-4-yl]carbamate (0.407 mmol) in DCM (6 mL) was added trifluoroacetic acid (0.93 mL, 12.2 mmol). The mixture was stirred for 2 h and was concentrated to afford a crude residue that was purified by preparative C18 HPLC (5-100% MeCN in water, 0.1% TFA) to provide Example 809.

Procedure 9 (Examples 10 and 11)

(3~{R},5~{S},12~{R})-18-[5-[(1~{R},2~{R},4~{S})-2-amino-7-azabicyclo[2.2.1]heptane-7-carbonyl]-7-methoxy-1-methyl-benzimidazol-2-yl]-4,4,12-trimethyl-7-oxa-1,11,20-triazatetracyclo[11.5.2.0ˆ{3,5}.0ˆ{16,19}]icosa-13(20),14,16(19),17-tetraen-10-one Example 10

(3~{S},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-4,4,12-trimethyl-7-oxa-1,11,20-triazatetracyclo[11.5.2.0ˆ{3,5}.0ˆ{16,19}]icosa-13(20),14,16(19),7-tetraen-10-one (Example 11)

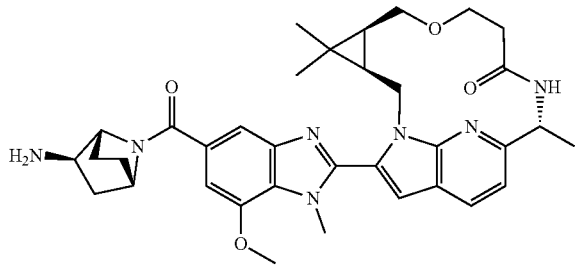

Example 10

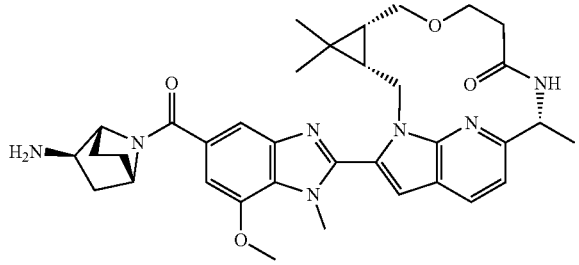

Example 11

The 1:1 diastereoisomeric mixture of Examples 10 and 11 was prepared using Procedure 8 using instead L10 instead of L1a. Examples 10 and 11 were separated via C18 preparative HPLC (5-100% MeCN in water, 0.1% TFA), and the first eluting peak was arbitrarily assigned as the (3R,5S)-configuration (Example 10), and the second eluting peak was assigned as the (3S,5R)-configuration (Example 11).

*In other instances, diastereoisomeric mixtures of Examples can be separated via preparative chiral HPLC or chiral SFC.

Procedure 10 (Examples 223 and 224)

(2~{R},5~{R},7~{R})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one (Example 223)

(2~{R},5~{S},7~{S})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one (Example 224)

Example 223

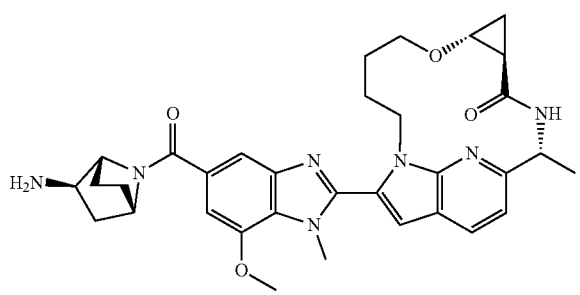

-continued

Example 224

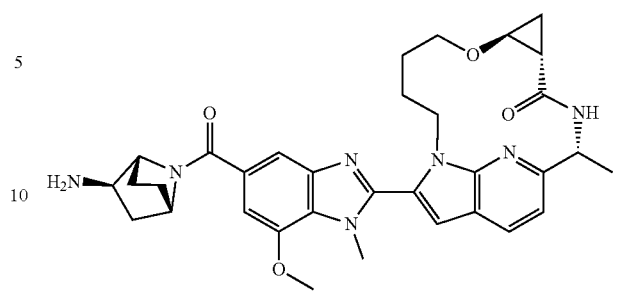

Examples 223 and 224 were prepared using Procedure 8 using L20b instead of L1a. After purification by silica gel chromatography at the macrocyclization step (step 3 of Procedure 8), the first eluting peak was arbitrarily assigned as the (5R,7R)-configuration, and the second eluting peak was assigned as the (5S,7S)-configuration. Both diastereoisomers were separately submitted to steps 4-6 of Procedure 8 to provide Examples 223 and 224.

Procedure 10—Additional Example (Examples 944 and 945)

(8~{R},11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one (Example 944)

(8~{S},11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one (Example 945)

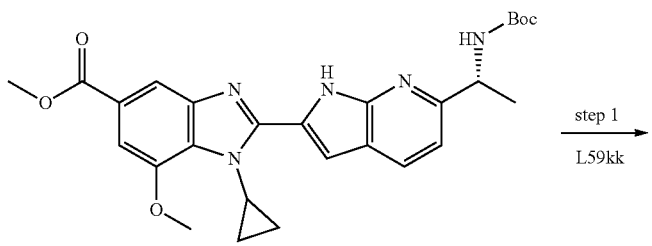

I-141i step 1
L59kk

-continued
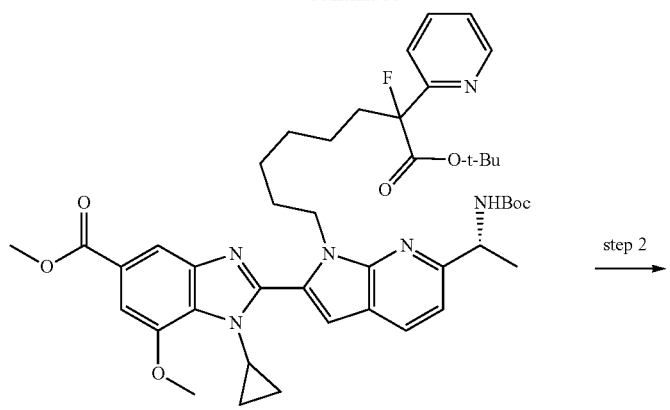
step 2
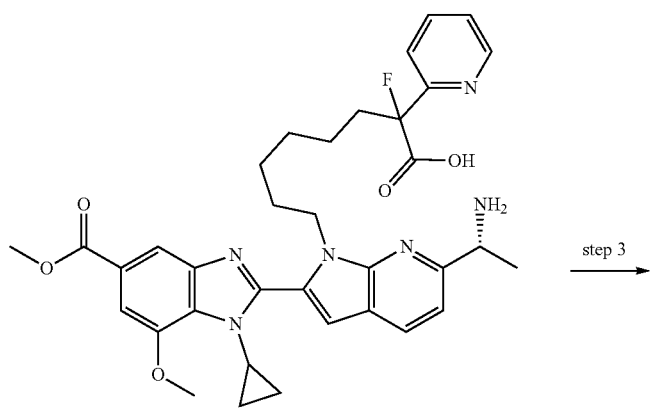
step 3
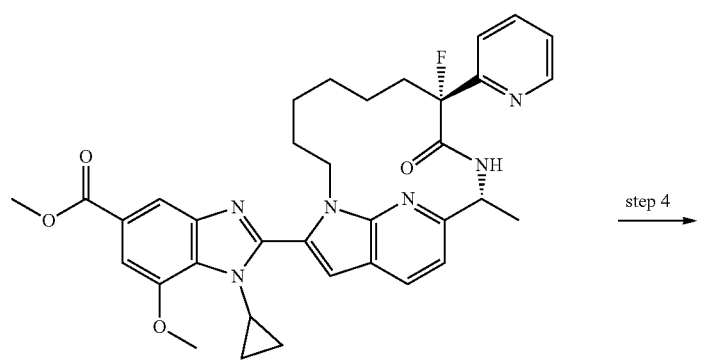
second eluting isomer
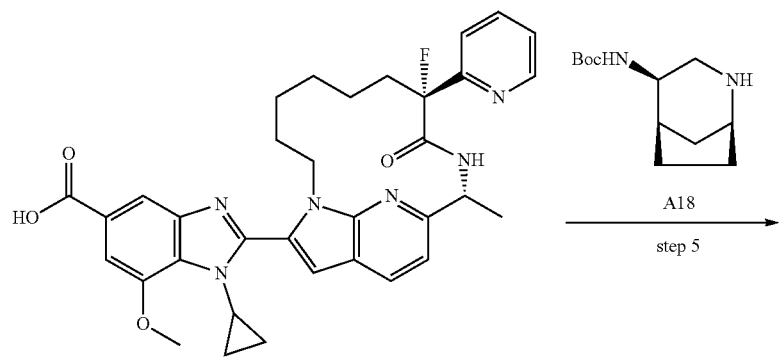
A18
step 5

-continued

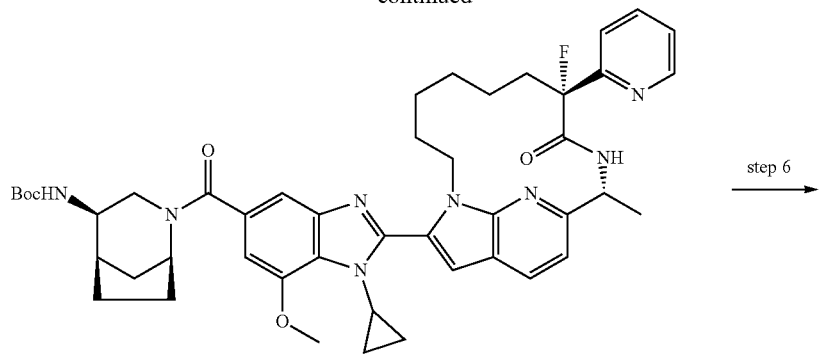

step 6

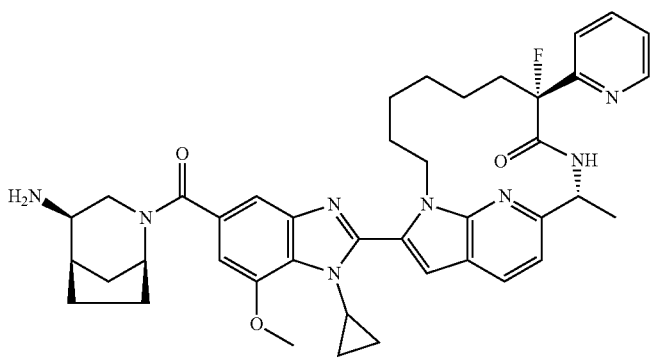

Example 944

Step 1

A mixture of methyl (R)-2-(6-(1-((tert-butoxycarbonyl)amino)ethyl)-1H-pyrrolo[2,3-b]pyridin-2-yl)-1-cyclopropyl-7-methoxy-1H-benzo[d]imidazole-5-carboxylate (I-141i, 0.740 g, 1.46 mmol), tert-butyl 2-fluoro-2-(pyridin-2-yl)-8-(tosyloxy)octanoate (L59kk, 0.748 g, 1.61 mmol), and cesium carbonate (1.43 g, 4.39 mmol) in DMF (9.7 mL) was stirred at 50° C. for 24 h. The mixture was cooled to rt and diluted with EtOAc and water. The aqueous layer was extracted with EtOAc. The organic layer was washed with brine, dried ($Na_2SO_4$), filtered, and concentrated. The residue was purified via flash column chromatography on silica gel to afford methyl 2-(1-(8-(tert-butoxy)-7-fluoro-8-oxo-7-(pyridin-2-yl)octyl)-6-((R)-1-((tert-butoxycarbonyl)amino)ethyl)-1H-pyrrolo[2,3-b]pyridin-2-yl)-1-cyclopropyl-7-methoxy-1H-benzo[d]imidazole-5-carboxylate. ES/MS: m/z 799.5 $[M+H]^+$.

Step 2

To a solution of methyl 2-(1-(8-(tert-butoxy)-7-fluoro-8-oxo-7-(pyridin-2-yl)octyl)-6-((R)-1-((tert-butoxycarbonyl)amino)ethyl)-1H-pyrrolo[2,3-b]pyridin-2-yl)-1-cyclopropyl-7-methoxy-1H-benzo[d]imidazole-5-carboxylate (0.849 g, 1.06 mmol) in DCM (11 mL) was added TFA (4.1 mL). The mixture was stirred at rt for 16 h. The mixture was concentrated. The resulting residue was taken up in DCM and concentrated twice, yielding crude 8-(6-((R)-1-aminoethyl)-2-(1-cyclopropyl-7-methoxy-5-(methoxycarbonyl)-1H-benzo[d]imidazol-2-yl)-1H-pyrrolo[2,3-b]pyridin-1-yl)-2-fluoro-2-(pyridin-2-yl)octanoic acid, which was used without purification. ES/MS: m/z 643.4 $[M+H]^+$.

Step 3

To a mixture of 8-(6-((R)-1-aminoethyl)-2-(1-cyclopropyl-7-methoxy-5-(methoxycarbonyl)-1H-benzo[d]imidazol-2-yl)-1H-pyrrolo[2,3-b]pyridin-1-yl)-2-fluoro-2-(pyridin-2-yl)octanoic acid (0.683 g, 1.06 mmol) and DIPEA (2.8 mL, 15.9 mmol) in DCM (53 mL) was added HATU (0.485 g, 1.28 mmol). The mixture was stirred at rt for 72 h. The mixture was concentrated onto silica gel and purified via flash column chromatography on silica gel. The first-eluting isomer was arbitrarily assigned as methyl 1-cyclopropyl-2-[(8S,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylate. ES/MS: m/z 625.3 $[M+H]^+$. The second-eluting isomer was arbitrarily assigned as methyl 1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylate. ES/MS: m/z 625.3 $[M+H]^+$.

Step 4

To a solution of methyl 1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylate (0.239 g, 0.383 mmol) in THF (3.1 mL) and MeOH (0.6 mL) was added LiOH (1.2 mL of a 1 M aq soln, 1.2 mmol). The mixture was stirred at 50° C. for 2 h. The mixture was cooled to rt and the resulting residue was dried en vacuo to give 1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylic acid. ES/MS: m/z 611.3 $[M+H]^+$.

Step 5

To a solution of 1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylic acid (0.234 g, 0.383 mmol), tert-butyl N-[(1S,4R,5R)-2-azabicyclo[3.2.1]octan-4-yl]carbamate (A18, 0.095 g, 0.421 mmol), and DIPEA (0.33 mL, 1.92 mmol) in DMF (1.9 mL) was added HATU (0.219 g, 0.575 mmol). The mixture was stirred at rt for 10 min and was then diluted with water (~10 mL). The resulting solid was collected via filtration, rinsed with water, and dried en vacuo to yield tert-butyl N-[(1S,4R,5R)-2-[1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carbonyl]-2-azabicyclo[3.2.1]octan-4-yl]carbamate. ES/MS: m/z 819.5 [M+H]$^+$.

Step 6

To a solution of tert-butyl N-[(1S,4R,5R)-2-[1-cyclopropyl-2-[(8R,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carbonyl]-2-azabicyclo[3.2.1]octan-4-yl]carbamate (0.271 g, 0.330 mmol) in DCM (1.6 mL) was added TFA (1.6 mL). The mixture sat at rt for 10 min. The mixture was concentrated and the resulting residue was purified via preparative reverse phase HPLC to give Example 944.

Example 945 was prepared following Steps 4-6 of the procedure described above, using methyl 1-cyclopropyl-2-[(8S,11R)-8-fluoro-11-methyl-9-oxo-8-(2-pyridyl)-1,10,19-triazatricyclo[10.5.2.015,18]nonadeca-12(19),13,15(18),16-tetraen-17-yl]-7-methoxy-benzimidazole-5-carboxylate (the first-eluting isomer from Step 3 of that procedure).

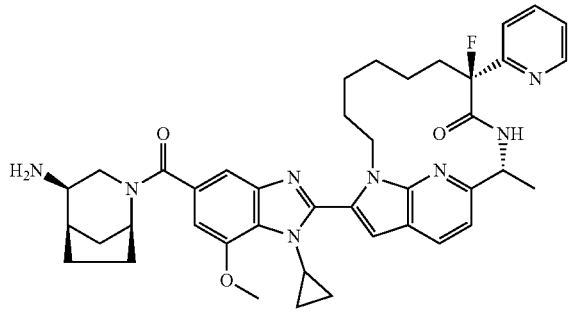

Example 945

Procedure 11 (Examples 261 and 262)

(11~{R})-17-[5-[(4~{a}~{R},8~{a}~{R})-2,3,4,4~{a},5,6,8,8~{a}-octahydro-1~{H}-1,7-naphthyridine-7-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one (Example 261)

(11~{R})-17-[5-[(4~{a}~{S},8~{a}~{S})-2,3,4,4~{a},5,6,8,8~{a}-octahydro-1~{H}-1,7-naphthyridine-7-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one (Example 262)

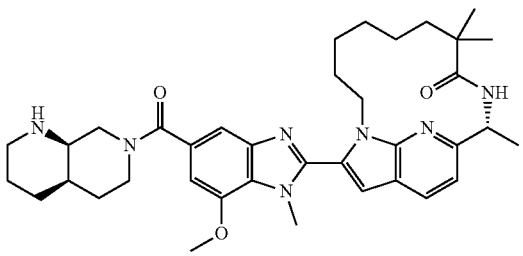

Example 261

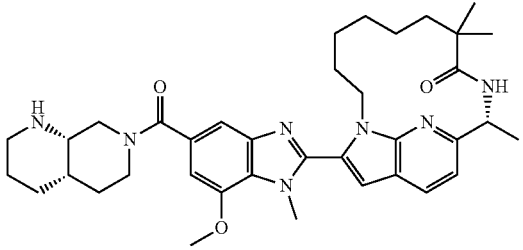

Example 262

The 1:1 diastereoisomeric mixture of Examples 261 and 262 was prepare following Procedure 8 using L4a and A7. Examples 261 and 262 were separated via chiral SFC. The first eluting peak was arbitrarily assigned as the (4aR,8aR)-configuration (Example 261), and the second eluting peak was assigned as the (4aS,8aS)-configuration (Example 262).

*In other instances, diastereoisomeric mixtures of Examples can be separated via preparative HPLC or preparative chiral HPLC.

Procedure 12 (Example 125)

(2~{R})-16-[5-[(1~{R},2~{R},4~{S})-2-amino-7-azabicyclo[2.2.1]heptane-7-carbonyl)-7-methoxy-1-methyl-benzimidazol-2-yl]-6,15,21-triazatetracyclo[13.5.2.0^{2,6}.0^{18,22}]docosa-1(21),16,18(22),19-tetraen-7-one

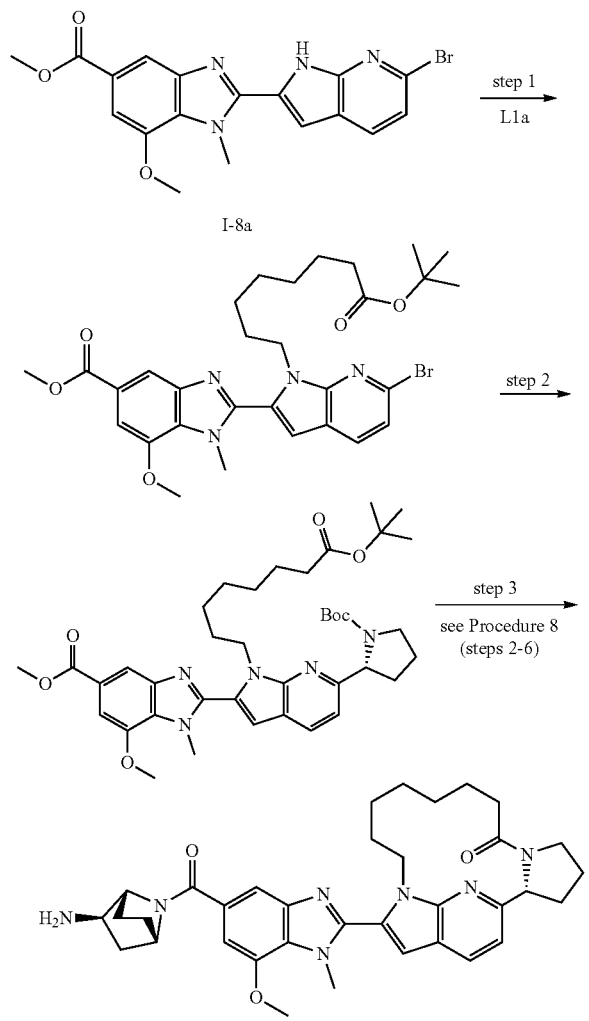

Example 125

Step 1

2-[6-bromo-1-(8-tert-butoxy-8-oxo-octyl)pyrrolo[2,3-b]pyridin-2-yl]-7-methoxy-1-methyl-benzimidazole-5-carboxylate was made according to Procedure 8, step 1, using methyl 2-(6-bromo-1H-pyrrolo[2,3-b]pyridin-2-yl)-7-methoxy-1-methyl-1H-benzo[d]imidazole-5-carboxylate (I-8a) and tert-butyl 8-bromooctanoate (L1a). ES/MS: m/z 613.1, 615.1 [M+H]+.

Step 2

To a solution of N-Boc-pyrrolidine (0.075 mL, 0.43 mmol) and (−)-sparteine (0.098 mL, 0.43 mmol) in MTBE (1 mL) at −78° C. was added s-BuLi (1.4 M in cyclohexane, 0.31 mL, 0.43 mmol) dropwise. The resulting solution was allowed to stir for 3 h at −78° C. A solution of ZnCl$_2$ (0.5 M in THF, 0.51 mL, 0.26 mmol) was added to the reaction dropwise with stirring. The resulting suspension was allowed to stir at −78° C. for 30 minutes and then allowed to warm to room temperature for 30 min. To this mixture was added methyl 2-[6-bromo-1-(8-tert-butoxy-8-oxo-octyl)pyrrolo[2,3-b]pyridin-2-yl]-7-methoxy-1-methyl-benzimidazole-5-carboxylate (120 mg, 0.19 mmol), palladium (II) acetate (5 mg, 0.02 mmol), tri-t-butylphosphonium tetrafluoroborate (7 mg, 0.02 mmol), and dioxane (1 mL). The mixture was stirred overnight at room temperature. The mixture was filtered through Celite and adsorbed onto silica gel. Purification by silica gel column chromatography (50-100% EtOAc in hexanes) provided methyl 2-[1-(8-tert-butoxy-8-oxo-octyl)-6-[(1R)-1-tert-butoxycarbonylpyrrolidin-2-yl]pyrrolo[2,3-b]pyridin-2-yl]-7-methoxy-1-methyl-benzimidazole-5-carboxylate. ES/MS: m/z 704.3 [M+H]+.

Step 3

Example 125 was made following steps 2-6 of Procedure 8 using methyl 2-[1-(8-tert-butoxy-8-oxo-octyl)-6-[(1R)-1-tert-butoxycarbonylpyrrolidin-2-yl]pyrrolo[2,3-b]pyridin-2-yl]-7-methoxy-1-methyl-benzimidazole-5-carboxylate.

Procedure 13 (Example 134)

16-[5-[(1~{R},2~{R},4~{S})-2-amino-7-azabicyclo[2.2.1]heptane-7-carbonyl]-7-methoxy-1-methyl-benzimidazol-2-yl]spiro[6,15,21-triazatetracyclo[13.5.2.0^{2,6}.0^{18,22}]docosa-1(21),16,18(22),19-tetraene-4,1'-cyclopropane]-7-one (1:1 Mixture of Epimers)

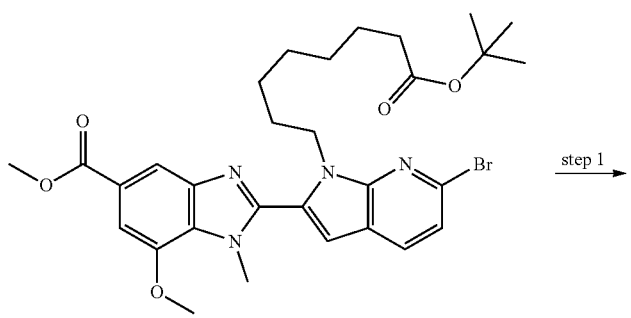

intermediate described in Procedure 12

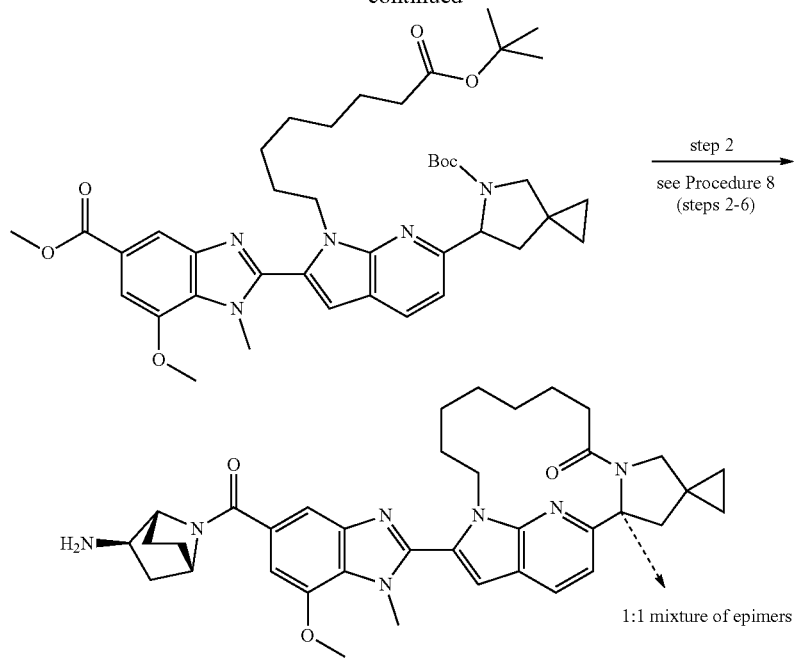

Example 134

Step 1

A solution of methyl 2-[6-bromo-1-(8-tert-butoxy-8-oxo-octyl)pyrrolo[2,3-b]pyridin-2-yl]-7-methoxy-1-methyl-benzimidazole-5-carboxylate (100 mg, 0.16 mmol), (6S)-5-tert-butoxycarbonyl-5-azaspiro[2.4]heptane-6-carboxylic acid (120 mg, 0.49 mmol), Ir[dF(CF$_3$)ppy]$_2$(dtbbpy) (5 mg, 0.0049 mmol), a solution of 4,4'-di-tert-butyl-2,2'-bipyridine and nickel(II) chloride, dimethoxyethane adduct in DMSO (0.01 M of both 4,4'-di-tert-butyl-2,2'-bipyridine and nickel (II) chloride, dimethoxyethane adduct, 0.13 mL, 0.0013 mmol) in DMSO (8 mL) was degassed by bubbling nitrogen through for 15 min. The reaction was sealed and allowed to stir in a blue LED reactor (ACS Cent. Sci. 2017, 36, 647-653) overnight. Brine was added to the mixture and the aqueous layer was washed twice with EtOAc. The combined organic layers were washed twice with brine, dried over Na$_2$SO$_4$, filtered and adsorbed onto silica gel and purified by silica gel chromatography (0-100 EtOAc in hex) to provide methyl 2-[6-(5-tert-butoxycarbonyl-5-azaspiro[2.4]heptan-6-yl)-1-(8-tert-butoxy-8-oxo-octyl)pyrrolo[2,3-b]pyridin-2-yl]-7-methoxy-1-methyl-benzimidazole-5-carboxylate. ES/MS: 730.3 (M+H)+.

Step 2

Example 134 was made following steps 2-6 of Procedure 8 using methyl 2-[6-(5-tert-butoxycarbonyl-5-azaspiro[2.4]heptan-6-yl)-1-(8-tert-butoxy-8-oxo-octyl)pyrrolo[2,3-b]pyridin-2-yl]-7-methoxy-1-methyl-benzimidazole-5-carboxylate.

Procedure 14 (Example 138)

(2~{R},6~{R})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.1^{3,6}.0^{16,20}]henicosa-1(19),14,16(20),17-tetraen-21-one

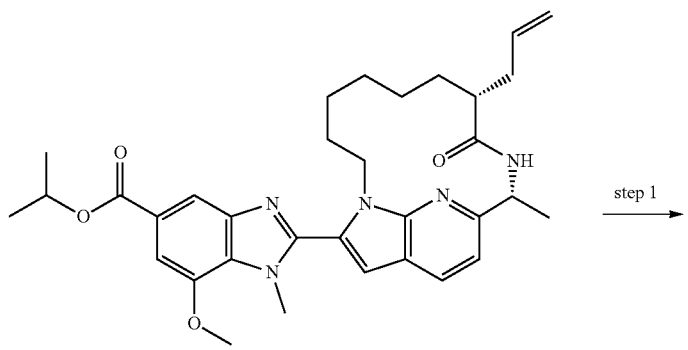

prepared following Procedure 8
(steps 1-3) using L5c

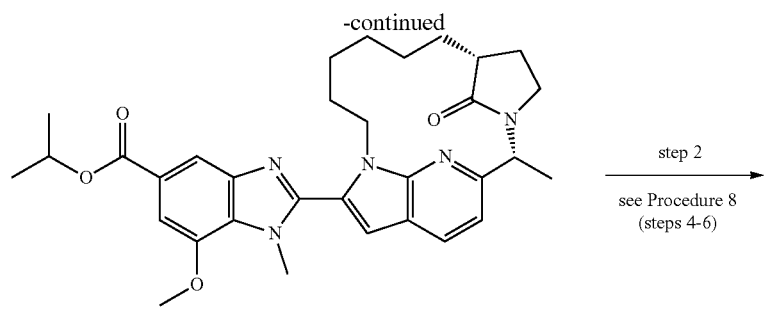

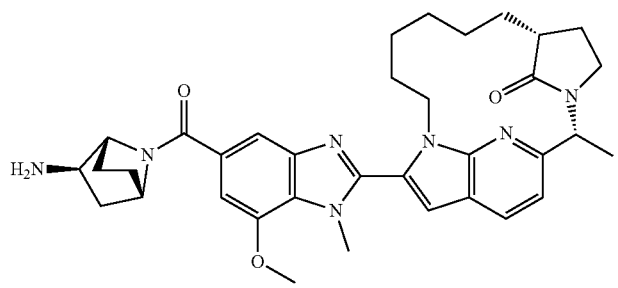

Example 138

Step 1

To a mixture of isopropyl 2-[(8R,11R)-8-allyl-11-methyl-9-oxo-1,10,19-triazatricyclo[10.5.2.015,18]nonadeca-12(19),13,15(18),16-tetraen-17-yl]-7-methoxy-1-methyl-benzimidazole-5-carboxylate (prepared following Procedure 8 (steps 1-3) using L5c) (140 mg, 0.25 mmol), 2,6-lutidine (0.056 mL, 0.49 mmol), and sodium periodate (210 mg, 1.0 mmol) in dioxane (3 mL) and water (1 mL) was added potassium osmate(VI) (5 mg, 0.012 mmol). The reaction mixture was allowed to stir overnight. Brine was added to the reaction mixture and the aqueous layer was washed with EtOAc three times. The combined organic layers were dried over Na$_2$SO$_4$, filtered and concentrated. The residue was brought up in DCM (1 mL) and cooled to 0° C. To this solution was added TFA (0.49 mL, 6.3 mmol) and triethylsilane (0.50 mL, 3.2 mmol). The solution stirred at 0° C. for 3 h and was concentrated. The residue was brought up in EtOAc and saturated sodium bicarbonate and washed with EtOAc twice. The combined organic layers were dried over Na$_2$SO$_4$, filtered and adsorbed onto silica gel. Purification by silica gel chromatography (50-100% EtOAc in hex, then 0-30% MeOH in EtOAc) provided isopropyl 7-methoxy-1-methyl-2-[(2R,6R)-2-methyl-21-oxo-3,13,19-triazatetracyclo[11.5.2.13,6.016,20]henicosa-1(19),14,16(20),17-tetraen-14-yl]benzimidazole-5-carboxylate. ES/MS: m/z 558.4 [M+H]$^+$.

Step 2

Example 138 was made following steps 4-6 of Procedure 8 using isopropyl 7-methoxy-1-methyl-2-[(2R,6R)-2-methyl-21-oxo-3,13,19-triazatetracyclo[11.5.2.13,6.016,20]henicosa-1(19),14,16(20),17-tetraen-14-yl]benzimidazole-5-carboxylate.

Procedure 15 (Example 91)

17-[5-[(1~{R},2~{R},4~{S})-2-amino-7-azabicyclo[2.2.1]heptane-7-carbonyl]-7-methoxy-1-methyl-benzimidazol-2-yl]-6,9,16,22-tetrazatetracyclo[14.5.2.0^{2,7}.0^{19,23}]tricosa-1(22),2,4,6,17,19(23),20-heptaen-8-one

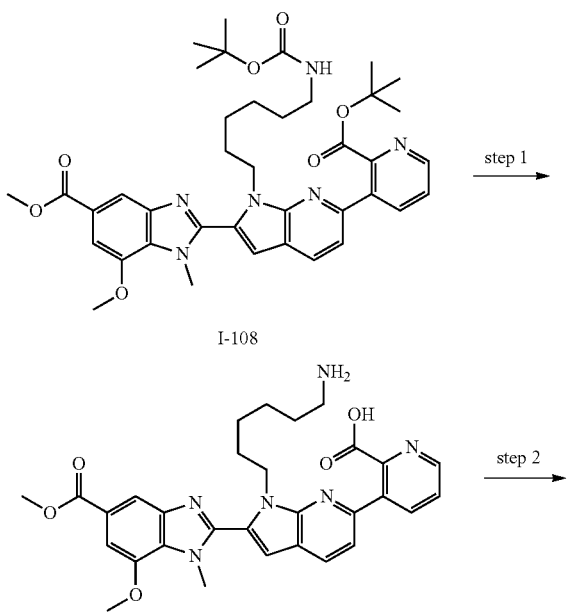

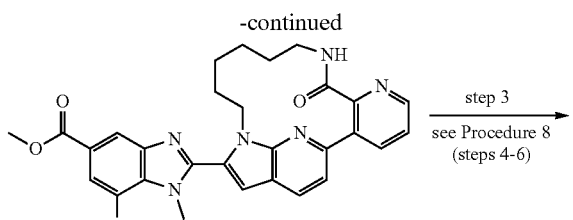

step 3
see Procedure 8
(steps 4-6)

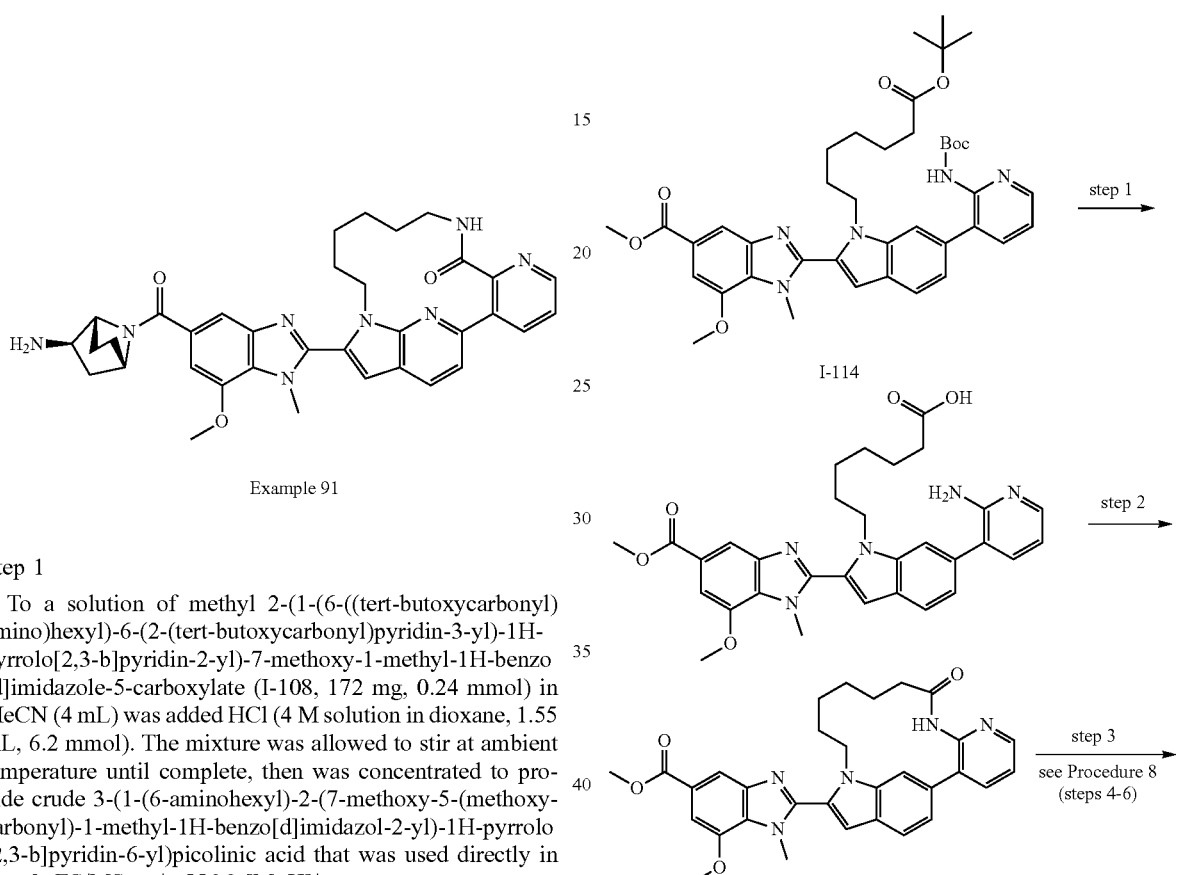

Example 91

Step 1

To a solution of methyl 2-(1-(6-((tert-butoxycarbonyl)amino)hexyl)-6-(2-(tert-butoxycarbonyl)pyridin-3-yl)-1H-pyrrolo[2,3-b]pyridin-2-yl)-7-methoxy-1-methyl-1H-benzo[d]imidazole-5-carboxylate (I-108, 172 mg, 0.24 mmol) in MeCN (4 mL) was added HCl (4 M solution in dioxane, 1.55 mL, 6.2 mmol). The mixture was allowed to stir at ambient temperature until complete, then was concentrated to provide crude 3-(1-(6-aminohexyl)-2-(7-methoxy-5-(methoxycarbonyl)-1-methyl-1H-benzo[d]imidazol-2-yl)-1H-pyrrolo[2,3-b]pyridin-6-yl)picolinic acid that was used directly in step 2. ES/MS: m/z 556.9 [M+H]⁺.

Step 2

To a solution of 3-(1-(6-aminohexyl)-2-(7-methoxy-5-(methoxycarbonyl)-1-methyl-1H-benzo[d]imidazol-2-yl)-1H-pyrrolo[2,3-b]pyridin-6-yl)picolinic acid (0.24 mmol, crude from previous rxn) in DCM (12 mL) was added N-methylmorpholine (0.21 mL, 1.92 mmol), followed by HATU (110 mg, 0.29 mmol). The mixture was allowed to stir at ambient temperature for 18 h, then was poured into water and extracted 3x with DCM. The combined extracts were adsorbed to isolute, concentrated, and purified by silica gel chromatography (eluent: 3:1 EtOAc/EtOH with 0.25% triethylamine in heptane) to give methyl 7-methoxy-1-methyl-2-(8-oxo-6,9,16,22-tetrazatetracyclo[14.5.2.02,7.019,23]tricosa-1(22),2(7),3,5,17,19(23),20-heptaen-17-yl)benzimidazole-5-carboxylate. ES/MS: m/z 539.2 [M+H]⁺.

Step 3

Example 91 was made following steps 4-6 of Procedure 8 using methyl 7-methoxy-1-methyl-2-(8-oxo-6,9,16,22-tetrazatetracyclo[14.5.2.02,7.019,23]tricosa-1(22),2(7),3,5,17,19(23),20-heptaen-17-yl)benzimidazole-5-carboxylate.

Procedure 16 (Example 88)

17-[5-[(1~{R},2~{R},4~{S})-2-amino-7-azabicyclo[2.2.1]heptane-7-carbonyl]-7-methoxy-1-methyl-benzimidazol-2-yl]-6,8,16-triazatetracyclo[14.5.2.0^{2,7}.0^{19,23}]tricosa-1(22),2,4,6,17,19(23),20-heptaen-9-one

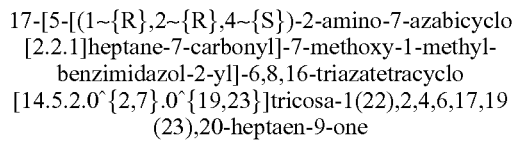

Example 88

Step 1

Followed step 1 of Procedure 15 using methyl 2-(1-(7-(tert-butoxy)-7-oxoheptyl)-6-(2-((tert-butoxycarbonyl)amino)pyridin-3-yl)-1H-indol-2-yl)-7-methoxy-1-methyl-1H-benzo[d]imidazole-5-carboxylate (I-114, 0.20 mmol). The reaction was concentrated to provide 7-(6-(2-aminopyridin-3-yl)-2-(7-methoxy-5-(methoxycarbonyl)-1-methyl-1H-benzo[d]imidazol-2-yl)-1H-indol-1-yl)heptanoic acid that was used in step 2 without purification. ES/MS: m/z 556.3 [M+H]⁺.

537

Step 2

To a solution of 7-(6-(2-aminopyridin-3-yl)-2-(7-methoxy-5-(methoxycarbonyl)-1-methyl-1H-benzo[d]imidazol-2-yl)-1H-indol-1-yl)heptanoic acid (0.20 mmol, crude from previous rxn) in DCM (8 mL) was added DIPEA (0.35 mL, 2.0 mmol), followed by HATU (114 mg, 0.30 mmol). The mixture was allowed to stir at ambient temperature for 5 days, then was concentrated, dissolved in EtOAc, and washed with water, aq. NaHCO$_3$, then brine. The aqueous washes were back-extracted 2× with DCM. The combined extracts were adsorbed to isolute, concentrated, and purified by silica gel chromatography (eluent: 3:1 EtOAc/EtOH with 0.25% triethylamine in heptane) to give methyl 7-methoxy-1-methyl-2-(9-oxo-6,8,16-triazatetracyclo[14.5.2.02,7.019,23]tricosa-1(22),2(7),3,5,17,19(23),20-heptaen-17-yl)benzimidazole-5-carboxylate. ES/MS: m/z 538.2 [M+H]$^+$.

Step 3

Example 88 was made following steps 4-6 of Procedure 8 using methyl 7-methoxy-1-methyl-2-(9-oxo-6,8,16-triazatetracyclo[14.5.2.02,7.019,23]tricosa-1(22),2(7),3,5,17,19(23),20-heptaen-17-yl)benzimidazole-5-carboxylate.

Procedure 17 (Example 85)

[(1~{R},2~{R},4~{S})-2-amino-7-azabicyclo[2.2.1]heptan-7-yl]-[7-methoxy-1-methyl-2-(8-oxa-6,16,22-triazatetracyclo[14.5.2.0^{2,7}.0^{19,23}]tricosa-1(22),2,4,6,17,19(23),20-heptaen-17-yl)benzimidazol-5-yl]methanone

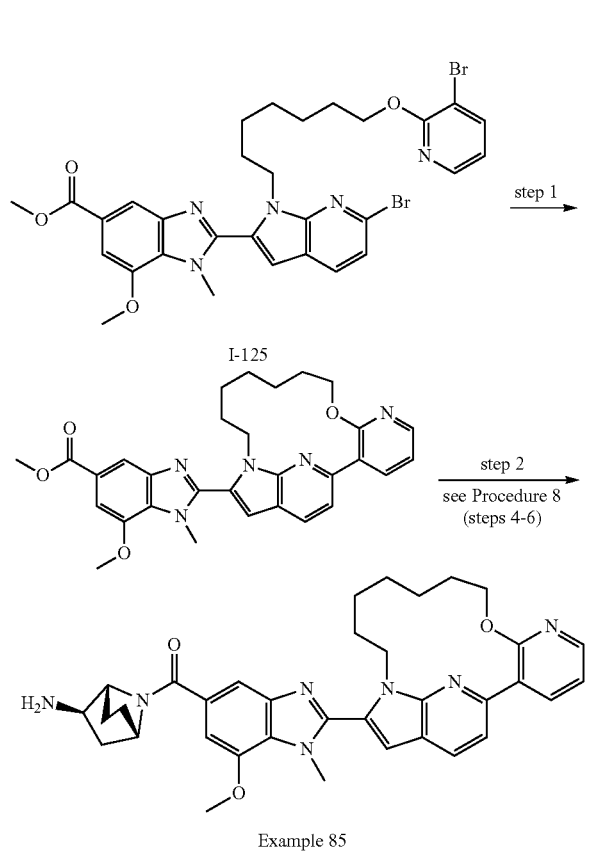

Example 85

Step 1

A mixture of methyl 2-(6-bromo-1-(7-((3-bromopyridin-2-yl)oxy)heptyl)-1H-pyrrolo[2,3-b]pyridin-2-yl)-7-methoxy-1-methyl-1H-benzo[d]imidazole-5-carboxylate (I-125, 52 mg, 0.076 mmol), 4,4,5,5-tetramethyl-2-(4,4,5,5-tetramethyl-1,3,2-dioxaborolan-2-yl)-1,3,2-dioxaborolane (23 mg, 0.091 mmol), dichloro 1,1'-bis(diphenylphosphino)ferrocene palladium(II) dichloromethane (6 mg, 0.008 mmol), and potassium acetate (22 mg, 0.23 mmol) were suspended in dioxane (6 mL). N$_2$ was bubbled through the mixture, and the reaction was then heated to 100° C. for 18 h. The reaction was adsorbed to isolute and purified by silica gel chromatography (eluent: EtOAc in hexane) to give methyl 7-methoxy-1-methyl-2-(8-oxa-6,16,22-triazatetracyclo[14.5.2.02,7.019,23]tricosa-1(22),2(7),3,5,17,19(23),20-heptaen-17-yl)benzimidazole-5-carboxylate. ES/MS: m/z 526.2 [M+H]$^+$.

Step 2

Example 85 was made following steps 4-6 of Procedure 8 using methyl 7-methoxy-1-methyl-2-(8-oxa-6,16,22-triazatetracyclo[14.5.2.02,7.019,23]tricosa-1(22),2(7),3,5,17,19(23),20-heptaen-17-yl)benzimidazole-5-carboxylate.

Procedure 18 (Example 96)

[(1~{R},2~{R},4~{S})-2-amino-7-azabicyclo[2.2.1]heptan-7-yl]-[7-methoxy-1-methyl-2-(6,8,15,21-tetrazatetracyclo[13.5.2.0^{2,7}.0^{18,22}]docosa-1(21),2,4,6,16,18(22),19-heptaen-16-yl)benzimidazol-5-yl]methanone

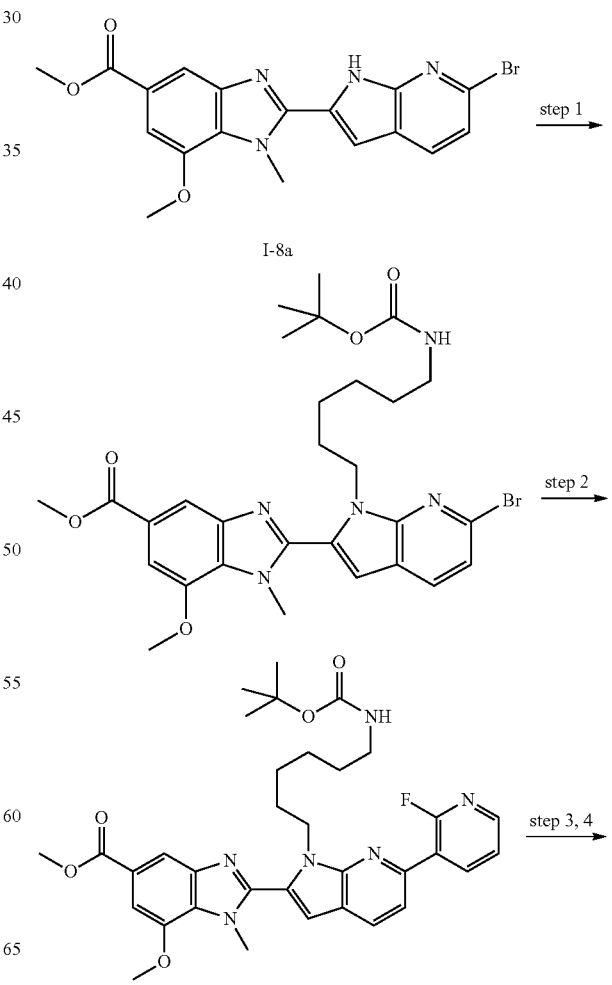

-continued

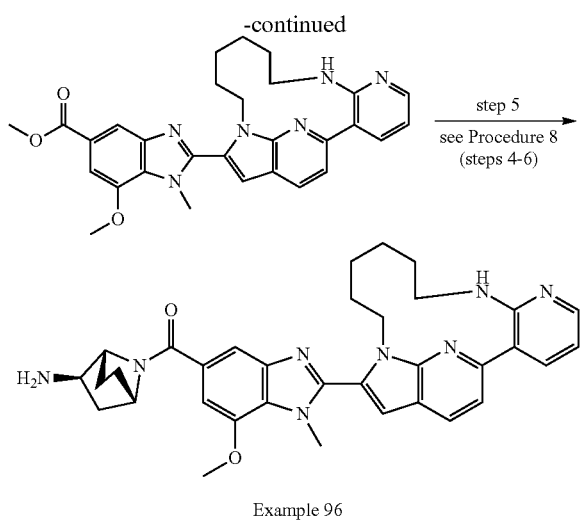

Example 96

Step 1

To a mixture of methyl 2-(6-bromo-1H-pyrrolo[2,3-b]pyridin-2-yl)-7-methoxy-1-methyl-1H-benzo[d]imidazole-5-carboxylate (I-8a, 250 mg, 0.60 mmol), tert-butyl N-(6-bromohexyl)carbamate (202 mg, 0.72 mmol), and cesium carbonate (588 mg, 1.8 mmol) was added 2.5 mL of DMF. The reaction mixture was stirred at ambient temperature overnight, then heated to 60° C. for 1 h. After cooling to ambient temperature, the mixture was poured into EtOAc and washed with water, then brine. The organic phase was concentrated, adsorbed to isolute, and purified by silica gel chromatography (eluent: EtOAc/hexane) to provide methyl 2-(6-bromo-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate. ES/MS: m/z 614.2 [M+H]+.

Step 2

Followed step 2 of I-108 using methyl 2-(6-bromo-1-(6-((tert-butoxycarbonyl)amino)hexyl)-1H-pyrrolo[2,3-b]pyridin-2-yl)-7-methoxy-1-methyl-1H-benzo[d]imidazole-5-carboxylate (100 mg, 0.16 mmol), 2-fluoropyridine-3-boronic acid (34 mg, 0.24 mmol) and stirring at 100° C. for 3 h. Purification by silica gel chromatography (eluent: 3:1 EtOAc/EtOH with 0.25% triethylamine in hexane) provided methyl 2-(1-(6-((tert-butoxycarbonyl)amino)hexyl)-6-(2-fluoropyridin-3-yl)-1H-pyrrolo[2,3-b]pyridin-2-yl)-7-methoxy-1-methyl-1H-benzo[d]imidazole-5-carboxylate. ES/MS: m/z 631.3 [M+H]+.

Step 3

Followed step 1 of Procedure 15 using methyl 2-(1-(6-((tert-butoxycarbonyl)amino)hexyl)-6-(2-fluoropyridin-3-yl)-1H-pyrrolo[2,3-b]pyridin-2-yl)-7-methoxy-1-methyl-1H-benzo[d]imidazole-5-carboxylate (96 mg, 0.15 mmol). The reaction was concentrated and used in step 4 without purification. ES/MS: m/z 531.2 [M+H]+.

Step 4

To a solution of methyl 2-(1-(6-aminohexyl)-6-(2-fluoropyridin-3-yl)-1H-pyrrolo[2,3-b]pyridin-2-yl)-7-methoxy-1-methyl-1H-benzo[d]imidazole-5-carboxylate (0.10 mmol, crude from previous rxn) in DMSO (5 mL) was added potassium carbonate (133 mg, 10.0 mmol). The mixture was heated to 100° C. for 18 h. After cooling, water was added to give a yellow solid, which was collected by filtration. The aqueous filtrate was extracted twice into EtOAc, dried over MgSO4, filtered, and concentrated. The solids and extracts were combined and used in the next step without purification. ES/MS: m/z 511.2 [M+H]+.

Step 5

Example 96 was made following steps 4-6 of Procedure 8 using methyl 7-methoxy-1-methyl-2-(6,8,15,21-tetrazatetracyclo[13.5.2.0²,⁷.0¹⁸,²²]docosa-1(21),2(7),3,5,16,18(22),19-heptaen-16-yl)benzimidazole-5-carboxylate.

Procedure 19 (Example 227)

17-[5-[(1~{R},2~{R},4~{S})-2-amino-7-azabicyclo[2.2.1]heptane-7-carbonyl]-7-methoxy-1-methyl-benzimidazol-2-yl]-11-methyl-1,8,19-triazatricyclo[10.5.2.0^{15,18}]nonadeca-12(19),13,15(18),16-tetraen-9-one (1:1 Mixture of Epimers)

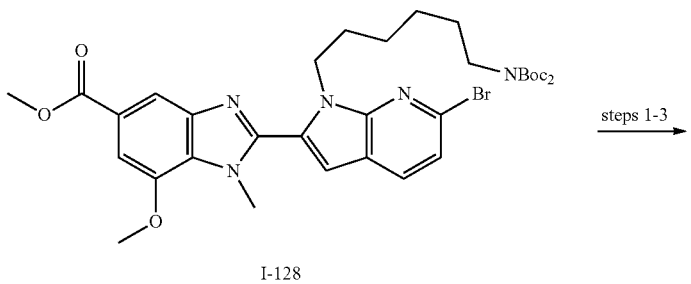

I-128 steps 1-3

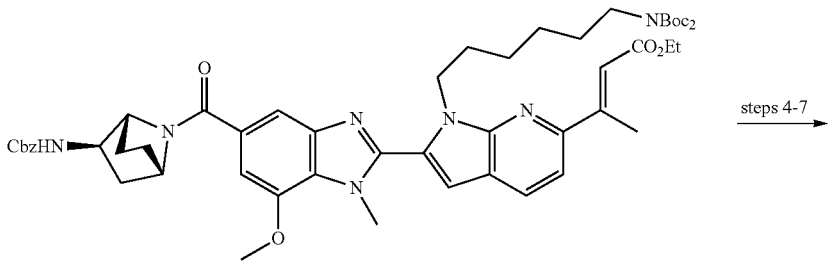

steps 4-7

-continued

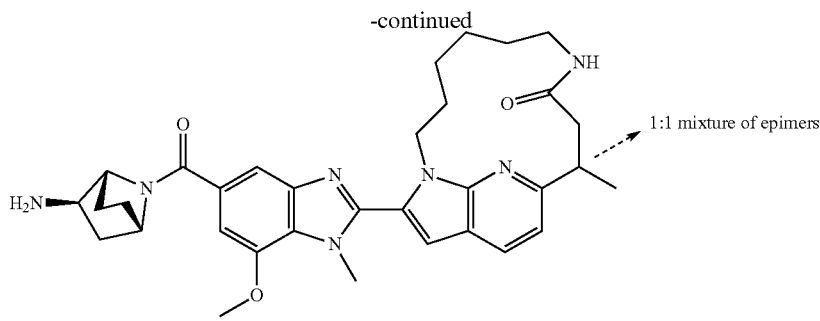

Example 227

Step 1

2-[1-[6-[bis(tert-butoxycarbonyl)amino]hexyl]-6-bromopyrrolo[2,3-b]pyridin-2-yl]-7-methoxy-1-methyl-benzimidazole-5-carboxylate (100 mg, 0.14 mmol), ethyl (Z)-3-(4,4,5,5-tetramethyl-1,3,2-dioxaborolan-2-yl)but-2-enoate (67 mg, 0.28 mmol) and $K_3PO_4$ (89 mg, 0.42 mmol) were charged in a vial and suspended in $THF/H_2O$ (10:1, 5.5 mL). The resulting mixture was degassed with Ar for 5 minutes before XPhos Pd G3 (5.9 mg, 0.07 mmol) was added and the vial was sealed. The mixture was heated to 90° C. for 5 h and then cooled back to room temperature. After aqueous workup, the residue was purified by flash chromatography over silica gel (Hexanes/EtOAc 0-15%) to afford methyl 2-[1-[6-[bis(tert-butoxycarbonyl)amino]hexyl]-6-[(E)-3-ethoxy-1-methyl-3-oxo-prop-1-enyl]pyrrolo[2,3-b]pyridin-2-yl]-7-methoxy-1-methyl-benzimidazole-5-carboxylate.

Step 2

2-[1-[6-[bis(tert-butoxycarbonyl)amino]hexyl]-6-[(E)-3-ethoxy-1-methyl-3-oxo-prop-1-enyl]pyrrolo[2,3-b]pyridin-2-yl]-7-methoxy-1-methyl-benzimidazole-5-carboxylate (91 mg, 0.12 mmol) was dissolved in THF (1.2 mL) and a solution of LiOH (2 M, 0.10 mL) was added. The resulting mixture was stirred at 50° C. overnight, then cool back to room temperature and quenched with HCl in dioxane (4 N, 0.1 mL). After evaporation to dryness, the residue was purified by flash chromatography over silica gel (DCM/MeOH 0-4%) to afford methyl 2-[1-[6-[bis(tert-butoxycarbonyl)amino]hexyl]-6-[(E)-3-ethoxy-1-methyl-3-oxo-prop-1-enyl]pyrrolo[2,3-b]pyridin-2-yl]-7-methoxy-1-methyl-benzimidazole-5-carboxylate.

Step 3

Methyl 2-[1-[6-[bis(tert-butoxycarbonyl)amino]hexyl]-6-[(E)-3-ethoxy-1-methyl-3-oxo-prop-1-enyl]pyrrolo[2,3-b]pyridin-2-yl]-7-methoxy-1-methyl-benzimidazole-5-carboxylate (45 mg, 0.06 mmol) was dissolved in DMF (0.5 mL) and DIPEA was added (23 mg, 0.15 mmol) followed by HATU (21 mg, 0.09 mmol) and benzyl ((1R,2R,4S)-7-azabicyclo[2.2.1]heptan-2-yl)carbamate (A4, 30 mg, 0.12 mmol). The reaction mixture was stirred for 1 h, then worked up and purified by flash chromatography over silica gel (Hexanes/EtOAc 5-100%) to afford ethyl (E)-3-[2-[5-[2-(benzyloxycarbonylamino)-7-azabicyclo[2.2.1]heptane-7-carbonyl]-7-methoxy-1-methyl-benzimidazol-2-yl]-1-[6-[bis(tert-butoxycarbonyl)amino]hexyl]pyrrolo[2,3-b]pyridin-6-yl]but-2-enoate.

Step 4

Pd/C (5% w/w, 50 mg) was added to a solution of ethyl (E)-3-[2-[5-[2-(benzyloxycarbonylamino)-7-azabicyclo[2.2.1]heptane-7-carbonyl]-7-methoxy-1-methyl-benzimidazol-2-yl]-1-[6-[bis(tert-butoxycarbonyl)amino]hexyl]pyrrolo[2,3-b]pyridin-6-yl]but-2-enoate (50 mg, 0.53 mmol) in EtOAc (1 mL). The reaction vessel was flushed with $N_2$ and then placed under an $H_2$ atmosphere until full conversion, as judged by LCMS analysis. The reaction vessel was flushed with $N_2$ and the heterogeneous mixture was filtered through a plug of celite. The filtrate was evaporated to afford a crude residue was used directly in the next step.

Step 5.

The residue above was dissolved in THF/MeOH (1:1, 1 mL) and a solution of LiOH (2 M, 0.2 mL) was added. The resulting solution was stirred vigorously at 90° C. for 48 h. The mixture was then evaporated to dryness and the residue was suspended in DCM. HCl in dioxane (4 N, 0.3 mL) was added and after 5 minutes the mixture was evaporated to dryness at 40° C. to afford crude 3-[1-(6-aminohexyl)-2-[5-[2-(benzyloxycarbonylamino)-7-azabicyclo[2.2.1]heptane-7-carbonyl]-7-methoxy-1-methyl-benzimidazol-2-yl]pyrrolo[2,3-b]pyridin-6-yl]butanoic acid.

Step 6

The crude acid from above was dissolved in DMF (0.5 mL) and DIPEA (21 mg, 0.16 mmol) was added followed by HATU (30 mg, 0.08 mmol). The resulting solution was stirred at room temperature for 1 h. Water and ethyl acetate were added. After usual work up, the crude mixture was purified by flash chromatography over silica gel (Hexanes/EtOAc 10-100%) to afford benzyl N-[(1R,2R,4S)-7-[7-methoxy-1-methyl-2-(11-methyl-9-oxo-1,8,19-triazatricyclo[10.5.2.015,18]nonadeca-12(19),13,15(18),16-tetraen-17-yl)benzimidazole-5-carbonyl]-7-azabicyclo[2.2.1]heptan-2-yl]carbamate.

Step 7

Benzyl N-[(1R,2R,4S)-7-[7-methoxy-1-methyl-2-(11-methyl-9-oxo-1,8,19-triazatricyclo[10.5.2.015,18]nonadeca-12(19),13,15(18),16-tetraen-17-yl)benzimidazole-5-carbonyl]-7-azabicyclo[2.2.1]heptan-2-yl]carbamate (16 mg, 0.02 mmol) was dissolved in EtOAc/MeOH (1:1, 1 mL) and a drop of TFA was added. Pd/C (5% w/w, 16 mg) was then added and the reaction vessel was flushed with $N_2$ and then placed under an $H_2$ atmosphere until full conversion. The crude mixture was then filtered and after evaporation the crude material was purified by reverse phase preparative HPLC to afford Example 227 as a 1:1 mixture of epimers.

Procedure 20 (Example 259)
17-[5-[(1~{R},2~{R},4~{S})-2-amino-7-azabicyclo[2.2.1]heptane-7-carbonyl]-7-methoxy-1-methyl-benzimidazol-2-yl]-11-cyclopropyl-1,10,19-triazatricyclo[10.5.2.0^{15,18}]nonadeca-12(19),13,15(18),16-tetraen-9-one (1:1 Mixture of Epimers)
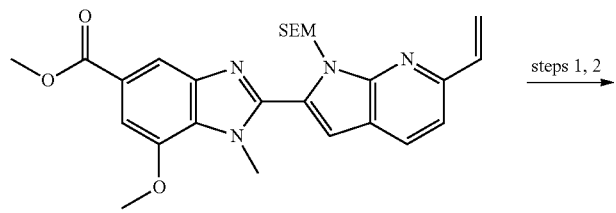
I-129
steps 1, 2 →
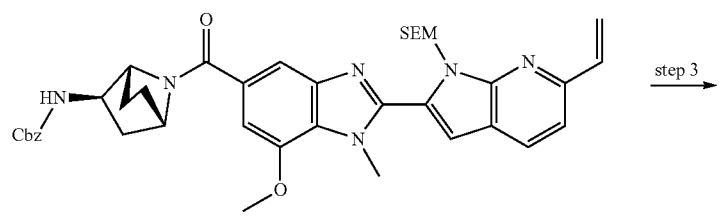
step 3 →
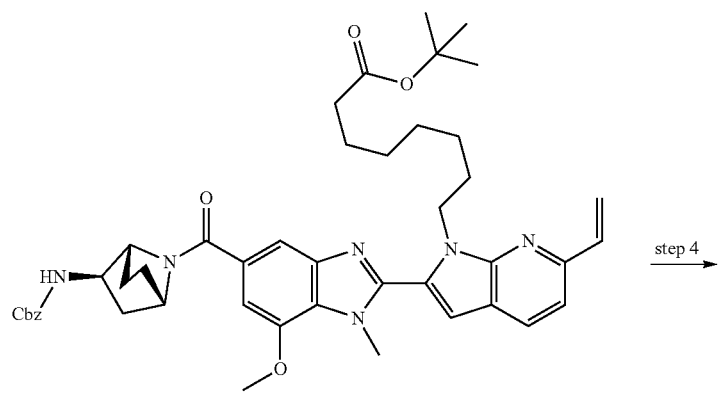
step 4 →
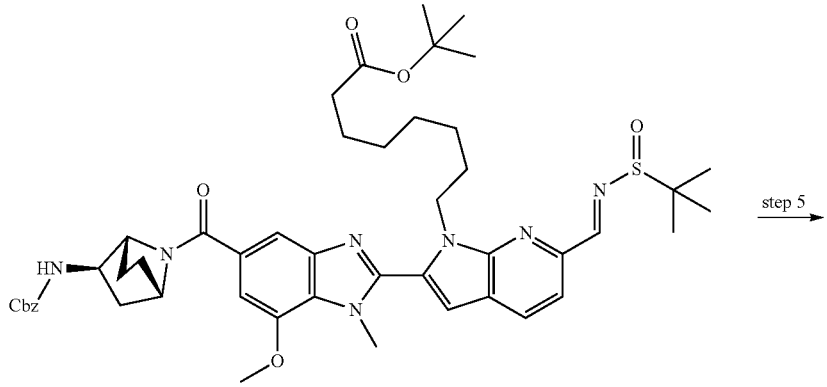
step 5 →

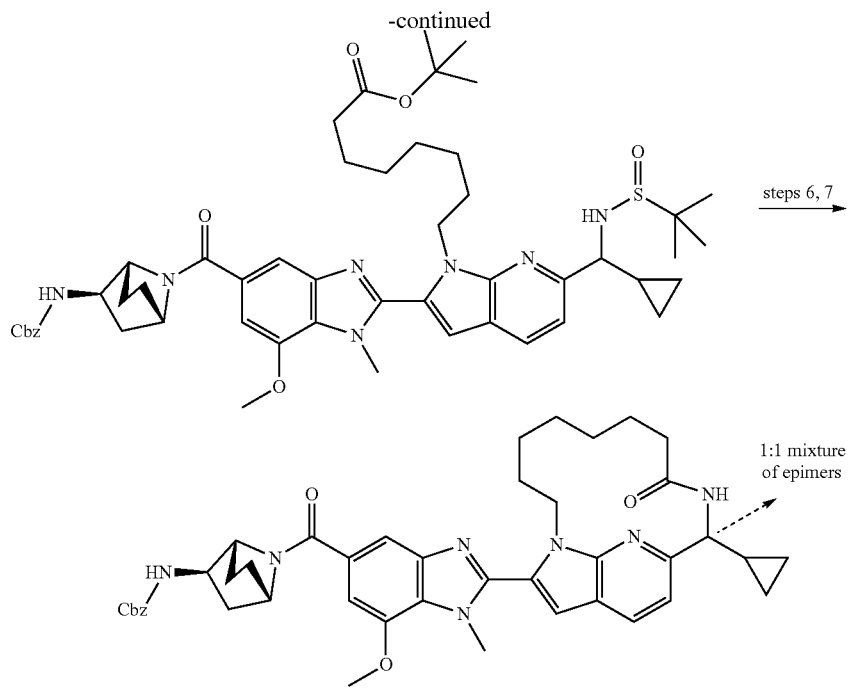

Example 259

Step 1.

Methyl 7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carboxylate (903 mg) was dissolved in THF (30 mL) and MeOH (15 mL). Water (15 mL) and LiOH·H$_2$O (630 mg, 15 mmol) were added. After stirring overnight, the reaction mixture was quenched with the addition of 6 N HCl aqueous solution (2.75 mL), and diluted with ethyl acetate and water. The layers were separated and the aqueous extracted with ethyl acetate. The combined organics were dried (MgSO$_4$), filtered, and concentrated under reduced pressure to yield 7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carboxylic acid.

Step 2

7-Methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carboxylic acid (877 mg) was dissolved in DMF (12 mL) and benzyl ((1R,2R,4S)-7-azabicyclo[2.2.1]heptan-2-yl)carbamate (A4, 550 mg, 1.95 mmol), N,N-Diisopropylethylamine (1.28 mL, 7.33 mmol) and HATU (1045 mg, 2.75 mmol) were added. After 30 minutes, the reaction mixture was diluted water and the resulting precipitate was filtered, washed with water, and dried in vacuo to yield benzyl ((1R,2R,4S)-7-(7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carbonyl)-7-azabicyclo[2.2.1]heptan-2-yl)carbamate. ES/MS: m/z 707.0 [M+H]$^+$.

Step 3

Trifluoroacetic acid (1.20 mL, 15.6 mmol) was added to a solution of benzyl ((1R,2R,4S)-7-(7-methoxy-1-methyl-2-(1-((2-(trimethylsilyl)ethoxy)methyl)-6-vinyl-1H-pyrrolo[2,3-b]pyridin-2-yl)-1H-benzo[d]imidazole-5-carbonyl)-7-azabicyclo[2.2.1]heptan-2-yl)carbamate (550 mg, 0.778 mmol). After 19 h, an additional 0.2 mL of TFA was added. After 1 h, the reaction mixture was concentrated and dried in vacuo. This residue was dissolved in DMF (5 mL) and tert-butyl 8-bromooctanoate (L1a, 522 mg, 1.87 mmol) and cesium carbonate (1288 mg, 3.96 mmol) were added. The reaction mixture was heated to 60° C. for 21 h and then cooled to rt. The reaction mixture was diluted with ethyl acetate and water. The layers were separated and the aqueous was extracted with ethyl acetate. The combined organics were washed with water, brine, dried (MgSO$_4$), filtered, and concentrated under reduced pressure to yield a residue that was purified via silica gel column chromatography (0-6% methanol in dichloromethane) to yield tert-butyl 8-(2-(5-(((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-vinyl-1H-pyrrolo[2,3-b]pyridin-1-yl)octanoate. ES/MS: m/z 775.0 [M+H]$^+$.

Step 4 tert-Butyl 8-(2-(5-((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-vinyl-1H-pyrrolo[2,3-b]pyridin-1-yl)octanoate (250 mg, 0.323 mmol) was taken up in THF (5.5 mL) and water (4 mL). Potassium osmate(IV) (6 mg, 0.0161 mmol) and sodium periodate (248 mg, 1.16 mmol) were added. After 4 h, water was added and the resulting solid was filtered, washed with water, and dried in vacuo to yield tert-butyl 8-(2-(5-((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-((E)-((tert-butylsulfinyl)imino)methyl)-1H-pyrrolo[2,3-b]pyridin-1-yl)octanoate. The residue was dissolved in DCM (8 mL), and CuSO$_4$ (487 mg, 1.95 mmol and 2-methylpropane-2-sulfinamide (123 mg, 1.01 mmol) were added. After stirring at 45° C. for 22 h, the reaction mixture was filtered over celite. The filtrate was concentrated and the resulting residue was purified via silica gel column chromatography (0-100% ethyl acetate in hexanes) to yield tert-butyl 8-(2-(5-(((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-((E)-((tert-butylsulfinyl)imino)methyl)-1H-pyrrolo[2,3-b]pyridin-1-yl)octanoate. ES/MS: m/z 880.0 [M+H]$^+$.

Step 5

To a solution of tert-butyl 8-(2-(5-(((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-((E)-((tert-butylsulfinyl)imino)methyl)-1H-pyrrolo[2,3-b]pyridin-1-yl)octanoate (76 mg, 0.086 mmol) at −40° C. in MeTHF (4 mL) was added a 1 M solution of cyclopropylmagnesium bromide in 2-MeTHF (0.7 mL, 0.7 mmol). The reaction mixture was warmed to rt and stirred 3 h. The reaction mixture was diluted with ethyl acetate and water. The layers were separated and the aqueous was extracted with ethyl acetate. The combined organics were washed with water, brine, dried (MgSO$_4$), filtered, and concentrated under reduced pressure to yield tert-butyl 8-(2-(5-(((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-(((tert-butylsulfinyl)amino)(cyclopropyl)methyl)-1H-pyrrolo[2,3-b]pyridin-1-yl)octanoate (74 mg, 90%), which was used without purification. ES/MS: m/z 922.1 [M+H]$^+$.

Step 6

A solution of HCl in dioxane (4 N, 0.40 mL, 1.6 mmol) was added to a solution of tert-butyl 8-(2-(5-(((1R,2R,4S)-2-(((benzyloxy)carbonyl)amino)-7-azabicyclo[2.2.1]heptane-7-carbonyl)-7-methoxy-1-methyl-1H-benzo[d]imidazol-2-yl)-6-(((tert-butylsulfinyl)amino)(cyclopropyl)methyl)-1H-pyrrolo[2,3-b]pyridin-1-yl)octanoate (74 mg, 0.0802 mmol) in DCM (5 mL). After 17 h, TFA (0.80 mL, 10.5 mmol) was added. After 5 h, the reaction mixture was concentrated under reduced pressure and dried in vacuo. The resulting residue was dissolved in DMF (4 mL) and DIPEA (0.11 mL, 0.64 mmol) and HATU (46 mg, 0.12 mmol) were added. After 2 h, the mixture was diluted with water and DCM and the layers were separated. The aqueous was extracted with DCM and the combined organics were dried (MgSO$_4$), filtered, and concentrated under reduced pressure to yield benzyl N-[(1R,2R,4S)-7-[2-(11-cyclopropyl-9-oxo-1,10,19-triazatricyclo[10.5.2.015,18]nonadeca-12(19),13,15(18),16-tetraen-17-yl)-7-methoxy-1-methyl-benzimidazole-5-carbonyl]-7-azabicyclo[2.2.1]heptan-2-yl]carbamate which was used without purification. ES/MS: m/z 744.5 [M+H]$^+$.

Step 7

A mixture of benzyl N-[(1R,2R,4S)-7-[2-(11-cyclopropyl-9-oxo-1,10,19-triazatricyclo[10.5.2.015,18]nonadeca-12(19),13,15(18),16-tetraen-17-yl)-7-methoxy-1-methyl-benzimidazole-5-carbonyl]-7-azabicyclo[2.2.1]heptan-2-yl]carbamate (60 mg, 0.08 mmol), TFA (2 drops), and 10% Pd/C (35 mg, 0.033 mmol) in ethanol (4 mL) was hydrogenated under an atmosphere of hydrogen for 21 h. The mixture was then heated at 45° C. for 3 h, cooled to rt, filtered over celite, and the filtrate concentrated under reduced pressure. The resulting residue was purified via preparative HPLC (eluent: water/MeCN*0.1% TFA) to yield Example 259.

Procedure 21 (Examples 235 and 236)

(11~{S})-17-[5-[(3~{R})-3-aminopiperidine-1-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one (Example 235)

(11~{R})-17-[5-[(3~{R})-3-aminopiperidine-1-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one (Example 236)

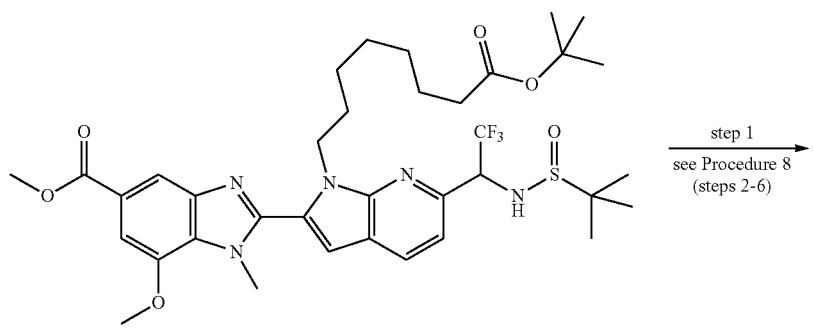

I-132

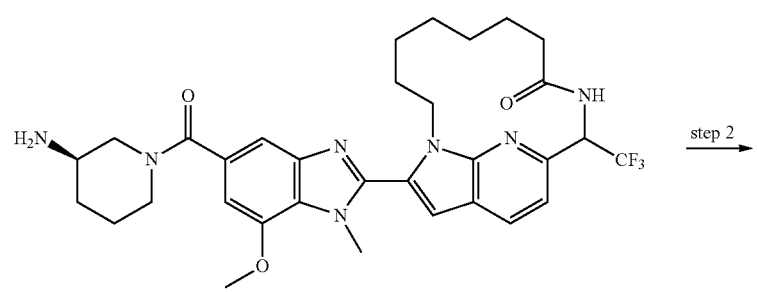

step 2

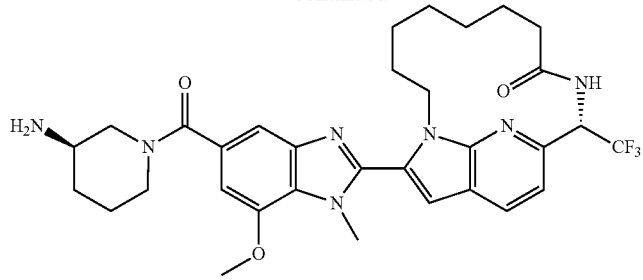

Example 235

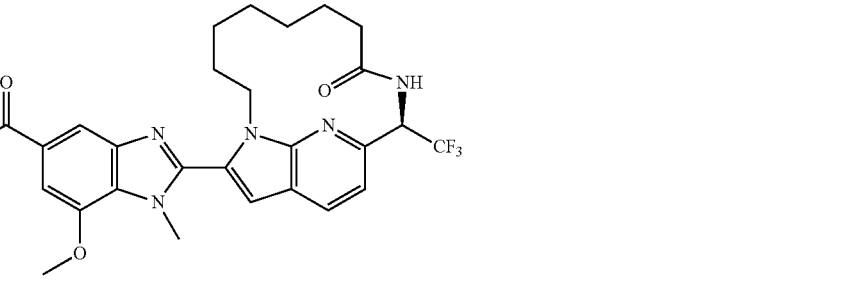

Example 236

Step 1.

17-[5-[(3R)-3-aminopiperidine-1-carbonyl]-7-methoxy-1-methyl-benzimidazol-2-yl]-11-(trifluoromethyl)-1,10,19-triazatricyclo[10.5.2.015,18]nonadeca-12(19),13,15(18),16-tetraen-9-one was made following steps 2-6 Procedure 8 using I-132 and A1.01.

Step 2

Examples 235 and 236 were separated via chiral SFC. The first eluting peak was assigned as the (11S)-configuration (Example 235), and the second eluting peak was assigned as the (11R)-configuration (Example 236). Note: Some Examples were not separated via chiral SFC and were tested as a epimeric mixtures.

Procedure 22 (Example 234)

17-[5-[(3~{R})-3-aminopiperidine-1-carbonyl]-7-methoxy-1-methyl-benzimidazol-2-yl]-10-methyl-1,10,19-triazatricyclo[10.5.2.0ˆ{15,18}]nonadeca-12(19),13,15(18),16-tetraen-9-one

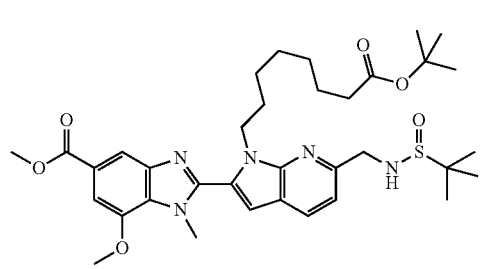

I-131

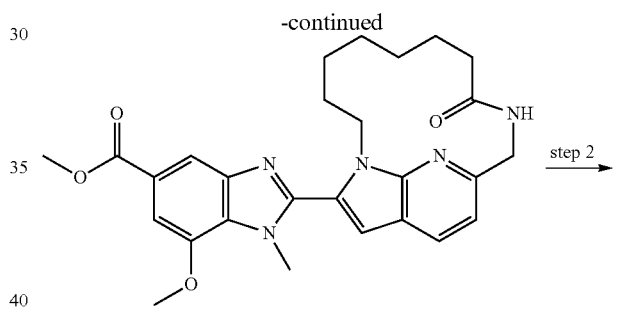

step 2

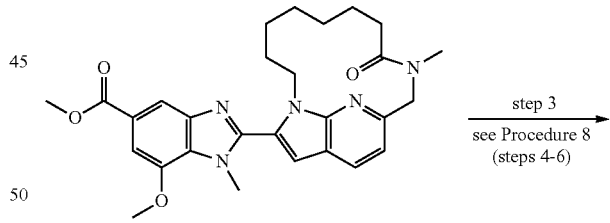

step 3
see Procedure 8
(steps 4-6)


Example 234

Step 1.

methyl 7-methoxy-1-methyl-2-(9-oxo-1,10,19-triazatricyclo[10.5.2.015,18]nonadeca-12(19),13,15(18),16-tetraen- 17-yl)benzimidazole-5-carboxylate was made following steps 2-3 of Procedure 8 using I-131. ES/MS: m/z 490.4 [M+H]⁺.

Step 2

Sodium hydride (60% dispersion, 20 mg, 0.50 mmol) was added to a cooled solution of methyl 7-methoxy-1-methyl-2-(9-oxo-1,10,19-triazatricyclo[10.5.2.015,18]nonadeca-12(19),13,15(18),16-tetraen-17-yl)benzimidazole-5-carboxylate (60 mg, 0.123 mmol) in THF (3 mL) at 0° C. After 20 minutes, iodomethane (0.031 mL, 0.490 mmol) was added and the reaction mixture was warmed to rt and stirred 48 h. The reaction mixture was diluted with ethyl acetate and water. The layers were separated and the aqueous was extracted with ethyl acetate. The combined organics were washed with water, brine, dried (MgSO₄), filtered, and concentrated under reduced pressure to yield methyl 7-methoxy-1-methyl-2-(10-methyl-9-oxo-1,10,19-triazatricyclo[10.5.2.015,18]nonadeca-12(19),13,15(18),16-tetraen-17-yl)benzimidazole-5-carboxylate, which was used without purification. ES/MS: m/z 504.4 [M+H]⁺.

Step 3

Example 234 was made following steps 4-6 of Procedure 8 using A1.01 and methyl 7-methoxy-1-methyl-2-(10-methyl-9-oxo-1,10,19-triazatricyclo[10.5.2.015,18]nonadeca-12(19),13,15(18),16-tetraen-17-yl)benzimidazole-5-carboxylate.

Procedure 23 (Example 291)

[(3~{R})-3-amino-1-piperidyl]-[7-methoxy-1-methyl-2-(11-methyl-10-oxa-1,19-diazatricyclo[10.5.2.0^{15,18}]nonadeca-12(19),13,15(18),16-tetraen-17-yl)benzimidazol-5-yl]methanone (1:1 Mixture of Epimers)

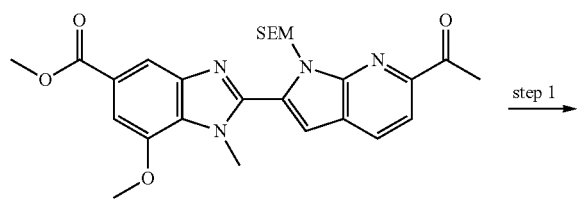

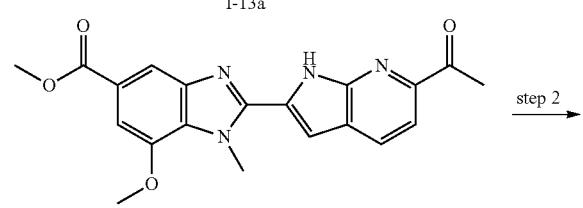

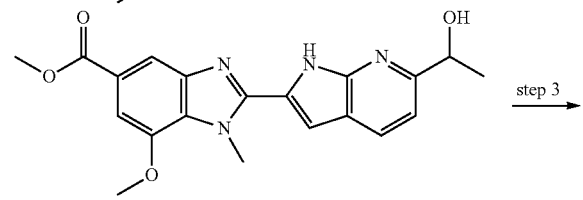

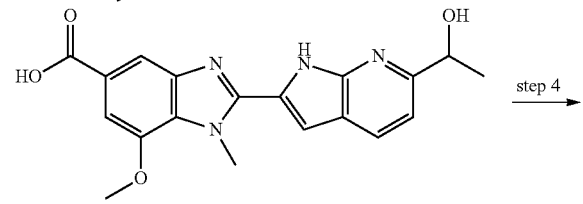

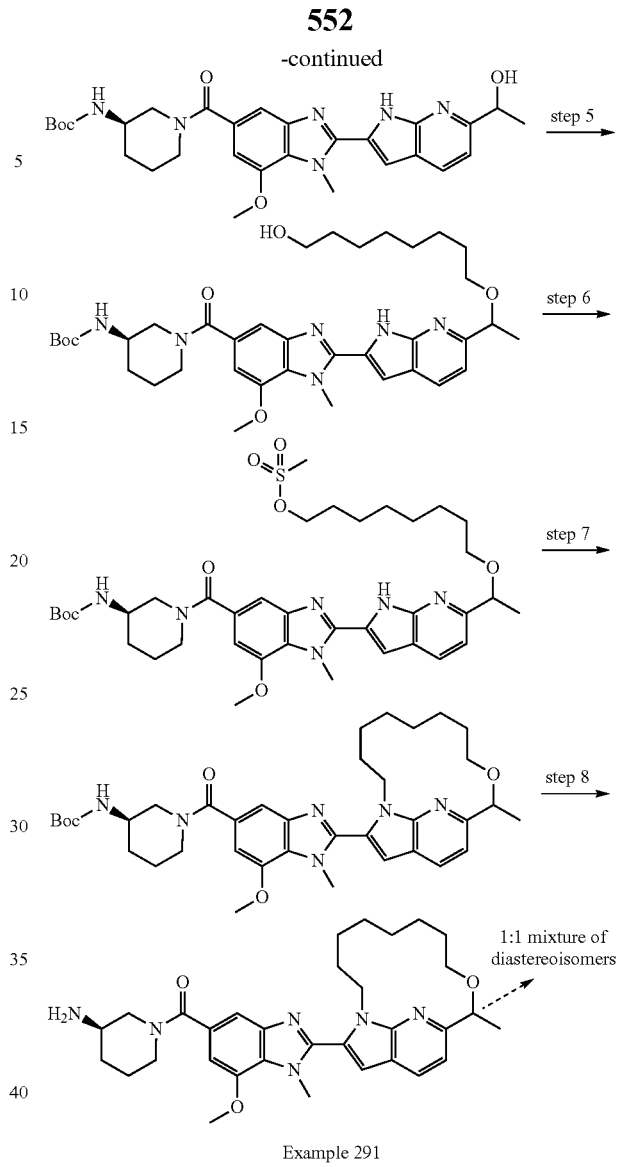

Example 291

Step 1

A solution of methyl 2-[6-acetyl-1-(2-trimethylsilylethoxymethyl)pyrrolo[2,3-b]pyridin-2-yl]-7-methoxy-1-methyl-benzimidazole-5-carboxylate (0.15 g, 0.29 mmol) in dichloromethane (1 mL) and trifluoroacetic acid (1 mL) was stirred for 6 h. The mixture was concentrated, diluted with MeTHF (10 mL) and washed with 1 M NaOH (5 mL) followed by water (2×5 mL). The organic layer was dried with Na₂SO₄, filtered, and concentrated. The crude methyl 2-(6-acetyl-1H-pyrrolo[2,3-b]pyridin-2-yl)-7-methoxy-1-methyl-1H-benzo[d]imidazole-5-carboxylate was taken to next step without further purification. ES/MS: m/z 379.2 [M+H]⁺.

Step 2.

To a solution of methyl 2-(6-acetyl-1H-pyrrolo[2,3-b]pyridin-2-yl)-7-methoxy-1-methyl-1H-benzo[d]imidazole-5-carboxylate (0.11 g, 0.29 mmol) in THF (4 mL) was added dropwise 1 M borane in THF (2.4 mL). The reaction was stirred at ambient temperature for 8 h. The mixture was quenched with methanol (10 mL) and concentrated. The crude product was dissolved in methanol and stirred at 60° C. for 1 h. The mixture was concentrated and the crude methyl 2-(6-(1-hydroxyethyl)-1H-pyrrolo[2,3-b]pyridin-2- yl)-7-methoxy-1-methyl-1H-benzo[d]imidazole-5-carboxylate was taken to next step without further purification. ES/MS: m/z 381.2 [M+H]⁺.

Step 3

A solution of methyl 2-(6-(1-hydroxyethyl)-1H-pyrrolo[2,3-b]pyridin-2-yl)-7-methoxy-1-methyl-1H-benzo[d]imidazole-5-carboxylate (0.11 g, 0.29 mmol), methanol (2 ml), and 10 M NaOH (0.2 mL) was stirred at 60° C. for 2 h. The mixture was concentrated, diluted with water, and acidified to pH~3 with 1 M HCl (aq). The solids were filtered and filtrate was extracted with MeTHF (10 mL). The organic layer was dried with Na₂SO₄, filtered, and concentrated. The solids were combined and the crude 2-(6-(1-hydroxyethyl)-1H-pyrrolo[2,3-b]pyridin-2-yl)-7-methoxy-1-methyl-1H-benzo[d]imidazole-5-carboxylic acid was taken to next step without further purification. ES/MS: m/z 367.1 [M+H]⁺.

Step 4

To a solution of 2-(6-(1-hydroxyethyl)-1H-pyrrolo[2,3-b]pyridin-2-yl)-7-methoxy-1-methyl-1H-benzo[d]imidazole-5-carboxylic acid (100 mg, 0.27 mmol), tert-butyl (R)-piperidin-3-ylcarbamate (A1.01, 82 mg, 0.41 mmol), and EtN(i-Pr)₂ (96 µL, 0.55 mmol) in DMF (1 mL) was added HATU (156 mg, 0.41 mmol). The mixture was stirred for 10 minutes, diluted with EtOAc (20 mL) and washed with 5% LiCl (aq, 20 mL). The organic layer was dried with Na₂SO₄, filtered, and concentrated. The crude product was purified by silica chromatography using methanol in dichloromethane (0-20%) to afford tert-butyl ((3R)-1-(2-(6-(1-hydroxyethyl)-1H-pyrrolo[2,3-b]pyridin-2-yl)-7-methoxy-1-methyl-1H-benzo[d]imidazole-5-carbonyl)piperidin-3-yl)carbamate. ES/MS: m/z 549.3 [M+H]⁺.

Step 5

To a solution of tert-butyl ((3R)-1-(2-(6-(1-((8-hydroxyoctyl)oxy)ethyl)-1H-pyrrolo[2,3-b]pyridin-2-yl)-7-methoxy-1-methyl-1H-benzo[d]imidazole-5-carbonyl)piperidin-3-yl)carbamate (65 mg, 0.12 mmol) and EtN(i-Pr)₂ (110 µL, 0.47 mmol) in DCE (0.3 mL) was added a solution of methanesulfonic anhydride (41 mg, 0.24 mmol) in DCE (0.2 mL) at 0° C. After stirring for 5 minutes, octane-1,8-diol (173 mg, 1.18 mmol) was added and the reaction was stirred at 60° C. for 1 h. The mixture was cooled to room temperature and tert-butoxycarbonyl tert-butyl carbonate (26 mg, 0.12 mmol) was added. After stirring for 5 minutes, the crude product was purified by silica chromatography using methanol in dichloromethane to afford tert-butyl ((3R)-1-(2-(6-(1-((8-hydroxyoctyl)oxy)ethyl)-1H-pyrrolo[2,3-b]pyridin-2-yl)-7-methoxy-1-methyl-H-benzo[d]imidazole-5-carbonyl)piperidin-3-yl)carbamate. ES/MS: m/z 677.4 [M+H]⁺.

Step 6

To a solution of tert-butyl ((3R)-1-(2-(6-(1-((8-hydroxyoctyl)oxy)ethyl)-1H-pyrrolo[2,3-b]pyridin-2-yl)-7-methoxy-1-methyl-1H-benzo[d]imidazole-5-carbonyl)piperidin-3-yl)carbamate (60 mg, 0.088 mmol) and EtN(i-Pr)₂ (41 µL, 176 µmol) in dichloromethane (1.3 mL) was added methanesulfonyl chloride (6.8 µL, 89 µmol). After stirring for 30 minutes, the crude product was purified by silica chromatography using methanol in dichloromethane to afford 8-(1-(2-(5-((R)-3-((tert-butoxycarbonyl)amino)piperidine-1-carbonyl)-7-methoxy-1-methyl-1H-benzo[d]imidazol-2-yl)-1H-pyrrolo[2,3-b]pyridin-6-yl)ethoxy)octyl methanesulfonate. ES/MS: m/z 755.4 [M+H]⁺.

Step 7

To a solution of tert-butyl ((3R)-1-(7-methoxy-1-methyl-2-(2-methyl-11H-3-oxa-1(6,1)-pyrrolo[2,3-b]pyridinacycloundecaphane-12-yl)-1H-benzo[d]imidazole-5-carbonyl)piperidin-3-yl)carbamate (60 mg, 79 µmol) in DMF (1.8 mL) was added sodium hydride (8 mg, 340 µmol). The mixture was stirred at 50° C. for 18 h. The mixture was poured into 5% LiCl (aq, 10 mL) was extracted with EtOAc (10 mL). The organic layer was washed with 5% LiCl (aq, 10 mL). The organic layer was dried with Na₂SO₄, filtered, and concentrated. The crude product was taken to next step without further purification. ES/MS: m/z 659.4 [M+H]⁺.

Step 8

A solution of tert-butyl N-[(3R)-1-[7-methoxy-1-methyl-2-(11-methyl-10-oxa-1,19-diazatricyclo[10.5.2.015,18]nonadeca-12(19),13,15(18),16-tetraen-17-yl)benzimidazole-5-carbonyl]-3-piperidyl]carbamate (60 mg, 91 µmol) was stirred in dichloromethane (0.5 mL) and trifluoroacetic acid (0.5 mL) for 30 minutes. The mixture was concentrated and the product was purified by RP-HPLC (eluent: water/MeCN with 0.1% TFA) to yield Example 291.

Procedure 24 (Examples 2 and 3)

(5~{E},8~{R},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0ˆ{15,18}]nonadeca-5,12(19),13,15(18),16-pentaen-9-one (Example 2)

(5~{E},8~{S},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0ˆ{15,18}]nonadeca-5,12(19),13,15(18),16-pentaen-9-one (Example 3)

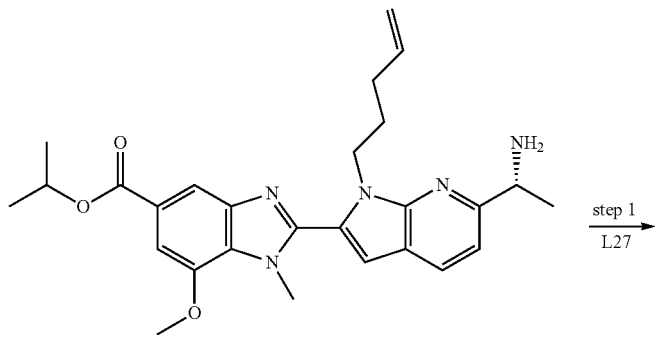

I-107a

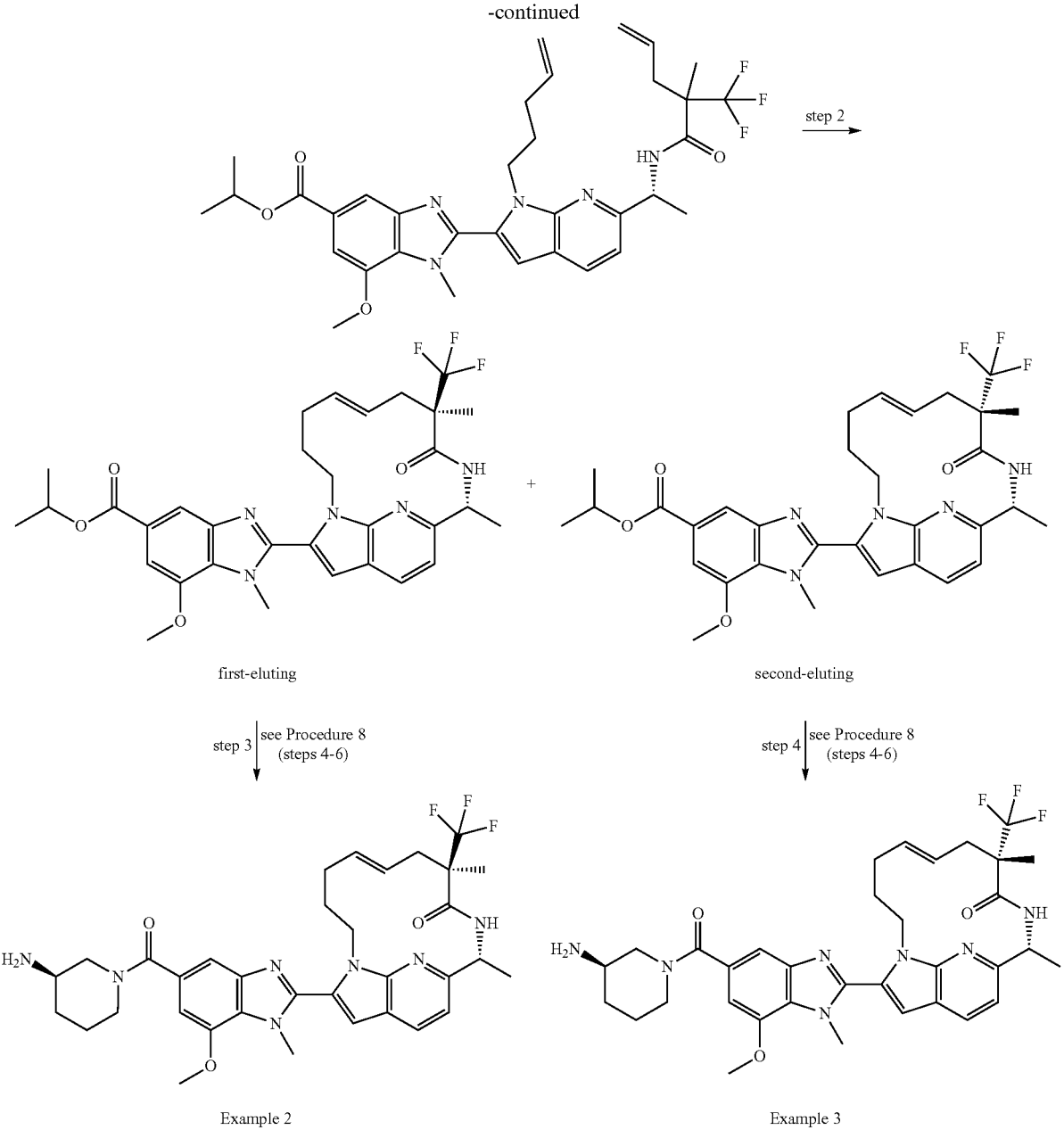

Step 1.

Isopropyl (R)-2-(6-(1-aminoethyl)-1-(pent-4-en-1-yl)-1H-pyrrolo[2,3-b]pyridin-2-yl)-7-methoxy-1-methyl-1H-benzo[d]imidazole-5-carboxylate, TFA salt (I-107a, 0.264 mmol) was dissolved in DMF (6 mL). 2-methyl-2-(trifluoromethyl)pent-4-enoic acid (L27, 195 mg, 1.07 mmol) was added followed by N,N-diisopropylethylamine (0.3 mL, 1.7 mmol) and HATU (130 mg, 0.34 mmol). The reaction mixture was stirred 4 h and partitioned between EtOAc and water. The phases were separated and the organic phase was washed with water, dried over $Na_2SO_4$, filtered, and concentrated. Purification by silica gel chromatography provided isopropyl 7-methoxy-1-methyl-2-(6-((1R)-1-(2-methyl-2-(trifluoromethyl)pent-4-enamido)ethyl)-1-(pent-4-en-1-yl)-1H-pyrrolo[2,3-b]pyridin-2-yl)-1H-benzo[id]imidazole-5-carboxylate. ES/MS: m/z 640.2 $[M+H]^+$.

Step 2

Isopropyl 7-methoxy-1-methyl-2-(6-((1R)-1-(2-methyl-2-(trifluoromethyl)pent-4-enamido)ethyl)-1-(pent-4-en-1-yl)-1H-pyrrolo[2,3-b]pyridin-2-yl)-1H-benzo[d]imidazole-5-carboxylate (148 mg, 0.23 mmol) was dissolved in 1,2-DCE (20 mL) and Zhan-1B catalyst (17 mg, 0.023 mmol) was added. The reaction headspace was purged with $N_2$, and the reaction mixture was heated to 90° C. After 1.25 h, the reaction mixture was concentrated. Purification by silica gel chromatography (20-60% acetone in hexanes) provided a first eluting diastereomer arbitrarily assigned as isopropyl 2-[(5E,8R,11R)-8,11-dimethyl-9-oxo-8-(trifluoromethyl)-1,10,19-triazatricyclo[10.5.2.015,18]nonadeca-5,12(19),13,15(18),16-pentaen-17-yl]-7-methoxy-1-methyl-benzimidazole-5-carboxylate along with a second eluting isomer arbitrarily assigned as isopropyl 2-[(5E,8S,11R)-8,11-dimethyl-9-oxo-8-(trifluoromethyl)-1,10,19-triazatricyclo [10.5.2.015,18]nonadeca-5,12(19),13,15(18),16-pentaen-17-yl]-7-methoxy-1-methyl-benzimidazole-5-carboxylate. First eluting isomer ES/MS: m/z 612.1 [M+H]⁺. Second eluting isomer ES/MS: m/z 612.1 [M+H]⁺.

Step 3

Example 2 was prepared following steps 4-6 of Procedure 8 using A1.01 and isopropyl 2-[(5E,8R,11R)-8,11-dimethyl-9-oxo-8-(trifluoromethyl)-1,10,19-triazatricyclo [10.5.2.015,18]nonadeca-5,12(19),13,15(18),16-pentaen-17-yl]-7-methoxy-1-methyl-benzimidazole-5-carboxylate.

Step 4

Example 3 was prepared following steps 4-6 of Procedure 8 using A1.01 and isopropyl 2-[(5E,8S,11R)-8,11-dimethyl-9-oxo-8-(trifluoromethyl)-1,10,19-triazatricyclo [10.5.2.015,18]nonadeca-5,12(19),13,15(18),16-pentaen-17-yl]-7-methoxy-1-methyl-benzimidazole-5-carboxylate.

Note:

The alkene resulting from the ring closing metathesis reaction (step 2) can be reduced using one of these two general procedures:

a) For Examples without a Cyclopropyl Moiety

Standard hydrogenation conditions (1 atm) with palladium on carbon (10% loading) in EtOH can be performed following step 2 or after step 5 of Procedure 8. The intermediate is typically used without further purification after filtration and concentration.

b) For Examples Containing a Cyclopropyl Moiety, this Alternate Procedure was Followed in Some Cases Reduction using p-toluenesulfonhydrazide (10 equiv.) and NaOAc (14 equiv.) in THF/water at 80° C. followed by workup with EtOAc and saturated aqueous NaHCO₃ can be performed following step 2. The intermediate is typically purified by silica gel chromatography.

Procedure 25 (Example 273)

(5~{E},11~{R})-17-[5-[(3~{R})-3-aminopiperidine-1-carbonyl]-7-methoxy-1-methyl-benzimidazol-2-yl]-8,8,11-trimethyl-1,10-diazatricyclo[10.5.2.0ˆ{15,18}]nonadeca-5,12(19),13,15(18),16-pentaen-9-one

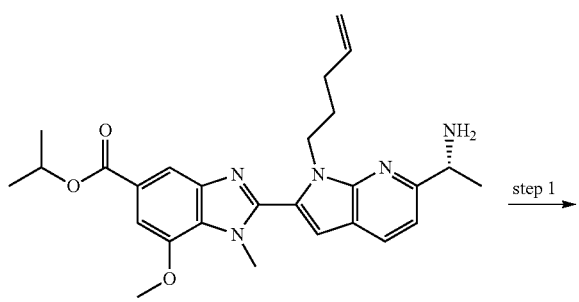

I-107c

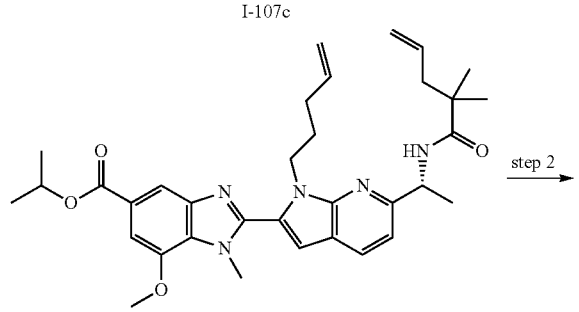

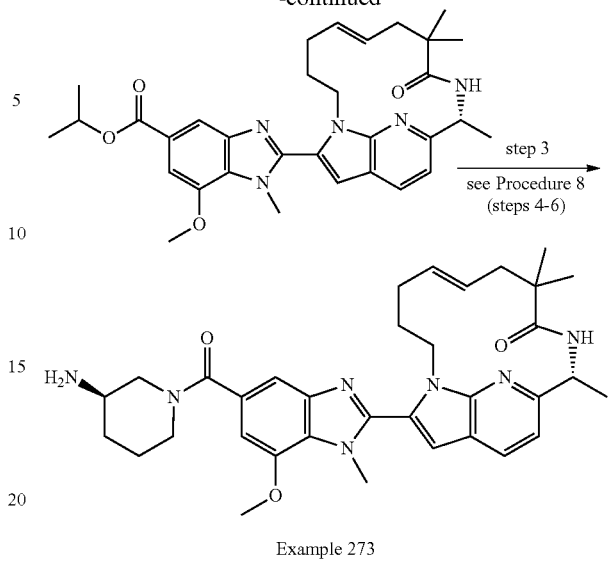

Example 273

Step 1

To a mixture of isopropyl (R)-2-(6-(1-aminoethyl)-1-(pent-4-en-1-yl)-1H-pyrrolo[2,3-b]pyridin-2-yl)-7-methoxy-1-methyl-H-benzo[d]imidazole-5-carboxylate (I-107c, 955 mg, 1.20 mmol) dissolved in dichloromethane (40 mL) was added N,N-diisopropylamine (2.10 mL, 12.08 mmol), 2,2-dimethyl-4-pentenoic acid (0.58 mL, 4.22 mmol) and HATU (1148 mg, 3.02 mmol), and stirred for 16 h. The reaction mixture was quenched with water and extracted with dichloromethane. The combined organics were combined, dried over magnesium sulfate. Filtration and evaporation of solvents yielded the crude product, which was purified on silica gel chromatography (eluent EtOAc/hexanes). ES/MS: m/z 585.3 [M+H]⁺.

Step 2

To a mixture of isopropyl 2-[6-[(1R)-1-(2,2-dimethyl-pent-4-enoylamino)ethyl]-1-pent-4-enyl-indol-2-yl]-7-methoxy-1-methyl-benzimidazole-5-carboxylate (270 mg, 0.46 mmol) in 1,2-dichloroethane (40 mL) was added Zhan-1B catalyst (34.6 mg, 0.046 mmol) under an atmosphere of argon. The mixture was heated at 90° C. for 75 minutes. The reaction mixture was concentrated in vacuo and purified by silica gel chromatography (eluent EtOAc/hexanes) to provide isopropyl 7-methoxy-1-methyl-2-[(5E,11R)-8,8,11-trimethyl-9-oxo-1,10-diazatricyclo[10.5.2.015,18]nonadeca-5,12(19),13,15(18),16-pentaen-17-yl]benzimidazole-5-carboxylate. ES/MS: m/z 557.2 [M+H]⁺.

Step 3

Example 273 was prepared following steps 4-6 of Procedure 8 using A1.01 and isopropyl 7-methoxy-1-methyl-2-[(5E,11R)-8,8,11-trimethyl-9-oxo-1,10-diazatricyclo [10.5.2.015,18]nonadeca-5,12(19),13,15(18),16-pentaen-17-yl]benzimidazole-5-carboxylate.

Note:

The alkene resulting from the ring closing metathesis reaction (step 2) can be reduced using one of these two general procedures:

a) For Examples without a Cyclopropyl Moiety

Standard hydrogenation conditions (1 atm) with palladium on carbon (10% loading) in EtOH can be performed following step 2 or after step 5 of Procedure 8. The intermediate is typically used without further purification after filtration and concentration. An example of this method is described below as Procedure 25a.

b) For Examples Containing a Cyclopropyl Moiety, this Alternate Procedure was Followed in Some Cases Reduction using p-toluenesulfonhydrazide (10 equiv.) and NaOAc (14 equiv.) in THF/water at 80° C. followed by usual saturated aqueous NaHCO$_3$ workup can be performed following step 2. The intermediate is typically purified by silica gel chromatography.

Procedure 25a (Example 216)

(11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one

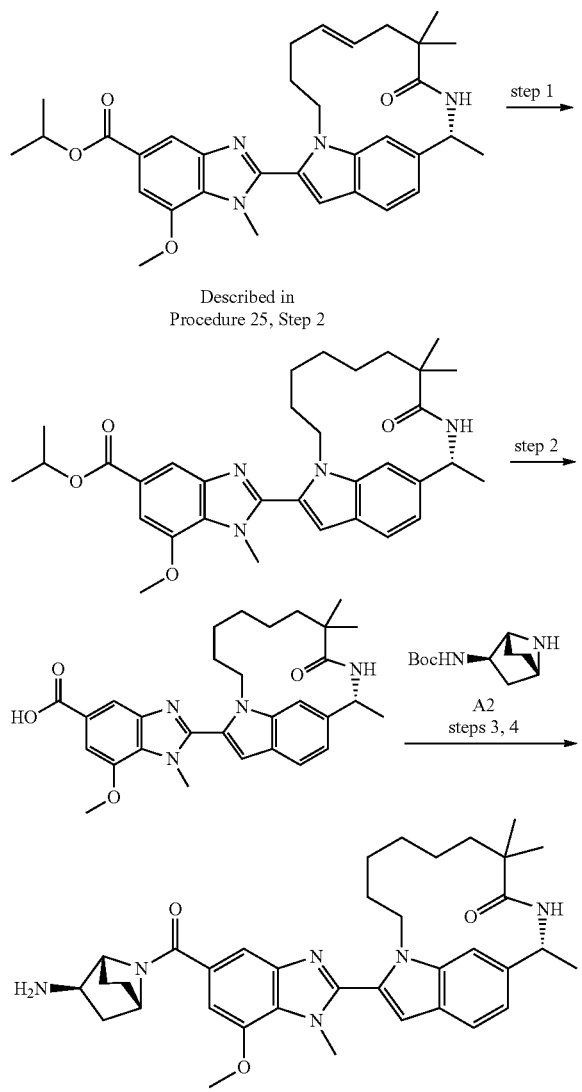

Example 216

Step 1 isopropyl 7-methoxy-1-methyl-2-[(5E,11R)-8,8,11-trimethyl-9-oxo-1,10-diazatricyclo[10.5.2.015,18]nonadeca-5,12(19),13,15(18),16-pentaen-17-yl]benzimidazole-5-carboxylate (described in procedure 25) (2.94 g, 5.28 mmol) was dissolved in EtOH (40 mL) and EtOAc (40 mL). Palladium on carbon (5 wt. %, 2.0 g, 0.94 mmol) was added and the vessel was purged with H$_2$. The mixture was stirred under 1 atm H$_2$ for 18 h and was then filtered through Celite. The filtrate was concentrated to afford isopropyl 7-methoxy-1-methyl-2-[(11R)-8,8,11-trimethyl-9-oxo-1,10-diazatricyclo[10.5.2.015,18]nonadeca-12(19),13,15(18),16-tetraen-17-yl]benzimidazole-5-carboxylate, which was used without further purification. ES/MS: m/z 559.22 [M+H]$^+$.

Step 2 isopropyl 7-methoxy-1-methyl-2-[(11R)-8,8,11-trimethyl-9-oxo-1,10-diazatricyclo[10.5.2.015,18]nonadeca-12(19),13,15(18),16-tetraen-17-yl]benzimidazole-5-carboxylate (2.53 g, 4.53 mmol) was dissolved in THF (40 mL), and MeOH (10 mL) and water (10 mL) were added. Lithium hydroxide monohydrate (950 mg, 23 mmol) was added, and the mixture was heated to 60° C. After 2 h, another portion of lithium hydroxide monohydrate (930 mg, 22 mmol) was added. After an additional 3 h, the mixture was acidified with HCl and was concentrated in vacuo to remove most volatiles. Methanol was added to provide a solution, and water was added to effect precipitation of solids. Solids were collected by filtration, washed with additional water, and dried to provide 7-methoxy-1-methyl-2-[(11R)-8,8,11-trimethyl-9-oxo-1,10-diazatricyclo[10.5.2.015,18]nonadeca-12(19),13,15(18),16-tetraen-17-yl]benzimidazole-5-carboxylic acid. ES/MS: m/z 517.32 [M+H]$^+$.

Step 3

7-methoxy-1-methyl-2-[(11R)-8,8,11-trimethyl-9-oxo-1,10-diazatricyclo[10.5.2.015,18]nonadeca-12(19),13,15(18),16-tetraen-17-yl]benzimidazole-5-carboxylic acid (2.17 g, 4.2 mmol) was dissolved in DMF (30 mL). tert-butyl N-[(2R)-7-azabicyclo[2.2.1]heptan-2-yl]carbamate (A2) (1.02 g, 4.8 mmol) was added followed by Hunig's base (3.66 mL, 21 mmol) and HATU (1.92 g, 5.0 mmol). The mixture was stirred for 45 min, and saturated aqueous NaHCO$_3$ was added to effect precipitation of solids. The mixture was diluted with water, and the solids were collected by filtration. The wet filter cake was dissolved in DCM, dried over Na$_2$SO$_4$, filtered, and concentrated to afford crude (11R)-17-[5-[(1R,2R,4S)-2-amino-7-azabicyclo[2.2.1]heptane-7-carbonyl]-7-methoxy-1-methyl-benzimidazol-2-yl]-8,8,11-trimethyl-1,10-diazatricyclo[10.5.2.015,18]nonadeca-12(19),13,15(18),16-tetraen-9-one that was used without further purification. ES/MS: m/z 711.75 [M+H]$^+$.

Step 4

(11R)-17-[5-[(1R,2R,4S)-2-amino-7-azabicyclo[2.2.1]heptane-7-carbonyl]-7-methoxy-1-methyl-benzimidazol-2-yl]-8,8,11-trimethyl-1,10-diazatricyclo[10.5.2.015,18]nonadeca-12(19),13,15(18),16-tetraen-9-one (ca. 4.2 mmol) was dissolved in DCM (40 mL) and TFA (20 mL) was added. The mixture was stirred for 30 min and was concentrated in vacuo. The obtained residue was purified by preparative HPLC (5%-100% MeCN in water, 0.1% TFA). To provide Example 216.

Procedure 26 (Example 66)

(11~{R})-17-[5-[(3~{S},4~{R})-3-amino-4-(hydroxymethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one

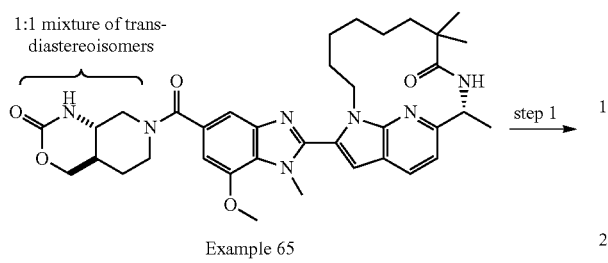

Example 65

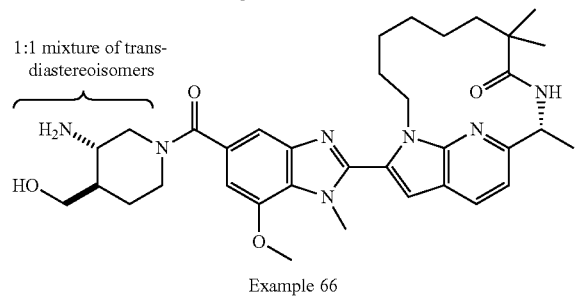

Example 66

Step 1.

(rac-(4aR,8aS))-7-[7-methoxy-1-methyl-2-[(11R)-8,8,11-trimethyl-9-oxo-1,10,19-triazatricyclo[10.5.2.015,18]nonadeca-12(19),13,15(18),16-tetraen-17-yl]benzimidazole-5-carbonyl]-4,4a,5,6,8,8a-hexahydro-1H-pyrido[3,4-d][1,3]oxazin-2-one (Example 65, 40 mg, 0.061 mmol) was combined with lithium hydroxide (0.35 mL of a 1 M aqueous solution, 0.35 mmol) in a mixture of THF (1.2 mL) and water (1.0 mL) and heated to 40° C. for 7 h. The mixture was frozen and lyophilized, then purified by reverse phase preparative HPLC to afford Example 66.

Procedure 27 (Example 274)

(3~{R},5~{R},12~{R})-18-[5-[(3~{R})-3-aminopiperidine-1-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one

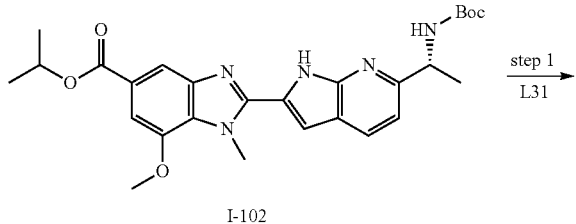

I-102

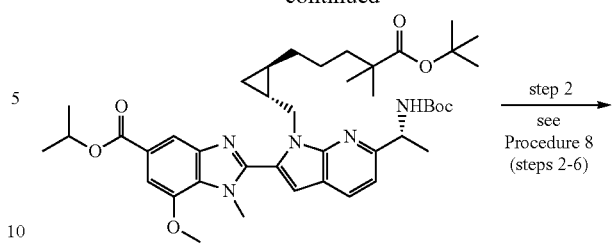

Example 274

Step 1.

To a solution of tert-butyl 5-[(1R,2R)-2-(hydroxymethyl)cyclopropyl]-2,2-dimethylpentanoate (L31, 50 mg, 0.20 mmol), isopropyl (R)-2-(6-(1-((tert-butoxycarbonyl)amino)ethyl)-1H-pyrrolo[2,3-b]pyridin-2-yl)-7-methoxy-1-methyl-H-benzo[d]imidazole-5-carboxylate (I-102, 76.1 mg, 0.15 mmol) and triphenylphosphine (118 mg, 0.45 mmol) in tetrahydrofuran (2 mL) was added diethyl azodicarboxylate (0.21 mL, 0.45 mmol) and the mixture was stirred at room temperature for 90 minutes. The resulting mixture was worked up with brine and extracted with ethyl acetate. The organics were collected, dried over magnesium sulfate and concentrated to yield the crude product, which was purified by silica gel chromatography (eluent: EtOAc/Hexanes) to provide isopropyl 2-[6-[(1R)-1-(tert-butoxycarbonylamino)ethyl]-1-[[(1R,2R)-2-(5-tert-butoxy-4,4-dimethyl-5-oxo-pentyl)cyclopropyl]methyl]pyrrolo[2,3-b]pyridin-2-yl]-7-methoxy-1-methyl-benzimidazole-5-carboxylate. ES/MS: m/z 746.2 [M+H]$^+$.

Step 2

Example 274 was prepared following steps 2-6 of to Procedure 8 using A1.01 and isopropyl 2-[6-[(1R)-1-(tert-butoxycarbonylamino)ethyl]-1-[[(1R,2R)-2-(5-tert-butoxy-4,4-dimethyl-5-oxo-pentyl)cyclopropyl]methyl]pyrrolo[2,3-b]pyridin-2-yl]-7-methoxy-1-methyl-benzimidazole-5-carboxylate.

Note:

For compounds made by this sequence, alternative reagents, solvent, temperature, or isolation methods may have been used. An additional example of this procedure is depicted below.

563

Procedure 27—Additional Example (Example 439)

(2~{R})-17-[5-[(1~{S},4~{R},5~{R})-4-amino-2-azabicyclo[3.2.1]octane-2-carbonyl]-7-methoxy-1-methyl-benzimidazol-2-yl]-2-methyl-3,16,22-triaza-tetracyclo[14.5.2.0^{5,10}.0^{19,23}]tricosa-1(22),5(10),6,8,17,19(23),20-heptaen-4-one

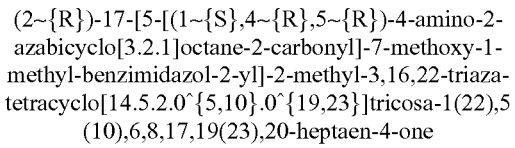

I-102 step 1
L50k

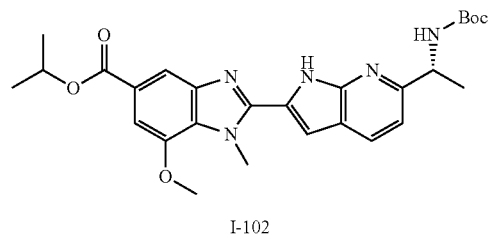

step 2

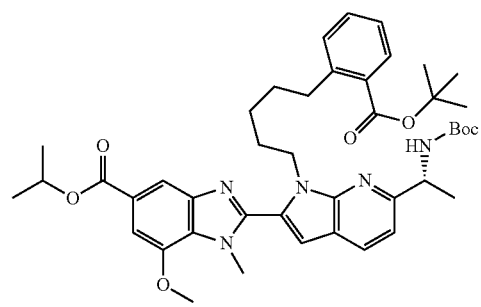

step 3

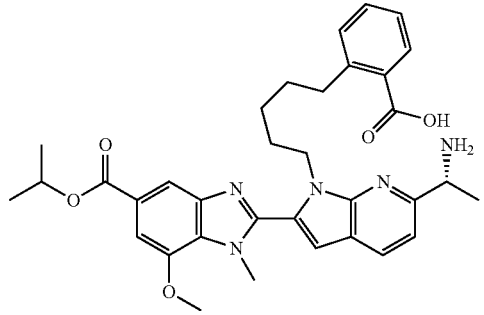

step 4

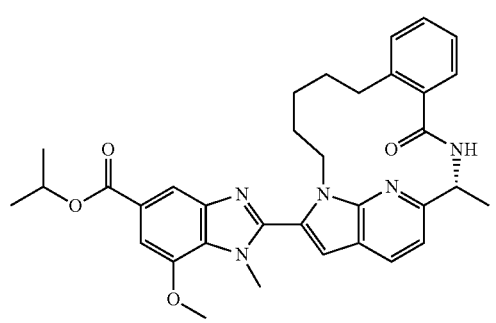

564

-continued

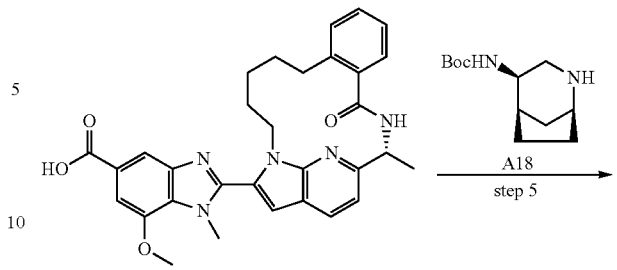

A18
step 5

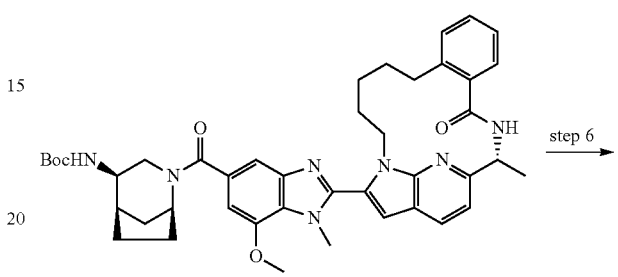

step 6

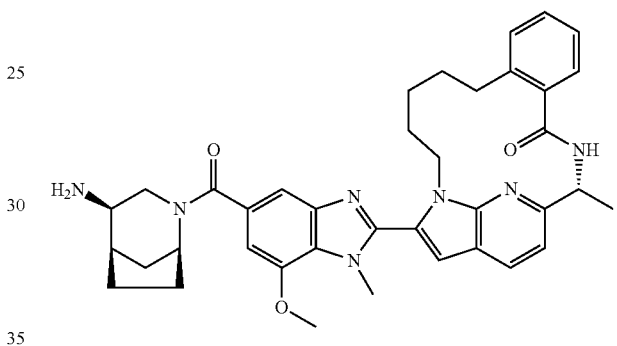

Example 439

Step 1

To a solution of isopropyl (R)-2-(6-(1-((tert-butoxycarbonyl)amino)ethyl)-1H-pyrrolo[2,3-b]pyridin-2-yl)-7-methoxy-1-methyl-H-benzo[d]imidazole-5-carboxylate (I-102, 0.500 g, 0.985 mmol), tert-butyl 2-(5-hydroxypentyl)benzoate (L50k, 0.312 g, 1.18 mmol), and triphenylphosphine (0.646 g, 2.46 mmol) in THF (10 mL) was added DIAD (0.49 mL, 2.46 mmol). The mixture was stirred at rt for 2 h. The mixture was concentrated onto silica gel and purified via flash column chromatography on silica gel to afford isopropyl (R)-2-(6-(1-((tert-butoxycarbonyl)amino)ethyl)-1-(5-(2-(tert-butoxycarbonyl)phenyl)pentyl)-1H-pyrrolo[2,3-b]pyridin-2-yl)-7-methoxy-1-methyl-1H-benzo[d]imidazole-5-carboxylate. ES/MS: m/z 754.4 [M+H]$^+$.

Step 2

To a solution of isopropyl (R)-2-(6-(1-((tert-butoxycarbonyl)amino)ethyl)-1-(5-(2-(tert-butoxycarbonyl)phenyl)pentyl)-1H-pyrrolo[2,3-b]pyridin-2-yl)-7-methoxy-1-methyl-1H-benzo[d]imidazole-5-carboxylate (0.743 g, 0.986 mmol) in DCM (10 mL) was added TFA (3.8 mL). The mixture sat at rt for 16 h. The mixture was concentrated. The resulting residue was taken up in DCM and concentrated twice, yielding crude (R)-2-(5-(6-(1-aminoethyl)-2-(5-(isopropoxycarbonyl)-7-methoxy-1-methyl-1H-benzo[d]imidazol-2-yl)-1H-pyrrolo[2,3-b]pyridin-1-yl)pentyl)benzoic acid, which was used without purification. ES/MS: m/z 598.4 [M+H]$^+$.

Step 3

To a mixture of (R)-2-(5-(6-(1-aminoethyl)-2-(5-(isopropoxycarbonyl)-7-methoxy-1-methyl-1H-benzo[d]imidazol-2-yl)-1H-pyrrolo[2,3-b]pyridin-1-yl)pentyl)benzoic acid (1.18 g, 1.97 mmol) and DIPEA (5.2 mL, 30 mmol) in DCM (80 mL) was added HATU (0.899 g, 2.37 mmol). The mixture was stirred at rt for 16 h. The mixture was concentrated onto silica gel and purified via flash column chromatography on silica gel to afford isopropyl 7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carboxylate. ES/MS: m/z 580.3 [M+H]$^+$.

Step 4

To a solution of isopropyl 7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carboxylate (0.811 g, 1.40 mmol) in THF (14 mL) and MeOH (2.8 mL) was added LiOH (4.2 mL of a 1 M aq soln, 2.9 mmol). The mixture was stirred at 50° C. for 16 h. The mixture was cooled to rt and neutralized via the addition of HCl (0.72 mL of a 6 M aq soln, 4.34 mmol) and was subsequently concentrated to remove THF/MeOH. The resulting solid was isolated via filtration, rinsed with water, and dried en vacuo to give 7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carboxylic acid. ES/MS: m/z 538.3 [M+H]$^+$.

Step 5

To a solution of 7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carboxylic acid (0.400 g, 0.744 mmol), tert-butyl N-[(1S,4R,5R)-2-azabicyclo[3.2.1]octan-4-yl]carbamate (A18, 0.168 g, 0.744 mmol), and DIPEA (0.65 mL, 3.72 mmol) in DMF (3.7 mL) was added HATU (0.424 g, 1.12 mmol). The mixture was stirred at rt for 10 min before an additional portion of tert-butyl N-[(1S,4R,5R)-2-azabicyclo[3.2.1]octan-4-yl]carbamate (A18, 0.010 g, 0.044 mmol) was added. The mixture was stirred at rt for 10 min and was then diluted with water (~20 mL). The resulting solid was collected via filtration, rinsed with water, and dried en vacuo to yield tert-butyl N-[(1S,4R,5R)-2-[7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carbonyl]-2-azabicyclo[3.2.1]octan-4-yl]carbamate. ES/MS: m/z 746.4 [M+H]$^+$.

Step 6

To a solution of tert-butyl N-[(1S,4R,5R)-2-[7-methoxy-1-methyl-2-[(2R)-2-methyl-4-oxo-3,16,22-triazatetracyclo[14.5.2.05,10.019,23]tricosa-1(22),5(10),6,8,17,19(23),20-heptaen-17-yl]benzimidazole-5-carbonyl]-2-azabicyclo[3.2.1]octan-4-yl]carbamate (0.555 g, 0.744 mmol) in DCM (3.7 mL) was added TFA (3.7 mL). The mixture sat at rt for 10 min. The mixture was concentrated and the resulting residue was purified via preparative reverse phase HPLC to give Example 439.

Procedure 28 (Examples 115 and 116)

(3~{S},5~{R},8~{R},10~{R},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one (Example 115)

(3~{S},5~{R},8~{S},10~{S},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one (Example 116)

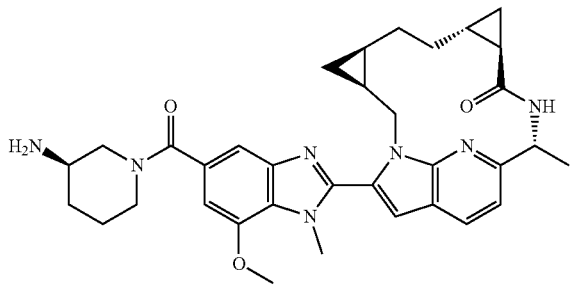

Example 115

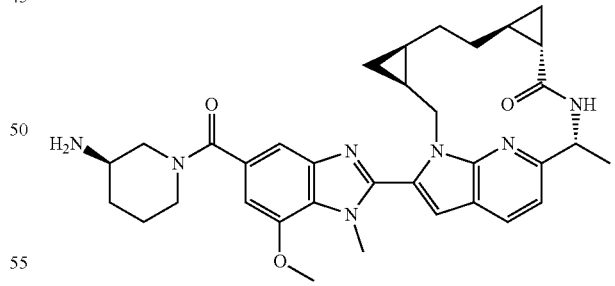

Example 116

Examples 115 and 116 were prepared using Procedure 27 using L45a instead of L31. After purification by silica gel chromatography at the macrocyclization step (step 3 of Procedure 8), the first eluting peak was arbitrarily assigned as the (8R,10R)-configuration, and the second eluting peak was assigned as the (8S,10S)-configuration. Both diastereoisomers were separately submitted to steps 4-6 of Procedure 8 to provide Examples 115 and 116.

567

Procedure 29 (Examples 312 and 313)

(3~{S},5~{R},9~{R},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0ˆ{3,5}.0ˆ{16,19}]icosa-13(20),14,16(19),17-tetraen-10-one (Example 312)

(3~{S},5~{R},9~{S},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0ˆ{3,5}.0ˆ{16,19}]icosa-13(20),14,16(19),17-tetraen-10-one (Example 313)

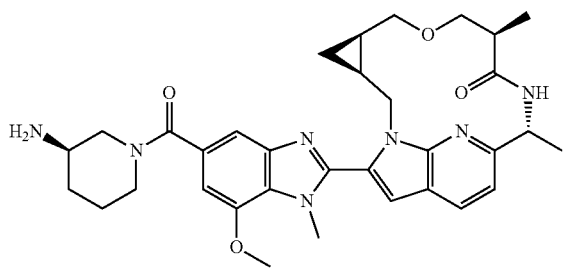

Example 312

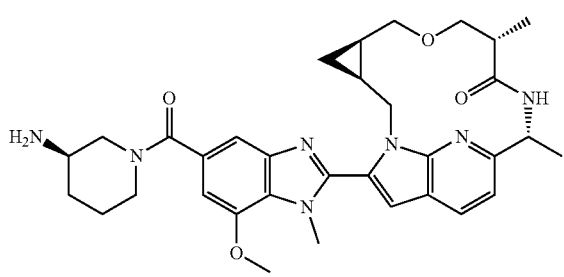

Example 313

The 1:1 diastereoisomeric mixture of Examples 312 and 313 was prepared using Procedure 27 using L13g instead of L31. Examples 312 and 313 were separated via C18 preparative HPLC (5-100% MeCN in water, 0.1% TFA), and the first eluting peak was arbitrarily assigned as the (9R)-configuration (Example 312), and the second eluting peak was assigned as the (9S)-configuration (Example 313).

*In other instances, diastereoisomeric mixtures of Examples can be separated via preparative chiral HPLC or chiral SFC.

568

Procedure 30 (Examples 245 and 246)

(3~{S},5~{R},12~{R})-18-[5-[(4~{a}~{S},8~{a}~{R})-2,3,4,4~{a},5,7,8,8~{a}-octahydro-pyrido[4,3-b][1,4]oxazine-6-carbonyl]-7-methoxy-1-methyl-benzimidazol-2-yl]-12-methyl-7-oxa-1,11,20-triazatetracyclo[11.5.2.0ˆ{3,5}.0ˆ{16,19}]icosa-13(20),14,16(19),17-tetraen-10-one (Example 245)

(3~{S},5~{R},12~{R})-18-[5-[(4~{a}~{R},8~{a}~{S})-2,3,4,4~{a},5,7,8,8~{a}-octahydro-pyrido[4,3-b][1,4]oxazine-6-carbonyl]-7-methoxy-1-methyl-benzimidazol-2-yl]-12-methyl-7-oxa-1,11,20-triazatetracyclo[11.5.2.0ˆ{3,5}.0ˆ{16,19}]icosa-13(20),14,16(19),17-tetraen-10-one (Example 246)

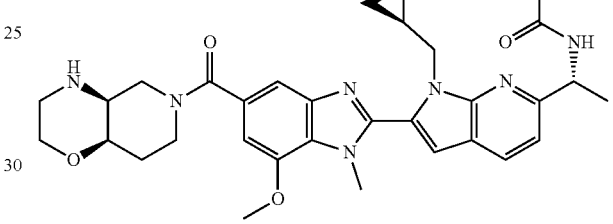

Example 245

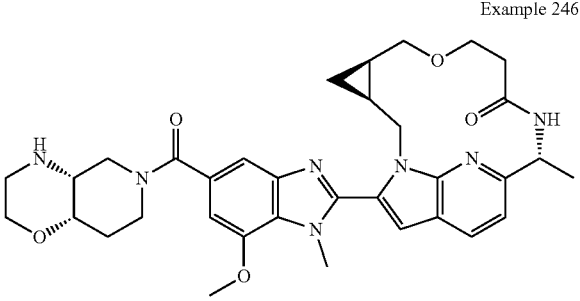

Example 246

The 1:1 diastereoisomeric mixture of Examples 245 and 246 was prepared following Procedure 27 using L13f and A1.17. Examples 245 and 246 were separated via chiral SFC. The first eluting peak was assigned as the (4aS,8aR)-configuration (Example 245), and the second eluting peak was as the (4aR,8aS)-configuration (Example 246).

*In other instances, diastereoisomeric mixtures of Examples can be separated via preparative HPLC or preparative chiral HPLC.

Procedure 31 (Example 252)

17-[5-[(1~{R},2~{R},4~{S})-2-amino-7-azabicyclo[2.2.1]heptane-7-carbonyl]-3-ethylpyrazolo[1,5-a]pyridin-2-yl]-11-methyl-1,10,19-triazatricyclo[10.5.2.0^{15,18}]nonadeca-12(19),13,15(18),16-tetraen-9-one

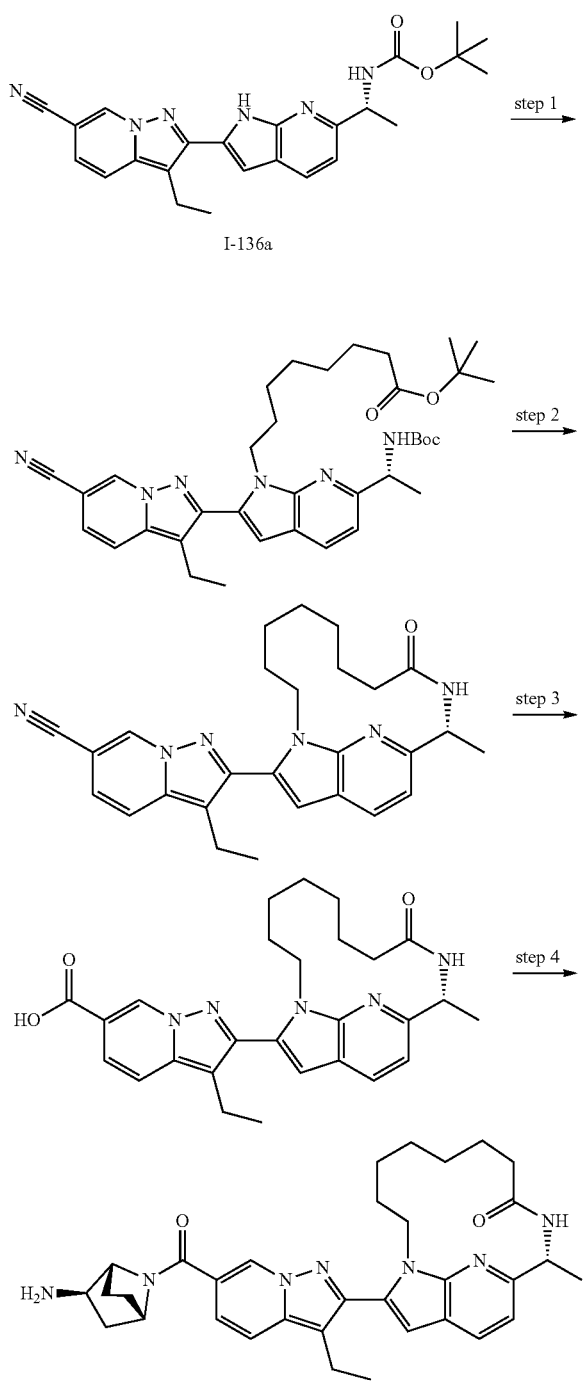

Step 1

A mixture of tert-butyl (R)-(1-(2-(6-cyano-3-ethylpyrazolo[1,5-a]pyridin-2-yl)-1H-pyrrolo[2,3-b]pyridin-6-yl)ethyl)carbamate (I-136a, 40 mg, 0.093 mmol), cesium carbonate (91 mg, 0.28 mmol), and tert-butyl 8-bromooctanoate (0.03 g, 0.11 mmol) in DMF (3 mL) was heated at 90° C. After 2 h, additional cesium carbonate (91 mg, 0.28 mmol), and tert-butyl 8-bromooctanoate (0.03 g, 0.11 mmol) were added and the mixture was again heated at 90° C. After 1 h, the reaction mixture was cooled to rt and diluted with ethyl acetate and water. The layers were separated and the aqueous was extracted with ethyl acetate. The combined organics washed with water, dried (MgSO$_4$), filtered, and concentrated under reduced pressure to yield tert-butyl (R)-8-(6-(1-((tert-butoxycarbonyl)amino)ethyl)-2-(6-cyano-3-ethylpyrazolo[1,5-a]pyridin-2-yl)-1H-pyrrolo[2,3-b]pyridin-1-yl)octanoate, that was used directly below without purification. ES/MS: m/z 629.0 [M+H]$^+$.

Step 2

To a solution of tert-butyl (R)-8-(6-(1-((tert-butoxycarbonyl)amino)ethyl)-2-(6-cyano-3-ethylpyrazolo[1,5-a]pyridin-2-yl)-1H-pyrrolo[2,3-b]pyridin-1-yl)octanoate (58 mg, 0.092 mmol) in DCM (4 mL) was added a solution of 4 M HCl in dioxane (0.92 mL, 3.69 mmol). After 24 h, the reaction mixture was concentrated under reduced pressure and dried in vacuo. This residue was dissolved in DMF (2 mL) and the solution was treated with N,N-Diisopropylethylamine (0.10 mL, 0.579 mmol) and HATU (53 mg, 0.138 mmol). After thirty minutes, the reaction mixture was diluted with ethyl acetate and water. The layers were separated and the aqueous was extracted with ethyl acetate. The combined organics washed with water, brine, dried (MgSO$_4$), filtered, and concentrated under reduced pressure to yield 3-ethyl-2-[(11R)-11-methyl-9-oxo-1,10,19-triazatricyclo[10.5.2.015,18]nonadeca-12(19),13,15(18),16-tetraen-17-yl]pyrazolo[1,5-a]pyridine-6-carbonitrile, that was used directly below without purification. ES/MS: m/z 455.3 [M+H]$^+$.

Step 3

A solution of 8.5 M sodium hydroxide in water (0.1 mL, 8.50 mmol) was added to a mixture of 3-ethyl-2-[(11R)-11-methyl-9-oxo-1,10,19-triazatricyclo[10.5.2.015,18]nonadeca-12(19),13,15(18),16-tetraen-17-yl]pyrazolo[1,5-a]pyridine-6-carbonitrile (42 mg, 0.092 mmol, crude above) in a mixture of ethanol (2 mL) and water (0.75 mL) at rt. The reaction mixture was heated at 80° C. After 3 h, an additional solution of 8.5 M sodium hydroxide in water (0.1 mL, 8.50 mmol) was added. After 3 h, a solution of 6 M hydrochloric acid (0.3 mL, 1.8 mmol) was added. The reaction mixture was diluted with ethyl acetate and water. The layers were separated and the aqueous was extracted with ethyl acetate. The combined organics washed with water, brine, dried (MgSO$_4$), filtered, and concentrated under reduced pressure to yield 3-ethyl-2-[(11R)-11-methyl-9-oxo-1,10,19-triazatricyclo[10.5.2.015,18]nonadeca-12(19),13,15(18),16-tetraen-17-yl]pyrazolo[1,5-a]pyridine-6-carboxylic acid (44 mg), that was used directly below without purification. ES/MS: m/z 474.33 [M+H]$^+$.

Step 4

Example 252 was prepared following steps 5-6 of Procedure 8 using A1.01 and 3-ethyl-2-[(11R)-11-methyl-9-oxo-1,10,19-triazatricyclo[10.5.2.015,18]nonadeca-12(19),13,15(18),16-tetraen-17-yl]pyrazolo[1,5-a]pyridine-6-carboxylic acid.

Procedure 32 (Example 275)

1-cyclopropyl-6,7-difluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide

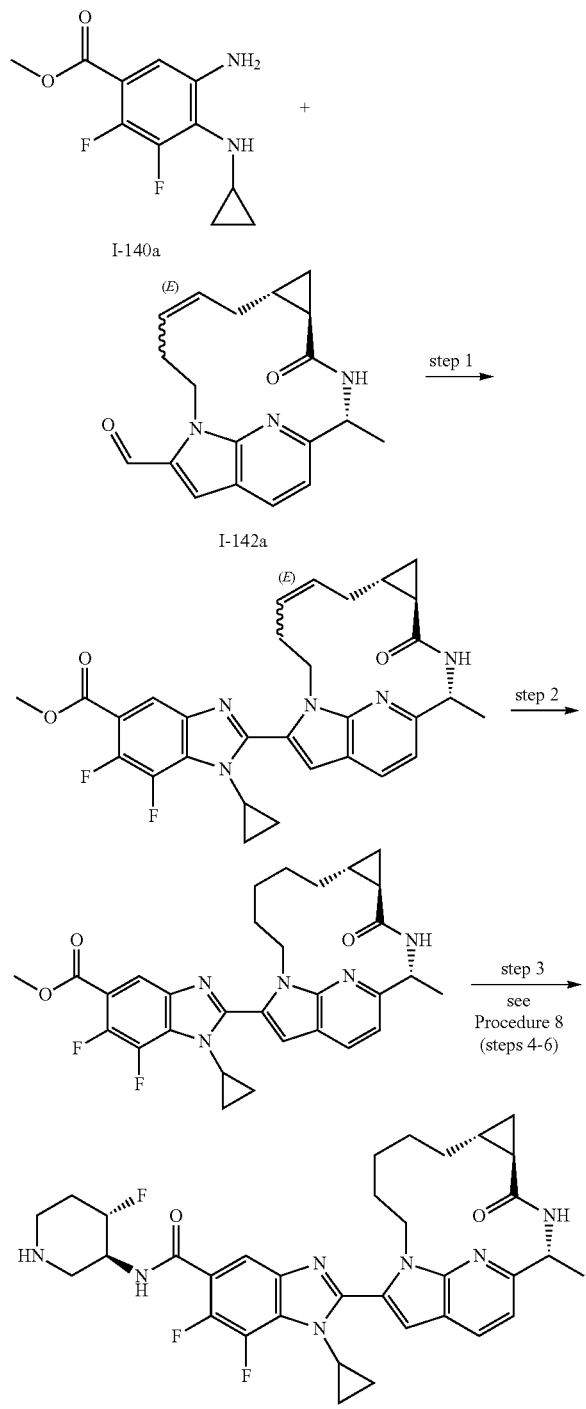

Example 275

Step 1.

Methyl 5-amino-4-(cyclopropylamino)-2,3-difluorobenzoate (I-140a, 43 mg, 0.18 mmol) and (2R,5R,7R,9E)-2-methyl-4-oxo-3,13,19-triazatetracyclo[11.5.2.05,7.016,20]icosa-1(19),9,14,16(20),17-pentaene-14-carbaldehyde (I-142a, 57.4 mg, 0.18 mmol) were charged in a glass vial. Acetic acid (mL) was added and the resulting mixture was stirred at 60° C. for 12 h. The reaction mixture was evaporated to dryness and the residue was purified by flash chromatography over silica gel (Hexanes/EtOAc 0-80%) to afford methyl 1-cyclopropyl-6,7-difluoro-2-[(2R,5R,7R,9E)-2-methyl-4-oxo-3,13,19-triazatetracyclo[11.5.2.05,7.016,20]icosa-1(19),9,14,16(20),17-pentaen-14-yl]benzimidazole-5-carboxylate. ES/MS: m/z 546.1 [M+H]$^+$.

Step 2 (Optional Alkene Reduction).

Note: If I-145a (or any other heteroaryl aldehyde intermediate without an alkene in the macrocyclic ring) is used in step 1, proceed to step 3 directly.

Methyl 1-cyclopropyl-6,7-difluoro-2-[(2R,5R,7R,9E)-2-methyl-4-oxo-3,13,19-triazatetracyclo[11.5.2.05,7.016,20]icosa-1(19),9,14,16(20),17-pentaen-14-yl]benzimidazole-5-carboxylate (71.3 mg, 0.13 mmol) was dissolved in a 2:1 mixture of tetrahydrofuran:water (4.5 mL). To the mixture was added p-toluenesulfonhydrazide (243 mg, 1.3 mmol) and sodium acetate (129 mg, 1.57 mmol), and the resulting mixture was stirred at 85° C. for 16 h. The reaction mixture was quenched with saturated sodium bicarbonate and extracted with ethyl acetate (2×). The organics were collected, dried over magnesium sulfate and concentrated to yield the crude material, which was carried over to the next step without further purification. ES/MS: m/z 548.2 [M+H]$^+$.

Note.

For Examples without a cyclopropyl moiety, standard hydrogenation conditions (1 atm H$_2$ with palladium on carbon (10% loading) in EtOH can be performed. The intermediate is typically used without further purification after filtration and concentration.

Step 3

Example 275 was prepared following steps 4-6 of Procedure 8 using A1.15 and methyl 1-cyclopropyl-6,7-difluoro-2-[(2R,5R,7R)-2-methyl-4-oxo-3,13,19-triazatetracyclo[11.5.2.05,7.016,20]icosa-1(19),14,16(20),17-tetraen-14-yl]benzimidazole-5-carboxylate.

Note:

For Examples 453 and 454, the intermediate carboxylic acid diastereoisomers (after step 4 of Procedure 8) were separated via chiral SFC. Each diastereoisomer was submitted separately to step 5-6 of Procedure 8. The absolute stereochemistry of was arbitrarily assigned for each diastereoisomer.

*In other instances, diastereoisomeric mixtures of Examples can be separated via preparative HPLC, preparative chiral HPLC or chiral SFC.

Procedure 33 (Example 188)

~{N}-[(3~{S},4~{S})-4-fluoro-3-piperidyl]-3-methyl-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]imidazo[4,5-b]pyridine-6-carboxamide

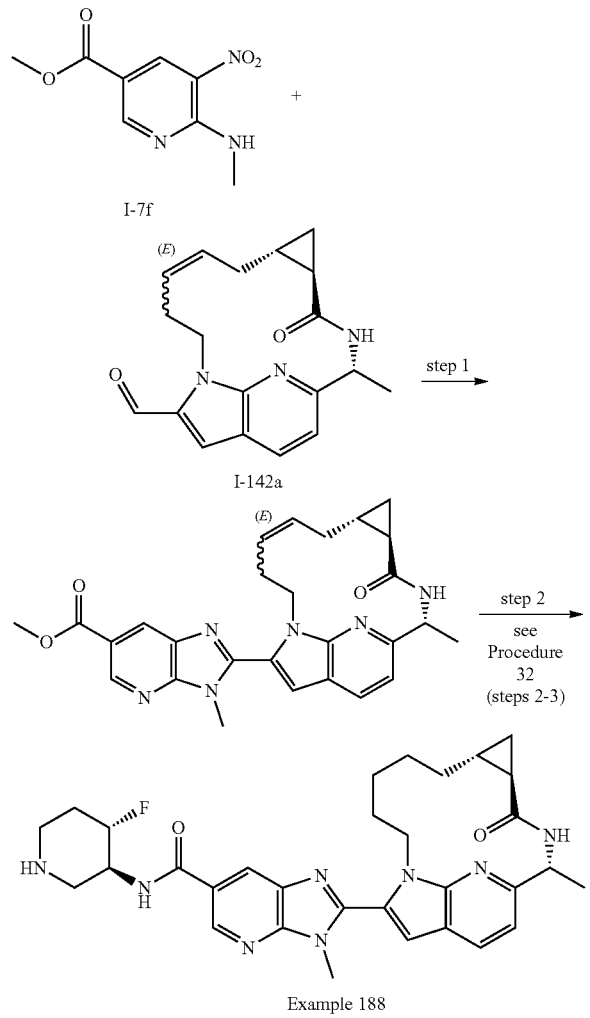

Example 188

Step 1

Methyl 6-(methylamino)-5-nitronicotinate (I-7f, 58 mg, 0.27 mmol) and (2R,5R,7R,9E)-2-methyl-4-oxo-3,13,19-triazatetracyclo[11.5.2.05,7.016,20]icosa-1(19),9,14,16(20),17-pentaene-14-carbaldehyde (I-142a, 89 mg, 0.27 mmol) were charged in a vial equipped with a stir bar. The mixture was suspended in EtOH/water (2:1, 2.7 mL) and sodium dithionite (190 mg, 1.1 mmol) was added. The vial was sealed, and the reaction was heated to 80° C. overnight. After usual work up, the residue was purified by chromatography over silica gel (DCM/EtOAc 5-100%) to afford methyl 3-methyl-2-[(2R,5R,7R,9E)-2-methyl-4-oxo-3,13,19-triazatetracyclo[11.5.2.05,7.016,20]icosa-1(19),9,14,16(20),17-pentaen-14-yl]imidazo[4,5-b]pyridine-6-carboxylate. ES/MS: m/z 485.3 [M+H]+.

Step 2

Example 188 was prepared following steps 2-3 of Procedure 32 using methyl 3-methyl-2-[(2R,5R,7R,9E)-2-methyl-4-oxo-3,13,19-triazatetracyclo[11.5.2.05,7.016,20]icosa-1(19),9,14,16(20),17-pentaen-14-yl]imidazo[4,5-b]pyridine-6-carboxylate.

*In other instances, diastereoisomeric mixtures of Examples can be separated via preparative HPLC, preparative chiral HPLC or chiral SFC.

Procedure 34 (Example 23)

[(1~{R},2~{R},4~{S})-2-amino-7-azabicyclo[2.2.1]heptan-7-yl]-[7-methoxy-1-methyl-2-[(11~{R})-11-methyl-9,9-dioxo-9$1^{6}-thia-1,10,19-triazatricyclo[10.5.2.0^{15,18}]nonadeca-3,12(19),13,15(18),16-pentaen-17-yl]benzimidazol-5-yl]methanone

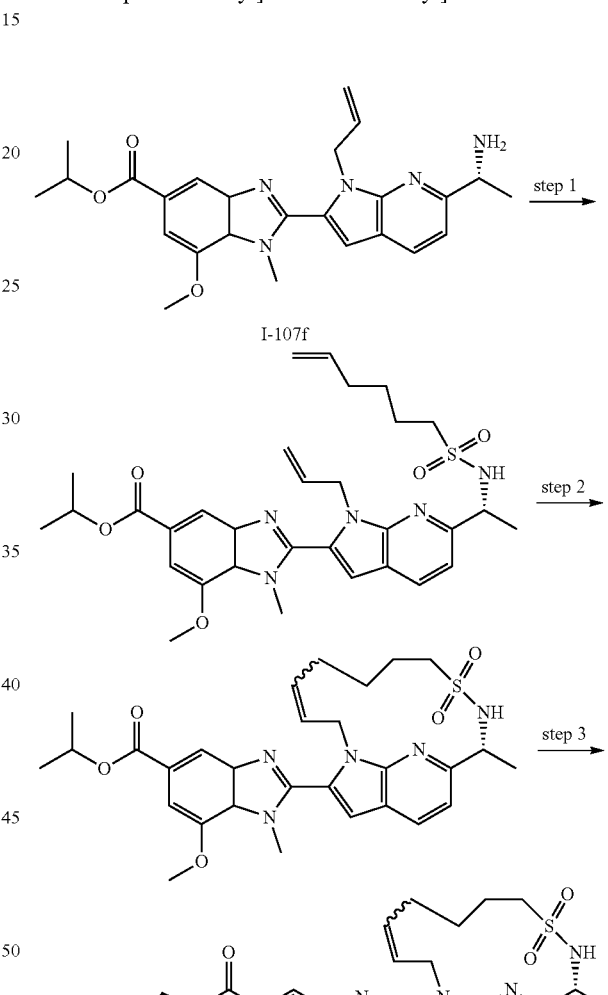

Example 23

Step 1.

To a mixture of isopropyl 2-(1-allyl-6-((R)-1-aminoethyl)-1H-pyrrolo[2,3-b]pyridin-2-yl)-7-methoxy-1-methyl-3a,7a-dihydro-1H-benzo[d]imidazole-5-carboxylate (I-107f, ca. 0.58 mmol) in DCM was added hex-5-ene-1-sulfonyl chloride (0.14 g, 0.75 mmol), followed by triethylamine (0.16 mL, 1.1 mmol) at rt. After 16 h the reaction was diluted with EtOAc, washed with brine, dried over sodium sulfate, filtered and concentrated. The crude material was purified on silica gel chromatography (0-100% EtOAc in hexanes) to give the desired material isopropyl 2-[1-allyl-6-[(1R)-1-(hex-5-enylsulfonylamino)ethyl]pyrrolo[2,3-b]pyridin-2-yl]-7-methoxy-1-methyl-benzimidazole-5-carboxylate. ES/MS: m/z 594.2 [M+H]⁺.

Step 2

To a mixture of isopropyl 2-[1-allyl-6-[(1R)-1-(hex-5-enylsulfonylamino)ethyl]pyrrolo[2,3-b]pyridin-2-yl]-7-methoxy-1-methyl-benzimidazole-5-carboxylate (0.20g, 0.33 mmol) in 1,2-dichloroethane (40 mL) was added Zhan-1B catalyst (25 mg, 0.03 mmol) under an atmosphere of argon. The mixture was heated at 90° C. for 75 minutes. The crude material was purified on silica gel chromatography (0-100% EtOAc in hexanes) to give isopropyl 7-methoxy-1-methyl-2-[(11R)-11-methyl-9,9-dioxo-9lambda6-thia-1,10,19-triazatricyclo[10.5.2.015,18]nonadeca-3,12(19),13,15(18),16-pentaen-17-yl]-3a,7a-dihydrobenzimidazole-5-carboxylate. ES/MS: m/z 566.2 [M+H]⁺.

Step 3

Example 23 was prepared following steps 4-6 of Procedure 8 using isopropyl 7-methoxy-1-methyl-2-[(11R)-11-methyl-9,9-dioxo-9lambda6-thia-1,10,19-triazatricyclo[10.5.2.015,18]nonadeca-3,12(19),13,15(18),16-pentaen-17-yl]-3a,7a-dihydrobenzimidazole-5-carboxylate. ES/MS: m/z 618.3 [M+H]⁺.

Procedure 35 (Example 25)

[(3~{R})-3-amino-1-piperidyl]-[7-methoxy-1-methyl-2-(2-methyl-3,4,5,13,19-pentazatetracyclo[11.5.2.1^{3,6}.0^{16,20}]henicosa-1(19),4,6(21),14,16(20),17-hexaen-14-yl)benzimidazol-5-yl]methanone

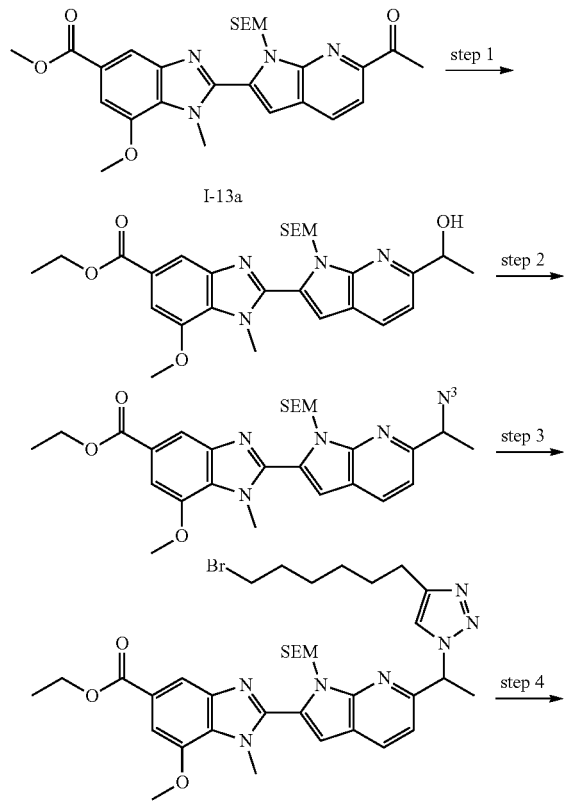

I-13a

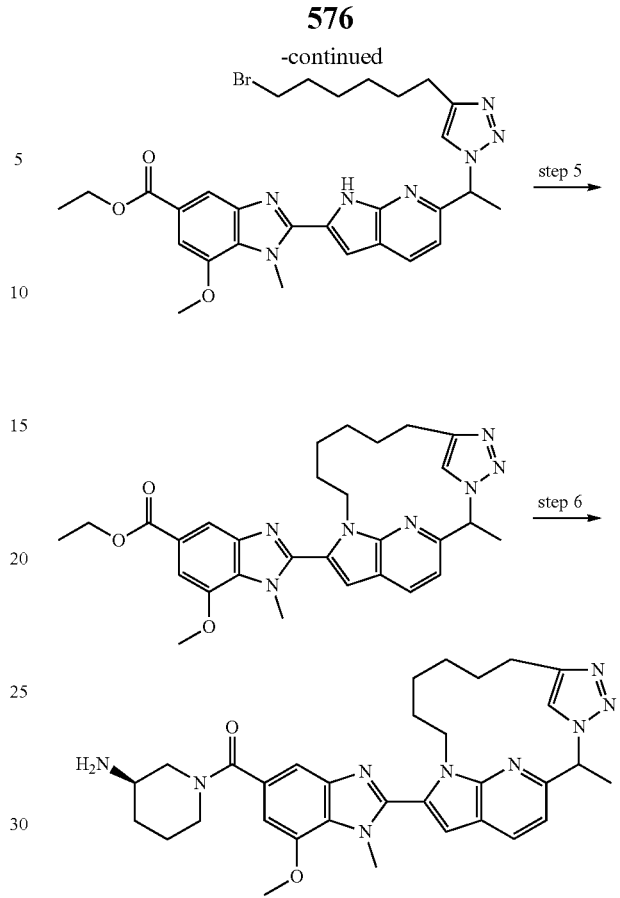

Example 25

Step 1

To a flask containing methyl 2-(6-acetyl-1-((2-(trimethylsilyl)ethoxy)methyl)-1H-pyrrolo[2,3-b]pyridin-2-yl)-7-methoxy-1-methyl-1H-benzo[d]imidazole-5-carboxylate (I-13a, 5.0 g, 9.83 mmol) in a 1:1 THF/ethanol mixture (6 mL) was added sodium borohydride (1.86 g, 49 mmol) at rt. After 4 h, the reaction mixture was carefully quenched with 1 M HCl (150 mL) and stirred for 16 h at rt. The mixture was diluted with EtOAc and the phases were separated. The organic phase was dried over MgSO₄, filtered, and concentrated to give ethyl 2-(6-(1-hydroxyethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. The material was used as is for next step. ES/MS: m/z 525.8 [M+H]⁺.

Step 2

Ethyl 2-(6-(1-hydroxyethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate (0.244 g, 0.4 mmol) and DBU (0.45 g, 2.9 mmol) in THF (30 mL) under nitrogen was treated with diphenyl phosphoryl azide (0.81 g, 2.9 mmol) at rt. After 16 h the reaction was quenched with water, diluted with EtOAc and washed once with sat. sodium bicarbonate solution (50 mL). The organic phase was dried over Na₂SO₄, filtered and concentrated. Purification by silica gel (10-60% EtOAc in hexanes) provided ethyl 2-(6-(1-azidoethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 550.2 [M+H]⁺.

Step 3

A mixture of ethyl 2-(6-(1-azidoethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate (0.22 g, 0.4 mmol), CuI (15 mg, 0.08 mmol), 8-bromooct-1-yne (0.1g, 0.5 mmol), triethylamine (0.05 mL, 0.4 mmol) was dissolved in MeCN (1.5 mL) and flushed under nitrogen. The resulting mixture was then heated to 50° C. for 3 h. The reaction was cooled to rt and diluted with EtOAc and water. The phases were separated, and the organic phase was dried over MgSO$_4$, filtered, and concentrated. The obtained residue was purified by silica gel chromatography (5-100% EtOAc in hexane) to afford ethyl 2-(6-(1-(4-(6-bromohexyl)-1H-1,2,3-triazol-1-yl)ethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate. ES/MS: m/z 738.1 [M+H]$^+$.

Step 4

A solution of ethyl 2-(6-(1-(4-(6-bromohexyl)-1H-1,2,3-triazol-1-yl)ethyl)-1-((2-(trimethylsilyl)ethoxy)methyl)-1H-pyrrolo[2,3-b]pyridin-2-yl)-7-methoxy-1-methyl-1H-benzo[d]imidazole-5-carboxylate (0.296 mg, 0.4 mmol) was dissolved in THF (10 mL) at 0° C.

TBAF 1M in THF (1.2 mmol, 1.2 mL) was added. After stirring 3 h, the reaction mixture was treated with 1 M HCl (3 mL) the reaction was diluted with EtOAc and washed with brine (30 mL), dried over sodium sulfate and concentrated in vacuo to provide crude ethyl 2-(6-(1-(4-(6-bromohexyl)-1H-1,2,3-triazol-1-yl)ethyl)-1H-pyrrolo[2,3-b]pyridin-2-yl)-5-methoxy-3-methylimidazo[1,2-a]pyridine-7-carboxylate which was used without further purification. ES/MS: m/z 608.0 [M+H]$^+$.

Step 5

The above crude mixture (ca. 0.2 mmol) was dissolved in DMF (1 mL). Cesium carbonate (0.39g, 1.2 mmol) was added The mixture was stirred at room temperature for 16 h. Water and EtOAc were added, phases were separated, and the aqueous phase was extracted with EtOAc, dried over sodium sulfate and the mixture was concentrated and purified by silica gel chromatography (0-100% EtOAc in hexane) to ethyl 7-methoxy-1-methyl-2-(2-methyl-3,4,5,13,19-pentazatetracyclo[11.5.2.13,6.016,20]henicosa-1(19),4,6(21),14,16(20),17-hexaen-14-yl)benzimidazole-5-carboxylate. ES/MS: m/z 527.9 [M+H]$^+$.

Step 6

Example 25 was prepared following steps 4-6 of Procedure 8 using ethyl 7-methoxy-1-methyl-2-(2-methyl-3,4,5,13,19-pentazatetracyclo[11.5.2.13,6.016,20]henicosa-1(19),4,6(21),14,16(20),17-hexaen-14-yl)benzimidazole-5-carboxylate.

Procedure 36 (Examples 364 and 365)

2-[(3~{R},5~{S},12~{R})-4,4-difluoro-9,9,12-trimethyl-10-oxo-1,11,20-triazatetracyclo[11.5.2.0^{3,5}].0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide (Example 364)

2-[(3~{S},5~{R},12~{R})-4,4-difluoro-9,9,12-trimethyl-10-oxo-1,11,20-triazatetracyclo[11.5.2.0^{3,5}].0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide Example 365

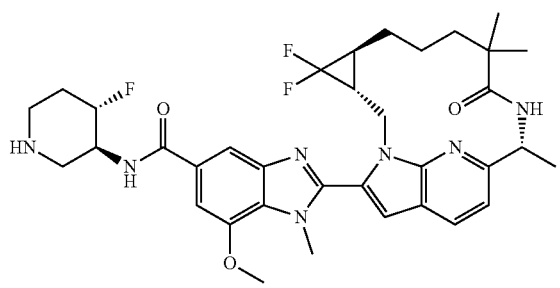

Example 364

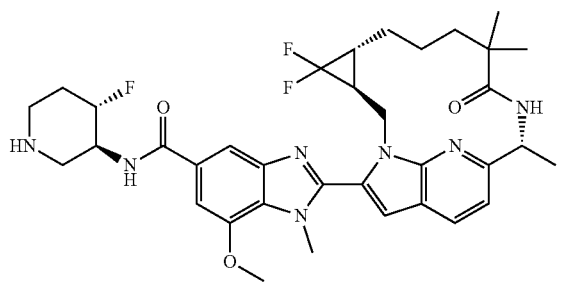

Example 365

The 1:1 diastereoisomeric mixture of Examples 364 and 365 was prepared using Procedure 25 using I-107i and 2,2-dimethyl-4-pentenoic acid. Examples 364 and 465 were separated via C18 preparative HPLC (5-100% MeCN in water, 0.1% TFA), and the first eluting peak was arbitrarily assigned as the (3S,5R)-configuration (Example 364), and the second eluting peak was assigned as the (3R,5S)-configuration (Example 365).

*In other instances, diastereoisomeric mixtures of Examples can be separated via preparative chiral HPLC or chiral SFC.

Procedure 37 (Example 381, 382 and 383)

2-[(2~{R},5~{R},7~{R})-6,6-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide (Example 381)

2-[(2~{R},5~{S},7~{R})-6,6-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide (Example 382)

2-[(2~{R},5~{R},7~{S})-6,6-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide Example 383

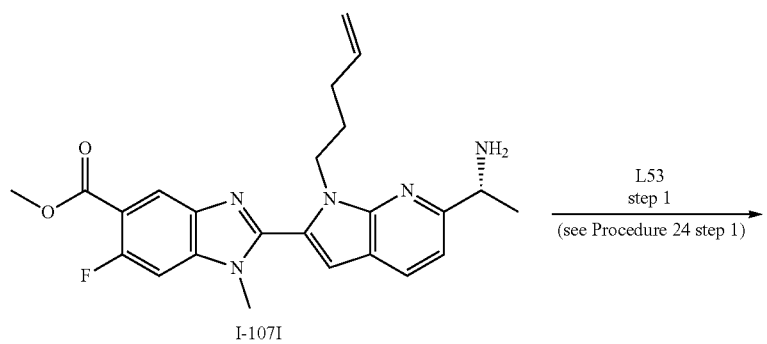

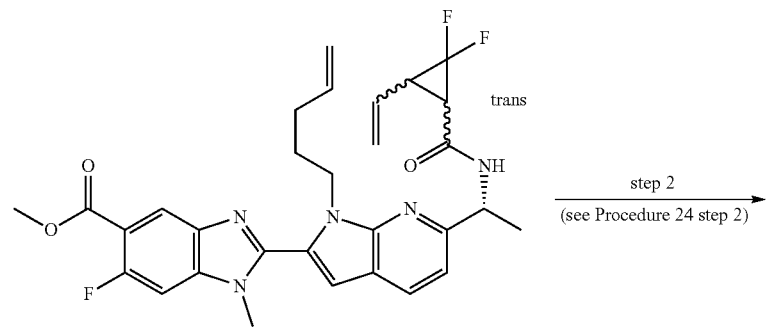

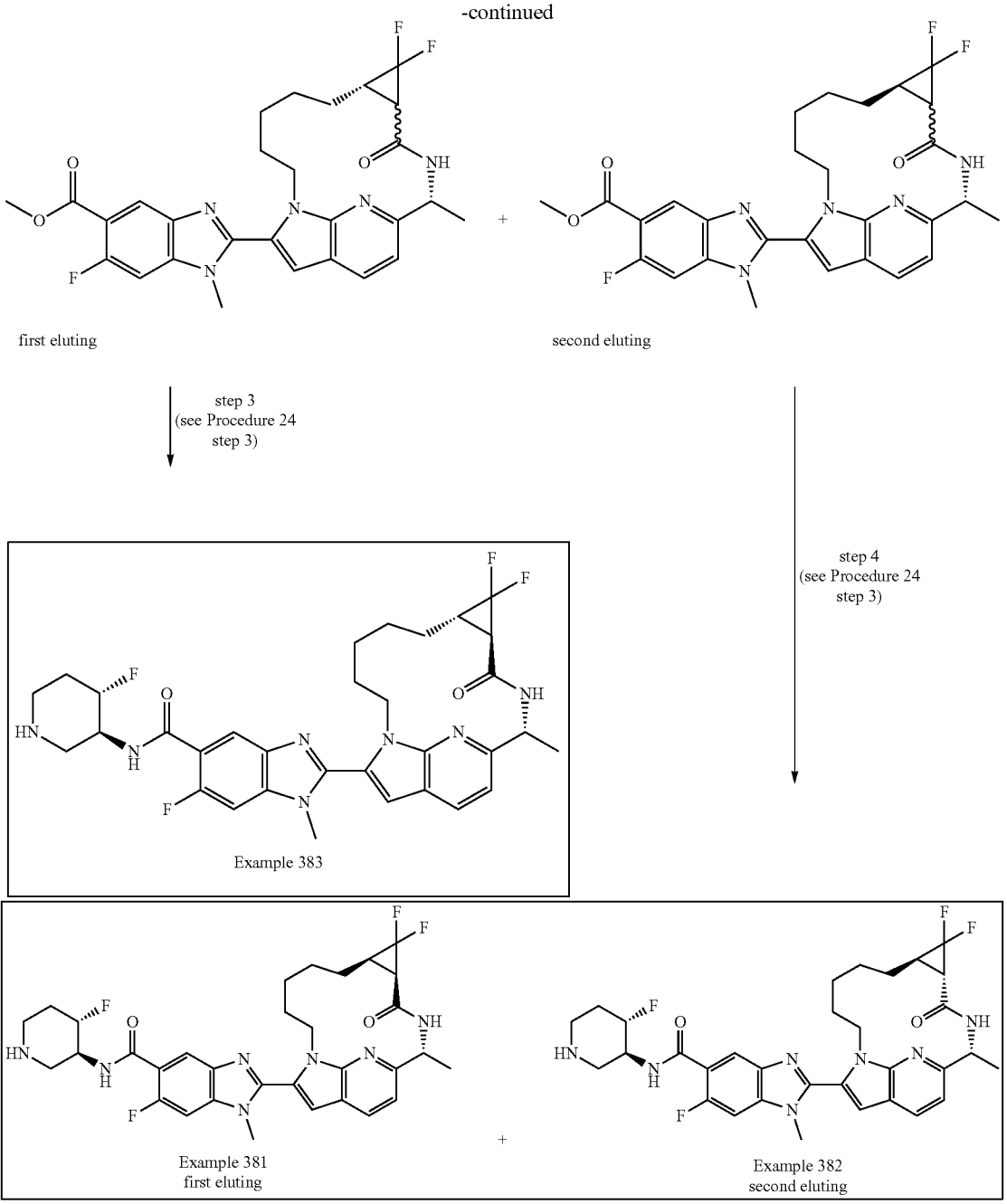

Step 1
Methyl 2-[6-[(1R)-1-[[(trans)-2,2-difluoro-3-vinyl-cyclopropanecarbonyl]amino]ethyl]-1-pent-4-enyl-pyrrolo[2,3-b]pyridin-2-yl]-6-fluoro-1-methyl-benzimidazole-5-carboxylate was prepared following step 1 of Procedure 24 using rac-(trans)-2,2-difluoro-3-vinylcyclopropane-1-carboxylic acid instead of 2-methyl-2-(trifluoromethyl)pent-4-enoic acid. ES/MS: m/z 566.3 [M+H]⁺.

Step 2
Methyl 2-[(2R,trans,8E)-6,6-difluoro-2-methyl-4-oxo-3,13,19-triazatetracyclo[11.5.2.0⁵,⁷.0¹⁶,²⁰]icosa-1(19),8,14,16(20),17-pentaen-14-yl]-6-fluoro-1-methyl-benzimidazole-5-carboxylate was prepared following step 2 of Procedure 24 using methyl 2-[6-[(1R)-1-[[(trans)-2,2-difluoro-3-vinyl-cyclopropanecarbonyl]amino]ethyl]-1-pent-4-enyl-pyrrolo[2,3-b]pyridin-2-yl]-6-fluoro-1-methyl-benzimidazole-5-carboxylate instead of isopropyl 7-methoxy-1-methyl-2-(6-((1R)-1-(2-methyl-2-(trifluoromethyl)pent-4-enamido)ethyl)-1-(pent-4-en-1-yl)-1H-pyrrolo[2,3-b]pyridin-2-yl)-1H-benzo[d]imidazole-5-carboxylate. First eluting isomer ES/MS: m/z 538.3 [M+H]⁺. Second eluting isomer ES/MS: m/z 538.3 [M+H]⁺. Stereochemistry of isomers were assigned by correlation by similarities to 1H NMR of other related Examples.

Note:
The isomers can be separated after step 2 or after the next step, which is olefin reduction using p-toluenesulfonhydrazide (10 equiv.) and NaOAc (14 equiv.) in THF/water at 80°

C. followed by usual saturated aqueous NaHCO₃ workup. The intermediate is purified by silica gel chromatography.

Step 3

Example 383 was prepared following steps 4-6 of Procedure 8 using A1.15 and methyl 2-[(2R,5S,7R)-6,6-difluoro-2-methyl-4-oxo-3,13,19-triazatetracyclo[11.5.2.05,7.016,20]icosa-1(19),14,16(20),17-tetraen-14-yl]-6-fluoro-1-methyl-benzimidazole-5-carboxylate.

Step 4

Example 381 and 382 were prepared following steps 4-6 of Procedure 8 using A1.15 and methyl 2-[(2R,5R,7S)-6,6-difluoro-2-methyl-4-oxo-3,13,19-triazatetracyclo[11.5.2.05,7.016,20]icosa-1(19),14,16(20),17-tetraen-14-yl]-6-fluoro-1-methyl-benzimidazole-5-carboxylate. During the reaction carried out in step 4 of Procedure 8, the stereochemistry alpha to the amide epimerizes. The resulting diastereoisomeric mixture is carried through step 5-6 of Procedure 8 and is separated by C18 preparative HPLC (5-100% MeCN in water, 0.1% TFA), and the first eluting peak was assigned as the (5R,7R)-configuration (Example 381), and the second eluting peak was assigned as the (5S,7R)-configuration (Example 382). Stereochemistry of isomers were assigned by correlation by similarities to 1H NMR of other related Examples.

Procedure 38 (Example 420)

1-cyclobutyl-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nona-deca-12(19),13,15(18),16-tetraen-17-yl]benzimidazole-5-carboxamide

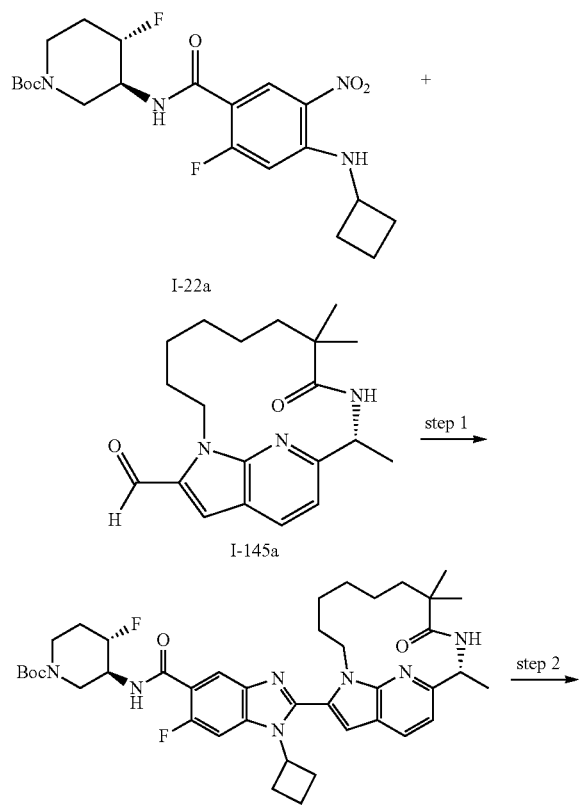

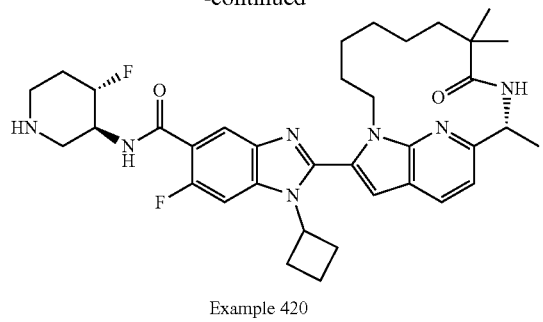

Example 420

Step 1 tert-butyl (3S,4S)-3-[[1-cyclobutyl-6-fluoro-2-[(11R)-8,8,11-trimethyl-9-oxo-1,10,19-triazatricyclo[10.5.2.015,18]nonadeca-12(19),13,15(18),16-tetraen-17-yl]benzimidazole-5-carbonyl]amino]-4-fluoro-piperidine-1-carboxylate was prepared following step 1 of Procedure 33. ES/MS: m/z 746.6 [M+H]⁺.

Step 2

Example 420 was prepared following step 6 of Procedure 8.

Note:

In some Examples, the aldehyde partner (e.g. I-142a and I-142c) contains a disubstituted alkene which can be reduced following step 1 using one of these two general procedures:

a) For Examples without a Cyclopropyl Moiety

Standard hydrogenation conditions (1 atm) with palladium on carbon (10% loading) in EtOH can be performed following step 2 or after step 5 of Procedure 8. The intermediate is typically used without further purification after filtration and concentration.

b) For Examples Containing a Cyclopropyl Moiety, this Alternate Procedure was Followed in Some Cases Reduction using p-toluenesulfonhydrazide (10 equiv.) and NaOAc (14 equiv.) in THF/water at 80° C. followed by usual saturated aqueous NaHCO₃ workup can be performed following step 2. The intermediate is typically purified by silica gel chromatography.

Procedure 39 (Example 413)

6-fluoro-~{N}-[(3~{S},4~{S})-4-fluoro-3-piperidyl]-1-[(1~{S},2~{S})-2-methylcyclopropyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide

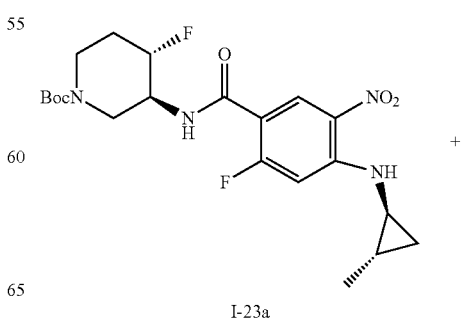

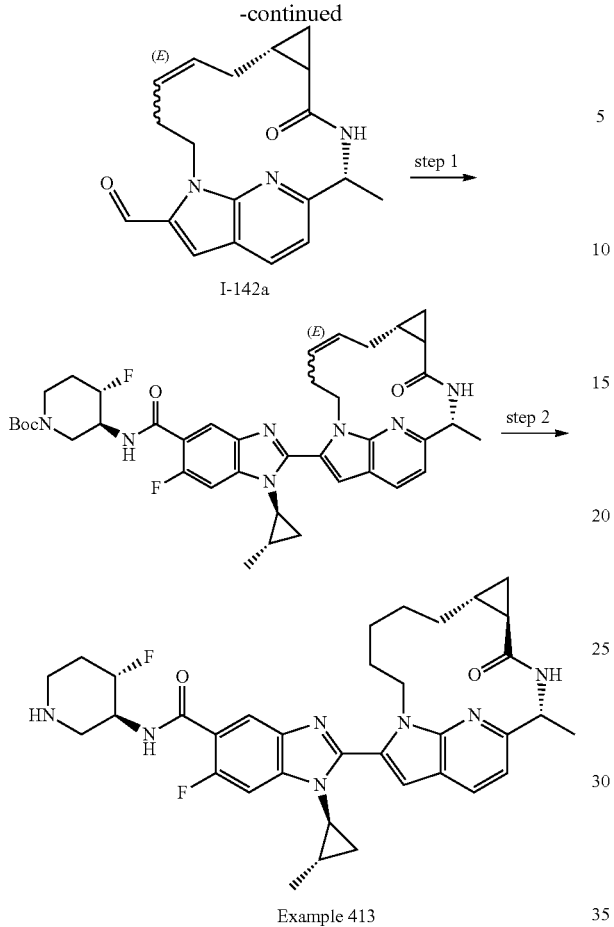

I-142a

Example 413

Step 1 tert-butyl (3S,4S)-4-fluoro-3-[[6-fluoro-1-[(1S,2S)-2-methylcyclopropyl]-2-[(2R,5R,7R,9E)-2-methyl-4-oxo-3,13,19-triazatetracyclo[11.5.2.05,7.016,20]icosa-1(19),9,14,16(20),17-pentaen-14-yl]benzimidazole-5-carbonyl]amino]piperidine-1-carboxylate was prepared following step 1 of Procedure 32. ES/MS: m/z 728.4 [M+H]⁺.

Step 2

Example 413 was prepared following step 6 of Procedure 8.

Note #1:

In some Examples (such as Example 413 above), the aldehyde partner (e.g. I-142a and I-142c) contains a disubstituted alkene which can be reduced following step 1 using one of these two general procedures:

a) For Examples without a Cyclopropyl Moiety

Standard hydrogenation conditions (1 atm) with palladium on carbon (10% loading) in EtOH can be performed following step 2 or after step 5 of Procedure 8. The intermediate is typically used without further purification after filtration and concentration.

b) For Examples Containing a Cyclopropyl Moiety, this Alternate Procedure was Followed in Some Cases Reduction using p-toluenesulfonhydrazide (10 equiv.) and NaOAc (14 equiv.) in THF/water at 80° C. followed by usual saturated aqueous NaHCO₃ workup can be performed following step 2. The intermediate is typically purified by silica gel chromatography.

Note #2:

The diastereoisomeric mixture of Examples 410 and 412 was prepared following this Procedure 32. Examples 410 and 412 were separated via chiral SFC. The absolute stereochemistry of was arbitrarily assigned for each diastereoisomer.

Procedure 40 (Examples 486 and 487)

~{N}-[(3~{S},4~{S})-4-fluoro-3-piperidyl]-7-methoxy-1-methyl-2-[(2~{R},5~{S},8~{S})-2-methyl-4-oxo-3,14,20-triazatetracyclo[12.5.2.0^{5,8}.0^{17,21}]henicosa-1(20),15,17(21),18-tetraen-15-yl]benzimidazole-5-carboxamide (Example 486)

~{N}-[(3~{S},4~{S})-4-fluoro-3-piperidyl]-7-methoxy-1-methyl-2-[(2~{R},5~{R},8~{R})-2-methyl-4-oxo-3,14,20-triazatetracyclo[12.5.2.0^{5,8}.0^{17,21}]henicosa-1(20),15,17(21),18-tetraen-15-yl]benzimidazole-5-carboxamide (Example 487)

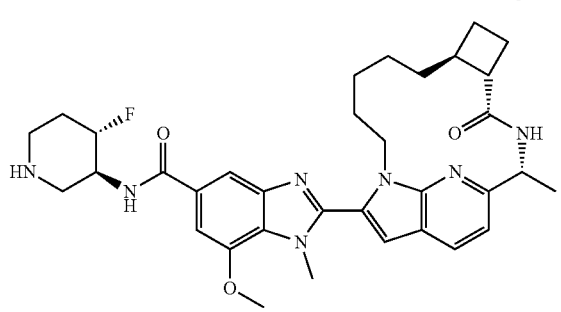

Example 486

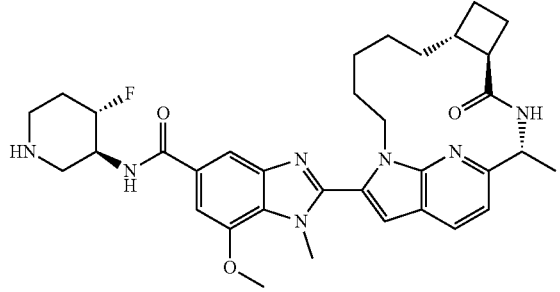

Example 487

Examples 486 and 487 were prepared using Procedure 25 using I-107c and L68. After purification by silica gel chromatography at the RCM step (step 2), the first eluting peak was arbitrarily assigned as the (5S,8S)-configuration, and the second eluting peak was assigned as the (5R,8R)-configuration. Both diastereoisomers were separately submitted to step 3 of Procedure 25 to provide Examples 486 and 487.

Procedure 41 (Example 615)

~{N}-[(3~{S},4~{S})-4-fluoro-3-piperidyl]-7-methoxy-2-[(8~{S},11~{R})-8-methoxy-11-methyl-9-oxo-1,10,19-triazatricyclo[10.5.2.0^{15,18}]nonadeca-12(19),13,15(18),16-tetraen-17-yl]-1-methyl-benzimidazole-5-carboxamide

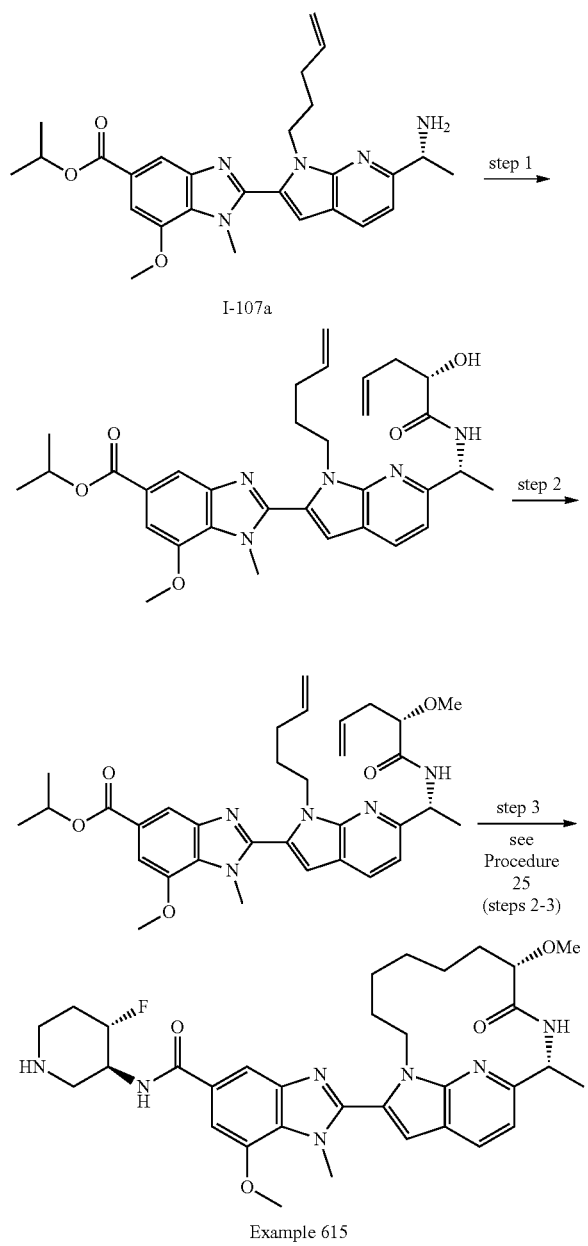

Step 1 isopropyl 2-(6-((R)-1-((S)-2-hydroxypent-4-enamido)ethyl)-1-(pent-4-en-1-yl)-1H-pyrrolo[2,3-b]pyridin-2-yl)-7-methoxy-1-methyl-1H-benzo[d]imidazole-5-carboxylate was prepared following step 1 of Procedure 25 using I-107a and (2S)-2-hydroxypent-4-enoic acid. ES/MS: m/z 574.4 [M+H]$^+$.

Step 2 isopropyl 7-methoxy-2-(6-((R)-1-((S)-2-methoxypent-4-enamido)ethyl)-1-(pent-4-en-1-yl)-1H-pyrrolo[2,3-b]pyridin-2-yl)-1-methyl-1H-benzo[d]imidazole-5-carboxylate was prepared following step 2 of Procedure 22 using isopropyl 2-(6-((R)-1-((S)-2-hydroxypent-4-enamido)ethyl)-1-(pent-4-en-1-yl)-1H-pyrrolo[2,3-b]pyridin-2-yl)-7-methoxy-1-methyl-1H-benzo[d]imidazole-5-carboxylate. ES/MS: m/z 588.4 [M+H]$^+$.

Step 3

Example 615 was prepared following steps 2-3 of Procedure 25 using isopropyl 7-methoxy-2-(6-((R)-1-((S)-2-methoxypent-4-enamido)ethyl)-1-(pent-4-en-1-yl)-1H-pyrrolo[2,3-b]pyridin-2-yl)-1-methyl-1H-benzo[d]imidazole-5-carboxylate.

Procedure 42 (Example 626)

1-(difluoromethyl)-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide

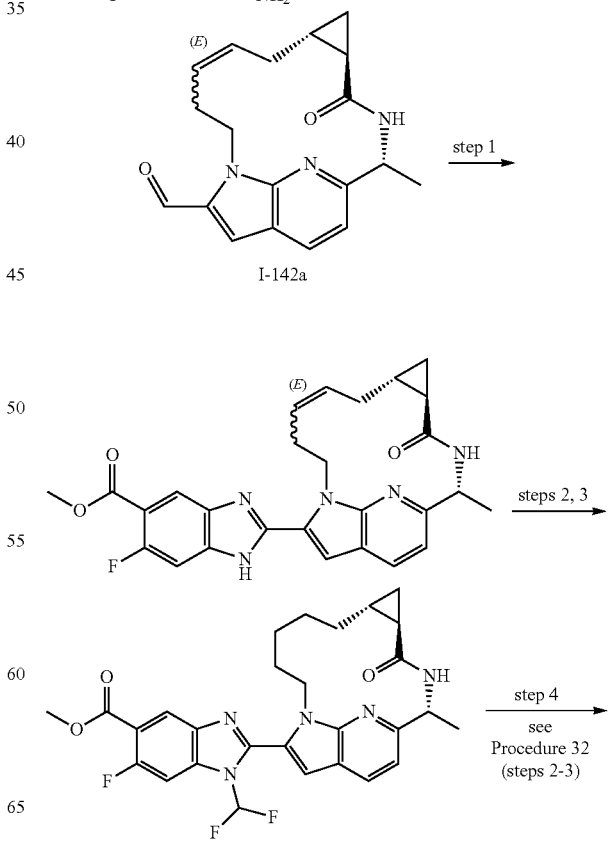

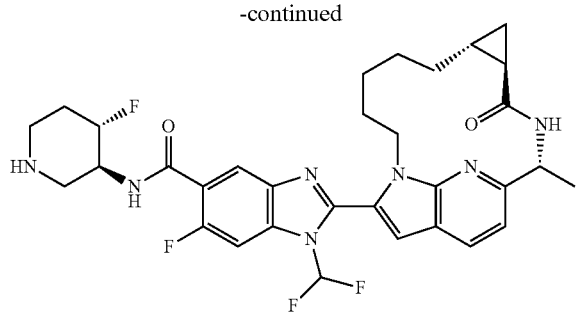

Example 626

Step 1.
methyl 6-fluoro-2-[(2R,5R,7R,9E)-2-methyl-4-oxo-3,13,19-triazatetracyclo[11.5.2.05,7.016,20]icosa-1(19),9,14,16(20),17-pentaen-14-yl]-1H-benzimidazole-5-carboxylate was prepared following step 1 of Procedure 33 using methyl 4-amino-2-fluoro-5-nitro-benzoate and I-142a. ES/MS: m/z 504.3 [M+H]$^+$.

Step 2
The alkene was reduced using standard hydrogenation conditions (1 atm)) with palladium on carbon (10% loading) in EtOAc/EtOH. ES/MS: m/z 506.3 [M+H]$^+$.

Step 3
A solution of methyl 6-fluoro-2-[(11R)-8,8,11-trimethyl-9-oxo-1,10,19-triazatricyclo[10.5.2.015,18]nonadeca-12(19),13,15(18),16-tetraen-17-yl]-1H-benzimidazole-5-carboxylate (88 mg, 0.174 mmol) and K$_2$CO$_3$ (120 mg, 0.870 mmol) in DMF (2 mL) at 90° C. was bubble chlorodifluoromethane for 10 minutes. Upon cooling, the reaction was partitioned between EtOAc and brine, dry with MgSO$_4$ and concentrated. The crude material was purified on silica gel chromatography (0-100% EtOAc in hexanes) to give a 2:1 mixture of methyl 1-(difluoromethyl)-6-fluoro-2-[(2R,5R,7R)-2-methyl-4-oxo-3,13,19-triazatetracyclo[11.5.2.05,7.016,20]icosa-1(19),14,16(20),17-tetraen-14-yl]benzimidazole-5-carboxylate (and methyl 3-(difluoromethyl)-6-fluoro-2-[(2R,5R,7R)-2-methyl-4-oxo-3,13,19-triazatetracyclo[11.5.2.05,7.016,20]icosa-1(19),14,16(20),17-tetraen-14-yl]-3H-indole-5-carboxylate). ES/MS: m/z 556.3 [M+H]$^+$.

Step 4
Example 626 was prepared following steps 2-3 of Procedure 32 using the 2:1 mixture of regioisomers describe above followed by purification by preparative HPLC (5-100% MeCN in water, 0.1% TFA).

Procedure 44 (Example 782)

(5~{R},7~{R})-14-[5-[(3~{S},4~{R})-3-amino-4-methoxy-piperidine-1-carbonyl]-7-methoxy-1-methyl-benzimidazol-2-yl]-2,2-dimethyl-3,13,19-triazatetracyclo[11.5.2.0ˆ{5,7}.0ˆ{16,20}]icosa-1(18),14,16,19-tetraen-4-one

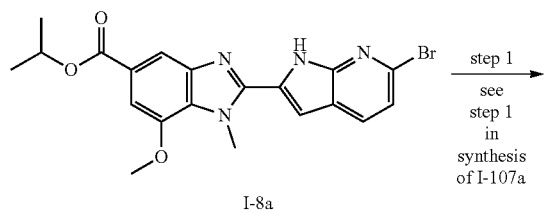

I-8a

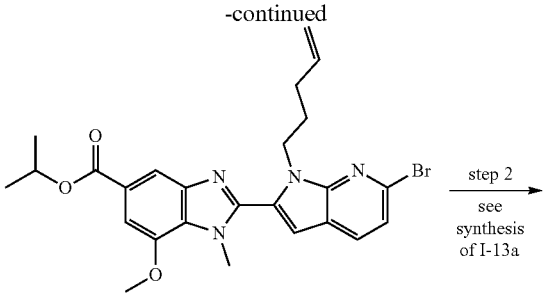

step 2
see synthesis of I-13a

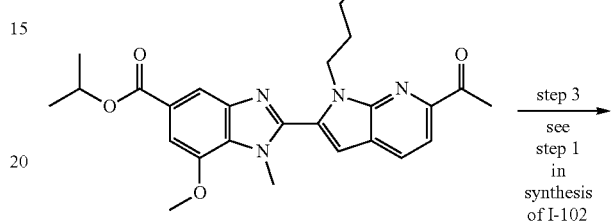

step 3
see step 1 in synthesis of I-102

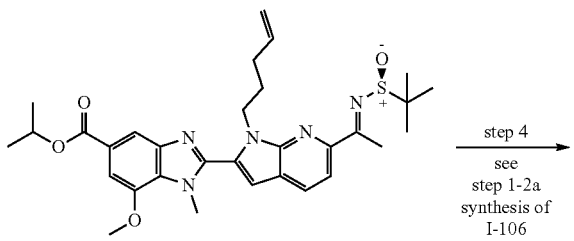

step 4
see step 1-2a synthesis of I-106

step 5
see Procedure 25 using L62a and A1.03

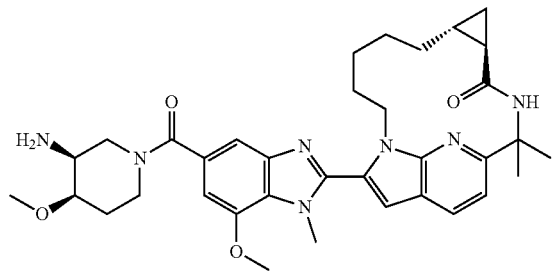

Example 782

Step 1
methyl 2-(6-bromo-1-(pent-4-en-1-yl)-1H-pyrrolo[2,3-b]pyridin-2-yl)-7-methoxy-1-methyl-1H-benzo[d]imidazole-5-carboxylate was prepared following a similar procedure to step 1 in the synthesis of I-107a using I-8a instead of I-102. ES/MS: m/z 483.0 [M+H]$^+$.

Step 2
methyl 2-(6-acetyl-1-(pent-4-en-1-yl)-1H-pyrrolo[2,3-b]pyridin-2-yl)-7-methoxy-1-methyl-1H-benzo[d]imidazole-5-carboxylate was prepared following a similar procedure to the synthesis of I-13a using methyl 2-(6-bromo-1-(pent-4-en-1-yl)-1H-pyrrolo[2,3-b]pyridin-2-yl)-7-methoxy-1-

591 methyl-1H-benzo[d]imidazole-5-carboxylate instead of I-10a. ES/MS: m/z 447.2 [M+H]+.

Step 3 isopropyl (E)-2-(6-(1-((tert-butylsulfinyl)imino)ethyl)-1-(pent-4-en-1-yl)-1H-pyrrolo[2,3-b]pyridin-2-yl)-7-methoxy-1-methyl-1H-benzo[d]imidazole-5-carboxylate was prepared following a similar procedure to step 1 of the synthesis of I-102 using methyl 2-(6-acetyl-1-(pent-4-en-1-yl)-1H-pyrrolo[2,3-b]pyridin-2-yl)-7-methoxy-1-methyl-1H-benzo[d]imidazole-5-carboxylate instead of I-13a. ES/MS: m/z 577.9 [M+H]+.

Step 4 isopropyl 2-(6-(2-aminopropan-2-yl)-1-(pent-4-en-1-yl)-1H-pyrrolo[2,3-b]pyridin-2-yl)-7-methoxy-1-methyl-1H-benzo[d]imidazole-5-carboxylate was prepared following a similar procedure to step 1 and 2a in the synthesis of I-106 using isopropyl (E)-2-(6-(1-((tert-butylsulfinyl)imino)ethyl)-1-(pent-4-en-1-yl)-1H-pyrrolo[2,3-b]pyridin-2-yl)-7-methoxy-1-methyl-1H-benzo[d]imidazole-5-carboxylate. ES/MS: m/z 490.4 [M+H]+.

Step 5

Example 782 was prepared following Procedure 25, utilizing isopropyl 2-(6-(2-aminopropan-2-yl)-1-(pent-4-en-1-yl)-1H-pyrrolo[2,3-b]pyridin-2-yl)-7-methoxy-1-methyl-1H-benzo[d]imidazole-5-carboxylate, L62a and A1.03.

Procedure 45 (Example 813)

(2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-cyclopropyl-2-methyl-3,9,16,22-tetrazatetracyclo[14.5.2.0^{5,10}.0^{19,23}]tricosa-1(21),5(10),6,8,17,19,22-heptaen-4-one

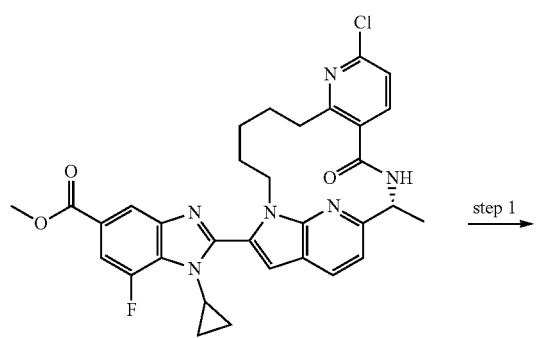

product of step 3 of Example 472

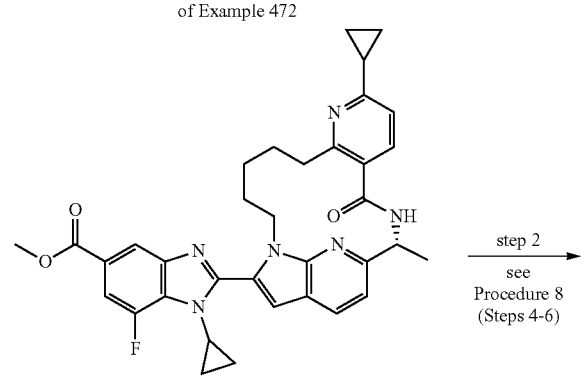

592

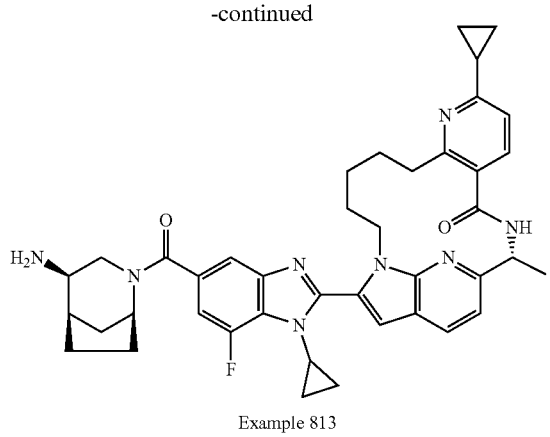

Example 813

Step 1.

A mixture of methyl 2-[(2R)-8-chloro-2-methyl-4-oxo-3,9,16,22-tetrazatetracyclo[14.5.2.0^5,10.0^19,23]tricosa-1(22),5(10),6,8,17,19(23),20-heptaen-17-yl]-1-cyclopropyl-7-fluoro-benzimidazole-5-carboxylate (75.0 mg, 0.125 mmol), potassium cyclopropyltrifluoroborate (56 mg, 0.375 mmol), cataCXium Pd G4 (10 mg, 0.013 mmol) and cesium carbonate (122 mg, 0.375 mmol) in dioxane (1 mL) and water (0.1 mL) was heated at 100 degrees overnight. After cooling to rt, the reaction mixture was diluted with DCM and water. The layers were separated and aqueous extracted with DCM. The combined organics were dried, filtered, and concentrated under reduced pressure. The resulting residue was purified via silica gel column chromatography (25-100% ethyl acetate in hexanes to yield methyl 1-cyclopropyl-2-[(2R)-8-cyclopropyl-2-methyl-4-oxo-3,9,16,22-tetrazatetracyclo[14.5.2.05,10.019,23]tricosa-1(22),5(10),6,8,17,19(23),20-heptaen-17-yl]-7-fluoro-benzimidazole-5-carboxylate. ES/MS: m/z 607.2 [M–H]+.

Step 2

Example 813 was synthesized following steps 4-6 of procedure 8 using methyl 1-cyclopropyl-2-[(2R)-8-cyclopropyl-2-methyl-4-oxo-3,9,16,22-tetrazatetracyclo[14.5.2.05,10.019,23]tricosa-1(22),5(10),6,8,17,19(23),20-heptaen-17-yl]-7-fluoro-benzimidazole-5-carboxylate and A18.

Procedure 46 (Example 820)

(2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-8-(2-phenylethynyl)-3,9,16,22-tetrazatetracyclo[14.5.2.0^{5,10}.0^{19,23}]tricosa-1(21),5(10),6,8,17,19,22-heptaen-4-one product of step 3 of Example 472

593
-continued

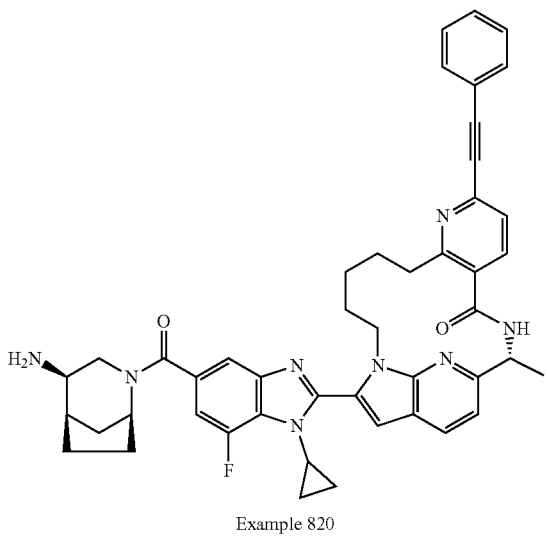

Example 820

Step 1.

A mixture of using methyl 2-[(2R)-8-chloro-2-methyl-4-oxo-3,9,16,22-tetrazatetracyclo[14.5.2.05,10.019,23]tricosa-1(22),5(10),6,8,17,19(23),20-heptaen-17-yl]-1-cyclopropyl-7-fluoro-benzimidazole-5-carboxylate (75.0 mg, 0.125 mmol), tricyclohexylphosphine (0.00140 g, 0.00499 mmol), and phenylacetylene (0.0206 mL, 0.188 mmol) in triethylamine (1 mL) was sparged with argon. CuI (0.000951 g, 0.00499 mmol) and PdCl$_2$(PPh$_3$)$_2$(0.00350 g, 0.00499 mmol) were added and the reaction mixture was heated at 75 degrees overnight. After cooling to rt, the reaction mixture was diluted with DCM and water. The layers were separated and aqueous extracted with DCM. The combined organics were dried, filtered, and concentrated under reduced pressure. The resulting residue was purified via silica gel column chromatography (25-100% ethyl acetate in hexanes to yield methyl 1-cyclopropyl-7-fluoro-2-[(2R)-2-methyl-4-oxo-8-(2-phenylethynyl)-3,9,16,22-tetrazatetracyclo[14.5.2.05,10.019,23]tricosa-1(22),5(10),6,8,17,19(23),20-heptaen-17-yl]benzimidazole-5-carboxylate. ES/MS: m/z 667.2 [M–H]$^+$.

Step 2

Example 820 was synthesized following steps 4-6 of procedure 8 using methyl 1-cyclopropyl-7-fluoro-2-[(2R)-2-methyl-4-oxo-8-(2-phenylethynyl)-3,9,16,22-tetrazatetracyclo[14.5.2.05,10.019,23]tricosa-1(22),5(10),6,8,17,19 (23),20-heptaen-17-yl]benzimidazole-5-carboxylate and A18.

594
Procedure 47 (Example 656)

(2~{R})-17-[5-[(3~{S},4~{R})-3-amino-4-methoxy-piperidine-1-carbonyl]-7-methoxy-1-methyl-benzimidazol-2-yl]-6-fluoro-2-methyl-3,9,16,22-tetrazatetracyclo[14.5.2.0^{5,10}.0^{19,23}]tricosa-1(22),5,7,9,17,19(23),20-heptaen-4-one

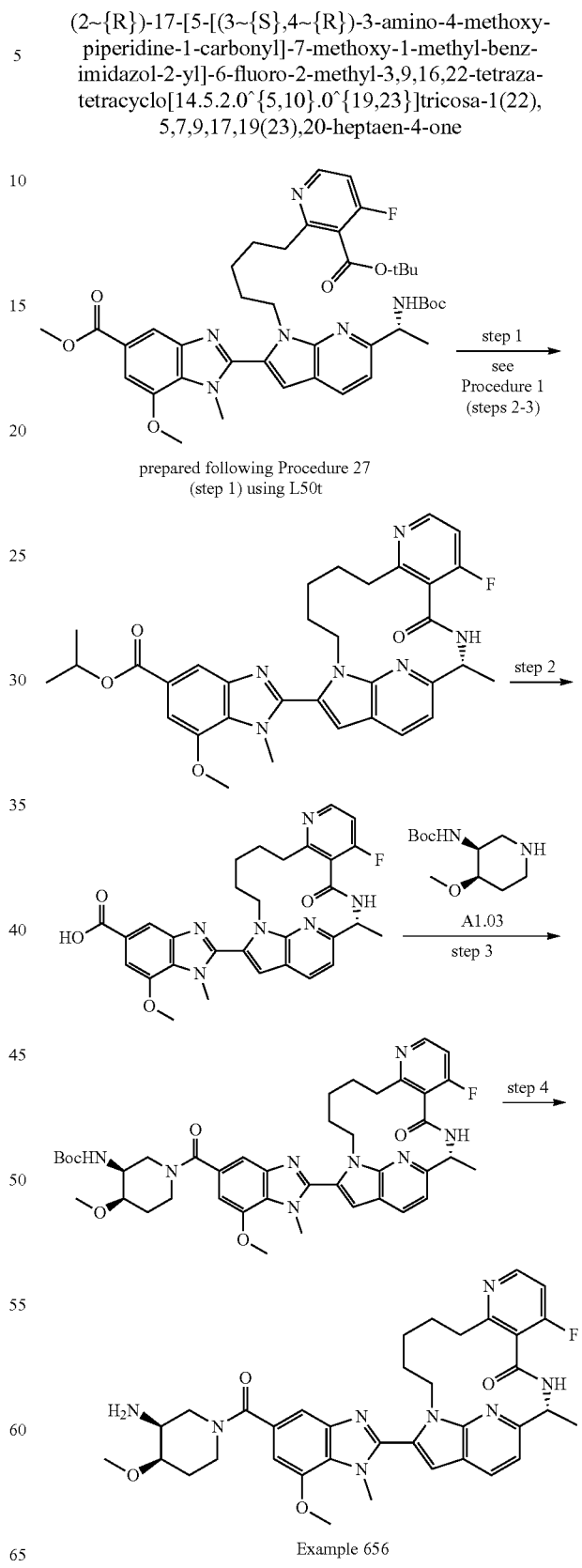

Example 656

Example 656

Step 1 isopropyl 2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carboxylate was prepared according to the procedures described in Steps 2-3 of Procedure 1, using isopropyl (R)-2-(1-(5-(3-(tert-butoxycarbonyl)-4-fluoropyridin-2-yl)pentyl)-6-(1-((tert-butoxycarbonyl)amino)ethyl)-1H-pyrrolo[2,3-b]pyridin-2-yl)-7-methoxy-1-methyl-1H-benzo[d]imidazole-5-carboxylate in place of ethyl (R)-2-(1-(8-(tert-butoxy)-8-oxooctyl)-6-(1-((tert-butoxycarbonyl)amino)ethyl)-1H-pyrrolo[2,3-b]pyridin-2-yl)-5-methoxy-3-methylimidazo[1,2-a]pyridine-7-carboxylate. ES/MS: m/z 599.3 [M+H]+.

Step 2

To isopropyl 2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carboxylate (0.042 g, 0.070 mmol) in DCE (0.9 mL) was added trimethyltin hydroxide (0.127 g, 0.702 mmol). The mixture was stirred at 80° C. for 2 weeks. The mixture was cooled to rt and concentrated to yield crude 2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carboxylic acid, which was used directly. ES/MS: m/z 557.3 [M+H]+.

Step 3 tert-butyl N-[(3S,4R)-1-[2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carbonyl]-4-methoxy-3-piperidyl]carbamate was prepared according to the procedure described in Step 5 of Procedure 8, using crude 2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carboxylic acid and A1.03 in place of 7-methoxy-1-methyl-2-[(11R)-11-methyl-9-oxo-1,10-diazatricyclo[10.5.2.015,18]nonadeca-12(19),13,15(18),16-tetraen-17-yl]benzimidazole-5-carboxylic acid and A2, respectively. ES/MS: m/z 769.4 [M+H]+.

Step 4

Crude tert-butyl N-[(3S,4R)-1-[2-[(2R)-6-fluoro-2-methyl-4-oxo-3,9,16,22-tetrazatetracyclo[14.5.2.05,10.019,23]tricosa-1(22),5(10),6,8,17,19(23),20-heptaen-17-yl]-7-methoxy-1-methyl-benzimidazole-5-carbonyl]-4-methoxy-3-piperidyl]carbamate (ca. 0.070 mmol) was dissolved in DCM (0.7 mL) and TFA (0.7 mL). The mixture sat at rt for 10 min and was then concentrated en vacuo. The residue was taken up in DMSO and water and purified via preparative reverse phase HPLC, producing Example 656.

Procedure 48 (Example 866)

(13~{R})-19-[5-[(3~{S},4~{R})-3-amino-4-methoxy-piperidine-1-carbonyl]-7-methoxy-1-methyl-benzimidazol-2-yl]-13-methyl-1,12,21-triazatetracyclo[12.5.2.1ˆ{5,9}.0ˆ{17,20}]docosa-5,7,9(22),14(21),15,17(20),18-heptaen-11-one

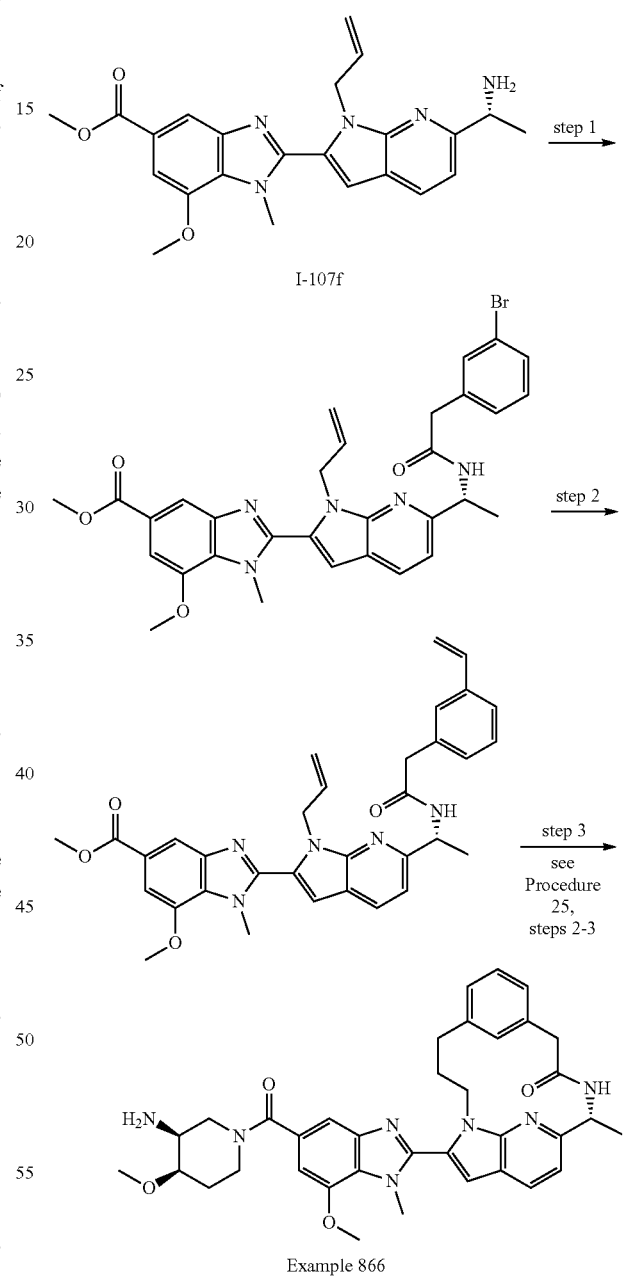

Example 866

Step 1.

methyl (R)-2-(1-allyl-6-(1-(2-(3-bromophenyl)acetamido)ethyl)-1H-pyrrolo[2,3-b]pyridin-2-yl)-7-methoxy-1-methyl-1H-benzo[d]imidazole-5-carboxylate was prepared following a similar procedure to step 1 of Procedure 25. ES/MS: m/z 644.4, 646.2 [M+H]+.

Step 2 methyl (R)-2-(1-allyl-6-(1-(2-(3-vinylphenyl)acetamido)ethyl)-1H-pyrrolo[2,3-b]pyridin-2-yl)-7-methoxy-1-methyl-1H-benzo[d]imidazole-5-carboxylate was prepared following a similar procedure to step 1 of L67a. ES/MS: m/z 592.3 [M+H]$^+$.

Step 3

Example 866 was synthesized following steps 2-3 of procedure 25 using methyl (R)-2-(1-allyl-6-(1-(2-(3-vinylphenyl)acetamido)ethyl)-1H-pyrrolo[2,3-b]pyridin-2-yl)-7-methoxy-1-methyl-1H-benzo[d]imidazole-5-carboxylate and A1.03.

Procedure 49 (Example 937)

[(3~{R})-3-amino-1-piperidyl]-[7-methoxy-1-methyl-2-(11-methyl-10,10-dioxo-10$]^{6}-thia-1,11,19-triazatricyclo[10.5.2.0^{15,18}]nonadeca-12(19),13,15(18),16-tetraen-17-yl)benzimidazol-5-yl]methanone

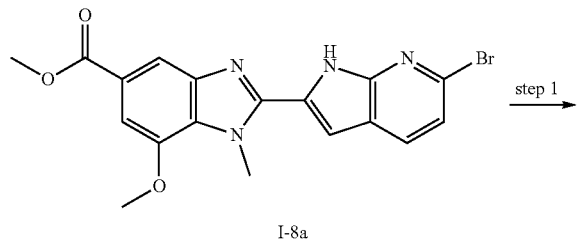

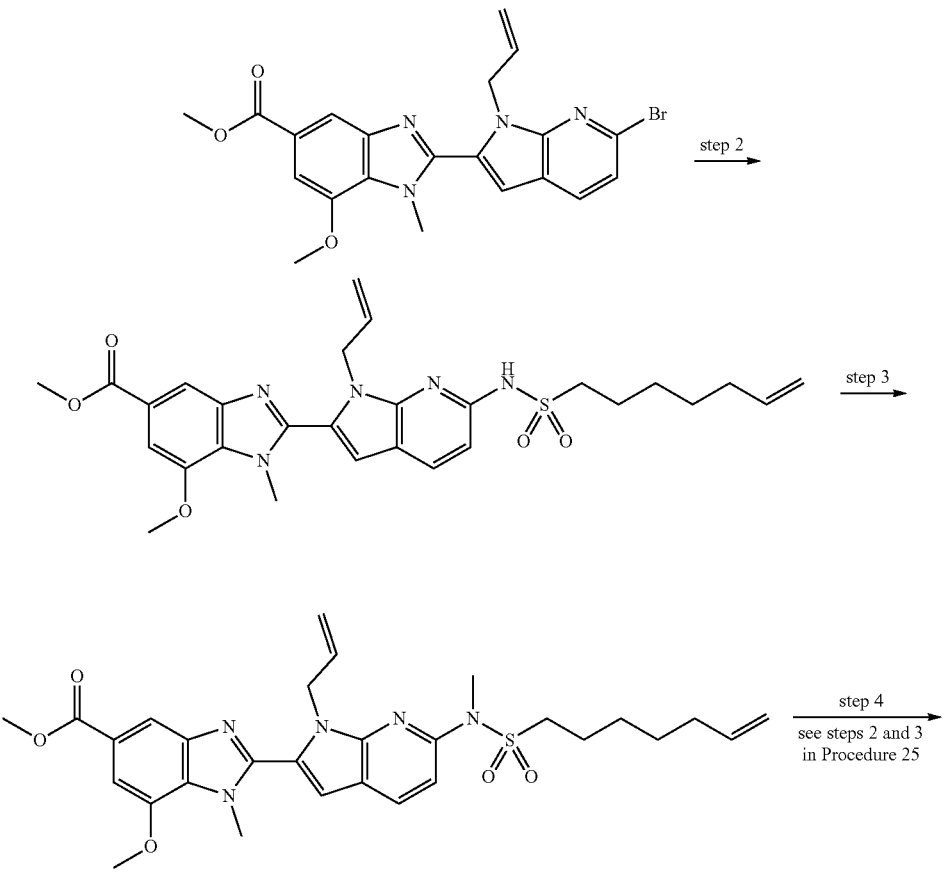

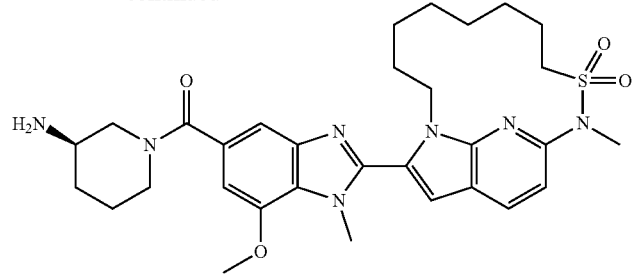

Example 937

Step 1
A mixture of I-8a (1000 mg, 2.41 mmol), allyl bromide (0.25 mL, 2.89 mmol), and cesium carbonate (2354 mg, 7.22 mmol) in DMF (60 mL) was stirred at rt. After 90 minutes, water was added. The precipitated solid was filtered, washed with water and dried in vacuo to yield methyl 2-(1-allyl-6-bromo-1H-pyrrolo[2,3-b]pyridin-2-yl)-7-methoxy-1-methyl-1H-benzo[d]imidazole-5-carboxylate. ES/MS: m/z 455.2 [M+H]$^+$.

Step 2
A mixture of methyl 2-(1-allyl-6-bromo-1H-pyrrolo[2,3-b]pyridin-2-yl)-7-methoxy-1-methyl-1H-benzo[d]imidazole-5-carboxylate (100 mg, 0.22 mmol), hept-6-ene-1-sulfonamide (0.100 g, 0.000564 mol), potassium carbonate (91.1 mg, 0.659 mmol), and tBuXPhos G3 (0.0262 g, 3.29e-5 mol) in dioxane (5 mL) was heated at 100 degrees under argon. After 6 hours, the reaction mixture was diluted with ethyl acetate and filtered over celite. The filtrate was concentrated under reduced pressure. The resulting residue was purified via silica gel column chromatography (5-60% ethyl acetate in hexanes) to yield methyl 2-(1-allyl-6-(hept-6-en-1-ylsulfonamido)-1H-pyrrolo[2,3-b]pyridin-2-yl)-7-methoxy-1-methyl-1H-benzo[d]imidazole-5-carboxylate. ES/MS: m/z 552.2 [M+H]$^+$.

Step 3
Iodomethane (0.036 mL, 0.580 mmol) was added to a mixture of methyl 2-(1-allyl-6-(hept-6-en-1-ylsulfonamido)-1H-pyrrolo[2,3-b]pyridin-2-yl)-7-methoxy-1-methyl-1H-benzo[d]imidazole-5-carboxylate (80 mg, 0.145 mmol) and potassium carbonate (202 mg, 1.46 mmol) in DMF (3 mL) at rt. After 2 hours, the reaction mixture was diluted with ethyl acetate and water. The layers were separated and aqueous was extracted with ethyl acetate. The combined organics were dried, filtered, and was concentrated under reduced pressure to yield methyl 2-(1-allyl-6-(N-methylhept-6-en-1-ylsulfonamido)-1H-pyrrolo[2,3-b]pyridin-2-yl)-7-methoxy-1-methyl-1H-benzo[d]imidazole-5-carboxylate. ES/MS: m/z 566.1 [M+H]$^+$.

Step 4
Example 937 was prepared following steps 2 and 3 of Procedure 25, utilizing methyl 2-(1-allyl-6-(N-methylhept-6-en-1-ylsulfonamido)-1H-pyrrolo[2,3-b]pyridin-2-yl)-7-methoxy-1-methyl-1H-benzo[d]imidazole-5-carboxylate and A1.

7. Example Tables

The Examples listed in Tables 1 and 1A were prepared according to the Procedures described herein (and indicated in Table 2 under Procedure) using the appropriate Intermediate 1, Intermediate 2 and Intermediate A (as indicated in Table 2). Compound characterizations (MS and $^1$H NMR) are listed in Table 3.

TABLE 1

| Example | Structure | Name |
| --- | --- | --- |
| 1 | 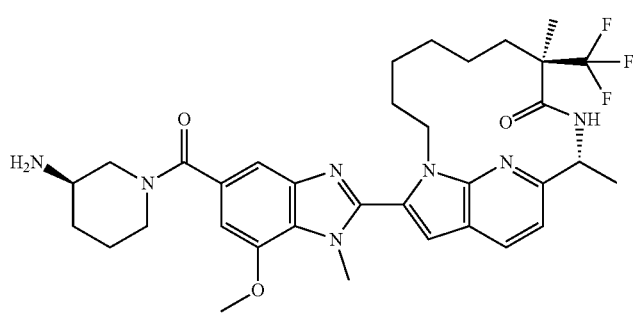 [SMILES: COc1cc(C(=O)N2CCC[C@@H](N)C2)cc2nc(-c3cc4ccc5nc4n3CCCCCC[C@@](C)(C(F)(F)F)C(=O)N[C@@H]5C)n(C)c12] | (8~{R},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |

TABLE 1-continued

| Example | Structure | Name |
|---|---|---|
| 2 | 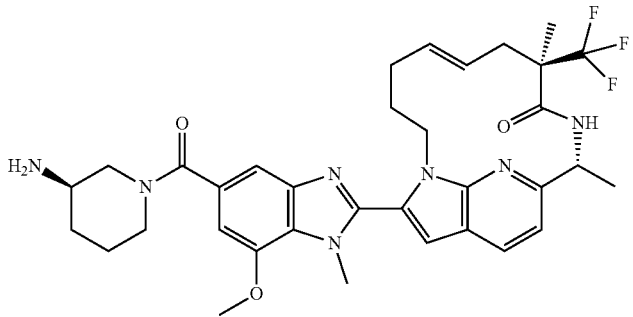 [SMILES: COc1cc(C(=O)N2CCC[C@@H](N)C2)cc2nc(-c3cc4ccc5nc4n3CCC/C=C/C[C@@](C)(C(F)(F)F)C(=O)N[C@@H]5C)n(C)c12] | (5~{E},8~{R},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-5,12(19),13,15(18),16-pentaen-9-one |
| 3 | 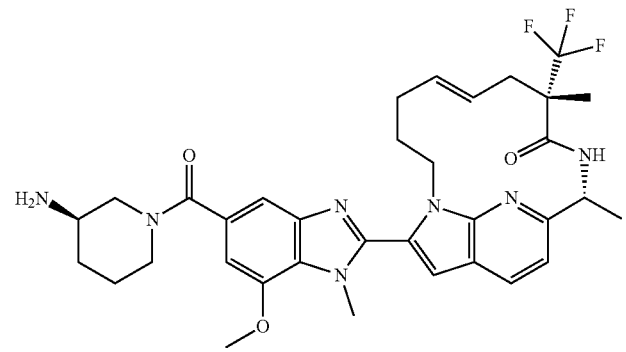 [SMILES: COc1cc(C(=O)N2CCC[C@@H](N)C2)cc2nc(-c3cc4ccc5nc4n3CCC/C=C/C[C@](C)(C(F)(F)F)C(=O)N[C@@H]5C)n(C)c12] | (5~{E},8~{S},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-5,12(19),13,15(18),16-pentaen-9-one |
| 4 | 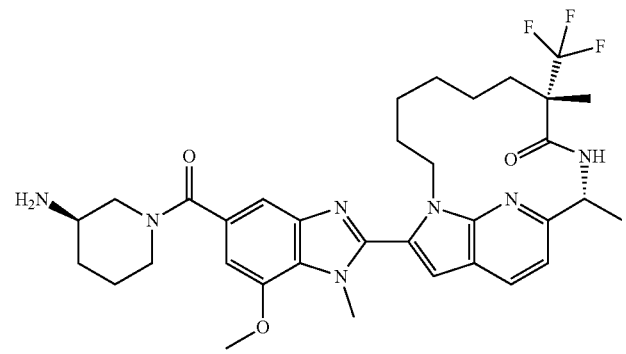 [SMILES: COc1cc(C(=O)N2CCC[C@@H](N)C2)cc2nc(-c3cc4ccc5nc4n3CCCCCC[C@](C)(C(F)(F)F)C(=O)N[C@@H]5C)n(C)c12] | (8~{S},11~{R})-17-[5-[(3~{R})-3-aminopiperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 5 | 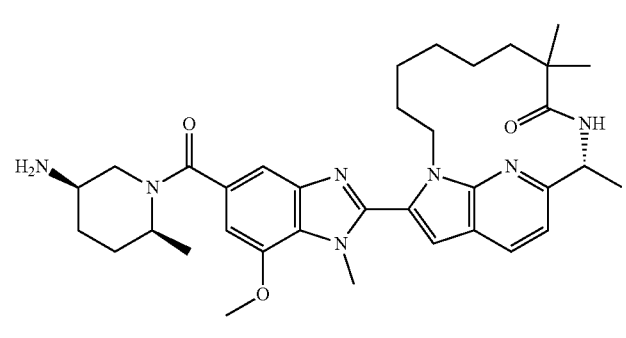 [SMILES: COc1cc(C(=O)N2C[C@H](N)CC[C@@H]2C)cc2nc(-c3cc4ccc5nc4n3CCCCCCC(C)(C)C(=O)N[C@@H]5C)n(C)c12] | (11~{R})-17-[5-[(2~{S},5~{R})-5-amino-2-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 6 | 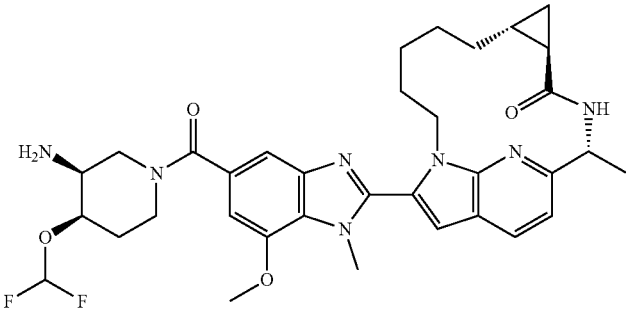 [SMILES: COc1cc(C(=O)N2CC[C@@H](OC(F)F)[C@@H](N)C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{S},4~{R})-3-amino-4-(difluoromethoxy)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 7 | 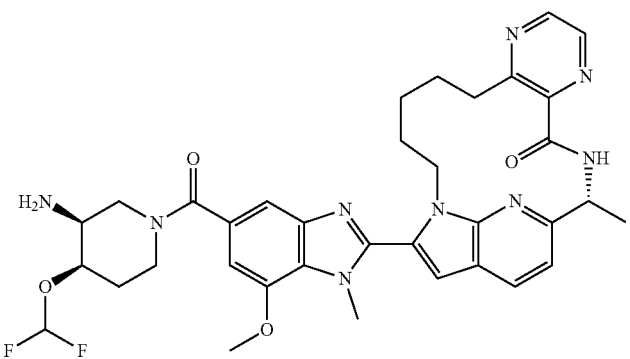 [SMILES: COc1cc(C(=O)N2CC[C@@H](OC(F)F)[C@@H](N)C2)cc2nc(-c3cc4ccc5nc4n3CCCCCc3nccnc3C(=O)N[C@@H]5C)n(C)c12] | (2~{R})-17-[5-[(3~{S},4~{R})-3-amino-4-(difluoromethoxy)piperidine-1-carbonyl]-7-methoxy-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 8 | 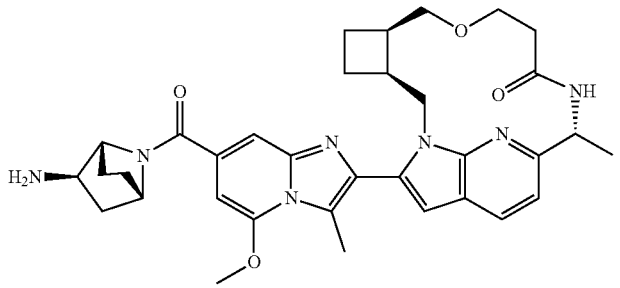 [SMILES: COc1cc(C(=O)N2[C@H]3CC[C@@H]2[C@H](N)C3)cc2nc(-c3cc4ccc5nc4n3C[C@H]3CC[C@H]3COCCC(=O)N[C@@H]5C)c(C)n12] | (3~{S},6~{R},13~{R})-19-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-13-methyl-8-oxa-1,12,21-triazatetracyclo[12.5.2.0^{3,6}.0^{17,20}]henicosa-14(21),15,17(20),18-tetraen-11-one |
| 9 | 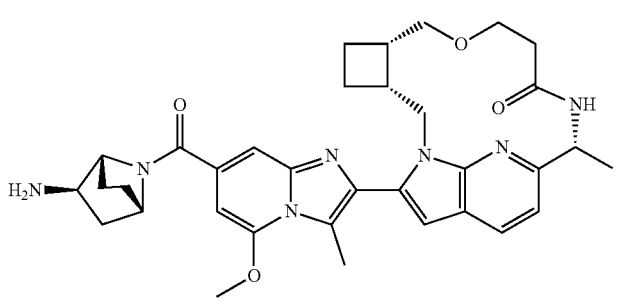 [SMILES: COc1cc(C(=O)N2[C@H]3CC[C@@H]2[C@H](N)C3)cc2nc(-c3cc4ccc5nc4n3C[C@@H]3CC[C@@H]3COCCC(=O)N[C@@H]5C)c(C)n12] | (3~{R},6~{S},13~{R})-19-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-13-methyl-8-oxa-1,12,21-triazatetracyclo[12.5.2.0^{3,6}.0^{17,20}]henicosa-14(21),15,17(20),18-tetraen-11-one |
| 10 | 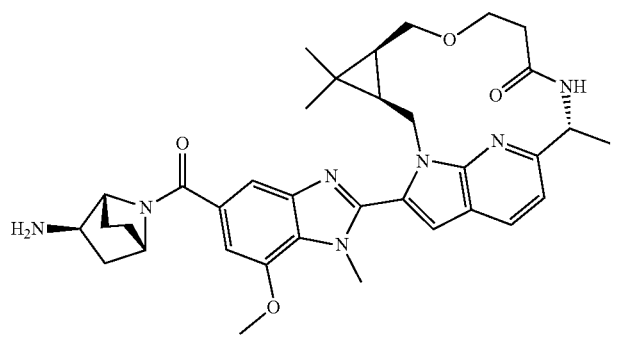 [SMILES: COc1cc(C(=O)N2[C@H]3CC[C@@H]2[C@H](N)C3)cc2nc(-c3cc4ccc5nc4n3C[C@@H]3[C@H](COCCC(=O)N[C@@H]5C)C3(C)C)n(C)c12] | (3~{R},5~{S},12~{R})-18-[5-[(1~{R},2~{R},4~{S})-2-amino-7-azabicyclo[2.2.1]heptane-7-carbonyl]-7-methoxy-1-methyl-benzimidazol-2-yl]-4,4,12-trimethyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 11 | 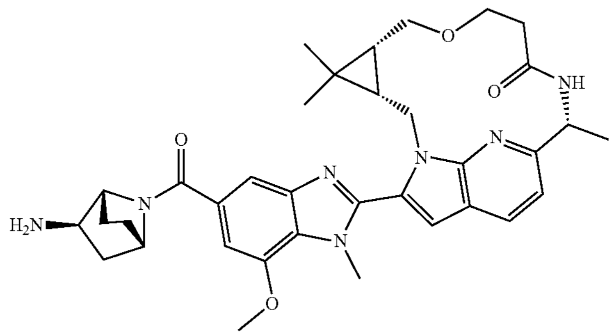 [SMILES: COc1cc(C(=O)N2[C@H]3CC[C@@H]2[C@H](N)C3)cc2nc(-c3cc4ccc5nc4n3C[C@H]3[C@@H](COCCC(=O)N[C@@H]5C)C3(C)C)n(C)c12] | (3~{S},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-4,4,12-trimethyl-7-oxa-1,11,20-triazatetracyclo[11.5.2.0^{3,5}.0^{16,19}]icosa-13(20),14,16(19),17-tetraen-10-one |
| 12 | 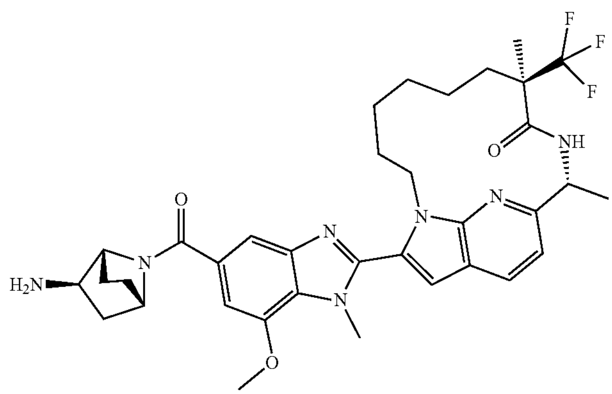 [SMILES: COc1cc(C(=O)N2[C@H]3CC[C@@H]2[C@H](N)C3)cc2nc(-c3cc4ccc5nc4n3CCCCCC[C@@](C)(C(F)(F)F)C(=O)N[C@@H]5C)n(C)c12] | (8~{R},11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 13 | 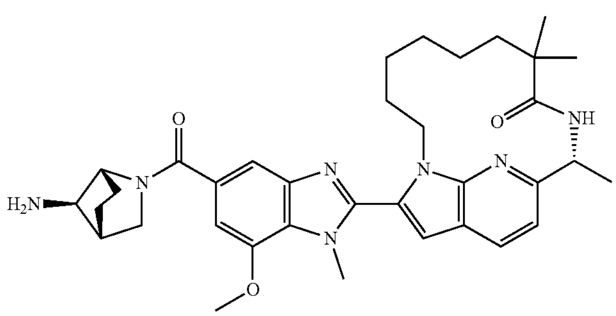 [SMILES: COc1cc(C(=O)N2C[C@H]3CC[C@@H]2[C@@H]3N)cc2nc(-c3cc4ccc5nc4n3CCCCCCC(C)(C)C(=O)N[C@@H]5C)n(C)c12] | (11~{R})-17-[5-[(1~{R},4~{R},7~{R})-7-amino-2-azabicyclo[2.2.1]heptane-2-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 14 | 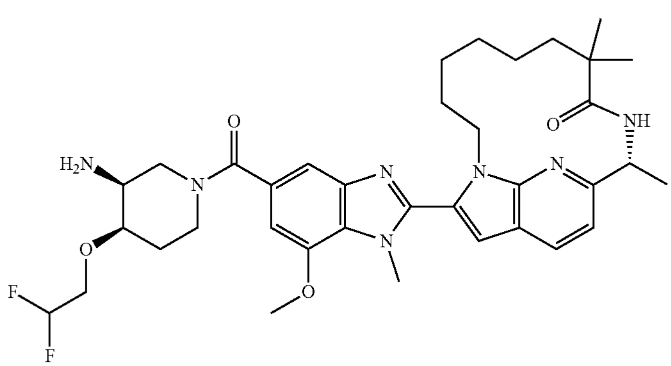 [SMILES: COc1cc(C(=O)N2CC[C@@H](OCC(F)F)[C@@H](N)C2)cc2nc(-c3cc4ccc5nc4n3CCCCCCC(C)(C)C(=O)N[C@@H]5C)n(C)c12] | (11~{R})-17-[5-[(3~{S},4~{R})-3-amino-4-(2,2-difluoroethoxy)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 15 | 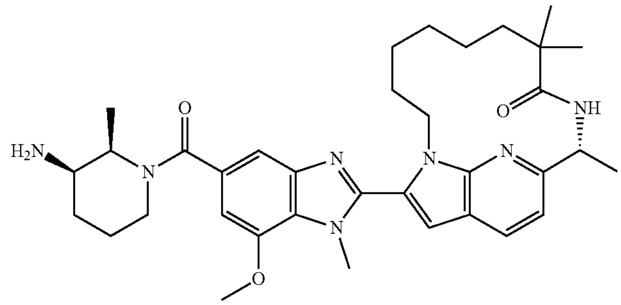 [SMILES: COc1cc(C(=O)N2CCC[C@@H](N)[C@H]2C)cc2nc(-c3cc4ccc5nc4n3CCCCCCC(C)(C)C(=O)N[C@@H]5C)n(C)c12] | (11~{R})-17-[5-[(2~{R},3~{R})-3-amino-2-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 16 | 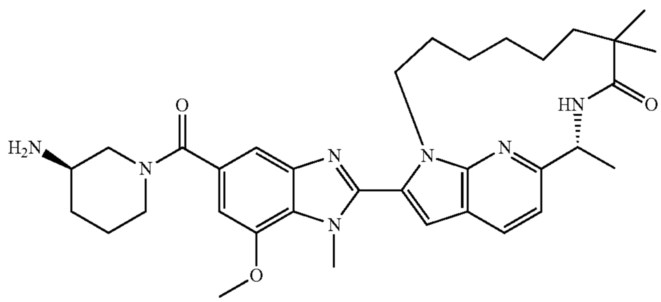 [SMILES: COc1cc(C(=O)N2CCC[C@@H](N)C2)cc2nc(-c3cc4ccc5nc4n3CCCCCCC(C)(C)C(=O)N[C@@H]5C)n(C)c12] | (11~{R})-17-[5-[(3~{R})-3-aminopiperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 17 | 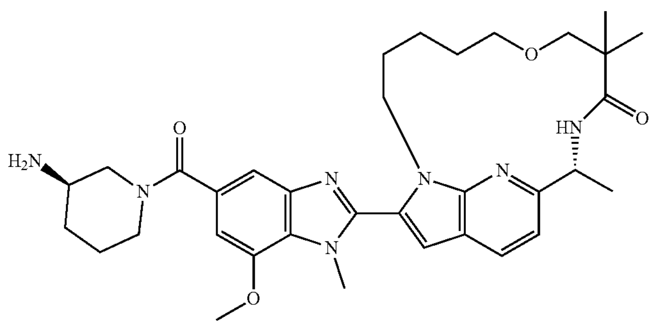 [SMILES: COc1cc(C(=O)N2CCC[C@@H](N)C2)cc2nc(-c3cc4ccc5nc4n3CCCCCOCC(C)(C)C(=O)N[C@@H]5C)n(C)c12] | (12~{R})-18-[5-[(3~{R})-3-aminopiperidine-1-carbonyl]-7-methoxy-1-methyl-benzimidazol-2-yl]-9,9,12-trimethyl-7-oxa-1,11,20-triazatricyclo[11.5.2.0^{16,19}]icosa-13(20),14,16(19),17-tetraen-10-one |
| 18 | 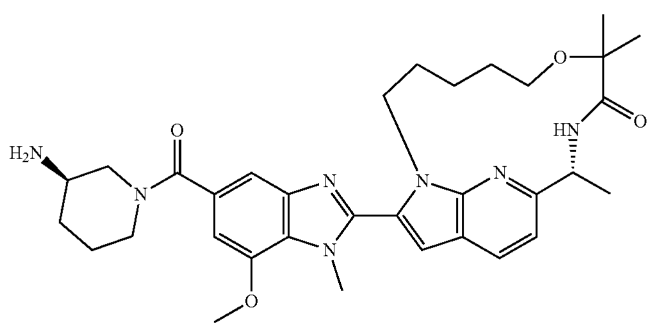 [SMILES: COc1cc(C(=O)N2CCC[C@@H](N)C2)cc2nc(-c3cc4ccc5nc4n3CCCCCOC(C)(C)C(=O)N[C@@H]5C)n(C)c12] | (11~{R})-17-[5-[(3~{R})-3-aminopiperidine-1-carbonyl]-7-methoxy-1-methyl-benzimidazol-2-yl]-8,8,11-trimethyl-7-oxa-1,10,19-triazatricyclo[10.5.2.0^{15,18}]nonadeca-12(19),13,15(18),16-tetraen-9-one |
| 19 | 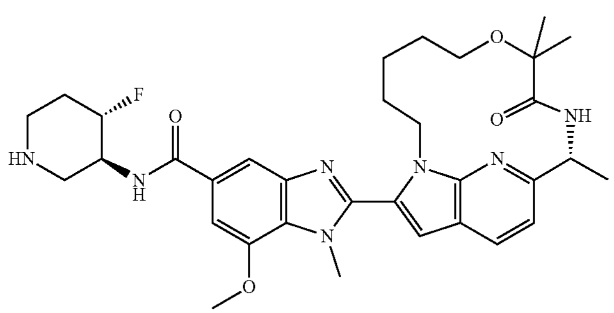 [SMILES: COc1cc(C(=O)N[C@H]2CNCC[C@@H]2F)cc2nc(-c3cc4ccc5nc4n3CCCCCOC(C)(C)C(=O)N[C@@H]5C)n(C)c12] | ~{N}-[(3~{S},4~{S})-4-fluoro-3-piperidyl]-7-methoxy-1-methyl-2-[(11~{R})-8,8,11-trimethyl-9-oxo-7-oxa-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 20 | 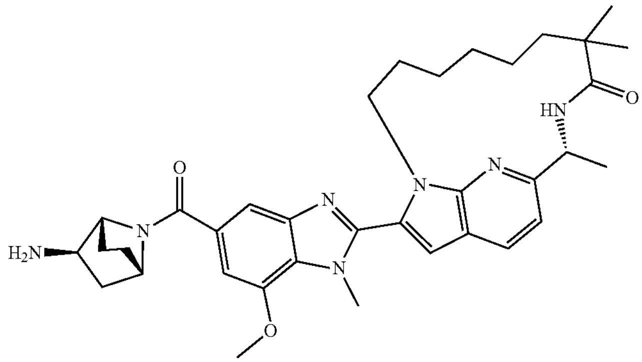 [SMILES: COc1cc(C(=O)N2[C@H]3CC[C@@H]2[C@H](N)C3)cc2nc(-c3cc4ccc5nc4n3CCCCCCC(C)(C)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 21 | 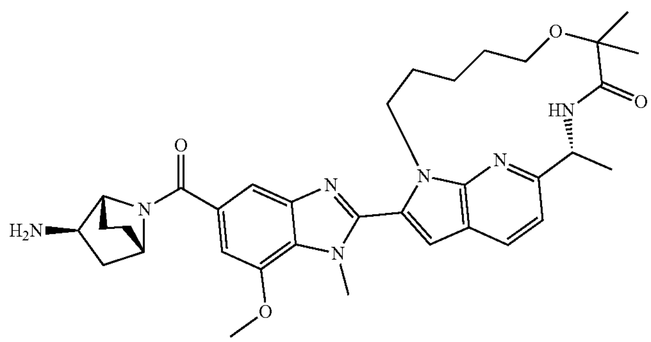 [SMILES: COc1cc(C(=O)N2[C@H]3CC[C@@H]2[C@H](N)C3)cc2nc(-c3cc4ccc5nc4n3CCCCCOC(C)(C)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,8,11-trimethyl-7-oxa-1,10,19-triazatricyclo[10.5.2.0^{15,18}]nonadeca-12(19),13,15(18),16-tetraen-9-one |
| 22 | 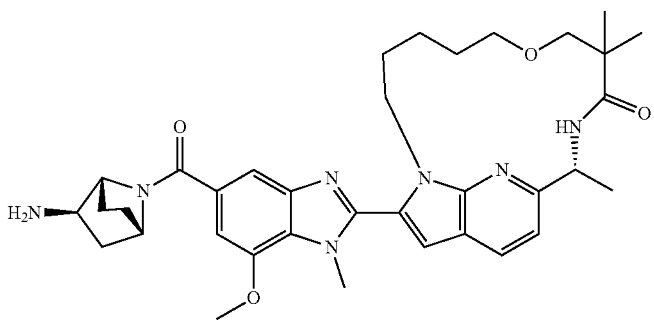 [SMILES: COc1cc(C(=O)N2[C@H]3CC[C@@H]2[C@H](N)C3)cc2nc(-c3cc4ccc5nc4n3CCCCCOCC(C)(C)C(=O)N[C@@H]5C)n(C)c12] | (12~{R})-18-[5-[(1~{R},2~{R},4~{S})-2-amino-7-azabicyclo[2.2.1]heptane-7-carbonyl]-7-methoxy-1-methyl-benzimidazol-2-yl]-9,9,12-trimethyl-7-oxa-1,11,20-triazatricyclo[11.5.2.0^{16,19}]icosa-13(20),14,16(19),17-tetraen-10-one |
| 23 | 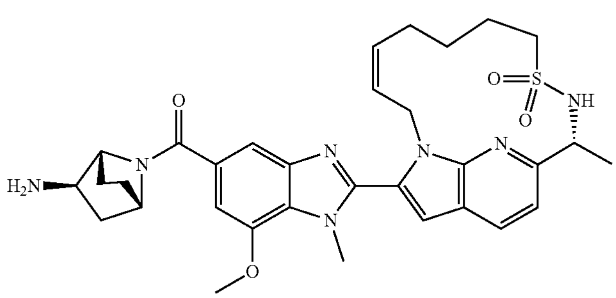 [SMILES: COc1cc(C(=O)N2[C@H]3CC[C@@H]2[C@H](N)C3)cc2nc(-c3cc4ccc5nc4n3C/C=C\CCCCS(=O)(=O)N[C@@H]5C)n(C)c12] | [(1~{R},2~{R},4~{S})-2-amino-7-azabicyclo[2.2.1]heptan-7-yl]-[7-methoxy-1-methyl-2-[(3~{Z},11~{R})-11-methyl-9,9-dioxo-9$1^{6}$-thia-1,10,19-triazatricyclo[10.5.2.0^{15,18}]nonadeca-3,12(19),13,15(18),16-pentaen-17-yl]benzimidazol-5-yl]methanone |

TABLE 1-continued

| Example | Structure | Name |
|---|---|---|
| 24 | 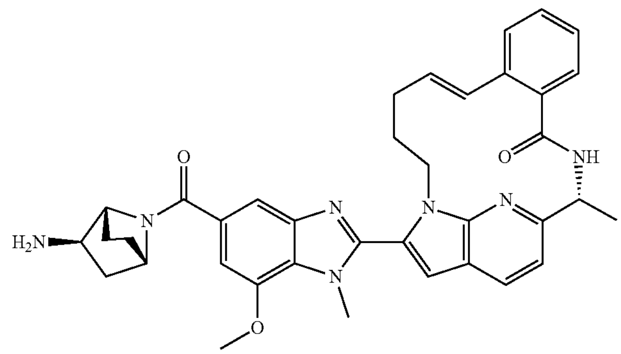 [SMILES: COc1cc(C(=O)N2[C@H]3CC[C@@H]2[C@H](N)C3)cc2nc(-c3cc4ccc5nc4n3CCC/C=C/c3ccccc3C(=O)N[C@@H]5C)n(C)c12] | (2~{R},11~{E})-17-[5-[(1~{R},2~{R},4~{S})-2-amino-7-azabicyclo[2.2.1]heptane-7-carbonyl]-7-methoxy-1-methyl-benzimidazol-2-yl]-2-methyl-3,16,22-triazatetracyclo[14.5.2.0^{5,10}.0^{19,23}]tricosa-1(22),5,7,9,11,17,19(23),20-octaen-4-one |
| 25 | 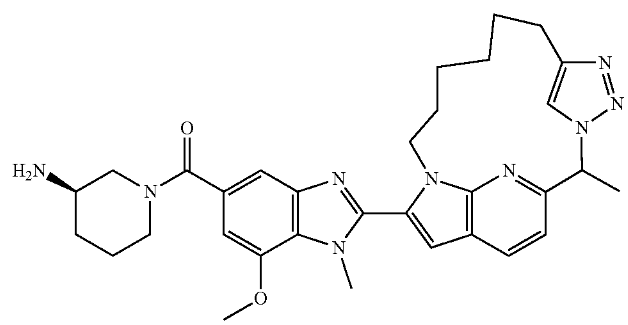 [SMILES: COc1cc(C(=O)N2CCC[C@@H](N)C2)cc2nc(-c3cc4ccc5nc4n3CCCCCCc3cn(nn3)C5C)n(C)c12] | [(3~{R})-3-amino-1-piperidyl]-[7-methoxy-1-methyl-2-(2-methyl-3,4,5,13,19-pentazatetracyclo[11.5.2.1^{3,6}.0^{16,20}]henicosa-1(19),4,6(21),14,16(20),17-hexaen-14-yl)benzimidazol-5-yl]methanone |
| 26 | 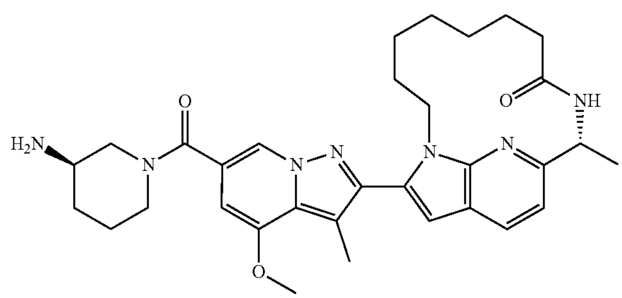 [SMILES: COc1cc(C(=O)N2CCC[C@@H](N)C2)cn2nc(-c3cc4ccc5nc4n3CCCCCCCC(=O)N[C@@H]5C)c(C)c12] | (11~{R})-17-[6-[(3~{R})-3-aminopiperidine-1-carbonyl]-4-methoxy-3-methyl-pyrazolo[1,5-a]pyridin-2-yl]-11-methyl-1,10,19-triazatricyclo[10.5.2.0^{15,18}]nonadeca-12(19),13,15(18),16-tetraen-9-one |
| 27 | 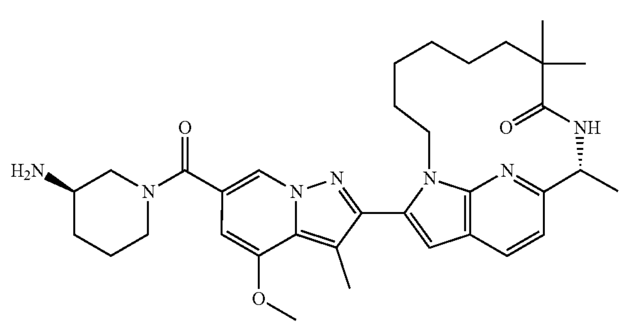 [SMILES: COc1cc(C(=O)N2CCC[C@@H](N)C2)cn2nc(-c3cc4ccc5nc4n3CCCCCCC(C)(C)C(=O)N[C@@H]5C)c(C)c12] | (11~{R})-17-[6-[(3~{R})-3-aminopiperidine-1-carbonyl]-4-methoxy-3-methyl-pyrazolo[1,5-a]pyridin-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 28 | 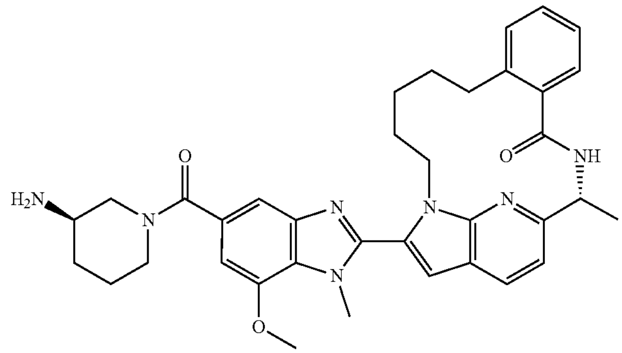 [SMILES: COc1cc(C(=O)N2CCC[C@@H](N)C2)cc2nc(-c3cc4ccc5nc4n3CCCCCc3ccccc3C(=O)N[C@@H]5C)n(C)c12] | (2~{R})-17-[5-[(3~{R})-3-aminopiperidine-1-carbonyl]-7-methoxy-1-methyl-benzimidazol-2-yl]-2-methyl-3,16,22-triazatetracyclo[14.5.2.0^{5,10}.0^{19,23}]tricosa-1(22),5,7,9,17,19(23),20-heptaen-4-one |
| 29 | 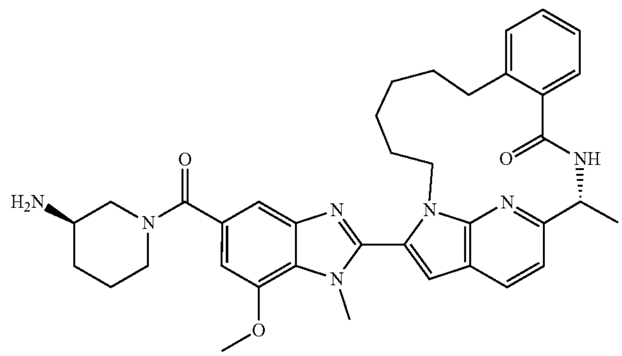 [SMILES: COc1cc(C(=O)N2CCC[C@@H](N)C2)cc2nc(-c3cc4ccc5nc4n3CCCCCCc3ccccc3C(=O)N[C@@H]5C)n(C)c12] | (2~{R})-18-[5-[(3~{R})-3-aminopiperidine-1-carbonyl]-7-methoxy-1-methyl-benzimidazol-2-yl]-2-methyl-3,17,23-triazatetracyclo[15.5.2.0^{5,10}.0^{20,24}]tetracosa-1(23),5,7,9,18,20(24),21-heptaen-4-one |
| 30 | 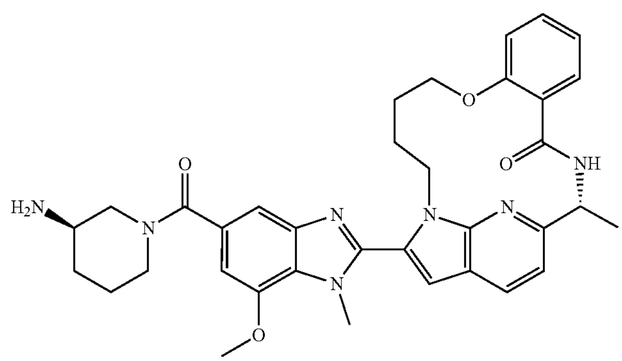 [SMILES: COc1cc(C(=O)N2CCC[C@@H](N)C2)cc2nc(-c3cc4ccc5nc4n3CCCCOc3ccccc3C(=O)N[C@@H]5C)n(C)c12] | (2~{R})-17-[5-[(3~{R})-3-aminopiperidine-1-carbonyl]-7-methoxy-1-methyl-benzimidazol-2-yl]-2-methyl-11-oxa-3,16,22-triazatetracyclo[14.5.2.0^{5,10}.0^{19,23}]tricosa-1(22),5,7,9,17,19(23),20-heptaen-4-one |
| 31 | 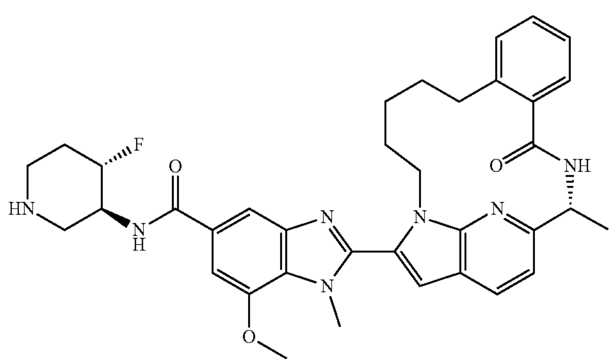 [SMILES: COc1cc(C(=O)N[C@H]2CNCC[C@@H]2F)cc2nc(-c3cc4ccc5nc4n3CCCCCc3ccccc3C(=O)N[C@@H]5C)n(C)c12] | ~{N}-[(3~{S},4~{S})-4-fluoro-3-piperidyl]-7-methoxy-1-methyl-2-[(2~{R})-2-methyl-4-oxo-3,16,22-triazatetracyclo[14.5.2.0^{5,10}.0^{19,23}]tricosa-1(22),5,7,9,17,19(23),20-heptaen-17-yl]benzimidazole-5-carboxamide |

TABLE 1-continued

| Example | Structure | Name |
|---|---|---|
| 32 | 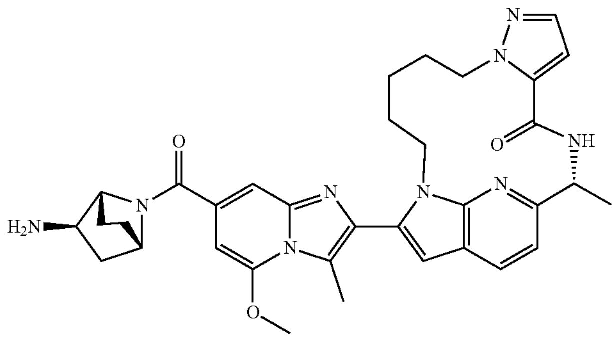 [SMILES: COc1cc(C(=O)N2[C@H]3CC[C@@H]2[C@H](N)C3)cc2nc(-c3cc4ccc5nc4n3CCCCCn3nccc3C(=O)N[C@@H]5C)c(C)n12] | (2~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-3,8,9,15,21-pentazatetracyclo[13.5.2.0^{5,9}.0^{18,22}]docosa-1(21),5,7,16,18(22),19-hexaen-4-one |
| 33 | 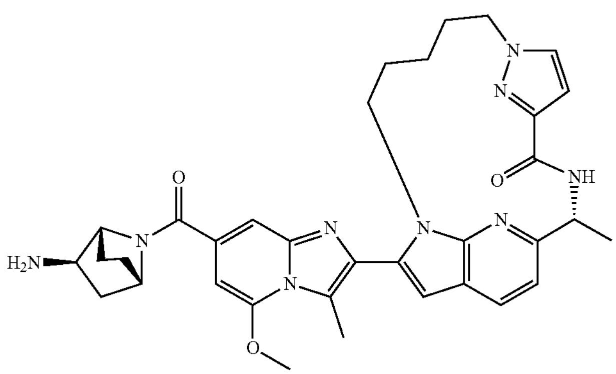 [SMILES: COc1cc(C(=O)N2[C@H]3CC[C@@H]2[C@H](N)C3)cc2nc(-c3cc4ccc5nc4n3CCCCCn3ccc(n3)C(=O)N[C@@H]5C)c(C)n12] | (2~{R})-15-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-3,8,14,20,22-pentazatetracyclo[12.5.2.1^{5,8}.0^{17,21}]docosa-1(20),5(22),6,15,17(21),18-hexaen-4-one |
| 34 | 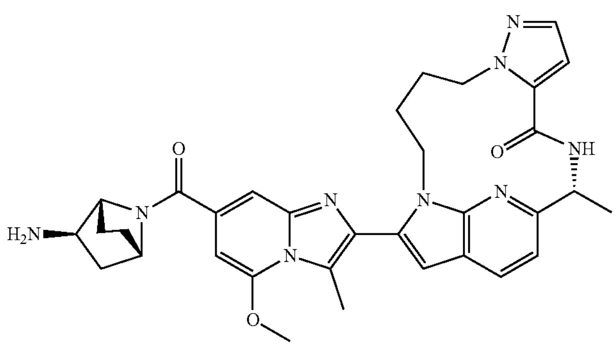 [SMILES: COc1cc(C(=O)N2[C@H]3CC[C@@H]2[C@H](N)C3)cc2nc(-c3cc4ccc5nc4n3CCCCn3nccc3C(=O)N[C@@H]5C)c(C)n12] | (2~{R})-15-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-3,8,9,14,20-pentazatetracyclo[12.5.2.0^{5,9}.0^{17,21}]henicosa-1(20),5,7,15,17(21),18-hexaen-4-one |
| 35 | 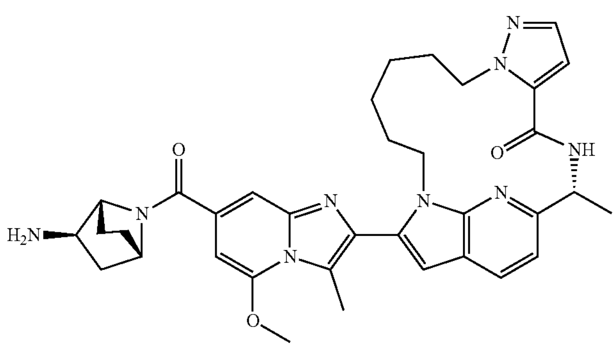 [SMILES: COc1cc(C(=O)N2[C@H]3CC[C@@H]2[C@H](N)C3)cc2nc(-c3cc4ccc5nc4n3CCCCCCn3nccc3C(=O)N[C@@H]5C)c(C)n12] | (2~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-3,8,9,16,22-pentazatetracyclo[14.5.2.0^{5,9}.0^{19,23}]tricosa-1(22),5,7,17,19(23),20-hexaen-4-one |

TABLE 1-continued

| Example | Structure | Name |
|---|---|---|
| 36 | 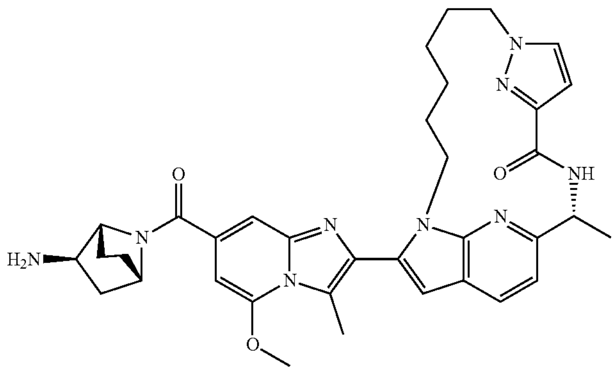 [SMILES: COc1cc(C(=O)N2[C@H]3CC[C@@H]2[C@H](N)C3)cc2nc(-c3cc4ccc5nc4n3CCCCCCn3ccc(n3)C(=O)N[C@@H]5C)c(C)n12] | (2~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-3,8,15,21,23-pentazatetracyclo[13.5.2.1ˆ{5,8}.0ˆ{18,22}]tricosa-1(21),5(23),6,16,18(22),19-hexaen-4-one |
| 37 | 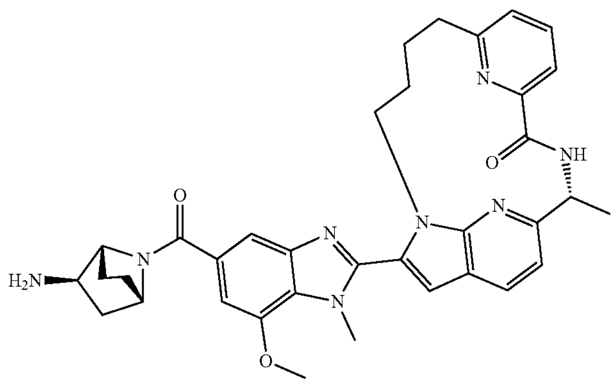 [SMILES: COc1cc(C(=O)N2[C@H]3CC[C@@H]2[C@H](N)C3)cc2nc(-c3cc4ccc5nc4n3CCCCc3cccc(n3)C(=O)N[C@@H]5C)n(C)c12] | (2~{R})-15-[5-[(1~{R},2~{R},4~{S})-2-amino-7-azabicyclo[2.2.1]heptane-7-carbonyl]-7-methoxy-1-methyl-benzimidazol-2-yl]-2-methyl-3,14,20,22-tetrazatetracyclo[12.5.2.1ˆ{5,9}.0ˆ{17,21}]docosa-1(20),5,7,9(22),15,17(21),18-heptaen-4-one |
| 38 | 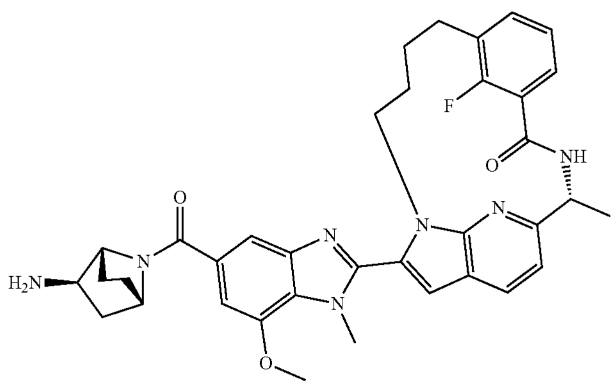 [SMILES: COc1cc(C(=O)N2[C@H]3CC[C@@H]2[C@H](N)C3)cc2nc(-c3cc4ccc5nc4n3CCCCc3cccc(c3F)C(=O)N[C@@H]5C)n(C)c12] | (2~{R})-15-[5-[(1~{R},2~{R},4~{S})-2-amino-7-azabicyclo[2.2.1]heptane-7-carbonyl]-7-methoxy-1-methyl-benzimidazol-2-yl]-22-fluoro-2-methyl-3,14,20-triazatetracyclo[12.5.2.1ˆ{5,9}.0ˆ{17,21}]docosa-1(20),5,7,9(22),15,17(21),18-heptaen-4-one |
| 39 | 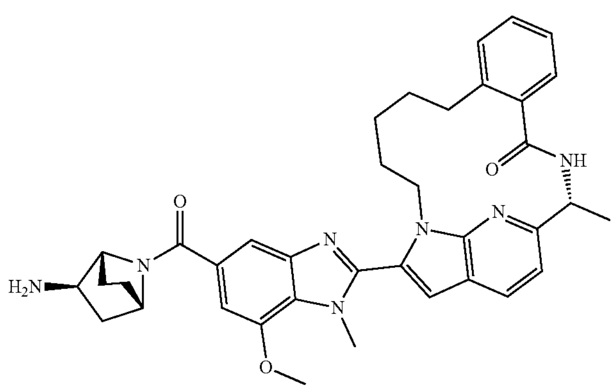 [SMILES: COc1cc(C(=O)N2[C@H]3CC[C@@H]2[C@H](N)C3)cc2nc(-c3cc4ccc5nc4n3CCCCCc3ccccc3C(=O)N[C@@H]5C)n(C)c12] | (2~{R})-17-[5-[(1~{R},2~{R},4~{S})-2-amino-7-azabicyclo[2.2.1]heptane-7-carbonyl]-7-methoxy-1-methyl-benzimidazol-2-yl]-2-methyl-3,16,22-triazatetracyclo[14.5.2.0ˆ{5,10}.0ˆ{19,23}]tricosa-1(22),5,7,9,17,19(23),20-heptaen-4-one |

TABLE 1-continued

| Example | Structure | Name |
|---|---|---|
| 40 | 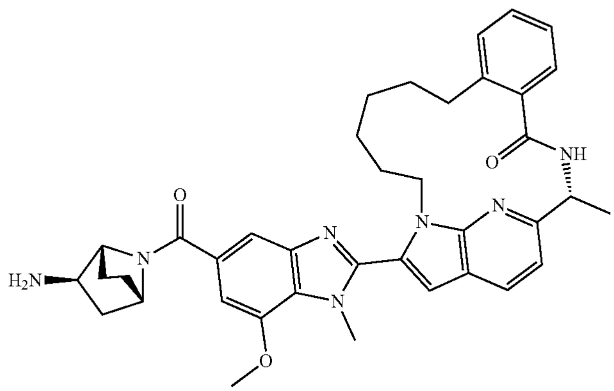 [SMILES: COc1cc(C(=O)N2[C@H]3CC[C@@H]2[C@H](N)C3)cc2nc(-c3cc4ccc5nc4n3CCCCCCc3ccccc3C(=O)N[C@@H]5C)n(C)c12] | (2~{R})-18-[5-[(1~{R},2~{R},4~{S})-2-amino-7-azabicyclo[2.2.1]heptane-7-carbonyl]-7-methoxy-1-methyl-benzimidazol-2-yl]-2-methyl-3,17,23-triazatetracyclo[15.5.2.0^{5,10}.0^{20,24}]tetracosa-1(23),5,7,9,18,20(24),21-heptaen-4-one |
| 41 | 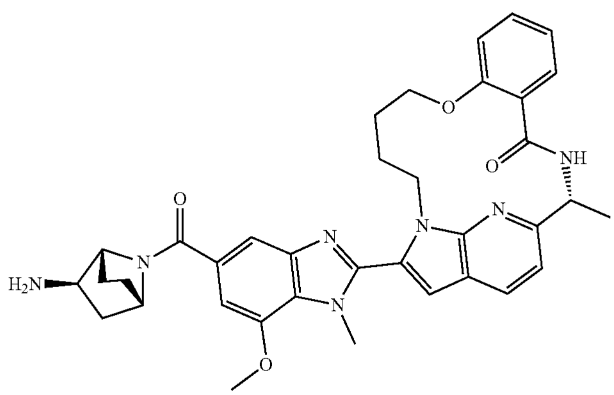 [SMILES: COc1cc(C(=O)N2[C@H]3CC[C@@H]2[C@H](N)C3)cc2nc(-c3cc4ccc5nc4n3CCCCOc3ccccc3C(=O)N[C@@H]5C)n(C)c12] | (2~{R})-17-[5-[(1~{R},2~{R},4~{S})-2-amino-7-azabicyclo[2.2.1]heptane-7-carbonyl]-7-methoxy-1-methyl-benzimidazol-2-yl]-2-methyl-11-oxa-3,16,22-triazatetracyclo[14.5.2.0^{5,10}.0^{19,23}]tricosa-1(22),5,7,9,17,19(23),20-heptaen-4-one |
| 42 | 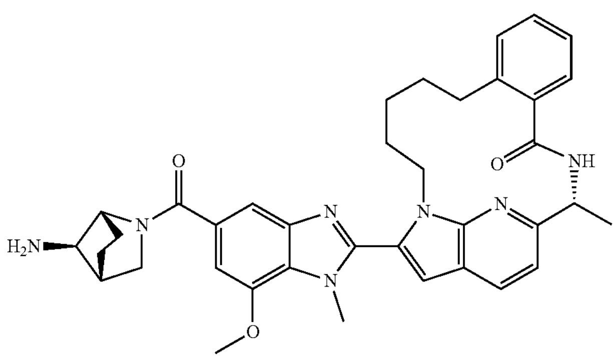 [SMILES: COc1cc(C(=O)N2C[C@H]3CC[C@@H]2[C@@H]3N)cc2nc(-c3cc4ccc5nc4n3CCCCCc3ccccc3C(=O)N[C@@H]5C)n(C)c12] | (2~{R})-17-[5-[(1~{R},4~{R},7~{R})-7-amino-2-azabicyclo[2.2.1]heptane-2-carbonyl]-7-methoxy-1-methyl-benzimidazol-2-yl]-2-methyl-3,16,22-triazatetracyclo[14.5.2.0^{5,10}.0^{19,23}]tricosa-1(22),5,7,9,17,19(23),20-heptaen-4-one |
| 43 | 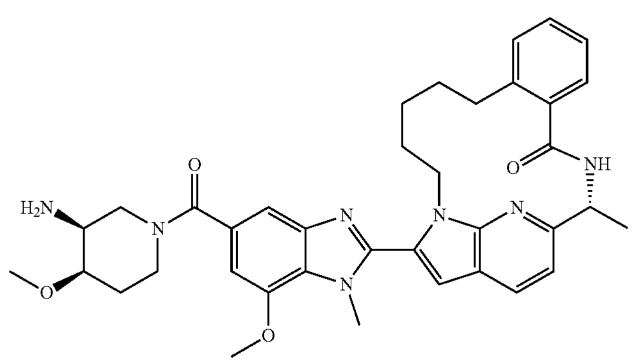 | (2~{R})-17-[5-[(3~{S},4~{R})-3-amino-4-methoxy-piperidine-1-carbonyl]-7-methoxy-1-methyl-benzimidazol-2-yl]-2-methyl-3,16,22-triazatetracyclo[14.5.2.0^{5,10}.0^{19,23}]tricosa-1(22),5,7,9,17,19(23),20-heptaen-4-one |

TABLE 1-continued

| Example | Structure | Name |
|---|---|---|
| 44 | 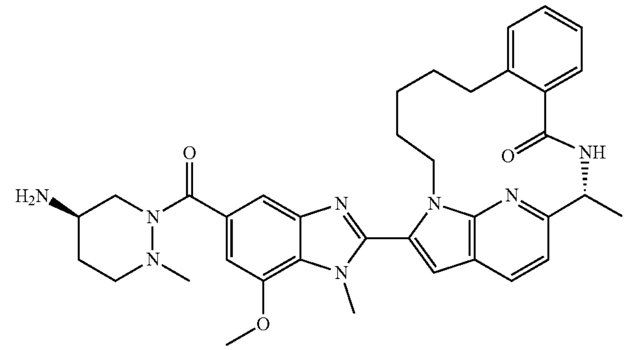 [SMILES: COc1cc(C(=O)N2C[C@H](N)CCN2C)cc2nc(-c3cc4ccc5nc4n3CCCCCc3ccccc3C(=O)N[C@@H]5C)n(C)c12] | (2~{R})-17-[5-[(5~{R})-5-amino-2-methyl-hexahydropyridazine-1-carbonyl]-7-methoxy-1-methyl-benzimidazol-2-yl]-2-methyl-3,16,22-triazatetracyclo[14.5.2.0^{5,10}.0^{19,23}]tricosa-1(22),5,7,9,17,19(23),20-heptaen-4-one |
| 45 | 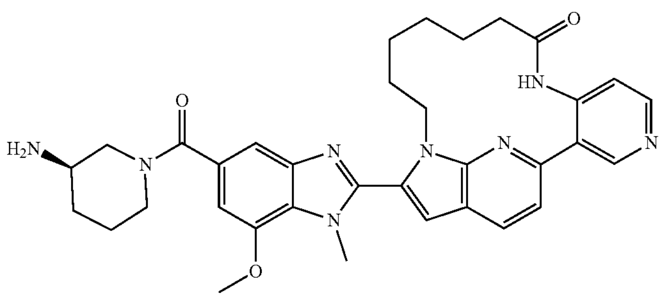 [SMILES: COc1cc(C(=O)N2CCC[C@@H](N)C2)cc2nc(-c3cc4ccc5nc4n3CCCCCCC(=O)Nc3ccncc3-5)n(C)c12] | 17-[5-[(3~{R})-3-aminopiperidine-1-carbonyl]-7-methoxy-1-methyl-benzimidazol-2-yl]-4,8,16,22-tetrazatetracyclo[14.5.2.0^{2,7}.0^{19,23}]tricosa-1(22),2,4,6,17,19(23),20-heptaen-9-one |
| 46 | 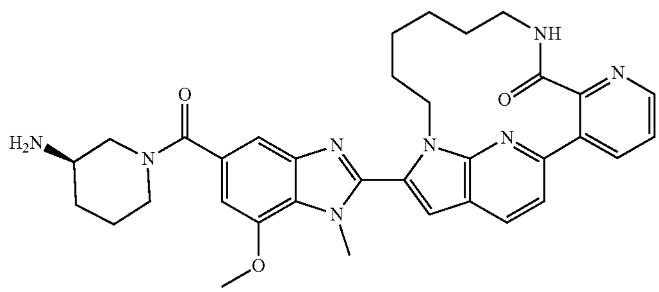 | 17-[5-[(3~{R})-3-aminopiperidine-1-carbonyl]-7-methoxy-1-methyl-benzimidazol-2-yl]-6,9,16,22-tetrazatetracyclo[14.5.2.0^{2,7}.0^{19,23}]tricosa-1(22),2,4,6,17,19(23),20-heptaen-8-one |
| 47 | 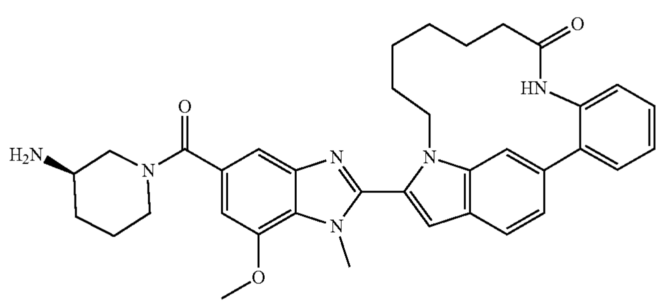 [SMILES: COc1cc(C(=O)N2CCC[C@@H](N)C2)cc2nc(-c3cc4ccc5cc4n3CCCCCCC(=O)Nc3ccccc3-5)n(C)c12] | 17-[5-[(3~{R})-3-aminopiperidine-1-carbonyl]-7-methoxy-1-methyl-benzimidazol-2-yl]-8,16-diazatetracyclo[14.5.2.0^{2,7}.0^{19,23}]tricosa-1(22),2,4,6,17,19(23),20-heptaen-9-one |
| 48 | 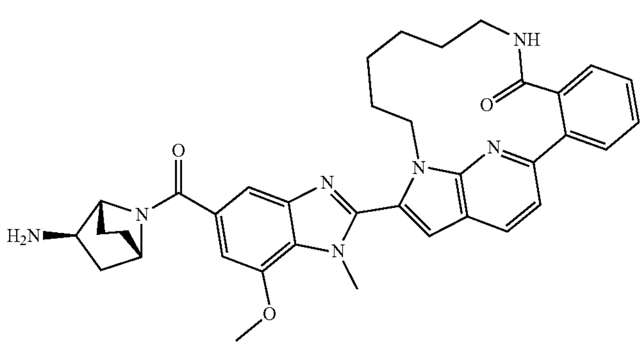 [SMILES: COc1cc(C(=O)N2[C@H]3CC[C@@H]2[C@H](N)C3)cc2nc(-c3cc4ccc5nc4n3CCCCCCNC(=O)c3ccccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-9,16,22-triazatetracyclo[14.5.2.0^{2,7}.0^{19,23}]tricosa-1(22),2,4,6,17,19(23),20-heptaen-8-one |

TABLE 1-continued

| Example | Structure | Name |
|---|---|---|
| 49 | 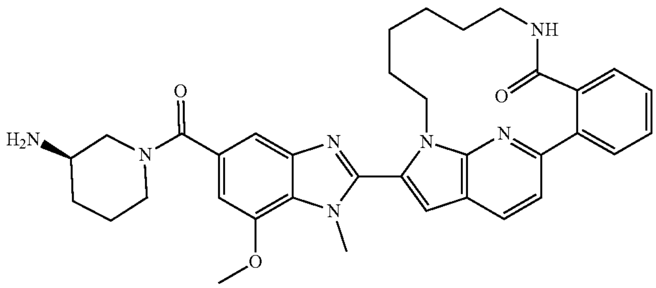 [SMILES: COc1cc(C(=O)N2CCC[C@@H](N)C2)cc2nc(-c3cc4ccc5nc4n3CCCCCCNC(=O)c3ccccc3-5)n(C)c12] | 17-[5-[(3~{R})-3-aminopiperidine-1-carbonyl]-7-methoxy-1-methyl-benzimidazol-2-yl]-9,16,22-triazatetracyclo[14.5.2.0^{2,7}.0^{19,23}]tricosa-1(22),2,4,6,17,19(23),20-heptaen-8-one |
| 50 | 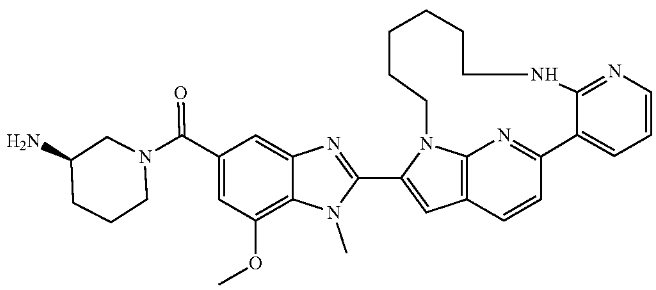 [SMILES: COc1cc(C(=O)N2CCC[C@@H](N)C2)cc2nc(-c3cc4ccc5nc4n3CCCCCCNc3ncccc3-5)n(C)c12] | [(3~{R})-3-amino-1-piperidyl]-[7-methoxy-1-methyl-2-(6,8,15,21-tetrazatetracyclo[13.5.2.0^{2,7}.0^{18,22}]docosa-1(21),2,4,6,16,18(22),19-heptaen-16-yl)benzimidazol-5-yl]methanone |
| 51 | 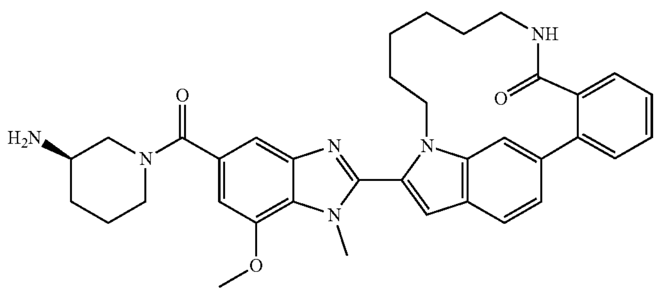 [SMILES: COc1cc(C(=O)N2CCC[C@@H](N)C2)cc2nc(-c3cc4ccc5cc4n3CCCCCCNC(=O)c3ccccc3-5)n(C)c12] | 17-[5-[(3~{R})-3-aminopiperidine-1-carbonyl]-7-methoxy-1-methyl-benzimidazol-2-yl]-9,16-diazatetracyclo[14.5.2.0^{2,7}.0^{19,23}]tricosa-1(22),2,4,6,17,19(23),20-heptaen-8-one |
| 52 | 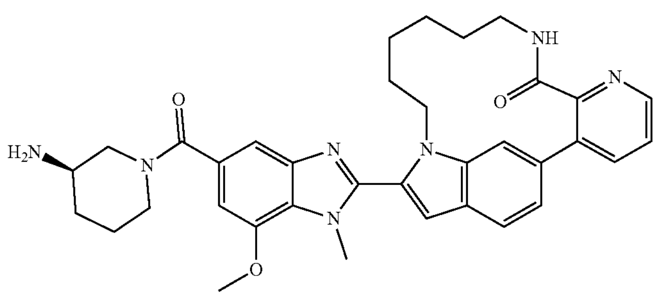 [SMILES: COc1cc(C(=O)N2CCC[C@@H](N)C2)cc2nc(-c3cc4ccc5cc4n3CCCCCCNC(=O)c3ncccc3-5)n(C)c12] | 17-[5-[(3~{R})-3-aminopiperidine-1-carbonyl]-7-methoxy-1-methyl-benzimidazol-2-yl]-6,9,16-triazatetracyclo[14.5.2.0^{2,7}.0^{19,23}]tricosa-1(22),2,4,6,17,19(23),20-heptaen-8-one |
| 53 | 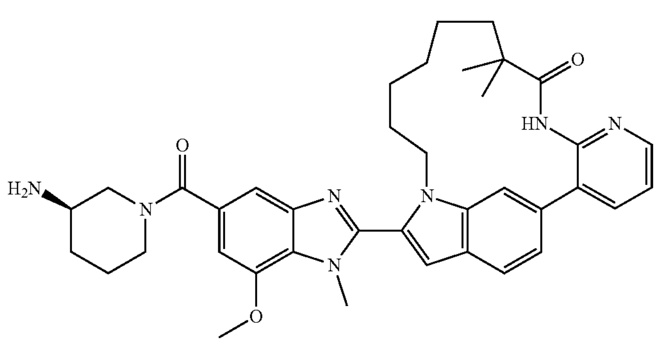 [SMILES: COc1cc(C(=O)N2CCC[C@@H](N)C2)cc2nc(-c3cc4ccc5cc4n3CCCCCCC(C)(C)C(=O)Nc3ncccc3-5)n(C)c12] | 18-[5-[(3~{R})-3-aminopiperidine-1-carbonyl]-7-methoxy-1-methyl-benzimidazol-2-yl]-10,10-dimethyl-6,8,17-triazatetracyclo[15.5.2.0^{2,7}.0^{20,24}]tetracosa-1(23),2,4,6,18,20(24),21-heptaen-9-one |

TABLE 1-continued

| Example | Structure | Name |
|---|---|---|
| 54 | 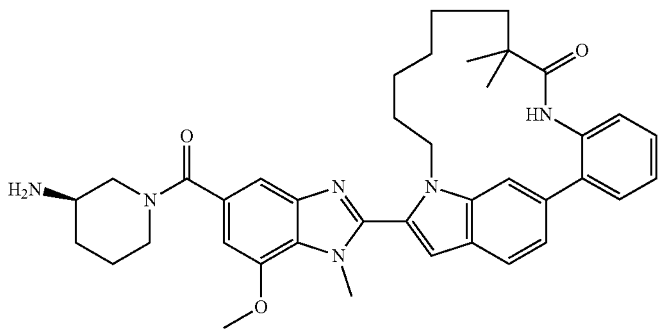 [SMILES: COc1cc(C(=O)N2CCC[C@@H](N)C2)cc2nc(-c3cc4ccc5cc4n3CCCCCCC(C)(C)C(=O)Nc3ccccc3-5)n(C)c12] | 18-[5-[(3~{R})-3-aminopiperidine-1-carbonyl]-7-methoxy-1-methyl-benzimidazol-2-yl]-10,10-dimethyl-8,17-diazatetracyclo[15.5.2.0^{2,7}.0^{20,24}]tetracosa-1(23),2,4,6,18,20(24),21-heptaen-9-one |
| 55 | 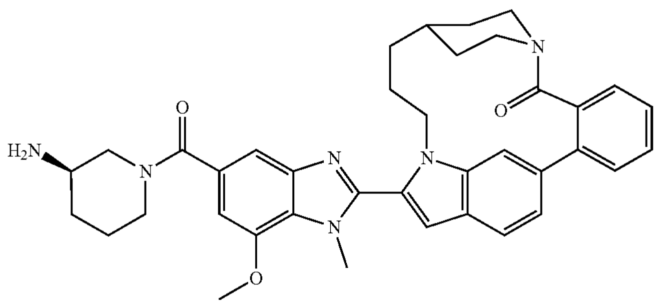 [SMILES: COc1cc(C(=O)N2CCC[C@@H](N)C2)cc2nc(-c3cc4ccc5cc4n3CCCC3CCN(CC3)C(=O)c3ccccc3-5)n(C)c12] | 17-[5-[(3~{R})-3-aminopiperidine-1-carbonyl]-7-methoxy-1-methyl-benzimidazol-2-yl]-9,16-diazapentacyclo[14.5.2.2^{9,12}.0^{2,7}.0^{19,23}]pentacosa-1(22),2,4,6,17,19(23),20-heptaen-8-one |
| 56 | 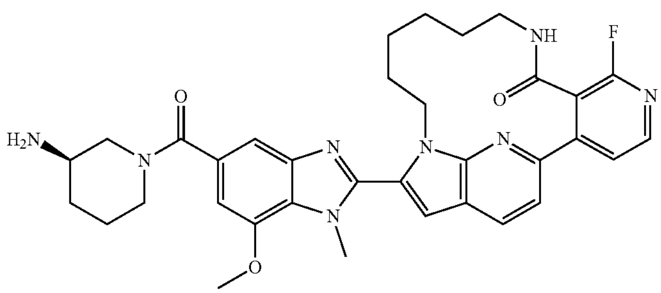 [SMILES: COc1cc(C(=O)N2CCC[C@@H](N)C2)cc2nc(-c3cc4ccc5nc4n3CCCCCCNC(=O)c3c-5ccnc3F)n(C)c12] | 17-[5-[(3~{R})-3-aminopiperidine-1-carbonyl]-7-methoxy-1-methyl-benzimidazol-2-yl]-6-fluoro-5,9,16,22-tetrazatetracyclo[14.5.2.0^{2,7}.0^{19,23}]tricosa-1(22),2,4,6,17,19(23),20-heptaen-8-one |
| 57 | 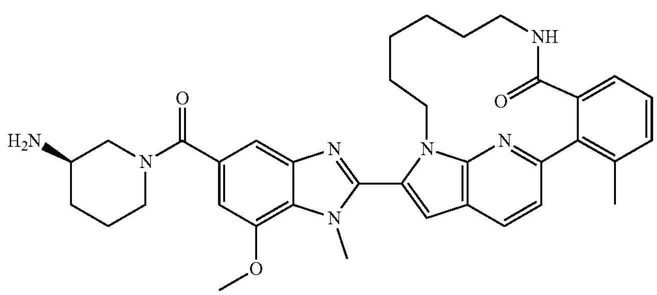 [SMILES: COc1cc(C(=O)N2CCC[C@@H](N)C2)cc2nc(-c3cc4ccc5nc4n3CCCCCCNC(=O)c3cccc(C)c3-5)n(C)c12] | 17-[5-[(3~{R})-3-aminopiperidine-1-carbonyl]-7-methoxy-1-methyl-benzimidazol-2-yl]-3-methyl-9,16,22-triazatetracyclo[14.5.2.0^{2,7}.0^{19,23}]tricosa-1(22),2,4,6,17,19(23),20-heptaen-8-one |
| 58 | 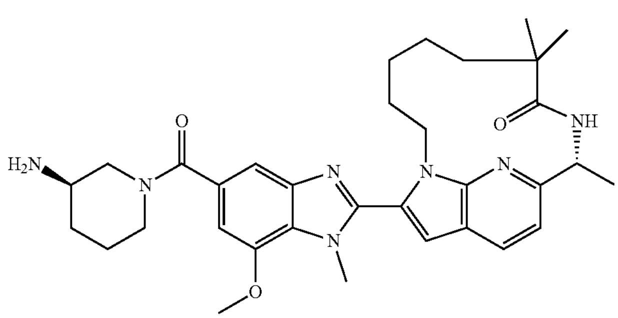 [SMILES: COc1cc(C(=O)N2CCC[C@@H](N)C2)cc2nc(-c3cc4ccc5nc4n3CCCCCC(C)(C)C(=O)N[C@@H]5C)n(C)c12] | (10~{R})-16-[5-[(3~{R})-3-aminopiperidine-1-carbonyl]-7-methoxy-1-methyl-benzimidazol-2-yl]-7,7,10-trimethyl-1,9,18-triazatricyclo[9.5.2.0^{14,17}]octadeca-11(18),12,14(17),15-tetraen-8-one |

TABLE 1-continued

| Example | Structure | Name |
| --- | --- | --- |
| 59 | 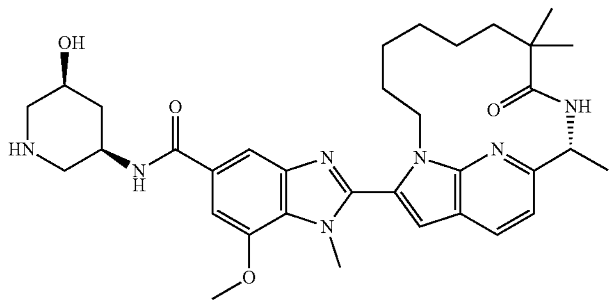 | ~{N}-[(3~{R},5~{S})-5-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 60 | 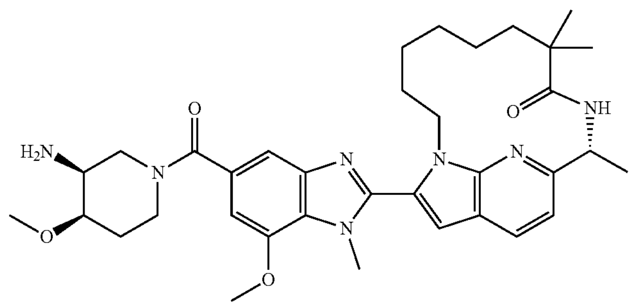 | (11~{R})-17-[5-[(3~{S},4~{R})-3-amino-4-methoxy-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 61 | 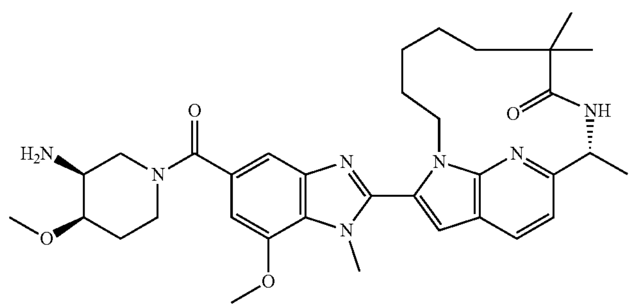 | (10~{R})-16-[5-[(3~{S},4~{R})-3-amino-4-methoxy-piperidine-1-carbonyl]-7-methoxy-1-methyl-benzimidazol-2-yl]-7,7,10-trimethyl-1,9,18-triazatricyclo[9.5.2.0^{14,17}]octadeca-11(18),12,14(17),15-tetraen-8-one |
| 62 | 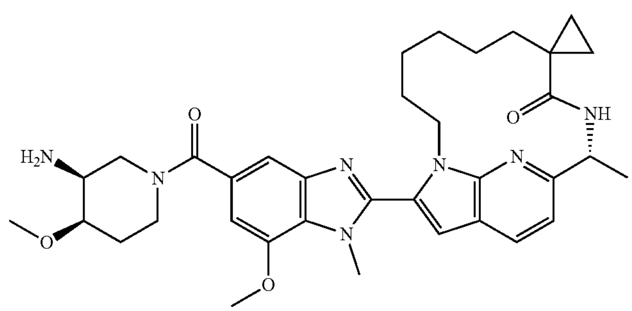 | (11~{R})-17-[5-[(3~{S},4~{R})-3-amino-4-methoxy-piperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |
| 63 | 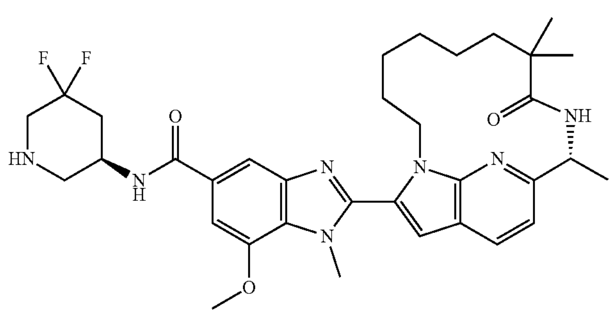 [SMILES: COc1cc(C(=O)N[C@H]2CNCC(F)(F)C2)cc2nc(-c3cc4ccc5nc4n3CCCCCCC(C)(C)C(=O)N[C@@H]5C)n(C)c12] | ~{N}-[(3~{R})-5,5-difluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 64 | 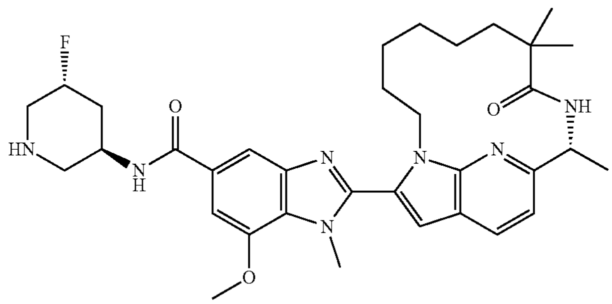 [SMILES: COc1cc(C(=O)N[C@H]2CNC[C@H](F)C2)cc2nc(-c3cc4ccc5nc4n3CCCCCCC(C)(C)C(=O)N[C@@H]5C)n(C)c12] | ~{N}-[(3~{R},5~{R})-5-fluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 65 | 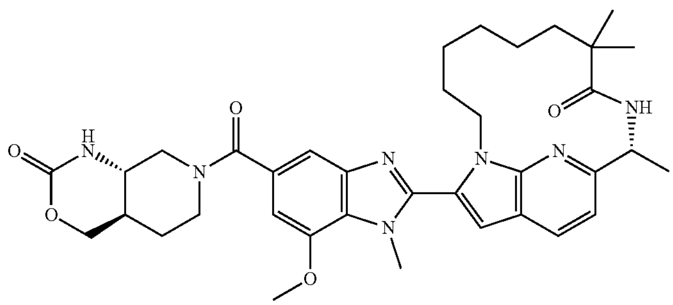 [SMILES: COc1cc(C(=O)N2CC[C@H]3COC(=O)N[C@@H]3C2)cc2nc(-c3cc4ccc5nc4n3CCCCCCC(C)(C)C(=O)N[C@@H]5C)n(C)c12] | (4~{a}~{R},8~{a}~{S})-7-[7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carbonyl]-4,4~{a},5,6,8,8~{a}-hexahydro-1~{H}-pyrido[3,4-d][1,3]oxazin-2-one |
| 66 | 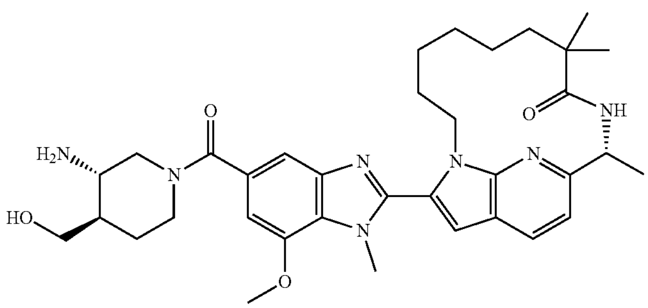 [SMILES: COc1cc(C(=O)N2CC[C@@H](CO)[C@H](N)C2)cc2nc(-c3cc4ccc5nc4n3CCCCCCC(C)(C)C(=O)N[C@@H]5C)n(C)c12] | (11~{R})-17-[5-[(3~{S},4~{R})-3-amino-4-(hydroxymethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 67 | 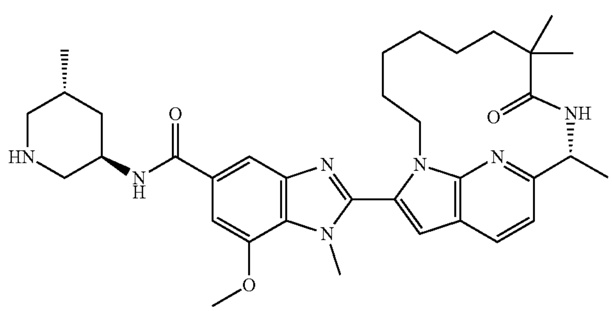 [SMILES: COc1cc(C(=O)N[C@H]2CNC[C@H](C)C2)cc2nc(-c3cc4ccc5nc4n3CCCCCCC(C)(C)C(=O)N[C@@H]5C)n(C)c12] | 7-methoxy-1-methyl-~{N}-[(3~{R},5~{R})-5-methyl-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 68 | 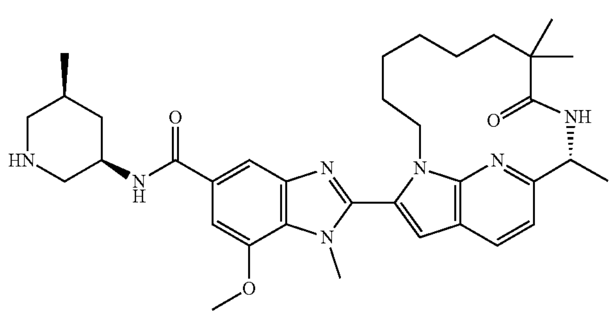 [SMILES: COc1cc(C(=O)N[C@H]2CNC[C@@H](C)C2)cc2nc(-c3cc4ccc5nc4n3CCCCCCC(C)(C)C(=O)N[C@@H]5C)n(C)c12] | 7-methoxy-1-methyl-~{N}-[(3~{R},5~{S})-5-methyl-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 69 | 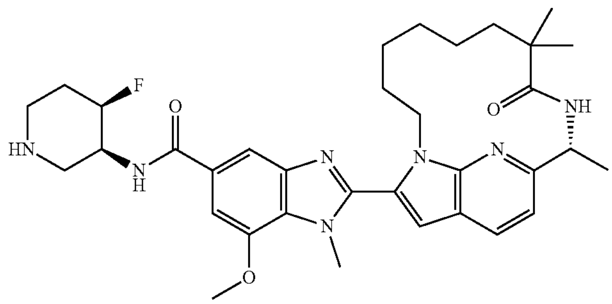 [SMILES: COc1cc(C(=O)N[C@H]2CNCC[C@H]2F)cc2nc(-c3cc4ccc5nc4n3CCCCCCC(C)(C)C(=O)N[C@@H]5C)n(C)c12] | ~{N}-[(3~{S},4~{R})-4-fluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 70 | 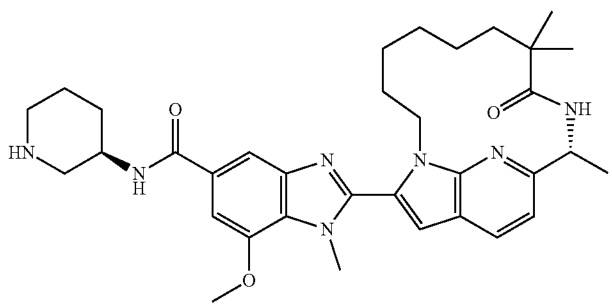 [SMILES: COc1cc(C(=O)N[C@@H]2CCCNC2)cc2nc(-c3cc4ccc5nc4n3CCCCCCC(C)(C)C(=O)N[C@@H]5C)n(C)c12] | 7-methoxy-1-methyl-~{N}-[(3~{R})-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 71 | 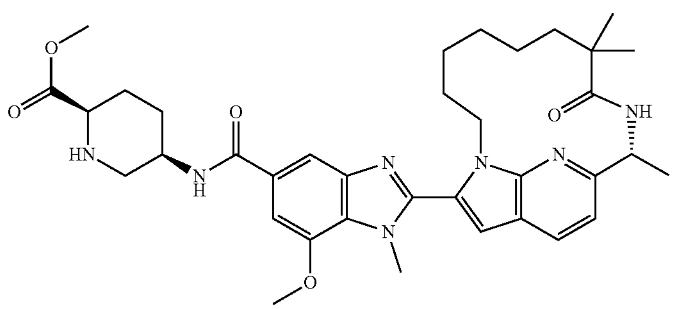 [SMILES: COC(=O)[C@H]1CC[C@@H](NC(=O)c2cc(OC)c3c(c2)nc(-c2cc4ccc5nc4n2CCCCCCC(C)(C)C(=O)N[C@@H]5C)n3C)CN1] | methyl (2~{R},5~{R})-5-[[7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carbonyl]amino]piperidine-2-carboxylate |
| 72 | 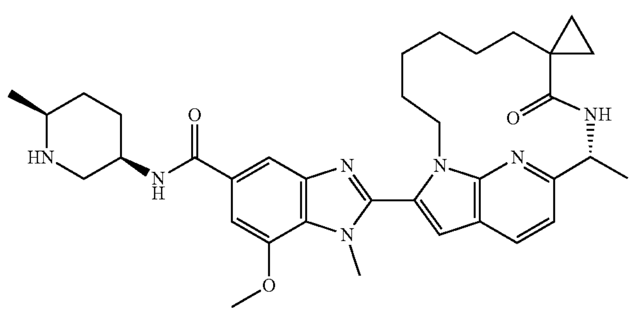 | 7-methoxy-1-methyl-2-[(11~{R})-11-methyl-9-oxo-spiro[1,10,19-triazatricyclo[10.5.2.0^{15,18}]nonadeca-12(19),13,15(18),16-tetraene-8,1'-cyclopropane]-17-yl]-~{N}-[(3~{R},6~{S})-6-methyl-3-piperidyl]benzimidazole-5-carboxamide |
| 73 | 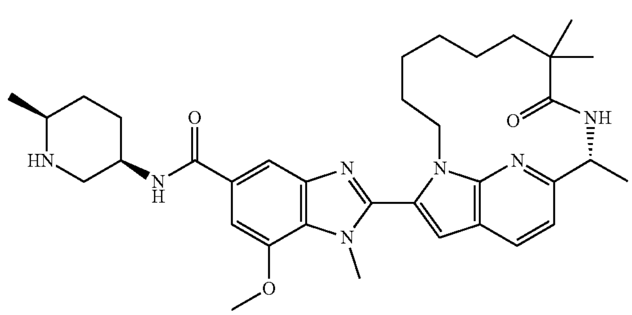 | 7-methoxy-1-methyl-~{N}-[(3~{R},6~{S})-6-methyl-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 74 | 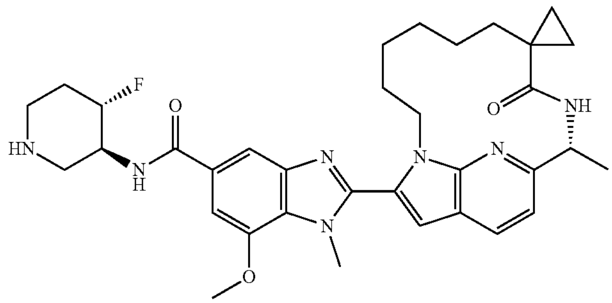 [SMILES: COc1cc(C(=O)N[C@H]2CNCC[C@@H]2F)cc2nc(-c3cc4ccc5nc4n3CCCCCCC3(CC3)C(=O)N[C@@H]5C)n(C)c12] | ~{N}-[(3~{S},4~{S})-4-fluoro-3-piperidyl]-7-methoxy-1-methyl-2-[(11~{R})-11-methyl-9-oxo-spiro[1,10,19-triazatricyclo[10.5.2.0^{15,18}]nonadeca-12(19),13,15(18),16-tetraene-8,1'-cyclopropane]-17-yl]benzimidazole-5-carboxamide |
| 75 | 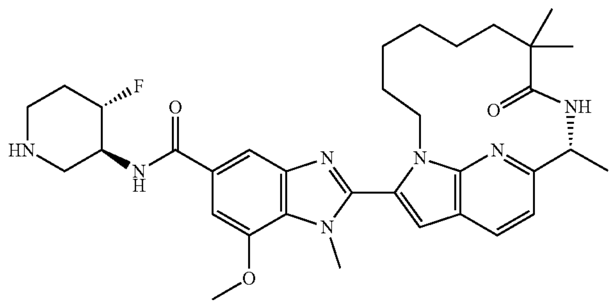 | ~{N}-[(3~{S},4~{S})-4-fluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 76 | 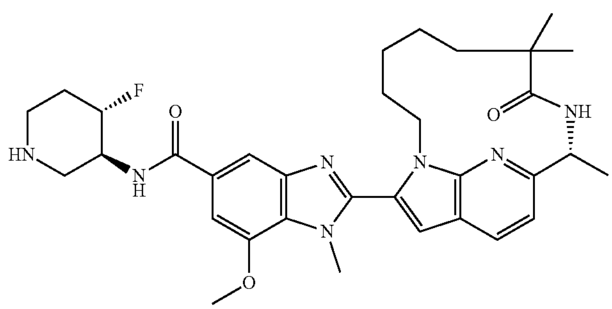 [SMILES: COc1cc(C(=O)N[C@H]2CNCC[C@@H]2F)cc2nc(-c3cc4ccc5nc4n3CCCCCC(C)(C)C(=O)N[C@@H]5C)n(C)c12] | ~{N}-[(3~{S},4~{S})-4-fluoro-3-piperidyl]-7-methoxy-1-methyl-2-[(10~{R})-7,7,10-trimethyl-8-oxo-1,9,18-triazatricyclo[9.5.2.0^{14,17}]octadeca-11(18),12,14(17),15-tetraen-16-yl]benzimidazole-5-carboxamide |
| 77 | 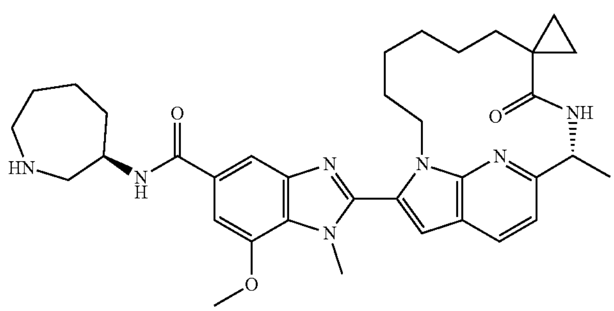 [SMILES: COc1cc(C(=O)N[C@@H]2CCCCNC2)cc2nc(-c3cc4ccc5nc4n3CCCCCCC3(CC3)C(=O)N[C@@H]5C)n(C)c12] | ~{N}-[(3~{R})-azepan-3-yl]-7-methoxy-1-methyl-2-[(11~{R})-11-methyl-9-oxo-spiro[1,10,19-triazatricyclo[10.5.2.0^{15,18}]nonadeca-12(19),13,15(18),16-tetraene-8,1'-cyclopropane]-17-yl]benzimidazole-5-carboxamide |
| 78 | 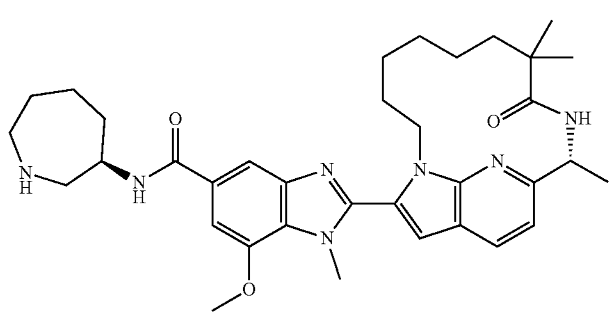 [SMILES: COc1cc(C(=O)N[C@@H]2CCCCNC2)cc2nc(-c3cc4ccc5nc4n3CCCCCCC(C)(C)C(=O)N[C@@H]5C)n(C)c12] | ~{N}-[(3~{R})-azepan-3-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 79 | 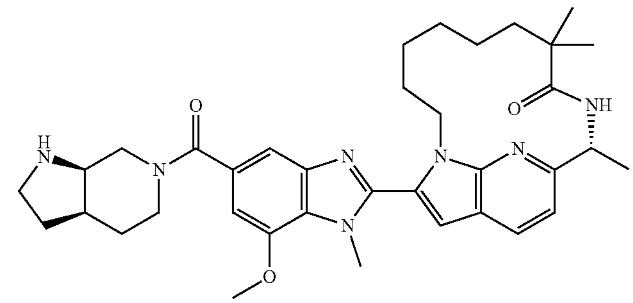 [SMILES: COc1cc(C(=O)N2CC[C@H]3CCN[C@H]3C2)cc2nc(-c3cc4ccc5nc4n3CCCCCCC(C)(C)C(=O)N[C@@H]5C)n(C)c12] | (11~{R})-17-[5-[(3~{a}~{R},7~{a}~{R})-1,2,3,3~{a},4,5,7,7~{a}-octahydropyrrolo[2,3-c]pyridine-6-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 80 | 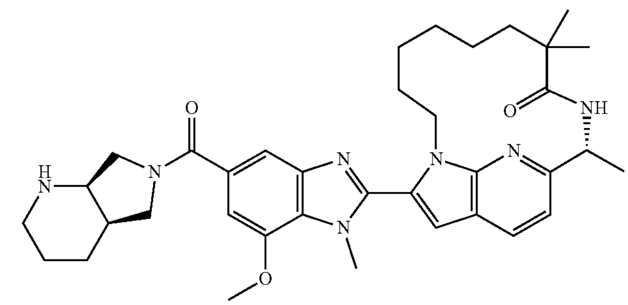 [SMILES: COc1cc(C(=O)N2C[C@H]3CCCN[C@H]3C2)cc2nc(-c3cc4ccc5nc4n3CCCCCCC(C)(C)C(=O)N[C@@H]5C)n(C)c12] | (11~{R})-17-[5-[(4~{a}~{R},7~{a}~{R})-1,2,3,4,4~{a},5,7,7~{a}-octahydropyrrolo[3,4-b]pyridine-6-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 81 | 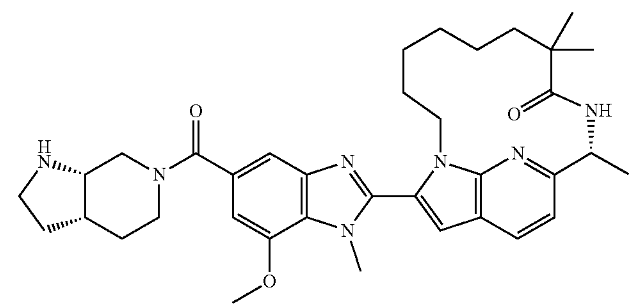 [SMILES: COc1cc(C(=O)N2CC[C@@H]3CCN[C@@H]3C2)cc2nc(-c3cc4ccc5nc4n3CCCCCCC(C)(C)C(=O)N[C@@H]5C)n(C)c12] | (11~{R})-17-[5-[(3~{a}~{S},7~{a}~{S})-1,2,3,3~{a},4,5,7,7~{a}-octahydropyrrolo[2,3-c]pyridine-6-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 82 | 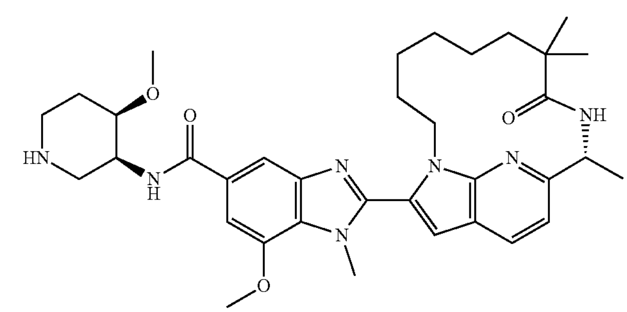 | 7-methoxy-~{N}-[(3~{S},4~{R})-4-methoxy-3-piperidyl]-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 83 | 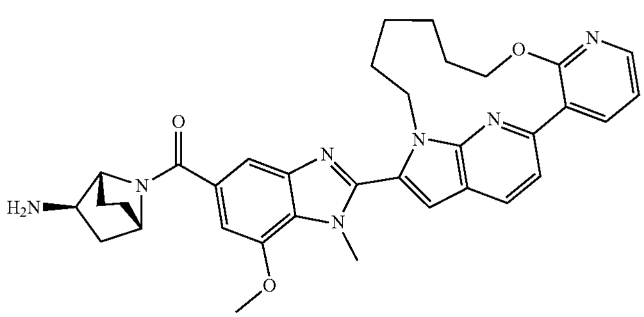 [SMILES: COc1cc(C(=O)N2[C@H]3CC[C@@H]2[C@H](N)C3)cc2nc(-c3cc4ccc5nc4n3CCCCCCOc3ncccc3-5)n(C)c12] | [(1~{R},2~{R},4~{S})-2-amino-7-azabicyclo[2.2.1]heptan-7-yl]-[7-methoxy-1-methyl-2-(8-oxa-6,15,21-triazatetracyclo[13.5.2.0^{2,7}.0^{18,22}]docosa-1(21),2,4,6,16,18(22),19-heptaen-16-yl)benzimidazol-5-yl]methanone |

TABLE 1-continued

| Example | Structure | Name |
|---|---|---|
| 84 | 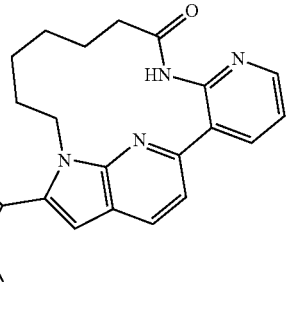 | 17-[5-[(1~{R},2~{R},4~{S})-2-amino-7-azabicyclo[2.2.1]heptane-7-carbonyl]-7-methoxy-1-methyl-benzimidazol-2-yl]-6,8,16,22-tetrazatetracyclo[14.5.2.0^{2,7}.0^{19,23}]tricosa-1(22),2,4,6,17,19(23),20-heptaen-9-one |
| 85 | 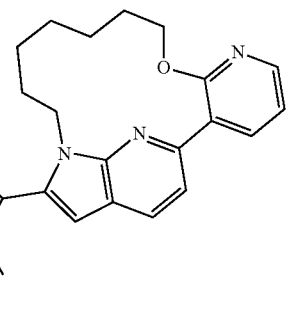 | [(1~{R},2~{R},4~{S})-2-amino-7-azabicyclo[2.2.1]heptan-7-yl]-[7-methoxy-1-methyl-2-(8-oxa-6,16,22-triazatetracyclo[14.5.2.0^{2,7}.0^{19,23}]tricosa-1(22),2,4,6,17,19(23),20-heptaen-17-yl)benzimidazol-5-yl]methanone |
| 86 | 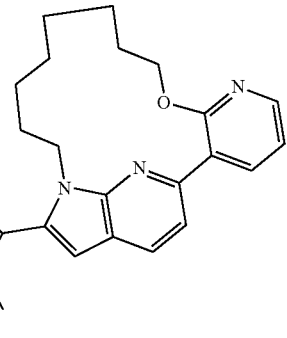 | [(1~{R},2~{R},4~{S})-2-amino-7-azabicyclo[2.2.1]heptan-7-yl]-[7-methoxy-1-methyl-2-(8-oxa-6,17,23-triazatetracyclo[15.5.2.0^{2,7}.0^{20,24}]tetracosa-1(23),2,4,6,18,20(24),21-heptaen-18-yl)benzimidazol-5-yl]methanone |
| 87 | 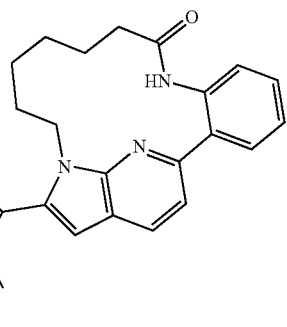 | 17-[5-[(1~{R},2~{R},4~{S})-2-amino-7-azabicyclo[2.2.1]heptane-7-carbonyl]-7-methoxy-1-methyl-benzimidazol-2-yl]-8,16,22-triazatetracyclo[14.5.2.0^{2,7}.0^{19,23}]tricosa-1(22),2,4,6,17,19(23),20-heptaen-9-one |

TABLE 1-continued

| Example | Structure | Name |
|---|---|---|
| 88 | 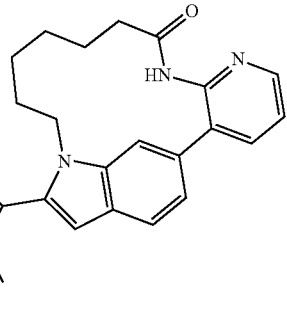 | 17-[5-[(1~{R},2~{R},4~{S})-2-amino-7-azabicyclo[2.2.1]heptane-7-carbonyl]-7-methoxy-1-methyl-benzimidazol-2-yl]-6,8,16-triazatetracyclo[14.5.2.0^{2,7}.0^{19,23}]tricosa-1(22),2,4,6,17,19(23),20-heptaen-9-one |
| 89 | 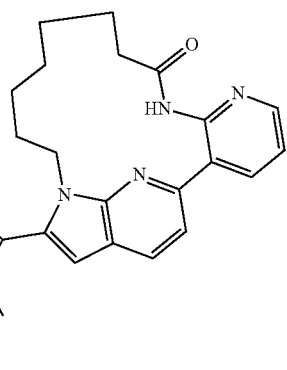 | 18-[5-[(1~{R},2~{R},4~{S})-2-amino-7-azabicyclo[2.2.1]heptane-7-carbonyl]-7-methoxy-1-methyl-benzimidazol-2-yl]-6,8,17,23-tetrazatetracyclo[15.5.2.0^{2,7}.0^{20,24}]tetracosa-1(23),2,4,6,18,20(24),21-heptaen-9-one |
| 90 | 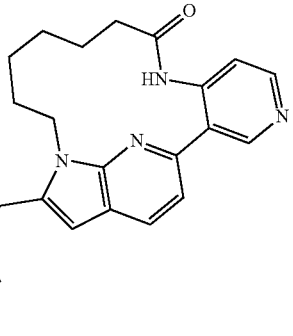 | 17-[5-[(1~{R},2~{R},4~{S})-2-amino-7-azabicyclo[2.2.1]heptane-7-carbonyl]-7-methoxy-1-methyl-benzimidazol-2-yl]-4,8,16,22-tetrazatetracyclo[14.5.2.0^{2,7}.0^{19,23}]tricosa-1(22),2,4,6,17,19(23),20-heptaen-9-one |
| 91 | 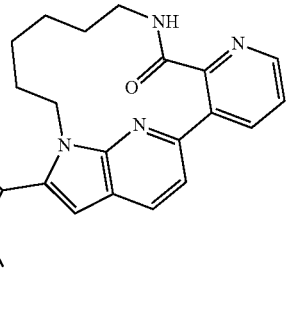 | 17-[5-[(1~{R},2~{R},4~{S})-2-amino-7-azabicyclo[2.2.1]heptane-7-carbonyl]-7-methoxy-1-methyl-benzimidazol-2-yl]-6,9,16,22-tetrazatetracyclo[14.5.2.0^{2,7}.0^{19,23}]tricosa-1(22),2,4,6,17,19(23),20-heptaen-8-one |

TABLE 1-continued

| Example | Structure | Name |
|---|---|---|
| 92 | 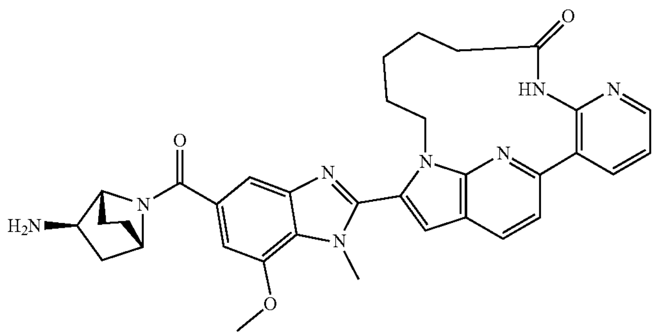 [SMILES: COc1cc(C(=O)N2[C@H]3CC[C@@H]2[C@H](N)C3)cc2nc(-c3cc4ccc5nc4n3CCCCCC(=O)Nc3ncccc3-5)n(C)c12] | 16-[5-[(1~{R},2~{R},4~{S})-2-amino-7-azabicyclo[2.2.1]heptane-7-carbonyl]-7-methoxy-1-methyl-benzimidazol-2-yl]-6,8,15,21-tetrazatetracyclo[13.5.2.0ˆ{2,7}.0ˆ{18,22}]docosa-1(21),2(7),3,5,16,18(22),19-heptaen-9-one |
| 93 | 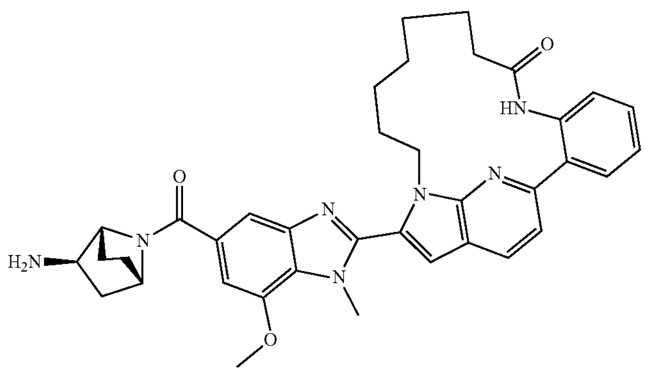 [SMILES: COc1cc(C(=O)N2[C@H]3CC[C@@H]2[C@H](N)C3)cc2nc(-c3cc4ccc5nc4n3CCCCCCCC(=O)Nc3ccccc3-5)n(C)c12] | 18-[5-[(1~{R},2~{R},4~{S})-2-amino-7-azabicyclo[2.2.1]heptane-7-carbonyl]-7-methoxy-1-methyl-benzimidazol-2-yl]-8,17,23-triazatetracyclo[15.5.2.0ˆ{2,7}.0ˆ{20,24}]tetracosa-1(23),2,4,6,18,20(24),21-heptaen-9-one |
| 94 | 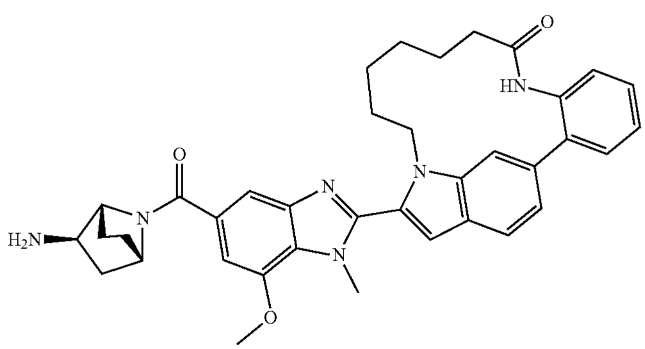 [SMILES: COc1cc(C(=O)N2[C@H]3CC[C@@H]2[C@H](N)C3)cc2nc(-c3cc4ccc5cc4n3CCCCCCC(=O)Nc3ccccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-8,16-diazatetracyclo[14.5.2.0ˆ{2,7}.0ˆ{19,23}]tricosa-1(22),2,4,6,17,19(23),20-heptaen-9-one |
| 95 | 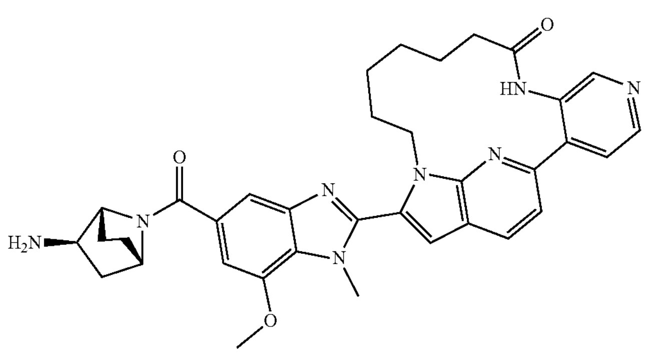 [SMILES: COc1cc(C(=O)N2[C@H]3CC[C@@H]2[C@H](N)C3)cc2nc(-c3cc4ccc5nc4n3CCCCCCC(=O)Nc3cnccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-5,8,16,22-tetrazatetracyclo[14.5.2.0ˆ{2,7}.0ˆ{19,23}]tricosa-1(22),2,4,6,17,19(23),20-heptaen-9-one |

TABLE 1-continued

| Example | Structure | Name |
|---|---|---|
| 96 | 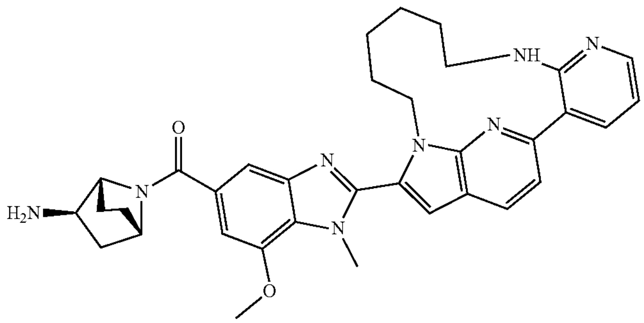 [SMILES: COc1cc(C(=O)N2[C@H]3CC[C@@H]2[C@H](N)C3)cc2nc(-c3cc4ccc5nc4n3CCCCCCNc3ncccc3-5)n(C)c12] | [(1~{R},2~{R},4~{S})-2-amino-7-azabicyclo[2.2.1]heptan-7-yl]-[7-methoxy-1-methyl-2-(6,8,15,21-tetrazatetracyclo[13.5.2.0^{2,7}.0^{18,22}]docosa-1(21),2,4,6,16,18(22),19-heptaen-16-yl)benzimidazol-5-yl]methanone |
| 97 | 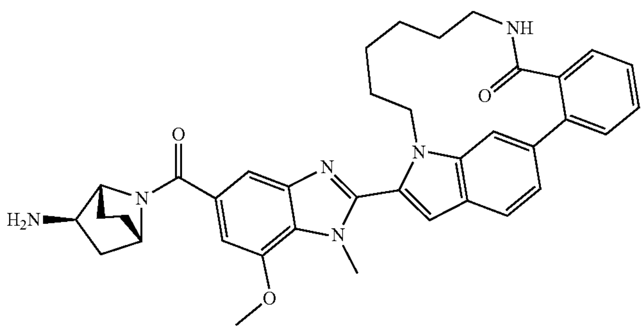 [SMILES: COc1cc(C(=O)N2[C@H]3CC[C@@H]2[C@H](N)C3)cc2nc(-c3cc4ccc5cc4n3CCCCCCNC(=O)c3ccccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-9,16-diazatetracyclo[14.5.2.0^{2,7}.0^{19,23}]tricosa-1(22),2,4,6,17,19(23),20-heptaen-8-one |
| 98 | 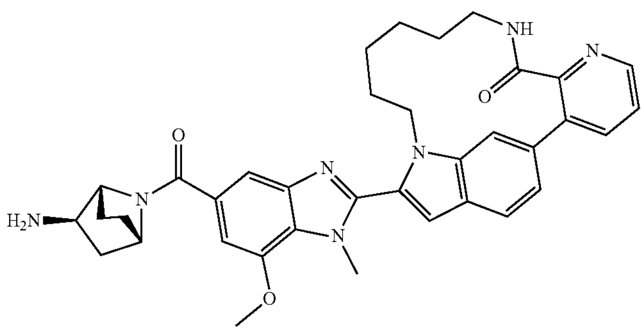 [SMILES: COc1cc(C(=O)N2[C@H]3CC[C@@H]2[C@H](N)C3)cc2nc(-c3cc4ccc5cc4n3CCCCCCNC(=O)c3ncccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-6,9,16-triazatetracyclo[14.5.2.0^{2,7}.0^{19,23}]tricosa-1(22),2,4,6,17,19(23),20-heptaen-8-one |
| 99 | 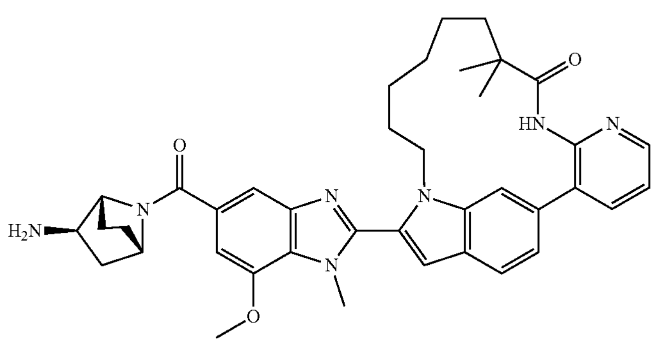 [SMILES: COc1cc(C(=O)N2[C@H]3CC[C@@H]2[C@H](N)C3)cc2nc(-c3cc4ccc5cc4n3CCCCCCC(C)(C)C(=O)Nc3ncccc3-5)n(C)c12] | 18-[5-[(1~{R},2~{R},4~{S})-2-amino-7-azabicyclo[2.2.1]heptane-7-carbonyl]-7-methoxy-1-methyl-benzimidazol-2-yl]-10,10-dimethyl-6,8,17-triazatetracyclo[15.5.2.0^{2,7}.0^{20,24}]tetracosa-1(23),2(7),3,5,18,20(24),21-heptaen-9-one |

TABLE 1-continued

| Example | Structure | Name |
|---|---|---|
| 100 | 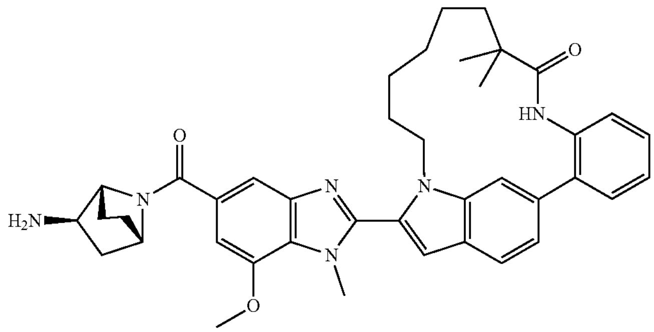 [SMILES: COc1cc(C(=O)N2[C@H]3CC[C@@H]2[C@H](N)C3)cc2nc(-c3cc4ccc5cc4n3CCCCCCC(C)(C)C(=O)Nc3ccccc3-5)n(C)c12] | 18-[5-[(1~{R},2~{R},4~{S})-2-amino-7-azabicyclo[2.2.1]heptane-7-carbonyl]-7-methoxy-1-methyl-benzimidazol-2-yl]-10,10-dimethyl-8,17-diazatetracyclo[15.5.2.0^{2,7}.0^{20,24}]tetracosa-1(23),2(7),3,5,18,20(24),21-heptaen-9-one |
| 101 | 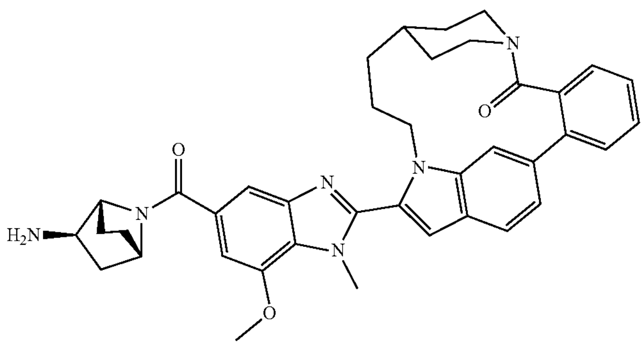 [SMILES: COc1cc(C(=O)N2[C@H]3CC[C@@H]2[C@H](N)C3)cc2nc(-c3cc4ccc5cc4n3CCCC3CCN(CC3)C(=O)c3ccccc3-5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-9,16-diazapentacyclo[14.5.2.2^{9,12}.0^{2,7}.0^{19,23}]pentacosa-1(22),2,4,6,17,19(23),20-heptaen-8-one |
| 102 | 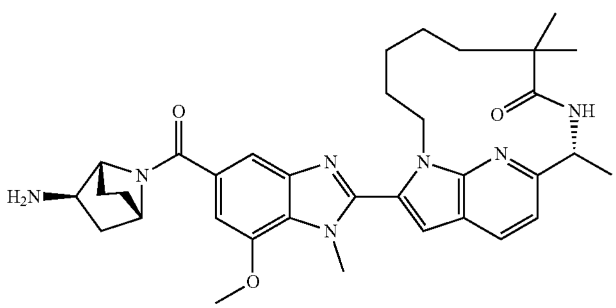 [SMILES: COc1cc(C(=O)N2[C@H]3CC[C@@H]2[C@H](N)C3)cc2nc(-c3cc4ccc5nc4n3CCCCCC(C)(C)C(=O)N[C@@H]5C)n(C)c12] | (10~{R})-16-[5-[(1~{R},2~{R},4~{S})-2-amino-7-azabicyclo[2.2.1]heptane-7-carbonyl]-7-methoxy-1-methyl-benzimidazol-2-yl]-7,7,10-trimethyl-1,9,18-triazatricyclo[9.5.2.0^{14,17}]octadeca-11(18),12,14(17),15-tetraen-8-one |
| 103 | 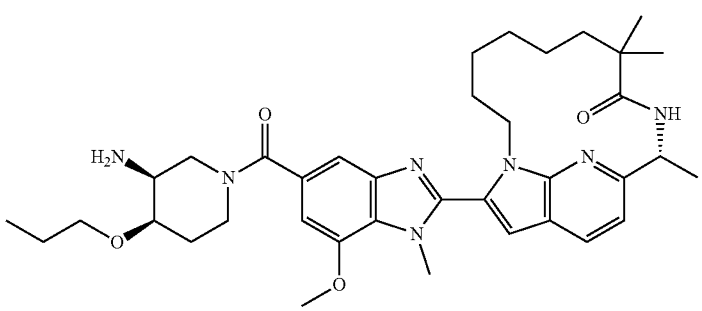 [SMILES: CCCO[C@@H]1CCN(C(=O)c2cc(OC)c3c(c2)nc(-c2cc4ccc5nc4n2CCCCCCC(C)(C)C(=O)N[C@@H]5C)n3C)C[C@@H]1N] | (11~{R})-17-[5-[(3~{S},4~{R})-3-amino-4-propoxy-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 104 | 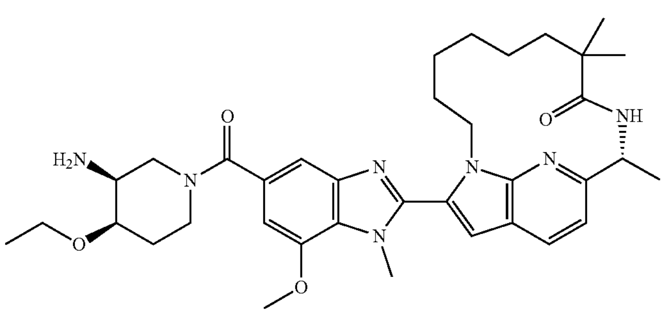 [SMILES: CCO[C@@H]1CCN(C(=O)c2cc(OC)c3c(c2)nc(-c2cc4ccc5nc4n2CCCCCCC(C)(C)C(=O)N[C@@H]5C)n3C)C[C@@H]1N] | (11~{R})-17-[5-[(3~{S},4~{R})-3-amino-4-ethoxy-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 105 | 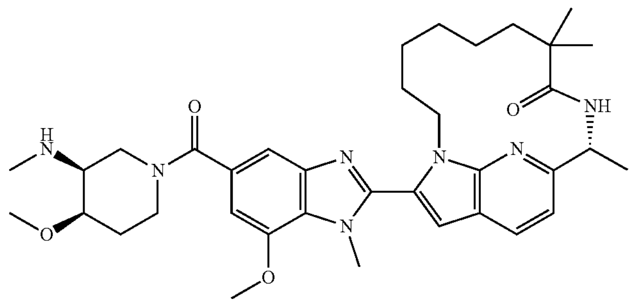 | (11~{R})-17-[7-methoxy-5-[(3~{S},4~{R})-4-methoxy-3-(methylamino)piperidine-1-carbonyl]-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 106 | 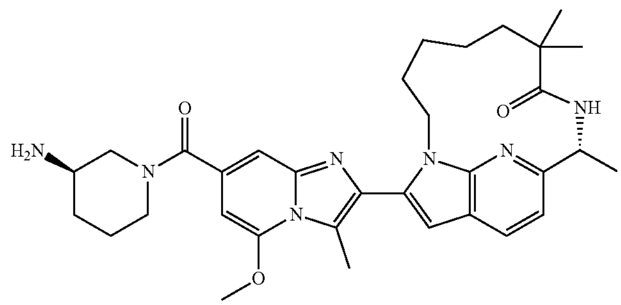 [SMILES: COc1cc(C(=O)N2CCC[C@@H](N)C2)cc2nc(-c3cc4ccc5nc4n3CCCCCC(C)(C)C(=O)N[C@@H]5C)c(C)n12] | (10~{R})-16-[7-[(3~{R})-3-aminopiperidine-1-carbonyl]-5-methoxy-3-methyl-imidazo[1,2-a]pyridin-2-yl]-7,7,10-trimethyl-1,9,18-triazatricyclo[9.5.2.0^{14,17}]octadeca-11(18),12,14(17),15-tetraen-8-one |
| 107 | 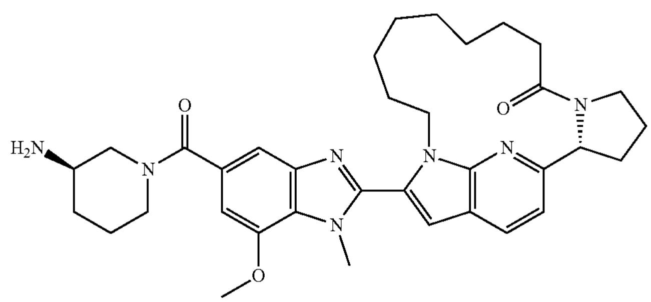 [SMILES: COc1cc(C(=O)N2CCC[C@@H](N)C2)cc2nc(-c3cc4ccc5nc4n3CCCCCCCCC(=O)N3CCC[C@H]53)n(C)c12] | (2~{R})-17-[5-[(3~{R})-3-aminopiperidine-1-carbonyl]-7-methoxy-1-methyl-benzimidazol-2-yl]-6,16,22-triazatetracyclo[14.5.2.0^{2,6}.0^{19,23}]tricosa-1(22),17,19(23),20-tetraen-7-one |
| 108 | 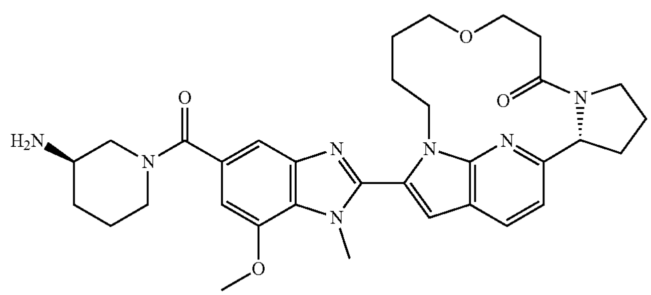 [SMILES: COc1cc(C(=O)N2CCC[C@@H](N)C2)cc2nc(-c3cc4ccc5nc4n3CCCCOCCC(=O)N3CCC[C@H]53)n(C)c12] | (2~{R})-16-[5-[(3~{R})-3-aminopiperidine-1-carbonyl]-7-methoxy-1-methyl-benzimidazol-2-yl]-10-oxa-6,15,21-triazatetracyclo[13.5.2.0^{2,6}.0^{18,22}]docosa-1(21),16,18(22),19-tetraen-7-one |
| 109 | 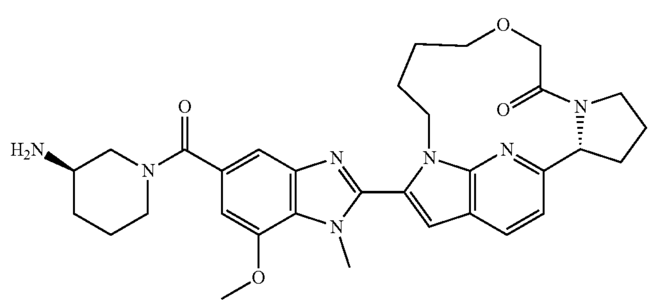 [SMILES: COc1cc(C(=O)N2CCC[C@@H](N)C2)cc2nc(-c3cc4ccc5nc4n3CCCCOCC(=O)N3CCC[C@H]53)n(C)c12] | (2~{R})-15-[5-[(3~{R})-3-aminopiperidine-1-carbonyl]-7-methoxy-1-methyl-benzimidazol-2-yl]-9-oxa-6,14,20-triazatetracyclo[12.5.2.0^{2,6}.0^{17,21}]henicosa-1(20),15,17(21),18-tetraen-7-one |

TABLE 1-continued

| Example | Structure | Name |
|---|---|---|
| 110 | 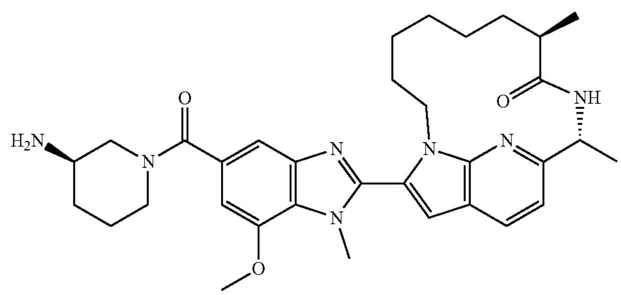 [SMILES: COc1cc(C(=O)N2CCC[C@@H](N)C2)cc2nc(-c3cc4ccc5nc4n3CCCCCC[C@@H](C)C(=O)N[C@@H]5C)n(C)c12] | (8~{R},11~{R})-17-[5-[(3~{R})-3-aminopiperidine-1-carbonyl]-7-methoxy-1-methyl-benzimidazol-2-yl]-8,11-dimethyl-1,10,19-triazatricyclo[10.5.2.0^{15,18}]nonadeca-12(19),13,15(18),16-tetraen-9-one |
| 111 | 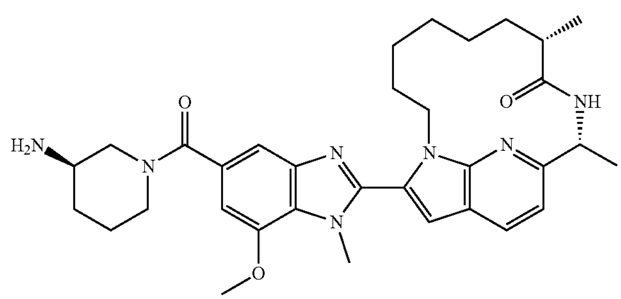 [SMILES: COc1cc(C(=O)N2CCC[C@@H](N)C2)cc2nc(-c3cc4ccc5nc4n3CCCCCC[C@H](C)C(=O)N[C@@H]5C)n(C)c12] | (8~{S},11~{R})-17-[5-[(3~{R})-3-aminopiperidine-1-carbonyl]-7-methoxy-1-methyl-benzimidazol-2-yl]-8,11-dimethyl-1,10,19-triazatricyclo[10.5.2.0^{15,18}]nonadeca-12(19),13,15(18),16-tetraen-9-one |
| 112 | 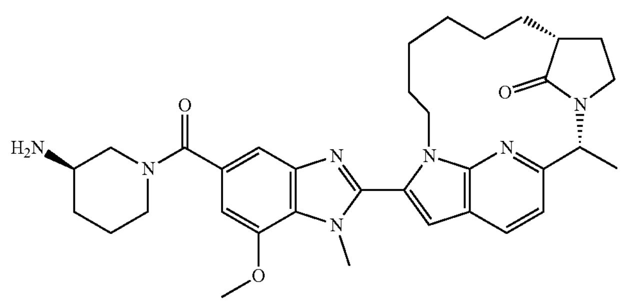 [SMILES: COc1cc(C(=O)N2CCC[C@@H](N)C2)cc2nc(-c3cc4ccc5nc4n3CCCCCC[C@@H]3CCN(C3=O)[C@@H]5C)n(C)c12] | (2~{R},6~{R})-14-[5-[(3~{R})-3-aminopiperidine-1-carbonyl]-7-methoxy-1-methyl-benzimidazol-2-yl]-2-methyl-3,13,19-triazatetracyclo[11.5.2.1^{3,6}.0^{16,20}]henicosa-1(19),14,16(20),17-tetraen-21-one |
| 113 | 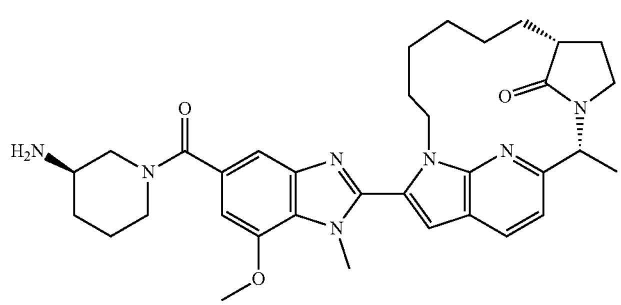 [SMILES: COc1cc(C(=O)N2CCC[C@@H](N)C2)cc2nc(-c3cc4ccc5nc4n3CCCCCC[C@@H]3CCN(C3=O)[C@@H]5C)n(C)c12] | (2~{R},6~{R})-14-[5-[(3~{R})-3-aminopiperidine-1-carbonyl]-7-methoxy-1-methyl-benzimidazol-2-yl]-2-methyl-3,13-diazatetracyclo[11.5.2.1^{3,6}.0^{16,20}]henicosa-1(19),14,16(20),17-tetraen-21-one |
| 114 | 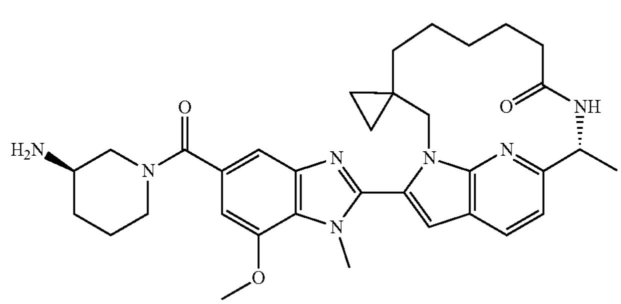 [SMILES: COc1cc(C(=O)N2CCC[C@@H](N)C2)cc2nc(-c3cc4ccc5nc4n3CC3(CCCCCC(=O)N[C@@H]5C)CC3)n(C)c12] | (11~{R})-17-[5-[(3~{R})-3-aminopiperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-3,1'-cyclopropane]-9-one |

TABLE 1-continued

| Example | Structure | Name |
|---|---|---|
| 115 | 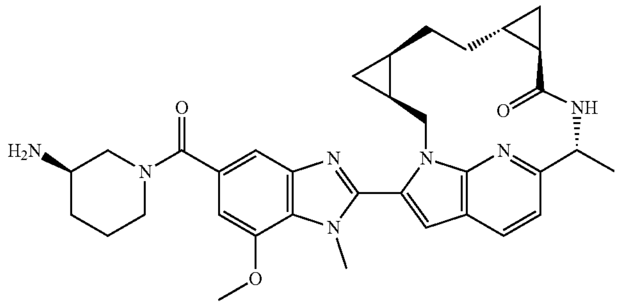 [SMILES: COc1cc(C(=O)N2CCC[C@@H](N)C2)cc2nc(-c3cc4ccc5nc4n3C[C@H]3C[C@H]3CC[C@@H]3C[C@H]3C(=O)N[C@@H]5C)n(C)c12] | (3~{S},5~{R},8~{R},10~{R},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |
| 116 | 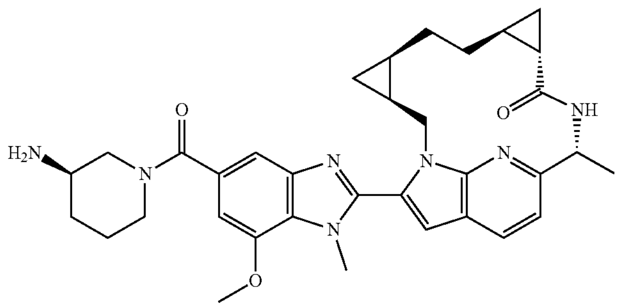 [SMILES: COc1cc(C(=O)N2CCC[C@@H](N)C2)cc2nc(-c3cc4ccc5nc4n3C[C@H]3C[C@H]3CC[C@H]3C[C@@H]3C(=O)N[C@@H]5C)n(C)c12] | (3~{S},5~{R},8~{S},10~{S},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |
| 117 | 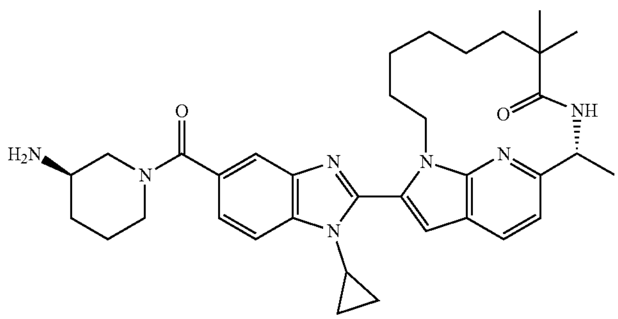 [SMILES: C[C@H]1NC(=O)C(C)(C)CCCCCCn2c(-c3nc4cc(C(=O)N5CCC[C@@H](N)C5)ccc4n3C3CC3)cc3ccc1nc32] | (11~{R})-17-[5-[(3~{R})-3-aminopiperidine-1-carbonyl]-1-cyclopropyl-benzimidazol-2-yl]-8,8,11-trimethyl-1,10,19-triazatricyclo[10.5.2.0^{15,18}]nonadeca-12(19),13,15(18),16-tetraen-9-one |
| 118 | 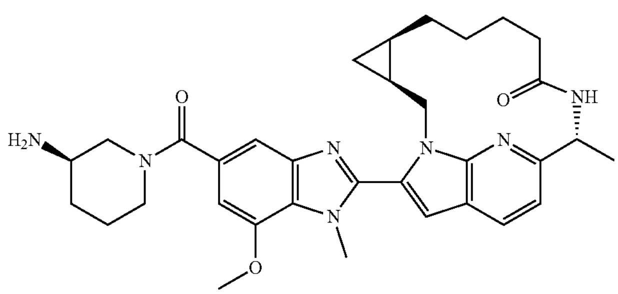 [SMILES: COc1cc(C(=O)N2CCC[C@@H](N)C2)cc2nc(-c3cc4ccc5nc4n3C[C@H]3C[C@H]3CCCCC(=O)N[C@@H]5C)n(C)c12] | (3~{S},5~{R},12~{R})-18-[5-[(3~{R})-3-aminopiperidine-1-carbonyl]-7-methoxy-1-methyl-benzimidazol-2-yl]-12-methyl-1,11,20-triazatetracyclo[11.5.2.0^{3,5}.0^{16,19}]icosa-13(20),14,16(19),17-tetraen-10-one |
| 119 | 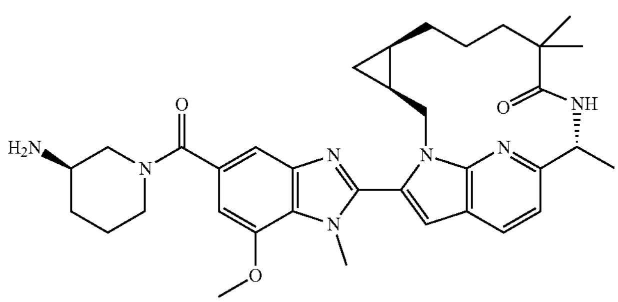 [SMILES: COc1cc(C(=O)N2CCC[C@@H](N)C2)cc2nc(-c3cc4ccc5nc4n3C[C@H]3C[C@H]3CCCC(C)(C)C(=O)N[C@@H]5C)n(C)c12] | (3~{S},5~{R},12~{R})-18-[5-[(3~{R})-3-aminopiperidine-1-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 120 | 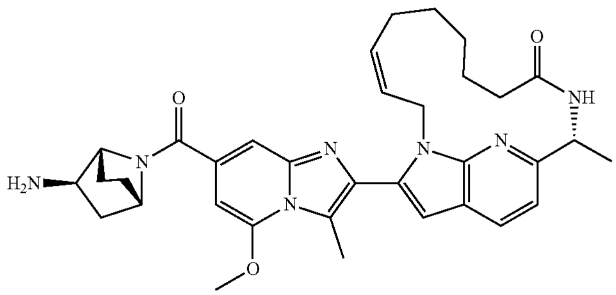 [SMILES: COc1cc(C(=O)N2[C@H]3CC[C@@H]2[C@H](N)C3)cc2nc(-c3cc4ccc5nc4n3C/C=C\CCCCCC(=O)N[C@@H]5C)c(C)n12] | (3~{2},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-1,11,20-triazatricyclo[11.5.2.0^{16,19}]icosa-3,13(20),14,16(19),17-pentaen-10-one |
| 121 | 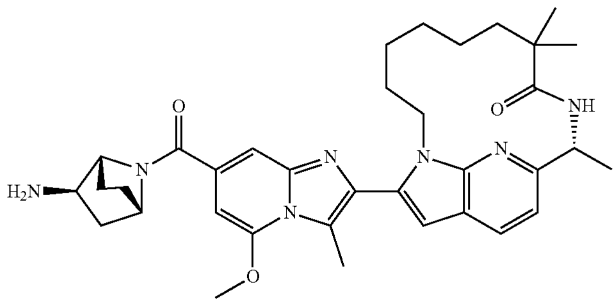 [SMILES: COc1cc(C(=O)N2[C@H]3CC[C@@H]2[C@H](N)C3)cc2nc(-c3cc4ccc5nc4n3CCCCCCC(C)(C)C(=O)N[C@@H]5C)c(C)n12] | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8,8,11-trimethyl-1,10,19-triazatricyclo[10.5.2.0^{15,18}]nonadeca-12(19),13,15(18),16-tetraen-9-one |
| 122 | 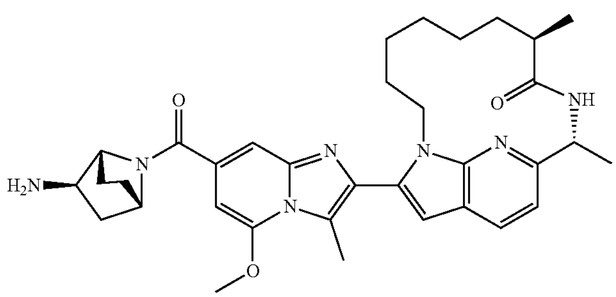 [SMILES: COc1cc(C(=O)N2[C@H]3CC[C@@H]2[C@H](N)C3)cc2nc(-c3cc4ccc5nc4n3CCCCCC[C@@H](C)C(=O)N[C@@H]5C)c(C)n12] | (8~{R},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8,11-dimethyl-1,10,19-triazatricyclo[10.5.2.0^{15,18}]nonadeca-12(19),13,15(18),16-tetraen-9-one |
| 123 | 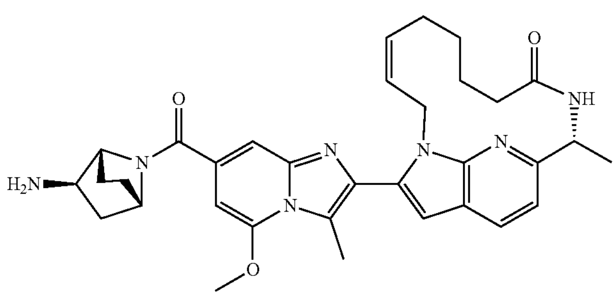 [SMILES: COc1cc(C(=O)N2[C@H]3CC[C@@H]2[C@H](N)C3)cc2nc(-c3cc4ccc5nc4n3C/C=C\CCCCC(=O)N[C@@H]5C)c(C)n12] | (3~{2},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-1,10,19-triazatricyclo[10.5.2.0^{15,18}]nonadeca-3,12(19),13,15(18),16-pentaen-9-one |
| 124 | 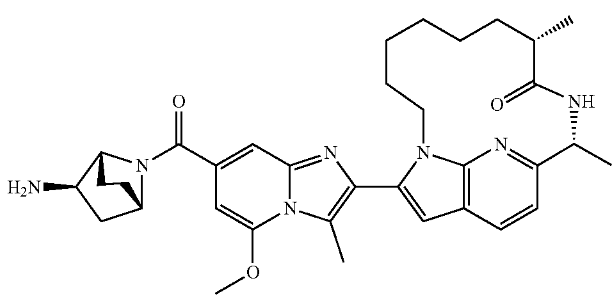 [SMILES: COc1cc(C(=O)N2[C@H]3CC[C@@H]2[C@H](N)C3)cc2nc(-c3cc4ccc5nc4n3CCCCCC[C@H](C)C(=O)N[C@@H]5C)c(C)n12] | (8~{S},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8,11-dimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 125 | 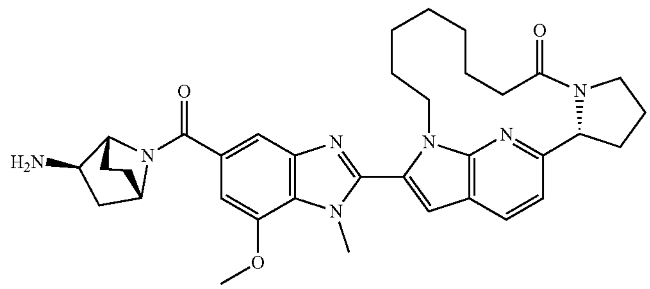 [SMILES: COc1cc(C(=O)N2[C@H]3CC[C@@H]2[C@H](N)C3)cc2nc(-c3cc4ccc5nc4n3CCCCCCCC(=O)N3CCC[C@H]53)n(C)c12] | (2~{R})-16-[5-[(1~{R},2~{R},4~{S})-2-amino-7-azabicyclo[2.2.1]heptane-7-carbonyl)-7-methoxy-1-methyl-benzimidazol-2-yl]-6,15,21-triazatetracyclo[13.5.2.0^{2,6}.0^{18,22}]docosa-1(21),16,18(22),19-tetraen-7-one |
| 126 | 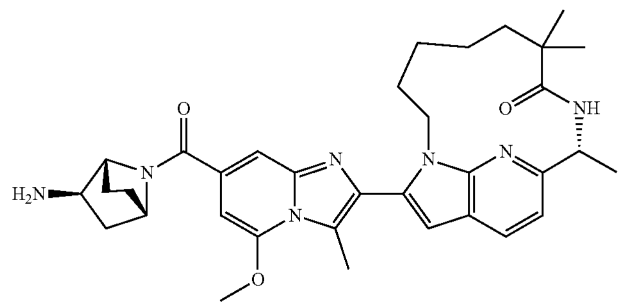 [SMILES: COc1cc(C(=O)N2[C@H]3CC[C@@H]2[C@H](N)C3)cc2nc(-c3cc4ccc5nc4n3CCCCCC(C)(C)C(=O)N[C@@H]5C)c(C)n12] | (10~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-7,7,10-trimethyl-1,9,18-triazatricyclo[9.5.2.0^{14,17}]octadeca-11(18),12,14(17),15-tetraen-8-one |
| 127 | 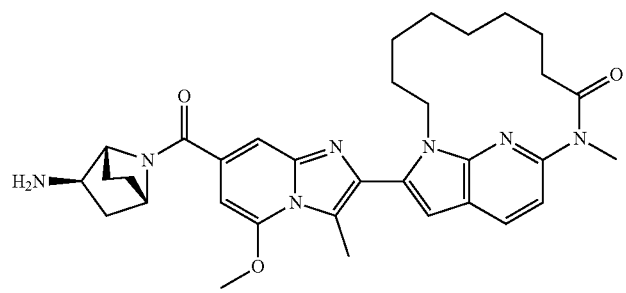 [SMILES: COc1cc(C(=O)N2[C@H]3CC[C@@H]2[C@H](N)C3)cc2nc(-c3cc4ccc5nc4n3CCCCCCCCC(=O)N5C)c(C)n12] | 17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-1,11,19-triazatricyclo[10.5.2.0^{15,18}]nonadeca-12(19),13,15(18),16-tetraen-10-one |
| 128 | 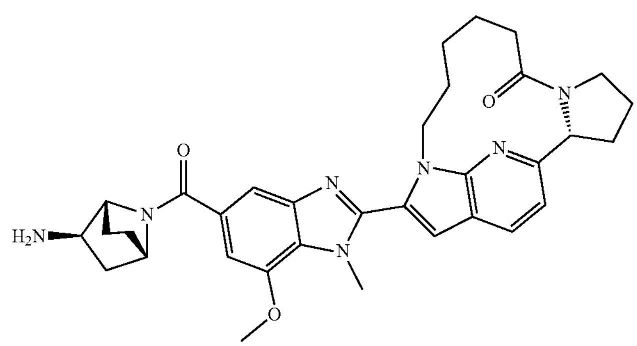 [SMILES: COc1cc(C(=O)N2[C@H]3CC[C@@H]2[C@H](N)C3)cc2nc(-c3cc4ccc5nc4n3CCCCCC(=O)N3CCC[C@H]53)n(C)c12] | (2~{R})-14-[5-[(1~{R},2~{R},4~{S})-2-amino-7-azabicyclo[2.2.1]heptane-7-carbonyl]-7-methoxy-1-methyl-benzimidazol-2-yl]-6,13,19-triazatetracyclo[11.5.2.0^{2,6}.0^{16,20}]icosa-1(19),14,16(20),17-tetraen-7-one |
| 129 | 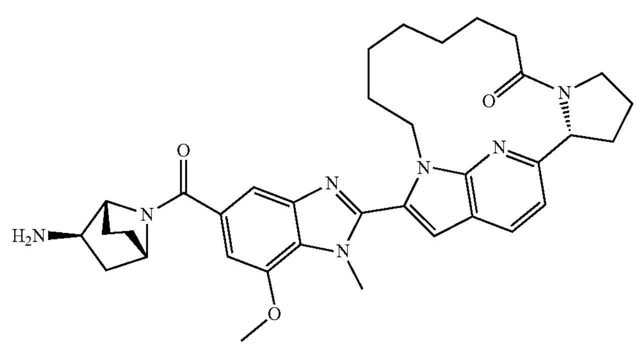 [SMILES: COc1cc(C(=O)N2[C@H]3CC[C@@H]2[C@H](N)C3)cc2nc(-c3cc4ccc5nc4n3CCCCCCCC(=O)N3CCC[C@H]53)n(C)c12] | (2~{R})-16-[5-[(1~{R},2~{R},4~{S})-2-amino-7-azabicyclo[2.2.1]heptane-7-carbonyl]-7-methoxy-1-methyl-benzimidazol-2-yl]-6,15-diazatetracyclo[13.5.2.0^{2,6}.0^{18,22}]docosa-1(21),16,18(22),19-tetraen-7-one |

TABLE 1-continued

| Example | Structure | Name |
|---|---|---|
| 130 | 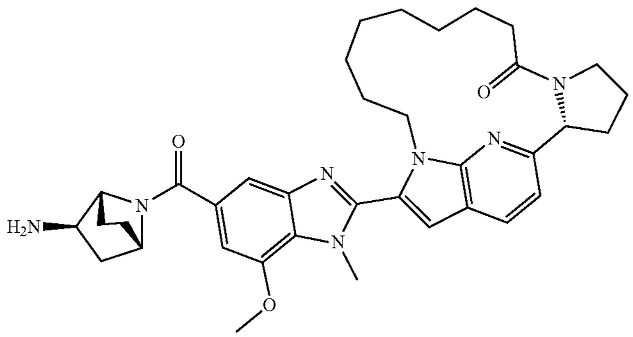 [SMILES: COc1cc(C(=O)N2[C@H]3CC[C@@H]2[C@H](N)C3)cc2nc(-c3cc4ccc5nc4n3CCCCCCCCC(=O)N3CCC[C@H]53)n(C)c12] | (2~{R})-17-[5-[(1~{R},2~{R},4~{S})-2-amino-7-azabicyclo[2.2.1]heptane-7-carbonyl]-7-methoxy-1-methyl-benzimidazol-2-yl]-6,16,22-triazatetracyclo[14.5.2.0^{2,6}.0^{19,23}]tricosa-1(22),17,19(23),20-tetraen-7-one |
| 131 | 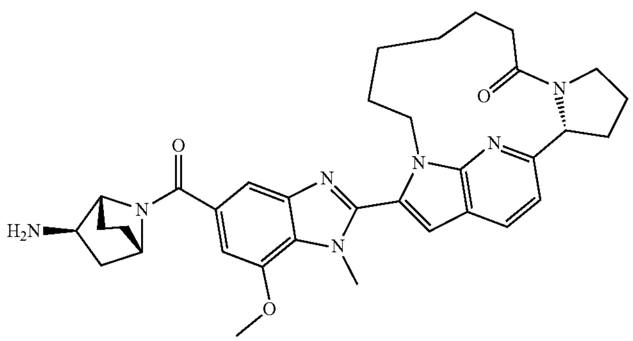 [SMILES: COc1cc(C(=O)N2[C@H]3CC[C@@H]2[C@H](N)C3)cc2nc(-c3cc4ccc5nc4n3CCCCCCC(=O)N3CCC[C@H]53)n(C)c12] | (2~{R})-15-[5-[(1~{R},2~{R},4~{S})-2-amino-7-azabicyclo[2.2.1]heptane-7-carbonyl]-7-methoxy-1-methyl-benzimidazol-2-yl]-6,14,20-triazatetracyclo[12.5.2.0^{2,6}.0^{17,21}]henicosa-1(20),15,17(21),18-tetraen-7-one |
| 132 | 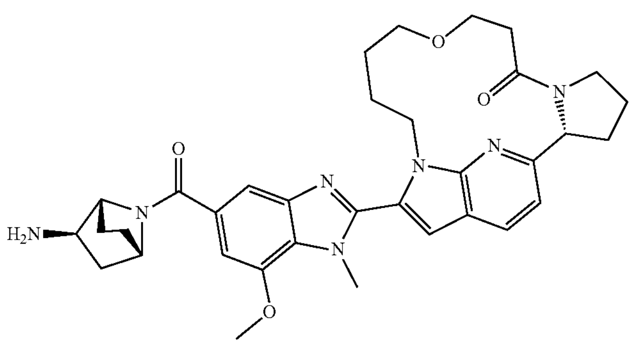 [SMILES: COc1cc(C(=O)N2[C@H]3CC[C@@H]2[C@H](N)C3)cc2nc(-c3cc4ccc5nc4n3CCCCOCCC(=O)N3CCC[C@H]53)n(C)c12] | (2~{R})-16-[5-[(1~{R},2~{R},4~{S})-2-amino-7-azabicyclo[2.2.1]heptane-7-carbonyl]-7-methoxy-1-methyl-benzimidazol-2-yl]-10-oxa-6,15,21-triazatetracyclo[13.5.2.0^{2,6}.0^{18,22}]docosa-1(21),16,18(22),19-tetraen-7-one |
| 133 | 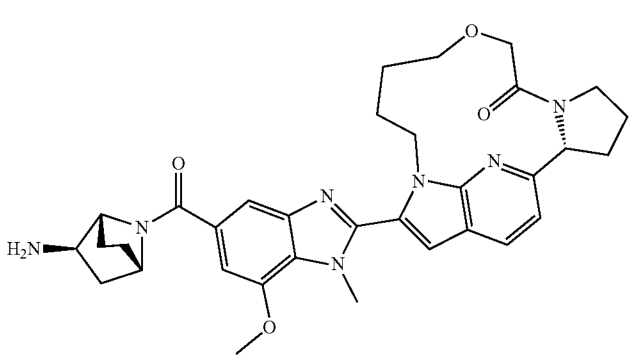 [SMILES: COc1cc(C(=O)N2[C@H]3CC[C@@H]2[C@H](N)C3)cc2nc(-c3cc4ccc5nc4n3CCCCOCC(=O)N3CCC[C@H]53)n(C)c12] | (2~{R})-15-[5-[(1~{R},2~{R},4~{S})-2-amino-7-azabicyclo[2.2.1]heptane-7-carbonyl]-7-methoxy-1-methyl-benzimidazol-2-yl]-9-oxa-6,14,20-triazatetracyclo[12.5.2.0^{2,6}.0^{17,21}]henicosa-1(20),15,17(21),18-tetraen-7-one |

TABLE 1-continued

| Example | Structure | Name |
|---|---|---|
| 134 | 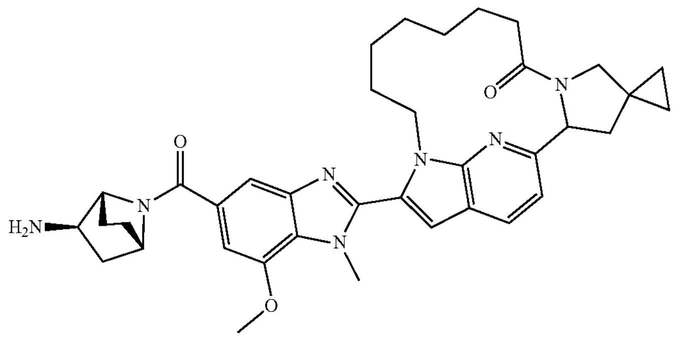 [SMILES: COc1cc(C(=O)N2[C@H]3CC[C@@H]2[C@H](N)C3)cc2nc(-c3cc4ccc5nc4n3CCCCCCCC(=O)N3CC4(CC4)CC53)n(C)c12] | 16-[5-[(1~{R},2~{R},4~{S})-2-amino-7-azabicyclo[2.2.1]heptane-7-carbonyl]-7-methoxy-1-methyl-benzimidazol-2-yl]spiro[6,15,21-triazatetracyclo[13.5.2.0^{2,6}.0^{18,22}]docosa-1(21),16,18(22),19-tetraene-4,1'-cyclopropane]-7-one |
| 135 | 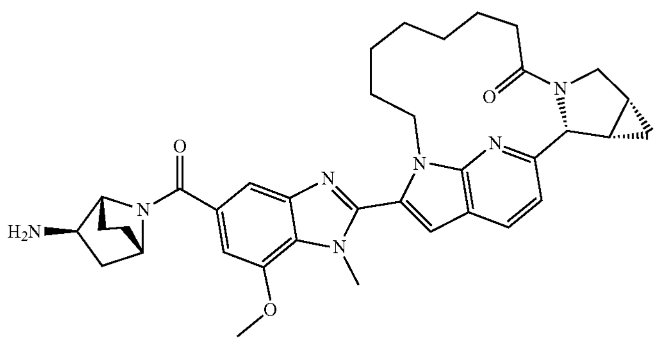 [SMILES: COc1cc(C(=O)N2[C@H]3CC[C@@H]2[C@H](N)C3)cc2nc(-c3cc4ccc5nc4n3CCCCCCCC(=O)N3C[C@@H]4C[C@@H]4[C@H]53)n(C)c12] | (2~{R},3~{S},5~{R})-17-[5-[(1~{R},2~{R},4~{S})-2-amino-7-azabicyclo[2.2.1]heptane-7-carbonyl]-7-methoxy-1-methyl-benzimidazol-2-yl]-7,16,22-triazapentacyclo[14.5.2.0^{2,7}.0^{3,5}.0^{19,23}]tricosa-1(22),17,19(23),20-tetraen-8-one |
| 136 | 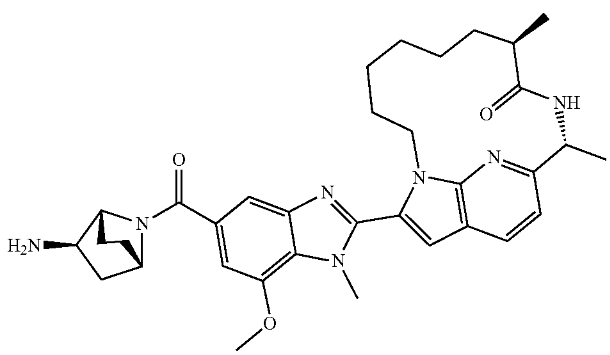 [SMILES: COc1cc(C(=O)N2[C@H]3CC[C@@H]2[C@H](N)C3)cc2nc(-c3cc4ccc5nc4n3CCCCCC[C@@H](C)C(=O)N[C@@H]5C)n(C)c12] | (8~{R},11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,11-dimethyl-1,10,19-triazatricyclo[10.5.2.0^{15,18}]nonadeca-12(19),13,15(18),16-tetraen-9-one |
| 137 | 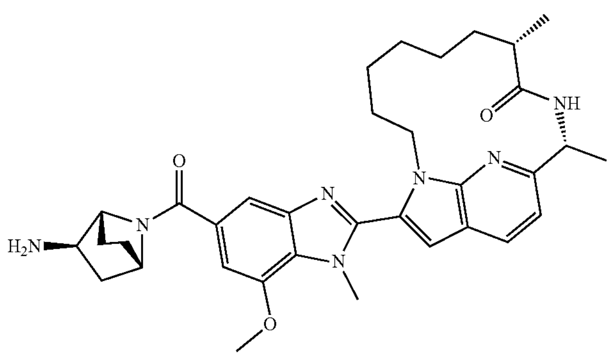 [SMILES: COc1cc(C(=O)N2[C@H]3CC[C@@H]2[C@H](N)C3)cc2nc(-c3cc4ccc5nc4n3CCCCCC[C@H](C)C(=O)N[C@@H]5C)n(C)c12] | (8~{S},11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,11-dimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 138 | 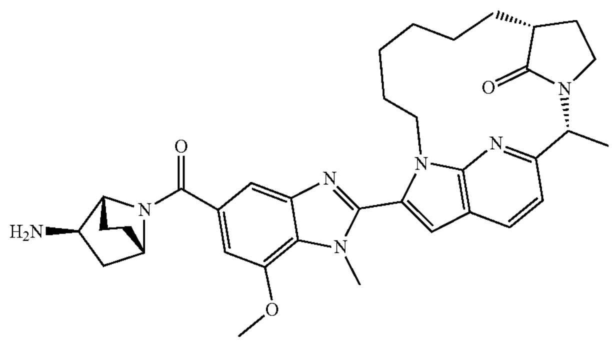 [SMILES: COc1cc(C(=O)N2[C@H]3CC[C@@H]2[C@H](N)C3)cc2nc(-c3cc4ccc5nc4n3CCCCCC[C@@H]3CCN(C3=O)[C@@H]5C)n(C)c12] | (2~{R},6~{R})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.1^{3,6}.0^{16,20}]henicosa-1(19),14,16(20),17-tetraen-21-one |
| 139 | 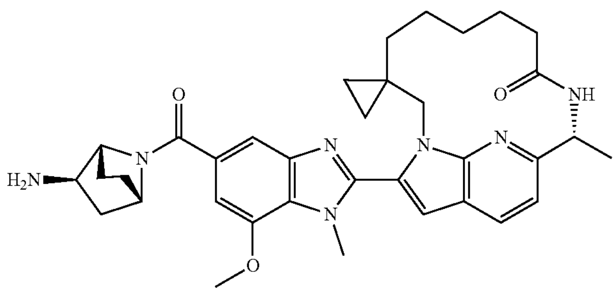 [SMILES: COc1cc(C(=O)N2[C@H]3CC[C@@H]2[C@H](N)C3)cc2nc(-c3cc4ccc5nc4n3CC3(CCCCCC(=O)N[C@@H]5C)CC3)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-3,1'-cyclopropane]-9-one |
| 140 | 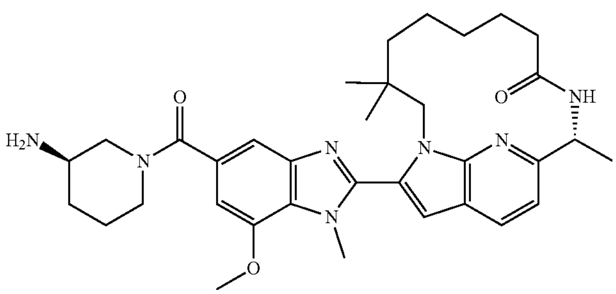 | (11~{R})-17-[5-[(3~{R})-3-aminopiperidine-1-carbonyl]-7-methoxy-1-methyl-benzimidazol-2-yl]-3,3,11-trimethyl-1,10,19-triazatricyclo[10.5.2.0^{15,18}]nonadeca-12(19),13,15(18),16-tetraen-9-one |
| 141 | 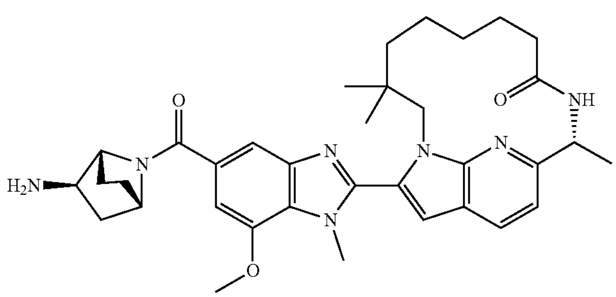 [SMILES: COc1cc(C(=O)N2[C@H]3CC[C@@H]2[C@H](N)C3)cc2nc(-c3cc4ccc5nc4n3CC(C)(C)CCCCCC(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-3,3,11-trimethyl-1,10,19-triazatricyclo[10.5.2.0^{15,18}]nonadeca-12(19),13,15(18),16-tetraen-9-one |
| 142 | 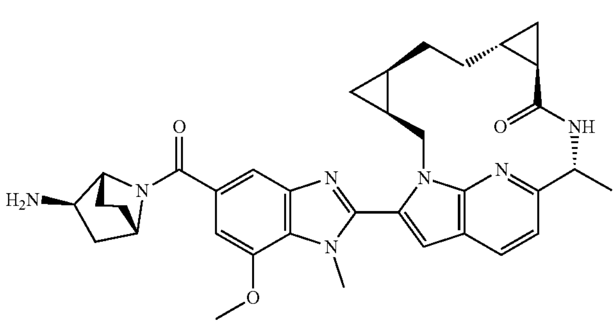 [SMILES: COc1cc(C(=O)N2[C@H]3CC[C@@H]2[C@H](N)C3)cc2nc(-c3cc4ccc5nc4n3C[C@H]3C[C@H]3CC[C@@H]3C[C@H]3C(=O)N[C@@H]5C)n(C)c12] | (3~{S},5~{R},8~{R},10~{R},13~{R})-19-[5-[(1~{R},2~{R},4~{S})-2-amino-7-azabicyclo[2.2.1]heptane-7-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |

TABLE 1-continued

| Example | Structure | Name |
|---|---|---|
| 143 | 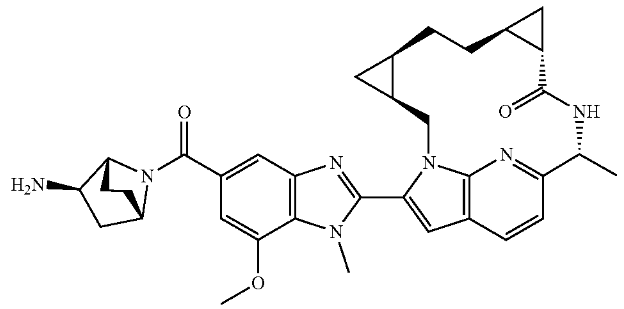 [SMILES: COc1cc(C(=O)N2[C@H]3CC[C@@H]2[C@H](N)C3)cc2nc(-c3cc4ccc5nc4n3C[C@H]3C[C@H]3CC[C@H]3C[C@@H]3C(=O)N[C@@H]5C)n(C)c12] | (3~{S},5~{R},8~{S},10~{S},13~{R})-19-[5-[(1~{R},2~{R},4~{S})-2-amino-7-azabicyclo[2.2.1]heptane-7-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |
| 144 | 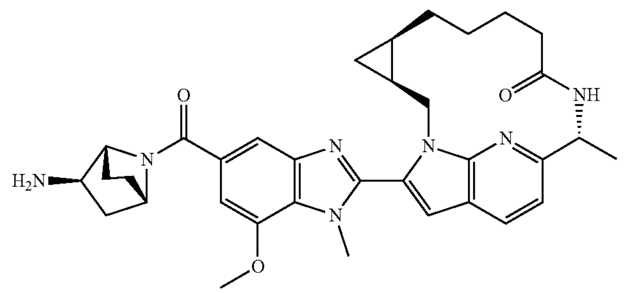 [SMILES: COc1cc(C(=O)N2[C@H]3CC[C@@H]2[C@H](N)C3)cc2nc(-c3cc4ccc5nc4n3C[C@H]3C[C@H]3CCCCC(=O)N[C@@H]5C)n(C)c12] | (3~{S},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-1,11,20-triazatetracyclo[11.5.2.0^{3,5}.0^{16,19}]icosa-13(20),14,16(19),17-tetraen-10-one |
| 145 | 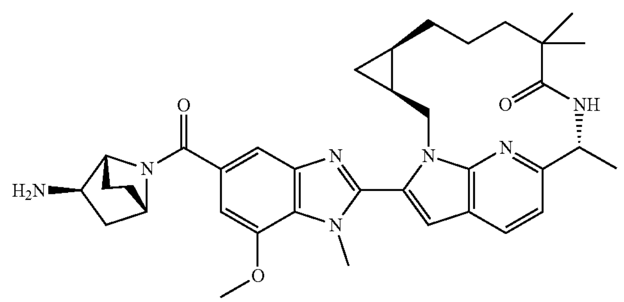 [SMILES: COc1cc(C(=O)N2[C@H]3CC[C@@H]2[C@H](N)C3)cc2nc(-c3cc4ccc5nc4n3C[C@H]3C[C@H]3CCCC(C)(C)C(=O)N[C@@H]5C)n(C)c12] | (3~{S},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one |
| 146 | 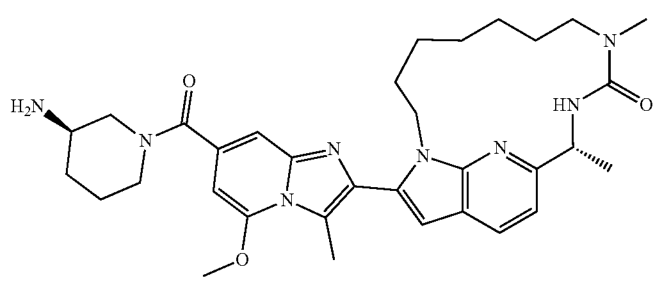 [SMILES: COc1cc(C(=O)N2CCC[C@@H](N)C2)cc2nc(-c3cc4ccc5nc4n3CCCCCCCN(C)C(=O)N[C@@H]5C)c(C)n12] | (12~{R})-18-[7-[(3~{R})-3-aminopiperidine-1-carbonyl]-5-methoxy-3-methyl-imidazo[1,2-a]pyridin-2-yl]-9,12-dimethyl-1,9,11,20-tetrazatricyclo[11.5.2.0^{16,19}]icosa-13(20),14,16(19),17-tetraen-10-one |
| 147 | 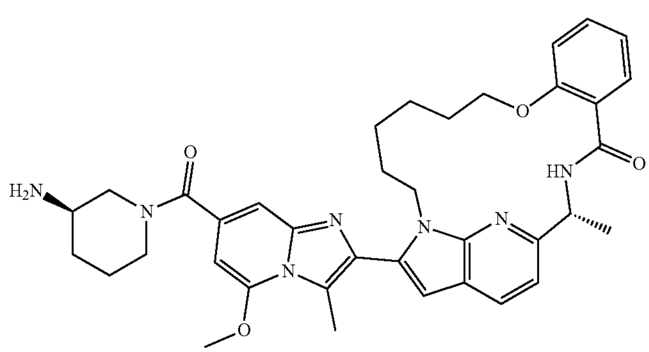 [SMILES: COc1cc(C(=O)N2CCC[C@@H](N)C2)cc2nc(-c3cc4ccc5nc4n3CCCCCCOc3ccccc3C(=O)N[C@@H]5C)c(C)n12] | (2~{R})-19-[7-[(3~{R})-3-aminopiperidine-1-carbonyl]-5-methoxy-3-methyl-imidazo[1,2-a]pyridin-2-yl]-2-methyl-11-oxa-3,18,24-triazatetracyclo[16.5.2.0^{5,10}.0^{21,25}]pentacosa-1(24),5(10),6,8,19,21(25),22-heptaen-4-one |

TABLE 1-continued

| Example | Structure | Name |
| --- | --- | --- |
| 148 | 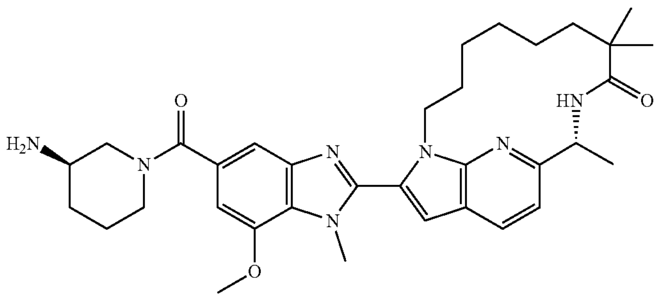 [SMILES: COc1cc(C(=O)N2CCC[C@@H](N)C2)cc2nc(-c3cc4ccc5nc4n3CCCCCCC(C)(C)C(=O)N[C@@H]5C)n(C)c12] | (11~{R})-17-[5-[(3~{R})-3-aminopiperidine-1-carbonyl]-7-methoxy-1-methyl-benzimidazol-2-yl]-8,8,11-trimethyl-1,10-diazatricyclo[10.5.2.0˜{15,18}]nonadeca-12(19),13,15(18),16-tetraen-9-one |
| 149 | 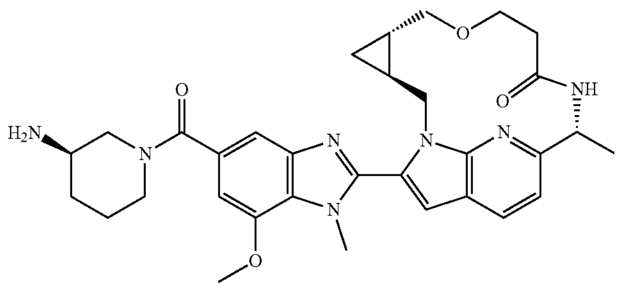 [SMILES: COc1cc(C(=O)N2CCC[C@@H](N)C2)cc2nc(-c3cc4ccc5nc4n3C[C@H]3C[C@@H]3COCCC(=O)N[C@@H]5C)n(C)c12] | (3~{S},5~{S},12~{R})-18-[5-[(3~{R})-3-aminopiperidine-1-carbonyl]-7-methoxy-1-methyl-benzimidazol-2-yl]-12-methyl-7-oxa-1,11,20-triazatetracyclo[11.5.2.0˜{3,5}.0˜{16,19}]icosa-13(20),14,16(19),17-tetraen-10-one |
| 150 | 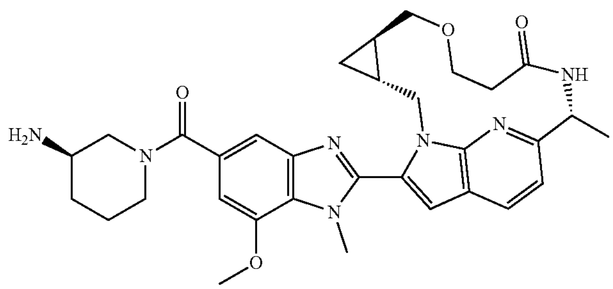 [SMILES: COc1cc(C(=O)N2CCC[C@@H](N)C2)cc2nc(-c3cc4ccc5nc4n3C[C@@H]3C[C@H]3COCCC(=O)N[C@@H]5C)n(C)c12] | (3~{R},5~{R},12~{R})-18-[5-[(3~{R})-3-aminopiperidine-1-carbonyl]-7-methoxy-1-methyl-benzimidazol-2-yl]-12-methyl-7-oxa-1,11,20-triazatetracyclo[11.5.2.0˜{3,5}.0˜{16,19}]icosa-13(20),14,16(19),17-tetraen-10-one |
| 151 | 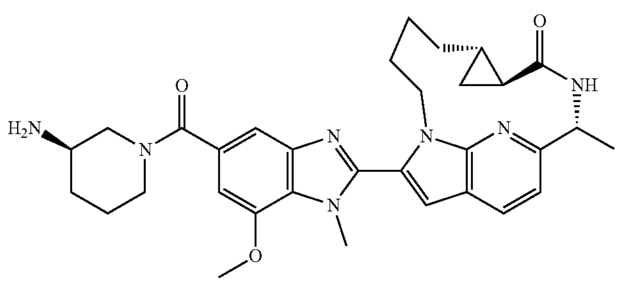 [SMILES: COc1cc(C(=O)N2CCC[C@@H](N)C2)cc2nc(-c3cc4ccc5nc4n3CCCC[C@H]3C[C@@H]3C(=O)N[C@@H]5C)n(C)c12] | (2~{R},5~{S},7~{S})-13-[5-[(3~{R})-3-aminopiperidine-1-carbonyl]-7-methoxy-1-methyl-benzimidazol-2-yl]-2-methyl-3,12,18-triazatetracyclo[10.5.2.0˜{5,7}.0˜{15,19}]nonadeca-1(18),13,15(19),16-tetraen-4-one |
| 152 | 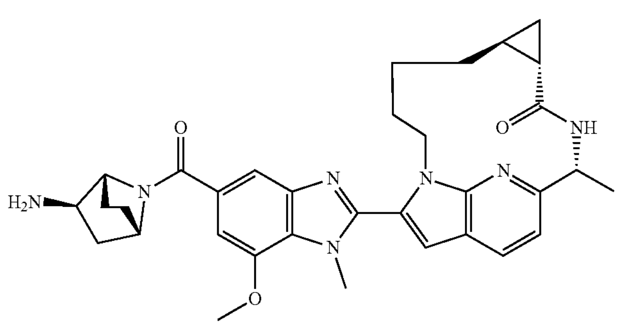 [SMILES: COc1cc(C(=O)N2[C@H]3CC[C@@H]2[C@H](N)C3)cc2nc(-c3cc4ccc5nc4n3CCCC[C@H]3C[C@@H]3C(=O)N[C@@H]5C)n(C)c12] | (2~{R},5~{S},7~{S})-13-[5-[(1~{R},2~{R},4~{S})-2-amino-7-azabicyclo[2.2.1]heptane-7-carbonyl]-7-methoxy-1-methyl-benzimidazol-2-yl]-2-methyl-3,12,18-triazatetracyclo[10.5.2.0˜{5,7}.0˜{15,19}]nonadeca-1(18),13,15(19),16-tetraen-4-one |

TABLE 1-continued

| Example | Structure | Name |
|---|---|---|
| 153 | 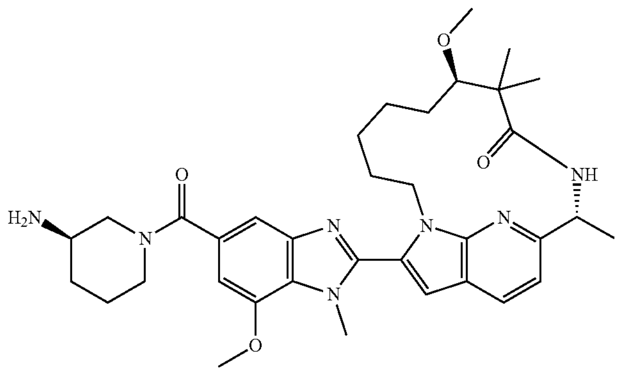 [SMILES: COc1cc(C(=O)N2CCC[C@@H](N)C2)cc2nc(-c3cc4ccc5nc4n3CCCCC[C@@H](OC)C(C)(C)C(=O)N[C@@H]5C)n(C)c12] | (7~{R},11~{R})-17-[5-[(3~{R})-3-aminopiperidine-1-carbonyl]-7-methoxy-1-methyl-benzimidazol-2-yl]-7-methoxy-8,8,11-trimethyl-1,10,19-triazatricyclo[10.5.2.0^{15,18}]nonadeca-12(19),13,15(18),16-tetraen-9-one |
| 154 | 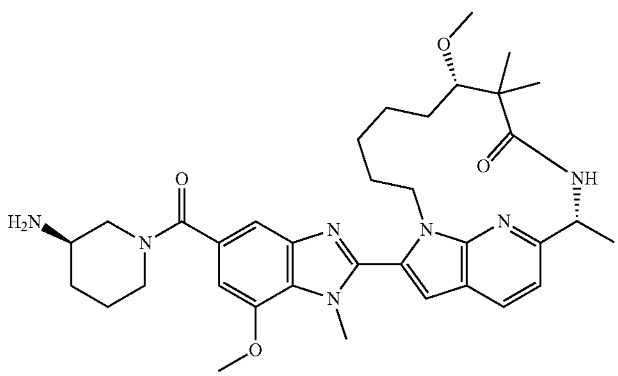 [SMILES: COc1cc(C(=O)N2CCC[C@@H](N)C2)cc2nc(-c3cc4ccc5nc4n3CCCCC[C@H](OC)C(C)(C)C(=O)N[C@@H]5C)n(C)c12] | (7~{S},11~{R})-17-[5-[(3~{R})-3-aminopiperidine-1-carbonyl]-7-methoxy-1-methyl-benzimidazol-2-yl]-7-methoxy-8,8,11-trimethyl-1,10,19-triazatricyclo[10.5.2.0^{15,18}]nonadeca-12(19),13,15(18),16-tetraen-9-one |
| 155 | 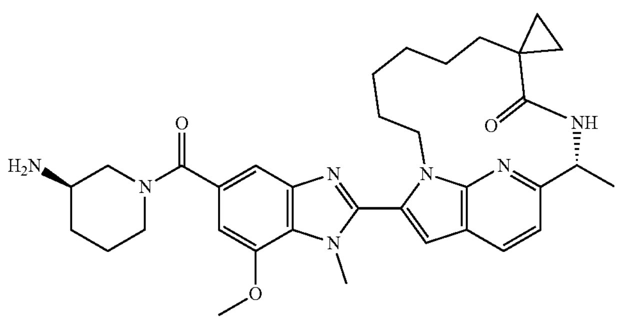 [SMILES: COc1cc(C(=O)N2CCC[C@@H](N)C2)cc2nc(-c3cc4ccc5nc4n3CCCCCCC3(CC3)C(=O)N[C@@H]5C)n(C)c12] | (11~{R})-17-[5-[(3~{R})-3-aminopiperidine-1-carbonyl]-7-methoxy-1-methyl-benzimidazol-2-yl]-11-methyl-spiro[1,10-diazatricyclo[10.5.2.0^{15,18}]nonadeca-12(19),13,15(18),16-tetraene-8,1'-cyclopropane]-9-one |
| 156 | 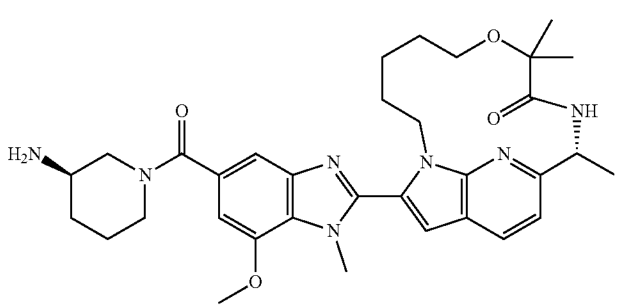 [SMILES: COc1cc(C(=O)N2CCC[C@@H](N)C2)cc2nc(-c3cc4ccc5nc4n3CCCCCOC(C)(C)C(=O)N[C@@H]5C)n(C)c12] | (11~{R})-17-[5-[(3~{R})-3-aminopiperidine-1-carbonyl]-7-methoxy-1-methyl-benzimidazol-2-yl]-8,8,11-trimethyl-7-oxa-1,10-diazatricyclo[10.5.2.0^{15,18}]nonadeca-12(19),13,15(18),16-tetraen-9-one |

TABLE 1-continued

| Example | Structure | Name |
|---|---|---|
| 157 | 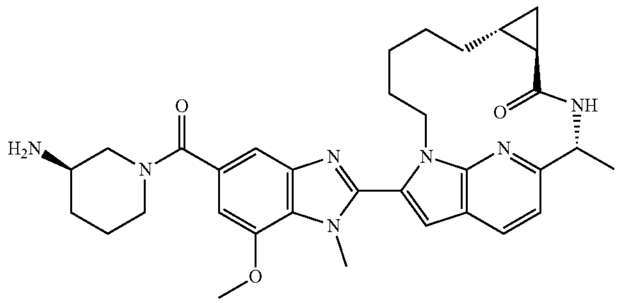 [SMILES: COc1cc(C(=O)N2CCC[C@@H](N)C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{R})-3-aminopiperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 158 | 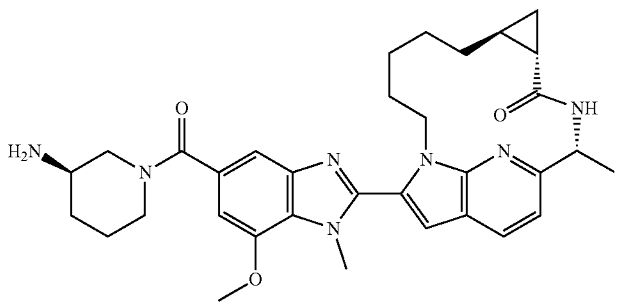 [SMILES: COc1cc(C(=O)N2CCC[C@@H](N)C2)cc2nc(-c3cc4ccc5nc4n3CCCCC[C@H]3C[C@@H]3C(=O)N[C@@H]5C)n(C)c12] | (2~{R},5~{S},7~{S})-14-[5-[(3~{R})-3-aminopiperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 159 | 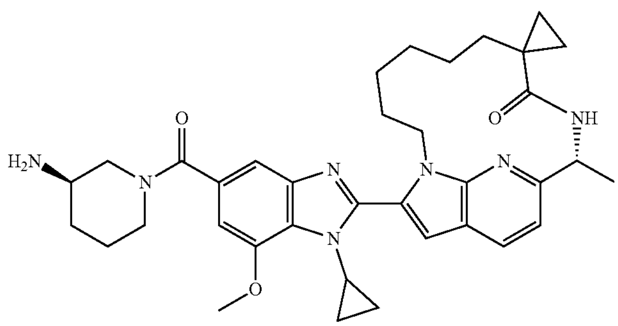 [SMILES: COc1cc(C(=O)N2CCC[C@@H](N)C2)cc2nc(-c3cc4ccc5nc4n3CCCCCCC3(CC3)C(=O)N[C@@H]5C)n(C3CC3)c12] | (11~{R})-17-[5-[(3~{R})-3-aminopiperidine-1-carbonyl]-1-cyclopropyl-7-methoxy-benzimidazol-2-yl]-11-methyl-spiro[1,10-diazatricyclo[10.5.2.0^{15,18}]nonadeca-12(19),13,15(18),16-tetraene-8,1'-cyclopropane]-9-one |
| 160 | 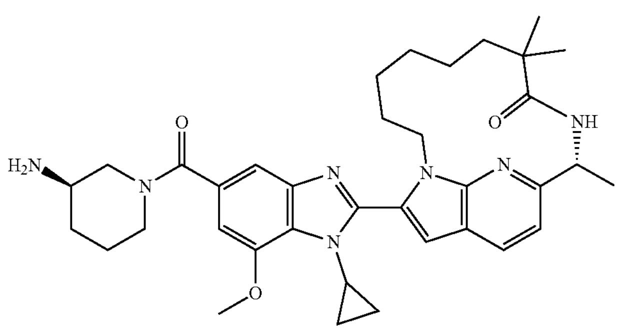 [SMILES: COc1cc(C(=O)N2CCC[C@@H](N)C2)cc2nc(-c3cc4ccc5nc4n3CCCCCCC(C)(C)C(=O)N[C@@H]5C)n(C3CC3)c12] | (11~{R})-17-[5-[(3~{R})-3-aminopiperidine-1-carbonyl]-1-cyclopropyl-7-methoxy-benzimidazol-2-yl]-8,8,11-trimethyl-1,10-diazatricyclo[10.5.2.0^{15,18}]nonadeca-12(19),13,15(18),16-tetraen-9-one |
| 161 | 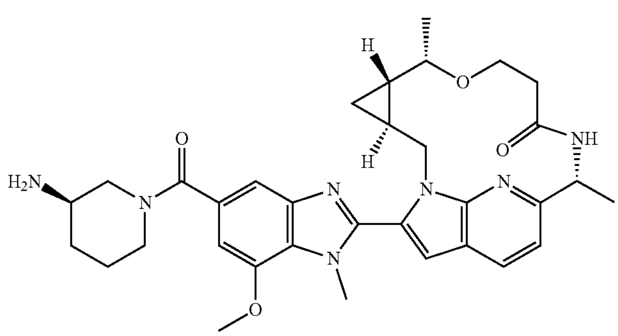 [SMILES: COc1cc(C(=O)N2CCC[C@@H](N)C2)cc2nc(-c3cc4ccc5nc4n3C[C@H]3C[C@@H]3[C@H](C)OCCC(=O)N[C@@H]5C)n(C)c12] | (3~{S},5~{S},6~{S},12~{R})-18-[5-[(3~{R})-3-aminopiperidine-1-carbonyl]-7-methoxy-1-methyl-benzimidazol-2-yl]-6,12-dimethyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 162 | 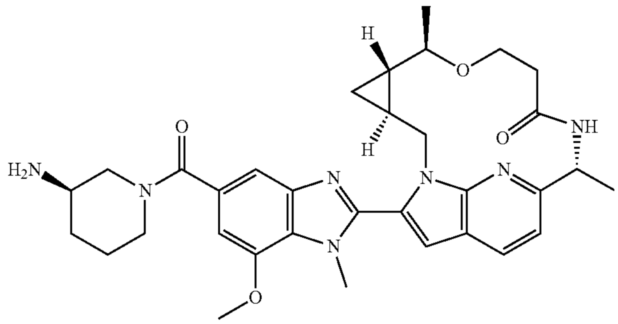 [SMILES: COc1cc(C(=O)N2CCC[C@@H](N)C2)cc2nc(-c3cc4ccc5nc4n3C[C@H]3C[C@@H]3[C@@H](C)OCCC(=O)N[C@@H]5C)n(C)c12] | (3~{S},5~{S},6~{R},12~{R})-18-[5-[(3~{R})-3-aminopiperidine-1-carbonyl]-7-methoxy-1-methyl-benzimidazol-2-yl]-6,12-dimethyl-7-oxa-1,11,20-triazatetracyclo[11.5.2.0^{3,5}.0^{16,19}]icosa-13(20),14,16(19),17-tetraen-10-one |
| 163 | 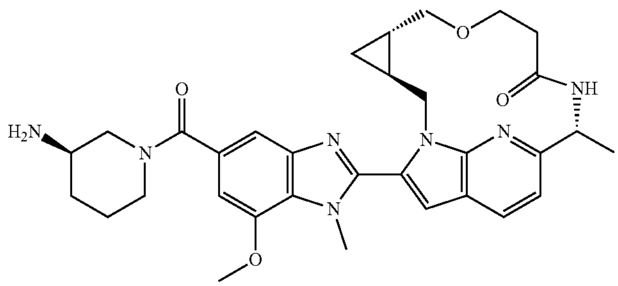 [SMILES: COc1cc(C(=O)N2CCC[C@@H](N)C2)cc2nc(-c3cc4ccc5nc4n3C[C@H]3C[C@@H]3COCCC(=O)N[C@@H]5C)n(C)c12] | (3~{S},5~{S},12~{R})-18-[5-[(3~{R})-3-aminopiperidine-1-carbonyl]-7-methoxy-1-methyl-benzimidazol-2-yl]-12-methyl-1,11,20-triazatetracyclo[11.5.2.0^{3,5}.0^{16,19}]icosa-13(20),14,16(19),17-tetraen-10-one |
| 164 | 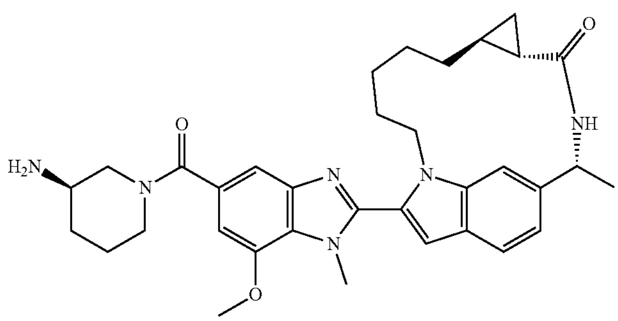 [SMILES: COc1cc(C(=O)N2CCC[C@@H](N)C2)cc2nc(-c3cc4ccc5cc4n3CCCCC[C@H]3C[C@@H]3C(=O)N[C@@H]5C)n(C)c12] | (2~{R},5~{S},7~{S})-14-[5-[(3~{R})-3-aminopiperidine-1-carbonyl]-7-methoxy-1-methyl-benzimidazol-2-yl]-2-methyl-3,13-diazatetracyclo[11.5.2.0^{5,7}.0^{16,20}]icosa-1(19),14,16(20),17-tetraen-4-one |
| 165 | 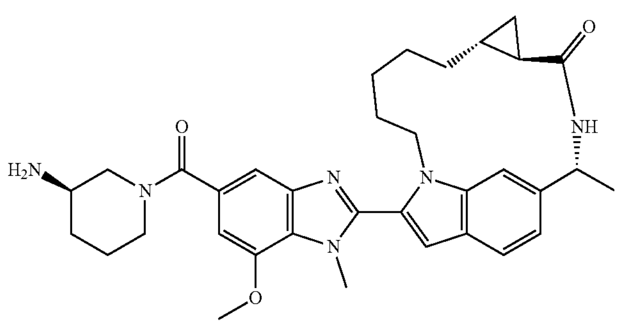 [SMILES: COc1cc(C(=O)N2CCC[C@@H](N)C2)cc2nc(-c3cc4ccc5cc4n3CCCCC[C@@H]3C[C@H]3C(=O)N[C@@H]5C)n(C)c12] | (2~{R},5~{R},7~{R})-14-[5-[(3~{R})-3-aminopiperidine-1-carbonyl]-7-methoxy-1-methyl-benzimidazol-2-yl]-2-methyl-3,13-diazatetracyclo[11.5.2.0^{5,7}.0^{16,20}]icosa-1(19),14,16(20),17-tetraen-4-one |
| 166 | 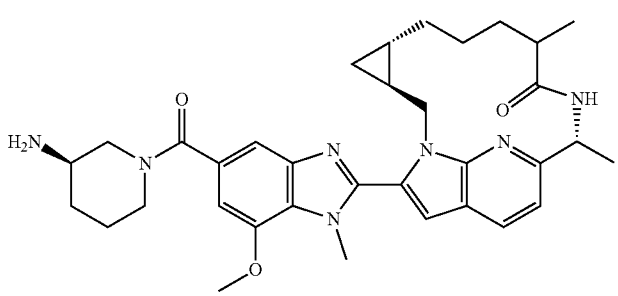 [SMILES: COc1cc(C(=O)N2CCC[C@@H](N)C2)cc2nc(-c3cc4ccc5nc4n3C[C@H]3C[C@@H]3CCCC(C)C(=O)N[C@@H]5C)n(C)c12] | (3~{S},5~{S},12~{R})-18-[5-[(3~{R})-3-aminopiperidine-1-carbonyl]-7-methoxy-1-methyl-benzimidazol-2-yl]-9,12-dimethyl-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 167 | 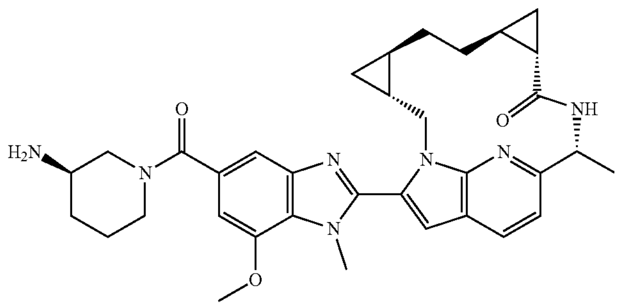 [SMILES: COc1cc(C(=O)N2CCC[C@@H](N)C2)cc2nc(-c3cc4ccc5nc4n3C[C@@H]3C[C@H]3CC[C@H]3C[C@@H]3C(=O)N[C@@H]5C)n(C)c12] | (3~{R},5~{R},8~{S},10~{S},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |
| 168 | 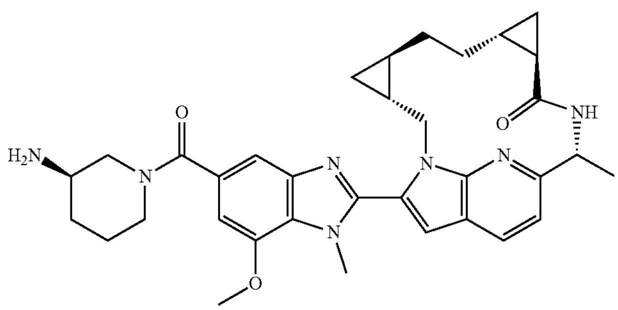 [SMILES: COc1cc(C(=O)N2CCC[C@@H](N)C2)cc2nc(-c3cc4ccc5nc4n3C[C@@H]3C[C@H]3CC[C@@H]3C[C@H]3C(=O)N[C@@H]5C)n(C)c12] | (3~{R},5~{R},8~{R},10~{R},13~{R})-19-[5-[(3~{R})-3-aminopiperidine-1-carbonyl]-7-methoxy-1-methyl-benzimidazol-2-yl]-13-methyl-1,12,21-triazapentacyclo[12.5.2.0^{3,5}.0^{8,10}.0^{17,20}]henicosa-14(21),15,17(20),18-tetraen-11-one |
| 169 | 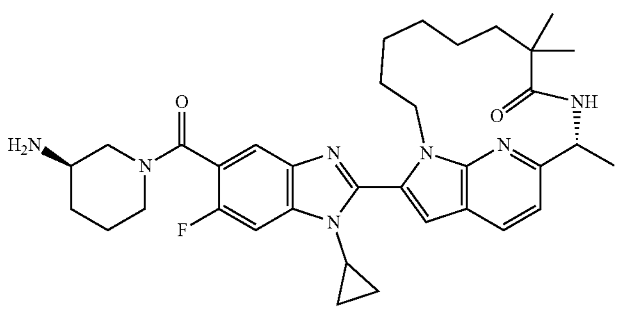 [SMILES: C[C@H]1NC(=O)C(C)(C)CCCCCCn2c(-c3nc4cc(C(=O)N5CCC[C@@H](N)C5)c(F)cc4n3C3CC3)cc3ccc1nc32] | (11~{R})-17-[5-[(3~{R})-3-aminopiperidine-1-carbonyl]-1-cyclopropyl-6-fluoro-benzimidazol-2-yl]-8,8,11-trimethyl-1,10,19-triazatricyclo[10.5.2.0^{15,18}]nonadeca-12(19),13,15(18),16-tetraen-9-one |
| 170 | 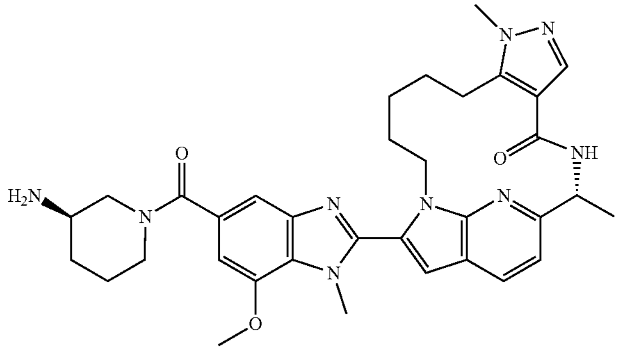 [SMILES: COc1cc(C(=O)N2CCC[C@@H](N)C2)cc2nc(-c3cc4ccc5nc4n3CCCCCc3c(cnn3C)C(=O)N[C@@H]5C)n(C)c12] | (2~{R})-16-[5-[(3~{R})-3-aminopiperidine-1-carbonyl]-7-methoxy-1-methyl-benzimidazol-2-yl]-2,8-dimethyl-3,7,8,15,21-pentazatetracyclo[13.5.2.0^{5,9}.0^{18,22}]docosa-1(21),5(9),6,16,18(22),19-hexaen-4-one |

TABLE 1-continued

| Example | Structure | Name |
|---|---|---|
| 171 | 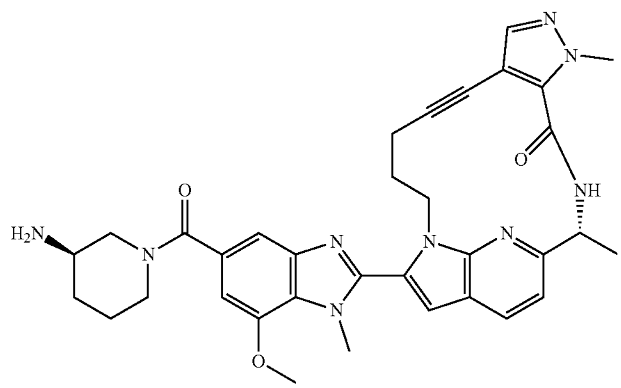 [SMILES: COc1cc(C(=O)N2CCC[C@@H](N)C2)cc2nc(-c3cc4ccc5nc4n3CCCC#Cc3cnn(C)c3C(=O)N[C@@H]5C)n(C)c12] | (2~{R})-16-[5-[(3~{R})-3-aminopiperidine-1-carbonyl]-7-methoxy-1-methyl-benzimidazol-2-yl]-2,6-dimethyl-3,6,7,15,21-pentazatetracyclo[13.5.2.0^{5,9}.0^{18,22}]docosa-1(21),5(9),7,16,18(22),19-hexaen-10-yn-4-one |
| 172 | 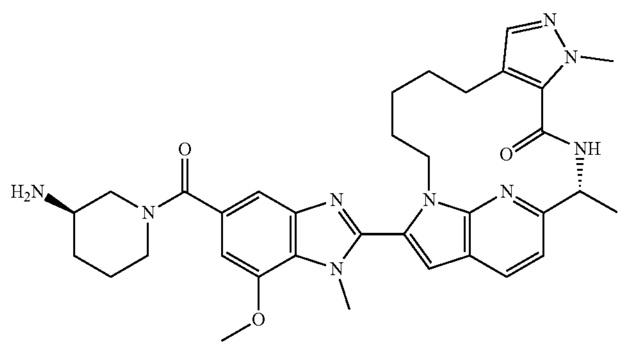 [SMILES: COc1cc(C(=O)N2CCC[C@@H](N)C2)cc2nc(-c3cc4ccc5nc4n3CCCCCc3cnn(C)c3C(=O)N[C@@H]5C)n(C)c12] | (2~{R})-16-[5-[(3~{R})-3-aminopiperidine-1-carbonyl]-7-methoxy-1-methyl-benzimidazol-2-yl]-2,6-dimethyl-3,6,7,15,21-pentazatetracyclo[13.5.2.0^{5,9}.0^{18,22}]docosa-1(21),5(9),7,16,18(22),19-hexaen-4-one |
| 173 | 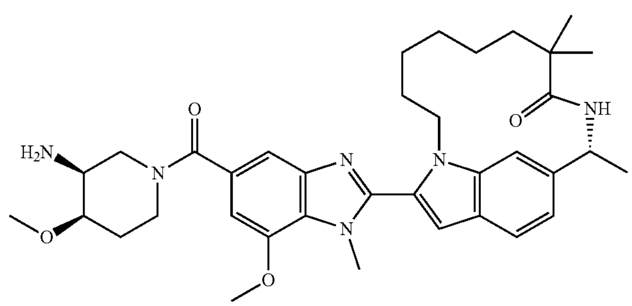 | (11~{R})-17-[5-[(3~{S},4~{R})-3-amino-4-methoxy-piperidine-1-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one |
| 174 | 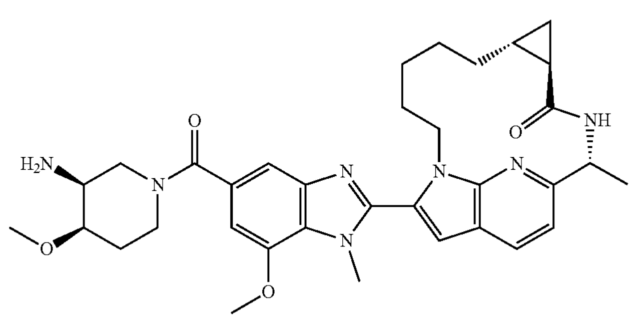 | (2~{R},5~{R},7~{R})-14-[5-[(3~{S},4~{R})-3-amino-4-methoxy-piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |

TABLE 1-continued

| Example | Structure | Name |
|---|---|---|
| 175 | 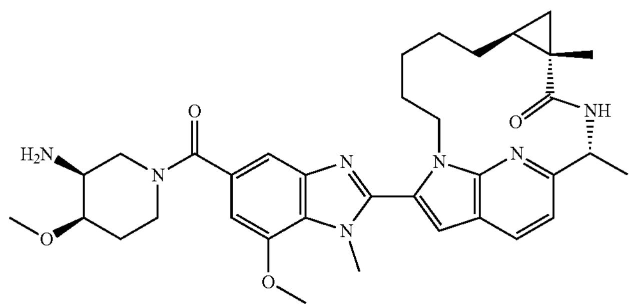 | [(3~{S},4~{R})-3-amino-4-methoxy-piperidine-1-carbonyl]-7-methoxy-1-methyl-benzimidazol-2-yl]-2,5-dimethyl-3,13,19-triazatetracyclo[11.5.2.0^{5,7}.0^{16,20}]icosa-1(19),14,16(20),17-tetraen-4-one |
| 176 | 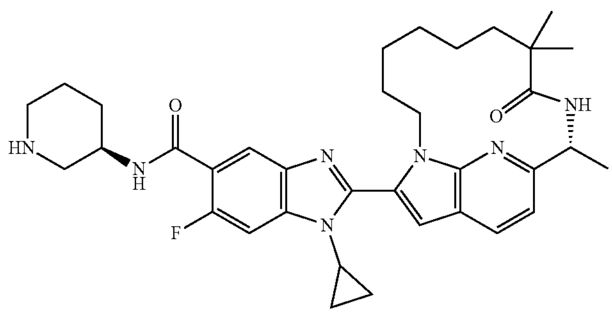 [SMILES: C[C@H]1NC(=O)C(C)(C)CCCCCCn2c(-c3nc4cc(C(=O)N[C@@H]5CCCNC5)c(F)cc4n3C3CC3)cc3ccc1nc32] | 1-cyclopropyl-6-fluoro-~{N}-[(3~{R})-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 177 | 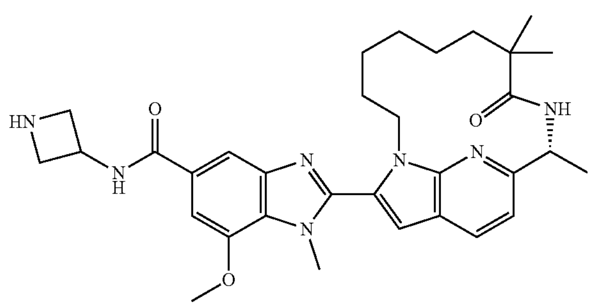 [SMILES: COc1cc(C(=O)NC2CNC2)cc2nc(-c3cc4ccc5nc4n3CCCCCCC(C)(C)C(=O)N[C@@H]5C)n(C)c12] | ~{N}-(azetidin-3-yl)-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 178 | 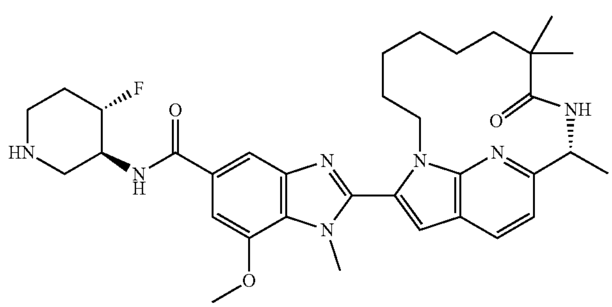 [SMILES: COc1cc(C(=O)N[C@H]2CNCC[C@@H]2F)cc2nc(-c3cc4ccc5nc4n3CCCCCCC(C)(C)C(=O)N[C@@H]5C)n(C)c12] | ~{N}-[(3~{S},4~{S})-4-fluoro-3-piperidyl]-7-methoxy-1-methyl-2-[(11~{R})-8,8,11-trimethyl-9-oxo-1,10-diazatricyclo[10.5.2.0^{15,18}]nonadeca-12(19),13,15(18),16-tetraen-17-yl]benzimidazole-5-carboxamide |
| 179 | 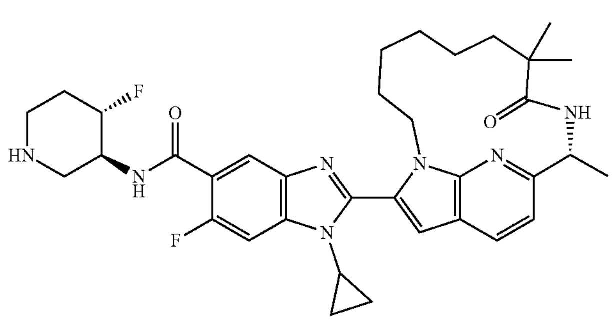 [SMILES: C[C@H]1NC(=O)C(C)(C)CCCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 180 | 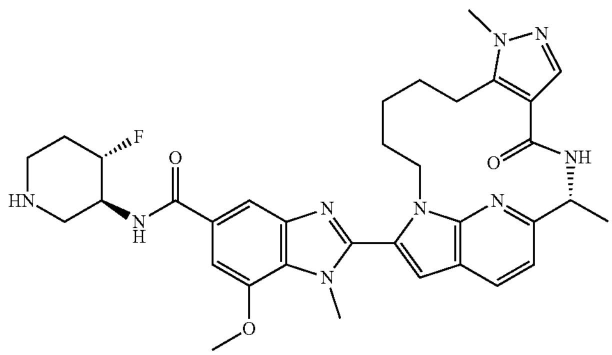 [SMILES: COc1cc(C(=O)N[C@H]2CNCC[C@@H]2F)cc2nc(-c3cc4ccc5nc4n3CCCCCc3c(cnn3C)C(=O)N[C@@H]5C)n(C)c12] | 2-[(2~{R})-2,8-dimethyl-4-oxo-3,7,8,15,21-pentazatetracyclo[13.5.2.0˄{5,9}.0˄{18,22}]docosa-1(21),5(9),6,16,18(22),19-hexaen-16-yl]-~{N}-[(3~{S},4~{S})-4-fluoro-3-piperidyl]-7-methoxy-1-methyl-benzimidazole-5-carboxamide |
| 181 | 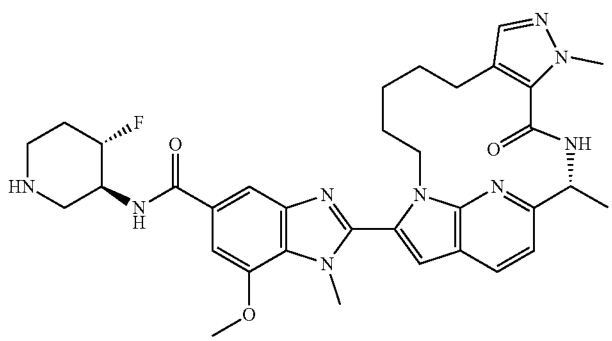 [SMILES: COc1cc(C(=O)N[C@H]2CNCC[C@@H]2F)cc2nc(-c3cc4ccc5nc4n3CCCCCc3cnn(C)c3C(=O)N[C@@H]5C)n(C)c12] | 2-[(2~{R})-2,6-dimethyl-4-oxo-3,6,7,15,21-pentazatetracyclo[13.5.2.0˄{5,9}.0˄{18,22}]docosa-1(21),5(9),7,16,18(22),19-hexaen-16-yl]-~{N}-[(3~{S},4~{S})-4-fluoro-3-piperidyl]-7-methoxy-1-methyl-benzimidazole-5-carboxamide |
| 182 | 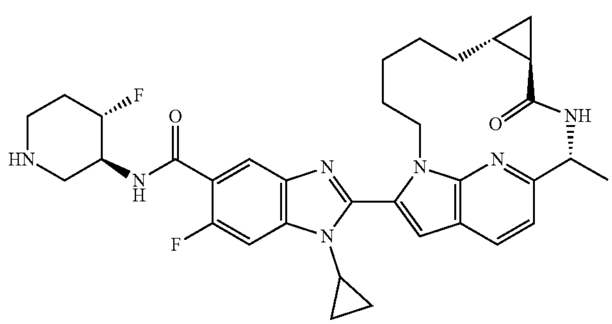 [SMILES: C[C@H]1NC(=O)[C@@H]2C[C@H]2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0˄{5,7}.0˄{16,20}]icosa-1(19),14,16(20),17-tetraen-14-yl]benzimidazole-5-carboxamide |
| 183 | 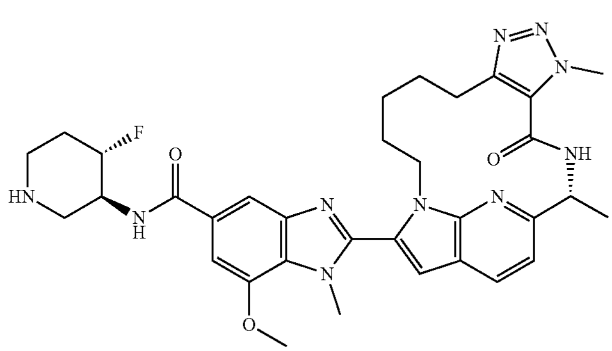 [SMILES: COc1cc(C(=O)N[C@H]2CNCC[C@@H]2F)cc2nc(-c3cc4ccc5nc4n3CCCCCc3nnn(C)c3C(=O)N[C@@H]5C)n(C)c12] | 2-[(2~{R})-2,6-dimethyl-4-oxo-3,6,7,8,15,21-hexazatetracyclo[13.5.2.0˄{5,9}.0˄{18,22}]docosa-1(21),5(9),7,16,18(22),19-hexaen-16-yl]-~{N}-[(3~{S},4~{S})-4-fluoro-3-piperidyl]-7-methoxy-1-methyl-benzimidazole-5-carboxamide |

| Example | Structure | Name |
|---|---|---|
| 184 | 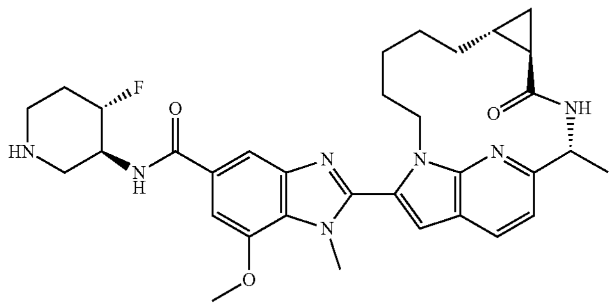 [SMILES: COc1cc(C(=O)N[C@H]2CNCC[C@@H]2F)cc2nc(-c3cc4ccc5nc4n3CCCCC[C@@H]3C[C@H]3C(=O)N[C@@H]5C)n(C)c12] | ~{N}-[(3~{S},4~{S})-4-fluoro-3-piperidyl]-7-methoxy-1-methyl-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 185 | 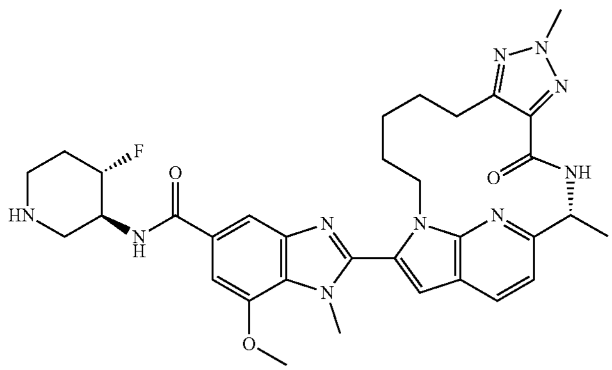 [SMILES: COc1cc(C(=O)N[C@H]2CNCC[C@@H]2F)cc2nc(-c3cc4ccc5nc4n3CCCCCc3nn(C)nc3C(=O)N[C@@H]5C)n(C)c12] | 2-[(2~{R})-2,7-dimethyl-4-oxo-3,6,7,8,15,21-hexazatetracyclo[13.5.2.0^{5,9}.0^{18,22}]docosa-1(21),5,8,16,18(22),19-hexaen-16-yl]-~{N}-[(3~{S},4~{S})-4-fluoro-3-piperidyl]-7-methoxy-1-methyl-benzimidazole-5-carboxamide |
| 186 | 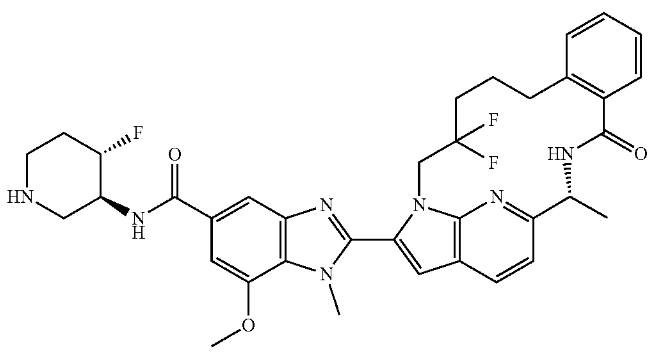 [SMILES: COc1cc(C(=O)N[C@H]2CNCC[C@@H]2F)cc2nc(-c3cc4ccc5nc4n3CC(F)(F)CCCc3ccccc3C(=O)N[C@@H]5C)n(C)c12] | 2-[(2~{R})-14,14-difluoro-2-methyl-4-oxo-3,16,22-triazatetracyclo[14.5.2.0^{5,10}.0^{19,23}]tricosa-1(22),5(10),6,8,17,19(23),20-heptaen-17-yl]-~{N}-[(3~{S},4~{S})-4-fluoro-3-piperidyl]-7-methoxy-1-methyl-benzimidazole-5-carboxamide |
| 187 | 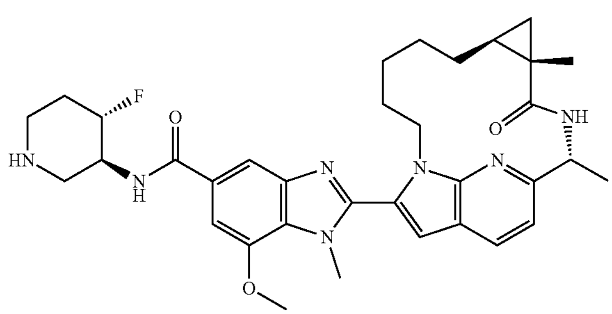 [SMILES: COc1cc(C(=O)N[C@H]2CNCC[C@@H]2F)cc2nc(-c3cc4ccc5nc4n3CCCCC[C@H]3C[C@]3(C)C(=O)N[C@@H]5C)n(C)c12] | 2-[(2~{R},5~{S},7~{S})-2,5-dimethyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]-7-methoxy-1-methyl-benzimidazole-5-carboxamide |
| 188 | 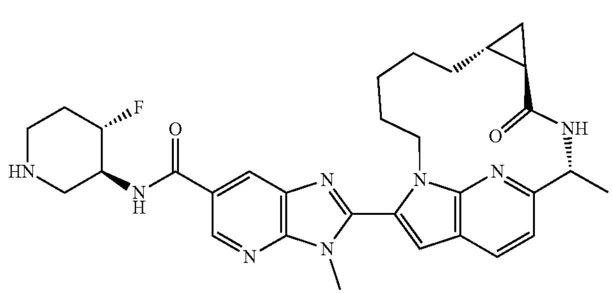 [SMILES: C[C@H]1NC(=O)[C@@H]2C[C@H]2CCCCCn2c(-c3nc4cc(C(=O)N[C@H]5CNCC[C@@H]5F)cnc4n3C)cc3ccc1nc32] | ~{N}-[(3~{S},4~{S})-4-fluoro-3-piperidyl]-3-methyl-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]imidazo[4,5-b]pyridine-6-carboxamide |

TABLE 1-continued

| Example | Structure | Name |
|---|---|---|
| 189 | 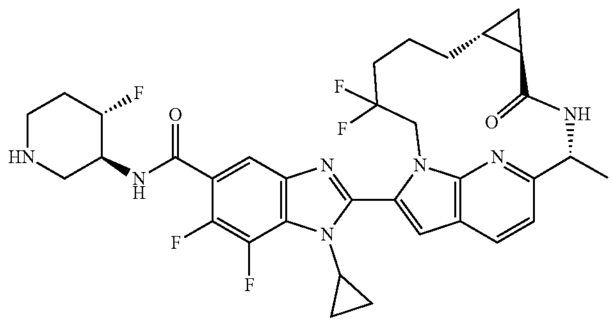 [SMILES: C[C@H]1NC(=O)[C@@H]2C[C@H]2CCCC(F)(F)Cn2c(-c3nc4cc(C(=O)N[C@H]5CNCC[C@@H]5F)c(F)c(F)c4n3C3CC3)cc3ccc1nc32] | 1-cyclopropyl-2-[(2~{R},5~{R},7~{R})-11,11-difluoro-2-methyl-4-oxo-3,13,19-triazatetracyclo[11.5.2.0^{5,7}.0^{16,20}]icosa-1(19),14,16(20),17-tetraen-14-yl]-6,7-difluoro-~{N}-[(3~{S},4~{S})-4-fluoro-3-piperidyl]benzimidazole-5-carboxamide |
| 190 | 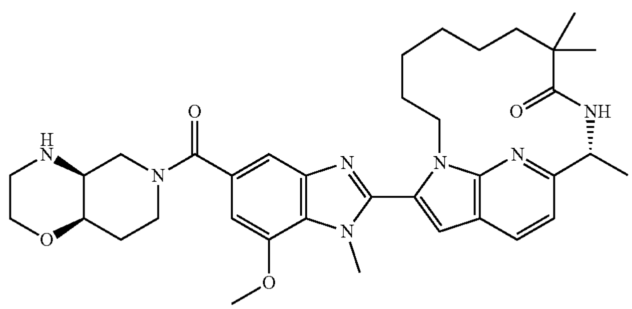 [SMILES: COc1cc(C(=O)N2CC[C@H]3OCCN[C@H]3C2)cc2nc(-c3cc4ccc5nc4n3CCCCCCC(C)(C)C(=O)N[C@@H]5C)n(C)c12] | (11~{R})-17-[5-[(4~{a}~{S},8~{a}~{R})-2,3,4,4~{a},5,7,8,8~{a}-octahydropyrido[4,3-b][1,4]oxazine-6-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one |
| 191 | 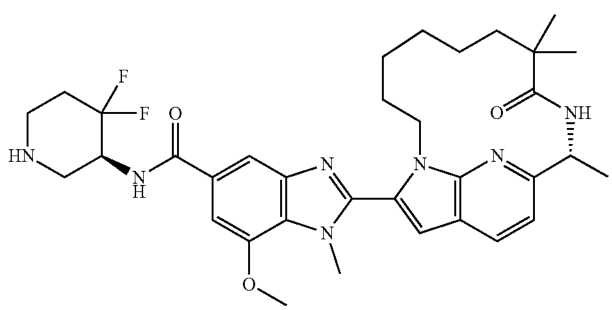 [SMILES: COc1cc(C(=O)N[C@H]2CNCCC2(F)F)cc2nc(-c3cc4ccc5nc4n3CCCCCCC(C)(C)C(=O)N[C@@H]5C)n(C)c12] | ~{N}-[(3~{S})-4,4-difluoro-3-piperidyl]-7-methoxy-1-methyl-2-[(11~{R})-8,8,11-trimethyl-9-oxo-1,10-diazatricyclo[10.5.2.0^{15,18}]nonadeca-12(19),13,15(18),16-tetraen-17-yl]benzimidazole-5-carboxamide |
| 192 | 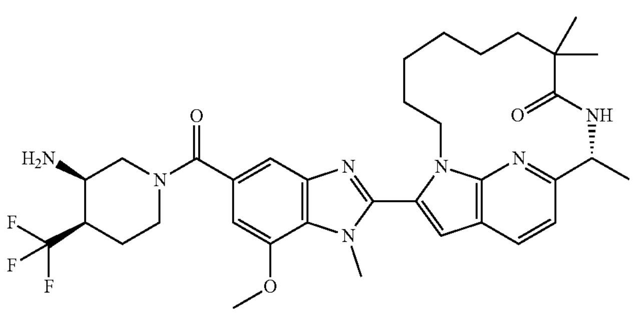 [SMILES: COc1cc(C(=O)N2CC[C@@H](C(F)(F)F)[C@@H](N)C2)cc2nc(-c3cc4ccc5nc4n3CCCCCCC(C)(C)C(=O)N[C@@H]5C)n(C)c12] | (11~{R})-17-[5-[(3~{R},4~{R})-3-amino-4-(trifluoromethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 193 | 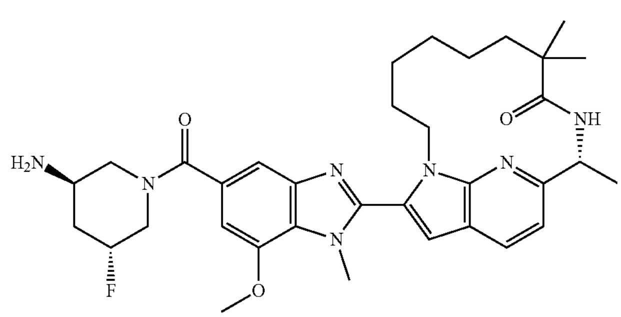 [SMILES: COc1cc(C(=O)N2C[C@H](N)C[C@@H](F)C2)cc2nc(-c3cc4ccc5nc4n3CCCCCCC(C)(C)C(=O)N[C@@H]5C)n(C)c12] | (11~{R})-17-[5-[(3~{R},5~{R})-3-amino-5-fluoro-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 194 | 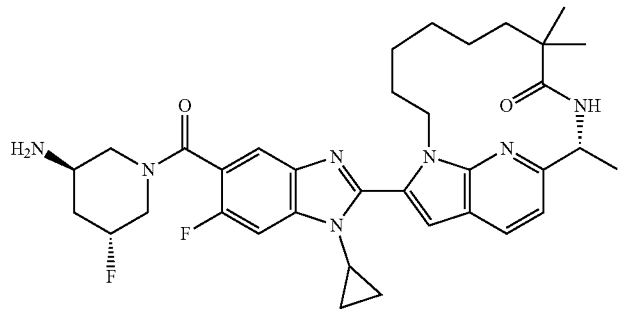 [SMILES: C[C@H]1NC(=O)C(C)(C)CCCCCCn2c(-c3nc4cc(C(=O)N5C[C@H](N)C[C@@H](F)C5)c(F)cc4n3C3CC3)cc3ccc1nc32] | (11~{R})-17-[5-[(3~{R},5~{R})-3-amino-5-fluoro-piperidine-1-carbonyl]-1-cyclopropyl-6-fluoro-benzimidazol-2-yl]-8,8,11-trimethyl-1,10,19-triazatricyclo[10.5.2.0^{15,18}]nonadeca-12(19),13,15(18),16-tetraen-9-one |
| 195 | 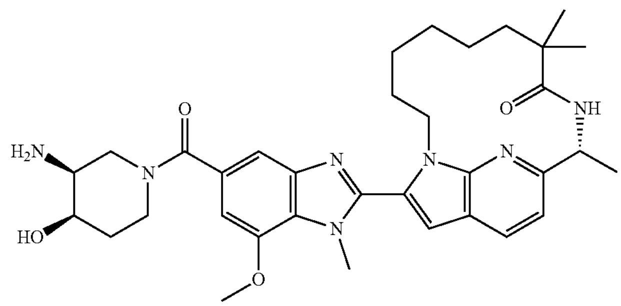 [SMILES: COc1cc(C(=O)N2CC[C@@H](O)[C@@H](N)C2)cc2nc(-c3cc4ccc5nc4n3CCCCCCC(C)(C)C(=O)N[C@@H]5C)n(C)c12] | (11~{R})-17-[5-[(3~{S},4~{R})-3-amino-4-hydroxy-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 196 | 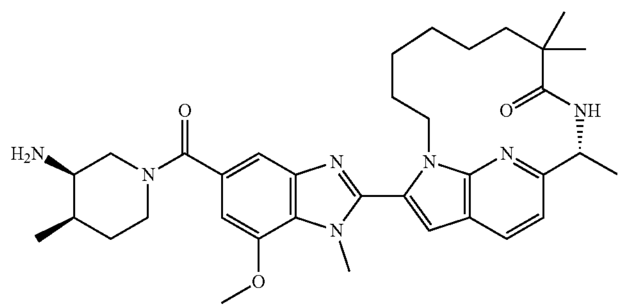 [SMILES: COc1cc(C(=O)N2CC[C@@H](C)[C@@H](N)C2)cc2nc(-c3cc4ccc5nc4n3CCCCCCC(C)(C)C(=O)N[C@@H]5C)n(C)c12] | (11~{R})-17-[5-[(3~{R},4~{R})-3-amino-4-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 197 | 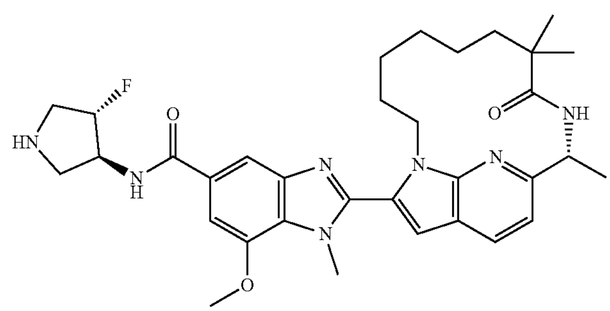 [SMILES: COc1cc(C(=O)N[C@H]2CNC[C@@H]2F)cc2nc(-c3cc4ccc5nc4n3CCCCCCC(C)(C)C(=O)N[C@@H]5C)n(C)c12] | ~{N}-[(3~{S},4~{S})-4-fluoropyrrolidin-3-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 198 | 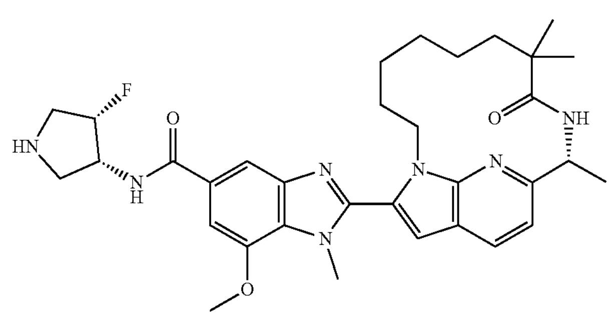 [SMILES: COc1cc(C(=O)N[C@@H]2CNC[C@@H]2F)cc2nc(-c3cc4ccc5nc4n3CCCCCCC(C)(C)C(=O)N[C@@H]5C)n(C)c12] | ~{N}-[(3~{R},4~{S})-4-fluoropyrrolidin-3-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 199 | 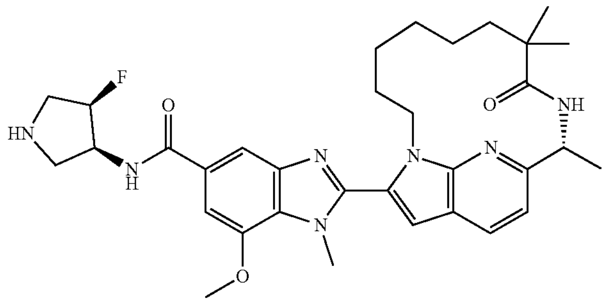 [SMILES: COc1cc(C(=O)N[C@H]2CNC[C@H]2F)cc2nc(-c3cc4ccc5nc4n3CCCCCCC(C)(C)C(=O)N[C@@H]5C)n(C)c12] | ~{N}-[(3~{S},4~{R})-4-fluoropyrrolidin-3-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 200 | 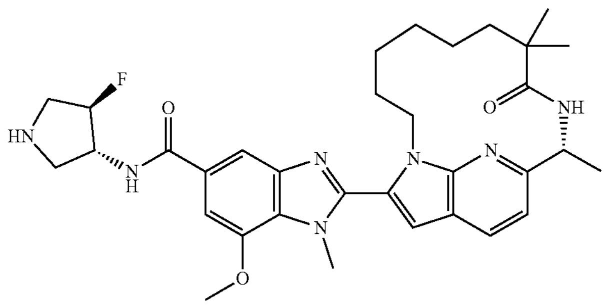 [SMILES: COc1cc(C(=O)N[C@@H]2CNC[C@H]2F)cc2nc(-c3cc4ccc5nc4n3CCCCCCC(C)(C)C(=O)N[C@@H]5C)n(C)c12] | ~{N}-[(3~{R},4~{R})-4-fluoropyrrolidin-3-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 201 | 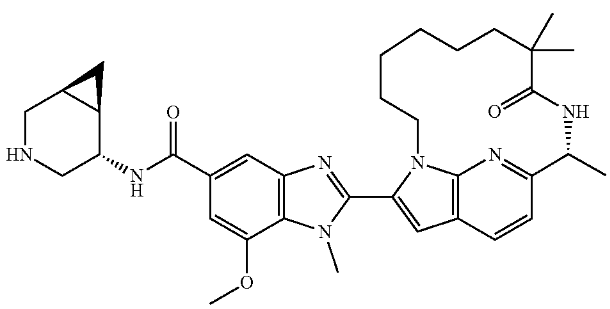 [SMILES: COc1cc(C(=O)N[C@@H]2CNC[C@H]3C[C@H]32)cc2nc(-c3cc4ccc5nc4n3CCCCCCC(C)(C)C(=O)N[C@@H]5C)n(C)c12] | ~{N}-[(1~{S},5~{S},6~{R})-3-azabicyclo[4.1.0]heptan-5-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 202 | 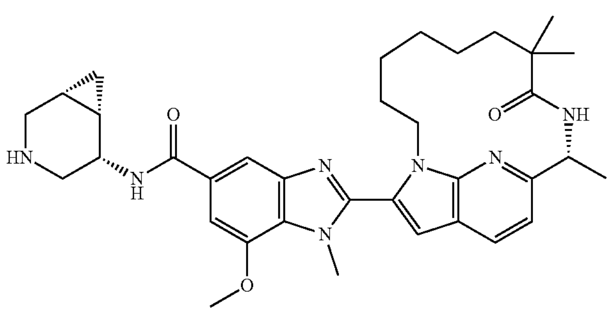 [SMILES: COc1cc(C(=O)N[C@@H]2CNC[C@@H]3C[C@@H]32)cc2nc(-c3cc4ccc5nc4n3CCCCCCC(C)(C)C(=O)N[C@@H]5C)n(C)c12] | ~{N}-[(1~{R},5~{S},6~{S})-3-azabicyclo[4.1.0]heptan-5-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 203 | 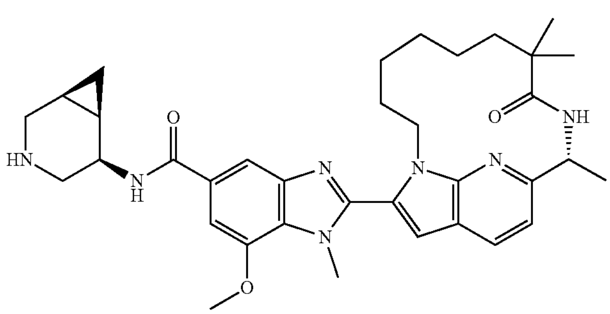 [SMILES: COc1cc(C(=O)N[C@H]2CNC[C@H]3C[C@H]32)cc2nc(-c3cc4ccc5nc4n3CCCCCCC(C)(C)C(=O)N[C@@H]5C)n(C)c12] | ~{N}-[(1~{S},5~{R},6~{R})-3-azabicyclo[4.1.0]heptan-5-yl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 204 | 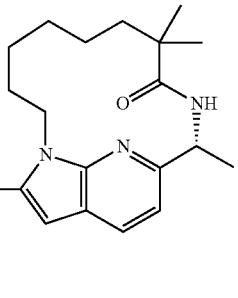 | (11~{R})-17-[5-(5-amino-3,3-difluoro-piperidine-1-carbonyl)-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 205 | 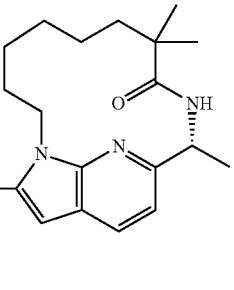 | ~{N}-(3-azabicyclo[3.2.1]octan-8-yl)-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 206 | 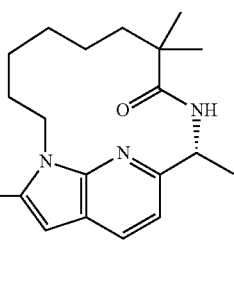 | (11~{R})-17-[5-[(1~{S},5~{R},6~{R})-5-amino-3-azabicyclo[4.1.0]heptane-3-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 207 | 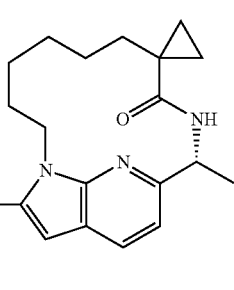 | (11~{R})-17-[5-[(1~{R},2~{S},3~{R},5~{S})-2-amino-3-hydroxy-8-azabicyclo[3.2.1]octane-8-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |
| 208 | 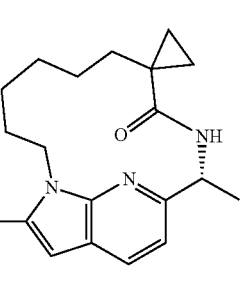 | (11~{R})-17-[5-[(4~{a}-{S},8~{a}~{R})-2,3,4,4~{a},5,7,8,8~{a}-octahydropyrido[4,3-b][1,4]oxazine-6-carbonyl]-7-methoxy-1-methyl-benzimidazol-2-yl]-11-methyl-spiro[1,10-diazatricyclo[10.5.2.0^{15,18}]nonadeca-12(19),13,15(18),16-tetraene-8,1'-cyclopropane]-9-one |

TABLE 1-continued

| Example | Structure | Name |
|---|---|---|
| 209 | 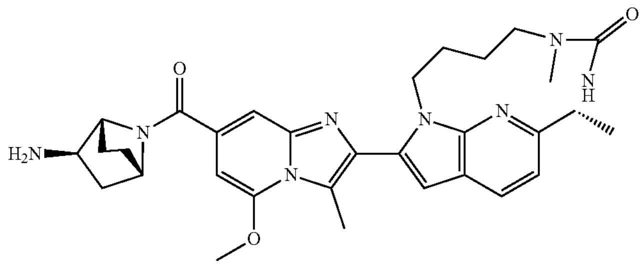 | (9~{R})-15-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-6,9-dimethyl-1,6,8,17-tetrazatricyclo[8.5.2.0^{13,16}]heptadeca-10(17),11,13(16),14-tetraen-7-one |
| 210 | 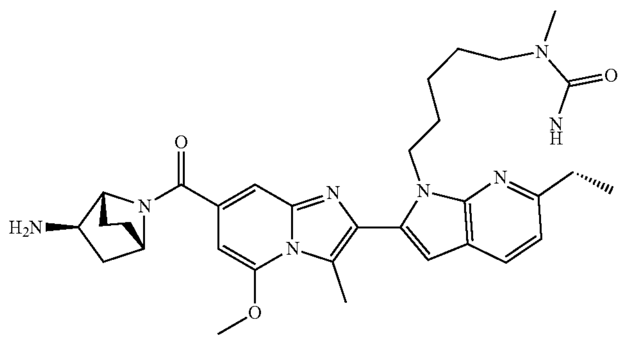 | (10~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-7,10-dimethyl-1,7,9,18-tetrazatricyclo[9.5.2.0^{14,17}]octadeca-11(18),12,14(17),15-tetraen-8-one |
| 211 | 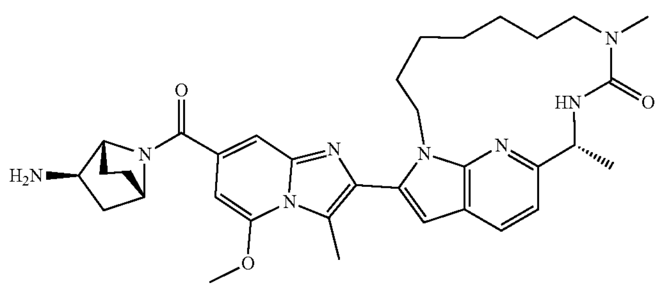 [SMILES: COc1cc(C(=O)N2[C@H]3CC[C@@H]2[C@H](N)C3)cc2nc(-c3cc4ccc5nc4n3CCCCCCCN(C)C(=O)N[C@@H]5C)c(C)n12] | (12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-9,12-dimethyl-1,9,11,20-tetrazatricyclo[11.5.2.0^{16,19}]icosa-13(20),14,16(19),17-tetraen-10-one |
| 212 | 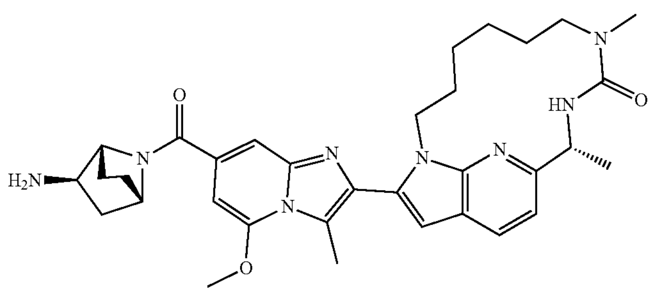 [SMILES: COc1cc(C(=O)N2[C@H]3CC[C@@H]2[C@H](N)C3)cc2nc(-c3cc4ccc5nc4n3CCCCCCN(C)C(=O)N[C@@H]5C)c(C)n12] | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8,11-dimethyl-1,8,10,19-tetrazatricyclo[10.5.2.0^{15,18}]nonadeca-12(19),13,15(18),16-tetraen-9-one |
| 213 | 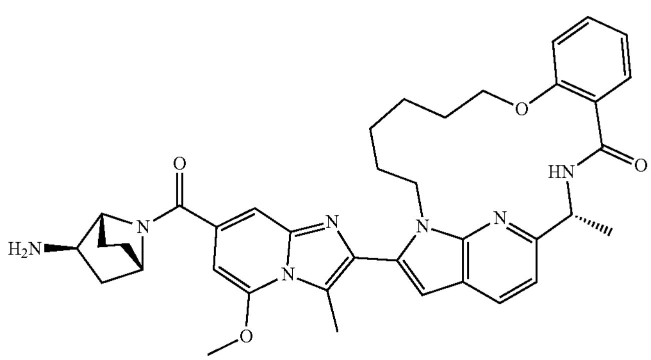 [SMILES: COc1cc(C(=O)N2[C@H]3CC[C@@H]2[C@H](N)C3)cc2nc(-c3cc4ccc5nc4n3CCCCCCOc3ccccc3C(=O)N[C@@H]5C)c(C)n12] | (2~{R})-19-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-2-methyl-11-oxa-3,18,24-triazatetracyclo[16.5.2.0^{5,10}.0^{21,25}]pentacosa-1(24),5(10),6,8,19,21(25),22-heptaen-4-one |

TABLE 1-continued

| Example | Structure | Name |
|---|---|---|
| 214 | 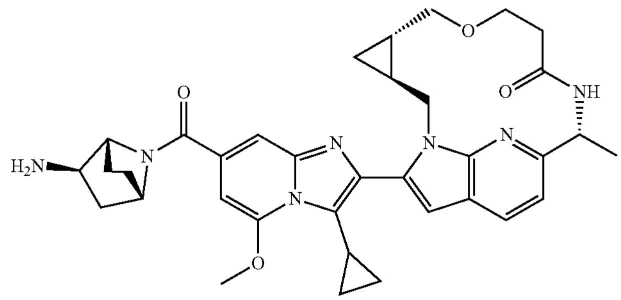 [SMILES: COc1cc(C(=O)N2[C@H]3CC[C@@H]2[C@H](N)C3)cc2nc(-c3cc4ccc5nc4n3C[C@H]3C[C@@H]3COCCC(=O)N[C@@H]5C)c(C3CC3)n12] | (3~{S},5~{S},12~{R})-18-[7-[(1~{R},2~{R},4~{S})-2-amino-7-azabicyclo[2.2.1]heptane-7-carbonyl]-3-cyclopropyl-5-methoxy-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one |
| 215 | 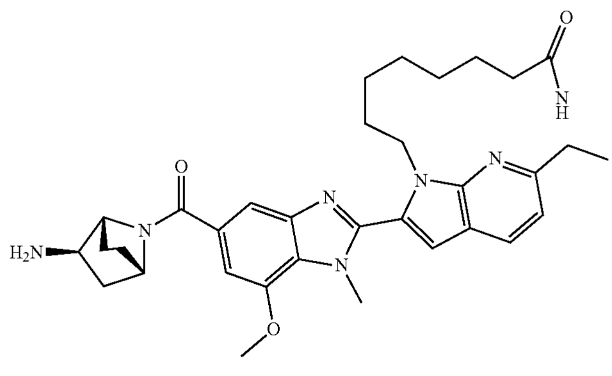 [SMILES: CCc1ccc2cc(-c3nc4cc(C(=O)N5[C@H]6CC[C@@H]5[C@H](N)C6)cc(OC)c4n3C)n(CCCCCCCC(N)=O)c2n1] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-1,10-diazatricyclo[10.5.2.0^{15,18}]nonadeca-12(19),13,15(18),16-tetraen-9-one |
| 216 | 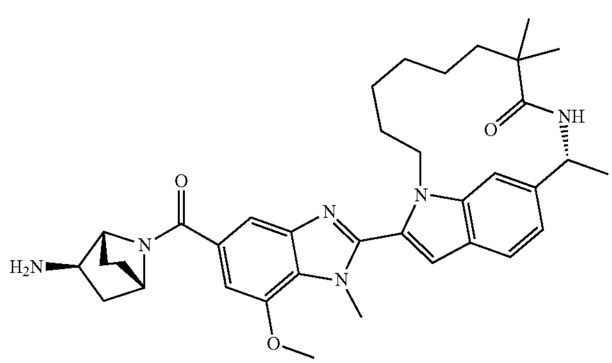 [SMILES: COc1cc(C(=O)N2[C@H]3CC[C@@H]2[C@H](N)C3)cc2nc(-c3cc4ccc5cc4n3CCCCCCC(C)(C)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one |
| 217 | 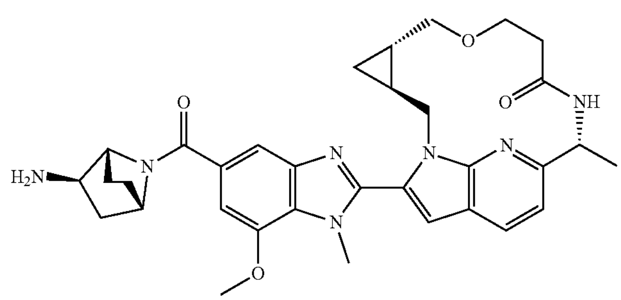 [SMILES: COc1cc(C(=O)N2[C@H]3CC[C@@H]2[C@H](N)C3)cc2nc(-c3cc4ccc5nc4n3C[C@H]3C[C@@H]3COCCC(=O)N[C@@H]5C)n(C)c12] | (3~{S},5~{S},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 218 | 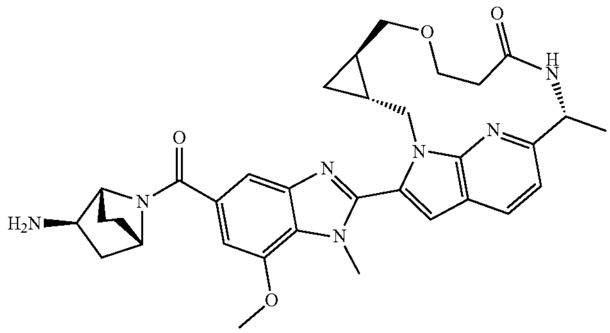 [SMILES: COc1cc(C(=O)N2[C@H]3CC[C@@H]2[C@H](N)C3)cc2nc(-c3cc4ccc5nc4n3C[C@@H]3C[C@H]3COCCC(=O)N[C@@H]5C)n(C)c12] | (3~{R},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 219 | 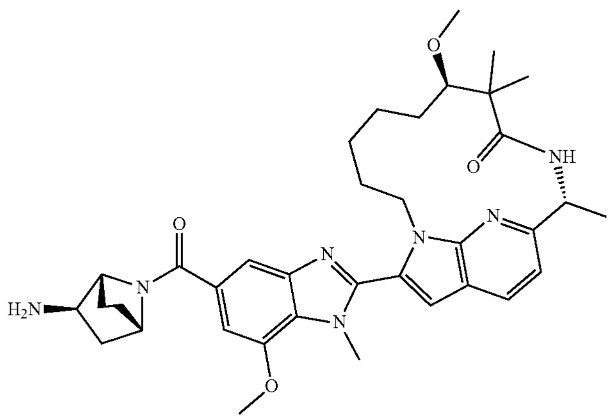 [SMILES: COc1cc(C(=O)N2[C@H]3CC[C@@H]2[C@H](N)C3)cc2nc(-c3cc4ccc5nc4n3CCCCC[C@@H](OC)C(C)(C)C(=O)N[C@@H]5C)n(C)c12] | (7~{R},11~{R})-17-[5-[(1~{R},2~{R},4~{S})-2-amino-7-azabicyclo[2.2.1]heptane-7-carbonyl]-7-methoxy-1-methyl-benzimidazol-2-yl]-7-methoxy-8,8,11-trimethyl-1,10,19-triazatricyclo[10.5.2.0^{15,18}]nonadeca-12(19),13,15(18),16-tetraen-9-one |
| 220 | 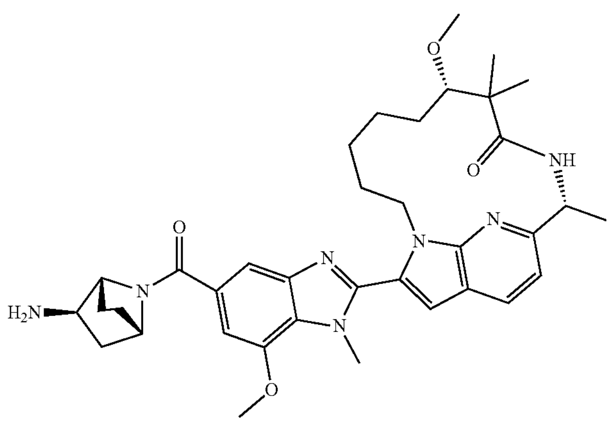 [SMILES: COc1cc(C(=O)N2[C@H]3CC[C@@H]2[C@H](N)C3)cc2nc(-c3cc4ccc5nc4n3CCCCC[C@H](OC)C(C)(C)C(=O)N[C@@H]5C)n(C)c12] | (7~{S},11~{R})-17-[5-[(1~{R},2~{R},4~{S})-2-amino-7-azabicyclo[2.2.1]heptane-7-carbonyl]-7-methoxy-1-methyl-benzimidazol-2-yl]-7-methoxy-8,8,11-trimethyl-1,10,19-triazatricyclo[10.5.2.0^{15,18}]nonadeca-12(19),13,15(18),16-tetraen-9-one |
| 221 | 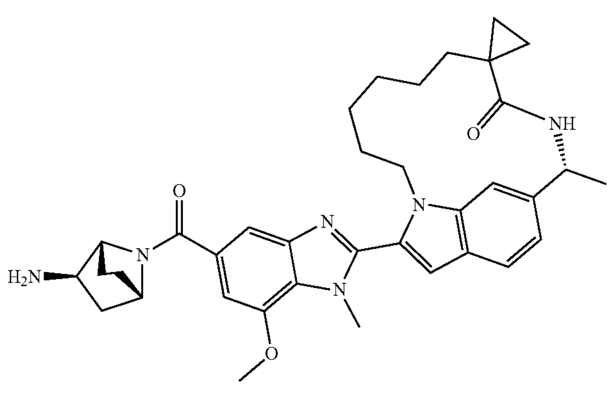 [SMILES: COc1cc(C(=O)N2[C@H]3CC[C@@H]2[C@H](N)C3)cc2nc(-c3cc4ccc5cc4n3CCCCCCC3(CC3)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-spiro[1,10-diazatricyclo[10.5.2.0^{15,18}]nonadeca-12(19),13,15(18),16-tetraene-8,1'-cyclopropane]-9-one |

TABLE 1-continued

| Example | Structure | Name |
|---|---|---|
| 222 | 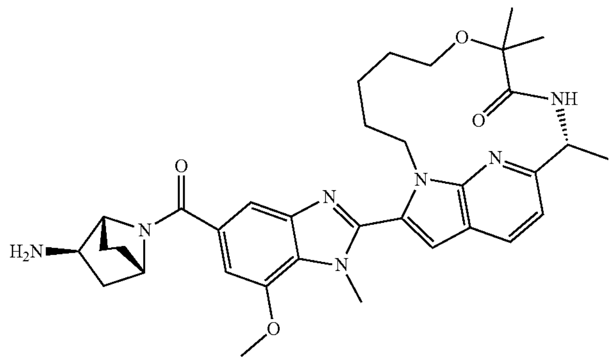 [SMILES: COc1cc(C(=O)N2[C@H]3CC[C@@H]2[C@H](N)C3)cc2nc(-c3cc4ccc5nc4n3CCCCCOC(C)(C)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-8,8,11-trimethyl-7-oxa-1,10-diazatricyclo[10.5.2.0^{15,18}]nonadeca-12(19),13,15(18),16-tetraen-9-one |
| 223 | 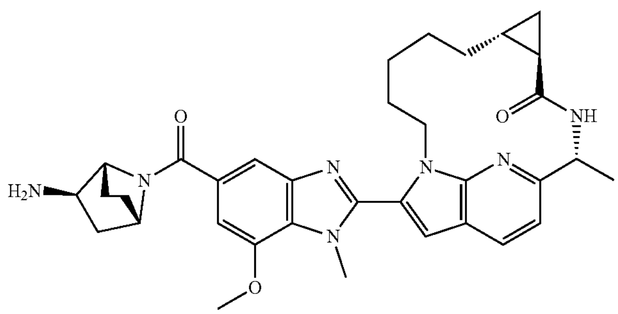 [SMILES: COc1cc(C(=O)N2[C@H]3CC[C@@H]2[C@H](N)C3)cc2nc(-c3cc4ccc5nc4n3CCCCC[C@@H]3C[C@H]3C(=O)N[C@@H]5C)n(C)c12] | (2~{R},5~{R},7~{R})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 224 | 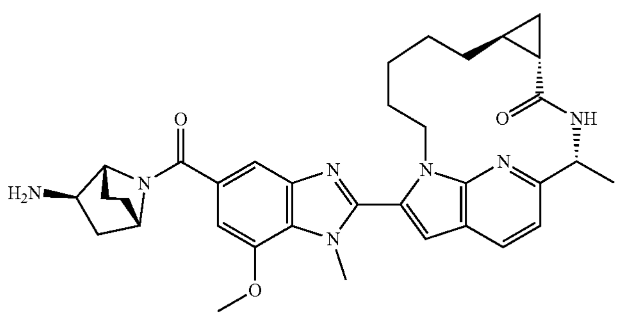 [SMILES: COc1cc(C(=O)N2[C@H]3CC[C@@H]2[C@H](N)C3)cc2nc(-c3cc4ccc5nc4n3CCCCC[C@H]3C[C@@H]3C(=O)N[C@@H]5C)n(C)c12] | (2~{R},5~{S},7~{S})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 225 | 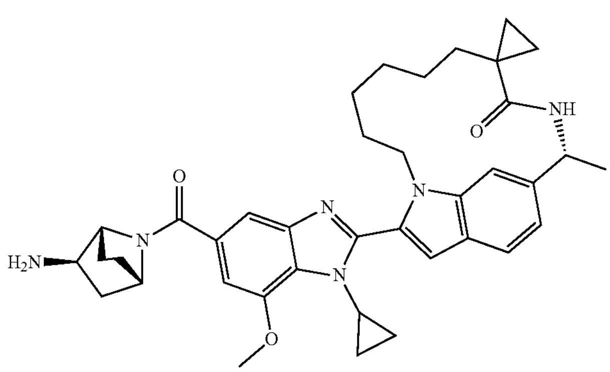 [SMILES: COc1cc(C(=O)N2[C@H]3CC[C@@H]2[C@H](N)C3)cc2nc(-c3cc4ccc5cc4n3CCCCCCC3(CC3)C(=O)N[C@@H]5C)n(C3CC3)c12] | (11~{R})-17-[5-[(1~{R},2~{R},4~{S})-2-amino-7-azabicyclo[2.2.1]heptane-7-carbonyl]-1-cyclopropyl-7-methoxy-benzimidazol-2-yl]-11-methyl-spiro[1,10-diazatricyclo[10.5.2.0^{15,18}]nonadeca-12(19),13,15(18),16-tetraene-8,1'-cyclopropane]-9-one |

TABLE 1-continued

| Example | Structure | Name |
|---|---|---|
| 226 | 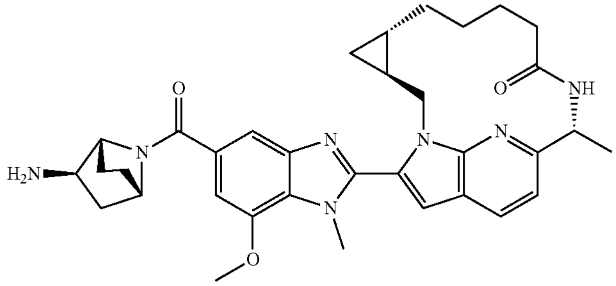 [SMILES: COc1cc(C(=O)N2[C@H]3CC[C@@H]2[C@H](N)C3)cc2nc(-c3cc4ccc5nc4n3C[C@H]3C[C@@H]3CCCCC(=O)N[C@@H]5C)n(C)c12] | (3~{S},5~{S},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-1,11,20-triazatetracyclo[11.5.2.0^{3,5}.0^{16,19}]icosa-13(20),14,16(19),17-tetraen-10-one |
| 227 | 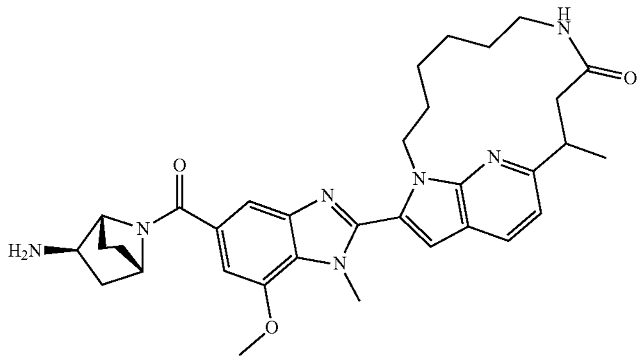 [SMILES: COc1cc(C(=O)N2[C@H]3CC[C@@H]2[C@H](N)C3)cc2nc(-c3cc4ccc5nc4n3CCCCCCNC(=O)CC5C)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-11-methyl-1,8,19-triazatricyclo[10.5.2.0^{15,18}]nonadeca-12(19),13,15(18),16-tetraen-9-one |
| 228 | 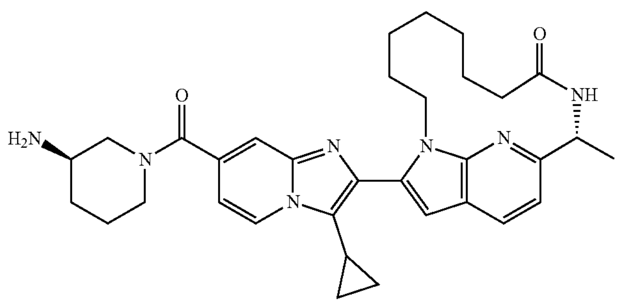 [SMILES: C[C@H]1NC(=O)CCCCCCCn2c(-c3nc4cc(C(=O)N5CCC[C@@H](N)C5)ccn4c3C3CC3)cc3ccc1nc32] | (11~{R})-17-[7-[(3~{R})-3-aminopiperidine-1-carbonyl]-3-cyclopropyl-imidazo[1,2-a]pyridin-2-yl]-11-methyl-1,10,19-triazatricyclo[10.5.2.0^{15,18}]nonadeca-12(19),13,15(18),16-tetraen-9-one |
| 229 | 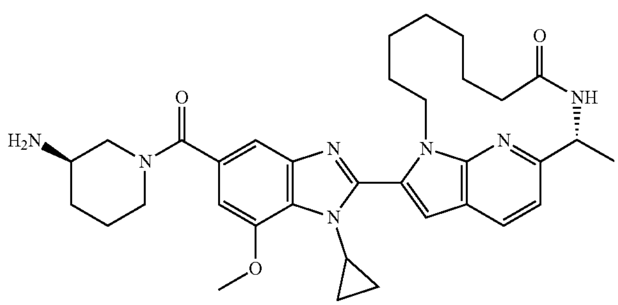 [SMILES: COc1cc(C(=O)N2CCC[C@@H](N)C2)cc2nc(-c3cc4ccc5nc4n3CCCCCCCC(=O)N[C@@H]5C)n(C3CC3)c12] | (11~{R})-17-[5-[(3~{R})-3-aminopiperidine-1-carbonyl]-1-cyclopropyl-7-methoxy-benzimidazol-2-yl]-11-methyl-1,10,19-triazatricyclo[10.5.2.0^{15,18}]nonadeca-12(19),13,15(18),16-tetraen-9-one |
| 230 | 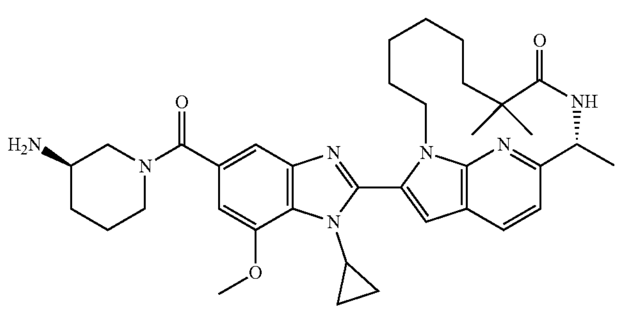 [SMILES: COc1cc(C(=O)N2CCC[C@@H](N)C2)cc2nc(-c3cc4ccc5nc4n3CCCCCCC(C)(C)C(=O)N[C@@H]5C)n(C3CC3)c12] | (11~{R})-17-[5-[(3~{R})-3-aminopiperidine-1-carbonyl]-1-cyclopropyl-7-methoxy-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 231 | 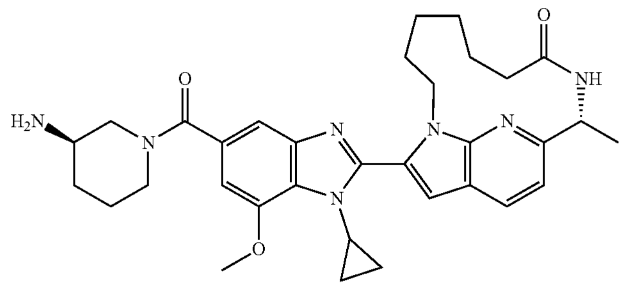 [SMILES: COc1cc(C(=O)N2CCC[C@@H](N)C2)cc2nc(-c3cc4ccc5nc4n3CCCCCCC(=O)N[C@@H]5C)n(C3CC3)c12] | (10~{R})-16-[5-[(3~{R})-3-aminopiperidine-1-carbonyl]-1-cyclopropyl-7-methoxy-benzimidazol-2-yl]-10-methyl-1,9,18-triazatricyclo[9.5.2.0^{14,17}]octadeca-11(18),12,14(17),15-tetraen-8-one |
| 232 | 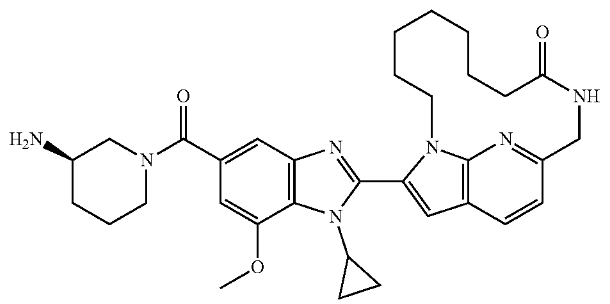 [SMILES: COc1cc(C(=O)N2CCC[C@@H](N)C2)cc2nc(-c3cc4ccc5nc4n3CCCCCCCC(=O)NC5)n(C3CC3)c12] | 17-[5-[(3~{R})-3-aminopiperidine-1-carbonyl]-7-methoxy-1-methyl-benzimidazol-2-yl]-1,10,19-triazatricyclo[10.5.2.0^{15,18}]nonadeca-12(19),13,15(18),16-tetraen-9-one |
| 233 | 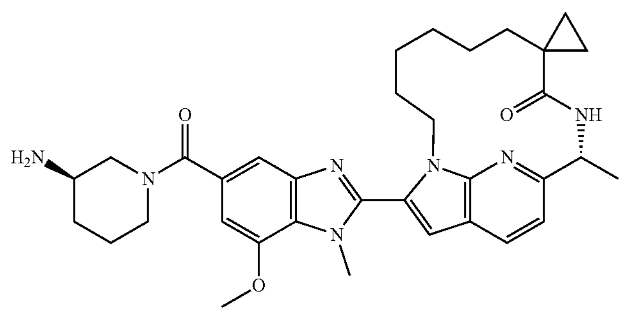 [SMILES: COc1cc(C(=O)N2CCC[C@@H](N)C2)cc2nc(-c3cc4ccc5nc4n3CCCCCCC3(CC3)C(=O)N[C@@H]5C)n(C)c12] | (11~{R})-17-[5-[(3~{R})-3-aminopiperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |
| 234 | 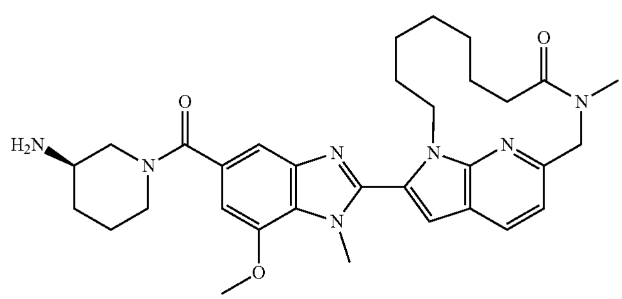 [SMILES: COc1cc(C(=O)N2CCC[C@@H](N)C2)cc2nc(-c3cc4ccc5nc4n3CCCCCCCC(=O)N(C)C5)n(C)c12] | 17-[5-[(3~{R})-3-aminopiperidine-1-carbonyl]-7-methoxy-1-methyl-benzimidazol-2-yl]-10-methyl-1,10,19-triazatricyclo[10.5.2.0^{15,18}]nonadeca-12(19),13,15(18),16-tetraen-9-one |
| 235 | 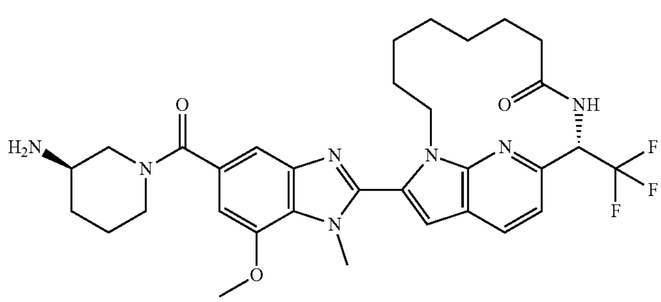 [SMILES: COc1cc(C(=O)N2CCC[C@@H](N)C2)cc2nc(-c3cc4ccc5nc4n3CCCCCCCC(=O)N[C@@H]5C(F)(F)F)n(C)c12] | (11~{S})-17-[5-[(3~{R})-3-aminopiperidine-1-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one |

TABLE 1-continued

| Example | Structure | Name |
|---|---|---|
| 236 | 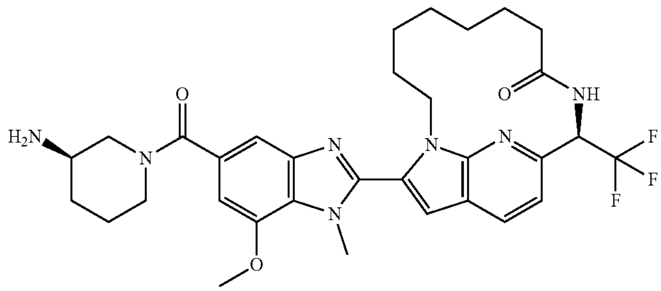 [SMILES: COc1cc(C(=O)N2CCC[C@@H](N)C2)cc2nc(-c3cc4ccc5nc4n3CCCCCCCC(=O)N[C@H]5C(F)(F)F)n(C)c12] | (11~{R})-17-[5-[(3~{R})-3-aminopiperidine-1-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one |
| 237 | 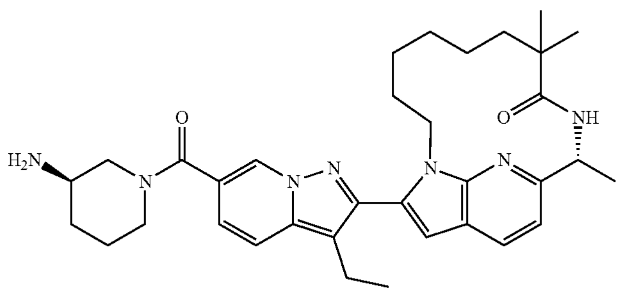 [SMILES: CCc1c(-c2cc3ccc4nc3n2CCCCCCC(C)(C)C(=O)N[C@@H]4C)nn2cc(C(=O)N3CCC[C@@H](N)C3)ccc12] | (11~{R})-17-[6-[(3~{R})-3-aminopiperidine-1-carbonyl]-3-ethyl-pyrazolo[1,5-a]pyridin-2-yl]-8,8,11-trimethyl-1,10,19-triazatricyclo[10.5.2.0^{15,18}]nonadeca-12(19),13,15(18),16-tetraen-9-one |
| 238 | 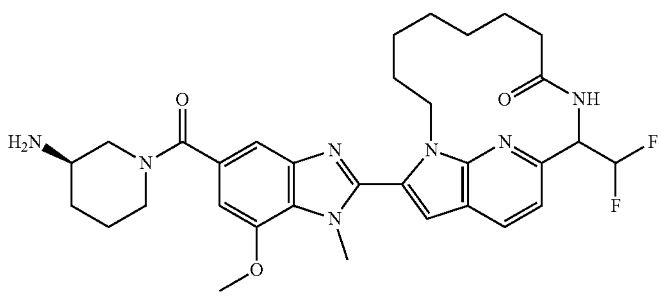 [SMILES: COc1cc(C(=O)N2CCC[C@@H](N)C2)cc2nc(-c3cc4ccc5nc4n3CCCCCCCC(=O)NC5C(F)F)n(C)c12] | 17-[5-[(3~{R})-3-aminopiperidine-1-carbonyl]-7-methoxy-1-methyl-benzimidazol-2-yl]-11-(difluoromethyl)-1,10,19-triazatricyclo[10.5.2.0^{15,18}]nonadeca-12(19),13,15(18),16-tetraen-9-one |
| 239 | 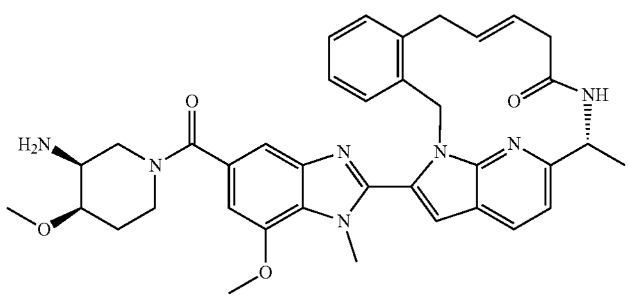 | (10~{E},15~{R})-21-[5-[(3~{S},4~{R})-3-amino-4-methoxy-piperidine-1-carbonyl]-7-methoxy-1-methyl-benzimidazol-2-yl]-15-methyl-1,14,23-triazatetracyclo[14.5.2.0^{3,8}.0^{19,22}]tricosa-3(8),4,6,10,16,18,20,22-octaen-13-one |
| 240 | 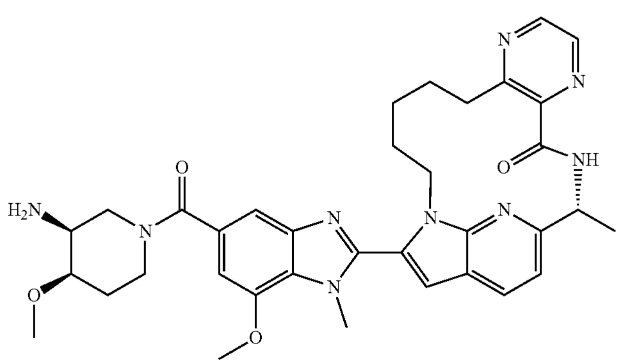 [SMILES: COc1cc(C(=O)N2CC[C@@H](OC)[C@@H](N)C2)cc2nc(-c3cc4ccc5nc4n3CCCCCc3nccnc3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-2-methyl-3,6,9,16,22-pentazatetracyclo[14.5.2.0^{5,10}.0^{19,23}]tricosa-1(21),5(10),6,8,17,19,22-heptaen-4-one |

TABLE 1-continued

| Example | Structure | Name |
|---|---|---|
| 241 | 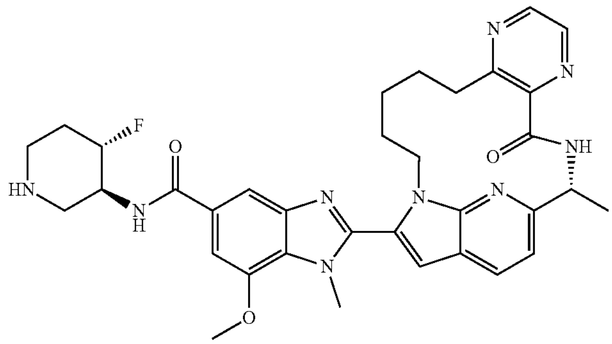 [SMILES: COc1cc(C(=O)N[C@H]2CNCC[C@@H]2F)cc2nc(-c3cc4ccc5nc4n3CCCCCc3nccnc3C(=O)N[C@@H]5C)n(C)c12] | ~{N}-[(3~{S},4~{S})-4-fluoro-3-piperidyl]-7-methoxy-1-methyl-2-[(2~{R})-2-methyl-4-oxo-3,6,9,16,22-pentazatetracyclo[14.5.2.0^{5,10}.0^{19,23}]tricosa-1(21),5(10),6,8,17,19,22-heptaen-17-yl]benzimidazole-5-carboxamide |
| 242 | 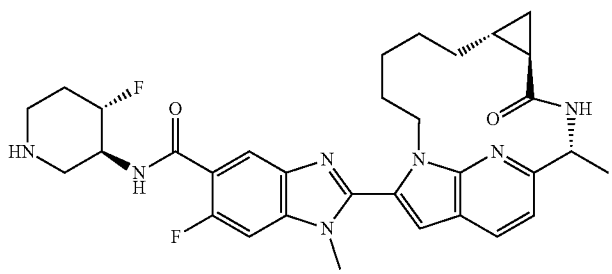 [SMILES: C[C@H]1NC(=O)[C@@H]2C[C@H]2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 243 | 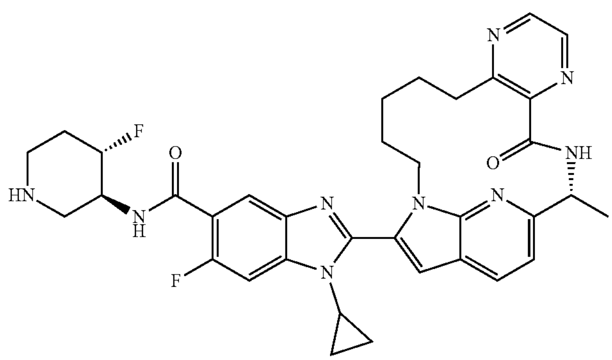 [SMILES: C[C@H]1NC(=O)c2nccnc2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R})-2-methyl-4-oxo-3,6,9,16,22-pentazatetracyclo[14.5.2.0^{5,10}.0^{19,23}]tricosa-1(21),5(10),6,8,17,19,22-heptaen-17-yl]benzimidazole-5-carboxamide |
| 244 | 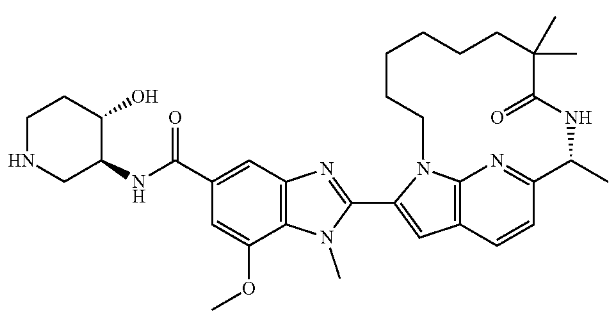 [SMILES: COc1cc(C(=O)N[C@H]2CNCC[C@@H]2O)cc2nc(-c3cc4ccc5nc4n3CCCCCCC(C)(C)C(=O)N[C@@H]5C)n(C)c12] | ~{N}-[(3~{S},4~{S})-4-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 245 | 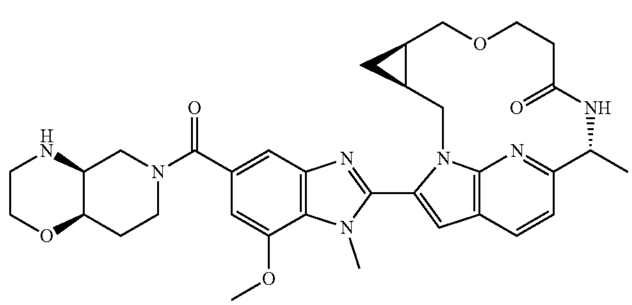 [SMILES: COc1cc(C(=O)N2CC[C@H]3OCCN[C@H]3C2)cc2nc(-c3cc4ccc5nc4n3C[C@H]3C[C@H]3COCCC(=O)N[C@@H]5C)n(C)c12] | (3~{S},5~{R},12~{R})-18-[5-[(4~{a}~{S},8~{a}~{R})-2,3,4,4~{a},5,7,8,8~{a}-octahydropyrido[4,3-b][1,4]oxazine-6-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 246 | 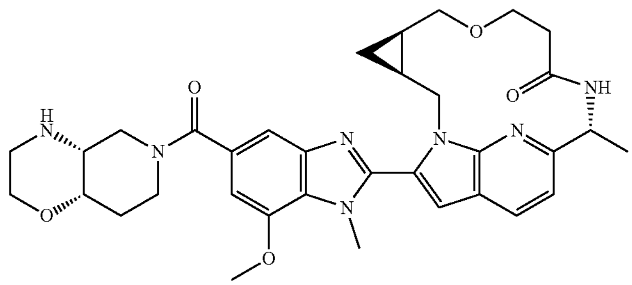 [SMILES: COc1cc(C(=O)N2CC[C@@H]3OCCN[C@@H]3C2)cc2nc(-c3cc4ccc5nc4n3C[C@H]3C[C@H]3COCCC(=O)N[C@@H]5C)n(C)c12] | (3~{S},5~{R},12~{R})-18-[5-[(4~{a}~{R},8~{a}~{S})-2,3,4,4~{a},5,7,8,8~{a}-octahydropyrido[4,3-b][1,4]oxazine-6-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 247 | 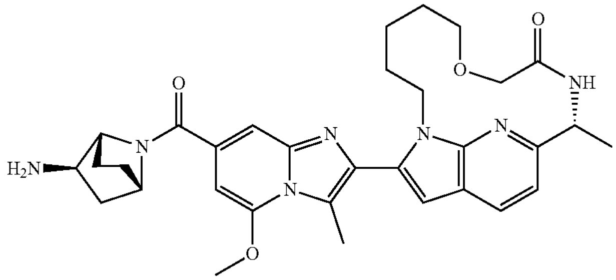 [SMILES: COc1cc(C(=O)N2[C@H]3CC[C@@H]2[C@H](N)C3)cc2nc(-c3cc4ccc5nc4n3CCCCCOCC(=O)N[C@@H]5C)c(C)n12] | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-7-oxa-1,10,19-triazatricyclo[10.5.2.0^{15,18}]nonadeca-12(19),13,15(18),16-tetraen-9-one |
| 248 | 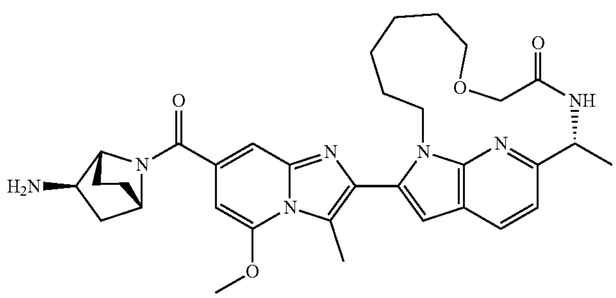 [SMILES: COc1cc(C(=O)N2[C@H]3CC[C@@H]2[C@H](N)C3)cc2nc(-c3cc4ccc5nc4n3CCCCCCOCC(=O)N[C@@H]5C)c(C)n12] | (12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-8-oxa-1,11,20-triazatricyclo[11.5.2.0^{16,19}]icosa-13(20),14,16(19),17-tetraen-10-one |
| 249 | 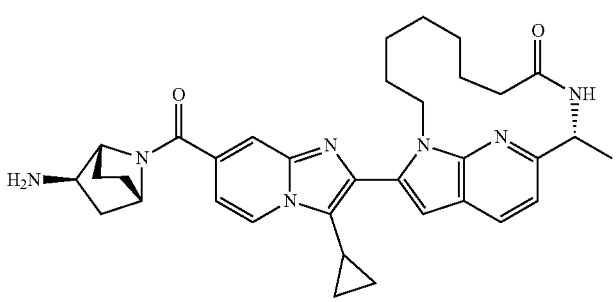 [SMILES: C[C@H]1NC(=O)CCCCCCCn2c(-c3nc4cc(C(=O)N5[C@H]6CC[C@@H]5[C@H](N)C6)ccn4c3C3CC3)cc3ccc1nc32] | (11~{R})-17-[7-[(1~{R},2~{R},4~{S})-2-amino-7-azabicyclo[2.2.1]heptane-7-carbonyl]-3-cyclopropyl-imidazo[1,2-a]pyridin-2-yl]-11-methyl-1,10,19-triazatricyclo[10.5.2.0^{15,18}]nonadeca-12(19),13,15(18),16-tetraen-9-one |
| 250 | 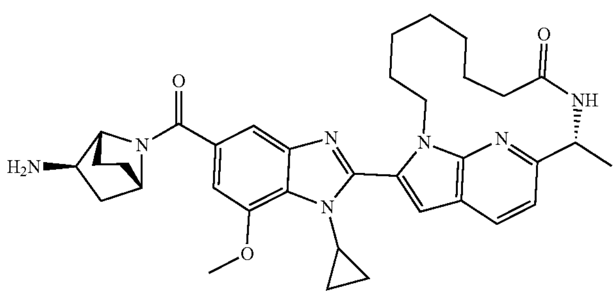 [SMILES: COc1cc(C(=O)N2[C@H]3CC[C@@H]2[C@H](N)C3)cc2nc(-c3cc4ccc5nc4n3CCCCCCCC(=O)N[C@@H]5C)n(C3CC3)c12] | (11~{R})-17-[5-[(1~{R},2~{R},4~{S})-2-amino-7-azabicyclo[2.2.1]heptane-7-carbonyl]-1-cyclopropyl-7-methoxy-benzimidazol-2-yl]-11-methyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 251 | 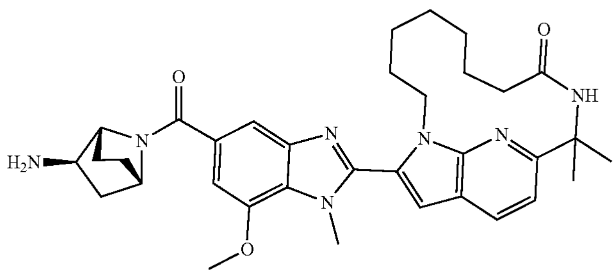 [SMILES: COc1cc(C(=O)N2[C@H]3CC[C@@H]2[C@H](N)C3)cc2nc(-c3cc4ccc5nc4n3CCCCCCCC(=O)NC5(C)C)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-11,11-dimethyl-1,10,19-triazatricyclo[10.5.2.0^{15,18}]nonadeca-12(19),13,15(18),16-tetraen-9-one |
| 252 | 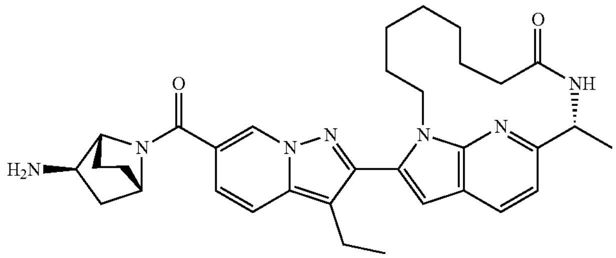 [SMILES: CCc1c(-c2cc3ccc4nc3n2CCCCCCCC(=O)N[C@@H]4C)nn2cc(C(=O)N3[C@H]4CC[C@@H]3[C@H](N)C4)ccc12] | 17-[5-[(1~{R},2~{R},4~{S})-2-amino-7-azabicyclo[2.2.1]heptane-7-carbonyl]-3-ethyl-pyrazolo[1,5-a]pyridin-2-yl]-11-methyl-1,10,19-triazatricyclo[10.5.2.0^{15,18}]nonadeca-12(19),13,15(18),16-tetraen-9-one |
| 253 | 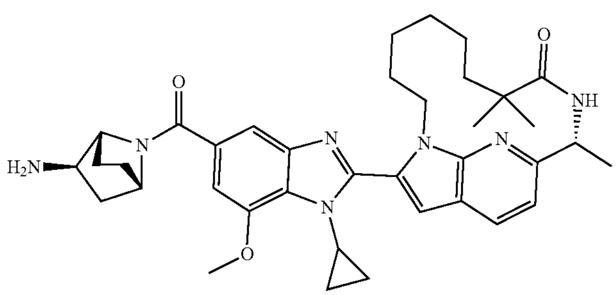 [SMILES: COc1cc(C(=O)N2[C@H]3CC[C@@H]2[C@H](N)C3)cc2nc(-c3cc4ccc5nc4n3CCCCCCC(C)(C)C(=O)N[C@@H]5C)n(C3CC3)c12] | (11~{R})-17-[5-[(1~{R},2~{R},4~{S})-2-amino-7-azabicyclo[2.2.1]heptane-7-carbonyl]-1-cyclopropyl-7-methoxy-benzimidazol-2-yl]-8,8,11-trimethyl-1,10,19-triazatricyclo[10.5.2.0^{15,18}]nonadeca-12(19),13,15(18),16-tetraen-9-one |
| 254 | 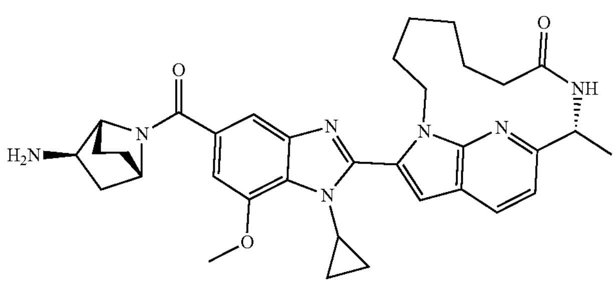 [SMILES: COc1cc(C(=O)N2[C@H]3CC[C@@H]2[C@H](N)C3)cc2nc(-c3cc4ccc5nc4n3CCCCCCC(=O)N[C@@H]5C)n(C3CC3)c12] | (10~{R})-16-[5-[(1~{R},2~{R},4~{S})-2-amino-7-azabicyclo[2.2.1]heptane-7-carbonyl]-1-cyclopropyl-7-methoxy-benzimidazol-2-yl]-10-methyl-1,9,18-triazatricyclo[9.5.2.0^{14,17}]octadeca-11(18),12,14(17),15-tetraen-8-one |
| 255 | 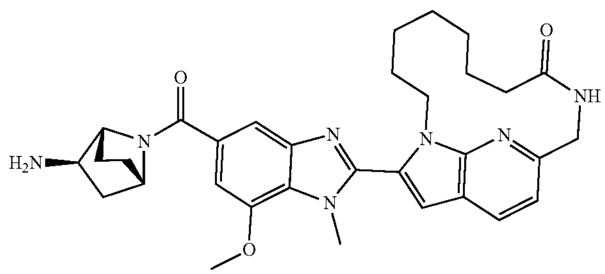 [SMILES: COc1cc(C(=O)N2[C@H]3CC[C@@H]2[C@H](N)C3)cc2nc(-c3cc4ccc5nc4n3CCCCCCCC(=O)NC5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-1,10,19-triazatricyclo[10.5.2.0^{15,18}]nonadeca-12(19),13,15(18),16-tetraen-9-one |

TABLE 1-continued

| Example | Structure | Name |
|---|---|---|
| 256 | 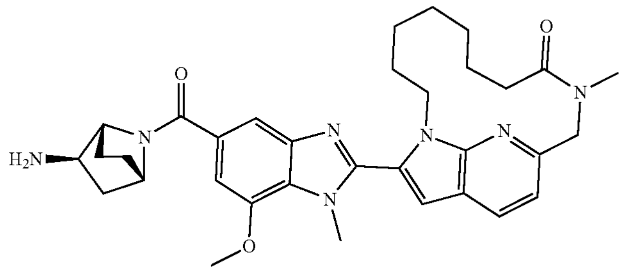 [SMILES: COc1cc(C(=O)N2[C@H]3CC[C@@H]2[C@H](N)C3)cc2nc(-c3cc4ccc5nc4n3CCCCCCCC(=O)N(C)C5)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-10-methyl-1,10,19-triazatricyclo[10.5.2.0^{15,18}]nonadeca-12(19),13,15(18),16-tetraen-9-one |
| 257 | 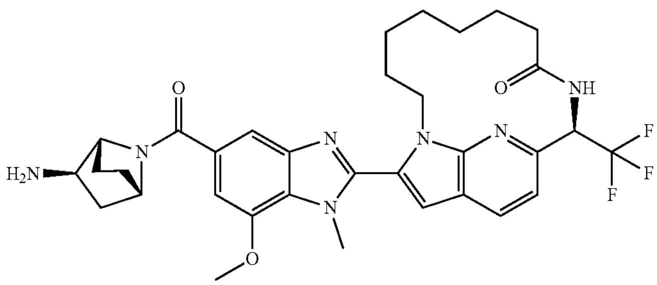 [SMILES: COc1cc(C(=O)N2[C@H]3CC[C@@H]2[C@H](N)C3)cc2nc(-c3cc4ccc5nc4n3CCCCCCCC(=O)N[C@H]5C(F)(F)F)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one |
| 258 | 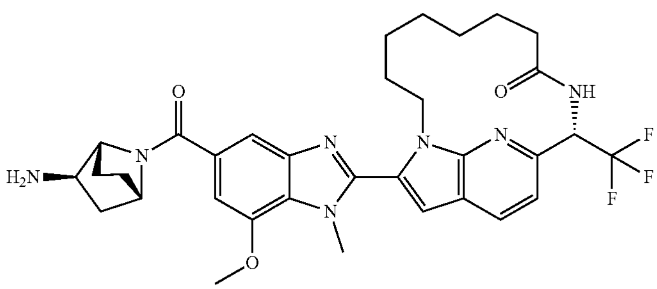 [SMILES: COc1cc(C(=O)N2[C@H]3CC[C@@H]2[C@H](N)C3)cc2nc(-c3cc4ccc5nc4n3CCCCCCCC(=O)N[C@@H]5C(F)(F)F)n(C)c12] | (11~{S})-17-[5-[(1~{R},2~{R},4~{S})-2-amino-7-azabicyclo[2.2.1]heptane-7-carbonyl]-7-methoxy-1-methyl-benzimidazol-2-yl]-11-(trifluoromethyl)-1,10,19-triazatricyclo[10.5.2.0^{15,18}]nonadeca-12(19),13,15(18),16-tetraen-9-one |
| 259 | 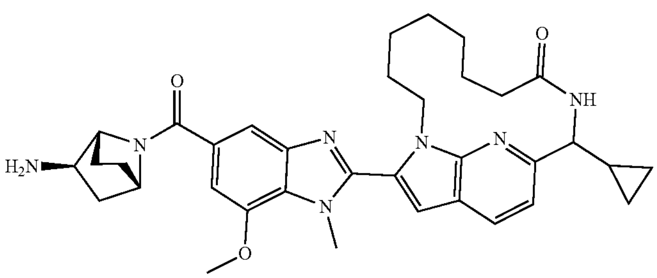 [SMILES: COc1cc(C(=O)N2[C@H]3CC[C@@H]2[C@H](N)C3)cc2nc(-c3cc4ccc5nc4n3CCCCCCCC(=O)NC5C3CC3)n(C)c12] | 17-[5-[(1~{R},2~{R},4~{S})-2-amino-7-azabicyclo[2.2.1]heptane-7-carbonyl]-7-methoxy-1-methyl-benzimidazol-2-yl]-11-cyclopropyl-1,10,19-triazatricyclo[10.5.2.0^{15,18}]nonadeca-12(19),13,15(18),16-tetraen-9-one |
| 260 | 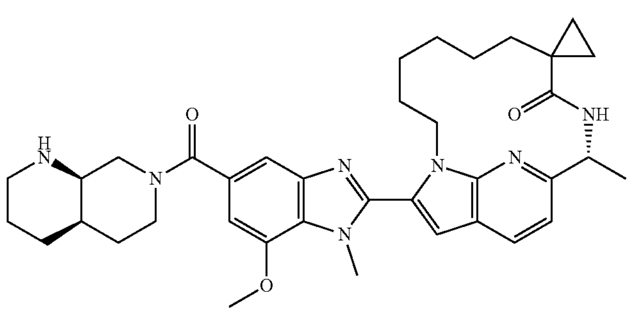 [SMILES: COc1cc(C(=O)N2CC[C@H]3CCCN[C@H]3C2)cc2nc(-c3cc4ccc5nc4n3CCCCCCC3(CC3)C(=O)N[C@@H]5C)n(C)c12] | (11~{R})-17-[5-[(4~{a}~{R},8~{a}~{R})-2,3,4,4~{a},5,6,8,8~{a}-octahydro-1~{H}-1,7-naphthyridine-7-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |

TABLE 1-continued

| Example | Structure | Name |
|---|---|---|
| 261 | 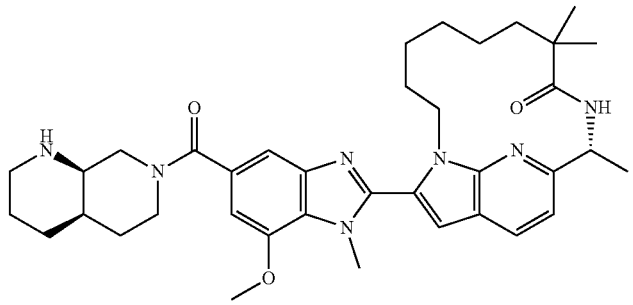 [SMILES: COc1cc(C(=O)N2CC[C@H]3CCCN[C@H]3C2)cc2nc(-c3cc4ccc5nc4n3CCCCCCC(C)(C)C(=O)N[C@@H]5C)n(C)c12] | (11~{R})-17-[5-[(4~{a}~{R},8~{a}~{R})-2,3,4,4~{a},5,6,8,8~{a}-octahydro-1~{H}-1,7-naphthyridine-7-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 262 | 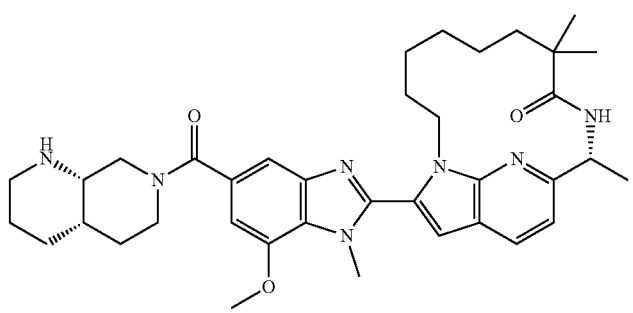 [SMILES: COc1cc(C(=O)N2CC[C@@H]3CCCN[C@@H]3C2)cc2nc(-c3cc4ccc5nc4n3CCCCCCC(C)(C)C(=O)N[C@@H]5C)n(C)c12] | (11~{R})-17-[5-[(4~{a}~{S},8~{a}~{S})-2,3,4,4~{a},5,6,8,8~{a}-octahydro-1~{H}-1,7-naphthyridine-7-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 263 | 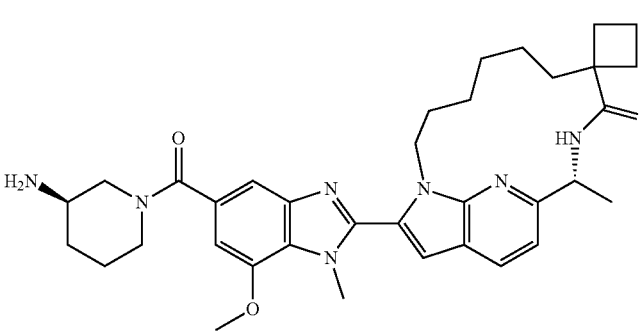 | (11~{R})-17-[5-[(3~{R})-3-aminopiperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclobutane]-9-one |
| 264 | 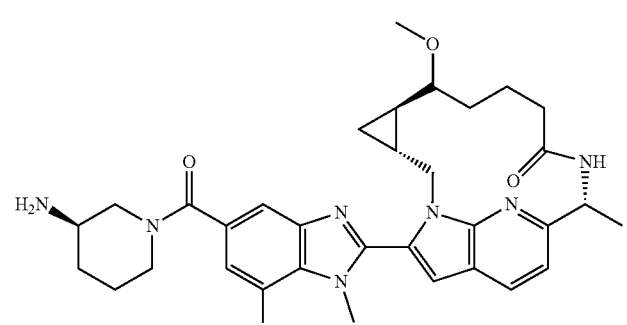 | (3~{R},5~{R},12~{R})-18-[5-[(3~{R})-3-aminopiperidine-1-carbonyl]-7-methoxy-1-methyl-benzimidazol-2-yl]-6-methoxy-12-methyl-1,11,20-triazatetracyclo[11.5.2.0^{3,5}.0^{16,19}]icosa-13(20),14,16(19),17-tetraen-10-one |
| 265 | 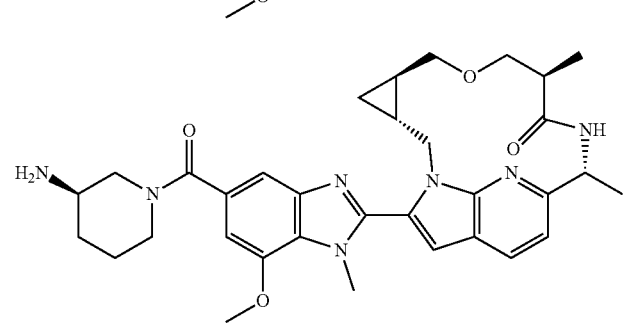 | (5~{R},9~{R},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 266 | 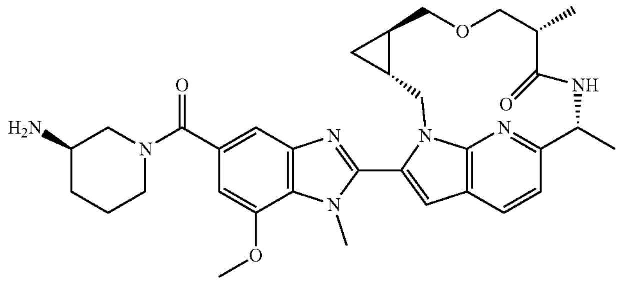 [SMILES: COc1cc(C(=O)N2CCC[C@@H](N)C2)cc2nc(-c3cc4ccc5nc4n3C[C@@H]3C[C@H]3COC[C@H](C)C(=O)N[C@@H]5C)n(C)c12] | (5~{R},9~{S},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0^{3,5}.0^{16,19}]icosa-13(20),14,16(19),17-tetraen-10-one |
| 267 | 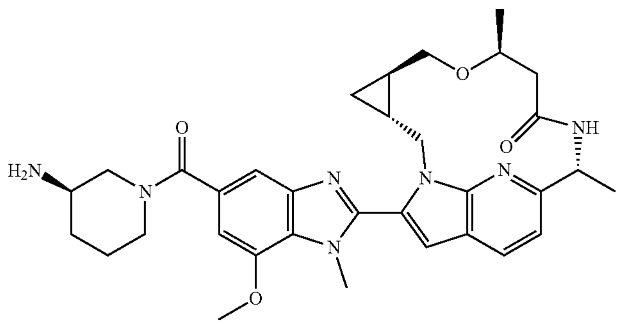 [SMILES: COc1cc(C(=O)N2CCC[C@@H](N)C2)cc2nc(-c3cc4ccc5nc4n3C[C@@H]3C[C@H]3CO[C@@H](C)CC(=O)N[C@@H]5C)n(C)c12] | (5~{R},8~{S},12~{R})-18-[5-[(3~{R})-3-aminopiperidine-1-carbonyl]-7-methoxy-1-methyl-benzimidazol-2-yl]-8,12-dimethyl-7-oxa-1,11,20-triazatetracyclo[11.5.2.0^{3,5}.0^{16,19}]icosa-13(20),14,16(19),17-tetraen-10-one |
| 268 | 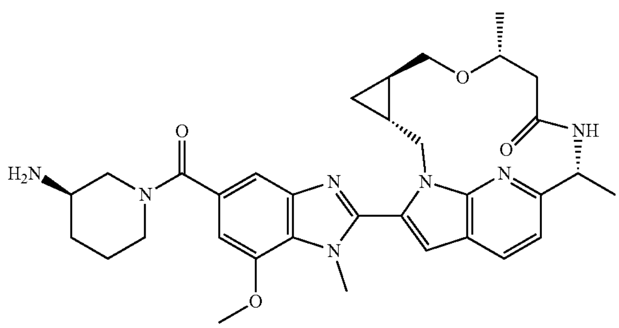 [SMILES: COc1cc(C(=O)N2CCC[C@@H](N)C2)cc2nc(-c3cc4ccc5nc4n3C[C@@H]3C[C@H]3CO[C@H](C)CC(=O)N[C@@H]5C)n(C)c12] | (5~{R},8~{R},12~{R})-18-[5-[(3~{R})-3-aminopiperidine-1-carbonyl]-7-methoxy-1-methyl-benzimidazol-2-yl]-8,12-dimethyl-7-oxa-1,11,20-triazatetracyclo[11.5.2.0^{3,5}.0^{16,19}]icosa-13(20),14,16(19),17-tetraen-10-one |
| 269 | 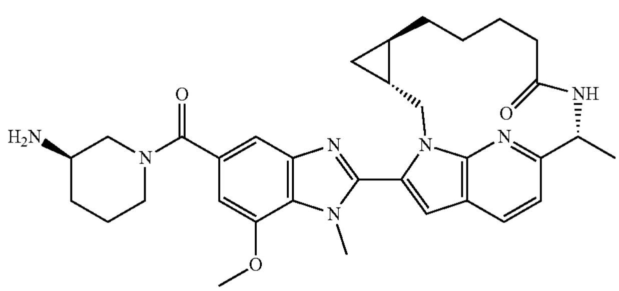 [SMILES: COc1cc(C(=O)N2CCC[C@@H](N)C2)cc2nc(-c3cc4ccc5nc4n3C[C@@H]3C[C@H]3CCCCC(=O)N[C@@H]5C)n(C)c12] | (3~{R},5~{R},12~{R})-18-[5-[(3~{R})-3-aminopiperidine-1-carbonyl]-7-methoxy-1-methyl-benzimidazol-2-yl]-12-methyl-1,11,20-triazatetracyclo[11.5.2.0^{3,5}.0^{16,19}]icosa-13(20),14,16(19),17-tetraen-10-one |
| 270 | 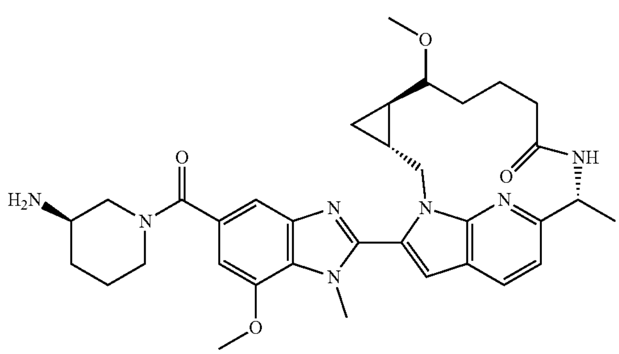 [SMILES: COc1cc(C(=O)N2CCC[C@@H](N)C2)cc2nc(-c3cc4ccc5nc4n3C[C@@H]3C[C@H]3C(OC)CCCC(=O)N[C@@H]5C)n(C)c12] | (3~{R},5~{R},12~{R})-18-[5-[(3~{R})-3-aminopiperidine-1-carbonyl]-7-methoxy-1-methyl-benzimidazol-2-yl]-6-methoxy-12-methyl-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 271 | 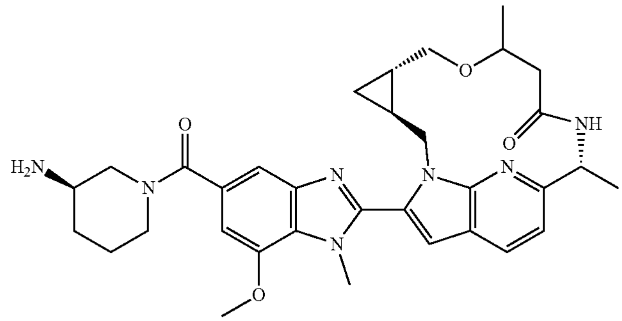 [SMILES: COc1cc(C(=O)N2CCC[C@@H](N)C2)cc2nc(-c3cc4ccc5nc4n3C[C@H]3C[C@@H]3COC(C)CC(=O)N[C@@H]5C)n(C)c12] | (3~{S},5~{S},12~{R})-18-[5-[(3~{R})-3-aminopiperidine-1-carbonyl]-7-methoxy-1-methyl-benzimidazol-2-yl]-8,12-dimethyl-7-oxa-1,11,20-triazatetracyclo[11.5.2.0^{3,5}.0^{16,19}]icosa-13(20),14,16(19),17-tetraen-10-one |
| 272 | 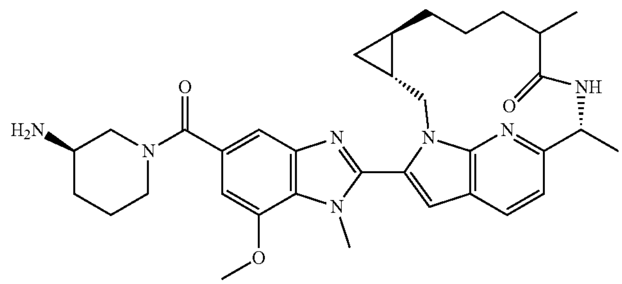 [SMILES: COc1cc(C(=O)N2CCC[C@@H](N)C2)cc2nc(-c3cc4ccc5nc4n3C[C@@H]3C[C@H]3CCCC(C)C(=O)N[C@@H]5C)n(C)c12] | (3~{R},5~{R},12~{R})-18-[5-[(3~{R})-3-aminopiperidine-1-carbonyl]-7-methoxy-1-methyl-benzimidazol-2-yl]-9,12-dimethyl-1,11,20-triazatetracyclo[11.5.2.0^{3,5}.0^{16,19}]icosa-13(20),14,16(19),17-tetraen-10-one |
| 273 | 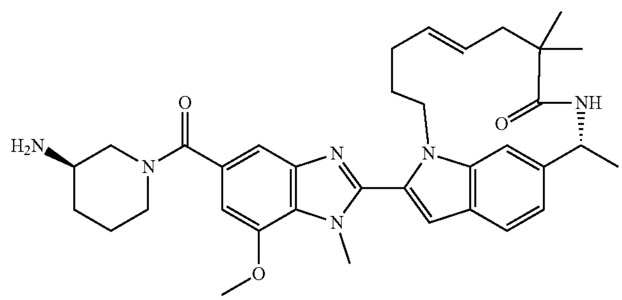 [SMILES: COc1cc(C(=O)N2CCC[C@@H](N)C2)cc2nc(-c3cc4ccc5cc4n3CCC/C=C/CC(C)(C)C(=O)N[C@@H]5C)n(C)c12] | (5~{E},11~{R})-17-[5-[(3~{R})-3-aminopiperidine-1-carbonyl]-7-methoxy-1-methyl-benzimidazol-2-yl]-8,8,11-trimethyl-1,10-diazatricyclo[10.5.2.0^{15,18}]nonadeca-5,12(19),13,15(18),16-pentaen-9-one |
| 274 | 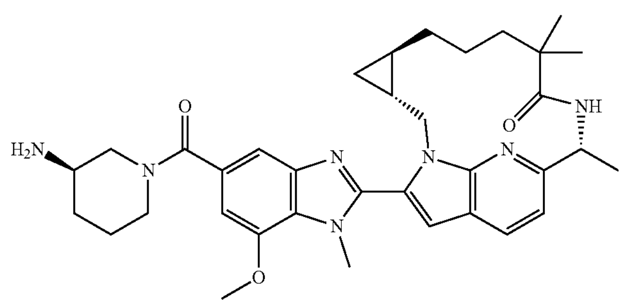 [SMILES: COc1cc(C(=O)N2CCC[C@@H](N)C2)cc2nc(-c3cc4ccc5nc4n3C[C@@H]3C[C@H]3CCCC(C)(C)C(=O)N[C@@H]5C)n(C)c12] | (3~{R},5~{R},12~{R})-18-[5-[(3~{R})-3-aminopiperidine-1-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one |
| 275 | 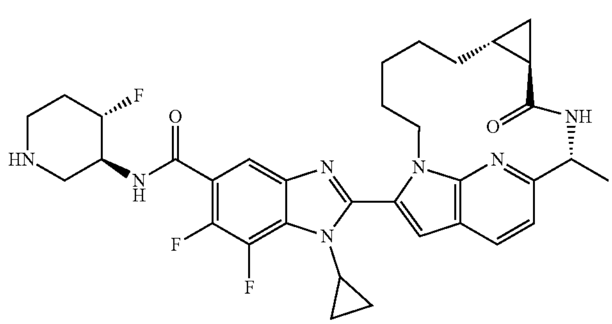 [SMILES: C[C@H]1NC(=O)[C@@H]2C[C@H]2CCCCCn2c(-c3nc4cc(C(=O)N[C@H]5CNCC[C@@H]5F)c(F)c(F)c4n3C3CC3)cc3ccc1nc32] | 1-cyclopropyl-6,7-difluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1-continued

| Example | Structure | Name |
|---|---|---|
| 276 | 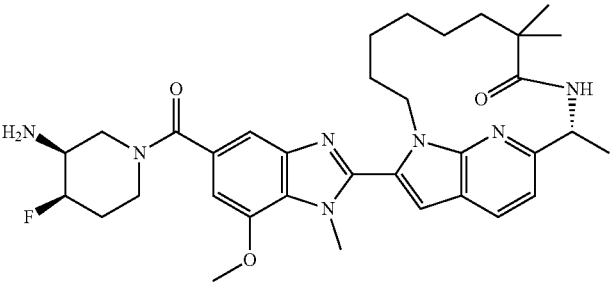 [SMILES: COc1cc(C(=O)N2CC[C@@H](F)[C@@H](N)C2)cc2nc(-c3cc4ccc5nc4n3CCCCCCC(C)(C)C(=O)N[C@@H]5C)n(C)c12] | (11~{R})-17-[5-[(3~{S},4~{R})-3-amino-4-fluoro-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 277 | 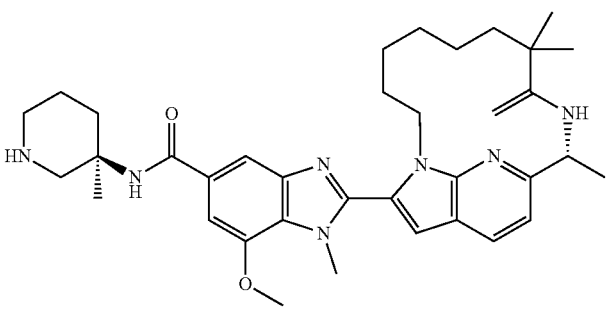 [SMILES: C=C1N[C@H](C)c2ccc3cc(-c4nc5cc(C(=O)N[C@]6(C)CCCNC6)cc(OC)c5n4C)n(c3n2)CCCCCCC1(C)C] | 7-methoxy-1-methyl-~{N}-[(3~{R})-3-methyl-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 278 | 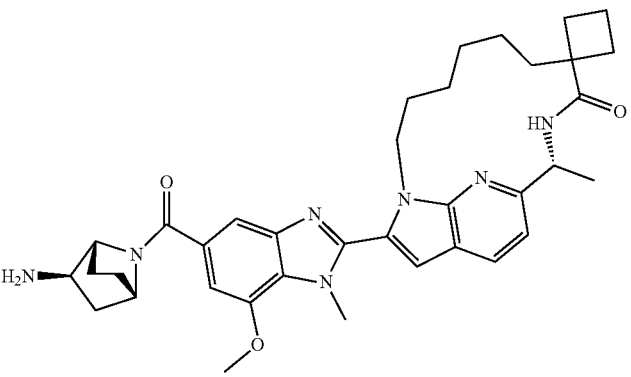 [SMILES: COc1cc(C(=O)N2[C@H]3CC[C@@H]2[C@H](N)C3)cc2nc(-c3cc4ccc5nc4n3CCCCCCC3(CCC3)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclobutane]-9-one |
| 279 | 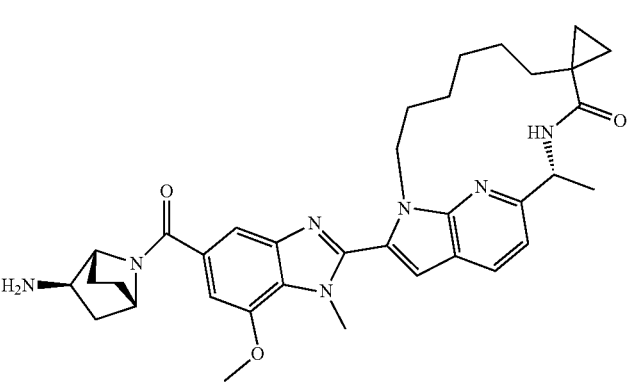 [SMILES: COc1cc(C(=O)N2[C@H]3CC[C@@H]2[C@H](N)C3)cc2nc(-c3cc4ccc5nc4n3CCCCCCC3(CC3)C(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |

TABLE 1-continued

| Example | Structure | Name |
| --- | --- | --- |
| 280 | 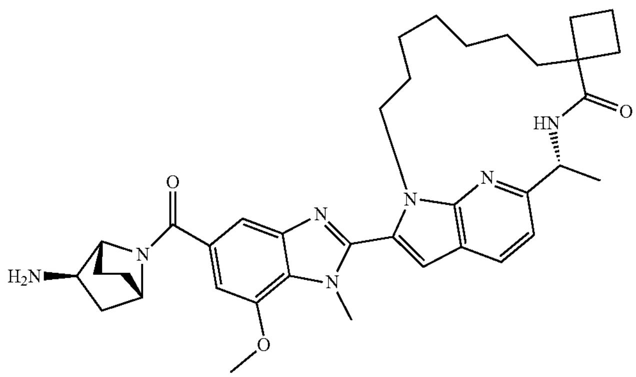 [SMILES: COc1cc(C(=O)N2[C@H]3CC[C@@H]2[C@H](N)C3)cc2nc(-c3cc4ccc5nc4n3CCCCCCCC3(CCC3)C(=O)N[C@@H]5C)n(C)c12] | 2-amino-7-azabicyclo[2.2.1]heptane-7-carbonyl]-7-methoxy-1-methyl-benzimidazol-2-yl]-12-methyl-spiro[1,11,20-triazatricyclo[11.5.2.0^{16,19}]icosa-13(20),14,16(19),17-tetraene-9,1'-cyclobutane]-10-one |
| 281 | 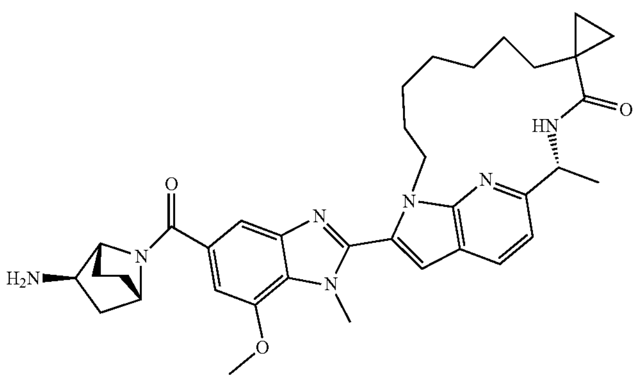 [SMILES: COc1cc(C(=O)N2[C@H]3CC[C@@H]2[C@H](N)C3)cc2nc(-c3cc4ccc5nc4n3CCCCCCCC3(CC3)C(=O)N[C@@H]5C)n(C)c12] | (12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-spiro[1,11,20-triazatricyclo[11.5.2.0^{16,19}]icosa-13(20),14,16(19),17-tetraene-9,1'-cyclopropane]-10-one |
| 282 | 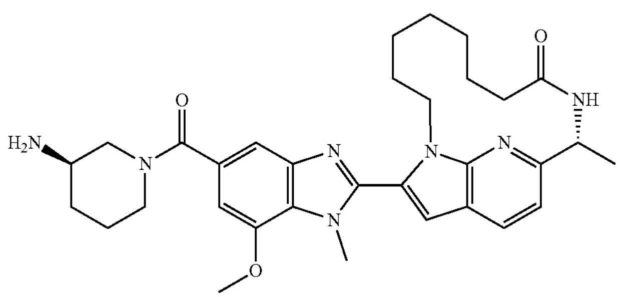 [SMILES: COc1cc(C(=O)N2CCC[C@@H](N)C2)cc2nc(-c3cc4ccc5nc4n3CCCCCCCC(=O)N[C@@H]5C)n(C)c12] | (11~{R})-17-[5-[(3~{R})-3-aminopiperidine-1-carbonyl]-7-methoxy-1-methyl-benzimidazol-2-yl]-11-methyl-1,10,19-triazatricyclo[10.5.2.0^{15,18}]nonadeca-12(19),13,15(18),16-tetraen-9-one |
| 283 | 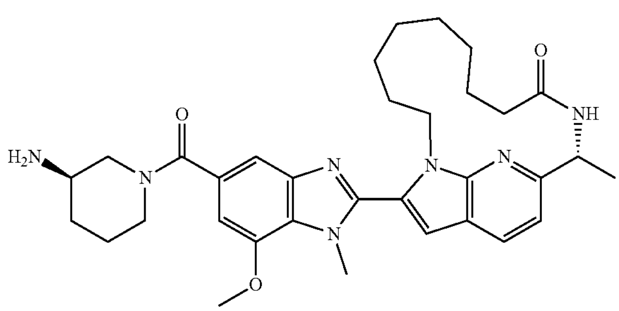 [SMILES: COc1cc(C(=O)N2CCC[C@@H](N)C2)cc2nc(-c3cc4ccc5nc4n3CCCCCCCCC(=O)N[C@@H]5C)n(C)c12] | (12~{R})-18-[5-[(3~{R})-3-aminopiperidine-1-carbonyl]-7-methoxy-1-methyl-benzimidazol-2-yl]-12-methyl-1,11,20-triazatricyclo[11.5.2.0^{16,19}]icosa-13(20),14,16(19),17-tetraen-10-one |

TABLE 1-continued

| Example | Structure | Name |
|---|---|---|
| 284 | 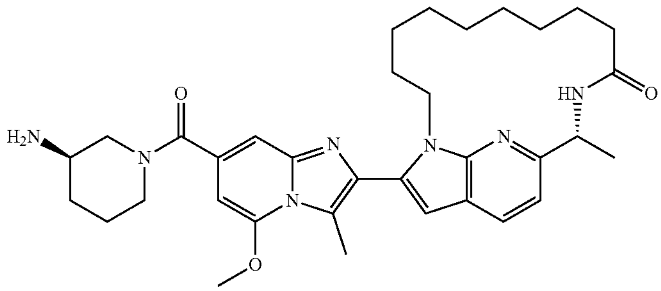 [SMILES: COc1cc(C(=O)N2CCC[C@@H](N)C2)cc2nc(-c3cc4ccc5nc4n3CCCCCCCCCC(=O)N[C@@H]5C)c(C)n12] | (13~{R})-19-[7-[(3~{R})-3-aminopiperidine-1-carbonyl]-5-methoxy-3-methyl-imidazo[1,2-a]pyridin-2-yl]-13-methyl-1,12,21-triazatricyclo[12.5.2.0^{17,20}]henicosa-14(21),15,17(20),18-tetraen-11-one |
| 285 | 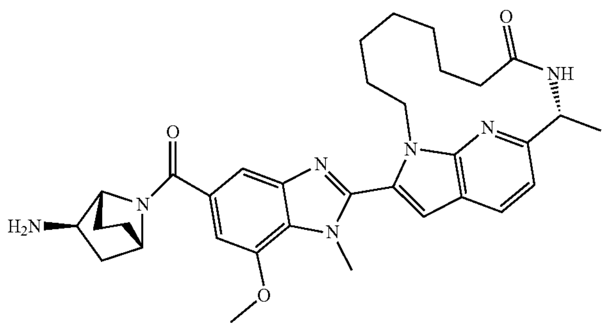 [SMILES: COc1cc(C(=O)N2[C@H]3CC[C@@H]2[C@H](N)C3)cc2nc(-c3cc4ccc5nc4n3CCCCCCCC(=O)N[C@@H]5C)n(C)c12] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-11-methyl-1,10,19-triazatricyclo[10.5.2.0^{15,18}]nonadeca-12(19),13,15(18),16-tetraen-9-one |
| 286 | 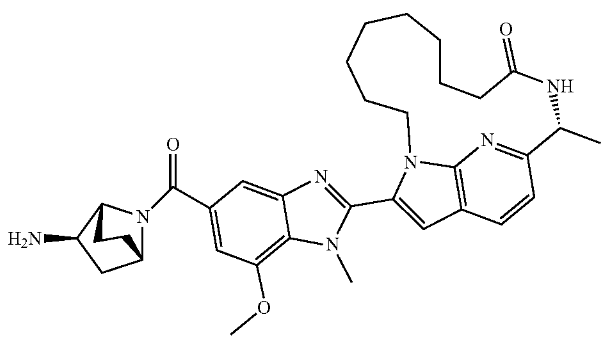 [SMILES: COc1cc(C(=O)N2[C@H]3CC[C@@H]2[C@H](N)C3)cc2nc(-c3cc4ccc5nc4n3CCCCCCCCC(=O)N[C@@H]5C)n(C)c12] | (12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-1,11,20-triazatricyclo[11.5.2.0^{16,19}]icosa-13(20),14,16(19),17-tetraen-10-one |
| 287 | 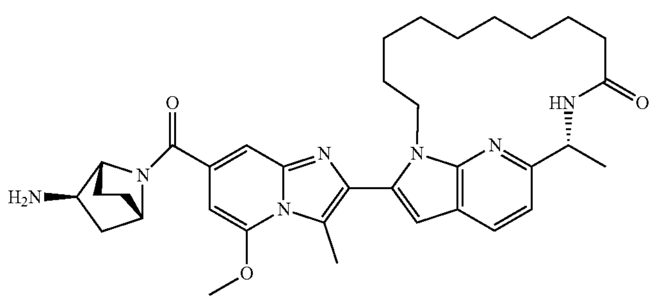 [SMILES: COc1cc(C(=O)N2[C@H]3CC[C@@H]2[C@H](N)C3)cc2nc(-c3cc4ccc5nc4n3CCCCCCCCCC(=O)N[C@@H]5C)c(C)n12] | (13~{R})-19-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-13-methyl-1,12,21-triazatricyclo[12.5.2.0^{17,20}]henicosa-14(21),15,17(20),18-tetraen-11-one |
| 288 | 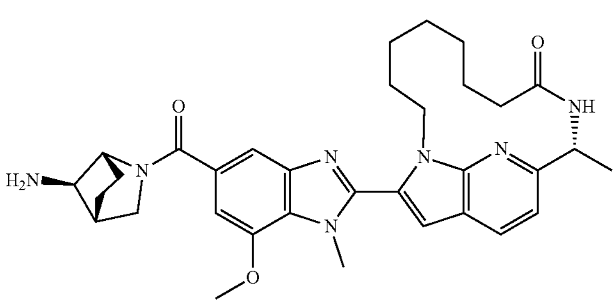 [SMILES: COc1cc(C(=O)N2C[C@H]3CC[C@@H]2[C@@H]3N)cc2nc(-c3cc4ccc5nc4n3CCCCCCCC(=O)N[C@@H]5C)n(C)c12] | (11~{R})-17-[5-[(1~{R},4~{R},7~{R})-7-amino-2-azabicyclo[2.2.1]heptane-2-carbonyl]-7-methoxy-1-methyl-benzimidazol-2-yl]-11-methyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 289 | 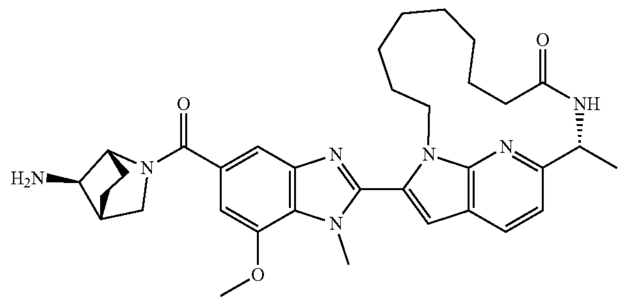 [SMILES: COc1cc(C(=O)N2C[C@H]3CC[C@@H]2[C@@H]3N)cc2nc(-c3cc4ccc5nc4n3CCCCCCCCC(=O)N[C@@H]5C)n(C)c12] | (12~{R})-18-[5-[(1~{R},4~{R},7~{R})-7-amino-2-azabicyclo[2.2.1]heptane-2-carbonyl]-7-methoxy-1-methyl-benzimidazol-2-yl]-12-methyl-1,11,20-triazatricyclo[11.5.2.0^{16,19}]icosa-13(20),14,16(19),17-tetraen-10-one |
| 290 | 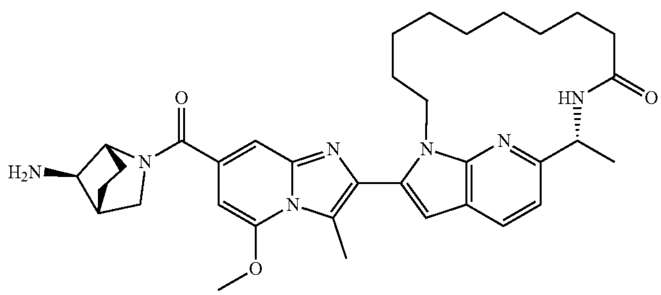 [SMILES: COc1cc(C(=O)N2C[C@H]3CC[C@@H]2[C@@H]3N)cc2nc(-c3cc4ccc5nc4n3CCCCCCCCCC(=O)N[C@@H]5C)c(C)n12] | (13~{R})-19-[7-[(1~{R},4~{R},7~{R})-7-amino-2-azabicyclo[2.2.1]heptane-2-carbonyl]-5-methoxy-3-methyl-imidazo[1,2-a]pyridin-2-yl]-13-methyl-1,12,21-triazatricyclo[12.5.2.0^{17,20}]henicosa-14(21),15,17(20),18-tetraen-11-one |
| 291 | 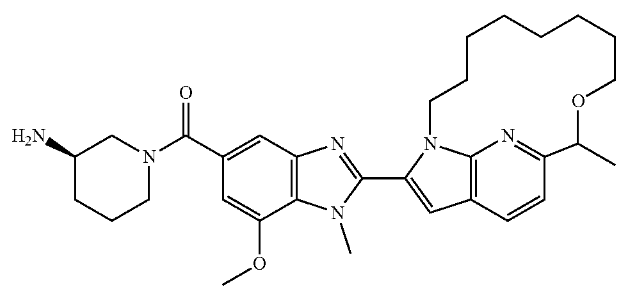 [SMILES: COc1cc(C(=O)N2CCC[C@@H](N)C2)cc2nc(-c3cc4ccc5nc4n3CCCCCCCCOC5C)n(C)c12] | [(3~{R})-3-amino-1-piperidyl]-[7-methoxy-1-methyl-2-(11-methyl-10-oxa-1,19-diazatricyclo[10.5.2.0^{15,18}]nonadeca-12(19),13,15(18),16-tetraen-17-yl)benzimidazol-5-yl]methanone |
| 292 | 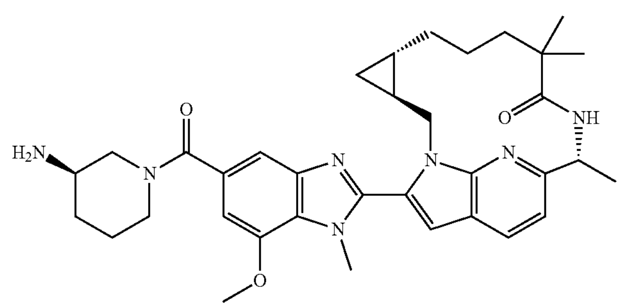 [SMILES: COc1cc(C(=O)N2CCC[C@@H](N)C2)cc2nc(-c3cc4ccc5nc4n3C[C@H]3C[C@@H]3CCCC(C)(C)C(=O)N[C@@H]5C)n(C)c12] | (3~{S},5~{S},12~{R})-18-[5-[(3~{R})-3-aminopiperidine-1-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one |
| 293 | 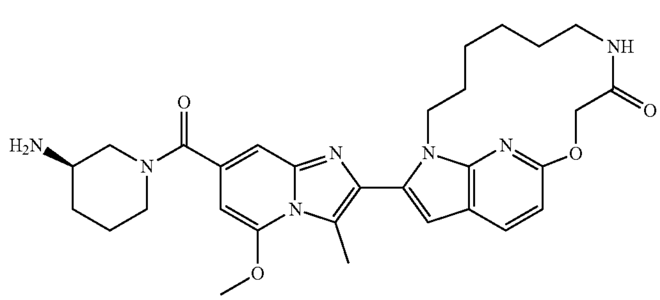 [SMILES: COc1cc(C(=O)N2CCC[C@@H](N)C2)cc2nc(-c3cc4ccc5nc4n3CCCCCCNC(=O)CO5)c(C)n12] | 17-[7-[(3~{R})-3-aminopiperidine-1-carbonyl]-5-methoxy-3-methyl-imidazo[1,2-a]pyridin-2-yl]-11-oxa-1,8,19-triazatricyclo[10.5.2.0^{15,18}]nonadeca-12(19),13,15(18),16-tetraen-9-one |

TABLE 1-continued

| Example | Structure | Name |
|---|---|---|
| 294 | 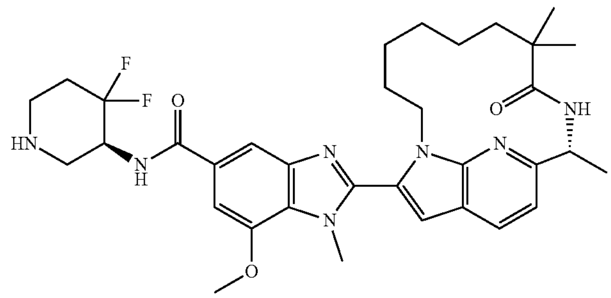 [SMILES: COc1cc(C(=O)N[C@H]2CNCCC2(F)F)cc2nc(-c3cc4ccc5nc4n3CCCCCCC(C)(C)C(=O)N[C@@H]5C)n(C)c12] | ~{N}-[(3~{S})-4,4-difluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 295 | 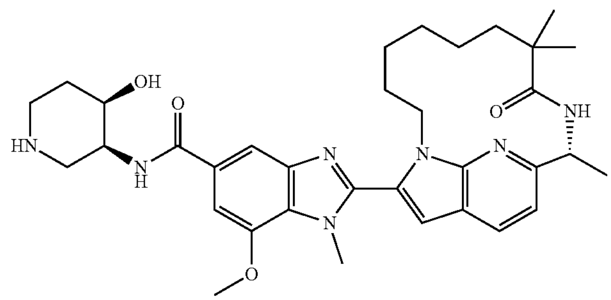 [SMILES: COc1cc(C(=O)N[C@H]2CNCC[C@H]2O)cc2nc(-c3cc4ccc5nc4n3CCCCCCC(C)(C)C(=O)N[C@@H]5C)n(C)c12] | ~{N}-[(3~{S},4~{R})-4-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 296 | 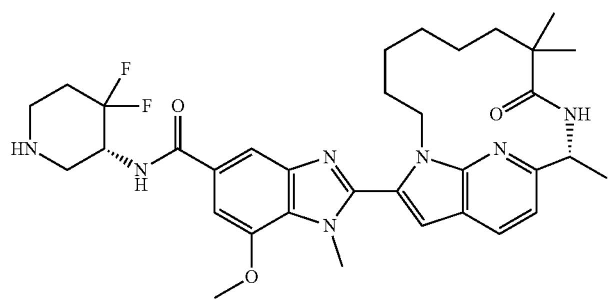 [SMILES: COc1cc(C(=O)N[C@@H]2CNCCC2(F)F)cc2nc(-c3cc4ccc5nc4n3CCCCCCC(C)(C)C(=O)N[C@@H]5C)n(C)c12] | ~{N}-[(3~{R})-4,4-difluoro-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 297 | 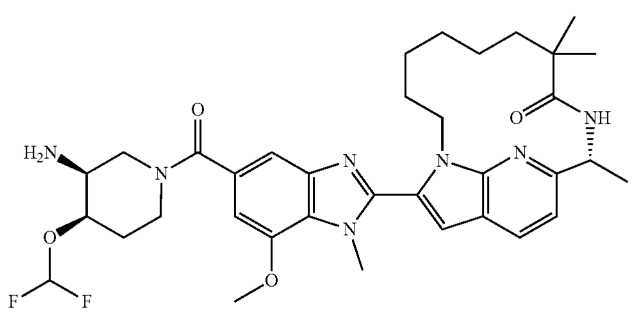 [SMILES: COc1cc(C(=O)N2CC[C@@H](OC(F)F)[C@@H](N)C2)cc2nc(-c3cc4ccc5nc4n3CCCCCCC(C)(C)C(=O)N[C@@H]5C)n(C)c12] | (11~{R})-17-[5-[(3~{S},4~{R})-3-amino-4-(difluoromethoxy)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 298 | 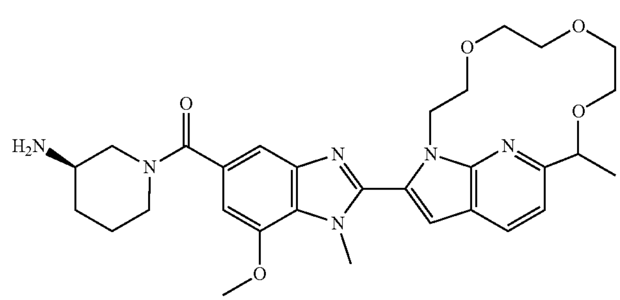 [SMILES: COc1cc(C(=O)N2CCC[C@@H](N)C2)cc2nc(-c3cc4ccc5nc4n3CCOCCOCCOC5C)n(C)c12] | [(3~{R})-3-amino-1-piperidyl]-[7-methoxy-1-methyl-2-(11-methyl-4,7,10-trioxa-1,19-diazatricyclo[10.5.2.0^{15,18}]nonadeca-12(19),13,15(18),16-tetraen-17-yl)benzimidazol-5-yl]methanone |

TABLE 1-continued

| Example | Structure | Name |
|---|---|---|
| 299 | 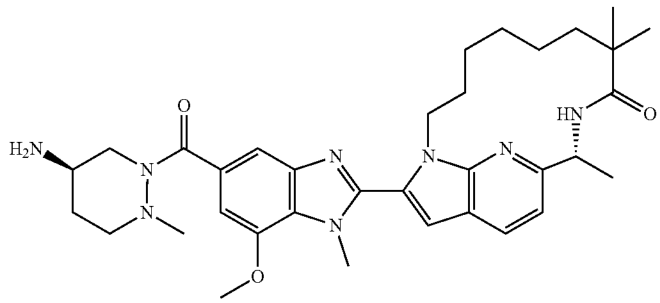 [SMILES: COc1cc(C(=O)N2C[C@H](N)CCN2C)cc2nc(-c3cc4ccc5nc4n3CCCCCCC(C)(C)C(=O)N[C@@H]5C)n(C)c12] | (11~{R})-17-[5-[(5~{R})-5-amino-2-methyl-hexahydropyridazine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 300 | 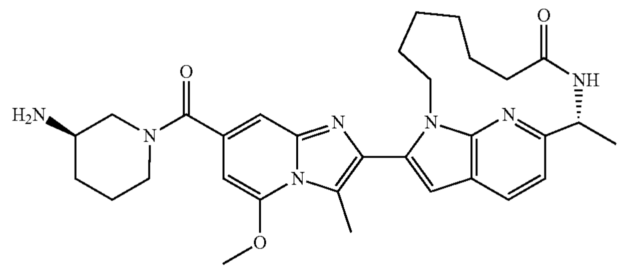 [SMILES: COc1cc(C(=O)N2CCC[C@@H](N)C2)cc2nc(-c3cc4ccc5nc4n3CCCCCCC(=O)N[C@@H]5C)c(C)n12] | (10~{R})-16-[7-[(3~{R})-3-aminopiperidine-1-carbonyl]-5-methoxy-3-methyl-imidazo[1,2-a]pyridin-2-yl]-10-methyl-1,9,18-triazatricyclo[9.5.2.0^{14,17}]octadeca-11(18),12,14(17),15-tetraen-8-one |
| 301 | 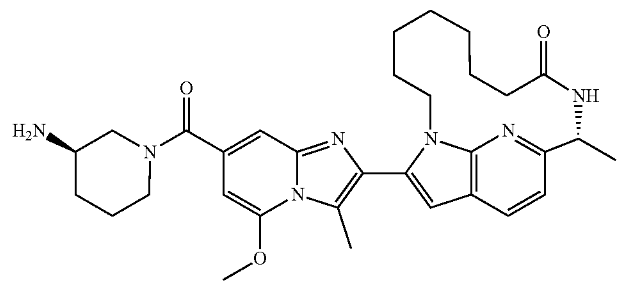 [SMILES: COc1cc(C(=O)N2CCC[C@@H](N)C2)cc2nc(-c3cc4ccc5nc4n3CCCCCCCC(=O)N[C@@H]5C)c(C)n12] | (11~{R})-17-[7-[(3~{R})-3-aminopiperidine-1-carbonyl]-5-methoxy-3-methyl-imidazo[1,2-a]pyridin-2-yl]-11-methyl-1,10,19-triazatricyclo[10.5.2.0^{15,18}]nonadeca-12(19),13,15(18),16-tetraen-9-one |
| 302 | 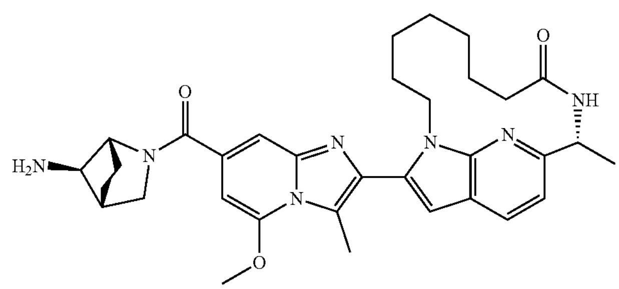 [SMILES: COc1cc(C(=O)N2C[C@H]3CC[C@@H]2[C@@H]3N)cc2nc(-c3cc4ccc5nc4n3CCCCCCCC(=O)N[C@@H]5C)c(C)n12] | (11~{R})-17-[7-[(1~{R},4~{R},7~{R})-7-amino-2-azabicyclo[2.2.1]heptane-2-carbonyl]-5-methoxy-3-methyl-imidazo[1,2-a]pyridin-2-yl]-11-methyl-1,10,19-triazatricyclo[10.5.2.0^{15,18}]nonadeca-12(19),13,15(18),16-tetraen-9-one |
| 303 | 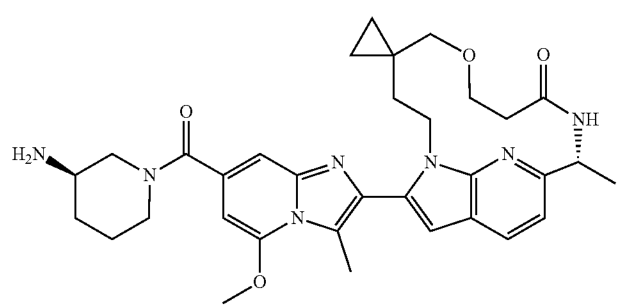 [SMILES: COc1cc(C(=O)N2CCC[C@@H](N)C2)cc2nc(-c3cc4ccc5nc4n3CCC3(CC3)COCCC(=O)N[C@@H]5C)c(C)n12] | (11~{R})-17-[7-[(3~{R})-3-aminopiperidine-1-carbonyl]-5-methoxy-3-methyl-imidazo[1,2-a]pyridin-2-yl]-11-methyl-spiro[6-oxa-1,10,19-triazatricyclo[10.5.2.0^{15,18}]nonadeca-12(19),13,15(18),16-tetraene-4,1'-cyclopropane]-9-one |

TABLE 1-continued

| Example | Structure | Name |
|---|---|---|
| 304 | 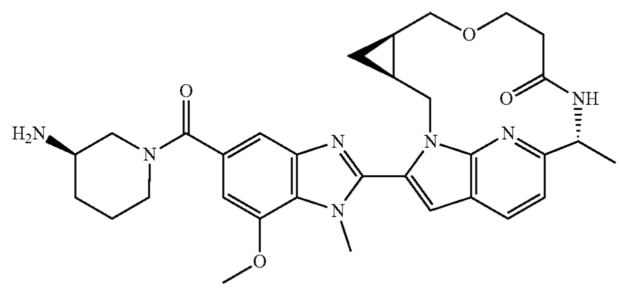 [SMILES: COc1cc(C(=O)N2CCC[C@@H](N)C2)cc2nc(-c3cc4ccc5nc4n3C[C@H]3C[C@H]3COCCC(=O)N[C@@H]5C)n(C)c12] | (3~{S},5~{R},12~{R})-18-[5-[(3~{R})-3-aminopiperidine-1-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 305 | 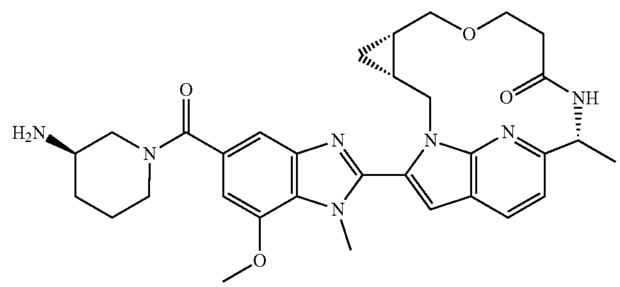 [SMILES: COc1cc(C(=O)N2CCC[C@@H](N)C2)cc2nc(-c3cc4ccc5nc4n3C[C@@H]3C[C@@H]3COCCC(=O)N[C@@H]5C)n(C)c12] | (3~{R},5~{S},12~{R})-18-[5-[(3~{R})-3-aminopiperidine-1-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 306 | 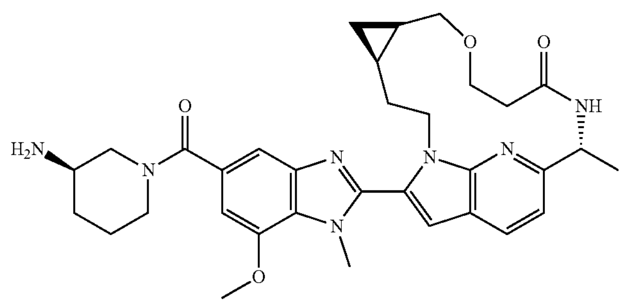 [SMILES: COc1cc(C(=O)N2CCC[C@@H](N)C2)cc2nc(-c3cc4ccc5nc4n3CC[C@H]3C[C@H]3COCCC(=O)N[C@@H]5C)n(C)c12] | (4~{R},6~{R},13~{R})-19-[5-[(3~{R})-3-aminopiperidine-1-carbonyl]-7-methoxy-1-methyl-benzimidazol-2-yl]-13-methyl-8-oxa-1,12,21-triazatetracyclo[12.5.2.0^{4,6}.0^{17,20}]henicosa-14(21),15,17(20),18-tetraen-11-one |
| 307 | 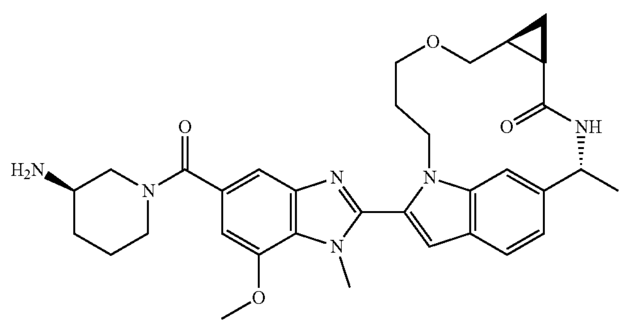 [SMILES: COc1cc(C(=O)N2CCC[C@@H](N)C2)cc2nc(-c3cc4ccc5cc4n3CCCOC[C@H]3C[C@H]3C(=O)N[C@@H]5C)n(C)c12] | (2~{R},5~{R},7~{S})-14-[5-[(3~{R})-3-aminopiperidine-1-carbonyl]-7-methoxy-1-methyl-benzimidazol-2-yl]-2-methyl-9-oxa-3,13-diazatetracyclo[11.5.2.0^{5,7}.0^{16,20}]icosa-1(19),14,16(20),17-tetraen-4-one |
| 308 | 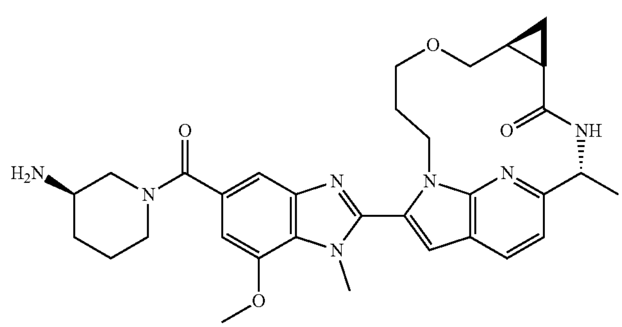 [SMILES: COc1cc(C(=O)N2CCC[C@@H](N)C2)cc2nc(-c3cc4ccc5nc4n3CCCOC[C@H]3C[C@H]3C(=O)N[C@@H]5C)n(C)c12] | (2~{R},5~{R},7~{S})-14-[5-[(3~{R})-3-aminopiperidine-1-carbonyl]-7-methoxy-1-methyl-benzimidazol-2-yl]-2-methyl-9-oxa-3,13,19-triazatetracyclo[11.5.2.0^{5,7}.0^{16,20}]icosa-1(19),14,16(20),17-tetraen-4-one |

| Example | Structure | Name |
|---|---|---|
| 309 | 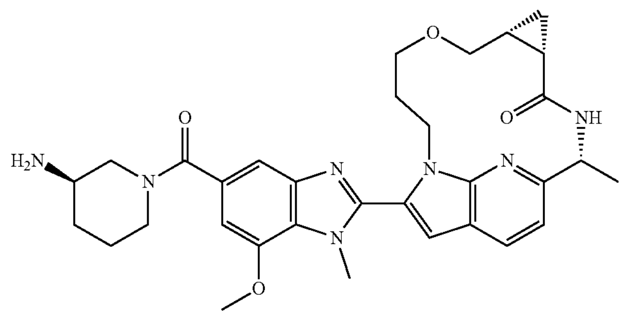 [SMILES: COc1cc(C(=O)N2CCC[C@@H](N)C2)cc2nc(-c3cc4ccc5nc4n3CCCOC[C@@H]3C[C@@H]3C(=O)N[C@@H]5C)n(C)c12] | (2~{R},5~{S},7~{R})-14-[5-[(3~{R})-3-aminopiperidine-1-carbonyl]-7-methoxy-1-methyl-benzimidazol-2-yl]-2-methyl-9-oxa-3,13,19-triazatetracyclo[11.5.2.0^{5,7}.0^{16,20}]icosa-1(19),14,16(20),17-tetraen-4-one |
| 310 | 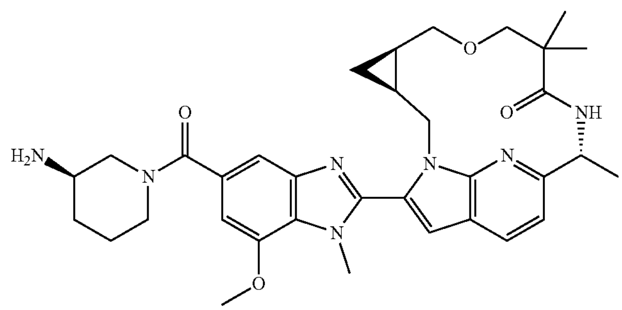 [SMILES: COc1cc(C(=O)N2CCC[C@@H](N)C2)cc2nc(-c3cc4ccc5nc4n3C[C@H]3C[C@H]3COCC(C)(C)C(=O)N[C@@H]5C)n(C)c12] | (3~{S},5~{R},12~{R})-18-[5-[(3~{R})-3-aminopiperidine-1-carbonyl]-7-methoxy-1-methyl-benzimidazol-2-yl]-9,9,12-trimethyl-7-oxa-1,11,20-triazatetracyclo[11.5.2.0^{3,5}.0^{16,19}]icosa-13(20),14,16(19),17-tetraen-10-one |
| 311 | 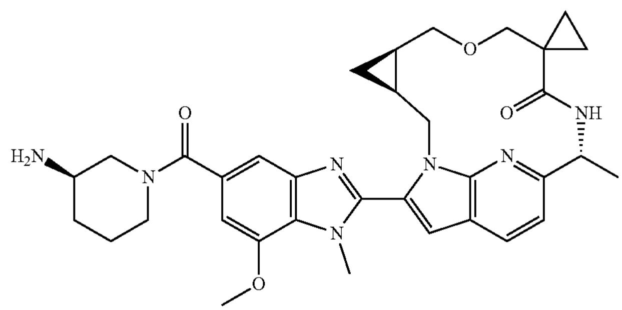 [SMILES: COc1cc(C(=O)N2CCC[C@@H](N)C2)cc2nc(-c3cc4ccc5nc4n3C[C@H]3C[C@H]3COCC3(CC3)C(=O)N[C@@H]5C)n(C)c12] | (3~{S},5~{R},12~{R})-18-[5-[(3~{R})-3-aminopiperidine-1-carbonyl]-7-methoxy-1-methyl-benzimidazol-2-yl]-12-methyl-spiro[7-oxa-1,11,20-triazatetracyclo[11.5.2.0^{3,5}.0^{16,19}]icosa-13(20),14,16(19),17-tetraene-9,1'-cyclopropane]-10-one |
| 312 | 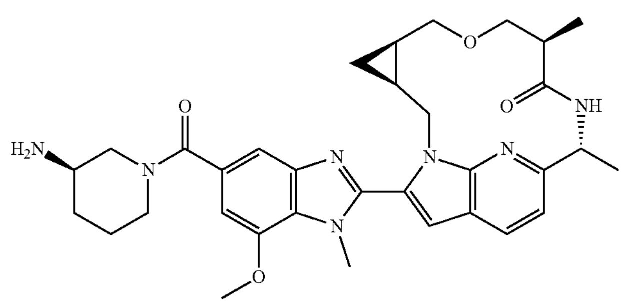 [SMILES: COc1cc(C(=O)N2CCC[C@@H](N)C2)cc2nc(-c3cc4ccc5nc4n3C[C@H]3C[C@H]3COC[C@@H](C)C(=O)N[C@@H]5C)n(C)c12] | (3~{S},5~{R},9~{R},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0^{3,5}.0^{16,19}]icosa-13(20),14,16(19),17-tetraen-10-one |
| 313 | 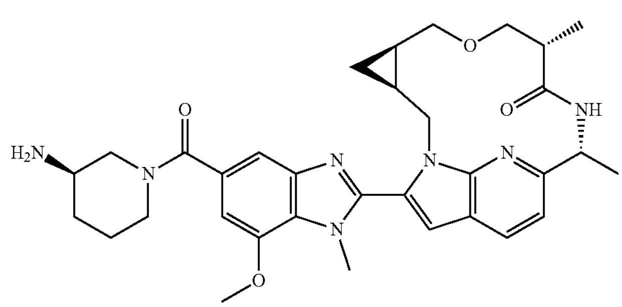 [SMILES: COc1cc(C(=O)N2CCC[C@@H](N)C2)cc2nc(-c3cc4ccc5nc4n3C[C@H]3C[C@H]3COC[C@H](C)C(=O)N[C@@H]5C)n(C)c12] | (3~{S},5~{R},9~{S},12~{R})-18-[5-[(3~{R})-3-aminopiperidine-1-carbonyl]-7-methoxy-1-methyl-benzimidazol-2-yl]-9,12-dimethyl-7-oxa-1,11,20-triazatetracyclo[11.5.2.0^{3,5}.0^{16,19}]icosa-13(20),14,16(19),17-tetraen-10-one |

TABLE 1-continued

| Example | Name |
|---|---|
| 314 | (3~{S},5~{R},12~{R})-18-[5-[(3~{S},4~{R})-3-amino-4-methoxy-piperidine-1-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 315 | ~{N}-[(3~{S},4~{S})-4-fluoro-3-piperidyl]-7-methoxy-1-methyl-2-[(3~{S},5~{R},12~{R})-12-methyl-10-oxo-7-oxa-1,11,20-triazatetracyclo[11.5.2.0^{3,5}.0^{16,19}]icosa-13(20),14,16(19),17-tetraen-18-yl]benzimidazole-5-carboxamide |
| 316 | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-1,10,19-triazatricyclo[10.5.2.0^{15,18}]nonadeca-12(19),13,15(18),16-tetraen-9-one |
| 317 | (10~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-10-methyl-1,9,18-triazatricyclo[9.5.2.0^{14,17}]octadeca-11(18),12,14(17),15-tetraen-8-one |
| 318 | (12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-1,11,20-triazatricyclo[11.5.2.0^{16,19}]icosa-13(20),14,16(19),17-tetraen-10-one |

TABLE 1-continued

| Example | Structure | Name |
|---|---|---|
| 319 | 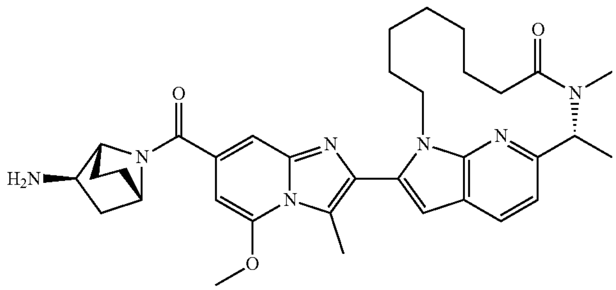 [SMILES: COc1cc(C(=O)N2[C@H]3CC[C@@H]2[C@H](N)C3)cc2nc(-c3cc4ccc5nc4n3CCCCCCCC(=O)N(C)[C@@H]5C)c(C)n12] | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-10,11-dimethyl-1,10,19-triazatricyclo[10.5.2.0^{15,18}]nonadeca-12(19),13,15(18),16-tetraen-9-one |
| 320 | 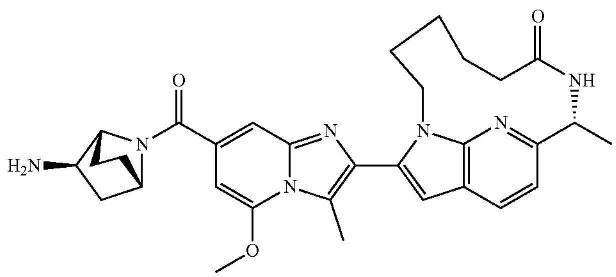 [SMILES: COc1cc(C(=O)N2[C@H]3CC[C@@H]2[C@H](N)C3)cc2nc(-c3cc4ccc5nc4n3CCCCCC(=O)N[C@@H]5C)c(C)n12] | (9~{R})-15-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-9-methyl-1,8,17-triazatricyclo[8.5.2.0^{13,16}]heptadeca-10(17),11,13(16),14-tetraen-7-one |
| 321 | 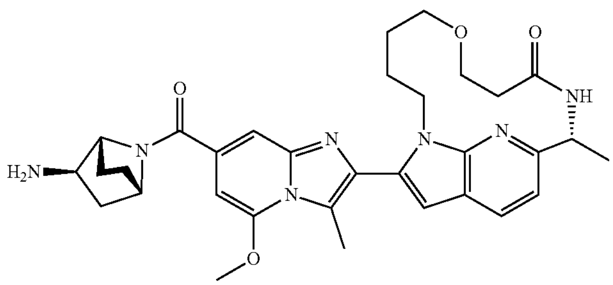 | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-6-oxa-1,10,19-triazatricyclo[10.5.2.0^{15,18}]nonadeca-12(19),13,15(18),16-tetraen-9-one |
| 322 | 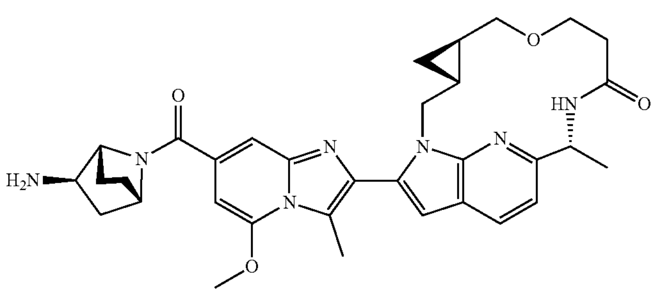 | (3~{R},5~{R},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one |
| 323 | 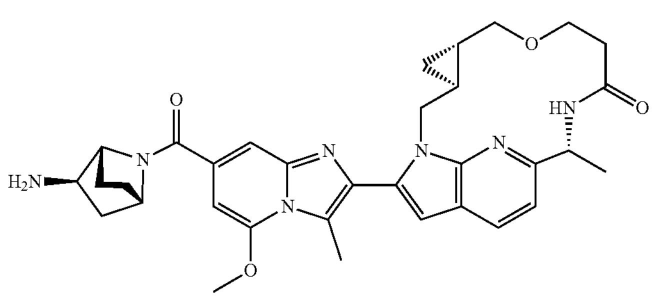 | (3~{S},5~{S},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 324 | 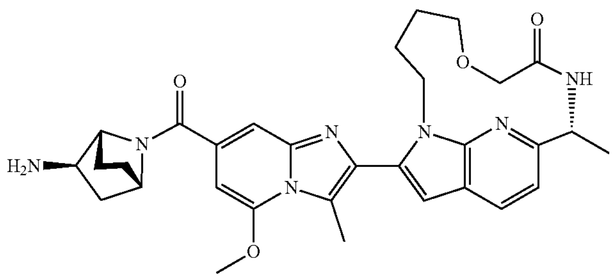 | (10~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-10-methyl-6-oxa-1,9,18-triazatricyclo[9.5.2.0^{14,17}]octadeca-11(18),12,14(17),15-tetraen-8-one |
| 325 | 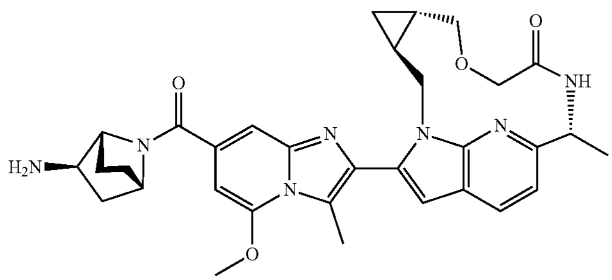 | (3~{S},5~{S},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-7-oxa-1,10,19-triazatetracyclo[10.5.2.0^{3,5}.0^{15,18}]nonadeca-12(19),13,15(18),16-tetraen-9-one |
| 326 | 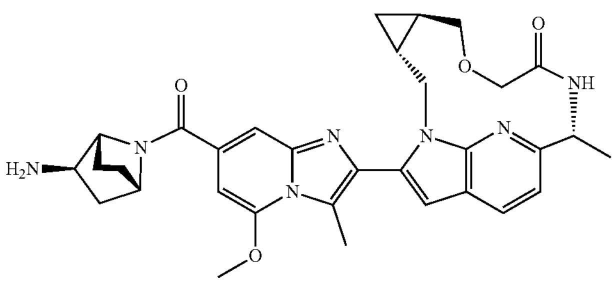 | (3~{R},5~{R},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-7-oxa-1,10,19-triazatetracyclo[10.5.2.0^{3,5}.0^{15,18}]nonadeca-12(19),13,15(18),16-tetraen-9-one |
| 327 | 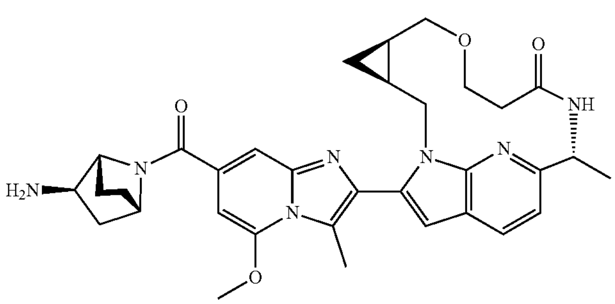 | (3~{S},5~{R},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one |
| 328 | 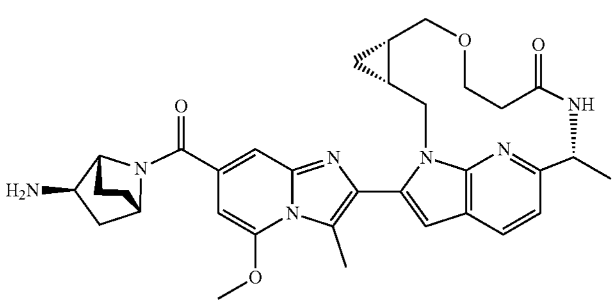 | (3~{R},5~{S},12~{R})-18-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-12-methyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
| --- | --- | --- |
| 329 | 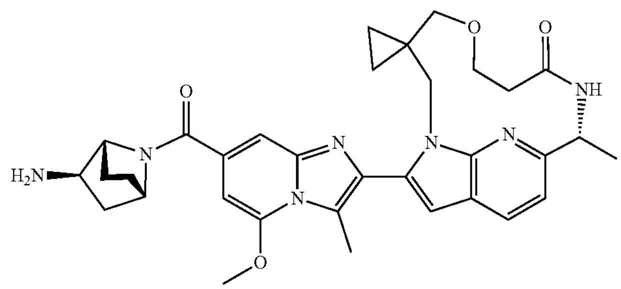 | (10~{R})-16-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-10-methyl-spiro[5-oxa-1,9,18-triazatricyclo[9.5.2.0^{14,17}]octadeca-11(18),12,14(17),15-tetraene-3,1'-cyclopropane]-8-one |
| 330 | 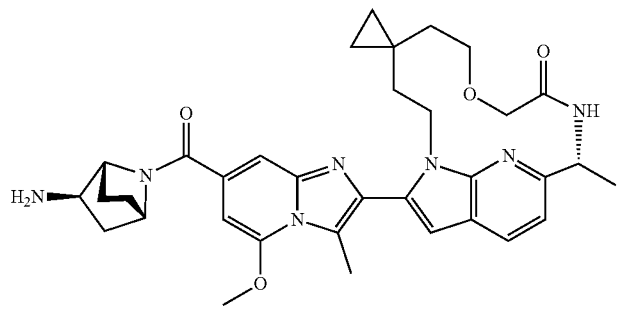 | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-spiro[7-oxa-1,10,19-triazatricyclo[10.5.2.0^{15,18}]nonadeca-12(19),13,15(18),16-tetraene-4,1'-cyclopropane]-9-one |
| 331 | 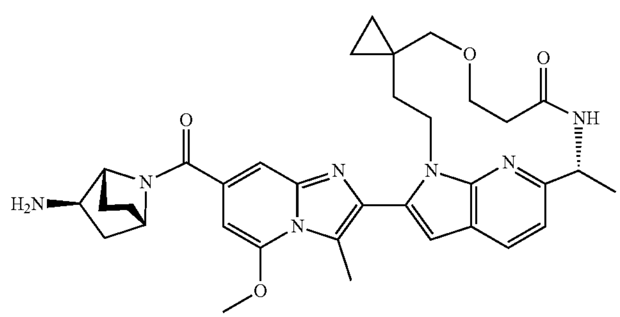 | (11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-11-methyl-spiro[6-oxa-1,10,19-triazatricyclo[10.5.2.0^{15,18}]nonadeca-12(19),13,15(18),16-tetraene-4,1'-cyclopropane]-9-one |
| 332 | 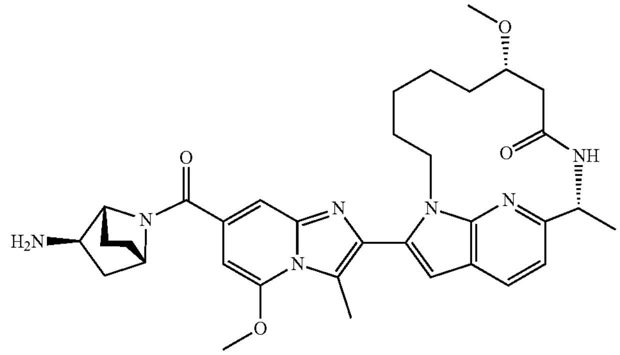 | (7~{S},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-7-methoxy-11-methyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 333 | 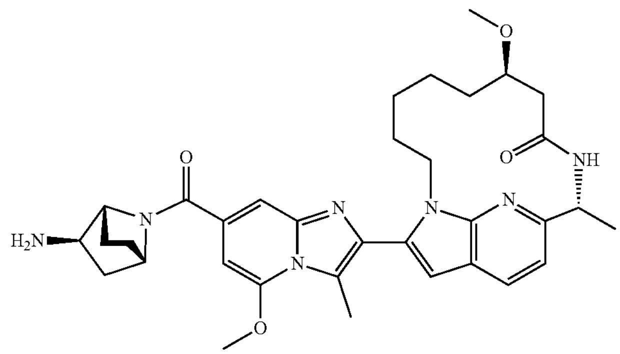 | (7~{R},11~{R})-17-[7-[(1~{R},2~{R},4~{S})-2-amino-7-azabicyclo[2.2.1]heptane-7-carbonyl)-5-methoxy-3-methyl-imidazo[1,2-a]pyridin-2-yl]-7-methoxy-11-methyl-1,10,19-triazatricyclo[10.5.2.0^{15,18}]nonadeca-12(19),13,15(18),16-tetraen-9-one |
| 334 | 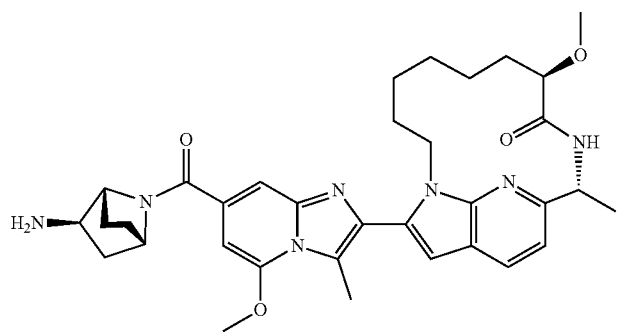 | (8~{R},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8-methoxy-11-methyl-1,10,19-triazatricyclo[10.5.2.0^{15,18}]nonadeca-12(19),13,15(18),16-tetraen-9-one |
| 335 | 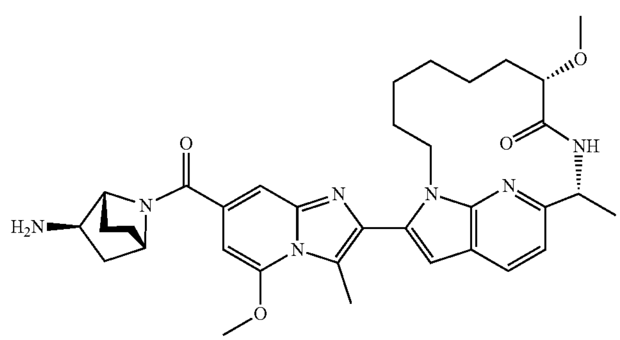 | (8~{S},11~{R})-17-[7-[(1~{R},2~{R},4~{S})-2-amino-7-azabicyclo[2.2.1]heptane-7-carbonyl]-5-methoxy-3-methyl-imidazo[1,2-a]pyridin-2-yl]-8-methoxy-11-methyl-1,10,19-triazatricyclo[10.5.2.0^{15,18}]nonadeca-12(19),13,15(18),16-tetraen-9-one |
| 336 | 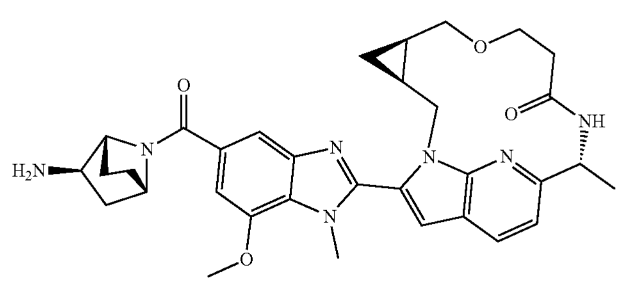 [SMILES: COc1cc(C(=O)N2[C@H]3CC[C@@H]2[C@H](N)C3)cc2nc(-c3cc4ccc5nc4n3C[C@H]3C[C@H]3COCCC(=O)N[C@@H]5C)n(C)c12] | (3~{S},5~{R},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |
| 337 | 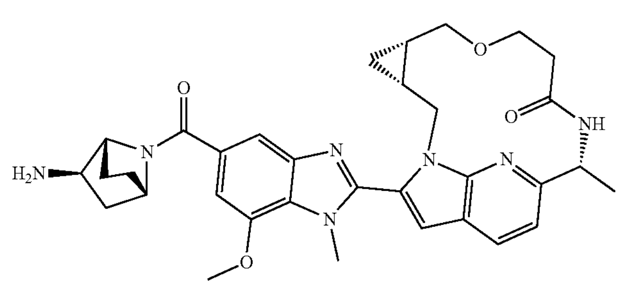 [SMILES: COc1cc(C(=O)N2[C@H]3CC[C@@H]2[C@H](N)C3)cc2nc(-c3cc4ccc5nc4n3C[C@@H]3C[C@@H]3COCCC(=O)N[C@@H]5C)n(C)c12] | (3~{R},5~{S},12~{R})-18-[5-[(1~{R},2~{R},4~{S})-2-amino-7-azabicyclo[2.2.1]heptane-7-carbonyl]-7-methoxy-1-methyl-benzimidazol-2-yl]-12-methyl-7-oxa-1,11,20-triazatetracyclo[11.5.2.0^{3,5}.0^{16,19}]icosa-13(20),14,16(19),17-tetraen-10-one |

TABLE 1-continued

| Example | Structure | Name |
|---|---|---|
| 338 | 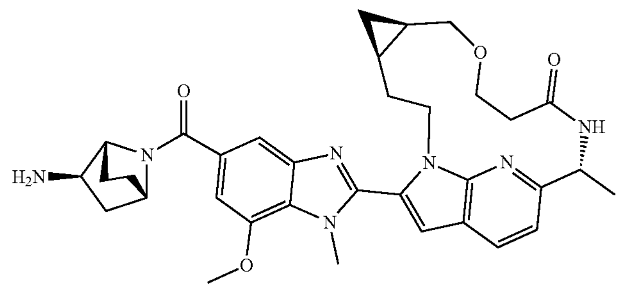 [SMILES: COc1cc(C(=O)N2[C@H]3CC[C@@H]2[C@H](N)C3)cc2nc(-c3cc4ccc5nc4n3CC[C@H]3C[C@H]3COCCC(=O)N[C@@H]5C)n(C)c12] | (4~{R},6~{R},13~{R})-19-[5-[(1~{R},2~{R},4~{S})-2-amino-7-azabicyclo[2.2.1]heptane-7-carbonyl]-7-methoxy-1-methyl-benzimidazol-2-yl]-13-methyl-8-oxa-1,12,21-triazatetracyclo[12.5.2.0^{4,6}.0^{17,20}]henicosa-14(21),15,17(20),18-tetraen-11-one |
| 339 | 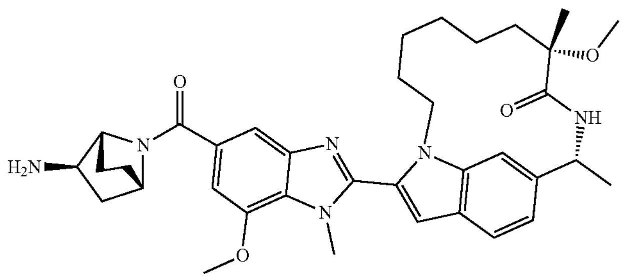 [SMILES: COc1cc(C(=O)N2[C@H]3CC[C@@H]2[C@H](N)C3)cc2nc(-c3cc4ccc5cc4n3CCCCCC[C@](C)(OC)C(=O)N[C@@H]5C)n(C)c12] | (8~{S},11~{R})-17-[5-[(1~{R},2~{R},4~{S})-2-amino-7-azabicyclo[2.2.1]heptane-7-carbonyl]-7-methoxy-1-methyl-benzimidazol-2-yl]-8-methoxy-8,11-dimethyl-1,10-diazatricyclo[10.5.2.0^{15,18}]nonadeca-12(19),13,15(18),16-tetraen-9-one |
| 340 | 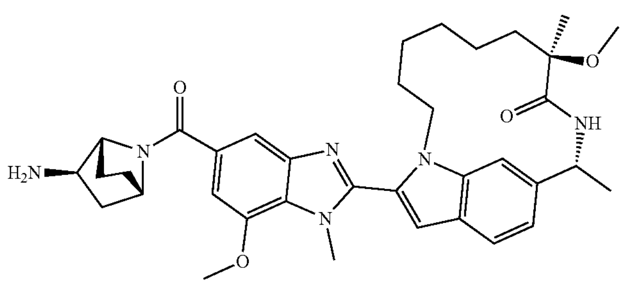 [SMILES: COc1cc(C(=O)N2[C@H]3CC[C@@H]2[C@H](N)C3)cc2nc(-c3cc4ccc5cc4n3CCCCCC[C@@](C)(OC)C(=O)N[C@@H]5C)n(C)c12] | (8~{R},11~{R})-17-[5-[(1~{R},2~{R},4~{S})-2-amino-7-azabicyclo[2.2.1]heptane-7-carbonyl]-7-methoxy-1-methyl-benzimidazol-2-yl]-8-methoxy-8,11-dimethyl-1,10-diazatricyclo[10.5.2.0^{15,18}]nonadeca-12(19),13,15(18),16-tetraen-9-one |
| 341 | 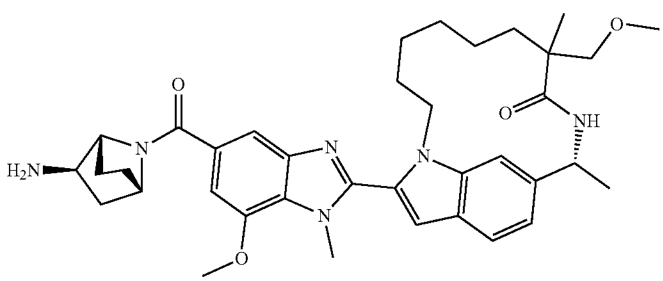 [SMILES: COCC1(C)CCCCCCn2c(-c3nc4cc(C(=O)N5[C@H]6CC[C@@H]5[C@H](N)C6)cc(OC)c4n3C)cc3ccc(cc32)[C@@H](C)NC1=O] | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-8-(methoxymethyl)-8,11-dimethyl-1,10-diazatricyclo[10.5.2.0^{15,18}]nonadeca-12(19),13,15(18),16-tetraen-9-one |
| 342 | 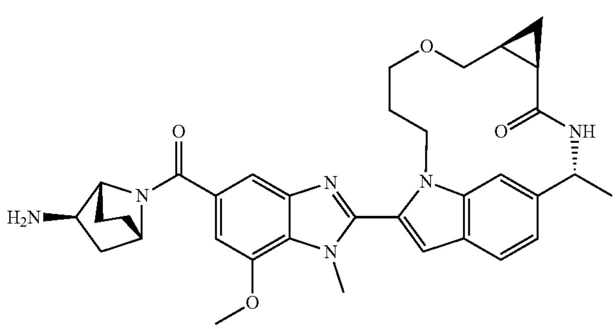 [SMILES: COc1cc(C(=O)N2[C@H]3CC[C@@H]2[C@H](N)C3)cc2nc(-c3cc4ccc5cc4n3CCCOC[C@H]3C[C@H]3C(=O)N[C@@H]5C)n(C)c12] | (2~{R},5~{R},7~{S})-14-[5-[(1~{R},2~{R},4~{S})-2-amino-7-azabicyclo[2.2.1]heptane-7-carbonyl]-7-methoxy-1-methyl-benzimidazol-2-yl]-2-methyl-9-oxa-3,13-diazatetracyclo[11.5.2.0^{5,7}.0^{16,20}]icosa-1(19),14,16(20),17-tetraen-4-one |

TABLE 1-continued

| Example | Structure | Name |
|---|---|---|
| 343 | 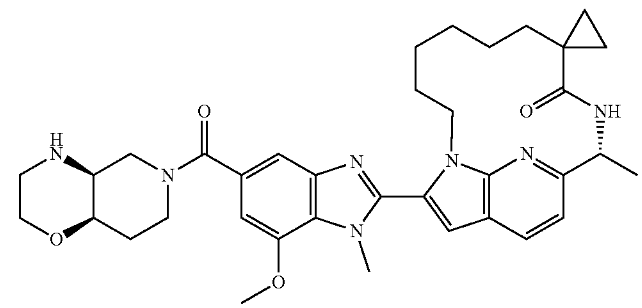 [SMILES: COc1cc(C(=O)N2CC[C@H]3OCCN[C@H]3C2)cc2nc(-c3cc4ccc5nc4n3CCCCCCC3(CC3)C(=O)N[C@@H]5C)n(C)c12] | (11~{R})-17-[5-[(4~{a}~{S},8~{a}~{R})-2,3,4,4~{a},5,7,8,8~{a}-octahydropyrido[4,3-b][1,4]oxazine-6-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |
| 344 | 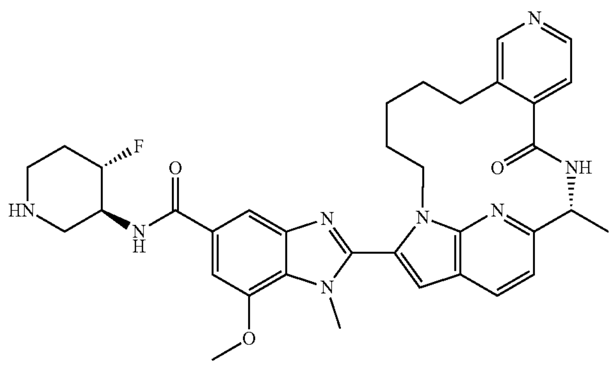 [SMILES: COc1cc(C(=O)N[C@H]2CNCC[C@@H]2F)cc2nc(-c3cc4ccc5nc4n3CCCCCc3cnccc3C(=O)N[C@@H]5C)n(C)c12] | ~{N}-[(3~{S},4~{S})-4-fluoro-3-piperidyl]-7-methoxy-1-methyl-2-[(2~{R})-2-methyl-4-oxo-3,8,16,22-tetrazatetracyclo[14.5.2.0^{5,10}.0^{19,23}]tricosa-1(22),5,7,9,17,19(23),20-heptaen-17-yl]benzimidazole-5-carboxamide |
| 345 | 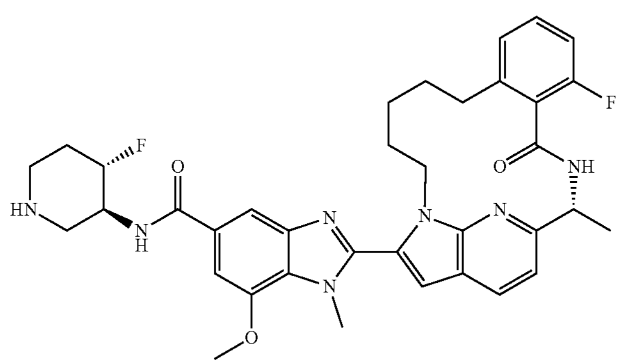 [SMILES: COc1cc(C(=O)N[C@H]2CNCC[C@@H]2F)cc2nc(-c3cc4ccc5nc4n3CCCCCc3cccc(F)c3C(=O)N[C@@H]5C)n(C)c12] | 2-[(2~{R})-6-fluoro-2-methyl-4-oxo-3,16,22-triazatetracyclo[14.5.2.0^{5,10}.0^{19,23}]tricosa-1(22),5,7,9,17,19(23),20-heptaen-17-yl]~{N}-[(3~{S},4~{S})-4-fluoro-3-piperidyl]-7-methoxy-1-methyl-benzimidazole-5-carboxamide |
| 346 | 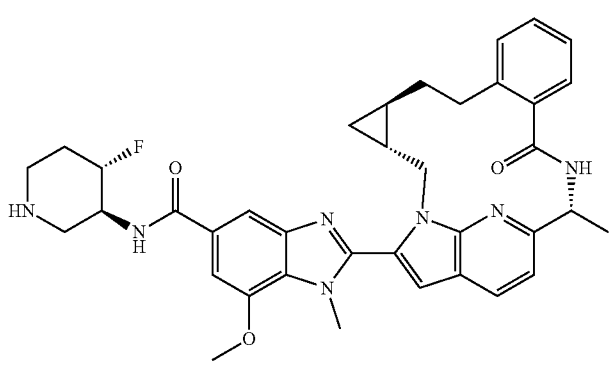 [SMILES: COc1cc(C(=O)N[C@H]2CNCC[C@@H]2F)cc2nc(-c3cc4ccc5nc4n3C[C@@H]3C[C@H]3CCc3ccccc3C(=O)N[C@@H]5C)n(C)c12] | ~{N}-[(3~{S},4~{S})-4-fluoro-3-piperidyl]-7-methoxy-1-methyl-2-[(3~{R},5~{R},16~{R})-16-methyl-14-oxo-1,15,24-triazapentacyclo[15.5.2.0^{3,5}.0^{8,13}.0^{20,23}]tetracosa-8,10,12,17(24),18,20(23),21-heptaen-22-yl]benzimidazole-5-carboxamide |

TABLE 1-continued

| Example | Structure | Name |
|---|---|---|
| 347 | 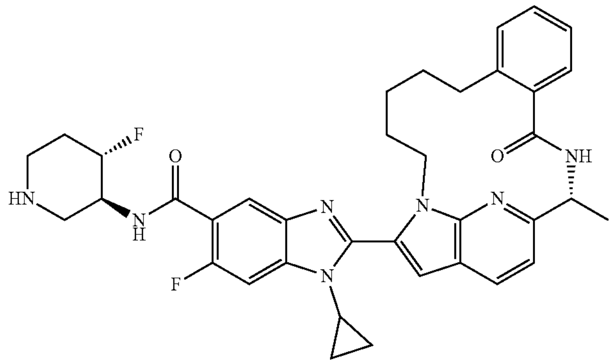 [SMILES: C[C@H]1NC(=O)c2ccccc2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R})-2-methyl-4-oxo-3,16,22-triazatetracyclo[14.5.2.0^{5,10}.0^{19,23}]tricosa-1(22),5,7,9,17,19(23),20-heptaen-17-yl]benzimidazole-5-carboxamide |
| 348 | 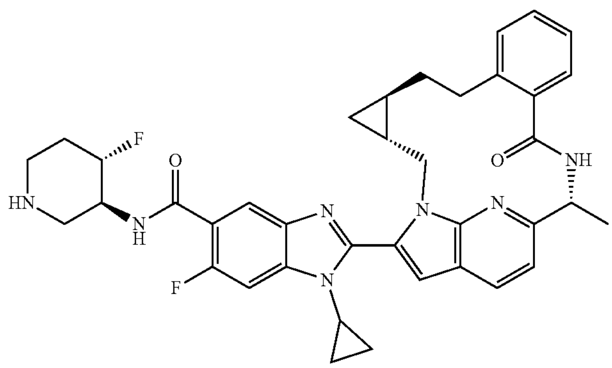 [SMILES: C[C@H]1NC(=O)c2ccccc2CC[C@@H]2C[C@H]2Cn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(3~{R},5~{R},16~{R})-16-methyl-14-oxo-1,15,24-triazapentacyclo[15.5.2.0^{3,5}.0^{8,13}.0^{20,23}]tetracosa-8,10,12,17(24),18,20(23),21-heptaen-22-yl]benzimidazole-5-carboxamide |
| 349 | 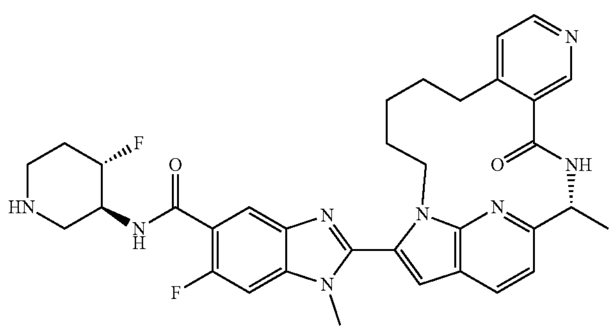 [SMILES: C[C@H]1NC(=O)c2cnccc2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R})-2-methyl-4-oxo-3,7,16,22-tetrazatetracyclo[14.5.2.0^{5,10}.0^{19,23}]tricosa-1(22),5,7,9,17,19(23),20-heptaen-17-yl]benzimidazole-5-carboxamide |
| 350 | 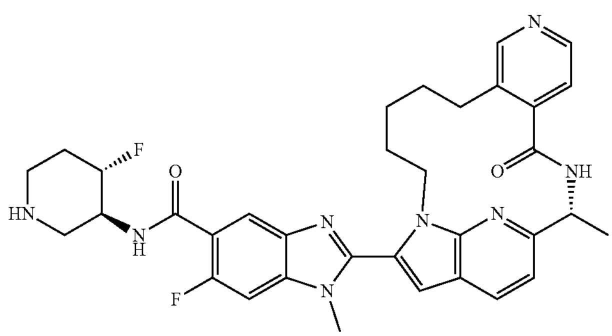 [SMILES: C[C@H]1NC(=O)c2ccncc2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R})-2-methyl-4-oxo-3,8,16,22-tetrazatetracyclo[14.5.2.0^{5,10}.0^{19,23}]tricosa-1(22),5,7,9,17,19(23),20-heptaen-17-yl]benzimidazole-5-carboxamide |

TABLE 1-continued

| Example | Structure | Name |
|---|---|---|
| 351 | 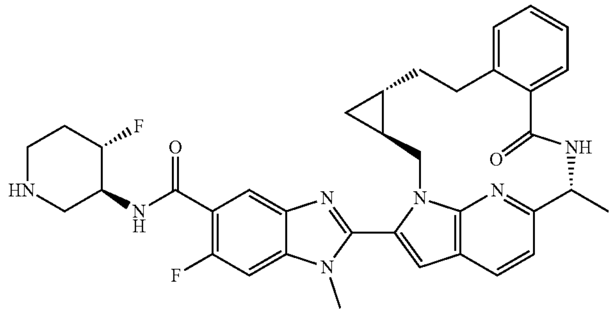 [SMILES: C[C@H]1NC(=O)c2ccccc2CC[C@H]2C[C@@H]2Cn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(3~{S},5~{S},16~{R})-16-methyl-14-oxo-1,15,24-triazapentacyclo[15.5.2.0^{3,5}.0^{8,13}.0^{20,23}]tetracosa-8,10,12,17(24),18,20(23),21-heptaen-22-yl]benzimidazole-5-carboxamide |
| 352 | 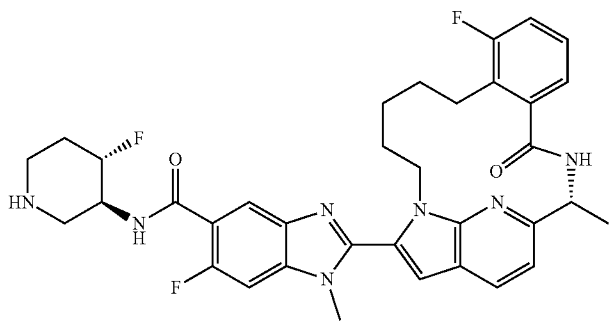 [SMILES: C[C@H]1NC(=O)c2cccc(F)c2CCCCCn2c(-c3nc4cc(C(=O)N[C@H]5CNCC[C@@H]5F)c(F)cc4n3C)cc3ccc1nc32] | 6-fluoro-2-[(2~{R})-9-fluoro-2-methyl-4-oxo-3,16,22-triazatetracyclo[14.5.2.0^{5,10}.0^{19,23}]tricosa-1(22),5,7,9,17,19(23),20-heptaen-17-yl]-~{N}-[(3~{S},4~{S})-4-fluoro-3-piperidyl]-1-methyl-benzimidazole-5-carboxamide |
| 353 | 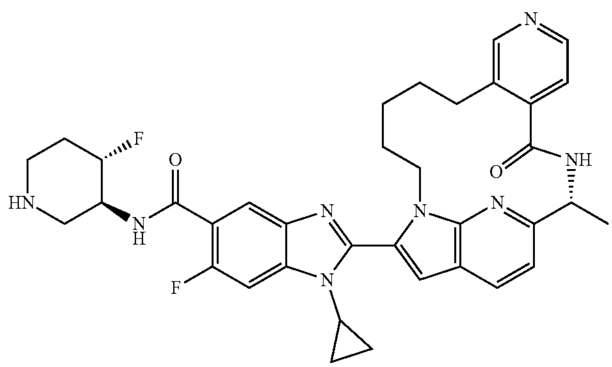 [SMILES: C[C@H]1NC(=O)c2ccncc2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R})-2-methyl-4-oxo-3,8,16,22-tetrazatetracyclo[14.5.2.0^{5,10}.0^{19,23}]tricosa-1(22),5,7,9,17,19(23),20-heptaen-17-yl]benzimidazole-5-carboxamide |
| 354 | 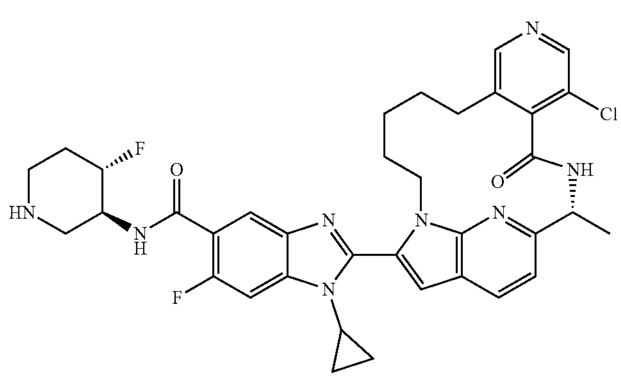 [SMILES: C[C@H]1NC(=O)c2c(Cl)cncc2CCCCCn2c(-c3nc4cc(C(=O)N[C@H]5CNCC[C@@H]5F)c(F)cc4n3C3CC3)cc3ccc1nc32] | 2-[(2~{R})-6-chloro-2-methyl-4-oxo-3,8,16,22-tetrazatetracyclo[14.5.2.0^{5,10}.0^{19,23}]tricosa-1(22),5,7,9,17,19(23),20-heptaen-17-yl]-1-cyclopropyl-6-fluoro-~{N}-[(3~{S},4~{S})-4-fluoro-3-piperidyl]benzimidazole-5-carboxamide |

TABLE 1-continued

| Example | Structure | Name |
|---|---|---|
| 355 | 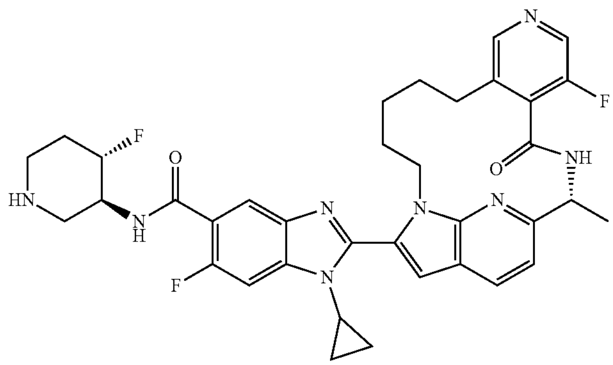 [SMILES: C[C@H]1NC(=O)c2c(F)cncc2CCCCCn2c(-c3nc4cc(C(=O)N[C@H]5CNCC[C@@H]5F)c(F)cc4n3C3CC3)cc3ccc1nc32] | 1-cyclopropyl-6-fluoro-2-[(2~{R})-6-fluoro-2-methyl-4-oxo-3,8,16,22-tetrazatetracyclo[14.5.2.0^{5,10}.0^{19,23}]tricosa-1(22),5,7,9,17,19(23),20-heptaen-17-yl]~{N}-[(3~{S},4~{S})-4-fluoro-3-piperidyl]benzimidazole-5-carboxamide |
| 356 | 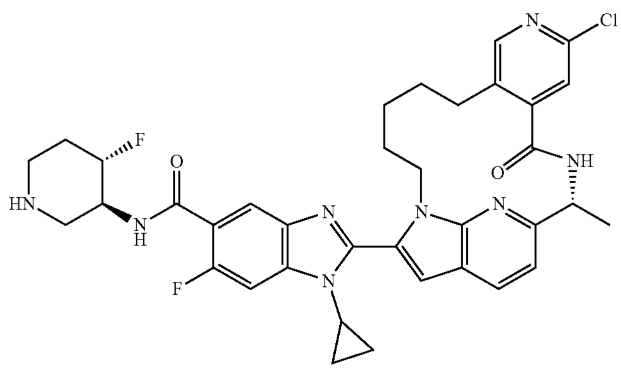 [SMILES: C[C@H]1NC(=O)c2cc(Cl)ncc2CCCCCn2c(-c3nc4cc(C(=O)N[C@H]5CNCC[C@@H]5F)c(F)cc4n3C3CC3)cc3ccc1nc32] | 2-[(2~{R})-7-chloro-2-methyl-4-oxo-3,8,16,22-tetrazatetracyclo[14.5.2.0^{5,10}.0^{19,23}]tricosa-1(22),5,7,9,17,19(23),20-heptaen-17-yl]-1-cyclopropyl-6-fluoro-~{N}-[(3~{S},4~{S})-4-fluoro-3-piperidyl]benzimidazole-5-carboxamide |
| 357 | 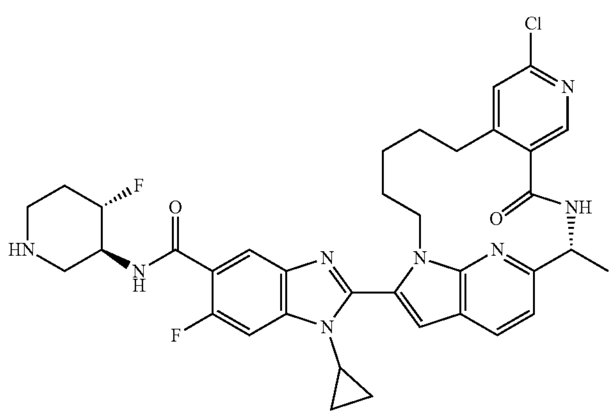 [SMILES: C[C@H]1NC(=O)c2cnc(Cl)cc2CCCCCn2c(-c3nc4cc(C(=O)N[C@H]5CNCC[C@@H]5F)c(F)cc4n3C3CC3)cc3ccc1nc32] | 2-[(2~{R})-8-chloro-2-methyl-4-oxo-3,7,16,22-tetrazatetracyclo[14.5.2.0^{5,10}.0^{19,23}]tricosa-1(22),5,7,9,17,19(23),20-heptaen-17-yl]-1-cyclopropyl-6-fluoro-~{N}-[(3~{S},4~{S})-4-fluoro-3-piperidyl]benzimidazole-5-carboxamide |
| 358 | 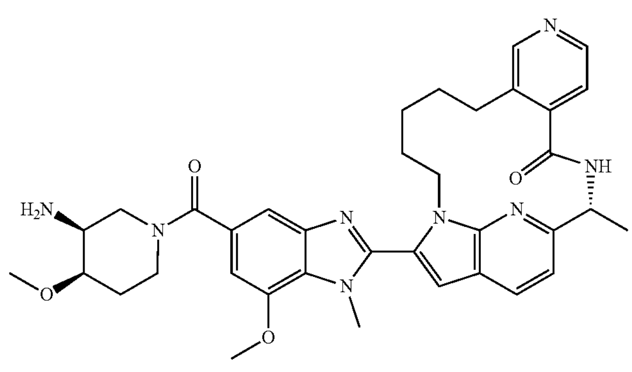 | (2~{R})-17-[5-[(3~{S},4~{R})-3-amino-4-methoxy-piperidine-1-carbonyl]-7-methoxy-1-methyl-benzimidazol-2-yl]-2-methyl-3,8,16,22-tetrazatetracyclo[14.5.2.0^{5,10}.0^{19,23}]tricosa-1(22),5,7,9,17,19(23),20-heptaen-4-one |

TABLE 1-continued

| Example | Structure | Name |
|---|---|---|
| 359 | 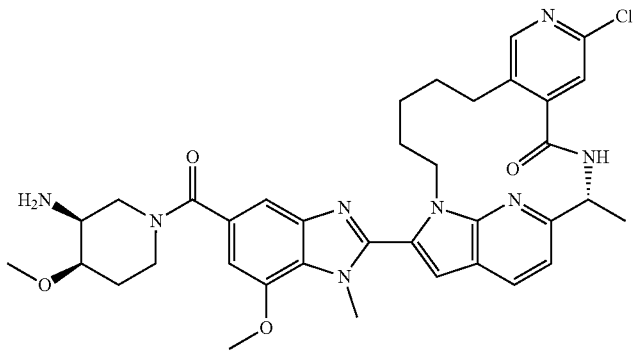 | (2~{R})-17-[5-[(3~{S},4~{R})-3-amino-4-methoxy-piperidine-1-carbonyl]-7-methoxy-1-methyl-benzimidazol-2-yl]-7-chloro-2-methyl-3,8,16,22-tetrazatetracyclo[14.5.2.0^{5,10}.0^{19,23}]tricosa-1(22),5,7,9,17,19(23),20-heptaen-4-one |
| 360 | 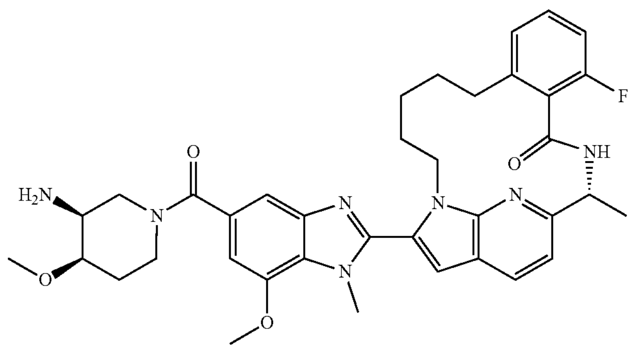 | (2~{R})-17-[5-[(3~{S},4~{R})-3-amino-4-methoxy-piperidine-1-carbonyl]-7-methoxy-1-methyl-benzimidazol-2-yl]-6-fluoro-2-methyl-3,16,22-triazatetracyclo[14.5.2.0^{5,10}.0^{19,23}]tricosa-1(22),5,7,9,17,19(23),20-heptaen-4-one |
| 361 | 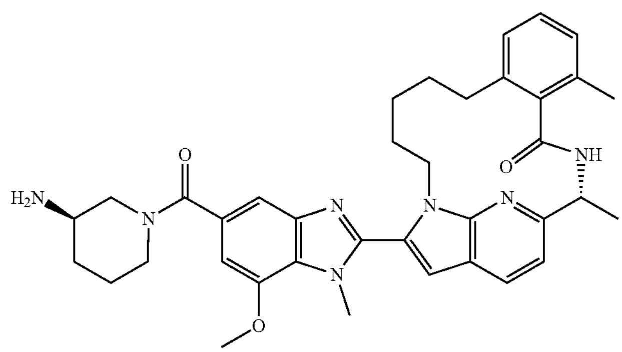 [SMILES: COc1cc(C(=O)N2CCC[C@@H](N)C2)cc2nc(-c3cc4ccc5nc4n3CCCCCc3cccc(C)c3C(=O)N[C@@H]5C)n(C)c12] | (2~{R})-17-[5-[(3~{R})-3-aminopiperidine-1-carbonyl]-7-methoxy-1-methyl-benzimidazol-2-yl]-2,6-dimethyl-3,16,22-triazatetracyclo[14.5.2.0^{5,10}.0^{19,23}]tricosa-1(22),5(10),6,8,17,19(23),20-heptaen-4-one |
| 362 | 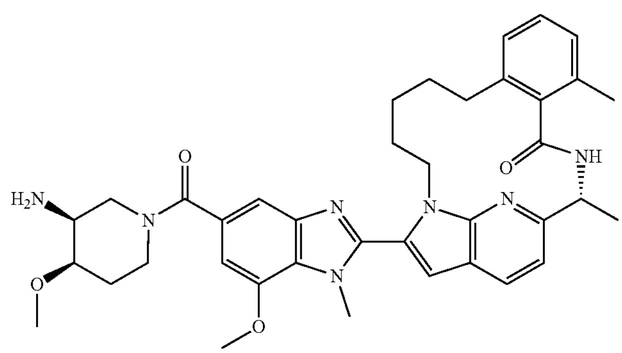 [SMILES: COc1cc(C(=O)N2CC[C@@H](OC)[C@@H](N)C2)cc2nc(-c3cc4ccc5nc4n3CCCCCc3cccc(C)c3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-2,6-dimethyl-3,16,22-triazatetracyclo[14.5.2.0^{5,10}.0^{19,23}]tricosa-1(22),5(10),6,8,17,19(23),20-heptaen-4-one |

TABLE 1-continued

| Example | Structure | Name |
|---|---|---|
| 363 | 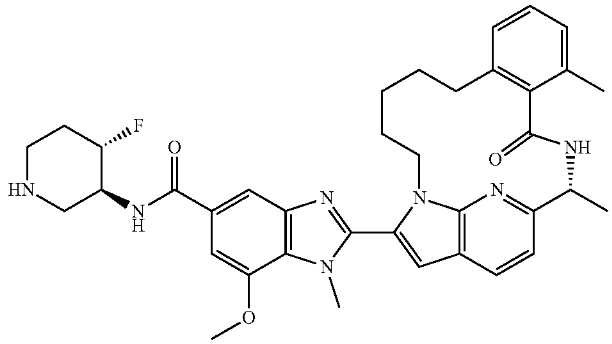 [SMILES: COc1cc(C(=O)N[C@H]2CNCC[C@@H]2F)cc2nc(-c3cc4ccc5nc4n3CCCCCc3cccc(C)c3C(=O)N[C@@H]5C)n(C)c12] | 2-[(2~{R})-2,6-dimethyl-4-oxo-3,16,22-triazatetracyclo[14.5.2.0^{5,10}.0^{19,23}]tricosa-1(22),5(10),6,8,17,19(23),20-heptaen-17-yl]-~{N}-[(3~{S},4~{S})-4-fluoro-3-piperidyl]-7-methoxy-1-methyl-benzimidazole-5-carboxamide |
| 364 | 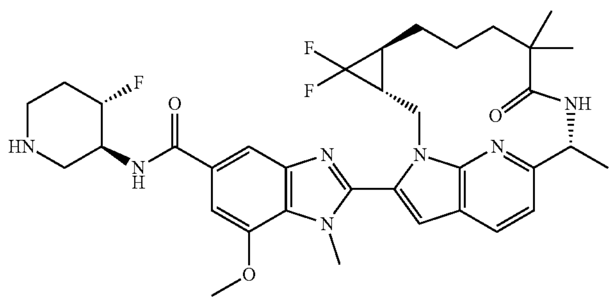 [SMILES: COc1cc(C(=O)N[C@H]2CNCC[C@@H]2F)cc2nc(-c3cc4ccc5nc4n3C[C@H]3[C@H](CCCC(C)(C)C(=O)N[C@@H]5C)C3(F)F)n(C)c12] | 2-[(3~{R},5~{S},12~{R})-4,4-difluoro-9,9,12-trimethyl-10-oxo-1,11,20-triazatetracyclo[11.5.2.0^{3,5}.0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide |
| 365 | 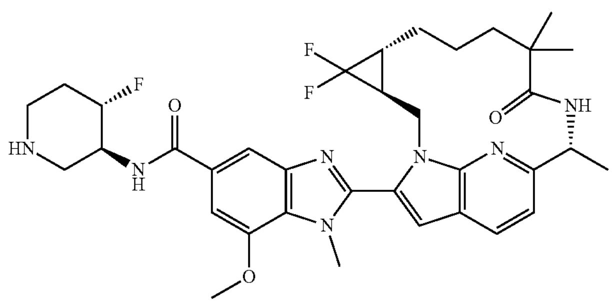 [SMILES: COc1cc(C(=O)N[C@H]2CNCC[C@@H]2F)cc2nc(-c3cc4ccc5nc4n3C[C@@H]3[C@@H](CCCC(C)(C)C(=O)N[C@@H]5C)C3(F)F)n(C)c12] | 2-[(3~{S},5~{R},12~{R})-4,4-difluoro-9,9,12-trimethyl-10-oxo-1,11,20-triazatetracyclo[11.5.2.0^{3,5}.0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide |
| 366 | 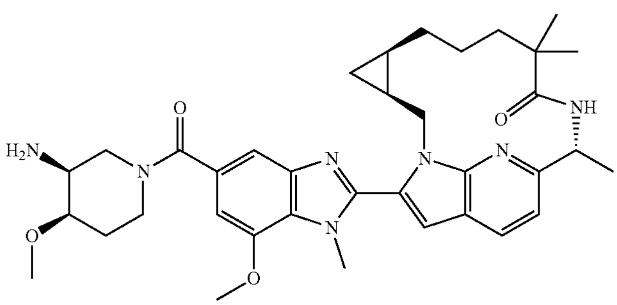 [SMILES: COc1cc(C(=O)N2CC[C@@H](OC)[C@@H](N)C2)cc2nc(-c3cc4ccc5nc4n3C[C@H]3C[C@H]3CCCC(C)(C)C(=O)N[C@@H]5C)n(C)c12] | (3~{S},5~{R},12~{R})-18-[5-[(3~{S},4~{R})-3-amino-4-methoxy-piperidine-1-carbonyl]-7-methoxy-1-methyl-benzimidazol-2-yl]-9,9,12-trimethyl-1,11,20-triazatetracyclo[11.5.2.0^{3,5}.0^{16,19}]icosa-13(20),14,16(19),17-tetraen-10-one |
| 367 | 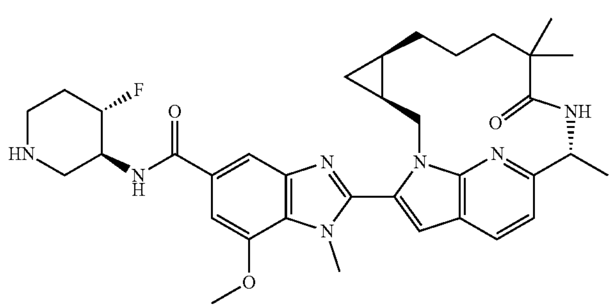 [SMILES: COc1cc(C(=O)N[C@H]2CNCC[C@@H]2F)cc2nc(-c3cc4ccc5nc4n3C[C@H]3C[C@H]3CCCC(C)(C)C(=O)N[C@@H]5C)n(C)c12] | ~{N}-[(3~{S},4~{S})-4-fluoro-3-piperidyl]-7-methoxy-1-methyl-2-[(3~{S},5~{R},12~{R})-9,9,12-trimethyl-10-oxo-1,11,20-triazatetracyclo[11.5.2.0^{3,5}.0^{16,19}]icosa-13(20),14,16(19),17-tetraen-18-yl]benzimidazole-5-carboxamide |

TABLE 1-continued

| Example | Structure | Name |
|---|---|---|
| 368 | 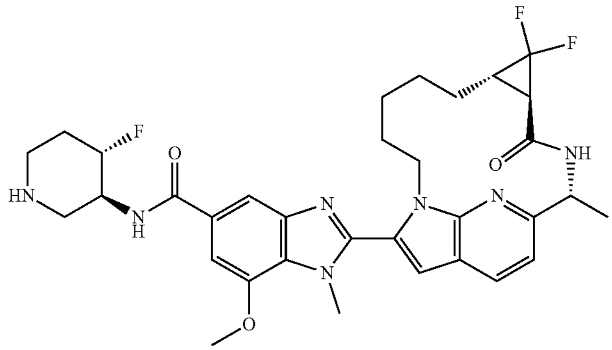 [SMILES: COc1cc(C(=O)N[C@H]2CNCC[C@@H]2F)cc2nc(-c3cc4ccc5nc4n3CCCCC[C@H]3[C@H](C(=O)N[C@@H]5C)C3(F)F)n(C)c12] | 2-[(2~{R},5~{R},7~{S})-6,6-difluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]-7-methoxy-1-methyl-benzimidazole-5-carboxamide |
| 369 | 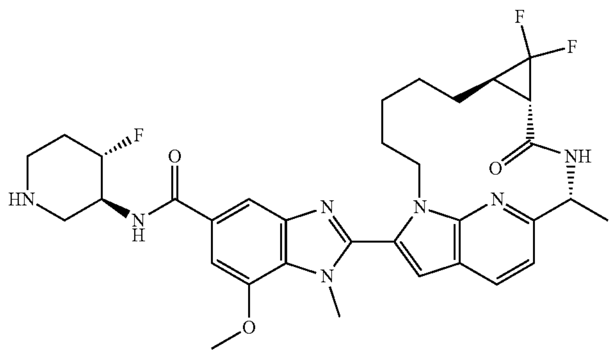 [SMILES: COc1cc(C(=O)N[C@H]2CNCC[C@@H]2F)cc2nc(-c3cc4ccc5nc4n3CCCCC[C@@H]3[C@@H](C(=O)N[C@@H]5C)C3(F)F)n(C)c12] | 2-[(2~{R},5~{S},7~{R})-6,6-difluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]-7-methoxy-1-methyl-benzimidazole-5-carboxamide |
| 370 | 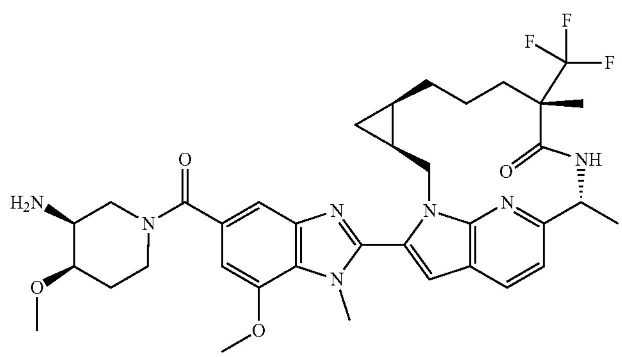 [SMILES: COc1cc(C(=O)N2CC[C@@H](OC)[C@@H](N)C2)cc2nc(-c3cc4ccc5nc4n3C[C@H]3C[C@H]3CCC[C@](C)(C(F)(F)F)C(=O)N[C@@H]5C)n(C)c12] | (3~{S},5~{R},9~{S},12~{R})-18-[5-[(3~{S},4~{R})-3-amino-4-methoxy-piperidine-1-carbonyl]-7-methoxy-1-methyl-benzimidazol-2-yl]-9,12-dimethyl-9-(trifluoromethyl)-1,11,20-triazatetracyclo[11.5.2.0^{3,5}.0^{16,19}]icosa-13(20),14,16(19),17-tetraen-10-one |
| 371 | 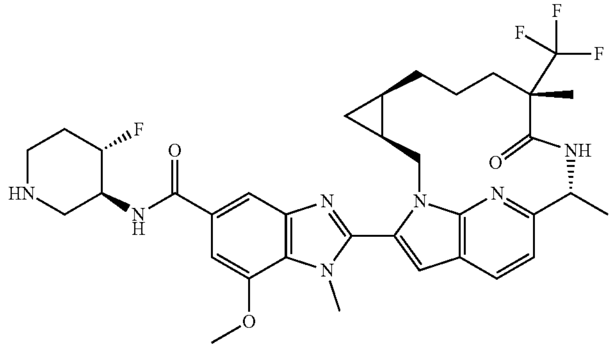 [SMILES: COc1cc(C(=O)N[C@H]2CNCC[C@@H]2F)cc2nc(-c3cc4ccc5nc4n3C[C@H]3C[C@H]3CCC[C@](C)(C(F)(F)F)C(=O)N[C@@H]5C)n(C)c12] | 2-[(3~{S},5~{R},9~{S},12~{R})-9,12-dimethyl-10-oxo-9-(trifluoromethyl)-1,11,20-triazatetracyclo[11.5.2.0^{3,5}.0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide |

TABLE 1-continued

| Example | Structure | Name |
|---|---|---|
| 372 | 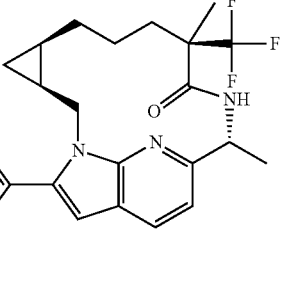 | (3~{S},5~{R},9~{R},12~{R})-18-[5-[(3~{S},4~{R})-3-amino-4-methoxy-piperidine-1-carbonyl]-7-methoxy-1-methyl-benzimidazol-2-yl]-9,12-dimethyl-9-(trifluoromethyl)-1,11,20-triazatetracyclo[11.5.2.0^{3,5}.0^{16,19}]icosa-13(20),14,16(19),17-tetraen-10-one |
| 373 | 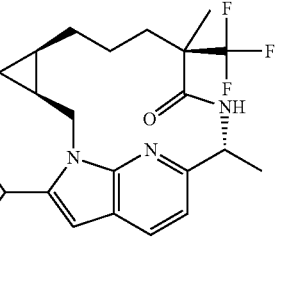 | 2-[(3~{S},5~{R},9~{R},12~{R})-9,12-dimethyl-10-oxo-9-(trifluoromethyl)-1,11,20-triazatetracyclo[11.5.2.0^{3,5}.0^{16,19}]icosa-13(20),14,16(19),17-tetraen-18-yl]-~{N}-[(3~{S},4~{S})-4-fluoro-3-piperidyl]-7-methoxy-1-methyl-benzimidazole-5-carboxamide |
| 374 | 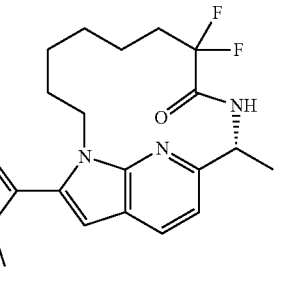 | (11~{R})-17-[5-[(3~{S},4~{R})-3-amino-4-methoxy-piperidine-1-carbonyl]-7-methoxy-1-methyl-benzimidazol-2-yl]-8,8-difluoro-11-methyl-1,10,19-triazatricyclo[10.5.2.0^{15,18}]nonadeca-12(19),13,15(18),16-tetraen-9-one |
| 375 | 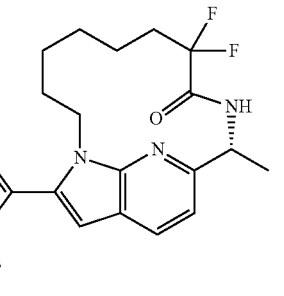 | 2-[(11~{R})-8,8-difluoro-11-methyl-9-oxo-1,10,19-triazatricyclo[10.5.2.0^{15,18}]nonadeca-12(19),13,15(18),16-tetraen-17-yl]-~{N}-[(3~{S},4~{S})-4-fluoro-3-piperidyl]-7-methoxy-1-methyl-benzimidazole-5-carboxamide |
| 376 | 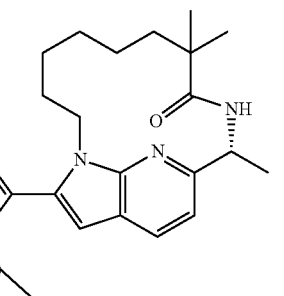 | 1-cyclopropyl-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 377 | 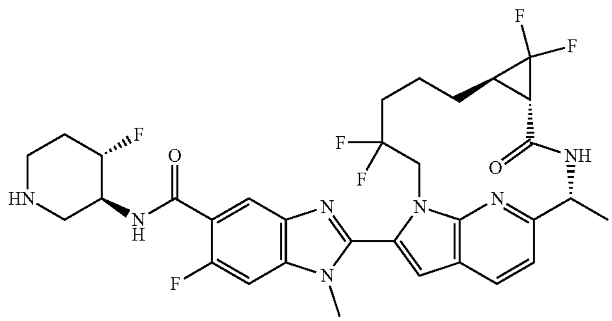 [SMILES: C[C@H]1NC(=O)[C@@H]2[C@@H](CCCC(F)(F)Cn3c(-c4nc5cc(C(=O)N[C@H]6CNCC[C@@H]6F)c(F)cc5n4C)cc4ccc1nc43)C2(F)F] | 6-fluoro-~{N}-[(3~{S},4~{S})-4-fluoro-3-piperidyl]-1-methyl-2-[(2~{R},5~{S},7~{R})-6,6,11,11-tetrafluoro-2-methyl-4-oxo-3,13,19-triazatetracyclo[11.5.2.0´{5,7}.0´{16,20}]icosa-1(19),14,16(20),17-tetraen-14-yl]benzimidazole-5-carboxamide |
| 378 | 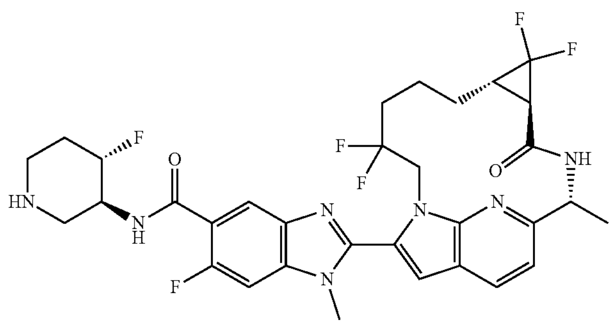 [SMILES: C[C@H]1NC(=O)[C@H]2[C@H](CCCC(F)(F)Cn3c(-c4nc5cc(C(=O)N[C@H]6CNCC[C@@H]6F)c(F)cc5n4C)cc4ccc1nc43)C2(F)F] | 6-fluoro-~{N}-[(3~{S},4~{S})-4-fluoro-3-piperidyl]-1-methyl-2-[(2~{R},5~{R},7~{S})-6,6,11,11-tetrafluoro-2-methyl-4-oxo-3,13,19-triazatetracyclo[11.5.2.0´{5,7}.0´{16,20}]icosa-1(19),14,16(20),17-tetraen-14-yl]benzimidazole-5-carboxamide |
| 379 | 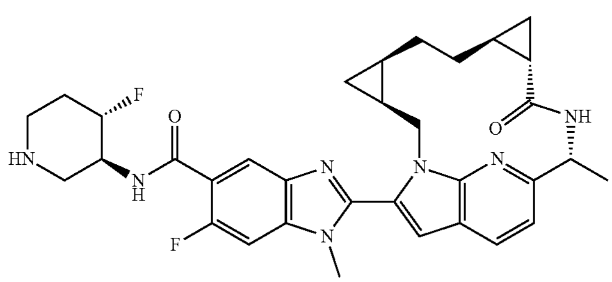 [SMILES: C[C@H]1NC(=O)[C@H]2C[C@@H]2CC[C@@H]2C[C@@H]2Cn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(3~{S},5~{R},8~{S},10~{S},13~{R})-13-methyl-11-oxo-1,12,21-triazapentacyclo[12.5.2.0´{3,5}.0´{8,10}.0´{17,20}]henicosa-14(21),15,17(20),18-tetraen-19-yl]benzimidazole-5-carboxamide |
| 380 | 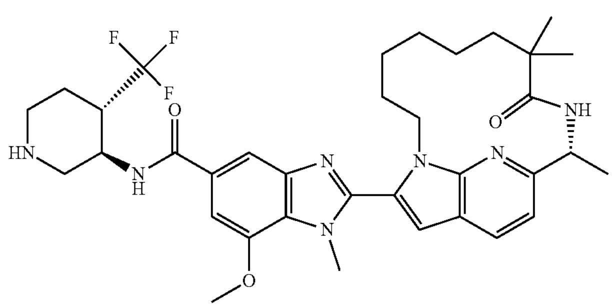 [SMILES: COc1cc(C(=O)N[C@H]2CNCC[C@@H]2C(F)(F)F)cc2nc(-c3cc4ccc5nc4n3CCCCCCC(C)(C)C(=O)N[C@@H]5C)n(C)c12] | 7-methoxy-1-methyl-~{N}-[(3~{R},4~{S})-4-(trifluoromethyl)-3-piperidyl]-2-[(11~{R})-8,8,11-trimethyl-9-oxo-1,10,19-triazatricyclo[10.5.2.0´{15,18}]nonadeca-12(19),13,15(18),16-tetraen-17-yl]benzimidazole-5-carboxamide |
| 381 | 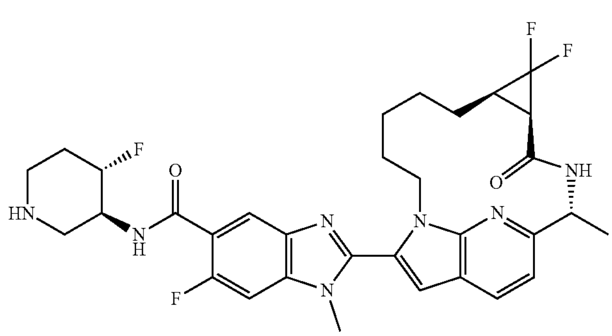 [SMILES: C[C@H]1NC(=O)[C@H]2[C@@H](CCCCCn3c(-c4nc5cc(C(=O)N[C@H]6CNCC[C@@H]6F)c(F)cc5n4C)cc4ccc1nc43)C2(F)F] | 2-[(2~{R},5~{R},7~{R})-6,6-difluoro-2-methyl-4-oxo-3,13,19-triazatetracyclo[11.5.2.0´{5,7}.0´{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |

TABLE 1-continued

| Example | Structure | Name |
|---|---|---|
| 382 | 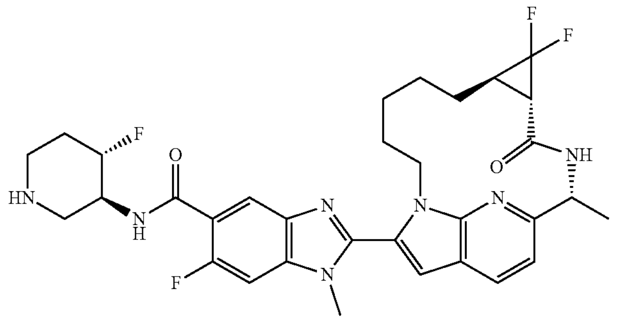 [SMILES: C[C@H]1NC(=O)[C@@H]2[C@@H](CCCCCn3c(-c4nc5cc(C(=O)N[C@H]6CNCC[C@@H]6F)c(F)cc5n4C)cc4ccc1nc43)C2(F)F] | 2-[(2~{R},5~{S},7~{R})-6,6-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 383 | 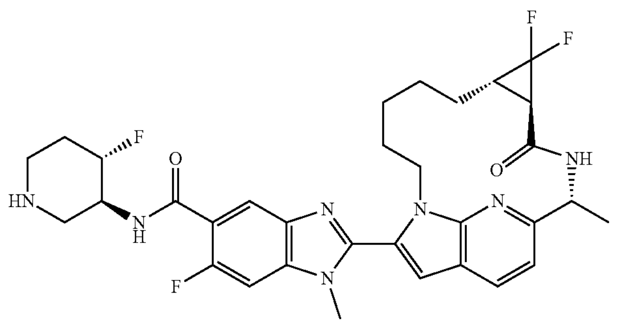 [SMILES: C[C@H]1NC(=O)[C@H]2[C@H](CCCCCn3c(-c4nc5cc(C(=O)N[C@H]6CNCC[C@@H]6F)c(F)cc5n4C)cc4ccc1nc43)C2(F)F] | 2-[(2~{R},5~{R},7~{S})-6,6-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 384 | 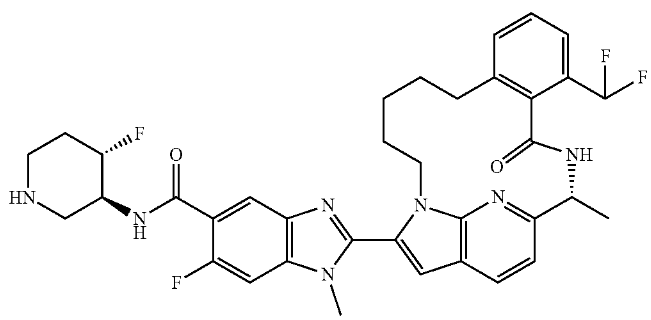 [SMILES: C[C@H]1NC(=O)c2c(cccc2C(F)F)CCCCCn2c(-c3nc4cc(C(=O)N[C@H]5CNCC[C@@H]5F)c(F)cc4n3C)cc3ccc1nc32] | 2-[(2~{R})-6-(difluoromethyl)-2-methyl-4-oxo-3,16,22-triazatetracyclo[14.5.2.0^{5,10}.0^{19,23}]tricosa-1(22),5(10),6,8,17,19(23),20-heptaen-17-yl]-6-fluoro-~{N}-[(3~{S},4~{S})-4-fluoro-3-piperidyl]-1-methyl-benzimidazole-5-carboxamide |
| 385 | 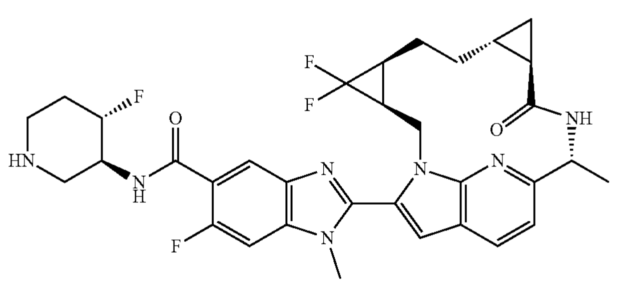 [SMILES: C[C@H]1NC(=O)[C@@H]2C[C@H]2CC[C@H]2[C@@H](Cn3c(-c4nc5cc(C(=O)N[C@H]6CNCC[C@@H]6F)c(F)cc5n4C)cc4ccc1nc43)C2(F)F] | 2-4,4-difluoro-13-methyl-11-oxo-1,12,21-triazapentacyclo[12.5.2.0^{3,5}.0^{8,10}.0^{17,20}]henicosa-14(21),15,17(20),18-tetraen-19-yl]-6-fluoro-~{N}-[(3~{S},4~{S})-4-fluoro-3-piperidyl]-1-methyl-benzimidazole-5-carboxamide |
| 386 | 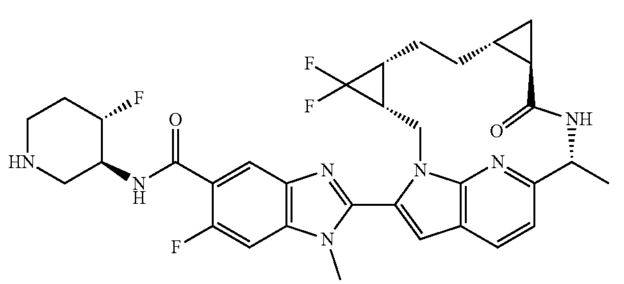 [SMILES: C[C@H]1NC(=O)[C@@H]2C[C@H]2CC[C@@H]2[C@H](Cn3c(-c4nc5cc(C(=O)N[C@H]6CNCC[C@@H]6F)c(F)cc5n4C)cc4ccc1nc43)C2(F)F] | 2-[(3~{R},5~{R},8~{R},10~{R},13~{R})-4,4-difluoro-13-methyl-11-oxo-1,12,21-triazapentacyclo[12.5.2.0^{3,5}.0^{8,10}.0^{17,20}]henicosa-14(21),15,17(20),18-tetraen-19-yl]-6-fluoro-~{N}-[(3~{S},4~{S})-4-fluoro-3-piperidyl]-1-methyl-benzimidazole-5-carboxamide |

TABLE 1-continued

| Example | Structure | Name |
|---|---|---|
| 387 | 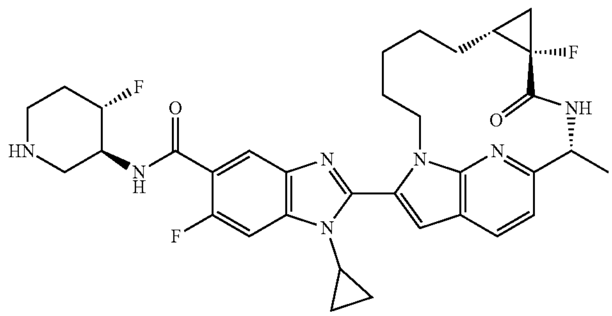 [SMILES: C[C@H]1NC(=O)[C@]2(F)C[C@H]2CCCCCn2c(-c3nc4cc(C(=O)N[C@H]5CNCC[C@@H]5F)c(F)cc4n3C3CC3)cc3ccc1nc32] | 1-cyclopropyl-6-fluoro-2-[(2~{R},5~{S},7~{R})-5-fluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]benzimidazole-5-carboxamide |
| 388 | 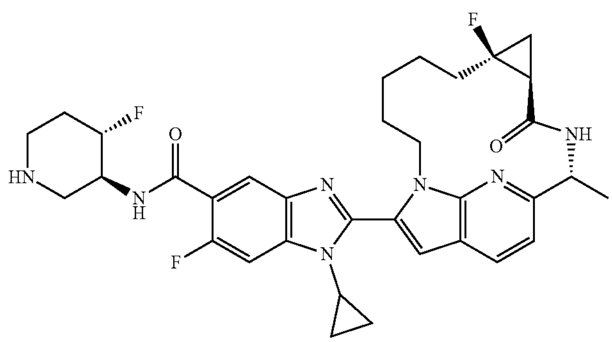 [SMILES: C[C@H]1NC(=O)[C@@H]2C[C@@]2(F)CCCCCn2c(-c3nc4cc(C(=O)N[C@H]5CNCC[C@@H]5F)c(F)cc4n3C3CC3)cc3ccc1nc32] | 1-cyclopropyl-6-fluoro-2-[2~{R},5~{S},7~{S})-7-fluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]benzimidazole-5-carboxamide |
| 389 | 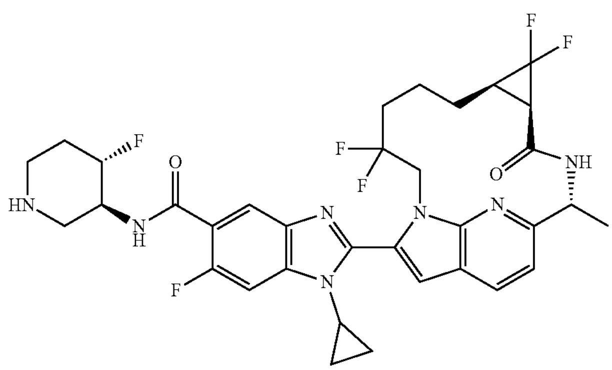 [SMILES: C[C@H]1NC(=O)[C@H]2[C@@H](CCCC(F)(F)Cn3c(-c4nc5cc(C(=O)N[C@H]6CNCC[C@@H]6F)c(F)cc5n4C4CC4)cc4ccc1nc43)C2(F)F] | 1-cyclopropyl-6-fluoro-~{N}-[(3~{S},4~{S})-4-fluoro-3-piperidyl]-2-[(2~{R},5~{R},7~{R})-6,6,11,11-tetrafluoro-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 390 | 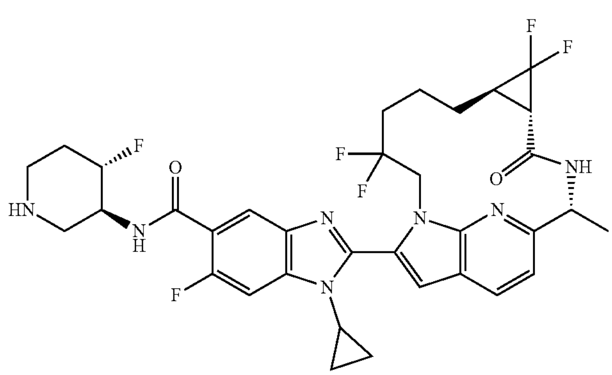 [SMILES: C[C@H]1NC(=O)[C@@H]2[C@@H](CCCC(F)(F)Cn3c(-c4nc5cc(C(=O)N[C@H]6CNCC[C@@H]6F)c(F)cc5n4C4CC4)cc4ccc1nc43)C2(F)F] | 1-cyclopropyl-6-fluoro-~{N}-[(3~{S},4~{S})-4-fluoro-3-piperidyl]-2-[(2~{R},5~{S},7~{R})-6,6,11,11-tetrafluoro-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1-continued

| Example | Structure | Name |
|---|---|---|
| 391 | 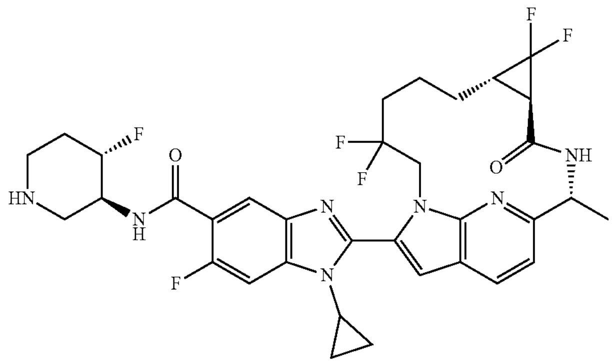 [SMILES: C[C@H]1NC(=O)[C@H]2[C@H](CCCC(F)(F)Cn3c(-c4nc5cc(C(=O)N[C@H]6CNCC[C@@H]6F)c(F)cc5n4C4CC4)cc4ccc1nc43)C2(F)F] | 1-cyclopropyl-6-fluoro-~{N}-[(3~{S},4~{S})-4-fluoro-3-piperidyl]-2-[(2~{R},5~{R},7~{S})-6,6,11,11-tetrafluoro-2-methyl-4-oxo-3,13,19-triazatetracyclo[11.5.2.0`{5,7}.0`{16,20}]icosa-1(19),14,16(20),17-tetraen-14-yl]benzimidazole-5-carboxamide |
| 392 | 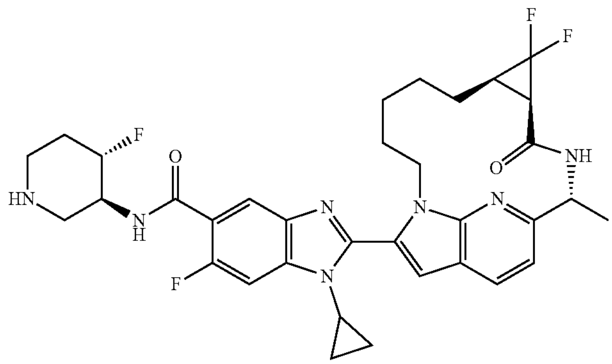 [SMILES: C[C@H]1NC(=O)[C@H]2[C@@H](CCCCCn3c(-c4nc5cc(C(=O)N[C@H]6CNCC[C@@H]6F)c(F)cc5n4C4CC4)cc4ccc1nc43)C2(F)F] | 1-cyclopropyl-2-[(2~{R},5~{R},7~{R})-6,6-difluoro-2-methyl-4-oxo-3,13,19-triazatetracyclo[11.5.2.0`{5,7}.0`{16,20}]icosa-1(19),14,16(20),17-tetraen-14-yl]-6-fluoro-~{N}-[(3~{S},4~{S})-4-fluoro-3-piperidyl]benzimidazole-5-carboxamide |
| 393 | 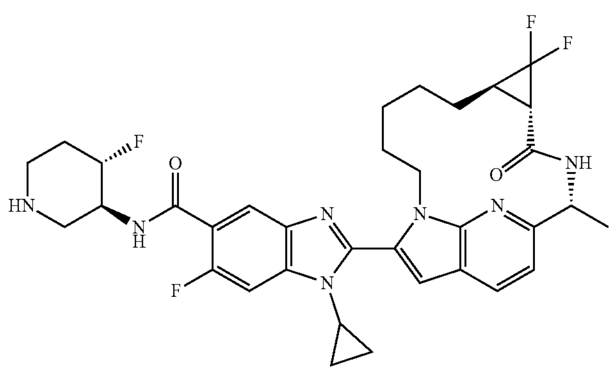 [SMILES: C[C@H]1NC(=O)[C@@H]2[C@@H](CCCCCn3c(-c4nc5cc(C(=O)N[C@H]6CNCC[C@@H]6F)c(F)cc5n4C4CC4)cc4ccc1nc43)C2(F)F] | 1-cyclopropyl-2-[(2~{R},5~{S},7~{R})-6,6-difluoro-2-methyl-4-oxo-3,13,19-triazatetracyclo[11.5.2.0`{5,7}.0`{16,20}]icosa-1(19),14,16(20),17-tetraen-14-yl]-6-fluoro-~{N}-[(3~{S},4~{S})-4-fluoro-3-piperidyl]benzimidazole-5-carboxamide |
| 394 | 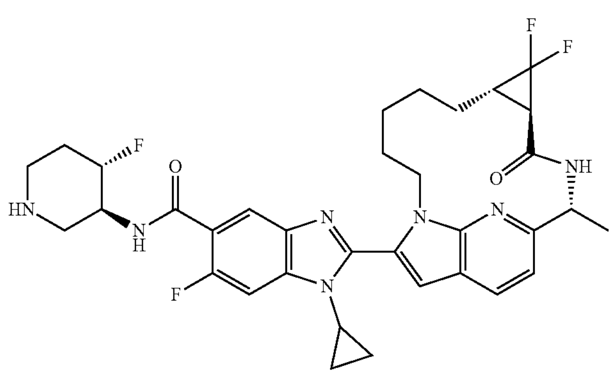 [SMILES: C[C@H]1NC(=O)[C@H]2[C@H](CCCCCn3c(-c4nc5cc(C(=O)N[C@H]6CNCC[C@@H]6F)c(F)cc5n4C4CC4)cc4ccc1nc43)C2(F)F] | 1-cyclopropyl-2-[(2~{R},5~{R},7~{S})-6,6-difluoro-2-methyl-4-oxo-3,13,19-triazatetracyclo[11.5.2.0`{5,7}.0`{16,20}]icosa-1(19),14,16(20),17-tetraen-14-yl]-6-fluoro-~{N}-[(3~{S},4~{S})-4-fluoro-3-piperidyl]benzimidazole-5-carboxamide |

TABLE 1-continued

| Example | Structure | Name |
|---|---|---|
| 395 | 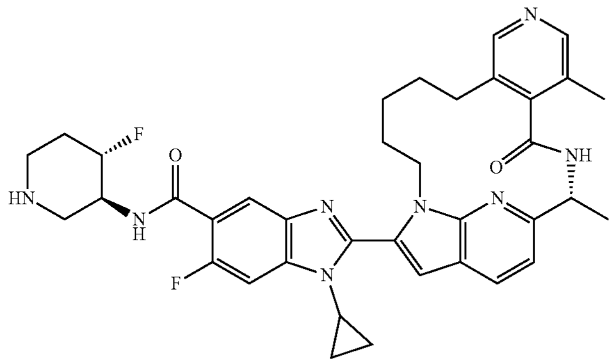 [SMILES: Cc1cncc2c1C(=O)N[C@H](C)c1ccc3cc(-c4nc5cc(C(=O)N[C@H]6CNCC[C@@H]6F)c(F)cc5n4C4CC4)n(c3n1)CCCCC2] | 1-cyclopropyl-2-[(2~{R})-2,6-dimethyl-4-oxo-3,8,16,22-tetrazatetracyclo[14.5.2.0^{5,10}.0^{19,23}]tricosa-1(22),5(10),6,8,17,19(23),20-heptaen-17-yl]-6-fluoro-~{N}-[(3~{S},4~{S})-4-fluoro-3-piperidyl]benzimidazole-5-carboxamide |
| 396 | 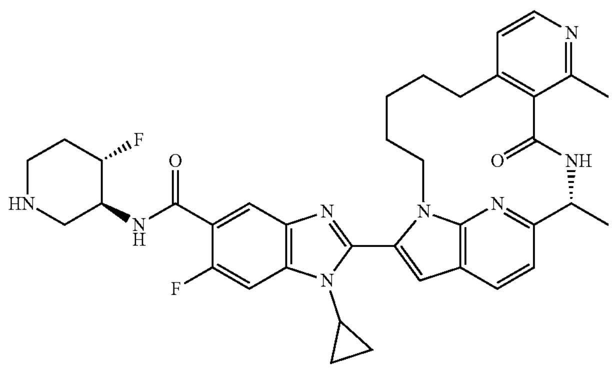 [SMILES: Cc1nccc2c1C(=O)N[C@H](C)c1ccc3cc(-c4nc5cc(C(=O)N[C@H]6CNCC[C@@H]6F)c(F)cc5n4C4CC4)n(c3n1)CCCCC2] | 1-cyclopropyl-2-[(2~{R})-2,6-dimethyl-4-oxo-3,7,16,22-tetrazatetracyclo[14.5.2.0^{5,10}.0^{19,23}]tricosa-1(22),5(10),6,8,17,19(23),20-heptaen-17-yl]-6-fluoro-~{N}-[(3~{S},4~{S})-4-fluoro-3-piperidyl]benzimidazole-5-carboxamide |
| 397 | 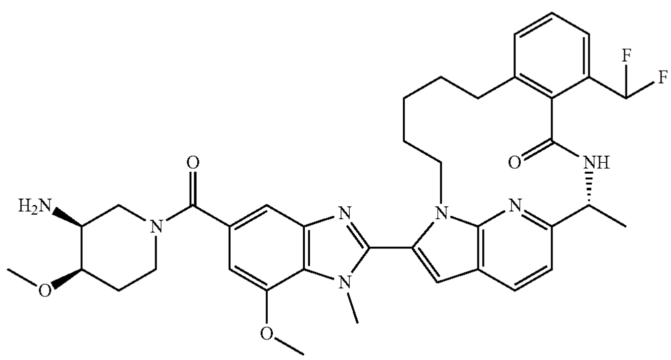 [SMILES: COc1cc(C(=O)N2CC[C@@H](OC)[C@@H](N)C2)cc2nc(-c3cc4ccc5nc4n3CCCCCc3cccc(C(F)F)c3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-6-(difluoromethyl)-2-methyl-3,16,22-triazatetracyclo[14.5.2.0^{5,10}.0^{19,23}]tricosa-1(22),5(10),6,8,17,19(23),20-heptaen-4-one |
| 398 | 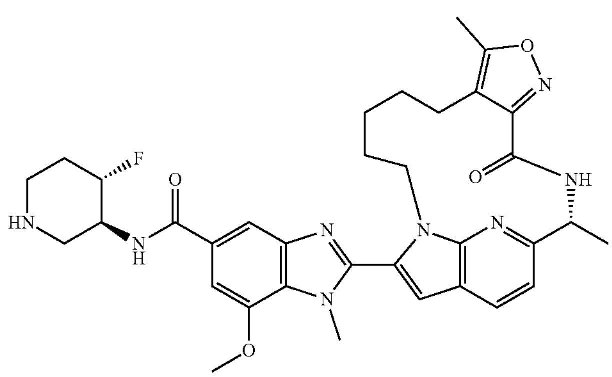 [SMILES: COc1cc(C(=O)N[C@H]2CNCC[C@@H]2F)cc2nc(-c3cc4ccc5nc4n3CCCCCc3c(noc3C)C(=O)N[C@@H]5C)n(C)c12] | 2-[(2~{R})-2,8-dimethyl-4-oxo-7-oxa-3,6,15,21-tetrazatetracyclo[13.5.2.0^{5,9}.0^{18,22}]docosa-1(21),5,8,16,18(22),19-hexaen-16-yl]-~{N}-[(3~{S},4~{S})-4-fluoro-3-piperidyl]-7-methoxy-1-methyl-benzimidazole-5-carboxamide |

TABLE 1-continued

| Example | Structure | Name |
|---|---|---|
| 399 | 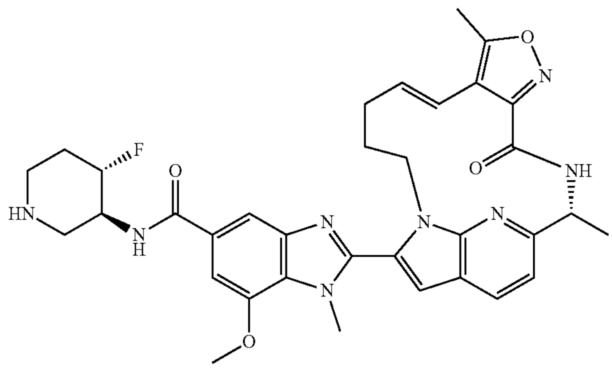 [SMILES: COc1cc(C(=O)N[C@H]2CNCC[C@@H]2F)cc2nc(-c3cc4ccc5nc4n3CCC/C=C/c3c(noc3C)C(=O)N[C@@H]5C)n(C)c12] | 2-[(2~{R},10~{E})-2,8-dimethyl-4-oxo-7-oxa-3,6,15,21-tetrazatetracyclo[13.5.2.0^{5,9}.0^{18,22}]docosa-1(21),5,8,10,16,18(22),19-heptaen-16-yl]-~{N}-[(3~{S},4~{S})-4-fluoro-3-piperidyl]-7-methoxy-1-methyl-benzimidazole-5-carboxamide |
| 400 | 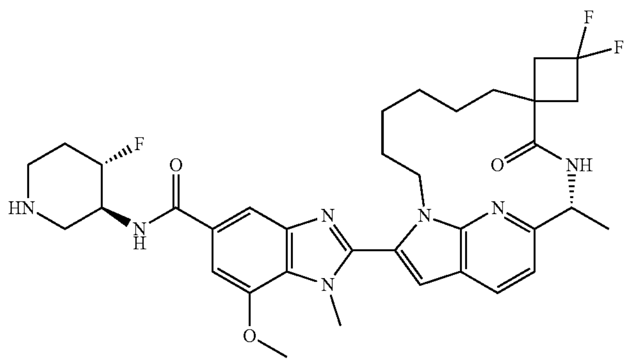 [SMILES: COc1cc(C(=O)N[C@H]2CNCC[C@@H]2F)cc2nc(-c3cc4ccc5nc4n3CCCCCCC3(CC(F)(F)C3)C(=O)N[C@@H]5C)n(C)c12] | 2-[(11~{R})-1',1'-difluoro-11-methyl-9-oxo-spiro[1,10,19-triazatricyclo[10.5.2.0^{15,18}]nonadeca-12(19),13,15(18),16-tetraene-8,3'-cyclobutane]-17-yl]-~{N}-[(3~{S},4~{S})-4-fluoro-3-piperidyl]-7-methoxy-1-methyl-benzimidazole-5-carboxamide |
| 401 | 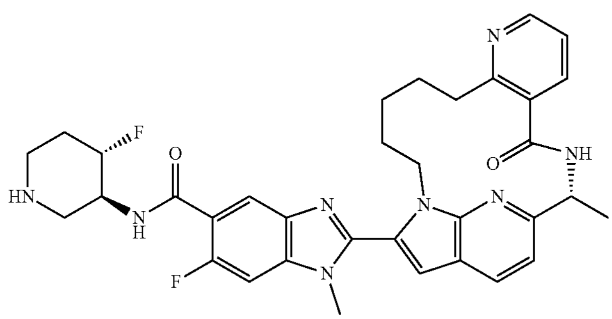 [SMILES: C[C@H]1NC(=O)c2cccnc2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R})-2-methyl-4-oxo-3,9,16,22-tetrazatetracyclo[14.5.2.0^{5,10}.0^{19,23}]tricosa-1(22),5(10),6,8,17,19(23),20-heptaen-17-yl]benzimidazole-5-carboxamide |
| 402 | 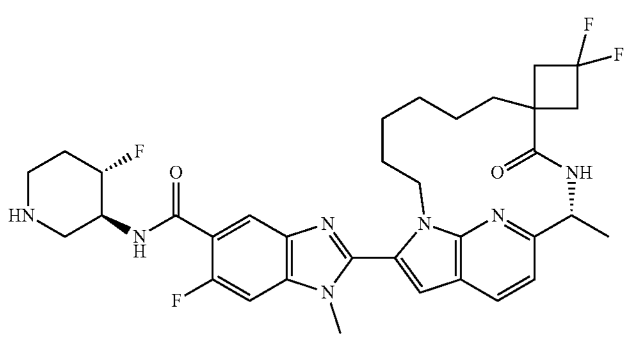 [SMILES: C[C@H]1NC(=O)C2(CCCCCCn3c(-c4nc5cc(C(=O)N[C@H]6CNCC[C@@H]6F)c(F)cc5n4C)cc4ccc1nc43)CC(F)(F)C2] | 2-[(11~{R})-1',1'-difluoro-11-methyl-9-oxo-spiro[1,10,19-triazatricyclo[10.5.2.0^{15,18}]nonadeca-12(19),13,15(18),16-tetraene-8,3'-cyclobutane]-17-yl]-6-fluoro-~{N}-[(3~{S},4~{S})-4-fluoro-3-piperidyl]-1-methyl-benzimidazole-5-carboxamide |

TABLE 1-continued

| Example | Structure | Name |
|---|---|---|
| 403 | 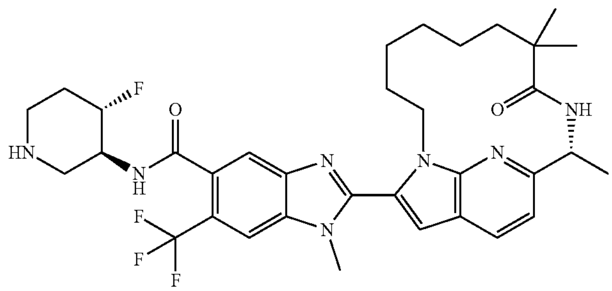 [SMILES: C[C@H]1NC(=O)C(C)(C)CCCCCCn2c(-c3nc4cc(C(=O)N[C@H]5CNCC[C@@H]5F)c(C(F)(F)F)cc4n3C)cc3ccc1nc32] | ~{N}-[(3~{S},4~{S})-4-fluoro-3-piperidyl]-1-methyl-6-(trifluoromethyl)-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 404 | 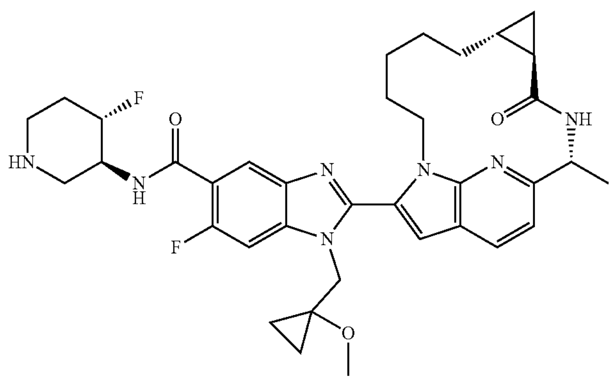 [SMILES: COC1(Cn2c(-c3cc4ccc5nc4n3CCCCC[C@@H]3C[C@H]3C(=O)N[C@@H]5C)nc3cc(C(=O)N[C@H]4CNCC[C@@H]4F)c(F)cc32)CC1] | 6-fluoro-~{N}-[(3~{S},4~{S})-4-fluoro-3-piperidyl]-1-[(1-methoxycyclopropyl)methyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 405 | 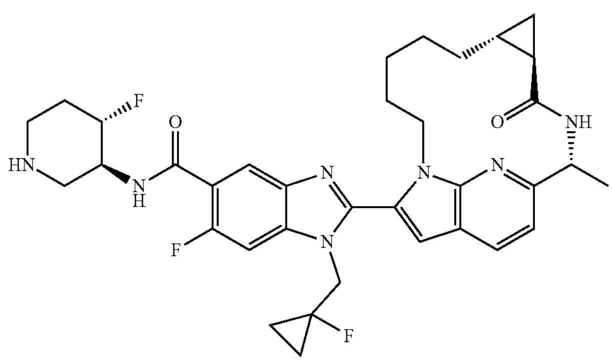 [SMILES: C[C@H]1NC(=O)[C@@H]2C[C@H]2CCCCCn2c(-c3nc4cc(C(=O)N[C@H]5CNCC[C@@H]5F)c(F)cc4n3CC3(F)CC3)cc3ccc1nc32] | 6-fluoro-1-[(1-fluorocyclopropyl)methyl]-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 406 | 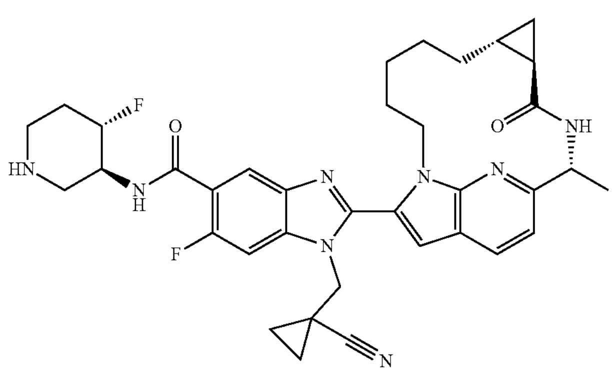 [SMILES: C[C@H]1NC(=O)[C@@H]2C[C@H]2CCCCCn2c(-c3nc4cc(C(=O)N[C@H]5CNCC[C@@H]5F)c(F)cc4n3CC3(C#N)CC3)cc3ccc1nc32] | 1-[(1-cyanocyclopropyl)methyl]-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1-continued

| Example | Structure | Name |
|---|---|---|
| 407 | 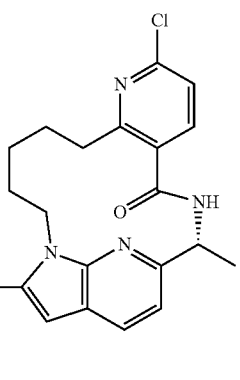 | (2~{R})-17-[5-[(3~{S},4~{R})-3-amino-4-methoxy-piperidine-1-carbonyl]-7-methoxy-1-methyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 408 | 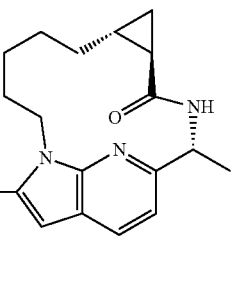 | (2~{R},5~{R},7~{R})-14-[5-[(2~{S},3~{R})-3-amino-2-(hydroxymethyl)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 409 | 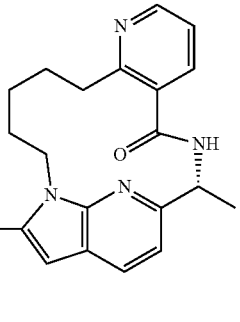 | (2~{R})-17-[5-[(3~{S},4~{R})-3-amino-4-methoxy-piperidine-1-carbonyl]-7-methoxy-1-methyl-benzimidazol-2-yl]-2-methyl-3,9,16,22-tetrazatetracyclo[14.5.2.0^{5,10}.0^{19,23}]tricosa-1(22),5(10),6,8,17,19(23),20-heptaen-4-one |
| 410 | 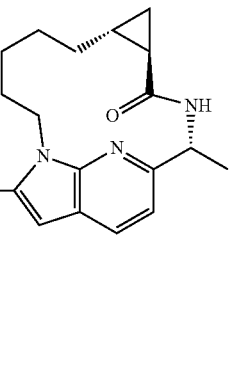 | 1-[(1~{R},2~{S})-2-(difluoromethyl)cyclopropyl]-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1-continued

| Example | Structure | Name |
|---|---|---|
| 411 | 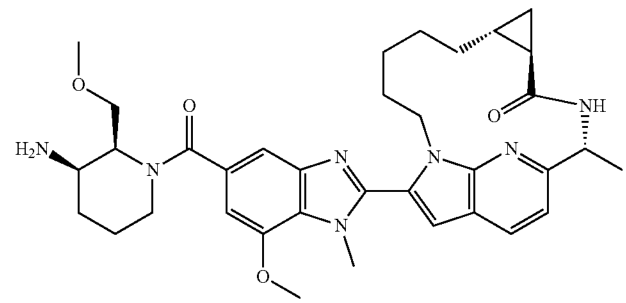 [SMILES: COC[C@@H]1[C@H](N)CCCN1C(=O)c1cc(OC)c2c(c1)nc(-c1cc3ccc4nc3n1CCCCC[C@@H]1C[C@H]1C(=O)N[C@@H]4C)n2C] | (2~{R},5~{R},7~{R})-14-[5-[(2~{S},3~{R})-3-amino-2-(methoxymethyl)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 412 | 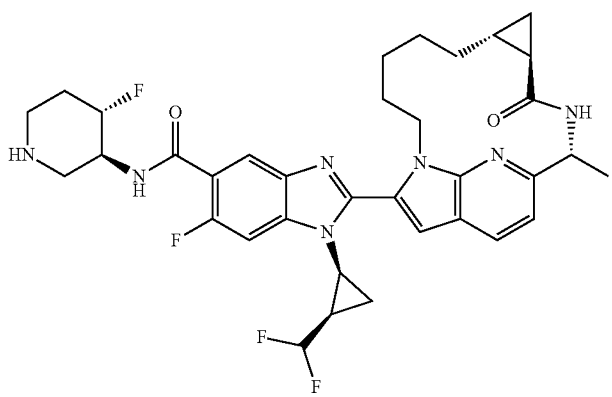 [SMILES: C[C@H]1NC(=O)[C@@H]2C[C@H]2CCCCCn2c(-c3nc4cc(C(=O)N[C@H]5CNCC[C@@H]5F)c(F)cc4n3[C@H]3C[C@H]3C(F)F)cc3ccc1nc32] | 1-[(1~{S},2~{R})-2-(difluoromethyl)cyclopropyl]-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 413 | 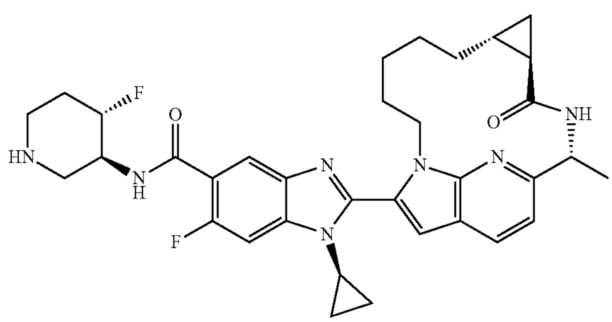 | 6-fluoro-~{N}-[(3~{S},4~{S})-4-fluoro-3-piperidyl]-1-[(1~{S},2~{S})-2-methylcyclopropyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 414 | 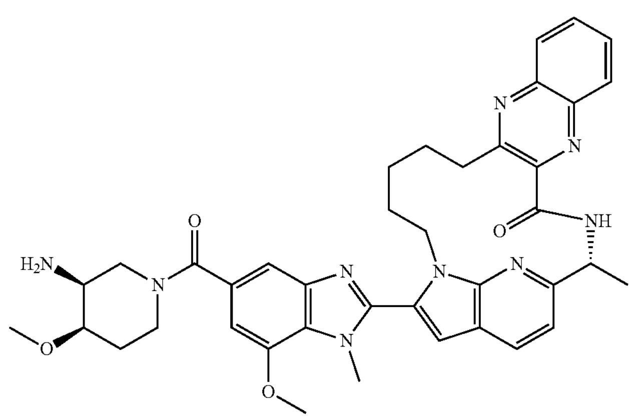 | (2~{R})-21-[5-[(3~{S},4~{R})-3-amino-4-methoxy-piperidine-1-carbonyl]-7-methoxy-1-methyl-benzimidazol-2-yl]-2-methyl-3,6,13,20,26-pentazapentacyclo[18.5.2.0^{5,14}.0^{7,12}.0^{23,27}]heptacosa-1(26),5(14),6,8,10,12,21,23(27),24-nonaen-4-one |

TABLE 1-continued

| Example | Structure | Name |
|---|---|---|
| 415 | 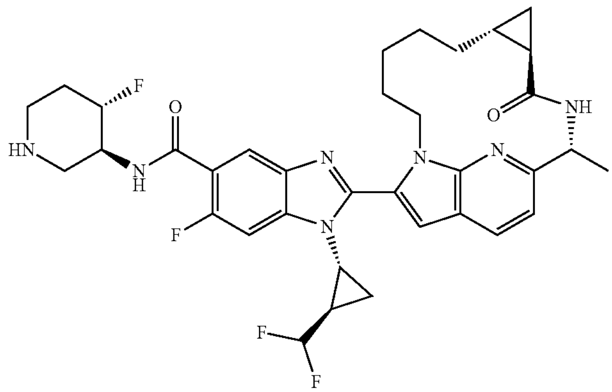 [SMILES: C[C@H]1NC(=O)[C@@H]2C[C@H]2CCCCCn2c(-c3nc4cc(C(=O)N[C@H]5CNCC[C@@H]5F)c(F)cc4n3[C@@H]3C[C@H]3C(F)F)cc3ccc1nc32] | 1-[(1~{R},2~{R})-2-(difluoromethyl)cyclopropyl]-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 416 | 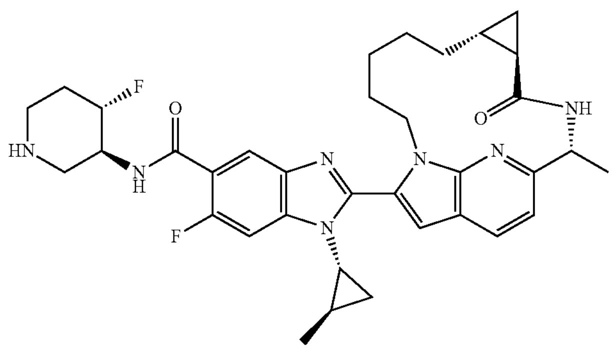 [SMILES: C[C@@H]1C[C@H]1n1c(-c2cc3ccc4nc3n2CCCCC[C@@H]2C[C@H]2C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-[(1~{R},2~{R})-2-methylcyclopropyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 417 | 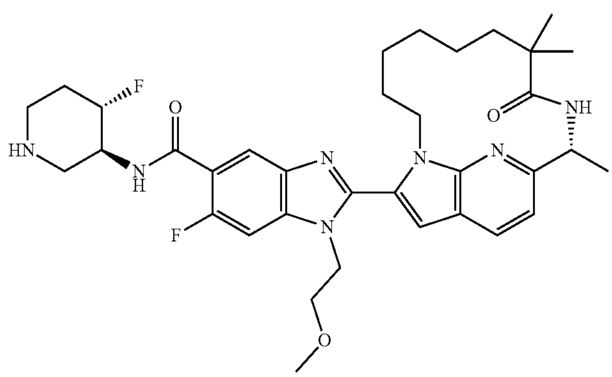 [SMILES: COCCn1c(-c2cc3ccc4nc3n2CCCCCCC(C)(C)C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-(2-methoxyethyl)-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 418 | 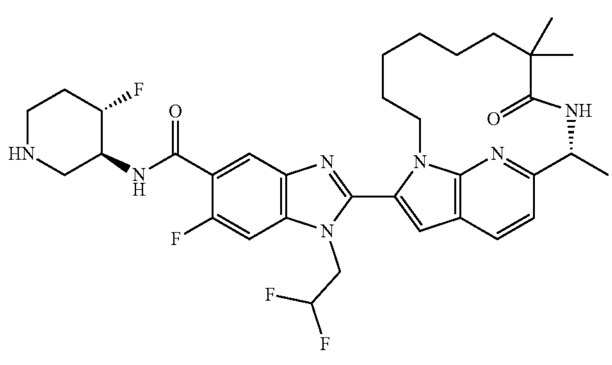 [SMILES: C[C@H]1NC(=O)C(C)(C)CCCCCCn2c(-c3nc4cc(C(=O)N[C@H]5CNCC[C@@H]5F)c(F)cc4n3CC(F)F)cc3ccc1nc32] | 1-(2,2-difluoroethyl)-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1-continued

| Example | Structure | Name |
|---|---|---|
| 419 | 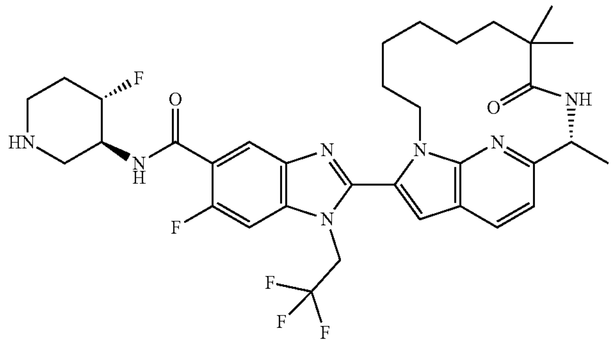 [SMILES: C[C@H]1NC(=O)C(C)(C)CCCCCCn2c(-c3nc4cc(C(=O)N[C@H]5CNCC[C@@H]5F)c(F)cc4n3CC(F)(F)F)cc3ccc1nc32] | 6-fluoro-~{N}-[(3~{S},4~{S})-4-fluoro-3-piperidyl]-1-(2,2,2-trifluoroethyl)-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 420 | 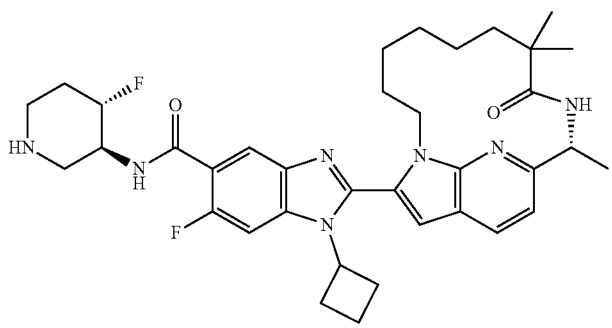 [SMILES: C[C@H]1NC(=O)C(C)(C)CCCCCCn2c(-c3nc4cc(C(=O)N[C@H]5CNCC[C@@H]5F)c(F)cc4n3C3CCC3)cc3ccc1nc32] | 1-cyclobutyl-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 421 | 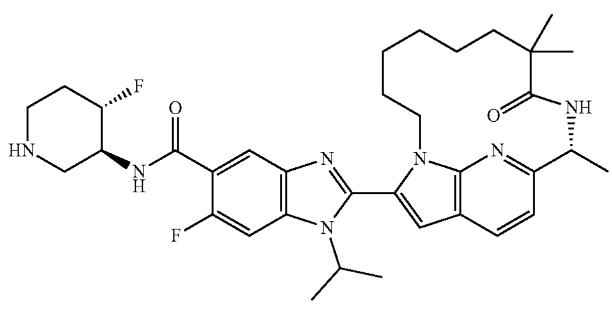 [SMILES: CC(C)n1c(-c2cc3ccc4nc3n2CCCCCCC(C)(C)C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-isopropyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 422 | 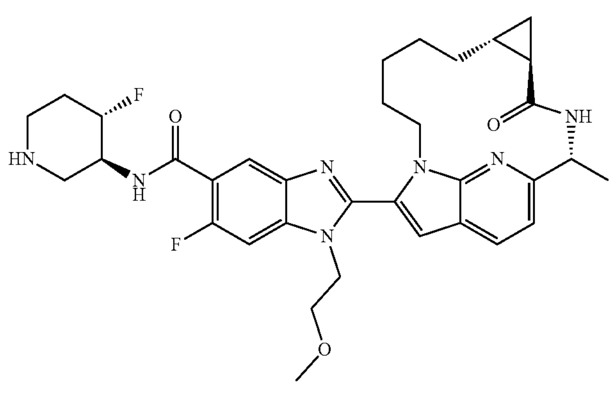 [SMILES: COCCn1c(-c2cc3ccc4nc3n2CCCCC[C@@H]2C[C@H]2C(=O)N[C@@H]4C)nc2cc(C(=O)N[C@H]3CNCC[C@@H]3F)c(F)cc21] | 6-fluoro-~{N}-[(4~{S})-4-fluoro-3-piperidyl]-1-(2-methoxyethyl)-2-[(2~{R},5~{R},7~{R})-2-methyl-4-oxo-3,13,19-triazatetracyclo[11.5.2.0^{5,7}.0^{16,20}]icosa-1(18),14,16,19-tetraen-14-yl]benzimidazole-5-carboxamide |

TABLE 1-continued

| Example | Structure | Name |
|---|---|---|
| 423 | 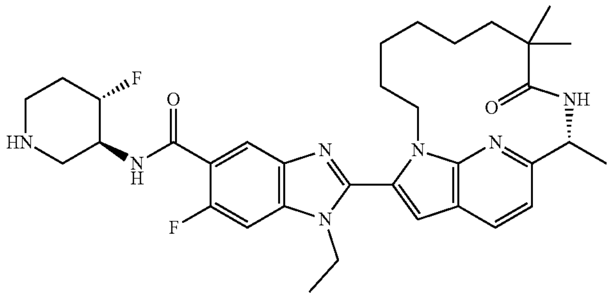 [SMILES: CCn1c(-c2cc3ccc4nc3n2CCCCCCC(C)(C)C(=O)N[C@@H]4C)nc2cc(C(=O)N[C@H]3CNCC[C@@H]3F)c(F)cc21] | 1-ethyl-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 424 | 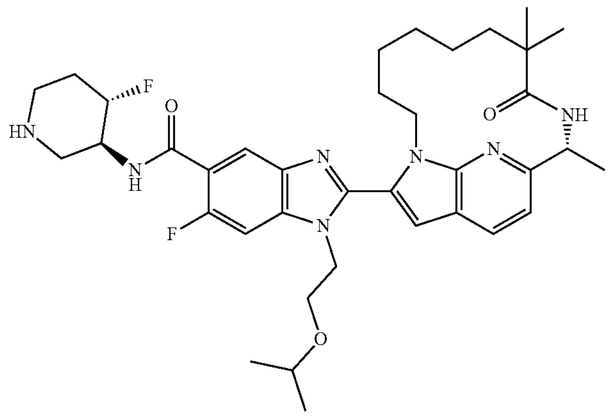 [SMILES: CC(C)OCCn1c(-c2cc3ccc4nc3n2CCCCCCC(C)(C)C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-(2-isopropoxyethyl)-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 425 | 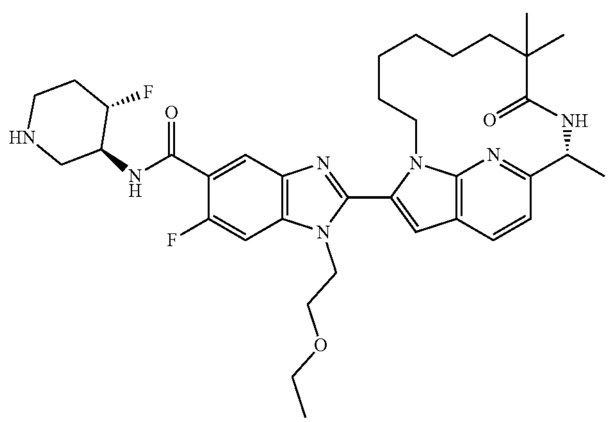 [SMILES: CCOCCn1c(-c2cc3ccc4nc3n2CCCCCCC(C)(C)C(=O)N[C@@H]4C)nc2cc(C(=O)N[C@H]3CNCC[C@@H]3F)c(F)cc21] | 1-(2-ethoxyethyl)-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 426 | 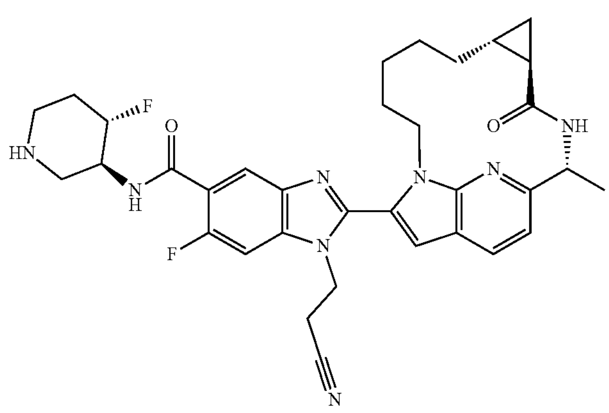 [SMILES: C[C@H]1NC(=O)[C@@H]2C[C@H]2CCCCCn2c(-c3nc4cc(C(=O)N[C@H]5CNCC[C@@H]5F)c(F)cc4n3CCC#N)cc3ccc1nc32] | 1-(2-cyanoethyl)-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1-continued

| Example | Structure | Name |
|---|---|---|
| 427 | 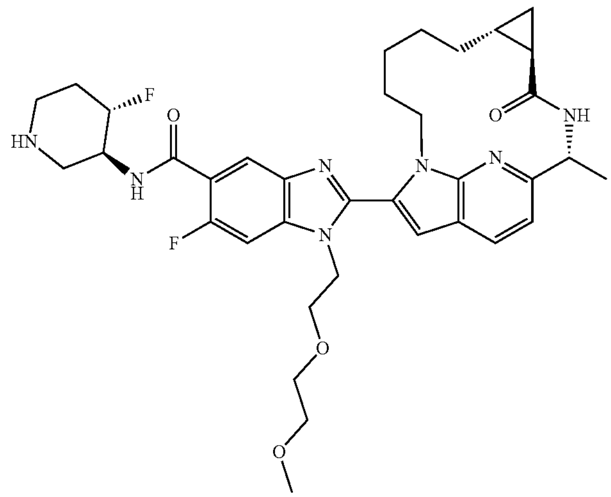 [SMILES: COCCOCCn1c(-c2cc3ccc4nc3n2CCCCC[C@@H]2C[C@H]2C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-[2-(2-methoxyethoxy)ethyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 428 | 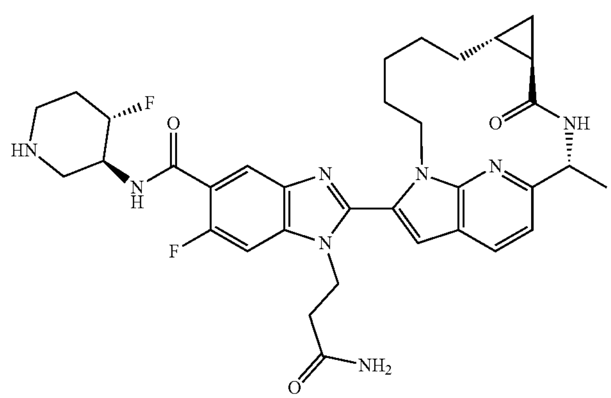 [SMILES: C[C@H]1NC(=O)[C@@H]2C[C@H]2CCCCCn2c(-c3nc4cc(C(=O)N[C@H]5CNCC[C@@H]5F)c(F)cc4n3CCC(N)=O)cc3ccc1nc32] | 1-(3-amino-3-oxo-propyl)-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 429 | 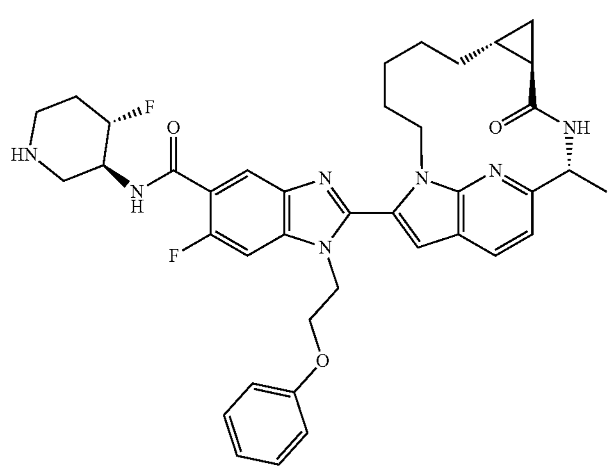 [SMILES: C[C@H]1NC(=O)[C@@H]2C[C@H]2CCCCCn2c(-c3nc4cc(C(=O)N[C@H]5CNCC[C@@H]5F)c(F)cc4n3CCOc3ccccc3)cc3ccc1nc32] | 6-fluoro-~{N}-[(3~{S},4~{S})-4-fluoro-3-piperidyl]-2-[2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-1-(2-phenoxyethyl)benzimidazole-5-carboxamide |

TABLE 1-continued

| Example | Structure | Name |
|---|---|---|
| 430 | 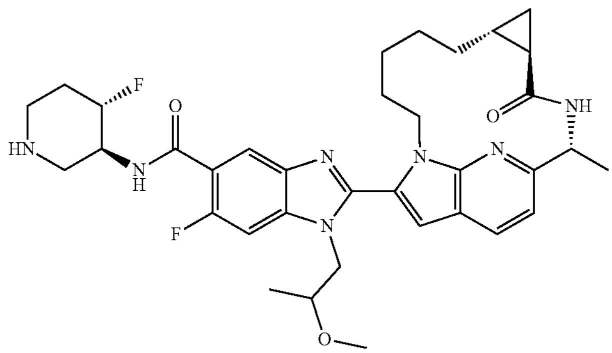 [SMILES: COC(C)Cn1c(-c2cc3ccc4nc3n2CCCCC[C@@H]2C[C@H]2C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-(2-methoxypropyl)-2-[(2~{R},5~{R},7~{R})-2-methyl-4-oxo-3,13,19-triazatetracyclo[11.5.2.0˄{5,7}.0˄{16,20}]icosa-1(19),14,16(20),17-tetraen-14-yl]benzimidazole-5-carboxamide |
| 431 | 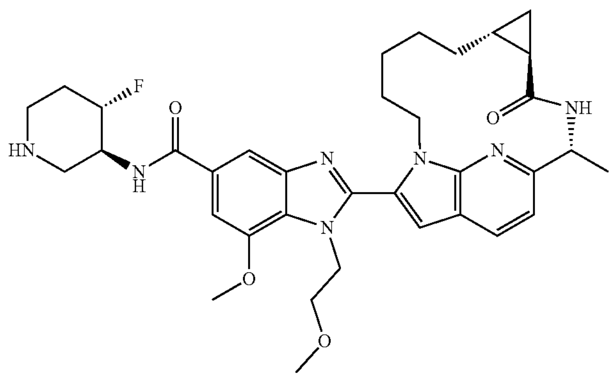 [SMILES: COCCn1c(-c2cc3ccc4nc3n2CCCCC[C@@H]2C[C@H]2C(=O)N[C@@H]4C)nc2cc(C(=O)N[C@H]3CNCC[C@@H]3F)cc(OC)c21] | ~{N}-[(3~{S},4~{S})-4-fluoro-3-piperidyl]-7-methoxy-1-(2-methoxyethyl)-2-[(2~{R},5~{R},7~{R})-2-methyl-4-oxo-3,13,19-triazatetracyclo[11.5.2.0˄{5,7}.0˄{16,20}]icosa-1(19),14,16(20),17-tetraen-14-yl]benzimidazole-5-carboxamide |
| 432 | 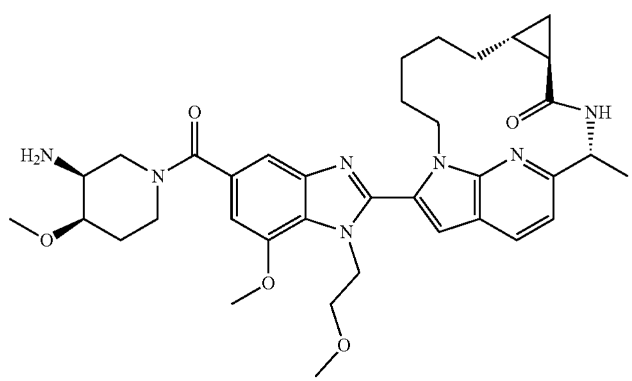 | (2~{R},5~{R},7~{R})-14-[5-[(3~{S},4~{R})-3-amino-4-methoxy-piperidine-1-carbonyl]-7-methoxy-1-(2-methoxyethyl)benzimidazol-2-yl]-2-methyl-3,13,19-triazatetracyclo[11.5.2.0˄{5,7}.0˄{16,20}]icosa-1(19),14,16(20),17-tetraen-4-one |
| 433 | 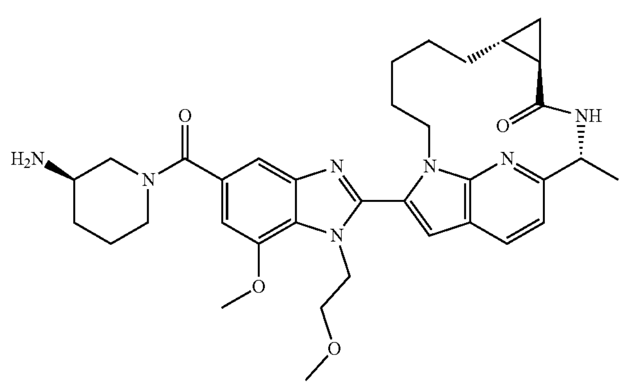 [SMILES: COCCn1c(-c2cc3ccc4nc3n2CCCCC[C@@H]2C[C@H]2C(=O)N[C@@H]4C)nc2cc(C(=O)N3CCC[C@@H](N)C3)cc(OC)c21] | (2~{R},5~{R},7~{R})-14-[5-[(3~{R})-3-aminopiperidine-1-carbonyl]-7-methoxy-1-(2-methoxyethyl)benzimidazol-2-yl]-2-methyl-3,13,19-triazatetracyclo[11.5.2.0˄{5,7}.0˄{16,20}]icosa-1(19),14,16(20),17-tetraen-4-one |

TABLE 1-continued

| Example | Structure | Name |
|---|---|---|
| 434 | 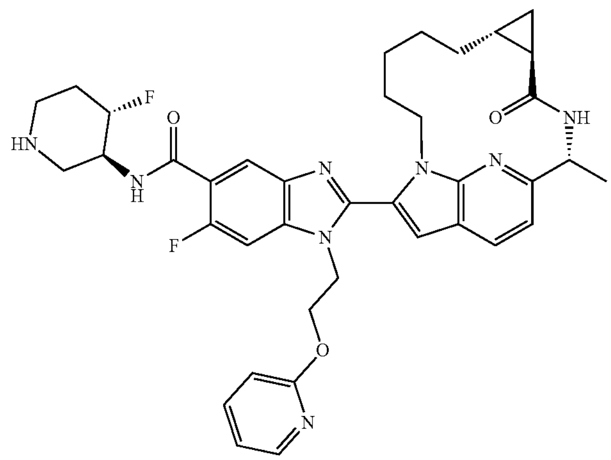 [SMILES: C[C@H]1NC(=O)[C@@H]2C[C@H]2CCCCCn2c(-c3nc4cc(C(=O)N[C@H]5CNCC[C@@H]5F)c(F)cc4n3CCOc3ccccn3)cc3ccc1nc32] | 6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-1-[2-(2-pyridyloxy)ethyl]benzimidazole-5-carboxamide |
| 435 | 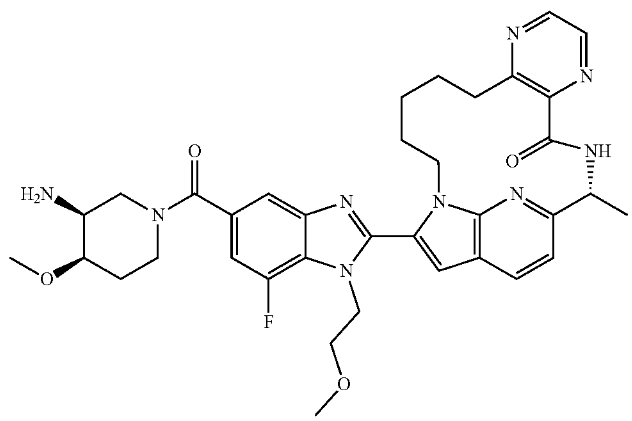 | (2~{R})-17-[5-[(3~{S},4~{R})-3-amino-4-methoxy-piperidine-1-carbonyl]-7-fluoro-1-(2-methoxyethyl)benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 436 | 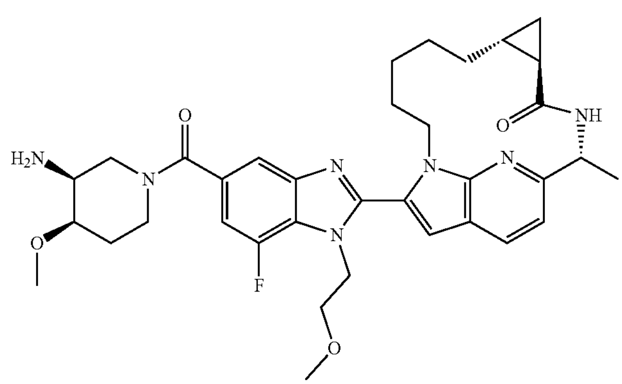 [SMILES: COCCn1c(-c2cc3ccc4nc3n2CCCCC[C@@H]2C[C@H]2C(=O)N[C@@H]4C)nc2cc(C(=O)N3CC[C@@H](OC)[C@@H](N)C3)cc(F)c21] | (2~{R},5~{R},7~{R})-14-[5-[(3~{S},4~{R})-3-amino-4-methoxy-piperidine-1-carbonyl]-7-fluoro-1-(2-methoxyethyl)benzimidazol-2-yl]-2-methyl-3,13,19-triazatetracyclo[11.5.2.0^{5,7}.0^{16,20}]icosa-1(19),14,16(20),17-tetraen-4-one |
| 437 | 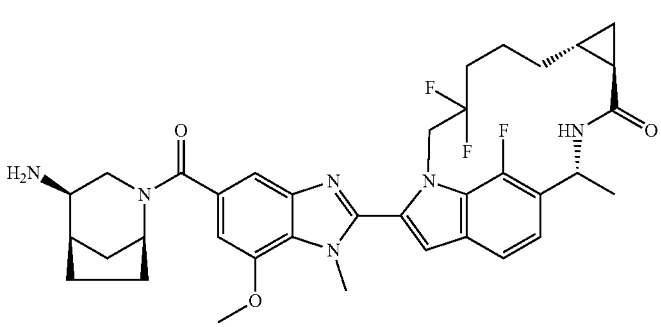 [SMILES: COc1cc(C(=O)N2C[C@H](N)[C@@H]3CC[C@H]2C3)cc2nc(-c3cc4ccc5c(F)c4n3CC(F)(F)CCC[C@@H]3C[C@H]3C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-11,11,19-trifluoro-2-methyl-3,13-diazatetracyclo[11.5.2.0^{5,7}.0^{16,20}]icosa-1(19),14,16(20),17-tetraen-4-one |

TABLE 1-continued

| Example | Structure | Name |
|---|---|---|
| 438 | 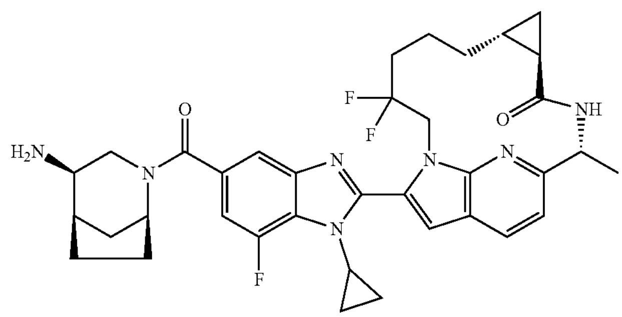 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 439 | 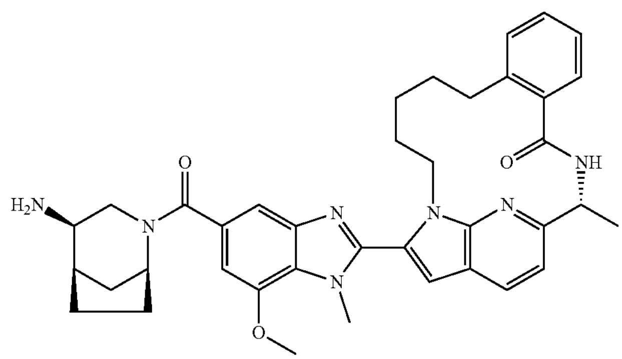 [SMILES: COc1cc(C(=O)N2C[C@H](N)[C@@H]3CC[C@H]2C3)cc2nc(-c3cc4ccc5nc4n3CCCCCc3ccccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-2-methyl-3,16,22-triazatetracyclo[14.5.2.0^{5,10}.0^{19,23}]tricosa-1(22),5(10),6,8,17,19(23),20-heptaen-4-one |
| 440 | 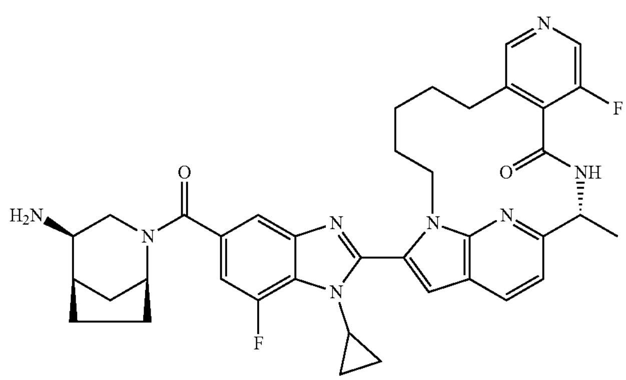 [SMILES: C[C@H]1NC(=O)c2c(F)cncc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-6-fluoro-2-methyl-3,8,16,22-tetrazatetracyclo[14.5.2.0^{5,10}.0^{19,23}]tricosa-1(22),5(10),6,8,17,19(23),20-heptaen-4-one |
| 441 | 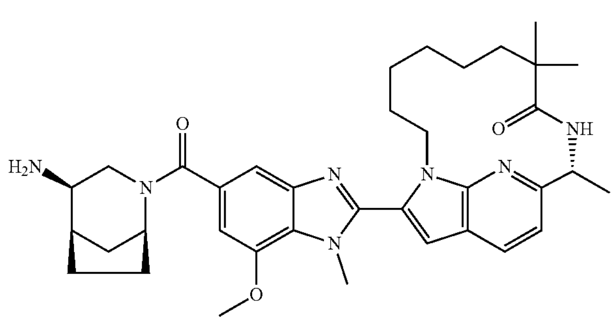 [SMILES: COc1cc(C(=O)N2C[C@H](N)[C@@H]3CC[C@H]2C3)cc2nc(-c3cc4ccc5nc4n3CCCCCCC(C)(C)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1-continued

| Example | Structure | Name |
|---|---|---|
| 442 | 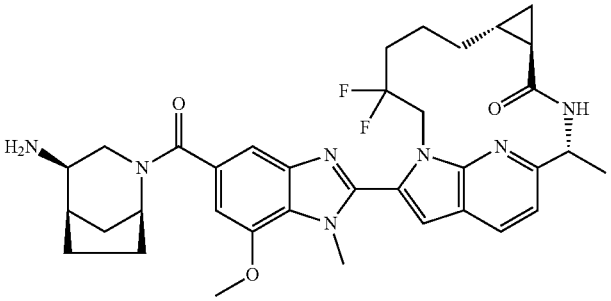 [SMILES: COc1cc(C(=O)N2C[C@H](N)[C@@H]3CC[C@H]2C3)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 443 | 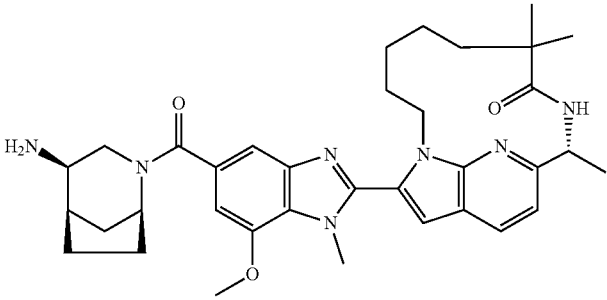 [SMILES: COc1cc(C(=O)N2C[C@H](N)[C@@H]3CC[C@H]2C3)cc2nc(-c3cc4ccc5nc4n3CCCCCC(C)(C)C(=O)N[C@@H]5C)n(C)c12] | (10~{R})-16-[5-[(1~{S},4~{R},5~{})-4-amino-2-azabicyclo[3.2.1]octane-2-carbonyl]-7-methoxy-1-methyl-benzimidazol-2-yl]-7,7,10-trimethyl-1,9,18-triazatricyclo[9.5.2.0^{14,17}]octadeca-11(18),12,14(17),15-tetraen-8-one |
| 444 | 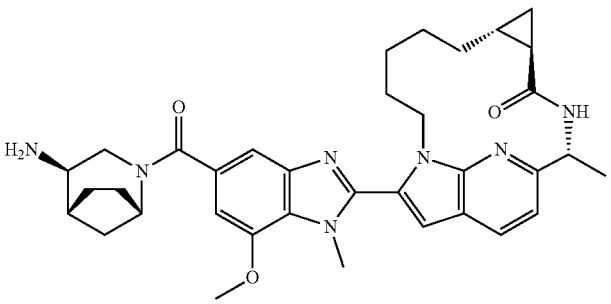 [SMILES: COc1cc(C(=O)N2C[C@H](N)[C@@H]3CC[C@H]2C3)cc2nc(-c3cc4ccc5nc4n3CCCCC[C@@H]3C[C@H]3C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 445 | 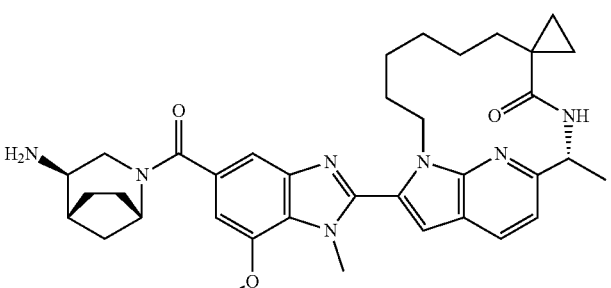 | (11~{R})-17-[5-[(1~{S},4~{R},5~{R})-4-amino-2-azabicyclo[3.2.1]octane-2-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,1'-cyclopropane]-9-one |
| 446 | 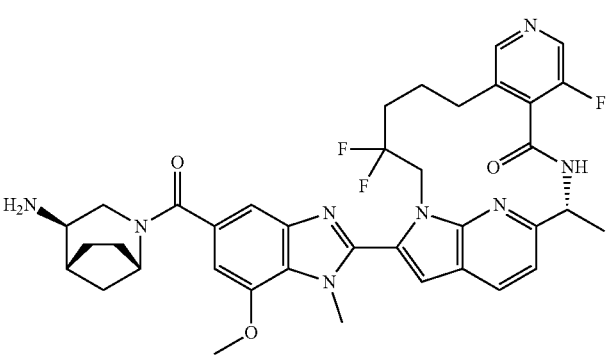 [SMILES: COc1cc(C(=O)N2C[C@H](N)[C@@H]3CC[C@H]2C3)cc2nc(-c3cc4ccc5nc4n3CC(F)(F)CCCc3cncc(F)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6,14,14-trifluoro-2-methyl-3,8,16,22-tetrazatetracyclo[14.5.2.0^{5,10}.0^{19,23}]tricosa-1(22),5(10),6,8,17,19(23),20-heptaen-4-one |

TABLE 1-continued

| Example | Structure | Name |
|---|---|---|
| 447 | 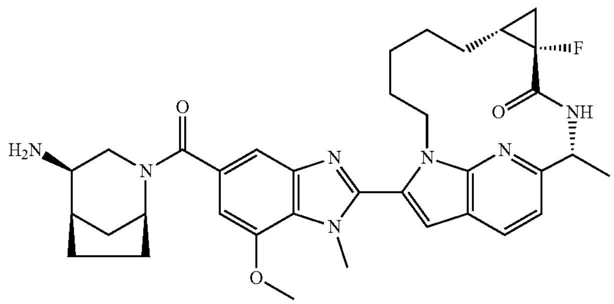 [SMILES: COc1cc(C(=O)N2C[C@H](N)[C@@H]3CC[C@H]2C3)cc2nc(-c3cc4ccc5nc4n3CCCCC[C@@H]3C[C@@]3(F)C(=O)N[C@@H]5C)n(C)c12] | (2~{R},5~{S},7~{R})-14-[5-[(1~{S},4~{R},5~{R})-4-amino-2-azabicyclo[3.2.1]octane-2-carbonyl]-7-methoxy-1-methyl-benzimidazol-2-yl]-5-fluoro-2-methyl-3,13,19-triazatetracyclo[11.5.2.0^{5,7}.0^{16,20}]icosa-1(19),14,16(20),17-tetraen-4-one |
| 448 | 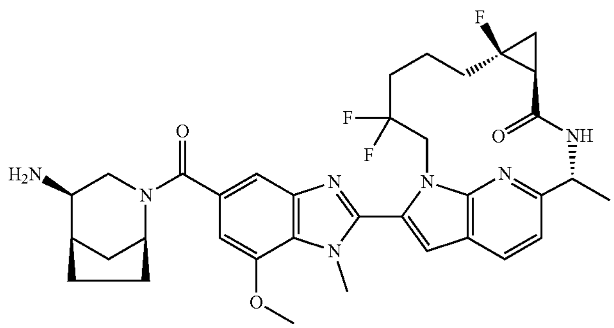 [SMILES: COc1cc(C(=O)N2C[C@H](N)[C@@H]3CC[C@H]2C3)cc2nc(-c3cc4ccc5nc4n3CC(F)(F)CCC[C@]3(F)C[C@H]3C(=O)N[C@@H]5C)n(C)c12] | (2~{R},5~{S},7~{S})-14-[5-[(1~{S},4~{R},5~{R})-4-amino-2-azabicyclo[3.2.1]octane-2-carbonyl]-7-methoxy-1-methyl-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 449 | 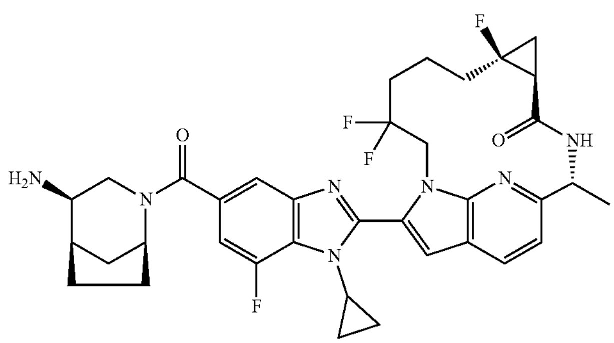 [SMILES: C[C@H]1NC(=O)[C@@H]2C[C@@]2(F)CCCC(F)(F)Cn2c(-c3nc4cc(C(=O)N5C[C@H](N)[C@@H]6CC[C@H]5C6)cc(F)c4n3C3CC3)cc3ccc1nc32] | (2~{R},5~{S},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 450 | 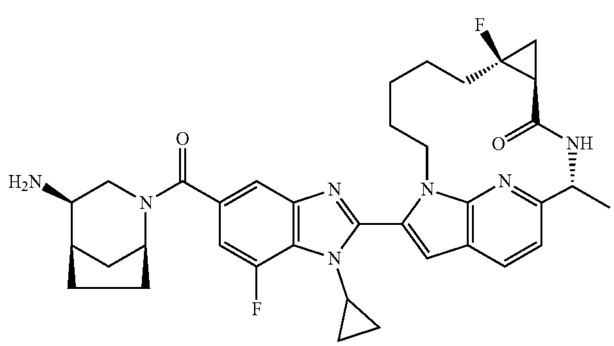 [SMILES: C[C@H]1NC(=O)[C@@H]2C[C@@]2(F)CCCCCn2c(-c3nc4cc(C(=O)N5C[C@H](N)[C@@H]6CC[C@H]5C6)cc(F)c4n3C3CC3)cc3ccc1nc32] | (2~{R},5~{S},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-7-fluoro-2-methyl-3,13,19-triazatetracyclo[11.5.2.0^{5,7}.0^{16,20}]icosa-1(19),14,16(20),17-tetraen-4-one |

TABLE 1-continued

| Example | Structure | Name |
|---|---|---|
| 451 | 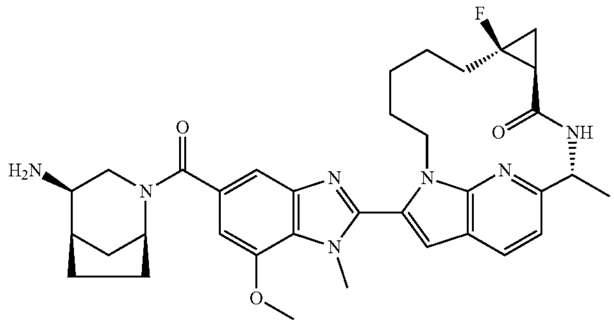 [SMILES: COc1cc(C(=O)N2C[C@H](N)[C@@H]3CC[C@H]2C3)cc2nc(-c3cc4ccc5nc4n3CCCCC[C@]3(F)C[C@H]3C(=O)N[C@@H]5C)n(C)c12] | (2~{R},5~{S},7~{S})-14-[5-[(1~{S},4~{R},5~{R})-4-amino-2-azabicyclo[3.2.1]octane-2-carbonyl]-7-methoxy-1-methyl-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 452 | 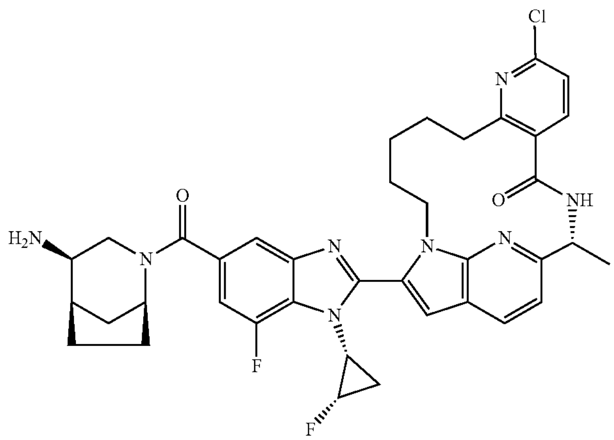 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3[C@@H]3C[C@@H]3F)cc3ccc1nc32] | (2~{R})-17-[(1~{R})-5-[(1~{S},4~{R},5~{R})-4-amino-2-azabicyclo[3.2.1]octane-2-carbonyl]-7-fluoro-1-[(2~{S})-2-fluorocyclopropyl]benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 453 | 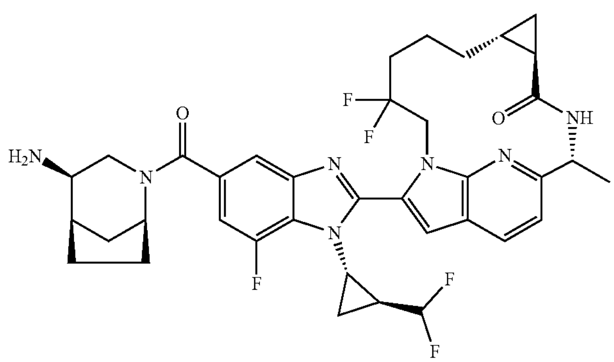 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@H]3C[C@@H]3C(F)F)cc3ccc1nc32] | (2~{R},5~{R},7~{R})-14-[5-[(1~{S},4~{R},5~{R})-4-amino-2-azabicyclo[3.2.1]octane-2-carbonyl]-1-[(1~{S},2~{S})-2-(difluoromethyl)cyclopropyl]-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 454 | 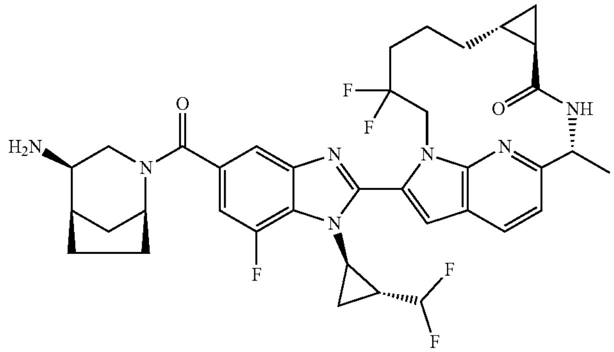 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@@H]3C[C@H]3C(F)F)cc3ccc1nc32] | (2~{R},5~{R},7~{R})-14-[5-[(1~{S},4~{R},5~{R})-4-amino-2-azabicyclo[3.2.1]octane-2-carbonyl]-1-[(1~{R},2~{R})-2-(difluoromethyl)cyclopropyl]-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1-continued

| Example | Structure | Name |
|---|---|---|
| 455 | 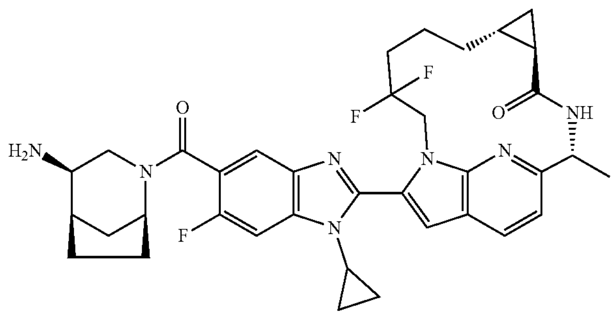 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)c(F)cc4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-6-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 456 | 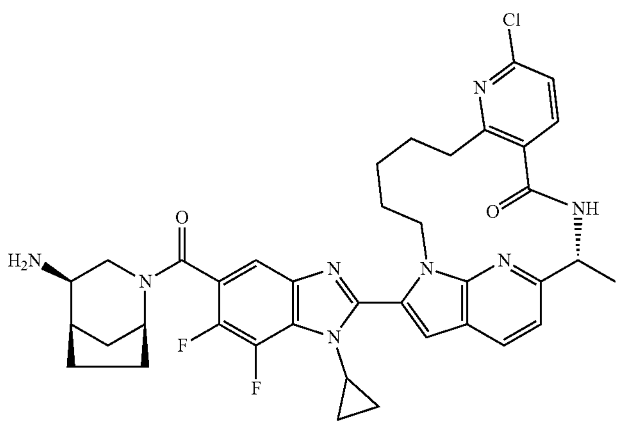 [SMILES: C[C@H]1NC(=O)c2ccc(Cl)nc2CCCCCn2c(-c3nc4cc(C(=O)N5C[C@H](N)[C@@H]6CC[C@H]5C6)c(F)c(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-6,7-difluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 457 | 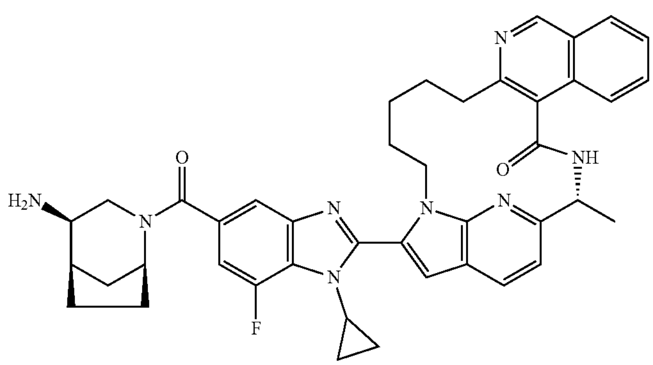 [SMILES: C[C@H]1NC(=O)c2c(ncc3ccccc23)CCCCCn2c(-c3nc4cc(C(=O)N5C[C@H](N)[C@@H]6CC[C@H]5C6)cc(F)c4n3C3CC3)cc3ccc1nc32] | (2~{R})-21-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,13,20,26-tetrazapentacyclo[18.5.2.0^{5,14}.0^{6,11}.0^{23,27}]heptacosa-1(26),5(14),6(11),7,9,12,21,23(27),24-nonaen-4-one |
| 458 | 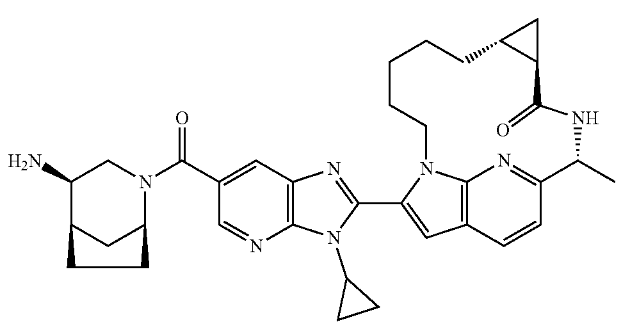 [SMILES: C[C@H]1NC(=O)[C@@H]2C[C@H]2CCCCCn2c(-c3nc4cc(C(=O)N5C[C@H](N)[C@@H]6CC[C@H]5C6)cnc4n3C3CC3)cc3ccc1nc32] | (2~{R},5~{R},7~{R})-14-[6-[(1~{S},4~{R},5~{R})-4-amino-2-azabicyclo[3.2.1]octane-2-carbonyl]-3-cyclopropyl-imidazo[4,5-b]pyridin-2-yl]-2-methyl-3,13,19-triazatetracyclo[11.5.2.0^{5,7}.0^{16,20}]icosa-1(19),14,16(20),17-tetraen-4-one |

TABLE 1-continued

| Example | Structure | Name |
|---|---|---|
| 459 | 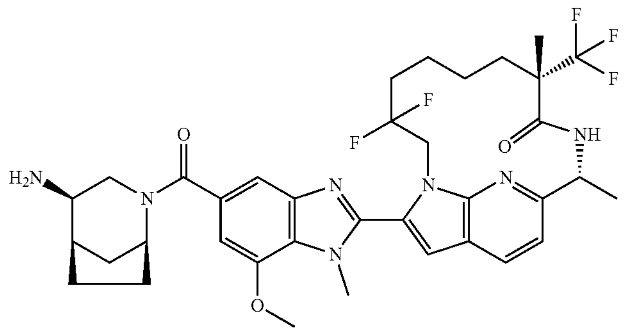 [SMILES: COc1cc(C(=O)N2C[C@H](N)[C@@H]3CC[C@H]2C3)cc2nc(-c3cc4ccc5nc4n3CC(F)(F)CCCC[C@](C)(C(F)(F)F)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-3,3-difluoro-8,11-dimethyl-8-(trifluoromethyl)-1,10,19-triazatricyclo[10.5.2.0^{15,18}]nonadeca-12(19),13,15(18),16-tetraen-9-one |
| 460 | 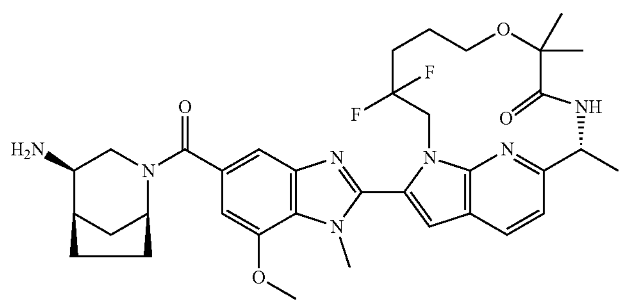 [SMILES: COc1cc(C(=O)N2C[C@H](N)[C@@H]3CC[C@H]2C3)cc2nc(-c3cc4ccc5nc4n3CC(F)(F)CCCOC(C)(C)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-3,3-difluoro-8,8,11-trimethyl-7-oxa-1,10,19-triazatricyclo[10.5.2.0^{15,18}]nonadeca-12(19),13,15(18),16-tetraen-9-one |
| 461 | 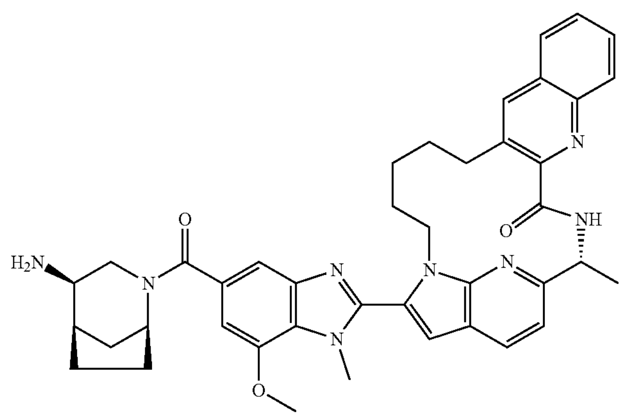 [SMILES: COc1cc(C(=O)N2C[C@H](N)[C@@H]3CC[C@H]2C3)cc2nc(-c3cc4ccc5nc4n3CCCCCc3cc4ccccc4nc3C(=O)N[C@@H]5C)n(C)c12] | (2~{R})-21-[5-[(1~{S},4~{R},5~{R})-4-amino-2-azabicyclo[3.2.1]octane-2-carbonyl]-7-methoxy-1-methyl-benzimidazol-2-yl]-2-methyl-3,6,20,26-tetrazapentacyclo[18.5.2.0^{5,14}.0^{7,12}.0^{23,27}]heptacosa-1(26),5(14),6,8,10,12,21,23(27),24-nonaen-4-one |
| 462 | 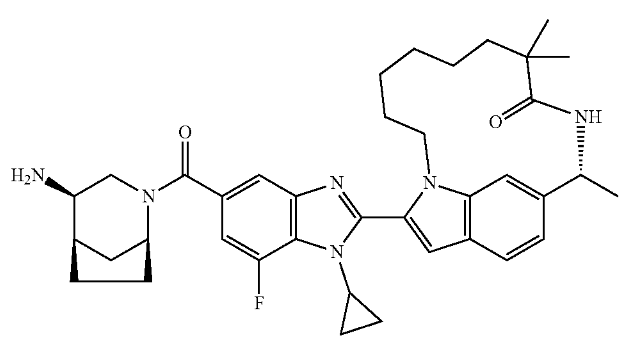 [SMILES: C[C@H]1NC(=O)C(C)(C)CCCCCCn2c(-c3nc4cc(C(=O)N5C[C@H](N)[C@@H]6CC[C@H]5C6)cc(F)c4n3C3CC3)cc3ccc1cc32] | (11~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8,8,11-trimethyl-1,10-diazatricyclo[10.5.2.0^{15,18}]nonadeca-12(19),13,15(18),16-tetraen-9-one |

TABLE 1-continued

| Example | Structure | Name |
|---|---|---|
| 463 | 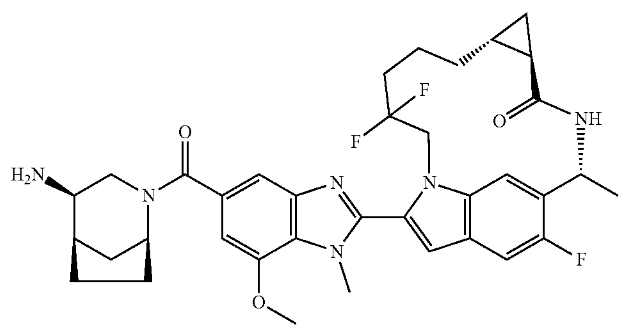 [SMILES: COc1cc(C(=O)N2C[C@H](N)[C@@H]3CC[C@H]2C3)cc2nc(-c3cc4cc(F)c5cc4n3CC(F)(F)CCC[C@@H]3C[C@H]3C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-11,11,18-trifluoro-2-methyl-3,13-diazatetracyclo[11.5.2.0^{5,7}.0^{16,20}]icosa-1(19),14,16(20),17-tetraen-4-one |
| 464 | 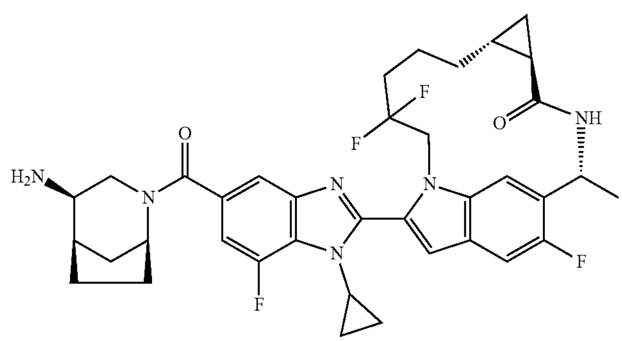 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3C3CC3)cc3cc(F)c1cc32] | (2~{R},5~{R},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-11,11,18-trifluoro-2-methyl-3,13-diazatetracyclo[11.5.2.0^{5,7}.0^{16,20}]icosa-1(19),14,16(20),17-tetraen-4-one |
| 465 | 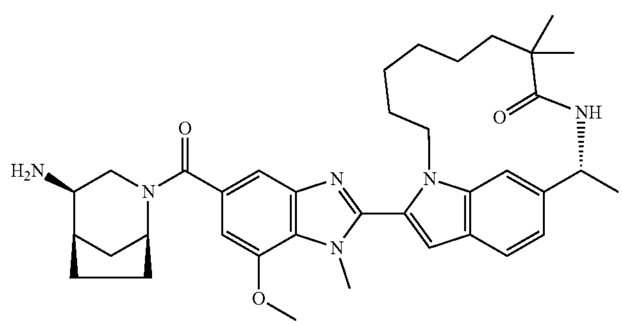 [SMILES: COc1cc(C(=O)N2C[C@H](N)[C@@H]3CC[C@H]2C3)cc2nc(-c3cc4ccc5cc4n3CCCCCCC(C)(C)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one |
| 466 | 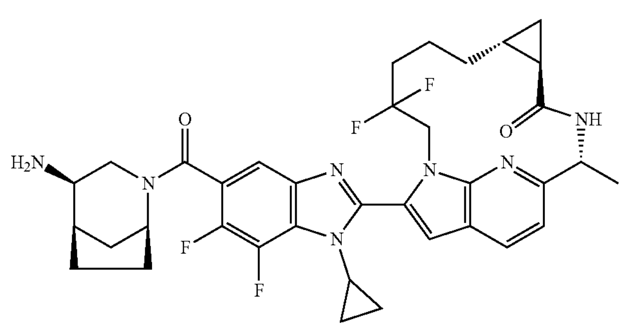 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)c(F)c(F)c4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-6,7-difluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1-continued

| Example | Structure | Name |
|---|---|---|
| 467 | 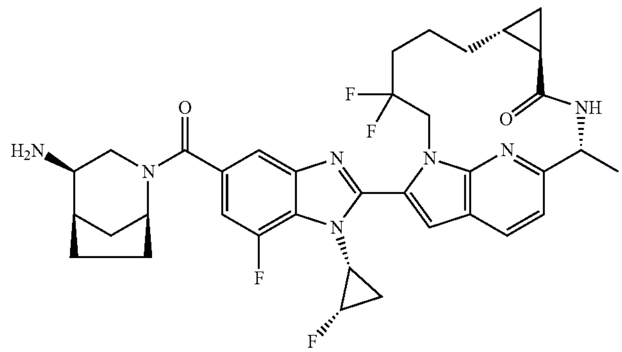 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@@H]3C[C@@H]3F)cc3ccc1nc32] | (2~{R},5~{R},7~{R})-14-[(1~{R})-5-[(1~{S},4~{R},5~{R})-4-amino-2-azabicyclo[3.2.1]octane-2-carbonyl]-7-fluoro-1-[(2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 468 | 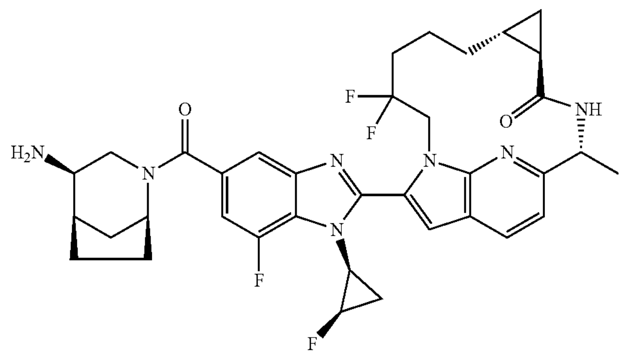 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@H]3C[C@H]3F)cc3ccc1nc32] | (2~{R},5~{R},7~{R})-14-[5-[(1~{S},4~{R},5~{R})-4-amino-2-azabicyclo[3.2.1]octane-2-carbonyl]-7-fluoro-1-[(1~{S},2~{R})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 469 | 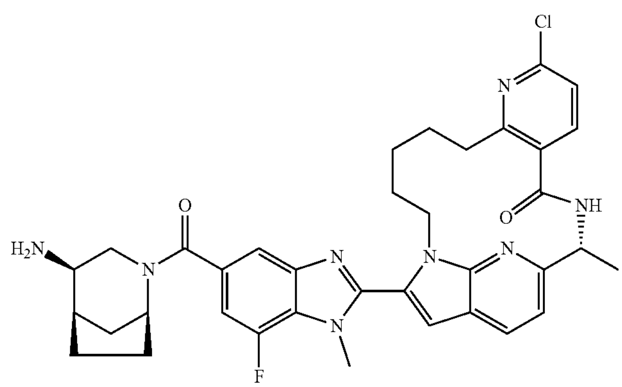 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3C)cc3ccc1nc32] | (2~{R})-17-[5-[(1~{S},4~{R},5~{R})-4-amino-2-azabicyclo[3.2.1]octane-2-carbonyl]-7-fluoro-1-methyl-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 470 | 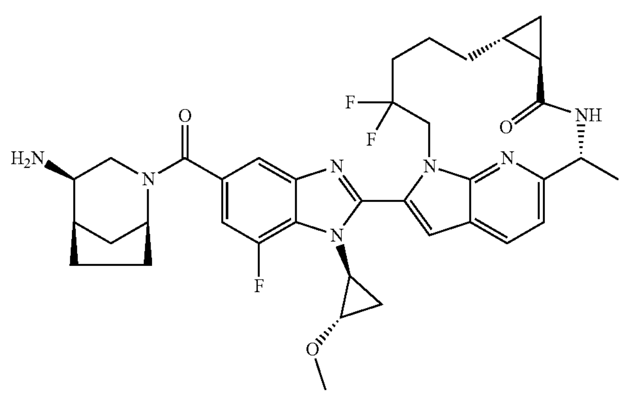 [SMILES: CO[C@H]1C[C@@H]1n1c(-c2cc3ccc4nc3n2CC(F)(F)CCC[C@@H]2C[C@H]2C(=O)N[C@@H]4C)nc2cc(C(=O)N3C[C@H](N)[C@@H]4CC[C@H]3C4)cc(F)c21] | (2~{R},5~{R},7~{R})-14-[5-[(1~{S},4~{R},5~{R})-4-amino-2-azabicyclo[3.2.1]octane-2-carbonyl]-7-fluoro-1-[(1~{S},2~{S})-2-methoxycyclopropyl]benzimidazol-2-yl]-11,11-difluoro-2-methyl-3,13,19-triazatetracyclo[11.5.2.0^{5,7}.0^{16,20}]icosa-1(18),14,16,19-tetraen-4-one |

| Example | Structure | Name |
| --- | --- | --- |
| 471 | 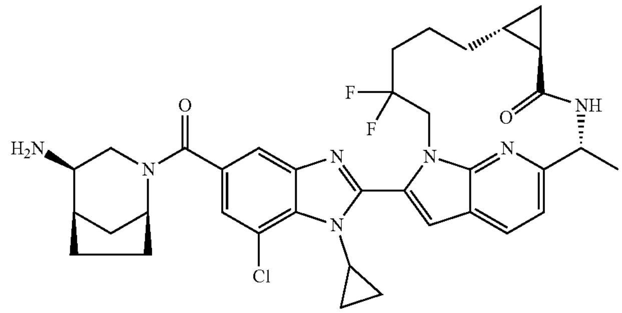 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(Cl)c4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-7-chloro-1-cyclopropyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 472 | 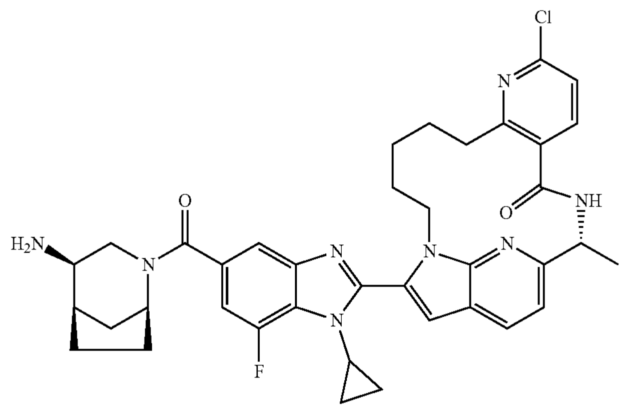 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 473 | 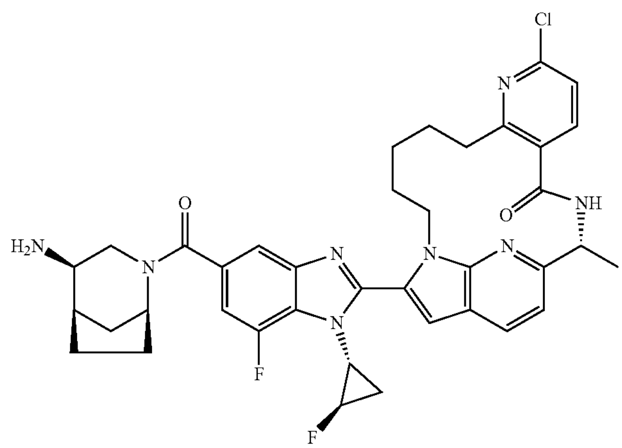 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3[C@@H]3C[C@H]3F)cc3ccc1nc32] | (2~{R})-17-[5-[(1~{S},4~{R},5~{R})-4-amino-2-azabicyclo[3.2.1]octane-2-carbonyl]-7-fluoro-1-[(1~{R},2~{R})-2-fluorocyclopropyl]benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 474 | 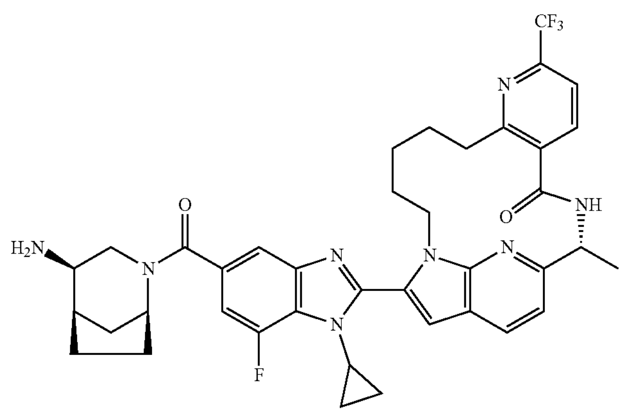 [SMILES: C[C@H]1NC(=O)c2ccc(C(F)(F)F)nc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-8-(trifluoromethyl)-3,9,16,22-tetrazatetracyclo[14.5.2.0^{5,10}.0^{19,23}]tricosa-1(22),5(10),6,8,17,19(23),20-heptaen-4-one |

TABLE 1-continued

| Example | Structure | Name |
|---|---|---|
| 475 | 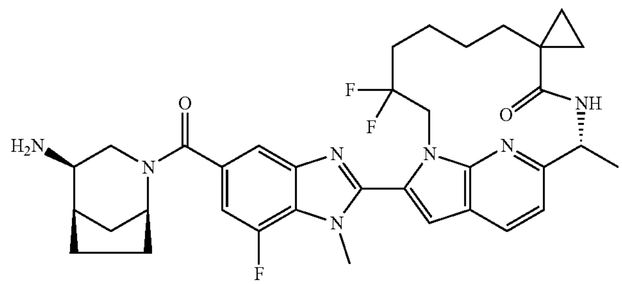 [SMILES: C[C@H]1NC(=O)C2(CCCCC(F)(F)Cn3c(-c4nc5cc(C(=O)N6C[C@H](N)[C@@H]7CC[C@H]6C7)cc(F)c5n4C)cc4ccc1nc43)CC2] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-3,3-difluoro-11-methyl-spiro[1,10,19-triazatricyclo[10.5.2.0^{15,18}]nonadeca-12(19),13,15(18),16-tetraene-8,1'-cyclopropane]-9-one |
| 476 | 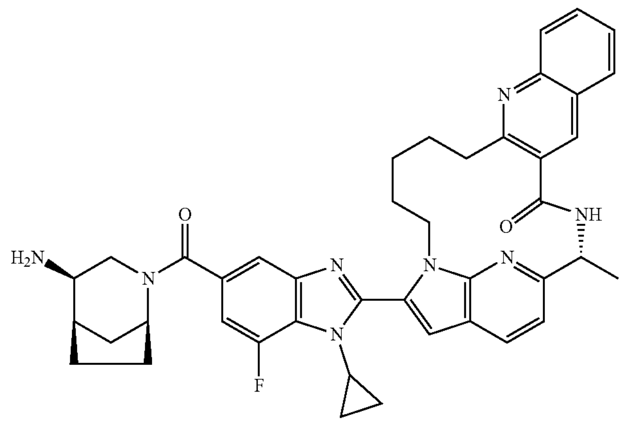 [SMILES: C[C@H]1NC(=O)c2cc3ccccc3nc2CCCCCn2c(-c3nc4cc(C(=O)N5C[C@H](N)[C@@H]6CC[C@H]5C6)cc(F)c4n3C3CC3)cc3ccc1nc32] | (2~{R})-21-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,13,20,26-tetrazapentacyclo[18.5.2.0^{5,14}.0^{7,12}.0^{23,27}]heptacosa-1(26),5(14),6,8,10,12,21,23(27),24-nonaen-4-one |
| 477 | 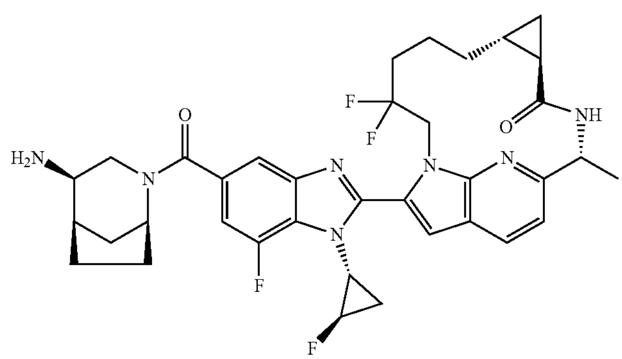 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@@H]3C[C@H]3F)cc3ccc1nc32] | (2~{R},5~{R},7~{R})-14-[5-[(1~{S},4~{R},5~{R})-4-amino-2-azabicyclo[3.2.1]octane-2-carbonyl]-7-fluoro-1-[(1~{R},2~{R})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 478 | 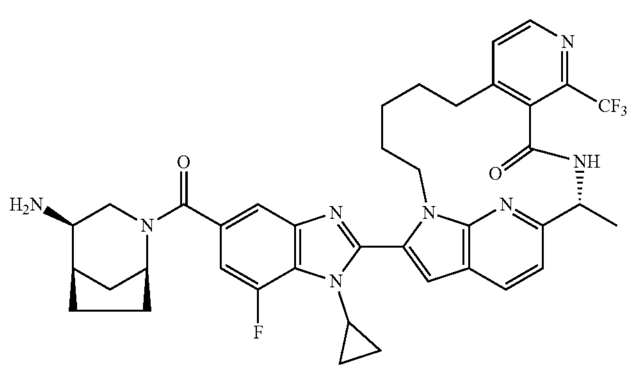 [SMILES: C[C@H]1NC(=O)c2c(ccnc2C(F)(F)F)CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-6-(trifluoromethyl)-3,7,16,22-tetrazatetracyclo[14.5.2.0^{5,10}.0^{19,23}]tricosa-1(22),5(10),6,8,17,19(23),20-heptaen-4-one |

TABLE 1-continued

| Example | Structure | Name |
|---|---|---|
| 479 | 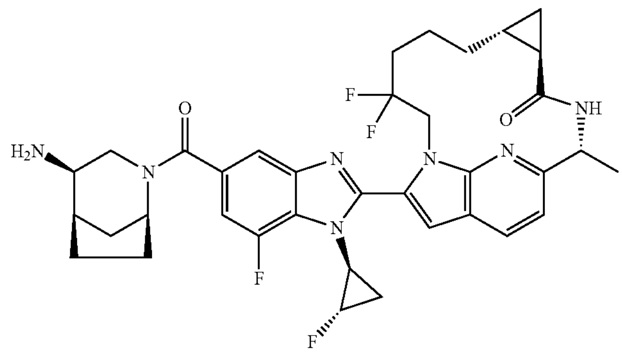 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@H]3C[C@@H]3F)cc3ccc1nc32] | (2~{R},5~{R},7~{R})-14-[5-[(1~{S},4~{R},5~{R})-4-amino-2-azabicyclo[3.2.1]octane-2-carbonyl]-7-fluoro-1-[(1~{S},2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 480 | 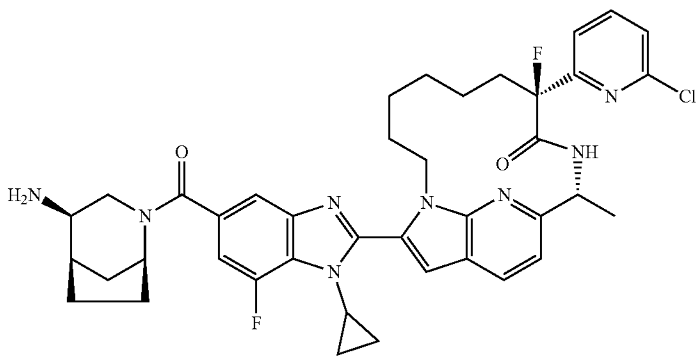 [SMILES: C[C@H]1NC(=O)[C@@](F)(c2cccc(Cl)n2)CCCCCCn2c(-c3nc4cc(C(=O)N5C[C@H](N)[C@@H]6CC[C@H]5C6)cc(F)c4n3C3CC3)cc3ccc1nc32] | (8~{S},11~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 481 | 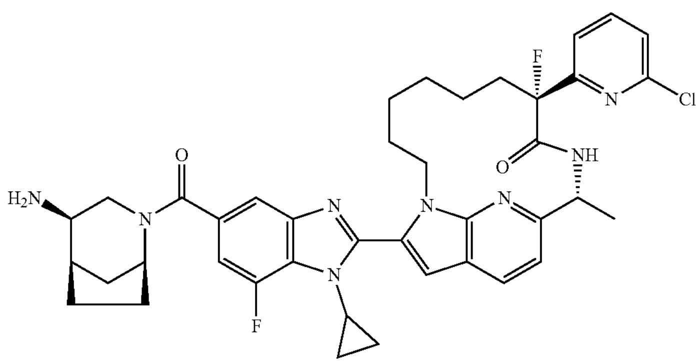 [SMILES: C[C@H]1NC(=O)[C@](F)(c2cccc(Cl)n2)CCCCCCn2c(-c3nc4cc(C(=O)N5C[C@H](N)[C@@H]6CC[C@H]5C6)cc(F)c4n3C3CC3)cc3ccc1nc32] | (8~{R},11~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 482 | 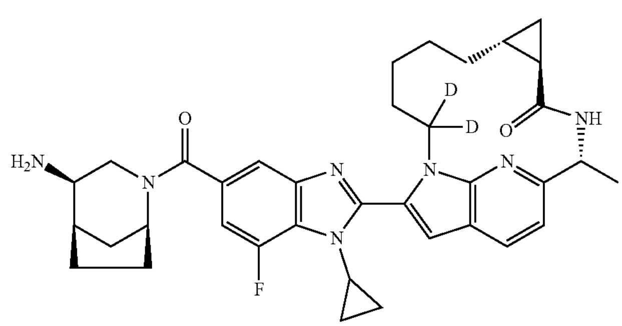 [SMILES: [2H]C1([2H])CCCC[C@@H]2C[C@H]2C(=O)N[C@H](C)c2ccc3cc(-c4nc5cc(C(=O)N6C[C@H](N)[C@@H]7CC[C@H]6C7)cc(F)c5n4C4CC4)n1c3n2] | (2~{R},5~{R},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-12,12-dideuterio-2-methyl-3,13,19-triazatetracyclo[11.5.2.0^{5,7}.0^{16,20}]icosa-1(19),14,16(20),17-tetraen-4-one |

| Example | Structure | Name |
|---|---|---|
| 483 | 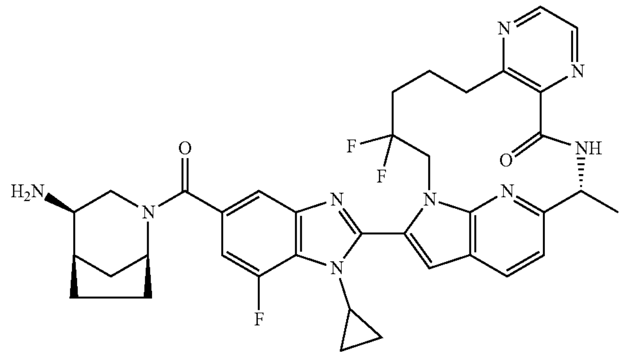 [SMILES: C[C@H]1NC(=O)c2nccnc2CCCC(F)(F)Cn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-14,14-difluoro-2-methyl-3,6,9,16,22-pentazatetracyclo[14.5.2.0^{5,10}.0^{19,23}]tricosa-1(22),5(10),6,8,17,19(23),20-heptaen-4-one |
| 484 | 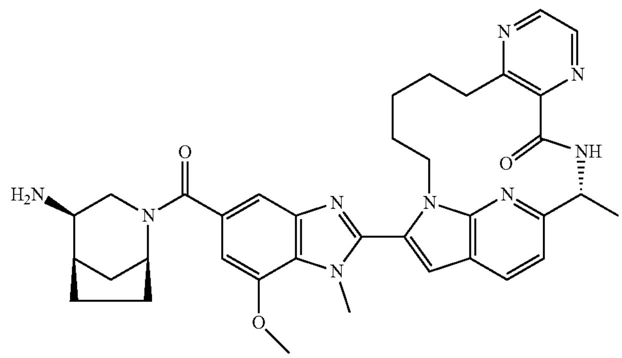 [SMILES: COc1cc(C(=O)N2C[C@H](N)[C@@H]3CC[C@H]2C3)cc2nc(-c3cc4ccc5nc4n3CCCCCc3nccnc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 485 | 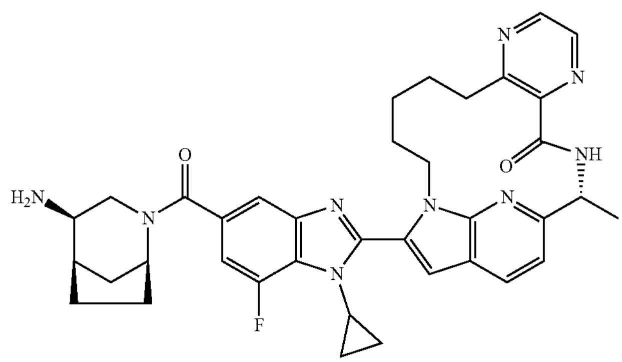 [SMILES: C[C@H]1NC(=O)c2nccnc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |

TABLE 1A

| Example | Structure | Name |
|---|---|---|
| 486 | 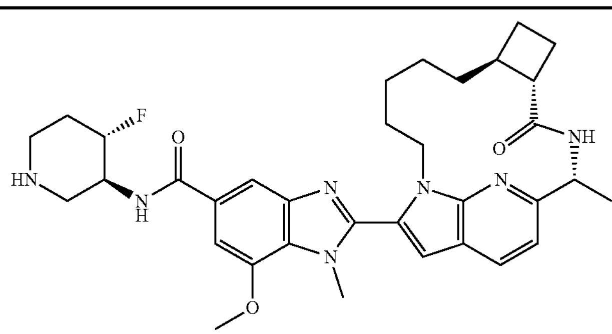 | ~{N}-[(3~{S},4~{S})-4-fluoro-3-piperidyl]-7-methoxy-1-methyl-2-[(2~{R},5~{S},8~{S})-2-methyl-4-oxo-3,14,20-triazatetracyclo[12.5.2.0^{5,8}.0^{17,21}]henicosa-1(20),15,17(21),18-tetraen-15-yl]benzimidazole-5-carboxamide |

TABLE 1A-continued

| Example | Structure | Name |
|---|---|---|
| 487 | 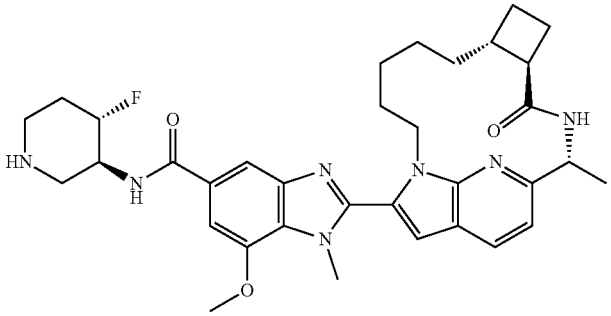 [SMILES: COc1cc(C(=O)N[C@H]2CNCC[C@@H]2F)cc2nc(-c3cc4ccc5nc4n3CCCCC[C@@H]3CC[C@H]3C(=O)N[C@@H]5C)n(C)c12] | ~{N}-[(3~{S},4~{S})-4-fluoro-3-piperidyl]-7-methoxy-1-methyl-2-[(2~{R},5~{R},8~{R})-2-methyl-4-oxo-3,14,20-triazatetracyclo [12.5.2.0^{5,8}.0^{17,21}] henicosa-1(20),15,17(21), 18-tetraen-15-yl] benzimidazole-5-carboxamide |
| 488 | 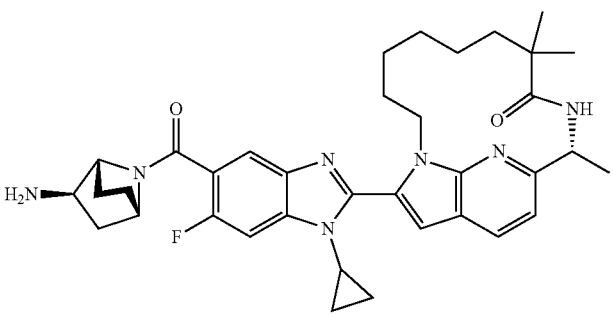 | (11~{R})-17-[5-[(1~{R},2~{R},4~{S})-2-amino-7-azabicyclo [2.2.1]heptane-7-carbonyl]-1-cyclopropyl-6-fluoro-benzimidazol-2-yl]-8,8,11-trimethyl-1,10,19-triazatricyclo [10.5.2.0^{15,18}]nonadeca-12(19),13,15(18),16-tetraen-9-one |
| 489 | 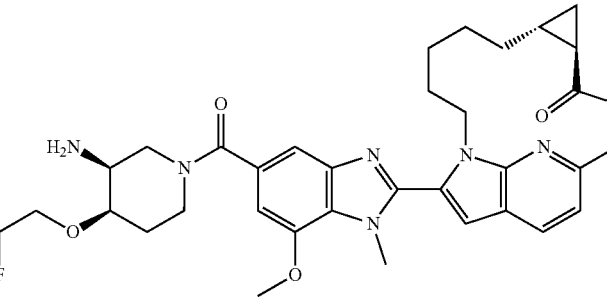 | (2~{R},5~{R},7~{R})-14-[5-[(3~{S},4~{R})-3-amino-4-(2,2-difluoroethoxy) piperidine-1-carbonyl]-7-methoxy-1-methyl-benzimidazol-2-yl]-2-methyl-3,13,19-triazatetracyclo [11.5.2.0^{5,7}.0^{16,20}] icosa-1(19),14,16(20), 17-tetraen-4-one |
| 490 | 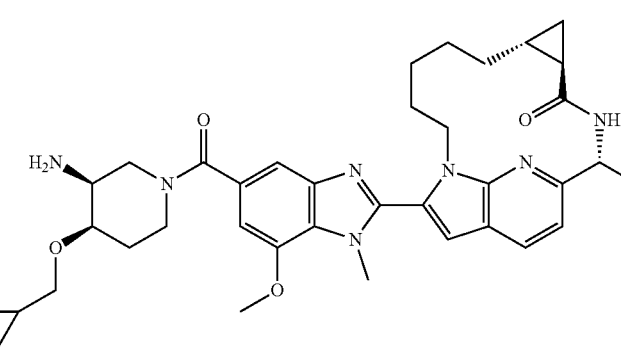 | (2~{R},5~{R},7~{R})-14-[5-[(3~{S},4~{R})-3-amino-4-(cyclopropylmethoxy) piperidine-1-carbonyl]-7-methoxy-1-methyl-benzimidazol-2-yl]-2-methyl-3,13,19-triazatetracyclo [11.5.2.0^{5,7}.0^{16,20}] icosa-1(19),14,16(20), 17-tetraen-4-one |

TABLE 1A-continued

| Example | Structure | Name |
|---|---|---|
| 491 | 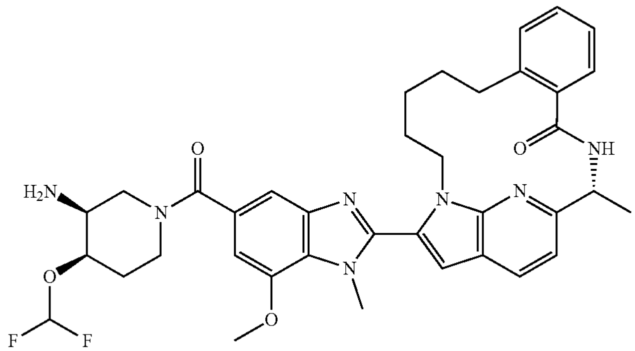 [SMILES: COc1cc(C(=O)N2CC[C@@H](OC(F)F)[C@@H](N)C2)cc2nc(-c3cc4ccc5nc4n3CCCCCc3ccccc3C(=O)N[C@@H]5C)n(C)c12] | (2~{R})-17-[5-[(3~{S},4~{R})-3-amino-4-(difluoromethoxy)piperidine-1-carbonyl]-7-methoxy-1-methyl-benzimidazol-2-yl]-2-methyl-3,16,22-triazatetracyclo[14.5.2.0^{5,10}.0^{19,23}]tricosa-1(22),5(10),6,8,17,19(23),20-heptaen-4-one |
| 492 | 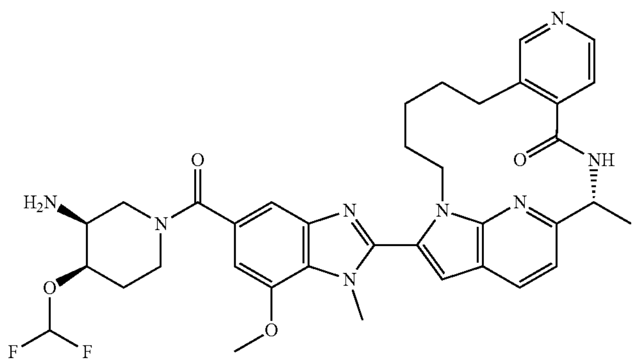 [SMILES: COc1cc(C(=O)N2CC[C@@H](OC(F)F)[C@@H](N)C2)cc2nc(-c3cc4ccc5nc4n3CCCCCc3cnccc3C(=O)N[C@@H]5C)n(C)c12] | (2~{R})-17-[5-[(3~{S},4~{R})-3-amino-4-(difluoromethoxy)piperidine-1-carbonyl]-7-methoxy-1-methyl-benzimidazol-2-yl]-2-methyl-3,8,16,22-tetrazatetracyclo[14.5.2.0^{5,10}.0^{19,23}]tricosa-1(22),5(10),6,8,17,19(23),20-heptaen-4-one |
| 493 | 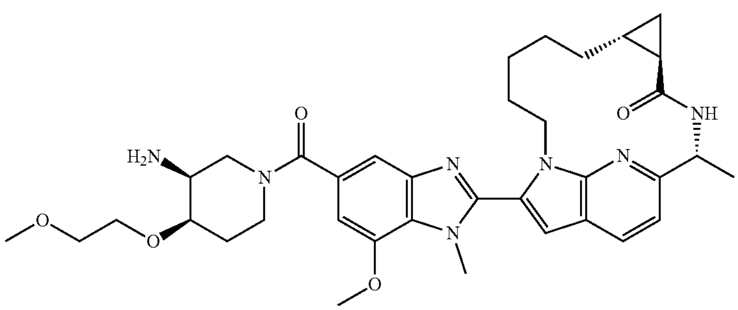 | (2~{R},5~{R},7~{R})-14-[5-[(3~{S},4~{R})-3-amino-4-(2-methoxyethoxy)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 494 | 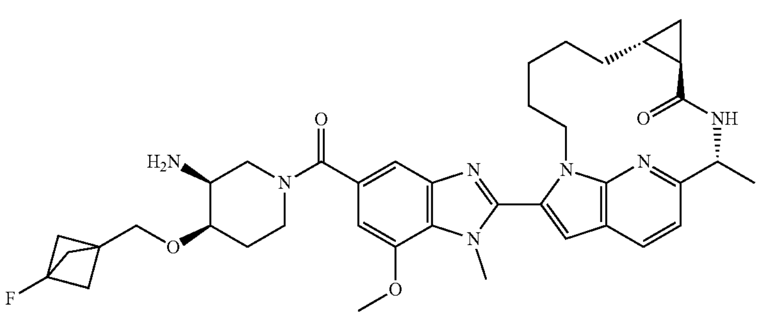 [SMILES: COc1cc(C(=O)N2CC[C@@H](OCC34CC(F)(C3)C4)[C@@H](N)C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{S},4~{R})-3-amino-4-[(3-fluoro-1-bicyclo[1.1.1]pentanyl)methoxy]piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 495 | 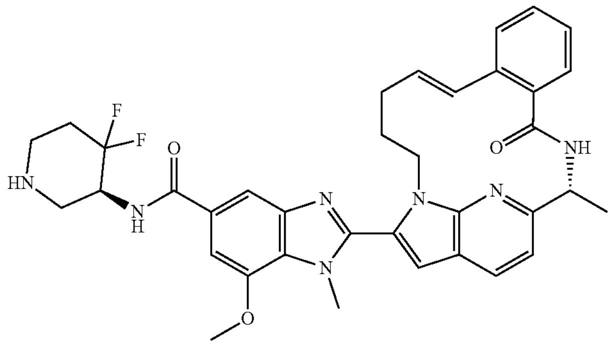 [SMILES: COc1cc(C(=O)N[C@H]2CNCCC2(F)F)cc2nc(-c3cc4ccc5nc4n3CCC/C=C/c3ccccc3C(=O)N[C@@H]5C)n(C)c12] | ~{N}-[(3~{S})-4,4-difluoro-3-piperidyl]-7-methoxy-1-methyl-2-[(2~{R},11~{E})-2-methyl-4-oxo-3,16,22-triazatetracyclo[14.5.2.0^{5,10}.0^{19,23}]tricosa-1(22),5(10),6,8,11,17,19(23),20-octaen-17-yl]benzimidazole-5-carboxamide |
| 496 | 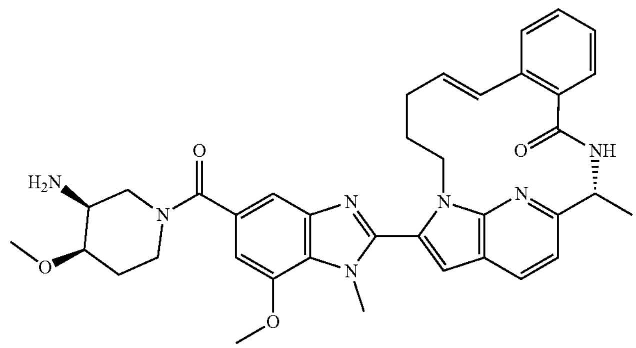 | (2~{R},11~{E})-17-[5-[(3~{S},4~{R})-3-amino-4-methoxy-piperidine-1-carbonyl]-7-methoxy-1-methyl-benzimidazol-2-yl]-2-methyl-3,16,22-triazatetracyclo[14.5.2.0^{5,10}.0^{19,23}]tricosa-1(22),5(10),6,8,11,17,19(23),20-octaen-4-one |
| 497 | 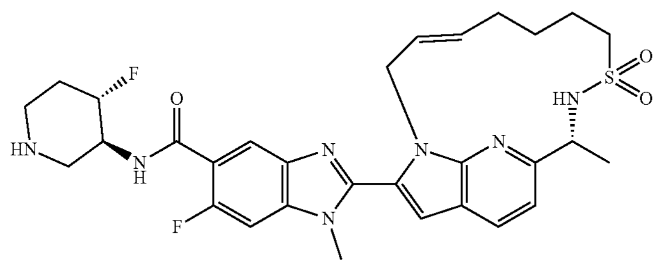 [SMILES: C[C@H]1NS(=O)(=O)CCCC/C=C/Cn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(3~{E},11~{R})-11-methyl-9,9-dioxo-9$1^{6}-thia-1,10,19-triazatricyclo[10.5.2.0^{15,18}]nonadeca-3,12(19),13,15(18),16-pentaen-17-yl]benzimidazole-5-carboxamide |
| 498 | 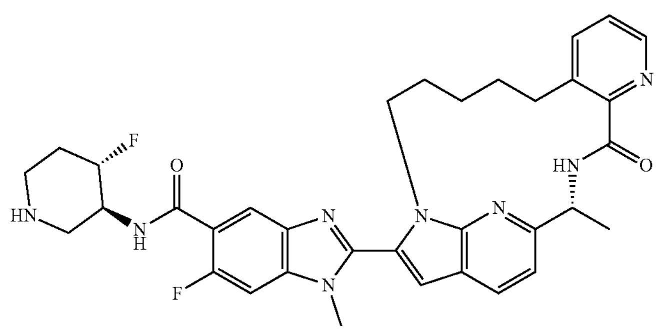 [SMILES: C[C@H]1NC(=O)c2ncccc2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R})-2-methyl-4-oxo-3,6,16,22-tetrazatetracyclo[14.5.2.0^{5,10}.0^{19,23}]tricosa-1(22),5,7,9,17,19(23),20-heptaen-17-yl]benzimidazole-5-carboxamide |
| 499 | 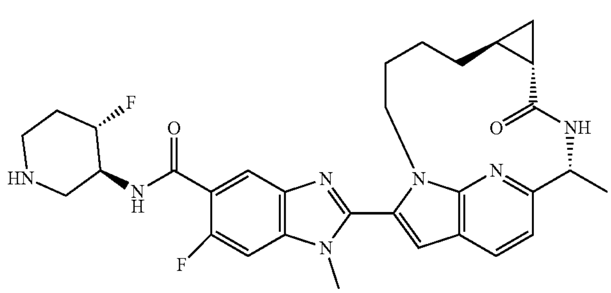 [SMILES: C[C@H]1NC(=O)[C@H]2C[C@@H]2CCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R},7~{S})-2-methyl-4-oxo-3,12,18-triazatetracyclo[10.5.2.0^{5,7}.0^{15,19}]nonadeca-1(18),13,15(19),16-tetraen-13-yl]benzimidazole-5-carboxamide |

TABLE 1A-continued

| Example | Structure | Name |
|---|---|---|
| 500 | 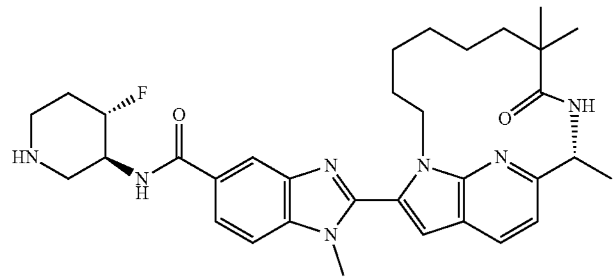 [SMILES: C[C@H]1NC(=O)C(C)(C)CCCCCCn2c(-c3nc4cc(C(=O)N[C@H]5CNCC[C@@H]5F)ccc4n3C)cc3ccc1nc32] | ~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 501 | 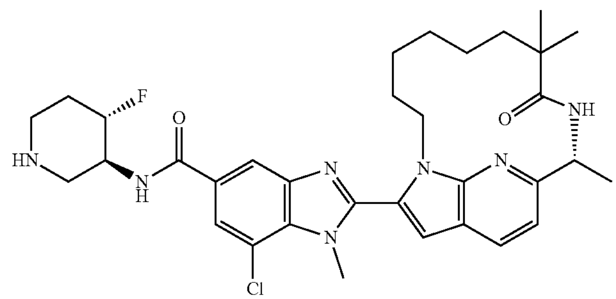 [SMILES: C[C@H]1NC(=O)C(C)(C)CCCCCCn2c(-c3nc4cc(C(=O)N[C@H]5CNCC[C@@H]5F)cc(Cl)c4n3C)cc3ccc1nc32] | 7-chloro-~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 502 | 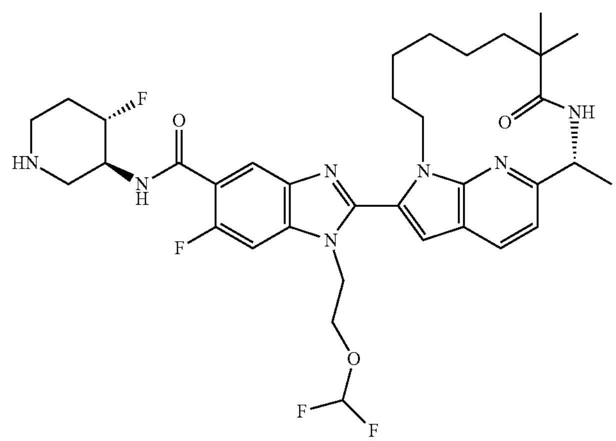 [SMILES: C[C@H]1NC(=O)C(C)(C)CCCCCCn2c(-c3nc4cc(C(=O)N[C@H]5CNCC[C@@H]5F)c(F)cc4n3CCOC(F)F)cc3ccc1nc32] | 1-[2-(difluoromethoxy)ethyl]-6-fluoro-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 503 | 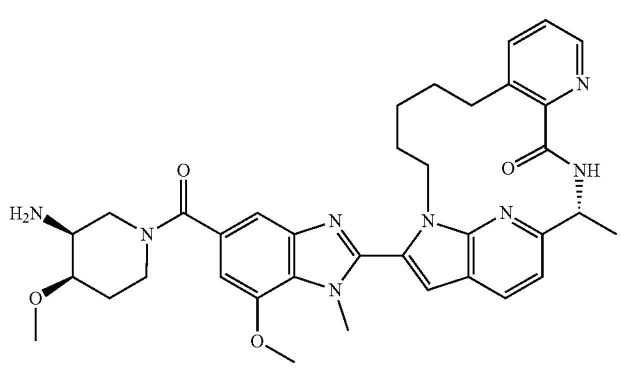 [SMILES: COc1cc(C(=O)N2CC[C@@H](OC)[C@@H](N)C2)cc2nc(-c3cc4ccc5nc4n3CCCCCc3cccnc3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-2-methyl-3,6,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 504 | 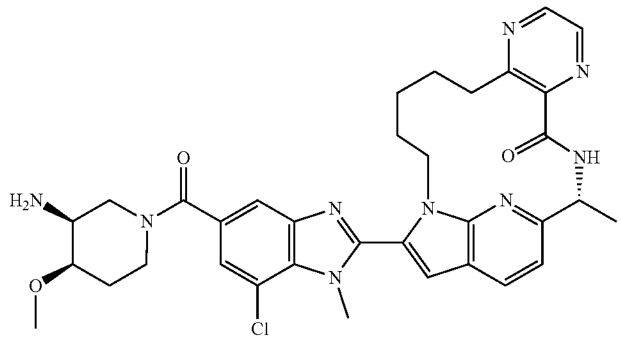 [SMILES: CO[C@@H]1CCN(C(=O)c2cc(Cl)c3c(c2)nc(-c2cc4ccc5nc4n2CCCCCc2nccnc2C(=O)N[C@@H]5C)n3C)C[C@@H]1N] | (2~{R})-17-[5-[(3~{S},4~{R})-3-amino-4-methoxy-piperidine-1-carbonyl]-7-chloro-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 505 | 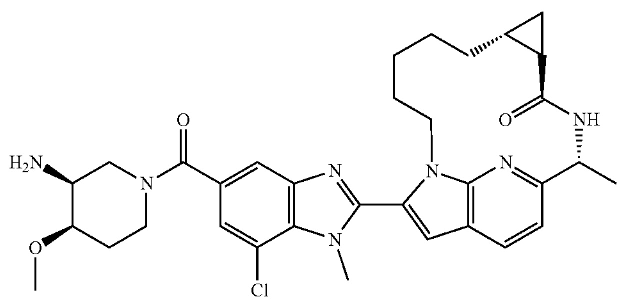 | (2~{R},7~{R})-14-[5-[(3~{S},4~{R})-3-amino-4-methoxy-piperidine-1-carbonyl]-7-chloro-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 506 | 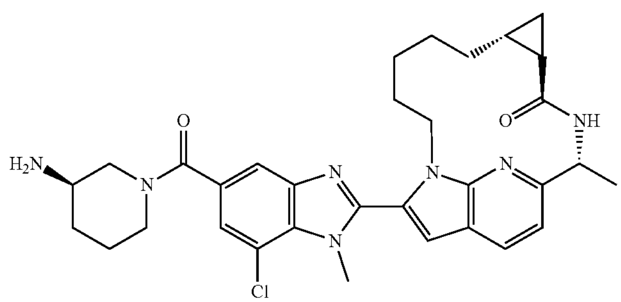 | (2~{R},7~{R})-14-[5-[(3~{R})-3-aminopiperidine-1-carbonyl]-7-chloro-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 507 | 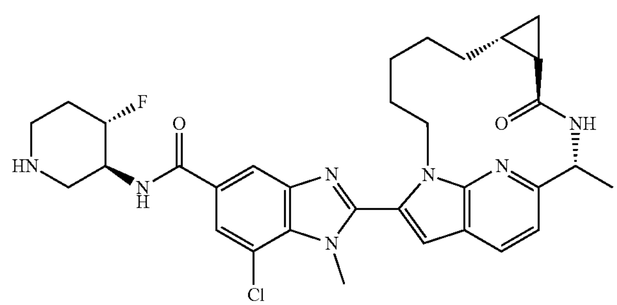 | 7-chloro-~{N}-[(3~{S},4~{S})-4-fluoro-3-piperidyl]-1-methyl-2-[(2~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 508 | 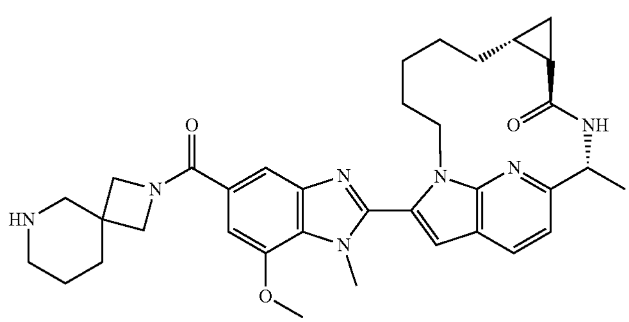 | (2~{R},7~{R})-14-[5-(2,8-diazaspiro[3.5]nonane-2-carbonyl)-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 509 | 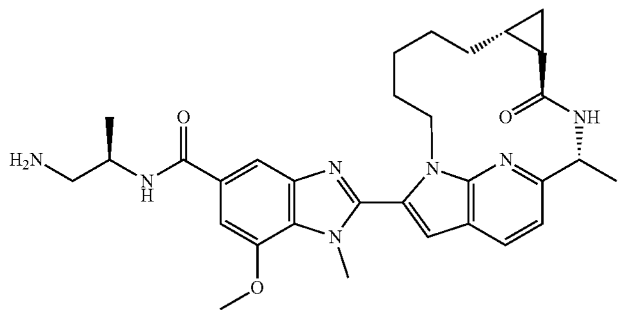 | ~{N}-[(1~{R})-2-amino-1-methyl-ethyl]-7-methoxy-1-methyl-2-[(2~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 510 | 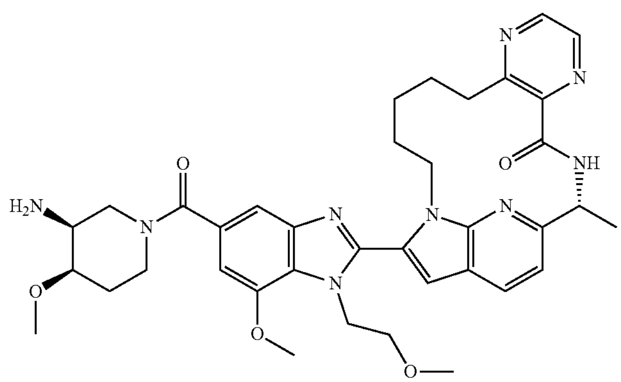 [SMILES: COCCn1c(-c2cc3ccc4nc3n2CCCCCc2nccnc2C(=O)N[C@@H]4C)nc2cc(C(=O)N3CC[C@@H](OC)[C@@H](N)C3)cc(OC)c21] | (2~{R})-17-[5-[(3~{S},4~{R})-3-amino-4-methoxy-piperidine-1-carbonyl]-7-methoxy-1-(2-methoxyethyl)benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 511 | 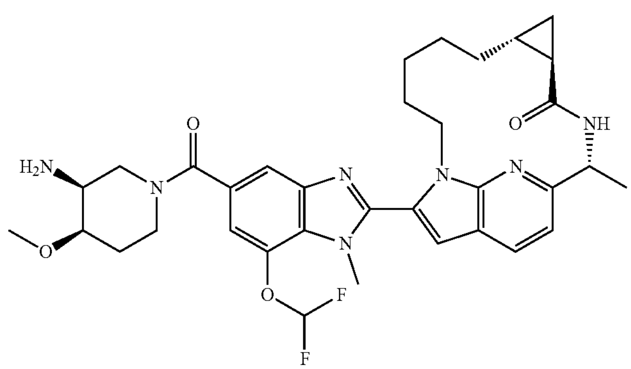 | (2~{R},5~{R},7~{R})-14-[5-[(3~{S},4~{R})-3-amino-4-methoxy-piperidine-1-carbonyl]-7-(difluoromethoxy)-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 512 | 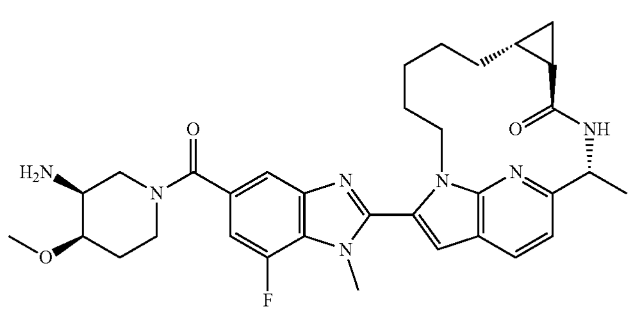 | (2~{R},5~{R},7~{R})-14-[5-[(3~{S},4~{R})-3-amino-4-methoxy-piperidine-1-carbonyl]-7-fluoro-1-methyl-benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 513 | 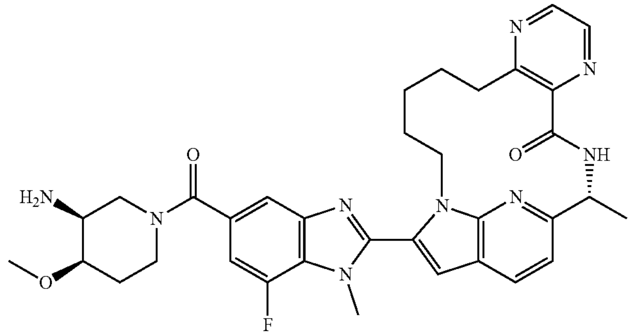 | (2~{R})-17-[5-[(3~{S},4~{R})-3-amino-4-methoxy-piperidine-1-carbonyl]-7-fluoro-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 514 | 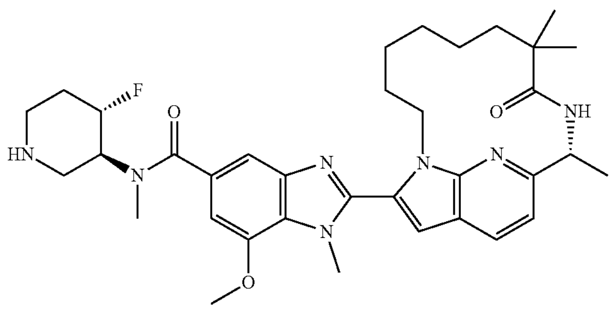 [SMILES: COc1cc(C(=O)N(C)[C@H]2CNCC[C@@H]2F)cc2nc(-c3cc4ccc5nc4n3CCCCCCC(C)(C)C(=O)N[C@@H]5C)n(C)c12] | ~{N}-[(3~{S},4~{S})-4-fluoro-3-piperidyl]-7-methoxy-~{N},1-dimethyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 515 | 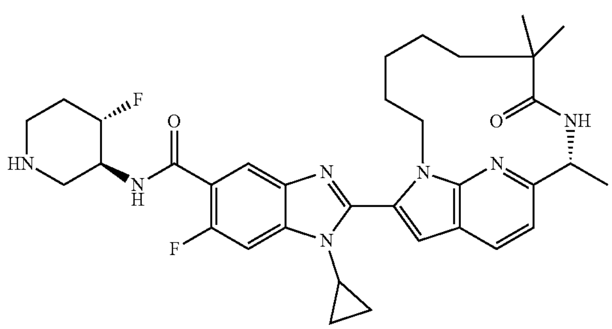 [SMILES: C[C@H]1NC(=O)C(C)(C)CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(10~{R})-7,7,10-trimethyl-8-oxo-1,9,18-triazatricyclo[9.5.2.0^{14,17}]octadeca-11(18),12,14(17),15-tetraen-16-yl]benzimidazole-5-carboxamide |
| 516 | 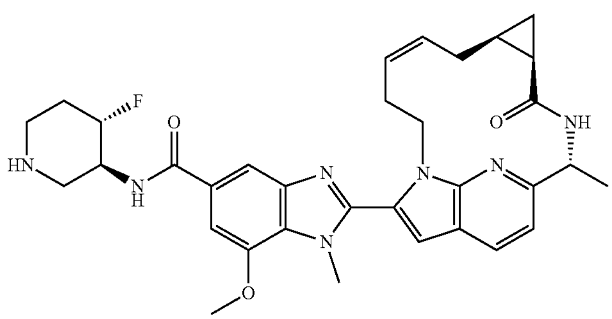 [SMILES: COc1cc(C(=O)N[C@H]2CNCC[C@@H]2F)cc2nc(-c3cc4ccc5nc4n3CC/C=C\C[C@H]3C[C@H]3C(=O)N[C@@H]5C)n(C)c12] | ~{N}-[(3~{S},4~{S})-4-fluoro-3-piperidyl]-7-methoxy-1-methyl-2-[(2~{R},5~{R},7~{S},9~{Z})-2-methyl-4-oxo-3,13,19-triazatetracyclo[11.5.2.0^{5,7}.0^{16,20}]icosa-1(19),9,14,16(20),17-pentaen-14-yl]benzimidazole-5-carboxamide |
| 517 | 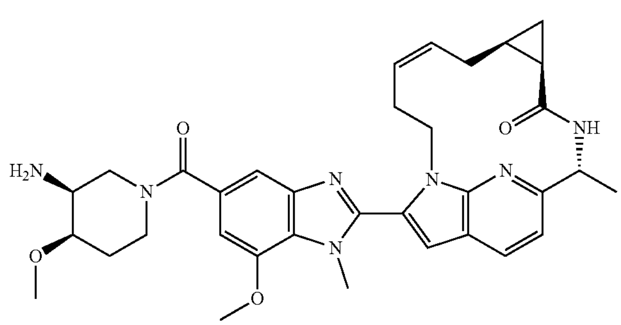 [SMILES: COc1cc(C(=O)N2CC[C@@H](OC)[C@@H](N)C2)cc2nc(-c3cc4ccc5nc4n3CC/C=C\C[C@H]3C[C@H]3C(=O)N[C@@H]5C)n(C)c12] | (2~{R},5~{R},7~{S},9~{Z})-14-[5-[(3~{S},4~{R})-3-amino-4-methoxy-piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),9,14,16(20),17-pentaen-4-one |

TABLE 1A-continued

| Example | Structure | Name |
|---|---|---|
| 518 | 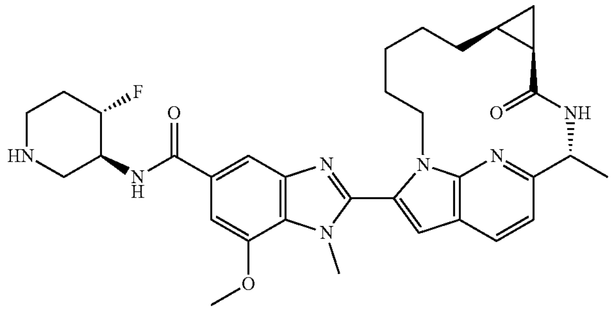 [SMILES: COc1cc(C(=O)N[C@H]2CNCC[C@@H]2F)cc2nc(-c3cc4ccc5nc4n3CCCCC[C@H]3C[C@H]3C(=O)N[C@@H]5C)n(C)c12] | ~{N}-[(3~{S},4~{S})-4-fluoro-3-piperidyl]-7-methoxy-1-methyl-2-3,13,19-triazatetracyclo[11.5.2.0^{5,7}.0^{16,20}]icosa-1(19),14,16(20),17-tetraen-14-yl]benzimidazole-5-carboxamide |
| 519 | 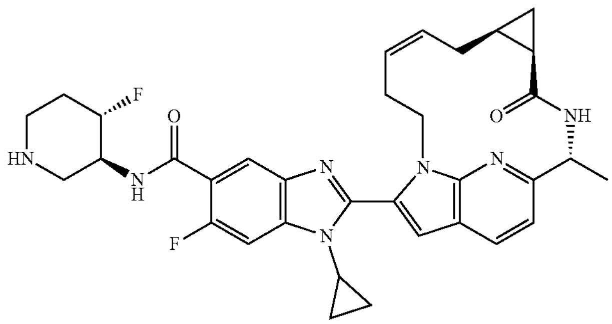 [SMILES: C[C@H]1NC(=O)[C@@H]2C[C@@H]2C/C=C\CCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R},5~{R},7~{S},9~{Z})-2-methyl-4-oxo-3,13,19-triazatetracyclo[11.5.2.0^{5,7}.0^{16,20}]icosa-1(19),9,14,16(20),17-pentaen-14-yl]benzimidazole-5-carboxamide |
| 520 | 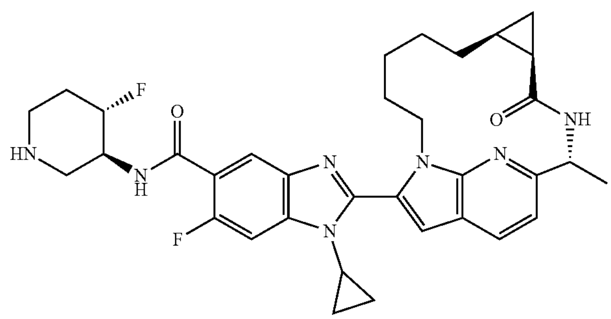 [SMILES: C[C@H]1NC(=O)[C@@H]2C[C@@H]2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R},5~{R},7~{S})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 521 | 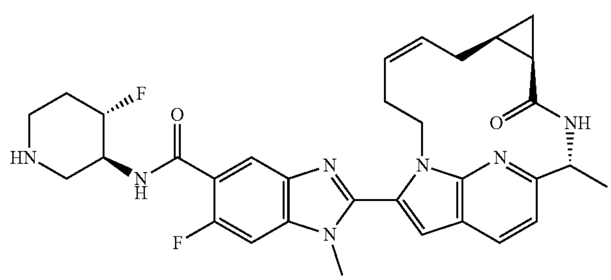 [SMILES: C[C@H]1NC(=O)[C@@H]2C[C@@H]2C/C=C\CCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R},5~{R},7~{S},9~{Z})-2-methyl-4-oxo-3,13,19-triazatetracyclo[11.5.2.0^{5,7}.0^{16,20}]icosa-1(19),9,14,16(20),17-pentaen-14-yl]benzimidazole-5-carboxamide |
| 522 | 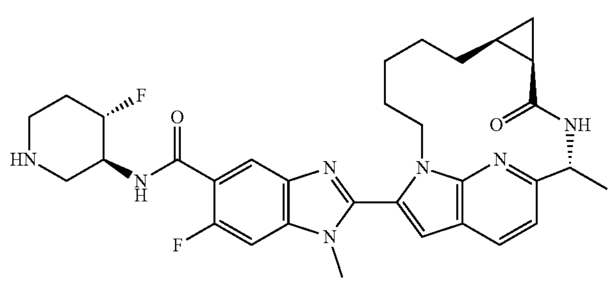 [SMILES: C[C@H]1NC(=O)[C@@H]2C[C@@H]2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R},5~{R},7~{S})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |

TABLE 1A-continued

| Example | Structure | Name |
|---|---|---|
| 523 | 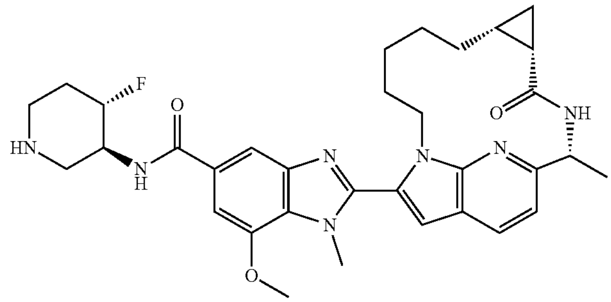 [SMILES: COc1cc(C(=O)N[C@H]2CNCC[C@@H]2F)cc2nc(-c3cc4ccc5nc4n3CCCCC[C@@H]3C[C@@H]3C(=O)N[C@@H]5C)n(C)c12] | ~{N}-[(3~{S},4~{S})-4-fluoro-3-piperidyl]-7-methoxy-1-methyl-2-[(2~{R},5~{S},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 524 | 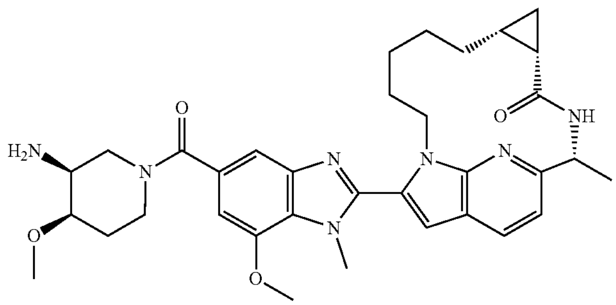 [SMILES: COc1cc(C(=O)N2CC[C@@H](OC)[C@@H](N)C2)cc2nc(-c3cc4ccc5nc4n3CCCCC[C@@H]3C[C@@H]3C(=O)N[C@@H]5C)n(C)c12] | (2~{R},5~{S},7~{R})-14-[5-[(3~{S},4~{R})-3-amino-4-methoxy-piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 525 | 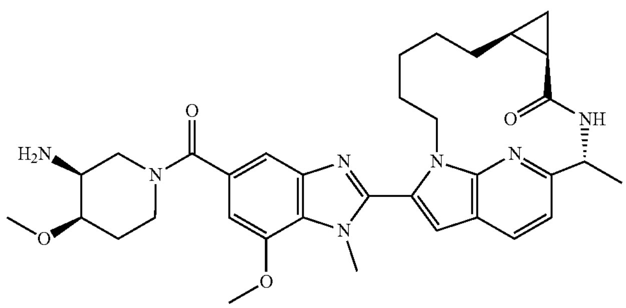 | (2~{R},5~{R},7~{S})-14-[5-[(3~{S},4~{R})-3-amino-4-methoxy-piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 526 | 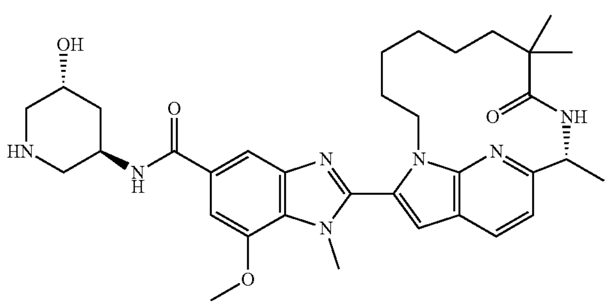 [SMILES: COc1cc(C(=O)N[C@H]2CNC[C@H](O)C2)cc2nc(-c3cc4ccc5nc4n3CCCCCCC(C)(C)C(=O)N[C@@H]5C)n(C)c12] | ~{N}-[(3~{R},5~{R})-5-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 527 | 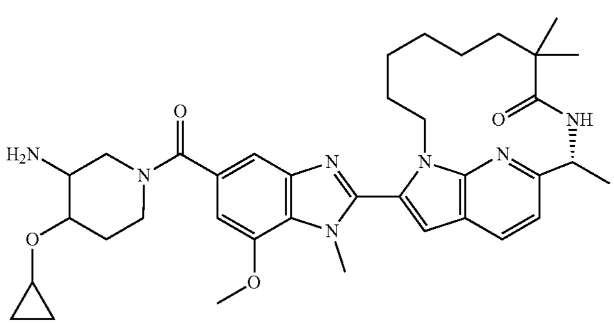 [SMILES: COc1cc(C(=O)N2CCC(OC3CC3)C(N)C2)cc2nc(-c3cc4ccc5nc4n3CCCCCCC(C)(C)C(=O)N[C@@H]5C)n(C)c12] | (11~{R})-17-[5-[3-amino-4-(cyclopropoxy)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 528 | 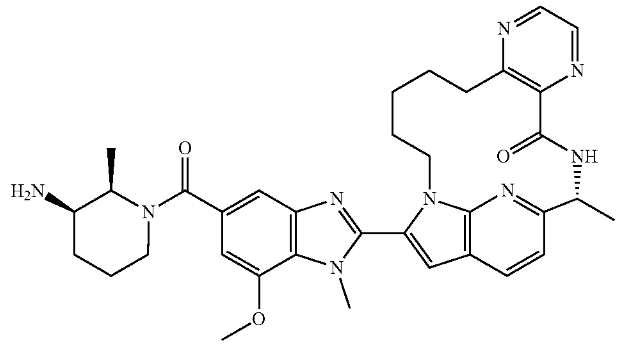 [SMILES: COc1cc(C(=O)N2CCC[C@@H](N)[C@H]2C)cc2nc(-c3cc4ccc5nc4n3CCCCCc3nccnc3C(=O)N[C@@H]5C)n(C)c12] | (2~{R})-17-[5-[(2~{R},3~{R})-3-amino-2-methyl-piperidine-1-carbonyl]-7-methoxy-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 529 | 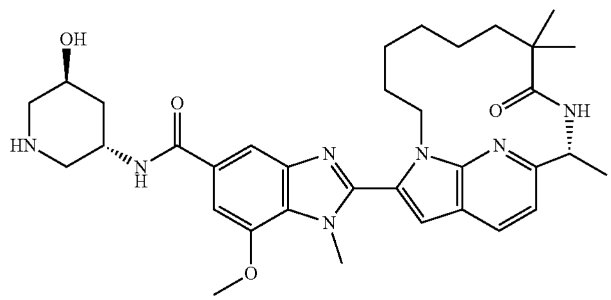 [SMILES: COc1cc(C(=O)N[C@@H]2CNC[C@@H](O)C2)cc2nc(-c3cc4ccc5nc4n3CCCCCCC(C)(C)C(=O)N[C@@H]5C)n(C)c12] | ~{N}-[(3~{S},5~{S})-5-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 530 | 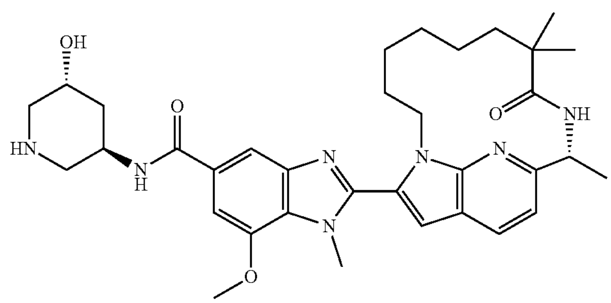 [SMILES: COc1cc(C(=O)N[C@H]2CNC[C@H](O)C2)cc2nc(-c3cc4ccc5nc4n3CCCCCCC(C)(C)C(=O)N[C@@H]5C)n(C)c12] | ~{N}-[(3~{R},5~{R})-5-hydroxy-3-piperidyl]-7-methoxy-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 531 | 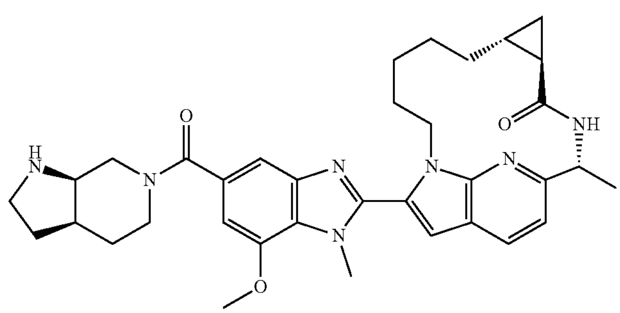 [SMILES: COc1cc(C(=O)N2CC[C@H]3CCN[C@H]3C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{a}-{R},7~{a}~{R})-1,2,3,3~{a},4,5,7,7~{a}-octahydropyrrolo[2,3-c]pyridine-6-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 532 | 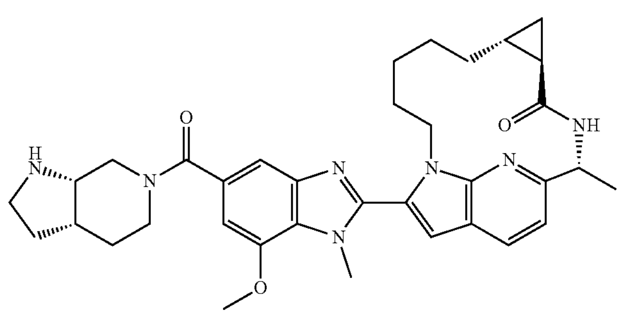 [SMILES: COc1cc(C(=O)N2CC[C@@H]3CCN[C@@H]3C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{a}~{S},7~{a}~{S})-1,2,3,3~{a},4,5,7,7~{a}-octahydropyrrolo[2,3-c]pyridine-6-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 533 | 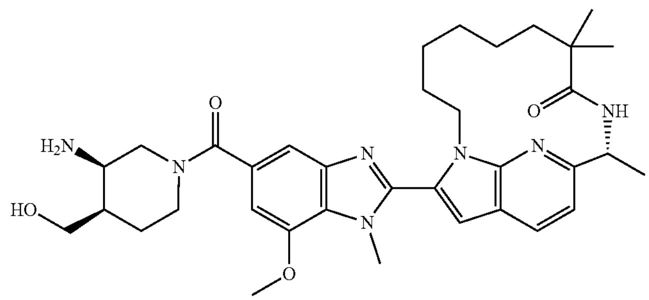 [SMILES: COc1cc(C(=O)N2CC[C@@H](CO)[C@@H](N)C2)cc2nc(-c3cc4ccc5nc4n3CCCCCCC(C)(C)C(=O)N[C@@H]5C)n(C)c12] | (11~{R})-17-[5-[(3~{R},4~{R})-3-amino-4-(hydroxymethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 534 | 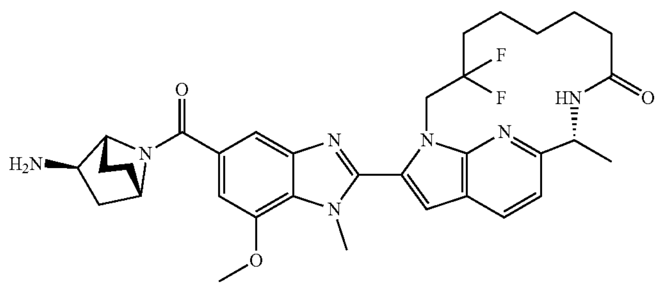 | (11~{R})-17-[5-[(1~{R},2~{R},4~{S})-2-amino-7-azabicyclo[2.2.1]heptane-7-carbonyl]-7-methoxy-1-methyl-benzimidazol-2-yl]-3,3-difluoro-11-methyl-1,10,19-triazatricyclo[10.5.2.0^{15,18}]nonadeca-12(19),13,15(18),16-tetraen-9-one |
| 535 | 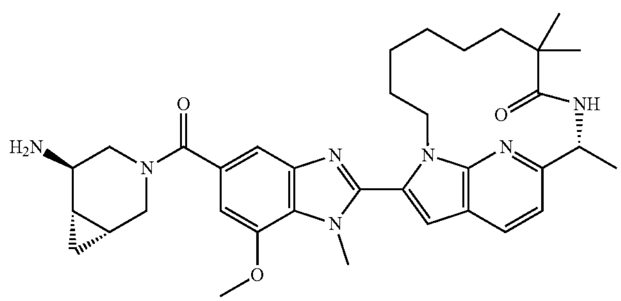 [SMILES: COc1cc(C(=O)N2C[C@@H]3C[C@@H]3[C@@H](N)C2)cc2nc(-c3cc4ccc5nc4n3CCCCCCC(C)(C)C(=O)N[C@@H]5C)n(C)c12] | (11~{R})-17-[5-[(1~{R},5~{R},6~{S})-5-amino-3-azabicyclo[4.1.0]heptane-3-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 536 | 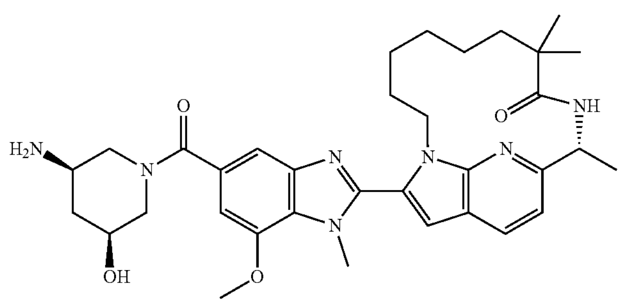 [SMILES: COc1cc(C(=O)N2C[C@H](N)C[C@H](O)C2)cc2nc(-c3cc4ccc5nc4n3CCCCCCC(C)(C)C(=O)N[C@@H]5C)n(C)c12] | (11~{R})-17-[5-[(3~{R},5~{S})-3-amino-5-hydroxy-piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 537 | 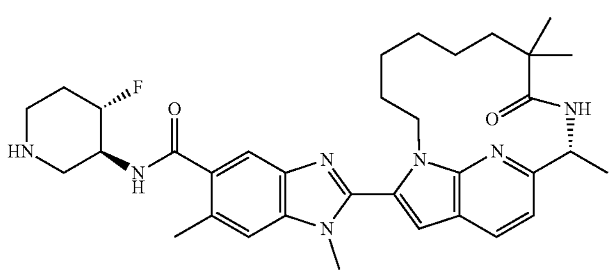 [SMILES: Cc1cc2c(cc1C(=O)N[C@H]1CNCC[C@@H]1F)nc(-c1cc3ccc4nc3n1CCCCCCC(C)(C)C(=O)N[C@@H]4C)n2C] | ~{N}-[(3~{S},4~{S})-4-fluoro-3-piperidyl]-1,6-dimethyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1A-continued

| Example | Structure | Name |
|---|---|---|
| 538 | 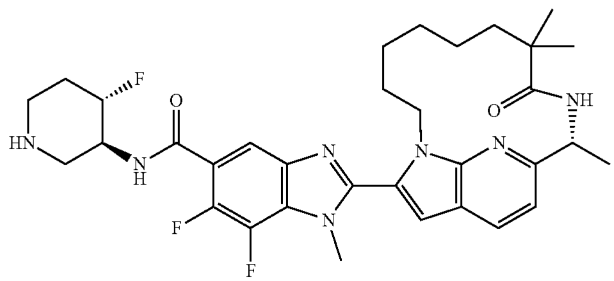 [SMILES: C[C@H]1NC(=O)C(C)(C)CCCCCCn2c(-c3nc4cc(C(=O)N[C@H]5CNCC[C@@H]5F)c(F)c(F)c4n3C)cc3ccc1nc32] | 6,7-difluoro-~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 539 | 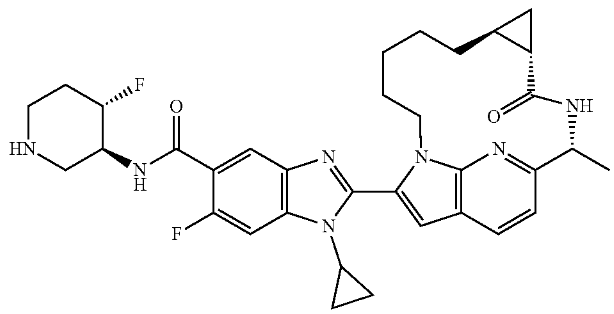 [SMILES: C[C@H]1NC(=O)[C@H]2C[C@@H]2CCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(2~{R},5~{S},7~{S})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 540 | 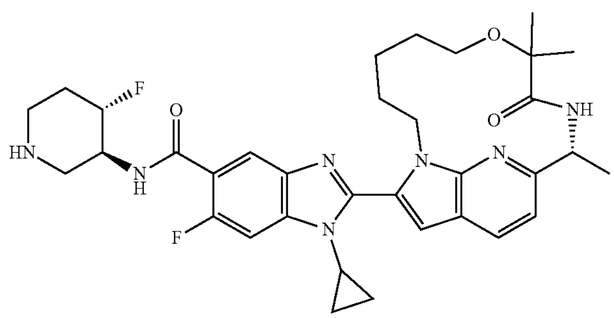 [SMILES: C[C@H]1NC(=O)C(C)(C)OCCCCCn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(11~{R})-8,8,11-trimethyl-9-oxo-7-oxa-1,10,19-triazatricyclo[10.5.2.0^{15,18}]nonadeca-12(19),13,15(18),16-tetraen-17-yl]benzimidazole-5-carboxamide |
| 541 | 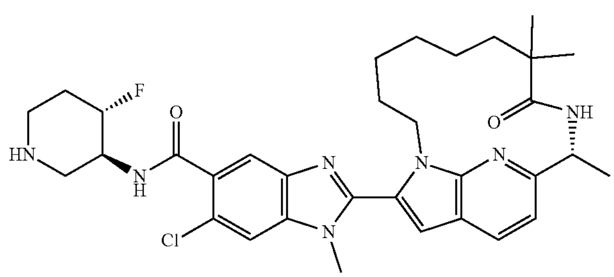 [SMILES: C[C@H]1NC(=O)C(C)(C)CCCCCCn2c(-c3nc4cc(C(=O)N[C@H]5CNCC[C@@H]5F)c(Cl)cc4n3C)cc3ccc1nc32] | 6-chloro-~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 542 | 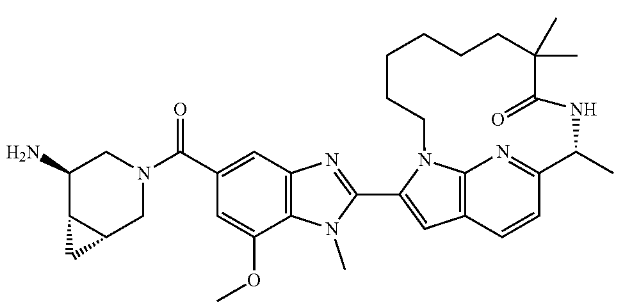 [SMILES: COc1cc(C(=O)N2C[C@@H]3C[C@@H]3[C@@H](N)C2)cc2nc(-c3cc4ccc5nc4n3CCCCCCC(C)(C)C(=O)N[C@@H]5C)n(C)c12] | (11~{R})-17-[5-[(1~{R},5~{R},6~{S})-5-amino-3-azabicyclo[4.1.0]heptane-3-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 543 | 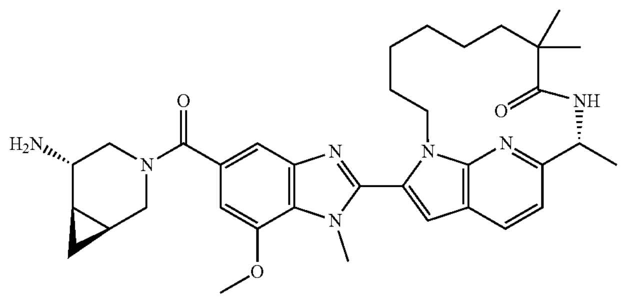 [SMILES: COc1cc(C(=O)N2C[C@H]3C[C@H]3[C@H](N)C2)cc2nc(-c3cc4ccc5nc4n3CCCCCCC(C)(C)C(=O)N[C@@H]5C)n(C)c12] | (11~{R})-17-[5-[(1~{S},5~{S},6~{R})-5-amino-3-azabicyclo[4.1.0]heptane-3-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 544 | 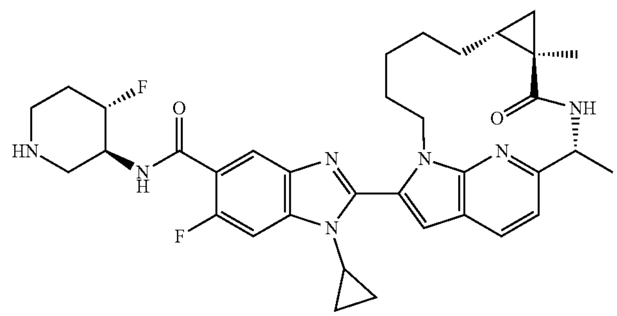 [SMILES: C[C@H]1NC(=O)[C@]2(C)C[C@H]2CCCCCn2c(-c3nc4cc(C(=O)N[C@H]5CNCC[C@@H]5F)c(F)cc4n3C3CC3)cc3ccc1nc32] | 1-cyclopropyl-2-[(2~{R},5~{R},7~{R})-2,5-dimethyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]benzimidazole-5-carboxamide |
| 545 | 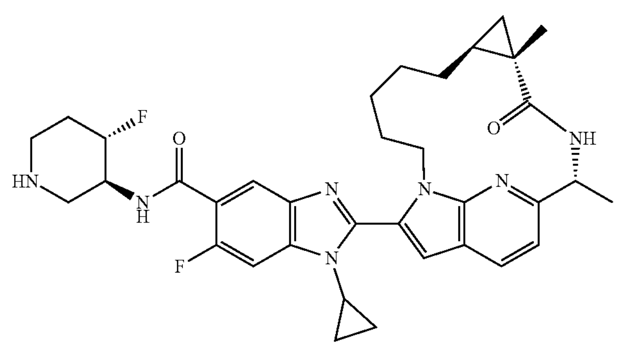 [SMILES: C[C@H]1NC(=O)[C@@]2(C)C[C@@H]2CCCCCn2c(-c3nc4cc(C(=O)N[C@H]5CNCC[C@@H]5F)c(F)cc4n3C3CC3)cc3ccc1nc32] | 1-cyclopropyl-2-[(2~{R},5~{S},7~{S})-2,5-dimethyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]benzimidazole-5-carboxamide |
| 546 | 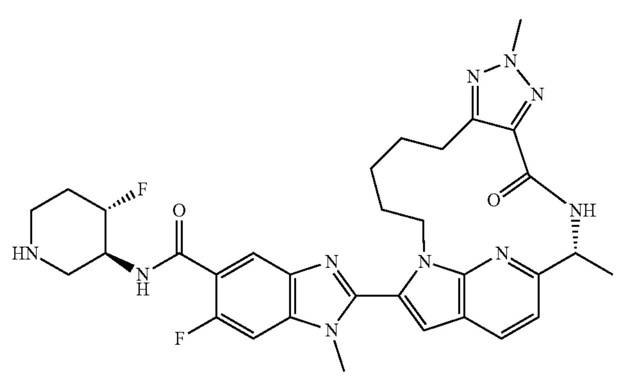 [SMILES: C[C@H]1NC(=O)c2nn(C)nc2CCCCCn2c(-c3nc4cc(C(=O)N[C@H]5CNCC[C@@H]5F)c(F)cc4n3C)cc3ccc1nc32] | 2-[(2~{R})-2,7-dimethyl-4-oxo-3,6,7,8,15,21-hexazatetracyclo[13.5.2.0^{5,9}.0^{18,22}]docosa-1(21),5,8,16,18(22),19-hexaen-16-yl]-6-fluoro-~{N}-[(3~{S},4~{S})-4-fluoro-3-piperidyl]-1-methyl-benzimidazole-5-carboxamide |

TABLE 1A-continued

| Example | Structure | Name |
|---|---|---|
| 547 | 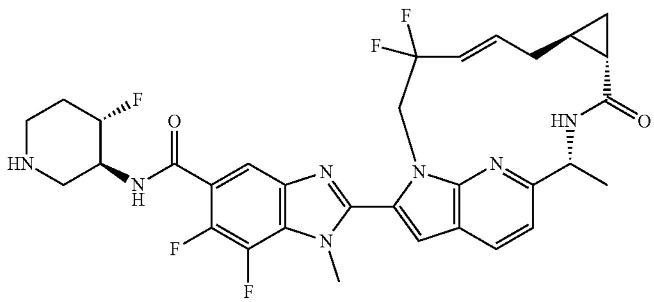 [SMILES: C[C@H]1NC(=O)[C@H]2C[C@@H]2C/C=C/C(F)(F)Cn2c(-c3nc4cc(C(=O)N[C@H]5CNCC[C@@H]5F)c(F)c(F)c4n3C)cc3ccc1nc32] | 2-[(2~{R},5~{S},7~{S},9~{E})-11,11-difluoro-2-methyl-4-oxo-3,13,19-triazatetracyclo[11.5.2.0^{5,7}.0^{16,20}]icosa-1(19),9,14,16(20),17-pentaen-14-yl]-6,7-difluoro-~{N}-[(3~{S},4~{S})-4-fluoro-3-piperidyl]-1-methyl-benzimidazole-5-carboxamide |
| 548 | 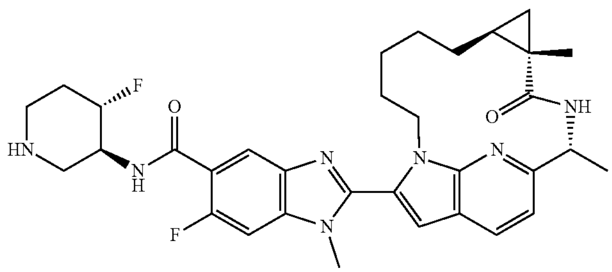 [SMILES: C[C@H]1NC(=O)[C@@]2(C)C[C@@H]2CCCCCn2c(-c3nc4cc(C(=O)N[C@H]5CNCC[C@@H]5F)c(F)cc4n3C)cc3ccc1nc32] | 2-[(2~{R},5~{S},7~{S})-2,5-dimethyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 549 | 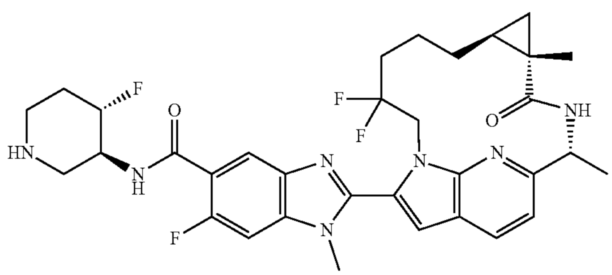 [SMILES: C[C@H]1NC(=O)[C@@]2(C)C[C@@H]2CCCC(F)(F)Cn2c(-c3nc4cc(C(=O)N[C@H]5CNCC[C@@H]5F)c(F)cc4n3C)cc3ccc1nc32] | 2-[(2~{R},5~{S},7~{S})-11,11-difluoro-2,5-dimethyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 550 | 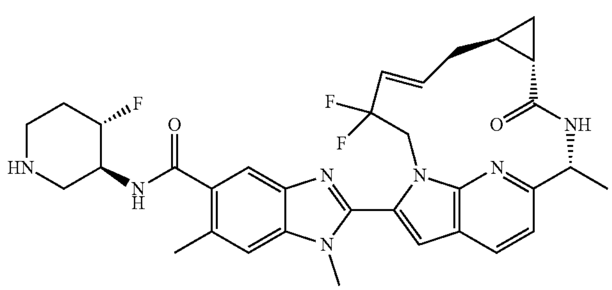 [SMILES: Cc1cc2c(cc1C(=O)N[C@H]1CNCC[C@@H]1F)nc(-c1cc3ccc4nc3n1CC(F)(F)/C=C/C[C@H]1C[C@@H]1C(=O)N[C@@H]4C)n2C] | 2-[(2~{R},5~{S},7~{S},9~{E})-11,11-difluoro-2-methyl-4-oxo-3,13,19-triazatetracyclo[11.5.2.0^{5,7}.0^{16,20}]icosa-1(19),9,14,16(20),17-pentaen-14-yl]-~{N}-[(3~{S},4~{S})-4-fluoro-3-piperidyl]-1,6-dimethyl-benzimidazole-5-carboxamide |
| 551 | 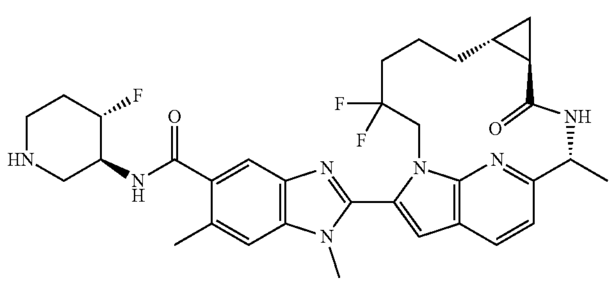 [SMILES: Cc1cc2c(cc1C(=O)N[C@H]1CNCC[C@@H]1F)nc(-c1cc3ccc4nc3n1CC(F)(F)CCC[C@@H]1C[C@H]1C(=O)N[C@@H]4C)n2C] | 2-[(2~{R},5~{R},7~{R})-11,11-difluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]-1,6-dimethyl-benzimidazole-5-carboxamide |

TABLE 1A-continued

| Example | Structure | Name |
|---|---|---|
| 552 | 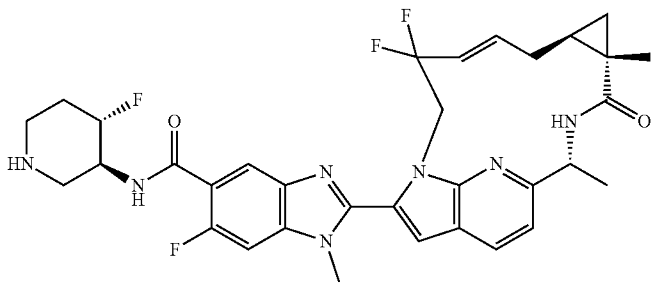 [SMILES: C[C@H]1NC(=O)[C@@]2(C)C[C@@H]2C/C=C/C(F)(F)Cn2c(-c3nc4cc(C(=O)N[C@H]5CNCC[C@@H]5F)c(F)cc4n3C)cc3ccc1nc32] | 2-[(2~{R},5~{S},7~{S},9~{E})-11,11-difluoro-2,5-dimethyl-4-oxo-3,13,19-triazatetracyclo[11.5.2.0^{5,7}.0^{16,20}]icosa-1(19),9,14,16(20),17-pentaen-14-yl]-6-fluoro-~{N}-[(3~{S},4~{S})-4-fluoro-3-piperidyl]-1-methyl-benzimidazole-5-carboxamide |
| 553 | 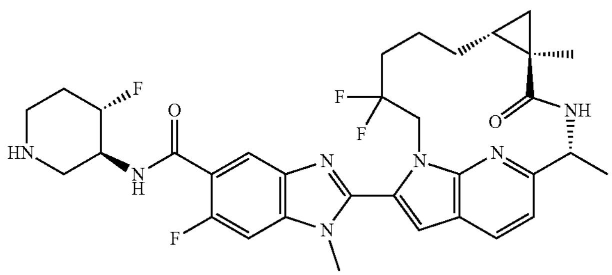 [SMILES: C[C@H]1NC(=O)[C@]2(C)C[C@H]2CCCC(F)(F)Cn2c(-c3nc4cc(C(=O)N[C@H]5CNCC[C@@H]5F)c(F)cc4n3C)cc3ccc1nc32] | 2-[(2~{R},5~{R},7~{R})-11,11-difluoro-2,5-dimethyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 554 | 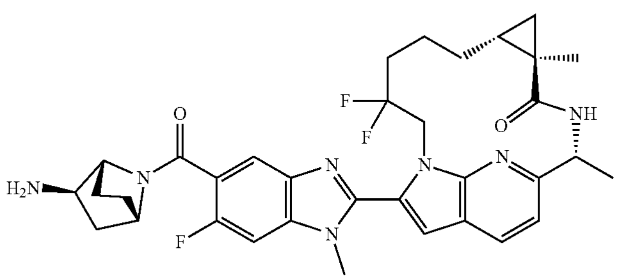 [SMILES: C[C@H]1NC(=O)[C@]2(C)C[C@H]2CCCC(F)(F)Cn2c(-c3nc4cc(C(=O)N5[C@H]6CC[C@@H]5[C@H](N)C6)c(F)cc4n3C)cc3ccc1nc32] | (2~{R},5~{R},7~{R})-14-[5-[(1~{R},2~{R},4~{S})-2-amino-7-azabicyclo[2.2.1]heptane-7-carbonyl]-6-fluoro-1-methyl-benzimidazol-2-yl]-11,11-difluoro-2,5-dimethyl-3,13,19-triazatetracyclo[11.5.2.0^{5,7}.0^{16,20}]icosa-1(19),14,16(20),17-tetraen-4-one |
| 555 | 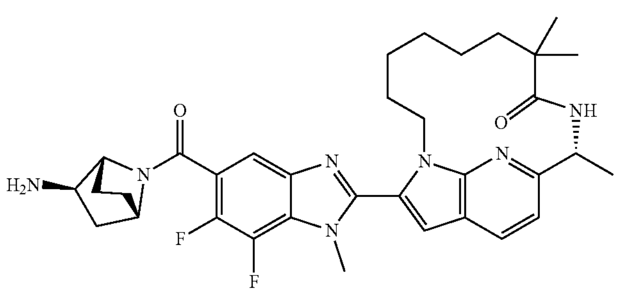 [SMILES: C[C@H]1NC(=O)C(C)(C)CCCCCCn2c(-c3nc4cc(C(=O)N5[C@H]6CC[C@@H]5[C@H](N)C6)c(F)c(F)c4n3C)cc3ccc1nc32] | (11~{R})-17-[5-[(1~{R},2~{R},4~{S})-2-amino-7-azabicyclo[2.2.1]heptane-7-carbonyl]-6,7-difluoro-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 556 | 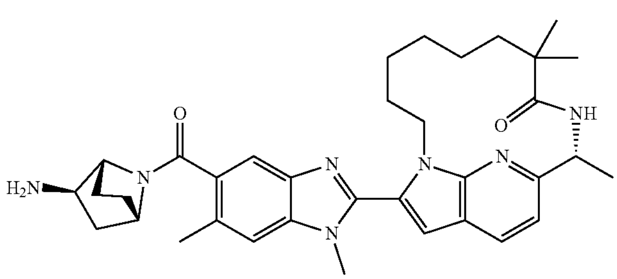 [SMILES: Cc1cc2c(cc1C(=O)N1[C@H]3CC[C@@H]1[C@H](N)C3)nc(-c1cc3ccc4nc3n1CCCCCCC(C)(C)C(=O)N[C@@H]4C)n2C] | (11~{R})-17-[5-[(1~{R},2~{R},4~{S})-2-amino-7-azabicyclo[2.2.1]heptane-7-carbonyl]-1,6-dimethyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 557 | 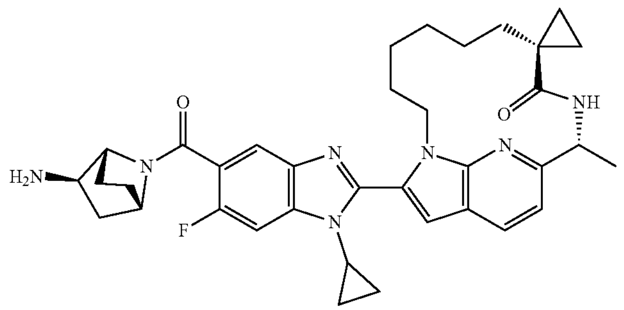 | (2~{R},5~{R},7~{R})-14-[5-[(1~{R},2~{R},4~{S})-2-amino-7-azabicyclo[2.2.1]heptane-7-carbonyl]-1-cyclopropyl-6-fluoro-benzimidazol-2-yl]-2-methyl-3,13,19-triazatetracyclo[11.5.2.0^{5,7}.0^{16,20}]icosa-1(19),14,16(20),17-tetraen-4-one |
| 558 | 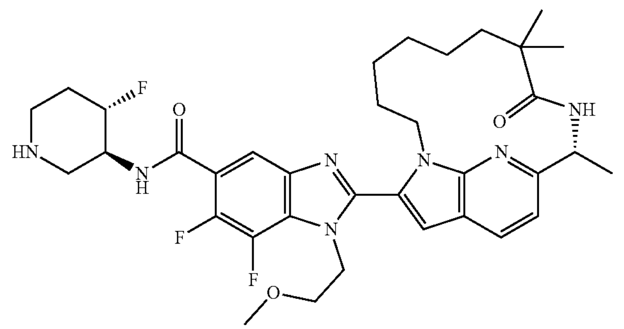 [SMILES: COCCn1c(-c2cc3ccc4nc3n2CCCCCCC(C)(C)C(=O)N[C@@H]4C)nc2cc(C(=O)N[C@H]3CNCC[C@@H]3F)c(F)c(F)c21] | 6,7-difluoro-~{N}-[(3~{S},4~{S})-4-fluoro-3-piperidyl]-1-(2-methoxyethyl)-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |
| 559 | 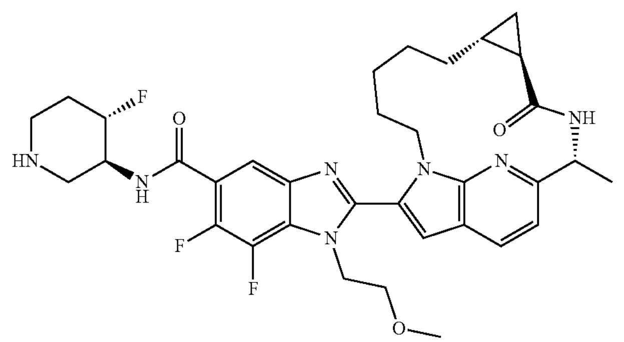 [SMILES: COCCn1c(-c2cc3ccc4nc3n2CCCCC[C@@H]2C[C@H]2C(=O)N[C@@H]4C)nc2cc(C(=O)N[C@H]3CNCC[C@@H]3F)c(F)c(F)c21] | 6,7-difluoro-~{N}-[(3~{S},4~{S})-4-fluoro-3-piperidyl]-1-(2-methoxyethyl)-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 560 | 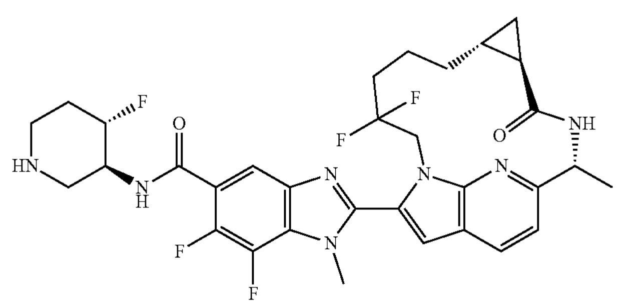 [SMILES: C[C@H]1NC(=O)[C@@H]2C[C@H]2CCCC(F)(F)Cn2c(-c3nc4cc(C(=O)N[C@H]5CNCC[C@@H]5F)c(F)c(F)c4n3C)cc3ccc1nc32] | 2-[(2~{R},5~{R},7~{R})-11,11-difluoro-2-methyl-4-oxo-3,13,19-triazatetracyclo[11.5.2.0^{5,7}.0^{16,20}]icosa-1(19),14,16(20),17-tetraen-14-yl]-6,7-difluoro-~{N}-[(3~{S},4~{S})-4-fluoro-3-piperidyl]-1-methyl-benzimidazole-5-carboxamide |
| 561 | 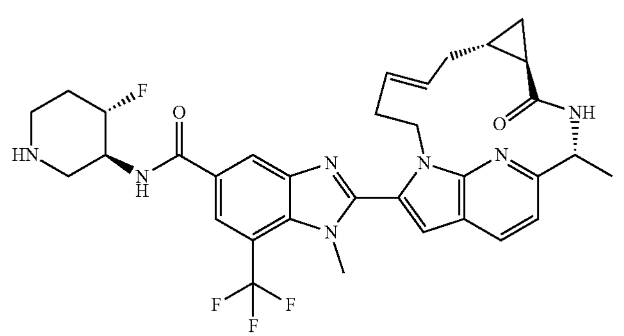 [SMILES: C[C@H]1NC(=O)[C@@H]2C[C@H]2C/C=C/CCn2c(-c3nc4cc(C(=O)N[C@H]5CNCC[C@@H]5F)cc(C(F)(F)F)c4n3C)cc3ccc1nc32] | ~{N}-[(3~{S},4~{S})-4-fluoro-3-piperidyl]-1-methyl-2-[(2~{R},5~{R},7~{R},9~{E})-2-methyl-4-oxo-3,13,19-triazatetracyclo[11.5.2.0^{5,7}.0^{16,20}]icosa-1(19),9,14,16(20),17-pentaen-14-yl]-7-(trifluoromethyl)benzimidazole-5-carboxamide |

TABLE 1A-continued

| Example | Structure | Name |
|---|---|---|
| 562 | 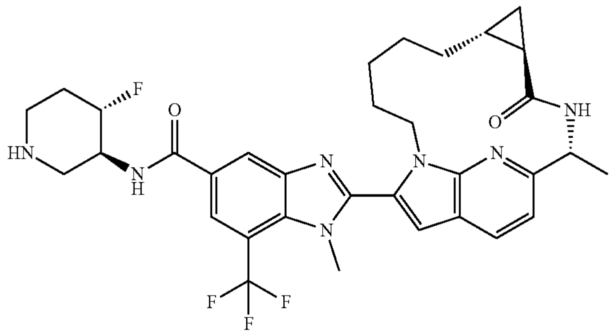 [SMILES: C[C@H]1NC(=O)[C@@H]2C[C@H]2CCCCCn2c(-c3nc4cc(C(=O)N[C@H]5CNCC[C@@H]5F)cc(C(F)(F)F)c4n3C)cc3ccc1nc32] | ~{N}-[(3~{S},4~{S})-4-fluoro-3-piperidyl]-1-methyl-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-7-(trifluoromethyl)benzimidazole-5-carboxamide |
| 563 | 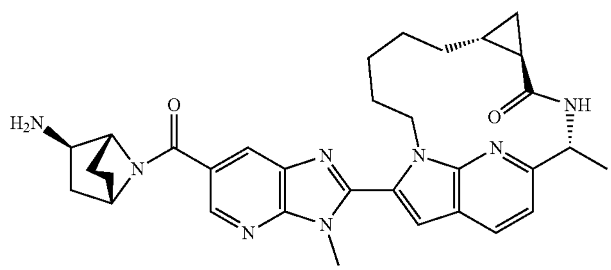 | (2~{R},5~{R},7~{R})-14-[6-[(1~{R},2~{R},4~{S})-2-amino-7-azabicyclo[2.2.1]heptane-7-carbonyl]-3-methyl-imidazo[4,5-b]pyridin-2-yl]-2-methyl-3,13,19-triazatetracyclo[11.5.2.0^{5,7}.0^{16,20}]icosa-1(19),14,16(20),17-tetraen-4-one |
| 564 | 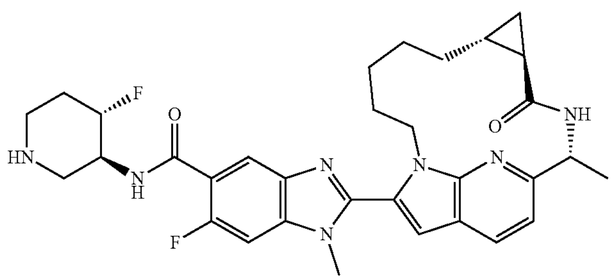 [SMILES: C[C@H]1NC(=O)[C@@H]2C[C@H]2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R},5~{R},7~{R})-2-methyl-4-oxo-3,13-diazatetracyclo[11.5.2.0^{5,7}.0^{16,20}]icosa-1(19),14,16(20),17-tetraen-14-yl]benzimidazole-5-carboxamide |
| 565 | 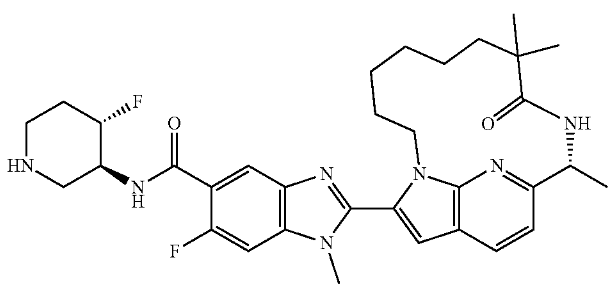 [SMILES: C[C@H]1NC(=O)C(C)(C)CCCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(11~{R})-8,8,11-trimethyl-9-oxo-1,10-diazatricyclo[10.5.2.0^{15,18}]nonadeca-12(19),13,15(18),16-tetraen-17-yl]benzimidazole-5-carboxamide |
| 566 | 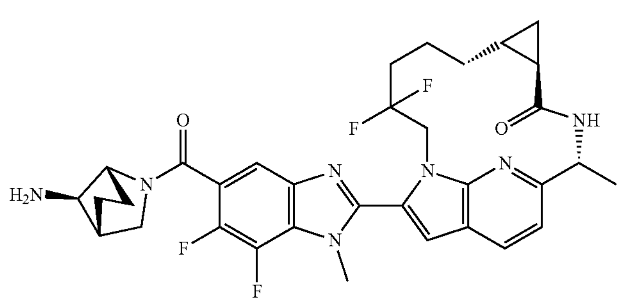 | (2~{R},5~{R},7~{R})-14-[5-[(1~{R},4~{R},7~{R})-7-amino-2-azabicyclo[2.2.1]heptane-2-carbonyl]-6,7-difluoro-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 567 | 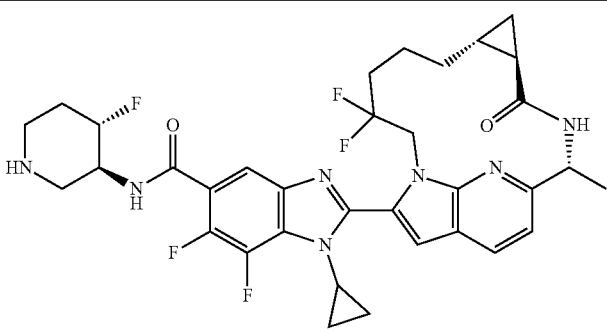 | 1-cyclopropyl-2-[(2~{R},5~{R},7~{R})-triazatetracyclo[11.5.2.0^{5,7}.0^{16,20}]icosa-1(19),14,16(20),17-tetraen-14-yl]-6,7-difluoro-~{N}-[(3~{S},4~{S})-4-fluoro-3-piperidyl]benzimidazole-5-carboxamide |
| 568 | 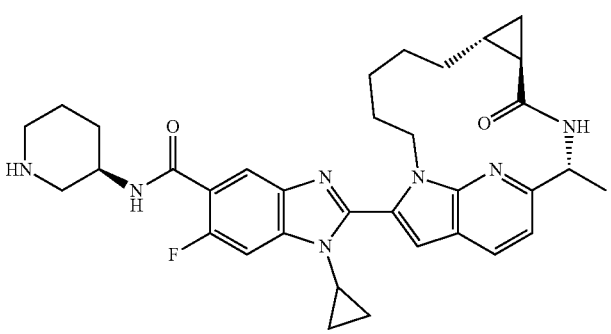 [SMILES: C[C@H]1NC(=O)[C@@H]2C[C@H]2CCCCCn2c(-c3nc4cc(C(=O)N[C@@H]5CCCNC5)c(F)cc4n3C3CC3)cc3ccc1nc32] | 1-cyclopropyl-6-fluoro-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-~{N}-[(3~{R})-3-piperidyl]benzimidazole-5-carboxamide11,11-difluoro-2-methyl-4-oxo-3,13,19- |
| 569 | 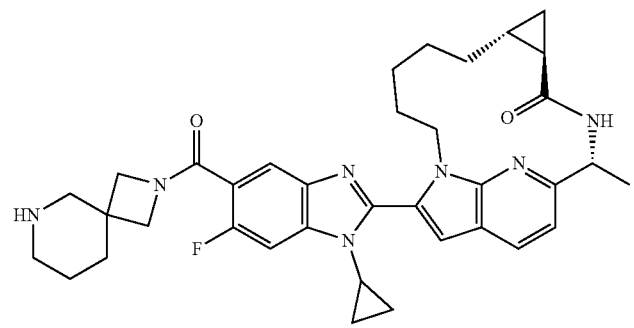 [SMILES: C[C@H]1NC(=O)[C@@H]2C[C@H]2CCCCCn2c(-c3nc4cc(C(=O)N5CC6(CCCNC6)C5)c(F)cc4n3C3CC3)cc3ccc1nc32] | (2~{R},5~{R},7~{R})-14-[1-cyclopropyl-5-(2,8-diazaspiro[3.5]nonane-2-carbonyl)-6-fluoro-benzimidazol-2-yl]-2-methyl-3,13,19-triazatetracyclo[11.5.2.0^{5,7}.0^{16,20}]icosa-1(19),14,16(20),17-tetraen-4-one |
| 570 | 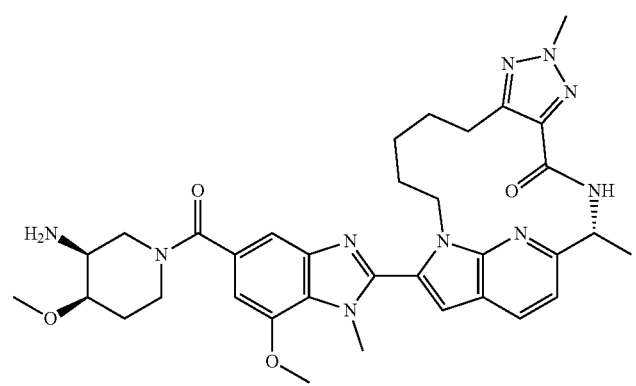 | (2~{R})-16-[5-[(3~{S},4~{R})-3-amino-4-methoxy-piperidine-1-carbonyl]-7-methoxy-1-methyl-benzimidazol-2-yl]-2,7-dimethyl-3,6,7,8,15,21-hexazatetracyclo[13.5.2.0^{5,9}.0^{18,22}]docosa-1(21),5,8,16,18(22),19-hexaen-4-one |

TABLE 1A-continued

| Example | Structure | Name |
|---|---|---|
| 571 | 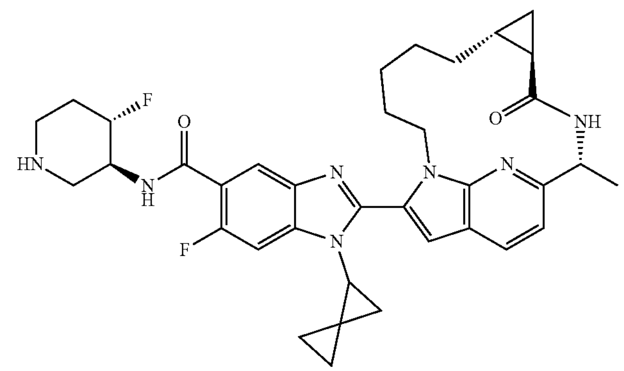 [SMILES: C[C@H]1NC(=O)[C@@H]2C[C@H]2CCCCCn2c(-c3nc4cc(C(=O)N[C@H]5CNCC[C@@H]5F)c(F)cc4n3C3CC34CC4)cc3ccc1nc32] | 6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-1-spiro[2.2]pentan-2-yl-benzimidazole-5-carboxamide |
| 572 | 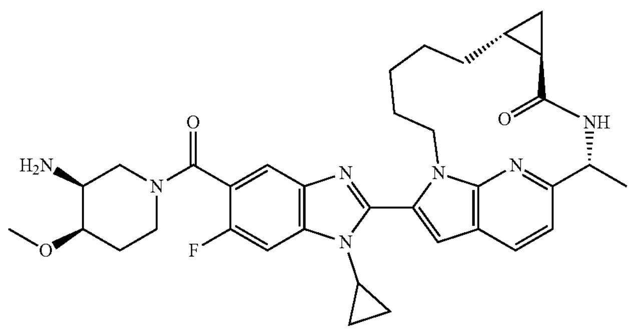 | (2~{R},5~{R},7~{R})-14-[5-[(3~{S},4~{R})-3-amino-4-methoxy-piperidine-1-carbonyl]-1-cyclopropyl-6-fluoro-benzimidazol-2-yl]-2-methyl-3,13,19-triazatetracyclo[11.5.2.0^{5,7}.0^{16,20}]icosa-1(19),14,16(20),17-tetraen-4-one |
| 573 | 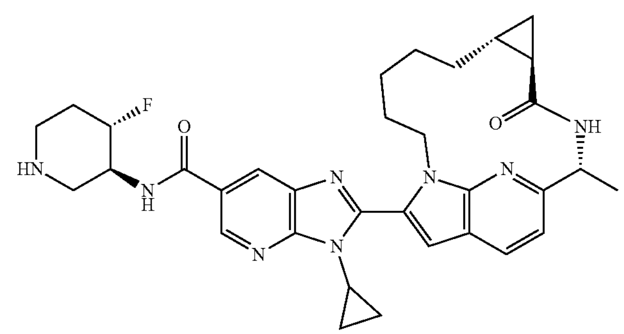 [SMILES: C[C@H]1NC(=O)[C@@H]2C[C@H]2CCCCCn2c(-c3nc4cc(C(=O)N[C@H]5CNCC[C@@H]5F)cnc4n3C3CC3)cc3ccc1nc32] | 3-cyclopropyl-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]imidazo[4,5-b]pyridine-6-carboxamide |
| 574 | 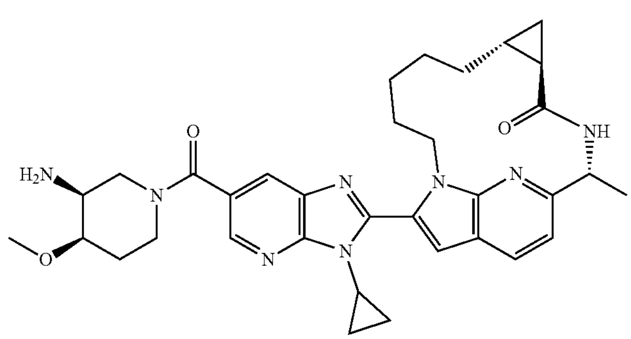 | (2~{R},5~{R},7~{R})-14-[6-[(3~{S},4~{R})-3-amino-4-methoxy-piperidine-1-carbonyl]-3-cyclopropyl-imidazo[4,5-b]pyridin-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---------|-----------|------|
| 575 | 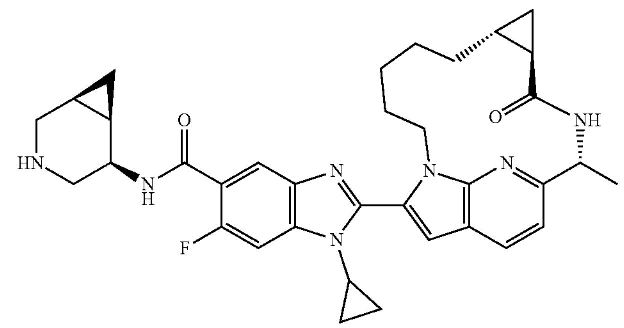 [SMILES: C[C@H]1NC(=O)[C@@H]2C[C@H]2CCCCCn2c(-c3nc4cc(C(=O)N[C@H]5CNC[C@H]6C[C@H]65)c(F)cc4n3C3CC3)cc3ccc1nc32] | ~{N}-[(1~{S},5~{R},6~{R})-3-azabicyclo[4.1.0]heptan-5-yl]-1-cyclopropyl-6-fluoro-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 576 | 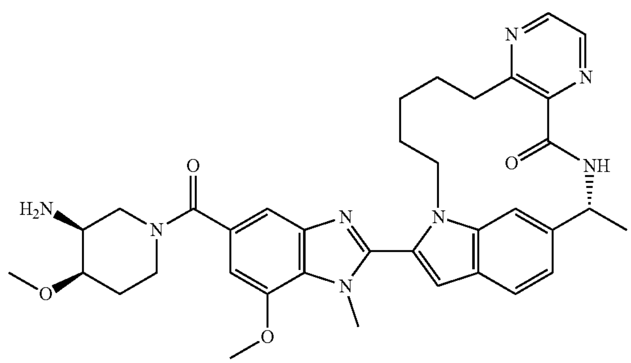 | (2~{R})-17-[5-[(3~{S},4~{R})-3-amino-4-methoxy-piperidine-1-carbonyl]-7-methoxy-1-methyl-benzimidazol-2-yl]-2-methyl-3,6,9,16-tetrazatetracyclo[14.5.2.0^{5,10}.0^{19,23}]tricosa-1(22),5(10),6,8,17,19(23),20-heptaen-4-one |
| 577 | 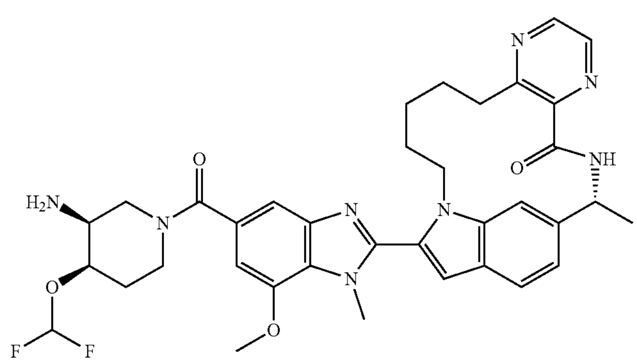 [SMILES: COc1cc(C(=O)N2CC[C@@H](OC(F)F)[C@@H](N)C2)cc2nc(-c3cc4ccc5cc4n3CCCCCc3nccnc3C(=O)N[C@@H]5C)n(C)c12] | (2~{R})-17-[5-[(3~{S},4~{R})-3-amino-4-(difluoromethoxy)piperidine-1-carbonyl]-7-methoxy-1-methyl-benzimidazol-2-yl]-2-methyl-3,6,9,16-tetrazatetracyclo[14.5.2.0^{5,10}.0^{19,23}]tricosa-1(22),5(10),6,8,17,19(23),20-heptaen-4-one |
| 578 | 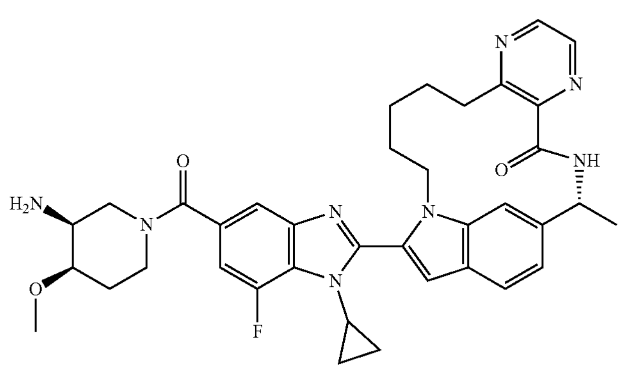 [SMILES: CO[C@@H]1CCN(C(=O)c2cc(F)c3c(c2)nc(-c2cc4ccc5cc4n2CCCCCc2nccnc2C(=O)N[C@@H]5C)n3C2CC2)C[C@@H]1N] | (2~{R})-17-[5-[(3~{S},4~{R})-3-amino-4-methoxy-piperidine-1-carbonyl]-1-cyclopropyl-7-fluoro-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 579 | 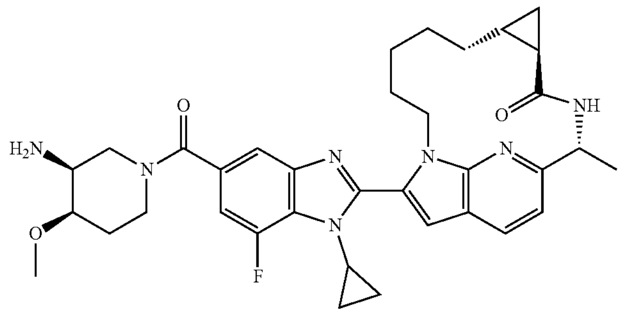 | (2~{R},5~{R},7~{R})-14-[5-[(3~{S},4~{R})-3-amino-4-methoxy-piperidine-1-carbonyl]-1-cyclopropyl-7-fluoro-benzimidazol-2-yl]-2-methyl-3,13,19-triazatetracyclo[11.5.2.0^{5,7}.0^{16,20}]icosa-1(19),14,16(20),17-tetraen-4-one |
| 580 | 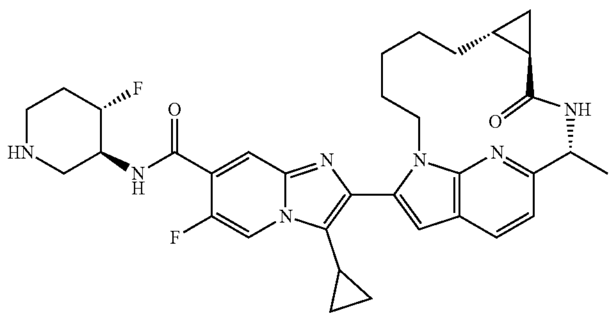 [SMILES: C[C@H]1NC(=O)[C@@H]2C[C@H]2CCCCCn2c(-c3nc4cc(C(=O)N[C@H]5CNCC[C@@H]5F)c(F)cn4c3C3CC3)cc3ccc1nc32] | 3-cyclopropyl-6-fluoro-{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]imidazo[1,2-a]pyridine-7-carboxamide |
| 581 | 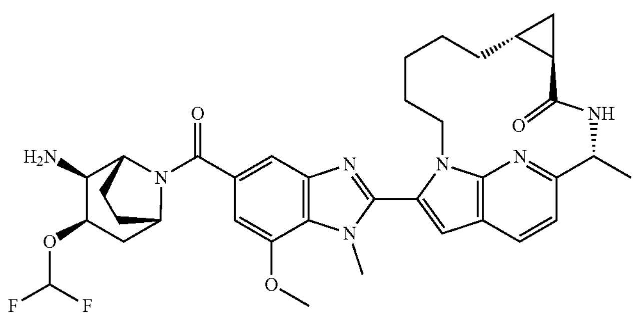 [SMILES: COc1cc(C(=O)N2[C@H]3CC[C@@H]2[C@H](N)[C@H](OC(F)F)C3)cc2nc(-c3cc4ccc5nc4n3CCCCC[C@@H]3C[C@H]3C(=O)N[C@@H]5C)n(C)c12] | (2~{R},5~{R},7~{R})-14-[5-[(1~{R},2~{S},3~{R},5~{S})-2-amino-3-(difluoromethoxy)-8-azabicyclo[3.2.1]octane-8-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 582 | 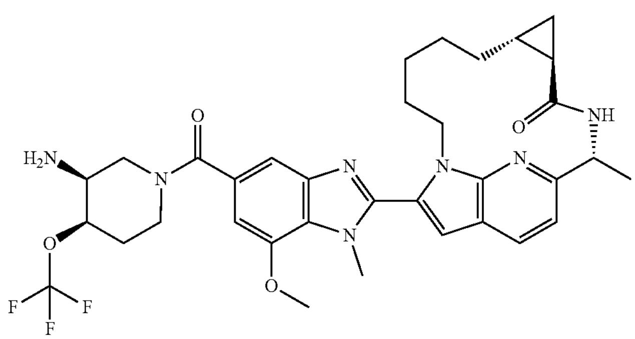 [SMILES: COc1cc(C(=O)N2CC[C@@H](OC(F)(F)F)[C@@H](N)C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{S},4~{R})-3-amino-4-(trifluoromethoxy)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 583 | 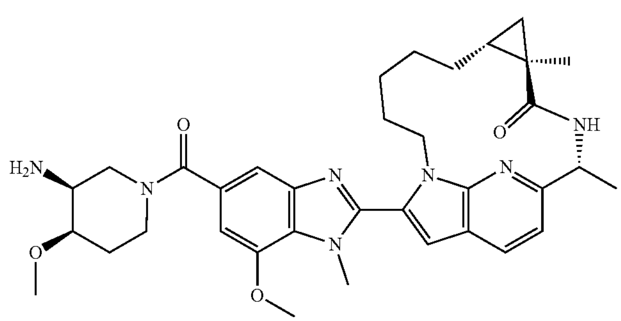 [SMILES: COc1cc(C(=O)N2CC[C@@H](OC)[C@@H](N)C2)cc2nc(-c3cc4ccc5nc4n3CCCCC[C@@H]3C[C@@]3(C)C(=O)N[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-2,5-dimethyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 584 | 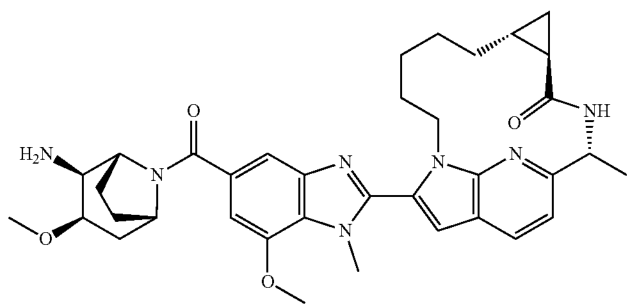 | (2~{R},5~{R},7~{R})-14-[5-[(1~{R},2~{S},3~{R},5~{S})-2-amino-3-methoxy-8-azabicyclo[3.2.1]octane-8-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 585 | 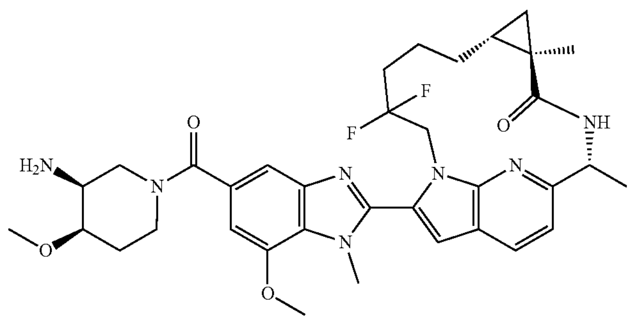 | (2~{R},5~{R},7~{R})-14-[5-[(3~{S},4~{R})-3-amino-4-methoxy-piperidine-1-carbonyl]-7-methoxy-1-methyl-benzimidazol-2-yl]-11,11-difluoro-2,5-dimethyl-3,13,19-triazatetracyclo[11.5.2.0^{5,7}.0^{16,20}]icosa-1(19),14,16(20),17-tetraen-4-one |
| 586 | 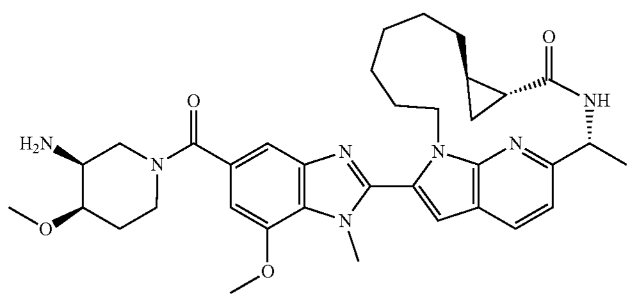 | (2~{R},5~{R},7~{R})-15-[5-(3~{S},4~{R})-3-[amino-4-methoxy-piperidine-1-carbonyl]-7-methoxy-1-methyl-benzimidazol-2-yl]-2-methyl-3,14,20-triazatetracyclo[12.5.2.0^{5,7}.0^{17,21}]henicosa-1(20),15,17(21),18-tetraen-4-one |
| 587 | 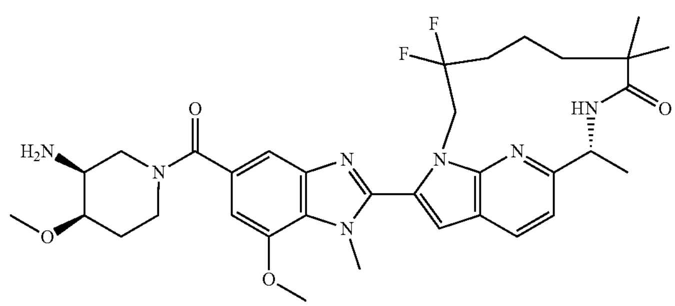 | (10~{R})-16-[5-[(3~{S},4~{R})-3-amino-4-methoxy-piperidine-1-carbonyl]-7-methoxy-1-methyl-benzimidazol-2-yl]-3,3-difluoro-7,7,10-trimethyl-1,9,18-triazatricyclo[9.5.2.0^{14,17}]octadeca-11(18),12,14(17),15-tetraen-8-one |
| 588 | 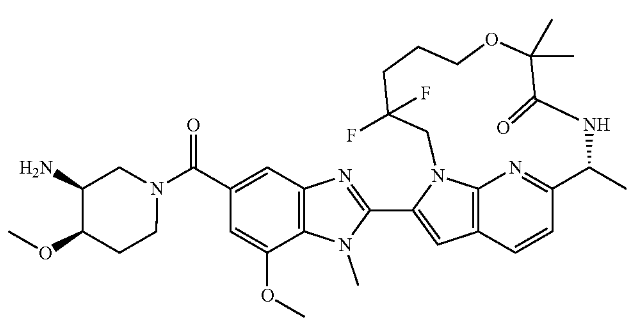 | (11~{R})-17-[5-[(3~{S},4~{R})-3-amino-4-methoxy-piperidine-1-carbonyl]-7-methoxy-1-methyl-benzimidazol-2-yl]-3,3-difluoro-8,8,11-trimethyl-7-oxa-1,10,19-triazatricyclo[10.5.2.0^{15,18}]nonadeca-12(19),13,15(18),16-tetraen-9-one |

| Example | Structure | Name |
| --- | --- | --- |
| 589 | 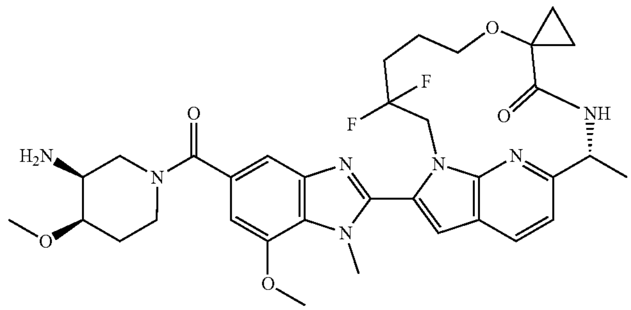 | (11~{R})-17-[5-[(3~{S},4~{R})-3-amino-4-methoxy-piperidine-1-carbonyl]-7-methoxy-1-methyl-benzimidazol-2-yl]-3,3-difluoro-11-methyl-spiro[7-oxa-1,10,19-triazatricyclo[10.5.2.0^{15,18}]nonadeca-12(19),13,15(18),16-tetraene-8,1'-cyclopropane]-9-one |
| 590 | 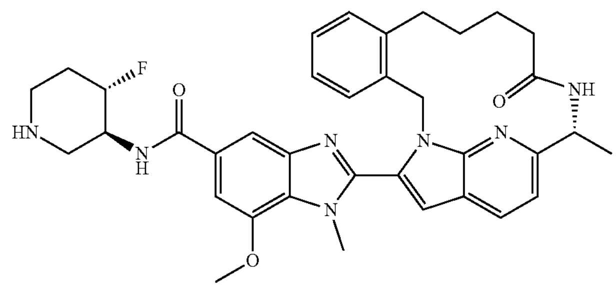 [SMILES: COc1cc(C(=O)N[C@H]2CNCC[C@@H]2F)cc2nc(-c3cc4ccc5nc4n3Cc3ccccc3CCCCC(=O)N[C@@H]5C)n(C)c12] | ~{N}-[(3~{S},4~{S})-4-fluoro-3-piperidyl]-7-methoxy-1-methyl-2-[(15~{R})-15-methyl-13-oxo-1,14,23-triazatetracyclo[14.5.2.0^{3,8}.0^{19,22}]tricosa-3(8),4,6,16,18,20,22-heptaen-21-yl]benzimidazole-5-carboxamide |
| 591 | 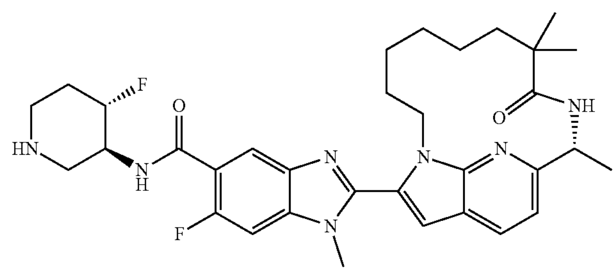 [SMILES: C[C@H]1NC(=O)C(C)(C)CCCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12,14,16,18-tetraen-17-yl]benzimidazole-5-carboxamide |
| 592 | 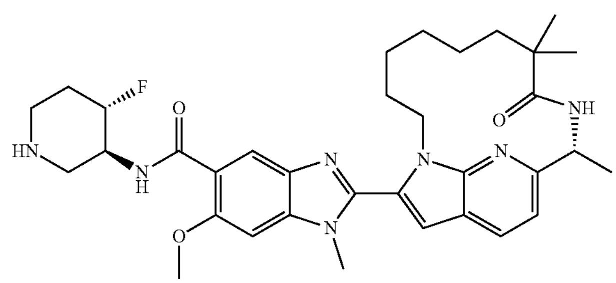 [SMILES: COc1cc2c(cc1C(=O)N[C@H]1CNCC[C@@H]1F)nc(-c1cc3ccc4nc3n1CCCCCCC(C)(C)C(=O)N[C@@H]4C)n2C] | ~{N}-[(3~{S},4~{S})-4-fluoro-3-piperidyl]-6-methoxy-1-methyl-2-[(11~{R})-8,8,11-trimethyl-9-oxo-1,10,19-triazatricyclo[10.5.2.0^{15,18}]nonadeca-12,14,16,18-tetraen-17-yl]benzimidazole-5-carboxamide |
| 593 | 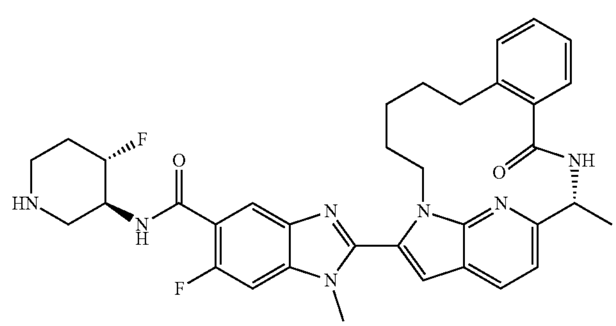 [SMILES: C[C@H]1NC(=O)c2ccccc2CCCCCn2c(-c3nc4cc(C(=O)N[C@H]5CNCC[C@@H]5F)c(F)cc4n3C)cc3ccc1nc32] | 6-fluoro-~{N}-[(3~{S},4~{S})-4-fluoro-3-piperidyl]-1-methyl-2-[(2~{R})-2-methyl-4-oxo-3,16,22-triazatetracyclo[14.5.2.0^{5,10}.0^{19,23}]tricosa-1(21),5(10),6,8,17,19,22-heptaen-17-yl]benzimidazole-5-carboxamide |

TABLE 1A-continued

| Example | Structure | Name |
|---|---|---|
| 594 | 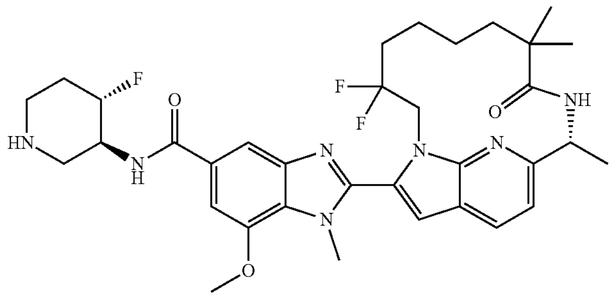 [SMILES: COc1cc(C(=O)N[C@H]2CNCC[C@@H]2F)cc2nc(-c3cc4ccc5nc4n3CC(F)(F)CCCCC(C)(C)C(=O)N[C@@H]5C)n(C)c12] | 2-[(11~{R})-3,3-difluoro-8,8,11-trimethyl-9-oxo-1,10,19-triazatricyclo[10.5.2.0^{15,18}]nonadeca-12,14,16,18-tetraen-17-yl]-~{N}-[(3~{S},4~{S})-4-fluoro-3-piperidyl]-7-methoxy-1-methyl-benzimidazole-5-carboxamide |
| 595 | 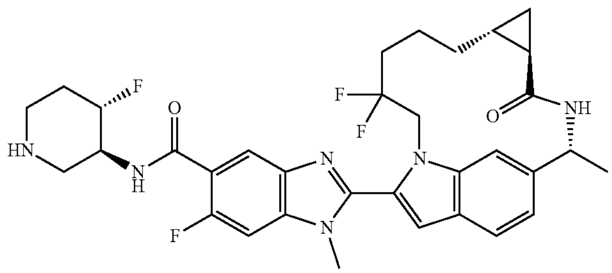 [SMILES: C[C@H]1NC(=O)[C@@H]2C[C@H]2CCCC(F)(F)Cn2c(-c3nc4cc(C(=O)N[C@H]5CNCC[C@@H]5F)c(F)cc4n3C)cc3ccc1cc32] | 2-[(2~{R},5~{R},7~{R})-11,11-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 596 | 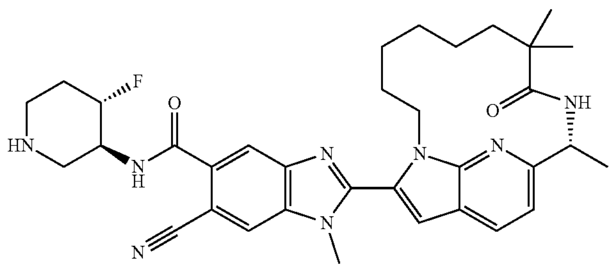 [SMILES: C[C@H]1NC(=O)C(C)(C)CCCCCCn2c(-c3nc4cc(C(=O)N[C@H]5CNCC[C@@H]5F)c(C#N)cc4n3C)cc3ccc1nc32] | 6-cyano-~{N}-[(3~{S},4~{S})-4-fluoro-3-piperidyl]-1-methyl-2-[(11~{R})-8,8,11-trimethyl-9-oxo-1,10,19-triazatricyclo[10.5.2.0^{15,18}]nonadeca-12,14,16,18-tetraen-17-yl]benzimidazole-5-carboxamide |
| 597 | 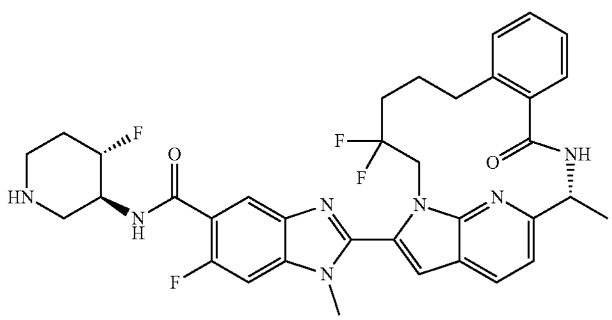 [SMILES: C[C@H]1NC(=O)c2ccccc2CCCC(F)(F)Cn2c(-c3nc4cc(C(=O)N[C@H]5CNCC[C@@H]5F)c(F)cc4n3C)cc3ccc1nc32] | 2-[(2~{R})-14,14-difluoro-2-methyl-4-oxo-3,16,22-triazatetracyclo[14.5.2.0^{5,10}.0^{19,23}]tricosa-1(21),5(10),6,8,17,19,22-heptaen-17-yl]-6-fluoro-~{N}-[(3~{S},4~{S})-4-fluoro-3-piperidyl]-1-methyl-benzimidazole-5-carboxamide |
| 598 | 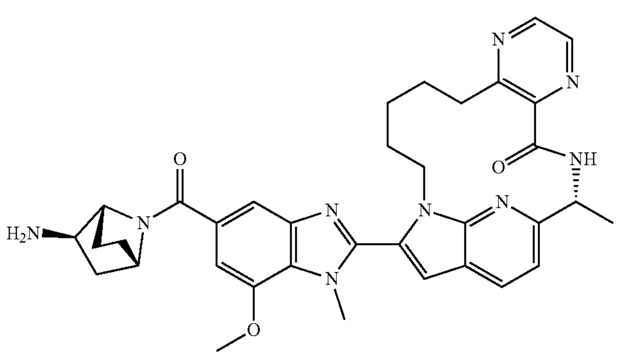 [SMILES: COc1cc(C(=O)N2[C@H]3CC[C@@H]2[C@H](N)C3)cc2nc(-c3cc4ccc5nc4n3CCCCCc3nccnc3C(=O)N[C@@H]5C)n(C)c12] | (2~{R})-17-[5-[(1~{R},2~{R},4~{S})-2-amino-7-azabicyclo[2.2.1]heptane-7-carbonyl]-7-methoxy-1-methyl-benzimidazol-2-yl]-2-methyl-3,6,9,16,22-pentazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 599 | 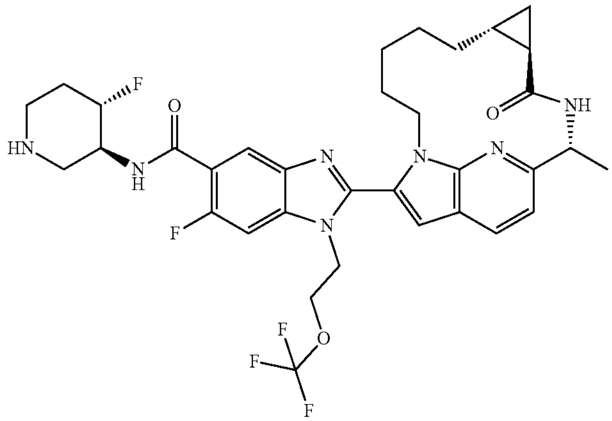 [SMILES: C[C@H]1NC(=O)[C@@H]2C[C@H]2CCCCCn2c(-c3nc4cc(C(=O)N[C@H]5CNCC[C@@H]5F)c(F)cc4n3CCOC(F)(F)F)cc3ccc1nc32] | 6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]-1-[2-(trifluoromethoxy)ethyl]benzimidazole-5-carboxamide |
| 600 | 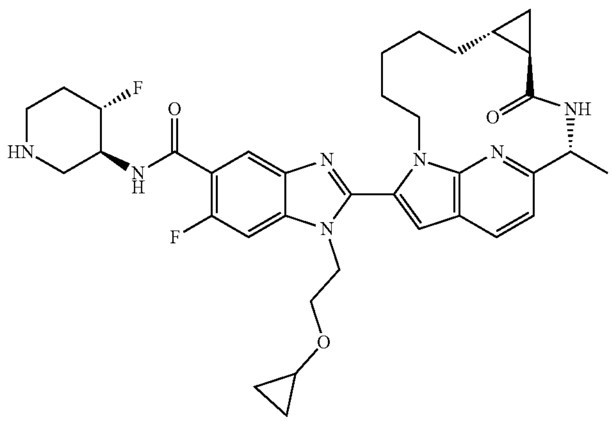 [SMILES: C[C@H]1NC(=O)[C@@H]2C[C@H]2CCCCCn2c(-c3nc4cc(C(=O)N[C@H]5CNCC[C@@H]5F)c(F)cc4n3CCOC3CC3)cc3ccc1nc32] | 1-[2-(cyclopropoxy)ethyl]-6-fluoro-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 601 | 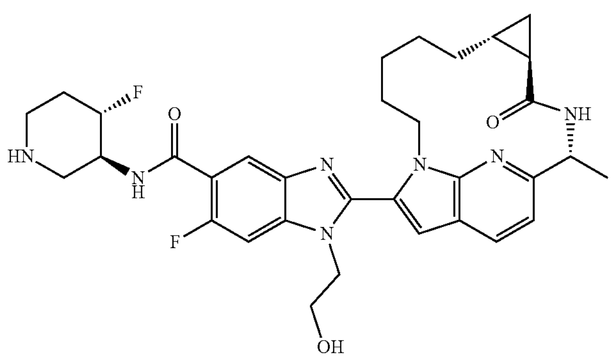 [SMILES: C[C@H]1NC(=O)[C@@H]2C[C@H]2CCCCCn2c(-c3nc4cc(C(=O)N[C@H]5CNCC[C@@H]5F)c(F)cc4n3CCO)cc3ccc1nc32] | 6-fluoro-~{N}-[(3~{S},4~{S})-4-fluoro-3-piperidyl]-1-(2-hydroxyethyl)-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 602 | 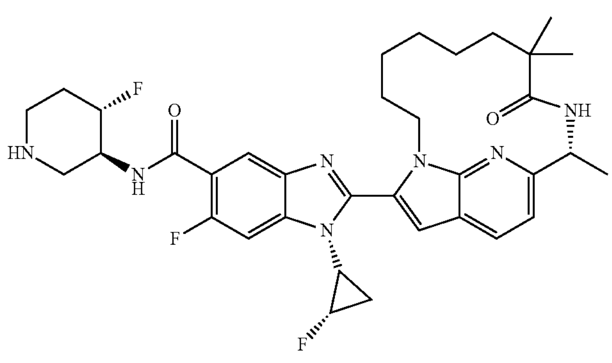 | (1~{R})-6-fluoro-1-[(2~{S})-2-fluorocyclopropyl]-~{N}-[(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12,14,16,18-tetraen-17-yl]benzimidazole-5-carboxamide |

TABLE 1A-continued

| Example | Structure | Name |
|---|---|---|
| 603 | 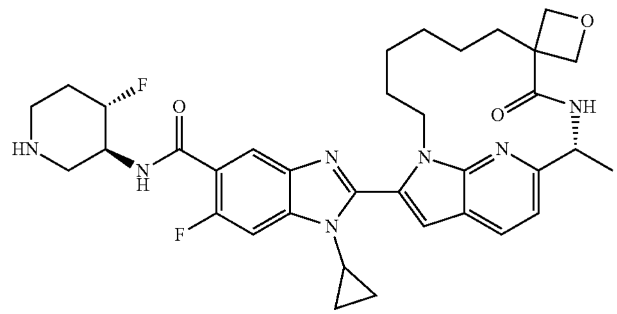 [SMILES: C[C@H]1NC(=O)C2(CCCCCCn3c(-c4nc5cc(C(=O)N[C@H]6CNCC[C@@H]6F)c(F)cc5n4C4CC4)cc4ccc1nc43)COC2] | 1-cyclopropyl-6-fluoro-~{N}-[(3~{S},4~{S})-4-fluoro-3-piperidyl]-2-[(11~{R})-11-methyl-9-oxo-spiro[1,10,19-triazatricyclo[10.5.2.0^{15,18}]nonadeca-12,14,16,18-tetraene-8,3'-oxetane]-17-yl]benzimidazole-5-carboxamide |
| 604 | 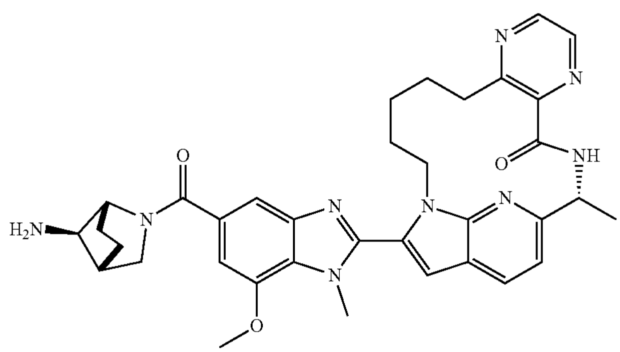 [SMILES: COc1cc(C(=O)N2C[C@H]3CC[C@@H]2[C@@H]3N)cc2nc(-c3cc4ccc5nc4n3CCCCCc3nccnc3C(=O)N[C@@H]5C)n(C)c12] | (2~{R})-17-[5-[(1~{R},4~{R},7~{R})-7-amino-2-azabicyclo[2.2.1]heptane-2-carbonyl]-7-methoxy-1-methyl-benzimidazol-2-yl]-2-methyl-3,6,9,16,22-pentazatetracyclo[14.5.2.0^{5,10}.0^{19,23}]tricosa-1(21),5(10),6,8,17,19,22-heptaen-4-one |
| 606 | 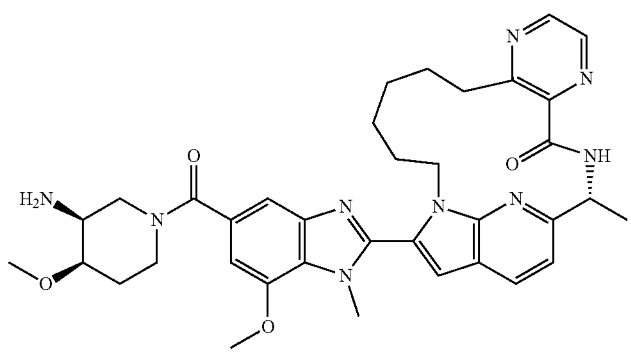 | (2~{R})-18-[5-[(3~{S},4~{R})-3-amino-4-methoxy-piperidine-1-carbonyl]-7-methoxy-1-methyl-benzimidazol-2-yl]-2-methyl-3,6,9,17,23-pentazatetracyclo[15.5.2.0^{5,10}.0^{20,24}]tetracosa-1(23),5(10),6,8,18,20(24),21-heptaen-4-one |
| 607 | 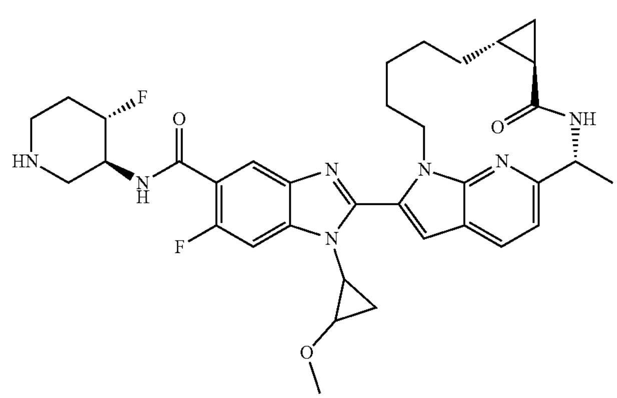 [SMILES: COC1CC1n1c(-c2cc3ccc4nc3n2CCCCC[C@@H]2C[C@H]2C(=O)N[C@@H]4C)nc2cc(C(=O)N[C@H]3CNCC[C@@H]3F)c(F)cc21] | 6-fluoro-~{N}-[(3~{S},4~{S})-4-fluoro-3-piperidyl]-1-(2-methoxycyclopropyl)-2-[(2~{R},5~{R},7~{R})-2-methyl-4-oxo-3,13,19-triazatetracyclo[11.5.2.0^{5,7}.0^{16,20}]icosa-1(18),14,16,19-tetraen-14-yl]benzimidazole-5-carboxamide |

TABLE 1A-continued

| Example | Structure | Name |
|---|---|---|
| 608 | 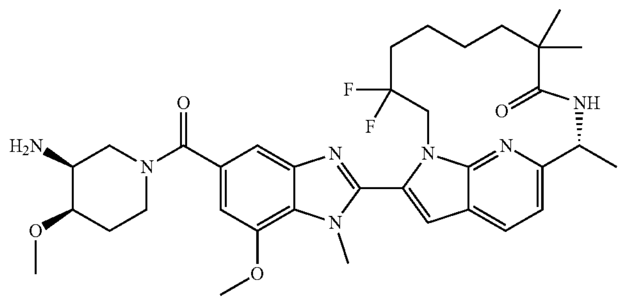 [SMILES: COc1cc(C(=O)N2CC[C@@H](OC)[C@@H](N)C2)cc2nc(-c3cc4ccc5nc4n3CC(F)(F)CCCCC(C)(C)C(=O)N[C@@H]5C)n(C)c12] | (11~{R})-17-[5-[(3~{S},4~{R})-3-amino-4-methoxy-piperidine-1-carbonyl]-7-methoxy-1-methyl-benzimidazol-2-yl]-3,3-difluoro-8,8,11-trimethyl-1,10,19-triazatricyclo[10.5.2.0^{15,18}]nonadeca-12,14,16,18-tetraen-9-one |
| 609 | 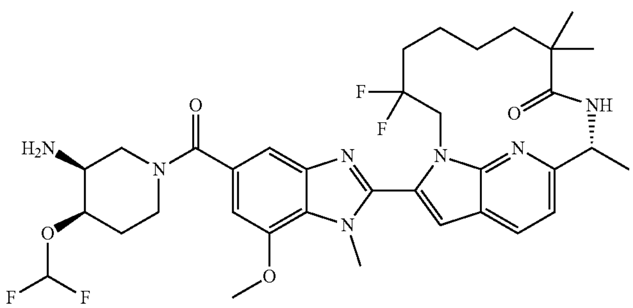 [SMILES: COc1cc(C(=O)N2CC[C@@H](OC(F)F)[C@@H](N)C2)cc2nc(-c3cc4ccc5nc4n3CC(F)(F)CCCCC(C)(C)C(=O)N[C@@H]5C)n(C)c12] | (11~{R})-17-[5-[(3~{S},4~{R})-3-amino-4-(difluoromethoxy)piperidine-1-carbonyl]-7-methoxy-1-methyl-benzimidazol-2-yl]-3,3-difluoro-8,8,11-trimethyl-1,10,19-triazatricyclo[10.5.2.0^{15,18}]nonadeca-12,14,16,18-tetraen-9-one |
| 610 | 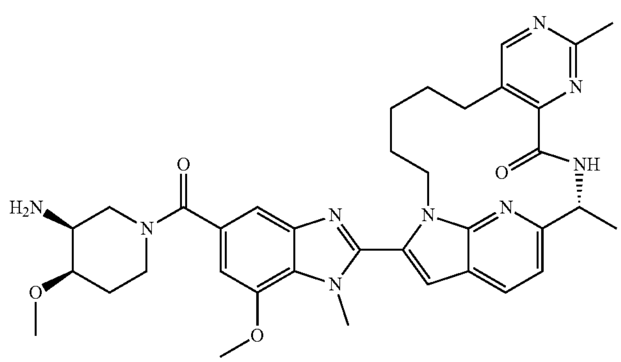 [SMILES: COc1cc(C(=O)N2CC[C@@H](OC)[C@@H](N)C2)cc2nc(-c3cc4ccc5nc4n3CCCCCc3cnc(C)nc3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-2,7-dimethyl-3,6,8,16,22-pentazatetracyclo[14.5.2.0^{5,10}.0^{19,23}]tricosa-1(21),5(10),6,8,17,19,22-heptaen-4-one |
| 611 | 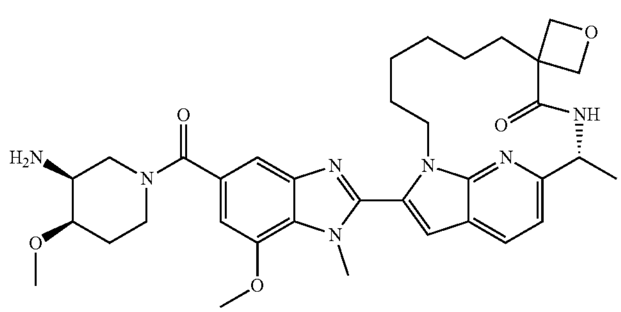 [SMILES: COc1cc(C(=O)N2CC[C@@H](OC)[C@@H](N)C2)cc2nc(-c3cc4ccc5nc4n3CCCCCCC3(COC3)C(=O)N[C@@H]5C)n(C)c12] | (11~{R})-17-[5-[(3~{S},4~{R})-3-amino-4-methoxy-piperidine-1-carbonyl]-7-methoxy-1-methyl-benzimidazol-2-yl]-11-methyl-spiro[1,10,19-triazatricyclo[10.5.2.0^{15,18}]nonadeca-12,14,16,18-tetraene-8,3'-oxetane]-9-one |

TABLE 1A-continued

| Example | Structure | Name |
|---|---|---|
| 612 | 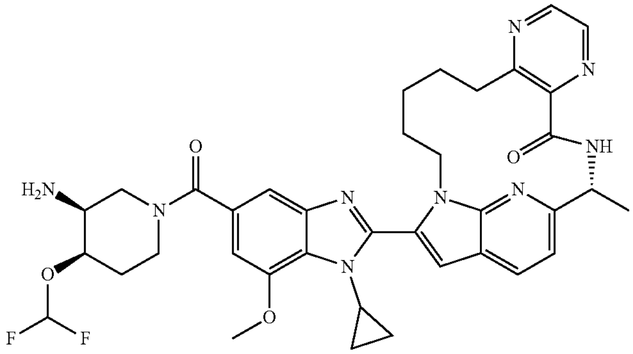 [SMILES: COc1cc(C(=O)N2CC[C@@H](OC(F)F)[C@@H](N)C2)cc2nc(-c3cc4ccc5nc4n3CCCCCc3nccnc3C(=O)N[C@@H]5C)n(C3CC3)c12] | (2~{R})-17-[5-[(3~{S},4~{R})-3-amino-4-(difluoromethoxy)piperidine-1-carbonyl]-1-cyclopropyl-7-methoxy-benzimidazol-2-yl]-2-methyl-3,6,9,16,22-pentazatetracyclo[14.5.2.0^{5,10}.0^{19,23}]tricosa-1(21),5(10),6,8,17,19,22-heptaen-4-one |
| 613 | 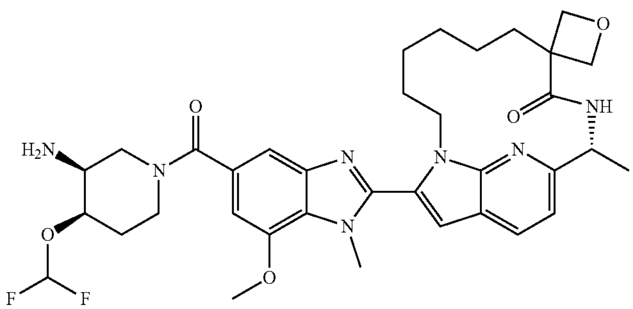 [SMILES: COc1cc(C(=O)N2CC[C@@H](OC(F)F)[C@@H](N)C2)cc2nc(-c3cc4ccc5nc4n3CCCCCCC3(COC3)C(=O)N[C@@H]5C)n(C)c12] | (11~{R})-17-[5-[(3~{S},4~{R})-3-amino-4-(difluoromethoxy)piperidine-1-carbonyl]-7-methoxy-1-methyl-benzimidazol-2-yl]-11-methyl-spiro[1,10,19-triazatricyclo[10.5.2.0^{15,18}]nonadeca-12,14,16,18-tetraene-8,3'-oxetane]-9-one |
| 614 | 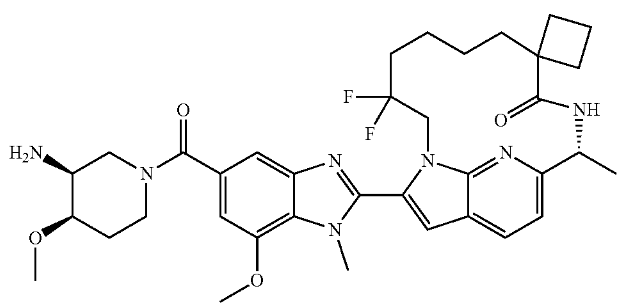 [SMILES: COc1cc(C(=O)N2CC[C@@H](OC)[C@@H](N)C2)cc2nc(-c3cc4ccc5nc4n3CC(F)(F)CCCCC3(CCC3)C(=O)N[C@@H]5C)n(C)c12] | (11~{R})-17-[5-[(3~{S},4~{R})-3-amino-4-methoxy-piperidine-1-carbonyl]-7-methoxy-1-methyl-benzimidazol-2-yl]-3,3-difluoro-11-methyl-spiro[1,10,19-triazatricyclo[10.5.2.0^{15,18}]nonadeca-12,14,16,18-tetraene-8,1'-cyclobutane]-9-one |
| 615 | 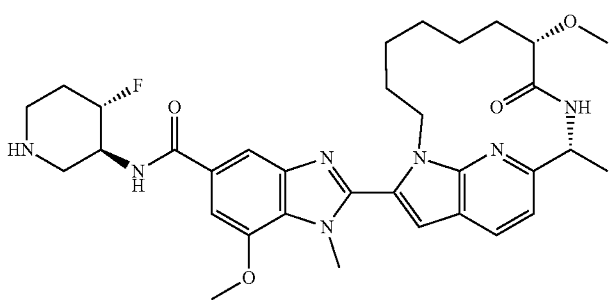 [SMILES: COc1cc(C(=O)N[C@H]2CNCC[C@@H]2F)cc2nc(-c3cc4ccc5nc4n3CCCCCC[C@H](OC)C(=O)N[C@@H]5C)n(C)c12] | ~{N}-[(3~{S},4~{S})-4-fluoro-3-piperidyl]-7-methoxy-2-[(8~{S},11~{R})-8-methoxy-11-methyl-9-oxo-1,10,19-triazatricyclo[10.5.2.0^{15,18}]nonadeca-12(19),13,15(18),16-tetraen-17-yl]-1-methyl-benzimidazole-5-carboxamide |
| 616 | 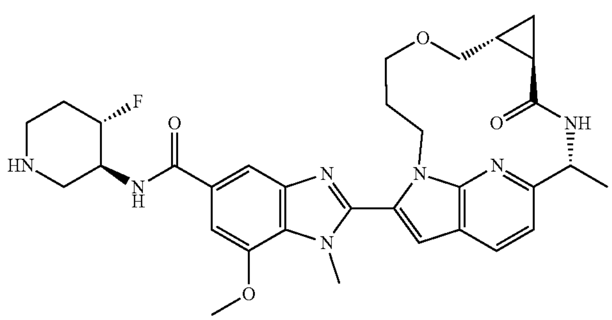 [SMILES: COc1cc(C(=O)N[C@H]2CNCC[C@@H]2F)cc2nc(-c3cc4ccc5nc4n3CCCOC[C@@H]3C[C@H]3C(=O)N[C@@H]5C)n(C)c12] | ~{N}-[(3~{S},4~{S})-4-fluoro-3-piperidyl]-7-methoxy-1-methyl-2-[(2~{R},5~{R},7~{R})-2-methyl-4-oxo-9-oxa-3,13,19-triazatetracyclo[11.5.2.0^{5,7}.0^{16,20}]icosa-1(19),14,16(20),17-tetraen-14-yl]benzimidazole-5-carboxamide |

TABLE 1A-continued

| Example | Structure | Name |
|---|---|---|
| 617 | 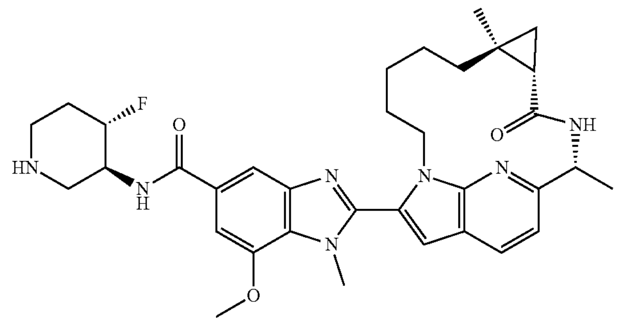 [SMILES: COc1cc(C(=O)N[C@H]2CNCC[C@@H]2F)cc2nc(-c3cc4ccc5nc4n3CCCCC[C@@]3(C)C[C@@H]3C(=O)N[C@@H]5C)n(C)c12] | 2-[(2~{R},5~{S},7~{S})-2,7-dimethyl-4-oxo-3,13,19-triazatetracyclo[11.5.2.0^{5,7}.0^{16,20}]icosa-1(19),14,16(20),17-tetraen-14-yl]-~{N}-[(3~{S},4~{S})-4-fluoro-3-piperidyl]-7-methoxy-1-methyl-benzimidazole-5-carboxamide |
| 618 | 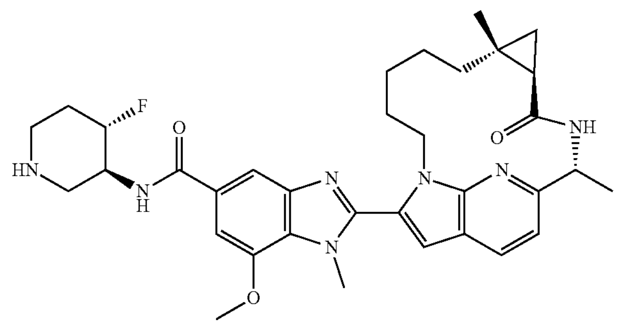 [SMILES: COc1cc(C(=O)N[C@H]2CNCC[C@@H]2F)cc2nc(-c3cc4ccc5nc4n3CCCCC[C@]3(C)C[C@H]3C(=O)N[C@@H]5C)n(C)c12] | 2-[(2~{R},5~{R},7~{R})-2,7-dimethyl-4-oxo-3,13,19-triazatetracyclo[11.5.2.0^{5,7}.0^{16,20}]]icosa-1(19),14,16(20),17-tetraen-14-yl]-~{N}-[(3~{S},4~{S})-4-fluoro-3-piperidyl]-7-methoxy-1-methyl-benzimidazole-5-carboxamide |
| 619 | 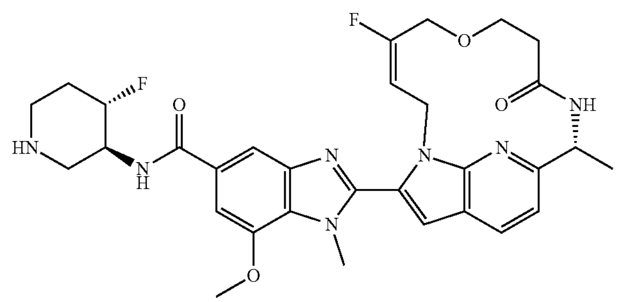 [SMILES: COc1cc(C(=O)N[C@H]2CNCC[C@@H]2F)cc2nc(-c3cc4ccc5nc4n3C/C=C(/F)COCCC(=O)N[C@@H]5C)n(C)c12] | 2-[(3~{E},11~{R})-4-fluoro-11-methyl-9-oxo-6-oxa-1,10,19-triazatricyclo[10.5.2.0^{15,18}]nonadeca-3,12(19),13,15(18),16-pentaen-17-yl]-~{N}-[(3~{S},4~{S})-4-fluoro-3-piperidyl]-7-methoxy-1-methyl-benzimidazole-5-carboxamide |
| 620 | 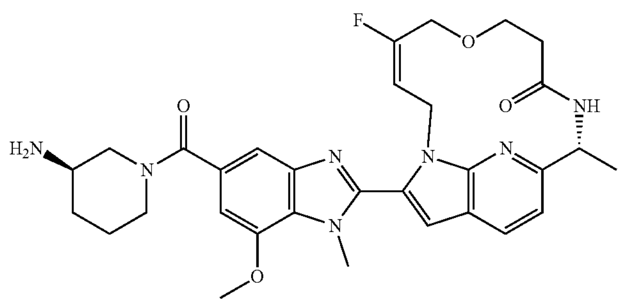 [SMILES: COc1cc(C(=O)N2CCC[C@@H](N)C2)cc2nc(-c3cc4ccc5nc4n3C/C=C(/F)COCCC(=O)N[C@@H]5C)n(C)c12] | (3~{E},11~{R})-17-[5-[(3~{R})-3-aminopiperidine-1-carbonyl]-7-methoxy-1-methyl-benzimidazol-2-yl]-4-fluoro-11-methyl-6-oxa-1,10,19-triazatricyclo[10.5.2.0^{15,18}]nonadeca-3,12(19),13,15(18),16-pentaen-9-one |
| 621 | 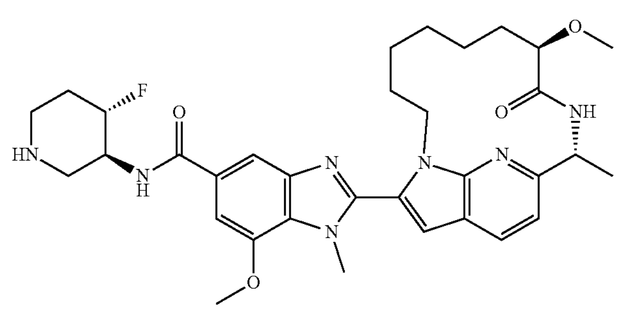 [SMILES: COc1cc(C(=O)N[C@H]2CNCC[C@@H]2F)cc2nc(-c3cc4ccc5nc4n3CCCCCC[C@@H](OC)C(=O)N[C@@H]5C)n(C)c12] | ~{N}-[(3~{S},4~{S})-4-fluoro-3-piperidyl]-7-methoxy-2-[(8~{R},11~{R})-8-methoxy-11-methyl-9-oxo-1,10,19-triazatricyclo[10.5.2.0^{15,18}]nonadeca-12(19),13,15(18),16-tetraen-17-yl]-1-methyl-benzimidazole-5-carboxamide |

TABLE 1A-continued

| Example | Structure | Name |
|---|---|---|
| 622 | 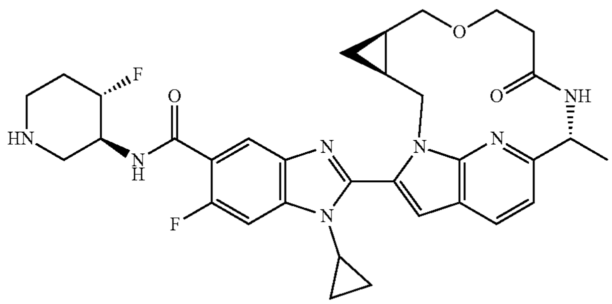 [SMILES: C[C@H]1NC(=O)CCOC[C@@H]2C[C@@H]2Cn2c(-c3nc4cc(C(=O)N[C@H]5CNCC[C@@H]5F)c(F)cc4n3C3CC3)cc3ccc1nc32] | 1-cyclopropyl-6-fluoro-~{N}-[(3~{S},4~{S})-4-fluoro-3-piperidyl]-2-[(3~{S},5~{R},12~{R})-12-methyl-10-oxo-7-oxa-1,11,20-triazatetracyclo[11.5.2.0^{3,5}.0^{16,19}]icosa-13(20),14,16(19),17-tetraen-18-yl]benzimidazole-5-carboxamide |
| 623 | 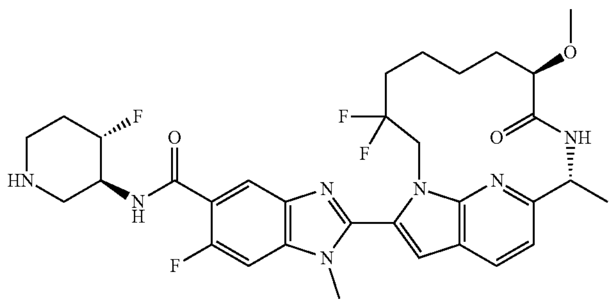 [SMILES: CO[C@@H]1CCCCC(F)(F)Cn2c(-c3nc4cc(C(=O)N[C@H]5CNCC[C@@H]5F)c(F)cc4n3C)cc3ccc(nc32)[C@@H](C)NC1=O] | 2-[(8~{R},11~{R})-3,3-difluoro-8-methoxy-11-methyl-9-oxo-1,10,19-triazatricyclo[10.5.2.0^{15,18}]nonadeca-12(19),13,15(18),16-tetraen-17-yl]-6-fluoro-~{N}-[(3~{S},4~{S})-4-fluoro-3-piperidyl]-1-methyl-benzimidazole-5-carboxamide |
| 624 | 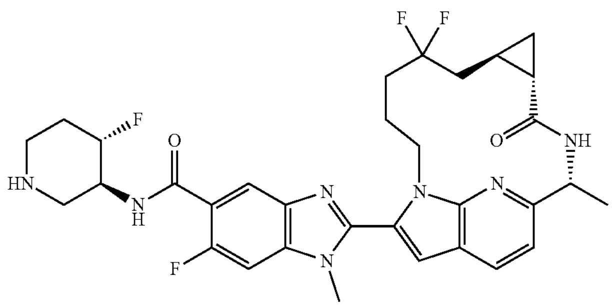 [SMILES: C[C@H]1NC(=O)[C@H]2C[C@@H]2CC(F)(F)CCCn2c(-c3nc4cc(C(=O)N[C@H]5CNCC[C@@H]5F)c(F)cc4n3C)cc3ccc1nc32] | 2-[(2~{R},5~{S},7~{R})-9,9-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 625 | 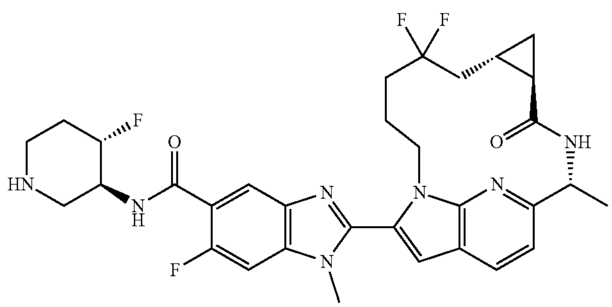 [SMILES: C[C@H]1NC(=O)[C@@H]2C[C@H]2CC(F)(F)CCCn2c(-c3nc4cc(C(=O)N[C@H]5CNCC[C@@H]5F)c(F)cc4n3C)cc3ccc1nc32] | 2-[(2~{R},5~{R},7~{S})-9,9-difluoro-2-methyl-4-oxo-3,13,19-triazatetracyclo[11.5.2.0^{5,7}.0^{16,20}]icosa-1(19),14,16(20),17-tetraen-14-yl]-6-fluoro-~{N}-[(3~{S},4~{S})-4-fluoro-3-piperidyl]-1-methyl-benzimidazole-5-carboxamide |
| 626 | 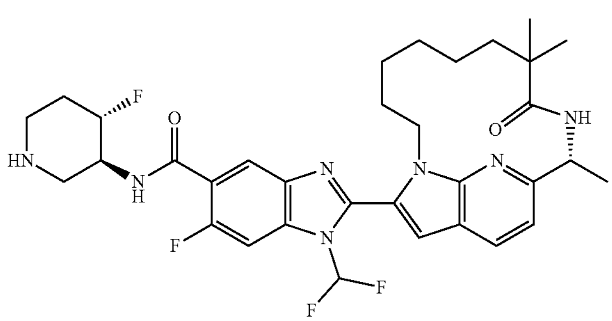 [SMILES: C[C@H]1NC(=O)C(C)(C)CCCCCCn2c(-c3nc4cc(C(=O)N[C@H]5CNCC[C@@H]5F)c(F)cc4n3C(F)F)cc3ccc1nc32] | [(3~{S},4~{S})-4-fluoro-3-piperidyl]-2-[(11~{R})-8,8,11-trimethyl-9-oxo-1,10,19-triazatricyclo[10.5.2.0^{15,18}]nonadeca-12(19),13,15(18),16-tetraen-17-yl]benzimidazole-5-carboxamide |

TABLE 1A-continued

| Example | Structure | Name |
|---|---|---|
| 627 | 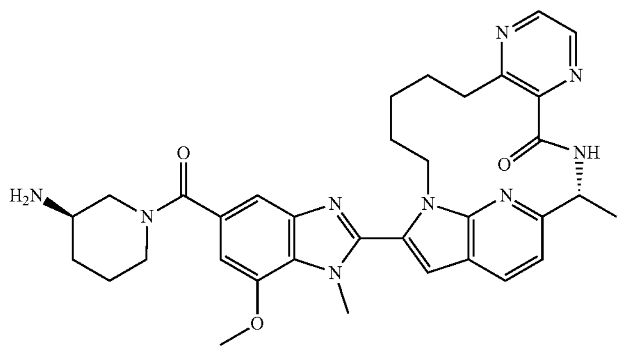 [SMILES: COc1cc(C(=O)N2CCC[C@@H](N)C2)cc2nc(-c3cc4ccc5nc4n3CCCCCc3nccnc3C(=O)N[C@@H]5C)n(C)c12] | (2~{R})-17-[5-[(3~{R})-3-aminopiperidine-1-carbonyl]-7-methoxy-1-methyl-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 628 | 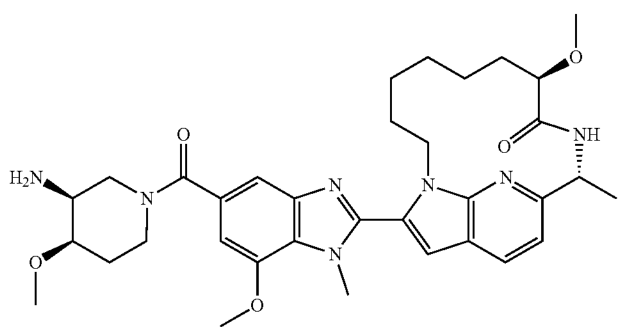 [SMILES: COc1cc(C(=O)N2CC[C@@H](OC)[C@@H](N)C2)cc2nc(-c3cc4ccc5nc4n3CCCCCC[C@@H](OC)C(=O)N[C@@H]5C)n(C)c12] | (8~{R},11~{R})-17-[5-[(3~{S},4~{R})-3-amino-4-methoxy-piperidine-1-carbonyl]-7-methoxy-1-methyl-benzimidazol-2-yl]-8-methoxy-11-methyl-1,10,19-triazatricyclo[10.5.2.0^{15,18}]nonadeca-12(19),13,15(18),16-tetraen-9-one |
| 629 | 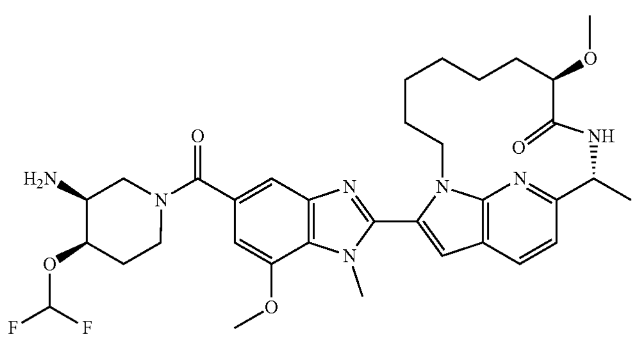 [SMILES: COc1cc(C(=O)N2CC[C@@H](OC(F)F)[C@@H](N)C2)cc2nc(-c3cc4ccc5nc4n3CCCCCC[C@@H](OC)C(=O)N[C@@H]5C)n(C)c12] | (8~{R},11~{R})-17-[5-[(3~{S},4~{R})-3-amino-4-(difluoromethoxy)piperidine-1-carbonyl]-7-methoxy-1-methyl-benzimidazol-2-yl]-8-methoxy-11-methyl-1,10,19-triazatricyclo[10.5.2.0^{15,18}]nonadeca-12(19),13,15(18),16-tetraen-9-one |
| 630 | 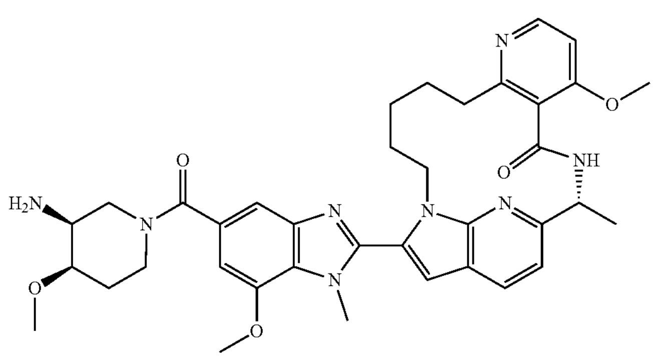 [SMILES: COc1ccnc2c1C(=O)N[C@H](C)c1ccc3cc(-c4nc5cc(C(=O)N6CC[C@@H](OC)[C@@H](N)C6)cc(OC)c5n4C)n(c3n1)CCCCC2] | (2~{R})-17-[5-[(3~{S},4~{R})-3-amino-4-methoxy-piperidine-1-carbonyl]-7-methoxy-1-methyl-benzimidazol-2-yl]-6-methoxy-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 631 | 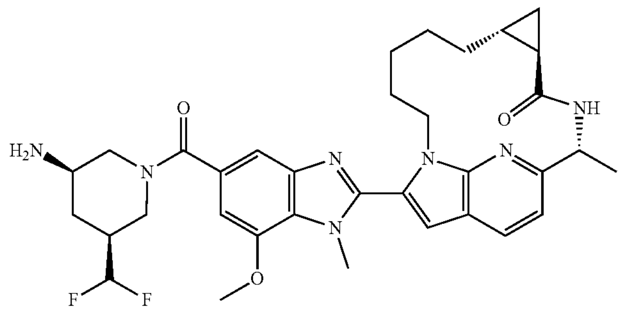 [SMILES: COc1cc(C(=O)N2C[C@H](N)C[C@H](C(F)F)C2)cc2nc(-c3cc4ccc5nc4n3CCCCC[C@@H]3C[C@H]3C(=O)N[C@@H]5C)n(C)c12] | (2~{R},5~{R},7~{R})-14-[5-[(3~{R},5~{S})-3-amino-5-(difluoromethyl)piperidine-1-carbonyl]-7-methoxy-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 632 | 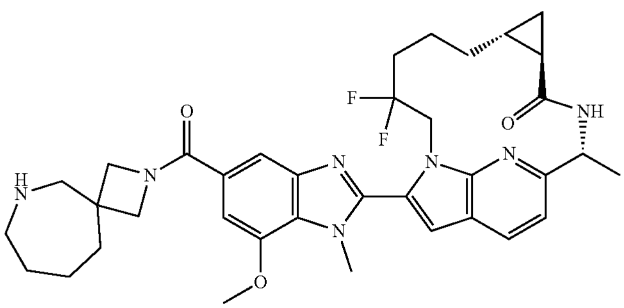 [SMILES: COc1cc(C(=O)N2CC3(CCCCNC3)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-(2,9-diazaspiro[3.6]decane-2-carbonyl)-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 633 | 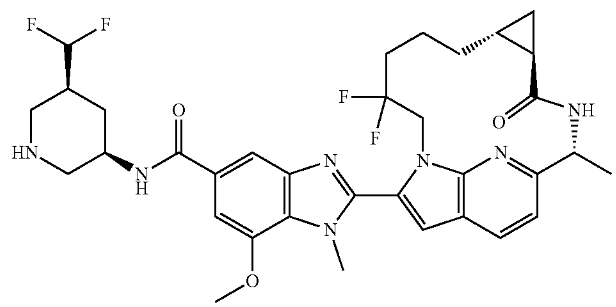 [SMILES: COc1cc(C(=O)N[C@H]2CNC[C@@H](C(F)F)C2)cc2nc(-c3cc4ccc5nc4n3CC(F)(F)CCC[C@@H]3C[C@H]3C(=O)N[C@@H]5C)n(C)c12] | 2-[(2~{R},5~{R},7~{R})-11,11-difluoro-2-methyl-4-oxo-3,13,19-triazatetracyclo[11.5.2.0^{5,7}.0^{16,20}]icosa-1(19),14,16(20),17-tetraen-14-yl]-~{N}-[(3~{R},5~{S})-5-(difluoromethyl)-3-piperidyl]-7-methoxy-1-methyl-benzimidazole-5-carboxamide |
| 634 | 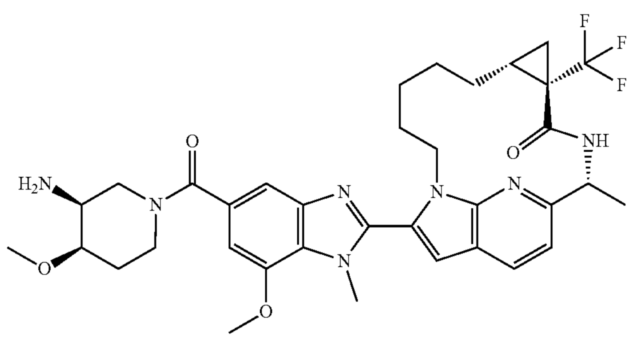 | (2~{R},5~{S},7~{R})-14-[5-[(3~{S},4~{R})-3-amino-4-methoxy-piperidine-1-carbonyl]-7-methoxy-1-methyl-benzimidazol-2-yl]-2-methyl-5-(trifluoromethyl)-3,13,19-triazatetracyclo[11.5.2.0^{5,7}.0^{16,20}]icosa-1(19),14,16(20),17-tetraen-4-one |
| 635 | 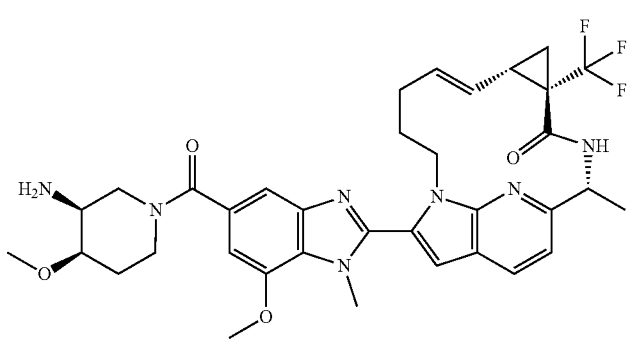 | (2~{R},5~{S},7~{S},8~{E})-14-[5-[(3~{S},4~{R})-3-amino-4-methoxy-piperidine-1-carbonyl]-7-methoxy-1-methyl-benzimidazol-2-yl]-2-methyl-5-(trifluoromethyl)-3,13,19-triazatetracyclo[11.5.2.0^{5,7}.0^{16,20}]icosa-1(19),8,14,16(20),17-pentaen-4-one |

TABLE 1A-continued

| Example | Structure | Name |
|---|---|---|
| 636 | 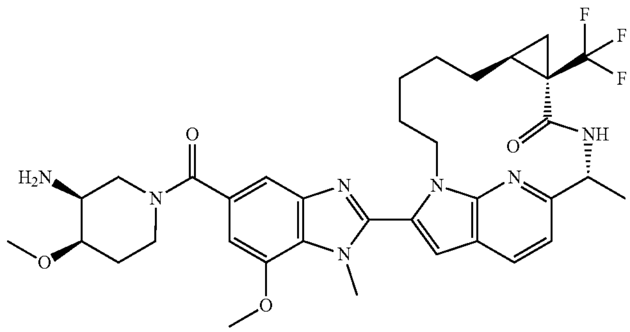 | (2~{R},5~{R},7~{S})-14-[5-[(3~{S},4~{R})-3-amino-4-methoxy-piperidine-1-carbonyl]-7-methoxy-1-methyl-benzimidazol-2-yl]-2-methyl-5-(trifluoromethyl)-3,13,19-triazatetracyclo[11.5.2.0^{5,7}.0^{16,20}]icosa-1(19),14,16(20),17-tetraen-4-one |
| 637 | 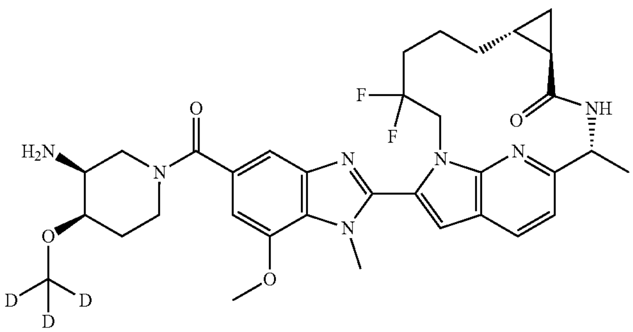 [SMILES: [2H]C([2H])([2H])O[C@@H]1CCN(C(=O)c2cc(OC)c3c(c2)nc(-c2cc4ccc5nc4n2CC(F)(F)CCC[C@@H]2C[C@H]2C(=O)N[C@@H]5C)n3C)C[C@@H]1N] | (2~{R},5~{R},7~{R})-14-[5-[(3~{S},4~{R})-3-amino-4-(trideuteriomethoxy)piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 638 | 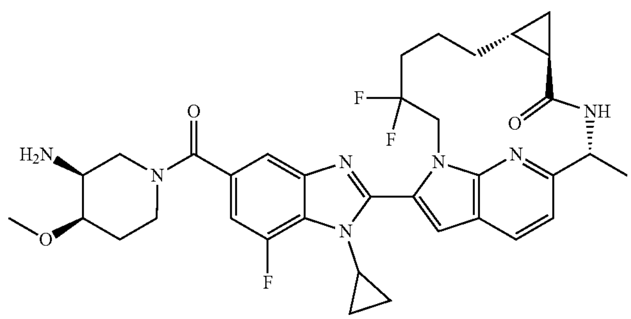 | (2~{R},5~{R},7~{R})-14-[5-[(3~{S},4~{R})-3-amino-4-methoxy-piperidine-1-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 639 | 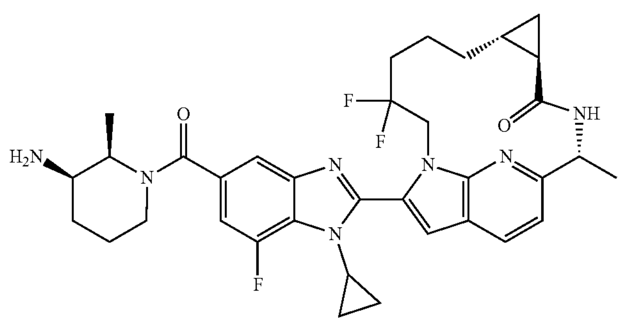 [SMILES: C[C@@H]1[C@H](N)CCCN1C(=O)c1cc(F)c2c(c1)nc(-c1cc3ccc4nc3n1CC(F)(F)CCC[C@@H]1C[C@H]1C(=O)N[C@@H]4C)n2C1CC1] | (2~{R},5~{R},7~{R})-14-[5-[(2~{R},3~{R})-3-amino-2-methyl-piperidine-1-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 640 | 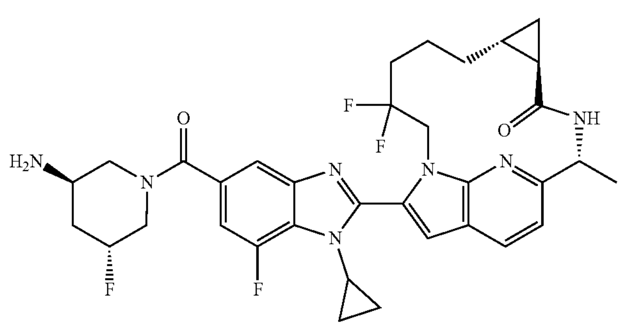 [SMILES: C[C@H]1NC(=O)[C@@H]2C[C@H]2CCCC(F)(F)Cn2c(-c3nc4cc(C(=O)N5C[C@H](N)C[C@@H](F)C5)cc(F)c4n3C3CC3)cc3ccc1nc32] | (2~{R},5~{R},7~{R})-14-[5-[(3~{R},5~{R})-3-amino-5-fluoro-piperidine-1-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 641 | 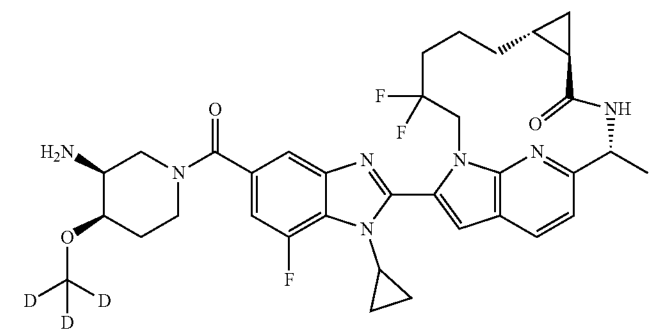 [SMILES: [2H]C([2H])([2H])O[C@@H]1CCN(C(=O)c2cc(F)c3c(c2)nc(-c2cc4ccc5nc4n2CC(F)(F)CCC[C@@H]2C[C@H]2C(=O)N[C@@H]5C)n3C2CC2)C[C@@H]1N] | (2~{R},5~{R},7~{R})-14-[5-[(3~{S},4~{R})-3-amino-4-(trideuteriomethoxy)piperidine-1-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 642 | 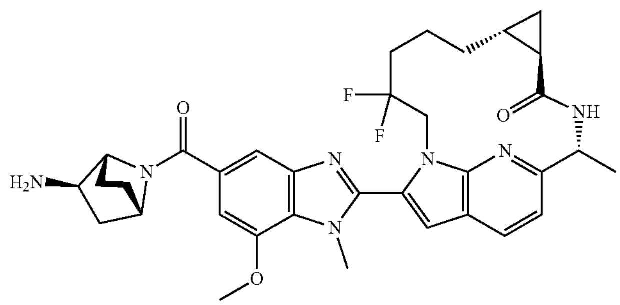 | (2~{R},5~{R},7~{R})-14-[5-[(1~{R},2~{R},4~{S})-2-amino-7-azabicyclo[2.2.1]heptane-7-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 643 | 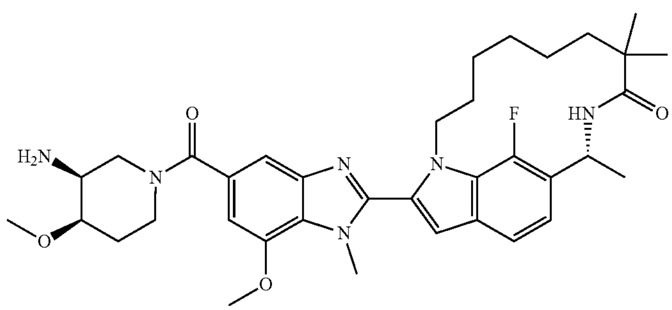 | (11~{R})-17-[5-[(3~{S},4~{R})-3-amino-4-methoxy-piperidine-1-carbonyl]-7-methoxy-1-methyl-benzimidazol-2-yl]-19-fluoro-8,8,11-trimethyl-1,10-diazatricyclo[10.5.2.0^{15,18}]nonadeca-12(19),13,15(18),16-tetraen-9-one |
| 644 | 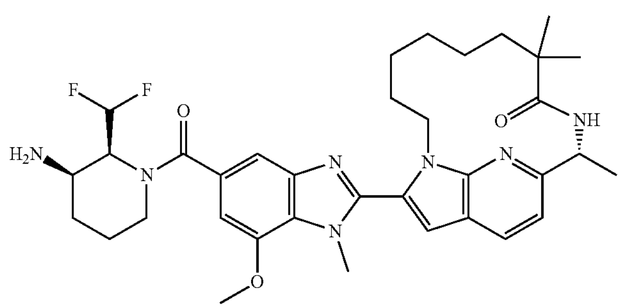 [SMILES: COc1cc(C(=O)N2CCC[C@@H](N)[C@H]2C(F)F)cc2nc(-c3cc4ccc5nc4n3CCCCCCC(C)(C)C(=O)N[C@@H]5C)n(C)c12] | (11~{R})-17-[5-[(2~{S},3~{R})-3-amino-2-(difluoromethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 645 | 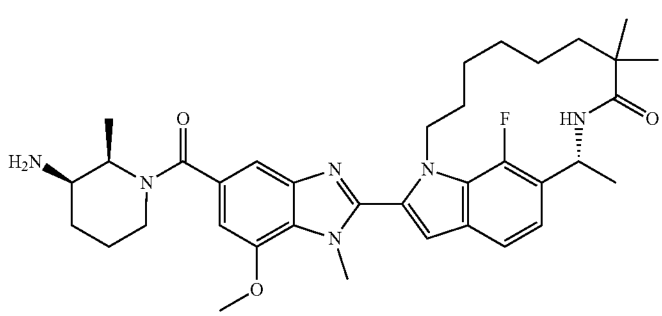 [SMILES: COc1cc(C(=O)N2CCC[C@@H](N)[C@H]2C)cc2nc(-c3cc4ccc5c(F)c4n3CCCCCCC(C)(C)C(=O)N[C@@H]5C)n(C)c12] | (11~{R})-17-[5-[(2~{R},3~{R})-3-amino-2-methyl-piperidine-1-carbonyl]-7-methoxy-1-methyl-benzimidazol-2-yl]-19-fluoro-8,8,11-trimethyl-1,10-diazatricyclo[10.5.2.0^{15,18}]nonadeca-12(19),13,15(18),16-tetraen-9-one |

TABLE 1A-continued

| Example | Structure | Name |
|---|---|---|
| 646 | 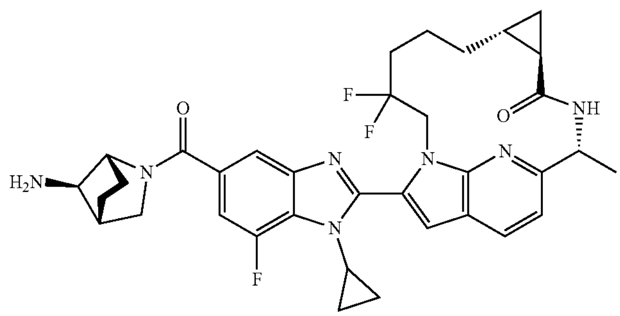 | (2~{R},5~{R},7~{R})-14-[5-[(1~{R},4~{R},7~{R})-7-amino-2-azabicyclo[2.2.1]heptane-2-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 647 | 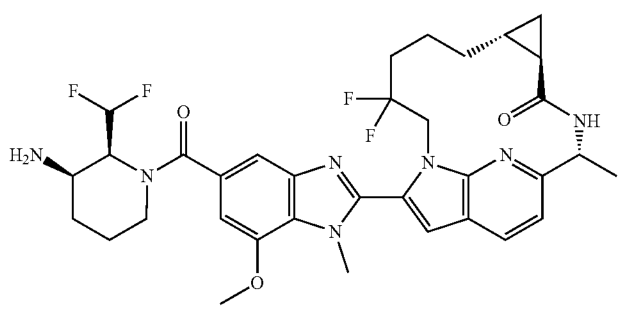 [SMILES: COc1cc(C(=O)N2CCC[C@@H](N)[C@H]2C(F)F)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(2~{S},3~{R})-3-amino-2-(difluoromethyl)piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 648 | 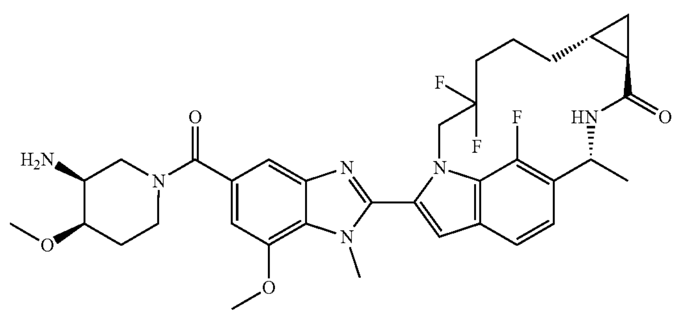 [SMILES: COc1cc(C(=O)N2CC[C@@H](OC)[C@@H](N)C2)cc2nc(-c3cc4ccc5c(F)c4n3CC(F)(F)CCC[C@@H]3C[C@H]3C(=O)N[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-11,11,19-trifluoro-2-methyl-3,13-diazatetracyclo[11.5.2.0^{5,7}.0^{16,20}]icosa-1(19),14,16(20),17-tetraen-4-one |
| 649 | 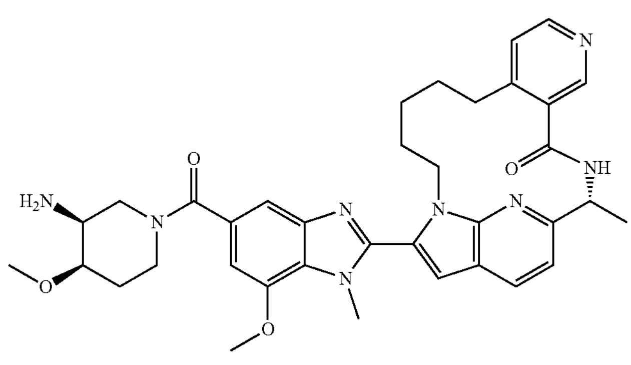 | (2~{R})-17-[5-[(3~{S},4~{R})-3-amino-4-methoxy-piperidine-1-carbonyl]-7-methoxy-1-methyl-benzimidazol-2-yl]-2-methyl-3,7,16,22-tetrazatetracyclo[14.5.2.0^{5,10}.0^{19,23}]tricosa-1(22),5,7,9,17,19(23),20-heptaen-4-one |

TABLE 1A-continued

| Example | Structure | Name |
|---|---|---|
| 650 | 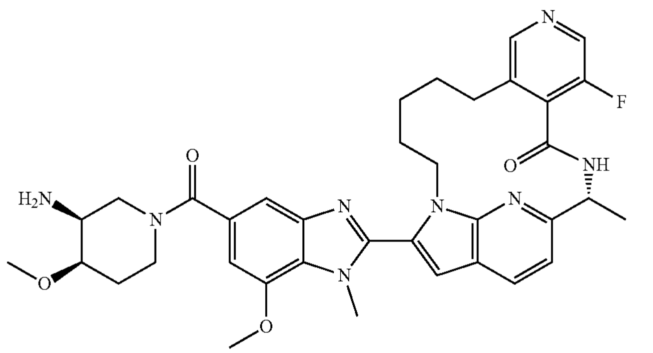 | (2~{R})-17-[5-[(3~{S},4~{R})-3-amino-4-methoxy-piperidine-1-carbonyl]-7-methoxy-1-methyl-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |
| 651 | 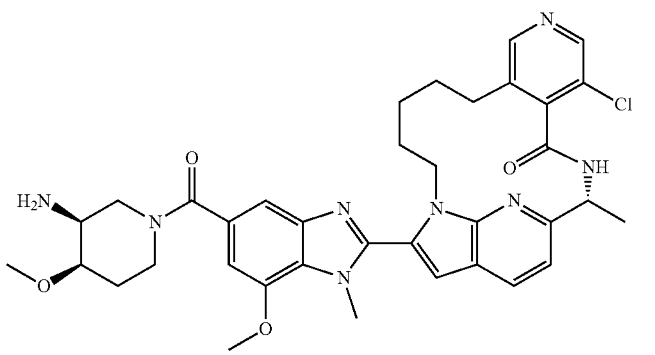 | (2~{R})-17-[5-[(3~{S},4~{R})-3-amino-4-methoxy-piperidine-1-carbonyl]-7-methoxy-1-methyl-benzimidazol-2-yl]-6-chloro-2-methyl-3,8,16,22-tetrazatetracyclo[14.5.2.0^{5,10}.0^{19,23}]tricosa-1(22),5,7,9,17,19(23),20-heptaen-4-one |
| 652 | 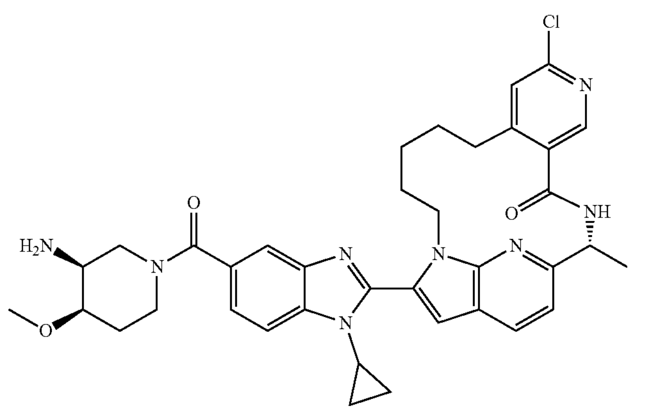 | 17-[5-[(3~{S},4~{R})-3-amino-4-methoxy-piperidine-1-carbonyl]-1-cyclopropyl-benzimidazol-2-yl]-8-chloro-2-methyl-3,7,16,22-tetrazatetracyclo[14.5.2.0^{5,10}.0^{19,23}]tricosa-1(22),5,7,9,17,19(23),20-heptaen-4-one |
| 653 | 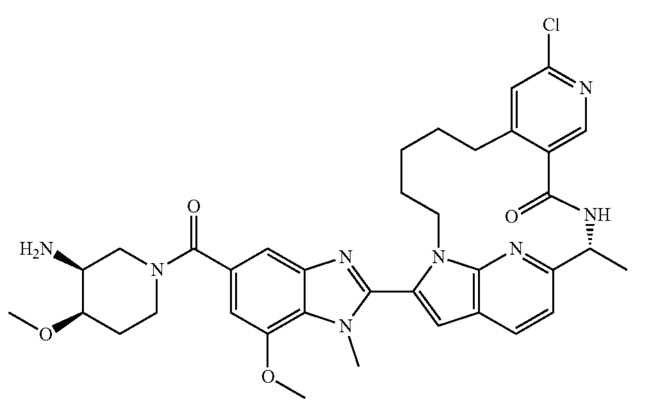 | 17-[5-[(3~{S},4~{R})-3-amino-4-methoxy-piperidine-1-carbonyl]-7-methoxy-1-methyl-benzimidazol-2-yl]-8-chloro-2-methyl-3,7,16,22-tetrazatetracyclo[14.5.2.0^{5,10}.0^{19,23}]tricosa-1(22),5,7,9,17,19(23),20-heptaen-4-one |

TABLE 1A-continued

| Example | Structure | Name |
|---|---|---|
| 654 | 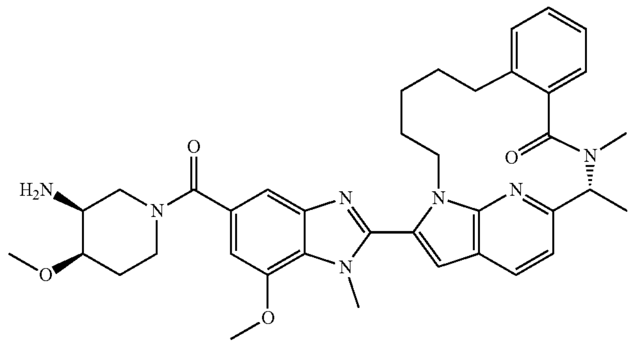 | (2~{R})-17-[5-[(3~{S},4~{R})-3-amino-4-methoxy-piperidine-1-carbonyl]-7-methoxy-1-methyl-benzimidazol-2-yl]-2,3-dimethyl-3,16,22-triazatetracyclo[14.5.2.0^{5,10}.0^{19,23}]tricosa-1(22),5,7,9,17,19(23),20-heptaen-4-one |
| 655 | 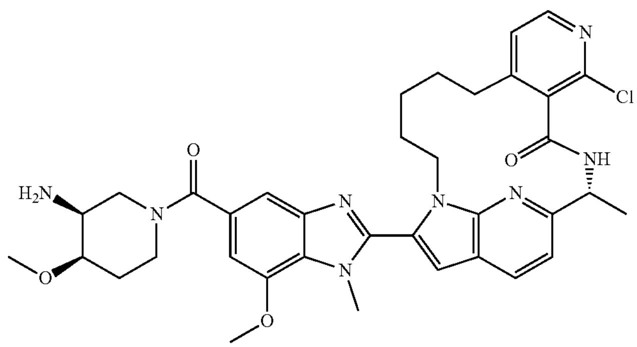 | (2~{R})-17-[5-[(3~{S},4~{R})-3-amino-4-methoxy-piperidine-1-carbonyl]-7-methoxy-1-methyl-benzimidazol-2-yl]-6-chloro-2-methyl-3,7,16,22-tetrazatetracyclo[14.5.2.0^{5,10}.0^{19,23}]tricosa-1(22),5,7,9,17,19(23),20-heptaen-one |
| 656 | 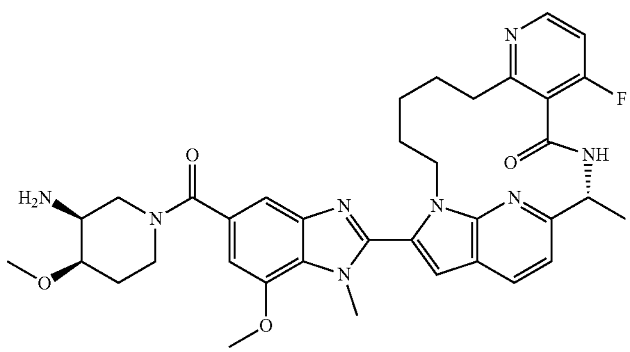 | (2~{R})-17-[5-[(3~{S},4~{R})-3-amino-4-methoxy-piperidine-1-carbonyl]-7-methoxy-1-methyl-benzimidazol-2-yl]-6-fluoro-2-methyl-3,9,16,22-tetrazatetracyclo[14.5.2.0^{5,10}.0^{19,23}]tricosa-1(22),5,7,9,17,19(23),20-heptaen-4-one |
| 657 | 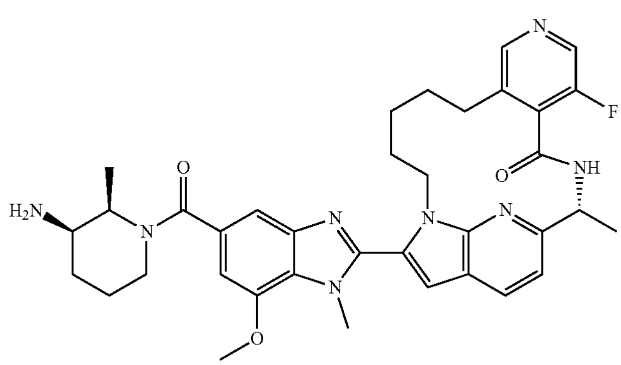 [SMILES: COc1cc(C(=O)N2CCC[C@@H](N)[C@H]2C)cc2nc(-c3cc4ccc5nc4n3CCCCCc3cncc(F)c3C(=O)N[C@@H]5C)n(C)c12] | (2~{R})-17-[5-[(2~{R},3~{R})-3-amino-2-methyl-piperidine-1-carbonyl]-7-methoxy-1-methyl-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |

TABLE 1A-continued

| Example | Structure | Name |
|---|---|---|
| 658 | 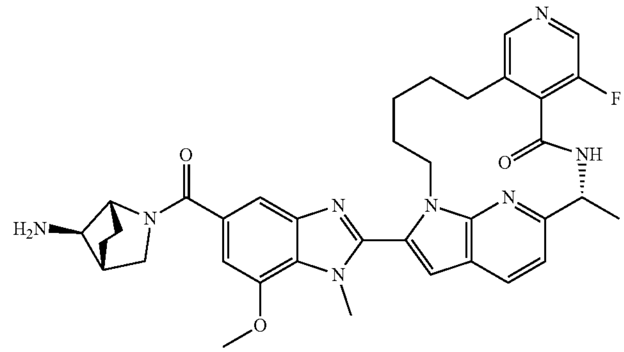 [SMILES: COc1cc(C(=O)N2C[C@H]3CC[C@@H]2[C@@H]3N)cc2nc(-c3cc4ccc5nc4n3CCCCCc3cncc(F)c3C(=O)N[C@@H]5C)n(C)c12] | (2~{R})-17-[5-[(1~{R},4~{R},7~{R})-7-amino-2-azabicyclo[2.2.1]heptane-2-carbonyl]-7-methoxy-1-methyl-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |
| 659 | 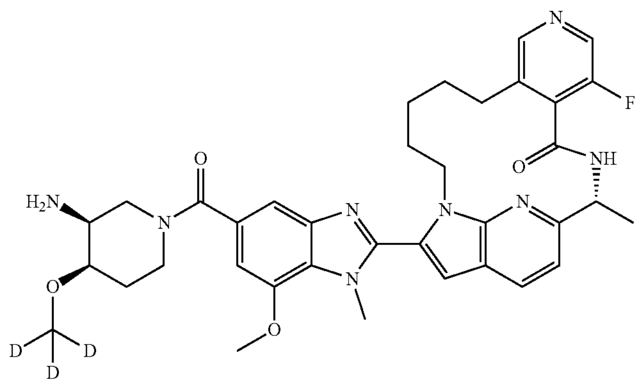 [SMILES: [2H]C([2H])([2H])O[C@@H]1CCN(C(=O)c2cc(OC)c3c(c2)nc(-c2cc4ccc5nc4n2CCCCCc2cncc(F)c2C(=O)N[C@@H]5C)n3C)C[C@@H]1N] | (2~{R})-17-[5-[(3~{S},4~{R})-3-amino-4-(trideuteriomethoxy)piperidine-1-carbonyl]-7-methoxy-1-methyl-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |
| 660 | 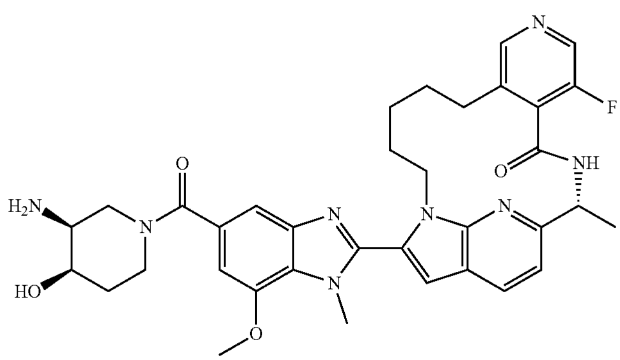 [SMILES: COc1cc(C(=O)N2CC[C@@H](O)[C@@H](N)C2)cc2nc(-c3cc4ccc5nc4n3CCCCCc3cncc(F)c3C(=O)N[C@@H]5C)n(C)c12] | (2~{R})-17-[5-[(3~{S},4~{R})-3-amino-4-hydroxy-piperidine-1-carbonyl]-7-methoxy-1-methyl-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |
| 661 | 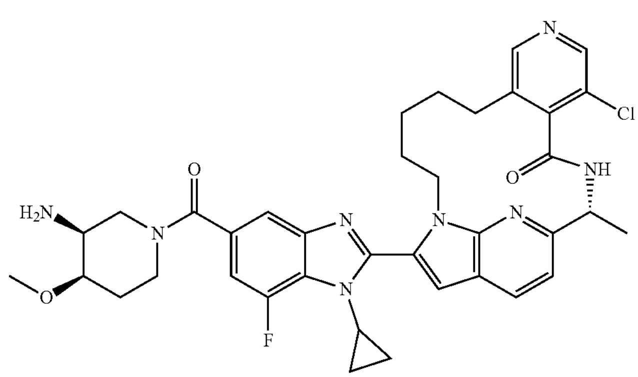 | (2~{R})-17-[5-[(3~{S},4~{R})-3-amino-4-methoxy-piperidine-1-carbonyl]-1-cyclopropyl-7-fluoro-benzimidazol-2-yl]-6-chloro-2-methyl-3,8,16,22-tetrazatetracyclo[14.5.2.0^{5,10}.0^{19,23}]tricosa-1(22),5,7,9,17,19(23),20-heptaen-4-one |

TABLE 1A-continued

| Example | Structure | Name |
|---|---|---|
| 662 | 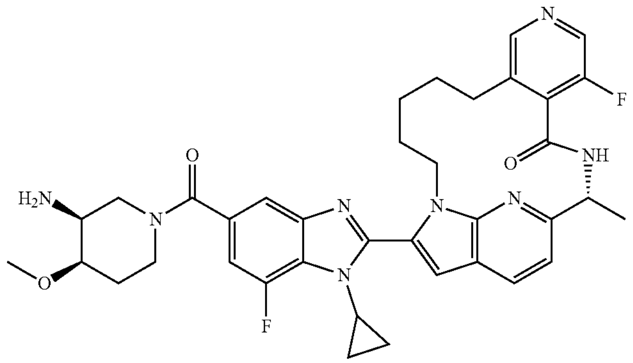 | (2~{R})-17-[5-[(3~{S},4~{R})-3-amino-4-methoxy-piperidine-1-carbonyl]-1-cyclopropyl-7-fluoro-benzimidazol-2-yl]-6-fluoro-2-methyl-3,8,16,22-tetrazatetracyclo[14.5.2.0^{5,10}.0^{19,23}]tricosa-1(22),5,7,9,17,19(23),20-heptaen-4-one |
| 663 | 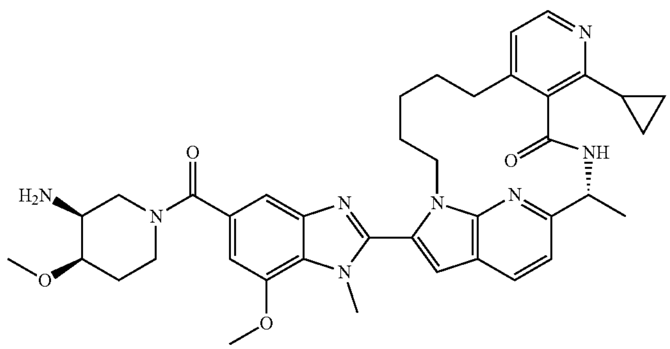 [SMILES: COc1cc(C(=O)N2CC[C@@H](OC)[C@@H](N)C2)cc2nc(-c3cc4ccc5nc4n3CCCCCc3ccnc(C4CC4)c3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-6-cyclopropyl-2-methyl-3,7,16,22-tetrazatetracyclo[14.5.2.0^{5,10}.0^{19,23}]tricosa-1(22),5,7,9,17,19(23),20-heptaen-4-one |
| 664 | 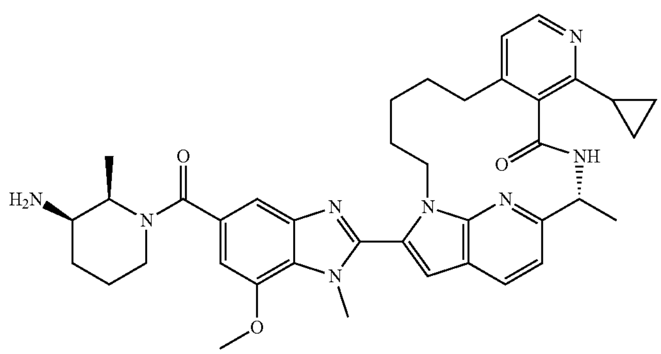 [SMILES: COc1cc(C(=O)N2CCC[C@@H](N)[C@H]2C)cc2nc(-c3cc4ccc5nc4n3CCCCCc3ccnc(C4CC4)c3C(=O)N[C@@H]5C)n(C)c12] | (2~{R})-17-[5-[(2~{R},3~{R})-3-amino-2-methyl-piperidine-1-carbonyl]-7-methoxy-1-methyl-benzimidazol-2-yl]-6-cyclopropyl-2-methyl-3,7,16,22-tetrazatetracyclo[14.5.2.0^{5,10}.0^{19,23}]tricosa-1(22),5,7,9,17,19(23),20-heptaen-4-one |
| 665 | 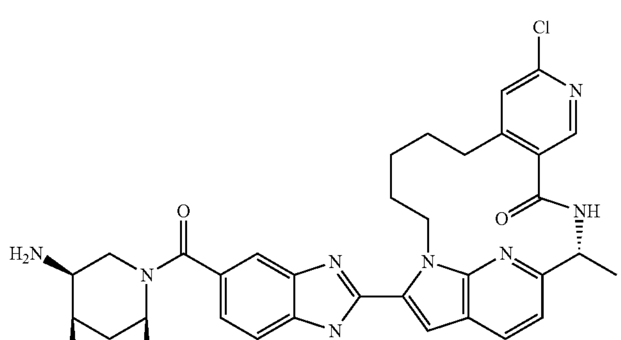 | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-chloro-2-methyl-3,7,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 666 | 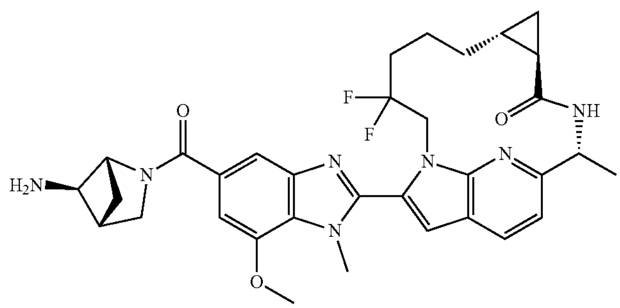 [SMILES: COc1cc(C(=O)N2C[C@H]3C[C@@H]2[C@@H]3N)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(1~{R},4~{R},5~{R})-5-amino-2-azabicyclo[2.1.1]hexane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 667 | 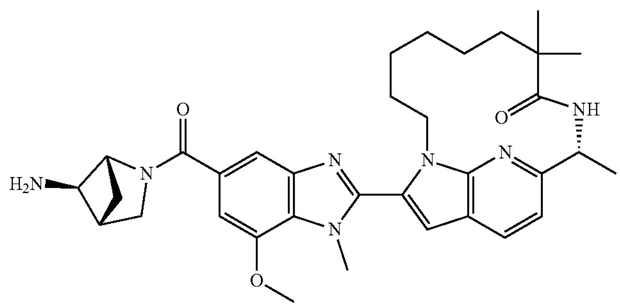 [SMILES: COc1cc(C(=O)N2C[C@H]3C[C@@H]2[C@@H]3N)cc2nc(-c3cc4ccc5nc4n3CCCCCCC(C)(C)C(=O)N[C@@H]5C)n(C)c12] | (11~{R})-17-[5-[(1~{R},4~{R},5~{R})-5-amino-2-azabicyclo[2.1.1]hexane-2-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 668 | 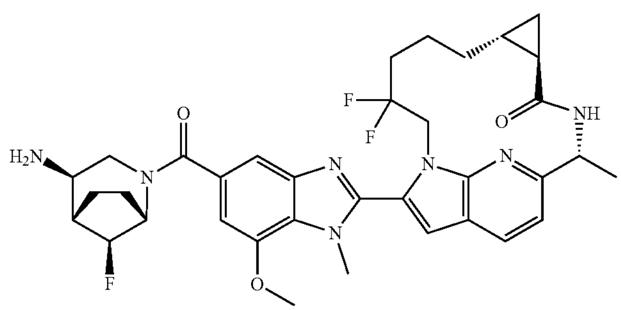 [SMILES: COc1cc(C(=O)N2C[C@H](N)[C@@H]3CC[C@H]2[C@H]3F)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(1~{S},4~{R},5~{S},8~{S})-4-amino-8-fluoro-2-azabicyclo[3.2.1]octane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 669 | 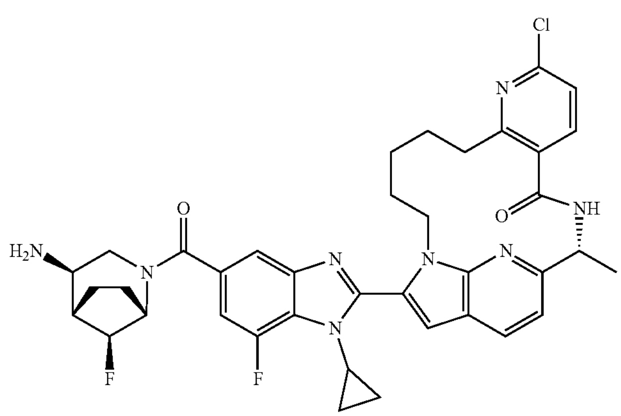 [SMILES: C[C@H]1NC(=O)c2ccc(Cl)nc2CCCCCn2c(-c3nc4cc(C(=O)N5C[C@H](N)[C@@H]6CC[C@H]5[C@H]6F)cc(F)c4n3C3CC3)cc3ccc1nc32] | (2~{R})-17-[5-[(1~{S},4~{R},5~{S},8~{S})-4-amino-8-fluoro-2-azabicyclo[3.2.1]octane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 670 | 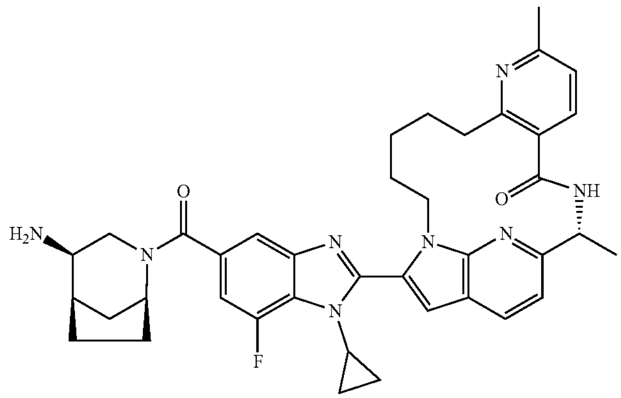 [SMILES: Cc1ccc2c(n1)CCCCCn1c(-c3nc4cc(C(=O)N5C[C@H](N)[C@@H]6CC[C@H]5C6)cc(F)c4n3C3CC3)cc3ccc(nc31)[C@@H](C)NC2=O] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2,8-dimethyl-3,9,16,22-tetrazatetracyclo[14.5.2.0^{5,10}.0^{19,23}]tricosa-1(22),5(10),6,8,17,19(23),20-heptaen-4-one |
| 671 | 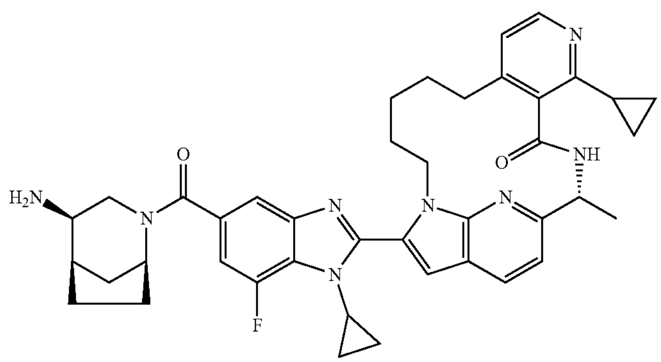 [SMILES: C[C@H]1NC(=O)c2c(ccnc2C2CC2)CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-6-cyclopropyl-2-methyl-3,7,16,22-tetrazatetracyclo[14.5.2.0^{5,10}.0^{19,23}]tricosa-1(22),5(10),6,8,17,19(23),20-heptaen-4-one |
| 672 | 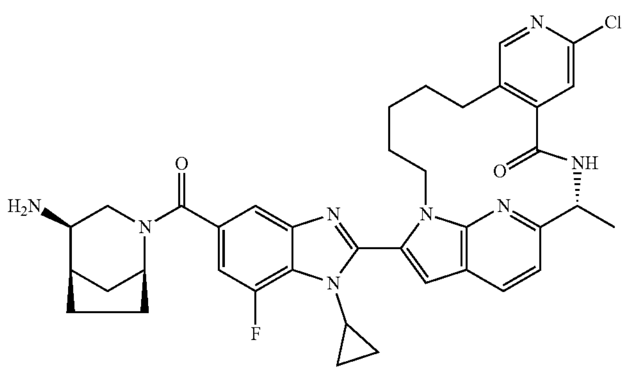 [SMILES: C[C@H]1NC(=O)c2cc(Cl)ncc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-7-chloro-2-methyl-3,8,16,22-tetrazatetracyclo[14.5.2.0^{5,10}.0^{19,23}]tricosa-1(22),5(10),6,8,17,19(23),20-heptaen-4-one |
| 673 | 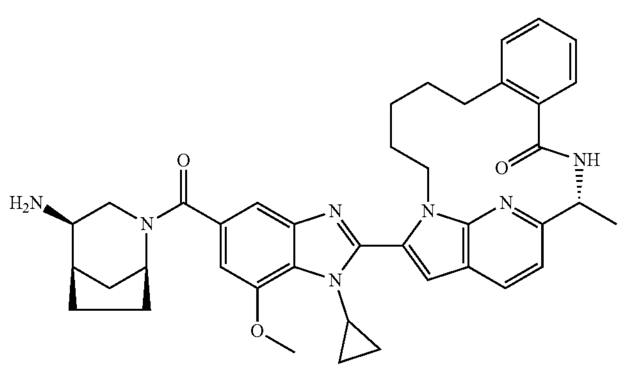 [SMILES: COc1cc(C(=O)N2C[C@H](N)[C@@H]3CC[C@H]2C3)cc2nc(-c3cc4ccc5nc4n3CCCCCc3ccccc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-2-methyl-3,16,22-triazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 674 | 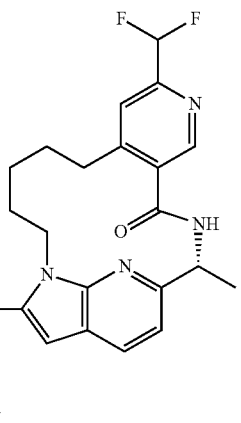 | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-(difluoromethyl)-2-methyl-3,7,16,22-tetrazatetracyclo[14.5.2.0^{5,10}.0^{19,23}]tricosa-1(22),5(10),6,8,17,19(23),20-heptaen-4-one |
| 675 | 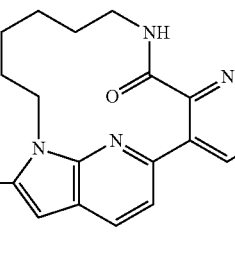 | 17-[5-[(3~{S},4~{R})-3-amino-4-methoxy-piperidine-1-carbonyl]-7-methoxy-1-methyl-benzimidazol-2-yl]-6,9,16,22-tetrazatetracyclo[14.5.2.0^{2,7}.0^{19,23}]tricosa-1(22),2,4,6,17,19(23),20-heptaen-8-one |
| 676 | 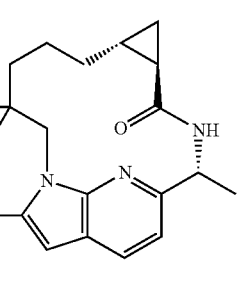 | (2~{R},5~{R},7~{R})-14-[5-[(2~{S},3~{R},4~{R})-3-amino-2,4-dimethyl-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 677 | 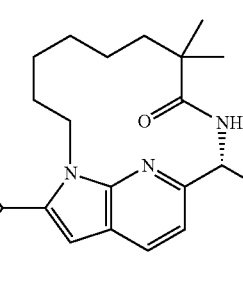 | (11~{R})-17-[5-[(3~{R},4~{S})-3-amino-4-(methoxymethyl)piperidine-1-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 678 | 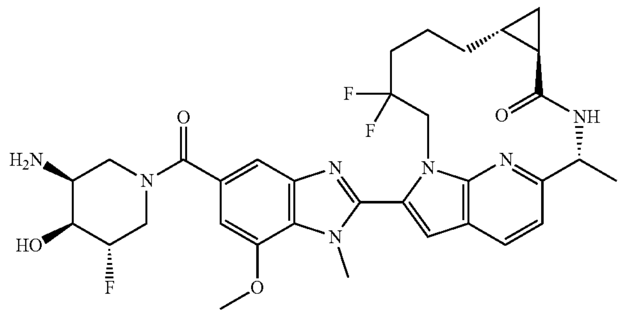 [SMILES: COc1cc(C(=O)N2C[C@H](N)[C@H](O)[C@@H](F)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(3~{S},4~{S},5~{S})-3-amino-5-fluoro-4-hydroxy-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 679 | 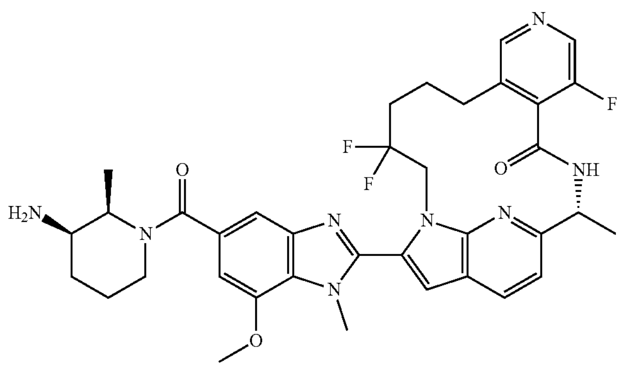 [SMILES: COc1cc(C(=O)N2CCC[C@@H](N)[C@H]2C)cc2nc(-c3cc4ccc5nc4n3CC(F)(F)CCCc3cncc(F)c3C(=O)N[C@@H]5C)n(C)c12] | (2~{R})-17-[5-[(2~{R},3~{R})-3-amino-2-methyl-piperidine-1-carbonyl]-7-methoxy-1-methyl-benzimidazol-2-yl]-6,14,14-trifluoro-2-methyl-3,8,16,22-tetrazatetracyclo[14.5.2.0^{5,10}.0^{19,23}]tricosa-1(22),5(10)6,8,17,19(23),20-heptaen-4-one |
| 680 | 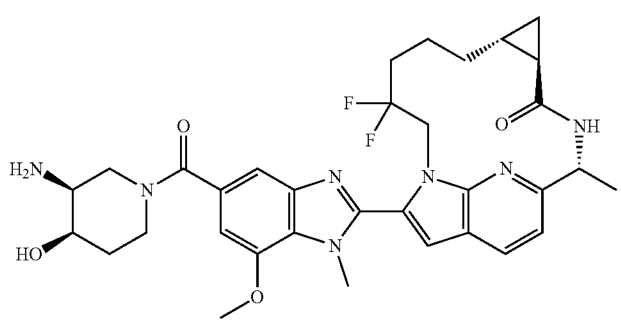 [SMILES: COc1cc(C(=O)N2CC[C@@H](O)[C@@H](N)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(3~{S},4~{R})-3-amino-4-hydroxy-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 681 | 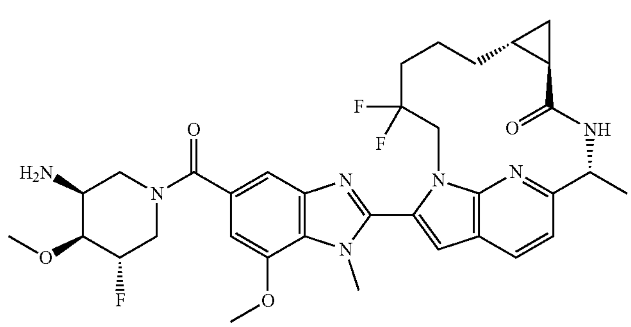 | (2~{R},5~{R},7~{R})-14-[5-[(3~{S},4~{S},5~{S})-3-amino-5-fluoro-4-methoxy-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 682 | 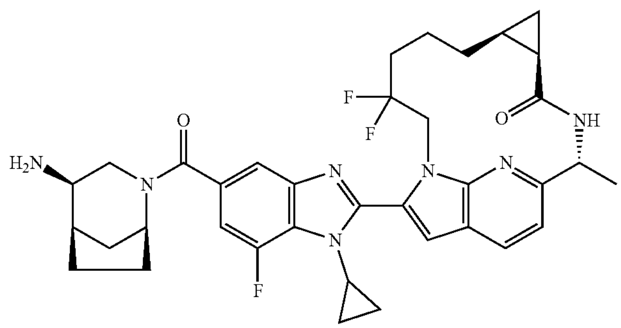 [SMILES: C[C@H]1NC(=O)[C@@H]2C[C@@H]2CCCC(F)(F)Cn2c(-c3nc4cc(C(=O)N5C[C@H](N)[C@@H]6CC[C@H]5C6)cc(F)c4n3C3CC3)cc3ccc1nc32] | (2~{R},5~{R},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 683 | 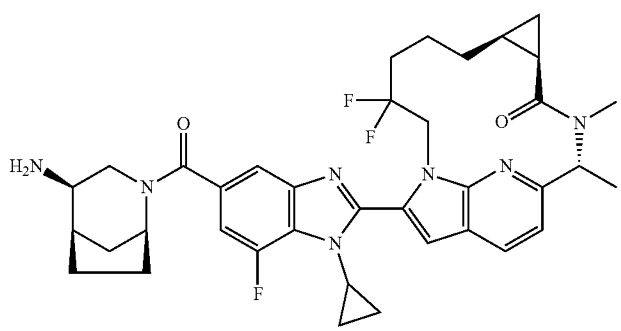 [SMILES: C[C@@H]1c2ccc3cc(-c4nc5cc(C(=O)N6C[C@H](N)[C@@H]7CC[C@H]6C7)cc(F)c5n4C4CC4)n(c3n2)CC(F)(F)CCC[C@H]2C[C@H]2C(=O)N1C] | (2~{R},5~{R},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-11,11-difluoro-2,3-dimethyl-3,13,19-triazatetracyclo[11.5.2.0^{5,7}.0^{16,20}]icosa-1(19),14,16(20),17-tetraen-4-one |
| 684 | 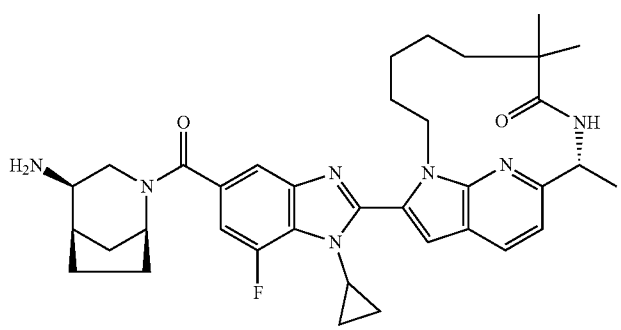 [SMILES: C[C@H]1NC(=O)C(C)(C)CCCCCn2c(-c3nc4cc(C(=O)N5C[C@H](N)[C@@H]6CC[C@H]5C6)cc(F)c4n3C3CC3)cc3ccc1nc32] | (10~{R})-16-[5-[(1~{S},4~{R},5~{R})-4-amino-2-azabicyclo[3.2.1]octane-2-carbonyl]-1-cyclopropyl-7-fluoro-benzimidazol-2-yl]-7,7,10-trimethyl-1,9,18-triazatricyclo[9.5.2.0^{14,17}]octadeca-11(18),12,14(17),15-tetraen-8-one |
| 685 | 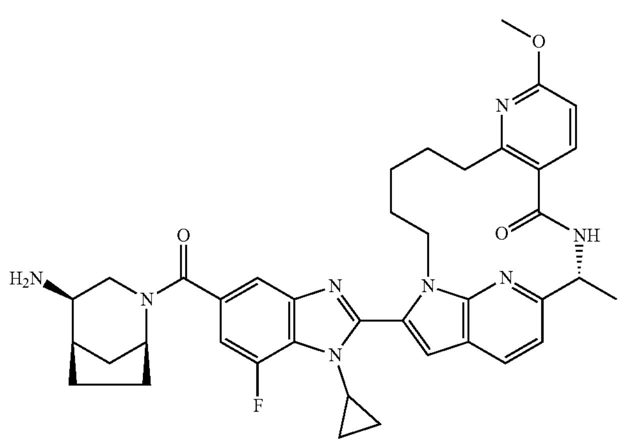 [SMILES: COc1ccc2c(n1)CCCCCn1c(-c3nc4cc(C(=O)N5C[C@H](N)[C@@H]6CC[C@H]5C6)cc(F)c4n3C3CC3)cc3ccc(nc31)[C@@H](C)NC2=O] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-methoxy-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 686 | 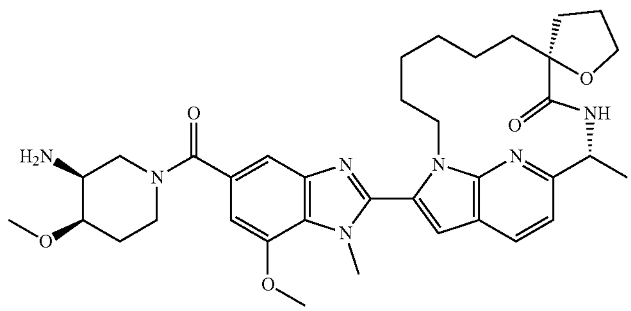 | (8~{S},11~{R})-17-[5-[(3~{S},4~{R})-3-amino-4-methoxy-piperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,2'-tetrahydrofuran]-9-one |
| 687 | 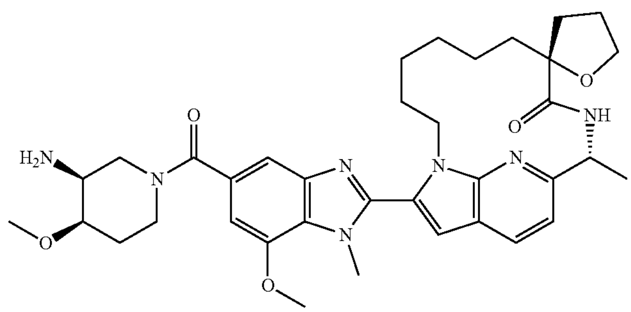 | (8~{R},11~{R})-17-[5-[(3~{S},4~{R})-3-amino-4-methoxy-piperidine-1-carbonyl]-7-methoxy-1-methyl-benzimidazol-2-yl]-11-methyl-spiro[1,10,19-triazatricyclo[10.5.2.0^{15,18}]nonadeca-12(19),13,15(18),16-tetraene-8,2'-tetrahydrofuran]-9-one |
| 688 | 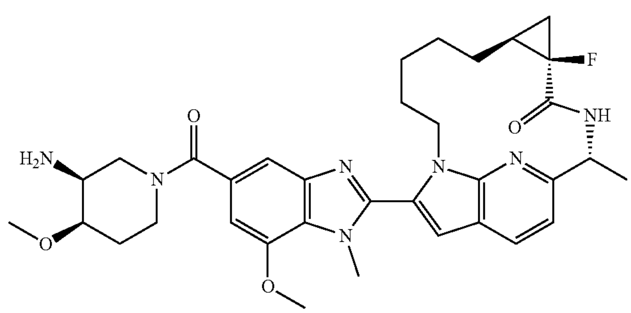 | (2~{R},5~{R},7~{S})-14-[5-[(3~{S},4~{R})-3-amino-4-methoxy-piperidine-1-carbonyl]-7-methoxy-1-methyl-benzimidazol-2-yl]-5-fluoro-2-methyl-3,13,19-triazatetracyclo[11.5.2.0^{5,7}.0^{16,20}]icosa-1(19),14,16(20),17-tetraen-4-one |
| 689 | 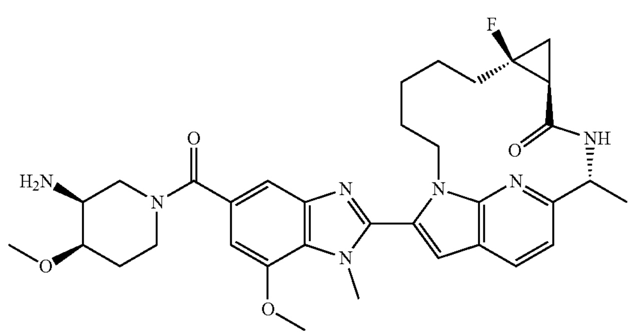 | (2~{R},5~{S},7~{S})-14-[5-[(3~{S},4~{R})-3-amino-4-methoxy-piperidine-1-carbonyl]-7-methoxy-1-methyl-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 690 | 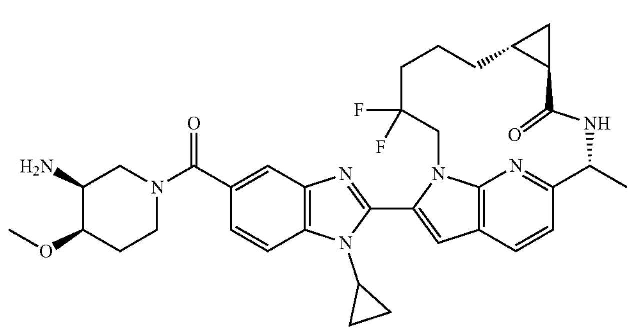 | (2~{R},5~{R},7~{R})-14-[5-[(3~{S},4~{R})-3-amino-4-methoxy-piperidine-1-carbonyl]-1-cyclopropyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 691 | 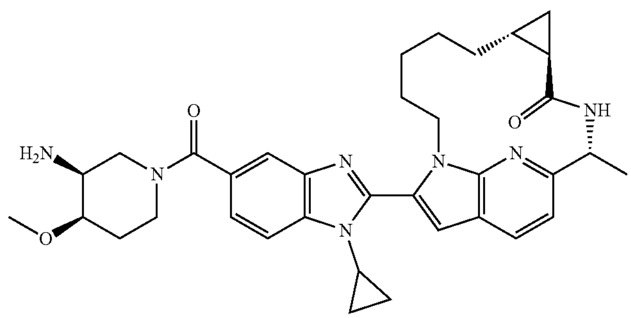 | (2~{R},5~{R},7~{R})-14-[5-[(3~{S},4~{R})-3-amino-4-methoxy-piperidine-1-carbonyl]-1-cyclopropyl-benzimidazol-2-yl]-2-methyl-3,13,19-triazatetracyclo[11.5.2.0^{5,7}.0^{16,20}]icosa-1(19),14,16(20),17-tetraen-4-one |
| 692 | 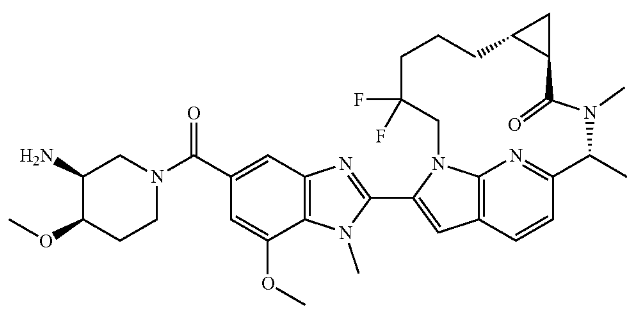 | (2~{R},5~{R},7~{R})-14-[5-[(3~{S},4~{R})-3-amino-4-methoxy-piperidine-1-carbonyl]-7-methoxy-1-methyl-benzimidazol-2-yl]-11,11-difluoro-2,3-dimethyl-3,13,19-triazatetracyclo[11.5.2.0^{5,7}.0^{16,20}]icosa-1(19),14,16(20),17-tetraen-4-one |
| 693 | 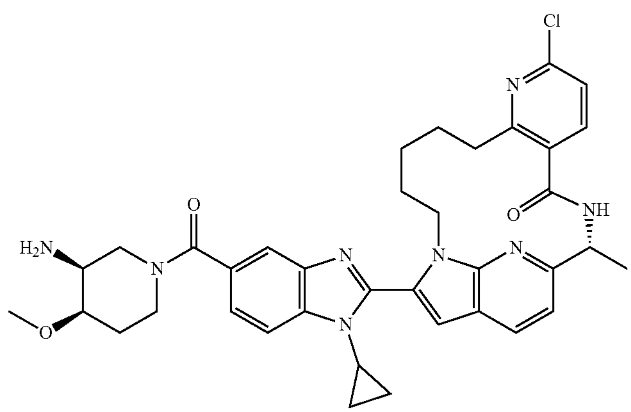 | (2~{R})-17-[5-[(3~{S},4~{R})-3-amino-4-methoxy-piperidine-1-carbonyl]-1-cyclopropyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 694 | 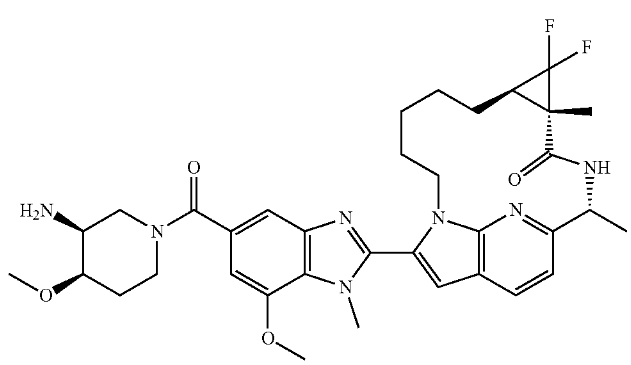 | (2~{R},5~{S},7~{R})-14-[5-[(3~{S},4~{R})-3-amino-4-methoxy-piperidine-1-carbonyl]-7-methoxy-1-methyl-benzimidazol-2-yl]-6,6-difluoro-2,5-dimethyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 695 | 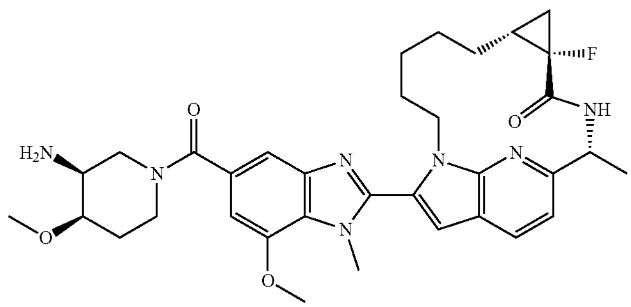 | (2~{R},5~{S},7~{R})-14-[5-[(3~{S},4~{R})-3-amino-4-methoxy-piperidine-1-carbonyl]-7-methoxy-1-methyl-benzimidazol-2-yl]-5-fluoro-2-methyl-3,13,19-triazatetracyclo[11.5.2.0^{5,7}.0^{16,20}]icosa-1(19),14,16(20),17-tetraen-4-one |
| 696 | 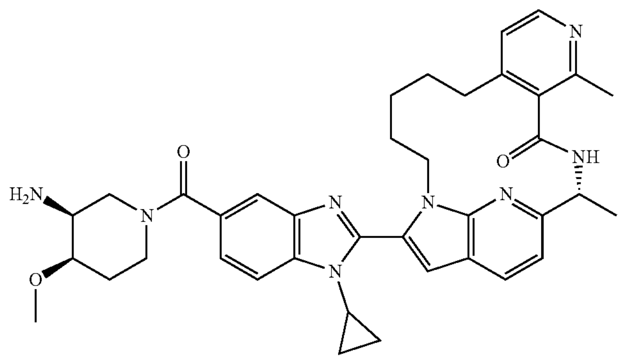 [SMILES: CO[C@@H]1CCN(C(=O)c2ccc3c(c2)nc(-c2cc4ccc5nc4n2CCCCCc2ccnc(C)c2C(=O)N[C@@H]5C)n3C2CC2)C[C@@H]1N] | (2~{R})-17-[5-[(3~{S},4~{R})-3-amino-4-methoxy-piperidine-1-carbonyl]-1-cyclopropyl-benzimidazol-2-yl]-2,6-dimethyl-3,7,16,22-tetrazatetracyclo[14.5.2.0^{5,10}.0^{19,23}]tricosa-1(22),5(10),6,8,17,19(23),20-heptaen-4-one |
| 697 | 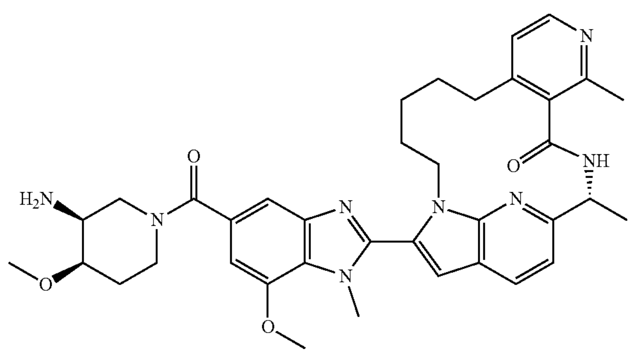 | (2~{R})-17-[5-[(3~{S},4~{R})-3-amino-4-methoxy-piperidine-1-carbonyl]-7-methoxy-1-methyl-benzimidazol-2-yl]-2,6-dimethyl-3,7,16,22-tetrazatetracyclo[14.5.2.0^{5,10}.0^{19,23}]tricosa-1(22),5(10),6,8,17,19(23),20-heptaen-4-one |
| 698 | 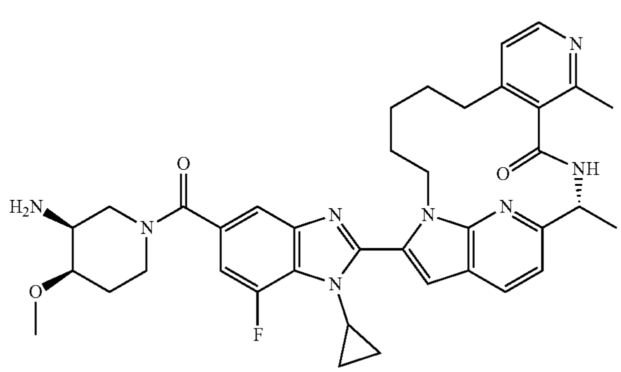 [SMILES: CO[C@@H]1CCN(C(=O)c2cc(F)c3c(c2)nc(-c2cc4ccc5nc4n2CCCCCc2ccnc(C)c2C(=O)N[C@@H]5C)n3C2CC2)C[C@@H]1N] | (2~{R})-17-[5-[(3~{S},4~{R})-3-amino-4-methoxy-piperidine-1-carbonyl]-1-cyclopropyl-7-fluoro-benzimidazol-2-yl]-2,6-dimethyl-3,7,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 699 | 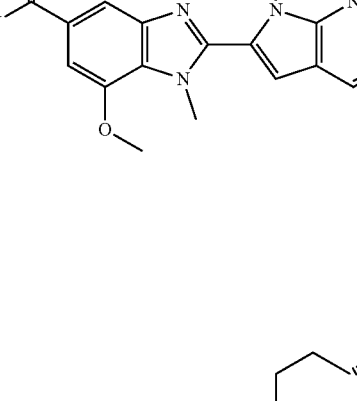 | [(3~{S},4~{R})-3-amino-4-methoxy-1-piperidyl]-[7-methoxy-1-methyl-2-[(9~{S},11~{R})-11-methyl-9-(trifluoromethyl)-1,10,19-triazatricyclo[10.5.2.0^{15,18}]nonadeca-12(19),13,15(18),16-tetraen-17-yl]benzimidazol-5-yl]methanone |
| 700 | 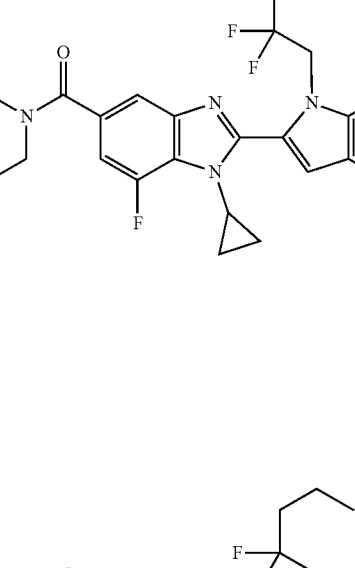 | (2~{R},5~{S},7~{S})-14-[5-[(3~{S},4~{R})-3-amino-4-methoxy-piperidine-1-carbonyl]-1-cyclopropyl-7-fluoro-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 701 | 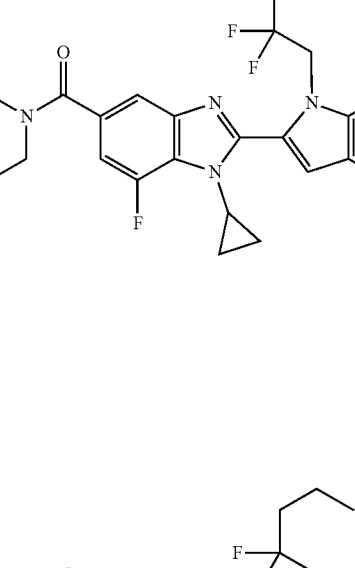 | (2~{R},5~{S},7~{S})-14-[5-[(2~{R},3~{R})-3-amino-2-methyl-piperidine-1-carbonyl]-1-cyclopropyl-7-fluoro-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 702 | 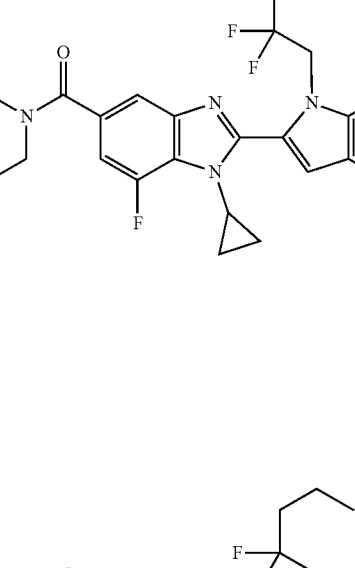 | (2~{R},5~{S},7~{S})-14-[5-[(3~{S},4~{R})-3-amino-4-methoxy-piperidine-1-carbonyl]-7-methoxy-1-methyl-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 703 | 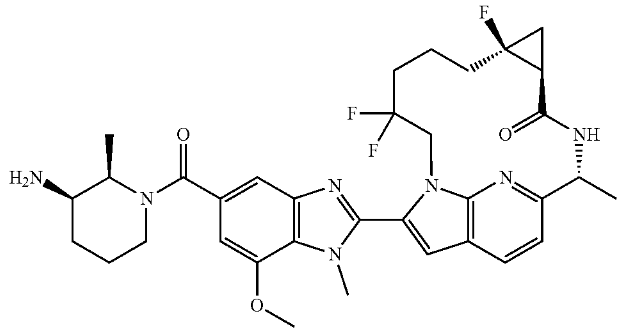 [SMILES: COc1cc(C(=O)N2CCC[C@@H](N)[C@H]2C)cc2nc(-c3cc4ccc5nc4n3CC(F)(F)CCC[C@]3(F)C[C@H]3C(=O)N[C@@H]5C)n(C)c12] | (2~{R},5~{S},7~{S})-14-[5-[(2~{R},3~{R})-3-amino-2-methyl-piperidine-1-carbonyl]-7-methoxy-1-methyl-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 704 | 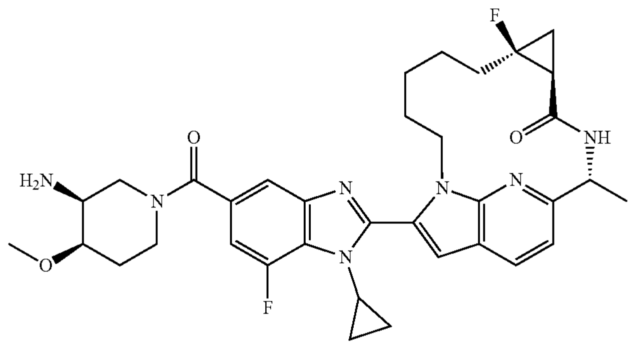 | (2~{R},5~{S},7~{S})-14-[5-[(3~{S},4~{R})-3-amino-4-methoxy-piperidine-1-carbonyl]-1-cyclopropyl-7-fluoro-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 705 | 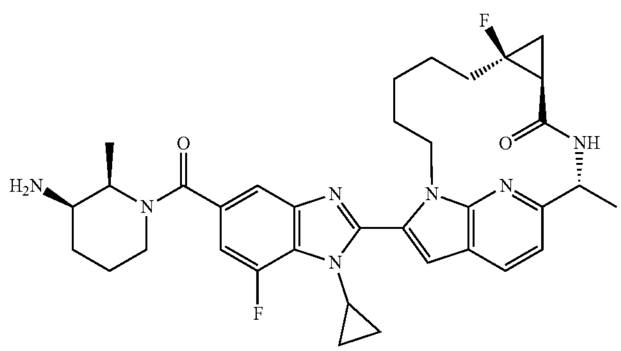 [SMILES: C[C@@H]1[C@H](N)CCCN1C(=O)c1cc(F)c2c(c1)nc(-c1cc3ccc4nc3n1CCCCC[C@]1(F)C[C@H]1C(=O)N[C@@H]4C)n2C1CC1] | (2~{R},5~{S},7~{S})-14-[5-[(2~{R},3~{R})-3-amino-2-methyl-piperidine-1-carbonyl]-1-cyclopropyl-7-fluoro-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 706 | 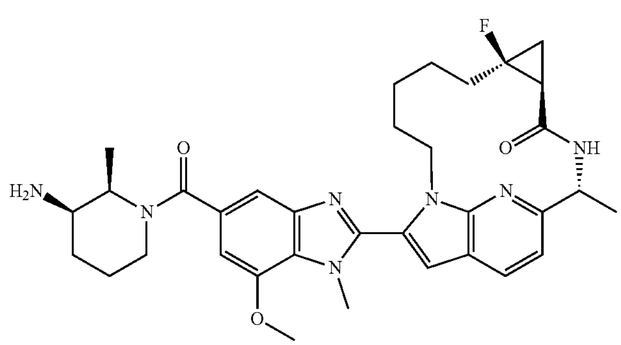 [SMILES: COc1cc(C(=O)N2CCC[C@@H](N)[C@H]2C)cc2nc(-c3cc4ccc5nc4n3CCCCC[C@]3(F)C[C@H]3C(=O)N[C@@H]5C)n(C)c12] | (2~{R},5~{S},7~{S})-14-[5-[(2~{R},3~{R})-3-amino-2-methyl-piperidine-1-carbonyl]-7-methoxy-1-methyl-benzimidazol-2-yl]-7-fluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 707 | 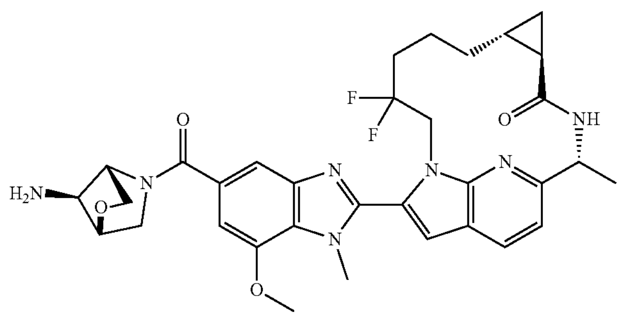 [SMILES: COc1cc(C(=O)N2C[C@H]3OC[C@@H]2[C@@H]3N)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(1~{R},4~{S},7~{S})-7-amino-2-oxa-5-azabicyclo[2.2.1]heptane-5-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 708 | 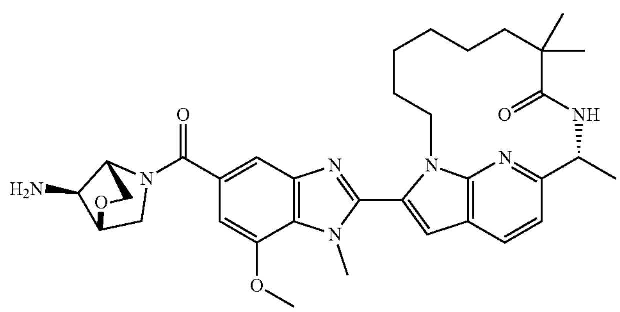 [SMILES: COc1cc(C(=O)N2C[C@H]3OC[C@@H]2[C@@H]3N)cc2nc(-c3cc4ccc5nc4n3CCCCCCC(C)(C)C(=O)N[C@@H]5C)n(C)c12] | (11~{R})-17-[5-[(1~{R},4~{S},7~{S})-7-amino-2-oxa-5-azabicyclo[2.2.1]heptane-5-carbonyl]-7-methoxy-1-methyl-benzimidazol-2-yl]-8,8,11-trimethyl-1,10,19-triazatricyclo[10.5.2.0^{15,18}]nonadeca-12(19),13,15(18),16-tetraen-9-one |
| 709 | 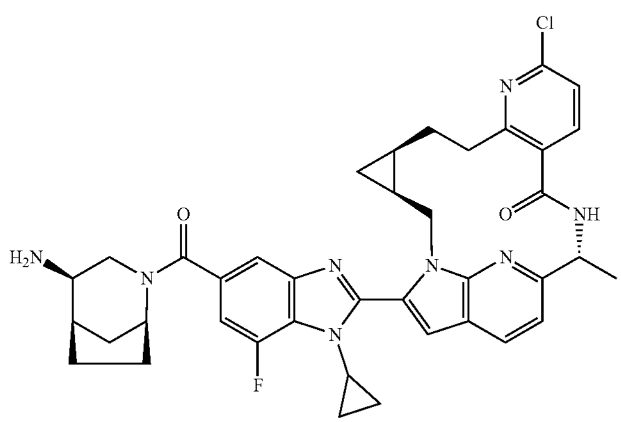 [SMILES: C[C@H]1NC(=O)c2ccc(Cl)nc2CC[C@@H]2C[C@@H]2Cn2c(-c3nc4cc(C(=O)N5C[C@H](N)[C@@H]6CC[C@H]5C6)cc(F)c4n3C3CC3)cc3ccc1nc32] | (3~{S},5~{R},16~{R})-22-[5-[(1~{S},4~{R},5~{R})-4-amino-2-azabicyclo[3.2.1]octane-2-carbonyl]-1-cyclopropyl-7-fluoro-benzimidazol-2-yl]-10-chloro-16-methyl-1,9,15,24-tetrazapentacyclo[15.5.2.0^{3,5}.0^{8,13}.0^{20,23}]tetracosa-8(13),9,11,17(24),18,20(23),21-heptaen-14-one |
| 710 | 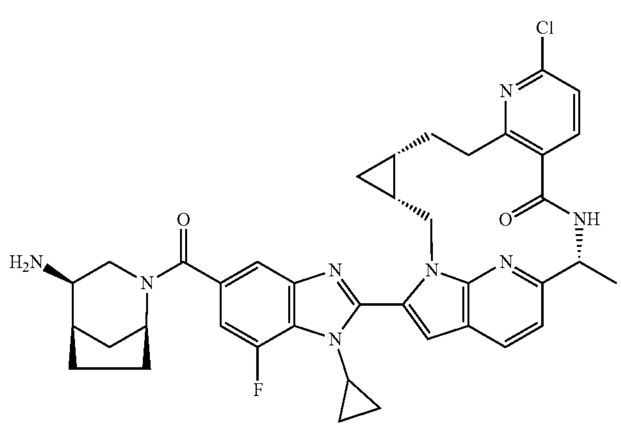 [SMILES: C[C@H]1NC(=O)c2ccc(Cl)nc2CC[C@H]2C[C@H]2Cn2c(-c3nc4cc(C(=O)N5C[C@H](N)[C@@H]6CC[C@H]5C6)cc(F)c4n3C3CC3)cc3ccc1nc32] | (3~{R},5~{S},16~{R})-22-[5-[(1~{S},4~{R},5~{R})-4-amino-2-azabicyclo[3.2.1]octane-2-carbonyl]-1-cyclopropyl-7-fluoro-benzimidazol-2-yl]-10-chloro-16-methyl-1,9,15,24-tetrazapentacyclo[15.5.2.0^{3,5}.0^{8,13}.0^{20,23}]tetracosa-8(13),9,11,17(24),18,20(23),21-heptaen-14-one |

TABLE 1A-continued

| Example | Structure | Name |
|---|---|---|
| 711 | 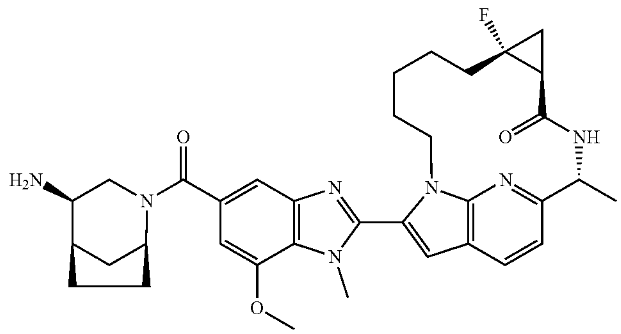 [SMILES: COc1cc(C(=O)N2C[C@H](N)[C@@H]3CC[C@H]2C3)cc2nc(-c3cc4ccc5nc4n3CCCCC[C@@]3(F)C[C@H]3C(=O)N[C@@H]5C)n(C)c12] | (2~{R},5~{S},7~{R})-14-[5-[(1~{S},4~{R},5~{R})-4-amino-2-azabicyclo[3.2.1]octane-2-carbonyl]-7-methoxy-1-methyl-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 712 | 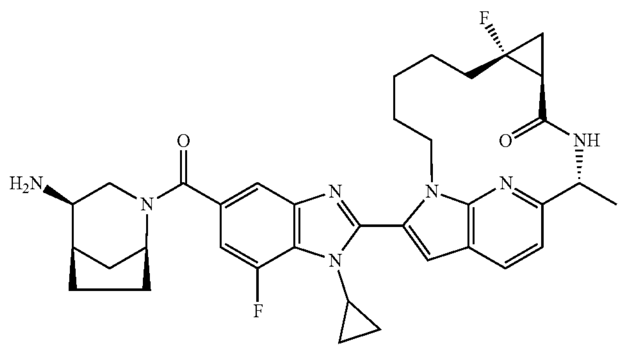 [SMILES: C[C@H]1NC(=O)[C@@H]2C[C@]2(F)CCCCCn2c(-c3nc4cc(C(=O)N5C[C@H](N)[C@@H]6CC[C@H]5C6)cc(F)c4n3C3CC3)cc3ccc1nc32] | (2~{R},5~{S},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 713 | 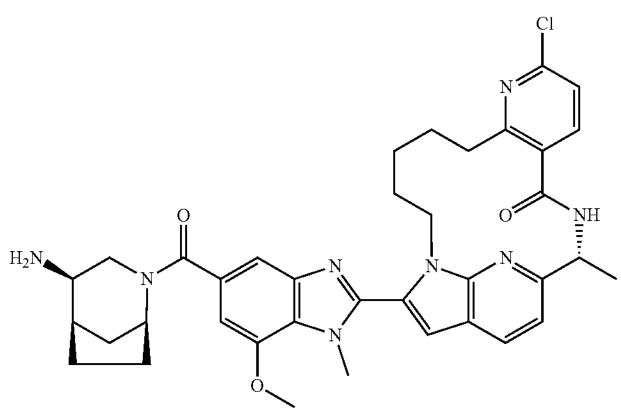 [SMILES: COc1cc(C(=O)N2C[C@H](N)[C@@H]3CC[C@H]2C3)cc2nc(-c3cc4ccc5nc4n3CCCCCc3nc(Cl)ccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 714 | 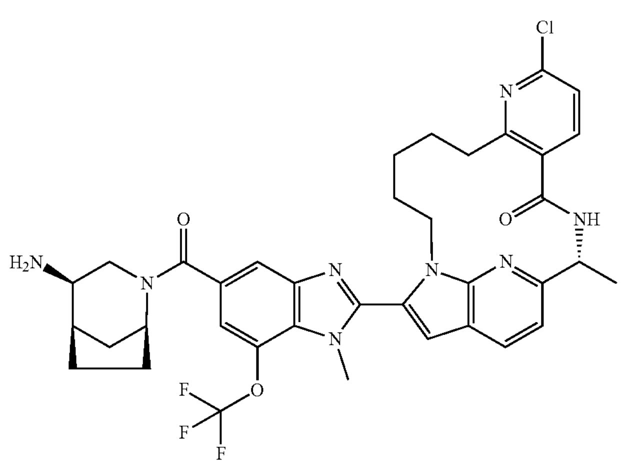 [SMILES: C[C@H]1NC(=O)c2ccc(Cl)nc2CCCCCn2c(-c3nc4cc(C(=O)N5C[C@H](N)[C@@H]6CC[C@H]5C6)cc(OC(F)(F)F)c4n3C)cc3ccc1nc32] | (2~{R})-17-[5-[(1~{S},4~{R},5~{R})-4-amino-2-azabicyclo[3.2.1]octane-2-carbonyl]-1-methyl-7-(trifluoromethoxy)benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 715 | 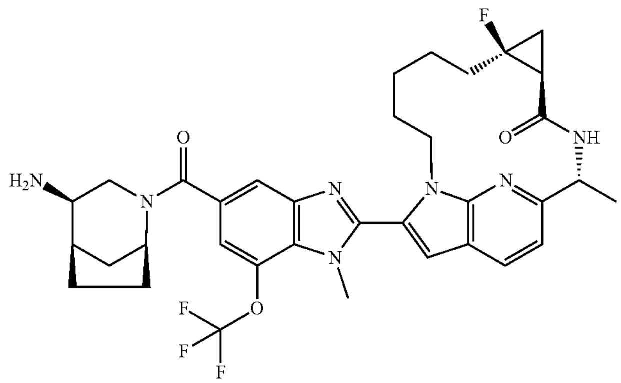 [SMILES: C[C@H]1NC(=O)[C@@H]2C[C@@]2(F)CCCCCn2c(-c3nc4cc(C(=O)N5C[C@H](N)[C@@H]6CC[C@H]5C6)cc(OC(F)(F)F)c4n3C)cc3ccc1nc32] | (2~{R},5~{S},7~{S})-14-[5-[(1~{S},4~{R},5~{R})-4-amino-2-azabicyclo[3.2.1]octane-2-carbonyl]-1-methyl-7-(trifluoromethoxy)benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 716 | 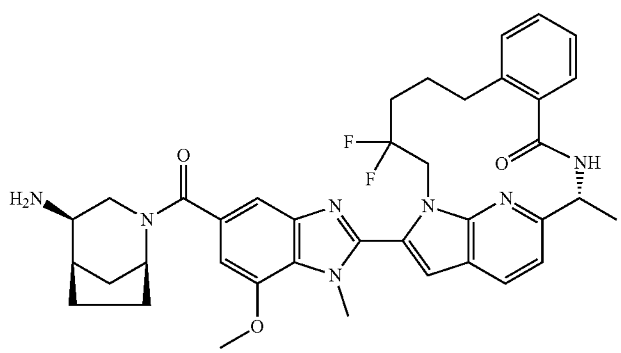 [SMILES: COc1cc(C(=O)N2C[C@H](N)[C@@H]3CC[C@H]2C3)cc2nc(-c3cc4ccc5nc4n3CC(F)(F)CCCc3ccccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-14,14-difluoro-2-methyl-3,16,22-triazatetracyclo[14.5.2.0^{5,10}.0^{19,23}]tricosa-1(22),5(10),6,8,17,19(23),20-heptaen-4-one |
| 717 | 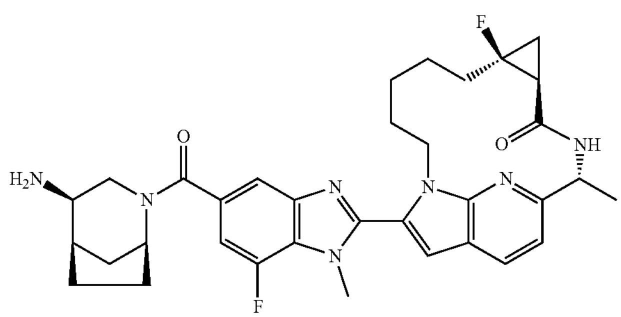 [SMILES: C[C@H]1NC(=O)[C@@H]2C[C@@]2(F)CCCCCn2c(-c3nc4cc(C(=O)N5C[C@H](N)[C@@H]6CC[C@H]5C6)cc(F)c4n3C)cc3ccc1nc32] | (2~{R},5~{S},7~{S})-14-[5-[(1~{S},4~{R},5~{R})-4-amino-2-azabicyclo[3.2.1]octane-2-carbonyl]-7-fluoro-1-methyl-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 718 | 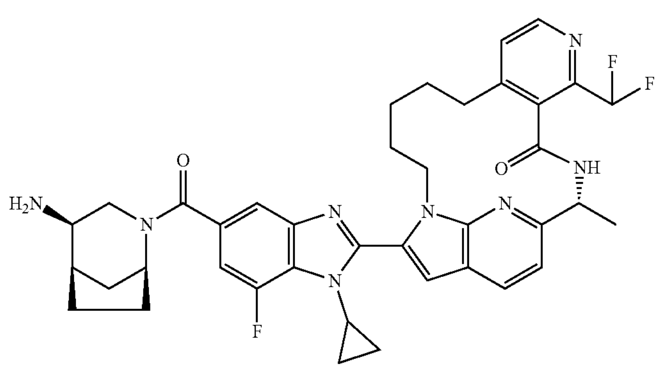 [SMILES: C[C@H]1NC(=O)c2c(ccnc2C(F)F)CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-6-(difluoromethyl)-2-methyl-3,7,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 719 | 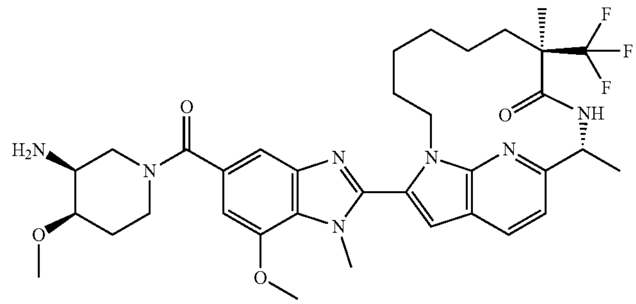 [SMILES: COc1cc(C(=O)N2CC[C@@H](OC)[C@@H](N)C2)cc2nc(-c3cc4ccc5nc4n3CCCCCC[C@@](C)(C(F)(F)F)C(=O)N[C@@H]5C)n(C)c12] | (8~{R},11~{R})-17-[5-[(3~{S},4~{R})-3-amino-4-methoxy-piperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 720 | 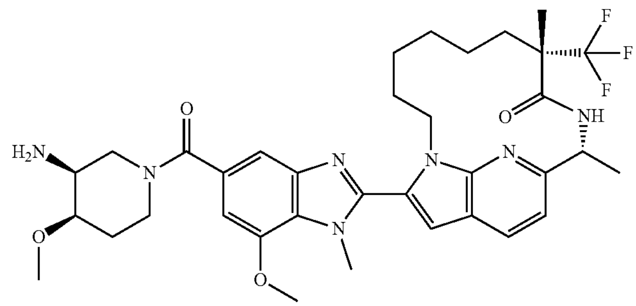 [SMILES: COc1cc(C(=O)N2CC[C@@H](OC)[C@@H](N)C2)cc2nc(-c3cc4ccc5nc4n3CCCCCC[C@](C)(C(F)(F)F)C(=O)N[C@@H]5C)n(C)c12] | (8~{S},11~{R})-17-[5-[(3~{S},4~{R})-3-amino-4-methoxy-piperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 721 | 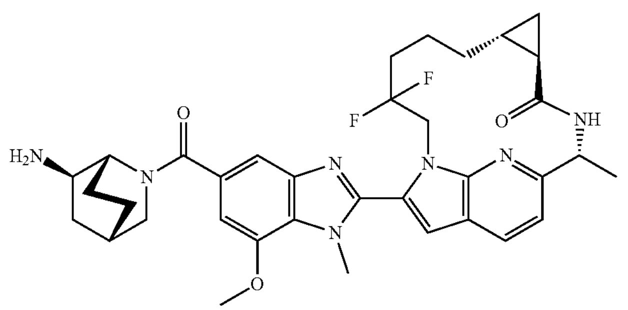 | (2~{R},5~{R},7~{R})-14-[5-[(1~{R},4~{S},6~{R})-6-amino-2-azabicyclo[2.2.2]octane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 722 | 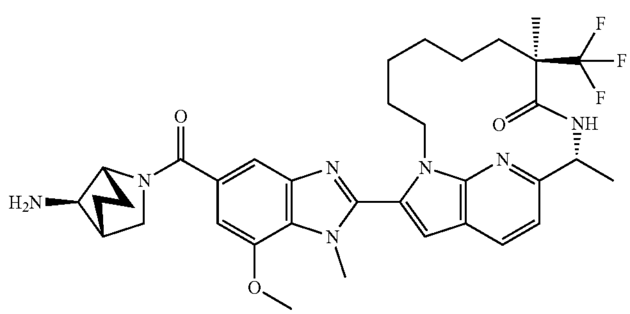 | (8~{R},11~{R})-17-[5-[(1~{R},4~{R},7~{R})-7-amino-2-azabicyclo[2.2.1]heptane-2-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 723 | 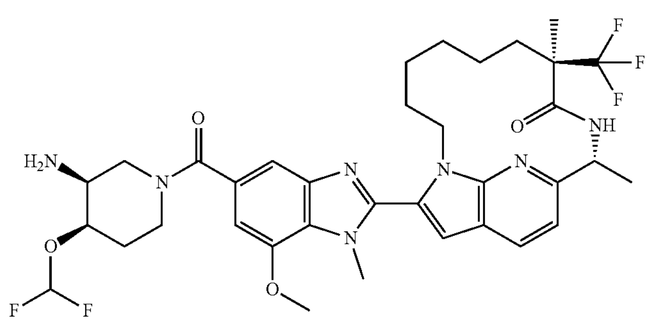 [SMILES: COc1cc(C(=O)N2CC[C@@H](OC(F)F)[C@@H](N)C2)cc2nc(-c3cc4ccc5nc4n3CCCCCC[C@@](C)(C(F)(F)F)C(=O)N[C@@H]5C)n(C)c12] | (8~{R},11~{R})-17-[5-[(3~{S},4~{R})-3-amino-4-(difluoromethoxy)piperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 724 | 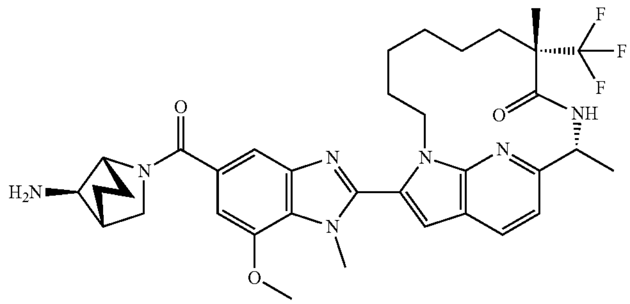 | (8~{S},11~{R})-17-[5-[(1~{R},4~{R},7~{R})-7-amino-2-azabicyclo[2.2.1]heptane-2-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 725 | 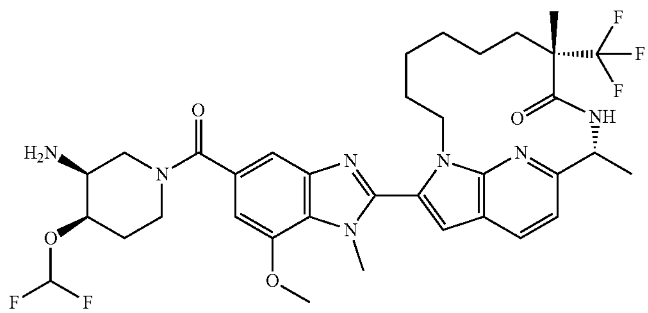 [SMILES: COc1cc(C(=O)N2CC[C@@H](OC(F)F)[C@@H](N)C2)cc2nc(-c3cc4ccc5nc4n3CCCCCC[C@](C)(C(F)(F)F)C(=O)N[C@@H]5C)n(C)c12] | (8~{S},11~{R})-17-[5-[(3~{S},4~{R})-3-amino-4-(difluoromethoxy)piperidine-1-carbonyl]-7-methoxy-1-methyl-benzimidazol-2-yl]-8,11-dimethyl-8-(trifluoromethyl)-1,10,19-triazatricyclo[10.5.2.0^{15,18}]nonadeca-12(19),13,15(18),16-tetraen-9-one |
| 726 | 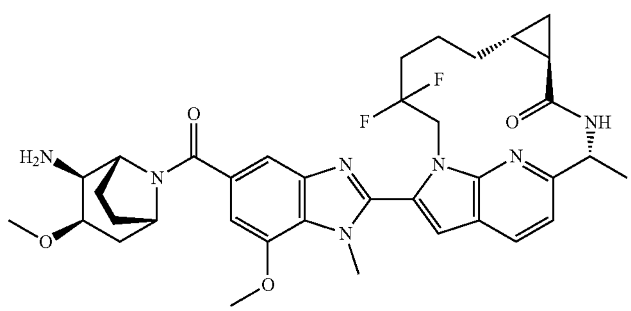 | (2~{R},5~{R},7~{R})-14-[5-[(1~{R},2~{S},3~{R},5~{S})-2-amino-3-methoxy-8-azabicyclo[3.2.1]octane-8-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 727 | 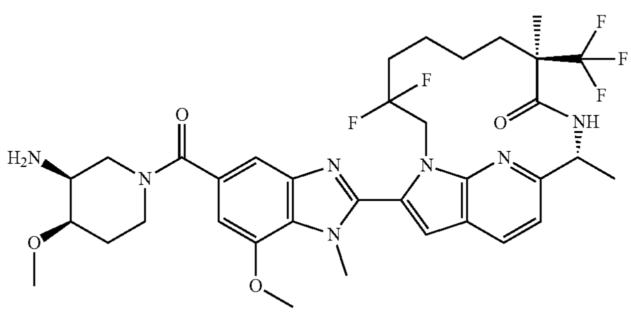 [SMILES: COc1cc(C(=O)N2CC[C@@H](OC)[C@@H](N)C2)cc2nc(-c3cc4ccc5nc4n3CC(F)(F)CCCC[C@@](C)(C(F)(F)F)C(=O)N[C@@H]5C)n(C)c12] | (8~{R},11~{R})-17-[5-[(3~{S},4~{R})-3-amino-4-methoxy-piperidine-1-carbonyl]-7-methoxy-1-methyl-benzimidazol-2-yl]-3,3-difluoro-8,11-dimethyl-8-(trifluoromethyl)-1,10,19-triazatricyclo[10.5.2.0^{15,18}]nonadeca-12(19),13,15(18),16-tetraen-9-one |
| 728 | 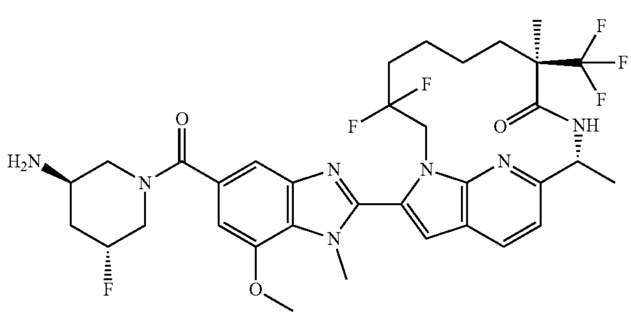 [SMILES: COc1cc(C(=O)N2C[C@H](N)C[C@@H](F)C2)cc2nc(-c3cc4ccc5nc4n3CC(F)(F)CCCC[C@@](C)(C(F)(F)F)C(=O)N[C@@H]5C)n(C)c12] | (8~{R},11~{R})-17-[5-[(3~{R},5~{R})-3-amino-5-fluoro-piperidine-1-carbonyl]-7-methoxy-1-methyl-benzimidazol-2-yl]-3,3-difluoro-8,11-dimethyl-8-(trifluoromethyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 729 | 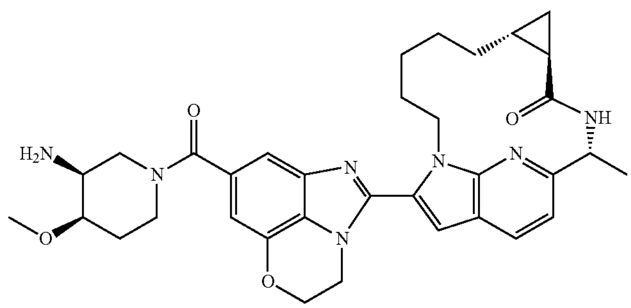 | (2~{R},5~{R},7~{R})-14-[6-[(3~{S},4~{R})-3-amino-4-methoxy-piperidine-1-carbonyl]-9-oxa-1,3-diazatricyclo[6.3.1.0^{4,12}]dodeca-2,4,6,8(12)-tetraen-2-yl]-2-methyl-3,13,19-triazatetracyclo[11.5.2.0^{5,7}.0^{16,20}]icosa-1(19),14,16(20),17-tetraen-4-one |
| 730 | 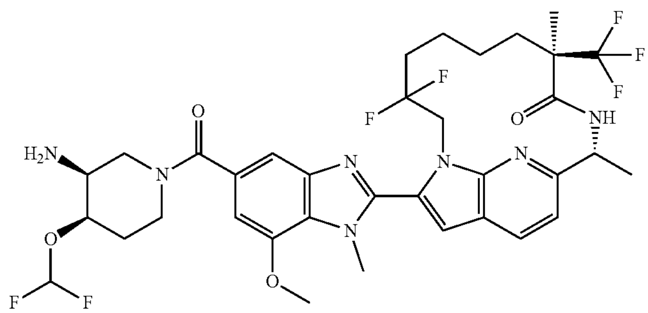 [SMILES: COc1cc(C(=O)N2CC[C@@H](OC(F)F)[C@@H](N)C2)cc2nc(-c3cc4ccc5nc4n3CC(F)(F)CCCC[C@@](C)(C(F)(F)F)C(=O)N[C@@H]5C)n(C)c12] | (8~{R},11~{R})-17-[5-[(3~{S},4~{R})-3-amino-4-(difluoromethoxy)piperidine-1-carbonyl]-7-methoxy-1-methyl-benzimidazol-2-yl]-3,3-difluoro-8,11-dimethyl-8-(trifluoromethyl)-1,10,19-triazatricyclo[10.5.2.0^{15,18}]nonadeca-12(19),13,15(18),16-tetraen-9-one |
| 731 | 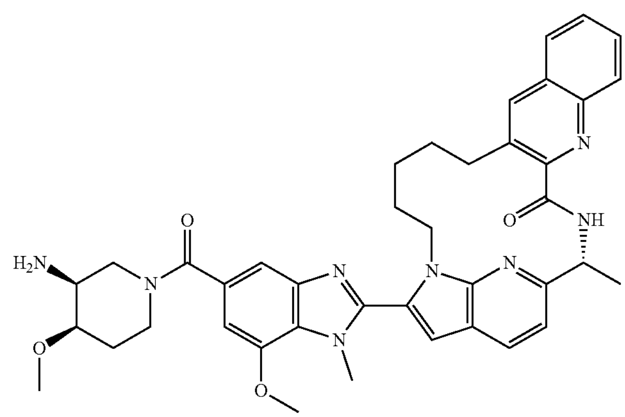 [SMILES: COc1cc(C(=O)N2CC[C@@H](OC)[C@@H](N)C2)cc2nc(-c3cc4ccc5nc4n3CCCCCc3cc4ccccc4nc3C(=O)N[C@@H]5C)n(C)c12] | (2~{R})-21-[5-[(3~{S},4~{R})-3-amino-4-methoxy-piperidine-1-carbonyl]-7-methoxy-1-methyl-benzimidazol-2-yl]-2-methyl-3,6,20,26-tetrazapentacyclo[18.5.2.0^{5,14}.0^{7,12}.0^{23,27}]heptacosa-1(26),5(14),6,8,10,12,21,23(27),24-nonaen-4-one |
| 732 | 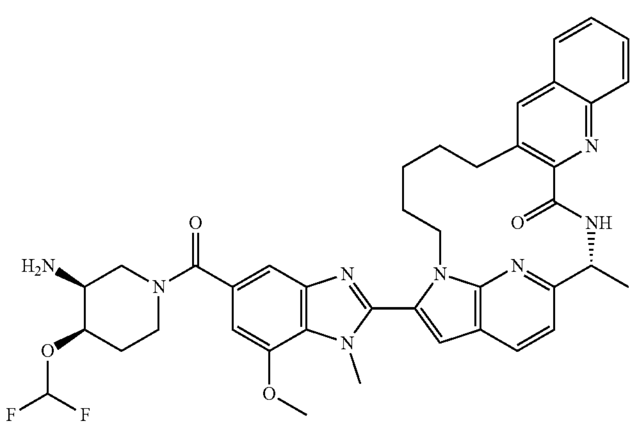 [SMILES: COc1cc(C(=O)N2CC[C@@H](OC(F)F)[C@@H](N)C2)cc2nc(-c3cc4ccc5nc4n3CCCCCc3cc4ccccc4nc3C(=O)N[C@@H]5C)n(C)c12] | (2~{R})-21-[5-[(3~{S},4~{R})-3-amino-4-(difluoromethoxy)piperidine-1-carbonyl]-7-methoxy-1-methyl-benzimidazol-2-yl]-2-methyl-3,6,20,26-tetrazapentacyclo[18.5.2.0^{5,14}.0^{7,12}.0^{23,27}]heptacosa-1(26),5(14),6,8,10,12,21,23(27),24-nonaen-4-one |

TABLE 1A-continued

| Example | Structure | Name |
|---|---|---|
| 733 | 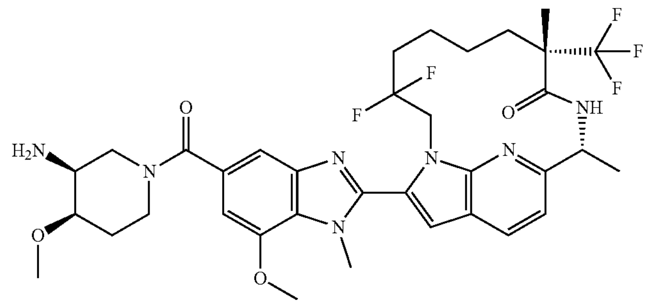 [SMILES: COc1cc(C(=O)N2CC[C@@H](OC)[C@@H](N)C2)cc2nc(-c3cc4ccc5nc4n3CC(F)(F)CCCC[C@](C)(C(F)(F)F)C(=O)N[C@@H]5C)n(C)c12] | (8~{S},11~{R})-17-[5-[(3~{S},4~{R})-3-amino-4-methoxy-piperidine-1-carbonyl]-7-methoxy-1-methyl-benzimidazol-2-yl]-3,3-difluoro-8,11-dimethyl-8-(trifluoromethyl)-1,10,19-triazatricyclo[10.5.2.0^{15,18}]nonadeca-12(19),13,15(18),16-tetraen-9-one |
| 734 | 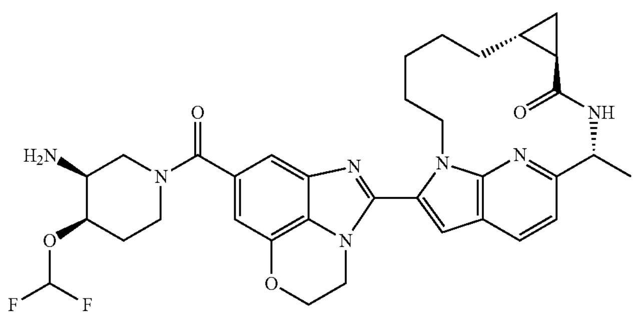 [SMILES: C[C@H]1NC(=O)[C@@H]2C[C@H]2CCCCCn2c(-c3nc4cc(C(=O)N5CC[C@@H](OC(F)F)[C@@H](N)C5)cc5c4n3CCO5)cc3ccc1nc32] | (2~{R},5~{R},7~{R})-14-[6-[(3~{S},4~{R})-3-amino-4-(difluoromethoxy)piperidine-1-carbonyl]-9-oxa-1,3-diazatricyclo[6.3.1.0^{4,12}]dodeca-2,4,6,8(12)-tetraen-2-yl]-2-methyl-3,13,19-triazatetracyclo[11.5.2.0^{5,7}.0^{16,20}]icosa-1(19),14,16(20),17-tetraen-4-one |
| 735 | 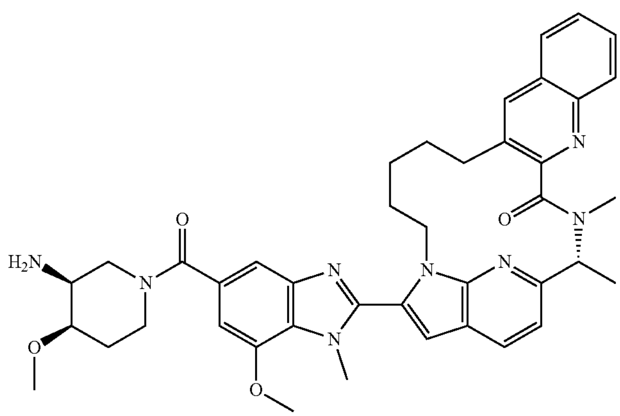 [SMILES: COc1cc(C(=O)N2CC[C@@H](OC)[C@@H](N)C2)cc2nc(-c3cc4ccc5nc4n3CCCCCc3cc4ccccc4nc3C(=O)N(C)[C@@H]5C)n(C)c12] | (2~{R})-21-[5-[(3~{S},4~{R})-3-amino-4-methoxy-piperidine-1-carbonyl]-7-methoxy-1-methyl-benzimidazol-2-yl]-2,3-dimethyl-3,6,20,26-tetrazapentacyclo[18.5.2.0^{5,14}.0^{7,12}.0^{23,27}]heptacosa-1(26),5(14),6,8,10,12,21,23(27),24-nonaen-4-one |
| 736 | 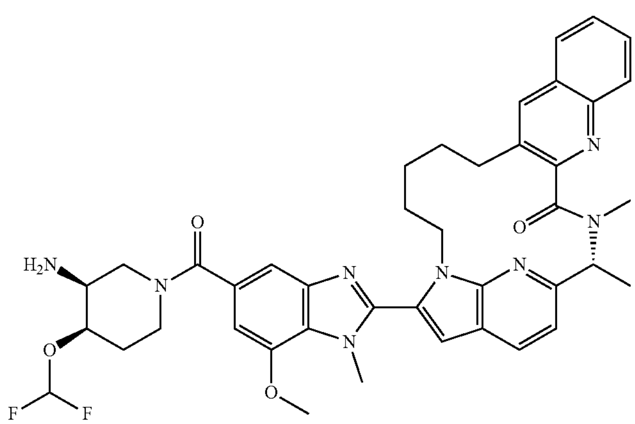 [SMILES: COc1cc(C(=O)N2CC[C@@H](OC(F)F)[C@@H](N)C2)cc2nc(-c3cc4ccc5nc4n3CCCCCc3cc4ccccc4nc3C(=O)N(C)[C@@H]5C)n(C)c12] | (2~{R})-21-[5-[(3~{S},4~{R})-3-amino-4-(difluoromethoxy)piperidine-1-carbonyl]-7-methoxy-1-methyl-benzimidazol-2-yl]-2,3-dimethyl-3,6,20,26-tetrazapentacyclo[18.5.2.0^{5,14}.0^{7,12}.0^{23,27}]heptacosa-1(26),5(14),6,8,10,12,21,23(27),24-nonaen-4-one |

TABLE 1A-continued

| Example | Structure | Name |
|---|---|---|
| 737 | 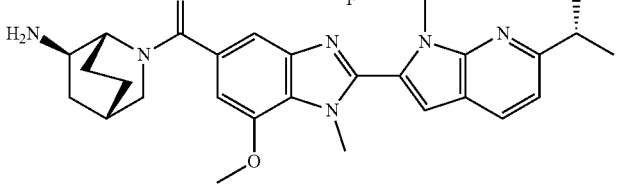 | (2~{R},5~{R},7~{R})-14-[5-[(1~{R},4~{S},6~{R})-6-amino-2-azabicyclo[2.2.2]octane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 738 | 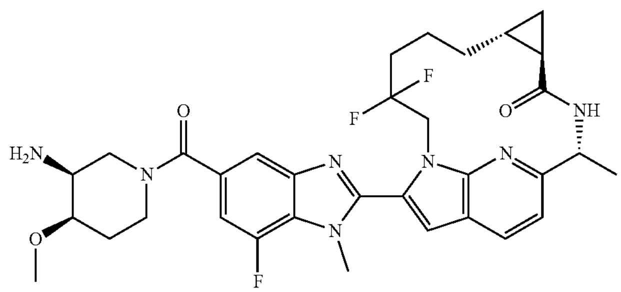 [SMILES: CO[C@@H]1CCN(C(=O)c2cc(F)c3c(c2)nc(-c2cc4ccc5nc4n2CC(F)(F)CCC[C@@H]2C[C@H]2C(=O)N[C@@H]5C)n3C)C[C@@H]1N] | (2~{R},5~{R},7~{R})-14-[5-[(3~{S},4~{R})-3-amino-4-methoxy-piperidine-1-carbonyl]-7-fluoro-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 739 | 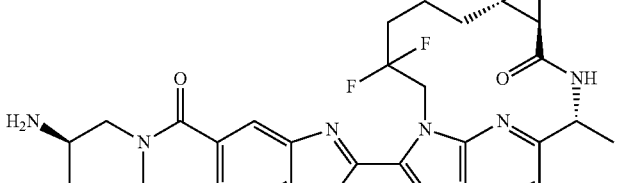 | (2~{R},5~{R},7~{R},9~{E})-14-[5-[3~{S},4~{R})-3-amino-4-methoxy-piperidine-1-carbonyl]-7-fluoro-1-methyl-benzimidazol-2-yl]-11,11-difluoro-2-methyl-3,13,19-triazatetracyclo[11.5.2.0^{5,7}.0^{16,20}]icosa-1(19),9,14,16(20),17-pentaen-4-one |
| 740 | 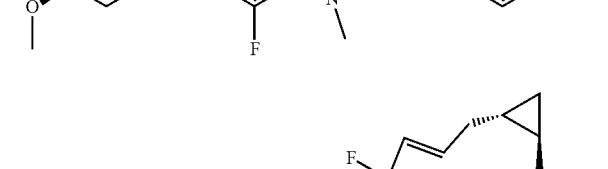 | (2~{R})-17-[5-[(3~{S},4~{R})-3-amino-4-methoxy-piperidine-1-carbonyl]-7-fluoro-1-methyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 741 | 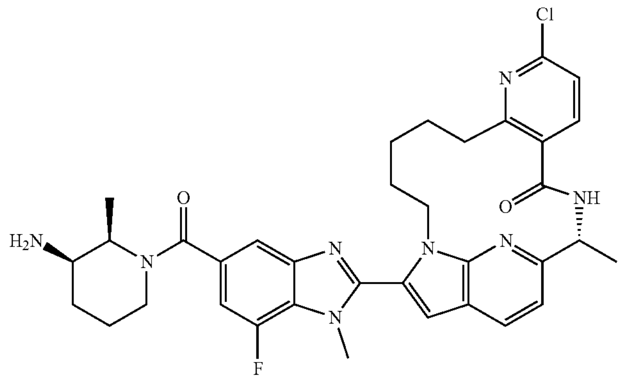 [SMILES: C[C@@H]1[C@H](N)CCCN1C(=O)c1cc(F)c2c(c1)nc(-c1cc3ccc4nc3n1CCCCCc1nc(Cl)ccc1C(=O)N[C@@H]4C)n2C] | (2~{R})-17-[5-[(2~{R},3~{R})-3-amino-2-methyl-piperidine-1-carbonyl]-7-fluoro-1-methyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 742 | 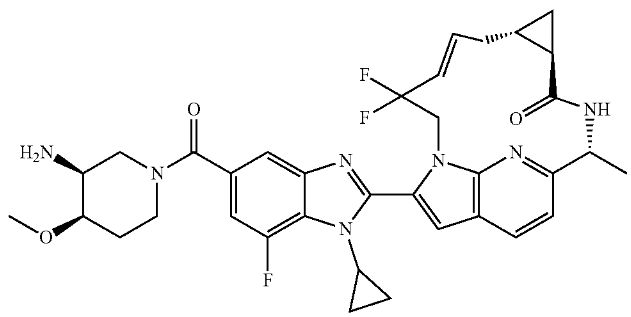 | (2~{R},5~{R},7~{R},9~{E})-14-[5-[(3~{S},4~{R})-3-amino-4-methoxy-piperidine-1-carbonyl]-1-cyclopropyl-7-fluoro-benzimidazol-2-yl]-11,11-difluoro-2-methyl-3,13,19-triazatetracyclo[11.5.2.0^{5,7}.0^{16,20}]icosa-1(19),9,14,16(20),17-pentaen-4-one |
| 743 | 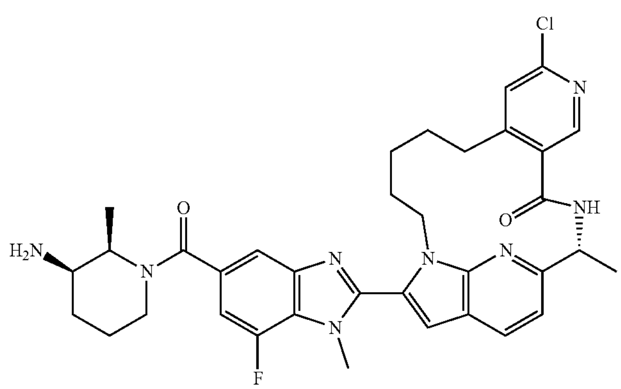 [SMILES: C[C@@H]1[C@H](N)CCCN1C(=O)c1cc(F)c2c(c1)nc(-c1cc3ccc4nc3n1CCCCCc1cc(Cl)ncc1C(=O)N[C@@H]4C)n2C] | (2~{R})-17-[5-[(2~{R},3~{R})-3-amino-2-methyl-piperidine-1-carbonyl]-7-fluoro-1-methyl-benzimidazol-2-yl]-8-chloro-2-methyl-3,7,16,22-tetrazatetracyclo[14.5.2.0^{5,10}.0^{19,23}]tricosa-1(22),5(10),6,8,17,19(23),20-heptaen-4-one |
| 744 | 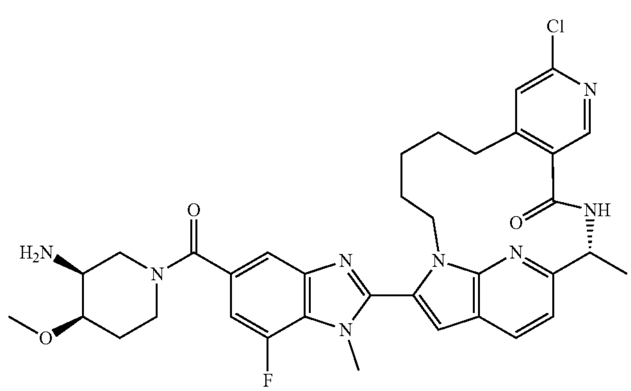 | (2~{R})-17-[5-[(3~{S},4~{R})-3-amino-4-methoxy-piperidine-1-carbonyl]-7-fluoro-1-methyl-benzimidazol-2-yl]-8-chloro-2-methyl-3,7,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 745 | 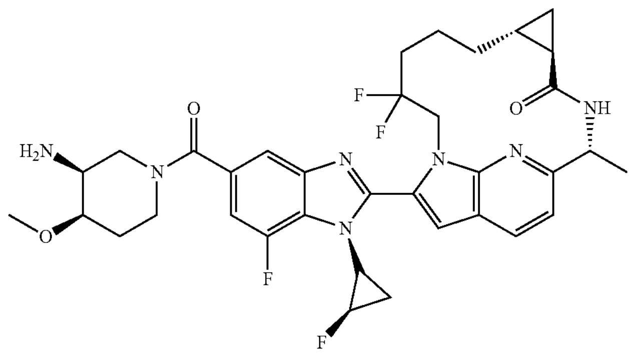 | (2~{R},5~{R},7~{R})-14-[5-[(3~{S},4~{R})-3-amino-4-methoxy-piperidine-1-carbonyl]-7-fluoro-1-[(1~{S},2~{R})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 746 | 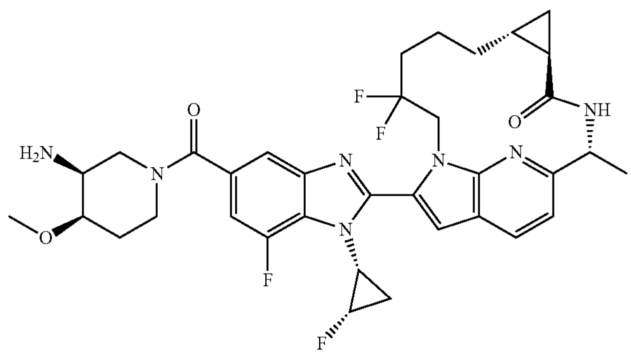 | (2~{R},5~{R},7~{R})-14-[5-[(3~{S},4~{R})-3-amino-4-methoxy-piperidine-1-carbonyl]-7-fluoro-1-[(1~{R},2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 747 | 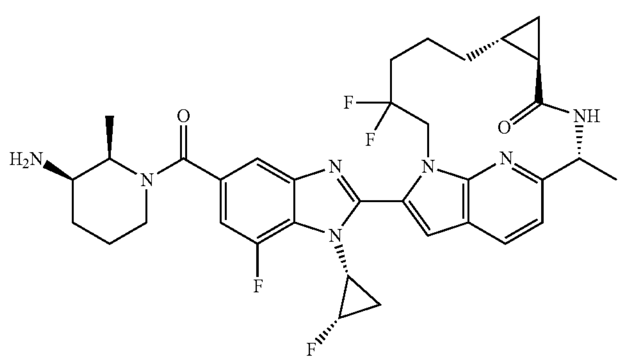 [SMILES: C[C@@H]1[C@H](N)CCCN1C(=O)c1cc(F)c2c(c1)nc(-c1cc3ccc4nc3n1CC(F)(F)CCC[C@@H]1C[C@H]1C(=O)N[C@@H]4C)n2[C@@H]1C[C@@H]1F] | (2~{R},5~{R},7~{R})-14-[5-[(2~{R},3~{R})-3-amino-2-methyl-piperidine-1-carbonyl]-7-fluoro-1-[(1~{R},2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 748 | 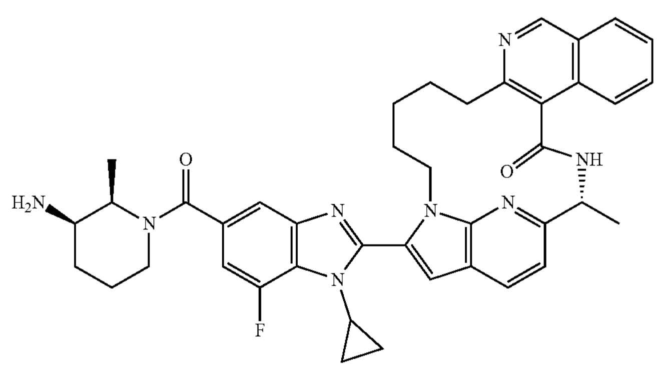 [SMILES: C[C@@H]1[C@H](N)CCCN1C(=O)c1cc(F)c2c(c1)nc(-c1cc3ccc4nc3n1CCCCCc1ncc3ccccc3c1C(=O)N[C@@H]4C)n2C1CC1] | (2~{R})-21-[5-[(2~{R},3~{R})-3-amino-2-methyl-piperidine-1-carbonyl]-1-cyclopropyl-7-fluoro-benzimidazol-2-yl]-2-methyl-3,13,20,26-tetrazapentacyclo[18.5.2.0^{5,14}.0^{6,11}.0^{23,27}]heptacosa-1(26),5(14),6(11),7,9,12,21,23(27),24-nonaen-4-one |

TABLE 1A-continued

| Example | Structure | Name |
|---|---|---|
| 749 | 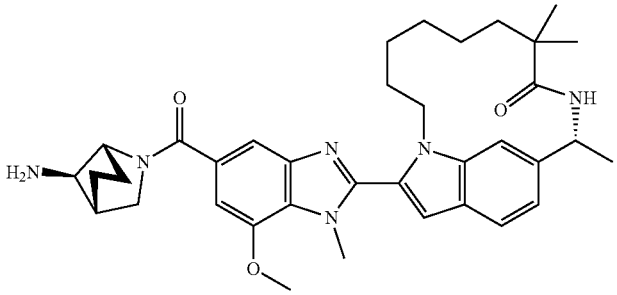 | (11~{R})-17-[5-[(1~{R},4~{R},7~{R})-7-amino-2-azabicyclo[2.2.1]heptane-2-carbonyl]-7-methoxy-1-methyl-benzimidazol-2-yl]-8,8,11-trimethyl-1,10-diazatricyclo[10.5.2.0^{15,18}]nonadeca-12(19),13,15(18),16-tetraen-9-one |
| 750 | 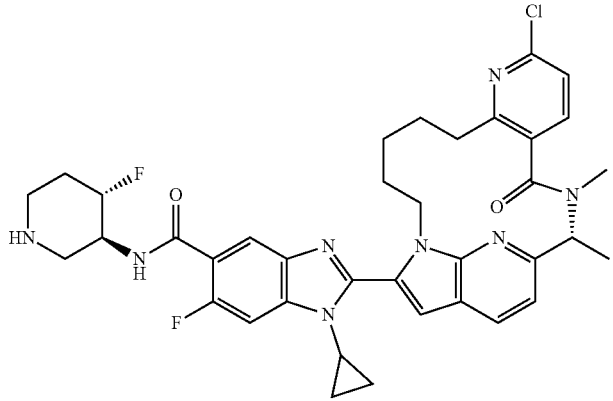 [SMILES: C[C@@H]1c2ccc3cc(-c4nc5cc(C(=O)N[C@H]6CNCC[C@@H]6F)c(F)cc5n4C4CC4)n(c3n2)CCCCCc2nc(Cl)ccc2C(=O)N1C] | 2-[(2~{R})-8-chloro-2,3-dimethyl-4-oxo-3,9,16,22-tetrazatetracyclo[14.5.2.0^{5,10}.0^{19,23}]tricosa-1(22),5(10),6,8,17,19(23),20-heptaen-17-yl]-1-cyclopropyl-6-fluoro-~{N}-[(3~{S},4~{S})-4-fluoro-3-piperidyl]benzimidazole-5-carboxamide |
| 751 | 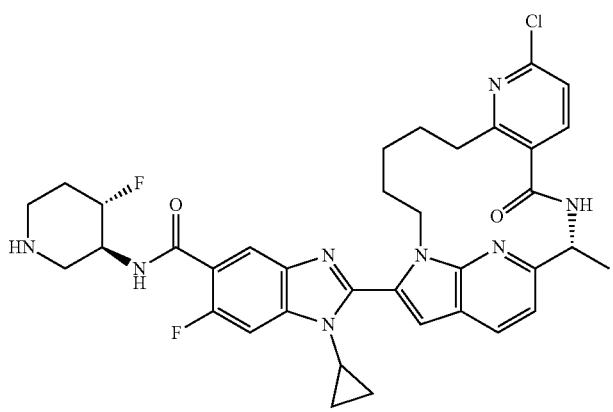 [SMILES: C[C@H]1NC(=O)c2ccc(Cl)nc2CCCCCn2c(-c3nc4cc(C(=O)N[C@H]5CNCC[C@@H]5F)c(F)cc4n3C3CC3)cc3ccc1nc32] | 2-[(2~{R})-8-chloro-2-methyl-4-oxo-3,9,16,22-tetrazatetracyclo[14.5.2.0^{5,10}.0^{19,23}]tricosa-1(22),5(10),6,8,17,19(23),20-heptaen-17-yl]-1-cyclopropyl-6-fluoro-~{N}-[(3~{S},4~{S})-4-fluoro-3-piperidyl]benzimidazole-5-carboxamide |
| 752 | 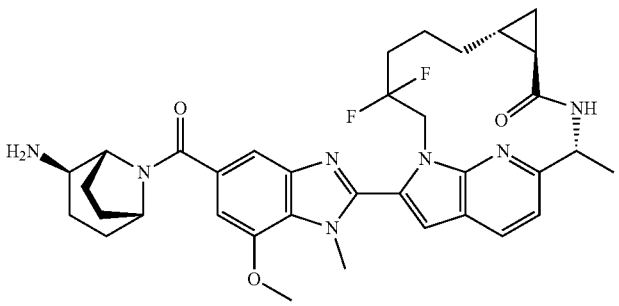 | (2~{R},5~{R},7~{R})-14-[5-[(1~{R},2~{R},5~{R})-2-amino-8-azabicyclo[3.2.1]octane-8-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 753 | 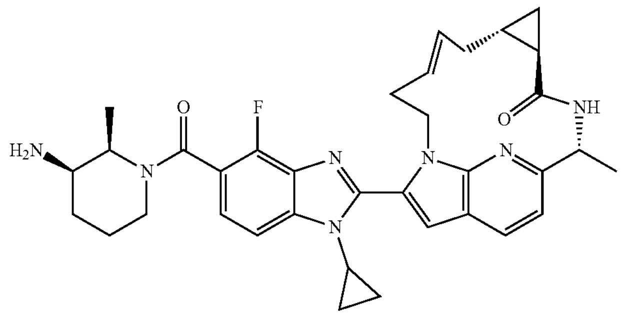 [SMILES: C[C@@H]1[C@H](N)CCCN1C(=O)c1ccc2c(nc(-c3cc4ccc5nc4n3CC/C=C/C[C@@H]3C[C@H]3C(=O)N[C@@H]5C)n2C2CC2)c1F] | (2~{R},5~{R},7~{R},9~{E})-14-[5-[(2~{R},3~{R})-3-amino-2-methyl-piperidine-1-carbonyl]-1-cyclopropyl-4-fluoro-benzimidazol-2-yl]-2-methyl-3,13,19-triazatetracyclo[11.5.2.0^{5,7}.0^{16,20}]icosa-1(19),9,14,16(20),17-pentaen-4-one |
| 754 | 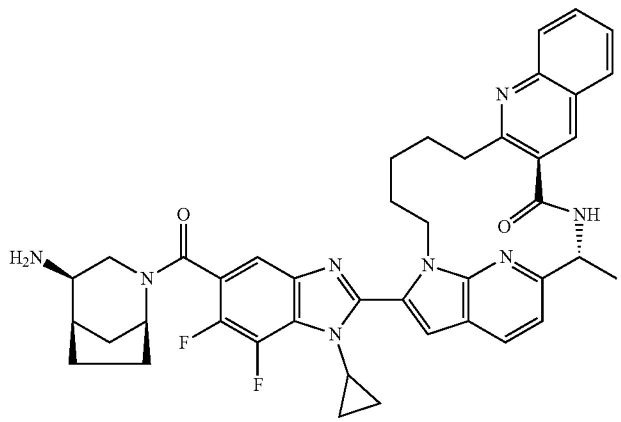 | (2~{R})-21-[5-[(1~{S},4~{R},5~{R})-4-amino-2-azabicyclo[3.2.1]octane-2-carbonyl]-1-cyclopropyl-6,7-difluoro-benzimidazol-2-yl]-2-methyl-3,13,20,26-tetrazapentacyclo[18.5.2.0^{5,14}.0^{7,12}.0^{23,27}]heptacosa-1(26),5(14),6,8,10,12,21,23(27),24-nonaen-4-one |
| 755 | 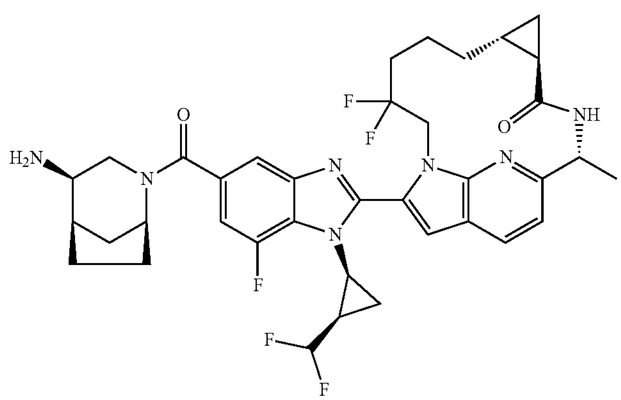 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@H]3C[C@H]3C(F)F)cc3ccc1nc32] | (2~{R},5~{R},7~{R})-14-[5-[(1~{S},4~{R},5~{R})-4-amino-2-azabicyclo[3.2.1]octane-2-carbonyl]-1-[(1~{S},2~{R})-2-(difluoromethyl)cyclopropyl]-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 756 | 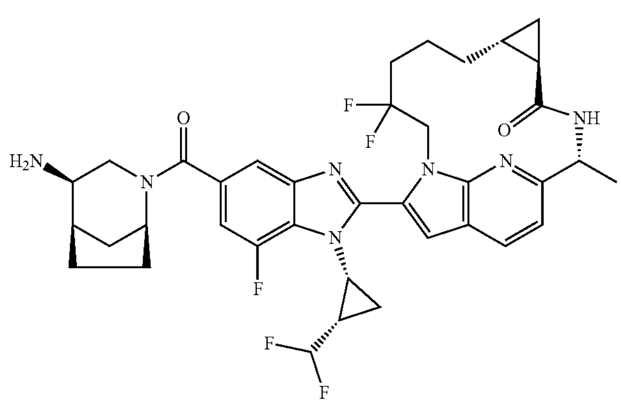 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3[C@@H]3C[C@@H]3C(F)F)cc3ccc1nc32] | (2~{R},5~{R},7~{R})-14-[5-[(1~{S},4~{R},5~{R})-4-amino-2-azabicyclo[3.2.1]octane-2-carbonyl]-1-[(1~{R},2~{S})-2-(difluoromethyl)cyclopropyl]-7-fluoro-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
| --- | --- | --- |
| 757 | 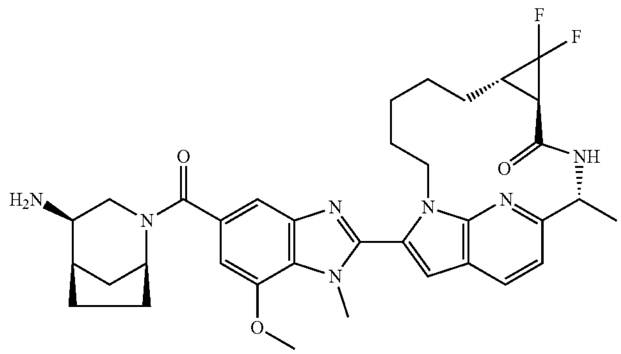 [SMILES: COc1cc(C(=O)N2C[C@H](N)[C@@H]3CC[C@H]2C3)cc2nc(-c3cc4ccc5nc4n3CCCCC[C@H]3[C@H](C(=O)N[C@@H]5C)C3(F)F)n(C)c12] | (2~{R},5~{R},7~{S})-14-[5-[(1~{S},4~{R},5~{R})-4-amino-2-azabicyclo[3.2.1]octane-2-carbonyl]-7-methoxy-1-methyl-benzimidazol-2-yl]-6,6-difluoro-2-methyl-3,13,19-triazatetracyclo[11.5.2.0^{5,7}.0^{16,20}]icosa-1(19),14,16(20),17-tetraen-4-one |
| 758 | 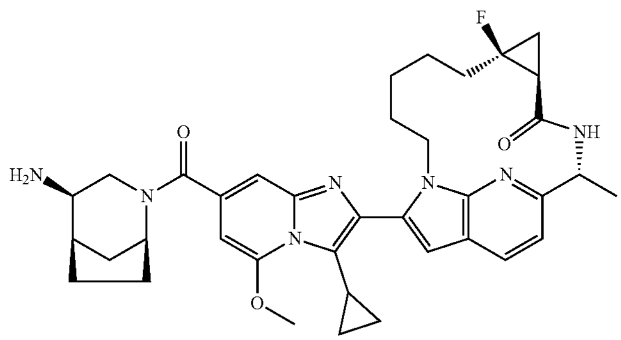 [SMILES: COc1cc(C(=O)N2C[C@H](N)[C@@H]3CC[C@H]2C3)cc2nc(-c3cc4ccc5nc4n3CCCCC[C@]3(F)C[C@H]3C(=O)N[C@@H]5C)c(C3CC3)n12] | (2~{R},5~{S},7~{S})-14-[7-[(1~{S},4~{R},5~{R})-4-amino-2-azabicyclo[3.2.1]octane-2-carbonyl]-3-cyclopropyl-5-methoxy-imidazo[1,2-a]pyridin-2-yl]-7-fluoro-2-methyl-3,13,19-triazatetracyclo[11.5.2.0^{5,7}.0^{16,20}]icosa-1(19),14,16(20),17-tetraen-4-one |
| 759 | 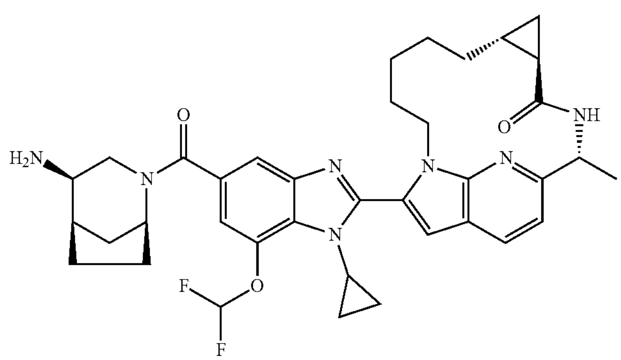 [SMILES: C[C@H]1NC(=O)[C@@H]2C[C@H]2CCCCCn2c(-c3nc4cc(C(=O)N5C[C@H](N)[C@@H]6CC[C@H]5C6)cc(OC(F)F)c4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-7-(difluoromethoxy)benzimidazol-2-yl]-2-methyl-3,13,19-triazatetracyclo[11.5.2.0^{5,7}.0^{16,20}]icosa-1(19),14,16(20),17-tetraen-4-one |
| 760 | 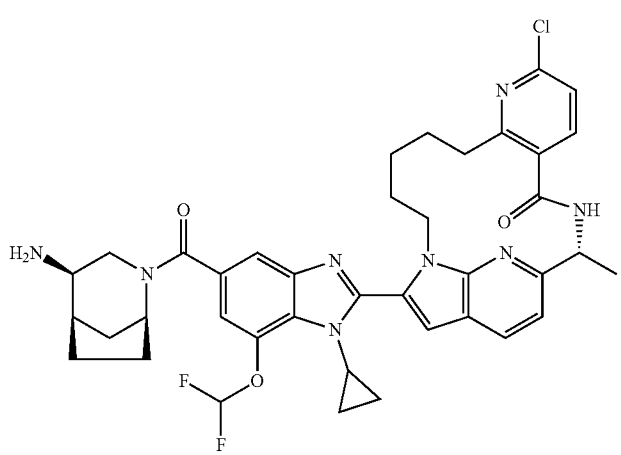 [SMILES: C[C@H]1NC(=O)c2ccc(Cl)nc2CCCCCn2c(-c3nc4cc(C(=O)N5C[C@H](N)[C@@H]6CC[C@H]5C6)cc(OC(F)F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-(difluoromethoxy)benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 761 | 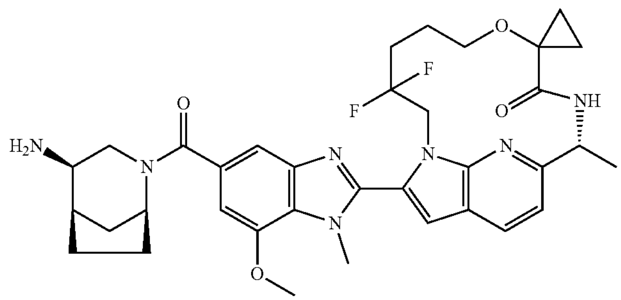 [SMILES: COc1cc(C(=O)N2C[C@H](N)[C@@H]3CC[C@H]2C3)cc2nc(-c3cc4ccc5nc4n3CC(F)(F)CCCOC3(CC3)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-3,3-difluoro-11-methyl-spiro[7-oxa-1,10,19-triazatricyclo[10.5.2.0^{15,18}]nonadeca-12(19),13,15(18),16-tetraene-8,1'-cyclopropane]-9-one |
| 762 | 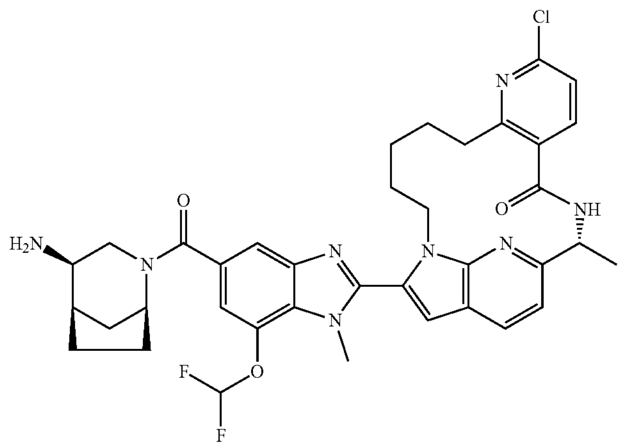 [SMILES: C[C@H]1NC(=O)c2ccc(Cl)nc2CCCCCn2c(-c3nc4cc(C(=O)N5C[C@H](N)[C@@H]6CC[C@H]5C6)cc(OC(F)F)c4n3C)cc3ccc1nc32] | (2~{R})-17-[5-[(1~{S},4~{R},5~{R})-4-amino-2-azabicyclo[3.2.1]octane-2-carbonyl]-7-(difluoromethoxy)-1-methyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 763 | 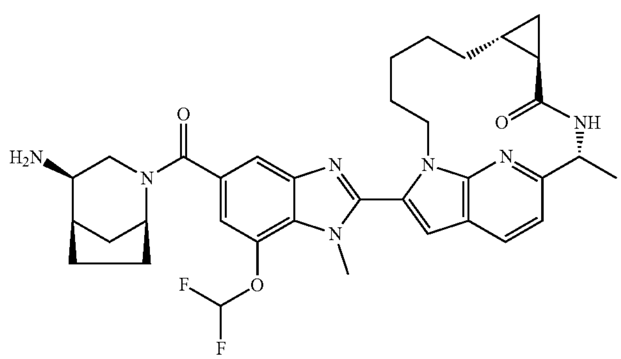 [SMILES: C[C@H]1NC(=O)[C@@H]2C[C@H]2CCCCCn2c(-c3nc4cc(C(=O)N5C[C@H](N)[C@@H]6CC[C@H]5C6)cc(OC(F)F)c4n3C)cc3ccc1nc32] | (2~{R},5~{R},7~{R})-14-[5-[(1~{S},4~{R},5~{R})-4-amino-2-azabicyclo[3.2.1]octane-2-carbonyl]-7-(difluoromethoxy)-1-methyl-benzimidazol-2-yl]-2-methyl-3,13,19-triazatetracyclo[11.5.2.0^{5,7}.0^{16,20}]icosa-1(19),14,16(20),17-tetraen-4-one |
| 764 | 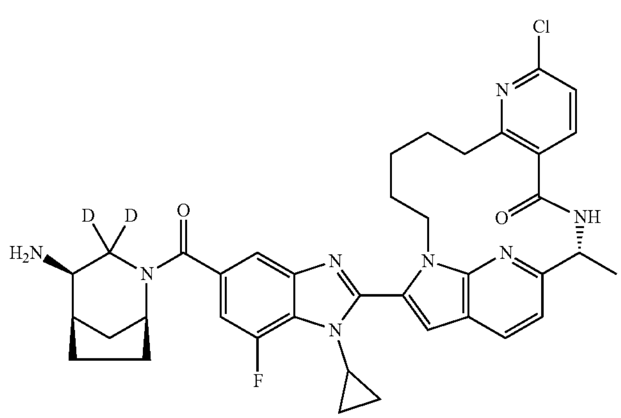 [SMILES: [2H]C1([2H])[C@H](N)[C@@H]2CC[C@@H](C2)N1C(=O)c1cc(F)c2c(c1)nc(-c1cc3ccc4nc3n1CCCCCc1nc(Cl)ccc1C(=O)N[C@@H]4C)n2C1CC1] | (2~{R})-17-[5-[(1~{S},4~{R},5~{R})-4-amino-3,3-dideuterio-2-azabicyclo[3.2.1]octane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 765 | 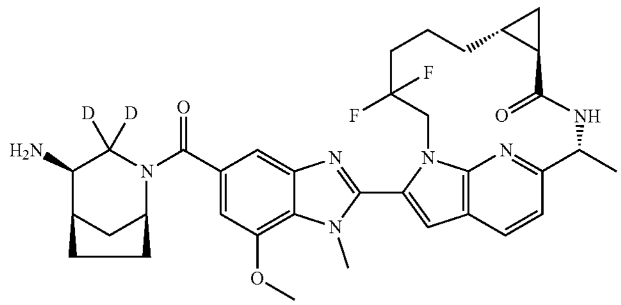 [SMILES: [2H]C1([2H])[C@H](N)[C@@H]2CC[C@@H](C2)N1C(=O)c1cc(OC)c2c(c1)nc(-c1cc3ccc4nc3n1CC(F)(F)CCC[C@@H]1C[C@H]1C(=O)N[C@@H]4C)n2C] | (2~{R},5~{R},7~{R})-14-[5-[(1~{S},4~{R},5~{R})-4-amino-3,3-dideuterio-2-azabicyclo[3.2.1]octane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 766 | 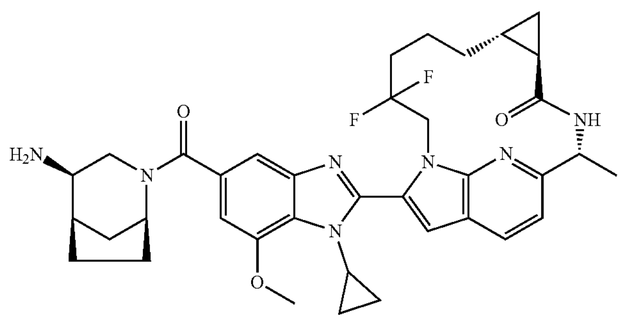 [SMILES: COc1cc(C(=O)N2C[C@H](N)[C@@H]3CC[C@H]2C3)cc2nc(-c3cc4ccc5nc4n3CC(F)(F)CCC[C@@H]3C[C@H]3C(=O)N[C@@H]5C)n(C3CC3)c12] | (2~{R},5~{R},7~{R})-14-[5-[(1~{S},4~{R},5~{R})-4-amino-2-azabicyclo[3.2.1]octane-2-carbonyl]-1-cyclopropyl-7-methoxy-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 767 | 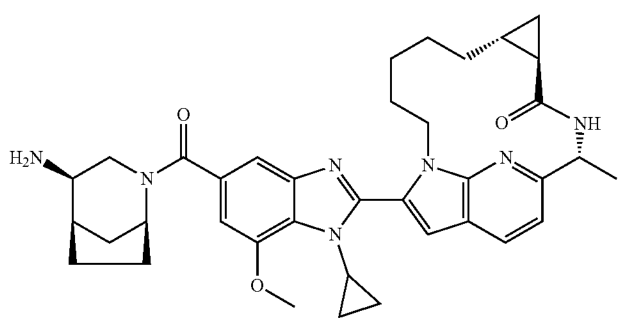 [SMILES: COc1cc(C(=O)N2C[C@H](N)[C@@H]3CC[C@H]2C3)cc2nc(-c3cc4ccc5nc4n3CCCCC[C@@H]3C[C@H]3C(=O)N[C@@H]5C)n(C3CC3)c12] | (2~{R},5~{R},7~{R})-14-[5-[(1~{S},4~{R},5~{R})-4-amino-2-azabicyclo[3.2.1]octane-2-carbonyl]-1-cyclopropyl-7-methoxy-benzimidazol-2-yl]-2-methyl-3,13,19-triazatetracyclo[11.5.2.0^{5,7}.0^{16,20}]icosa-1(19),14,16(20),17-tetraen-4-one |
| 768 | 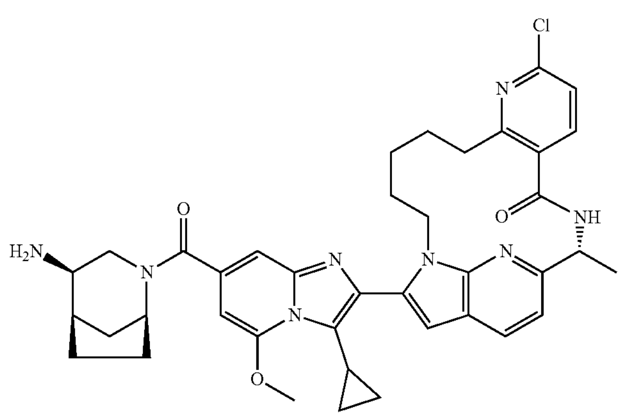 [SMILES: COc1cc(C(=O)N2C[C@H](N)[C@@H]3CC[C@H]2C3)cc2nc(-c3cc4ccc5nc4n3CCCCCc3nc(Cl)ccc3C(=O)N[C@@H]5C)c(C3CC3)n12] | (2~{R})-17-[7-[(1~{S},4~{R},5~{R})-4-amino-2-azabicyclo[3.2.1]octane-2-carbonyl]-3-cyclopropyl-5-methoxy-imidazo[1,2-a]pyridin-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 769 | 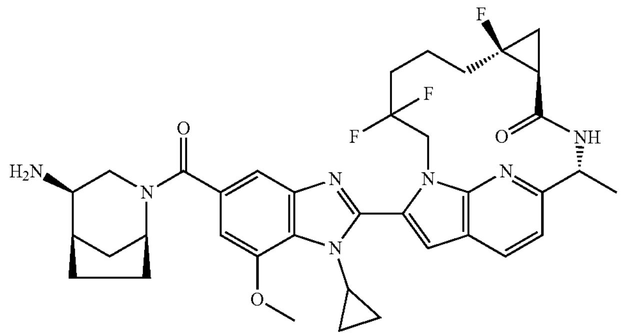 [SMILES: COc1cc(C(=O)N2C[C@H](N)[C@@H]3CC[C@H]2C3)cc2nc(-c3cc4ccc5nc4n3CC(F)(F)CCC[C@]3(F)C[C@H]3C(=O)N[C@@H]5C)n(C3CC3)c12] | (2~{R},5~{S},7~{S})-14-[5-[(1~{S},4~{R},5~{R})-4-amino-2-azabicyclo[3.2.1]octane-2-carbonyl]-1-cyclopropyl-7-methoxy-benzimidazol-2-yl]-7,11,11-trifluoro-2-methyl-3,13,19-triazatetracyclo[11.5.2.0^{5,7}.0^{16,20}]icosa-1(19),14,16(20),17-tetraen-4-one |
| 770 | 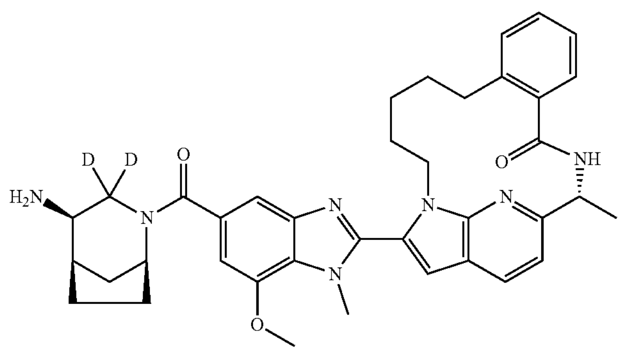 [SMILES: [2H]C1([2H])[C@H](N)[C@@H]2CC[C@@H](C2)N1C(=O)c1cc(OC)c2c(c1)nc(-c1cc3ccc4nc3n1CCCCCc1ccccc1C(=O)N[C@@H]4C)n2C] | (2~{R})-17-[5-[(1~{S},4~{R},5~{R})-4-amino-3,3-dideuterio-2-azabicyclo[3.2.1]octane-2-carbonyl]-7-methoxy-1-methyl-benzimidazol-2-yl]-2-methyl-3,16,22-triazatetracyclo[14.5.2.0^{5,10}.0^{19,23}]tricosa-1(22),5(10),6,8,17,19(23),20-heptaen-4-one |
| 771 | 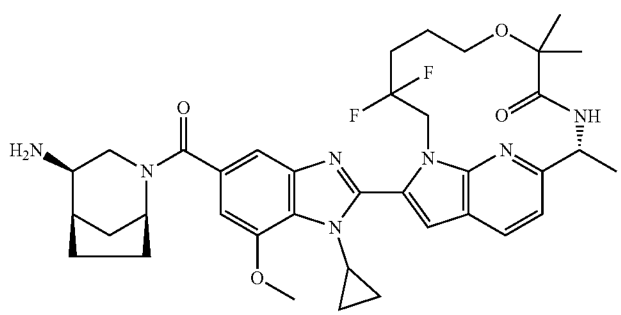 [SMILES: COc1cc(C(=O)N2C[C@H](N)[C@@H]3CC[C@H]2C3)cc2nc(-c3cc4ccc5nc4n3CC(F)(F)CCCOC(C)(C)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-3,3-difluoro-8,8,11-trimethyl-7-oxa-1,10,19-triazatricyclo[10.5.2.0^{15,18}]nonadeca-12(19),13,15(18),16-tetraen-9-one |
| 772 | 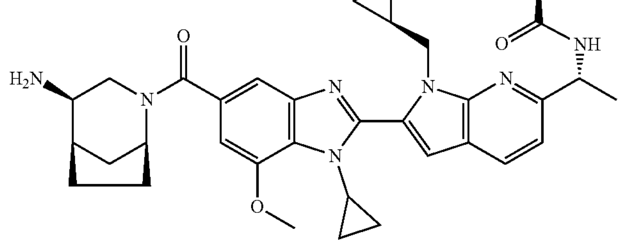 | (3~{S},5~{R},8~{S},10~{S},13~{R})-19-[5-[(1~{S},4~{R},5~{R})-4-amino-2-azabicyclo[3.2.1]octane-2-carbonyl]-1-cyclopropyl-7-methoxy-benzimidazol-2-yl]-8-fluoro-13-methyl-1,12,21-triazapentacyclo[12.5.2.0^{3,5}.0^{8,10}.0^{17,20}]henicosa-14(21),15,17(20),18-tetraen-11-one |

TABLE 1A-continued

| Example | Structure | Name |
|---|---|---|
| 773 | 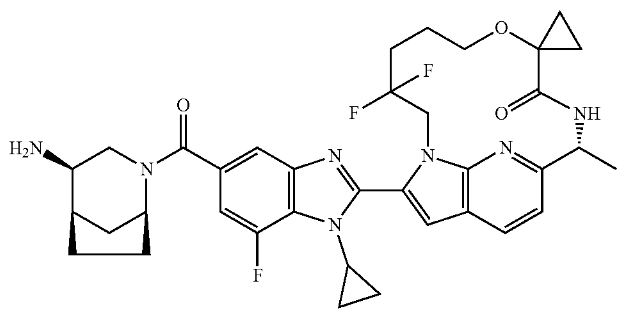 [SMILES: C[C@H]1NC(=O)C2(CC2)OCCCC(F)(F)Cn2c(-c3nc4cc(C(=O)N5C[C@H](N)[C@@H]6CC[C@H]5C6)cc(F)c4n3C3CC3)cc3ccc1nc32] | (11~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-3,3-difluoro-11-methyl-spiro[7-oxa-1,10,19-triazatricyclo[10.5.2.0^{15,18}]nonadeca-12(19),13,15(18),16-tetraene-8,1'-cyclopropane]-9-one |
| 774 | 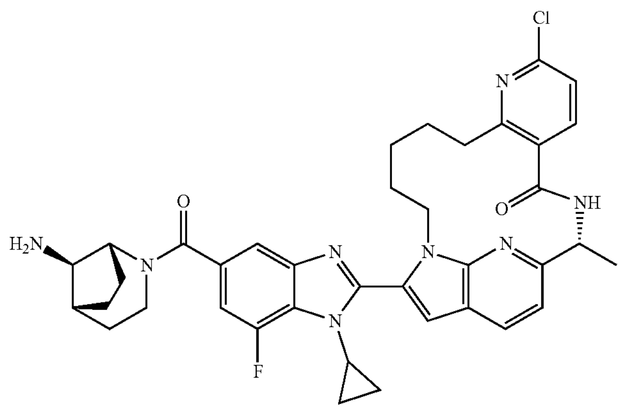 [SMILES: C[C@H]1NC(=O)c2ccc(Cl)nc2CCCCCn2c(-c3nc4cc(C(=O)N5CC[C@H]6CC[C@@H]5[C@@H]6N)cc(F)c4n3C3CC3)cc3ccc1nc32] | (2~{R})-17-[5-[(1~{R},5~{R},8~{R})-8-amino-2-azabicyclo[3.2.1]octane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 775 | 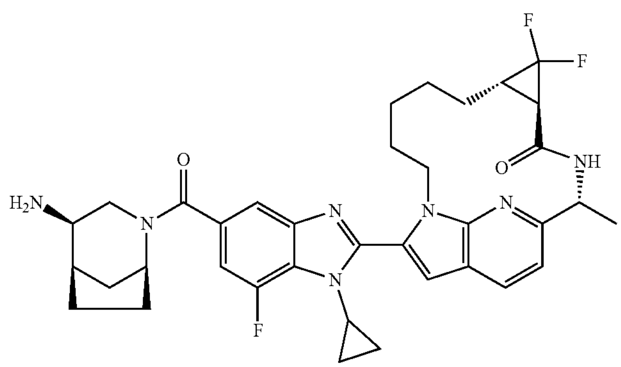 [SMILES: C[C@H]1NC(=O)[C@H]2[C@H](CCCCCn3c(-c4nc5cc(C(=O)N6C[C@H](N)[C@@H]7CC[C@H]6C7)cc(F)c5n4C4CC4)cc4ccc1nc43)C2(F)F] | (2~{R},5~{R},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-6,6-difluoro-2-methyl-3,13,19-triazatetracyclo[11.5.2.0^{5,7}.0^{16,20}]icosa-1(19),14,16(20),17-tetraen-4-one |
| 776 | 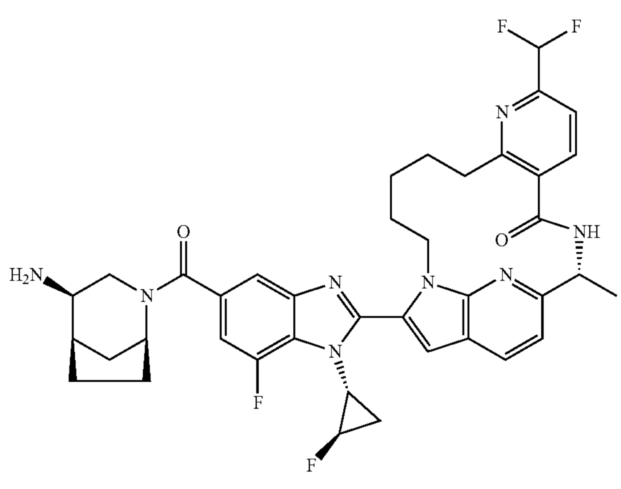 [SMILES: C[C@H]1NC(=O)c2ccc(C(F)F)nc2CCCCCn2c(-c3nc4cc(C(=O)N5C[C@H](N)[C@@H]6CC[C@H]5C6)cc(F)c4n3[C@@H]3C[C@H]3F)cc3ccc1nc32] | (2~{R})-17-[5-[(1~{S},4~{R},5~{R})-4-amino-2-azabicyclo[3.2.1]octane-2-carbonyl]-7-fluoro-1-[(1~{R},2~{R})-2-fluorocyclopropyl]benzimidazol-2-yl]-8-(difluoromethyl)-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 777 | 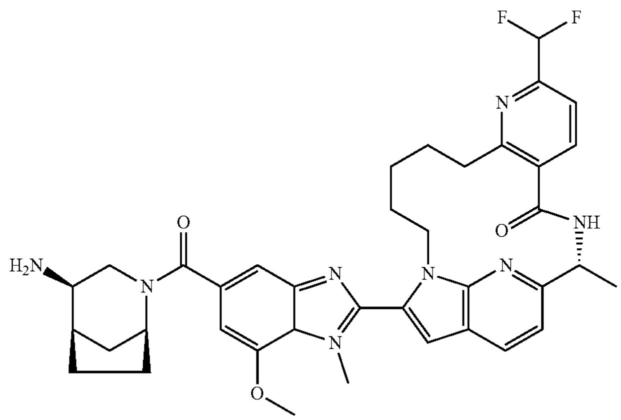 | (2~{R})-17-[7-[(1~{S},4~{R},5~{R})-4-amino-2-azabicyclo[3.2.1]octane-2-carbonyl]-5-methoxy-3-methyl-imidazo[1,2-a]pyridin-2-yl]-8-(difluoromethyl)-2-methyl-3,9,16,22-tetrazatetracyclo[14.5.2.0^{5,10}.0^{19,23}]tricosa-1(22),5(10),6,8,17,19(23),20-heptaen-4-one |
| 778 | 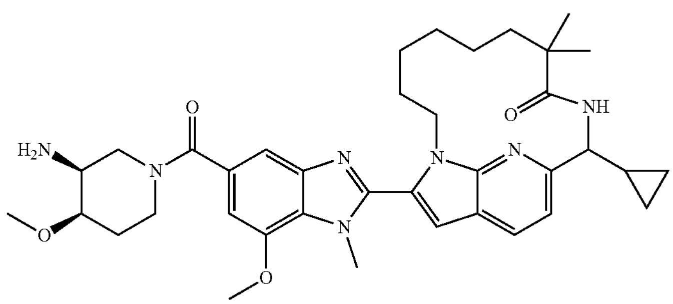 [SMILES: COc1cc(C(=O)N2CC[C@@H](OC)[C@@H](N)C2)cc2nc(-c3cc4ccc5nc4n3CCCCCCC(C)(C)C(=O)NC5C3CC3)n(C)c12] | 17-[5-[(3~{S},4~{R})-3-amino-4-methoxy-piperidine-1-carbonyl]-7-methoxy-1-methyl-benzimidazol-2-yl]-11-cyclopropyl-8,8-dimethyl-1,10,19-triazatricyclo[10.5.2.0^{15,18}]nonadeca-12,14,16,18-tetraen-9-one |
| 779 | 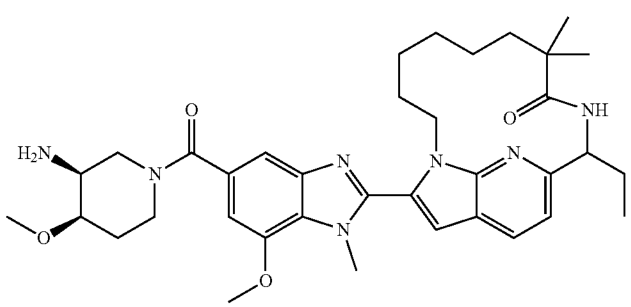 [SMILES: CCC1NC(=O)C(C)(C)CCCCCCn2c(-c3nc4cc(C(=O)N5CC[C@@H](OC)[C@@H](N)C5)cc(OC)c4n3C)cc3ccc1nc32] | 17-[5-[(3~{S},4~{R})-3-amino-4-methoxy-piperidine-1-carbonyl]-7-methoxy-1-methyl-benzimidazol-2-yl]-11-ethyl-8,8-dimethyl-1,10,19-triazatricyclo[10.5.2.0^{15,18}]nonadeca-12,14,16,18-tetraen-9-one |
| 780 | 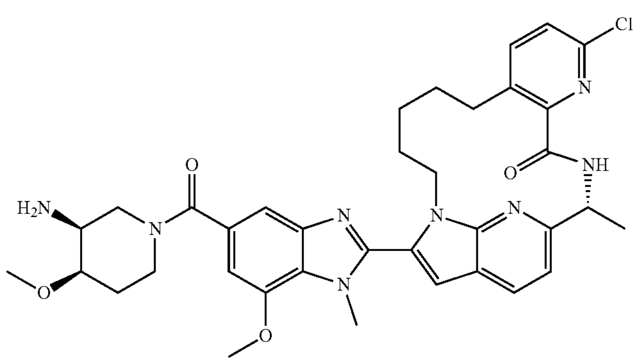 | (2~{R})-17-[5-[(3~{S},4~{R})-3-amino-4-methoxy-piperidine-1-carbonyl]-7-methoxy-1-methyl-benzimidazol-2-yl]-7-chloro-2-methyl-3,6,16,22-tetrazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 781 | 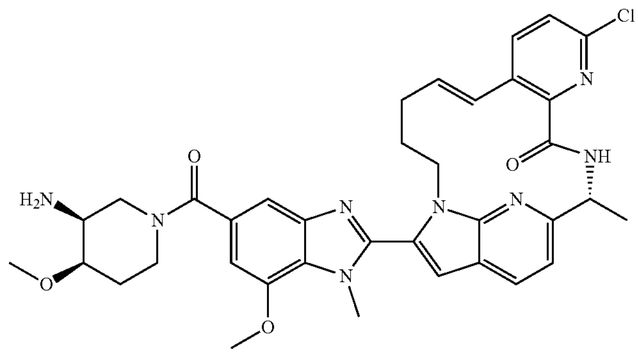 | (2~{R},11~{E})-17-[5-[(3~{S},4~{R})-3-amino-4-methoxy-piperidine-1-carbonyl]-7-methoxy-1-methyl-benzimidazol-2-yl]-7-chloro-2-methyl-3,6,16,22-tetrazatetracyclo[14.5.2.0^{5,10}.0^{19,23}]tricosa-1(21),5(10),6,8,11,17,19,22-octaen-4-one |
| 782 | 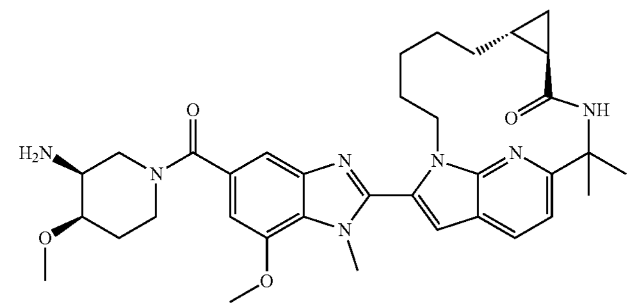 | (5~{R},7~{R})-14-[5-[(3~{S},4~{R})-3-amino-4-methoxy-piperidine-1-carbonyl]-7-methoxy-1-methyl-benzimidazol-2-yl]-2,2-dimethyl-3,13,19-triazatetracyclo[11.5.2.0^{5,7}.0^{16,20}]icosa-1(18),14,16,19-tetraen-4-one |
| 783 | 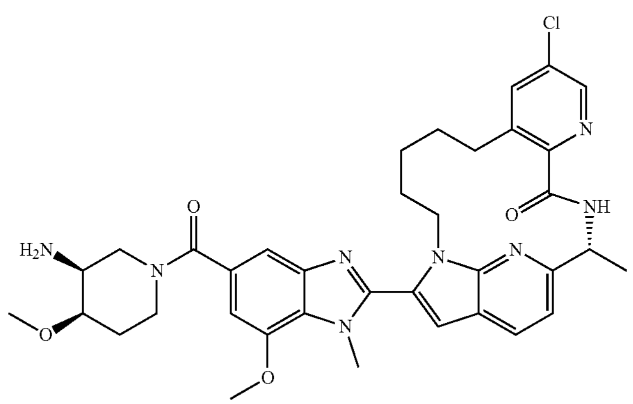 | (2~{R})-17-[5-[(3~{S},4~{R})-3-amino-4-methoxy-piperidine-1-carbonyl]-7-methoxy-1-methyl-benzimidazol-2-yl]-8-chloro-2-methyl-3,6,16,22-tetrazatetracyclo[14.5.2.0^{5,10}.0^{19,23}]tricosa-1(21),5(10),6,8,17,19,22-heptaen-4-one |
| 784 | 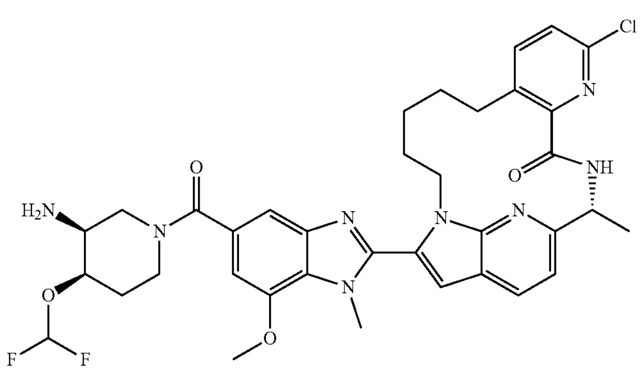 [SMILES: COc1cc(C(=O)N2CC[C@@H](OC(F)F)[C@@H](N)C2)cc2nc(-c3cc4ccc5nc4n3CCCCCc3ccc(Cl)nc3C(=O)N[C@@H]5C)n(C)c12] | (2~{R})-17-[5-[(3~{S},4~{R})-3-amino-4-(difluoromethoxy)piperidine-1-carbonyl]-7-methoxy-1-methyl-benzimidazol-2-yl]-7-chloro-2-methyl-3,6,16,22-tetrazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 785 | 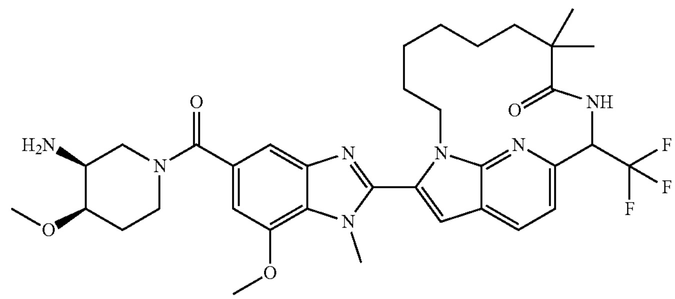 [SMILES: COc1cc(C(=O)N2CC[C@@H](OC)[C@@H](N)C2)cc2nc(-c3cc4ccc5nc4n3CCCCCCC(C)(C)C(=O)NC5C(F)(F)F)n(C)c12] | 17-[5-[(3~{S},4~{R})-3-amino-4-methoxy-piperidine-1-carbonyl]-7-methoxy-1-methyl-benzimidazol-2-yl]-8,8-dimethyl-11-(trifluoromethyl)-1,10,19-triazatricyclo[10.5.2.0^{15,18}]nonadeca-12,14,16,18-tetraen-9-one |
| 786 | 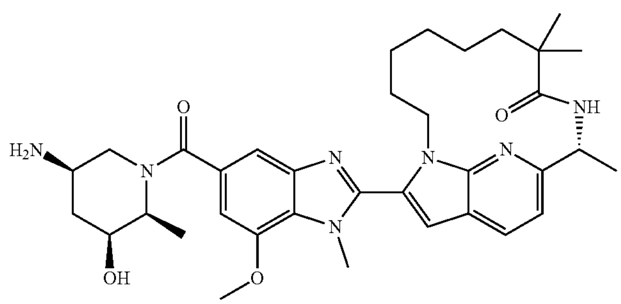 [SMILES: COc1cc(C(=O)N2C[C@H](N)C[C@H](O)[C@@H]2C)cc2nc(-c3cc4ccc5nc4n3CCCCCCC(C)(C)C(=O)N[C@@H]5C)n(C)c12] | (11~{R})-17-[5-[(2~{S},3~{S},5~{R})-5-amino-3-hydroxy-2-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12,14,16,18-tetraen-9-one |
| 787 | 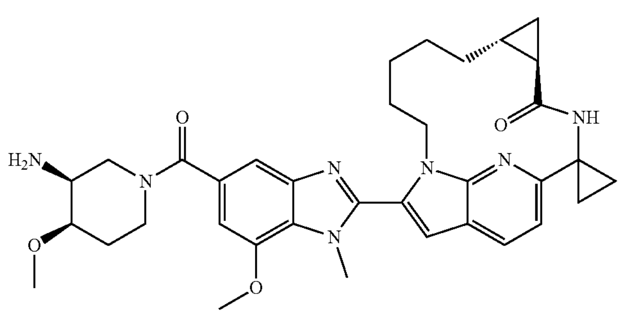 [SMILES: COc1cc(C(=O)N2CC[C@@H](OC)[C@@H](N)C2)cc2nc(-c3cc4ccc5nc4n3CCCCC[C@@H]3C[C@H]3C(=O)NC53CC3)n(C)c12] | (5~{R},7~{R})-14-[5-[(3~{S},4~{R})-3-amino-4-methoxy-piperidine-1-carbonyl]-7-methoxy-1-methyl-benzimidazol-2-yl]spiro[3,13,19-triazatetracyclo[11.5.2.0^{5,7}.0^{16,20}]icosa-1(18),14,16,19-tetraene-2,1'-cyclopropane]-4-one |
| 788 | 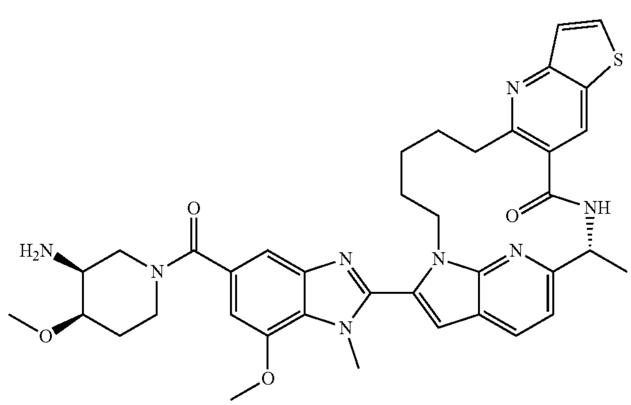 | (2~{R})-20-[5-[(3~{S},4~{R})-3-amino-4-methoxy-piperidine-1-carbonyl]-7-methoxy-1-methyl-benzimidazol-2-yl]-2-methyl-8-thia-3,12,19,25-tetrazapentacyclo[17.5.2.0^{5,13}.0^{7,11}.0^{22,26}]hexacosa-1(24),5(13),6,9,11,20,22,25-octaen-4-one |

TABLE 1A-continued

| Example | Structure | Name |
|---|---|---|
| 789 | 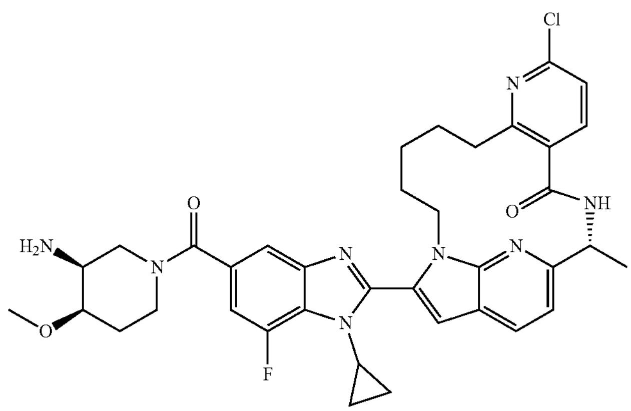 | (2~{R})-17-[5-[(3~{S},4~{R})-3-amino-4-methoxy-piperidine-1-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 790 | 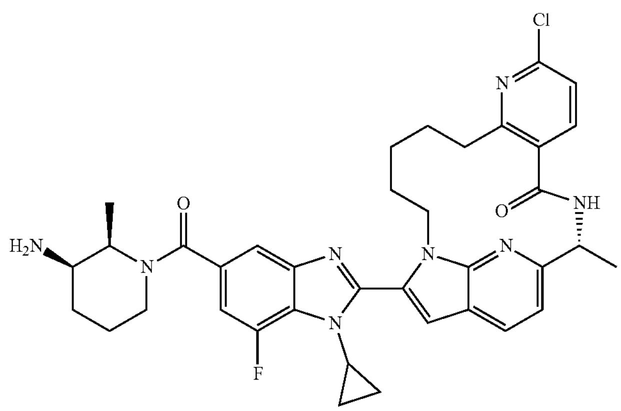 [SMILES: C[C@@H]1[C@H](N)CCCN1C(=O)c1cc(F)c2c(c1)nc(-c1cc3ccc4nc3n1CCCCCc1nc(Cl)ccc1C(=O)N[C@@H]4C)n2C1CC1] | (2~{R})-17-[5-[(2~{R},3~{R})-3-amino-2-methyl-piperidine-1-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 791 | 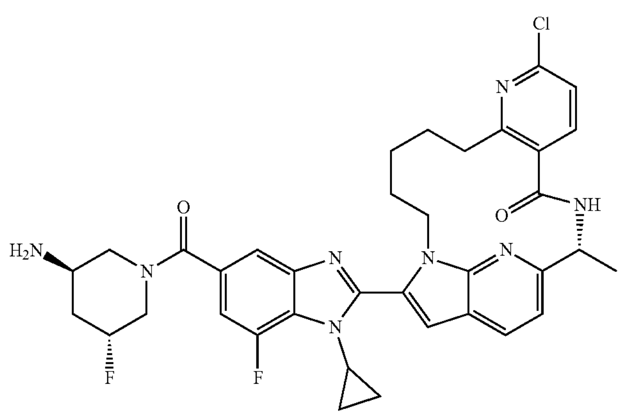 [SMILES: C[C@H]1NC(=O)c2ccc(Cl)nc2CCCCCn2c(-c3nc4cc(C(=O)N5C[C@H](N)C[C@@H](F)C5)cc(F)c4n3C3CC3)cc3ccc1nc32] | (2~{R})-17-[5-[(3~{R},5~{R})-3-amino-5-fluoro-piperidine-1-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 792 | 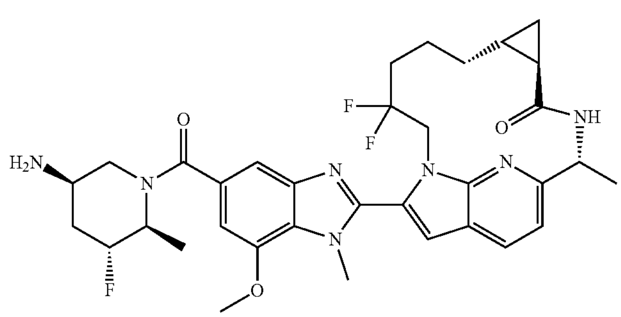 | (2~{R},5~{R},7~{R})-14-[5-[(2~{S},3~{R},5~{R})-5-amino-3-fluoro-2-methyl-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |

TABLE 1A-continued

| Example | Structure | Name |
| --- | --- | --- |
| 793 | 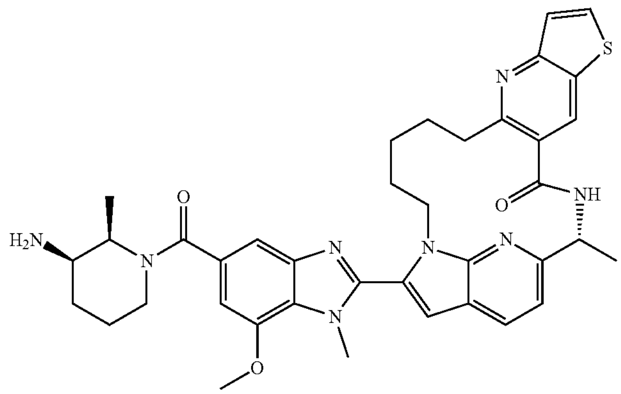 [SMILES: COc1cc(C(=O)N2CCC[C@@H](N)[C@H]2C)cc2nc(-c3cc4ccc5nc4n3CCCCCc3nc4ccsc4cc3C(=O)N[C@@H]5C)n(C)c12] | (2~{R})-20-[5-[(2~{R},3~{R})-3-amino-2-methyl-piperidine-1-carbonyl]-7-methoxy-1-methyl-benzimidazol-2-yl]-2-methyl-8-thia-3,12,19,25-tetrazapentacyclo[17.5.2.0^{5,13}.0^{7,11}.0^{22,26}]hexacosa-1(24),5(13),6,9,11,20,22,25-octaen-4-one |
| 794 | 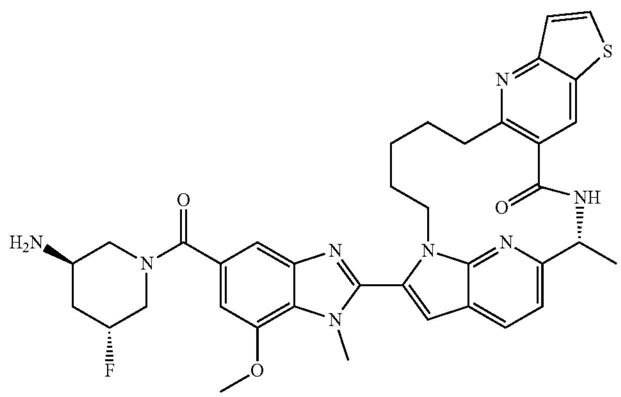 [SMILES: COc1cc(C(=O)N2C[C@H](N)C[C@@H](F)C2)cc2nc(-c3cc4ccc5nc4n3CCCCCc3nc4ccsc4cc3C(=O)N[C@@H]5C)n(C)c12] | (2~{R})-20-[5-[(3~{R},5~{R})-3-amino-5-fluoro-piperidine-1-carbonyl]-7-methoxy-1-methyl-benzimidazol-2-yl]-2-methyl-8-thia-3,12,19,25-tetrazapentacyclo[17.5.2.0^{5,13}.0^{7,11}.0^{22,26}]hexacosa-1(24),5(13),6,9,11,20,22,25-octaen-4-one |
| 795 | 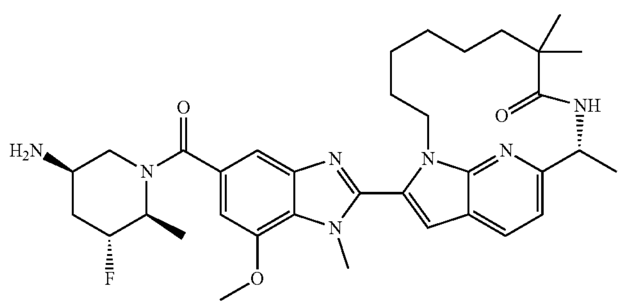 [SMILES: COc1cc(C(=O)N2C[C@H](N)C[C@@H](F)[C@@H]2C)cc2nc(-c3cc4ccc5nc4n3CCCCCCC(C)(C)C(=O)N[C@@H]5C)n(C)c12] | (11~{R})-17-[5-[(2~{S},3~{R},5~{R})-5-amino-3-fluoro-2-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12,14,16,18-tetraen-9-one |
| 796 | 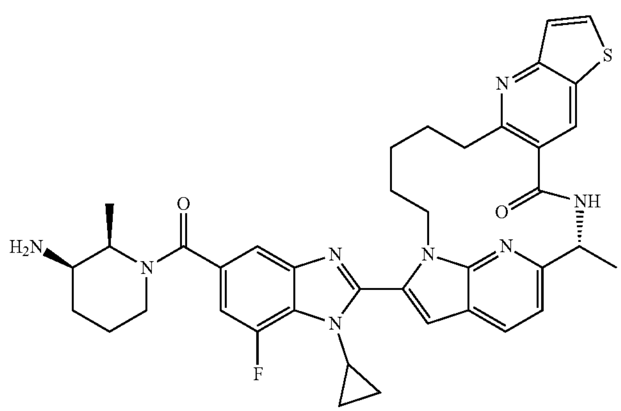 [SMILES: C[C@@H]1[C@H](N)CCCN1C(=O)c1cc(F)c2c(c1)nc(-c1cc3ccc4nc3n1CCCCCc1nc3ccsc3cc1C(=O)N[C@@H]4C)n2C1CC1] | (2~{R})-20-[5-[(2~{R},3~{R})-3-amino-2-methyl-piperidine-1-carbonyl]-1-cyclopropyl-7-fluoro-benzimidazol-2-yl]-2-methyl-8-thia-3,12,19,25-tetrazapentacyclo[17.5.2.0^{5,13}.0^{7,11}.0^{22,26}]hexacosa-1(24),5(13),6,9,11,20,22,25-octaen-4-one |

TABLE 1A-continued

| Example | Structure | Name |
|---|---|---|
| 797 | 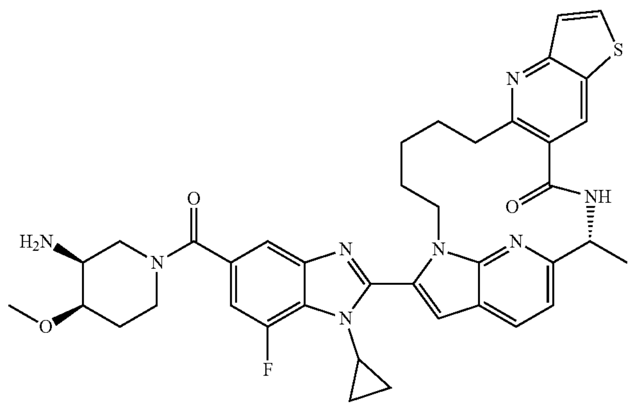 | (2~{R})-20-[5-[(3~{S},4~{R})-3-amino-4-methoxy-piperidine-1-carbonyl]-1-cyclopropyl-7-fluoro-benzimidazol-2-yl]-2-methyl-8-thia-3,12,19,25-tetrazapentacyclo[17.5.2.0^{5,13}.0^{7,11}.0^{22,26}]hexacosa-1(24),5(13),6,9,11,20,22,25-octaen-4-one |
| 798 | 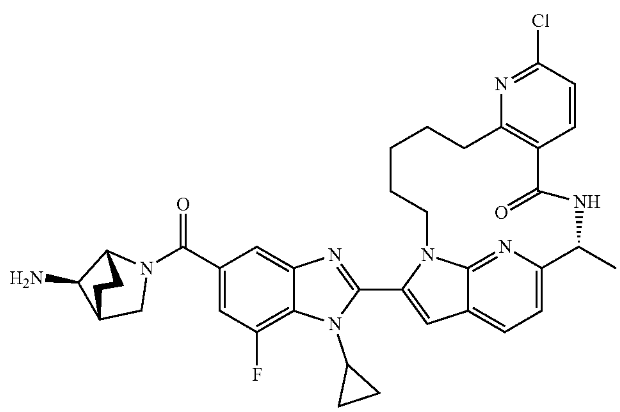 | (2~{R})-17-[5-[(1~{R},4~{R},7~{R})-7-amino-2-azabicyclo[2.2.1]heptane-2-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 799 | 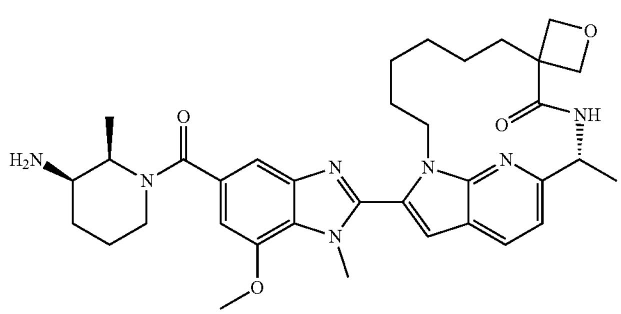 [SMILES: COc1cc(C(=O)N2CCC[C@@H](N)[C@H]2C)cc2nc(-c3cc4ccc5nc4n3CCCCCCC3(COC3)C(=O)N[C@@H]5C)n(C)c12] | (11~{R})-17-[5-[(2~{R},3~{R})-3-amino-2-methyl-piperidine-1-carbonyl]-7-methoxy-1-methyl-benzimidazol-2-yl]-11-methyl-spiro[1,10,19-triazatricyclo[10.5.2.0^{15,18}]nonadeca-12,14,16,18-tetraene-8,3'-oxetane]-9-one |
| 800 | 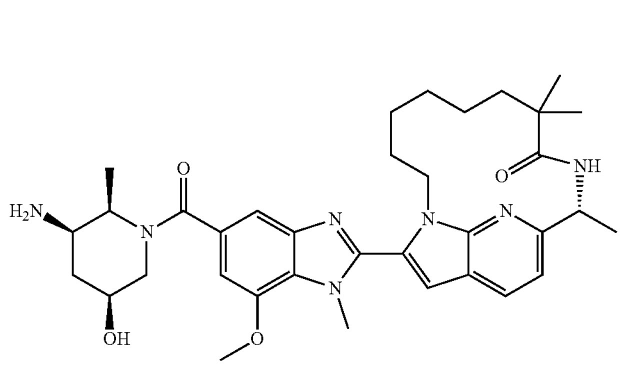 [SMILES: COc1cc(C(=O)N2C[C@@H](O)C[C@@H](N)[C@H]2C)cc2nc(-c3cc4ccc5nc4n3CCCCCCC(C)(C)C(=O)N[C@@H]5C)n(C)c12] | (11~{R})-17-[5-[(2~{R},3~{R},5~{S})-3-amino-5-hydroxy-2-methyl-piperidine-1-carbonyl]-7-methoxy-1-methyl-benzimidazol-2-yl]-8,8,11-trimethyl-1,10,19-triazatricyclo[10.5.2.0^{15,18}]nonadeca-12,14,16,18-tetraen-9-one |

TABLE 1A-continued

| Example | Structure | Name |
|---|---|---|
| 801 | 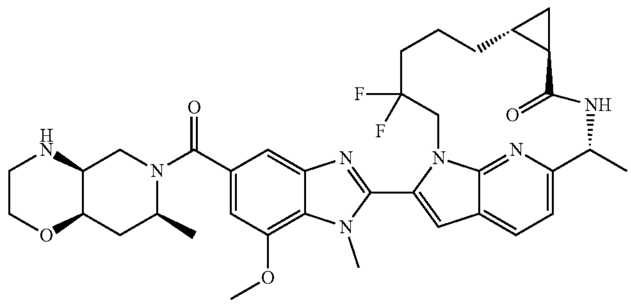 [SMILES: COc1cc(C(=O)N2C[C@@H]3NCCO[C@@H]3C[C@@H]2C)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(4~{a}~{S},7~{S},8~{a}~{R})-7-methyl-2,3,4,4~{a},5,7,8,8~{a}-octahydropyrido[4,3-b][1,4]oxazine-6-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 802 | 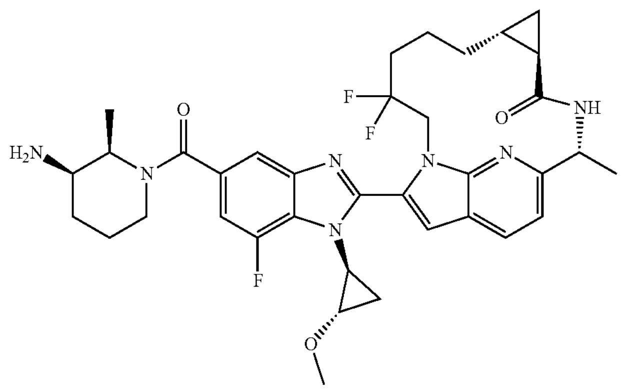 [SMILES: CO[C@H]1C[C@@H]1n1c(-c2cc3ccc4nc3n2CC(F)(F)CCC[C@@H]2C[C@H]2C(=O)N[C@@H]4C)nc2cc(C(=O)N3CCC[C@@H](N)[C@H]3C)cc(F)c21] | (2~{R},5~{R},7~{R})-14-[5-[(2~{R},3~{R})-3-amino-2-methyl-piperidine-1-carbonyl]-7-fluoro-1-[(1~{S},2~{S})-2-methoxycyclopropyl]benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 803 | 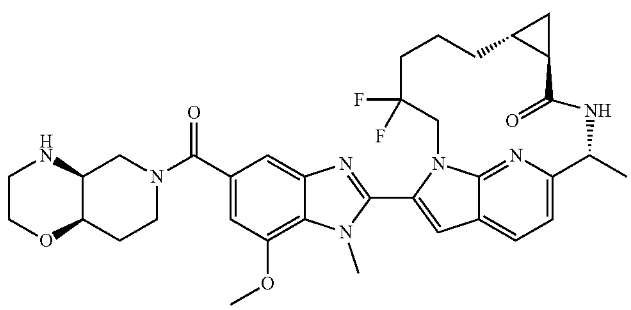 [SMILES: COc1cc(C(=O)N2CC[C@H]3OCCN[C@H]3C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(4~{a}~{S},8~{a}~{R})-2,3,4,4~{a},5,7,8,8~{a}-octahydropyrido[4,3-b][1,4]oxazine-6-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 804 | 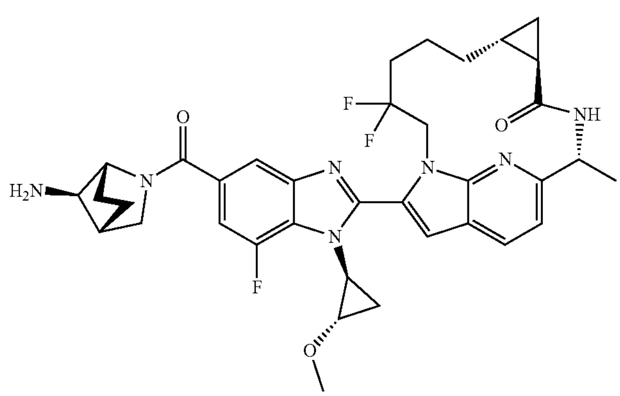 | (2~{R},5~{R},7~{R})-14-[5-[(1~{R},4~{R},7~{R})-7-amino-2-azabicyclo[2.2.1]heptane-2-carbonyl]-7-fluoro-1-[(1~{S},2~{S})-2-methoxycyclopropyl]benzimidazol-2-yl]-11,11-difluoro-2-methyl-3,13,19-triazatetracyclo[11.5.2.0^{5,7}.0^{16,20}]icosa-1(18),14,16,19-tetraen-4-one |

TABLE 1A-continued

| Example | Structure | Name |
|---|---|---|
| 805 | 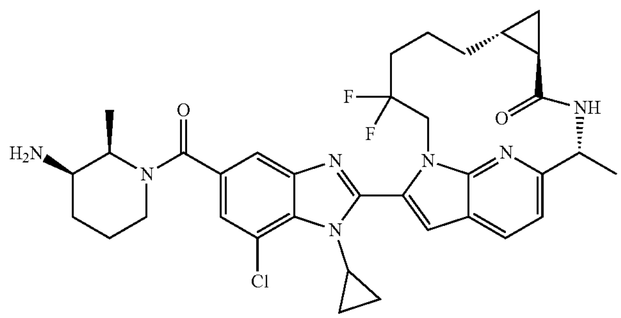 [SMILES: C[C@@H]1[C@H](N)CCCN1C(=O)c1cc(Cl)c2c(c1)nc(-c1cc3ccc4nc3n1CC(F)(F)CCC[C@@H]1C[C@H]1C(=O)N[C@@H]4C)n2C1CC1] | (2~{R},5~{R},7~{R})-14-[5-[(2~{R},3~{R})-3-amino-2-methyl-piperidine-1-carbonyl]-7-chloro-1-cyclopropyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 806 | 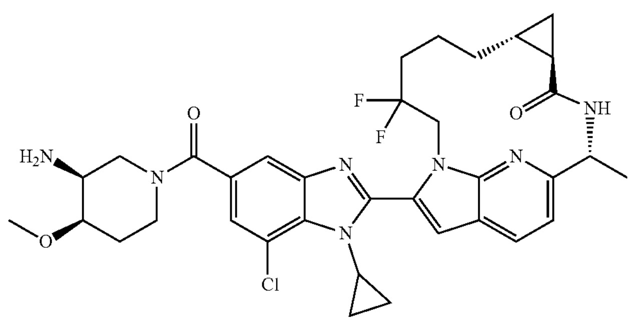 | (2~{R},5~{R},7~{R})-14-[5-[(3~{S},4~{R})-3-amino-4-methoxy-piperidine-1-carbonyl]-7-chloro-1-cyclopropyl-benzimidazol-2-yl]-11,11-difluoro-2-methyl-3,13,19-triazatetracyclo[11.5.2.0^{5,7}.0^{16,20}]icosa-1(18),14,16,19-tetraen-4-one |
| 807 | 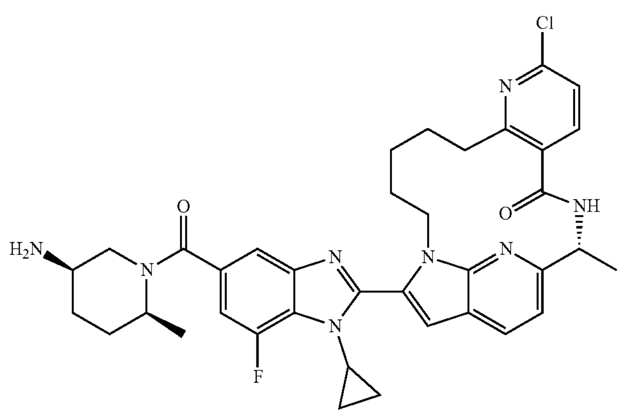 [SMILES: C[C@H]1NC(=O)c2ccc(Cl)nc2CCCCCn2c(-c3nc4cc(C(=O)N5C[C@H](N)CC[C@@H]5C)cc(F)c4n3C3CC3)cc3ccc1nc32] | (2~{R})-17-[5-[(2~{S},5~{R})-5-amino-2-methyl-piperidine-1-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 808 | 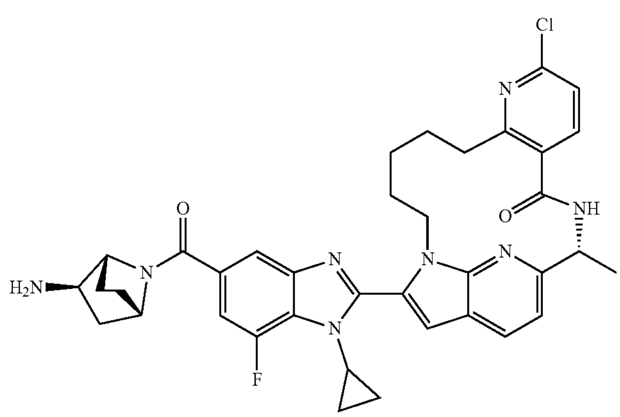 [SMILES: C[C@H]1NC(=O)c2ccc(Cl)nc2CCCCCn2c(-c3nc4cc(C(=O)N5[C@H]6CC[C@@H]5[C@H](N)C6)cc(F)c4n3C3CC3)cc3ccc1nc32] | (2~{R})-17-[5-[(1~{R},2~{R},4~{S})-2-amino-7-azabicyclo[2.2.1]heptane-7-carbonyl]-1-cyclopropyl-7-fluoro-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 809 | 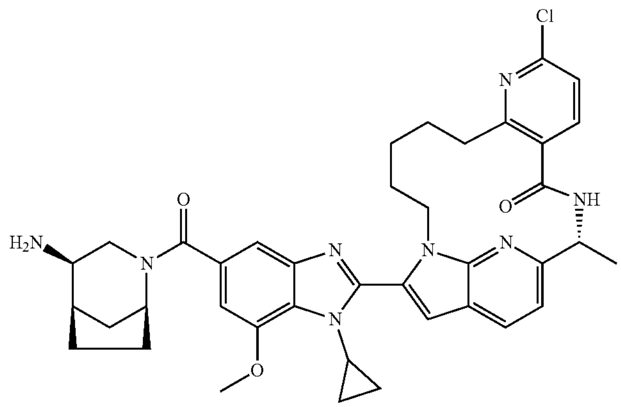 [SMILES: COc1cc(C(=O)N2C[C@H](N)[C@@H]3CC[C@H]2C3)cc2nc(-c3cc4ccc5nc4n3CCCCCc3nc(Cl)ccc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |
| 810 | 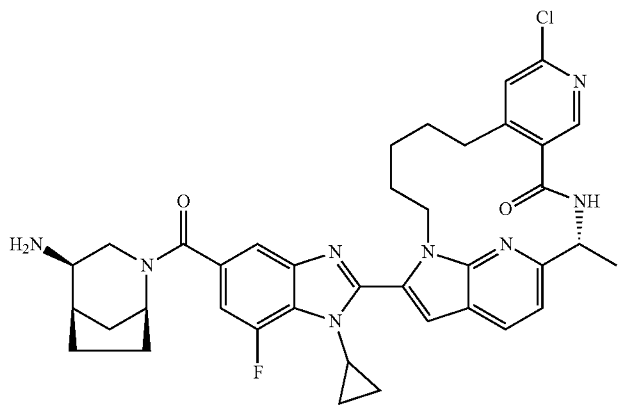 [SMILES: C[C@H]1NC(=O)c2cnc(Cl)cc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-2-methyl-3,7,16,22-tetrazatetracyclo[14.5.2.0^{5,10}.0^{19,23}]tricosa-1(21),5(10),6,8,17,19,22-heptaen-4-one |
| 811 | 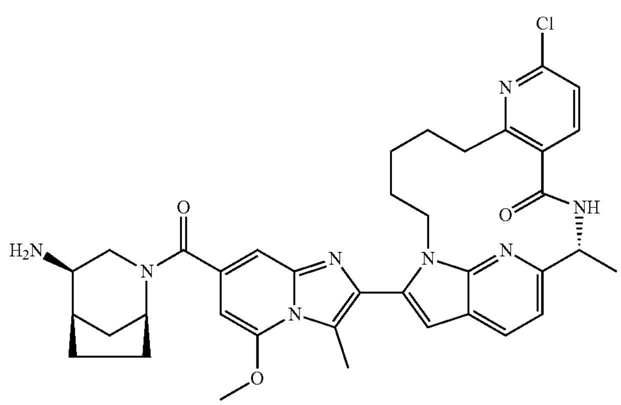 [SMILES: COc1cc(C(=O)N2C[C@H](N)[C@@H]3CC[C@H]2C3)cc2nc(-c3cc4ccc5nc4n3CCCCCc3nc(Cl)ccc3C(=O)N[C@@H]5C)c(C)n12] | (2~{R})-17-[7-[(1~{S},4~{R},5~{R})-4-amino-2-azabicyclo[3.2.1]octane-2-carbonyl]-5-methoxy-3-methyl-imidazo[1,2-a]pyridin-2-yl]-8-chloro-2-methyl-3,9,16,22-tetrazatetracyclo[14.5.2.0^{5,10}).0^{19,23}]tricosa-1(21),5(10),6,8,17,19,22-heptaen-4-one |
| 812 | 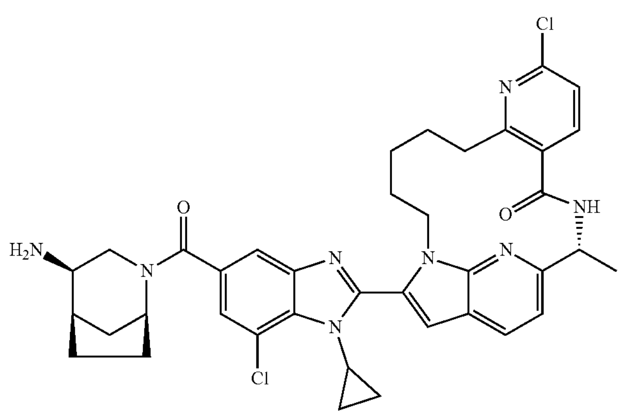 [SMILES: C[C@H]1NC(=O)c2ccc(Cl)nc2CCCCCn2c(-c3nc4cc(C(=O)N5C[C@H](N)[C@@H]6CC[C@H]5C6)cc(Cl)c4n3C3CC3)cc3ccc1nc32] | (2~{R})-17-[5-[(1~{S},4~{R},5~{R})-4-amino-2-azabicyclo[3.2.1]octane-2-carbonyl]-7-chloro-1-cyclopropyl-benzimidazol-2-yl]-8-chloro-2-methyl-3,9,16,22-tetrazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 813 | 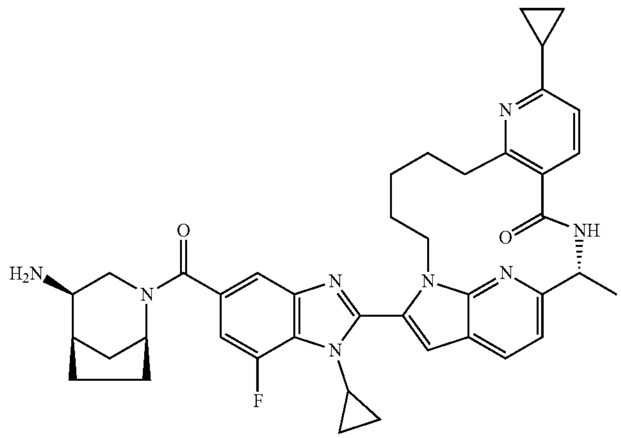 [SMILES: C[C@H]1NC(=O)c2ccc(C3CC3)nc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-cyclopropyl-2-methyl-3,9,16,22-tetrazatetracyclo[14.5.2.0^{5,10}.0^{19,23}]tricosa-1(21),5(10),6,8,17,19,22-heptaen-4-one |
| 814 | 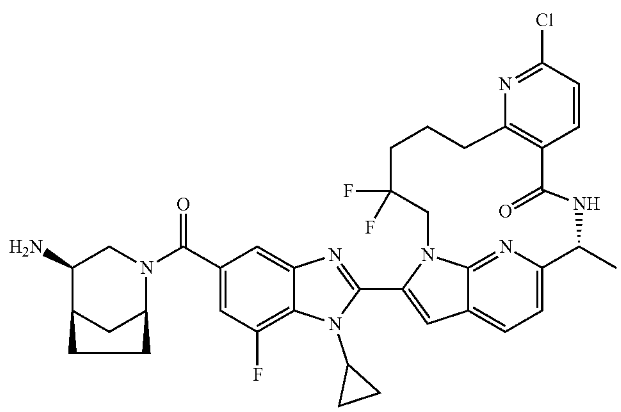 [SMILES: C[C@H]1NC(=O)c2ccc(Cl)nc2CCCC(F)(F)Cn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-14,14-difluoro-2-methyl-3,9,16,22-tetrazatetracyclo[14.5.2.0^{5,10}.0^{19,23}]tricosa-1(21),5(10),6,8,17,19,22-heptaen-4-one |
| 815 | 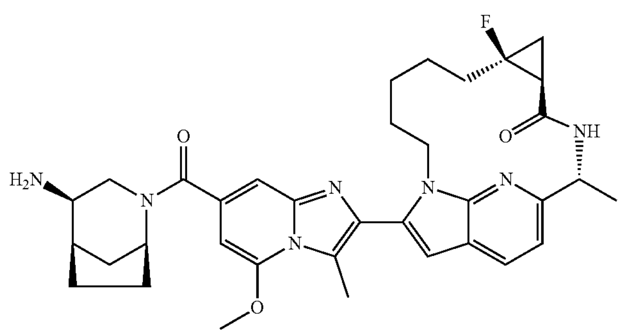 [SMILES: COc1cc(C(=O)N2C[C@H](N)[C@@H]3CC[C@H]2C3)cc2nc(-c3cc4ccc5nc4n3CCCCC[C@]3(F)C[C@H]3C(=O)N[C@@H]5C)c(C)n12] | (2~{R},5~{S},7~{S})-14-[7-[(1~{S},4~{R},5~{R})-4-amino-2-azabicyclo[3.2.1]octane-2-carbonyl]-5-methoxy-3-methyl-imidazo[1,2-a]pyridin-2-yl]-7-fluoro-2-methyl-3,13,19-triazatetracyclo[11.5.2.0^{5,7}.0^{16,20}]icosa-1(18),14,16,19-tetraen-4-one |
| 816 | 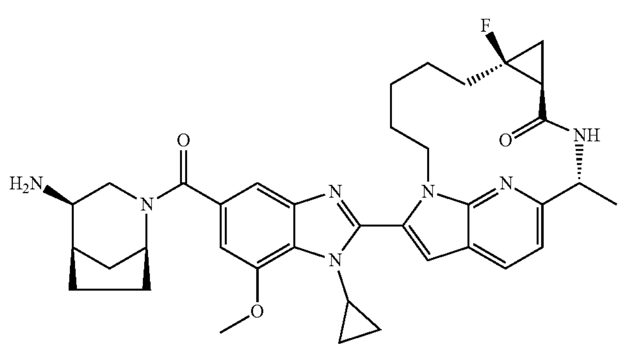 [SMILES: COc1cc(C(=O)N2C[C@H](N)[C@@H]3CC[C@H]2C3)cc2nc(-c3cc4ccc5nc4n3CCCCC[C@]3(F)C[C@H]3C(=O)N[C@@H]5C)n(C3CC3)c12] | (2~{R},5~{S},7~{S})-14-[5-[(1~{S},4~{R},5~{R})-4-amino-2-azabicyclo[3.2.1]octane-2-carbonyl]-1-cyclopropyl-7-methoxy-benzimidazol-2-yl]-7-fluoro-2-methyl-3,13,19-triazatetracyclo[11.5.2.0^{5,7}.0^{16,20}]icosa-1(18),14,16,19-tetraen-4-one |

TABLE 1A-continued

| Example | Structure | Name |
|---|---|---|
| 817 | 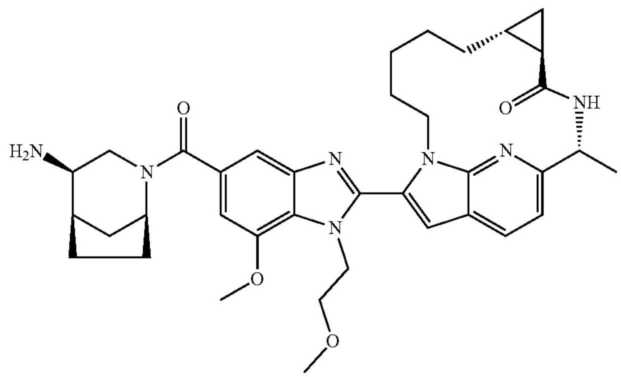 [SMILES: COCCn1c(-c2cc3ccc4nc3n2CCCCC[C@@H]2C[C@H]2C(=O)N[C@@H]4C)nc2cc(C(=O)N3C[C@H](N)[C@@H]4CC[C@H]3C4)cc(OC)c21] | (2~{R},5~{R},7~{R})-14-[5-[(1~{S},4~{R},5~{R})-4-amino-2-[3.2.1]octane-2-carbonyl]-7-methoxy-1-(2-methoxyethyl)benzimidazol-2-yl]-2-methyl-3,13,19-triazatetracyclo[11.5.2.0^{5,7}.0^{16,20}]icosa-1(18),14,16,19-tetraen-4-one |
| 818 | 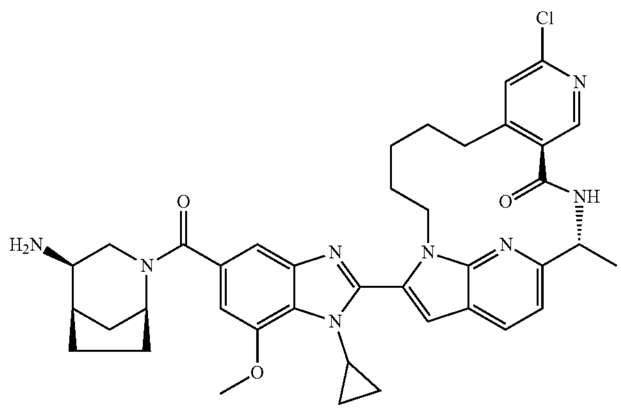 | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-chloro-2-methyl-3,7,16,22-tetrazatetracyclo[14.5.2.0^{5,10}.0^{19,23}]tricosa-1(21),5(10),6,8,17,19,22-heptaen-4-one |
| 819 | 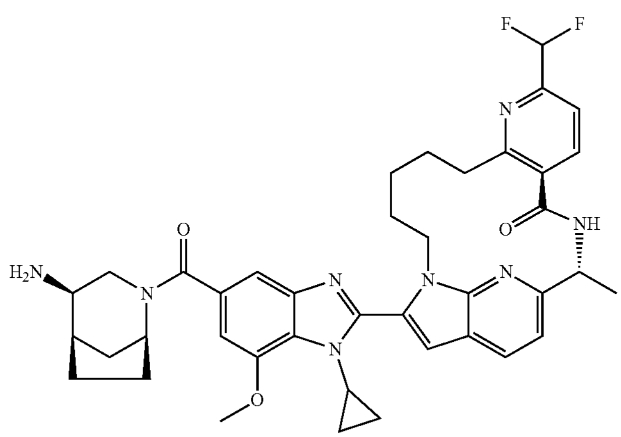 | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-(difluoromethyl)-2-methyl-3,9,16,22-tetrazatetracyclo[14.5.2.0^{5,10}.0^{19,23}]tricosa-1(21),5(10),6,8,17,19,22-heptaen-4-one |

TABLE 1A-continued

| Example | Structure | Name |
|---|---|---|
| 820 | 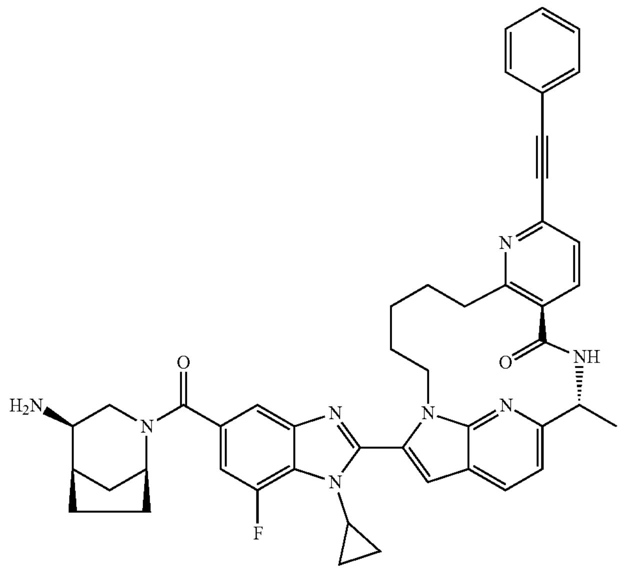 | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-8-(2-phenylethynyl)-3,9,16,22-tetrazatetracyclo[14.5.2.0^{5,10}.0^{19,23}]tricosa-1(21),5(10),6,8,17,19,22-heptaen-4-one |
| 821 | 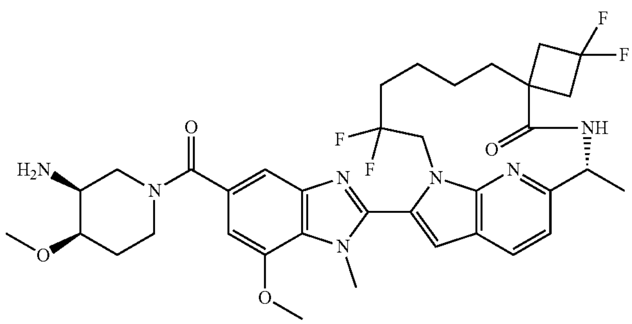 | (11~{R})-17-[5-[(3~{S},4~{R})-3-amino-4-methoxy-piperidine-1-carbonyl]-7-methoxy-1-methyl-benzimidazol-2-yl]-1',1',3,3-tetrafluoro-11-methyl-spiro[1,10,19-triazatricyclo[10.5.2.0^{15,18}]nonadeca-12(19),13,15(18),16-tetraene-8,3'-cyclobutane]-9-one |
| 822 | 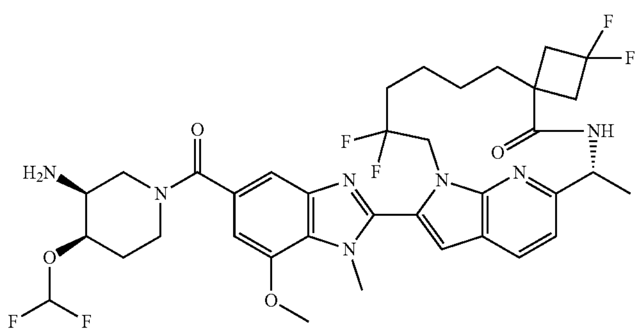 [SMILES: COc1cc(C(=O)N2CC[C@@H](OC(F)F)[C@@H](N)C2)cc2nc(-c3cc4ccc5nc4n3CC(F)(F)CCCCC3(CC(F)(F)C3)C(=O)N[C@@H]5C)n(C)c12] | (11~{R})-17-[5-[(3~{S},4~{R})-3-amino-4-(difluoromethoxy)piperidine-1-carbonyl]-7-methoxy-1-methyl-benzimidazol-2-yl]-1',1',3,3-tetrafluoro-11-methyl-spiro[1,10,19-triazatricyclo[10.5.2.0^{15,18}]nonadeca-12(19),13,15(18),16-tetraene-8,3'-cyclobutane]-9-one |
| 823 | 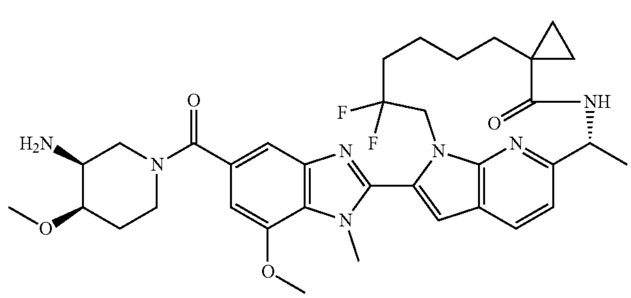 | (11~{R})-17-[5-[(3~{S},4~{R})-3-amino-4-methoxy-piperidine-1-carbonyl]-7-methoxy-1-methyl-benzimidazol-2-yl]-3,3-difluoro-11-methyl-spiro[1,10,19-triazatricyclo[10.5.2.0^{15,18}]nonadeca-12(19),13,15(18),16-tetraene-8,1'-cyclopropane]-9-one |

TABLE 1A-continued

| Example | Structure | Name |
|---|---|---|
| 824 | 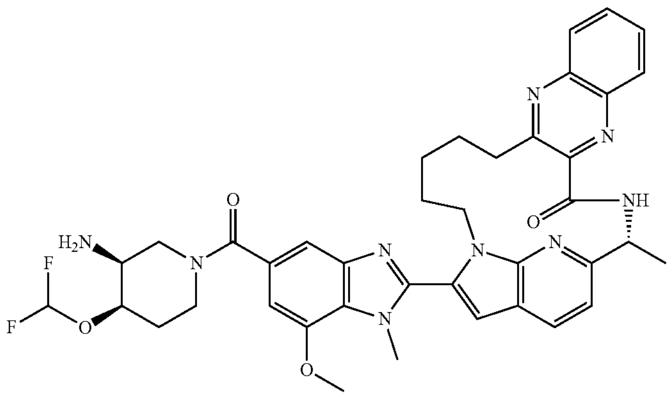 [SMILES: COc1cc(C(=O)N2CC[C@@H](OC(F)F)[C@@H](N)C2)cc2nc(-c3cc4ccc5nc4n3CCCCCc3nc4ccccc4nc3C(=O)N[C@@H]5C)n(C)c12] | (2~{R})-21-[5-[(3~{S},4~{R})-3-amino-4-(difluoromethoxy)piperidine-1-carbonyl]-7-methoxy-1-methyl-benzimidazol-2-yl]-2-methyl-3,6,13,20,26-pentazapentacyclo[18.5.2.0^{5,14}.0^{7,12}.0^{23,27}]heptacosa-1(26),5,7(12),8,10,13,21,23(27),24-nonaen-4-one |
| 825 | 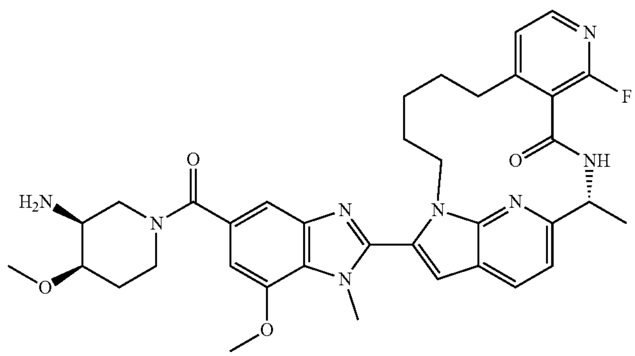 [SMILES: COc1cc(C(=O)N2CC[C@@H](OC)[C@@H](N)C2)cc2nc(-c3cc4ccc5nc4n3CCCCCc3ccnc(F)c3C(=O)N[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-6-fluoro-2-methyl-3,7,16,22-tetrazatetracyclo[14.5.2.0^{5,10}.0^{19,23}]tricosa-1(21),5,7,9,17,19,22-heptaen-4-one |
| 826 | 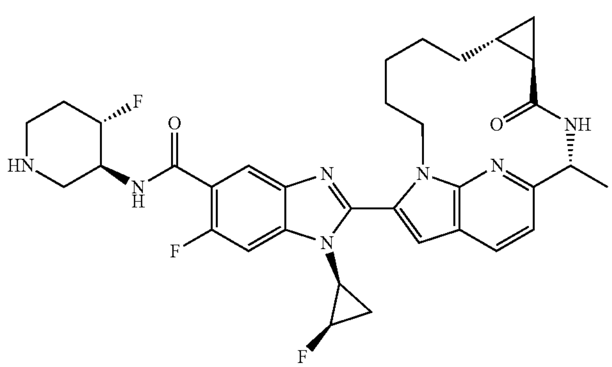 [SMILES: C[C@H]1NC(=O)[C@@H]2C[C@H]2CCCCCn2c(-c3nc4cc(C(=O)N[C@H]5CNCC[C@@H]5F)c(F)cc4n3[C@H]3C[C@H]3F)cc3ccc1nc32] | 6-fluoro-1-[(1~{S},2~{R})-2-fluorocyclopropyl]-~{N}-[(3~{S},4~{S})-4-fluoro-3-piperidyl]-2-[(2~{R},5~{R},7~{R})-2-methyl-4-oxo-3,13,19-triazatetracyclo[11.5.2.0^{5,7}.0^{16,20}]icosa-1(19),14,16(20),17-tetraen-14-yl]benzimidazole-5-carboxamide |
| 827 | 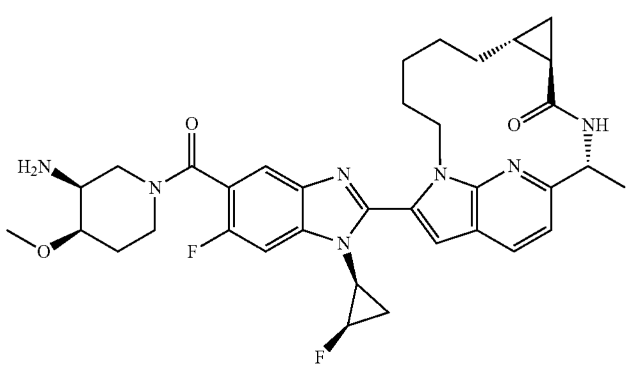 | (2~{R},5~{R},7~{R})-14-[5-[(3~{S},4~{R})-3-amino-4-methoxy-piperidine-1-carbonyl]-6-fluoro-1-[(1~{S},2~{R})-2-fluorocyclopropyl]benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 828 | 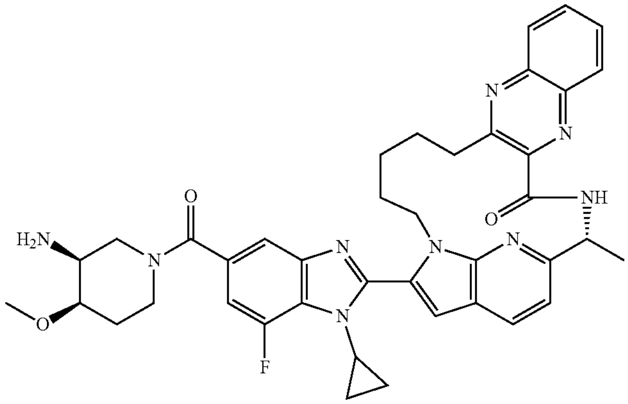 | (2~{R})-21-[5-[(3~{S}, 4~{R})-3-amino-4-methoxy-piperidine-1-carbonyl]-1-cyclopropyl-7-fluoro-benzimidazol-2-yl]-2-methyl-3,6,13,20,26-pentazapentacyclo [18.5.2.0^{5,14}.0^{7,12}.0^{23,27}]heptacosa-1(26),5(14),6,8,10,12,21,23(27),24-nonaen-4-one |
| 829 | 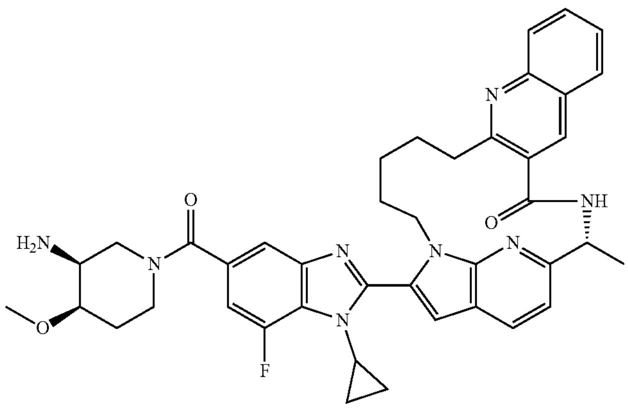 | (2~{R})-21-[5-[(3~{S},4~{R})-3-amino-4-methoxy-piperidine-1-carbonyl]-1-cyclopropyl-7-fluoro-benzimidazol-2-yl]-2-methyl-3,13,20,26-tetrazapentacyclo [18.5.2.0^{5,14}.0^{7,12}.0^{23,27}]heptacosa-1(26),5(14),6,8,10,12,21,23(27),24-nonaen-4-one |
| 830 | 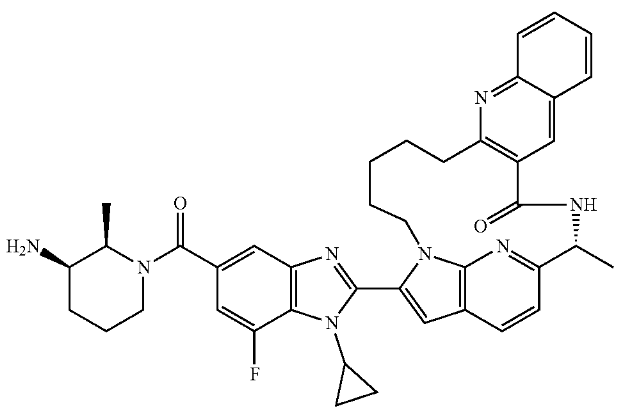 [SMILES: C[C@@H]1[C@H](N)CCCN1C(=O)c1cc(F)c2c(c1)nc(-c1cc3ccc4nc3n1CCCCCc1nc3ccccc3cc1C(=O)N[C@@H]4C)n2C1CC1] | (2~{R})-21-[5-[(2~{R}, 3~{R})-3-amino-2-methyl-piperidine-1-carbonyl]-1-cyclopropyl-7-fluoro-benzimidazol-2-yl]-2-methyl-3,13,20,26-tetrazapentacyclo[18.5.2.0^{5,14}.0^{7,12}.0^{23,27}]heptacosa-1(26),5(14),6,8,10,12,21,23(27),24-nonaen-4-one |
| 831 | 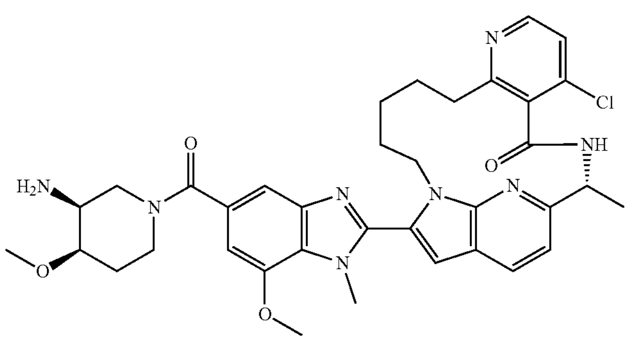 | (2~{R})-17-[5-[(3~{S}, 4~{R})-3-amino-4-methoxy-piperidine-1-carbonyl]-7-methoxy-1-methyl-benzimidazol-2-yl]-6-chloro-2-methyl-3,9,16,22-tetrazatetracyclo [14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 832 | 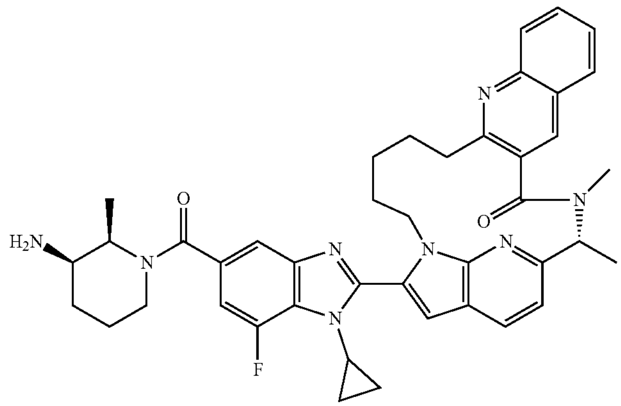 [SMILES: C[C@@H]1c2ccc3cc(-c4nc5cc(C(=O)N6CCC[C@@H](N)[C@H]6C)cc(F)c5n4C4CC4)n(c3n2)CCCCCc2nc3ccccc3cc2C(=O)N1C] | (2~{R})-21-[5-[(2~{R},3~{R})-3-amino-2-methyl-piperidine-1-carbonyl]-1-cyclopropyl-7-fluoro-benzimidazol-2-yl]-2,3-dimethyl-3,13,20,26-tetrazapentacyclo[18.5.2.0^{5,14}.0^{7,12}.0^{23,27}]heptacosa-1(26),5(14),6,8,10,12,21,23(27),24-nonaen-4-one |
| 833 | 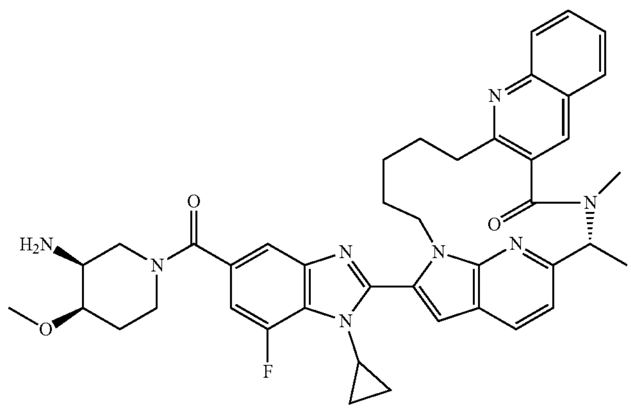 | (2~{R})-21-[5-[(3~{S},4~{R})-3-amino-4-methoxy-piperidine-1-carbonyl]-1-cyclopropyl-7-fluoro-benzimidazol-2-yl]-2,3-dimethyl-3,13,20,26-tetrazapentacyclo[18.5.2.0^{5,14}.0^{7,12}.0^{23,27}]heptacosa-1(26),5(14),6,8,10,12,21,23(27),24-nonaen-4-one |
| 834 | 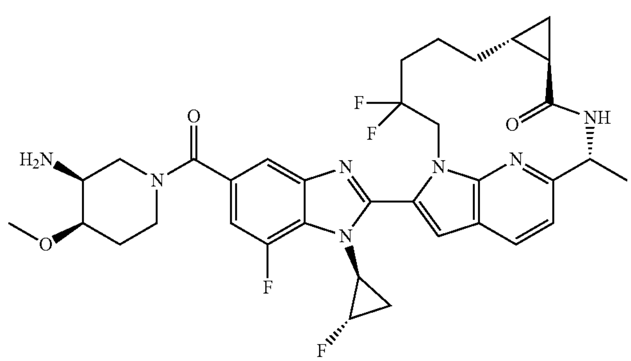 | (2~{R},5~{R},7~{R})-14-[5-[(3~{S},4~{R})-3-amino-4-methoxy-piperidine-1-carbonyl]-7-fluoro-1-[(1~{S},2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 835 | 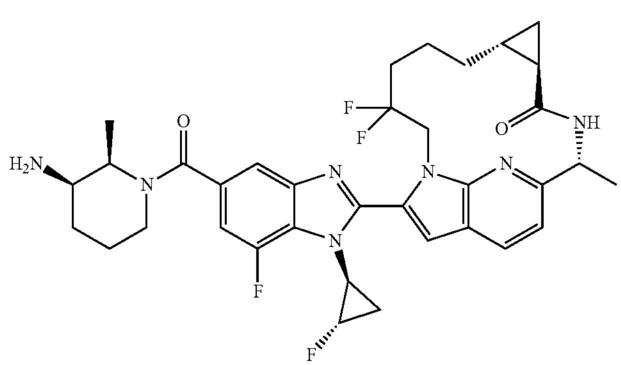 [SMILES: C[C@@H]1[C@H](N)CCCN1C(=O)c1cc(F)c2c(c1)nc(-c1cc3ccc4nc3n1CC(F)(F)CCC[C@@H]1C[C@H]1C(=O)N[C@@H]4C)n2[C@H]1C[C@@H]1F] | (2~{R},5~{R},7~{R})-14-[5-[(2~{R},3~{R})-3-amino-2-methyl-piperidine-1-carbonyl]-7-fluoro-1-[(1~{S},2~{S})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 836 | 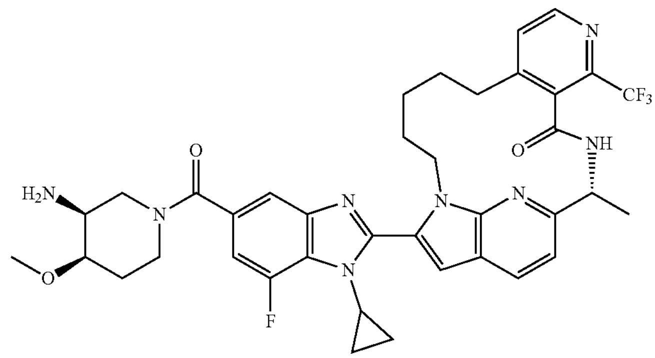 | (2~{R})-17-[5-[(3~{S},4~{R})-3-amino-4-methoxy-piperidine-1-carbonyl]-1-cyclopropyl-7-fluoro-benzimidazol-2-yl]-2-methyl-6-(trifluoromethyl)-3,7,16,22-tetrazatetracyclo[14.5.2.0^{5,10}.0^{19,23}]tricosa-1(22),5(10),6,8,17,19(23),20-heptaen-4-one |
| 837 | 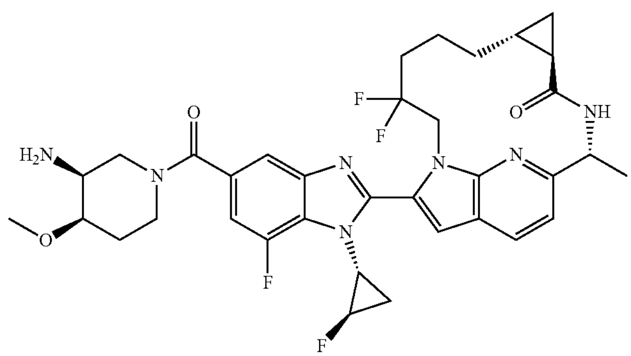 | (2~{R},5~{R},7~{R})-14-[5-[(3~{S},4~{R})-3-amino-4-methoxy-piperidine-1-carbonyl]-7-fluoro-1-[(1~{R},2~{R})-2-fluorocyclopropyl]benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 838 | 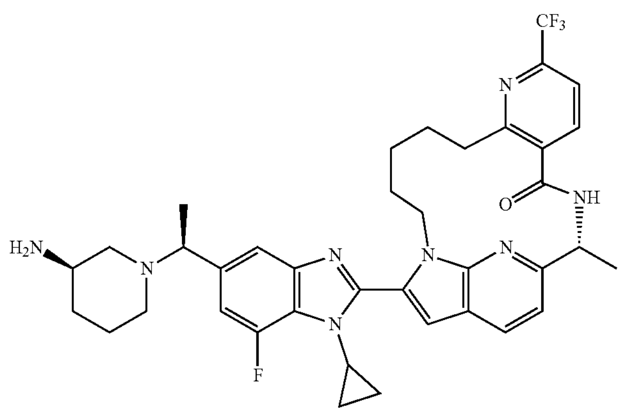 [SMILES: C[C@H]1NC(=O)c2ccc(C(F)(F)F)nc2CCCCCn2c(-c3nc4cc([C@H](C)N5CCC[C@@H](N)C5)cc(F)c4n3C3CC3)cc3ccc1nc32] | (2~{R})-17-[5-[(2~{R},3~{R})-3-amino-2-methyl-piperidine-1-carbonyl]-1-cyclopropyl-7-fluoro-benzimidazol-2-yl]-2-methyl-8-(trifluoromethyl)-3,9,16,22-tetrazatetracyclo[14.5.2.0^{5,10}.0^{19,23}]tricosa-1(22),5(10),6,8,17,19(23),20-heptaen-4-one |
| 839 | | (2~{R})-21-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,6,13,20,26-pentazapentacyclo[18.5.2.0^{5,14}.0^{7,12}.0^{23,27}]heptacosa-1(26),5(14),6,8,10,12,21,23(27),24-nonaen-4-one |

## TABLE 1A-continued

| Example | Structure | Name |
|---|---|---|
| 840 | 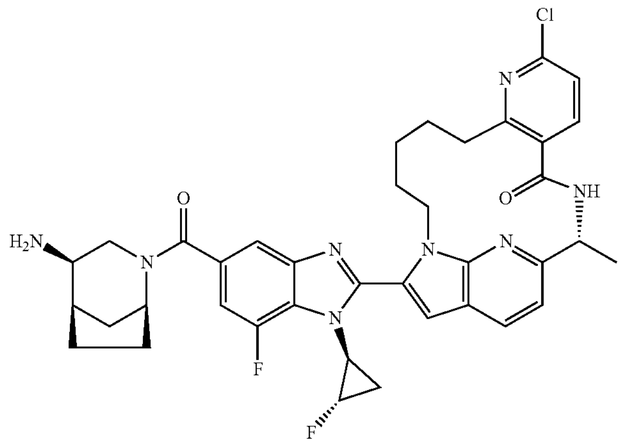 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3[C@H]3C[C@@H]3F)cc3ccc1nc32] | (2~{R})-17-[5-[(1~{S},4~{R},5~{R})-4-amino-2-azabicyclo[3.2.1]octane-2-carbonyl]-7-fluoro-1-[(1~{S},2~{S})-2-fluorocyclopropyl]benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 841 | 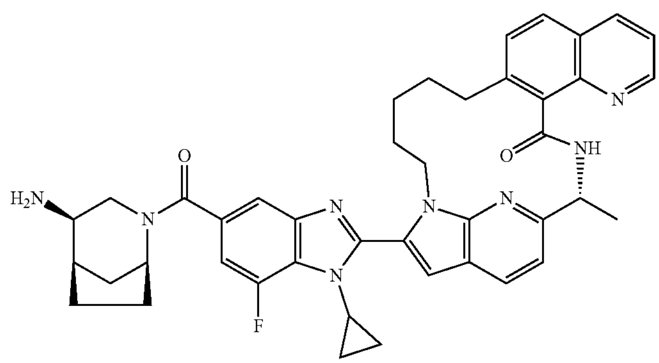 [SMILES: C[C@H]1NC(=O)c2c(ccc3cccnc23)CCCCCn2c(-c3nc4cc(C(=O)N5C[C@H](N)[C@@H]6CC[C@H]5C6)cc(F)c4n3C3CC3)cc3ccc1nc32] | (2~{R})-21-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,7,20,26-tetrazapentacyclo[18.5.2.0^{5,14}.0^{6,11}.0^{23,27}]heptacosa-1(26),5(14),6(11),7,9,12,21,23(27),24-nonaen-4-one |
| 842 | 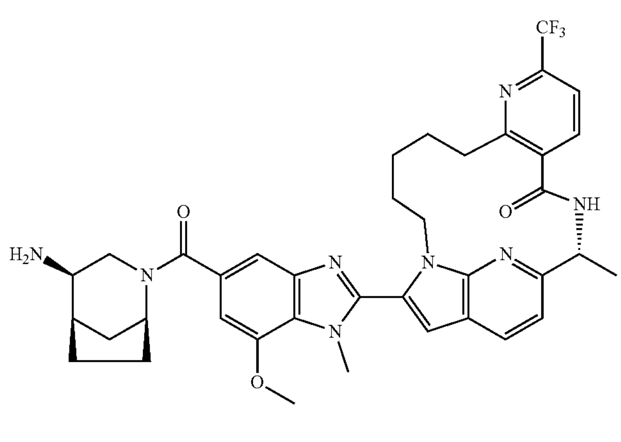 [SMILES: COc1cc(C(=O)N2C[C@H](N)[C@@H]3CC[C@H]2C3)cc2nc(-c3cc4ccc5nc4n3CCCCCc3nc(C(F)(F)F)ccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-2-methyl-8-(trifluoromethyl)-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 843 | 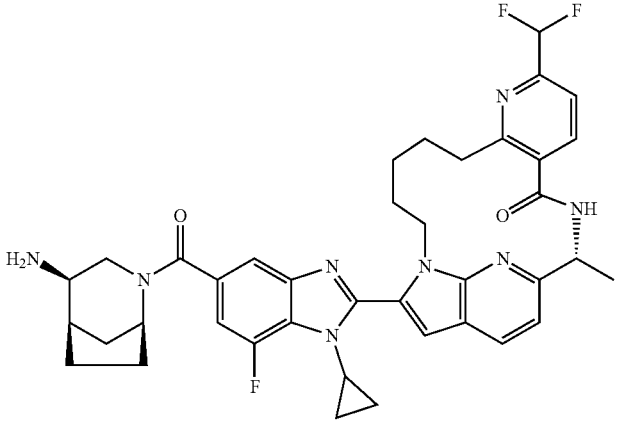 [SMILES: C[C@H]1NC(=O)c2ccc(C(F)F)nc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-(difluoromethyl)-2-methyl-3,9,16,22-tetrazatetracyclo[14.5.2.0^{5,10}.0^{19,23}]tricosa-1(22),5(10),6,8,17,19(23),20-heptaen-4-one |
| 844 | 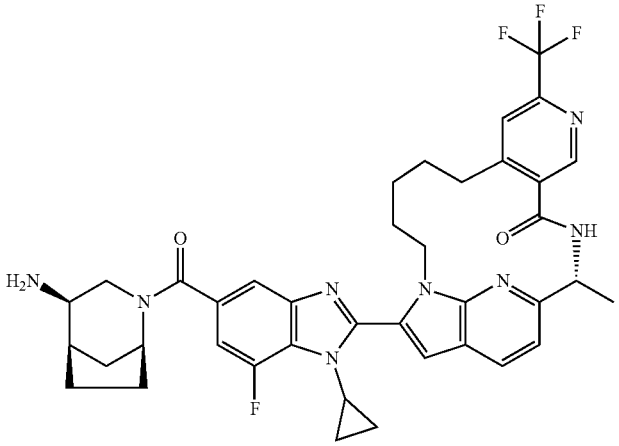 [SMILES: C[C@H]1NC(=O)c2cnc(C(F)(F)F)cc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-8-(trifluoromethyl)-3,7,16,22-tetrazatetracyclo[14.5.2.0^{5,10}.0^{19,23}]tricosa-1(22),5(10),6,8,17,19(23),20-heptaen-4-one |
| 845 | 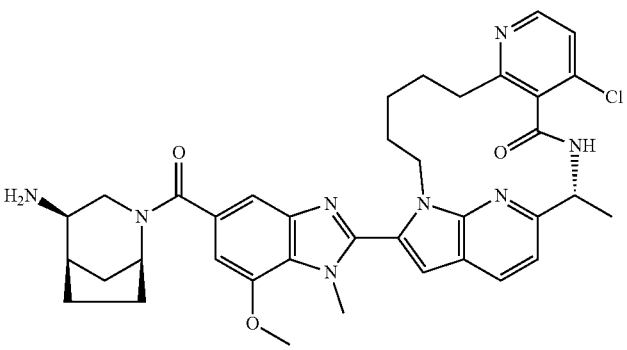 [SMILES: COc1cc(C(=O)N2C[C@H](N)[C@@H]3CC[C@H]2C3)cc2nc(-c3cc4ccc5nc4n3CCCCCc3nccc(Cl)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 846 | 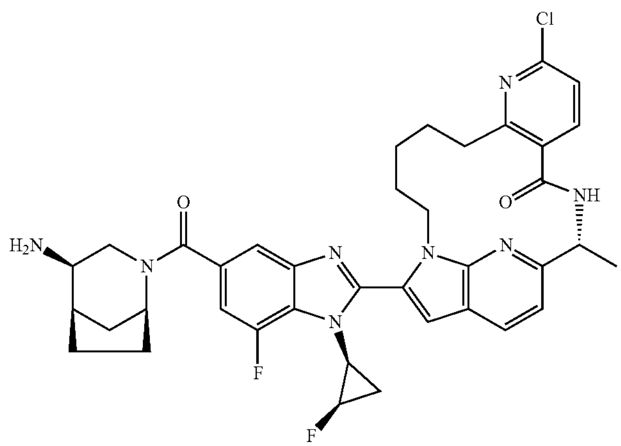 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3[C@H]3C[C@H]3F)cc3ccc1nc32] | (2~{R})-17-[5-[(1~{S},4~{R},5~{R})-4-amino-2-azabicyclo[3.2.1]octane-2-carbonyl]-7-fluoro-1-[(1~{S},2~{R})-2-fluorocyclopropyl]benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 847 | 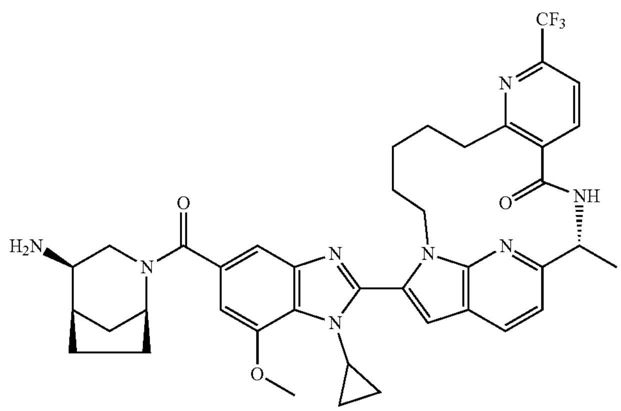 [SMILES: COc1cc(C(=O)N2C[C@H](N)[C@@H]3CC[C@H]2C3)cc2nc(-c3cc4ccc5nc4n3CCCCCc3nc(C(F)(F)F)ccc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-2-methyl-8-(trifluoromethyl)-3,9,16,22-tetrazatetracyclo[14.5.2.0^{5,10}.0^{19,23}]tricosa-1(22),5(10),6,8,17,19(23),20-heptaen-4-one |
| 848 | 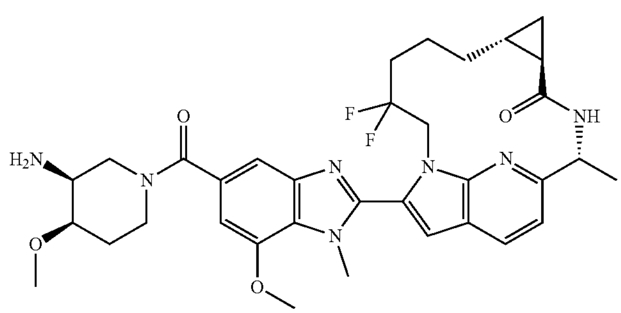 [SMILES: COc1cc(C(=O)N2CC[C@@H](OC)[C@@H](N)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 849 | 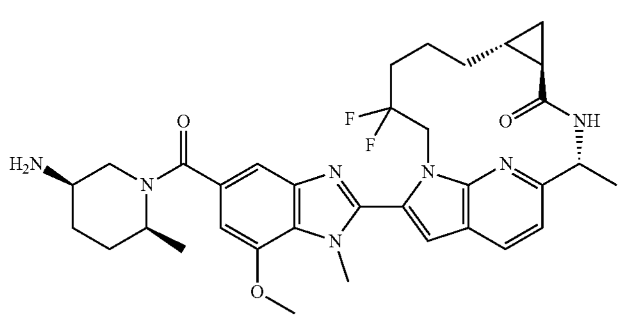 [SMILES: COc1cc(C(=O)N2C[C@H](N)CC[C@@H]2C)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(2~{S},5~{R})-5-amino-2-methyl-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 850 | 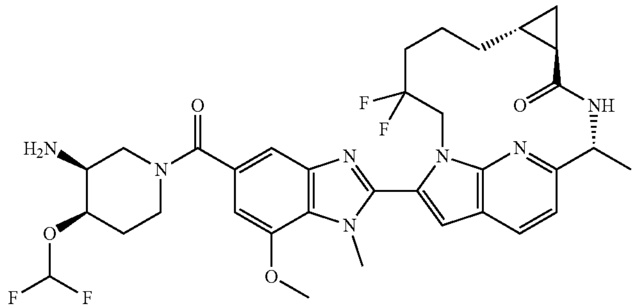 [SMILES: COc1cc(C(=O)N2CC[C@@H](OC(F)F)[C@@H](N)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(3~{S},4~{R})-3-amino-4-(difluoromethoxy)piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 851 | 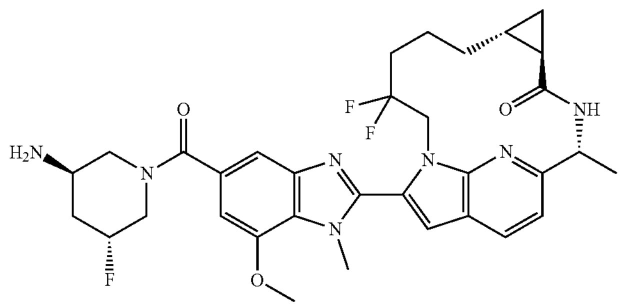 [SMILES: COc1cc(C(=O)N2C[C@H](N)C[C@@H](F)C2)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(3~{R},5~{R})-3-amino-5-fluoro-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 852 | 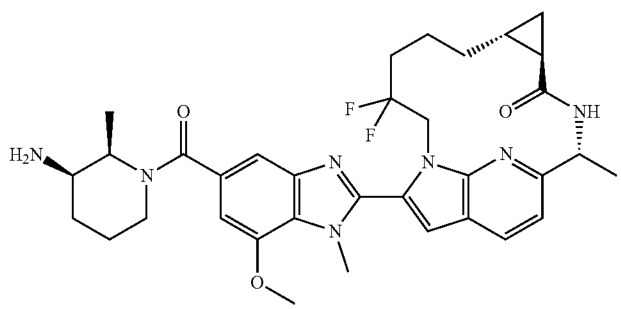 [SMILES: COc1cc(C(=O)N2CCC[C@@H](N)[C@H]2C)cc2nc(-c3cc4ccc5nc4n3CC(F)(F)CCC[C@@H]3C[C@H]3C(=O)N[C@@H]5C)n(C)c12] | (2~{R},5~{R},7~{R})-14-[5-[(2~{R},3~{R})-3-amino-2-methyl-piperidine-1-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 853 | 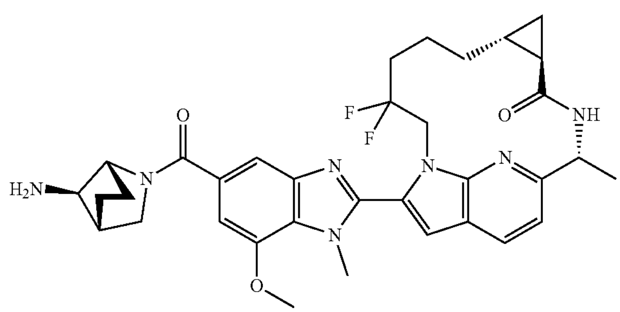 | (2~{R},5~{R},7~{R})-14-[5-[(1~{R},4~{R},7~{R})-7-amino-2-azabicyclo[2.2.1]heptane-2-carbonyl]-7-methoxy-1-methyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 854 | 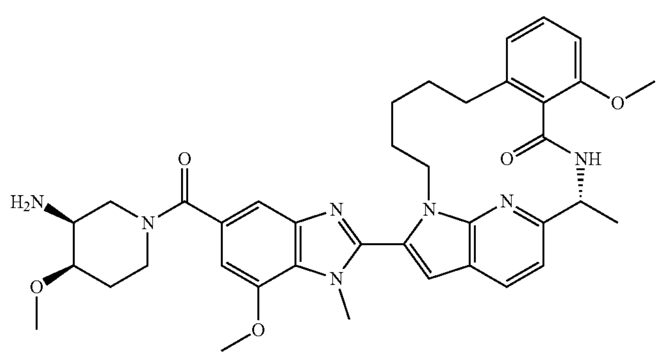 [SMILES: COc1cccc2c1C(=O)N[C@H](C)c1ccc3cc(-c4nc5cc(C(=O)N6CC[C@@H](OC)[C@@H](N)C6)cc(OC)c5n4C)n(c3n1)CCCCC2] | (2~{R})-17-[5-[(3~{S},4~{R})-3-amino-4-methoxy-piperidine-1-carbonyl]-7-methoxy-1-methyl-benzimidazol-2-yl]-6-methoxy-2-methyl-3,16,22-triazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 855 | 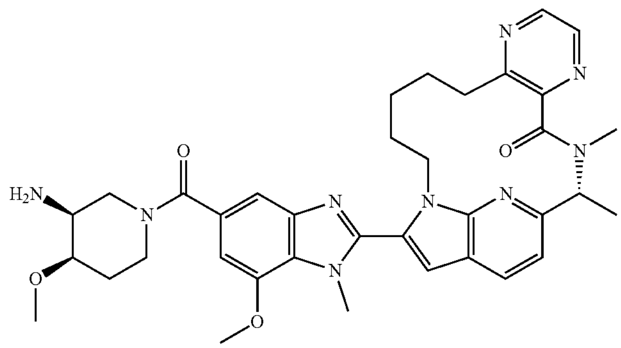 [SMILES: COc1cc(C(=O)N2CC[C@@H](OC)[C@@H](N)C2)cc2nc(-c3cc4ccc5nc4n3CCCCCc3nccnc3C(=O)N(C)[C@@H]5C)n(C)c12] | (2~{R})-17-[5-[(3~{S},4~{R})-3-amino-4-methoxy-piperidine-1-carbonyl]-7-methoxy-1-methyl-benzimidazol-2-yl]-2,3-dimethyl-3,6,9,16,22-pentazatetracyclo[14.5.2.0^{5,10}.0^{1923}]tricosa-1(22),,5(10),6,8,17,19(23),20-heptaen-4-one |
| 856 | 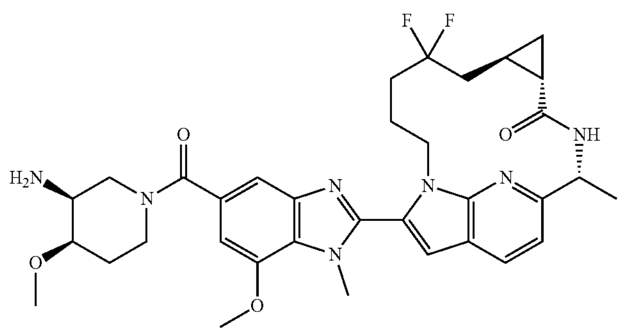 [SMILES: COc1cc(C(=O)N2CC[C@@H](OC)[C@@H](N)C2)cc2nc(-c3cc4ccc5nc4n3CCCC(F)(F)C[C@H]3C[C@@H]3C(=O)N[C@@H]5C)n(C)c12] | (2~{R},5~{S},7~{R})-14-[5-[(3~{S},4~{R})-3-amino-4-methoxy-piperidine-1-carbonyl]-7-methoxy-1-methyl-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |
| 857 | 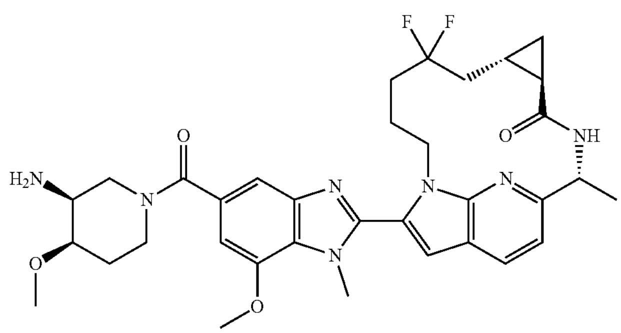 [SMILES: COc1cc(C(=O)N2CC[C@@H](OC)[C@@H](N)C2)cc2nc(-c3cc4ccc5nc4n3CCCC(F)(F)C[C@@H]3C[C@H]3C(=O)N[C@@H]5C)n(C)c12] | (2~{R},5~{R},7~{S})-14-15-[(3~{S},4~{R})-3-amino-4-methoxy-piperidine-1-carbonyl]-7-methoxy-1-methyl-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |
| 858 | 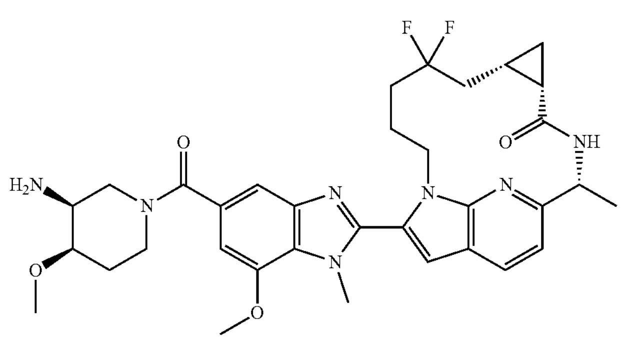 [SMILES: COc1cc(C(=O)N2CC[C@@H](OC)[C@@H](N)C2)cc2nc(-c3cc4ccc5nc4n3CCCC(F)(F)C[C@@H]3C[C@@H]3C(=O)N[C@@H]5C)n(C)c12] | (2~{R},5~{S},7~{S})-14-[5-[(3~{S},4~{R})-3-amino-4-methoxy-piperidine-1-carbonyl]-7-methoxy-1-methyl-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 859 | 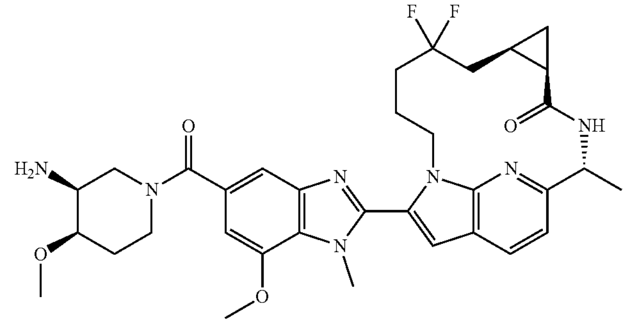 [SMILES: COc1cc(C(=O)N2CC[C@@H](OC)[C@@H](N)C2)cc2nc(-c3cc4ccc5nc4n3CCCC(F)(F)C[C@H]3C[C@H]3C(=O)N[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |
| 860 | 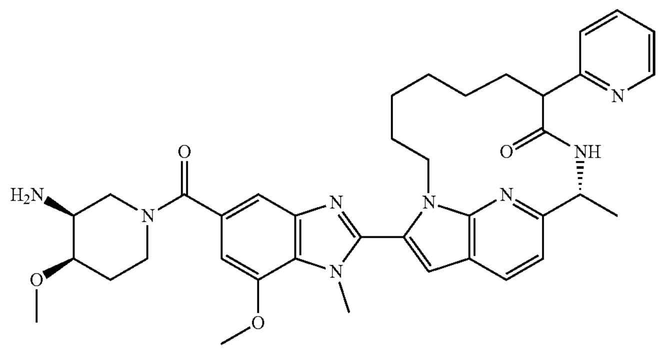 [SMILES: COc1cc(C(=O)N2CC[C@@H](OC)[C@@H](N)C2)cc2nc(-c3cc4ccc5nc4n3CCCCCCC(c3ccccn3)C(=O)N[C@@H]5C)n(C)c12] | (11~{R})-17-[5-[(3~{S},4~{R})-3-amino-4-methoxy-piperidine-1-carbonyl]-7-methoxy-1-methyl-benzimidazol-2-yl]-11-methyl-8-(2-pyridyl)-1,10,19-triazatricyclo[10.5.2.0^{15,18}]nonadeca-12(19),13,15(18),16-tetraen-9-one |
| 861 | 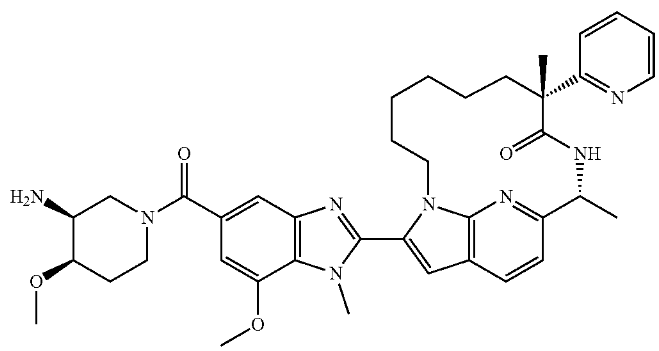 [SMILES: COc1cc(C(=O)N2CC[C@@H](OC)[C@@H](N)C2)cc2nc(-c3cc4ccc5nc4n3CCCCCC[C@](C)(c3ccccn3)C(=O)N[C@@H]5C)n(C)c12] | (8~{R},11~{R})-17-[5-[(3~{S},4~{R})-3-amino-4-methoxy-piperidine-1-carbonyl]-7-methoxy-1-methyl-benzimidazol-2-yl]-8,11-dimethyl-8-(2-pyridyl)-1,10,19-triazatricyclo[10.5.2.0^{15,18}]nonadeca-12(19),13,15(18),16-tetraen-9-one |
| 862 | 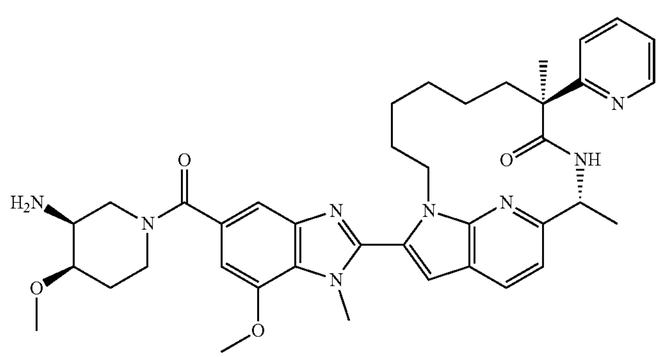 [SMILES: COc1cc(C(=O)N2CC[C@@H](OC)[C@@H](N)C2)cc2nc(-c3cc4ccc5nc4n3CCCCCC[C@@](C)(c3ccccn3)C(=O)N[C@@H]5C)n(C)c12] | (8~{S},11~{R})-17-[5-[(3~{S},4~{R})-3-amino-4-methoxy-piperidine-1-carbonyl]-7-methoxy-1-methyl-benzimidazol-2-yl]-8,11-dimethyl-8-(2-pyridyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 863 | 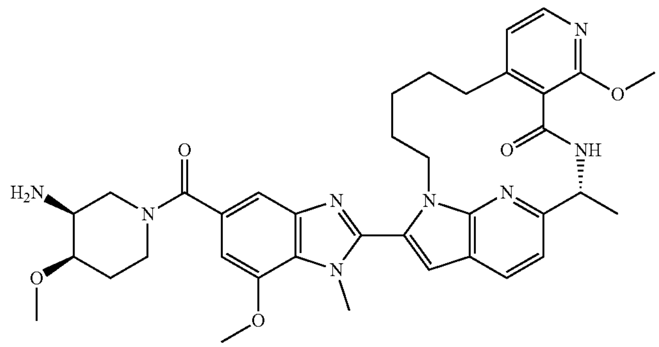 [SMILES: COc1nccc2c1C(=O)N[C@H](C)c1ccc3cc(-c4nc5cc(C(=O)N6CC[C@@H](OC)[C@@H](N)C6)cc(OC)c5n4C)n(c3n1)CCCCC2] | (2~{R})-17-[5-[(3~{S},4~{R})-3-amino-4-methoxy-piperidine-1-carbonyl]-7-methoxy-1-methyl-benzimidazol-2-yl]-6-methoxy-2-methyl-3,7,16,22-tetrazatetracyclo[14.5.2.0^{5,10}.0^{19,23}]tricosa-1(22),5(10),6,8,17,19(23),20-heptaen-4-one |
| 864 | 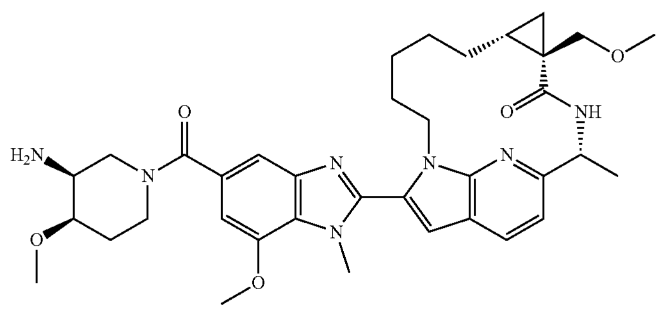 [SMILES: COC[C@]12C[C@H]1CCCCCn1c(-c3nc4cc(C(=O)N5CC[C@@H](OC)[C@@H](N)C5)cc(OC)c4n3C)cc3ccc(nc31)[C@@H](C)NC2=O] | (2~{R},5~{S},7~{R})-14-[5-[(3~{S},4~{R})-3-amino-4-methoxy-piperidine-1-carbonyl]-7-methoxy-1-methyl-benzimidazol-2-yl]-5-(methoxymethyl)-2-methyl-3,13,19-triazatetracyclo[11.5.2.0^{5,7}.0^{16,20}]icosa-1(19),14,16(20),17-tetraen-4-one |
| 865 | 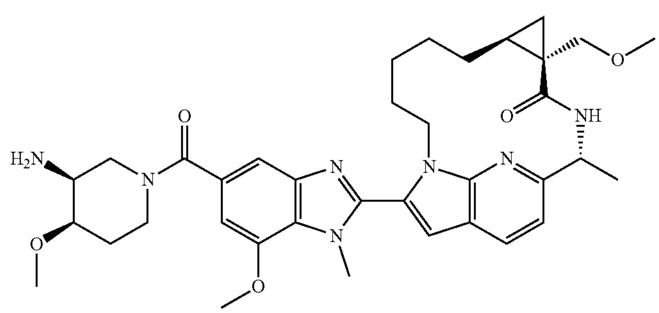 [SMILES: COC[C@@]12C[C@@H]1CCCCCn1c(-c3nc4cc(C(=O)N5CC[C@@H](OC)[C@@H](N)C5)cc(OC)c4n3C)cc3ccc(nc31)[C@@H](C)NC2=O] | (2~{R},5~{R},7~{S})-14-[5-[(3~{S},4~{R})-3-amino-4-methoxy-piperidine-1-carbonyl]-7-methoxy-1-methyl-benzimidazol-2-yl]-5-(methoxymethyl)-2-methyl-3,13,19-triazatetracyclo[11.5.2.0^{5,7}.0^{16,20}]icosa-1(19),14,16(20),17-tetraen-4-one |
| 866 | 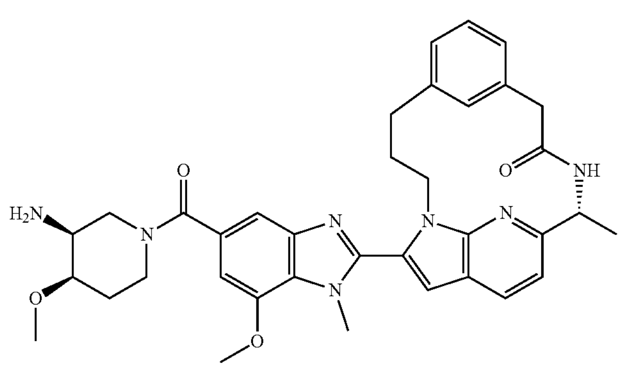 [SMILES: COc1cc(C(=O)N2CC[C@@H](OC)[C@@H](N)C2)cc2nc(-c3cc4ccc5nc4n3CCCc3cccc(c3)CC(=O)N[C@@H]5C)n(C)c12] | (13~{R})-19-[5-[(3~{S},4~{R})-3-amino-4-methoxy-piperidine-1-carbonyl]-7-methoxy-1-methyl-benzimidazol-2-yl]-13-methyl-1,12,21-triazatetracyclo[12.5.2.1^{5,9}.0^{17,20}]docosa-5,7,9(22),14(21),15,17(20),18-heptaen-11-one |

TABLE 1A-continued

| Example | Structure | Name |
|---|---|---|
| 867 | 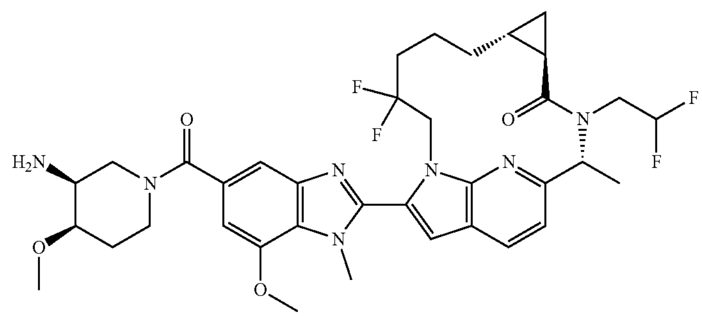 [SMILES: COc1cc(C(=O)N2CC[C@@H](OC)[C@@H](N)C2)cc2nc(-c3cc4ccc5nc4n3CC(F)(F)CCC[C@@H]3C[C@H]3C(=O)N(CC(F)F)[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-3-(2,2-difluoroethyl)-11,11-difluoro-2-methyl-3,13,19-triazatetracyclo[11.5.2.0^{5,7}.0^{16,20}]icosa-1(19),14,16(20),17-tetraen-4-one |
| 868 | 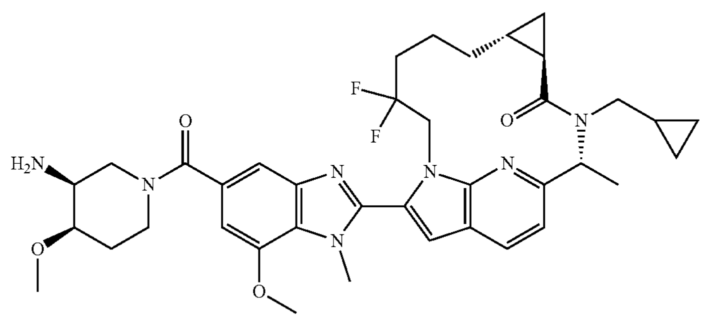 [SMILES: COc1cc(C(=O)N2CC[C@@H](OC)[C@@H](N)C2)cc2nc(-c3cc4ccc5nc4n3CC(F)(F)CCC[C@@H]3C[C@H]3C(=O)N(CC3CC3)[C@@H]5C)n(C)c12] | (2~{R},5~{R},7~{R})-14-[5-[(3~{S},4~{R})-3-amino-4-methoxy-piperidine-1-carbonyl]-7-methoxy-1-methyl-benzimidazol-2-yl]-3-(cyclopropylmethyl)-11,11-difluoro-2-methyl-3,13,19-triazatetracyclo[11.5.2.0^{5,7}.0^{16,20}]icosa-1(19),14,16(20),17-tetraen-4-one |
| 869 | 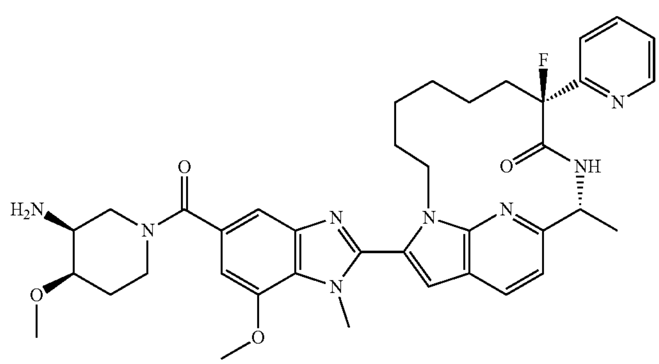 [SMILES: COc1cc(C(=O)N2CC[C@@H](OC)[C@@H](N)C2)cc2nc(-c3cc4ccc5nc4n3CCCCCC[C@](F)(c3ccccn3)C(=O)N[C@@H]5C)n(C)c12] | (8~{S},11~{R})-17-[5-[(3~{S},4~{R})-3-amino-4-methoxy-piperidine-1-carbonyl]-7-methoxy-1-methyl-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |
| 870 | 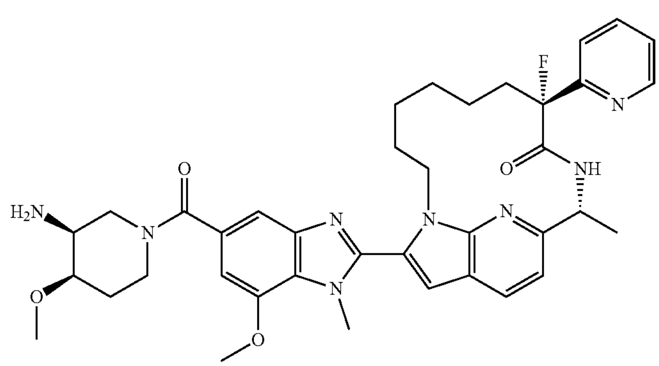 [SMILES: COc1cc(C(=O)N2CC[C@@H](OC)[C@@H](N)C2)cc2nc(-c3cc4ccc5nc4n3CCCCCC[C@@](F)(c3ccccn3)C(=O)N[C@@H]5C)n(C)c12] | (8~{R},11~{R})-17-[5-[(3~{S},4~{R})-3-amino-4-methoxy-piperidine-1-carbonyl]-7-methoxy-1-methyl-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 871 | 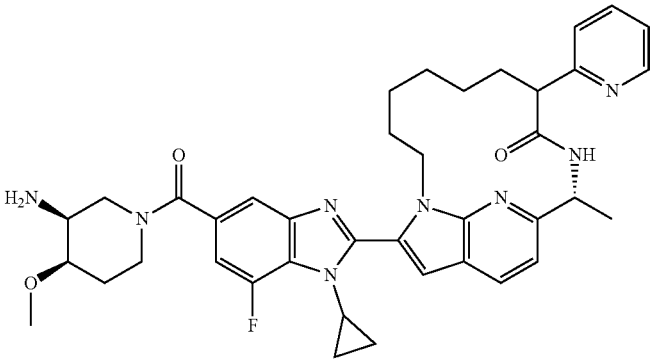 [SMILES: CO[C@@H]1CCN(C(=O)c2cc(F)c3c(c2)nc(-c2cc4ccc5nc4n2CCCCCCC(c2ccccn2)C(=O)N[C@@H]5C)n3C2CC2)C[C@@H]1N] | (11~{R})-17-[5-[(3~{S},4~{R})-3-amino-4-methoxy-piperidine-1-carbonyl]-1-cyclopropyl-7-fluoro-benzimidazol-2-yl]-11-methyl-8-(2-pyridyl)-1,10,19-triazatricyclo[10.5.2.0^{15,18}]nonadeca-12(19),13,15(18),16-tetraen-9-one |
| 872 | 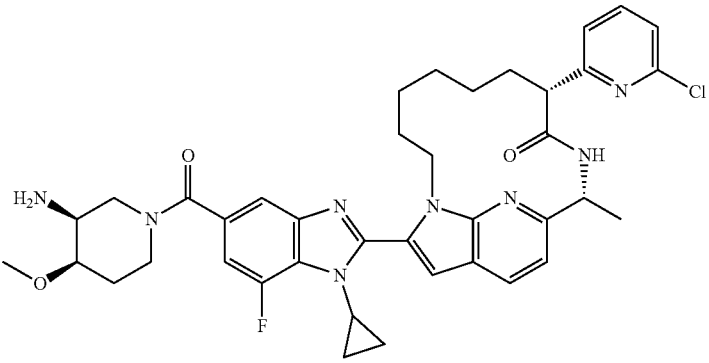 [SMILES: CO[C@@H]1CCN(C(=O)c2cc(F)c3c(c2)nc(-c2cc4ccc5nc4n2CCCCCC[C@H](c2cccc(Cl)n2)C(=O)N[C@@H]5C)n3C2CC2)C[C@@H]1N] | (8~{R},11~{R})-17-[5-[(3~{S},4~{R})-3-amino-4-methoxy-piperidine-1-carbonyl]-1-cyclopropyl-7-fluoro-benzimidazol-2-yl]-8-(6-chloro-2-pyridyl)-11-methyl-1,10,19-triazatricyclo[10.5.2.0^{15,18}]nonadeca-12(19),13,15(18),16-tetraen-9-one |
| 873 | 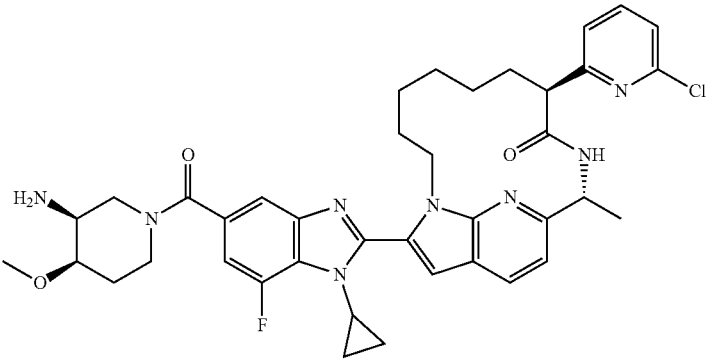 [SMILES: CO[C@@H]1CCN(C(=O)c2cc(F)c3c(c2)nc(-c2cc4ccc5nc4n2CCCCCC[C@@H](c2cccc(Cl)n2)C(=O)N[C@@H]5C)n3C2CC2)C[C@@H]1N] | (8~{S},11~{R})-17-[5-[(3~{S},4~{R})-3-amino-4-methoxy-piperidine-1-carbonyl]-1-cyclopropyl-7-fluoro-benzimidazol-2-yl]-8-(6-chloro-2-pyridyl)-11-methyl-1,10,19-triazatricyclo[10.5.2.0^{15,18}]nonadeca-12(19),13,15(18),16-tetraen-9-one |
| 874 | 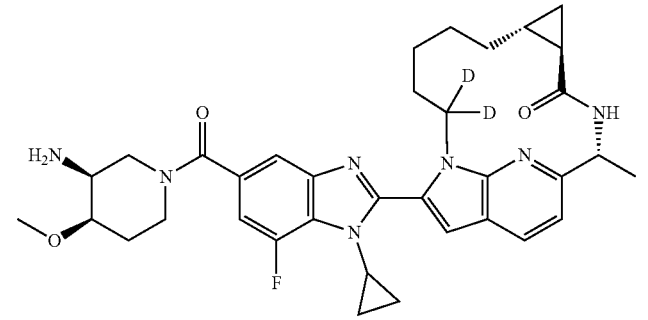 | (2~{R},5~{R},7~{R})-14-[5-[(3~{S},4~{R})-3-amino-4-methoxy-piperidine-1-carbonyl]-1-cyclopropyl-7-fluoro-benzimidazol-2-yl]-12,12-dideuterio-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 875 | 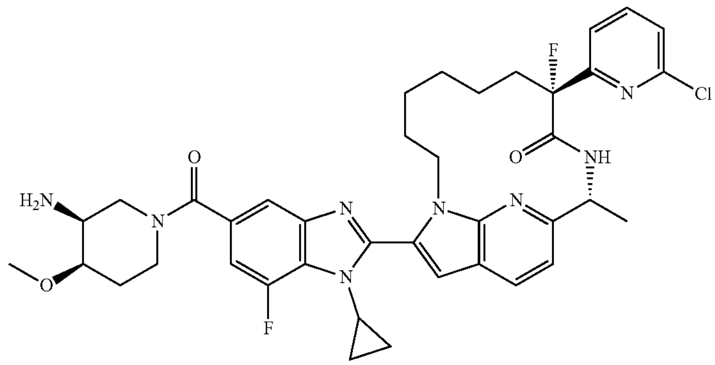 [SMILES: CO[C@@H]1CCN(C(=O)c2cc(F)c3c(c2)nc(-c2cc4ccc5nc4n2CCCCCC[C@@](F)(c2cccc(Cl)n2)C(=O)N[C@@H]5C)n3C2CC2)C[C@@H]1N] | (8~{R},11~{R})-17-[5-[(3~{S},4~{R})-3-amino-4-methoxy-piperidine-1-carbonyl]-1-cyclopropyl-7-fluoro-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 876 | 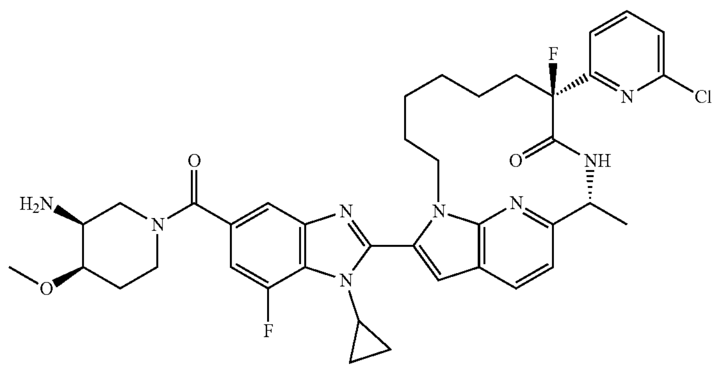 [SMILES: CO[C@@H]1CCN(C(=O)c2cc(F)c3c(c2)nc(-c2cc4ccc5nc4n2CCCCCC[C@](F)(c2cccc(Cl)n2)C(=O)N[C@@H]5C)n3C2CC2)C[C@@H]1N] | (8~{S},11~{R})-17-[5-[(3~{S},4~{R})-3-amino-4-methoxy-piperidine-1-carbonyl]-1-cyclopropyl-7-fluoro-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 877 | 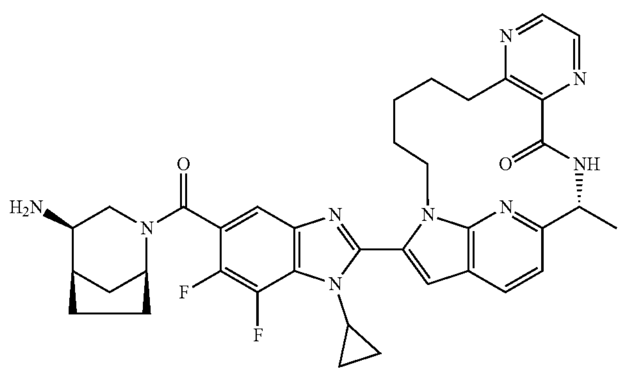 [SMILES: C[C@H]1NC(=O)c2nccnc2CCCCCn2c(-c3nc4cc(C(=O)N5C[C@H](N)[C@@H]6CC[C@H]5C6)c(F)c(F)c4n3C3CC3)cc3ccc1nc32] | (2~{R})-17-[5-[(1~{S},4~{R},5~{})-4-amino-2-azabicyclo[3.2.1]octane-2-carbonyl]-1-cyclopropyl-6,7-difluoro-benzimidazol-2-yl]-2-methyl-3,6,9,16,22-pentazatetracyclo[14.5.2.0^{5,10}.0^{19,23}]tricosa-1(22),5(10),6,8,17,19(23),20-heptaen-4-one |
| 878 | 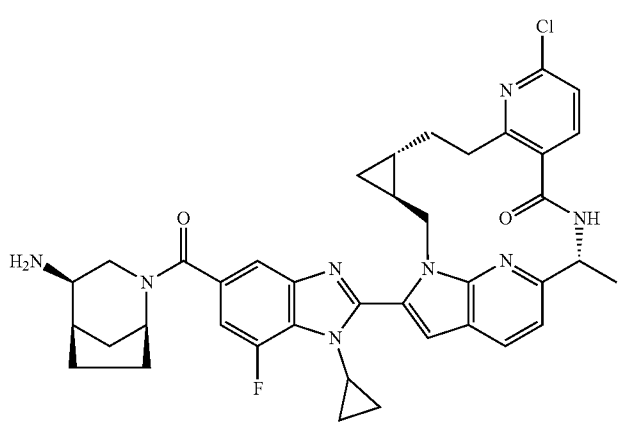 [SMILES: C[C@H]1NC(=O)c2ccc(Cl)nc2CC[C@H]2C[C@@H]2Cn2c(-c3nc4cc(C(=O)N5C[C@H](N)[C@@H]6CC[C@H]5C6)cc(F)c4n3C3CC3)cc3ccc1nc32] | (3~{S},5~{S},16~{R})-22-[5-[(1~{S},4~{R},5~{R})-4-amino-2-azabicyclo[3.2.1]octane-2-carbonyl]-1-cyclopropyl-7-fluoro-benzimidazol-2-yl]-10-chloro-16-methyl-1,9,15,24-tetrazapentacyclo[15.5.2.0^{3,5}.0^{8,13}.0^{20,23}]tetracosa-8(13),9,11,17(24),18,20(23),21-heptaen-14-one |

TABLE 1A-continued

| Example | Structure | Name |
|---|---|---|
| 879 | 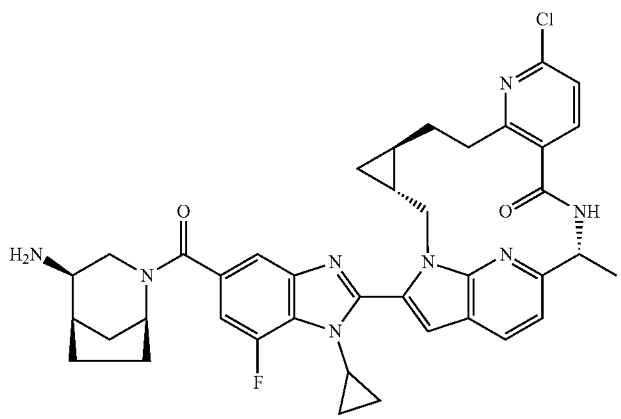 [SMILES: C[C@H]1NC(=O)c2ccc(Cl)nc2CC[C@@H]2C[C@H]2Cn2c(-c3nc4cc(C(=O)N5C[C@H](N)[C@@H]6CC[C@H]5C6)cc(F)c4n3C3CC3)cc3ccc1nc32] | (3~{R},5~{R},16~{R})-22-[5-[(1~{S},4~{R},5~{R})-4-amino-2-azabicyclo[3.2.1]octane-2-carbonyl]-1-cyclopropyl-7-fluoro-benzimidazol-2-yl]-10-chloro-16-methyl-1,9,15,24-tetrazapentacyclo[15.5.2.0^{3,5}.0^{8,13}.0^{20,23}]tetracosa-8(13),9,11,17(24),18,20(23),21-heptaen-14-one |
| 880 | 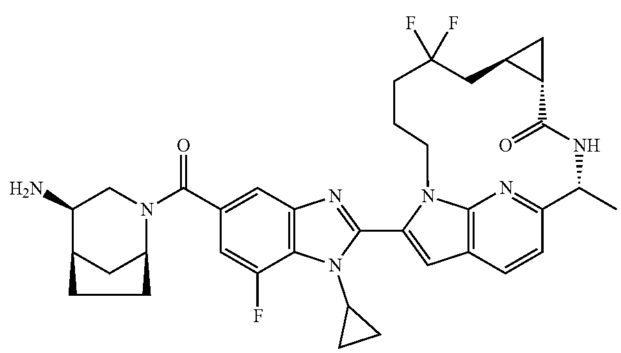 [SMILES: C[C@H]1NC(=O)[C@H]2C[C@@H]2CC(F)(F)CCCn2c(-c3nc4cc(C(=O)N5C[C@H](N)[C@@H]6CC[C@H]5C6)cc(F)c4n3C3CC3)cc3ccc1nc32] | (2~{R},5~{S},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |
| 881 | 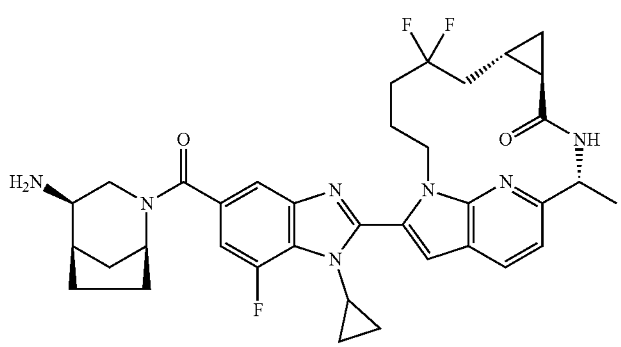 [SMILES: C[C@H]1NC(=O)[C@@H]2C[C@H]2CC(F)(F)CCCn2c(-c3nc4cc(C(=O)N5C[C@H](N)[C@@H]6CC[C@H]5C6)cc(F)c4n3C3CC3)cc3ccc1nc32] | (2~{R},5~{R},7~{S})-14-[5-[(1~{S},4~{R},5~{R})-4-amino-2-azabicyclo[3.2.1]octane-2-carbonyl]-1-cyclopropyl-7-fluoro-benzimidazol-2-yl]-9,9-difluoro-2-methyl-3,13,19-triazatetracyclo[11.5.2.0^{5,7}.0^{16,20}]icosa-1(19),14,16(20),17-tetraen-4-one |
| 882 | 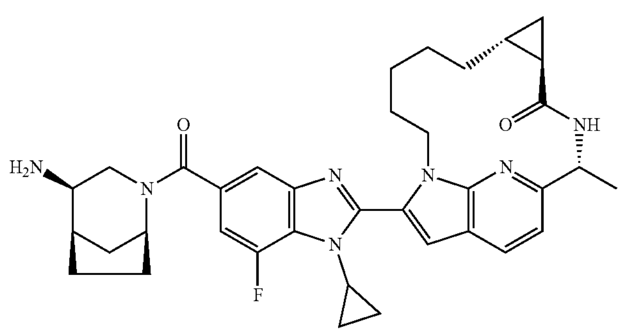 [SMILES: C[C@H]1NC(=O)[C@@H]2C[C@H]2CCCCCn2c(-c3nc4cc(C(=O)N5C[C@H](N)[C@@H]6CC[C@H]5C6)cc(F)c4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 883 | 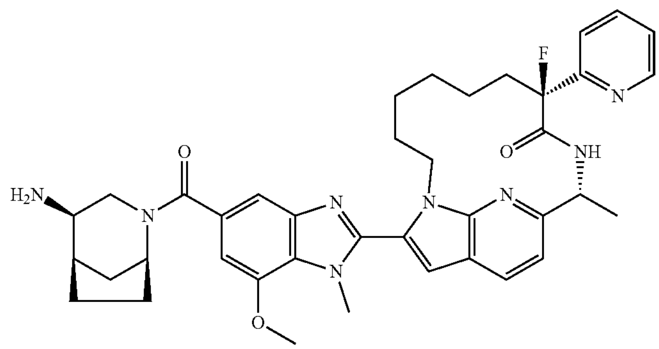 [SMILES: COc1cc(C(=O)N2C[C@H](N)[C@@H]3CC[C@H]2C3)cc2nc(-c3cc4ccc5nc4n3CCCCCC[C@](F)(c3ccccn3)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |
| 884 | 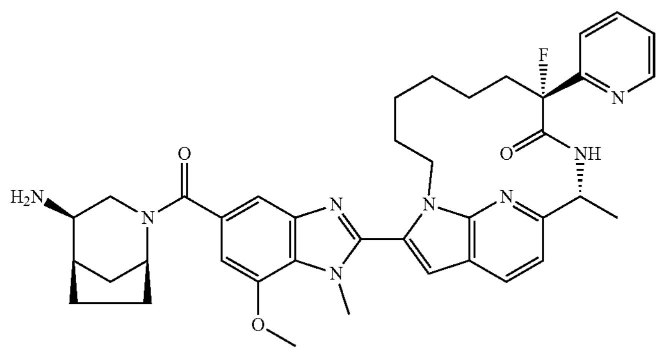 [SMILES: COc1cc(C(=O)N2C[C@H](N)[C@@H]3CC[C@H]2C3)cc2nc(-c3cc4ccc5nc4n3CCCCCC[C@@](F)(c3ccccn3)C(=O)N[C@@H]5C)n(C)c12] | (8~{R},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |
| 885 | 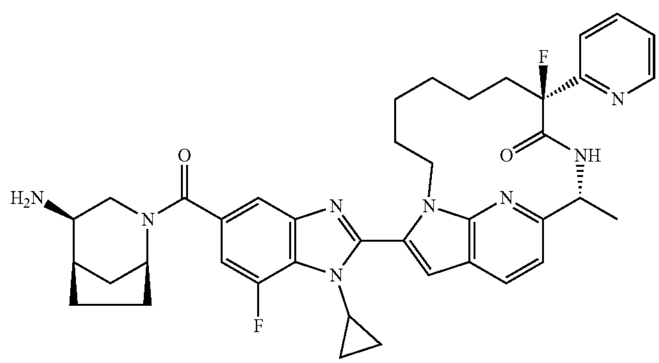 [SMILES: C[C@H]1NC(=O)[C@@](F)(c2ccccn2)CCCCCCn2c(-c3nc4cc(C(=O)N5C[C@H](N)[C@@H]6CC[C@H]5C6)cc(F)c4n3C3CC3)cc3ccc1nc32] | (8~{S},11~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |
| 886 | 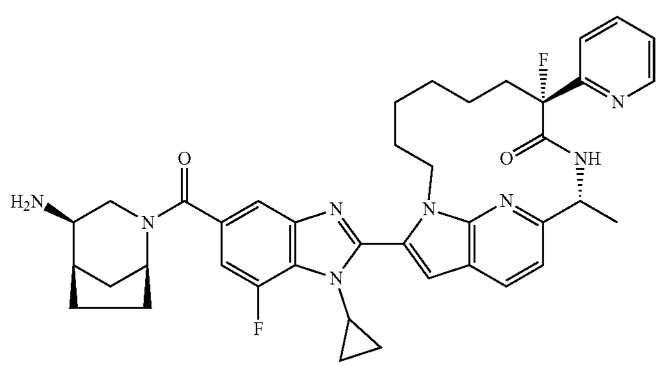 [SMILES: C[C@H]1NC(=O)[C@](F)(c2ccccn2)CCCCCCn2c(-c3nc4cc(C(=O)N5C[C@H](N)[C@@H]6CC[C@H]5C6)cc(F)c4n3C3CC3)cc3ccc1nc32] | (8~{R},11~{R})-17-[5-[(1~{S},4~{R},5~{R))-4-amino-2-azabicyclo[3.2.1]octane-2-carbonyl]-1-cyclopropyl-7-fluoro-benzimidazol-2-yl]-8-fluoro-11-methyl-8-(2-pyridyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 887 | 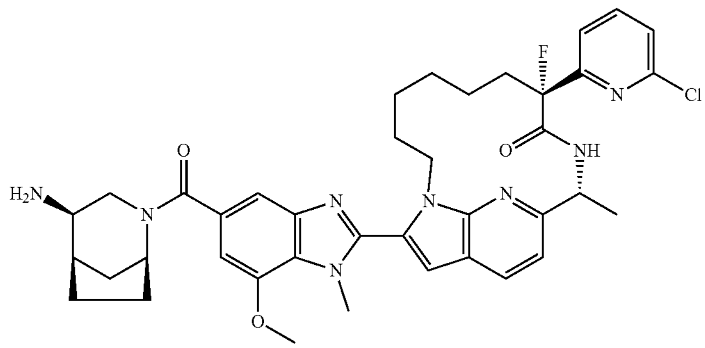 [SMILES: COc1cc(C(=O)N2C[C@H](N)[C@@H]3CC[C@H]2C3)cc2nc(-c3cc4ccc5nc4n3CCCCCC[C@@](F)(c3cccc(Cl)n3)C(=O)N[C@@H]5C)n(C)c12] | (8~{R},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 888 | 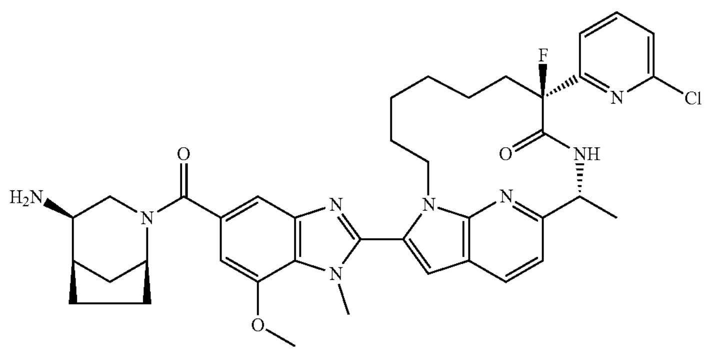 [SMILES: COc1cc(C(=O)N2C[C@H](N)[C@@H]3CC[C@H]2C3)cc2nc(-c3cc4ccc5nc4n3CCCCCC[C@](F)(c3cccc(Cl)n3)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-(6-chloro-2-pyridyl)-8-fluoro-11-methyl-1,10,19-triazatricyclo[10.5.2.0^{15,18}]nonadeca-12(19),13,15(18),16-tetraen-9-one |
| 889 | 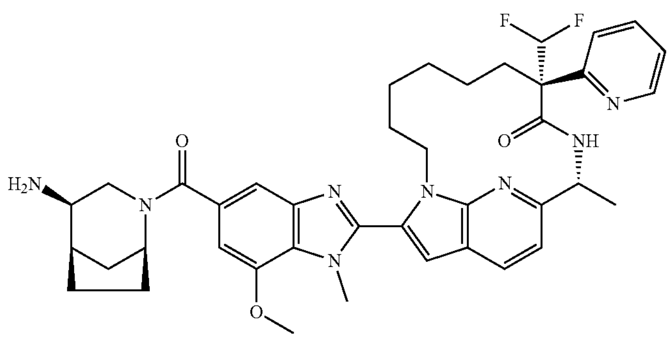 [SMILES: COc1cc(C(=O)N2C[C@H](N)[C@@H]3CC[C@H]2C3)cc2nc(-c3cc4ccc5nc4n3CCCCCC[C@](c3ccccn3)(C(F)F)C(=O)N[C@@H]5C)n(C)c12] | (8~{R},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-(difluoromethyl)-11-methyl-8-(2-pyridyl)-1,10,19-triazatricyclo[10.5.2.0^{15,18}]nonadeca-12(19),13,15(18),16-tetraen-9-one |
| 890 | 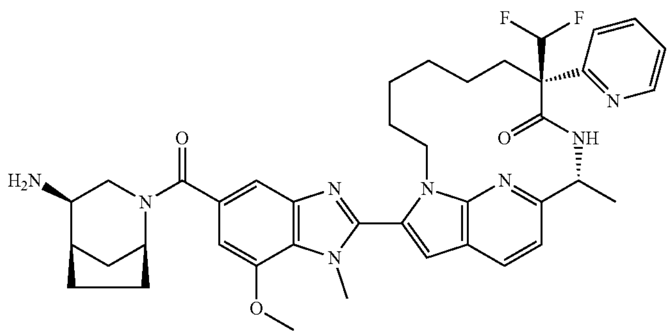 [SMILES: COc1cc(C(=O)N2C[C@H](N)[C@@H]3CC[C@H]2C3)cc2nc(-c3cc4ccc5nc4n3CCCCCC[C@@](c3ccccn3)(C(F)F)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-(difluoromethyl)-11-methyl-8-(2-pyridyl)-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 891 | 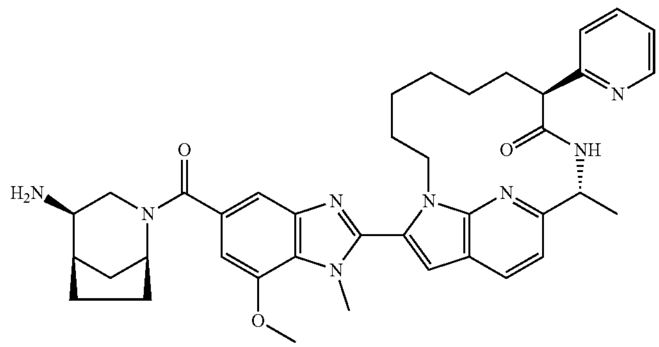 [SMILES: COc1cc(C(=O)N2C[C@H](N)[C@@H]3CC[C@H]2C3)cc2nc(-c3cc4ccc5nc4n3CCCCCC[C@@H](c3ccccn3)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-11-methyl-8-(2-pyridyl)-1,10,19-triazatricyclo[10.5.2.0^{15,18}]nonadeca-12(19),13,15(18),16-tetraen-9-one |
| 892 | 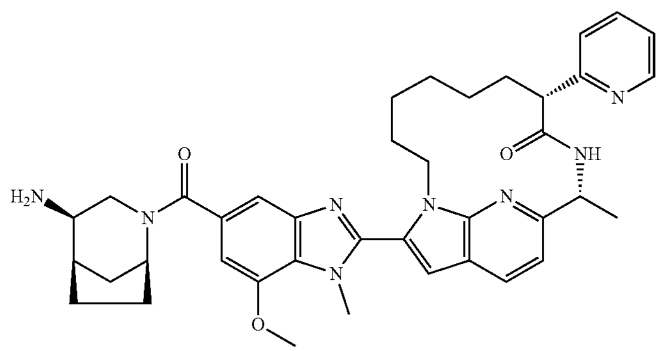 [SMILES: COc1cc(C(=O)N2C[C@H](N)[C@@H]3CC[C@H]2C3)cc2nc(-c3cc4ccc5nc4n3CCCCCC[C@H](c3ccccn3)C(=O)N[C@@H]5C)n(C)c12] | (8~{R},11~{R})-17-[5-[(1~{S},4~{R},5~{R})-4-amino-2-azabicyclo[3.2.1]octane-2-carbonyl]-7-methoxy-1-methyl-benzimidazol-2-yl]-11-methyl-8-(2-pyridyl)-1,10,19-triazatricyclo[10.5.2.0^{15,18}]nonadeca-12(19),13,15(18),16-tetraen-9-one |
| 893 | 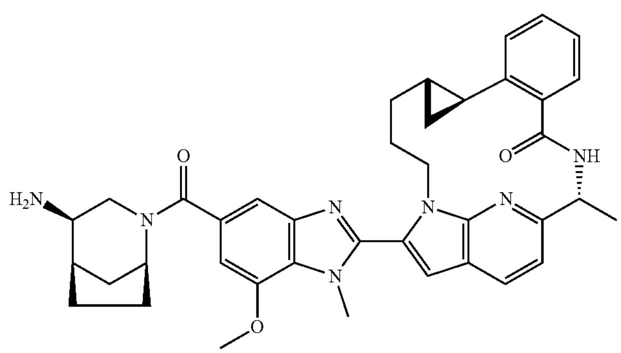 [SMILES: COc1cc(C(=O)N2C[C@H](N)[C@@H]3CC[C@H]2C3)cc2nc(-c3cc4ccc5nc4n3CCC[C@H]3C[C@@H]3c3ccccc3C(=O)N[C@@H]5C)n(C)c12] | (5~{S},7~{S},16~{R})-22-[5-[(1~{S},4~{R},5~{R})-4-amino-2-azabicyclo[3.2.1]octane-2-carbonyl]-7-methoxy-1-methyl-benzimidazol-2-yl]-16-methyl-1,15,24-triazapentacyclo[15.5.2.0^{5,7}.0^{8,13}0^{{20,23}}]tetracosa-8(13),9,11,17(24),18,20(23),21-heptaen-14-one |
| 894 | 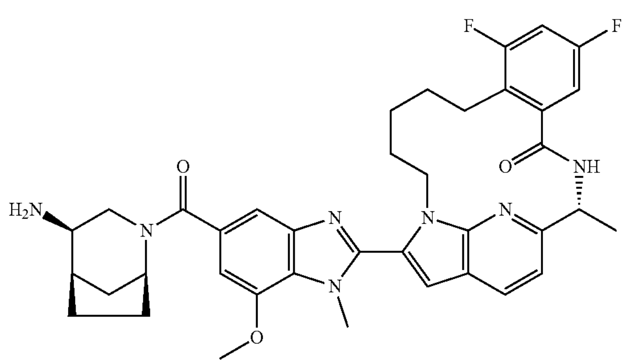 [SMILES: COc1cc(C(=O)N2C[C@H](N)[C@@H]3CC[C@H]2C3)cc2nc(-c3cc4ccc5nc4n3CCCCCc3c(F)cc(F)cc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-7,9-difluoro-2-methyl-3,16,22-triazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 895 | 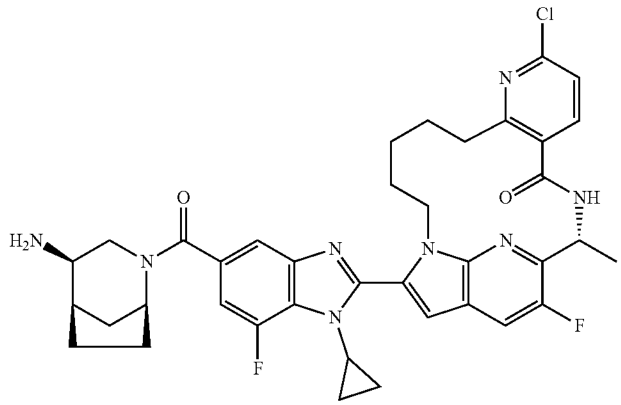 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3C3CC3)cc3cc(F)c1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-21-fluoro-2-methyl-3,9,16,22-tetrazatetracyclo[14.5.2.0^{5,10}.0^{19,23}]tricosa-1(22),5(10),6,8,17,19(23),20-heptaen-4-one |
| 896 | 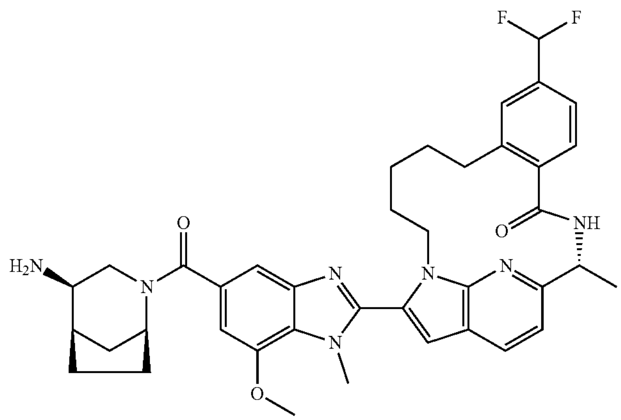 [SMILES: COc1cc(C(=O)N2C[C@H](N)[C@@H]3CC[C@H]2C3)cc2nc(-c3cc4ccc5nc4n3CCCCCc3cc(C(F)F)ccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-(difluoromethyl)-2-methyl-3,16,22-triazatetracyclo[14.5.2.0^{5,10}.0^{19,23}]tricosa-1(22),5(10),6,8,17,19(23),20-heptaen-4-one |
| 897 | 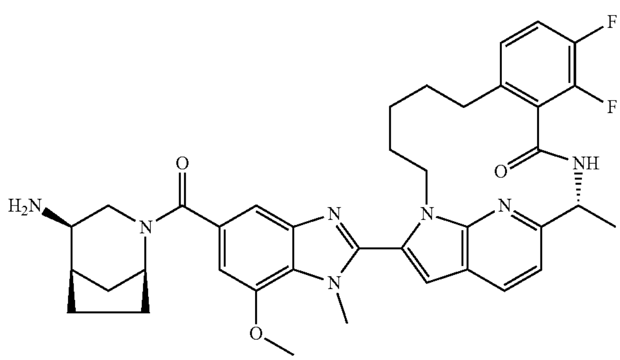 [SMILES: COc1cc(C(=O)N2C[C@H](N)[C@@H]3CC[C@H]2C3)cc2nc(-c3cc4ccc5nc4n3CCCCCc3ccc(F)c(F)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6,7-difluoro-2-methyl-3,16,22-triazatetracyclo[14.5.2.0^{5,10}.0^{19,23}]tricosa-1(22),5(10),6,8,17,19(23),20-heptaen-4-one |
| 898 | 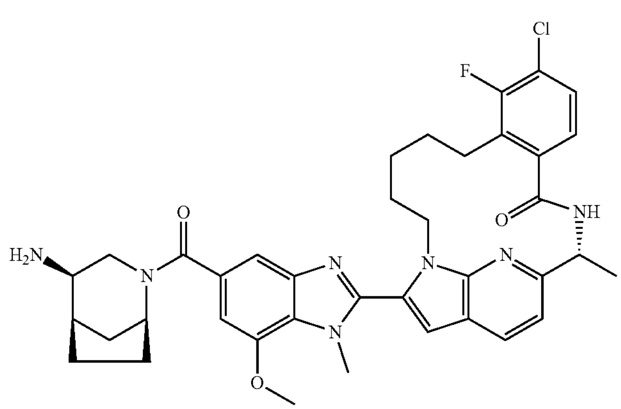 [SMILES: COc1cc(C(=O)N2C[C@H](N)[C@@H]3CC[C@H]2C3)cc2nc(-c3cc4ccc5nc4n3CCCCCc3c(ccc(Cl)c3F)C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-chloro-9-fluoro-2-methyl-3,16,22-triazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 899 | 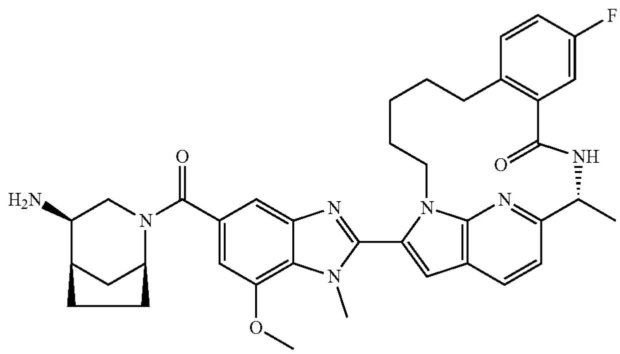 [SMILES: COc1cc(C(=O)N2C[C@H](N)[C@@H]3CC[C@H]2C3)cc2nc(-c3cc4ccc5nc4n3CCCCCc3ccc(F)cc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-7-fluoro-2-methyl-3,16,22-triazatetracyclo[14.5.2.0^{5,10}.0^{19,23}]tricosa-1(22),5(10),6,8,17,19(23),20-heptaen-4-one |
| 900 | 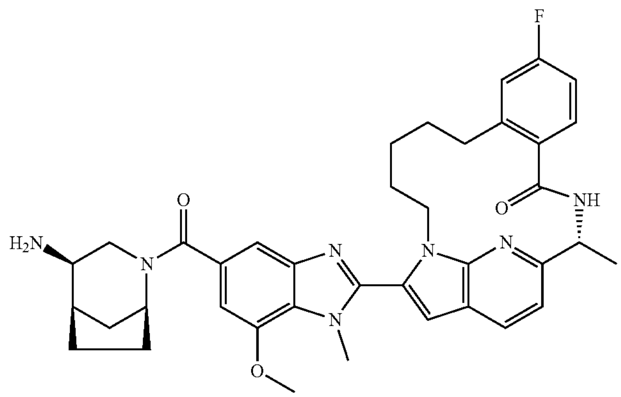 [SMILES: COc1cc(C(=O)N2C[C@H](N)[C@@H]3CC[C@H]2C3)cc2nc(-c3cc4ccc5nc4n3CCCCCc3cc(F)ccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-fluoro-2-methyl-3,16,22-triazatetracyclo[14.5.2.0^{5,10}.0^{19,23}]tricosa-1(22),5(10),6,8,17,19(23),20-heptaen-4-one |
| 901 | 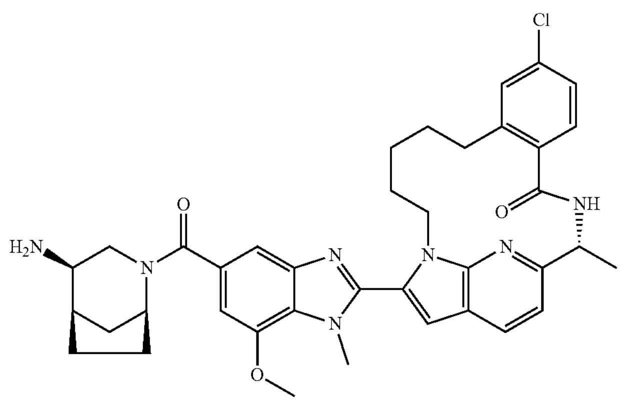 [SMILES: COc1cc(C(=O)N2C[C@H](N)[C@@H]3CC[C@H]2C3)cc2nc(-c3cc4ccc5nc4n3CCCCCc3cc(Cl)ccc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8-chloro-2-methyl-3,16,22-triazatetracyclo[14.5.2.0^{5,10}.0^{19,23}]tricosa-1(22),5(10),6,8,17,19(23),20-heptaen-4-one |
| 902 | 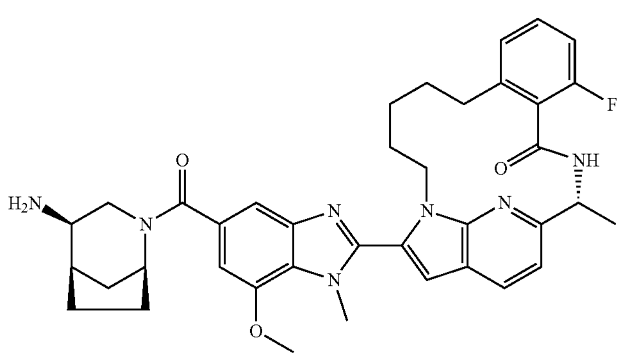 [SMILES: COc1cc(C(=O)N2C[C@H](N)[C@@H]3CC[C@H]2C3)cc2nc(-c3cc4ccc5nc4n3CCCCCc3cccc(F)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6-fluoro-2-methyl-3,16,22-triazatetracyclo[14.5.2.0^{5,10}.0^{19,23}]tricosa-1(22),5(10),6,8,17,19(23),20-heptaen-4-one |

| Example | Structure | Name |
|---|---|---|
| 903 | 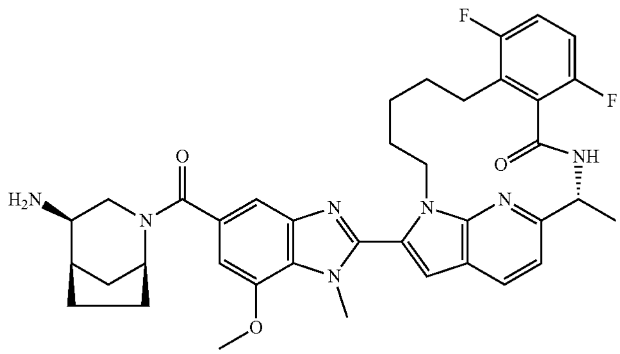 [SMILES: COc1cc(C(=O)N2C[C@H](N)[C@@H]3CC[C@H]2C3)cc2nc(-c3cc4ccc5nc4n3CCCCCc3c(F)ccc(F)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6,9-difluoro-2-methyl-3,16,22-triazatetracyclo[14.5.2.0˄{5,10}.0˄{19,23}]tricosa-1(22),5(10),6,8,17,19(23),20-heptaen-4-one |
| 904 | 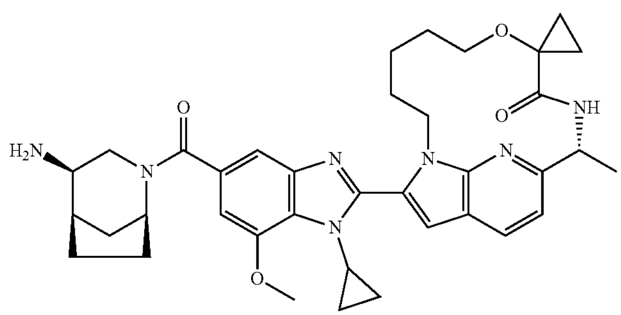 [SMILES: COc1cc(C(=O)N2C[C@H](N)[C@@H]3CC[C@H]2C3)cc2nc(-c3cc4ccc5nc4n3CCCCCOC3(CC3)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-11-methyl-spiro[7-oxa-1,10,19-triazatricyclo[10.5.2.0˄{15,18}]nonadeca-12(19),13,15(18),16-tetraene-8,1'-cyclopropane]-9-one |
| 905 | 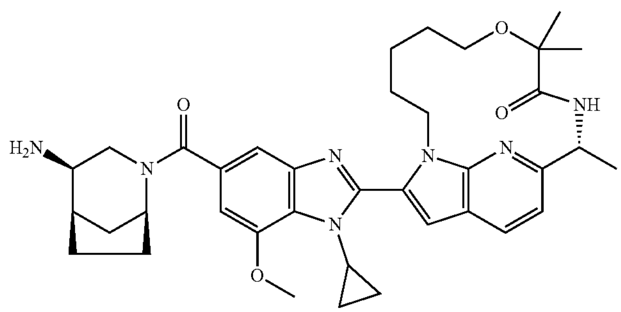 [SMILES: COc1cc(C(=O)N2C[C@H](N)[C@@H]3CC[C@H]2C3)cc2nc(-c3cc4ccc5nc4n3CCCCCOC(C)(C)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8,8,11-trimethyl-7-oxa-1,10,19-triazatricyclo[10.5.2.0˄{15,18}]nonadeca-12(19),13,15(18),16-tetraen-9-one |
| 906 | 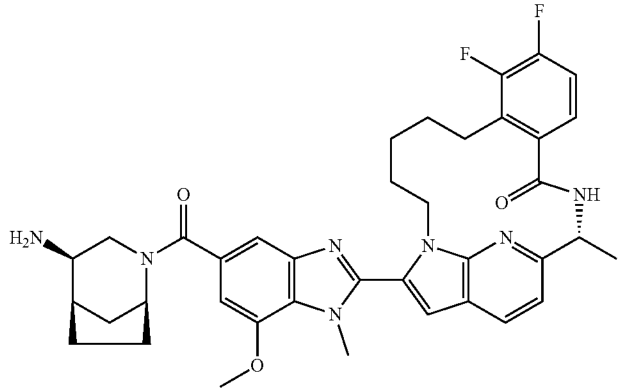 [SMILES: COc1cc(C(=O)N2C[C@H](N)[C@@H]3CC[C@H]2C3)cc2nc(-c3cc4ccc5nc4n3CCCCCc3c(ccc(F)c3F)C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-8,9-difluoro-2-methyl-3,16,22-triazatetracyclo[14.5.2.0˄{5,10}.0˄{19,23}]tricosa-1(22),5(10),6,8,17,19(23),20-heptaen-4-one |

TABLE 1A-continued

| Example | Structure | Name |
|---|---|---|
| 907 | 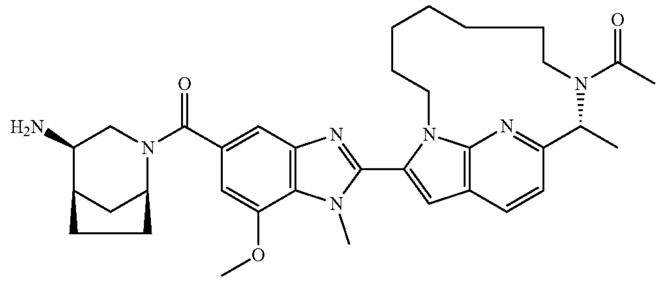 [SMILES: COc1cc(C(=O)N2C[C@H](N)[C@@H]3CC[C@H]2C3)cc2nc(-c3cc4ccc5nc4n3CCCCCCCN(C(C)=O)[C@@H]5C)n(C)c12] | 1-[(10~{R})-16-[5-[(1~{S},4~{R},5~{R})-4-amino-2-azabicyclo[3.2.1]octane-2-carbonyl]-7-methoxy-1-methyl-benzimidazol-2-yl]-10-methyl-1,9,18-triazatricyclo[9.5.2.0^{14,17}]octadeca-11(18),12,14(17),15-tetraen-9-yl]ethanone |
| 908 | 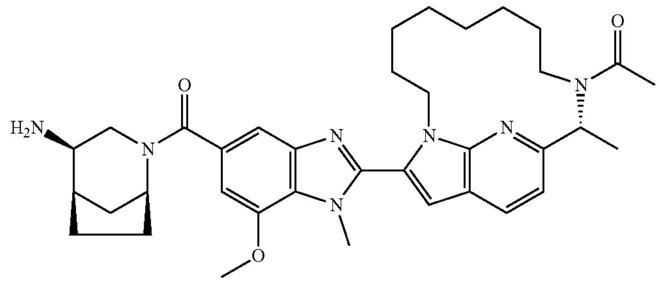 [SMILES: COc1cc(C(=O)N2C[C@H](N)[C@@H]3CC[C@H]2C3)cc2nc(-c3cc4ccc5nc4n3CCCCCCCCN(C(C)=O)[C@@H]5C)n(C)c12] | 1-[(11~{R})-17-[5-[(1~{S},4~{R},5~{R})-4-amino-2-azabicyclo[3.2.1]octane-2-carbonyl]-7-methoxy-1-methyl-benzimidazol-2-yl]-11-methyl-1,10,19-triazatricyclo[10.5.2.0^{15,18}]nonadeca-12(19),13,15(18),16-tetraen-10-yl]ethanone |
| 909 | 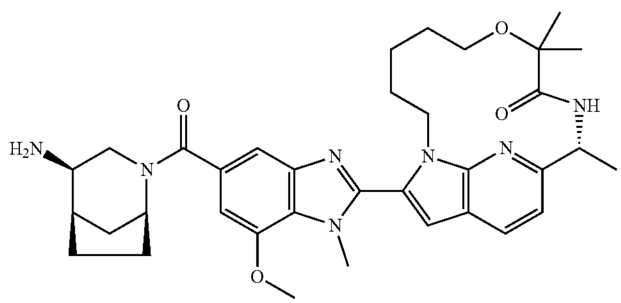 [SMILES: COc1cc(C(=O)N2C[C@H](N)[C@@H]3CC[C@H]2C3)cc2nc(-c3cc4ccc5nc4n3CCCCCOC(C)(C)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-8,8,11-trimethyl-7-oxa-1,10,19-triazatricyclo[10.5.2.0^{15,18}]nonadeca-12(19),13,15(18),16-tetraen-9-one |
| 910 | 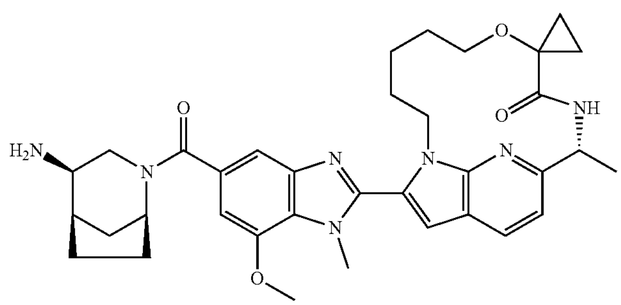 [SMILES: COc1cc(C(=O)N2C[C@H](N)[C@@H]3CC[C@H]2C3)cc2nc(-c3cc4ccc5nc4n3CCCCCOC3(CC3)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-11-methyl-spiro[7-oxa-1,10,19-triazatricyclo[10.5.2.0^{15,18}]nonadeca-12(19),13,15(18),16-tetraene-8,1'-cyclopropane]-9-one |
| 911 | 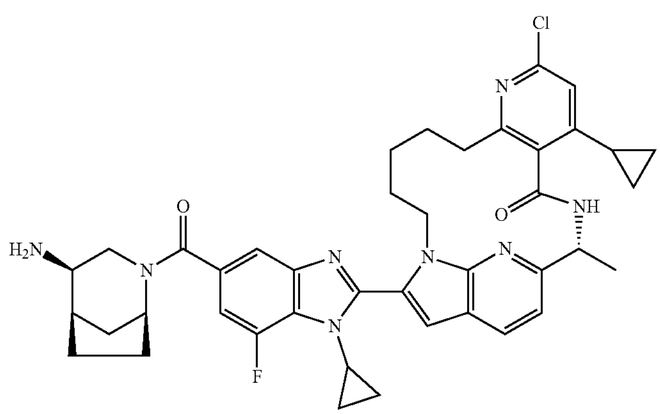 [SMILES: C[C@H]1NC(=O)c2c(C3CC3)cc(Cl)nc2CCCCCn2c(-c3nc4cc(C(=O)N5C[C@H](N)[C@@H]6CC[C@H]5C6)cc(F)c4n3C3CC3)cc3ccc1nc32] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-6-cyclopropyl-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 912 | 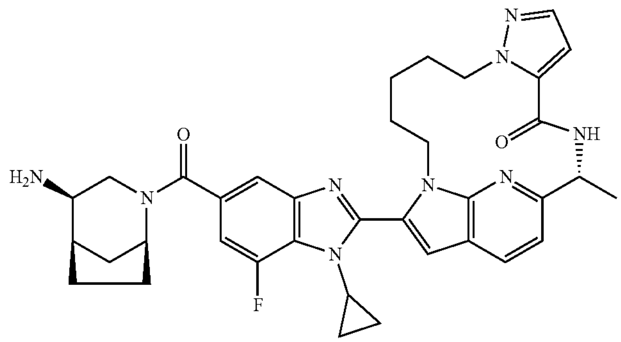 [SMILES: C[C@H]1NC(=O)c2ccnn2CCCCCn2c(-c3nc4cc(C(=O)N5C[C@H](N)[C@@H]6CC[C@H]5C6)cc(F)c4n3C3CC3)cc3ccc1nc32] | (2~{R})-16-[5-[(1~{S},4~{R},5~{R})-4-amino-2-azabicyclo[3.2.1]octane-2-carbonyl]-1-cyclopropyl-7-fluoro-benzimidazol-2-yl]-2-methyl-3,8,9,15,21-pentazatetracyclo[13.5.2.0^{5,9}.0^{18,22}]docosa-1(21),5,7,16,18(22),19-hexaen-4-one |
| 913 | 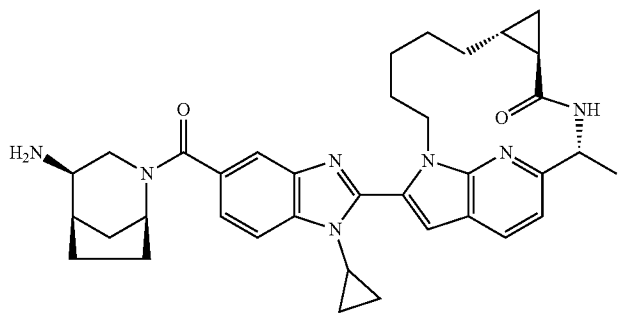 [SMILES: C[C@H]1NC(=O)[C@@H]2C[C@H]2CCCCCn2c(-c3nc4cc(C(=O)N5C[C@H](N)[C@@H]6CC[C@H]5C6)ccc4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-benzimidazol-2-yl]-2-methyl-3,13,19-triazatetracyclo[11.5.2.0^{5,7}.0^{16,20}]icosa-1(19),14,16(20),17-tetraen-4-one |
| 914 | 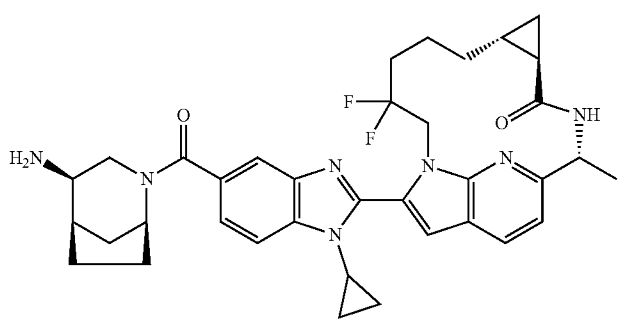 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)ccc4n3C3CC3)cc3ccc1nc32] | (2~{R},5~{R},7~{R})-14-[5-[(1~{S},4~{R},5~{R})-4-amino-2-azabicyclo[3.2.1]octane-2-carbonyl]-1-cyclopropyl-benzimidazol-2-yl]-11,11-difluoro-2-methyl-3,13,19-triazatetracyclo[11.5.2.0^{5,7}.0^{16,20}]icosa-1(19),14,16(20),17-tetraen-4-one |
| 915 | 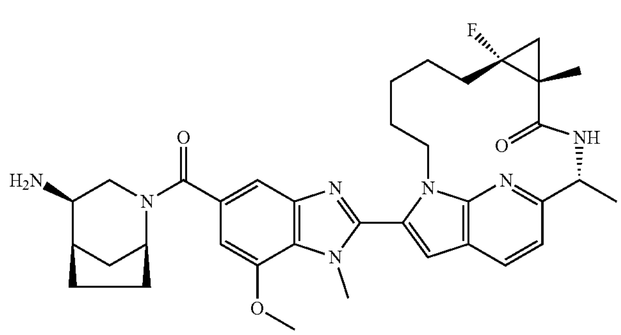 [SMILES: COc1cc(C(=O)N2C[C@H](N)[C@@H]3CC[C@H]2C3)cc2nc(-c3cc4ccc5nc4n3CCCCC[C@@]3(F)C[C@]3(C)C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-7-fluoro-2,5-dimethyl-3,13,19-triazatetracyclo[11.5.2.0^{5,7}.0^{16,20}]icosa-1(19),14,16(20),17-tetraen-4-one |

TABLE 1A-continued

| Example | Structure | Name |
|---|---|---|
| 916 | 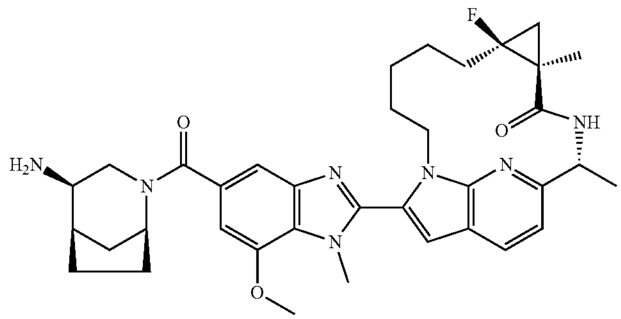 [SMILES: COc1cc(C(=O)N2C[C@H](N)[C@@H]3CC[C@H]2C3)cc2nc(-c3cc4ccc5nc4n3CCCCC[C@]3(F)C[C@@]3(C)C(=O)N[C@@H]5C)n(C)c12] | (2~{R},5~{S},7~{S})-14-[5-[(1~{S},4~{R},5~{R})-4-amino-2-azabicyclo[3.2.1]octane-2-carbonyl]-7-methoxy-1-methyl-benzimidazol-2-yl]-7-fluoro-2,5-dimethyl-3,13,19-triazatetracyclo[11.5.2.0^{5,7}.0^{16,20}]icosa-1(19),14,16(20),17-tetraen-4-one |
| 917 | 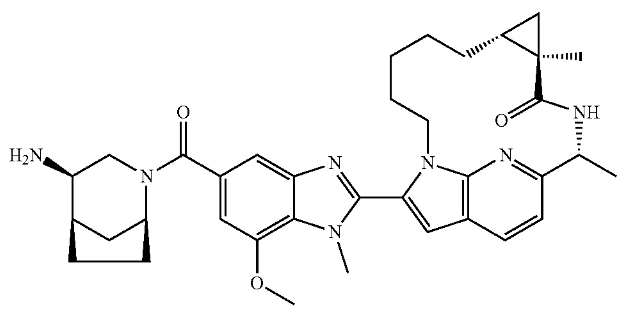 [SMILES: COc1cc(C(=O)N2C[C@H](N)[C@@H]3CC[C@H]2C3)cc2nc(-c3cc4ccc5nc4n3CCCCC[C@@H]3C[C@@]3(C)C(=O)N[C@@H]5C)n(C)c12] | (2~{R},5~{R},7~{R})-14-[5-[(1~{S},4~{R},5~{R})-4-amino-2-azabicyclo[3.2.1]octane-2-carbonyl]-7-methoxy-1-methyl-benzimidazol-2-yl]-2,5-dimethyl-3,13,19-triazatetracyclo[11.5.2.0^{5,7}.0^{16,20}]icosa-1(19),14,16(20),17-tetraen-4-one |
| 918 | 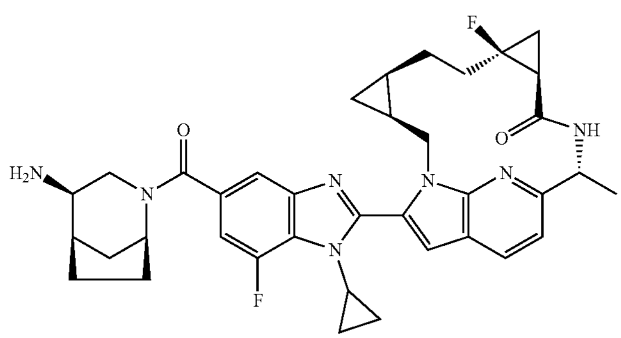 [SMILES: C[C@H]1NC(=O)[C@@H]2C[C@@]2(F)CC[C@@H]2C[C@@H]2Cn2c(-c3nc4cc(C(=O)N5C[C@H](N)[C@@H]6CC[C@H]5C6)cc(F)c4n3C3CC3)cc3ccc1nc32] | (3~{S},5~{R},8~{S},10~{S},13~{R})-19-[5-[(1~{S},4~{R},5~{R})-4-amino-2-azabicyclo[3.2.1]octane-2-carbonyl]-1-cyclopropyl-7-fluoro-benzimidazol-2-yl]-8-fluoro-13-methyl-1,12,21-triazapentacyclo[12.5.2.0^{3,5}.0^{8,10}.0^{17,20}]henicosa-14(21),15,17(20),18-tetraen-11-one |
| 919 | 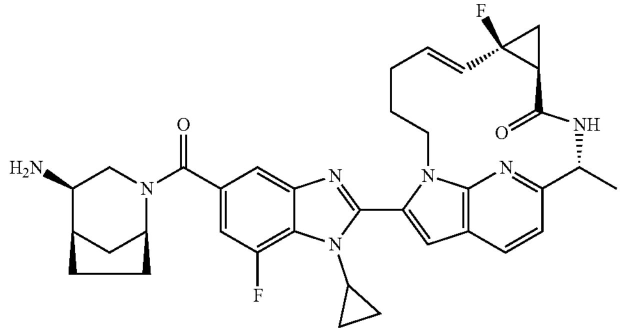 [SMILES: C[C@H]1NC(=O)[C@@H]2C[C@@]2(F)/C=C/CCCn2c(-c3nc4cc(C(=O)N5C[C@H](N)[C@@H]6CC[C@H]5C6)cc(F)c4n3C3CC3)cc3ccc1nc32] | (2~{R},5~{S},7~{R},8~{E})-14-[5-[(1~{S},4~{R},5~{R})-4-amino-2-azabicyclo[3.2.1]octane-2-carbonyl]-1-cyclopropyl-7-fluoro-benzimidazol-2-yl]-7-fluoro-2-methyl-3,13,19-triazatetracyclo[11.5.2.0^{5,7}.0^{16,20}]icosa-1(19),8,14,16(20),17-pentaen-4-one |

TABLE 1A-continued

| Example | Structure | Name |
|---|---|---|
| 920 | 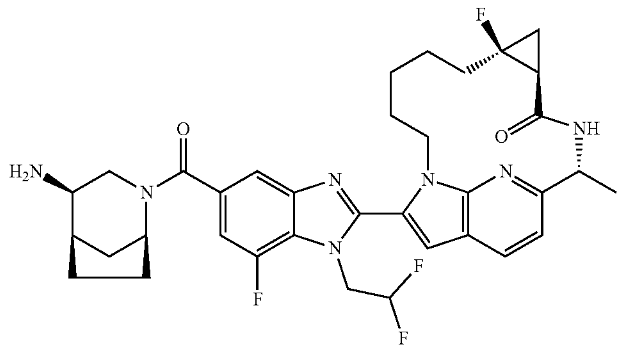 [SMILES: C[C@H]1NC(=O)[C@@H]2C[C@@]2(F)CCCCCn2c(-c3nc4cc(C(=O)N5C[C@H](N)[C@@H]6CC[C@H]5C6)cc(F)c4n3CC(F)F)cc3ccc1nc32] | (2~{R},5~{S},7~{S})-14-[5-[(1~{S},4~{R},5~{R})-4-amino-2-azabicyclo[3.2.1]octane-2-carbonyl]-1-(2,2-difluoroethyl)-7-fluoro-benzimidazol-2-yl]-7-fluoro-2-methyl-3,13,19-triazatetracyclo [11.5.2.0^{5,7}.0^{16,20}] icosa-1(19),14,16(20),17-tetraen-4-one |
| 921 | 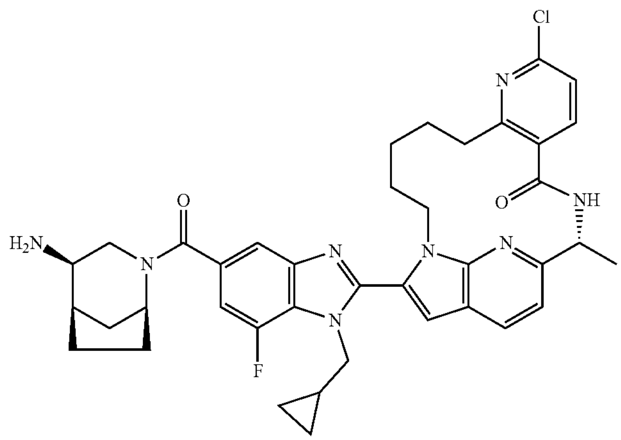 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3CC3CC3)cc3ccc1nc32] | (2~{R})-17-[5-[(1~{S},4~{R},5~{R})-4-amino-2-azabicyclo [3.2.1]octane-2-carbonyl]-1-(cyclopropylmethyl)-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 922 | 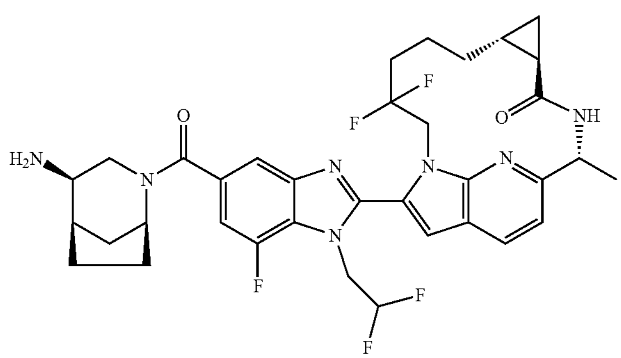 [SMILES: C[C@H]1NC(=O)[C@@H]2C[C@H]2CCCC(F)(F)Cn2c(-c3nc4cc(C(=O)N5C[C@H](N)[C@@H]6CC[C@H]5C6)cc(F)c4n3CC(F)F)cc3ccc1nc32] | (2~{R},5~{R},7~{R})-14-[5-[(1~{S},4~{R},5~{R})-4-amino-2-azabicyclo[3.2.1]octane-2-carbonyl]-1-(2,2-difluoroethyl)-7-fluoro-benzimidazol-2-yl]-11,11-difluoro-2-methyl-3,13,19-triazatetracyclo [11.5.2.0^{5,7}.0^{16,20}] icosa-1(19),14,16(20),17-tetraen-4-one |
| 923 | 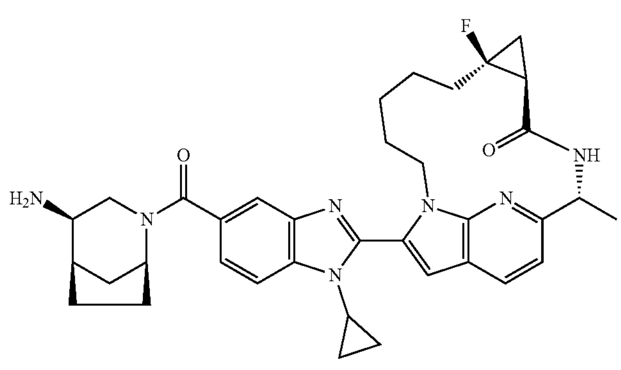 [SMILES: C[C@H]1NC(=O)[C@@H]2C[C@@]2(F)CCCCCn2c(-c3nc4cc(C(=O)N5C[C@H](N)[C@@H]6CC[C@H]5C6)ccc4n3C3CC3)cc3ccc1nc32] | (2~{R},5~{S},7~{S})-14-[5-[(1~{S},4~{R},5~{R})-4-amino-2-azabicyclo[3.2.1]octane-2-carbonyl]-1-cyclopropyl-benzimidazol-2-yl]-7-fluoro-2-methyl-3,13,19-triazatetracyclo [11.5.2.0^{5,7}.0^{16,20}] icosa-1(19),14,16(20),17-tetraen-4-one |

| Example | Structure | Name |
|---------|-----------|------|
| 924 | 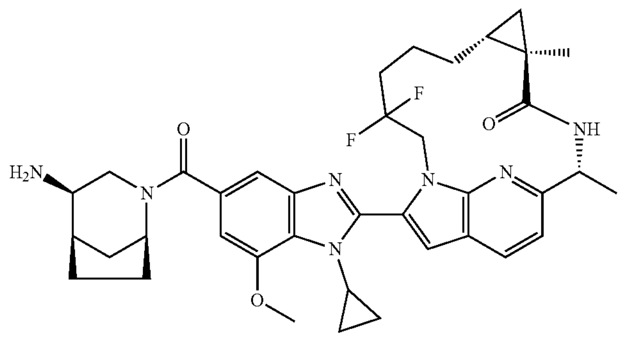 [SMILES: COc1cc(C(=O)N2C[C@H](N)[C@@H]3CC[C@H]2C3)cc2nc(-c3cc4ccc5nc4n3CC(F)(F)CCC[C@@H]3C[C@@]3(C)C(=O)N[C@@H]5C)n(C3CC3)c12] | (2~{R},5~{R},7~{R})-14-[5-[(1~{S},4~{R},5~{R})-4-amino-2-azabicyclo[3.2.1]octane-2-carbonyl]-1-cyclopropyl-7-methoxy-benzimidazol-2-yl]-11,11-difluoro-2,5-dimethyl-3,13,19-triazatetracyclo[11.5.2.0^{5,7}.0^{16,20}]icosa-1(19),14,16(20),17-tetraen-4-one |
| 925 | 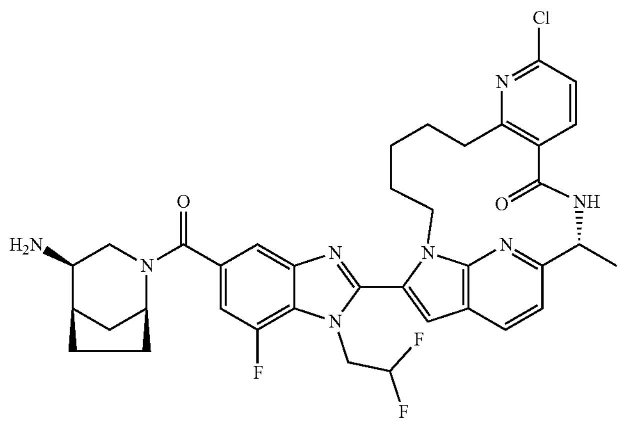 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3CC(F)F)cc3ccc1nc32] | (2~{R})-17-[5-[(1~{S},4~{R},5~{R})-4-amino-2-azabicyclo[3.2.1]octane-2-carbonyl]-1-(2,2-difluoroethyl)-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 926 | 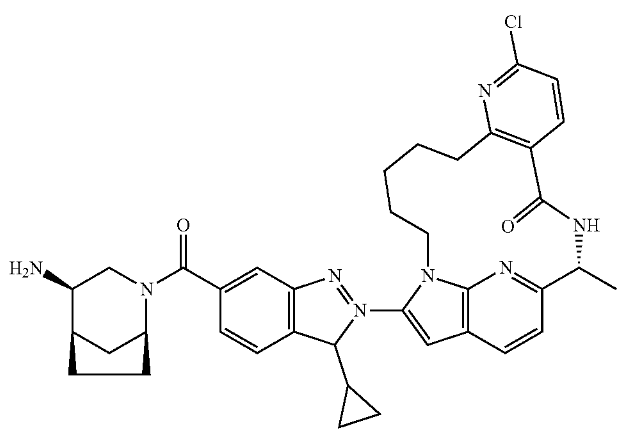 | (2~{R})-17-[5-[(1~{S},4~{R},5~{R})-4-amino-2-azabicyclo[3.2.1]octane-2-carbonyl]-1-cyclopropyl-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |
| 927 | 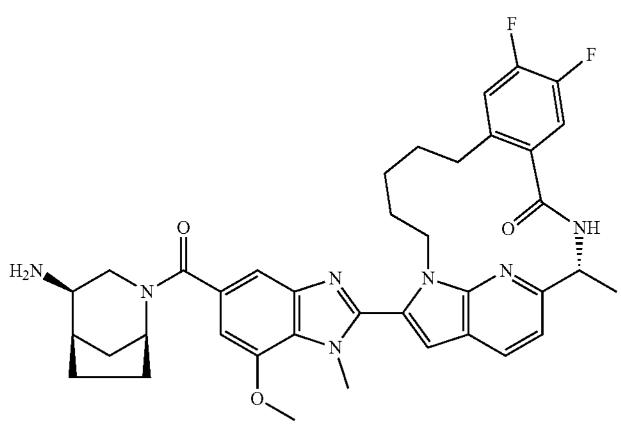 [SMILES: COc1cc(C(=O)N2C[C@H](N)[C@@H]3CC[C@H]2C3)cc2nc(-c3cc4ccc5nc4n3CCCCCc3cc(F)c(F)cc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-7,8-difluoro-2-methyl-3,16,22-triazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 928 | 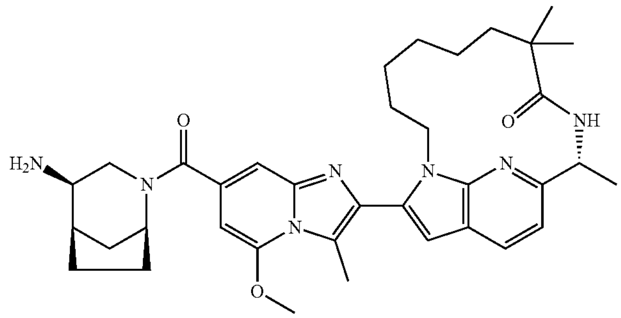 [SMILES: COc1cc(C(=O)N2C[C@H](N)[C@@H]3CC[C@H]2C3)cc2nc(-c3cc4ccc5nc4n3CCCCCCC(C)(C)C(=O)N[C@@H]5C)c(C)n12] | (11~{R})-17-[7-[(1~{S},4~{R},5~{R})-4-amino-2-azabicyclo[3.2.1]octane-2-carbonyl]-5-methoxy-3-methyl-imidazo[1,2-a]pyridin-2-yl]-8,8,11-trimethyl-1,10,19-triazatricyclo[10.5.2.0^{15,18}]nonadeca-12(19),13,15(18),16-tetraen-9-one |
| 929 | 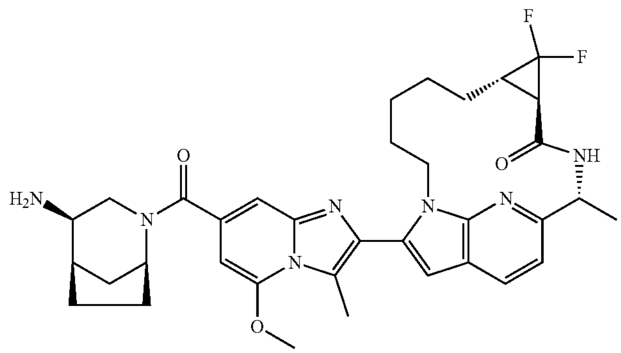 [SMILES: COc1cc(C(=O)N2C[C@H](N)[C@@H]3CC[C@H]2C3)cc2nc(-c3cc4ccc5nc4n3CCCCC[C@H]3[C@H](C(=O)N[C@@H]5C)C3(F)F)c(C)n12] | (2~{R},5~{R},7~{S})-14-[7-[(1~{S},4~{R},5~{R})-4-amino-2-azabicyclo[3.2.1]octane-2-carbonyl]-5-methoxy-3-methyl-imidazo[1,2-a]pyridin-2-yl]-6,6-difluoro-2-methyl-3,13,19-triazatetracyclo[11.5.2.0^{5,7}.0^{16,20}]icosa-1(19),14,16(20),17-tetraen-4-one |
| 930 | 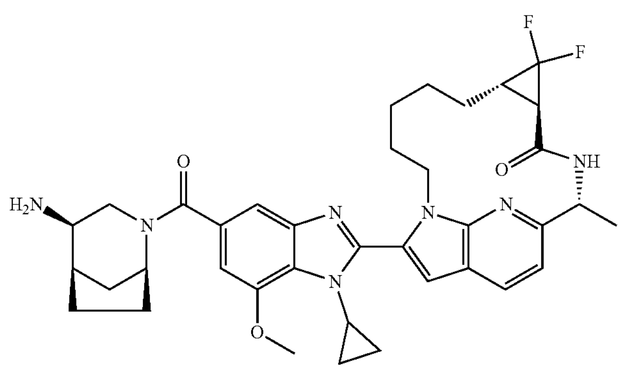 [SMILES: COc1cc(C(=O)N2C[C@H](N)[C@@H]3CC[C@H]2C3)cc2nc(-c3cc4ccc5nc4n3CCCCC[C@H]3[C@H](C(=O)N[C@@H]5C)C3(F)F)n(C3CC3)c12] | (2~{R},5~{R},7~{S})-14-[5-[(1~{S},4~{R},5~{R})-4-amino-2-azabicyclo[3.2.1]octane-2-carbonyl]-1-cyclopropyl-7-methoxy-benzimidazol-2-yl]-6,6-difluoro-2-methyl-3,13,19-triazatetracyclo[11.5.2.0^{5,7}.0^{16,20}]icosa-1(19),14,16(20),17-tetraen-4-one |
| 931 | 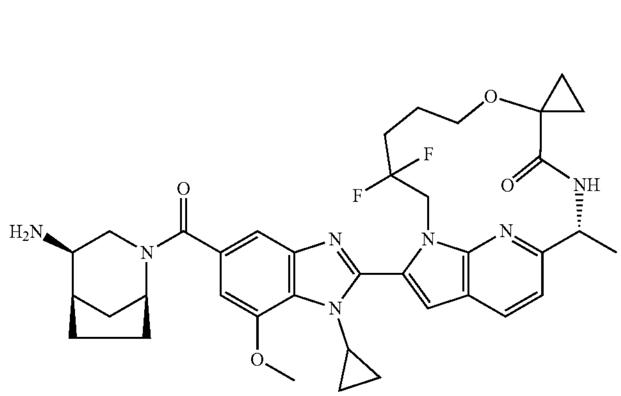 [SMILES: COc1cc(C(=O)N2C[C@H](N)[C@@H]3CC[C@H]2C3)cc2nc(-c3cc4ccc5nc4n3CC(F)(F)CCCOC3(CC3)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-3,3-difluoro-11-methyl-spiro[7-oxa-1,10,19-triazatricyclo[10.5.2.0^{15,18}]nonadeca-12(19),13,15(18),16-tetraene-8,1'-cyclopropane]-9-one |

TABLE 1A-continued

| Example | Structure | Name |
|---|---|---|
| 932 | 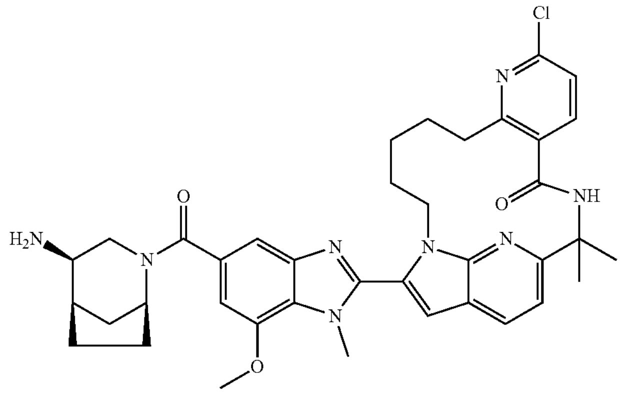 [SMILES: COc1cc(C(=O)N2C[C@H](N)[C@@H]3CC[C@H]2C3)cc2nc(-c3cc4ccc5nc4n3CCCCCc3nc(Cl)ccc3C(=O)NC5(C)C)n(C)c12] | 17-[5-[(1~{S},4~{R},5~{R})-4-amino-2-azabicyclo[3.2.1]octane-2-carbonyl]-7-methoxy-1-methyl-benzimidazol-2-yl]-8-chloro-2,2-dimethyl-3,9,16,22-tetrazatetracyclo[14.5.2.0^{5,10}.0^{19,23}]tricosa-1(21),5(10),6,8,17,19,22-heptaen-4-one |
| 933 | 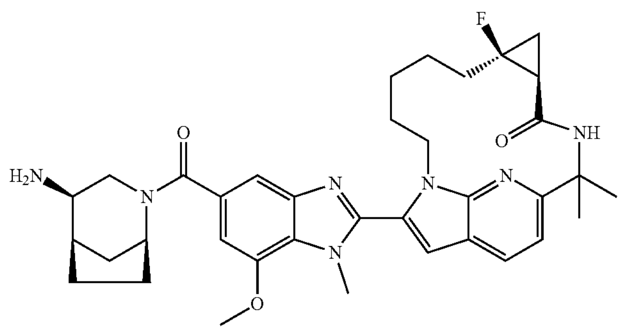 [SMILES: COc1cc(C(=O)N2C[C@H](N)[C@@H]3CC[C@H]2C3)cc2nc(-c3cc4ccc5nc4n3CCCCC[C@]3(F)C[C@H]3C(=O)NC5(C)C)n(C)c12] | (5~{S},7~{S})-14-[5-[(1~{S},4~{R},5~{R})-4-amino-2-azabicyclo[3.2.1]octane-2-carbonyl]-7-methoxy-1-methyl-benzimidazol-2-yl]-7-fluoro-2,2-dimethyl-3,13,19-triazatetracyclo[11.5.2.0^{5,7}.0^{16,20}]icosa-1(18),14,16,19-tetraen-4-one |
| 934 | 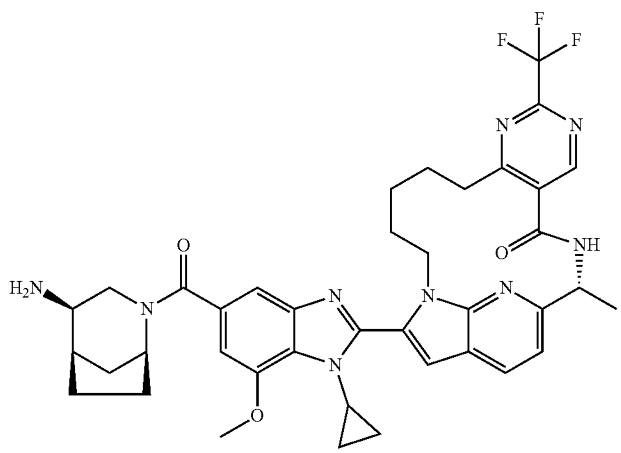 [SMILES: COc1cc(C(=O)N2C[C@H](N)[C@@H]3CC[C@H]2C3)cc2nc(-c3cc4ccc5nc4n3CCCCCc3nc(C(F)(F)F)ncc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-2-methyl-8-(trifluoromethyl)-3,7,9,16,22-pentazatetracyclo[14.5.2.0^{5,10}.0^{19,23}]tricosa-1(21),5(10),6,8,17,19,22-heptaen-4-one |
| 935 | 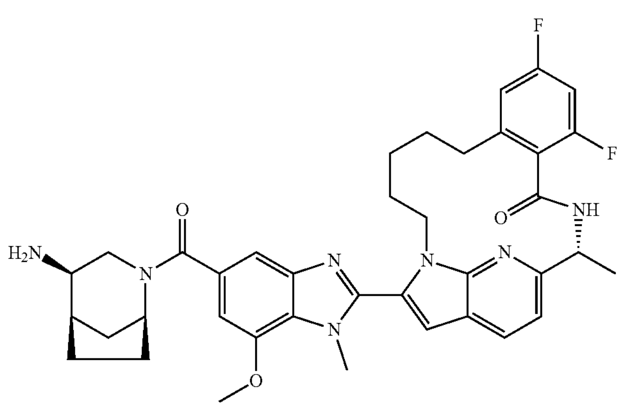 [SMILES: COc1cc(C(=O)N2C[C@H](N)[C@@H]3CC[C@H]2C3)cc2nc(-c3cc4ccc5nc4n3CCCCCc3cc(F)cc(F)c3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-6,8-difluoro-2-methyl-3,16,22-triazatetracyclo[14.5.2.0^{5,10}.0^{19,23}]tricosa-1(21),5(10),6,8,17,19,22-heptaen-4-one |

US 11,976,083 B2

TABLE 1A-continued

| Example | Structure | Name |
|---|---|---|
| 936 | 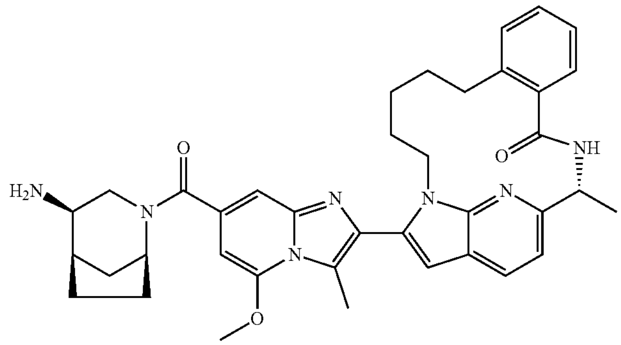 [SMILES: COc1cc(C(=O)N2C[C@H](N)[C@@H]3CC[C@H]2C3)cc2nc(-c3cc4ccc5nc4n3CCCCCc3ccccc3C(=O)N[C@@H]5C)c(C)n12] | (2~{R})-17-[7-[(1~{S},4~{R},5~{R})-4-amino-2-azabicyclo[3.2.1]octane-2-carbonyl]-5-methoxy-3-methyl-imidazo[1,2-a]pyridin-2-yl]-2-methyl-3,16,22-triazatetracyclo[14.5.2.0^{5,10}.0^{19,23}]tricosa-1(21),5(10),6,8,17,19,22-heptaen-4-one |
| 937 | 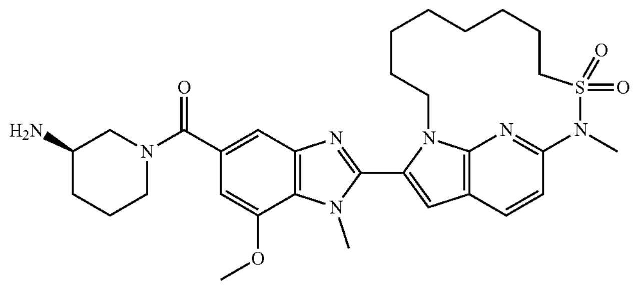 [SMILES: COc1cc(C(=O)N2CCC[C@@H](N)C2)cc2nc(-c3cc4ccc5nc4n3CCCCCCCCS(=O)(=O)N5C)n(C)c12] | [(3~{R})-3-amino-1-piperidyl]-[7-methoxy-1-methyl-2-(11-methyl-10,10-dioxo-10$1^{6}-thia-1,11,19-triazatricyclo[10.5.2.0^{15,18}]nonadeca-12(19),13,15(18),16-tetraen-17-yl)benzimidazol-5-yl]methanone |
| 938 | 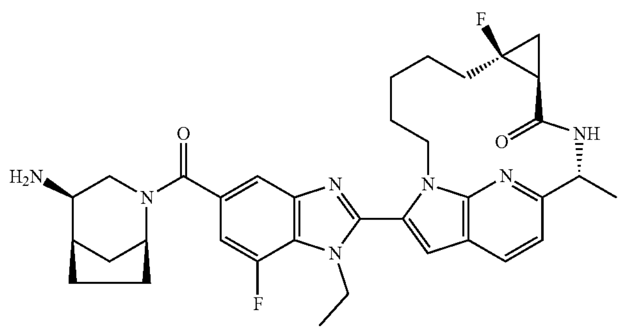 [SMILES: CCn1c(-c2cc3ccc4nc3n2CCCCC[C@]2(F)C[C@H]2C(=O)N[C@@H]4C)nc2cc(C(=O)N3C[C@H](N)[C@@H]4CC[C@H]3C4)cc(F)c21] | (2~{R},5~{S},7~{S})-14-[5-[(1~{S},4~{R},5~{R})-4-amino-2-azabicyclo[3.2.1]octane-2-carbonyl]-1-ethyl-7-fluoro-benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 939 | 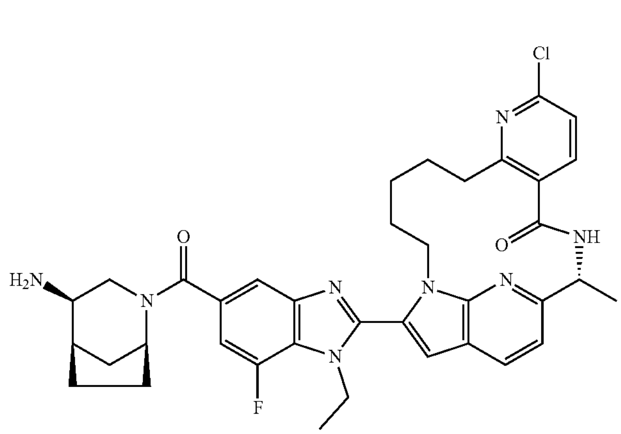 [SMILES: CCn1c(-c2cc3ccc4nc3n2CCCCCc2nc(Cl)ccc2C(=O)N[C@@H]4C)nc2cc(C(=O)N3C[C@H](N)[C@@H]4CC[C@H]3C4)cc(F)c21] | (2~{R})-17-[5-[(1~{S},4~{R},5~{R})-4-amino-2-azabicyclo[3.2.1]octane-2-carbonyl]-1-ethyl-7-fluoro-benzimidazol-2-yl]-8-chloro-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 940 | 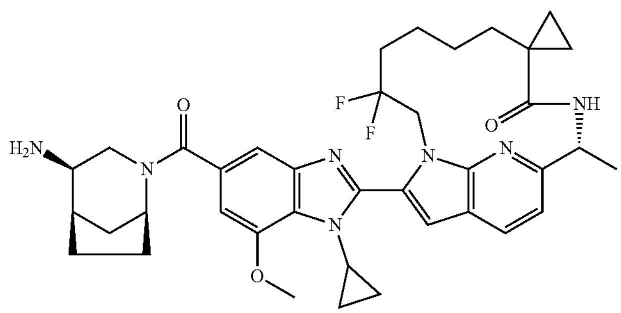 [SMILES: COc1cc(C(=O)N2C[C@H](N)[C@@H]3CC[C@H]2C3)cc2nc(-c3cc4ccc5nc4n3CC(F)(F)CCCCC3(CC3)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-3,3-difluoro-11-methyl-spiro[1,10,19-triazatricyclo[10.5.2.0^{15,18}]nonadeca-12(19),13,15(18),16-tetraene-8,1'-cyclopropane]-9-one |
| 941 | 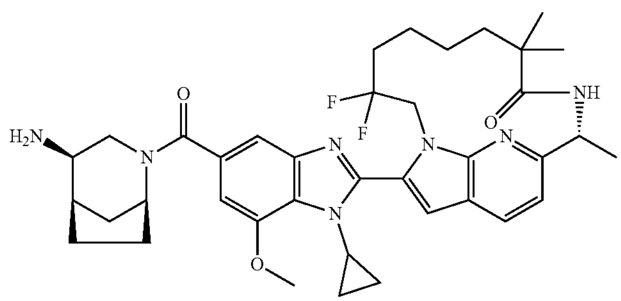 [SMILES: COc1cc(C(=O)N2C[C@H](N)[C@@H]3CC[C@H]2C3)cc2nc(-c3cc4ccc5nc4n3CC(F)(F)CCCCC(C)(C)C(=O)N[C@@H]5C)n(C3CC3)c12] | (11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-3,3-difluoro-8,8,11-trimethyl-1,10,19-triazatricyclo[10.5.2.0^{15,18}]nonadeca-12(19),13,15(18),16-tetraen-9-one |
| 942 | 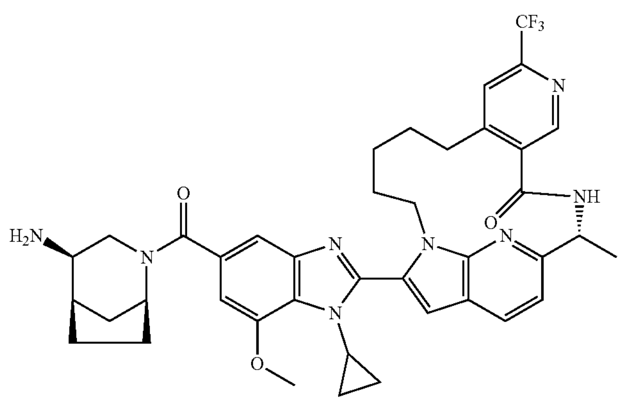 [SMILES: COc1cc(C(=O)N2C[C@H](N)[C@@H]3CC[C@H]2C3)cc2nc(-c3cc4ccc5nc4n3CCCCCc3cc(C(F)(F)F)ncc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-2-methyl-8-(trifluoromethyl)-3,7,16,22-tetrazatetracyclo[14.5.2.0^{5,10}.0^{19,23}]tricosa-1(22),5(10),6,8,17,19(23),20-heptaen-4-one |
| 943 | 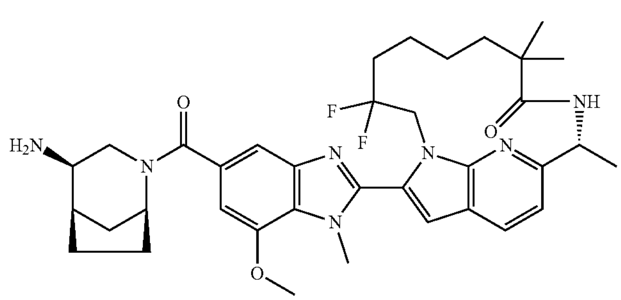 [SMILES: COc1cc(C(=O)N2C[C@H](N)[C@@H]3CC[C@H]2C3)cc2nc(-c3cc4ccc5nc4n3CC(F)(F)CCCCC(C)(C)C(=O)N[C@@H]5C)n(C)c12] | (11~{R})-17-[5-[(1~{S},4~{R},5~{R})-4-amino-2-azabicyclo[3.2.1]octane-2-carbonyl]-7-methoxy-1-methyl-benzimidazol-2-yl]-3,3-difluoro-8,8,11-trimethyl-1,10,19-triazatricyclo[10.5.2.0^{15,18}]nonadeca-12(19),13,15(18),16-tetraen-9-one |

TABLE 1A-continued

| Example | Structure | Name |
|---|---|---|
| 944 | 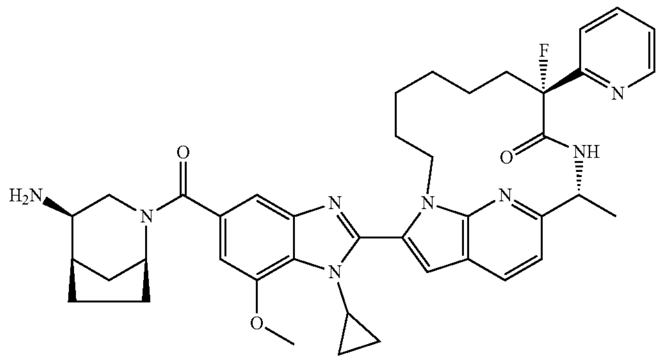 [SMILES: COc1cc(C(=O)N2C[C@H](N)[C@@H]3CC[C@H]2C3)cc2nc(-c3cc4ccc5nc4n3CCCCCC[C@@](F)(c3ccccn3)C(=O)N[C@@H]5C)n(C3CC3)c12] | (8~{R},11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-fluoro-11-methyl-8-(2-pyridyl)-1,10,19-triazatricyclo[10.5.2.0ˆ{15,18}]nonadeca-12(19),13,15(18),16-tetraen-9-one |
| 945 | 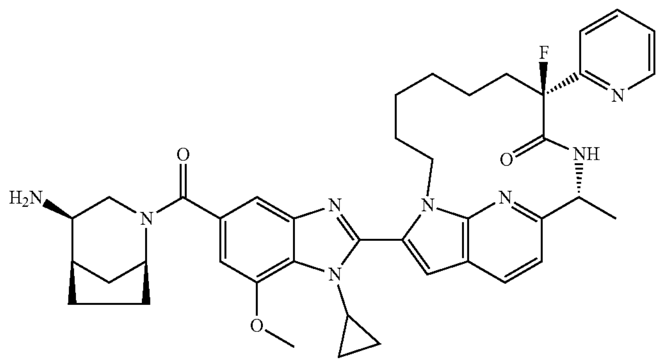 [SMILES: COc1cc(C(=O)N2C[C@H](N)[C@@H]3CC[C@H]2C3)cc2nc(-c3cc4ccc5nc4n3CCCCCC[C@](F)(c3ccccn3)C(=O)N[C@@H]5C)n(C3CC3)c12] | (8~{S},11~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-8-fluoro-11-methyl-8-(2-pyridyl)-1,10,19-triazatricyclo[10.5.2.0ˆ{15,18}]nonadeca-12(19),13,15(18),16-tetraen-9-one |
| 946 | 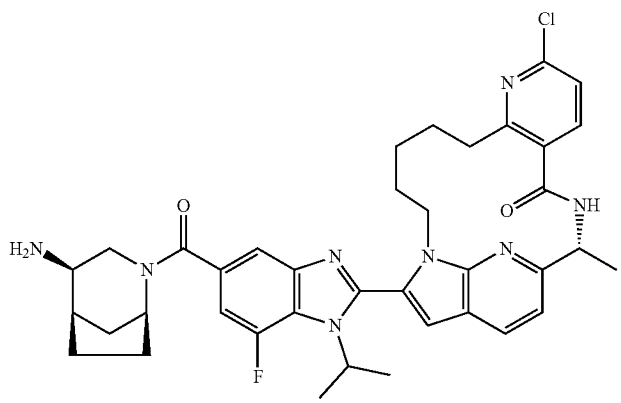 [SMILES: CC(C)n1c(-c2cc3ccc4nc3n2CCCCCc2nc(Cl)ccc2C(=O)N[C@@H]4C)nc2cc(C(=O)N3C[C@H](N)[C@@H]4CC[C@H]3C4)cc(F)c21] | (2~{R})-17-[5-[(1~{S},4~{R},5~{R})-4-amino-2-azabicyclo[3.2.1]octane-2-carbonyl]-7-fluoro-1-isopropyl-benzimidazol-2-yl]-8-chloro-2-methyl-3,9,16,22-tetrazatetracyclo[14.5.2.0ˆ{5,10}.0ˆ{19,23}]tricosa-1(22),5(10),6,8,17,19(23),20-heptaen-4-one |
| 947 | 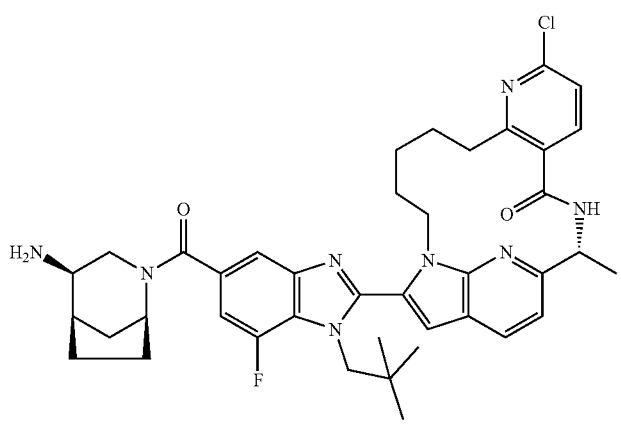 [SMILES: C[C@H]1NC(=O)c2ccc(Cl)nc2CCCCCn2c(-c3nc4cc(C(=O)N5C[C@H](N)[C@@H]6CC[C@H]5C6)cc(F)c4n3CC(C)(C)C)cc3ccc1nc32] | (2~{R})-17-[5-[(1~{S},4~{R},5~{R})-4-amino-2-azabicyclo[3.2.1]octane-2-carbonyl]-1-(2,2-dimethylpropyl)-7-fluoro-benzimidazol-2-yl]-8-chloro-2-methyl-3,9,16,22-tetrazatetracyclo[14.5.2.0ˆ{5,10}.0ˆ{19,23}]tricosa-1(22),5(10),6,8,17,19(23),20-heptaen-4-one |

TABLE 1A-continued

| Example | Structure | Name |
|---|---|---|
| 948 | 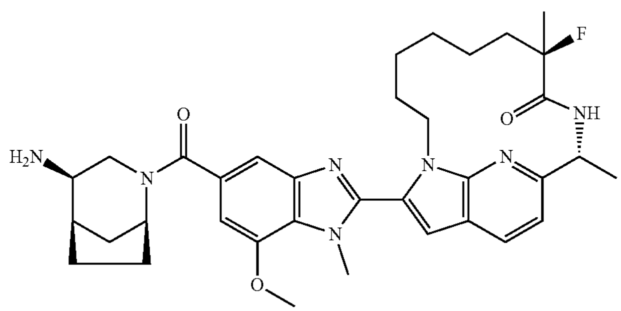 [SMILES: COc1cc(C(=O)N2C[C@H](N)[C@@H]3CC[C@H]2C3)cc2nc(-c3cc4ccc5nc4n3CCCCCC[C@@](C)(F)C(=O)N[C@@H]5C)n(C)c12] | (8~{R},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-fluoro-8,11-dimethyl-1,10,19-triazatricyclo[10.5.2.0^{15,18}]nonadeca-12(19),13,15(18),16-tetraen-9-one |
| 949 | 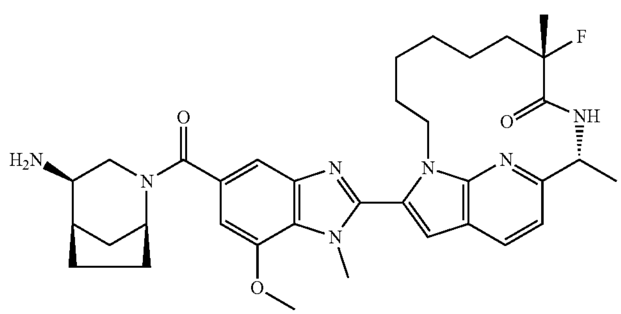 [SMILES: COc1cc(C(=O)N2C[C@H](N)[C@@H]3CC[C@H]2C3)cc2nc(-c3cc4ccc5nc4n3CCCCCC[C@](C)(F)C(=O)N[C@@H]5C)n(C)c12] | (8~{S},11~{R})-17-[5-[(1~{S},4~{R},5~{R})-4-amino-2-azabicyclo[3.2.1]octane-2-carbonyl]-7-methoxy-1-methyl-benzimidazol-2-yl]-8-fluoro-8,11-dimethyl-1,10,19-triazatricyclo[10.5.2.0^{15,18}]nonadeca-12(19),13,15(18),16-tetraen-9-one |
| 950 | 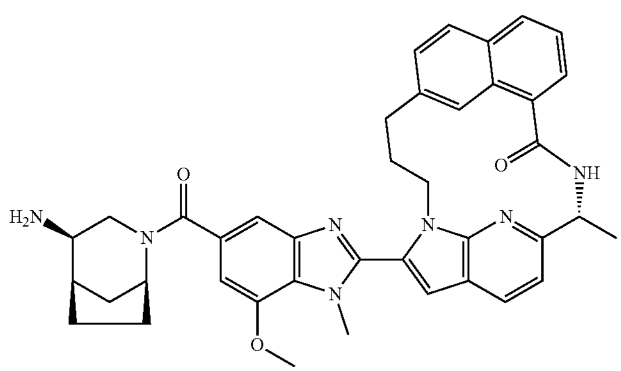 [SMILES: COc1cc(C(=O)N2C[C@H](N)[C@@H]3CC[C@H]2C3)cc2nc(-c3cc4ccc5nc4n3CCCc3ccc4cccc(c4c3)C(=O)N[C@@H]5C)n(C)c12] | (4~{R})-10-[5-[(1~{S},4~{R},5~{R})-4-amino-2-azabicyclo[3.2.1]octane-2-carbonyl]-7-methoxy-1-methyl-benzimidazol-2-yl]-4-methyl-3,6,11-triazapentacyclo[13.6.2.2^{5,8}.0^{7,11}.0^{18,22}]pentacosa-1(22),5,7,9,15(23),16,18,20,24-nonaen-2-one |
| 951 | 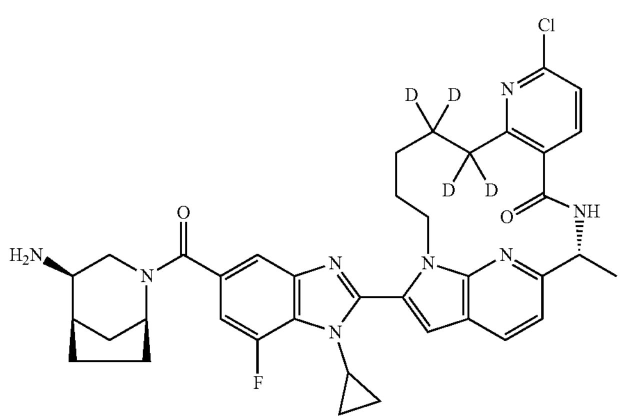 [SMILES: [2H]C1([2H])CCCn2c(-c3nc4cc(C(=O)N5C[C@H](N)[C@@H]6CC[C@H]5C6)cc(F)c4n3C3CC3)cc3ccc(nc32)[C@@H](C)NC(=O)c2ccc(Cl)nc2C1([2H])[2H]] | (2~{R})-17-[5-[(1~{S},4~{R},5~{R})-4-amino-2-azabicyclo[3.2.1]octane-2-carbonyl]-1-cyclopropyl-7-fluoro-benzimidazol-2-yl]-8-chloro-11,11,12,12-tetradeuterio-2-methyl-3,9,16,22-tetrazatetracyclo[14.5.2.0^{5,10}.0^{19,23}]tricosa-1(22),5(10),6,8,17,19(23),20-heptaen-4-one |

TABLE 1A-continued

| Example | Structure | Name |
|---|---|---|
| 952 | 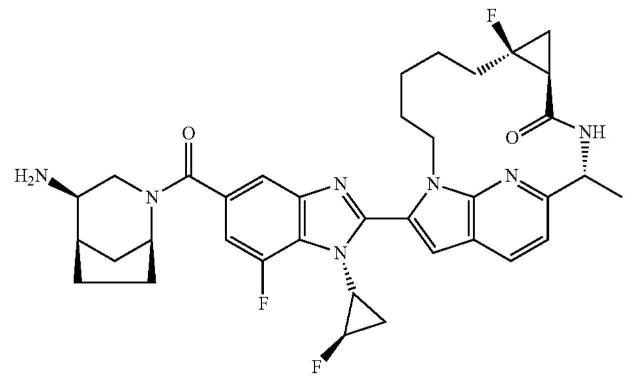 | (2~{R},5~{S},7~{S})-14-[5-[(1~{S},4~{R},5~{R})-4-amino-2-azabicyclo[3.2.1]octane-2-carbonyl]-7-fluoro-1-[(1~{R},2~{R})-2-fluorocyclopropyl]benzimidazol-2-yl]-7-fluoro-2-methyl-3,13,19-triazatetracyclo[11.5.2.0^{5,7}.0^{16,20}]icosa-1(19),14,16(20),17-tetraen-4-one |
| 953 | 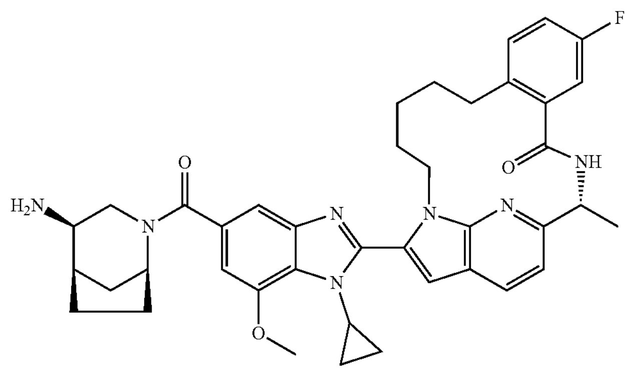 [SMILES: COc1cc(C(=O)N2C[C@H](N)[C@@H]3CC[C@H]2C3)cc2nc(-c3cc4ccc5nc4n3CCCCCc3ccc(F)cc3C(=O)N[C@@H]5C)n(C3CC3)c12] | (2~{R})-17-[5-[(1~{S},4~{R},5~{R})-4-amino-2-azabicyclo[3.2.1]octane-2-carbonyl]-1-cyclopropyl-7-methoxy-benzimidazol-2-yl]-7-fluoro-2-methyl-3,16,22-triazatetracyclo[14.5.2.0^{5,10}.0^{19,23}]tricosa-1(22),5(10),6,8,17,19(23),20-heptaen-4-one |
| 954 | 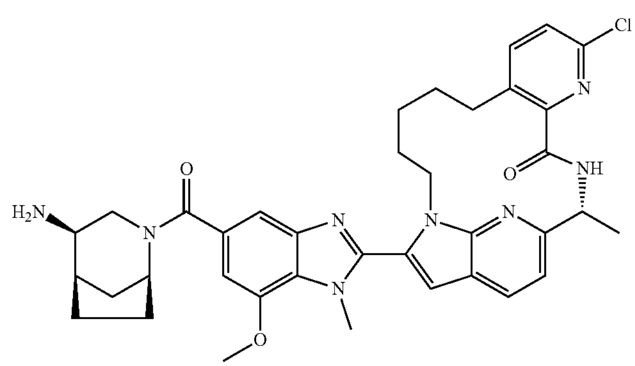 [SMILES: COc1cc(C(=O)N2C[C@H](N)[C@@H]3CC[C@H]2C3)cc2nc(-c3cc4ccc5nc4n3CCCCCc3ccc(Cl)nc3C(=O)N[C@@H]5C)n(C)c12] | (2~{R})-17-[5-[(1~{S},4~{R},5~{R})-4-amino-2-azabicyclo[3.2.1]octane-2-carbonyl]-7-methoxy-1-methyl-benzimidazol-2-yl]-7-chloro-2-methyl-3,6,16,22-tetrazatetracyclo[14.5.2.0^{5,10}.0^{19,23}]tricosa-1(21),5(10),6,8,17,19,22-heptaen-4-one |
| 955 | 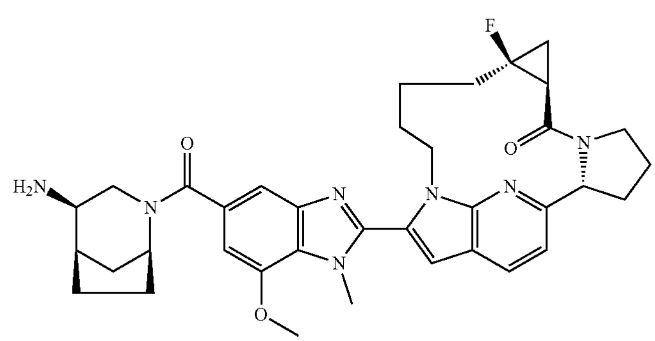 [SMILES: COc1cc(C(=O)N2C[C@H](N)[C@@H]3CC[C@H]2C3)cc2nc(-c3cc4ccc5nc4n3CCCC[C@]3(F)C[C@H]3C(=O)N3CCC[C@H]53)n(C)c12] | (2~{R},8~{S},10~{S})-16-[5-[(1~{S},4~{R},5~{R})-4-amino-2-azabicyclo[3.2.1]octane-2-carbonyl]-7-methoxy-1-methyl-benzimidazol-2-yl]-10-fluoro-6,15,21-triazapentacyclo[13.5.2.0^{2,6}.0^{8,10}.0^{18,22}]docosa-1(21),16,18(22),19-tetraen-7-one |

TABLE 2

| Example | Intermediate 1 | Intermediate 2 | A | Procedure |
|---|---|---|---|---|
| 1 | I-107a | L27 | A1.01 | 24 |
| 2 | I-107a | L27 | A1.01 | 24 |
| 3 | I-107a | L27 | A1.01 | 24 |
| 4 | I-107a | L27 | A1.01 | 24 |
| 5 | I-102 | L4a | A1.11 | 8 |
| 6 | I-107d | L48 | A13 | 25 |
| 7 | I-102 | L39a | A13 | 27 |
| 8 | I-100 | L11 | A2 | 2 |
| 9 | I-100 | L11 | A2 | 2 |
| 10 | I-102 | L10 | A2 | 29 |
| 11 | I-102 | L10 | A2 | 29 |
| 12 | I-107a | L27 | A2 | 24 |
| 13 | I-102 | L4a | A3 | 8 |
| 14 | I-102 | L4a | A5a | 8 |
| 15 | I-102 | L4a | A6 | 8 |
| 16 | I-102 | L4a | A1.01 | 8 |
| 17 | I-102 | L6b | A1.01 | 8 |
| 18 | I-102 | L6a | A1.01 | 8 |
| 19 | I-102 | L6a | A1.15 | 8 |
| 20 | I-102 | L4a | A2 | 8 |
| 21 | I-102 | L6a | A2 | 8 |
| 22 | I-102 | L6b | A2 | 8 |
| 23 | I-107f | hex-5-ene-1-sulfonyl chloride | A2 | 34 |
| 24 | I-107a | 2-vinylbenzoic acid | A2 | 25 |
| 25 | I-13a | 8-bromooct-1-yne | A1.01 | 35 |
| 26 | I-136b | L1a | A1.01 | 31 |
| 27 | I-136b | L4a | A1.01 | 31 |
| 28 | I-102 | L28a | A1.01 | 8 |
| 29 | I-102 | L28b | A1.01 | 8 |
| 30 | I-102 | L29 | A1.01 | 8 |
| 31 | I-102 | L28a | A1.15 | 8 |
| 32 | I-100 | L7a | A2 | 1 |
| 33 | I-100 | L7b | A2 | 1 |
| 34 | I-100 | L7c | A2 | 1 |
| 35 | I-100 | L7d | A2 | 1 |
| 36 | I-100 | L7e | A2 | 1 |
| 37 | I-102 | L9a | A2 | 8 |
| 38 | I-102 | L8a | A2 | 8 |
| 39 | I-102 | L28a | A2 | 8 |
| 40 | I-102 | L28b | A2 | 8 |
| 41 | I-102 | L29 | A2 | 8 |
| 42 | I-102 | L28a | A3 | 8 |
| 43 | I-102 | L28a | A1.03 | 8 |
| 44 | I-102 | L28a | A8 | 8 |
| 45 | I-118 | blank | A1.01 | 16 |
| 46 | I-108 | blank | A1.01 | 15 |
| 47 | I-120 | blank | A1.01 | 16 |
| 48 | I-109 | blank | A2 | 15 |
| 49 | I-109 | blank | A1.01 | 15 |
| 50 | I-8a | tert-butyl N-(6-bromohexyl)carbamate | A1.01 | 18 |
| 51 | I-110a | blank | A1.01 | 15 |
| 52 | I-111 | blank | A1.01 | 15 |
| 53 | I-122 | blank | A1.01 | 16 |
| 54 | I-123 | blank | A1.01 | 16 |
| 55 | I-110b | blank | A1.01 | 15 |
| 56 | I-113 | blank | A1.01 | 15 |
| 57 | I-112 | blank | A1.01 | 15 |
| 58 | I-102 | L4b | A1.01 | 8 |
| 59 | I-102 | L4a | A1.02 | 8 |
| 60 | I-102 | L4a | A1.03 | 8 |
| 61 | I-102 | L4b | A1.03 | 8 |
| 62 | I-102 | L4d | A1.03 | 8 |
| 63 | I-102 | L4a | A1.04 | 8 |
| 64 | I-102 | L4a | A1.05 | 8 |
| 65 | I-102 | L4a | A1.06 | 8 |
| 66 | I-102 | L4a | A1.06 | 26 |
| 67 | I-102 | L4a | A1.07 | 8 |
| 68 | I-102 | L4a | A1.08 | 8 |
| 69 | I-102 | L4a | A1.09 | 8 |
| 70 | I-102 | L4a | A1.10 | 8 |
| 71 | I-102 | L4a | A1.13 | 8 |
| 72 | I-102 | L4d | A1.14 | 8 |
| 73 | I-102 | L4a | A1.14 | 8 |
| 74 | I-102 | L4d | A1.15 | 8 |
| 75 | I-102 | L4a | A1.15 | 8 |
| 76 | I-102 | L4b | A1.15 | 8 |
| 77 | I-102 | L4d | A1.22 | 8 |
| 78 | I-102 | L4a | A1.22 | 8 |
| 79 | I-102 | L4a | A1.28 | 11 |
| 80 | I-102 | L4a | A1.29 | 8 |
| 81 | I-102 | L4a | A1.28 | 11 |
| 82 | I-102 | L4a | A10 | 8 |
| 83 | I-126 | blank | A2 | 17 |
| 84 | I-115 | blank | A2 | 16 |
| 85 | I-125 | blank | A2 | 17 |
| 86 | I-127 | blank | A2 | 17 |
| 87 | I-116 | blank | A2 | 16 |
| 88 | I-114 | blank | A2 | 16 |
| 89 | I-117 | blank | A2 | 16 |
| 90 | I-118 | blank | A2 | 16 |
| 91 | I-108 | blank | A2 | 15 |
| 92 | I-124 | blank | A2 | 16 |
| 93 | I-119 | blank | A2 | 16 |
| 94 | I-120 | blank | A2 | 16 |
| 95 | I-121 | blank | A2 | 16 |
| 96 | I-8a | tert-butyl N-(6-bromohexyl)carbamate | A2 | 18 |
| 97 | I-110a | blank | A2 | 15 |
| 98 | I-111 | blank | A2 | 15 |
| 99 | I-122 | blank | A2 | 16 |
| 100 | I-123 | blank | A2 | 16 |
| 101 | I-110b | blank | A2 | 15 |
| 102 | I-102 | L4b | A2 | 8 |
| 103 | I-102 | L4a | A5b | 8 |
| 104 | I-102 | L4a | A5c | 8 |
| 105 | I-102 | L4a | A9 | 8 |
| 106 | I-100 | L4b | A1.01 | 1 |
| 107 | I-8a | L1c | A1.01 | 12 |
| 108 | I-8a | L2a | A1.01 | 12 |
| 109 | I-8a | L3a | A1.01 | 12 |
| 110 | I-102 | L5a | A1.01 | 8 |
| 111 | I-102 | L5b | A1.01 | 8 |
| 112 | I-102 | L5c | A1.01 | 14 |
| 113 | I-104a | L5c | A1.01 | 14 |
| 114 | I-102 | L47 | A1.01 | 8 |
| 115 | I-102 | L45a | A1.01 | 28 |
| 116 | I-102 | L45a | A1.01 | 28 |
| 117 | I-104c | L4a | A1.01 | 8 |
| 118 | I-102 | L43 | A1.01 | 27 |
| 119 | I-102 | L44a | A1.01 | 27 |
| 120 | I-107g | oct-7-enoic acid | A2 | 4 |
| 121 | I-100 | L4a | A2 | 1 |
| 122 | I-100 | L5a | A2 | 1 |
| 123 | I-107g | hept-6-enoic acid | A2 | 4 |
| 124 | I-100 | L5b | A2 | 1 |
| 125 | I-8a | L1a | A2 | 12 |
| 126 | I-100 | L4b | A2 | 1 |
| 127 | I-3 | L25 | A2 | 5 |
| 128 | I-8a | L1d | A2 | 12 |
| 129 | I-8b | L1a | A2 | 12 |
| 130 | I-8a | L1c | A2 | 12 |
| 131 | I-8a | L1b | A2 | 12 |
| 132 | I-8a | L2a | A2 | 12 |
| 133 | I-8a | L3a | A2 | 12 |
| 134 | I-8a | L1a | A2 | 13 |
| 135 | I-8a | L1a | A2 | 12 |
| 136 | I-102 | L5a | A2 | 8 |
| 137 | I-102 | L5b | A2 | 8 |
| 138 | I-102 | L5c | A2 | 14 |
| 139 | I-102 | L47 | A2 | 8 |
| 140 | I-102 | L46 | A1.01 | 8 |
| 141 | I-102 | L46 | A2 | 8 |
| 142 | I-102 | L45a | A2 | 28 |
| 143 | I-102 | L45a | A2 | 28 |
| 144 | I-102 | L43 | A2 | 27 |
| 145 | I-102 | L44a | A2 | 27 |
| 146 | I-100 | L26b | A1.01 | 6 |
| 147 | I-100 | L12 | A1.01 | 1 |
| 148 | I-104a | L4a | A1.01 | 8 |
| 149 | I-102 | L19b | A1.01 | 8 |
| 150 | I-102 | L19a | A1.01 | 8 |
| 151 | I-102 | L20a | A1.01 | 8 |
| 152 | I-102 | L20a | A2 | 8 |
| 153 | I-102 | L21 | A1.01 | 10 |

TABLE 2-continued

| Example | Intermediate 1 | Intermediate 2 | A | Procedure |
|---|---|---|---|---|
| 154 | I-102 | L21 | A1.01 | 10 |
| 155 | I-104a | L4d | A1.01 | 8 |
| 156 | I-104a | L6a | A1.01 | 8 |
| 157 | I-102 | L20b | A1.01 | 10 |
| 158 | I-102 | L20b | A1.01 | 10 |
| 159 | I-104b | L4d | A1.01 | 8 |
| 160 | I-104b | L4a | A1.01 | 8 |
| 161 | I-102 | L42a | A1.01 | 27 |
| 162 | I-102 | L42b | A1.01 | 27 |
| 163 | I-102 | L40 | A1.01 | 27 |
| 164 | I-102 | L20b | A1.01 | 10 |
| 165 | I-102 | L20b | A1.01 | 10 |
| 166 | I-102 | L41 | A1.01 | 27 |
| 167 | I-102 | L45b | A1.01 | 28 |
| 168 | I-102 | L45b | A1.01 | 28 |
| 169 | I-105b | L4a | A1.01 | 8 |
| 170 | I-102 | L38a | A1.01 | 27 |
| 171 | I-102 | L38b | A1.01 | 27 |
| 172 | I-102 | L38c | A1.01 | 8 |
| 173 | I-104a | L4a | A1.03 | 8 |
| 174 | I-107d | L48 | A1.03 | 25 |
| 175 | I-102 | L37 | A1.03 | 27 |
| 176 | I-105b | L4a | A1.10 | 8 |
| 177 | I-102 | L4a | A1.12 | 8 |
| 178 | I-104a | L4a | A1.15 | 8 |
| 179 | I-105b | L4a | A1.15 | 8 |
| 180 | I-102 | L38a | A1.15 | 27 |
| 181 | I-102 | L38c | A1.15 | 27 |
| 182 | I-107e | L48 | A1.15 | 25 |
| 183 | I-102 | L38e | A1.15 | 27 |
| 184 | I-107d | L48 | A1.15 | 25 |
| 185 | I-102 | L38d | A1.15 | 27 |
| 186 | I-135a | 2-vinylbenzoic acid | A1.15 | 25 |
| 187 | I-102 | L37 | A1.15 | 27 |
| 188 | I-7f | I-142a | A1.15 | 33 |
| 189 | I-135b | L48 | A1.15 | 25 |
| 190 | I-104a | L4a | A1.17 | 30 |
| 191 | I-104a | L4a | A1.20 | 8 |
| 192 | I-102 | L4a | A1.24 | 8 |
| 193 | I-102 | L4a | A1.25 | 8 |
| 194 | I-105b | L4a | A1.25 | 8 |
| 195 | I-102 | L4a | A1.26 | 8 |
| 196 | I-102 | L4a | A1.27 | 8 |
| 197 | I-102 | L4a | A1.30 | 8 |
| 198 | I-102 | L4a | A1.31 | 8 |
| 199 | I-102 | L4a | A1.32 | 8 |
| 200 | I-102 | L4a | A1.33 | 8 |
| 201 | I-102 | L4a | A1.34 | 8 |
| 202 | I-102 | L4a | A1.35 | 11 |
| 203 | I-102 | L4a | A1.35 | 11 |
| 204 | I-102 | L4a | A1.36 | 8 |
| 205 | I-102 | L4a | A1.37 | 8 |
| 206 | I-102 | L4a | A11a | 8 |
| 207 | I-102 | L4d | A12 | 8 |
| 208 | I-104a | L4d | A14 | 8 |
| 209 | I-100 | L26c | A2 | 6 |
| 210 | I-100 | L26a | A2 | 6 |
| 211 | I-100 | L26b | A2 | 6 |
| 212 | I-100 | L26d | A2 | 6 |
| 213 | I-100 | L12 | A2 | 1 |
| 214 | I-101b | L13b | A2 | 1 |
| 215 | I-104a | L1a | A2 | 8 |
| 216 | I-104a | L4a | A2 | 8 |
| 217 | I-102 | L19b | A2 | 8 |
| 218 | I-102 | L19a | A2 | 8 |
| 219 | I-102 | L21 | A2 | 10 |
| 220 | I-102 | L21 | A2 | 10 |
| 221 | I-104a | L4d | A2 | 8 |
| 222 | I-104a | L6a | A2 | 8 |
| 223 | I-102 | L20b | A2 | 10 |
| 224 | I-102 | L20b | A2 | 10 |
| 225 | I-104b | L4d | A2 | 8 |
| 226 | I-102 | L40 | A2 | 27 |
| 227 | I-128 | blank | A4 | 19 |
| 228 | I-101a | L1a | A1.01 | 1 |
| 229 | I-103a | L1a | A1.01 | 8 |
| 230 | I-103a | L4a | A1.01 | 8 |
| 231 | I-103a | L1b | A1.01 | 8 |
| 232 | I-131 | blank | A1.01 | 8 |
| 233 | I-131 | L4d | A1.01 | 8 |
| 234 | I-131 | blank | A1.01 | 22 |
| 235 | I-132 | blank | A1.01 | 21 |
| 236 | I-132 | blank | A1.01 | 21 |
| 237 | I-136a | L4a | A1.01 | 31 |
| 238 | I-133 | blank | A1.01 | 8 |
| 239 | I-107b | but-3-enoic acid | A1.03 | 25 |
| 240 | I-102 | L39a | A1.03 | 27 |
| 241 | I-102 | L39a | A1.15 | 27 |
| 242 | I-102 | L20b | A1.15 | 10 |
| 243 | I-105b | L49 | A1.15 | 8 |
| 244 | I-102 | L4a | A1.16 | 8 |
| 245 | I-102 | L13f | A1.17 | 30 |
| 246 | I-102 | L13f | A1.17 | 30 |
| 247 | I-100 | L22 | A2 | 1 |
| 248 | I-100 | L23 | A2 | 1 |
| 249 | I-101a | L1a | A2 | 1 |
| 250 | I-103a | L1a | A2 | 8 |
| 251 | I-106 | L1a | A2 | 8 |
| 252 | I-136a | L1a | A2 | 31 |
| 253 | I-103a | L4a | A2 | 8 |
| 254 | I-103a | L1b | A2 | 8 |
| 255 | I-131 | blank | A2 | 8 |
| 256 | I-131 | blank | A2 | 22 |
| 257 | I-132 | blank | A2 | 21 |
| 258 | I-132 | blank | A2 | 21 |
| 259 | I-129 | L1a | A4 | 20 |
| 260 | I-102 | L4d | A7 | 8 |
| 261 | I-102 | L4a | A7 | 11 |
| 262 | I-102 | L4a | A7 | 11 |
| 263 | I-102 | L4c | A1.01 | 8 |
| 264 | I-102 | L30a | A1.01 | 8 |
| 265 | I-102 | L19c | A1.01 | 29 |
| 266 | I-102 | L19c | A1.01 | 29 |
| 267 | I-102 | L19d | A1.01 | 29 |
| 268 | I-102 | L19d | A1.01 | 29 |
| 269 | I-102 | L31 | A1.01 | 27 |
| 270 | I-102 | L30b | A1.01 | 8 |
| 271 | I-102 | L19e | A1.01 | 27 |
| 272 | I-102 | L32 | A1.01 | 27 |
| 273 | I-107c | 2,2-dimethyl-4-pentenoic acid | A1.01 | 25 |
| 274 | I-102 | L33 | A1.01 | 27 |
| 275 | I-140a | I-142a | A1.15 | 32 |
| 276 | I-102 | L4a | A1.18 | 8 |
| 277 | I-102 | L4a | A1.19 | 8 |
| 278 | I-102 | L4c | A2 | 8 |
| 279 | I-102 | L4d | A2 | 8 |
| 280 | I-102 | L4e | A2 | 8 |
| 281 | I-102 | L4f | A2 | 8 |
| 282 | I-102 | L1a | A1.01 | 8 |
| 283 | I-102 | L1c | A1.01 | 8 |
| 284 | I-100 | L1e | A1.01 | 1 |
| 285 | I-102 | L1a | A2 | 8 |
| 286 | I-102 | L1c | A2 | 8 |
| 287 | I-100 | L1e | A2 | 1 |
| 288 | I-102 | L1a | A3 | 8 |
| 289 | I-102 | L1c | A3 | 8 |
| 290 | I-100 | L1e | A3 | 1 |
| 291 | I-13a | octane-1,8-diol | A1.01 | 23 |
| 292 | I-102 | L44b | A1.01 | 27 |
| 293 | I-138 | tert-butyl N-(6-iodohexyl)carbamate | A1.01 | 7 |
| 294 | I-102 | L4a | A1.20 | 8 |
| 295 | I-102 | L4a | A1.21 | 8 |
| 296 | I-102 | L4a | A1.23 | 8 |
| 297 | I-102 | L4a | A13 | 8 |
| 298 | I-13a | 2,2'-(ethane-1,2-diylbis(oxy))bis(ethan-1-ol) | A1.01 | 23 |
| 299 | I-102 | L4a | A8 | 8 |
| 300 | I-100 | L1b | A1.01 | 1 |
| 301 | I-100 | L1a | A1.01 | 1 |
| 302 | I-100 | L1a | A3 | 1 |
| 303 | I-100 | L15a | A1.01 | 1 |
| 304 | I-102 | L13d | A1.01 | 8 |
| 305 | I-102 | L13e | A1.01 | 8 |
| 306 | I-102 | L15b | A1.01 | 8 |

TABLE 2-continued

| Example | Intermediate 1 | Intermediate 2 | A | Procedure |
|---|---|---|---|---|
| 307 | I-104a | L35d | A1.01 | 27 |
| 308 | I-102 | L35d | A1.01 | 27 |
| 309 | I-102 | L35c | A1.01 | 27 |
| 310 | I-102 | L36a | A1.01 | 27 |
| 311 | I-102 | L36b | A1.01 | 27 |
| 312 | I-102 | L13g | A1.01 | 29 |
| 313 | I-102 | L13g | A1.01 | 29 |
| 314 | I-102 | L13f | A1.03 | 27 |
| 315 | I-102 | L13f | A1.15 | 27 |
| 316 | I-100 | L1a | A2 | 1 |
| 317 | I-100 | L1b | A2 | 1 |
| 318 | I-100 | L1c | A2 | 1 |
| 319 | I-100 | L1a | A2 | 22 |
| 320 | I-100 | L1d | A2 | 1 |
| 321 | I-100 | L2a | A2 | 1 |
| 322 | I-100 | L13b | A2 | 2 |
| 323 | I-100 | L13b | A2 | 2 |
| 324 | I-100 | L3a | A2 | 1 |
| 325 | I-100 | L14a | A2 | 2 |
| 326 | I-100 | L14a | A2 | 2 |
| 327 | I-100 | L13a | A2 | 2 |
| 328 | I-100 | L13a | A2 | 2 |
| 329 | I-100 | L13c | A2 | 1 |
| 330 | I-100 | L14b | A2 | 1 |
| 331 | I-100 | L15a | A2 | 1 |
| 332 | I-100 | L16b | A2 | 1 |
| 333 | I-100 | L16a | A2 | 1 |
| 334 | I-100 | L18 | A2 | 3 |
| 335 | I-100 | L18 | A2 | 3 |
| 336 | I-102 | L13d | A2 | 8 |
| 337 | I-102 | L13e | A2 | 8 |
| 338 | I-102 | L15b | A2 | 8 |
| 339 | I-104a | L17 | A2 | 9 |
| 340 | I-104a | L17 | A2 | 9 |
| 341 | I-104a | L34 | A2 | 8 |
| 342 | I-104a | L35d | A2 | 27 |
| 343 | I-102 | L4d | A14 | 8 |
| 344 | 143a | L50a | A1.15 | 27 |
| 345 | 143a | L50b | A1.15 | 27 |
| 346 | I-102 | L52a | A1.15 | 27 |
| 347 | I-141b | L28a | A1.15 | 8 |
| 348 | I-141b | L52a | A1.15 | 27 |
| 349 | I-105a | L50c | A1.15 | 27 |
| 350 | I-105a | L50a | A1.15 | 27 |
| 351 | I-105a | L52b | A1.15 | 27 |
| 352 | I-105a | L50d | A1.15 | 27 |
| 353 | I-141b | L50a | A1.15 | 27 |
| 354 | I-141b | L50f | A1.15 | 27 |
| 355 | I-141b | L50e | A1.15 | 27 |
| 356 | I-141b | L50v | A1.15 | 27 |
| 357 | I-141b | L50w | A1.15 | 27 |
| 358 | I-102 | L50a | A1.03 | 27 |
| 359 | I-102 | L50v | A1.03 | 27 |
| 360 | I-102 | L50b | A1.03 | 27 |
| 361 | I-102 | L50g | A1.01 | 27 |
| 362 | I-102 | L50g | A1.03 | 27 |
| 363 | I-102 | L50g | A1.15 | 27 |
| 364 | I-107i | 2,2-Dimethyl-4-pentenoic acid | A1.15 | 36 |
| 365 | I-107i | 2,2-Dimethyl-4-pentenoic acid | A1.15 | 36 |
| 366 | I-107h | 2,2-Dimethyl-4-pentenoic acid | A1.03 | 25 |
| 367 | I-107h | 2,2-Dimethyl-4-pentenoic acid | A1.15 | 25 |
| 368 | I-107a | L53 | A1.15 | 36 |
| 369 | I-107a | L53 | A1.15 | 36 |
| 370 | I-107h | L27 | A1.03 | 24 |
| 371 | I-107h | L27 | A1.15 | 24 |
| 372 | I-107h | L27 | A1.03 | 24 |
| 373 | I-107h | L27 | A1.15 | 24 |
| 374 | I-107a | 2,2-Difluoro-4-pentenoic acid | A1.03 | 25 |
| 375 | I-107a | 2,2-Difluoro-4-pentenoic acid | A.15 | 25 |
| 376 | I-104c | L4a | A1.15 | 8 |
| 377 | I-135d | L53 | A1.15 | 36 |
| 378 | I-135d | L53 | A1.15 | 36 |
| 379 | I-107j | L62b | A1.15 | 25 |
| 380 | I-102 | L4a | A1.38 | 8 |
| 381 | I-107l | L53 | A1.15 | 37 |
| 382 | I-107l | L53 | A1.15 | 37 |
| 383 | I-107l | L53 | A1.15 | 37 |
| 384 | I-105a | L50h | A1.15 | 27 |
| 385 | I-107k | L62a | A1.15 | 36 |
| 386 | I-107k | L62a | A1.15 | 36 |
| 387 | I-107m | L54a | A1.15 | 25 |
| 388 | I-107m | L55a | A1.15 | 25 |
| 389 | I-135c | L53 | A1.15 | 37 |
| 390 | I-135c | L53 | A1.15 | 37 |
| 391 | I-135c | L53 | A1.15 | 37 |
| 392 | I-107m | L53 | A1.15 | 37 |
| 393 | I-107m | L53 | A1.15 | 37 |
| 394 | I-107m | L53 | A1.15 | 37 |
| 395 | I-105b | L50j | A1.15 | 27 |
| 396 | I-105b | L50i | A1.15 | 27 |
| 397 | I-102 | L50h | A1.03 | 27 |
| 398 | I-102 | L56a | A1.15 | 27 |
| 399 | I-102 | L57a | A1.15 | 27 |
| 400 | I-144a | L61a | A15 | 25 |
| 401 | I-105a | L59b | A1.15 | 8 |
| 402 | I-144b | L61a | A15 | 25 |
| 403 | I-21 | I-142b | A1.15 | 33 |
| 404 | I-7l | I-142a | A1.15 | 33 |
| 405 | I-22m | I-142a | blank | 38 |
| 406 | I-22n | I-142a | blank | 38 |
| 407 | I-102 | L59n | A1.03 | 8 |
| 408 | I-107d | L48 | A16 | 25 |
| 409 | I-102 | L59b | A1.03 | 8 |
| 410 | I-23f | I-142a | blank | 39 |
| 411 | I-107d | L48 | A17 | 8 |
| 412 | I-23f | I-142a | blank | 39 |
| 413 | I-23g | I-142a | blank | 39 |
| 414 | I-102 | L59a | A1.03 | 8 |
| 415 | I-23i | I-142a | blank | 39 |
| 416 | I-23h | I-142a | blank | 39 |
| 417 | I-7h | I-145a | A1.15 | 33 |
| 418 | I-143c | L4a | A1.15 | 8 |
| 419 | I-143d | L4a | A1.15 | 8 |
| 420 | I-22a | I-145a | blank | 38 |
| 421 | I-22b | I-145a | blank | 38 |
| 422 | I-107n | L48 | A1.15 | 25 |
| 423 | I-22c | I-145a | blank | 38 |
| 424 | I-22l | I-142b | blank | 38 |
| 425 | I-22d | I-145a | blank | 38 |
| 426 | I-22e | I-142a | blank | 38 |
| 427 | I-22f | I-142a | blank | 38 |
| 428 | I-22g | I-142a | blank | 38 |
| 429 | I-22h | I-142a | blank | 38 |
| 430 | I-23a | I-142a | blank | 39 |
| 431 | I-140p | I-142a | A1.15 | 32 |
| 432 | I-140p | I-142a | A1.03 | 32 |
| 433 | I-140p | I-142a | A1.01 | 32 |
| 434 | I-23c | I-142a | blank | 39 |
| 435 | I-23d | I-145b | blank | 39 |
| 436 | I-23d | I-142a | blank | 39 |
| 437 | I-135f | L48 | A18 | 25 |
| 438 | I-140c | I-142c | A18 | 32 |
| 439 | I-102 | L50k | A18 | 27 |
| 440 | I-141c | L50e | A18 | 27 |
| 441 | I-102 | L4a | A18 | 8 |
| 442 | I-135g | L48 | A18 | 25 |
| 443 | I-102 | L4b | A18 | 8 |
| 444 | I-107d | L48 | A18 | 25 |
| 445 | I-102 | L4d | A18 | 8 |
| 446 | I-135a | L63 | A18 | 25 |
| 447 | I-107a | L54a | A18 | 25 |
| 448 | I-135a | L55a | A18 | 25 |
| 449 | I-135e | L55a | A18 | 25 |
| 450 | I-107o | L55a | A18 | 25 |
| 451 | I-107a | L55a | A18 | 25 |
| 452 | I-140f | I-145c | A18 | 32 |
| 453 | I-140g | I-142c | A18 | 32 |
| 454 | I-140g | I-142c | A18 | 32 |
| 455 | I-135h | L48 | A18 | 25 |
| 456 | I-140a | I-145c | A18 | 32 |

TABLE 2-continued

| Example | Intermediate 1 | Intermediate 2 | A | Procedure |
|---|---|---|---|---|
| 457 | I-141c | L59f | A18 | 8 |
| 458 | I-140h | I-142a | A18 | 32 |
| 459 | I-135a | L27 | A18 | 24 |
| 460 | I-135f | L66a | A18 | 25 |
| 461 | I-102 | L59g | A18 | 8 |
| 462 | I-141f | L4a | A18 | 8 |
| 463 | I-135j | L48 | A18 | 25 |
| 464 | I-135i | L48 | A18 | 25 |
| 465 | I-141g | L4a | A18 | 8 |
| 466 | I-135b | L48 | A18 | 25 |
| 467 | I-140f | I-142c | A18 | 32 |
| 468 | I-140i | I-142c | A18 | 32 |
| 469 | I-141d | L59n | A18 | 8 |
| 470 | I-140l | I-142c | A18 | 32 |
| 471 | I-140k | I-142c | A18 | 32 |
| 472 | I-141c | L59n | A18 | 8 |
| 473 | I-140d | I-145c | A18 | 32 |
| 474 | I-141c | L59d | A18 | 8 |
| 475 | I-135a | 1-allylcyclopropane-1-carboxylic acid | A18 | 25 |
| 476 | I-141c | L59c | A18 | 8 |
| 477 | I-140d | I-142c | A18 | 32 |
| 478 | I-141c | L59e | A18 | 8 |
| 479 | I-140e | I-142c | A18 | 32 |
| 480 | I-141c | L65c | A18 | 29 |
| 481 | I-141c | L65c | A18 | 29 |
| 482 | I-107p | L62a | A18 | 25 |
| 483 | I-135e | L67a | A18 | 25 |
| 484 | I-143a | L50l | A18 | 27 |
| 485 | I-141c | L50l | A18 | 27 |
| 486 | I-107a | L68 | A1.15 | 40 |
| 487 | I-107a | L68 | A1.15 | 40 |
| 488 | I-105b | L4a | A2 | 8 |
| 489 | I-107d | L48 | A5a | 25 |
| 490 | I-107d | L48 | A5d | 25 |
| 491 | I-102 | L50k | A13 | 27 |
| 492 | I-102 | L50a | A13 | 27 |
| 493 | I-107d | L48 | A5f | 25 |
| 494 | I-107d | L48 | A5e | 25 |
| 495 | I-107a | 2-vinylbenzoic acid | A1.20 | 25 |
| 496 | I-107a | 2-vinylbenzoic acid | A1.03 | 25 |
| 497 | I-107q | hex-5-ene-1-sulfonyl chloride | A1.15 | 34 |
| 498 | I-105a | L50m | A1.15 | 27 |
| 499 | I-107z | L48b | A1.15 | 25 |
| 500 | I-104d | L4a | A1.15 | 8 |
| 501 | I-7r | I-145a | A1.15 | 33 |
| 502 | I-22v | I-145a | A1.15 | 38 |
| 503 | I-102 | L50m | A1.03 | 27 |
| 504 | I-7r | I-145b | A1.03 | 33 |
| 505 | I-7r | I-142a | A1.03 | 33 |
| 506 | I-7r | I-142a | A1.01 | 33 |
| 507 | I-7r | I-142a | A1.15 | 33 |
| 508 | I-107d | L48 | A1.43 | 25 |
| 509 | I-107d | L48 | A1.42 | 25 |
| 510 | I-22k | I-145b | blank | 38 |
| 511 | I-27a | I-142a | A1.03 | 33 |
| 512 | I-7s | I-142a | A1.03 | 33 |
| 513 | I-7s | I-145b | A1.03 | 33 |
| 514 | I-102 | L4a | A19 | 8 |
| 515 | I-105b | L4b | A1.15 | 8 |
| 516 | I-102 | L69a | A1.15 | 27 |
| 517 | I-102 | L69a | A1.03 | 27 |
| 518 | I-102 | L69a | A1.15 | 27 |
| 519 | I-141b | L69a | A1.15 | 27 |
| 520 | I-141b | L69a | A1.15 | 27 |
| 521 | I-105a | L69a | A1.15 | 27 |
| 522 | I-105a | L69a | A1.15 | 27 |
| 523 | I-102 | L69b | A1.15 | 27 |
| 524 | I-102 | L69b | A1.03 | 27 |
| 525 | I-102 | L69a | A1.03 | 27 |
| 526 | I-102 | L4a | A1.39 | 8 |
| 527 | I-102 | L4a | A23 | 8 |
| 528 | I-102 | L49 | A1.41 | 8 |
| 529 | I-102 | L4a | A1.40 | 11 |
| 530 | I-102 | L4a | A1.40 | 11 |
| 531 | I-107d | L48 | A1.28 | 36 |
| 532 | I-107d | L48 | A1.28 | 36 |
| 533 | I-102 | L4a | A20 | 8 |
| 534 | I-135k | (E)-but-2-enoic acid | A2 | 25 |
| 535 | I-102 | L4a | A11b | 8 |
| 536 | I-102 | L4a | A1.44 | 8 |
| 537 | I-143h | L4a | A1.15 | 8 |
| 538 | I-143i | L4a | A1.15 | 8 |
| 539 | I-105b | L20b | A1.15 | 10 |
| 540 | I-107e | L66a | A1.15 | 25 |
| 541 | I-141h | L4a | A1.15 | 8 |
| 542 | I-102 | L4a | A11b | 11 |
| 543 | I-102 | L4a | A11b | 11 |
| 544 | I-105b | L37 | A1.15 | 10 |
| 545 | I-105b | L37 | A1.15 | 10 |
| 546 | I-105a | L38d | A1.15 | 27 |
| 547 | I-135l | L48 | A1.15 | 25 |
| 548 | I-105a | L37 | A1.15 | 10 |
| 549 | I-135m | L48d | A1.15 | 25 |
| 550 | I-135n | L48b | A1.15 | 25 |
| 551 | I-135n | L48 | A1.15 | 25 |
| 552 | I-135m | L48d | A1.15 | 25 |
| 553 | I-135m | L48c | A1.15 | 25 |
| 554 | I-135m | L48c | A2 | 25 |
| 555 | I-143i | L4a | A2 | 8 |
| 556 | I-143h | L4a | A2 | 8 |
| 557 | I-107e | L48 | A2 | 25 |
| 558 | I-7p | I-145a | A1.15 | 33 |
| 559 | I-7p | I-142a | A1.15 | 33 |
| 560 | I-135l | L48 | A1.15 | 25 |
| 561 | I-22w | I-142a | blank | 38 |
| 562 | I-22w | I-142a | blank | 38 |
| 563 | I-7f | I-142a | A2 | 33 |
| 564 | I-105c | L48 | A1.15 | 25 |
| 565 | I-105c | 2,2-dimethyl-4-pentenoic acid | A1.15 | 25 |
| 566 | I-135l | L48 | A3 | 25 |
| 567 | I-135b | L48 | A1.15 | 25 |
| 568 | I-107e | L48 | A1.10 | 25 |
| 569 | I-107e | L48 | A1.43 | 25 |
| 570 | I-102 | L38d | A1.03 | 27 |
| 571 | I-23k | I-142a | blank | 39 |
| 572 | I-107e | L48 | A1.03 | 25 |
| 573 | I-140h | I-142a | A1.15 | 32 |
| 574 | I-140h | I-142a | A1.03 | 32 |
| 575 | I-107e | L48 | A1.35 | 36 |
| 576 | I-104a | L39 | A1.03 | 27 |
| 577 | I-104a | L39 | A13 | 27 |
| 578 | I-141c | L39 | A1.03 | 27 |
| 579 | I-23m | I-142a | blank | 39 |
| 580 | I-107s | L48 | A1.15 | 25 |
| 581 | I-107d | L48 | A21 | 25 |
| 582 | I-107d | L48 | A31 | 25 |
| 583 | I-107d | L48c | A1.03 | 25 |
| 584 | I-107d | L48 | A22 | 36 |
| 585 | I-135g | L48c | A1.03 | 25 |
| 586 | I-107c | L48 | A1.03 | 25 |
| 587 | I-135g | 2,2-dimethyl-4-pentenoic acid | A1.03 | 25 |
| 588 | I-135g | L66a | A1.03 | 25 |
| 589 | I-135g | L66b | A1.03 | 25 |
| 590 | I-107b | but-3-enoic acid | A1.15 | 25 |
| 591 | I-105a | L4a | A1.15 | 8 |
| 592 | I-143f | L4a | A1.15 | 8 |
| 593 | I-105a | L50n | A1.15 | 27 |
| 594 | I-135a | 2,2-dimethyl-4-pentenoic acid | A1.15 | 25 |
| 595 | I-135d | L62a | A1.15 | 25 |
| 596 | I-143g | L4a | A1.15 | 8 |
| 597 | I-135d | 2-vinylbenzoic acid | A1.15 | 25 |
| 598 | I-102 | L39a | A2 | 27 |
| 599 | I-22t | I-142a | A1.15 | 38 |
| 600 | I-22u | I-142a | A1.15 | 38 |
| 601 | I-22u | I-142a | A1.15 | 38 (from byproduct of step 1 of example 600) |

TABLE 2-continued

| Example | Intermediate 1 | Intermediate 2 | A | Procedure |
|---|---|---|---|---|
| 602 | I-140m | I-145a | A1.15 | 32 |
| 603 | I-107m | 3-allyloxetane-3-carboxylic acid | A1.15 | 25 |
| 604 | I-102 | L39a | A3 | 27 |
| 606 | I-102 | L39b | A1.03 | 27 |
| 607 | I-140n | I-142a | A1.15 | 32 |
| 608 | I-135a | 2,2-dimethyl-4-pentenoic acid | A1.03 | 25 |
| 609 | I-135a | 2,2-dimethyl-4-pentenoic acid | A13 | 25 |
| 610 | I-102 | L50o | A1.03 | 27 |
| 611 | I-107a | 3-allyloxetane-3-carboxylic acid | A1.03 | 25 |
| 612 | I-103a | L39a | A13 | 27 |
| 613 | I-107a | 3-allyloxetane-3-carboxylic acid | A13 | 25 |
| 614 | I-135a | 1-allylcyclobutanecarboxylic acid | A1.03 | 25 |
| 615 | I-107a | (2S)-2-hydroxypent-4-enoic acid | A1.15 | 41 |
| 616 | I-102 | L35b | A1.15 | 27 |
| 617 | I-102 | L72 | A1.15 | 28 |
| 618 | I-102 | L72 | A1.15 | 28 |
| 619 | I-102 | L70 | A1.15 | 27 |
| 620 | I-102 | L70 | A1.01 | 27 |
| 621 | I-107a | (2R)-2-hydroxypent-4-enoic acid | A1.15 | 41 |
| 622 | I-105b | L13f | A1.15 | 27 |
| 623 | I-135d | (2R)-2-hydroxypent-4-enoic acid | A1.15 | 41 |
| 624 | I-105a | L73 | A1.15 | 29 |
| 625 | I-105a | L73 | A1.15 | 29 |
| 626 | I-142b | methyl 4-amino-2-fluoro-5-nitro-benzoate | A1.15 | 42 |
| 627 | I-102 | L39a | A1.01 | 27 |
| 628 | I-107a | (2R)-2-hydroxypent-4-enoic acid | A1.03 | 41 |
| 629 | I-107a | (2R)-2-hydroxypent-4-enoic acid | A13 | 41 |
| 630 | I-107a | L71a | A1.03 | 25 |
| 631 | I-107d | L48 | A1.45 | 25 |
| 632 | I-135g | L48 | A15b | 25 |
| 633 | I-135g | L48 | A15b | 25 |
| 634 | I-107a | L74 | A1.03 | 24 |
| 635 | I-107a | L74 | A1.03 | 24 |
| 636 | I-107a | L74 | A1.03 | 24 |
| 637 | I-135g | L48 | A5g | 25 |
| 638 | I-135o | L48 | A1.03 | 25 |
| 639 | I-135o | L48 | A6 | 25 |
| 640 | I-135o | L48 | A1.46 | 25 |
| 641 | I-135o | L48 | A5g | 25 |
| 642 | I-135g | L48 | A2 | 25 |
| 643 | I-146a | L4a | A1.03 | 8 |
| 644 | I-102 | L4a | A27 | 11 |
| 645 | I-146a | L4a | A6 | 8 |
| 646 | I-135o | L48 | A3 | 25 |
| 647 | I-135g | L48 | A27 | 36 |
| 648 | I-135f | L48 | A1.03 | 25 |
| 649 | I-143a | L50c | A1.03 | 27 |
| 650 | I-143a | L50e | A1.03 | 27 |
| 651 | I-143a | L50f | A1.03 | 27 |
| 652 | I-104c | L50w | A1.03 | 27 |
| 653 | I-143a | L50w | A1.03 | 27 |
| 654 | I-143a | L50n | A1.03 | 27 + 22 |
| 655 | I-143a | L50s | A1.03 | 27 |
| 656 | I-143a | L50t | A1.03 | 47 |
| 657 | I-143a | L50r | A6 | 27 |
| 658 | I-143a | L50r | A3 | 27 |
| 659 | I-143a | L50r | A5g | 27 |
| 660 | I-143a | L50r | A1.26 | 27 |
| 661 | I-141c | L50f | A1.03 | 27 |
| 662 | I-141c | L50r | A1.03 | 27 |
| 663 | I-143a | L60a | A1.03 | 27 |
| 664 | I-143a | L60a | A6 | 27 |
| 665 | I-143a | L59k | A18 | 8 |
| 666 | I-135g | L48 | A28 | 36 |
| 667 | I-143a | 2,2-dimethyl-4-pentenoic acid | A28 | 11 |
| 668 | I-135g | L48 | A29 | 25 |
| 669 | I-141c | L59n | A29 | 27 |
| 670 | I-141c | L59o | A18 | 8 |
| 671 | I-141c | L59m | A18 | 8 |
| 672 | I-141c | L59l | A18 | 8 |
| 673 | I-141i | L59x | A18 | 8 |
| 674 | I-141c | L59p | A18 | 8 |
| 675 | I-108 | blank | A1.03 | 15 |
| 676 | I-135g | L48 | A1.47 | 36 |
| 677 | I-102 | L4a | A32 | 11 |
| 678 | I-135g | L48 | A33 | 36 |
| 679 | I-135a | L63 | A6 | 25 |
| 680 | I-135g | L48 | A1.26 | 25 |
| 681 | I-135g | L48 | A34b | 36 |
| 682 | I-135e | L79 | A18 | 25 |
| 683 | I-135e | L79 | A18 | 25 + 22 |
| 684 | I-141c | L4b | A18 | 8 |
| 685 | I-107o | L78 | A18 | 25 |
| 686 | I-107c | L66c | A1.03 | 24 |
| 687 | I-107c | L66c | A1.03 | 24 |
| 688 | I-107c | L54b | A1.03 | 25 |
| 689 | I-107c | L55a | A1.03 | 25 |
| 690 | I-135p | L48 | A1.03 | 25 |
| 691 | I-107v | L48 | A1.03 | 25 |
| 692 | I-135g | L48 | A1.03 | 25 + 22 |
| 693 | I-104c | L59n | A1.03 | 8 |
| 694 | I-107d | L51a | A1.03 | 25 |
| 695 | I-107d | L54a | A1.03 | 25 |
| 696 | I-104c | L50i | A1.03 | 27 |
| 697 | I-143a | L50i | A1.03 | 27 |
| 698 | I-141c | L50i | A1.03 | 27 |
| 699 | I-152 | blank | A1.03 | 24 |
| 700 | I-135e | L55a | A1.03 | 25 |
| 701 | I-135e | L55a | A6 | 25 |
| 702 | I-135a | L55a | A1.03 | 25 |
| 703 | I-135a | L55a | A6 | 25 |
| 704 | I-107o | L55a | A1.03 | 25 |
| 705 | I-107o | L55a | A6 | 25 |
| 706 | I-107a | L55a | A6 | 25 |
| 707 | I-135g | L48 | A30 | 25 |
| 708 | I-102 | L4a | A30 | 8 |
| 709 | I-141c | L75a | A18 | 27 |
| 710 | I-141c | L75b | A18 | 27 |
| 711 | I-107a | L55b | A18 | 25 |
| 712 | I-107o | L55b | A18 | 25 |
| 713 | I-102 | L59n | A18 | 8 |
| 714 | I-31 | I-145c | A18 | 33 |
| 715 | I-31 | I-142d | A18 | 33 |
| 716 | I-135a | 2-vinylbenozic acid | A18 | 25 |
| 717 | I-107w | L55a | A18 | 25 |
| 718 | I-141c | L76a | A18 | 27 |
| 719 | I-107a | L27 | A1.03 | 24 |
| 720 | I-107a | L27 | A1.03 | 24 |
| 721 | I-135g | L48 | A37 | 36 |
| 722 | I-107a | L27 | A3 | 24 |
| 723 | I-107a | L27 | A13 | 24 |
| 724 | I-107a | L27 | A3 | 24 |
| 725 | I-107a | L27 | A13 | 24 |
| 726 | I-135g | L48 | A22 | 36 |
| 727 | I-135a | L27 | A1.03 | 24 |
| 728 | I-135a | L27 | A1.46 | 24 |
| 729 | I-140aa | I-142a | A1.03 | 32 |
| 730 | I-135a | L27 | A13 | 24 |
| 731 | I-143a | L59g | A1.03 | 8 |
| 732 | I-143a | L59g | A13 | 8 |
| 733 | I-135a | L27 | A1.03 | 24 |
| 734 | I-140aa | I-142a | A13 | 32 |
| 735 | I-143a | L59g | A1.03 | 8 + 22 |
| 736 | I-143a | L59g | A13 | 8 + 22 |
| 737 | I-135g | L48 | A37 | 36 |
| 738 | I-135q | L48 | A1.03 | 25 |
| 739 | I-135q | L48 | A1.03 | 25 |
| 740 | I-143j | L59n | A1.03 | 8 |
| 741 | I-143j | L59n | A6 | 8 |
| 742 | I-135o | L48 | A1.03 | 25 |
| 743 | I-143j | L59k | A6 | 8 |
| 744 | I-143j | L59k | A1.03 | 8 |

TABLE 2-continued

| Example | Intermediate 1 | Intermediate 2 | A | Procedure |
|---|---|---|---|---|
| 745 | I-140i | I-142c | A1.03 | 32 |
| 746 | I-140m | I-142c | A1.03 | 32 |
| 747 | I-140m | I-142c | A6 | 32 |
| 748 | I-141c | L59f | A6 | 8 |
| 749 | I-104a | L4a | A3 | 8 |
| 750 | I-105b | L59n | A1.15 | 8 + 22 |
| 751 | I-105b | L59n | A1.15 | 8 |
| 752 | I-135g | L48 | A38 | 25 |
| 753 | I-140w | I-142a | A6 | 25 |
| 754 | I-141a | L59c | A18 | 8 |
| 755 | I-140x | I-142c | A18 | 32 |
| 756 | I-140x | I-142c | A18 | 32 |
| 757 | I-107a | L53 | A18 | 25 |
| 758 | I-107aa | L55a | A18 | 25 |
| 759 | I-140y | I-142a | A18 | 32 |
| 760 | I-140y | I-145c | A18 | 32 |
| 761 | I-135g | L66b | A18 | 25 |
| 762 | I-140z | I-145c | A18 | 32 |
| 763 | I-140z | I-142a | A18 | 32 |
| 764 | I-141c | L59n | A35 | 8 |
| 765 | I-135g | L48 | A35 | 25 |
| 766 | I-140r | L48 | A18 | 25 |
| 767 | I-107x | L48 | A18 | 25 |
| 768 | I-101b | L59n | A18 | 1 |
| 769 | I-135s | L55a | A18 | 25 |
| 770 | I-143a | L50k | A35 | 27 |
| 771 | I-135r | L66a | A18 | 25 |
| 772 | I-107y | L55a | A18 | 25 |
| 773 | I-135o | L66b | A18 | 25 |
| 774 | I-141c | L59n | A36 | 8 |
| 775 | I-107o | L53 | A18 | 25 |
| 776 | I-141j | L59v | A18 | 8 |
| 777 | I-100 | L59v | A18 | 1 |
| 778 | I-150a | blank | A1.03 | 21 |
| 779 | I-150b | blank | A1.03 | 21 |
| 780 | I-102 | L59i | A1.03 | 8 |
| 781 | I-102 | L59i | A1.03 | 8 |
| 782 | I-8a | blank | A1.03 | 44 |
| 783 | I-102 | L59h | A1.03 | 8 |
| 784 | I-102 | L59i | A13 | 8 |
| 785 | I-132b | blank | A1.03 | 21 |
| 786 | I-143a | L4a | A25a | 8 |
| 787 | I-151a | L62a | A1.03 | 25 |
| 788 | I-143a | L59j | A1.03 | 8 |
| 789 | I-141c | L59n | A1.03 | 8 |
| 790 | I-141c | L59n | A6 | 8 |
| 791 | I-141c | L59n | A1.25 | 8 |
| 792 | I-135g | L48 | A24 | 25 |
| 793 | I-143a | L59j | A6 | 8 |
| 794 | I-143a | L59j | A1.25 | 8 |
| 795 | I-143a | L4a | A24 | 8 |
| 796 | I-141c | L59j | A6 | 8 |
| 797 | I-141c | L59j | A1.03 | 8 |
| 798 | I-141c | L59n | A3 | 8 |
| 799 | I-107a | 3-allyloxetane-3-carboxylic acid | A6 | 25 |
| 800 | I-143a | L4a | A25b | 8 |
| 801 | I-135g | L48 | A26 | 25 |
| 802 | I-140l | I-142c | A6 | 32 |
| 803 | I-135g | L48 | A14 | 25 |
| 804 | I-140l | I-142c | A3 | 32 |
| 805 | I-140k | I-142c | A6 | 32 |
| 806 | I-140k | I-142c | A1.03 | 32 |
| 807 | I-141c | L59n | A1.11 | 8 |
| 808 | I-141c | L59n | A2 | 8 |
| 809 | I-141i | L59n | A18 | 8 |
| 810 | I-141c | L59k | A18 | 8 |
| 811 | I-100 | L59n | A18 | 1 |
| 812 | I-141e | L59n | A18 | 8 |
| 813 | I-141c | L59n | A18 | 45 |
| 814 | I-135e | I-29 | A18 | 25 |
| 815 | I-107t | L55a | A18 | 25 |
| 816 | I-107u | L55a | A18 | 25 |
| 817 | I-140p | I-142a | A18 | 32 |
| 818 | I-141i | L59k | A18 | 8 |
| 819 | I-141i | L59v | A18 | 8 |
| 820 | I-141c | L59n | A18 | 8 + 46 |
| 821 | I-135a | L61a | A1.03 | 25 |
| 822 | I-135a | L61a | A13 | 25 |
| 823 | I-135a | 1-allylcyclopropanecarboxylic acid | A1.03 | 25 |
| 824 | I-102 | L59a | A13 | 8 |
| 825 | I-153 | L59q | blank | 8 |
| 826 | I-140s | I-142a | A1.15 | 32 |
| 827 | I-140s | I-142a | A1.03 | 32 |
| 828 | I-141c | L59a | A1.03 | 8 |
| 829 | I-141c | L59c | A1.03 | 8 |
| 830 | I-141c | L59c | A6 | 8 |
| 831 | I-102 | L59r | A1.03 | 8 |
| 832 | I-141c | L59c | A6 | 22 + 8 |
| 833 | I-141c | L59c | A1.03 | 22 + 8 |
| 834 | I-140t | I-142c | A1.03 | 32 |
| 835 | I-140t | I-142c | A6 | 32 |
| 836 | I-141c | L59s | A1.03 | 8 |
| 837 | I-140u | I-142c | A1.03 | 32 |
| 838 | I-141c | L59t | A6 | 8 |
| 839 | I-141c | L59a | A18 | 8 |
| 840 | I-140t | L59n | A18 | 8 |
| 841 | I-141c | L59u | A18 | 8 |
| 842 | I-102 | L59t | A18 | 8 |
| 843 | I-141c | L59v | A18 | 8 |
| 844 | I-141c | L59w | A18 | 8 |
| 845 | I-141c | L59r | A18 | 8 |
| 846 | I-140v | I-145c | A18 | 32 |
| 847 | I-141i | L59t | A18 | 8 |
| 848 | I-135g | L48 | A1.03 | 25 |
| 849 | I-135g | L48 | A1.11 | 25 |
| 850 | I-135g | L48 | A13 | 25 |
| 851 | I-135g | L48 | A1.46 | 25 |
| 852 | I-135g | L48 | A1.41 | 25 |
| 853 | I-135g | L48 | A3 | 25 |
| 854 | I-102 | L50aa | A1.03 | 27 |
| 855 | I-102 | L49 | A1.03 | 22 + 8 |
| 856 | I-102 | L73b | A1.03 | 29 |
| 857 | I-102 | L73b | A1.03 | 29 |
| 858 | I-102 | L73a | A1.03 | 29 |
| 859 | I-102 | L73a | A1.03 | 29 |
| 860 | I-102 | L64a | A1.03 | 27 |
| 861 | I-102 | L65a | A1.03 | 28 |
| 862 | I-102 | L65a | A1.03 | 28 |
| 863 | I-107a | L71a | A1.03 | 25 |
| 864 | I-107a | L77 | A1.03 | 24 |
| 865 | I-107a | L77 | A1.03 | 24 |
| 866 | I-107f | 2-(3-bromophenyl)acetic acid | A1.03 | 48 |
| 867 | I-154a | L62a | A1.03 | 25 |
| 868 | I-155a | L62a | A1.03 | 25 |
| 869 | I-102 | L65b | A1.03 | 28 |
| 870 | I-102 | L65b | A1.03 | 28 |
| 871 | I-141c | L64a | A1.03 | 27 |
| 872 | I-141c | L64b | A1.03 | 29 |
| 873 | I-141c | L64b | A1.03 | 29 |
| 874 | I-107p | L62a | A1.03 | 25 |
| 875 | I-141c | L65c | A1.03 | 29 |
| 876 | I-141c | L65c | A1.03 | 29 |
| 877 | I-141a | L39b | A18 | 27 |
| 878 | I-141c | L75c | A18 | 27 |
| 879 | I-141c | L75d | A18 | 27 |
| 880 | I-141c | L73b | A18 | 29 |
| 881 | I-141c | L73b | A18 | 29 |
| 882 | I-107o | L62a | A18 | 25 |
| 883 | I-102 | L65b | A18 | 28 |
| 884 | I-102 | L65b | A18 | 28 |
| 885 | I-141c | L65b | A18 | 28 |
| 886 | I-141c | L65b | A18 | 28 |
| 887 | I-102 | L65c | A18 | 29 |
| 888 | I-102 | L65c | A18 | 29 |
| 889 | I-102 | L65d | A18 | 29 |
| 890 | I-102 | L65d | A18 | 29 |
| 891 | I-102 | L64a | A18 | 29 |
| 892 | I-102 | L64a | A18 | 29 |
| 893 | I-143a | L80 | A18 | 10 |
| 894 | I-143a | L80 | A18 | 8 |
| 895 | I-156 | L59n | A18 | 8 |
| 896 | I-143a | L59aa | A18 | 8 |

TABLE 2-continued

| Example | Intermediate 1 | Intermediate 2 | A | Procedure |
|---|---|---|---|---|
| 897 | I-143a | L59bb | A18 | 8 |
| 898 | I-143a | L59cc | A18 | 8 |
| 899 | I-143a | L59dd | A18 | 8 |
| 900 | I-143a | L59ee | A18 | 8 |
| 901 | I-143a | L59ff | A18 | 8 |
| 902 | I-143a | L59gg | A18 | 8 |
| 903 | I-143a | L59y | A18 | 8 |
| 904 | I-107x | L66b | A18 | 25 |
| 905 | I-107x | L66a | A18 | 25 |
| 906 | I-143a | L59z | A18 | 8 |
| 907 | I-153a | blank | A18 | 25 (from byproduct in step 2) |
| 908 | I-153a | blank | A18 | 25 |
| 909 | I-107a | L66a | A18 | 25 |
| 910 | I-107a | L66b | A18 | 25 |
| 911 | I-141c | L82 | A18 | 27 |
| 912 | I-141c | L7a | A18 | 8 |
| 913 | I-107v | L48 | A18 | 25 |
| 914 | I-135p | L48 | A18 | 25 |
| 915 | I-107a | L83 | A18 | 24 |
| 916 | I-107a | L83 | A18 | 24 |
| 917 | I-107d | L48c | A18 | 25 |
| 918 | I-107cc | L55a | A18 | 25 |
| 919 | I-140c | I-142d | A18 | 32 |
| 920 | I-140ee | I-142d | A18 | 32 |
| 921 | I-140ff | I-145c | A18 | 32 |
| 922 | I-140ee | I-142c | A18 | 32 |
| 923 | I-140gg | I-142d | A18 | 32 |
| 924 | I-135r | L48c | A18 | 25 |
| 925 | I-140ee | I-145c | A18 | 32 |
| 926 | I-140gg | I-145c | A18 | 32 |
| 927 | I-143a | L59jj | A18 | 8 |
| 928 | I-100 | L4a | A18 | 1 |
| 929 | I-107t | L53 | A18 | 37 |
| 930 | I-107u | L53 | A18 | 37 |
| 931 | I-135r | L66b | A18 | 25 |
| 932 | I-141k | L59n | A18 | 8 |
| 933 | I-107bb | L55a | A18 | 25 |
| 934 | I-141i | L58b | A18 | 27 |
| 935 | I-143a | L59ii | A18 | 8 |
| 936 | I-100 | L28a | A18 | 1 |
| 937 | I-8a | blank | A1 | 49 |
| 938 | I-140dd | I-142d | A18 | 32 |
| 939 | I-140dd | I-145c | A18 | 32 |
| 940 | I-135s | 1-allylcyclopropanecarboxylic acid | A18 | 25 |
| 941 | I-135s | 2,2-dimethylpent-4-enoic acid | A18 | 25 |
| 942 | I-103a | L59w | A18 | 8 |
| 943 | I-135a | 2,2-dimethylpent-4-enoic acid | A18 | 25 |
| 944 | I-141i | L59kk | A18 | 10 |
| 945 | I-141i | L59kk | A18 | 10 |
| 946 | I-107t | I-145c | A18 | 33 |
| 947 | I-107u | I-145c | A18 | 33 |
| 948 | I-107a | L81 | A18 | 24 |
| 949 | I-107a | L81 | A18 | 24 |
| 950 | I-143a | L59mm | A18 | 8 |
| 951 | I-141c | L59hh | A18 | 8 |
| 952 | I-140u | I-142d | A18 | 32 |
| 953 | I-141i | L59dd | A18 | 8 |
| 954 | I-143a | L50s | A18 | 27 |
| 955 | I-157 | L55a | A18 | 25 |

TABLE 3

| Example | ES/MS m/z [M + H]+ | $^1$H NMR |
|---|---|---|
| 1 | 654.3 | 1H NMR (400 MHz, DMSO-d6) δ 8.33 (d, J = 7.8 Hz, 1H), 8.06 (d, J = 8.0 Hz, 1H), 7.93 (s, 3H), 7.42 (s, 1H), 7.21 (d, J = 8.1 Hz, 1H), 7.04 (s, 1H), 6.92 (d, J = 1.2 Hz, 1H), 5.29-5.19 (m, 1H), 4.96-4.81 (m, 1H), 4.46-4.30 (m, 1H), 4.12 (s, 3H), 3.99 (s, 3H), 3.27 (s, 3H), 2.08-1.96 (m, 1H), 1.76 (s, 2H), 1.61 (d, J = 10.4 Hz, 4H), 1.47 (d, J = 7.1 Hz, 3H), 1.39 (s, 4H), 1.16 (s, 3H), 1.05 (s, 2H). |
| 2 | 652.3 | 1H NMR (400 MHz, DMSO-d6) δ 8.43 (d, J = 7.2 Hz, 1H), 8.08 (d, J = 8.1 Hz, 1H), 7.93 (s, 3H), 7.42 (s, 1H), 7.23 (d, J = 8.2 Hz, 1H), 7.05 (s, 1H), 6.92 (d, J = 1.2 Hz, 1H), 6.37-6.24 (m, 1H), 5.80 (d, J = 15.7 Hz, 1H), 5.25-5.13 (m, 1H), 4.79-4.69 (m, 1H), 4.54-4.41 (m, 1H), 4.13 (s, 3H), 4.00 (s, 3H), 3.47-3.38 (m, 1H), 3.33-3.08 (m, 2H), 2.24 (dd, J = 14.2, 9.3 Hz, 1H), 2.07-1.99 (m, 1H), 1.99-1.88 (m, 1H), 1.89-1.79 (m, 2H), 1.80-1.72 (m, 1H), 1.72-1.56 (m, 3H), 1.54 (d, J = 7.2 Hz, 3H), 1.15 (s, 3H). |
| 3 | 652.4 | 1H NMR (400 MHz, DMSO-d6) δ 8.15-8.06 (m, 2H), 7.93 (s, 3H), 7.42 (s, 1H), 7.26 (d, J = 8.2 Hz, 1H), 7.07 (s, 1H), 6.92 (d, J = 1.2 Hz, 1H), 5.62-5.53 (m, 1H), 5.41-5.20 (m, 2H), 4.96-4.83 (m, 1H), 4.50-4.40 (m, 1H), 4.12 (s, 3H), 4.00 (s, 3H), 3.25-3.09 (m, 3H), 2.85-2.75 (m, 1H), 2.30-2.20 (m, 1H), 2.07-1.97 (m, 1H), 1.92-1.69 (m, 2H), 1.70-1.32 (m, 10H). |
| 4 | 654.7 | 1H NMR (400 MHz, DMSO-d6) δ 8.29 (d, J = 7.4 Hz, 1H), 8.07 (d, J = 8.1 Hz, 1H), 7.94 (s, 3H), 7.42 (s, 1H), 7.22 (d, J = 8.1 Hz, 1H), 7.05 (s, 1H), 6.92 (d, J = 1.2 Hz, 1H), 5.22-5.11 (m, 1H), 4.84-4.73 (m, 1H), 4.52-4.40 (m, 1H), 4.12 (s, 3H), 3.99 (s, 3H), 3.34-3.08 (m, 3H), 2.07-1.92 (m, 2H), 1.92-1.82 (m, 1H), 1.81-1.71 (m, 1H), 1.70-1.54 (m, 4H), 1.50 (d, J = 7.1 Hz, 3H), 1.46 (s, 3H), 1.34 (s, 4H), 1.03 (s, 1H). |
| 5 | 614.3 | 1H NMR (400 MHz, DMSO-d6) δ 8.05 (d, J = 8.1 Hz, 1H), 7.90 (s, 3H), 7.84 (d, J = 7.4 Hz, 1H), 7.35 (d, J = 1.1 Hz, 1H), 7.19 (d, J = 8.1 Hz, 1H), 7.03 (s, 1H), 6.87 (d, J = 1.2 Hz, 1H), 5.12 (p, J = 7.1 Hz, 1H), 4.87-4.75 (m, 1H), 4.44-4.33 (m, 1H), 4.11 (s, 3H), 3.99 (s, 3H), 3.26-3.11 (m, 1H), 3.04-2.91 (m, 1H), 1.98-1.84 (m, 2H), 1.84-1.53 (m, 5H), 1.45 (d, J = 7.1 Hz, 3H), 1.42-1.27 (m, 4H), 1.24-1.18 (m, 6H), 1.15-1.01 (m, 2H), 0.95 (s, 3H). |
| 6 | 650.4 | 1H NMR (400 MHz, DMSO-d6) δ 8.44 (d, J = 8.6 Hz, 1H), 8.21 (s, 3H), 7.99 (d, J = 8.0 Hz, 1H), 7.47 (s, 1H), 7.14 (d, J = 8.1 Hz, 1H), 7.02 (s, 1H), 6.94 (d, J = 1.2 Hz, 1H), 6.86 (t, J = 74.9 Hz, 1H), 5.07-4.95 (m, |

TABLE 3-continued

| Example | ES/MS m/z [M + H]+ | ¹H NMR |
|---|---|---|
| | | 1H), 4.76-4.64 (m, 2H), 4.64-4.54 (m, 1H), 4.12 (s, 3H), 4.00 (s, 3H), 3.71-3.51 (m, 2H), 3.51-3.36 (m, 1H), 2.06-1.80 (m, 3H), 1.72-1.46 (m, 4H), 1.43 (d, J = 7.1 Hz, 3H), 1.42-1.32 (m, 1H), 1.31-1.15 (m, 1H), 0.93-0.79 (m, 1H), 0.77-0.58 (m, 2H), 0.53-0.41 (m, 1H) |
| 7 | 688.5 | 1H NMR (400 MHz, DMSO-d6) δ 9.24 (d, J = 7.0 Hz, 1H), 8.61 (d, J = 2.6 Hz, 1H), 8.50 (d, J = 2.5 Hz, 1H), 8.20 (s, 3H), 8.10 (d, J = 8.0 Hz, 1H), 7.46 (s, 1H), 7.28 (d, J = 8.1 Hz, 1H), 7.10 (s, 1H), 6.95 (d, J = 1.1 Hz, 1H), 6.86 (t, J = 74.8 Hz, 1H), 5.25 (p, J = 7.0 Hz, 1H), 4.90-4.78 (m, 1H), 4.72-4.64 (m, 1H), 4.63-4.51 (m, 1H), 4.13 (s, 3H), 4.00 (s, 3H), 3.70-3.51 (m, 2H), 3.52-3.37 (m, 1H), 2.74-2.63 (m, 1H), 2.49-2.32 (m, 2H), 2.06-1.86 (m, 2H), 1.52 (d, J = 7.1 Hz, 3H), 1.49-1.32 (m, 2H), 1.30-1.15 (m, 1H), 0.72-0.55 (m, 1H). |
| 8 | 612.3 | NA |
| 9 | 612.3 | NA |
| 10 | 626.4 | 1H NMR (400 MHz, DMSO-d6) δ 8.77 (d, J = 6.5 Hz, 1H), 8.10 (s, 3H), 8.06 (d, J = 8.0 Hz, 1H), 7.58 (d, J = 1.2 Hz, 1H), 7.19 (d, J = 8.1 Hz, 1H), 7.10 (s, 1H), 7.04 (s, 1H), 4.98 (p, J = 6.8 Hz, 1H), 4.76-4.66 (m, 2H), 4.16 (s, 3H), 4.02 (s, 3H), 3.84 (dd, J = 10.7, 7.3 Hz, 1H), 3.79-3.64 (m, 3H), 3.10 (dd, J = 10.6, 7.3 Hz, 1H), 2.38-2.23 (m, 2H), 1.94-1.76 (m, 4H), 1.69-1.57 (m, 1H), 1.42 (d, J = 6.9 Hz, 3H), 1.35 (dd, J = 12.9, 4.4 Hz, 1H), 1.09 (s, 3H), 0.89 (s, 3H), 0.79-0.62 (m, 2H). |
| 11 | 626.4 | 1H NMR (400 MHz, DMSO-d6) δ 8.74 (d, J = 7.8 Hz, 1H), 8.20-8.05 (m, 4H), 7.58 (s, 1H), 7.28 (d, J = 8.2 Hz, 1H), 7.12 (s, 1H), 7.04 (d, J = 1.2 Hz, 1H), 5.17 (p, J = 7.0 Hz, 1H), 4.60 (dd, J = 14.0, 6.1 Hz, 1H), 4.55-4.45 (m, 1H), 4.18 (s, 3H), 4.02 (s, 3H), 3.85-3.64 (m, 4H), 3.46-3.36 (m, 1H), 2.37-2.24 (m, 2H), 1.93-1.75 (m, 3H), 1.67-1.60 (m, 1H), 1.57 (d, J = 6.9 Hz, 3H), 1.35 (dd, J = 12.9, 4.4 Hz, 1H), 0.89 (s, 3H), 0.86 (s, 3H), 0.83-0.77 (m, 1H), 0.67-0.57 (m, 1H). |
| 12 | 666.4 | 1H NMR (400 MHz, DMSO-d6) δ 8.34 (d, J = 7.9 Hz, 1H), 8.14-8.00 (m, 4H), 7.59 (s, 1H), 7.21 (d, J = 8.1 Hz, 1H), 7.05 (s, 1H), 7.04 (d, J = 1.2 Hz, 1H), 5.29-5.18 (m, 1H), 4.95-4.84 (m, 1H), 4.64-4.29 (m, 2H), 4.12 (s, 3H), 4.01 (s, 3H), 3.80-3.68 (m, 1H), 2.48-2.40 (m, 1H), 1.93-1.74 (m, 4H), 1.73-1.54 (m, 3H), 1.47 (d, J = 7.1 Hz, 3H), 1.45-1.28 (m, 4H), 1.16 (s, 3H), 1.04 (s, 3H). |
| 13 | 612.4 | 1H NMR (400 MHz, DMSO-d6) (NOTE: Rotamers observed, in a 0.6:0.4 ratio. Partial proton counts reported where diagnostic) δ 8.08 (s, 1.2H), 8.05 (d, J = 8.1 Hz, 1H), 7.93 (d, J = 5.4 Hz, 1.8H), 7.84 (d, J = 7.5 Hz, 1H), 7.55 (s, 0.4H), 7.41 (s, 0.6H), 7.19 (d, J = 8.1 Hz, 1H), 7.04 (s, 1H), 7.00 (s, 0.4H), 6.96 (s, 0.6H), 5.12 (p, J = 7.0 Hz, 1H), 4.89-4.76 (m, 1H), 4.53 (s, 0.4H), 4.47-4.37 (m, 1H), 4.21 (s, 0.6H), 4.12 (s, 3H), 4.00 (s, 3H), 3.83-3.75 (m, 0.4H), 3.69-3.51 (m, 1.6H), 3.24-3.13 (m, 1H), 2.05-1.80 (m, 4H), 1.76-1.52 (m, 3H), 1.45 (d, J = 7.1 Hz, 3H), 1.44-1.27 (m, 4H), 1.21 (s, 3H), 1.15-0.99 (m, 2H), 0.95 (s, 3H). |
| 14 | 680.6 | 1H NMR (400 MHz, DMSO-d6) δ 8.05 (d, J = 8.1 Hz, 1H), 8.02 (s, 3H), 7.84 (d, J = 7.4 Hz, 1H), 7.45 (s, 1H), 7.19 (d, J = 8.1 Hz, 1H), 7.04 (s, 1H), 6.94 (d, J = 1.2 Hz, 1H), 6.19 (tt, J = 55.0, 3.8 Hz, 1H), 5.12 (p, J = 7.1 Hz, 1H), 4.87-4.76 (m, 1H), 4.40 (dt, J = 13.7, 7.1 Hz, 1H), 4.12 (s, 3H), 3.99 (s, 3H), 3.98-3.93 (m, 1H), 3.90-3.76 (m, 2H), 3.49-3.39 (m, 3H), 1.93 (t, J = 12.0 Hz, 2H), 1.86-1.74 (m, 1H), 1.74-1.56 (m, 2H), 1.45 (d, J = 7.1 Hz, 3H), 1.42-1.26 (m, 4H), 1.21 (s, 3H), 1.08 (s, 2H), 0.95 (s, 3H). |
| 15 | 614.4 | 1H NMR (400 MHz, DMSO-d6) δ 8.05 (d, J = 8.1 Hz, 1H), 7.91 (s, 3H), 7.83 (d, J = 7.4 Hz, 1H), 7.36 (d, J = 1.1 Hz, 1H), 7.19 (d, J = 8.1 Hz, 1H), 7.03 (s, 1H), 6.88 (s, 1H), 5.18-5.07 (m, 1H), 4.87-4.76 (m, 1H), 4.48-4.35 (m, 1H), 4.12 (t, 3H), 3.99 (s, 3H), 3.42-3.33 (m, 2H), 1.93 (t, J = 12.3 Hz, 1H), 1.85-1.53 (m, 5H), 1.45 (d, J = 7.1 Hz, 3H), 1.41-1.28 (m, 4H), 1.26-1.16 (m, 6H), 1.14-1.02 (m, 3H), 0.95 (s, 3H). |
| 16 | 600.3 | 1H NMR (400 MHz, DMSO-d6) δ 8.05 (d, J = 8.1 Hz, 1H), 7.95 (m, 3H), 7.84 (d, J = 7.5 Hz, 1H), 7.42 (s, 1H), 7.19 (d, J = 8.2 Hz, 1H), 7.04 (s, 1H), 6.92 (m, 1H), 5.12 (m, 1H), 4.82 (m, 1H), 4.40 (m, 1H), 4.12 (s, 3H), 3.99 (s, 3H), 3.37-3.00 (m, 2H), 2.90 (s, 1H), 2.74 (s, 1H), 1.95-1.85 (m, 2H), 1.79-1.52 (m, 3H), 1.48-1.25 (m, 7H), 1.21 (s, 3H), 1.15-1.07 (m, 2H), 0.95 (s, 3H). |
| 17 | 616.4 | 1H NMR (400 MHz, Methanol-d4) δ 8.45 (d, J = 8.0 Hz, 1H), 8.07 (d, J = 8.0 Hz, 1H), 7.47 (d, J = 1.2 Hz, 1H), 7.18 (d, J = 8.1 Hz, 1H), 7.07-6.93 (m, 2H), 5.32-5.10 (m, 1H), 4.82 (m, 1H), 4.40 (m, 1H), 4.15 (s, 3H), 4.08 (s, 3H), 3.63-3.45 (m, 3H), 3.48-3.35 (m, 6H), 2.25-2.15 (m, 1H), 2.07-1.60 (m, 6H), 1.60-1.32 (m, 7H), 1.25 (s, 3H), 1.07 (s, 3H). |
| 18 | 602.4 | 1H NMR (400 MHz, CD3OD ) d 8.10 (d, J = 8.1 Hz, 1H), 7.47 (s, 1H), 7.23 (d, J = 8.2 Hz, 1H), 7.09-6.93 (m, 1H), 5.30 (q, J = 6.7 Hz, 1H), 5.00 (m, 1H), 4.48-4.32 (m, 1H), 4.16 (s, 3H) 4.09 (m, 4H), 3.51-3.38 (m, 4H), 2.87 (m, 1H), 2.41 (m, 1H), 2.21 (m, 1H), 1.98-1.50 (m, 11H), 1.43 (s, 3H), 1.33 (m, 5H), 1.12-0.64 (m, 2H). |
| 19 | 620.3 | 1H NMR (400 MHz, CD3OD ) d 8.45 (d, J = 9.2 Hz, 1H), 8.09 (d, J = 8.0 Hz, 1H), 7.92 (s, 1H), 7.44 (s, 1H), 7.22 (d, J = 8.1 Hz, 1H), 7.01 (s, 1H), 5.30 (m, 1 H), 5.08-4.94 (m, 1H), 4.61-4.29 (m, 2H), 4.14 (s, 3H), 4.11 |

TABLE 3-continued

| Example | ES/MS m/z [M + H]+ | 1H NMR |
|---|---|---|
| | | (s, 3H), 3.68 (d, 1H), 3.62-3.42 (m, 2H), 3.18 (m, 2H)), 2.95-2.77 (m, 1H), 2.67-2.32 (m, 2H), 2.20-1.88 (m, 1H), 1.78-1.50 (m, 6H), 1.38 (s, 3H), 1.34 (m, 4H) 0.92-0.57 (m, 1H). |
| 20 | 612.4 | 1H NMR (400 MHz, DMSO-d6) δ 8.16-8.00 (m, 4H), 7.84 (d, J = 7.4 Hz, 1H), 7.59 (s, 1H), 7.19 (d, J = 8.1 Hz, 1H), 7.04 (d, J = 1.6 Hz, 1H), 5.12 (m, 1H), 4.88-4.75 (m, 1H), 4.46-4.30 (m, 4H), 4.12 (s, 3H), 4.01 (s, 3H), 2.33 (m, 2H), 2.04-1.73 (m, 4H), 1.72-1.50 (m, 3H), 1.49-1.25 (m, 7H), 1.21 (s, 3H), 1.11 (m, 2H), 0.95 (s, 3H). |
| 21 | 614.4 | 1H NMR (400 MHz, DMSO-d6) δ 8.13 (s, 3H), 8.05 (d, J = 8.1 Hz, 1H), 7.84 (d, J = 7.4 Hz, 1H), 7.59 (s, 1H), 7.19 (d, J = 8.2 Hz, 1H), 7.04 (s, 1H), 5.12 (m, 1H), 4.82 (m, 1H), 4.70-4.33 (m, 4H), 4.12 (s, 3H), 4.01 (s, 3H), 2.90 (s, 1H), 2.74 (s, 1H), 2.02-1.52 (m, 5H), 1.52-1.26 (m, 8H), 1.21 (s, 3H), 1.09 (m, 2H), 0.95 (s, 3H). |
| 22 | 628.4 | 1H NMR (400 MHz, Methanol-d4) δ 8.17-7.97 (m, 1H), 7.62 (d, J = 1.2 Hz, 1H), 7.27-7.11 (m, 2H), 7.01 (s, 1H), 5.31-5.08 (m, 1H), 4.86-4.70 (m, 1H), 4.72-4.31 (m, 1H), 4.16 (s, 3H), 4.09 (s, 3H), 3.95-3.81 (m, 1H), 3.64-3.54 (m, 1H), 3.46-3.34 (m, 6H), 2.59-2.40 (m, 1H), 2.19-1.83 (m, 3H), 1.81-1.63 (m, 3H), 1.61-1.33 (m, 7H), 1.25 (s, 3H), 1.07 (s, 3H). |
| 23 | 618.3 | 1H NMR (400 MHz, CD3OD ) d 8.15 (d, J = 8.2 Hz, 1H), 7.62 (d, J = 1.3 Hz, 1H), 7.26 (d, J = 8.2 Hz, 1H), 7.14 (d, J = 1.3 Hz, 1H), 7.08 (s, 1H), 5.65-5.53 (m, 1H), 5.30-5.00 (m, 2H), 4.86-4.50 (m, 4H), 4.45-4.32 (m, 1H), 4.20 (s, 3H), 4.09 (s, 3H), 3.92-3.79 (m, 1H), 2.91-2.74 (m, 1H), 2.58-2.37 (m, 2H), 2.13-1.54 (m, 10 H), 1.56-1.38 (m, 2H), 0.96-0.82 (m, 2H). |
| 24 | 630.3 | NA |
| 25 | 582.4 | 1H NMR (400 MHz, CD3OD ) d 8.00 (s, 1H), 7.94 (d, J = 8.0 Hz, 1H), 7.10 (d, J = 8.0 Hz, 1H), 6.63, (s, 1H), 6.60 (m, 1H), 6.16 (s, 2H), 5.04 (m, 1H), 4.63-4.38 (m, 4H), 4.11 (s, 3H), 3.41 (m, 2H), 2.91 (s, 3H), 1.72-1.54 (m, 10 H), 1.52-1.37 (m, 4H), 1.0-0.95 (m, 1H), 0.80-0.71 (m, 2H). |
| 26 | 572.4 | 1H NMR (400 MHz, DMSO-d6) δ 8.46 (d, J = 1.1 Hz, 1H), 8.29 (d, J = 8.5 Hz, 1H), 7.96 (d, J = 8.0 Hz, 1H), 7.91 (s, 3H), 7.12 (d, J = 8.1 Hz, 1H), 6.76 (s, 1H), 6.61 (d, J = 1.0 Hz, 1H), 5.25-5.11 (m, 1H), 4.94 (dt, J = 14.3, 7.7 Hz, 1H), 4.49-4.36 (m, 1H), 4.16-4.01 (m, 1H), 3.98 (s, 3H), 3.36-3.12 (m, 4H), 2.52 (s, 3H), 2.15-1.93 (m, 4H), 1.84-1.33 (m, 9H), 1.29-0.92 (m, 5H), 0.76-0.58 (m, 1H). |
| 27 | 600.4 | 1H NMR (400 MHz, DMSO-d6) δ 8.46 (d, J = 1.0 Hz, 1H), 7.96 (d, J = 8.0 Hz, 1H), 7.92 (s, 3H), 7.78 (d, J = 7.5 Hz, 1H), 7.12 (d, J = 8.1 Hz, 1H), 6.75 (s, 1H), 6.61 (d, J = 1.1 Hz, 1H), 5.12 (p, J = 7.0 Hz, 1H), 4.87-4.73 (m, 1H), 4.41-4.26 (m, 1H), 4.13-4.01 (m, 1H), 3.98 (s, 3H), 3.39-3.09 (m, 4H), 2.52 (s, 3H), 2.08-1.85 (m, 2H), 1.83-1.24 (m, 12H), 1.20 (s, 3H), 1.17-0.99 (m, 3H), 0.95 (s, 3H). |
| 28 | 620.3 | 1H NMR (400 MHz, DMSO-d6) δ 8.82 (d, J = 6.9 Hz, 1H), 8.07 (d, J = 8.0 Hz, 1H), 7.95 (s, 3H), 7.40 (s, 1H), 7.37-7.27 (m, 2H), 7.27-7.15 (m, 3H), 7.07 (s, 1H), 6.92 (s, 1H), 5.18 (p, J = 7.0 Hz, 1H), 4.93-4.79 (m, 1H), 4.64-4.50 (m, 1H), 4.11 (s, 3H), 3.99 (s, 3H), 3.33-3.04 (m, 5H), 2.43-2.29 (m, 1H), 2.29-2.15 (m, 1H), 2.09-1.95 (m, 1H), 1.82-1.05 (m, 11H), 0.61-0.43 (m, 1H). |
| 29 | 634.3 | 1H NMR (400 MHz, DMSO-d6) δ 8.57 (d, J = 7.7 Hz, 1H), 8.08 (d, J = 8.1 Hz, 1H), 7.93 (s, 3H), 7.41 (s, 1H), 7.39-7.27 (m, 3H), 7.27-7.17 (m, 2H), 7.04 (s, 1H), 6.91 (s, 1H), 5.35 (p, J = 7.0 Hz, 1H), 4.72-4.49 (m, 2H), 4.11 (s, 3H), 3.99 (s, 3H), 3.37-3.01 (m, 3H), 2.96-2.82 (m, 1H), 2.48-2.37 (m, 2H), 2.04 (d, J = 25.5 Hz, 1H), 1.75 (s, 1H), 1.67-1.15 (m, 12H), 1.10-0.88 (m, 2H). |
| 30 | 622.3 | 1H NMR (400 MHz, DMSO-d6) δ 9.73 (d, J = 6.8 Hz, 1H), 8.14 (d, J = 8.0 Hz, 1H), 8.07 (dd, J = 7.8, 1.9 Hz, 1H), 7.94 (s, 3H), 7.55-7.46 (m, 1H), 7.45 (s, 1H), 7.33 (d, J = 8.1 Hz, 1H), 7.20 (d, J = 8.4 Hz, 1H), 7.13-7.03 (m, 2H), 6.93 (s, 1H), 5.34 (p, J = 6.6 Hz, 1H), 4.77-4.63 (m, 1H), 4.48-4.34 (m, 3H), 4.33-4.23 (m, 2H), 4.13 (s, 3H), 4.00 (s, 3H), 3.35-3.02 (m, 3H), 2.74-2.58 (m, 1H), 2.37-2.20 (m, 1H), 2.11-1.49 (m, 9H). |
| 31 | 638.3 | 1H NMR (400 MHz, DMSO-d6) δ 8.85-8.64 (m, 4H), 8.08 (d, J = 8.0 Hz, 1H), 7.99 (d, J = 1.3 Hz, 1H), 7.40-7.17 (m, 6H), 7.12 (s, 1H), 5.19 (p, J = 7.0 Hz, 1H), 4.98-4.73 (m, 2H), 4.65-4.54 (m, 1H), 4.52-4.36 (m, 1H), 4.14 (s, 3H), 4.02 (s, 3H), 3.53-3.32 (m, 2H), 3.15-2.89 (m, 2H), 2.44-2.29 (m, 2H), 2.29-2.17 (m, 1H), 2.00-1.83 (m, 1H), 1.65-1.06 (m, 8H), 0.65-0.47 (m, 1H). |
| 32 | 622.3 | 1H NMR (400 MHz, DMSO-d6) δ 8.89 (d, J = 6.7 Hz, 1H), 8.05 (s, 3H), 7.96 (d, J = 8.0 Hz, 1H), 7.49 (d, J = 1.8 Hz, 1H), 7.42 (s, 1H), 7.15 (d, J = 8.1 Hz, 1H), 6.68 (d, J = 1.9 Hz, 1H), 6.59 (s, 1H), 6.35 (s, 1H), 5.13-5.01 (m, 1H), 4.66-4.30 (m, 5H), 4.15-3.97 (m, 4H), 3.82-3.65 (m, 1H), 2.81 (s, 3H), 2.35-2.24 (m, 1H), 2.01-1.76 (m, 4H), 1.76-1.59 (m, 2H), 1.55 (d, J = 7.0 Hz, 3H), 1.52-1.41 (m, 1H), 1.42-1.26 (m, 2H), 1.13-0.85 (m, 2H). |
| 33 | 622.3 | 1H NMR (400 MHz, DMSO-d6) δ 9.07 (d, J = 7.7 Hz, 1H), 8.08 (s, 3H), 8.00 (d, J = 8.0 Hz, 1H), 7.79 (s, 1H), 7.46 (s, 1H), 7.22 (d, J = 8.0 Hz, |

TABLE 3-continued

| Example | ES/MS m/z [M + H]+ | 1H NMR |
|---|---|---|
| | | 1H), 6.60 (s, 1H), 6.58 (s, 1H), 6.37 (s, 1H), 5.15 (p, J = 7.0 Hz, 1H), 4.69-4.23 (m, 5H), 4.23-4.05 (m, 4H), 3.85-3.69 (m, 1H), 2.81 (s, 3H), 2.33 (s, 1H), 2.14-1.92 (m, 2H), 1.92-1.68 (m, 5H), 1.70-1.40 (m, 6H), 1.40-1.29 (m, 1H). |
| 34 | 608.3 | 1H NMR (400 MHz, DMSO-d6) δ 9.13 (d, J = 6.9 Hz, 1H), 8.07 (s, 3H), 7.95 (d, J = 8.0 Hz, 1H), 7.44 (s, 1H), 7.41 (d, J = 2.5 Hz, 1H), 7.18 (d, J = 8.0 Hz, 1H), 6.61 (d, J = 2.0 Hz, 1H), 6.39 (s, 1H), 6.36 (s, 1H), 5.21-5.05 (m, 1H), 4.72-4.22 (m, 6H), 4.09 (s, 3H), 3.91-3.62 (m, 1H), 2.81 (s, 3H), 2.38-2.25 (m, 1H), 2.10-1.94 (m, 1H), 1.94-1.71 (m, 4H), 1.71-1.59 (m, 1H), 1.59-1.29 (m, 6H). |
| 35 | 636.4 | 1H NMR (400 MHz, DMSO-d6) δ 8.77 (d, J = 8.2 Hz, 1H), 8.09 (s, 3H), 7.98 (d, J = 8.0 Hz, 1H), 7.46 (s, 1H), 7.42 (s, 1H), 7.20 (d, J = 8.0 Hz, 1H), 6.80 (s, 1H), 6.61 (s, 1H), 6.37 (s, 1H), 5.39-5.23 (m, 1H), 4.86-4.67 (m, 1H), 4.68-4.23 (m, 4H), 4.21-3.99 (m, 4H), 3.88-3.62 (m, 1H), 2.80 (s, 3H), 2.40-2.19 (m, 1H), 1.95-1.72 (m, 3H), 1.71-1.41 (m, 6H), 1.42-1.21 (m, 3H), 1.14-0.80 (m, 4H). |
| 36 | 636.3 | 1H NMR (400 MHz, DMSO-d6) δ 9.16-9.04 (m, 1H), 8.08 (s, 3H), 8.04 (d, J = 8.2 Hz, 1H), 7.83 (d, J = 3.0 Hz, 1H), 7.47 (s, 1H), 7.24 (d, J = 8.0 Hz, 1H), 6.64 (s, 1H), 6.62 (d, J = 2.3 Hz, 1H), 6.37 (s, 1H), 5.31-5.18 (m, 1H), 4.69-4.24 (m, 6H), 4.10 (s, 3H), 3.89-3.64 (m, 1H), 2.82 (s, 3H), 2.39-2.24 (m, 1H), 2.01-1.59 (m, 9H), 1.59-1.42 (m, 4H), 1.35 (d, J = 13.0 Hz, 1H), 1.30-1.16 (m, 1H), 1.07-0.87 (m, 1H). |
| 37 | 619.3 | 1H NMR (400 MHz, DMSO-d6) δ 11.05 (d, J = 7.0 Hz, 1H), 8.16 (d, J = 8.2 Hz, 1H), 8.05 (s, 3H), 7.97-7.81 (m, 2H), 7.63 (s, 1H), 7.46 (d, J = 7.5 Hz, 1H), 7.35 (d, J = 8.2 Hz, 1H), 7.12-6.98 (m, 2H), 5.26-5.15 (m, 1H), 4.72-4.34 (m, 4H), 4.15 (s, 3H), 4.02 (s, 3H), 3.88-3.67 (m, 1H), 3.17-3.04 (m, 1H), 2.94-2.70 (m, 2H), 2.40-2.25 (m, 1H), 2.15-1.98 (m, 1H), 1.96-1.54 (m, 9H), 1.40-1.28 (m, 1H). |
| 38 | 636.3 | 1H NMR (400 MHz, DMSO-d6) δ 8.74 (d, J = 9.5 Hz, 1H), 8.14 (d, J = 8.2 Hz, 1H), 8.05 (s, 3H), 7.60 (s, 1H), 7.35 (d, J = 8.2 Hz, 1H), 7.32-7.15 (m, 3H), 7.04 (s, 1H), 6.97 (s, 1H), 5.41-5.28 (m, 1H), 4.68-4.15 (m, 4H), 4.08 (s, 3H), 4.01 (s, 3H), 3.74 (s, 1H), 2.82-2.71 (m, 1H), 2.41-2.12 (m, 2H), 2.08-1.94 (m, 1H), 1.91-1.71 (m, 4H), 1.70-1.28 (m, 6H), 0.99-0.85 (m, 1H). |
| 39 | 632.3 | 1H NMR (400 MHz, DMSO-d6) δ 8.81 (d, J = 6.9 Hz, 1H), 8.08 (d, J = 8.1 Hz, 1H), 8.04 (s, 3H), 7.58 (s, 1H), 7.38-7.27 (m, 2H), 7.27-7.17 (m, 3H), 7.08 (s, 1H), 7.03 (s, 1H), 5.25-5.11 (m, 1H), 4.94-4.78 (m, 1H), 4.66-4.27 (m, 3H), 4.11 (s, 3H), 4.01 (s, 3H), 3.81-3.65 (m, 1H), 2.44-2.36 (m, 2H), 2.29-2.13 (m, 1H), 1.90-1.72 (m, 4H), 1.70-1.55 (m, 1H), 1.57-1.05 (m, 8H), 0.60-0.45 (m, 1H). |
| 40 | 646.3 | 1H NMR (400 MHz, DMSO-d6) δ 8.57 (d, J = 7.7 Hz, 1H), 8.09 (d, J = 8.1 Hz, 1H), 8.06 (s, 3H), 7.59 (s, 1H), 7.39-7.26 (m, 3H), 7.26-7.16 (m, 2H), 7.05 (s, 1H), 7.03 (s, 1H), 5.35 (p, J = 7.1 Hz, 1H), 4.74-4.35 (m, 4H), 4.10 (s, 3H), 4.00 (s, 3H), 3.81-3.67 (m, 1H), 2.95-2.81 (m, 1H), 2.47-2.23 (m, 2H), 1.91-1.71 (m, 3H), 1.69-1.16 (m, 11H), 1.09-0.88 (m, 2H). |
| 41 | 634.3 | 1H NMR (400 MHz, DMSO-d6) δ 9.72 (d, J = 6.8 Hz, 1H), 8.22-7.97 (m, 5H), 7.62 (s, 1H), 7.55-7.44 (m, 1H), 7.33 (d, J = 8.1 Hz, 1H), 7.20 (d, J = 8.4 Hz, 1H), 7.14-7.00 (m, 3H), 5.34 (p, J = 6.5 Hz, 1H), 4.77-4.63 (m, 1H), 4.56-4.34 (m, 4H), 4.32-4.22 (m, 1H), 4.13 (s, 3H), 4.01 (s, 3H), 3.83-3.68 (m, 1H), 2.75-2.59 (m, 1H), 2.39-2.18 (m, 2H), 2.00-1.51 (m, 9H), 1.35 (dd, J = 12.9, 4.4 Hz, 1H). |
| 42 | 632.3 | 1H NMR (400 MHz, DMSO-d6) δ 8.82 (d, J = 6.9 Hz, 1H), 8.11-7.84 (m, 4H), 7.57-7.15 (m, 6H), 7.08 (s, 1H), 7.02-6.92 (m, 1H), 5.18 (p, J = 7.0 Hz, 1H), 4.93-4.79 (m, 1H), 4.68-4.55 (m, 1H), 4.11 (s, 3H), 4.00 (s, 3H), 3.81-3.50 (m, 3H), 3.18 (t, J = 11.4 Hz, 1H), 2.72-2.53 (m, 2H), 2.44-2.14 (m, 2H), 2.04-1.76 (m, 3H), 1.67 (d, J = 15.0 Hz, 1H), 1.56-1.31 (m, 5H), 1.31-1.05 (m, 2H), 0.61-0.41 (m, 1H). |
| 43 | 650.3 | 1H NMR (400 MHz, DMSO-d6) δ 8.82 (d, J = 6.9 Hz, 1H), 8.07 (d, J = 8.0 Hz, 1H), 7.96 (s, 3H), 7.43 (s, 1H), 7.38-7.27 (m, 2H), 7.27-7.15 (m, 3H), 7.07 (s, 1H), 6.93 (s, 1H), 5.18 (p, J = 6.9 Hz, 1H), 4.92-4.77 (m, 1H), 4.63-4.52 (m, 1H), 4.11 (s, 3H), 3.99 (s, 3H), 3.75-3.48 (m, 5H), 3.46-3.31 (m, 4H), 2.46-2.15 (m, 2H), 2.01-1.87 (m, 1H), 1.83-1.68 (m, 1H), 1.59-1.33 (m, 5H), 1.33-1.06 (m, 3H), 0.63-0.45 (m, 1H). |
| 44 | 635.3 | 1H NMR (400 MHz, DMSO-d6) δ 8.82 (d, J = 7.0 Hz, 1H), 8.16-7.94 (m, 4H), 7.48 (s, 1H), 7.38-7.26 (m, 2H), 7.26-7.16 (m, 3H), 7.06 (s, 1H), 7.00 (s, 1H), 5.18 (p, J = 6.9 Hz, 1H), 4.93-4.79 (m, 1H), 4.66-4.53 (m, 1H), 4.53-4.42 (m, 1H), 4.10 (s, 3H), 3.98 (s, 3H), 3.70-3.26 (m, 2H), 3.16-2.99 (m, 2H), 2.94-2.81 (m, 1H), 2.55 (s, 3H), 2.45-2.12 (m, 2H), 2.02-1.86 (m, 1H), 1.73-1.62 (m, 1H), 1.59-1.32 (m, 5H), 1.32-1.08 (m, 2H), 0.65-0.44 (m, 1H). |
| 45 | 607.3 | 1H NMR (400 MHz, DMSO-d6) δ 10.49 (s, 1H), 8.94 (s, 1H), 8.73 (d, J = 6.8 Hz, 1H), 8.68 (d, J = 6.7 Hz, 1H), 8.41 (d, J = 7.5 Hz, 1H), 8.00 (s, 3H), 7.67 (d, J = 7.8 Hz, 1H), 7.43 (s, 1H), 7.24 (s, 1H), 6.94 (s, 1H), 4.67 (t, J = 6.1 Hz, 2H), 4.34-4.16 (m, 2H), 4.14 (s, 3H), 4.00 (s, 3H), 3.36- |

TABLE 3-continued

| Example | ES/MS m/z [M + H]+ | 1H NMR |
|---|---|---|
| | | 3.02 (m, 3H), 2.48-2.40 (m, 2H), 2.05-2.00 (m, 1H), 1.82-1.64 (m, 3H), 1.62-1.49 (m, 7H), 1.30-1.25 (m, 2H). |
| 46 | 607.3 | 1H NMR (400 MHz, DMSO-d6) δ 8.64-8.58 (m, 1H), 8.50 (t, J = 6.0 Hz, 1H), 8.23 (d, J = 7.6 Hz, 1H), 8.01 (d, J = 7.8 Hz, 1H), 7.94 (s, 3H), 7.64-7.56 (m, 1H), 7.45 (d, J = 7.9 Hz, 1H), 7.41 (s, 1H), 7.14 (s, 1H), 6.92 (s, 1H), 4.64 (t, J = 7.0 Hz, 2H), 4.16 (s, 3H), 4.12-4.02 (m, 2H), 4.00 (s, 3H), 3.32-3.08 (m, 5H), 2.04-1.99 (m, 1H), 1.79-1.74 (m, 1H), 1.61-1.56 (m, 2H), 1.48 (s, 4H), 1.45-1.38 (m, 2H), 1.15-1.10 (m, 2H). |
| 47 | 605.3 | 1H NMR (400 MHz, DMSO-d6) δ 9.17 (s, 1H), 7.94 (s, 3H), 7.80 (d, J = 8.2 Hz, 1H), 7.59 (d, J = 8.0 Hz, 1H), 7.55 (s, 1H), 7.44-7.38 (m, 2H), 7.35 (td, J = 7.6, 1.8 Hz, 1H), 7.28 (td, J = 7.4, 1.4 Hz, 1H), 7.18 (dd, J = 8.2, 1.3 Hz, 1H), 7.11 (s, 1H), 6.91 (s, 1H), 4.54-4.48 (m, 2H), 4.10 (s, 3H), 3.99 (s, 3H), 3.34-3.07 (m, 5H), 2.30-2.22 (m, 2H), 2.10-1.97 (m, 2H), 1.81-1.37 (m, 8H), 1.18-1.09 (m, 2H). |
| 48 | 618.3 | 1H NMR (400 MHz, DMSO-d6) δ 8.28 (t, J = 5.8 Hz, 1H), 8.20 (d, J = 8.1 Hz, 1H), 8.11 (s, 3H), 7.59 (s, 1H), 7.58-7.43 (m, 4H), 7.41 (d, J = 8.1 Hz, 1H), 7.13 (s, 1H), 7.04 (d, J = 1.2 Hz, 1H), 4.68 (t, J = 6.4 Hz, 2H), 4.59-4.22 (m, 2H), 4.16 (s, 3H), 4.02 (s, 3H), 3.81-3.62 (m, 1H), 3.15 (q, J = 5.5 Hz, 2H), 2.38-2.25 (m, 1H), 1.90-1.72 (m, 4H), 1.67-1.59 (m, 1H), 1.53-1.28 (m, 7H), 1.08-0.97 (m, 2H). |
| 49 | 606.3 | 1H NMR (400 MHz, DMSO-d6) δ 8.29 (t, J = 5.7 Hz, 1H), 8.20 (d, J = 8.1 Hz, 1H), 7.95 (s, 3H), 7.58-7.44 (m, 4H), 7.41 (d, J = 8.1 Hz, 1H), 7.41 (s, 1H), 7.12 (s, 1H), 6.92 (d, J = 1.1 Hz, 1H), 4.68 (t, J = 6.5 Hz, 2H), 4.58-4.27 (m, 2H), 4.15 (s, 3H), 4.00 (s, 3H), 3.34-3.10 (m, 5H), 2.05-1.98 (m, 1H), 1.85-1.70 (m, 1H), 1.64-1.55 (m, 2H), 1.49-1.33 (m, 7H), 1.09-0.97 (m, 2H). |
| 50 | 579.3 | 1H NMR (400 MHz, DMSO-d6) δ 10.72 (br. s, 1H), 8.61 (br. d, J = 7.5 Hz, 1H), 8.38 (d, J = 8.4 Hz, 1H), 8.10 (dd, J = 6.0, 1.5 Hz, 1H), 8.02 (s, 3H), 7.97 (d, J = 8.5 Hz, 1H), 7.44 (s, 1H), 7.21 (s, 1H), 7.00 (t, J = 6.8 Hz, 1H), 6.95-6.91 (m, 1H), 4.53 (t, J = 7.8 Hz, 2H), 4.18 (s, 3H), 4.00 (s, 3H), 3.48-3.42 (m, 3H), 3.35-2.92 (m, 4H), 2.09-1.92 (m, 3H), 1.92-1.68 (m, 6H), 1.65-1.50 (m, 2H), 1.49-1.44 (m, 2H). |
| 51 | 605.3 | 1H NMR (400 MHz, DMSO-d6) δ 8.41 (t, J = 5.7 Hz, 1H), 7.97 (br. s, 3H), 7.76 (d, J = 8.2 Hz, 1H), 7.58 (s, 1H), 7.50 (ddd, J = 7.8, 5.7, 2.9 Hz, 1H), 7.48-7.35 (m, 4H), 7.23 (dd, J = 8.2, 1.4 Hz, 1H), 7.11 (s, 1H), 6.91 (d, J = 1.2 Hz, 1H), 4.49 (t, J = 6.4 Hz, 2H), 4.41-4.18 (m, 2H), 4.12 (s, 3H), 3.99 (s, 3H), 3.34-3.02 (m, 5H), 2.07-1.97 (m, 1H), 1.83-1.68 (m, 1H), 1.66-1.55 (m, 1H), 1.54-1.39 (m, 5H), 1.38-1.28 (m, 2H), 1.04-0.91 (m, 2H). |
| 52 | 606.3 | 1H NMR (400 MHz, DMSO-d6) δ 8.64 (t, J = 5.6 Hz, 1H), 8.55 (dd, J = 4.8, 1.6 Hz, 1H), 7.94 (br. s, 3H), 7.91 (dd, J = 7.9, 1.6 Hz, 1H), 7.79 (d, J = 8.2 Hz, 1H), 7.64 (s, 1H), 7.56 (dd, J = 7.9, 4.8 Hz, 1H), 7.40 (s, 1H), 7.24 (dd, J = 8.1, 1.4 Hz, 1H), 7.12 (s, 1H), 6.91 (d, J = 1.2 Hz, 1H), 4.53-4.45 (m, 2H), 4.12 (s, 3H), 3.99 (s, 3H), 3.81-3.37 (m, 2H buried under water peak), 3.33-3.06 (m, 5H), 2.08-1.96 (m, 1H), 1.83-1.68 (m, 1H), 1.65-1.37 (m, 8H), 1.12-0.99 (m, 2H). |
| 53 | 648.3 | 1H NMR (400 MHz, DMSO-d6) δ 9.33 (s, 1H), 8.49 (dd, J = 4.8, 1.8 Hz, 1H), 7.96 (s, 3H), 7.82 (dd, J = 7.6, 1.9 Hz, 1H), 7.78 (d, J = 8.2 Hz, 1H), 7.67 (s, 1H), 7.43 (dd, J = 7.6, 4.8 Hz, 1H), 7.40 (s, 1H), 7.18 (d, J = 8.2, 1.3 Hz, 1H), 7.10 (s, 1H), 6.92 (d, J = 1.1 Hz, 1H), 4.49 (t, J = 6.7 Hz, 2H), 4.43-4.33 (m, 2H), 4.12 (s, 3H), 3.99 (s, 3H), 3.33-3.03 (m, 3H), 2.08-1.99 (m, 1H), 1.82-1.70 (m, 1H), 1.64-1.54 (m, 2H), 1.49-1.41 (m, 2H), 1.40-1.31 (m, 2H), 1.10-0.98 (m, 2H), 1.01 (s, 6H), 0.92-0.84 (m, 2H), 0.81-0.70 (m, 2H). |
| 54 | 647.4 | 1H NMR (400 MHz, DMSO-d6) δ 7.96 (br. s, 3H), 7.94 (s, 1H), 7.82 (d, J = 8.1 Hz, 1H), 7.77 (dd, J = 8.0, 1.2 Hz, 1H), 7.64 (s, 1H), 7.44-7.32 (m, 3H), 7.26 (td, J = 7.5, 1.3 Hz, 1H), 7.14 (dd, J = 8.1, 1.3 Hz, 1H), 7.11 (s, 1H), 6.92 (d, J = 1.1 Hz, 1H), 4.51 (t, J = 6.4 Hz, 2H), 4.39-4.15 (m, 1H), 4.11 (s, 3H), 4.00 (s, 3H), 3.36-3.05 (m, 4H), 2.08-1.98 (m, 1H), 1.84-1.69 (m, 1H), 1.66-1.52 (m, 4H), 0.98 (s, 6H), 1.05-0.90 (m, 4H), 0.88-0.81 (m, 4H). |
| 55 | 631.6 | 1H NMR (400 MHz, DMSO-d6) δ 8.06-7.84 (m, 3H), 7.77-7.63 (m, 1H), 7.61-7.34 (m, 5H), 7.33-7.14 (m, 2H), 7.12-6.93 (m, 1H), 6.93-6.87 (m, 1H), 4.76-4.43 (m, 1H), 4.42-4.17 (m, 2H), 4.15-4.04 (m, 3H), 4.03-3.88 (m, 3H), 3.82-2.97 (m, 8H), 2.84-2.33 (m, 1H), 2.15-1.83 (m, 2H), 1.83-1.20 (m, 5H), 1.18-0.93 (m, 1H), 0.90-0.18 (m, 2H), 0.09--0.99 (m, 2H). |
| 56 | 625.3 | 1H NMR (400 MHz, DMSO-d6) δ 8.71 (t, J = 5.8 Hz, 1H), 8.37 (d, J = 5.1 Hz, 1H), 8.29 (d, J = 8.1 Hz, 1H), 7.96 (br. s, 3H), 7.58 (dd, J = 5.1, 1.2 Hz, 1H), 7.50 (d, J = 8.1 Hz, 1H), 7.42 (s, 1H), 7.18 (s, 1H), 6.93 (d, J = 1.2 Hz, 1H), 4.71 (t, J = 6.4 Hz, 2H), 4.39-4.01 (m, 2H), 4.15 (s, 3H), 4.00 (s, 3H), 3.36-3.04 (m, 5H), 2.10-1.98 (m, 1H), 1.80-1.72 (m, 1H), 1.66-1.51 (m, 2H), 1.48-1.27 (m, 6H), 1.08-0.97 (m, 2H). |
| 57 | 620.3 | 1H NMR (400 MHz, DMSO-d6) δ 8.19-7.99 (m, 1H), 8.12 (d, J = 8.0 Hz, 1H), 7.92 (br. s, 3H), 7.43-7.32 (m, 3H), 7.32-7.26 (m, 1H), 7.22 |

TABLE 3-continued

| Example | ES/MS m/z [M + H]+ | ¹H NMR |
|---|---|---|
| | | (d, J = 8.1 Hz, 1H), 7.13 (s, 1H), 6.92 (d, J = 1.2 Hz, 1H), 5.00-4.46 (m, 3H), 4.16 (s, 3H), 4.00 (s, 3H), 3.65-2.98 (m, 5H), 2.96-2.61 (m, 1H), 2.13 (s, 3H), 2.08-1.95 (m, 1H), 1.85-1.68 (m, 1H), 1.66-1.50 (m, 2H), 1.47-1.16 (m, 4H), 1.15-0.40 (m, 4H). |
| 58 | 586.3 | 1H NMR (400 MHz, DMSO-d6) δ 8.04 (d, J = 8.1 Hz, 1H), 7.96 (br. s, 3H), 7.64 (d, J = 8.0 Hz, 1H), 7.41 (s, 1H), 7.21 (d, J = 8.1 Hz, 1H), 7.03 (s, 1H), 6.91 (d, J = 1.1 Hz, 1H), 5.16 (p, J = 7.2 Hz, 1H), 4.68-4.54 (m, 2H), 4.10 (s, 3H), 3.99 (s, 3H), 3.94-3.45 (m, 3H), 3.33-3.04 (m, 2H), 2.10-1.97 (m, 1H), 1.89-1.43 (m, 7H), 1.53 (d, J = 7.1 Hz, 3H), 1.40-1.28 (m, 1H), 1.17 (s, 3H), 1.17-1.07 (m, 1H), 1.00 (s, 3H), 0.90-0.78 (m, 2H). |
| 59 | 616.4 | 1H NMR (400 MHz, DMSO-d6) δ 9.02-8.93 (m, 1H), 8.92-8.78 (m, 1H), 8.51 (d, J = 7.7 Hz, 1H), 8.05 (d, J = 8.1 Hz, 1H), 7.95 (d, J = 1.3 Hz, 1H), 7.81 (d, J = 7.4 Hz, 1H), 7.35 (d, J = 1.3 Hz, 1H), 7.19 (d, J = 8.1 Hz, 1H), 7.07 (s, 1H), 5.12 (p, J = 7.1 Hz, 1H), 4.87-4.76 (m, 1H), 4.47-4.36 (m, 1H), 4.35-4.22 (m, 1H), 4.14 (s, 3H), 4.02 (s, 3H), 3.96-3.84 (m, 1H), 3.35 (d, J = 10.8 Hz, 1H), 3.27 (d, J = 11.0 Hz, 1H), 2.82 (q, J = 9.9 Hz, 1H), 2.70 (q, J = 9.7 Hz, 1H), 2.20-2.12 (m, 1H), 1.92 (t, J = 12.1 Hz, 1H), 1.73-1.60 (m, 3H), 1.45 (d, J = 7.1 Hz, 3H), 1.54-1.26 (m, 4H), 1.21 (s, 3H), 1.18-0.98 (m, 3H), 0.95 (s, 3H). |
| 60 | 630.4 | 1H NMR (400 MHz, DMSO-d6) δ 8.10-7.90 (m, 4H), 7.82 (d, J = 7.4 Hz, 1H), 7.44 (s, 1H), 7.19 (d, J = 8.1 Hz, 1H), 7.03 (s, 1H), 6.94 (s, 1H), 5.12 (p, J = 7.1 Hz, 1H), 4.87-4.75 (m, 1H), 4.44-4.35 (m, 1H), 4.12 (s, 3H), 3.99 (s, 3H), 3.95-3.76 (m, 2H), 3.75-3.68 (m, 1H), 3.54 (s, 2H), 3.45-3.29 (m, 1H), 3.37 (s, 3H), 2.02-1.85 (m, 2H), 1.81-1.53 (m, 3H), 1.45 (d, J = 7.1 Hz, 3H), 1.42-1.26 (m, 5H), 1.21 (s, 3H), 1.17-0.99 (m, 2H), 0.95 (s, 3H). |
| 61 | 616.4 | 1H NMR (400 MHz, DMSO-d6) δ 8.04 (d, J = 8.1 Hz, 1H), 7.98 (br. s, 3H), 7.64 (d, J = 8.0 Hz, 1H), 7.44 (s, 1H), 7.21 (d, J = 8.1 Hz, 1H), 7.03 (s, 1H), 6.93 (s, 1H), 5.16 (p, J = 7.2 Hz, 1H), 4.68-4.54 (m, 2H), 4.10 (s, 3H), 3.98 (s, 3H), 3.90-3.31 (m, 6H), 3.36 (s, 3H), 2.03-1.86 (m, 1H), 1.86-1.45 (m, 5H), 1.53 (d, J = 7.1 Hz, 3H), 1.41-1.27 (m, 1H), 1.17 (s, 3H), 1.16-1.08 (m, 1H), 1.00 (s, 3H), 0.92-0.76 (m, 2H). |
| 62 | 628.4 | 1H NMR (400 MHz, DMSO-d6) δ 8.11 (d, J = 8.1 Hz, 1H), 8.08 (d, J = 7.9 Hz, 1H), 8.02 (br. s, 3H), 7.46 (s, 1H), 7.25 (d, J = 8.1 Hz, 1H), 7.06 (s, 1H), 6.94 (s, 1H), 5.27 (p, J = 7.0 Hz, 1H), 4.88-4.76 (m, 1H), 4.48-4.35 (m, 1H), 4.13 (s, 3H), 3.99 (s, 3H), 3.95-3.76 (m, 1H), 3.75-3.67 (m, 1H), 3.66-3.48 (m, 2H), 3.37 (s, 3H), 3.47-3.31 (m, 1H), 2.32-2.21 (m, 1H), 2.12-1.87 (m, 2H), 1.85-1.69 (m, 3H), 1.68-1.53 (m, 1H), 1.45 (d, J = 6.8 Hz, 3H), 1.50-1.33 (m, 2H), 1.31-0.99 (m, 4H), 0.99-0.89 (m, 1H), 0.65-0.56 (m, 1H), 0.52-0.42 (m, 1H). |
| 63 | 636.4 | 1H NMR (400 MHz, DMSO-d6) δ 9.89-9.18 (m, 2H), 8.70 (d, J = 7.4 Hz, 1H), 8.05 (d, J = 8.1 Hz, 1H), 7.98 (s, 1H), 7.80 (d, J = 7.4 Hz, 1H), 7.35 (s, 1H), 7.19 (d, J = 8.1 Hz, 1H), 7.07 (s, 1H), 5.12 (p, J = 7.1 Hz, 1H), 4.87-4.77 (m, 1H), 4.50-4.34 (m, 2H), 4.14 (s, 3H), 4.02 (s, 3H), 3.84-3.71 (m, 3H), 3.71-3.54 (m, 1H), 3.49-3.41 (m, 1H), 3.01 (t, J = 11.6 Hz, 1H), 2.64-2.53 (m, 1H), 2.41-2.21 (m, 1H), 1.92 (t, J = 12.2 Hz, 1H), 1.76-1.58 (m, 2H), 1.45 (d, J = 7.1 Hz, 3H), 1.51-1.27 (m, 3H), 1.21 (s, 3H), 1.18-1.00 (m, 2H), 0.95 (s, 3H). |
| 64 | 618.4 | 1H NMR (400 MHz, DMSO-d6) δ 9.30-9.02 (m, 2H), 8.60 (d, J = 7.7 Hz, 1H), 8.05 (d, J = 8.1 Hz, 1H), 7.98 (s, 1H), 7.80 (d, J = 7.4 Hz, 1H), 7.35 (s, 1H), 7.19 (d, J = 8.1 Hz, 1H), 7.07 (s, 1H), 5.25 (d, J = 45.2 Hz, 1H), 5.12 (p, J = 7.1 Hz, 1H), 4.87-4.76 (m, 1H), 4.55-4.34 (m, 2H), 4.14 (s, 3H), 4.27-3.80 (m, 2H), 4.01 (s, 3H), 3.53 (t, J = 12.7 Hz, 1H), 3.43-3.16 (m, 2H), 2.90 (q, J = 11.3 Hz, 1H), 2.36-2.23 (m, 1H), 2.11-1.86 (m, 2H), 1.76-1.60 (m, 2H), 1.45 (d, J = 7.1 Hz, 3H), 1.53-1.25 (m, 3H), 1.21 (s, 3H), 1.18-0.99 (m, 2H), 0.95 (s, 3H). |
| 65 | 656.3 | 1H NMR (400 MHz, DMSO-d6) δ 8.04 (d, J = 8.1 Hz, 1H), 7.83 (d, J = 7.5 Hz, 1H), 7.54 (br. s, 1H), 7.34 (d, J = 1.1 Hz, 1H), 7.18 (d, J = 8.2 Hz, 1H), 7.04 (s, 1H), 6.87 (d, J = 1.2 Hz, 1H), 5.12 (p, J = 7.1 Hz, 1H), 4.86-4.76 (m, 1H), 4.48-4.33 (m, 1H), 4.18 (dd, J = 10.4, 4.1 Hz, 1H), 4.11 (s, 3H), 4.14-3.79 (m, 7H), 3.99 (s, 3H), 3.22-3.12 (m, 1H), 1.92 (t, J = 12.2 Hz, 1H), 1.89-1.76 (m, 1H), 1.76-1.50 (m, 3H), 1.45 (d, J = 7.1 Hz, 3H), 1.42-1.23 (m, 5H), 1.20 (s, 3H), 1.17-0.97 (m, 2H), 0.94 (s, 3H). |
| 66 | 630.4 | 1H NMR (400 MHz, DMSO-d6) δ 8.04 (d, J = 8.1 Hz, 1H), 7.92 (br. s, 3H), 7.82 (d, J = 7.5 Hz, 1H), 7.39 (d, J = 1.1 Hz, 1H), 7.19 (d, J = 8.2 Hz, 1H), 7.03 (s, 1H), 6.90 (d, J = 1.3 Hz, 1H), 5.12 (p, J = 7.1 Hz, 1H), 4.86-4.76 (m, 1H), 4.71-4.21 (m, 3H), 4.46-4.35 (m, 1H), 4.11 (s, 3H), 3.99 (s, 3H), 3.60-3.51 (m, 2H), 3.22-3.08 (m, 1H), 3.07-2.91 (m, 2H), 1.92 (t, J = 11.9 Hz, 1H), 1.88-1.78 (m, 1H), 1.79-1.51 (m, 2H), 1.45 (d, J = 7.1 Hz, 3H), 1.51-1.26 (m, 7H), 1.21 (s, 3H), 1.17-0.98 (m, 2H), 0.94 (s, 3H). |
| 67 | 614.4 | 1H NMR (400 MHz, DMSO-d6) δ 8.04 (d, J = 8.1 Hz, 1H), 7.99 (br. s, 3H), 7.82 (d, J = 7.5 Hz, 1H), 7.46 (s, 1H), 7.19 (d, J = 8.2 Hz, 1H), 7.03 (s, 1H), 6.94 (d, J = 1.2 Hz, 1H), 5.12 (p, J = 7.1 Hz, 1H), 4.86-4.75 (m, |

TABLE 3-continued

| Example | ES/MS m/z [M + H]+ | ¹H NMR |
|---|---|---|
| | | 1H), 4.44-4.35 (m, 1H), 4.12 (s, 3H), 3.98 (s, 3H), 3.95-3.61 (m, 1H), 3.58-3.41 (m, 3H), 2.93-2.83 (m, 1H), 2.09-1.97 (m, 1H), 1.97-1.82 (m, 2H), 1.78-1.54 (m, 3H), 1.46-1.43 (m, 3H), 1.53-1.26 (m, 4H), 1.21 (s, 3H), 1.18-0.98 (m, 3H), 0.95 (s, 3H), 0.86 (s, 3H). |
| 68 | 614.4 | 1H NMR (400 MHz, DMSO-d6) δ 8.89 (br. d, J = 11.2 Hz, 1H), 8.72 (br. q, J = 11.3 Hz, 1H), 8.52 (d, J = 7.6 Hz, 1H), 8.05 (d, J = 8.1 Hz, 1H), 7.97 (d, J = 1.3 Hz, 1H), 7.81 (d, J = 7.5 Hz, 1H), 7.35 (d, J = 1.3 Hz, 1H), 7.19 (d, J = 8.1 Hz, 1H), 7.06 (s, 1H), 5.12 (p, J = 7.1 Hz, 1H), 4.87-4.76 (m, 1H), 4.47-4.36 (m, 1H), 4.29-4.16 (m, 1H), 4.13 (s, 3H), 4.01 (s, 3H), 3.41 (d, J = 11.6 Hz, 1H), 3.23 (d, J = 11.6 Hz, 1H), 2.69 (q, J = 11.2 Hz, 1H), 2.56-2.43 (m, 1H), 2.06-1.86 (m, 3H), 1.76-1.56 (m, 3H), 1.45 (d, J = 7.1 Hz, 3H), 1.54-1.22 (m, 5H), 1.21 (s, 3H), 1.18-1.01 (m, 2H), 0.97 (d, J = 6.6 Hz, 3H), 0.95 (s, 3H). |
| 69 | 618.4 | 1H NMR (400 MHz, DMSO-d6) δ 8.91 (br. d, J = 10.9 Hz, 1H), 8.86-8.73 (m, 1H), 8.67 (d, J = 7.8 Hz, 1H), 8.05 (d, J = 8.1 Hz, 1H), 8.03 (s, 1H), 7.81 (d, J = 7.4 Hz, 1H), 7.38 (s, 1H), 7.19 (d, J = 8.1 Hz, 1H), 7.07 (s, 1H), 5.13 (p, J = 7.1 Hz, 1H), 5.11-4.93 (m, 1H), 4.87-4.76 (m, 1H), 4.61-4.36 (m, 2H), 4.14 (s, 3H), 4.02 (s, 3H), 3.42-3.15 (m, 3H), 3.03 (q, J = 12.1, 11.6 Hz, 1H), 2.28-2.18 (m, 1H), 2.17-1.94 (m, 1H), 1.92 (t, J = 12.5 Hz, 1H), 1.77-1.57 (m, 2H), 1.45 (d, J = 7.1 Hz, 3H), 1.54-1.30 (m, 4H), 1.21 (s, 3H), 1.26-1.06 (m, 3H), 0.95 (s, 3H). |
| 70 | 600.4 | 1H NMR (400 MHz, DMSO-d6) δ 8.74-8.61 (m, 2H), 8.49 (d, J = 7.4 Hz, 1H), 8.05 (d, J = 8.1 Hz, 1H), 7.99 (s, 1H), 7.80 (d, J = 7.4 Hz, 1H), 7.35 (s, 1H), 7.19 (d, J = 8.1 Hz, 1H), 7.06 (s, 1H), 5.12 (p, J = 7.1 Hz, 1H), 4.87-4.76 (m, 1H), 4.46-4.37 (m, 1H), 4.27-4.17 (m, 1H), 4.14 (s, 3H), 4.01 (s, 3H), 3.41-3.33 (m, 1H), 3.23 (d, J = 12.5 Hz, 1H), 2.95-2.80 (m, 2H), 2.01-1.86 (m, 3H), 1.80-1.59 (m, 4H), 1.45 (d, J = 7.1 Hz, 3H), 1.54-1.27 (m, 4H), 1.21 (s, 3H), 1.27-1.00 (m, 3H), 0.95 (s, 3H). |
| 71 | 658.4 | 1H NMR (400 MHz, DMSO-d6) δ 9.56 (br. s, 1H), 9.14 (br. s, 1H), 8.40 (d, J = 7.1 Hz, 1H), 8.05 (d, J = 8.1 Hz, 1H), 8.01 (s, 1H), 7.79 (d, J = 7.4 Hz, 1H), 7.33 (s, 1H), 7.19 (d, J = 8.1 Hz, 1H), 7.07 (s, 1H), 5.12 (p, J = 7.1 Hz, 1H), 4.88-4.76 (m, 1H), 4.47-4.24 (m, 3H), 4.14 (s, 3H), 4.01 (s, 3H), 3.83 (s, 3H), 3.46-3.23 (m, 2H), 2.26-1.86 (m, 4H), 1.84-1.57 (m, 3H), 1.45 (d, J = 7.1 Hz, 3H), 1.54-1.26 (m, 5H), 1.21 (s, 3H), 1.17-1.00 (m, 2H), 0.95 (s, 3H). |
| 72 | 612.4 | 1H NMR (400 MHz, DMSO-d6) δ 8.85 (br. d, J = 11.2 Hz, 1H), 8.34 (d, J = 6.5 Hz, 1H), 8.28 (d, J = 10.1 Hz, 1H), 8.12 (d, J = 8.1 Hz, 1H), 8.09-8.01 (m, 2H), 7.36 (d, J = 1.3 Hz, 1H), 7.26 (d, J = 8.2 Hz, 1H), 7.10 (s, 1H), 5.27 (p, J = 6.9 Hz, 1H), 4.89-4.77 (m, 1H), 4.52-4.39 (m, 1H), 4.27-4.21 (m, 2H), 4.17 (s, 3H), 4.02 (s, 3H), 3.43-3.16 (m, 2H), 2.32-2.21 (m, 1H), 2.12-1.98 (m, 1H), 1.95-1.72 (m, 6H), 1.69-1.61 (m, 1H), 1.45 (d, J = 6.9 Hz, 3H), 1.49-1.38 (m, 2H), 1.28 (d, J = 6.6 Hz, 3H), 1.33-1.20 (m, 2H), 1.18-0.99 (m, 2H), 0.99-0.89 (m, 1H), 0.65-0.56 (m, 1H), 0.52-0.43 (m, 1H). |
| 73 | 614.4 | 1H NMR (400 MHz, DMSO-d6) δ 8.83 (br. d, J = 11.3 Hz, 1H), 8.33 (d, J = 6.5 Hz, 1H), 8.27 (br. d, J = 10.2 Hz, 1H), 8.08-8.01 (m, 2H), 7.80 (d, J = 7.4 Hz, 1H), 7.35 (s, 1H), 7.19 (d, J = 8.1 Hz, 1H), 7.07 (s, 1H), 5.12 (p, J = 7.1 Hz, 1H), 4.88-4.76 (m, 1H), 4.50-4.38 (m, 1H), 4.28-4.21 (m, 2H), 4.15 (s, 3H), 4.01 (s, 3H), 3.43-3.27 (m, 2H), 3.27-3.17 (m, 1H), 1.97-1.73 (m, 4H), 1.72-1.58 (m, 2H), 1.45 (d, J = 7.1 Hz, 3H), 1.43-1.30 (m, 6H), 1.28 (d, J = 6.6 Hz, 3H), 1.21 (s, 3H), 1.16-1.01 (m, 2H), 0.95 (s, 3H). |
| 74 | 616.3 | 1H NMR (400 MHz, DMSO-d6) δ 8.82 (br. s, 2H), 8.72 (d, J = 8.0 Hz, 1H), 8.12 (d, J = 8.1 Hz, 1H), 8.08 (d, J = 7.9 Hz, 1H), 8.01 (d, J = 1.3 Hz, 1H), 7.37 (d, J = 1.3 Hz, 1H), 7.26 (d, J = 8.2 Hz, 1H), 7.10 (s, 1H), 5.27 (p, J = 6.9 Hz, 1H), 4.98-4.75 (m, 2H), 4.52-4.37 (m, 2H), 4.16 (s, 3H), 4.03 (s, 3H), 3.49-3.35 (m, 2H), 3.14-2.91 (m, 2H), 2.42-2.22 (m, 2H), 2.10-2.02 (m, 1H), 2.00-1.58 (m, 3H), 1.45 (d, J = 6.9 Hz, 3H), 1.51-1.36 (m, 2H), 1.33-1.17 (m, 3H), 1.17-0.99 (m, 2H), 0.99-0.89 (m, 1H), 0.66-0.56 (m, 1H), 0.53-0.43 (m, 1H). |
| 75 | 618.4 | 1H NMR (400 MHz, DMSO-d6) δ 8.79 (br. s, 2H), 8.71 (d, J = 7.9 Hz, 1H), 8.05 (d, J = 8.1 Hz, 1H), 7.99 (d, J = 1.2 Hz, 1H), 7.80 (d, J = 7.4 Hz, 1H), 7.35 (d, J = 1.2 Hz, 1H), 7.19 (d, J = 8.1 Hz, 1H), 7.07 (s, 1H), 5.12 (p, J = 7.1 Hz, 1H), 4.97-4.76 (m, 2H), 4.52-4.33 (m, 2H), 4.14 (s, 3H), 4.02 (s, 3H), 3.49-3.35 (m, 2H), 3.14-2.93 (m, 2H), 2.42-2.29 (m, 1H), 1.92 (t, J = 11.8 Hz, 2H), 1.76-1.59 (m, 2H), 1.45 (d, J = 7.1 Hz, 3H), 1.53-1.32 (m, 4H), 1.21 (s, 3H), 1.17-1.00 (m, 3H), 0.95 (s, 3H). |
| 76 | 604.3 | 1H NMR (400 MHz, DMSO-d6) δ 8.86 (br. s, 2H), 8.71 (d, J = 8.0 Hz, 1H), 8.05 (d, J = 8.1 Hz, 1H), 7.99 (d, J = 1.3 Hz, 1H), 7.64 (d, J = 8.0 Hz, 1H), 7.35 (d, J = 1.3 Hz, 1H), 7.21 (d, J = 8.2 Hz, 1H), 7.08 (s, 1H), 5.17 (p, J = 7.2 Hz, 1H), 4.86 (dtd, J = 48.9, 9.4, 4.6 Hz, 1H), 4.70-4.55 (m, 2H), 4.49-4.37 (m, 1H), 4.14 (s, 3H), 4.02 (s, 3H), 3.49-3.35 (m, 2H), 3.16-2.91 (m, 2H), 2.42-2.28 (m, 1H), 2.01-1.84 (m, 1H), 1.85-1.63 (m, 3H), 1.63-1.47 (m, 1H), 1.54 (d, J = 7.1 Hz, 3H), 1.42-1.30 (m, 1H), 1.18 (s, 3H), 1.18-1.09 (m, 1H), 1.01 (s, 3H), 0.87 (s, 2H). |

TABLE 3-continued

| Example | ES/MS m/z [M + H]+ | ¹H NMR |
|---|---|---|
| 77 | 612.4 | 1H NMR (400 MHz, DMSO-d6) δ 8.85 (br. s, 2H), 8.57 (d, J = 7.4 Hz, 1H), 8.11 (d, J = 8.1 Hz, 1H), 8.08 (d, J = 7.9 Hz, 1H), 7.99 (d, J = 1.3 Hz, 1H), 7.36 (d, J = 1.3 Hz, 1H), 7.25 (d, J = 8.1 Hz, 1H), 7.09 (s, 1H), 5.27 (p, J = 6.9 Hz, 1H), 4.88-4.76 (m, 1H), 4.49-4.38 (m, 1H), 4.37-4.27 (m, 1H), 4.16 (s, 3H), 4.02 (s, 3H), 3.42-3.32 (m, 1H), 3.27-3.08 (m, 3H), 2.33-2.22 (m, 1H), 2.13-1.96 (m, 2H), 1.94-1.69 (m, 4H), 1.68-1.53 (m, 3H), 1.45 (d, J = 6.9 Hz, 3H), 1.51-1.35 (m, 2H), 1.34-1.00 (m, 5H), 0.99-0.89 (m, 1H), 0.65-0.56 (m, 1H), 0.52-0.43 (m, 1H). |
| 78 | 614.4 | 1H NMR (400 MHz, DMSO-d6) δ 8.81 (br. t, J = 4.9 Hz, 2H), 8.55 (d, J = 7.4 Hz, 1H), 8.05 (d, J = 8.1 Hz, 1H), 7.97 (d, J = 1.2 Hz, 1H), 7.80 (d, J = 7.4 Hz, 1H), 7.35 (d, J = 1.2 Hz, 1H), 7.19 (d, J = 8.1 Hz, 1H), 7.06 (s, 1H), 5.12 (p, J = 7.1 Hz, 1H), 4.87-4.76 (m, 1H), 4.48-4.24 (m, 2H), 4.14 (s, 3H), 4.01 (s, 3H), 3.41-3.31 (m, 1H), 3.25-3.09 (m, 4H), 2.10-1.51 (m, 7H), 1.45 (d, J = 7.1 Hz, 3H), 1.51-1.26 (m, 4H), 1.21 (s, 3H), 1.16-1.01 (m, 3H), 0.95 (s, 3H). |
| 79 | 626.4 | 1H NMR (400 MHz, DMSO-d6) δ 9.03 (br. s, 1H), 8.49 (br. s, 1H), 8.04 (d, J = 8.1 Hz, 1H), 7.81 (d, J = 7.5 Hz, 1H), 7.45 (s, 1H), 7.18 (d, J = 8.2 Hz, 1H), 7.02 (s, 1H), 6.94 (d, J = 1.1 Hz, 1H), 5.12 (p, J = 7.1 Hz, 1H), 4.86-4.76 (m, 1H), 4.43-4.33 (m, 1H), 4.11 (s, 3H), 3.98 (s, 3H), 3.85-3.48 (m, 4H), 3.30-3.15 (m, 2H), 2.98-2.88 (m, 1H), 2.17-2.05 (m, 1H), 1.92 (t, J = 12.3 Hz, 1H), 1.88-1.55 (m, 4H), 1.45 (d, J = 7.1 Hz, 3H), 1.54-1.27 (m, 6H), 1.21 (s, 3H), 1.13-0.98 (m, 3H), 0.94 (s, 3H). |
| 80 | 626.4 | 1H NMR (400 MHz, DMSO-d6) δ 9.12-8.77 (m, 1H), 8.62-8.41 (m, 1H), 8.04 (d, J = 8.0 Hz, 1H), 7.82 (d, J = 7.5 Hz, 1H), 7.62-7.51 (m, 1H), 7.19 (d, J = 8.1 Hz, 1H), 7.05-6.98 (m, 2H), 5.13 (p, J = 7.3 Hz, 1H), 4.86-4.75 (m, 1H), 4.42-4.26 (m, 1H), 4.11 (s, 3H), 3.99 (s, 3H), 3.90-3.44 (m, 4H), 3.33-3.14 (m, 1H), 3.03-2.84 (m, 1H), 2.75-2.56 (m, 1H), 1.92 (t, J = 12.6 Hz, 1H), 1.84-1.54 (m, 7H), 1.45 (d, J = 7.1 Hz, 3H), 1.49-1.30 (m, 4H), 1.21 (s, 3H), 1.27-1.00 (m, 3H), 0.95 (s, 3H). |
| 81 | 626.4 | 1H NMR (400 MHz, DMSO-d6) δ 9.02 (br. s, 1H), 8.47 (br. s, 1H), 8.04 (d, J = 8.0 Hz, 1H), 7.81 (d, J = 7.4 Hz, 1H), 7.45 (s, 1H), 7.18 (d, J = 8.2 Hz, 1H), 7.03 (s, 1H), 6.94 (d, J = 1.2 Hz, 1H), 5.12 (p, J = 7.2 Hz, 1H), 4.87-4.76 (m, 1H), 4.48-4.36 (m, 1H), 4.11 (s, 3H), 3.99 (s, 3H), 3.84-3.51 (m, 4H), 3.45-3.03 (m, 3H), 2.17-2.04 (m, 1H), 1.92 (t, J = 11.9 Hz, 1H), 1.88-1.51 (m, 4H), 1.45 (d, J = 7.1 Hz, 3H), 1.54-1.25 (m, 6H), 1.21 (s, 3H), 1.17-0.98 (m, 3H), 0.94 (s, 3H). |
| 82 | 630.4 | 1H NMR (400 MHz, DMSO-d6) δ 8.68 (br. s, 2H), 8.35 (d, J = 7.9 Hz, 1H), 8.05 (d, J = 8.1 Hz, 1H), 8.02 (s, 1H), 7.81 (d, J = 7.4 Hz, 1H), 7.37 (s, 1H), 7.19 (d, J = 8.1 Hz, 1H), 7.07 (s, 1H), 5.12 (p, J = 7.1 Hz, 1H), 4.88-4.76 (m, 1H), 4.51-4.37 (m, 2H), 4.14 (s, 3H), 4.02 (s, 3H), 3.71-3.64 (m, 1H), 3.34 (s, 3H), 3.28-3.07 (m, 3H), 3.07-2.92 (m, 1H), 2.21-2.11 (m, 1H), 1.92 (t, J = 12.2 Hz, 1H), 1.87-1.75 (m, 1H), 1.71-1.60 (m, 2H), 1.45 (d, J = 7.0 Hz, 3H), 1.53-1.27 (m, 5H), 1.21 (s, 3H), 1.16-1.03 (m, 2H), 0.95 (s, 3H). |
| 83 | 592.3 | 1H NMR (400 MHz, DMSO-d6) δ 8.24-8.16 (m, 2H), 8.11 (br. s, 3H), 7.95 (d, J = 6.8 Hz, 1H), 7.60 (s, 1H), 7.40 (d, J = 8.1 Hz, 1H), 7.15-7.09 (m, 2H), 7.05 (s, 1H), 4.69 (t, J = 6.0 Hz, 2H), 4.22 (t, J = 5.3 Hz, 2H), 4.16 (s, 3H), 4.02 (s, 3H), 3.75 (s, 1H), 2.38-2.27 (m, 2H), 1.91-1.76 (m, 6H), 1.67-1.53 (m, 6H), 1.35 (dd, J = 12.9, 4.4 Hz, 1H), 1.27-1.16 (m, 2H). |
| 84 | 619.3 | 1H NMR (400 MHz, DMSO-d6) δ 10.32 (s, 1H), 8.47 (d, J = 4.9 Hz, 1H), 8.23 (d, J = 8.1 Hz, 1H), 8.07 (br. s, 3H), 7.91 (d, J = 7.6 Hz, 1H), 7.59 (s, 1H), 7.43-7.34 (m, 2H), 7.13 (s, 1H), 7.04 (s, 1H), 4.73 (t, J = 5.6 Hz, 2H), 4.46-4.41 (m, 3H), 4.15 (s, 3H), 4.01 (s, 3H), 2.40-2.23 (m, 1H), 2.19-2.12 (m, 2H), 1.85-1.80 (m, 3H), 1.66-1.59 (m, 1H), 1.41-1.23 (m, 8H), 0.89-0.84 (m, 2H). |
| 85 | 606.3 | 1H NMR (400 MHz, DMSO-d6) δ 8.26-8.18 (m, 2H), 8.08 (br. s, 3H), 7.84 (d, J = 7.3 Hz, 1H), 7.61 (s, 1H), 7.36 (d, J = 8.0 Hz, 1H), 7.15 (s, 1H), 7.14-7.08 (m, 1H), 7.05 (s, 1H), 4.71 (t, J = 6.7 Hz, 2H), 4.62-4.24 (m, 2H), 4.40 (t, J = 5.4 Hz, 2H), 4.16 (s, 3H), 4.02 (s, 3H), 3.82-3.69 (m, 1H), 2.39-2.19 (m, 2H), 1.91-1.42 (m, 12H), 1.34 (dd, J = 13.3, 4.2 Hz, 1H), 1.13-1.02 (m, 2H). |
| 86 | 620.3 | 1H NMR (400 MHz, DMSO-d6) δ 8.27-8.17 (m, 2H), 8.08 (br. s, 3H), 7.76 (d, J = 7.1 Hz, 1H), 7.61 (s, 1H), 7.27 (d, J = 8.1 Hz, 1H), 7.14-7.07 (m, 2H), 7.05 (s, 1H), 4.56 (t, J = 7.4 Hz, 2H), 4.49-4.38 (m, 2H), 4.30 (t, J = 5.3 Hz, 2H), 4.15 (s, 3H), 4.02 (s, 3H), 3.83-3.68 (m, 1H), 2.39-2.23 (m, 2H), 1.91-1.57 (m, 8H), 1.40-1.29 (m, 7H), 1.26-1.13 (m, 2H). |
| 87 | 618.3 | 1H NMR (400 MHz, DMSO-d6) δ 9.53 (s, 1H), 8.27 (d, J = 8.0 Hz, 1H), 8.14-8.02 (m, 4H), 7.60 (s, 1H), 7.47 (d, J = 7.7 Hz, 1H), 7.45-7.36 (m, 2H), 7.24 (t, J = 7.6 Hz, 1H), 7.17 (s, 1H), 7.05 (s, 1H), 4.75-4.65 (m, 2H), 4.57-4.28 (m, 1H), 4.14 (s, 3H), 4.02 (s, 3H), 3.95-3.52 (m, 2H), 2.27-2.21 (m, 2H), 1.94-1.73 (m, 4H), 1.67-1.59 (m, 1H), 1.58-1.41 (m, 5H), 1.39-1.29 (m, 1H), 1.19-1.04 (m, 3H). |

TABLE 3-continued

| Example | ES/MS m/z [M + H]+ | ¹H NMR |
|---|---|---|
| 88 | 618.3 | 1H NMR (400 MHz, DMSO-d6) δ 9.99 (s, 1H), 8.46 (br. d, J = 4.8 Hz, 1H), 8.10 (br. s, 3H), 7.93 (d, J = 7.7 Hz, 1H), 7.80 (d, J = 7.9 Hz, 1H), 7.65 (s, 1H), 7.57 (s, 1H), 7.48-7.39 (m, 1H), 7.20 (d, J = 8.2 Hz, 1H), 7.12 (s, 1H), 7.03 (s, 1H), 5.01-4.31 (m, 2H), 4.58-4.50 (m, 2H), 4.11 (s, 3H), 4.01 (s, 3H), 3.81-3.67 (m, 1H), 2.38-2.18 (m, 3H), 1.90-1.56 (m, 5H), 1.51-1.27 (m, 7H), 1.07-0.95 (m, 2H). |
| 89 | 633.3 | 1H NMR (400 MHz, DMSO-d6) δ 10.44 (s, 1H), 8.52-8.46 (m, 1H), 8.27 (d, J = 8.1 Hz, 1H), 8.19-8.00 (m, 4H), 7.60 (s, 1H), 7.52 (d, J = 8.2 Hz, 1H), 7.43 (t, J = 6.5 Hz, 1H), 7.16 (s, 1H), 7.05 (s, 1H), 4.69-4.61 (m, 2H), 4.56-4.16 (m, 2H), 4.15 (s, 3H), 4.02 (s, 3H), 3.75 (s, 1H), 2.39-2.21 (m, 3H), 1.86-1.81 (m, 3H), 1.68-1.54 (m, 3H), 1.44-1.13 (m, 5H), 1.11-0.83 (m, 5H). |
| 90 | 619.3 | 1H NMR (400 MHz, DMSO-d6) δ 10.45 (s, 1H), 8.93 (s, 1H), 8.72 (d, J = 6.4 Hz, 1H), 8.66 (d, J = 7.0 Hz, 1H), 8.41 (d, J = 8.3 Hz, 1H), 8.15 (s, 3H), 7.66 (d, J = 8.4 Hz, 1H), 7.60 (s, 1H), 7.24 (s, 1H), 7.06 (s, 1H), 4.67 (t, J = 6.3 Hz, 2H), 4.60-4.15 (m, 2H), 4.14 (s, 3H), 4.02 (s, 3H), 3.77-3.72 (m, 1H), 2.46-2.39 (m, 1H), 2.38-2.27 (m, 1H), 1.91-1.75 (m, 4H), 1.73-1.47 (m, 8H), 1.35 (d, J = 12.6 Hz, 1H), 1.29-1.24 (m, 2H). |
| 91 | 619.3 | 1H NMR (400 MHz, DMSO-d6) δ 8.64-8.58 (m, 1H), 8.49 (t, J = 6.0 Hz, 1H), 8.23 (d, J = 8.1 Hz, 1H), 8.08 (s, 3H), 8.01 (d, J = 7.9 Hz, 1H), 7.65-7.56 (m, 2H), 7.46 (d, J = 8.4 Hz, 1H), 7.15 (s, 1H), 7.04 (s, 1H), 4.69-4.64 (m, 2H), 4.47-4.42 (m, 1H), 4.16 (s, 3H), 4.02 (s, 3H), 3.82-3.63 (m, 2H), 3.20 (s, 2H), 2.35-2.30 (m, 1H), 1.85-1.80 (m, 4H), 1.66-1.59 (m, 1H), 1.48 (s, 4H), 1.44-1.39 (m, 2H), 1.34 (d, J = 13.2 Hz, 1H), 1.14-1.08 (m, 2H). |
| 92 | 605.3 | 1H NMR (400 MHz, DMSO-d6) δ 10.66 (s, 1H), 8.43 (s, 1H), 8.24 (d, J = 8.8 Hz, 1H), 8.14-8.04 (m, 4H), 7.60 (s, 1H), 7.53 (d, J = 9.0 Hz, 1H), 7.40-7.32 (m, 1H), 7.15 (s, 1H), 7.04 (s, 1H), 4.70 (s, 2H), 4.65-4.29 (m, 2H), 4.15 (s, 3H), 4.01 (s, 3H), 3.88-3.70 (m, 3H), 2.17-2.10 (m, 2H), 1.91-1.69 (m, 5H), 1.64-1.59 (m, 1H), 1.43 (s, 2H), 1.34 (d, J = 13.4 Hz, 1H), 0.96-0.91 (m, 2H). |
| 93 | 632.3 | 1H NMR (400 MHz, DMSO-d6) δ 10.61 (s, 1H), 8.38-8.31 (m, 1H), 8.30 (d, J = 8.2 Hz, 1H), 8.09 (s, 3H), 7.67 (d, J = 7.8 Hz, 1H), 7.61 (s, 1H), 7.62-7.56 (m, 1H), 7.42 (t, J = 7.6 Hz, 1H), 7.26-7.21 (m, 1H), 7.17 (s, 1H), 7.05 (s, 1H), 4.65-4.60 (m, 2H), 4.56-4.33 (m, 2H), 4.16 (s, 3H), 4.02 (s, 3H), 3.90-3.55 (m, 1H), 2.34-2.28 (m, 3H), 1.89-1.69 (m, 5H), 1.64-1.59 (m, 3H), 1.39-1.29 (m, 5H), 1.26-1.21 (m, 2H). |
| 94 | 617.3 | 1H NMR (400 MHz, DMSO-d6) δ 9.17 (s, 1H), 8.13 (s, 3H), 7.80 (d, J = 8.1 Hz, 1H), 7.63-7.52 (m, 3H), 7.40 (dd, J = 7.5, 1.8 Hz, 1H), 7.35 (td, J = 7.6, 1.8 Hz, 1H), 7.28 (td, J = 7.4, 1.5 Hz, 1H), 7.18 (dd, J = 8.1, 1.3 Hz, 1H), 7.12 (s, 1H), 7.03 (s, 1H), 4.54-4.48 (m, 2H), 4.58-4.33 (m, 2H), 4.10 (s, 3H), 4.03-3.98 (m, 3H), 3.83-3.70 (m, 1H), 2.38-2.22 (m, 3H), 1.91-1.79 (m, 3H), 1.69-1.39 (m, 8H), 1.35 (dd, J = 12.9, 4.4 Hz, 1H), 1.20-1.11 (m, 2H). |
| 95 | 619.3 | 1H NMR (400 MHz, DMSO-d6) δ 9.80 (s, 1H), 9.16 (s, 1H), 8.51 (d, J = 5.2 Hz, 1H), 8.34 (d, J = 8.1 Hz, 1H), 8.09 (s, 3H), 7.65 (d, J = 5.2 Hz, 1H), 7.60 (s, 1H), 7.52 (d, J = 8.1 Hz, 1H), 7.21 (s, 1H), 7.05 (s, 1H), 4.68 (t, J = 6.2 Hz, 2H), 4.56-4.32 (m, 2H), 4.14 (s, 3H), 4.02 (s, 3H), 3.82-3.57 (m, 1H), 2.33-2.25 (m, 3H), 1.93-1.72 (m, 4H), 1.70-1.38 (m, 6H), 1.34 (dd, J = 12.9, 4.4 Hz, 1H), 1.20-1.07 (m, 2H). |
| 96 | 591.3 | 1H NMR (400 MHz, DMSO-d6) δ 10.84 (br. s, 1H), 8.67 (d, J = 7.6 Hz, 1H), 8.40 (d, J = 8.4 Hz, 1H), 8.19 (s, 3H), 8.10 (dd, J = 6.1, 1.5 Hz, 1H), 7.99 (d, J = 8.6 Hz, 1H), 7.63-7.57 (m, 1H), 7.22 (s, 1H), 7.08-7.00 (m, 2H), 4.54 (t, J = 7.8 Hz, 2H), 4.48-4.25 (m, 2H), 4.18 (s, 3H), 4.02 (s, 3H), 3.77-3.72 (m, 1H), 3.46 (s, 2H), 2.38-2.23 (m, 1H), 2.03-1.96 (m, 2H), 1.90-1.72 (m, 7H), 1.69-1.56 (m, 1H), 1.51-1.41 (m, 2H), 1.36 (dd, J = 12.8, 4.4 Hz, 1H). |
| 97 | 617.3 | 1H NMR (400 MHz, DMSO-d6) δ 8.40 (t, J = 5.7 Hz, 1H), 8.12 (br. s, 3H), 7.76 (d, J = 8.2 Hz, 1H), 7.61-7.55 (m, 2H), 7.53-7.47 (m, 1H), 7.47-7.35 (m, 3H), 7.23 (dd, J = 8.1, 1.4 Hz, 1H), 7.11 (s, 1H), 7.03 (d, J = 1.3 Hz, 1H), 4.50 (t, J = 6.4 Hz, 2H), 4.44-4.17 (m, 2H), 4.12 (s, 3H), 4.01 (s, 3H), 3.82-3.63 (m, 1H), 3.21-3.12 (m, 2H), 2.39-2.25 (m, 1H), 1.90-1.72 (m, 3H), 1.70-1.57 (m, 1H), 1.55-1.39 (m, 4H), 1.39-1.25 (m, 3H), 1.03-0.92 (m, 2H). |
| 98 | 618.3 | 1H NMR (400 MHz, DMSO-d6) δ 8.64 (t, J = 5.7 Hz, 1H), 8.55 (dd, J = 4.8, 1.6 Hz, 1H), 8.08 (br. s, 3H), 7.91 (dd, J = 7.9, 1.6 Hz, 1H), 7.79 (d, J = 8.2 Hz, 1H), 7.65 (s, 1H), 7.58 (s, 1H), 7.57-7.52 (m, 1H), 7.24 (dd, J = 8.1, 1.4 Hz, 1H), 7.13 (s, 1H), 7.03 (d, J = 1.2 Hz, 1H), 4.50 (t, J = 6.5 Hz, 2H), 4.60-4.35 (m, 1H), 4.12 (s, 3H), 4.01 (s, 3H), 3.87-3.44 (m, 2H buried under water peak), 3.23-3.18 (m, 2H), 2.38-2.25 (m, 1H), 1.92-1.73 (m, 3H), 1.69-1.38 (m, 7H), 1.34 (dd, J = 12.8, 4.4 Hz, 1H), 1.10-0.98 (m, 2H). |
| 99 | 660.4 | 1H NMR (400 MHz, DMSO-d6) δ 9.33 (s, 1H), 8.49 (dd, J = 4.8, 1.8 Hz, 1H), 8.11 (s, 3H), 7.82 (dd, J = 7.6, 1.9 Hz, 1H), 7.78 (d, J = 8.2 Hz, 1H), 7.67 (s, 1H), 7.58 (s, 1H), 7.44 (dd, J = 7.6, 4.8 Hz, 1H), 7.18 (dd, J = 8.2, 1.3 Hz, 1H), 7.10 (s, 1H), 7.04 (s, 1H), 4.49 (t, J = 6.7 Hz, 2H), 4.43- |

TABLE 3-continued

| Example | ES/MS m/z [M + H]+ | ¹H NMR |
|---|---|---|
|  |  | 4.27 (m, 1H), 4.12 (s, 3H), 4.01 (s, 3H), 3.82-3.66 (m, 2H), 2.39-2.25 (m, 1H), 1.91-1.74 (m, 3H), 1.69-1.57 (m, 1H), 1.49-1.41 (m, 2H), 1.39-1.30 (m, 3H), 1.10-0.98 (m, 2H), 1.01 (s, 6H), 0.97-0.84 (m, 2H), 0.82-0.69 (m, 2H). |
| 100 | 659.3 | 1H NMR (400 MHz, DMSO-d6) δ 8.10 (br. s, 3H), 7.94 (s, 1H), 7.83 (d, J = 8.2 Hz, 1H), 7.77 (dd, J = 8.1, 1.2 Hz, 1H), 7.64 (s, 1H), 7.59 (s, 1H), 7.39 (td, J = 7.7, 1.7 Hz, 1H), 7.35 (dd, J = 7.6, 1.7 Hz, 1H), 7.26 (td, J = 7.5, 1.3 Hz, 1H), 7.15 (dd, J = 8.1, 1.3 Hz, 1H), 7.11 (s, 1H), 7.04 (d, J = 1.2 Hz, 1H), 4.51 (t, J = 6.3 Hz, 2H), 4.47-4.33 (m, 1H), 4.11 (s, 3H), 4.01 (s, 3H), 3.84-3.43 (m, 2H), 2.37-2.27 (m, 1H), 1.92-1.75 (m, 3H), 1.69-1.49 (m, 4H), 1.34 (dd, J = 12.8, 4.4 Hz, 1H), 0.98 (s, 6H), 1.06-0.90 (m, 3H), 0.87-0.80 (m, 4H). |
| 101 | 643.5 | 1H NMR (400 MHz, DMSO-d6) δ 8.18-8.07 (m, 3H), 7.79-7.36 (m, 6H), 7.34-7.14 (m, 2H), 7.13-6.92 (m, 2H), 4.82-4.47 (m, 2H), 4.46-4.27 (m, 2H), 4.24-4.06 (m, 3H), 4.05-3.86 (m, 3H), 3.85-3.41 (m, 5H), 3.16-2.24 (m, 2H), 1.98-1.73 (m, 4H), 1.74-1.21 (m, 3H), 1.16-0.96 (m, 1H), 0.89-0.46 (m, 2H), 0.31-0.13 (m, 1H), 0.09--1.10 (m, 2H). |
| 102 | 598.4 | 1H NMR (400 MHz, DMSO-d6) δ 8.13 (br. s, 3H), 8.04 (d, J = 8.1 Hz, 1H), 7.64 (d, J = 8.0 Hz, 1H), 7.58 (s, 1H), 7.21 (d, J = 8.2 Hz, 1H), 7.06-7.01 (m, 2H), 5.16 (p, J = 7.2 Hz, 1H), 4.69-4.55 (m, 2H), 4.54-4.29 (m, 2H), 4.10 (s, 3H), 4.00 (s, 3H), 4.07-3.66 (m, 2H), 2.39-2.26 (m, 1H), 1.90-1.68 (m, 6H), 1.68-1.58 (m, 2H), 1.53 (d, J = 7.1 Hz, 3H), 1.57-1.42 (m, 1H), 1.39-1.27 (m, 2H), 1.17 (s, 3H), 1.17-1.08 (m, 1H), 1.00 (s, 3H), 0.91-0.76 (m, 2H). |
| 103 | 658.4 | 1H NMR (400 MHz, DMSO-d6) δ 8.04 (d, J = 8.1 Hz, 1H), 7.97 (br. s, 3H), 7.82 (d, J = 7.4 Hz, 1H), 7.44 (s, 1H), 7.19 (d, J = 8.1 Hz, 1H), 7.03 (s, 1H), 6.93 (s, 1H), 5.12 (p, J = 7.1 Hz, 1H), 4.86-4.75 (m, 1H), 4.44-4.33 (m, 1H), 4.28-3.84 (m, 2H), 4.11 (s, 3H), 3.99 (s, 3H), 3.83-3.75 (m, 1H), 3.60-3.31 (m, 5H), 1.92 (t, J = 11.9 Hz, 2H), 1.82-1.51 (m, 4H), 1.45 (d, J = 7.1 Hz, 3H), 1.52-1.27 (m, 5H), 1.21 (s, 3H), 1.26-1.00 (m, 3H), 0.95 (s, 3H), 0.91 (t, J = 7.4 Hz, 3H). |
| 104 | 644.4 | 1H NMR (400 MHz, DMSO-d6) δ 8.04 (d, J = 8.1 Hz, 1H), 7.96 (br. s, 3H), 7.82 (d, J = 7.4 Hz, 1H), 7.44 (s, 1H), 7.19 (d, J = 8.1 Hz, 1H), 7.03 (s, 1H), 6.93 (s, 1H), 5.12 (p, J = 7.1 Hz, 1H), 4.88-4.74 (m, 1H), 4.45-4.33 (m, 1H), 4.11 (s, 3H), 4.26-3.86 (m, 1H), 3.99 (s, 3H), 3.84-3.76 (m, 1H), 3.67-3.32 (m, 6H), 1.92 (t, J = 11.9 Hz, 2H), 1.81-1.50 (m, 3H), 1.45 (d, J = 7.1 Hz, 3H), 1.42-1.26 (m, 5H), 1.23-1.16 (m, 6H), 1.15-1.00 (m, 2H), 0.95 (s, 3H). |
| 105 | 644.4 | 1H NMR (400 MHz, DMSO-d6) δ 8.60 (br. s, 1H), 8.50 (br. s, 1H), 8.04 (d, J = 8.1 Hz, 1H), 7.81 (d, J = 7.4 Hz, 1H), 7.43 (d, J = 1.1 Hz, 1H), 7.19 (d, J = 8.1 Hz, 1H), 7.03 (s, 1H), 6.91 (d, J = 1.2 Hz, 1H), 5.12 (p, J = 7.2 Hz, 1H), 4.86-4.76 (m, 1H), 4.44-4.34 (m, 1H), 4.11 (s, 3H), 3.99 (s, 3H), 4.23-3.74 (m, 2H), 3.89-3.84 (m, 1H), 3.54-3.44 (m, 2H), 3.38 (s, 3H), 3.43-3.25 (m, 1H), 2.66-2.54 (m, 3H), 2.08-1.96 (m, 1H), 1.92 (t, J = 12.3 Hz, 1H), 1.74-1.56 (m, 3H), 1.45 (d, J = 7.1 Hz, 3H), 1.50-1.25 (m, 4H), 1.21 (s, 3H), 1.17-0.98 (m, 3H), 0.94 (s, 3H). |
| 106 | 586.4 | 1H NMR (400 MHz, DMSO-d6) δ 8.01-7.85 (m, 4H), 7.58 (d, J = 8.2 Hz, 1H), 7.29 (s, 1H), 7.14 (d, J = 8.1 Hz, 1H), 6.59 (s, 1H), 6.36 (s, 1H), 5.16 (dd, J = 15.2, 7.7 Hz, 1H), 4.58-4.48 (m, 2H), 4.08 (s, 3H), 3.34-3.10 (m, 4H), 2.78 (s, 3H), 2.09-1.96 (m, 1H), 1.90-1.41 (m, 10H), 1.41-1.27 (m, 1H), 1.19-1.07 (m, 4H), 1.00 (s, 3H), 0.94-0.66 (m, 2H). |
| 107 | 612.4 | Exists as a 6:4 ratio of rotamers. 1H NMR (400 MHz, DMSO-d6) δ 8.15 (d, J = 8.2 Hz, 0.4H), 8.00 (d, J = 8.0 Hz, 0.6H), 7.98-7.87 (m, 3H), 7.42 (s, 1H), 7.19 (d, J = 8.1 Hz, 0.6H), 7.17 (d, J = 8.2 Hz, 0.4H), 7.10 (s, 0.4H), 6.99 (s, 0.6H), 6.92 (s, 0.4H), 6.91 (s, 0.6H), 5.16-5.08 (m, 1H), 4.88-4.76 (m, 0.4H), 4.73-4.63 (m, 0.6H), 4.54-4.45 (m, 2H), 4.12 (s, 1.2H), 4.10 (s, 1.8H), 3.99 (s, 3H), 3.93-3.83 (m, 1H), 3.80-3.62 (m, 2H), 3.34-3.02 (m, 3H), 2.63-2.53 (m, 2H)2.38-2.23 (m, 2H), 2.12-0.71 (m, 17H), 0.63-0.49 (m, 1H). |
| 108 | 600.3 | Exists as a 7:3 mixture of rotamers. 1H NMR (400 MHz, DMSO-d6) δ 8.14 (d, J = 8.0 Hz, 0.3H), 8.03 (d, J = 8.1 Hz, 0.7H), 7.99-7.86 (m, 3H), 7.42 (s, 1H), 7.25 (d, J = 8.1 Hz, 0.3H), 7.14 (d, J = 8.1 Hz, 0.7H), 7.11 (s, 0.3H), 6.99 (s, 0.7H), 6.91 (s, 1H), 5.37 (d, J = 7.7 Hz, 0.3H), 5.28-5.23 (m, 0.7H), 4.90-4.76 (m, 0.3H), 4.69-4.48 (m, 1.7H), 4.42-4.29 (m, 1H), 4.12 (s, 3H), 4.02-3.91 (m, 4H), 3.82-3.51 (m, 5H), 3.41-2.90 (m, 6H), 2.40-1.34 (m, 11H), 1.30-1.09 (m, 1H). |
| 109 | 586.3 | Exists as a 1:1 mixture of rotamers. 1H NMR (400 MHz, DMSO-d6) δ 8.16 (d, J = 8.2 Hz, 0.5H), 8.05 (d, J = 8.1 Hz, 0.5H), 8.01-7.86 (m, 3H), 7.42 (s, 1H), 7.29 (d, J = 8.2 Hz, 0.5H), 7.19 (d, J = 8.1 Hz, 0.5H), 7.10 (s, 0.5H), 7.02 (s, 0.5H), 6.91 (d, J = 2.7 Hz, 1H), 5.28-5.19 (m, 1H), 4.70-4.59 (m, 1H), 4.53-4.31 (m, 3H), 4.13 (s, 1.5H), 4.11 (s, 1.5H), 4.07-3.96 (m, 4H), 3.93-3.39 (m, 5H), 3.33-3.05 (m, 3H), 2.47-2.30 (m, 1H), 2.08-1.11 (m, 10H), 1.05-0.90 (m, 1H). |

TABLE 3-continued

| Example | ES/MS m/z [M + H]+ | 1H NMR |
|---|---|---|
| 110 | 586.3 | 1H NMR (400 MHz, DMSO-d6) δ 8.34 (d, J = 8.8 Hz, 1H), 8.04 (dd, J = 8.2, 2.5 Hz, 1H), 7.99-7.87 (m, 3H), 7.41 (s, 1H), 7.18 (dd, J = 8.0, 2.3 Hz, 1H), 7.04 (d, J = 2.6 Hz, 1H), 6.91 (d, J = 2.5 Hz, 1H), 5.26-5.15 (m, 1H), 5.04-4.92 (m, 1H), 4.59-4.46 (m, 1H), 4.10 (s, 3H), 3.99 (s, 3H), 3.34-3.03 (m, 4H), 2.70-2.58 (m, 1H), 2.13-1.96 (m, 2H), 1.82-0.74 (m, 18H), 0.59-0.42 (m, 1H). |
| 111 | 586.4 | 1H NMR (400 MHz, DMSO-d6) δ 8.05 (d, J = 8.1 Hz, 1H), 7.99-7.90 (m, 3H), 7.88 (d, J = 7.2 Hz, 1H), 7.41 (s, 1H), 7.20 (d, J = 8.1 Hz, 1H), 7.03 (s, 1H), 6.91 (s, 1H), 5.15-5.05 (m, 1H), 4.83-4.70 (m, 1H), 4.47-4.35 (m, 1H), 4.11 (s, 3H), 3.99 (s, 3H), 3.35-3.02 (m, 4H), 2.25-2.14 (m, 1H), 2.08-1.95 (m, 1H), 1.85-1.70 (m, 3H), 1.70-1.28 (m, 9H), 1.25-0.94 (m, 6H). |
| 112 | 598.3 | 1H NMR (400 MHz, DMSO-d6) δ 8.10 (d, J = 8.2 Hz, 1H), 7.93 (s, 4H), 7.42 (s, 1H), 7.26 (d, J = 8.2 Hz, 1H), 7.05 (s, 1H), 6.91 (d, J = 1.2 Hz, 1H), 5.44 (q, J = 7.3 Hz, 1H), 4.69-4.48 (m, 2H), 4.10 (s, 3H), 3.99 (s, 3H), 3.47 (t, J = 7.4 Hz, 2H), 3.34-3.06 (m, 4H), 2.64-2.55 (m, 1H), 2.25-2.11 (m, 1H), 2.07-1.97 (m, 1H), 1.94-1.82 (m, 1H), 1.81-1.21 (m, 12H), 1.16-0.89 (m, 4H). |
| 113 | 597.3 | 1H NMR (400 MHz, DMSO-d6) δ 7.93 (s, 3H), 7.66 (d, J = 8.2 Hz, 1H), 7.41 (s, 1H), 7.39 (s, 1H), 7.16 (dd, J = 8.2, 1.3 Hz, 1H), 7.01 (s, 1H), 6.90 (d, J = 1.1 Hz, 1H), 5.51 (q, J = 7.2 Hz, 1H), 4.54-4.44 (m, 1H), 4.37-4.27 (m, 1H), 4.10 (s, 3H), 3.98 (s, 3H), 3.41 (td, J = 9.5, 3.6 Hz, 1H), 3.35-3.07 (m, 3H), 3.02 (q, J = 8.7 Hz, 1H), 2.58-2.50 (m, 2H), 2.21-2.08 (m, 1H), 2.08-1.95 (m, 1H), 1.80-1.02 (m, 17H), 0.92-0.74 (m, 1H). |
| 114 | 598.3 | 1H NMR (400 MHz, DMSO-d6) δ 8.49 (d, J = 9.1 Hz, 1H), 8.04 (d, J = 8.0 Hz, 1H), 7.99-7.85 (m, 3H), 7.37 (s, 1H), 7.19 (d, J = 8.0 Hz, 1H), 7.03 (s, 1H), 6.92 (d, J = 1.2 Hz, 1H), 5.50 (d, J = 14.0 Hz, 1H), 5.30-5.17 (m, 1H), 4.09 (s, 3H), 4.00 (s, 3H), 3.81 (d, J = 14.1 Hz, 1H), 3.32-3.20 (m, 1H), 3.20-3.08 (m, 4H), 2.32-2.16 (m, 1H), 2.13-1.95 (m, 2H), 1.84-1.50 (m, 4H), 1.39 (d, J = 7.0 Hz, 3H), 1.30 (t, J = 12.7 Hz, 1H), 0.87 (dt, J = 28.1, 12.9 Hz, 2H), 0.53 (t, J = 12.7 Hz, 2H), 0.20 (dt, J = 26.7, 7.8 Hz, 4H). |
| 115 | 596.3 | 1H NMR (400 MHz, DMSO-d6) δ 8.37 (d, J = 9.2 Hz, 1H), 8.03 (d, J = 8.1 Hz, 1H), 7.99-7.83 (m, 3H), 7.43 (s, 1H), 7.17 (d, J = 8.2 Hz, 1H), 7.06 (s, 1H), 6.91 (d, J = 1.2 Hz, 1H), 5.23-5.10 (m, 1H), 4.86 (dd, J = 13.9, 5.3 Hz, 1H), 4.76-4.66 (m, 1H), 4.14 (s, 3H), 3.99 (s, 3H), 3.35-3.04 (m, 5H), 2.00 (d, J = 14.3 Hz, 3H), 1.80-1.70 (m, 3H), 1.52 (dd, J = 54.8, 8.5 Hz, 7H), 1.09-0.97 (m, 2H), 0.93-0.72 (m, 2H), 0.70-0.61 (m, 1H), 0.33 (q, J = 5.3 Hz, 1H), 0.17-0.05 (m, 1H). |
| 116 | 596.3 | 1H NMR (400 MHz, DMSO-d6) δ 8.15 (d, J = 8.2 Hz, 1H), 8.00-7.84 (m, 4H), 7.45 (s, 1H), 7.27 (d, J = 8.2 Hz, 1H), 7.10 (s, 1H), 6.91 (d, J = 1.3 Hz, 1H), 5.02-4.92 (m, 2H), 4.52-4.40 (m, 1H), 4.28-4.02 (m, 5H), 3.99 (s, 3H), 3.37-2.99 (m, 3H), 2.01 (s, 1H), 1.92-1.81 (m, 1H), 1.81-1.69 (m, 1H), 1.66-1.48 (m, 7H), 1.34-1.21 (m, 1H), 1.03-0.71 (m, 3H), 0.65-0.28 (m, 5H). |
| 117 | 596.4 | 1H NMR (400 MHz, DMSO-d6) δ 8.04 (d, J = 8.1 Hz, 1H), 7.98-7.86 (m, 3H), 7.86-7.81 (m, 2H), 7.76 (d, J = 8.3 Hz, 1H), 7.42 (dd, J = 8.3, 1.5 Hz, 1H), 7.27 (s, 1H), 7.18 (d, J = 8.1 Hz, 1H), 5.11 (q, J = 7.1 Hz, 1H), 4.96-4.83 (m, 1H), 4.73-4.62 (m, 1H), 3.89-3.70 (m, 2H), 3.33-3.07 (m, 4H), 2.09-1.88 (m, 3H), 1.81-1.22 (m, 13H), 1.21 (s, 3H), 1.15-0.98 (m, 3H), 0.94 (s, 3H), 0.93-0.85 (m, 1H), 0.60-0.49 (m, 1H). |
| 118 | 584.3 | 1H NMR (400 MHz, DMSO-d6) δ 8.18 (d, J = 8.5 Hz, 1H), 8.06 (d, J = 8.1 Hz, 1H), 7.98-7.79 (m, 3H), 7.44 (s, 1H), 7.20 (d, J = 8.2 Hz, 1H), 7.08 (s, 1H), 6.91 (s, 1H), 5.19 (p, J = 7.4 Hz, 1H), 4.83 (dd, J = 14.4, 6.6 Hz, 1H), 4.79-4.67 (m, 1H), 4.14 (s, 3H), 3.99 (s, 3H), 3.43-3.05 (m, 5H), 2.32-2.23 (m, 1H), 2.23-2.10 (m, 1H), 2.08-1.95 (m, 1H), 1.87-1.70 (m, 2H), 1.70-1.31 (m, 10H), 0.91-0.78 (m, 1H), 0.70-0.55 (m, 1H), 0.20-0.09 (m, 1H), −0.52-−0.64 (m, 1H). |
| 119 | 612.4 | 1H NMR (400 MHz, DMSO-d6) δ 8.05 (d, J = 8.1 Hz, 1H), 7.96-7.84 (m, 3H), 7.79 (d, J = 7.9 Hz, 1H), 7.43 (s, 1H), 7.19 (d, J = 8.1 Hz, 1H), 7.07 (s, 1H), 6.91 (s, 1H), 5.08 (p, J = 7.3 Hz, 1H), 4.80-4.70 (m, 1H), 4.70-4.55 (m, 1H), 4.14 (s, 3H), 3.98 (s, 3H), 3.23 (d, J = 37.0 Hz, 5H), 2.08-1.94 (m, 2H), 1.82-1.18 (m, 11H), 1.12 (s, 3H), 1.01 (s, 3H), 0.74-0.61 (m, 2H), 0.26-0.16 (m, 1H), −0.33-−0.47 (m, 1H). |
| 120 | 596.3 | 1H NMR (400 MHz, DMSO-d6) δ 8.18 (d, J = 7.0 Hz, 1H), 8.07 (s, 3H), 7.90 (d, J = 7.9 Hz, 1H), 7.44 (s, 1H), 7.10 (d, J = 7.9 Hz, 1H), 6.60 (s, 1H), 6.37 (s, 1H), 5.56-5.45 (m, 1H), 5.19-4.86 (m, 4H), 4.47 (s, 2H), 4.09 (s, 1H), 3.76 (s, 2H), 2.81 (s, 3H), 2.38-2.13 (m, 2H), 2.09-1.70 (m, 7H), 1.70-1.57 (m, 1H), 1.51-1.15 (m, 6H), 1.12-0.74 (m, 3H). |

TABLE 3-continued

| Example | ES/MS m/z [M + H]+ | ¹H NMR |
|---|---|---|
| 121 | 612.4 | 1H NMR (400 MHz, DMSO-d6) δ 8.11 (s, 3H), 7.94 (d, J = 8.0 Hz, 1H), 7.77 (d, J = 7.5 Hz, 1H), 7.45 (s, 1H), 7.11 (d, J = 8.1 Hz, 1H), 6.60 (s, 1H), 6.39 (s, 1H), 5.11 (p, J = 7.2 Hz, 1H), 4.80-4.67 (m, 1H), 4.64-4.24 (m, 3H), 4.10 (s, 3H), 3.87-3.63 (m, 1H), 2.80 (s, 3H), 2.40-2.23 (m, 1H), 1.97-1.75 (m, 4H), 1.74-1.24 (m, 11H), 1.20 (s, 3H), 1.15-0.98 (m, 3H), 0.95 (s, 3H). |
| 122 | 598.4 | 1H NMR (400 MHz, DMSO-d6) δ 8.28 (d, J = 8.6 Hz, 1H), 8.10-8.00 (m, 3H), 7.93 (d, J = 7.9 Hz, 1H), 7.44 (s, 1H), 7.10 (d, J = 8.0 Hz, 1H), 6.60 (s, 1H), 6.36 (s, 1H), 5.25-5.13 (m, 1H), 4.98-4.86 (m, 1H), 4.56-4.41 (m, 2H), 4.09 (s, 3H), 3.83-3.46 (m, 2H), 2.80 (s, 3H), 2.66-2.56 (m, 1H), 2.39-2.24 (m, 1H), 2.15-1.98 (m, 1H), 1.89-1.74 (m, 3H), 1.68-1.56 (m, 1H), 1.51-0.74 (m, 15H), 0.60-0.42 (m, 1H). |
| 123 | 582.4 | 1H NMR (400 MHz, DMSO-d6) δ 8.33 (d, J = 8.4 Hz, 1H), 8.10-8.03 (m, 3H), 7.94 (d, J = 7.9 Hz, 1H), 7.45 (s, 1H), 7.12 (d, J = 8.0 Hz, 1H), 6.63 (s, 1H), 6.36 (s, 1H), 5.80-5.69 (m, 1H), 5.38-5.13 (m, 3H), 5.02-4.92 (m, 1H), 4.56-4.42 (m, 3H), 4.10 (s, 3H), 2.83 (d, J = 14.9 Hz, 5H), 2.40-2.25 (m, 1H), 2.17-2.03 (m, 1H), 1.92-1.17 (m, 12H), 1.12-1.00 (m, 1H). |
| 124 | 598.4 | 1H NMR (400 MHz, DMSO-d6) δ 8.09-8.01 (m, 3H), 7.94 (d, J = 8.2 Hz, 1H), 7.83 (d, J = 7.7 Hz, 1H), 7.44 (s, 1H), 7.14-7.08 (m, 1H), 6.58 (s, 1H), 6.35 (s, 1H), 5.15-5.03 (m, 1H), 4.74-4.63 (m, 1H), 4.60-4.27 (m, 2H), 4.09 (s, 3H), 3.80-3.60 (m, 2H), 2.81 (s, 3H), 2.36-2.28 (m, 1H), 2.24-2.11 (m, 1H), 1.90-0.92 (m, 21H). |
| 125 | 610.3 | Exists as 7:3 mixture of rotamers. 1H NMR (400 MHz, DMSO-d6) δ 8.14 (d, J = 8.1 Hz, 0.3H), 8.12-8.06 (m, 3H), 8.04 (d, J = 8.1 Hz, 0.7H), 7.59 (s, 1H), 7.23 (d, J = 8.2 Hz, 0.3H), 7.16 (d, J = 8.1 Hz, 0.7H), 7.13 (s, 0.3H), 7.05-7.01 (m, 1.7H), 5.28 (dt, J = 8.0, 4.2 Hz, 1H), 4.96-4.84 (m, 0.3H), 4.81-4.62 (m, 1.7H), 4.59-4.33 (m, 2H), 4.12 (s, 0.9H), 4.11 (s, 2.1H), 4.00 (s, 3H), 3.96-3.86 (m, 0.7H), 3.81-3.67 (m, 2H), 3.64-3.53 (m, 0.3H), 2.73-2.61 (m, 1H), 2.37-2.24 (m, 2H), 2.19-2.07 (m, 1H), 2.05-1.02 (m, 17H), 0.96-0.71 (m, 1H). |
| 126 | 598.4 | 1H NMR (400 MHz, DMSO-d6) δ 8.15-8.03 (m, 3H), 7.93 (d, J = 8.0 Hz, 1H), 7.58 (d, J = 8.2 Hz, 1H), 7.44 (s, 1H), 7.13 (d, J = 8.1 Hz, 1H), 6.59 (s, 1H), 6.37 (d, J = 1.3 Hz, 1H), 5.17 (p, J = 7.1 Hz, 1H), 4.63-4.35 (m, 4H), 4.09 (s, 3H), 3.81-3.64 (m, 1H), 2.79 (s, 3H), 2.39-2.26 (m, 1H), 1.92-1.39 (m, 11H), 1.39-1.25 (m, 2H), 1.20-1.07 (m, 4H), 1.00 (s, 3H), 0.92-0.67 (m, 2H). |
| 127 | 584.3 | 1H NMR (400 MHz, DMSO-d6) δ 8.15 (d, J = 8.1 Hz, 1H), 8.13-8.04 (m, 3H), 7.46 (s, 1H), 7.15 (d, J = 8.1 Hz, 1H), 6.75 (s, 1H), 6.37 (d, J = 1.3 Hz, 1H), 4.71 (t, J = 6.4 Hz, 2H), 4.61-4.37 (m, 2H), 4.10 (s, 3H), 3.85-3.69 (m, 1H), 3.23 (s, 3H), 2.84 (s, 3H), 2.39-2.25 (m, 1H), 2.04-1.94 (m, 2H), 1.92-1.59 (m, 5H), 1.41-1.15 (m, 8H), 0.99-0.87 (m, 2H), 0.79-0.67 (m, 2H). |
| 128 | 582.5 | 1H NMR (400 MHz, DMSO-d6) δ 8.15-8.02 (m, 3H), 8.00 (d, J = 8.0 Hz, 1H), 7.57 (s, 1H), 7.11 (d, J = 8.1 Hz, 1H), 7.03 (s, 1H), 7.01 (s, 1H), 5.16 (dd, J = 8.2, 4.3 Hz, 1H), 4.71-4.58 (m, 1H), 4.51-4.37 (m, 3H), 4.12 (s, 3H), 4.06-3.91 (m, 4H), 3.81-3.62 (m, 1H), 2.81 (d, J = 11.9 Hz, 1H), 2.47-2.36 (m, 2H), 2.37-2.22 (m, 1H), 2.10-1.70 (m, 8H), 1.69-1.56 (m, 1H), 1.55-1.40 (m, 2H), 1.34 (dd, J = 12.8, 4.4 Hz, 1H), 1.29-1.03 (m, 2H). |
| 129 | 609.4 | Exists as a 2:8 mixture of rotamers. 1H NMR (400 MHz, DMSO-d6) δ 8.15-7.91 (m, 3H), 7.69 (d, J = 8.3 Hz, 0.2H), 7.63 (d, J = 8.2 Hz, 0.8H), 7.57 (s, 0.8H), 7.49 (s, 0.2H), 7.13-7.00 (m, 2.2H), 6.97 (s, 0.8H), 5.30-5.23 (m, 0.8H), 5.20-5.13 (m, 0.2H), 4.75-4.35 (m, 3H), 4.30-4.19 (m, 1H), 4.11 (s, 0.6H), 4.10 (s, 2.4H), 4.02-3.93 (m, 4H), 3.83-3.56 (m, 2H), 2.86-2.74 (m, 1H), 2.38-2.26 (m, 2H), 2.17-1.10 (m, 18H), 0.66-0.49 (m, 1H). |
| 130 | 624.3 | Exists as a 1:1 mixture of rotamers. 1H NMR (400 MHz, DMSO-d6) δ 8.15 (d, J = 8.2 Hz, 0.5H), 8.13-8.04 (m, 3H), 8.01 (d, J = 8.0 Hz, 0.5H), 7.59 (s, 1H), 7.19 (d, J = 8.0 Hz, 0.5H), 7.18 (d, J = 8.2 Hz, 0.5H), 7.11 (s, 0.5H), 7.05-7.01 (m, 1H), 7.00 (s, 0.5H), 5.17-5.08 (m, 1H), 4.88-4.76 (m, 0.5H), 4.75-4.63 (m, 0.5H), 4.61-4.35 (m, 3H), 4.12 (s, 1.5H), 4.10 (s, 1.5H), 4.00 (d, J = 1.8 Hz, 3H), 3.92-3.82 (m, 0.5H), 3.81-3.60 (m, 2.5H), 2.63-2.52 (m, 2H), 2.39-2.19 (m, 4H), 2.14-0.69 (m, 17H), 0.63-0.49 (m, 1H). |
| 131 | 596.3 | Exists as a mixture of 1:1 rotamers. 1H NMR (400 MHz, DMSO-d6) δ 8.14 (d, J = 8.2 Hz, 0.5H), 8.10-8.03 (m, 3H), 8.00 (d, J = 8.0 Hz, 0.5H), 7.59 (s, 1H), 7.27 (d, J = 8.2 Hz, 0.5H), 7.16 (d, J = 8.1 Hz, 0.5H), 7.09 (s, 0.5H), 7.03 (s, 1H), 7.02 (s, 0.5H), 5.27 (d, J = 7.5 Hz, 0.5H), 5.13 (dd, J = 8.0, 4.6 Hz, 0.5H), 4.77-4.61 (m, 1H), 4.60-4.36 (m, 2H), 4.10 (s, 3H), 4.00 (s, 3H), 4.00-3.40 (m, 3H), 2.41-1.04 (m, 17H), 1.02-0.85 (m, 1H), 0.85-0.53 (m, 2H). |
| 132 | 612.3 | 1H NMR (400 MHz, DMSO-d6) δ 8.14 (d, J = 8.2 Hz, 0.3H), 8.12-8.06 (m, 3H), 8.03 (d, J = 8.1 Hz, 0.7H), 7.59 (s, 1H), 7.25 (d, J = 8.1 Hz, 0.3H), 7.15 (d, J = 8.1 Hz, 0.7H), 7.11 (s, 0.3H), 7.03 (s, 1H), 7.00 (s, 0.7H), 5.40-5.34 (m, 0.3H), 5.29-5.22 (m, 0.7H), 4.88-4.78 (m, |

TABLE 3-continued

| Example | ES/MS m/z [M + H]+ | 1H NMR |
|---|---|---|
| | | 0.3H), 4.69-4.27 (m, 3.7H), 4.12 (s, 3H), 4.00 (s, 3H), 3.99-3.91 (m, 0.7H), 3.83-3.52 (m, 4.3H), 3.39-3.29 (m, 0.3H), 3.26-3.14 (m, 0.7H), 3.07-2.90 (m, 1H), 2.39-2.04 (m, 4H), 1.98-1.56 (m, 8H), 1.52-1.09 (m, 4H). |
| 133 | 598.3 | Exists as a 1:1 mixture of rotamers. 1H NMR (400 MHz, DMSO-d6) δ 8.16 (d, J = 8.2 Hz, 0.5H), 8.09 (s, 3H), 8.05 (d, J = 8.1 Hz, 0.5H), 7.59 (s, 1H), 7.29 (d, J = 8.2 Hz, 0.5H), 7.19 (d, J = 8.1 Hz, 0.5H), 7.11 (s, 0.5H), 7.06-6.99 (m, 1.5H), 5.26-5.19 (m, 1H), 4.65 (t, J = 13.3 Hz, 0.5H), 4.55-4.31 (m, 4.5H), 4.12 (s, 1.5H), 4.10 (s, 1.5H), 4.00 (s, 3H), 3.91-3.69 (m, 3H), 3.65 (d, J = 12.6 Hz, 0.5H), 3.60-3.36 (m, 2.5H), 2.49-2.25 (m, 4H), 2.01-1.56 (m, 6H), 1.53-1.10 (m, 3.5H), 1.04-0.89 (m, 0.5H). |
| 134 | 636.4 | Exists as a 7:3 ratio of rotamers. 1H NMR (400 MHz, DMSO-d6) δ 8.15 (d, J = 8.2 Hz, 0.3H), 8.11-7.99 (m, 3.7H), 7.59 (s, 1H), 7.31 (d, J = 8.1 Hz, 0.3H), 7.14 (d, J = 7.6 Hz, 0.7H), 7.13 (s, 0.3H), 7.03 (s, 1.7H), 5.43-5.36 (m, 1H), 4.92-4.70 (m, 1H), 4.57-4.38 (m, 2H), 4.14 (s, 0.9H), 4.12 (s, 2.1H), 4.00 (s, 3H), 3.89-3.62 (m, 3H), 2.43-2.35 (m, 1H), 2.18-2.06 (m, 1H), 1.92-0.79 (m, 18H), 0.70-0.50 (m, 3H), 0.34-0.23 (m, 1H). |
| 135 | 622.3 | 1H NMR (400 MHz, DMSO-d6) δ 8.16-7.99 (m, 4H), 7.59 (s, 1H), 7.19 (d, J = 8.2 Hz, 1H), 7.06-6.99 (m, 2H), 5.31 (d, J = 5.6 Hz, 1H), 4.53 (d, J = 97.4 Hz, 4H), 4.19-3.67 (m, 9H), 2.36-2.26 (m, 1H), 2.09-1.96 (m, 2H), 1.82 (s, 4H), 1.68-0.93 (m, 13H), 0.73-0.65 (m, 1H), 0.53-0.43 (m, 1H). |
| 136 | 598.4 | 1H NMR (400 MHz, DMSO-d6) δ 8.33 (d, J = 8.6 Hz, 1H), 8.12-7.99 (m, 4H), 7.58 (s, 1H), 7.19 (d, J = 7.4 Hz, 1H), 7.05 (s, 1H), 7.03 (s, 1H), 5.27-5.16 (m, 1H), 5.06-4.92 (m, 1H), 4.58-4.30 (m, 3H), 4.10 (s, 3H), 4.00 (s, 3H), 3.80-3.67 (m, 1H), 2.70-2.59 (m, 1H), 2.36-2.23 (m, 1H), 2.16-2.00 (m, 1H), 1.91-1.75 (m, 4H), 1.71-1.58 (m, 1H), 1.53-0.75 (m, 14H), 0.58-0.42 (m, 1H). |
| 137 | 598.4 | 1H NMR (400 MHz, DMSO-d6) δ 8.13-7.99 (m, 4H), 7.88 (d, J = 7.9 Hz, 1H), 7.59 (s, 1H), 7.20 (dd, J = 8.5, 2.6 Hz, 1H), 7.03 (s, 2H), 5.16-5.04 (m, 1H), 4.83-4.70 (m, 1H), 4.61-4.32 (m, 3H), 4.12 (s, 3H), 4.01 (s, 3H), 3.81-3.66 (m, 1H), 2.39-2.25 (m, 1H), 2.25-2.14 (m, 1H), 1.92-0.94 (m, 20H). |
| 138 | 610.4 | 1H NMR (400 MHz, DMSO-d6) δ 8.10 (d, J = 8.1 Hz, 1H), 8.08-7.98 (m, 3H), 7.60 (s, 1H), 7.26 (d, J = 8.2 Hz, 1H), 7.05 (s, 1H), 7.03 (s, 1H), 5.44 (q, J = 7.2 Hz, 1H), 4.70-4.33 (m, 4H), 4.10 (s, 3H), 4.00 (s, 3H), 3.81-3.66 (m, 1H), 3.46 (t, J = 7.4 Hz, 2H), 2.65-2.55 (m, 1H), 2.36-2.23 (m, 1H), 2.26-2.11 (m, 1H), 1.94-0.89 (m, 19H). |
| 139 | 610.3 | 1H NMR (400 MHz, DMSO-d6) δ 8.48 (d, J = 9.1 Hz, 1H), 8.11-8.00 (m, 4H), 7.55 (s, 1H), 7.19 (d, J = 8.1 Hz, 1H), 7.04 (s, 2H), 5.50 (d, J = 14.1 Hz, 1H), 5.30-5.15 (m, 1H), 4.65-4.24 (m, 2H), 4.09 (s, 3H), 4.01 (s, 3H), 3.80 (d, J = 14.2 Hz, 1H), 3.77-3.64 (m, 1H), 2.39-2.18 (m, 3H), 2.13-2.01 (m, 1H), 1.91-1.75 (m, 2H), 1.76-1.58 (m, 2H), 1.45-1.20 (m, 5H), 1.01-0.77 (m, 2H), 0.62-0.45 (m, 2H), 0.29-0.11 (m, 3H), −0.18--0.29 (m, 1H). |
| 140 | 600.4 | 1H NMR (400 MHz, DMSO-d6) δ 8.45 (d, J = 9.1 Hz, 1H), 8.05 (d, J = 8.1 Hz, 1H), 8.00-7.89 (m, 3H), 7.41 (s, 1H), 7.20 (d, J = 8.1 Hz, 1H), 7.05 (s, 1H), 6.91 (s, 1H), 5.38-5.26 (m, 1H), 5.00 (d, J = 13.9 Hz, 1H), 4.69 (d, J = 13.9 Hz, 1H), 4.17 (s, 3H), 3.99 (s, 3H), 3.31-3.20 (m, 2H), 3.20-3.05 (m, 3H), 2.37-2.23 (m, 1H), 2.14-1.94 (m, 2H), 1.81-1.67 (m, 2H), 1.66-1.51 (m, 2H), 1.36 (d, J = 7.0 Hz, 3H), 1.04-0.89 (m, 2H), 0.81 (s, 3H), 0.76-0.48 (m, 3H), 0.16 (s, 3H). |
| 141 | 612.3 | 1H NMR (400 MHz, DMSO-d6) δ 8.44 (d, J = 9.0 Hz, 1H), 8.13-8.01 (m, 4H), 7.59 (s, 1H), 7.20 (d, J = 8.1 Hz, 1H), 7.06 (s, 1H), 7.03 (s, 1H), 5.40-5.24 (m, 1H), 5.00 (d, J = 13.9 Hz, 1H), 4.69 (d, J = 14.0 Hz, 1H), 4.61-4.27 (m, 2H), 4.17 (s, 3H), 4.00 (s, 3H), 3.79-3.67 (m, 1H), 2.41-2.22 (m, 3H), 2.14-2.05 (m, 1H), 1.91-1.56 (m, 5H), 1.43-1.30 (m, 5H), 1.05-0.89 (m, 2H), 0.81 (s, 3H), 0.76-0.63 (m, 2H), 0.63-0.52 (m, 1H), 0.15 (s, 3H). |
| 142 | 608.3 | 1H NMR (400 MHz, DMSO-d6) δ 8.37 (d, J = 9.1 Hz, 1H), 8.11-8.05 (m, 3H), 8.04 (d, J = 8.1 Hz, 1H), 7.64-7.60 (m, 1H), 7.17 (d, J = 8.2 Hz, 1H), 7.06 (s, 1H), 7.03 (d, J = 1.2 Hz, 1H), 5.21-5.11 (m, 1H), 4.88 (dd, J = 13.7, 5.4 Hz, 1H), 4.77-4.66 (m, 1H), 4.60-3.63 (m, 9H), 2.39-2.25 (m, 1H), 2.08-1.92 (m, 2H), 1.92-1.70 (m, 3H), 1.69-1.29 (m, 7H), 1.07-0.97 (m, 2H), 0.92-0.71 (m, 2H), 0.70-0.57 (m, 1H), 0.32 (q, J = 5.4 Hz, 1H), 0.19-0.05 (m, 1H). |
| 143 | 608.3 | 1H NMR (400 MHz, DMSO-d6) δ 8.16 (d, J = 8.2 Hz, 1H), 8.12-8.00 (m, 3H), 7.90 (d, J = 8.2 Hz, 1H), 7.62 (s, 1H), 7.27 (d, J = 8.2 Hz, 1H), 7.11 (s, 1H), 7.03 (d, J = 1.2 Hz, 1H), 5.05-4.90 (m, 1H), 4.52-4.40 (m, 1H), 4.14 (s, 3H), 4.00 (s, 3H), 3.97-3.62 (m, 3H), 2.38-2.27 (m, 1H), 1.92-1.76 (m, 5H), 1.66-1.56 (m, 1H), 1.53 (d, J = 6.9 Hz, 3H), 1.40-1.21 (m, 2H), 1.00-0.71 (m, 3H), 0.64-0.31 (m, 6H). |
| 144 | 596.4 | 1H NMR (400 MHz, DMSO-d6) δ 8.17 (d, J = 8.4 Hz, 1H), 8.09-7.99 (m, 4H), 7.61 (s, 1H), 7.20 (d, J = 8.1 Hz, 1H), 7.09 (s, 1H), 7.03 (s, 1H), |

TABLE 3-continued

| Example | ES/MS m/z [M + H]+ | ¹H NMR |
|---|---|---|
| | | 5.17 (p, J = 7.3 Hz, 1H), 4.90-4.79 (m, 1H), 4.79-4.66 (m, 1H), 4.62-4.35 (m, 3H), 4.15 (s, 3H), 4.00 (s, 3H), 3.82-3.67 (m, 1H), 2.39-2.24 (m, 2H), 2.24-2.11 (m, 1H), 1.89-1.73 (m, 4H), 1.66-1.28 (m, 10H), 0.90-0.78 (m, 1H), 0.69-0.55 (m, 1H), 0.18-0.09 (m, 1H), −0.53-−0.65 (m, 1H). |
| 145 | 624.4 | 1H NMR (400 MHz, DMSO-d6) δ 8.11-8.02 (m, 4H), 7.79 (d, J = 7.8 Hz, 1H), 7.61 (s, 1H), 7.20 (d, J = 8.2 Hz, 1H), 7.08 (s, 1H), 7.03 (s, 1H), 5.10 (p, J = 7.2 Hz, 1H), 4.81-4.72 (m, 1H), 4.69-4.58 (m, 1H), 4.57-4.34 (m, 2H), 4.15 (s, 3H), 4.00 (s, 3H), 3.85-3.64 (m, 1H), 2.38-2.24 (m, 1H), 1.92-1.18 (m, 14H), 1.12 (s, 3H), 1.00 (s, 3H), 0.74-0.59 (m, 2H), 0.25-0.15 (m, 1H), −0.35-−0.48 (m, 1H). |
| 146 | 601.4 | 1H NMR (400 MHz, DMSO-d6) δ 8.00 (brs, 3H), 7.95 (d, J = 8.0 Hz, 1H), 7.32 (s, 1H), 7.12 (d, J = 8.0 Hz, 1H), 6.63 (s, 1H), 6.40 (s, 1H), 6.33 (d, J = 7.5 Hz, 1H), 5.08-4.99 (m, 1H), 4.73-4.63 (m, 1H), 4.48-4.39 (m, 1H), 4.09 (s, 3H), 3.53-3.42 (m, 1H), 3.36-3.03 (m, 3H), 2.80 (s, 3H), 2.78 (s, 3H), 2.08-2.98 (m, 1H), 1.89-1.71 (m, 2H), 1.67-1.48 (m, 5H), 1.49-1.39 (m, 1H), 1.42 (d, J = 6.8 Hz, 3H), 1.32-1.09 (m, 5H), 1.04-0.90 (m, 1H). |
| 147 | 650.4 | 1H NMR (400 MHz, DMSO-d6) δ 8.62 (d, J = 7.4 Hz, 1H), 8.07 (dd, J = 7.9, 1.9 Hz, 1H), 8.02 (d, J = 7.9 Hz, 1H), 7.93 (brs, 3H), 7.54-7.47 (m, 1H), 7.30 (s, 1H), 7.23 (d, J = 8.1 Hz, 1H), 7.17 (d, J = 8.1 Hz, 1H), 7.09 (dd, J = 7.9, 7.9 Hz, 1H), 6.68 (s, 1H), 6.34 (s, 1H), 5.45-5.35 (m, 1H), 4.95-4.81 (m, 1H), 4.69-4.57 (m, 1H), 4.21-4.14 (m, 1H), 4.09 (s, 3H), 4.07-3.99 (m, 1H), 2.85 (s, 3H), 2.07-1.85 (m, 2H), 1.83-1.58 (m, 4H), 1.53 (d, J = 6.5 Hz, 3H), 1.49-1.33 (m, 4H), 1.27-1.10 (m, 3H), 0.72-0.59 (m, 2H). |
| 148 | 599.6 | 1H NMR (400 MHz, DMSO-d6) δ 8.05 (d, J = 7.7 Hz, 1H), 7.94 (brs, 3H), 7.61 (d, J = 8.2 Hz, 1H), 7.40 (s, 1H), 7.34 (s, 1H), 7.08 (dd, J = 8.3, 1.2 Hz, 1H), 6.99 (s, 1H), 6.91 (d, J = 1.2 Hz, 1H), 5.11-5.00 (m, 1H), 4.69-4.56 (m, 1H), 4.23-4.13 (m, 1H), 4.11 (s, 3H), 3.99 (s, 3H), 3.35-3.02 (m, 4H), 2.14-1.95 (m, 3H), 1.83-1.52 (m, 5H), 1.51-1.36 (m, 2H), 1.45 (d, J = 7.1 Hz, 3H), 1.24 (s, 3H), 1.19-1.01 (m, 3H), 0.95 (s, 3H). |
| 149 | 586.3 | 1H NMR (400 MHz, DMSO-d6) δ 8.50 (d, J = 7.3 Hz, 1H), 8.05 (d, J = 8.1 Hz, 1H), 7.95 (brs, 3H), 7.42 (s, 1H), 7.22 (d, J = 8.1 Hz, 1H), 7.01 (s, 1H), 6.92 (d, J = 1.2 Hz, 1H), 5.10-5.00 (m, 1H), 4.97 (dd, J = 14.2, 4.1 Hz, 1H), 4.79 (dd, J = 14.2, 3.5 Hz, 1H), 4.12 (s, 3H), 3.99 (s, 3H), 3.78-3.70 (m, 1H), 3.50-3.42 (m, 2H), 3.33-3.05 (m, 4H), 2.75 (t, J = 9.8 Hz, 1H), 2.61-2.56 (m, 1H), 2.14-1.96 (m, 2H), 1.83-1.68 (m, 1H), 1.67-1.52 (m, 2H), 1.49-1.37 (m, 1H), 1.46 (d, J = 6.8 Hz, 3H), 0.32-0.10 (m, 2H), 0.09-0.00 (m, 1H). |
| 150 | 586.3 | 1H NMR (400 MHz, DMSO-d6) δ 8.54 (d, J = 6.6 Hz, 1H), 8.04 (d, J = 8.0 Hz, 1H), 7.96 (brs, 3H), 7.43 (s, 1H), 7.20 (d, J = 8.1 Hz, 1H), 7.02 (s, 1H), 6.92 (d, J = 1.2 Hz, 1H), 5.02-4.94 (m, 1H), 4.68 (dd, J = 14.0, 3.5 Hz, 1H), 4.15 (s, 3H), 4.04-3.94 (m, 1H), 4.00 (s, 3H), 3.67-3.55 (m, 2H), 3.41 (dd, J = 11.1, 5.6 Hz, 1H), 3.35-3.09 (m, 3H), 2.83 (dd, J = 11.1, 8.3 Hz, 1H), 2.70-2.60 (m, 1H), 2.12 (ddd, J = 15.0, 5.0, 2.5 Hz, 1H), 2.07-1.98 (m, 1H), 1.85-1.70 (m, 2H), 1.67-1.53 (m, 2H), 1.44 (d, J = 6.9 Hz, 3H), 1.01-0.89 (m, 1H), 0.52-0.44 (m, 1H), 0.37-0.29 (m, 1H). |
| 151 | 570.4 | 1H NMR (400 MHz, DMSO-d6) δ 8.24 (d, J = 9.2 Hz, 1H), 8.03 (d, J = 8.1 Hz, 1H), 7.94 (brs, 3H), 7.44 (s, 1H), 7.18 (d, J = 8.2 Hz, 1H), 6.97 (s, 1H), 6.92 (d, J = 1.2 Hz, 1H), 5.09 (dq, J = 9.2, 7.2 Hz, 1H), 4.76-4.64 (m, 1H), 4.26-4.17 (m, 1H), 4.14 (s, 3H), 3.99 (s, 3H), 3.35-3.06 (m, 3H), 2.25-2.10 (m, 1H), 2.08-1.97 (m, 1H), 1.91-1.65 (m, 4H), 1.64-1.43 (m, 2H), 1.48 (d, J = 7.2 Hz, 3H), 1.06-0.96 (m, 1H), 0.95-0.82 (m, 2H), 0.71-0.58 (m, 1H). |
| 152 | 582.4 | 1H NMR (400 MHz, DMSO-d6) δ 8.24 (d, J = 9.3 Hz, 1H), 8.07 (brs, 3H), 8.03 (d, J = 8.1 Hz, 1H), 7.61 (s, 1H), 7.18 (d, J = 8.2 Hz, 1H), 7.04 (d, J = 1.2 Hz, 1H), 6.98 (s, 1H), 5.15-5.03 (m, 1H), 4.77-4.64 (m, 1H), 4.45 (brs, 2H), 4.29-4.18 (m, 1H), 4.14 (s, 3H), 4.01 (s, 3H), 2.35-2.25 (m, 1H), 2.23-2.09 (m, 1H), 1.92-1.51 (m, 9H), 1.48 (d, J = 7.2 Hz, 3H), 1.34 (dd, J = 12.9, 4.4 Hz, 1H), 1.07-0.97 (m, 1H), 0.95-0.82 (m, 2H), 0.69-0.60 (m, 1H). |
| 153 | 630.5 | 1H NMR (400 MHz, DMSO-d6) δ 8.06 (d, J = 8.1 Hz, 1H), 7.95 (brs, 3H), 7.73 (d, J = 8.5 Hz, 1H), 7.43 (s, 1H), 7.21 (d, J = 8.1 Hz, 1H), 7.04 (s, 1H), 6.92 (d, J = 1.2 Hz, 1H), 5.26-5.11 (m, 1H), 4.83-4.72 (m, 1H), 4.46-4.33 (m, 1H), 4.12 (s, 3H), 3.99 (s, 3H), 3.53 (s, 3H), 3.38-3.01 (m, 5H), 2.07-1.96 (m, 1H), 1.95-1.69 (m, 3H), 1.69-1.53 (m, 3H), 1.51-1.39 (m, 2H), 1.45 (d, J = 7.1 Hz, 3H), 1.39-1.28 (m, 2H), 1.26 (s, 3H), 1.23-1.12 (m, 1H), 1.00 (s, 3H). |
| 154 | 630.4 | 1H NMR (400 MHz, DMSO-d6) δ 8.02 (d, J = 8.1 Hz, 1H), 7.97 (d, J = 6.3 Hz, 1H), 7.95 (brs, 3H), 7.41 (s, 1H), 7.16 (d, J = 8.1 Hz, 1H), 7.03 (s, 1H), 6.92 (d, J = 1.2 Hz, 1H), 5.04-4.94 (m, 1H), 4.92-4.80 (m, 1H), 4.49-4.38 (m, 1H), 4.11 (s, 3H), 3.99 (s, 3H), 3.73 (d, J = 9.0 Hz, 1H), 3.31-3.08 (m, 2H), 2.10-1.85 (m, 3H), 1.83-1.68 (m, 2H), 1.67-1.49 |

TABLE 3-continued

| Example | ES/MS m/z [M + H]+ | 1H NMR |
|---|---|---|
| | | (m, 5H), 1.45 (d, J = 7.1 Hz, 3H), 1.40-1.26 (m, 4H), 1.25 (s, 3H), 1.02-0.88 (m, 1H), 0.84-0.69 (m, 1H), 0.80 (s, 3H). |
| 155 | 597.6 | 1H NMR (400 MHz, DMSO-d6) δ 8.24 (d, J = 8.6 Hz, 1H), 7.94 (s, 3H), 7.61 (d, J = 8.2 Hz, 1H), 7.55 (s, 1H), 7.41 (s, 1H), 7.08 (dd, J = 8.3, 1.2 Hz, 1H), 7.00 (s, 1H), 6.91 (d, J = 1.2 Hz, 1H), 5.25-5.15 (m, 1H), 4.68-4.56 (m, 1H), 4.29-4.18 (m, 1H), 4.12 (s, 3H), 3.99 (s, 3H), 3.34-3.00 (m, 3H), 2.42-2.30 (m, 1H), 2.07-1.85 (m, 1H), 1.85-1.68 (m, 3H), 1.26-1.52 (m, 2H), 1.51-1.33 (m, 4H), 1.46 (d, J = 7.1 Hz, 3H), 1.25-1.07 (m, 3H), 1.06-0.95 (m, 1H), 0.84-0.73 (m, 1H), 0.68-0.57 (m, 1H), 0.38-0.28 (m, 1H). |
| 156 | 601.4 | 1H NMR (400 MHz, DMSO-d6) δ 8.51 (d, J = 9.4 Hz, 1H), 7.94 (brs, 3H), 7.69 (s, 1H), 7.57 (d, J = 8.1 Hz, 1H), 7.40 (s, 1H), 7.07 (dd, J = 8.2, 1.2 Hz, 1H), 7.01 (s, 1H), 6.91 (d, J = 1.2 Hz, 1H), 5.25-5.06 (m, 1H), 4.79-4.65 (m, 1H), 4.35-4.24 (m, 1H), 4.09 (s, 3H), 3.99 (s, 3H), 3.38-3.02 (m, 4H), 2.61-2.50 (m, 1H), 2.36-2.20 (m, 1H), 2.07-1.97 (m, 1H), 1.83-1.71 (m, 1H), 1.69-1.52 (m, 4H), 1.54-1.42 (m, 1H), 1.47 (d, J = 7.1 Hz, 3H), 1.38 (s, 3H), 1.36-1.20 (m, 1H), 1.18 (s, 3H), 0.65-0.49 (m, 1H). |
| 157 | 584.4 | 1H NMR (400 MHz, DMSO-d6) δ 8.45 (d, J = 8.5 Hz, 1H), 7.99 (d, J = 8.0 Hz, 1H), 7.95 (brs, 3H), 7.42 (s, 1H), 7.14 (d, J = 8.0 Hz, 1H), 7.02 (s, 1H), 6.92 (d, J = 1.2 Hz, 1H), 5.06-4.93 (m, 1H), 4.78-4.64 (m, 1H), 4.65-4.54 (m, 1H), 4.12 (s, 3H), 3.99 (s, 3H), 3.37-2.97 (m, 4H), 2.09-1.97 (m, 1H), 1.92-1.81 (m, 1H), 1.81-1.72 (m, 1H), 1.70-1.48 (m, 7H), 1.47-1.32 (m, 1H), 1.43 (d, J = 7.1 Hz, 3H), 1.29-1.11 (m, 1H), 0.91-0.81 (m, 1H), 0.79-0.59 (m, 2H), 0.53-0.44 (m, 1H). |
| 158 | 584.4 | 1H NMR (400 MHz, DMSO-d6) δ 8.41 (d, J = 7.2 Hz, 1H), 8.02 (d, J = 8.1 Hz, 1H), 7.95 (brs, 3H), 7.42 (s, 1H), 7.22 (d, J = 8.3 Hz, 1H), 7.03 (s, 1H), 6.92 (d, J = 1.2 Hz, 1H), 4.75-4.52 (m, 2H), 4.53-4.43 (m, 1H), 4.13 (s, 3H), 4.00 (s, 3H), 3.35-3.02 (m, 4H), 2.08-1.97 (m, 1H), 1.88-1.76 (m, 2H), 1.74 (d, J = 7.1 Hz, 3H), 1.71-1.36 (m, 5H), 1.35-1.26 (m, 3H), 0.92-0.83 (m, 2H), 0.82-0.65 (m, 1H), 0.49 (dd, J = 7.8, 2.9 Hz, 1H). |
| 159 | 623.8 | 1H NMR (400 MHz, DMSO-d6) δ 8.24 (d, J = 8.6 Hz, 1H), 7.94 (brs, 3H), 7.59 (d, J = 8.2 Hz, 1H), 7.55 (s, 1H), 7.37 (s, 1H), 7.12 (s, 1H), 7.06 (dd, J = 8.2, 1.2 Hz, 1H), 6.91 (d, J = 1.2 Hz, 1H), 5.23-5.13 (m, 1H), 4.88-4.76 (m, 1H), 4.34-4.21 (m, 1H), 3.99 (s, 3H), 3.92-3.84 (m, 1H), 3.33-3.07 (m, 1H), 2.41-2.29 (m, 1H), 2.08-1.96 (m, 1H), 1.85-1.70 (m, 2H), 1.70-1.52 (m, 3H), 1.46 (d, J = 7.1 Hz, 3H), 1.44-1.32 (m, 4H), 1.26-0.92 (m, 6H), 0.85-0.71 (m, 2H), 0.67-0.58 (m, 1H), 0.54-0.44 (m, 1H), 0.37-0.27 (m, 1H). |
| 160 | 625.5 | 1H NMR (400 MHz, DMSO-d6) δ 8.06 (d, J = 7.6 Hz, 1H), 7.95 (brs, 3H), 7.59 (d, J = 8.1 Hz, 1H), 7.36 (s, 1H), 7.35 (s, 1H), 7.12 (s, 1H), 7.06 (dd, J = 8.1, 1.2 Hz, 1H), 6.91 (d, J = 1.2 Hz, 1H), 5.09-4.99 (m, 1H), 4.90-4.78 (m, 1H), 4.28-4.15 (m, 1H), 3.99 (s, 3H), 3.91-3.83 (m, 1H), 3.32-3.01 (m, 4H), 2.13-1.92 (m, 2H), 1.79-1.70 (m, 1H), 1.69-1.52 (m, 3H), 1.49-1.28 (m, 4H), 1.46 (d, J = 7.2 Hz, 3H), 1.24 (s, 3H), 1.16-0.92 (m, 4H), 0.94 (s, 3H), 0.83-0.71 (m, 1H), 0.51-0.40 (m, 1H). |
| 161 | 600.3 | 1H NMR (400 MHz, DMSO-d6) δ 8.35 (d, J = 8.4 Hz, 1H), 8.05 (d, J = 8.1 Hz, 1H), 7.95 (brs, 3H), 7.42 (s, 1H), 7.22 (d, J = 8.1 Hz, 1H), 7.01 (s, 1H), 6.92 (d, J = 1.2 Hz, 1H), 5.18-5.10 (m, 1H), 5.07 (dd, J = 14.1, 4.2 Hz, 1H), 4.92 (dd, J = 14.1, 2.6 Hz, 1H), 4.23-4.13 (m, 2H), 4.12 (s, 3H), 4.00 (s, 3H), 3.56-3.49 (m, 1H), 3.33-3.12 (m, 2H), 2.70-2.54 (m, 2H), 2.15-1.97 (m, 2H), 2.15-1.96 (m, 2H), 1.48-1.37 (m, 1H), 1.44 (d, J = 7.0 Hz, 3H), 0.82 (d, J = 6.2 Hz, 3H), 0.02--0.04 (m, 1H), -0.04--0.11 (m, 1H), -0.16--0.25 (m, 1H). |
| 162 | 600.4 | 1H NMR (400 MHz, DMSO-d6) δ 8.51 (d, J = 6.6 Hz, 1H), 8.03 (d, J = 8.1 Hz, 1H), 7.95 (brs, 3H), 7.41 (s, 1H), 7.20 (d, J = 8.1 Hz, 1H), 6.99 (s, 1H), 6.92 (d, J = 1.2 Hz, 1H), 5.04-4.93 (m, 1H), 4.80 (dd, J = 14.1, 4.2 Hz, 1H), 4.60 (dd, J = 14.1, 5.6 Hz, 1H), 4.11 (s, 3H), 3.99 (s, 3H), 3.68-3.61 (m, 1H), 3.41-3.09 (m, 5H), 2.15-1.95 (m, 3H), 1.81-1.69 (m, 1H), 1.65-1.52 (m, 1H), 1.44 (d, J = 6.9 Hz, 3H), 0.78 (d, J = 6.2 Hz, 3H), 0.56-0.48 (m, 1H), 0.31-0.24 (m, 1H), 0.01--0.03 (m, 1H). |
| 163 | 584.4 | 1H NMR (400 MHz, DMSO-d6) δ 8.29 (d, J = 8.4 Hz, 1H), 8.01 (d, J = 8.1 Hz, 1H), 7.96 (brs, 3H), 7.40 (s, 1H), 7.19 (d, J = 8.1 Hz, 1H), 6.97 (s, 1H), 6.92 (d, J = 1.2 Hz, 1H), 5.22-5.00 (m, 1H), 4.91 (dd, J = 14.1, 4.6 Hz, 1H), 4.57 (dd, J = 14.1, 5.2 Hz, 1H), 4.11 (s, 3H), 3.99 (s, 3H), 3.65-3.37 (m, 3H), 3.34-3.06 (m, 3H), 2.40-2.33 (m, 1H), 2.09-1.97 (m, 1H), 1.87-1.68 (m, 2H), 1.66-1.41 (m, 3H), 1.46 (d, J = 7.0 Hz, 3H), 1.18-1.02 (m, 1H), 0.90-0.76 (m, 1H), 0.65-0.52 (m, 1H), 0.10-0.01 (m, 1H), 0.00--0.14 (m, 2H). |
| 164 | 583.4 | 1H NMR (400 MHz, DMSO-d6) δ 8.68 (d, J = 8.8 Hz, 1H), 7.96 (brs, 3H), 7.62 (s, 1H), 7.55 (d, J = 8.1 Hz, 1H), 7.39 (s, 1H), 7.02 (dd, J = 8.2, 1.3 Hz, 1H), 6.99 (s, 1H), 6.91 (s, 1H), 5.02-4.89 (m, 1H), 4.85-4.74 (m, 1H), 4.23-4.13 (m, 1H), 4.10 (s, 3H), 3.99 (s, 3H), 3.85-3.58 (m, 3H), 3.29-3.06 (m, 2H), 2.07-1.95 (m, 1H), 1.92-1.65 (m, 3H), 1.65- |

TABLE 3-continued

| Example | ES/MS m/z [M + H]+ | 1H NMR |
|---|---|---|
| | | 1.51 (m, 3H), 1.43 (d, J = 7.1 Hz, 3H), 1.41-1.22 (m, 2H), 0.97-0.90 (m, 1H), 0.87-0.65 (m, 2H), 0.58-0.51 (m, 1H). |
| 165 | 583.5 | 1H NMR (400 MHz, DMSO-d6) δ 8.58 (d, J = 6.9 Hz, 0.6H 1st rotamer), 7.95 (brs, 3H), 7.66 (d, J = 8.3 Hz, 0.4H 2nd rotamer), 7.62 (s, 0.4H 2nd rotamer), 7.60 (s, 0.6H 1st rotamer), 7.58 (d, J = 8.3 Hz, 0.6H 1st rotamer), ), 7.54 (d, J = 6.1 Hz, 0.4H 2nd rotamer), 7.40 (s, 1H), 7.15 (d, J = 8.6 Hz, 0.4H 2nd rotamer), 7.12 (d, J = 8.6 Hz, 0.6H 1st rotamer), 7.04 (s, 0.4H 2nd rotamer), 7.01 (s, 0.6H 1st rotamer), 6.95 (s, 1H), 5.06-4.95 (m, 1H), 4.78-4.63 (m, 1H), 4.58-4.48 (m, 1H), 4.29-4.17 (m, 1H), 4.11 (s, 1.8H 1st rotamer), 4.10 (s, 1.2H 2nd rotamer), 3.99 (s, 3H), 3.36-3.06 (m, 3H), 2.07-1.96 (m, 2H), 1.86-1.70 (m, 1H), 1.75 (d, J = 7.1 Hz, 3H), 1.70-1.49 (m, 4H), 1.47-1.30 (m, 4H), 1.20-1.02 (m, 1H), 1.02-0.72 (m, 2H), 0.61-0.27 (m, 1H). |
| 166 | 598.4 | 1H NMR (400 MHz, DMSO-d6) δ 8.24 (d, J = 8.2 Hz, 0.5H), 8.06 (d, J = 8.1 Hz, 0.5H), 8.00 (d, J = 8.0 Hz, 0.5H), 7.96 (brs, 3H), 7.95 (d, J = 8.0 Hz, 0.5H), 7.42 (s, 0.5H), 7.39 (s, 0.5H), 7.24 (d, J = 8.2 Hz, 0.5H), 7.18 (d, J = 8.1 Hz, 0.5H), 7.01 (s, 0.5H), 6.96 (s, 0.5H), 6.93 (d, J = 1.2 Hz, 0.5H), 6.91 (d, J = 1.2 Hz, 0.5H), 5.22 (dd, J = 14.1, 3.7 Hz, 0.5H), 5.19-5.11 (m, 0.5H), 5.09-4.98 (m, 1H), 4.82 (dd, J = 14.1, 4.9 Hz, 0.5H), 4.40 (dd, J = 14.1, 6.1 Hz, 0.5H), 4.13 (s, 1.5H), 4.09 (s, 1.5H), 4.00 (s, 1.5H), 3.99 (s, 1.5H), 3.34-3.06 (m, 4H), 2.21-1.98 (m, 2H), 1.83-1.49 (m, 2H), 1.48 (d, J = 7.1 Hz, 1.5H), 1.48 (d, J = 7.1 Hz, 1.5H), 1.43-0.96 (m, 3H), 0.94-0.77 (m, 3H), 0.71-0.54 (m, 2H), 0.45-0.29 (m, 1H), 0.18-0.11 (m, 1H), 0.10--0.02 (m, 1H), -0.13--0.21 (m, 1H), -0.29--0.36 (m, 1H), -0.46--0.58 (m, 1H). |
| 167 | 596.4 | 1H NMR (400 MHz, DMSO-d6) δ 8.04 (d, J = 8.1 Hz, 1H), 7.97 (brs, 3H), 7.39 (s, 1H), 7.18 (d, J = 8.2 Hz, 1H), 7.15 (d, J = 7.8 Hz, 1H), 7.00 (s, 1H), 6.91 (d, J = 1.2 Hz, 1H), 5.06-4.99 (m, 1H), 4.96 (d, J = 12.8 Hz, 1H), 4.12 (s, 3H), 3.99 (s, 3H), 3.97-3.38 (m, 2H), 3.32-3.09 (m, 3H), 2.13-1.86 (m, 4H), 1.83-1.70 (m, 1H), 1.67-1.52 (m, 3H), 1.48 (d, J = 7.2 Hz, 3H), 1.27-1.16 (m, 1H), 1.14-1.06 (m, 1H), 0.78-0.68 (m, 1H), 0.63-0.46 (m, 3H), 0.25-0.16 (m, 1H), 0.04--0.02 (m, 1H). |
| 168 | 596.4 | 1H NMR (400 MHz, DMSO-d6) δ 7.99 (d, J = 8.0 Hz, 1H), 7.95 (brs, 3H), 7.46 (s, 1H), 7.13 (d, J = 8.1 Hz, 1H), 7.03 (s, 1H), 6.92 (d, J = 1.2 Hz, 1H), 5.18-5.01 (m, 1H), 4.76-4.09 (m, 1H), 4.15 (s, 3H), 4.01-3.92 (m, 2H), 4.00 (s, 3H), 3.36-3.01 (m, 3H), 2.08-1.97 (m, 2H), 1.94-1.85 (m, 1H), 1.83-1.68 (m, 1H), 1.66-1.64 (m, 1H), 1.54-1.42 (m, 1H), 1.40 (d, J = 7.1 Hz, 3H), 1.36-1.28 (m, 1H), 1.16-1.09 (m, 1H), 0.88-0.79 (m, 1H), 0.73-0.53 (m, 5H), 0.57-0.43 (m, 1H), 0.23-0.14 (m, 1H). |
| 169 | 614.4 | 1H NMR (400 MHz, DMSO-d6) δ 8.04 (d, J = 8.1 Hz, 1H), 8.02 (brs, 1H), 7.85 (d, J = 7.4 Hz, 1H), 7.81 (brs, 3H), 7.68-7.58 (m, 1H), 7.29 (s, 1H), 7.19 (d, J = 8.2 Hz, 1H), 5.16-5.06 (m, 1H), 4.95-4.82 (m, 1H), 4.71-4.59 (m, 1H), 3.81 (s, 2H), 3.38-3.01 (m, 4H), 2.11-1.86 (m, 2H), 1.87-1.48 (m, 5H), 1.46 (d, J = 7.1 Hz, 3H), 1.42-1.26 (m, 3H), 1.28-1.22 (m, 1H), 1.21 (s, 3H), 1.17-0.99 (m, 2H), 0.98-0.86 (m, 1H), 0.95 (s, 3H), 0.63-0.49 (m, 1H). |
| 170 | 624.4 | 1H NMR (400 MHz, DMSO-d6) δ 8.10 (d, J = 8.1 Hz, 1H), 8.09 (d, J = 6.4 Hz, 1H), 7.95 (brs, 3H), 7.69 (s, 1H), 7.42 (s, 1H), 7.26 (d, J = 8.2 Hz, 1H), 7.07 (s, 1H), 6.92 (d, J = 1.2 Hz, 1H), 5.14-5.05 (m, 1H), 4.62-4.50 (m, 2H), 4.13 (s, 3H), 4.00 (s, 4H), 3.77 (s, 3H), 3.35-3.04 (m, 4H), 2.92-2.80 (m, 1H), 2.76-2.65 (m, 1H), 2.07-1.97 (m, 1H), 1.87-1.69 (m, 3H), 1.68-1.46 (m, 2H), 1.55 (d, J = 6.8 Hz, 3H), 1.28-1.06 (m, 1H). |
| 171 | 620.3 | 1H NMR (400 MHz, DMSO-d6) δ 9.66 (d, J = 5.6 Hz, 1H), 8.22 (d, J = 8.1 Hz, 1H), 7.96 (brs, 3H), 7.72 (s, 1H), 7.44 (s, 1H), 7.38 (d, J = 8.2 Hz, 1H), 7.17 (s, 1H), 6.93 (d, J = 1.1 Hz, 1H), 5.34-5.25 (m, 1H), 5.00 4.88 (m, 1H), 4.80-4.70 (m, 1H), 4.15 (s, 3H), 4.15 (s, 3H), 4.00 (s, 3H), 3.37-3.04 (m, 3H), 2.48-2.39 (m, 2H), 2.07-1.89 (m, 3H), 1.80-1.70 (m, 1H), 1.66-1.50 (m, 1H), 1.59 (d, J = 6.5 Hz, 3H). |
| 172 | 624.4 | 1H NMR (400 MHz, DMSO-d6) δ 8.50 (d, J = 7.5 Hz, 1H), 8.15 (d, J = 8.1 Hz, 1H), 7.98 (brs, 3H), 7.43 (s, 1H), 7.34 (s, 1H), 7.31 (d, J = 8.1 Hz, 1H), 7.10 (s, 1H), 6.93 (d, J = 1.2 Hz, 1H), 5.39-5.29 (m, 1H), 4.77-4.67 (m, 2H), 4.61-4.50 (m, 2H), 4.13 (s, 3H), 4.00 (s, 3H), 3.93 (s, 3H), 3.36-3.04 (m, 3H), 2.60-2.50 (m, 1H), 2.38-2.24 (m, 1H), 2.09-1.92 (m, 1H), 1.82-1.51 (m, 4H), 1.57 (d, J = 6.8 Hz, 3H), 1.29-1.14 (m, 1H), 1.14-0.96 (m, 1H). |
| 173 | 629.5 | 1H NMR (400 MHz, DMSO-d6) δ 8.06 (d, J = 7.7 Hz, 1H), 8.00 (brs, 3H), 7.61 (d, J = 8.2 Hz, 1H), 7.43 (s, 1H), 7.35 (s, 1H), 7.08 (dd, J = 8.3, 1.2 Hz, 1H), 7.00 (s, 1H), 6.92 (d, J = 1.2 Hz, 1H), 5.12-5.01 (m, 1H), 4.67-4.57 (m, 1H), 4.24-4.13 (m, 2H), 4.11 (s, 3H), 3.99 (s, 3H), 3.74-3.68 (m, 1H), 3.60-3.50 (m, 2H), 3.37 (s, 3H), 2.13-1.89 (m, 2H), 1.81-1.57 (m, 3H), 1.52-1.32 (m, 3H), 1.45 (d, J = 7.1 Hz, 3H), 1.24 (s, 3H), 1.19-0.99 (m, 3H), 0.95 (s, 3H). |
| 174 | 614.4 | 1H NMR (400 MHz, DMSO-d6) δ 8.45 (d, J = 8.6 Hz, 1H), 7.99 (d, J = 8.0 Hz, 1H), 7.99 (brs, 3H), 7.45 (s, 1H), 7.14 (d, J = 8.1 Hz, 1H), 7.02 (s, |

TABLE 3-continued

| Example | ES/MS m/z [M + H]+ | 1H NMR |
|---|---|---|
| | | 1H), 6.93 (d, J = 1.2 Hz, 1H), 5.06-4.96 (m, 1H), 4.75-4.55 (m, 2H), 4.12 (s, 3H), 3.99 (s, 3H), 3.74-3.68 (m, 1H), 3.62-3.49 (m, 2H), 3.45-3.35 (m, 1H), 3.37 (s, 3H), 2.01-1.71 (m, 3H), 1.70-1.48 (m, 4H), 1.43 (d, J = 7.1 Hz, 3H), 1.42-1.32 (m, 1H), 1.27-1.14 (m, 1H), 0.92-0.81 (m, 1H), 0.78-0.59 (m, 2H), 0.52-0.43 (m, 1H). |
| 175 | 628.3 | 1H NMR (400 MHz, DMSO-d6) δ 8.02 (d, J = 8.1 Hz, 1H), 7.96 (brs, 3H), 7.45 (s, 1H), 7.24 (d, J = 7.6 Hz, 1H), 7.17 (d, J = 8.1 Hz, 1H), 7.01 (s, 1H), 6.93 (s, 1H), 4.96-4.85 (m, 1H), 4.63-4.52 (m, 1H), 4.52-4.44 (m, 1H), 4.13 (s, 3H), 3.99 (s, 3H), 3.76-3.68 (m, 1H), 3.63-3.47 (m, 2H), 3.37 (s, 3H), 2.02-1.83 (m, 3H), 1.82-1.56 (m, 3H), 1.55-1.43 (m, 3H), 1.51 (d, J = 7.2 Hz, 3H), 1.41-1.19 (m, 2H), 1.15 (s, 3H), 0.36 (dd, J = 6.5, 4.4 Hz, 1H). |
| 176 | 614.7 | 1H NMR (400 MHz, DMSO-d6) δ 8.65 (brs, 2H), 8.45 (d, J = 7.4 Hz, 1H), 8.05 (d, J = 8.1 Hz, 1H), 7.99 (d, J = 6.3 Hz, 1H), 7.84 (d, J = 7.3 Hz, 1H), 7.60 (d, J = 10.5 Hz, 1H), 7.31 (s, 1H), 7.19 (d, J = 8.1 Hz, 1H), 5.16-5.05 (m, 1H), 4.96-4.82 (m, 1H), 4.75-4.59 (m, 1H), 4.22-4.13 (m, 1H), 3.88-3.76 (m, 1H), 3.44-3.32 (m, 1H), 3.28-3.17 (m, 1H), 2.95-2.78 (m, 2H), 2.03-1.86 (m, 3H), 1.80-1.52 (m, 4H), 1.46 (d, J = 7.1 Hz, 3H), 1.43-1.23 (m, 3H), 1.22 (s, 4H), 1.17-0.99 (m, 3H), 0.95 (s, 3H), 0.92-0.83 (m, 1H), 0.59-0.48 (m, 1H). |
| 177 | 572.6 | 1H NMR (400 MHz, DMSO-d6) δ 9.14 (d, J = 6.6 Hz, 1H), 8.72 (brs, 2H), 8.06 (d, J = 8.1 Hz, 1H), 8.00 (d, J = 1.2 Hz, 1H), 7.82 (d, J = 7.4 Hz, 1H), 7.36 (d, J = 1.3 Hz, 1H), 7.20 (d, J = 8.1 Hz, 1H), 7.07 (s, 1H), 5.18-5.08 (m, 1H), 4.91-4.77 (m, 2H), 4.47-4.36 (m, 2H), 4.26-4.14 (m, 2H), 4.14 (s, 3H), 4.02 (s, 3H), 1.93 (t, J = 12.4 Hz, 1H), 1.76-1.61 (m, 2H), 1.54-1.28 (m, 3H), 1.45 (d, J = 7.1 Hz, 3H), 1.21 (s, 3H), 1.18-1.03 (m, 2H), 0.95 (s, 4H). |
| 178 | 617.9 | 1H NMR (400 MHz, DMSO-d6) δ 8.78 (brs, 2H), 8.72 (d, J = 7.9 Hz, 1H), 8.05 (d, J = 7.6 Hz, 1H), 7.62 (d, J = 8.2 Hz, 1H), 7.35 (d, J = 1.3 Hz, 1H), 7.34 (s, 1H), 7.08 (dd, J = 8.3, 1.2 Hz, 1H), 7.04 (s, 1H), 5.13-5.03 (m, 1H), 4.96-4.88 (m, 1H), 4.85-4.76 (m, 1H), 4.69-4.59 (m, 1H), 4.51-4.39 (m, 1H), 4.24-4.15 (m, 1H), 4.14 (s, 3H), 4.02 (s, 3H), 3.51-3.31 (m, 2H), 3.15-2.91 (m, 3H), 2.40-2.31 (m, 2H), 2.14-2.02 (m, 1H), 2.00-1.73 (m, 2H), 1.71-1.55 (m, 1H), 1.54-1.35 (m, 2H), 1.45 (d, J = 7.1 Hz, 3H), 1.25 (s, 3H), 1.20-1.04 (m, 3H), 0.95 (s, 3H). |
| 179 | 632.4 | 1H NMR (400 MHz, DMSO-d6) δ 8.82 (brs, 2H), 8.65 (d, J = 8.1 Hz, 1H), 8.05 (d, J = 8.1 Hz, 1H), 8.00 (d, J = 6.4 Hz, 1H), 7.86 (d, J = 7.3 Hz, 1H), 7.63 (d, J = 10.6 Hz, 1H), 7.31 (s, 1H), 7.19 (d, J = 8.1 Hz, 1H), 5.16-5.06 (m, 1H), 4.96-4.84 (m, 2H), 4.81-4.73 (m, 1H), 4.71-4.60 (m, 1H), 4.42-4.35 (m, 1H), 3.52-3.28 (m, 2H), 3.13-2.90 (m, 2H), 2.42-2.27 (m, 1H), 2.00-1.83 (m, 2H), 1.77-1.49 (m, 2H), 1.46 (d, J = 7.1 Hz, 3H), 1.44-1.22 (m, 5H), 1.22 (s, 3H), 1.17-0.99 (m, 3H), 0.94 (s, 3H), 0.93-0.83 (m, 1H), 0.60-0.49 (m, 1H). |
| 180 | 642.4 | 1H NMR (400 MHz, DMSO-d6) δ 9.62 (brs, 2H), 8.71 (d, J = 8.0 Hz, 1H), 8.11 (d, J = 8.1 Hz, 1H), 8.09 (d, J = 6.9 Hz, 1H), 8.00 (d, J = 1.1 Hz, 1H), 7.70 (s, 1H), 7.37 (d, J = 1.3 Hz, 1H), 7.27 (d, J = 8.1 Hz, 1H), 7.11 (s, 1H), 5.15-5.05 (m, 1H), 4.95-4.86 (m, 1H), 4.85-4.74 (m, 1H), 4.61-4.51 (m, 2H), 4.50-4.36 (m, 1H), 4.16 (s, 3H), 4.03 (s, 3H), 3.78 (s, 3H), 3.49-3.36 (m, 2H), 3.14-2.81 (m, 3H), 2.78-2.64 (m, 2H), 1.98-1.72 (m, 2H), 1.67-1.54 (m, 2H), 1.54 (d, J = 6.9 Hz, 3H), 1.29-1.14 (m, 2H). |
| 181 | 642.2 | 1H NMR (400 MHz, DMSO-d6) δ 8.78 (brs, 2H), 8.72 (d, J = 7.9 Hz, 1H), 8.49 (d, J = 7.4 Hz, 1H), 8.16 (d, J = 8.1 Hz, 1H), 8.01 (d, J = 1.3 Hz, 1H), 7.37 (d, J = 1.3 Hz, 1H), 7.34 (s, 1H), 7.33 (d, J = 8.3 Hz, 1H), 7.14 (s, 1H), 5.39-5.29 (m, 1H), 4.97-4.67 (m, 3H), 4.63-4.36 (m, 2H), 4.16 (s, 3H), 4.03 (s, 3H), 3.94 (s, 3H), 3.50-3.34 (m, 2H), 3.14-2.91 (m, 2H), 2.64-2.51 (m, 1H), 2.42-2.27 (m, 2H), 2.06-1.86 (m, 2H), 1.86-1.74 (m, 1H), 1.73-1.62 (m, 1H), 1.57 (d, J = 6.8 Hz, 3H), 1.28-1.21 (m, 1H), 1.17-1.03 (m, 1H). |
| 182 | 616.3 | 1H NMR (400 MHz, DMSO-d6) δ 8.78 (s, 2H), 8.63 (d, J = 8.0 Hz, 1H), 8.45 (d, J = 8.5 Hz, 1H), 8.00 (d, J = 6.2 Hz, 1H), 7.99 (d, J = 8.0 Hz, 1H), 7.62 (d, J = 10.6 Hz, 1H), 7.30 (s, 1H), 7.14 (d, J = 8.1 Hz, 1H), 5.08-4.95 (m, 1H), 4.94-4.70 (m, 3H), 4.51-4.35 (m, 1H), 3.96-3.79 (m, 1H), 3.51-3.30 (m, 2H), 3.13-2.89 (m, 2H), 2.40-2.26 (m, 1H), 2.04-1.80 (m, 2H), 1.73-1.31 (m, 5H), 1.44 (d, J = 7.1 Hz, 3H), 1.31-1.08 (m, 3H), 0.95-0.82 (m, 2H), 0.78-0.54 (m, 3H), 0.52-0.42 (m, 1H). |
| 183 | 643.3 | 1H NMR (400 MHz, DMSO-d6) δ 8.79 (d, J = 7.4 Hz, 1H), 8.76 (brs, 2H), 8.71 (d, J = 7.9 Hz, 1H), 8.16 (d, J = 8.1 Hz, 1H), 8.01 (d, J = 1.3 Hz, 1H), 7.37 (d, J = 1.3 Hz, 1H), 7.33 (d, J = 8.1 Hz, 1H), 7.14 (s, 1H), 5.39-5.29 (m, 1H), 4.98-4.76 (m, 1H), 4.73-4.62 (m, 1H), 4.62-4.51 (m, 1H), 4.51-4.40 (m, 1H), 4.17 (s, 3H), 4.13 (s, 3H), 4.09-3.99 (m, 1H), 4.03 (s, 3H), 3.51-3.32 (m, 2H), 3.16-2.92 (m, 2H), 2.91-2.53 (m, 3H), 2.44-2.29 (m, 1H), 2.04-1.63 (m, 3H), 1.59 (d, J = 6.9 Hz, 3H), 1.37-1.15 (m, 2H). |
| 184 | 602.6 | 1H NMR (400 MHz, DMSO-d6) δ 8.76 (brs, 2H), 8.71 (d, J = 7.9 Hz, 1H), 8.43 (d, J = 8.6 Hz, 1H), 8.01 (d, J = 1.3 Hz, 1H), 7.96 (d, J = 8.1 Hz, |

TABLE 3-continued

| Example | ES/MS m/z [M + H]+ | ¹H NMR |
|---|---|---|
| | | 1H), 7.36 (d, J = 1.3 Hz, 1H), 7.14 (d, J = 8.1 Hz, 1H), 7.06 (s, 1H), 5.07-4.97 (m, 1H), 4.92 (td, J = 9.4, 4.5 Hz, 1H), 4.80 (td, J = 9.4, 4.5 Hz, 1H), 4.74-4.63 (m, 1H), 4.62-4.52 (m, 1H), 4.52-4.38 (m, 1H), 4.15 (s, 3H), 4.03 (s, 3H), 3.51-3.34 (m, 2H), 3.14-2.88 (m, 2H), 2.41-2.31 (m, 1H), 2.02-1.81 (m, 1H), 1.75-1.53 (m, 5H), 1.43 (d, J = 7.1 Hz, 3H), 1.35-1.11 (m, 1H), 0.92-0.81 (m, 1H), 0.77-0.60 (m, 2H), 0.54-0.43 (m, 1H). |
| 185 | 643.5 | 1H NMR (400 MHz, DMSO-d6) δ 8.77 (brs, 2H), 8.70 (d, J = 7.9 Hz, 1H), 8.56 (d, J = 6.9 Hz, 1H), 8.09 (d, J = 8.1 Hz, 1H), 8.00 (s, 1H), 7.36 (s, 1H), 7.25 (d, J = 8.1 Hz, 1H), 7.08 (s, 1H), 5.20-5.10 (m, 1H), 4.97-4.88 (m, 1H), 4.84-4.74 (m, 1H), 4.59-4.36 (m, 3H), 4.16 (s, 3H), 4.16 (s, 3H), 4.02 (s, 3H), 3.50-3.28 (m, 1H), 3.16-2.88 (m, 1H), 2.87-2.61 (m, 2H), 2.42-2.26 (m, 1H), 2.01-1.79 (m, 2H), 1.75-1.41 (m, 2H), 1.58 (d, J = 7.0 Hz, 3H), 1.34-1.14 (m, 2H), 1.08-0.92 (m, 1H). |
| 186 | 674.7 | 1H NMR (400 MHz, DMSO-d6) δ 8.92 (d, J = 7.1 Hz, 1H), 8.84-8.72 (m, 1H), 8.75 (brs, 2H), 8.69 (d, J = 8.0 Hz, 1H), 8.16 (d, J = 8.0 Hz, 1H), 7.98 (s, 1H), 7.42-7.31 (m, 4H), 7.28 (d, J = 7.4 Hz, 1H), 7.26-7.21 (m, 2H), 5.36-5.10 (m, 3H), 4.97-4.74 (m, 1H), 4.49-4.37 (m, 1H), 4.14 (s, 3H), 4.03 (s, 3H), 3.51-3.31 (m, 1H), 3.14-2.88 (m, 2H), 2.41-2.21 (m, 2H), 1.97-1.83 (m, 1H), 1.73-1.55 (m, 1H), 1.54-1.39 (m, 1H).1.47 (d, J = 7.1 Hz, 3H), 1.28-1.05 (m, 1H). |
| 187 | 616.7 | 1H NMR (400 MHz, DMSO-d6) δ 8.77 (brs, 2H), 8.70 (d, J = 7.9 Hz, 1H), 8.06-7.99 (m, 2H), 7.36 (s, 1H), 7.22 (d, J = 7.6 Hz, 1H), 7.17 (d, J = 8.2 Hz, 1H), 7.05 (s, 1H), 4.97-4.86 (m, 1H), 4.91-4.76 (m, 1H), 4.64-4.54 (m, 1H), 4.53-4.37 (m, 2H), 4.16 (s, 3H), 4.03 (s, 3H), 3.50-3.30 (m, 1H), 3.18-2.87 (m, 2H), 2.40-2.32 (m, 1H), 2.00-1.85 (m, 2H), 1.74-1.58 (m, 3H), 1.57-1.44 (m, 2H), 1.51 (d, J = 7.2 Hz, 3H), 1.44-1.22 (m, 4H), 1.16 (s, 3H), 0.40-0.33 (m, 1H). |
| 188 | 574.4 | 1H NMR (400 MHz, DMSO-d6) δ 8.95 (d, J = 1.9 Hz, 1H), 8.88 (d, J = 8.1 Hz, 1H), 8.86 (brs, 2H), 8.68 (d, J = 1.9 Hz, 1H), 8.46 (d, J = 8.5 Hz, 1H), 8.04 (d, J = 8.0 Hz, 1H), 7.27 (s, 1H), 7.17 (d, J = 8.1 Hz, 1H), 5.09-4.98 (m, 1H), 4.97-4.70 (m, 3H), 4.51-4.43 (m, 1H), 4.06 (s, 3H), 3.47 (d, J = 12.6 Hz, 1H), 3.40 (d, J = 12.6 Hz, 1H), 3.15-2.96 (m, 2H), 2.44-2.30 (m, 1H), 2.03-1.53 (m, 7H), 1.53-1.39 (m, 1H), 1.44 (d, J = 7.1 Hz, 3H), 1.37-1.19 (m, 1H), 0.90-0.82 (m, 1H), 0.77-0.59 (m, 2H), 0.52-0.45 (m, 1H). |
| 189 | 670.5 | 1H NMR (400 MHz, DMSO-d6) δ 8.81 (d, J = 8.0 Hz, 1H), 8.80 (brs, 2H), 8.58 (d, J = 8.8 Hz, 1H), 8.08 (d, J = 8.0 Hz, 1H), 7.82 (dd, J = 5.2, 1.2 Hz, 1H), 7.40 (s, 1H), 7.25 (d, J = 8.1 Hz, 1H), 5.85-5.73 (m, 1H), 5.26-5.16 (m, 1H), 5.12-5.00 (m, 1H), 4.94-4.69 (m, 1H), 4.46-4.35 (m, 1H), 4.12-4.01 (m, 1H), 3.43 (dd, J = 37.5, 12.5 Hz, 2H), 3.28-2.86 (m, 2H), 2.43-2.28 (m, 1H), 2.23-2.02 (m, 2H), 2.01-1.87 (m, 1H), 1.70-1.50 (m, 2H), 1.44 (d, J = 7.0 Hz, 3H), 1.38-1.18 (m, 2H), 1.15-0.99 (m, 2H), 0.90-0.81 (m, 1H), 0.73-0.57 (m, 1H), 0.54-0.44 (m, 3H). |
| 190 | 641.7 | 1H NMR (400 MHz, DMSO-d6) δ 9.38 (brs, 1H), 8.89 (brs, 1H), 8.05 (d, J = 7.7 Hz, 1H), 7.61 (d, J = 8.2 Hz, 1H), 7.41 (dd, J = 2.2, 1.1 Hz, 1H), 7.35 (s, 1H), 7.08 (dd, J = 8.3, 1.2 Hz, 1H), 7.00 (s, 1H), 6.92 (s, 1H), 5.12-4.99 (m, 1H), 4.69-4.54 (m, 2H), 4.25-4.14 (m, 1H), 4.11 (s, 3H), 4.05-3.94 (m, 2H), 3.99 (s, 3H), 3.78-3.53 (m, 3H), 3.38-2.97 (m, 2H), 2.14-2.00 (m, 1H), 1.92-1.80 (m, 2H), 1.75-1.62 (m, 2H), 1.49-1.30 (m, 4H), 1.45 (d, J = 7.1 Hz, 3H), 1.24 (s, 2H), 1.18-0.99 (s, 5H), 0.94 (s, 3H). |
| 191 | 635.5 | 1H NMR (400 MHz, DMSO-d6) δ 9.00 (s, 1H), 8.90 (s, 1H), 8.72 (d, J = 9.0 Hz, 1H), 8.06-7.99 (m, 2H), 7.62 (d, J = 8.2 Hz, 1H), 7.37 (d, J = 1.2 Hz, 1H), 7.34 (s, 1H), 7.08 (d, J = 8.4 Hz, 1H), 7.04 (s, 1H), 5.12-5.02 (m, 1H), 5.01-4.85 (m, 1H), 4.71-4.58 (m, 1H), 4.23-4.14 (m, 1H), 4.14 (s, 3H), 4.02 (s, 3H), 3.60-3.44 (m, 4H), 3.28-3.07 (m, 2H), 2.41-2.21 (m, 1H), 2.15-2.01 (m, 1H), 1.86-1.74 (m, 1H), 1.71-1.58 (m, 1H), 1.54-1.36 (m, 2H), 1.45 (d, J = 7.1 Hz, 4H), 1.25 (s, 3H), 1.19-1.04 (m, 2H), 0.95 (s, 3H). |
| 192 | 668.4 | 1H NMR (400 MHz, DMSO-d6) δ 8.33 (brs, 3H), 8.05 (d, J = 8.1 Hz, 1H), 7.84 (d, J = 7.4 Hz, 1H), 7.47 (d, J = 1.1 Hz, 1H), 7.19 (d, J = 8.2 Hz, 1H), 7.04 (s, 1H), 6.96 (s, 1H), 5.18-5.05 (m, 1H), 4.90-4.74 (m, 1H), 4.50-4.34 (m, 2H), 4.12 (s, 3H), 4.00 (s, 3H), 3.55 (brs, 1H), 3.29-3.03 (m, 2H), 2.94-2.80 (m, 1H), 2.14-1.85 (m, 2H), 1.75-1.54 (m, 2H), 1.52-1.26 (m, 3H), 1.45 (d, J = 7.1 Hz, 3H), 1.21 (s, 3H), 1.17-1.00 (m, 3H), 0.95 (s, 3H). |
| 193 | 618.4 | 1H NMR (400 MHz, DMSO-d6) δ 8.06 (brs, 3H), 8.05 (d, J = 8.1 Hz, 1H), 7.84 (d, J = 7.5 Hz, 1H), 7.39 (d, J = 1.1 Hz, 1H), 7.19 (d, J = 8.1 Hz, 1H), 7.04 (s, 1H), 6.89 (d, J = 1.2 Hz, 1H), 5.17-5.08 (m, 1H), 4.94 (brs, 1H), 4.87-4.77 (m, 1H), 4.48-4.35 (m, 1H), 4.12 (s, 3H), 3.99 (s, 3H), 3.88-3.66 (m, 4H), 3.49-3.33 (m, 1H), 3.06-2.84 (m, 1H), 2.42-2.31 (m, 1H), 2.00-1.84 (m, 1H), 1.85-1.52 (m, 2H), 1.45 (d, J = 7.1 Hz, 3H), 1.43-1.27 (m, 4H), 1.21 (s, 3H), 1.16-1.00 (m, 1H), 0.95 (s, 3H). |

TABLE 3-continued

| Example | ES/MS m/z [M + H]+ | ¹H NMR |
|---|---|---|
| 194 | 632.3 | 1H NMR (400 MHz, DMSO-d6) δ 8.11 (brs, 3H), 8.04 (d, J = 8.1 Hz, 1H), 7.90 (brs, 1H), 7.86 (d, J = 7.4 Hz, 1H), 7.76-7.66 (m, 1H), 7.63 (d, J = 9.6 Hz, 1H), 7.29 (d, J = 4.9 Hz, 1H), 7.19 (d, J = 8.1 Hz, 1H), 5.16-5.06 (m, 1H), 5.03-4.55 (m, 4H), 3.91-3.77 (m, 2H), 3.46-3.29 (m, 2H), 3.19-2.81 (m, 2H), 2.43-2.27 (m, 1H), 2.02-1.52 (m, 4H), 1.46 (d, J = 7.1 Hz, 3H), 1.43-1.24 (m, 4H), 1.21 (s, 3H), 1.15-0.99 (m, 2H), 0.94 (s, 3H), 0.65-0.47 (m, 1H). |
| 195 | 616.4 | 1H NMR (400 MHz, DMSO-d6) δ 8.05 (d, J = 8.0 Hz, 1H), 7.91 (brs, 3H), 7.83 (d, J = 7.5 Hz, 1H), 7.44 (s, 1H), 7.19 (d, J = 8.1 Hz, 1H), 7.03 (s, 1H), 6.93 (d, J = 1.1 Hz, 1H), 5.72 (brs, 1H), 5.18-5.08 (m, 1H), 4.86-4.76 (m, 1H), 4.51-4.32 (m, 2H), 4.12 (s, 3H), 4.09-4.01 (m, 1H), 3.99 (s, 3H), 3.60-3.28 (m, 4H), 1.93 (t, J = 12.2 Hz, 1H), 1.86-1.53 (m, 3H), 1.45 (d, J = 7.1 Hz, 3H), 1.42-1.26 (m, 3H), 1.21 (s, 3H), 1.18-1.00 (m, 2H), 0.95 (s, 3H). |
| 196 | 614.4 | 1H NMR (400 MHz, DMSO-d6) δ 8.05 (d, J = 8.1 Hz, 1H), 7.92 (brs, 3H), 7.84 (d, J = 7.5 Hz, 1H), 7.49 (s, 1H), 7.19 (d, J = 8.1 Hz, 1H), 7.04 (s, 1H), 6.94 (d, J = 1.2 Hz, 1H), 5.19-5.05 (m, 1H), 4.88-4.77 (m, 1H), 4.45-4.33 (m, 1H), 4.12 (s, 3H), 3.99 (s, 3H), 3.89-3.69 (m, 1H), 3.49-3.33 (m, 2H), 3.24-3.08 (m, 1H), 2.16-2.03 (m, 1H), 1.99-1.86 (m, 1H), 1.74-1.53 (m, 4H), 1.45 (d, J = 7.1 Hz, 3H), 1.44-1.27 (m, 4H), 1.21 (s, 3H), 1.17-1.03 (m, 2H), 1.01 (d, J = 7.0 Hz, 3H), 0.95 (s, 3H). |
| 197 | 604.4 | 1H NMR (400 MHz, DMSO-d6) δ 9.47 (brs, 1H), 9.26 (brs, 1H), 8.69 (d, J = 6.3 Hz, 1H), 8.05 (d, J = 8.1 Hz, 1H), 7.98 (d, J = 1.3 Hz, 1H), 7.82 (d, J = 7.4 Hz, 1H), 7.35 (d, J = 1.3 Hz, 1H), 7.19 (d, J = 8.1 Hz, 1H), 7.08 (s, 1H), 5.49-5.32 (m, 1H), 5.17-5.07 (m, 1H), 4.88-4.61 (m, 2H), 4.48-4.37 (m, 1H), 4.15 (s, 3H), 4.02 (s, 3H), 3.81-3.55 (m, 3H), 3.54-3.41 (m, 1H), 1.92 (t, J = 12.3 Hz, 1H), 1.75-1.61 (m, 1H), 1.53-1.28 (m, 3H), 1.45 (d, J = 7.1 Hz, 3H), 1.21 (s, 3H), 1.18-1.02 (m, 2H), 0.95 (s, 3H). |
| 198 | 604.4 | 1H NMR (400 MHz, DMSO-d6) δ 9.42 (brs, 1H), 9.02 (brs, 1H), 8.76 (d, J = 7.1 Hz, 1H), 8.09-8.06 (d, J = 8.2 Hz, 1H), 8.04 (s, 1H), 7.82 (d, J = 7.4 Hz, 1H), 7.39 (d, J = 1.2 Hz, 1H), 7.19 (d, J = 8.2 Hz, 1H), 7.07 (s, 1H), 5.43-5.24 (m, 1H), 5.18-5.08 (m, 1H), 4.90-4.68 (m, 2H), 4.49-4.37 (m, 2H), 4.15 (s, 3H), 4.03 (s, 3H), 3.83-3.53 (m, 3H), 3.49-3.34 (m, 1H), 1.93 (t, J = 12.4 Hz, 1H), 1.75-1.60 (m, 2H), 1.54-1.28 (m, 3H), 1.45 (d, J = 7.1 Hz, 3H), 1.21 (s, 3H), 1.16-1.04 (m, 2H), 0.95 (s, 3H). |
| 199 | 604.4 | 1H NMR (400 MHz, DMSO-d6) δ 9.43 (brs, 1H), 9.03 (brs, 1H), 8.76 (d, J = 7.1 Hz, 1H), 8.06 (d, J = 8.1 Hz, 1H), 8.04 (s, 1H), 7.82 (d, J = 7.4 Hz, 1H), 7.39 (d, J = 1.3 Hz, 1H), 7.19 (d, J = 8.1 Hz, 1H), 7.08 (s, 1H), 5.44-5.23 (m, 1H), 5.18-5.08 (m, 1H), 4.89-4.69 (m, 2H), 4.52-4.37 (m, 1H), 4.15 (s, 3H), 4.03 (s, 3H), 3.72-3.55 (m, 3H), 3.50-3.37 (m, 1H), 1.93 (t, J = 12.4 Hz, 1H), 1.75-1.59 (m, 2H), 1.53-1.27 (m, 3H), 1.45 (d, J = 7.1 Hz, 3H), 1.21 (s, 3H), 1.19-1.01 (m, 3H), 0.95 (s, 3H). |
| 200 | 605.2 | 1H NMR (400 MHz, DMSO-d6) δ 9.43 (s, 1H), 9.19 (s, 1H), 8.67 (d, J = 6.4 Hz, 1H), 8.05 (d, J = 8.1 Hz, 1H), 7.98 (d, J = 1.3 Hz, 1H), 7.80 (d, J = 7.4 Hz, 1H), 7.35 (d, J = 1.3 Hz, 1H), 7.19 (d, J = 8.1 Hz, 1H), 7.08 (s, 1H), 5.48-5.32 (m, 1H), 5.19-5.07 (m, 1H), 4.88-4.76 (m, 1H), 4.75-4.63 (m, 1H), 4.49-4.36 (m, 1H), 4.15 (s, 3H), 4.02 (s, 3H), 3.78-3.56 (m, 3H), 3.55-3.42 (m, 1H), 1.92 (t, J = 12.3 Hz, 1H), 1.75-1.59 (m, 2H), 1.53-1.27 (m, 3H), 1.45 (d, J = 7.1 Hz, 3H), 1.21 (s, 3H), 1.17-1.00 (m, 2H), 0.95 (s, 3H). |
| 201 | 612.7 | 1H NMR (400 MHz, DMSO-d6) δ 8.71 (d, J = 7.3 Hz, 1H), 8.58 (brs, 1H), 8.34 (brs, 1H), 8.09-8.04 (m, 2H), 7.81 (d, J = 7.4 Hz, 1H), 7.38 (s, 1H), 7.20 (d, J = 8.1 Hz, 1H), 7.08 (s, 1H), 5.18-5.07 (m, 1H), 4.88-4.77 (m, 1H), 4.50-4.38 (m, 2H), 4.15 (s, 3H), 4.03 (s, 3H), 3.65-3.51 (m, 1H), 3.15-2.96 (m, 2H), 2.01-1.85 (m, 1H), 1.77-1.61 (m, 3H), 1.49-1.22 (m, 5H), 1.45 (d, J = 7.1 Hz, 3H), 1.22 (s, 3H), 1.14-1.02 (m, 3H), 0.96 (s, 3H), 0.96-0.85 (m, 1H), 0.66-0.59 (m, 1H). |
| 202 | 612.7 | |
| 203 | 612.6 | 1H NMR (400 MHz, DMSO-d6) δ 8.53 (brs, 2H), 8.42 (d, J = 7.9 Hz, 1H), 8.05 (d, J = 8.1 Hz, 1H), 8.02 (s, 1H), 7.81 (d, J = 7.4 Hz, 1H), 7.37 (d, J = 1.3 Hz, 1H), 7.19 (d, J = 8.1 Hz, 1H), 7.07 (s, 1H), 5.18-5.07 (m, 1H), 4.97-4.74 (m, 2H), 4.50-4.38 (m, 1H), 4.15 (s, 3H), 4.02 (s, 3H), 3.62-3.52 (m, 1H), 3.30-3.18 (m, 1H), 3.01-2.99 (m, 1H), 1.98-1.87 (m, 1H), 1.75-1.61 (m, 3H), 1.53-1.27 (m, 5H), 1.45 (d, J = 7.1 Hz, 3H), 1.22 (s, 3H), 1.16-1.01 (m, 2H), 0.95 (s, 3H), 0.88-0.76 (m, 2H). |
| 204 | 636.5 | 1H NMR (400 MHz, DMSO-d6) δ 8.14 (brs, 3H), 8.05 (d, J = 8.1 Hz, 1H), 7.84 (d, J = 7.5 Hz, 1H), 7.44 (dd, J = 2.4, 1.2 Hz, 1H), 7.19 (d, J = 8.2 Hz, 1H), 7.04 (d, J = 1.5 Hz, 1H), 6.93 (s, 1H), 5.18-5.07 (m, 1H), 4.89-4.75 (m, 1H), 4.36-4.35 (m, 2H), 4.13 (s, 3H), 4.00 (s, 3H), 3.58-3.41 (m, 1H), 3.40-3.29 (m, 1H), 2.63-2.50 (m, 1H), 2.31-2.11 (m, 2H), 1.98-1.87 (m, 2H), 1.78-1.54 (m, 3H), 1.44-1.25 (m, 4H), 1.21 (s, 3H), 1.17-1.02 (m, 3H), 0.95 (s, 3H). |
| 205 | 626.5 | Major conformer: 1H NMR (400 MHz, DMSO-d6) δ 8.63 (d, J = 12.5 Hz, 1H), 8.56 (d, J = 4.0 Hz, 1H), 8.39-8.21 (m, 1H), 8.10 (d, J = 1.3 Hz, |

TABLE 3-continued

| Example | ES/MS m/z [M + H]+ | ¹H NMR |
|---|---|---|
| | | 1H), 8.05 (d, J = 8.1 Hz, 1H), 7.82 (d, J = 7.5 Hz, 1H), 7.36 (d, J = 1.3 Hz, 1H), 7.20 (d, J = 8.2 Hz, 1H), 7.07 (s, 1H), 5.18-5.07 (m, 1H), 4.89-4.76 (m, 1H), 4.50-4.39 (m, 1H), 4.15 (s, 3H), 4.02 (s, 3H), 3.83-3.76 (m, 1H), 3.48-3.34 (m, 2H), 3.03-2.90 (m, 2H), 2.62-2.52 (m, 2H), 1.97-1.85 (m, 3H), 1.85-1.58 (m, 4H), 1.45 (d, J = 7.1 Hz, 3H), 1.42-1.25 (m, 3H), 1.21 (s, 3H), 1.17-1.02 (m, 2H), 0.95 (s, 3H). |
| 206 | 612.8 | 1H NMR (400 MHz, DMSO-d6) δ 8.05 (d, J = 8.1 Hz, 1H), 7.94 (brs, 3H), 7.83 (d, J = 7.4 Hz, 1H), 7.39 (s, 1H), 7.20 (d, J = 8.1 Hz, 1H), 7.04 (d, J = 2.4 Hz, 1H), 6.91 (s, 1H), 5.19-5.07 (m, 1H), 4.87-4.77 (m, 1H), 4.48-4.33 (m, 1H), 4.12 (s, 3H), 3.99 (s, 3H), 3.58-3.45 (m, 2H), 1.98-1.87 (m, 1H), 1.77-1.50 (m, 1H), 1.45 (d, J = 7.1 Hz, 3H), 1.50-1.26 (m, 5H), 1.21 (s, 3H), 1.17-0.99 (m, 1H), 0.95 (s, 3H), 0.90-0.79 (m, 1H), 0.77-0.67 (m, 1H). |
| 207 | 640.5 | 1H NMR (400 MHz, DMSO-d6) δ 8.12 (d, J = 8.1 Hz, 1H), 8.09 (d, J = 8.0 Hz, 1H), 7.90 (brs, 2H), 7.47 (s, 1H), 7.26 (d, J = 8.2 Hz, 1H), 7.06 (s, 1H), 6.97 (d, J = 1.1 Hz, 1H), 5.70 (s, 1H), 5.32-5.21 (m, 1H), 4.89-4.77 (m, 1H), 4.76-4.57 (m, 1H), 4.49-4.35 (m, 1H), 4.14 (s, 3H), 4.07 (s, 1H), 4.01 (s, 3H), 3.56-3.40 (m, 2H), 2.45-2.20 (m, 2H), 2.18-1.91 (m, 4H), 1.93-1.69 (m, 3H), 1.69-1.53 (m, 1H), 1.46 (d, J = 6.9 Hz, 3H), 1.46-1.31 (m, 2H), 1.30-1.00 (m, 4H), 0.99-0.89 (m, 1H), 0.65-0.55 (m, 1H), 0.53-0.43 (m, 1H). |
| 208 | 639.5 | 1H NMR (400 MHz, DMSO-d6) δ 9.37 (brs, 1H), 8.89 (brs, 1H), 8.24 (d, J = 8.6 Hz, 1H), 7.61 (d, J = 8.2 Hz, 1H), 7.55 (s, 1H), 7.42 (d, J = 1.2 Hz, 1H), 7.08 (dd, J = 8.2, 1.2 Hz, 1H), 7.00 (s, 1H), 6.91 (d, J = 1.2 Hz, 1H), 5.25-5.14 (m, 1H), 4.70-4.58 (m, 1H), 4.31-4.19 (m, 1H), 4.12 (s, 3H), 4.06-3.98 (m, 2H), 4.00 (s, 3H), 3.90-3.47 (m, 6H), 3.36-2.93 (m, 2H), 2.38-2.28 (m, 1H), 1.94-1.66 (m, 4H), 1.52-1.33 (m, 2H), 1.46 (d, J = 7.1 Hz, 3H), 1.27-1.07 (m, 3H), 1.07-0.97 (m, 1H), 0.85-0.73 (m, 1H), 0.69-0.56 (m, 1H), 0.38-0.30 (m, 1H). |
| 209 | 571.4 | 1H NMR (400 MHz, DMSO-d6) δ 8.11 (brs, 3H), 7.91 (d, J = 8.0 Hz, 1H), 7.44 (s, 1H), 7.09 (d, J = 8.1 Hz, 1H), 6.59 (s, 1H), 6.55 (brs, 1H), 6.38 (s, 1H), 4.98-4.88 (m, 1H), 4.73-4.55 (m, 2H), 4.54-4.40 (m, 2H), 4.10 (s, 3H), 3.18-3.00 (m, 1H), 2.83 (s, 3H), 2.61 (s, 3H), 1.96-1.74 (m, 4H), 1.71-1.53 (m, 2H), 1.48 (d, J = 7.1 Hz, 3H), 1.36 (dd, J = 12.9, 4.4 Hz, 1H), 1.07-1.87 (m, 1H). |
| 210 | 585.3 | 1H NMR (400 MHz, DMSO-d6) δ 8.11 (brs, 3H), 7.90 (d, J = 8.0 Hz, 1H), 7.45 (s, 1H), 7.09 (d, J = 8.1 Hz, 1H), 6.59 (s, 1H), 6.39 (s, 1H), 6.10 (d, J = 8.4 Hz, 1H), 4.90-4.81 (m, 1H), 4.55-4.35 (m, 4H), 4.10 (s, 3H), 3.23-3.13 (m, 1H), 2.81 (s, 3H), 2.75 (s, 3H), 1.95-1.78 (m, 4H), 1.70-1.59 (m, 2H), 1.50 (d, J = 7.1 Hz, 3H), 1.36 (dd, J = 12.8, 4.3 Hz, 1H), 1.26-1.18 (m, 3H). |
| 211 | 613.4 | 1H NMR (400 MHz, DMSO-d6) δ 8.11 (brs, 3H), 7.95 (d, J = 8.0 Hz, 1H), 7.46 (s, 1H), 7.11 (d, J = 8.0 Hz, 1H), 6.62 (s, 1H), 6.39 (s, 1H), 6.33 (d, J = 7.4 Hz, 1H), 5.09-4.98 (m, 1H), 4.75-4.65 (m, 1H), 4.52-4.43 (m, 1H), 4.10 (s, 3H), 3.54-3.44 (m, 1H), 3.14-3.05 (m, 1H), 2.81 (s, 3H), 2.78 (s, 3H), 1.91-1.76 (m, 5H), 1.70-1.52 (m, 4H), 1.48-1.42 (m, 1H), 1.42 (d, J = 6.8 Hz, 3H), 1.35 (dd, J = 12.9, 4.3 Hz, 1H)1.30-1.08 (m, 5H), 1.01-0.90 (m, 1H). |
| 212 | 599.3 | 1H NMR (400 MHz, DMSO-d6) δ 8.13 (brs, 3H), 7.99 (d, J = 8.1 Hz, 1H), 7.47 (s, 1H), 7.16 (d, J = 8.1 Hz, 1H), 6.71 (d, J = 7.3 Hz, 1H), 6.63 (s, 1H), 6.40 (s, 1H), 5.09-5.01 (m, 1H), 4.74-4.64 (m, 1H), 4.42-4.31 (m, 1H), 4.11 (s, 3H), 3.76 (brs, 1H), 3.46-3.35 (m, 1H), 3.22-3.10 (m, 1H), 2.88 (s, 3H), 2.81 (s, 3H), 1.91-1.74 (m, 4H), 1.71-1.48 (m, 5H), 1.45 (d, J = 6.9 Hz, 3H), 1.44-1.33 (m, 2H), 1.36 (dd, J = 12.7, 4.3 Hz, 1H), 1.29-1.16 (m, 2H). |
| 213 | 662.5 | 1H NMR (400 MHz, DMSO-d6) δ 8.61 (d, J = 7.3 Hz, 1H), 8.11 (brs, 3H), 8.07 (dd, J = 7.9, 1.9 Hz, 1H), 8.02 (d, J = 7.9 Hz, 1H), 7.55-7.48 (m, 1H), 7.47 (s, 1H), 7.23 (d, J = 8.1 Hz, 1H), 7.17 (d, J = 8.1 Hz, 1H), 7.09 (dd, J = 7.9, 7.9 Hz, 1H), 6.69 (s, 1H), 6.37 (s, 1H), 5.45-5.35 (m, 1H), 4.95-4.81 (m, 1H), 4.69-4.40 (m, 3H), 4.21-4.14 (m, 1H), 4.11 (s, 3H), 4.06-3.98 (m, 1H), 2.85 (s, 3H), 1.91-1.94 (m, 5H), 1.73-1.61 (m, 2H), 1.53 (d, J = 6.5 Hz, 3H), 1.49-1.39 (m, 2H), 1.35 (dd, J = 12.7, 4.4 Hz, 1H), 1.19-1.10 (m, 1H), 0.70-0.55 (m, 2H). |
| 214 | 624.4 | 1H NMR (400 MHz, Acetonitrile-d3) δ 8.79 (dd, J = 4.5, 1.4 Hz, 0.5H, 1st isomer), 8.50 (dd, J = 8.4, 1.4 Hz, 0.5H 2nd isomer), 8.35 (d, J = 6.8 Hz, 1H), 8.26 (d, J = 7.1 Hz, 1H), 8.04 (d, J = 6.8 Hz, 1H), 8.02 (d, J = 6.8 Hz, 1H), 7.85 (s, 1.5H, 1st isomer), 7.79 (s, 1.5H, 2nd isomer), 7.55 (dd, J = 8.4, 4.4 Hz, 0.5H 1st isomer), 7.21 (s, 0.5H 1st isomer), 7.19 (s, 0.5H, 2nd isomer), 6.77 (s, 0.5H, 1st isomer), 6.75 (s, 0.5H, 2nd isomer), 6.74 (s, 0.5H, 1st isomer), 6.70 (s, 0.5H, 2nd isomer), 5.20-5.09 (m, 1H), 4.91-4.50 (m, 2H), 4.80 (dd, J = 14.3, 4.5 Hz, 1H), 4.38-4.06 (m, 2H), 4.23 (s, 1.5H, 1st isomer), 4.22 (s, 1.5H, 2nd isomer), 4.00-3.50 (m, 4H), 2.87-2.50 (m, 2H), 2.50-2.38 (m, 2H), 2.33-2.21 (m, 1H), 1.83-1.71 (m, 1H), 1.60-1.48 (m, 1H), 1.54 (d, J = 6.6 Hz, 1.5H, 1st isomer), 1.52 (d, J = 6.6 Hz, 1.5H, 2nd isomer), 1.01-0.85 (m, 2H), 0.60-0.41 (m, 2H), 0.40-0.26 (m, 1H), 0.21-0.12 (m, 1H). |

TABLE 3-continued

| Example | ES/MS m/z [M + H]+ | ¹H NMR |
|---|---|---|
| 215 | 583.5 | 1H NMR (400 MHz, DMSO-d6) δ 8.40 (d, J = 8.3 Hz, 1H), 8.09 (brs, 3H), 7.61 (d, J = 8.2 Hz, 1H), 7.58 (s, 1H), 7.48 (s, 1H), 7.09 (d, J = 8.2 Hz, 1H), 7.03 (s, 1H), 7.01 (s, 1H), 5.15-5.05 (m, 1H), 4.73-4.62 (m, 1H), 4.59-4.34 (m, 2H), 4.27-4.16 (m, 1H), 4.11 (s, 3H), 4.01 (s, 3H), 2.37-2.27 (m, 1H) 2.15-2.06 (m, 1H), 1.91-1.51 (m, 7H), 1.44 (d, J = 7.0 Hz, 3H), 1.41-1.29 (m, 1H), 1.34 (dd, J = 12.9, 4.3 Hz, 1H), 1.29-0.95 (m, 6H). |
| 216 | 611.6 | 1H NMR (400 MHz, DMSO-d6) δ 8.08 (brs, 3H), 8.06 (d, J = 8.1 Hz, 1H), 7.61 (d, J = 8.2 Hz, 1H), 7.57 (s, 1H), 7.34 (s, 1H), 7.09 (dd, J = 8.3, 1.2 Hz, 1H), 7.02 (d, J = 1.2 Hz, 1H), 7.00 (s, 1H), 5.11-5.00 (m, 1H), 4.69-4.57 (m, 1H), 4.54-4.36 (m, 2H), 4.23-4.15 (m, 1H), 4.10 (s, 3H), 4.00 (s, 3H), 3.84-3.69 (m, 1H), 2.34-2.24 (m, 1H), 2.34-2.24 (m, 1H), 2.13-2.01 (m, 1H), 1.91-1.57 (m, 5H), 1.51-1.37 (m, 1H), 1.45 (d, J = 7.1 Hz, 3H), 1.34 (dd, J = 12.9, 4.4 Hz, 1H), 1.24 (s, 3H), 1.17-1.01 (m, 3H), 0.94 (s, 3H). |
| 217 | 598.3 | 1H NMR (400 MHz, DMSO-d6) δ 8.49 (d, J = 7.3 Hz, 1H), 8.09 (brs, 3H), 8.06 (d, J = 8.0 Hz, 1H), 7.60 (s, 1H), 7.22 (d, J = 8.1 Hz, 1H), 7.04 (d, J = 1.2 Hz, 1H), 7.02 (s, 1H), 5.10-5.00 (m, 1H), 4.98 (dd, J = 14.2, 4.1 Hz, 1H), 4.81 (dd, J = 14.2, 3.4 Hz, 1H), 4.64-4.34 (m, 2H), 4.12 (s, 3H), 4.01 (s, 3H), 3.92-3.69 (m, 1H), 3.50-3.41 (m, 2H), 2.75 (t, J = 9.8 Hz, 1H), 2.63-2.53 (m, 1H), 2.37-2.25 (m, 1H), 2.09 (ddd, J = 14.4, 5.8, 2.5 Hz, 1H), 1.93-1.76 (m, 3H), 1.69-1.58 (m, 1H), 1.49-1.39 (m, 1H), 1.46 (d, J = 6.8 Hz, 3H), 1.35 (dd, J = 12.9, 4.4 Hz, 1H), 0.35-0.11 (m, 2H), 0.07-0.09 (m, 1H). |
| 218 | 598.3 | 1H NMR (400 MHz, DMSO-d6) δ 8.54 (d, J = 6.5 Hz, 1H), 8.08 (brs, 3H), 8.04 (d, J = 8.0 Hz, 1H), 7.60 (s, 1H), 7.20 (d, J = 8.0 Hz, 1H), 7.04 (d, J = 1.2 Hz, 1H), 7.03 (s, 1H), 5.02-4.94 (m, 1H), 4.69 (dd, J = 14.0, 3.6 Hz, 1H), 4.47 (br, 1H), 4.14 (s, 3H), 4.05-3.96 (m, 1H), 4.01 (s, 3H), 3.69-3.54 (m, 2H), 3.44-3.37 (m, 2H), 2.83 (dd, J = 11.1, 8.2 Hz, 1H), 2.69-2.61 (m, 1H), 2.39-2.24 (m, 1H), 2.17-2.08 (m, 1H), 1.92-1.71 (m, 4H), 1.68-1.57 (m, 1H), 1.44 (d, J = 6.9 Hz, 3H), 1.34 (dd, J = 12.8, 4.4 Hz, 1H), 1.01-0.87 (m, 1H), 0.51-0.43 (m, 1H), 0.37-0.30 (m, 1H). |
| 219 | 642.5 | 1H NMR (400 MHz, DMSO-d6) δ 8.09 (brs, 3H), 8.06 (d, J = 8.1 Hz, 1H), 7.72 (d, J = 8.5 Hz, 1H), 7.60 (s, 1H), 7.22 (d, J = 8.2 Hz, 1H), 7.04 (s, 2H), 5.25-5.11 (m, 1H), 4.83-4.72 (m, 1H), 4.44-4.33 (m, 1H), 4.11 (s, 3H), 4.01 (s, 3H), 3.84-3.69 (m, 2H), 3.53 (s, 3H), 3.10 (dd, J = 9.8, 2.6 Hz, 1H), 2.38-2.27 (m, 1H), 1.96-1.72 (m, 4H), 1.69-1.55 (m, 3H), 1.51-1.39 (m, 2H), 1.45 (d, J = 7.1 Hz, 3H), 1.38-1.28 (m, 3H), 1.26 (s, 3H), 1.23-1.10 (m, 1H), 1.00 (s, 3H). |
| 220 | 642.4 | 1H NMR (400 MHz, DMSO-d6) δ 8.08 (brs, 3H), 8.03 (d, J = 8.0 Hz, 1H), 7.96 (d, J = 6.2 Hz, 1H), 7.59 (s, 1H), 7.16 (d, J = 8.1 Hz, 1H), 7.04 (s, 2H), 5.04-4.94 (m, 1H), 4.91-4.79 (m, 1H), 4.48-4.37 (m, 2H), 4.11 (s, 3H), 4.01 (s, 3H), 3.73 (d, J = 8.9 Hz, 1H), 3.50 (s, 3H), 2.37-2.27 (m, 1H), 2.03-1.73 (m, 5H), 1.68-1.49 (m, 3H), 1.45 (d, J = 7.1 Hz, 3H), 1.38-1.25 (m, 2H), 1.25 (s, 3H), 1.03-0.89 (m, 2H), 0.80 (s, 3H), 0.82-0.69 (m, 1H). |
| 221 | 609.5 | 1H NMR (400 MHz, DMSO-d6) δ 8.24 (d, J = 8.6 Hz, 1H), 8.10 (brs, 3H), 7.61 (d, J = 8.2 Hz, 1H), 7.58 (s, 1H), 7.55 (s, 1H), 7.08 (dd, J = 8.3, 1.2 Hz, 1H), 7.03 (d, J = 1.2 Hz, 1H), 7.01 (s, 1H), 5.25-5.13 (m, 1H), 4.68-4.56 (m, 1H), 4.46 (brs, 2H), 4.29-4.18 (m, 1H), 4.12 (s, 3H), 4.01 (s, 3H), 3.79 (brs, 1H), 2.41-2.22 (m, 2H), 1.93-1.54 (m, 6H), 1.52-1.38 (m, 2H), 1.46 (d, J = 7.1 Hz, 3H), 1.34 (dd, J = 12.9, 4.4 Hz, 1H), 1.26-1.06 (m, 3H), 1.06-0.99 (m, 1H), 0.84-0.76 (m, 1H), 0.67-0.59 (m, 1H), 0.37-0.29 (m, 1H). |
| 222 | 613.5 | 1H NMR (400 MHz, DMSO-d6) δ 8.50 (d, J = 9.4 Hz, 1H), 8.09 (brs, 3H), 7.70 (s, 1H), 7.57 (d, J = 8.1 Hz, 1H), 7.57 (s, 1H), 7.07 (dd, J = 8.1, 1.2 Hz, 1H), 7.02 (d, J = 1.2 Hz, 1H), 7.01 (s, 1H), 5.26-5.06 (m, 1H), 4.80-4.65 (m, 1H), 4.45 (brs, 2H), 4.35-4.21 (m, 1H), 4.09 (s, 3H), 4.00 (s, 3H), 3.33-3.21 (m, 1H), 2.38-2.20 (m, 2H), 1.91-1.73 (m, 3H), 1.69-1.64 (m, 3H), 1.54-1.42 (m, 1H), 1.47 (d, J = 7.1 Hz, 3H), 1.38 (s, 3H), 1.34 (dd, J = 13.0, 4.6 Hz, 1H), 1.30-1.21 (m, 1H), 1.18 (s, 3H), 0.64-0.49 (m, 1H). |
| 223 | 596.5 | 1H NMR (400 MHz, DMSO-d6) δ 8.45 (d, J = 8.5 Hz, 1H), 8.10 (brs, 3H), 8.00 (d, J = 8.0 Hz, 1H), 7.59 (s, 1H), 7.14 (d, J = 8.0 Hz, 1H), 7.04 (d, J = 1.3 Hz, 1H), 7.03 (s, 1H), 5.08-4.94 (m, 1H), 4.75-4.66 (m, 1H), 4.64-4.56 (m, 1H), 4.43 (brs, 2H), 4.12 (s, 3H), 4.01 (s, 3H), 3.76 (brs, 2H), 2.38-2.27 (m, 1H), 1.92-1.73 (m, 4H), 1.72-1.48 (m, 5H), 1.43 (d, J = 7.1 Hz, 3H), 1.34 (dd, J = 12.8, 4.3 Hz, 1H), 1.29-1.16 (m, 1H), 0.91-0.82 (m, 1H), 0.77-0.57 (m, 2H), 0.52-0.44 (m, 1H). |
| 224 | 596.4 | 1H NMR (400 MHz, DMSO-d6) δ 8.40 (d, J = 7.1 Hz, 1H), 8.08 (brs, 3H), 8.02 (d, J = 8.2 Hz, 1H), 7.59 (s, 1H), 7.22 (d, J = 8.2 Hz, 1H), 7.04 (d, J = 1.2 Hz, 1H), 7.03 (s, 1H), 4.71-4.53 (m, 2H), 4.52-4.43 (m, 1H), 4.30 (brs, 2H), 4.13 (s, 3H), 4.01 (s, 3H), 3.75 (brs, 1H), 2.38-2.26 |

TABLE 3-continued

| Example | ES/MS m/z [M + H]+ | ¹H NMR |
|---|---|---|
| | | (m, 1H), 1.89-1.76 (m, 4H), 1.73 (d, J = 7.0 Hz, 3H), 1.68-1.39 (m, 5H), 1.36-1.21 (m, 3H), 0.94-0.84 (m, 2H), 0.82-0.65 (m, 1H), 0.49 (dd, J = 8.3, 3.0 Hz, 1H). |
| 225 | 635.6 | 1H NMR (400 MHz, DMSO-d6) δ 8.24 (d, J = 8.6 Hz, 1H), 8.10 (brs, 3H), 7.59 (d, J = 8.2 Hz, 1H), 7.55 (s, 1H), 7.54 (s, 1H), 7.13 (s, 1H), 7.06 (dd, J = 8.2, 1.2 Hz, 1H), 7.04 (d, J = 1.2 Hz, 1H), 5.24-5.13 (m, 1H), 4.88-4.75 (m, 1H), 4.43 (brs, 4H), 4.34-4.21 (m, 1H), 4.01 (s, 3H), 3.93-3.84 (m, 1H), 3.75 (brs, 1H), 2.41-2.21 (m, 2H), 1.92-1.72 (m, 3H), 1.70-1.56 (m, 2H), 1.46 (d, J = 7.0 Hz, 3H), 1.44-1.26 (m, 3H), 1.23-0.94 (m, 5H), 0.88-0.72 (m, 2H), 0.70-0.58 (m, 1H), 0.54-0.43 (m, 1H), 0.39-0.26 (m, 1H). |
| 226 | 596.4 | 1H NMR (400 MHz, DMSO-d6) δ 8.28 (d, J = 8.4 Hz, 1H), 8.08 (brs, 3H), 8.02 (d, J = 8.0 Hz, 1H), 7.58 (s, 1H), 7.19 (d, J = 8.0 Hz, 1H), 7.03 (d, J = 1.2 Hz, 1H), 6.98 (s, 1H), 5.13-5.02 (m, 1H), 4.93 (dd, J = 14.1, 4.5 Hz, 1H), 4.57 (dd, J = 14.1, 5.1 Hz, 1H), 4.52-4.39 (m, 2H), 4.10 (s, 3H), 4.01 (s, 3H), 3.94-3.68 (m, 3H), 2.43-2.26 (m, 1H), 1.90-1.70 (m, 4H), 1.69-1.56 (m, 1H), 1.58-1.39 (m, 2H), 1.46 (d, J = 7.0 Hz, 3H), 1.34 (dd, J = 12.9, 4.3 Hz, 1H), 1.17-1.03 (m, 1H), 0.90-0.72 (m, 1H), 0.65-0.52 (m, 1H), 0.11-0.02 (m, 1H), −0.01-−0.18 (m, 2H). |
| 227 | 585.4 | 1H NMR (400 MHz, DMSO-d6) δ 12.76 (s, 1H), 8.18 (brs, 3H), 8.02 (d, J = 8.1 Hz, 1H), 7.78-7.70 (m, 1H), 7.60 (d, J = 9.8 Hz, 1H), 7.17 (d, J = 8.1 Hz, 1H), 7.05 (d, J = 8.1 Hz, 1H), 7.04 (s, 1H), 4.91-4.81 (m, 1H), 4.68-4.60 (m, 1H), 4.58-4.34 (m, 1H), 4.12 (s, 3H), 4.07-4.01 (m, 1H), 4.02 (s, 3H), 3.94-3.83 (m, 1H), 3.24-3.14 (m, 2H), 2.81-2.63 (m, 1H), 2.49-2.38 (m, 1H), 1.92-1.60 (m, 4H), 1.45-1.22 (m, 3H), 1.32 (d, J = 7.1 Hz, 3H), 1.21-0.99 (m, 3H), 0.90-0.75 (m, 2H). |
| 228 | 568.4 | 1H NMR (400 MHz, DMSO-d6) δ 8.61 (d, J = 7.2 Hz, 1H), 8.27 (d, J = 8.6 Hz, 1H), 7.95 (s, 3H), 7.93 (d, J = 8.0 Hz, 2H), 7.74 (s, 1H), 7.14-7.03 (m, 2H), 6.76 (s, 1H), 5.16 (p, J = 7.2 Hz, 1H), 5.03-4.87 (m, 1H), 4.68-4.53 (m, 1H), 4.21-3.35 (m, 4H), 3.33-3.17 (m, 3H), 2.46-2.39 (m, 0H), 2.21-2.09 (m, 1H), 2.09-1.85 (m, 3H), 1.84-1.69 (m, 1H), 1.71-1.48 (m, 2H), 1.40 (d, J = 7.1 Hz, 3H), 1.35-1.19 (m, 1H), 1.20-1.01 (m, 2H), 1.03-0.88 (m, 2H), 0.70-0.49 (m, 1H), 0.49-0.35 (m, 1H), 0.36-0.19 (m, 1H). |
| 229 | 598.4 | 1H NMR (400 MHz, DMSO-d6) δ 8.32 (d, J = 8.5 Hz, 1H), 8.01 (d, J = 8.0 Hz, 1H), 7.91 (s, 3H), 7.36 (s, 1H), 7.16 (d, J = 8.0 Hz, 1H), 7.14 (s, 1H), 6.90 (s, 1H), 5.17 (p, J = 7.2 Hz, 1H), 5.10-4.90 (m, 1H), 4.78-4.62 (m, 1H), 4.39 (d, J = 133.1 Hz, 4H), 3.97 (s, 3H), 3.93-3.80 (m, 1H), 3.30-3.00 (m, 3H), 2.12-1.90 (m, 4H), 1.79-1.60 (m, 1H), 1.62-1.52 (m, 1H), 1.51-1.43 (m, 1H), 1.41 (d, J = 7.1 Hz, 3H), 1.34-1.23 (m, 1H), 1.23-1.06 (m, 2H), 1.03-0.92 (m, 3H), 0.88-0.76 (m, 1H), 0.72-0.55 (m, 1H), 0.47-0.31 (m, 1H). |
| 230 | 626.5 | 1H NMR (400 MHz, DMSO-d6) δ 8.00 (d, J = 8.1 Hz, 1H), 7.91 (s, 3H), 7.81 (d, J = 7.4 Hz, 1H), 7.36 (s, 1H), 7.15 (d, J = 8.2 Hz, 1H), 7.13 (s, 1H), 6.90 (s, 1H), 5.09 (p, J = 7.1 Hz, 1H), 4.92-4.77 (m, 1H), 4.67 4.48 (m, 1H), 3.97 (s, 3H), 3.93-3.83 (m, 1H), 3.76-3.40 (m, 6H), 3.30-3.20 (m, 1H), 3.19-2.98 (m, 1H), 2.07-1.95 (m, 1H), 1.90 (t, J = 11.6 Hz, 1H), 1.82-1.59 (m, 1H), 1.61-1.48 (m, 2H), 1.43 (d, J = 7.1 Hz, 3H), 1.41-1.24 (m, 3H), 1.19 (s, 3H), 1.14-0.94 (m, 2H), 0.93 (s, 3H), 0.86-0.73 (m, 1H), 0.51-0.37 (m, 1H). |
| 231 | 584.3 | 1H NMR (400 MHz, DMSO-d6) δ 8.30 (d, J = 7.3 Hz, 1H), 8.05 (s, 3H), 7.97 (d, J = 8.0 Hz, 1H), 7.35 (s, 1H), 6.90 (s, 1H), 5.03-4.89 (m, 1H), 4.86-4.66 (m, 2H), 3.97 (s, 3H), 3.92-3.80 (m, 1H), 3.11-2.92 (m, 6H), 2.28-2.10 (m, 2H), 2.06-1.92 (m, 1H), 1.92-1.83 (m, 1H), 1.78-1.68 (m, 1H), 1.63-1.47 (m, 3H), 1.46 (d, J = 7.1 Hz, 3H), 1.30-0.93 (m, 7H), 0.85-0.64 (m, 2H), 0.53-0.35 (m, 1H). |
| 232 | 558.3 | 1H NMR (400 MHz, DMSO-d6) δ 8.39 (t, J = 6.2 Hz, 1H), 8.02 (d, J = 8.1 Hz, 1H), 7.90 (s, 3H), 7.39 (s, 1H), 7.12 (d, J = 8.1 Hz, 1H), 7.01 (s, 1H), 6.89 (s, 1H), 4.61 (t, J = 7.5 Hz, 2H), 4.55 (d, J = 6.1 Hz, 2H), 4.10 (s, 3H), 3.97 (s, 3H), 3.31-2.93 (m, 2H), 2.29-2.20 (m, 2H), 2.06-1.94 (m, 1H), 1.79-1.69 (m, 1H), 1.64-1.42 (m, 8H), 1.42-1.29 (m, 2H), 1.15-1.03 (m, 3H). |
| 233 | 598.4 | 1H NMR (400 MHz, DMSO-d6) δ 8.09 (d, J = 8.1 Hz, 1H), 8.06 (d, J = 7.9 Hz, 1H), 7.96 (s, 3H), 7.44-7.36 (m, 2H), 7.30-7.19 (m, 2H), 7.04 (s, 1H), 6.90 (s, 1H), 5.25 (p, J = 7.0 Hz, 1H), 4.90-4.69 (m, 1H), 4.49-4.30 (m, 1H), 4.11 (s, 3H), 3.97 (s, 3H), 3.38-2.98 (m, 3H), 2.34-2.15 (m, 1H), 2.11-1.91 (m, 2H), 1.83-1.68 (m, 4H), 1.68-1.49 (m, 2H), 1.43 (d, J = 6.9 Hz, 3H), 1.42-1.30 (m, 1H), 1.28-1.15 (m, 1H), 1.15-0.97 (m, 2H), 0.92 (ddd, J = 9.6, 6.4, 3.3 Hz, 1H), 0.58 (ddd, J = 9.3, 6.2, 3.2 Hz, 1H), 0.45 (ddd, J = 9.2, 6.1, 3.1 Hz, 1H). |
| 234 | 572.4 | 1H NMR (400 MHz, DMSO-d6) δ 8.11 (d, J = 8.0 Hz, 0.4H, rotamer), 8.04 (d, J = 8.1 Hz, 0.69H, rotamer), 7.89 (s, 3H), 7.40 (s, 1H), 7.22 (d, J = 8.1 Hz, 0.42H, rotamer), 7.11 (d, J = 8.1 Hz, 0.72H, rotamer), 7.06 (s, 0.36H, rotamer), 7.00 (s, 0.61H, rotamer), 6.94-6.85 (m, 1H), 6.59-6.33 (m, 1H), 5.61 (d, J = 16.6 Hz, 1H), 4.78 (s, 1H), 4.69-4.61 (m, 1H), 4.61-4.51 (m, 1H), 4.48-4.31 (m, 1H), 4.09 (d, J = 1.4 Hz, 3H), 3.97 (s, |

TABLE 3-continued

| Example | ES/MS m/z [M + H]+ | ¹H NMR |
|---|---|---|
| | | 3H), 3.16 (s, 2H, rotamer), 2.97 (s, 1H, rotamer), 2.91-2.81 (m, 1H), 2.18-2.07 (m, 1H), 2.06-1.94 (m, 1H), 1.82-1.66 (m, 1H), 1.66-1.38 (m, 7H), 1.32 (s, 2H), 1.30-1.18 (m, 1H), 1.19-1.12 (m, 1H), 1.10-0.96 (m, 1H), 0.89-0.68 (m, 1H). |
| 235 | 626.3 | 1H NMR (400 MHz, DMSO-d6) δ 9.05 (d, J = 9.8 Hz, 1H), 8.19 (d, J = 8.1 Hz, 1H), 7.96 (s, 3H), 7.45 (d, J = 8.6 Hz, 2H), 7.16 (s, 1H), 6.93 (d, J = 1.2 Hz, 1H), 6.19-6.05 (m, 1H), 5.26-5.09 (m, 1H), 4.70-4.51 (m, 1H), 4.12 (s, 3H), 4.00 (s, 3H), 3.37-3.03 (m, 3H), 2.87-2.72 (m, 1H), 2.31-2.10 (m, 2H), 2.10-1.94 (m, 1H), 1.83-1.68 (m, 2H), 1.66-1.52 (m, 2H), 1.51-1.31 (m, 3H), 1.24 (d, J = 2.6 Hz, 1H), 1.16-0.99 (m, 2H), 0.95-0.77 (m, 2H), 0.72-0.52 (m, 1H), 0.34--0.03 (m, 1H). |
| 236 | 626.3 | 1H NMR (400 MHz, DMSO-d6) δ 9.05 (d, J = 9.8 Hz, 1H), 8.19 (d, J = 8.1 Hz, 1H), 7.95 (s, 3H), 7.45 (d, J = 8.6 Hz, 2H), 7.16 (s, 1H), 6.93 (s, 1H), 6.12 (p, J = 8.9 Hz, 1H), 5.28-5.08 (m, 1H), 4.69-4.58 (m, 1H), 4.12 (s, 3H), 4.00 (s, 3H), 3.36-3.00 (m, 3H), 2.87-2.72 (m, 1H), 2.32-2.11 (m, 2H), 2.12-1.89 (m, 1H), 1.86-1.68 (m, 2H), 1.68-1.50 (m, 2H), 1.51-1.31 (m, 3H), 1.24 (d, 1H), 1.16-0.98 (m, 2H), 0.98-0.77 (m, 2H), 0.75-0.46 (m, 1H), 0.31-0.08 (m, 1H). |
| 237 | 584.3 | 1H NMR (400 MHz, DMSO-d6) δ 8.85 (d, J = 1.5 Hz, 1H), 7.95 (d, J = 8.0 Hz, 1H), 7.89 (s, 3H), 7.82 (d, J = 9.2 Hz, 1H), 7.76 (d, J = 7.5 Hz, 1H), 7.25 (dd, J = 9.2, 1.4 Hz, 1H), 7.11 (d, J = 8.1 Hz, 1H), 6.74 (s, 1H), 5.09 (q, J = 7.2 Hz, 1H), 4.86-4.71 (m, 1H), 4.44-4.22 (m, 1H), 4.16-3.86 (m, 1H), 3.41-3.16 (m, 3H), 3.15-3.03 (m, 1H), 2.98-2.71 (m, 2H), 2.05-1.95 (m, 1H), 1.94-1.79 (m, 1H), 1.82-1.67 (m, 1H), 1.70-1.50 (m, 3H), 1.42 (d, J = 7.1 Hz, 3H), 1.39-1.25 (m, 4H), 1.18 (s, 3H), 1.17-1.11 (m, 4H), 1.11-0.97 (m, 2H), 0.93 (s, 3H). |
| 238 | 608.3 | 1H NMR (400 MHz, DMSO-d6) δ 8.69 (d, J = 9.4 Hz, 1H), 8.12 (d, J = 8.1 Hz, 1H), 7.90 (s, 3H), 7.40 (s, 1H), 7.36 (d, J = 8.1 Hz, 1H), 7.09 (s, 1H), 6.90 (s, 1H), 6.54-6.18 (m, 1H), 5.81-5.52 (m, 1H), 5.17-4.97 (m, 1H), 4.66-4.38 (m, 1H), 4.20-4.11 (m, 2H), 4.09 (s, 3H), 3.97 (s, 3H), 3.67-2.95 (m, 6H), 2.23-2.08 (m, 2H), 2.07-1.94 (m, 1H), 1.81-1.65 (m, 2H), 1.65-1.48 (m, 2H), 1.51-1.29 (m, 1H), 1.16-0.98 (m, 1H), 1.01-0.61 (m, 3H), 0.57-0.21 (m, 1H). |
| 239 | 648.5 | 1H NMR (400 MHz, DMSO-d6) δ 8.15 (d, J = 8.2 Hz, 1H), 7.93 (s, 3H), 7.36 (s, 1H), 7.29-7.21 (m, 2H), 7.22-7.13 (m, 1H), 7.08 (t, J = 7.4 Hz, 1H), 6.96 (t, J = 7.6 Hz, 1H), 6.90 (s, 1H), 6.54-6.26 (m, 1H), 6.26-5.52 (m, 3H), 5.04-4.90 (m, 1H), 4.29 (s, 3H), 3.98 (s, 3H), 3.86-3.63 (m, 4H), 3.54-3.38 (m, 9H), 3.19-2.95 (m, 1H), 2.78-2.62 (m, 1H), 2.01-1.84 (m, 1H), 1.82-1.64 (m, 1H), 1.44 (d, J = 7.0 Hz, 3H). |
| 240 | 652.4 | 1H NMR (400 MHz, DMSO-d6) δ 9.24 (d, J = 7.0 Hz, 1H), 8.61 (d, J = 2.6 Hz, 1H), 8.50 (d, J = 2.6 Hz, 1H), 8.10 (d, J = 8.0 Hz, 1H), 7.99 (s, 3H), 7.44 (s, 1H), 7.28 (d, J = 8.1 Hz, 1H), 7.09 (s, 1H), 6.94 (s, 1H), 5.25 (p, J = 7.0 Hz, 1H), 4.96-4.73 (m, 1H), 4.58 (dt, J = 13.6, 4.6 Hz, 1H), 4.13 (s, 3H), 4.00 (s, 3H), 3.83 (s, 5H), 3.71 (dt, J = 6.0, 2.7 Hz, 3H), 3.37 (s, 3H), 2.75-2.63 (m, 1H), 2.47-2.28 (m, 1H), 2.03-1.88 (m, 1H), 1.84-1.69 (m, 1H), 1.64-1.28 (m, 2H), 1.52 (d, J = 7.1 Hz, 3H), 1.31-1.09 (m, 1H), 0.72-0.51 (m, 1H). |
| 241 | 460.5 | 1H NMR (400 MHz, DMSO-d6) δ 9.23 (d, J = 7.0 Hz, 1H), 8.78 (s, 3H), 8.70 (d, J = 7.9 Hz, 1H), 8.61 (d, J = 2.6 Hz, 1H), 8.50 (d, J = 2.6 Hz, 1H), 8.11 (d, J = 8.0 Hz, 1H), 8.00 (d, J = 1.3 Hz, 1H), 7.36 (d, J = 1.3 Hz, 1H), 7.28 (d, J = 8.1 Hz, 1H), 7.14 (s, 1H), 5.26 (p, J = 7.1 Hz, 1H), 5.04-4.70 (m, 2H), 4.67-4.56 (m, 1H), 4.53-4.37 (m, 1H), 4.16 (s, 3H), 4.03 (s, 3H), 3.53-3.32 (m, 3H), 3.18-2.88 (m, 3H), 2.78-2.64 (m, 1H), 2.48-2.29 (m, 2H), 2.03-1.84 (m, 1H), 1.52 (d, J = 7.1 Hz, 3H), 1.70-1.31 (m, 1H), 1.29-1.06 (m, 1H), 0.85-0.39 (m, 1H). |
| 242 | 590.4 | 1H NMR (400 MHz, DMSO-d6) δ 8.76 (s, 2H), 8.65 (d, J = 8.0 Hz, 1H), 8.44 (d, J = 8.5 Hz, 1H), 8.01 (dd, J = 8.4, 7.2 Hz, 2H), 7.76 (d, J = 10.8 Hz, 1H), 7.15 (d, J = 8.2 Hz, 1H), 7.13 (s, 1H), 5.02 (p, J = 7.2 Hz, 1H), 4.94-4.74 (m, 1H), 4.74-4.67 (m, 2H), 4.40 (dt, J = 13.8, 9.1 Hz, 1H), 3.98 (s, 3H), 3.53-3.44 (m, 1H), 3.44-3.28 (m, 1H), 3.19-2.89 (m, 2H), 2.43-2.26 (m, 1H), 2.02-1.82 (m, 1H), 1.71-1.61 (m, 3H), 1.56 (dt, J = 8.2, 4.7 Hz, 1H), 1.43 (d, J = 7.1 Hz, 3H), 1.36-1.09 (m, 2H), 0.91-0.83 (m, 1H), 0.79-0.58 (m, 1H), 0.53-0.36 (m, 1H). |
| 243 | 654.5 | 1H NMR (400 MHz, DMSO-d6) δ 9.25 (d, J = 6.9 Hz, 1H), 8.74 (s, 2H), 8.66-8.61 (m, 1H), 8.60 (d, J = 2.6 Hz, 1H), 8.50 (d, J = 2.6 Hz, 1H), 8.10 (d, J = 8.0 Hz, 1H), 8.00 (d, J = 6.4 Hz, 1H), 7.64 (d, J = 10.6 Hz, 1H), 7.37 (s, 1H), 7.28 (d, J = 8.1 Hz, 1H), 5.23 (p, J = 7.1 Hz, 1H), 5.00-4.71 (m, 3H), 4.52-4.35 (m, 2H), 4.37-3.90 (m, 1H), 3.85 (tt, J = 7.2, 3.9 Hz, 1H), 3.55-3.32 (m, 2H), 3.14-2.91 (m, 2H), 2.71-2.62 (m, 1H), 2.46-2.26 (m, 2H), 1.92 (t, J = 12.0 Hz, 1H), 1.52 (d, J = 7.0 Hz, 3H), 1.50-1.35 (m, 4H), 1.34-1.07 (m, 2H), 1.01-0.87 (m, 1H), 0.68-0.52 (m, 1H), 0.53-0.36 (m, 1H). |
| 244 | 616.6 | 1H NMR (400 MHz, DMSO-d6) δ 8.64 (s, 2H), 8.38 (d, J = 7.7 Hz, 1H), 8.15-7.97 (m, 2H), 7.81 (d, J = 7.4 Hz, 1H), 7.35 (s, 1H), 7.19 (d, J = 8.1 Hz, 1H), 7.07 (s, 1H), 5.13 (p, J = 7.0 Hz, 1H), 4.91-4.75 (m, 1H), 4.51-4.35 (m, 1H), 4.15 (s, 3H), 4.12-4.04 (m, 1H), 4.02 (s, 3H), 3.83-3.71 |

TABLE 3-continued

| Example | ES/MS m/z [M + H]+ | 1H NMR |
|---|---|---|
| | | (m, 1H), 3.43-3.22 (m, 2H), 3.05-2.92 (m, 1H), 2.93-2.78 (m, 1H), 2.16-2.03 (m, 1H), 1.98-1.85 (m, 1H), 1.75-1.60 (m, 5H), 1.45 (d, J = 7.1 Hz, 3H), 1.43-1.27 (m, 2H), 1.22 (s, 3H), 1.17-1.03 (m, 3H), 0.96 (s, 3H). |
| 245 | 628.4 | 1H NMR (400 MHz, DMSO-d6) δ 9.40 (s, 1H), 8.91 (s, 1H), 8.38 (d, J = 7.4 Hz, 1H), 8.07 (d, J = 8.1 Hz, 1H), 7.45 (d, J = 1.2 Hz, 1H), 7.25-7.16 (m, 1H), 7.08 (d, J = 2.3 Hz, 1H), 6.93 (s, 1H), 5.07 (p, J = 7.0 Hz, 1H), 5.02-4.82 (m, 1H), 4.76-4.62 (m, 1H), 4.16 (s, 3H), 4.07-4.01 (m, 2H), 4.00 (s, 3H), 3.89 (t, J = 9.8 Hz, 1H), 3.83-3.66 (m, 3H), 3.66-3.47 (m, 3H), 3.38-3.00 (m, 2H), 2.72-2.56 (m, 1H), 2.32-2.13 (m, 1H), 1.96-1.70 (m, 2H), 1.49 (d, J = 7.1 Hz, 3H), 1.32-1.18 (m, 2H), 0.98-0.73 (m, 3H), 0.29-0.09 (m, 2H). |
| 246 | 628.4 | NA |
| 247 | 586.4 | 1H NMR (400 MHz, DMSO-d6) δ 8.42 (d, J = 8.3 Hz, 1H), 8.04 (s, 3H), 7.99 (d, J = 7.9 Hz, 1H), 7.43 (s, 1H), 7.17 (d, J = 7.9 Hz, 1H), 6.87 (s, 1H), 6.60 (s, 1H), 6.34 (s, 1H), 5.27-5.13 (m, 1H), 4.57-4.48 (m, 2H), 4.15 (d, J = 15.7 Hz, 1H), 4.08 (s, 3H), 3.65 (d, J = 15.7 Hz, 1H), 3.45 (t, J = 7.4 Hz, 2H), 2.80 (s, 3H), 2.05 (s, 2H), 1.94-1.73 (m, 4H), 1.75-1.52 (m, 1H), 1.45 (d, J = 6.7 Hz, 3H), 1.32 (s, 6H), 1.27-1.17 (m, 2H). |
| 248 | 600.5 | 1H NMR (400 MHz, DMSO-d6) δ 8.42 (d, J = 7.1 Hz, 1H), 8.07 (s, 3H), 8.00 (d, J = 8.0 Hz, 1H), 7.44 (s, 1H), 7.18 (d, J = 8.0 Hz, 1H), 6.64 (s, 1H), 6.36 (s, 1H), 5.09 (p, J = 6.5 Hz, 1H), 4.74-4.59 (m, 1H), 4.58-4.40 (m, 1H), 4.40-4.11 (m, 6H), 4.08 (s, 3H), 4.05 (d, J = 15.2 Hz, 1H), 3.78 (d, J = 15.2 Hz, 1H), 3.63-3.50 (m, 1H), 3.51-3.40 (m, 1H), 2.80 (s, 3H), 1.94-1.71 (m, 4H), 1.71-1.57 (m, 1H), 1.59-1.46 (m, 1H), 1.43 (d, J = 6.6 Hz, 3H), 1.33 (dd, J = 12.9, 4.3 Hz, 1H), 1.29-1.15 (m, 2H). |
| 249 | 580.4 | 1H NMR (400 MHz, DMSO-d6) δ 8.61-8.56 (m, 1H), 8.27 (d, J = 8.5 Hz, 1H), 8.09 (s, 3H), 7.93 (d, J = 8.0 Hz, 1H), 7.87 (s, 1H), 7.20 (dd, J = 7.0, 1.6 Hz, 1H), 7.09 (d, J = 8.1 Hz, 1H), 6.77 (s, 1H), 5.24-5.08 (m, 1H), 5.03-4.86 (m, 1H), 4.71-4.58 (m, 1H), 4.10-3.72 (m, 2H), 2.46-2.40 (m, 1H), 2.37-2.25 (m, 1H), 2.22-2.11 (m, 1H), 2.11-2.00 (m, 1H), 2.01-1.87 (m, 1H), 1.92-1.71 (m, 4H), 1.71-1.55 (m, 3H), 1.40 (d, J = 7.1 Hz, 3H), 1.37-1.27 (m, 2H), 1.29-1.20 (m, 1H), 1.20-1.10 (m, 1H), 1.11-1.00 (m, 1H), 1.02-0.87 (m, 2H), 0.69-0.46 (m, 1H), 0.49-0.36 (m, 1H), 0.36-0.22 (m, 1H). |
| 250 | 610.5 | 1H NMR (400 MHz, DMSO-d6) δ 8.31 (d, J = 8.5 Hz, 1H), 8.05 (s, 3H), 8.01 (d, J = 8.1 Hz, 1H), 7.53 (s, 1H), 7.17 (d, J = 8.5 Hz, 1H), 7.15 (s, 1H), 7.03 (s, 1H), 5.17 (p, J = 7.2 Hz, 1H), 5.07-4.94 (m, 1H), 4.78-4.65 (m, 1H), 4.61-4.26 (m, 1H), 3.99 (s, 3H), 3.93-3.84 (m, 1H), 3.81-3.65 (m, 2H), 3.61-3.17 (m, 2H), 2.37-2.22 (m, 1H), 2.13-2.02 (m, 1H), 2.03-1.91 (m, 1H), 1.88-1.73 (m, 3H), 1.72-1.54 (m, 2H), 1.51-1.44 (m, 1H), 1.41 (d, J = 7.1 Hz, 3H), 1.32 (dd, J = 12.9, 4.5 Hz, 1H), 1.24-1.06 (m, 2H), 1.06-0.90 (m, 3H), 0.91-0.80 (m, 3H), 0.73-0.54 (m, 1H), 0.46-0.31 (m, 1H). |
| 251 | 598.4 | 1H NMR (400 MHz, DMSO-d6) δ 8.14 (s, 1H), 8.04 (d, J = 8.3 Hz, 2H), 8.02 (s, 3H), 7.57 (s, 1H), 7.27 (d, J = 8.3 Hz, 1H), 7.01 (s, 2H), 4.69-4.54 (m, 2H), 4.10 (s, 3H), 3.99 (s, 3H), 2.25-2.17 (m, 2H), 1.88-1.78 (m, 3H), 1.65 (s, 6H), 1.63-1.56 (m, 2H), 1.54-1.37 (m, 6H), 1.36-1.27 (m, 1H), 1.27-1.18 (m, 2H), 1.13-0.97 (m, 2H). |
| 252 | 568.5 | 1H NMR (400 MHz, DMSO-d6) δ 8.96 (s, 1H), 8.27 (d, J = 8.5 Hz, 1H), 8.05 (s, 3H), 7.95 (d, J = 8.0 Hz, 1H), 7.80 (d, J = 9.0 Hz, 1H), 7.36 (dd, J = 9.2, 1.5 Hz, 1H), 7.11 (d, J = 8.1 Hz, 1H), 6.77 (s, 1H), 5.18 (p, J = 7.5 Hz, 1H), 5.02-4.78 (m, 1H), 4.58-4.35 (m, 3H), 3.78-3.67 (m, 3H), 3.59-3.29 (m, 2H), 3.00-2.77 (m, 2H), 2.46-2.40 (m, 2H), 2.13-2.02 (m, 1H), 2.01-1.90 (m, 1H), 1.83 (s, 3H), 1.73-1.56 (m, 2H), 1.40 (d, J = 7.1 Hz, 3H), 1.33 (dd, J = 13.0, 4.2 Hz, 1H), 1.12 (t, J = 7.5 Hz, 3H), 1.04-0.83 (m, 2H), 0.73-0.49 (m, 1H). |
| 253 | 638.5 | 1H NMR (400 MHz, DMSO-d6) δ 8.06 (s, 3H), 8.01 (d, J = 8.1 Hz, 1H), 7.81 (d, J = 7.4 Hz, 1H), 7.52 (d, J = 8.2 Hz, 1H), 7.15 (d, J = 8.2 Hz, 1H), 7.13 (s, 1H), 7.03 (s, 1H), 5.09 (p, J = 7.1 Hz, 1H), 4.93-4.79 (m, 1H), 4.67-4.54 (m, 1H), 4.54-4.30 (m, 2H), 3.99 (s, 3H), 3.93-3.83 (m, 1H), 3.78-3.64 (m, 1H), 3.59-3.33 (m, 2H), 2.37-2.23 (m, 1H), 1.96-1.74 (m, 4H), 1.71-1.56 (m, 1H), 1.56-1.47 (m, 1H), 1.44 (d, J = 7.1 Hz, 3H), 1.40-1.23 (m, 4H), 1.19 (s, 3H), 1.16-0.95 (m, 4H), 0.93 (s, 3H), 0.87-0.75 (m, 1H), 0.51-0.35 (m, 1H). |
| 254 | 596.6 | 1H NMR (400 MHz, DMSO-d6) δ 8.30 (d, J = 7.2 Hz, 1H), 8.18-8.00 (m, 3H), 7.98 (d, J = 8.1 Hz, 1H), 7.52 (s, 1H), 7.15 (d, J = 7.2 Hz, 1H), 7.13 (s, 2H), 7.03 (s, 1H), 4.95 (p, J = 7.1 Hz, 1H), 4.83-4.70 (m, 2H), 4.59-4.27 (m, 1H), 3.99 (s, 3H), 3.96-3.83 (m, 1H), 2.37-2.21 (m, 4H), 2.21-2.10 (m, 1H), 1.95-1.86 (m, 1H), 1.86-1.72 (m, 3H), 1.67-1.48 (m, 1H), 1.46 (d, J = 7.1 Hz, 3H), 1.43-1.34 (m, 1H), 1.32 (dd, J = 12.9, 4.4 Hz, 1H), 1.19-0.94 (m, 5H), 0.83-0.65 (m, 3H), 0.51-0.37 (m, 1H). |
| 255 | 570.4 | 1H NMR (400 MHz, DMSO-d6) δ 8.39 (t, J = 6.2 Hz, 1H), 8.04 (s, 3H), 8.02 (d, J = 8.0 Hz, 2H), 7.56 (s, 1H), 7.12 (d, J = 8.1 Hz, 1H), 7.01 (s, 2H), 4.62 (t, J = 7.5 Hz, 2H), 4.55 (d, J = 6.1 Hz, 2H), 4.09 (s, 3H), 3.99 |

TABLE 3-continued

| Example | ES/MS m/z [M + H]+ | 1H NMR |
|---|---|---|
| | | (s, 3H), 2.27-2.20 (m, 2H), 1.88-1.68 (m, 4H), 1.67-1.41 (m, 8H), 1.40-1.27 (m, 3H), 1.14-0.93 (m, 2H). |
| 256 | 584.4 | 1H NMR (400 MHz, DMSO-d6) δ 8.11 (d, J = 8.0 Hz, .33H, rotamer), 8.04 (d, J = 8.1 Hz, 0.67H, rotamer), 8.02 (s, 3H), 7.57 (s, 1H), 7.23 (d, J = 8.1 Hz, 0.42H, rotamer), 7.11 (d, J = 8.0 Hz, 0.60H, rotamer), 7.07 (s, .0.32H, rotamer), 7.01 (d, J = 8.1 Hz, 1H), 7.00 (s, 0.70H, rotamer), 5.61 (d, J = 16.6 Hz, 1H), 4.79 (s, 1H), 4.71-4.33 (m, 2H), 4.09 (s, 3H), 3.99 (s, 3H), 3.81-3.65 (m, 1H), 3.17 (s, 2H, rotamer), 2.98 (s, 1H, rotamer), 2.92-2.78 (m, 1H), 2.20-2.06 (m, 1H), 1.85 (s, 3H), 1.72-1.36 (m, 7H), 1.37-1.18 (m, 2H), 1.19-1.11 (m, 1H), 1.08-0.93 (m, 1H), 0.94-0.59 (m, 1H). |
| 257 | 638.4 | 1H NMR (400 MHz, DMSO-d6) δ 9.05 (d, J = 9.8 Hz, 1H), 8.19 (d, J = 8.1 Hz, 1H), 8.13 (s, 3H), 7.61 (s, 1H), 7.45 (d, J = 8.1 Hz, 1H), 7.27-6.96 (m, 1H), 7.16 (s, 1H), 7.05 (d, J = 1.2 Hz, 1H), 6.20-6.00 (m, 1H), 5.26-5.11 (m, 1H), 4.72-4.60 (m, 1H), 4.58-4.27 (m, 5H), 4.12 (s, 3H), 4.02 (s, 3H), 3.88-3.50 (m, 1H), 2.88-2.73 (m, 1H), 2.40-2.12 (m, 1H), 1.95-1.69 (m, 3H), 1.69-1.55 (m, 1H), 1.52-1.30 (m, 4H), 1.14-0.98 (m, 2H), 0.96-0.77 (m, 0H), 0.72-0.49 (m, 1H), 0.28-0.11 (m, 1H). |
| 258 | 638.4 | 1H NMR (400 MHz, DMSO-d6) δ 9.01 (d, J = 9.8 Hz, 1H), 8.16 (d, J = 8.1 Hz, 1H), 8.06 (s, 3H), 7.58 (d, J = 1.2 Hz, 1H), 7.42 (d, J = 8.1 Hz, 1H), 7.13 (s, 1H), 7.20-6.90 (m, 2H), 7.02 (d, J = 1.2 Hz, 1H), 6.17-6.00 (m, 1H), 5.27-5.04 (m, 1H), 4.67-4.57 (m, 1H), 4.57-4.21 (m, 2H), 4.09 (s, 3H), 3.99 (s, 3H), 3.80-3.64 (m, 2H), 2.82-2.69 (m, 1H), 2.31-2.06 (m, 1H), 1.91-1.54 (m, 5H), 1.50-1.27 (m, 4H), 1.25-0.96 (m, 3H), 0.96-0.74 (m, 1H), 0.72-0.46 (m, 1H), 0.41--0.08 (m, 1H). |
| 259 | 610.4 | 1H NMR (400 MHz, DMSO-d6) δ 8.39 (d, J = 8.5 Hz, 1H), 8.08 (s, 3H), 8.03 (d, J = 8.1 Hz, 1H), 7.57 (s, 1H), 7.24 (d, J = 8.1 Hz, 1H), 7.03 (d, J = 8.1 Hz, 2H), 5.08-4.87 (m, 1H), 4.51 (t, J = 8.7 Hz, 1H), 4.09 (s, 3H), 3.99 (s, 3H), 3.80-3.55 (m, 1H), 2.13-1.92 (m, 2H), 1.89-1.72 (m, 3H), 1.72-1.55 (m, 1H), 1.53-1.33 (m, 4H), 1.32 (s, 3H), 1.28-1.18 (m, 2H), 1.20-1.09 (m, 3H), 1.02-0.72 (m, 2H), 0.64-0.53 (m, 1H), 0.53-0.47 (m, 2H), 0.43-0.31 (m, 1H). |
| 260 | 638.4 | 1H NMR (400 MHz, DMSO-d6) δ 8.89 (s, 1H), 8.09 (d, J = 8.1 Hz, 1H), 8.06 (d, J = 8.1 Hz, 1H), 7.53 (s, 1H), 7.23 (d, J = 8.2 Hz, 1H), 7.10-6.99 (m, 1H), 6.93 (s, 1H), 5.25 (p, J = 7.0 Hz, 1H), 4.80 (t, J = 12.4 Hz, 1H), 4.50-4.25 (m, 1H), 4.12 (s, 3H), 3.97 (s, 3H), 3.66-3.33 (m, 2H), 3.29-3.18 (m, 2H), 3.13-2.97 (m, 1H), 3.01-2.86 (m, 1H), 2.25 (t, J = 12.6 Hz, 1H), 2.19-2.08 (m, 1H), 2.09-1.95 (m, 1H), 1.95-1.83 (m, 1H), 1.82-1.68 (m, 4H), 1.69-1.52 (m, 2H), 1.43 (d, J = 6.9 Hz, 4H), 1.49-1.26 (m, 2H), 1.28-1.16 (m, 2H), 1.16-1.02 (m, 1H), 1.05-0.94 (m, 1H), 0.97-0.87 (m, 1H), 0.65-0.55 (m, 1H), 0.50-0.39 (m, 1H). |
| 261 | 640.4 | 1H NMR (400 MHz, DMSO-d6) δ 8.92 (s, 1H), 8.15 (s, 1H), 8.05 (d, J = 8.1 Hz, 1H), 7.82 (d, J = 7.5 Hz, 1H), 7.53 (s, 1H), 7.27 (s, 2H), 7.19 (d, J = 8.1 Hz, 1H), 7.14 (s, 2H), 7.04 (s, 1H), 7.01 (s, 2H), 6.94 (d, J = 1.1 Hz, 1H), 5.13 (p, J = 7.1 Hz, 1H), 4.90-4.72 (m, 1H), 4.49-4.33 (m, 1H), 4.12 (s, 3H), 3.99 (s, 3H), 3.55-3.39 (m, 1H), 3.29-3.16 (m, 3H), 3.14-2.87 (m, 2H), 2.23-2.08 (m, 1H), 2.01-1.83 (m, 2H), 1.81-1.53 (m, 5H), 1.45 (d, J = 7.1 Hz, 3H), 1.43-1.27 (m, 2H), 1.21 (s, 3H), 1.18-1.00 (m, 1H), 0.95 (s, 3H). |
| 262 | 640.6 | 1H NMR (400 MHz, DMSO-d6) δ 9.03 (s, 1H), 8.23 (d, J = 11.7 Hz, 1H), 8.05 (d, J = 8.1 Hz, 1H), 7.82 (d, J = 7.4 Hz, 1H), 7.54 (s, 1H), 7.27 (s, 2H), 7.19 (d, J = 8.1 Hz, 1H), 7.14 (s, 2H), 7.04 (s, 1H), 7.01 (s, 2H), 6.95 (s, 1H), 5.12 (p, J = 7.2 Hz, 1H), 4.90-4.75 (m, 1H), 4.55-4.35 (m, 1H), 4.13 (s, 3H), 3.99 (s, 3H), 3.55-3.35 (m, 1H), 3.35-3.18 (m, 2H), 3.14-2.82 (m, 2H), 2.23-2.10 (m, 1H), 2.00-1.84 (m, 2H), 1.81-1.54 (m, 5H), 1.45 (d, J = 7.1 Hz, 3H), 1.42-1.26 (m, 3H), 1.21 (s, 3H), 1.17-0.98 (m, 2H), 0.95 (s, 3H). |
| 263 | 612.3 | 1H NMR (400 MHz, Chloroform-d) δ 7.99 (d, J = 8.2 Hz, 1H), 7.48 (s, 1H), 7.19 (d, J = 8.2 Hz, 1H), 6.99 (s, 1H), 6.88 (d, J = 8.1 Hz, 1H), 5.42 (q, J = 7.2 Hz, 1H), 4.89 (m, J = 14.7, 7.6 Hz, 1H), 4.16 (s, 3H), 4.05 (s, 3H), 3.18 (s, 14H), 2.64 (q, J = 9.4 Hz, 1H), 2.42 (q, J = 9.2 Hz, 1H), 2.15-1.66 (m, 2H), 1.59 (d, J = 7.0 Hz, 3H), 1.48-1.22 (m, 5H), 0.92 (s, 1H). |
| 264 | 614.2 | 1H NMR (400 MHz, DMSO-d6) δ 8.01 (d, J = 8.0 Hz, 1H), 7.44 (s, 1H), 7.18 (d, J = 8.1 Hz, 1H), 7.02 (s, 1H), 6.92 (d, J = 1.2 Hz, 1H), 4.96 (t, J = 7.1 Hz, 1H), 4.53 (d, J = 10.3 Hz, 2H), 4.13 (s, 3H), 4.00 (s, 3H), 3.02 (s, 3H), 1.91-1.81 (m, 2H), 1.76 (d, J = 2.7 Hz, 1H), 1.68-1.53 (m, 3H), 1.43 (d, J = 7.0 Hz, 4H), 1.26 (d, J = 18.2 Hz, 4H), 1.06 (t, J = 7.0 Hz, 3H), 0.38 (d, J = 9.0 Hz, 2H), 0.34-0.26 (m, 2H). |
| 265 | 600.2 | 1H NMR (400 MHz, DMSO-d6) δ 8.48 (d, J = 6.7 Hz, 1H), 8.01 (d, J = 8.0 Hz, 1H), 7.43 (s, 1H), 7.17 (d, J = 8.1 Hz, 1H), 7.02 (s, 1H), 6.92 (d, J = 1.2 Hz, 1H), 4.95 (p, J = 6.8 Hz, 2H), 4.70 (m, J = 14.1, 3.4 Hz, 2H), 4.14 (s, 3H), 4.00 (s, 3H), 3.98-3.91 (m, 1H), 3.51 (m, J = 10.8, 5.1 Hz, 1H), 3.39 (t, J = 10.3 Hz, 1H), 3.22 (m, J = 10.8, 3.7 Hz, 3H), 2.76 (m, J = 13.4, 7.9, 3.5 Hz, 2H), 2.02 (s, 1H), 1.85 (m, J = 9.3, 4.7 Hz, 1H), 1.76 (m, J = 8.9, 4.9 Hz, 1H), 1.59 (d, J = 8.8 Hz, 2H), 1.44 (d, J = 6.9 Hz, 3H), |

TABLE 3-continued

| Example | ES/MS m/z [M + H]+ | ¹H NMR |
|---|---|---|
| | | 0.97-0.82 (m, 4H), 0.44 (m, J = 9.0, 4.7 Hz, 1H), 0.30 (m, J = 8.5, 5.0 Hz, 1H). |
| 266 | 600.4 | 1H NMR (400 MHz, DMSO-d6) δ 8.50 (d, J = 6.9 Hz, 1H), 8.08 (d, J = 8.0 Hz, 1H), 7.43 (s, 1H), 7.24 (d, J = 8.1 Hz, 1H), 7.05 (s, 1H), 6.93 (d, J = 1.2 Hz, 1H), 5.06 (p, J = 6.7 Hz, 1H), 4.70 (m, J = 14.2, 3.1 Hz, 1H), 4.14 (s, 3H), 4.12-4.05 (m, 1H), 4.00 (s, 3H), 3.72 (m, J = 9.8, 8.1 Hz, 1H), 3.62 (m, J = 11.0, 3.5 Hz, 1H), 3.49 (m, J = 9.7, 3.2 Hz, 1H), 3.24 (d, J = 34.6 Hz, 4H), 2.85 (m, J = 11.0, 9.3 Hz, 1H), 2.43-2.31 (m, 1H), 2.02 (s, 1H), 1.75 (d, J = 6.9 Hz, 1H), 1.66-1.50 (m, 2H), 1.46 (d, J = 6.7 Hz, 3H), 1.15 (d, J = 7.3 Hz, 3H), 1.01 (d, J = 5.3 Hz, 1H), 0.50 (m, J = 9.3, 4.9 Hz, 1H), 0.37 (m, J = 9.6, 5.1 Hz, 1H). |
| 267 | 600.3 | 1H NMR (400 MHz, DMSO-d6) δ 8.52 (d, J = 6.1 Hz, 1H), 8.03 (d, J = 8.0 Hz, 1H), 7.44 (s, 1H), 7.19 (d, J = 8.1 Hz, 1H), 7.01 (s, 1H), 6.92 (d, J = 1.2 Hz, 1H), 4.95 (p, J = 6.8 Hz, 1H), 4.68 (m, J = 13.9, 3.9 Hz, 1H), 4.13 (s, 3H), 3.99 (s, 3H), 3.85-3.74 (m, 2H), 3.27 (s, 3H), 3.12 (m, J = 10.6, 8.4 Hz, 2H), 2.94 (m, J = 10.6, 6.0 Hz, 1H), 2.17 (d, J = 14.5 Hz, 1H), 2.01 (s, 1H), 1.85 (d, J = 5.5 Hz, 1H), 1.81-1.71 (m, 2H), 1.58 (d, J = 8.7 Hz, 2H), 1.43 (d, J = 7.0 Hz, 3H), 1.09 (d, J = 6.3 Hz, 3H), 0.81 (m, J = 8.6, 4.3 Hz, 1H), 0.50 (m, J = 8.6, 4.8 Hz, 1H), 0.36 (m, J = 8.5, 5.0 Hz, 1H). |
| 268 | 600.3 | 1H NMR (400 MHz, DMSO-d6) δ 8.53 (d, J = 6.6 Hz, 1H), 8.06 (d, J = 8.0 Hz, 1H), 7.45 (s, 1H), 7.21 (d, J = 8.1 Hz, 1H), 7.04 (s, 1H), 6.93 (d, J = 1.2 Hz, 1H), 5.03 (t, J = 6.7 Hz, 1H), 4.80 (m, J = 14.3, 2.6 Hz, 2H), 4.15 (s, 3H), 4.00 (s, 3H), 3.95-3.82 (m, 3H), 3.60 (m, J = 11.0, 4.4 Hz, 1H), 3.27 (s, 3H), 2.93 (m, J = 11.0, 9.2 Hz, 1H), 2.60 (m, J = 15.1, 3.0 Hz, 1H), 2.08-1.95 (m, 2H), 1.75 (m, J = 9.0, 8.5, 4.0 Hz, 2H), 1.59 (d, J = 8.8 Hz, 2H), 1.48 (d, J = 6.7 Hz, 3H), 1.09-1.01 (m, 1H), 0.97 (d, J = 6.1 Hz, 3H), 0.48 (m, J = 9.0, 4.8 Hz, 1H), 0.36 (m, J = 8.7, 5.0 Hz, 1H). |
| 269 | 584.3 | 1H NMR (400 MHz, DMSO-d6) δ 8.26 (d, J = 7.0 Hz, 1H), 7.43 (s, 1H), 7.17 (d, J = 8.0 Hz, 1H), 7.01 (s, 1H), 6.92 (s, 1H), 4.98 (p, J = 7.0 Hz, 1H), 4.57 (m, J = 14.0, 3.7 Hz, 1H), 4.13 (s, 3H), 4.00 (s, 3H), 3.24 (d, J = 31.9 Hz, 5H), 2.03 (d, J = 11.6 Hz, 1H), 1.88 (m, J = 13.6, 6.9 Hz, 1H), 1.81-1.50 (m, 5H), 1.43 (d, J = 7.0 Hz, 3H), 1.35-1.18 (m, 3H), 1.02 (q, J = 7.6, 6.6 Hz, 1H), 0.73 (m, J = 16.2, 12.4, 8.2, 4.0 Hz, 2H), 0.31 (m, J = 8.7, 4.5 Hz, 1H), 0.16 (m, J = 9.3, 4.8 Hz, 1H). |
| 270 | 614.3 | 1H NMR (400 MHz, DMSO-d6) δ 8.05 (d, J = 8.1 Hz, 1H), 7.41 (s, 1H), 7.20 (d, J = 8.1 Hz, 1H), 7.05 (s, 1H), 6.92 (d, J = 1.2 Hz, 1H), 5.04 (p, J = 7.0 Hz, 1H), 4.83 (d, J = 13.9 Hz, 1H), 4.34 (m, J = 13.5, 4.7 Hz, 1H), 4.13 (s, 3H), 4.00 (s, 3H), 3.28 (d, J = 9.4 Hz, 1H), 3.22-3.13 (m, 3H), 3.12 (s, 3H), 2.44-2.25 (m, 2H), 2.01 (d, J = 12.0 Hz, 1H), 1.86 (d, J = 8.4 Hz, 2H), 1.75 (d, J = 7.0 Hz, 1H), 1.61 (d, J = 15.5 Hz, 4H), 1.43 (d, J = 7.1 Hz, 3H), 0.80 (m, J = 8.8, 5.0 Hz, 1H), 0.44 (d, J = 5.8 Hz, 2H), 0.30 (d, J = 8.3 Hz, 1H). |
| 271 | 600.3 | 1H NMR (400 MHz, DMSO-d6) δ 8.05 (t, J = 8.1 Hz, 1H), 7.42 (s, 1H), 7.22 (t, J = 8.1 Hz, 1H), 7.01 (d, J = 7.2 Hz, 1H), 6.93 (d, J = 1.3 Hz, 1H), 5.13-5.04 (m, 1H), 5.03-4.94 (m, 1H), 4.89 (d, J = 14.3 Hz, 1H), 4.12 (d, J = 5.7 Hz, 3H), 4.00 (d, J = 1.2 Hz, 3H), 3.67-3.50 (m, 2H), 3.34-3.07 (m, 3H), 2.87 (t, J = 9.5 Hz, 1H), 2.70-2.62 (m, 1H), 2.09-1.94 (m, 2H), 1.76 (s, 1H), 1.59 (d, J = 8.2 Hz, 2H), 1.44 (m, J = 9.8, 6.8 Hz, 3H), 1.22 (m, J = 25.7, 5.7 Hz, 2H), 1.03 (m, J = 6.1, 4.8 Hz, 3H), 0.23-- 0.15 (m, 4H). |
| 272 | 598.3 | 1H NMR (400 MHz, DMSO-d6) δ 8.01 (d, J = 8.0 Hz, 1H), 7.43 (d, J = 2.9 Hz, 1H), 7.17 (d, J = 8.1 Hz, 1H), 7.02 (d, J = 1.2 Hz, 1H), 6.92 (d, J = 1.3 Hz, 1H), 4.98 (m, J = 7.5, 3.8 Hz, 1H), 4.71-4.62 (m, 1H), 4.50 (m, J = 14.0, 4.2 Hz, 1H), 4.13 (d, J = 1.2 Hz, 3H), 4.00 (s, 3H), 3.33-3.09 (m, 4H), 2.03 (m, J = 11.4, 5.8 Hz, 2H), 1.80-1.67 (m, 2H), 1.66-1.51 (m, 3H), 1.44 (t, J = 7.3 Hz, 3H), 1.23 (m, J = 40.1, 15.7 Hz, 5H), 0.92 (d, J = 6.7 Hz, 3H), 0.78 (s, 1H), 0.67-0.52 (m, 1H), 0.37 (m, J = 8.9, 4.5 Hz, 1H), 0.19 (m, J = 32.7, 13.3, 8.9, 4.6 Hz, 2H). |
| 273 | 597.8 | 1H NMR (400 MHz, DMSO-d6) δ 7.85 (d, J = 7.9 Hz, 1H), 7.59 (d, J = 8.2 Hz, 1H), 7.43-7.37 (m, 2H), 7.08 (m, J = 8.4, 1.3 Hz, 1H), 7.01 (s, 1H), 6.91 (d, J = 1.2 Hz, 1H), 5.61 (m, J = 13.7, 6.3 Hz, 1H), 5.23 (m, J = 14.7, 6.7 Hz, 1H), 5.09 (p, J = 7.2 Hz, 1H), 4.65-4.54 (m, 1H), 4.22 (m, J = 14.2, 7.4 Hz, 1H), 4.10 (s, 3H), 3.99 (s, 3H), 3.20 (m, J = 29.0, 14.5 Hz, 4H), 2.30 (d, J = 5.9 Hz, 1H), 2.02 (s, 1H), 1.87 (s, 1H), 1.75 (d, J = 6.3 Hz, 2H), 1.58 (d, J = 8.3 Hz, 3H), 1.48 (d, J = 7.1 Hz, 4H), 1.32 (s, 3H), 1.07 (s, 3H). |
| 274 | 612.4 | 1H NMR (400 MHz, DMSO-d6) δ 7.99 (t, J = 7.7 Hz, 2H), 7.43 (s, 1H), 7.16 (d, J = 8.0 Hz, 1H), 7.01 (s, 1H), 6.92 (d, J = 1.1 Hz, 1H), 4.96 (p, J = 7.1 Hz, 1H), 4.68 (d, J = 13.8 Hz, 1H), 4.13 (s, 3H), 4.00 (s, 3H), 3.93 (dd, J = 14.0, 8.7 Hz, 3H), 2.21 (t, J = 12.8 Hz, 2H), 2.02 (s, 1H), 1.76 (s, 1H), 1.59 (d, J = 8.2 Hz, 2H), 1.44 (d, J = 7.0 Hz, 3H), 1.41-1.28 (m, 2H), 1.23 (s, 3H), 1.19 (d, J = 9.8 Hz, 2H), 0.87 (s, 3H), 0.81-0.71 (m, 3H), 0.67-0.56 (m, 2H), 0.38 (dt, J = 9.2, 4.5 Hz, 1H), 0.19 (dt, J = 9.4, 4.9 Hz, 1H). |

TABLE 3-continued

| Example | ES/MS m/z [M + H]+ | ¹H NMR |
|---|---|---|
| 275 | 634.5 | 1H NMR (400 MHz, DMSO-d6) δ 8.78 (d, J = 8.0 Hz, 1H), 8.45 (d, J = 8.5 Hz, 1H), 8.01 (d, J = 8.0 Hz, 1H), 7.82 (m, J = 5.2, 1.3 Hz, 1H), 7.29 (s, 1H), 7.15 (d, J = 8.1 Hz, 1H), 5.06-4.96 (m, 1H), 4.88 (m, J = 9.5, 4.6 Hz, 1H), 4.77 (q, J = 4.8 Hz, 2H), 4.40 (m, J = 13.7, 9.4 Hz, 1H), 4.03 (m, J = 7.2, 3.8 Hz, 2H), 3.47 (d, J = 12.3 Hz, 1H), 3.39 (d, J = 13.1 Hz, 1H), 3.13-2.89 (m, 2H), 2.41-2.29 (m, 1H), 1.99-1.80 (m, 2H), 1.72-1.53 (m, 3H), 1.49-1.41 (m, 4H), 1.36 (m, J = 11.9, 7.1 Hz, 1H), 1.30-1.20 (m, 1H), 1.20-1.06 (m, 2H), 0.96 (d, J = 5.7 Hz, 1H), 0.91-0.82 (m, 1H), 0.79-0.58 (m, 3H), 0.49 (m, J = 9.1, 5.8, 3.6 Hz, 1H). |
| 276 | 618.4 | 1H NMR (400 MHz, DMSO-d6) δ 8.05 (d, J = 8.1 Hz, 1H), 7.84 (d, J = 7.4 Hz, 1H), 7.45 (s, 1H), 7.19 (d, J = 8.2 Hz, 1H), 7.04 (s, 1H), 6.94 (d, J = 1.0 Hz, 1H), 5.19 (d, J = 4.1 Hz, 1H), 5.13 (q, J = 7.1 Hz, 1H), 5.08 (d, J = 7.2 Hz, 1H), 4.82 (t, J = 11.0 Hz, 1H), 4.41 (d, J = 10.1 Hz, 1H), 4.12 (s, 3H), 4.00 (s, 3H), 3.41-3.28 (m, 1H), 2.12-2.01 (m, 2H), 1.92 (t, J = 12.0 Hz, 1H), 1.73-1.55 (m, 2H), 1.45 (d, J = 7.1 Hz, 3H), 1.37 (m, J = 20.8, 7.5 Hz, 4H), 1.21 (s, 3H), 1.08 (s, 2H), 0.95 (s, 3H). |
| 277 | 614.4 | 1H NMR (400 MHz, DMSO-d6) δ 7.91 (s, 1H), 7.81 (d, J = 7.4 Hz, 1H), 7.32 (d, J = 1.3 Hz, 1H), 7.19 (d, J = 8.1 Hz, 1H), 7.08 (s, 1H), 5.12 (p, J = 7.1 Hz, 1H), 4.84 (t, J = 10.9 Hz, 2H), 4.51-4.38 (m, 2H), 4.15 (s, 3H), 4.12-4.03 (m, 2H), 4.01 (s, 3H), 3.19 (d, J = 13.3 Hz, 1H), 2.93 (m, J = 22.7, 11.6 Hz, 2H), 2.40 (d, J = 13.8 Hz, 2H), 2.00 (s, 1H), 1.92 (t, J = 12.7 Hz, 2H), 1.70 (m, J = 31.8, 16.8 Hz, 3H), 1.55 (m, J = 13.4, 3.9 Hz, 2H), 1.47 (d, J = 4.4 Hz, 2H), 1.42 (s, 3H), 1.35 (d, J = 12.0 Hz, 1H), 1.20 (d, J = 13.2 Hz, 3H), 1.10 (d, J = 14.9 Hz, 2H), 0.95 (s, 3H). |
| 278 | 624.5 | 1H NMR (400 MHz, Chloroform-d) δ 7.98 (d, J = 8.1 Hz, 1H), 7.66 (s, 1H), 7.15 (d, J = 8.2 Hz, 1H), 7.03-6.88 (m, 2H), 5.40 (t, J = 7.3 Hz, 1H), 4.90 (s, 1H), 4.17 (s, 3H), 4.05 (s, 3H), 3.85 (s, 4H), 2.61 (q, J = 9.4, 6.8 Hz, 1H), 2.39 (m, J = 21.2, 12.0 Hz, 2H), 2.11-1.65 (m, 10H), 1.57 (d, J = 6.9 Hz, 3H), 1.42 (s, 2H), 1.28 (s, 5H), 0.89 (s, 1H). |
| 279 | 610.5 | 1H NMR (400 MHz, Chloroform-d) δ 8.04 (d, J = 8.2 Hz, 1H), 7.71 (s, 1H), 7.17 (d, J = 8.3 Hz, 2H), 7.01 (d, J = 10.8 Hz, 1H), 5.41 (p, J = 6.9 Hz, 1H), 4.90 (t, J = 12.1 Hz, 1H), 4.22 (s, 3H), 4.08 (s, 3H), 3.84 (s, 1H), 2.44-1.63 (m, 10H), 1.56 (d, J = 6.7 Hz, 3H), 1.52-1.08 (m, 9H), 0.63 (m, J = 35.3, 5.9 Hz, 2H). |
| 280 | 638.6 | 1H NMR (400 MHz, Chloroform-d) δ 8.05 (d, J = 8.1 Hz, 1H), 7.69 (s, 1H), 7.26 (s, 1H), 7.19 (s, 1H), 7.01 (d, J = 9.5 Hz, 1H), 5.62 (d, J = 62.5 Hz, 4H), 5.28 (q, J = 7.1 Hz, 1H), 4.89 (m, J = 14.8, 7.5 Hz, 1H), 4.30 (s, 1H), 4.20 (s, 3H), 4.07 (s, 3H), 3.84 (s, 1H), 2.60 (q, J = 9.4 Hz, 1H), 2.34 (m, J = 17.1, 9.1 Hz, 2H), 2.13-1.63 (m, 10H), 1.59 (t, J = 6.3 Hz, 3H), 1.36 (d, J = 7.6 Hz, 2H), 1.31-1.09 (m, 5H), 0.99 (s, 3H). |
| 281 | 624.5 | 1H NMR (400 MHz, Chloroform-d) δ 8.04 (d, J = 8.1 Hz, 1H), 7.72 (s, 1H), 7.54 (s, 1H), 7.18 (d, J = 8.1 Hz, 1H), 7.02 (d, J = 4.4 Hz, 1H), 5.29 (p, J = 6.7 Hz, 1H), 4.86-4.70 (m, 2H), 4.28 (s, 1H), 4.21 (s, 3H), 4.08 (s, 3H), 3.85 (s, 1H), 2.39 (s, 1H), 2.15-2.03 (m, 2H), 1.98-1.65 (m, 4H), 1.56 (d, J = 6.6 Hz, 7H), 1.30 (d, J = 47.0 Hz, 8H), 0.66 (d, J = 5.6 Hz, 1H), 0.56 (d, J = 5.7 Hz, 1H). |
| 282 | 572.3 | 1H NMR (400 MHz, DMSO-d6) δ 8.35 (d, J = 8.5 Hz, 1H), 8.04 (d, J = 8.1 Hz, 1H), 7.94 (bs, 3H), 7.41 (s, 1H), 7.19 (d, J = 8.1 Hz, 1H), 7.04 (s, 1H), 6.91 (d, J = 1.2 Hz, 1H), 5.29-5.11 (m, 1H), 5.04-4.86 (m, 1H), 4.60-4.46 (m, 1H), 4.11 (s, 3H), 3.98 (s, 3H), 3.28-3.06 (m, 2H), 2.15-1.94 (m, 2H), 1.81-1.08 (m, 14H), 1.06-0.94 (m, 2H), 0.72-0.52 (m, 1H). |
| 283 | 586.4 | 1H NMR (400 MHz, DMSO-d6) δ 8.26 (d, J = 7.2 Hz, 1H), 8.03 (d, J = 8.0 Hz, 1H), 7.95 (bs, 3H), 7.42 (s, 1H), 7.19 (d, J = 8.1 Hz, 1H), 7.01 (s, 1H), 6.91 (d, J = 1.2 Hz, 1H), 5.13-4.94 (m, 1H), 4.63-4.44 (m, 1H), 4.10 (s, 3H), 3.98 (s, 3H), 3.37-3.10 (m, 4H), 2.36-2.20 (m, 1H), 2.09-1.86 (m, 3H), 1.82-1.68 (m, 1H), 1.65-1.49 (m, 4H), 1.46 (d, J = 7.0 Hz, 3H), 1.42-1.31 (m, 3H), 1.26-0.83 (m, 7H). |
| 284 | 600.5 | 1H NMR (400 MHz, DMSO-d6) δ 8.16 (d, J = 7.9 Hz, 1H), 8.08-7.86 (m, 4H), 7.32 (s, 1H), 7.15 (d, J = 8.1 Hz, 1H), 6.64 (s, 1H), 6.44 (s, 1H), 5.37-5.03 (m, 1H), 4.80-4.60 (m, 1H), 4.52-4.39 (m, 1H), 4.09 (s, 3H), 3.36-3.16 (m, 3H), 2.79 (s, 3H), 2.41-2.28 (m, 1H), 2.20-2.00 (m, 2H), 1.81-1.71 (m, 1H), 1.70-1.56 (m, 3H), 1.53-1.29 (m, 8H), 1.29-0.98 (m, 10H). |
| 285 | 584.4 | 1H NMR (400 MHz, DMSO-d6) δ 8.35 (d, J = 8.5 Hz, 1H), 8.13-8.01 (m, 4H), 7.58 (s, 1H), 7.19 (d, J = 8.1 Hz, 1H), 7.11-6.91 (m, 2H), 5.28-5.12 (m, 1H), 5.07-4.89 (m, 1H), 4.68-4.30 (m, 2H), 4.11 (s, 3H), 4.00 (s, 3H), 3.80-3.68 (m, 2H), 2.37-2.24 (m, 1H), 2.13-1.94 (m, 2H), 1.92-1.73 (m, 3H), 1.71-1.59 (m, 2H), 1.54-1.08 (m, 10H), 1.05-0.91 (m, 2H), 0.66-0.51 (m, 1H). |
| 286 | 598.4 | 1H NMR (400 MHz, DMSO-d6) δ 8.25 (d, J = 7.1 Hz, 1H), 8.08 (bs, 3H), 8.03 (d, J = 8.1 Hz, 1H), 7.59 (s, 1H), 7.20 (d, J = 8.1 Hz, 1H), 7.06-6.94 (m, 2H), 5.12-4.92 (m, 1H), 4.68-4.35 (m, 3H), 4.10 (s, 3H), 4.00 (s, 3H), 2.37-2.23 (m, 2H), 2.06-1.73 (m, 5H), 1.68-1.48 (m, 3H), 1.46 (d, J = 7.0 Hz, 3H), 1.41-1.29 (m, 4H), 1.25-0.90 (m, 7H). |

TABLE 3-continued

| Example | ES/MS m/z [M + H]+ | ¹H NMR |
|---|---|---|
| 287 | 612.5 | 1H NMR (400 MHz, DMSO-d6) δ 8.28-8.11 (m, 4H), 7.98 (d, J = 8.0 Hz, 1H), 7.47 (s, 1H), 7.15 (d, J = 8.1 Hz, 1H), 6.64 (s, 1H), 6.44 (s, 1H), 5.23-5.07 (m, 1H), 4.80-4.63 (m, 1H), 4.57-4.39 (m, 1H), 4.11 (s, 3H), 2.80 (s, 3H), 2.42-2.27 (m, 2H), 2.15-1.98 (m, 1H), 1.92-1.76 (m, 4H), 1.72-1.55 (m, 2H), 1.52-1.29 (m, 8H), 1.27-0.97 (m, 10H). |
| 288 | 584.4 | 1H NMR (400 MHz, DMSO-d6) δ 8.35 (d, J = 8.7 Hz, 1H), 8.10-8.02 (m, 1H), 7.95-7.86 (m, 2H), 7.59-7.33 (m, 1H), 7.19 (d, J = 8.1 Hz, 1H), 7.05 (s, 1H), 7.01-6.92 (m, 1H), 5.26-5.15 (m, 1H), 5.04-4.86 (m, 1H), 4.63-4.50 (m, 1H), 4.11 (s, 3H), 3.99 (s, 3H), 3.67-3.49 (m, 3H), 3.26-3.03 (m, 2H), 2.14-1.82 (m, 5H), 1.72-1.60 (m, 2H), 1.55-1.07 (m, 10H), 1.04-0.92 (m, 2H), 0.70-0.53 (m, 1H). |
| 289 | 598.5 | 1H NMR (400 MHz, DMSO-d6) δ 8.25 (d, J = 7.1 Hz, 1H), 8.07 (d, J = 5.6 Hz, 1H), 8.03 (d, J = 8.1 Hz, 1H), 7.92 (bs, 2H), 7.61-7.34 (m, 1H), 7.19 (d, J = 8.1 Hz, 1H), 7.01 (s, 1H), 7.00-6.91 (m, 1H), 5.15-4.90 (m, 1H), 4.72-4.43 (m, 2H), 4.10 (s, 3H), 3.99 (s, 3H), 3.28-3.11 (m, 1H), 2.72-2.63 (m, 1H), 2.38-2.20 (m, 1H), 2.05-1.84 (m, 5H), 1.72-1.50 (m, 3H), 1.46 (d, J = 7.0 Hz, 3H), 1.43-1.29 (m, 4H), 1.25-0.84 (m, 7H). |
| 290 | 612.5 | 1H NMR (400 MHz, DMSO-d6) δ 8.23-8.04 (m, 2H), 8.03-7.88 (m, 3H), 7.52-7.23 (m, 1H), 7.14 (d, J = 8.1 Hz, 1H), 6.61 (s, 1H), 6.48-6.25 (m, 1H), 5.24-5.07 (m, 1H), 4.83-4.62 (m, 1H), 4.56-4.20 (m, 3H), 4.10-4.04 (m, 3H), 3.28-3.17 (m, 1H), 2.80 (s, 3H), 2.16-1.79 (m, 5H), 1.71-1.54 (m, 2H), 1.52-1.32 (m, 8H), 1.27-0.96 (m, 10H). |
| 291 | 559.3 | 1H NMR (400 MHz, Methanol-d4) δ 8.12 (d, J = 8.1 Hz, 1H), 7.47 (d, J = 1.2 Hz, 1H), 7.23 (d, J = 8.1 Hz, 1H), 7.07 (s, 1H), 7.05 (d, J = 1.2 Hz, 1H), 4.89-4.76 (m, 2H), 4.67-4.53 (m, 1H), 4.50-4.28 (m, 1H), 4.19 (s, 3H), 4.09 (s, 3H), 3.98-3.64 (m, 1H), 3.49-3.36 (m, 3H), 3.31-3.23 (m, 1H), 2.30-2.12 (m, 1H), 1.93-1.64 (m, 5H), 1.63-1.18 (m, 11H), 1.04-0.83 (m, 3H). |
| 292 | 612.3 | 1H NMR (400 MHz, Methanol-d4) δ 8.10 (d, J = 8.1 Hz, 1H), 7.47 (d, J = 1.1 Hz, 1H), 7.26 (d, J = 8.1 Hz, 1H), 7.04 (d, J = 1.3 Hz, 1H), 6.99 (s, 1H), 5.38-5.24 (m, 2H), 4.88-4.82 (m, 1H), 4.56-4.26 (m, 1H), 4.19 (s, 3H), 4.09 (s, 3H), 3.97-3.60 (m, 1H), 3.50-3.35 (m, 2H), 2.41-2.28 (m, 1H), 2.27-2.14 (m, 1H), 1.95-1.67 (m, 4H), 1.57 (d, J = 7.0 Hz, 3H), 1.47-1.27 (m, 5H), 1.12 (s, 3H), 0.91-0.78 (m, 2H), 0.49-0.31 (m, 1H), −0.08-−0.16 (m, 1H), −0.27-−0.35 (m, 1H), −0.48-−0.62 (m, 1H). |
| 293 | 560.3 | 1H NMR (400 MHz, Methanol-d4) δ 8.09 (t, J = 6.3 Hz, 1H), 8.00 (d, J = 8.5 Hz, 1H), 7.46 (s, 1H), 6.82 (s, 2H), 6.79 (d, J = 4.4 Hz, 1H), 4.85-4.74 (m, 2H), 4.55-4.38 (m, 2H), 4.25 (s, 3H), 4.18-3.81 (m, 1H), 3.75-3.55 (m, 1H), 3.56-3.38 (m, 2H), 3.30-3.20 (m, 2H), 3.05-2.86 (m, 1H), 2.81 (s, 3H), 2.30-2.12 (m, 1H), 2.06-1.64 (m, 3H), 1.61-1.45 (m, 2H), 1.45-1.33 (m, 2H), 1.33-1.15 (m, 2H), 0.98-0.82 (m, 2H). |
| 294 | 636.3 | 1H NMR (400 MHz, Methanol-d4) δ 8.06 (d, J = 8.1 Hz, 1H), 7.94 (d, J = 1.3 Hz, 1H), 7.45 (d, J = 1.3 Hz, 1H), 7.23 (d, J = 8.1 Hz, 1H), 7.00 (s, 1H), 5.33-5.17 (m, 1H), 5.06-4.94 (m, 2H), 4.37-4.21 (m, 1H), 4.17 (s, 3H), 4.11 (s, 3H), 3.77-3.54 (m, 2H), 3.38 (d, J = 12.3 Hz, 1H), 3.30-3.24 (m, 1H), 2.68-2.54 (m, 1H), 2.50-2.29 (m, 1H), 1.96-1.83 (m, 1H), 1.83-1.68 (m, 1H), 1.61-1.20 (m, 13H), 1.15-0.99 (m, 4H). |
| 295 | | 1H NMR (400 MHz, Methanol-d4) δ 8.07 (d, J = 8.1 Hz, 1H), 7.92 (d, J = 1.3 Hz, 1H), 7.46 (d, J = 1.3 Hz, 1H), 7.23 (d, J = 8.1 Hz, 1H), 7.01 (s, 1H), 5.26 (q, J = 7.0 Hz, 1H), 5.05-4.94 (m, 1H), 4.50-4.38 (m, 1H), 4.30-4.20 (m, 2H), 4.17 (s, 3H), 4.11 (s, 3H), 3.48-3.35 (m, 2H), 3.31-3.23 (m, 1H), 2.15-2.03 (m, 2H), 1.98-1.85 (m, 1H), 1.84-1.69 (m, 1H), 1.61-1.18 (m, 13H), 1.15-1.00 (m, 4H). |
| 296 | 636.4 | 1H NMR (400 MHz, Methanol-d4) δ 8.07 (d, J = 8.1 Hz, 1H), 7.94 (d, J = 1.3 Hz, 1H), 7.47 (d, J = 1.4 Hz, 1H), 7.23 (d, J = 8.2 Hz, 1H), 7.03 (s, 1H), 5.26 (q, J = 7.0 Hz, 1H), 5.07-4.93 (m, 2H), 4.32-4.20 (m, 1H), 4.17 (s, 3H), 4.12 (s, 3H), 3.73-3.56 (m, 2H), 3.39 (d, J = 12.3 Hz, 1H), 3.31-3.26 (m, 1H), 2.68-2.54 (m, 1H), 2.51-2.30 (m, 1H), 1.90 (t, J = 12.1 Hz, 1H), 1.83-1.69 (m, 1H), 1.63-1.19 (m, 13H), 1.15-0.99 (m, 4H). |
| 297 | 666.3 | 1H NMR (400 MHz, Methanol-d4) δ 8.04 (d, J = 8.1 Hz, 1H), 7.47 (d, J = 1.2 Hz, 1H), 7.21 (d, J = 8.1 Hz, 1H), 7.04 (d, J = 1.2 Hz, 1H), 6.99 (s, 1H), 6.63 (t, J = 73.7 Hz, 1H), 5.23 (q, J = 7.0 Hz, 1H), 5.01-4.89 (m, 1H), 4.83-4.77 (m, 1H), 4.29-4.16 (m, 2H), 4.14 (s, 3H), 4.06 (s, 3H), 3.82-3.52 (m, 4H), 2.11-1.95 (m, 2H), 1.95-1.81 (m, 1H), 1.81-1.67 (m, 1H), 1.58-1.17 (m, 14H), 1.07 (s, 4H) .; 1H NMR (400 MHz, Chloroform-d) δ 7.41-7.28 (m, 5H), 5.19-5.09 (m, 2H), 4.88 (d, J = 7.6 Hz, 1H), 4.03-3.91 (m, 1H), 3.86-3.29 (m, 6H), 1.87-1.65 (m, 2H), 1.44 (s, 9H). |
| 298 | 563.3 | 1H NMR (400 MHz, Methanol-d4) δ 8.56 (d, J = 8.1 Hz, 1H), 7.55 (d, J = 8.1 Hz, 1H), 7.47 (d, J = 1.2 Hz, 1H), 7.34 (s, 1H), 7.04 (d, J = 1.2 Hz, 1H), 5.05-4.95 (m, 2H), 4.81-4.67 (m, 1H), 4.63-4.30 (m, 1H), 4.24 (s, 3H), 4.09 (s, 3H), 4.00-3.87 (m, 2H), 3.81-3.34 (m, 11H), 2.30-2.17 (m, 1H), 2.00-1.70 (m, 3H), 1.68 (d, J = 6.6 Hz, 3H). |

TABLE 3-continued

| Example | ES/MS m/z [M + H]+ | ¹H NMR |
|---|---|---|
| 299 | 615.4 | 1H NMR (400 MHz, Methanol-d4) δ 8.05 (d, J = 8.1 Hz, 1H), 7.61 (s, 1H), 7.29-7.12 (m, 2H), 7.01 (s, 1H), 5.29-5.16 (m, 1H), 5.03-4.90 (m, 1H), 4.74-4.58 (m, 1H), 4.25-4.11 (m, 4H), 4.06 (s, 3H), 3.55-3.40 (m, 1H), 3.27-3.12 (m, 2H), 3.07-2.93 (m, 1H), 2.70 (s, 3H), 2.14-2.02 (m, 1H), 1.80-1.66 (m, 1H), 1.63-1.20 (m, 15H), 1.06 (s, 4H).; 1H NMR (400 MHz, Methanol-d4) δ 8.07 (d, J = 8.2 Hz, 1H), 7.98-7.90 (m, 2H), 7.61-7.54 (m, 2H), 7.54-7.46 (m, 2H), 7.31 (d, J = 8.1 Hz, 1H), 6.94 (s, 1H), 6.86 (s, 1H), 5.44 (q, J = 7.0 Hz, 1H), 4.65 (dd, J = 12.7, 4.7 Hz, 1H), 4.39-4.18 (m, 5H), 3.61-3.43 (m, 1H), 3.26 (q, J = 11.7 Hz, 2H), 3.08-2.96 (m, 1H), 2.82 (s, 3H), 2.73 (s, 3H), 2.23-2.02 (m, 1H), 1.93-1.82 (m, 1H), 1.70 (d, J = 7.0 Hz, 3H), 1.13-0.98 (m, 1H), 0.43-0.25 (m, 2H), 0.25-0.12 (m, 2H). |
| 300 | 558.3 | 1H NMR (400 MHz, DMSO-d6) δ 8.24 (d, J = 7.4 Hz, 1H), 8.09-7.82 (m, 5H), 7.29 (s, 1H), 7.09 (d, J = 8.0 Hz, 1H), 6.61-6.54 (m, 1H), 6.38 (s, 1H), 4.96 (p, J = 7.2 Hz, 1H), 4.63 (dt, J = 13.5, 6.8 Hz, 1H), 4.46 (s, 1H), 4.08 (d, J = 1.5 Hz, 3H), 3.26 (s, 2H), 2.78 (s, 3H), 2.20 (t, J = 11.4 Hz, 2H), 2.08-1.87 (m, 2H), 1.76 (s, 1H), 1.67-1.37 (m, 9H), 1.25-1.00 (m, 2H), 0.82 (s, 1H). |
| 301 | 572.3 | 1H NMR (400 MHz, DMSO-d6) δ 8.29 (d, J = 8.5 Hz, 1H), 8.16-7.85 (m, 4H), 7.31 (s, 1H), 7.11 (d, J = 8.0 Hz, 1H), 6.63 (s, 1H), 6.43 (s, 1H), 5.18 (p, J = 7.2 Hz, 1H), 4.89 (dt, J = 14.2, 7.9 Hz, 1H), 4.44-4.33 (m, 1H), 4.09 (s, 3H), 3.30-3.10 (m, 4H), 2.79 (s, 3H), 2.13-1.91 (m, 3H), 1.83-1.52 (m, 3H), 1.46-1.35 (m, 5H), 1.28-0.92 (m, 5H), 0.63 (s, 1H). |
| 302 | 584.3 | 1H NMR (400 MHz, DMSO-d6) δ 8.28 (d, J = 8.6 Hz, 1H), 8.05 (s, 1H), 7.93 (d, J = 8.1 Hz, 2H), 7.43 (s, 0H), 7.25 (s, 1H), 7.10 (d, J = 8.0 Hz, 1H), 6.60 (s, 1H), 6.34 (d, J = 5.5 Hz, 1H), 5.18 (q, J = 7.3 Hz, 1H), 4.97-4.84 (m, 1H), 4.51 (d, J = 18.8 Hz, 1H), 4.08 (s, 3H), 3.22 (dd, J = 18.1, 9.8 Hz, 1H), 2.80 (s, 3H), 2.14-1.82 (m, 5H), 1.66 (s, 2H), 1.41 (d, J = 7.1 Hz, 4H), 1.28-0.92 (m, 4H), 0.62 (s, 1H). |
| 303 | 600.3 | 1H NMR (400 MHz, DMSO-d6) δ 8.73 (d, J = 6.5 Hz, 1H), 7.99 (d, J = 8.0 Hz, 1H), 7.27 (s, 1H), 7.16 (d, J = 8.0 Hz, 1H), 6.60 (s, 1H), 6.36 (s, 1H), 5.06 (p, J = 6.6 Hz, 1H), 4.69 (t, J = 11.5 Hz, 1H), 4.50 (d, J = 16.9 Hz, 1H), 4.08 (s, 3H), 3.86 (d, J = 9.9 Hz, 1H), 3.71 (dt, J = 27.2, 8.9 Hz, 2H), 3.37-3.07 (m, 2H), 2.95 (d, J = 9.9 Hz, 1H), 2.84 (s, 3H), 2.39 (dd, J = 15.7, 7.4 Hz, 1H), 2.23 (d, J = 12.3 Hz, 1H), 2.02 (s, 1H), 1.76 (s, 1H), 1.58 (d, J = 14.2 Hz, 4H), 1.48 (d, J = 6.7 Hz, 3H), 0.41-0.20 (m, 4H). |
| 304 | 586.3 | 1H NMR (400 MHz, DMSO-d6) δ 8.37 (d, J = 7.4 Hz, 1H), 8.06 (d, J = 8.2 Hz, 1H), 7.93 (s, 3H), 7.43 (s, 1H), 7.20 (d, J = 8.3 Hz, 1H), 7.07 (d, J = 1.9 Hz, 1H), 6.91 (s, 1H), 5.06 (t, J = 7.2 Hz, 1H), 4.93-4.81 (m, 1H), 4.74-4.63 (m, 1H), 4.15 (s, 3H), 3.99 (s, 3H), 3.88 (t, J = 9.9 Hz, 1H), 3.77 (d, J = 11.5 Hz, 1H), 3.62-3.52 (m, 2H), 3.35-3.05 (m, 4H), 2.23 (dd, J = 24.9, 11.7 Hz, 2H), 2.23 (dd, J = 14.5, 5.1 Hz, 1H), 2.07-2.00 (m, 1H), 1.79-1.70 (m, 1H), 1.66-1.55 (m, 3H), 1.49 (d, J = 7.1 Hz, 3H), 0.91 (d, J = 7.5 Hz, 2H), 0.19 (t, J = 7.4 Hz, 2H). |
| 305 | 586.3 | 1H NMR (400 MHz, DMSO-d6) δ 8.61 (d, J = 6.9 Hz, 1H), 8.03 (dd, J = 8.2, 1.8 Hz, 1H), 7.93 (s, 3H), 7.42 (s, 1H), 7.20-7.15 (m, 1H), 7.08 (s, 1H), 6.91 (s, 1H), 5.01-4.91 (m, 2H), 4.49 (t, J = 12.3 Hz, 1H), 4.15 (s, 3H), 3.99 (s, 3H), 3.79-3.68 (m, 3H), 3.34-3.03 (m, 5H), 2.20 (d, J = 15.1 Hz, 1H), 2.05-1.98 (m, 1H), 1.80-1.70 (m, 1H), 1.63-1.53 (m, 2H), 1.41 (d, J = 7.0 Hz, 3H), 1.07-0.79 (m, 2H), 0.65-0.56 (m, 1H), 0.24-0.16 (m, 1H). |
| 306 | 600.3 | 1H NMR (400 MHz, DMSO-d6) δ 8.56-8.49 (m, 1H), 8.09-8.02 (m, 1H), 7.94 (s, 3H), 7.43 (s, 1H), 7.19 (dd, J = 8.6, 2.3 Hz, 1H), 7.03 (t, J = 1.8 Hz, 1H), 6.93 (s, 1H), 5.01 (t, J = 7.0 Hz, 1H), 4.89 (t, J = 12.3 Hz, 1H), 4.61-4.49 (m, 1H), 4.13 (s, 3H), 4.00 (s, 3H), 3.69-3.49 (m, 3H), 3.34-3.05 (m, 4H), 2.34-2.24 (m, 1H), 2.02 br (s, 1H), 1.75 br (s, 2H), 1.59 (br s, 2H), 1.47-1.38 (m, 4H), 1.06 (br s, 1H), 0.63 (br s, 1H), 0.50 (br s, 1H), −0.26 br s, 1H). |
| 307 | 585.3 | 1H NMR (400 MHz, DMSO-d6) δ 8.67 (d, J = 7.2 Hz, 1H), 7.93 (s, 3H), 7.58 (d, J = 8.2 Hz, 1H), 7.48 (s, 1H), 7.38 (s, 1H), 7.05-6.99 (m, 2H), 6.89 (s, 1H), 4.96 (p, J = 7.0 Hz, 1H), 4.74-4.65 (m, 1H), 4.43-4.33 (m, 1H), 4.08 (s, 3H), 3.98 (s, 3H), 3.58 (dd, J = 9.5, 3.0 Hz, 1H), 3.32-3.07 (m, 3H), 2.98 (t, J = 10.1 Hz, 1H), 2.76-2.65 (m, 1H), 2.06-1.96 (m, 2H), 1.89-1.71 (m, 3H), 1.64-1.45 (m, 3H), 1.42 (d, J = 7.0 Hz, 3H), 0.90-0.82 (m, 1H), 0.80-0.73 (m, 1H). |
| 308 | 586.3 | 1H NMR (400 MHz, DMSO-d6) δ 8.64 (d, J = 6.2 Hz, 1H), 7.99 (d, J = 8.1 Hz, 1H), 7.94 (br s, 3H), 7.39 (s, 1H), 7.12 (d, J = 8.1 Hz, 1H), 7.04 (s, 1H), 6.91 (d, J = 1.1 Hz, 1H), 5.16 (t, J = 12.8 Hz, 1H), 4.88 (p, J = 6.9 Hz, 1H), 4.63-4.53 (m, 1H), 4.11 (s, 3H), 3.98 (s, 3H), 3.48 (dd, J = 9.5, 2.9 Hz, 1H), 3.30-3.08 (m, 3H), 2.99-2.92 (m, 1H), 2.80 (t, J = 10.1 Hz, 1H), 2.07-1.88 (m, 2H), 1.80-1.52 (m, 5H), 1.42 (d, J = 7.1 Hz, 3H), 1.40-1.28 (m, 2H), 0.82-0.75 (m, 1H), 0.69-0.62 (m, 1H). |
| 309 | 586.3 | 1H NMR (400 MHz, DMSO-d6) δ 8.67 (d, J = 7.3 Hz, 1H), 8.04 (d, J = 8.2 Hz, 1H), 7.95 (s, 3H), 7.40 (s, 1H), 7.23 (d, J = 8.3 Hz, 1H), 7.06 (s, 1H), 6.91 (d, J = 1.1 Hz, 1H), 5.03-4.91 (m, 1H), 4.69-4.56 (m, 2H), |

TABLE 3-continued

| Example | ES/MS m/z [M + H]+ | ¹H NMR |
|---|---|---|
| | | 4.12 (s, 3H), 3.99 (s, 3H), 3.42 (dd, J = 9.6, 4.5 Hz, 1H), 3.33-3.03 (m, 3H), 3.01-2.91 (m, 2H), 2.74-2.65 (m, 1H), 2.06-1.98 (m, 1H), 1.81-1.28 (m, 8H), 0.85-0.73 (m, 2H). |
| 310 | 614.3 | 1H NMR (400 MHz, DMSO-d6) δ 8.74 (d, J = 6.1 Hz, 1H), 8.11 (d, J = 8.1 Hz, 1H), 7.95 (s, 3H), 7.43 (s, 1H), 7.24 (d, J = 8.2 Hz, 1H), 7.10 (s, 1H), 6.92 (d, J = 1.2 Hz, 1H), 5.05 (p, J = 6.6 Hz, 1H), 4.77-4.64 (m, 2H), 4.17 (s, 3H), 3.99 (s, 3H), 3.90 (dd, J = 11.2, 3.8 Hz, 1H), 3.69-3.61 (m, 1H), 3.57 (d, J = 9.9 Hz, 1H), 3.50 (d, J = 9.9 Hz, 1H), 3.34-3.02 (m, 3H), 2.06-1.98 (m, 1H), 1.81-1.71 (m, 1H), 1.66-1.52 (m, 2H), 1.46 (d, J = 6.7 Hz, 3H), 1.30-1.18 (m, 1H), 1.17 (s, 3H), 1.07 (s, 3H), 0.43-0.28 (m, 2H). |
| 311 | 612.3 | 1H NMR (400 MHz, DMSO-d6) δ 9.18 (br s, 1H), 8.15 (d, J = 8.2 Hz, 1H), 7.95 (s, 3H), 7.44 (br s, 1H), 7.27 (d, J = 8.2 Hz, 1H), 7.14 (s, 1H), 6.92 (d, J = 1.2 Hz, 1H), 5.05 (p, J = 6.5 Hz, 1H), 4.83-4.63 (m, 2H), 4.19 (s, 3H), 4.00 (s, 3H), 3.88 (dd, J = 11.0, 4.2 Hz, 1H), 3.81-3.71 (m, 1H), 3.34-3.05 (m, 4H), 2.06-1.99 (m, 1H), 1.76 (d, J = 5.2 Hz, 1H), 1.65-1.53 (m, 2H), 1.45 (d, J = 6.6 Hz, 3H), 1.35-1.25 (m, 1H), 1.10-1.00 (m, 2H), 0.78-0.65 (m, 2H), 0.45 (d, J = 25.2 Hz, 2H). |
| 312 | 600.3 | 1H NMR (400 MHz, DMSO-d6) δ 8.29 (d, J = 7.5 Hz, 1H), 8.05 (d, J = 8.2 Hz, 1H), 7.93 (s, 3H), 7.42 (s, 1H), 7.18 (d, J = 8.2 Hz, 1H), 7.06 (s, 1H), 6.91 (d, J = 1.2 Hz, 1H), 5.05 (p, J = 7.2 Hz, 1H), 4.93-4.84 (m, 1H), 4.74-4.66 (m, 1H), 4.14 (s, 3H), 3.99 (s, 3H), 3.84-3.77 (m, 1H), 3.68 (t, J = 9.7 Hz, 1H), 3.54 (dd, J = 11.9, 5.4 Hz, 1H), 3.31-3.08 (m, 4H), 2.81-2.70 (m, 1H), 2.06-1.98 (m, 1H), 1.80-1.70 (m, 1H), 1.65-1.53 (m, 2H), 1.48 (d, J = 7.1 Hz, 3H), 0.96 (d, J = 7.0 Hz, 3H), 0.92-0.84 (m, 2H), 0.19-0.10 (m, 2H). |
| 313 | 600.3 | 1H NMR (400 MHz, DMSO-d6) δ 8.62 (d, J = 6.4 Hz, 1H), 8.10 (d, J = 8.1 Hz, 1H), 7.94 (s, 3H), 7.43 (s, 1H), 7.24 (d, J = 8.2 Hz, 1H), 7.10 (s, 1H), 6.92 (d, J = 1.2 Hz, 1H), 4.98 (p, J = 6.7 Hz, 1H), 4.75 (d, J = 14.3, 7.4 Hz, 1H), 4.66 (dd, J = 14.1, 7.0 Hz, 1H), 4.17 (s, 3H), 3.99 (s, 3H), 3.82 (dd, J = 11.0, 4.7 Hz, 1H), 3.70-3.54 (m, 3H), 3.32-3.07 (m, 4H), 2.06-1.99 (m, 1H), 1.80-1.70 (m, 1H), 1.66-1.53 (m, 2H), 1.50 (d, J = 6.8 Hz, 3H), 1.25-1.15 (m, 1H), 1.12 (d, J = 7.4 Hz, 3H), 0.43-0.29 (m, 2H). |
| 314 | 616.3 | 1H NMR (400 MHz, DMSO-d6) δ 8.37 (d, J = 7.4 Hz, 1H), 8.06 (d, J = 8.2 Hz, 1H), 7.97 (s, 3H), 7.46 (s, 1H), 7.20 (d, J = 8.2 Hz, 1H), 7.07 (s, 1H), 6.93 (s, 1H), 5.06 (p, J = 7.1 Hz, 1H), 4.93-4.83 (m, 1H), 4.74-4.65 (m, 1H), 4.15 (s, 3H), 3.99 (s, 3H), 3.88 (t, J = 9.8 Hz, 1H), 3.81-3.48 (m, 6H), 3.36 (s, 3H), 2.69-2.57 (m, 1H), 2.23 (dd, J = 14.2, 5.0 Hz, 1H), 2.00-1.89 (m, 1H), 1.80-1.70 (m, 1H), 1.49 (d, J = 7.0 Hz, 3H), 0.96-0.87 (m, 2H), 0.19 (t, J = 7.4 Hz, 2H). |
| 315 | 604.3 | 1H NMR (400 MHz, DMSO-d6) δ 8.76 (s, 2H), 8.70 (d, J = 7.9 Hz, 1H), 8.35 (d, J = 7.4 Hz, 1H), 8.07 (d, J = 8.1 Hz, 1H), 8.01 (d, J = 1.2 Hz, 1H), 7.35 (d, J = 1.2 Hz, 1H), 7.20 (d, J = 8.2 Hz, 1H), 7.12 (s, 1H), 5.07 (p, J = 7.1 Hz, 1H), 4.96-4.76 (m, 2H), 4.72 (dd, J = 13.9, 6.2 Hz, 1H), 4.50-4.37 (m, 1H), 4.18 (s, 3H), 4.02 (s, 3H), 3.94-3.85 (m, 1H), 3.78 (dd, J = 11.7, 3.5 Hz, 1H), 3.63-3.50 (m, 2H), 3.49-3.32 (dd, J = 25.1, 12.5 Hz, 2H), 3.13-2.90 (m, 2H), 2.69-2.57 (m, 1H), 2.24 (dd, J = 14.3, 5.1 Hz, 1H), 1.937-1.84 (m, 1H), 1.49 (d, J = 7.1 Hz, 3H), 1.05-0.88 (, 2H), 0.26-0.15 (m, 2H). |
| 316 | 584.4 | 1H NMR (400 MHz, DMSO-d6) δ 8.28 (d, J = 8.6 Hz, 1H), 8.11 (s, 3H), 7.94 (d, J = 8.0 Hz, 1H), 7.45 (s, 1H), 7.10 (d, J = 8.0 Hz, 1H), 6.61 (s, 1H), 6.39 (s, 1H), 5.18 (p, J = 7.4 Hz, 1H), 4.90 (dt, J = 14.4, 7.8 Hz, 1H), 4.55-4.40 (m, 2H), 4.10 (s, 3H), 3.75 (s, 1H), 2.80 (s, 3H), 2.33 (s, 1H), 2.14-1.55 (m, 8H), 1.52-1.29 (m, 7H), 1.27-0.90 (m, 5H), 0.63 (s, 1H) |
| 317 | 570.3 | 1H NMR (400 MHz, DMSO-d6) δ 8.23 (d, J = 7.4 Hz, 1H), 8.18-8.03 (m, 3H), 7.90 (d, J = 8.0 Hz, 1H), 7.44 (s, 1H), 7.09 (d, J = 8.0 Hz, 1H), 6.58 (s, 1H), 6.38 (s, 1H), 4.96 (p, J = 7.1 Hz, 1H), 4.70-4.39 (m, 2H), 4.10 (s, 3H), 2.79 (s, 3H), 2.20 (t, J = 11.4 Hz, 2H), 1.96-1.77 (m, 4H), 1.69-1.30 (m, 9H), 1.27-0.97 (m, 2H), 0.82 (s, 1H). |
| 318 | 598.4 | 1H NMR (400 MHz, DMSO-d6) δ 8.17 (d, J = 7.2 Hz, 1H), 8.10 (s, 4H), 7.92 (d, J = 8.0 Hz, 1H), 7.45 (s, 1H), 7.12 (d, J = 8.0 Hz, 1H), 6.58 (s, 1H), 6.39 (s, 1H), 5.02 (p, J = 7.2 Hz, 1H), 4.46 (dtd, J = 27.3, 13.5, 6.8 Hz, 2H), 4.10 (s, 3H), 2.79 (s, 3H), 2.29 (dd, J = 23.7, 11.3 Hz, 2H), 2.04-1.73 (m, 5H), 1.62 (t, J = 16.1 Hz, 2H), 1.46 (d, J = 7.0 Hz, 3H), 1.39-1.27 (m, 3H), 1.27-0.88 (m, 8H). |
| 319 | 598.4 | 1H NMR (400 MHz, DMSO-d6) δ 8.28 (d, J = 8.5 Hz, 1H), 7.94 (d, J = 8.0 Hz, 1H), 7.44 (s, 1H), 7.11 (d, J = 8.0 Hz, 1H), 6.61 (s, 1H), 6.38 (s, 1H), 5.18 (p, J = 7.1 Hz, 1H), 4.90 (dt, J = 14.4, 7.7 Hz, 1H), 4.45 (d, J = 15.6 Hz, 2H), 4.10 (s, 3H), 3.71 (s, 1H), 2.80 (s, 3H), 2.64 (q, J = 7.6, 5.5 Hz, 3H), 2.13-1.80 (m, 5H), 1.75-1.57 (m, 2H), 1.53-1.31 (m, 7H), 1.28-0.90 (m, 5H), 0.63 (s, 1H). |
| 320 | 556.3 | 1H NMR (400 MHz, DMSO-d6) δ 8.08 (s, 4H), 7.90 (d, J = 8.3 Hz, 1H), 7.87 (d, J = 8.0 Hz, 1H), 7.42 (s, 1H), 7.05 (d, J = 8.1 Hz, 1H), 6.56 (s, 1H), 6.36 (d, J = 1.4 Hz, 1H), 4.88 (p, J = 7.2 Hz, 1H), 4.65-4.30 (m, |

TABLE 3-continued

| Example | ES/MS m/z [M + H]+ | ¹H NMR |
|---|---|---|
| | | 4H), 4.09 (s, 3H), 2.80 (s, 3H), 1.88 (d, J = 35.3 Hz, 5H), 1.66 (dt, J = 23.8, 10.3 Hz, 2H), 1.46 (d, J = 7.2 Hz, 3H), 1.35 (dd, J = 12.9, 4.4 Hz, 1H), 1.28-1.08 (m, 3H). |
| 321 | 586.3 | 1H NMR (400 MHz, DMSO-d6) δ 8.59 (d, J = 6.8 Hz, 1H), 8.20-8.04 (m, 3H), 7.98 (d, J = 8.0 Hz, 1H), 7.46 (s, 1H), 7.15 (d, J = 8.0 Hz, 1H), 6.61 (s, 1H), 6.40 (s, 1H), 5.08 (p, J = 6.7 Hz, 1H), 4.69-4.33 (m, 4H), 4.11 (s, 3H), 3.94-3.60 (m, 4H), 3.37 (q, J = 6.6, 6.0 Hz, 1H), 2.81 (s, 3H), 2.71-2.55 (m, 1H), 2.38-2.21 (m, 2H), 1.87 (d, J = 19.9 Hz, 5H), 1.75-1.58 (m, 1H), 1.55-1.35 (m, 5H), 1.35 (dd, J = 12.9, 4.3 Hz, 1H). |
| 322 | 598.3 | 1H NMR (400 MHz, DMSO-d6) δ 8.50 (d, J = 6.7 Hz, 1H), 8.08 (s, 4H), 7.96-7.88 (m, 1H), 7.44 (s, 1H), 7.11 (d, J = 8.0 Hz, 1H), 6.58 (d, J = 1.7 Hz, 1H), 6.37 (s, 1H), 5.01-4.92 (m, 1H), 4.64 (d, J = 13.8 Hz, 1H), 4.48 (s, 2H), 4.10 (d, J = 1.8 Hz, 3H), 3.97 (dd, J = 14.2, 7.3 Hz, 1H), 3.60 (d, J = 6.4 Hz, 2H), 3.43 (dd, J = 11.0, 5.1 Hz, 1H), 2.82 (s, 3H), 2.13 (d, J = 15.4 Hz, 1H), 1.83 (s, 3H), 1.76-1.58 (m, 2H), 1.43 (d, J = 6.7 Hz, 3H), 1.40-1.25 (m, 1H), 0.88 (dd, J = 15.1, 7.4 Hz, 3H), 0.43 (d, J = 7.1 Hz, 1H), 0.30 (d, J = 7.8 Hz, 1H). |
| 323 | 598.3 | 1H NMR (400 MHz, DMSO-d6) δ 8.47 (d, J = 7.3 Hz, 1H), 8.09 (s, 4H), 7.94 (d, J = 7.9 Hz, 1H), 7.45 (s, 1H), 7.13 (d, J = 7.9 Hz, 1H), 6.56 (d, J = 1.5 Hz, 1H), 6.36 (s, 1H), 5.03 (t, J = 6.9 Hz, 1H), 4.92 (d, J = 12.1 Hz, 1H), 4.79 (d, J = 14.0 Hz, 1H), 4.49 (s, 1H), 4.10 (s, 3H), 3.73 (s, 1H), 3.46 (q, J = 12.8, 10.0 Hz, 3H), 2.80 (s, 3H), 2.72 (t, J = 9.9 Hz, 1H), 2.10 (d, J = 12.4 Hz, 1H), 1.84 (s, 3H), 1.64 (d, J = 9.7 Hz, 1H), 1.44 (d, J = 6.7 Hz, 3H), 1.40-1.25 (m, 3H), 0.88 (dt, J = 21.9, 7.7 Hz, 3H), 0.23-0.12 (m, 1H), 0.07 (d, J = 4.5 Hz, 1H). |
| 324 | 572.3 | 1H NMR (400 MHz, DMSO-d6) δ 8.26 (d, J = 7.5 Hz, 1H), 8.15-8.02 (m, 3H), 7.99 (dd, J = 8.2, 2.1 Hz, 1H), 7.43 (s, 1H), 7.21 (dd, J = 7.8, 2.3 Hz, 1H), 6.62 (d, J = 2.5 Hz, 1H), 6.36 (s, 1H), 5.07 (t, J = 7.4 Hz, 1H), 4.60-4.25 (m, 4H), 4.16-3.97 (m, 5H), 2.82 (d, J = 2.4 Hz, 3H), 2.33 (s, 1H), 1.98 (s, 1H), 1.90-1.61 (m, 4H), 1.59-1.52 (m, 3H), 1.52-1.41 (m, 4H), 1.34 (d, J = 12.9 Hz, 1H). |
| 325 | 584.3 | 1H NMR (400 MHz, DMSO-d6) δ 8.64 (d, J = 7.9 Hz, 1H), 8.08 (br s, 3H), 7.97 (d, J = 8.0 Hz, 1H), 7.45 (s, 1H), 7.18 (d, J = 8.1 Hz, 1H), 6.59 (s, 1H), 6.37 (d, J = 1.3 Hz, 1H), 5.08 (p, J = 6.9 Hz, 1H), 4.85 (dd, J = 14.2, 3.5 Hz, 1H), 4.48 (s, 3H), 4.21 (dd, J = 14.2, 7.3 Hz, 1H), 4.12 (d, J = 14.9 Hz, 1H), 4.09 (br s, 3H), 3.58 (d, J = 14.7 Hz, 1H), 3.40 (dd, J = 10.9, 3.6 Hz, 1H), 3.31-3.25 (m, 1H), 2.79 (s, 3H), 1.90-1.57 (m, 5H), 1.52 (d, J = 6.9 Hz, 3H), 1.34 (dd, J = 12.9, 4.4 Hz, 1H), 0.91 (s, 1H), 0.38 (dt, J = 9.2, 5.0 Hz, 1H), 0.17 (td, J = 8.8, 8.2, 4.2 Hz, 1H). |
| 326 | 584.3 | 1H NMR (400 MHz, DMSO-d6) δ 8.73-8.65 (m, 1H), 8.07 (s, 3H), 7.97 (d, J = 8.0 Hz, 1H), 7.45 (s, 1H), 7.17 (d, J = 8.1 Hz, 1H), 6.59 (s, 1H), 6.37 (d, J = 1.3 Hz, 1H), 5.17 (p, J = 7.0 Hz, 1H), 4.85 (d, J = 13.7 Hz, 1H), 4.49 (s, 3H), 4.22 (d, J = 14.7 Hz, 1H), 4.09 (s, 3H), 3.77-3.65 (m, 2H), 3.24-3.19 (m, 1H), 3.14 (dd, J = 10.6, 4.1 Hz, 1H), 2.81 (s, 3H), 1.97 (s, 1H), 1.84 (s, 3H), 1.64 (d, J = 8.7 Hz, 1H), 1.47 (d, J = 6.9 Hz, 3H), 1.34 (dd, J = 12.8, 4.4 Hz, 1H), 0.73 (s, 1H), 0.64 (dt, J = 9.2, 4.8 Hz, 1H), 0.49 (dt, J = 9.2, 5.2 Hz, 1H). |
| 327 | 598.3 | 1H NMR (400 MHz, DMSO-d6) δ 8.61 (d, J = 6.9 Hz, 1H), 7.91 (d, J = 8.0 Hz, 1H), 7.33 (s, 1H), 7.08 (d, J = 8.0 Hz, 1H), 6.62 (s, 1H), 6.31 (s, 1H), 4.94 (t, J = 7.0 Hz, 1H), 4.43 (dd, J = 14.2, 10.4 Hz, 1H), 4.08 (s, 2H), 3.80-3.65 (m, 3H), 3.48 (s, 1H), 2.84 (s, 3H), 2.29-2.06 (m, 3H), 1.85-1.48 (m, 2H), 1.40 (d, J = 7.0 Hz, 3H), 0.97 (s, 2H), 0.82 (dt, J = 14.8, 7.4 Hz, 1H), 0.58 (dt, J = 8.8, 4.5 Hz, 1H), 0.20-0.11 (m, 1H). |
| 328 | 598.3 | 1H NMR (400 MHz, DMSO-d6) δ 8.39 (d, J = 7.5 Hz, 1H), 7.95 (d, J = 8.0 Hz, 1H), 7.46 (s, 1H), 7.12 (d, J = 8.1 Hz, 1H), 6.63 (s, 1H), 6.35 (d, J = 1.4 Hz, 1H), 5.06 (p, J = 7.0 Hz, 1H), 4.81 (dd, J = 14.0, 7.5 Hz, 1H), 4.63 (dd, J = 13.8, 6.1 Hz, 1H), 4.09 (s, 3H), 3.92-3.53 (m, 4H), 2.85 (s, 3H), 2.38-2.17 (m, 1H), 1.84 (s, 4H), 1.64 (d, J = 9.0 Hz, 1H), 1.48 (d, J = 7.0 Hz, 3H), 1.43-1.30 (m, 1H), 1.02-0.80 (m, 1H), 0.30-0.12 (m, 2H). |
| 329 | 598.3 | 1H NMR (400 MHz, DMSO-d6) δ 8.40 (d, J = 7.7 Hz, 1H), 8.07 (s, 3H), 7.91 (d, J = 8.0 Hz, 1H), 7.42 (s, 1H), 7.11 (d, J = 8.1 Hz, 1H), 6.58 (s, 1H), 6.36 (s, 1H), 5.33 (d, J = 14.1 Hz, 1H), 4.99 (p, J = 7.2 Hz, 1H), 4.47 (s, 2H), 4.21 (d, J = 14.2 Hz, 1H), 4.10 (s, 3H), 2.81 (s, 3H), 2.26 (d, J = 9.4 Hz, 1H), 2.02 (d, J = 15.3 Hz, 1H), 1.84 (s, 4H), 1.64 (d, J = 9.6 Hz, 1H), 1.46 (d, J = 7.1 Hz, 3H), 1.34 (dd, J = 12.9, 4.4 Hz, 1H), 0.28 (dt, J = 9.6, 4.9 Hz, 1H), 0.22-0.15 (m, 1H), −0.04--0.12 (m, 1H), −0.44--0.51 (m, 1H). |
| 330 | 612.3 | 1H NMR (400 MHz, DMSO-d6) δ 8.67 (d, J = 8.2 Hz, 1H), 8.10 (s, 3H), 8.02 (d, J = 8.0 Hz, 1H), 7.38 (s, 1H), 7.21 (d, J = 8.0 Hz, 1H), 6.63 (s, 1H), 6.36 (s, 1H), 5.25 (p, J = 7.1 Hz, 1H), 4.80 (t, J = 12.4 Hz, 1H), 4.49 (s, 3H), 4.17 (d, J = 15.6 Hz, 1H), 4.10 (s, 3H), 3.91 (d, J = 6.9 Hz, 1H), 3.72 (d, J = 15.6 Hz, 1H), 3.53 (q, J = 7.9 Hz, 1H), 2.84 (s, 3H), 2.33 (s, 1H), 2.16 (t, J = 12.1 Hz, 1H), 1.84 (s, 3H), 1.64 (d, J = 9.4 Hz, 1H), 1.48 (d, J = 6.8 Hz, 3H), 1.41-1.23 (m, 2H), 1.19-1.04 (m, 1H), 0.29 (s, 3H), 0.20 (s, 1H). |

TABLE 3-continued

| Example | ES/MS m/z [M + H]+ | ¹H NMR |
|---|---|---|
| 331 | 612.3 | 1H NMR (400 MHz, DMSO-d6) δ 8.72 (d, J = 6.4 Hz, 1H), 8.09 (s, 3H), 7.99 (d, J = 8.0 Hz, 1H), 7.40 (s, 1H), 7.16 (d, J = 8.1 Hz, 1H), 6.61 (s, 1H), 6.38 (s, 1H), 5.07 (p, J = 6.8 Hz, 1H), 4.75-4.65 (m, 1H), 4.10 (s, 3H), 3.87 (d, J = 9.8 Hz, 1H), 3.71 (dt, J = 27.3, 8.7 Hz, 3H), 2.93 (d, J = 9.8 Hz, 1H), 2.84 (s, 3H), 2.64-2.53 (m, 3H), 2.43-2.28 (m, 1H), 2.26-2.15 (m, 1H), 1.84 (s, 3H), 1.64 (d, J = 9.9 Hz, 1H), 1.48 (d, J = 6.8 Hz, 4H), 1.35 (dd, J = 13.0, 4.3 Hz, 1H), 0.39-0.18 (m, 4H). |
| 332 | 614.3 | 1H NMR (400 MHz, DMSO-d6) δ 8.18 (d, J = 7.1 Hz, 1H), 8.11 (s, 3H), 7.93 (d, J = 7.9 Hz, 1H), 7.45 (s, 1H), 7.10 (d, J = 8.0 Hz, 1H), 6.59 (s, 1H), 6.37 (s, 1H), 5.03 (q, J = 7.0 Hz, 1H), 4.71 (dt, J = 14.5, 7.6 Hz, 1H), 4.65-4.35 (m, 2H), 4.10 (s, 3H), 3.70 (d, J = 51.4 Hz, 2H), 3.28 (s, 3H), 2.85-2.78 (m, 1H), 2.80 (s, 3H), 2.01 (dd, J = 13.0, 8.6 Hz, 1H), 1.79 (d, J = 34.7 Hz, 3H), 1.62 (q, J = 13.5, 11.2 Hz, 2H), 1.40 (dd, J = 25.9, 5.8 Hz, 5H), 1.20 (dd, J = 20.2, 9.5 Hz, 2H), 1.02-0.85 (m, 1H). |
| 333 | 614.4 | 1H NMR (400 MHz, DMSO-d6) δ 8.46 (d, J = 8.7 Hz, 1H), 8.19-8.05 (m, 3H), 7.93 (d, J = 8.0 Hz, 1H), 7.45 (s, 1H), 7.10 (d, J = 8.0 Hz, 1H), 6.61 (s, 1H), 6.38 (s, 1H), 5.16 (p, J = 7.3 Hz, 1H), 4.90 (dd, J = 14.2, 7.5 Hz, 1H), 4.49 (d, J = 14.2 Hz, 2H), 4.10 (s, 3H), 3.76 (s, 1H), 3.53-3.41 (m, 1H), 3.19 (s, 3H), 2.81 (s, 3H), 1.90 (d, J = 47.7 Hz, 4H), 1.61 (q, J = 12.8, 11.7 Hz, 2H), 1.41 (d, J = 7.1 Hz, 3H), 1.39-1.31 (m, 1H), 1.16 (d, J = 9.4 Hz, 1H), 1.05 (d, J = 13.0 Hz, 2H), 0.57 (s, 1H). |
| 334 | 614.4 | 1H NMR (400 MHz, DMSO-d6) δ 8.08 (s, 3H), 7.97 (d, J = 8.0 Hz, 1H), 7.89 (d, J = 8.7 Hz, 1H), 7.45 (s, 1H), 7.16 (d, J = 8.0 Hz, 1H), 6.61 (s, 1H), 6.37 (s, 1H), 5.25 (q, J = 7.5 Hz, 1H), 4.73-4.63 (m, 1H), 4.50-4.40 (m, 2H), 4.10 (s, 3H), 3.76 (d, J = 4.8 Hz, 2H), 3.37 (s, 3H), 2.80 (s, 3H), 1.91-1.58 (m, 8H), 1.56-1.29 (m, 7H), 1.12 (d, J = 27.0 Hz, 3H), 0.80 (s, 1H). |
| 335 | 614.4 | 1H NMR (400 MHz, DMSO-d6) δ 8.60 (d, J = 8.4 Hz, 1H), 8.08 (s, 3H), 7.95 (d, J = 7.9 Hz, 1H), 7.44 (s, 1H), 7.13 (d, J = 8.0 Hz, 1H), 6.61 (s, 1H), 6.37 (s, 1H), 5.27 (q, J = 7.4 Hz, 1H), 4.86 (dt, J = 14.6, 7.4 Hz, 1H), 4.48 (d, J = 14.3 Hz, 2H), 4.10 (s, 3H), 3.94 (t, J = 7.7 Hz, 1H), 3.22 (s, 3H), 2.80 (s, 3H), 1.91 (d, J = 54.7 Hz, 5H), 1.60 (d, J = 23.8 Hz, 3H), 1.51-1.22 (m, 7H), 1.06 (s, 3H), 0.84 (s, 1H), 0.58 (s, 1H). |
| 336 | 598.3 | 1H NMR (400 MHz, DMSO-d6) δ 8.36 (d, J = 7.4 Hz, 1H), 8.06 (d, J = 7.9 Hz, 4H), 7.61 (s, 1H), 7.20 (d, J = 8.4 Hz, 1H), 7.08 (s, 1H), 7.03 (s, 1H), 5.06 (t, J = 7.2 Hz, 1H), 4.92-4.85 (m, 1H), 4.70 (dm, J = 13.6 Hz, 1H), 4.60-4.35 (s, 4H), 4.15 (s, 3H), 4.00 (s, 3H), 3.88 (t, J = 9.9 Hz, 1H), 3.75 (t, J = 13.9 Hz, 2H), 3.58 (d, J = 15.4 Hz, 2H), 2.28-2.20 (m, 1H), 1.83 (br s, 4H), 1.68-1.57br (m, 1H), 1.49 (d, J = 7.0 Hz, 3H), 1.38-1.29 (m, 1H), 0.91 (s, 2H), 0.18 (t, J = 7.4 Hz, 2H). |
| 337 | 598.3 | 1H NMR (400 MHz, DMSO-d6) δ 8.60 (d, J = 6.8 Hz, 1H), 8.15-8.00 (m, 4H), 7.60 (s, 1H), 7.18 (d, J = 8.7 Hz, 1H), 7.08 (s, 1H), 7.04 (s, 1H), 5.03-4.91 (m, 2H), 4.60-4.35 (t, J = 12.9 Hz, 2H), 4.15 (d, J = 2.0 Hz, 3H), 4.01 (d, J = 2.1 Hz, 3H), 3.83-3.65 (m, 4H), 3.12-3.04 (m, J = 9.7 Hz, 1H), 2.20 (d, J = 15.2 Hz, 1H), 1.83 (br s, 4H), 1.63 (d, J = 10.0 Hz, 1H), 1.41 (d, J = 7.0 Hz, 3H), 1.34 (d, J = 12.8 Hz, 1H), 1.05-0.79 (m, 2H), 0.61 (br s, 1H), 0.19 (br s, 1H). |
| 338 | 612.3 | 1H NMR (400 MHz, DMSO-d6) δ 8.52 (d, J = 6.5 Hz, 1H), 8.18-8.01 (m, 4H), 7.60 (s, 1H), 7.19 (d, J = 8.2 Hz, 1H), 7.07-7.00 (m, 2H), 5.01 (t, J = 7.1 Hz, 1H), 4.95-4.79 (m, 1H), 4.63-4.32 (m, 3H), 4.13 (d, J = 2.2 Hz, 3H), 4.01 (d, J = 2.2 Hz, 3H), 3.74 (s, 3H), 3.68-3.57 (m, 2H), 3.53 (d, J = 10.7 Hz, 1H), 3.16 (t, J = 10.3 Hz, 1H), 2.38-2.24 (m, 2H), 1.93-1.57 (m, 6H), 1.42 (d, J = 7.0 Hz, 3H), 1.38-1.28 (m, 1H), 1.05 (s, 1H), 0.66-0.42 (m, 2H), −0.21-−0.32 (m, 1H). |
| 339 | 627.3 | 1H NMR (400 MHz, DMSO-d6) δ 8.11 (d, J = 7.2 Hz, 1H), 8.05 (s, 3H), 7.62 (d, J = 8.2 Hz, 1H), 7.57 (s, 1H), 7.34 (s, 1H), 7.08 (dd, J = 8.3, 1.3 Hz, 1H), 7.02 (d, J = 1.2 Hz, 1H), 6.99 (s, 1H), 4.93 (p, J = 7.0 Hz, 1H), 4.60-4.34 (m, 3H), 4.27-4.16 (m, 1H), 4.10 (s, 3H), 4.00 (s, 3H), 3.74 (br s, 1H), 3.20 (s, 3H), 2.03-1.92 (m, 1H), 1.90-1.71 (m, 4H), 1.68-1.43 (m, 5H), 1.42 (s, 3H), 1.33 (dd, J = 12.7, 4.4 Hz, 1H), 1.26-1.13 (m, 4H). |
| 340 | 627.3 | 1H NMR (400 MHz, DMSO-d6) δ 8.18 (d, J = 7.7 Hz, 1H), 8.05 (s, 4H), 7.61 (d, J = 8.2 Hz, 1H), 7.57 (s, 1H), 7.38 (s, 1H), 7.09 (d, J = 8.2 Hz, 1H), 7.02 (s, 1H), 6.99 (s, 1H), 5.08 (p, J = 7.0 Hz, 1H), 4.64-4.31 (m, 3H), 4.24-4.16 (m, 1H), 4.09 (s, 3H), 4.00 (s, 3H), 3.74 (br s, 1H), 2.06-1.96 (m, 1H), 1.89-1.75 (m, 2H), 1.74-1.53 (m, 2H), 1.51 (d, J = 7.1 Hz, 3H), 1.46-1.29 (m, 3H), 1.22 (s, 3H), 1.15 (d, J = 8.1 Hz, 2H). |
| 341 | 641.4 | 1H NMR (400 MHz, DMSO-d6) δ 8.07 (br s, 3H), 7.97 (d, J = 7.3 Hz, 1H), 7.60 (d, J = 8.2 Hz, 1H), 7.57 (s, 1H), 7.35 (s, 1H), 7.06 (dd, J = 8.3, 1.3 Hz, 1H), 7.02 (d, J = 1.2 Hz, 1H), 6.99 (s, 1H), 5.08-4.98 (m, 1H), 4.65-4.37 (m, 3H), 4.23-4.14 (m, 1H), 4.10 (s, 3H), 4.00 (s, 3H), 3.75 (br s, 1H), 3.53 (d, J = 9.3 Hz, 1H), 3.33 (d, J = 9.6 Hz, 1H), 3.31 (s, 3H), 2.36-2.25 (m, 1H), 2.06-1.97 (m, 1H), 1.88-1.57 (m, 6H), 1.50-1.30 (m, 8H), 1.15-1.03 (m, 3H), 0.94 (s, 3H). |
| 342 | 597.3 | 1H NMR (400 MHz, DMSO-d6) δ 8.67 (d, J = 7.1 Hz, 1H), 8.06 (s, 3H), 7.60-7.55 (m, 2H), 7.48 (s, 1H), 7.05-6.99 (m, 3H), 4.96 (p, J = 6.9 Hz, |

TABLE 3-continued

| Example | ES/MS m/z [M + H]+ | ¹H NMR |
|---|---|---|
| | | 1H), 4.75-4.66 (m, 1H), 4.55-4.32 (m, 2H), 4.08 (s, 3H), 4.00 (s, 3H), 3.12 (d, J = 9.3 Hz, 1H), 2.98 (t, J = 10.1 Hz, 1H), 2.76-2.66 (m, 1H), 2.36-2.25 (m, 1H), 2.04-1.98 (m, 1H), 1.90-1.73 (m, 6H), 1.67-1.46 (m, 2H), 1.42 (d, J = 7.1 Hz, 3H), 1.33 (dd, J = 12.9, 4.4 Hz, 1H), 0.89-0.74 (m, 2H). |
| 343 | 640.5 | 1H NMR (400 MHz, DMSO-d6) δ 9.32 (s, 1H), 8.84 (s, 1H), 8.09 (d, J = 8.1 Hz, 1H), 8.05 (d, J = 7.8 Hz, 1H), 7.42 (d, J = 1.1 Hz, 1H), 7.23 (d, J = 8.2 Hz, 1H), 7.04 (s, 1H), 6.91 (s, 1H), 5.25 (p, J = 7.0 Hz, 1H), 4.87-4.72 (m, 1H), 4.48-4.32 (m, 1H), 4.11 (s, 3H), 4.04-4.01 (m, 2H), 3.98 (s, 3H), 3.79-3.64 (m, 2H), 3.11-2.94 (m, 2H), 2.25 (t, J = 12.6 Hz, 1H), 2.12-1.93 (m, 1H), 1.89-1.81 (m, 2H), 1.81-1.67 (m, 3H), 1.43 (d, J = 6.9 Hz, 3H), 1.41-1.30 (m, 1H), 1.29-1.15 (m, 3H), 1.15-0.98 (m, 1H), 0.96-0.88 (m, 1H), 0.62-0.53 (m, 1H), 0.50-0.40 (m, 1H). |
| 344 | 639.3 | 1H NMR (400 MHz, DMSO-d6) δ 9.20 (d, J = 6.9 Hz, 1H), 8.83 (s, 2H), 8.72 (d, J = 7.9 Hz, 1H), 8.57 (d, J = 5.1 Hz, 1H), 8.55 (s, 1H), 8.10 (d, J = 8.0 Hz, 1H), 7.99 (s, 1H), 7.49 (d, J = 5.1 Hz, 1H), 7.36 (s, 1H), 7.26 (d, J = 8.1 Hz, 1H), 7.13 (s, 1H), 5.21 (p, J = 7.0 Hz, 1H), 4.99-4.72 (m, 2H), 4.69-4.56 (m, 1H), 4.50-4.38 (m, 1H), 4.15 (s, 3H), 4.03 (s, 3H), 3.56-3.31 (m, 2H), 3.17-2.88 (m, 2H), 2.46-2.26 (m, 4H), 2.03-1.82 (m, 1H), 1.66-1.06 (m, 7H), 0.66-0.48 (m, 1H). |
| 345 | 656.3 | 1H NMR (400 MHz, DMSO-d6) δ 9.17 (d, J = 7.4 Hz, 1H), 8.76 (s, 2H), 8.70 (d, J = 7.9 Hz, 1H), 8.08 (d, J = 8.0 Hz, 1H), 7.99 (d, J = 1.2 Hz, 1H), 7.35 (d, J = 1.2 Hz, 1H), 7.34-7.28 (m, 1H), 7.25 (d, J = 8.1 Hz, 1H), 7.13 (s, 1H), 7.11-6.97 (m, 2H), 5.28 (p, J = 7.1 Hz, 1H), 5.01-4.73 (m, 2H), 4.69-4.55 (m, 1H), 4.54-4.35 (m, 1H), 4.14 (s, 3H), 4.02 (s, 3H), 3.41-3.27 (m, 1H), 3.15-2.86 (m, 2H), 2.43-2.12 (m, 4H), 2.02-1.82 (m, 1H), 1.67-1.07 (m, 8H), 0.56-0.33 (m, 1H). |
| 346 | 650.3 | 1H NMR (400 MHz, DMSO-d6) δ 8.92-8.76 (m, 3H), 8.72 (d, J = 7.9 Hz, 1H), 8.06 (d, J = 8.0 Hz, 1H), 8.01 (s, 1H), 7.44-7.31 (m, 3H), 7.31-7.18 (m, 3H), 7.07 (s, 1H), 5.18 (p, J = 7.0 Hz, 1H), 4.86 (dtd, J = 48.8, 9.4, 4.5 Hz, 1H), 4.69 (dd, J = 14.0, 2.7 Hz, 1H), 4.54-4.38 (m, 1H), 4.17 (s, 3H), 4.02 (s, 3H), 3.89-3.78 (m, 2H), 3.51-3.30 (m, 2H), 3.15-2.87 (m, 2H), 2.73-2.56 (m, 1H), 2.43-2.28 (m, 1H), 2.02-1.84 (m, 1H), 1.74-1.59 (m, 1H), 1.50 (d, J = 7.1 Hz, 3H), 1.41-1.28 (m, 1H), 1.28-1.07 (m, 2H), 0.31 (dt, J = 8.9, 4.6 Hz, 1H), 0.23 (dt, J = 9.3, 4.9 Hz, 1H). |
| 347 | 652.3 | 1H NMR (400 MHz, DMSO-d6) δ 8.84 (d, J = 6.8 Hz, 1H), 8.73 (s, 2H), 8.62 (d, J = 8.0 Hz, 1H), 8.08 (d, J = 8.0 Hz, 1H), 7.98 (d, J = 6.3 Hz, 1H), 7.63 (d, J = 10.5 Hz, 1H), 7.40-7.27 (m, 3H), 7.27-7.15 (m, 3H), 5.16 (p, J = 7.0 Hz, 1H), 5.02-4.68 (m, 3H), 4.50-4.34 (m, 1H), 3.91-3.81 (m, 1H), 3.53-3.29 (m, 2H), 3.15-2.84 (m, 2H), 2.44-2.27 (m, 2H), 2.27-2.11 (m, 1H), 1.97-1.81 (m, 1H), 1.58-1.36 (m, 5H), 1.36-1.03 (m, 5H), 0.94 (d, J = 5.9 Hz, 1H), 0.58-0.34 (m, 2H). |
| 348 | 664.3 | 1H NMR (400 MHz, DMSO-d6) δ 8.82 (d, J = 6.9 Hz, 1H), 8.72 (s, 2H), 8.63 (d, J = 8.1 Hz, 1H), 8.06 (d, J = 8.0 Hz, 1H), 8.02 (d, J = 6.4 Hz, 1H), 7.62 (d, J = 10.6 Hz, 1H), 7.41-7.32 (m, 2H), 7.30 (s, 1H), 7.28-7.19 (m, 3H), 5.18 (p, J = 7.0 Hz, 1H), 4.97-4.69 (m, 2H), 4.50-4.32 (m, 1H), 3.95-3.80 (m, 2H), 3.52-3.30 (m, 2H), 3.14-2.87 (m, 2H), 2.65-2.53 (m, 2H), 2.41-2.26 (m, 1H), 2.04-1.80 (m, 1H), 1.76-1.59 (m, 1H), 1.51 (d, J = 7.0 Hz, 3H), 1.37-1.11 (m, 4H), 1.11-0.97 (m, 1H), 0.88-0.70 (m, 2H), 0.40-0.26 (m, 1H), 0.26-0.17 (m, 1H). |
| 349 | 627.3 | 1H NMR (400 MHz, DMSO-d6) δ 9.14 (d, J = 6.8 Hz, 1H), 8.73 (s, 2H), 8.64 (d, J = 8.0 Hz, 1H), 8.57 (s, 1H), 8.52 (d, J = 5.1 Hz, 1H), 8.10 (d, J = 8.0 Hz, 1H), 8.00 (d, J = 6.4 Hz, 1H), 7.76 (d, J = 10.8 Hz, 1H), 7.34 (d, J = 5.2 Hz, 1H), 7.26 (d, J = 8.1 Hz, 1H), 7.20 (s, 1H), 5.20 (p, J = 7.1 Hz, 1H), 4.96-4.66 (m, 3H), 4.47-4.30 (m, 1H), 3.98 (s, 3H), 3.53-3.30 (m, 2H), 3.14-2.85 (m, 2H), 2.40-2.24 (m, 4H), 2.01-1.82 (m, 1H), 1.66-1.37 (m, 5H), 1.37-1.06 (m, 2H), 0.72-0.48 (m, 1H). |
| 350 | 627.3 | 1H NMR (400 MHz, DMSO-d6) δ 9.15 (d, J = 6.9 Hz, 1H), 8.72 (s, 2H), 8.64 (d, J = 8.1 Hz, 1H), 8.50 (d, J = 4.9 Hz, 1H), 8.48 (s, 1H), 8.10 (d, J = 8.0 Hz, 1H), 8.00 (d, J = 6.4 Hz, 1H), 7.77 (d, J = 10.8 Hz, 1H), 7.38 (d, J = 5.0 Hz, 1H), 7.26 (d, J = 8.1 Hz, 1H), 7.20 (s, 1H), 5.20 (p, J = 7.0 Hz, 1H), 4.96-4.67 (m, 3H), 4.48-4.34 (m, 1H), 3.98 (s, 3H), 3.51-3.31 (m, 2H), 3.13-2.86 (m, 2H), 2.43-2.25 (m, 4H), 2.00-1.84 (m, 1H), 1.65-1.36 (m, 5H), 1.36-1.06 (m, 2H), 0.64-0.48 (m, 1H). |
| 351 | 638.3 | 1H NMR (400 MHz, DMSO-d6) δ 8.81-8.68 (m, 3H), 8.65 (d, J = 8.2 Hz, 1H), 8.06 (d, J = 8.0 Hz, 1H), 8.03 (d, J = 6.4 Hz, 1H), 7.76 (d, J = 10.8 Hz, 1H), 7.34-7.04 (m, 6H), 5.22 (p, J = 7.0 Hz, 1H), 4.96-4.70 (m, 2H), 4.49-4.31 (m, 1H), 4.24 (dd, J = 14.2, 7.5 Hz, 1H), 3.95 (s, 3H), 3.43-3.34 (m, 2H), 3.14-2.87 (m, 3H), 2.74 (ddd, J = 14.6, 10.6, 4.1 Hz, 1H), 2.41-2.25 (m, 2H), 2.01-1.71 (m, 2H), 1.62 (d, J = 7.0 Hz, 3H), 1.58-1.45 (m, 1H), 1.18-1.01 (m, 0H), 0.88-0.72 (m, 1H), 0.44-0.29 (m, 2H). |
| 352 | 644.3 | 1H NMR (400 MHz, DMSO-d6) δ 8.98 (d, J = 7.1 Hz, 1H), 8.75 (s, 2H), 8.65 (d, J = 8.0 Hz, 1H), 8.09 (d, J = 8.0 Hz, 1H), 8.01 (d, J = 6.4 Hz, 1H), 7.76 (d, J = 10.8 Hz, 1H), 7.35-7.14 (m, 5H), 5.22 (p, J = 7.1 Hz, 1H), 4.98-4.66 (m, 3H), 4.48-4.33 (m, 1H), 3.98 (s, 3H), 3.52-3.31 (m, |

TABLE 3-continued

| Example | ES/MS m/z [M + H]+ | ¹H NMR |
|---|---|---|
| | | 2H), 3.12-2.88 (m, 2H), 2.48-2.15 (m, 4H), 2.01-1.79 (m, 1H), 1.67-1.36 (m, 5H), 1.36-1.08 (m, 2H), 0.61-0.41 (m, 1H). |
| 353 | 653.3 | 1H NMR (400 MHz, DMSO-d6) δ 9.14 (d, J = 6.8 Hz, 1H), 8.72 (s, 2H), 8.63 (d, J = 8.2 Hz, 1H), 8.48 (d, J = 4.9 Hz, 1H), 8.45 (s, 1H), 8.09 (d, J = 8.0 Hz, 1H), 7.99 (d, J = 6.4 Hz, 1H), 7.63 (d, J = 10.5 Hz, 1H), 7.36 (s, 1H), 7.34 (d, J = 4.9 Hz, 1H), 7.25 (d, J = 8.1 Hz, 1H), 5.23-5.12 (m, 1H), 5.01-4.68 (m, 3H), 4.48-4.32 (m, 1H), 3.91-3.80 (m, 1H), 3.12-2.88 (m, 2H), 2.41-2.25 (m, 3H), 2.01-1.78 (m, 1H), 1.58-1.37 (m, 5H), 1.36-1.06 (m, 5H), 1.03-0.86 (m, 1H), 0.60-0.35 (m, 2H). |
| 354 | 687.3 | 1H NMR (400 MHz, DMSO-d6) δ 9.41 (d, J = 7.7 Hz, 1H), 8.74 (s, 2H), 8.63 (d, J = 8.0 Hz, 1H), 8.53 (s, 1H), 8.42 (s, 1H), 8.09 (d, J = 8.0 Hz, 1H), 7.99 (d, J = 6.3 Hz, 1H), 7.63 (d, J = 10.6 Hz, 1H), 7.37 (s, 1H), 7.27 (d, J = 8.1 Hz, 1H), 5.41-5.24 (m, 1H), 5.04-4.67 (m, 3H), 4.49-4.32 (m, 2H), 3.91-3.76 (m, 1H), 3.56-3.29 (m, 2H), 3.13-2.84 (m, 2H), 2.40-2.23 (m, 2H), 2.14-1.80 (m, 2H), 1.60-1.37 (m, 5H), 1.37-1.05 (m, 4H), 1.02-0.86 (m, 1H), 0.55-0.28 (m, 2H). |
| 355 | 671.3 | 1H NMR (400 MHz, DMSO-d6) δ 9.46 (d, J = 7.1 Hz, 1H), 8.82 (d, J = 8.1 Hz, 2H), 8.63 (d, J = 8.1 Hz, 1H), 8.49 (s, 1H), 8.33 (s, 1H), 8.09 (d, J = 8.0 Hz, 1H), 7.99 (d, J = 6.4 Hz, 1H), 7.63 (d, J = 10.5 Hz, 1H), 7.37 (s, 1H), 7.26 (d, J = 8.0 Hz, 1H), 5.26 (p, J = 7.0 Hz, 1H), 5.02-4.70 (m, 3H), 4.47-4.33 (m, 2H), 3.85 (tt, J = 7.2, 3.9 Hz, 1H), 3.53-3.31 (m, 2H), 3.14-2.87 (m, 2H), 2.43-2.24 (m, 2H), 2.14 (td, J = 12.6, 3.8 Hz, 1H), 2.00-1.81 (m, 1H), 1.58-1.37 (m, 5H), 1.37-1.06 (m, 4H), 1.02-0.88 (m, 1H), 0.51-0.29 (m, 2H). |
| 356 | 687.3 | 1H NMR (400 MHz, DMSO-d6) δ 9.25 (d, J = 6.6 Hz, 1H), 8.73 (s, 2H), 8.66-8.56 (m, 1H), 8.28 (s, 1H), 8.08 (d, J = 8.1 Hz, 1H), 7.99 (d, J = 6.4 Hz, 1H), 7.63 (d, J = 10.6 Hz, 1H), 7.47 (s, 1H), 7.36 (s, 1H), 7.25 (d, J = 8.1 Hz, 1H), 5.14 (p, J = 7.0 Hz, 1H), 4.98-4.68 (m, 3H), 4.47-4.32 (m, 1H), 3.89-3.80 (m, 1H), 3.55-3.29 (m, 2H), 3.15-2.87 (m, 2H), 2.42-2.23 (m, 5H), 2.01-1.81 (m, 1H), 1.57-1.36 (m, 5H), 1.36-1.03 (m, 3H), 1.03-0.86 (m, 1H), 0.56-0.35 (m, 2H). |
| 357 | 687.3 | 1H NMR (400 MHz, DMSO-d6) δ 9.20 (d, J = 6.7 Hz, 1H), 8.74 (s, 2H), 8.65-8.56 (m, 1H), 8.37 (s, 1H), 8.08 (d, J = 8.0 Hz, 1H), 7.98 (d, J = 6.4 Hz, 1H), 7.63 (d, J = 10.6 Hz, 1H), 7.44 (s, 1H), 7.36 (s, 1H), 7.25 (d, J = 8.1 Hz, 1H), 5.15 (p, J = 7.0 Hz, 1H), 4.98-4.68 (m, 3H), 4.49-4.32 (m, 1H), 3.91-3.76 (m, 1H), 3.54-3.29 (m, 2H), 3.17-2.86 (m, 2H), 2.49-2.44 (m, 1H), 2.41-2.23 (m, 3H), 2.00-1.79 (m, 1H), 1.61-1.05 (m, 9H), 1.03-0.87 (m, 1H), 0.61-0.33 (m, 2H). |
| 358 | 651.3 | 1H NMR (400 MHz, DMSO-d6) δ 9.16 (d, J = 6.9 Hz, 1H), 8.51 (d, J = 5.0 Hz, 1H), 8.49 (s, 1H), 8.08 (d, J = 8.0 Hz, 1H), 7.96 (s, 3H), 7.43 (s, 1H), 7.40 (d, J = 5.0 Hz, 1H), 7.25 (d, J = 8.1 Hz, 1H), 7.09 (s, 1H), 6.93 (d, J = 1.2 Hz, 1H), 5.20 (p, J = 7.0 Hz, 1H), 4.92-4.76 (m, 1H), 4.69-4.54 (m, 1H), 4.12 (s, 3H), 3.99 (s, 3H), 3.92-3.79 (m, 1H), 3.76-3.64 (m, 1H), 3.61-3.46 (m, 2H), 3.46-3.27 (m, 4H), 2.42-2.29 (m, 3H), 2.03-1.87 (m, 1H), 1.83-1.68 (m, 1H), 1.62-1.07 (m, 8H), 0.63-0.43 (m, 1H). |
| 359 | 685.3 | 1H NMR (400 MHz, DMSO-d6) δ 9.23 (d, J = 6.7 Hz, 1H), 8.29 (s, 1H), 8.08 (d, J = 8.0 Hz, 1H), 7.97 (s, 3H), 7.47 (s, 1H), 7.43 (s, 1H), 7.25 (d, J = 8.1 Hz, 1H), 7.08 (s, 1H), 6.93 (d, J = 1.1 Hz, 1H), 5.16 (p, J = 6.9 Hz, 1H), 4.89-4.77 (m, 1H), 4.66-4.53 (m, 1H), 4.11 (s, 3H), 3.99 (s, 3H), 3.92-3.80 (m, 1H), 3.76-3.65 (m, 1H), 3.63-3.46 (m, 2H), 3.46-3.30 (m, 4H), 2.42-2.26 (m, 3H), 2.02-1.85 (m, 1H), 1.83-1.68 (m, 1H), 1.57-1.32 (m, 5H), 1.31-1.06 (m, 3H), 0.60-0.42 (m, 1H). |
| 360 | 668.4 | 1H NMR (400 MHz, DMSO-d6) δ 9.18 (d, J = 7.4 Hz, 1H), 8.08 (d, J = 8.0 Hz, 1H), 7.96 (s, 3H), 7.43 (s, 1H), 7.32 (td, J = 8.0, 6.0 Hz, 1H), 7.25 (d, J = 8.1 Hz, 1H), 7.08 (s, 1H), 7.07-6.99 (m, 2H), 6.93 (d, J = 1.2 Hz, 1H), 5.28 (p, J = 7.1 Hz, 1H), 4.96-4.83 (m, 1H), 4.64-4.53 (m, 1H), 4.12 (s, 3H), 3.99 (s, 3H), 3.74-3.67 (m, 2H), 3.58-3.48 (m, 3H), 3.45-3.31 (m, 4H), 2.30-2.12 (m, 2H), 2.02-1.86 (m, 1H), 1.84-1.68 (m, 1H), 1.59-1.33 (m, 5H), 1.33-1.10 (m, 3H), 0.52-0.32 (m, 1H). |
| 361 | 634.3 | 1H NMR (400 MHz, DMSO-d6) δ 8.92 (d, J = 7.9 Hz, 1H), 8.07 (d, J = 8.0 Hz, 1H), 8.01-7.85 (m, 3H), 7.40 (s, 1H), 7.25 (d, J = 8.1 Hz, 1H), 7.17 (t, J = 7.5 Hz, 1H), 7.08 (s, 1H), 7.05 (d, J = 7.5 Hz, 1H), 7.01 (d, J = 7.6 Hz, 1H), 6.92 (d, J = 1.1 Hz, 1H), 5.37 (p, J = 7.1 Hz, 1H), 4.96-4.84 (m, 1H), 4.62-4.51 (m, 1H), 4.30-4.04 (m, 4H), 3.99 (s, 3H), 3.33-3.01 (m, 4H), 2.66-2.52 (m, 1H), 2.31 (s, 3H), 2.25-2.06 (m, 2H), 2.06-1.92 (m, 1H), 1.83-1.71 (m, 1H), 1.67-1.34 (m, 7H), 1.32-1.12 (m, 2H), 0.52-0.34 (m, 1H). |
| 362 | 664.3 | 1H NMR (400 MHz, DMSO-d6) δ 8.92 (d, J = 7.9 Hz, 1H), 8.07 (d, J = 8.0 Hz, 1H), 8.03-7.88 (m, 3H), 7.43 (s, 1H), 7.25 (d, J = 8.1 Hz, 1H), 7.17 (t, J = 7.5 Hz, 1H), 7.08 (s, 1H), 7.05 (d, J = 7.5 Hz, 1H), 7.01 (d, J = 7.6 Hz, 1H), 6.93 (d, J = 1.2 Hz, 1H), 5.37 (p, J = 7.1 Hz, 1H), 4.97-4.86 (m, 1H), 4.62-4.50 (m, 1H), 4.11 (s, 3H), 3.99 (s, 3H), 3.96-3.78 (m, |

TABLE 3-continued

| Example | ES/MS m/z [M + H]+ | 1H NMR |
|---|---|---|
| | | 1H), 3.75-3.67 (m, 1H), 3.59-3.47 (m, 3H), 3.49-3.31 (m, 5H), 2.62-2.52 (m, 1H), 2.31 (s, 3H), 2.25-2.04 (m, 2H), 2.00-1.89 (m, 1H), 1.83-1.68 (m, 1H), 1.65-1.36 (m, 5H), 1.34-0.98 (m, 2H), 0.52-0.33 (m, 1H). |
| 363 | 652.3 | 1H NMR (400 MHz, DMSO-d6) δ 8.90 (d, J = 7.9 Hz, 1H), 8.80-8.65 (m, 3H), 8.08 (d, J = 8.0 Hz, 1H), 7.99 (d, J = 1.3 Hz, 1H), 7.35 (d, J = 1.3 Hz, 1H), 7.25 (d, J = 8.1 Hz, 1H), 7.17 (t, J = 7.5 Hz, 1H), 7.12 (s, 1H), 7.05 (d, J = 7.5 Hz, 1H), 7.01 (d, J = 7.5 Hz, 1H), 5.37 (p, J = 7.1 Hz, 1H), 4.97-4.75 (m, 2H), 4.63-4.54 (m, 1H), 4.52-4.36 (m, 1H), 4.14 (s, 3H), 4.02 (s, 3H), 3.50-3.31 (m, 2H), 3.13-2.89 (m, 2H), 2.60-2.51 (m, 1H), 2.40-2.27 (m, 4H), 2.27-2.06 (m, 2H), 2.02-1.83 (m, 1H), 1.71-1.54 (m, 1H), 1.51-1.38 (m, 4H), 1.33-1.08 (m, 2H), 0.57-0.37 (m, 1H). |
| 364 | 666.3 | 1H NMR (400 MHz, DMSO-d6) δ 8.80-8.64 (m, 3H), 8.10 (d, J = 7.0 Hz, 1H), 8.03 (d, J = 8.0 Hz, 1H), 7.97 (d, J = 1.3 Hz, 1H), 7.36 (d, J = 1.3 Hz, 1H), 7.18 (d, J = 8.0 Hz, 1H), 7.12 (s, 1H), 5.02-4.74 (m, 3H), 4.50-4.28 (m, 2H), 4.20 (s, 3H), 4.03 (s, 3H), 3.53-3.30 (m, 2H), 3.16-2.89 (m, 2H), 2.41-2.14 (m, 4H), 1.92 (d, J = 23.8 Hz, 2H), 1.51-1.37 (m, 4H), 1.32-1.06 (m, 5H), 0.88 (s, 3H), 0.69-0.51 (m, 1H). |
| 365 | 666.3 | 1H NMR (400 MHz, DMSO-d6) δ 8.83-8.65 (m, 3H), 8.08 (d, J = 8.1 Hz, 1H), 7.97 (d, J = 1.3 Hz, 1H), 7.90 (d, J = 7.9 Hz, 1H), 7.34 (d, J = 1.3 Hz, 1H), 7.28 (d, J = 8.1 Hz, 1H), 7.10 (s, 1H), 5.17-5.02 (m, 2H), 5.01-4.73 (m, 2H), 4.53-4.35 (m, 1H), 4.14 (s, 3H), 4.02 (s, 3H), 3.53-3.30 (m, 2H), 3.14-2.84 (m, 2H), 2.43-2.24 (m, 1H), 2.08-1.76 (m, 3H), 1.74-1.61 (m, 1H), 1.53 (d, J = 7.0 Hz, 3H), 1.42-1.31 (m, 1H), 1.24-0.76 (m, 10H). |
| 366 | 642.4 | 1H NMR (400 MHz, DMSO-d6) δ 8.05 (d, J = 8.1 Hz, 1H), 8.02-7.86 (m, 3H), 7.79 (d, J = 7.9 Hz, 1H), 7.46 (s, 1H), 7.19 (d, J = 8.2 Hz, 1H), 7.07 (s, 1H), 6.92 (d, J = 1.2 Hz, 1H), 5.09 (p, J = 7.1 Hz, 1H), 4.80-4.69 (m, 1H), 4.67-4.54 (m, 1H), 4.14 (s, 3H), 3.98 (s, 3H), 3.92-3.78 (m, 1H), 3.75-3.68 (m, 1H), 3.64-3.49 (m, 2H), 3.48-3.32 (m, 5H), 2.01-1.89 (m, 1H), 1.82-1.62 (m, 2H), 1.57-1.17 (m, 8H), 1.12 (s, 3H), 1.01 (s, 3H), 0.75-0.57 (m, 2H), 0.26-0.14 (m, 1H), −0.40 (d, J = 5.4 Hz, 1H). |
| 367 | 630.4 | 1H NMR (400 MHz, DMSO-d6) δ 8.83-8.73 (m, 2H), 8.69 (d, J = 7.9 Hz, 1H), 8.06 (d, J = 8.1 Hz, 1H), 8.02 (d, J = 1.3 Hz, 1H), 7.78 (d, J = 7.9 Hz, 1H), 7.35 (d, J = 1.2 Hz, 1H), 7.20 (d, J = 8.2 Hz, 1H), 7.12 (s, 1H), 5.10 (p, J = 7.3 Hz, 1H), 4.92 (td, J = 9.3, 4.5 Hz, 1H), 4.85-4.72 (m, 1H), 4.62 (dd, J = 14.1, 7.8 Hz, 1H), 4.51-4.36 (m, 1H), 4.17 (s, 3H), 4.02 (s, 3H), 3.53-3.33 (m, 2H), 3.15-2.87 (m, 2H), 2.42-2.25 (m, 1H), 2.01-1.80 (m, 1H), 1.79-1.61 (m, 1H), 1.60-1.19 (m, 8H), 1.12 (s, 3H), 1.01 (s, 3H), 0.79-0.56 (m, 2H), 0.27-0.15 (m, 1H), −0.31--0.47 (m, 1H). |
| 368 | 638.3 | 1H NMR (400 MHz, DMSO-d6) δ 8.78-8.62 (m, 4H), 8.04-7.94 (m, 2H), 7.35 (d, J = 1.3 Hz, 1H), 7.16 (d, J = 8.1 Hz, 1H), 7.06 (s, 1H), 5.02-4.72 (m, 2H), 4.60-4.51 (m, 2H), 4.50-4.35 (m, 1H), 4.15 (s, 3H), 4.02 (s, 3H), 3.50-3.30 (m, 2H), 3.14-2.84 (m, 2H), 2.48-2.29 (m, 2H), 2.00-1.04 (m, 13H). |
| 369 | 638.3 | 1H NMR (400 MHz, DMSO-d6) δ 8.80-8.62 (m, 4H), 8.02 (d, J = 8.0 Hz, 1H), 7.99 (d, J = 1.3 Hz, 1H), 7.34 (d, J = 1.3 Hz, 1H), 7.13 (d, J = 8.1 Hz, 1H), 7.08 (s, 1H), 4.91-4.73 (m, 2H), 4.68-4.59 (m, 1H), 4.53-4.37 (m, 1H), 4.13 (s, 3H), 4.02 (s, 3H), 3.51-3.31 (m, 2H), 3.15-2.86 (m, 2H), 2.72-2.58 (m, 1H), 2.42-2.24 (m, 1H), 2.13-1.82 (m, 4H), 1.56-1.32 (m, 6H), 1.32-1.06 (m, 2H), 1.05-0.92 (m, 1H), 0.65-0.49 (m, 1H). |
| 370 | 696.4 | 1H NMR (400 MHz, DMSO-d6) δ 8.31 (d, J = 7.9 Hz, 1H), 8.08 (d, J = 8.1 Hz, 1H), 8.04-7.90 (m, 3H), 7.47 (s, 1H), 7.25 (d, J = 8.2 Hz, 1H), 7.09 (s, 1H), 6.93 (s, 1H), 5.10 (p, J = 7.1 Hz, 1H), 4.85-4.76 (m, 1H), 4.58 (t, J = 11.7 Hz, 2H), 4.15 (s, 3H), 3.99 (s, 3H), 3.94-3.77 (m, 1H), 3.76-3.67 (m, 1H), 3.63-3.47 (m, 2H), 3.46-3.31 (m, 4H), 2.20-2.06 (m, 1H), 2.04-1.89 (m, 1H), 1.85-1.69 (m, 2H), 1.64-1.33 (m, 7H), 1.29 (s, 3H), 0.80-0.53 (m, 2H), 0.38-0.24 (m, 1H), −0.27--0.42 (m, 1H). |
| 371 | 684.3 | 1H NMR (400 MHz, DMSO-d6) δ 8.81-8.72 (m, 2H), 8.69 (d, J = 7.9 Hz, 1H), 8.30 (d, J = 7.9 Hz, 1H), 8.09 (d, J = 8.2 Hz, 1H), 8.02 (d, J = 3.0 Hz, 1H), 7.35 (s, 1H), 7.25 (d, J = 8.2 Hz, 1H), 7.14 (s, 1H), 5.11 (p, J = 7.3 Hz, 1H), 4.97-4.74 (m, 2H), 4.64-4.52 (m, 1H), 4.51-4.34 (m, 1H), 4.18 (s, 3H), 4.02 (s, 3H), 3.49-3.31 (m, 2H), 3.17-2.85 (m, 2H), 2.41-2.29 (m, 1H), 2.19-2.05 (m, 1H), 2.03-1.83 (m, 1H), 1.81-1.70 (m, 1H), 1.67-1.36 (m, 7H), 1.28 (s, 3H), 0.83-0.67 (m, 1H), 0.67-0.57 (m, 1H), 0.39-0.22 (m, 1H), −0.22--0.37 (m, 1H). |
| 372 | 696.4 | 1H NMR (400 MHz, DMSO-d6) δ 8.34 (d, J = 8.2 Hz, 1H), 8.06 (d, J = 8.1 Hz, 1H), 8.04-7.88 (m, 3H), 7.46 (s, 1H), 7.21 (d, J = 8.1 Hz, 1H), 7.09 (s, 1H), 6.93 (s, 1H), 5.18 (p, J = 7.2 Hz, 1H), 4.90-4.77 (m, 1H), 4.65-4.52 (m, 2H), 4.15 (s, 3H), 3.98 (s, 3H), 3.94-3.76 (m, 1H), 3.73-3.64 (m, 1H), 3.62-3.48 (m, 2H), 3.46-3.30 (m, 4H), 2.38-2.24 (m, |

TABLE 3-continued

| Example | ES/MS m/z [M + H]+ | ¹H NMR |
|---|---|---|
| | | 1H), 2.03-1.88 (m, 1H), 1.82-1.68 (m, 1H), 1.67-1.31 (m, 7H), 1.30-1.07 (m, 4H), 0.80-0.67 (m, 2H), 0.32-0.17 (m, 1H), −0.33-−0.46 (m, 1H). |
| 373 | 684.3 | 1H NMR (400 MHz, DMSO-d6) δ 8.82-8.70 (m, 2H), 8.68 (d, J = 8.0 Hz, 1H), 8.33 (d, J = 8.1 Hz, 1H), 8.07 (d, J = 8.1 Hz, 1H), 8.02 (s, 1H), 7.34 (s, 1H), 7.21 (d, J = 8.1 Hz, 1H), 7.13 (s, 1H), 5.19 (p, J = 7.2 Hz, 1H), 4.96-4.73 (m, 2H), 4.65-4.50 (m, 1H), 4.50-4.34 (m, 1H), 4.17 (s, 3H), 4.02 (s, 3H), 3.51-3.27 (m, 2H), 3.14-2.89 (m, 2H), 2.42-2.22 (m, 2H), 2.03-1.83 (m, 1H), 1.67-1.08 (m, 11H), 0.84-0.60 (m, 2H), 0.33-0.21 (m, 1H), −0.29-−0.43 (m, 1H). |
| 374 | 638.3 | 1H NMR (400 MHz, DMSO-d6) δ 9.04 (d, J = 7.9 Hz, 1H), 8.09 (d, J = 8.1 Hz, 1H), 8.04-7.88 (m, 3H), 7.44 (s, 1H), 7.25 (d, J = 8.1 Hz, 1H), 7.05 (s, 1H), 6.93 (s, 1H), 5.25 (p, J = 7.2 Hz, 1H), 4.81-4.69 (m, 1H), 4.55-4.44 (m, 1H), 4.11 (s, 3H), 3.99 (s, 3H), 3.95-3.78 (m, 2H), 3.75-3.68 (m, 1H), 3.64-3.46 (m, 2H), 3.46-3.30 (m, 4H), 2.23-2.02 (m, 2H), 2.02-1.89 (m, 1H), 1.86-1.70 (m, 2H), 1.66-1.08 (m, 9H), 0.98-0.81 (m, 1H). |
| 375 | 626.3 | 1H NMR (400 MHz, DMSO-d6) δ 9.03 (d, J = 7.9 Hz, 1H), 8.81-8.72 (m, 2H), 8.70 (d, J = 7.9 Hz, 1H), 8.09 (d, J = 8.1 Hz, 1H), 8.00 (s, 1H), 7.35 (s, 1H), 7.25 (d, J = 8.1 Hz, 1H), 7.10 (s, 1H), 5.26 (p, J = 7.2 Hz, 1H), 4.99-4.69 (m, 2H), 4.60-4.36 (m, 2H), 4.14 (s, 3H), 4.02 (s, 3H), 3.50-3.32 (m, 2H), 3.16-2.88 (m, 2H), 2.42-2.28 (m, 1H), 2.23-2.03 (m, 2H), 2.01-1.85 (m, 1H), 1.85-1.69 (m, 1H), 1.69-1.38 (m, 6H), 1.38-1.12 (m, 3H), 1.02-0.87 (m, 1H). |
| 376 | 614.4 | 1H NMR (400 MHz, DMSO-d6) δ 8.79-8.63 (m, 3H), 8.33 (s, 1H), 8.05 (d, J = 8.1 Hz, 1H), 7.90 (d, J = 8.3 Hz, 1H), 7.82 (d, J = 7.3 Hz, 1H), 7.78 (d, J = 8.5 Hz, 1H), 7.31 (s, 1H), 7.18 (d, J = 8.1 Hz, 1H), 5.11 (p, J = 7.0 Hz, 1H), 4.96-4.75 (m, 2H), 4.75-4.58 (m, 1H), 4.53-4.36 (m, 1H), 3.91-3.82 (m, 1H), 3.50-3.33 (m, 2H), 3.15-3.02 (m, 1H), 3.02-2.85 (m, 1H), 2.41-2.26 (m, 1H), 2.00-1.84 (m, 1H), 1.80-1.56 (m, 2H), 1.52-1.00 (m, 15H), 0.95 (s, 3H), 0.92-0.82 (m, 1H), 0.63-0.46 (m, 1H). |
| 377 | 662.3 | 1H NMR (400 MHz, DMSO-d6) δ 8.79 (d, J = 5.4 Hz, 1H), 8.77-8.69 (m, 2H), 8.67 (d, J = 8.2 Hz, 1H), 8.10 (d, J = 8.1 Hz, 1H), 8.00 (d, J = 6.4 Hz, 1H), 7.76 (d, J = 10.7 Hz, 1H), 7.25-7.21 (m, 2H), 5.55-5.40 (m, 1H), 5.10 (dd, J = 31.2, 14.6 Hz, 1H), 4.94-4.71 (m, 2H), 4.47-4.32 (m, 1H), 3.93 (s, 3H), 3.52-3.30 (m, 2H), 3.14-2.87 (m, 2H), 2.38-2.30 (m, 1H), 2.21-1.85 (m, 3H), 1.61-1.22 (m, 9H). |
| 378 | 662.3 | 1H NMR (400 MHz, DMSO-d6) δ 8.77 (d, J = 7.8 Hz, 1H), 8.74-8.63 (m, 3H), 8.08 (d, J = 8.1 Hz, 1H), 8.01 (d, J = 6.4 Hz, 1H), 7.77 (d, J = 10.8 Hz, 1H), 7.26 (d, J = 8.1 Hz, 1H), 7.23 (s, 1H), 5.68 (t, J = 13.6 Hz, 1H), 5.14-4.94 (m, 2H), 4.94-4.70 (m, 1H), 4.40 (s, 1H), 3.94 (s, 3H), 3.46-3.32 (m, 1H), 3.12-2.87 (m, 2H), 2.39-2.25 (m, 1H), 2.14-1.83 (m, 4H), 1.82-1.54 (m, 2H), 1.52-1.30 (m, 5H), 1.16-0.98 (m, 1H). |
| 379 | 602.3 | 1H NMR (400 MHz, DMSO-d6) δ 8.79-8.69 (m, 2H), 8.65 (d, J = 8.0 Hz, 1H), 8.17 (d, J = 8.2 Hz, 1H), 8.05 (d, J = 6.4 Hz, 1H), 7.91 (d, J = 8.3 Hz, 1H), 7.76 (d, J = 10.8 Hz, 1H), 7.28 (d, J = 8.2 Hz, 1H), 7.22 (s, 1H), 5.09 (dd, J = 14.4, 4.0 Hz, 2H), 4.98 (p, J = 7.1 Hz, 1H), 4.81 (dtd, J = 49.0, 9.4, 4.6 Hz, 1H), 4.49 (dd, J = 14.4, 11.6 Hz, 1H), 4.44-4.35 (m, 1H), 3.52-3.32 (m, 2H), 3.12-2.89 (m, 2H), 2.39-2.27 (m, 1H), 1.99-1.84 (m, 2H), 1.53 (d, J = 6.9 Hz, 3H), 1.37-1.21 (m, 3H), 0.71-0.31 (m, 5H), 0.04-0.01 (m, 1H). |
| 380 | 668.4 | 1H NMR (400 MHz, DMSO-d6) δ 8.90-8.66 (m, 3H), 8.05 (d, J = 8.1 Hz, 1H), 7.91 (d, J = 1.2 Hz, 1H), 7.80 (d, J = 7.4 Hz, 1H), 7.32 (d, J = 1.3 Hz, 1H), 7.19 (d, J = 8.2 Hz, 1H), 7.07 (d, J = 2.5 Hz, 1H), 5.12 (p, J = 7.1 Hz, 1H), 4.87-4.76 (m, 1H), 4.63-4.51 (m, 1H), 4.49-4.34 (m, 1H), 4.14 (d, J = 2.2 Hz, 3H), 4.01 (s, 3H), 3.48-3.33 (m, 2H), 3.06-2.79 (m, 3H), 2.23-2.13 (m, 1H), 1.97-1.86 (m, 1H), 1.85-1.57 (m, 3H), 1.55-1.26 (m, 8H), 1.21 (s, 3H), 1.17-0.98 (m, 2H), 0.95 (s, 3H). |
| 381 | 626.3 | 1H NMR (400 MHz, DMSO-d6) δ 8.76-8.70 (m, 2H), 8.69 (d, J = 5.4 Hz, 1H), 8.64 (d, J = 7.4 Hz, 1H), 8.03 (d, J = 8.1 Hz, 1H), 8.00 (d, J = 6.5 Hz, 1H), 7.75 (d, J = 10.9 Hz, 1H), 7.15 (s, 1H), 7.14 (d, J = 8.1 Hz, 1H), 4.93-4.71 (m, 4H), 4.48-4.33 (m, 1H), 3.96 (s, 3H), 3.52-3.32 (m, 2H), 3.13-2.88 (m, 2H), 2.69-2.55 (m, 1H), 2.39-2.27 (m, 1H), 2.10-1.85 (m, 3H), 1.54-1.36 (m, 6H), 1.31-1.07 (m, 2H), 1.02-0.90 (m, 1H), 0.63-0.48 (m, 1H). |
| 382 | 626.3 | 1H NMR (400 MHz, DMSO-d6) δ 8.79 (d, J = 7.2 Hz, 1H), 8.76-8.68 (m, 2H), 8.64 (d, J = 8.0 Hz, 2H), 8.05 (d, J = 8.2 Hz, 1H), 8.02 (d, J = 6.5 Hz, 1H), 7.76 (d, J = 10.9 Hz, 1H), 7.26 (d, J = 8.2 Hz, 1H), 7.14 (s, 1H), 4.93-4.64 (m, 2H), 4.64-4.51 (m, 2H), 4.47-4.33 (m, 1H), 4.01-3.95 (m, 2H), 3.51-3.31 (m, 2H), 3.10-2.88 (m, 2H), 2.39-2.20 (m, 1H), 2.06-1.85 (m, 3H), 1.75 (d, J = 7.0 Hz, 3H), 1.70-1.61 (m, 2H), 1.56-1.33 (m, 4H), 1.23-1.07 (m, 1H). |
| 383 | 626.3 | 1H NMR (400 MHz, DMSO-d6) δ 8.77-8.72 (m, 2H), 8.70 (d, J = 7.6 Hz, 1H), 8.64 (d, J = 7.9 Hz, 1H), 8.04-7.99 (m, 2H), 7.75 (d, J = 10.8 Hz, 1H), 7.17 (d, J = 8.1 Hz, 1H), 7.13 (s, 1H), 4.97 (p, J = 7.1 Hz, 1H), |

TABLE 3-continued

| Example | ES/MS m/z [M + H]+ | ¹H NMR |
|---|---|---|
| | | 4.92-4.66 (m, 2H), 4.58 (dt, J = 12.9, 5.8 Hz, 1H), 4.47-4.34 (m, 1H), 3.97 (s, 3H), 3.50-3.42 (m, 1H), 3.42-3.32 (m, 1H), 3.11-2.89 (m, 2H), 2.40-2.29 (m, 1H), 2.00-1.76 (m, 4H), 1.74-1.61 (m, 2H), 1.61-1.48 (m, 2H), 1.45 (d, J = 7.1 Hz, 3H), 1.41-1.26 (m, 2H), 1.26-1.05 (m, 1H). |
| 384 | 676.3 | 1H NMR (400 MHz, DMSO-d6) δ 9.19 (d, J = 8.0 Hz, 1H), 8.81-8.70 (m, 2H), 8.68-8.61 (m, 1H), 8.10 (d, J = 8.0 Hz, 1H), 8.01 (d, J = 6.4 Hz, 1H), 7.76 (d, J = 10.8 Hz, 1H), 7.52-7.37 (m, 3H), 7.27 (d, J = 8.1 Hz, 1H), 7.20 (s, 1H), 6.99 (t, J = 55.3 Hz, 1H), 5.40 (p, J = 7.1 Hz, 1H), 5.00-4.66 (m, 3H), 4.47-4.34 (m, 1H), 3.98 (s, 3H), 3.53-3.33 (m, 1H), 3.12-2.89 (m, 2H), 2.63-2.51 (m, 1H), 2.42-2.25 (m, 2H), 2.19 (td, J = 12.5, 4.3 Hz, 1H), 2.01-1.82 (m, 1H), 1.73-1.56 (m, 1H), 1.54-1.39 (m, 4H), 1.39-1.10 (m, 2H), 0.57-0.39 (m, 1H). |
| 385 | 638.3 | 1H NMR (400 MHz, DMSO-d6) δ 8.79-8.70 (m, 2H), 8.63 (d, J = 7.9 Hz, 1H), 8.38 (d, J = 9.4 Hz, 1H), 8.05 (d, J = 8.0 Hz, 1H), 8.02 (d, J = 6.4 Hz, 1H), 7.78 (d, J = 10.8 Hz, 1H), 7.26 (s, 1H), 7.17 (d, J = 8.1 Hz, 1H), 5.25-5.05 (m, 2H), 4.94-4.70 (m, 2H), 4.48-4.34 (m, 1H), 4.03 (s, 3H), 3.53-3.43 (m, 1H), 3.43-3.34 (m, 2H), 3.11-2.88 (m, 2H), 2.39-2.24 (m, 1H), 1.98-1.65 (m, 3H), 1.64-1.47 (m, 2H), 1.42 (d, J = 7.1 Hz, 3H), 1.32-1.10 (m, 2H), 1.07-0.97 (m, 1H), 0.77-0.63 (m, 3H). |
| 386 | 638.3 | 1H NMR (400 MHz, DMSO-d6) δ 8.63 (d, J = 8.0 Hz, 1H), 8.49 (d, J = 7.9 Hz, 1H), 8.09 (d, J = 8.1 Hz, 1H), 8.04 (d, J = 6.4 Hz, 1H), 7.77 (d, J = 10.8 Hz, 1H), 7.20 (d, J = 8.1 Hz, 1H), 7.14 (s, 1H), 5.09 (q, J = 7.2 Hz, 1H), 4.93-4.63 (m, 3H), 4.45-4.30 (m, 1H), 3.99 (s, 3H), 3.51-3.34 (m, 2H), 3.15-2.77 (m, 2H), 2.36-2.25 (m, 1H), 1.96-1.82 (m, 2H), 1.60-0.68 (m, 11H), 0.59-0.49 (m, 1H). |
| 387 | 634.3 | 1H NMR (400 MHz, DMSO-d6) δ 8.76-8.68 (m, 2H), 8.62 (d, J = 8.0 Hz, 1H), 8.38 (dd, J = 8.5, 1.8 Hz, 1H), 8.03-7.97 (m, 2H), 7.61 (d, J = 10.6 Hz, 1H), 7.30 (s, 1H), 7.18 (d, J = 8.1 Hz, 1H), 5.13 (p, J = 7.2 Hz, 1H), 4.92-4.70 (m, 2H), 4.66-4.53 (m, 1H), 4.48-4.31 (m, 1H), 3.81 (tt, J = 7.3, 3.9 Hz, 1H), 3.51-3.30 (m, 2H), 3.11-2.88 (m, 2H), 2.40-2.27 (m, 1H), 1.98-1.84 (m, 2H), 1.76-1.44 (m, 6H), 1.42-1.13 (m, 6H), 1.09-0.91 (m, 3H), 0.85-0.76 (m, 1H), 0.71-0.62 (m, 1H). |
| 388 | 634.3 | 1H NMR (400 MHz, DMSO-d6) δ 8.83-8.69 (m, 2H), 8.63 (d, J = 8.1 Hz, 1H), 8.42 (d, J = 9.5 Hz, 1H), 8.03-7.97 (m, 2H), 7.62 (d, J = 10.6 Hz, 1H), 7.31 (s, 1H), 7.16 (d, J = 8.0 Hz, 1H), 5.19 (dq, J = 9.7, 7.0 Hz, 1H), 4.93-4.71 (m, 3H), 4.47-4.33 (m, 1H), 3.82 (tt, J = 7.1, 3.8 Hz, 1H), 3.51-3.33 (m, 2H), 3.11-2.87 (m, 2H), 2.41-2.20 (m, 2H), 2.03 (ddd, J = 9.4, 7.6, 3.7 Hz, 1H), 1.98-1.83 (m, 1H), 1.83-1.04 (m, 13H), 0.95 (ddd, J = 11.2, 9.4, 6.1 Hz, 1H), 0.88-0.80 (m, 1H), 0.67-0.57 (m, 1H). |
| 389 | 688.3 | 1H NMR (400 MHz, DMSO-d6) δ 8.80 (d, J = 5.2 Hz, 1H), 8.71 (s, 2H), 8.66 (d, J = 8.0 Hz, 1H), 8.10 (d, J = 8.0 Hz, 1H), 7.98 (d, J = 6.4 Hz, 1H), 7.63 (d, J = 10.4 Hz, 1H), 7.37 (s, 1H), 7.23 (d, J = 8.1 Hz, 1H), 5.66-5.55 (m, 1H), 5.12 (dd, J = 32.0, 14.7 Hz, 1H), 4.96-4.69 (m, 2H), 4.46-4.30 (m, 1H), 3.85-3.79 (m, 1H), 3.51-3.32 (m, 2H), 3.13-2.86 (m, 2H), 2.71-2.63 (m, 1H), 2.40-2.27 (m, 1H), 2.20-1.80 (m, 4H), 1.63-1.19 (m, 8H), 1.05-0.95 (m, 1H), 0.94-0.84 (m, 1H), 0.44-0.32 (m, 1H). |
| 390 | 688.3 | 1H NMR (400 MHz, DMSO-d6) δ 8.98 (d, J = 7.2 Hz, 1H), 8.75-8.68 (m, 2H), 8.66 (d, J = 8.3 Hz, 1H), 8.11 (d, J = 8.2 Hz, 1H), 7.99 (d, J = 6.2 Hz, 1H), 7.65 (d, J = 10.4 Hz, 1H), 7.40 (s, 1H), 7.34 (d, J = 8.2 Hz, 1H), 5.89-5.76 (m, 1H), 5.12 (dd, J = 27.3, 14.5 Hz, 1H), 4.92-4.68 (m, 1H), 4.57-4.47 (m, 1H), 4.46-4.33 (m, 1H), 3.90-3.81 (m, 1H), 3.51-3.32 (m, 2H), 3.11-2.86 (m, 2H), 2.40-2.22 (m, 1H), 2.08-1.73 (m, 8H), 1.66-1.53 (m, 1H), 1.51-1.24 (m, 3H), 1.17-1.00 (m, 2H), 0.96-0.85 (m, 1H), 0.53-0.43 (m, 1H). |
| 391 | 688.3 | 1H NMR (400 MHz, DMSO-d6) δ 8.79 (d, J = 7.7 Hz, 1H), 8.81-8.73 (m, 2H), 8.66 (d, J = 7.4 Hz, 1H), 8.08 (d, J = 8.0 Hz, 1H), 7.99 (d, J = 6.3 Hz, 1H), 7.64 (d, J = 10.5 Hz, 1H), 7.40 (s, 1H), 7.26 (d, J = 8.1 Hz, 1H), 5.89 (t, J = 13.8 Hz, 1H), 5.10 (dd, J = 27.3, 14.7 Hz, 1H), 4.99 (p, J = 7.3 Hz, 1H), 4.82 (dtd, J = 49.0, 9.6, 4.6 Hz, 1H), 4.46-4.34 (m, 1H), 3.89-3.80 (m, 1H), 3.53-3.30 (m, 2H), 3.11-2.86 (m, 2H), 2.41-2.28 (m, 1H), 2.17-1.56 (m, 7H), 1.49-1.26 (m, 5H), 1.16-0.86 (m, 3H), 0.48-0.37 (m, 1H). |
| 392 | 652.3 | 1H NMR (400 MHz, DMSO-d6) δ 8.76-8.68 (m, 3H), 8.62 (d, J = 8.0 Hz, 1H), 8.02 (d, J = 8.0 Hz, 1H), 7.98 (d, J = 6.4 Hz, 1H), 7.62 (d, J = 10.6 Hz, 1H), 7.31 (s, 1H), 7.13 (d, J = 8.1 Hz, 1H), 4.92-4.71 (m, 4H), 4.46-4.33 (m, 1H), 3.86-3.79 (m, 1H), 3.51-3.32 (m, 2H), 3.11-2.88 (m, 2H), 2.39-2.27 (m, 1H), 2.14-1.79 (m, 3H), 1.49-0.86 (m, 13H), 0.48-0.32 (m, 2H). |
| 393 | 652.3 | 1H NMR (400 MHz, DMSO-d6) δ 8.79 (d, J = 7.4 Hz, 1H), 8.80-8.69 (m, 2H), 8.65-8.59 (m, 1H), 8.05 (d, J = 8.2 Hz, 1H), 8.00 (d, J = 6.4 Hz, 1H), 7.62 (d, J = 10.6 Hz, 1H), 7.31 (d, J = 1.2 Hz, 1H), 7.25 (d, J = 8.2 Hz, 1H), 4.93-4.71 (m, 2H), 4.70-4.52 (m, 2H), 4.47-4.32 (m, 1H), 3.82 (tt, J = 7.0, 3.9 Hz, 1H), 3.51-3.32 (m, 2H), 3.10-2.89 (m, 2H), |

TABLE 3-continued

| Example | ES/MS m/z [M + H]+ | ¹H NMR |
|---|---|---|
| | | 2.39-2.23 (m, 1H), 2.09-1.82 (m, 3H), 1.75 (d, J = 7.0 Hz, 3H), 1.70-1.09 (m, 10H), 0.90-0.80 (m, 1H), 0.70-0.59 (m, 1H). |
| 394 | 652.3 | 1H NMR (400 MHz, DMSO-d6) δ 8.78-8.72 (m, 2H), 8.71 (d, J = 7.6 Hz, 1H), 8.62 (d, J = 8.4 Hz, 1H), 8.03-7.98 (m, 2H), 7.62 (d, J = 10.6 Hz, 1H), 7.31 (s, 1H), 7.16 (d, J = 8.1 Hz, 1H), 4.97 (p, J = 7.2 Hz, 1H), 4.92-4.71 (m, 2H), 4.67-4.57 (m, 1H), 4.47-4.34 (m, 1H), 3.82 (tt, J = 7.1, 3.9 Hz, 1H), 3.51-3.31 (m, 2H), 3.00 (d, J = 33.8 Hz, 2H), 2.40-2.28 (m, 1H), 1.98-1.76 (m, 3H), 1.72-1.48 (m, 4H), 1.46 (d, J = 7.1 Hz, 3H), 1.41-1.26 (m, 2H), 1.26-1.10 (m, 4H), 0.89-0.80 (m, 1H), 0.69-0.61 (m, 1H). |
| 395 | 667.3 | 1H NMR (400 MHz, DMSO-d6) δ 9.30 (d, J = 7.5 Hz, 1H), 8.83-8.72 (m, 2H), 8.67-8.59 (m, 1H), 8.45 (s, 1H), 8.41 (s, 1H), 8.10 (d, J = 8.0 Hz, 1H), 7.99 (d, J = 6.4 Hz, 1H), 7.63 (d, J = 10.6 Hz, 1H), 7.38 (s, 1H), 7.27 (d, J = 8.1 Hz, 1H), 5.35 (p, J = 7.1 Hz, 1H), 5.01-4.71 (m, 3H), 4.49-4.35 (m, 1H), 3.90-3.79 (m, 1H), 3.52-3.31 (m, 2H), 3.10-2.88 (m, 2H), 2.40-2.28 (m, 5H), 2.15-2.02 (m, 1H), 1.97-1.86 (m, 1H), 1.57-1.37 (m, 4H), 1.36-1.05 (m, 5H), 0.94 (q, J = 5.8, 5.4 Hz, 1H), 0.51-0.32 (m, 3H). |
| 396 | 667.3 | 1H NMR (400 MHz, DMSO-d6) δ 9.28 (d, J = 7.7 Hz, 1H), 8.81-8.72 (m, 2H), 8.63 (dd, J = 8.2, 1.7 Hz, 1H), 8.50 (d, J = 5.5 Hz, 1H), 8.10 (d, J = 8.0 Hz, 1H), 7.99 (d, J = 6.3 Hz, 1H), 7.63 (d, J = 10.6 Hz, 1H), 7.40 (s, 1H), 7.38 (s, 1H), 7.28 (d, J = 8.1 Hz, 1H), 5.36 (p, J = 7.1 Hz, 1H), 5.01-4.68 (m, 3H), 4.50-4.32 (m, 1H), 3.89-3.79 (m, 1H), 3.50-3.33 (m, 2H), 3.09-2.89 (m, 2H), 2.59 (s, 3H), 2.41-2.28 (m, 3H), 2.25-2.13 (m, 1H), 2.01-1.84 (m, 1H), 1.56-1.39 (m, 4H), 1.38-1.07 (m, 5H), 0.94 (d, J = 6.0 Hz, 1H), 0.50-0.37 (m, 2H). |
| 397 | 700.3 | 1H NMR (400 MHz, DMSO-d6) δ 9.19 (d, J = 8.0 Hz, 1H), 8.09 (d, J = 8.0 Hz, 1H), 8.04-7.91 (m, 3H), 7.52-7.37 (m, 4H), 7.26 (d, J = 8.1 Hz, 1H), 7.08 (s, 1H), 6.99 (s, 0H), 6.93 (d, J = 1.1 Hz, 1H), 5.39 (p, J = 7.1 Hz, 1H), 4.95-4.85 (m, 1H), 4.63-4.53 (m, 1H), 4.12 (s, 3H), 3.99 (s, 3H), 3.95-3.79 (m, 1H), 3.74-3.67 (m, 1H), 3.63-3.47 (m, 2H), 3.47-3.31 (m, 5H), 2.62-2.52 (m, 1H), 2.36-2.25 (m, 1H), 2.24-2.11 (m, 1H), 2.02-1.88 (m, 1H), 1.83-1.69 (m, 1H), 1.68-1.15 (m, 7H), 0.52-0.39 (m, 1H). |
| 398 | 643.7 | 1H NMR (400 MHz, DMSO-d6) δ 9.23 (d, J = 6.6 Hz, 1H), 8.69 (d, J = 8.0 Hz, 1H), 8.08 (d, J = 8.1 Hz, 1H), 8.00 (d, J = 1.3 Hz, 1H), 7.36 (d, J = 1.2 Hz, 1H), 7.24 (d, J = 8.1 Hz, 1H), 7.10 (s, 1H), 5.12 (p, J = 6.9 Hz, 1H), 4.96-4.88 (m, 1H), 4.79 (m, J = 9.5, 4.9 Hz, 1H), 4.68 (t, J = 10.4 Hz, 1H), 4.63-4.54 (m, 1H), 4.43 (d, J = 10.9 Hz, 1H), 4.15 (s, 3H), 4.03 (s, 3H), 3.42 (m, J = 25.1, 12.7 Hz, 2H), 3.07 (d, J = 10.3 Hz, 1H), 2.96 (d, J = 9.9 Hz, 1H), 2.35 (s, 3H), 2.12 (m, J = 14.4, 8.1 Hz, 1H), 1.98-1.88 (m, 1H), 1.74 (d, J = 17.2 Hz, 1H), 1.53 (d, J = 7.1 Hz, 3H), 1.45 (d, J = 8.3 Hz, 1H), 1.26 (q, J = 7.3, 6.6 Hz, 3H), 1.01 (d, J = 11.6 Hz, 2H). |
| 399 | 641.4 | 1H NMR (400 MHz, DMSO-d6) δ 9.45 (d, J = 6.9 Hz, 1H), 8.70 (d, J = 7.9 Hz, 1H), 8.13 (d, J = 8.1 Hz, 1H), 8.01 (d, J = 1.3 Hz, 1H), 7.36 (d, J = 1.3 Hz, 1H), 7.28 (d, J = 8.2 Hz, 1H), 7.16 (s, 1H), 6.48 (ddd, J = 16.1, 8.1, 5.4 Hz, 1H), 6.21 (d, J = 16.3 Hz, 1H), 5.25 (p, J = 7.0 Hz, 1H), 4.92 (dd, J = 14.0, 8.7 Hz, 2H), 4.80 (td, J = 9.3, 4.5 Hz, 0H), 4.70-4.61 (m, 1H), 4.43 (d, J = 12.3 Hz, 1H), 4.18 (s, 3H), 4.04 (s, 3H), 3.43 (dd, J = 26.2, 12.5 Hz, 2H), 3.02 (dd, J = 42.4, 10.5 Hz, 2H), 2.44 (s, 3H), 1.94 (d, J = 7.7 Hz, 2H), 1.54 (d, J = 7.0 Hz, 5H). |
| 400 | 666.3 | 1H NMR (400 MHz, DMSO-d6) δ 8.20 (d, J = 7.1 Hz, 1H), 8.07 (d, J = 8.1 Hz, 1H), 8.00 (d, J = 1.3 Hz, 1H), 7.36 (d, J = 1.3 Hz, 1H), 7.21 (d, J = 8.2 Hz, 1H), 7.07 (s, 1H), 5.14 (p, J = 7.1 Hz, 1H), 4.97-4.88 (m, 1H), 4.85-4.71 (m, 2H), 4.51-4.35 (m, 2H), 4.15 (s, 3H), 4.02 (s, 3H), 3.15-2.81 (m, 6H), 2.67-2.56 (m, 1H), 2.22 (m, J = 24.6, 12.8 Hz, 3H), 2.00-1.84 (m, 2H), 1.68 (s, 3H), 1.48 (d, J = 7.1 Hz, 3H), 1.35 (d, J = 21.0 Hz, 3H), 1.29-1.10 (m, 3H). |
| 401 | 627.2 | 1H NMR (400 MHz, DMSO-d6) δ 9.08 (d, J = 7.1 Hz, 1H), 8.75 (s, 2H), 8.65 (d, J = 8.1 Hz, 1H), 8.54 (dd, J = 5.0, 1.7 Hz, 1H), 8.11 (d, J = 8.0 Hz, 1H), 8.01 (d, J = 6.4 Hz, 1H), 7.84 (d, J = 7.6 Hz, 1H), 7.77 (d, J = 10.9 Hz, 1H), 7.37 (dd, J = 7.8, 4.9 Hz, 1H), 7.28 (d, J = 8.1 Hz, 1H), 7.21 (s, 1H), 5.23 (p, J = 7.0 Hz, 1H), 4.95-4.84 (m, 1H), 4.73 (t, J = 10.8 Hz, 1H), 4.40 (d, J = 11.3 Hz, 2H), 3.99 (s, 3H), 3.63 (td, J = 6.6, 3.9 Hz, 1H), 3.52-3.43 (m, 1H), 3.38 (d, J = 12.5 Hz, 1H), 3.20-3.10 (m, 1H), 3.10-2.91 (m, 2H), 1.60 (dd, J = 16.2, 7.8 Hz, 2H), 1.50 (d, J = 7.0 Hz, 3H), 1.26 (q, J = 7.3, 6.7 Hz, 6H). |
| 402 | 654.3 | 1H NMR (400 MHz, DMSO-d6) δ 8.66 (d, J = 8.1 Hz, 1H), 8.22 (d, J = 7.1 Hz, 1H), 8.07 (d, J = 8.1 Hz, 1H), 8.02 (d, J = 6.4 Hz, 1H), 7.76 (d, J = 10.9 Hz, 1H), 7.22 (d, J = 8.2 Hz, 1H), 7.15 (s, 1H), 5.14 (p, J = 7.1 Hz, 1H), 4.89 (m, J = 9.6, 4.6 Hz, 1H), 4.78 (m, J = 13.7, 10.3 Hz, 2H), 4.52 (p, J = 7.0, 6.5 Hz, 1H), 4.41 (m, J = 13.7, 9.2, 4.5 Hz, 1H), 3.97 (s, 3H), 3.13-3.02 (m, 2H), 3.02-2.91 (m, 1H), 2.85 (m, J = 13.7, 2.9 Hz, 1H), |

TABLE 3-continued

| Example | ES/MS m/z [M + H]+ | ¹H NMR |
|---|---|---|
| | | 2.70-2.55 (m, 1H), 2.28 (m, J = 45.3, 25.4, 12.0, 3.8 Hz, 3H), 2.00-1.85 (m, 1H), 1.74-1.58 (m, 3H), 1.48 (d, J = 7.1 Hz, 2H), 1.36 (m, J = 7.7 Hz, 3H), 1.26 (q, J = 5.2, 4.1 Hz, 2H), 1.22-1.09 (m, 2H), 1.01 (d, J = 6.6 Hz, 1H). |
| 403 | 656.5 | 1H NMR (400 MHz, DMSO-d6) δ 8.90 (d, J = 7.8 Hz, 1H), 8.08 (dd, J = 8.3, 6.7 Hz, 2H), 7.86 (d, J = 7.5 Hz, 1H), 7.40 (d, J = 8.3 Hz, 1H), 7.27-7.18 (m, 2H), 5.15 (p, J = 7.1 Hz, 1H), 4.95-4.78 (m, 2H), 4.75-4.65 (m, 1H), 4.60 (d, J = 10.3 Hz, 1H), 4.33 (s, 2H), 4.08 (s, 3H), 3.48 (s, 1H), 3.40 (d, J = 13.0 Hz, 1H), 3.06 (d, J = 11.6 Hz, 1H), 2.89 (d, J = 10.8 Hz, 1H), 2.01-1.81 (m, 3H), 1.64 (dd, J = 40.9, 11.9 Hz, 3H), 1.46 (d, J = 7.1 Hz, 3H), 1.40 (d, J = 11.1 Hz, 4 H), 1.22 (s, 3H), 0.97 (s, 3H). |
| 404 | 660.6 | 1H NMR (400 MHz, DMSO-d6) δ 8.66 (d, J = 8.0 Hz, 1H), 8.44 (d, J = 8.6 Hz, 1H), 7.99 (dd, J = 13.2, 7.2 Hz, 2H), 7.89 (d, J = 11.0 Hz, 1H), 7.15-7.07 (m, 2H), 5.06-4.97 (m, 1H), 4.88 (td, J = 9.4, 4.5 Hz, 0H), 4.79-4.68 (m, 3H), 4.67-4.57 (m, 1H), 4.40 (dt, J = 13.5, 9.4 Hz, 1H), 3.12-2.92 (m, 3H), 2.67 (s, 3H), 2.40-2.29 (m, 0H), 2.01-1.63 (m, 5H), 1.55 (tt, J = 10.6, 4.3 Hz, 5H), 1.49-1.35 (m, 5H), 1.30-1.17 (m, 2H), 0.87 (p, J = 4.0 Hz, 1H), 0.77-0.37 (m, 7H). |
| 405 | 648.3 | 1H NMR (400 MHz, DMSO-d6) δ 8.83 (s, 2H), 8.68 (d, J = 8.0 Hz, 1H), 8.44 (d, J = 8.6 Hz, 1H), 8.03 (d, J = 6.4 Hz, 1H), 7.98 (d, J = 8.0 Hz, 1H), 7.88 (d, J = 10.9 Hz, 1H), 7.14 (d, J = 8.1 Hz, 1H), 7.07 (s, 1H), 5.05-4.93 (m, 3H), 4.88 (ddd, J = 14.1, 9.3, 4.6 Hz, 1H), 4.74 (dt, J = 12.1, 9.1 Hz, 2H), 4.63-4.55 (m, 1H), 4.48-4.36 (m, 2H), 3.47 (d, J = 12.3 Hz, 1H), 3.39 (d, J = 12.7 Hz, 1H), 3.00 (dt, J = 32.8, 10.6 Hz, 2H), 2.40-2.28 (m, 1H), 1.92 (t, J = 10.9 Hz, 1H), 1.82 (d, J = 9.8 Hz, 1H), 1.75-1.47 (m, 3H), 1.43 (d, J = 7.1 Hz, 3H), 1.40-1.29 (m, 1H), 1.20 (dt, J = 19.6, 6.2 Hz, 1H), 1.01-0.80 (m, 3H), 0.79-0.52 (m, 4H), 0.48 (q, J = 5.8, 3.9 Hz, 1H). |
| 406 | 655.7 | 1H NMR (400 MHz, DMSO-d6) δ 8.45 (d, J = 8.6 Hz, 1H), 8.05 (d, J = 6.4 Hz, 1H), 8.01-7.95 (m, 2H), 7.16 (d, J = 8.1 Hz, 1H), 7.09 (s, 1H), 5.08-4.98 (m, 1H), 4.95 (d, J = 15.5 Hz, 1H), 4.88 (td, J = 9.4, 4.5 Hz, 1H), 4.73 (dd, J = 13.9, 9.6 Hz, 2H), 4.59 (d, J = 15.6 Hz, 2H), 4.54 (d, J = 4.2 Hz, 1H), 4.42 (dt, J = 12.1, 6.1 Hz, 1H), 3.13-2.91 (m, 3H), 2.41-2.28 (m, 2H), 2.00-1.82 (m, 3H), 1.80-1.59 (m, 3H), 1.56 (dt, J = 8.2, 4.5 Hz, 2H), 1.44 (d, J = 7.1 Hz, 3H), 1.22 (ddd, J = 9.5, 7.2, 4.2 Hz, 1H), 1.12-0.96 (m, 2H), 0.92-0.79 (m, 2H), 0.77-0.59 (m, 1H), 0.52-0.44 (m, 1H). |
| 407 | 685.5 | 1H NMR (400 MHz, DMSO-d6) δ 9.09 (d, J = 7.2 Hz, 1H), 8.10 (d, J = 8.0 Hz, 1H), 7.97 (s, 3H), 7.82 (d, J = 8.0 Hz, 1H), 7.48-7.38 (m, 2H), 7.27 (d, J = 8.1 Hz, 1H), 7.09 (s, 1H), 6.94 (d, J = 1.1 Hz, 1H), 5.23 (p, J = 7.0 Hz, 1H), 4.90-4.78 (m, 1H), 4.63-4.53 (m, 1H), 4.12 (s, 3H), 4.00 (s, 3H), 3.40 (s, 1H), 3.37 (s, 3H), 2.70-2.59 (m, 1H), 2.41-2.28 (m, 3H), 1.93 (d, J = 8.5 Hz, 2H), 1.76 (s, 2H), 1.50 (d, J = 7.0 Hz, 6H), 1.23 (d, J = 13.2 Hz, 2H), 0.61 (d, J = 12.3 Hz, 2H). |
| 408 | 614.3 | 1H NMR (400 MHz, DMSO-d6) δ 8.44 (d, J = 8.5 Hz, 1H), 7.99 (d, J = 8.0 Hz, 1H), 7.42 (s, 1H), 7.14 (d, J = 8.0 Hz, 1H), 7.01 (s, 1H), 5.06-4.97 (m, 1H), 4.69 (d, J = 10.5 Hz, 1H), 4.62 (s, 1H), 4.12 (d, J = 2.5 Hz, 3H), 3.99 (s, 3H), 3.80 (d, J = 9.4 Hz, 1H), 3.66 (s, 1H), 3.40 (s, 2H), 1.80 (d, J = 30.2 Hz, 4H), 1.58 (s, 7H), 1.43 (d, J = 7.1 Hz, 3H), 1.26 (q, J = 7.2, 6.7 Hz, 2H), 0.90-0.82 (m, 1H), 0.69 (d, J = 23.4 Hz, 2H), 0.47 (d, J = 9.1 Hz, 1H). |
| 409 | 651.3 | 1H NMR (400 MHz, DMSO-d6) δ 9.15 (d, J = 7.1 Hz, 1H), 8.60 (dd, J = 5.1, 1.7 Hz, 1H), 8.10 (d, J = 8.0 Hz, 1H), 8.02-7.96 (m, 3H), 7.51-7.40 (m, 2H), 7.27 (d, J = 8.1 Hz, 1H), 7.10 (s, 1H), 6.94 (d, J = 1.2 Hz, 1H), 5.23 (t, J = 7.1 Hz, 1H), 4.84 (t, J = 11.5 Hz, 1H), 4.63-4.52 (m, 1H), 4.12 (s, 3H), 4.00 (s, 3H), 3.37 (s, 3H), 2.73-2.62 (m, 1H), 1.93 (d, J = 12.7 Hz, 1H), 1.76 (d, J = 2.7 Hz, 1H), 1.51 (d, J = 7.0 Hz, 3H), 1.46 (s, 2H), 1.28-1.13 (m, 2H), 0.61 (d, J = 13.0 Hz, 1H). |
| 410 | 666.5 | 1H NMR (400 MHz, DMSO-d6) δ 8.76 (s, 2H), 8.68 (d, J = 8.0 Hz, 1H), 8.45 (d, J = 8.5 Hz, 1H), 8.00 (dd, J = 7.2, 3.5 Hz, 2H), 7.73 (d, J = 10.4 Hz, 1H), 7.21 (s, 1H), 7.15 (d, J = 8.1 Hz, 1H), 5.06-4.97 (m, 1H), 4.93-4.83 (m, 1H), 4.75 (dd, J = 9.4, 4.6 Hz, 1H), 4.39 (d, J = 11.9 Hz, 1H), 4.19 (s, 1H), 4.04 (q, J = 7.1 Hz, 2H), 3.45 (s, 2H), 3.38 (d, J = 13.1 Hz, 1H), 3.02 (d, J = 34.3 Hz, 2H), 2.08 (s, 2H), 2.00 (s, 2H), 1.96-1.81 (m, 1H), 1.73-1.53 (m, 4H), 1.45 (d, J = 7.1 Hz, 3H), 1.24 (s, 1H), 1.18 (t, J = 7.1 Hz, 2H), 0.87 (h, J = 3.8 Hz, 1H), 0.70 (d, J = 24.7 Hz, 2H), 0.49 (t, J = 7.1 Hz, 1H). |
| 411 | 628.6 | 1H NMR (400 MHz, DMSO-d6) δ 8.44 (d, J = 8.6 Hz, 1H), 7.99 (d, J = 8.0 Hz, 1H), 7.14 (d, J = 8.1 Hz, 1H), 7.02 (s, 1H), 6.92 (d, J = 16.5 Hz, 1H), 5.01 (p, J = 7.2 Hz, 1H), 4.65 (d, J = 34.5 Hz, 2H), 4.12 (s, 3H), 3.99 (s, 3H), 3.84 (s, 8H), 3.38 (d, J = 48.2 Hz, 4H), 1.93-1.72 (m, 3H), 1.56 (d, J = 8.8 Hz, 4H), 1.43 (d, J = 7.1 Hz, 3H), 1.31-1.12 (m, 2H), 0.87 (m, J = 8.7, 4.6 Hz, 1H), 0.69 (d, J = 22.3 Hz, 2H), 0.54-0.42 (m, 1H). |
| 412 | 666.6 | 1H NMR (400 MHz, DMSO-d6) δ 8.74 (s, 2H), 8.66 (d, J = 8.1 Hz, 1H), 8.45 (d, J = 8.6 Hz, 1H), 7.99 (dd, J = 7.2, 3.0 Hz, 2H), 7.67 (d, J = 10.7 Hz, 1H), 7.31 (s, 1H), 7.14 (d, J = 8.1 Hz, 1H), 5.07-4.96 (m, 1H), 4.92- |

TABLE 3-continued

| Example | ES/MS m/z [M + H]+ | ¹H NMR |
|---|---|---|
| | | 4.84 (m, 1H), 4.76 (m, J = 9.3, 4.5 Hz, 2H), 4.40 (s, 1H), 4.22 (s, 1H), 3.40 (s, 3H), 3.01 (d, J = 36.1 Hz, 3H), 2.09 (d, J = 4.6 Hz, 2H), 1.91 (t, J = 12.4 Hz, 3H), 1.73 (d, J = 26.8 Hz, 3H), 1.56 (m, J = 8.4, 4.5 Hz, 1H), 1.44 (d, J = 7.1 Hz, 3H), 1.32 (s, 1H), 1.24 (s, 2H), 0.91-0.83 (m, 1H), 0.77-0.56 (m, 3H), 0.49 (q, J = 5.4, 4.6 Hz, 1H). |
| 413 | 630.6 | 1H NMR (400 MHz, DMSO-d6) δ 8.87 (d, J = 24.9 Hz, 2H), 8.64 (dd, J = 8.1, 1.5 Hz, 1H), 8.46 (d, J = 8.6 Hz, 1H), 8.01 (dd, J = 8.6, 7.2 Hz, 2H), 7.52 (d, J = 10.5 Hz, 1H), 7.27 (s, 1H), 7.14 (d, J = 8.1 Hz, 1H), 5.08-4.97 (m, 1H), 4.94-4.70 (m, 3H), 4.41 (d, J = 13.9, 9.4 Hz, 1H), 3.56 (m, J = 7.1, 3.6 Hz, 1H), 3.43 (m, J = 32.7, 12.5 Hz, 2H), 3.00 (m, J = 31.6, 10.8 Hz, 2H), 2.35 (m, J = 13.7, 11.4, 6.5 Hz, 1H), 2.00-1.80 (m, 2H), 1.76-1.63 (m, 1H), 1.56 (m, J = 12.0, 4.9 Hz, 3H), 1.44 (d, J = 7.1 Hz, 3H), 1.34 (m, J = 11.7, 5.2 Hz, 1H), 1.28-1.15 (m, 2H), 1.11 (d, J = 5.9 Hz, 3H), 1.08-0.98 (m, 2H), 0.96-0.82 (m, 2H), 0.78-0.60 (m, 2H), 0.49 (m, J = 9.0, 5.6, 3.6 Hz, 1H). |
| 414 | 702.3 | 1H NMR (400 MHz, DMSO-d6) δ 9.49 (d, J = 6.9 Hz, 1H), 8.18-8.09 (m, 2H), 8.07-8.00 (m, 1H), 7.98 (s, 2H), 7.91-7.84 (m, 2H), 7.44 (s, 1H), 7.32 (d, J = 8.1 Hz, 1H), 7.11 (s, 1H), 6.94 (d, J = 1.2 Hz, 1H), 5.30 (p, J = 6.9 Hz, 1H), 4.88 (t, J = 11.0 Hz, 1H), 4.60 (d, J = 13.6 Hz, 1H), 4.13 (s, 3H), 4.00 (s, 3H), 3.54 (s, 4H), 3.37 (s, 3H), 2.84 (dd, J = 12.6, 8.1 Hz, 1H), 2.60 (d, J = 8.3 Hz, 2H), 1.95 (s, 1H), 1.76 (s, 1H), 1.56 (d, J = 7.0 Hz, 3H), 1.54-1.21 (m, 4H), 0.59 (d, J = 12.5 Hz, 1H). |
| 415 | 666.6 | 1H NMR (400 MHz, DMSO-d6) δ 8.77 (s, 2H), 8.65 (d, J = 8.0 Hz, 1H), 8.44 (t, J = 9.3 Hz, 1H), 8.06-7.95 (m, 2H), 7.54 (m, J = 10.6, 5.4 Hz, 1H), 7.24 (d, J = 4.9 Hz, 1H), 7.14 (m, J = 8.1, 1.1 Hz, 1H), 5.09-4.96 (m, 1H), 4.90 (d, J = 9.6 Hz, 1H), 4.78 (d, J = 10.4 Hz, 1H), 4.66 (t, J = 11.3 Hz, 1H), 4.56 (d, J = 13.0 Hz, 1H), 4.41 (s, 1H), 4.15 (m, J = 8.0, 4.0 Hz, 1H), 3.38 (s, 3H), 3.12-2.90 (m, 3H), 2.34 (m, J = 3.9, 2.1 Hz, 1H), 2.26-2.14 (m, 1H), 2.03-1.87 (m, 3H), 1.86-1.62 (m, 3H), 1.61-1.46 (m, 3H), 1.44 (m, J = 7.1, 2.5 Hz, 3H), 1.35-1.14 (m, 2H), 0.98-0.90 (m, 1H), 0.90-0.82 (m, 1H), 0.69 (s, 2H), 0.49 (p, J = 3.9 Hz, 1H). |
| 416 | 630.6 | 1H NMR (400 MHz, DMSO-d6) δ 8.75 (s, 3H), 8.63 (d, J = 8.1 Hz, 1H), 8.45 (m, J = 8.6, 4.3 Hz, 1H), 8.04-7.96 (m, 2H), 7.52 (m, J = 9.7, 2.7 Hz, 1H), 7.27 (d, J = 1.4 Hz, 1H), 7.17-7.11 (m, 1H), 5.02 (m, J = 7.3 Hz, 1H), 4.92-4.82 (m, 2H), 4.81-4.68 (m, 2H), 4.42 (d, J = 12.0 Hz, 1H), 3.01 (d, J = 35.5 Hz, 3H), 1.99-1.79 (m, 3H), 1.68 (s, 2H), 1.56 (d, J = 7.2 Hz, 3H), 1.44 (d, J = 7.1, 1.6 Hz, 3H), 1.30-1.20 (m, 2H), 1.18 (s, 1H), 1.11 (d, J = 5.9 Hz, 2H), 1.08-0.97 (m, 2H), 0.97-0.92 (m, 1H), 0.92-0.84 (m, 2H), 0.75-0.60 (m, 3H), 0.53-0.44 (m, 1H). |
| 417 | 649.8 | 1H NMR (400 MHz, DMSO-d6) δ 8.76 (s, 2H), 8.66 (d, J = 8.0 Hz, 1H), 8.03 (dd, J = 17.4, 7.3 Hz, 2H), 7.81 (dd, J = 11.4, 9.2 Hz, 2H), 7.19 (d, J = 8.1 Hz, 1H), 7.14 (s, 1H), 5.14 (q, J = 7.3 Hz, 1H), 4.91-4.55 (m, 6H), 4.43 (d, J = 11.4 Hz, 3H), 3.61 (dt, J = 21.7, 6.0 Hz, 2H), 3.51-3.31 (m, 3H), 1.92 (t, J = 11.7 Hz, 2H), 1.45 (d, J = 7.1 Hz, 3H), 1.38 (d, J = 12.7 Hz, 2H), 1.33 (s, 2H), 1.21 (s, 3H), 1.10 (d, J = 7.0 Hz, 1H), 0.95 (s, 3H). |
| 418 | 656.5 | 1H NMR (400 MHz, DMSO-d6) δ 8.77 (s, 2H), 8.70 (d, J = 8.1 Hz, 1H), 8.05 (dd, J = 10.3, 7.2 Hz, 2H), 7.83 (dd, J = 9.1, 5.1 Hz, 2H), 7.20 (d, J = 8.2 Hz, 1H), 7.11 (s, 1H), 6.41 (s, 1H), 5.19-4.71 (m, 6H), 4.40 (d, J = 10.5 Hz, 2H), 3.01 (d, J = 33.1 Hz, 3H), 2.34 (s, 1H), 1.92 (t, J = 12.1 Hz, 2H), 1.58 (d, J = 8.2 Hz, 3H), 1.51-1.42 (m, 4H), 1.37 (d, J = 23.5 Hz, 5H), 1.21 (s, 3H), 1.08 (s, 3H), 0.95 (s, 3H). |
| 419 | 674.6 | 1H NMR (400 MHz, DMSO-d6) 8.73 (d, J = 9.1 Hz, 2H), 8.12-8.02 (m, 2H), 7.97 (d, J = 10.6 Hz, 1H), 7.83 (d, J = 7.4 Hz, 1H), 7.21 (t, J = 4.1 Hz, 2H), 5.68-5.44 (m, 3H), 5.13 (t, J = 7.2 Hz, 1H), 4.91-4.70 (m, 3H), 4.42 (d, J = 8.0 Hz, 3H), 3.42 (d, J = 36.1 Hz, 3H), 3.01 (d, J = 40.7 Hz, 3H), 1.92 (t, J = 11.6 Hz, 2H), 1.76-1.50 (m, 3H), 1.45 (d, J = 7.2 Hz, 3H), 1.42-1.26 (m, 5H), 1.21 (s, 3H), 1.07 (s, 3H), 0.95 (s, 3H). |
| 420 | 646.6 | 1H NMR (400 MHz, DMSO-d6) δ 8.75 (s, 1H), 8.66 (d, J = 8.1 Hz, 1H), 8.04 (t, J = 7.0 Hz, 2H), 7.85 (dd, J = 18.1, 9.2 Hz, 2H), 7.20 (d, J = 8.1 Hz, 1H), 6.95 (s, 1H), 5.22 (s, 1H), 5.12 (t, J = 7.3 Hz, 2H), 4.86-4.72 (m, 3H), 4.47-4.23 (m, 5H), 3.53-3.34 (m, 4H), 3.17-2.90 (m, 4H), 2.70 (d, J = 18.4 Hz, 2H), 2.39-2.24 (m, 3H), 1.94-1.84 (m, 2H), 1.82-1.61 (m, 3H), 1.46 (d, J = 7.0 Hz, 2H), 1.39-1.26 (m, 4H), 1.21 (s, 2H), 0.94 (s, 2H). |
| 421 | 634.5 | 1H NMR (400 MHz, DMSO-d6) δ 8.73 (s, 1H), 8.65 (d, J = 8.0 Hz, 1H), 8.04 (dd, J = 14.0, 7.3 Hz, 2H), 7.95 (d, J = 11.2 Hz, 1H), 7.81 (d, J = 7.3 Hz, 1H), 7.20 (d, J = 8.1 Hz, 1H), 6.93 (s, 1H), 5.11 (t, J = 7.2 Hz, 1H), 4.99-4.89 (m, 2H), 4.80 (s, 1H), 4.41 (s, 1H), 4.24 (s, 1H), 3.47 (d, J = 11.8 Hz, 2H), 3.39 (d, J = 12.9 Hz, 2H), 2.96 (s, 1H), 1.91 (t, J = 13.0 Hz, 2H), 1.68 (d, J = 7.0 Hz, 2H), 1.48 (dd, J = 21.1, 7.0 Hz, 4H), 1.37 (d, J = 12.0 Hz, 2H), 1.30 (s, 1H), 1.20 (d, J = 4.9 Hz, 2H), 1.15 (s, 1H), 0.95 (d, J = 10.9 Hz, 2H). |
| 422 | 634.3 | 1H NMR (400 MHz, DMSO-d6) δ 8.11 (d, J = 6.3 Hz, 1H), 7.99 (d, J = 8.0 Hz, 1H), 7.65 (d, J = 10.9 Hz, 1H), 7.15 (d, J = 8.0 Hz, 1H), 7.03 (s, 1H), 5.11 (q, J = 7.0 Hz, 1H), 4.71-4.59 (m, 1H), 4.59-4.51 (m, 2H), 4.49 (s, 1H), 3.72 (ddt, J = 16.9, 14.3, 7.1 Hz, 3H), 3.55 (d, J = 13.5 Hz, |

TABLE 3-continued

| Example | ES/MS m/z [M + H]+ | ¹H NMR |
|---|---|---|
| | | 1H), 3.25-3.10 (m, 5H), 2.50 (tt, J = 9.7, 4.4 Hz, 1H), 2.08 (s, 1H), 1.93 (s, 1H), 1.75 (s, 1H), 1.65-1.48 (m, 7H), 1.31 (s, 3H), 1.09 (dt, J = 8.5, 4.5 Hz, 1H), 0.82 (s, 2H), 0.60 (dd, J = 8.4, 3.5 Hz, 1H). |
| 423 | 620.6 | 1H NMR (400 MHz, DMSO-d6) δ 8.13 (d, J = 6.3 Hz, 1H), 8.07 (d, J = 8.1 Hz, 1H), 7.65 (d, J = 10.8 Hz, 1H), 7.23 (d, J = 8.1 Hz, 1H), 7.02 (s, 1H), 5.51 (s, 1H), 5.26 (q, J = 6.9, 6.3 Hz, 1H), 5.04-4.91 (m, 2H), 4.57-4.31 (m, 5H), 3.71 (d, J = 13.0 Hz, 1H), 3.55 (d, J = 13.5 Hz, 2H), 3.17 (dt, J = 23.4, 11.9 Hz, 3H), 2.50 (tt, J = 9.6, 4.5 Hz, 2H), 2.07 (s, 2H), 1.91 (dd, J = 24.3, 11.5 Hz, 2H), 1.78 (s, 2H), 1.57 (d, J = 7.0 Hz, 3H), 1.49 (d, J = 11.9 Hz, 2H), 1.42 (t, J = 7.2 Hz, 5H), 1.31 (s, 3H), 1.09 (s, 3H). |
| 424 | 678.7 | 1H NMR (400 MHz, MeOD) δ 8.12 (d, J = 6.3 Hz, 1H), 8.05 (d, J = 8.1 Hz, 1H), 7.68 (d, J = 11.0 Hz, 1H), 7.22 (d, J = 8.2 Hz, 1H), 7.13 (s, 1H), 5.27 (dd, J = 7.2, 5.1 Hz, 1H), 4.96 (dd, J = 9.8, 4.5 Hz, 2H), 4.57 (s, 1H), 4.50 (dd, J = 10.0, 4.7 Hz, 1H), 4.35 (ddd, J = 14.2, 9.2, 5.7 Hz, 1H), 3.80 (h, J = 6.0 Hz, 2H), 3.70 (d, J = 12.9 Hz, 1H), 3.59-3.44 (m, 2H), 3.24-3.09 (m, 2H), 2.50 (tt, J = 9.9, 4.2 Hz, 1H), 1.90 (t, J = 11.5 Hz, 1H), 1.77 (s, 1H), 1.57 (d, J = 7.0 Hz, 3H), 1.54-1.32 (m, 4H), 1.31 (s, 2H), 1.09 (s, 3H), 1.00 (dd, J = 18.7, 6.1 Hz, 4H). |
| 425 | 664.6 | 1H NMR (400 MHz, MeOD) δ 8.12 (d, J = 6.3 Hz, 1H), 8.05 (d, J = 8.1 Hz, 1H), 7.67 (d, J = 11.0 Hz, 1H), 7.22 (d, J = 8.2 Hz, 1H), 7.10 (s, 1H), 5.30-5.22 (m, 1H), 4.96 (dt, J = 9.4, 4.9 Hz, 2H), 4.67-4.45 (m, 3H), 4.34 (ddd, J = 14.0, 9.3, 5.7 Hz, 1H), 3.85-3.67 (m, 3H), 3.55 (d, J = 13.2 Hz, 2H), 3.46-3.34 (m, 2H), 3.24-3.10 (m, 2H), 2.50 (tt, J = 9.6, 4.4 Hz, 1H), 2.07 (s, 2H), 1.90 (t, J = 11.4 Hz, 1H), 1.78 (s, 2H), 1.57 (d, J = 7.1 Hz, 3H), 1.52-1.33 (m, 4H), 1.31 (s, 3H), 1.12-1.01 (m, 5H). |
| 426 | 629.5 | 1H NMR (400 MHz, MeOD) δ 8.15 (d, J = 6.3 Hz, 1H), 8.01 (d, J = 8.1 Hz, 1H), 7.76 (d, J = 10.8 Hz, 1H), 7.17 (d, J = 8.1 Hz, 1H), 7.08 (s, 1H), 5.11 (q, J = 7.0 Hz, 1H), 4.96 (dt, J = 9.5, 4.8 Hz, 1H), 4.77 (t, J = 6.4 Hz, 1H), 4.49 (dt, J = 16.2, 10.9 Hz, 2H), 3.75-3.67 (m, 1H), 3.55 (d, J = 13.2 Hz, 1H), 3.25-3.15 (m, 1H), 3.06-2.91 (m, 2H), 2.49 (td, J = 9.7, 5.0 Hz, 1H), 1.71 (s, 1H), 1.64-1.43 (m, 4H), 1.32 (s, 1H), 1.09 (dt, J = 8.8, 4.5 Hz, 1H), 0.85-0.76 (m, 1H), 0.60 (q, J = 7.1, 5.6 Hz, 1H). |
| 427 | 678.6 | 1H NMR (400 MHz, MeOD) δ 8.12 (d, J = 6.3 Hz, 1H), 7.99 (d, J = 8.0 Hz, 1H), 7.69 (d, J = 11.0 Hz, 1H), 7.15 (d, J = 8.1 Hz, 1H), 7.08 (s, 1H), 5.11 (q, J = 7.0 Hz, 1H), 4.58 (t, J = 5.0 Hz, 1H), 4.54-4.43 (m, 2H), 3.84 (t, J = 5.1 Hz, 2H), 3.74-3.66 (m, 1H), 3.59-3.44 (m, 3H), 3.43-3.35 (m, 2H), 3.29-3.10 (m, 11H), 2.50 (tt, J = 9.5, 4.2 Hz, 1H), 2.13-1.90 (m, 2H), 1.68 (ddd, J = 11.8, 10.0, 6.3 Hz, 8H), 1.56 (dd, J = 7.6, 4.9 Hz, 5H), 1.44 (h, J = 7.4 Hz, 8H), 1.31 (s, 2H), 1.05 (t, J = 7.4 Hz, 11H), 0.82 (s, 1H), 0.64-0.55 (m, 1H). |
| 428 | 647.8 | 1H NMR (400 MHz, MeOD) δ 8.11 (d, J = 6.3 Hz, 1H), 8.10-7.97 (m, 1H), 7.70 (d, J = 10.9 Hz, 1H), 7.16 (d, J = 8.1 Hz, 1H), 7.04 (s, 1H), 5.11 (q, J = 7.0 Hz, 1H), 4.68 (t, J = 7.0 Hz, 2H), 4.48 (ddt, J = 23.9, 18.7, 9.3 Hz, 2H), 3.70 (dd, J = 12.5, 4.9 Hz, 1H), 3.55 (d, J = 13.2 Hz, 1H), 3.25-3.10 (m, 2H), 2.71 (td, J = 6.9, 2.5 Hz, 2H), 2.50 (tt, J = 9.6, 4.4 Hz, 1H), 2.07 (s, 1H), 1.96 (q, J = 7.7, 6.4 Hz, 1H), 1.67-1.58 (m, 3H), 1.32 (d, J = 10.8 Hz, 2H), 1.09 (dt, J = 8.7, 4.4 Hz, 1H), 0.83 (s, 2H), 0.59 (ddd, J = 7.8, 5.7, 4.0 Hz, 1H). |
| 429 | 696.6 | 1H NMR (400 MHz, MeOD) δ 8.13 (d, J = 6.3 Hz, 1H), 7.98 (d, J = 8.0 Hz, 1H), 7.74 (d, J = 10.9 Hz, 1H), 7.18-7.11 (m, 3H), 7.08 (s, 1H), 6.91-6.82 (m, 1H), 6.73-6.63 (m, 2H), 5.10 (q, J = 7.0 Hz, 1H), 4.83 (tt, J = 9.1, 3.2 Hz, 4H), 4.58-4.40 (m, 2H), 4.32 (dt, J = 10.7, 4.1 Hz, 1H), 4.22 (ddd, J = 10.9, 6.8, 4.2 Hz, 1H), 3.75-3.64 (m, 1H), 3.59-3.50 (m, 1H), 3.18 (td, J = 13.3, 12.8, 10.1 Hz, 2H), 2.49 (tt, J = 14.1, 4.0 Hz, 1H), 2.16-2.00 (m, 1H), 1.86 (ddd, J = 11.6, 7.3, 3.4 Hz, 1H), 1.66 (s, 1H), 1.59-1.42 (m, 6H), 1.42-1.28 (m, 2H), 1.25-1.13 (m, 1H), 1.08 (dt, J = 8.8, 4.6 Hz, 1H), 0.78 (s, 1H), 0.58 (ddd, J = 7.8, 5.7, 4.0 Hz, 1H). |
| 430 | 648.5 | 1H NMR (400 MHz, MeOD) δ 8.11 (dd, J = 6.3, 1.1 Hz, 2H), 7.99 (dd, J = 8.1, 1.6 Hz, 1H), 7.65 (dd, J = 11.0, 7.6 Hz, 2H), 7.15 (dd, J = 8.0, 1.3 Hz, 1H), 7.08 (s, 1H), 5.16-5.06 (m, 2H), 4.82 (dd, J = 9.6, 4.3 Hz, 2H), 4.57-4.43 (m, 5H), 4.41-4.31 (m, 2H), 3.74 (ddt, J = 30.4, 11.9, 4.0 Hz, 4H), 3.55 (d, J = 13.5 Hz, 2H), 3.25-3.08 (m, 4H), 3.07 (d, J = 4.5 Hz, 4H), 2.50 (tt, J = 9.8, 4.4 Hz, 2H), 2.07 (s, 2H), 1.73 (s, 3H), 1.56 (d, J = 7.0 Hz, 9H), 1.32 (s, 2H), 1.16 (dd, J = 6.2, 3.7 Hz, 4H), 1.09 (dt, J = 8.7, 4.5 Hz, 2H), 0.82 (s, 4H), 0.59 (s, 2H). |
| 431 | 646.5 | 1H NMR (400 MHz, MeOD) δ 7.99 (d, J = 8.0 Hz, 1H), 7.48 (s, 1H), 7.15 (d, J = 8.1 Hz, 1H), 7.04 (ddt, J = 14.4, 3.1, 1.6 Hz, 2H), 5.11 (q, J = 7.0 Hz, 1H), 4.85-4.68 (m, 3H), 4.39 (d, J = 14.6 Hz, 1H), 4.09 (s, 3H), 3.74 (q, J = 4.9 Hz, 2H), 3.42 (s, 2H), 3.12 (s, 3H), 2.22 (d, J = 12.6 Hz, 1H), 2.01-1.82 (m, 2H), 1.73 (q, J = 14.9, 13.5 Hz, 4H), 1.61-1.51 (m, 6H), 1.32 (s, 1H), 1.09 (dt, J = 8.8, 4.4 Hz, 1H), 0.82 (d, J = 8.3 Hz, 2H), 0.60 (ddd, J = 7.8, 5.6, 4.0 Hz, 1H). |
| 432 | 658.9 | 1H NMR (400 MHz, MeOD) δ 7.99 (d, J = 8.0 Hz, 1H), 7.93 (d, J = 1.3 Hz, 1H), 7.47 (d, J = 1.3 Hz, 1H), 7.15 (d, J = 8.1 Hz, 1H), 7.02 (s, 1H), 5.11 (q, J = 7.1 Hz, 1H), 4.78 (tdd, J = 14.7, 9.0, 4.3 Hz, 2H), 4.50 (qd, J = 9.5, 4.7 Hz, 1H), 4.43-4.34 (m, 1H), 4.11 (s, 2H), 3.80-3.61 (m, 3H), |

TABLE 3-continued

| Example | ES/MS m/z [M + H]+ | ¹H NMR |
|---|---|---|
| | | 3.55 (d, J = 13.4 Hz, 1H), 3.27-3.06 (m, 4H), 2.51 (ddd, J = 14.2, 10.2, 4.1 Hz, 1H), 1.73 (s, 1H), 1.67-1.41 (m, 6H), 1.36-1.29 (m, 1H), 1.09 (dt, J = 8.8, 4.4 Hz, 1H), 0.60 (ddd, J = 7.8, 5.7, 4.0 Hz, 1H). |
| 433 | 628.6 | 1H NMR (400 MHz, MeOD) δ 7.99 (d, J = 8.0 Hz, 1H), 7.48 (s, 1H), 7.15 (d, J = 8.1 Hz, 1H), 7.04 (ddt, J = 14.4, 3.1, 1.6 Hz, 2H), 5.11 (q, J = 7.0 Hz, 1H), 4.85-4.68 (m, 3H), 4.39 (d, J = 14.6 Hz, 1H), 4.09 (s, 3H), 3.74 (q, J = 4.9 Hz, 2H), 3.42 (s, 2H), 3.12 (s, 3H), 2.22 (d, J = 12.6 Hz, 1H), 2.01-1.82 (m, 2H), 1.73 (q, J = 14.9, 13.5 Hz, 4H), 1.61-1.51 (m, 6H), 1.32 (s, 1H), 1.09 (dt, J = 8.8, 4.4 Hz, 1H), 0.82 (d, J = 8.3 Hz, 2H), 0.60 (ddd, J = 7.8, 5.6, 4.0 Hz, 1H). |
| 434 | 697.6 | 1H NMR (400 MHz, MeOD) δ 8.11 (d, J = 6.3 Hz, 1H), 7.95-7.86 (m, 2H), 7.69 (d, J = 10.9 Hz, 1H), 7.46 (ddd, J = 8.3, 7.1, 2.0 Hz, 1H), 7.12 (d, J = 8.1 Hz, 1H), 6.96 (s, 1H), 6.78 (ddd, J = 7.0, 5.0, 0.9 Hz, 1H), 6.43 (dt, J = 8.4, 0.9 Hz, 1H), 5.11 (q, J = 7.0 Hz, 1H), 4.96 (dt, J = 9.5, 4.9 Hz, 1H), 4.81 (dd, J = 13.8, 9.3 Hz, 1H), 4.66-4.39 (m, 4H), 3.70 (dt, J = 13.0, 4.2 Hz, 1H), 3.55 (d, J = 13.3 Hz, 1H), 3.23-3.09 (m, 2H), 2.50 (tt, J = 9.7, 4.3 Hz, 1H), 2.16-2.00 (m, 1H), 1.96-1.87 (m, 1H), 1.56 (t, J = 8.3 Hz, 8H), 1.33-1.20 (m, 1H), 1.09 (dt, J = 8.7, 4.5 Hz, 1H), 0.79 (t, J = 8.5 Hz, 2H), 0.63-0.54 (m, 1H). |
| 435 | 684.7 | 1H NMR (400 MHz, MeOD) δ 8.60 (d, J = 2.6 Hz, 1H), 8.50 (d, J = 2.6 Hz, 1H), 8.12 (d, J = 8.1 Hz, 1H), 7.72 (d, J = 1.2 Hz, 1H), 7.35-7.28 (m, 2H), 7.19 (s, 1H), 5.38 (q, J = 7.0 Hz, 1H), 5.07-4.96 (m, 2H), 4.81 (d, J = 4.9 Hz, 1H), 4.73 (ddd, J = 14.8, 6.7, 3.8 Hz, 2H), 4.61-4.53 (m, 1H), 3.84-3.52 (m, 9H), 3.49 (s, 4H), 3.20 (s, 3H), 2.81-2.69 (m, 2H), 2.60-2.45 (m, 2H), 1.83 (d, J = 13.8 Hz, 2H), 1.65 (d, J = 7.1 Hz, 6H), 1.54-1.41 (m, 2H), 1.31 (s, 2H), 0.72 (q, J = 12.3 Hz, 2H). |
| 436 | 646.7 | 1H NMR (400 MHz, MeOD) δ 8.00 (d, J = 8.1 Hz, 1H), 7.73 (d, J = 1.2 Hz, 1H), 7.32 (dd, J = 11.6, 1.3 Hz, 1H), 7.16 (d, J = 8.1 Hz, 1H), 7.07 (s, 1H), 5.11 (q, J = 7.0 Hz, 1H), 4.75 (tdd, J = 21.3, 13.4, 5.0 Hz, 2H), 4.50 (dt, J = 14.2, 4.1 Hz, 1H), 3.82 (dt, J = 6.1, 3.1 Hz, 1H), 3.73 (q, J = 5.0 Hz, 3H), 3.63 (s, 1H), 3.49 (s, 3H), 3.15 (s, 3H), 1.72 (d, J = 10.7 Hz, 2H), 1.57 (t, J = 5.4 Hz, 6H), 1.47 (s, 1H), 1.31 (s, 1H), 1.09 (dt, J = 8.7, 4.4 Hz, 1H), 0.88-0.74 (m, 2H), 0.60 (ddd, J = 7.9, 5.7, 4.0 Hz, 1H). |
| 437 | 663.2 | 1H NMR (400 MHz, DMSO-d6) δ 8.52 (d, J = 7.9 Hz, 1H), 7.97 (s, 2H), 7.73 (s, 1H), 7.43-7.36 (m, 2H), 7.19 (d, J = 1.7 Hz, 1H), 7.10 (t, J = 7.2 Hz, 1H), 6.91 (s, 1H), 5.60-5.45 (m, 1H), 4.95 (dd, J = 30.0, 15.6 Hz, 1H), 4.86-4.74 (m, 1H), 4.54 (s, 0H), 4.25 (s, 1H), 4.09 (s, 3H), 3.99 (s, 3H), 3.44-3.22 (m, 1H), 2.75 (d, J = 13.3 Hz, 0H), 1.98 (s, 1H), 1.92-1.73 (m, 3H), 1.65 (s, 5H), 1.59 (d, J = 7.2 Hz, 3H), 1.52-1.43 (m, 1H), 1.37-1.20 (m, 1H), 0.85-0.75 (m, 1H), 0.75-0.61 (m, 1H), 0.54-0.38 (m, 2H). |
| 438 | 660.6 | 1H NMR (400 MHz, DMSO-d6) δ 8.59 (d, J = 8.8 Hz, 1H), 8.08 (d, J = 8.0 Hz, 1H), 7.98 (s, 2H), 7.73 (s, 1H), 7.69-7.58 (m, 2H), 7.37 (s, 1H), 7.33-7.28 (m, 1H), 7.25 (d, J = 8.1 Hz, 1H), 5.84 (t, J = 13.7 Hz, 1H), 5.20 (dd, J = 27.9, 14.6 Hz, 1H), 5.12-5.01 (m, 1H), 5.01-4.94 (m, 0.4H), 4.52 (m, 0.6H), 4.19 (s, 1H), 4.09-4.00 (m, 2H), 3.43-3.21 (m, 1H), 3.17 (s, 0H), 2.84-2.74 (m, 0.6H), 2.27-2.04 (m, 2H), 2.02-1.90 (m, 2H), 1.80 (d, J = 29.5 Hz, 1H), 1.65 (d, J = 14.5 Hz, 2H), 1.58-1.51 (m, 2H), 1.45 (d, J = 7.1 Hz, 3H), 1.40-1.29 (m, 1H), 1.29-1.19 (m, 1H), 1.11-0.95 (m, 2H), 0.89-0.80 (m, 1H), 0.72-0.58 (m, 1H), 0.49 (dtd, J = 16.6, 8.4, 5.5 Hz, 3H). |
| 439 | 646.3 | 1H NMR (400 MHz, DMSO-d6) δ 8.82 (d, J = 6.9 Hz, 1H), 8.07 (d, J = 8.0 Hz, 1H), 8.04-7.63 (m, 3H), 7.43-7.27 (m, 3H), 7.27-7.15 (m, 3H), 7.07 (s, 1H), 6.89 (s, 1H), 5.18 (p, J = 7.0 Hz, 1H), 5.04-4.92 (m, 1H), 4.92-4.78 (m, 1H), 4.67-4.47 (m, 2H), 4.30-4.17 (m, 1H), 4.11 (s, 3H), 3.99 (s, 3H), 3.47-2.95 (m, 2H), 2.85-2.70 (m, 1H), 2.44-2.29 (m, 1H), 2.22 (td, J = 12.4, 4.4 Hz, 1H), 2.06-1.32 (m, 11H), 1.32-1.05 (m, 2H), 0.62-0.42 (m, 1H). |
| 440 | 679.2 | 1H NMR (400 MHz, DMSO-d6) δ 9.47 (d, J = 7.1 Hz, 1H), 8.49 (s, 1H), 8.34 (d, J = 1.1 Hz, 1H), 8.10 (d, J = 8.0 Hz, 1H), 7.96 (s, 2H), 7.85-7.50 (m, 2H), 7.37-7.15 (m, 3H), 5.26 (p, J = 7.0 Hz, 1H), 5.04-4.78 (m, 2H), 4.59-4.46 (m, 1H), 4.25-4.14 (m, 1H), 4.08-3.98 (m, 2H), 3.44-3.02 (m, 2H), 2.82-2.69 (m, 1H), 2.43-2.29 (m, 1H), 2.23-2.08 (m, 1H), 2.05-1.37 (m, 11H), 1.37-0.94 (m, 5H), 0.53-0.30 (m, 2H). |
| 441 | 626.4 | 1H NMR (400 MHz, DMSO-d6) δ 8.04 (d, J = 8.1 Hz, 1H), 7.95 (s, 2H), 7.82 (d, J = 7.4 Hz, 1H), 7.73 (s, 1H), 7.37 (s, 1H), 7.18 (d, J = 8.1 Hz, 1H), 7.02 (s, 1H), 6.89 (s, 1H), 5.12 (p, J = 7.0 Hz, 1H), 4.87-4.74 (m, 1H), 4.63-4.33 (m, 2H), 4.29-4.18 (m, 1H), 4.11 (s, 3H), 3.98 (s, 3H), 3.46-2.96 (m, 2H), 2.84-2.69 (m, 1H), 2.03-1.48 (m, 9H), 1.48-1.26 (m, 8H), 1.21 (s, 3H), 1.16-0.98 (m, 2H), 0.94 (s, 3H). |
| 442 | 646.3 | 1H NMR (400 MHz, DMSO-d6) δ 8.55 (d, J = 8.8 Hz, 1H), 8.05 (d, J = 8.0 Hz, 1H), 8.02-7.61 (m, 3H), 7.39 (s, 1H), 7.23 (d, J = 8.0 Hz, 1H), 7.13 (s, 1H), 6.91 (s, 1H), 5.51 (t, J = 13.6 Hz, 1H), 5.24-4.88 (m, 2H), |

TABLE 3-continued

| Example | ES/MS m/z [M + H]+ | 1H NMR |
|---|---|---|
| | | 4.64-4.45 (m, 1H), 4.32-4.18 (m, 1H), 4.09 (s, 3H), 3.99 (s, 3H), 3.46-3.03 (m, 2H), 2.85-2.68 (m, 1H), 2.28-1.48 (m, 10H), 1.44 (d, J = 7.1 Hz, 3H), 1.38-1.15 (m, 2H), 0.93-0.77 (m, 1H), 0.73-0.55 (m, 1H), 0.55-0.38 (m, 2H). |
| 443 | 612.3 | 1H NMR (400 MHz, DMSO-d6) δ 8.04 (d, J = 8.1 Hz, 1H), 8.02-7.67 (m, 3H), 7.64 (d, J = 8.0 Hz, 1H), 7.36 (br. s, 1H), 7.21 (d, J = 8.1 Hz, 1H), 7.02 (s, 1H), 6.89 (s, 1H), 5.16 (p, J = 7.1 Hz, 1H), 5.06-4.17 (m, 1H), 4.61 (br. t, J = 5.8 Hz, 2H), 4.09 (s, 3H), 3.98 (s, 3H), 3.40-3.01 (m, 2H), 2.85-2.68 (m, 1H), 2.02-1.89 (m, 1H), 1.89-1.70 (m, 7H), 1.63 (s, 3H), 1.55-1.51 (m, 3H), 1.40-1.27 (m, 1H), 1.17 (s, 3H), 1.21-1.07 (m, 1H), 1.00 (s, 3H), 0.89-0.77 (m, 2H). |
| 444 1 | 610.3 | 1H NMR (400 MHz, DMSO-d6) δ 8.43 (d, J = 8.6 Hz, 1H), 7.98 (d, J = 8.0 Hz, 1H), 8.09-7.69 (m, 3H), 7.36 (br. s, 1H), 7.13 (d, J = 8.1 Hz, 1H), 7.01 (s, 1H), 6.89 (s, 1H), 5.07-4.94 (m, 1H), 4.76-4.47 (m, 2H), 4.11 (s, 3H), 3.99 (s, 3H), 3.92-3.18 (m, 3H), 3.18-2.69 (m, 1H), 2.03-1.92 (m, 1H), 1.91-1.72 (m, 3H), 1.72-1.44 (m, 9H), 1.43 (d, J = 7.1 Hz, 3H), 1.41-1.30 (m, 1H), 1.29-1.14 (m, 1H), 0.90-0.81 (m, 1H), 0.76-0.57 (m, 2H), 0.52-0.43 (m, 1H). |
| 445 | 624.3 | 1H NMR (400 MHz, DMSO-d6) δ 8.11 (d, J = 8.1 Hz, 1H), 8.08 (d, J = 7.9 Hz, 1H), 8.05-7.70 (m, 3H), 7.38 (s, 1H), 7.25 (d, J = 8.1 Hz, 1H), 7.06 (s, 1H), 6.90 (s, 1H), 5.27 (p, J = 7.0 Hz, 1H), 5.07-4.91 (m, 0.5H), 4.88-4.76 (m, 1H), 4.49-4.37 (m, 1H), 4.13 (s, 3H), 4.29-3.68 (m, 1.5H), 3.99 (s, 3H), 3.46-2.68 (m, 2H), 2.32-2.20 (m, 1H), 2.07-1.92 (m, 2H), 1.90-1.70 (m, 5H), 1.69-1.50 (m, 4H), 1.45 (d, J = 6.9 Hz, 3H), 1.48-1.37 (m, 2H), 1.30-1.17 (m, 2H), 1.16-0.98 (m, 2H), 0.98-0.89 (m, 1H), 0.65-0.56 (m, 1H), 0.52-0.42 (m, 1H). |
| 446 | 701.4 | 1H NMR (400 MHz, DMSO-d6) δ 9.54 (d, J = 7.5 Hz, 1H), 8.52 (s, 1H), 8.39 (d, J = 1.1 Hz, 1H), 8.17 (d, J = 8.0 Hz, 1H), 8.08-7.65 (m, 3H), 7.41-7.31 (m, 2H), 7.19 (s, 1H), 6.90 (s, 1H), 5.38 (p, J = 7.4 Hz, 1H), 5.32-5.23 (m, 1H), 5.17 (dd, J = 31.4, 14.6 Hz, 1H), 5.05-4.43 (m, 1H), 4.31-4.18 (m, 1H), 4.11 (s, 3H), 4.00 (s, 3H), 3.50-3.05 (m, 1H), 2.85-2.52 (m, 1H), 2.45 (dd, J = 13.2, 4.3 Hz, 1H), 2.15 (td, J = 12.6, 3.7 Hz, 1H), 2.03-1.92 (m, 1H), 1.90-1.49 (m, 9H), 1.46 (d, J = 7.0 Hz, 3H), 1.27-0.99 (m, 1H). |
| 447 | 628.3 | 1H NMR (400 MHz, DMSO-d6) δ 8.36 (d, J = 7.6 Hz, 1H), 8.01 (d, J = 8.0 Hz, 1H), 7.96 (s, 2H), 7.73 (s, 1H), 7.37 (s, 1H), 7.19 (d, J = 8.1 Hz, 1H), 7.01 (s, 1H), 6.89 (s, 1H), 5.13 (p, J = 7.3 Hz, 1H),   5.04-4.91 (m, 0.5H),   4.66-4.48 (m, 3H),   4.21-4.11 (m, 0.5H),   4.11 (s, 3H), 3.98 (s, 3H),   3.80-3.60 (m, 0.5H),   3.44-3.21 (m, 0.5H), 3.18-3.02 (m, 0.5H), 2.84-2.69 (m, 0.5H),   2.05-1.15 (m, 19H), 1.09-0.88 (m, 2H). |
| 448 | 664.3 | 1H NMR (400 MHz, DMSO-d6) δ 8.57 (d, J = 9.6 Hz, 1H), 8.07 (d, J = 8.0 Hz, 1H), 7.96 (br s, 2H), 7.72 (br s, 1H), 7.39 (s, 1H), 7.25 (d, J = 8.0 Hz, 1H), 7.15 (s, 1H), 6.91 (s, 1H), 5.53 (t, J = 13.5 Hz, 1H), 5.28-5.13 (m, 2H),   5.04-4.91 (m, 0.5H),   4.58-4.49 (m, 1H),   4.21-4.11 (m, 0.5H),   4.10 (s, 3H), 3.99 (s, 3H),   3.80-3.60 (m, 0.5H), 3.44-3.21 (m, 0.5H), 3.18-3.02 (m, 0.5H), 2.84-2.69 (m, 0.5H), 2.42-1.37 (m, 17H), 1.28-0.90 (m, 2H). |
| 449 | 678.3 | 1H NMR (400 MHz, DMSO-d6) δ 8.60 (d, J = 9.6 Hz, 1H), 8.09 (d, J = 8.0 Hz, 1H), 7.98 (s, 2H), 7.79-7.58 (m, 2H), 7.37 (s, 1H), 7.34-7.17 (m, 2H), 5.82 (t, J = 13.7 Hz, 1H), 5.34-5.17 (m, 2H), 5.02-4.92 (m, 0.5H), 4.58-4.47 (m, 1H), 4.23-4.14 (m, 0.5H), 4.07-3.98 (m, 1H), 2.44-1.37 (m, 14H),  3.80-3.60 (m, 0.5H), 3.44-3.21 (m, 0.5H), 3.18-3.02 (m, 0.5H), 2.84-2.69 (m, 0.5H),   1.30-0.91 (m, 6H),   0.50-0.36 (m, 1H). |
| 450 | 642.3 | 1H NMR (400 MHz, DMSO-d6) δ 8.43 (d, J = 9.5 Hz, 1H), 8.01 (d, J = 8.0 Hz, 1H), 7.98 (s, 2H), 7.81-7.54 (m, 2H), 7.31-7.19 (m, 2H), 7.17 (d, J = 8.0 Hz, 1H), 5.26-5.13 (m, 1H), 5.03-4.95 (m, 0.5H), 4.89-4.78 (m, 2H), 4.59-4.44 (m, 1H), 4.22-4.11 (m, 0.5H), 4.03-3.95 (m, 1H), 3.80-3.61 (m, 0.5H), 3.43-3.21 (m, 0.5H), 3.19-3.02 (m, 0.5H), 2.84-2.70 (m, 0.5H), 2.31-2.20 (m, 1H), 2.08-1.01 (m, 20H), 1.00-0.80 (m, 2H), 0.67-0.56 (m, 1H). |
| 451 | 628.3 | 1H NMR (400 MHz, DMSO-d6) δ 8.41 (d, J = 9.5 Hz, 1H), 8.00 (d, J = 8.0 Hz, 1H), 7.97 (s, 2H), 7.74 (s, 1H), 7.37 (s, 1H), 7.16 (d, J = 8.1 Hz, 1H), 7.03 (s, 1H), 6.89 (s, 1H), 5.25-5.14 (m, 1H), 5.07-4.92 (m, 0.5H), 4.80-4.59 (m, 2H), 4.59-4.47 (m, 1H), 4.30-4.18 (m, 0.5H), 4.12 (s, 3H), 3.99 (s, 3H), 3.88-3.70 (m, 0.5H), 3.46-3.22 (m, 0.5H),   3.18-3.02 (m, 0.5H),   2.85-2.69 (m, 0.5H), 2.32-2.19 (m, 1H), 2.08-1.08 (m, 19H), 0.94 (td, J = 9.9, 6.0 Hz, 1H). |
| 452 | 713.2 | 1H NMR (400 MHz, DMSO-d6) δ 9.12 (d, J = 6.2 Hz, 1H), 8.12 (d, J = 8.1 Hz, 0.3H minor rotamer), 8.09 (d, J = 8.1 Hz, 0.7H major rotamer), 7.99 (brs, 2H), 7.82 (d, J = 8.0 Hz, 1H), 7.80-7.57 (m, 3H), 7.46-7.37 (m, 2H), 7.33-7.19 (m, 2H), 5.28-5.15 (m, 1H), 5.12-4.78 (m, 4H), 4.53 (brs, 1H), 4.26-4.12 (m, 1H), 2.88-2.61 (m, 2H), 2.46-2.29 (m, 3H), 2.08-1.34 (m, 9H), 1.55-1.46 (m, 3H), 1.30-1.05 (m, 2H), 0.63 (brs, 1H). |

TABLE 3-continued

| Example | ES/MS m/z [M + H]+ | 1H NMR |
|---|---|---|
| 453 | 710.2 | 1H NMR (400 MHz, DMSO-d6) δ 8.60 (d, J = 8.7 Hz, 1H), 8.17-8.05 (m, 1H), 7.98 (brs, 2H), 7.85-7.57 (m, 3H), 7.37 (s, 1H), 7.35-7.17 (m, 2H), 6.22 (td, J = 56.8, 3.7 Hz, 1H), 5.79 (t, J = 13.7 Hz, 0.7H major rotamer), 6.63 (t, J = 13.7 Hz, 0.3H minor rotamer), 5.28-5.15 (m, 1H), 5.14-5.01 (m, 1H), 4.98 (s, 0.3H minor rotamer), 4.53 (brs, 0.7H major rotamer), 4.33 (brs, 0.7H major rotamer), 4.18 (s, 0.3H minor rotamer), 3.73 (brs, 1H), 3.14 (brs, 1H) 2.75 (brs, 1H), 2.46-1.46 (m, 9H), 1.45 (d, J = 7.1 Hz, 3H), 1.41-1.18 (m, 2H), 0.95-0.58 (m, 4H), 0.58-0.48 (m, 2H). |
| 454 | 710.2 | 1H NMR (400 MHz, DMSO-d6) δ 8.58 (d, J = 9.0 Hz, 1H), 8.08 (d, J = 8.0 Hz, 1H), 7.99 (brs, 2H), 7.86-7.58 (m, 3H), 7.33 (brs, 1H), 7.30 (s, 1H), 7.24 (d, J = 8.1 Hz, 1H), 5.91 (t, J = 56 Hz, 1H), 5.63 (t, J = 13.7 Hz, 1H), 5.22 (dd, J = 27.5, 14.6 Hz, 1H), 5.14-5.06 (m, 1H), 4.98 (brs, 1H), 4.53 (brs, 1H), 4.40-4.19 (m, 1H), 3.73 (brs, 1H), 3.22-3.04 (m, 1H), 2.31-2.05 (m, 2H), 2.04-1.89 (m, 2H), 1.89-1.45 (m, 8H), 1.44 (d, J = 7.1 Hz, 3H), 1.39-1.18 (m, 2H), 0.94-0.84 (m, 1H), 0.76-0.60 (m, 1H), 0.59-0.47 (m, 2H). |
| 455 | 660.2 | 1H NMR (400 MHz, DMSO-d6) δ 8.59 (d, J = 8.8 Hz, 1H), 8.06 (d, J = 8.0 Hz, 1H), 7.99 (d, J = 5.5 Hz, 2H), 7.81 (d, J = 5.9 Hz, 0.4H minor rotamer), 7.73 (brs, 1H + 0.6H major rotamer), 7.67 (d, J = 8.2 Hz, 0.4H minor isomer) 7.65 (d, J = 9.5 Hz, 0.6H majo rotamer), 7.38 (s, 0.4H minor rotamer), 7.37 (s, 0.6H major rotamer), 7.23 (d, J = 8.1 Hz, 1H), 5.86 (t, J = 13.8 Hz, 1H), 5.18 (dd, J = 27.7, 14.6 Hz, 1H), 5.12-4.99 (m, 1H), 4.64 (brs, 0.6H major rotamer), 4.11-3.91 (m, 1H), 3.83 (brs, 1H), 3.40-3.20 (m, 1H), 3.09 (brs, 0.4H minor isomer), 2.84-2.72 (m, 1H), 2.29-1.92 (m, 5H), 1.86-1.49 (m, 7H), 1.44 (d, J = 7.0 Hz, 3H), 1.41-1.18 (m, 2H), 1.15-0.94 (m, 2H), 0.91-0.76 (m, 1H), 0.72-0.55 (m, 1H), 0.57-0.39 (m, 3H). |
| 456 | 713.2 | 1H NMR (400 MHz, DMSO-d6) δ 9.16-9.10 (m, 1H), 8.11 (dd, J = 8.1, 1.3 Hz, 1H), 8.02 (d, J = 5.5 Hz, 2H), 7.82 (d, J = 8.1 Hz, 1H), 7.78 (d, J = 5.5 Hz, 1H), 7.63 (d, J = 4.8 Hz, 0.4H minor rotamer), 7.56 (brs, 0.6H major rotamer), 7.41 (d, J = 8.0 Hz, 1H), 7.34 (s, 0.4H minor rotamer), 7.33 (s, 0.6H major rotamer), 7.28 (d, J = 8.1 Hz, 0.4H minor rotamer), 7.27 (d, J = 8.1 Hz, 0.6H major rotamer), 5.25-5.16 (m, 1H), 5.06 (s, 0.4H minor rotamer), 4.99-4.85 (m, 1H), 4.84-4.74 (m, 1H), 4.62 (dd, J = 13.2, 6.1 Hz, 0.6H major rotamer), 4.11-3.94 (m, 2H), 3.39 (brs, 0.6H major rotamer), 3.26 (brs, 0.4H minor rotamer), 3.07 (t, J = 12.0 Hz, 0.4H minor rotamer), 2.78 (t, J = 12.2 Hz, 0.6H major rotamer), 2.72-2.57 (m, 1H), 2.47-2.27 (m, 2H), 2.07-1.91 (m, 2H), 1.88-1.36 (m, 8H), 1.50 (d, J = 7.0 Hz, 3H), 1.33-1.01 (m, 4H), 0.65-0.39 (m, 2H). |
| 457 | 711.3 | 1H NMR (400 MHz, DMSO-d6) δ 9.35 (s, 1.3H major rotamer), 9.34 (s, 0.7H minor rotamer), 8.19 (d, J = 8.2 Hz, 0.7H minor rotamer), 8.14 (d, J = 8.0 Hz, 1.3H major rotamer), 7.97 (brs, 1H), 7.94-7.87 (m, 2H), 7.79-7.66 (m, 2H), 7.68-7.56 (m, 1H), 7.34 (s, 0.65H major rotamer), 7.32 (s, 0.35H minor rotamer), 7.32-7.17 (m, 1H), 5.61-5.48 (m, 1H), 5.08-4.91 (m, 1H), 4.90-4.70 (m, 1H), 4.53 (brs, 0.65H major rotamer), 4.18 (brs, 0.65H major rotamer), 4.07-3.98 (m, 1H), 3.74 (brs, 2H), 3.16 (brs, 0.35H minor rotamer), 2.61 (brs, 0.35H minor rotamer), 2.59-2.53 (m, 2H), 2.47-2.37 (m, 1H), 2.03-1.48 (m, 9H), 1.54 (d, J = 7.0 Hz, 3H), 1.39-0.94 (m, 5H), 0.65-0.42 (m, 2H). |
| 458 | 607.7 | 1H NMR (400 MHz, DMSO-d6) δ 8.48 (brs, 1H), 8.46 (d, J = 8.7 Hz, 1H), 8.24 (brs, 0.4H minor rotamer), 8.15 (brs, 0.6H major rotamer), 8.04-7.94 (m, 1H), 8.02 (d, J = 8.0 Hz, 2H), 7.97 (s, 1H), 7.73 (bs, 1H), 7.38 (s, 1H), 7.15 (d, J = 8.1 Hz, 1H), 5.08-4.97 (m, 1H), 4.96-4.91 (m, 2H), 4.57 (brs, 0.4H minor rotamer), 4.18 (brs, 0.6H major rotamer), 3.89-3.77 (m, 1H), 3.46-3.25 (m, 2H), 3.23-3.08 (m, 0.4H minor rotamer), 2.86-2.75 (m, 0.6H major rotamer), 2.05-1.32 (m, 12H), 1.45 (d, J = 7.1 Hz, 3H), 1.32-0.99 (m, 4H), 0.91-0.59 (m, 4H), 0.53-0.44 (m, 1H). |
| 459 | 716.2 | 1H NMR (400 MHz, DMSO-d6) δ 8.81 (brs, 0.2H minor rotamer), 8.61 (d, J = 8.6 Hz, 0.2H mimor rotamer), 8.39 (d, J = 7.4 Hz, 0.8H major rotamer), 8.21 (d, J = 7.5 Hz, 0.2H minor rotamer), 8.12 (d, J = 8.0 Hz, 1H), 7.98 (brs, 1H), 7.75 (brs, 1H), 7.56 (brs, 0.2H minor rotamer), 7.36 (brs, 0.8H major rotamer), 7.29 (d, J = 8.3 Hz, 0.8H major rotamer), 7.16 (s, 0.8H major rotamer), 6.90 (s, 0.8H major rotamer), 5.75 (brs, 0.2H minor rotamer), 5.44-5.08 (m, 3H), 4.99 (brs, 0.2H minor rotamer), 4.53 (brs, 0.8H major rotamer), 4.24 (brs, 0.8H major rotamer), 4.10 (s, 3H), 3.99 (s, 3H), 3.80 (brs, 0.2H minor rotamer), 2.76 (brs, 0.8H major rotamer), 2.27-1.37 (m, 16H), 1.45 (d, J = 15.5 Hz, 3H), 1.36-0.92 (m, 4H). |
| 460 | 664.2 | 1H NMR (400 MHz, DMSO-d6) δ 8.13 (d, J = 8.0 Hz, 1H), 8.09 (d, J = 9.6 Hz, 1H), 7.99 (brs, 2H), 7.75 (brs, 1H), 7.40 (brs, 1H), 7.30 (d, J = 8.2 Hz, 1H), 7.18 (s, 1H), 6.91 (brs, 1H), 5.52-5.23 (m, 3H), 4.99 (brs, 0.35H minor rotamer), 4.53 (s, 0.65H major rotamer), 4.36-4.09 (m, 2H), |

TABLE 3-continued

| Example | ES/MS m/z [M + H]+ | ¹H NMR |
|---|---|---|
| | | 4.09 (s, 3H), 3.99 (s, 3H), 3.47-3.06 (m, 3H), 2.86-2.54 (m, 2H), 2.04-1.50 (m, 7H), 1.45 (d, J = 6.8 Hz, 3H), 1.34 (s, 3H), 1.20 (s, 3H), 1.17-0.97 (m, 1H). |
| 461 | 697.2 | 1H NMR (400 MHz, DMSO-d6) δ 9.24 (d, J = 6.6 Hz, 1H), 8.18 (s, 1H), 8.15-8.03 (m, 2H), 7.97 (brs, 2H), 7.91 (d, J = 8.3 Hz, 1H), 7.80-7.72 (m, 1H), 7.72 (brs, 1H), 7.65-7.58 (m, 1H), 7.37 (brs, 1H), 7.30 (d, J = 8.1 Hz, 1H), 7.10 (s, 1H), 6.90 (brs, 1H), 5.32-5.18 (m, 1H), 4.99 (brs, 0.35H minor rotamer), 4.88 (t, J = 12.8 Hz, 0.65H major rotamer), 4.72-4.56 (m, 0.65H major rotamer), 4.52 (brs, 0.35H minor rotamer), 4.23 (brs, 1H), 4.13 (s, 3H), 4.00 (s, 3H), 3.47-3.05 (m, 3H), 2.86-2.65 (m, 2H), 2.09-1.58 (m, 8H), 1.55 (d, J = 7.0 Hz, 3H), 1.53-1.34 (m, 1H), 1.33-1.13 (m, 2H), 0.60-0.42 (m, 1H). |
| 462 | 639.4 | 1H NMR (400 MHz, DMSO-d6) δ 8.05 (d, J = 7.6 Hz, 1H), 7.97 (brs, 2H), 7.74 (brs, 1H), 7.61 (d, J = 8.4 Hz, 1H), 7.58 (brs, 1H), 7.36 (s, 1H), 7.22 (s, 1H), 7.20 (brs, 1H) 7.07 (d, J = 8.3 Hz, 1H), 5.12-5.00 (m, 1H), 4.98 (brs, 0.35H minor rotamer), 4.88 (brs, 1H), 4.52 (brs, 0.65H major rotamer), 4.32-4.14 (m, 2H), 4.02-3.92 (m, 1H), 3.44-2.98 (m, 3H), 2.90-2.63 (m, 1H), 2.08 (t, J = 12.7 Hz, 1H), 2.03-1.50 (m, 7H), 1.46 (d, J = 7.3 Hz, 3H), 1.44-1.30 (m, 3H), 1.24 (s, 3H), 1.20-1.00 (m, 4H), 0.94 (s, 3H), 0.91 (brs, 1H), 0.56 (s, 1H). |
| 463 | 663.2 | 1H NMR (400 MHz, DMSO-d6) δ 8.74 (d, J = 9.0 Hz, 0.2H minor rotamer), 8.68 (d, J = 9.0 Hz, 0.8H major rotamer), 7.97 (brs, 2H), 7.82-7.62 (m, 2H), 7.44 (d, J = 10.4 Hz, 1H), 7.38 (brs, 1H), 7.10 (s, 1H), 6.90 (brs, 1H), 5.75-5.64 (m, 1H), 5.26-5.09 (m, 1H), 4.99 (brs, 0.2H minor rotamer), 4.73 (dd, J = 28.8, 15.5 Hz, 0.8H major rotamer), 4.53 (brs, 0.2H minor rotamer), 4.24 (brs, 0.8H major rotamer), 4.07 (s, 3H), 3.99 (s, 3H), 3.53-2.99 (m, 3H), 2.92-2.57 (m, 1H), 2.07-1.49 (m, 11H), 1.45 (d, J = 7.1 Hz, 3H), 1.31-1.21 (m, 1H), 1.02-0.69 (m, 2H), 0.68-0.53 (m, 2H). |
| 464 | 677.3 | 1H NMR (400 MHz, DMSO-d6) δ 8.71 (d, J = 8.9 Hz, 1H), 7.97 (brs, 2H), 7.75 (d, J = 6.2 Hz, 1H), 7.72 (brs, 1H), 7.69-7.65 (m, 1H), 7.45 (d, J = 10.2 Hz, 1H), 7.34 (s, 1H), 7.32-7.15 (m, 1H), 6.01 (t, J = 14.0 Hz, 1H), 5.25-5.11 (m, 1H), 4.97 (brs, 0.35H minor rotamer), 4.77 (dd, J = 28.8, 15.5 Hz, 1H), 4.52 (brs, 0.35H minor rotamer), 4.20 (brs, 0.65H major rotamer), 4.00 (brs, 1H), 3.74 (brs, 0.65H major rotamer), 3.29-2.71 (m, 2H), 2.22-1.48 (m, 11H), 1.45 (d, J = 7.1 Hz, 3H), 1.32-1.18 (m, 2H), 1.11-0.73 (m, 5H), 0.73-0.55 (m, 2H), 0.52-0.34 (m, 1H). |
| 465 | 625.4 | 1H NMR (400 MHz, DMSO-d6) δ 8.04 (d, J = 7.9 Hz, 1H), 7.98 (brs, 2H), 7.75 (s, 1H), 7.61 (d, J = 8.3 Hz, 1H), 7.37 (brs, 1H), 7.35 (s, 1H), 7.07 (d, J = 8.3 Hz, 1H), 6.99 (s, 1H), 6.88 (s, 1H), 5.13-5.00 (m, 1H), 4.99 (brs, 0.35H minor rotamer), 4.71-4.44 (m, 2H), 4.35-4.13 (m, 1H + 0.65H major rotamer), 4.10 (s, 3H), 3.99 (s, 3H), 3.49-2.63 (m, 2H), 2.16-1.53 (m, 10H), 1.52-1.31 (m, 3H), 1.45 (d, J = 7.2 Hz, 3H), 1.19 (s, 3H), 1.08-0.98 (m, 3H), 0.94 (s, 3H). |
| 466 | 678.3 | 1H NMR (400 MHz, DMSO-d6) δ 8.59 (d, J = 8.7 Hz, 1H), 8.08 (d, J = 7.8 Hz, 0.35H minor rotamer), 8.08 (d, J = 7.8 Hz, 0.65H major rotamer), 8.00 (d, J = 5.5 Hz, 1H), 7.99 (brs, 1H), 7.74 (brs, 1H), 7.66 (d, J = 4.6 Hz, 0.35H minor rotamer), 7.58 (brs, 0.65H major rotamer), 7.39 (s, 0.35H minor rotamer), 7.38 (s, 0.65H major rotamer), 7.25 (d, J = 8.1 Hz, 0.35H minor rotamer), 7.25 (d, J = 8.1 Hz, 0.65H major rotamer), 5.81 (t, J = 13.9 Hz, 1H), 5.20 (dd, J = 27.7, 14.6 Hz, 1H), 5.12-5.00 (m, 1H), 4.69-4.57 (m, 1H), 4.04 (brs, 2H), 3.35-2.99 (m, 2H), 2.82-2.67 (m, 1H), 2.23-1.50 (m, 10H), 1.44 (d, J = 7.0 Hz, 3H), 1.38-0.98 (m, 4H), 0.93-0.80 (m, 3H), 0.74-0.41 (m, 4H). |
| 467 | 678.3 | 1H NMR (400 MHz, DMSO-d6) δ 8.58 (d, J = 8.8 Hz, 1H), 8.08 (d, J = 8.3 Hz, 0.35H minor rotamer), 8.05 (d, J = 8.3 Hz, 0.65H major rotamer), 8.03-7.92 (m, 2H), 7.88-7.56 (m, 2H), 7.49 (s, 0.65H major rotamer), 7.43 (s, 0.35H minor rotamer), 7.29 (brs, 1H), 7.24 (d, J = 8.3 Hz, 1H), 6.10 (brs, 1H), 5.27-4.91 (m, 3H), 4.87 (s, 0.35H minor rotamer), 4.54 (brs, 0.65H major rotamer), 4.28-4.06 (m, 2H), 3.48-3.06 (m, 3H), 2.86-2.66 (m, 1H), 2.42-2.04 (m, 2H), 2.03-1.47 (m, 9H), 1.44 (d, J = 7.1 Hz, 3H), 1.36-1.20 (m, 1H), 0.84 (brs, 1H), 0.73-0.59 (m, 1H), 0.56-0.45 (m, 2H). |
| 468 | 678.3 | 1H NMR (400 MHz, DMSO-d6) δ 8.60 (d, J = 8.8 Hz, 1H), 8.08 (d, J = 7.6 Hz, 1H), 7.98 (brs, 2H), 7.85-7.59 (m, 2H), 7.40-7.18 (m, 3H), 5.81 (t, J = 13.7 Hz, 1H), 5.33-5.02 (m, 3H + 0.35H minor rotamer), 4.97 (brs, 0.35H minor rotamer), 4.53 (brs, 0.65H major rotamer), 4.18 (brs, 0.65H major rotamer), 4.13-4.01 (m, 1H), 3.72 (brs, 2H), 3.34-3.09 (m, 1H), 2.79 (brs, 1H), 2.31-1.48 (m, 10H), 1.45 (d, J = 7.2 Hz, 3H), 1.39-1.20 (m, 1H), 0.91-0.73 (m, 2H), 0.73-0.57 (m, 1H), 0.58-0.47 (m, 2H). |
| 469 | 669.5 | 1H NMR (400 MHz, DMSO-d6) δ 9.11 (d, J = 7.2 Hz, 1H), 8.12 (d, J = 8.0 Hz, 1H), 8.09 (s, 2H), 7.84 (s, 1H), 7.82 (d, J = 8.0 Hz, 1H), 7.72-7.55 (m, 1H), 7.41 (d, J = 8.0 Hz, 1H), 7.28 (d, J = 8.1 Hz, 1H), 7.26 (s, 1H), 7.16 (s, 1H), 5.23 (p, J = 7.0 Hz, 1H), 5.10-4.92 (m, 0H), 4.87 (ddd, J = 14.6, 10.8, 4.7 Hz, 1H), 4.71-4.60 (m, 1H), 4.60-4.45 (m, 0H), 4.22- |

TABLE 3-continued

| Example | ES/MS m/z [M + H]+ | ¹H NMR |
|---|---|---|
| | | 4.14 (m, 1H), 4.11 (s, 3H), 3.87-3.65 (m, 0H), 3.47-3.24 (m, 1H), 3.24-3.03 (m, 0H), 2.88-2.72 (m, 0H), 2.70-2.59 (m, 1H), 2.46-2.29 (m, 2H), 2.07-1.94 (m, 1H), 1.91-1.73 (m, 1H), 1.71-1.53 (m, 7H), 1.50 (d, J = 7.1 Hz, 3H), 1.46-1.30 (m, 1H), 1.31-1.13 (m, 1H), 0.73-0.51 (m, 1H). |
| 470 | 690.3 | 1H NMR (400 MHz, DMSO-d6) δ 8.59 (d, J = 8.8 Hz, 1H), 8.12-8.03 (m, 1H), 7.97 (s, 2H), 7.71 (s, 2H), 7.62 (s, 1H), 7.42 (s, 1H), 7.36-7.17 (m, 3H), 5.79 (t, J = 13.8 Hz, 1H), 5.19 (dd, J = 28.0, 14.6 Hz, 1H), 5.11- 5.03 (m, 1H), 5.01-4.86 (m, 0.4H), 4.63-4.39 (m, 0.6H), 4.29-4.13 (m, 1H), 3.74 (s, 3H), 3.58-3.55 (m, 3H), 3.44-3.34 (m, 0.5H), 2.87-2.70 (m, 0.5H), 2.28-2.03 (m, 1H), 1.96 (d, J = 12.2 Hz, 3H), 1.90-1.73 (m, 1H), 1.71-1.60 (m, 2H), 1.55 (q, J = 6.1, 5.5 Hz, 1H), 1.45 (t, J = 7.4 Hz, 3H), 1.40-1.14 (m, 3H), 1.01-0.81 (m, 1H), 0.74-0.46 (m, 5H). |
| 471 | 676.5 | 1H NMR (400 MHz, DMSO-d6) δ 8.60 (d, J = 8.7 Hz, 1H), 8.08 (d, J = 8.0 Hz, 1H), 7.97 (s, 2H), 7.80 (s, 0.4H), 7.73 (s, 1.6H), 7.48 (s, 0.5H), 7.42 (s, 0.5H), 7.36 (s, 1H), 7.25 (d, J = 8.0 Hz, 1H), 5.87 (t, J = 13.7 Hz, 1H), 5.20 (dd, J = 28.0, 14.6 Hz, 1H), 5.07 (p, 1H), 5.01-4.90 (m, 0.4H), 4.61-4.42 (m, 0.5H), 4.26-4.14 (m, 0.6H), 4.10-3.99 (m, 1H), 3.46-3.34 (m, 0.3H), 3.34-3.22 (m, 1H), 3.19 (m, 0.3H), 2.86-2.70 (m, 0.5H), 2.28-2.03 (m, 2H), 2.05-1.92 (m, 3H), 1.91-1.75 (m, 1H), 1.72-1.59 (m, 3H), 1.59-1.50 (m, 1H), 1.44 (d, J = 7.0 Hz, 3H), 1.32 (d, J = 17.5 Hz, 3H), 1.13-0.90 (m, 2H), 0.89-0.79 (m, 1H), 0.75-0.60 (m, 1H), 0.58-0.45 (m, 3H). |
| 472 | 695.4 | 1H NMR (400 MHz, DMSO-d6) δ 9.13 (d, J = 7.0 Hz, 1H), 8.11 (d, J = 8.1 Hz, 1H), 7.96 (s, 2H), 7.82 (d, J = 8.0 Hz, 1H), 7.79-7.52 (m, 1H), 7.42 (d, J = 8.0 Hz, 1H), 7.32 (s, 1H), 7.28 (t, J = 7.6 Hz, 1H), 7.35-7.11 (m, 1H), 5.21 (p, J = 6.9 Hz, 1H), 5.05-4.70 (m, 2H), 4.64-4.43 (m, 0.5H, rotamer), 4.26-4.13 (m, 0.5H, rotamer), 4.09-3.93 (m, 1H), 3.64-3.16 (m, 4H), 2.71-2.59 (m, 1H), 2.41-2.25 (m, 1H), 2.06-1.90 (m, 1H), 1.90-1.72 (m, 1H), 1.73-1.57 (m, 4H), 1.60-1.29 (m, 1H), 1.50 (d, J = 7.0 Hz, 3H), 1.29-1.15 (m, 2H), 1.15-0.89 (m, 2H), 0.68-0.37 (m, 2H). |
| 473 | 714.2 | 1H NMR (400 MHz, DMSO-d6) δ 9.11 (d, J = 7.1 Hz, 1H), 8.12 (dd, J = 8.1, 3.6 Hz, 1H), 7.97 (s, 1H), 7.87-7.81 (m, 1H), 7.42 (d, J = 8.1 Hz, 1H), 7.38 (s, 1H), 7.28 (d, J = 8.1 Hz, 1H), 5.23 (p, J = 7.2 Hz, 1H), 4.98 (s, 1H), 4.90 (t, J = 10.4 Hz, 1H), 4.79 (s, 1H), 4.66 (s, 1H), 4.63-4.46 (m, 2H), 4.15 (s, 1H), 3.73 (s, 1H), 3.14 (m, 1H) 2.76 (s, 1H), 2.72-2.61 (m, 1H), 2.46-2.28 (m, 3H), 2.02-1.89 (m, 2H), 1.84 (d, J = 10.0 Hz, 2H), 1.76 (s, 1H), 1.67 (s, 2H), 1.50 (dd, J = 7.1, 4.1 Hz, 3H), 1.24 (s, 1H), 0.85 (s, 1H), 0.66 (s, 1H), 0.53 (m, 1H). |
| 474 | 729.3 | 1H NMR (400 MHz, DMSO-d6) δ 9.27 (d, J = 7.0 Hz, 1H), 8.12 (d, J = 8.0 Hz, 1H), 8.04 (d, J = 7.8 Hz, 1H), 7.96 (s, 2H), 7.81 (d, J = 7.9 Hz, 1H), 7.73 (s, 1H), 7.59 (s, 1H), 7.36-7.26 (m, 2H), 5.23 (p, J = 6.9 Hz, 1H), 5.01-4.88 (m, 2H), 4.85 (s, 1H), 4.52 (s, 1H), 4.18 (s, 1H), 4.02 (p, J = 6.0, 5.5 Hz, 1H), 3.76 (m, 1H) 3.15 (d, J = 15.9 Hz, 2H), 2.76 (s, 1H), 2.68 (m, J = 5.2, 2.6 Hz, 1H), 1.95 (d, J = 10.5 Hz, 2H), 1.76 (s, 2H), 1.65 (s, 2H), 1.51 (d, J = 7.0 Hz, 4H), 1.31-1.15 (m, 2H), 1.08 (s, 3H), 0.59-0.38 (m, 2H). |
| 475 | 660.2 | 1H NMR (400 MHz, DMSO-d6) δ 8.14 (d, J = 8.1 Hz, 1H), 7.97 (d, J = 8.5 Hz, 1H), 7.74 (s, 1H), 7.38 (s, 1H), 7.29 (d, J = 8.2 Hz, 1H), 7.16 (s, 1H), 6.90 (s, 1H), 5.52 (q, J = 16.1 Hz, 1H), 5.31 (p, J = 7.1 Hz, 1H), 5.20 (q, J = 12.9, 12.1 Hz, 1H), 4.99 (s, 1H), 4.53 (s, 1H), 4.26 (d, J = 14.7 Hz, 1H), 4.10 (s, 3H), 4.00 (s, 3H), 3.92 (s, 1H), 3.20-3.05 (m, 1H), 2.77 (s, 1H), 2.12-1.89 (m, 3H), 1.79 (d, J = 19.8 Hz, 3H), 1.58 (s, 3H), 1.44 (d, J = 7.0 Hz, 3H), 1.35-1.18 (m, 3H), 1.03 (m, J = 9.6, 6.2, 3.5 Hz, 1H), 0.96 (m, J = 9.4, 4.5 Hz, 1H), 0.59 (m, J = 6.1, 3.7 Hz, 1H), 0.42 (m, J = 9.4, 6.1, 3.3 Hz, 1H). |
| 476 | 711.3 | 1H NMR (400 MHz, DMSO-d6) δ 9.29 (d, J = 6.6 Hz, 1H), 8.43 (s, 1H), 8.10 (dd, J = 20.3, 8.1 Hz, 2H), 7.95 (d, J = 8.5 Hz, 2H), 7.80 (t, J = 7.7 Hz, 1H), 7.74 (s, 1H), 7.64 (t, J = 7.5 Hz, 1H), 7.59 (s, 1H), 7.37-7.26 (m, 2H), 7.24 (s, 1H), 5.22 (p, J = 6.9 Hz, 1H), 5.02-4.79 (m, 2H), 4.52 (s, 1H), 4.18 (s, 1H), 4.04 (p, J = 10.6, 5.6, 4.8 Hz, 2H), 2.92 (dd, J = 12.8, 8.0 Hz, 2H), 2.59-2.52 (m, 2H), 1.95 (d, J = 11.3 Hz, 2H), 1.79 (d, J = 20.7 Hz, 2H), 1.65 (s, 2H), 1.55 (d, J = 7.1 Hz, 3H), 1.47 (d, J = 7.3 Hz, 2H), 1.37 (d, J = 10.3 Hz, 2H), 1.23 (d, J = 8.5 Hz, 2H), 1.09 (s, 2H), 0.50 (d, J = 34.9 Hz, 2H). |
| 477 | 678.3 | 1H NMR (400 MHz, DMSO-d6) δ 8.59 (d, J = 8.8 Hz, 1H), 8.10 (d, J = 8.0 Hz, 1H), 7.96 (s, 2H), 7.67 (d, J = 31.6 Hz, 2H), 7.43 (s, 1H), 7.26 (d, J = 8.1 Hz, 1H), 5.77 (t, J = 13.9 Hz, 1H), 5.23 (dd, J = 27.4, 14.6 Hz, 1H), 5.14-5.03 (m, 1H), 4.97 (s, 1H), 4.60 (t, J = 14.7 Hz, 1H), 4.46 (s, 1H), 4.30 (d, J = 6.2 Hz, 1H), 4.16 (s, 1H), 2.77 (s, 1H), 2.15 (m, J = 30.7, 27.6, 15.2 Hz, 3H), 1.95 (q, J = 12.7, 9.6 Hz, 3H), 1.76 (s, 2H), 1.62 (d, J = 13.4 Hz, 3H), 1.55 (m, J = 8.2, 4.5 Hz, 2H), 1.45 (d, J = 7.1 Hz, 3H), 1.38 (d, J = 12.7 Hz, 2H), 0.87 (p, J = 4.0 Hz, 1H), 0.66 (d, J = 10.9 Hz, 1H), 0.60 (d, J = 9.0 Hz, 1H), 0.51 (m, J = 6.9, 5.8, 3.6 Hz, 1H). |

TABLE 3-continued

| Example | ES/MS m/z [M + H]+ | ¹H NMR |
|---|---|---|
| 478 | 729.2 | 1H NMR (400 MHz, DMSO-d6) δ 9.39 (d, J = 8.0 Hz, 1H), 8.64 (d, J = 5.0 Hz, 1H), 8.11 (d, J = 8.0 Hz, 1H), 7.98 (s, 1H), 7.74 (s, 1H), 7.63 (d, J = 5.0 Hz, 1H), 7.37-7.17 (m, 3H), 5.41 (t, J = 7.4 Hz, 1H), 4.96 (t, J = 11.4 Hz, 1H), 4.85 (d, J = 13.0 Hz, 1H), 4.52 (s, 1H), 4.18 (s, 1H), 4.02 (t, J = 6.5 Hz, 1H), 2.61 (d, J = 10.7 Hz, 1H), 2.45-2.35 (m, 2H), 2.15 (t, J = 12.1 Hz, 2H), 1.94 (d, J = 22.3 Hz, 2H), 1.79 (d, J = 21.7 Hz, 2H), 1.58 (d, J = 59.5 Hz, 3H), 1.47 (d, J = 7.1 Hz, 3H), 1.39-1.13 (m, 4H), 1.08 (s, 3H), 0.45 (s, 2H). |
| 479 | 678.3 | 1H NMR (400 MHz, DMSO-d6) δ 8.59 (d, J = 8.7 Hz, 1H), 8.09 (d, J = 8.0 Hz, 1H), 7.98 (s, 1H), 7.69 (d, J = 44.5 Hz, 2H), 7.43 (s, 1H), 7.25 (d, J = 8.1 Hz, 1H), 5.78 (t, J = 14.1 Hz, 1H), 5.41 (s, 1H), 5.19 (dd, J = 27.7, 14.6 Hz, 1H), 5.12-5.01 (m, 1H), 4.98 (s, 1H), 4.62-4.45 (m, 2H), 4.19 (s, 1H), 2.77 (s, 1H), 2.19-2.03 (m, 2H), 2.03-1.91 (m, 2H), 1.77 (d, J = 19.9 Hz, 3H), 1.64 (d, J = 14.7 Hz, 3H), 1.54 (q, J = 5.3 Hz, 2H), 1.44 (d, J = 7.0 Hz, 3H), 1.40-1.26 (m, 2H), 0.85 (q, J = 7.1, 6.1 Hz, 1H), 0.77 (m, J = 13.7, 6.5 Hz, 1H), 0.65 (d, J = 11.4 Hz, 1H), 0.56-0.44 (m, 2H). |
| 480 | 741.3 | 1H NMR (400 MHz, DMSO-d6) δ 8.38 (d, J = 7.2 Hz, 1H), 8.08 (d, J = 8.1 Hz, 1H), 7.99 (t, J = 7.7 Hz, 1H), 7.98 (br s, 2H), 7.75 (br s, 1H), 7.61-7.57 (m, 2H), 7.27 (s, 1H), 7.22 (d, J = 8.1 Hz, 1H), 5.10 (p, J = 7.0 Hz, 1H), 5.03-4.85 (m, 1.5H), 4.63 (br s, 1H), 4.53 (s, 0.5H), 4.18 (br s, 0.5H), 4.04-3.96 (m, 1H), 3.38 (br s, 1H), 2.87-2.64 (m, 2H), 2.24-1.35 (m, 6H), 1.47 (d, J = 7.1 Hz, 3H), 1.35-1.01 (m, 3H), 0.92 (brs, 1H), 0.64 (br s, 1H). |
| 481 | 741.2 | 1H NMR (400 MHz, DMSO-d6) δ 8.84-8.78 (m, 1H), 8.09 (d, J = 8.1 Hz, 1H), 7.98 (t, J = 7.8 Hz, 1H), 8.03-7.51 (m, 3H), 7.64 (d, J = 7.7 Hz, 1H), 7.57 (d, J = 7.9 Hz, 1H), 7.29 (s, 1H), 7.31-7.18 (m, 1H), 7.24 (d, J = 8.1 Hz, 1H), 5.27 (p, J = 7.3 Hz, 1H), 4.95 (dt, J = 14.4, 7.6 Hz, 1H), 4.83-4.73 (m, 1H), 4.52 (br s, 0.5H), 4.18 (br s, 0.5H), 4.05-3.96 (m, 1H), 3.16 (br s, 0.5H), 2.76 (br s, 0.5H), 2.12-1.44 (m, 4H), 1.55 (d, J = 7.1 Hz, 3H), 1.43-1.02 (m, 3H), 0.95 (br s, 1H), 0.81 (br s, 1H), 0.56 (br s, 1H). |
| 482 | 626.3 | 1H NMR (400 MHz, DMSO-d6) δ 8.45 (d, J = 8.5 Hz, 1H), 8.00 (d, J = 8.0 Hz, 1H), 8.03-7.55 (m, 3H), 7.25 (s, 1H), 7.30-7.19 (m, 1H), 7.14 (d, J = 8.1 Hz, 1H), 5.00 (p, J = 7.1 Hz, 1H), 4.52 (br s, 0.5H), 4.17 (brs, 0.5H), 4.02-3.96 (m, 1H), 3.74 (br s, 0.3H), 3.36 (br s, 0.7H), 3.12 (br s, 0.3H), 2.76 (br s, 0.7H), 2.02-1.46 (m, 7H), 1.44 (d, J = 7.1 Hz, 3H), 1.40-0.82 (m, 4H), 0.78-0.53 (m, 3H), 0.53-0.44 (m, 1H). |
| 483 | 698.3 | 1H NMR (400 MHz, DMSO-d6) δ 9.33 (d, J = 7.2 Hz, 1H), 8.63 (d, J = 2.6 Hz, 1H), 8.54 (d, J = 2.5 Hz, 1H), 8.19 (d, J = 8.0 Hz, 1H), 7.96 (s, 2H), 7.81-7.56 (m, 2H), 7.41-7.36 (m, 2H), 7.35-7.18 (m, 1H), 5.57-5.45 (m, 1H), 5.37-5.15 (m, 2H), 4.96 (br s, 0.3H), 4.51 (br s, 0.7H), 4.18 (br s, 0.7H), 4.07-3.99 (m, 1H), 3.75 (br s, 0.3H), 3.44-3.07 (m, 2H), 2.83-2.61 (m, 2H), 2.02-1.51 (m, 8H), 1.49 (d, J = 7.0 Hz, 3H), 1.34-1.16 (m, 2H), 1.11-0.89 (m, 1H), 0.50 (br s, 1H). |
| 484 | 648.4 | 1H NMR (400 MHz, DMSO-d6) δ 9.23 (d, J = 7.0 Hz, 1H), 8.60 (d, J = 2.6 Hz, 1H), 8.49 (d, J = 2.6 Hz, 1H), 8.09 (d, J = 8.0 Hz, 1H), 7.99 br (s, 2H), 7.76 (br s, 1H), 7.36 (br s, 1H), 7.28 (d, J = 8.1 Hz, 1H), 7.09 (s, 1H), 6.90 (s, 1H), 5.24 (p, J = 7.0 Hz, 1H), 4.90-4.79 (m, 1H), 4.63-4.48 (m, 2H), 4.12 (s, 3H), 3.99 (s, 3H), 3.44-3.07 (m, 1H), 2.76 (br s, 1H), 2.46-2.30 (m, 1H), 2.01-1.92 (m, 1H), 1.88-1.32 (m, 8H), 1.51 (d, J = 7.0 Hz, 3H), 1.21 (br s, 1H), 0.61 (br s, 1H). |
| 485 | 662.4 | 1H NMR (400 MHz, DMSO-d6) δ 9.26 (d, J = 6.9 Hz, 1H), 8.60 (d, J = 2.6 Hz, 1H), 8.50 (d, J = 2.6 Hz, 1H), 8.11 (d, J = 8.1 Hz, 1H), 7.96 (br s, 2H), 7.80-7.54 (m, 1H), 7.32 (s, 2H), 7.28 (d, J = 8.1 Hz, 1H), 7.23 (br s, 1H), 5.23 (p, J = 7.0 Hz, 1H), 5.02-4.76 (m, 2H), 4.52 (br s, 0.5H), 4.17 (br s, 0.5H), 4.05-3.98 (m, 1H), 2.02-1.33 (m, 6H),  1.52 (d, J = 7.0 Hz, 3H),  1.28-1.14 (m, 2H), 1.14-0.95 (m, 3H), 0.66-0.42 (m, 2H). |
| 486 | 616.6 | 1H NMR (400 MHz, DMSO-d6) δ 8.76 (s, 2H), 8.70 (d, J = 7.9 Hz, 1H), 8.09 (d, J = 7.7 Hz, 1H), 8.07 (d, J = 8.2 Hz, 1H), 7.99 (d, J = 1.3 Hz, 1H), 7.35 (d, J = 1.2 Hz, 1H), 7.23 (d, J = 8.2 Hz, 1H), 7.11 (s, 1H), 4.96-4.87 (m, 1H), 4.87-4.70 (m, 3H), 4.50-4.38 (m, 1H), 4.15 (s, 3H), 4.03 (s, 3H), 3.51-3.33 (m, 2H), 3.14-3.02 (m, 2H), 3.02-2.92 (m, 1H), 2.41-2.30 (m, 1H), 2.30-2.18 (m, 1H), 2.04-1.86 (m, 4H), 1.67-1.51 (m, 4H), 1.49-1.33 (m, 3H), 1.32-1.15 (m, 3H), 0.84-0.71 (m, 1H), 0.68-0.53 (m, 1H). |
| 487 | 616.6 | 1H NMR (400 MHz, DMSO-d6) δ 8.77 (s, 2H), 8.70 (d, J = 8.0 Hz, 1H), 8.32 (d, J = 7.5 Hz, 1H), 8.05 (d, J = 8.0 Hz, 1H), 7.99 (d, J = 1.3 Hz, 1H), 7.35 (d, J = 1.3 Hz, 1H), 7.17 (d, J = 8.1 Hz, 1H), 7.11 (s, 1H), 5.10 (p, J = 7.1 Hz, 1H), 5.03-4.88 (m, 2H), 4.83-4.76 (m, 1H), 4.68-4.60 (m, 1H), 4.49-4.38 (m, 1H), 4.14 (s, 3H), 4.02 (s, 3H), 3.50-3.34 (m, 2H), 3.22-3.14 (m, 1H), 3.13-3.02 (m, 1H), 3.02-2.90 (m, 1H), 2.49-2.43 (m, 1H), 2.41-2.30 (m, 1H), 2.28-2.12 (m, 1H), 1.98-1.85 (m, 3H), 1.86-1.70 (m, 2H), 1.50-1.29 (m, 1H), 1.38 (d, J = 7.0 Hz, 3H), 1.11-0.68 (m, 4H), 0.15 (d, J = 13.2 Hz, 1H). |

TABLE 3-continued

| Example | ES/MS m/z [M + H]+ | ¹H NMR |
|---|---|---|
| 488 | 626.4 | 1H NMR (400 MHz, DMSO-d6) δ 8.21-8.07 (m, 2H), 8.09-7.98 (m, 2H), 7.89-7.79 (m, 2H), 7.63 (d, J = 9.9 Hz, 1H), 7.29 (s, 1H), 7.19 (d, J = 8.1 Hz, 1H), 5.11 (p, J = 7.1 Hz, 1H), 4.95-4.83 (m, 1H), 4.76-4.58 (m, 2H), 4.02-3.90 (m, 1H), 3.86-3.77 (m, 1H), 3.66 (s, 1H), 2.26 (s, 1H), 1.99-1.52 (m, 7H), 1.46 (d, J = 7.1 Hz, 3H), 1.42-1.28 (m, 4H), 1.29-1.22 (m, 1H), 1.22 (s, 3H), 1.18-0.99 (m, 3H), 0.95 (s, 3H), 0.93-0.84 (m, 1H), 0.62-0.49 (m, 1H). |
| 489 | 664.6 | 1H NMR (400 MHz, DMSO-d6) δ 8.43 (d, J = 8.6 Hz, 1H), 8.12-7.94 (m, 4H), 7.45 (s, 1H), 7.14 (d, J = 8.1 Hz, 1H), 7.02 (s, 1H), 6.94 (d, J = 1.2 Hz, 1H), 6.19 (tt, J = 55.0, 3.7 Hz, 1H), 5.01 (p, J = 7.3 Hz, 1H), 4.75-4.65 (m, 1H), 4.59 (d, J = 13.9 Hz, 1H), 4.12 (s, 3H), 3.99 (s, 3H), 3.95 (s, 1H), 3.90-3.78 (m, 2H), 3.60 (s, 1H), 3.44 (s, 1H), 2.02-1.91 (m, 1H), 1.90-1.75 (m, 2H), 1.72-1.49 (m, 5H), 1.43 (d, J = 7.1 Hz, 3H), 1.41-1.34 (m, 1H), 1.30-1.17 (m, 1H), 0.91-0.82 (m, 1H), 0.78-0.58 (m, 2H), 0.53-0.43 (m, 1H). |
| 490 | 654.7 | 1H NMR (400 MHz, DMSO-d6) δ 8.44 (d, J = 8.5 Hz, 1H), 7.99 (d, J = 8.0 Hz, 1H), 7.95 (s, 3H), 7.45 (s, 1H), 7.14 (d, J = 8.1 Hz, 1H), 7.02 (s, 1H), 6.94 (d, J = 1.2 Hz, 1H), 5.06-4.96 (m, 1H), 4.75-4.65 (m, 1H), 4.64-4.54 (m, 1H), 4.12 (s, 3H), 3.99 (s, 3H), 3.85 (dd, J = 6.5, 3.3 Hz, 2H), 3.67-3.48 (m, 2H), 3.45-3.37 (m, 2H), 3.32 (dd, J = 10.5, 7.1 Hz, 1H), 1.99-1.81 (m, 2H), 1.81-1.69 (m, 1H), 1.69-1.48 (m, 4H), 1.43 (d, J = 7.1 Hz, 3H), 1.40-1.35 (m, 1H), 1.31-1.17 (m, 1H), 1.14-1.01 (m, 1H), 0.91-0.83 (m, 1H), 0.76-0.59 (m, 2H), 0.56-0.43 (m, 3H), 0.31-0.20 (m, 2H). |
| 491 | 686.4 | 1H NMR (400 MHz, DMSO-d6) δ 8.83 (d, J = 6.9 Hz, 1H), 8.19 (s, 3H), 8.08 (d, J = 8.0 Hz, 1H), 7.45 (s, 1H), 7.35 (dd, J = 7.4, 1.6 Hz, 1H), 7.31 (dd, J = 7.5, 1.6 Hz, 1H), 7.25 (d, J = 8.1 Hz, 2H), 7.22-7.18 (m, 1H), 7.08 (s, 1H), 6.95 (d, J = 1.2 Hz, 1H), 6.86 (t, J = 74.9 Hz, 1H), 5.19 (p, J = 7.0 Hz, 1H), 4.87 (t, J = 12.5 Hz, 1H), 4.67 (s, 1H), 4.59 (d, J = 13.6 Hz, 1H), 4.12 (s, 3H), 4.00 (s, 3H), 3.62 (s, 2H), 3.45 (s, 1H), 2.45-2.35 (m, 1H), 2.28-2.15 (m, 1H), 2.04-1.86 (m, 2H), 1.49 (d, J = 7.1 Hz, 3H), 1.45-1.36 (m, 1H), 1.33-1.10 (m, 2H), 0.61-0.47 (m, 1H). |
| 492 | 687.3 | 1H NMR (400 MHz, DMSO-d6) δ 9.25 (d, J = 6.9 Hz, 1H), 8.63-8.55 (m, 2H), 8.20 (s, 3H), 8.10 (d, J = 8.0 Hz, 1H), 7.54 (d, J = 5.2 Hz, 1H), 7.45 (s, 1H), 7.27 (d, J = 8.1 Hz, 1H), 7.10 (s, 1H), 6.95 (d, J = 1.2 Hz, 1H), 6.86 (t, J = 74.9 Hz, 1H), 5.22 (p, J = 7.0 Hz, 1H), 4.91-4.79 (m, 1H), 4.72-4.56 (m, 2H), 4.13 (s, 3H), 4.00 (s, 3H), 3.69-3.50 (m, 3H), 3.51-3.39 (m, 1H), 2.43-2.34 (m, 2H), 1.96 (s, 2H), 1.51 (d, J = 7.0 Hz, 3H), 1.48-1.38 (m, 1H), 1.37-1.23 (m, 1H), 1.24-1.13 (m, 2H), 0.64-0.46 (m, 1H). |
| 493 | 658.6 | 1H NMR (400 MHz, DMSO-d6) δ 8.44 (d, J = 8.6 Hz, 1H), 7.99 (d, J = 8.0 Hz, 1H), 7.94 (s, 3H), 7.45 (s, 1H), 7.14 (d, J = 8.1 Hz, 1H), 7.02 (s, 1H), 6.93 (d, J = 1.2 Hz, 1H), 5.07-4.95 (m, 1H), 4.75-4.64 (m, 1H), 4.64-4.55 (m, 1H), 4.12 (s, 3H), 3.99 (s, 3H), 3.84 (d, J = 6.1 Hz, 2H), 3.76-3.67 (m, 1H), 3.61 (ddd, J = 11.2, 5.4, 3.6 Hz, 1H), 3.57-3.48 (m, 2H), 3.45 (d, J = 11.4 Hz, 1H), 3.29 (s, 3H), 1.98-1.81 (m, 2H), 1.81-1.69 (m, 1H), 1.70-1.48 (m, 4H), 1.43 (d, J = 7.1 Hz, 3H), 1.31-1.16 (m, 1H), 0.90-0.82 (m, 1H), 0.79-0.57 (m, 2H), 0.53-0.42 (m, 1H). |
| 494 | 698.7 | 1H NMR (400 MHz, DMSO-d6) δ 8.44 (d, J = 8.5 Hz, 1H), 7.99 (d, J = 8.0 Hz, 1H), 7.95 (s, 3H), 7.45 (s, 1H), 7.14 (d, J = 8.1 Hz, 1H), 7.02 (s, 1H), 6.93 (d, J = 1.2 Hz, 1H), 5.08-4.96 (m, 1H), 4.76-4.64 (m, 1H), 4.64-4.54 (m, 1H), 4.12 (s, 3H), 3.99 (s, 3H), 3.87-3.75 (m, 2H), 3.71 (d, J = 11.0 Hz, 1H), 3.64-3.48 (m, 2H), 3.39 (s, 1H), 2.04 (d, J = 2.8 Hz, 7H), 1.87 (d, J = 7.8 Hz, 2H), 1.76 (s, 1H), 1.70-1.46 (m, 4H), 1.43 (d, J = 7.1 Hz, 3H), 1.41-1.34 (m, 1H), 1.30-1.18 (m, 1H), 0.92-0.83 (m, 1H), 0.77-0.59 (m, 2H), 0.52-0.45 (m, 1H). |
| 495 | 654.5 | 1H NMR (400 MHz, Methanol-d4) δ 8.95 (d, J = 7.9 Hz, 1H), 8.11 (dd, J = 26.4, 8.1 Hz, 1H), 7.77-7.14 (m, 6H), 7.05 (s, 1H), 7.03-6.97 (m, 1H), 6.66 (d, J = 15.6 Hz, 1H), 6.35-6.19 (m, 1H), 5.55-5.45 (m, 1H), 5.04 (d, J = 10.5 Hz, 1H), 4.47 (d, J = 14.2 Hz, 1H), 4.19 (d, J = 4.4 Hz, 3H), 4.08 (d, J = 2.4 Hz, 3H), 3.82 (s, 2H), 3.68 (d, J = 35.7 Hz, 2H), 3.49 (d, J = 1.4 Hz, 4H), 2.08 (d, J = 21.0 Hz, 2H), 1.86 (s, 2H), 1.68 (d, J = 6.8 Hz, 2H), 1.60 (d, J = 6.9 Hz, 3H). |
| 496 | 648.7 | 1H NMR (400 MHz, Methanol-d4) δ 8.96 (d, J = 8.0 Hz, 1H), 8.14 (d, J = 8.1 Hz, 1H), 7.94 (d, J = 1.3 Hz, 1H), 7.82-7.48 (m, 2H), 7.49-7.18 (m, 6H), 7.04 (d, J = 24.5 Hz, 1H), 6.68 (d, J = 15.7 Hz, 1H), 6.28 (dd, J = 8.8, 4.1 Hz, 1H), 5.60-5.44 (m, 1H), 4.49 (d, J = 14.2 Hz, 1H), 4.20 (d, J = 4.5 Hz, 3H), 4.11 (d, J = 2.4 Hz, 3H), 3.61 (d, J = 15.1 Hz, 4H), 2.58 (s, 2H), 2.40 (d, J = 12.9 Hz, 2H), 1.64 (dd, J = 31.1, 6.9 Hz, 5H). |
| 497 | 612.2 | 1H NMR (400 MHz, Methanol-d4) δ 8.15 (t, J = 7.4 Hz, 2H), 7.59 (d, J = 10.7 Hz, 1H), 7.26 (d, J = 8.1 Hz, 1H), 7.11 (s, 1H), 5.62 (d, J = 15.4 Hz, 1H), 5.22 (t, J = 13.5 Hz, 2H), 4.95 (td, J = 9.8, 4.7 Hz, 1H), 4.80 (q, J = 7.0 Hz, 1H), 4.50 (tt, J = 9.7, 4.8 Hz, 1H), 4.46-4.22 (m, 1H), 4.00 (s, 3H), 3.70 (dt, J = 12.3, 4.5 Hz, 1H), 3.63-3.46 (m, 1H), 3.25-3.06 (m, |

TABLE 3-continued

| Example | ES/MS m/z [M + H]+ | 1H NMR |
|---|---|---|
| | | 2H), 2.83 (ddd, J = 13.9, 11.6, 5.1 Hz, 1H), 2.60-2.33 (m, 2H), 2.19-1.78 (m, 4H), 1.68 (ddd, J = 15.7, 10.0, 5.4 Hz, 1H), 1.62 (d, J = 7.0 Hz, 3H), 1.46 (dt, J = 9.5, 5.2 Hz, 1H), 1.01-0.80 (m, 1H). |
| 498 | 627.1 | 1H NMR (400 MHz, Methanol-d4) δ 8.43 (dd, J = 4.9, 1.5 Hz, 1H), 8.11 (dd, J = 7.1, 4.0 Hz, 2H), 7.78 (dd, J = 7.9, 1.6 Hz, 1H), 7.59 (d, J = 10.7 Hz, 1H), 7.46 (dd, J = 7.8, 4.9 Hz, 1H), 7.30 (d, J = 8.1 Hz, 1H), 7.09 (s, 1H), 5.36 (q, J = 7.0 Hz, 1H), 5.08 (dt, J = 14.7, 7.8 Hz, 1H), 4.71-4.36 (m, 2H), 3.98 (s, 3H), 3.70 (dd, J = 12.9, 4.5 Hz, 1H), 3.55 (d, J = 13.1 Hz, 1H), 3.17 (ddd, J = 18.3, 13.2, 10.4 Hz, 2H), 2.62-2.28 (m, 5H), 2.22-1.99 (m, 2H), 1.65 (d, J = 7.0 Hz, 3H), 1.45 (s, 2H), 1.41-1.04 (m, 1H), 0.58 (s, 1H). |
| 499 | 576.2 | 1H NMR (400 MHz, Methanol-d4) δ 8.15 (d, J = 6.1 Hz, 1H), 8.04 (d, J = 8.1 Hz, 1H), 7.66 (d, J = 10.5 Hz, 1H), 7.20 (d, J = 8.1 Hz, 1H), 7.02 (d, J = 3.2 Hz, 1H), 5.22 (q, J = 7.0 Hz, 1H), 4.54 (qd, J = 9.1, 8.3, 3.4 Hz, 2H), 4.39 (dd, J = 13.3, 9.2 Hz, 1H), 4.00 (d, J = 4.3 Hz, 3H), 3.67 (dt, J = 11.5, 4.2 Hz, 1H), 3.60-3.49 (m, 1H), 3.38-3.30 (m, 2H), 3.27-3.06 (m, 2H), 2.49 (ddt, J = 14.6, 9.9, 4.6 Hz, 1H), 2.28 (dt, J = 10.7, 5.6 Hz, 1H), 2.17-2.01 (m, 3H), 2.00-1.88 (m, 1H), 1.87-1.68 (m, 2H), 1.60 (d, J = 7.1 Hz, 4H), 1.54-1.20 (m, 3H), 1.15-1.02 (m, 1H), 1.00-0.89 (m, 1H), 0.81-0.70 (m, 1H). |
| 500 | 588.4 | 1H NMR (400 MHz, Methanol-d4) δ 8.32 (d, J = 1.6 Hz, 1H), 8.21-7.94 (m, 2H), 7.76 (dd, J = 8.6, 3.8 Hz, 1H), 7.24 (dd, J = 9.8, 8.2 Hz, 1H), 7.06 (d, J = 21.2 Hz, 1H), 5.41-5.18 (m, 1H), 5.07-4.92 (m, 1H), 4.71-4.29 (m, 2H), 4.01 (d, J = 7.3 Hz, 3H), 3.68 (d, J = 12.8 Hz, 2H), 3.59-3.43 (m, 2H), 3.29-3.04 (m, 2H), 2.69-2.36 (m, 1H), 2.10 (dd, J = 24.7, 11.7 Hz, 1H), 1.97-1.70 (m, 1H), 1.65-1.15 (m, 14H), 1.10 (s, 2H). |
| 501 | 622.1 | 1H NMR (400 MHz, Methanol-d4) δ 8.25 (d, J = 1.5 Hz, 1H), 8.09 (dd, J = 14.5, 8.1 Hz, 1H), 7.93 (t, J = 1.8 Hz, 1H), 7.24 (dd, J = 9.8, 8.1 Hz, 1H), 7.04 (d, J = 22.0 Hz, 1H), 5.68-5.17 (m, 1H), 5.18-4.91 (m, 1H), 4.71 (dtd, J = 48.6, 9.3, 4.5 Hz, 1H), 4.49 (qd, J = 9.3, 4.6 Hz, 1H), 4.39-4.03 (m, 4H), 3.66 (d, J = 12.9 Hz, 1H), 3.62-3.38 (m, 2H), 3.32-3.10 (m, 3H), 2.98 (dd, J = 12.8, 10.2 Hz, 1H), 2.83 (s, 1H), 2.46 (d, J = 36.4 Hz, 0H), 2.22-1.66 (m, 5H), 1.74-1.18 (m, 10H), 1.10 (s, 3H). |
| 502 | 686.6 | 1H NMR (400 MHz, Methanol-d4) δ 8.13 (d, J = 6.3 Hz, 1H), 8.04 (dd, J = 16.4, 7.9 Hz, 1H), 7.67 (d, J = 10.8 Hz, 1H), 7.22 (d, J = 8.1 Hz, 1H), 7.04 (s, 1H), 6.28 (t, J = 74.4 Hz, 1H), 5.39-5.22 (m, 1H), 5.03-4.88 (m, 6H), 4.83-4.66 (m, 2H), 4.58-4.44 (m, 1H), 4.34 (ddd, J = 14.2, 9.5, 5.8 Hz, 1H), 4.19 (tdd, J = 11.0, 8.9, 3.8 Hz, 2H), 3.81-3.61 (m, 1H), 3.60-3.46 (m, 1H), 3.25-3.08 (m, 1H), 2.62-2.39 (m, 1H), 2.07 (t, J = 11.1 Hz, 1H), 1.97-1.67 (m, 2H), 1.67-1.20 (m, 10H), 1.10 (s, 3H). |
| 503 | 651.1 | NA |
| 504 | 656.6 | 1H NMR (400 MHz, Methanol-d4) δ 8.59 (d, J = 2.6 Hz, 1H), 8.50 (d, J = 2.6 Hz, 1H), 8.16-8.07 (m, 1H), 7.82 (d, J = 1.3 Hz, 1H), 7.54 (d, J = 1.4 Hz, 1H), 7.32 (d, J = 8.1 Hz, 1H), 7.07 (s, 1H), 5.37 (q, J = 7.0 Hz, 1H), 5.04 (dt, J = 15.2, 7.7 Hz, 1H), 4.54-4.42 (m, 1H), 4.26 (s, 3H), 3.87-3.52 (m, 8H), 3.49 (s, 3H), 2.88-2.64 (m, 1H), 2.61-2.39 (m, 1H), 2.19-1.94 (m, 2H), 1.85 (s, 1H), 1.65 (d, J = 7.0 Hz, 3H), 1.55-1.40 (m, 3H), 1.29 (d, J = 12.1 Hz, 1H), 0.67 (s, 1H). |
| 505 | 618.9 | 1H NMR (400 MHz, Methanol-d4) δ 8.01 (d, J = 8.0 Hz, 1H), 7.82 (d, J = 1.3 Hz, 1H), 7.53 (d, J = 1.4 Hz, 1H), 7.17 (d, J = 8.1 Hz, 1H), 6.98 (s, 1H), 5.11 (q, J = 7.0 Hz, 1H), 4.44 (d, J = 14.4 Hz, 1H), 4.23 (s, 3H), 3.94-3.54 (m, 7H), 3.49 (m, 4H), 2.20-1.67 (m, 4H), 1.56 (d, J = 7.1 Hz, 5H), 1.32 (d, J = 9.5 Hz, 1H), 1.09 (dt, J = 8.8, 4.6 Hz, 1H), 0.81 (d, J = 6.3 Hz, 2H), 0.59 (q, J = 7.7, 5.9 Hz, 1H). |
| 506 | 588.5 | 1H NMR (400 MHz, Methanol-d4) δ 8.01 (d, J = 8.1 Hz, 1H), 7.82 (d, J = 1.4 Hz, 1H), 7.52 (d, J = 1.4 Hz, 1H), 7.17 (d, J = 8.1 Hz, 1H), 6.98 (s, 1H), 5.11 (q, J = 7.0 Hz, 1H), 4.45 (d, J = 14.5 Hz, 1H), 4.24 (s, 3H), 3.39 (d, J = 31.6 Hz, 3H), 2.20 (s, 1H), 2.06-1.62 (m, 7H), 1.65-1.22 (m, 10H), 1.09 (dt, J = 8.8, 4.5 Hz, 1H), 0.86-0.72 (m, 2H), 0.65-0.51 (m, 1H). |
| 507 | 606.4 | 1H NMR (400 MHz, Methanol-d4) δ 8.24 (d, J = 1.5 Hz, 1H), 8.01 (d, J = 8.1 Hz, 1H), 7.93 (d, J = 1.5 Hz, 1H), 7.17 (d, J = 8.0 Hz, 1H), 6.99 (s, 1H), 5.11 (q, J = 7.1 Hz, 1H), 4.59-4.32 (m, 3H), 4.24 (s, 3H), 3.66 (d, J = 12.8 Hz, 1H), 3.58-3.42 (m, 2H), 3.25-3.05 (m, 3H), 2.63-2.29 (m, 1H), 2.24-1.89 (m, 1H), 1.74 (s, 1H), 1.65-1.23 (m, 12H), 1.09 (dt, J = 8.6, 4.5 Hz, 1H), 0.82 (s, 2H), 0.59 (dt, J = 8.0, 4.4 Hz, 1H). |
| 508 | 610.1 | 1H NMR (400 MHz, Chloroform-d) δ 8.21 (d, J = 1.3 Hz, 1H), 7.90 (d, J = 8.0 Hz, 1H), 7.47 (d, J = 1.3 Hz, 1H), 7.08 (d, J = 8.0 Hz, 1H), 6.76 (s, 1H), 6.68 (d, J = 9.5 Hz, 1H), 5.27 (dq, J = 9.9, 8.0, 7.0 Hz, 1H), 4.79-4.61 (m, 2H), 4.14 (d, J = 6.8 Hz, 4H), 4.05 (s, 3H), 3.98 (s, 3H), 2.06 (s, 2H), 1.99 (ddt, J = 12.7, 5.6, 2.8 Hz, 2H), 1.53 (d, J = 7.1 Hz, 6H), 1.46-1.38 (m, 2H), 1.31-1.19 (m, 7H), 0.86 (dt, J = 4.4, 2.0 Hz, 1H), 0.75-0.65 (m, 2H), 0.58-0.44 (m, 1H). |
| 509 | 558.4 | 1H NMR (400 MHz, Methanol-d4) δ 8.5 (s, 1H), 8.00 (d, J = 8.0 Hz, 1H), 7.94 (d, J = 1.3 Hz, 1H), 7.46 (d, J = 1.3 Hz, 1H), 7.16 (d, J = 8.1 Hz, 1H), 6.96 (s, 1H), 5.11 (q, J = 7.0 Hz, 1H), 4.64-4.29 (m, 2H), 4.12 (d, J = |

TABLE 3-continued

| Example | ES/MS m/z [M + H]+ | 1H NMR |
|---|---|---|
| | | 10.4 Hz, 6H), 3.26-2.93 (m, 2H), 1.95 (dd, J = 10.4, 6.6 Hz, 1H), 1.74 (s, 1H), 1.64-1.20 (m, 13H), 1.13-0.97 (m, 1H), 0.80 (d, J = 12.3 Hz, 2H), 0.60 (q, J = 6.7, 5.6 Hz, 1H). |
| 510 | 696.4 | 1H NMR (400 MHz, Methanol-d4) δ 8.61 (d, J = 2.6 Hz, 1H), 8.51 (d, J = 2.6 Hz, 1H), 8.11 (d, J = 8.0 Hz, 1H), 7.60-7.43 (m, 1H), 7.30 (d, J = 8.1 Hz, 1H), 7.12 (d, J = 7.6 Hz, 1H), 7.05 (d, J = 1.2 Hz, 2H), 5.39 (q, J = 6.8 Hz, 1H), 5.02 (d, J = 13.4 Hz, 1H), 4.87-4.70 (m, 3H), 4.49 (d, J = 14.2 Hz, 1H), 4.10 (s, 5H), 3.98-3.55 (m, 5H), 3.50 (d, J = 1.8 Hz, 3H), 3.19 (s, 4H), 2.89-2.69 (m, 1H), 2.63-2.42 (m, 2H), 1.86 (s, 1H), 1.80-1.37 (m, 6H), 1.29 (s, 2H), 0.74 (d, J = 12.2 Hz, 1H). |
| 511 | 650.6 | 1H NMR (400 MHz, Methanol-d4) δ 8.67 (d, J = 8.4 Hz, 1H), 8.00 (d, J = 8.0 Hz, 1H), 7.76 (d, J = 1.2 Hz, 1H), 7.41-7.29 (m, 1H), 7.22-7.08 (m, 2H), 6.97 (d, J = 10.3 Hz, 1H), 5.30-5.06 (m, 1H), 4.46 (d, J = 14.5 Hz, 1H), 4.13 (s, 3H), 3.90-3.56 (m, 4H), 3.49 (s, 4H), 2.83 (s, 1H), 1.89 (dd, J = 81.3, 41.1 Hz, 5H), 1.65-1.25 (m, 8H), 1.12 (dd, J = 29.2, 5.8 Hz, 1H), 0.81 (s, 2H), 0.59 (s, 1H). |
| 512 | 602.5 | 1H NMR (400 MHz, Methanol-d4) δ 8.00 (d, J = 8.0 Hz, 1H), 7.71 (d, J = 1.2 Hz, 1H), 7.29 (d, J = 11.3 Hz, 1H), 7.16 (d, J = 8.1 Hz, 1H), 7.00 (s, 1H), 5.10 (q, J = 7.1 Hz, 1H), 4.52 (d, J = 14.5 Hz, 1H), 4.13 (d, J = 1.0 Hz, 3H), 3.81 (d, J = 4.5 Hz, 1H), 3.63 (s, 1H), 3.56-3.43 (m, 4H), 2.34-1.70 (m, 1H), 1.66-1.22 (m, 16H), 1.11-1.00 (m, 1H), 0.81 (s, 2H), 0.59 (s, 1H). |
| 513 | 640.4 | NA |
| 514 | 632.4 | 1H NMR (400 MHz, DMSO-d6) δ 9.18-8.45 (m, 2H), 8.04 (d, J = 8.1 Hz, 1H), 7.82 (d, J = 7.4 Hz, 1H), 7.41-7.26 (m, 1H), 7.19 (d, J = 8.1 Hz, 1H), 7.03 (s, 1H), 6.85 (s, 1H), 5.12 (p, J = 7.1 Hz, 1H), 4.86-4.74 (m, 1H), 4.45-4.19 (m, 2H), 4.12 (s, 3H), 3.99 (s, 3H), 3.54-3.35 (m, 2H), 3.31-3.18 (m, 2H), 3.09-2.88 (m, 1H), 2.98 (s, 3H), 2.46-2.19 (m, 1H), 1.92 (t, J = 12.1 Hz, 1H), 1.75-1.53 (m, 2H), 1.45 (d, J = 7.1 Hz, 3H), 1.53-1.31 (m, 4H), 1.21 (s, 3H), 1.17-0.99 (m, 4H), 0.95 (s, 3H). |
| 515 | 618.4 | 1H NMR (400 MHz, DMSO-d6) δ 8.74 (br. s, 2H), 8.63 (d, J = 8.2 Hz, 1H), 8.05 (d, J = 8.1 Hz, 1H), 8.00 (d, J = 6.4 Hz, 1H), 7.67-7.58 (m, 2H), 7.30 (s, 1H), 7.21 (d, J = 8.2 Hz, 1H), 5.16 (p, J = 7.2 Hz, 1H), 4.92-4.70 (m, 3H), 4.47-4.34 (m, 1H), 3.86-3.76 (m, 1H), 3.42 (br. dd, J = 34.5, 12.3 Hz, 2H), 3.13-2.88 (m, 2H), 2.40-2.25 (m, 1H), 1.99-1.63 (m, 4H), 1.54 (d, J = 7.1 Hz, 3H), 1.63-1.38 (m, 1H), 1.37-1.26 (m, 1H), 1.21-1.07 (m, 6H), 1.00 (s, 3H), 0.86-0.74 (m, 2H), 0.70-0.64 (m, 2H). |
| 516 | 600.3 | 1H NMR (400 MHz, DMSO-d6) δ 8.90-8.77 (m, 2H), 8.72 (d, J = 8.0 Hz, 1H), 8.37 (d, J = 6.3 Hz, 1H), 8.06 (d, J = 8.2 Hz, 1H), 8.01 (d, J = 1.2 Hz, 1H), 7.36 (d, J = 1.2 Hz, 1H), 7.19 (d, J = 8.2 Hz, 1H), 7.06 (s, 1H), 5.61 (td, J = 10.8, 4.3 Hz, 1H), 5.32 (td, J = 11.0, 3.3 Hz, 1H), 5.05-4.76 (m, 2H), 4.65 (td, J = 12.6, 6.2 Hz, 1H), 4.42 (dtd, J = 25.3, 12.7, 11.0, 5.2 Hz, 2H), 4.17 (s, 3H), 4.02 (s, 3H), 3.49-3.35 (m, 1H), 3.14-2.90 (m, 3H), 2.74-2.61 (m, 1H), 2.61-2.47 (m, 1H), 2.42-2.29 (m, 1H), 2.20-2.08 (m, 1H), 1.98-1.88 (m, 2H), 1.83 (td, J = 8.3, 5.4 Hz, 1H), 1.50 (d, J = 7.2 Hz, 3H), 1.15-1.02 (m, 1H), 0.88 (td, J = 8.5, 3.6 Hz, 1H), 0.73-0.64 (m, 1H). |
| 517 | 612.3 | 1H NMR (400 MHz, DMSO-d6) δ 8.39 (d, J = 6.2 Hz, 1H), 8.05 (d, J = 8.1 Hz, 1H), 8.01 (br. s, 3H), 7.46 (s, 1H), 7.19 (d, J = 8.2 Hz, 1H), 7.03 (s, 1H), 6.94 (s, 1H), 5.60 (td, J = 10.9, 4.3 Hz, 1H), 5.36-5.25 (m, 1H), 4.99 (p, J = 7.0 Hz, 1H), 4.62 (td, J = 12.6, 6.2 Hz, 1H), 4.38 (td, J = 12.7, 3.6 Hz, 1H), 4.15 (s, 3H), 3.99 (s, 3H), 3.95-3.76 (m, 1H), 3.75-3.67 (m, 1H), 3.62-3.28 (m, 4H), 3.36 (s, 3H), 2.72-2.52 (m, 2H), 2.14-1.87 (m, 3H), 1.86-1.69 (m, 2H), 1.50 (d, J = 7.2 Hz, 3H), 1.15-1.01 (m, 1H), 0.88 (td, J = 8.5, 3.6 Hz, 1H), 0.73-0.64 (m, 1H). |
| 518 | 602.3 | 1H NMR (400 MHz, DMSO-d6) δ 8.75 (br. s, 2H), 8.69 (d, J = 7.9 Hz, 1H), 8.53 (d, J = 5.5 Hz, 1H), 8.03-7.96 (m, 2H), 7.34 (s, 1H), 7.11 (d, J = 8.0 Hz, 1H), 7.07 (s, 1H), 4.96-4.74 (m, 2H), 4.68-4.60 (m, 1H), 4.50-4.36 (m, 1H), 4.11 (s, 3H), 4.02 (s, 3H), 3.70-3.20 (m, 3H), 3.13-2.88 (m, 2H), 2.42-2.28 (m, 1H), 2.23-2.06 (m, 1H), 1.97-1.87 (m, 1H), 1.85-1.74 (m, 1H), 1.40 (d, J = 7.1 Hz, 3H), 1.46-1.32 (m, 2H), 1.10-0.83 (m, 4H), 0.74-0.60 (m, 3H), 0.39-0.23 (m, 1H). |
| 519 | 614.3 | 1H NMR (400 MHz, DMSO-d6) δ 8.88-8.76 (m, 2H), 8.63 (d, J = 7.0 Hz, 1H), 8.40 (d, J = 6.2 Hz, 1H), 8.05 (d, J = 8.1 Hz, 1H), 8.01 (d, J = 6.4 Hz, 1H), 7.62 (d, J = 10.5 Hz, 1H), 7.31 (s, 1H), 7.18 (d, J = 8.2 Hz, 1H), 5.61 (td, J = 10.9, 4.2 Hz, 1H), 5.32 (td, J = 10.8, 3.3 Hz, 1H), 4.98 (p, J = 7.0 Hz, 1H), 4.93-4.83 (m, 2H), 4.76 (td, J = 9.6, 4.6 Hz, 1H), 4.52-4.34 (m, 2H), 3.82 (tt, J = 7.1, 3.9 Hz, 1H), 3.46 (br. d, J = 12.4 Hz, 1H), 3.38 (br. d, J = 12.6 Hz, 1H), 3.12-2.90 (m, 2H), 2.72-2.58 (m, 1H), 2.48-2.28 (m, 2H), 2.08-1.87 (m, 3H), 1.84 (td, J = 8.3, 5.4 Hz, 1H), 1.50 (d, J = 7.2 Hz, 3H), 1.29-1.02 (m, 2H), 0.93-0.81 (m, 2H), 0.74-0.62 (m, 2H). |
| 520 | 616.3 | 1H NMR (400 MHz, DMSO-d6) δ 8.74 (br. s, 2H), 8.62 (d, J = 7.1 Hz, 1H), 8.56 (d, J = 5.4 Hz, 1H), 7.99 (d, J = 7.9 Hz, 1H), 7.97 (d, J = 6.4 Hz, 1H), 7.61 (d, J = 10.6 Hz, 1H), 7.29 (s, 1H), 7.11 (d, J = 8.1 Hz, 1H), 5.01- |

TABLE 3-continued

| Example | ES/MS m/z [M + H]+ | ¹H NMR |
|---|---|---|
| | | 4.69 (m, 4H), 4.48-4.33 (m, 1H), 3.86-3.78 (m, 1H), 3.45-3.34 (m, 1H), 3.12-2.88 (m, 2H), 2.40-2.11 (m, 2H), 2.00-1.82 (m, 1H), 1.79 (td, J = 8.2, 5.3 Hz, 1H), 1.41 (d, J = 7.0 Hz, 3H), 1.46-1.19 (m, 5H), 1.14-0.81 (m, 4H), 0.74-0.53 (m, 2H), 0.38-0.12 (m, 4H). |
| 521 | 588.3 | 1H NMR (400 MHz, DMSO-d6) δ 8.87-8.70 (m, 2H), 8.65 (d, J = 7.9 Hz, 1H), 8.38 (d, J = 6.3 Hz, 1H), 8.06 (d, J = 8.1 Hz, 1H), 8.03 (d, J = 6.4 Hz, 1H), 7.76 (d, J = 10.9 Hz, 1H), 7.19 (d, J = 8.2 Hz, 1H), 7.14 (s, 1H), 5.61 (td, J = 11.0, 4.3 Hz, 1H), 5.33 (td, J = 10.9, 3.3 Hz, 1H), 4.99 (p, J = 7.0 Hz, 1H), 4.93-4.70 (m, 2H), 4.49-4.34 (m, 2H), 3.99 (s, 3H), 3.47 (d, J = 12.2 Hz, 1H), 3.38 (d, J = 12.8 Hz, 1H), 3.11-2.91 (m, 2H), 2.73-2.60 (m, 1H), 2.58-2.41 (m, 1H), 2.40-2.28 (m, 1H), 2.17-2.04 (m, 1H), 1.93 (d, J = 13.5 Hz, 2H), 1.83 (td, J = 8.2, 5.4 Hz, 1H), 1.50 (d, J = 7.2 Hz, 3H), 1.15-1.02 (m, 1H), 0.88 (td, J = 8.6, 3.7 Hz, 1H), 0.68 (ddd, J = 7.0, 5.3, 3.7 Hz, 1H). |
| 522 | 590.3 | 1H NMR (400 MHz, DMSO-d6) δ 8.86-8.70 (m, 2H), 8.64 (d, J = 7.9 Hz, 1H), 8.55 (d, J = 5.5 Hz, 1H), 8.00 (d, J = 8.1 Hz, 1H), 8.00 (d, J = 6.4 Hz, 1H), 7.74 (d, J = 10.8 Hz, 1H), 7.14 (s, 1H), 7.12 (d, J = 8.1 Hz, 1H), 4.98-4.71 (m, 3H), 4.41 (tq, J = 14.1, 5.0 Hz, 1H), 4.02-3.93 (m, 1H), 3.95 (s, 3H), 3.46 (d, J = 12.6 Hz, 1H), 3.38 (d, J = 12.7 Hz, 1H), 3.11-2.90 (m, 2H), 2.41-2.27 (m, 1H), 2.22-2.08 (m, 1H), 2.00-1.84 (m, 1H), 1.79 (ddd, J = 9.0, 7.6, 5.3 Hz, 1H), 1.40 (d, J = 7.0 Hz, 3H), 1.44-1.34 (m, 3H), 1.10-0.84 (m, 3H), 0.74-0.56 (m, 3H), 0.38-0.22 (m, 1H). |
| 523 | 602.3 | 1H NMR (400 MHz, DMSO-d6) δ 8.76 (br. s, 2H), 8.69 (d, J = 8.0 Hz, 1H), 8.47 (d, J = 7.5 Hz, 1H), 8.04 (d, J = 8.2 Hz, 1H), 7.98 (d, J = 1.3 Hz, 1H), 7.34 (d, J = 1.3 Hz, 1H), 7.24 (d, J = 8.2 Hz, 1H), 7.08 (s, 1H), 4.97-4.74 (m, 2H), 4.70-4.59 (m, 2H), 4.51-4.36 (m, 1H), 4.13 (s, 3H), 4.02 (s, 3H), 3.49-3.34 (m, 2H), 3.13-2.90 (m, 2H), 2.42-2.29 (m, 1H), 2.00-1.77 (m, 2H), 1.68 (d, J = 7.0 Hz, 3H), 1.60 (td, J = 8.2, 5.5 Hz, 1H), 1.50-1.28 (m, 3H), 1.19-0.88 (m, 3H), 0.86-0.61 (m, 3H), 0.48-0.33 (m, 1H). |
| 524 | 614.4 | 1H NMR (400 MHz, DMSO-d6) δ 8.50 (d, J = 7.4 Hz, 1H), 8.03 (d, J = 8.2 Hz, 1H), 8.02-7.88 (m, 3H), 7.43 (s, 1H), 7.24 (d, J = 8.3 Hz, 1H), 7.04 (s, 1H), 6.93 (d, J = 1.2 Hz, 1H), 4.86-4.73 (m, 1H), 4.68-4.55 (m, 3H), 4.15-4.06 (m, 1H), 4.10 (s, 3H), 3.98 (s, 3H), 3.74-3.50 (m, 4H), 3.36 (s, 3H), 2.02-1.82 (m, 2H), 1.81-1.70 (m, 1H), 1.68 (d, J = 7.0 Hz, 3H), 1.59 (td, J = 8.2, 5.5 Hz, 1H), 1.49-1.20 (m, 3H), 1.18-0.87 (m, 3H), 0.83-0.62 (m, 3H), 0.43-0.30 (m, 1H). |
| 525 | 614.4 | 1H NMR (400 MHz, DMSO-d6) δ 8.55 (d, J = 5.5 Hz, 1H), 7.99 (d, J = 8.1 Hz, 1H), 8.08-7.89 (br. s, 3H), 7.42 (s, 1H), 7.11 (d, J = 8.1 Hz, 1H), 7.03 (s, 1H), 6.92 (d, J = 1.1 Hz, 1H), 4.95-4.77 (m, 2H), 4.66-4.58 (m, 1H), 4.18-4.03 (m, 2H), 4.09 (s, 3H), 3.98 (s, 3H), 3.74-3.66 (m, 1H), 3.55-3.50 (m, 2H), 3.44-3.36 (m, 1H), 3.36 (s, 3H), 2.22-2.06 (m, 1H), 2.04-1.85 (m, 1H), 1.84-1.64 (m, 2H), 1.40 (d, J = 7.1 Hz, 3H), 1.35 (s, 3H), 1.07-0.84 (m, 3H), 0.76-0.54 (m, 3H), 0.37-0.21 (m, 1H). |
| 526 | 616.4 | 1H NMR (400 MHz, DMSO-d6) δ 8.90-8.82 (m, 1H), 8.79-8.68 (m, 1H), 8.47 (d, J = 7.8 Hz, 1H), 8.05 (d, J = 8.1 Hz, 1H), 7.97 (s, 1H), 7.80 (d, J = 7.4 Hz, 1H), 7.34 (d, J = 1.2 Hz, 1H), 7.19 (d, J = 8.1 Hz, 1H), 7.06 (s, 1H), 5.52 (br. s, 1H), 5.12 (p, J = 7.1 Hz, 1H), 4.87-4.75 (m, 1H), 4.63-4.34 (m, 2H), 4.21-4.16 (m, 1H), 4.14 (s, 3H), 4.01 (s, 3H), 3.29 (br. d, J = 10.8 Hz, 1H), 3.12-2.97 (m, 2H), 2.82 (br. q, J = 11.0 Hz, 1H), 2.02-1.77 (m, 3H), 1.75-1.58 (m, 3H), 1.45 (d, J = 7.1 Hz, 3H), 1.51-1.25 (m, 5H), 1.21 (s, 3H), 1.18-0.99 (m, 2H), 0.95 (s, 3H) |
| 527 | 656.4 | 1H NMR (400 MHz, DMSO-d6) δ 8.04 (d, J = 8.1 Hz, 1H), 7.93 (br. s, 3H), 7.82 (d, J = 7.4 Hz, 1H), 7.44 (s, 1H), 7.19 (d, J = 8.2 Hz, 1H), 7.03 (d, J = 1.0 Hz, 1H), 6.93 (d, J = 1.2 Hz, 1H), 5.12 (p, J = 7.1 Hz, 1H), 4.86-4.76 (m, 1H), 4.48-4.33 (m, 1H), 4.11 (s, 3H), 3.99 (s, 3H), 3.94-3.86 (m, 2H), 3.60-3.30 (m, 3H), 2.10-1.97 (m, 1H), 1.92 (t, J = 12.1 Hz, 1H), 1.85-1.72 (m, 1H), 1.75-1.53 (m, 2H), 1.45 (d, J = 7.1 Hz, 3H), 1.49-1.26 (m, 6H), 1.21 (s, 3H), 1.18-0.97 (m, 3H), 0.94 (s, 3H), 0.73-0.40 (m, 4H). |
| 528 | 636.3 | 1H NMR (400 MHz, DMSO-d6) δ 9.23 (d, J = 7.0 Hz, 1H), 8.60 (d, J = 2.5 Hz, 1H), 8.49 (d, J = 2.5 Hz, 1H), 8.09 (d, J = 8.0 Hz, 1H), 7.95 (br. s, 3H), 7.34 (d, J = 1.1 Hz, 1H), 7.28 (d, J = 8.1 Hz, 1H), 7.09 (s, 1H), 6.88 (s, 1H), 5.24 (p, J = 7.0 Hz, 1H), 4.89-4.78 (m, 1H), 4.63-4.54 (m, 1H), 4.12 (s, 3H), 3.99 (s, 3H), 3.87-3.48 (m, 1H), 3.41-3.29 (m, 1H), 3.26-2.81 (m, 2H), 2.73-2.61 (m, 1H), 2.50-2.30 (m, 1H), 1.88-1.64 (m, 3H), 1.51 (d, J = 7.0 Hz, 3H), 1.64-1.29 (m, 4H), 1.20 (d, J = 6.9 Hz, 3H), 1.28-1.13 (m, 1H), 0.62 (dd, J = 24.3, 12.2 Hz, 1H). |
| 529 | 616.4 | 1H NMR (400 MHz, DMSO-d6) δ 8.90 (br. d, J = 11.5 Hz, 1H), 8.81-8.67 (m, 1H), 8.47 (d, J = 7.8 Hz, 1H), 8.05 (d, J = 8.1 Hz, 1H), 7.97 (d, J = 1.3 Hz, 1H), 7.80 (d, J = 7.5 Hz, 1H), 7.35 (d, J = 1.3 Hz, 1H), 7.19 (d, J = 8.2 Hz, 1H), 7.06 (s, 1H), 5.69-5.35 (m, 1H), 5.12 (p, J = 7.1 Hz, 1H), 4.87-4.76 (m, 1H), 4.60-4.49 (m, 1H), 4.46-4.36 (m, 1H), 4.22-4.15 (m, 1H), 4.14 (s, 3H), 4.01 (s, 3H), 3.29 (d, J = 11.5 Hz, 1H), 3.11-2.95 |

TABLE 3-continued

| Example | ES/MS m/z [M + H]+ | ¹H NMR |
|---|---|---|
| | | (m, 2H), 2.82 (q, J = 10.7 Hz, 1H), 2.02-1.78 (m, 3H), 1.76-1.54 (m, 3H), 1.45 (d, J = 7.1 Hz, 3H), 1.51-1.25 (m, 4H), 1.21 (s, 3H), 1.17-0.98 (m, 3H), 0.95 (s, 3H). |
| 530 | 616.4 | 1H NMR (400 MHz, DMSO-d6) δ 8.94 (br. d, J = 11.5 Hz, 1H), 8.79-8.71 (m, 1H), 8.48 (d, J = 7.8 Hz, 1H), 8.05 (d, J = 8.1 Hz, 1H), 7.97 (d, J = 1.3 Hz, 1H), 7.80 (d, J = 7.4 Hz, 1H), 7.35 (d, J = 1.3 Hz, 1H), 7.19 (d, J = 8.2 Hz, 1H), 7.07 (s, 1H), 5.12 (p, J = 7.1 Hz, 1H), 4.87-4.76 (m, 1H), 4.64-4.48 (m, 1H), 4.46-4.35 (m, 1H), 4.22-4.16 (m, 1H), 4.14 (s, 3H), 4.02 (s, 3H), 3.29 (d, J = 10.6 Hz, 1H), 3.11-2.98 (m, 2H), 2.83 (q, J = 10.9 Hz, 1H), 2.02-1.78 (m, 3H), 1.67 (t, J = 8.7 Hz, 3H), 1.45 (d, J = 7.1 Hz, 3H), 1.52-1.27 (m, 4H), 1.21 (s, 3H), 1.16-1.00 (m, 3H), 0.95 (s, 3H). |
| 531 | 610.4 | 1H NMR (400 MHz, DMSO-d6) δ 9.08 (br. s, 1H), 8.51 (br. s, 1H), 8.43 (d, J = 8.6 Hz, 1H), 7.99 (d, J = 8.0 Hz, 1H), 7.45 (s, 1H), 7.13 (d, J = 8.1 Hz, 1H), 7.01 (s, 1H), 6.95 (d, J = 1.1 Hz, 1H), 5.01 (p, J = 7.2 Hz, 1H), 4.77-4.51 (m, 3H), 4.11 (s, 3H), 3.99 (s, 3H), 3.83-3.51 (m, 3H), 3.43-3.10 (m, 3H), 2.50-2.41 (m, 1H), 2.18-2.03 (m, 1H), 1.96-1.29 (m, 9H), 1.43 (d, J = 7.1 Hz, 3H), 1.29-1.16 (m, 1H), 0.92-0.81 (m, 1H), 0.77-0.57 (m, 3H), 0.52-0.43 (m, 1H). |
| 532 | 610.4 | 1H NMR (400 MHz, DMSO-d6) δ 9.12 (br. s, 1H), 8.52 (br. s, 1H), 8.43 (d, J = 8.6 Hz, 1H), 7.99 (d, J = 8.0 Hz, 1H), 7.45 (s, 1H), 7.13 (d, J = 8.1 Hz, 1H), 7.02 (s, 1H), 6.95 (d, J = 1.1 Hz, 1H), 5.01 (p, J = 7.2 Hz, 1H), 4.76-4.53 (m, 3H), 4.12 (s, 3H), 3.99 (s, 3H), 3.81-3.55 (m, 3H), 3.43-3.10 (m, 3H), 2.50-2.42 (m, 1H), 2.16-2.05 (m, 1H), 1.96-1.30 (m, 9H), 1.43 (d, J = 7.1 Hz, 3H), 1.29-1.15 (m, 1H), 0.90-0.81 (m, 1H), 0.77-0.56 (m, 3H), 0.52-0.43 (m, 1H). |
| 533 | 630.4 | 1H NMR (400 MHz, DMSO-d6) δ 8.04 (d, J = 8.1 Hz, 1H), 7.85 (br. s, 3H), 7.81 (d, J = 7.4 Hz, 1H), 7.51 (br. s, 1H), 7.19 (d, J = 8.1 Hz, 1H), 7.03 (s, 1H), 6.95 (s, 1H), 5.12 (p, J = 7.1 Hz, 1H), 4.86-4.75 (m, 1H), 4.46-4.33 (m, 1H), 4.11 (s, 3H), 3.98 (s, 3H), 3.64-3.51 (m, 2H), 3.52 (dd, J = 11.1, 5.7 Hz, 1H), 3.45 (dd, J = 11.1, 7.3 Hz, 1H), 3.32-3.15 (m, 1H), 3.05 (t, J = 11.7 Hz, 1H), 2.08-1.97 (m, 1H), 1.93 (t, J = 11.8 Hz, 1H), 1.75-1.49 (m, 4H), 1.45 (d, J = 7.1 Hz, 3H), 1.48-1.26 (m, 5H), 1.21 (s, 3H), 1.17-0.99 (m, 3H), 0.95 (s, 3H). |
| 534 | 620.3 | 1H NMR (400 MHz, DMSO-d6) δ 8.54 (d, J = 9.0 Hz, 1H), 8.12 (d, J = 8.1 Hz, 1H), 8.10 (brs, 3H), 7.60 (s, 1H), 7.29 (d, J = 8.1 Hz, 1H), 7.16 (s, 1H), 7.04 (s, 1H), 5.50 (dd, J = 30.1, 14.4 Hz, 1H), 5.38-5.27 (m, 1H), 5.26-5.10 (m, 1H), 4.62-4.40 (m, 3H), 4.10 (s, 3H), 4.01 (s, 3H), 3.75 (brs, 1H), 2.40-2.23 (m, 2H), 2.19-2.07 (m, 1H), 1.96-1.50 (m, 5H), 1.40 (d, J = 7.0 Hz, 3H), 1.38-1.31 (m, 2H), 1.23-1.06 (m, 2H), 1.03-0.67 (m, 2H). |
| 535 | 612.7 | NA |
| 536 | 616.7 | 1H NMR (400 MHz, DMSO-d6) δ 8.05 (d, J = 8.1 Hz, 1H), 7.93 (brs, 3H), 7.82 (d, J = 7.4 Hz, 1H), 7.42 (s, 1H), 7.19 (d, J = 8.1 Hz, 1H), 7.03 (s, 1H), 6.94 (s, 1H), 5.18-5.08 (m, 1H), 4.87-4.76 (m, 1H), 4.45-4.33 (m, 2H), 4.12 (s, 3H), 4.00 (s, 3H), 3.74-3.67 (m, 1H), 3.35-3.23 (m, 1H), 3.0-3.08 (m, 1H), 2.20 (d, J = 12.5 Hz, 1H), 1.98-1.87 m, 2H), 1.73-1.48 (m, 3H), 1.45 (d, J = 7.1 Hz, 3H), 1.43-1.26 (m, 5H), 1.21 (s, 3H), 1.18-0.98 (m, 3H), 0.95 (s, 3H). |
| 537 | 602.6 | 1H NMR (400 MHz, DMSO-d6) δ 8.80 (brs, 2H), 8.62 (d, J = 8.0 Hz, 1H), 8.05 (d, J = 8.1 Hz, 1H), 7.84 (s, 1H), 7.82 (d, J = 7.5 Hz, 1H), 7.59 (s, 1H), 7.19 (d, J = 8.1 Hz, 1H), 7.11 (s, 1H), 5.18-5.08 (m, 1H), 4.91-4.71 (m, 2H), 4.59-4.34 (m, 2H), 3.96 (s, 3H), 3.48 (d, J = 12.4 Hz, 1H), 3.37 (d, J = 12.4 Hz, 1H), 3.14-2.89 (m, 2H), 2.54 (s, 3H), 2.41-2.29 (m, 1H), 1.93 (t, J = 12.3 Hz, 2H), 1.75-1.59 (m, 2H), 1.45 (d, J = 7.1 Hz, 3H), 1.51-1.28 (m, 4H), 1.21 (s, 3H), 1.18-1.05 (m, 3H), 0.95 (s, 3H). |
| 538 | 624.2 | 1H NMR (400 MHz, DMSO-d6) δ 8.82 (s, 1H), 8.79 (brs, 2H), 8.08 (d, J = 8.1 Hz, 1H), 7.85 (d, J = 4.7 Hz, 1H), 7.83 (d, J = 7.5 Hz, 1H), 7.21 (d, J = 8.2 Hz, 1H), 7.13 (s, 1H), 5.19-5.08 (m, 1H), 4.95-4.72 (m, 2H), 4.51-4.33 (m, 2H), 4.11 (s, 3H), 3.53-3.32 (m, 2H), 3.13-2.91 (m, 2H), 2.40-2.27 (m, 1H), 2.02-1.84 (m, 2H), 1.76-1.62 (m, 2H), 1.54-1.28 (m, 3H), 1.45 (d, J = 7.1 Hz, 3H), 1.22 (s, 3H), 1.18-1.05 (m, 2H), 0.95 (s, 3H). |
| 539 | 616.4 | 1H NMR (400 MHz, DMSO-d6) δ 8.77 (brs, 2H), 8.63 (d, J = 8.0 Hz, 1H), 8.40 (d, J = 7.2 Hz, 1H), 8.02 (d, J = 8.5 Hz, 1H), 8.00 (d, J = 7.3 Hz, 2H), 7.63 (d, J = 10.6 Hz, 1H), 7.30 (s, 1H), 7.22 (d, J = 8.2 Hz, 1H), 4.95-4.69 (m, 3H), 4.53-4.32 (m, 2H), 3.87-3.78 (m, 1H), 3.47 (d, J = 12.5 Hz, 1H), 3.38 (d, J = 12.5 Hz, 1H), 3.14-2.93 (m, 2H), 2.40-2.28 (m, 1H), 1.99-1.78 (m, 1H), 1.74 (d, J = 7.1 Hz, 3H), 1.69-1.06 (m, 5H), 0.97-0.69 (m, 4H), 0.67-0.58 (m, 4H), 0.58-0.45 (m, 1H). |
| 540 | 634.3 | 1H NMR (400 MHz, DMSO-d6) δ 8.77 (brs, 2H), 8.65 (d, J = 7.4 Hz, 1H), 8.09 (d, J = 8.0 Hz, 1H), 8.05 (d, J = 9.4 Hz, 1H), 8.02 (d, J = 6.5 Hz, 1H), 7.63 (d, J = 10.5 Hz, 1H), 7.34 (s, 1H), 7.23 (d, J = 8.1 Hz, 1H), 5.24 (dq, J = 8.9, 6.8 Hz, 1H), 4.96-4.72 (m, 4H), 4.47-4.36 (m, 1H), 3.88-3.78 (m, 1H), 3.52-3.29 (m, 4H), 3.15-2.91 (m, 2H), 2.88-2.76 (m, |

TABLE 3-continued

| Example | ES/MS m/z [M + H]+ | ¹H NMR |
|---|---|---|
| | | 1H), 2.45-2.29 (m, 3H), 1.99-1.83 (m, 1H), 1.46 (d, J = 6.8 Hz, 3H), 1.34 (s, 3H), 1.22 (s, 3H), 1.20-1.09 (m, 2H), 0.93-0.83 (m, 1H), 0.72 (brs, 2H), 0.62-0.51 (m, 1H). |
| 541 | 622.4 | 1H NMR (400 MHz, DMSO-d6) δ 8.81 (d, J = 7.9 Hz, 1H), 8.75 (brs, 2H), 8.07 (d, J = 8.1 Hz, 1H), 7.98 (s, 1H), 7.89 (s, 1H), 7.83 (d, J = 7.4 Hz, 1H), 7.20 (d, J = 7.4 Hz, 1H), 7.16 (s, 1H), 5.18-5.08 (m, 1H), 4.93-4.80 (m, 2H), 4.78-4.67 (m, 1H), 4.60-4.49 (m, 1H), 4.44-4.31 (m, 1H), 3.99 (s, 3H), 3.57-3.36 (m, 2H), 3.16-2.89 (m, 3H), 2.34 (brs, 1H), 2.00-1.84 (m, 2H), 1.79-1.59 (m, 2H), 1.46 (d, J = 7.1 Hz, 3H), 1.43-1.26 (m, 3H), 1.22 (s, 3H), 1.15-1.03 (m, 2H), 0.95 (s, 3H). |
| 542 | 612.7 | 1H NMR (400 MHz, DMSO-d6) δ 8.10 (brs, 3H), 8.05 (d, J = 8.1 Hz, 1H), 7.82 (d, J = 7.4 Hz, 1H), 7.42 (s, 1H), 7.19 (d, J = 8.1 Hz, 1H), 7.04 (s, 1H), 6.90 (s, 1H), 5.19-5.06 (m, 1H), 4.89-4.77 (m, 1H), 4.48-4.35 (m, 1H), 4.12 (s, 3H), 3.99 (s, 3H), 3.93-3.80 (m, 1H), 3.65-3.49 (m, 2H), 1.98-1.86 (m, 1H), 1.76-1.52 (m, 3H), 1.45 (d, J = 7.1 Hz, 3H), 1.43-1.22 (m, 6H), 1.21 (s, 3H), 1.18-0.99 (m, 4H), 0.95 (s, 3H), 0.89-0.77 (m, 1H), 0.53-0.44 (m, 1H). |
| 543 | 612.7 | 1H NMR (400 MHz, DMSO-d6) δ 8.10 (brs, 3H), 8.05 (d, J = 8.1 Hz, 1H), 7.82 (d, J = 7.4 Hz, 1H), 7.42 (s, 1H), 7.19 (d, J = 8.1 Hz, 1H), 7.04 (s, 1H), 6.90 (s, 1H), 5.19-5.06 (m, 1H), 4.89-4.77 (m, 1H), 4.48-4.35 (m, 1H), 4.12 (s, 3H), 3.99 (s, 3H), 3.93-3.80 (m, 1H), 3.65-3.49 (m, 2H), 1.98-1.86 (m, 1H), 1.76-1.52 (m, 3H), 1.45 (d, J = 7.1 Hz, 3H), 1.43-1.22 (m, 6H), 1.21 (s, 3H), 1.18-0.99 (m, 4H), 0.95 (s, 3H), 0.89-0.77 (m, 1H), 0.53-0.44 (m, 1H). |
| 544 | 630.3 | 1H NMR (400 MHz, DMSO-d6) δ 8.82 (brs, 2H), 8.63 (dd, J = 8.1, 1.6 Hz, 1H), 8.01 (d, J = 1.7 Hz, 1H), 8.00 (s, 1H), 7.62 (d, J = 10.6 Hz, 1H), 7.56 (d, J = 8.4 Hz, 1H), 7.30 (s, 1H), 7.15 (d, J = 8.1 Hz, 1H), 5.12-5.02 (m, 1H), 4.94-4.72 (m, 3H), 4.49-4.33 (m, 1H), 3.87-3.75 (m, 1H), 3.47 (d, J = 11.9 Hz, 1H), 3.39 (d, J = 13.2 Hz, 1H), 3.15-2.93 (m, 2H), 2.41-2.28 (m, 1H), 2.01-1.82 (m, 1H), 1.74-1.48 (m, 4H), 1.50 (d, J = 7.2 Hz, 3H), 1.47 (s, 3H), 1.36-1.08 (m, 6H), 0.93-0.86 (m, 1H), 0.75-0.49 (m, 2H), 0.19 (dd, J = 6.7, 3.4 Hz, 1H). |
| 545 | 630.6 | 1H NMR (400 MHz, DMSO-d6) δ 8.79 (brs, 2H), 8.63 (dd, J = 8.2, 1.5 Hz, 1H), 8.02 (d, J = 6.2 Hz, 1H), 8.01 (d, J = 4.4 Hz, 1H), 7.62 (d, J = 10.6 Hz, 1H), 7.28 (s, 1H), 7.25 (d, J = 7.6 Hz, 1H), 7.17 (d, J = 8.2 Hz, 1H), 4.95-4.73 (m, 3H), 4.66-4.34 (m, 2H), 3.89-3.78 (m, 2H), 3.47 (d, J = 12.1 Hz, 1H), 3.39 (d, J = 13.1 Hz, 1H), 3.12-2.92 (m, 2H), 2.42-2.27 (m, 1H), 2.03-1.82 (m, 2H), 1.76-1.43 (m, 5H), 1.51 (d, J = 7.2 Hz, 3H), 1.43-1.17 (m, 4H), 1.16 (s, 3H), 0.83-0.70 (m, 2H), 0.37 (dd, J = 6.5, 4.3 Hz, 1H). |
| 546 | 631.6 | 1H NMR (400 MHz, DMSO-d6) δ 8.79 (brs, 2H), 8.64 (dd, J = 8.0, 1.5 Hz, 1H), 8.57 (d, J = 6.9 Hz, 1H), 8.09 (d, J = 8.1 Hz, 1H), 8.02 (d, J = 6.4 Hz, 1H), 7.76 (d, J = 10.8 Hz, 1H), 7.25 (d, J = 8.2 Hz, 1H), 7.15 (s, 1H), 5.20-5.09 (m, 1H), 4.94-4.72 (m, 1H), 4.67-4.58 (m, 1H), 4.51-4.35 (m, 2H), 4.16 (s, 3H), 3.98 (s, 3H), 3.47 (d, J = 12.3 Hz, 1H), 3.38 (d, J = 12.8 Hz, 1H), 3.13-2.89 (m, 2H), 2.88-2.63 (m, 2H), 2.42-2.28 (m, 1H), 1.99-1.81 (m, 2H), 1.76-1.63 (m, 1H), 1.58 (d, J = 7.0 Hz, 3H), 1.56-1.41 (m, 1H), 1.33-1.13 (m, 1H), 1.10-0.92 (m, 1H). |
| 547 | 642.2 | 1H NMR (400 MHz, DMSO-d6) δ 8.84 (d, J = 8.0 Hz, 1H), 8.82 (brs, 2H), 8.65 (d, J = 8.0 Hz, 1H), 8.11 (d, J = 8.0 Hz, 1H), 7.91-7.84 (m, 1H), 7.27 (d, J = 8.1 Hz, 1H), 7.25 (s, 1H), 6.41-6.30 (m, 1H), 5.93-5.77 (m, 1H), 5.66-5.55 (m, 1H), 5.31-5.17 (m, 1H), 5.07-4.96 (m, 1H), 4.81 (ddt, J = 49.1, 9.7, 4.9 Hz, 1H), 4.47-4.32 (m, 1H), 4.09 (s, 3H), 3.49 (d, J = 12.1 Hz, 1H), 3.39 (d, J = 13.1 Hz, 1H), 3.13-2.91 (m, 2H), 2.61 (dd, J = 18.3, 8.5 Hz, 1H), 2.44-2.34 (m, 1H), 2.06-1.84 (m, 1H), 1.59-1.38 (m, 2H), 1.43 (d, J = 7.1 Hz, 3H), 0.96-0.86 (m, 1H), 0.83-0.60 (m, 2H). |
| 548 | 604.5 | 1H NMR (400 MHz, DMSO-d6) δ 8.82 (brs, 2H), 8.65 (dd, J = 8.1, 1.5 Hz, 1H), 8.02 (d, J = 6.4 Hz, 1H), 8.02 (d, J = 8.1 Hz, 1H), 7.76 (d, J = 10.8 Hz, 1H), 7.54 (d, J = 8.5 Hz, 1H), 7.16 (d, J = 8.1 Hz, 1H), 7.13 (s, 1H), 5.14-5.03 (m, 1H), 4.91-4.65 (m, 3H), 4.49-4.34 (m, 2H), 3.97 (s, 3H), 3.47 (d, J = 12.3 Hz, 1H), 3.44-3.35 (m, 1H), 3.15-2.89 (m, 2H), 2.42-2.29 (m, 1H), 2.00-1.83 (m, 1H), 1.73-1.51 (m, 3H), 1.49 (d, J = 7.1 Hz, 3H), 1.47 (s, 3H), 1.44-1.13 (m, 5H), 0.78-0.64 (m, 1H), 0.18 (dd, J = 6.7, 3.4 Hz, 1H). |
| 549 | 640.6 | 1H NMR (400 MHz, DMSO-d6) δ 8.84 (brs, 2H), 8.68 (d, J = 8.0 Hz, 1H), 8.10 (d, J = 8.1 Hz, 1H), 8.02 (d, J = 6.3 Hz, 1H), 7.77 (d, J = 10.8 Hz, 1H), 7.29 (d, J = 8.2 Hz, 1H), 7.23 (s, 1H), 5.59-5.17 (m, 2H), 4.95-4.68 (m, 2H), 4.52-4.34 (m, 1H), 3.94 (s, 3H), 3.47 (d, J = 12.5 Hz, 1H), 3.38 (d, J = 13.1 Hz, 1H), 3.14-2.90 (m, 2H), 2.42-2.26 (m, 1H), 2.12-1.71 (m, 5H), 1.64 (d, J = 7.1 Hz, 3H), 1.59-1.38 (m, 2H), 1.30-0.98 (m, 3H), 1.18 (s, 3H), 0.32 (dd, J = 6.8, 4.0 Hz, 1H). |
| 550 | 620.2 | 1H NMR (400 MHz, DMSO-d6) δ 8.76 (brs, 2H), 8.65 (d, J = 8.0 Hz, 1H), 8.63 (d, J = 8.8 Hz, 1H), 8.08 (d, J = 8.0 Hz, 1H), 7.83 (s, 1H), 7.60 (s, 1H), 7.25 (d, J = 8.1 Hz, 1H), 7.20 (s, 1H), 6.40-6.28 (m, 1H), 5.94-5.70 (m, 2H), 5.22 (dd, J = 28.1, 14.5 Hz, 1H), 5.07-4.96 (m, 1H), 4.92- |

TABLE 3-continued

| Example | ES/MS m/z [M + H]+ | ¹H NMR |
|---|---|---|
| | | 4.67 (m, 1H), 4.48-4.30 (m, 1H), 3.49 (d, J = 12.7 Hz, 1H), 3.38 (d, J = 12.7 Hz, 1H), 3.11-2.88 (m, 2H), 2.66-2.55 (m, 1H), 2.54 (s, 3H), 2.43-2.25 (m, 2H), 2.01-1.85 (m, 1H), 1.59-1.45 (m, 2H), 1.43 (d, J = 7.1 Hz, 3H), 0.95-0.87 (m, 1H), 0.78-0.59 (m, 2H). |
| 551 | 622.4 | 1H NMR (400 MHz, DMSO-d6) δ 8.80 (brs, 2H), 8.65 (d, J = 8.0 Hz, 1H), 8.55 (d, J = 8.8 Hz, 1H), 8.06 (d, J = 8.0 Hz, 1H), 7.83 (s, 1H), 7.60 (s, 1H), 7.23 (d, J = 8.0 Hz, 1H), 7.19 (s, 1H), 5.69 (t, J = 13.6 Hz, 1H), 5.23-5.00 (m, 2H), 4.80 (dtd, J = 49.0, 9.4, 4.5 Hz, 1H), 4.46-4.32 (m, 1H), 3.93 (s, 3H), 3.49 (d, J = 12.5 Hz, 1H), 3.38 (d, J = 12.8 Hz, 1H), 3.18-2.86 (m, 2H), 2.54 (s, 3H), 2.42-1.88 (m, 5H), 1.69-1.50 (m, 2H), 1.45 (d, J = 7.1 Hz, 3H), 1.39-1.22 (m, 1H), 0.90-0.80 (m, 1H), 0.70-0.44 (m, 3H). |
| 552 | 638.2 | 1H NMR (400 MHz, DMSO-d6) δ 8.75 (brs, 2H), 8.69 (d, J = 8.0 Hz, 1H), 8.09 (d, J = 8.0 Hz, 1H), 8.03 (d, J = 6.3 Hz, 1H), 7.79 (s, 1H), 7.68 (d, J = 8.4 Hz, 1H), 7.27 (d, J = 8.1 Hz, 1H), 7.24 (s, 1H), 6.45-6.35 (m, 1H), 5.87 (t, J = 17.9 Hz, 1H), 5.69 (t, J = 12.5 Hz, 1H), 5.27 (dd, J = 28.3, 14.5 Hz, 1H), 5.19-5.08 (m, 1H), 4.96-4.72 (m, 1H), 4.49-4.35 (m, 1H), 3.92 (s, 3H), 3.48 (d, J = 12.4 Hz, 1H), 3.38 (d, J = 12.9 Hz, 1H), 3.20-2.91 (m, 3H), 2.41-2.29 (m, 1H), 2.04-1.71 (m, 2H), 1.49 (d, J = 7.1 Hz, 3H), 1.37 (s, 3H), 1.22 (dd, J = 9.4, 3.7 Hz, 1H), 0.88-0.75 (m, 1H), 0.38 (dd, J = 6.5, 3.6 Hz, 1H). |
| 553 | 640.5 | 1H NMR (400 MHz, DMSO-d6) δ 8.80 (brs, 2H), 8.68 (d, J = 8.0 Hz, 1H), 8.07 (d, J = 8.1 Hz, 1H), 8.02 (d, J = 6.4 Hz, 1H), 7.77 (d, J = 10.8 Hz, 1H), 7.63 (d, J = 8.5 Hz, 1H), 7.24 (d, J = 8.1 Hz, 1H), 7.22 (s, 1H), 5.67-5.51 (m, 1H), 5.25 (dd, J = 26.9, 14.6 Hz, 1H), 5.18-5.05 (m, 1H), 4.97-4.72 (m, 1H), 4.50-4.35 (m, 1H), 3.94 (s, 3H), 3.48 (d, J = 12.3 Hz, 1H), 3.44-3.34 (m, 1H), 3.13-2.90 (m, 2H), 2.44-2.30 (m, 1H), 2.16-1.52 (m, 5H), 1.48 (d, J = 7.1 Hz, 3H), 1.43 (s, 3H), 1.39-1.03 (m, 3H), 0.54-0.42 (m, 1H), 0.21 (dd, J = 6.9, 3.6 Hz, 1H). |
| 554 | 634.3 | 1H NMR (400 MHz, DMSO-d6) δ 8.16 (brs, 2H), 8.07 (d, J = 8.1 Hz, 1H), 8.03 (brs, 1H), 7.88 (brs, 1H), 7.78 (d, J = 9.8 Hz, 1H), 7.64 (d, J = 8.4 Hz, 1H), 7.24 (d, J = 8.1 Hz, 1H), 7.20 (s, 1H), 5.55 (t, J = 13.5 Hz, 1H), 5.25 (dd, J = 26.9, 14.6 Hz, 1H), 5.18-5.04 (m, 1H), 4.69 (d, J = 35.9 Hz, 1H), 3.99 (s, 1H), 3.94 (s, 3H), 3.66 (brs, 1H), 2.36-2.24 (m, 1H), 2.17-1.55 (m, 6H), 1.48 (d, J = 7.1 Hz, 3H), 1.43 (s, 3H), 1.40-1.07 (m, 4H), 0.56-0.45 (m, 1H), 0.21 (dd, J = 6.9, 3.6 Hz, 1H). |
| 555 | 618.3 | 1H NMR (400 MHz, DMSO-d6) δ 8.16 (brs, 2H), 8.08 (d, J = 8.1 Hz, 1H), 8.05 (brs, 1H), 7.83 (d, J = 7.4 Hz, 1H), 7.72 (d, J = 14.5 Hz, 1H), 7.21 (d, J = 8.1 Hz, 1H), 7.11 (s, 1H), 5.18-5.08 (m, 1H), 4.94-4.63 (m, 2H), 4.50-4.36 (m, 1H), 4.10 (s, 3H), 4.06-3.95 (m, 1H), 3.76-3.63 (m, 1H), 2.27 (brs, 1H), 2.13-1.59 (m, 7H), 1.54-1.26 (m, 4H), 1.45 (d, J = 7.1 Hz, 3H), 1.25-1.05 (m, 3H), 1.22 (s, 3H), 0.95 (s, 3H). |
| 556 | 596.5 | 1H NMR (400 MHz, DMSO-d6) δ 8.18 (brs, 2H), 8.05 (d, J = 8.1 Hz, 1H), 8.02 (s, 1H), 7.82 (d, J = 7.5 Hz, 1H), 7.72 (d, J = 16.4 Hz, 1H), 7.61 (s, 1H), 7.19 (d, J = 8.1 Hz, 1H), 7.08 (s, 1H), 5.18-5.07 (m, 1H), 4.90-4.47 (m, 4H), 3.94 (s, 3H), 3.85-3.61 (m, 2H), 2.45 (s, 3H), 2.35-2.19 (m, 1H), 2.00-1.54 (m, 7H), 1.52-1.26 (m, 5H), 1.45 (d, J = 7.1 Hz, 3H), 1.22 (s, 3H), 1.17-1.01 (m, 1H), 0.95 (s, 3H). |
| 557 | 610.5 | 1H NMR (400 MHz, DMSO-d6) δ 8.45 (d, J = 8.5 Hz, 1H), 8.17 (brs, 1H), 8.05 (s, 1H), 7.99 (d, J = 8.0 Hz, 1H), 7.83 (brs, 1H), 7.63 (d, J = 9.8 Hz, 1H), 7.28 (s, 1H), 7.14 (d, J = 8.1 Hz, 1H), 5.08-4.97 (m, 1H), 4.88-4.58 (m, 4H), 3.95 (d, J = 17.6 Hz, 1H), 3.86-3.76 (m, 1H), 3.74-3.59 (m, 1H), 2.43-2.17 (m, 1H), 1.95-1.46 (m, 9H), 1.44 (d, J = 7.1 Hz, 3H), 1.41-1.08 (m, 4H), 0.96-0.85 (m, 2H), 0.82-0.56 (m, 4H), 0.52-0.45 (m, 1H). |
| 558 | 668.6 | 1H NMR (400 MHz, DMSO-d6) δ 8.87 (brs, 1H), 8.83 (d, J = 8.1 Hz, 1H), 8.07 (d, J = 8.1 Hz, 1H), 7.86 (dd, J = 5.2, 1.2 Hz, 1H), 7.83 (d, J = 7.5 Hz, 1H), 7.20 (d, J = 8.2 Hz, 1H), 7.17 (s, 1H), 5.20-5.07 (m, 1H), 4.91-4.59 (m, 5H), 4.46-4.34 (m, 2H), 3.71-3.57 (m, 2H), 3.48 (d, J = 12.0 Hz, 1H), 3.39 (d, J = 12.4 Hz, 1H), 3.06 (s, 3H), 3.03-2.88 (m, 1H), 2.42-2.30 (m, 1H), 2.00-1.84 (m, 2H), 1.76-1.54 (m, 2H), 1.53-1.25 (m, 4H), 1.45 (d, J = 7.1 Hz, 3H), 1.21 (s, 3H), 1.15-1.00 (m, 2H), 0.95 (s, 3H). |
| 559 | 652.3 | 1H NMR (400 MHz, DMSO-d6) δ 8.82 (d, J = 8.0 Hz, 1H), 8.81 (brs, 1H), 8.44 (d, J = 8.5 Hz, 1H), 8.01 (d, J = 8.1 Hz, 1H), 7.87 (d, J = 4.9 Hz, 1H), 7.15 (d, J = 8.1 Hz, 1H), 7.13 (s, 1H), 5.07-4.96 (m, 1H), 4.94-4.32 (m, 7H), 3.48 (d, J = 12.3 Hz, 1H), 3.39 (d, J = 13.2 Hz, 1H), 3.13-2.91 (m, 2H), 3.05 (s, 3H), 2.42-2.26 (m, 1H), 2.03-1.77 (m, 3H), 1.74-1.33 (m, 7H), 1.43 (d, J = 7.1 Hz, 3H), 1.30-1.16 (m, 1H), 0.92-0.84 (m, 1H), 0.81-0.58 (m, 2H), 0.56-0.46 (m, 1H). |
| 560 | 644.5 | 1H NMR (400 MHz, DMSO-d6) δ 8.84 (d, J = 8.1 Hz, 1H), 8.82 (brs, 2H), 8.57 (d, J = 8.8 Hz, 1H), 8.09 (d, J = 8.0 Hz, 1H), 7.86 (d, J = 4.8 Hz, 1H), 7.27 (s, 1H), 7.23 (s, 1H), 5.54 (t, J = 13.5 Hz, 1H), 5.18 (dd, J = 27.7, 14.6 Hz, 1H), 5.10-4.99 (m, 1H), 4.95-4.69 (m, 1H), 4.48-4.32 (m, 1H), 4.09 (s, 3H), 3.54-3.43 (m, 1H), 3.39 (d, J = 13.3 Hz, 1H), 3.14-2.90 (m, 2H), 2.42-2.31 (m, 1H), 2.25-1.84 (m, 4H), 1.71-1.51 (m, |

TABLE 3-continued

| Example | ES/MS m/z [M + H]+ | ¹H NMR |
|---|---|---|
| | | 2H), 1.45 (d, J = 7.0 Hz, 3H), 1.39-1.25 (m, 1H), 0.90-0.80 (m, 1H), 0.73-0.57 (m, 1H), 0.55-0.42 (m, 2H). |
| 561 | 638.6 | 1H NMR (400 MHz, DMSO-d6) δ 8.98 (d, J = 7.8 Hz, 1H), 8.81 (brs, 2H), 8.70 (s, 1H), 8.52 (d, J = 8.2 Hz, 1H), 8.27 (s, 1H), 8.06 (d, J = 8.0 Hz, 1H), 7.20 (d, J = 8.2 Hz, 1H), 7.19 (s, 1H), 5.78-5.70 (m, 1H), 5.59 (d, J = 15.9 Hz, 1H), 5.16-4.77 (m, 2H), 4.77-4.58 (m, 2H), 4.56-4.48 (m, 1H), 4.04 (s, 3H), 3.49 (d, J = 12.2 Hz, 1H), 3.41 (d, J = 12.9 Hz, 1H), 3.15-2.90 (m, 2H), 2.75-2.60 (m, 1H), 2.49-2.33 (m, 2H), 2.02-1.85 (m, 1H), 1.56-1.45 (m, 1H), 1.42 (d, J = 7.1 Hz, 3H), 1.41-1.28 (m, 2H), 0.95-0.79 (m, 1H), 0.64-0.54 (m, 1H). |
| 562 | 640.5 | 1H NMR (400 MHz, DMSO-d6) δ 8.98 (d, J = 7.8 Hz, 1H), 8.83 (brs, 2H), 8.71 (s, 1H), 8.45 (d, J = 8.5 Hz, 1H), 8.27 (s, 1H), 8.03 (d, J = 8.0 Hz, 1H), 7.17 (d, J = 8.2 Hz, 1H), 7.15 (s, 1H), 5.13-5.02 (m, 1H), 5.00-4.80 (m, 1H), 4.76-4.66 (m, 1H), 4.63-4.38 (m, 2H), 4.03 (s, 3H), 3.54-3.47 (m, 1H), 3.47-3.37 (m, 1H), 3.19-2.89 (m, 2H), 2.47-2.32 (m, 1H), 2.06-1.55 (m, 6H), 1.54-1.34 (m, 1H), 1.44 (d, J = 7.1 Hz, 3H), 1.35-1.16 (m, 1H), 0.93-0.82 (m, 1H), 0.80-0.62 (m, 2H), 0.56-0.44 (m, 1H). |
| 563 | 567.5 | 1H NMR (400 MHz, DMSO-d6) δ 8.69 (d, J = 1.9 Hz, 1H), 8.45 (d, J = 8.5 Hz, 1H), 8.36 (s, 1H), 8.10 (brs, 3H), 8.04 (d, J = 8.0 Hz, 1H), 7.25 (s, 1H), 7.17 (d, J = 8.1 Hz, 1H), 5.08-4.97 (m, 1H), 4.90-4.72 (m, 2H), 4.04 (s, 3H), 2.43-2.23 (m, 1H), 1.92-1.52 (m, 10H), 1.44 (d, J = 7.1 Hz, 3H), 1.40-1.18 (m, 4H), 0.93-0.62 (m, 4H), 0.53-0.46 (m, 1H). |
| 564 | 589.6 | 1H NMR (400 MHz, DMSO-d6) δ 8.80 (brs, 2H), 8.68 (d, J = 8.8 Hz, 1H), 8.64 (d, J = 8.1 Hz, 1H), 8.00 (d, J = 6.4 Hz, 1H), 7.74 (d, J = 10.8 Hz, 1H), 7.62 (s, 1H), 7.56 (d, J = 8.1 Hz, 1H), 7.11 (s, 1H), 7.03 (d, J = 8.3 Hz, 1H), 5.03-4.74 (m, 3H), 4.52-4.35 (m, 1H), 4.24-4.12 (m, 1H), 3.95 (s, 3H), 3.47 (d, J = 12.2 Hz, 1H), 3.38 (d, J = 13.1 Hz, 1H), 3.17-2.91 (m, 2H), 2.42-2.28 (m, 1H), 2.04-1.73 (m, 3H), 1.73-1.53 (m, 2H), 1.43 (d, J = 7.0 Hz, 3H), 1.43-1.28 (m, 3H), 1.01-0.68 (m, 3H), 0.59-0.51 (m, 1H). |
| 565 | 605.5 | 1H NMR (400 MHz, DMSO-d6) δ 8.81 (brs, 2H), 8.65 (d, J = 8.1 Hz, 1H), 8.05 (d, J = 7.7 Hz, 1H), 8.00 (d, J = 6.4 Hz, 1H), 7.74 (d, J = 10.8 Hz, 1H), 7.62 (d, J = 8.2 Hz, 1H), 7.35 (s, 1H), 7.11 (s, 1H), 7.08 (dd, J = 8.3, 1.2 Hz, 1H), 5.13-5.02 (m, 1H), 4.95-4.74 (m, 2H), 4.48-4.35 (m, 1H), 4.20 (t, J = 11.8 Hz, 1H), 3.96 (s, 3H), 3.47 (d, J = 12.6 Hz, 1H), 3.38 (d, J = 13.0 Hz, 1H), 3.13-2.89 (m, 2H), 2.43-2.31 (m, 1H), 2.16-1.58 (m, 5H), 1.54-1.36 (m, 3H), 1.46 (d, J = 7.1 Hz, 3H), 1.25 (s, 3H), 1.20-1.04 (m, 3H), 0.95 (s, 3H). |
| 566 | 638.3 | 1H NMR (400 MHz, DMSO-d6) δ 8.60 (d, J = 8.8 Hz, 1H), 8.18 (s, 1H), 8.08 (dd, J = 8.0, 2.2 Hz, 1H), 8.03 (brs, 3H), 7.68 (dd, J = 16.8, 4.6 Hz, 1H), 7.31-7.24 (m, 1H), 7.20 (d, J = 2.5 Hz, 1H), 5.57-5.44 (m, 1H), 5.18 (ddd, J = 27.6, 14.6, 3.2 Hz, 1H), 5.11-5.00 (m, 1H), 4.08 (s, 3H), 3.27 (d, J = 11.0 Hz, 1H), 2.74-2.57 (m, 1H), 2.27-1.75 (m, 8H), 1.72-1.53 (m, 3H), 1.44 (d, J = 7.1 Hz, 3H), 1.40-1.20 (m, 1H), 0.92-0.79 (m, 1H), 0.71-0.56 (m, 1H), 0.55-0.43 (m, 2H). |
| 567 | 670.5 | 1H NMR (400 MHz, DMSO-d6) δ 8.81 (d, J = 8.0 Hz, 1H), 8.80 (brs, 2H), 8.58 (d, J = 8.8 Hz, 1H), 8.08 (d, J = 8.0 Hz, 1H), 7.82 (dd, J = 5.2, 1.2 Hz, 1H), 7.40 (s, 1H), 7.25 (d, J = 8.1 Hz, 1H), 5.85-5.73 (m, 1H), 5.26-5.16 (m, 1H), 5.12-5.00 (m, 1H), 4.94-4.69 (m, 1H), 4.46-4.35 (m, 1H), 4.12-4.01 (m, 1H), 3.43 (dd, J = 37.5, 12.5 Hz, 2H), 3.28-2.86 (m, 2H), 2.43-2.28 (m, 1H), 2.23-2.02 (m, 2H), 2.01-1.87 (m, 2H), 1.70-1.50 (m, 2H), 1.44 (d, J = 7.0 Hz, 3H), 1.38-1.18 (m, 2H), 1.15-0.99 (m, 2H), 0.90-0.81 (m, 1H), 0.73-0.57 (m, 1H), 0.54-0.44 (m, 3H). |
| 568 | 598.7 | 1H NMR (400 MHz, DMSO-d6) δ 8.62 (brs, 3H), 8.45 (d, J = 4.1 Hz, 1H), 8.43 (s, 1H), 8.00 (d, J = 1.2 Hz, 1H), −7.98 (s, 1H), 7.60 (d, J = 8.0 Hz, 1H), 7.30 (s, 1H), 7.14 (d, J = 8.0 Hz, 1H), 5.07-4.95 (m, 1H), 4.88-4.68 (m, 2H), 4.22-4.10 (m, 1H), 3.87-3.77 (m, 2H), 3.44-3.32 (m, 2H), 3.27-3.17 (m, 2H), 2.96-2.80 (m, 2H), 2.01-1.81 (m, 3H), 1.80-1.48 (m, 5H), 1.44 (d, J = 7.1 Hz, 3H), 1.42-1.11 (m, 3H), 0.92-0.80 (m, 2H), 0.77-0.44 (m, 3H). |
| 569 | 624.8 | 1H NMR (400 MHz, DMSO-d6) δ 8.57 (s, 1H), 8.49 (s, 1H), 8.45 (d, J = 8.5 Hz, 1H), 7.99 (d, J = 8.0 Hz, 1H), 7.86 (d, J = 6.1 Hz, 1H), 7.61 (d, J = 10.1 Hz, 1H), 7.28 (s, 1H), 7.14 (d, J = 8.0 Hz, 1H), 5.07-4.95 (m, 1H), 4.92-4.72 (m, 2H), 4.02-3.85 (m, 2H), 3.86-3.74 (m, 2H), 3.29 (brs, 2H), 2.96 (brs, 2H), 1.90-1.47 (m, 10H), 1.52-1.31 (m, 1H), 1.44 (d, J = 7.1 Hz, 3H), 1.27-1.07 (m, 3H), 0.98-0.53 (m, 5H), 0.53-0.38 (m, 1H). |
| 570 | 655.7 | 1H NMR (400 MHz, DMSO-d6) δ 8.57 (d, J = 6.9 Hz, 1H), 8.08 (d, J = 8.1 Hz, 1H), 7.97 (brs, 3H), 7.44 (s, 1H), 7.25 (d, J = 8.2 Hz, 1H), 7.04 (s, 1H), 6.93 (d, J = 1.1 Hz, 1H), 5.19-5.09 (m, 1H), 4.56-4.35 (m, 2H), 4.16 (s, 3H), 4.13 (s, 3H), 3.99 (s, 3H), 3.75-3.68 (m, 3H), 3.37 (s, 3H), 2.82-2.64 (m, 2H), 2.02-1.87 (m, 1H), 1.86-1.64 (m, 3H), 1.61-1.51 (m, 1H), 1.58 (d, J = 7.0 Hz, 3H), 1.50-1.35 (m, 1H), 1.29-1.11 (m, 1H), 1.08-0.90 (m, 1H). |

TABLE 3-continued

| Example | ES/MS m/z [M + H]+ | ¹H NMR |
|---|---|---|
| 571 | 642.7 | 1H NMR (400 MHz, DMSO-d6) δ 8.77 (brs, 2H), 8.69-8.59 (m, 1H), 8.51-8.42 (m, 1H), 8.05-7.96 (m, 2H), 7.75-7.59 (m, 1H), 7.58-7.34 (m, 1H), 7.19-7.09 (m, 2H), 5.17 (d, J = 13.3 Hz, 1H), 5.09-4.63 (m, 3H), 4.54-4.28 (m, 2H), 3.47 (d, J = 12.3 Hz, 1H), 3.39 (d, J = 13.0 Hz, 1H), 3.14-2.91 (m, 1H), 2.40-2.29 (m, 1H), 2.02-1.50 (m, 8H), 1.45 (d, J = 7.1 Hz, 1.5H), 1.43 (d, J = 7.2 Hz, 1.5H), 1.36-1.14 (m, 2H), 1.01-0.45 (m, 8H), −0.17 (dd, J = 9.3, 4.9 Hz, 0.5H), −0.38 (dd, J = 9.2, 4.9 Hz, 0.5H). |
| 572 | 628.3 | 1H NMR (400 MHz, DMSO-d6) δ 8.46 (s, 1H), 8.07 (s, 1H), 7.99 (d, J = 8.0 Hz, 1H), 7.87 (brs, 3H), 7.63 (d, J = 8.0 Hz, 1H), 7.28 (s, 1H), 7.14 (d, J = 8.1 Hz, 1H), 5.07-4.96 (m, 1H), 4.90-4.69 (m, 2H), 3.84-3.76 (m, 1H), 3.75-3.67 (m, 1H), 3.62-3.47 (m, 1H), 3.41-3.37 (m, 1H), 3.37 (s, 3H), 3.31-3.18 (m, 1H), 1.93-1.79 (m, 1H), 1.73-1.53 (m, 5H), 1.44 (d, J = 7.1 Hz, 3H), 1.42-1.31 (m, 2H), 1.31-1.03 (m, 4H), 0.92-0.82 (m, 2H), 0.77-0.55 (m, 3H), 0.53-0.42 (m, 1H). |
| 573 | 599.7 | 1H NMR (400 MHz, DMSO-d6) δ 8.92 (d, J = 2.0 Hz, 1H), 8.85 (d, J = 7.8 Hz, 1H), 8.78 (brs, 2H), 8.63 (d, J = 2.0 Hz, 1H), 8.46 (d, J = 8.5 Hz, 1H), 8.02 (d, J = 8.0 Hz, 1H), 7.42 (s, 1H), 7.16 (d, J = 8.1 Hz, 1H), 5.08-4.96 (m, 1H), 4.95-4.72 (m, 3H), 4.49-4.35 (m, 1H), 3.86-3.79 (m, 1H), 3.51-3.38 (m, 3H), 3.18-2.92 (m, 2H), 2.42-2.32 (m, 1H), 2.02-1.81 (m, 2H), 1.77-1.61 (m, 3H), 1.62-1.52 (m, 1H), 1.45 (d, J = 7.1 Hz, 3H), 1.44-1.35 (m, 1H), 1.33-1.13 (m, 3H), 1.08-0.97 (m, 1H), 0.93-0.80 (m, 2H), 0.78-0.60 (m, 2H), 0.55-0.45 (m, 1H). |
| 574 | 611.6 | 1H NMR (400 MHz, DMSO-d6) δ 8.52 (d, J = 1.9 Hz, 1H), 8.46 (d, J = 8.5 Hz, 1H), 8.24 (d, J = 1.9 Hz, 1H), 8.02 (d, J = 8.0 Hz, 1H), 7.97 (brs, 3H), 7.38 (s, 1H), 7.16 (d, J = 8.1 Hz, 1H), 5.09-4.96 (m, 1H), 4.92-4.74 (m, 2H), 3.84-3.76 (m, 2H), 3.62-3.50 (m, 2H), 3.50-3.37 (m, 1H), 3.37 (s, 3H), 2.04-1.73 (m, 4H), 1.73-1.49 (m, 4H), 1.45 (d, J = 7.1 Hz, 3H), 1.45-1.35 (m, 1H), 1.31-1.03 (m, 4H), 0.92-0.82 (m, 1H), 0.83-0.58 (m, 3H), 0.55-0.42 (m, 1H). |
| 575 | 610.5 | 1H NMR (400 MHz, DMSO-d6) δ 8.55 (brs, 2H), 8.45 (d, J = 8.5 Hz, 1H), 8.35 (d, J = 8.0 Hz, 1H), 7.99 (d, J = 8.1 Hz, 1H), 7.98-7.96 (m, 1H), 7.60 (d, J = 10.5 Hz, 1H), 7.30 (s, 1H), 7.14 (d, J = 8.1 Hz, 1H), 5.05-4.95 (m, 1H), 4.93-4.70 (m, 3H), 3.64-3.50 (m, 2H), 3.30-3.20 (m, 1H), 3.00-2.89 (m, 1H), 2.50-2.40 (m, 1H), 1.92-1.79 (m, 1H), 1.75-1.42 (m, 6H), 1.45 (d, J = 7.0 Hz, 3H), 1.41-1.33 (m, 1H), 1.29-1.11 (m, 3H), 0.92-0.72 (m, 5H), 0.71-0.53 (m, 3H), 0.53-0.43 (m, 1H). |
| 576 | 651.3 | 1H NMR (400 MHz, DMSO-d6) δ 9.25 (d, J = 7.9 Hz, 1H), 8.68 (d, J = 2.6 Hz, 1H), 8.55 (d, J = 2.6 Hz, 1H), 7.98 (brs, 3H), 7.65 (d, J = 8.1 Hz, 1H), 7.60 (s, 1H), 7.42 (s, 1H), 7.17 (dd, J = 8.3, 1.2 Hz, 1H), 7.06 (s, 1H), 6.93 (d, J = 1.1 Hz, 1H), 5.29-5.16 (m, 1H), 4.81-4.66 (m, 1H), 4.30-4.15 (m, 1H), 4.11 (s, 3H), 3.99 (s, 3H), 3.75-3.67 (m, 1H), 3.60-3.48 (m, 2H), 3.46-3.34 (m, 1H), 3.37 (s, 3H), 2.76-2.62 (m, 1H), 2.49-2.41 (m, 1H), 2.03-1.84 (m, 2H), 1.83-1.62 (m, 2H), 1.62-1.47 (m, 2H), 1.53 (d, J = 7.0 Hz, 3H), 1.42-1.27 (m, 1H), 0.89-0.71 (m, 1H). |
| 577 | 687.3 | 1H NMR (400 MHz, DMSO-d6) δ 9.25 (d, J = 7.9 Hz, 1H), 8.68 (d, J = 2.6 Hz, 1H), 8.55 (d, J = 2.6 Hz, 1H), 8.19 (brs, 3H), 7.66 (d, J = 8.2 Hz, 1H), 7.60 (s, 1H), 7.44 (s, 1H), 7.17 (dd, J = 8.3, 1.2 Hz, 1H), 7.07 (s, 1H), 6.94 (d, J = 1.2 Hz, 1H), 6.86 (t, J = 74.7 Hz, 1H), 5.28-5.16 (m, 1H), 4.79-4.71 (m, 1H), 4.70-4.65 (m, 1H), 4.23-4.14 (m, 1H), 4.12 (s, 3H), 4.00 (s, 3H), 3.98-3.89 (m, 2H), 3.68-3.34 (m, 4H), 2.77-2.64 (m, 1H), 2.50-2.41 (m, 1H), 2.04-1.84 (m, 2H), 1.76-1.49 (m, 2H), 1.53 (d, J = 6.2 Hz, 3H), 1.42-1.28 (m, 1H), 0.86-0.73 (m, 1H). |
| 578 | 666.4 | 1H NMR (400 MHz, DMSO-d6) δ 9.26 (d, J = 6.8 Hz, 1H), 8.61 (d, J = 2.6 Hz, 1H), 8.50 (d, J = 2.6 Hz, 1H), 8.11 (d, J = 8.1 Hz, 1H), 7.98 (brs, 3H), 7.68 (s, 1H), 7.33 (s, 1H), 7.32-7.27 (m, 2H), 5.29-5.18 (m, 1H), 5.01-4.74 (m, 2H), 4.08-3.98 (m, 2H), 3.74-3.69 (m, 2H), 3.63-3.39 (m, 4H), 3.37 (s, 3H), 2.73-2.64 (m, 1H), 2.46-2.32 (m, 1H), 2.01-1.88 (m, 1H), 1.82-1.69 (m, 1H), 1.63-1.34 (m, 2H), 1.52 (d, J = 7.1 Hz, 3H), 1.29-0.98 (m, 4H), 0.67-0.44 (m, 2H). |
| 579 | 628.3 | 1H NMR (400 MHz, DMSO-d6) δ 8.46 (d, J = 8.5 Hz, 1H), 8.00 (d, J = 8.1 Hz, 1H), 7.95 (brs, 3H), 7.68 (s, 1H), 7.28 (dd, J = 11.6, 1.2 Hz, 1H), 7.25 (s, 1H), 7.15 (d, J = 8.1 Hz, 1H), 5.07-4.96 (m, 1H), 4.86-4.71 (m, 2H), 4.05-3.96 (m, 1H), 3.61-3.48 (m, 2H), 3.48-3.37 (m, 2H), 3.37 (s, 3H), 2.02-1.46 (m, 8H), 1.44 (d, J = 7.1 Hz, 3H), 1.42-1.01 (m, 6H), 0.99-0.82 (m, 2H), 0.80-0.55 (m, 3H), 0.53-0.46 (m, 1H). |
| 580 | 616.7 | 1H NMR (400 MHz, DMSO-d6) δ 8.91 (d, J = 8.0 Hz, 1H), 8.83 (brs, 3H), 8.80 (d, J = 5.7 Hz, 1H), 8.39 (d, J = 8.6 Hz, 1H), 7.99 (d, J = 6.6 Hz, 1H), 7.90 (d, J = 8.0 Hz, 1H), 7.06 (d, J = 8.0 Hz, 1H), 6.82 (s, 1H), 5.04-4.93 (m, 1H), 4.93-4.82 (td, J = 9.6, 4.6 Hz, 1H), 4.81-4.64 (m, 3H), 4.46-4.33 (m, 1H), 3.48 (d, J = 12.5 Hz, 1H), 3.39 (d, J = 13.1 Hz, 1H), 3.14-2.91 (m, 2H), 2.43-2.28 (m, 2H), 2.21-2.07 (m, 1H), 2.01-1.79 (m, 2H), 1.70-1.47 (m, 2H), 1.43 (d, J = 7.0 Hz, 3H), 1.47-1.29 (m, 1H), 1.27-1.05 (m, 3H), 0.92-0.80 (m, 1H), 0.76-0.56 (m, 2H), 0.51-0.34 (m, 3H). |

TABLE 3-continued

| Example | ES/MS m/z [M + H]+ | ¹H NMR |
|---|---|---|
| 581 | 676.6 | 1H NMR (400 MHz, DMSO-d6) δ 8.44 (d, J = 8.6 Hz, 1H), 8.31 (s, 3H), 7.99 (d, J = 8.0 Hz, 1H), 7.48 (t, J = 1.5 Hz, 1H), 7.14 (d, J = 8.1 Hz, 1H), 7.02 (s, 1H), 6.98 (s, 1H), 6.76 (t, J = 76.3 Hz, 1H), 5.07-4.93 (m, 1H), 4.81-4.52 (m, 3H), 4.12 (s, 3H), 4.01 (s, 3H), 3.69-3.61 (m, 2H), 2.40-2.19 (m, 2H), 2.10-1.79 (m, 5H), 1.77-1.31 (m, 6H), 1.43 (d, J = 7.1 Hz, 3H), 1.32-1.14 (m, 2H), 0.94-0.80 (m, 1H), 0.80-0.56 (m, 2H), 0.55-0.42 (m, 1H). |
| 582 | 668.4 | 1H NMR (400 MHz, DMSO-d6) δ 8.44 (d, J = 8.6 Hz, 1H), 8.36 (brs, 3H), 7.99 (d, J = 8.0 Hz, 1H), 7.48 (s, 1H), 7.14 (d, J = 8.1 Hz, 1H), 7.02 (s, 1H), 6.95 (d, J = 1.1 Hz, 1H), 5.08-4.95 (m, 2H), 4.76-4.64 (m, 1H), 4.64-4.54 (m, 1H), 4.12 (s, 3H), 4.03-3.89 (m, 1H), 4.00 (s, 3H), 3.80-3.41 (m, 4H), 2.13-1.94 (m, 2H), 1.93-1.83 (m, 1H), 1.72-1.48 (m, 5H), 1.48-1.32 (m, 1H), 1.43 (d, J = 7.1 Hz, 3H), 1.31-1.16 (m, 1H), 0.97-0.80 (m, 1H), 0.79-0.58 (m, 2H), 0.54-0.44 (m, 1H). |
| 583 | 628.9 | 1H NMR (400 MHz, DMSO-d6) δ 8.00 (d, J = 8.1 Hz, 1H), 7.99 (brs, 3H), 7.54 (d, J = 8.4 Hz, 1H), 7.44 (s, 1H), 7.15 (d, J = 8.1 Hz, 1H), 7.02 (s, 1H), 6.93 (d, J = 1.1 Hz, 1H), 5.13-5.01 (m, 1H), 4.77-4.70 (m, 1H), 4.60-4.53 (m, 1H), 4.11 (s, 3H), 3.99 (s, 3H), 3.75-3.68 (m, 1H), 3.65-3.52 (m, 3H), 3.45-3.33 (m, 1H), 3.37 (s, 3H), 2.02-1.88 (m, 1H), 1.83-1.51 (m, 5H), 1.49 (s, 3H), 1.47 (s, 3H), 1.42-1.12 (m, 5H), 0.74-0.65 (m, 1H), 0.18 (dd, J = 6.7, 3.4 Hz, 1H). |
| 584 | 640.7 | 1H NMR (400 MHz, DMSO-d6) δ 8.44 (d, J = 8.6 Hz, 1H), 8.11 (brs, 3H), 7.99 (d, J = 8.0 Hz, 1H), 7.47 (d, J = 1.2 Hz, 1H), 7.14 (d, J = 8.1 Hz, 1H), 6.97 (d, J = 1.2 Hz, 1H), 5.09-4.92 (m, 1H), 4.79-4.55 (m, 3H), 4.12 (s, 3H), 4.00 (s, 3H), 3.69-3.61 (m, 2H), 3.32 (s, 3H), 2.34-1.70 (m, 8H), 1.70-1.47 (m, 4H), 1.43 (d, J = 7.1 Hz, 3H), 1.46-1.35 (m, 1H), 1.30-1.17 (m, 2H), 0.91-0.84 (m, 1H), 0.78-0.58 (m, 3H), 0.54-0.42 (m, 1H). |
| 585 | 664.5 | 1H NMR (400 MHz, DMSO-d6) δ 8.06 (d, J = 8.0 Hz, 1H), 7.98 (brs, 3H), 7.64 (d, J = 8.5 Hz, 1H), 7.44 (s, 1H), 7.24 (d, J = 8.1 Hz, 1H), 7.13 (s, 1H), 6.95 (d, J = 1.2 Hz, 1H), 5.45 (t, J = 13.5 Hz, 1H), 5.34-5.03 (m, 2H), 4.10 (s, 3H), 4.00 (s, 3H), 3.73-3.68 (m, 1H), 3.59-3.49 (m, 2H), 3.47-3.36 (m, 1H), 3.37 (s, 3H), 2.22-1.66 (m, 6H), 1.66-1.52 (m, 1H), 1.48 (d, J = 7.1 Hz, 3H), 1.43 (s, 3H), 1.40-1.23 (m, 1H), 1.23-1.05 (m, 2H), 0.56-0.45 (m, 1H), 0.21 (dd, J = 6.9, 3.6 Hz, 1H). |
| 586 | 628.6 | 1H NMR (400 MHz, DMSO-d6) δ 8.44 (d, J = 8.8 Hz, 1H), 8.05 (d, J = 8.1 Hz, 1H), 7.98 (s, 3H), 7.45 (s, 1H), 7.21 (d, J = 8.1 Hz, 1H), 7.04 (s, 1H), 6.94 (d, J = 1.2 Hz, 1H), 5.27-5.12 (m, 1H), 4.94-4.83 (m, 1H), 4.61-4.50 (m, 1H), 4.12 (s, 3H), 3.99 (s, 3H), 3.74-3.68 (m, 2H), 3.55 (s, 2H), 3.60-3.48 (m, 1H), 3.47-3.35 (m, 1H), 3.37 (s, 3H), 2.02-1.90 (m, 2H), 1.82-1.66 (m, 2H), 1.61-1.48 (m, 2H), 1.47 (d, J = 6.9 Hz, 3H), 1.45-1.33 (m, 2H), 1.32-1.16 (m, 2H), 1.15-1.04 (m, 1H), 1.03-0.93 (m, 1H), 0.91-0.79 (m, 2H), 0.68-0.56 (m, 1H), 0.50-0.41 (m, 1H). |
| 587 | 652.6 | 1H NMR (400 MHz, DMSO-d6) δ 8.12 (d, J = 8.1 Hz, 1H), 7.98 (brs, 3H), 7.75 (d, J = 7.9 Hz, 1H), 7.46 (s, 1H), 7.31 (d, J = 8.2 Hz, 1H), 7.15 (s, 1H), 6.94 (d, J = 1.2 Hz, 1H), 5.38-5.07 (m, 3H), 4.08 (s, 3H), 3.99 (s, 3H), 3.76-3.50 (m, 3H), 3.37 (s, 3H), 2.10-1.70 (m, 4H), 1.54 (d, J = 7.1 Hz, 3H), 1.42-1.18 (m, 4H), 1.18 (s, 3H), 1.01 (s, 3H). |
| 588 | 668.4 | 1H NMR (400 MHz, DMSO-d6) δ 8.13 (d, J = 8.0 Hz, 1H), 8.09 (d, J = 9.4 Hz, 1H), 7.99 (brs, 3H), 7.45 (s, 1H), 7.30 (d, J = 8.0 Hz, 1H), 7.18 (s, 1H), 6.95 (d, J = 1.2 Hz, 1H), 5.46-5.22 (m, 3H), 4.09 (s, 3H), 3.99 (s, 3H), 3.74-3.68 (m, 2H), 3.59-3.48 (m, 2H), 3.47-3.33 (m, 2H), 3.37 (s, 3H), 2.61-2.53 (m, 2H), 2.02-1.88 (m, 1H), 1.82-1.60 (m, 3H), 1.45 (d, J = 6.9 Hz, 3H), 1.34 (s, 3H), 1.20 (s, 3H), 1.18-1.02 (m, 1H). |
| 589 | 666.4 | 1H NMR (400 MHz, DMSO-d6) δ 8.26 (d, J = 9.4 Hz, 1H), 8.16 (d, J = 8.0 Hz, 1H), 8.00 (brs, 3H), 7.45 (s, 1H), 7.34 (d, J = 8.1 Hz, 1H), 7.19 (s, 1H), 6.95 (d, J = 1.2 Hz, 1H), 5.56-5.29 (m, 3H), 4.10 (s, 3H), 4.00 (s, 3H), 3.73-3.68 (m, 1H), 3.57-3.48 (m, 3H), 3.47-3.39 (m, 1H), 3.48-3.36 (m, 3H), 3.37 (s, 3H), 3.13-3.00 (m, 1H), 2.03-1.69 (m, 5H), 1.48 (d, J = 6.9 Hz, 3H), 1.17-0.94 (m, 4H). |
| 590 | 638.6 | 1H NMR (400 MHz, DMSO-d6) δ 8.89 (s, 2H), 8.70 (d, J = 7.9 Hz, 1H), 8.10 (d, J = 8.2 Hz, 1H), 8.05 (s, 2H), 7.95 (s, 1H), 7.37 (d, J = 1.3 Hz, 1H), 7.25-7.18 (m, 2H), 7.04 (dt, J = 14.6, 7.4 Hz, 2H), 6.81 (s, 1H), 6.41 (s, 1H), 6.10 (d, J = 15.7 Hz, 1H), 5.86 (d, J = 15.7 Hz, 1H), 5.05 (p, J = 7.1 Hz, 1H), 4.94-4.68 (m, 1H), 4.54-4.35 (m, 1H), 4.16 (s, 3H), 4.03 (s, 3H), 3.47-3.27 (m, 2H), 3.15-2.86 (m, 2H), 2.86-2.64 (m, 2H), 2.41-2.25 (m, 2H), 2.18-2.06 (m, 1H), 2.01-1.78 (m, 2H), 1.73-1.49 (m, 2H), 1.45 (d, J = 7.2 Hz, 3H). |
| 591 | 606.4 | 1H NMR (400 MHz, DMSO-d6) δ 8.74 (s, 3H), 8.66 (d, J = 8.1 Hz, 1H), 8.06 (d, J = 8.1 Hz, 1H), 8.02 (d, J = 6.4 Hz, 1H), 7.82 (d, J = 7.4 Hz, 1H), 7.76 (d, J = 10.9 Hz, 1H), 7.20 (d, J = 8.2 Hz, 1H), 7.15 (s, 1H), 5.13 (p, J = 7.1 Hz, 1H), 4.95-4.72 (m, 2H), 4.62-4.49 (m, 1H), 4.42 (s, 1H), 3.97 (s, 3H), 3.48-3.27 (m, 1H), 3.15-2.88 (m, 3H), 2.03-1.84 (m, 2H), 1.79-1.58 (m, 3H), 1.45 (d, J = 7.1 Hz, 3H), 1.43-1.29 (m, 3H), 1.22 (s, 3H), 1.19-1.02 (m, 3H), 0.95 (s, 3H). |

TABLE 3-continued

| Example | ES/MS m/z [M + H]+ | ¹H NMR |
|---|---|---|
| 592 | 618.5 | 1H NMR (400 MHz, DMSO-d6) δ 8.79 (s, 3H), 8.45 (d, J = 8.1 Hz, 1H), 8.14-7.97 (m, 2H), 7.83 (d, J = 7.4 Hz, 1H), 7.42 (s, 1H), 7.19 (d, J = 8.2 Hz, 1H), 7.11 (s, 1H), 5.17-5.06 (m, 1H), 5.01-4.79 (m, 2H), 4.62-4.51 (m, 1H), 4.50-4.38 (m, 1H), 4.00 (s, 3H), 3.98 (s, 3H), 3.54-3.32 (m, 2H), 3.10-2.92 (m, 2H), 2.44-2.29 (m, 1H), 2.03-1.86 (m, 2H), 1.74-1.56 (m, 1H), 1.45 (d, J = 7.1 Hz, 3H), 1.43-1.28 (m, 4H), 1.21 (s, 3H), 1.16-1.00 (m, 4H), 0.95 (s, 3H). |
| 593 | 626.5 | 1H NMR (400 MHz, DMSO-d6) δ 8.83 (d, J = 7.0 Hz, 1H), 8.81 (s, 3H), 8.65 (d, J = 8.0 Hz, 1H), 8.09 (d, J = 8.0 Hz, 1H), 8.01 (d, J = 6.4 Hz, 1H), 7.77 (d, J = 10.8 Hz, 1H), 7.38-7.28 (m, 2H), 7.28-7.16 (m, 4H), 5.19 (p, J = 7.0 Hz, 1H), 5.00-4.83 (m, 2H), 4.83-4.66 (m, 2H), 4.51-4.34 (m, 1H), 3.98 (s, 3H), 3.43 (dd, J = 35.0, 12.5 Hz, 2H), 3.17-2.88 (m, 2H), 2.46-2.29 (m, 2H), 2.30-2.14 (m, 1H), 2.00-1.83 (m, 1H), 1.64-1.52 (m, 1H), 1.49 (d, J = 7.1 Hz, 3H), 1.47-1.37 (m, 1H), 1.34-1.06 (m, 2H), 0.66-0.37 (m, 1H). |
| 594 | 654.5 | 1H NMR (400 MHz, DMSO-d6) δ 8.92 (s, 2H), 8.72 (d, J = 8.0 Hz, 1H), 8.10 (d, J = 8.0 Hz, 1H), 7.98 (d, J = 1.2 Hz, 1H), 7.89 (d, J = 7.4 Hz, 1H), 7.35 (d, J = 1.2 Hz, 1H), 7.25 (d, J = 8.1 Hz, 1H), 7.19 (s, 1H), 5.46-5.29 (m, 1H), 5.29-5.18 (m, 1H), 5.18-5.06 (m, 1H), 5.00-4.75 (m, 1H), 4.74-4.50 (m, 4H), 4.52-4.39 (m, 1H), 4.11 (s, 3H), 4.02 (s, 3H), 3.53.3.35 (m, 2H), 3.17-2.91 (m, 2H), 2.44-2.28 (m, 1H), 2.02-1.78 (m, 3H), 1.78-1.59 (m, 1H), 1.44 (d, J = 7.1 Hz, 3H), 1.42-1.33 (m, 0H), 1.19 (s, 3H), 0.91 (s, 3H), 0.88-0.67 (m, 1H). |
| 595 | 626.3 | 1H NMR (400 MHz, DMSO-d6) δ 8.79 (s, 2H), 8.71-8.61 (m, 1H), 8.56 (d, J = 8.8 Hz, 1H), 8.07 (d, J = 8.0 Hz, 1H), 8.02 (d, J = 6.4 Hz, 1H), 7.78 (d, J = 10.7 Hz, 1H), 7.25 (d, J = 8.0 Hz, 1H), 7.23 (s, 1H), 5.66 (t, J = 13.6 Hz, 1H), 5.16 (dd, J = 27.7, 14.5 Hz, 1H), 5.10-4.98 (m, 1H), 4.83 (dtd, J = 49.1, 9.4, 4.5 Hz, 1H), 4.51-4.27 (m, 1H), 3.94 (s, 3H), 3.80-3.50 (m, 1H), 3.52-3.32 (m, 1H), 3.16-2.90 (m, 3H), 2.41-2.26 (m, 1H), 2.25-1.99 (m, 1H), 2.00-1.83 (m, 2H), 1.69-1.50 (m, 2H), 1.45 (d, J = 7.0 Hz, 3H), 1.38-1.19 (m, 1H), 0.95-0.77 (m, 1H), 0.74-0.56 (m, 1H), 0.56-0.38 (m, 2H). |
| 596 | 613.6 | 1H NMR (400 MHz, DMSO-d6) δ 8.73 (s, 2H), 8.45 (s, 1H), 8.26 (s, 1H), 8.09 (d, J = 8.2 Hz, 1H), 7.86 (d, J = 7.4 Hz, 1H), 7.26 (d, J = 1.8 Hz, 1H), 7.22 (d, J = 8.2 Hz, 1H), 5.13 (t, J = 7.2 Hz, 1H), 4.89 (s, 1H), 4.71-4.48 (m, 2H), 4.11 (s, 3H), 3.69-3.42 (m, 3H), 3.19 (s, 3H), 2.02-1.86 (m, 2H), 1.84-1.54 (m, 1H), 1.46 (d, J = 7.1, 2.3 Hz, 3H), 1.42-1.28 (m, 5H), 1.22 (s, 3H), 1.19-1.02 (m, 3H), 0.95 (s, 3H), 0.93-0.83 (m, 1H). |
| 597 | 662.3 | 1H NMR (400 MHz, DMSO-d6) δ 8.93 (d, J = 7.2 Hz, 1H), 8.77 (s, 2H), 8.68 (d, J = 8.0 Hz, 1H), 8.17 (d, J = 8.1 Hz, 1H), 8.00 (d, J = 6.4 Hz, 1H), 7.78 (d, J = 10.7 Hz, 1H), 7.39-7.31 (m, 3H), 7.31-7.19 (m, 3H), 5.44-5.32 (m, 1H), 5.32-5.26 (m, 1H), 5.25-5.09 (m, 1H), 4.82 (dtd, J = 49.0, 9.4, 4.6 Hz, 1H), 4.69-4.46 (m, 4H), 4.48-4.30 (m, 1H), 3.96 (s, 3H), 3.54-3.43 (m, 1H), 3.44-3.32 (m, 1H), 3.12-2.86 (m, 2H), 2.41-2.18 (m, 1H), 2.04-1.83 (m, 1H), 1.74-1.54 (m, 1H), 1.47 (d, J = 7.1 Hz, 3H), 1.27-0.83 (m, 1H). |
| 598 | 634.3 | 1H NMR (400 MHz, DMSO-d6) δ 9.23 (d, J = 7.0 Hz, 1H), 8.55 (dd, J = 41.6, 2.6 Hz, 2H), 8.12-8.09 (m, 1H), 8.08 (s, 3H), 7.59 (s, 1H), 7.28 (d, J = 8.1 Hz, 1H), 7.10 (s, 1H), 7.04 (d, J = 1.2 Hz, 1H), 5.25 (p, J = 7.1 Hz, 1H), 4.92-4.77 (m, 1H), 4.67-4.54 (m, 1H), 4.54-4.34 (m, 3H), 4.13 (s, 3H), 4.02 (s, 3H), 3.84-3.63 (m, 1H), 2.72-2.64 (m, 1H), 2.48-2.22 (m, 3H), 1.95-1.72 (m, 3H), 1.69-1.58 (m, 1H), 1.52 (d, J = 7.1 Hz, 3H), 1.50-1.37 (m, 2H), 1.34 (dd, J = 12.8, 4.4 Hz, 1H), 1.29-1.12 (m, 1H), 0.69-0.56 (m, 1H). |
| 599 | 688.7 | 1H NMR (400 MHz, DMSO-d6) δ 8.71 (s, 2H), 8.69 (d, J = 8.2 Hz, 1H), 8.44 (d, J = 8.6 Hz, 1H), 8.04 (d, J = 6.4 Hz, 1H), 8.00 (d, J = 8.0 Hz, 1H), 7.88 (d, J = 10.8 Hz, 1H), 7.15 (d, J = 8.1 Hz, 1H), 7.07 (s, 1H), 5.08-4.97 (m, 1H), 4.97-4.64 (m, 3H), 4.59-4.48 (m, 1H), 4.49-4.26 (m, 3H), 3.60-3.14 (m, 2H), 3.15-2.86 (m, 3H), 2.42-2.26 (m, 1H), 1.90 (dd, J = 28.1, 9.1 Hz, 2H), 1.74-1.46 (m, 5H), 1.43 (d, J = 7.1 Hz, 3H), 1.41-1.13 (m, 2H), 0.91-0.81 (m, 1H), 0.78-0.57 (m, 2H), 0.55-0.41 (m, 1H). |
| 600 | 660.7 | 1H NMR (400 MHz, DMSO-d6) δ 8.73 (s, 3H), 8.66 (d, J = 8.0 Hz, 1H), 8.43 (d, J = 8.6 Hz, 1H), 8.02 (d, J = 6.5 Hz, 1H), 7.99 (d, J = 8.0 Hz, 1H), 7.79 (d, J = 10.9 Hz, 1H), 7.14 (d, J = 8.1 Hz, 1H), 7.07 (s, 1H), 5.00 (p, 1H), 4.95-4.71 (m, 1H), 4.71-4.52 (m, 3H), 4.50-4.29 (m, 1H), 3.83-3.66 (m, 2H), 3.67-3.19 (m, 1H), 3.15-2.89 (m, 4H), 2.41-2.28 (m, 1H), 2.02-1.79 (m, 2H), 1.74-1.60 (m, 2H), 1.61-1.47 (m, 2H), 1.43 (d, J = 7.1 Hz, 3H), 1.41-1.31 (m, 1H), 1.24 (s, 2H), 0.91-0.80 (m, 1H), 0.79-0.57 (m, 2H), 0.52-0.44 (m, 1H), 0.33-0.23 (m, 2H), 0.22-0.08 (m, 2H). |
| 601 | 620.6 | 1H NMR (400 MHz, DMSO-d6) δ 8.74 (s, 2H), 8.64 (d, J = 8.1 Hz, 1H), 8.43 (d, J = 8.5 Hz, 1H), 7.77 (d, J = 10.9 Hz, 1H), 7.13 (t, J = 4.0 Hz, 2H), 5.00 (p, J = 7.5 Hz, 1H), 4.94-4.72 (m, 1H), 4.73-4.30 (m, 5H), 3.83-3.64 (m, 2H), 3.12-2.86 (m, 4H), 2.01-1.80 (m, 3H), 1.74-1.59 (m, 3H), 1.60-1.46 (m, 2H), 1.44 (d, J = 7.1 Hz, 3H), 1.40-1.29 (m, |

TABLE 3-continued

| Example | ES/MS m/z [M + H]+ | 1H NMR |
|---|---|---|
| | | 1H), 1.32-1.08 (m, 2H), 0.91-0.82 (m, 1H), 0.78-0.56 (m, 3H), 0.53-0.43 (m, 1H). |
| 602 | 650.6 | 1H NMR (400 MHz, DMSO-d6) δ 8.65 (d, J = 7.9 Hz, 1H), 8.19 (s, 1H), 8.02 (t, J = 7.3 Hz, 2H), 7.83 (d, J = 7.1 Hz, 1H), 7.65 (d, J = 10.5 Hz, 1H), 7.35 (s, 1H), 7.18 (d, J = 8.1 Hz, 1H), 5.22-4.98 (m, 1H), 4.98-4.66 (m, 4H), 4.47-4.26 (m, 1H), 4.08-3.85 (m, 1H), 3.71-3.55 (m, 1H), 3.53-3.40 (m, 3H), 3.21-3.09 (m, 1H), 3.09-2.91 (m, 1H), 2.03-1.85 (m, 2H), 1.85-1.61 (m, 2H), 1.45 (d, J = 7.0 Hz, 3H), 1.30-1.24 (m, 6H), 1.24-1.19 (m, 2H), 1.22 (s, 3H), 0.93 (s, 3H). |
| 603 | 646.7 | 1H NMR (400 MHz, DMSO-d6) δ 8.46 (s, 1H), 8.18 (d, J = 7.1 Hz, 1H), 8.06 (d, J = 8.1 Hz, 1H), 7.60 (d, J = 10.5 Hz, 1H), 7.30 (s, 1H), 7.21 (d, J = 8.2 Hz, 1H), 6.53 (s, 1H), 5.17 (p, J = 7.1 Hz, 1H), 4.88-4.70 (m, 1H), 4.81 (d, J = 5.5 Hz, 1H), 4.74 (d, J = 6.3 Hz, 1H), 4.68 (d, J = 22.1 Hz, 2H), 4.41 (d, J = 6.3 Hz, 1H), 4.19 (d, J = 5.6 Hz, 1H), 4.17-4.05 (m, 1H), 3.91-3.70 (m, 1H), 3.61-3.28 (m, 7H), 3.24-2.98 (m, 1H), 2.83-2.56 (m, 1H), 2.28-2.10 (m, 2H), 2.10-1.89 (m, 1H), 1.84-1.53 (m, 3H), 1.49 (d, J = 7.1 Hz, 3H), 1.45-1.27 (m, 2H), 1.27-1.17 (m, 1H), 1.19-1.00 (m, 1H), 0.95-0.79 (m, 1H), 0.66-0.43 (m, 1H). |
| 604 | 634.4 | 1H NMR (400 MHz, DMSO-d6) δ 9.24 (d, J = 7.0 Hz, 1H), 8.60 (d, J = 2.6 Hz, 1H), 8.50 (d, J = 2.6 Hz, 1H), 8.10 (d, J = 8.0 Hz, 2H), 7.95 (s, 2H), 7.48 (d, 1H), 7.28 (d, J = 8.1 Hz, 1H), 7.10 (s, 1H), 6.98 (d, J = 15.9 Hz, 1H), 5.25 (p, J = 7.0 Hz, 1H), 4.83 (d, J = 13.5 Hz, 1H), 4.65-4.54 (m, 1H), 4.27-4.19 (m, 1H), 4.12 (s, 3H), 4.00 (s, 3H), 3.86-3.70 (m, 1H), 3.70-3.48 (m, 2H), 3.26-3.08 (m, 1H), 2.74-2.62 (m, 2H), 2.48-2.26 (m, 2H), 2.11-1.79 (m, 3H), 1.76-1.58 (m, 1H), 1.52 (d, J = 7.1 Hz, 3H), 1.49-1.31 (m, 3H), 1.30-1.09 (m, 1H), 0.75-0.45 (m, 1H). |
| 624 | 626.3 | 1H NMR (400 MHz, DMSO-d6) δ 8.74 (br s, 3H), 8.67 (d, J = 7.1 Hz, 1H), 8.64 (d, J = 8.2 Hz, 1H), 8.06 (d, J = 1.8 Hz, 1H), 8.04 (s, 1H), 7.76 (d, J = 10.8 Hz, 1H), 7.25 (d, J = 8.2 Hz, 1H), 7.18 (s, 1H), 4.93-4.70 (m, 2H), 4.64-4.55 (m, 1H), 4.49-4.35 (m, 2H), 3.99 (s, 3H), 3.51-3.42 (m, 1H), 3.41-3.33 (m, 1H), 3.11-2.91 (m, 2H), 2.40-2.29 (m, 2H), 2.26-1.85 (m, 2H), 1.76 (d, J = 7.1 Hz, 3H), 1.55 (dt, J = 8.9, 4.6 Hz, 1H), 1.45-1.27 (m, 2H), 0.96-0.78 (m, 2H), 0.69-0.60 (m, 1H). |
| 625 | 626.3 | 1H NMR (400 MHz, DMSO-d6) δ 8.73 (br s, 3H), 8.65 (d, J = 8.1 Hz, 1H), 8.61 (d, J = 8.6 Hz, 1H), 8.06 (d, J = 6.4 Hz, 1H), 8.02 (d, J = 8.0 Hz, 1H), 7.76 (d, J = 10.8 Hz, 1H), 7.18 (d, J = 8.1 Hz, 1H), 7.17 (s, 1H), 5.03 (p, J = 7.2 Hz, 1H), 4.93-4.66 (m, 2H), 4.60-4.51 (m, 1H), 4.46-4.35 (m, 1H), 3.99 (s, 3H), 3.51-3.42 (m, 1H), 3.41-3.33 (m, 1H), 3.02 (d, J = 27.1 Hz, 2H), 2.45-2.27 (m, 2H), 2.14-2.01 (m, 2H), 1.98-1.86 (m, 1H), 1.82-1.73 (m, 1H), 1.43 (d, J = 7.1 Hz, 3H), 0.95-0.88 (m, 1H), 0.70-0.62 (m, 2H). |
| 626 | 642.3 | 1H NMR (400 MHz, DMSO-d6) δ 8.82-8.67 (m, 4H), 8.21-7.90 (m, 3H), 7.826-7.79 (m, 2H), 7.23 (d, J = 8.2 Hz, 1H), 7.00 (s, 1H), 5.12 (p, J = 7.1 Hz, 1H), 4.92-4.70 (m, 2H), 4.46-4.32 (m, 2H), 3.52-3.43 (m, 1H), 3.42-3.33 (m, 1H), 3.12-2.89 (m, 2H), 1.99-1.86 (m, 2H), 1.76-1.62 (m, 2H), 1.52-1.29 (m, 7H), 1.21 (s, 3H), 1.17-1.04 (s, 2H), 0.94 (s, 3H). |
| 627 | 622.3 | 1H NMR (400 MHz, DMSO-d6) δ 9.23 (d, J = 7.0 Hz, 1H), 8.60 (d, J = 2.6 Hz, 1H), 8.49 (d, J = 2.6 Hz, 1H), 8.10 (d, J = 8.0 Hz, 1H), 7.97 (s, 4H), 7.40 (s, 1H), 7.28 (d, J = 8.1 Hz, 1H), 7.09 (s, 1H), 6.92 (d, J = 1.2 Hz, 1H), 5.25 (p, J = 7.0 Hz, 1H), 4.90-4.75 (m, 1H), 4.63-4.51 (m, 1H), 4.12 (s, 3H), 3.99 (s, 3H), 3.32-3.04 (m, 2H), 2.74-2.62 (m, 1H), 2.48-2.30 (m, 1H), 2.06-2.97 (m, 1H), 1.81-1.71 (m, 1H), 1.66-1.31 (m, 6H), 1.298-1.14 (m, 1H), 0.69-0.56 (m, 1H). |
| 628 | 632.4 | 1H NMR (400 MHz, DMSO-d6) δ 8.65 (d, J = 8.4 Hz, 1H), 8.06 (d, J = 8.0 Hz, 1H), 7.97 (s, 3H), 7.44 (s, 1H), 7.21 (d, J = 8.1 Hz, 1H), 7.05 (s, 1H), 6.93 (d, J = 1.2 Hz, 1H), 5.34-5.24 (m, 1H), 4.96-4.86 (m, 1H), 4.59-4.49 (m, 1H), 4.11 (s, 3H), 4.01-3.92 (m, 4H), 3.73-3.68 (m, 1H), 3.54 (s, 2H), 3.43-3.34 (m, 4H), 3.23 (s, 3H), 2.03-1.89 (m, 2H), 1.81-1.71 (m, 1H), 1.63-1.54 (m, 2H), 1.52-1.35 (m, 4H), 1.35-1.22 (m, 1H), 1.17-1.00 (m, 2H), 0.91-0.78 (m, 1H), 0.64-0.52 (m, 1H). |
| 629 | 668.3 | 1H NMR (400 MHz, DMSO-d6) δ 8.65 (d, J = 8.4 Hz, 1H), 8.18 (br s, 3H), 8.06 (d, J = 8.1 Hz, 1H), 7.45 (s, 1H), 7.21 (d, J = 8.1 Hz, 1H), 7.05 (s, 1H), 6.94 (d, J = 1.2 Hz, 1H), 6.85 (t, J = 74.9 Hz, 1H), 5.29 (p, J = 7.1 Hz, 1H), 4.97-4.87 (m, 1H), 4.69-4.64 (m, 1H), 4.59-4.48 (m, 1H), 4.11 (s, 3H), 3.99 (s, 3H), 3.95 (dd, J = 9.0, 5.8 Hz, 1H), 3.61 (br s, 2H), 3.45 (br s, 1H), 3.23 (s, 3H), 2.03-1.88 (m, 4H), 1.62-1.52 (m, 2H), 1.47 (d, J = 7.0 Hz, 3H), 1.51-1.38 (m, 1H), 1.35-1.18 (m, 1H), 1.18-0.98 (m, 1H), 0.91-0.78 (m, 1H), 0.65-0.53 (m, 1H). |
| 630 | 681.5 | 1H NMR (400 MHz, DMSO-d6) δ 9.27 (br s, 1H), 8.69 (br s, 1H), 8.10 (d, J = 8.0 Hz, 1H), 7.98 (br s, 3H), 7.47 (br s, 1H), 7.42 (s, 1H), 7.27 (d, J = 8.1 Hz, 1H), 7.10 (s, 1H), 6.94 (d, J = 1.1 Hz, 1H), 5.29 (p, J = 7.4 Hz, 1H), 4.92-4.81 (m, 1H), 4.65-4.56 (m, 1H), 4.11 (s, 3H), 4.07 (s, 3H), 3.99 (s, 3H), 3.36 (s, 3H), 2.29-2.20 m, 1H), 2.00-1.89 (m, 1H), 1.80- |
| 606 | 666.3 | 1H NMR (400 MHz, DMSO-d6) δ 9.01 (d, J = 7.8 Hz, 1H), 8.63 (d, J = 2.6 Hz, 1H), 8.51 (d, J = 2.5 Hz, 1H), 8.10 (d, J = 8.1 Hz, 1H), 7.97 (s, |

TABLE 3-continued

| Example | ES/MS m/z [M + H]+ | 1H NMR |
|---|---|---|
| | | 3H), 7.44 (s, 1H), 7.32 (d, J = 8.1 Hz, 1H), 7.05 (s, 1H), 6.93 (d, J = 1.2 Hz, 1H), 5.39 (p, J = 7.1 Hz, 1H), 4.68-4.57 (m, 1H), 4.57-4.42 (m, 1H), 4.11 (s, 3H), 3.99 (s, 3H), 3.96-3.44 (m, 8H), 3.37 (s, 3H), 3.21-3.00 (m, 1H), 2.65-2.55 (m, 1H), 2.07-1.88 (m, 1H), 1.83-1.70 (m, 1H), 1.63 (d, J = 7.0 Hz, 3H), 1.60-1.38 (m, 2H), 1.34-1.12 (m, 2H), 1.11-0.91 (m, 2H). |
| 607 | 646.5 | 1H NMR (400 MHz, DMSO-d6) δ 8.75 (s, 3H), 8.69-8.58 (m, 1H), 8.45 (t, J = 8.3 Hz, 1H), 8.07-7.91 (m, 2H), 7.62-7.44 (m, 1H), 7.30 (d, J = 11.8 Hz, 1H), 7.22-7.05 (m, 1H), 5.09-4.96 (m, 1H), 4.94-4.82 (m, 1H), 4.83-4.63 (m, 2H), 4.50-4.26 (m, 1H), 4.06-3.91 (m, 1H), 3.70-3.62 (m, 1H), 3.30 (s, 1H), 3.18 (s, 1H), 3.11-2.94 (m, 2H), 2.93 (s, 1H), 2.42-2.25 (m, 1H), 2.04-1.79 (m, 4H), 1.75-1.48 (m, 4H), 1.44 (dd, J = 7.1, 2.4 Hz, 3H), 1.41-1.16 (m, 3H), 1.15-0.99 (m, 1H), 0.94-0.80 (m, 2H), 0.79-0.55 (m, 3H), 0.49 (s, 1H). |
| 608 | 666.4 | 1H NMR (400 MHz, DMSO-d6) δ 8.09 (d, J = 8.0 Hz, 1H), 7.99 (s, 3H), 7.90 (d, J = 7.5 Hz, 1H), 7.42 (s, 1H), 7.25 (d, J = 8.1 Hz, 1H), 7.14 (s, 1H), 6.94 (d, J = 1.2 Hz, 1H), 5.35 (p, J = 14.9 Hz, 1H), 5.13 (p, J = 7.4 Hz, 2H), 5.03-4.15 (m, 3H), 4.10 (s, 3H), 3.99 (s, 3H), 3.76-3.68 (m, 1H), 3.60-3.47 (m, 3H), 3.48-3.39 (m, 1H), 3.37 (s, 3H), 2.00-1.60 (m, 5H), 1.44 (d, J = 7.1 Hz, 3H), 1.43-1.35 (m, 2H), 1.30-1.21 (m, 1H), 1.19 (s, 3H), 0.91 (s, 3H). |
| 609 | 702.3 | 1H NMR (400 MHz, DMSO-d6) δ 8.19 (s, 3H), 8.09 (d, J = 8.0 Hz, 1H), 7.90 (d, J = 7.5 Hz, 1H), 7.43 (s, 1H), 7.25 (d, J = 8.1 Hz, 1H), 7.15 (s, 1H), 6.95 (d, J = 1.2 Hz, 1H), 6.86 (t, J = 74.9 Hz, 1H), 5.35 (p, J = 15.2, 14.7 Hz, 1H), 5.14 (p, J = 7.7, 7.2 Hz, 2H), 4.10 (s, 3H), 4.00 (s, 3H), 3.93-3.74 (m, 6H), 3.68-3.52 (m, 2H), 3.52-3.28 (m, 1H), 2.06-1.59 (m, 5H), 1.44 (d, J = 7.1 Hz, 3H), 1.41-1.35 (m, 1H), 1.29-1.21 (m, 1H), 1.19 (s, 3H), 0.91 (s, 3H). |
| 610 | 666.7 | 1H NMR (400 MHz, DMSO-d6) δ 9.23 (d, J = 6.9 Hz, 1H), 8.60 (s, 1H), 8.09 (d, J = 8.0 Hz, 1H), 7.97 (d, J = 9.0 Hz, 3H), 7.44 (s, 1H), 7.27 (d, J = 8.1 Hz, 1H), 7.09 (s, 1H), 6.94 (d, J = 1.2 Hz, 1H), 5.23 (p, J = 7.0 Hz, 1H), 4.92-4.78 (m, 1H), 4.68-4.50 (m, 0H), 4.12 (s, 3H), 4.00 (s, 3H), 3.97-3.77 (m, 1H), 3.75-3.63 (m, 1H), 3.65-3.42 (m, 2H), 3.37 (s, 3H), 3.50-3.18 (m, 1H), 2.63 (s, 3H), 2.42-2.17 (m, 2H), 2.06-1.86 (m, 1H), 1.84-1.70 (m, 1H), 1.54 (s, 2H), 1.50 (d, J = 7.1 Hz, 3H), 1.48-1.35 (m, 2H), 1.30-1.12 (m, 3H), 0.62-0.39 (m, 1H). |
| 611 | 644.6 | 1H NMR (400 MHz, DMSO-d6) δ 8.16 (d, J = 7.2 Hz, 1H), 8.06 (d, J = 8.1 Hz, 1H), 7.98 (s, 3H), 7.45 (s, 1H), 7.22 (d, J = 8.2 Hz, 1H), 7.03 (s, 1H), 6.93 (s, 1H), 5.18 (p, J = 7.0 Hz, 1H), 4.82 (d, J = 5.6 Hz, 1H), 4.74 (d, J = 6.3 Hz, 1H), 4.73-4.62 (m, 1H), 4.41 (d, J = 6.4 Hz, 1H), 4.49-4.27 (m, 1H), 4.33-4.26 (m, 2H), 4.20 (d, J = 5.7 Hz, 1H), 4.11 (s, 3H), 3.99 (s, 3H), 3.98-3.77 (m, 1H), 3.76-3.67 (m, 1H), 3.65-3.46 (m, 2H), 3.37 (s, 3H), 2.28-2.15 (m, 1H), 2.06-1.88 (m, 2H), 1.83-1.69 (m, 1H), 1.69-1.53 (m, 2H), 1.49 (d, J = 7.1 Hz, 3H), 1.45-1.28 (m, 4H), 1.30-1.04 (m, 2H). |
| 612 | 714.3 | 1H NMR (400 MHz, DMSO-d6) δ 9.25 (d, J = 6.9 Hz, 1H), 8.60 (d, J = 2.6 Hz, 1H), 8.50 (d, J = 2.6 Hz, 1H), 8.18 (s, 3H), 8.09 (d, J = 8.1 Hz, 1H), 7.43 (s, 1H), 7.27 (d, J = 8.1 Hz, 1H), 7.23 (s, 1H), 6.96 (d, J = 1.2 Hz, 1H), 6.86 (t, 1H), 5.23 (t, J = 7.0 Hz, 1H), 4.96-4.73 (m, 3H), 4.70 4.60 (m, 1H), 4.00 (s, 3H), 3.98-3.84 (m, 1H), 3.70-3.53 (m, 2H), 3.53-3.35 (m, 1H), 2.72-2.61 (m, 1H), 2.46-2.31 (m, 1H), 2.06-1.84 (m, 2H), 1.52 (d, J = 7.0 Hz, 3H), 1.50-1.33 (m, 5H), 1.29-1.12 (m, 2H), 1.09-0.97 (m, 1H), 0.97-0.82 (m, 1H), 0.73-0.51 (m, 1H), 0.44-0.30 (m, 1H). |
| 613 | 680.6 | 1H NMR (400 MHz, DMSO-d6) δ 8.21 (s, 3H), 8.17 (d, J = 7.2 Hz, 1H), 8.06 (d, J = 8.1 Hz, 1H), 7.46 (s, 1H), 7.22 (d, J = 8.2 Hz, 1H), 7.03 (s, 1H), 6.95 (d, J = 1.2 Hz, 1H), 6.86 (t, J = 74.9 Hz, 1H), 5.18 (p, J = 7.1 Hz, 1H), 4.82 (d, J = 5.6 Hz, 1H), 4.74 (d, J = 6.3 Hz, 1H), 4.73-4.64 (m, 1H), 4.41 (d, J = 6.3 Hz, 1H), 4.49-4.33 (m, 1H), 4.20 (d, J = 5.6 Hz, 1H), 4.12 (s, 3H), 4.09-4.02 (m, 1H), 3.99 (s, 3H), 3.70-3.34 (m, 4H), 2.28-2.15 (m, 1H), 2.08-1.86 (m, 4H), 1.69-1.54 (m, 2H), 1.49 (d, J = 7.1 Hz, 3H), 1.45-1.28 (m, 4H), 1.28-1.04 (m, 2H). |
| 614 | 678.4 | 1H NMR (400 MHz, DMSO-d6) δ 8.11 (d, J = 8.1 Hz, 1H), 8.02 (s, 3H), 7.89 (d, J = 7.8 Hz, 1H), 7.42 (s, 1H), 7.28 (d, J = 8.1 Hz, 1H), 7.14 (s, 1H), 6.94 (d, J = 1.2 Hz, 1H), 6.71-5.53 (m, 3H), 5.37 (q, J = 15.2 Hz, 1H), 5.24 (p, J = 7.4 Hz, 1H), 5.19-5.04 (m, 1H), 4.09 (s, 3H), 3.99 (s, 3H), 3.76-3.63 (m, 1H), 3.64-3.46 (m, 2H), 3.44-3.37 (m, 1H), 3.37 (s, 3H), 2.37 (p, J = 8.3, 7.7 Hz, 2H), 2.02-1.81 (m, 5H), 1.81-1.63 (m, 3H), 1.65-1.54 (m, 2H), 1.47 (d, J = 7.0 Hz, 3H), 1.31-1.08 (m, 2H), 1.06-0.76 (m, 1H). |
| 615 | 620.4 | 1H NMR (400 MHz, DMSO-d6) δ 8.78 (s, 3H), 8.70 (d, J = 7.9 Hz, 1H), 8.08 (d, J = 8.1 Hz, 1H), 8.00 (s, 1H), 7.92 (d, J = 8.6 Hz, 1H), 7.35 (s, 1H), 7.24 (d, J = 8.1 Hz, 1H), 7.09 (s, 1H), 5.28 (p, J = 7.1 Hz, 1H), 4.92 |

TABLE 3-continued

| Example | ES/MS m/z [M + H]+ | ¹H NMR |
|---|---|---|
| | | (td, J = 9.4, 4.5 Hz, 1H), 4.83-4.70 (m, 2H), 4.59-4.50 (m, 1H), 4.50-4.38 (m, 1H), 4.14 (s, 3H), 4.02 (s, 3H), 3.78 (t, J = 4.1 Hz, 1H), 3.48-3.34 (m, 1H), 3.37 (s, 3H), 3.14-2.90 (m, 2H), 2.41-2.31 (m, 1H), 2.00-1.64 (m, 4H), 1.61-1.38 (m, 6H), 1.26-1.06 (m, 3H), 0.90-0.79 (m, 1H). |
| 616 | 604.3 | 1H NMR (400 MHz, DMSO-d6) δ 8.77 (s, 3H), 8.70 (d, J = 7.9 Hz, 1H), 8.44 (d, J = 8.8 Hz, 1H), 8.05-7.98 (m, 2H), 7.36 (s, 1H), 7.17 (d, J = 8.0 Hz, 1H), 7.07 (s, 1H), 5.07 (p, J = 7.3 Hz, 1H), 4.96-4.76 (m, 2H), 4.59-4.51 (m, 1H), 4.49-4.39 (m, 1H), 4.16 (s, 3H), 4.02 (s, 3H), 3.90-3.85 (m, 1H), 3.66-3.56 (m, 1H), 3.52-3.34 (m, 3H), 3.14-2.91 (m, 2H), 2.82 (t, J = 11.8 Hz, 1H), 2.40-2.30 (m, 1H), 1.99-1.81 (m, 4H), 1.45 (d, J = 7.1 Hz, 3H), 1.17-1.07 (m, 1H), 0.92 (dt, J = 9.0, 4.4 Hz, 1H), 0.62-0.56 (m, 1H). |
| 617 | 616.3 | 1H NMR (400 MHz, DMSO-d6) δ 8.76 (s, 3H), 8.69 (d, J = 7.9 Hz, 1H), 8.17 (d, J = 8.2 Hz, 1H), 8.00 (d, J = 1.3 Hz, 1H), 7.92 (d, J = 7.8 Hz, 1H), 7.35 (s, 1H), 7.31 (d, J = 8.2 Hz, 1H), 7.15 (s, 1H), 5.06-4.86 (m, 2H), 4.83-4.66 (m, 1H), 4.50-4.38 (m, 2H), 4.17 (s, 3H), 4.02 (s, 3H), 3.49-3.34 (m, 2H), 3.13-2.92 (m, 2H), 2.41-2.29 (m, 1H), 2.00-1.58 (m, 4H), 1.51 (d, J = 6.9 Hz, 3H), 1.43-1.21 (m, 1H), 1.19-1.04 (m, 1H), 0.98-0.81 (m, 2H), 0.74-0.54 (m, 2H), 0.52 (s, 2H), 0.40-0.28 (m, 1H). |
| 618 | 616.3 | 1H NMR (400 MHz, DMSO-d6) δ 8.83-8.68 (m, 4H), 8.14 (d, J = 9.7 Hz, 1H), 8.04-7.99 (m, 2H), 7.37 (d, J = 1.3 Hz, 1H), 7.15 (d, J = 8.0 Hz, 1H), 7.06 (s, 1H), 5.25-5.15 (m, 1H), 4.96-4.87 (m, 0.5HH), 4.83-4.74 (m, 0.5H), 4.66-4.39 (m, 3H), 4.15 (s, 3H), 4.02 (s, 3H), 3.51-3.34 (m, 2H), 3.13-2.91 (m, 2H), 2.41-2.30 (m, 1H), 2.00-1.56 (m, 5H), 1.43 (d, J = 7.0 Hz, 3H), 1.41-1.18 (m, 3H), 0.78-0.68 (m, 1H), 0.63 (s, 3H), 0.53 (dd, J = 8.2, 3.9 Hz, 1H). |
| 619 | 608.3 | 1H NMR (400 MHz, DMSO-d6) δ 8.77 (d, J = 6.8 Hz, 3H), 8.70 (d, J = 7.9 Hz, 1H), 8.13 (d, J = 8.1 Hz, 1H), 8.03 (d, J = 1.3 Hz, 1H), 7.37 (d, J = 1.3 Hz, 1H), 7.27 (d, J = 8.1 Hz, 1H), 7.18 (s, 1H), 5.86 (ddd, J = 19.8, 10.5, 5.4 Hz, 1H), 5.49 (t, J = 12.6 Hz, 1H), 5.18-5.03 (m, 2H), 4.95-4.76 (m, 2H), 4.51-4.38 (m, 1H), 4.22 (s, 3H), 4.18-4.07 (m, 1H), 4.03 (s, 3H), 3.90-3.77 (m, 1H), 3.49-3.34 (m, 2H), 3.13-2.91 (m, 2H), 2.68-2.59 (m, 1H), 2.44-2.30 (m, 2H), 1.99-1.85 (m, 1H), 1.44 (d, J = 6.7 Hz, 3H). |
| 620 | 590.3 | 1H NMR (400 MHz, DMSO-d6) δ 8.77 (d, J = 6.8 Hz, 1H), 8.12 (d, J = 8.1 Hz, 1H), 7.94 (s, 3H), 7.44 (s, 1H), 7.27 (d, J = 8.2 Hz, 1H), 7.15 (s, 1H), 6.92 (d, J = 1.2 Hz, 1H), 5.75 (ddd, J = 19.6, 10.5, 5.4 Hz, 1H), 5.54-5.43 (m, 1H), 5.18-5.05 (m, 2H), 4.892-4.76 (m, 1H), 4.20 (s, 3H), 4.18-4.04 (m, 1H), 4.00 (s, 3H), 3.91-3.75 (m, 3H), 3.33-3.04 (m, 4H), 2.69-2.58 (m, 1H), 2.39 (ddd, J = 16.2, 7.7, 3.2 Hz, 1H), 2.07-1.98 (m, 1H), 1.80-1.71 (m, 1H), 1.64-1.51 (m, 2H), 1.44 (d, J = 6.8 Hz, 3H). |
| 621 | 620.3 | 1H NMR (400 MHz, DMSO-d6) δ 8.78 (s, 3H), 8.70 (d, J = 7.9 Hz, 1H), 8.64 (d, J = 8.4 Hz, 1H), 8.07 (d, J = 8.1 Hz, 1H), 7.99 (d, J = 1.3 Hz, 1H), 7.35 (d, J = 1.3 Hz, 1H), 7.22 (d, J = 8.2 Hz, 1H), 7.10 (s, 1H), 5.34-5.24 (m, 1H), 4.98-4.76 (m, 2H), 4.62-4.51 (m, 1H), 4.50-4.38 (m, 1H), 4.14 (s, 3H), 4.02 (s, 3H), 3.95 (dd, J = 9.2, 5.6 Hz, 1H), 3.42 (dd, J = 25.2, 12.7 Hz, 2H), 3.23 (s, 3H), 3.14-2.90 (m, 3H), 2.41-2.30 (m, 1H), 2.05-1.85 (m, 2H), 1.64-1.50 (m, 2H), 1.47 (d, J = 7.0 Hz, 3H), 1.36-1.21 (m, 1H), 1.23-0.99 (m, 2H), 0.93-0.80 (m, 1H), 0.68-0.57 (m, 1H). |
| 622 | 618.3 | 1H NMR (400 MHz, DMSO-d6) δ 8.78 (s, 2H), 8.63 (d, J = 8.1 Hz, 1H), 8.35 (d, J = 7.2 Hz, 1H), 8.06 (dd, J = 8.2, 1.6 Hz, 1H), 8.02 (dd, J = 6.4, 1.6 Hz, 1H), 7.62 (dd, J = 10.7, 1.6 Hz, 1H), 7.34 (d, J = 1.6 Hz, 1H), 7.19 (dd, J = 8.2, 1.5 Hz, 1H), 5.10-4.72 (m, 4H), 4.46-4.34 (m, 1H), 3.95-3.77 (m, 3H), 3.60 (dd, J = 12.0, 5.3 Hz, 1H), 3.57-3.33 (m, 3H), 3.12-2.89 (m, 2H), 2.68-2.57 (m, 1H), 2.39-2.28 (m, 1H), 2.28-2.18 (m, 1H), 1.998-1.85 (m, 1H), 1.48 (d, J = 7.0 Hz, 3H), 1.30-1.20 (m, 1H), 1.18-1.10 (m, 3H), 0.95-0.81 (m, 3H), 0.665-0.55 (m, 1H), 0.28-0.20 (m, 1H), 0.17-0.08 (m, 1H). |
| 623 | 644.3 | 1H NMR (400 MHz, DMSO-d6) δ 8.86 (d, J = 9.1 Hz, 1H), 8.72 (s, 3H), 8.68 (d, J = 8.2 Hz, 1H), 8.15 (d, J = 8.1 Hz, 1H), 8.00 (d, J = 6.4 Hz, 1H), 7.76 (d, J = 10.7 Hz, 1H), 7.32 (d, J = 8.1 Hz, 1H), 7.25 (s, 1H), 5.59-5.29 (m, 2H), 4.92-4.72 (m, 1H), 4.46-4.34 (m, 1H), 4.02 (t, J = 8.0 Hz, 1H), 3.93 (s, 3H), 3.55-3.33 (m, 2H), 3.25 (s, 3H), 3.10-2.90 (m, 2H), 2.39-2.22 (m, 1H), 1.98-1.86 (m, 1H), 1.63-1.43 (m, 3H), 1.45 (d, J = 7.0 Hz, 3H), 1.30-1.06 (m, 2H), 0.93-0.73 (m, 1H), 0.68-0.52 (m, 1H). 1.70 (m, 1H), 1.60-1.33 (m, 3H), 1.46 (d, J = 7.0 Hz, 3H), 1.29-1.17 (m, 1H), 0.49-0.37 (m, 1H). |
| 631 | 634.4 | 1H NMR (400 MHz, DMSO-d6) δ 8.44 (d, J = 8.5 Hz, 1H), 8.19-7.91 (br-s, 3H), 7.99 (d, J = 8.0 Hz, 1H), 7.43 (d, J = 1.1 Hz, 1H), 7.14 (d, J = 8.1 Hz, 1H), 7.02 (s, 1H), 6.94 (d, J = 1.1 Hz, 1H), 6.34-5.94 (m, 1H), 5.09-4.95 (m, 1H), 4.74-4.63 (m, 1H), 4.62-4.51 (m, 1H), 4.13 (s, 3H), 4.00 (s, 3H), 3.39-3.26 (m, 1H), 2.47-2.34 (m, 1H), 2.23-2.12 |

TABLE 3-continued

| Example | ES/MS m/z [M + H]+ | ¹H NMR |
|---|---|---|
| | | (m, 1H), 1.91-1.80 (m, 1H), 1.71-1.46 (m, 6H), 1.43 (d, J = 7.1 Hz, 3H), 1.41-1.35 (m, 1H), 1.31-1.15 (m, 1H), 0.95-0.82 (m, 1H), 0.79-0.57 (m, 2H), 0.54-0.41 (m, 1H). |
| 632 | 660.5 | 1H NMR (400 MHz, DMSO-d6) δ 8.73-8.56 (m, 2H), 8.54 (d, J = 8.8 Hz, 1H), 8.06 (d, J = 8.0 Hz, 1H), 7.65 (d, J = 1.2 Hz, 1H), 7.24 (d, J = 8.0 Hz, 1H), 7.15 (s, 2H), 5.59-5.45 (m, 1H), 5.23-4.98 (m, 2H), 4.39-4.30 (m, 1H), 4.23-4.15 (m, 1H), 4.10 (s, 3H), 4.01 (s, 3H), 4.00-3.93 (m, 1H), 3.84-3.79 (m, 1H), 3.48-3.38 (m, 2H), 3.13-3.02 (m, 2H), 2.23-2.03 (m, 2H), 2.03-1.90 (m, 3H), 1.80-1.69 (m, 2H), 1.69-1.57 (m, 2H), 1.56-1.48 (m, 1H), 1.44 (d, J = 7.1 Hz, 3H), 1.38-1.21 (m, 1H), 0.91-0.80 (m, 1H), 0.71-0.57 (m, 1H), 0.56-0.43 (m, 2H). |
| 633 | 670.5 | 1H NMR (400 MHz, DMSO-d6) δ 9.12-9.00 (m, 1H), 8.91-8.76 (m, 1H), 8.59 (d, J = 7.6 Hz, 1H), 8.54 (d, J = 8.8 Hz, 1H), 8.06 (d, J = 8.0 Hz, 1H), 7.98 (d, J = 1.2 Hz, 1H), 7.35 (d, J = 1.3 Hz, 1H), 7.24 (d, J = 8.1 Hz, 1H), 7.17 (s, 1H), 6.15 (td, J = 55.6, 3.5 Hz, 1H), 5.61-5.48 (m, 1H), 5.23-5.00 (m, 2H), 4.38-4.21 (m, 1H), 4.11 (s, 3H), 4.03 (s, 3H), 3.54-3.35 (m, 2H), 2.92-2.71 (m, 2H), 2.21-2.01 (m, 3H), 2.00-1.89 (m, 1H), 1.68-1.49 (m, 3H), 1.44 (d, J = 7.1 Hz, 3H), 1.32 (s, 2H), 0.92-0.78 (m, 1H), 0.70-0.56 (m, 1H), 0.55-0.42 (m, 2H). |
| 634 | 683.3 | 1H NMR (400 MHz, DMSO-d6) δ 8.09 (d, J = 8.0 Hz, 1H), 8.00 (s, 3H), 7.55 (d, J = 8.5 Hz, 1H), 7.45 (s, 1H), 7.23 (d, J = 8.1 Hz, 1H), 7.08 (s, 1H), 6.94 (d, J = 1.1 Hz, 1H), 5.27-5.07 (m, 1H), 4.77-4.64 (m, 1H), 4.63-4.52 (m, 1H), 4.12 (s, 3H), 3.99 (s, 3H), 3.55 (s, 1H), 3.44-3.39 (m, 1H), 3.37 (s, 3H), 1.95 (s, 1H), 1.84-1.70 (m, 3H), 1.64 (s, 2H), 1.59-1.52 (m, 1H), 1.49 (d, J = 6.9 Hz, 3H), 1.46-1.26 (m, 4H), 1.23-1.08 (m, 2H). |
| 635 | 681.0 | 1H NMR (400 MHz, DMSO-d6) δ 8.08 (d, J = 8.1 Hz, 1H), 7.98 (s, 3H), 7.47 (s, 1H), 7.43 (d, J = 8.4 Hz, 1H), 7.25 (d, J = 8.1 Hz, 1H), 7.05 (s, 1H), 6.94 (s, 1H), 5.84-5.73 (m, 1H), 5.26-5.12 (m, 2H), 4.60-4.41 (m, 2H), 4.13 (s, 3H), 3.99 (s, 3H), 3.94-379 (m, 1H), 3.84 (d, J = 22.0 Hz, 1H), 3.75-3.68 (m, 1H), 3.37 (s, 3H), 2.31-2.18 (m, 2H), 2.05-1.89 (m, 3H), 1.88-1.71 (m, 3H), 1.58 (d, J = 7.0 Hz, 3H), 1.47 (dd, J = 7.6, 5.2 Hz, 1H). |
| 636 | 683.2 | 1H NMR (400 MHz, DMSO-d6) δ 8.06 (d, J = 8.1 Hz, 1H), 7.98 (s, 3H), 7.53 (d, J = 7.4 Hz, 1H), 7.46 (s, 1H), 7.19 (d, J = 8.1 Hz, 1H), 7.04 (s, 1H), 6.93 (d, J = 1.2 Hz, 1H), 5.08 (p, J = 7.2 Hz, 1H), 4.63-4.47 (m, 2H), 4.14 (s, 3H), 3.99 (s, 3H), 3.92-3.80 (m, 1H), 3.75-3.67 (m, 1H), 3.57-3.52 (m, 2H), 3.37 (s, 3H), 2.24-2.19 (m, 2H), 1.96-1.91 (m, 2H), 1.79-1.66 (m, 2H), 1.58-1.51 (m, 4H), 1.47 (d, J = 7.2 Hz, 3H), 1.46-1.38 (m, 1H), 1.29-1.23 (m, 1H). |
| 637 | 653.5 | 1H NMR (400 MHz, DMSO-d6) δ 8.56 (d, J = 8.8 Hz, 1H), 8.06 (d, J = 8.0 Hz, 1H), 7.97 (d, J = 10.1 Hz, 3H), 7.44 (s, 1H), 7.24 (d, J = 8.1 Hz, 1H), 7.14 (s, 1H), 6.95 (d, J = 1.1 Hz, 1H), 5.51 (t, J = 13.6 Hz, 1H), 5.14 (dd, J = 27.8, 14.6 Hz, 1H), 5.08-4.98 (m, 1H), 4.10 (s, 3H), 4.00 (s, 3H), 3.74-3.67 (m, 1H), 3.60-3.48 (m, 2H), 3.47-3.35 (m, 1H), 2.23-2.00 (m, 2H), 2.00-1.89 (m, 2H), 1.82-1.69 (m, 3H), 1.69-1.57 (m, 1H), 1.57-1.50 (m, 1H), 1.44 (d, J = 7.1 Hz, 3H), 1.39-1.26 (m, 1H), 0.91-0.78 (m, 1H), 0.72-0.57 (m, 1H), 0.56-0.39 (m, 2H). |
| 638 | 664.3 | 1H NMR (400 MHz, DMSO-d6) δ 8.59 (d, J = 8.7 Hz, 1H), 8.08 (d, J = 8.0 Hz, 1H), 7.97 (s, 3H), 7.69 (s, 1H), 7.37 (s, 1H), 7.31 (dd, J = 11.5, 1.2 Hz, 1H), 7.25 (d, J = 8.1 Hz, 1H), 5.90-5.78 (m, 1H), 5.20 (dd, J = 27.8, 14.5 Hz, 1H), 5.11-5.01 (m, 1H), 4.08-4.00 (m, 1H), 3.74-3.68 (m, 1H), 3.59-3.51 (m, 1H), 3.48-3.40 (m, 1H), 3.37 (s, 3H), 2.25-2.02 (m, 2H), 2.01-1.88 (m, 2H), 1.82-1.71 (m, 1H), 1.69-1.58 (m, 1H), 1.58-1.52 (m, 1H), 1.45 (d, J = 7.1 Hz, 3H), 1.38-1.29 (m, 1H), 1.29-1.20 (m, 2H), 1.09-0.96 (m, 2H), 0.90-0.80 (m, 1H), 0.72-0.58 (m, 1H), 0.58-0.41 (m, 4H). |
| 639 | 648.3 | 1H NMR (400 MHz, DMSO-d6) δ 8.59 (d, J = 8.8 Hz, 1H), 8.08 (d, J = 8.0 Hz, 1H), 7.92 (s, 3H), 7.63 (d, J = 1.1 Hz, 1H), 7.37 (s, 1H), 7.30-7.22 (m, 2H), 5.91-5.78 (m, 1H), 5.20 (dd, J = 27.9, 14.6 Hz, 1H), 5.12-5.01 (m, 1H), 4.07-3.99 (m, 1H), 3.43-3.32 (m, 1H), 3.14-2.94 (m, 1H), 2.29-2.03 (m, 2H), 2.02-1.91 (m, 1H), 1.86-1.49 (m, 5H), 1.45 (d, J = 7.1 Hz, 3H), 1.40-1.28 (m, 1H), 1.28-1.23 (m, 2H), 1.21 (d, J = 6.9 Hz, 3H), 1.10-0.97 (m, 2H), 0.89-0.81 (m, 1H), 0.75-0.57 (m, 1H), 0.58-0.41 (m, 3H). |
| 640 | 652.2 | 1H NMR (400 MHz, DMSO-d6) δ 8.60 (d, J = 8.8 Hz, 1H), 8.1-7.96 (m, 3H), 8.08 (d, J = 8.0 Hz, 1H), 7.63 (d, J = 1.2 Hz, 1H), 7.37 (s, 1H), 7.30-7.22 (m, 2H), 5.90-5.75 (m, 1H), 5.20 (dd, J = 27.8, 14.6 Hz, 1H), 5.12-5.01 (m, 1H), 4.98-4.70 (m, 1H), 4.08-4.00 (m, 1H), 3.47-3.33 (m, 1H), 3.03-2.83 (m, 1H), 2.42-2.34 (m, 1H), 2.26-2.02 (m, 1H), 2.02-1.85 (m, 2H), 1.85-1.74 (m, 1H), 1.71-1.58 (m, 1H), 1.58-1.51 (m, 1H), 1.45 (d, J = 7.1 Hz, 3H), 1.40-1.18 (m, 3H), 1.11-0.96 (m, 2H), 0.90-0.80 (m, 1H), 0.72-0.58 (m, 1H), 0.58-0.42 (m, 3H). |
| 641 | 667.3 | 1H NMR (400 MHz, DMSO-d6) δ 8.59 (d, J = 8.8 Hz, 1H), 8.08 (d, J = 8.0 Hz, 1H), 8.05-7.86 (m, 3H), 7.69 (s, 1H), 7.37 (s, 1H), 7.31 (dd, J = 11.6, 1.2 Hz, 1H), 7.25 (d, J = 8.1 Hz, 1H), 5.90-5.77 (m, 1H), 5.20 (dd, |

TABLE 3-continued

| Example | ES/MS m/z [M + H]+ | 1H NMR |
|---|---|---|
| | | J = 27.8, 14.5 Hz, 1H), 5.11-5.01 (m, 1H), 4.08-3.99 (m, 1H), 3.74-3.69 (m, 1H), 3.59-3.52 (m, 1H), 3.50-3.34 (m, 1H), 2.25-2.03 (m, 2H), 2.03-1.87 (m, 2H), 1.82-1.71 (m, 1H), 1.71-1.58 (m, 1H), 1.58-1.51 (m, 1H), 1.45 (d, J = 7.1 Hz, 3H), 1.38-1.29 (m, 1H), 1.30-1.20 (m, 1H), 1.08-0.97 (m, 2H), 0.91-0.82 (m, 1H), 0.72-0.59 (m, 1H), 0.57-0.42 (m, 3H). |
| 642 | 632.3 | 1H NMR (400 MHz, DMSO-d6) δ 8.55 (d, J = 8.8 Hz, 1H), 8.17-8.01 (m, 4H), 7.60 (s, 1H), 7.24 (d, J = 8.1 Hz, 1H), 7.15 (s, 1H), 7.05 (d, J = 1.2 Hz, 1H), 5.55-5.44 (m, 1H), 5.14 (dd, J = 27.9, 14.5 Hz, 1H), 5.09-5.01 (m, 1H), 4.60-4.37 (m, 1H), 4.10 (s, 3H), 4.02 (s, 3H), 3.79-3.71 (m, 1H), 2.38-2.26 (m, 1H), 2.24-1.99 (m, 2H), 1.99-1.90 (m, 1H), 1.90-1.77 (m, 3H), 1.64 (s, 2H), 1.57-1.50 (m, 1H), 1.45 (d, J = 7.1 Hz, 3H), 1.39-1.28 (m, 2H), 0.90-0.79 (m, 1H), 0.73-0.56 (m, 1H), 0.54-0.41 (m, 2H). |
| 643 | 647.4 | 1H NMR (400 MHz, DMSO-d6) δ 8.09-7.89 (m, 4H), 7.43 (s, 1H), 7.38 (d, J = 8.1 Hz, 1H), 7.09 (d, J = 1.5 Hz, 1H), 7.08-7.03 (m, 1H), 6.93 (s, 1H), 4.95-4.83 (m, 1H), 4.68-4.53 (m, 2H), 4.07 (s, 3H), 3.99 (s, 3H), 3.73-3.69 (m, 2H), 3.59-3.50 (m, 2H), 3.40 (d, J = 11.5 Hz, 1H), 3.37 (s, 3H), 2.03-1.88 (m, 1H), 1.76 (t, J = 6.6 Hz, 2H), 1.58 (d, J = 7.2 Hz, 3H), 1.47-1.20 (m, 3H), 1.22-1.12 (m, 1H), 1.17 (s, 3H), 1.11-1.02 (m, 1H), 0.98-0.88 (m, 1H), 0.85 (s, 3H), 0.49-0.31 (m, 2H). |
| 644 | 650.3 | 1H NMR (400 MHz, DMSO-d6) δ 8.28 (s, 2H), 8.10 (s, 1H), 8.05 (d, J = 8.1 Hz, 1H), 7.82 (d, J = 7.4 Hz, 1H), 7.38 (s, 1H), 7.19 (d, J = 8.1 Hz, 1H), 7.04 (s, 1H), 6.88 (s, 1H), 6.66 (t, J = 54.3 Hz, 1H), 5.34 (s, 1H), 5.13 (p, J = 7.1 Hz, 1H), 4.91-4.73 (m, 1H), 4.50-4.33 (m, 2H), 4.13 (s, 3H), 4.00 (s, 3H), 3.74-3.55 (m, 2H), 3.37-2.83 (m, 1H), 2.01-1.85 (m, 3H), 1.82-1.56 (m, 3H), 1.45 (d, J = 7.1 Hz, 3H), 1.43-1.28 (m, 3H), 1.21 (s, 3H), 1.18-1.01 (m, 2H), 0.95 (s, 3H). |
| 645 | 631.4 | NA |
| 646 | 645.4 | 1H NMR (400 MHz, DMSO-d6) δ 8.59 (d, J = 8.8 Hz, 1H), 8.13-8.03 (m, 2H), 7.96-7.87 (m, 2H), 7.80 (s, 0.4H), 7.66 (s, 0.6H), 7.40-7.30 (m, 0.4H), 7.37 (s, 1H), 7.29 (d, J = 11.5 Hz, 0.6H), 7.25 (d, J = 8.2 Hz, 1H), 5.90-5.76 (m, 1H), 5.20 (dd, J = 27.7, 14.7 Hz, 1H), 5.12-5.01 (m, 1H), 4.54 (s, 0.5H), 4.15 (s, 1H), 4.07-3.99 (m, 0.5H), 3.79-3.73 (m, 0.5H), 3.64-3.51 (m, 2H), 3.28-3.13 (m, 1H), 2.71-2.64 (m, 1H), 2.60-2.56 (m, 0.5H), 2.26-2.03 (m, 1H), 2.03-1.82 (m, 4H), 1.74-1.58 (m, 2H), 1.58-1.52 (m, 1H), 1.45 (d, J = 7.1 Hz, 3H), 1.38-1.29 (m, 1H), 1.29-1.20 (m, 1H), 1.08-0.94 (m, 2H), 0.89-0.80 (m, 1H), 0.71-0.58 (m, 1H), 0.56-0.37 (m, 3H). |
| 647 | 670.3 | 1H NMR (400 MHz, DMSO-d6) δ 8.56 (d, J = 8.9 Hz, 1H), 8.28 (s, 2H), 8.16-8.08 (s, 1H), 8.06 (d, J = 8.0 Hz, 1H), 7.38 (d, J = 1.1 Hz, 1H), 7.24 (d, J = 8.1 Hz, 1H), 7.15 (s, 1H), 6.97-6.87 (m, 1H), 6.67 (td, J = 54.2, 5.7 Hz, 1H), 5.58-5.45 (m, 1H), 5.34 (s, 1H), 5.14 (dd, J = 27.8, 14.5 Hz, 1H), 5.08-5.01 (m, 1H), 4.43 (s, 1H), 4.11 (s, 3H), 4.00 (s, 3H), 3.34-3.18 (m, 1H), 2.26-2.00 (m, 2H), 2.00-1.85 (m, 3H), 1.82-1.66 (m, 1H), 1.68-1.56 (m, 1H), 1.56-1.50 (m, 1H), 1.44 (d, J = 7.1 Hz, 3H), 1.39-1.24 (m, 1H), 0.90-0.79 (m, 1H), 0.73-0.56 (m, 1H), 0.54-0.42 (m, 2H). |
| 648 | 667.2 | 1H NMR (400 MHz, DMSO-d6) δ 8.52 (d, J = 8.3 Hz, 1H), 7.96 (s, 3H), 7.44 (s, 1H), 7.40 (d, J = 8.1 Hz, 1H), 7.19 (d, J = 1.8 Hz, 1H), 7.11 (t, J = 7.3 Hz, 1H), 6.95 (s, 1H), 5.58-5.47 (m, 1H), 5.04-4.88 (m, 1H), 4.87-4.78 (m, 1H), 4.09 (s, 3H), 3.99 (s, 3H), 3.73-3.68 (m, 1H), 3.48-3.38 (m, 1H), 3.37 (s, 3H), 2.01-1.82 (m, 3H), 1.76 (s, 2H), 1.65-1.55 (m, 1H), 1.59 (d, J = 7.2 Hz, 3H), 1.53-1.44 (m, 1H), 1.40-1.27 (m, 1H), 0.86-0.77 (m, 1H), 0.74-0.62 (m, 1H), 0.53-0.42 (m, 2H). |
| 649 | 651.4 | 1H NMR (400 MHz, DMSO-d6) δ 9.16 (d, J = 6.8 Hz, 1H), 8.61 (s, 1H), 8.55 (d, J = 5.2 Hz, 1H), 8.09 (d, J = 8.0 Hz, 1H), 7.97 (s, 3H), 7.42 (s, 1H), 7.40 (d, J = 5.2 Hz, 1H), 7.26 (d, J = 8.1 Hz, 1H), 7.08 (s, 1H), 6.93 (s, 1H), 5.20 (p, J = 6.9 Hz, 1H), 4.89-4.74 (m, 1H), 4.65-4.52 (m, 1H), 4.12 (s, 3H), 3.99 (s, 3H), 3.93-3.77 (m, 1H), 3.76-3.65 (m, 1H), 3.63-3.25 (m, 7H), 2.41-2.26 (m, 2H), 2.03-1.85 (m, 1H), 1.83-1.67 (m, 1H), 1.59-1.35 (m, 6H), 1.35-1.08 (m, 2H), 0.68-0.48 (m, 1H). |
| 650 | 669.3 | 1H NMR (400 MHz, DMSO-d6) δ 9.44 (d, J = 7.3 Hz, 1H), 8.48 (s, 1H), 8.34 (d, J = 1.1 Hz, 1H), 8.09 (d, J = 8.0 Hz, 1H), 7.96 (s, 3H), 7.43 (s, 1H), 7.27 (d, J = 8.1 Hz, 1H), 7.09 (s, 1H), 6.93 (d, J = 1.2 Hz, 1H), 5.28 (p, J = 7.2 Hz, 1H), 4.95-4.80 (m, 1H), 4.67-4.53 (m, 1H), 4.12 (s, 3H), 3.99 (s, 3H), 3.45-3.32 (m, 4H), 2.43-2.33 (m, 1H), 2.24-2.05 (m, 1H), 2.03-1.86 (m, 1H), 1.82-1.67 (m, 1H), 1.60-1.36 (m, 5H), 1.36-1.08 (m, 3H), 0.56-0.35 (m, 1H). |
| 651 | 685.3 | 1H NMR (400 MHz, DMSO-d6) δ 9.40 (d, J = 7.8 Hz, 1H), 8.53 (s, 1H), 8.42 (s, 1H), 8.09 (d, J = 8.0 Hz, 1H), 7.96 (s, 3H), 7.43 (s, 1H), 7.27 (d, J = 8.1 Hz, 1H), 7.09 (s, 1H), 6.93 (d, J = 1.1 Hz, 1H), 5.42-5.28 (m, 1H), 4.95-4.83 (m, 1H), 4.65-4.55 (m, 1H), 4.12 (s, 3H), 3.99 (s, 3H), 3.74-3.66 (m, 2H), 3.63-3.47 (m, 3H), 3.47-3.30 (m, 4H), 2.42-2.33 (m, 1H), 2.13-1.85 (m, 2H), 1.83-1.65 (m, 1H), 1.65-1.36 (m, 5H), 1.36-1.08 (m, 3H), 0.54-0.33 (m, 1H). |

TABLE 3-continued

| Example | ES/MS m/z [M + H]+ | 1H NMR |
|---|---|---|
| 652 | 681.3 | 1H NMR (400 MHz, DMSO-d6) δ 9.20 (d, J = 6.7 Hz, 1H), 8.37 (s, 1H), 8.08 (d, J = 8.0 Hz, 1H), 7.97 (s, 3H), 7.83 (s, 1H), 7.77 (d, J = 8.3 Hz, 1H), 7.48-7.40 (m, 2H), 7.32 (s, 1H), 7.25 (d, J = 8.1 Hz, 1H), 5.16 (p, J = 7.0 Hz, 1H), 4.96-4.77 (m, 2H), 4.01-3.76 (m, 2H), 3.76-3.65 (m, 1H), 3.65-3.46 (m, 2H), 3.46-3.28 (m, 5H), 2.40-2.23 (m, 2H), 2.01-1.85 (m, 1H), 1.82-1.66 (m, 1H), 1.51 (d, J = 7.0 Hz, 3H), 1.48-1.37 (m, 2H), 1.37-1.20 (m, 2H), 1.20-1.04 (m, 2H), 1.02-0.89 (m, 1H), 0.61-0.36 (m, 2H). |
| 653 | 685.3 | 1H NMR (400 MHz, DMSO-d6) δ 9.18 (d, J = 6.8 Hz, 1H), 8.36 (s, 1H), 8.08 (d, J = 8.0 Hz, 1H), 7.96 (s, 3H), 7.44 (s, 1H), 7.42 (s, 1H), 7.25 (d, J = 8.1 Hz, 1H), 7.08 (s, 1H), 6.93 (d, J = 1.2 Hz, 1H), 5.17 (p, J = 7.0 Hz, 1H), 4.88-4.73 (m, 1H), 4.66-4.53 (m, 1H), 4.11 (s, 3H), 3.99 (s, 3H), 3.90-3.81 (m, 2H), 3.74-3.67 (m, 1H), 3.62-3.47 (m, 2H), 3.45-3.28 (m, 5H), 2.39-2.24 (m, 2H), 2.02-1.85 (m, 1H), 1.81-1.65 (m, 1H), 1.59-1.34 (m, 5H), 1.34-1.02 (m, 2H), 0.64-0.47 (m, 1H). |
| 654 | 664.3 | 1H NMR (400 MHz, DMSO-d6) δ 8.11 (d, J = 8.1 Hz, 1H), 7.96 (s, 3H), 7.44 (s, 1H), 7.36-7.22 (m, 5H), 7.07 (s, 1H), 6.93 (d, J = 1.2 Hz, 1H), 5.89 (q, J = 7.3 Hz, 1H), 4.81-4.67 (m, 1H), 4.59-4.48 (m, 1H), 4.11 (s, 3H), 3.99 (s, 3H), 3.89-3.81 (m, 1H), 3.74-3.66 (m, 2H), 3.58-3.50 (m, 2H), 3.47-3.31 (m, 4H), 3.10 (s, 3H), 2.30-2.11 (m, 2H), 2.04-1.86 (m, 1H), 1.84-1.70 (m, 1H), 1.70-1.41 (m, 6H), 1.41-1.10 (m, 2H), 0.76-0.59 (m, 1H). |
| 655 | 685.2 | 1H NMR (400 MHz, DMSO-d6) δ 9.33 (d, J = 7.9 Hz, 1H), 8.30 (d, J = 5.0 Hz, 1H), 8.09 (d, J = 8.0 Hz, 1H), 7.96 (s, 3H), 7.43 (s, 1H), 7.31 (d, J = 5.1 Hz, 1H), 7.27 (d, J = 8.1 Hz, 1H), 7.09 (s, 1H), 6.93 (d, J = 1.1 Hz, 1H), 5.45-5.27 (m, 1H), 4.96-4.80 (m, 1H), 4.65-4.48 (m, 1H), 4.11 (s, 3H), 3.99 (s, 3H), 3.73-3.66 (m, 3H), 3.60-3.48 (m, 2H), 3.46-3.27 (m, 4H), 2.39-2.25 (m, 1H), 2.17-2.01 (m, 1H), 2.01-1.87 (m, 1H), 1.83-1.67 (m, 1H), 1.64-1.36 (m, 6H), 1.36-1.10 (m, 2H), 0.54-0.34 (m, 1H). |
| 656 | 669.3 | 1H NMR (400 MHz, DMSO-d6) δ 9.35 (d, J = 7.5 Hz, 1H), 8.50 (dd, J = 8.7, 5.7 Hz, 1H), 8.09 (d, J = 8.0 Hz, 1H), 7.96 (s, 3H), 7.43 (s, 1H), 7.27 (d, J = 8.1 Hz, 1H), 7.25 (dd, J = 9.0, 5.7 Hz, 1H), 7.09 (s, 1H), 6.93 (d, J = 1.1 Hz, 1H), 5.29 (p, J = 6.9 Hz, 1H), 4.97-4.80 (m, 1H), 4.66-4.51 (m, 1H), 4.12 (s, 3H), 3.99 (s, 3H), 3.74-3.64 (m, 2H), 3.61-3.46 (m, 2H), 3.46-3.28 (m, 4H), 2.45-2.36 (m, 2H), 2.02-1.88 (m, 1H), 1.84-1.68 (m, 1H), 1.61-1.33 (m, 7H), 1.32-1.13 (m, 1H), 0.61-0.39 (m, 1H). |
| 657 | 653.3 | 1H NMR (400 MHz, DMSO-d6) δ 9.45 (d, J = 7.2 Hz, 1H), 8.48 (s, 1H), 8.34 (s, 1H), 8.09 (d, J = 8.0 Hz, 1H), 7.91 (s, 3H), 7.34 (s, 1H), 7.26 (d, J = 8.0 Hz, 1H), 7.09 (s, 1H), 6.88 (s, 1H), 5.28 (p, J = 7.1 Hz, 1H), 4.94-4.80 (m, 1H), 4.68-4.53 (m, 1H), 4.12 (s, 3H), 3.99 (s, 3H), 3.43-3.29 (m, 2H), 3.18-2.77 (m, 1H), 2.43-2.29 (m, 1H), 2.23-2.09 (m, 1H), 1.87-1.34 (m, 9H), 1.34-1.09 (m, 5H), 0.53-0.34 (m, 1H). |
| 658 | 651.3 | 1H NMR (400 MHz, DMSO-d6) δ 9.44 (d, J = 7.3 Hz, 1H), 8.48 (s, 1H), 8.33 (s, 1H), 8.09 (d, J = 8.0 Hz, 1H), 8.07-7.80 (m, 3H), 7.58-7.36 (m, 1H), 7.27 (d, J = 8.0 Hz, 1H), 7.10 (s, 1H), 7.02-6.91 (m, 1H), 5.28 (p, J = 6.9 Hz, 1H), 4.88 (s, 1H), 4.68-4.57 (m, 1H), 4.57-4.16 (m, 1H), 4.12 (s, 3H), 4.00 (s, 3H), 3.84-3.73 (m, 1H), 3.24-3.11 (m, 1H), 2.72-2.63 (m, 1H), 2.61-2.53 (m, 1H), 2.37 (dd, J = 16.3, 12.3 Hz, 1H), 2.12 (dd, J = 22.6, 11.5 Hz, 1H), 2.04-1.78 (m, 3H), 1.74-1.56 (m, 1H), 1.55-1.36 (m, 5H), 1.36-1.10 (m, 2H), 0.57-0.34 (m, 1H). |
| 659 | 672.3 | 1H NMR (400 MHz, DMSO-d6) δ 9.44 (d, J = 7.3 Hz, 1H), 8.48 (s, 1H), 8.34 (s, 1H), 8.09 (d, J = 8.0 Hz, 1H), 7.97 (s, 3H), 7.43 (s, 1H), 7.27 (d, J = 8.1 Hz, 1H), 7.09 (s, 1H), 6.93 (s, 1H), 5.28 (p, J = 7.0 Hz, 1H), 4.95-4.81 (m, 1H), 4.67-4.53 (m, 1H), 4.12 (s, 3H), 3.99 (s, 3H), 3.94-3.81 (m, 1H), 3.76-3.66 (m, 2H), 3.65-3.47 (m, 2H), 3.47-3.29 (m, 1H), 2.43-2.30 (m, 1H), 2.22-2.05 (m, 1H), 2.02-1.84 (m, 1H), 1.83-1.69 (m, 1H), 1.61-1.36 (m, 5H), 1.36-1.08 (m, 3H), 0.55-0.33 (m, 1H). |
| 660 | 655.2 | 1H NMR (400 MHz, DMSO-d6) δ 9.44 (d, J = 7.3 Hz, 1H), 8.48 (s, 1H), 8.34 (s, 1H), 8.09 (d, J = 7.8 Hz, 1H), 7.89 (s, 3H), 7.42 (s, 1H), 7.27 (d, J = 8.0 Hz, 1H), 7.09 (s, 1H), 6.93 (s, 1H), 5.79-5.60 (m, 1H), 5.28 (p, J = 7.1 Hz, 1H), 4.96-4.79 (m, 1H), 4.69-4.55 (m, 1H), 4.12 (s, 3H), 4.08-4.02 (m, 2H), 3.99 (s, 3H), 3.63-3.25 (m, 4H), 2.43-2.29 (m, 1H), 2.22-2.08 (m, 1H), 1.88-1.65 (m, 2H), 1.61-1.10 (m, 8H), 0.56-0.37 (m, 1H). |
| 661 | 699.3 | 1H NMR (400 MHz, DMSO-d6) δ 9.42 (d, J = 7.6 Hz, 1H), 8.53 (s, 1H), 8.42 (s, 1H), 8.10 (d, J = 8.0 Hz, 1H), 7.97 (s, 3H), 7.67 (s, 1H), 7.33 (s, 1H), 7.31-7.22 (m, 2H), 5.41-5.26 (m, 1H), 5.03-4.89 (m, 1H), 4.89-4.77 (m, 1H), 4.06-3.94 (m, 1H), 3.94-3.26 (m, 9H), 2.61-2.52 (m, 1H), 2.44-2.28 (m, 1H), 2.13-1.98 (m, 1H), 1.98-1.84 (m, 1H), 1.83-1.69 (m, 1H), 1.60-1.39 (m, 5H), 1.39-0.91 (m, 5H), 0.56-0.31 (m, 2H). |
| 662 | 683.3 | 1H NMR (400 MHz, DMSO-d6) δ 9.47 (d, J = 7.1 Hz, 1H), 8.49 (s, 1H), 8.34 (s, 1H), 8.10 (d, J = 8.0 Hz, 1H), 7.97 (s, 3H), 7.67 (s, 1H), 7.33 (s, 1H), 7.31-7.22 (m, 2H), 5.27 (p, J = 7.0 Hz, 1H), 5.02-4.90 (m, 1H), |

TABLE 3-continued

| Example | ES/MS m/z [M + H]+ | ¹H NMR |
|---|---|---|
| | | 4.90-4.79 (m, 1H), 4.07-3.97 (m, 1H), 3.97-3.28 (m, 9H), 2.47-2.30 (m, 2H), 2.22-2.08 (m, 1H), 1.99-1.84 (m, 1H), 1.83-1.68 (m, 1H), 1.57-1.38 (m, 5H), 1.38-0.96 (m, 5H), 0.52-0.35 (m, 2H). |
| 663 | 691.3 | 1H NMR (400 MHz, DMSO-d6) δ 9.26 (d, J = 8.1 Hz, 1H), 8.30 (d, J = 5.1 Hz, 1H), 8.09 (d, J = 8.0 Hz, 1H), 7.97 (s, 3H), 7.43 (s, 1H), 7.27 (d, J = 8.0 Hz, 1H), 7.08 (s, 1H), 7.07 (s, 1H), 6.93 (s, 1H), 5.42 (p, J = 6.9, 6.5 Hz, 1H), 4.98-4.82 (m, 1H), 4.63-4.49 (m, 1H), 4.12 (s, 3H), 3.99 (s, 3H), 3.94-3.82 (m, 1H), 3.76-3.65 (m, 1H), 3.65-3.46 (m, 3H), 3.46-3.27 (m, 4H), 2.63-2.53 (m, 1H), 2.31-2.20 (m, 1H), 2.20-2.01 (m, 2H), 2.01-1.85 (m, 1H), 1.83-1.70 (m, 1H), 1.67-1.37 (m, 5H), 1.37-1.15 (m, 2H), 1.15-0.88 (m, 4H), 0.57-0.35 (m, 1H). |
| 664 | 675.3 | 1H NMR (400 MHz, DMSO-d6) δ 9.27 (d, J = 8.1 Hz, 1H), 8.31 (d, J = 5.1 Hz, 1H), 8.09 (d, J = 8.0 Hz, 1H), 7.93 (s, 3H), 7.35 (d, J = 1.1 Hz, 1H), 7.27 (d, J = 8.0 Hz, 1H), 7.10 (s, 1H), 7.08 (s, 1H), 6.88 (s, 1H), 5.49-5.35 (m, 1H), 4.97-4.82 (m, 1H), 4.66-4.50 (m, 1H), 4.11 (s, 3H), 3.99 (s, 3H), 3.44-3.27 (m, 1H), 3.19-2.84 (m, 1H), 2.61-2.53 (m, 1H), 2.36-2.21 (m, 1H), 2.21-2.00 (m, 2H), 1.88-1.38 (m, 10H), 1.38-1.14 (m, 6H), 1.14-0.88 (m, 4H), 0.56-0.34 (m, 1H). |
| 665 | 681.3 | 1H NMR (400 MHz, DMSO-d6) δ 9.18 (d, J = 6.8 Hz, 1H), 8.36 (s, 1H), 8.08 (d, J = 8.0 Hz, 1H), 8.04-7.64 (m, 3H), 7.44 (s, 1H), 7.35 (s, 1H), 7.25 (d, J = 8.1 Hz, 1H), 7.08 (s, 1H), 6.89 (s, 1H), 5.17 (p, J = 7.0 Hz, 1H), 5.11-4.90 (m, 0.5H), 4.87-4.72 (m, 1H), 4.69-4.44 (m, 1.5H), 4.27-4.17 (m, 0.5H), 4.11 (s, 3H), 3.99 (s, 3H), 3.88-3.74 (m, 0.5H), 3.45-3.04 (m, 2H), 2.86-2.70 (m, 1H), 2.39-2.24 (m, 2H), 2.03-1.34 (m, 12H), 1.34-1.21 (m, 1H), 1.21-1.06 (m, 1H), 0.63-0.45 (m, 1H). |
| 666 | 618.3 | 1H NMR (400 MHz, DMSO-d6) δ 8.54 (d, J = 8.8 Hz, 1H), 8.49-8.19 (m, 3H), 8.06 (d, J = 8.0 Hz, 1H), 7.73 (s, 0.5H), 7.47 (s, 0.5H), 7.23 (d, J = 8.0 Hz, 1H), 7.14 (m, 1.5H), 6.99 (s, 0.5H), 5.53 (t, J = 13.6 Hz, 1H), 5.13 (dd, J = 27.7, 14.4 Hz, 1H), 5.08-4.97 (m, 1H), 4.82-4.64 (m, 0.5H), 4.58-4.43 (m, 0.5H), 4.10 (s, 3H), 4.01 (s, 3H), 3.51-3.29 (m, 1H), 3.07-2.87 (m, 1H), 2.82-2.70 (m, 1H), 2.26-1.68 (m, 4H), 1.68-1.49 (m, 2H), 1.44 (d, J = 7.1 Hz, 3H), 1.39-1.16 (m, 2H), 0.91-0.77 (m, 1H), 0.73-0.56 (m, 1H), 0.56-0.39 (m, 2H). |
| 667 | 598.3 | 1H NMR (400 MHz, DMSO-d6) δ 8.35 (d, J = 36.4 Hz, 3H), 8.04 (d, J = 8.1 Hz, 1H), 7.81 (d, J = 7.4 Hz, 1H), 7.72 (s, 0.5H), 7.45 (s, 0.5H), 7.19 (d, J = 8.1 Hz, 1H), 7.12 (s, 0.5H), 7.04 (s, 1H), 6.98 (s, 0.5H), 5.12 (p, J = 6.7 Hz, 1H), 4.90-4.65 (m, 1.5H), 4.57-4.28 (m, 1.5H), 4.12 (s, 3H), 4.00 (s, 3H), 3.53-3.30 (m, 1H), 3.08-2.88 (m, 1H), 2.81-2.69 (m, 1H), 2.00-1.23 (m, 13H), 1.21 (s, 3H), 1.17-0.98 (m, 2H), 0.94 (s, 3H). |
| 668 | 664.3 | 1H NMR (400 MHz, DMSO-d6) δ 8.55 (d, J = 8.8 Hz, 1H), 8.21-7.73 (m, 4H), 7.47 (s, 1H), 7.23 (d, J = 8.0 Hz, 1H), 7.14 (s, 1H), 6.96 (s, 1H), 5.52 (t, J = 13.6 Hz, 1H), 5.32-4.76 (m, 3H), 4.58-4.20 (m, 1H), 4.10 (s, 3H), 4.00 (s, 3H), 3.88-3.73 (m, 0.5H), 3.57-3.25 (m, 1H), 3.07 (s, 0.5H), 2.82-2.67 (m, 1H), 2.27-1.17 (m, 14H), 0.89-0.76 (m, 1H), 0.73-0.55 (m, 1H), 0.55-0.40 (m, 2H). |
| 669 | 713.2 | 1H NMR (400 MHz, DMSO-d6) δ 9.12 (d, J = 7.1 Hz, 1H), 8.30-7.76 (m, 5H), 7.69 (s, 1H), 7.41 (d, J = 8.0 Hz, 1H), 7.38-7.16 (m, 3H), 5.20 (p, J = 7.0 Hz, 1H), 5.14-4.75 (m, 4H), 4.57-4.12 (m, 1H), 4.07-3.93 (m, 1H), 3.84-3.58 (m, 0.5H), 3.55-3.27 (m, 1H), 3.17-2.89 (m, 0.5H), 2.82-2.56 (m, 2H), 2.45-2.26 (m, 2H), 2.19-1.59 (m, 4H), 1.59-1.32 (m, 6H), 1.32-0.89 (m, 4H), 0.66-0.39 (m, 2H). |
| 670 | 675.4 | 1H NMR (400 MHz, DMSO-d6) δ 9.09 (s, 1H), 8.10 (d, J = 8.0 Hz, 1H), 8.06-7.50 (m, 5H), 7.41-7.14 (m, 4H), 5.19 (p, J = 6.9 Hz, 1H), 5.05-4.76 (m, 3H), 4.57-4.45 (m, 1H), 4.23-4.11 (m, 1H), 4.07-3.96 (m, 1H), 3.80-3.67 (m, 0.5H), 3.45-3.01 (m, 2H), 2.85-2.71 (m, 0.5H), 2.70-2.61 (m, 1H), 2.47-2.33 (m, 2H), 2.04-1.31 (m, 14H), 1.27-0.96 (m, 4H), 0.64-0.37 (m, 2H). |
| 671 | 701.3 | 1H NMR (400 MHz, DMSO-d6) δ 9.27 (d, J = 7.9 Hz, 1H), 8.30 (d, J = 5.1 Hz, 1H), 8.10 (d, J = 8.0 Hz, 1H), 8.06-7.50 (m, 4H), 7.37-7.15 (m, 3H), 7.05 (d, J = 5.1 Hz, 1H), 5.47-5.33 (m, 1H), 5.05-4.88 (m, 2H), 4.88-4.73 (m, 1H), 4.60-4.41 (m, 1H), 4.27-4.11 (m, 1H), 4.07-3.94 (m, 1H), 3.85-3.65 (m, 0.5H), 3.46-3.04 (m, 1.5H), 2.84-2.68 (m, 1H), 2.31-1.38 (m, 14H), 1.38-0.84 (m, 9H), 0.55-0.29 (m, 2H). |
| 672 | 695.2 | 1H NMR (400 MHz, DMSO-d6) δ 9.26 (d, J = 6.6 Hz, 1H), 8.29 (s, 1H), 8.09 (d, J = 8.1 Hz, 1H), 8.04-7.53 (m, 4H), 7.48 (s, 1H), 7.32 (s, 1H), 7.29-7.15 (m, 2H), 5.21-5.09 (m, 1H), 5.03-4.76 (m, 3H), 4.58-4.44 (m, 1H), 4.24-4.12 (m, 1H), 4.06-3.94 (m, 1H), 3.81-3.62 (m, 1H), 3.45-3.13 (m, 2H), 2.85-2.59 (m, 1H), 2.41-2.25 (m, 3H), 2.04-1.36 (m, 8H), 1.31-0.92 (m, 6H), 0.55-0.36 (m, 2H). |
| 673 | 672.3 | 1H NMR (400 MHz, DMSO-d6) δ 8.85 (d, J = 6.8 Hz, 1H), 8.05 (d, J = 8.1 Hz, 1H), 8.02-7.62 (m, 3H), 7.38-7.27 (m, 3H), 7.26-7.15 (m, 4H), 6.90 (s, 1H), 5.15 (p, J = 7.0 Hz, 1H), 5.03-4.76 (m, 3H), 4.60-4.43 (m, 1H), 4.32-4.15 (m, 1H), 3.99 (s, 3H), 3.91 (tt, J = 7.2, 3.9 Hz, 1H), 3.87-3.74 (m, 0.5H), 3.48-2.99 (m, 1.5H), 2.87-2.67 (m, 1H), |

TABLE 3-continued

| Example | ES/MS m/z [M + H]+ | ¹H NMR |
|---|---|---|
| | | 2.46-2.29 (m, 1H), 2.21 (td, J = 12.1, 4.5 Hz, 1H), 2.03-1.32 (m, 11H), 1.32-1.07 (m, 3H), 1.07-0.74 (m, 2H), 0.59-0.42 (m, 1H), 0.42-0.28 (m, 1H). |
| 674 | 711.3 | 1H NMR (400 MHz, DMSO-d6) δ 9.25 (d, J = 6.8 Hz, 1H), 8.61 (s, 1H), 8.10 (d, J = 8.1 Hz, 1H), 8.06-7.69 (m, 3H), 7.69-7.52 (m, 2H), 7.32 (s, 1H), 7.30-7.17 (m, 2H), 6.95 (t, J = 54.9 Hz, 1H), 5.20 (p, J = 6.9 Hz, 1H), 5.10-4.78 (m, 3H), 4.61-4.45 (m, 1H), 4.25-4.11 (m, 1H), 4.07 3.95 (m, 1H), 3.84-3.66 (m, 1H), 3.45-3.04 (m, 3H), 2.86-2.68 (m, 1H), 2.45-2.28 (m, 2H), 2.03-1.38 (m, 9H), 1.38-0.89 (m, 5H), 0.62-0.35 (m, 2H). |
| 675 | 637.3 | 1H NMR (400 MHz, DMSO-d6) δ 8.61 (dd, J = 4.8, 1.6 Hz, 1H), 8.49 (t, J = 5.8 Hz, 1H), 8.23 (d, J = 8.1 Hz, 1H), 8.01 (dd, J = 7.8, 1.6 Hz, 1H), 7.97 (br. s, 3H), 7.60 (dd, J = 7.8, 4.8 Hz, 1H), 7.49-7.42 (m, 2H), 7.14 (s, 1H), 6.94 (d, J = 1.2 Hz, 1H), 4.65 (t, J = 6.4 Hz, 2H), 4.16 (s, 3H), 4.00 (s, 3H), 3.94-3.75 (m, 2H), 3.70 (dd, J = 6.2, 3.1 Hz, 1H), 3.58-3.49 (m, 2H), 3.47-3.32 (m, 1H), 3.36 (s, 3H), 3.23-3.16 (m, 2H), 2.00-1.90 (m, 1H), 1.82-1.69 (m, 1H), 1.52-1.45 (m, 4H), 1.45-1.37 (m, 2H), 1.16-1.07 (m, 2H). |
| 676 | 648.3 | 1H NMR (400 MHz, DMSO-d6) δ 8.55 (dd, J = 8.9, 2.7 Hz, 1H), 8.05 (d, J = 8.0 Hz, 1H), 7.98 (br. d, J = 5.9 Hz, 3H), 7.37 (d, J = 3.5 Hz, 1H), 7.23 (d, J = 8.1 Hz, 1H), 7.13 (d, J = 1.4 Hz, 1H), 6.89 (s, 1H), 5.58-5.44 (m, 1H), 5.13 (dd, J = 27.7, 14.5 Hz, 1H), 5.09-4.98 (m, 1H), 4.63-4.50 (m, 1H), 4.09 (s, 3H), 4.00 (s, 3H), 3.87-3.70 (m, 1H), 3.31-3.17 (m, 2H), 2.30-2.19 (m, 1H), 2.18-1.80 (m, 4H), 1.68-1.49 (m, 2H), 1.53 (q, J = 5.5 Hz, 1H), 1.44 (d, J = 7.0 Hz, 3H), 1.39-1.16 (m, 1H), 1.29 (t, J = 7.2 Hz, 3H), 1.12 (d, J = 7.3 Hz, 3H), 0.88-0.80 (m, 1H), 0.71-0.56 (m, 1H), 0.54-0.43 (m, 2H). |
| 677 | 644.4 | 1H NMR (400 MHz, DMSO-d6) δ 8.04 (d, J = 8.1 Hz, 1H), 7.88 (s, 3H), 7.81 (d, J = 7.5 Hz, 1H), 7.57-7.37 (m, 1H), 7.19 (d, J = 8.1 Hz, 1H), 7.03 (s, 1H), 6.97-6.88 (m, 1H), 5.18-5.07 (m, 1H), 4.86-4.76 (m, 1H), 4.47-4.33 (m, 1H), 4.11 (s, 3H), 3.99 (s, 3H), 3.58-3.49 (m, 1H), 3.48-3.39 (m, 1H), 3.37 (d, J = 6.5 Hz, 1H), 3.29 (s, 3H), 3.20-2.92 (m, 3H), 2.26-2.17 (m, 1H), 2.04-1.86 (m, 2H), 1.81-1.49 (m, 4H), 1.45 (d, J = 7.1 Hz, 3H), 1.42-1.25 (m, 5H), 1.21 (s, 3H), 1.17-0.98 (m, 3H), 0.94 (s, 3H). |
| 678 | 654.3 | 1H NMR (400 MHz, DMSO-d6) δ 8.57 (d, J = 8.8 Hz, 1H), 8.10 (br. s, 3H), 8.05 (d, J = 8.0 Hz, 1H), 7.43-7.38 (m, 1H), 7.23 (d, J = 8.1 Hz, 1H), 7.13 (s, 1H), 6.91 (dd, J = 3.9, 1.2 Hz, 1H), 6.61-6.16 (m, 1H), 5.50 (t, J = 13.5 Hz, 1H), 5.14 (dd, J = 27.8, 14.5 Hz, 1H), 5.09-4.99 (m, 1H), 4.70 (d, J = 44.4 Hz, 1H), 4.94-4.20 (m, 2H), 4.10 (s, 3H), 4.10-4.06 (m, 1H), 3.99 (s, 3H), 3.72-3.35 (m, 2H), 3.36-3.17 (m, 1H), 2.26-1.98 (m, 2H), 1.99-1.90 (m, 1H), 1.66-1.56 (m, 1H), 1.53 (q, J = 5.3 Hz, 1H), 1.44 (d, J = 7.0 Hz, 3H), 1.38-1.23 (m, 1H), 0.88-0.79 (m, 1H), 0.72-0.56 (m, 1H), 0.56-0.44 (m, 2H). |
| 679 | 689.3 | 1H NMR (400 MHz, DMSO-d6) δ 9.54 (d, J = 7.5 Hz, 1H), 8.52 (s, 1H), 8.39 (d, J = 1.1 Hz, 1H), 8.17 (d, J = 8.0 Hz, 1H), 7.96 (br. s, 3H), 7.37 (d, J = 8.1 Hz, 1H), 7.35 (d, J = 1.1 Hz, 1H), 7.19 (s, 1H), 6.89 (s, 1H), 5.38 (p, J = 7.1 Hz, 1H), 5.34-5.22 (m, 1H), 5.17 (dd, J = 31.4, 14.6 Hz, 1H), 4.12 (s, 3H), 4.00 (s, 3H), 3.42-3.31 (m, 2H), 3.14-2.89 (m, 1H), 2.70-2.52 (m, 1H), 2.45 (dd, J = 13.0, 4.4 Hz, 1H), 2.16 (dt, J = 13.5, 6.6 Hz, 1H), 1.88-1.63 (m, 4H), 1.61-1.48 (m, 3H), 1.46 (d, J = 7.0 Hz, 3H), 1.21 (d, J = 6.9 Hz, 3H), 1.18-0.98 (m, 1H). |
| 680 | 636.3 | 1H NMR (400 MHz, DMSO-d6) δ 8.56 (d, J = 8.8 Hz, 1H), 8.05 (d, J = 8.0 Hz, 1H), 7.92 (br. s, 3H), 7.43 (s, 1H), 7.23 (d, J = 8.1 Hz, 1H), 7.13 (s, 1H), 6.95 (d, J = 1.2 Hz, 1H), 5.51 (t, J = 13.4 Hz, 1H), 5.13 (dd, J = 27.7, 14.5 Hz, 1H), 5.09-4.99 (m, 1H), 4.84-4.41 (m, 2H), 4.10 (s, 3H), 4.08-4.00 (m, 1H), 3.99 (s, 3H), 3.60-3.41 (m, 3H), 3.41-3.28 (m, 1H), 2.21-1.99 (m, 2H), 1.95 (dt, J = 13.8, 4.5 Hz, 1H), 1.87-1.66 (m, 2H), 1.66-1.56 (m, 1H), 1.53 (q, J = 5.3 Hz, 1H), 1.44 (d, J = 7.1 Hz, 3H), 1.39-1.23 (m, 1H), 0.89-0.79 (m, 1H), 0.72-0.56 (m, 1H), 0.54-0.44 (m, 2H). |
| 681 | 668.3 | 1H NMR (400 MHz, DMSO-d6) δ 8.57 (d, J = 8.9 Hz, 1H), 8.05 (d, J = 8.0 Hz, 1H), 7.36 (s, 1H), 7.22 (d, J = 8.0 Hz, 1H), 7.12 (s, 1H), 6.90 (s, 1H), 5.51 (t, J = 13.5 Hz, 1H), 5.13 (dd, J = 27.7, 14.5 Hz, 1H), 5.09-4.98 (m, 1H), 4.87 (d, J = 47.0 Hz, 1H), 4.09 (s, 3H), 3.98 (s, 3H), 3.80-3.68 (m, 1H), 3.49-3.42 (m, 1H), 3.42 (s, 3H), 3.37-3.26 (m, 1H), 3.12-3.01 (m, 1H), 2.25-1.99 (m, 2H), 1.94 (dt, J = 13.4, 4.3 Hz, 1H), 1.66-1.55 (m, 1H), 1.53 (q, J = 5.3 Hz, 1H), 1.44 (d, J = 7.1 Hz, 3H), 1.39-1.24 (m, 1H), 0.88-0.80 (m, 1H), 0.70-0.55 (m, 1H), 0.54-0.45 (m, 2H). |
| 682 | 660.3 | 1H NMR (400 MHz, DMSO-d6) δ 8.66 (d, J = 5.5 Hz, 1H), 8.09 (d, J = 8.0 Hz, 1H), 7.88 (d, J = 98.0 Hz, 3H), 7.69-7.55 (m, 1H), 7.33 (s, 1H), 7.37-7.17 (m, 1H), 7.23 (d, J = 8.1 Hz, 1H), 5.52 (dt, J = 14.3, 6.9 Hz, 1H), 5.17 (dd, J = 33.0, 14.6 Hz, 1H), 4.89 (p, J = 6.9 Hz, 1H), 5.02-4.45 (m, 1H), 4.25-4.13 (m, 1H), 4.05-3.95 (m, 1H), 3.44-2.68 (m, 2H), 2.19-2.05 (m, 1H), 2.03-1.91 (m, 1H), 1.83 (td, J = 8.1, 5.3 Hz, 1H), |

TABLE 3-continued

| Example | ES/MS m/z [M + H]+ | 1H NMR |
|---|---|---|
| | | 1.90-1.57 (m, 7H), 1.57-1.29 (m, 2H), 1.40 (d, J = 7.1 Hz, 3H), 1.27-1.21 (m, 1H), 1.15-0.87 (m, 4H), 0.82-0.70 (m, 2H), 0.70-0.63 (m, 1H), 0.50-0.39 (m, 1H). |
| 683 | 674.3 | 1H NMR (400 MHz, DMSO-d6) δ 8.11 (d, J = 8.1 Hz, 1H), 8.07-7.70 (m, 3H), 7.70-7.60 (m, 1H), 7.32 (s, 1H), 7.27 (d, J = 8.1 Hz, 1H), 7.29-7.17 (m, 1H), 5.65 (q, J = 7.3 Hz, 1H), 5.48 (dt, J = 14.2, 6.9 Hz, 1H), 5.18 (dd, J = 33.0, 14.7 Hz, 1H), 5.03-4.43 (m, 1H), 4.24-3.94 (m, 2H), 3.51 (s, 3H), 3.42-2.68 (m, 2H), 2.17-2.05 (m, 1H), 2.04-1.91 (m, 2H), 1.91-1.71 (m, 2H), 1.55 (d, J = 7.3 Hz, 3H), 1.71-1.35 (m, 5H), 1.34-1.18 (m, 3H), 1.05-0.88 (m, 4H), 0.85 (q, J = 5.2 Hz, 1H), 0.77 (td, J = 8.0, 3.9 Hz, 1H), 0.56-0.38 (m, 2H). |
| 684 | 626.3 | 1H NMR (400 MHz, DMSO-d6) δ 8.05 (d, J = 8.1 Hz, 1H), 8.01-7.68 (m, 3H), 7.64 (d, J = 8.0 Hz, 1H), 7.68-7.53 (m, 1H), 7.33-7.15 (m, 1H), 7.25 (s, 1H), 7.21 (d, J = 8.1 Hz, 1H), 5.16 (p, J = 6.9 Hz, 1H), 4.78 (qd, J = 13.8, 5.2 Hz, 2H), 5.05-4.45 (m, 1H), 3.98 (dq, J = 9.6, 2.9 Hz, 1H), 4.24-3.69 (m, 1H), 3.46-3.21 (m, 1H), 3.21-2.73 (m, 1H), 2.02-1.91 (m, 1H), 1.89-1.39 (m, 7H), 1.54 (d, J = 7.1 Hz, 3H), 1.39-1.27 (m, 1H), 1.17 (s, 3H), 1.14-1.06 (m, 4H), 1.00 (s, 3H), 0.80 (dt, J = 14.7, 8.8 Hz, 4H), 0.74-0.65 (m, 2H). |
| 685 | 691.3 | 1H NMR (400 MHz, DMSO-d6) δ 8.83 (d, J = 7.0 Hz, 1H), 8.09 (d, J = 8.0 Hz, 1H), 8.06-7.71 (m, 3H), 7.68 (d, J = 8.3 Hz, 1H), 7.70-7.56 (m, 1H), 7.31 (s, 1H), 7.25 (d, J = 8.1 Hz, 1H), 7.33-7.16 (m, 1H), 6.67 (d, J = 8.3 Hz, 1H), 5.19 (p, J = 7.0 Hz, 1H), 4.91 (dt, J = 14.4, 7.7 Hz, 1H), 4.85-4.77 (m, 1H), 4.61-4.43 (m, 1H), 4.01 (tt, J = 7.1, 3.9 Hz, 1H), 4.20-3.67 (m, 1H), 3.84 (s, 3H), 3.46-3.20 (m, 1H), 3.19-2.70 (m, 1H), 2.68 (dd, J = 12.3, 8.0 Hz, 1H), 2.41-2.28 (m, 2H), 2.03-1.91 (m, 1H), 1.91-1.39 (m, 8H), 1.49 (d, J = 7.0 Hz, 3H), 1.28-0.89 (m, 5H), 0.72-0.54 (m, 1H), 0.52-0.43 (m, 1H). |
| 686 | 658.4 | 1H NMR (400 MHz, DMSO-d6) δ 8.11 (d, J = 7.0 Hz, 1H), 8.05 (d, J = 8.1 Hz, 1H), 8.02-7.91 (m, 3H), 7.44 (s, 1H), 7.20 (d, J = 8.2 Hz, 1H), 7.02 (s, 1H), 6.93 (d, J = 1.1 Hz, 1H), 4.93 (p, J = 7.0 Hz, 1H), 4.72-4.59 (m, 1H), 4.49-4.36 (m, 1H), 4.12 (s, 3H), 3.99 (s, 3H), 3.91-3.66 (m, 5H), 3.66-3.46 (m, 2H), 3.43-3.26 (m, 4H), 2.24-1.07 (m, 19H). |
| 687 | 658.3 | 1H NMR (400 MHz, DMSO-d6) δ 8.07 (d, J = 8.1 Hz, 1H), 8.04-7.98 (m, 4H), 7.44 (s, 1H), 7.23 (d, J = 8.2 Hz, 1H), 7.06 (s, 1H), 6.93 (d, J = 1.2 Hz, 1H), 5.25 (dq, J = 9.1, 6.9 Hz, 1H), 4.88-4.76 (m, 1H), 4.60-4.50 (m, 1H), 4.10 (s, 3H), 4.01-3.94 (m, 4H), 3.89 (q, J = 7.4 Hz, 1H), 3.74-3.67 (m, 1H), 3.58-3.48 (m, 3H), 3.44-3.32 (m, 4H), 2.26 (ddd, J = 12.1, 7.4, 4.5 Hz, 1H), 2.03-1.61 (m, 7H), 1.51-1.28 (m, 6H), 1.14-0.92 (m, 4H), 0.66-0.53 (m, 1H). |
| 688 | 632.3 | 1H NMR (400 MHz, DMSO-d6) δ 8.76 (d, J = 8.4 Hz, 1H), 8.04 (d, J = 8.2 Hz, 1H), 8.01-7.90 (m, 3H), 7.44 (s, 1H), 7.26 (d, J = 8.2 Hz, 1H), 7.03 (s, 1H), 6.93 (d, J = 1.2 Hz, 1H), 4.63 (p, J = 7.1 Hz, 1H), 4.58-4.50 (m, 2H), 4.13 (s, 3H), 3.99 (s, 3H), 3.93-3.77 (m, 1H), 3.74-3.66 (m, 1H), 3.60-3.48 (m, 2H), 3.46-3.29 (m, 5H), 2.02-1.07 (m, 15H), 0.91 (dt, J = 19.8, 6.8 Hz, 1H). |
| 689 | 632.3 | 1H NMR (400 MHz, DMSO-d6) δ 8.41 (d, J = 9.5 Hz, 1H), 8.00 (d, J = 8.0 Hz, 1H), 7.45 (s, 1H), 7.16 (d, J = 8.0 Hz, 1H), 7.03 (s, 1H), 6.93 (d, J = 1.2 Hz, 1H), 5.19 (dq, J = 9.5, 7.0 Hz, 1H), 4.79-4.69 (m, 1H), 4.69-4.57 (m, 1H), 4.12 (s, 3H), 3.99 (s, 3H), 3.90-3.67 (m, 3H), 3.60-3.47 (m, 2H), 3.47-3.29 (m, 4H), 2.31-2.19 (m, 1H), 2.08-1.87 (m, 2H), 1.80-1.07 (m, 12H), 0.94 (ddd, J = 11.1, 9.3, 6.0 Hz, 1H). |
| 690 | 646.3 | 1H NMR (400 MHz, DMSO-d6) δ 8.58 (d, J = 8.8 Hz, 1H), 8.06 (d, J = 8.0 Hz, 1H), 8.04-7.90 (m, 3H), 7.86 (s, 1H), 7.78 (d, J = 8.3 Hz, 1H), 7.46 (dd, J = 8.3, 1.5 Hz, 1H), 7.36 (s, 1H), 7.23 (d, J = 8.0 Hz, 1H), 5.96-5.84 (m, 1H), 5.18 (dd, J = 27.7, 14.6 Hz, 1H), 5.12-4.99 (m, 1H), 3.98-3.81 (m, 2H), 3.76-3.67 (m, 1H), 3.65-3.46 (m, 3H), 3.46-3.31 (m, 4H), 2.30-1.88 (m, 4H), 1.80-1.70 (m, 1H), 1.67-1.50 (m, 2H), 1.44 (d, J = 7.1 Hz, 3H), 1.39-1.25 (m, 2H), 1.09-0.90 (m, 2H), 0.89-0.81 (m, 1H), 0.71-0.57 (m, 1H), 0.56-0.39 (m, 3H). |
| 691 | 610.3 | 1H NMR (400 MHz, DMSO-d6) δ 8.44 (d, J = 8.5 Hz, 1H), 8.03-7.89 (m, 4H), 7.84 (s, 1H), 7.76 (d, J = 8.3 Hz, 1H), 7.43 (dd, J = 8.4, 1.5 Hz, 1H), 7.26 (s, 1H), 7.13 (d, J = 8.1 Hz, 1H), 5.00 (p, J = 7.2 Hz, 1H), 4.92-4.81 (m, 1H), 4.81-4.71 (m, 1H), 3.99-3.77 (m, 2H), 3.73-3.67 (m, 1H), 3.64-3.46 (m, 3H), 3.46-3.29 (m, 4H), 2.02-1.08 (m, 15H), 0.94-0.82 (m, 2H), 0.76-0.53 (m, 3H), 0.50-0.43 (m, 1H). |
| 692 | 664.3 | 1H NMR (400 MHz, DMSO-d6) δ 8.07 (d, J = 8.1 Hz, 1H), 8.02-7.89 (m, 3H), 7.45 (s, 1H), 7.25 (d, J = 8.1 Hz, 1H), 7.12 (s, 1H), 6.94 (s, 1H), 5.81 (q, J = 7.4 Hz, 1H), 5.44 (t, J = 14.2 Hz, 1H), 5.10 (dd, J = 25.6, 14.8 Hz, 1H), 4.08 (s, 3H), 3.99 (s, 3H), 3.74-3.67 (m, 1H), 3.59-3.50 (m, 3H), 3.48 (s, 3H), 3.46-3.38 (m, 2H), 3.36 (s, 3H), 2.33-1.86 (m, 5H), 1.81-1.72 (m, 1H), 1.64-1.52 (m, 4H), 1.45-1.31 (m, 1H), 0.99 (t, J = 5.3 Hz, 1H), 0.92-0.75 (m, 1H), 0.68-0.57 (m, 2H). |
| 693 | 681.2 | 1H NMR (400 MHz, DMSO-d6) δ 9.11 (d, J = 7.1 Hz, 1H), 8.09 (d, J = 8.0 Hz, 1H), 8.05-7.90 (m, 3H), 7.84 (s, 1H), 7.82 (d, J = 8.1 Hz, 1H), 7.77 (d, J = 8.4 Hz, 1H), 7.47-7.43 (m, 1H), 7.41 (d, J = 8.0 Hz, 1H), |

TABLE 3-continued

| Example | ES/MS m/z [M + H]+ | ¹H NMR |
|---|---|---|
| | | 7.33 (s, 1H), 7.25 (d, J = 8.0 Hz, 1H), 5.20 (p, J = 6.9 Hz, 1H), 4.96-4.80 (m, 2H), 3.94-3.80 (m, 3H), 3.74-3.66 (m, 1H), 3.65-3.48 (m, 2H), 3.47-3.29 (m, 4H), 2.71-2.55 (m, 1H), 2.43-2.29 (m, 2H), 2.03-1.88 (m, 1H), 1.82-1.69 (m, 1H), 1.56-1.06 (m, 8H), 1.00-0.89 (m, 1H), 0.63-0.40 (m, 3H). |
| 694 | 664.3 | 1H NMR (400 MHz, Chloroform-d) δ 8.08 (d, J = 8.1 Hz, 1H), 8.02-7.89 (m, 4H), 7.45 (s, 1H), 7.25 (d, J = 8.1 Hz, 1H), 7.04 (s, 1H), 6.93 (s, 1H), 5.01 (p, J = 6.9 Hz, 1H), 4.61-4.41 (m, 2H), 4.13 (s, 3H), 3.99 (s, 3H), 3.93-3.77 (m, 1H), 3.74-3.67 (m, 1H), 3.64-3.48 (m, 2H), 3.44-3.29 (m, 5H), 2.02-1.68 (m, 5H), 1.62-1.32 (m, 9H), 1.25 (s, 3H). |
| 695 | 632.3 | 1H NMR (400 MHz, DMSO-d6) δ 8.36 (dd, J = 8.3, 1.9 Hz, 1H), 8.01 (d, J = 8.0 Hz, 1H), 8.00-7.89 (m, 3H), 7.45 (s, 1H), 7.19 (d, J = 8.1 Hz, 1H), 7.02 (s, 1H), 6.92 (s, 1H), 5.13 (p, J = 7.3 Hz, 1H), 4.59-4.50 (m, 2H), 4.11 (s, 3H), 3.98 (s, 3H), 3.91-3.75 (m, 1H), 3.74-3.67 (m, 1H), 3.62-3.48 (m, 2H), 3.47-3.27 (m, 5H), 2.02-1.85 (m, 2H), 1.82-0.88 (m, 14H). |
| 696 | 661.3 | 1H NMR (400 MHz, DMSO-d6) δ 9.35 (d, J = 7.7 Hz, 1H), 8.60 (d, J = 5.8 Hz, 1H), 8.11 (d, J = 8.0 Hz, 1H), 8.06-7.90 (m, 3H), 7.83 (s, 1H), 7.77 (d, J = 8.3 Hz, 1H), 7.58 (d, J = 5.6 Hz, 1H), 7.45 (d, J = 8.7 Hz, 1H), 7.35 (s, 1H), 7.28 (d, J = 8.0 Hz, 1H), 5.36 (p, J = 7.1 Hz, 1H), 4.95-4.84 (m, 2H), 3.95-3.82 (m, 2H), 3.74-3.65 (m, 1H), 3.65-3.47 (m, 1H), 3.47-3.30 (m, 4H), 2.69 (s, 3H), 2.68-2.60 (m, 3H), 2.26-2.16 (m, 1H), 1.99-1.88 (m, 1H), 1.81-1.69 (m, 1H), 1.55-1.06 (m, 9H), 0.99-0.91 (m, 1H), 0.50-0.37 (m, 2H). |
| 697 | 665.3 | 1H NMR (400 MHz, DMSO-d6) δ 9.31 (d, J = 7.9 Hz, 1H), 8.56 (d, J = 5.6 Hz, 1H), 8.10 (d, J = 8.0 Hz, 1H), 8.05-7.85 (m, 3H), 7.51 (s, 1H), 7.42 (s, 1H), 7.28 (d, J = 8.1 Hz, 1H), 7.10 (s, 1H), 6.94 (s, 1H), 5.39 (q, J = 7.3 Hz, 1H), 4.91-4.80 (m, 1H), 4.66-4.56 (m, 1H), 4.12 (s, 3H), 3.99 (s, 3H), 3.91-3.79 (m, 1H), 3.76-3.66 (m, 1H), 3.59-3.44 (m, 2H), 3.45-3.29 (m, 5H), 2.72-2.64 (m, 3H), 2.61 (s, 3H), 2.25-2.14 (m, 1H), 1.99-1.87 (m, 1H), 1.83-1.67 (m, 1H), 1.63-1.18 (m, 7H), 0.56-0.40 (m, 1H). |
| 698 | 679.3 | 1H NMR (400 MHz, DMSO-d6) δ 9.31 (d, J = 7.6 Hz, 1H), 8.55 (d, J = 5.5 Hz, 1H), 8.11 (d, J = 8.0 Hz, 1H), 8.07-7.86 (m, 3H), 7.66 (s, 1H), 7.48 (s, 1H), 7.37-7.22 (m, 3H), 5.36 (p, J = 7.1 Hz, 1H), 5.01-4.80 (m, 2H), 4.07-3.97 (m, 1H), 3.95-3.75 (m, 1H), 3.75-3.66 (m, 1H), 3.66-3.46 (m, 2H), 3.46-3.29 (m, 5H), 2.61 (s, 3H), 2.46-2.36 (m, 2H), 2.28-2.16 (m, 1H), 1.99-1.86 (m, 1H), 1.82-1.71 (m, 1H), 1.59-0.91 (m, 10H), 0.52-0.39 (m, 2H). |
| 699 | 656.3 | 1H NMR (400 MHz, DMSO-d6) δ 8.09 (d, J = 8.0 Hz, 1H), 7.97 (br s, 3H), 7.45 (s, 1H), 7.16 (d, J = 8.0 Hz, 1H), 7.08 (s, 1H), 6.93 (d, J = 1.2 Hz, 1H), 4.95-4.84 (m, 1H), 4.61-4.51 (m, 1H), 4.24 (s, 1H), 4.12 (s, 3H), 3.99 (s, 3H), 3.83-3.66 (m, 3H), 3.58-3.48 (m, 2H), 3.45-3.31 (m, 4H), 3.07-2.91 (m, 1H), 2.02-1.88 (m, 1H), 1.81-1.70 (m, 1H), 1.59 (s, 4H), 1.42-0.96 (m, 10H), 0.76-0.62 (m, 1H). |
| 700 | 682.3 | 1H NMR (400 MHz, DMSO-d6) δ 8.59 (d, J = 9.6 Hz, 1H), 8.09 (d, J = 8.0 Hz, 1H), 7.96 (br s, 3H), 7.69 (s, 1H), 7.37 (s, 1H), 7.31 (dd, J = 11.5, 1.2 Hz, 1H), 7.26 (d, J = 8.1 Hz, 1H), 5.82 (t, J = 13.7 Hz, 1H), 5.35-5.18 (m, 2H), 4.07-3.99 (m, 1H), 3.93-3.80 (m, 2H), 3.74-3.67 (m, 1H), 3.36 (s, 6H), 2.45-1.67 (m, 7H), 1.54-1.40 (m, 5H), 1.30-0.92 (m, 5H), 0.50-0.40 (m, 1H). |
| 701 | 666.3 | 1H NMR (400 MHz, DMSO-d6) δ 8.59 (d, J = 9.6 Hz, 1H), 8.09 (d, J = 8.0 Hz, 1H), 7.90 (br s, 3H), 7.63 (d, J = 1.1 Hz, 1H), 7.37 (s, 1H), 7.26 (d, J = 8.0 Hz, 2H), 7.24 (s, 1H), 5.82 (t, J = 13.7 Hz, 1H), 5.33-5.17 (m, 2H), 4.05-3.98 (m, 1H), 3.37 (s, 1H), 2.45-1.96 (m, 4H), 1.86-1.38 (m, 9H), 1.29-0.92 (m, 7H), 0.49-0.39 (m, 1H). |
| 702 | 668.3 | 1H NMR (400 MHz, DMSO-d6) δ 8.57 (d, J = 9.6 Hz, 1H), 8.07 (d, J = 8.0 Hz, 1H), 7.96 (br s, 3H), 7.44 (s, 1H), 7.25 (d, J = 8.1 Hz, 1H), 7.15 (s, 1H), 6.95 (d, J = 1.2 Hz, 1H), 5.52 (t, J = 13.5 Hz, 1H), 5.27-5.13 (m, 2H), 4.10 (s, 3H), 3.99 (s, 3H), 3.88-3.67 (m, 3H), 3.37 (s, 6H), 2.43-1.89 (m, 5H), 1.72 (t, J = 15.9 Hz, 2H), 1.52-1.37 (m, 5H), 1.28-0.90 (m, 2H). |
| 703 | 652.3 | 1H NMR (400 MHz, DMSO-d6) δ 8.57 (d, J = 9.6 Hz, 1H), 8.07 (d, J = 8.0 Hz, 1H), 7.91 (br s, 3H), 7.37 (d, J = 1.1 Hz, 1H), 7.25 (d, J = 8.0 Hz, 1H), 7.15 (s, 1H), 6.89 (s, 1H), 5.53 (t, J = 13.5 Hz, 1H), 5.29-5.09 (m, 2H), 4.10 (s, 3H), 4.00 (s, 3H), 3.43-3.29 (m, 1H), 3.09-2.88 (m, 1H), 2.44-1.96 (m, 5H), 1.86-1.36 (m, 10H), 1.22 (d, J = 6.9 Hz, 4H), 1.01-0.89 (m, 1H). |
| 704 | 646.3 | 1H NMR (400 MHz, DMSO-d6) δ 8.43 (d, J = 9.5 Hz, 1H), 8.01 (d, J = 8.0 Hz, 1H), 7.97 (br s, 3H), 7.69 (s, 1H), 7.28 (dd, J = 11.6, 1.2 Hz, 1H), 7.26 (s, 1H), 7.17 (d, J = 8.1 Hz, 1H), 5.26-5.13 (m, 2H), 4.86-4.77 (m, 2H), 4.02-3.95 (m, 1H), 3.89-3.66 (m, 2H), 3.60-3.50 (m, 1H), 3.45-3.30 (m, 4H), 2.31-2.20 (m, 1H), 2.03 (ddd, J = 11.4, 8.0, 3.7 Hz, 1H), 1.90 (d, J = 7.7 Hz, 15H), 1.00-0.82 (m, 2H), 0.67-0.59 (m, 1H). |
| 705 | 630.3 | 1H NMR (400 MHz, DMSO-d6) δ 8.43 (d, J = 9.5 Hz, 1H), 8.01 (d, J = 8.0 Hz, 1H), 7.92 (br s, 3H), 7.60 (d, J = 1.3 Hz, 1H), 7.26 (s, 1H), 7.23 |

TABLE 3-continued

| Example | ES/MS m/z [M + H]+ | ¹H NMR |
|---|---|---|
| | | (d, J = 11.9 Hz, 1H), 7.17 (d, J = 8.1 Hz, 1H), 5.26-5.14 (m, 1H), 4.87-4.77 (m, 2H), 3.99 (tt, J = 7.2, 3.8 Hz, 1H), 3.43-3.31 (m, 1H), 3.17-2.86 (m, 1H), 2.31-2.20 (m, 1H), 2.03 (ddd, J = 9.3, 7.6, 3.7 Hz, 1H), 1.86-0.83 (m, 22H), 0.67-0.57 (m, 1H). |
| 706 | 616.3 | 1H NMR (400 MHz, DMSO-d6) δ 8.41 (d, J = 9.5 Hz, 1H), 8.00 (d, J = 8.0 Hz, 1H), 7.91 (br s, 3H), 7.35 (d, J = 1.1 Hz, 1H), 7.16 (d, J = 8.1 Hz, 1H), 7.03 (s, 1H), 6.87 (s, 1H), 5.25-5.14 (m, 1H), 4.80-4.59 (m, 2H), 4.12 (s, 3H), 3.99 (s, 3H), 3.43-3.30 (m, 1H), 2.32-2.20 (m, 1H), 2.07-1.98 (m, 1H), 1.87-1.08 (m, 18H), 0.99-0.89 (m, 1H). |
| 707 | 634.3 | 1H NMR (400 MHz, DMSO-d6) δ 8.54 (d, J = 8.8 Hz, 1H), 8.37-8.09 (m, 3H), 8.06 (d, J = 8.0 Hz, 1H), 7.64-7.43 (m, 1H), 7.23 (d, J = 8.0 Hz, 1H), 7.14 (s, 1H), 7.08-6.93 (m, 1H), 5.58-5.43 (m, 1H), 5.19-5.00 (m, 2H), 4.87 (br s, 0.5H), 4.65 (br s, 0.5H), 4.59-4.51 (m, 1H), 4.26-3.39 (m, 11H), 2.22-1.88 (m, 3H), 1.67-1.48 (m, 2H), 1.44 (d, J = 7.0 Hz, 3H), 1.37-1.20 (m, 1H), 0.89-0.79 (m, 1H), 0.69-0.55 (m, 1H), 0.55-0.42 (m, 2H). |
| 708 | 614.3 | 1H NMR (400 MHz, DMSO-d6) δ 8.32 (br s, 1.5H), 8.16 (br s, 1.5H), 8.04 (d, J = 8.1 Hz, 1H), 7.81 (d, J = 7.5 Hz, 1H), 7.60 (s, 0.5H), 7.47 (s, 0.5H), 7.19 (d, J = 8.1 Hz, 1H), 7.06-6.92 (m, 2H), 5.12 (p, J = 7.1 Hz, 1H), 4.90-4.74 (m, 1.5H), 4.68-4.51 (m, 1.5H), 4.47-4.36 (m, 1H), 4.22-3.69 (m, 10H), 3.50-3.41 (m, 1H), 1.91 (t, J = 12.0 Hz, 1H), 1.74-1.52 (m, 2H), 1.50-0.99 (m, 14H), 0.94 (s, 3H). |
| 709 | 707.2 | 1H NMR (400 MHz, DMSO-d6) δ 8.97 (d, J = 6.9 Hz, 1H), 8.11 (d, J = 8.1 Hz, 1H), 7.95 (s, 2H), 7.89 (d, J = 8.0 Hz, 1H), 7.78-7.55 (m, 2H), 7.46 (d, J = 8.0 Hz, 1H), 7.35 (s, 1H), 7.31-7.16 (m, 2H), 5.27-5.10 (m, 2H), 5.02-4.90 (m, 0.5H), 4.70 (dd, J = 14.6, 8.6 Hz, 1H), 4.59-4.45 (m, 0.5H), 4.21-4.14 (m, 1H), 4.08-3.98 (m, 1H), 3.42-3.20 (m, 2H), 2.81-2.57 (m, 2H), 2.05-1.46 (m, 12H), 1.27-1.06 (m, 3H), 1.04-0.88 (m, 2H), 0.68-0.57 (m, 1H), 0.11-0.02 (m, 1H), −0.61-−0.70 (m, 1H). |
| 710 | 707.2 | 1H NMR (400 MHz, DMSO-d6) δ 9.06 (d, J = 7.0 Hz, 1H), 8.10 (d, J = 8.0 Hz, 1H), 7.95 (br s, 2H), 7.81 (d, J = 8.0 Hz, 1H), 7.77-7.53 (m, 2H), 7.42 (d, J = 8.0 Hz, 1H), 7.35 (s, 1H), 7.31-7.17 (m, 2H), 5.17 (p, J = 6.5 Hz, 1H), 5.11-4.91 (m, 1.5H), 4.66-4.43 (m, 1.5H), 4.22-4.12 (m, 0.5H), 4.07-3.96 (m, 1H), 3.83-3.68 (m, 0.5H), 3.46-3.00 (m, 2.5H), 2.81-2.55 (m, 2.5H), 2.12-1.44 (m, 12H), 1.30-0.91 (m, 3H), 0.84-0.43 (m, 4H), −0.07-−0.16 (m, 1H). |
| 711 | 628.3 | 1H NMR (400 MHz, DMSO-d6) δ 8.85 (d, J = 5.5 Hz, 1H), 8.00 (d, J = 8.0 Hz, 1H), 7.96 (br s, 2H), 7.73 (br s, 1H), 7.36 (s, 1H), 7.12 (d, J = 8.1 Hz, 1H), 7.04 (s, 1H), 6.89 (s, 1H), 5.08-4.79 (m, 2.5H), 4.70-4.61 (m, 1H), 4.57-4.47 (m, 0.5H), 4.28-4.18 (m, 0.5H), 4.09 (s, 3H), 3.98 (s, 3H), 3.80-3.60 (m, 0.5H),  3.45-3.06 (m, 1.5H), 2.84-2.70 (m, 0.5H), 2.37-2.20 (m, 2H), 2.04-1.22 (m, 14H), 1.10-0.88 (m, 3H), 0.44-0.28 (m, 1H). |
| 712 | 642.3 | 1H NMR (400 MHz, DMSO-d6) δ 8.87 (d, J = 5.3 Hz, 1H), 8.01 (d, J = 8.0 Hz, 1H), 7.96 (br s, 2H), 7.78-7.53 (m, 2H), 7.27 (s, 1H), 7.26-7.15 (m, 1H), 7.13 (d, J = 8.1 Hz, 1H), 5.03-4.87 (m, 2.5H), 4.83 (p, J = 6.3 Hz, 1H), 4.57-4.45 (m, 0.5H), 4.22-4.14 (m, 0.5H), 4.05-3.95 (m, 1H), 3.81-3.68 (m, 0.5H), 3.43-3.07 (m, 1.5H), 2.81-2.70 (m, 0.5H), 2.35-2.20 (m, 2H), 2.03-0.85 (m, 20H), 0.41-0.22 (m, 2H). |
| 713 | 681.2 | 1H NMR (400 MHz, DMSO-d6) δ 9.12-9.05 (m, 1H), 8.09 (d, J = 8.0 Hz, 1H), 7.97 (br s, 2H), 7.82 (d, J = 8.0 Hz, 1H), 7.74 (br s, 1H), 7.40 (d, J = 8.1 Hz, 1H), 7.36 (s, 1H), 7.26 (d, J = 8.1 Hz, 1H), 7.08 (s, 1H), 6.90 (s, 1H), 5.22 (p, J = 7.0 Hz, 1H), 5.07-4.92 (m, 0.5H), 4.90-4.77 (m, 1H), 4.64-4.44 (m, 1.5H), 4.30-4.16 (m, 0.5H), 4.11 (s, 3H), 3.99 (s, 3H), 3.86-3.66 (m, 0H), 3.48-3.03 (m, 1.5H), 2.84-2.71 (m, 0.5H), 2.70-2.57 (m, 1H), 2.41-2.26 (m, 2H), 2.05-1.34 (m, 12H), 1.20 (s, 1H), 0.68-0.50 (m, 1H). |
| 714 | 735.2 | 1H NMR (400 MHz, DMSO-d6) δ 9.10 (d, J = 7.2 Hz, 1H), 8.12 (d, J = 8.0 Hz, 1H), 8.05-7.65 (m, 5H), 7.41 (d, J = 8.0 Hz, 1H), 7.38 (s, 1H), 7.28 (d, J = 8.1 Hz, 1H), 7.18 (s, 1H), 5.23 (p, J = 7.1 Hz, 1H), 5.05-4.77 (m, 1.5H), 4.68-4.44 (m, 1.5H), 4.19-4.10 (m, 0.5H), 4.08 (s, 3H), 3.81-3.68 (m, 0.5H), 3.49-3.10 (m, 1.5H), 2.86-2.71 (m, 0.5H), 2.45-2.29 (m, 2H), 2.03-1.36 (m, 11H), 1.28-1.16 (m, 1H), 0.72-0.49 (m, 1H). |
| 715 | 682.3 | 1H NMR (400 MHz, DMSO-d6) δ 8.42 (d, J = 9.5 Hz, 1H), 8.03 (d, J = 8.0 Hz, 1H), 8.00-7.66 (m, 4H), 7.38 (br s, 1H), 7.18 (d, J = 8.1 Hz, 1H), 7.12 (s, 1H), 5.28-5.14 (m, 1H), 5.04-4.92 (m, 0.5H), 4.82-4.45 (m, 2.5H), 4.17-4.11 (m, 0.5H), 4.08 (s, 3H), 3.80-3.66 (m, 0.5H), 3.50-3.08 (m, 1.5H), 2.87-2.71 (m, 0.5H), 2.36-2.21 (m, 1H), 2.09-1.08 (m, 18H), 1.00-0.87 (m, 1H). |
| 716 | 682.3 | 1H NMR (400 MHz, DMSO-d6) δ 8.92 (d, J = 7.2 Hz, 1H), 8.15 (d, J = 8.0 Hz, 1H), 8.03-7.60 (m, 3H), 7.40-7.30 (m, 4H), 7.30-7.20 (m, 2H), 7.17 (s, 1H), 6.90 (s, 1H), 5.35-5.10 (m, 3H), 5.08-4.90 (m, |

TABLE 3-continued

| Example | ES/MS m/z [M + H]+ | 1H NMR |
|---|---|---|
| | | 0.5H), 4.58-4.44 (m, 0.5H), 4.31-4.19 (m, 0.5H), 4.11 (s, 3H), 3.99 (s, 3H), 3.92-3.73 (m, 0.5H), 3.44-3.06 (m, 1.5H), 2.81-2.68 (m, 0.5H), 2.36-2.23 (m, 2H), 2.05-1.39 (m, 12H), 1.30-1.00 (m, 2H). |
| 717 | 616.3 | 1H NMR (400 MHz, DMSO-d6) δ 8.42 (d, J = 9.5 Hz, 1H), 8.03 (d, J = 8.0 Hz, 1H), 8.00-7.90 (m, 2H), 7.80-7.57 (m, 2H), 7.29-7.20 (m, 1H), 7.18 (d, J = 8.1 Hz, 1H), 7.10 (s, 1H), 5.21 (dq, J = 9.4, 7.0 Hz, 1H), 5.04-4.92 (m, 0.5H), 4.85-4.62 (m, 2H), 4.59-4.46 (m, 0.5H), 4.19-4.12 (m, 0.5H), 4.10 (s, 3H), 3.79-3.69 (m, 0.5H), 3.43-3.02 (m, 1.5H), 2.81-2.70 (m, 0.5H), 2.31-2.22 (m, 1H), 2.07-1.08 (m, 18H), 0.99-0.89 (m, 1H). |
| 718 | 616.3 | 1H NMR (400 MHz, DMSO-d6) δ 8.42 (d, J = 9.5 Hz, 1H), 8.03 (d, J = 8.0 Hz, 1H), 8.00-7.90 (m, 2H), 7.80-7.57 (m, 2H), 7.29-7.20 (m, 1H), 7.18 (d, J = 8.1 Hz, 1H), 7.10 (s, 1H), 5.21 (dq, J = 9.4, 7.0 Hz, 1H), 5.04-4.92 (m, 0.5H), 4.85-4.62 (m, 2H), 4.59-4.46 (m, 0.5H), 4.19-4.12 (m, 0.5H), 4.10 (s, 3H), 3.79-3.69 (m, 0.5H), 3.43-3.02 (m, 1.5H), 2.81-2.70 (m, 0.5H), 2.31-2.22 (m, 1H), 2.07-1.08 (m, 18H), 0.99-0.89 (m, 1H). |
| 719 | 684.4 | 1H NMR (400 MHz, DMSO-d6) δ 8.33 (d, J = 7.8 Hz, 1H), 8.06 (d, J = 8.1 Hz, 1H), 8.00 (brs, 3H), 7.45 (brs, 1H), 7.21 (d, J = 8.1 Hz, 1H), 7.04 (s, 1H), 6.94 (s, 1H), 5.29-5.17 (m, 1H), 4.98-4.82 (m, 1H), 4.44-4.33 (m, 1H), 4.12 (s, 3H), 3.99 (s, 3H), 3.76-3.69 (m, 2H), 3.61-3.47 (m, 2H), 3.46-3.33 (m, 1H), 3.37 (s, 3H), 2.51-2.39 (m, 1H), 2.02-1.55 (m, 6H), 1.49-1.45 (m, 3H), 1.45-1.29 (m, 3H), 1.16 (s, 3H), 1.11-0.97 (m, 2H). |
| 720 | 684.4 | 1H NMR (400 MHz, DMSO-d6) δ 8.28 (d, J = 7.4 Hz, 1H), 8.07 (d, J = 8.1 Hz, 1H), 7.98 (s, 3H), 7.44 (s, 1H), 7.22 (d, J = 8.1 Hz, 1H), 7.05 (s, 1H), 6.94 (s, 1H), 5.21-5.11 (m, 1H), 4.85-4.72 (m, 1H), 4.52-4.39 (m, 1H), 4.12 (s, 3H), 3.99 (s, 3H), 3.88 (brs, 1H), 3.76-3.66 (m, 1H), 3.37 (s, 3H), 2.51-2.43 (m, 1H), 2.14-1.58 (m, 5H), 2.03-1.52 (m, 5H), 1.50 (d, J = 7.1 Hz, 3H), 1.46 (s, 3H), 1.43-1.22 (m, 4H), 1.11-0.96 (m, 1H). |
| 721 | 645.7 | NA |
| 722 | 666.2 | 1H NMR (400 MHz, DMSO-d6) δ 8.33 (d, J = 7.7 Hz, 1H), 8.06 (d, J = 8.0 Hz, 1H), 8.06 (brs, 1H 1st rotamer), 7.91 (brs, 2H 2nd rotamer), 7.55 (s, 0.4H 1st rotamer), 7.42 (s, 0.6H 2nd rotamer), 7.21 (d, J = 8.1 Hz, 1H), 7.05 (s, 1H), 7.00 (s, 0.4H 1st rotamer), 6.96 (s, 0.6H 2nd rotamer), 5.28-5.18 (m, 1H), 4.97-4.84 (s, 1H), 4.54 (s, 0.4H 1st rotamer), 4.40 (dt, J = 13.8, 7.6 Hz, 1H), 4.21 (s, 0.6H 2nd rotamer), 4.12 (s, 3H), 4.00 (s, 3H), 3.85-3.73 (m, 0.4H 1st rotamer), 3.69-3.56 (m, 0.6H 2nd rotamer), 3.24-3.13 (m 1H), 2.67 (s, 0.6H 2nd rotamer), 2.50 (s, 0.4H 1st rotamer), 2.48-2.37 (m, 1H), 2.04-1.51 (m, 7H), 1.47 (d, J = 7.1 Hz, 3H), 1.44-1.23 (m, 4H), 1.16 (s, 3H), 1.13-0.91 (m, 2H). |
| 723 | 720.2 | 1H NMR (400 MHz, DMSO-d6) δ 8.33 (d, J = 7.8 Hz, 1H), 8.18 (brs, 3H), 8.06 (d, J = 8.1 Hz, 1H), 7.47 (s, 1H), 7.21 (d, J = 8.1 Hz, 1H), 7.04 (s, 1H), 6.95 (s, 1H), 6.86 (t, J = 74.7 Hz, 1H), 5.29-5.17 (m, 1H), 4.97-4.84 (m, 1H), 4.71-4.64 (m, 1H), 4.45-4.32 (m, 1H), 4.12 (s, 3H), 4.00 (s, 3H), 3.62 (brs, 2H), 2.49-2.39 (m, 1H), 2.04-1.54 (m, 7H), 1.47 (d, J = 7.1 Hz, 3H), 1.46-1.29 (m, 4H), 1.16 (s, 3H), 1.14-0.95 (m, 2H). |
| 724 | 666.2 | 1H NMR (400 MHz, DMSO-d6) δ 8.28 (d, J = 7.3 Hz, 1H), 8.07 (d, J = 8.1 Hz, 1H), 8.06 (brs, 1H 1st rotamer), 7.92 (brs, 2H 2nd rotamer), 7.55 (s, 0.4H 1st rotamer), 7.41 (s, 0.6H 2nd rotamer), 7.22 (d, J = 8.1 Hz, 1H), 7.05 (s, 1H), 7.00 (s, 0.4H 1st ortamer), 6.96 (s, 0.6H 2nd rotamer), 5.21-5.11 (m, 1H), 4.85-4.71 (m, 1H), 4.54 (s, 0.4H 1st rotamer), 4.52-4.43 (m, 1H), 4.21 (s, 0.6H 2nd rotamer), 4.12 (s, 3H), 4.00 (d, J = 2.4 Hz, 3H), 3.84-3.73 (m, 0.4H 1st rotamer), 3.61 (d, J = 12.0 Hz, 0.6H 2nd rotamer), 3.24-3.13 (m, 1H), 2.68 (s, 0.6H 2nd rotamer), 2.58 (s, 0.4H 1st rotamer), 2.11-1.52 (m, 7H), 1.50 (d, J = 7.1 Hz, 3H), 1.46 (s, 3H), 1.44-1.21 (m, 4H), 1.08-0.95 (m, 2H). |
| 725 | 720.2 | 1H NMR (400 MHz, DMSO-d6) δ 8.28 (d, J = 7.4 Hz, 1H), 8.18 (brs, 3H), 8.07 (d, J = 8.1 Hz, 1H), 7.46 (s, 1H), 7.22 (d, J = 8.2 Hz, 1H), 7.05 (s, 1H), 6.95 (s, 1H), 6.86 (t, J = 74.7 Hz, 1H), 5.21-5.12 (m, 1H), 4.86-4.73 (m, 1H), 4.70-4.63 (m, 1H), 4.53-4.40 (m, 1H), 4.12 (s, 3H), 4.00 (s, 3H), 3.60 (brs, 2H), 2.06-1.55 (m, 7H), 1.50 (d, J = 7.1 Hz, 3H), 1.46 (s, 3H), 1.42-1.21 (m, 5H), 1.13-0.97 (m, 2H). |
| 726 | 676.2 | 1H NMR (400 MHz, DMSO-d6) δ 8.56 (d, J = 8.8 Hz, 1H), 8.10 (s, 2H), 8.06 (d, J = 8.0 Hz, 1H), 7.93 (brs, 1H), 7.48 (s, 1H), 7.24 (d, J = 8.1 Hz, 1H), 7.14 (s, 1H), 6.98 (d, J = 1.2 Hz, 1H), 5.51 (t, J = 13.5 Hz, 1H), 5.27-5.02 (m, 2H), 4.69 (brs, 1H), 4.19 (brs, 1H), 4.10 (s, 3H), 4.01 (s, 3H), 3.66 (brs, 2H), 3.32 (s, 3H), 2.34-1.49 (m, 10H), 1.44 (d, J = 7.1 Hz, 3H), 1.41-1.15 (m, 1H), 0.89-0.82 (m, 1H), 0.72-0.53 (m, 1H), 0.55-0.43 (m, 2H). |
| 727 | 720.2 | 1H NMR (400 MHz, DMSO-d6) δ 8.40 (d, J = 7.9 Hz, 1H), 8.11 (d, J = 8.0 Hz, 1H), 7.99 (brs, 3H), 7.41 (s, 1H), 7.27 (d, J = 8.1 Hz, 1H), 7.15 (s, 1H), 6.94 (d, J = 1.1 Hz, 1H), 5.52-5.33 (m, 1H), 5.28-5.10 (m, 2H), |

TABLE 3-continued

| Example | ES/MS m/z [M + H]+ | ¹H NMR |
|---|---|---|
| | | 4.10 (s, 3H), 3.99 (s, 3H), 3.63-3.37 (m, 3H), 3.36 (s, 3H), 2.44-2.29 (m, 1H), 2.15-1.57 (m, 6H), 1.56-1.39 (m, 1H), 1.46 (d, J = 7.1 Hz, 3H), 1.30-1.06 (m, 2H), 1.12 (s, 3H), 1.03-0.77 (m, 1H). |
| 728 | 708.5 | 1H NMR (400 MHz, DMSO-d6) δ 8.41 (d, J = 7.9 Hz, 1H), 8.11 (d, J = 8.0 Hz, 1H), 8.09 (s, 1H), 8.05 (s, 3H), 7.37 (d, J = 1.1 Hz, 1H), 7.27 (d, J = 8.1 Hz, 1H), 7.15 (s, 1H), 6.89 (s, 1H), 5.51-5.32 (m, 1H), 5.34-4.85 (m, 3H), 4.09 (s, 3H), 3.99 (s, 3H), 3.50-3.29 (m, 3H), 2.90 (brs, 1H), 2.41-2.30 (m, 2H), 2.15-1.56 (m, 5H), 1.55-1.40 (m, 1H), 1.46 (d, J = 7.2 Hz, 3H), 1.28-1.14 (m, 2H), 1.12 (s, 3H), 1.04-0.87 (m, 1H). |
| 729 | 612.3 | 1H NMR (400 MHz, DMSO-d6) δ 8.45 (d, J = 8.6 Hz, 1H), 8.00 (d, J = 8.1 Hz, 1H), 7.96 (brs, 3H), 7.44 (s, 1H), 7.16 (s, 1H), 7.15 (d, J = 8.5 Hz, 1H), 6.87 (s, 1H), 5.07-4.96 (m, 2H), 4.88-4.66 (m, 3H), 4.63-4.52 (m, 2H), 3.84 (brs, 2H), 3.76-3.65 (m, 2H), 3.36 (s, 3H), 2.04-1.47 (m, 8H), 1.43 (d, J = 7.1 Hz, 3H), 1.33-1.19 (m, 2H), 0.92-0.79 (m, 1H), 0.79-0.61 (m, 2H), 0.55-0.41 (m, 1H). |
| 730 | 756.1 | 1H NMR (400 MHz, DMSO-d6) δ 8.40 (d, J = 7.9 Hz, 1H), 8.20 (brs, 3H), 8.11 (d, J = 8.0 Hz, 1H), 7.84 (s, 1H), 7.82 (s, 1H), 7.52 (s, 1H), 7.50 (s, 1H), 7.43 (s, 1H), 7.27 (d, J = 8.1 Hz, 1H), 7.15 (s, 1H), 6.95 (d, J = 1.2 Hz, 1H), 6.86 (t, J = 74.8 Hz, 1H), 5.54-5.32 (m, 1H), 5.26-5.11 (m, 2H), 4.70-4.63 (m, 1H), 4.10 (s, 3H), 4.00 (s, 3H), 3.52-3.38 (m, 1H), 2.44 (s, 3H), 2.42-2.27 (m, 1H), 2.20-1.56 (m, 4H), 1.46 (d, J = 7.1 Hz, 3H), 1.32-1.15 (m, 1H), 1.12 (s, 3H), 1.05-0.82 (m, 1H). |
| 731 | 701.2 | 1H NMR (400 MHz, DMSO-d6) δ 9.24 (d, J = 6.6 Hz, 1H), 8.18 (s, 1H), 8.10 (d, J = 8.0 Hz, 1H), 8.07 (d, J = 8.5 Hz, 1H), 7.98 (s, 3H), 7.91 (dd, J = 8.2, 1.3 Hz, 1H), 7.80-7.73 (m, 1H), 7.65-7.59 (m, 1H), 7.44 (s, 1H), 7.30 (d, J = 8.1 Hz, 1H), 7.10 (s, 1H), 6.94 (d, J = 1.1 Hz, 1H), 5.31-5.17 (m, 1H), 4.97-4.80 (m, 1H), 4.64-4.52 (m, 1H), 4.13 (s, 3H), 4.00 (s, 3H), 3.96-3.69 (m, 3H), 3.37 (s, 3H), 3.29-3.22 (m, 1H), 2.81-2.55 (m, 1H), 2.64-2.38 (m, 2H), 2.04-1.84 (m, 1H), 1.82-1.69 (m, 1H), 1.55 (d, J = 7.1 Hz, 3H), 1.55-1.15 (m, 4H), 0.60-0.45 (m, 1H). |
| 732 | 737.3 | 1H NMR (400 MHz, DMSO-d6) δ 9.24 (d, J = 6.6 Hz, 1H), 8.20 (brs, 3H), 8.18 (s, 1H), 8.10 (d, J = 8.0 Hz, 1H), 8.07 (d, J = 8.4 Hz, 1H), 7.92 (dd, J = 8.3, 1.3 Hz, 1H), 7.80-7.72 (m, 1H), 7.65-7.59 (m, 1H), 7.46 (s, 1H), 7.30 (d, J = 8.1 Hz, 1H), 7.10 (s, 1H), 6.95 (d, J = 1.2 Hz, 1H), 6.86 (t, J = 74.8 Hz, 1H), 5.31-5.20 (m, 1H), 4.97-4.82 (m, 1H), 4.73-4.52 (m, 2H), 4.13 (s, 3H), 4.00 (s, 3H), 3.68-3.27 (m, 4H), 2.72-2.35 (m, 2H), 2.10-2.88 (m, 1H), 1.61-1.36 (m, 1H), 1.55 (d, J = 7.1 Hz, 3H), 1.32-1.12 (m, 3H), 0.66-0.43 (m, 1H). |
| 733 | 720.2 | 1H NMR (400 MHz, DMSO-d6) δ 8.39 (d, J = 7.4 Hz, 1H), 8.12 (d, J = 8.0 Hz, 1H), 7.99 (brs, 3H), 7.41 (s, 1H), 7.29 (d, J = 8.1 Hz, 1H), 7.16 (s, 1H), 6.96-6.93 (m, 1H), 5.44-5.06 (m, 4H), 4.10 (s, 3H), 3.99 (s, 3H), 3.58-3.37 (m, 3H), 3.37 (s, 3H), 2.50-2.41 (m, 1H), 2.00-1.59 (m, 7H), 1.56-1.41 (m, 1H), 1.48 (d, J = 7.4 Hz, 3H), 1.43 (s, 3H), 1.37-0.96 (m, 3H). |
| 734 | 648.3 | 1H NMR (400 MHz, DMSO-d6) δ 8.45 (d, J = 8.6 Hz, 1H), 8.18 (brs, 3H), 8.01 (d, J = 8.0 Hz, 1H), 7.46 (s, 1H), 7.16 (s, 1H), 7.15 (d, J = 8.5 Hz, 1H), 6.88 (s, 1H), 6.85 (t, J = 74.8 Hz, 1H), 5.10-4.98 (m, 2H), 4.79-4.55 (m, 6H), 3.91 (brs, 1H), 3.46 (brs, 1H), 2.06-1.39 (m, 10H), 1.43 (d, J = 7.1 Hz, 3H), 1.34-1.18 (m, 1H), 0.99-0.83 (m, 1H), 0.78-0.60 (m, 2H), 0.53-0.44 (m, 1H). |
| 735 | 715.2 | 1H NMR (400 MHz, DMSO-d6) δ 8.28 (s, 1H), 8.15 (d, J = 8.1 Hz, 1H), 8.05 (d, J = 8.5 Hz, 1H), 7.99 (brs, 3H), 7.94 (dd, J = 8.3, 1.4 Hz, 1H), 7.77 (ddd, J = 8.5, 6.8, 1.5 Hz, 1H), 7.64 (ddd, J = 8.1, 6.8, 1.2 Hz, 1H), 7.45 (s, 1H), 7.35 (d, J = 8.2 Hz, 1H), 7.11 (s, 1H), 6.94 (d, J = 1.1 Hz, 1H), 5.95 (q, J = 7.2 Hz, 1H), 4.86-4.73 (m, 1H), 4.61-4.53 (m, 1H), 4.13 (s, 3H), 4.00 (s, 3H), 3.55 (brs, 2H), 3.46-3.33 (m, 1H), 3.37 (s, 3H), 3.14 (s, 3H), 2.74-2.60 (m, 1H), 2.43-2.27 (m, 1H), 2.05-1.88 (m, 1H), 1.82-1.68 (m, 1H), 1.71 (d, J = 7.3 Hz, 3H), 1.67-1.21 (m, 8H), 0.79-0.65 (m, 1H). |
| 736 | 751.3 | 1H NMR (400 MHz, DMSO-d6) δ 8.28 (s, 1H), 8.19 (brs, 3H), 8.15 (d, J = 8.1 Hz, 1H), 8.05 (d, J = 8.4 Hz, 1H), 7.94 (dd, J = 8.3, 1.4 Hz, 1H), 7.77 (ddd, J = 8.5, 6.8, 1.5 Hz, 1H), 7.64 (ddd, J = 8.1, 6.8, 1.2 Hz, 1H), 7.47 (s, 1H), 7.35 (d, J = 8.2 Hz, 1H), 7.11 (s, 1H), 6.95 (d, J = 1.2 Hz, 1H), 6.84 (t, J = 74.8 Hz, 1H), 5.95 (q, J = 7.3 Hz, 1H), 4.95-4.75 (m, 1H), 4.73-4.62 (m, 1H), 4.62-4.52 (m, 1H), 4.17-4.13 (m, 1H), 4.13 (s, 3H), 4.00 (s, 3H), 3.99-3.93 (m, 1H), 3.50-3.34 (m, 3H), 3.13 (s, 3H), 2.80-2.58 (m, 1H), 2.45-2.27 (m, 1H), 2.12-1.89 (m, 4H), 1.71 (d, J = 7.3 Hz, 3H), 1.64-1.19 (m, 3H), 0.80-0.62 (m, 1H). |
| 737 | 646.2 | 1H NMR (400 MHz, DMSO-d6) δ 8.56 (d, J = 8.6 Hz, 1H), 8.06 (d, J = 8.0 Hz, 1H), 7.84 (brs, 2H), 7.55 (s, 0.3H 1st rotamer), 7.37 (s, 0.7H 2nd rotamer), 7.24 (d, J = 8.1 Hz, 1H), 7.14 (s, 0.3H 1st rotamer), 7.13 (s, 0.7H 2nd rotamer), 7.00 (s, 0.3 H 1st rotamer), 6.92 (s, 0.7H 2nd rotamer), 5.59-5.43 (m, 1H), 5.22-5.09 (m, 1H), 5.09-4.97 (m, 1H), 4.57 (s, 0.3H 1st rotamer), 4.10 (s, 3H), 4.00 (s, 3H), 3.90 (s, 0.7H 2nd rotamer), |

TABLE 3-continued

| Example | ES/MS m/z [M + H]+ | ¹H NMR |
|---|---|---|
| | | 3.51-3.33 (m, 3H), 2.23-1.76 (m, 4H), 1.77-1.50 (m, 3H), 1.48-1.18 (m, 2H), 1.44 (d, J = 7.1 Hz, 3H), 0.89-0.78 (m, 1H), 0.73-0.56 (m, 1H), 0.56-0.42 (m, 2H). |
| 738 | 638.2 | 1H NMR (400 MHz, DMSO-d6) δ 8.57 (d, J = 8.8 Hz, 1H), 8.09 (d, J = 8.0 Hz, 1H), 7.98 (brs, 3H), 7.72 (s, 1H), 7.71 (d, J = 8.3 Hz, 1H), 7.37 (d, J = 8.0 Hz, 1H), 7.33 (d, J = 11.8 Hz, 1H), 7.27 (s, 1H), 7.26 (d, J = 8.5 Hz, 1H), 7.21 (s, 1H), 5.55 (t, J = 13.6 Hz, 1H), 5.18 (dd, J = 27.8, 14.6 Hz, 1H), 5.11-5.01 (m, 1H), 4.09 (s, 3H), 3.73-3.67 (m, 2H), 3.63-3.40 (m, 2H), 3.37 (s, 3H), 2.28-1.87 (m, 4H), 1.82-1.50 (m, 2H), 1.45 (d, J = 7.1 Hz, 3H), 1.40-1.24 (m, 1H), 0.89-0.83 (m, 1H), 0.73-0.54 (m, 1H), 0.56-0.44 (m, 2H). |
| 739 | 636.2 | 1H NMR (400 MHz, DMSO-d6) δ 8.66 (d, J = 8.0 Hz, 1H), 8.11 (d, J = 8.0 Hz, 1H), 7.98 (brs, 3H), 7.72 (s, 1H), 7.33 (dd, J = 11.7, 1.2 Hz, 1H), 7.27 (d, J = 8.1 Hz, 1H), 7.22 (s, 1H), 6.42-6.29 (m, 1H), 5.86 (t, J = 18.3 Hz, 1H), 5.68-5.57 (m, 1H), 5.25 (dd, J = 28.2, 14.6 Hz, 1H), 5.07-4.97 (m 1H), 4.08 (s, 3H), 3.94-3.68 (m, 2H), 3.48-3.38 (m, 2H), 3.37 (s, 3H), 2.75-2.55 (m, 1H), 2.00-1.73 (m, 2H), 1.60-1.45 (m, 1H), 1.44 (d, J = 7.1 Hz, 3H), 1.23 (s, 3H), 1.00-0.89 (m, 1H), 0.78-0.58 (m, 2H). |
| 740 | 673.2 | 1H NMR (400 MHz, DMSO-d6) δ 9.10 (d, J = 7.2 Hz, 1H), 8.12 (d, J = 8.0 Hz, 1H), 7.98 (brs, 3H), 7.83 (d, J = 8.1 Hz, 1H), 7.71 (s, 1H), 7.42 (d, J = 8.0 Hz, 1H), 7.30 (d, J = 11.2 Hz, 1H), 7.28 (d, J = 8.1 Hz, 1H), 7.16 (s, 1H), 5.30-5.16 (m, 1H), 4.94-4.76 (m, 1H), 4.70-4.57 (m, 1H), 4.11 (s, 3H), 3.95-3.53 (m, 5H), 3.37 (s, 3H), 2.74-2.58 (m, 1H), 2.43-2.29 (m, 2H), 2.02-1.86 (m 1H), 1.82-1.72 (m, 1H), 1.66-1.40 (m, 2H), 1.50 (d, J = 7.1 Hz, 3H), 1.31-1.13 (m, 1H), 0.73-0.55 (m, 1H). |
| 741 | 657.3 | 1H NMR (400 MHz, DMSO-d6) δ 9.11 (d, J = 7.2 Hz, 1H), 8.12 (d, J = 8.0 Hz, 1H), 7.93 (brs, 3H), 7.83 (d, J = 8.0 Hz, 1H), 7.63 (s, 1H), 7.41 (d, J = 8.0 Hz, 1H), 7.28 (d, J = 8.1 Hz, 1H), 7.25 (d, J = 12 Hz, 1H), 7.16 (s, 1H), 5.31-5.15 (m, 1H), 4.94-4.82 (m, 1H), 4.71-4.59 (m, 1H), 4.11 (s, 3H), 3.02 (brs, 2H), 2.71-2.57 (m, 1H), 2.44-2.31 (m, 2H), 1.88-1.36 (m, 6H), 1.50 (d, J = 7.1 Hz, 3H), 1.29-1.11 (m, 1H), 1.20 (d, J = 7.0 Hz, 3H), 0.70-0.54 (m, 1H). |
| 742 | 662.3 | 1H NMR (400 MHz, DMSO-d6) δ 8.68 (d, J = 8.0 Hz, 1H), 8.09 (d, J = 8.1 Hz, 1H), 7.97 (s, 3H), 7.70 (s, 1H), 7.38 (s, 1H), 7.32 (dd, J = 11.5, 1.2 Hz, 1H), 7.26 (d, J = 8.1 Hz, 1H), 6.43-6.31 (m, 1H), 5.96-5.79 (m, 2H), 5.27 (dd, J = 28.4, 14.6 Hz, 1H), 5.10-4.97 (m, 1H), 4.07-4.01 (m, 1H), 3.87 (brs, 2H), 3.74-3.49 (m, 5H), 2.67-2.55 (m, 1H), 2.02-1.88 (m, 1H), 1.84-1.73 (m, 1H), 1.61-1.46 (m, 2H), 1.43 (d, J = 7.1 Hz, 3H), 1.29-1.21 (m, 1H), 1.07-0.90 (m, 3H), 0.84-0.70 (m, 1H), 0.70-0.59 (m, 1H), 0.51-0.40 (m, 1H). |
| 743 | 658.2 | 1H NMR (400 MHz, DMSO-d6) δ 9.20 (d, J = 6.8 Hz, 1H), 8.38 (s, 1H), 8.11 (d, J = 8.0 Hz, 1H), 7.99 (brs, 3H), 7.70 (s, 1H), 7.45 (s, 1H), 7.30 (d, J = 12.3 Hz, 1H), 7.28 (d, J = 8.0 Hz, 1H), 7.16 (s, 1H), 5.26-5.12 (m, 1H), 4.92-4.78 (m, 1H), 4.69-4.61 (m, 1H), 4.11 (s, 3H), 3.63-3.59 (m, 2H), 3.48-3.38 (m, 2H), 3.37 (s, 3H), 2.44-2.26 (m, 2H), 1.97 (brs, 1H), 1.84-1.68 (m, 4H), 1.67-1.09 (m, 4H), 1.50 (d, J = 7.1 Hz, 3H), 0.67-0.49 (m, 1H). |
| 744 | 673.2 | 1H NMR (400 MHz, DMSO-d6) δ 9.20 (d, J = 6.8 Hz, 1H), 8.38 (s, 1H), 8.11 (d, J = 8.0 Hz, 1H), 7.99 (brs, 3H), 7.70 (s, 1H), 7.45 (s, 1H), 7.35-7.25 (m, 2H), 7.16 (s, 1H), 5.26-5.11 (m, 1H), 4.96-4.81 (m, 1H), 4.75-4.62 (m, 1H), 4.11 (s, 3H), 3.64-3.58 (m, 2H), 3.48-3.38 (m, 1H), 3.37 (s, 3H), 2.41-2.29 (m, 2H), 1.99-1.85 (m, 1H), 1.87-1.72 (m, 4H), 1.66-1.42 (m, 5H), 1.37-1.12 (m, 2H), 0.68-0.51 (m, 1H). |
| 745 | 682.3 | 1H NMR (400 MHz, DMSO-d6) δ 8.60 (d, J = 8.7 Hz, 1H), 8.08 (d, J = 8.0 Hz, 1H), 7.97 (brs, 3H), 7.72 (s, 1H), 7.32 (dd, J = 11.4, 1.2 Hz, 1H), 7.28 (s, 1H), 7.25 (d, J = 8.1 Hz, 1H), 5.81 (t, J = 13.6 Hz, 1H), 5.33-5.00 (m, 3H), 4.10-4.00 (m, 1H), 3.77-3.68 (m, 2H), 3.47-3.38 (m, 1H), 3.37 (s, 3H), 2.32-1.46 (m, 8H), 1.45 (d, J = 7.1 Hz, 3H), 1.39-1.20 (m, 2H), 0.95-0.75 (m, 2H), 0.73-0.56 (m, 1H), 0.57-0.44 (m, 2H). |
| 746 | 682.5 | 1H NMR (400 MHz, DMSO-d6) δ 8.58 (d, J = 8.8 Hz, 1H), 8.05 (d, J = 8.0 Hz, 1H), 7.98 (brs, 3H), 7.72 (s, 1H), 7.50 (s, 1H), 7.32 (dd, J = 11.6, 1.2 Hz, 1H), 7.24 (d, J = 8.0 Hz, 1H), 6.16-6.00 (m, 1H), 5.25-4.84 (m, 3H), 4.18-4.09 (m, 1H), 3.78-3.68 (m, 2H), 3.63-3.39 (m, 2H), 3.37 (s, 3H), 2.38-1.48 (m, 9H), 1.44 (d, J = 7.1 Hz, 3H), 1.39-1.21 (m, 1H), 0.91-0.80 (m, 1H), 0.73-0.58 (m, 1H), 0.56-0.47 (m, 2H). |
| 747 | 666.3 | 1H NMR (400 MHz, DMSO-d6) δ 8.58 (d, J = 8.7 Hz, 1H), 8.05 (d, J = 8.0 Hz, 1H), 7.96 (brs, 3H), 7.66-7.64 (m, 1H), 7.50 (s, 1H), 7.32-7.21 (m, 2H), 6.19-6.01 (m, 1H), 5.31-4.81 (m, 3H), 4.17-4.05 (m, 1H), 3.47-3.32 (m, 1H), 3.10 (brs, 1H), 2.40-1.94 (m, 4H), 1.92-1.49 (m, 8H), 1.44 (d, J = 7.0 Hz, 3H), 1.39-1.21 (m, 1H), 1.21 (d, J = 6.9 Hz, 3H), 0.89-0.81 (m, 1H), 0.74-0.58 (m, 1H), 0.56-0.43 (m, 2H). |
| 748 | 699.3 | 1H NMR (400 MHz, DMSO-d6) δ 9.36 (s, 1H), 9.34 (s, 1H), 8.20 (d, J = 8.3 Hz, 1H), 8.14 (d, J = 8.2 Hz, 1H), 7.96 (brs, 3H), 7.92 (s, 1H), 7.78-7.69 (m, 1H), 7.61 (s, 1H), 7.34 (s, 1H), 7.33 (s, 1H), 7.25 (d, J = 11.3 Hz, |

TABLE 3-continued

| Example | ES/MS m/z [M + H]+ | 1H NMR |
|---|---|---|
| | | 1H), 5.61-5.49 (m, 1H), 5.08-4.92 (m, 1H), 4.89-4.73 (m, 1H), 4.08-4.00 (m, 4H), 3.37 (brs, 2H), 3.03 (brs, 1H), 2.64-2.52 (m, 2H), 1.88-1.44 (m, 5H), 1.54 (d, J = 7.0 Hz, 3H), 1.28 (brs, 1H), 1.20 (d, J = 6.9 Hz, 3H), 1.14-0.93 (m, 2H), 0.67-0.39 (m, 2H). |
| 749 | 611.3 | 1H NMR (400 MHz, DMSO-d6) δ 8.08 (s, 1H), 8.04 (d, J = 8.1 Hz, 1H), 7.92 (s, 1H), 7.61 (d, J = 8.1 Hz, 1H), 7.53 (s, 0.35H minor rotamer), 7.40 (s, 0.35H minor rotamer), 7.35 (s, 0.65H major rotamer), 7.07 (d, J = 8.3 Hz, 0.65H major rotamer), 6.99 (s, 0.65H major rotamer), 6.94 (s, 0.35H minor rotamer), 5.13-5.01 (m, 1H), 4.77-4.51 (m, 2H), 4.25-4.11 (m, 2H), 4.10 (s, 3H), 3.99 (s, 3H), 3.67-3.49 (m, 4H), 3.25-3.13 (m, 1H), 2.67 (brs, 1H), 2.13-1.84 (m, 4H), 1.76-1.56 (m, 3H), 1.51-1.30 (m, 4H), 1.45 (d, J = 7.3 Hz, 3H), 1.24 (s, 2H), 1.18-0.99 (m, 4H), 0.94 (s, 2H). |
| 750 | 701.1 | 1H NMR (400 MHz, DMSO-d6) δ 8.75 (brs, 2H), 8.64 (d, J = 8.1 Hz, 1H), 8.14 (d, J = 8.2 Hz, 1H), 8.02 (d, J = 6.2 Hz, 1H), 7.85 (d, J = 8.0 Hz, 1H), 7.63 (d, J = 10.7 Hz, 1H), 7.47 (d, J = 8.3 Hz, 1H), 7.37 (s, 1H), 7.31 (d, J = 8.4 Hz, 1H), 5.97-5.86 (m, 1H), 4.96-4.69 (m, 3H), 4.51-4.32 (m, 1H), 3.42 (dd, J = 35.2, 12.1 Hz, 2H), 3.08 (s, 3H), 3.05-2.91 (m, 1H), 2.80-2.64 (m, 2H), 2.47-2.26 (m, 2H), 2.13 (brs, 1H), 2.02-1.82 (m, 1H), 1.68 (d, J = 7.3 Hz, 3H), 1.63-1.49 (m, 3H), 1.35-1.09 (m, 3H), 0.95-0.72 (m, 2H), 0.61-0.47 (m, 1H). |
| 751 | 687.2 | 1H NMR (400 MHz, DMSO-d6) δ 9.12 (d, J = 7.1 Hz, 1H), 8.83 (brs, 3H), 8.64 (dd, J = 8.2 Hz, 1H), 8.10 (d, J = 8.1 Hz, 1H), 8.00 (d, J = 6.4 Hz, 1H), 7.82 (d, J = 8.1 Hz, 1H), 7.63 (d, J = 10.5 Hz, 1H), 7.41 (d, J = 8.0 Hz, 1H), 7.36 (s, 1H), 7.26 (d, J = 8.1 Hz, 1H), 5.27-5.16 (m, 1H), 4.98-4.68 (m, 3H), 4.47-4.33 (m, 1H), 3.88-3.82 (m, 2H), 3.42 (dd, J = 32.9, 12.5 Hz, 1H), 3.13-2.90 (m, 2H), 2.71-2.55 (m, 1H), 2.45-2.27 (m, 2H), 2.01-1.83 (m, 1H), 1.50 (d, J = 7.1 Hz, 3H), 1.48-1.10 (m, 5H), 1.04-0.90 (m, 1H), 0.62-0.41 (m, 2H). |
| 752 | 646.2 | 1H NMR (400 MHz, DMSO-d6) δ 8.56 (d, J = 8.8 Hz, 1H), 8.06 (d, J = 8.0 Hz, 1H), 7.98 (brs, 2H), 7.81 (brs, 1H), 7.48 (s, 1H), 7.24 (d, J = 8.0 Hz, 1H), 7.14 (s, 1H), 6.98 (s, 1H), 5.51 (t, J = 13.6 Hz, 1H), 5.26-4.99 (m, 2H), 4.76 (brs, 0.6H major rotamer), 4.21 (brs, 0.4 H, minor rotamer), 4.10 (s, 3H), 4.01 (s, 3H), 2.26-1.49 (m, 13H), 1.44 (d, J = 7.1 Hz, 3H), 1.38-1.23 (m, 1H), 0.90-0.81 (m, 1H), 0.73-0.55 (m, 1H), 0.55-0.44 (m, 2H). |
| 753 | 610.2 | 1H NMR (400 MHz, DMSO-d6) δ 8.55 (d, J = 8.2 Hz, 1H), 8.05 (brs, 1H), 8.03 (d, J = 8.0 Hz, 1H), 7.82 (brs, 1H), 7.61 (d, J = 7.9 Hz, 1H), 7.37 (s, 1H), 7.31 (brs, 1H), 7.17 (d, J = 8.0 Hz, 1H), 5.80-5.51 (m, 2H), 5.16 (brs, 0.6H major rotamer), 5.09-4.94 (m, 1H), 4.87-4.70 (m, 1H), 4.42 (d, J = 13.4 Hz, 0.4H minor rotamer), 4.05 (brs, 2H), 3.43-3.01 (m, 2H), 2.93-2.81 (m, 0.4H minor rotamer), 2.47 (brs, 0.6H major rotamer), 1.92-1.45 (m, 6H), 1.43 (d, J = 7.1 Hz, 3H), 1.35-1.10 (m, 7H), 0.99-0.55 (m, 5H). |
| 754 | 729.2 | 1H NMR (400 MHz, DMSO-d6) δ 9.29 (d, J = 6.6 Hz, 1H), 8.43 (s, 1H), 8.12 (d, J = 8.1 Hz, 1H), 8.07 (dd, J = 8.3, 1.4 Hz, 1H), 8.01 (d, J = 5.4 Hz, 2H), 7.95 (d, J = 8.4 Hz, 1H), 7.82-7.78 (m, 1H), 7.76 (brs, 0.4H minor rotamer), 7.67-7.60 (m, 2H), 7.55 (brs, 0.6H major rotamer), 7.35 (d, J = 5.8 Hz, 1H), 7.30 (d, J = 8.1 Hz, 1H), 5.26-5.17 (m, 1H), 5.06 (brs, 0.4H minor rotamer), 5.02-4.76 (m, 2H), 4.62 (dd, J = 13.3, 6.0 Hz, 0.6H major rotamer), 4.03 (s, 2H), 3.44-3.01 (m, 2H), 2.98-2.70 (m, 2H), 2.64-2.49 (m, 1H), 1.98 (brs, 1H), 1.90-1.31 (m, 8H), 1.55 (d, J = 7.0 Hz, 3H), 1.31-1.03 (m, 4H), 0.64-0.39 (m, 2H). |
| 755 | 710.2 | 1H NMR (400 MHz, DMSO-d6) δ 8.58 (d, J = 8.8 Hz, 1H), 8.06 (d, J = 8.0 Hz, 1H), 7.99 (s, 2H), 7.76 (brs, 0.6H major rotamer), 7.69 (brs, 0.4H minor rotamer), 7.62 (brs, 0.4H minor rotamer), 7.54 (brs, 0.6H major rotamer), 7.30 (brs, 1H), 7.24 (d, J = 8.0 Hz, 1H), 6.24 (brs, 1H), 5.27-4.88 (m, 4H), 4.52 (brs, 0.4H minor rotamer), 4.42 (brs, 1H), 4.18 (brs, 0.6H major rotamer), 3.41-3.09 (m, 3H), 2.82-2.74 (m, 1H), 2.29-1.49 (m, 13H), 1.44 (d, J = 7.1 Hz, 3H), 1.37-1.20 (m, 1H), 0.92-0.80 (m, 1H), 0.76-0.59 (m, 1H), 0.56-0.34 (m, 2H). |
| 756 | 710.3 | 1H NMR (400 MHz, DMSO-d6) δ 8.60 (d, J = 8.8 Hz, 1H), 8.09 (d, J = 8.0 Hz, 1H), 7.97 (brs, 2H), 7.76 (brs, 1H), 7.69 (brs, 0.4H minor rotamer), 7.63 (brs, 0.6H major rotamer), 7.32 (brs, 1H), 7.26 (d, J = 8.1 Hz, 1H), 7.22 (s, 1H), 5.82-5.63 (s, 1H), 5.37-4.90 (m, 4H), 4.53 (brs, 0.4H minor rotamer), 4.41 (brs, 1H), 4.16 (brs, 0.6H major rotamer), 3.70 (brs, 1H), 3.16 (brs, 2H), 2.77 (brs, 1H), 2.31-1.47 (m, 13H), 1.44 (d, J = 7.0 Hz, 3H), 1.41-1.24 (m, 1H), 0.94-0.79 (m, 1H), 0.74-0.69 (m, 1H), 0.60-0.40 (m, 2H). |
| 757 | 646.2 | 1H NMR (400 MHz, DMSO-d6) δ 8.70 (d, J = 7.6 Hz, 1H), 8.01 (d, J = 8.1 Hz, 1H), 7.99 (brs, 1H), 7.76 (brs, 1H), 7.37 (brs, 1H), 7.16 (d, J = 8.1 Hz, 1H), 7.02 (s, 1H), 6.89 (s, 1H), 5.03-4.91 (m, 1H), 4.71-4.48 (m, 3H), 4.24 (brs, 1H), 4.12 (s, 3H), 3.99 (s, 3H), 3.44-3.02 (m, 3H), 2.77 (brs, 1H), 2.47-2.42 (m, 1H), 2.03-1.48 (m, 9H), 1.46 (d, J = 7.1 Hz, 3H), 1.41-1.09 (m, 4H). |

TABLE 3-continued

| Example | ES/MS m/z [M + H]+ | ¹H NMR |
|---|---|---|
| 758 | 654.3 | 1H NMR (400 MHz, DMSO-d6) δ 8.37 (d, J = 9.5 Hz, 1H), 8.00 (s, 2H), 7.91 (d, J = 8.0 Hz, 1H), 7.78 (s, 1H), 7.64 (d, J = 8.0 Hz, 0.4H minor rotamer), 7.29 (d, J = 8.0 Hz, 0.6H major rotamer), 7.23 (brs, 1H), 7.09 (d, J = 8.0 Hz, 1H), 6.65 (s, 1H), 6.43 (s, 1H), 5.23-5.10 (m, 1H), 4.98 (brs, 1H), 4.72 (t, J = 12.0 Hz, 1H), 4.60-4.43 (m, 2H), 4.23 (brs, 1H), 4.12 (s, 3H), 3.48-3.04 (m, 2H), 2.84-2.65 (m, 1H), 2.42-2.15 (m, 2H), 2.05-1.48 (m, 10H), 1.45 (d, J = 7.0 Hz, 3H), 1.39-1.05 (m, 2H), 1.00-0.80 (m, 3H), 0.42 (brs, 1H), 0.30-0.17 (m, 1H). |
| 759 | 672.2 | 1H NMR (400 MHz, DMSO-d6) δ 8.46 (d, J = 8.5 Hz, 1H), 8.04 (brs, 1H), 8.00 (d, J = 8.0 Hz, 1H), 7.77 (brs, 1H), 7.46 (t, J = 73.8 Hz, 1H), 7.22 (s, 1H), 7.18 (brs, 1H), 7.14 (d, J = 8.1 Hz, 1H), 5.11-4.96 (m, 1H), 4.80 (brs, 2H), 4.53 (brs, 1H), 4.20 (brs, 1H), 3.96-3.09 (m, 4H), 2.78 (s, 1H), 2.05-1.49 (m, 11H), 1.44 (d, J = 7.1 Hz, 3H), 1.41-0.45 (m, 11H). |
| 760 | 743.2 | 1H NMR (400 MHz, DMSO-d6) δ 9.13 (d, J = 7.1 Hz, 1H), 8.10 (d, J = 8.0 Hz, 1H), 8.00 (brs, 2H), 7.82 (d, J = 8.0 Hz, 1H), 7.76 (brs, 1H), 7.45 (t, J = 73.9 Hz, 1H), 7.42 (d, J = 8.0 Hz, 1H), 7.30-7.22 (m, 2H), 7.17 (brs, 1H), 5.25-5.15 (m, 1H), 5.04-4.77 (m, 2H), 4.53 (brs, 1H), 4.21 (brs, 1H), 3.99-3.90 (m, 1H), 3.39-3.08 (m, 2H), 2.84-2.56 (m, 2H), 2.48-2.30 (m, 2H), 2.07-1.34 (m, 8H), 1.50 (d, J = 7.0 Hz, 3H), 1.29-0.88 (m, 5H), 0.63-0.34 (m, 2H). |
| 761 | 662.2 | 1H NMR (400 MHz, DMSO-d6) δ 8.26 (d, J = 9.4 Hz, 1H), 8.17 (d, J = 8.0 Hz, 1H), 7.97 (brs, 2H), 7.74 (brs, 1H), 7.41 (brs, 1H), 7.34 (d, J = 8.1 Hz, 1H), 7.19 (s, 1H), 6.91 (s, 1H), 5.57-5.30 (m, 3H), 5.00 (brs, 1H), 4.53 (brs, 1H), 4.25 (brs, 1H), 4.10 (s, 3H), 4.00 (s, 3H), 3.14-2.96 (m, 1H), 2.80 (brs, 1H), 2.03-1.34 (m, 11H), 1.48 (d, J = 6.8 Hz, 3H), 1.30-0.92 (m, 4H). |
| 762 | 712.4 | 1H NMR (400 MHz, DMSO-d6) δ 9.10 (d, J = 7.2 Hz, 1H), 8.12 (d, J = 8.0 Hz, 1H), 7.97 (s, 1H), 7.83 (d, J = 8.1 Hz, 1H), 7.74 (brs, 2H), 7.45 (t, J = 73.4 Hz, 1H), 7.41 (d, J = 8.0 Hz, 1H), 7.28 (d, J = 8.1 Hz, 1H), 7.18 (brs, 1H), 7.14 (s, 1H), 5.28-5.16 (m, 1H), 4.99 (brs, 1H), 4.93-4.77 (m, 1H), 4.68-4.55 (m, 1H), 4.54 (brs, 1H), 4.20 (s, 1H), 4.09 (s, 3H), 3.45-2.55 (m, 3H), 2.45-2.31 (m, 2H), 2.04-1.37 (m, 9H), 1.50 (d, J = 7.0 Hz, 3H), 1.23 (brs, 1H), 0.62 (s, 1H). |
| 763 | 646.3 | 1H NMR (400 MHz, DMSO-d6) δ 8.45 (d, J = 8.5 Hz, 1H), 8.01 (d, J = 8.0 Hz, 1H), 7.98 (brs, 2H), 7.74 (brs, 2H), 7.68 (brs, 1H), 7.45 (t, J = 73.4 Hz, 1H), 7.20 (brs, 1H), 7.16 (d, J = 8.1 Hz, 1H), 7.07 (s, 1H), 5.06-4.95 (m, 1H), 4.74-4.47 (m, 2H), 4.20 (brs, 1H), 4.09 (s, 3H), 2.78 (brs, 1H), 2.01-1.51 (m, 13H), 1.44 (d, J = 7.1 Hz, 3H), 1.42-1.17 (m, 2H), 0.90-0.81 (m, 1H), 0.77-0.60 (m, 2H), 0.53-0.45 (m, 1H). |
| 764 | 697.4 | 1H NMR (400 MHz, DMSO-d6) δ 9.13 (d, J = 7.0 Hz, 1H), 8.11 (d, J = 8.1 Hz, 1H), 7.97 (brs, 1H), 7.79-7.55 (m, 2H), 7.42 (d, J = 8.0 Hz, 1H), 7.32 (s, 1H), 7.27 (d, J = 8.1 Hz, 1H), 7.25 (brs, 1H), 5.26-5.16 (m, 1H), 5.04-4.77 (m, 2H), 4.18 (brs, 1H), 4.07-3.97 (m, 1H), 2.72-2.59 (m, 1H), 2.45-2.31 (m, 2H), 2.01-1.34 (m, 11H), 1.50 (d, J = 7.0 Hz, 3H), 1.29-0.90 (m, 4H), 0.65-0.38 (m, 2H). |
| 765 | 648.2 | 1H NMR (400 MHz, DMSO-d6) δ 8.56 (d, J = 8.8 Hz, 1H), 8.06 (d, J = 7.9 Hz, 1H), 7.96 (brs, 2H), 7.72 (brs, 1H), 7.39 (s, 1H), 7.24 (d, J = 8.0 Hz, 1H), 7.14 (s, 1H), 6.91 (s, 1H), 5.52 (t, J = 13.6 Hz, 1H), 5.21-4.98 (m, 2H), 4.26 (brs, 1H), 4.10 (s, 3H), 4.00 (s, 3H), 2.25-1.49 (m, 11H), 1.44 (d, J = 7.1 Hz, 3H), 1.39-1.21 (m, 2H), 0.88-0.80 (m, 1H), 0.72-0.56 (m, 1H), 0.57-0.46 (m, 2H). |
| 766 | 672.3 | 1H NMR (400 MHz, DMSO-d6) δ 8.59 (d, J = 8.8 Hz, 1H), 8.05 (d, J = 8.0 Hz, 1H), 7.97 (brs, 2H), 7.73 (s, 1H), 7.35 (s, 1H), 7.28 (s, 1H), 7.22 (d, J = 8.1 Hz, 1H), 6.92 (s, 1H), 5.88 (t, J = 13.7 Hz, 1H), 5.27-4.91 (m, 2H), 4.53 (s, 1H), 4.26 (s, 1H), 4.00 (s, 3H), 3.97-3.89 (m, 1H), 3.81 (brs, 1H), 2.77 (brs, 1H), 2.29-1.49 (m, 11H), 1.44 (d, J = 7.1 Hz, 3H), 1.38-1.16 (m, 2H), 1.00-0.79 (m, 3H), 0.73-0.57 (m, 1H), 0.59-0.38 (m, 3H). |
| 767 | 636.3 | 1H NMR (400 MHz, DMSO-d6) δ 8.45 (d, J = 8.5 Hz, 1H), 7.97 (d, J = 8.0 Hz, 1H), 7.73 (s, 1H), 7.33 (s, 1H), 7.15 (s, 1H), 7.12 (d, J = 8.1 Hz, 1H), 6.90 (s, 1H), 5.07-4.93 (m, 1H), 4.78 (brs, 2H), 4.53 (s, 1H), 4.25 (s, 1H), 3.94-3.85 (m, 1H), 2.76 (brs, 1H), 2.13-1.49 (m, 12H), 1.44 (d, J = 7.1 Hz, 3H), 1.39-1.17 (m, 3H), 1.18-0.94 (m, 3H), 0.92-0.59 (m, 5H), 0.54-0.40 (m, 3H). |
| 768 | 707.3 | 1H NMR (400 MHz, DMSO-d6) δ 9.07 (d, J = 7.2 Hz, 1H), 8.01 (brs, 1H), 7.99 (d, J = 8.1 Hz, 1H), 7.81 (d, J = 8.0 Hz, 1H), 7.79 (brs, 1H), 7.40 (d, J = 8.0 Hz, 0.4H minor rotamer), 7.29 (s, 0.4H minor rotamer), 7.22 (brs, 0.6H major rotamer), 7.18 (d, J = 8.0 Hz, 1H), 6.71 (s, 1H), 6.43 (s, 1H), 5.25-5.15 (m, 1H), 4.98 (s, 1H), 4.87-4.75 (m, 1H), 4.60-4.48 (m, 2H), 4.24 (s, 1H), 4.12 (s, 3H), 3.84 (brs, 1H), 3.44-3.08 (m, 2H), 2.84-2.54 (m, 1H), 2.46-2.29 (m, 3H), 2.08-1.55 (m, 6H), 1.49 (d, J = 7.0 Hz, 3H), 1.45-1.27 (m, 2H), 1.21-1.07 (m, 1H), 1.00-0.80 (m, 2H), 0.62-0.39 (m, 2H), 0.25-0.16 (m, 1H). |
| 769 | 690.2 | 1H NMR (400 MHz, DMSO-d6) δ 8.59 (d, J = 9.6 Hz, 1H), 8.06 (d, J = 8.0 Hz, 1H), 7.96 (brs, 2H), 7.72 (brs, 1H), 7.36 (brs, 1H), 7.28 (s, 1H), 7.25 (d, J = 8.1 Hz, 1H), 6.92 (s, 1H), 5.87 (t, J = 13.8 Hz, 1H), 5.34- |

TABLE 3-continued

| Example | ES/MS m/z [M + H]+ | ¹H NMR |
|---|---|---|
| | | 5.16 (m, 2H), 4.99 (s, 1H), 4.53 (s, 1H), 4.26 (s, 1H), 4.00 (s, 3H), 3.97-3.87 (m, 1H), 3.44-2.80 (m, 3H), 2.45-1.38 (m, 11H), 1.46 (d, J = 7.1 Hz, 3H), 1.29-1.08 (m, 2H), 1.04-0.81 (m, 3H), 0.44-0.35 (m, 1H). |
| 770 | 648.2 | 1H NMR (400 MHz, DMSO-d6) δ 8.83 (d, J = 6.9 Hz, 1H), 8.08 (d, J = 8.0 Hz, 1H), 7.96 (brs, 2H), 7.73 (brs, 1H), 7.37 (brs, 1H), 7.35 (dd, J = 7.4, 1.6 Hz, 1H), 7.30 (dd, J = 7.5, 1.6 Hz, 1H), 7.24 (d, J = 8.1 Hz, 2H), 7.20 (d, J = 7.8 Hz, 1H), 7.08 (s, 1H), 6.90 (brs, 1H), 5.25-5.14 (m, 1H), 5.00 (brs, 1H), 4.93-4.79 (m, 1H), 4.60 (d, J = 13.3 Hz, 1H), 4.23 (s, 1H), 4.12 (s, 3H), 4.00 (s, 3H), 2.41-2.16 (m, 3H), 2.05-1.37 (m, 7H), 1.49 (d, J = 7.1 Hz, 3H), 1.29-1.05 (m, 2H), 0.60-0.42 (m, 1H). |
| 771 | 690.4 | 1H NMR (400 MHz, DMSO-d6) δ 8.12 (s, 0.6H major rotamer), 8.10 (s, 1H), 8.08 (s, 0.4H minor rotamer), 8.00 (s, 2H), 7.79 (brs, 1H), 7.37 (brs, 1H), 7.29 (d, J = 8.2 Hz, 1H), 7.27 (s, 1H), 6.92 (s, 1H), 5.68-5.54 (m, 1H), 5.50-5.22 (m, 2H), 4.99 (brs, 0.4H minor rotamer), 4.53 (brs, 0.6H major rotamer), 4.26 (brs, 0.6H major rotamer), 4.00 (s, 3H), 3.96-3.86 (m, 1H), 3.44-3.03 (m, 4H), 2.77 (brs, 0.4H minor rotamer), 2.66-2.52 (m, 1H), 2.05-1.50 (m, 8H), 1.45 (d, J = 6.9 Hz, 3H), 1.35 (s, 3H), 1.21 (s, 3H), 1.19-1.02 (m, 1H), 0.97-0.80 (m, 2H), 0.45-0.35 (m, 1H). |
| 772 | 666.2 | 1H NMR (400 MHz, DMSO-d6) δ 8.51 (d, J = 9.7 Hz, 1H), 8.04 (d, J = 8.1 Hz, 1H), 8.00 (brs, 1H), 7.77 (brs, 1H), 7.36 (s, 1H), 7.20 (d, J = 8.1 Hz, 1H), 7.19 (s, 1H), 6.91 (s, 1H), 5.38-5.25 (m, 1H), 5.15-4.82 (m, 2H), 4.65-4.23 (m, 1H), 4.00 (s, 3H), 3.95-3.84 (m, 3H), 3.46-2.74 (m, 4H), 2.36-2.15 (m, 2H), 2.10-1.90 (m, 3H), 1.90-1.31 (m, 5H), 1.46 (d, J = 7.1 Hz, 3H), 1.20-1.04 (m, 2H), 1.02-0.88 (m, 2H), 0.87-0.70 (m, 2H), 0.54-0.42 (m, 1H), 0.17-0.05 (m, 1H), 0.05--0.01 (m, 1H). |
| 773 | 676.3 | 1H NMR (400 MHz, DMSO-d6) δ 8.27 (d, J = 9.5 Hz, 1H), 8.17 (d, J = 8.0 Hz, 1H), 8.00 (brs, 2H), 7.76 (brs, 1H), 7.72-7.59 (m, 1H), 7.39 (s, 1H), 7.34 (J = 8.0 Hz, , 1H), 7.32-7.20 (m, 1H), 5.60-5.48 (m, 2H), 5.44-5.32 (m, 1H), 4.97 (brs, 0.4H minor rotamer), 4.52 (brs, 0.6H major rotamer), 4.19 (brs, 1H), 4.06-3.97 (m, 1H), 3.21-3.08 (m, 1H), 2.77 (brs, 1H), 2.04-1.42 (m, 8H), 1.49 (d, J = 6.8 Hz, 3H), 1.29-0.90 (m, 7H), 0.99 (h, J = 6.4, 5.8 Hz, 4H), 0.52-0.41 (m, 1H). |
| 774 | 695.1 | 1H NMR (400 MHz, DMSO-d6) δ 9.12 (d, J = 7.1 Hz, 1H), 8.10 (d, J = 8.1 Hz, 1H), 7.90 (brs, 2H), 7.83 (d, J = 8.1 Hz, 1H), 7.71 (brs, 1H), 7.65 (brs, 1H), 7.42 (d, J = 8.1 Hz, 1H), 7.32 (s, 1H), 7.27 (d, J = 8.1 Hz, 1H), 7.25 (d, J = 11.8 Hz, 1H), 6.52 (brs, 1H), 5.28-5.12 (m, 1H), 5.09 (brs, 1H), 5.01-4.75 (m, 2H), 4.27 (brs, 1H), 4.06-3.96 (m, 1H), 2.67-2.58 (m, 1H), 2.42-2.36 (m, 2H), 2.09-1.92 (m, 3H), 1.71 (brs, 2H), 1.50 (d, J = 7.0 Hz, 3H), 1.44 (brs, 2H), 1.31-0.94 (m, 4H), 0.69-0.43 (m, 2H) 0.14-0.03 (m, 1H). |
| 775 | 660.5 | 1H NMR (400 MHz, DMSO-d6) δ 8.72 (d, J = 7.6 Hz, 1H), 8.02 (d, J = 8.0 Hz, 1H), 7.99 (s, 2H), 7.75 (s, 1H), 7.68-7.55 (m, 1H), 7.27 (s, 1H), 7.23 (brs, 1H), 7.17 (d, J = 8.1 Hz, 1H), 5.03-4.92 (p, J = 7.0 Hz, 1H), 4.84 (brs, 1H), 4.70-4.59 (m, 1H), 4.53 (brs, 0.4H minor rotamer), 4.17 (brs, 0.6H major rotamer), 4.04-3.96 (m, 1H), 3.73 (brs, 2H), 3.12 (brs, 1H), 2.77 (brs, 1H), 2.48-2.43 (m, 2H), 2.03-1.50 (m, 10H), 1.46 (d, J = 7.0 Hz, 3H), 1.42-1.06 (m, 5H), 0.91 (brs, 1H), 0.65 (brs, 1H). |
| 776 | 729.5 | 1H NMR (400 MHz, DMSO-d6) δ 9.19 (d, J = 7.1 Hz, 1H), 8.13 (d, J = 8.0 Hz, 1H), 8.00 (brs, 2H), 7.95 (d, J = 7.8 Hz, 1H), 7.77 (brs, 1H), 7.66 (brs, 0.4H minor rotamer), 7.60 (d, J = 7.8 Hz, 1H), 7.39 (s, 1H), 7.29 (d, J = 8.1 Hz, 1H), 7.24 (brs, 0.6H major rotamer), 6.93 (t, J = 55.0 Hz, 1H), 5.30-5.18 (m, 1H), 5.05-4.86 (m, 1H), 4.85-4.72 (m, 1H), 4.70-4.43 (m, 3H), 4.15 (brs, 1H), 3.75 (m, 1H), 3.15 (brs, 1H), 2.84-2.65 (m, 2H), 2.48-2.30 (m, 2H), 2.03-1.39 (m, 10H), 1.51 (d, J = 7.0 Hz, 3H), 1.32-1.16 (m, 1H), 0.73-0.55 (m, 1H). |
| 777 | 697.2 | 1H NMR (400 MHz, DMSO-d6) δ 9.11 (d, J = 7.3 Hz, 1H), 7.98 (d, J = 7.9 Hz, 1H), 7.93 (d, J = 7.8 Hz, 1H), 7.77 (brs, 1H), 7.58 (d, J = 7.8 Hz, 1H), 7.35 7.21 (m, 1H), 7.18 (d, J = 8.0 Hz, 1H), 6.92 (t, J = 55.0 Hz, 1H), 6.65 (brs, 1H), 6.34 (s, 1H), 5.29-5.17 (m, 1H), 4.98 (brs, 0.4H minor rotamer), 4.86-4.76 (m, 1H), 4.53 (d, J = 13.0 Hz, 2H), 4.24 (brs, 0.6H major rotamer), 4.09 (s, 3H), 3.78 (brs, 2H), 3.15 (brs, 2H), 2.81 (s, 3H), 2.71-2.59 (m, 1H), 2.47-2.36 (m, 2H), 2.03-1.46 (m, 6H), 1.49 (d, J = 7.0 Hz, 3H), 1.49-1.33 (m, 2H), 1.27-1.12 (m, 1H), 0.65-0.48 (m, 1H). |
| 778 | 656.4 | 1H NMR (400 MHz, DMSO-d6) δ 8.06 (d, J = 8.1 Hz, 1H), 7.98 (s, 3H), 7.89 (d, J = 7.7 Hz, 1H), 7.45 (s, 1H), 7.28 (d, J = 8.1 Hz, 1H), 7.04 (s, 1H), 6.94 (d, J = 1.2 Hz, 1H), 4.89-4.72 (m, 1H), 4.52-4.35 (m, 2H), 4.12 (s, 3H), 3.99 (s, 3H), 3.94-3.84 (m, 5H), 3.77-3.65 (m, 3H), 3.61 3.46 (m, 2H), 3.37 (s, 3H), 2.04-1.85 (m, 2H), 1.86-1.51 (m, 1H), 1.33 (dt, J = 35.8, 7.2 Hz, 5H), 1.22 (s, 3H), 1.19-0.99 (m, 1H), 0.96 (s, 3H), 0.63-0.46 (m, 3H), 0.42-0.29 (m, 1H). |
| 779 | 644.4 | 1H NMR (400 MHz, DMSO-d6) δ 8.04 (d, J = 8.1 Hz, 1H), 7.99 (s, 3H), 7.68 (d, J = 8.0 Hz, 1H), 7.19 (d, J = 8.1 Hz, 1H), 7.04 (s, 1H), 6.93 (s, 1H), 4.99-4.91 (m, 1H), 4.91-4.74 (m, 1H), 4.49-4.34 (m, 1H), 4.12 (s, 3H), 3.99 (s, 3H), 3.82-3.44 (m, 5H), 3.37 (s, 4H), 2.07-1.88 (m, |

TABLE 3-continued

| Example | ES/MS m/z [M + H]+ | ¹H NMR |
|---|---|---|
| | | 2H), 1.91-1.66 (m, 3H), 1.65-1.50 (m, 1H), 1.44-1.28 (m, 5H), 1.23 (s, 3H), 1.10-0.98 (m, 4H), 0.98-0.91 (m, 6H). |
| 780 | 685.3 | 1H NMR (400 MHz, DMSO-d6) δ 9.16 (d, J = 7.0 Hz, 1H), 8.08 (d, J = 8.1 Hz, 1H), 7.99 (s, 3H), 7.75 (d, J = 8.2 Hz, 1H), 7.49 (d, J = 8.1 Hz, 1H), 7.43 (s, 1H), 7.27 (d, J = 8.1 Hz, 1H), 7.08 (s, 1H), 6.94 (d, J = 1.2 Hz, 1H), 5.22 (p, J = 7.0 Hz, 1H), 4.96-4.75 (m, 1H), 4.65-4.51 (m, 1H), 4.12 (s, 3H), 4.00 (s, 3H), 3.84-3.59 (m, 3H), 3.58-3.45 (m, 1H), 3.37 (s, 3H), 2.46-2.20 (m, 3H), 2.04-1.89 (m, 1H), 1.76 (s, 1H), 1.51 (d, J = 7.0 Hz, 3H), 1.49-1.32 (m, 3H), 1.33-1.08 (m, 3H), 0.65-0.33 (m, 1H). |
| 781 | 685.3 | 1H NMR (400 MHz, DMSO-d6) δ 9.16 (d, J = 7.0 Hz, 1H), 8.08 (d, J = 8.1 Hz, 1H), 7.99 (s, 3H), 7.75 (d, J = 8.2 Hz, 1H), 7.49 (d, J = 8.1 Hz, 1H), 7.43 (s, 1H), 7.27 (d, J = 8.1 Hz, 1H), 7.08 (s, 1H), 6.94 (d, J = 1.2 Hz, 1H), 5.22 (p, J = 7.0 Hz, 1H), 4.96-4.75 (m, 1H), 4.65-4.51 (m, 1H), 4.12 (s, 3H), 4.00 (s, 3H), 3.84-3.59 (m, 3H), 3.58-3.45 (m, 1H), 3.37 (s, 3H), 2.46-2.20 (m, 3H), 2.04-1.89 (m, 1H), 1.76 (s, 1H), 1.51 (d, J = 7.0 Hz, 3H), 1.49-1.32 (m, 3H), 1.33-1.08 (m, 3H), 0.65-0.33 (m, 1H). |
| 782 | 628.3 | NA |
| 783 | 685.3 | 1H NMR (400 MHz, DMSO-d6) δ 9.06 (d, J = 6.7 Hz, 1H), 8.47 (d, J = 2.3 Hz, 1H), 8.08 (d, J = 8.0 Hz, 1H), 7.93 (s, 3H), 7.87 (d, J = 2.3 Hz, 1H), 7.43 (s, 1H), 7.26 (d, J = 8.1 Hz, 1H), 7.08 (s, 1H), 6.93 (s, 1H), 5.20 (p, J = 6.9 Hz, 1H), 4.93-4.76 (m, 1H), 4.68-4.49 (m, 1H), 4.12 (s, 3H), 4.00 (s, 3H), 3.96-3.77 (m, 1H), 3.75-3.68 (m, 1H), 3.67-3.46 (m, 3H), 3.20-3.02 (m, 1H), 2.48-2.38 (m, 1H), 2.39-2.24 (m, 2H), 2.04-1.86 (m, 1H), 1.82-1.70 (m, 1H), 1.50 (d, J = 7.0 Hz, 3H), 1.47-1.36 (m, 1H), 1.35-1.20 (m, 3H), 1.25 (d, 3H), 0.63-0.36 (m, 1H). |
| 784 | 721.3 | 1H NMR (400 MHz, DMSO-d6) δ 9.16 (d, J = 7.0 Hz, 1H), 8.19 (s, 3H), 8.09 (d, J = 8.0 Hz, 1H), 7.75 (d, J = 8.2 Hz, 1H), 7.49 (d, J = 8.1 Hz, 1H), 7.45 (s, 1H), 7.27 (d, J = 8.1 Hz, 1H), 7.09 (s, 1H), 6.95 (d, J = 1.2 Hz, 1H), 6.86 (t, J = 74.8 Hz, 1H), 5.22 (p, J = 7.1 Hz, 1H), 4.96-4.78 (m, 1H), 4.72-4.62 (m, 1H), 4.63-4.53 (m, 1H), 4.12 (s, 3H), 4.00 (s, 3H), 3.70-3.50 (m, 3H), 3.49-3.35 (m, 1H), 2.42-2.20 (m, 4H), 2.05-1.88 (m, 2H), 1.51 (d, J = 7.1 Hz, 3H), 1.47-1.33 (m, 1H), 1.32-1.08 (m, 3H), 0.53 (d, J = 12.0 Hz, 1H). |
| 785 | 684.3 | 1H NMR (400 MHz, DMSO-d6) δ 8.21 (d, J = 8.2 Hz, 1H), 8.16 (d, J = 9.0 Hz, 1H), 7.98 (s, 3H), 7.48 (d, J = 7.7 Hz, 2H), 7.14 (d, J = 0.9 Hz, 1H), 6.95 (d, J = 1.1 Hz, 1H), 6.26-5.96 (m, 1H), 4.96-4.76 (m, 1H), 4.59-4.34 (m, 1H), 4.13 (s, 3H), 4.00 (s, 3H), 3.97-3.78 (m, 4H), 3.75-3.66 (m, 1H), 3.63-3.46 (m, 2H), 3.37 (s, 3H), 2.24-2.06 (m, 1H), 2.01-1.88 (m, 1H), 1.83-1.70 (m, 2H), 1.69-1.53 (m, 1H), 1.52-1.33 (m, 5H), 1.25 (s, 3H), 1.21-1.06 (m, 1H), 1.04 (s, 3H). |
| 786 | 630.4 | 1H NMR (400 MHz, DMSO-d6) δ 8.05 (d, J = 8.1 Hz, 1H), 7.93 (s, 4H), 7.82 (d, J = 7.4 Hz, 1H), 7.36 (d, J = 1.1 Hz, 1H), 7.19 (d, J = 8.2 Hz, 1H), 7.03 (d, J = 1.8 Hz, 1H), 6.88 (d, J = 1.1 Hz, 1H), 5.13 (p, J = 7.1 Hz, 1H), 4.88-4.74 (m, 1H), 4.49-4.33 (m, 1H), 4.12 (d, J = 1.4 Hz, 3H), 4.00 (s, 3H), 3.97-3.81 (m, 3H), 3.79-3.71 (m, 1H), 3.38-3.11 (m, 1H), 2.04-1.85 (m, 2H), 1.74-1.55 (m, 1H), 1.45 (d, J = 7.1 Hz, 3H), 1.43-1.26 (m, 3H), 1.21 (s, 3H), 1.13 (d, J = 6.9 Hz, 3H), 1.10-1.00 (m, 3H), 0.95 (s, 3H). |
| 787 | 626.5 | 1H NMR (400 MHz, DMSO-d6) δ 8.88 (s, 1H), 8.02 (s, 3H), 7.96 (d, J = 8.3 Hz, 1H), 7.45 (s, 1H), 6.99 (s, 1H), 6.93 (d, J = 1.2 Hz, 1H), 6.84 (d, J = 8.4 Hz, 1H), 4.72-4.60 (m, 1H), 4.58-4.41 (m, 1H), 4.13 (s, 3H), 3.99 (s, 3H), 3.94-3.76 (m, 3H), 3.77-3.66 (m, 1H), 3.62-3.46 (m, 2H), 3.37 (s, 3H), 2.02-1.83 (m, 3H), 1.83-1.75 (m, 1H), 1.75-1.56 (m, 4H), 1.56-1.42 (m, 2H), 1.42-1.32 (m, 1H), 1.32-1.22 (m, 1H), 1.23-1.14 (m, 1H), 1.01-0.67 (m, 4H), 0.55-0.41 (m, 1H). |
| 788 | 707.3 | 1H NMR (400 MHz, DMSO-d6) δ 9.11 (d, J = 7.0 Hz, 1H), 8.48 (s, 1H), 8.19 (d, J = 5.4 Hz, 1H), 8.10 (d, J = 8.1 Hz, 1H), 7.98 (s, 3H), 7.51 (d, J = 5.5 Hz, 1H), 7.44 (s, 1H), 7.28 (d, J = 8.1 Hz, 1H), 7.10 (s, 1H), 6.94 (d, J = 1.2 Hz, 1H), 5.23 (p, J = 6.9 Hz, 1H), 4.97-4.76 (m, 1H), 4.13 (s, 3H), 4.00 (s, 3H), 3.73-3.68 (m, 4H), 3.63-3.48 (m, 5H), 3.37 (s, 3H), 2.83 (dd, J = 12.5, 7.9 Hz, 1H), 2.03-1.88 (m, 1H), 1.84-1.69 (m, 1H), 1.52 (d, J = 7.1 Hz, 3H), 1.50-1.33 (m, 1H), 1.29-1.12 (m, 2H), 0.74-0.46 (m, 1H). |
| 789 | 699.4 | 1H NMR (400 MHz, DMSO-d6) δ 9.13 (d, J = 7.1 Hz, 1H), 8.11 (d, J = 8.0 Hz, 1H), 7.98 (s, 3H), 7.83 (d, J = 8.0 Hz, 1H), 7.68 (s, 1H), 7.42 (d, J = 8.1 Hz, 1H), 7.32 (d, J = 6.5 Hz, 1H), 7.29 (s, 1H), 5.21 (p, J = 7.0 Hz, 1H), 4.99-4.87 (m, 1H), 4.86-4.76 (m, 1H), 4.07-3.97 (m, 1H), 3.74-3.68 (m, 1H), 3.65-3.40 (m, 7H), 3.37 (s, 3H), 2.71-2.55 (m, 1H), 2.46-2.25 (m, 2H), 2.04-1.87 (m, 1H), 1.83-1.69 (m, 1H), 1.50 (d, J = 7.0 Hz, 3H), 1.48-1.34 (m, 2H), 1.27-1.16 (m, 2H), 1.14-0.96 (m, 2H), 0.66-0.53 (m, 1H), 0.53-0.38 (m, 1H). |
| 790 | 683.4 | 1H NMR (400 MHz, DMSO-d6) δ 9.13 (d, J = 7.1 Hz, 1H), 8.11 (d, J = 8.0 Hz, 1H), 7.92 (s, 3H), 7.83 (d, J = 8.1 Hz, 1H), 7.60 (d, J = 1.1 Hz, 1H), 7.42 (d, J = 8.0 Hz, 1H), 7.32 (s, 1H), 7.27 (d, J = 8.2 Hz, 1H), 5.32- |

TABLE 3-continued

| Example | ES/MS m/z [M + H]+ | ¹H NMR |
|---|---|---|
| | | 5.10 (m, 1H), 5.00-4.77 (m, 2H), 4.10-3.93 (m, 1H), 3.65-3.24 (m, 6H), 2.67-2.56 (m, 2H), 2.43-2.34 (m, 2H), 1.87-1.62 (m, 2H), 1.50 (d, J = 7.0 Hz, 3H), 1.68-1.31 (m, 2H), 1.32-1.13 (m, 1H), 1.20 (d, J = 6.9 Hz, 4H), 1.08 (d, J = 43.1 Hz, 3H), 0.70-0.32 (m, 2H). |
| 791 | 687.3 | 1H NMR (400 MHz, DMSO-d6) δ 9.13 (d, J = 7.1 Hz, 1H), 8.11 (d, J = 8.0 Hz, 1H), 8.06 (s, 3H), 7.82 (d, J = 8.0 Hz, 1H), 7.61 (d, J = 1.2 Hz, 1H), 7.42 (d, J = 8.0 Hz, 1H), 7.33 (s, 1H), 7.27 (d, J = 8.1 Hz, 1H), 7.23 (d, J = 11.5 Hz, 1H), 5.21 (p, J = 7.0 Hz, 1H), 5.13-4.99 (m, 1H), 5.00-4.87 (m, 1H), 4.87-4.77 (m, 1H), 4.08-3.97 (m, 1H), 3.68-3.48 (m, 1H), 3.45-3.27 (m, 1H), 3.07-2.81 (m, 1H), 2.70-2.58 (m, 1H), 2.45-2.25 (m, 4H), 1.96-1.72 (m, 1H), 1.50 (d, J = 7.0 Hz, 3H), 1.66-1.32 (m, 2H), 1.30-1.14 (m, 3H), 1.15-0.97 (m, 3H), 0.64-0.53 (m, 1H), 0.53-0.38 (m, 1H). |
| 792 | 652.2 | 1H NMR (400 MHz, DMSO-d6) δ 8.56 (d, J = 8.8 Hz, 1H), 8.07 (d, 1H), 8.03 (s, 3H), 7.42 (dd, J = 2.7, 1.1 Hz, 1H), 7.24 (d, J = 8.0 Hz, 1H), 7.14 (d, J = 1.4 Hz, 1H), 6.92 (d, J = 1.1 Hz, 1H), 5.58-5.44 (m, 1H), 5.22-5.02 (m, 2H), 5.01-4.82 (m, 1H), 4.10 (s, 3H), 4.08-4.01 (m, 3H), 4.01 (s, 3H), 3.51-3.21 (m, 1H), 3.11-2.90 (m, 1H), 2.37-2.24 (m, 1H), 2.18-1.87 (m, 3H), 1.68-1.56 (m, 1H), 1.54 (q, J = 5.3 Hz, 1H), 1.44 (d, J = 7.1 Hz, 3H), 1.40-1.28 (m, 1H), 1.22 (dt, J = 6.9, 2.0 Hz, 3H), 0.92-0.76 (m, 1H), 0.73-0.56 (m, 1H), 0.54-0.41 (m, 2H). |
| 793 | 691.5 | 1H NMR (400 MHz, DMSO-d6) δ 9.12 (d, J = 7.0 Hz, 1H), 8.49 (s, 1H), 8.20 (d, J = 5.5 Hz, 1H), 8.10 (d, J = 8.0 Hz, 1H), 7.93 (s, 3H), 7.51 (d, J = 5.5 Hz, 1H), 7.35 (d, J = 1.1 Hz, 1H), 7.28 (d, J = 8.1 Hz, 1H), 7.10 (s, 1H), 6.89 (s, 1H), 5.31-5.16 (m, 1H), 4.96-4.77 (m, 1H), 4.66-4.54 (m, 1H), 4.13 (s, 3H), 4.00 (s, 3H), 3.93-3.44 (m, 7H), 3.44-3.25 (m, 2H), 2.89-2.76 (m, 1H), 1.87-1.63 (m, 2H), 1.52 (d, J = 7.0 Hz, 3H), 1.33 (d, J = 5.6 Hz, 2H), 1.21 (d, J = 6.9 Hz, 3H), 1.34-1.05 (m, 1H), 0.77-0.43 (m, 1H). |
| 794 | 695.4 | 1H NMR (400 MHz, DMSO-d6) δ 9.12 (d, J = 7.0 Hz, 1H), 8.48 (s, 1H), 8.19 (d, J = 5.5 Hz, 1H), 8.10 (d, J = 8.0 Hz, 1H), 8.02 (s, 3H), 7.51 (d, J = 5.5 Hz, 1H), 7.38 (s, 1H), 7.28 (d, J = 8.1 Hz, 1H), 7.10 (s, 1H), 6.89 (s, 1H), 5.23 (p, J = 7.0 Hz, 1H), 5.11-4.91 (m, 1H), 4.92-4.78 (m, 1H), 4.66-4.51 (m, 1H), 4.13 (s, 3H), 3.99 (s, 3H), 3.48-3.29 (m, 2H), 3.01-2.87 (m, 1H), 2.89-2.76 (m, 1H), 2.43-2.20 (m, 2H), 2.08-1.71 (m, 3H), 1.52 (d, J = 7.0 Hz, 3H), 1.50-1.32 (m, 2H), 1.30-1.13 (m, 2H), 0.71-0.45 (m, 1H). |
| 795 | 632.4 | 1H NMR (400 MHz, DMSO-d6) δ 8.13 (s, 3H), 8.05 (d, J = 8.1 Hz, 1H), 7.83 (d, J = 7.4 Hz, 1H), 7.41 (d, J = 1.1 Hz, 1H), 7.19 (d, J = 8.1 Hz, 1H), 7.04 (d, J = 2.3 Hz, 1H), 6.92 (d, J = 1.1 Hz, 1H), 5.73-5.18 (m, 2H), 5.20-5.07 (m, 1H), 4.97 (dt, J = 10.9, 5.2 Hz, 1H), 4.82 (ddq, J = 13.6, 8.8, 4.9, 4.3 Hz, 1H), 4.52-4.33 (m, 1H), 4.12 (d, J = 1.3 Hz, 3H), 4.00 (s, 3H), 3.48-3.27 (m, 1H), 3.11-2.93 (m, 1H), 2.31 (dt, J = 11.6, 5.8 Hz, 1H), 2.06-1.84 (m, 2H), 1.74-1.54 (m, 2H), 1.45 (d, J = 7.1 Hz, 3H), 1.36 (td, J = 12.8, 5.1 Hz, 3H), 1.25-1.19 (m, 6H), 1.16-1.01 (m, 4H), 0.95 (d, J = 1.9 Hz, 3H). |
| 796 | 705.4 | 1H NMR (400 MHz, DMSO-d6) δ 9.15 (d, J = 6.8 Hz, 1H), 8.50 (s, 1H), 8.20 (d, J = 5.5 Hz, 1H), 8.11 (d, J = 8.0 Hz, 1H), 7.93 (s, 3H), 7.59 (d, J = 1.2 Hz, 1H), 7.51 (d, J = 5.5 Hz, 1H), 7.33 (s, 1H), 7.29 (d, J = 8.1 Hz, 1H), 7.25 (d, J = 11.4 Hz, 1H), 5.21 (p, J = 7.0 Hz, 1H), 5.02-4.88 (m, 1H), 4.88-4.75 (m, 1H), 4.79-4.13 (m, 3H), 4.10-3.91 (m, 1H), 3.44-3.29 (m, 1H), 3.19-2.91 (m, 1H), 2.90-2.77 (m, 1H), 1.85-1.63 (m, 3H), 1.64-1.54 (m, 1H), 1.53 (d, J = 7.0 Hz, 3H), 1.51-1.28 (m, 3H), 1.34-1.23 (m, 2H), 1.20 (d, J = 6.9 Hz, 3H), 1.16-0.95 (m, 2H), 0.64-0.38 (m, 2H). |
| 797 | 721.3 | 1H NMR (400 MHz, DMSO-d6) δ 9.15 (d, J = 6.8 Hz, 1H), 8.51 (s, 1H), 8.21 (d, J = 5.5 Hz, 1H), 8.11 (d, J = 8.0 Hz, 1H), 7.99 (s, 3H), 7.68 (s, 1H), 7.52 (d, J = 5.5 Hz, 1H), 7.33 (s, 1H), 7.29 (dd, J = 9.7, 3.6 Hz, 2H), 5.21 (p, J = 6.9 Hz, 1H), 5.00-4.88 (m, 1H), 4.88-4.76 (m, 1H), 4.09-3.97 (m, 1H), 3.95-3.75 (m, 1H), 3.75-3.64 (m, 1H), 3.66-3.47 (m, 4H), 3.46-3.39 (m, 2H), 3.37 (s, 3H), 2.83 (dd, J = 12.6, 7.9 Hz, 1H), 2.02-1.87 (m, 1H), 1.82-1.66 (m, 1H), 1.53 (d, J = 7.1 Hz, 3H), 1.51-1.32 (m, 4H), 1.28-1.16 (m, 2H), 1.16-0.94 (m, 2H), 0.52 (d, J = 32.5 Hz, 2H). |
| 798 | 681.4 | 1H NMR (400 MHz, DMSO-d6) δ 9.12 (d, J = 6.9 Hz, 1H), 8.11 (d, J = 8.0 Hz, 1H), 7.99 (s, 3H), 7.64 (s, 1H), 7.42 (d, J = 8.0 Hz, 1H), 7.33 (s, 1H), 7.31-7.23 (m, 2H), 5.21 (p, J = 7.1 Hz, 1H), 5.02-4.76 (m, 2H), 4.02 (s, 1H), 3.81-3.71 (m, 1H), 3.68-3.31 (m, 2H), 3.26-3.14 (m, 1H), 2.73-2.56 (m, 2H), 2.44-2.28 (m, 2H), 2.03-1.80 (m, 4H), 1.57-1.36 (m, 3H), 1.50 (d, J = 7.0 Hz, 3H), 1.28-1.14 (m, 2H), 1.14-0.96 (m, 2H), 0.86-0.73 (m, 1H), 0.66-0.35 (m, 2H). |
| 799 | 628.6 | 1H NMR (400 MHz, DMSO-d6) δ 8.17 (d, J = 7.1 Hz, 1H), 8.06 (d, J = 8.1 Hz, 1H), 7.89 (s, 3H), 7.36 (d, J = 1.2 Hz, 1H), 7.22 (d, J = 8.2 Hz, 1H), 7.02 (s, 1H), 6.88 (s, 1H), 5.17 (p, J = 6.8 Hz, 1H), 4.81 (d, J = 5.6 Hz, 1H), 4.74 (d, J = 6.3 Hz, 1H), 4.73-4.61 (m, 1H), 4.50-4.31 (m, 1H), 4.19 (d, J = 5.6 Hz, 1H), 4.11 (d, J = 2.5 Hz, 3H), 3.99 (s, 3H), 3.89- |

TABLE 3-continued

| Example | ES/MS m/z [M + H]+ | 1H NMR |
|---|---|---|
| | | 3.73 (m, 2H), 3.44-3.23 (m, 2H), 2.27-2.12 (m, 1H), 2.06-1.93 (m, 1H), 1.88-1.66 (m, 3H), 1.66-1.52 (m, 3H), 1.49 (d, J = 7.1 Hz, 3H), 1.41-1.26 (m, 4H), 1.20 (d, J = 6.9 Hz, 3H), 1.17-0.91 (m, 3H). |
| 800 | 630.6 | 1H NMR (400 MHz, DMSO-d6) δ 8.05 (d, J = 8.1 Hz, 1H), 7.82 (d, J = 7.4 Hz, 1H), 7.37 (d, J = 1.2 Hz, 1H), 7.19 (d, J = 8.2 Hz, 1H), 7.03 (d, J = 2.1 Hz, 1H), 6.89 (s, 1H), 5.13 (p, J = 7.2 Hz, 1H), 5.07-4.90 (m, 2H), 4.92-4.75 (m, 1H), 4.53-4.31 (m, 2H), 4.12 (d, J = 1.9 Hz, 3H), 4.00 (s, 3H), 3.90-3.54 (m, 5H), 3.49-3.28 (m, 4H), 2.09-1.97 (m, 1H), 1.98-1.86 (m, 2H), 1.75-1.53 (m, 2H), 1.45 (d, J = 7.1 Hz, 3H), 1.44-1.26 (m, 3H), 1.21 (s, 3H), 1.27-1.15 (m, 2H), 1.15-0.99 (m, 2H), 0.95 (s, 3H). |
| 801 | 676.7 | 1H NMR (400 MHz, DMSO-d6) δ 9.29 (s, 1H), 8.97 (s, 1H), 8.56 (d, J = 8.8 Hz, 1H), 8.06 (d, J = 8.1 Hz, 1H), 7.39 (d, J = 1.1 Hz, 1H), 7.24 (d, J = 8.1 Hz, 1H), 7.14 (d, J = 2.0 Hz, 1H), 6.92-6.87 (m, 1H), 5.64-5.41 (m, 1H), 5.22-4.99 (m, 2H), 4.10 (d, J = 1.4 Hz, 3H), 4.09-3.92 (m, 1H), 4.00 (s, 3H), 3.65 (d, J = 12.4 Hz, 3H), 3.56-3.48 (m, 4H), 3.45-3.17 (m, 3H), 3.12-2.95 (m, 1H), 2.28-1.91 (m, 2H), 1.83-1.68 (m, 1H), 1.67-1.57 (m, 0H), 1.54 (q, J = 5.2 Hz, 1H), 1.44 (d, J = 7.1 Hz, 3H), 1.33 (d, J = 7.0 Hz, 3H), 1.31-1.18 (m, 1H), 0.90-0.81 (m, 1H), 0.73-0.58 (m, 1H), 0.55-0.43 (m, 2H). |
| 802 | 678.5 | 1H NMR (400 MHz, DMSO-d6) δ 8.59 (d, J = 8.8 Hz, 1H), 8.08 (d, J = 8.0 Hz, 1H), 7.94 (s, 3H), 7.63 (d, J = 1.2 Hz, 1H), 7.42 (s, 1H), 7.28 (d, J = 11.3 Hz, 1H), 7.25 (d, J = 8.1 Hz, 1H), 5.79 (t, J = 13.8 Hz, 1H), 5.19 (dd, J = 28.0, 14.6 Hz, 1H), 5.07 (p, J = 8.6, 6.8 Hz, 1H), 4.72-4.25 (m, 4H), 4.23-4.16 (m, 1H), 4.14-3.82 (m, 4H), 3.83-3.74 (m, 1H), 3.44-3.33 (m, 1H), 3.31 (d, J = 1.5 Hz, 3H), 2.28-2.02 (m, 1H), 2.03-1.90 (m, 1H), 1.83-1.59 (m, 3H), 1.55 (q, J = 5.1 Hz, 1H), 1.44 (d, J = 7.1 Hz, 3H), 1.40-1.26 (m, 1H), 1.21 (d, J = 6.9 Hz, 3H), 0.92-0.78 (m, 1H), 0.75-0.55 (m, 1H), 0.55-0.45 (m, 2H). |
| 803 | 662.3 | 1H NMR (400 MHz, DMSO-d6) δ 9.34 (s, 1H), 8.87 (s, 1H), 8.56 (d, J = 8.8 Hz, 1H), 8.06 (d, J = 8.1 Hz, 1H), 7.44 (d, J = 1.1 Hz, 1H), 7.24 (d, J = 8.1 Hz, 1H), 7.14 (s, 1H), 7.01-6.92 (m, 1H), 5.51 (t, J = 13.6 Hz, 1H), 5.25-5.10 (m, 1H), 5.05 (dq, J = 9.3, 7.1, 6.2 Hz, 1H), 4.10 (s, 3H), 4.01 (s, 5H), 3.82 (s, 3H), 3.75 (d, J = 11.3 Hz, 3H), 3.63 (s, 2H), 3.38-3.15 (m, 1H), 3.07 (s, 1H), 2.22-2.01 (m, 1H), 1.99-1.77 (m, 2H), 1.67-1.57 (m, 1H), 1.44 (d, J = 7.1 Hz, 3H), 1.38-1.17 (m, 1H), 0.91-0.77 (m, 1H), 0.72-0.55 (m, 1H), 0.53-0.44 (m, 2H). |
| 804 | 676.3 | 1H NMR (400 MHz, DMSO-d6) δ 8.58 (d, J = 8.7 Hz, 1H), 8.08 (d, J = 8.1 Hz, 1H), 7.91 (s, 2H), 7.80 (s, 0H), 7.66 (s, 1H), 7.42 (s, 1H), 7.41-7.20 (m, 2H), 5.79 (t, J = 13.8 Hz, 1H), 5.19 (dd, J = 28.0, 14.6 Hz, 1H), 5.12-4.94 (m, 1H), 4.31-4.09 (m, 1H), 3.84-3.73 (m, 1H), 3.65-3.51 (m, 2H), 3.47-3.34 (m, 3H), 3.31 (s, 3H), 3.20 (t, J = 8.8 Hz, 3H), 2.71-2.62 (m, 1H), 2.62-2.54 (m, 1H), 2.28-2.05 (m, 1H), 2.07-1.79 (m, 3H), 1.74-1.59 (m, 2H), 1.59-1.49 (m, 1H), 1.44 (d, J = 7.0 Hz, 3H), 1.40-1.26 (m, 2H), 0.86 (t, J = 5.3 Hz, 1H), 0.74-0.42 (m, 4H). |
| 805 | 664.5 | 1H NMR (400 MHz, DMSO-d6) δ 8.60 (d, J = 8.8 Hz, 1H), 8.07 (d, J = 8.0 Hz, 1H), 8.01 (s, 3H), 7.75 (d, J = 1.4 Hz, 1H), 7.43 (d, J = 1.3 Hz, 1H), 7.36 (s, 1H), 7.24 (d, J = 8.1 Hz, 1H), 5.95-5.72 (m, 1H), 5.20 (dd, J = 28.0, 14.6 Hz, 1H), 5.06 (p, 1H), 4.76-4.15 (m, 2H), 4.10-3.98 (m, 1H), 3.45-3.27 (m, 1H), 3.26-2.77 (m, 2H), 2.31-2.04 (m, 2H), 2.05-1.87 (m, 1H), 1.88-1.51 (m, 4H), 1.44 (d, J = 7.0 Hz, 3H), 1.43-1.24 (m, 2H), 1.22 (d, J = 6.9 Hz, 3H), 1.12-1.02 (m, 1H), 1.02-0.92 (m, 2H), 0.92-0.80 (m, 1H), 0.77-0.59 (m, 1H), 0.59-0.41 (m, 3H). |
| 806 | 680.3 | 1H NMR (400 MHz, DMSO-d6) δ 8.60 (d, J = 8.8 Hz, 1H), 8.07 (d, J = 8.0 Hz, 1H), 8.02 (s, 3H), 7.81 (s, 1H), 7.50 (d, J = 1.4 Hz, 1H), 7.36 (s, 1H), 7.24 (d, J = 8.1 Hz, 1H), 5.94-5.78 (m, 1H), 5.21 (dd, J = 28.0, 14.6 Hz, 1H), 5.06 (p, 1H), 4.08-4.00 (m, 1H), 3.97-3.75 (m, 3H), 3.71 (dt, J = 6.5, 3.1 Hz, 1H), 3.66-3.49 (m, 1H), 3.48-3.38 (m, 2H), 3.37 (s, 3H), 2.33-2.04 (m, 1H), 2.03-1.85 (m, 1H), 1.85-1.70 (m, 1H), 1.70-1.60 (m, 1H), 1.59-1.51 (m, 1H), 1.44 (d, J = 7.1 Hz, 3H), 1.40-1.18 (m, 2H), 1.12-0.92 (m, 2H), 0.91-0.79 (m, 1H), 0.75-0.59 (m, 1H), 0.58-0.43 (m, 3H). |
| 807 | 683.4 | 1H NMR (400 MHz, DMSO-d6) δ 9.13 (d, J = 7.1 Hz, 1H), 8.11 (d, J = 8.1 Hz, 1H), 7.90 (s, 3H), 7.83 (d, J = 8.0 Hz, 1H), 7.59 (d, J = 1.2 Hz, 1H), 7.42 (d, J = 8.0 Hz, 1H), 7.32 (s, 1H), 7.27 (d, J = 8.3 Hz, 1H), 7.26 (d, 1H), 5.21 (p, J = 7.0 Hz, 1H), 4.98-4.85 (m, 1H), 4.86-4.74 (m, 1H), 4.08-3.98 (m, 1H), 3.95-3.44 (m, 4H), 3.25-3.09 (m, 1H), 3.10-2.83 (m, 1H), 2.72-2.57 (m, 1H), 2.47-2.23 (m, 2H), 1.94-1.71 (m, 3H), 1.66-1.53 (m, 1H), 1.50 (d, J = 7.0 Hz, 3H), 1.50-1.34 (m, 2H), 1.30-1.14 (m, 1H), 1.20 (d, J = 6.9 Hz, 3H), 1.17-0.94 (m, 2H), 0.69-0.34 (m, 2H). |
| 808 | 681.6 | 1H NMR (400 MHz, DMSO-d6) δ 9.12 (d, J = 7.1 Hz, 1H), 8.11 (d, J = 8.1 Hz, 3H), 8.08 (s, 3H), 7.83 (d, J = 8.1 Hz, 1H), 7.81 (s, 1H), 7.42 (d, J = 8.0 Hz, 2H), 7.38 (d, 1H), 7.33 (s, 1H), 7.27 (d, J = 8.1 Hz, 1H), 5.21 (p, J = 7.1 Hz, 1H), 5.01-4.74 (m, 2H), 4.71-4.24 (m, 2H), 4.08-3.97 (m, 1H), 3.89-3.09 (m, 1H), 2.70-2.57 (m, 1H), 2.45-2.23 (m, 2H), 1.92- |

TABLE 3-continued

| Example | ES/MS m/z [M + H]+ | ¹H NMR |
|---|---|---|
| | | 1.72 (m, 3H), 1.68-1.56 (m, 1H), 1.51 (d, J = 7.1 Hz, 3H), 1.48-1.45 (m, 2H), 1.28-1.14 (m, 2H), 1.14-0.95 (m, 2H), 0.65-0.38 (m, 2H). |
| 809 | 707.3 | 1H NMR (400 MHz, DMSO-d6) δ 9.12 (d, J = 7.1 Hz, 1H), 8.08 (d, J = 8.0 Hz, 1H), 7.99 (s, 2H), 7.82 (d, J = 8.0 Hz, 1H), 7.76 (s, 1H), 7.41 (d, J = 8.1 Hz, 1H), 7.33 (s, 1H), 7.25 (d, J = 8.1 Hz, 1H), 7.22 (s, 1H), 6.91 (s, 1H), 5.20 (p, J = 7.0 Hz, 1H), 5.05-4.70 (m, 2H), 4.61-4.44 (m, 0.5H), 4.35-4.20 (m, 0.5H), 4.00 (s, 3H), 3.96-3.88 (m, 1H), 3.87-3.63 (m, 2H), 3.43-3.34 (m, 0.5H), 3.18-3.13 (m, 0.3H), 2.83-2.70 (m, 0.4H), 2.71-2.56 (m, 1H), 2.44-2.25 (m, 2H), 2.06-1.89 (m, 1H), 1.90-1.73 (m, 1H), 1.73-1.56 (m, 5H), 1.50 (d, J = 7.1 Hz, 3H), 1.46-1.31 (m, 3H), 1.28-1.09 (m, 1H), 1.07-0.96 (m, 1H), 0.95-0.76 (m, 1H), 0.63-0.47 (m, 1H), 0.46-0.20 (m, 1H). |
| 810 | 695.5 | 1H NMR (400 MHz, DMSO-d6) δ 9.22 (d, J = 6.6 Hz, 1H), 8.37 (s, 1H), 8.10 (d, J = 8.0 Hz, 1H), 7.99 (s, 2H), 7.76 (s, 1H), 7.58 (s, 0.5H), 7.45 (s, 1H), 7.32 (s, 1H), 7.30 (s, 0.5H), 7.26 (d, J = 8.1 Hz, 1H), 5.16 (p, J = 6.9 Hz, 1H), 5.05-4.94 (m, 0.4H), 4.95-4.79 (m, 2H), 4.61-4.44 (m, 0.6H), 4.25-4.13 (m, 1H), 4.07-3.98 (m, 1H), 3.98-3.85 (m, 3H), 3.82-3.66 (m, 1H), 3.43-3.21 (m, 1H), 3.21-2.96 (m, 0.5H), 2.85-2.71 (m, 0.5H), 2.40-2.23 (m, 2H), 2.06-1.89 (m, 1H), 1.89-1.71 (m, 1H), 1.73-1.56 (m, 3H), 1.51 (d, J = 7.0 Hz, 3H), 1.48-1.35 (m, 3H), 1.39-0.90 (m, 4H), 0.63-0.36 (m, 2H). |
| 811 | 681.3 | 1H NMR (400 MHz, DMSO-d6) δ 9.04 (d, J = 7.3 Hz, 1H), 7.98 (d, J = 8.0 Hz, 1H), 7.81 (d, J = 8.1 Hz, 1H), 7.76 (s, 2H), 7.40 (d, J = 8.0 Hz, 1H), 7.35-7.20 (m, 1H), 7.18 (d, J = 8.0 Hz, 1H), 6.65 (s, 1H), 6.35 (s, 1H), 5.21 (p, J = 7.0 Hz, 1H), 5.07-4.89 (m, 0.6H), 4.85-4.71 (m, 1H), 4.65-4.43 (m, 1H), 4.30-4.17 (m, 0.7H), 4.09 (s, 3H), 3.68-3.44 (m, 2H), 2.81 (s, 3H), 2.66-2.55 (m, 0.6H), 2.45-2.30 (m, 3H), 2.03-1.91 (m, 2H), 1.81-1.73 (m, 4H), 1.55 (s, 3H), 1.48 (d, J = 7.0 Hz, 3H), 1.46-1.32 (m, 1H), 1.23-1.07 (m, 1H), 0.70-0.45 (m, 1H). |
| 812 | 711.3 | 1H NMR (400 MHz, DMSO-d6) δ 9.13 (d, J = 7.1 Hz, 1H), 8.10 (d, J = 8.1 Hz, 1H), 7.97 (s, 2H), 7.83 (d, J = 8.1 Hz, 1H), 7.75 (s, 1H), 7.48 (s, 1H), 7.42 (d, J = 8.0 Hz, 1H), 7.30 (s, 1H), 7.27 (d, J = 8.1 Hz, 1H), 5.21 (p, J = 7.0 Hz, 1H), 5.04-4.75 (m, 2H), 4.64-4.43 (m, 0.57H, rotamer), 4.27-4.11 (m, 0.53H, rotamer), 4.10-3.98 (m, 1H), 3.83-3.63 (m, 0.56H, rotamer), 3.59-3.14 (m, 4H), 2.82-2.72 (m, 0.56H, rotamer), 2.70-2.58 (m, 1H), 2.44-2.27 (m, 2H), 2.06-1.89 (m, 1H), 1.91-1.73 (m, 1H), 1.72-1.56 (m, 1H), 1.50 (d, J = 7.1 Hz, 3H), 1.48-1.38 (m, 1H), 1.30-1.06 (m, 3H), 1.05-0.87 (m, 1H), 0.66-0.51 (m, 1H), 0.52-0.35 (m, 1H). |
| 813 | 701.3 | 1H NMR (400 MHz, DMSO-d6) δ 8.92 (s, 1H), 8.10 (d, J = 8.1 Hz, 1H), 7.96 (s, 1H), 7.73 (s, 1H), 7.62 (s, 2H), 7.31 (s, 1H), 7.25 (d, J = 8.1 Hz, 1H), 7.16 (d, J = 7.9 Hz, 1H), 5.18 (p, J = 6.9 Hz, 1H), 5.03-4.86 (m, 1H), 4.86-4.71 (m, 1H), 4.62-4.38 (m, 0.48H, rotamer), 4.28-4.11 (m, 1H), 4.09-3.97 (m, 1H), 3.90-3.32 (m, 3H), 3.21-2.97 (m, 0.34H, rotamer), 2.72-2.60 (m, 2H), 2.39-2.26 (m, 2H), 2.17-2.06 (m, 1H), 2.04-1.91 (m, 1H), 1.90-1.72 (m, 1H), 1.60 (d, J = 39.2 Hz, 1H), 1.49 (d, J = 7.1 Hz, 3H), 1.59-1.41 (m, 3H), 1.41-1.31 (m, 1H), 1.29-1.13 (m, 3H), 1.13-1.01 (m, 1H), 1.01-0.83 (m, 5H), 0.63-0.52 (m, 1H), 0.51-0.40 (m, 1H). |
| 814 | 731.3 | 1H NMR (400 MHz, DMSO-d6) δ 9.19 (d, J = 7.4 Hz, 1H), 8.19 (d, J = 8.1 Hz, 1H), 7.98 (s, 2H), 7.87 (d, J = 8.0 Hz, 1H), 7.75 (s, 1H), 7.61 (s, 1H), 7.46 (d, J = 8.0 Hz, 1H), 7.39 (s, 1H), 7.38 (d, J = 8.2 Hz, 1H), 7.25 (s, 1H), 5.63-5.44 (m, 0.62H, rotamer), 5.31 (p, J = 7.0 Hz, 1H), 5.25-5.14 (m, 0.42H, rotamer), 4.99 (m, 0.53H, rotamer), 4.60-4.42 (m, 0.47H, rotamer), 4.29-4.12 (m, 0.59H, rotamer), 4.09-3.97 (m, 1H), 3.85-3.65 (m, 0H), 3.45-3.03 (m, 1H), 2.86-2.71 (m, 1H), 2.69-2.58 (m, 1H), 2.55-2.41 (m, 1H), 2.05-1.91 (m, 1H), 1.89-1.72 (m, 2H), 1.70-1.53 (m, 5H), 1.48 (d, J = 7.1 Hz, 3H), 1.35-1.13 (m, 2H), 1.11-0.89 (m, 2H), 0.65-0.33 (m, 1H). |
| 815 | 628.3 | 1H NMR (400 MHz, DMSO-d6) δ 8.35 (d, J = 9.5 Hz, 1H), 7.96 (s, 2H), 7.90 (d, J = 8.0 Hz, 1H), 7.75 (s, 1H), 7.30 (s, 0H), 7.23 (s, 1H), 7.08 (d, J = 8.0 Hz, 1H), 6.60 (s, 1H), 6.35 (s, 1H), 5.16 (p, J = 9.4, 6.8 Hz, 1H), 5.08-4.88 (m, 0.42H, rotamer), 4.74-4.62 (m, 0.62H, rotamer), 4.61-4.44 (m, 2H), 4.29-4.18 (m, 1H), 4.09 (s, 3H), 3.91-3.41 (m, 2H), 3.42-3.23 (m, 3H), 3.21-3.00 (m, 1H), 2.80 (s, 3H), 2.31-2.20 (m, 1H), 2.08-1.91 (m, 2H), 1.90-1.78 (m, 1H), 1.74-1.64 (m, 2H), 1.62-1.52 (m, 3H), 1.44 (d, J = 7.1 Hz, 3H), 1.38-1.29 (m, 3H), 1.29-1.20 (m, 1H), 1.19-1.07 (m, 1H), 0.99-0.86 (m, 1H). |
| 816 | 654.6 | 1H NMR (400 MHz, DMSO-d6) δ 8.95 (s, 1H), 8.10 (d, J = 8.0 Hz, 1H), 7.97 (s, 2H), 7.74 (s, 1H), 7.66 (s, 1H), 7.59 (s, 1H), 7.32 (s, 1H), 7.26 (d, J = 8.1 Hz, 2H), 7.18 (d, J = 8.0 Hz, 1H), 5.18 (p, J = 6.9 Hz, 1H), 5.07-4.76 (m, 2H), 4.60-4.46 (m, 0.78H, rotamer), 4.25-4.15 (m, 0.78H, rotamer), 4.08-3.98 (m, 1H), 3.80-3.54 (m, 2H), 3.38 (m, 0.23H, rotamer), 3.15 (m, 0.25H, rotamer), 2.86-2.72 (m, 0.40H, rotamer), 2.68-2.59 (m, 1H), 2.40-2.24 (m, 3H), 2.17-2.06 (m, 1H), 2.03-1.90 (m, 1H), 1.88-1.72 (m, 1H), 1.65 (s, 1H), 1.49 (d, J = 7.1 Hz, 3H), 1.47- |

TABLE 3-continued

| Example | ES/MS m/z [M + H]+ | 1H NMR |
|---|---|---|
| | | 1.41 (m, 2H), 1.41 (s, 1H), 1.32-1.14 (m, 3H), 1.13-1.03 (m, 1H), 1.02-0.85 (m, 5H), 0.63-0.52 (m, 1H), 0.49-0.39 (m, 1H). |
| 817 | 654.6 | 1H NMR (400 MHz, DMSO-d6) δ 8.43 (d, J = 8.6 Hz, 1H), 8.02 (s, 1H), 7.98 (d, J = 8.1 Hz, 1H), 7.82 (d, J = 45.0 Hz, 1H), 7.39 (s, 1H), 7.13 (d, J = 8.1 Hz, 1H), 7.02 (s, 1H), 6.93 (s, 1H), 5.09-4.94 (m, 1H), 4.84-4.64 (m, 2H), 4.64-4.47 (m, 2H), 4.35-4.21 (m, 4H), 4.20-4.02 (m, 3H), 4.00 (s, 3H), 3.92-3.73 (m, 2H), 3.70-3.50 (m, 2H), 3.48-3.21 (m, 1H), 3.22-3.07 (m, 0.56H, rotamer), 3.03 (s, 3H), 2.85-2.71 (m, 0.44H, rotamer), 2.06-1.92 (m, 1H), 1.91-1.78 (m, 1H), 1.73-1.59 (m, 4H), 1.58-1.47 (m, 1H), 1.43 (d, J = 7.1 Hz, 3H), 1.39-1.31 (m, 1H), 1.30-1.13 (m, 1H), 0.92-0.81 (m, 1H), 0.78-0.57 (m, 2H), 0.52-0.39 (m, 1H). |
| 818 | 707.4 | 1H NMR (400 MHz, DMSO-d6) δ 9.21 (d, J = 6.6 Hz, 1H), 8.37 (s, 1H), 8.07 (d, J = 8.0 Hz, 1H), 7.98 (s, 2H), 7.75 (s, 1H), 7.45 (s, 1H), 7.32 (s, 1H), 7.24 (d, J = 8.1 Hz, 1H), 7.22 (s, 1H), 6.91 (s, 1H), 5.16 (p, J = 6.9 Hz, 1H), 5.08-4.92 (m, 0.58H, rotamer), 4.94-4.78 (m, 2H), 4.61-4.45 (m, 0.47H, rotamer), 4.38-4.14 (m, 0.61H, rotamer), 4.00 (s, 3H), 3.96-3.87 (m, 1H), 3.82-3.38 (m, 4H), 2.87-2.70 (m, 0.60H, rotamer), 2.42-2.22 (m, 2H), 2.06-1.92 (m, 1H), 1.89-1.75 (m, 1H), 1.72-1.55 (m, 1H), 1.51 (d, J = 7.0 Hz, 3H), 1.46-1.36 (m, 2H), 1.33-1.22 (m, 1H), 1.21-1.09 (m, 2H), 1.08-0.96 (m, 1H), 0.95-0.82 (m, 1H), 0.63-0.45 (m, 1H), 0.41-0.27 (m, 1H). |
| 819 | 723.3 | 1H NMR (400 MHz, DMSO-d6) δ 9.19 (d, J = 7.0 Hz, 1H), 8.08 (d, J = 8.0 Hz, 1H), 7.96 (s, 2H), 7.95 (d, J = 7.8 Hz, 1H), 7.73 (s, 1H), 7.33 (s, 1H), 6.93 (t, J = 55.0 Hz, 1H), 6.91 (s, 1H), 5.22 (p, J = 6.9 Hz, 1H), 5.07-4.76 (m, 2H), 4.63-4.42 (m, 0.35H, rotamer), 4.32-4.20 (m, 0.33H, rotamer), 3.99 (s, 3H), 3.97-3.88 (m, 1H), 3.86-3.56 (m, 5H), 3.45-3.04 (m, 0.36H, rotamer), 2.72-2.62 (m, 1H), 2.46-2.40 (m, 3H), 2.05-1.90 (m, 1H), 1.91-1.77 (m, 1H), 1.72-1.55 (m, 5H), 1.51 (d, J = 7.1 Hz, 3H), 1.45-1.30 (m, 2H), 1.31-1.10 (m, 2H), 1.08-0.97 (m, 1H), 0.96-0.80 (m, 1H), 0.65-0.46 (m, 1H), 0.44-0.24 (m, 1H). |
| 820 | 761.4 | 1H NMR (400 MHz, DMSO-d6) δ 9.15 (d, J = 7.0 Hz, 1H), 8.11 (d, J = 8.1 Hz, 1H), 7.98 (s, 2H), 7.81 (d, J = 7.8 Hz, 1H), 7.75 (s, 1H), 7.64-7.61 (m, 2H), 7.55 (d, J = 7.8 Hz, 1H), 7.48 (qd, J = 4.5, 1.4 Hz, 3H), 7.33 (s, 1H), 7.28 (d, J = 8.1 Hz, 1H), 7.25 (s, 1H), 5.21 (p, J = 7.0 Hz, 1H), 5.03-4.90 (m, 1H), 4.90-4.76 (m, 1H), 4.61-4.44 (m, 0.52H, rotamer), 4.25-4.12 (m, 0.80H, rotamer), 4.08-3.99 (m, 1H), 3.96-3.51 (m, 4H), 3.44-3.23 (m, 0.50H, rotamer), 3.21-2.97 (m, 0.71H, rotamer), 2.84-2.70 (m, 1H), 2.71-2.63 (m, 1H), 2.44-2.37 (m, 2H), 2.03-1.93 (m, 1H), 1.89-1.77 (m, 1H), 1.70-1.55 (m, 2H), 1.52 (d, J = 7.1 Hz, 3H), 1.30-1.16 (m, 2H), 1.14-0.93 (m, 3H), 0.62-0.52 (m, 1H), 0.51-0.37 (m, 1H). |
| 821 | 714.2 | 1H NMR (400 MHz, DMSO-d6) δ 8.27 (d, J = 7.4 Hz, 1H), 8.11 (d, J = 8.1 Hz, 1H), 7.42 (s, 1H), 7.29 (d, J = 8.1 Hz, 1H), 7.14 (s, 1H), 6.94 (d, J = 1.1 Hz, 1H), 5.38 (q, J = 15.8 Hz, 1H), 5.26-5.08 (m, 2H), 4.09 (s, 3H), 3.99 (s, 3H), 3.91 (s, 2H), 3.75-3.67 (m, 2H), 3.37 (s, 3H), 3.00 (dq, J = 25.9, 13.4 Hz, 3H), 2.64-2.54 (m, 1H), 2.26 (q, J = 13.0 Hz, 2H), 2.11-2.01 (m, 1H), 1.94 (s, 1H), 1.84 (s, 1H), 1.76 (s, 3H), 1.55-1.41 (m, 3H), 1.28 (dd, J = 15.0, 9.1 Hz, 2H), 1.17 (d, J = 9.3 Hz, 1H), 1.08 (s, 1H). |
| 822 | 750.2 | 1H NMR (400 MHz, DMSO-d6) δ 8.27 (d, J = 7.3 Hz, 1H), 8.12 (d, J = 8.1 Hz, 1H), 7.44 (s, 1H), 7.29 (d, J = 8.2 Hz, 1H), 7.15 (s, 1H), 6.95 (d, J = 1.2 Hz, 1H), 6.86 (s, 1H), 5.38 (q, J = 15.6 Hz, 1H), 5.26-5.06 (m, 2H), 4.67 (s, 1H), 4.10 (s, 3H), 4.00 (s, 3H), 3.61 (s, 2H), 3.47 (s, 1H), 3.00 (m, J = 26.0, 13.4 Hz, 2H), 2.58 (s, 1H), 2.25 (d, J = 13.1 Hz, 2H), 2.12-2.00 (m, 2H), 1.94 (d, J = 16.9 Hz, 2H), 1.85 (s, 1H), 1.76 (s, 2H), 1.47 (d, J = 7.0 Hz, 3H), 1.25 (d, J = 9.0 Hz, 1H), 1.19 (s, 1H), 1.08 (s, 1H). |
| 823 | 664.3 | 1H NMR (400 MHz, DMSO-d6) δ 8.14 (d, J = 8.1 Hz, 1H), 7.98 (t, J = 8.3 Hz, 2H), 7.43 (s, 1H), 7.29 (d, J = 8.1 Hz, 1H), 7.16 (s, 1H), 6.93 (d, J = 5.5 Hz, 1H), 5.52 (d, J = 16.1 Hz, 1H), 5.37-5.25 (m, 1H), 5.20 (d, J = 13.3 Hz, 1H), 4.11 (s, 3H), 4.00 (s, 3H), 3.71 (d, J = 5.9 Hz, 2H), 3.60-3.49 (m, 2H), 3.43 (d, J = 10.0 Hz, 1H), 3.37 (s, 3H), 2.03 (s, 2H), 1.96 (d, J = 8.7 Hz, 2H), 1.84 (s, 1H), 1.82-1.71 (m, 2H), 1.54 (d, J = 14.5 Hz, 2H), 1.44 (d, J = 6.9 Hz, 3H), 1.28 (m, J = 15.3, 11.5, 5.8 Hz, 2H), 1.03 (q, J = 4.6, 3.5 Hz, 1H), 0.96 (dd, J = 6.1, 3.2 Hz, 1H), 0.59 (m, J = 6.1, 3.9 Hz, 1H), 0.47-0.36 (m, 1H). |
| 824 | 738.2 | 1H NMR (400 MHz, DMSO-d6) δ 9.49 (d, J = 6.9 Hz, 1H), 8.24-8.08 (m, 4H), 8.05-7.98 (m, 1H), 7.93-7.82 (m, 2H), 7.46 (s, 1H), 7.32 (d, J = 8.1 Hz, 1H), 7.12 (s, 1H), 6.95 (s, 1H), 6.86 (t, J = 74.9 Hz, 1H), 5.30 (p, J = 7.0 Hz, 1H), 4.88 (t, J = 11.4 Hz, 1H), 4.67 (m, J = 6.3, 3.2 Hz, 1H), 4.63-4.52 (m, 1H), 4.14 (s, 3H), 4.00 (s, 3H), 2.84 (dd, J = 12.7, 8.1 Hz, 1H), 2.60 (d, J = 8.4 Hz, 2H), 2.03-1.85 (m, 2H), 1.76 (s, 1H), 1.56 (d, J = 7.1 Hz, 3H), 1.52-1.32 (m, 2H), 1.24 (d, J = 30.6 Hz, 1H), 1.17 (d, J = 7.1 Hz, 1H), 0.60 (d, J = 12.4 Hz, 1H). |

TABLE 3-continued

| Example | ES/MS m/z [M + H]+ | ¹H NMR |
|---|---|---|
| 825 | 669.3 | 1H NMR (400 MHz, DMSO-d6) δ 9.34 (d, J = 7.4 Hz, 1H), 8.17-8.05 (m, 2H), 7.97 (s, 3H), 7.44 (d, J = 3.0 Hz, 1H), 7.30-7.19 (m, 2H), 7.10 (s, 1H), 6.94 (s, 1H), 5.76 (s, 1H), 5.29 (p, J = 7.1 Hz, 1H), 4.88 (t, J = 12.4 Hz, 1H), 4.60 (d, J = 13.5 Hz, 1H), 4.12 (s, 3H), 4.00 (s, 3H), 3.71 (d, J = 5.8 Hz, 4H), 3.37 (s, 4H), 2.34 (m, J = 4.5, 3.8, 2.7 Hz, 1H), 2.30-2.15 (m, 1H), 1.94 (t, J = 11.3 Hz, 1H), 1.83-1.69 (m, 2H), 1.47 (d, J = 7.0 Hz, 4H), 1.37-1.14 (m, 3H), 0.48 (d, J = 12.4 Hz, 1H). |
| 826 | 634.3 | 1H NMR (400 MHz, DMSO-d6) δ 8.75 (s, 2H), 8.67 (d, J = 8.0 Hz, 1H), 8.45 (d, J = 8.5 Hz, 1H), 8.01 (dd, J = 10.5, 7.2 Hz, 2H), 7.69 (d, J = 10.3 Hz, 1H), 7.25 (s, 1H), 7.15 (d, J = 8.1 Hz, 1H), 5.21-5.13 (m, 1H), 5.06-4.97 (m, 1H), 4.93-4.82 (m, 1H), 4.75 (m, J = 21.1, 10.8, 5.7 Hz, 1H), 4.60 (d, J = 13.8 Hz, 1H), 4.41 (s, 1H), 3.89 (m, J = 9.9, 5.5 Hz, 1H), 3.46 (s, 1H), 2.98 (dd, J = 38.9, 26.4 Hz, 3H), 1.98-1.80 (m, 2H), 1.74-1.60 (m, 4H), 1.56 (m, J = 8.2, 4.8 Hz, 2H), 1.48-1.39 (m, 3H), 1.30-1.20 (m, 2H), 1.13 (d, J = 3.5 Hz, 1H), 1.06 (d, J = 2.8 Hz, 1H), 0.86 (q, J = 3.9 Hz, 1H), 0.70 (d, J = 24.1 Hz, 2H), 0.48 (d, J = 6.3 Hz, 1H). |
| 827 | 646.3 | 1H NMR (400 MHz, DMSO-d6) δ 8.44 (d, J = 8.5 Hz, 1H), 8.06 (s, 2H), 7.99 (d, J = 8.0 Hz, 1H), 7.86 (s, 1H), 7.69 (d, J = 9.4 Hz, 1H), 7.23 (s, 1H), 7.15 (d, J = 8.0 Hz, 1H), 5.17 (s, 1H), 5.07-4.96 (m, 2H), 4.69 (s, 1H), 4.60 (s, 1H), 4.04 (q, J = 7.1 Hz, 0H), 3.87 (dt, J = 9.2, 5.5 Hz, 1H), 3.37 (d, J = 10.6 Hz, 3H), 1.89 (d, J = 12.4 Hz, 2H), 1.69 (dd, J = 32.6, 15.3 Hz, 6H), 1.57 (dt, J = 8.3, 4.4 Hz, 1H), 1.44 (d, J = 7.1 Hz, 3H), 1.34-1.22 (m, 1H), 1.18 (t, J = 7.1 Hz, 0H), 0.87 (p, J = 4.1 Hz, 1H), 0.79-0.60 (m, 2H), 0.53-0.44 (m, 1H). |
| 828 | 716.5 | 1H NMR (400 MHz, DMSO-d6) δ 9.51 (d, J = 6.8 Hz, 1H), 8.17-8.09 (m, 1H), 8.06-8.00 (m, 1H), 7.97 (s, 1H), 7.92-7.84 (m, 2H), 7.68 (s, 1H), 7.38-7.28 (m, 2H), 5.29 (p, J = 7.0 Hz, 1H), 4.95 (q, J = 7.4 Hz, 1H), 4.84 (d, J = 13.6 Hz, 1H), 4.04 (m, J = 7.1, 3.9 Hz, 1H), 3.41 (s, 2H), 3.37 (s, 3H), 2.84 (dd, J = 12.7, 8.0 Hz, 1H), 2.61 (d, J = 8.4 Hz, 2H), 1.91 (s, 2H), 1.77 (dd, J = 6.3, 3.0 Hz, 2H), 1.57 (d, J = 7.0 Hz, 3H), 1.54-1.45 (m, 3H), 1.40 (d, J = 9.3 Hz, 2H), 1.33-1.16 (m, 3H), 1.16-0.99 (m, 2H), 0.56 (s, 1H), 0.48 (s, 1H). |
| 829 | 715.6 | 1H NMR (400 MHz, DMSO-d6) δ 9.28 (d, J = 6.6 Hz, 1H), 8.41 (s, 1H), 8.12 (d, J = 8.0 Hz, 1H), 8.06 (d, J = 8.1 Hz, 1H), 7.95 (d, J = 8.5 Hz, 2H), 7.79 (dd, J = 8.4, 6.9 Hz, 1H), 7.64 (dd, J = 16.6, 9.0 Hz, 2H), 7.36-7.25 (m, 2H), 5.22 (p, J = 7.0 Hz, 1H), 5.01-4.88 (m, 1H), 4.88-4.78 (m, 1H), 4.03 (td, J = 7.1, 3.6 Hz, 1H), 3.82 (s, 2H), 3.75-3.66 (m, 1H), 2.92 (dd, J = 12.5, 7.7 Hz, 2H), 2.56 (d, J = 7.8 Hz, 1H), 1.92 (s, 2H), 1.77 (d, J = 7.7 Hz, 2H), 1.55 (d, J = 7.1 Hz, 3H), 1.48 (s, 2H), 1.37 (d, J = 9.3 Hz, 2H), 1.30-1.17 (m, 2H), 1.17-0.99 (m, 2H), 0.54 (s, 1H), 0.47 (s, 1H). |
| 830 | 699.5 | 1H NMR (400 MHz, DMSO-d6) δ 9.29 (d, J = 6.6 Hz, 1H), 8.42 (s, 1H), 8.12 (d, J = 8.0 Hz, 1H), 8.07 (d, J = 8.1 Hz, 1H), 7.95 (d, J = 8.4 Hz, 2H), 7.80 (t, J = 7.7 Hz, 1H), 7.63 (t, J = 7.5 Hz, 1H), 7.59 (s, 1H), 7.34 (s, 1H), 7.30 (d, J = 8.1 Hz, 1H), 7.25 (d, J = 11.3 Hz, 1H), 5.22 (p, J = 6.9 Hz, 1H), 4.93 (s, 2H), 4.89-4.79 (m, 1H), 4.03 (m, J = 7.3, 4.0 Hz, 1H), 2.92 (dd, J = 12.8, 7.9 Hz, 2H), 2.56 (d, J = 9.1 Hz, 2H), 1.85-1.64 (m, 4H), 1.55 (d, J = 7.1 Hz, 3H), 1.47 (d, J = 9.2 Hz, 2H), 1.38 (s, 2H), 1.31-1.16 (m, 5H), 1.09 (dd, J = 20.7, 10.2 Hz, 3H), 0.50 (d, J = 34.4 Hz, 2H). |
| 831 | 685.2 | 1H NMR (400 MHz, DMSO-d6) δ 9.34 (d, J = 7.9 Hz, 1H), 8.44 (d, J = 5.4 Hz, 1H), 8.22 (s, 1H), 8.10 (d, J = 8.1 Hz, 1H), 7.98 (s, 1H), 7.45 (d, J = 5.3 Hz, 1H), 7.28 (d, J = 8.1 Hz, 1H), 7.10 (s, 1H), 6.94 (d, J = 1.2 Hz, 1H), 5.36 (d, J = 7.8 Hz, 1H), 4.91 (t, J = 11.9 Hz, 2H), 4.58 (d, J = 13.7 Hz, 1H), 4.12 (s, 3H), 4.00 (s, 3H), 3.69 (s, 3H), 3.37 (s, 3H), 3.15 (m, J = 7.4, 4.3 Hz, 2H), 2.39 (m, J = 11.9, 5.2 Hz, 2H), 1.95 (s, 1H), 1.76 (s, 1H), 1.48 (d, J = 6.9 Hz, 5H), 0.50 (d, J = 13.6 Hz, 2H). |
| 832 | 713.4 | 1H NMR (400 MHz, DMSO-d6) δ 8.39 (s, 1H), 8.16 (d, J = 8.2 Hz, 1H), 8.02 (d, J = 8.1 Hz, 1H), 7.97 (d, J = 8.4 Hz, 1H), 7.80 (ddd, J = 8.5, 6.9, 1.5 Hz, 1H), 7.68-7.59 (m, 2H), 7.38-7.31 (m, 2H), 7.25 (d, J = 11.4 Hz, 1H), 5.95 (q, J = 7.1 Hz, 1H), 4.84 (d, J = 15.7 Hz, 2H), 4.04 (q, J = 7.1 Hz, 2H), 3.21 (s, 3H), 2.95 (t, J = 11.7 Hz, 1H), 1.75 (dd, J = 17.1, 8.5 Hz, 4H), 1.57 (s, 4H), 1.33 (s, 0H), 1.29-1.22 (m, 1H), 1.22-1.14 (m, 5H), 1.10 (d, J = 6.6 Hz, 0H), 1.00 (s, 1H), 0.75 (s, 1H), 0.51 (s, 1H). |
| 833 | 729.3 | 1H NMR (400 MHz, DMSO-d6) δ 8.39 (s, 1H), 8.16 (d, J = 8.1 Hz, 1H), 8.02 (d, J = 8.1 Hz, 1H), 7.97 (d, J = 8.4 Hz, 2H), 7.80 (m, J = 8.4, 6.8, 1.5 Hz, 1H), 7.70 (s, 1H), 7.63 (t, J = 7.5 Hz, 1H), 7.35 (d, J = 8.7 Hz, 2H), 7.29 (d, J = 11.6 Hz, 1H), 5.96 (q, J = 7.3 Hz, 1H), 4.90-4.73 (m, 2H), 3.70 (dd, J = 6.6, 3.3 Hz, 1H), 3.37 (s, 3H), 3.21 (s, 3H), 3.01-2.89 (m, 1H), 2.61 (m, J = 12.2, 3.9 Hz, 1H), 1.91 (s, 1H), 1.76 (s, 1H), 1.73 (d, J = 7.3 Hz, 3H), 1.58 (s, 3H), 1.32 (s, 1H), 1.10 (p, J = 8.2, 7.2 Hz, 1H), 1.01 (d, J = 11.5 Hz, 1H), 0.77 (s, 1H), 0.52 (d, J = 10.2 Hz, 1H). |
| 834 | 682.3 | 1H NMR (400 MHz, DMSO-d6) δ 8.58 (d, J = 8.9 Hz, 1H), 8.09 (d, J = 8.1 Hz, 1H), 7.71 (s, 1H), 7.44 (s, 1H), 7.36 (d, J = 11.3 Hz, 1H), 7.26 (d, J = 8.1 Hz, 1H), 5.78 (t, J = 13.8 Hz, 1H), 5.19 (dd, J = 27.6, 14.4 Hz, 1H), 5.12-5.01 (m, 1H), 4.57 (ddd, J = 15.3, 9.4, 5.6 Hz, 1H), 3.37 (s, 3H), 2.23-2.01 (m, 1H), 1.96 (d, J = 13.8 Hz, 1H), 1.78 (dt, J = 12.4, 4.7 Hz, 2H), 1.63 (s, 0H), 1.54 (q, J = 5.3 Hz, 1H), 1.49-1.40 (m, 4H), 1.33 |

TABLE 3-continued

| Example | ES/MS m/z [M + H]+ | 1H NMR |
|---|---|---|
| | | (s, 1H), 0.86 (t, J = 5.1 Hz, 1H), 0.78 (dt, J = 13.3, 6.9 Hz, 1H), 0.65 (d, J = 11.3 Hz, 1H), 0.57-0.46 (m, 2H). |
| 835 | 666.3 | 1H NMR (400 MHz, DMSO-d6) δ 8.58 (d, J = 8.8 Hz, 1H), 8.09 (d, J = 8.0 Hz, 1H), 7.64 (s, 1H), 7.44 (s, 1H), 7.31 (d, J = 11.2 Hz, 1H), 7.25 (d, J = 8.1 Hz, 1H), 5.84-5.71 (m, 1H), 5.19 (dd, J = 27.7, 14.4 Hz, 1H), 5.06 (p, J = 7.3 Hz, 1H), 4.57 (ddd, J = 15.3, 9.4, 5.7 Hz, 1H), 2.24-2.01 (m, 1H), 1.96 (d, J = 13.6 Hz, 1H), 1.76 (dd, J = 16.2, 12.9 Hz, 2H), 1.69-1.58 (m, 1H), 1.54 (q, J = 5.3 Hz, 1H), 1.49-1.40 (m, 4H), 1.34 (d, J = 6.8 Hz, 0H), 1.21 (d, J = 6.9 Hz, 3H), 0.86 (t, J = 5.1 Hz, 1H), 0.79 (dt, J = 13.4, 6.5 Hz, 0H), 0.65 (d, J = 11.6 Hz, 1H), 0.57-0.46 (m, 2H). |
| 836 | 733.3 | 1H NMR (400 MHz, DMSO-d6) δ 9.39 (d, J = 8.1 Hz, 1H), 8.64 (d, J = 5.0 Hz, 1H), 8.11 (d, J = 8.1 Hz, 1H), 7.97 (s, 3H), 7.68 (s, 1H), 7.63 (d, J = 5.0 Hz, 1H), 7.33 (s, 1H), 7.31-7.25 (m, 2H), 5.41 (t, J = 7.4 Hz, 1H), 4.96 (t, J = 11.8 Hz, 1H), 4.89-4.79 (m, 1H), 4.02 (m, J = 7.1, 3.7 Hz, 1H), 3.75-3.67 (m, 1H), 3.37 (s, 3H), 2.61 (d, J = 12.1 Hz, 1H), 2.45-2.36 (m, 1H), 2.21-2.10 (m, 2H), 1.91 (d, J = 8.0 Hz, 2H), 1.76 (s, 2H), 1.52 (s, 2H), 1.47 (d, J = 7.2 Hz, 3H), 1.40-1.22 (m, 3H), 1.19 (d, J = 7.0 Hz, 2H), 1.10 (q, J = 6.4 Hz, 1H), 1.01 (s, 1H), 0.44 (d, J = 25.2 Hz, 2H). |
| 837 | 682.3 | 1H NMR (400 MHz, DMSO-d6) δ 8.59 (d, J = 8.8 Hz, 1H), 8.10 (d, J = 8.0 Hz, 1H), 7.97 (s, 2H), 7.71 (s, 1H), 7.43 (s, 1H), 7.33 (d, J = 11.4 Hz, 1H), 7.26 (d, J = 8.1 Hz, 1H), 5.77 (t, J = 13.8 Hz, 1H), 5.23 (dd, J = 27.4, 14.6 Hz, 1H), 5.15-5.04 (m, 1H), 4.60 (m, J = 15.0, 9.7, 5.6 Hz, 1H), 4.51-4.43 (m, 1H), 4.31 (t, J = 5.3 Hz, 1H), 3.84 (s, 2H), 3.71 (m, J = 6.4, 3.0 Hz, 1H), 3.37 (s, 3H), 2.23 (d, J = 19.4 Hz, 1H), 2.18-2.04 (m, 1H), 1.96 (dd, J = 18.7, 9.5 Hz, 3H), 1.76 (s, 2H), 1.68-1.58 (m, 2H), 1.56 (m, J = 8.3, 4.6 Hz, 1H), 1.45 (d, J = 7.1 Hz, 3H), 1.42-1.31 (m, 1H), 0.91-0.81 (m, 1H), 0.66 (d, J = 11.0 Hz, 1H), 0.63-0.55 (m, 2H), 0.51 (m, J = 6.8, 5.8, 3.6 Hz, 1H). |
| 838 | 717.3 | 1H NMR (400 MHz, DMSO-d6) δ 9.27 (d, J = 7.0 Hz, 1H), 8.11 (d, J = 8.0 Hz, 1H), 8.04 (d, J = 7.8 Hz, 1H), 7.91 (s, 3H), 7.81 (d, J = 7.9 Hz, 1H), 7.59 (d, J = 1.2 Hz, 1H), 7.33 (s, 1H), 7.28 (d, J = 8.1 Hz, 1H), 7.25 (d, J = 11.4 Hz, 1H), 5.23 (p, J = 7.0 Hz, 1H), 4.92 (d, J = 10.4 Hz, 1H), 4.84 (d, J = 13.4 Hz, 1H), 4.02 (m, J = 7.0, 3.9 Hz, 1H), 2.47 (s, 4H), 1.74 (q, J = 12.9, 11.6 Hz, 4H), 1.51 (d, J = 7.0 Hz, 7H), 1.20 (d, J = 6.9 Hz, 5H), 1.15-0.98 (m, 3H), 0.60-0.39 (m, 3H). |
| 839 | 712.2 | 1H NMR (400 MHz, DMSO-d6) δ 9.52 (d, J = 6.7 Hz, 1H), 8.19-8.09 (m, 2H), 8.07-8.00 (m, 1H), 7.96 (s, 1H), 7.93-7.83 (m, 2H), 7.73-7.62 (m, 1H), 7.39-7.30 (m, 2H), 7.25 (s, 1H), 5.29 (p, J = 7.0 Hz, 1H), 5.02-4.89 (m, 0.5H), 4.84 (d, J = 13.5 Hz, 1H), 4.52 (s, 0.43H), 4.18 (s, 0.5H), 4.08-3.98 (m, 1H), 3.85-3.72 (m, 1H), 3.20-3.01 (m, 1H), 2.84 (dd, J = 12.7, 8.0 Hz, 1H), 2.61 (d, J = 8.3 Hz, 2H), 1.94 (d, J = 20.1 Hz, 2H), 1.79 (d, J = 22.6 Hz, 2H), 1.65 (s, 2H), 1.57 (d, J = 7.1 Hz, 3H), 1.49 (d, J = 11.4 Hz, 2H), 1.41 (s, 1H), 1.24 (s, 2H), 1.09 (s, 2H), 0.55 (s, 1H), 0.47 (s, 1H). |
| 840 | 714.2 | 1H NMR (400 MHz, DMSO-d6) δ 9.12 (d, J = 7.0 Hz, 1H), 8.11 (d, J = 8.1 Hz, 1H), 7.96 (s, 2H), 7.82 (d, J = 8.1 Hz, 1H), 7.73 (s, 1H), 7.61 (s, 1H), 7.42 (d, J = 8.0 Hz, 1H), 7.38 (s, 1H), 7.28 (d, J = 8.1 Hz, 1H), 5.31 (s, 0.36H), 5.20 (q, J = 7.2 Hz, 1H), 4.90 (d, J = 6.9 Hz, 0.27H), 4.85 (s, 1H), 4.63-4.49 (m, 2H), 4.17 (s, 0.5H), 3.83-3.69 (m, 0.5H), 3.15 (dd, J = 7.2, 4.0 Hz, 0.5H), 2.77 (s, 0.28H), 2.66-2.60 (m, 1H), 2.60-2.54 (m, 1H), 2.38 (d, J = 7.9 Hz, 2H), 2.03-1.90 (m, 2H), 1.76 (s, 3H), 1.74-1.57 (m, 3H), 1.50 (d, J = 7.1 Hz, 3H), 1.46-1.42 (m, 2H), 1.33-1.16 (m, 3H), 0.85 (s, 2H), 0.52 (s, 2H). |
| 841 | 711.1 | 1H NMR (400 MHz, DMSO-d6) δ 9.02-8.89 (m, 1H), 8.37 (dd, J = 8.4, 1.8 Hz, 1H), 8.11 (d, J = 7.9 Hz, 1H), 7.96 (s, 1H), 7.92 (d, J = 8.5 Hz, 1H), 7.80-7.57 (m, 1H), 7.54 (dd, J = 8.3, 4.2 Hz, 1H), 7.47 (d, J = 8.4 Hz, 1H), 7.34 (s, 1H), 7.31 (d, J = 8.0 Hz, 1H), 7.24 (s, 1H), 5.45 (t, J = 7.3 Hz, 1H), 5.09-4.92 (m, 2H), 4.83 (d, J = 13.0 Hz, 1H), 4.53 (s, 0.42H), 4.19 (s, 0.45H), 4.04 (m, J = 8.5, 4.2 Hz, 2H), 3.82-3.72 (m, 1H), 3.19-3.08 (m, 1H), 2.77 (s, 0.32H), 2.59 (d, J = 13.1 Hz, 0.37H), 2.42-2.35 (m, 1H), 2.31-2.19 (m, 1H), 2.02-1.89 (m, 2H), 1.76 (s, 2H), 1.65 (s, 3H), 1.49 (d, J = 7.1 Hz, 3H), 1.32-1.15 (m, 2H), 1.23 (d, J = 8.3 Hz, 2H), 1.09 (s, 2H), 0.46 (s, 2H). |
| 842 | 715.3 | 1H NMR (400 MHz, DMSO-d6) δ 9.25 (d, J = 7.2 Hz, 1H), 8.10 (d, J = 8.0 Hz, 1H), 8.04 (d, J = 7.8 Hz, 1H), 7.81 (d, J = 7.9 Hz, 1H), 7.37 (s, 1H), 7.28 (d, J = 8.1 Hz, 1H), 7.10 (s, 1H), 6.90 (s, 1H), 5.25 (t, J = 7.1 Hz, 1H), 5.00 (s, 0.48H), 4.86 (m, J = 14.8, 7.8 Hz, 1H), 4.60 (d, J = 13.6 Hz, 1H), 4.55-4.48 (m, 0.56H) 4.23 (s, 0.41H), 4.12 (s, 3H), 4.00 (s, 3H), 3.40 (s, 1H), 3.31-3.21 (m, 1H), 3.14 (s, 0.34H), 2.75 (d, J = 10.7 Hz, 0.62H), 2.68 (m, J = 10.7, 7.5, 4.7 Hz, 1H), 2.46 (s, 1H), 1.98 (dd, J = 12.5, 7.2 Hz, 2H), 1.90-1.73 (m, 2H), 1.62 (s, 3H), 1.50 (d, J = 7.0 Hz, 3H), 1.40 (d, J = 10.2 Hz, 1H), 1.24 (s, 1H), 0.56 (s, 1H). |
| 843 | 711.2 | 1H NMR (400 MHz, DMSO-d6) δ 9.20 (d, J = 7.0 Hz, 1H), 8.11 (d, J = 8.0 Hz, 1H), 7.94 (s, 1H), 7.74 (s, 1H), 7.59 (d, J = 7.9 Hz, 1H), 7.33 (s, 1H), 7.28 (d, J = 8.1 Hz, 1H), 6.93 (t, J = 55.0 Hz, 1H), 5.22 (p, J = 7.0 Hz, 1H), 4.94 (dd, J = 16.6, 7.1 Hz, 1H), 4.85 (s, 1H), 4.52 (s, 0.45H), |

TABLE 3-continued

| Example | ES/MS m/z [M + H]+ | ¹H NMR |
|---|---|---|
| | | 4.18 (s, 0.44H), 4.06-3.99 (m, 1H), 3.81-3.71 (m, 0.89H), 3.20-3.10 (m, 1H), 2.75 (d, J = 9.9 Hz, 0.48H), 2.72-2.62 (m, 1H), 2.44 (d, J = 8.0 Hz, 3H), 1.98 (d, J = 11.1 Hz, 2H), 1.76 (s, 2H), 1.65 (s, 2H), 1.51 (d, J = 7.0 Hz, 3H), 1.47 (s, 1H), 1.42 (s, 1H), 1.29-1.14 (m, 3H), 1.03 (d, J = 41.5 Hz, 3H), 0.53 (s, 1H), 0.46 (s, 1H). |
| 844 | 729.6 | 1H NMR (400 MHz, DMSO-d6) δ 9.32 (d, J = 6.8 Hz, 1H), 8.71 (s, 1H), 8.11 (d, J = 8.1 Hz, 1H), 7.97 (s, 1H), 7.85 (s, 1H), 7.74 (s, 1H), 7.59 (s, 1H), 7.33 (s, 1H), 7.28 (d, J = 8.1 Hz, 1H), 7.24 (s, 1H), 5.22 (p, J = 7.0 Hz, 1H), 4.96 (s, 0.56H), 4.96-4.80 (m, 2H), 4.52 (s, 0.48H), 4.17 (s, 1H), 4.02 (m, J = 6.7, 3.5 Hz, 3H), 3.37 (s, 2H), 3.14 (s, 0.50H), 2.76 (s, 0.65H), 2.43-2.36 (m, 1H), 1.95 (q, J = 10.5 Hz, 1H), 1.79 (d, J = 20.4 Hz, 1H), 1.72-1.56 (m, 3H), 1.52 (d, J = 7.1 Hz, 3H), 1.47 (s, 2H), 1.32 (m, J = 11.5, 5.7 Hz, 1H), 1.20 (s, 2H), 1.07 (s, 2H), 0.59-0.39 (m, 1H). |
| 845 | 681.2 | 1H NMR (400 MHz, DMSO-d6) δ 9.34 (d, J = 7.9 Hz, 1H), 8.45 (d, J = 5.4 Hz, 1H), 8.10 (d, J = 8.0 Hz, 1H), 7.98 (s, 2H), 7.75 (s, 1H), 7.45 (d, J = 5.4 Hz, 1H), 7.37 (s, 1H), 7.28 (d, J = 8.1 Hz, 1H), 7.10 (s, 1H), 6.90 (s, 1H), 5.43-5.30 (m, 1H), 5.0 (s, 0.4H) 4.97-4.85 (m, 1H), 4.59 (d, J = 13.8 Hz, 2H), 4.23 (s, 0.75H), 4.12 (s, 3H), 4.00 (s, 3H), 2.77 (s, 1H), 2.44-2.26 (m, 3H), 1.96 (d, J = 9.5 Hz, 1H), 1.79 (d, J = 20.2 Hz, 1H), 1.62 (s, 3H), 1.48 (d, J = 7.1 Hz, 5H), 1.25 (s, 2H), 0.49 (s, 2H). |
| 846 | 714.1 | 1H NMR (400 MHz, DMSO-d6) δ 9.14 (d, J = 7.0 Hz, 1H), 8.11 (d, J = 8.1 Hz, 1H), 7.98 (s, 2H), 7.83 (d, J = 8.1 Hz, 1H), 7.42 (d, J = 8.0 Hz, 1H), 7.32-7.23 (m, 2H), 5.26-5.13 (m, 1H), 5.03 (s, 0.47H), 4.93 (t, J = 12.8 Hz, 0.69H), 4.80 (s, 0.27H), 4.51 (s, 2H), 4.18 (s, 0.32H), 4.09 (m, J = 10.0, 5.5 Hz, 2H), 3.76 (s, 0.38H), 3.33 (d, J = 34.8 Hz, 2H), 3.16 (s, 0.42H), 2.76 (d, J = 14.4 Hz, 0.40H), 2.62 (dd, J = 12.5, 7.5 Hz, 1H), 2.38 (d, J = 7.8 Hz, 1H), 1.96 (d, J = 11.4 Hz, 2H), 1.76 (s, 2H), 1.61 (dd, J = 16.6, 7.4 Hz, 4H), 1.50 (d, J = 7.0 Hz, 3H), 1.42 (s, 2H), 1.29-1.10 (m, 2H), 0.81 (d, J = 26.0 Hz, 1H), 0.55 (s, 1H). |
| 847 | 741.2 | 1H NMR (400 MHz, DMSO-d6) δ 9.27 (d, J = 7.0 Hz, 1H), 8.09 (d, J = 8.0 Hz, 1H), 8.04 (d, J = 7.9 Hz, 1H), 7.96 (s, 1H), 7.81 (d, J = 7.9 Hz, 1H), 7.73 (s, 1H), 7.33 (s, 1H), 7.26 (d, J = 8.1 Hz, 1H), 7.23 (s, 1H), 6.91 (s, 1H), 5.23 (p, J = 7.1 Hz, 1H), 5.02 (s, 0.66H), 4.90 (m, J = 23.4, 13.2 Hz, 2H), 4.53 (s, 0.45H), 4.25 (s, 0.52H), 4.00 (s, 3H), 3.93 (m, J = 7.1, 3.9 Hz, 1H), 3.83 (s, 1H) 2.75 (s, 0.69H), 2.72-2.63 (m, 1H), 2.46 (s, 2H), 1.96 (d, J = 11.1 Hz, 2H), 1.79 (d, J = 20.0 Hz, 2H), 1.59 (s, 3H), 1.51 (d, J = 7.1 Hz, 3H), 1.41 (s, 2H), 1.29-1.09 (m, 2H), 1.03 (d, J = 7.8 Hz, 3H), 0.90 (s, 1H), 0.53 (d, J = 12.2 Hz, 1H), 0.37 (m, 1H). |
| 848 | 650.4 | 1H NMR (400 MHz, DMSO-d6) δ 8.56 (d, J = 8.9 Hz, 1H), 8.06 (d, J = 8.0 Hz, 1H), 8.00 (s, 2H), 7.44 (s, 1H), 7.23 (d, J = 8.1 Hz, 1H), 7.14 (s, 1H), 6.96 (s, 1H), 5.51 (t, J = 13.6 Hz, 1H), 5.22-4.99 (m, 2H), 4.10 (s, 3H), 4.00 (s, 3H), 3.74-3.67 (m, 1H), 3.56-3.51 (m, 2H), 3.46-3.40 (m, 1H), 3.37 (s, 3H), 2.26-2.01 (m, 2H), 2.01-1.89 (m, 2H), 1.83-1.70 (m, 1H), 1.68-1.57 (m, 1H), 1.57-1.51 (m, 1H), 1.44 (d, J = 7.1 Hz, 3H), 1.38-1.21 (m, 1H), 0.94-0.78 (m, 1H), 0.72-0.59 (m, 1H), 0.56-0.45 (m, 2H). |
| 849 | 634.5 | 1H NMR (400 MHz, DMSO-d6) δ 8.56 (d, J = 8.9 Hz, 1H), 8.06 (d, J = 8.0 Hz, 1H), 7.92 (s, 2H), 7.36 (s, 1H), 7.24 (d, J = 8.1 Hz, 1H), 7.13 (s, 1H), 6.89 (s, 1H), 5.50 (t, J = 13.6 Hz, 1H), 5.25-4.99 (m, 2H), 4.10 (s, 3H), 4.00 (s, 3H), 3.27-2.86 (m, 1H), 2.29-1.69 (m, 5H), 1.69-1.49 (m, 3H), 1.44 (d, J = 7.1 Hz, 3H), 1.38-1.14 (m, 6H), 0.94-0.78 (m, 1H), 0.64 (d, J = 12.3 Hz, 1H), 0.50 (d, J = 7.4 Hz, 2H). |
| 850 | 686.6 | 1H NMR (400 MHz, DMSO-d6) δ 8.56 (d, J = 8.8 Hz, 1H), 8.19 (s, 2H), 8.06 (d, J = 8.0 Hz, 1H), 7.46 (s, 1H), 7.24 (d, J = 8.1 Hz, 1H), 7.14 (s, 1H), 7.07-6.56 (m, 2H), 5.52 (t, J = 13.4 Hz, 1H), 5.24-5.00 (m, 2H), 4.67 (s, 1H), 4.10 (s, 3H), 4.00 (s, 3H), 3.54 (d, J = 53.9 Hz, 3H), 2.96-2.69 (m, 1H), 2.03 (d, J = 53.2 Hz, 4H), 1.71-1.50 (m, 2H), 1.44 (d, J = 7.0 Hz, 3H), 1.37-1.22 (m, 1H), 0.85 (t, J = 5.1 Hz, 1H), 0.72-0.58 (m, 1H), 0.50 (d, J = 7.3 Hz, 2H). |
| 851 | 638.4 | 1H NMR (400 MHz, DMSO-d6) δ 8.57 (d, J = 8.9 Hz, 1H), 8.13-7.93 (m, 3H), 7.40 (s, 1H), 7.24 (d, J = 8.0 Hz, 1H), 7.14 (s, 1H), 6.91 (s, 1H), 5.51 (t, J = 13.6 Hz, 1H), 5.23-4.88 (m, 3H), 4.10 (s, 3H), 3.99 (s, 3H), 3.40 (s, 2H), 2.35 (d, J = 11.8 Hz, 2H), 2.25-1.74 (m, 4H), 1.70-1.50 (m, 2H), 1.44 (d, J = 7.1 Hz, 3H), 1.32 (s, 1H), 0.85 (t, J = 5.1 Hz, 1H), 0.64 (s, 1H), 0.50 (d, J = 7.5 Hz, 2H). |
| 852 | 634.5 | 1H NMR (400 MHz, DMSO-d6) δ 8.56 (d, J = 8.8 Hz, 1H), 8.06 (d, J = 8.0 Hz, 1H), 7.95 (s, 2H), 7.37 (s, 1H), 7.23 (d, J = 8.1 Hz, 1H), 7.14 (s, 1H), 6.90 (s, 1H), 5.52 (t, J = 13.8 Hz, 1H), 5.29-4.96 (m, 2H), 4.10 (s, 3H), 4.00 (s, 3H), 3.44-3.30 (m, 1H), 2.25-1.90 (m, 2H), 1.86-1.49 (m, 5H), 1.44 (d, J = 7.1 Hz, 3H), 1.37-1.26 (m, 1H), 1.22 (d, J = 6.9 Hz, 3H), 0.85 (t, J = 5.1 Hz, 1H), 0.64 (d, J = 11.5 Hz, 1H), 0.50 (d, J = 7.5 Hz, 2H). |
| 853 | 632.7 | 1H NMR (400 MHz, DMSO-d6) δ 8.56 (d, J = 8.7 Hz, 1H), 8.06 (d, J = 8.0 Hz, 1H), 7.99-7.88 (m, 2H), 7.24 (d, J = 8.0 Hz, 1H), 7.14 (s, 1H), 7.08-6.94 (m, 1H), 5.59-5.42 (m, 1H), 5.22-4.99 (m, 2H), 4.58-4.15 (m, 1H), 4.10 (s, 3H), 4.01 (s, 3H), 3.84-3.51 (m, 2H), 3.23-3.14 (m, |

TABLE 3-continued

| Example | ES/MS m/z [M + H]+ | ¹H NMR |
|---|---|---|
| | | 1H), 2.91-2.55 (m, 2H), 2.21-1.86 (m, 6H), 1.78-1.49 (m, 3H), 1.45 (d, J = 7.0 Hz, 3H), 1.32 (s, 1H), 0.85 (t, J = 5.1 Hz, 1H), 0.70-0.56 (m, 1H), 0.50 (d, J = 7.3 Hz, 2H). |
| 854 | 680.3 | 1H NMR (400 MHz, DMSO-d6) δ 8.78 (d, J = 7.6 Hz, 1H), 8.06 (d, J = 8.0 Hz, 1H), 7.98 (s, 3H), 7.43 (s, 1H), 7.22 (dt, J = 7.9, 3.9 Hz, 2H), 7.07 (s, 1H), 6.93 (d, J = 1.2 Hz, 1H), 6.87 (d, J = 8.3 Hz, 1H), 6.76 (d, J = 7.5 Hz, 1H), 5.33-5.23 (m, 1H), 4.91 (t, J = 12.7 Hz, 1H), 4.56 (d, J = 13.4 Hz, 1H), 4.11 (s, 3H), 3.99 (s, 3H), 3.78 (s, 3H), 3.70 (s, 1H), 3.53 (s, 2H), 3.36 (s, 3H), 2.19-2.01 (m, 2H), 2.00-1.90 (m, 1H), 1.82-1.70 (m, 1H), 1.57-1.36 (m, 2H), 1.43 (d, J = 7.1 Hz, 3H), 1.29-1.10 (m, 3H), 0.42-0.30 (m, 1H) |
| 855 | 666.3 | 1H NMR (400 MHz, DMSO-d6) δ 8.63 (d, J = 2.6 Hz, 1H), 8.54 (d, J = 2.6 Hz, 1H), 8.14 (d, J = 8.1 Hz, 1H), 7.98 (br s, 4H), 7.45 (s, 1H), 7.33 (d, J = 8.1 Hz, 1H), 7.09 (s, 1H), 6.93 (d, J = 1.2 Hz, 1H), 5.94 (q, J = 7.3 Hz, 1H), 4.74 (dt, J = 14.9, 7.8 Hz, 1H), 4.57-4.48 (m, 1H), 4.12 (s, 3H), 3.99 (s, 4H), 3.71 (br s, 1H), 3.54 (br s, 2H), 3.36 (s, 4H), 3.04 (s, 3H), 2.81 (td, J = 12.9, 4.2 Hz, 1H), 2.24-2.10 (m, 1H), 2.00-1.90 (m, 1H), 1.80-1.70 (m, 1H), 1.68 (d, J = 7.3 Hz, 3H), 1.64-1.53 (m, 3H), 1.339-1.29 (m, 1H), 0.92-0.80 (m, 1H). |
| 856 | 650.3 | 1H NMR (400 MHz, DMSO-d6) δ 8.65 (d, J = 7.0 Hz, 1H), 8.04 (d, J = 8.2 Hz, 1H), 7.98 (br s, 3H), 7.46 (s, 1H), 7.24 (d, J = 8.2 Hz, 1H), 7.06 (s, 1H), 6.93 (d, J = 1.1 Hz, 1H), 4.70-4.51 (m, 2H), 4.45 (p, J = 7.1 Hz, 1H), 4.13 (s, 3H), 3.99 (s, 3H), 3.86 (br s, 1H), 3.70 (br s, 1H), 3.54 (br s, 2H), 3.36 (s, 3H), 2.42-2.06 (m, 3H), 1.96 (br s, 3H), 1.81-1.72 (m, 1H), 1.75 (d, J = 7.0 Hz, 3H), 1.54 (dt, J = 8.7, 4.7 Hz, 1H), 1.44-1.27 (m, 1H), 0.95-0.78 (m, 2H), 0.67-0.59 (m, 1H). |
| 857 | 650.3 | 1H NMR (400 MHz, DMSO-d6) δ 8.60 (d, J = 8.6 Hz, 1H), 8.01 (d, J = 8.0 Hz, 1H), 7.96 (br s, 3H), 7.48 (s, 1H), 7.17 (d, J = 8.1 Hz, 1H), 7.05 (s, 1H), 6.92 (d, J = 1.1 Hz, 1H), 5.08-4.98 (m, 1H), 4.64-4.46 (m, 2H), 4.13 (s, 3H), 3.99 (s, 3H), 3.81 (br s, 1H), 3.70 (br s, 1H), 3.56 (br s, 2H), 3.36 (s, 3H), 2.44-2.24 (m, 2H), 2.06-1.90 (m, 3H), 1.83-1.67 (m, 3H), 1.43 (d, J = 7.1 Hz, 3H), 0.92 (t, J = 5.4 Hz, 1H), 0.70--0.62 m, 2H). |
| 858 | 650.3 | 1H NMR (400 MHz, DMSO-d6) δ 8.75 (d, J = 7.3 Hz, 1H), 8.07 (d, J = 8.2 Hz, 1H), 7.98 (br s, 3H), 7.46 (s, 1H), 7.25 (d, J = 8.3 Hz, 1H), 7.06 (s, 1H), 6.93 (d, J = 1.2 Hz, 1H), 4.74-4.48 (m, 3H), 4.13 (s, 3H), 3.99 (s, 3H), 3.86 (br s, 1H), 3.71 (br s, 1H), 3.54 (br s, 2H), 3.36 (s, 3H), 2.32-1.66 (m, 6H), 1.71 (d, J = 7.0 Hz, 3H), 1.56-1.33 (m, 1H), 1.23-1.11 (m, 1H), 0.99-0.89 (m, 1H), 0.79-0.72 (m, 1H). |
| 859 | 650.3 | 1H NMR (400 MHz, DMSO-d6) δ 8.73 (d, J = 6.4 Hz, 1H), 8.03 (d, J = 8.1 Hz, 1H), 7.97 (br s, 3H), 7.47 (s, 1H), 7.16 (d, J = 8.1 Hz, 1H), 7.04 (s, 1H), 6.92 (d, J = 1.2 Hz, 1H), 4.91 (p, J = 7.0 Hz, 1H), 4.71-4.63 (m, 1H), 4.52 (t, J = 12.5 Hz, 1H), 4.13 (s, 3H), 3.99 (s, 3H), 3.83 (br s, 1H), 3.70 (br s, 1H), 3.55 (br s, 2H), 3.36 (s, 3H), 2.19-1.69 (m, 5H), 1.58-1.39 (m, 1H), 1.46 (d, J = 7.1 Hz, 3H), 1.22-1.13 (m, 1H), 0.98 (td, J = 8.7, 3.7 Hz, 1H), 0.62 (q, J = 5.6 Hz, 1H). |
| 860 | 679.3 | 1H NMR (400 MHz, DMSO-d6) δ 8.90 (d, J = 8.3 Hz, 1H), 8.59 (br s, 1H), 8.07 (d, J = 8.1 Hz, 1H), 7.98 br (s, 4.5H), 7.72-7.63 (m, 1H), 7.51-7.40 (m, 2H), 7.21 (d, J = 8.1 Hz, 1H), 7.07 (s, 1H), 6.94 (d, J = 1.2 Hz, 1H), 5.22 (p, J = 7.2 Hz, 1H), 5.13-5.00 (m, 1H), 4.64-4.54 (m, 1H), 4.24-4.16 (m, 1H), 4.12 (s, 3H), 3.99 (s, 3H), 3.85 (br s, 1H), 3.71 (brs, 1H), 3.54 (s, 3H), 3.37 (s, 3H), 2.29-1.89 (m, 3H), 1.83-1.32 (m, 5H), 1.41 (d, J = 7.1 Hz, 3H), 1.25-0.92 (m, 3H), 0.62-0.47 (m, 1H). |
| 861 | 693.3 | 1H NMR (400 MHz, DMSO-d6) δ 8.58 (dt, J = 4.7, 1.5 Hz, 1H), 8.06 (d, J = 8.1 Hz, 1H), 8.03-7.90 (m, 5H), 7.83 (td, J = 7.8, 1.9 Hz, 1H), 7.47-7.41 (m, 2H), 7.31 (ddd, J = 7.5, 4.8, 1.0 Hz, 1H), 7.20 (d, J = 8.1 Hz, 1H), 7.04 (s, 1H), 6.93 (d, J = 1.2 Hz, 1H), 5.15 (p, J = 7.1 Hz, 1H), 4.91-4.81 (m, 1H), 4.43-4.34 (m, 1H), 4.12 (s, 3H), 3.99 (s, 3H), 3.87 (br s, 2H), 3.70 (br s, 1H), 3.54 (br s, 2H), 3.07 (s, 3H), 2.03-1.59 (m, 6H), 1.42 (br s, 4H), 1.35 (d, J = 7.0 Hz, 3H), 1.29 (s, 3H), 1.21-1.00 (m, 2H). |
| 862 | 693.3 | 1H NMR (400 MHz, DMSO-d6) δ 8.60-8.54 (m, 1H), 8.26 (d, J = 7.2 Hz, 1H), 8.09 (d, J = 8.1 Hz, 1H), 8.04-7.85 (m, 4H), 7.54-7.35 (m, 3H), 7.26 (d, J = 8.2 Hz, 1H), 7.05 (s, 1H), 6.93 (d, J = 1.2 Hz, 1H), 5.23 (p, J = 7.1 Hz, 1H), 4.80-4.70 (m, 1H), 4.53-4.43 (m, 1H), 4.12 (s, 3H), 3.99 (s, 3H), 3.87 (s, 1H), 3.71 (br s, 1H), 3.54 (br s, 2H), 3.36 (s, 3H), 2.15-2.06 (m, 2H), 2.00-1.90 (m, 1H), 1.80-1.51 (m, 4H), 1.65 (s, 3H), 1.57 (d, J = 7.0 Hz, 3H), 1.50-1.22 (m, 4H), 1.12 (br s, 1H). |
| 863 | 681.3 | 1H NMR (400 MHz, DMSO-d6) δ 8.97 (d, J = 7.6 Hz, 1H), 8.07 (d, J = 8.0 Hz, 1H), 8.04 (d, J = 5.2 Hz, 1H), 7.98 (br s, 3H), 7.43 (s, 1H), 7.23 (d, J = 8.0 Hz, 1H), 7.08 (s, 1H), 6.93 (d, J = 1.1 Hz, 1H), 6.84 (d, J = 5.3 Hz, 1H), 5.28 (p, J = 7.1 Hz, 1H), 4.94-4.84 (m, 1H), 4.60-4.52 (m, 1H), 4.11 (s, 3H), 3.99 (s, 3H), 3.88 (s, 3H), 3.71 (br s, 1H), 3.53 (br s, 2H), 3.36 (s, 3H), 2.17 (dt, J = 12.4, 6.4 Hz, 1H), 2.12-2.03 (m, 1H), 1.94 (br s, 1H), 1.81-1.70 (s, 1H), 1.57-1.38 (m, sH), 1.44 (d, J = 7.0 Hz, 3H), 1.34-1.11 (m, 2H), 0.48-0.34 (m, 1H). |
| 864 | 658.2 | 1H NMR (400 MHz, DMSO-d6) δ 8.04-7.90 (m, 3.5H), 7.70 (d, J = 8.2 Hz, 0.5H), 7.43 (s, 1H), 7.36 (d, J = 8.1 Hz, 0.5H), 7.26 (s, 0.5H), 7.15 (d, |

TABLE 3-continued

| Example | ES/MS m/z [M + H]+ | ¹H NMR |
|---|---|---|
| | | J = 8.1 Hz, 1H), 7.04 (s, 1H), 6.92 (d, J = 1.1 Hz, 1H), 5.00-4.89 (m, 2H), 4.65-4.57 (m, 1H), 4.08 (s, 3H), 3.98 (s, 3H), 3.73-3.68 (br s, 1H), 3.59 (d, J = 10.6 Hz, 1H), 3.53 (br s, 2H), 3.43 (d, J = 10.6 Hz, 1H), 3.38 (s, 3H), 3.36 (s, 3H), 2.29-2.17 (m, 1H), 1.99-1.90 (m, 1H), 1.81 1.71 (m, 1H), 1.43 (d, J = 7.0 Hz, 3H), 1.40-1.29 (m, 4H), 1.07-0.86 (m, 4H), 0.57 (dd, J = 8.6, 3.9 Hz, 1H), 0.41-0.30 (m, 1H), 0.15-0.03 (m, 1H). |
| 865 | 658.3 | 1H NMR (400 MHz, DMSO-d6) δ 8.05 (d, J = 8.2 Hz, 1H), 8.03-7.91 (m, 4H), 7.44 (s, 1H), 7.23 (d, J = 8.2 Hz, 1H), 7.03 (s, 1H), 6.93 (d, J = 1.1 Hz, 1H), 5.11 (p, J = 7.2 Hz, 1H), 4.70-4.50 (m, 2H), 4.10 (s, 3H), 3.98 (s, 3H), 3.95 (d, J = 10.1 Hz, 1H), 3.73-3.67 (m, 1H), 3.54 (br s, 2H), 3.36 (s, 3H), 3.26 (s, 3H), 2.90 (d, J = 10.0 Hz, 1H), 1.94 (br s, 1H), 1.75 (br s, 1H), 1.58 (d, J = 7.1 Hz, 3H), 1.67-1.26 (m, 5H), 1.22 (t, J = 5.6 Hz, 1H), 1.08-0.69 (m, 6H). |
| 866 | 636.3 | 1H NMR (400 MHz, DMSO-d6) δ 8.10 (d, J = 8.1 Hz, 1H), 8.05 (d, J = 6.8 Hz, 1H), 7.98 (br s, 4H), 7.50 (s, 1H),  7.48 (s, 1H), 7.32-7.23 (m, 2H), 7.19-7.12 (m, 2H), 7.05 (s, 1H), 6.94 (s, 1H), 5.10 (p, J = 6.7 Hz, 1H), 4.39-4.26 (m, 2H), 4.13 (s, 3H), 4.00 (s, 3H), 3.74-3.69 (m, 1H), 3.67 (d, J = 15.9 Hz, 1H), 3.52 (d, J = 15.7 Hz, 1H), 3.37 (s, 3H), 2.20-2.10 (m, 1H), 2.02-1.73 (m, 3H), 1.38 (d, J = 6.8 Hz, 3H). |
| 867 | 714.3 | 1H NMR (400 MHz, DMSO-d6) δ 8.09 (d, J = 8.1 Hz, 1H), 7.98 (br s, 4H), 7.45 (s, 1H), 7.27 (d, J = 8.2 Hz, 1H), 7.12 (s, 1H), 6.94 (s, 1H), 6.46-6.15 (m, 1H), 5.88 (q, J = 7.5 Hz, 1H), 5.45 (t, J = 14.1 Hz, 1H), 5.11 (dd, J = 26.2, 14.9 Hz, 1H), 4.79-4.65 (m, 1H), 4.27-4.12 (m, 1H), 4.08 (s, 3H), 3.99 (s, 3H), 3.70 (br 2, 1H), 3.53 (br s, 1H), 3.45-3.36 (m, 1H), 3.36 (s, 1H), 2.28-2.05 (m, 1H), 2.01-1.86 (m, 4H), 1.80-1.70 (m, 1H), 1.63-1.51 (m, 1H), 1.59 (d, J = 7.4 Hz, 3H), 1.40-1.29 (m, 1H), 1.04-0.95 (m, 1H), 0.97-0.78 (m, 1H), 0.71-0.60 (m, 1H). |
| 868 | 704.3 | 1H NMR (400 MHz, DMSO-d6) δ 8.06 (d, J = 8.1 Hz, 1H), 7.97 (s, 4H), 7.45 (s, 1H), 7.25 (d, J = 8.1 Hz, 1H), 7.11 (s, 1H), 6.94 (s, 1H), 5.89 (q, J = 7.4 Hz, 1H), 5.43 (t, J = 14.3 Hz, 1H), 5.06 (dd, J = 25.6, 14.8 Hz, 1H), 4.20 (dd, J = 16.2, 5.7 Hz, 1H), 4.07 (s, 3H), 3.99 (s, 4H), 3.70 (br s, 1H), 3.59-3.38 (m, 5H), 3.36 (s, 3H), 2.35-1.83 (m, 5H), 1.81-1.71 (m, 1H), 1.60 (d, J = 7.5 Hz, 3H), 1.63-1.51 (m, 1H), 1.42-1.28 (m, 1H), 1.22-1.11 (m, 1H), 0.98 (t, J = 5.3 Hz, 1H), 0.91-0.80 (m, 1H), 0.72-0.63 (m, 2H), 0.61-0.55 (m, 2H), 0.47-0.39 (t, J = 5.7 Hz, 2H). |
| 869 | 697.3 | 1H NMR (400 MHz, DMSO-d6) δ 8.66 (d, J = 4.8 Hz, 1H), 8.31 (d, J = 7.1 Hz, 1H), 8.07 (d, J = 8.0 Hz, 1H), 7.98 (s, 3H), 7.92 (td, J = 7.8, 1.6 Hz, 1H), 7.58 (d, J = 7.9 Hz, 1H), 7.48-7.42 (m, 2H), 7.21 (d, J = 8.1 Hz, 1H), 7.05 (s, 1H), 6.93 (s, 1H), 5.08 (p, J = 7.0 Hz, 1H), 4.87-4.78 (m, 1H), 4.41 (d, J = 10.8 Hz, 1H), 4.13 (s, 3H), 3.99 (s, 3H), 3.71 (brs, 1H), 3.55 (br s, 2H), 3.37 (s, 3H), 2.81 (dt, J = 41.9, 12.5 Hz, 1H), 2.19-1.90 (m, 3H), 1.81-1.65 (m, 3H), 1.52-1.35 (m, 2H), 1.43 (d, J = 7.0 Hz, 3H), 1.33-1.15 (m, 3H). |
| 870 | 697.3 | 1H NMR (400 MHz, DMSO-d6) δ 8.70 (dd, J = 8.5, 3.4 Hz, 1H), 8.60 (d, J = 4.8 Hz, 1H), 8.09 (d, J = 8.1 Hz, 1H), 7.98 (s, 3H), 7.90 (td, J = 7.8, 1.7 Hz, 1H), 7.61 (d, J = 8.0 Hz, 1H), 7.48-7.40 (m, 2H), 7.24 (d, J = 8.1 Hz, 1H), 7.07 (s, 1H), 6.94 (s, 1H), 5.27 (p, J = 7.3 Hz, 1H), 4.89 (dt, J = 14.7, 7.9 Hz, 1H), 4.63-4.54 (m, 1H), 4.12 (s, 3H), 3.99 (s, 3H), 3.70 (br s, 1H), 3.54 (br s, 2H), 3.37 (s, 3H), 2.70-2.58 (m, 1H), 2.16-1.89 (m, 3H), 1.81-1.62 (m, 2H), 1.55 (d, J = 7.1 Hz, 3H), 1.46-1.33 (m, 1H), 1.32-1.06 (m, 3H). |
| 871 | 693.4 | 1H NMR (400 MHz, DMSO-d6) δ 8.91 (d, J = 8.6 Hz, 1H), 8.60-8.56 (m, 1H), 8.08 (d, J = 8.1 Hz, 1H), 8.05-7.92 (d, J = 7.5 Hz, 4H), 7.69 (s, 1H), 7.65 (d, J = 8.0 Hz, 1H), 7.44 (t, J = 6.4 Hz, 1H), 7.32-7.27 (m, 2H), 7.21 (d, J = 8.2 Hz, 1H), 5.27-5.17 (m, 1H), 5.17-5.08 (m, 1H), 4.85-4.75 (m, 1H), 4.18 (dd, J = 12.7, 3.7 Hz, 1H), 4.05-3.98 (m, 1H), 3.75-3.67 (m, 1H), 3.55 (br s, 2H), 3.40 (br s, 2H), 3.36 (s, 3H), 2.21 (br s, 1H), 2.12-2.03 (m, 1H), 1.92 (br s, 1H), 1.82-1.71 (m, 2H), 1.68-1.50 (m, 1H), 1.42 (d, J = 7.1 Hz, 3H), 1.45-1.34 (m, 2H), 1.27-0.95 (m, 4H), 0.62-0.45 (m, 2H). |
| 872 | 727.3 | 1H NMR (400 MHz, DMSO-d6) δ 8.89 (d, J = 8.6 Hz, 1H), 8.07 (d, J = 8.1 Hz, 1H), 7.97 (s, 3H), 7.83 (t, J = 7.8 Hz, 1H), 7.69 (s, 1H), 7.52 (d, J = 7.6 Hz, 1H), 7.39 (dd, J = 7.9, 0.8 Hz, 1H), 7.32-7.26 (m, 2H), 7.20 (d, J = 8.1 Hz, 1H), 5.27-5.07 (m, 2H), 4.84-4.73 (m, 1H), 4.11-3.97 (m, 2H), 3.70 (br s, 1H), 3.56 (br s, 1H), 3.41 (br s, 1H), 3.36 (s, 3H), 2.20 (br s, 1H), 2.07-1.87 (m, 1H), 1.82-1.72 (m, 1H), 1.62-1.49 (m, 2H), 1.45-1.31 (m, 2H), 1.42 (d, J = 7.1 Hz, 3H), 1.27-0.90 (m, 7H), 0.60-0.44 (m, 2H). |
| 873 | 727.3 | 1H NMR (400 MHz, DMSO-d6) δ 8.89 (d, J = 8.6 Hz, 1H), 8.07 (d, J = 8.1 Hz, 1H), 7.97 (s, 3H), 7.83 (t, J = 7.8 Hz, 1H), 7.69 (s, 1H), 7.52 (d, J = 7.6 Hz, 1H), 7.39 (dd, J = 7.9, 0.8 Hz, 1H), 7.32-7.26 (m, 2H), 7.20 (d, J = 8.1 Hz, 1H), 5.27-5.07 (m, 2H), 4.84-4.73 (m, 1H), 4.11-3.97 (m, 2H), 3.70 (br s, 1H), 3.56 (br s, 1H), 3.41 (br s, 1H), 3.36 (s, 3H), 2.20 (br |

TABLE 3-continued

| Example | ES/MS m/z [M + H]+ | ¹H NMR |
|---|---|---|
| | | s, 1H), 2.07-1.87 (m, 1H), 1.82-1.72 (m, 1H), 1.62-1.49 (m, 2H), 1.45-1.31 (m, 2H), 1.42 (d, J = 7.1 Hz, 3H), 1.27-0.90 (m, 7H), 0.60-0.44 (m, 2H). |
| 874 | 630.3 | 1H NMR (400 MHz, DMSO-d6) δ 8.45 (d, J = 8.5 Hz, 1H), 8.00 (d, J = 8.0 Hz, 1H), 7.98 (br s, 3H), 7.68 (s, 1H), 7.28 (d, J = 11.4 Hz, 1H), 7.25 (s, 1H), 7.14 (d, J = 8.1 Hz, 1H), 5.05-4.96 (m, 1H), 4.02-3.96 (m, 1H), 3.81 (br s, 1H), 3.73-3.67 (m, 1H), 3.55 (br s, 1H), 3.38 (br s, 1H), 3.36 (s, 3H), 1.99-1.46 (m, 7H), 1.44 (d, J = 7.1 Hz, 3H), 1.40-1.04 (m, 3H), 0.98-0.82 (m, 2H), 0.77-0.55 (m, 2H), 0.52-0.45 (m, 1H). |
| 875 | 745.2 | 1H NMR (400 MHz, DMSO-d6) δ 8.81 (dd, J = 8.3, 3.1 Hz, 1H), 8.10 (d, J = 8.1 Hz, 1H), 7.98 (t, J = 7.8 Hz, 1H), 7.97 (br s, 3H), 7.70 (s, 1H), 7.64 (d, J = 7.7 Hz, 1H), 7.57 (d, J = 7.9 Hz, 1H), 7.32-7.22 (m, 3H), 5.26 (p, J = 7.4 Hz, 1H), 5.00-4.90 (m, 1H), 4.83-4.72 (m, 1H), 4.04-3.98 (m, 1H), 3.82 (br s, 1H), 3.70 (br s, 1H), 3.56 (br s, 1H), 3.40 (s, 2H), 3.36 (s, 3H), 2.13-1.87 (m, 2H), 1.76 (s, 1H), 1.55 (d, J = 7.1 Hz, 3H), 1.44-1.03 (m, 4H), 0.94 (br s, 1H), 0.82 (br s, 1H), 0.61-0.53 (m, 1H). |
| 876 | 745.2 | 1H NMR (400 MHz, DMSO-d6) δ 8.81 (d, J = 8.7 Hz, 0H), 8.38 (d, J = 7.2 Hz, 1H), 8.09 (d, J = 8.1 Hz, 1H), 7.99 (t, J = 7.8 Hz, 1H), 7.98 (br s, 3H), 7.70 (s, 1H), 7.59 (d, J = 7.8 Hz, 2H), 7.32-7.20 (m, 3H), 5.10 (p, J = 7.0 Hz, 1H), 4.96-4.85 m, 1H), 4.62 (s, 1H), 4.04-3.97 (m, 1H), 3.82 (br s, 1H), 3.70 (br s, 1H), 3.56 (br s, 1H), 3.40 (br 2s, 1H), 3.36 (s, 3H), 2.86-2.66 (m, 1H), 2.23-1.85 (m, 3H), 1.73 (d, J = 29.1 Hz, 3H), 1.47 (d, J = 7.1 Hz, 3H), 1.35-1.03 (m, 3H), 0.91 (br s, 1H), 0.69-0.61 (m, 1H). |
| 877 | 680.3 | 1H NMR (400 MHz, DMSO-d6) δ 9.25 (d, J = 6.9 Hz, 1H), 8.60 (d, J = 2.5 Hz, 1H), 8.50 (d, J = 2.5 Hz, 1H), 8.11 (dd, J = 8.1, 1.2 Hz, 1H), 7.99 (br s, 2H), 7.74 (br s, 1H), 7.63 (d, J = 4.8 Hz, 0.3H), 7.55 (br s, 0.7H), 7.36-7.26 (m, 2H), 5.23 (p, J = 7.0 Hz, 1H), 5.05 (br s, 0.3H), 4.95-4.74 (m, 2H), 4.61 (dd, J = 13.4, 6.1 Hz, 0.7H), 4.08-3.96 (m, 2H), 3.59 (br s, 0.3H), 3.37 (br s, 0.7H), 3.25 (br s, 0.3H), 3.06 (t, J = 12.0 Hz, 0.3H), 2.77 (t, J = 12.3 Hz, 0.7H), 2.72-2.62 (m, 0.7H), 2.46-2.30 (m, 2H), 2.03-1.92 (m, 2H), 1.88-1.34 (m, 4H), 1.51 (d, J = 7.1 Hz, 3H), 1.32-1.03 (m, 4H), 0.66-0.44 (m, 2H). |
| 878 | 707.3 | 1H NMR (400 MHz, DMSO-d6) δ 9.01 (d, J = 7.2 Hz, 1H), 8.07 (d, J = 8.0 Hz, 1H), 8.00 (br s, 2H), 7.77 (br s, 1H), 7.72 (d, J = 8.1 Hz, 1H), 7.69-7.56 (m, 1H), 7.37-7.18 (m, 3H), 7.19 (s, 1H), 5.18 (p, J = 7.0 Hz, 1H), 4.98 (br s, 0.5H), 4.75 (dd, J = 14.2, 5.1 Hz, 1H), 4.53 (br s, 0.5H), 4.29 (dd, J = 14.3, 7.8 Hz, 1H), 4.16 (br s, 0.5H), 3.95 (br s, 0.5H), 3.75 (br s, 0.5H), 3.43-3.07 (m, 1H), 2.80 (ddd, J = 14.5, 10.3, 4.1 Hz, 1H), 2.45-2.30 (m, 1H), 2.10-1.89 (m, 2H), 1.89-1.44 (m, 5H), 1.64 (d, J = 7.0 Hz, 3H), 1.17-0.99 (m, 3H), 0.77 (br s, 4H), 0.46-0.36 (m, 2H). |
| 879 | 707.3 | 1H NMR (400 MHz, DMSO-d6) δ 9.15 (d, J = 6.9 Hz, 1H), 8.08 (d, J = 8.0 Hz, 1H), 7.99 (br s, 2H), 7.84 (d, J = 8.1 Hz, 1H), 7.79-7.56 (m, 2H), 7.41 (d, J = 8.0 Hz, 1H), 7.30-7.18 (m, 3H), 5.16 (p, J = 7.0 Hz, 1H), 4.98 (s, 0.5H), 4.87 (br s, 1H), 4.53 (br s, 0.5H), 4.17 (br s, 0.5H), 4.04-3.96 (m, 1H), 3.89 (dd, J = 14.1, 9.1 Hz, 1H), 3.75 (br s, 0.5 H), 3.42-3.04 (m, 1H), 2.83-2.55 (m, 2H), 2.06-1.44 (m, 5H), 1.50 (d, J = 7.0 Hz, 3H), 1.20-0.94 (m, 6H), 0.81 (br s, 2H), 0.41-0.31 (m, 1H), 0.31-0.22 (m, 1H). |
| 880 | 660.3 | 1H NMR (400 MHz, DMSO-d6) δ 8.67 (d, J = 7.1 Hz, 1H), 8.05 (d, J = 8.2 Hz, 1H), 7.99 (br s, 2H), 7.83-7.55 (m, 2H), 7.33-7.17 (m, 3H), 4.98 (s, 0.5H), 4.93-4.84 (m, 1H), 4.70-4.60 (m, 1H), 4.57-4.41 (m, 1H), 4.46 (p, J = 7.2 Hz, 1H), 4.18 (br s, 0.5H), 3.99 (br s, 1H), 3.43-3.07 (m, 2H), 2.76 (br s, 0.5H), 2.41-2.29 (m, 1H), 1.76 (d, J = 7.1 Hz, 3H), 2.22-1.47 (m, 7H), 1.44-1.25 (m, 1H), 1.12 (br s, 2H), 0.95-0.76 (m, 3H), 0.76-0.60 (m, 2H). |
| 881 | 660.3 | 1H NMR (400 MHz, DMSO-d6) δ 8.62 (d, J = 8.5 Hz, 1H), 8.02 (d, J = 8.0 Hz, 3H), 7.97 (br s, 2H), 7.78-7.57 (m, 2H), 7.29 (s, 1H), 7.23 (br s, 2H), 7.17 (d, J = 8.1 Hz, 1H), 5.03 (p, J = 7.2 Hz, 1H), 4.96-4.78 (m, 2H), 4.66-4.56 (m, 1H), 4.56 (br s, 0.5H), 4.16 (br s, 0.5H), 4.04-3.95 (m, 1H), 2.44-2.29 (m, 1H), 2.06-1.48 (m, 6H), 1.45 (d, J = 7.1 Hz, 3H), 1.42-1.20 (m, 1H), 1.18-1.06 (m, 2H), 0.97-0.59 (m, 6H). |
| 882 | 624.4 | 1H NMR (400 MHz, DMSO-d6) δ 8.46 (d, J = 8.5 Hz, 1H), 8.09-7.53 (m, 5H), 7.30-7.17 (m, 2H), 7.14 (d, J = 8.0 Hz, 1H), 5.00 (p, J = 7.2 Hz, 1H), 4.89-4.72 (m, 2H), 4.52 (br s, 0.5H), 4.17 (br s, 0, 5H), 3.99 (tt, J = 7.2, 3.8 Hz, 1H), 3.75 (br, 0.5H), 3.43-3.02 (m, 2H), 2.77 (br s, 0.5H), 1.44 (d, J = 7.1 Hz, 3H), 2.03-0.80 (m, 15H), 0.80-0.43 (m, 4H). |
| 883 | 693.4 | 1H NMR (400 MHz, DMSO-d6) δ 8.66 (d, J = 4.8 Hz, 1H), 8.31 (d, J = 7.1 Hz, 1H), 8.07 (d, J = 8.0 Hz, 1H), 7.99 (br s, 2H), 7.92 (dd, J = 8.8, 7.1 Hz, 1H), 7.76 (br s, 1H), 7.58 (d, J = 7.9 Hz, 1H), 7.45 (dd, J = 7.6, 4.9 Hz, 1H), 7.38 (s, 1H), 7.21 (d, J = 8.1 Hz, 1H), 7.04 (s, 1H), 6.90 (s, 1H), 5.07 (p, J = 7.0 Hz, 1H), 5.00 (br s, 0.6H), 4.83 (t, J = 12.0 Hz, 1H), 4.54 (br s, 0.4H), 4.47-4.36 (m, 1H), 4.24 (br s, 0.4H), 4.13 (s, 3H), 3.99 (s, 3H), 3.45-3.03 (m, 1H), 2.80 (dt, J = 41.9, 12.7 Hz, 1H), 2.19-1.91 (m, 2H), 1.89-1.52 (m, 7H), 1.43 (d, J = 7.0 Hz, 3H), 1.52-1.12 (m, 2H). |

TABLE 3-continued

| Example | ES/MS m/z [M + H]+ | 1H NMR |
|---|---|---|
| 884 | 693.4 | 1H NMR (400 MHz, DMSO-d6) δ 8.70 (dd, J = 9.0, 3.3 Hz, 1H), 8.60 (d, J = 4.9 Hz, 1H), 8.08 (d, J = 8.1 Hz, 1H), 7.98 (br s, 3H), 7.90 (td, J = 7.8, 1.8 Hz, 1H), 7.76 (br s, 1H), 7.61 (d, J = 8.0 Hz, 1H), 7.45-7.35 (m, 2H), 7.24 (d, J = 8.1 Hz, 1H), 7.07 (s, 1H), 6.90 (s, 1H), 5.27 (p, J = 7.4 Hz, 1H), 4.99 (br s, 0.4H), 4.89 (dt, J = 14.5, 7.7 Hz, 1H), 4.66-4.46 (m, 1.6H), 4.23 (br s, 0.4H), 4.12 (s, 3H), 3.99 (s, 3H), 3.46-3.04 (m, 1.6H), 2.77 (s, 0.4H), 2.17-1.44 (m, 7H), 1.55 (d, J = 7.1 Hz, 3H), 1.45-1.05 (m, 4H), 0.76 (br s, 1H). |
| 885 | 707.4 | 1H NMR (400 MHz, DMSO-d6) δ 8.66 (d, J = 4.8 Hz, 1H), 8.33 (d, J = 7.0 Hz, 1H), 8.08 (d, J = 8.1 Hz, 1H), 8.01 (br s, 2H), 7.95-7.89 (m, 1H), 7.86-7.55 (m, 2H), 7.45 (dd, J = 7.6, 4.8 Hz, 1H), 7.31-7.17 (m, 3H), 5.07 (p, J = 7.0 Hz, 1H), 4.92 (t, J = 11.5 Hz, 1H), 4.64 (br s, 1H), 4.53 (br s, 0.5H), 4.18 (br s, 1H), 4.04-3.97 m, 1H),  2.81 (dt, J = 42.2, 13.0 Hz, 1H), 2.20-1.34 (m, 11H), 1.44 (d, J = 7.1 Hz, 3H), 1.34-1.03 (m, 2H), 0.94 (br s, 1H), 0.62 (br s, 1H). |
| 886 | 707.4 | 1H NMR (400 MHz, DMSO-d6) δ 8.76-8.69 (m, 1H), 8.60 (d, J = 4.8 Hz, 1H), 8.09 (d, J = 8.1 Hz, 1H), 7.99 (br s, 2H), 7.90 (td, J = 7.7, 1.6 Hz, 1H), 7.95-7.58 (m, J = 34.1 Hz, 2H), 7.62 (d, J = 7.9 Hz, 1H), 7.42 (dd, J = 7.5, 4.9 Hz, 1H), 7.32-7.18 (m, 3H), 5.27 (p, J = 7.3 Hz, 1H), 5.02-4.02 (m, 1.5H), 4.84-4.73 (m, 1H), 4.52 (br s, 0.5H), 4.18 (br s, 0.5H), 4.05-3.97 (m, 1.5H), 3.77 (br s, 0.5H), 3.43-3.07 (m, 1.5H), 2.84-2.58 (m, 1H), 2.18-1.45 (m, 6H), 1.55 (d, J = 7.1 Hz, 3H), 1.43-1.02 (m, 6H), 0.96 (br s, 1H), 0.78 (br s, 1H), 0.55 (br s, 1H). |
| 887 | 727.3 | 1H NMR (400 MHz, DMSO-d6) δ 8.83-8.75 (m, 1H), 8.08 (d, J = 8.0 Hz, 1H), 7.97 (t, J = 7.8 Hz, 2H), 8.03-7.67 (m, 2H), 7.63 (d, J = 7.7 Hz, 1H), 7.57 (d, J = 7.9 Hz, 1H), 7.38 (s, 1H), 7.24 (d, J = 8.1 Hz, 1H), 7.07 (s, 1H), 6.90 (s, 1H), 5.27 (p, J = 7.2 Hz, 1H), 4.99 (br s, 0.5H), 4.87 (dt, J = 14.4, 7.8 Hz, 1H), 4.65-4.48 (m, 1.5H), 4.23 (br s, 0.5H), 4.12 (s, 3H), 3.99 (s, 3H), 3.44-3.04 (m, 2H), 2.77 (br s, 0.5H), 2.11-1.45 (m, 5H), 1.54 (d, J = 7.1 Hz, 3H), 1.43-1.05 (m, 5H), 0.78 (brs, 1H). |
| 888 | 727.3 | 1H NMR (400 MHz, DMSO-d6) δ 8.37 (d, J = 7.3 Hz, 1H), 8.07 (d, J = 8.1 Hz, 1H), 7.99 (t, J = 7.9 Hz, 1H), 7.75 (br s, 1H), 7.60 (s, 1H), 7.58 (s, 1H), 7.38 (br s, 2H), 7.22 (d, J = 8.1 Hz, 1H), 7.04 (s, 1H), 6.90 (s, 1H), 5.10 (p, J = 7.1 Hz, 1H), 5.00 (br s, 0.5H), 4.82 (t, J = 12.0 Hz, 1H), 4.63-4.36 (m, 2H), 4.24 (br s, 1H), 4.13 (s, 3H), 3.99 (s, 3H), 3.44-3.04 (m, 2H), 2.85-2.64 (m, 2H), 2.23-1.33 (m, 6H), 1.46 (d, J = 7.1 Hz, 3H), 1.33-1.14 (s, 3H). |
| 889 | 725.3 | 1H NMR (400 MHz, DMSO-d6) δ 8.53 (ddd, J = 4.9, 1.9, 0.9 Hz, 1H), 8.44 (d, J = 7.1 Hz, 1H), 8.09 (d, J = 8.1 Hz, 1H), 8.05-7.68 (m, 3H), 7.73 (td, J = 7.8, 1.9 Hz, 1H), 7.43-7.23 (m, 4H), 7.04 (s, 1H), 6.89 (s, 1H), 6.69 (t, J = 55.5 Hz, 1H), 5.18 (p, J = 6.9 Hz, 1H), 4.99 (br s, 0.5H), 4.82-4.72 (m, 1H), 4.60-4.42 (m, 1H), 4.23 (br s, 0.5H), 4.11 (s, 3H), 3.98 (s, 3H), 3.45-3.05 (m, 1.5H), 2.76 (br s, 0.5H), 2.46-2.22 (m, 2H), 2.05-1.21 (m, 11H), 1.57 (d, J = 7.0 Hz, 3H), 1.22-0.97 (m, 2H). |
| 890 | 725.3 | 1H NMR (400 MHz, DMSO-d6) δ 8.61 (ddd, J = 4.8, 1.9, 0.9 Hz, 1H), 8.24 (d, J = 7.1 Hz, 1H), 8.06 (d, J = 8.1 Hz, 1H), 8.09-7.71 (m, 3H), 7.85 (td, J = 7.7, 1.9 Hz, 1H), 7.47 (d, J = 8.0 Hz, 1H), 7.37 (ddd, J = 7.5, 4.8, 1.0 Hz, 1H), 7.21 (d, J = 8.2 Hz, 1H), 7.04 (s, 1H), 6.90 (s, 1H), 6.47 (t, J = 55.2 Hz, 1H), 5.20 (p, J = 7.0 Hz, 1H), 5.00 (s, 0.5H), 4.83 (t, J = 10.2 Hz, 1H), 4.61-4.35 (m, 1.5H), 4.23 (br s, 0.5H), 4.11 (s, 3H), 3.99 (s, 3H), 3.45-3.03 (m, 1.5H), 2.77 (br s, 0.5H), 2.55-2.38 (m, 2H), 2.03-1.23 (m, 13H), 1.33 (d, J = 7.0 Hz, 3H), 1.00 (br s, 1H). |
| 891 | 675.3 | 1H NMR (400 MHz, DMSO-d6) δ 8.90 (d, J = 8.6 Hz, 1H), 8.58 (d, J = 5.1 Hz, 1H), 8.07 (d, J = 8.1 Hz, 1H), 8.03-7.69 (m, 4H), 7.66 (d, J = 8.3 Hz, 1H), 7.44 (s, 1H), 7.38 (s, 1H), 7.21 (d, J = 8.1 Hz, 1H), 7.07 (s, 1H), 6.90 (s, 1H), 5.22 (p, J = 7.2 Hz, 1H), 5.11-4.95 (m, 1.5H), 4.66-4.46 (m, 1.5H), 4.29-4.14 (m, 1.5H), 4.12 (s, 3H), 3.99 (s, 3H), 3.45-3.04 (m, 1.5H), 2.77 (br s, 0.5H), 2.21 (br s, 0.5H), 2.13-1.30 (m, 9H), 1.41 (d, J = 7.0 Hz, 3H), 1.21-0.90 (m, 3H), 0.53 (br s, 1H). |
| 892 | 675.3 | 1H NMR (400 MHz, DMSO-d6) δ 8.61-8.57 (m, 1H), 8.29 (d, J = 7.4 Hz, 1H), 8.07 (d, J = 8.1 Hz, 1H), 8.02-7.65 (m, 5H), 7.53 (d, J = 7.9 Hz, 1H), 7.41-7.34 m, 2.5H), 7.21 (d, J = 8.1 Hz, 1H), 7.05 (s, 1H), 6.90 (s, 1.5H), 5.11 (p, J = 7.1 Hz, 1H), 4.98 (brs, 0.5H), 4.85-4.75 (m, 1H), 4.61-4.39 (m, 1.5H), 4.24 (br s, 1H), 4.13 (s, 3H), 3.99 (s, 3H), 3.65 (dd, J = 12.6, 3.6 Hz, 1H), 3.45-3.04 (m, 1.5H), 2.76 (br s, 0.5H), 2.37-2.30 (m, 1H), 2.05-1.29 (m, 15H), 1.46 (d, J = 7.1 Hz, 3H), 1.29-1.15 (m, 2H). |
| 893 | 658.6 | 1H NMR (400 MHz, DMSO-d6) δ 8.84 (d, J = 7.1 Hz, 1H), 8.06 (d, J = 8.1 Hz, 1H), 8.04-7.93 (m, 2H), 7.77 (s, 1H), 7.42-7.33 (m, 1H), 7.33-7.24 (m, 3H), 7.20-7.09 (m, 1H), 7.00 (s, 1H), 6.90 (s, 1H), 6.78 (d, J = 7.8 Hz, 1H), 5.20 (p, J = 7.0 Hz, 1H), 5.07-4.93 (m, 0.4H), 4.66-4.58 (m, 1H), 4.56-4.48 (m, 0.5H), 4.47-4.34 (m, 1H), 4.29-4.17 (m, 0.5H), 4.08 (s, 3H), 3.99 (s, 3H), 3.87-3.76 (m, 0.3H), 3.46-3.22 (m, 1H), 3.21-3.03 (m, 0.4H), 2.81-2.75 (m, 0.5H), 2.61-2.54 (m, 1H), 2.04-1.92 (m, 1H), 1.89-1.73 (m, 3H), 1.73-1.45 (m, 7H), 1.12-1.01 (m, 1H), 0.80-0.69 (m, 1H), 0.61-0.47 (m, 1H), 0.36-0.19 (m, 1H). |

TABLE 3-continued

| Example | ES/MS m/z [M + H]+ | 1H NMR |
|---|---|---|
| 894 | 682.6 | 1H NMR (400 MHz, DMSO-d6) δ 9.08 (d, J = 7.1 Hz, 1H), 8.09 (d, J = 8.0 Hz, 1H), 8.06-7.67 (m, 3H), 7.43-7.33 (m, 1H), 7.31-7.21 (m, 2H), 7.11 (d, J = 14.7 Hz, 2H), 6.90 (s, 1H), 5.20 (p, J = 7.0 Hz, 1H), 4.99 (s, 0.2H), 4.92-4.80 (m, 1H), 4.67-4.58 (m, 1H), 4.58-4.48 (m, 0.4H), 4.27-4.20 (m, 1H), 4.12 (s, 3H), 4.00 (s, 3H), 3.45-3.20 (m, 1H), 3.17-3.10 (m, 0.2H), 2.82-2.74 (m, 0.4H), 2.46-2.27 (m, 2H), 2.21-2.12 (m, 1H), 2.03-1.92 (m, 1H), 1.88-1.73 (m, 1H), 1.63 (s, 5H), 1.52-1.38 (m, 4H), 1.30-1.11 (m, 2H), 0.54-0.40 (m, 1H). |
| 895 | 713.8 | 1H NMR (400 MHz, DMSO-d6) δ 9.27 (d, J = 6.8 Hz, 1H), 8.04 (d, J = 10.4 Hz, 1H), 7.99 (s, 2H), 7.85 (d, J = 8.1 Hz, 1H), 7.82-7.71 (m, 1H), 7.70-7.55 (m, 1H), 7.43 (d, J = 8.0 Hz, 1H), 7.32 (s, 1H), 7.30-7.19 (m, 1H), 5.48-5.35 (m, 1H), 5.02-4.91 (m, 0.5H), 4.93-4.76 (m, 2H), 4.56-4.48 (s, 0.5H), 4.23-4.12 (m, 0.5H), 4.08-3.97 (m, 1H), 3.84-3.68 (m, 0.3H), 3.45-3.21 (m, 1H), 3.20-3.07 (m, 0.3H), 2.82-2.72 (m, 0.5H), 2.71-2.62 (m, 1H), 2.41-2.29 (m, 2H), 2.03-1.91 (m, 1H), 1.90-1.74 (m, 1H), 1.65 (s, 5H), 1.55-1.42 (m, 4H), 1.42-1.30 (m, 1H), 1.29-1.14 (m, 0H), 1.13-0.99 (m, 2H), 0.61-0.34 (m, 2H). |
| 896 | 696.2 | 1H NMR (400 MHz, DMSO-d6) δ 8.97 (d, J = 7.0 Hz, 1H), 8.08 (d, J = 8.0 Hz, 1H), 7.84 (d, J = 91.2 Hz, 3H), 7.52-7.30 (m, 4H), 7.25 (d, J = 8.1 Hz, 1H), 7.18-6.98 (m, 2H), 6.89 (s, 1H), 5.20 (p, J = 7.1 Hz, 1H), 5.06-4.92 (m, 0.5H), 4.92-4.78 (m, 1H), 4.68-4.46 (m, 1.5H), 4.29-4.19 (m, 0.5H), 4.11 (s, 3H), 3.99 (s, 3H), 3.44-2.99 (m, 1.5H), 2.86-2.66 (m, 0.5H), 2.47-2.23 (m, 3H), 2.06-1.35 (m, 12H), 1.35-1.06 (m, 2H), 0.62-0.41 (m, 1H). |
| 897 | 682.2 | 1H NMR (400 MHz, DMSO-d6) δ 9.32 (d, J = 7.2 Hz, 1H), 8.08 (d, J = 8.0 Hz, 1H), 8.05-7.62 (m, 3H), 7.42-7.29 (m, 2H), 7.26 (d, J = 8.1 Hz, 1H), 7.09 (s, 1H), 7.05 (dd, J = 8.5, 4.5 Hz, 1H), 6.89 (s, 1H), 5.27 (p, J = 7.0 Hz, 1H), 5.05-4.95 (m, 0.5H), 4.95-4.81 (m, 1H), 4.68-4.46 (m, 1.5H), 4.28-4.18 (m, 0.5H), 4.11 (s, 3H), 3.99 (s, 3H), 3.87-3.75 (m, 0.5H), 3.47-3.01 (m, 1.5H), 2.85-2.68 (m, 0.5H), 2.48-2.38 (m, 1H), 2.31-2.08 (m, 2H), 2.04-1.33 (m, 12H), 1.33-1.06 (m, 2H), 0.48-0.31 (m, 1H). |
| 898 | 698.2 | 1H NMR (400 MHz, DMSO-d6) δ 9.05 (d, J = 7.1 Hz, 1H), 8.08 (d, J = 8.0 Hz, 1H), 8.03-7.62 (m, 3H), 7.54-7.43 (m, 1H), 7.36 (s, 1H), 7.28-7.20 (m, 2H), 7.08 (s, 1H), 6.89 (s, 1H), 5.20 (p, J = 6.9 Hz, 1H), 5.07-4.92 (m, 0.5H), 4.91-4.78 (m, 1H), 4.68-4.45 (m, 1.5H), 4.28-4.17 (m, 0.5H), 4.12 (s, 3H), 3.99 (s, 3H), 3.87-3.73 (m, 0.5H), 3.46-3.04 (m, 1.5H), 2.86-2.69 (m, 0.5H), 2.44-2.18 (m, 2H), 2.05-1.36 (m, 12H), 1.36-1.09 (m, 2H), 0.58-0.40 (m, 1H). |
| 899 | 664.3 | 1H NMR (400 MHz, DMSO-d6) δ 8.93 (d, J = 6.8 Hz, 1H), 8.07 (d, J = 8.0 Hz, 1H), 8.04-7.63 (m, 3H), 7.36 (s, 1H), 7.28-7.19 (m, 2H), 7.19-7.11 (m, 2H), 7.07 (s, 1H), 6.89 (s, 1H), 5.16 (p, J = 7.0 Hz, 1H), 5.07-4.91 (m, 0.5H), 4.91-4.79 (m, 1H), 4.68-4.45 (m, 1.5H), 4.29-4.17 (m, 0.5H), 4.11 (s, 3H), 3.99 (s, 3H), 3.87-3.71 (m, 0.5H), 3.48-3.02 (m, 1.5H), 2.86-2.69 (m, 0.5H), 2.47-2.28 (m, 2H), 2.28-2.16 (m, 1H), 2.05-1.31 (m, 12H), 1.31-1.06 (m, 2H), 0.58-0.43 (m, 1H). |
| 900 | 664.3 | 1H NMR (400 MHz, DMSO-d6) δ 8.86 (d, J = 6.9 Hz, 1H), 8.07 (d, J = 8.1 Hz, 1H), 8.04-7.63 (m, 3H), 7.45-7.31 (m, 2H), 7.24 (d, J = 8.1 Hz, 1H), 7.11-7.02 (m, 3H), 6.89 (s, 1H), 5.16 (p, J = 7.0 Hz, 1H), 5.03-4.92 (m, 0.5H), 4.90-4.78 (m, 1H), 4.68-4.45 (m, 1.5H), 4.27-4.17 (m, 0.5H), 4.11 (s, 3H), 3.99 (s, 3H), 3.89-3.74 (m, 0.5H), 3.45-3.04 (m, 1.5H), 2.84-2.69 (m, 0.5H), 2.44-2.18 (m, 2H), 2.04-1.34 (m, 12H), 1.34-1.07 (m, 2H), 0.61-0.44 (m, 1H). |
| 901 | 680.2 | 1H NMR (400 MHz, DMSO-d6) δ 8.92 (d, J = 6.9 Hz, 1H), 8.07 (d, J = 8.0 Hz, 1H), 8.03-7.63 (m, 3H), 7.42-7.32 (m, 2H), 7.32-7.27 (m, 2H), 7.24 (d, J = 8.1 Hz, 1H), 7.07 (s, 1H), 6.89 (s, 1H), 5.17 (p, J = 6.9 Hz, 1H), 5.05-4.92 (m, 0.5H), 4.91-4.79 (m, 1H), 4.68-4.46 (m, 1.5H), 4.29-4.16 (m, 0.5H), 4.11 (s, 3H), 3.99 (s, 3H), 3.87-3.72 (m, 0.5H), 3.45-3.03 (m, 1.5H), 2.84-2.69 (m, 0.5H), 2.47-2.18 (m, 3H), 2.03-1.33 (m, 12H), 1.33-1.06 (m, 2H), 0.62-0.42 (m, 1H). |
| 902 | 664.3 | 1H NMR (400 MHz, DMSO-d6) δ 9.18 (d, J = 7.4 Hz, 1H), 8.08 (d, J = 8.0 Hz, 1H), 8.04-7.65 (m, 3H), 7.44-7.27 (m, 2H), 7.25 (d, J = 8.1 Hz, 1H), 7.11-7.00 (m, 3H), 6.90 (s, 1H), 5.27 (p, J = 7.1 Hz, 1H), 5.07-4.83 (m, 1.5H), 4.69-4.46 (m, 1.5H), 4.28-4.17 (m, 0.5H), 4.11 (s, 3H), 3.99 (s, 3H), 3.89-3.74 (m, 0.5H), 3.47-3.00 (m, 1.5H), 2.86-2.67 (m, 0.5H), 2.31-2.13 (m, 2H), 2.06-1.33 (m, 12H), 1.33-1.10 (m, 2H), 0.49-0.32 (m, 1H). |
| 903 | 682.3 | 1H NMR (400 MHz, DMSO-d6) δ 9.32 (d, J = 7.5 Hz, 1H), 8.08 (d, J = 8.0 Hz, 1H), 8.05-7.64 (m, 3H), 7.36 (br. s, 1H), 7.26 (d, J = 8.1 Hz, 1H), 7.22 (td, J = 9.1, 4.5 Hz, 1H), 7.15 (ddd, J = 9.0, 8.3, 4.0 Hz, 1H), 7.09 (s, 1H), 6.90 (s, 1H), 5.29 (p, J = 7.1 Hz, 1H), 5.02-4.97 (m, 0.5H), 4.95-4.84 (m, 1H), 4.62 (d, J = 13.4 Hz, 1H), 4.56-4.51 (m, 0.5H), 4.31-4.15 (m, 0.5H), 4.12 (s, 3H), 3.99 (s, 3H), 3.92-3.68 (m, 0.5H), 3.49-2.59 (m, 2H), 2.47-2.35 (m, 3H), 2.04-1.87 (m, 3H), 1.88-1.33 (m, 6H), 1.46 (d, J = 7.0 Hz, 3H), 1.34-1.10 (m, 2H), 0.47-0.28 (m, 1H). |

TABLE 3-continued

| Example | ES/MS m/z [M + H]+ | ¹H NMR |
|---|---|---|
| 904 | 652.3 | 1H NMR (400 MHz, DMSO-d6) δ 8.38 (d, J = 8.9 Hz, 1H), 8.10 (d, J = 8.1 Hz, 1H), 8.08-7.70 (m, 3H), 7.35 (br. s, 1H), 7.27 (d, J = 8.1 Hz, 1H), 7.18 (s, 1H), 6.91 (s, 1H), 5.32 (dq, J = 8.9, 6.8 Hz, 1H), 5.10-4.86 (m, 0.5H), 4.84-4.64 (m, 2H), 4.63-4.44 (m, 0.5H), 4.32-4.15 (m, 0.5H), 3.99 (s, 3H), 3.89 (tt, J = 7.3, 3.9 Hz, 1H), 3.86-3.75 (m, 0.5H), 3.43 (t, J = 8.1 Hz, 2H), 3.51-2.98 (m, 1H), 2.88-2.68 (m, 1H), 2.33-2.21 (m, 1H), 2.04-1.93 (m, 1H), 1.92-1.53 (m, 11H), 1.49 (d, J = 6.8 Hz, 3H), 1.47-1.37 (m, 1H), 1.20-0.93 (m, 6H), 0.85-0.68 (m, 1H), 0.53 (h, J = 5.0 Hz, 1H). |
| 905 | 654.3 | 1H NMR (400 MHz, DMSO-d6) δ 8.06 (d, J = 8.0 Hz, 1H), 8.05 (d, J = 9.1 Hz, 1H), 8.02-7.62 (m, 3H), 7.34 (br. s, 1H), 7.21 (d, J = 8.1 Hz, 1H), 7.18 (s, 1H), 6.91 (s, 1H), 5.29-5.16 (m, 1H), 5.06-4.92 (m, 0.5H), 4.86 (dt, J = 14.1, 7.4 Hz, 1H), 4.83-4.74 (m, 0.5H), 4.61-4.45 (m, 0.5H), 4.32-4.17 (m, 0.5H), 3.99 (s, 3H), 3.89 (tt, J = 7.2, 3.9 Hz, 1H), 3.83-3.75 (m, 0.5H), 3.39-3.28 (m, 1H), 3.51-3.00 (m, 1H), 2.85-2.72 (m, 1H), 2.44-2.27 (m, 1H), 2.03-1.90 (m, 1H), 1.88-1.50 (m, 9H), 1.46 (d, J = 6.9 Hz, 3H), 1.33 (s, 3H), 1.30-1.25 (m, 2H), 1.22 (s, 3H), 1.14-1.03 (m, 1H), 1.03-0.92 (m, 1H), 0.89-0.76 (m, 1H), 0.75-0.62 (m, 1H), 0.48-0.38 (m, 1H). |
| 906 | 682.2 | 1H NMR (400 MHz, DMSO-d6) δ 9.02 (d, J = 7.0 Hz, 1H), 8.08 (d, J = 8.0 Hz, 1H), 8.05-7.67 (m, 3H), 7.42-7.27 (m, 2H), 7.24 (d, J = 8.0 Hz, 1H), 7.27-7.19 (m, 1H), 7.08 (s, 1H), 6.90 (s, 1H), 5.18 (p, J = 7.0 Hz, 1H), 5.05-4.92 (m, 0.5H), 4.91-4.80 (m, 1H), 4.66-4.58 (m, 1H), 4.58-4.46 (m, 0.5H), 4.28-4.16 (m, 0.5H), 4.12 (s, 3H), 3.99 (s, 3H), 3.92-3.71 (m, 0.5H), 3.48-3.00 (m, 2H), 2.88-2.68 (m, 1H), 2.59-2.23 (m, 2H), 2.02-1.92 (m, 1H), 1.90-1.35 (m, 8H), 1.48 (d, J = 7.0 Hz, 3H), 1.34-1.10 (m, 2H), 0.57-0.43 (m, 1H). |
| 907 | 612.3 | 1H NMR (400 MHz, DMSO-d6) δ 8.13 (d, J = 8.0 Hz, 0.4 of 1H), 8.09 (d, J = 8.0 Hz, 0.6 of 1H), 8.03-7.64 (m, 3H), 7.39 (br. s, 1H), 7.32 (d, J = 8.0 Hz, 0.4 of 1H), 7.14 (s, 0.4 of 1H), 7.13 (s, 0.6 of 1H), 7.11 (d, J = 8.0 Hz, 0.6 of 1H), 6.90 (s, 1H), 6.12 (q, J = 7.0 Hz, 0.6 of 1H), 5.29 (dd, J = 13.4, 6.5 Hz, 0.4 of 1H), 5.06-4.94 (m, 1H), 4.64 (br. d, J = 13.4 Hz, 1H), 4.59-4.14 (m, 2H), 4.12 (s, 3H), 3.99 (s, 3H), 3.87-3.59 (m, 1H), 3.45-3.35 (m, 0.4 of 1H), 3.35-3.21 (m, 1H), 3.21-3.09 (m, 1H), 2.82-2.69 (m, 0.6 of 1H), 2.29 (s, 1H of 3H), 2.02 (s, 2H of 3H), 2.02-1.91 (m, 2H), 1.90-1.45 (m, 5H), 1.63 (d, J = 6.7 Hz, 1H of 3H), 1.54 (d, J = 7.0 Hz, 2H of 3H), 1.43-1.03 (m, 6H), 0.98-0.74 (m, 2H), 0.19--0.30 (m, 2H). |
| 908 | 626.3 | 1H NMR (400 MHz, DMSO-d6) δ 8.13 (d, J = 8.0 Hz, 0.33H of 1H), 8.09 (d, J = 8.0 Hz, 0.66H of 1H), 8.03 (br. s, 2H of 3H), 7.81 (br. s, 1H of 3H), 7.39 (s, 1H), 7.31 (d, J = 8.1 Hz, 0.33H of 1H), 7.12 (s, 0.33 H of 1H), 7.11 (d, J = 8.1 Hz, 0.66H of 1H), 7.11 (s, 0.66H of 1H), 6.91 (s, 1H), 6.05 (q, J = 6.9 Hz, 0.66H of 1H), 5.40 (q, J = 6.8 Hz, 0.33H of 1H), 5.05-4.94 (m, 1H), 4.73-4.63 (m, 1H), 4.89-4.42 (m, 1H), 4.29-4.18 (m, 0.66H of 1H), 4.13 (s, 1H of 3H), 4.12 (s, 2H of 3H), 3.99 (s, 3H), 3.92-3.69 (m, 0.33H of 1H), 3.45-3.25 (m, 1H), 3.23-3.11 (m, 1H), 2.89-2.69 (m, 2H), 2.31 (s, 1H of 3H), 2.04 (s, 2H of 3H), 2.04-1.93 (m, 1H), 1.92-1.73 (m, 1H), 1.71 (d, J = 6.8 Hz, 1H of 3H), 1.61 (d, J = 6.9 Hz, 2H of 3H), 1.67-1.49 (m, 7H), 1.48-1.00 (m, 6H), 1.00-0.63 (m, 3H), 0.62-0.42 (m, 1H). |
| 909 | 628.3 | 1H NMR (400 MHz, DMSO-d6) δ 8.08 (d, J = 8.0 Hz, 1H), 8.06 (d, J = 9.0 Hz, 1H), 7.94-7.75 (m, 3H), 7.41-7.35 (m, 1H), 7.23 (d, J = 8.1 Hz, 1H), 7.06 (s, 1H), 6.90 (s, 1H), 5.23 (dq, J = 9.0, 6.8 Hz, 1H), 5.02-4.97 (m, 0.5H), 4.87-4.75 (m, 1H), 4.61-4.50 (m, 2H), 4.27-4.18 (m, 0.5H), 4.10 (s, 3H), 3.99 (s, 3H), 3.91-3.73 (m, 0.5H), 3.35 (ddd, J = 10.5, 8.3, 5.5 Hz, 1H), 3.49-3.04 (m, 0.5H), 2.89-2.49 (m, 2H), 2.42-2.27 (m, 1H), 2.05-1.93 (m, 1H), 1.92-1.72 (m, 2H), 1.72-1.50 (m, 7H), 1.45 (d, J = 6.9 Hz, 3H), 1.33 (s, 3H), 1.37-1.20 (m, 1H), 1.22 (s, 3H), 0.80-0.66 (m, 1H). |
| 910 | 626.3 | 1H NMR (400 MHz, DMSO-d6) δ 8.39 (d, J = 8.8 Hz, 1H), 8.13 (d, J = 8.0 Hz, 1H), 8.08-7.67 (m, 3H), 7.38 (s, 1H), 7.28 (d, J = 8.1 Hz, 1H), 7.07 (s, 1H), 6.90 (s, 1H), 5.32 (dq, J = 8.6, 6.7 Hz, 1H), 5.06-4.92 (m, 0.5H), 4.79-4.67 (m, 1H), 4.61-4.49 (m, 2H), 4.29-4.18 (m, 0.5H), 4.12 (s, 3H), 3.99 (s, 3H), 3.91-3.68 (m, 1H), 3.51-3.37 (m, 1H), 3.37-3.06 (m, 1H), 2.86-2.69 (m, 1H), 2.34-2.19 (m, 1H), 2.04-1.92 (m, 2H), 1.90-1.51 (m, 8H), 1.47 (d, J = 6.8 Hz, 3H), 1.43 (q, J = 6.8 Hz, 1H), 1.19-0.97 (m, 5H). |
| 911 | 735.3 | 1H NMR (400 MHz, DMSO-d6) δ 9.25 (d, J = 8.1 Hz, 1H), 8.10 (d, J = 8.0 Hz, 1H), 7.95 (s, 2H), 7.82-7.54 (m, 2H), 7.32 (s, 1H), 7.27 (d, J = 8.1 Hz, 1H), 7.24-7.17 (m, 1H), 6.86 (s, 1H), 5.45-5.33 (m, 1H), 5.06-4.93 (m, 1.5H), 4.88-4.74 (m, 1H), 4.58-4.47 (m, 0.5H), 4.22-4.12 (m, 0.5H), 4.05-3.95 (m, 1H), 3.79-3.68 (m, 0.5H), 3.45-3.04 (m, 1.5H), 2.81-2.70 (m, 0.5H), 2.31-2.16 (m, 2H), 2.05-1.37 (m, 14H), 1.30-0.83 (m, 8H), 0.54-0.30 (m, 2H). |
| 912 | 650.3 | 1H NMR (400 MHz, DMSO-d6) δ 8.98 (d, J = 6.6 Hz, 1H), 8.08 (d, J = 8.1 Hz, 1H), 7.97 (s, 2H), 7.79-7.52 (m, 3H), 7.50 (d, J = 1.9 Hz, 1H), |

TABLE 3-continued

| Example | ES/MS m/z [M + H]+ | ¹H NMR |
|---|---|---|
| | | 7.29-7.17 (m, 3H), 6.68 (d, J = 1.9 Hz, 1H), 5.08 (p, J = 7.0 Hz, 1H), 5.03-4.89 (m, 0.5H), 4.86-4.70 (m, 1H), 4.58-4.40 (m, 2.5H), 4.23-4.09 (m, 0.5H), 4.09-3.94 (m, 2H), 3.79-3.67 (m, 0.5H), 3.43-3.01 (m, 1.5H), 2.80-2.68 (m, 0.5H), 2.03-1.34 (m, 12H), 1.19-0.81 (m, 6H), 0.65-0.55 (m, 1H). |
| 913 | 606.3 | 1H NMR (400 MHz, DMSO-d6) δ 8.45 (d, J = 8.5 Hz, 1H), 8.02-7.89 (m, 3H), 7.82-7.66 (m, 3H), 7.39 (d, J = 8.3 Hz, 1H), 7.26 (s, 1H), 7.13 (d, J = 8.1 Hz, 1H), 5.00 (p, J = 7.1 Hz, 1H), 4.95-4.69 (m, 2.5H), 4.59-4.47 (m, 0.5H), 4.27-4.15 (m, 0.5H), 3.87-3.68 (m, 1.5H), 3.46-2.98 (m, 1.5H), 2.83-2.69 (m, 0.5H), 2.05-1.05 (m, 19H), 0.95-0.80 (m, 2H), 0.77-0.41 (m, 4H). |
| 914 | 642.3 | 1H NMR (400 MHz, DMSO-d6) δ 8.58 (d, J = 8.8 Hz, 1H), 8.06 (d, J = 8.0 Hz, 1H), 7.97 (s, 2H), 7.85-7.63 (m, 3H), 7.41 (d, J = 8.2 Hz, 1H), 7.36 (s, 1H), 7.23 (d, J = 8.1 Hz, 1H), 5.90 (t, J = 13.8 Hz, 1H), 5.18 (dd, J = 27.7, 14.6 Hz, 1H), 5.11-4.89 (m, 1.5H), 4.59-4.46 (m, 0.5H), 4.27-4.17 (m, 0.5H), 3.91-3.69 (m, 1.5H), 3.46-3.07 (m, 1.5H), 2.83-2.69 (m, 0.5H), 2.30-1.21 (m, 16H), 1.09-0.80 (m, 3H), 0.71-0.56 (m, 1H), 0.56-0.37 (m, 3H). |
| 915 | 642.3 | 1H NMR (400 MHz, DMSO-d6) δ 8.10 (d, J = 8.1 Hz, 1H), 8.02-7.68 (m, 3H), 7.69-7.60 (m, 1H), 7.38 (s, 1H), 7.25 (d, J = 8.2 Hz, 1H), 7.04 (s, 1H), 6.90 (s, 1H), 5.04-4.88 (m, 1.5H), 4.64-4.50 (m, 1.5H), 4.45-4.37 (m, 1H), 4.25-4.19 (m, 0.5H), 4.13 (s, 3H), 3.99 (s, 3H), 3.86-3.76 (m, 0.5H), 3.45-3.00 (m, 1.5H), 2.83-2.70 (m, 0.5H), 2.40-2.28 (m, 1H), 2.03-1.42 (m, 17H), 1.24 (d, J = 2.0 Hz, 3H), 0.80 (dd, J = 13.1, 6.8 Hz, 1H). |
| 916 | 642.3 | 1H NMR (400 MHz, DMSO-d6) δ 8.04 (d, J = 8.0 Hz, 1H), 7.96 (s, 2H), 7.82 (d, J = 8.8 Hz, 1H), 7.73 (s, 1H), 7.37 (s, 1H), 7.18 (d, J = 8.1 Hz, 1H), 7.05 (s, 1H), 6.89 (s, 1H), 5.29-5.19 (m, 1H), 5.05-4.94 (m, 0.5H), 4.91-4.81 (m, 1H), 4.69-4.60 (m, 1H), 4.60-4.45 (m, 0.5H), 4.29-4.18 (m, 0.5H), 4.12 (s, 3H), 3.99 (s, 3H), 3.89-3.73 (m, 0.5H), 3.43-3.03 (m, 1.5H), 2.84-2.70 (m, 0.5H), 2.13-1.31 (m, 21H), 0.58 (dd, J = 12.7, 6.4 Hz, 1H). |
| 917 | 624.4 | 1H NMR (400 MHz, DMSO-d6) δ 8.00 (d, J = 8.1 Hz, 1H), 7.99 (brs, 1H), 7.76 (s, 1H), 7.54 (d, J = 8.5 Hz, 1H), 7.37 (s, 1H), 7.15 (d, J = 8.1 Hz, 1H), 7.02 (s, 1H), 6.90 (s, 1H), 5.13-5.03 (m, 1H), 5.00 (brs, 1H), 4.87-4.52 (m, 4H), 4.11 (s, 3H), 3.99 (s, 3H), 3.42-2.70 (m, 3H), 2.06 1.51 (m, 10H), 1.49 (s, 3H), 1.47 (s, 3H), 1.39-1.08 (m, 5H), 0.75-0.61 (m, 1H), 0.25-0.14 (m, 1H). |
| 918 | 654.5 | 1H NMR (400 MHz, DMSO-d6) δ 8.52 (d, J = 9.7 Hz, 1H), 8.07 (d, J = 8.1 Hz, 1H), 7.97 (brs, 2H), 7.83-7.55 (m, 2H), 7.29 (s, 1H), 7.24 (brs, 1H), 7.22 (d, J = 8.1 Hz, 1H), 5.41-5.26 (m, 1H), 5.18-4.82 (m, 2H), 4.53 (brs, 1H), 4.19 (brs, 1H), 4.00 (brs, 1H), 3.31-3.02 (m, 1H), 2.91-2.73 (m, 1H), 2.36-2.17 (m, 2H), 2.15-1.50 (m, 8H), 1.46 (d, J = 7.1 Hz, 3H), 1.40-0.67 (m, 8H), 0.57 (brs, 1H), 0.20--0.14 (m, 2H). |
| 919 | 640.5 | 1H NMR (400 MHz, DMSO-d6) δ 8.45 (d, J = 9.3 Hz, 1H), 8.06 (brs, 2H), 8.02 (d, J = 8.1 Hz, 1H), 7.83 (brs, 2H), 7.70-7.54 (m, 1H), 7.26 (brs, 1H), 7.24 (s, 1H), 7.19 (d, J = 8.1 Hz, 1H), 5.85-5.68 (m, 1H), 5.60-5.40 (m, 1H), 5.26-5.13 (m, 1H), 5.08-4.84 (m, 1H), 4.72 (brs, 2H), 4.54 (brs, 1H), 4.17 (brs, 1H), 3.98 (brs, 1H), 3.76 (brs, 1H), 3.49-3.02 (m, 2H), 2.94-2.58 (m, 2H), 2.47-2.24 (m, 1H), 2.20-1.53 (m, 6H), 1.56-1.39 (m, 3H), 1.24-0.99 (m, 4H), 0.92-0.65 (m, 2H). |
| 920 | 666.5 | 1H NMR (400 MHz, DMSO-d6) δ 8.43 (d, J = 9.5 Hz, 1H), 8.04 (d, J = 8.0 Hz, 1H), 8.03 (brs, 1H), 7.90-7.62 (m, 3H), 7.31 (brs, 1H), 7.19 (d, J = 8.1 Hz, 1H), 7.07 (s, 1H), 6.45 (t, J = 56.0 Hz, 1H), 5.29-4.90 (m, 4H), 4.85-4.44 (m, 3H), 4.17 (brs, 1H), 3.77 (brs, 1H), 3.48-3.09 (m, 1H), 2.76 (brs, 1H), 2.39-2.20 (m, 1H), 2.13-1.48 (m, 11H), 1.45 (d, J = 7.1 Hz, 3H), 1.40-1.09 (m, 3H), 1.01-0.86 (m, 1H) |
| 921 | 710.2 | 1H NMR (400 MHz, DMSO-d6) δ 9.12 (d, J = 7.1 Hz, 1H), 8.11 (d, J = 8.0 Hz, 1H), 7.99 (brs, 2H), 7.83 (d, J = 8.0 Hz, 1H), 7.76-7.61 (m, 3H), 7.42 (d, J = 8.0 Hz, 1H), 7.32 (brs, 1H), 7.28 (d, J = 8.1 Hz, 1H), 7.15 (s, 1H), 5.29-5.16 (m, 1H), 5.04-4.83 (m, 2H), 4.675-4.48 (m, 1H), 4.46 (d, J = 7.0 Hz, 2H), 4.20 (brs, 1H), 2.84-2.57 (m, 2H), 2.46-2.30 (m, 2H), 2.04-1.32 (m, 8H), 1.50 (d, J = 7.1 Hz, 4H), 1.29-1.04 (m, 2H), 0.60 (brs, 1H), 0.51-0.31 (m, 2H), 0.33-0.20 (m, 1H), 0.09--0.09 (m, 1H) |
| 922 | 684.4 | 1H NMR (400 MHz, DMSO-d6) δ 8.57 (d, J = 8.8 Hz, 1H), 8.10 (d, J = 8.0 Hz, 1H), 7.98 (brs, 2H), 7.84-7.63 (m, 2H), 7.47-7.28 (m, 1H), 7.26 (d, J = 8.1 Hz, 1H), 7.22 (s, 1H), 6.44 (t, J = 54.3 Hz, 1H), 5.52-5.31 (m, 1H), 5.32-4.93 (m, 3H), 4.83 (q, J = 14.6 Hz, 1H), 4.54 (brs, 1H), 4.18 (brs, 1H), 3.48-3.09 (m, 3H), 2.78 (brs, 1H), 2.23-1.49 (m, 9H), 1.45 (d, J = 7.0 Hz, 3H), 1.43-1.23 (m, 2H), 0.90-0.80 (m, 1H), 0.71-0.57 (m, 1H), 0.56-0.45 (m, 2H). |
| 923 | 624.7 | 1H NMR (400 MHz, DMSO-d6) δ 8.43 (d, J = 9.5 Hz, 1H), 8.01 (d, J = 8.0 Hz, 1H), 7.98 (brs, 1H), 7.77 (d, J = 8.3 Hz, 2H), 7.76 (brs, 2H), 7.40 (d, J = 8.3 Hz, 1H), 7.28 (s, 1H), 7.16 (d, J = 8.0 Hz, 1H), 5.24-5.15 (m, 1H), 5.07-4.73 (m, 2H), 4.54 (brs, 1H), 4.20 (brs, 1H), 3.50-2.71 (m, |

TABLE 3-continued

| Example | ES/MS m/z [M + H]+ | 1H NMR |
|---|---|---|
| | | 3H), 2.37-2.20 (m, 1H), 2.14-1.90 (m, 3H), 1.89-1.50 (m, 10H), 1.46 (d, J = 7.0 Hz, 3H), 1.40-1.10 (m, 4H), 1.01-0.80 (m, 2H), 0.61 (brs, 1H). |
| 924 | 686.2 | 1H NMR (400 MHz, DMSO-d6) δ 8.04 (d, J = 8.1 Hz, 1H), 7.96 (brs, 2H), 7.72 (brs, 2H), 7.66 (d, J = 8.5 Hz, 1H), 7.36 (brs, 1H), 7.26 (s, 1H), 7.22 (d, J = 8.1 Hz, 1H), 6.92 (s, 1H), 5.86-5.72 (m, 1H), 5.24 (dd, J = 27.2, 14.6 Hz, 1H), 5.17-5.05 (m, 1H), 4.99 (brs, 1H), 4.53 (brs, 1H), 4.26 (brs, 1H), 4.00 (s, 3H), 3.96-3.87 (dt, J = 7.1, 4.1 Hz, 1H), 3.44-2.66 (m, 3H), 2.20-1.51 (m, 8H), 1.47 (d, J = 7.1 Hz, 3H), 1.44 (s, 3H), 1.40-1.04 (m, 4H), 1.01-0.82 (m, 2H), 0.62-0.38 (m, 2H), 0.26-0.18 (m, 1H). |
| 925 | 720.3 | 1H NMR (400 MHz, DMSO-d6) δ 9.10 (d, J = 7.1 Hz, 1H), 8.12 (d, J = 8.1 Hz, 1H), 8.02-7.92 (m, 2H), 7.82 (d, J = 8.1 Hz, 1H), 7.80-7.62 (m, 2H), 7.41 (d, J = 8.0 Hz, 1H), 7.34 (brs, 1H), 7.28 (d, J = 8.1 Hz, 1H), 7.15 (s, 1H), 6.46 (t, J = 54.0 Hz, 1H), 5.27-4.81 (m, 5H), 4.73-4.43 (m, 1H), 4.17 (brs, 1H), 3.33-3.01 (m, 1H), 2.90-2.58 (m, 2H), 2.44-2.32 (m, 2H), 2.05-1.34 (m, 10H), 1.49 (d, J = 7.1 Hz, 3H), 1.29-1.09 (m, 1H), 0.72-0.56 (m, 1H). |
| 926 | 678.2 | 1H NMR (400 MHz, DMSO-d6) δ 9.12 (d, J = 7.1 Hz, 1H), 8.10 (d, J = 8.0 Hz, 1H), 7.98 (brs, 2H), 7.82 (d, J = 8.0 Hz, 1H), 7.78 (d, J = 8.4 Hz, 1H), 7.75 (brs, 1H), 7.41 (d, J = 8.0 Hz, 1H), 7.33 (s, 1H), 7.26 (d, J = 8.0 Hz, 1H), 5.26-5.16 (m, 1H), 5.09-4.80 (m, 2H), 4.54 (brs, 1H), 4.21 (brs, 1H), 3.94-3.81 (m, 1H), 3.46-3.03 (m, 2H), 2.82-2.58 (m, 2H), 2.47-2.27 (m, 2H), 2.08-1.35 (m, 10H), 1.50 (d, J = 7.1 Hz, 3H), 1.35-0.84 (m, 4H), 0.66-0.37 (m, 2H). |
| 927 | 682.3 | 1H NMR (400 MHz, DMSO-d6) δ 8.95 (d, J = 6.8 Hz, 1H), 8.08 (d, J = 8.0 Hz, 1H), 7.97 (brs, 2H), 7.74 (brs, 1H), 7.44 (dd, J = 10.8, 8.3 Hz, 1H), 7.36 (brs, 1H), 7.32 (dd, J = 11.7, 7.9 Hz, 1H), 7.25 (d, J = 8.1 Hz, 1H), 7.08 (s, 1H), 6.90 (brs, 1H), 5.22-5.18 (m, 1H), 4.99 (brs, 0.4H minor rotamer), 4.91-4.78 (m, 1H), 4.68-4.46 (m, 1H), 4.26 (brs, 0.6H major rotamer), 4.12 (s, 3H), 4.00 (s, 3H), 2.77 (brs, 1H), 2.49-2.19 (m, 2H), 2.04-1.62 (m 9H), 1.49 (d, J = 7.1 Hz, 3H), 1.48-1.34 (m, 1H), 1.36-1.06 (m, 3H), 0.60-0.42 (m, 1H). |
| 928 | 626.3 | 1H NMR (400 MHz, DMSO-d6) δ 7.99 (brs, 2H), 7.95 (d, J = 8.0 Hz, 1H), 7.78 (d, J = 7.6 Hz, 2H), 7.36-7.24 (m, 1H), 7.12 (d, J = 8.1 Hz, 1H), 6.61 (s, 1H), 6.40 (s, 1H), 5.11 (p, J = 7.1 Hz, 1H), 4.98 (brs, 0.4H minor rotamer), 4.82-4.67 (m, 1H), 4.53 (brs, 0.6H minor rotamer), 4.36-4.20 (m, 2H), 4.09 (s, 3H), 3.45-3.03 (m, 2H), 2.79 (s, 3H), 2.10-1.49 (m, 12H), 1.44 (d, J = 7.1 Hz, 3H), 1.41-1.23 (m, 2H), 1.21 (s, 3H), 1.15-0.99 (m, 2H), 0.95 (s, 3H). |
| 929 | 646.3 | 1H NMR (400 MHz, DMSO-d6) δ 8.65 (d, J = 7.6 Hz, 1H), 7.98 (brs, 2H), 7.90 (d, J = 8.0 Hz, 1H), 7.75 (brs, 1H), 7.38-7.19 (m, 2H), 7.08 (d, J = 8.0 Hz, 1H), 6.59 (s, 1H), 6.36 (s, 1H), 5.04-4.89 (m, 1H), 4.51 (brs, 2H), 4.23 (brs, 1H), 4.09 (s, 3H), 3.68-3.54 (m, 2H), 3.36 (brs, 1H), 3.17 (s, 3H), 2.81 (s, 3H), 2.23-1.52 (m, 9H), 1.44 (d, J = 7.1 Hz, 3H), 1.37-0.99 (m, 4H). |
| 930 | 672.3 | 1H NMR (400 MHz, DMSO-d6) δ 8.71 (d, J = 7.6 Hz, 1H), 7.99 (d, J = 8.0 Hz, 1H), 7.97 (brs, 1H), 7.75 (brs, 1H), 7.33 (brs, 1H), 7.16 (s, 1H), 7.15 (d, J = 7.6 Hz, 1H), 6.90 (s, 1H), 5.05-4.92 (m, 1H), 4.90-4.21 (m, 4H), 3.99 (s, 3H), 3.93-3.84 (m, 2H), 3.45-3.02 (m, 3H), 2.85-2.68 (m, 1H), 2.49-2.40 (m, 2H), 2.06-1.42 (m, 10H), 1.46 (d, J = 7.1 Hz, 3H), 1.38-0.96 (m, 5H), 0.78 (brs, 1H), 0.53 (brs, 1H). |
| 931 | 688.3 | 1H NMR (400 MHz, DMSO-d6) δ 8.27 (s, 1H), 8.14 (d, J = 8.0 Hz, 1H), 7.97 (brs, 2H), 7.74 (brs, 1H), 7.37 (brs, 1H), 7.32 (d, J = 8.1 Hz, 1H), 7.28 (s, 1H), 6.92 (s, 1H), 5.69-5.29 (m, 3H), 4.98 (brs, 1H), 4.53 (brs, 1H), 4.26 (brs, 1H), 4.00 (s, 3H), 3.95-3.88 (m, 2H), 3.56-3.05 (m, 4H), 2.77 (brs, 1H), 2.16-1.50 (m, 8H), 1.49 (d, J = 6.9 Hz, 3H), 1.30-0.79 (m, 7H), 0.50-0.34 (m, 1H). |
| 932 | 695.4 | 1H NMR (400 MHz, DMSO-d6) δ 8.96 (s, 1H), 8.10 (d, J = 8.2 Hz, 1H), 8.02 (s, 2H), 7.80 (d, J = 8.0 Hz, 1H), 7.40 (d, J = 8.1 Hz, 1H), 7.36 (d, J = 8.3 Hz, 1H), 7.09 (s, 1H), 6.91 (s, 1H), 5.05-4.94 (m, 0.65H, rotamer), 4.75-4.66 (m, 2H), 4.64-4.34 (m, 3H), 4.28-4.18 (m, 0.32H, rotamer), 4.13 (s, 3H), 4.00 (s, 3H), 3.70-3.56 (m, 0.31H, rotamer), 3.48-3.21 (m, 1H), 3.20-3.09 (m, 0.42H, rotamer), 2.87-2.70 (m, 0.33H, rotamer), 2.66-2.56 (m, 2H), 2.05-1.93 (m, 1H), 1.75 (s, 6H), 1.64 (s, 4H), 1.51-1.35 (m, 2H), 1.26 (q, J = 7.2, 6.6 Hz, 3H), 0.98-0.77 (m, 2H). |
| 933 | 642.6 | 1H NMR (400 MHz, DMSO-d6) δ 8.35 (s, 1H), 8.02 (d, J = 8.2 Hz, 1H), 7.98 (s, 2H), 7.75 (s, 1H), 7.37 (s, 1H), 7.28 (d, J = 8.2 Hz, 1H), 7.03 (s, 1H), 6.90 (s, 1H), 5.12-4.91 (m, 0.55H, rotamer), 4.77-4.65 (m, 1H), 4.65-4.47 (m, 2H), 4.30-4.19 (m, 3H), 4.12 (s, 3H), 3.99 (s, 3H), 3.86-3.73 (m, 0.15H, rotamer), 3.69-3.56 (m, 0.14H, rotamer), 3.47-3.22 (m, 0.59H, rotamer), 3.22-3.06 (m, 0.13H, rotamer), 2.87-2.71 (m, 0.59H, rotamer), 2.30-2.18 (m, 1H), 2.09-1.85 (m, 1H), 1.95 (s, 3H), 1.81 (m, 2H), 1.74-1.57 (m, 3H), 1.53 (s, 3H), 1.44-1.29 (m, 2H), 1.29-1.22 (m, 2H), 1.23-1.02 (m, 1H), 0.98-0.80 (m, 1H). |

TABLE 3-continued

| Example | ES/MS m/z [M + H]+ | 1H NMR |
|---|---|---|
| 934 | 742.3 | 1H NMR (400 MHz, DMSO-d6) δ 9.43 (d, J = 7.0 Hz, 1H), 9.04 (s, 1H), 8.10 (d, J = 8.0 Hz, 1H), 7.88 (d, J = 91.6 Hz, 3H), 7.33 (s, 1H), 7.28 (d, J = 8.1 Hz, 1H), 7.23 (s, 1H), 6.91 (s, 1H), 5.25 (p, J = 7.0 Hz, 1H), 5.08-4.94 (m, 0.42H, rotamers), 4.93-4.77 (m, 2H), 4.64-4.45 (m, 0.51H, rotamers), 4.35-4.18 (m, 0.57H, rotamers), 4.00 (s, 3H), 3.96-3.87 (m, 1H), 3.85-3.57 (m, 3H), 2.77-2.65 (m, 1H), 2.48-2.32 (m, 1H), 2.05-1.89 (m, 1H), 1.88-1.77 (m, 1H), 1.73-1.58 (m, 7H), 1.53 (d, J = 7.1 Hz, 3H), 1.47 (s, 1H), 1.45-1.34 (m, 1H), 1.33-1.21 (m, 1H), 1.20-1.11 (m, 1H), 1.11-0.97 (m, 1H), 0.97-0.82 (m, 1H), 0.72-0.49 (m, 1H), 0.48-0.30 (m, 1H). |
| 935 | 682.4 | 1H NMR (400 MHz, DMSO-d6) δ 9.22 (d, J = 7.3 Hz, 1H), 8.08 (d, J = 8.0 Hz, 1H), 8.03 (s, 2H), 7.79 (s, 1H), 7.37 (s, 1H), 7.25 (d, J = 8.0 Hz, 1H), 7.13 (dd, J = 9.4, 2.4 Hz, 1H), 7.09 (s, 1H), 6.98 (dd, J = 9.7, 2.4 Hz, 1H), 6.90 (s, 1H), 5.26 (p, J = 7.1 Hz, 1H), 4.99 (m, 0.17H, rotamer), 4.96-4.84 (m, 1H), 4.62 (d, J = 13.6 Hz, 1H), 4.32 (d, J = 72.1 Hz, 7H), 4.12 (s, 3H), 4.00 (s, 3H), 3.81 (m, 0.17H, rotamer), 3.49-3.02 (m, 1H), 2.77 (s, 1H), 2.33-2.14 (m, 2H), 2.05-1.91 (m, 1H), 1.90-1.77 (m, 1H), 1.64 (d, J = 21.7 Hz, 3H), 1.46 (d, J = 7.1 Hz, 3H), 1.43-1.35 (m, 1H), 1.34-1.23 (m, 1H), 1.21-1.09 (m, 1H), 0.57-0.20 (m, 1H). |
| 936 | 646.4 | 1H NMR (400 MHz, DMSO-d6) δ 8.77 (d, J = 7.0 Hz, 1H), 8.02 (s, 2H), 7.98 (d, J = 8.0 Hz, 1H), 7.82 (s, 1H), 7.37-7.29 (m, 2H), 7.24 (d, J = 7.4, 1.3 Hz, 1H), 7.20 (d, 1H), 7.17 (d, J = 8.0 Hz, 1H), 6.66 (s, 1H), 6.40 (s, 1H), 5.18 (p, J = 7.0 Hz, 1H), 5.05-4.90 (m, 0.43H, rotamer), 4.91-4.72 (m, 1H), 4.62-4.41 (m, 1H), 4.33-4.21 (m, 0.50H, rotamer), 4.10 (s, 3H), 4.08-3.83 (m, 5H), 3.37 (s, 1H), 3.22-3.05 (m, 0.35H, rotamer), 2.80 (s, 3H), 2.48-2.31 (m, 2H), 2.29-2.17 (m, 1H), 2.06-1.91 (m, 1H), 1.90-1.73 (m, 1H), 1.74-1.59 (m, 2H), 1.48 (d, J = 7.0 Hz, 3H), 1.42-1.05 (m, 3H), 0.67-0.37 (m, 1H). |
| 937 | 608.3 | 1H NMR (400 MHz, DMSO-d6) δ 8.55 (s, 1H), 8.43 (s, 1H), 8.19 (d, J = 8.4 Hz, 1H), 7.44 (d, J = 1.1 Hz, 1H), 7.27 (d, J = 8.3 Hz, 1H), 7.15 (s, 1H), 6.92 (s, 1H), 5.82 (s, 1H), 4.69 (t, J = 6.4 Hz, 2H), 4.19 (s, 1H), 4.13 (s, 3H), 4.00 (s, 3H), 3.83-3.36 (m, 4H), 3.51 (s, 3H), 3.40-3.21 (m, 3H), 2.67-2.55 (m, 2H), 1.81-1.64 (m, 3H), 1.56-1.40 (m, 4H), 1.38-1.22 (m, 2H), 1.22-1.08 (m, 2H), 1.00-0.71 (m, 2H). |
| 938 | 630.6 | 1H NMR (400 MHz, DMSO-d6) δ 8.43 (d, J = 9.5 Hz, 1H), 8.04 (d, J = 8.0 Hz, 1H), 7.85-7.61 (m, 2H), 7.26 (d, J = 15.0 Hz, 1H), 7.19 (d, J = 8.0 Hz, 1H), 7.05 (s, 1H), 5.20 (m, J = 9.6, 7.0 Hz, 1H), 4.99 (s, 0.45H), 4.78 (m, J = 13.8, 9.4 Hz, 1H), 4.56 (d, J = 8.9 Hz, 0.24H), 4.47 (m, J = 21.7, 7.2 Hz, 3H), 4.18 (s, 0.61H), 3.38 (s, 0.73H), 3.29 (s, 0.69H), 3.14 (s, 0.45H), 2.76 (d, J = 16.0 Hz, 0.53H), 2.30-2.19 (m, 1H), 2.07-1.91 (m, 2H), 1.76 (s, 3H), 1.59 (s, 7H), 1.49-1.38 (m, 7H), 1.35 (d, J = 10.0 Hz, 1H), 1.30-1.20 (m, 1H), 1.15 (m, J = 13.8, 9.4, 3.5 Hz, 1H), 0.95 (m, J = 11.3, 9.4, 6.0 Hz, 1H). |
| 939 | 684.2 | 1H NMR (400 MHz, DMSO-d6) δ 9.12 (d, J = 7.1 Hz, 1H), 8.13 (d, J = 8.1 Hz, 1H), 8.00 (s, 1H), 7.82 (d, J = 8.0 Hz, 1H), 7.79-7.60 (m, 2H), 7.41 (d, J = 8.0 Hz, 1H), 7.29 (d, J = 8.1 Hz, 1H), 7.12 (s, 1H), 5.22 (p, J = 7.0 Hz, 1H), 4.98 (s, 0.44H), 4.92-4.81 (m, 1H), 4.56 (m, J = 14.2, 6.9 Hz, 2H), 4.44 (m, J = 14.4, 7.2 Hz, 2H), 4.19 (s, 0.69H), 3.77 (s, 0.35H), 3.37 (s, 0.71H), 3.29 (s, 1H), 3.15 (s, 0.31H), 2.76 (d, J = 15.7 Hz, 0.63H), 2.70-2.56 (m, 1H), 2.43-2.29 (m, 2H), 1.97 (q, J = 6.9, 3.7 Hz, 1H), 1.79 (d, J = 25.5 Hz, 2H), 1.67 (s, 3H), 1.50 (d, J = 7.1 Hz, 3H), 1.47 (s, 1H), 1.45 (s, 4H), 1.20 (s, 1H), 0.58 (d, J = 12.3 Hz, 1H). |
| 940 | 686.3 | 1H NMR (400 MHz, DMSO-d6) δ 8.12 (d, J = 8.1 Hz, 1H), 7.99 (d, J = 8.5 Hz, 2H), 7.75 (s, 1H), 7.35 (s, 1H), 7.28 (d, J = 8.1 Hz, 1H), 7.25 (s, 1H), 6.91 (s, 1H), 5.57 (q, J = 16.2 Hz, 1H), 5.38 (q, J = 10.7, 9.0 Hz, 1H), 5.30 (q, J = 7.4 Hz, 1H), 4.99 (s, 0.36H), 4.53 (s, 0.54H), 4.26 (s, 0.59H), 4.00 (s, 3H), 3.91 (m, J = 7.2, 3.8 Hz, 1H), 3.81 (s, 1H), 2.75 (d, J = 12.1 Hz, 0.58H), 2.09-1.92 (m, 3H), 1.92-1.75 (m, 3H), 1.66 (s, 4H), 1.48 (d, J = 9.4 Hz, 2H), 1.44 (d, J = 7.0 Hz, 3H), 1.25 (m, J = 14.2, 13.2, 6.2 Hz, 2H), 1.20-1.10 (m, 1H), 1.05-0.97 (m, 2H), 0.92 (t, J = 8.1 Hz, 1H), 0.81 (s, 1H), 0.63-0.55 (m, 1H), 0.49 (q, J = 7.4, 4.6 Hz, 1H), 0.41 (m, J = 8.6, 3.2 Hz, 1H). 19F NMR Peak Table: 19F NMR (376 MHz, DMSO-d6) 8-94.94 (d, J = 241.2 Hz). |
| 941 | 688.2 | 1H NMR (400 MHz, DMSO-d6) δ 8.08 (d, J = 8.0 Hz, 1H), 8.00 (s, 1H), 7.91 (d, J = 7.4 Hz, 1H), 7.77 (s, 1H), 7.33 (s, 1H), 7.24 (t, J = 4.0 Hz, 2H), 6.90 (s, 1H), 5.39 (t, J = 13.7 Hz, 2H), 5.12 (p, J = 7.1 Hz, 1H), 4.98 (s, 0.39H), 4.53 (s, 0.54H), 4.26 (s, 0.54H), 3.99 (s, 3H), 3.90 (m, J = 7.3, 3.9 Hz, 2H), 3.40 (s, 0.41H), 2.75 (d, J = 12.8 Hz, 0.54H), 2.02-1.92 (m, 2H), 1.83 (m, J = 30.4, 14.8 Hz, 4H), 1.62 (s, 3H), 1.52-1.34 (m, 5H), 1.19 (s, 6H), 0.91 (s, 5H), 0.81 (s, 1H), 0.49 (dt, J = 8.1, 4.5 Hz, 1H). |
| 942 | 741.2 | 1H NMR (400 MHz, DMSO-d6) δ 9.32 (d, J = 6.9 Hz, 1H), 8.70 (s, 1H), 8.08 (d, J = 8.0 Hz, 1H), 7.99 (s, 2H), 7.85 (s, 1H), 7.76 (s, 1H), 7.32 (s, 1H), 7.26 (d, J = 8.1 Hz, 1H), 7.22 (s, 1H), 6.91 (s, 1H), 5.22 (t, J = 7.0 Hz, 1H), 4.99 (s, 0.52H), 4.93-4.77 (m, 2H), 4.53 (s, 0.53H), 4.24 (s, 0.55H), 4.00 (s, 3H), 3.92 (m, J = 7.3, 3.9 Hz, 1H), 3.82 (s, 0.93H), 2.75 (d, J = 10.9 Hz, 0.54H), 2.49-2.29 (m, 4H), 1.97 (m, J = 9.5, 9.0, 4.6 Hz, |

TABLE 3-continued

| Example | ES/MS m/z [M + H]+ | 1H NMR |
|---|---|---|
| | | 2H), 1.78 (d, J = 18.7 Hz, 2H), 1.64 (d, J = 18.4 Hz, 3H), 1.52 (d, J = 7.0 Hz, 3H), 1.45 (d, J = 19.8 Hz, 2H), 1.33 (m, J = 11.4, 10.8, 6.3 Hz, 1H), 1.17 (p, J = 7.8, 6.6 Hz, 2H), 1.01 (p, J = 7.1 Hz, 1H), 0.90 (s, 1H), 0.52 (d, J = 12.4 Hz, 1H), 0.36 (m, J = 13.5, 5.4 Hz, 1H). |
| 943 | 662.3 | 1H NMR (400 MHz, DMSO-d6) δ 8.09 (d, J = 8.0 Hz, 1H), 7.96 (s, 1H), 7.91 (d, J = 7.5 Hz, 1H), 7.74 (s, 1H), 7.37 (s, 1H), 7.25 (d, J = 8.1 Hz, 1H), 7.14 (s, 1H), 6.89 (s, 1H), 5.35 (q, J = 15.1 Hz, 1H), 5.24-5.09 (m, 2H), 4.99 (s, 0.62H), 4.53 (s, 0.77H), 4.25 (d, J = 11.1 Hz, 0.88H), 4.09 (s, 3H), 3.99 (s, 3H), 3.83 (s, 0.84H), 2.77 (s, 1H), 1.96 (d, J = 12.1 Hz, 2H), 1.84 (t, J = 11.5 Hz, 2H), 1.71 (d, J = 41.5 Hz, 5H), 1.42 (s, 3H), 1.41-1.32 (m, 1H), 1.19 (s, 5H), 0.91 (s, 3H), 0.83 (m, 1H). |
| 944 | 719.3 | 1H NMR (400 MHz, DMSO-d6) δ 8.71 (dd, J = 8.3, 2.6 Hz, 2H), 8.60 (dt, J = 4.8, 1.3 Hz, 1H), 8.07 (d, J = 8.1 Hz, 1H), 7.90 (td, J = 7.8, 1.8 Hz, 1H), 7.99-7.65 (m, 3H), 7.62 (d, J = 8.0 Hz, 1H), 7.42 (dd, J = 7.6, 4.8 Hz, 1H), 7.35 (s, 1H), 7.22 (d, J = 8.1 Hz, 1H), 7.19 (s, 1H), 6.91 (s, 1H), 5.27 (p, J = 7.2 Hz, 1H), 5.06-4.86 (m, 1.5H), 4.86-4.69 (m, 1H), 4.63-4.41 (m, 0.5H), 4.35-4.18 (m, 0.5H), 3.99 (s, 3H), 3.96-3.73 (m, 1.5H), 3.50-3.02 (m, 1.5H), 2.88-2.69 (m, 0.5H), 2.22-1.43 (m, 14H), 1.41-1.19 (m, 3H), 1.19-0.93 (m, 3H), 0.91-0.69 (m, 2H), 0.53-0.36 (m, 1H). |
| 945 | 719.3 | 1H NMR (400 MHz, DMSO-d6) δ 8.70-8.61 (m, 1H), 8.32 (d, J = 7.0 Hz, 1H), 8.05 (d, J = 8.1 Hz, 1H), 7.92 (td, J = 7.8, 1.8 Hz, 1H), 8.00-7.63 (m, 3H), 7.58 (d, J = 7.4 Hz, 1H), 7.45 (ddd, J = 7.7, 4.8, 1.0 Hz, 1H), 7.41-7.28 (m, 1H), 7.19 (d, J = 8.2 Hz, 1H), 7.17 (s, 1H), 6.91 (s, 1H), 5.12-4.82 (m, 2.5H), 4.71-4.43 (m, 1.5H), 4.33-4.19 (m, 0.5H), 3.99 (s, 3H), 3.95-3.75 (m, 1.5H), 3.47-3.01 (m, 1.5H), 2.94-2.68 (m, 1.5H), 2.22-0.92 (m, 21H), 0.90-0.70 (m, 1H), 0.57-0.45 (m, 1H). |
| 946 | 697.2 | 1H NMR (400 MHz, DMSO-d6) δ 9.11 (d, J = 7.0 Hz, 1H), 8.12 (d, J = 8.1 Hz, 1H), 8.01-7.89 (m, 2H), 7.82 (d, J = 8.1 Hz, 1H), 7.79-7.65 (m, 3H), 7.41 (d, J = 8.0 Hz, 1H), 7.29 (d, J = 8.1 Hz, 1H), 7.00 (s, 1H), 5.20 (p, J = 7.0 Hz, 1H), 5.05-4.93 (m, 1.5H), 4.89-4.76 (m, 1H), 4.58-4.37 (m, 1.5H), 4.25-4.12 (m, 0.5H), 3.82-3.05 (m, 1.5H), 2.83-2.71 (m, 0.5H), 2.67-2.56 (m, 1H), 2.41-2.31 (m, 2H), 2.04-1.32 (m, 15H), 1.26-1.16 (m, 0H), 0.68-0.52 (m, 1H). |
| 947 | 725.3 | 1H NMR (400 MHz, DMSO-d6) δ 9.08 (s, 1H), 8.10 (d, J = 8.0 Hz, 1H), 8.01-7.88 (m, 2H), 7.83 (d, J = 8.1 Hz, 1H), 7.78-7.56 (m, 3H), 7.42 (d, J = 8.0 Hz, 1H), 7.34-7.19 (m, 2H), 5.31-5.17 (m, 1H), 5.05-4.74 (m, 1.5H), 4.60-4.35 (m, 2H), 4.23-4.13 (m, 0.5H), 3.75-3.08 (m, 5.5H), 2.83-2.69 (m, 0.5H), 2.01-1.14 (m, 15H), 0.70 (s, 9H). |
| 948 | 630.3 | 1H NMR (400 MHz, DMSO-d6) δ 8.22 (d, J = 7.2 Hz, 1H), 8.06 (d, J = 8.1 Hz, 1H), 8.02-7.66 (m, 3H), 7.37 (s, 1H), 7.22 (d, J = 8.2 Hz, 1H), 7.03 (s, 1H), 6.89 (s, 1H), 5.07 (p, J = 7.0 Hz, 1H), 5.02-4.94 (m, 0.5H), 4.79-4.68 (m, 1H), 4.62-4.35 (m, 2H), 4.27-4.19 (m, 0.5H), 4.11 (s, 3H), 3.99 (s, 3H), 3.86-3.76 (m, 0H), 3.49-3.03 (m, 1H), 2.82-2.70 (m, 0.5H), 2.19 (dt, J = 39.4, 11.8 Hz, 1H), 2.03-1.27 (m, 18H), 1.26-1.07 (m, 2H). |
| 949 | 630.3 | 1H NMR (400 MHz, DMSO-d6) δ 8.24 (dd, J = 8.7, 3.6 Hz, 1H), 8.07 (d, J = 8.1 Hz, 1H), 8.04-7.64 (m, 3H), 7.37 (s, 1H), 7.23 (d, J = 8.2 Hz, 1H), 7.05 (s, 1H), 6.89 (s, 1H), 5.28 (p, J = 7.3 Hz, 1H), 5.03-4.94 (m, 0.5H), 4.82 (dt, J = 14.5, 7.8 Hz, 1H), 4.60-4.47 (m, 2H), 4.27-4.19 (m, 0.5H), 4.10 (s, 3H), 3.98 (s, 3H), 3.89-3.74 (m, 0.5H), 3.45-3.02 (m, 1H), 2.84-2.70 (m, 0.5H), 2.03-0.98 (m, 21H), 0.75-0.60 (m, 1H). |
| 950 | 668.4 | 1H NMR (400 MHz, DMSO-d6) δ 9.03 (d, J = 7.9 Hz, 1H), 8.59 (brs, 1H), 8.17 (d, J = 8.1 Hz, 1H), 7.98 (brs, 2H), 7.94 (dd, J = 7.9, 1.6 Hz, 1H), 7.90 (d, J = 8.5 Hz, 1H), 7.76 (brs, 1H), 7.56-7.48 (m, 2H), 7.40 (brs, 1H), 7.36 (d, J = 8.2 Hz, 2H), 7.13 (s, 1H), 6.92 (s, 1H), 5.57-5.44 (m, 1H), 5.01 (brs, 1H), 4.94-4.81 (m, 1H), 4.63-4.44 (m, 1H), 4.26 (brs, 1H), 4.18 (s, 3H), 4.01 (s, 3H), 3.45-3.05 (m, 4H), 2.89-2.71 (m, 1H), 2.19-1.56 (m, 8H), 1.53 (d, J = 7.1 Hz, 3H). |
| 951 | 700.2 | 1H NMR (400 MHz, DMSO-d6) δ 9.13 (d, J = 7.0 Hz, 1H), 8.11 (d, J = 8.1 Hz, 1H), 7.96 (s, 1H), 7.82 (d, J = 8.0 Hz, 1H), 7.73 (s, 1H), 7.59 (s, 1H), 7.42 (d, J = 8.0 Hz, 1H), 7.32 (s, 1H), 7.27 (d, J = 8.1 Hz, 1H), 5.21 (p, J = 7.1 Hz, 1H), 5.01-4.87 (m, 1H), 4.84 (s, 1H), 4.53 (s, 0.49H), 4.18 (s, 0.63H), 4.02 (m, J = 6.8, 3.1 Hz, 1H), 3.37 (s, 2H), 3.27 (s, 3H), 3.17 (s, 1H), 2.75 (d, J = 11.8 Hz, 0.51H), 1.95 (d, J = 11.6 Hz, 1H), 1.79 (d, J = 21.4 Hz, 2H), 1.66 (s, 2H), 1.50 (d, J = 7.0 Hz, 3H), 1.19 (q, J = 6.7 Hz, 2H), 1.07 (s, 3H), 0.54 (s, 1H), 0.47 (s, 1H). |
| 952 | 660.5 | 1H NMR (400 MHz, DMSO-d6) δ 8.42 (d, J = 9.5 Hz, 1H), 8.04 (d, J = 8.1 Hz, 1H), 7.97 (s, 1H), 7.74 (s, 1H), 7.68 (s, 0.59H), 7.61 (s, 0.52H), 7.32 (s, 1H), 7.27 (s, 1H), 7.18 (d, J = 8.1 Hz, 1H), 5.22 (m, J = 9.7, 7.0 Hz, 1H), 4.99 (s, 0.46H), 4.91 (s, 0.47H), 4.76 (s, 3H), 4.55 (t, J = 10.2 Hz, 2H), 4.14 (s, 0.61H), 3.12 (s, 0.50H), 2.75 (d, J = 12.3 Hz, 0.58H), 2.29 (s, 0.63H), 2.09-2.00 (m, 1H), 1.94 (d, J = 20.9 Hz, 1H), 1.90-1.67 (m, 6H), 1.63 (s, 2H), 1.50 (d, J = 6.7 Hz, 1H), 1.48-1.38 (m, 4H), 1.38-1.21 (m, 2H), 1.16 (t, J = 12.1 Hz, 1H), 1.01-0.89 (m, 1H). |

TABLE 3-continued

| Example | ES/MS m/z [M + H]+ | 1H NMR |
|---|---|---|
| 953 | 690.3 | 1H NMR (400 MHz, DMSO-d6) δ 8.95 (d, J = 6.7 Hz, 1H), 8.06 (d, J = 8.0 Hz, 1H), 8.03-7.62 (m, 3H), 7.32 (s, 1H), 7.27-7.10 (m, 5H), 6.90 (s, 1H), 5.14 (p, J = 7.0 Hz, 1H), 5.07-4.75 (m, 2.5H), 4.62-4.45 (m, 0.5H), 4.31-4.14 (m, 0.5H), 3.99 (s, 3H), 3.91 (tt, J = 7.2, 3.9 Hz, 1H), 3.86-3.75 (m, 0.5H), 3.46-3.02 (m, 1.5H), 2.85-2.68 (m, 0.5H), 2.47-2.28 (m, 2H), 2.28-2.14 (m, 1H), 2.03-1.30 (m, 12H), 1.30-1.05 (m, 3H), 1.06-0.78 (m, 2H), 0.56-0.39 (m, 1H), 0.39-0.27 (m, 1H). |
| 954 | 681.4 | 1H NMR (400 MHz, DMSO-d6) δ 9.16 (d, J = 7.0 Hz, 1H), 8.08 (d, J = 8.0 Hz, 1H), 7.97 (s, 2H), 7.75 (d, J = 8.1 Hz, 1H), 7.75 (s, 1H), 7.49 (d, J = 8.1 Hz, 1H), 7.37 (s, 1H), 7.27 (d, J = 8.1 Hz, 1H), 7.08 (s, 1H), 6.90 (s, 1H), 5.21 (p, J = 7.0 Hz, 1H), 5.13-4.92 (m, 0.36H, rotamer), 4.93-4.80 (m, 1H), 4.68-4.43 (m, 1H), 4.35-4.17 (m, 1H), 4.12 (s, 3H), 4.00 (s, 3H), 3.65-3.57 (m, 0.32H, rotamer), 3.46-3.30 (m, 0.66H, rotamer), 3.29-3.01 (m, 1H), 2.88-2.70 (m, 1H), 2.42-2.19 (m, 3H), 2.07-1.91 (m, 1H), 1.91-1.70 (m, 2H), 1.69-1.56 (m, 3H), 1.51 (d, J = 7.0 Hz, 3H), 1.48-1.32 (m, 2H), 1.34-1.08 (m, 3H), 0.61-0.35 (m, 1H). |
| 955 | 640.3 | 1H NMR (400 MHz, DMSO-d6) δ 8.21 (d, J = 8.2 Hz, 1H), 8.03-7.63 (m, 3H), 7.41-7.33 (m, 2H), 7.13 (s, 1H), 6.90 (s, 1H), 5.06-4.86 (m, 2H), 4.77-4.65 (m, 1H), 4.60-4.46 (m, 0.5H), 4.28-4.18 (m, 0.5H), 4.13 (s, 3H), 3.99 (s, 3H), 3.85 (ddd, J = 11.7, 7.6, 4.2 Hz, 1H), 3.56 (dt, J = 11.7, 7.4 Hz, 1H), 3.44-3.22 (m, 2H), 3.17-3.06 (m, 0.5H), 2.81-2.69 (m, 0.5H), 2.66-2.57 (m, 1H), 2.31-2.11 (m, 2H), 2.08-1.40 (m, 12H), 1.19 (dt, J = 21.7, 7.3 Hz, 1H), 1.00-0.85 (m, 1H), 0.69-0.56 (m, 1H), 0.36 (q, J = 8.1 Hz, 1H), −0.51 (q, J = 12.9 Hz, 1H). |

BIOLOGICAL EXAMPLE

Protein Expression and Purification

The open reading frame of human PAD4 (NM_012387), A2-P663, was PCR amplified from a DNA template purchased from OriGene (catalog number RC206501) using Taq polymerase with the following pair of 5' (GCCCAGGGGACATTGATCCGT (SEQ ID NO: 1)) and 3' (TCAGGGCACCATGTTCCACCA (SEQ ID NO: 2)) primer that contains a stop codon. The PCR product was ligated into linearized pET-SUMO vector (Invitrogen, Carlsbad, CA), which is part of the Champion™ pET SUMO Protein Expression System. After sequence verification for the correct orientation, the pET-SUMO-hPAD4 expression plasmid was transformed into BL21(DE3) cells.

E. Coli BL21(DE3) cells were inoculated in LB medium with kanamycin at 37° C. until A600 nm reached about 0.5. Protein expression was induced by addition of 0.5 mM IPTG (final) and continued overnight at 16° C. at 220 rpm.

Cells were harvested by centrifugation at 5000 rpm for 10 minutes at 4° C. The pellet was resuspended in 300 ml lysis buffer (20 mM Tris-HCl, pH 8.0, 1 mM EDTA, 500 mM NaCl, 1 mM (tris(2-carboxyethyl)phosphine) (TCEP), 10% glycerol, and 1% Triton X100 and EDTA free protease inhibitor) and lysed by 3× passage through a microfluidizer (Microfluidics, Newton, MA) at 18,000 psi. The cell lysate was clarified by centrifugation at 30,000 rpm for 60 minutes at 4° C. The supernatant was applied to a 5 ml Ni-HP (GE HealthCare Cat #17524701) column preequilibrated in Ni-A buffer (20 mM Tris-HCl, pH 8.0, 20 mM Imidazole, 1 mM TCEP, 10% glycerol, and 400 mM NaCl). Bound protein was eluted with a 0-100% linear gradient of 100 mL Ni-B buffer (Ni A buffer+0.5 M Imidazole).

The His-Sumo tag was cleaved using sumo protease (Thermo Fisher Cat #: 12588018) while dialyzing in buffer (20 mM Tris-HCl, pH 8.0, 1 mM EDTA, 500 mM NaCl, 1 mM TCEP, 10% glycerol). The protein was then reloaded onto a Ni-HP column for a reverse purification step and recovered in flow through fraction. The protein with His-Sumo tag removed was then polished using a 16/60 Superdex-200 gel filtration column with gel filtration buffer (20 mM Tris pH 8.0, NaCl 400 mM and 1 mM TCEP). The fractions containing the protein were pulled and frozen at −80° C.

In Vitro PAD4 BAEE Biochemical Assay

The enzymatic activity of human PAD4 was monitored in a biochemical assay in the presence or absence of compounds using the small peptidyl arginine mimic BAEE (Nα-Benzoyl-L-arginine ethyl ester hydrochloride) as substrate. PAD4 activity led to deimination of BAEE and release of ammonia. Levels of ammonia were monitored by using an amine coupling reaction and were indicative of PAD4 enzymatic activity.

One hundred nanoliters of test compounds dissolved in DMSO at various concentrations were dispensed into a 384-well black OptiPlate using a Labcyte Echo instrument. Ten microliters of a solution of recombinant PAD4 and calcium chloride diluted in PAD4 assay buffer (50 mM MOPS [3-(N-morpholino) propanesulfonic acid], pH 7.6; 50 mM sodium chloride; 0.05% Tween-20; 2 mM dithiothreitol) was added to the compound-containing plate and was incubated for 30 minutes at 25° C. Ten microliters of a solution of BAEE (Sigma-Aldrich #B4500) diluted in PAD4 assay buffer was then added to start the reaction. Final concentrations were 5 nM PAD4, 2 mM calcium chloride, and 3 mM BAEE. The reaction mixture was incubated at 25° C. for 2 hours and was stopped with the addition of 10 microliters of a solution of 75 mM EDTA (Ethylenediaminetetraacetic acid) in PAD4 assay buffer. Thirty microliters of detection solution (5 mM o-phthalaldehyde, 50 mM MOPS [3-(N-morpholino) propanesulfonic acid], pH 7.6; 50 mM sodium chloride; 0.05% Tween-20; 5 mM dithiothreitol) was then added and the reaction was incubated for 1 hour at 25° C. The level of fluorescent thiol-substituted isoindole resulting from the reaction of ammonia, o-phthalaldehyde, and dithiothreitol was measured on an Envision plate reader (PerkinElmer) with 405 nm excitation and 535 nm emission.

Data were normalized based on maximum inhibition (50 micromolar of the covalent PAD inhibitor BB-Cl-Amidine (Bicker, K. L.; Anguish, L.; Chumanevich, A. A.; Cameron, M. D.; Cui, X.; Witalison, E.; Subramanian, V.; Zhang, X.; Chumanevich, A. P.; Hofseth, L. J.; Coonrod, S. A.; Thompson, P. R. ACS Med. Chem. Lett. 2012, 3, 1081-1085). and no inhibition (DMSO) controls. Least squares curve fittings were performed using a four-parameter variable slope non-linear regression model. $IC_{50}$ is defined as the concentration of compound required to inhibit 50% of maximum activity. $IC_{50}$ values from multiple experiments were averaged by geometric mean and the standard deviation was calculated. Data is shown in Table 4.

TABLE 4

| Example | PAD4 $IC_{50}$ (nM) |
|---|---|
| 1 | 104 |
| 2 | 75 |
| 3 | 110 |
| 4 | 69 |
| 5 | 76 |
| 6 | 105 |
| 7 | 101 |
| 8 | 71 |
| 9 | 53 |
| 10 | 56 |
| 11 | 251 |
| 12 | 120 |
| 13 | 121 |
| 14 | 121 |
| 15 | 60 |
| 16 | 67 |
| 17 | 74 |
| 18 | 85 |
| 19 | 76 |
| 20 | 62 |
| 21 | 63 |
| 22 | 62 |
| 23 | 40 |
| 24 | 56 |
| 25 | 775 |
| 26 | 86 |
| 27 | 201 |
| 28 | 46 |
| 29 | 70 |
| 30 | 1777 |
| 31 | 81 |
| 32 | 12 |
| 33 | 248 |
| 34 | 54 |
| 35 | 34 |
| 36 | 372 |
| 37 | 553 |
| 38 | 1203 |
| 39 | 23 |
| 40 | 24 |
| 41 | 268 |
| 42 | 108 |
| 43 | 118 |
| 44 | 64 |
| 45 | 4958 |
| 46 | 277 |
| 47 | 458 |
| 48 | 75 |
| 49 | 112 |
| 50 | 10000 |
| 51 | 215 |
| 52 | 424 |
| 53 | 283 |
| 54 | 1380 |
| 55 | 4677 |
| 56 | 193 |
| 57 | 213 |
| 58 | 77 |
| 59 | 161 |
| 60 | 118 |
| 61 | 231 |
| 62 | 150 |
| 63 | 24987 |

TABLE 4-continued

| Example | PAD4 $IC_{50}$ (nM) |
|---|---|
| 64 | 315 |
| 65 | 50000 |
| 66 | 1156 |
| 67 | 1301 |
| 68 | 287 |
| 69 | 201 |
| 70 | 137 |
| 71 | 560 |
| 72 | 308 |
| 73 | 125 |
| 74 | 221 |
| 75 | 103 |
| 76 | 87 |
| 77 | 367 |
| 78 | 80 |
| 79 | 76 |
| 80 | 255 |
| 81 | 505 |
| 82 | 8113 |
| 83 | 204 |
| 84 | 89 |
| 85 | 406 |
| 86 | 643 |
| 87 | 83 |
| 88 | 97 |
| 89 | 113 |
| 90 | 497 |
| 91 | 82 |
| 92 | 175 |
| 93 | 161 |
| 94 | 165 |
| 95 | 86 |
| 96 | 3131 |
| 97 | 57 |
| 98 | 122 |
| 99 | 111 |
| 100 | 833 |
| 101 | 7447 |
| 102 | 45 |
| 103 | 166 |
| 104 | 115 |
| 105 | 27425 |
| 106 | 201 |
| 107 | 24 |
| 108 | 150 |
| 109 | 303 |
| 110 | 70 |
| 111 | 49 |
| 112 | 81 |
| 113 | 302 |
| 114 | 61 |
| 115 | 40 |
| 116 | 255 |
| 117 | 54 |
| 118 | 41 |
| 119 | 60 |
| 120 | 22 |
| 121 | 46 |
| 122 | 16 |
| 123 | 12 |
| 124 | 12 |
| 125 | 21 |
| 126 | 25 |
| 127 | 31 |
| 128 | 13 |
| 129 | 13 |
| 130 | 21 |
| 131 | 15 |
| 132 | 28 |
| 133 | 47 |
| 134 | 125 |
| 135 | 37 |
| 136 | 40 |
| 137 | 35 |
| 138 | 18 |
| 139 | 40 |
| 140 | 97 |
| 141 | 68 |

TABLE 4-continued

| Example | PAD4 IC$_{50}$ (nM) |
|---|---|
| 142 | 28 |
| 143 | 158 |
| 144 | 31 |
| 145 | 58 |
| 146 | 47 |
| 147 | 365 |
| 148 | 45 |
| 149 | 46 |
| 150 | 107 |
| 151 | 123 |
| 152 | 43 |
| 153 | 116 |
| 154 | 57 |
| 155 | 77 |
| 156 | 56 |
| 157 | 36 |
| 158 | 241 |
| 159 | 62 |
| 160 | 53 |
| 161 | 108 |
| 162 | 55 |
| 163 | 51 |
| 164 | 33 |
| 165 | 235 |
| 166 | 49 |
| 167 | 90 |
| 168 | 39 |
| 169 | 69 |
| 170 | 118 |
| 171 | 804 |
| 172 | 101 |
| 173 | 109 |
| 174 | 80 |
| 175 | 231 |
| 176 | 196 |
| 177 | 30488 |
| 178 | 50 |
| 179 | 62 |
| 180 | 75 |
| 181 | 171 |
| 182 | 31 |
| 183 | 121 |
| 184 | 42 |
| 185 | 66 |
| 186 | 139 |
| 187 | 109 |
| 188 | 49 |
| 189 | 33 |
| 190 | 94 |
| 191 | 140 |
| 192 | 6686 |
| 193 | 66 |
| 194 | 150 |
| 195 | 56 |
| 196 | 116 |
| 197 | 6493 |
| 198 | 5955 |
| 199 | 18388 |
| 200 | 50000 |
| 201 | 737 |
| 202 | 5126 |
| 203 | 114 |
| 204 | 3348 |
| 205 | 50000 |
| 206 | 850 |
| 207 | 187 |
| 208 | 136 |
| 209 | 74 |
| 210 | 39 |
| 211 | 34 |
| 212 | 22 |
| 213 | 385 |
| 214 | 15 |
| 215 | 20 |
| 216 | 33 |
| 217 | 32 |
| 218 | 29 |
| 219 | 72 |

TABLE 4-continued

| Example | PAD4 IC$_{50}$ (nM) |
|---|---|
| 220 | 49 |
| 221 | 32 |
| 222 | 64 |
| 223 | 28 |
| 224 | 57 |
| 225 | 73 |
| 226 | 24 |
| 227 | 154 |
| 228 | 131 |
| 229 | 72 |
| 230 | 84 |
| 231 | 84 |
| 232 | 549 |
| 233 | 82 |
| 234 | 622 |
| 235 | 113 |
| 236 | 858 |
| 237 | 62 |
| 238 | 87 |
| 239 | 583 |
| 240 | 137 |
| 241 | 82 |
| 242 | 31 |
| 243 | 68 |
| 244 | 2577 |
| 245 | 411 |
| 246 | 3325 |
| 247 | 18 |
| 248 | 44 |
| 249 | 51 |
| 250 | 44 |
| 251 | 74 |
| 252 | 45 |
| 253 | 103 |
| 254 | 32 |
| 255 | 59 |
| 256 | 48 |
| 257 | 2474 |
| 258 | 39 |
| 259 | 37 |
| 260 | 453 |
| 261 | 106 |
| 262 | 4444 |
| 263 | 69 |
| 264 | 91 |
| 265 | 81 |
| 266 | 153 |
| 267 | 88 |
| 268 | 137 |
| 269 | 36 |
| 270 | 90 |
| 271 | 65 |
| 272 | 69 |
| 273 | 68 |
| 274 | 104 |
| 275 | 24 |
| 276 | 343 |
| 277 | 50000 |
| 278 | 47 |
| 279 | 82 |
| 280 | 64 |
| 281 | 88 |
| 282 | 13 |
| 283 | 13 |
| 284 | 52 |
| 285 | 7 |
| 286 | 9 |
| 287 | 55 |
| 288 | 36 |
| 289 | 25 |
| 290 | 221 |
| 291 | 335 |
| 292 | 53 |
| 293 | 548 |
| 294 | 275 |
| 295 | 3346 |
| 296 | 23734 |
| 297 | 129 |

TABLE 4-continued

| Example | PAD4 IC$_{50}$ (nM) |
|---|---|
| 298 | 914 |
| 299 | 58 |
| 300 | 50 |
| 301 | 36 |
| 302 | 67 |
| 303 | 525 |
| 304 | 70 |
| 305 | 65 |
| 306 | 85 |
| 307 | 82 |
| 308 | 72 |
| 309 | 1378 |
| 310 | 135 |
| 311 | 175 |
| 312 | 56 |
| 313 | 85 |
| 314 | 156 |
| 315 | 45 |
| 316 | 14 |
| 317 | 16 |
| 318 | 18 |
| 319 | 266 |
| 320 | 17 |
| 321 | 32 |
| 322 | 15 |
| 323 | 14 |
| 324 | 36 |
| 325 | 16 |
| 326 | 30 |
| 327 | 12 |
| 328 | 25 |
| 329 | 48 |
| 330 | 80 |
| 331 | 69 |
| 332 | 20 |
| 333 | 33 |
| 334 | 39 |
| 335 | 32 |
| 336 | 34 |
| 337 | 32 |
| 338 | 53 |
| 339 | 39 |
| 340 | 61 |
| 341 | 59 |
| 342 | 43 |
| 343 | 371 |
| 344 | 51 |
| 345 | 60 |
| 346 | 97 |
| 347 | 51 |
| 348 | 66 |
| 349 | 34 |
| 350 | 38 |
| 351 | 97 |
| 352 | 53 |
| 353 | 29 |
| 354 | 26 |
| 355 | 18 |
| 356 | 37 |
| 357 | 31 |
| 358 | 83 |
| 359 | 104 |
| 360 | 58 |
| 361 | 74 |
| 362 | 137 |
| 363 | 110 |
| 364 | 203 |
| 365 | 119 |
| 366 | 120 |
| 367 | 82 |
| 368 | 34 |
| 369 | 37 |
| 370 | 163 |
| 371 | 222 |
| 372 | 183 |
| 373 | 254 |
| 374 | 121 |
| 375 | 109 |
| 376 | 82 |
| 377 | 32 |
| 378 | 41 |
| 379 | 2045 |
| 380 | 1269 |
| 381 | 29 |
| 382 | 108 |
| 383 | 28 |
| 384 | 62 |
| 385 | — |
| 386 | 24 |
| 387 | 25 |
| 388 | 12 |
| 389 | 31 |
| 390 | 88 |
| 391 | 34 |
| 392 | 22 |
| 393 | 63 |
| 394 | 23 |
| 395 | 29 |
| 396 | 17 |
| 397 | 91 |
| 398 | 74 |
| 399 | 86 |
| 400 | 150 |
| 401 | 90 |
| 402 | 91 |
| 403 | 50000 |
| 404 | 83 |
| 405 | 27 |
| 406 | 22 |
| 407 | 70 |
| 408 | 255 |
| 409 | 83 |
| 410 | 51 |
| 411 | 398 |
| 412 | 42 |
| 413 | 37 |
| 414 | 125 |
| 415 | 52 |
| 416 | 34 |
| 417 | 62 |
| 418 | 122 |
| 419 | 370 |
| 420 | 184 |
| 421 | 304 |
| 422 | 39 |
| 423 | 64 |
| 424 | 111 |
| 425 | 104 |
| 426 | 25 |
| 427 | 54 |
| 428 | 29 |
| 429 | 68 |
| 430 | 44 |
| 431 | 41 |
| 432 | 161 |
| 433 | 46 |
| 434 | 41 |
| 435 | 394 |
| 436 | 93 |
| 437 | 30 |
| 438 | 25 |
| 439 | 32 |
| 440 | 27 |
| 441 | 37 |
| 442 | 32 |
| 443 | 37 |
| 444 | 20 |
| 445 | 72 |
| 446 | 38 |
| 447 | 37 |
| 448 | 26 |
| 449 | 22 |
| 450 | 21 |
| 451 | 19 |
| 452 | 37 |
| 453 | 53 |

TABLE 4-continued

| Example | PAD4 IC$_{50}$ (nM) |
|---|---|
| 454 | 31 |
| 455 | 36 |
| 456 | 57 |
| 457 | 38 |
| 458 | 23 |
| 459 | 130 |
| 460 | 71 |
| 461 | 51 |
| 462 | 31 |
| 463 | 29 |
| 464 | 28 |
| 465 | 23 |
| 466 | 55 |
| 467 | 27 |
| 468 | 28 |
| 469 | 21 |
| 470 | 43 |
| 471 | 44 |
| 472 | 42 |
| 473 | 44 |
| 474 | 49 |
| 475 | 62 |
| 476 | 38 |
| 477 | 35 |
| 478 | 50 |
| 479 | 47 |
| 480 | 134 |
| 481 | 231 |
| 482 | 26 |
| 483 | 33 |
| 484 | 44 |
| 485 | 29 |
| 486 | 110 |
| 487 | 82 |
| 488 | 64 |
| 489 | 78 |
| 490 | 86 |
| 491 | 253 |
| 492 | 156 |
| 493 | 76 |
| 494 | 136 |
| 495 | 518 |
| 496 | 125 |
| 497 | 54 |
| 498 | 67 |
| 499 | 163 |
| 500 | 90 |
| 501 | 271 |
| 502 | 128 |
| 503 | 110 |
| 504 | 172 |
| 505 | 97 |
| 506 | 39 |
| 507 | 32 |
| 508 | 57 |
| 509 | 146 |
| 510 | 277 |
| 511 | 95 |
| 512 | 65 |
| 513 | 161 |
| 514 | 371 |
| 515 | 74 |
| 516 | 48 |
| 517 | 128 |
| 518 | 49 |
| 519 | 44 |
| 520 | 35 |
| 521 | 76 |
| 522 | 40 |
| 523 | 205 |
| 524 | 388 |
| 525 | 78 |
| 526 | 65 |
| 527 | 215 |
| 528 | 55 |
| 529 | 409 |
| 530 | 51 |
| 531 | 36 |
| 532 | 239 |
| 533 | 398 |
| 534 | 56 |
| 535 | 384 |
| 536 | 137 |
| 537 | 87 |
| 538 | 90 |
| 539 | 175 |
| 540 | 90 |
| 541 | 123 |
| 542 | 479 |
| 543 | 405 |
| 544 | 40 |
| 545 | 56 |
| 546 | 59 |
| 547 | 50 |
| 548 | 56 |
| 549 | 129 |
| 550 | 60 |
| 551 | 43 |
| 552 | 61 |
| 553 | 47 |
| 554 | 34 |
| 555 | 56 |
| 556 | 69 |
| 557 | 31 |
| 558 | 80 |
| 559 | 47 |
| 560 | 52 |
| 561 | 523 |
| 562 | 466 |
| 563 | 26 |
| 564 | 24 |
| 565 | 41 |
| 566 | 97 |
| 567 | 33 |
| 568 | 33 |
| 569 | 109 |
| 570 | 94 |
| 571 | 31 |
| 572 | 53 |
| 573 | 23 |
| 574 | 117 |
| 575 | 26 |
| 576 | 68 |
| 577 | 84 |
| 578 | 78 |
| 579 | 50 |
| 580 | 24 |
| 581 | 176 |
| 582 | 271 |
| 583 | 69 |
| 584 | 51 |
| 585 | 74 |
| 586 | 88 |
| 587 | 163 |
| 588 | 193 |
| 589 | 145 |
| 590 | 683 |
| 591 | 81 |
| 592 | 175 |
| 593 | 44 |
| 594 | 112 |
| 595 | 37 |
| 596 | 3577 |
| 597 | 42 |
| 598 | 42 |
| 599 | 67 |
| 600 | 46 |
| 601 | 45 |
| 602 | 97 |
| 603 | 44 |
| 604 | 86 |
| 605 | 129 |
| 606 | 129 |
| 607 | 51 |
| 608 | 115 |
| 609 | 172 |
| 610 | 190 |

TABLE 4-continued

| Example | PAD4 IC$_{50}$ (nM) |
|---|---|
| 611 | 85 |
| 612 | 157 |
| 613 | 108 |
| 614 | 114 |
| 615 | 94 |
| 616 | 71 |
| 617 | 1121 |
| 618 | 69 |
| 619 | 38 |
| 620 | 36 |
| 621 | 43 |
| 622 | 59 |
| 623 | 47 |
| 624 | 70 |
| 625 | 9 |
| 626 | 48 |
| 627 | 49 |
| 628 | 83 |
| 629 | 108 |
| 630 | 122 |
| 631 | 211 |
| 632 | 46 |
| 633 | 57 |
| 634 | 251 |
| 635 | 682 |
| 636 | 52 |
| 637 | 31 |
| 638 | — |
| 639 | 15 |
| 640 | 24 |
| 641 | 49 |
| 642 | 23 |
| 643 | 54 |
| 644 | 76 |
| 645 | 36 |
| 646 | 22 |
| 647 | 58 |
| 648 | 41 |
| 649 | 52 |
| 650 | 59 |
| 651 | 59 |
| 652 | 42 |
| 653 | 44 |
| 654 | 51 |
| 655 | 60 |
| 656 | 124 |
| 657 | 14 |
| 658 | 25 |
| 659 | 32 |
| 660 | 16 |
| 661 | 27 |
| 662 | 32 |
| 663 | 71 |
| 664 | 51 |
| 665 | 26 |
| 666 | 86 |
| 667 | 70 |
| 668 | 22 |
| 669 | 45 |
| 670 | 6 |
| 671 | 20 |
| 672 | 28 |
| 673 | 27 |
| 674 | 17 |
| 675 | 559 |
| 676 | 83 |
| 677 | 82 |
| 678 | 15 |
| 679 | 33 |
| 680 | 34 |
| 681 | 39 |
| 682 | 28 |
| 683 | 16 |
| 684 | 20 |
| 685 | 13 |
| 686 | 44 |
| 687 | 64 |
| 688 | 719 |
| 689 | 39 |
| 690 | 54 |
| 691 | 33 |
| 692 | 27 |
| 693 | 18 |
| 694 | 268 |
| 695 | 57 |
| 696 | 48 |
| 697 | 74 |
| 698 | 68 |
| 699 | 640 |
| 700 | 22 |
| 701 | 5 |
| 702 | 21 |
| 703 | 11 |
| 704 | 31 |
| 705 | 20 |
| 706 | 19 |
| 707 | 21 |
| 708 | 91 |
| 709 | 25 |
| 710 | 18 |
| 711 | 19 |
| 712 | 24 |
| 713 | 19 |
| 714 | 40 |
| 715 | 19 |
| 716 | 13 |
| 717 | 11 |
| 718 | 18 |
| 719 | 91 |
| 720 | 65 |
| 721 | 246 |
| 722 | 174 |
| 723 | 309 |
| 724 | 94 |
| 725 | 136 |
| 726 | 23 |
| 727 | 93 |
| 728 | 75 |
| 729 | 307 |
| 730 | 270 |
| 731 | 140 |
| 732 | 214 |
| 733 | 96 |
| 734 | 185 |
| 735 | 143 |
| 736 | 304 |
| 737 | 75 |
| 738 | 48 |
| 739 | 62 |
| 740 | 30 |
| 741 | 33 |
| 742 | 58 |
| 743 | — |
| 744 | 96 |
| 745 | 22 |
| 746 | 25 |
| 747 | 10 |
| 748 | 25 |
| 749 | 17 |
| 750 | 28 |
| 751 | 32 |
| 752 | 30 |
| 753 | 113 |
| 754 | 59 |
| 755 | 29 |
| 756 | 31 |
| 757 | 5 |
| 758 | 17 |
| 759 | 17 |
| 760 | 70 |
| 761 | 67 |
| 762 | 26 |
| 763 | 13 |
| 764 | 22 |
| 765 | 16 |
| 766 | 28 |

TABLE 4-continued

| Example | PAD4 IC$_{50}$ (nM) |
|---|---|
| 767 | 18 |
| 768 | 59 |
| 769 | 13 |
| 770 | 5 |
| 771 | 28 |
| 772 | 6 |
| 773 | 16 |
| 774 | 33 |
| 775 | 29 |
| 776 | 17 |
| 777 | 17 |
| 778 | 338 |
| 779 | 339 |
| 780 | 53 |
| 781 | 73 |
| 782 | 63 |
| 783 | 109 |
| 784 | 97 |
| 785 | 954 |
| 786 | 237 |
| 787 | 94 |
| 788 | 35 |
| 789 | 22 |
| 790 | 23 |
| 791 | 17 |
| 792 | 342 |
| 793 | 24 |
| 794 | 18 |
| 795 | 661 |
| 796 | 5 |
| 797 | 16 |
| 798 | 17 |
| 799 | 12 |
| 800 | 74 |
| 801 | 334 |
| 802 | 22 |
| 803 | 118 |
| 804 | 27 |
| 805 | 6 |
| 806 | 42 |
| 807 | 31 |
| 808 | 15 |
| 809 | 39 |
| 810 | 25 |
| 811 | 26 |
| 812 | 31 |
| 813 | 26 |
| 814 | 38 |
| 815 | 26 |
| 816 | 19 |
| 817 | 13 |
| 818 | 12 |
| 819 | 10 |
| 820 | 168 |
| 821 | 102 |
| 822 | 205 |
| 823 | 146 |
| 824 | 43 |
| 825 | 38 |
| 826 | 31 |
| 827 | 36 |
| 828 | 24 |
| 829 | 15 |
| 830 | 19 |
| 831 | 75 |
| 832 | 13 |
| 833 | 61 |
| 834 | 126 |
| 835 | 16 |
| 836 | 32 |
| 837 | 30 |
| 838 | 49 |
| 839 | 13 |
| 840 | 61 |
| 841 | 17 |
| 842 | 49 |
| 843 | 18 |
| 844 | 35 |
| 845 | 16 |
| 846 | 27 |
| 847 | 82 |
| 848 | 33 |
| 849 | 15 |
| 850 | 64 |
| 851 | 20 |
| 852 | 16 |
| 853 | 48 |
| 854 | 68 |
| 855 | 65 |
| 856 | 156 |
| 857 | 13 |
| 858 | 459 |
| 859 | 38 |
| 860 | 44 |
| 861 | 39 |
| 862 | 78 |
| 863 | 69 |
| 864 | 68 |
| 865 | 230 |
| 866 | 79 |
| 867 | 44 |
| 868 | 37 |
| 869 | 24 |
| 870 | 83 |
| 871 | 31 |
| 872 | 90 |
| 873 | 120 |
| 874 | 29 |
| 875 | 148 |
| 876 | 122 |
| 877 | 40 |
| 878 | 26 |
| 879 | 34 |
| 880 | 39 |
| 881 | 24 |
| 882 | 22 |
| 883 | 18 |
| 884 | 24 |
| 885 | 11 |
| 886 | 29 |
| 887 | 52 |
| 888 | 37 |
| 889 | 54 |
| 890 | 10 |
| 891 | 13 |
| 892 | 27 |
| 893 | 28 |
| 894 | 72 |
| 895 | 34 |
| 896 | 56 |
| 897 | 40 |
| 898 | 156 |
| 899 | 30 |
| 900 | 28 |
| 901 | 59 |
| 902 | 48 |
| 903 | 55 |
| 904 | 101 |
| 905 | 72 |
| 906 | 55 |
| 907 | 82 |
| 908 | 151 |
| 909 | 52 |
| 910 | 49 |
| 911 | 61 |
| 912 | 17 |
| 913 | 22 |
| 914 | 16 |
| 915 | 47 |
| 916 | 26 |
| 917 | 27 |
| 918 | 31 |
| 919 | 20 |
| 920 | 21 |
| 921 | 30 |
| 922 | 35 |

TABLE 4-continued

| Example | PAD4 IC$_{50}$ (nM) |
|---|---|
| 923 | 24 |
| 924 | 46 |
| 925 | 40 |
| 926 | 23 |
| 927 | 49 |
| 928 | 51 |
| 929 | 18 |
| 930 | 22 |
| 931 | 64 |
| 932 | 58 |
| 933 | 27 |
| 934 | 103 |
| 935 | 29 |
| 936 | 39 |
| 937 | 187 |
| 938 | 28 |
| 939 | 44 |
| 940 | 80 |
| 941 | 68 |
| 942 | 72 |
| 943 | 48 |
| 944 | 64 |
| 945 | 34 |
| 946 | 69 |
| 947 | 92 |
| 948 | 28 |
| 949 | 31 |
| 950 | 38 |
| 951 | 24 |
| 952 | 21 |
| 953 | 68 |
| 954 | 32 |
| 955 | 81 |

What is claimed is:

1. A compound of Formula (I):

$$\text{(I)}$$

[chemical structure diagram showing: $R^{11}$, $R^{10}$, N, O, $R^1$, $X^4$, $X^1$, $X^2$, $X^3$, N, $L^1{}_{m1}L^2{}_{m2}L^3{}_{m3}L^4{}_{m4}L^5{}_{m5}$, $X^5$, $L^6{}_{m6}$, $X^7$]

or a pharmaceutically acceptable salt, stereoisomer, mixture of stereoisomers, or tautomer thereof, wherein:

$X^1$ and $X^2$ are C or N;

$X^3$ is N—$R^3$ or C—$R^3$; provided that two of $X^1$, $X^2$, and $X^3$ are C; where each dashed line represents an optional bond to complete valency requirements of each $X^1$, $X^2$ and $X^3$;

$X^4$ is N or C—$R^2$;

$X^5$ is N or $CR^6$;

$X^7$ is N or $CR^7$;

$R^1$ is hydrogen, halo, —CN, —$OR^{12}$, —$N(R^{12})_2$, —$SR^{12}$, —$C_{1-8}$ alkyl optionally substituted with 1 to 3 $Z^1$, $C_{3-6}$ cycloalkyl optionally substituted with 1 to 3 $Z^1$, or 4-6 membered heterocyclyl optionally substituted with 1 to 3 $Z^1$;

$R^2$ is hydrogen, halo, —CN, —$OR^{12}$, —$N(R^{12})_2$, —$SR^{12}$, —$C_{1-8}$ alkyl optionally substituted with 1 to 3 $Z^2$, $C_{3-6}$ cycloalkyl optionally substituted with 1 to 3 $Z^2$, or 4-6 membered heterocyclyl optionally substituted with 1 to 3 $Z^2$;

when $X^3$ is N—$R^3$, $R^3$ is hydrogen, $C_{1-8}$ alkyl optionally substituted with 1 to 3 $Z^3$, $C_{3-10}$ alkenyl optionally substituted with 1 to 3 $Z^3$, $C_{3-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; and when $X^3$ is C—$R^3$; $R^3$ is hydrogen, halo, —CN, —$OR^{12}$, —$N(R^{12})_2$, —$SR^{12}$, $C_{1-8}$ alkyl optionally substituted with 1 to 3 $Z^3$, $C_{2-10}$ alkenyl optionally substituted with 1 to 3 $Z^3$, $C_{2-10}$ alkynyl optionally substituted with 1 to 3 $Z^3$, $C_{3-10}$ cycloalkyl optionally substituted with 1 to 3 $Z^3$, or 4-10 membered heterocyclyl optionally substituted with 1 to 3 $Z^3$; or when $R^2$ is —$C_{1-8}$ alkyl, —$OR^{12}$, or —$N(R^{12})_2$, and $R^3$ is $C_{1-8}$ alkyl, then $R^2$ and $R^3$ may be taken together with the atoms to which they are attached to form an optionally substituted 6 to 8 membered ring;

$R^6$ is hydrogen, halo, —CN, —$OR^{12}$, —$C_{1-8}$ alkyl optionally substituted with 1 to 3 $Z^6$, $C_{3-6}$ cycloalkyl optionally substituted with 1 to 3 $Z^6$, or 4-6 membered heterocyclyl optionally substituted with 1 to 3 $Z^6$;

$R^7$ is hydrogen, halo, —CN, —$OR^{12}$, —$C_{1-8}$ alkyl optionally substituted with 1 to 3 $Z^7$, $C_{3-6}$ cycloalkyl optionally substituted with 1 to 3 $Z^7$, or 4-6 membered heterocyclyl optionally substituted with 1 to 3 $Z^7$;

$L^1$, $L^2$, $L^3$, $L^4$, $L^5$, and $L^6$ are each independently:

$C_{1-10}$ alkylene, optionally substituted with 1 to 3 $Z^8$;
$C_{2-10}$ alkenylene, optionally substituted with 1 to 3 $Z^8$;
$C_{2-10}$ alkynylene, optionally substituted with 1 to 3 $Z^8$;
2-6 membered heteroalkylene, optionally substituted with 1 to 3 $Z^8$;
$C_3$-$C_{10}$ cycloalkylene, optionally substituted with 1 to 3 $Z^8$;
4-10 membered heterocyclene, optionally substituted with 1 to 3 $Z^8$;
$C_{6-10}$ arylene, optionally substituted with 1 to 3 $Z^8$;
5-10 membered heteroarylene, optionally substituted with 1 to 3 $Z^8$; or
—O—, —$N(R^8)$—, —S—, —C(O)—, —C(O)O—, —$C(O)N(R^8)$—, —SO—, —$SO_2$—, —$SO_2N(R^8)$—, —$N(R^8)C(O)O$—, —OC(O)O—, —$N(R^8)C(O)N(R^8)$—, —$N(R^8)S(O)_2N(R^8)$—, —$N(R^8)C(N—CN)$—, —$S(O)(NR^8)$—, or —$S(O)(NR^8)N(R^8)$—; and m1, m2, m3, m4, m5, and m6 are each independently 0 or 1;

provided that $L^1{}_{m1}$, $L^2{}_{m2}$, $L^3{}_{m3}$, $L^4{}_{m4}$, $L^5{}_{m5}$, and $L^6{}_{m6}$ taken together with the four consecutive atoms between which they are attached form an optionally substituted 11 to 20 membered macrocyclic ring;

each $R^8$ and $R^9$ is independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$R^{10}$ is hydrogen, —$C_{1-8}$ alkyl optionally substituted with 1 to 3 $Z^{10}$, or $C_{3-6}$ cycloalkyl optionally substituted with 1 to 3 $Z^{10}$;

$R^{11}$ is hydrogen, —$C_{1-8}$ alkyl optionally substituted with 1 to 4 $Z^{11}$, —$C_{3-8}$ cycloalkyl optionally substituted with 1 to 4 $Z^{11}$, or 4-12-membered heterocyclyl optionally substituted with 1 to 4 $Z^{11}$; or $R^{10}$ and $R^{11}$ are taken together with nitrogen to which they are attached to form a 4-12-membered heterocyclyl optionally substituted with 1 to 4 $Z^{11}$;

each $R^{12}$ and $R^{13}$ are independently hydrogen, $C_{1-8}$ alkyl optionally substituted with 1 to 3 $Z^{1b}$, $C_{2-8}$ alkenyl optionally substituted with 1 to 3 $Z^{1b}$, $C_{2-8}$ alkynyl optionally substituted with 1 to 3 $Z^{1b}$, $C_{3-10}$ cycloalkyl optionally substituted with 1 to 3 $Z^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

each $Z^1$, $Z^2$, $Z^3$, $Z^6$, $Z^7$, and $Z^8$ is independently oxo, halo, —$NO_2$, —$N_3$, —CN, $C_{1-8}$ alkyl optionally substituted by 1 to 3 $Z^{1a}$, $C_{2-8}$ alkenyl optionally substituted by 1 to 3 $Z^{1a}$, $C_{2-8}$ alkynyl optionally substituted by 1 to 3 $Z^{1a}$, $C_{3-8}$ cycloalkyl optionally substituted by 1 to 3 $Z^{1a}$, 6-10 membered aryl optionally substituted by 1 to 3 $Z^{1a}$, 4-10 membered heterocyclyl optionally substituted by 1 to 3 $Z^{1a}$, 5-10 membered heteroaryl optionally substituted with 1 to 3 $Z^{1a}$, —$OR^9$, —$C(O)R^9$, —$C(O)OR^9$, —$C(O)N(R^9)_2$, —$N(R^9)_2$, —$N(R^9)_3^+$, —$N(R^9)C(O)R^9$, —$N(R^9)C(O)OR^9$, —$N(R^9)C(O)N(R^9)_2$, —$N(R^9)S(O)_2(R^9)$, —$NR^9S(O)_2N(R^9)_2$, —$NR^9S(O)_2O(R^9)$, —$NS(O)(R^9)_2$, —$OC(O)R^9$, —$OC(O)OR^9$, —$OC(O)N(R^9)_2$, —$Si(R^9)_3$, —$SR^9$, —$S(O)R^9$, —$SF_5$, —$S(O)(NR^9)R^9$, —$S(NR^9)(NR^9)R^9$, —$S(O)(NR^9)N(R^9)_2$, —$S(O)(NCN)R^9$, —$S(O)_2R^9$, —$S(O)_2N(R^9)_2$, —$C(O)N(R^9)S(O)_2R^9$, or —$S(O)_2N(R^9)C(O)R^9$, wherein each $Z^2$, $Z^3$, $Z^6$, $Z^7$, and $Z^8$ is independently optionally substituted with 1 to 3 $Z^{1a}$;

each $Z^{1a}$ is independently oxo, halo, —$NO_2$, —$N_3$, —CN, $C_{1-8}$ alkyl optionally substituted by 1 to 3 $Z^{1b}$, $C_{2-8}$ alkenyl optionally substituted by 1 to 3 $Z^{1b}$, $C_{2-8}$ alkynyl optionally substituted by 1 to 3 $Z^{1b}$, $C_{3-8}$ cycloalkyl optionally substituted by 1 to 3 $Z^{1b}$, 6-10 membered aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{13}$, —$C(O)R^{13}$, —$C(O)OR^{13}$, —$C(O)N(R^{13})_2$, —$N(R^{13})_2$, —$N(R^{13})_3^+$, —$N(R^{13})C(O)R^{13}$, —$N(R^{13})C(O)OR^{13}$, —$N(R^{13})C(O)N(R^{13})_2$, —$N(R^{13})S(O)_2(R^{13})$, —$NR^{13}S(O)_2N(R^{13})_2$, —$NR^{13}S(O)_2O(R^{13})$, —$NS(O)(R^{13})_2$, —$OC(O)R^{13}$, —$OC(O)OR^{13}$, —$OC(O)N(R^{13})_2$, —$Si(R^{13})_3$, —$SR^{13}$, —$S(O)R^{13}$, —$SF_5$, —$S(O)(NR^{13})R^{13}$, —$S(NR^{13})(NR^{13})R^{13}$, —$S(O)(NR^{13})N(R^{13})_2$, —$S(O)(NCN)R^{13}$, —$S(O)_2R^{13}$, —$S(O)_2N(R^{13})_2$, —$C(O)N(R^{13})S(O)_2R^{13}$, or —$S(O)_2N(R^{13})C(O)R^{13}$;

each $Z^{10}$ and $Z^{11}$ is independently selected from oxo, halo, —CN, $C_{1-9}$ alkyl optionally substituted by 1 to 3 $Z^{1b}$, $C_{3-8}$ cycloalkyl optionally substituted by 1 to 3 $Z^{1b}$, aryl optionally substituted by 1 to 3 $Z^{1b}$, 4-10 membered heterocyclyl optionally substituted by 1 to 3 $Z^{1b}$, 5-10 membered heteroaryl optionally substituted with 1 to 3 $Z^{1b}$, —$OR^{13}$, —$C(O)R^{13}$, —$C(O)OR^{13}$, —$C(O)N(R^{13})_2$, —$N(R^{13})_2$, —$N(R^{13})_3^+$, —$N(R^{13})C(O)R^{13}$, —$N(R^{13})C(O)OR^{13}$, —$N(R^{13})C(O)N(R^{13})_2$, —$OC(O)R^{13}$, —$OC(O)OR^{13}$, —$OC(O)$—$N(R^{13})_2$, and —$S$—$R^{13}$; and each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —$O(C_{1-9}$ alkyl), —$O(C_{2-6}$ alkenyl), —$O(C_{2-6}$ alkynyl), —$O(C_{3-15}$ cycloalkyl), —$O(C_{1-8}$ haloalkyl), —$O(aryl)$, —$O(heteroaryl)$, —$O(heterocyclyl)$, —$OC(O)$ ($C_{1-9}$ alkyl), —$OC(O)(C_{2-6}$ alkenyl), —$OC(O)(C_{2-6}$ alkenyl), —$OC(O)(C_{2-6}$ alkynyl), —$OC(O)(C_{3-15}$ cycloalkyl), —$OC(O)(C_{1-8}$ haloalkyl), —$OC(O)(aryl)$, —$OC(O)(heteroaryl)$, —$OC(O)(heterocyclyl)$, —$NH_2$, —$NH(C_{1-9}$ alkyl), —$NH(C_{2-6}$ alkenyl), —$NH(C_{2-6}$ alkynyl), —$NH(C_{3-15}$ cycloalkyl), —$NH(C_{1-8}$ haloalkyl), —$NH(aryl)$, —$NH(heteroaryl)$, —$NH(heterocyclyl)$, —$N(C_{1-9}$ alkyl)$_2$, —$N(C_{3-15}$ cycloalkyl)$_2$, —$N(C_{2-6}$ alkenyl)$_2$, —$N(C_{2-6}$ alkynyl)$_2$, —$N(C_{3-15}$ cycloalkyl)$_2$, —$N(C_{1-8}$ haloalkyl)$_2$, —$N(aryl)_2$, —$N(heteroaryl)_2$, —$N(heterocyclyl)_2$, —$N(C_{1-9}$ alkyl)($C_{3-15}$ cycloalkyl), —$N(C_{1-9}$ alkyl)($C_{2-6}$ alkenyl), —$N(C_{1-9}$ alkyl)($C_{2-6}$ alkynyl), —$N(C_{1-9}$ alkyl)($C_{1-8}$ haloalkyl), —$N(C_{1-9}$ alkyl)(aryl), —$N(C_{1-9}$ alkyl)(heteroaryl), —$N(C_{1-9}$ alkyl)(heterocyclyl), —$C(O)(C_{1-9}$ alkyl), —$C(O)(C_{2-6}$ alkenyl), —$C(O)(C_{2-6}$ alkynyl), —$C(O)(C_{3-15}$ cycloalkyl), —$C(O)(C_{1-8}$ haloalkyl), —$C(O)(aryl)$, —$C(O)(heteroaryl)$, —$C(O)(heterocyclyl)$, —$C(O)O(C_{1-9}$ alkyl), —$C(O)O(C_{2-6}$ alkenyl), —$C(O)O(C_{2-6}$ alkynyl), —$C(O)O(C_{3-15}$ cycloalkyl), —$C(O)O(C_{1-8}$ haloalkyl), —$C(O)O(aryl)$, —$C(O)O(heteroaryl)$, —$C(O)O(heterocyclyl)$, —$C(O)NH_2$, —$C(O)NH(C_{1-9}$ alkyl), —$C(O)NH(C_{2-6}$ alkenyl), —$C(O)NH(C_{2-6}$ alkynyl), —$C(O)NH(C_{3-15}$ cycloalkyl), —$C(O)NH(C_{1-8}$ haloalkyl), —$C(O)NH(aryl)$, —$C(O)NH(heteroaryl)$, —$C(O)NH(heterocyclyl)$, —$C(O)N(C_{1-9}$ alkyl)$_2$, —$C(O)N(C_{3-15}$ cycloalkyl)$_2$, —$C(O)N(C_{2-6}$ alkenyl)$_2$, —$C(O)N(C_{2-6}$ alkynyl)$_2$, —$C(O)N(C_{1-8}$ haloalkyl)$_2$, —$C(O)N(aryl)_2$, —$C(O)N(heteroaryl)_2$, —$C(O)N(heterocyclyl)_2$, —$NHC(O)(C_{1-9}$ alkyl), —$NHC(O)(C_{2-6}$ alkenyl), —$NHC(O)(C_{2-6}$ alkynyl), —$NHC(O)(C_{3-15}$ cycloalkyl), —$NHC(O)(C_{1-8}$ haloalkyl), —$NHC(O)(aryl)$, —$NHC(O)(heteroaryl)$, —$NHC(O)(heterocyclyl)$, —$NHC(O)O(C_{1-9}$ alkyl), —$NHC(O)O(C_{2-6}$ alkenyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O(aryl)$, —$NHC(O)O(heteroaryl)$, —$NHC(O)O(heterocyclyl)$, —$NHC(O)NH(C_{1-9}$ alkyl), —$NHC(O)NH(C_{2-6}$ alkenyl), —$NHC(O)NH(C_{2-6}$ alkynyl), —$NHC(O)NH(C_{3-15}$ cycloalkyl), —$NHC(C_{1-8}$ haloalkyl), —$NHC(O)NH(aryl)$, —$NHC(O)NH(heteroaryl)$, —$NHC(O)NH(heterocyclyl)$, —SH, —$S(C_{1-9}$ alkyl), —$S(C_{2-6}$ alkenyl), —$S(C_{2-6}$ alkynyl), —$S(C_{3-15}$ cycloalkyl), —$S(C_{1-8}$ haloalkyl), —$S(aryl)$, —$S(heteroaryl)$, —$S(heterocyclyl)$, —$NHS(O)(C_{1-9}$ alkyl), —$N(C_{1-9}$ alkyl)($S(O)(C_{1-9}$ alkyl), —$S(O)N(C_{1-9}$ alkyl)$_2$, —$S(O)(C_{1-9}$ alkyl), —$S(O)(NH)(C_{1-9}$ alkyl), —$S(O)(C_{2-6}$ alkenyl), —$S(O)(C_{2-6}$ alkynyl), —$S(O)(C_{3-15}$ cycloalkyl), —$S(O)(C_{1-8}$ haloalkyl), —$S(O)(aryl)$, —$S(O)(heteroaryl)$, —$S(O)(heterocyclyl)$, —$S(O)_2(C_{1-9}$ alkyl), —$S(O)_2(C_{2-6}$ alkenyl), —$S(O)_2(C_{2-6}$ alkynyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), or —$S(O)_2N(C_{1-9}$ alkyl)$_2$;

wherein any alkyl, cycloalkyl, aryl, heteroaryl, or heterocyclyl of $Z^{1b}$ is optionally substituted with one or more halo, $C_{1-9}$ alkyl, $C_{1-8}$ haloalkyl, —OH, —$NH_2$, —$NH(C_{1-9}$ alkyl), —$NH(C_{3-15}$ cycloalkyl), —$NH(C_{1-8}$ haloalkyl), —$NH(aryl)$, —$NH(heteroaryl)$, —$NH(heterocyclyl)$, —$N(C_{1-9}$ alkyl)$_2$, —$N(C_{3-15}$ cycloalkyl)$_2$, —$NHC(O)(C_{3-15}$ cycloalkyl), —$NHC(O)(C_{1-8}$ haloalkyl), —$NHC(O)(aryl)$, —$NHC(O)(heteroaryl)$, —$NHC(O)(heterocyclyl)$, —$NHC(O)O(C_{1-9}$ alkyl), —$NHC(O)O(C_{2-6}$ alkynyl), —$NHC(O)O(C_{3-15}$ cycloalkyl), —$NHC(O)O(C_{1-8}$ haloalkyl), —$NHC(O)O(aryl)$, —$NHC(O)O(heteroaryl)$, —$NHC(O)O(heterocyclyl)$, —$NHC(O)NH(C_{1-9}$ alkyl), —$S(O)(NH)(C_{1-9}$ alkyl), —$S(O)_2(C_{1-9}$ alkyl), —$S(O)_2(C_{3-15}$ cycloalkyl), —$S(O)_2(C_{1-8}$ haloalkyl), —$S(O)_2(aryl)$, —$S(O)_2(heteroaryl)$, —$S(O)_2(heterocyclyl)$, —$S(O)_2NH(C_{1-9}$ alkyl), —$S(O)_2N(C_{1-9}$ alkyl)$_2$, —$O(C_{3-15}$ cycloalkyl), —$O(C_{1-8}$ haloalkyl), —$O(aryl)$, —$O(heteroaryl)$, —$O(heterocyclyl)$, or —$O(C_{1-9}$ alkyl).

2. The compound of claim 1, or a pharmaceutically acceptable salt, stereoisomer, mixture of stereoisomers, or tautomer thereof, wherein $R^1$ is hydrogen, fluoro, chloro, —CN, —$OR^{12}$, —$C_{1-6}$ alkyl, or $C_{3-5}$ cycloalkyl;

$R^2$ is hydrogen, fluoro, chloro, —$OR^{12}$, —$N(R^{12})_2$, —$C_{1-5}$ alkyl optionally substituted with 1 to 3 halo, or $C_{3-5}$ cycloalkyl;

$X^1$ and $X^2$ are each C;

$X^3$ is N—$R^3$, and $R^3$ is hydrogen, $C_{1-6}$ alkyl optionally substituted with 1 to 3 $Z^3$, $C_{3-6}$ alkenyl optionally substituted with 1 to 3 $Z^3$, $C_{3-6}$ alkynyl optionally substituted with 1 to 3 $Z^3$, $C_{3-6}$ cycloalkyl optionally substituted with 1 to 3 $Z^3$, or 4-6 membered heterocyclyl optionally substituted with 1 to 3 $Z^3$;

$X^4$ is C—$R^2$, wherein $R^2$ is hydrogen, —F, —Cl, —$CH_3$, —$CF_3$, —$CHF_2$, cyclopropyl, —$OCH_3$, —O— ethyl, —O-propyl, —O-isopropyl, —O-cyclopropyl, —$OCF_3$, or —$OCHF_2$; and $X^5$ is N.

3. The compound of claim 1, or a pharmaceutically acceptable salt, stereoisomer, mixture of stereoisomers, or tautomer thereof, wherein $L^1$, $L^2$, $L^3$, $L^4$, $L^5$, and $L^6$ are each independently:

$C_{1-10}$ alkylene optionally substituted with 1 to 2 $Z^8$;

$C_{2-10}$ alkenylene optionally substituted with 1 to 2 $Z^8$;

$C_{2-10}$ alkynylene optionally substituted with 1 to 2 $Z^8$;

2 to 6 membered heteroalkylene having 1 to 2 heteroatoms selected from O and N and optionally substituted with 1 to 2 $Z^8$;

$C_3$-$C_{10}$ cycloalkylene optionally substituted with 1 to 2 $Z^8$;

4-8 membered heterocyclene having 1 to 2 heteroatoms selected from O and N and optionally substituted with 1 to 2 $Z^8$;

$C_{6-10}$ arylene optionally substituted with 1 to 3 $Z^8$;

5-10 membered heteroarylene having 1 to 3 heteroatoms selected from O, N, and S and optionally substituted with 1 to 3 $Z^8$; or —O—, —N($R^8$)—, —C(O)—, —C(O)O—, —C(O)N($R^8$)—, —SO$_2$N($R^8$)—, —SO$_2$—, —N($R^8$)C(O)O—, —OC(O)O—, or —N($R^8$)C(O)N($R^8$); and m1, m2, m3, m4, m5, and m6 are each independently 0 or 1;

provided that $L^1_{m1}$, $L^2_{m2}$, $L^3_{m3}$, $L^4_{m4}$, $L^5_{m5}$, and $L^6_{m6}$ taken together with the four consecutive atoms between which they are attached form an optionally substituted 11 to 20 membered macrocyclic ring.

4. The compound of claim 1, or a pharmaceutically acceptable salt, stereoisomer, mixture of stereoisomers, or tautomer thereof, wherein $R^{10}$ is hydrogen or —CH$_3$, and $R^{11}$ is hydrogen, $C_{1-6}$ alkyl optionally substituted with 1 to 3 $Z^{11}$, $C_{3-6}$ cycloalkyl optionally substituted with 1 to 3 $Z^{11}$, or 4-12 membered heterocyclyl optionally substituted with 1 to 3 $Z^{11}$; or $R^{10}$ and $R^{11}$ taken together with the nitrogen to which they are attached form a 4-10 membered heterocyclyl optionally substituted with 1 to 3 $Z^{11}$.

5. The compound of claim 1, represented by Formula (Id):

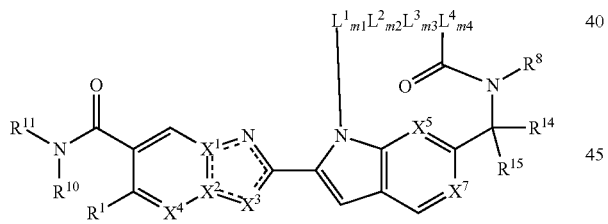

(Id)

or a pharmaceutically acceptable salt, stereoisomer, mixture of stereoisomers, or tautomer thereof, wherein:

$R^{14}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$; and $R^{15}$ is hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$;

or $R^{14}$ and $R^{15}$ can be taken together with the carbon to which they are attached to form a 3-6 membered cycloalkyl that is optionally substituted with 1 to 3 $Z^{1a}$ or 4-6 membered heterocyclyl containing 1-2 heteroatoms independently selected from O, N, or S that is optionally substituted with 1-3 $Z^{1a}$.

6. The compound of claim 1, represented by Formula (Iv-1):

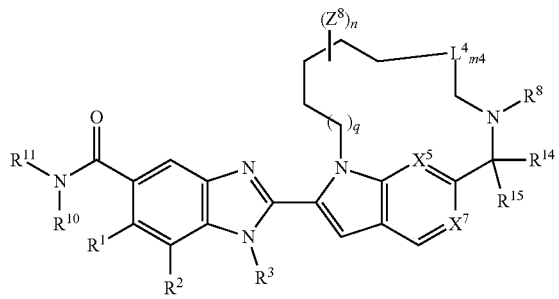

(Iv-1)

or a pharmaceutically acceptable salt, stereoisomer, mixture of stereoisomers, or tautomer thereof, wherein:

$L^4$ is methylene optionally substituted with 1 to 2 $Z^8$, $C_{3-6}$ cycloalkylene optionally substituted with 1 to 2 $Z^8$, 4-10 membered heterocyclene optionally substituted with 1 to 2 $Z^8$, 6-10 membered arylene optionally substituted with 1 to 2 $Z^8$, or 5-10 membered heteroarylene optionally substituted with 1 to 2 $Z^8$;

m4 is 1;

q is 0, 1 or 2;

n is 0, 1, 2, 3, or 4; and $R^{14}$ and $R^{15}$ are each independently hydrogen, $C_{1-8}$ alkyl optionally substituted with 1-3 $Z^{1a}$, $C_{3-8}$ cycloalkyl optionally substituted with 1-3 $Z^{1a}$, $C_{4-6}$ heterocyclyl having 1-3 heteroatoms selected from O, N, and S, optionally substituted with 1-3 $Z^{1a}$.

7. The compound of claim 6, or a pharmaceutically acceptable salt, stereoisomer, mixture of stereoisomers, or tautomer thereof, wherein $L^4$ is selected from the group consisting of:

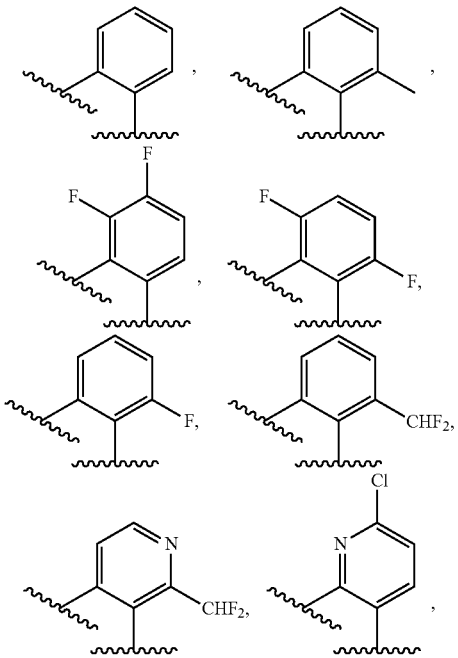

1259
-continued
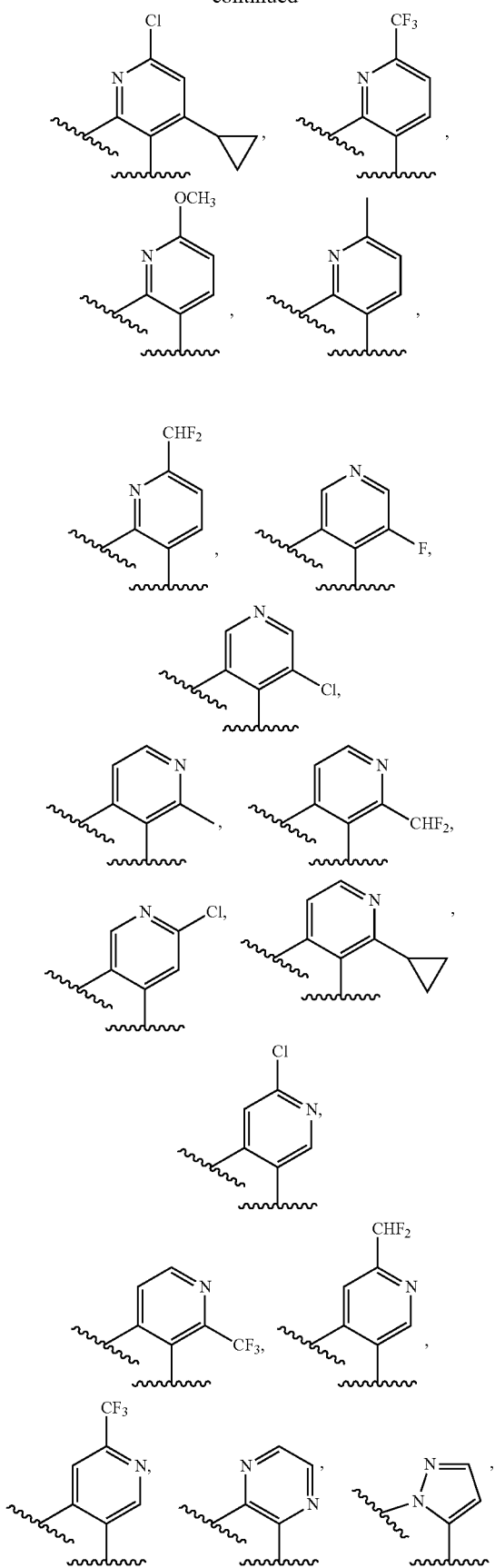
1260
-continued
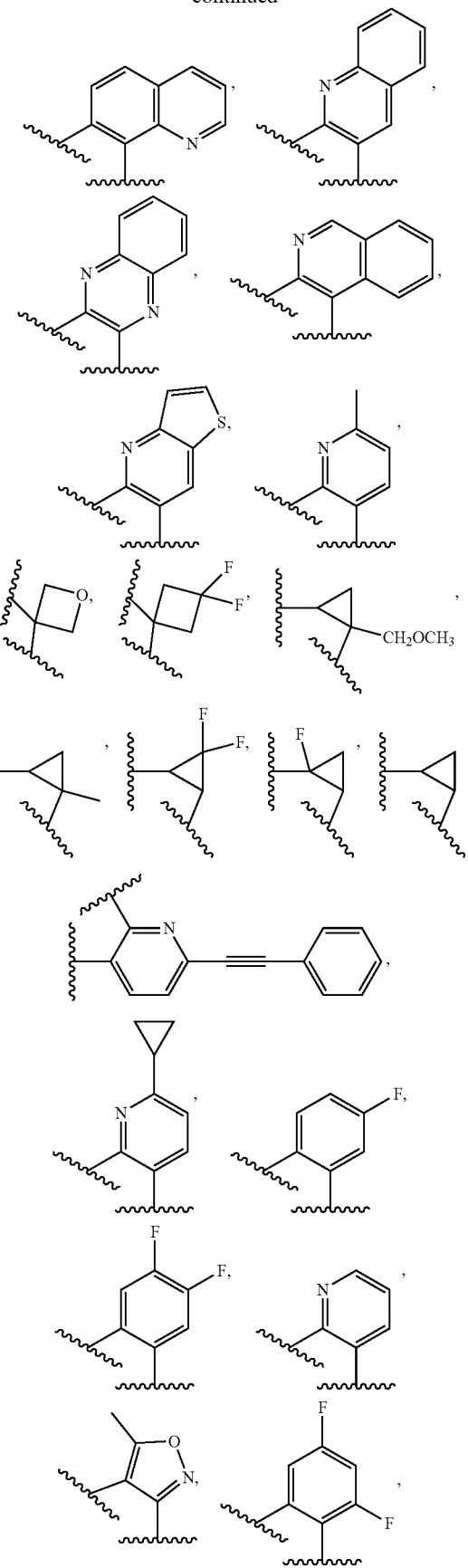

-continued

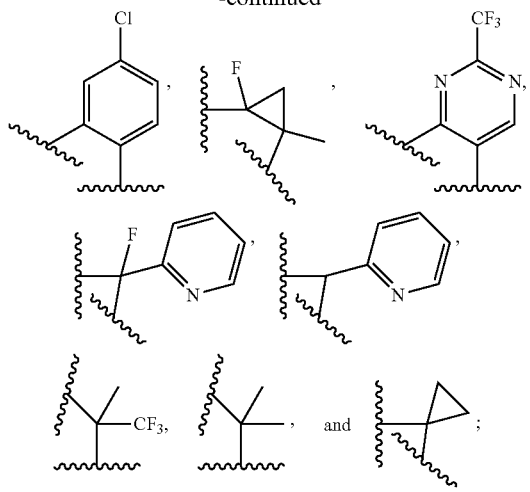

wherein either of the two broken bonds may be attached to —CO— in —CO—NR$^8$—.

8. A compound of Formula (Iu):

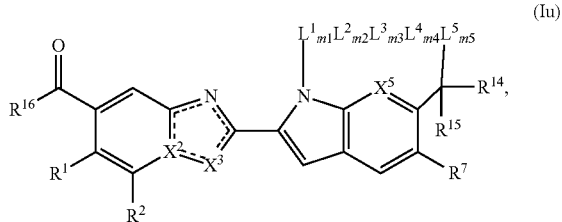

or a pharmaceutically acceptable salt, stereoisomer, mixture of stereoisomers, or tautomer thereof,
wherein
the moiety

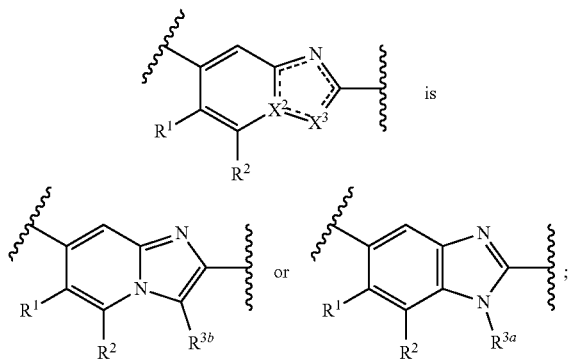

R$^1$ is hydrogen or fluoro;
R$^2$ is hydrogen, —OCH$_3$, —CH$_3$, fluoro, chloro, —OCHF$_2$, or —OCF$_3$;
R$^{3a}$ is —CH$_3$, —CH$_2$CH$_3$, —CH$_2$-cyclopropyl, —CH$_2$CHF$_2$, —CH$_2$CH$_2$OCH$_3$, or cyclopropyl optionally substituted with 1 to 3 fluoro or —CHF$_2$;
R$^{3b}$ is —CH$_3$ or cyclopropyl;
X$^5$ is CH, N, or CF;
R$^7$ is hydrogen or fluoro;

R$^{14}$ and R$^{15}$ are each independently hydrogen, C$_{1-6}$ alkyl, cyclopropyl, or —CF$_3$; or R$^{14}$ and R$^{15}$ taken together with the carbon to which they are attached form a C$_{3-6}$ cycloalkyl;
R$^{16}$ is

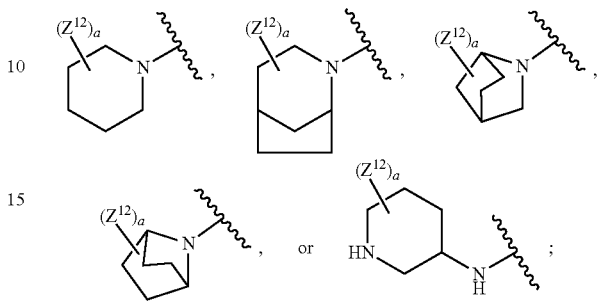

each Z$^{12}$ is independently —NH$_2$, fluoro, —OH, C$_{1-6}$ alkyl optionally substituted with 1 to 3 fluoro, or —OCH$_3$ optionally substituted with 1 to 3 fluoro; a is 1, 2, or 3;
L$^1$ is C$_{1-10}$ alkylene optionally substituted with 1 to 3 Z$^8$;
L$^2$ is C$_3$-C$_6$ cycloalkylene optionally substituted with 1 to 3 Z$^8$, or C$_{2-6}$ alkenylene optionally substituted with 1 to 3 Z$^8$;
L$^3$ is —O—, —O—C$_{1-8}$ alkylene optionally substituted with 1 to 3 Z$^8$, or C$_{1-8}$ alkylene optionally substituted with 1 to 3 Z$^8$;
L$^4$ is C$_{1-10}$ alkylene optionally substituted with 1 to 3 Z$^8$, 4-10 membered heterocyclene optionally substituted with 1 to 3 Z$^8$, C$_3$-C$_{10}$ cycloalkylene optionally substituted with 1 to 3 Z$^8$, 5-10 membered heteroarylene optionally substituted with 1 to 3 Z$^8$, or C$_{6-10}$ arylene optionally substituted with 1 to 3 Z$^8$;
each Z$^8$ is independently halo, —CN, C$_{1-8}$ alkyl optionally substituted with 1 to 3 Z$^{1a}$, C$_{2-8}$ alkenyl optionally substituted with 1 to 3 Z$^{1a}$, C$_{2-8}$ alkynyl optionally substituted with 1 to 3 Z$^{1a}$, C$_{3-8}$ cycloalkyl optionally substituted with 1 to 3 Z$^{1a}$, 6-10 membered aryl optionally substituted with 1 to 3 Z$^{1a}$, 4-10 membered heterocyclyl optionally substituted with 1 to 3 Z$^{1a}$, 5-10 membered heteroaryl optionally substituted with 1 to 3 Z$^{1a}$, —OR$^9$, —C(O)R$^9$, or —C(O)OR$^9$;
each Z$^{1a}$ is independently halo, —CN, C$_{1-8}$ alkyl optionally substituted with 1 to 3 Z$^{1b}$, C$_{2-8}$ alkenyl optionally substituted with 1 to 3 Z$^{1b}$, or C$_{2-8}$ alkynyl optionally substituted with 1 to 3 Z$^{1b}$; C$_{3-8}$ cycloalkyl optionally substituted with 1 to 3 Z$^{1b}$, 6-10 membered aryl optionally substituted with 1 to 3 Z$^{1b}$, 4-10 membered heterocyclyl optionally substituted with 1 to 3 Z$^{1b}$, 5-10 membered heteroaryl optionally substituted with 1 to 3 Z$^{1b}$, —OR$^{13}$, —C(O)R$^{13}$, or —C(O)OR$^{13}$;
each Z$^{1b}$ is independently hydroxy, halo, —CN, C$_{1-9}$ alkyl, C$_{2-6}$ alkenyl, C$_{2-6}$ alkynyl, C$_{3-15}$ cycloalkyl, C$_{1-8}$ haloalkyl, 6-10 membered aryl, 5-10 membered heteroaryl, 4-10 membered heterocyclyl, —O(C$_{1-9}$ alkyl), —O(C$_{3-15}$ cycloalkyl), —O(C$_{1-8}$ haloalkyl), —C(O)O (C$_{1-9}$ alkyl), —C(O)O(C$_{3-15}$ cycloalkyl), or —C(O)O (C$_{1-8}$ haloalkyl);
each R$^9$ and R$^{13}$ are independently hydrogen, C$_{1-8}$ alkyl optionally substituted with 1 to 3 Z$^{1b}$, C$_{2-8}$ alkenyl optionally substituted with 1 to 3 Z$^{1b}$, C$_{2-8}$ alkynyl optionally substituted with 1 to 3 Z$^{1b}$, C$_{3-10}$ cycloalkyl optionally substituted with 1 to 3 Z$^{1b}$, 4-10 membered heterocyclyl optionally substituted with 1 to 3 $Z^{1b}$, $C_{6-10}$ aryl optionally substituted with 1 to 3 $Z^{1b}$, or 5-10 membered heteroaryl optionally substituted with 1 to 3 $Z^{1b}$;

$L^5$ is —NHCO—, —N(CH$_3$)CO—, or —N(COCH$_3$)—;

m1 is 1;
m2 is 0 or 1;
m3 is 0 or 1;
m4 is 0 or 1; and
m5 is 1.

9. The compound of claim 8, represented by Formula (Iu-1)

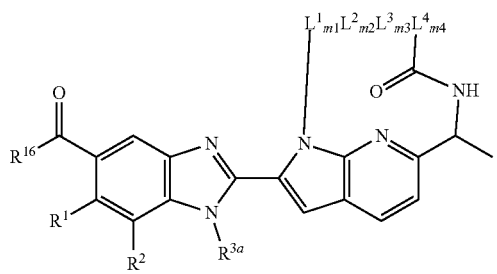

(Iu-1)

or a pharmaceutically acceptable salt, stereoisomer, mixture of stereoisomers, or tautomer thereof.

10. The compound of claim 9, or a pharmaceutically acceptable salt, stereoisomer, mixture of stereoisomers, or tautomer thereof, wherein $L^1$ is $C_{1-10}$ alkylene optionally substituted with 1 to 3 halo;
$L^2$ is $C_3$-$C_6$ cycloalkylene optionally substituted with 1 to 3 halo, or $C_{2-6}$ alkenylene optionally substituted with 1 to 3 halo;
$L^3$ is —O—, —O—$C_{1-8}$ alkylene optionally substituted with 1 to 3 halo, or $C_{1-8}$ alkylene optionally substituted with 1 to 3 halo;
$L^4$ is $C_{1-6}$ alkylene optionally substituted with 1 to 3 $Z^{8a}$, 5-10 membered nitrogen-containing heteroarylene optionally substituted with 1 to 3 $Z^{8b}$, $C_{6-10}$ arylene optionally substituted with 1 to 3 $Z^{8b}$, or $C_3$-$C_6$ cycloalkylene optionally substituted with 1 to 3 $Z^{8b}$;
each $Z^{8a}$ is independently halo, or 5-10 membered heteroaryl optionally substituted with 1-2 halo; and
each $Z^{8b}$ is independently halo, $C_{1-6}$ alkyl, $C_{1-6}$ haloalkyl, —O($C_{1-6}$ alkyl), —O($C_{1-6}$ haloalkyl), —O($C_{3-6}$ cycloalkyl), cyclopropyl, or phenylethynyl.

11. The compound of claim 10, or a pharmaceutically acceptable salt, stereoisomer, mixture of stereoisomers, or tautomer thereof, wherein $L^4$ is selected from the group consisting of

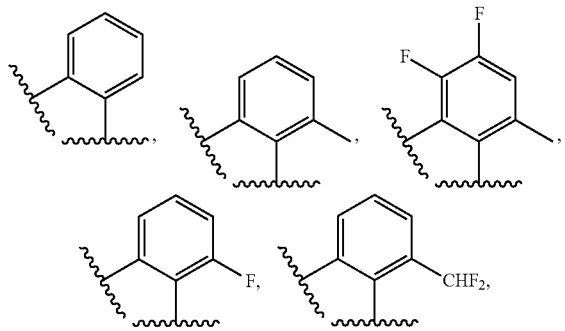

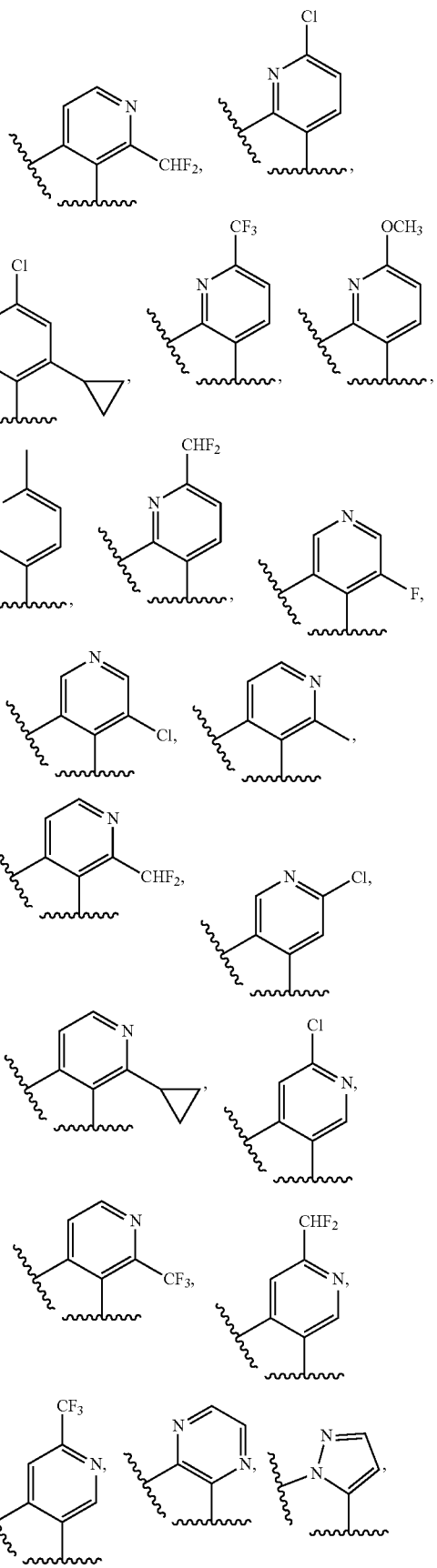

1265
-continued

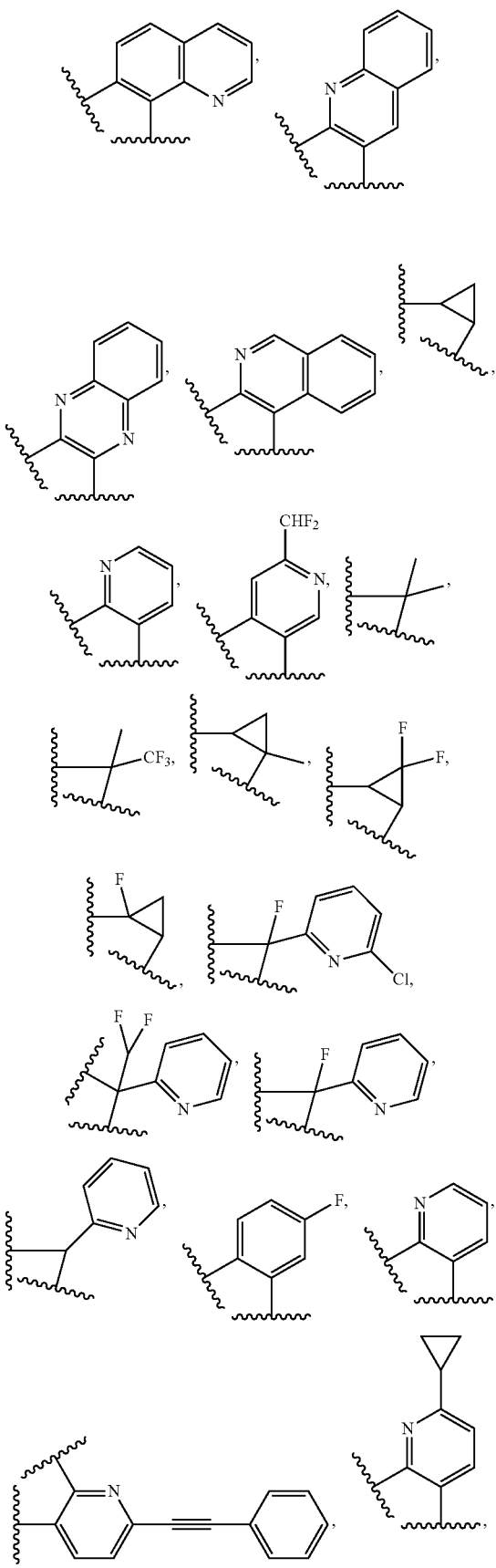

1266
-continued

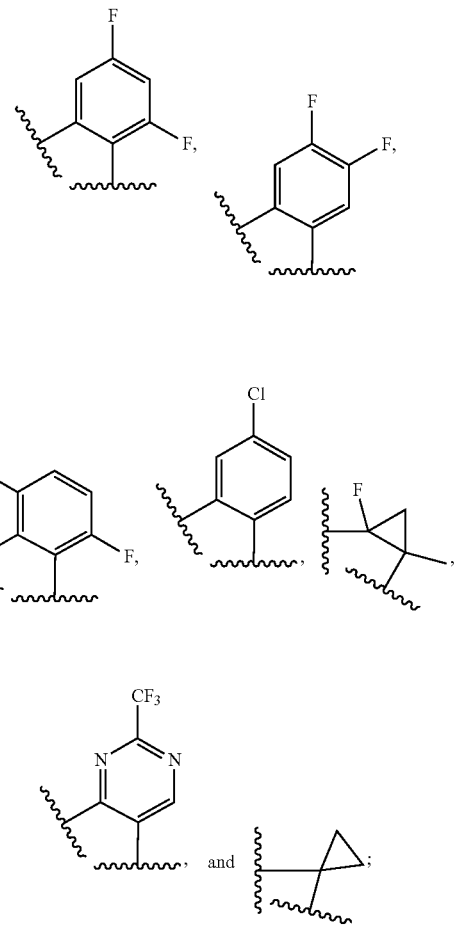

either of the two broken bonds may be attached to $L^5$, or —CO— in —CO—NH—.

12. The compound of claim 8, or a pharmaceutically acceptable salt, stereoisomer, mixture of stereoisomers, or tautomer thereof, wherein $R^1$ is hydrogen;
$R^2$ is fluoro, hydrogen or —OCH$_3$;
$R^{3a}$ is —CH$_3$ or cyclopropyl; and
$R^{16}$ is

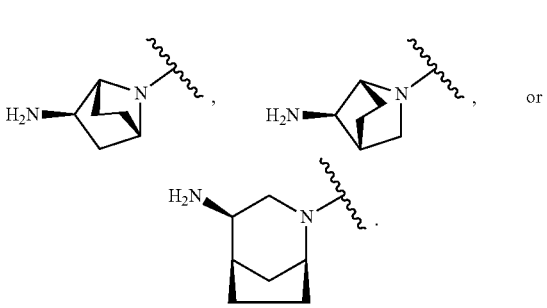

13. The compound of claim 1, or a pharmaceutically acceptable salt, stereoisomer, mixture of stereoisomers, or tautomer thereof, wherein the compound having a structure of:

1267
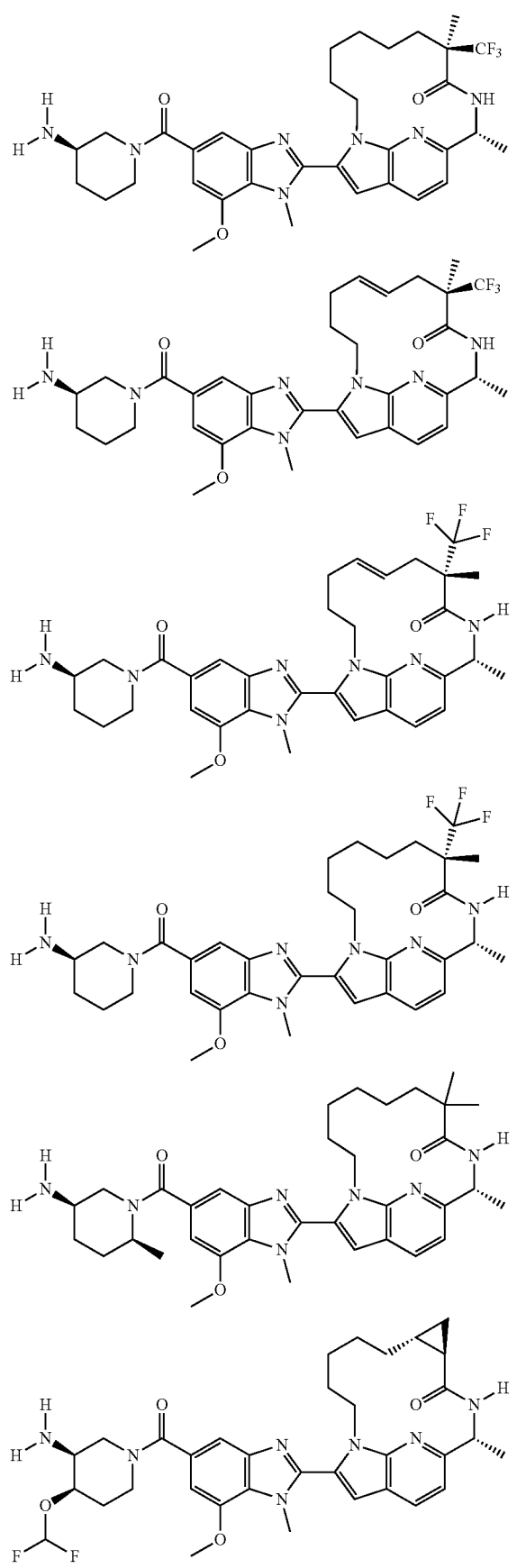
1268
-continued
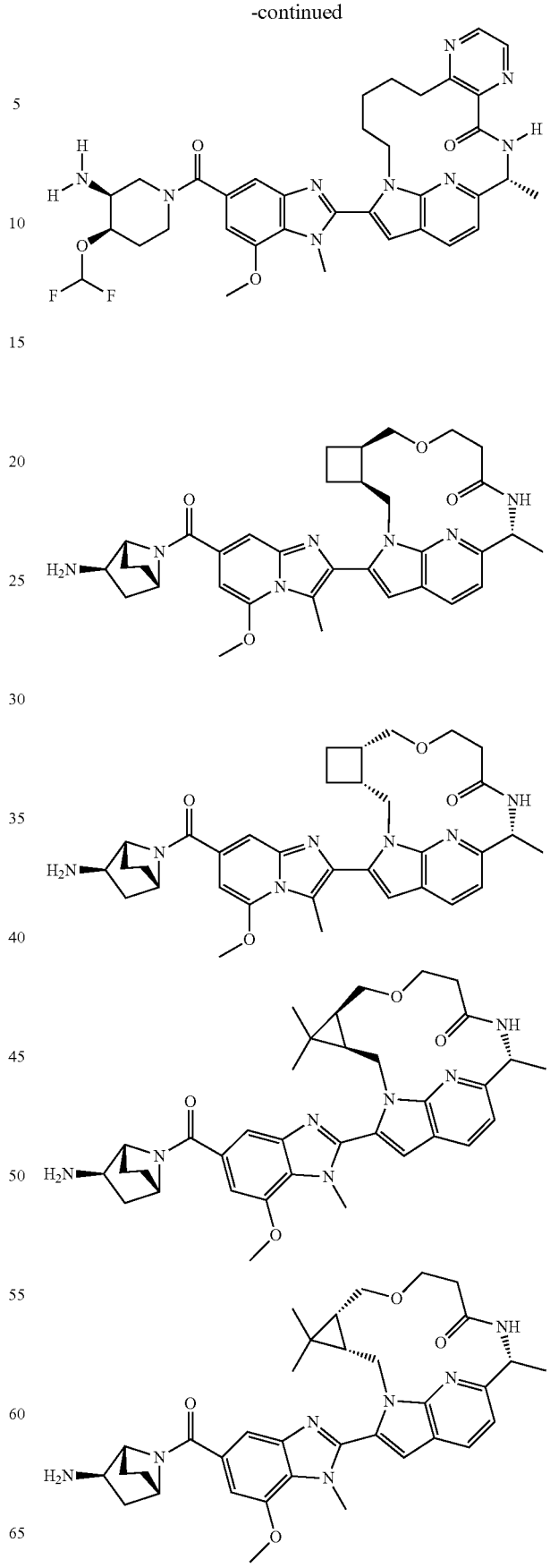

1269
-continued
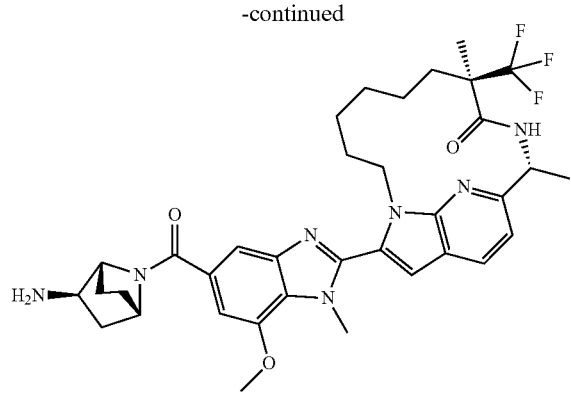
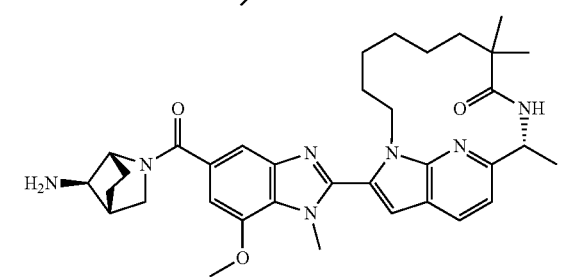
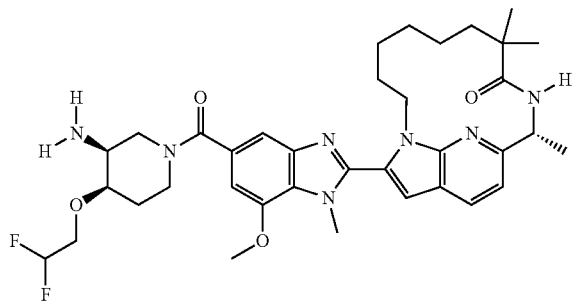
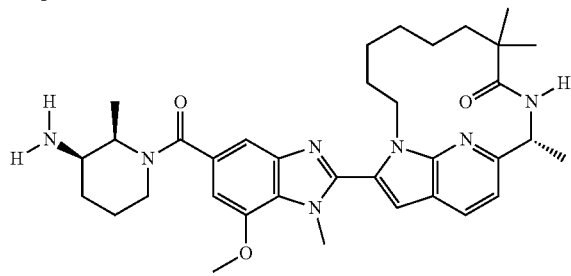
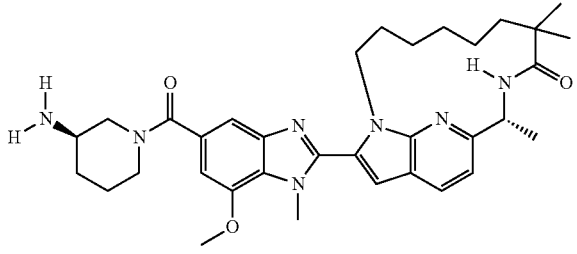
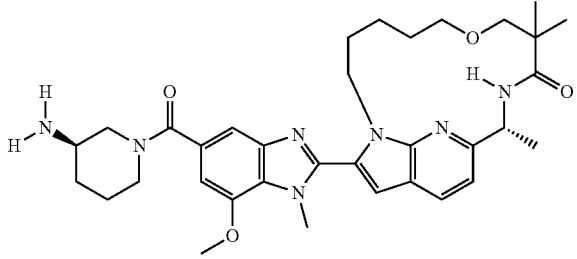
1270
-continued
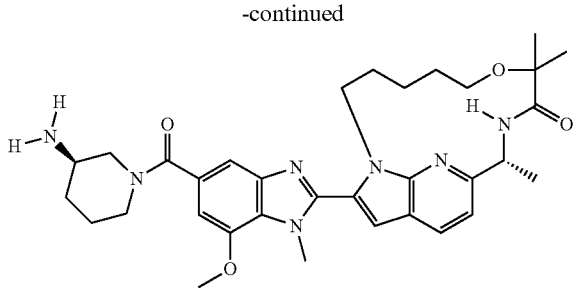
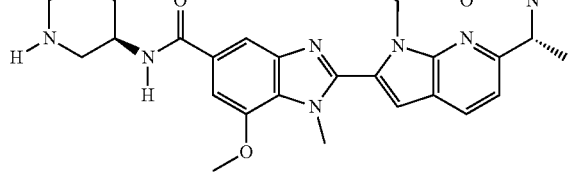
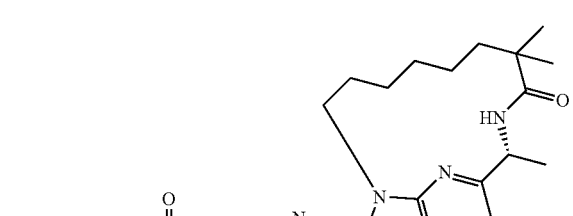
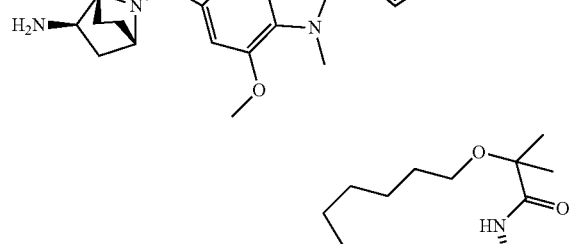
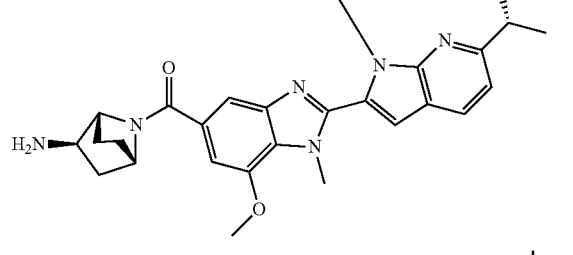
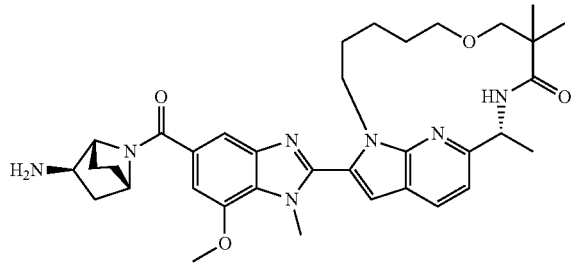

1271
-continued
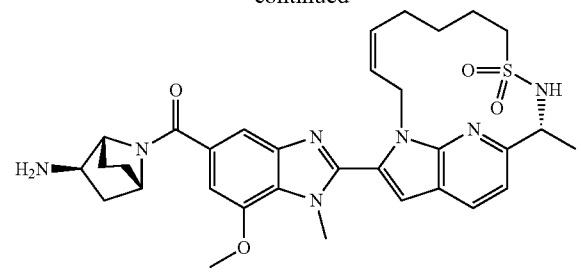
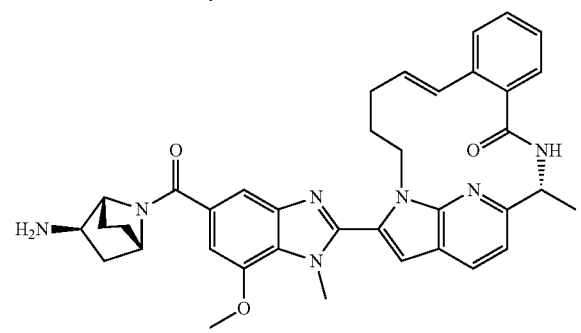
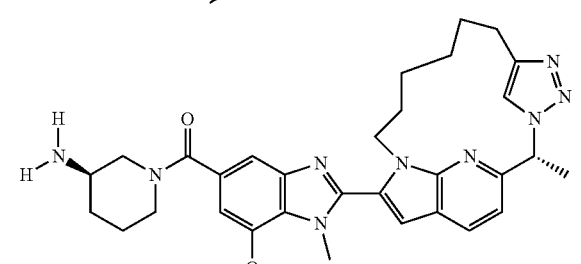
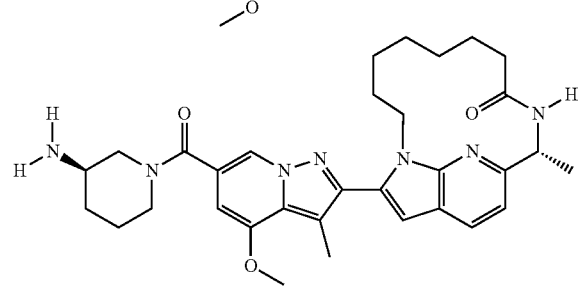
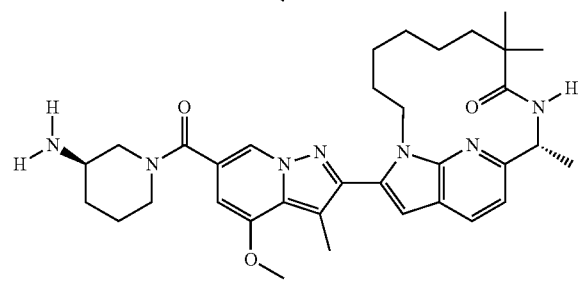
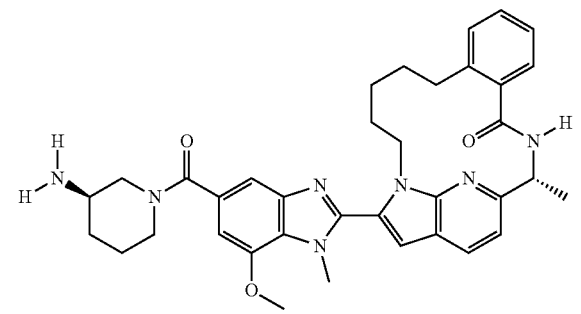
1272
-continued
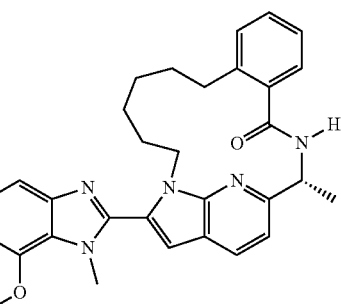
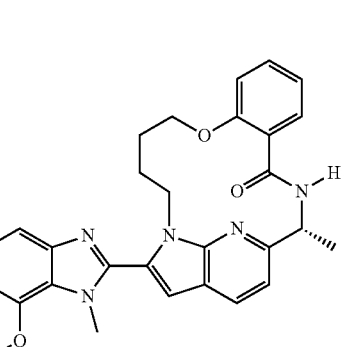
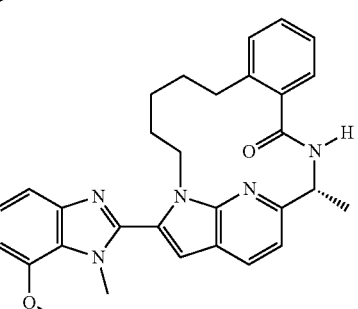
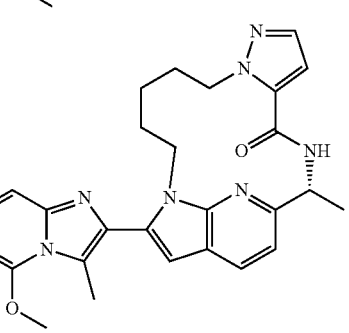
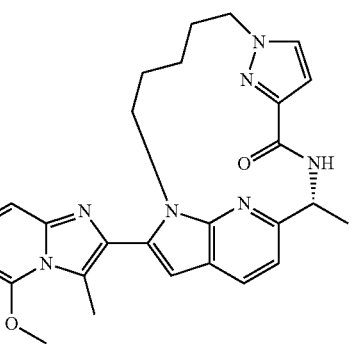

1273
-continued
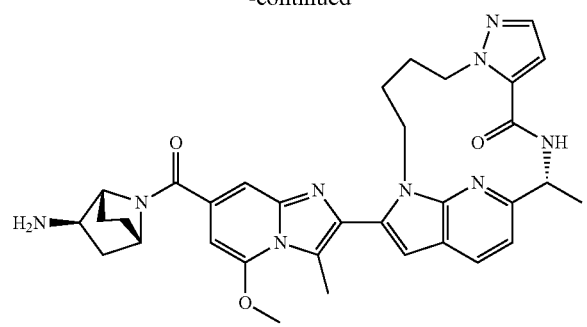
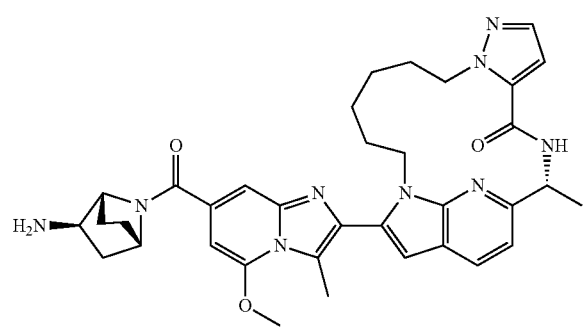
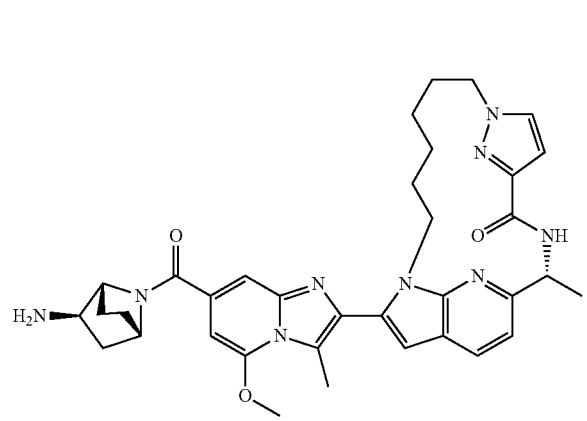
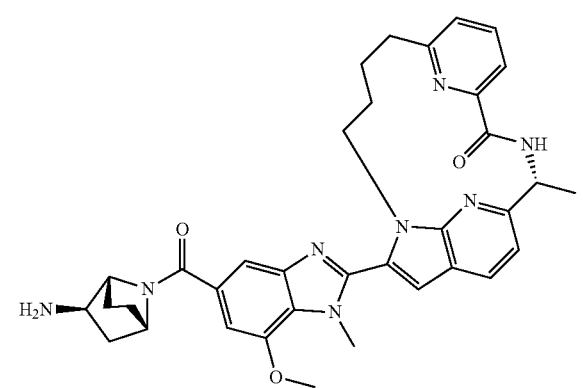
1274
-continued
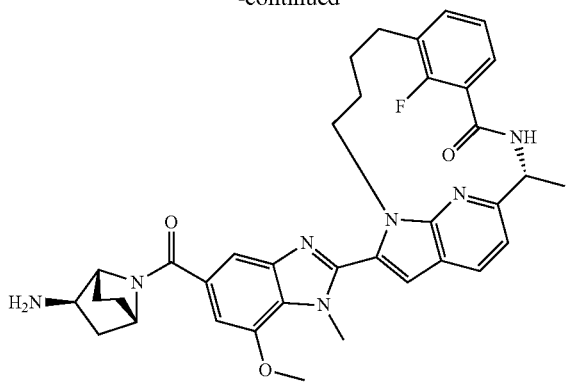
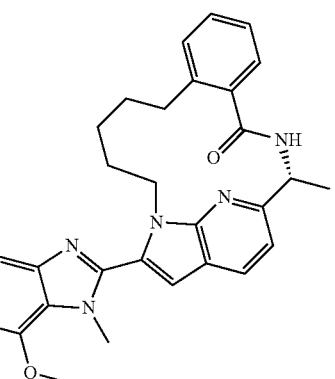
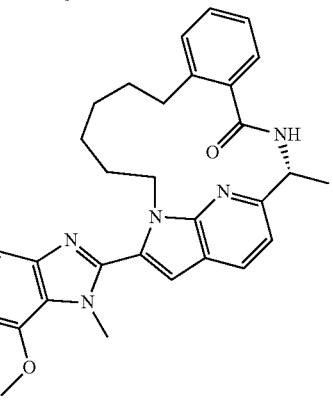
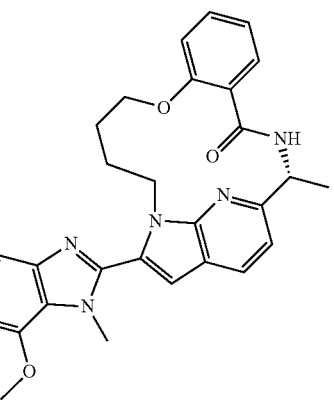

1275
-continued
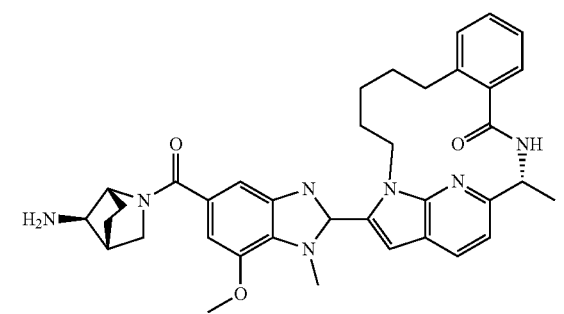
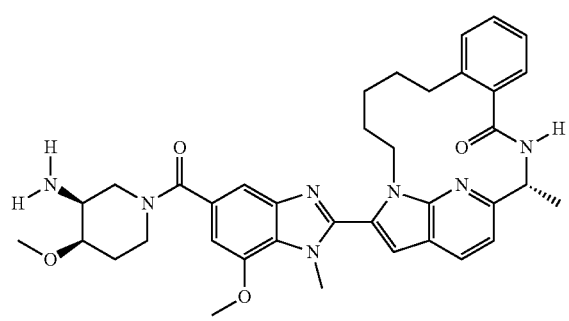
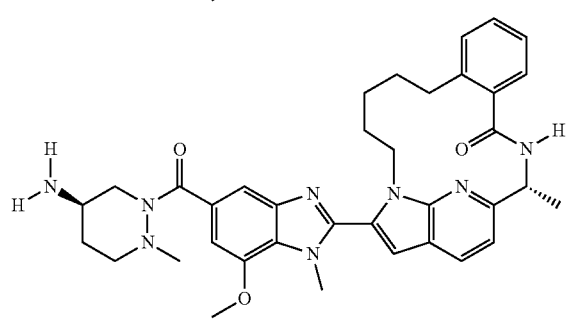
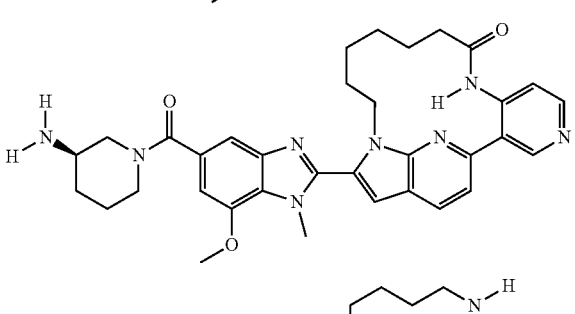
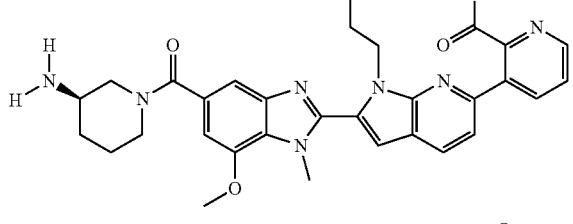
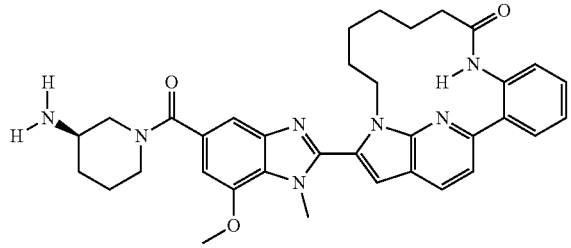
1276
-continued
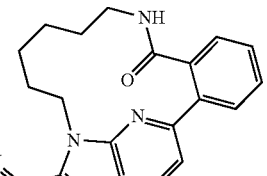
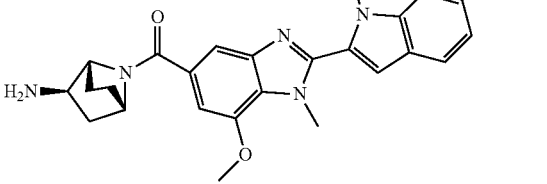
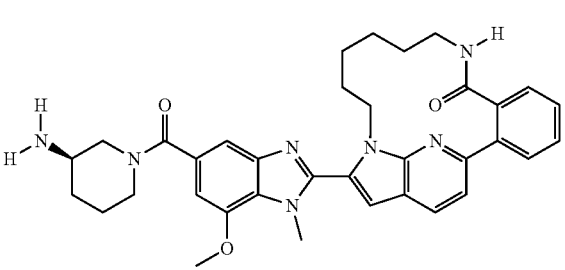
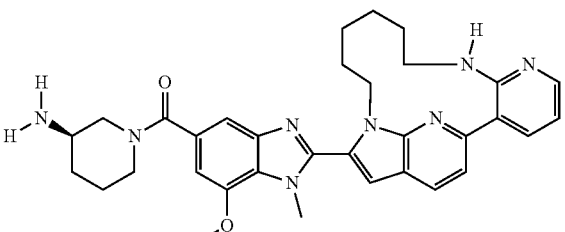
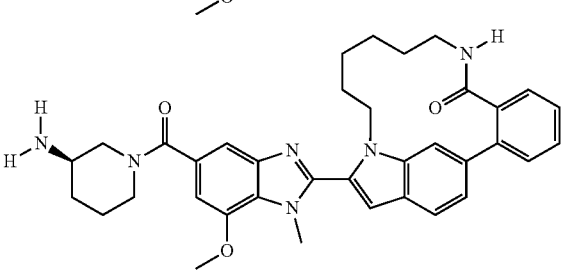
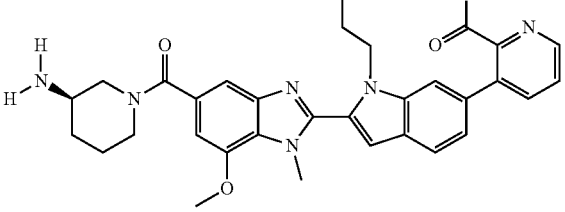
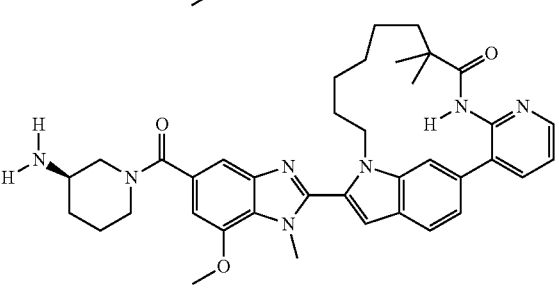

1277
-continued
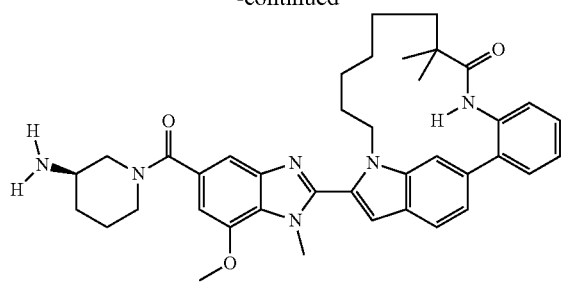
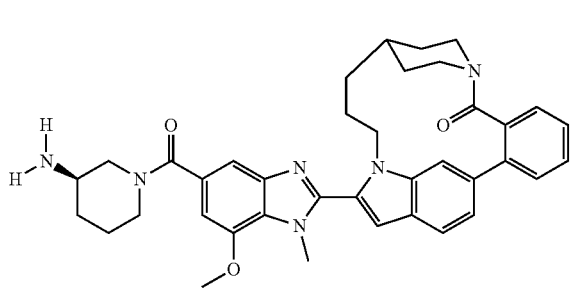
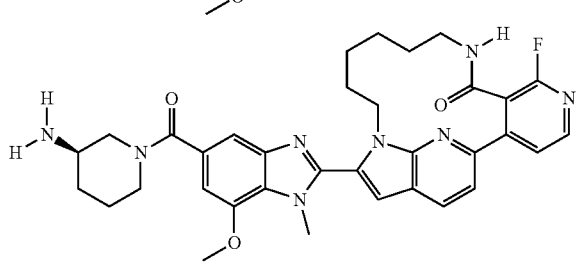
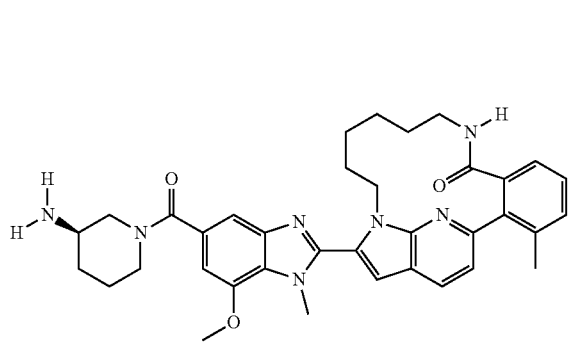
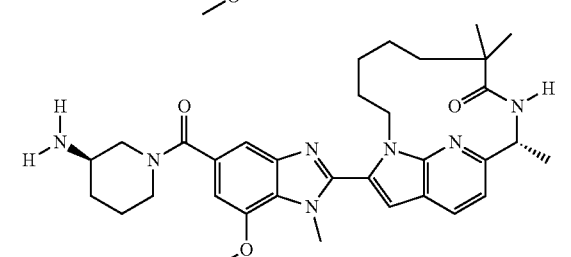
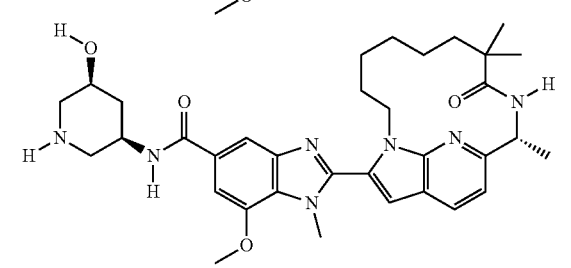
1278
-continued
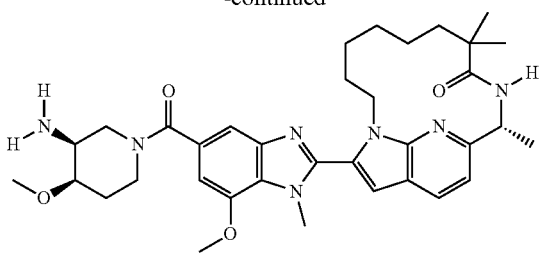
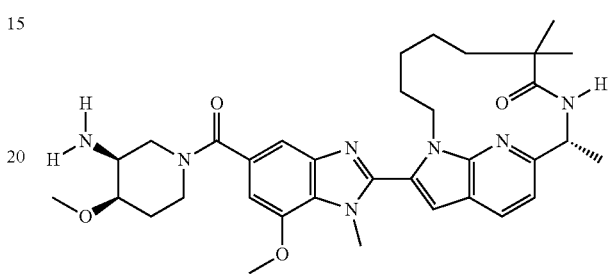
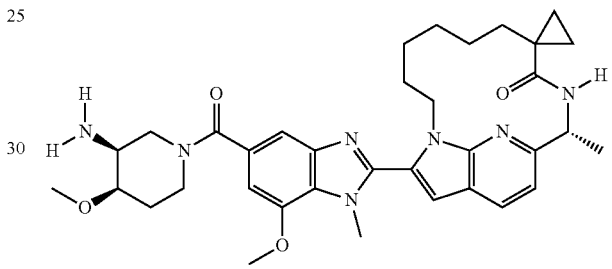
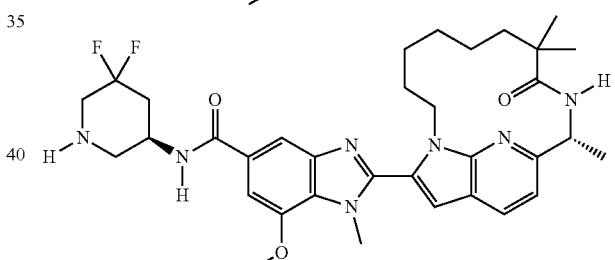
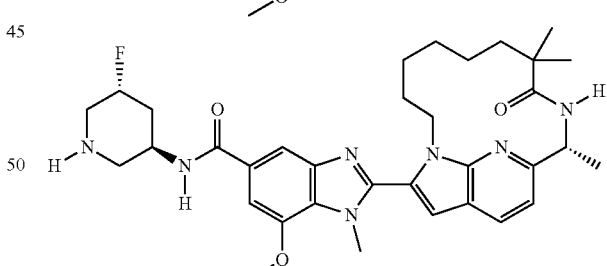
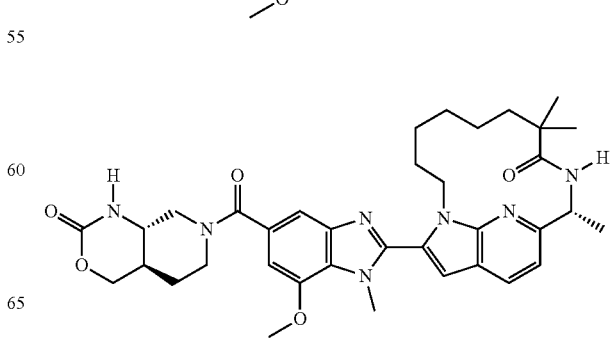

US 11,976,083 B2
1279
-continued
1280
-continued
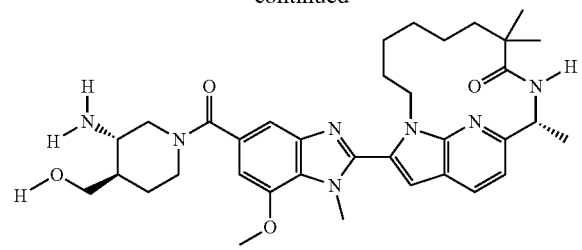
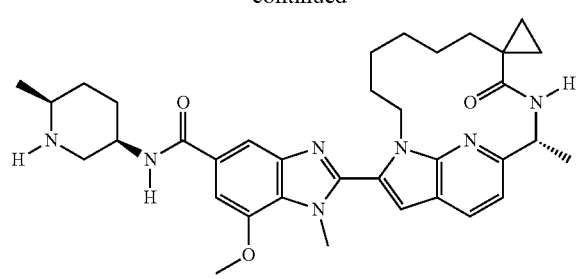
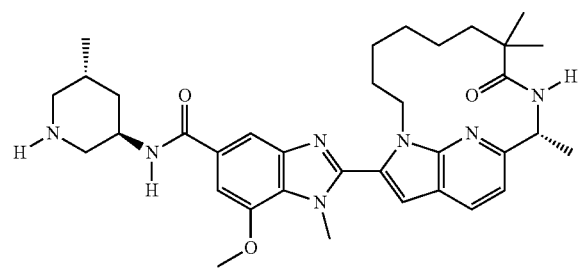
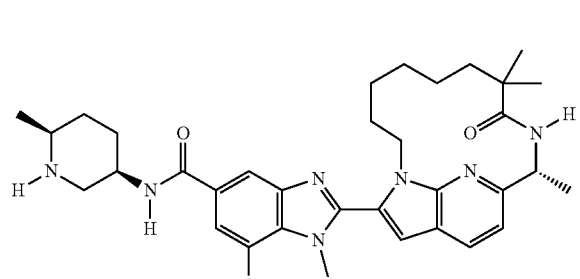
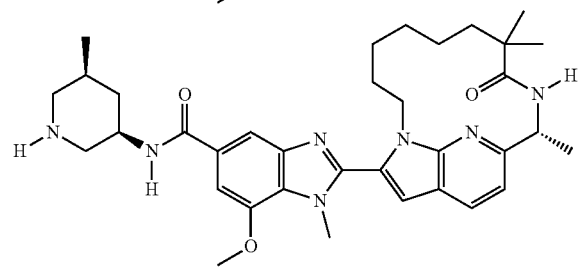
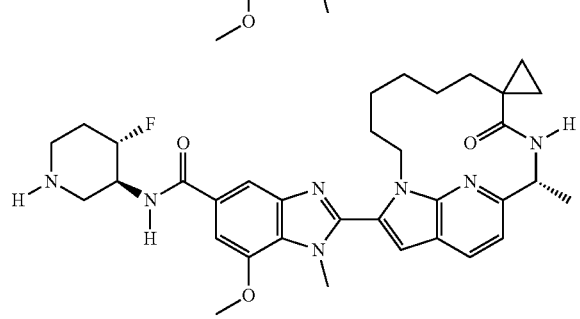
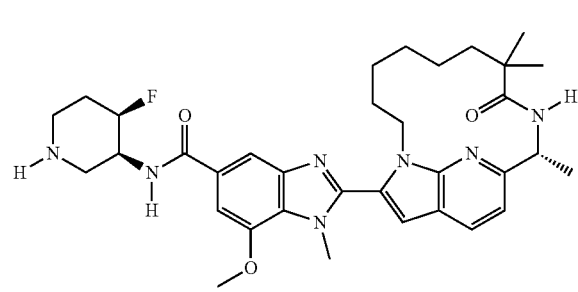
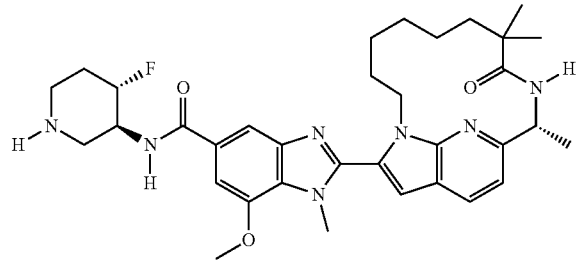
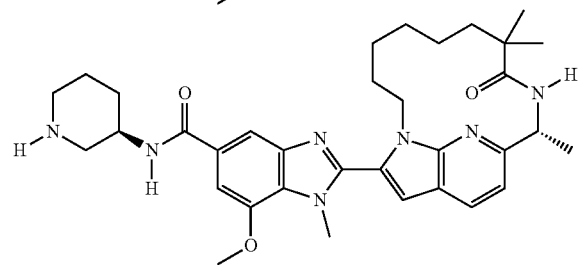
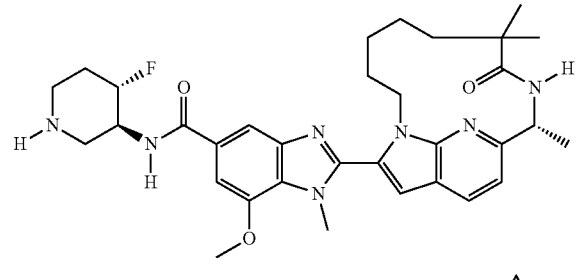
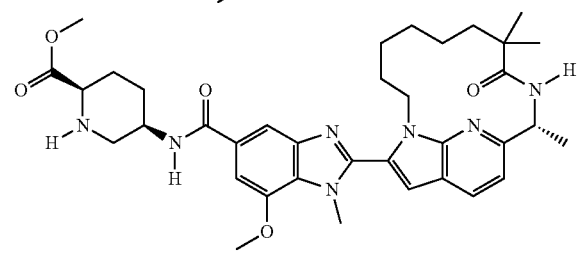
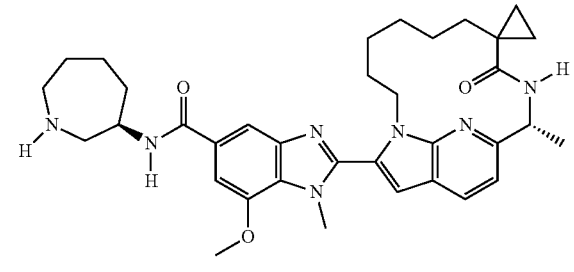

1281
-continued
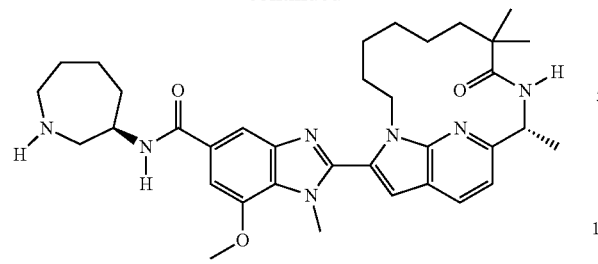
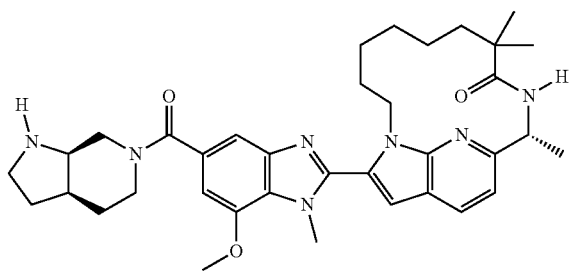
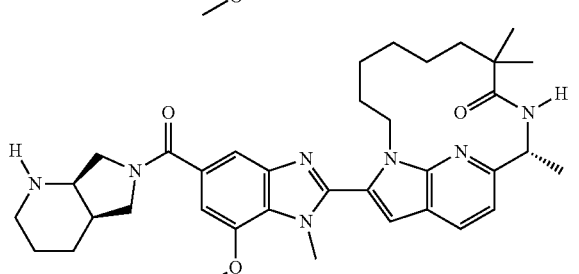
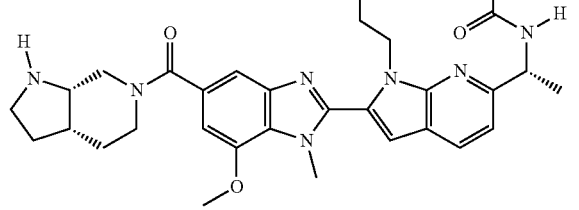
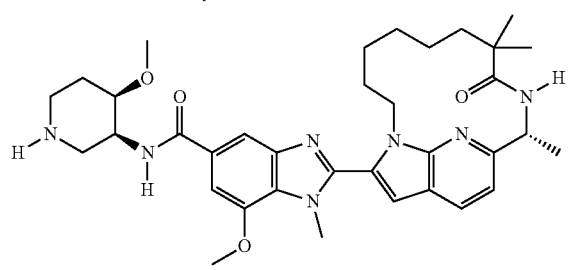
1282
-continued
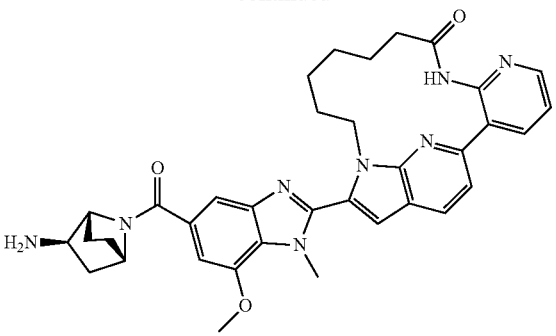
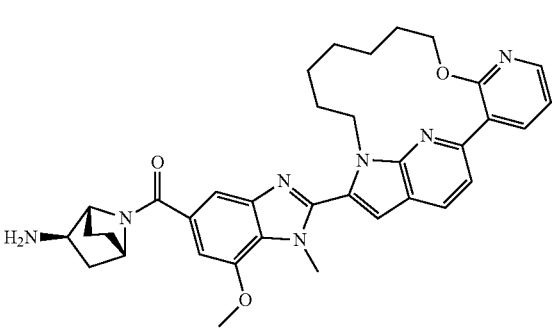
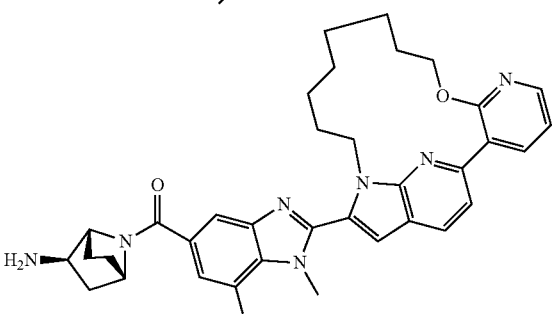
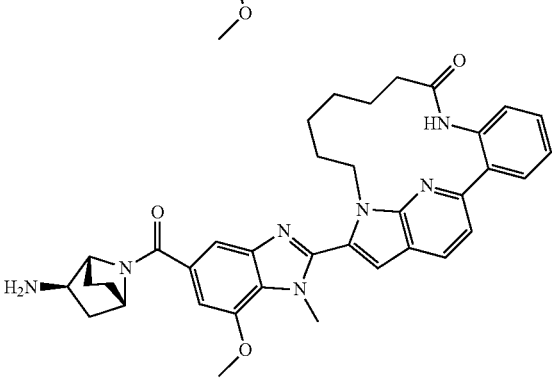
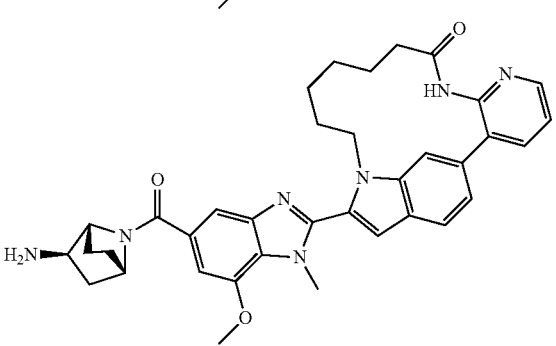

1283
-continued
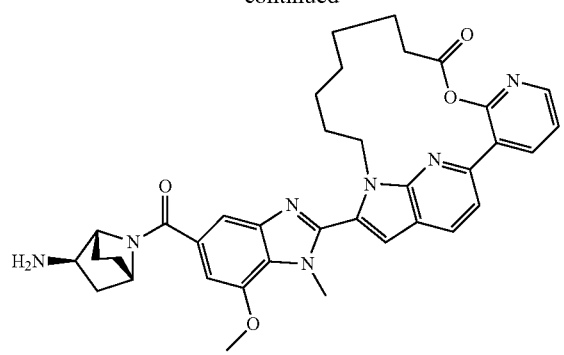
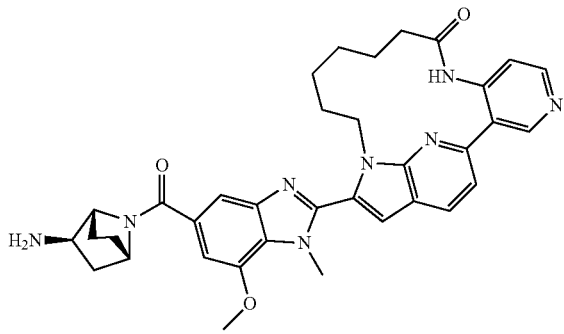
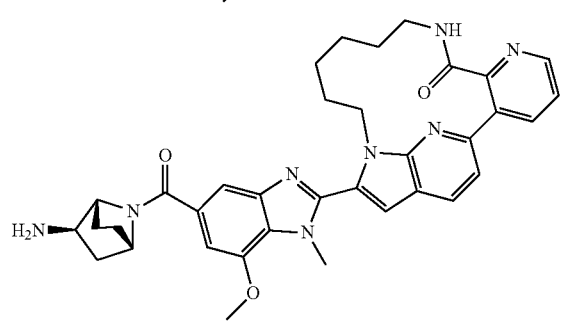
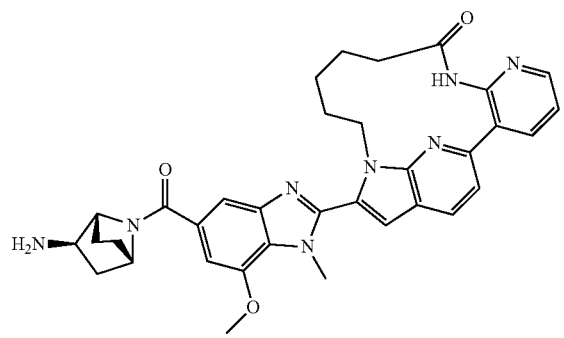
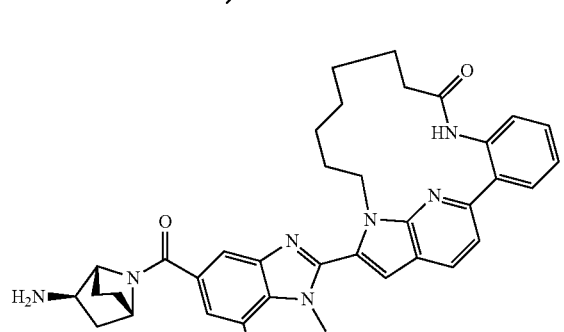
1284
-continued
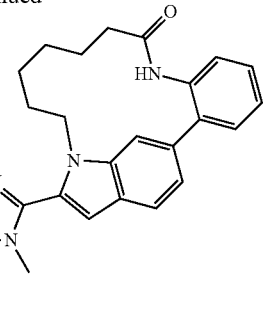
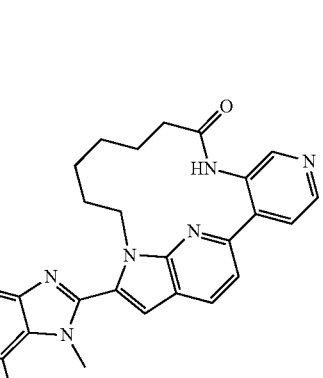
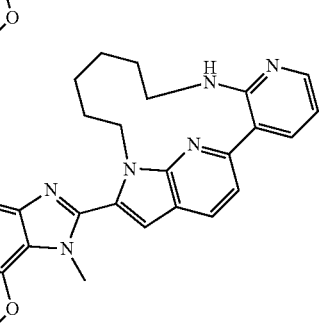
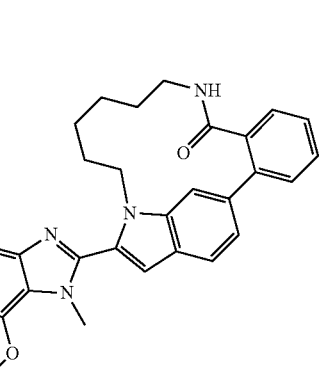
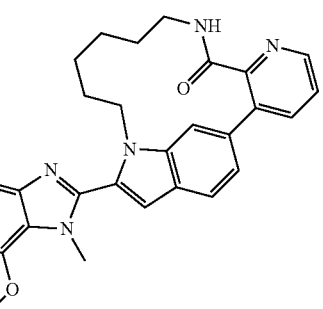

1285
-continued
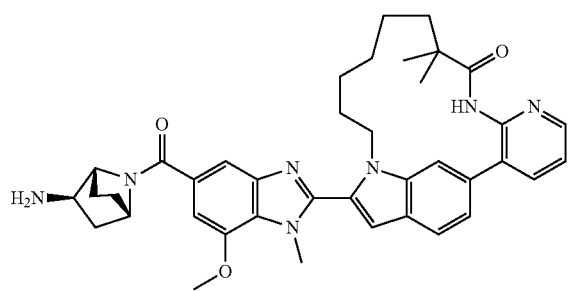
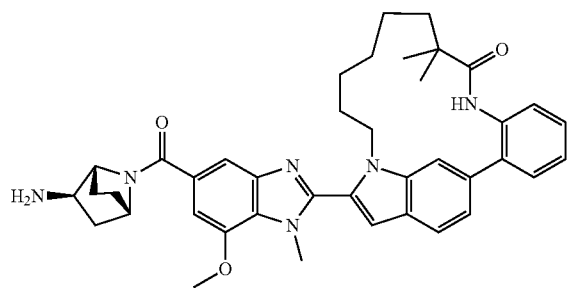
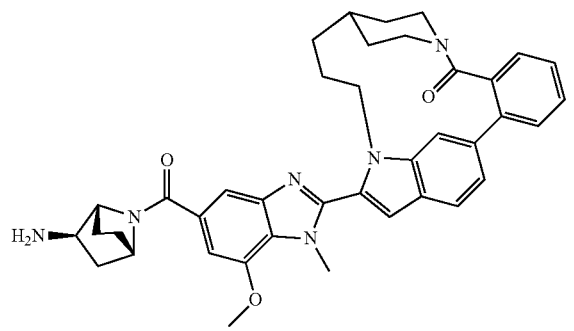
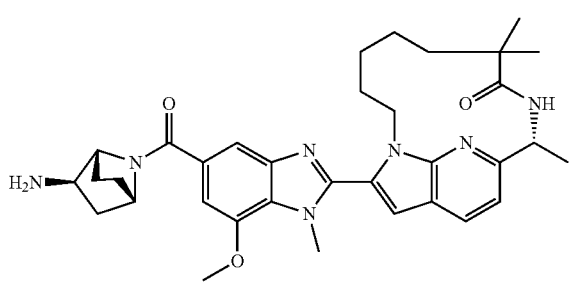
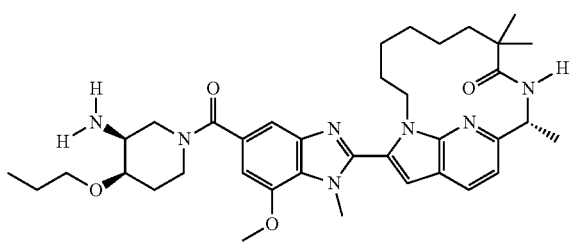
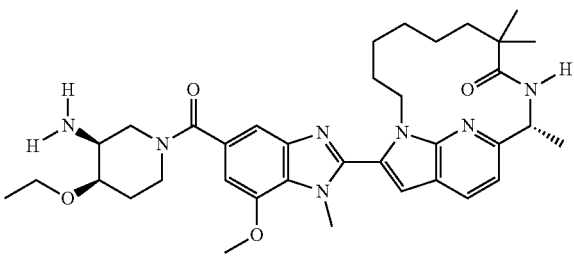
1286
-continued
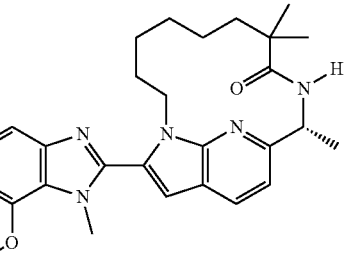
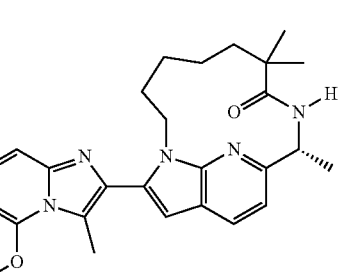
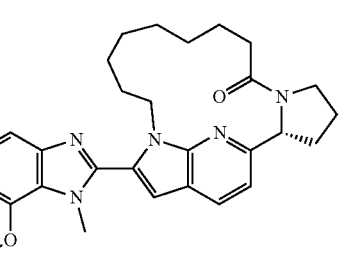
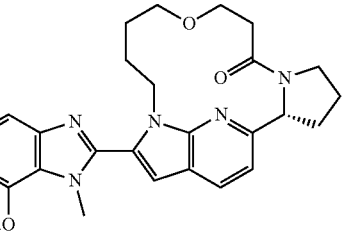
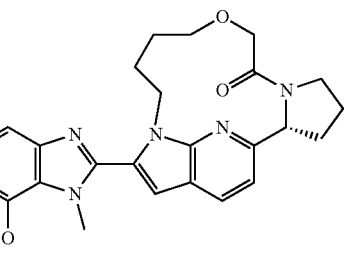
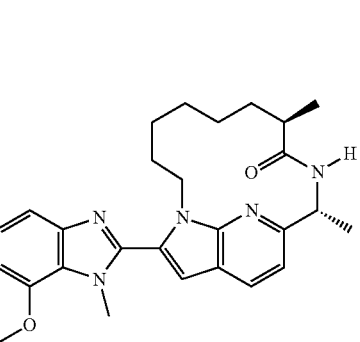

1287
-continued
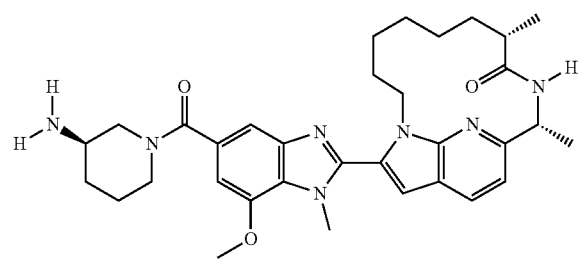
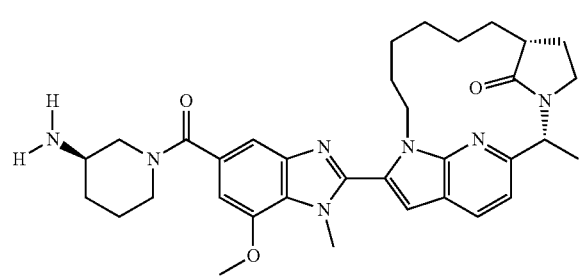
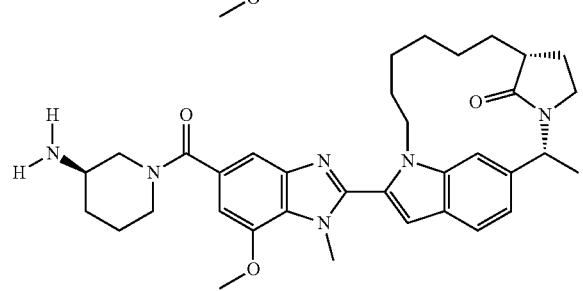
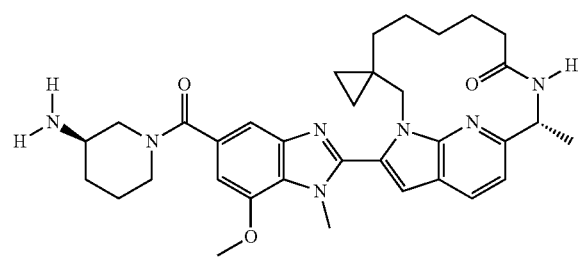
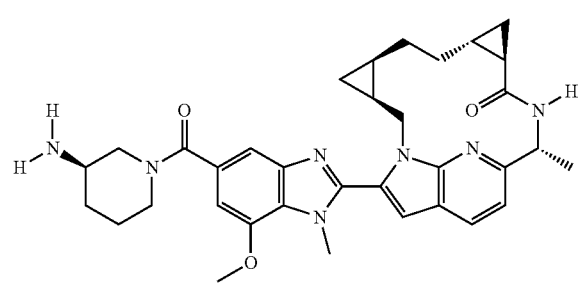
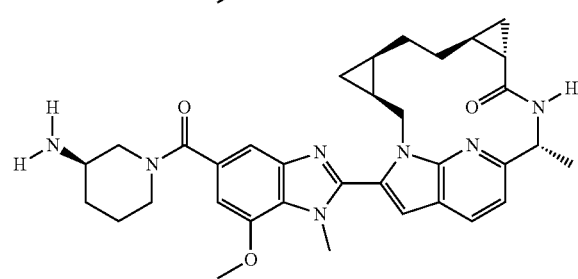
1288
-continued
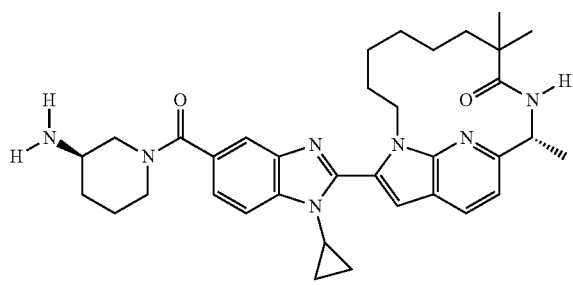
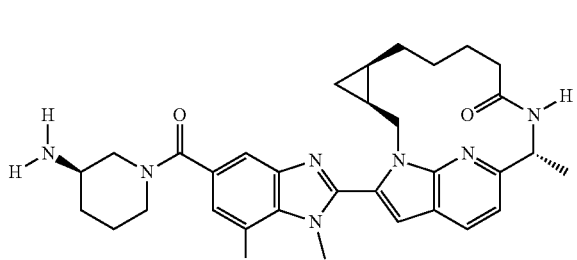
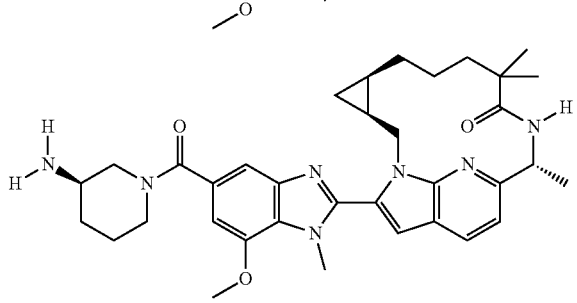
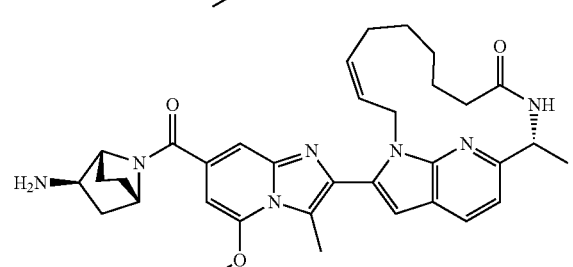
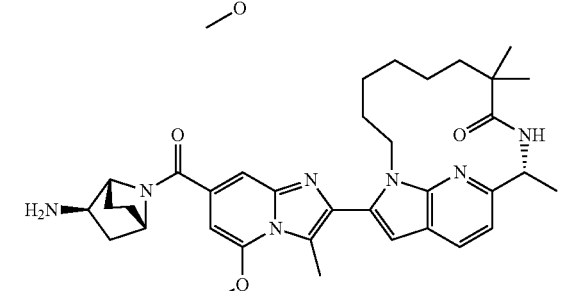
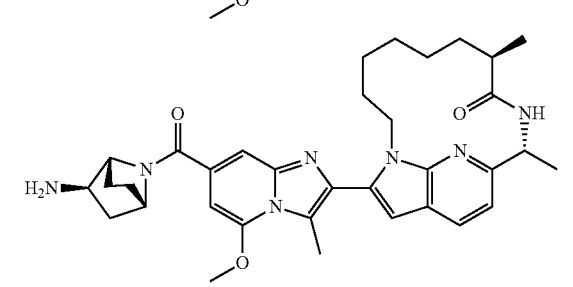

1289
-continued
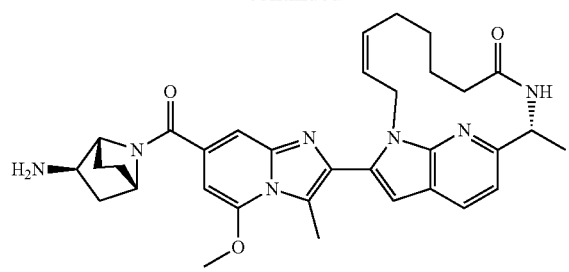
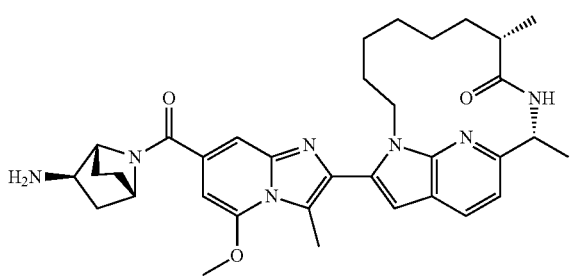
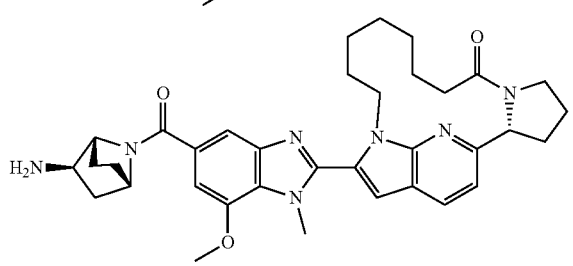
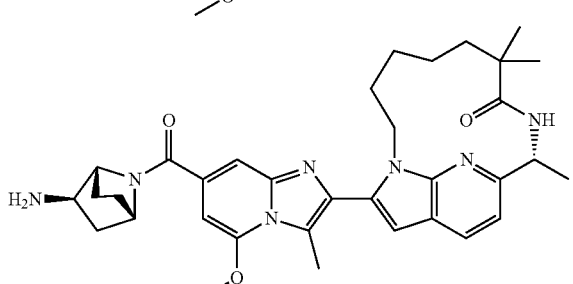
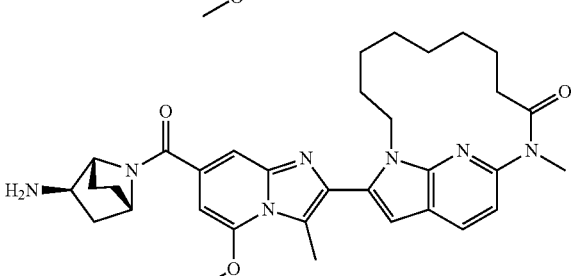
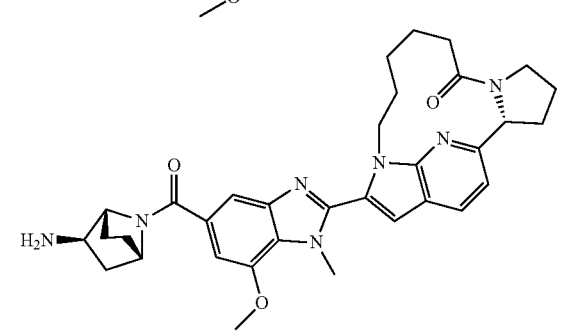
1290
-continued
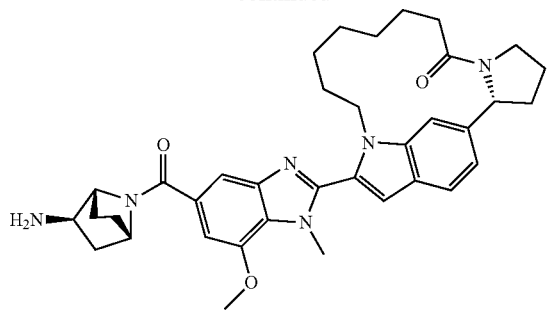
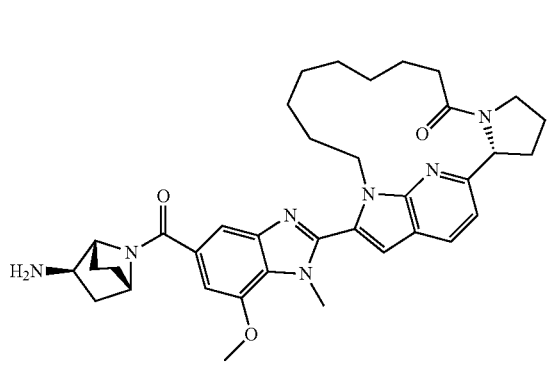
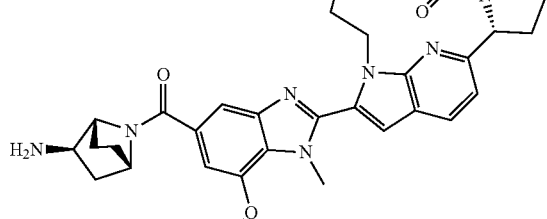
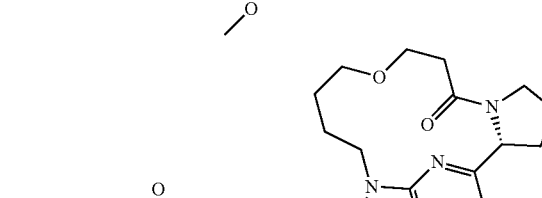
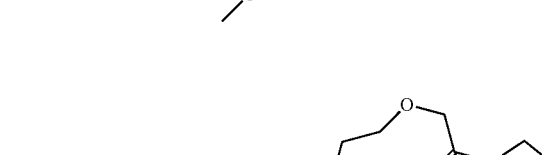
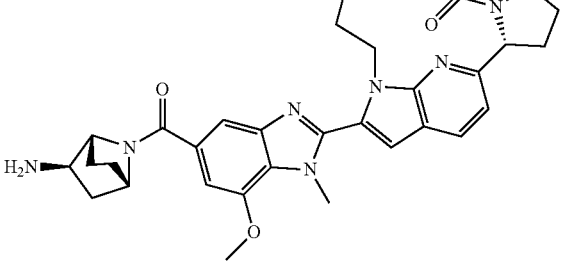

1291
-continued
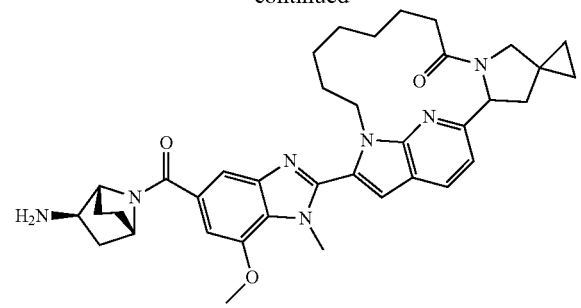
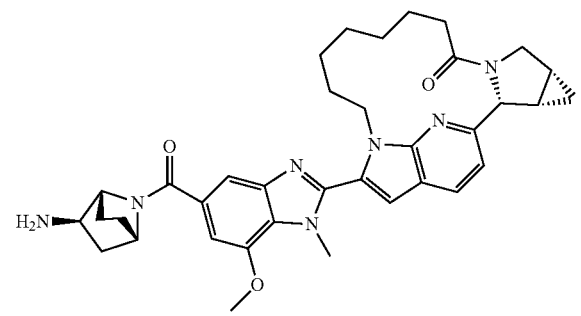
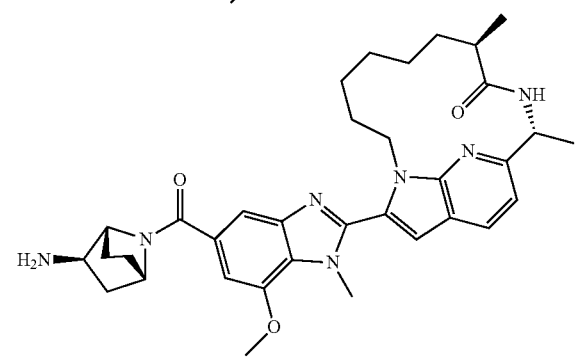
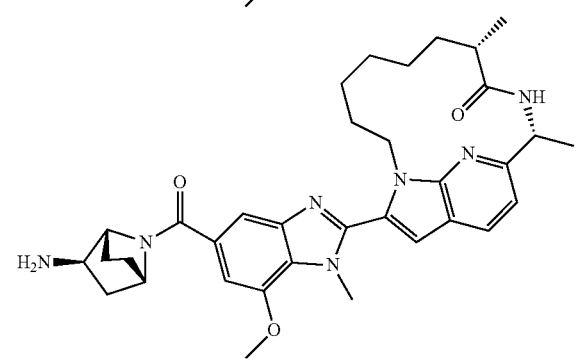
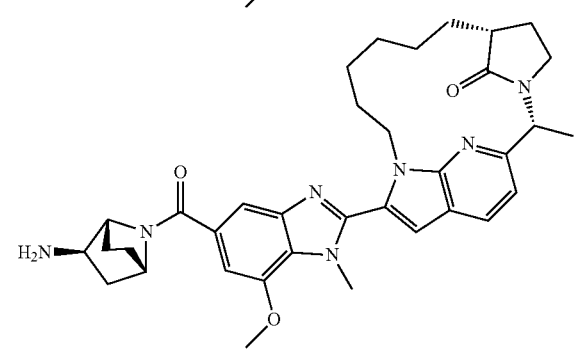
1292
-continued
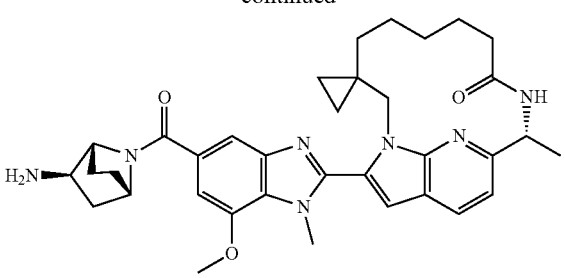
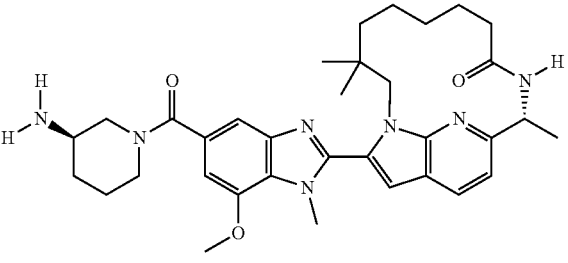
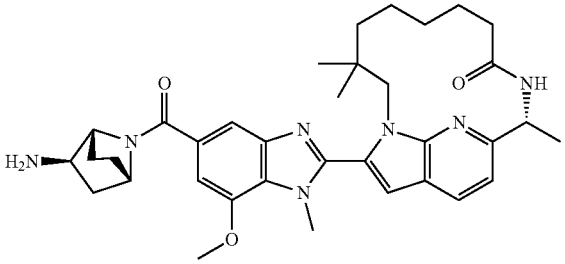
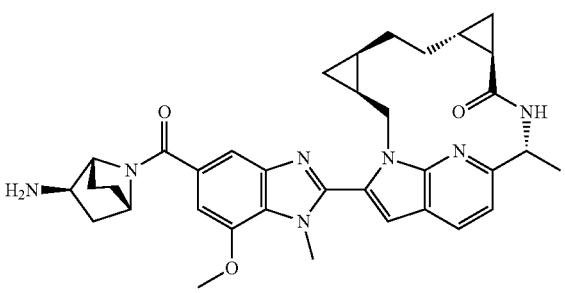
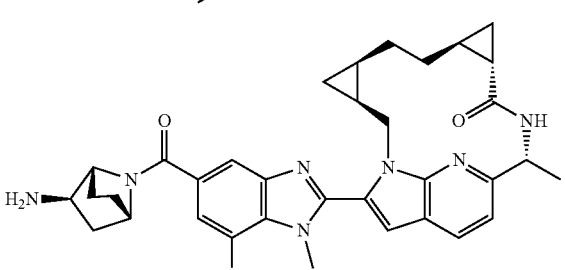
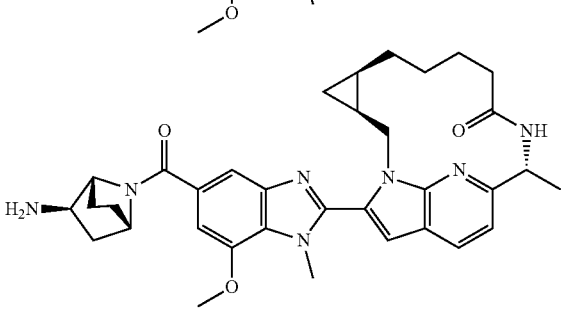

1293
-continued
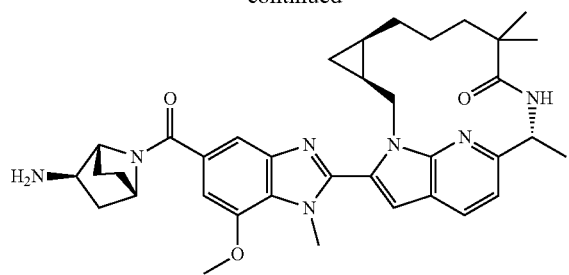
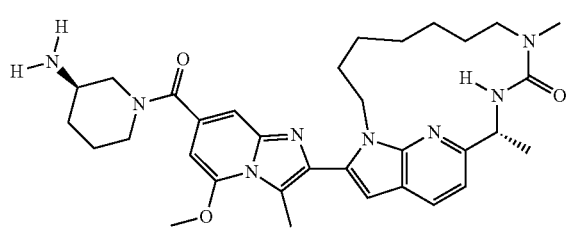
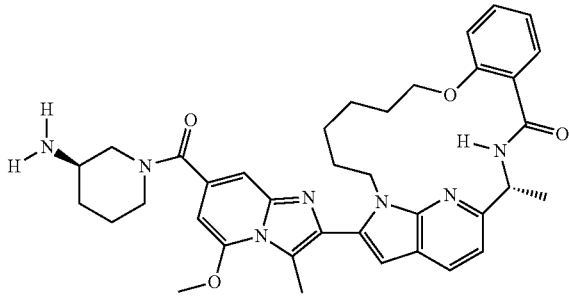
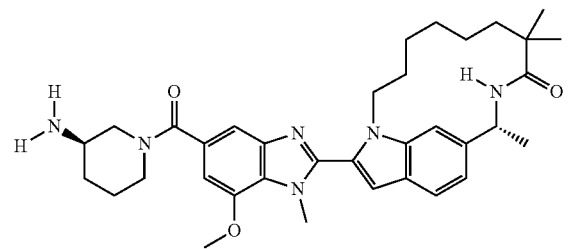
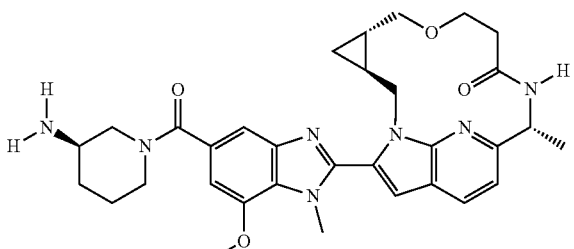
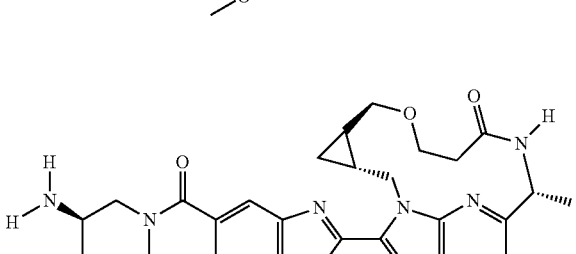
1294
-continued
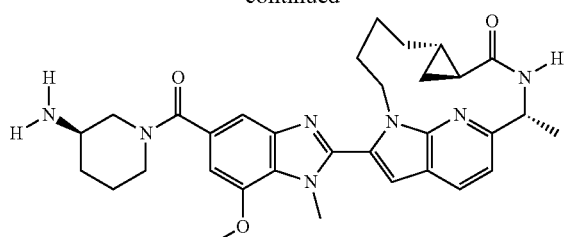
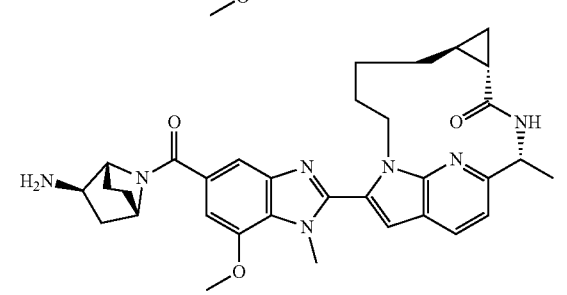
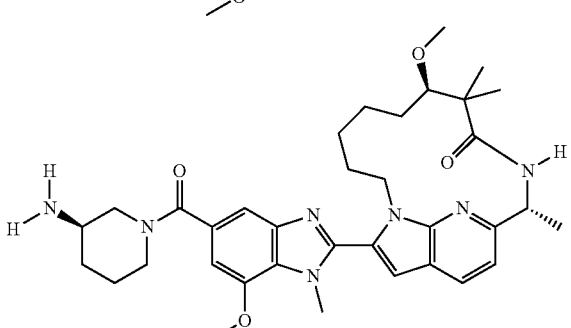
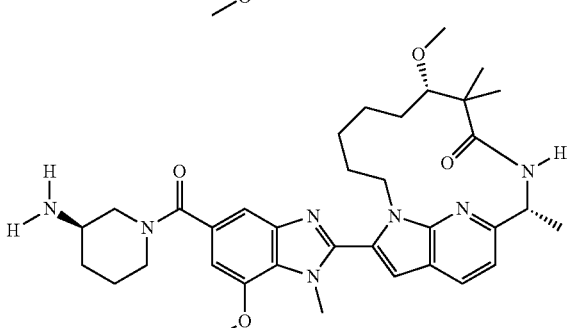
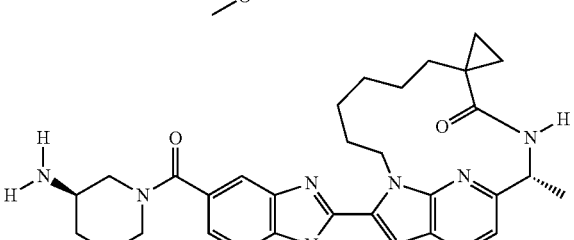
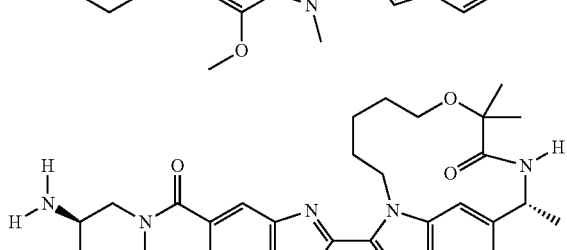

1295
-continued
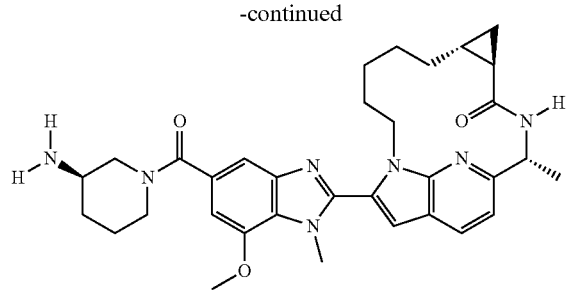
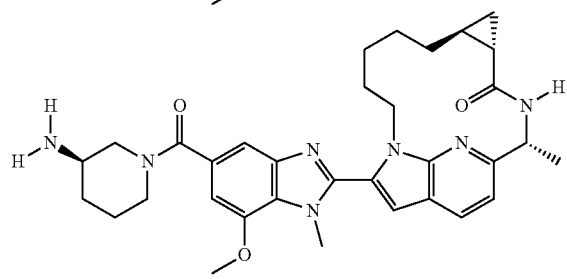
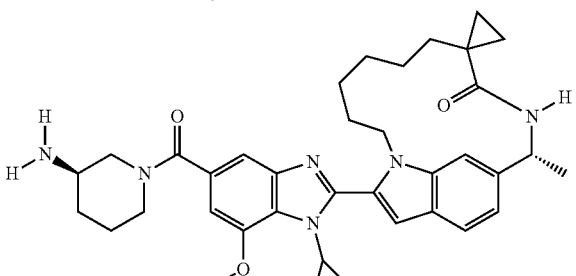
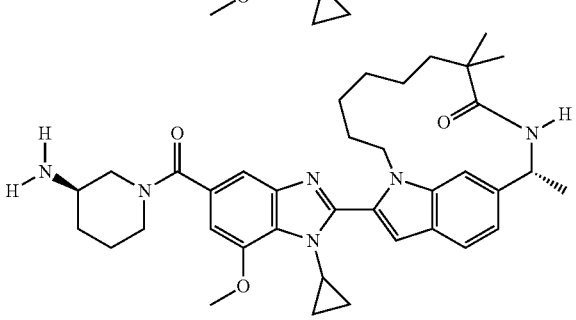
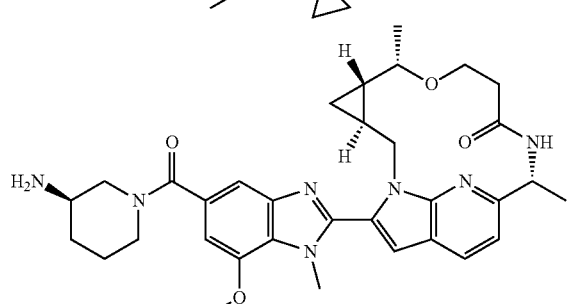
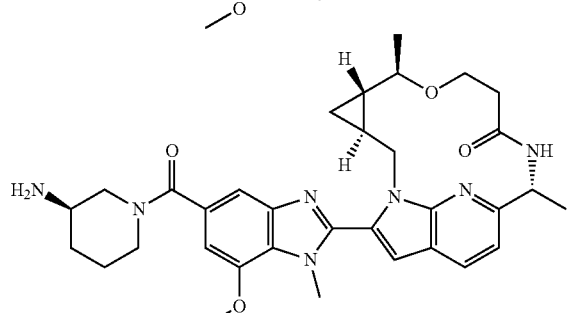
1296
-continued
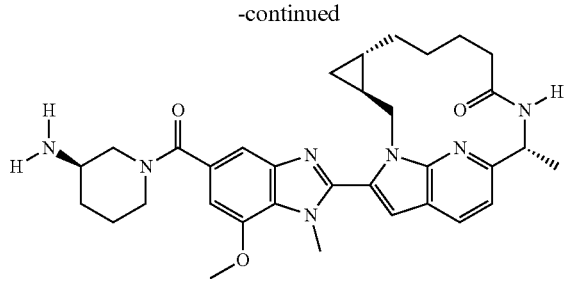
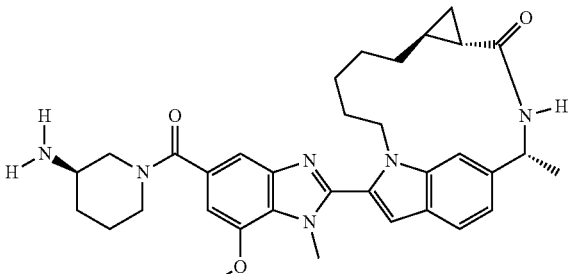
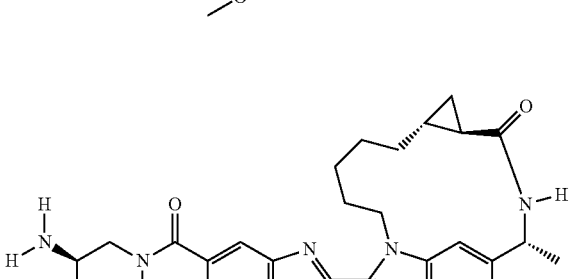
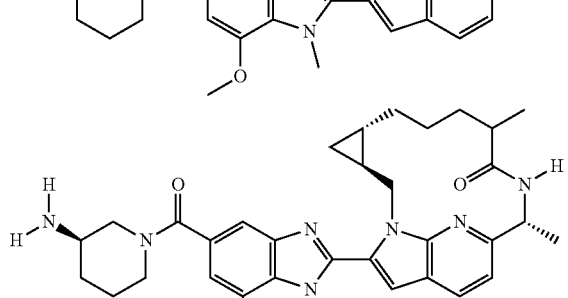
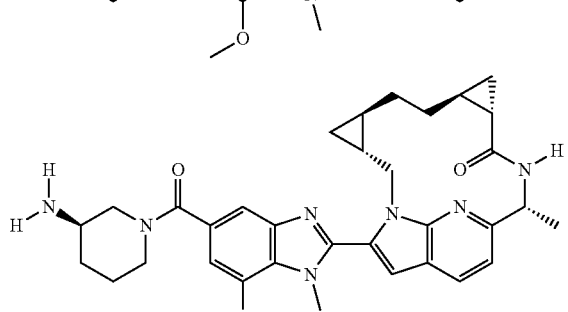
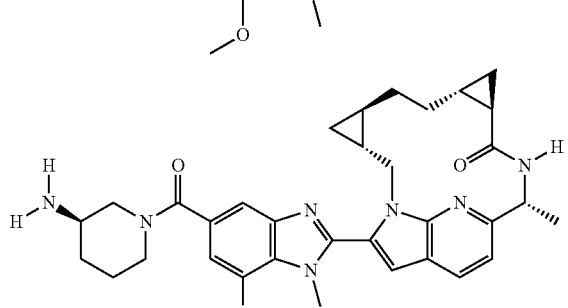

1297
-continued
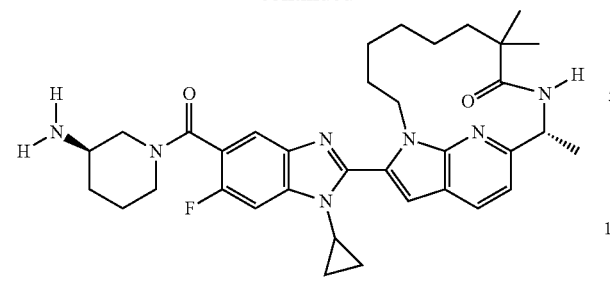
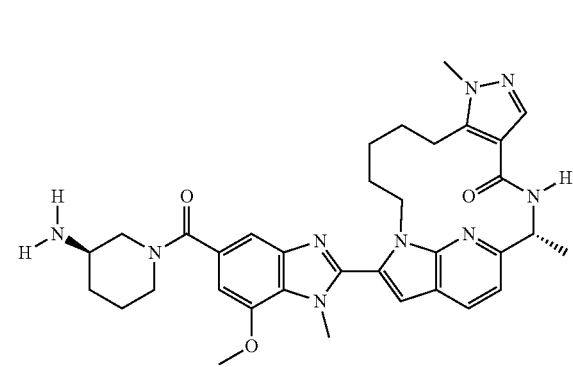
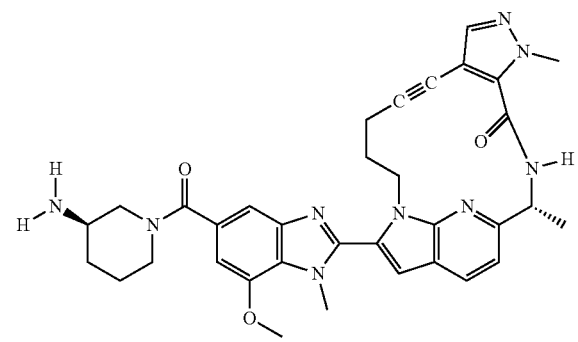
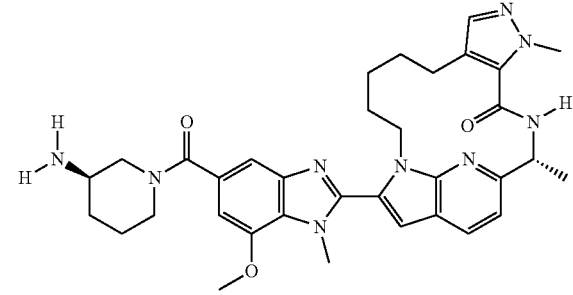
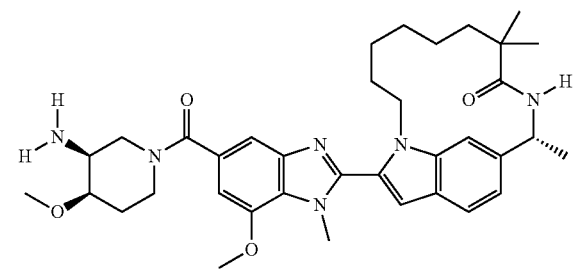
1298
-continued
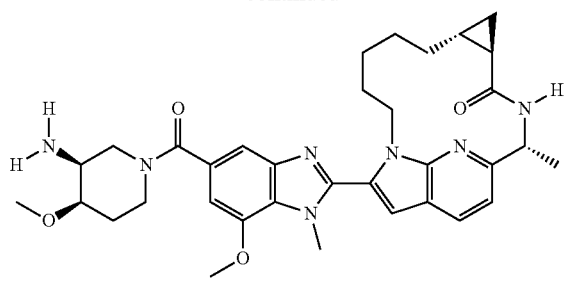
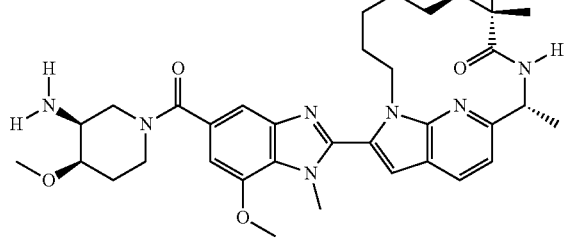
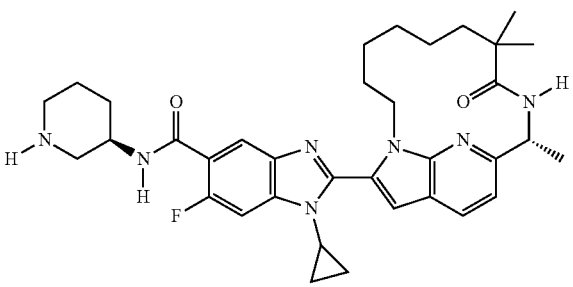
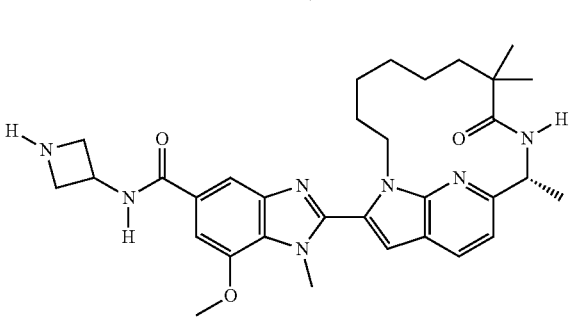
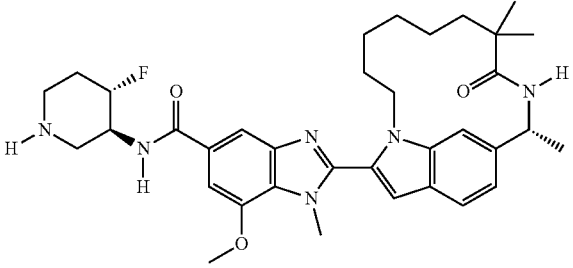
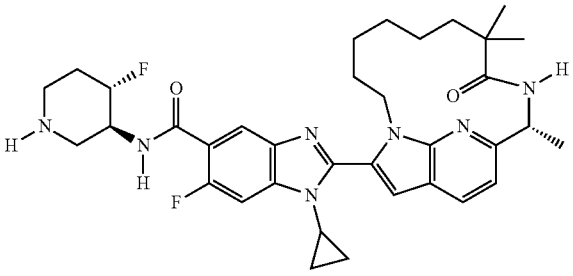

1299
-continued
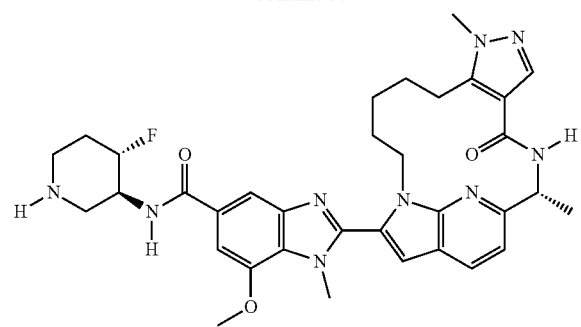
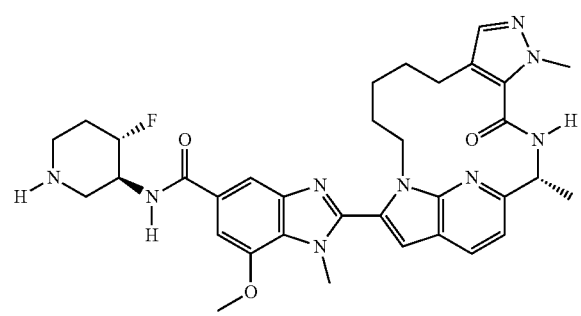
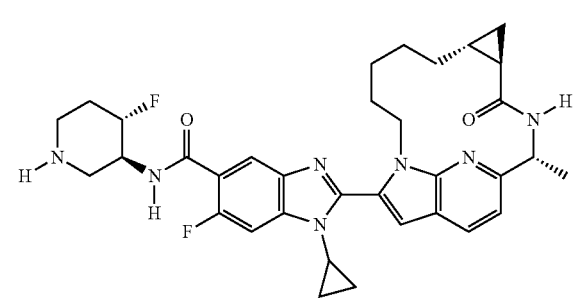
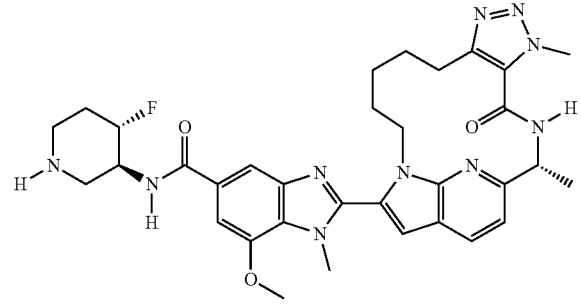
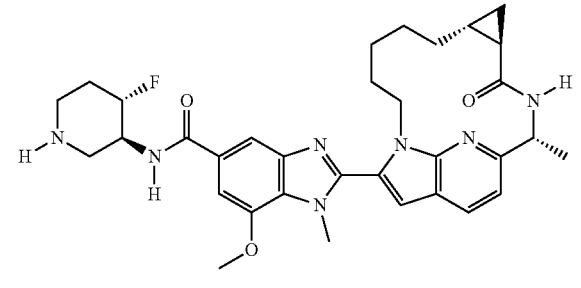
1300
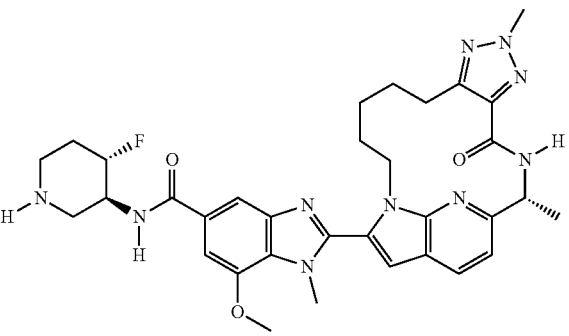
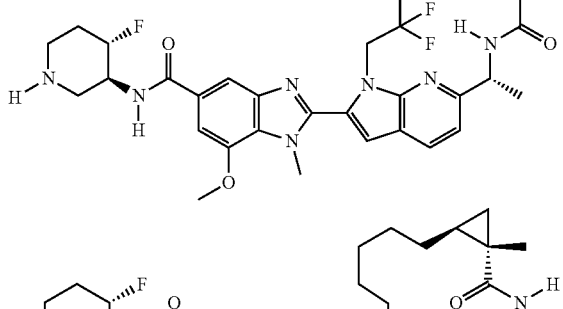
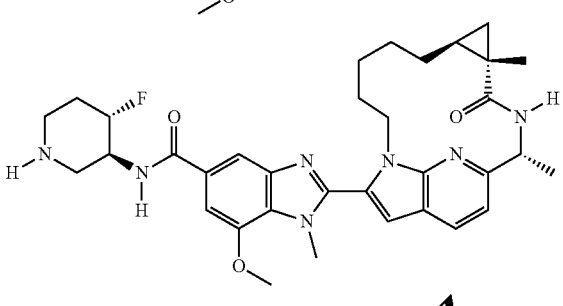
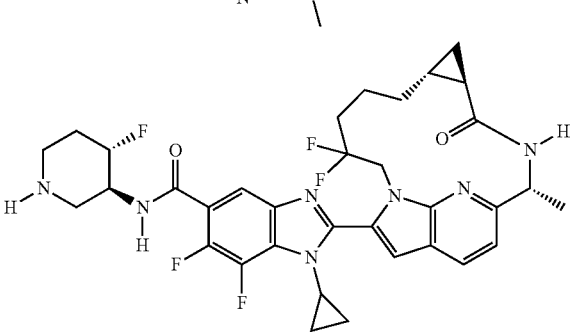
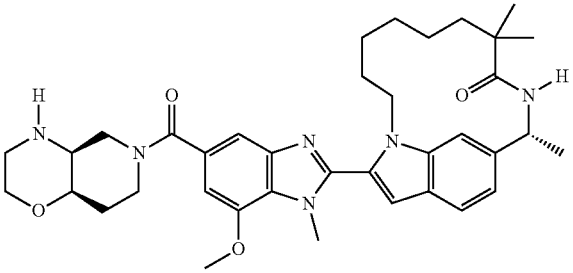

1301
-continued
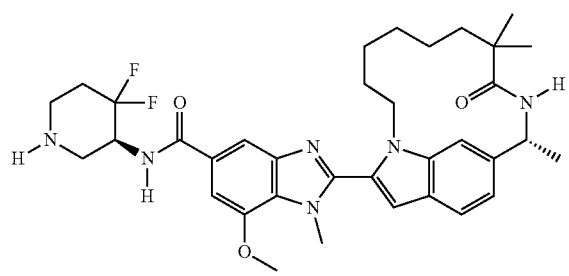
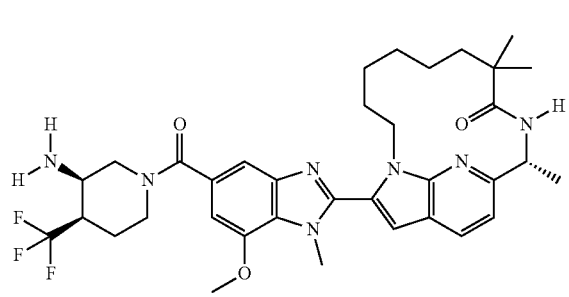
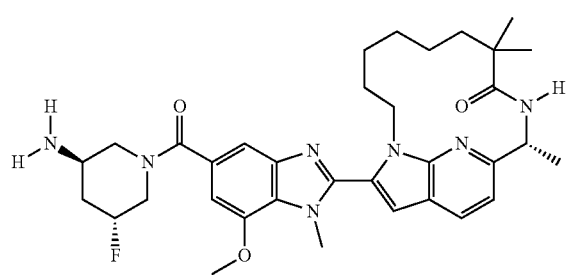
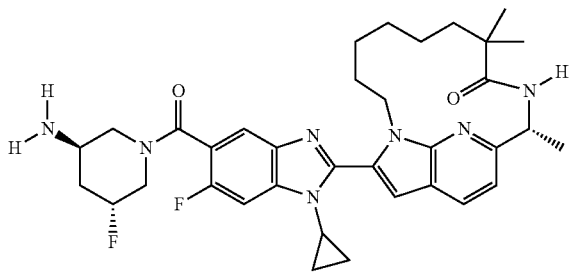
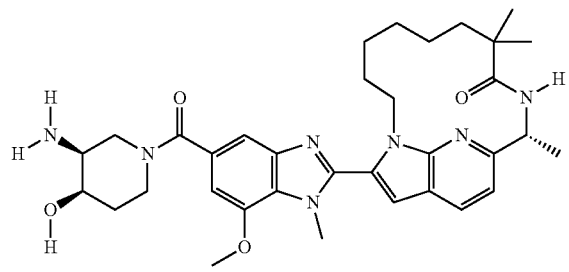
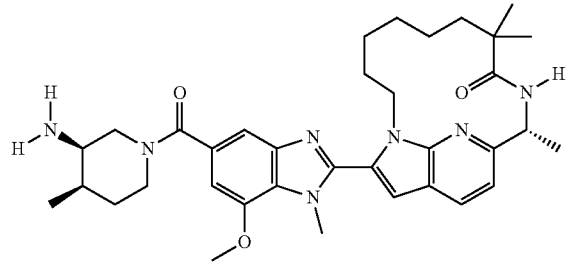
1302
-continued
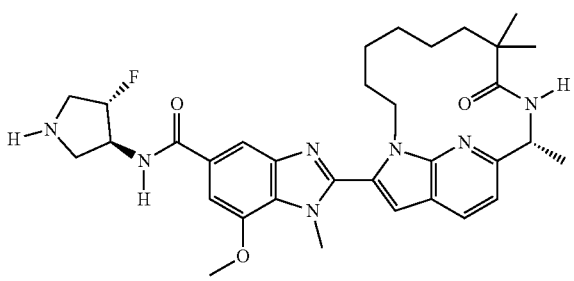
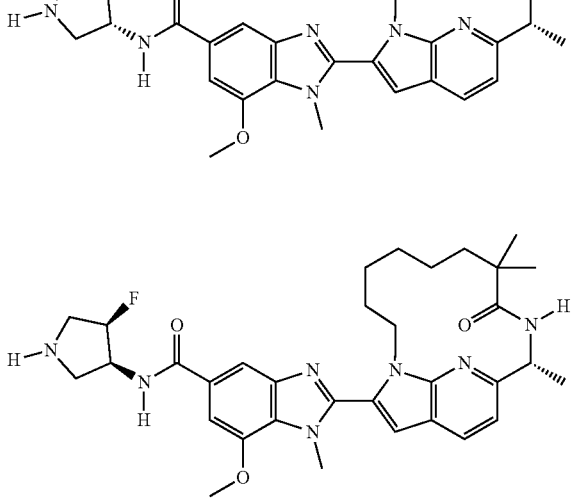
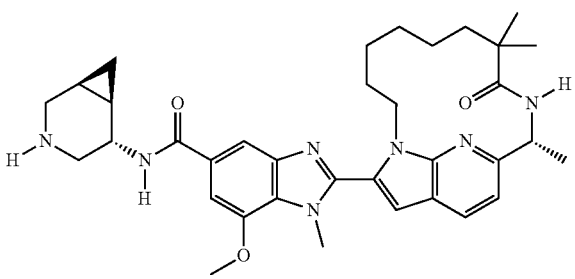
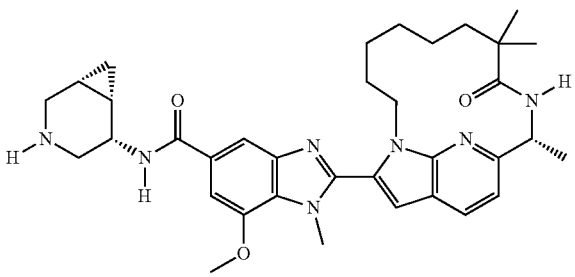

1303
-continued
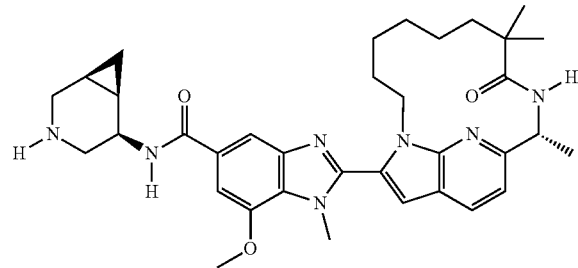
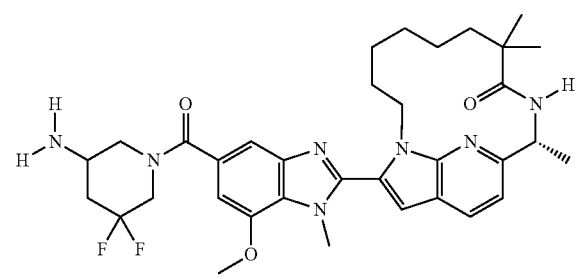
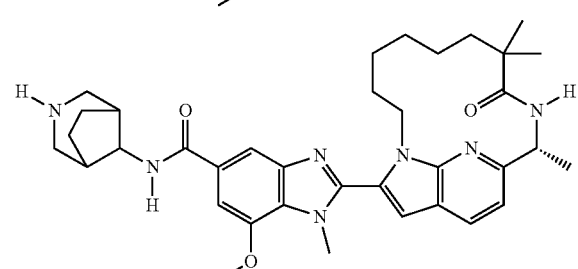
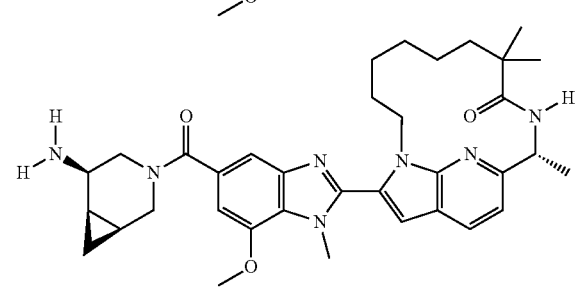
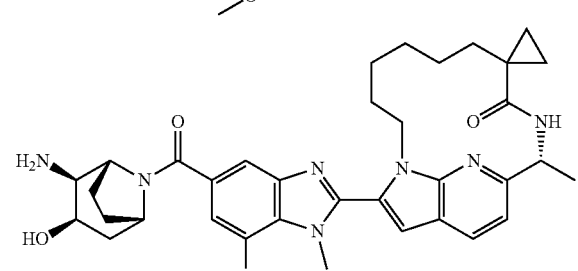
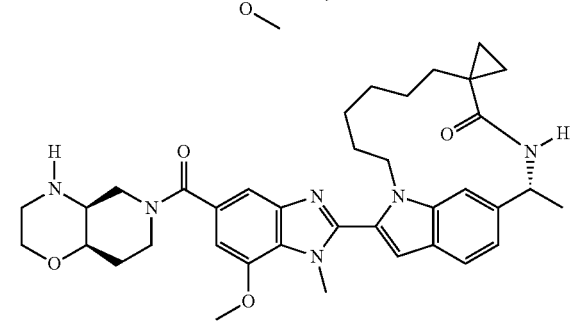
1304
-continued
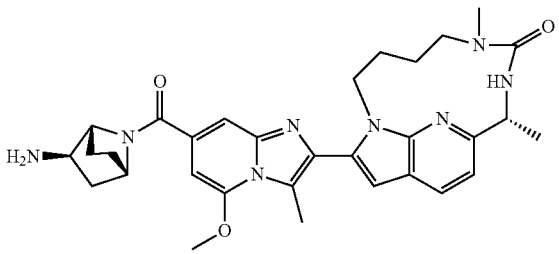
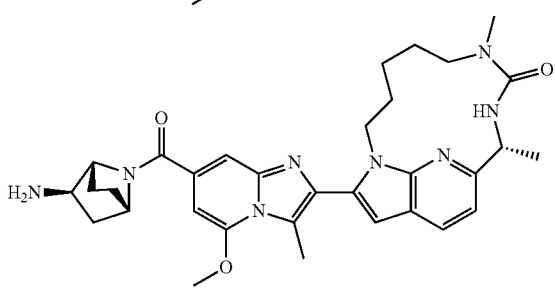
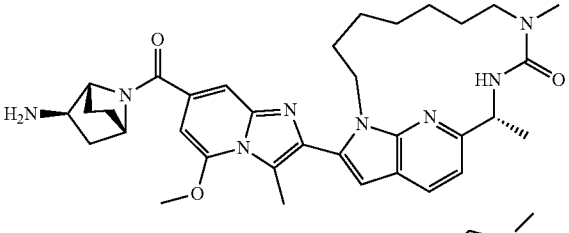
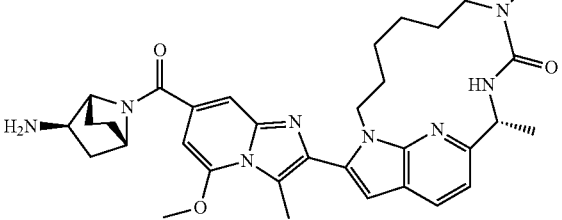
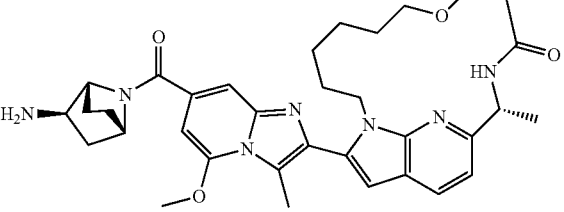
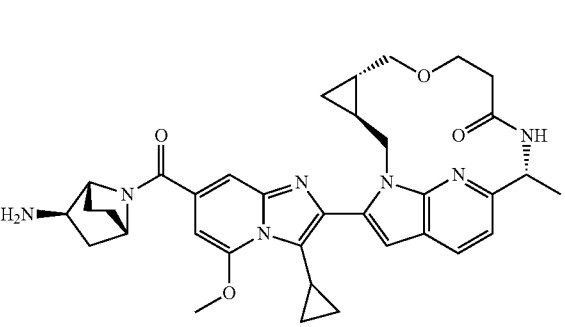

1305
-continued
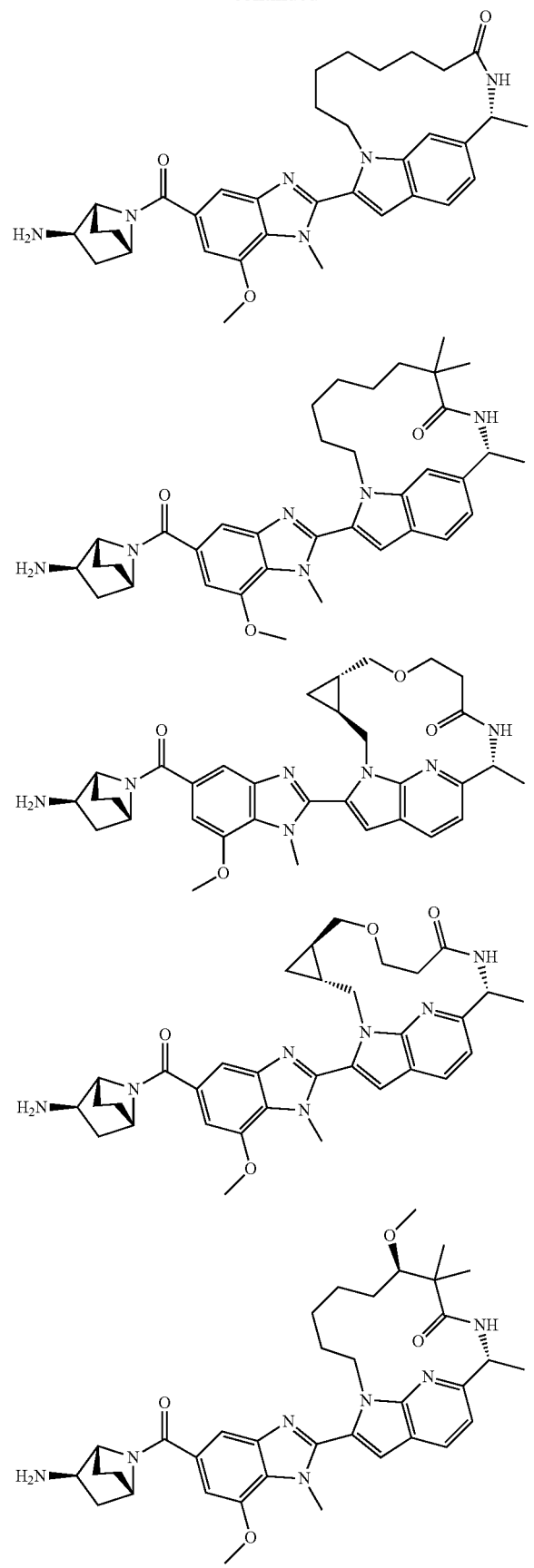
1306
-continued
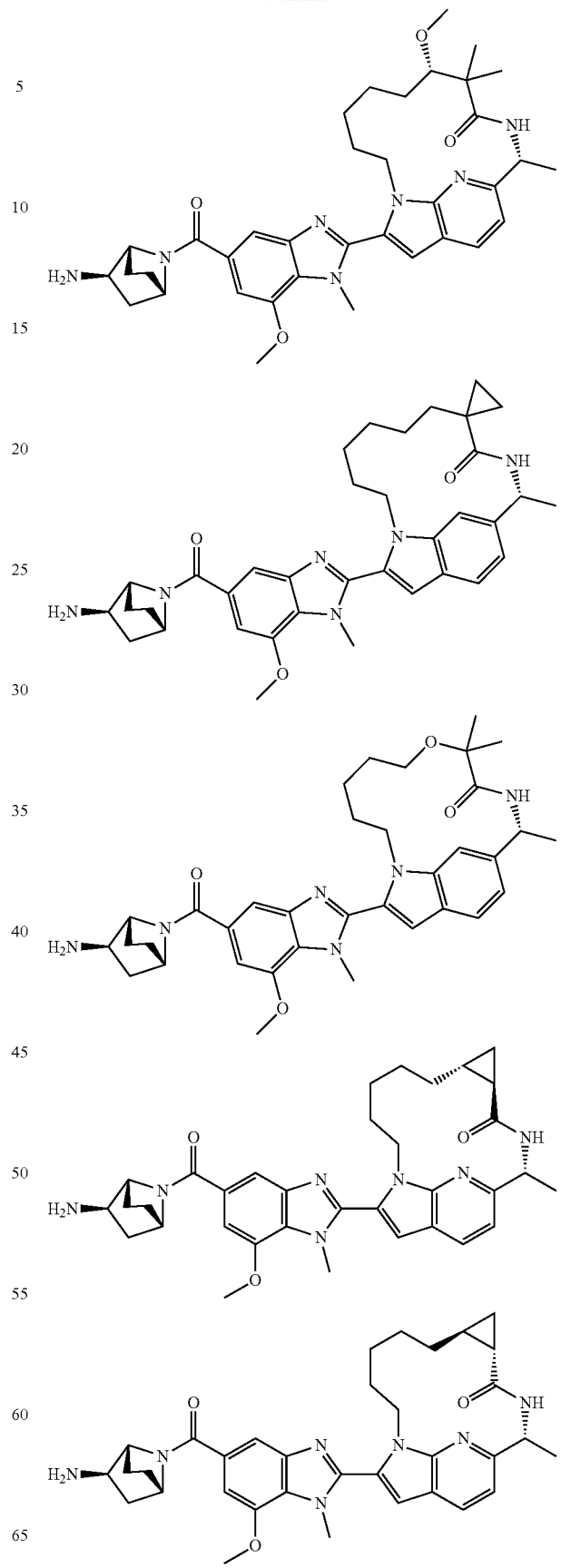

1307
-continued
1308
-continued
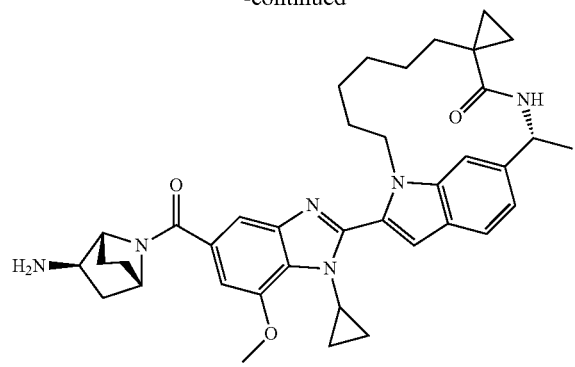
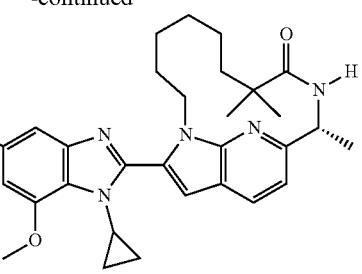

1309
-continued
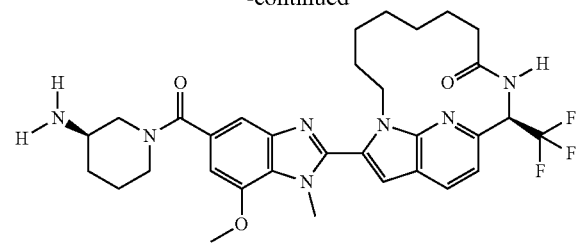
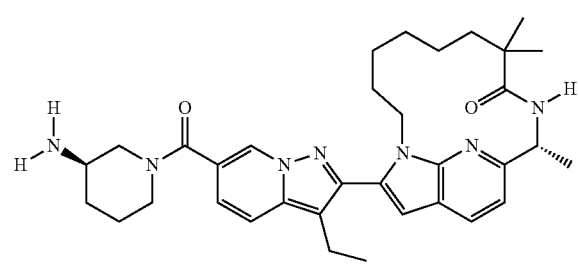
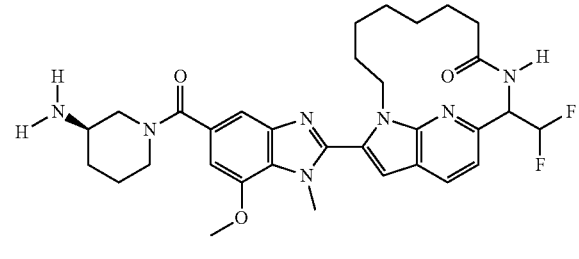
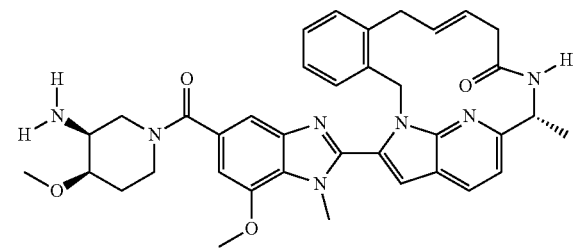
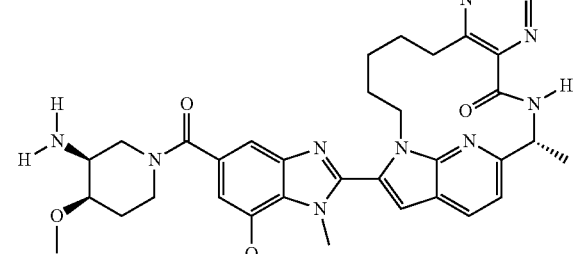
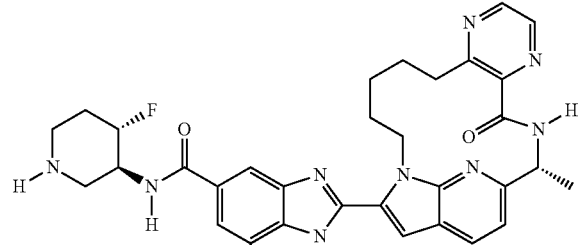
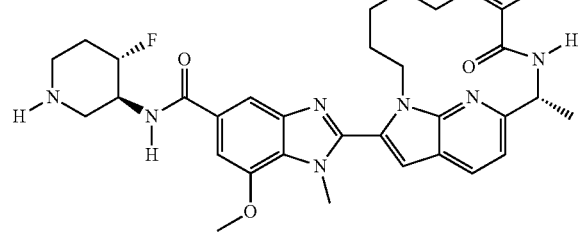
1310
-continued
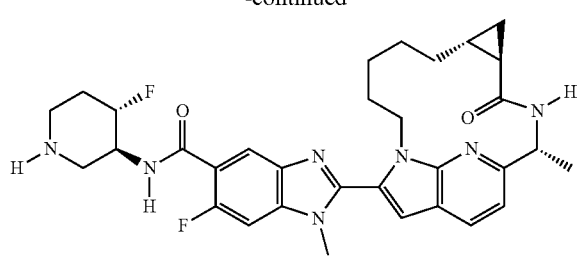
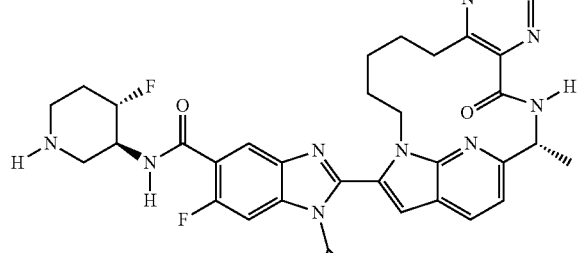
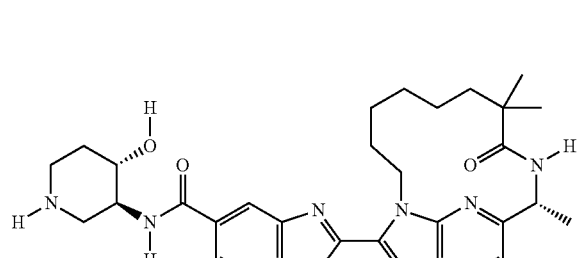
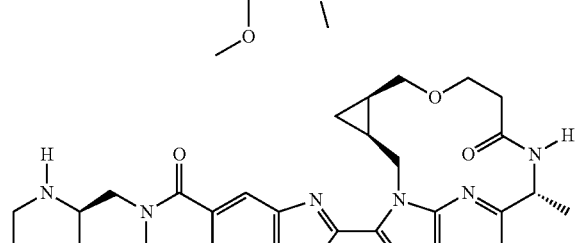
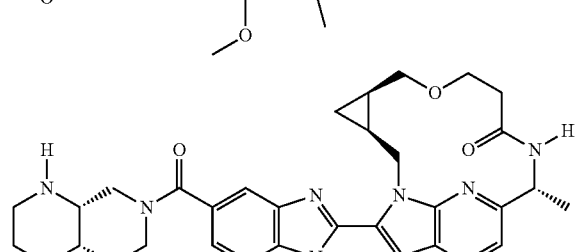
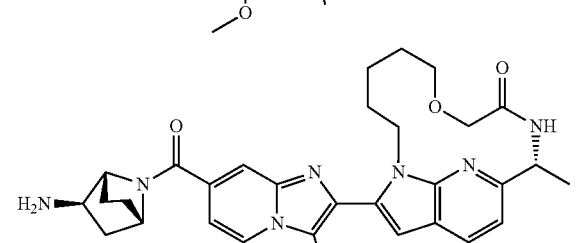
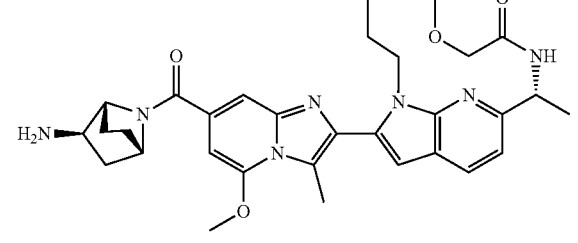

1311
-continued
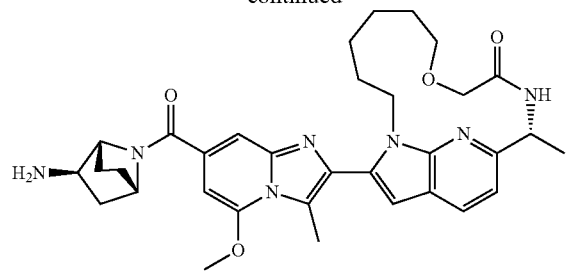
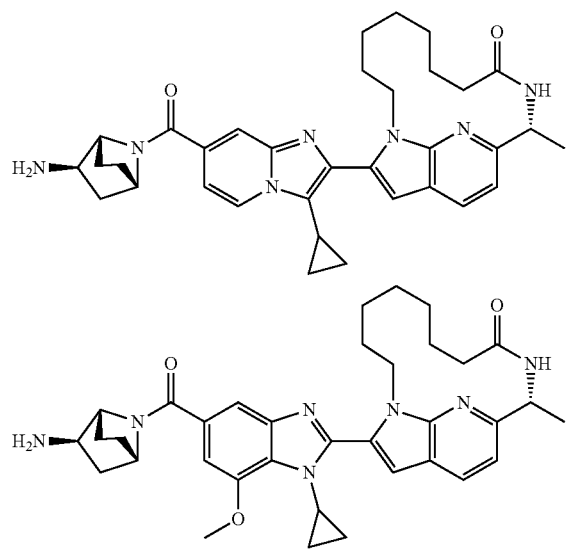
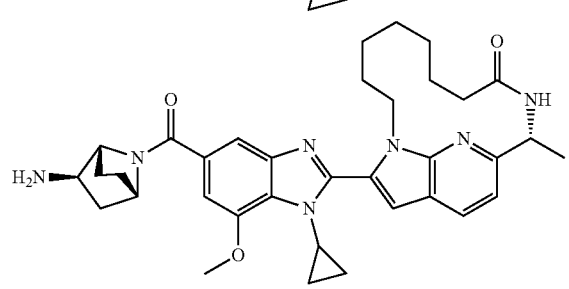
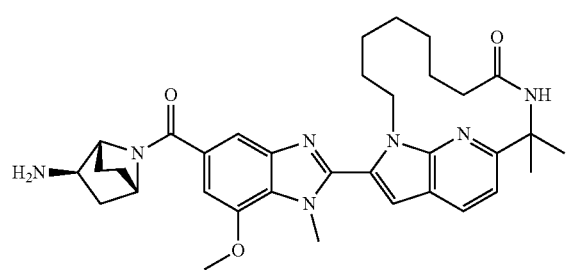
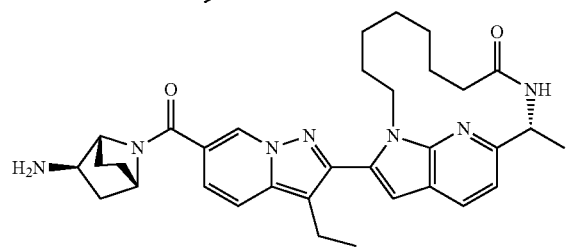
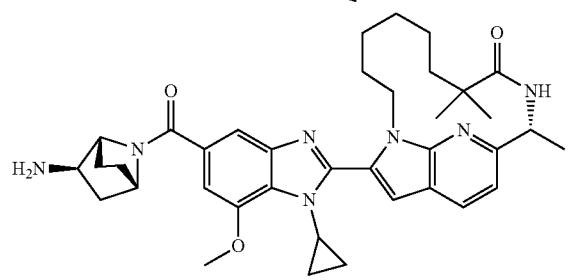
1312
-continued
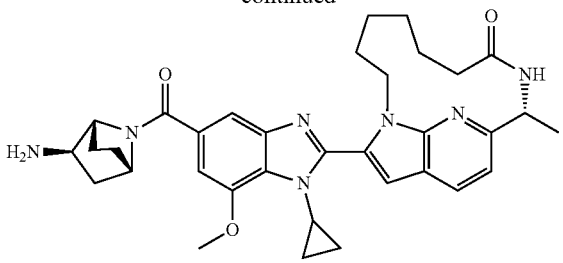
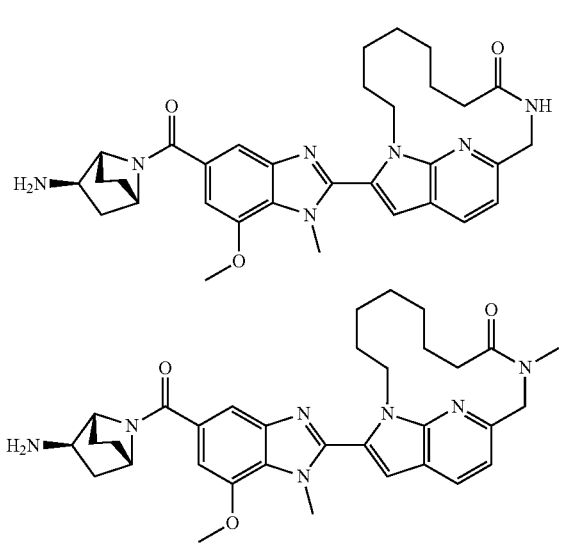
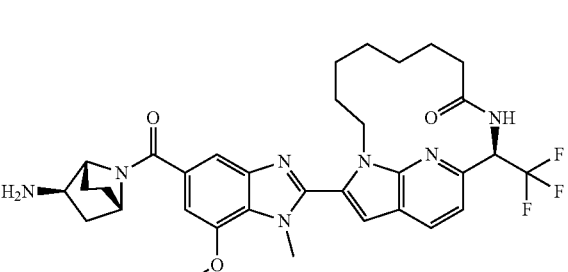
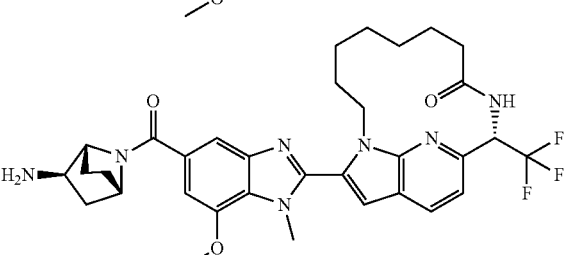
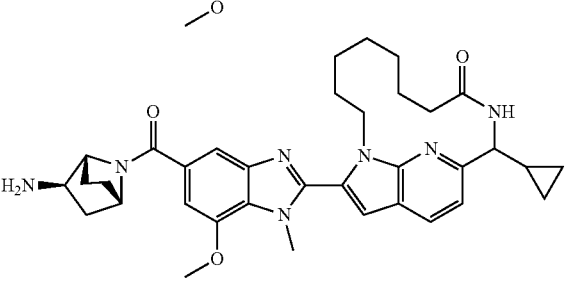

1313
-continued
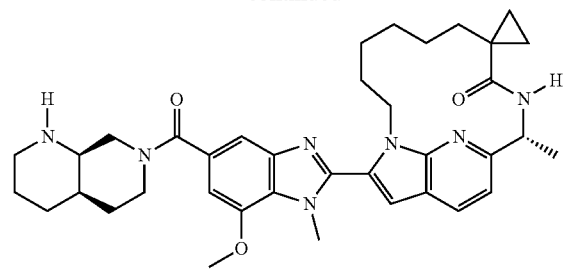
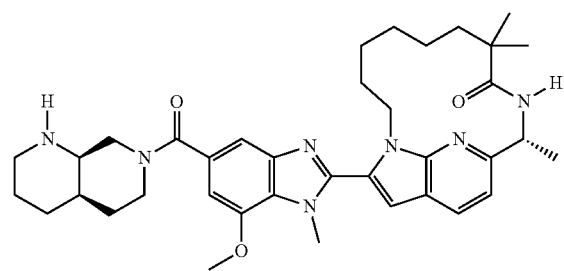
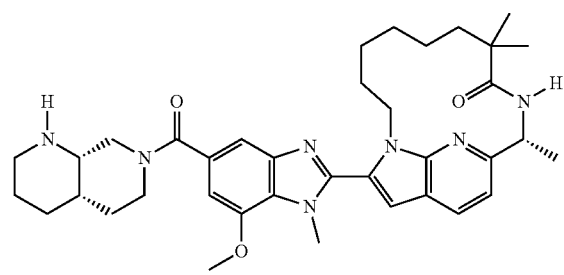
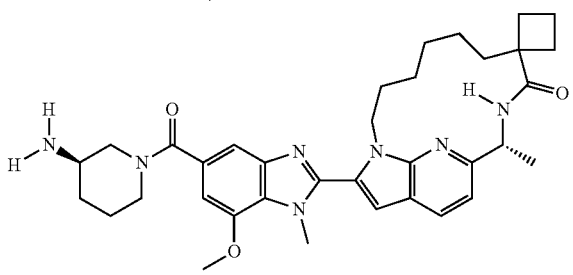
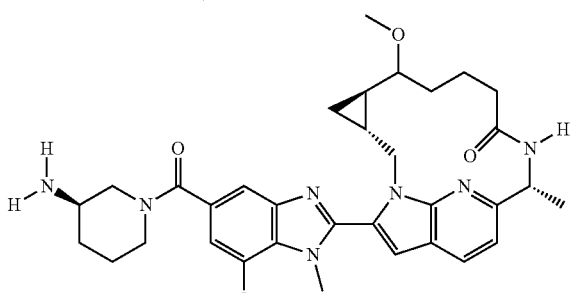
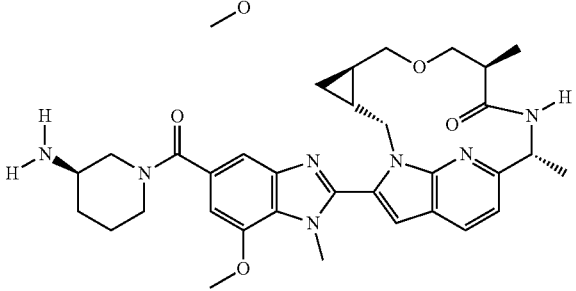
1314
-continued
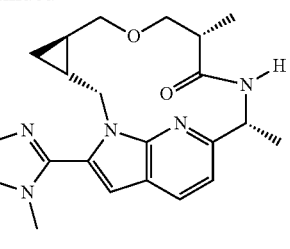
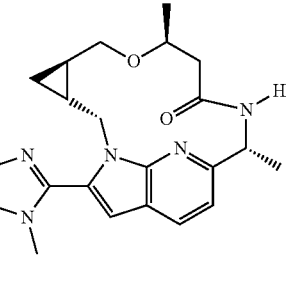
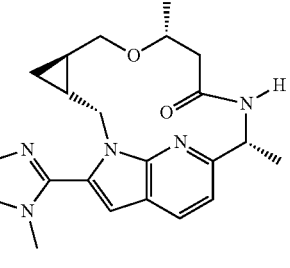
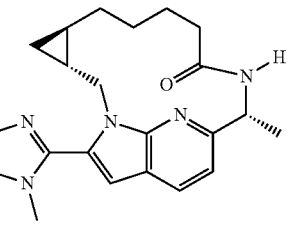
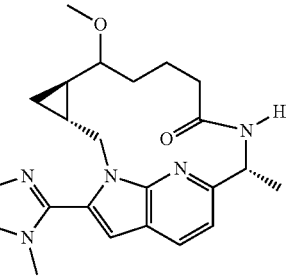
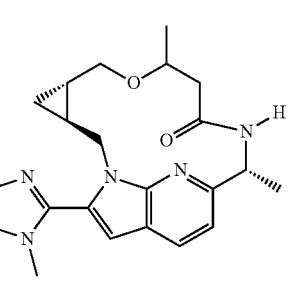

1315
-continued
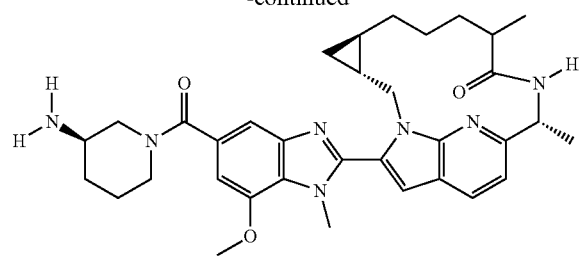
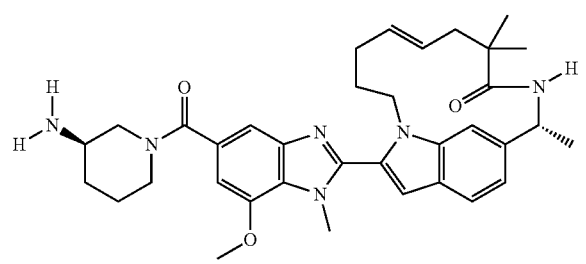
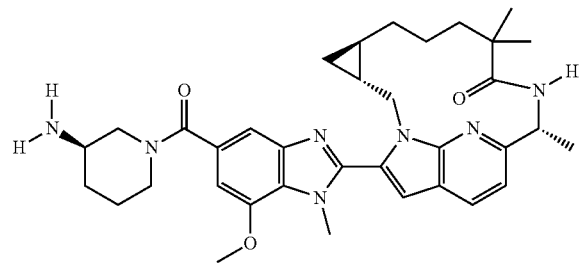
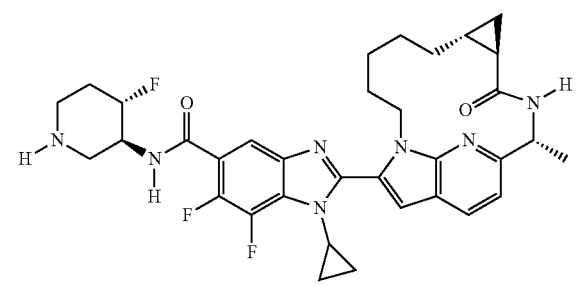
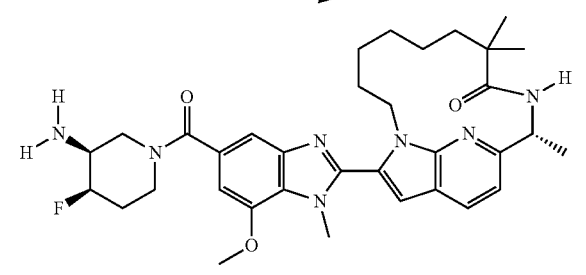
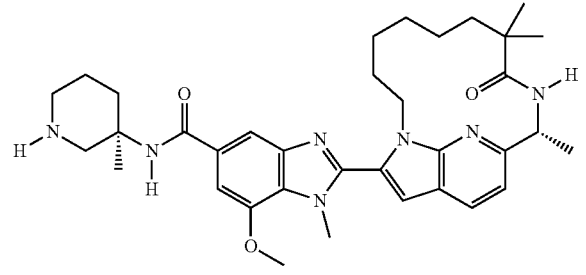
1316
-continued
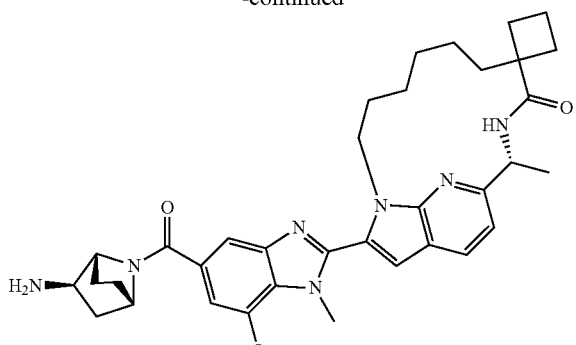
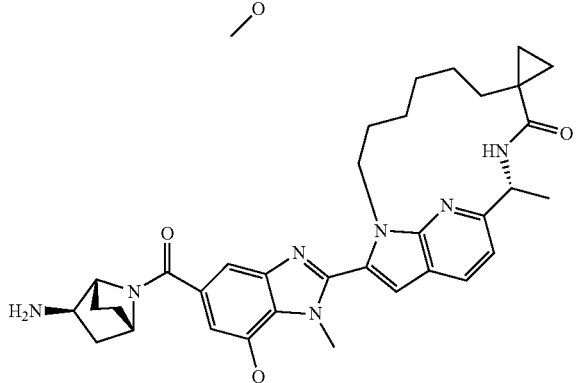
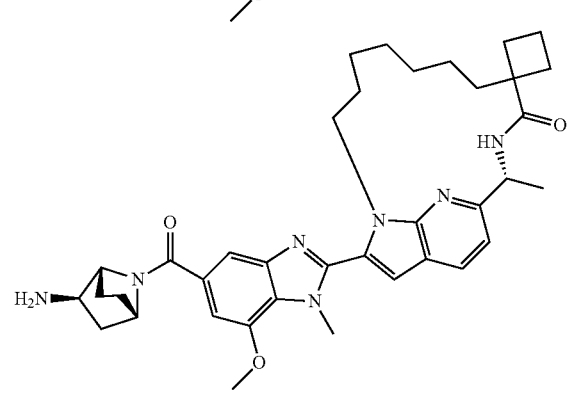
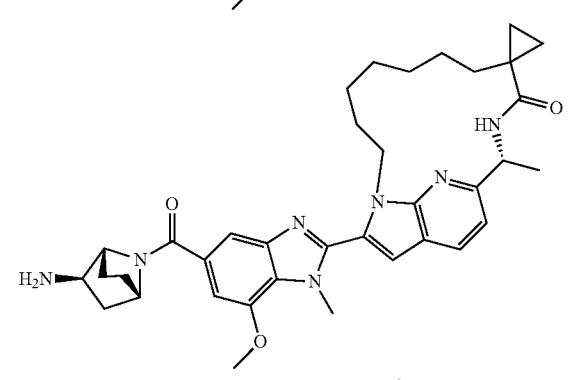
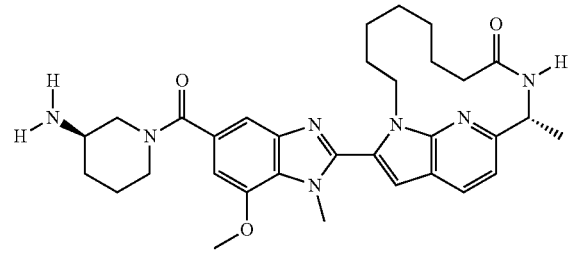

1317
-continued
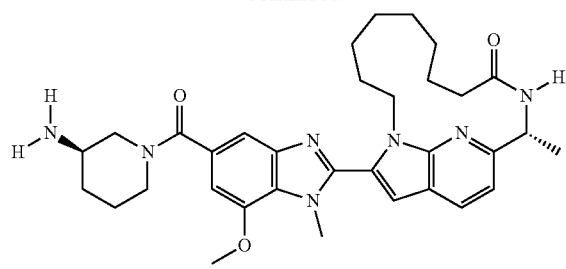
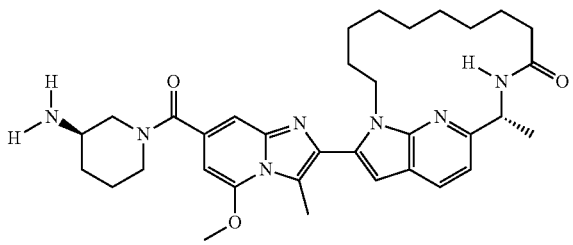
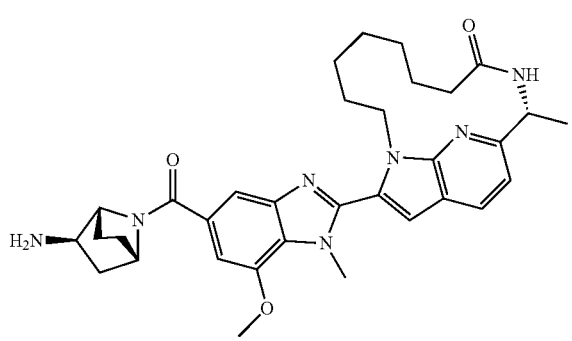
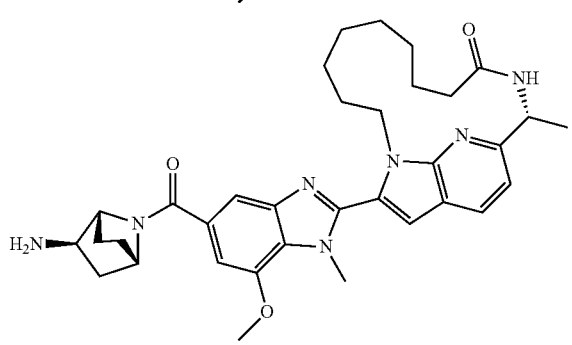
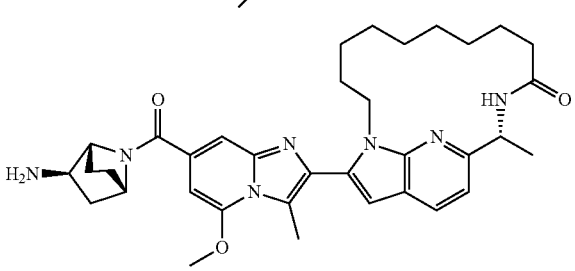
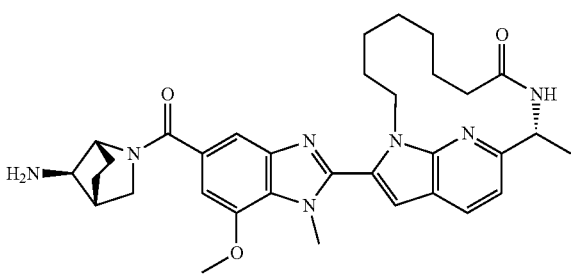
1318
-continued
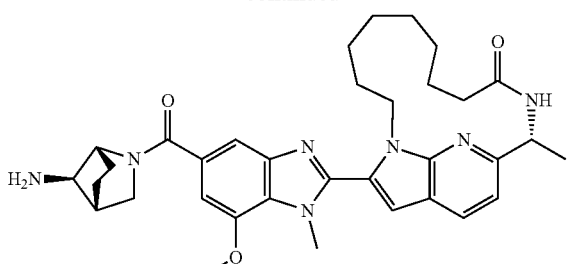
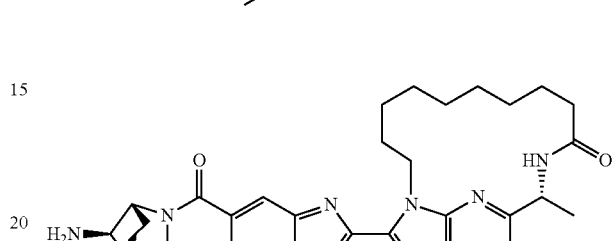
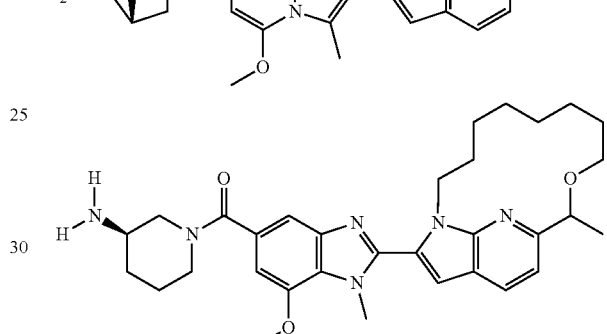
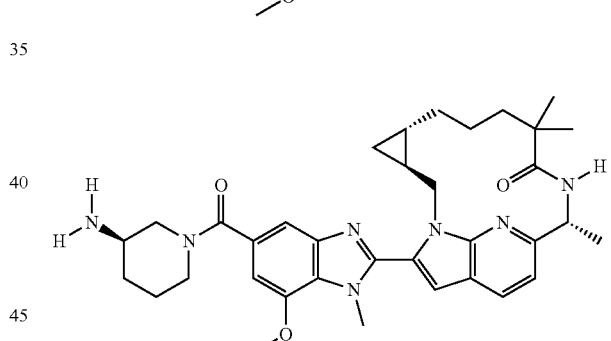
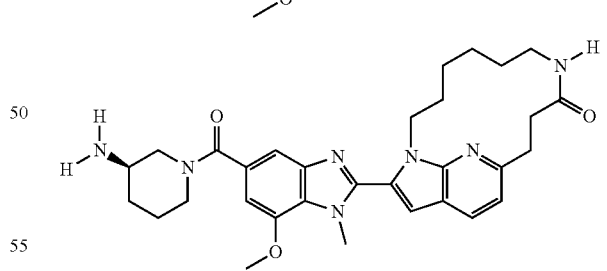
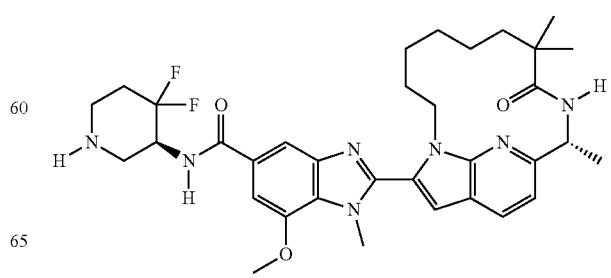

| 1319 | 1320 |
|---|---|
| 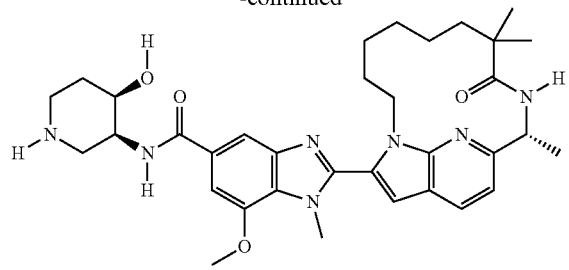 | 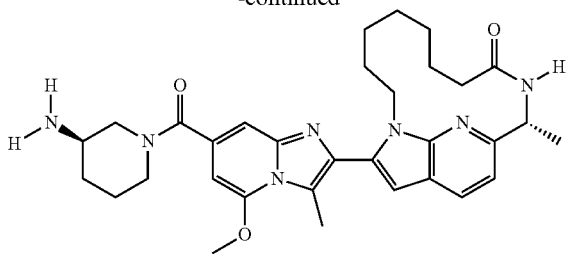 |
| 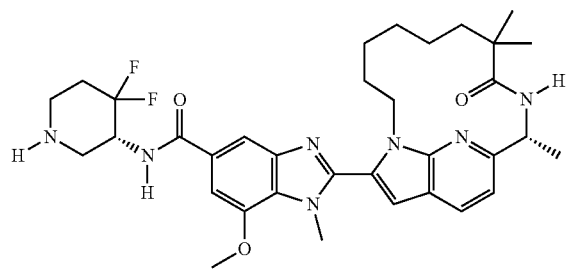 | |
| 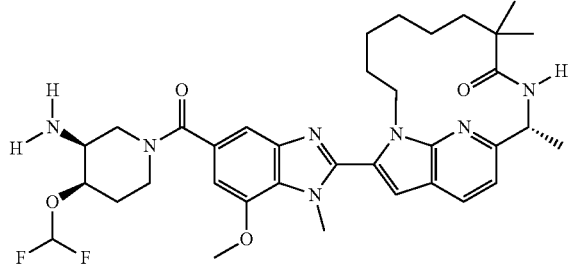 | 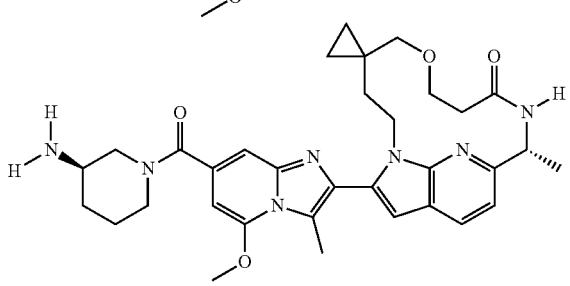 |
| 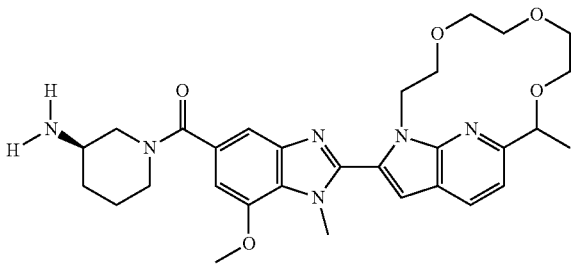 | 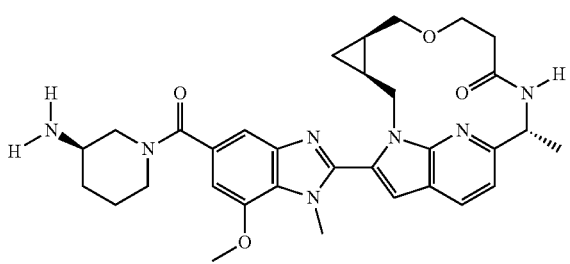 |
| 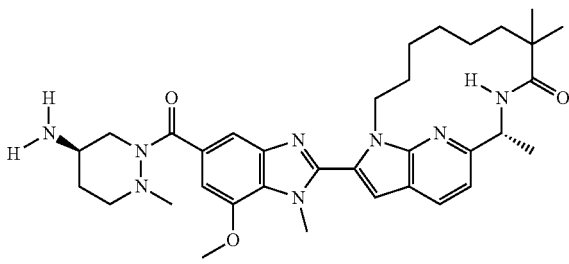 | 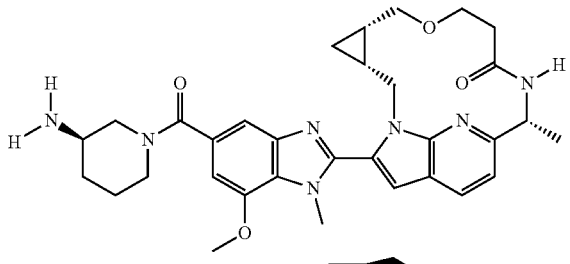 |
| 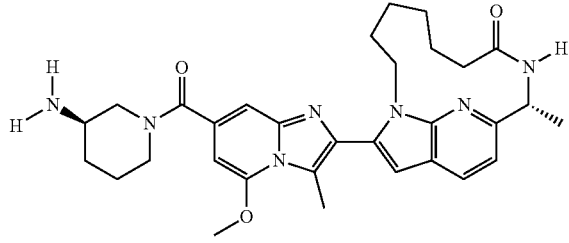 | 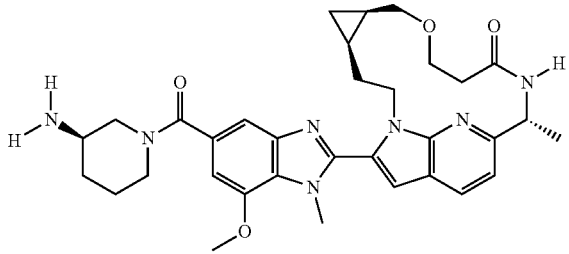 |

1321
-continued
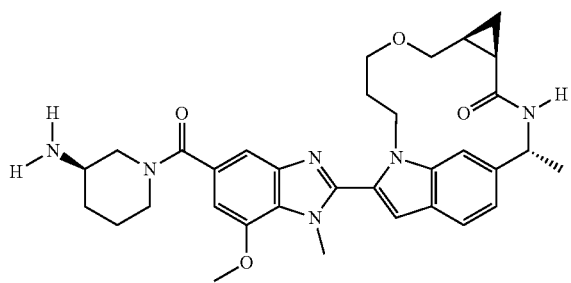
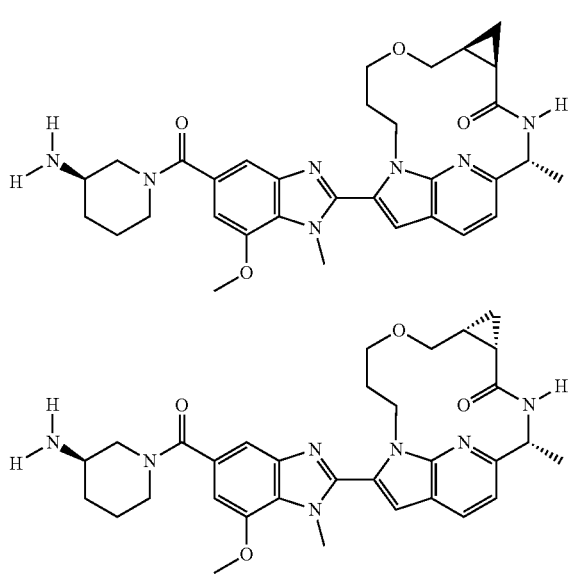
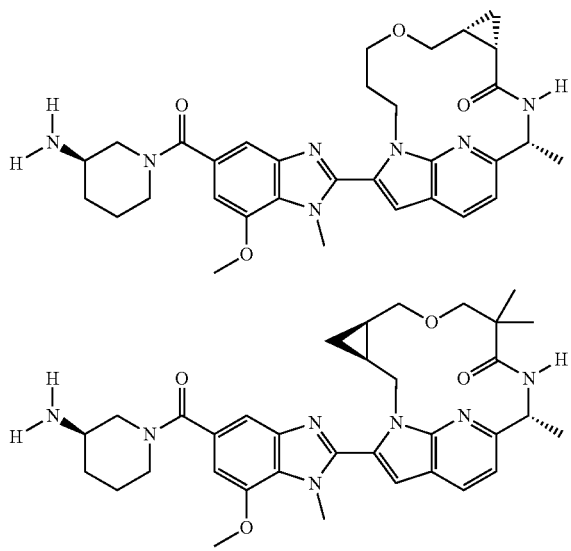
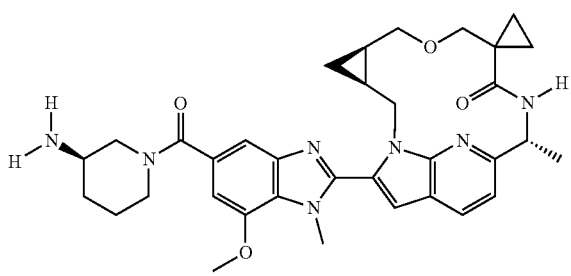
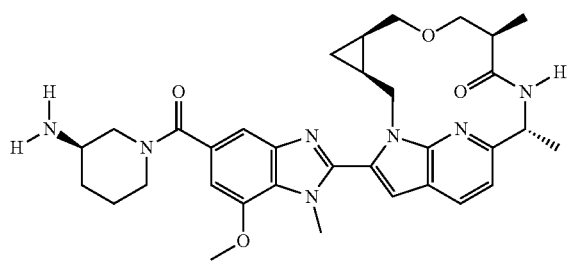
1322
-continued
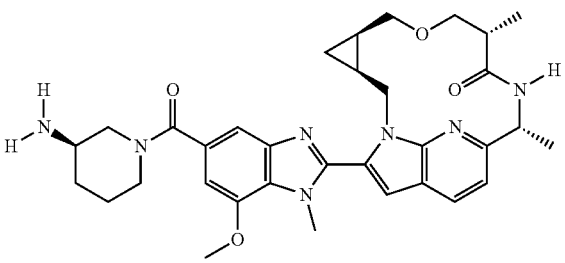
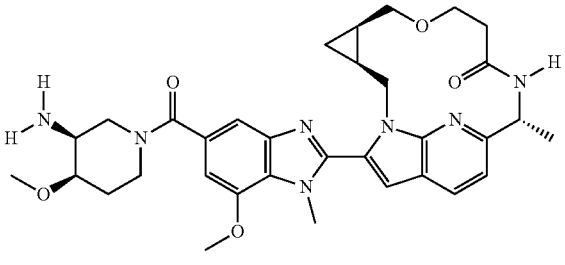
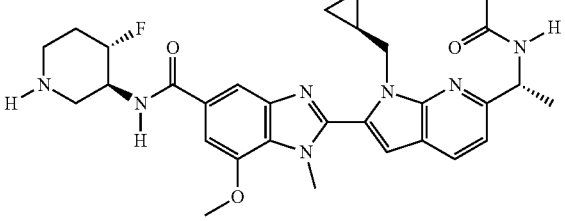
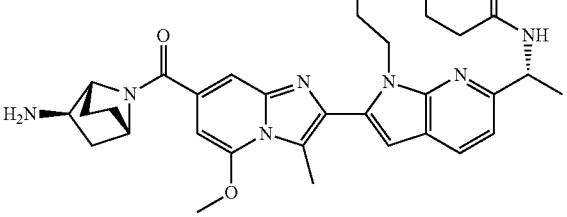
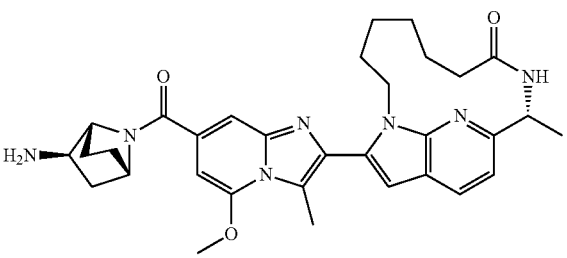
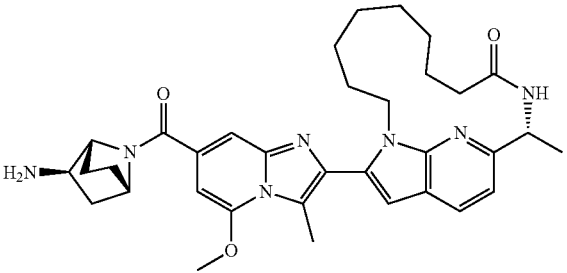

1323
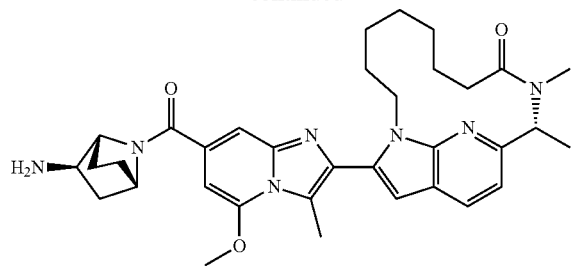
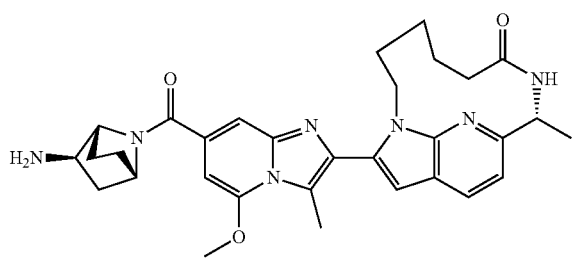
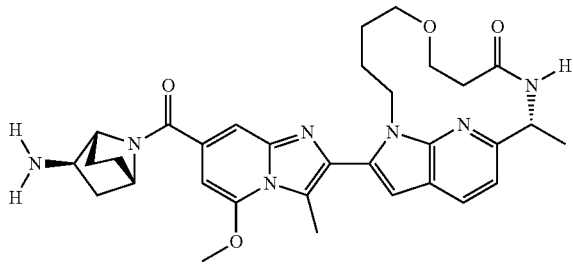
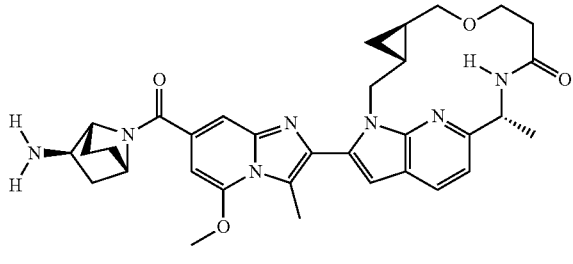
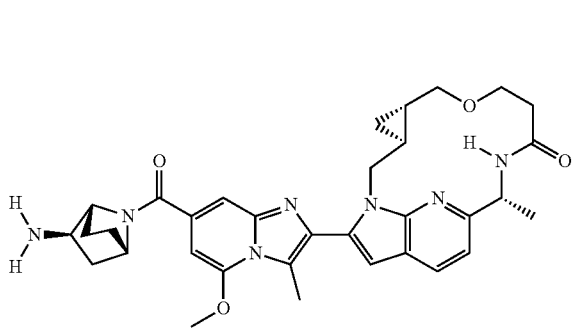
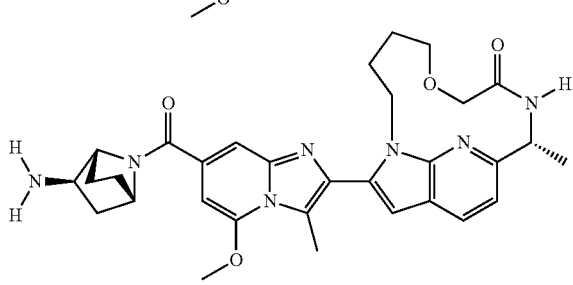
1324
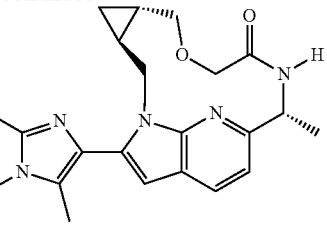
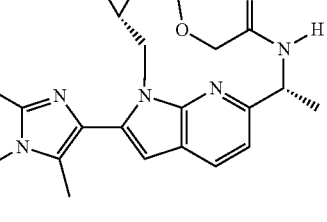
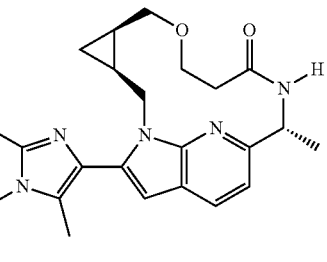
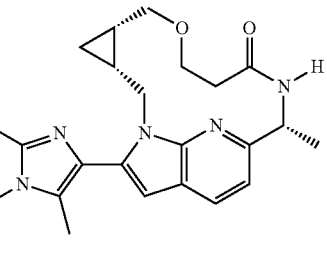
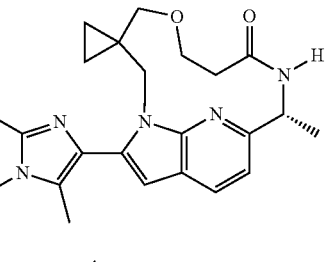
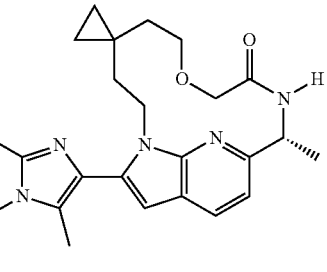

1325
-continued
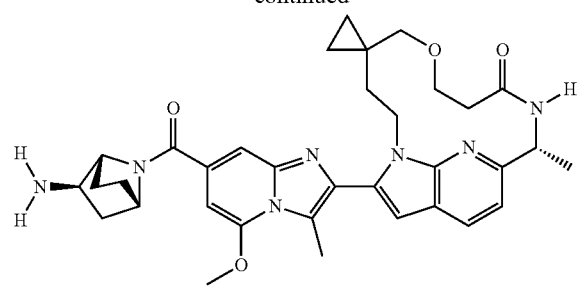
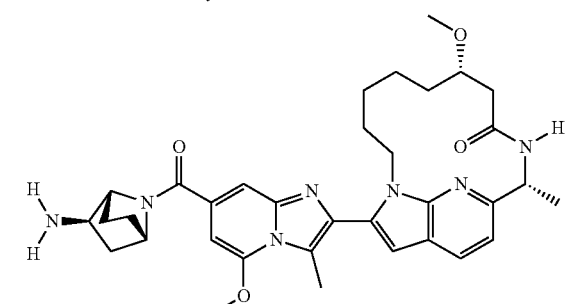
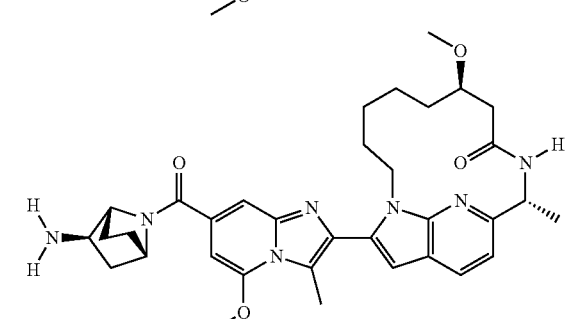
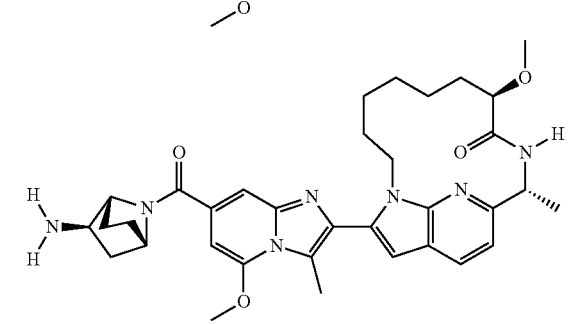
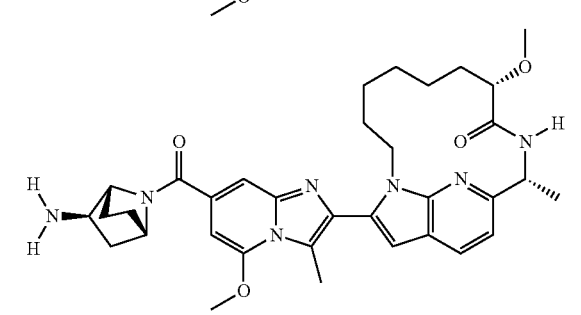
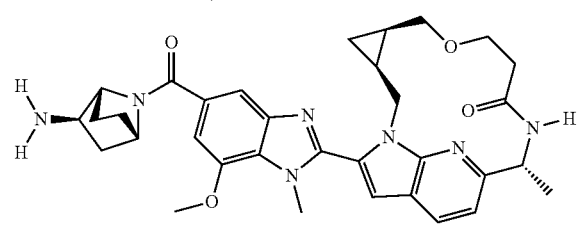
1326
-continued
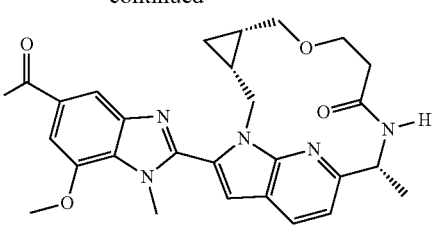
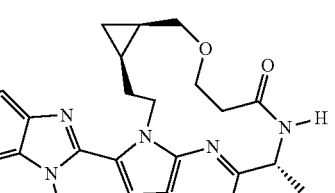
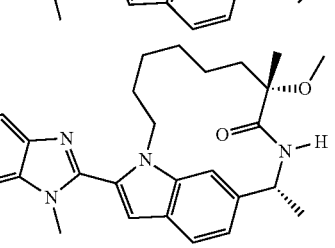
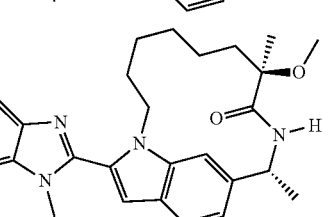
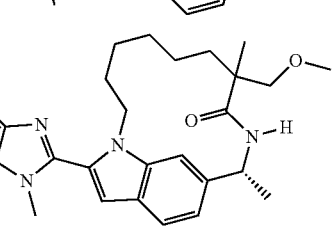
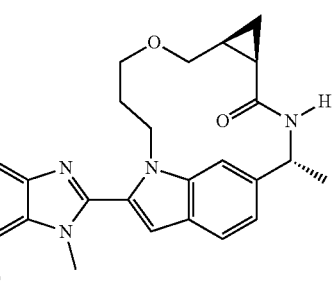
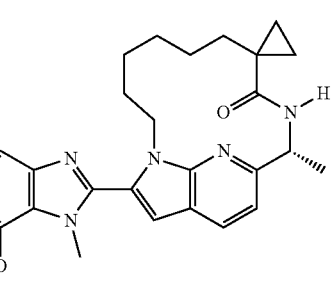

1327
-continued
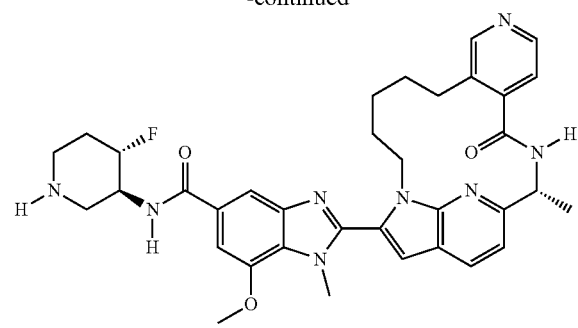
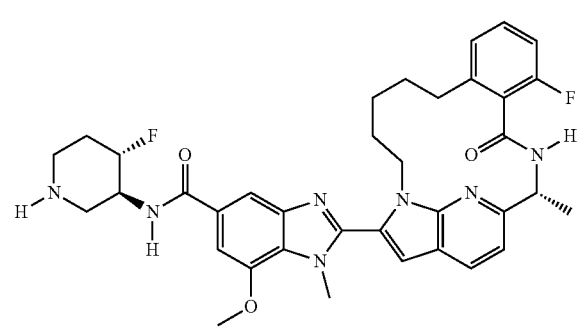
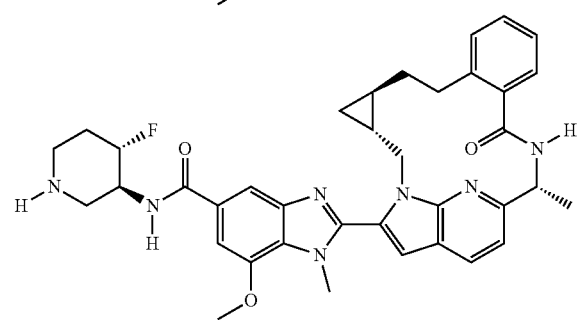
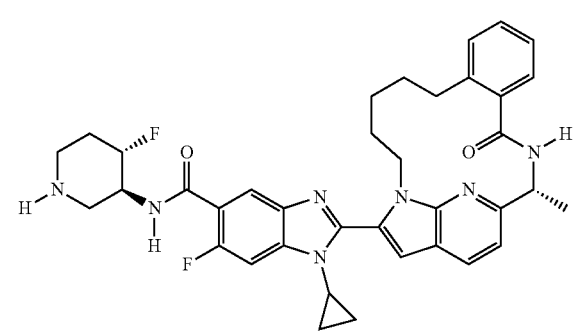
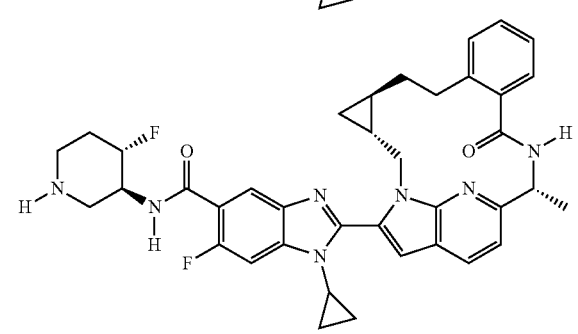
1328
-continued
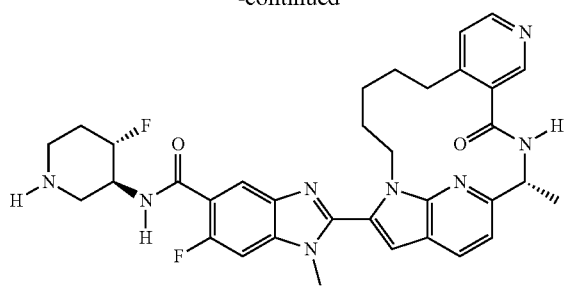
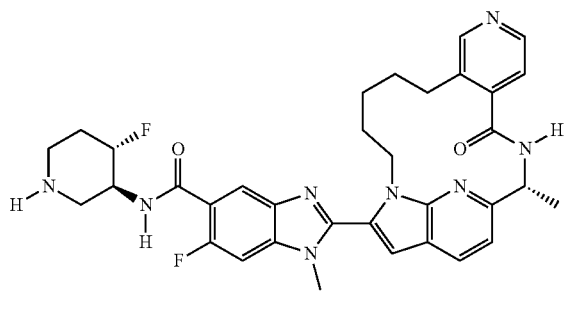
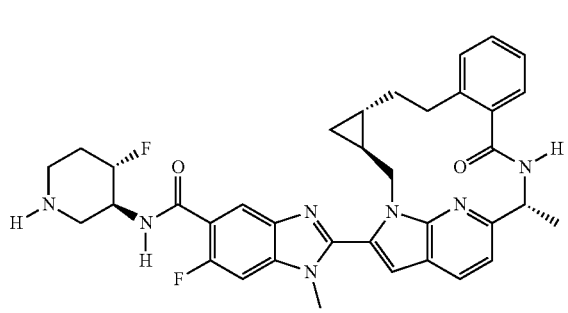
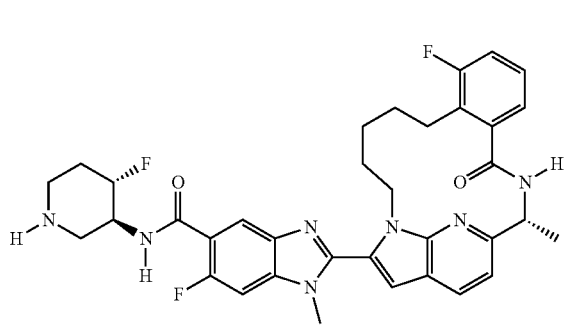
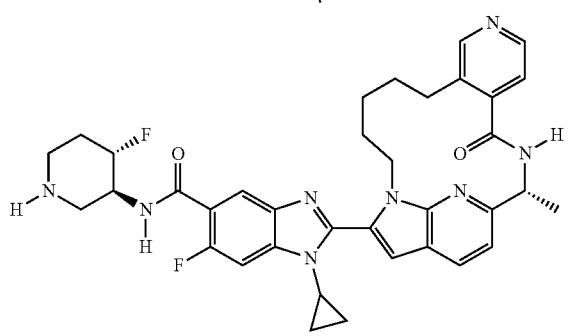

1329
-continued
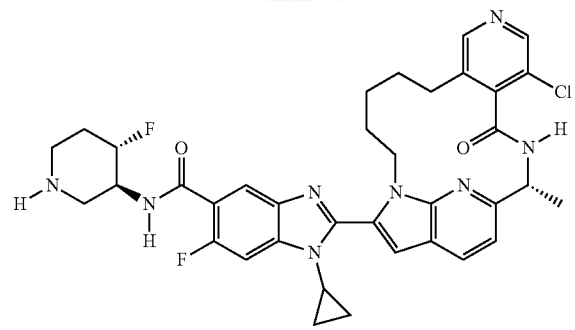
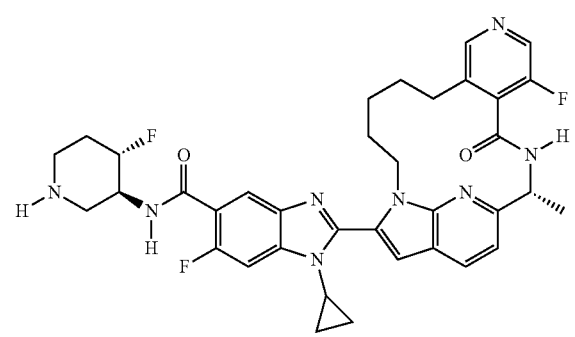
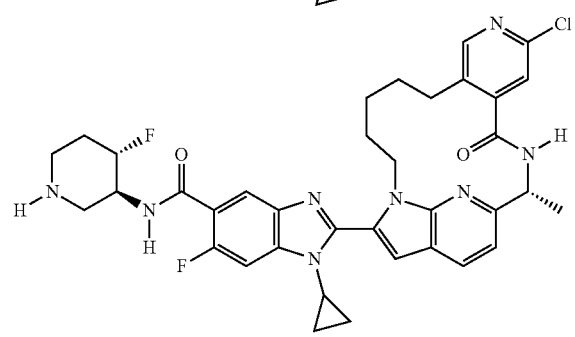
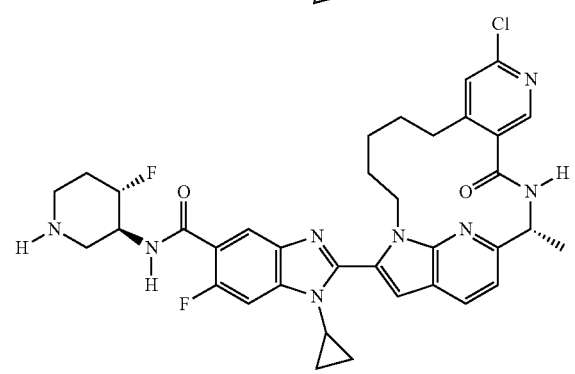
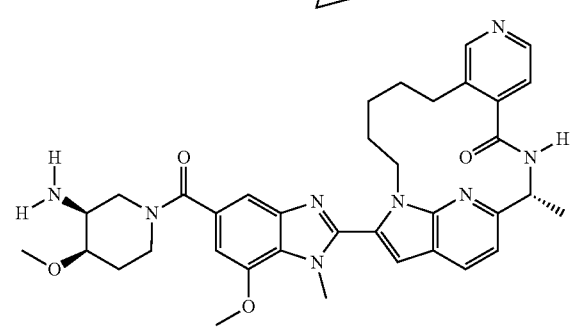
1330
-continued
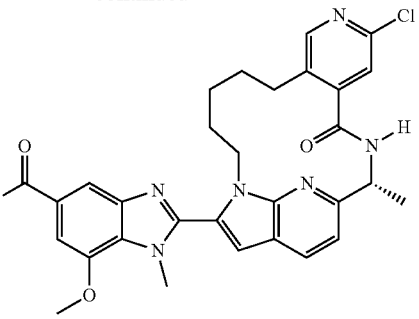
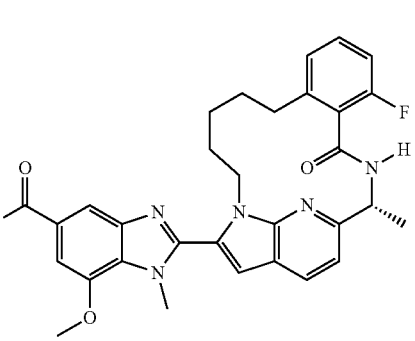
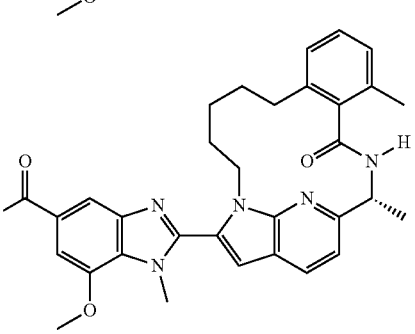
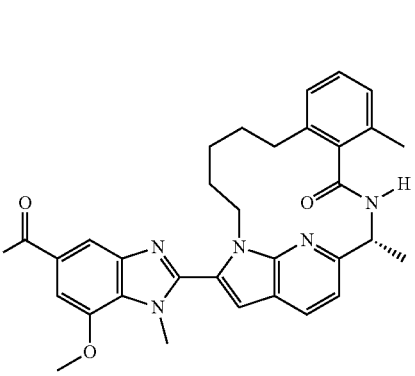
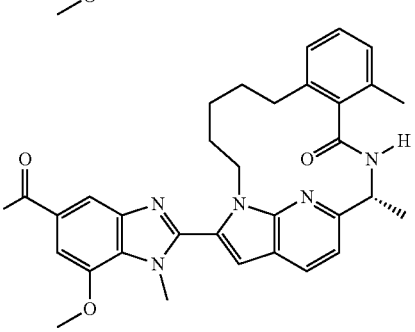

1331
-continued
1332
-continued
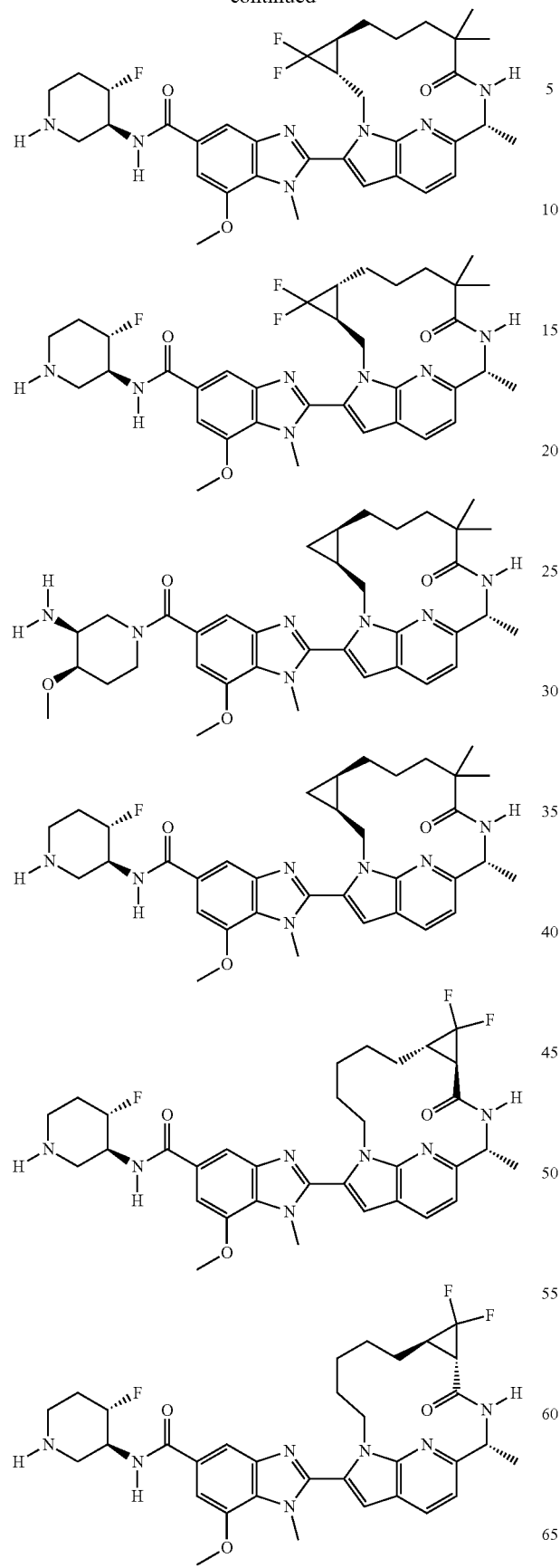
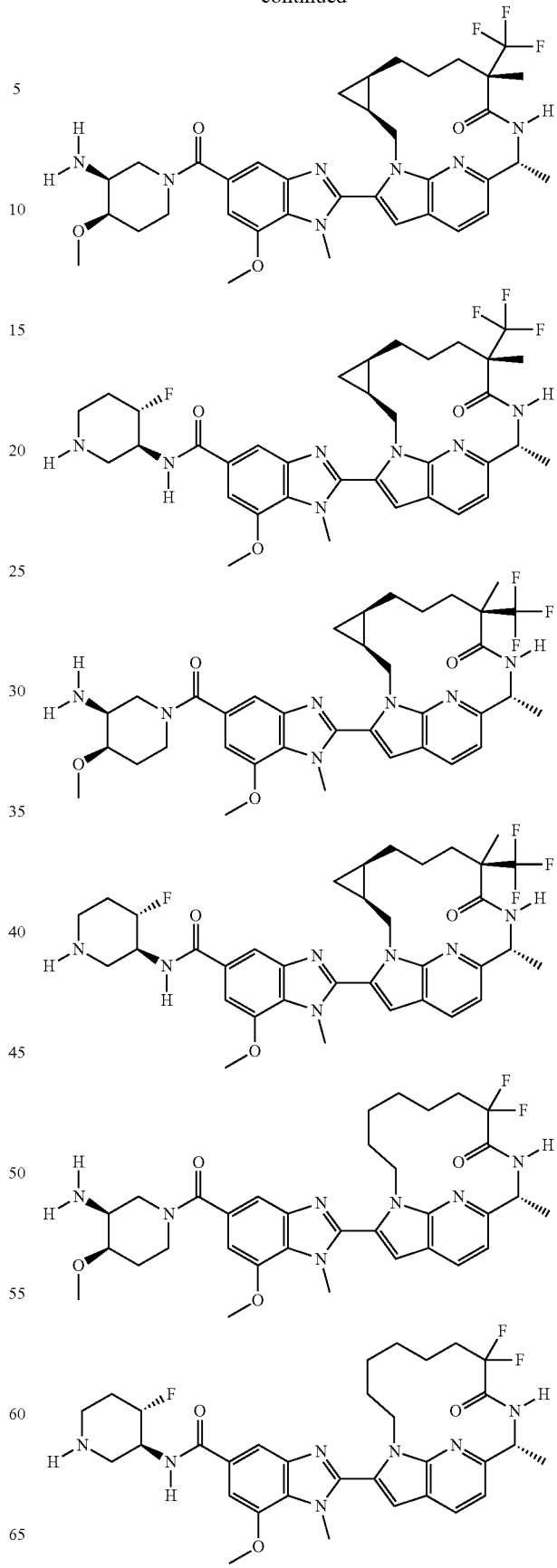

1333
-continued
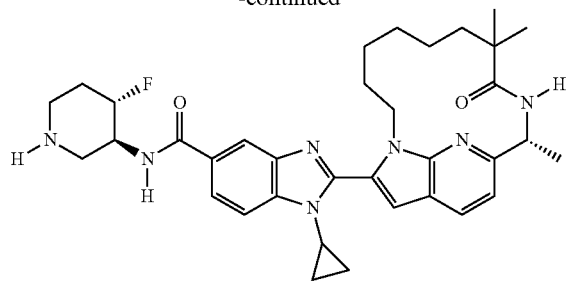
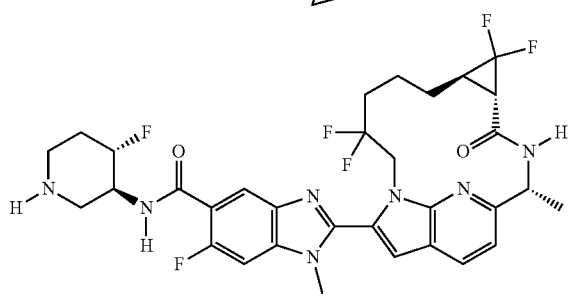
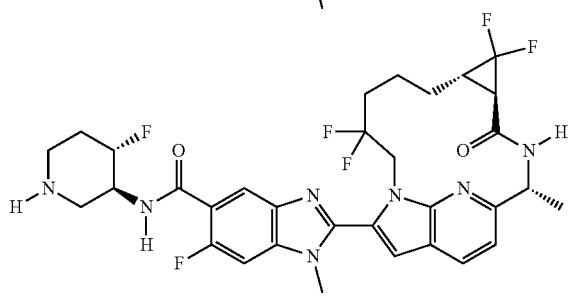
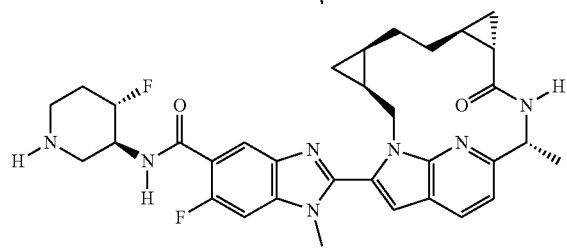
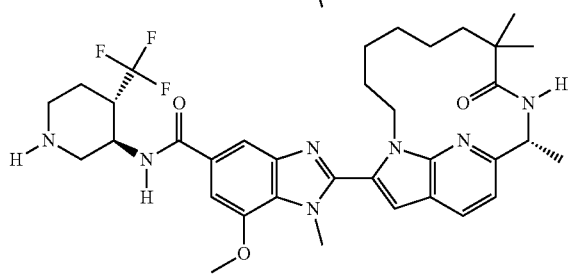
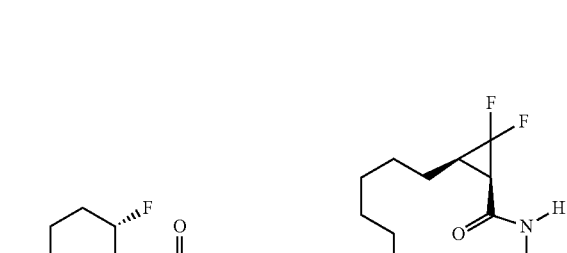
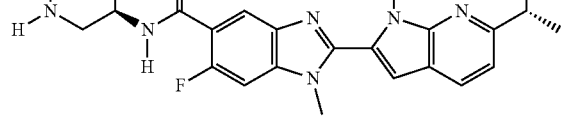
1334
-continued
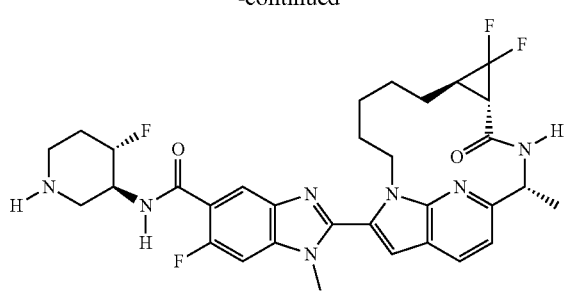
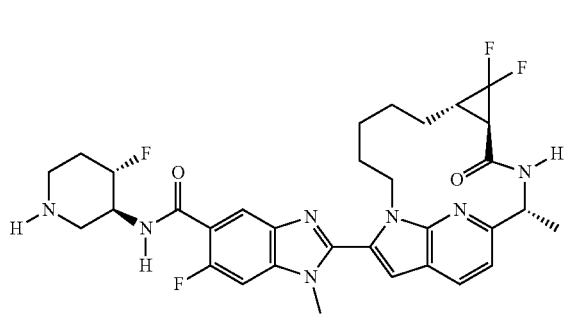
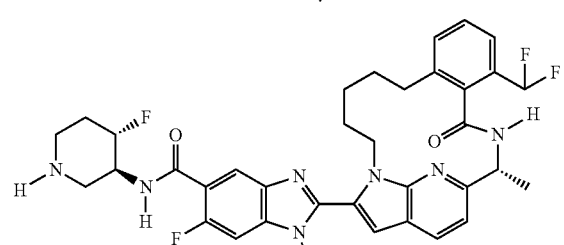
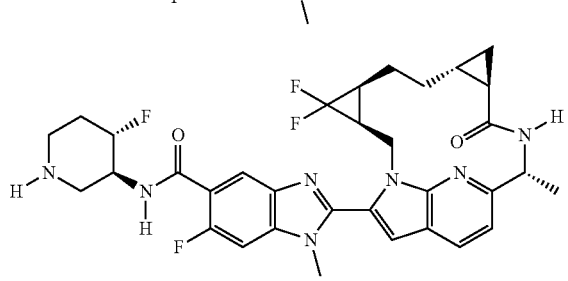
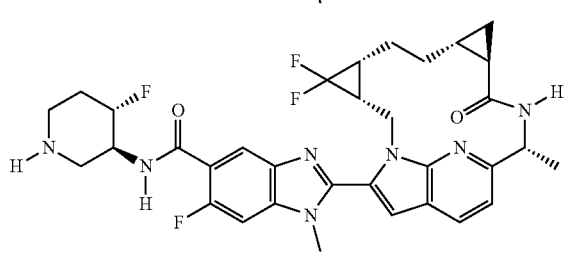
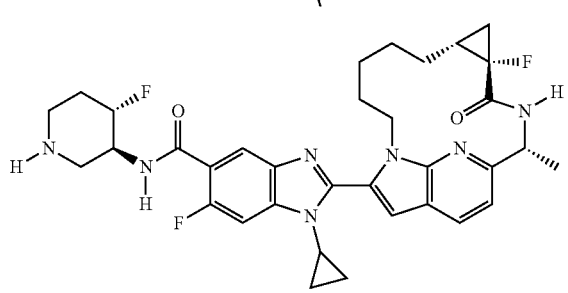

1335
-continued
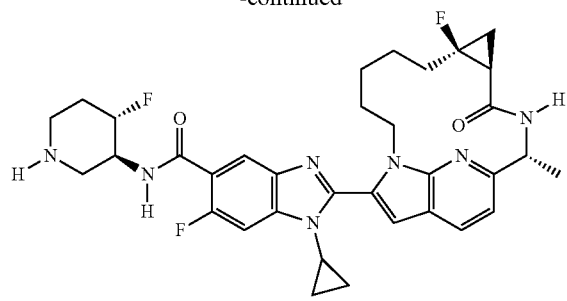
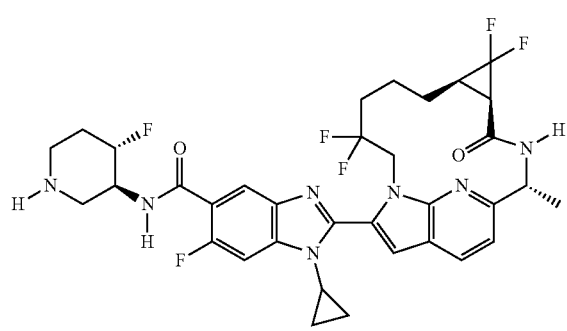
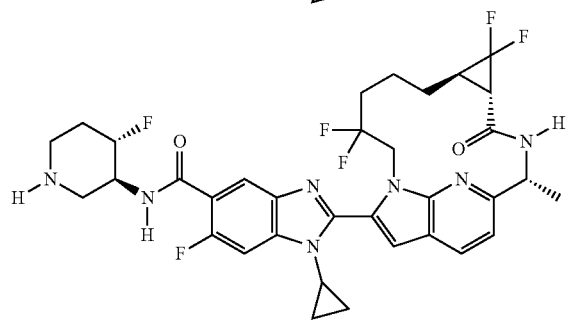
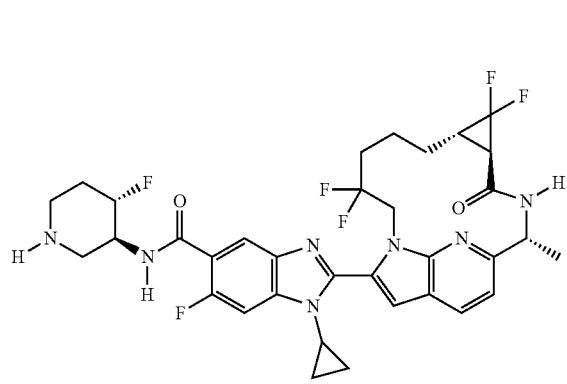
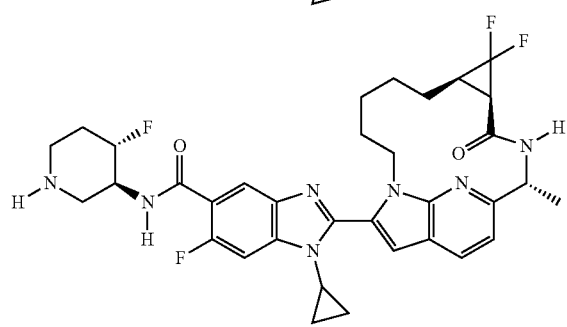
1336
-continued
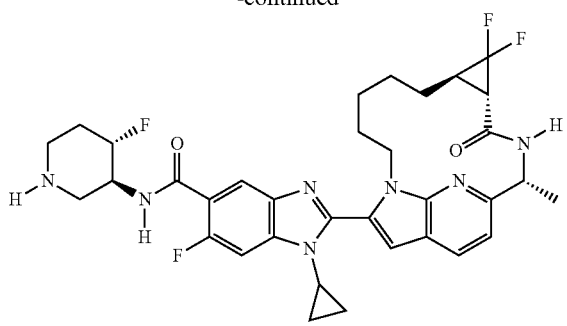
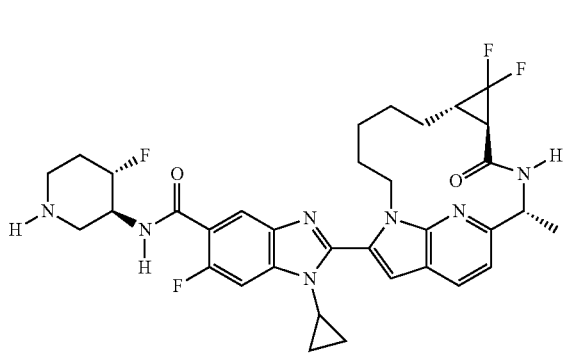
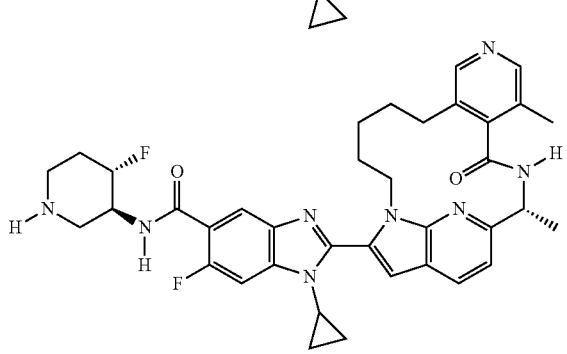
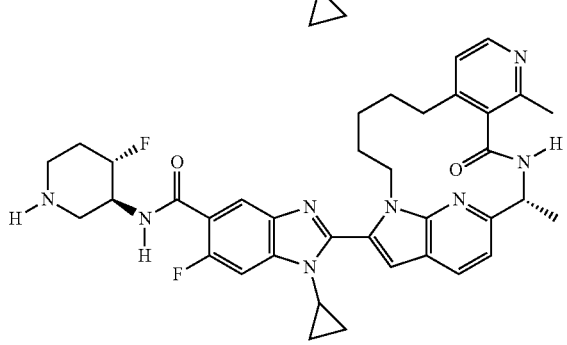
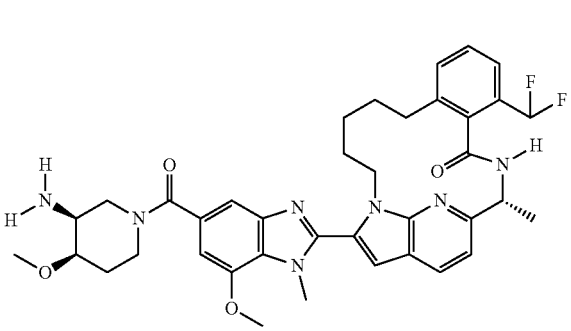

1337
-continued
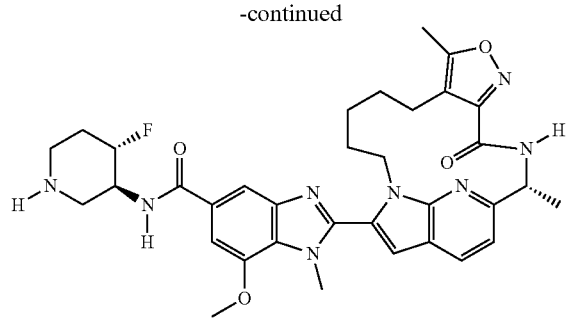
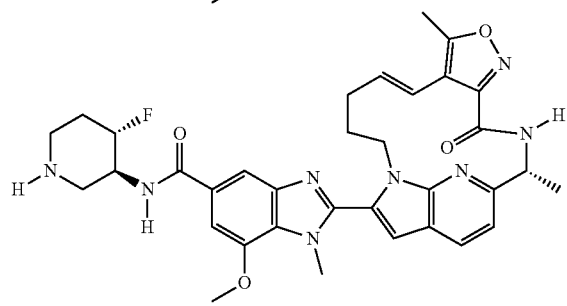
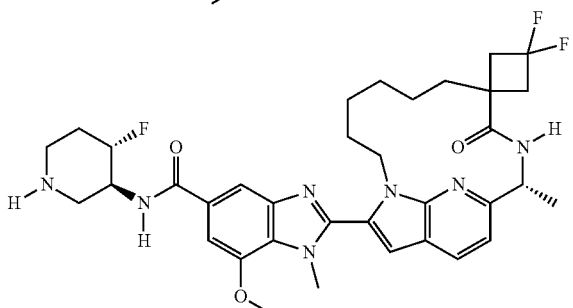
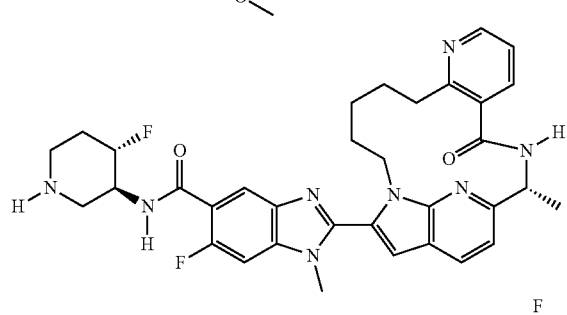
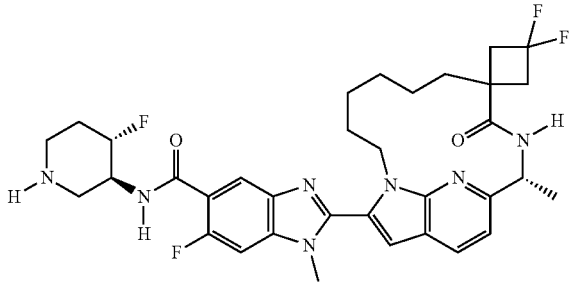
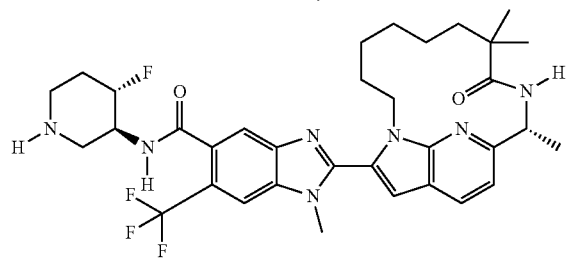
1338
-continued
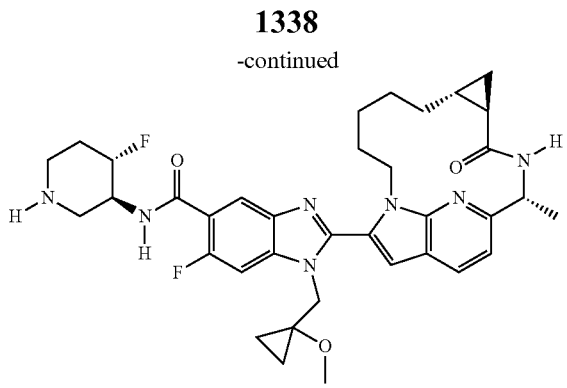
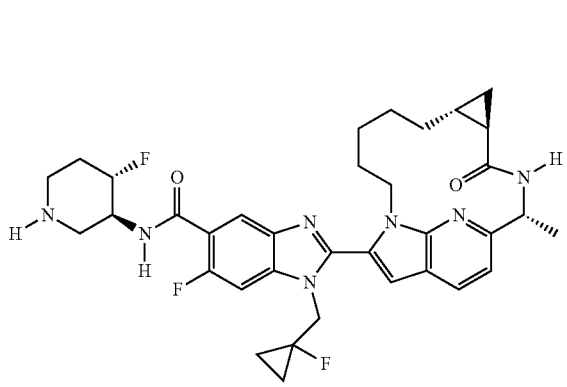
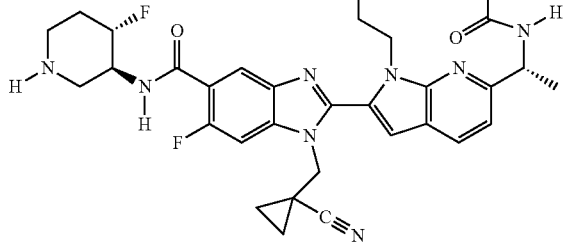
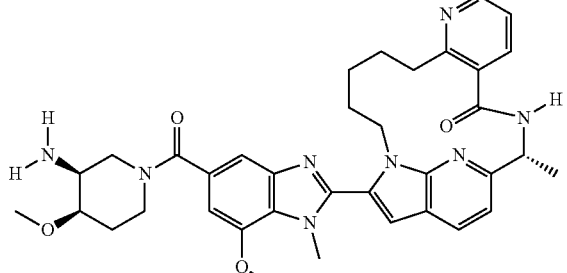
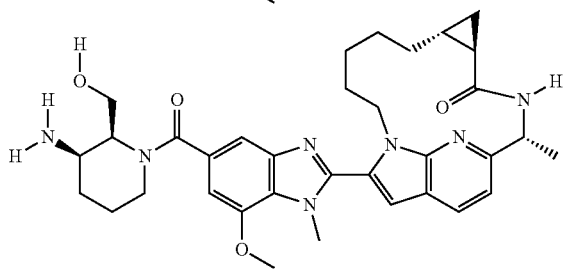

1339
-continued
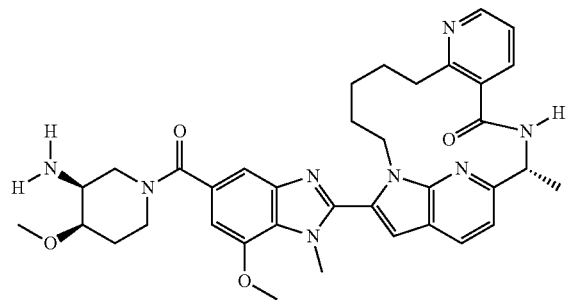
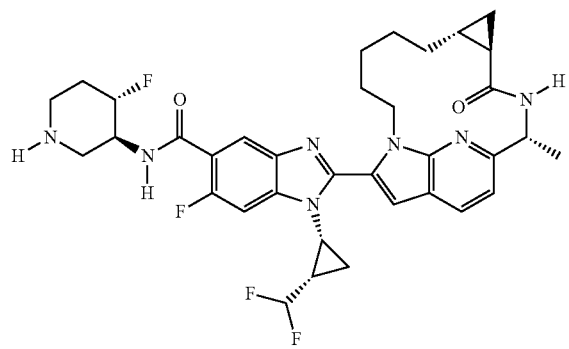
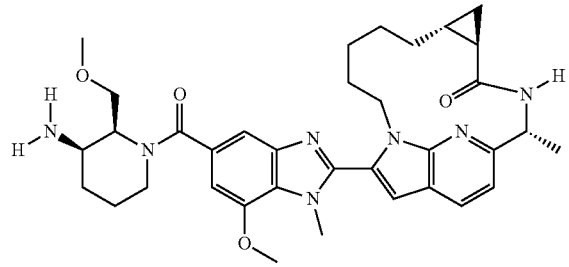
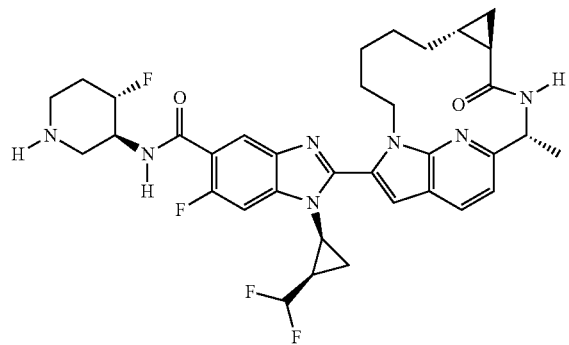
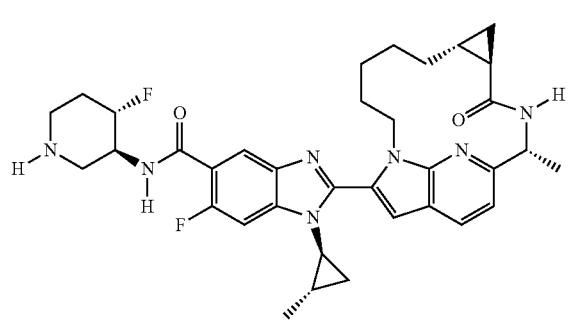
1340
-continued
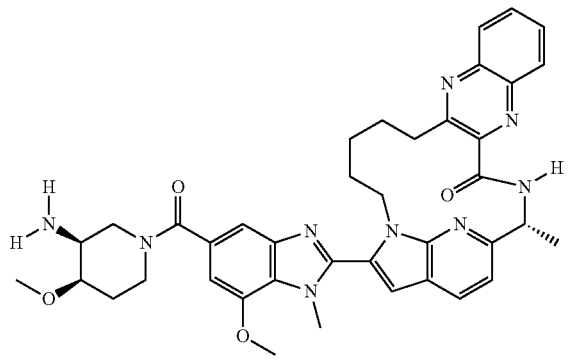
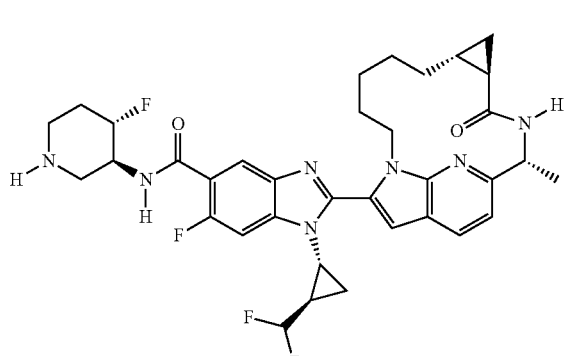
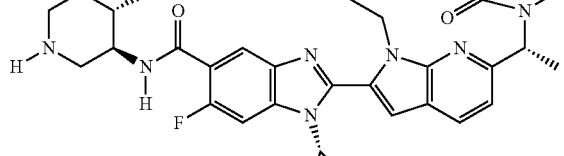
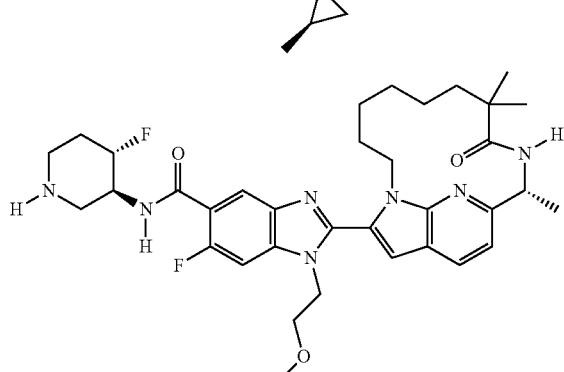
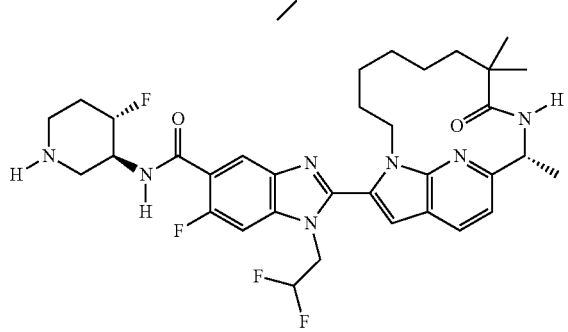

1341
-continued
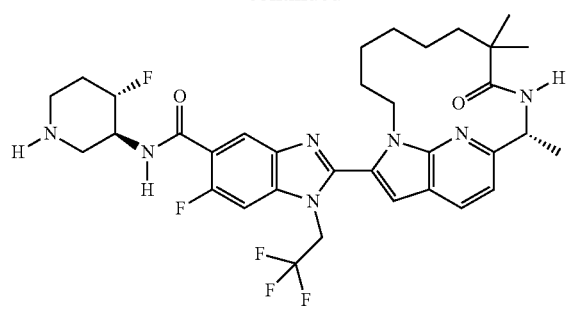
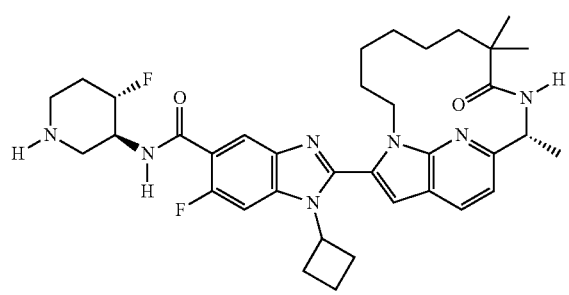
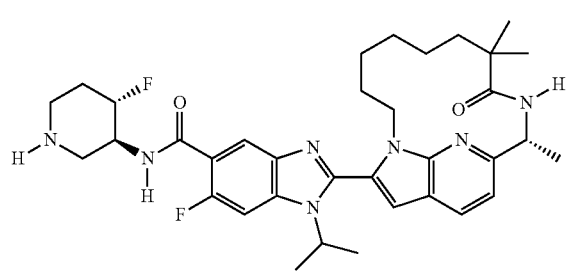
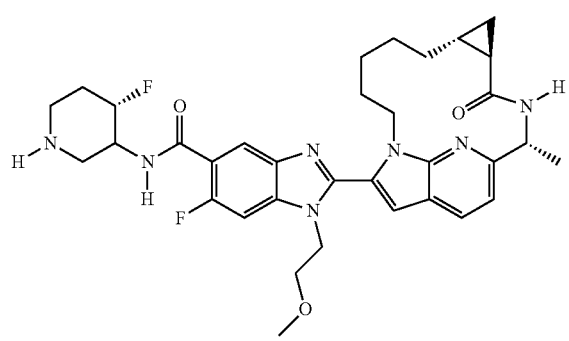
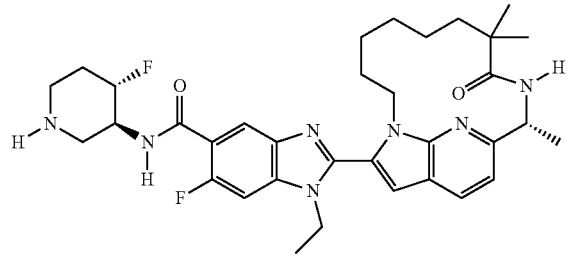
1342
-continued
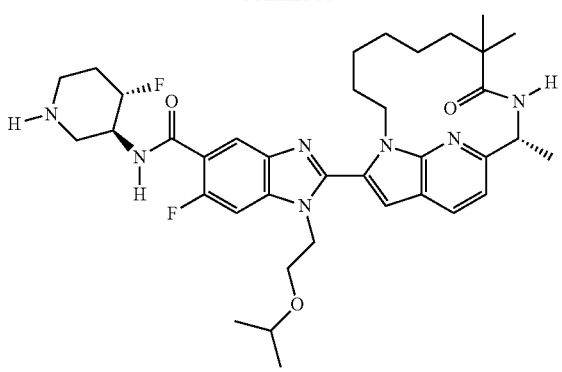
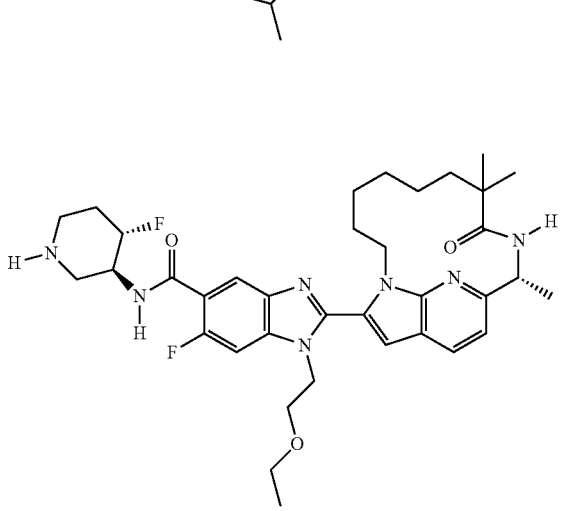
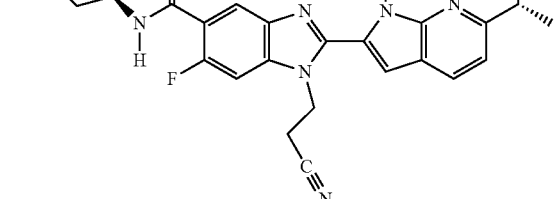
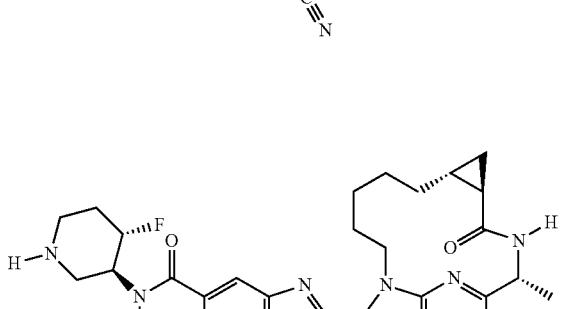
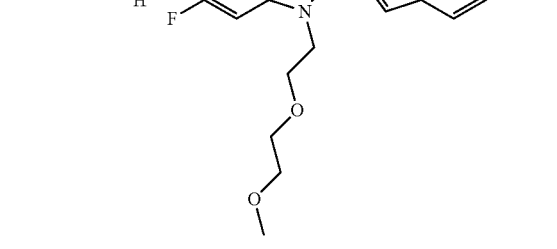

1343
-continued
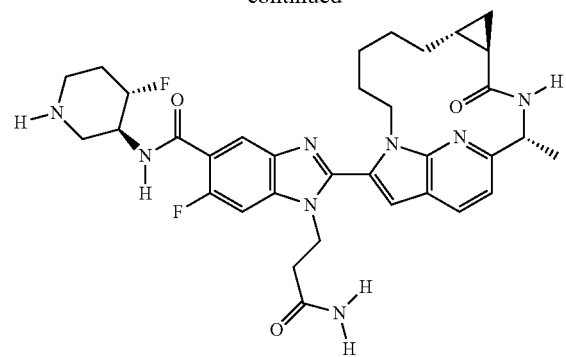
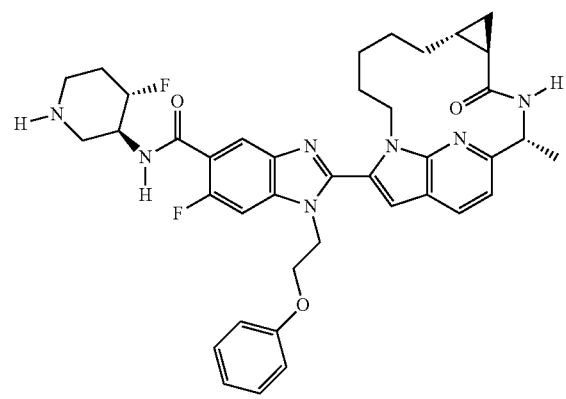
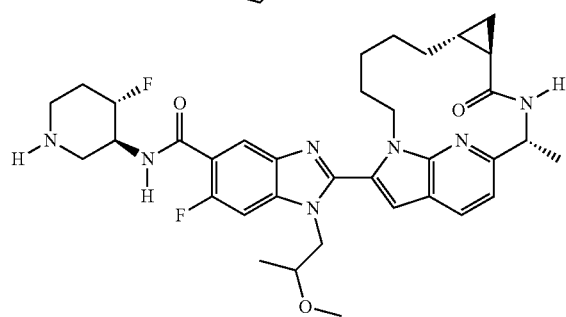
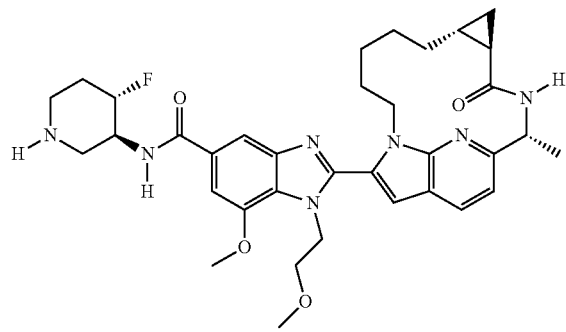
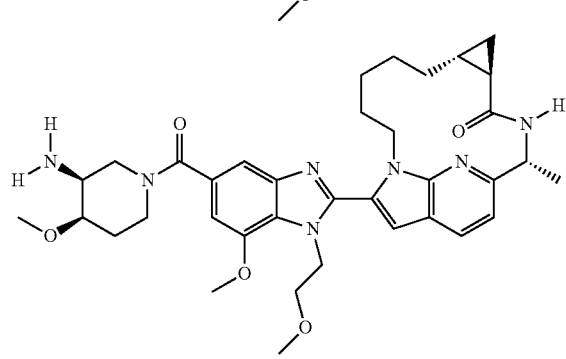
1344
-continued
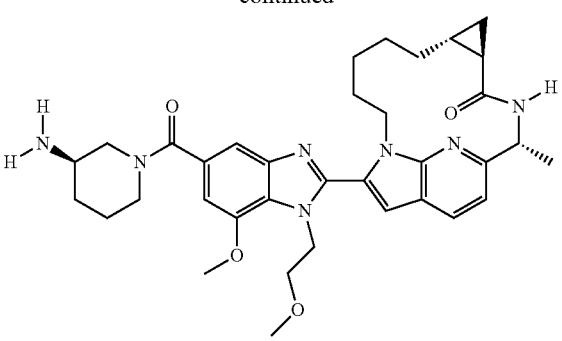
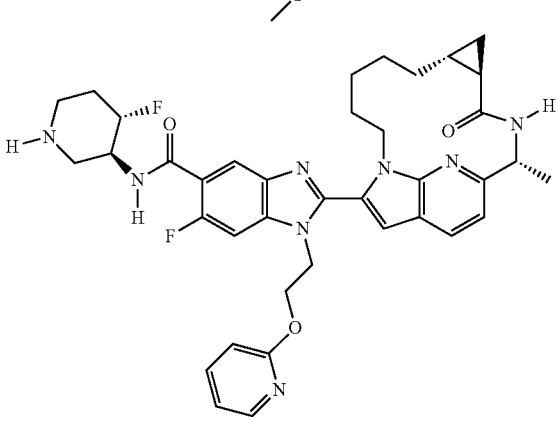
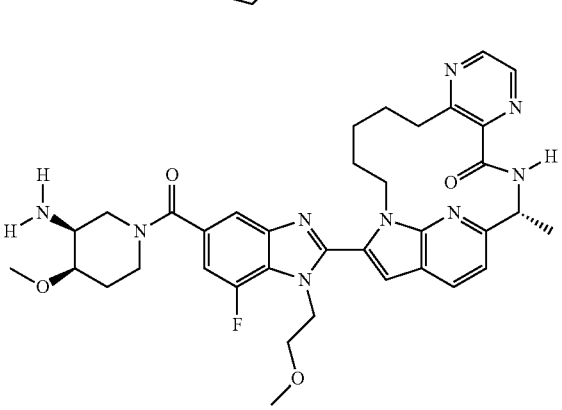
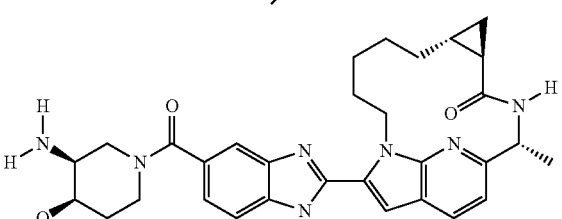
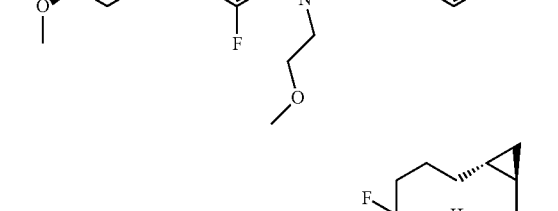

1345
-continued
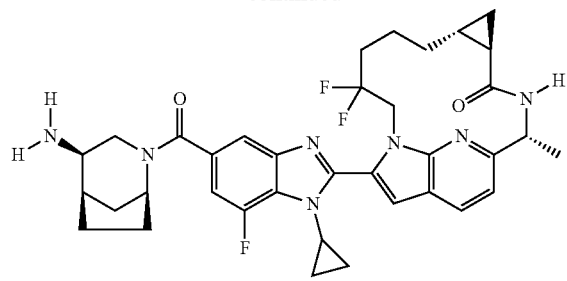
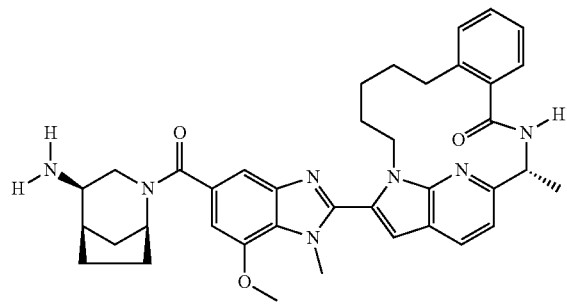
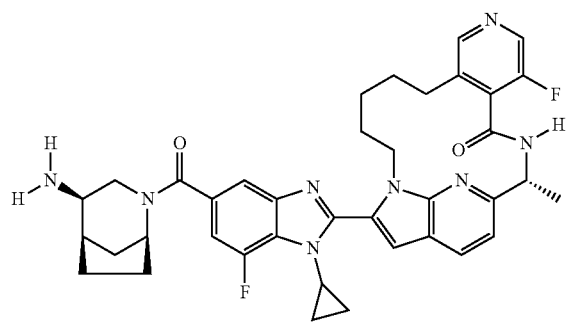
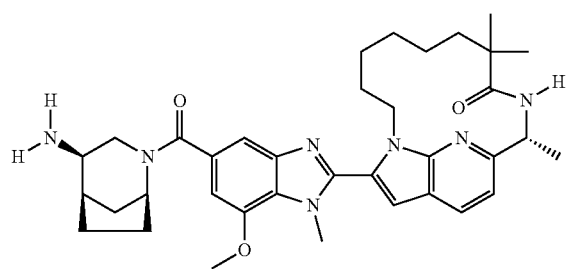
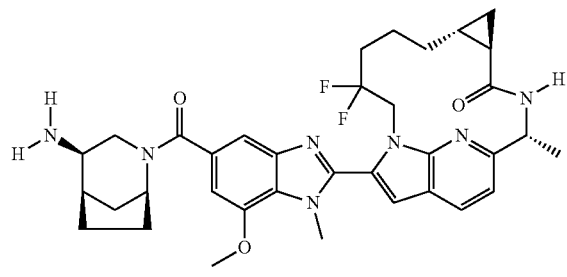
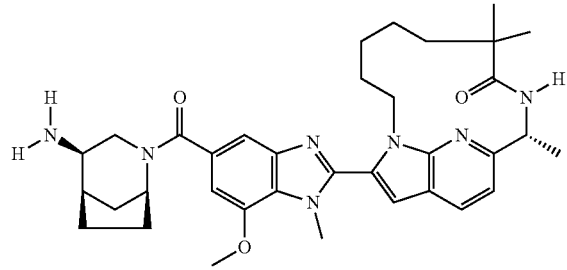
1346
-continued
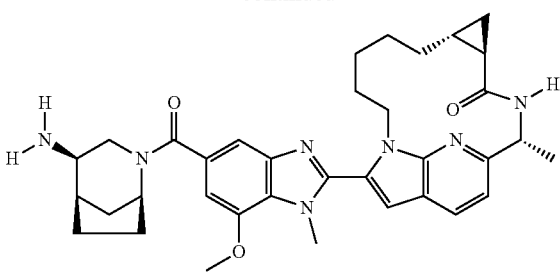
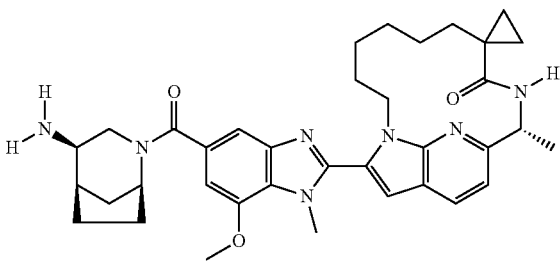
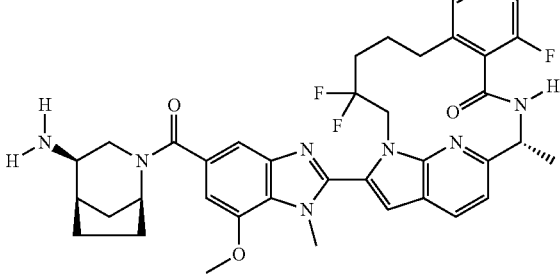
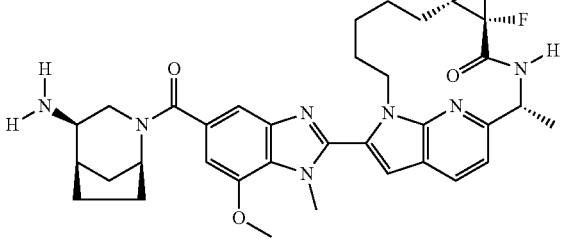
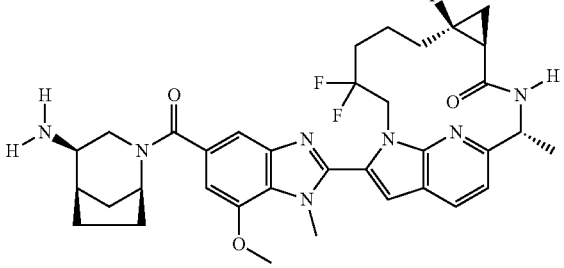
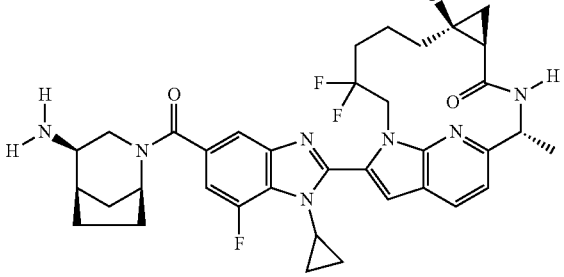

1347
-continued
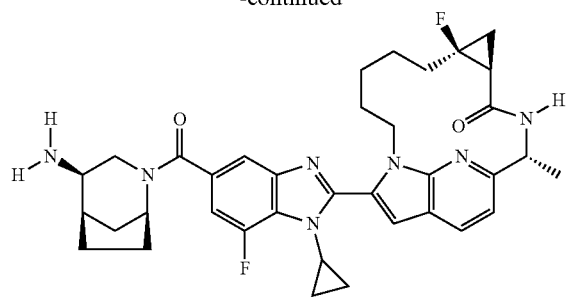
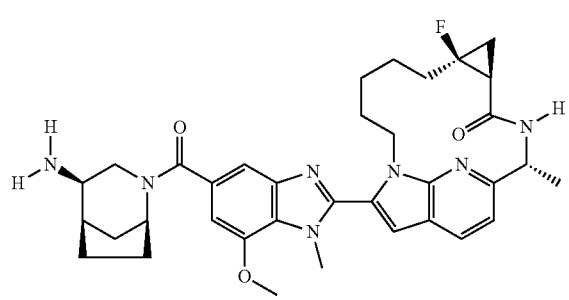
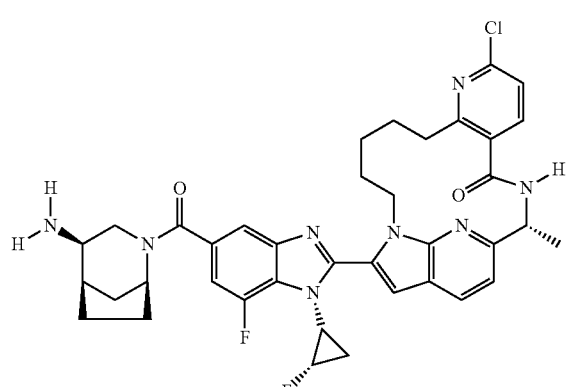
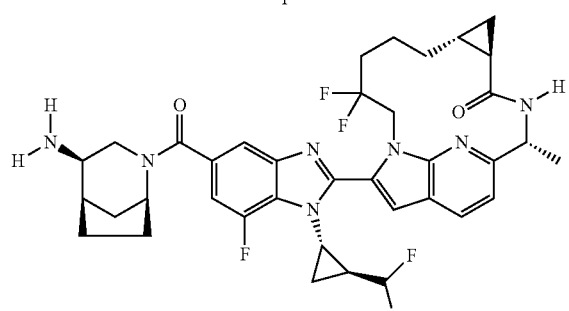
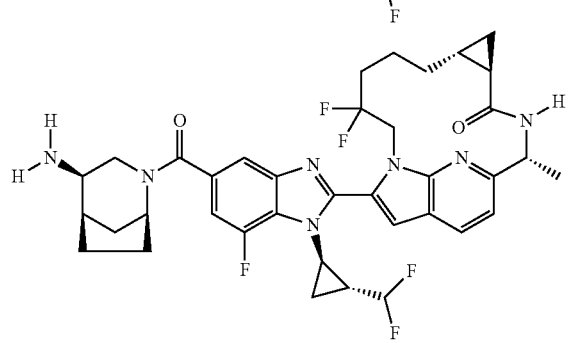
1348
-continued
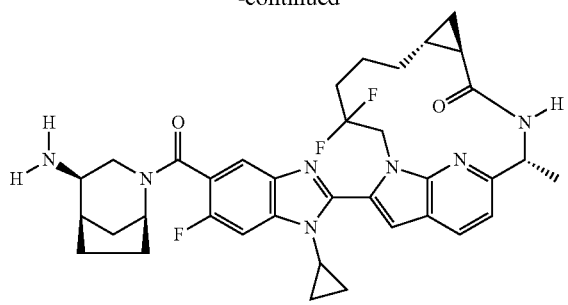
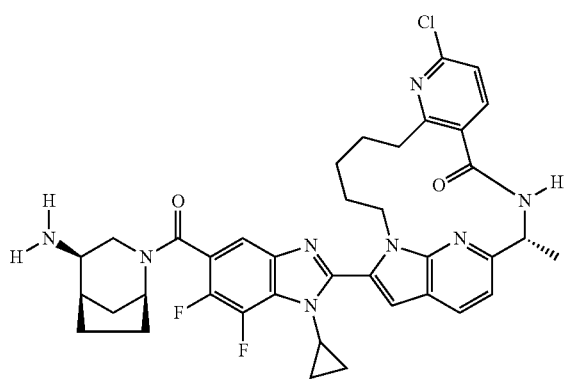
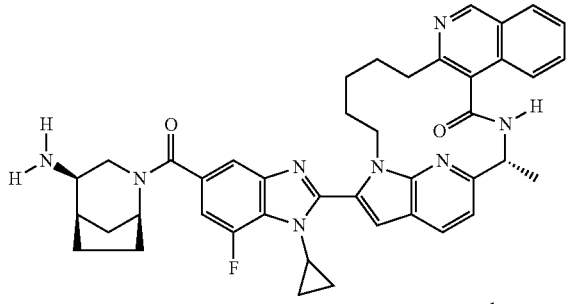
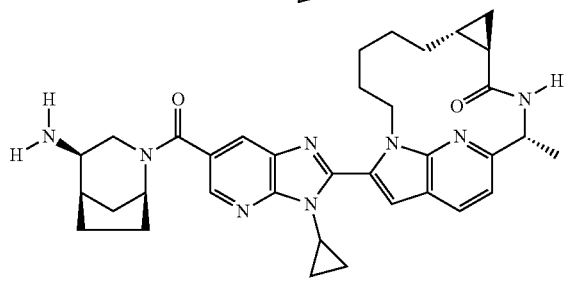
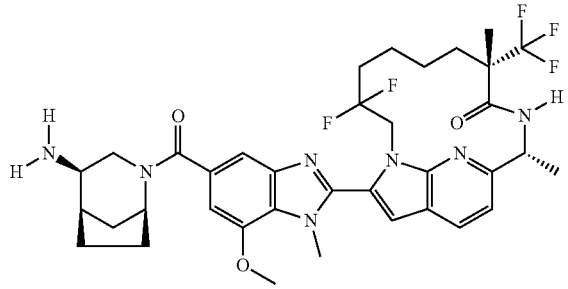

1349 -continued
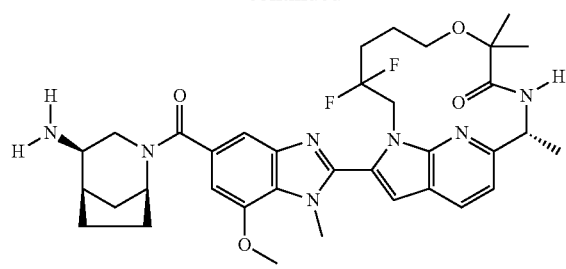
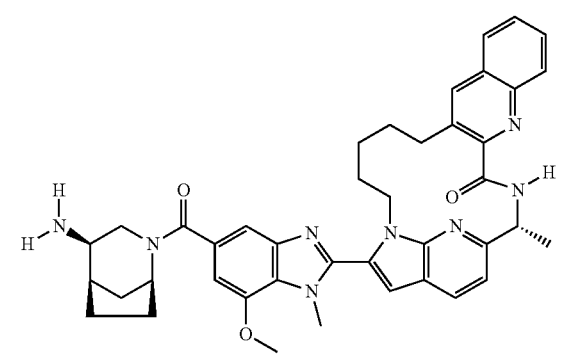
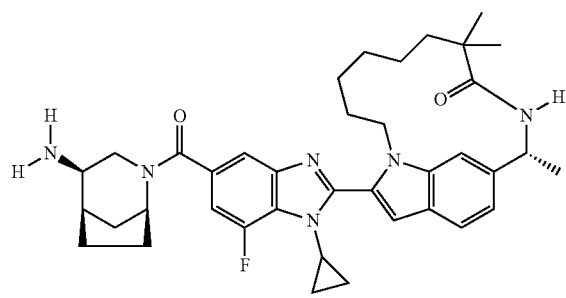
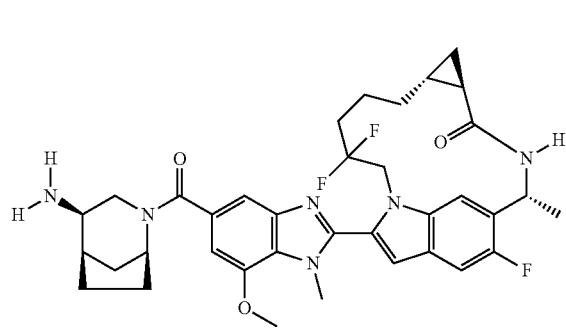
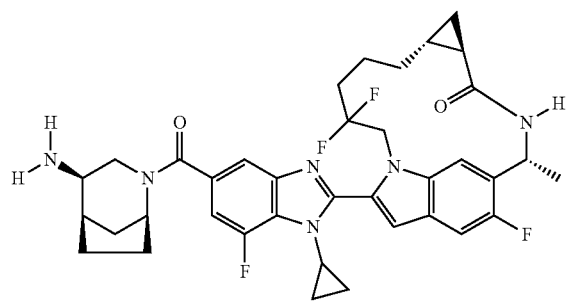
1350 -continued
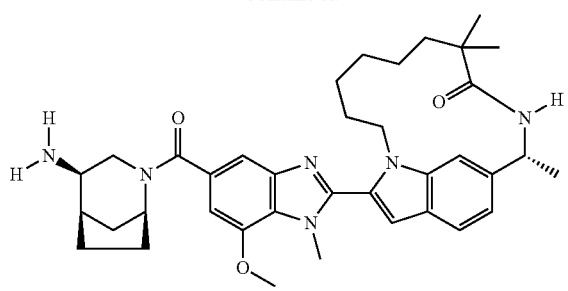
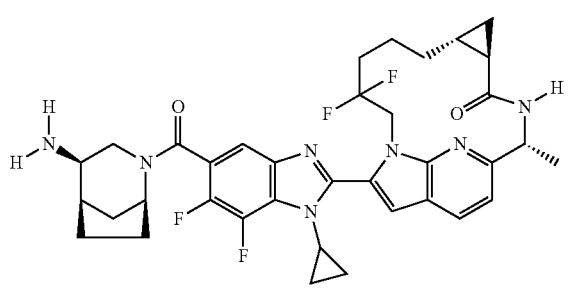
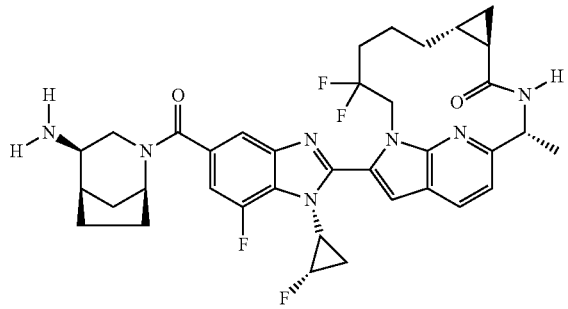
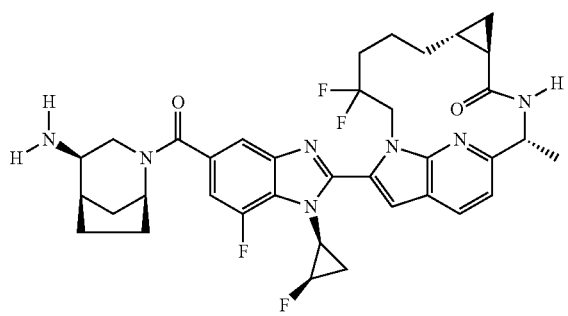
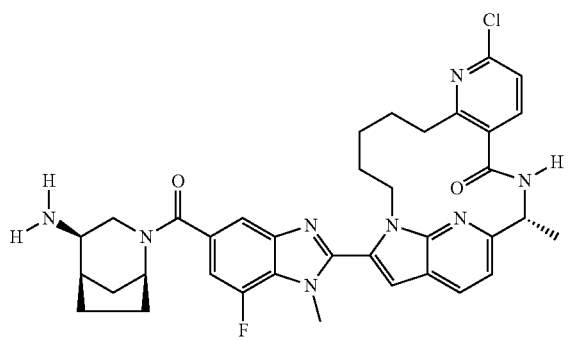

1351
-continued
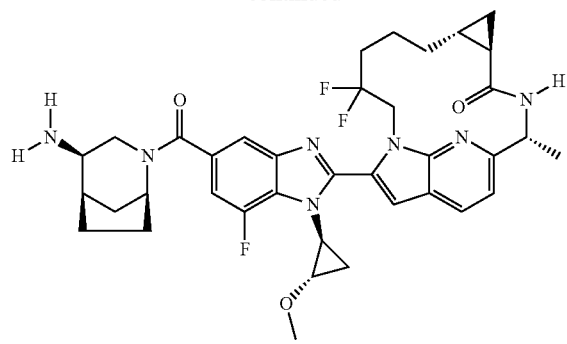
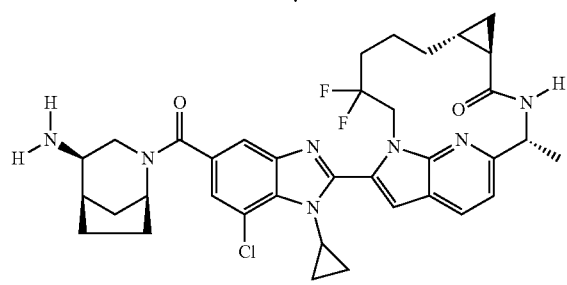
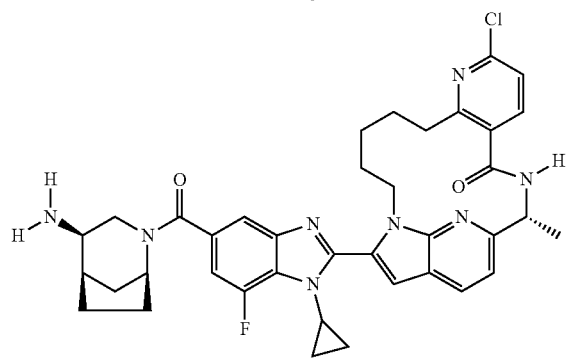
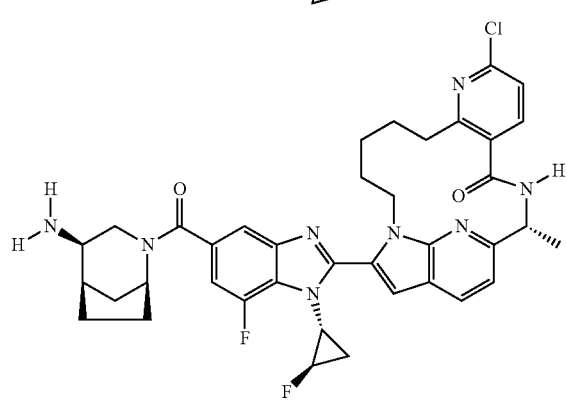
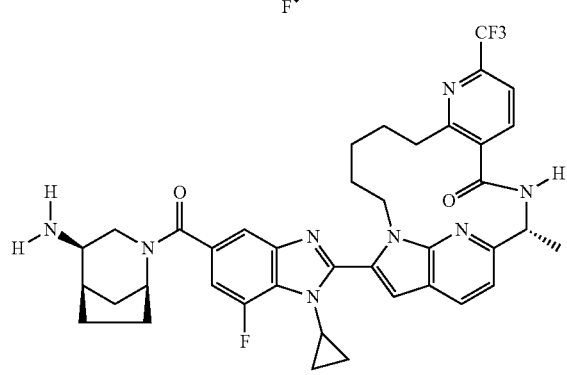
1352
-continued
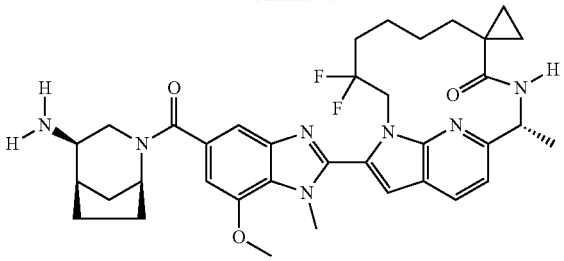
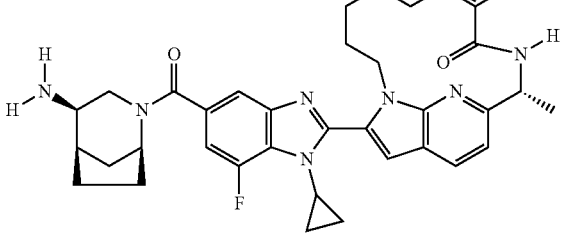
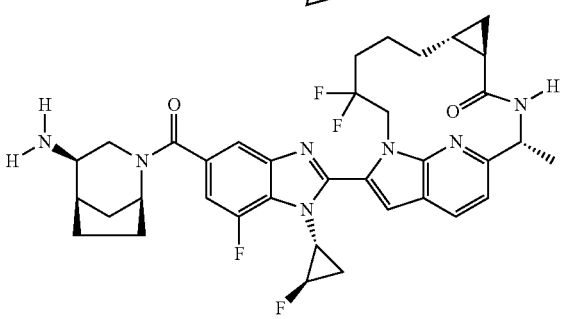
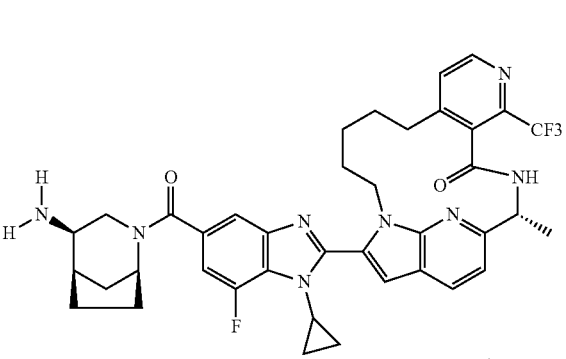
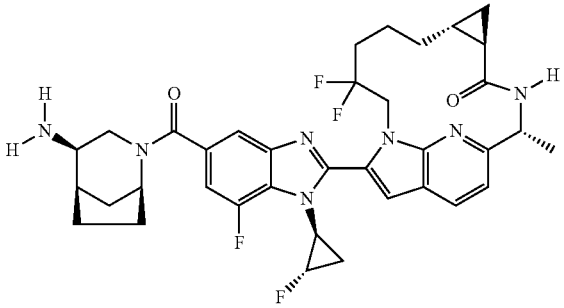

1353
-continued
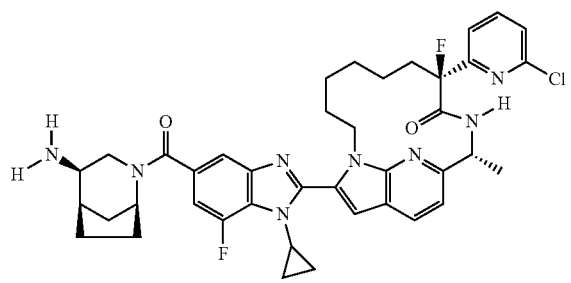
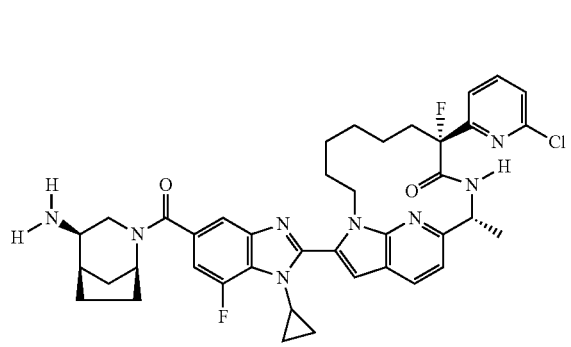
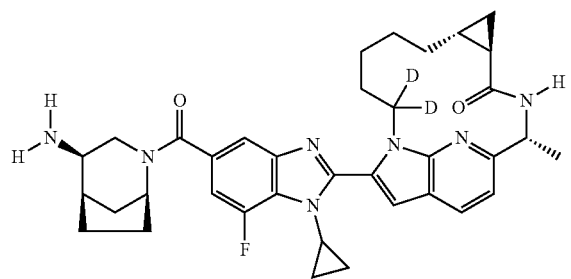
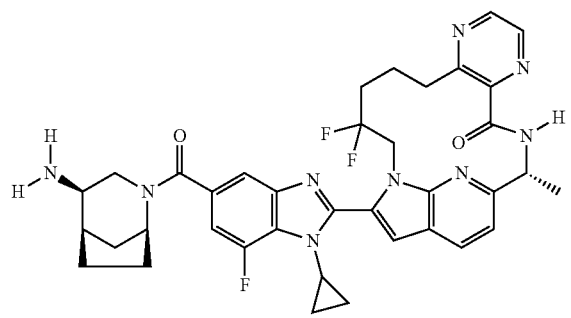
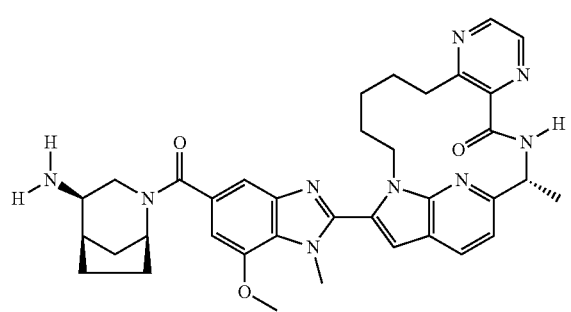
1354
-continued
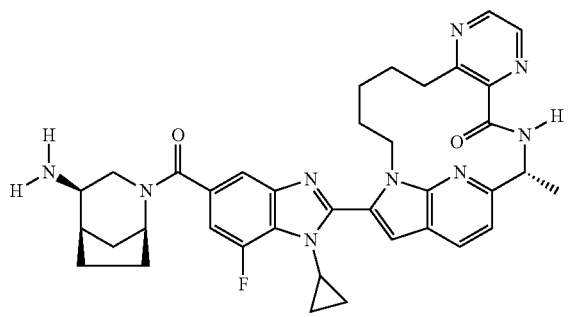
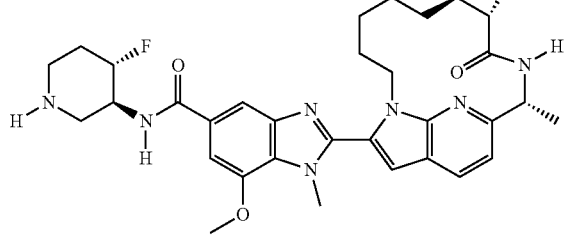
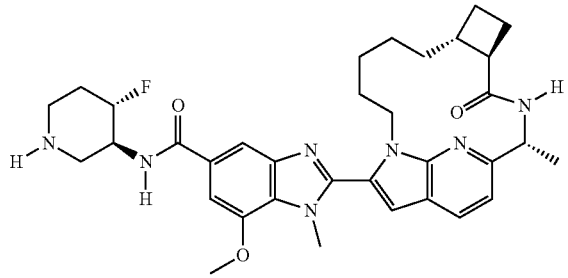
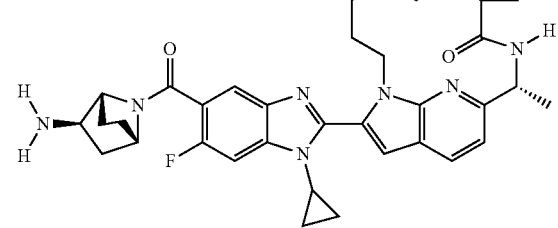
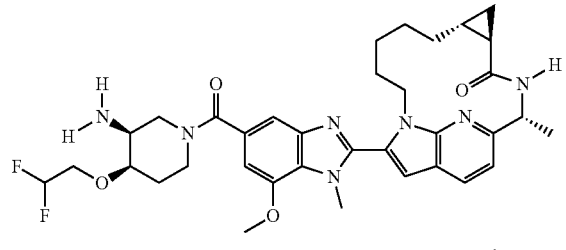
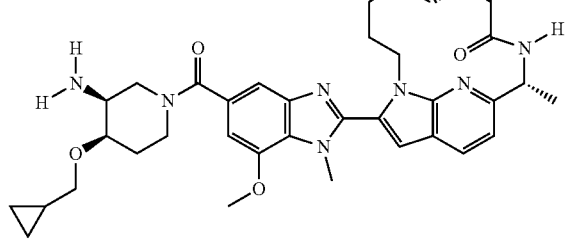

1355
-continued
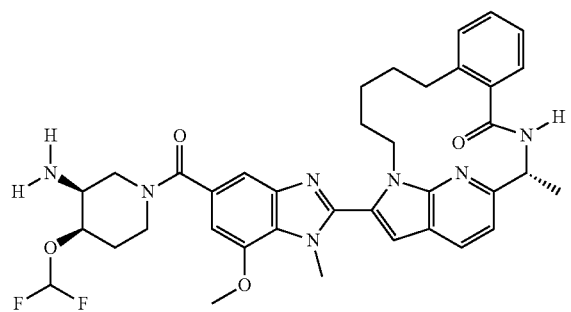
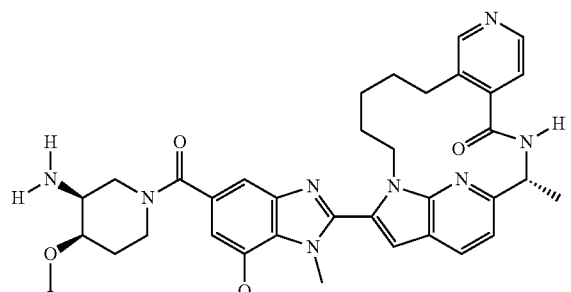
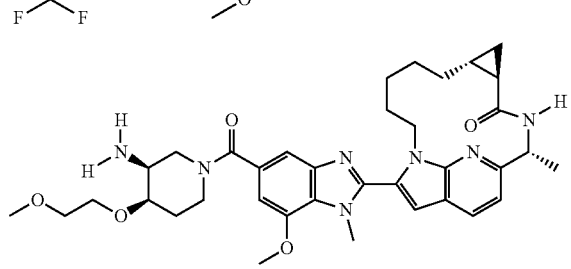
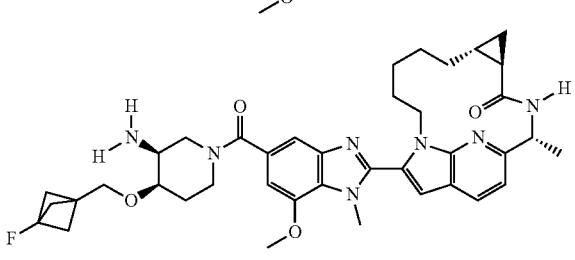
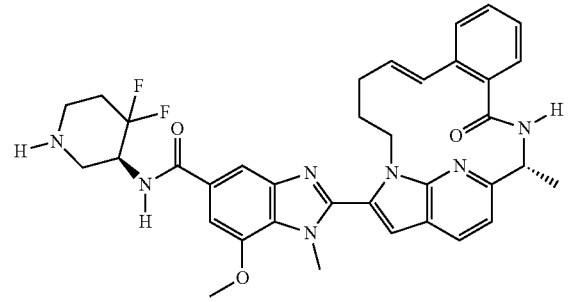
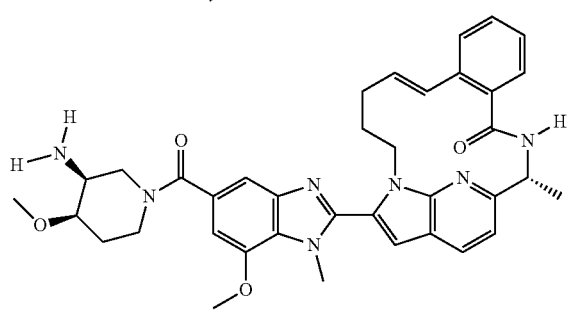
1356
-continued
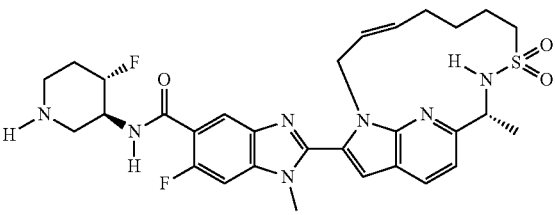
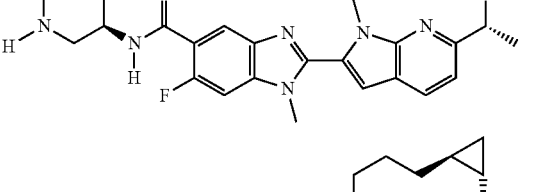
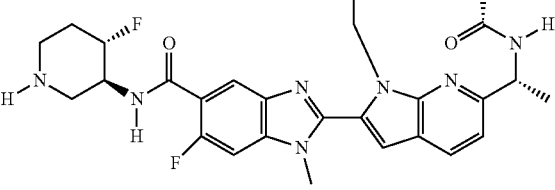
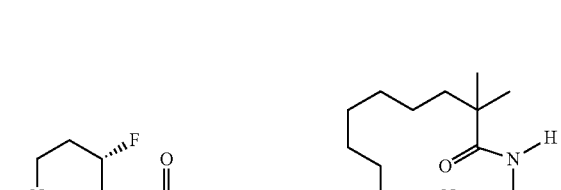
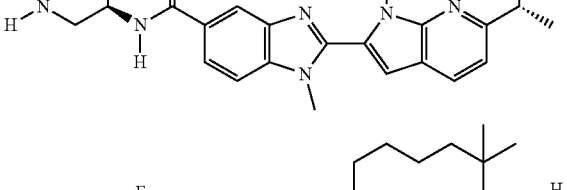
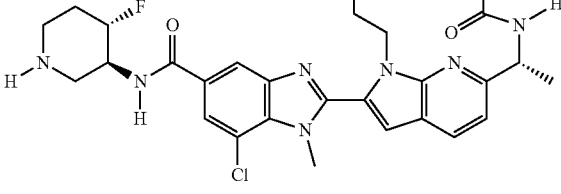
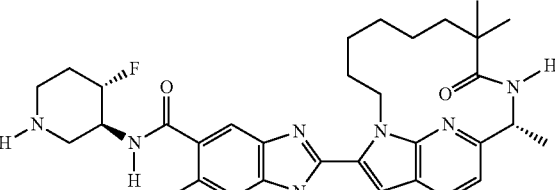
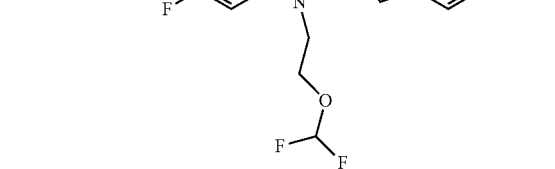

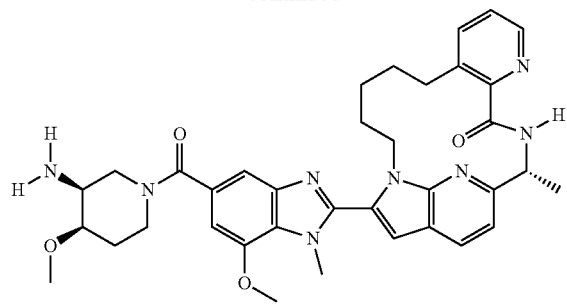
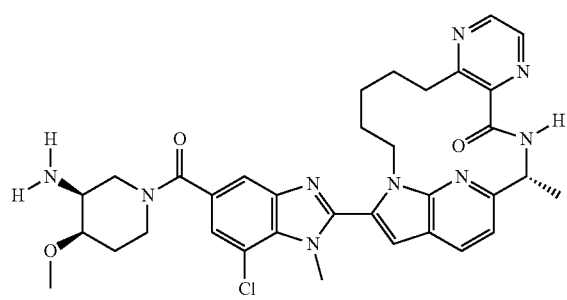
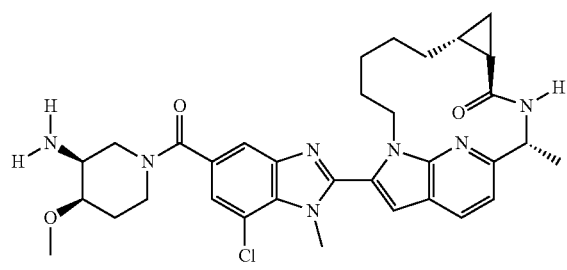
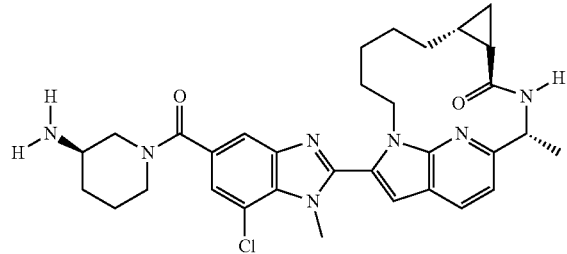
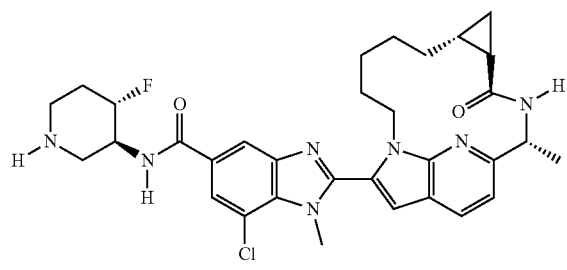
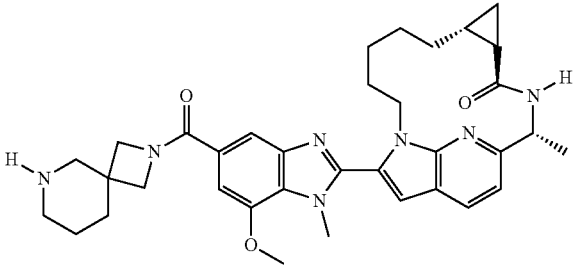
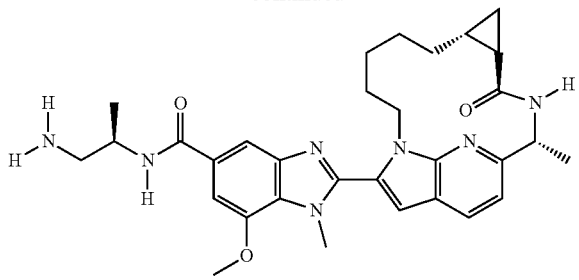
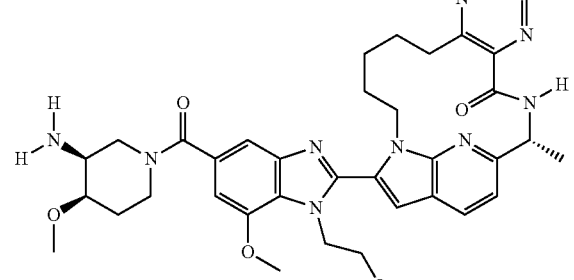
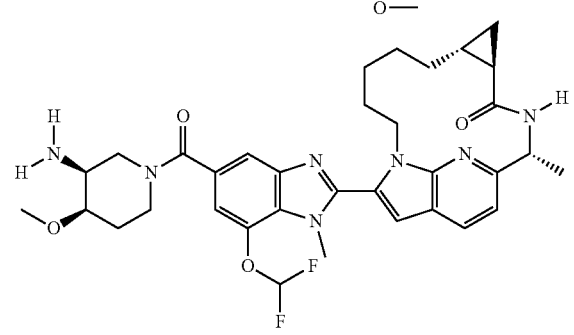
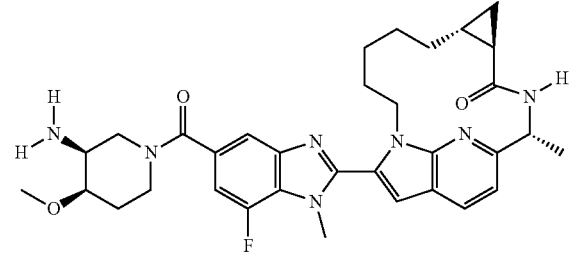
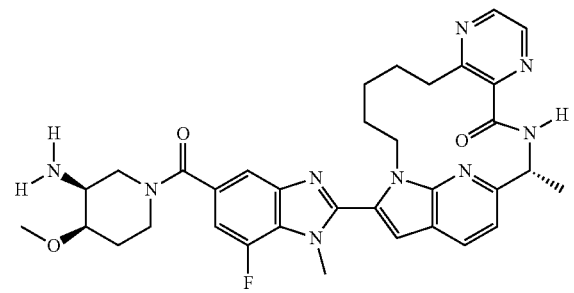
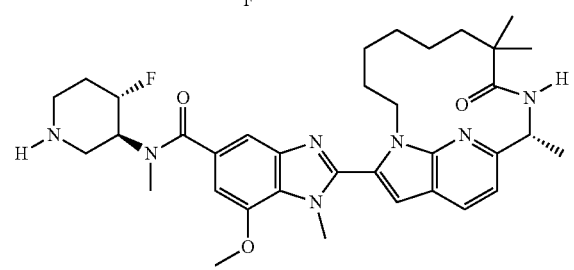

1359                                  1360
-continued                           -continued
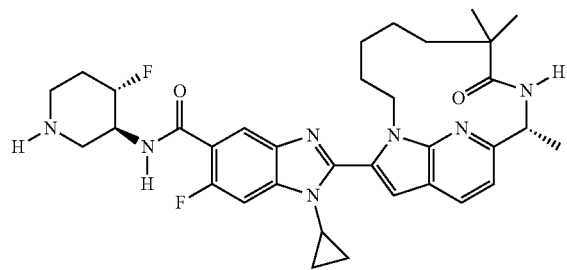
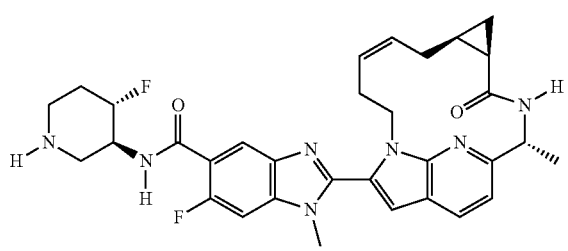
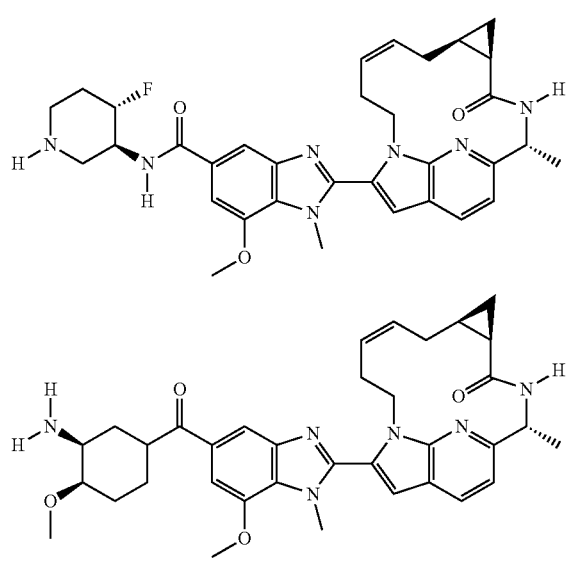
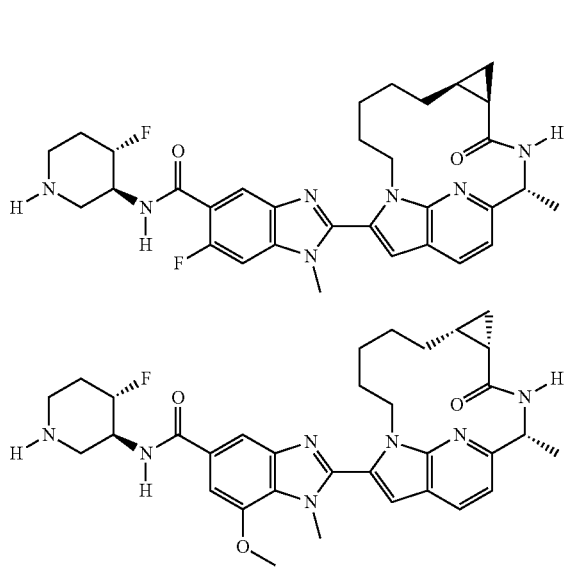
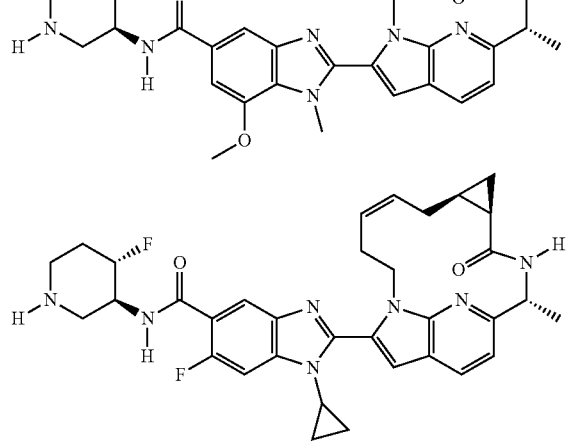
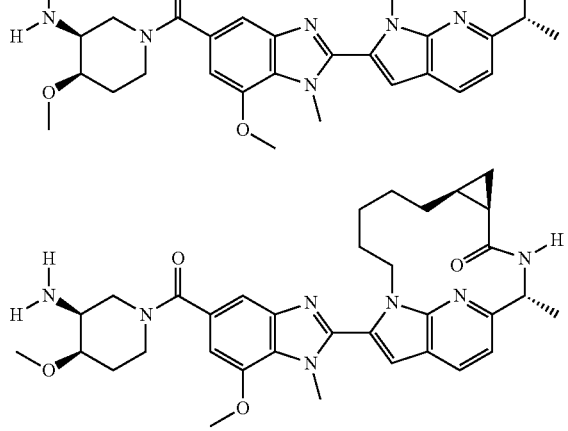
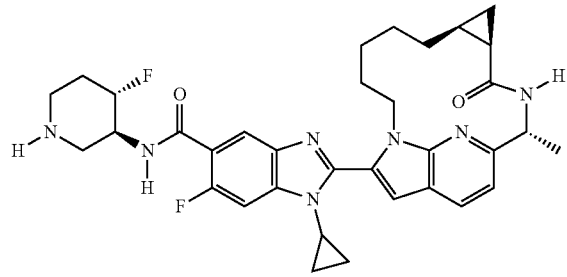
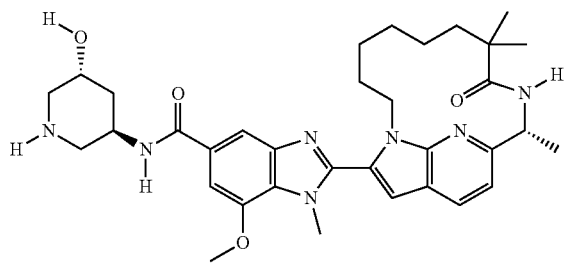

1361
-continued
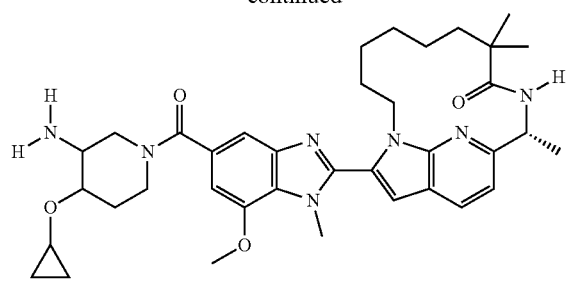
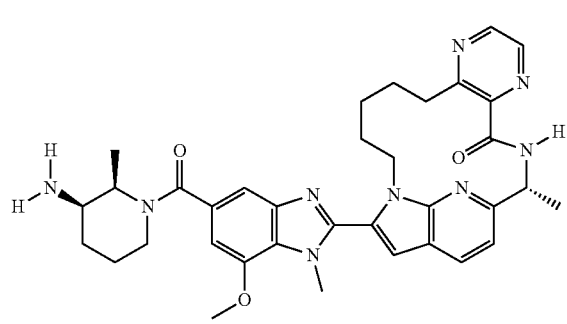
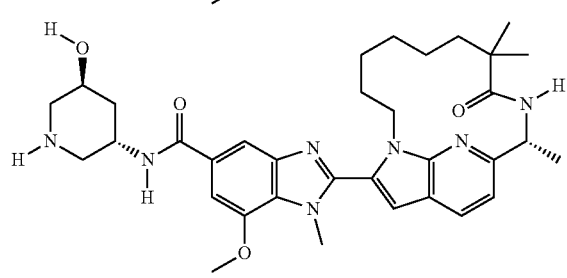
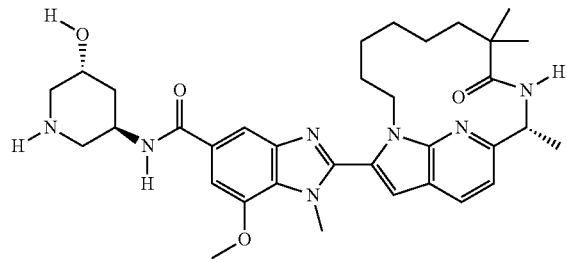
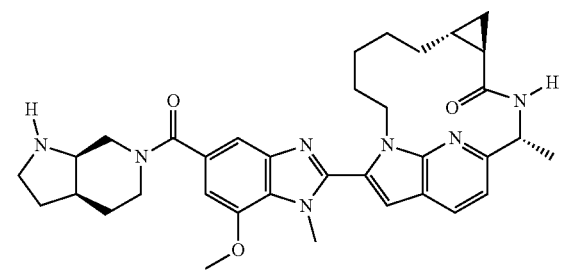
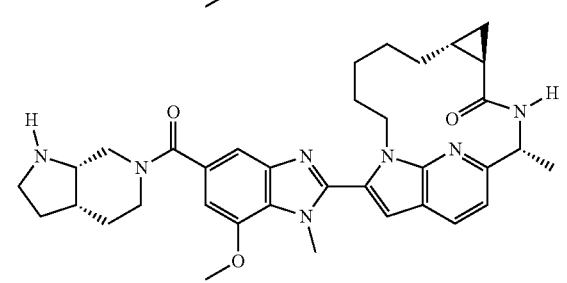
1362
-continued
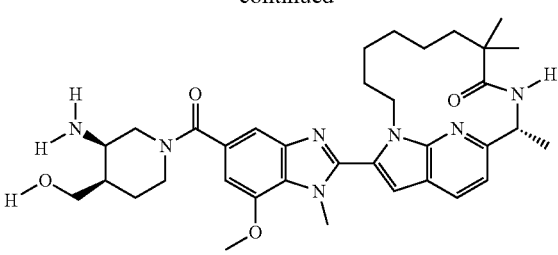
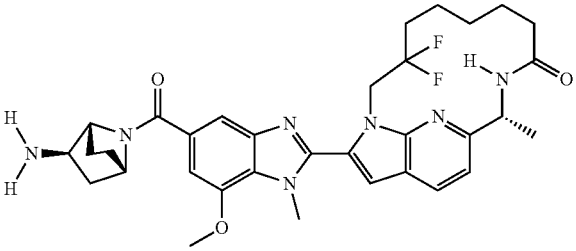
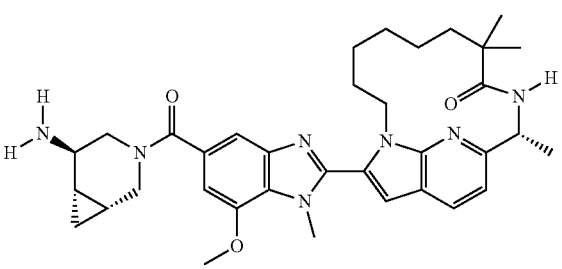
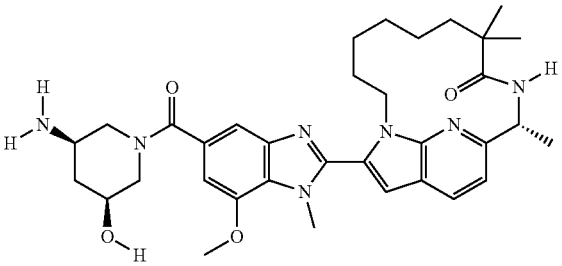
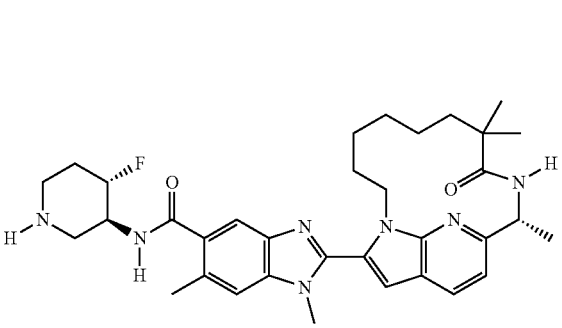
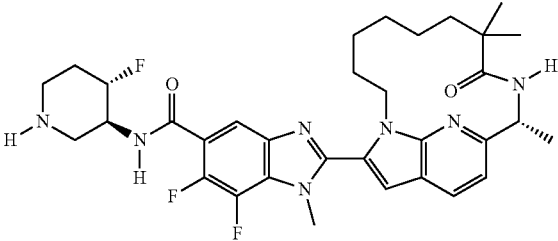

1363
-continued
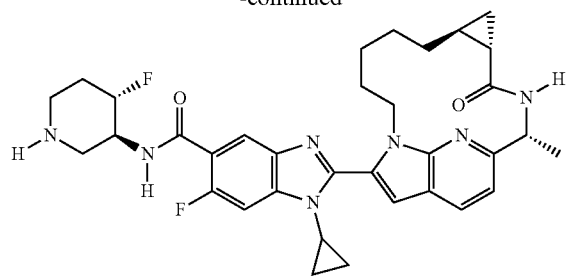
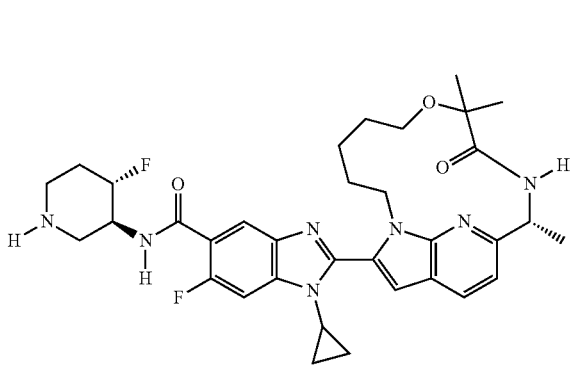
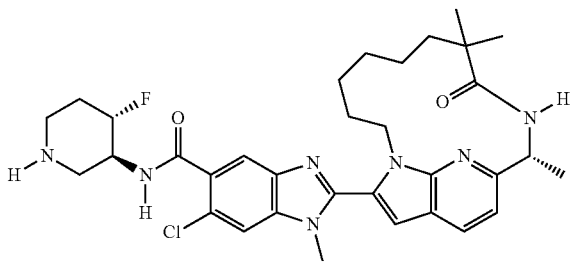
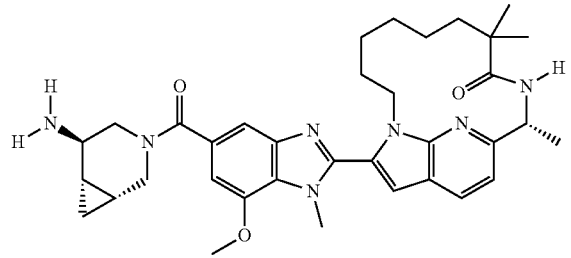
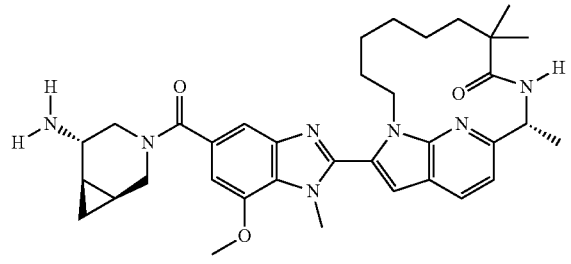
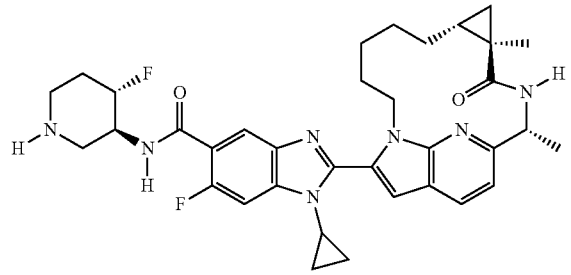
1364
-continued
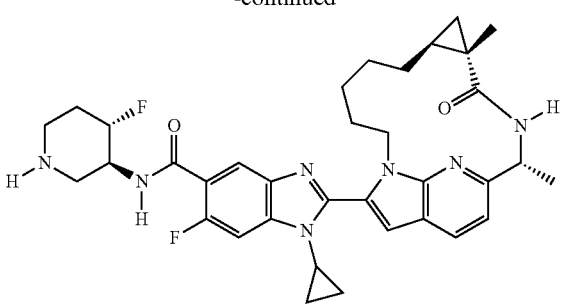
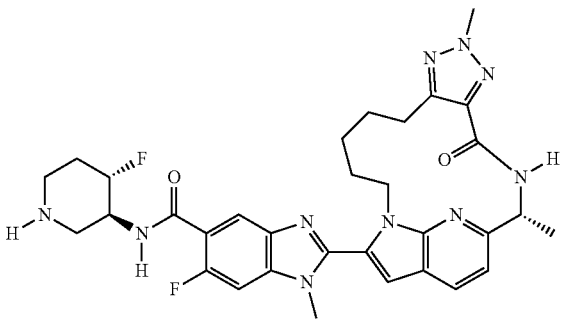
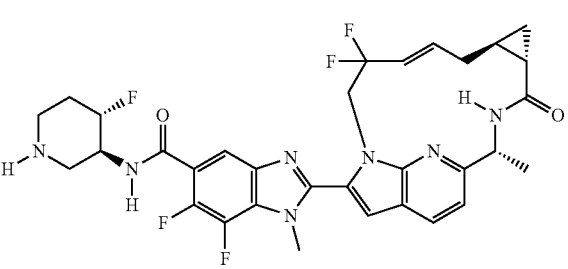
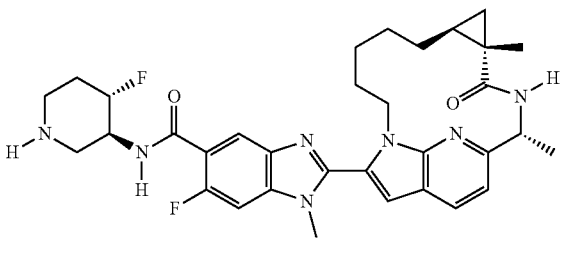
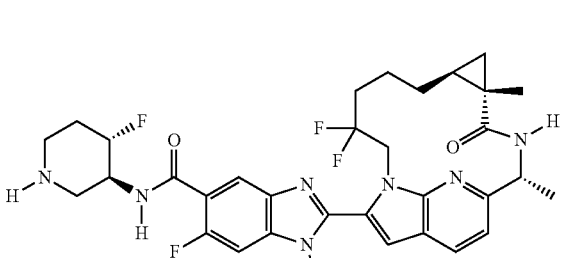
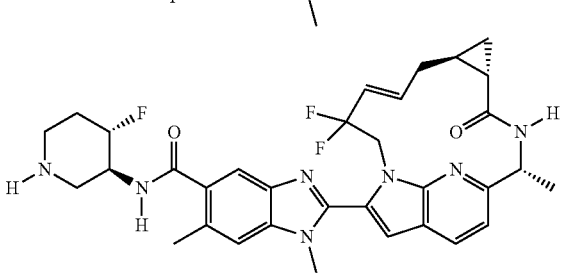

1365
-continued
1366
-continued
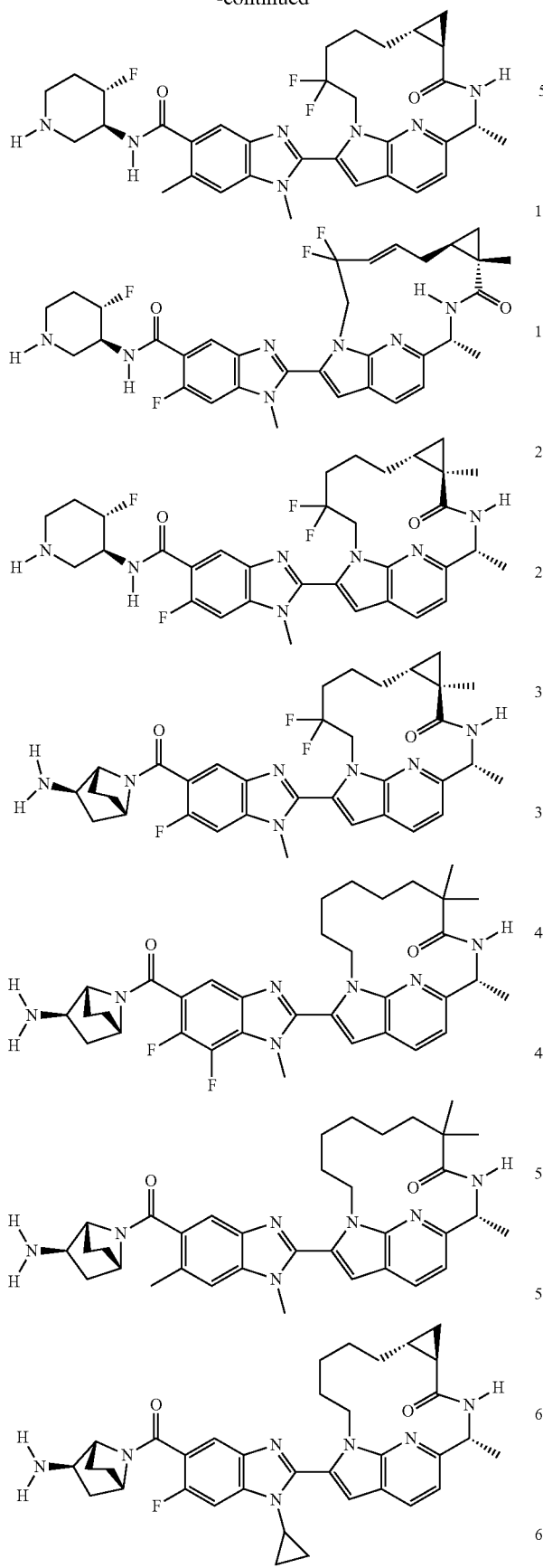
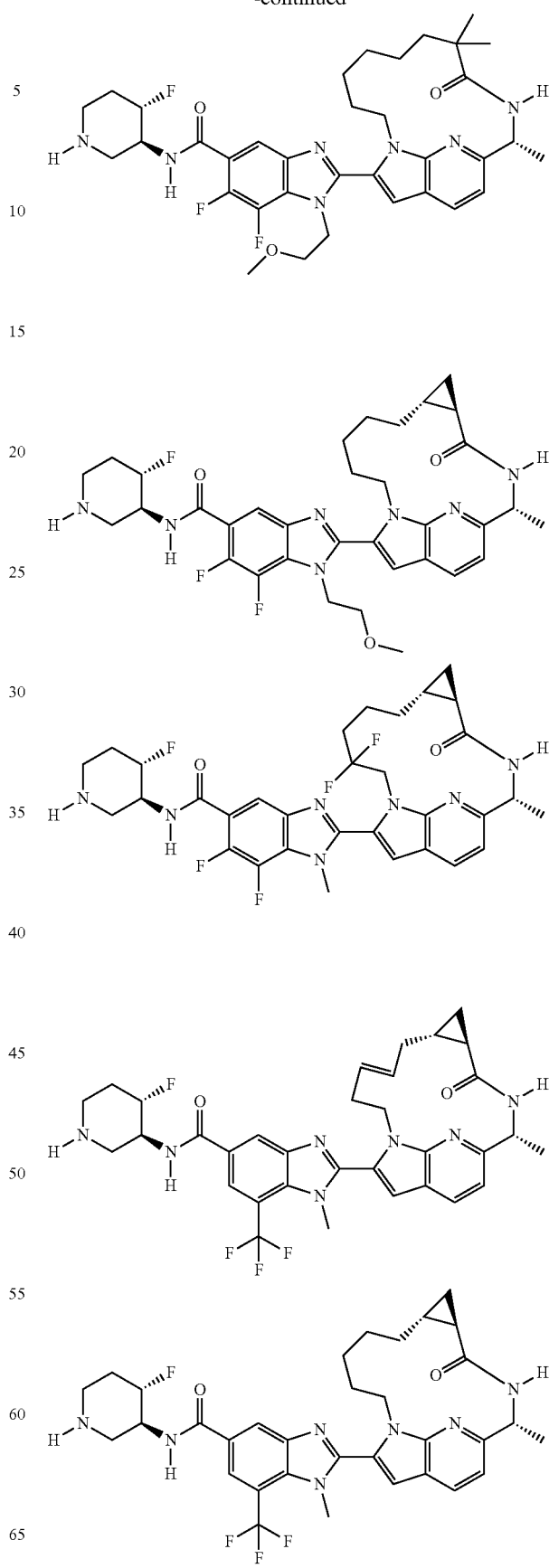

1367
-continued
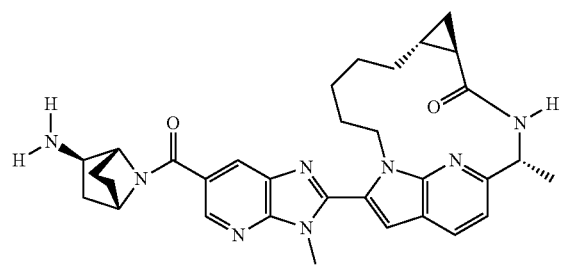
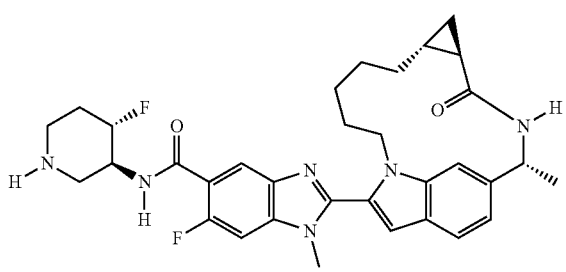
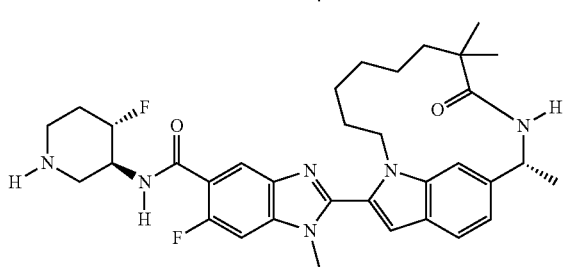
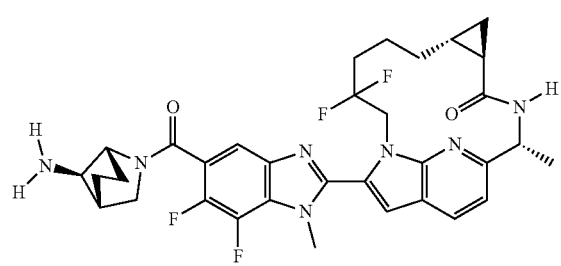
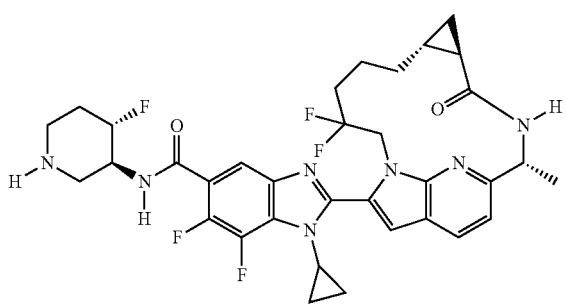
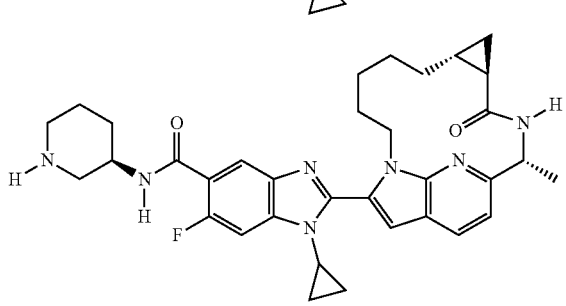
1368
-continued
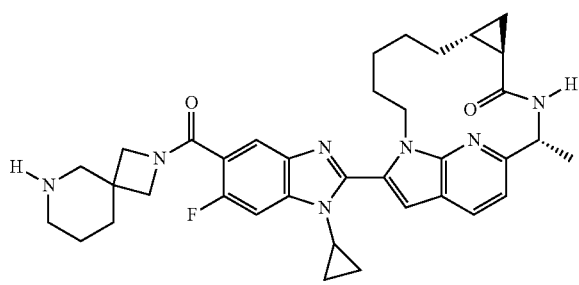
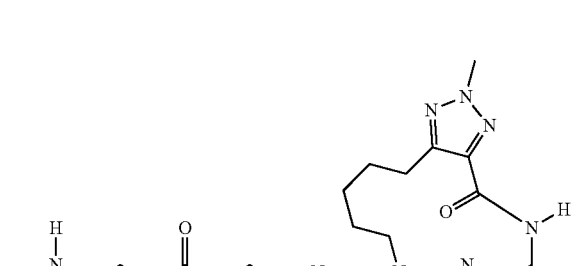
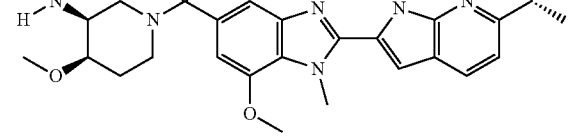
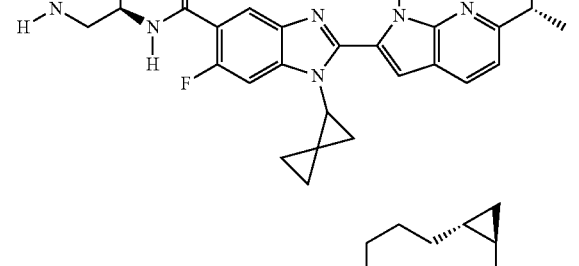
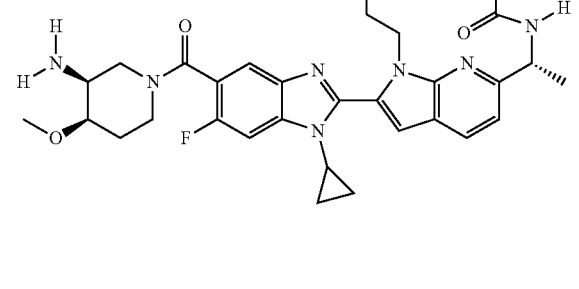
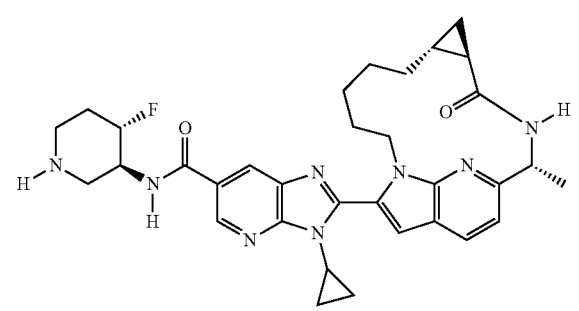

1369
-continued
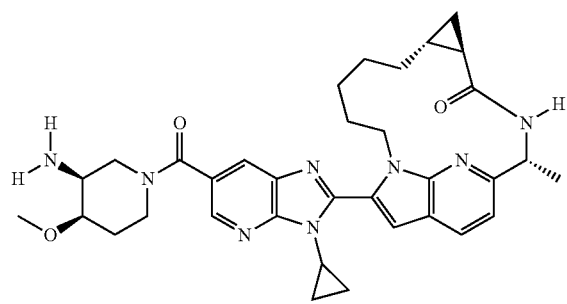
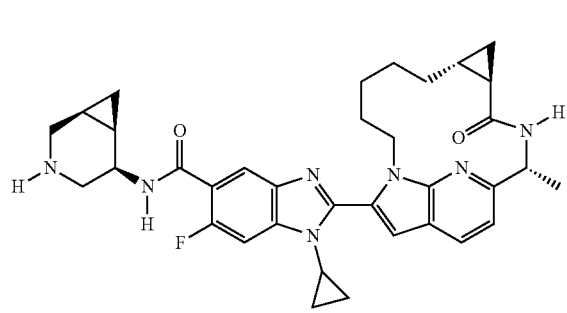
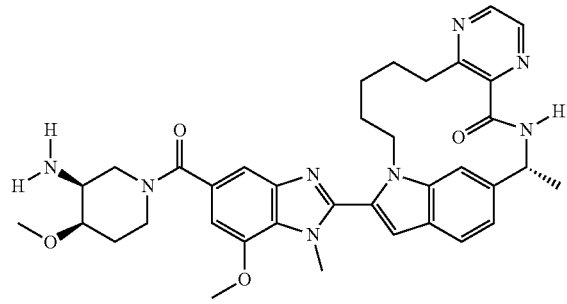
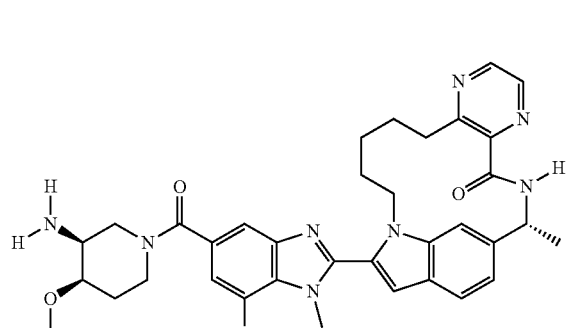
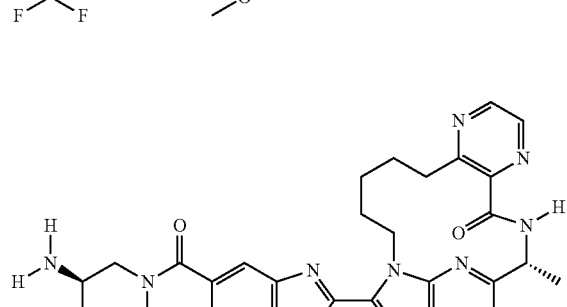
1370
-continued
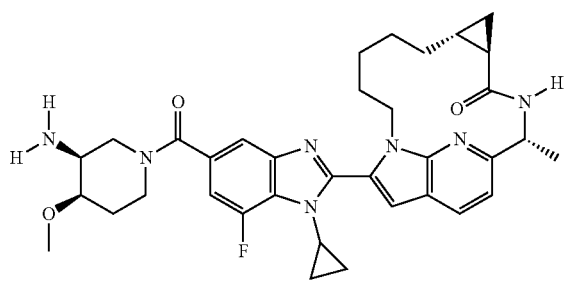
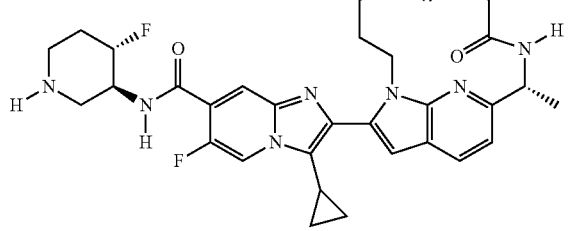
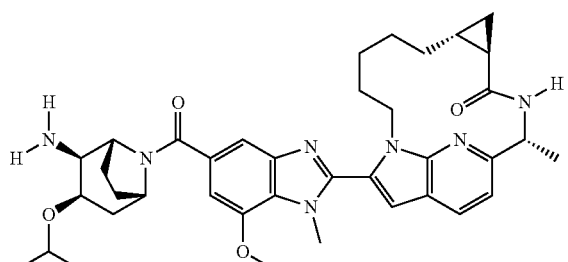
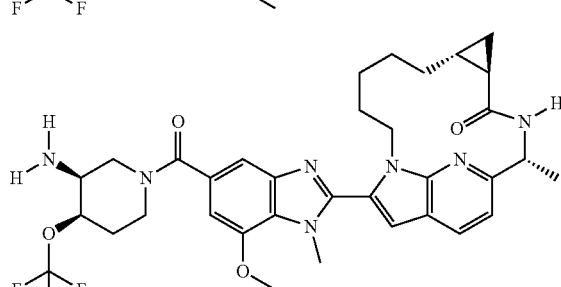
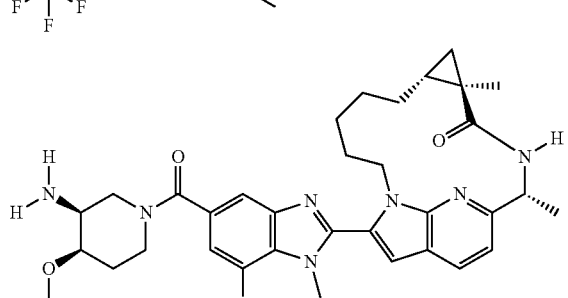
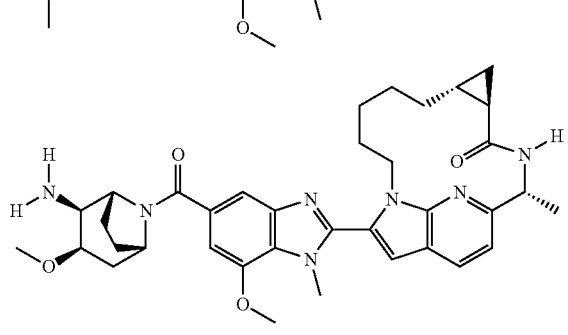

1371
-continued
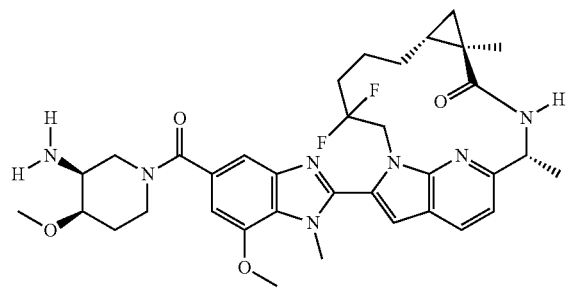
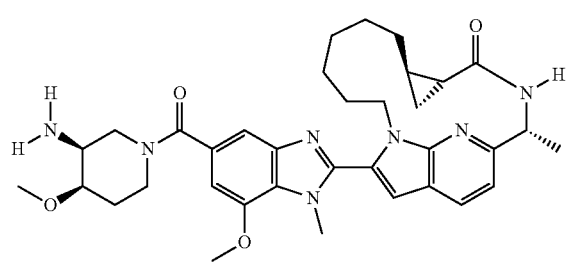
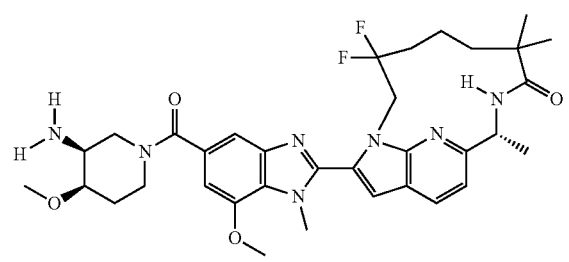
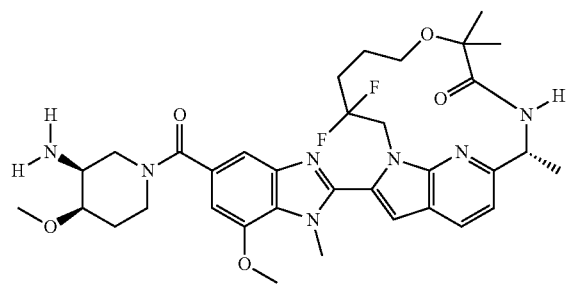
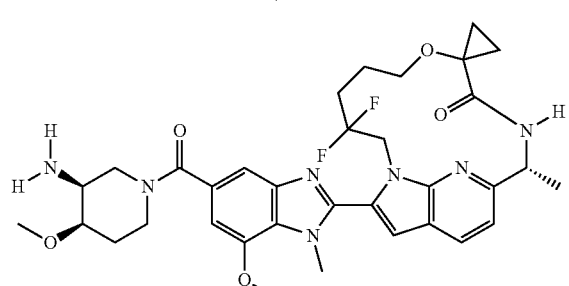
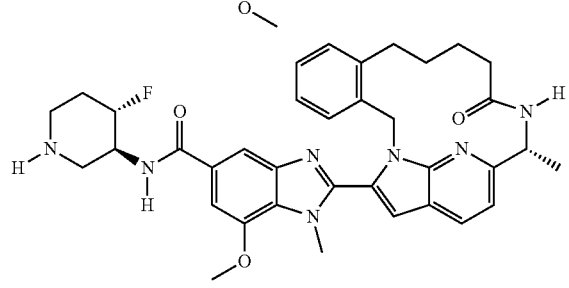
1372
-continued
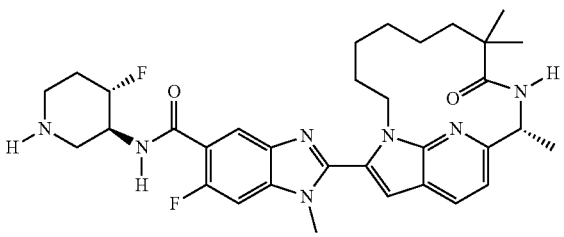
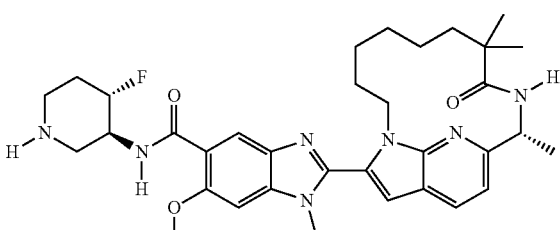
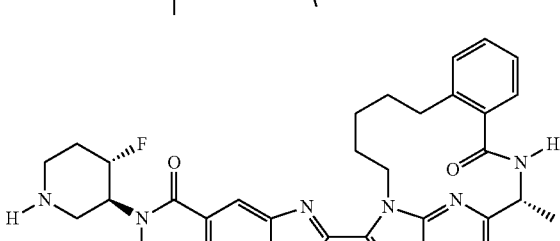
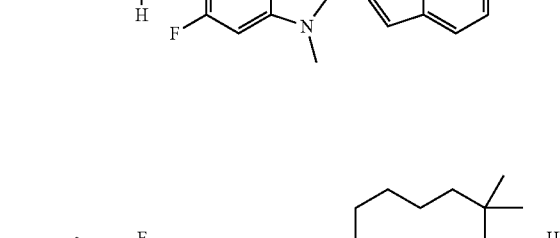
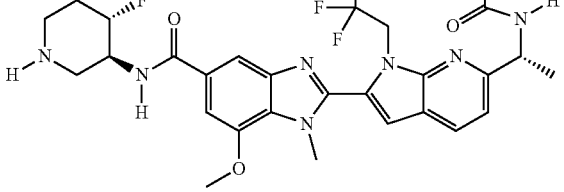
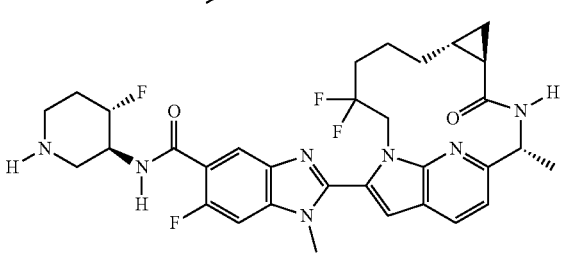
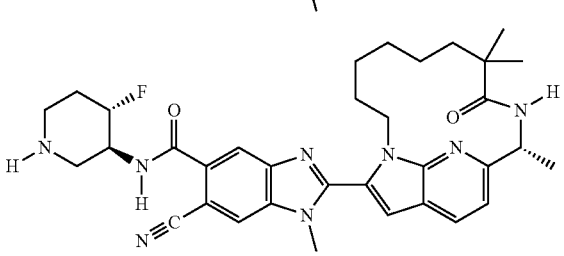

1373
-continued
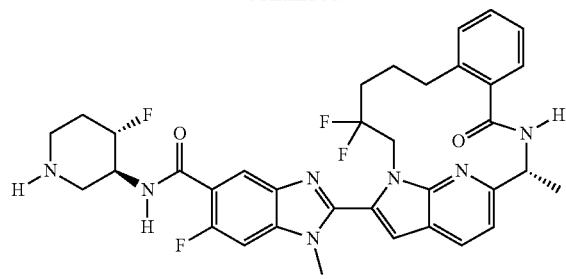
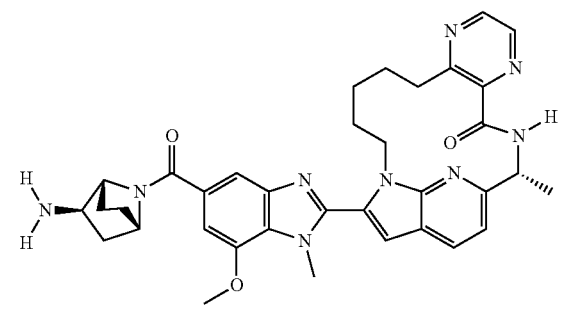
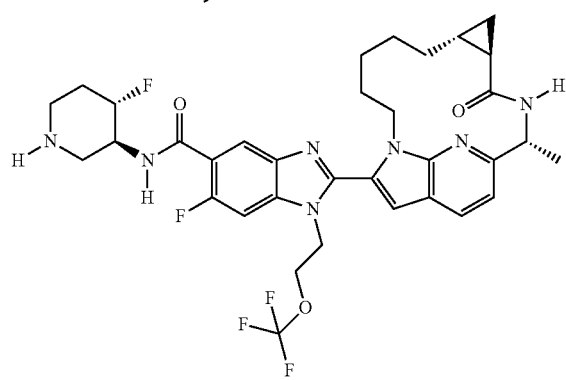
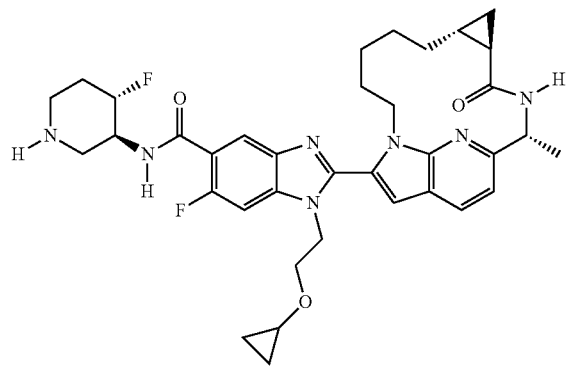
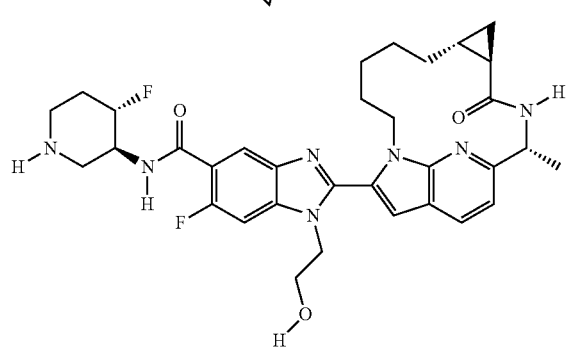
1374
-continued
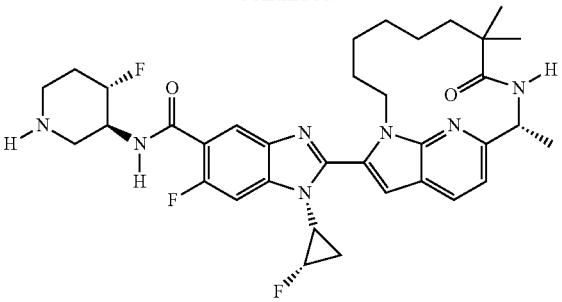
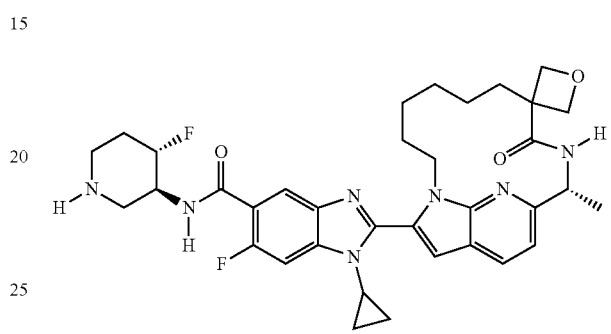
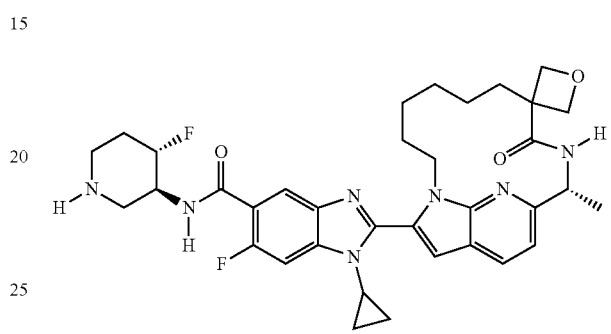
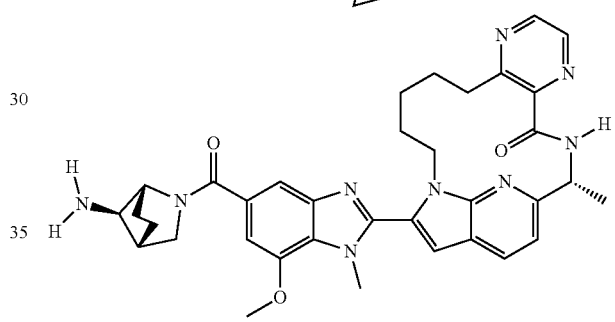
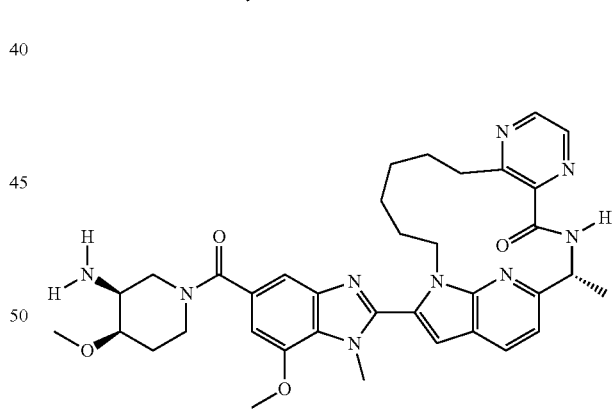

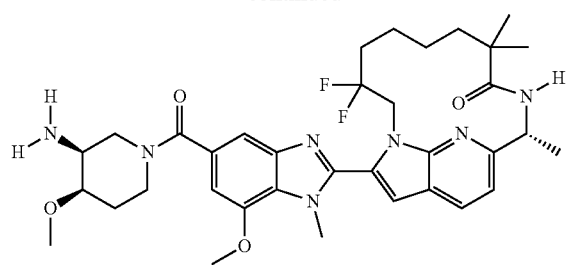
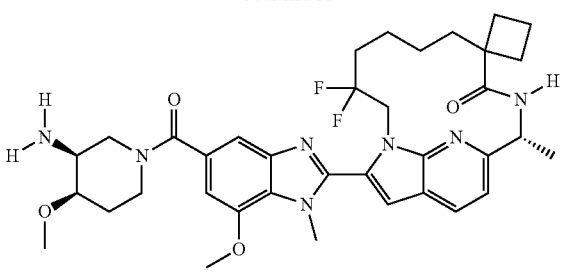
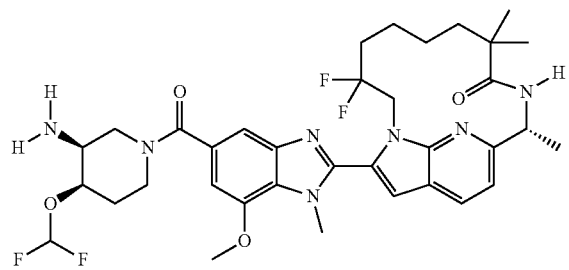
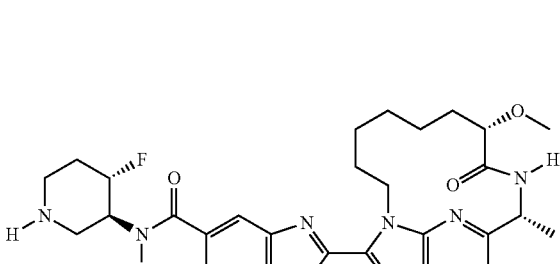
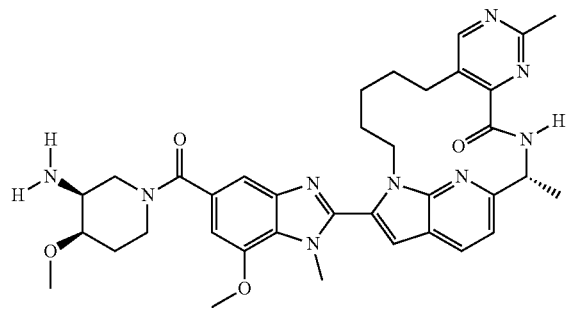
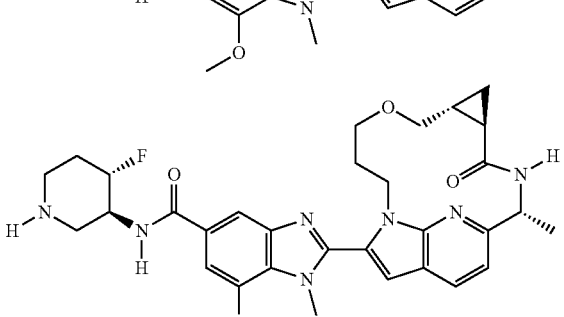
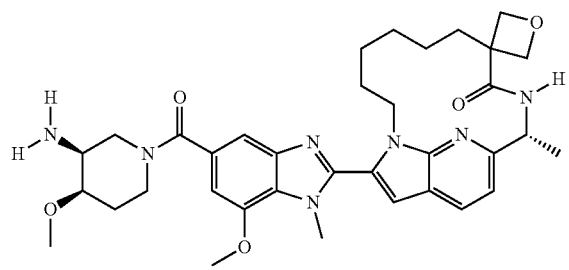
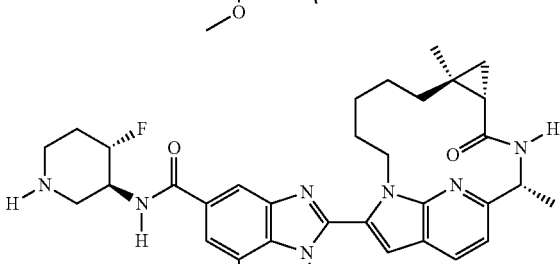
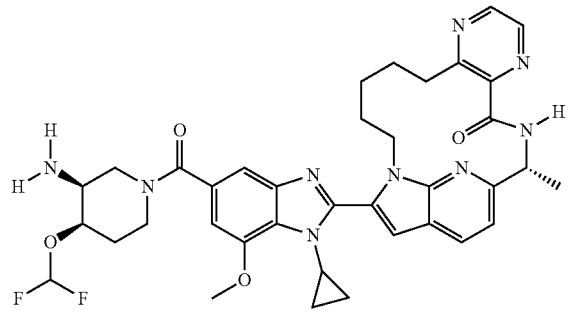
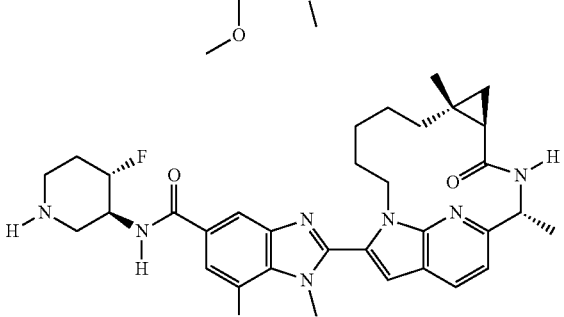
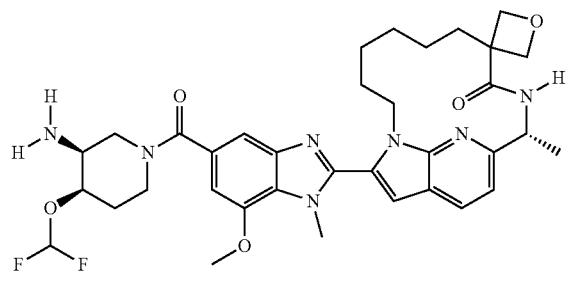
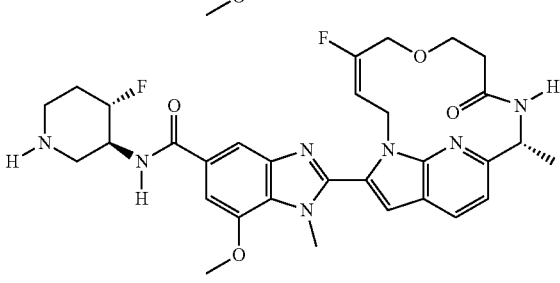

1377
-continued
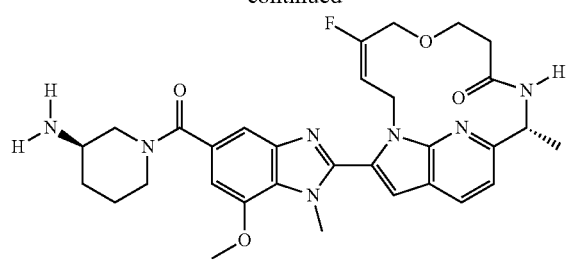
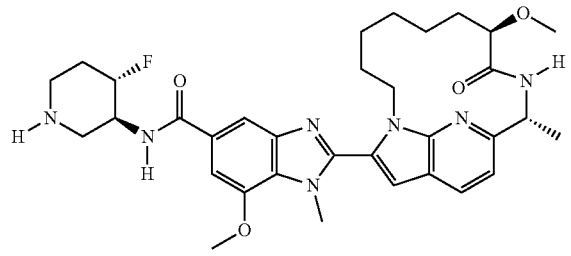
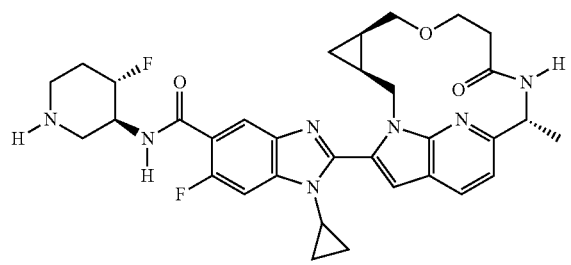
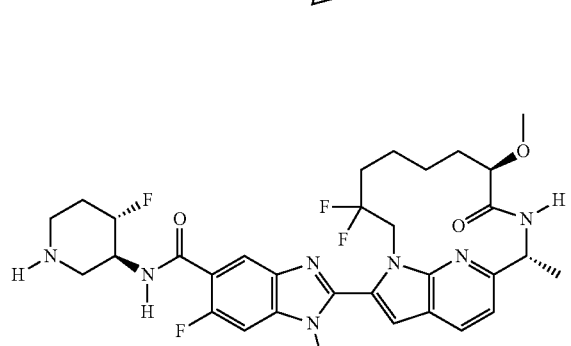
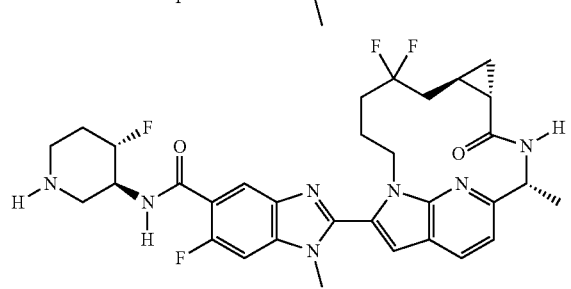
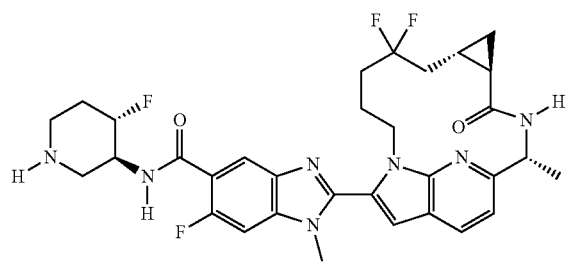
1378
-continued
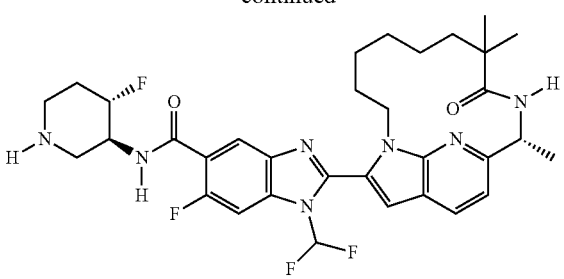
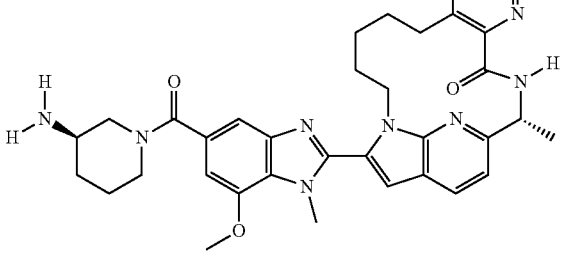
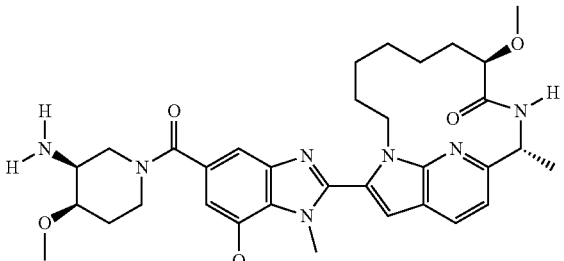
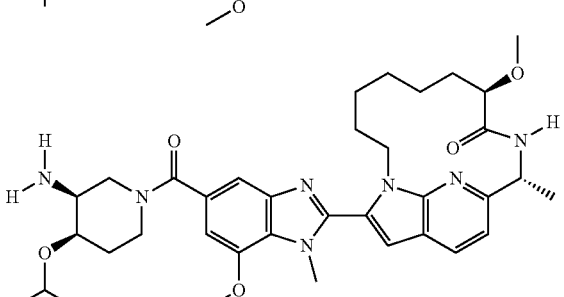
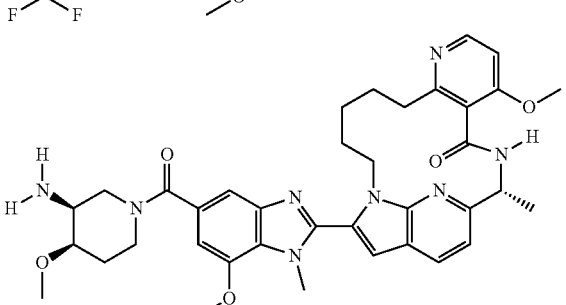
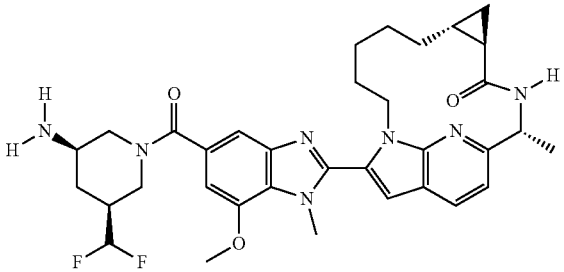

1379
-continued
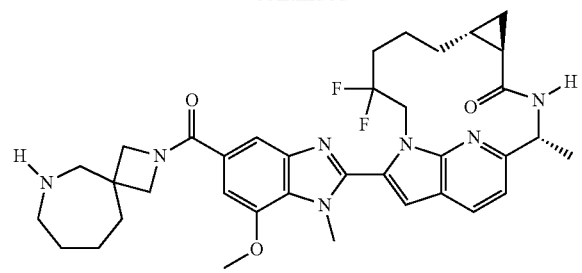
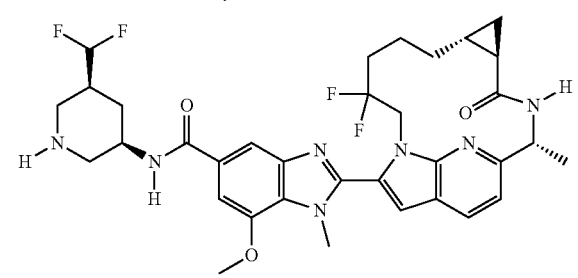
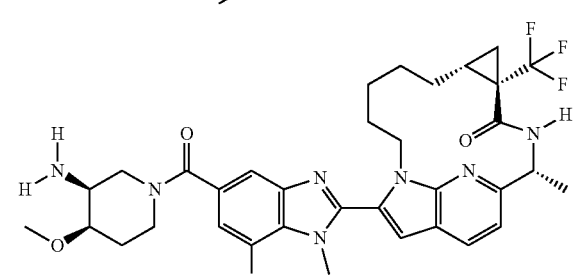
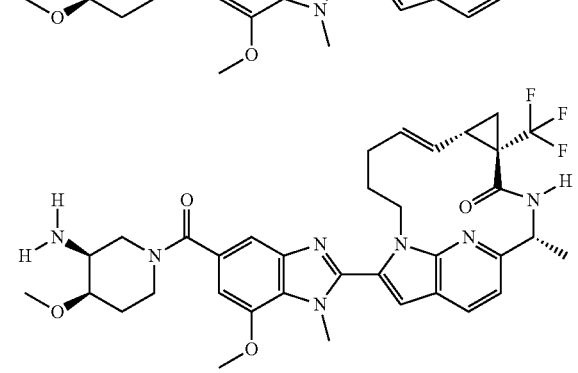
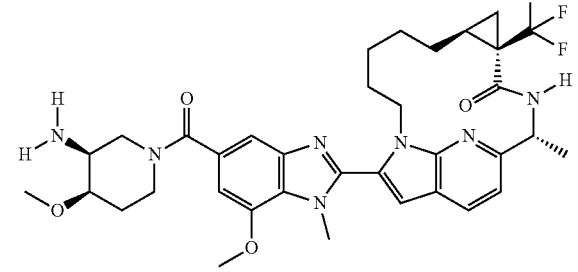
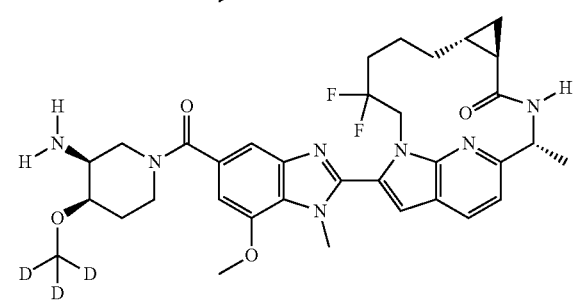
1380
-continued
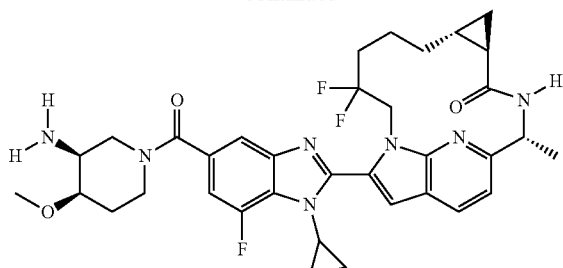
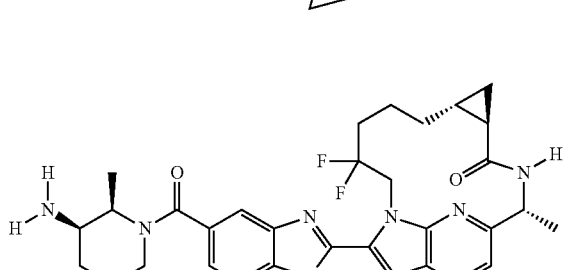
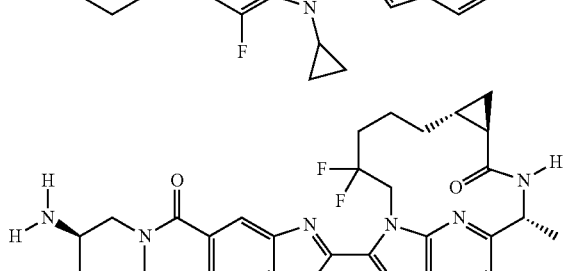
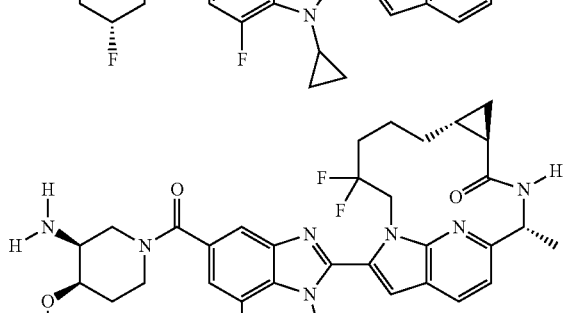
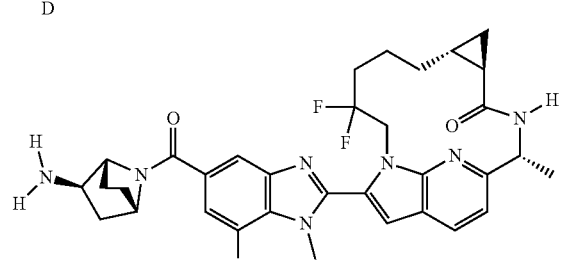
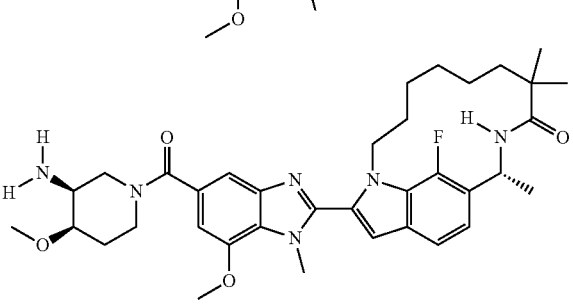

1381
-continued
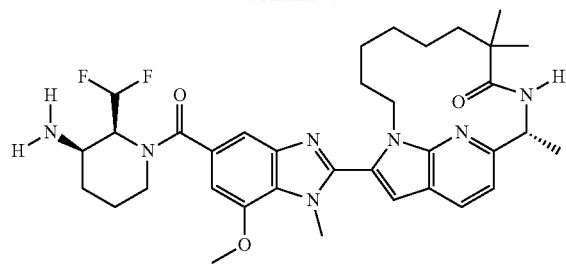
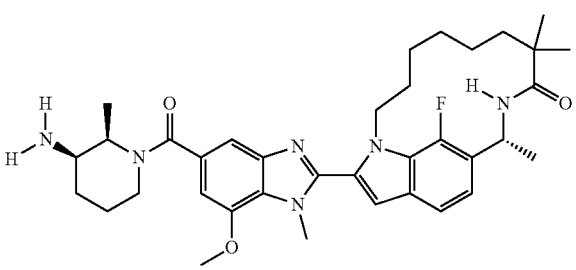
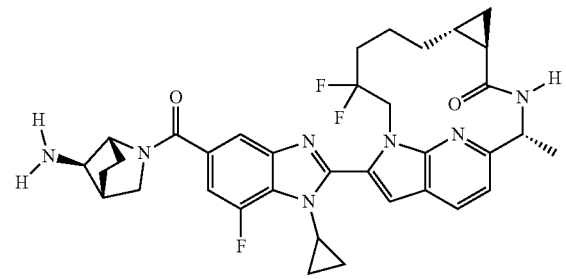
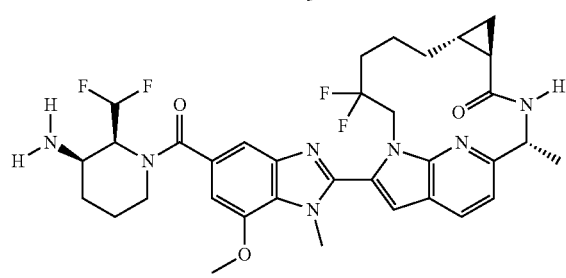
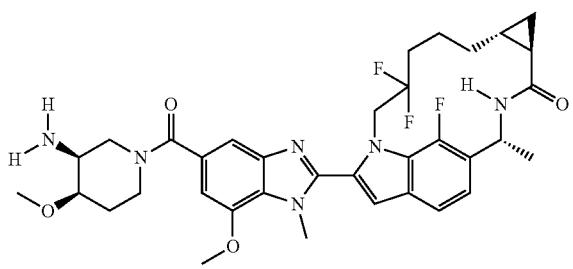
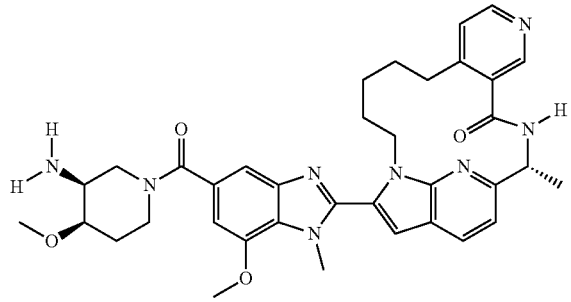
1382
-continued
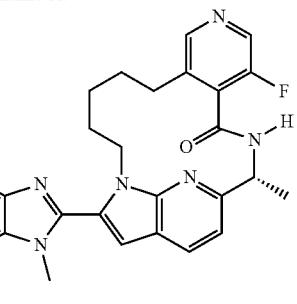
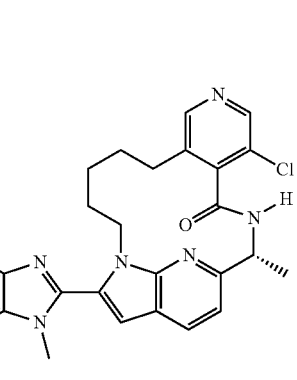
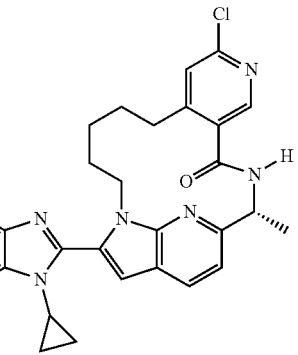
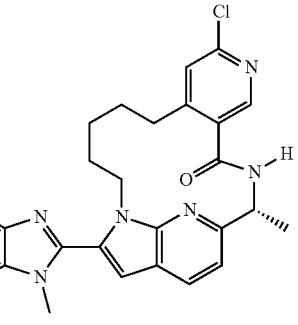
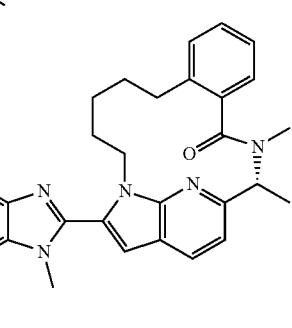

1383
-continued
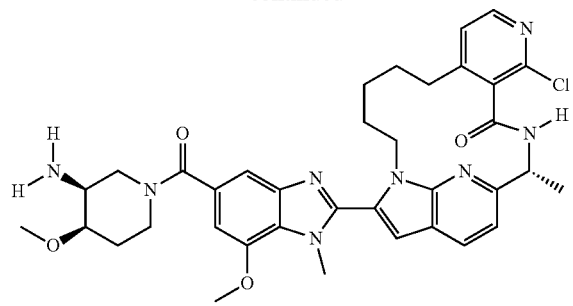
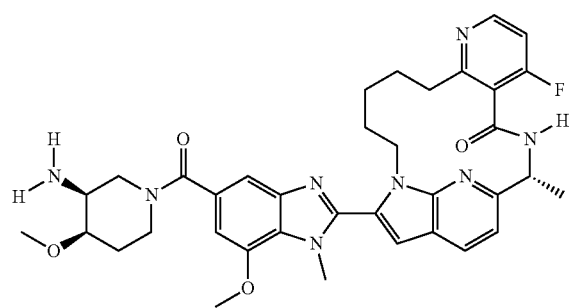
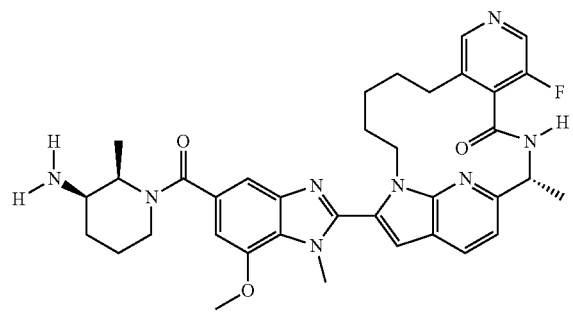
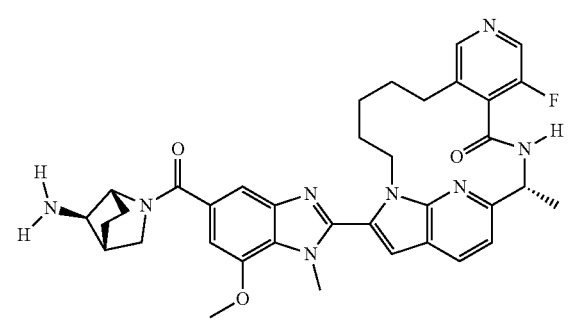
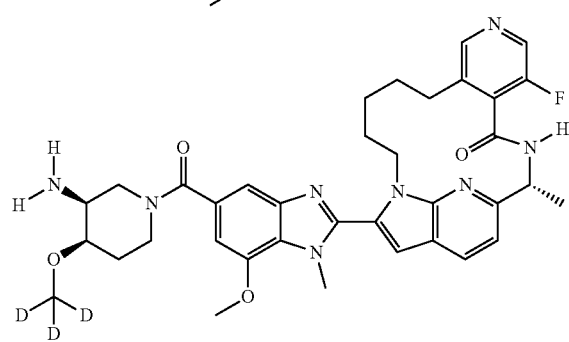
1384
-continued
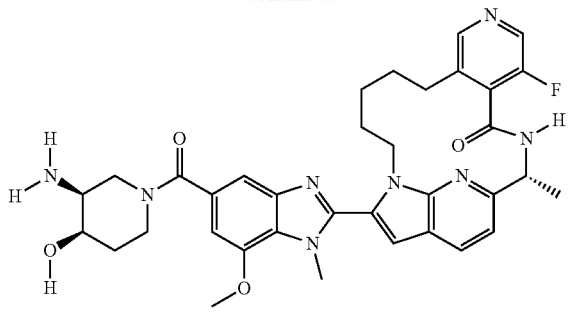
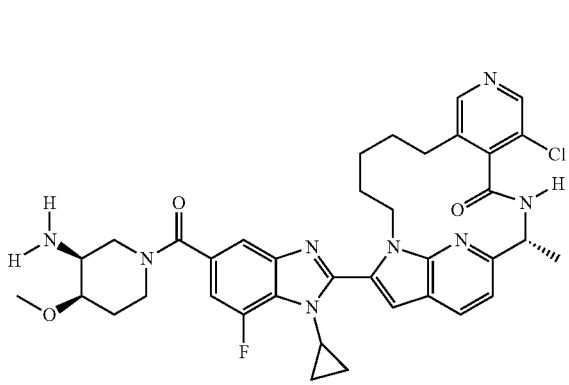
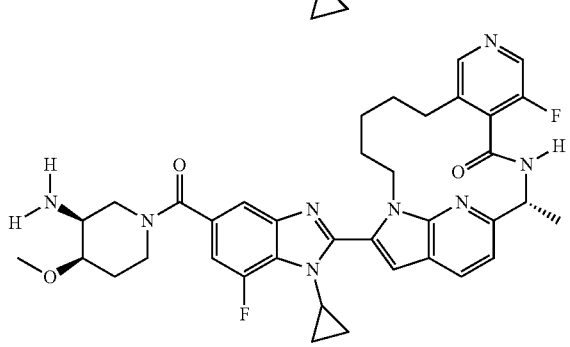
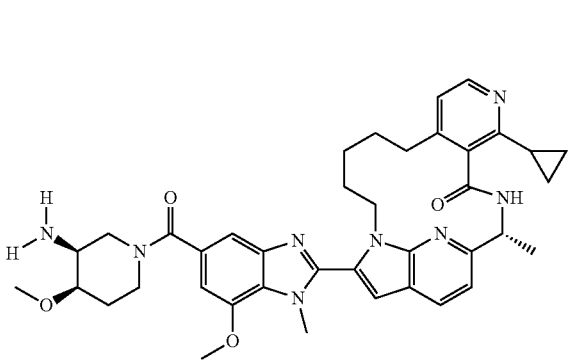
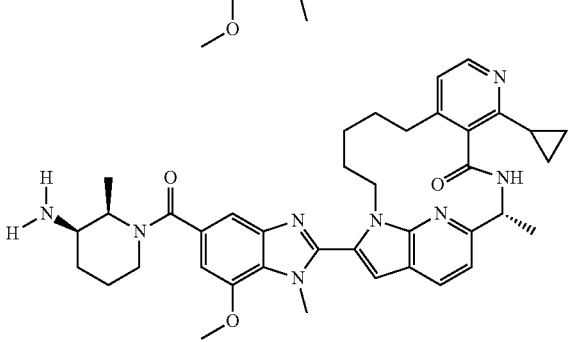

1385
-continued
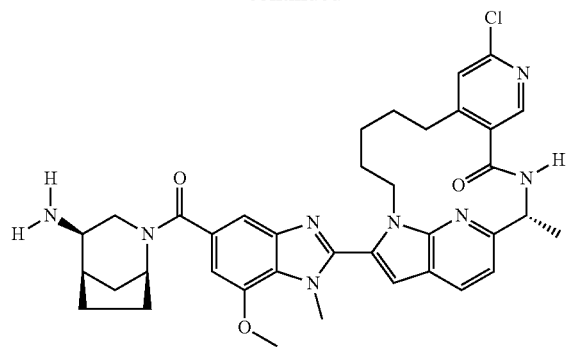
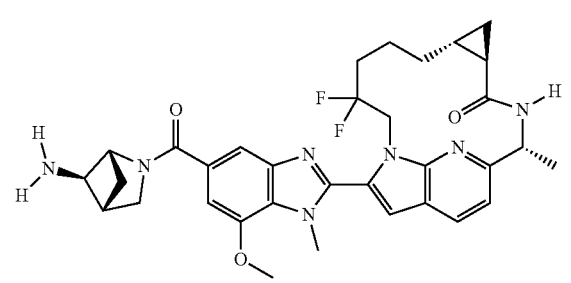
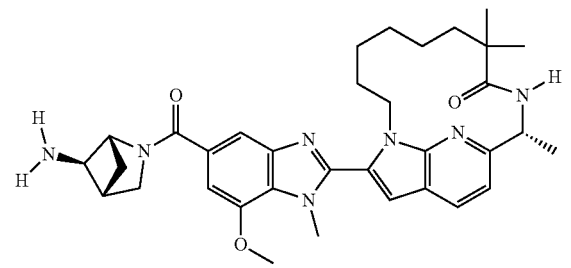
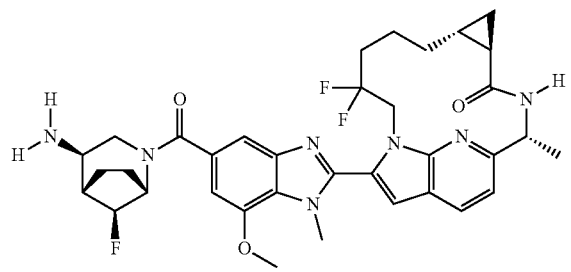
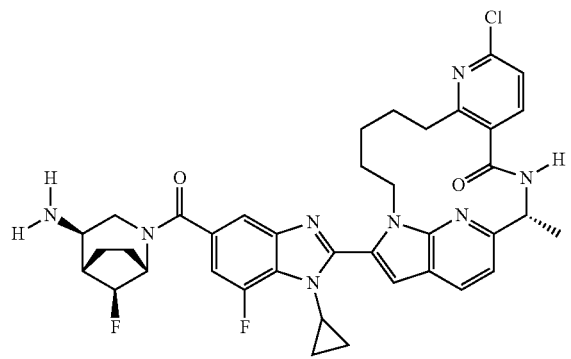
1386
-continued
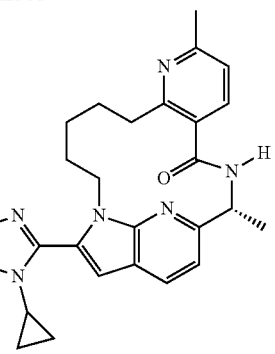
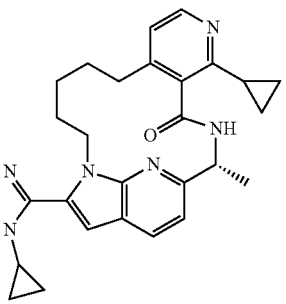
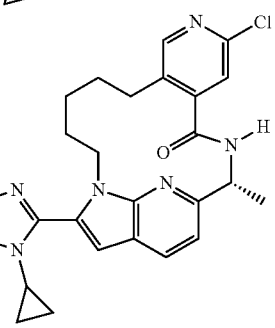
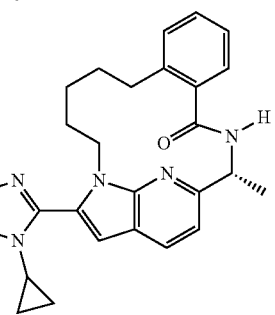
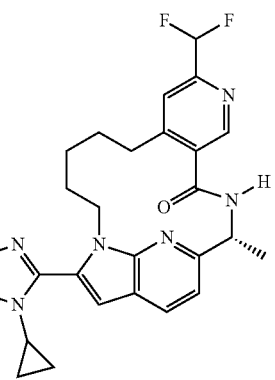

1387
-continued
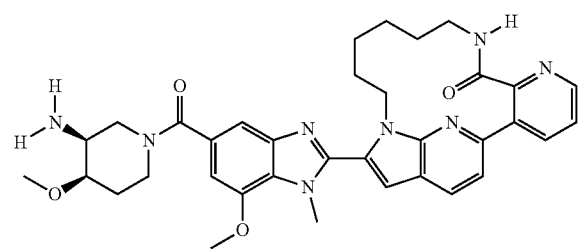
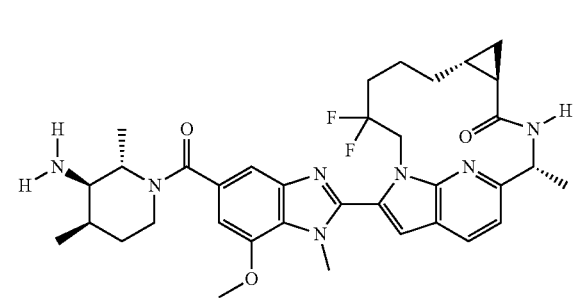
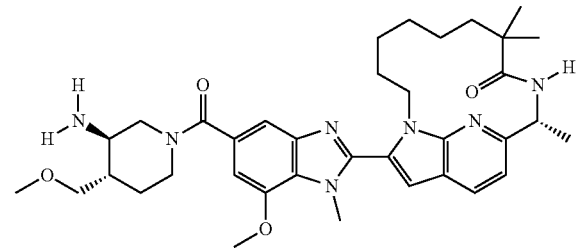
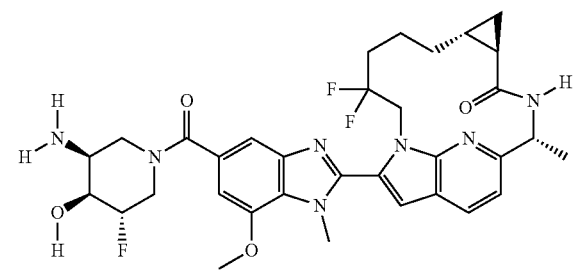
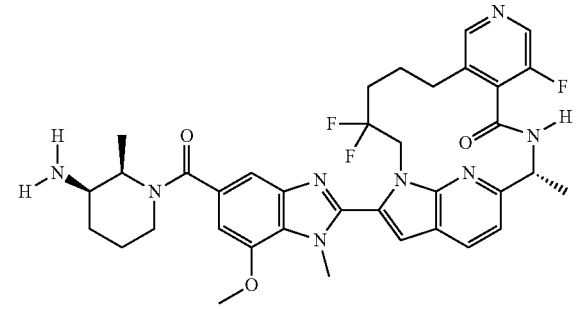
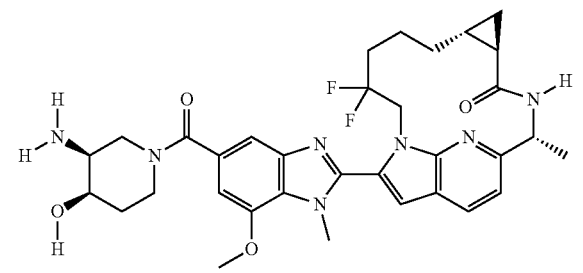
1388
-continued
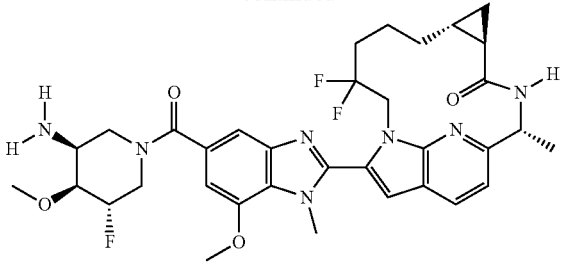
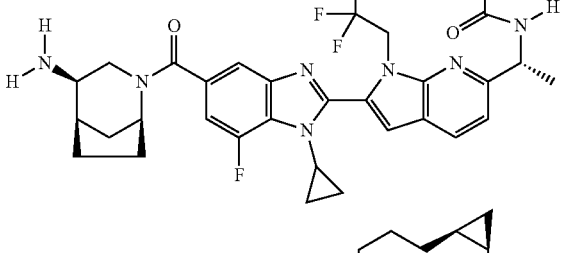
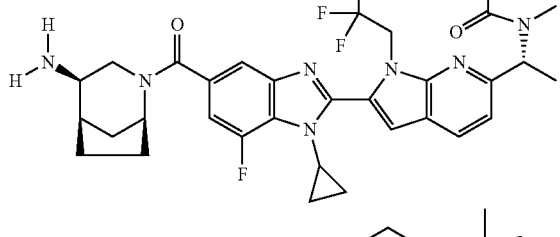
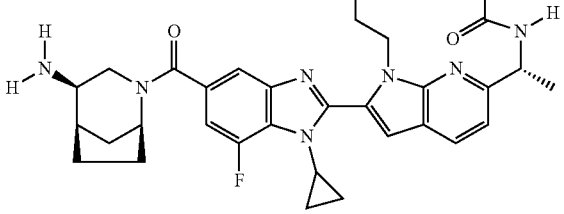
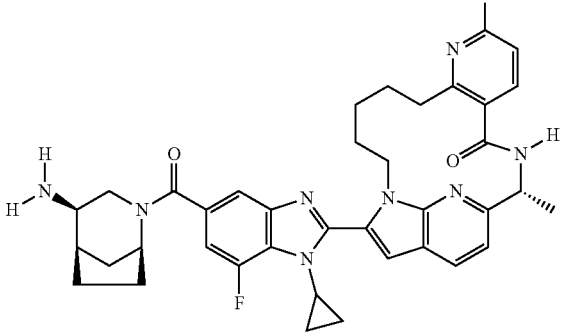
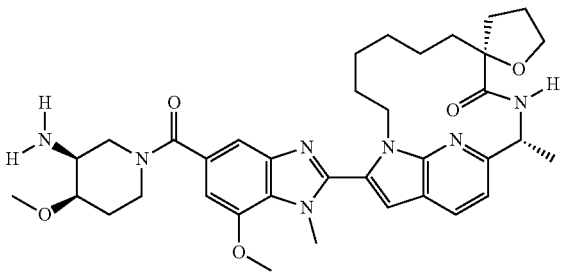

1389
-continued
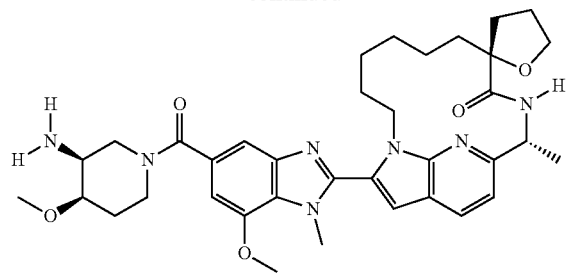
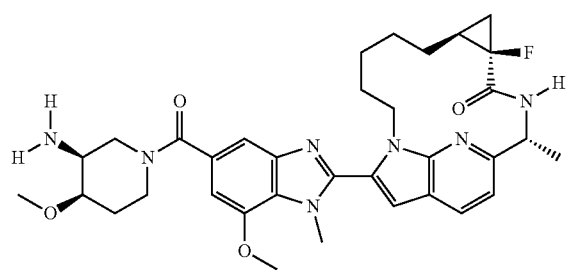
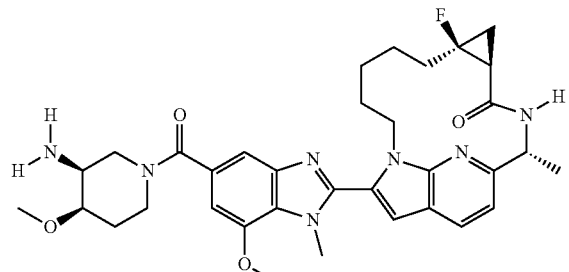
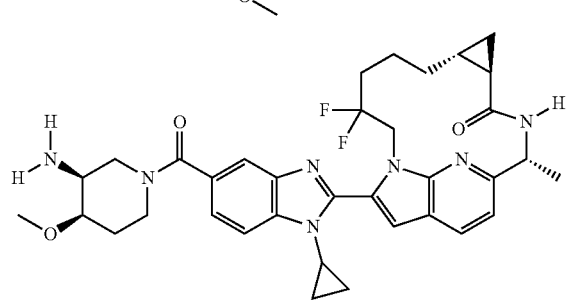
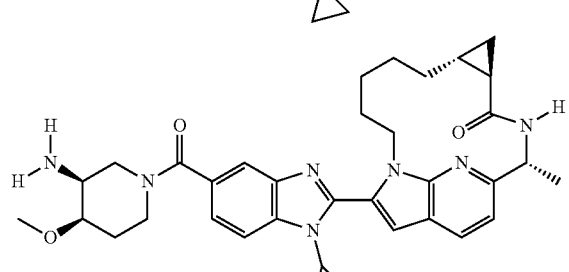
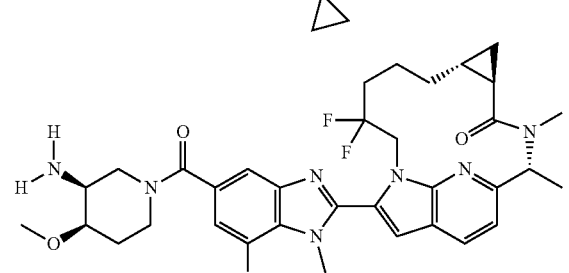
1390
-continued
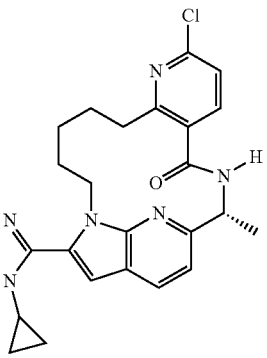
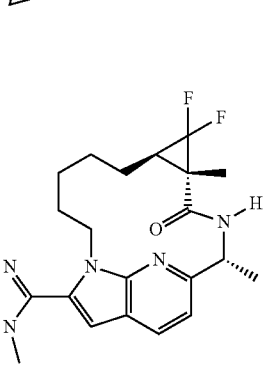
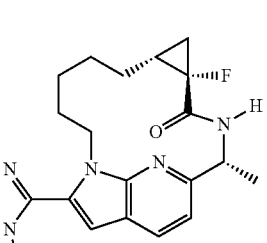
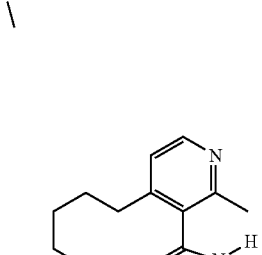
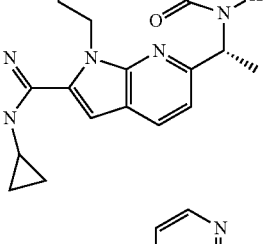
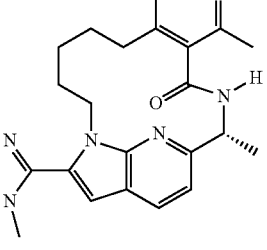

1391
-continued
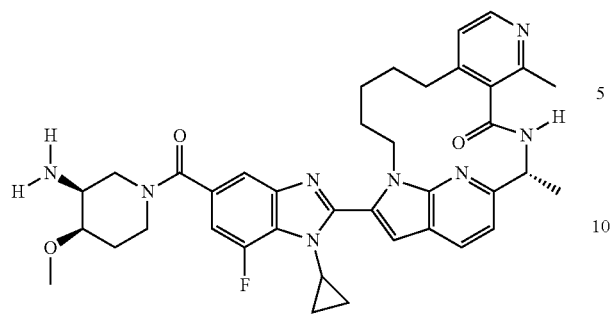
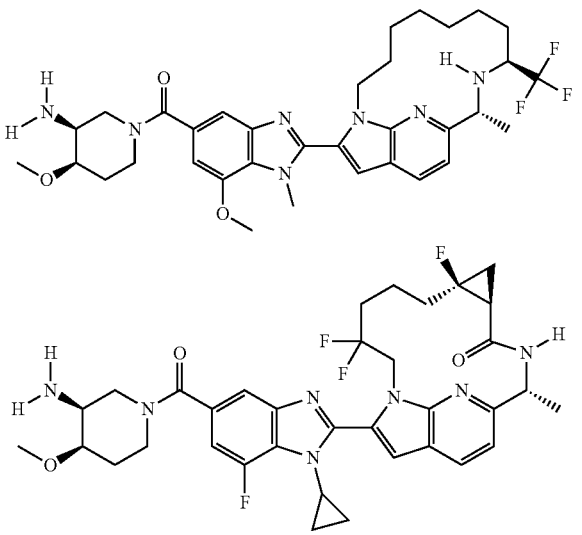
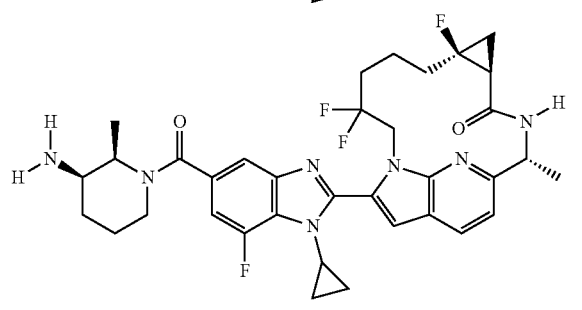
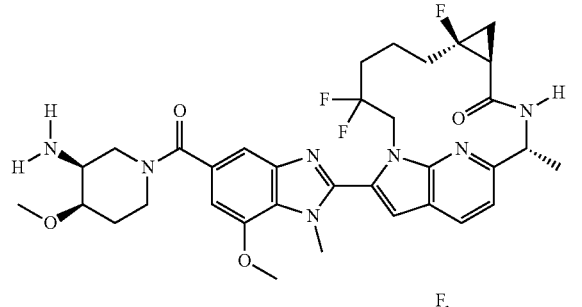
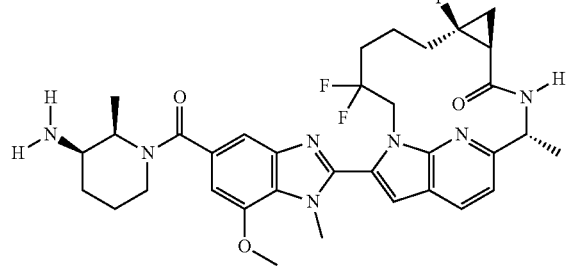
1392
-continued
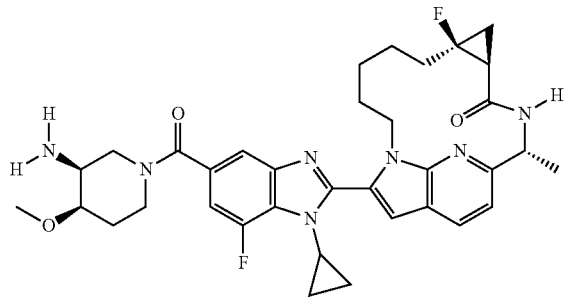
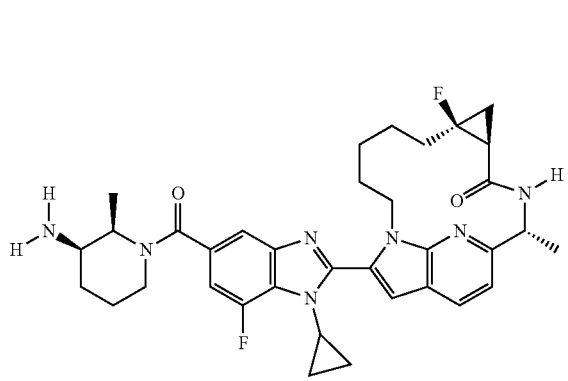
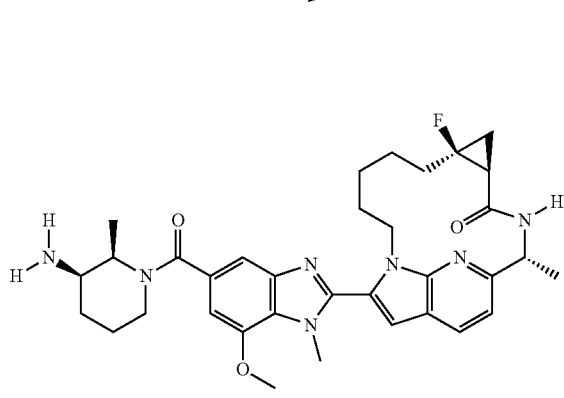

-continued
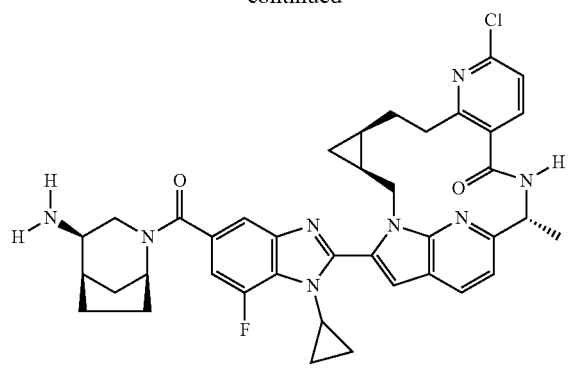
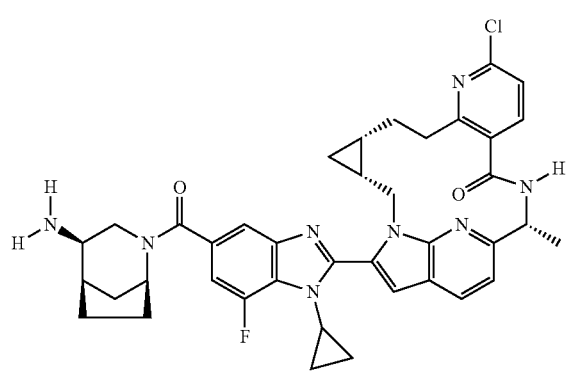
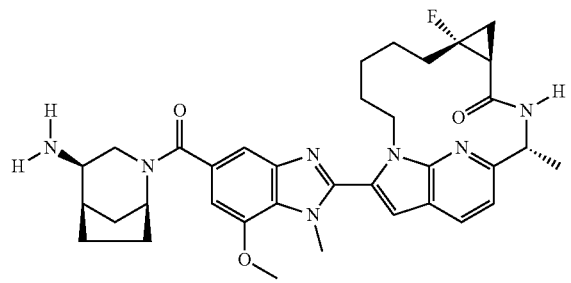
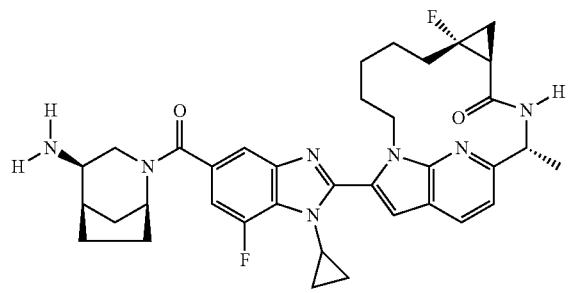
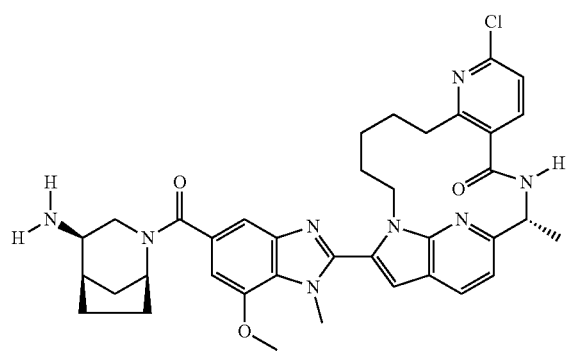
-continued
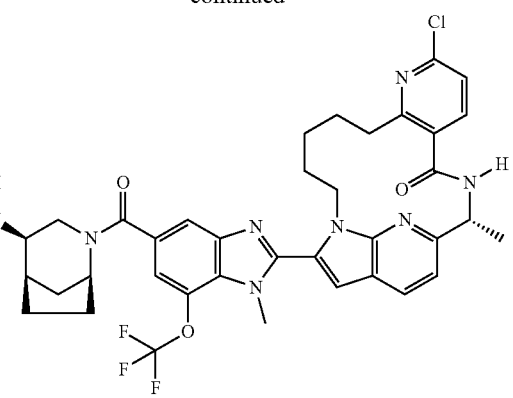
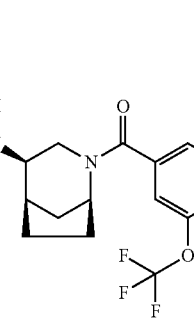
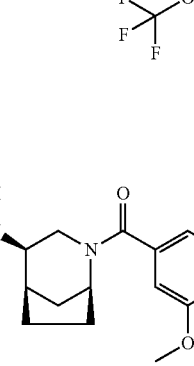
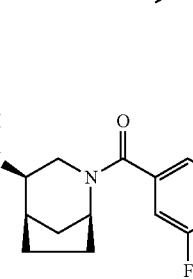
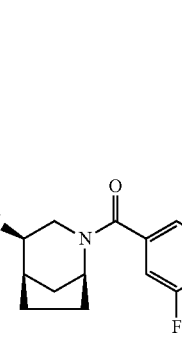

1395
-continued
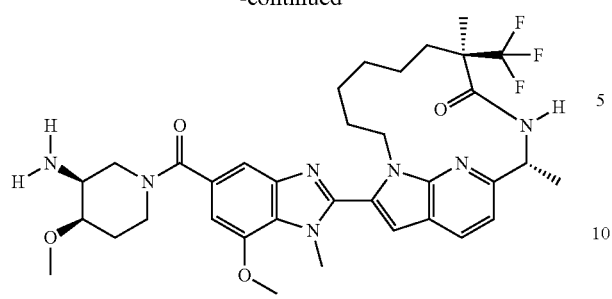
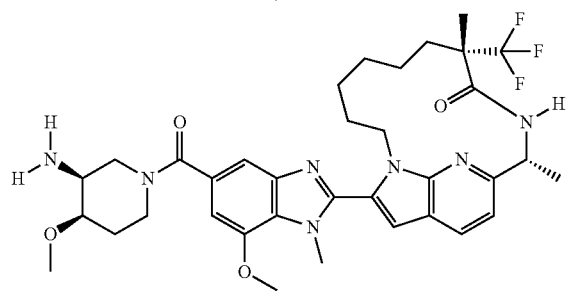
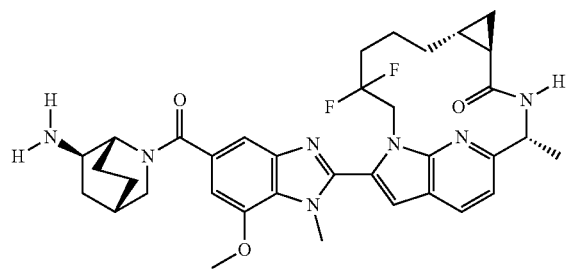
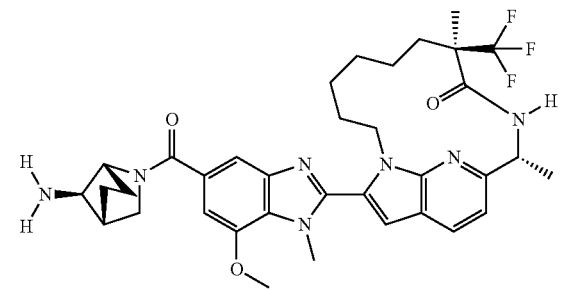
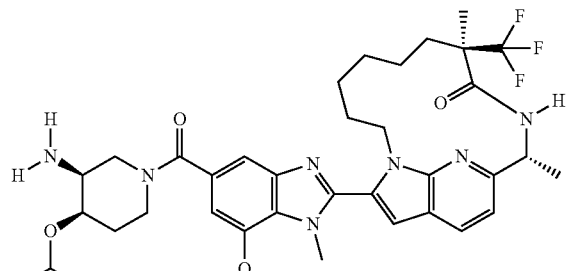
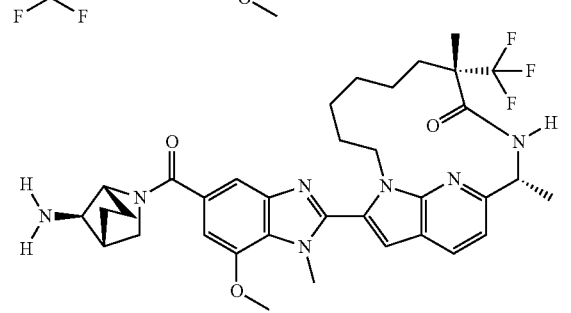
1396
-continued
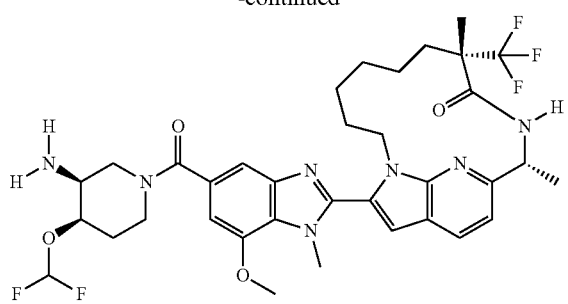
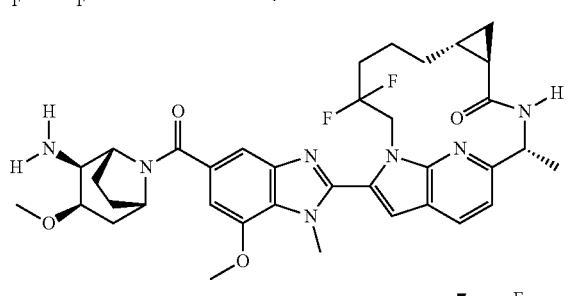
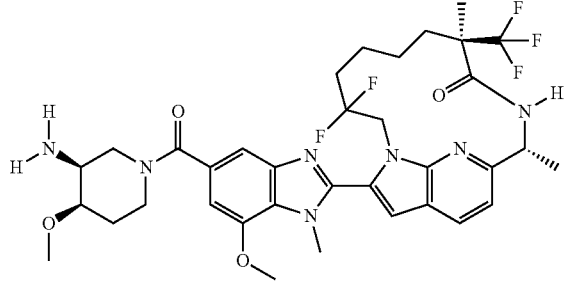
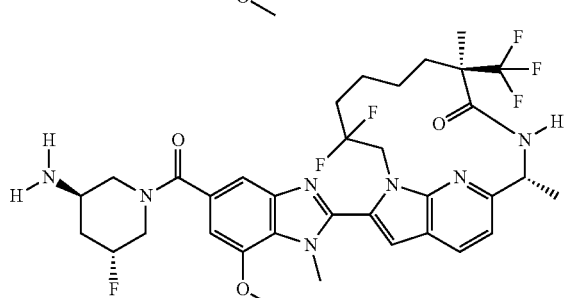
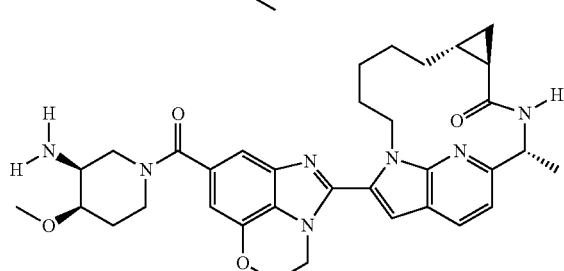
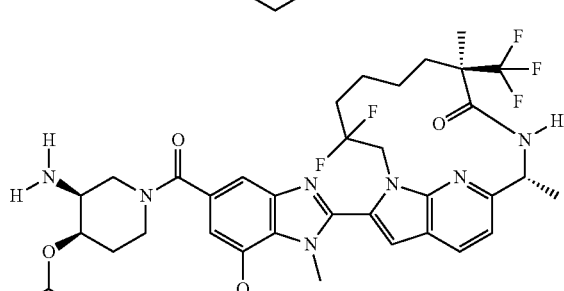

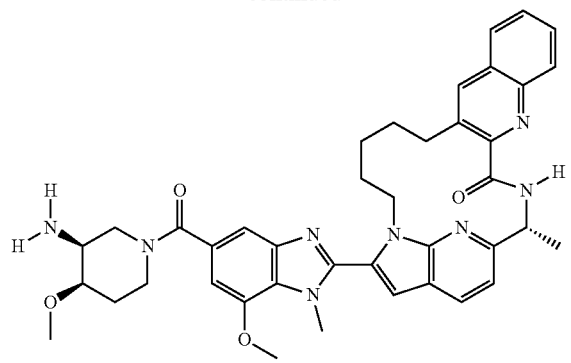
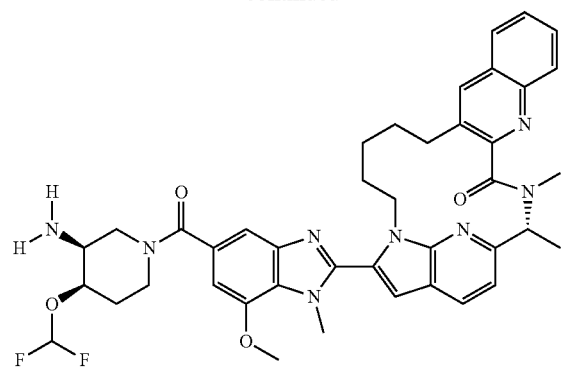

1399
-continued
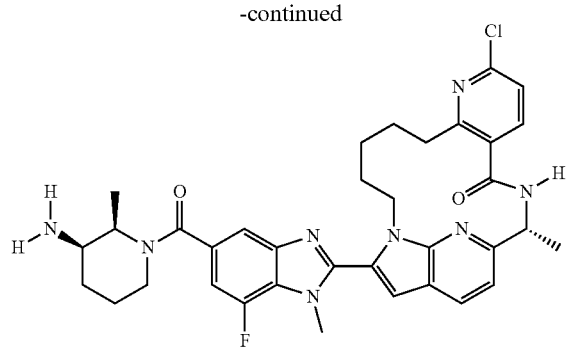
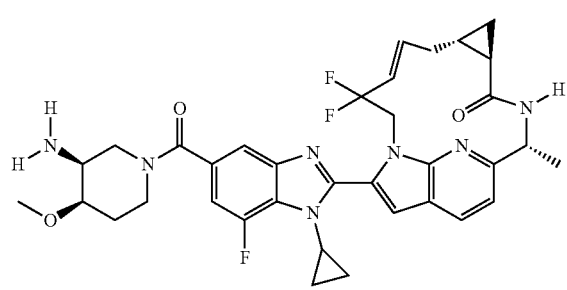
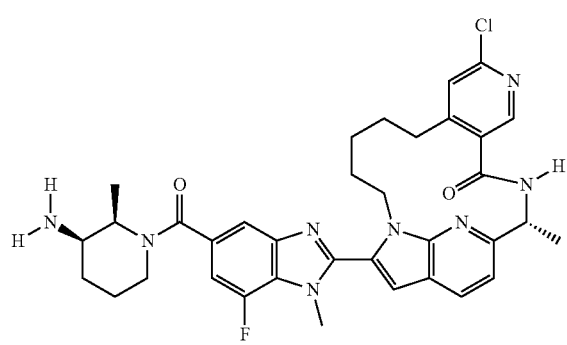
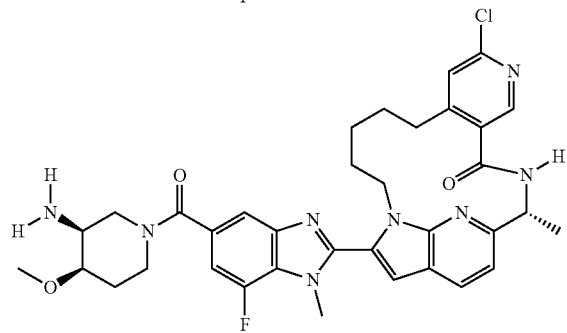
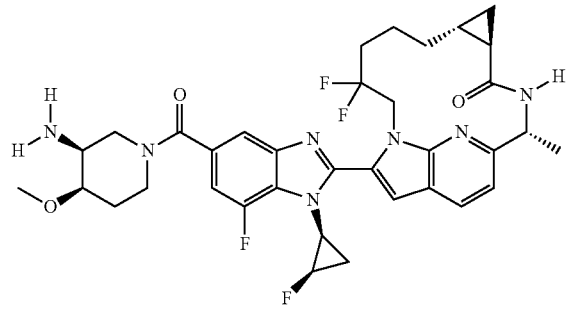
1400
-continued
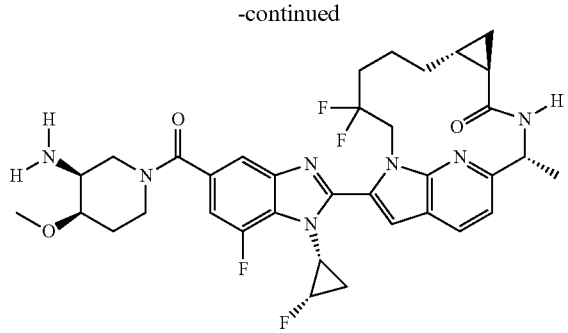
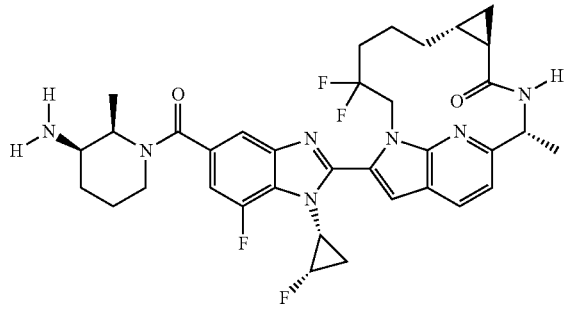
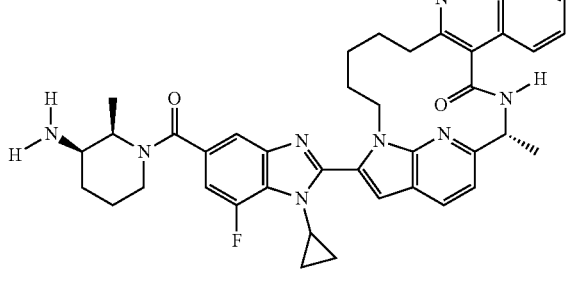
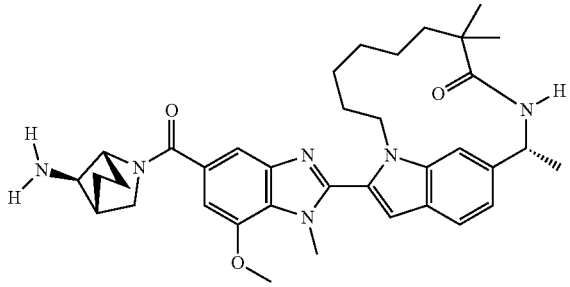
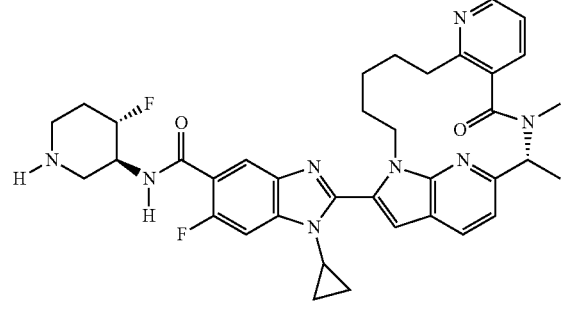

-continued
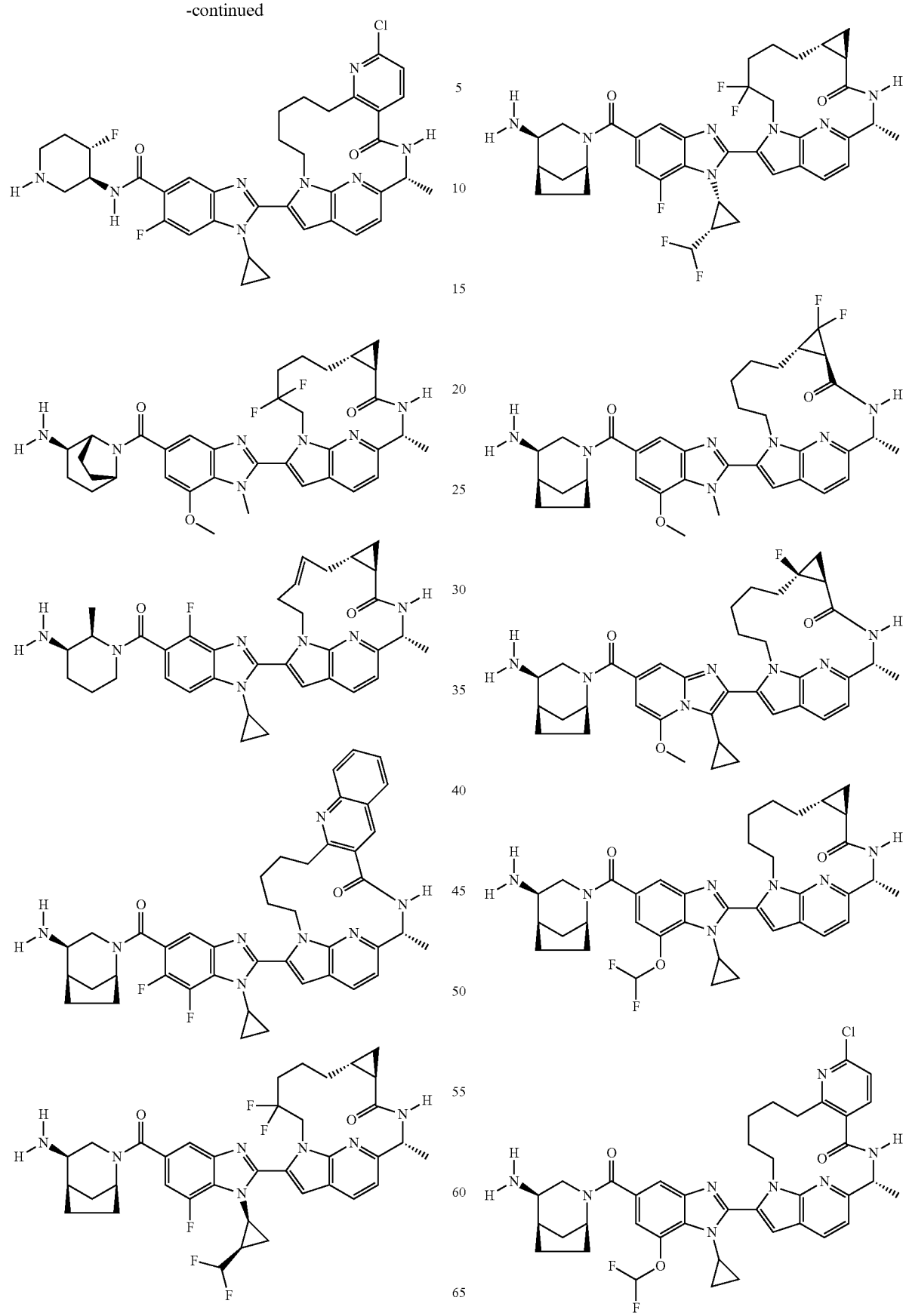

1403
-continued
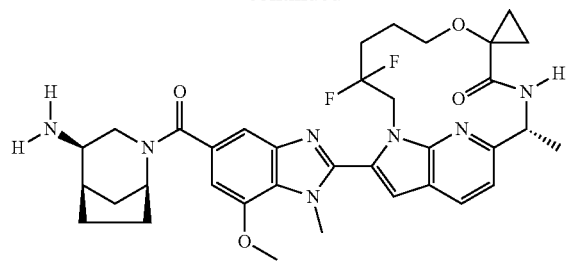
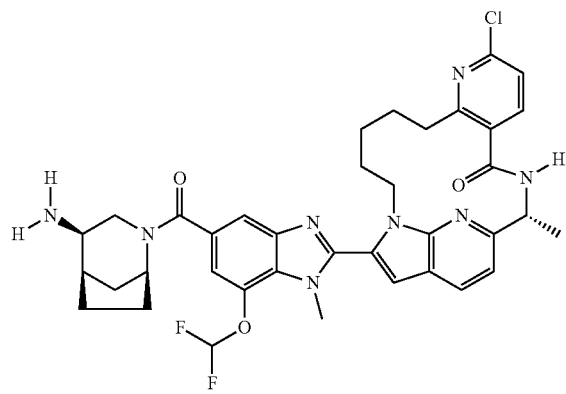
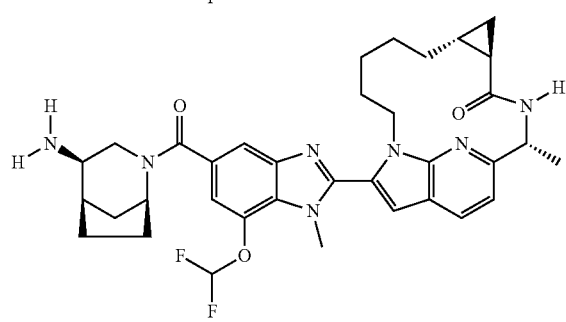
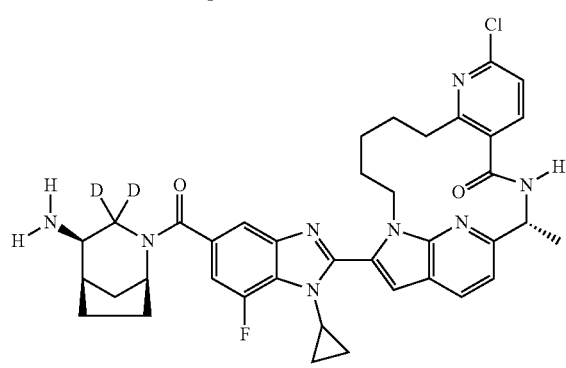
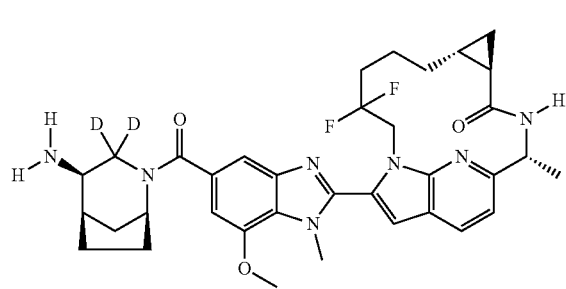
1404
-continued
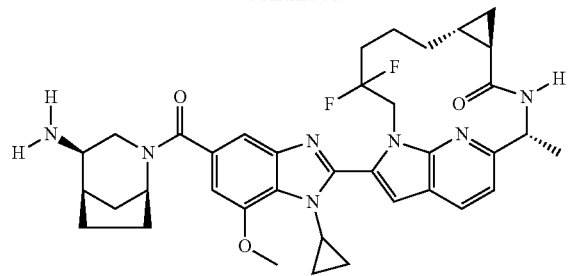
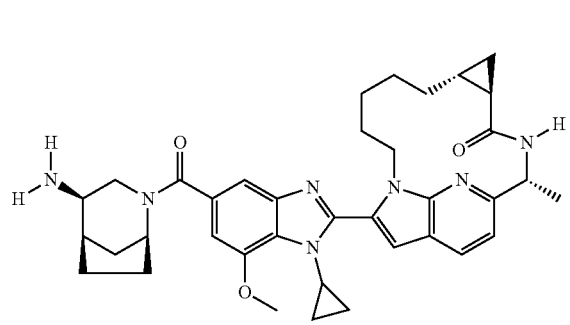
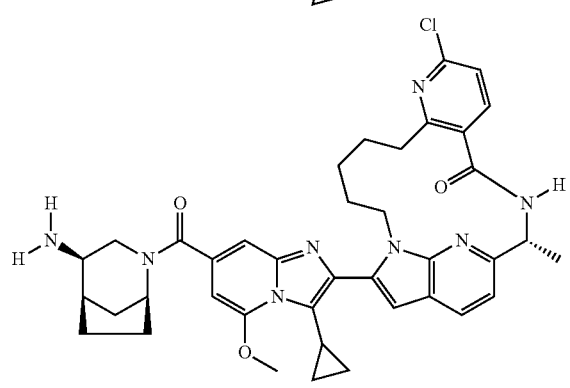
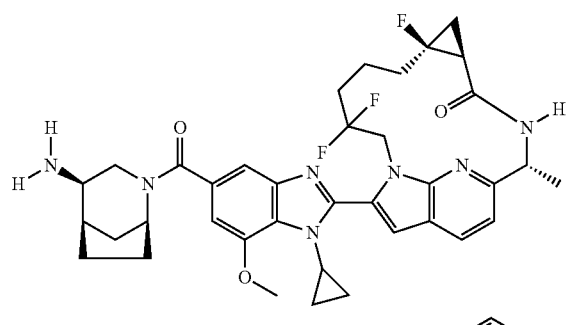
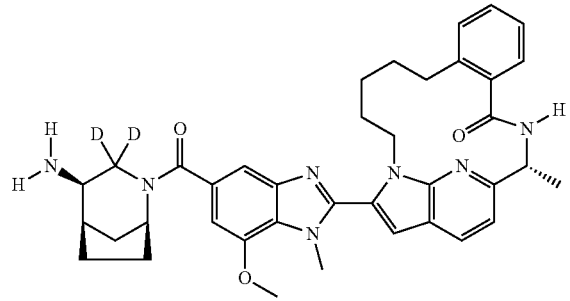

1405
-continued
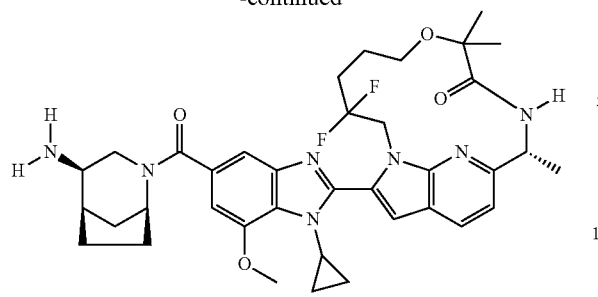
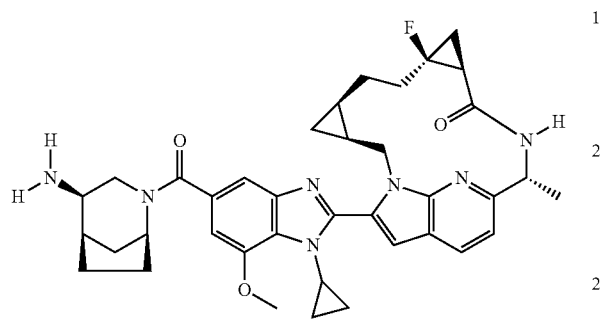
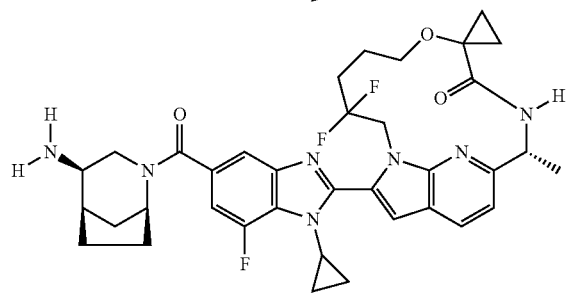
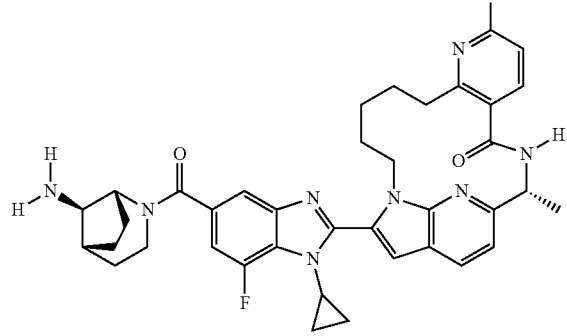
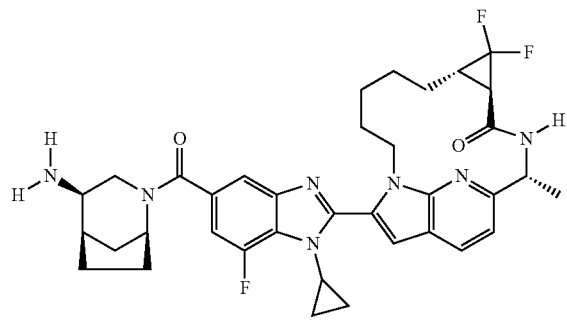
1406
-continued
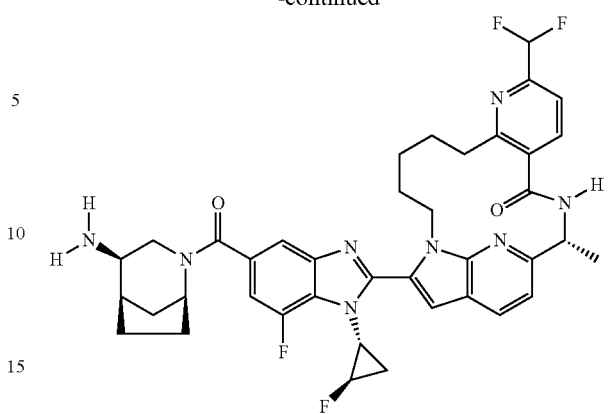
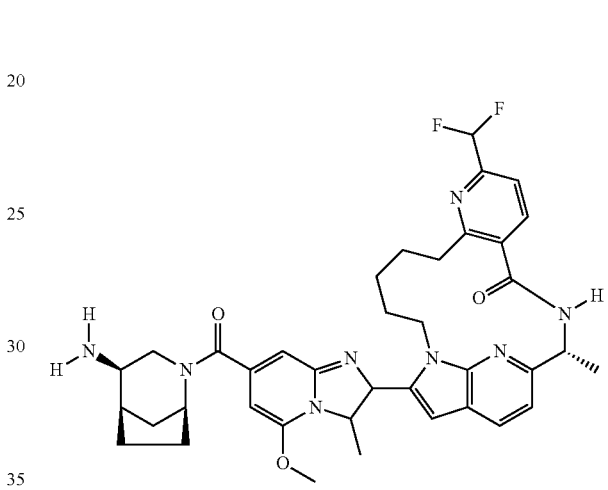
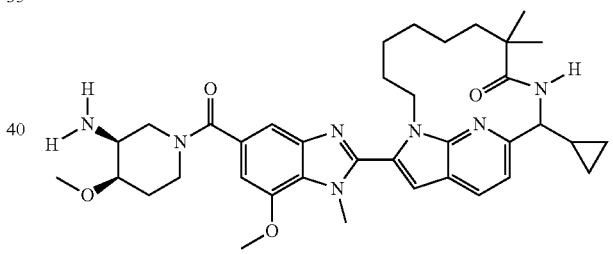
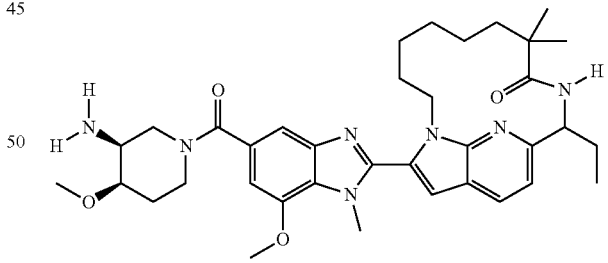
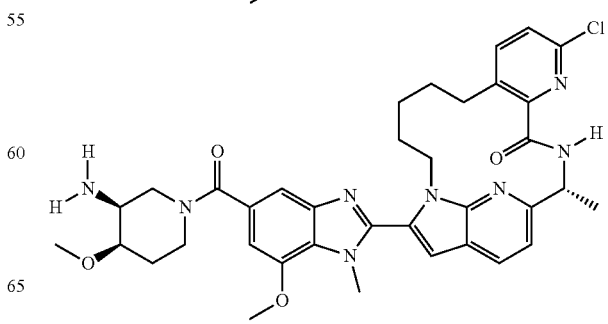

1407
-continued
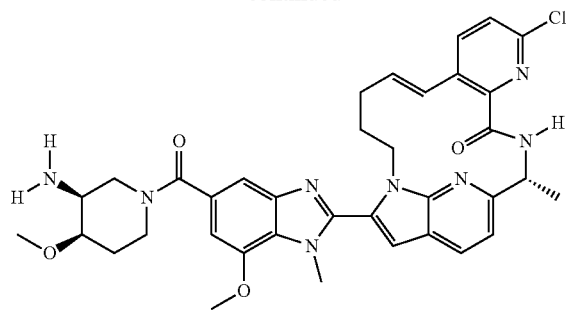
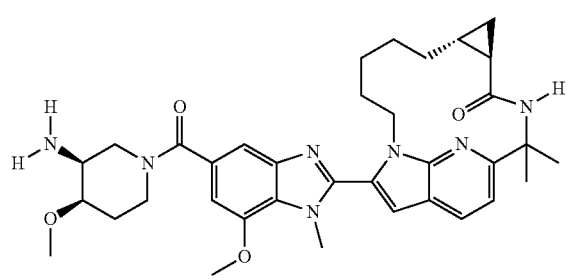
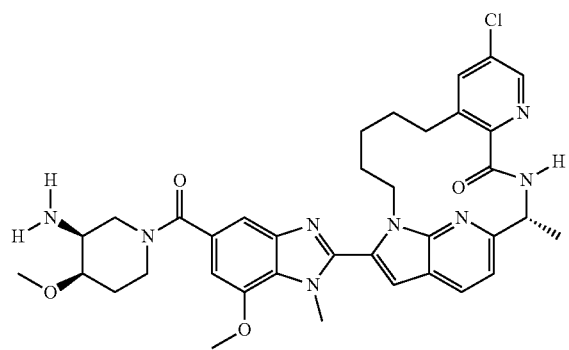
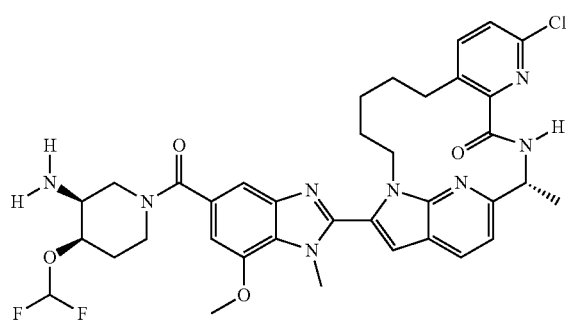
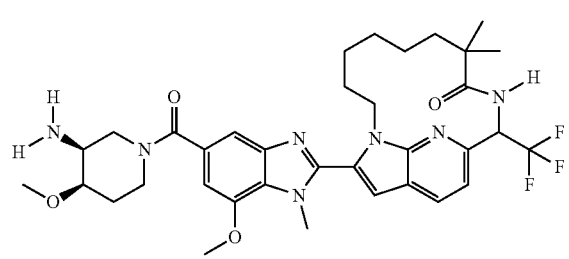
1408
-continued
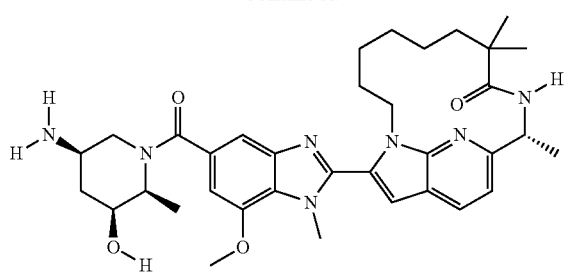
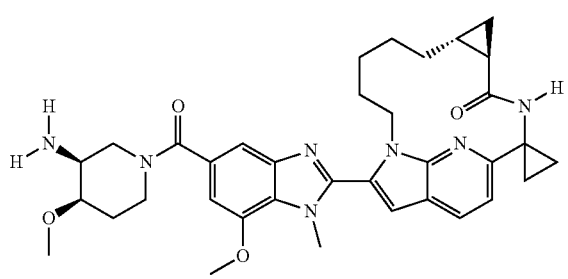
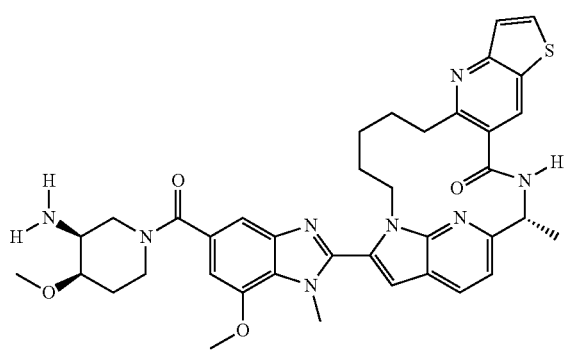
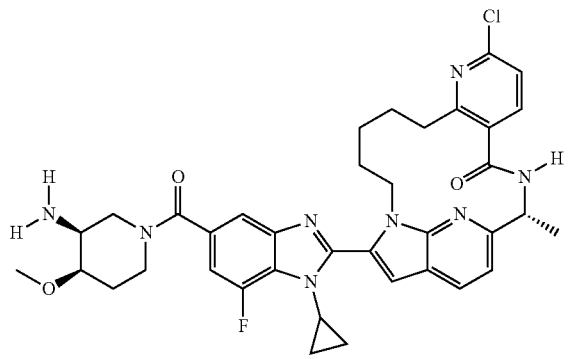
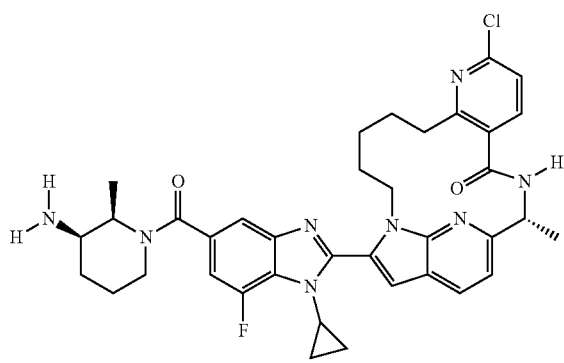

1409
-continued
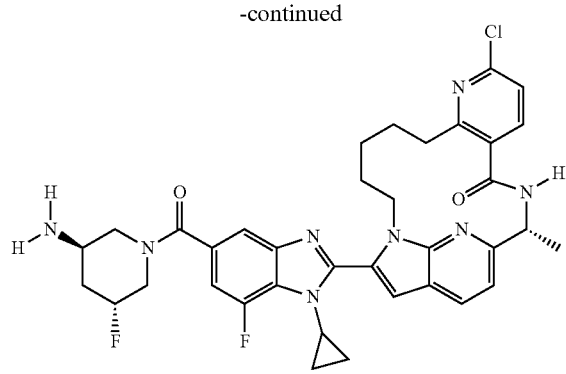
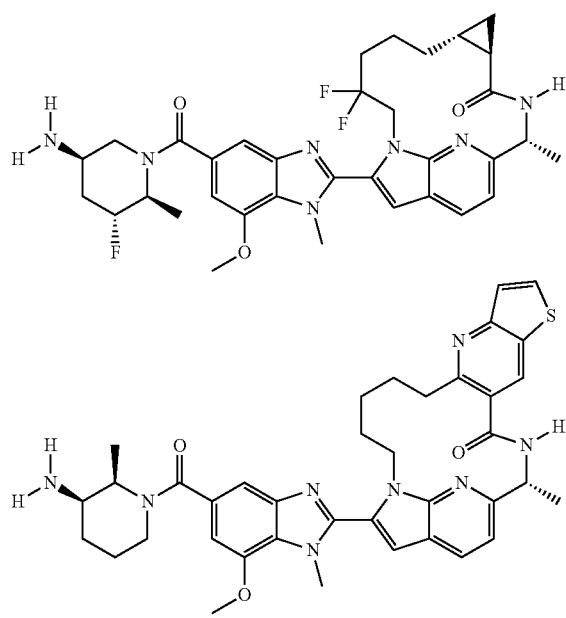
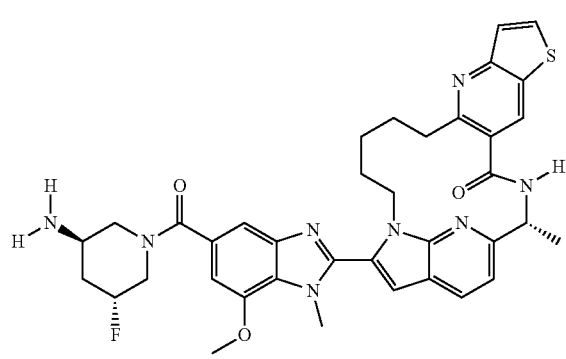
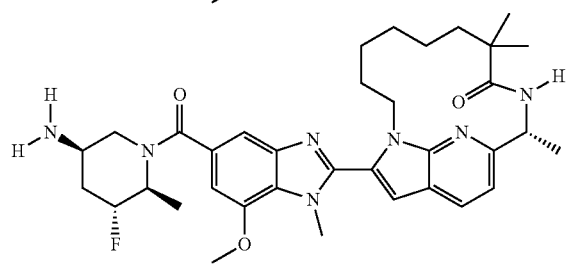
1410
-continued
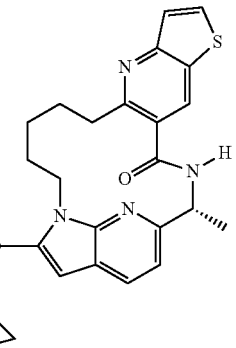
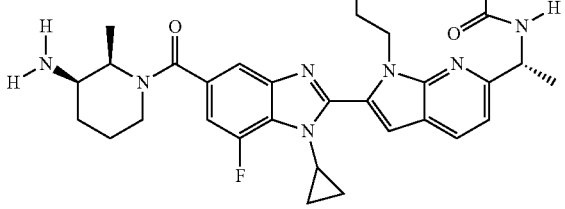
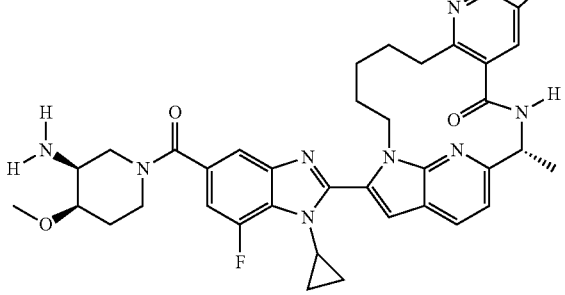
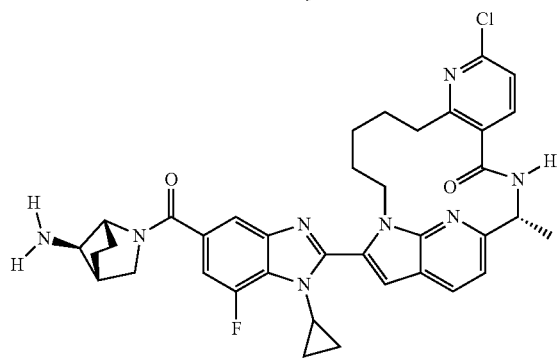
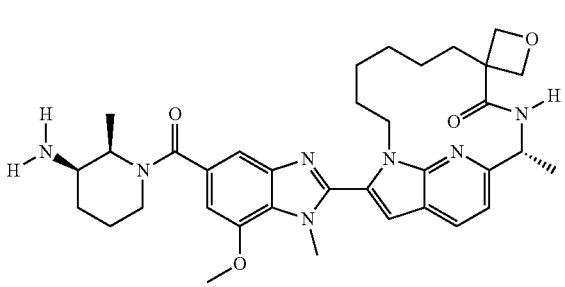
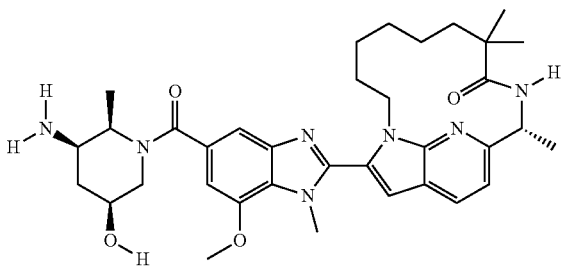

1411
-continued
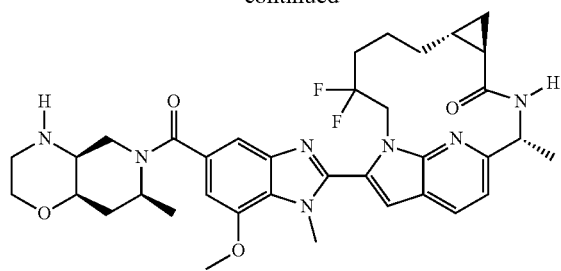
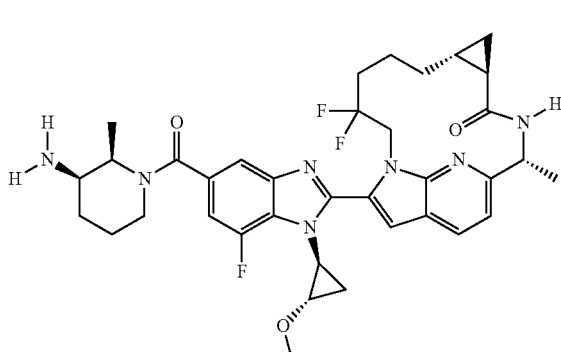
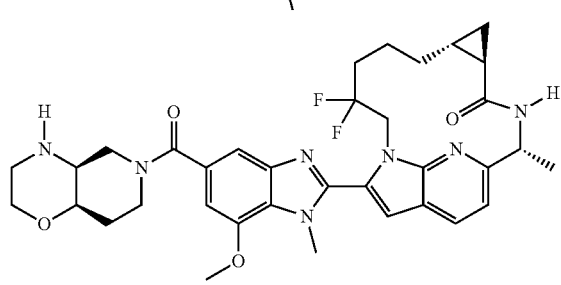
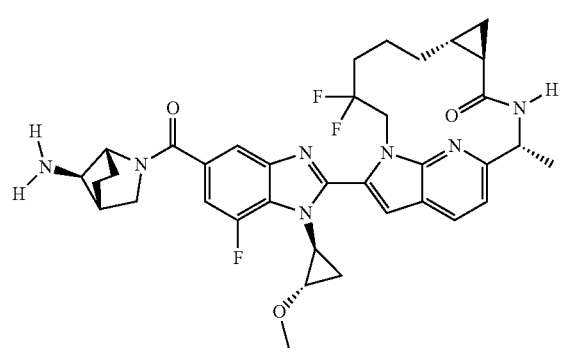
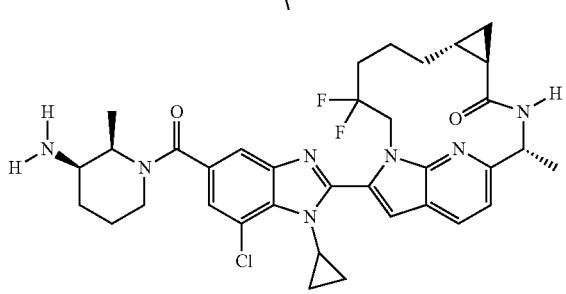
1412
-continued
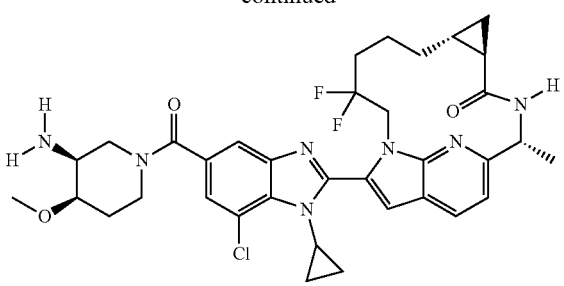
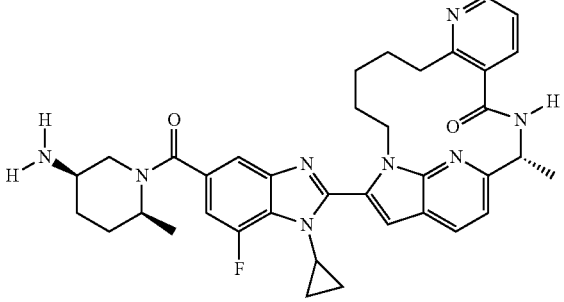
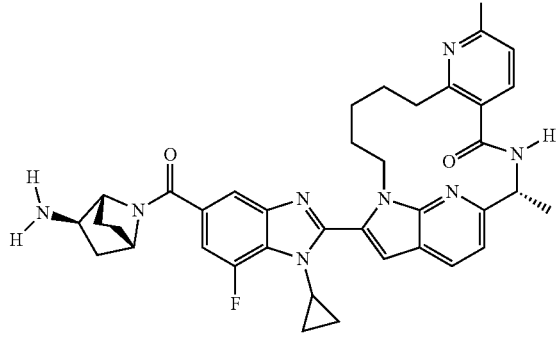
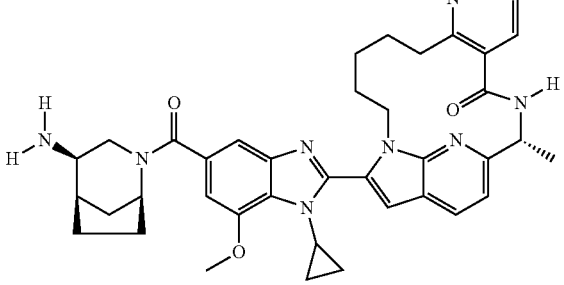
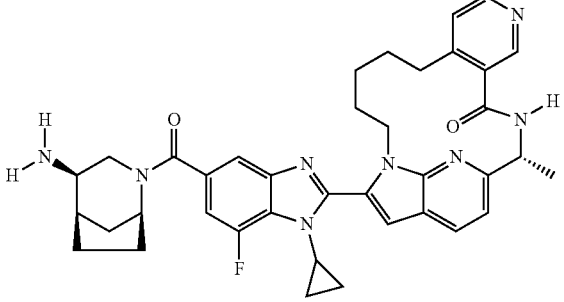

1413
-continued
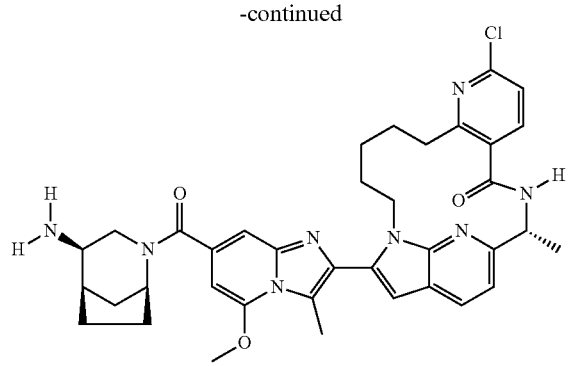
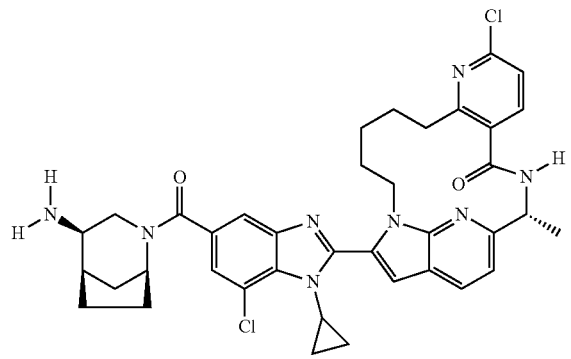
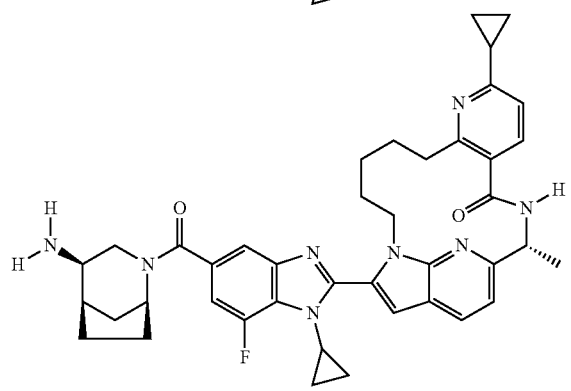
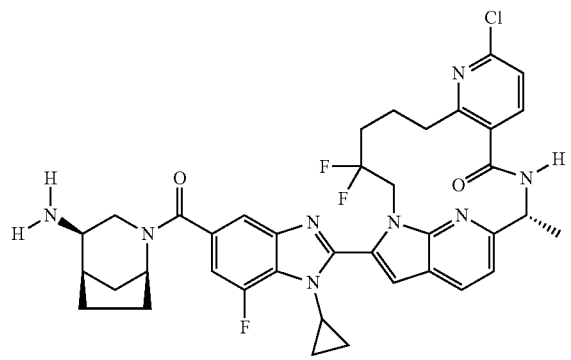
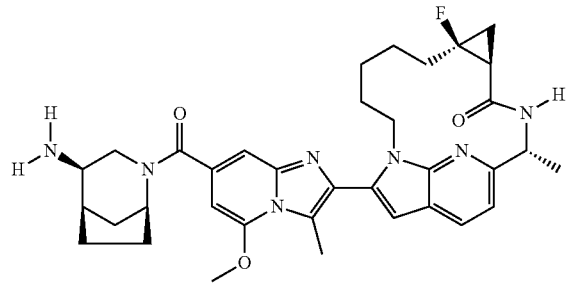
1414
-continued
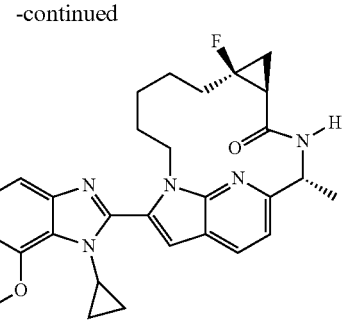
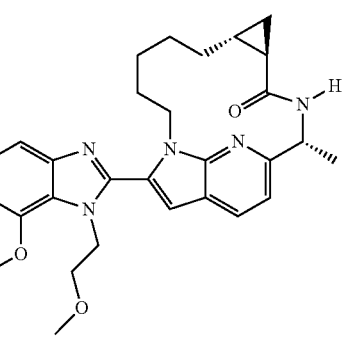
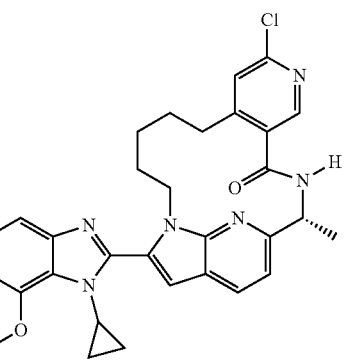
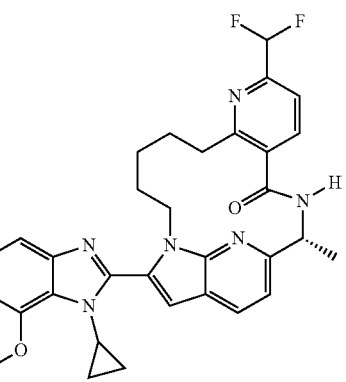

1415
-continued
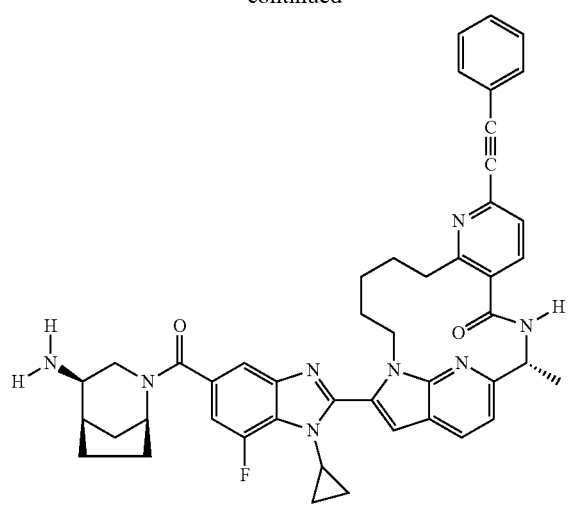
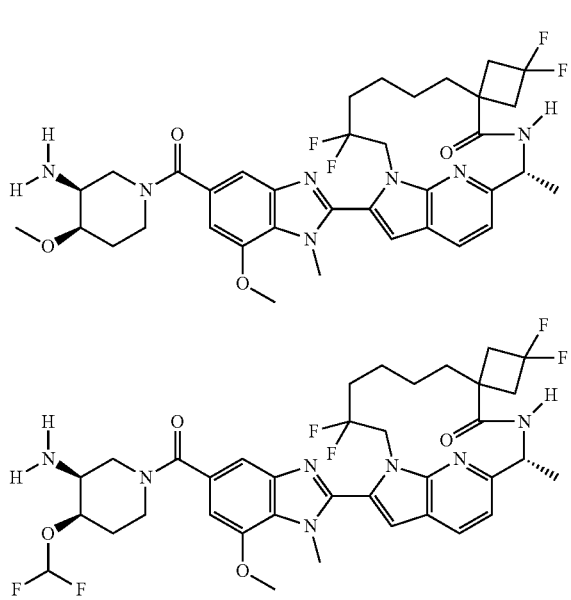
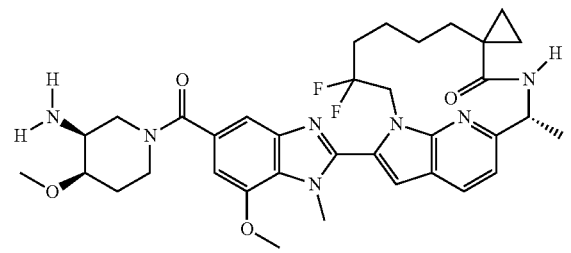
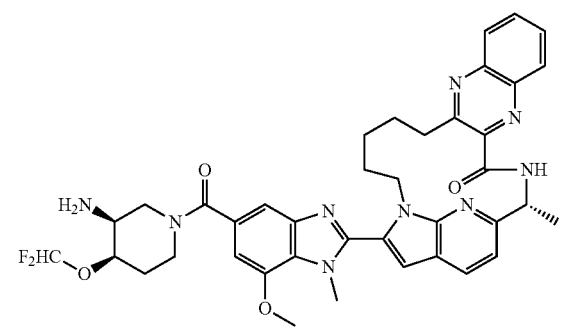
1416
-continued
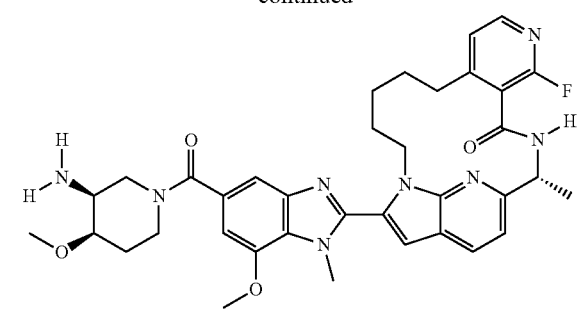
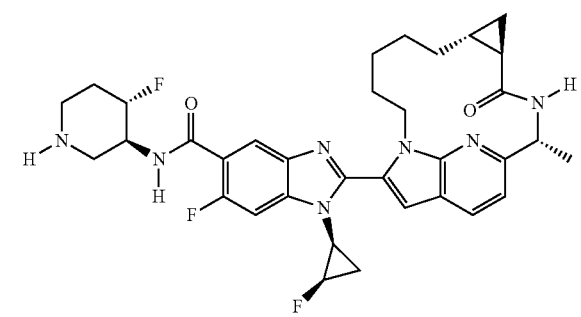
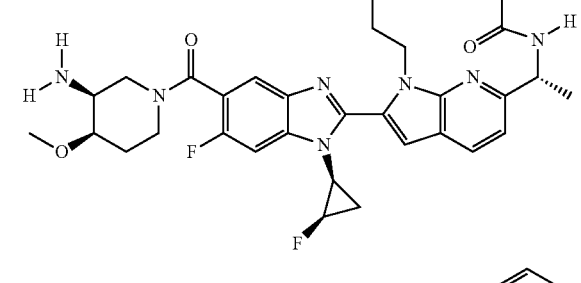
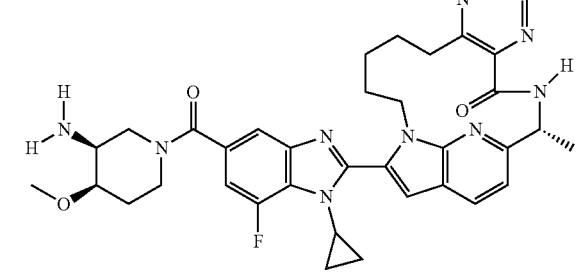
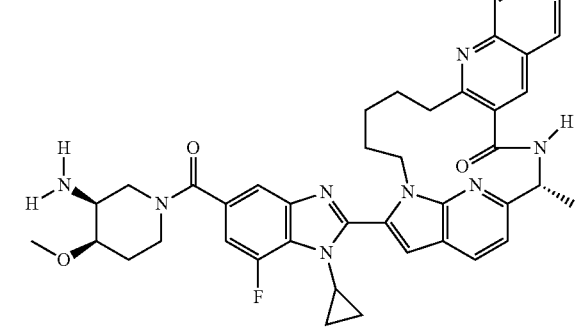

1417
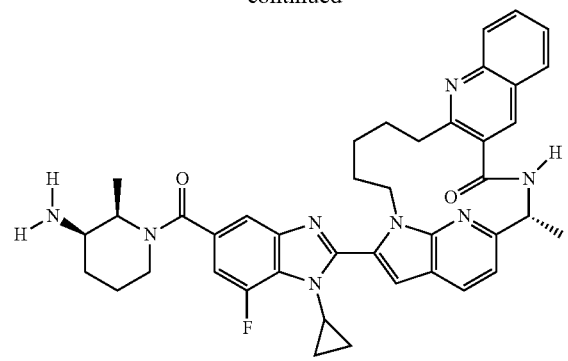
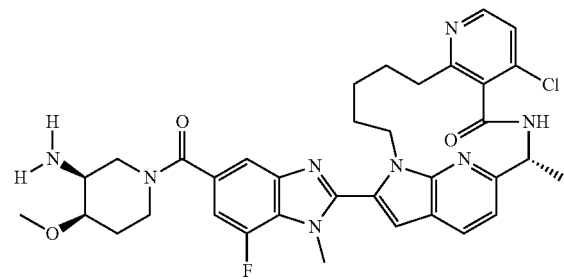
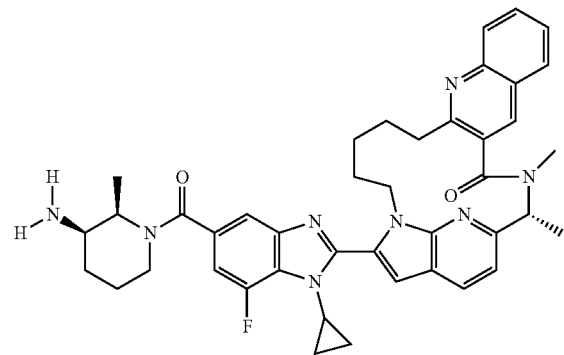
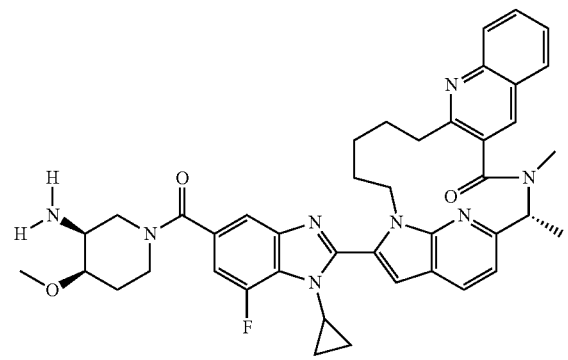
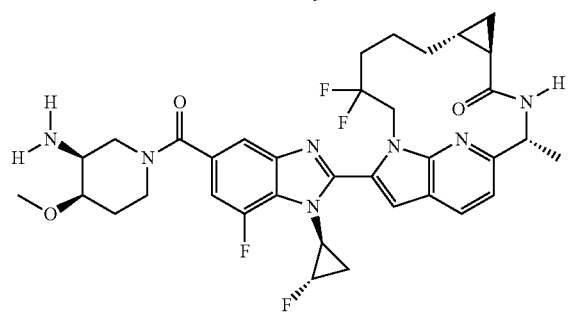
1418
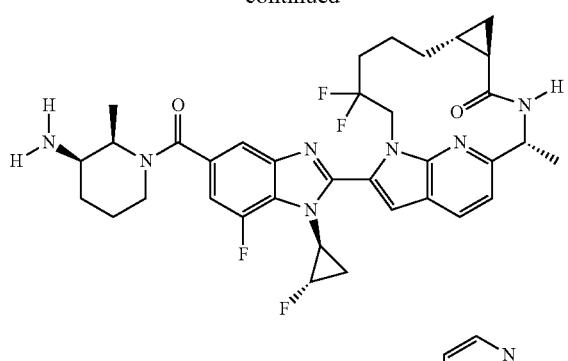
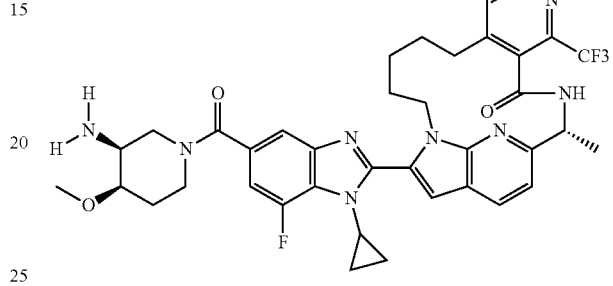
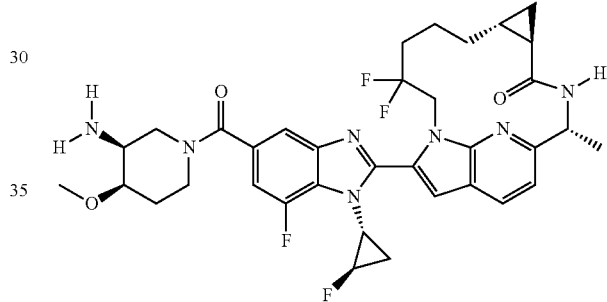
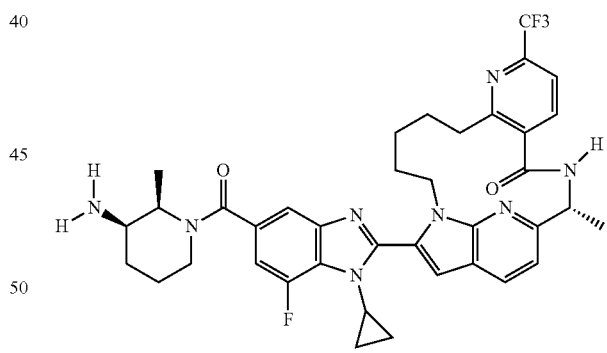
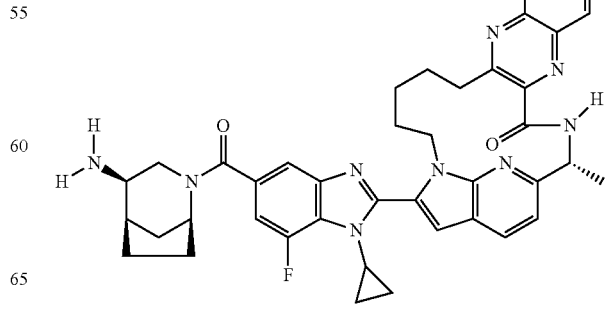

1419
-continued
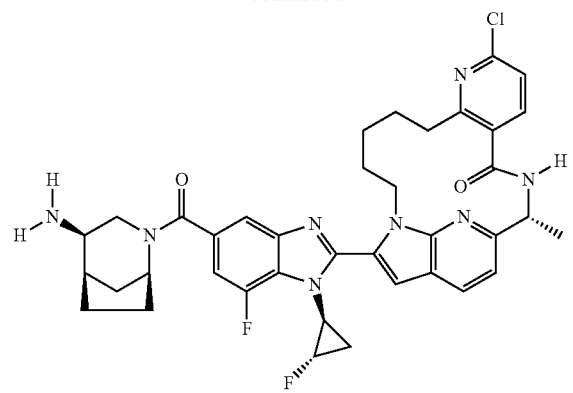
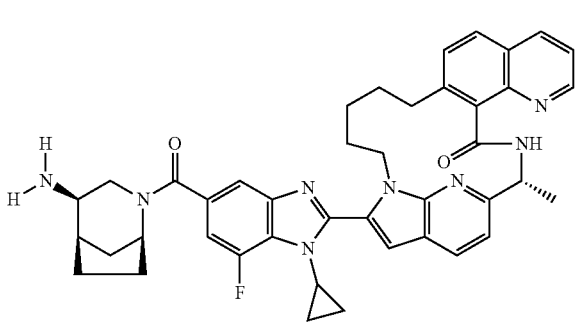
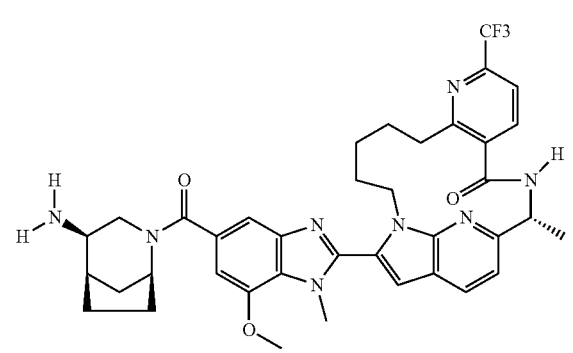
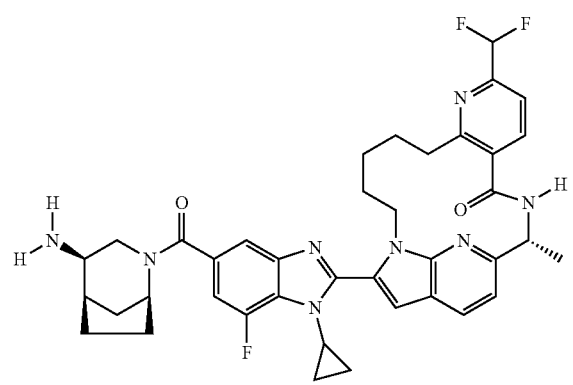
1420
-continued
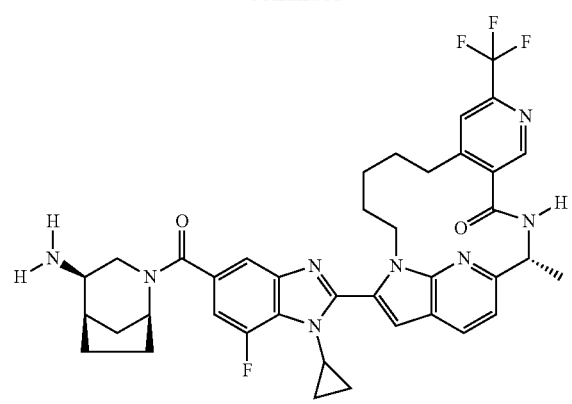
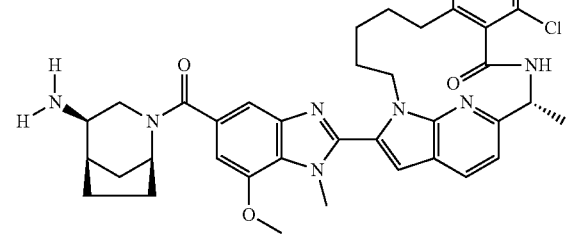
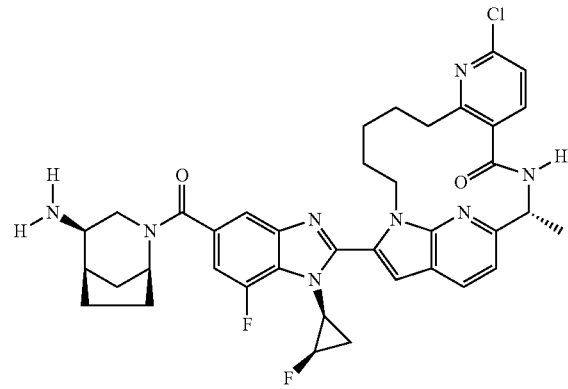
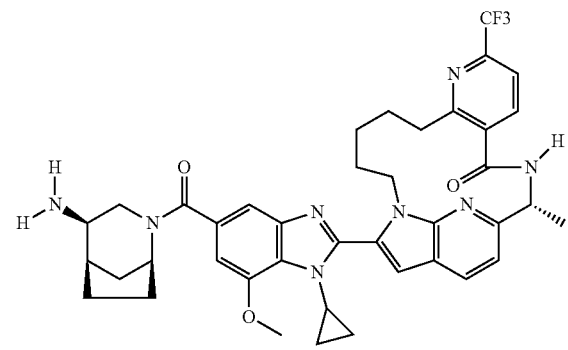
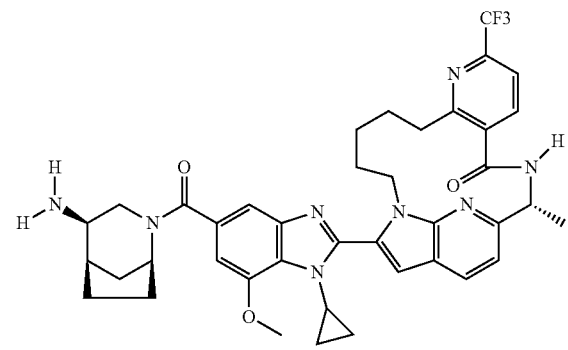

1421
-continued
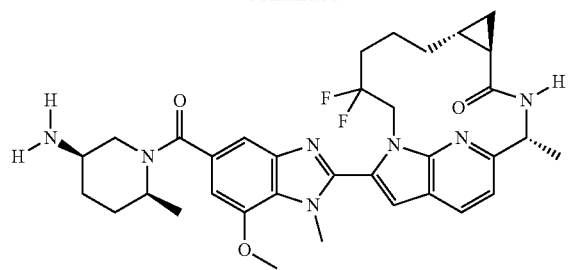
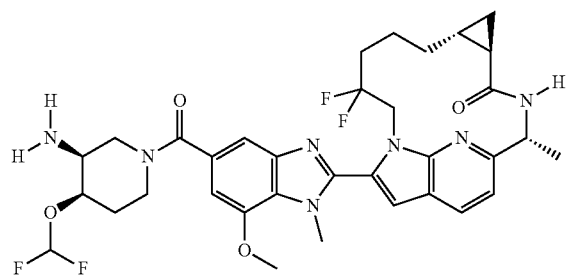
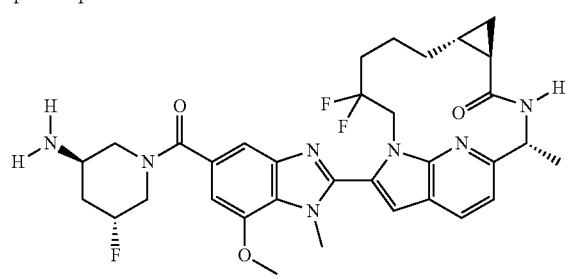
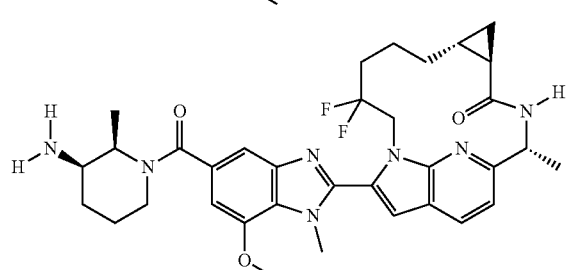
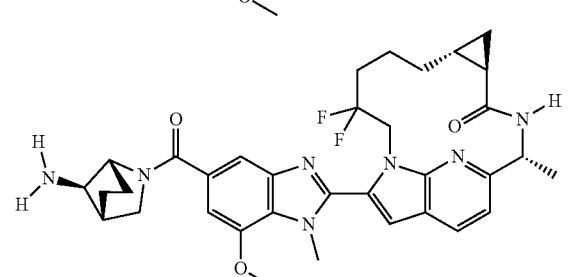
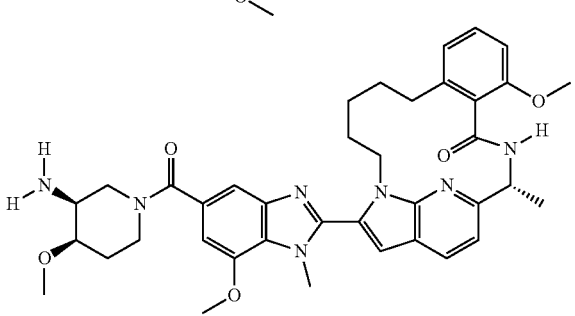
1422
-continued
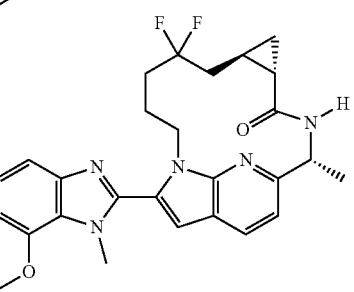
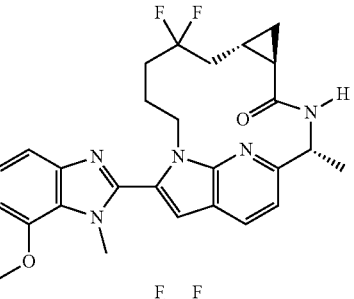
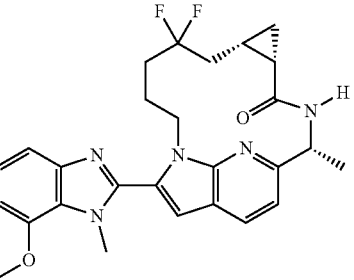
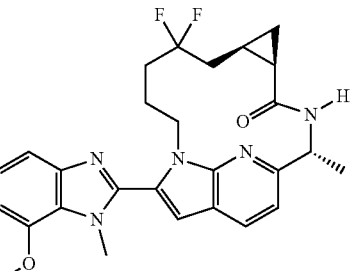
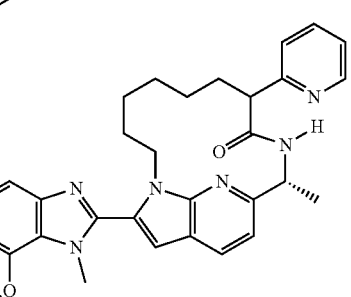

1423
-continued
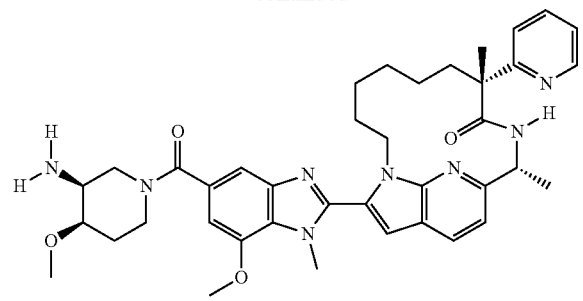
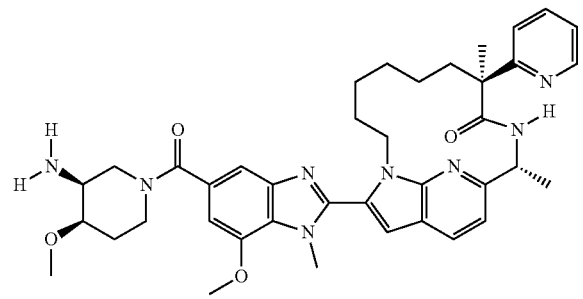
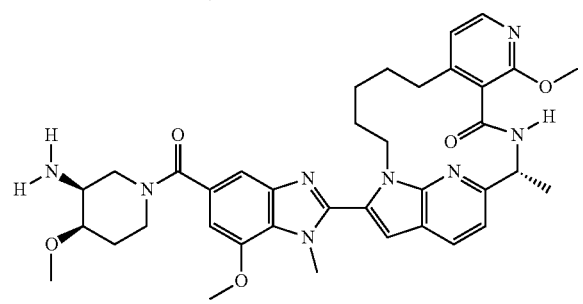
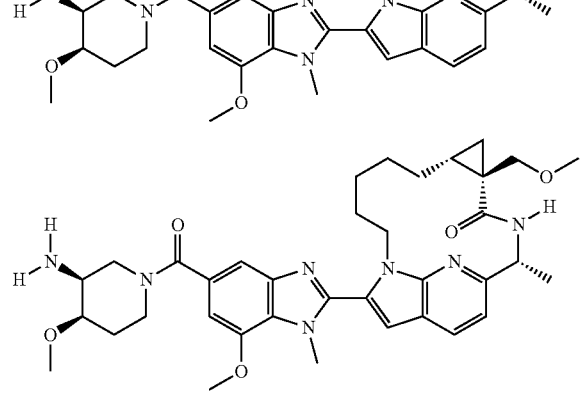
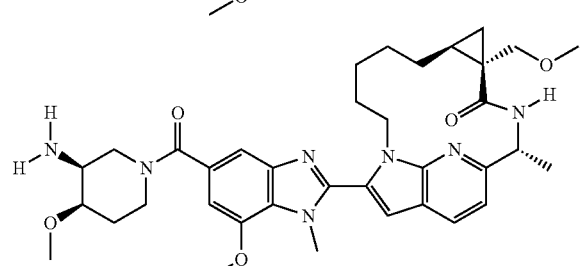
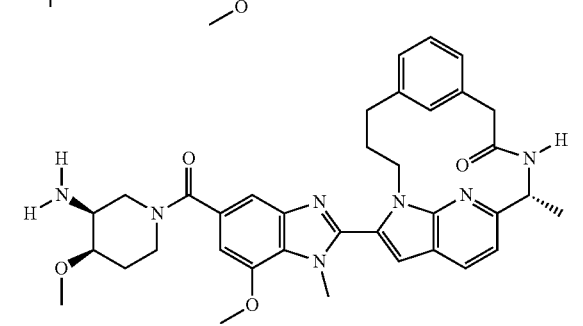
1424
-continued
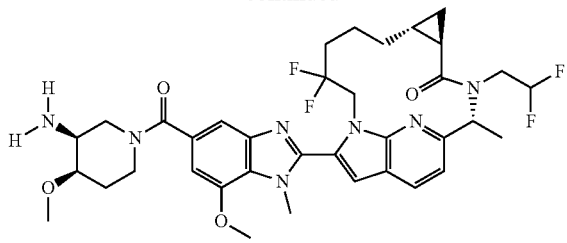
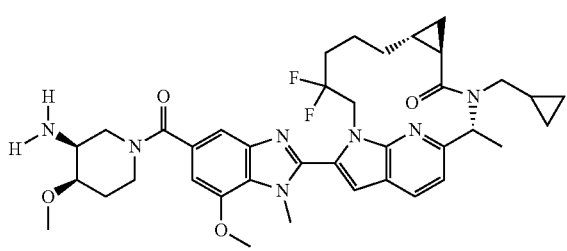
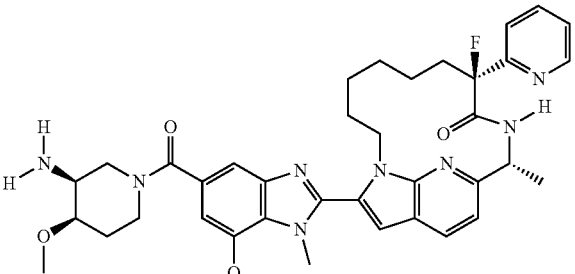
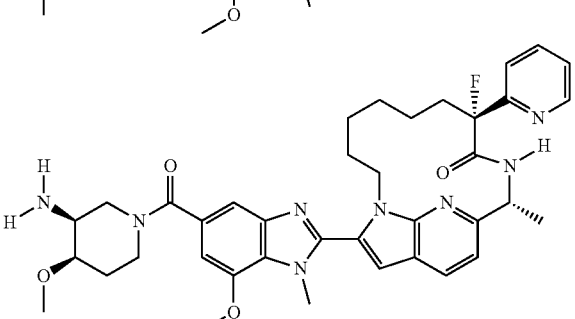
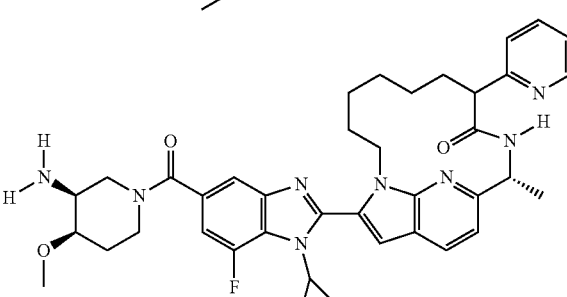
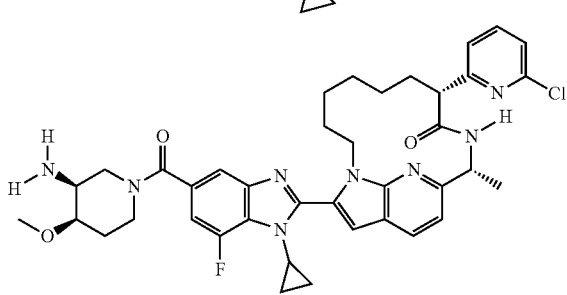

1425
-continued
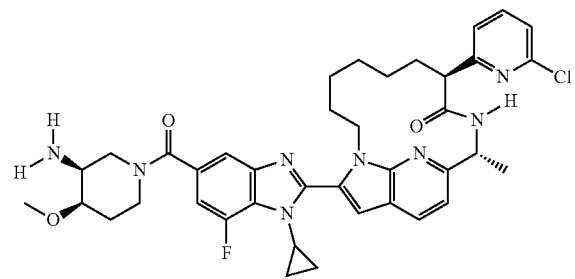
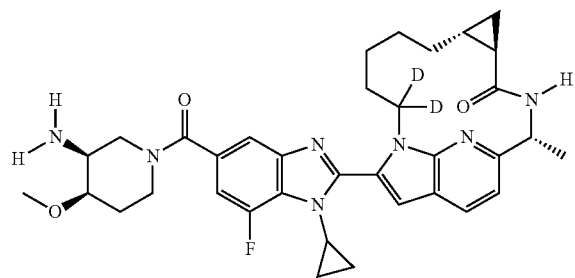
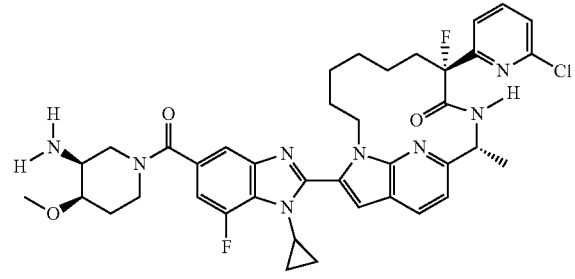
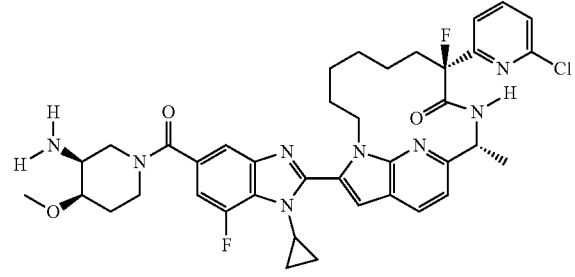
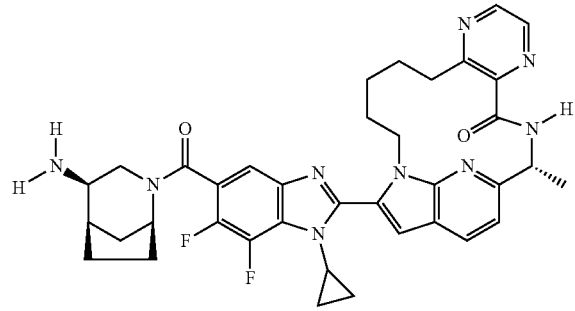
1426
-continued
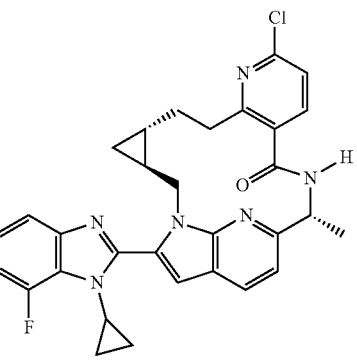
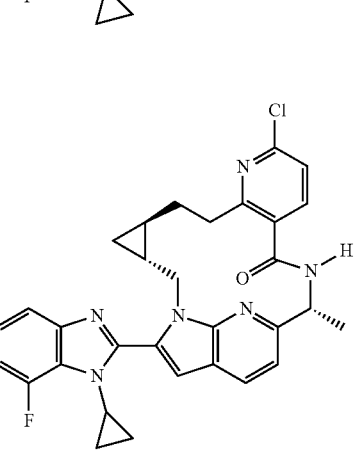
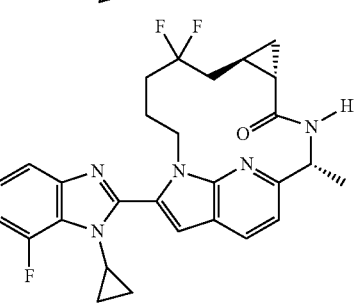
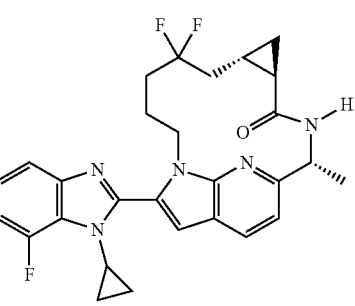
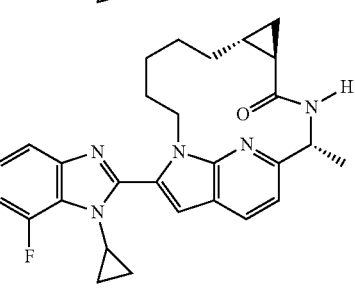

1427
-continued
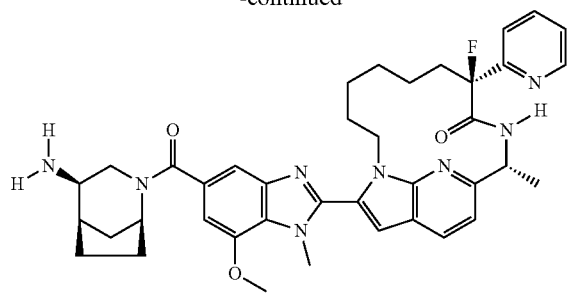
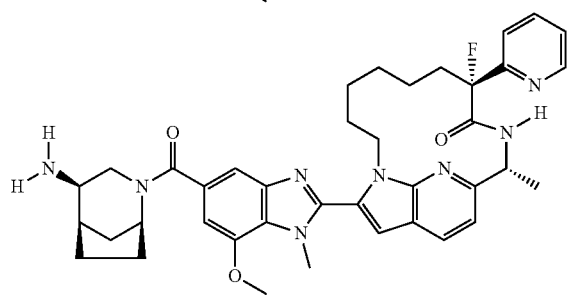
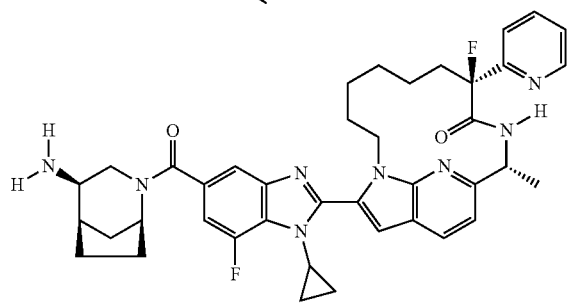
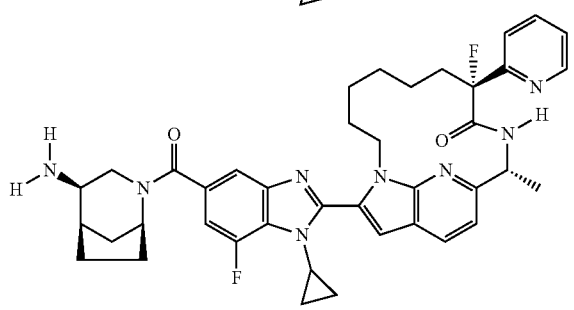
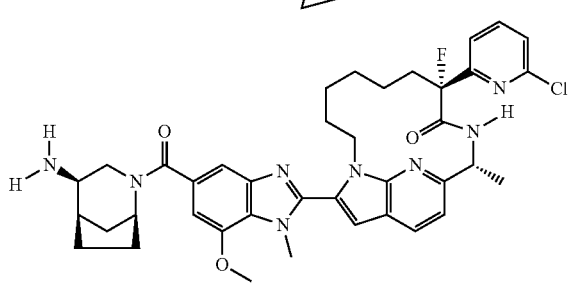
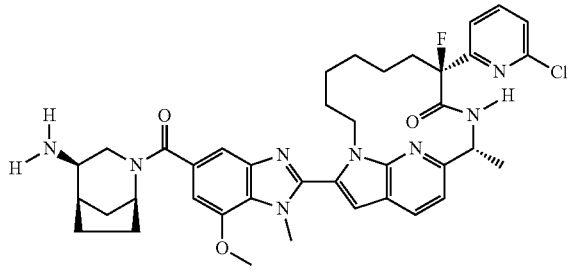
1428
-continued
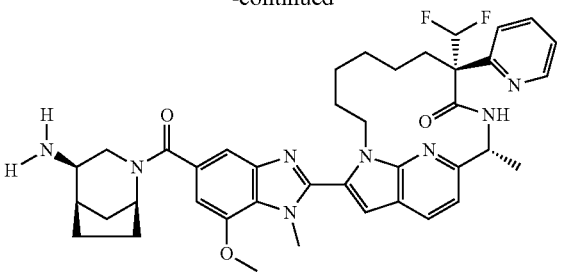
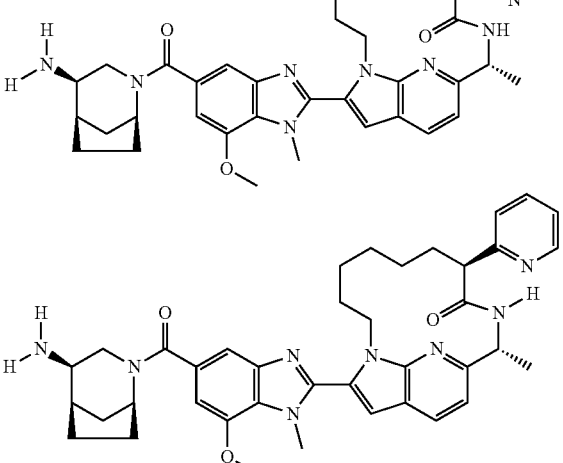
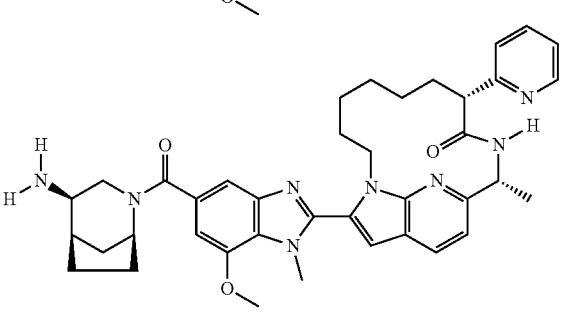
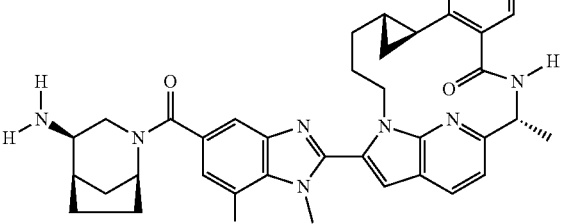
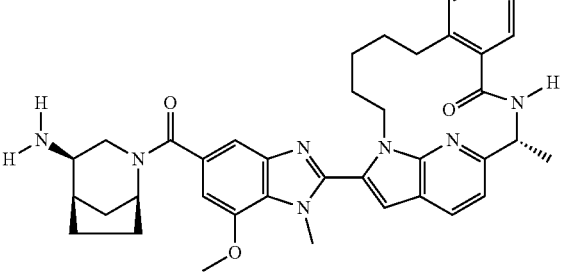

1429
-continued
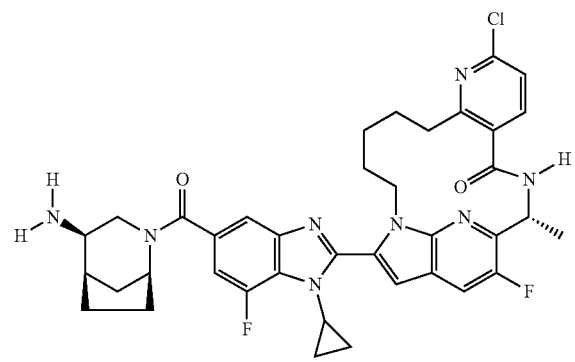
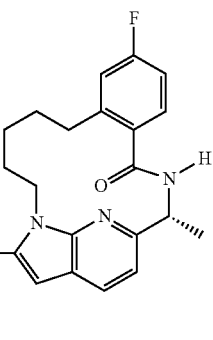
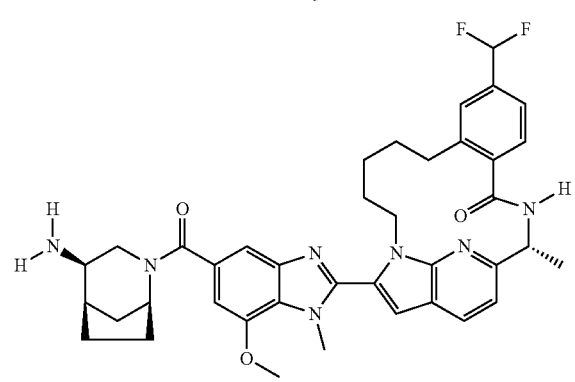
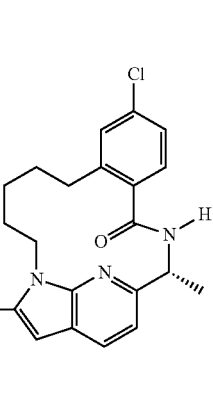
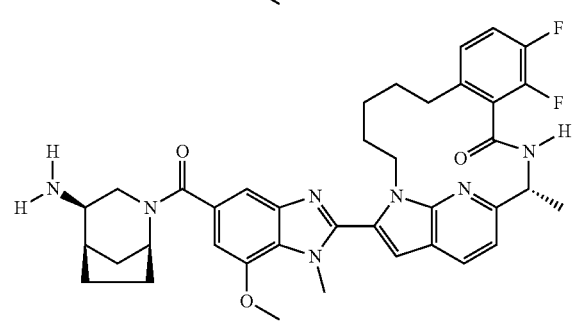
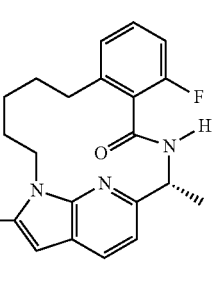
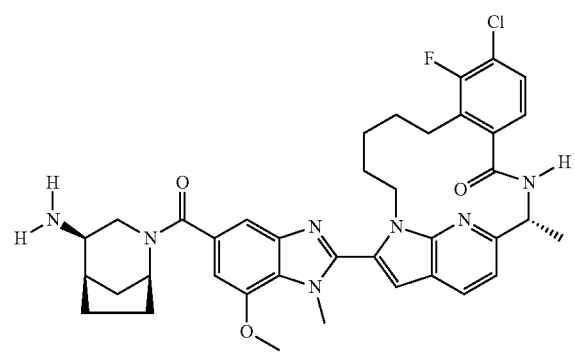
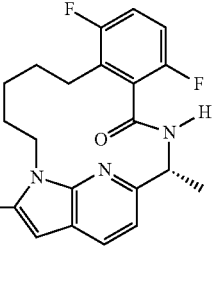
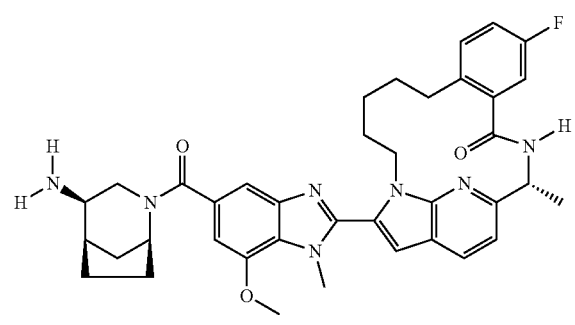
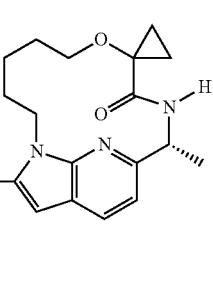
1430
-continued 1431
-continued
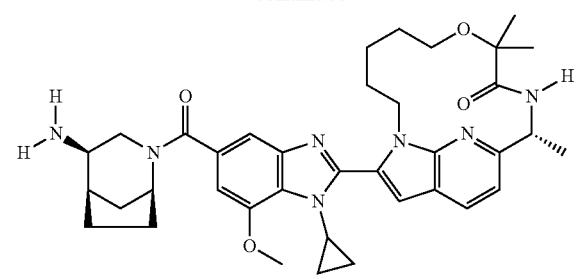
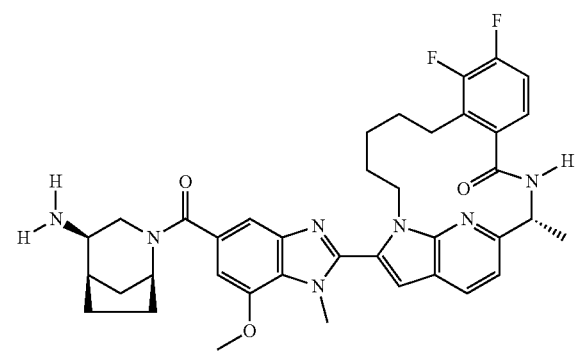
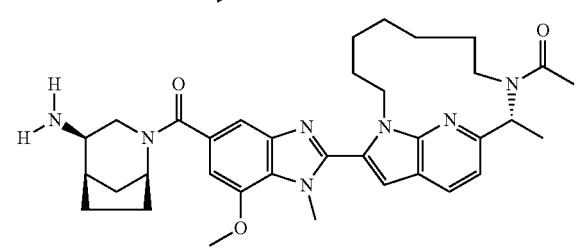
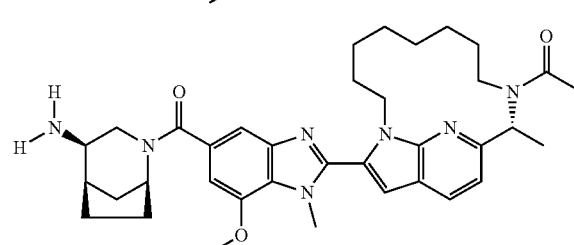
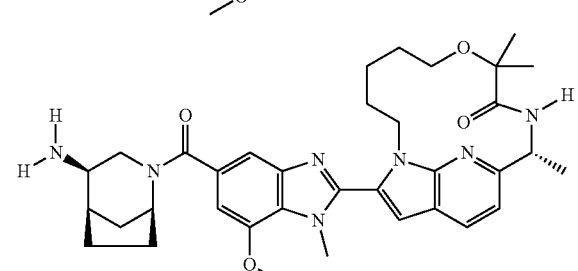
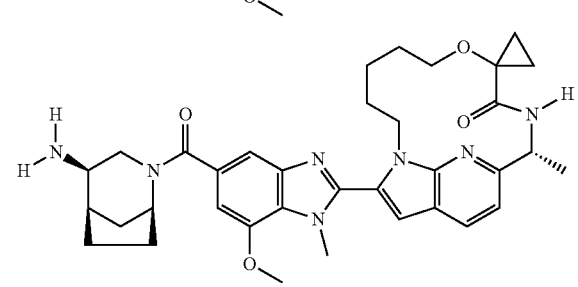
1432
-continued
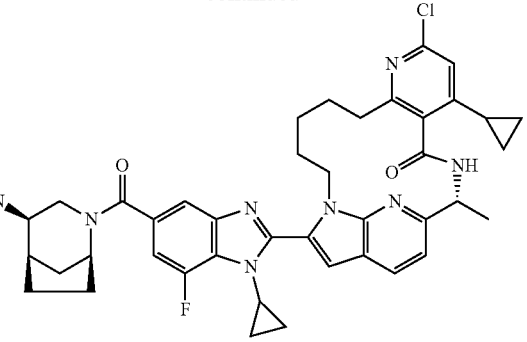
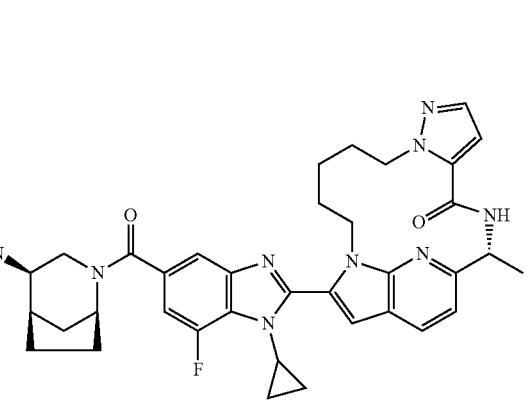
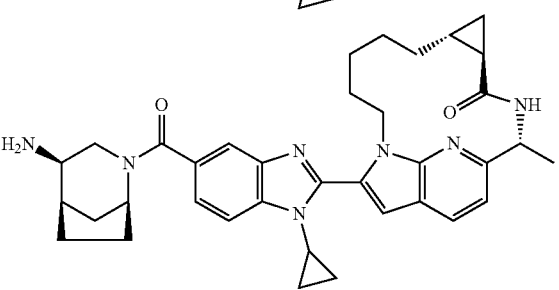
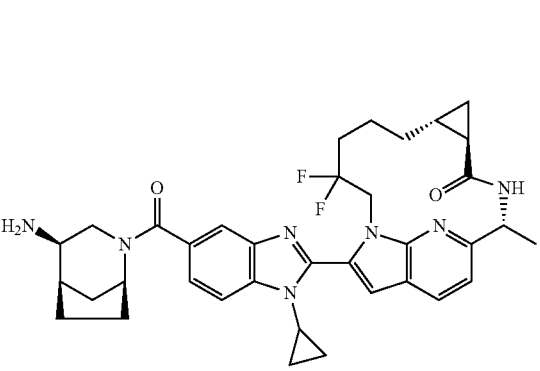
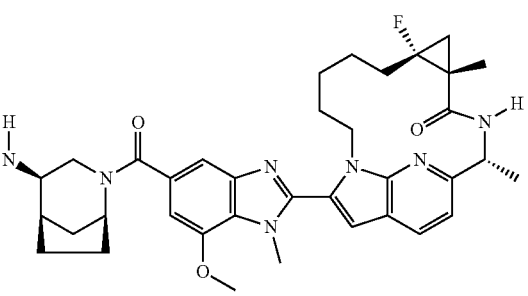

1433
-continued
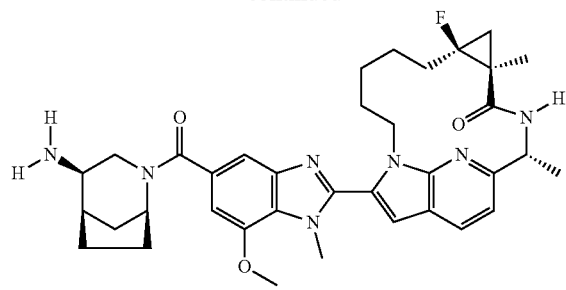
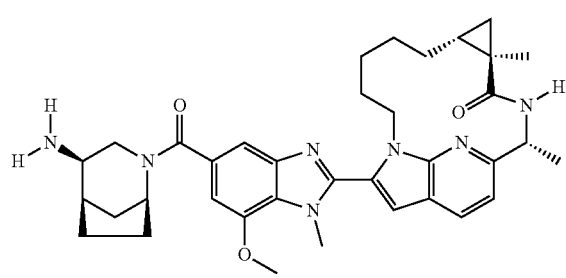
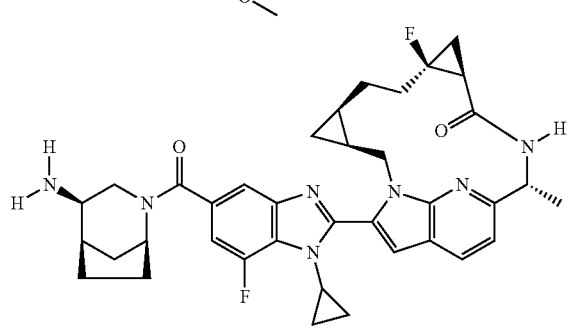
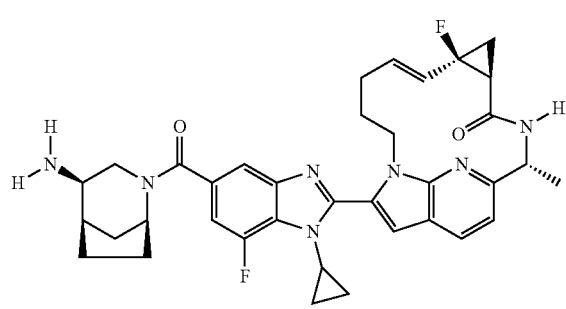
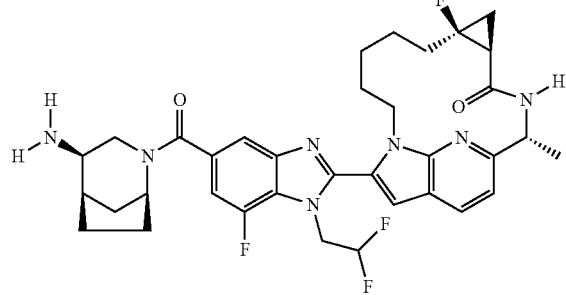
1434
-continued
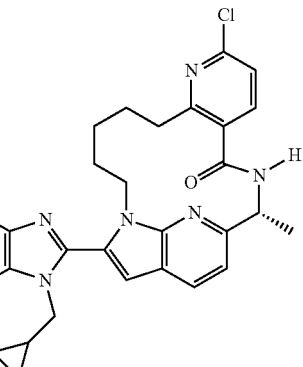
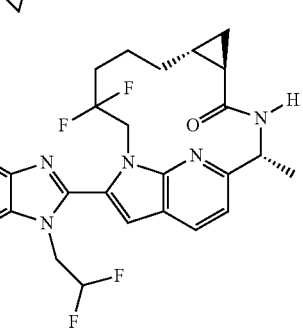
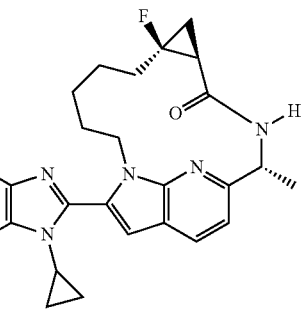
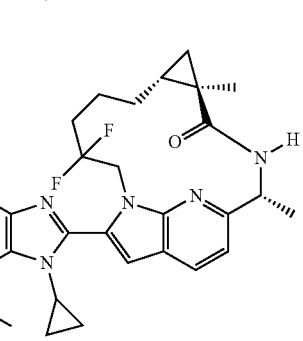

1435
-continued
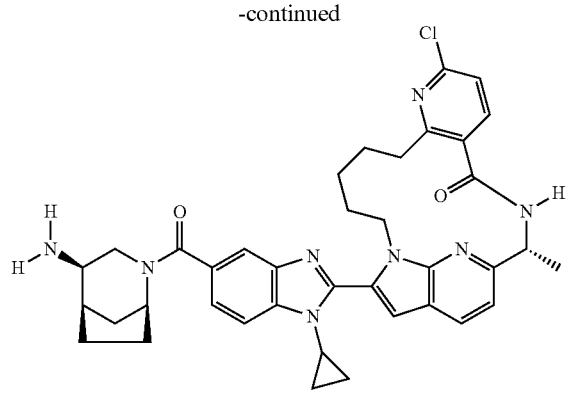
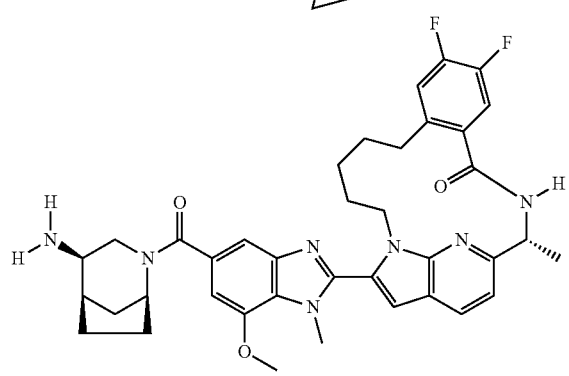
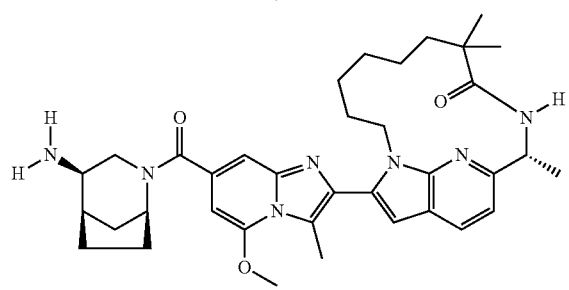
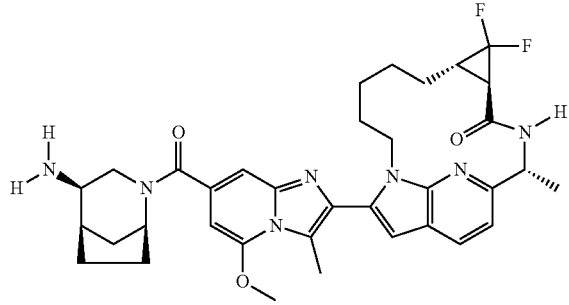
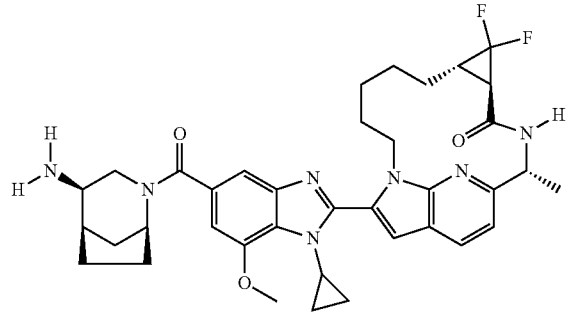
1436
-continued
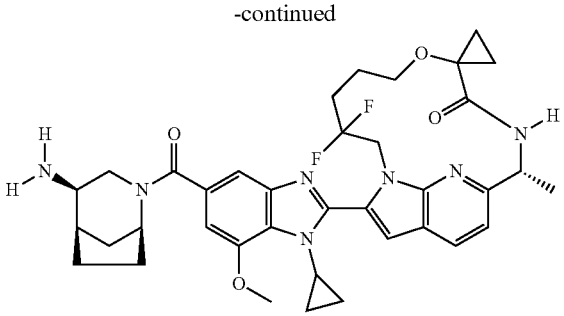
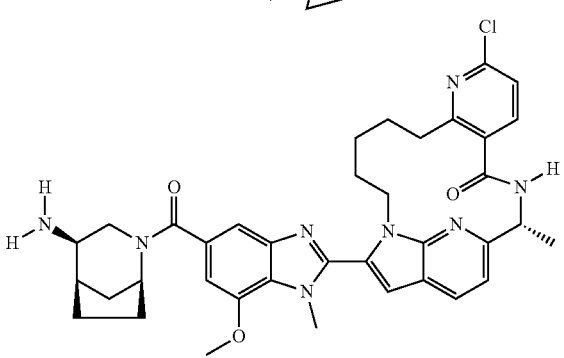
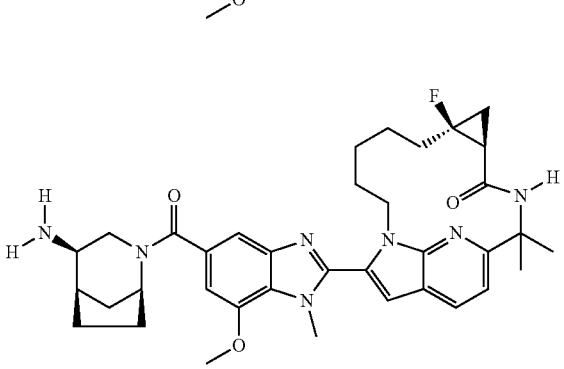
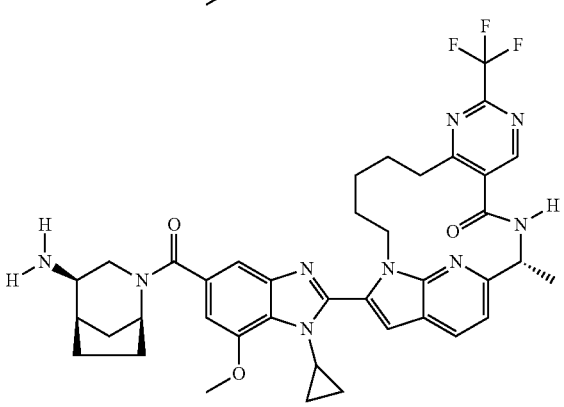
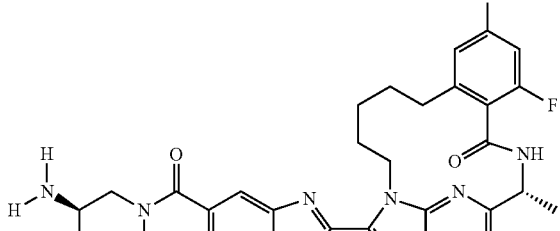
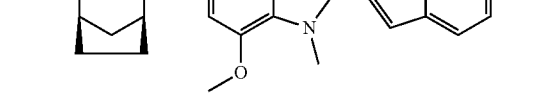

1437
-continued
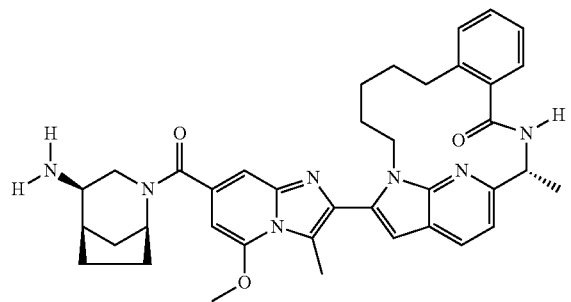
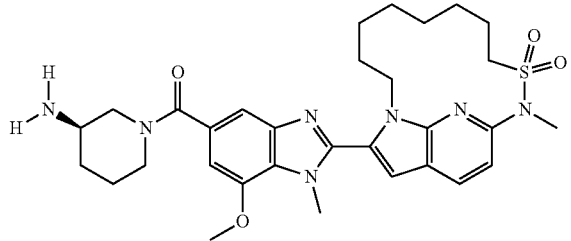
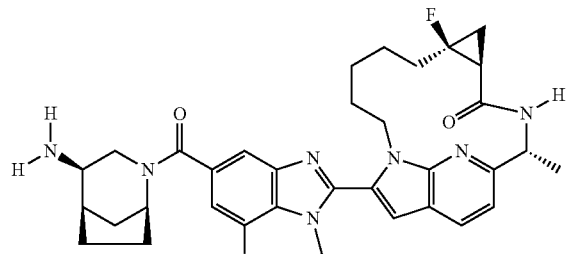
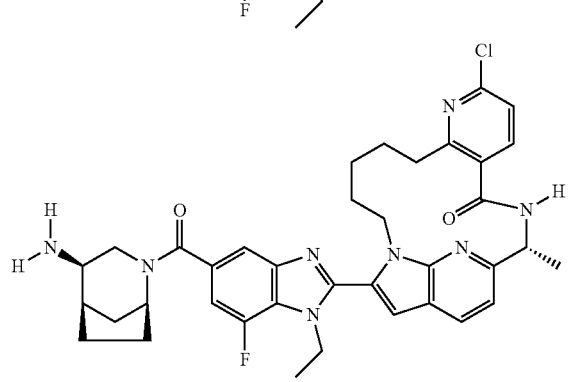
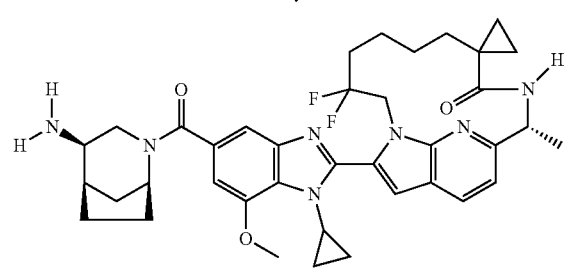
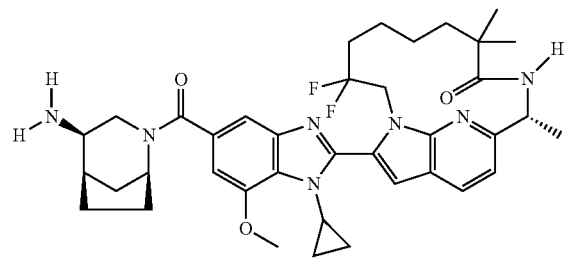
1438
-continued
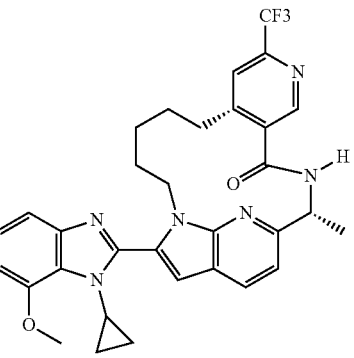
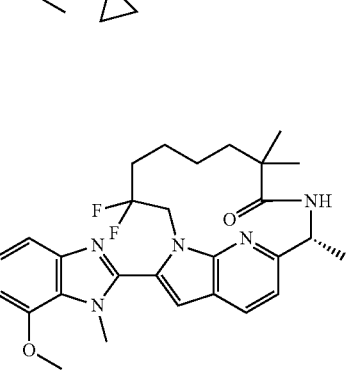
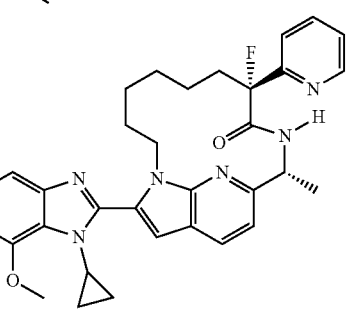
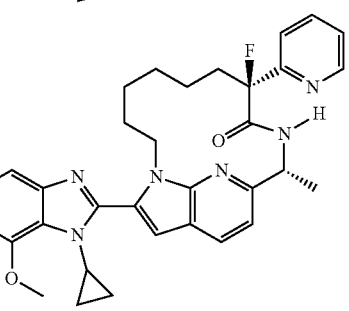
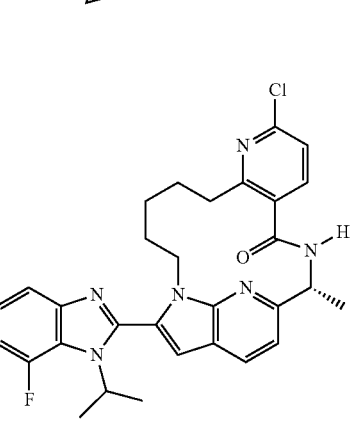

1439
-continued
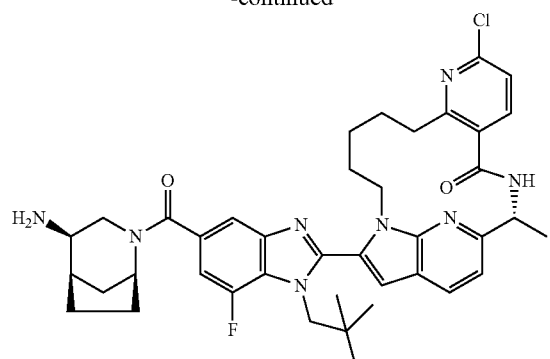
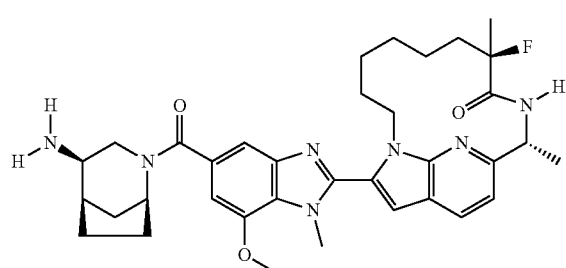
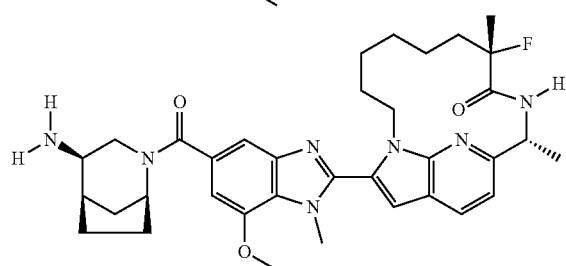
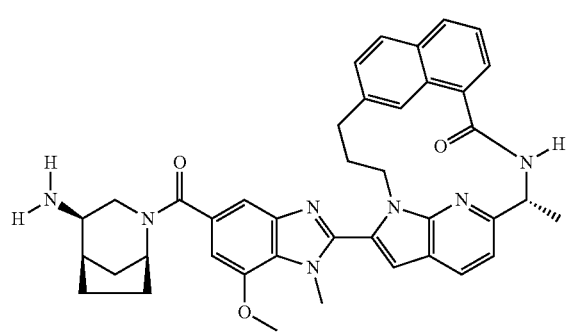
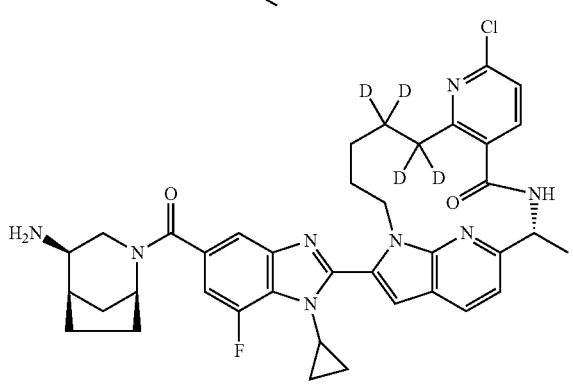
1440
-continued
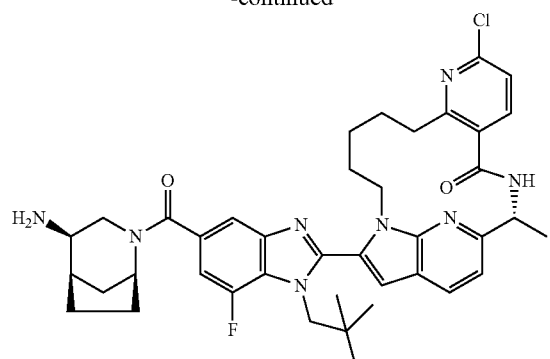
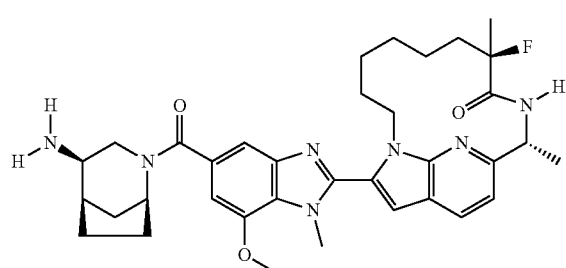
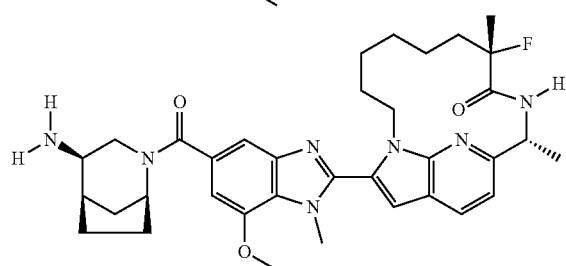
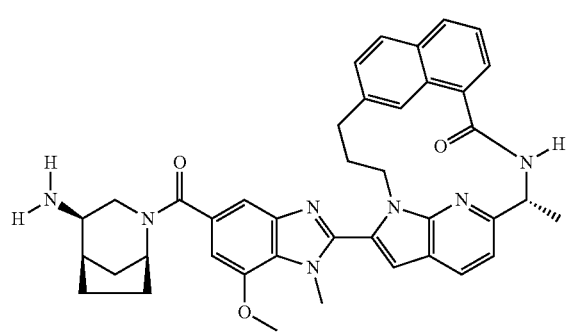
or
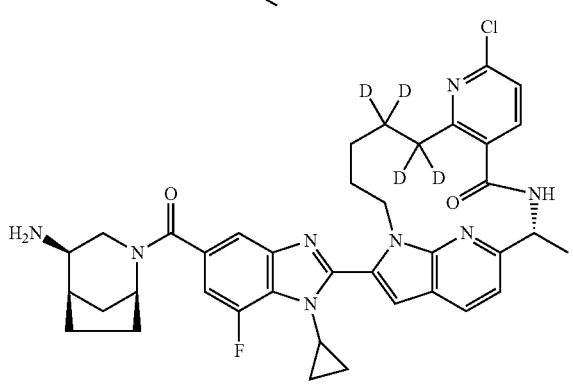
or a pharmaceutically acceptable salt, stereoisomer, mixture of stereoisomers, or tautomer thereof.
14. A pharmaceutical composition comprising a compound according to claim 1 or a pharmaceutically acceptable salt, stereoisomer, mixture of stereoisomers, or tautomer thereof, and at least one pharmaceutically acceptable excipient.

15. The method of claim 1, or a pharmaceutically acceptable salt thereof, having the structure of
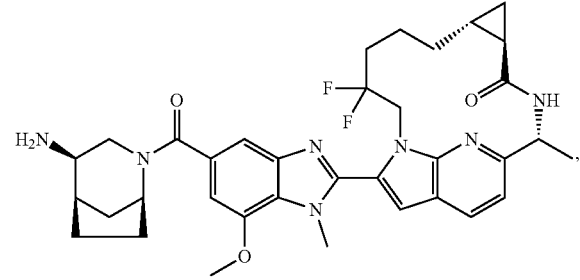
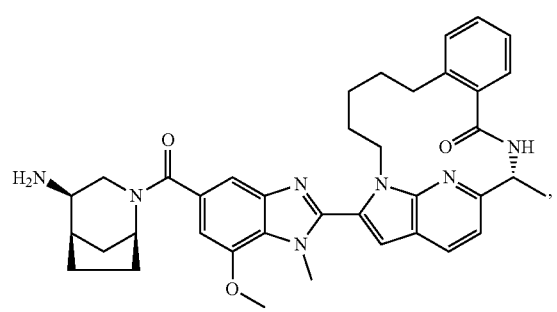
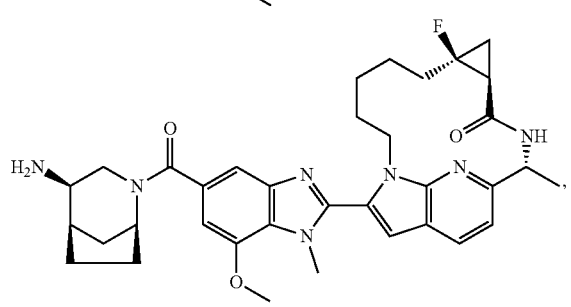
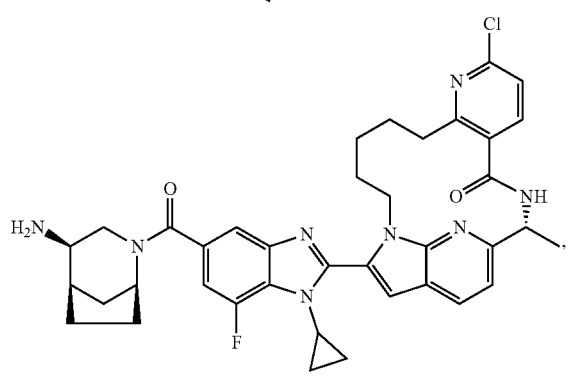
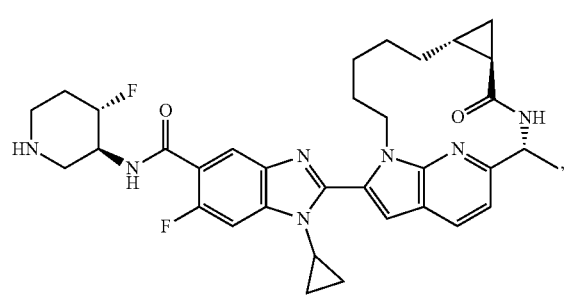
-continued
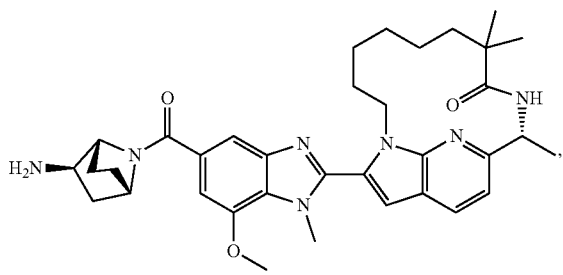
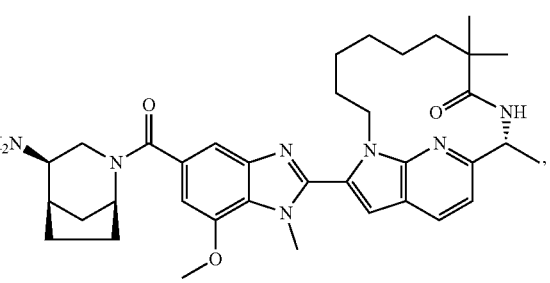
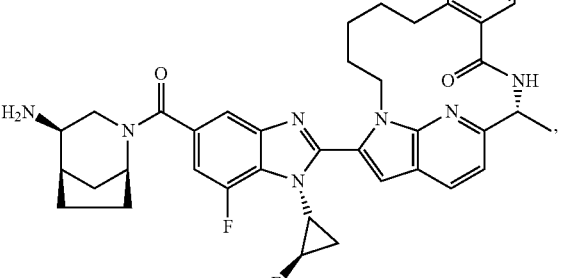
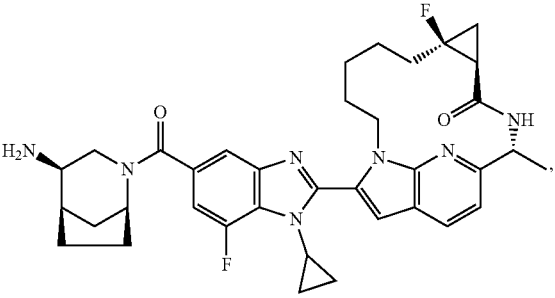
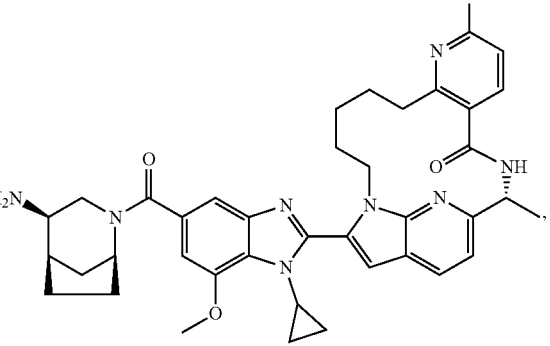

1443
-continued
1444
-continued
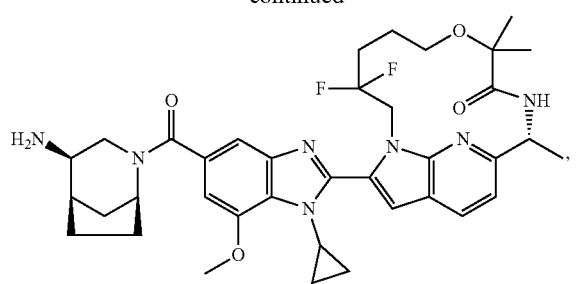
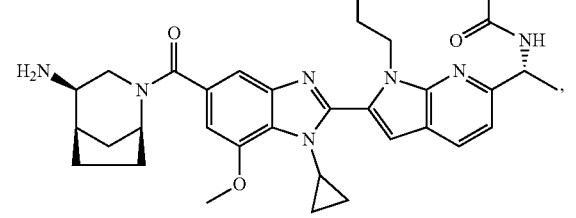
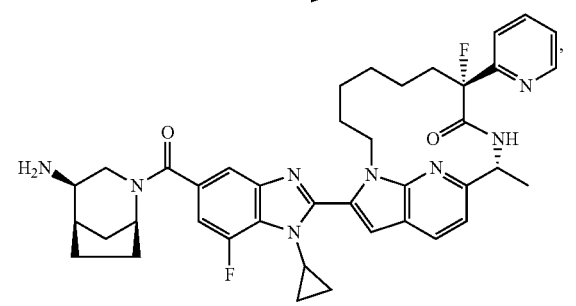
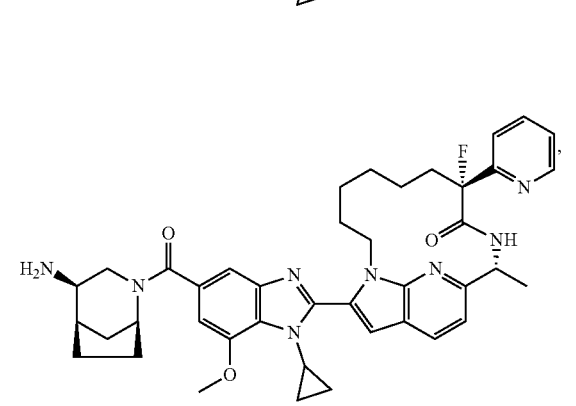
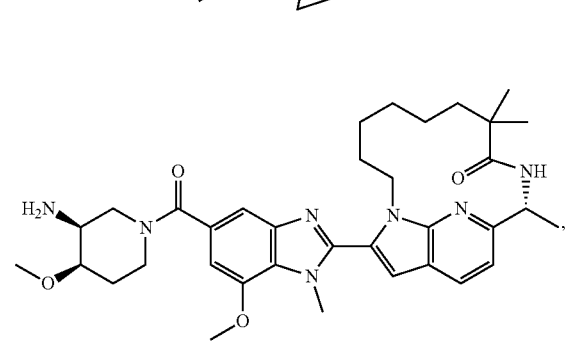
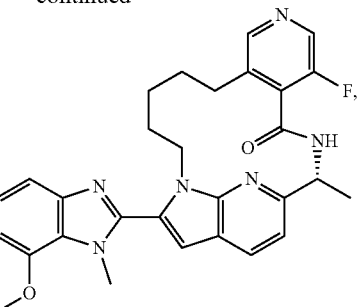

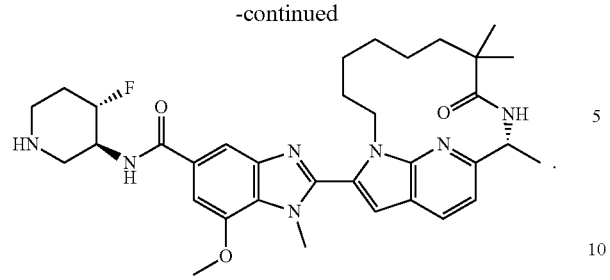
* * * * *